United States Patent
Benson et al.

(10) Patent No.: US 6,356,845 B1
(45) Date of Patent: Mar. 12, 2002

(54) **CRYSTALLIZATION AND STRUCTURE DETERMINATION OF *STAPHYLOCOCCUS AUREUS* UDP-N-ACETYLENOLPYRUVYLGLUCOSAMINE REDUCTASE (*S. AUREUS* MURB)**

(75) Inventors: Timothy E. Benson, Kalamazoo; Melissa S. Harris, Marshall, both of MI (US)

(73) Assignee: Pharmacia & Upjohn Company, Kalamazoo, MI (US)

(*) Notice: Subject to any disclaimer, the term of this patent is extended or adjusted under 35 U.S.C. 154(b) by 0 days.

(21) Appl. No.: 09/632,947

(22) Filed: Aug. 4, 2000

Related U.S. Application Data

(60) Provisional application No. 60/147,164, filed on Aug. 4, 1999.

(51) Int. Cl.$^7$ .................. G01N 33/48; G01N 33/50; C12N 9/00
(52) U.S. Cl. .................. 702/19; 435/183; 702/27
(58) Field of Search .................. 435/183, 174, 435/69.2; 702/19, 27

(56) References Cited

FOREIGN PATENT DOCUMENTS

| | | |
|---|---|---|
| EP | 0 786 519 A2 | 7/1997 |
| EP | 0899335 A2 | 3/1999 |
| WO | WO 99/47639 | 9/1999 |
| WO | WO 99/47662 | 9/1999 |
| WO | WO 00/12678 | 3/2000 |
| WO | WO 01/16292 A2 | 3/2001 |

OTHER PUBLICATIONS

P. A. Bartlett et al., "CAVEAT: A program to facilitate the structure–derived design of Biologically active molecules", *Molecular Recognition in Chemical and Biological Problems,* Special Publ., Royal Chem. Soc., 78 182–196 (1989).

T.E. Benson et al., "Overexpression, Purification, and Mechanistic Study of UDP–N–Acetylenolpyruvylglucosamine Reductase", *Biochemistry,* 32 2024–2030 (1993).

T.E. Benson et al., "Kinetic Characterization of Wild–Type and S229A Mutant MurB: Evidence for the role of Ser 229 as a General Acid", *Biochemistry,* 36 796–805 (1997).

T.E. Benson et al., "X–ray Crystal Structures of the S229A Mutant and Wild–Type MurB in the Presence of the Substrate Enolpyruvyl–UDP–N–acetylglucosamine at 1.8 Å Resolution", *Biochemistry,* 36 806–811 (1997).

T.E. Benson et al., "An enzyme–substrate complex involved in bacterial cell wall biosynthesis", *Nat. Struct. Biol.,* 2 644–653 (1995).

T.E. Benson et al., "Crystallization and preliminary X–ray crystallographic studies of UDP–N–acetylenolpyruvylglucosamine reductase", *Protein Science,* 3 1125–1127 (1994).

T. E. Benson et al., "The structure of the substrate–free form of MurB, an essential enzyme for the synthesis of bacterial cell walls", *Structure,* 4 47–54 (1996).

T.L. Blundell et al., *Protein Crystallography,* Academic Press (1976) (cover page, publication page and table of contents).

H.–J. Bohm, "The computer program LUDI: A new method for the de novo design of enzyme inhibitors", *J. Comp. Aid. Molec. Design,* 6 61–78 (1992).

E.D. Brown et al., "MurA (MurZ), the Enzyme that catalyzes the first committed step in peptidoglycan biosynthesis is essential in *Escherichia coli*", *J. Bacteriol.,* 177 4194–7 (1995).

A. T. Brunger, "Recent developments for crystallographic refinement of macromolecules", *Methods. Mol. Biol,* 56 245–66 (1996).

A.T. Brunger, "Crystallographic Refinement by Simulated Annealing Application to a 2.8 Å Resolution Structure of Aspartate Aminotransferase", *J. Mol. Biol.,* 203 803–16 (1988).

A. T. Brunger, "Free R value: a novel statistical quantity for assessing the accuracy of crystal structures", *Nature,* 355 472–75 (1992).

A.T. Brunger, "X–PLOR version 3.1: A system for X–ray Crystallography and NMR", New Haven: Yale Univ. Press, (1992), (Cover Page, Publication Page and Table of Contents).

K. Bupp et al., "The final step of peptidoglycan subunit assembly in *Escherichia coli* occurs in the cytoplasm", *J. Bacteriol.,* 175 1841–3 (1993).

D. Chamberlain et al, "Possible arrangement of the five domains in human complement factor I as determined by a combination of X–ray and neutron scattering and homology modeling", *Biochemistry,* 37 13918–29 (1998).

M. L. Cohen, "Epidemiology of Drug Resistance: Implications for a Post–Antimicrobial Era", *Science,* 257 1050–5 (1992).

Collaborative Computational Project, N.4, "The CCP4 Suite: Programs for Protine Crystallography", *Acta Cryst.,* D50 760–63 (1994).

K.D. Cowtan et al., "Improvement of Macromolecular Electron–Density Maps by the Simultaneous Application of Real and Reciprocal Space Constraints", *Acta Cryst.,* D49 148–57 (1993).

K.D. Cowtan et al., "Miscellaneous Algorithms for Density Modification", *Acta Cryst.,* D54 487–93 (1998).

(List continued on next page.)

*Primary Examiner*—Ardin H. Marschel
*Assistant Examiner*—Shubo "Joe" Zhou
(74) *Attorney, Agent, or Firm*—Mueting, Raasch & Gebhardt, P.A.

(57) ABSTRACT

The substrate free form of *Staphylococcus aureus* UDP-N-acetylenolpyruvylglucosamine reductase (*S. aureus* MurB) has been crystallized, and the three dimensional x-ray crystal structure has been solved to 2.3 Å resolution. The x-ray crystal structure is useful for solving the structure of other molecules or molecular complexes, and designing inhibitors of *S. aureus* MurB.

7 Claims, 625 Drawing Sheets

OTHER PUBLICATIONS

H. Dobbek et al., "Crystal structure and mechanism of CO dehydrogenase, an molybdo iron–sulfur flavoprotein containing S–selanycysteine", *Proc. Natl. Acad. Sci USA, 96* 8884–89 (cover date: Aug. 3, 1999).

T. J. Doughery et al., "The *Escherichia coli* Mutant Requiring D–Glutamic Acid is the Result of Mutations in Two Distinct Genetic Loci" *J. Bacteriol., 175* 111–6 (1993).

R.J. Doyle et al., "Elastic, flexible peptidoglycan and bacterial cell wall properties", *Trends Microbiol., 2* 57–60 (1994).

K. Duncan et al., "Purification and characterization of the D–Alanyl–D–alanine–Adding enzyme from *Escherichia coli*", *Biochemistry, 29* 2379–86 (1990).

K. Ehlert et al., "Specificities of FemA and FemB for different glycine residues: FemB cannot substitute for FemA in staphylococcal peptidoglycan pentaglycine side chain formation", *J. Bacteriol., 179* 7573–6 (1997).

M.B. Eisen et al., "Hook: A program for finding novel molecular architectures that satisfy the chemical and steric requirements of a macromolecule binding site", *Proteins: Struc., Funct., Genet., 19* 199–221 (1994).

S. V. Evans "SETOR: Hardware–lighted three–dimensional solid model representations of macromolecules", *J. Mol. Graph., 11* 134–8 (1993).

V. Gillet et al., "Sprout: A program for structure generation", *J. Comput. Aided Mol. Design, 7* 127–153 (1993).

P.J. Goodford, "A computational procedure for determining energetically favorable binding sites on biologically important macromolecules", *J. Med. Chem., 28* 849–857 (1985).

D.S. Goodsell et al., "Automated Docking of Substrates to Proteings by Simulated Annealing", *Proteins: Struct. Funct. Genet., 8* 195–202 (1990).

D. A. Gschwend et al., "Molecular Docking Towards Drug Discovery", *Journal of Molecular Recognition, 9,* 175–186 (1996).

M. Gubler et al., "Overexpression, Purification, and Characterization of UDP–N–Acetylmuramyl: L–Alanine Ligase for *Escherichia coli*", *J. Bacteriol., 178* 906–10 (1996).

W.A. Hendrickson et al., "Selenomethionyl proteins produced for analysis by multiwavelength anomalous diffraction (MAD): a vehicle for direct determination of three–dimensional structure", *EMBO J., 9*(5):1665–1672 (1990).

W. A. Hendrickson, "Determination of Macromolecular Structures from Anomalous Diffraction of Synchrotron Radiation", *Science, 254* 51–8 (1991).

M. Ikeda et al., "The *Escherichia coli mra* Y Gene Encoding UDP–N–Acetylmuramoyl–Pentapeptide: Undecaprenyl–Phosphate Phospho–N–Acetylmuramoyl–Pentapeptide Transferase", *J. Bacteriol., 173* 1021–6 (1991).

J.–S. Jiang et al., "Protein Hydration Observed by X–ray Diffraction Solvation Properties of Penicillpepsin and Neuraminidase Crystal Structures", *J. Mol. Biol., 243* 100–15 (1994).

U. Kopp et al., "Staphylococcal Peptidoglycan Interpeptide Bridge Biosynthesis: A Novel Antistaphylococcal Target?", *Microb. Drug. Resist., 2* 29–41 (1996).

P. Kraulis, "MOLSCRIPT: a program to produce both detailed and schematic plots of protein structures", *J. Appl. Cryst., 24* 946–950 (1991).

I.D. Kuntz et al., "A Geometric Approach to Macromolecule–Ligand Interactions", *J. Mol. Biol., 161* 269–288 (1982).

I.D. Kuntz et al., "Structure–based Molecular Design", *Accounts of Chemical Research, US, American Chemical Society, 27* 117–23 (1994).

R.A. Laskowski et al., "PROCHECK: a program to check the stereochemical quality of protein structures." *J. Appl. Cryst., 26* 283–91 (1993).

E. Lattman, "Use of the Rotation and Translation Functions," *Meth. Enzymol., 115* 55–77 (1985).

G. Lauri et al., "CAVEAT: A program to facilitate the design of organic molecules", *J. Comput. Aided Mol. Des., 8* 51–66 (1994).

W. J. Lees et al., "(E)–Enolbutyryl–UDP–N–acetylglucosamine as a Mechanistic Probe of UDP–N–acetylenolpyruvylglucosamine Reductase (MurB)", *Biochemistry 35,* 1342–1351 (1996).

D. Liger et al., "Over–production, purification and properties of the uridine–diphosphate–N–acetylmuramate:L–alanine ligase for *Escherichia coli*", *Eur. J. Biochem., 230* 80–7 (1995)

H. Maidhof et al., "femA, Which encodes a factor essential for expression of methicillin resistance, affects glycine content of peptidoglycan in methicillin–resistant and methicillin–susceptible *Staphylococcus aureus* Strains", *J. Bacteriol., 173* 3507–13 (1991).

J. L. Marquardt et al., "Cloning and sequencing of *Escherichia coli* murZ and purification of its product, a UDP–N–Acetylglucosamine Enolpyruvyl Transferase", *J. Bacteriol., 174* 5748–52 (1992).

Y.C. Martin, "3D Database Searching in Drug Design", *J. Med. Chem., 35* 2145–2154 (1992).

I. N. Maruyama et al., "Determination of Gene Products and coding Regions from the murE–murF Region of *Escherichia cole*", *J. Bacteriol., 170* 3786–8 (1988).

A. Mattevi et al., "Crytsal structures and inhibitor binding int he octameric flavoenzyme vanillyl–alcohol oxidase; the shape of the active–site cavity controls substrate specificity", *Structure, 5* 907–20 (1997).

F.S. Matthews et al., "Three–Dimensional Structure of p–Cresol Methylhydroxylase (Flavocytochrome c) from *Pseudomonas putida* at 3.0–Å Resolution", *Biochemistry, 30* 238–47 (1991).

E.C. Meng et al., "Automated Docking with Grid–Based Energy Evaluation", *J. Comp. Chem., 13* 505–524 (1992).

D. Mengin–Lecreulx et al., "The murG Gene of *Escherichia coli* Codes for the UDP–N–Acetylglucosamine:N–Acetylmuramyl–(Pentapeptide) Pyrophosphoryl–Undecaprenol N–Acetylglucosamine Transferase Involved in the Membrane steps of Peptidoglycan Synthesis", *J. Bacteriol., 173* 4625–36 (1991).

E. A. Merrit et al., "Raster3D: Photorealistic Molecular Graphics", *Meth. Enzymol., 277* 505–24 (1997).

*Meth. Enzymol., 114 & 115,* H.W. Wycokoff et al., eds., Academic Press (1985) (Cover page, publication page, and table of contents).

C. Michaud et al., "Over–production, purification and properties of the uridine–diphosphate–N–acetylmuramoyl–L–alanyl–D–glutamate: meso–2,6–diaminopimelate ligase from *Eschericha coli*", *Eur. J. Biochem., 194* 853–61 (1990).

M. Michel et al., "Methicillin–resistant *Staphylococus aureus* and vanocomycin–resistant enterococci: therapeutic realities and possibilites", *Lancet, 349* 1901–1906 (1997).

A. Miranker et al., "Functionality Maps of Binding Sites: A Multiple Copy Simultaneous Search Method", *Proteins: Struct. Funct. Gen., 11* 29–34 (1991).

A.G. Murzin, "Structural classificaiton of proteins: new superfamilies", *Cur. Op. Struct. Biol., 6* 386–94 (1996).

Y. Nishibata et al., "Automatic Creation of Drug Candidate Structures Based on Receptor Structure. Starting Point for Artificial Lead Generation.", *Tetrahedron, 47* 8985–8990 (1991).

C.J. Noren et al., "A General Method for Site–Specific Incorporation of Unnatural Amino Acids into Proteins", *Science, 244* 182–188 (1989).

S. L. Ohringer et al., "Crystallization and preliminary crystallographic analysis of *E. coli* uridine 5'–diphospho–N–acetylenolpyruvylglucasamine reductase in two new crystal forms", *Acta Cryst, D52* 586–588 (1996).

M. J. Pucci et al., "Cloning and Identification of the *Escherichai coli murB* DNA Sequence, Which Encodes UDP–N–Acetylenolpyruvoylglucosamine Reductase", *J. Bacteriol., 174* 1690–3 (1992).

V. Ramakrishnan et al., "Crystal structure of globular domain of histone H5 and its implications for nucleosome binding", *Nature, 362* 219–23 (1993).

W. J. Ray, Jr., "Effect of Polyethylene Glycol–400 at Low Concentrations on Long–Term Growth of Muscle Phosphoglucomutase Crystals from Concentrated Salt Solutions", *Proteins: Structure Function and Genetics, 14* 300–308; (1992) (abstract only).

P. E. Reynolds, "The Essential Nature of Staphylococcal Penicillin–Binding Proteins", in *Antibiotic Inhibition of Bacterial Cell Surface Assembly and Function* (P. Actor et al., Eds.) 343–51, American Society for Microbiology, Washington (1988).

L.M. Rice et al., "Torsion Angle Dynamics: Reduced Variable Conformational Sampling Enhances Crystallographic Structure Refinement", *Proteins, 19* 277–90 (1994).

M.G. Rossman, ed., "The Molecular Replacement Method: A Collection of Papers on the Use of Noncrystallographic Symmetry," *Int. Sci. Rev. Ser.,* No. 13, Gordon & Breach, New York (1972) (Cover page, publication page, and table of contents).

M. G. Rossman et al., "Chemical and biological evolution of a nucleotide–binding protein", *Nature, 250* 194–9 (1974).

Ryuichi et al., "Homology modeling of gelatinase catalytic domains and docking simulations of novel sulfonamide inhibitors", *Journal of Medicinal Chemistry, 42* 1723–38 (May 20, 1999) (abstract only).

J. S. Sack, "Chain–A Crystallographic Modeling Program", *J. Mol. Graph., 6* 224–25 (1988).

G.M Sheldrick et al., "Structure Solution by Iterative Peaklist Optimization and Tangent Expansion in Space Group P1", *Acta Cryst., B51* 423–31 (1995).

T. Tatusove et al., "Blast 2 Sequences, a new tool for comparing protein and nucleotide sequences", *FEMS Microbiol Lett, 714* 247–50 (1999) (program available at http://www.ncbi.nlm.nih.gov/gorf/b12.html).

J. Travis, "Proteins and Organic Solvents Make an Eye–Opening Mix", *Science, 262,* 1374 (1993).

G.D. Van Duyne et al., "Atomic Structures of the Human Immunophilin FKBP–12 Complexes with FK506 and Rapamycin", *J. Mol. Biol., 229* 105–24 (1993).

A. Wada et al., "Penicillin–Binding Protein 1 of *Staphylococcus aureus* Is Essential for Growth", *J. Bacteriol., 180* 2759–65 (1998).

W. Wikoff et al., "Crystallization and preliminary X–ray analysis of the dsDNA bacteriophage HK97 mature empty capsid", *Virology, 243* 113–18 (1998) (abstract only).

A.W. Wyke et al., "A Role in vivo for Penicillin–Binding Protein–4 of *Staphylococcus aureus"*, *Eur. J. Bioch., 119* 389–93 (1981).

Erli Zhang et al., "Crystallizaiton and initial spectroscopic characterization of the heme–containing dehaloperoxidase from the marine polychaete Amphitrite ornata", *Acta Crystallographica Section D Biological Crystallography, 52* 1191–93 (1996) (abstract only).

T. Arakawa et al., "Theory of Protein Solubility," *Methods in Enzymology, 114,* 49–76 (1985).

J. Drenth, "Principles of Protein X–ray Crystallography, " Springer–Verlag New york, Inc., (1994), (Cover Page, Publication Page, Table of Contents and Chapters 1–2).

R. Kiyama et al., "Homology modeling of gelatinase catalytic domains and docking simulations of novel sulfonamide inhibitors," *J. Med. Chem., 42,* 1723–1738 (1999).

W.J. Ray Jr., "Effect of Polyethylene Glycol–400 at Low Concentrations on Long–Term Growth of Muscle Phosphoglucomutase Crystals from Concentrated Salt Solutions," *Proteins Structure Function and Genetics, 14,* 300–308 (1992).

W. Wikoff et al., "Crystallization and Preliminary X–ray Analysis of the dsDNA Bacteriophage HK97 Mature Empty Capsid," *Virology, 243,* 113–118 (1998).

E. Zhang et al., "Crystallization and initial spectroscopic characterization of the heme–containing dehaloperoxidase from the marine polychaete Amphitrite ornata," *Acta Crystallographica Section D Biological Crystallography, 52,* 1191–93 (1996).

Z Otwinowski, *Isomorphous replacement and anomalous scattering,* (W. Wolf et al., eds.) 80–86, SERC Daresbury Laboratory, Warrington (1991).

```
SEQ. ID NO:1    1  MRGSHHHHHHTDPINKDIYQALQQLIPNEKIKVDEPLKRYTYTKTGGNAD          50
SEQ. ID NO:2    1  .................................................          18
                                                                      MDHSLKPWNTFGIDHNAQ

51  FYITPTKNEEVQAVVKYAYQNEIPVTYLGNGSNIIIREGGIRGIVISLLS         100
               19  HIVCAEDEQQLLNAWQYATAEGQPVLILGEGSNVLFLEDYRGTVIINRIK          68

101  LDHIEVSDDA..IIAGSGAAIIDVSRVARDYALTGLEFACGIPGSIGGAV         148
               69  GIEIHDEPDAWYLHVGAGENWHRLVKYTLQEGMPGLENLALIPGCVGSSP         118

149  YMNAGAYGGEVKDCIDYALCVN.EQGSLIKLTTKELELDYRNSIIQKEH.         196
              119  IQNIGAYGVELQRVCAYVDSVELATGKQVRLTAKECRFGYRDSIFKHEYQ         168

197  ..LVVLEAAFTLAP.........GK........MTEIQAKMDDLTERRESKQ         229
              169  DRFAIVAVGLRLRLPKEWQPVLTYGDLTRLDPTTVTPQQVFNAVCHMRTTKL         218

230  P..LEYPSCGSVFQRP........PG.......................HFAGKL         251
              219  PDPKVNGNAGSFFKNPVVSAETAKALLSQFPTAPNYPQADGSVKLAAGWL         268

252  IQDSNLQGHRIGGVESTKHAGFMVNVDNGTATDYENLIHYVQKTVKEKF         301
              269  IDQCQLKGMQIGGAAVHRQQALVLINEDNAKSEDVVQLAHHVRQKVGEKF         318

302  GIELNREVRIIGEHPKESLQPSLIS                                 
              319  NVWLEPEVRFIGASGEVSAVETIS.                                 
```

*Fig. 2*

```
REMARK  S. aureus MurB coordinates
REMARK  r= 0.20077 free_r= 0.223209
CRYST1   178.900   178.900   178.900   90.00   90.00   90.00 I213

X        Y        Z     Occ     B
ATOM      1   N    ASN    15       201.698  143.566  184.594  1.00  45.97
ATOM      2   CA   ASN    15       200.334  143.153  184.224  1.00  44.15
ATOM      3   CB   ASN    15       200.319  142.647  182.778  1.00  44.95
ATOM      4   CG   ASN    15       200.140  143.780  181.789  1.00  46.93
ATOM      5   OD1  ASN    15       199.427  144.755  182.053  1.00  47.83
ATOM      6   ND2  ASN    15       200.770  143.655  180.637  1.00  47.45
ATOM      7   C    ASN    15       199.782  142.098  185.183  1.00  43.98
ATOM      8   O    ASN    15       198.584  141.857  185.266  1.00  42.86
ATOM      9   N    LYS    16       200.677  141.450  185.924  1.00  43.58
ATOM     10   CA   LYS    16       200.269  140.451  186.894  1.00  42.80
ATOM     11   CB   LYS    16       201.459  140.096  187.786  1.00  45.32
ATOM     12   CG   LYS    16       202.387  138.990  187.303  1.00  48.30
ATOM     13   CD   LYS    16       203.472  138.663  188.388  1.00  50.61
ATOM     14   CE   LYS    16       204.414  137.547  187.898  1.00  52.44
ATOM     15   NZ   LYS    16       205.480  137.124  188.856  1.00  52.81
ATOM     16   C    LYS    16       199.213  141.080  187.820  1.00  41.48
ATOM     17   O    LYS    16       198.194  140.483  188.155  1.00  41.29
ATOM     18   N    ASP    17       199.528  142.309  188.207  1.00  40.25
ATOM     19   CA   ASP    17       198.748  143.094  189.144  1.00  40.20
ATOM     20   CB   ASP    17       199.481  144.426  189.412  1.00  43.40
ATOM     21   CG   ASP    17       200.614  144.278  190.410  1.00  46.45
ATOM     22   OD1  ASP    17       200.647  143.204  191.054  1.00  47.62
ATOM     23   OD2  ASP    17       201.451  145.212  190.568  1.00  47.70
ATOM     24   C    ASP    17       197.323  143.378  188.683  1.00  39.05
ATOM     25   O    ASP    17       196.352  143.332  189.478  1.00  39.81
ATOM     26   N    ILE    18       197.195  143.712  187.409  1.00  35.30
ATOM     27   CA   ILE    18       195.904  144.026  186.833  1.00  33.03
ATOM     28   CB   ILE    18       196.043  144.623  185.411  1.00  31.39
ATOM     29   CG2  ILE    18       194.660  144.772  184.769  1.00  29.11
ATOM     30   CG1  ILE    18       196.677  146.007  185.487  1.00  27.59
ATOM     31   CD1  ILE    18       197.153  146.554  184.157  1.00  25.73
ATOM     32   C    ILE    18       195.072  142.762  186.755  1.00  33.59
ATOM     33   O    ILE    18       193.906  142.761  187.129  1.00  33.78
ATOM     34   N    TYR    19       195.695  141.698  186.267  1.00  33.71
ATOM     35   CA   TYR    19       195.035  140.416  186.126  1.00  35.14
ATOM     36   CB   TYR    19       196.039  139.398  185.596  1.00  33.99
ATOM     37   CG   TYR    19       195.407  138.109  185.157  1.00  36.04
ATOM     38   CD1  TYR    19       194.067  138.063  184.775  1.00  36.31
ATOM     39   CE1  TYR    19       193.477  136.869  184.376  1.00  38.09
ATOM     40   CD2  TYR    19       196.140  136.929  185.127  1.00  37.77
ATOM     41   CE2  TYR    19       195.561  135.731  184.730  1.00  39.07
ATOM     42   CZ   TYR    19       194.230  135.708  184.357  1.00  39.30
ATOM     43   OH   TYR    19       193.659  134.522  183.964  1.00  40.97
ATOM     44   C    TYR    19       194.499  139.969  187.476  1.00  35.90
ATOM     45   O    TYR    19       193.343  139.578  187.583  1.00  35.95
ATOM     46   N    GLN    20       195.342  140.038  188.504  1.00  37.67
ATOM     47   CA   GLN    20       194.945  139.624  189.847  1.00  39.12
ATOM     48   CB   GLN    20       196.123  139.767  190.811  1.00  42.40
ATOM     49   CG   GLN    20       197.096  138.601  190.798  1.00  49.42
ATOM     50   CD   GLN    20       198.228  138.785  191.792  1.00  55.01
ATOM     51   OE1  GLN    20       198.943  137.837  192.118  1.00  57.28
ATOM     52   NE2  GLN    20       198.396  140.013  192.280  1.00  56.93
```

*FIG. 4A - 1*

| ATOM | 53 | C | GLN | 20 | 193.784 | 140.472 | 190.338 | 1.00 | 37.84 |
| --- | --- | --- | --- | --- | --- | --- | --- | --- | --- |
| ATOM | 54 | O | GLN | 20 | 192.851 | 139.969 | 190.963 | 1.00 | 37.86 |
| ATOM | 55 | N | ALA | 21 | 193.851 | 141.766 | 190.046 | 1.00 | 35.78 |
| ATOM | 56 | CA | ALA | 21 | 192.814 | 142.699 | 190.461 | 1.00 | 34.25 |
| ATOM | 57 | CB | ALA | 21 | 193.247 | 144.120 | 190.160 | 1.00 | 31.04 |
| ATOM | 58 | C | ALA | 21 | 191.499 | 142.393 | 189.759 | 1.00 | 33.86 |
| ATOM | 59 | O | ALA | 21 | 190.456 | 142.293 | 190.403 | 1.00 | 34.09 |
| ATOM | 60 | N | LEU | 22 | 191.555 | 142.245 | 188.439 | 1.00 | 33.57 |
| ATOM | 61 | CA | LEU | 22 | 190.364 | 141.950 | 187.651 | 1.00 | 33.18 |
| ATOM | 62 | CB | LEU | 22 | 190.731 | 141.772 | 186.179 | 1.00 | 30.11 |
| ATOM | 63 | CG | LEU | 22 | 191.123 | 143.065 | 185.464 | 1.00 | 29.39 |
| ATOM | 64 | CD1 | LEU | 22 | 191.745 | 142.750 | 184.117 | 1.00 | 28.83 |
| ATOM | 65 | CD2 | LEU | 22 | 189.895 | 143.934 | 185.296 | 1.00 | 28.33 |
| ATOM | 66 | C | LEU | 22 | 189.701 | 140.687 | 188.169 | 1.00 | 34.27 |
| ATOM | 67 | O | LEU | 22 | 188.475 | 140.592 | 188.216 | 1.00 | 35.65 |
| ATOM | 68 | N | GLN | 23 | 190.518 | 139.721 | 188.570 | 1.00 | 35.07 |
| ATOM | 69 | CA | GLN | 23 | 190.005 | 138.457 | 189.079 | 1.00 | 35.67 |
| ATOM | 70 | CB | GLN | 23 | 191.145 | 137.455 | 189.224 | 1.00 | 37.02 |
| ATOM | 71 | CG | GLN | 23 | 191.916 | 137.250 | 187.937 | 1.00 | 40.99 |
| ATOM | 72 | CD | GLN | 23 | 193.067 | 136.286 | 188.096 | 1.00 | 44.64 |
| ATOM | 73 | OE1 | GLN | 23 | 192.936 | 135.256 | 188.750 | 1.00 | 46.80 |
| ATOM | 74 | NE2 | GLN | 23 | 194.205 | 136.613 | 187.495 | 1.00 | 47.51 |
| ATOM | 75 | C | GLN | 23 | 189.290 | 138.638 | 190.406 | 1.00 | 35.26 |
| ATOM | 76 | O | GLN | 23 | 188.485 | 137.800 | 190.804 | 1.00 | 35.24 |
| ATOM | 77 | N | GLN | 24 | 189.585 | 139.734 | 191.092 | 1.00 | 35.79 |
| ATOM | 78 | CA | GLN | 24 | 188.939 | 140.015 | 192.365 | 1.00 | 37.19 |
| ATOM | 79 | CB | GLN | 24 | 189.759 | 141.024 | 193.178 | 1.00 | 39.85 |
| ATOM | 80 | CG | GLN | 24 | 191.089 | 140.514 | 193.707 | 1.00 | 44.87 |
| ATOM | 81 | CD | GLN | 24 | 191.072 | 139.033 | 194.028 | 1.00 | 49.06 |
| ATOM | 82 | OE1 | GLN | 24 | 190.249 | 138.562 | 194.816 | 1.00 | 49.73 |
| ATOM | 83 | NE2 | GLN | 24 | 191.986 | 138.289 | 193.414 | 1.00 | 51.86 |
| ATOM | 84 | C | GLN | 24 | 187.568 | 140.616 | 192.076 | 1.00 | 35.93 |
| ATOM | 85 | O | GLN | 24 | 186.656 | 140.538 | 192.896 | 1.00 | 36.23 |
| ATOM | 86 | N | LEU | 25 | 187.431 | 141.200 | 190.890 | 1.00 | 35.15 |
| ATOM | 87 | CA | LEU | 25 | 186.199 | 141.868 | 190.485 | 1.00 | 33.40 |
| ATOM | 88 | CB | LEU | 25 | 186.550 | 143.157 | 189.746 | 1.00 | 30.36 |
| ATOM | 89 | CG | LEU | 25 | 187.422 | 144.135 | 190.523 | 1.00 | 28.18 |
| ATOM | 90 | CD1 | LEU | 25 | 187.978 | 145.196 | 189.592 | 1.00 | 28.52 |
| ATOM | 91 | CD2 | LEU | 25 | 186.591 | 144.763 | 191.616 | 1.00 | 27.16 |
| ATOM | 92 | C | LEU | 25 | 185.188 | 141.094 | 189.645 | 1.00 | 33.42 |
| ATOM | 93 | O | LEU | 25 | 183.993 | 141.358 | 189.730 | 1.00 | 34.74 |
| ATOM | 94 | N | ILE | 26 | 185.641 | 140.152 | 188.829 | 1.00 | 33.21 |
| ATOM | 95 | CA | ILE | 26 | 184.708 | 139.413 | 187.983 | 1.00 | 32.14 |
| ATOM | 96 | CB | ILE | 26 | 184.614 | 140.062 | 186.590 | 1.00 | 32.83 |
| ATOM | 97 | CG2 | ILE | 26 | 184.023 | 141.452 | 186.690 | 1.00 | 32.16 |
| ATOM | 98 | CG1 | ILE | 26 | 186.010 | 140.169 | 185.985 | 1.00 | 33.96 |
| ATOM | 99 | CD1 | ILE | 26 | 186.034 | 140.004 | 184.495 | 1.00 | 37.35 |
| ATOM | 100 | C | ILE | 26 | 185.096 | 137.952 | 187.796 | 1.00 | 30.90 |
| ATOM | 101 | O | ILE | 26 | 186.272 | 137.602 | 187.869 | 1.00 | 29.35 |
| ATOM | 102 | N | PRO | 27 | 184.105 | 137.079 | 187.546 | 1.00 | 30.29 |
| ATOM | 103 | CD | PRO | 27 | 182.663 | 137.362 | 187.437 | 1.00 | 30.50 |
| ATOM | 104 | CA | PRO | 27 | 184.397 | 135.655 | 187.352 | 1.00 | 30.09 |
| ATOM | 105 | CB | PRO | 27 | 183.095 | 135.101 | 186.789 | 1.00 | 30.08 |
| ATOM | 106 | CG | PRO | 27 | 182.046 | 135.986 | 187.391 | 1.00 | 29.59 |
| ATOM | 107 | C | PRO | 27 | 185.582 | 135.467 | 186.413 | 1.00 | 30.80 |
| ATOM | 108 | O | PRO | 27 | 185.603 | 135.986 | 185.301 | 1.00 | 30.97 |
| ATOM | 109 | N | ASN | 28 | 186.568 | 134.715 | 186.880 | 1.00 | 31.22 |

*FIG. 4A - 2*

```
ATOM    110  CA   ASN    28        187.795 134.471 186.137  1.00 30.54
ATOM    111  CB   ASN    28        188.688 133.532 186.940  1.00 35.27
ATOM    112  CG   ASN    28        190.078 133.433 186.366  1.00 41.45
ATOM    113  OD1  ASN    28        190.807 134.424 186.303  1.00 45.99
ATOM    114  ND2  ASN    28        190.455 132.234 185.936  1.00 45.33
ATOM    115  C    ASN    28        187.705 133.956 184.705  1.00 27.46
ATOM    116  O    ASN    28        188.462 134.402 183.843  1.00 25.64
ATOM    117  N    GLU    29        186.803 133.019 184.440  1.00 25.78
ATOM    118  CA   GLU    29        186.691 132.464 183.095  1.00 25.39
ATOM    119  CB   GLU    29        185.701 131.297 183.080  1.00 24.35
ATOM    120  CG   GLU    29        184.252 131.715 183.021  1.00 25.81
ATOM    121  CD   GLU    29        183.674 132.010 184.391  1.00 27.90
ATOM    122  OE1  GLU    29        182.437 132.172 184.489  1.00 29.93
ATOM    123  OE2  GLU    29        184.452 132.083 185.368  1.00 27.77
ATOM    124  C    GLU    29        186.279 133.499 182.058  1.00 25.44
ATOM    125  O    GLU    29        186.400 133.269 180.856  1.00 26.44
ATOM    126  N    LYS    30        185.801 134.645 182.522  1.00 23.71
ATOM    127  CA   LYS    30        185.371 135.691 181.613  1.00 22.22
ATOM    128  CB   LYS    30        184.245 136.500 182.264  1.00 20.40
ATOM    129  CG   LYS    30        183.006 135.651 182.550  1.00 18.91
ATOM    130  CD   LYS    30        181.898 136.435 183.233  1.00 19.38
ATOM    131  CE   LYS    30        180.744 135.525 183.612  1.00 16.96
ATOM    132  NZ   LYS    30        179.739 136.231 184.450  1.00 19.00
ATOM    133  C    LYS    30        186.528 136.592 181.198  1.00 22.88
ATOM    134  O    LYS    30        186.343 137.532 180.423  1.00 21.66
ATOM    135  N    ILE    31        187.722 136.286 181.702  1.00 24.29
ATOM    136  CA   ILE    31        188.924 137.056 181.375  1.00 25.60
ATOM    137  CB   ILE    31        189.697 137.493 182.636  1.00 25.05
ATOM    138  CG2  ILE    31        190.872 138.359 182.229  1.00 23.00
ATOM    139  CG1  ILE    31        188.787 138.247 183.603  1.00 24.21
ATOM    140  CD1  ILE    31        189.338 138.301 185.012  1.00 22.98
ATOM    141  C    ILE    31        189.920 136.259 180.529  1.00 27.34
ATOM    142  O    ILE    31        190.404 135.212 180.957  1.00 29.03
ATOM    143  N    LYS    32        190.229 136.759 179.336  1.00 27.91
ATOM    144  CA   LYS    32        191.192 136.110 178.448  1.00 26.27
ATOM    145  CB   LYS    32        190.615 135.971 177.039  1.00 24.74
ATOM    146  CG   LYS    32        189.645 134.814 176.846  1.00 21.71
ATOM    147  CD   LYS    32        189.171 134.768 175.396  1.00 22.53
ATOM    148  CE   LYS    32        188.529 133.439 175.043  1.00 19.73
ATOM    149  NZ   LYS    32        187.307 133.239 175.845  1.00 22.97
ATOM    150  C    LYS    32        192.405 137.037 178.412  1.00 28.45
ATOM    151  O    LYS    32        192.248 138.259 178.383  1.00 28.91
ATOM    152  N    VAL    33        193.611 136.474 178.415  1.00 28.74
ATOM    153  CA   VAL    33        194.821 137.295 178.405  1.00 28.11
ATOM    154  CB   VAL    33        195.723 136.942 179.609  1.00 27.94
ATOM    155  CG1  VAL    33        197.001 137.758 179.570  1.00 26.87
ATOM    156  CG2  VAL    33        194.974 137.202 180.903  1.00 24.11
ATOM    157  C    VAL    33        195.624 137.159 177.111  1.00 28.81
ATOM    158  O    VAL    33        195.727 136.070 176.546  1.00 28.42
ATOM    159  N    ASP    34        196.192 138.271 176.650  1.00 29.48
ATOM    160  CA   ASP    34        196.973 138.280 175.418  1.00 30.64
ATOM    161  CB   ASP    34        198.328 137.621 175.644  1.00 32.74
ATOM    162  CG   ASP    34        199.050 138.184 176.843  1.00 37.31
ATOM    163  OD1  ASP    34        199.102 139.426 176.977  1.00 38.98
ATOM    164  OD2  ASP    34        199.564 137.385 177.654  1.00 42.05
ATOM    165  C    ASP    34        196.197 137.505 174.371  1.00 30.08
ATOM    166  O    ASP    34        196.705 136.551 173.782  1.00 30.60
```

*FIG. 4A - 3*

| | | | | | | | | |
|---|---|---|---|---|---|---|---|---|
| ATOM | 167 | N | GLU | 35 | 194.958 | 137.929 | 174.150 | 1.00 28.83 |
| ATOM | 168 | CA | GLU | 35 | 194.066 | 137.272 | 173.207 | 1.00 27.13 |
| ATOM | 169 | CB | GLU | 35 | 192.659 | 137.222 | 173.804 | 1.00 26.46 |
| ATOM | 170 | CG | GLU | 35 | 191.651 | 136.476 | 172.962 | 1.00 27.85 |
| ATOM | 171 | CD | GLU | 35 | 191.719 | 134.986 | 173.171 | 1.00 28.10 |
| ATOM | 172 | OE1 | GLU | 35 | 190.861 | 134.270 | 172.616 | 1.00 29.80 |
| ATOM | 173 | OE2 | GLU | 35 | 192.632 | 134.533 | 173.889 | 1.00 28.74 |
| ATOM | 174 | C | GLU | 35 | 194.015 | 137.934 | 171.834 | 1.00 26.49 |
| ATOM | 175 | O | GLU | 35 | 193.669 | 139.107 | 171.711 | 1.00 27.77 |
| ATOM | 176 | N | PRO | 36 | 194.372 | 137.184 | 170.781 | 1.00 25.48 |
| ATOM | 177 | CD | PRO | 36 | 194.847 | 135.793 | 170.828 | 1.00 25.03 |
| ATOM | 178 | CA | PRO | 36 | 194.357 | 137.710 | 169.411 | 1.00 24.71 |
| ATOM | 179 | CB | PRO | 36 | 194.882 | 136.547 | 168.568 | 1.00 24.63 |
| ATOM | 180 | CG | PRO | 36 | 195.600 | 135.659 | 169.542 | 1.00 25.14 |
| ATOM | 181 | C | PRO | 36 | 192.947 | 138.116 | 169.005 | 1.00 24.38 |
| ATOM | 182 | O | PRO | 36 | 192.025 | 137.301 | 169.040 | 1.00 24.04 |
| ATOM | 183 | N | LEU | 37 | 192.789 | 139.376 | 168.616 | 1.00 24.08 |
| ATOM | 184 | CA | LEU | 37 | 191.492 | 139.906 | 168.217 | 1.00 23.83 |
| ATOM | 185 | CB | LEU | 37 | 191.526 | 141.431 | 168.284 | 1.00 22.04 |
| ATOM | 186 | CG | LEU | 37 | 191.584 | 141.951 | 169.723 | 1.00 23.81 |
| ATOM | 187 | CD1 | LEU | 37 | 192.144 | 143.363 | 169.762 | 1.00 23.31 |
| ATOM | 188 | CD2 | LEU | 37 | 190.192 | 141.908 | 170.318 | 1.00 21.77 |
| ATOM | 189 | C | LEU | 37 | 191.026 | 139.456 | 166.835 | 1.00 24.88 |
| ATOM | 190 | O | LEU | 37 | 189.834 | 139.506 | 166.535 | 1.00 24.16 |
| ATOM | 191 | N | LYS | 38 | 191.958 | 139.009 | 165.998 | 1.00 26.69 |
| ATOM | 192 | CA | LYS | 38 | 191.610 | 138.555 | 164.655 | 1.00 27.46 |
| ATOM | 193 | CB | LYS | 38 | 192.864 | 138.081 | 163.904 | 1.00 29.51 |
| ATOM | 194 | CG | LYS | 38 | 193.456 | 136.768 | 164.406 | 1.00 37.35 |
| ATOM | 195 | CD | LYS | 38 | 194.976 | 136.757 | 164.274 | 1.00 41.56 |
| ATOM | 196 | CE | LYS | 38 | 195.562 | 135.418 | 164.694 | 1.00 44.25 |
| ATOM | 197 | NZ | LYS | 38 | 196.682 | 135.604 | 165.652 | 1.00 46.35 |
| ATOM | 198 | C | LYS | 38 | 190.574 | 137.434 | 164.692 | 1.00 26.34 |
| ATOM | 199 | O | LYS | 38 | 189.826 | 137.244 | 163.733 | 1.00 27.07 |
| ATOM | 200 | N | ARG | 39 | 190.526 | 136.699 | 165.800 | 1.00 23.79 |
| ATOM | 201 | CA | ARG | 39 | 189.577 | 135.599 | 165.947 | 1.00 22.22 |
| ATOM | 202 | CB | ARG | 39 | 189.897 | 134.783 | 167.212 | 1.00 19.50 |
| ATOM | 203 | CG | ARG | 39 | 188.903 | 133.650 | 167.525 | 1.00 17.87 |
| ATOM | 204 | CD | ARG | 39 | 189.362 | 132.802 | 168.720 | 1.00 18.47 |
| ATOM | 205 | NE | ARG | 39 | 188.399 | 131.757 | 169.061 | 1.00 19.16 |
| ATOM | 206 | CZ | ARG | 39 | 188.366 | 131.116 | 170.227 | 1.00 18.78 |
| ATOM | 207 | NH1 | ARG | 39 | 189.246 | 131.405 | 171.173 | 1.00 17.38 |
| ATOM | 208 | NH2 | ARG | 39 | 187.446 | 130.188 | 170.451 | 1.00 18.15 |
| ATOM | 209 | C | ARG | 39 | 188.147 | 136.115 | 166.032 | 1.00 23.42 |
| ATOM | 210 | O | ARG | 39 | 187.202 | 135.397 | 165.709 | 1.00 23.05 |
| ATOM | 211 | N | TYR | 40 | 187.990 | 137.370 | 166.440 | 1.00 23.44 |
| ATOM | 212 | CA | TYR | 40 | 186.658 | 137.936 | 166.614 | 1.00 25.02 |
| ATOM | 213 | CB | TYR | 40 | 186.490 | 138.367 | 168.070 | 1.00 22.89 |
| ATOM | 214 | CG | TYR | 40 | 186.981 | 137.339 | 169.056 | 1.00 21.61 |
| ATOM | 215 | CD1 | TYR | 40 | 188.165 | 137.533 | 169.763 | 1.00 21.86 |
| ATOM | 216 | CE1 | TYR | 40 | 188.624 | 136.581 | 170.676 | 1.00 22.06 |
| ATOM | 217 | CD2 | TYR | 40 | 186.263 | 136.168 | 169.281 | 1.00 21.75 |
| ATOM | 218 | CE2 | TYR | 40 | 186.710 | 135.210 | 170.189 | 1.00 21.84 |
| ATOM | 219 | CZ | TYR | 40 | 187.889 | 135.423 | 170.881 | 1.00 22.44 |
| ATOM | 220 | OH | TYR | 40 | 188.334 | 134.474 | 171.772 | 1.00 24.93 |
| ATOM | 221 | C | TYR | 40 | 186.204 | 139.081 | 165.714 | 1.00 26.20 |
| ATOM | 222 | O | TYR | 40 | 185.005 | 139.316 | 165.590 | 1.00 28.00 |
| ATOM | 223 | N | THR | 41 | 187.130 | 139.800 | 165.093 | 1.00 26.43 |

*FIG. 4A - 4*

| | | | | | | | | |
|---|---|---|---|---|---|---|---|---|
| ATOM | 224 | CA | THR | 41 | 186.729 | 140.913 | 164.239 | 1.00 25.56 |
| ATOM | 225 | CB | THR | 41 | 187.905 | 141.853 | 163.969 | 1.00 23.93 |
| ATOM | 226 | OG1 | THR | 41 | 188.961 | 141.130 | 163.328 | 1.00 24.17 |
| ATOM | 227 | CG2 | THR | 41 | 188.408 | 142.441 | 165.270 | 1.00 23.28 |
| ATOM | 228 | C | THR | 41 | 186.135 | 140.473 | 162.905 | 1.00 25.88 |
| ATOM | 229 | O | THR | 41 | 186.541 | 139.467 | 162.328 | 1.00 24.62 |
| ATOM | 230 | N | TYR | 42 | 185.164 | 141.244 | 162.426 | 1.00 26.64 |
| ATOM | 231 | CA | TYR | 42 | 184.490 | 140.959 | 161.166 | 1.00 25.84 |
| ATOM | 232 | CB | TYR | 42 | 183.366 | 141.972 | 160.945 | 1.00 26.33 |
| ATOM | 233 | CG | TYR | 42 | 182.535 | 141.731 | 159.708 | 1.00 27.66 |
| ATOM | 234 | CD1 | TYR | 42 | 181.296 | 141.093 | 159.785 | 1.00 28.83 |
| ATOM | 235 | CE1 | TYR | 42 | 180.511 | 140.902 | 158.649 | 1.00 30.12 |
| ATOM | 236 | CD2 | TYR | 42 | 182.971 | 142.169 | 158.462 | 1.00 29.40 |
| ATOM | 237 | CE2 | TYR | 42 | 182.198 | 141.983 | 157.322 | 1.00 31.51 |
| ATOM | 238 | CZ | TYR | 42 | 180.969 | 141.352 | 157.420 | 1.00 33.36 |
| ATOM | 239 | OH | TYR | 42 | 180.200 | 141.183 | 156.286 | 1.00 37.88 |
| ATOM | 240 | C | TYR | 42 | 185.469 | 140.997 | 159.998 | 1.00 26.35 |
| ATOM | 241 | O | TYR | 42 | 185.270 | 140.321 | 158.988 | 1.00 24.47 |
| ATOM | 242 | N | THR | 43 | 186.528 | 141.787 | 160.137 | 1.00 25.81 |
| ATOM | 243 | CA | THR | 43 | 187.537 | 141.898 | 159.090 | 1.00 27.25 |
| ATOM | 244 | CB | THR | 43 | 188.257 | 143.245 | 159.161 | 1.00 27.00 |
| ATOM | 245 | OG1 | THR | 43 | 188.900 | 143.365 | 160.435 | 1.00 27.16 |
| ATOM | 246 | CG2 | THR | 43 | 187.270 | 144.392 | 158.979 | 1.00 26.57 |
| ATOM | 247 | C | THR | 43 | 188.590 | 140.803 | 159.230 | 1.00 28.75 |
| ATOM | 248 | O | THR | 43 | 189.440 | 140.633 | 158.359 | 1.00 29.45 |
| ATOM | 249 | N | LYS | 44 | 188.530 | 140.069 | 160.336 | 1.00 29.60 |
| ATOM | 250 | CA | LYS | 44 | 189.479 | 138.999 | 160.612 | 1.00 29.64 |
| ATOM | 251 | CB | LYS | 44 | 189.403 | 137.925 | 159.524 | 1.00 30.16 |
| ATOM | 252 | CG | LYS | 44 | 188.102 | 137.127 | 159.522 | 1.00 32.82 |
| ATOM | 253 | CD | LYS | 44 | 187.785 | 136.533 | 160.892 | 1.00 35.20 |
| ATOM | 254 | CE | LYS | 44 | 186.556 | 135.627 | 160.831 | 1.00 38.37 |
| ATOM | 255 | NZ | LYS | 44 | 185.774 | 135.624 | 162.106 | 1.00 40.28 |
| ATOM | 256 | C | LYS | 44 | 190.909 | 139.529 | 160.728 | 1.00 29.11 |
| ATOM | 257 | O | LYS | 44 | 191.839 | 138.974 | 160.146 | 1.00 30.41 |
| ATOM | 258 | N | THR | 45 | 191.077 | 140.615 | 161.476 | 1.00 26.93 |
| ATOM | 259 | CA | THR | 45 | 192.393 | 141.205 | 161.681 | 1.00 26.74 |
| ATOM | 260 | CB | THR | 45 | 192.666 | 142.368 | 160.688 | 1.00 27.36 |
| ATOM | 261 | OG1 | THR | 45 | 191.760 | 143.447 | 160.943 | 1.00 25.55 |
| ATOM | 262 | CG2 | THR | 45 | 192.494 | 141.895 | 159.245 | 1.00 26.41 |
| ATOM | 263 | C | THR | 45 | 192.486 | 141.735 | 163.108 | 1.00 26.76 |
| ATOM | 264 | O | THR | 45 | 191.473 | 141.858 | 163.795 | 1.00 26.69 |
| ATOM | 265 | N | GLY | 46 | 193.700 | 142.033 | 163.557 | 1.00 26.13 |
| ATOM | 266 | CA | GLY | 46 | 193.871 | 142.549 | 164.903 | 1.00 26.05 |
| ATOM | 267 | C | GLY | 46 | 194.823 | 141.734 | 165.757 | 1.00 26.45 |
| ATOM | 268 | O | GLY | 46 | 194.772 | 140.506 | 165.762 | 1.00 26.47 |
| ATOM | 269 | N | GLY | 47 | 195.689 | 142.426 | 166.491 | 1.00 26.87 |
| ATOM | 270 | CA | GLY | 47 | 196.649 | 141.754 | 167.344 | 1.00 26.14 |
| ATOM | 271 | C | GLY | 47 | 196.093 | 141.355 | 168.696 | 1.00 26.75 |
| ATOM | 272 | O | GLY | 47 | 194.880 | 141.273 | 168.886 | 1.00 26.49 |
| ATOM | 273 | N | ASN | 48 | 196.997 | 141.115 | 169.640 | 1.00 26.89 |
| ATOM | 274 | CA | ASN | 48 | 196.637 | 140.700 | 170.990 | 1.00 26.88 |
| ATOM | 275 | CB | ASN | 48 | 197.872 | 140.188 | 171.729 | 1.00 28.23 |
| ATOM | 276 | CG | ASN | 48 | 198.368 | 138.869 | 171.201 | 1.00 29.44 |
| ATOM | 277 | OD1 | ASN | 48 | 199.403 | 138.370 | 171.640 | 1.00 31.31 |
| ATOM | 278 | ND2 | ASN | 48 | 197.639 | 138.291 | 170.258 | 1.00 29.60 |
| ATOM | 279 | C | ASN | 48 | 196.014 | 141.789 | 171.848 | 1.00 27.15 |
| ATOM | 280 | O | ASN | 48 | 196.440 | 142.943 | 171.818 | 1.00 26.71 |

*FIG. 4A - 5*

| | | | | | | | | |
|---|---|---|---|---|---|---|---|---|
| ATOM | 281 | N   | ALA | 49 | 195.006 | 141.404 | 172.623 | 1.00 26.07 |
| ATOM | 282 | CA  | ALA | 49 | 194.353 | 142.312 | 173.550 | 1.00 25.97 |
| ATOM | 283 | CB  | ALA | 49 | 192.849 | 142.079 | 173.556 | 1.00 25.15 |
| ATOM | 284 | C   | ALA | 49 | 194.960 | 141.880 | 174.875 | 1.00 26.08 |
| ATOM | 285 | O   | ALA | 49 | 194.904 | 140.700 | 175.218 | 1.00 26.46 |
| ATOM | 286 | N   | ASP | 50 | 195.570 | 142.806 | 175.605 | 1.00 26.47 |
| ATOM | 287 | CA  | ASP | 50 | 196.180 | 142.445 | 176.881 | 1.00 26.83 |
| ATOM | 288 | CB  | ASP | 50 | 196.608 | 143.695 | 177.650 | 1.00 25.98 |
| ATOM | 289 | CG  | ASP | 50 | 197.804 | 144.379 | 177.024 | 1.00 25.09 |
| ATOM | 290 | OD1 | ASP | 50 | 198.239 | 145.418 | 177.559 | 1.00 26.47 |
| ATOM | 291 | OD2 | ASP | 50 | 198.309 | 143.881 | 175.994 | 1.00 25.49 |
| ATOM | 292 | C   | ASP | 50 | 195.162 | 141.660 | 177.689 | 1.00 27.65 |
| ATOM | 293 | O   | ASP | 50 | 195.463 | 140.584 | 178.212 | 1.00 28.71 |
| ATOM | 294 | N   | PHE | 51 | 193.953 | 142.209 | 177.779 | 1.00 27.05 |
| ATOM | 295 | CA  | PHE | 51 | 192.855 | 141.572 | 178.495 | 1.00 25.70 |
| ATOM | 296 | CB  | PHE | 51 | 192.633 | 142.242 | 179.851 | 1.00 24.94 |
| ATOM | 297 | CG  | PHE | 51 | 193.834 | 142.194 | 180.743 | 1.00 25.35 |
| ATOM | 298 | CD1 | PHE | 51 | 194.728 | 143.254 | 180.776 | 1.00 25.38 |
| ATOM | 299 | CD2 | PHE | 51 | 194.099 | 141.069 | 181.518 | 1.00 25.98 |
| ATOM | 300 | CE1 | PHE | 51 | 195.874 | 143.196 | 181.565 | 1.00 26.51 |
| ATOM | 301 | CE2 | PHE | 51 | 195.241 | 141.003 | 182.309 | 1.00 25.07 |
| ATOM | 302 | CZ  | PHE | 51 | 196.129 | 142.069 | 182.330 | 1.00 26.49 |
| ATOM | 303 | C   | PHE | 51 | 191.611 | 141.698 | 177.636 | 1.00 24.75 |
| ATOM | 304 | O   | PHE | 51 | 191.273 | 142.782 | 177.167 | 1.00 25.91 |
| ATOM | 305 | N   | TYR | 52 | 190.948 | 140.573 | 177.417 | 1.00 23.16 |
| ATOM | 306 | CA  | TYR | 52 | 189.745 | 140.525 | 176.606 | 1.00 22.66 |
| ATOM | 307 | CB  | TYR | 52 | 189.988 | 139.591 | 175.415 | 1.00 21.58 |
| ATOM | 308 | CG  | TYR | 52 | 188.861 | 139.498 | 174.416 | 1.00 21.47 |
| ATOM | 309 | CD1 | TYR | 52 | 188.564 | 140.560 | 173.566 | 1.00 21.89 |
| ATOM | 310 | CE1 | TYR | 52 | 187.538 | 140.467 | 172.632 | 1.00 21.66 |
| ATOM | 311 | CD2 | TYR | 52 | 188.101 | 138.335 | 174.305 | 1.00 20.07 |
| ATOM | 312 | CE2 | TYR | 52 | 187.074 | 138.232 | 173.376 | 1.00 20.26 |
| ATOM | 313 | CZ  | TYR | 52 | 186.797 | 139.301 | 172.544 | 1.00 22.16 |
| ATOM | 314 | OH  | TYR | 52 | 185.766 | 139.206 | 171.637 | 1.00 22.84 |
| ATOM | 315 | C   | TYR | 52 | 188.666 | 139.979 | 177.533 | 1.00 23.48 |
| ATOM | 316 | O   | TYR | 52 | 188.643 | 138.787 | 177.838 | 1.00 23.13 |
| ATOM | 317 | N   | ILE | 53 | 187.781 | 140.862 | 177.987 | 1.00 23.40 |
| ATOM | 318 | CA  | ILE | 53 | 186.720 | 140.488 | 178.917 | 1.00 23.42 |
| ATOM | 319 | CB  | ILE | 53 | 186.641 | 141.522 | 180.064 | 1.00 23.20 |
| ATOM | 320 | CG2 | ILE | 53 | 185.713 | 141.028 | 181.163 | 1.00 21.95 |
| ATOM | 321 | CG1 | ILE | 53 | 188.051 | 141.769 | 180.611 | 1.00 24.13 |
| ATOM | 322 | CD1 | ILE | 53 | 188.111 | 142.683 | 181.806 | 1.00 26.33 |
| ATOM | 323 | C   | ILE | 53 | 185.343 | 140.341 | 178.283 | 1.00 24.38 |
| ATOM | 324 | O   | ILE | 53 | 184.888 | 141.213 | 177.540 | 1.00 25.15 |
| ATOM | 325 | N   | THR | 54 | 184.684 | 139.227 | 178.585 | 1.00 24.23 |
| ATOM | 326 | CA  | THR | 54 | 183.351 | 138.949 | 178.061 | 1.00 23.55 |
| ATOM | 327 | CB  | THR | 54 | 183.318 | 137.607 | 177.298 | 1.00 23.73 |
| ATOM | 328 | OG1 | THR | 54 | 184.271 | 137.644 | 176.229 | 1.00 25.62 |
| ATOM | 329 | CG2 | THR | 54 | 181.936 | 137.353 | 176.714 | 1.00 23.77 |
| ATOM | 330 | C   | THR | 54 | 182.371 | 138.887 | 179.226 | 1.00 23.04 |
| ATOM | 331 | O   | THR | 54 | 182.074 | 137.810 | 179.746 | 1.00 22.02 |
| ATOM | 332 | N   | PRO | 55 | 181.858 | 140.047 | 179.657 | 1.00 22.60 |
| ATOM | 333 | CD  | PRO | 55 | 182.112 | 141.399 | 179.125 | 1.00 21.12 |
| ATOM | 334 | CA  | PRO | 55 | 180.913 | 140.076 | 180.772 | 1.00 21.88 |
| ATOM | 335 | CB  | PRO | 55 | 180.866 | 141.545 | 181.163 | 1.00 19.89 |
| ATOM | 336 | CG  | PRO | 55 | 181.128 | 142.257 | 179.887 | 1.00 20.42 |
| ATOM | 337 | C   | PRO | 55 | 179.546 | 139.579 | 180.346 | 1.00 22.66 |

*FIG. 4A - 6*

| ATOM | 338 | O   | PRO | 55 | 179.198 | 139.635 | 179.167 | 1.00 | 22.17 |
| ATOM | 339 | N   | THR | 56 | 178.777 | 139.088 | 181.309 | 1.00 | 22.09 |
| ATOM | 340 | CA  | THR | 56 | 177.433 | 138.625 | 181.024 | 1.00 | 23.14 |
| ATOM | 341 | CB  | THR | 56 | 177.231 | 137.165 | 181.465 | 1.00 | 22.71 |
| ATOM | 342 | OG1 | THR | 56 | 177.583 | 137.022 | 182.846 | 1.00 | 22.87 |
| ATOM | 343 | CG2 | THR | 56 | 178.097 | 136.241 | 180.629 | 1.00 | 21.53 |
| ATOM | 344 | C   | THR | 56 | 176.434 | 139.517 | 181.758 | 1.00 | 24.34 |
| ATOM | 345 | O   | THR | 56 | 175.224 | 139.352 | 181.606 | 1.00 | 26.45 |
| ATOM | 346 | N   | LYS | 57 | 176.948 | 140.469 | 182.541 | 1.00 | 23.68 |
| ATOM | 347 | CA  | LYS | 57 | 176.106 | 141.389 | 183.311 | 1.00 | 24.63 |
| ATOM | 348 | CB  | LYS | 57 | 176.004 | 140.923 | 184.760 | 1.00 | 24.47 |
| ATOM | 349 | CG  | LYS | 57 | 175.472 | 139.518 | 184.910 | 1.00 | 29.48 |
| ATOM | 350 | CD  | LYS | 57 | 175.316 | 139.141 | 186.364 | 1.00 | 33.62 |
| ATOM | 351 | CE  | LYS | 57 | 176.670 | 138.991 | 187.006 | 1.00 | 37.45 |
| ATOM | 352 | NZ  | LYS | 57 | 176.535 | 138.846 | 188.473 | 1.00 | 41.27 |
| ATOM | 353 | C   | LYS | 57 | 176.596 | 142.832 | 183.308 | 1.00 | 24.48 |
| ATOM | 354 | O   | LYS | 57 | 177.785 | 143.098 | 183.148 | 1.00 | 25.61 |
| ATOM | 355 | N   | ASN | 58 | 175.665 | 143.761 | 183.503 | 1.00 | 24.02 |
| ATOM | 356 | CA  | ASN | 58 | 175.982 | 145.182 | 183.538 | 1.00 | 23.14 |
| ATOM | 357 | CB  | ASN | 58 | 174.698 | 145.999 | 183.703 | 1.00 | 23.03 |
| ATOM | 358 | CG  | ASN | 58 | 173.734 | 145.821 | 182.542 | 1.00 | 24.26 |
| ATOM | 359 | OD1 | ASN | 58 | 174.055 | 145.175 | 181.546 | 1.00 | 24.61 |
| ATOM | 360 | ND2 | ASN | 58 | 172.544 | 146.394 | 182.668 | 1.00 | 24.20 |
| ATOM | 361 | C   | ASN | 58 | 176.935 | 145.504 | 184.687 | 1.00 | 23.15 |
| ATOM | 362 | O   | ASN | 58 | 177.874 | 146.287 | 184.529 | 1.00 | 23.56 |
| ATOM | 363 | N   | GLU | 59 | 176.688 | 144.896 | 185.844 | 1.00 | 22.37 |
| ATOM | 364 | CA  | GLU | 59 | 177.510 | 145.126 | 187.026 | 1.00 | 22.19 |
| ATOM | 365 | CB  | GLU | 59 | 177.001 | 144.279 | 188.192 | 1.00 | 22.89 |
| ATOM | 366 | CG  | GLU | 59 | 175.603 | 144.648 | 188.645 | 1.00 | 26.47 |
| ATOM | 367 | CD  | GLU | 59 | 174.532 | 143.869 | 187.909 | 1.00 | 31.14 |
| ATOM | 368 | OE1 | GLU | 59 | 174.791 | 143.435 | 186.765 | 1.00 | 31.25 |
| ATOM | 369 | OE2 | GLU | 59 | 173.432 | 143.687 | 188.475 | 1.00 | 35.51 |
| ATOM | 370 | C   | GLU | 59 | 178.972 | 144.807 | 186.769 | 1.00 | 21.38 |
| ATOM | 371 | O   | GLU | 59 | 179.862 | 145.462 | 187.308 | 1.00 | 20.87 |
| ATOM | 372 | N   | GLU | 60 | 179.215 | 143.796 | 185.943 | 1.00 | 20.46 |
| ATOM | 373 | CA  | GLU | 60 | 180.575 | 143.392 | 185.619 | 1.00 | 20.33 |
| ATOM | 374 | CB  | GLU | 60 | 180.559 | 142.042 | 184.902 | 1.00 | 19.12 |
| ATOM | 375 | CG  | GLU | 60 | 180.356 | 140.871 | 185.845 | 1.00 | 19.52 |
| ATOM | 376 | CD  | GLU | 60 | 180.101 | 139.575 | 185.120 | 1.00 | 21.42 |
| ATOM | 377 | OE1 | GLU | 60 | 179.845 | 139.622 | 183.902 | 1.00 | 23.86 |
| ATOM | 378 | OE2 | GLU | 60 | 180.156 | 138.508 | 185.765 | 1.00 | 23.41 |
| ATOM | 379 | C   | GLU | 60 | 181.260 | 144.443 | 184.757 | 1.00 | 20.35 |
| ATOM | 380 | O   | GLU | 60 | 182.456 | 144.688 | 184.893 | 1.00 | 21.64 |
| ATOM | 381 | N   | VAL | 61 | 180.497 | 145.065 | 183.868 | 1.00 | 20.90 |
| ATOM | 382 | CA  | VAL | 61 | 181.045 | 146.096 | 183.002 | 1.00 | 20.81 |
| ATOM | 383 | CB  | VAL | 61 | 180.018 | 146.548 | 181.946 | 1.00 | 19.94 |
| ATOM | 384 | CG1 | VAL | 61 | 180.529 | 147.782 | 181.214 | 1.00 | 18.23 |
| ATOM | 385 | CG2 | VAL | 61 | 179.757 | 145.418 | 180.965 | 1.00 | 18.95 |
| ATOM | 386 | C   | VAL | 61 | 181.415 | 147.283 | 183.873 | 1.00 | 22.79 |
| ATOM | 387 | O   | VAL | 61 | 182.470 | 147.885 | 183.699 | 1.00 | 23.98 |
| ATOM | 388 | N   | GLN | 62 | 180.535 | 147.608 | 184.816 | 1.00 | 23.28 |
| ATOM | 389 | CA  | GLN | 62 | 180.749 | 148.722 | 185.734 | 1.00 | 23.75 |
| ATOM | 390 | CB  | GLN | 62 | 179.548 | 148.873 | 186.669 | 1.00 | 23.31 |
| ATOM | 391 | CG  | GLN | 62 | 178.297 | 149.424 | 186.023 | 1.00 | 23.57 |
| ATOM | 392 | CD  | GLN | 62 | 177.227 | 149.740 | 187.042 | 1.00 | 24.43 |
| ATOM | 393 | OE1 | GLN | 62 | 176.373 | 148.906 | 187.346 | 1.00 | 25.47 |
| ATOM | 394 | NE2 | GLN | 62 | 177.270 | 150.951 | 187.586 | 1.00 | 25.90 |

*FIG. 4A - 7*

| | | | | | | | | | |
|---|---|---|---|---|---|---|---|---|---|
| ATOM | 395 | C   | GLN | 62 | 181.999 | 148.513 | 186.579 | 1.00 | 23.48 |
| ATOM | 396 | O   | GLN | 62 | 182.829 | 149.407 | 186.711 | 1.00 | 24.45 |
| ATOM | 397 | N   | ALA | 63 | 182.117 | 147.326 | 187.163 | 1.00 | 23.21 |
| ATOM | 398 | CA  | ALA | 63 | 183.256 | 146.999 | 188.008 | 1.00 | 23.08 |
| ATOM | 399 | CB  | ALA | 63 | 183.118 | 145.586 | 188.539 | 1.00 | 21.88 |
| ATOM | 400 | C   | ALA | 63 | 184.570 | 147.143 | 187.261 | 1.00 | 24.17 |
| ATOM | 401 | O   | ALA | 63 | 185.545 | 147.658 | 187.808 | 1.00 | 26.16 |
| ATOM | 402 | N   | VAL | 64 | 184.597 | 146.688 | 186.012 | 1.00 | 24.25 |
| ATOM | 403 | CA  | VAL | 64 | 185.809 | 146.769 | 185.206 | 1.00 | 23.57 |
| ATOM | 404 | CB  | VAL | 64 | 185.694 | 145.916 | 183.921 | 1.00 | 22.67 |
| ATOM | 405 | CG1 | VAL | 64 | 186.873 | 146.201 | 183.000 | 1.00 | 19.87 |
| ATOM | 406 | CG2 | VAL | 64 | 185.657 | 144.436 | 184.277 | 1.00 | 19.88 |
| ATOM | 407 | C   | VAL | 64 | 186.140 | 148.203 | 184.815 | 1.00 | 25.38 |
| ATOM | 408 | O   | VAL | 64 | 187.293 | 148.621 | 184.899 | 1.00 | 27.94 |
| ATOM | 409 | N   | VAL | 65 | 185.134 | 148.960 | 184.391 | 1.00 | 26.61 |
| ATOM | 410 | CA  | VAL | 65 | 185.354 | 150.346 | 183.987 | 1.00 | 26.35 |
| ATOM | 411 | CB  | VAL | 65 | 184.088 | 150.959 | 183.369 | 1.00 | 24.39 |
| ATOM | 412 | CG1 | VAL | 65 | 184.325 | 152.419 | 183.048 | 1.00 | 22.95 |
| ATOM | 413 | CG2 | VAL | 65 | 183.711 | 150.196 | 182.114 | 1.00 | 23.28 |
| ATOM | 414 | C   | VAL | 65 | 185.798 | 151.212 | 185.157 | 1.00 | 27.43 |
| ATOM | 415 | O   | VAL | 65 | 186.693 | 152.041 | 185.014 | 1.00 | 27.96 |
| ATOM | 416 | N   | LYS | 66 | 185.169 | 151.023 | 186.311 | 1.00 | 28.37 |
| ATOM | 417 | CA  | LYS | 66 | 185.528 | 151.792 | 187.498 | 1.00 | 31.01 |
| ATOM | 418 | CB  | LYS | 66 | 184.624 | 151.406 | 188.677 | 1.00 | 30.16 |
| ATOM | 419 | CG  | LYS | 66 | 185.021 | 152.037 | 190.003 | 1.00 | 31.06 |
| ATOM | 420 | CD  | LYS | 66 | 183.817 | 152.284 | 190.890 | 1.00 | 32.82 |
| ATOM | 421 | CE  | LYS | 66 | 184.135 | 151.991 | 192.346 | 1.00 | 34.63 |
| ATOM | 422 | NZ  | LYS | 66 | 182.909 | 151.992 | 193.186 | 1.00 | 35.45 |
| ATOM | 423 | C   | LYS | 66 | 186.988 | 151.510 | 187.848 | 1.00 | 31.91 |
| ATOM | 424 | O   | LYS | 66 | 187.777 | 152.429 | 188.072 | 1.00 | 32.06 |
| ATOM | 425 | N   | TYR | 67 | 187.340 | 150.228 | 187.876 | 1.00 | 33.25 |
| ATOM | 426 | CA  | TYR | 67 | 188.696 | 149.812 | 188.198 | 1.00 | 34.11 |
| ATOM | 427 | CB  | TYR | 67 | 188.814 | 148.286 | 188.140 | 1.00 | 36.62 |
| ATOM | 428 | CG  | TYR | 67 | 190.246 | 147.808 | 188.171 | 1.00 | 39.45 |
| ATOM | 429 | CD1 | TYR | 67 | 190.941 | 147.722 | 189.376 | 1.00 | 39.81 |
| ATOM | 430 | CE1 | TYR | 67 | 192.277 | 147.342 | 189.410 | 1.00 | 41.02 |
| ATOM | 431 | CD2 | TYR | 67 | 190.925 | 147.496 | 186.992 | 1.00 | 40.26 |
| ATOM | 432 | CE2 | TYR | 67 | 192.263 | 147.114 | 187.014 | 1.00 | 41.21 |
| ATOM | 433 | CZ  | TYR | 67 | 192.933 | 147.041 | 188.229 | 1.00 | 41.81 |
| ATOM | 434 | OH  | TYR | 67 | 194.257 | 146.670 | 188.272 | 1.00 | 42.60 |
| ATOM | 435 | C   | TYR | 67 | 189.721 | 150.426 | 187.254 | 1.00 | 33.21 |
| ATOM | 436 | O   | TYR | 67 | 190.741 | 150.945 | 187.691 | 1.00 | 33.38 |
| ATOM | 437 | N   | ALA | 68 | 189.449 | 150.354 | 185.957 | 1.00 | 32.90 |
| ATOM | 438 | CA  | ALA | 68 | 190.363 | 150.894 | 184.960 | 1.00 | 33.67 |
| ATOM | 439 | CB  | ALA | 68 | 189.863 | 150.558 | 183.567 | 1.00 | 32.97 |
| ATOM | 440 | C   | ALA | 68 | 190.505 | 152.400 | 185.120 | 1.00 | 34.07 |
| ATOM | 441 | O   | ALA | 68 | 191.594 | 152.954 | 184.972 | 1.00 | 32.81 |
| ATOM | 442 | N   | TYR | 69 | 189.396 | 153.061 | 185.424 | 1.00 | 35.16 |
| ATOM | 443 | CA  | TYR | 69 | 189.398 | 154.504 | 185.611 | 1.00 | 36.20 |
| ATOM | 444 | CB  | TYR | 69 | 187.974 | 154.988 | 185.880 | 1.00 | 37.11 |
| ATOM | 445 | CG  | TYR | 69 | 187.878 | 156.461 | 186.173 | 1.00 | 39.32 |
| ATOM | 446 | CD1 | TYR | 69 | 188.020 | 157.403 | 185.156 | 1.00 | 39.67 |
| ATOM | 447 | CE1 | TYR | 69 | 187.943 | 158.761 | 185.423 | 1.00 | 41.33 |
| ATOM | 448 | CD2 | TYR | 69 | 187.652 | 156.917 | 187.470 | 1.00 | 41.12 |
| ATOM | 449 | CE2 | TYR | 69 | 187.572 | 158.272 | 187.749 | 1.00 | 41.93 |
| ATOM | 450 | CZ  | TYR | 69 | 187.719 | 159.188 | 186.723 | 1.00 | 42.53 |
| ATOM | 451 | OH  | TYR | 69 | 187.641 | 160.532 | 186.999 | 1.00 | 45.35 |

*FIG. 4A - 8*

| | | | | | | | | | |
|---|---|---|---|---|---|---|---|---|---|
| ATOM | 452 | C | TYR | 69 | 190.299 | 154.870 | 186.788 | 1.00 | 36.45 |
| ATOM | 453 | O | TYR | 69 | 191.136 | 155.766 | 186.698 | 1.00 | 35.81 |
| ATOM | 454 | N | GLN | 70 | 190.123 | 154.155 | 187.892 | 1.00 | 35.88 |
| ATOM | 455 | CA | GLN | 70 | 190.905 | 154.390 | 189.096 | 1.00 | 35.72 |
| ATOM | 456 | CB | GLN | 70 | 190.458 | 153.438 | 190.198 | 1.00 | 34.82 |
| ATOM | 457 | CG | GLN | 70 | 189.197 | 153.858 | 190.912 | 1.00 | 35.37 |
| ATOM | 458 | CD | GLN | 70 | 188.576 | 152.712 | 191.683 | 1.00 | 38.91 |
| ATOM | 459 | OE1 | GLN | 70 | 189.038 | 151.570 | 191.601 | 1.00 | 40.40 |
| ATOM | 460 | NE2 | GLN | 70 | 187.524 | 153.008 | 192.437 | 1.00 | 38.97 |
| ATOM | 461 | C | GLN | 70 | 192.406 | 154.228 | 188.891 | 1.00 | 36.57 |
| ATOM | 462 | O | GLN | 70 | 193.198 | 154.986 | 189.450 | 1.00 | 37.20 |
| ATOM | 463 | N | ASN | 71 | 192.796 | 153.235 | 188.097 | 1.00 | 36.33 |
| ATOM | 464 | CA | ASN | 71 | 194.207 | 152.967 | 187.851 | 1.00 | 36.54 |
| ATOM | 465 | CB | ASN | 71 | 194.477 | 151.477 | 188.030 | 1.00 | 35.46 |
| ATOM | 466 | CG | ASN | 71 | 193.993 | 150.961 | 189.370 | 1.00 | 37.54 |
| ATOM | 467 | OD1 | ASN | 71 | 194.757 | 150.894 | 190.332 | 1.00 | 42.36 |
| ATOM | 468 | ND2 | ASN | 71 | 192.720 | 150.600 | 189.442 | 1.00 | 36.38 |
| ATOM | 469 | C | ASN | 71 | 194.685 | 153.428 | 186.481 | 1.00 | 37.61 |
| ATOM | 470 | O | ASN | 71 | 195.723 | 152.985 | 185.994 | 1.00 | 38.28 |
| ATOM | 471 | N | GLU | 72 | 193.918 | 154.319 | 185.865 | 1.00 | 39.04 |
| ATOM | 472 | CA | GLU | 72 | 194.252 | 154.871 | 184.558 | 1.00 | 40.11 |
| ATOM | 473 | CB | GLU | 72 | 195.417 | 155.847 | 184.692 | 1.00 | 45.05 |
| ATOM | 474 | CG | GLU | 72 | 195.173 | 156.977 | 185.669 | 1.00 | 52.33 |
| ATOM | 475 | CD | GLU | 72 | 196.386 | 157.869 | 185.828 | 1.00 | 56.92 |
| ATOM | 476 | OE1 | GLU | 72 | 196.420 | 158.947 | 185.196 | 1.00 | 59.82 |
| ATOM | 477 | OE2 | GLU | 72 | 197.308 | 157.490 | 186.583 | 1.00 | 60.85 |
| ATOM | 478 | C | GLU | 72 | 194.589 | 153.854 | 183.475 | 1.00 | 37.93 |
| ATOM | 479 | O | GLU | 72 | 195.527 | 154.054 | 182.709 | 1.00 | 38.03 |
| ATOM | 480 | N | ILE | 73 | 193.831 | 152.767 | 183.406 | 1.00 | 36.15 |
| ATOM | 481 | CA | ILE | 73 | 194.066 | 151.758 | 182.380 | 1.00 | 34.96 |
| ATOM | 482 | CB | ILE | 73 | 193.831 | 150.331 | 182.914 | 1.00 | 35.13 |
| ATOM | 483 | CG2 | ILE | 73 | 194.067 | 149.313 | 181.803 | 1.00 | 35.65 |
| ATOM | 484 | CG1 | ILE | 73 | 194.771 | 150.055 | 184.085 | 1.00 | 35.63 |
| ATOM | 485 | CD1 | ILE | 73 | 194.281 | 148.970 | 185.007 | 1.00 | 36.36 |
| ATOM | 486 | C | ILE | 73 | 193.106 | 152.010 | 181.225 | 1.00 | 33.43 |
| ATOM | 487 | O | ILE | 73 | 191.893 | 152.069 | 181.414 | 1.00 | 34.64 |
| ATOM | 488 | N | PRO | 74 | 193.635 | 152.178 | 180.010 | 1.00 | 31.24 |
| ATOM | 489 | CD | PRO | 74 | 195.053 | 152.173 | 179.607 | 1.00 | 29.27 |
| ATOM | 490 | CA | PRO | 74 | 192.726 | 152.420 | 178.886 | 1.00 | 29.89 |
| ATOM | 491 | CB | PRO | 74 | 193.661 | 152.659 | 177.704 | 1.00 | 29.36 |
| ATOM | 492 | CG | PRO | 74 | 194.979 | 152.118 | 178.118 | 1.00 | 28.88 |
| ATOM | 493 | C | PRO | 74 | 191.791 | 151.242 | 178.648 | 1.00 | 29.28 |
| ATOM | 494 | O | PRO | 74 | 192.197 | 150.091 | 178.791 | 1.00 | 30.28 |
| ATOM | 495 | N | VAL | 75 | 190.542 | 151.541 | 178.290 | 1.00 | 28.41 |
| ATOM | 496 | CA | VAL | 75 | 189.532 | 150.514 | 178.018 | 1.00 | 26.87 |
| ATOM | 497 | CB | VAL | 75 | 188.361 | 150.597 | 179.013 | 1.00 | 27.40 |
| ATOM | 498 | CG1 | VAL | 75 | 187.383 | 149.471 | 178.733 | 1.00 | 25.27 |
| ATOM | 499 | CG2 | VAL | 75 | 188.871 | 150.512 | 180.445 | 1.00 | 26.72 |
| ATOM | 500 | C | VAL | 75 | 188.987 | 150.704 | 176.608 | 1.00 | 26.73 |
| ATOM | 501 | O | VAL | 75 | 188.681 | 151.829 | 176.201 | 1.00 | 26.50 |
| ATOM | 502 | N | THR | 76 | 188.887 | 149.597 | 175.870 | 1.00 | 25.57 |
| ATOM | 503 | CA | THR | 76 | 188.406 | 149.592 | 174.497 | 1.00 | 25.04 |
| ATOM | 504 | CB | THR | 76 | 189.447 | 148.971 | 173.554 | 1.00 | 24.30 |
| ATOM | 505 | OG1 | THR | 76 | 190.480 | 149.931 | 173.321 | 1.00 | 26.31 |
| ATOM | 506 | CG2 | THR | 76 | 188.792 | 148.557 | 172.238 | 1.00 | 23.39 |
| ATOM | 507 | C | THR | 76 | 187.135 | 148.783 | 174.450 | 1.00 | 25.22 |
| ATOM | 508 | O | THR | 76 | 187.131 | 147.651 | 174.882 | 1.00 | 24.53 |

*FIG. 4A - 9*

```
ATOM  509  N    TYR  77    186.043 149.383 173.978  1.00 23.94
ATOM  510  CA   TYR  77    184.767 148.668 173.898  1.00 23.24
ATOM  511  CB   TYR  77    183.614 149.615 174.189  1.00 20.71
ATOM  512  CG   TYR  77    183.756 150.353 175.494  1.00 21.39
ATOM  513  CD1  TYR  77    183.702 151.742 175.535  1.00 19.31
ATOM  514  CE1  TYR  77    183.872 152.430 176.727  1.00 20.40
ATOM  515  CD2  TYR  77    183.979 149.664 176.688  1.00 21.13
ATOM  516  CE2  TYR  77    184.150 150.352 177.888  1.00 22.05
ATOM  517  CZ   TYR  77    184.099 151.732 177.894  1.00 21.89
ATOM  518  OH   TYR  77    184.310 152.414 179.068  1.00 23.51
ATOM  519  C    TYR  77    184.606 148.085 172.509  1.00 24.36
ATOM  520  O    TYR  77    184.748 148.788 171.507  1.00 26.17
ATOM  521  N    LEU  78    184.272 146.805 172.448  1.00 23.57
ATOM  522  CA   LEU  78    184.138 146.146 171.160  1.00 23.59
ATOM  523  CB   LEU  78    185.323 145.201 170.979  1.00 26.78
ATOM  524  CG   LEU  78    185.993 145.054 169.618  1.00 30.83
ATOM  525  CD1  LEU  78    186.643 146.366 169.228  1.00 32.06
ATOM  526  CD2  LEU  78    187.035 143.940 169.683  1.00 32.08
ATOM  527  C    LEU  78    182.848 145.371 170.914  1.00 22.74
ATOM  528  O    LEU  78    182.273 144.773 171.821  1.00 22.60
ATOM  529  N    GLY  79    182.418 145.383 169.657  1.00 22.35
ATOM  530  CA   GLY  79    181.240 144.650 169.246  1.00 20.32
ATOM  531  C    GLY  79    181.735 143.538 168.334  1.00 21.11
ATOM  532  O    GLY  79    182.584 142.737 168.734  1.00 20.12
ATOM  533  N    ASN  80    181.237 143.496 167.103  1.00 19.99
ATOM  534  CA   ASN  80    181.651 142.468 166.156  1.00 18.80
ATOM  535  CB   ASN  80    180.493 142.119 165.234  1.00 15.57
ATOM  536  CG   ASN  80    179.370 141.438 165.962  1.00 15.24
ATOM  537  OD1  ASN  80    179.449 140.254 166.270  1.00 18.15
ATOM  538  ND2  ASN  80    178.314 142.182 166.248  1.00 16.69
ATOM  539  C    ASN  80    182.859 142.881 165.324  1.00 20.01
ATOM  540  O    ASN  80    183.361 142.096 164.520  1.00 20.92
ATOM  541  N    GLY  81    183.321 144.113 165.514  1.00 20.24
ATOM  542  CA   GLY  81    184.474 144.593 164.774  1.00 21.43
ATOM  543  C    GLY  81    184.226 144.777 163.288  1.00 23.76
ATOM  544  O    GLY  81    185.116 144.538 162.470  1.00 23.93
ATOM  545  N    SER  82    183.021 145.206 162.926  1.00 23.90
ATOM  546  CA   SER  82    182.703 145.416 161.523  1.00 24.30
ATOM  547  CB   SER  82    181.258 144.994 161.229  1.00 22.23
ATOM  548  OG   SER  82    180.320 145.842 161.860  1.00 21.40
ATOM  549  C    SER  82    182.931 146.863 161.090  1.00 25.78
ATOM  550  O    SER  82    182.703 147.206 159.932  1.00 27.34
ATOM  551  N    ASN  83    183.384 147.712 162.009  1.00 25.39
ATOM  552  CA   ASN  83    183.644 149.098 161.652  1.00 26.74
ATOM  553  CB   ASN  83    182.431 149.979 161.942  1.00 29.33
ATOM  554  CG   ASN  83    182.423 151.238 161.094  1.00 32.00
ATOM  555  OD1  ASN  83    182.581 151.176 159.877  1.00 35.65
ATOM  556  ND2  ASN  83    182.247 152.385 161.733  1.00 34.48
ATOM  557  C    ASN  83    184.872 149.722 162.292  1.00 27.53
ATOM  558  O    ASN  83    184.822 150.853 162.777  1.00 27.55
ATOM  559  N    ILE  84    185.970 148.976 162.292  1.00 28.70
ATOM  560  CA   ILE  84    187.252 149.445 162.816  1.00 30.05
ATOM  561  CB   ILE  84    187.407 149.282 164.344  1.00 31.85
ATOM  562  CG2  ILE  84    186.933 150.534 165.063  1.00 31.87
ATOM  563  CG1  ILE  84    186.743 147.980 164.780  1.00 32.79
ATOM  564  CD1  ILE  84    186.218 147.991 166.190  1.00 38.26
ATOM  565  C    ILE  84    188.318 148.559 162.216  1.00 28.35
```

*FIG. 4A - 10*

```
ATOM    566  O    ILE  84     188.024 147.536 161.611  1.00 27.43
ATOM    567  N    ILE  85     189.563 148.966 162.394  1.00 27.13
ATOM    568  CA   ILE  85     190.685 148.189 161.925  1.00 24.74
ATOM    569  CB   ILE  85     191.329 148.824 160.687  1.00 25.47
ATOM    570  CG2  ILE  85     192.642 148.119 160.364  1.00 23.51
ATOM    571  CG1  ILE  85     190.369 148.703 159.497  1.00 24.34
ATOM    572  CD1  ILE  85     190.554 149.768 158.438  1.00 25.69
ATOM    573  C    ILE  85     191.635 148.195 163.105  1.00 23.80
ATOM    574  O    ILE  85     192.056 149.253 163.567  1.00 22.55
ATOM    575  N    ILE  86     191.928 147.013 163.627  1.00 23.75
ATOM    576  CA   ILE  86     192.819 146.898 164.766  1.00 24.48
ATOM    577  CB   ILE  86     192.267 145.893 165.801  1.00 23.81
ATOM    578  CG2  ILE  86     193.070 145.980 167.089  1.00 24.06
ATOM    579  CG1  ILE  86     190.798 146.200 166.096  1.00 21.88
ATOM    580  CD1  ILE  86     190.154 145.222 167.062  1.00 20.82
ATOM    581  C    ILE  86     194.190 146.442 164.283  1.00 25.81
ATOM    582  O    ILE  86     194.316 145.392 163.658  1.00 25.21
ATOM    583  N    ARG  87     195.212 147.241 164.575  1.00 27.74
ATOM    584  CA   ARG  87     196.576 146.939 164.161  1.00 28.42
ATOM    585  CB   ARG  87     197.508 148.062 164.598  1.00 27.28
ATOM    586  CG   ARG  87     197.189 149.384 163.926  1.00 28.41
ATOM    587  CD   ARG  87     198.393 150.298 163.905  1.00 31.58
ATOM    588  NE   ARG  87     198.239 151.370 162.931  1.00 34.81
ATOM    589  CZ   ARG  87     197.895 152.612 163.248  1.00 37.84
ATOM    590  NH1  ARG  87     197.669 152.930 164.515  1.00 38.55
ATOM    591  NH2  ARG  87     197.789 153.538 162.305  1.00 37.69
ATOM    592  C    ARG  87     197.085 145.603 164.680  1.00 29.71
ATOM    593  O    ARG  87     196.655 145.116 165.725  1.00 29.55
ATOM    594  N    GLU  88     198.016 145.018 163.936  1.00 30.71
ATOM    595  CA   GLU  88     198.585 143.726 164.282  1.00 32.31
ATOM    596  CB   GLU  88     199.467 143.239 163.129  1.00 33.25
ATOM    597  CG   GLU  88     198.668 142.854 161.888  1.00 38.46
ATOM    598  CD   GLU  88     197.376 142.106 162.225  1.00 41.61
ATOM    599  OE1  GLU  88     197.380 141.326 163.202  1.00 44.03
ATOM    600  OE2  GLU  88     196.359 142.293 161.518  1.00 40.61
ATOM    601  C    GLU  88     199.357 143.705 165.602  1.00 31.64
ATOM    602  O    GLU  88     199.729 142.636 166.091  1.00 31.72
ATOM    603  N    GLY  89     199.594 144.878 166.179  1.00 30.32
ATOM    604  CA   GLY  89     200.301 144.941 167.447  1.00 28.08
ATOM    605  C    GLY  89     199.336 144.681 168.590  1.00 27.89
ATOM    606  O    GLY  89     199.744 144.473 169.736  1.00 27.88
ATOM    607  N    GLY  90     198.043 144.695 168.274  1.00 27.37
ATOM    608  CA   GLY  90     197.027 144.453 169.281  1.00 26.48
ATOM    609  C    GLY  90     196.631 145.711 170.027  1.00 26.32
ATOM    610  O    GLY  90     196.930 146.818 169.584  1.00 26.65
ATOM    611  N    ILE  91     195.961 145.543 171.163  1.00 26.11
ATOM    612  CA   ILE  91     195.518 146.676 171.972  1.00 25.92
ATOM    613  CB   ILE  91     193.974 146.751 172.030  1.00 24.62
ATOM    614  CG2  ILE  91     193.542 147.824 173.017  1.00 22.45
ATOM    615  CG1  ILE  91     193.412 147.060 170.643  1.00 22.49
ATOM    616  CD1  ILE  91     191.908 147.067 170.591  1.00 21.61
ATOM    617  C    ILE  91     196.040 146.610 173.407  1.00 27.23
ATOM    618  O    ILE  91     195.885 145.599 174.094  1.00 28.20
ATOM    619  N    ARG  92     196.659 147.697 173.851  1.00 26.62
ATOM    620  CA   ARG  92     197.187 147.782 175.203  1.00 27.30
ATOM    621  CB   ARG  92     198.218 148.908 175.296  1.00 27.78
ATOM    622  CG   ARG  92     199.538 148.612 174.608  1.00 27.28
```

*FIG. 4A-11*

| ATOM | 623 | CD | ARG | 92 | 200.218 | 147.397 | 175.216 | 1.00 | 30.86 |
|------|-----|-----|-----|-----|---------|---------|---------|------|-------|
| ATOM | 624 | NE | ARG | 92 | 199.611 | 146.156 | 174.736 | 1.00 | 32.57 |
| ATOM | 625 | CZ | ARG | 92 | 199.636 | 145.760 | 173.468 | 1.00 | 31.04 |
| ATOM | 626 | NH1 | ARG | 92 | 200.238 | 146.504 | 172.553 | 1.00 | 30.59 |
| ATOM | 627 | NH2 | ARG | 92 | 199.052 | 144.629 | 173.108 | 1.00 | 29.88 |
| ATOM | 628 | C | ARG | 92 | 196.042 | 148.080 | 176.158 | 1.00 | 27.80 |
| ATOM | 629 | O | ARG | 92 | 195.180 | 148.900 | 175.860 | 1.00 | 29.92 |
| ATOM | 630 | N | GLY | 93 | 196.029 | 147.415 | 177.305 | 1.00 | 27.62 |
| ATOM | 631 | CA | GLY | 93 | 194.974 | 147.665 | 178.268 | 1.00 | 27.54 |
| ATOM | 632 | C | GLY | 93 | 193.856 | 146.646 | 178.275 | 1.00 | 27.68 |
| ATOM | 633 | O | GLY | 93 | 194.062 | 145.478 | 177.944 | 1.00 | 27.53 |
| ATOM | 634 | N | ILE | 94 | 192.662 | 147.096 | 178.648 | 1.00 | 26.93 |
| ATOM | 635 | CA | ILE | 94 | 191.500 | 146.223 | 178.725 | 1.00 | 26.84 |
| ATOM | 636 | CB | ILE | 94 | 190.725 | 146.471 | 180.026 | 1.00 | 26.15 |
| ATOM | 637 | CG2 | ILE | 94 | 189.440 | 145.663 | 180.030 | 1.00 | 27.04 |
| ATOM | 638 | CG1 | ILE | 94 | 191.591 | 146.094 | 181.226 | 1.00 | 26.06 |
| ATOM | 639 | CD1 | ILE | 94 | 191.212 | 146.814 | 182.503 | 1.00 | 25.80 |
| ATOM | 640 | C | ILE | 94 | 190.523 | 146.377 | 177.567 | 1.00 | 26.98 |
| ATOM | 641 | O | ILE | 94 | 190.127 | 147.488 | 177.216 | 1.00 | 27.87 |
| ATOM | 642 | N | VAL | 95 | 190.137 | 145.251 | 176.977 | 1.00 | 26.43 |
| ATOM | 643 | CA | VAL | 95 | 189.173 | 145.252 | 175.886 | 1.00 | 24.97 |
| ATOM | 644 | CB | VAL | 95 | 189.667 | 144.459 | 174.654 | 1.00 | 24.71 |
| ATOM | 645 | CG1 | VAL | 95 | 188.570 | 144.412 | 173.598 | 1.00 | 22.13 |
| ATOM | 646 | CG2 | VAL | 95 | 190.915 | 145.093 | 174.083 | 1.00 | 23.63 |
| ATOM | 647 | C | VAL | 95 | 187.936 | 144.547 | 176.418 | 1.00 | 25.02 |
| ATOM | 648 | O | VAL | 95 | 188.011 | 143.385 | 176.813 | 1.00 | 24.88 |
| ATOM | 649 | N | ILE | 96 | 186.808 | 145.249 | 176.455 | 1.00 | 23.82 |
| ATOM | 650 | CA | ILE | 96 | 185.571 | 144.640 | 176.924 | 1.00 | 22.67 |
| ATOM | 651 | CB | ILE | 96 | 184.780 | 145.574 | 177.868 | 1.00 | 21.74 |
| ATOM | 652 | CG2 | ILE | 96 | 183.495 | 144.894 | 178.303 | 1.00 | 19.52 |
| ATOM | 653 | CG1 | ILE | 96 | 185.609 | 145.909 | 179.105 | 1.00 | 20.88 |
| ATOM | 654 | CD1 | ILE | 96 | 184.920 | 146.873 | 180.045 | 1.00 | 19.00 |
| ATOM | 655 | C | ILE | 96 | 184.696 | 144.334 | 175.716 | 1.00 | 22.33 |
| ATOM | 656 | O | ILE | 96 | 184.333 | 145.236 | 174.967 | 1.00 | 22.44 |
| ATOM | 657 | N | SER | 97 | 184.379 | 143.059 | 175.518 | 1.00 | 22.08 |
| ATOM | 658 | CA | SER | 97 | 183.529 | 142.642 | 174.409 | 1.00 | 21.79 |
| ATOM | 659 | CB | SER | 97 | 183.960 | 141.265 | 173.906 | 1.00 | 21.29 |
| ATOM | 660 | OG | SER | 97 | 183.011 | 140.715 | 173.010 | 1.00 | 22.88 |
| ATOM | 661 | C | SER | 97 | 182.111 | 142.580 | 174.959 | 1.00 | 23.28 |
| ATOM | 662 | O | SER | 97 | 181.869 | 141.942 | 175.985 | 1.00 | 24.15 |
| ATOM | 663 | N | LEU | 98 | 181.173 | 143.246 | 174.292 | 1.00 | 22.46 |
| ATOM | 664 | CA | LEU | 98 | 179.790 | 143.268 | 174.766 | 1.00 | 21.21 |
| ATOM | 665 | CB | LEU | 98 | 179.164 | 144.639 | 174.500 | 1.00 | 18.28 |
| ATOM | 666 | CG | LEU | 98 | 179.742 | 145.866 | 175.210 | 1.00 | 19.27 |
| ATOM | 667 | CD1 | LEU | 98 | 179.811 | 145.614 | 176.705 | 1.00 | 17.05 |
| ATOM | 668 | CD2 | LEU | 98 | 181.120 | 146.175 | 174.658 | 1.00 | 16.52 |
| ATOM | 669 | C | LEU | 98 | 178.921 | 142.199 | 174.123 | 1.00 | 20.70 |
| ATOM | 670 | O | LEU | 98 | 177.713 | 142.150 | 174.358 | 1.00 | 21.26 |
| ATOM | 671 | N | LEU | 99 | 179.541 | 141.334 | 173.329 | 1.00 | 19.62 |
| ATOM | 672 | CA | LEU | 99 | 178.822 | 140.288 | 172.612 | 1.00 | 20.23 |
| ATOM | 673 | CB | LEU | 99 | 179.807 | 139.505 | 171.743 | 1.00 | 17.15 |
| ATOM | 674 | CG | LEU | 99 | 180.440 | 140.356 | 170.644 | 1.00 | 17.36 |
| ATOM | 675 | CD1 | LEU | 99 | 181.166 | 139.464 | 169.646 | 1.00 | 18.38 |
| ATOM | 676 | CD2 | LEU | 99 | 179.357 | 141.156 | 169.947 | 1.00 | 16.53 |
| ATOM | 677 | C | LEU | 99 | 177.961 | 139.316 | 173.410 | 1.00 | 21.16 |
| ATOM | 678 | O | LEU | 99 | 177.123 | 138.625 | 172.833 | 1.00 | 23.43 |
| ATOM | 679 | N | SER | 100 | 178.152 | 139.247 | 174.722 | 1.00 | 19.24 |

*FIG. 4A - 12*

| | | | | | | | | | |
|---|---|---|---|---|---|---|---|---|---|
| ATOM | 680 | CA | SER | 100 | 177.340 | 138.324 | 175.518 | 1.00 | 19.50 |
| ATOM | 681 | CB | SER | 100 | 178.157 | 137.719 | 176.651 | 1.00 | 19.05 |
| ATOM | 682 | OG | SER | 100 | 178.711 | 136.477 | 176.245 | 1.00 | 21.06 |
| ATOM | 683 | C | SER | 100 | 176.095 | 138.997 | 176.083 | 1.00 | 19.80 |
| ATOM | 684 | O | SER | 100 | 175.180 | 138.319 | 176.537 | 1.00 | 20.77 |
| ATOM | 685 | N | LEU | 101 | 176.084 | 140.317 | 176.080 | 1.00 | 18.90 |
| ATOM | 686 | CA | LEU | 101 | 174.913 | 141.045 | 176.564 | 1.00 | 19.65 |
| ATOM | 687 | CB | LEU | 101 | 175.263 | 142.498 | 176.851 | 1.00 | 16.22 |
| ATOM | 688 | CG | LEU | 101 | 176.386 | 142.669 | 177.857 | 1.00 | 15.48 |
| ATOM | 689 | CD1 | LEU | 101 | 176.511 | 144.090 | 178.377 | 1.00 | 16.79 |
| ATOM | 690 | CD2 | LEU | 101 | 176.126 | 141.735 | 179.017 | 1.00 | 13.64 |
| ATOM | 691 | C | LEU | 101 | 173.978 | 140.940 | 175.362 | 1.00 | 21.11 |
| ATOM | 692 | O | LEU | 101 | 173.766 | 141.922 | 174.659 | 1.00 | 20.29 |
| ATOM | 693 | N | ASP | 102 | 173.422 | 139.737 | 175.123 | 1.00 | 22.71 |
| ATOM | 694 | CA | ASP | 102 | 172.565 | 139.532 | 173.952 | 1.00 | 22.86 |
| ATOM | 695 | CB | ASP | 102 | 173.119 | 138.364 | 173.141 | 1.00 | 24.01 |
| ATOM | 696 | CG | ASP | 102 | 172.796 | 137.005 | 173.715 | 1.00 | 28.13 |
| ATOM | 697 | OD1 | ASP | 102 | 173.160 | 136.004 | 173.084 | 1.00 | 32.63 |
| ATOM | 698 | OD2 | ASP | 102 | 172.187 | 136.906 | 174.775 | 1.00 | 33.07 |
| ATOM | 699 | C | ASP | 102 | 171.039 | 139.465 | 173.991 | 1.00 | 21.60 |
| ATOM | 700 | O | ASP | 102 | 170.411 | 139.335 | 172.933 | 1.00 | 20.85 |
| ATOM | 701 | N | HIS | 103 | 170.416 | 139.686 | 175.151 | 1.00 | 21.98 |
| ATOM | 702 | CA | HIS | 103 | 168.952 | 139.614 | 175.210 | 1.00 | 22.94 |
| ATOM | 703 | CB | HIS | 103 | 168.441 | 139.963 | 176.605 | 1.00 | 24.19 |
| ATOM | 704 | CG | HIS | 103 | 168.539 | 141.421 | 176.932 | 1.00 | 28.16 |
| ATOM | 705 | CD2 | HIS | 103 | 167.610 | 142.411 | 176.946 | 1.00 | 28.53 |
| ATOM | 706 | ND1 | HIS | 103 | 169.723 | 142.002 | 177.329 | 1.00 | 29.74 |
| ATOM | 707 | CE1 | HIS | 103 | 169.523 | 143.285 | 177.572 | 1.00 | 29.81 |
| ATOM | 708 | NE2 | HIS | 103 | 168.250 | 143.559 | 177.348 | 1.00 | 28.05 |
| ATOM | 709 | C | HIS | 103 | 168.214 | 140.510 | 174.216 | 1.00 | 22.82 |
| ATOM | 710 | O | HIS | 103 | 168.733 | 141.545 | 173.815 | 1.00 | 22.45 |
| ATOM | 711 | N | ILE | 104 | 166.996 | 140.104 | 173.843 | 1.00 | 22.72 |
| ATOM | 712 | CA | ILE | 104 | 166.099 | 140.847 | 172.949 | 1.00 | 22.69 |
| ATOM | 713 | CB | ILE | 104 | 166.157 | 140.370 | 171.485 | 1.00 | 22.71 |
| ATOM | 714 | CG2 | ILE | 104 | 165.213 | 141.209 | 170.626 | 1.00 | 20.31 |
| ATOM | 715 | CG1 | ILE | 104 | 167.582 | 140.470 | 170.950 | 1.00 | 21.60 |
| ATOM | 716 | CD1 | ILE | 104 | 167.715 | 139.981 | 169.525 | 1.00 | 19.81 |
| ATOM | 717 | C | ILE | 104 | 164.726 | 140.470 | 173.484 | 1.00 | 23.10 |
| ATOM | 718 | O | ILE | 104 | 164.371 | 139.291 | 173.487 | 1.00 | 20.75 |
| ATOM | 719 | N | GLU | 105 | 163.968 | 141.450 | 173.960 | 1.00 | 23.51 |
| ATOM | 720 | CA | GLU | 105 | 162.647 | 141.177 | 174.505 | 1.00 | 25.25 |
| ATOM | 721 | CB | GLU | 105 | 162.687 | 141.257 | 176.031 | 1.00 | 28.35 |
| ATOM | 722 | CG | GLU | 105 | 163.448 | 140.111 | 176.672 | 1.00 | 36.37 |
| ATOM | 723 | CD | GLU | 105 | 162.767 | 138.775 | 176.443 | 1.00 | 41.87 |
| ATOM | 724 | OE1 | GLU | 105 | 161.522 | 138.728 | 176.545 | 1.00 | 46.70 |
| ATOM | 725 | OE2 | GLU | 105 | 163.467 | 137.776 | 176.159 | 1.00 | 41.11 |
| ATOM | 726 | C | GLU | 105 | 161.639 | 142.169 | 173.954 | 1.00 | 24.44 |
| ATOM | 727 | O | GLU | 105 | 161.947 | 143.348 | 173.786 | 1.00 | 23.87 |
| ATOM | 728 | N | VAL | 106 | 160.433 | 141.687 | 173.671 | 1.00 | 24.48 |
| ATOM | 729 | CA | VAL | 106 | 159.386 | 142.536 | 173.122 | 1.00 | 23.88 |
| ATOM | 730 | CB | VAL | 106 | 158.906 | 142.001 | 171.759 | 1.00 | 23.49 |
| ATOM | 731 | CG1 | VAL | 106 | 157.885 | 142.947 | 171.160 | 1.00 | 22.76 |
| ATOM | 732 | CG2 | VAL | 106 | 160.085 | 141.839 | 170.823 | 1.00 | 21.17 |
| ATOM | 733 | C | VAL | 106 | 158.178 | 142.659 | 174.043 | 1.00 | 24.64 |
| ATOM | 734 | O | VAL | 106 | 157.787 | 141.703 | 174.710 | 1.00 | 25.47 |
| ATOM | 735 | N | SER | 107 | 157.600 | 143.854 | 174.080 | 1.00 | 24.24 |
| ATOM | 736 | CA | SER | 107 | 156.416 | 144.123 | 174.889 | 1.00 | 23.57 |

*FIG. 4A - 13*

```
ATOM    737  CB   SER   107     156.792 144.790 176.212  1.00 22.57
ATOM    738  OG   SER   107     155.687 144.788 177.099  1.00 24.31
ATOM    739  C    SER   107     155.532 145.051 174.074  1.00 21.97
ATOM    740  O    SER   107     155.776 146.253 173.997  1.00 21.65
ATOM    741  N    ASP   108     154.508 144.473 173.459  1.00 20.43
ATOM    742  CA   ASP   108     153.589 145.214 172.610  1.00 22.12
ATOM    743  CB   ASP   108     152.851 146.298 173.393  1.00 21.96
ATOM    744  CG   ASP   108     151.651 146.846 172.632  1.00 23.48
ATOM    745  OD1  ASP   108     150.907 147.672 173.196  1.00 26.61
ATOM    746  OD2  ASP   108     151.449 146.450 171.465  1.00 24.62
ATOM    747  C    ASP   108     154.336 145.843 171.443  1.00 22.03
ATOM    748  O    ASP   108     154.753 145.144 170.525  1.00 24.44
ATOM    749  N    ASP   109     154.507 147.159 171.479  1.00 21.58
ATOM    750  CA   ASP   109     155.196 147.860 170.403  1.00 24.01
ATOM    751  CB   ASP   109     154.428 149.132 170.028  1.00 24.38
ATOM    752  CG   ASP   109     154.344 150.117 171.176  1.00 27.09
ATOM    753  OD1  ASP   109     153.856 151.251 170.966  1.00 29.79
ATOM    754  OD2  ASP   109     154.766 149.759 172.296  1.00 29.10
ATOM    755  C    ASP   109     156.630 148.227 170.775  1.00 24.28
ATOM    756  O    ASP   109     157.337 148.852 169.987  1.00 24.37
ATOM    757  N    ALA   110     157.057 147.832 171.971  1.00 24.09
ATOM    758  CA   ALA   110     158.402 148.137 172.443  1.00 23.19
ATOM    759  CB   ALA   110     158.340 148.667 173.865  1.00 21.36
ATOM    760  C    ALA   110     159.338 146.939 172.386  1.00 23.91
ATOM    761  O    ALA   110     158.929 145.802 172.628  1.00 24.28
ATOM    762  N    ILE   111     160.602 147.212 172.074  1.00 23.63
ATOM    763  CA   ILE   111     161.633 146.183 171.994  1.00 21.28
ATOM    764  CB   ILE   111     162.083 145.919 170.541  1.00 20.76
ATOM    765  CG2  ILE   111     163.110 144.795 170.522  1.00 19.54
ATOM    766  CG1  ILE   111     160.891 145.567 169.655  1.00 19.89
ATOM    767  CD1  ILE   111     161.287 145.235 168.222  1.00 20.02
ATOM    768  C    ILE   111     162.879 146.653 172.739  1.00 21.68
ATOM    769  O    ILE   111     163.301 147.795 172.573  1.00 21.97
ATOM    770  N    ILE   112     163.461 145.788 173.563  1.00 20.22
ATOM    771  CA   ILE   112     164.690 146.139 174.267  1.00 20.10
ATOM    772  CB   ILE   112     164.535 146.100 175.812  1.00 21.14
ATOM    773  CG2  ILE   112     163.636 147.234 176.267  1.00 21.03
ATOM    774  CG1  ILE   112     163.966 144.757 176.271  1.00 21.70
ATOM    775  CD1  ILE   112     163.961 144.597 177.785  1.00 20.79
ATOM    776  C    ILE   112     165.736 145.124 173.834  1.00 19.97
ATOM    777  O    ILE   112     165.417 143.959 173.614  1.00 18.26
ATOM    778  N    ALA   113     166.982 145.558 173.702  1.00 19.65
ATOM    779  CA   ALA   113     168.030 144.648 173.267  1.00 20.00
ATOM    780  CB   ALA   113     168.122 144.669 171.743  1.00 18.37
ATOM    781  C    ALA   113     169.383 144.984 173.873  1.00 19.68
ATOM    782  O    ALA   113     169.746 146.155 173.980  1.00 19.29
ATOM    783  N    GLY   114     170.120 143.949 174.273  1.00 18.64
ATOM    784  CA   GLY   114     171.438 144.153 174.848  1.00 17.95
ATOM    785  C    GLY   114     172.384 144.651 173.775  1.00 17.39
ATOM    786  O    GLY   114     172.227 144.312 172.607  1.00 18.74
ATOM    787  N    SER   115     173.376 145.446 174.154  1.00 17.23
ATOM    788  CA   SER   115     174.301 145.991 173.173  1.00 19.08
ATOM    789  CB   SER   115     175.269 146.961 173.847  1.00 16.94
ATOM    790  OG   SER   115     176.054 146.304 174.819  1.00 20.43
ATOM    791  C    SER   115     175.086 144.947 172.386  1.00 20.08
ATOM    792  O    SER   115     175.714 145.273 171.380  1.00 20.80
ATOM    793  N    GLY   116     175.048 143.696 172.831  1.00 20.13
```

*FIG. 4A - 14*

| ATOM | 794 | CA | GLY | 116 | 175.778 | 142.654 | 172.129 | 1.00 | 18.28 |
|------|-----|-----|-----|-----|---------|---------|---------|------|-------|
| ATOM | 795 | C | GLY | 116 | 174.942 | 141.957 | 171.074 | 1.00 | 17.71 |
| ATOM | 796 | O | GLY | 116 | 175.461 | 141.241 | 170.221 | 1.00 | 18.17 |
| ATOM | 797 | N | ALA | 117 | 173.635 | 142.161 | 171.128 | 1.00 | 17.67 |
| ATOM | 798 | CA | ALA | 117 | 172.750 | 141.535 | 170.165 | 1.00 | 18.78 |
| ATOM | 799 | CB | ALA | 117 | 171.301 | 141.760 | 170.564 | 1.00 | 17.27 |
| ATOM | 800 | C | ALA | 117 | 172.997 | 142.093 | 168.773 | 1.00 | 19.95 |
| ATOM | 801 | O | ALA | 117 | 173.256 | 143.287 | 168.605 | 1.00 | 19.43 |
| ATOM | 802 | N | ALA | 118 | 172.922 | 141.221 | 167.776 | 1.00 | 19.62 |
| ATOM | 803 | CA | ALA | 118 | 173.114 | 141.636 | 166.401 | 1.00 | 18.85 |
| ATOM | 804 | CB | ALA | 118 | 173.279 | 140.417 | 165.518 | 1.00 | 16.94 |
| ATOM | 805 | C | ALA | 118 | 171.876 | 142.424 | 165.985 | 1.00 | 19.20 |
| ATOM | 806 | O | ALA | 118 | 170.750 | 141.965 | 166.180 | 1.00 | 19.45 |
| ATOM | 807 | N | ILE | 119 | 172.074 | 143.605 | 165.411 | 1.00 | 19.26 |
| ATOM | 808 | CA | ILE | 119 | 170.944 | 144.420 | 164.982 | 1.00 | 19.68 |
| ATOM | 809 | CB | ILE | 119 | 171.415 | 145.786 | 164.402 | 1.00 | 19.28 |
| ATOM | 810 | CG2 | ILE | 119 | 172.103 | 145.591 | 163.065 | 1.00 | 16.78 |
| ATOM | 811 | CG1 | ILE | 119 | 170.220 | 146.726 | 164.259 | 1.00 | 20.00 |
| ATOM | 812 | CD1 | ILE | 119 | 170.605 | 148.174 | 164.133 | 1.00 | 20.63 |
| ATOM | 813 | C | ILE | 119 | 170.093 | 143.674 | 163.950 | 1.00 | 18.91 |
| ATOM | 814 | O | ILE | 119 | 168.892 | 143.911 | 163.844 | 1.00 | 18.72 |
| ATOM | 815 | N | ILE | 120 | 170.714 | 142.766 | 163.201 | 1.00 | 18.03 |
| ATOM | 816 | CA | ILE | 120 | 169.996 | 141.984 | 162.201 | 1.00 | 16.99 |
| ATOM | 817 | CB | ILE | 120 | 170.972 | 141.153 | 161.327 | 1.00 | 16.61 |
| ATOM | 818 | CG2 | ILE | 120 | 170.251 | 139.967 | 160.698 | 1.00 | 13.57 |
| ATOM | 819 | CG1 | ILE | 120 | 171.561 | 142.036 | 160.224 | 1.00 | 16.84 |
| ATOM | 820 | CD1 | ILE | 120 | 172.707 | 141.404 | 159.460 | 1.00 | 12.97 |
| ATOM | 821 | C | ILE | 120 | 169.047 | 141.046 | 162.937 | 1.00 | 18.83 |
| ATOM | 822 | O | ILE | 120 | 167.956 | 140.744 | 162.457 | 1.00 | 19.15 |
| ATOM | 823 | N | ASP | 121 | 169.466 | 140.593 | 164.112 | 1.00 | 19.19 |
| ATOM | 824 | CA | ASP | 121 | 168.644 | 139.698 | 164.913 | 1.00 | 20.34 |
| ATOM | 825 | CB | ASP | 121 | 169.469 | 139.098 | 166.056 | 1.00 | 20.20 |
| ATOM | 826 | CG | ASP | 121 | 170.351 | 137.943 | 165.603 | 1.00 | 20.77 |
| ATOM | 827 | OD1 | ASP | 121 | 171.126 | 137.430 | 166.434 | 1.00 | 21.97 |
| ATOM | 828 | OD2 | ASP | 121 | 170.274 | 137.547 | 164.425 | 1.00 | 21.92 |
| ATOM | 829 | C | ASP | 121 | 167.458 | 140.479 | 165.478 | 1.00 | 20.77 |
| ATOM | 830 | O | ASP | 121 | 166.347 | 139.957 | 165.575 | 1.00 | 21.07 |
| ATOM | 831 | N | VAL | 122 | 167.700 | 141.731 | 165.854 | 1.00 | 20.22 |
| ATOM | 832 | CA | VAL | 122 | 166.642 | 142.572 | 166.402 | 1.00 | 20.06 |
| ATOM | 833 | CB | VAL | 122 | 167.210 | 143.873 | 167.006 | 1.00 | 18.18 |
| ATOM | 834 | CG1 | VAL | 122 | 166.108 | 144.648 | 167.702 | 1.00 | 15.98 |
| ATOM | 835 | CG2 | VAL | 122 | 168.310 | 143.545 | 167.987 | 1.00 | 16.47 |
| ATOM | 836 | C | VAL | 122 | 165.675 | 142.920 | 165.280 | 1.00 | 20.07 |
| ATOM | 837 | O | VAL | 122 | 164.461 | 142.941 | 165.471 | 1.00 | 20.32 |
| ATOM | 838 | N | SER | 123 | 166.224 | 143.188 | 164.103 | 1.00 | 18.21 |
| ATOM | 839 | CA | SER | 123 | 165.406 | 143.511 | 162.947 | 1.00 | 19.17 |
| ATOM | 840 | CB | SER | 123 | 166.302 | 143.817 | 161.751 | 1.00 | 18.64 |
| ATOM | 841 | OG | SER | 123 | 165.567 | 143.770 | 160.545 | 1.00 | 19.41 |
| ATOM | 842 | C | SER | 123 | 164.496 | 142.327 | 162.626 | 1.00 | 19.73 |
| ATOM | 843 | O | SER | 123 | 163.345 | 142.500 | 162.229 | 1.00 | 19.63 |
| ATOM | 844 | N | ARG | 124 | 165.023 | 141.122 | 162.812 | 1.00 | 20.21 |
| ATOM | 845 | CA | ARG | 124 | 164.274 | 139.902 | 162.550 | 1.00 | 19.02 |
| ATOM | 846 | CB | ARG | 124 | 165.234 | 138.717 | 162.432 | 1.00 | 17.61 |
| ATOM | 847 | CG | ARG | 124 | 165.785 | 138.531 | 161.032 | 1.00 | 18.34 |
| ATOM | 848 | CD | ARG | 124 | 166.937 | 137.540 | 160.982 | 1.00 | 18.68 |
| ATOM | 849 | NE | ARG | 124 | 167.685 | 137.689 | 159.737 | 1.00 | 22.31 |
| ATOM | 850 | CZ | ARG | 124 | 168.805 | 137.039 | 159.440 | 1.00 | 23.20 |

*FIG. 4A - 15*

```
ATOM    851  NH1  ARG  124    169.334  136.180  160.299  1.00  23.30
ATOM    852  NH2  ARG  124    169.409  137.263  158.281  1.00  23.65
ATOM    853  C    ARG  124    163.241  139.627  163.636  1.00  19.34
ATOM    854  O    ARG  124    162.241  138.958  163.387  1.00  20.99
ATOM    855  N    VAL  125    163.487  140.126  164.844  1.00  18.82
ATOM    856  CA   VAL  125    162.544  139.937  165.941  1.00  17.81
ATOM    857  CB   VAL  125    163.186  140.264  167.313  1.00  16.05
ATOM    858  CG1  VAL  125    162.110  140.552  168.347  1.00  14.45
ATOM    859  CG2  VAL  125    164.028  139.096  167.780  1.00  13.40
ATOM    860  C    VAL  125    161.376  140.883  165.687  1.00  19.62
ATOM    861  O    VAL  125    160.217  140.542  165.922  1.00  20.29
ATOM    862  N    ALA  126    161.693  142.074  165.194  1.00  19.75
ATOM    863  CA   ALA  126    160.675  143.067  164.886  1.00  21.04
ATOM    864  CB   ALA  126    161.318  144.301  164.273  1.00  18.04
ATOM    865  C    ALA  126    159.666  142.469  163.913  1.00  21.88
ATOM    866  O    ALA  126    158.456  142.606  164.098  1.00  22.73
ATOM    867  N    ARG  127    160.167  141.802  162.877  1.00  21.00
ATOM    868  CA   ARG  127    159.294  141.192  161.883  1.00  19.02
ATOM    869  CB   ARG  127    160.111  140.657  160.708  1.00  17.07
ATOM    870  CG   ARG  127    159.299  139.767  159.778  1.00  18.34
ATOM    871  CD   ARG  127    159.597  138.301  160.041  1.00  20.59
ATOM    872  NE   ARG  127    160.662  137.869  159.149  1.00  25.26
ATOM    873  CZ   ARG  127    161.776  137.261  159.531  1.00  21.54
ATOM    874  NH1  ARG  127    162.667  136.925  158.613  1.00  25.80
ATOM    875  NH2  ARG  127    161.995  136.972  160.807  1.00  21.15
ATOM    876  C    ARG  127    158.479  140.059  162.483  1.00  18.82
ATOM    877  O    ARG  127    157.296  139.905  162.186  1.00  20.09
ATOM    878  N    ASP  128    159.121  139.257  163.321  1.00  18.74
ATOM    879  CA   ASP  128    158.449  138.141  163.961  1.00  17.56
ATOM    880  CB   ASP  128    159.393  137.463  164.949  1.00  17.55
ATOM    881  CG   ASP  128    160.426  136.594  164.269  1.00  18.99
ATOM    882  OD1  ASP  128    161.462  136.310  164.902  1.00  21.64
ATOM    883  OD2  ASP  128    160.208  136.192  163.108  1.00  21.51
ATOM    884  C    ASP  128    157.212  138.625  164.709  1.00  19.71
ATOM    885  O    ASP  128    156.263  137.866  164.911  1.00  21.18
ATOM    886  N    TYR  129    157.232  139.890  165.123  1.00  19.49
ATOM    887  CA   TYR  129    156.125  140.480  165.869  1.00  18.58
ATOM    888  CB   TYR  129    156.662  141.184  167.115  1.00  20.31
ATOM    889  CG   TYR  129    157.048  140.216  168.208  1.00  22.09
ATOM    890  CD1  TYR  129    158.314  139.633  168.235  1.00  21.66
ATOM    891  CE1  TYR  129    158.658  138.707  169.213  1.00  21.62
ATOM    892  CD2  TYR  129    156.133  139.849  169.193  1.00  23.78
ATOM    893  CE2  TYR  129    156.467  138.924  170.177  1.00  23.90
ATOM    894  CZ   TYR  129    157.730  138.359  170.181  1.00  24.14
ATOM    895  OH   TYR  129    158.058  137.451  171.159  1.00  26.35
ATOM    896  C    TYR  129    155.314  141.451  165.032  1.00  17.88
ATOM    897  O    TYR  129    154.502  142.209  165.553  1.00  17.35
ATOM    898  N    ALA  130    155.542  141.420  163.726  1.00  18.06
ATOM    899  CA   ALA  130    154.823  142.283  162.800  1.00  17.32
ATOM    900  CB   ALA  130    153.359  141.878  162.744  1.00  14.09
ATOM    901  C    ALA  130    154.941  143.747  163.174  1.00  17.83
ATOM    902  O    ALA  130    153.954  144.481  163.154  1.00  18.57
ATOM    903  N    LEU  131    156.152  144.164  163.527  1.00  18.15
ATOM    904  CA   LEU  131    156.413  145.552  163.884  1.00  16.75
ATOM    905  CB   LEU  131    157.154  145.630  165.217  1.00  15.25
ATOM    906  CG   LEU  131    156.353  145.229  166.454  1.00  15.73
ATOM    907  CD1  LEU  131    157.269  145.195  167.666  1.00  14.72
```

*FIG. 4A - 16*

| ATOM | 908 | CD2 | LEU | 131 | 155.228 | 146.220 | 166.670 | 1.00 | 12.48 |
| --- | --- | --- | --- | --- | --- | --- | --- | --- | --- |
| ATOM | 909 | C | LEU | 131 | 157.280 | 146.123 | 162.772 | 1.00 | 16.92 |
| ATOM | 910 | O | LEU | 131 | 158.291 | 145.527 | 162.412 | 1.00 | 17.26 |
| ATOM | 911 | N | THR | 132 | 156.884 | 147.265 | 162.220 | 1.00 | 16.03 |
| ATOM | 912 | CA | THR | 132 | 157.638 | 147.881 | 161.135 | 1.00 | 16.11 |
| ATOM | 913 | CB | THR | 132 | 156.685 | 148.435 | 160.047 | 1.00 | 15.76 |
| ATOM | 914 | OG1 | THR | 132 | 157.446 | 148.944 | 158.945 | 1.00 | 15.92 |
| ATOM | 915 | CG2 | THR | 132 | 155.818 | 149.539 | 160.612 | 1.00 | 16.02 |
| ATOM | 916 | C | THR | 132 | 158.520 | 149.001 | 161.665 | 1.00 | 17.34 |
| ATOM | 917 | O | THR | 132 | 158.172 | 149.666 | 162.640 | 1.00 | 19.13 |
| ATOM | 918 | N | GLY | 133 | 159.676 | 149.196 | 161.038 | 1.00 | 18.19 |
| ATOM | 919 | CA | GLY | 133 | 160.570 | 150.248 | 161.481 | 1.00 | 17.67 |
| ATOM | 920 | C | GLY | 133 | 162.036 | 149.867 | 161.556 | 1.00 | 19.44 |
| ATOM | 921 | O | GLY | 133 | 162.890 | 150.741 | 161.704 | 1.00 | 20.71 |
| ATOM | 922 | N | LEU | 134 | 162.344 | 148.576 | 161.461 | 1.00 | 18.79 |
| ATOM | 923 | CA | LEU | 134 | 163.738 | 148.137 | 161.519 | 1.00 | 17.75 |
| ATOM | 924 | CB | LEU | 134 | 164.009 | 147.363 | 162.816 | 1.00 | 15.33 |
| ATOM | 925 | CG | LEU | 134 | 164.203 | 148.217 | 164.071 | 1.00 | 14.91 |
| ATOM | 926 | CD1 | LEU | 134 | 164.246 | 147.340 | 165.306 | 1.00 | 12.47 |
| ATOM | 927 | CD2 | LEU | 134 | 165.481 | 149.012 | 163.947 | 1.00 | 15.14 |
| ATOM | 928 | C | LEU | 134 | 164.134 | 147.283 | 160.317 | 1.00 | 18.03 |
| ATOM | 929 | O | LEU | 134 | 165.173 | 146.627 | 160.329 | 1.00 | 19.51 |
| ATOM | 930 | N | GLU | 135 | 163.307 | 147.295 | 159.277 | 1.00 | 17.89 |
| ATOM | 931 | CA | GLU | 135 | 163.600 | 146.528 | 158.072 | 1.00 | 17.97 |
| ATOM | 932 | CB | GLU | 135 | 162.472 | 146.680 | 157.044 | 1.00 | 16.62 |
| ATOM | 933 | CG | GLU | 135 | 161.105 | 146.184 | 157.505 | 1.00 | 18.54 |
| ATOM | 934 | CD | GLU | 135 | 160.237 | 147.301 | 158.061 | 1.00 | 20.00 |
| ATOM | 935 | OE1 | GLU | 135 | 160.793 | 148.218 | 158.699 | 1.00 | 20.46 |
| ATOM | 936 | OE2 | GLU | 135 | 159.003 | 147.265 | 157.862 | 1.00 | 21.36 |
| ATOM | 937 | C | GLU | 135 | 164.901 | 147.030 | 157.458 | 1.00 | 18.50 |
| ATOM | 938 | O | GLU | 135 | 165.678 | 146.254 | 156.906 | 1.00 | 19.90 |
| ATOM | 939 | N | PHE | 136 | 165.135 | 148.332 | 157.567 | 1.00 | 19.25 |
| ATOM | 940 | CA | PHE | 136 | 166.335 | 148.948 | 157.009 | 1.00 | 20.20 |
| ATOM | 941 | CB | PHE | 136 | 166.333 | 150.457 | 157.283 | 1.00 | 19.52 |
| ATOM | 942 | CG | PHE | 136 | 166.737 | 150.822 | 158.690 | 1.00 | 20.57 |
| ATOM | 943 | CD1 | PHE | 136 | 168.081 | 150.955 | 159.032 | 1.00 | 21.54 |
| ATOM | 944 | CD2 | PHE | 136 | 165.777 | 151.008 | 159.679 | 1.00 | 17.43 |
| ATOM | 945 | CE1 | PHE | 136 | 168.462 | 151.270 | 160.336 | 1.00 | 21.07 |
| ATOM | 946 | CE2 | PHE | 136 | 166.148 | 151.321 | 160.983 | 1.00 | 18.05 |
| ATOM | 947 | CZ | PHE | 136 | 167.496 | 151.450 | 161.313 | 1.00 | 19.98 |
| ATOM | 948 | C | PHE | 136 | 167.602 | 148.340 | 157.582 | 1.00 | 20.66 |
| ATOM | 949 | O | PHE | 136 | 168.668 | 148.427 | 156.974 | 1.00 | 21.25 |
| ATOM | 950 | N | ALA | 137 | 167.483 | 147.727 | 158.754 | 1.00 | 20.11 |
| ATOM | 951 | CA | ALA | 137 | 168.634 | 147.129 | 159.415 | 1.00 | 19.36 |
| ATOM | 952 | CB | ALA | 137 | 168.569 | 147.414 | 160.916 | 1.00 | 17.12 |
| ATOM | 953 | C | ALA | 137 | 168.784 | 145.632 | 159.183 | 1.00 | 20.18 |
| ATOM | 954 | O | ALA | 137 | 169.656 | 145.000 | 159.780 | 1.00 | 20.88 |
| ATOM | 955 | N | CYS | 138 | 167.964 | 145.059 | 158.308 | 1.00 | 19.71 |
| ATOM | 956 | CA | CYS | 138 | 168.034 | 143.621 | 158.067 | 1.00 | 19.71 |
| ATOM | 957 | CB | CYS | 138 | 166.897 | 143.184 | 157.144 | 1.00 | 19.52 |
| ATOM | 958 | SG | CYS | 138 | 166.971 | 143.834 | 155.468 | 1.00 | 17.96 |
| ATOM | 959 | C | CYS | 138 | 169.366 | 143.131 | 157.509 | 1.00 | 20.76 |
| ATOM | 960 | O | CYS | 138 | 169.648 | 141.931 | 157.524 | 1.00 | 21.13 |
| ATOM | 961 | N | GLY | 139 | 170.195 | 144.053 | 157.034 | 1.00 | 21.31 |
| ATOM | 962 | CA | GLY | 139 | 171.469 | 143.648 | 156.473 | 1.00 | 19.88 |
| ATOM | 963 | C | GLY | 139 | 172.675 | 144.377 | 157.025 | 1.00 | 20.92 |
| ATOM | 964 | O | GLY | 139 | 173.773 | 144.226 | 156.498 | 1.00 | 22.08 |

*FIG. 4A - 17*

```
ATOM    965   N    ILE   140      172.482 145.172 158.072  1.00 20.37
ATOM    966   CA   ILE   140      173.587 145.906 158.683  1.00 20.22
ATOM    967   CB   ILE   140      173.078 147.135 159.472  1.00 19.51
ATOM    968   CG2  ILE   140      174.236 147.818 160.190  1.00 17.75
ATOM    969   CG1  ILE   140      172.401 148.125 158.525  1.00 19.17
ATOM    970   CD1  ILE   140      171.682 149.241 159.244  1.00 17.44
ATOM    971   C    ILE   140      174.330 144.981 159.648  1.00 20.60
ATOM    972   O    ILE   140      173.760 144.504 160.627  1.00 20.85
ATOM    973   N    PRO   141      175.616 144.714 159.385  1.00 19.60
ATOM    974   CD   PRO   141      176.453 145.181 158.271  1.00 17.26
ATOM    975   CA   PRO   141      176.365 143.832 160.282  1.00 20.38
ATOM    976   CB   PRO   141      177.672 143.566 159.524  1.00 18.35
ATOM    977   CG   PRO   141      177.441 144.074 158.134  1.00 16.54
ATOM    978   C    PRO   141      176.619 144.483 161.637  1.00 20.15
ATOM    979   O    PRO   141      176.380 145.673 161.820  1.00 20.55
ATOM    980   N    GLY   142      177.089 143.692 162.592  1.00 20.02
ATOM    981   CA   GLY   142      177.398 144.245 163.895  1.00 18.78
ATOM    982   C    GLY   142      176.340 144.165 164.973  1.00 18.41
ATOM    983   O    GLY   142      175.252 143.633 164.773  1.00 17.85
ATOM    984   N    SER   143      176.680 144.733 166.125  1.00 17.82
ATOM    985   CA   SER   143      175.822 144.731 167.296  1.00 18.78
ATOM    986   CB   SER   143      176.680 144.513 168.530  1.00 17.63
ATOM    987   OG   SER   143      177.679 145.514 168.587  1.00 18.95
ATOM    988   C    SER   143      175.016 146.006 167.491  1.00 18.79
ATOM    989   O    SER   143      175.231 147.007 166.812  1.00 19.34
ATOM    990   N    ILE   144      174.093 145.954 168.444  1.00 18.20
ATOM    991   CA   ILE   144      173.253 147.091 168.765  1.00 18.59
ATOM    992   CB   ILE   144      172.166 146.690 169.800  1.00 18.07
ATOM    993   CG2  ILE   144      171.674 147.910 170.565  1.00 17.74
ATOM    994   CG1  ILE   144      170.994 146.016 169.083  1.00 16.11
ATOM    995   CD1  ILE   144      170.220 146.939 168.167  1.00 15.65
ATOM    996   C    ILE   144      174.122 148.213 169.332  1.00 19.49
ATOM    997   O    ILE   144      173.910 149.388 169.032  1.00 21.15
ATOM    998   N    GLY   145      175.103 147.847 170.150  1.00 19.55
ATOM    999   CA   GLY   145      175.977 148.846 170.743  1.00 18.89
ATOM   1000   C    GLY   145      176.731 149.627 169.687  1.00 19.57
ATOM   1001   O    GLY   145      176.911 150.840 169.795  1.00 18.14
ATOM   1002   N    GLY   146      177.177 148.924 168.654  1.00 20.17
ATOM   1003   CA   GLY   146      177.905 149.580 167.588  1.00 19.61
ATOM   1004   C    GLY   146      176.978 150.420 166.738  1.00 20.39
ATOM   1005   O    GLY   146      177.370 151.477 166.244  1.00 21.56
ATOM   1006   N    ALA   147      175.744 149.953 166.568  1.00 19.55
ATOM   1007   CA   ALA   147      174.760 150.670 165.767  1.00 19.45
ATOM   1008   CB   ALA   147      173.498 149.827 165.601  1.00 19.57
ATOM   1009   C    ALA   147      174.422 151.994 166.433  1.00 19.91
ATOM   1010   O    ALA   147      174.279 153.017 165.769  1.00 21.64
ATOM   1011   N    VAL   148      174.290 151.971 167.751  1.00 18.15
ATOM   1012   CA   VAL   148      173.980 153.183 168.490  1.00 18.50
ATOM   1013   CB   VAL   148      173.719 152.872 169.977  1.00 16.40
ATOM   1014   CG1  VAL   148      173.533 154.162 170.752  1.00 16.21
ATOM   1015   CG2  VAL   148      172.496 151.985 170.115  1.00 14.12
ATOM   1016   C    VAL   148      175.164 154.139 168.384  1.00 20.05
ATOM   1017   O    VAL   148      174.997 155.329 168.138  1.00 22.02
ATOM   1018   N    TYR   149      176.365 153.602 168.564  1.00 20.68
ATOM   1019   CA   TYR   149      177.587 154.392 168.502  1.00 20.75
ATOM   1020   CB   TYR   149      178.799 153.461 168.653  1.00 20.36
ATOM   1021   CG   TYR   149      180.153 154.135 168.539  1.00 20.56
```

*FIG. 4A - 18*

| | | | | | | | | |
|---|---|---|---|---|---|---|---|---|
| ATOM | 1022 | CD1 | TYR | 149 | 180.872 | 154.504 | 169.677 | 1.00 20.58 |
| ATOM | 1023 | CE1 | TYR | 149 | 182.133 | 155.092 | 169.571 | 1.00 21.00 |
| ATOM | 1024 | CD2 | TYR | 149 | 180.730 | 154.374 | 167.292 | 1.00 20.95 |
| ATOM | 1025 | CE2 | TYR | 149 | 181.985 | 154.959 | 167.175 | 1.00 19.37 |
| ATOM | 1026 | CZ | TYR | 149 | 182.680 | 155.314 | 168.313 | 1.00 22.18 |
| ATOM | 1027 | OH | TYR | 149 | 183.921 | 155.891 | 168.182 | 1.00 23.46 |
| ATOM | 1028 | C | TYR | 149 | 177.693 | 155.190 | 167.204 | 1.00 20.41 |
| ATOM | 1029 | O | TYR | 149 | 178.114 | 156.347 | 167.211 | 1.00 18.78 |
| ATOM | 1030 | N | MET | 150 | 177.296 | 154.568 | 166.098 | 1.00 20.71 |
| ATOM | 1031 | CA | MET | 150 | 177.370 | 155.188 | 164.775 | 1.00 21.46 |
| ATOM | 1032 | CB | MET | 150 | 177.965 | 154.198 | 163.763 | 1.00 21.73 |
| ATOM | 1033 | CG | MET | 150 | 179.280 | 153.560 | 164.167 | 1.00 20.73 |
| ATOM | 1034 | SD | MET | 150 | 180.667 | 154.567 | 163.689 | 1.00 12.78 |
| ATOM | 1035 | CE | MET | 150 | 180.320 | 154.843 | 162.031 | 1.00 16.09 |
| ATOM | 1036 | C | MET | 150 | 176.028 | 155.638 | 164.219 | 1.00 21.88 |
| ATOM | 1037 | O | MET | 150 | 175.971 | 156.160 | 163.106 | 1.00 22.27 |
| ATOM | 1038 | N | ASN | 151 | 174.957 | 155.449 | 164.983 | 1.00 20.86 |
| ATOM | 1039 | CA | ASN | 151 | 173.622 | 155.775 | 164.495 | 1.00 19.82 |
| ATOM | 1040 | CB | ASN | 151 | 173.422 | 157.280 | 164.311 | 1.00 19.88 |
| ATOM | 1041 | CG | ASN | 151 | 172.004 | 157.623 | 163.870 | 1.00 21.85 |
| ATOM | 1042 | OD1 | ASN | 151 | 171.052 | 156.923 | 164.220 | 1.00 20.62 |
| ATOM | 1043 | ND2 | ASN | 151 | 171.858 | 158.695 | 163.094 | 1.00 20.29 |
| ATOM | 1044 | C | ASN | 151 | 173.528 | 155.080 | 163.146 | 1.00 18.51 |
| ATOM | 1045 | O | ASN | 151 | 173.183 | 155.688 | 162.139 | 1.00 18.59 |
| ATOM | 1046 | N | ALA | 152 | 173.872 | 153.798 | 163.140 | 1.00 19.24 |
| ATOM | 1047 | CA | ALA | 152 | 173.849 | 152.994 | 161.932 | 1.00 19.13 |
| ATOM | 1048 | CB | ALA | 152 | 173.949 | 151.525 | 162.293 | 1.00 18.73 |
| ATOM | 1049 | C | ALA | 152 | 172.579 | 153.254 | 161.141 | 1.00 19.84 |
| ATOM | 1050 | O | ALA | 152 | 171.495 | 153.345 | 161.709 | 1.00 19.91 |
| ATOM | 1051 | N | GLY | 153 | 172.717 | 153.379 | 159.828 | 1.00 19.38 |
| ATOM | 1052 | CA | GLY | 153 | 171.559 | 153.630 | 158.995 | 1.00 18.89 |
| ATOM | 1053 | C | GLY | 153 | 171.760 | 153.076 | 157.604 | 1.00 20.29 |
| ATOM | 1054 | O | GLY | 153 | 172.895 | 152.855 | 157.175 | 1.00 19.10 |
| ATOM | 1055 | N | ALA | 154 | 170.656 | 152.846 | 156.902 | 1.00 20.29 |
| ATOM | 1056 | CA | ALA | 154 | 170.708 | 152.316 | 155.551 | 1.00 19.64 |
| ATOM | 1057 | CB | ALA | 154 | 171.149 | 150.874 | 155.580 | 1.00 16.43 |
| ATOM | 1058 | C | ALA | 154 | 169.351 | 152.425 | 154.883 | 1.00 20.98 |
| ATOM | 1059 | O | ALA | 154 | 168.320 | 152.267 | 155.530 | 1.00 22.64 |
| ATOM | 1060 | N | TYR | 155 | 169.364 | 152.707 | 153.584 | 1.00 21.32 |
| ATOM | 1061 | CA | TYR | 155 | 168.150 | 152.818 | 152.782 | 1.00 19.64 |
| ATOM | 1062 | CB | TYR | 155 | 167.595 | 151.421 | 152.513 | 1.00 18.08 |
| ATOM | 1063 | CG | TYR | 155 | 168.631 | 150.513 | 151.902 | 1.00 20.69 |
| ATOM | 1064 | CD1 | TYR | 155 | 169.076 | 149.377 | 152.574 | 1.00 22.26 |
| ATOM | 1065 | CE1 | TYR | 155 | 170.087 | 148.580 | 152.047 | 1.00 22.62 |
| ATOM | 1066 | CD2 | TYR | 155 | 169.220 | 150.828 | 150.675 | 1.00 23.05 |
| ATOM | 1067 | CE2 | TYR | 155 | 170.232 | 150.037 | 150.138 | 1.00 23.89 |
| ATOM | 1068 | CZ | TYR | 155 | 170.661 | 148.917 | 150.832 | 1.00 25.02 |
| ATOM | 1069 | OH | TYR | 155 | 171.677 | 148.145 | 150.315 | 1.00 29.32 |
| ATOM | 1070 | C | TYR | 155 | 167.063 | 153.712 | 153.354 | 1.00 19.26 |
| ATOM | 1071 | O | TYR | 155 | 165.882 | 153.366 | 153.315 | 1.00 18.83 |
| ATOM | 1072 | N | GLY | 156 | 167.468 | 154.864 | 153.878 | 1.00 19.09 |
| ATOM | 1073 | CA | GLY | 156 | 166.512 | 155.806 | 154.430 | 1.00 20.07 |
| ATOM | 1074 | C | GLY | 156 | 166.189 | 155.638 | 155.900 | 1.00 20.19 |
| ATOM | 1075 | O | GLY | 156 | 165.548 | 156.502 | 156.495 | 1.00 20.44 |
| ATOM | 1076 | N | GLY | 157 | 166.623 | 154.529 | 156.488 | 1.00 20.29 |
| ATOM | 1077 | CA | GLY | 157 | 166.359 | 154.292 | 157.896 | 1.00 20.16 |
| ATOM | 1078 | C | GLY | 157 | 167.573 | 154.562 | 158.765 | 1.00 21.36 |

*FIG. 4A - 19*

```
ATOM   1079  O    GLY  157     168.705 154.512 158.291  1.00 21.94
ATOM   1080  N    GLU  158     167.334 154.839 160.043  1.00 22.58
ATOM   1081  CA   GLU  158     168.400 155.129 160.996  1.00 24.00
ATOM   1082  CB   GLU  158     168.633 156.641 161.086  1.00 25.77
ATOM   1083  CG   GLU  158     169.433 157.255 159.962  1.00 31.67
ATOM   1084  CD   GLU  158     169.939 158.644 160.316  1.00 35.40
ATOM   1085  OE1  GLU  158     169.260 159.338 161.107  1.00 34.66
ATOM   1086  OE2  GLU  158     171.016 159.035 159.806  1.00 35.81
ATOM   1087  C    GLU  158     167.999 154.630 162.382  1.00 24.01
ATOM   1088  O    GLU  158     166.820 154.617 162.727  1.00 24.45
ATOM   1089  N    VAL  159     168.982 154.231 163.180  1.00 23.09
ATOM   1090  CA   VAL  159     168.713 153.774 164.536  1.00 20.95
ATOM   1091  CB   VAL  159     170.033 153.565 165.304  1.00 18.88
ATOM   1092  CG1  VAL  159     169.825 153.798 166.786  1.00 16.38
ATOM   1093  CG2  VAL  159     170.556 152.168 165.055  1.00 18.33
ATOM   1094  C    VAL  159     167.898 154.868 165.226  1.00 21.17
ATOM   1095  O    VAL  159     167.023 154.604 166.044  1.00 21.38
ATOM   1096  N    LYS  160     168.195 156.107 164.862  1.00 21.90
ATOM   1097  CA   LYS  160     167.530 157.271 165.424  1.00 22.40
ATOM   1098  CB   LYS  160     168.194 158.536 164.888  1.00 23.49
ATOM   1099  CG   LYS  160     167.686 159.809 165.516  1.00 26.04
ATOM   1100  CD   LYS  160     168.129 161.018 164.721  1.00 29.43
ATOM   1101  CE   LYS  160     168.208 162.247 165.611  1.00 32.06
ATOM   1102  NZ   LYS  160     167.375 163.358 165.076  1.00 33.62
ATOM   1103  C    LYS  160     166.024 157.353 165.181  1.00 21.95
ATOM   1104  O    LYS  160     165.313 157.983 165.961  1.00 23.43
ATOM   1105  N    ASP  161     165.534 156.735 164.110  1.00 20.68
ATOM   1106  CA   ASP  161     164.105 156.775 163.799  1.00 20.09
ATOM   1107  CB   ASP  161     163.784 155.955 162.539  1.00 18.84
ATOM   1108  CG   ASP  161     164.484 156.462 161.302  1.00 19.98
ATOM   1109  OD1  ASP  161     164.990 157.597 161.327  1.00 19.67
ATOM   1110  OD2  ASP  161     164.524 155.717 160.298  1.00 21.08
ATOM   1111  C    ASP  161     163.233 156.210 164.914  1.00 21.66
ATOM   1112  O    ASP  161     162.190 156.770 165.247  1.00 22.02
ATOM   1113  N    CYS  162     163.673 155.099 165.493  1.00 22.80
ATOM   1114  CA   CYS  162     162.880 154.401 166.495  1.00 25.05
ATOM   1115  CB   CYS  162     162.506 153.033 165.924  1.00 28.11
ATOM   1116  SG   CYS  162     163.935 152.210 165.152  1.00 38.25
ATOM   1117  C    CYS  162     163.445 154.197 167.894  1.00 24.57
ATOM   1118  O    CYS  162     162.782 153.589 168.733  1.00 23.81
ATOM   1119  N    ILE  163     164.654 154.678 168.163  1.00 24.28
ATOM   1120  CA   ILE  163     165.223 154.486 169.490  1.00 23.74
ATOM   1121  CB   ILE  163     166.757 154.611 169.457  1.00 22.96
ATOM   1122  CG2  ILE  163     167.162 156.051 169.245  1.00 21.74
ATOM   1123  CG1  ILE  163     167.346 154.064 170.756  1.00 21.48
ATOM   1124  CD1  ILE  163     168.834 153.827 170.682  1.00 19.32
ATOM   1125  C    ILE  163     164.655 155.451 170.532  1.00 23.52
ATOM   1126  O    ILE  163     164.408 156.622 170.243  1.00 23.95
ATOM   1127  N    ASP  164     164.443 154.942 171.743  1.00 21.43
ATOM   1128  CA   ASP  164     163.909 155.739 172.843  1.00 20.72
ATOM   1129  CB   ASP  164     162.867 154.932 173.627  1.00 20.15
ATOM   1130  CG   ASP  164     161.587 154.706 172.839  1.00 20.48
ATOM   1131  OD1  ASP  164     161.194 155.601 172.063  1.00 22.40
ATOM   1132  OD2  ASP  164     160.970 153.633 172.995  1.00 19.42
ATOM   1133  C    ASP  164     165.041 156.168 173.779  1.00 21.09
ATOM   1134  O    ASP  164     165.107 157.323 174.199  1.00 21.52
ATOM   1135  N    TYR  165     165.930 155.232 174.101  1.00 21.39
```

*FIG. 4A - 20*

| | | | | | | | | |
|---|---|---|---|---|---|---|---|---|
| ATOM | 1136 | CA | TYR | 165 | 167.063 | 155.512 | 174.978 | 1.00 21.10 |
| ATOM | 1137 | CB | TYR | 165 | 166.600 | 155.690 | 176.429 | 1.00 20.02 |
| ATOM | 1138 | CG | TYR | 165 | 165.869 | 154.499 | 177.003 | 1.00 19.60 |
| ATOM | 1139 | CD1 | TYR | 165 | 166.564 | 153.412 | 177.534 | 1.00 20.26 |
| ATOM | 1140 | CE1 | TYR | 165 | 165.887 | 152.304 | 178.053 | 1.00 19.90 |
| ATOM | 1141 | CD2 | TYR | 165 | 164.475 | 154.452 | 177.009 | 1.00 20.71 |
| ATOM | 1142 | CE2 | TYR | 165 | 163.790 | 153.351 | 177.526 | 1.00 20.82 |
| ATOM | 1143 | CZ | TYR | 165 | 164.502 | 152.283 | 178.042 | 1.00 21.38 |
| ATOM | 1144 | OH | TYR | 165 | 163.828 | 151.186 | 178.523 | 1.00 22.12 |
| ATOM | 1145 | C | TYR | 165 | 168.091 | 154.396 | 174.924 | 1.00 21.38 |
| ATOM | 1146 | O | TYR | 165 | 167.835 | 153.320 | 174.384 | 1.00 20.67 |
| ATOM | 1147 | N | ALA | 166 | 169.259 | 154.666 | 175.491 | 1.00 21.37 |
| ATOM | 1148 | CA | ALA | 166 | 170.331 | 153.690 | 175.548 | 1.00 21.45 |
| ATOM | 1149 | CB | ALA | 166 | 171.389 | 154.012 | 174.515 | 1.00 20.62 |
| ATOM | 1150 | C | ALA | 166 | 170.924 | 153.768 | 176.946 | 1.00 22.55 |
| ATOM | 1151 | O | ALA | 166 | 171.216 | 154.858 | 177.435 | 1.00 23.15 |
| ATOM | 1152 | N | LEU | 167 | 171.075 | 152.621 | 177.598 | 1.00 23.19 |
| ATOM | 1153 | CA | LEU | 167 | 171.653 | 152.584 | 178.937 | 1.00 22.98 |
| ATOM | 1154 | CB | LEU | 167 | 171.111 | 151.387 | 179.719 | 1.00 22.41 |
| ATOM | 1155 | CG | LEU | 167 | 171.673 | 151.190 | 181.129 | 1.00 24.75 |
| ATOM | 1156 | CD1 | LEU | 167 | 171.218 | 152.327 | 182.029 | 1.00 22.77 |
| ATOM | 1157 | CD2 | LEU | 167 | 171.213 | 149.849 | 181.682 | 1.00 25.88 |
| ATOM | 1158 | C | LEU | 167 | 173.160 | 152.451 | 178.761 | 1.00 23.29 |
| ATOM | 1159 | O | LEU | 167 | 173.622 | 151.564 | 178.043 | 1.00 21.36 |
| ATOM | 1160 | N | CYS | 168 | 173.923 | 153.331 | 179.405 | 1.00 23.44 |
| ATOM | 1161 | CA | CYS | 168 | 175.379 | 153.298 | 179.283 | 1.00 23.73 |
| ATOM | 1162 | CB | CYS | 168 | 175.873 | 154.457 | 178.411 | 1.00 23.39 |
| ATOM | 1163 | SG | CYS | 168 | 174.899 | 154.828 | 176.932 | 1.00 23.95 |
| ATOM | 1164 | C | CYS | 168 | 176.107 | 153.381 | 180.616 | 1.00 24.54 |
| ATOM | 1165 | O | CYS | 168 | 175.502 | 153.620 | 181.662 | 1.00 25.36 |
| ATOM | 1166 | N | VAL | 169 | 177.419 | 153.178 | 180.559 | 1.00 24.34 |
| ATOM | 1167 | CA | VAL | 169 | 178.280 | 153.274 | 181.731 | 1.00 24.69 |
| ATOM | 1168 | CB | VAL | 169 | 179.003 | 151.940 | 182.035 | 1.00 22.87 |
| ATOM | 1169 | CG1 | VAL | 169 | 179.874 | 152.096 | 183.263 | 1.00 20.10 |
| ATOM | 1170 | CG2 | VAL | 169 | 177.998 | 150.833 | 182.255 | 1.00 21.23 |
| ATOM | 1171 | C | VAL | 169 | 179.330 | 154.316 | 181.351 | 1.00 26.72 |
| ATOM | 1172 | O | VAL | 169 | 179.965 | 154.195 | 180.302 | 1.00 25.97 |
| ATOM | 1173 | N | ASN | 170 | 179.502 | 155.353 | 182.165 | 1.00 28.46 |
| ATOM | 1174 | CA | ASN | 170 | 180.508 | 156.353 | 181.831 | 1.00 31.28 |
| ATOM | 1175 | CB | ASN | 170 | 180.202 | 157.707 | 182.492 | 1.00 30.82 |
| ATOM | 1176 | CG | ASN | 170 | 180.032 | 157.614 | 183.995 | 1.00 31.37 |
| ATOM | 1177 | OD1 | ASN | 170 | 179.235 | 158.349 | 184.579 | 1.00 32.20 |
| ATOM | 1178 | ND2 | ASN | 170 | 180.781 | 156.722 | 184.631 | 1.00 29.07 |
| ATOM | 1179 | C | ASN | 170 | 181.885 | 155.845 | 182.246 | 1.00 33.02 |
| ATOM | 1180 | O | ASN | 170 | 181.995 | 154.867 | 182.985 | 1.00 33.02 |
| ATOM | 1181 | N | GLU | 171 | 182.932 | 156.502 | 181.759 | 1.00 36.08 |
| ATOM | 1182 | CA | GLU | 171 | 184.303 | 156.101 | 182.057 | 1.00 38.23 |
| ATOM | 1183 | CB | GLU | 171 | 185.288 | 157.091 | 181.433 | 1.00 41.83 |
| ATOM | 1184 | CG | GLU | 171 | 185.629 | 158.265 | 182.325 | 1.00 50.67 |
| ATOM | 1185 | CD | GLU | 171 | 186.001 | 159.502 | 181.534 | 1.00 57.00 |
| ATOM | 1186 | OE1 | GLU | 171 | 185.253 | 160.505 | 181.606 | 1.00 58.71 |
| ATOM | 1187 | OE2 | GLU | 171 | 187.041 | 159.467 | 180.839 | 1.00 58.58 |
| ATOM | 1188 | C | GLU | 171 | 184.587 | 155.970 | 183.547 | 1.00 37.04 |
| ATOM | 1189 | O | GLU | 171 | 185.543 | 155.305 | 183.941 | 1.00 37.08 |
| ATOM | 1190 | N | GLN | 172 | 183.763 | 156.605 | 184.373 | 1.00 35.88 |
| ATOM | 1191 | CA | GLN | 172 | 183.949 | 156.543 | 185.817 | 1.00 35.98 |
| ATOM | 1192 | CB | GLN | 172 | 183.444 | 157.834 | 186.471 | 1.00 39.05 |

*FIG. 4A - 21*

```
ATOM   1193  CG   GLN  172      184.376 159.040 186.286  1.00 44.08
ATOM   1194  CD   GLN  172      184.260 159.688 184.905  1.00 48.60
ATOM   1195  OE1  GLN  172      185.184 160.362 184.438  1.00 50.38
ATOM   1196  NE2  GLN  172      183.121 159.485 184.247  1.00 49.06
ATOM   1197  C    GLN  172      183.228 155.327 186.393  1.00 34.62
ATOM   1198  O    GLN  172      183.357 155.016 187.577  1.00 33.74
ATOM   1199  N    GLY  173      182.458 154.644 185.551  1.00 32.87
ATOM   1200  CA   GLY  173      181.765 153.446 185.995  1.00 30.37
ATOM   1201  C    GLY  173      180.320 153.557 186.442  1.00 30.15
ATOM   1202  O    GLY  173      179.764 152.594 186.976  1.00 28.23
ATOM   1203  N    SER  174      179.700 154.712 186.226  1.00 30.06
ATOM   1204  CA   SER  174      178.309 154.898 186.630  1.00 29.64
ATOM   1205  CB   SER  174      178.086 156.331 187.121  1.00 29.67
ATOM   1206  OG   SER  174      179.013 156.680 188.132  1.00 31.97
ATOM   1207  C    SER  174      177.327 154.602 185.498  1.00 28.54
ATOM   1208  O    SER  174      177.670 154.704 184.319  1.00 27.86
ATOM   1209  N    LEU  175      176.106 154.231 185.870  1.00 27.97
ATOM   1210  CA   LEU  175      175.056 153.943 184.903  1.00 27.35
ATOM   1211  CB   LEU  175      174.003 153.022 185.509  1.00 26.60
ATOM   1212  CG   LEU  175      174.217 151.513 185.541  1.00 27.87
ATOM   1213  CD1  LEU  175      173.059 150.892 186.292  1.00 27.20
ATOM   1214  CD2  LEU  175      174.294 150.947 184.132  1.00 29.17
ATOM   1215  C    LEU  175      174.376 155.251 184.530  1.00 28.32
ATOM   1216  O    LEU  175      174.098 156.079 185.395  1.00 28.95
ATOM   1217  N    ILE  176      174.119 155.441 183.243  1.00 28.13
ATOM   1218  CA   ILE  176      173.442 156.639 182.779  1.00 28.50
ATOM   1219  CB   ILE  176      174.435 157.721 182.260  1.00 29.87
ATOM   1220  CG2  ILE  176      175.423 157.111 181.285  1.00 29.98
ATOM   1221  CG1  ILE  176      173.661 158.842 181.561  1.00 33.57
ATOM   1222  CD1  ILE  176      174.354 160.193 181.577  1.00 35.57
ATOM   1223  C    ILE  176      172.505 156.236 181.655  1.00 28.18
ATOM   1224  O    ILE  176      172.901 155.547 180.716  1.00 27.98
ATOM   1225  N    LYS  177      171.249 156.644 181.777  1.00 27.36
ATOM   1226  CA   LYS  177      170.248 156.353 180.767  1.00 26.09
ATOM   1227  CB   LYS  177      168.905 156.042 181.428  1.00 23.91
ATOM   1228  CG   LYS  177      167.839 155.580 180.460  1.00 25.18
ATOM   1229  CD   LYS  177      166.463 155.611 181.098  1.00 26.15
ATOM   1230  CE   LYS  177      165.907 154.211 181.260  1.00 29.01
ATOM   1231  NZ   LYS  177      164.468 154.240 181.638  1.00 29.99
ATOM   1232  C    LYS  177      170.129 157.596 179.895  1.00 25.17
ATOM   1233  O    LYS  177      169.705 158.652 180.361  1.00 24.48
ATOM   1234  N    LEU  178      170.528 157.475 178.635  1.00 25.13
ATOM   1235  CA   LEU  178      170.465 158.598 177.711  1.00 24.32
ATOM   1236  CB   LEU  178      171.780 158.718 176.929  1.00 24.43
ATOM   1237  CG   LEU  178      173.052 159.053 177.723  1.00 25.30
ATOM   1238  CD1  LEU  178      174.212 159.291 176.774  1.00 25.18
ATOM   1239  CD2  LEU  178      172.817 160.288 178.577  1.00 27.45
ATOM   1240  C    LEU  178      169.304 158.407 176.746  1.00 25.28
ATOM   1241  O    LEU  178      169.242 157.413 176.024  1.00 25.57
ATOM   1242  N    THR  179      168.378 159.359 176.748  1.00 25.38
ATOM   1243  CA   THR  179      167.220 159.301 175.868  1.00 26.08
ATOM   1244  CB   THR  179      166.145 160.299 176.330  1.00 26.24
ATOM   1245  OG1  THR  179      166.720 161.606 176.428  1.00 28.94
ATOM   1246  CG2  THR  179      165.615 159.906 177.695  1.00 22.22
ATOM   1247  C    THR  179      167.666 159.643 174.450  1.00 25.42
ATOM   1248  O    THR  179      168.823 160.000 174.237  1.00 24.98
ATOM   1249  N    THR  180      166.754 159.538 173.488  1.00 25.78
```

*FIG. 4A - 22*

| ATOM | 1250 | CA  | THR | 180 | 167.071 | 159.830 | 172.092 | 1.00 | 26.50 |
| ATOM | 1251 | CB  | THR | 180 | 165.818 | 159.893 | 171.222 | 1.00 | 27.03 |
| ATOM | 1252 | OG1 | THR | 180 | 164.915 | 158.852 | 171.603 | 1.00 | 31.60 |
| ATOM | 1253 | CG2 | THR | 180 | 166.192 | 159.728 | 169.760 | 1.00 | 27.44 |
| ATOM | 1254 | C   | THR | 180 | 167.799 | 161.144 | 171.885 | 1.00 | 26.23 |
| ATOM | 1255 | O   | THR | 180 | 168.837 | 161.184 | 171.228 | 1.00 | 27.10 |
| ATOM | 1256 | N   | LYS | 181 | 167.248 | 162.224 | 172.427 | 1.00 | 24.70 |
| ATOM | 1257 | CA  | LYS | 181 | 167.868 | 163.526 | 172.259 | 1.00 | 25.42 |
| ATOM | 1258 | CB  | LYS | 181 | 166.977 | 164.627 | 172.832 | 1.00 | 26.63 |
| ATOM | 1259 | CG  | LYS | 181 | 167.179 | 165.975 | 172.147 | 1.00 | 30.96 |
| ATOM | 1260 | CD  | LYS | 181 | 166.366 | 167.076 | 172.801 | 1.00 | 33.60 |
| ATOM | 1261 | CE  | LYS | 181 | 166.869 | 167.377 | 174.202 | 1.00 | 38.01 |
| ATOM | 1262 | NZ  | LYS | 181 | 167.409 | 168.763 | 174.296 | 1.00 | 42.60 |
| ATOM | 1263 | C   | LYS | 181 | 169.241 | 163.601 | 172.901 | 1.00 | 24.41 |
| ATOM | 1264 | O   | LYS | 181 | 170.170 | 164.162 | 172.321 | 1.00 | 24.22 |
| ATOM | 1265 | N   | GLU | 182 | 169.373 | 163.034 | 174.094 | 1.00 | 24.10 |
| ATOM | 1266 | CA  | GLU | 182 | 170.644 | 163.065 | 174.804 | 1.00 | 23.70 |
| ATOM | 1267 | CB  | GLU | 182 | 170.454 | 162.546 | 176.226 | 1.00 | 24.64 |
| ATOM | 1268 | CG  | GLU | 182 | 169.428 | 163.336 | 177.018 | 1.00 | 26.08 |
| ATOM | 1269 | CD  | GLU | 182 | 169.158 | 162.738 | 178.381 | 1.00 | 28.77 |
| ATOM | 1270 | OE1 | GLU | 182 | 169.278 | 161.505 | 178.531 | 1.00 | 30.74 |
| ATOM | 1271 | OE2 | GLU | 182 | 168.824 | 163.504 | 179.306 | 1.00 | 32.18 |
| ATOM | 1272 | C   | GLU | 182 | 171.739 | 162.273 | 174.097 | 1.00 | 22.87 |
| ATOM | 1273 | O   | GLU | 182 | 172.924 | 162.552 | 174.276 | 1.00 | 23.48 |
| ATOM | 1274 | N   | LEU | 183 | 171.342 | 161.288 | 173.296 | 1.00 | 20.96 |
| ATOM | 1275 | CA  | LEU | 183 | 172.302 | 160.472 | 172.560 | 1.00 | 20.78 |
| ATOM | 1276 | CB  | LEU | 183 | 171.620 | 159.231 | 171.981 | 1.00 | 18.97 |
| ATOM | 1277 | CG  | LEU | 183 | 171.358 | 158.085 | 172.962 | 1.00 | 18.71 |
| ATOM | 1278 | CD1 | LEU | 183 | 170.461 | 157.043 | 172.310 | 1.00 | 16.75 |
| ATOM | 1279 | CD2 | LEU | 183 | 172.677 | 157.465 | 173.387 | 1.00 | 17.42 |
| ATOM | 1280 | C   | LEU | 183 | 172.918 | 161.281 | 171.430 | 1.00 | 21.83 |
| ATOM | 1281 | O   | LEU | 183 | 173.933 | 160.894 | 170.861 | 1.00 | 22.55 |
| ATOM | 1282 | N   | GLU | 184 | 172.290 | 162.406 | 171.106 | 1.00 | 23.10 |
| ATOM | 1283 | CA  | GLU | 184 | 172.772 | 163.284 | 170.049 | 1.00 | 23.29 |
| ATOM | 1284 | CB  | GLU | 184 | 174.003 | 164.046 | 170.534 | 1.00 | 24.87 |
| ATOM | 1285 | CG  | GLU | 184 | 173.649 | 165.220 | 171.428 | 1.00 | 30.01 |
| ATOM | 1286 | CD  | GLU | 184 | 174.842 | 165.770 | 172.177 | 1.00 | 35.06 |
| ATOM | 1287 | OE1 | GLU | 184 | 175.964 | 165.731 | 171.625 | 1.00 | 36.91 |
| ATOM | 1288 | OE2 | GLU | 184 | 174.655 | 166.245 | 173.319 | 1.00 | 37.57 |
| ATOM | 1289 | C   | GLU | 184 | 173.092 | 162.512 | 168.782 | 1.00 | 23.20 |
| ATOM | 1290 | O   | GLU | 184 | 174.157 | 162.674 | 168.186 | 1.00 | 21.86 |
| ATOM | 1291 | N   | LEU | 185 | 172.153 | 161.669 | 168.372 | 1.00 | 22.96 |
| ATOM | 1292 | CA  | LEU | 185 | 172.331 | 160.873 | 167.174 | 1.00 | 22.82 |
| ATOM | 1293 | CB  | LEU | 185 | 171.180 | 159.875 | 167.043 | 1.00 | 21.22 |
| ATOM | 1294 | CG  | LEU | 185 | 171.096 | 158.916 | 168.236 | 1.00 | 20.24 |
| ATOM | 1295 | CD1 | LEU | 185 | 169.752 | 158.226 | 168.242 | 1.00 | 20.18 |
| ATOM | 1296 | CD2 | LEU | 185 | 172.214 | 157.889 | 168.160 | 1.00 | 19.24 |
| ATOM | 1297 | C   | LEU | 185 | 172.408 | 161.796 | 165.963 | 1.00 | 22.98 |
| ATOM | 1298 | O   | LEU | 185 | 171.569 | 162.675 | 165.776 | 1.00 | 22.85 |
| ATOM | 1299 | N   | ASP | 186 | 173.432 | 161.589 | 165.147 | 1.00 | 23.52 |
| ATOM | 1300 | CA  | ASP | 186 | 173.655 | 162.411 | 163.968 | 1.00 | 22.71 |
| ATOM | 1301 | CB  | ASP | 186 | 174.797 | 163.384 | 164.255 | 1.00 | 23.43 |
| ATOM | 1302 | CG  | ASP | 186 | 174.812 | 164.580 | 163.322 | 1.00 | 25.88 |
| ATOM | 1303 | OD1 | ASP | 186 | 175.634 | 165.486 | 163.574 | 1.00 | 26.20 |
| ATOM | 1304 | OD2 | ASP | 186 | 174.024 | 164.628 | 162.349 | 1.00 | 26.91 |
| ATOM | 1305 | C   | ASP | 186 | 174.024 | 161.512 | 162.799 | 1.00 | 22.67 |
| ATOM | 1306 | O   | ASP | 186 | 173.944 | 160.290 | 162.900 | 1.00 | 21.51 |

*FIG. 4A - 23*

```
ATOM  1307  N    TYR  187    174.430  162.118  161.690  1.00  22.70
ATOM  1308  CA   TYR  187    174.820  161.347  160.523  1.00  23.26
ATOM  1309  CB   TYR  187    174.957  162.261  159.307  1.00  21.82
ATOM  1310  CG   TYR  187    175.526  161.573  158.090  1.00  19.89
ATOM  1311  CD1  TYR  187    174.839  160.531  157.470  1.00  19.68
ATOM  1312  CE1  TYR  187    175.362  159.892  156.357  1.00  19.32
ATOM  1313  CD2  TYR  187    176.754  161.959  157.562  1.00  18.63
ATOM  1314  CE2  TYR  187    177.286  161.326  156.449  1.00  18.14
ATOM  1315  CZ   TYR  187    176.585  160.297  155.853  1.00  19.34
ATOM  1316  OH   TYR  187    177.102  159.676  154.742  1.00  21.73
ATOM  1317  C    TYR  187    176.153  160.680  160.828  1.00  25.07
ATOM  1318  O    TYR  187    177.183  161.345  160.914  1.00  24.89
ATOM  1319  N    ARG  188    176.127  159.363  161.004  1.00  26.98
ATOM  1320  CA   ARG  188    177.336  158.598  161.308  1.00  27.45
ATOM  1321  CB   ARG  188    178.302  158.635  160.116  1.00  28.34
ATOM  1322  CG   ARG  188    177.834  157.858  158.886  1.00  32.31
ATOM  1323  CD   ARG  188    177.009  156.622  159.265  1.00  38.48
ATOM  1324  NE   ARG  188    176.750  155.757  158.115  1.00  42.01
ATOM  1325  CZ   ARG  188    175.539  155.459  157.654  1.00  42.08
ATOM  1326  NH1  ARG  188    175.407  154.661  156.601  1.00  42.54
ATOM  1327  NH2  ARG  188    174.459  155.956  158.242  1.00  41.06
ATOM  1328  C    ARG  188    178.054  159.100  162.562  1.00  26.50
ATOM  1329  O    ARG  188    179.281  159.095  162.625  1.00  26.43
ATOM  1330  N    ASN  189    177.291  159.526  163.564  1.00  25.15
ATOM  1331  CA   ASN  189    177.886  160.022  164.797  1.00  23.45
ATOM  1332  CB   ASN  189    178.380  161.453  164.600  1.00  25.54
ATOM  1333  CG   ASN  189    179.430  161.851  165.616  1.00  29.26
ATOM  1334  OD1  ASN  189    179.865  162.999  165.650  1.00  34.10
ATOM  1335  ND2  ASN  189    179.843  160.903  166.451  1.00  28.64
ATOM  1336  C    ASN  189    176.900  159.987  165.949  1.00  22.03
ATOM  1337  O    ASN  189    175.696  159.842  165.744  1.00  21.87
ATOM  1338  N    SER  190    177.425  160.127  167.162  1.00  20.27
ATOM  1339  CA   SER  190    176.619  160.122  168.376  1.00  20.28
ATOM  1340  CB   SER  190    176.073  158.723  168.650  1.00  18.96
ATOM  1341  OG   SER  190    177.050  157.921  169.295  1.00  19.71
ATOM  1342  C    SER  190    177.488  160.556  169.544  1.00  21.28
ATOM  1343  O    SER  190    178.704  160.698  169.410  1.00  21.80
ATOM  1344  N    ILE  191    176.861  160.759  170.693  1.00  22.92
ATOM  1345  CA   ILE  191    177.582  161.179  171.881  1.00  24.09
ATOM  1346  CB   ILE  191    176.607  161.713  172.965  1.00  24.32
ATOM  1347  CG2  ILE  191    176.070  160.566  173.812  1.00  23.02
ATOM  1348  CG1  ILE  191    177.324  162.750  173.833  1.00  25.76
ATOM  1349  CD1  ILE  191    176.521  163.226  175.029  1.00  27.06
ATOM  1350  C    ILE  191    178.415  160.040  172.458  1.00  25.38
ATOM  1351  O    ILE  191    179.301  160.270  173.276  1.00  25.59
ATOM  1352  N    ILE  192    178.121  158.812  172.040  1.00  27.27
ATOM  1353  CA   ILE  192    178.865  157.652  172.521  1.00  28.76
ATOM  1354  CB   ILE  192    178.320  156.341  171.926  1.00  26.09
ATOM  1355  CG2  ILE  192    178.978  155.166  172.607  1.00  25.40
ATOM  1356  CG1  ILE  192    176.797  156.277  172.079  1.00  23.83
ATOM  1357  CD1  ILE  192    176.314  156.175  173.513  1.00  22.46
ATOM  1358  C    ILE  192    180.312  157.813  172.079  1.00  31.56
ATOM  1359  O    ILE  192    181.248  157.447  172.791  1.00  31.92
ATOM  1360  N    GLN  193    180.481  158.370  170.886  1.00  34.29
ATOM  1361  CA   GLN  193    181.799  158.601  170.324  1.00  36.56
ATOM  1362  CB   GLN  193    181.687  159.012  168.855  1.00  34.95
ATOM  1363  CG   GLN  193    180.700  158.194  168.043  1.00  34.49
```

*FIG. 4A - 24*

| | | | | | | | |
|---|---|---|---|---|---|---|---|
| ATOM | 1364 | CD | GLN | 193 | 181.078 | 158.119 | 166.577 | 1.00 | 35.08 |
| ATOM | 1365 | OE1 | GLN | 193 | 182.130 | 158.611 | 166.169 | 1.00 | 36.46 |
| ATOM | 1366 | NE2 | GLN | 193 | 180.218 | 157.502 | 165.774 | 1.00 | 36.56 |
| ATOM | 1367 | C | GLN | 193 | 182.487 | 159.713 | 171.096 | 1.00 | 39.76 |
| ATOM | 1368 | O | GLN | 193 | 183.581 | 159.535 | 171.633 | 1.00 | 40.78 |
| ATOM | 1369 | N | LYS | 194 | 181.823 | 160.860 | 171.160 | 1.00 | 42.70 |
| ATOM | 1370 | CA | LYS | 194 | 182.365 | 162.025 | 171.830 | 1.00 | 45.42 |
| ATOM | 1371 | CB | LYS | 194 | 181.409 | 163.213 | 171.643 | 1.00 | 49.23 |
| ATOM | 1372 | CG | LYS | 194 | 180.891 | 163.369 | 170.192 | 1.00 | 54.76 |
| ATOM | 1373 | CD | LYS | 194 | 181.810 | 164.224 | 169.306 | 1.00 | 59.11 |
| ATOM | 1374 | CE | LYS | 194 | 181.047 | 164.801 | 168.107 | 1.00 | 61.43 |
| ATOM | 1375 | NZ | LYS | 194 | 181.787 | 165.889 | 167.396 | 1.00 | 62.48 |
| ATOM | 1376 | C | LYS | 194 | 182.772 | 161.858 | 173.298 | 1.00 | 44.79 |
| ATOM | 1377 | O | LYS | 194 | 183.772 | 162.450 | 173.705 | 1.00 | 45.31 |
| ATOM | 1378 | N | GLU | 195 | 182.048 | 161.090 | 174.114 | 1.00 | 43.73 |
| ATOM | 1379 | CA | GLU | 195 | 182.527 | 160.954 | 175.484 | 1.00 | 44.07 |
| ATOM | 1380 | CB | GLU | 195 | 181.662 | 161.741 | 176.482 | 1.00 | 45.48 |
| ATOM | 1381 | CG | GLU | 195 | 180.180 | 161.459 | 176.585 | 1.00 | 48.14 |
| ATOM | 1382 | CD | GLU | 195 | 179.516 | 162.481 | 177.500 | 1.00 | 51.43 |
| ATOM | 1383 | OE1 | GLU | 195 | 179.802 | 163.680 | 177.312 | 1.00 | 51.84 |
| ATOM | 1384 | OE2 | GLU | 195 | 178.739 | 162.107 | 178.411 | 1.00 | 54.06 |
| ATOM | 1385 | C | GLU | 195 | 182.797 | 159.552 | 175.982 | 1.00 | 42.89 |
| ATOM | 1386 | O | GLU | 195 | 182.684 | 159.264 | 177.163 | 1.00 | 43.16 |
| ATOM | 1387 | N | HIS | 196 | 183.224 | 158.695 | 175.064 | 1.00 | 41.71 |
| ATOM | 1388 | CA | HIS | 196 | 183.593 | 157.329 | 175.392 | 1.00 | 40.45 |
| ATOM | 1389 | CB | HIS | 196 | 185.059 | 157.332 | 175.829 | 1.00 | 43.28 |
| ATOM | 1390 | CG | HIS | 196 | 185.706 | 155.981 | 175.819 | 1.00 | 45.16 |
| ATOM | 1391 | CD2 | HIS | 196 | 186.380 | 155.317 | 176.787 | 1.00 | 46.04 |
| ATOM | 1392 | ND1 | HIS | 196 | 185.745 | 155.176 | 174.704 | 1.00 | 46.00 |
| ATOM | 1393 | CE1 | HIS | 196 | 186.417 | 154.074 | 174.979 | 1.00 | 46.41 |
| ATOM | 1394 | NE2 | HIS | 196 | 186.814 | 154.134 | 176.239 | 1.00 | 47.06 |
| ATOM | 1395 | C | HIS | 196 | 182.731 | 156.621 | 176.457 | 1.00 | 36.84 |
| ATOM | 1396 | O | HIS | 196 | 183.224 | 156.211 | 177.514 | 1.00 | 35.76 |
| ATOM | 1397 | N | LEU | 197 | 181.441 | 156.493 | 176.178 | 1.00 | 32.72 |
| ATOM | 1398 | CA | LEU | 197 | 180.537 | 155.799 | 177.084 | 1.00 | 27.73 |
| ATOM | 1399 | CB | LEU | 197 | 179.137 | 156.413 | 177.035 | 1.00 | 27.16 |
| ATOM | 1400 | CG | LEU | 197 | 178.893 | 157.823 | 177.570 | 1.00 | 27.34 |
| ATOM | 1401 | CD1 | LEU | 197 | 177.881 | 158.553 | 176.683 | 1.00 | 26.31 |
| ATOM | 1402 | CD2 | LEU | 197 | 178.367 | 157.723 | 178.988 | 1.00 | 28.50 |
| ATOM | 1403 | C | LEU | 197 | 180.471 | 154.405 | 176.493 | 1.00 | 25.69 |
| ATOM | 1404 | O | LEU | 197 | 180.823 | 154.215 | 175.332 | 1.00 | 26.15 |
| ATOM | 1405 | N | VAL | 198 | 180.044 | 153.426 | 177.276 | 1.00 | 23.70 |
| ATOM | 1406 | CA | VAL | 198 | 179.904 | 152.080 | 176.743 | 1.00 | 20.83 |
| ATOM | 1407 | CB | VAL | 198 | 180.698 | 151.037 | 177.570 | 1.00 | 20.21 |
| ATOM | 1408 | CG1 | VAL | 198 | 180.256 | 151.056 | 179.018 | 1.00 | 20.15 |
| ATOM | 1409 | CG2 | VAL | 198 | 180.509 | 149.658 | 176.973 | 1.00 | 18.07 |
| ATOM | 1410 | C | VAL | 198 | 178.413 | 151.771 | 176.788 | 1.00 | 20.21 |
| ATOM | 1411 | O | VAL | 198 | 177.771 | 151.956 | 177.820 | 1.00 | 19.70 |
| ATOM | 1412 | N | VAL | 199 | 177.858 | 151.340 | 175.659 | 1.00 | 19.82 |
| ATOM | 1413 | CA | VAL | 199 | 176.437 | 151.017 | 175.576 | 1.00 | 18.75 |
| ATOM | 1414 | CB | VAL | 199 | 175.935 | 151.109 | 174.125 | 1.00 | 17.87 |
| ATOM | 1415 | CG1 | VAL | 199 | 174.453 | 150.774 | 174.059 | 1.00 | 14.17 |
| ATOM | 1416 | CG2 | VAL | 199 | 176.177 | 152.505 | 173.589 | 1.00 | 16.61 |
| ATOM | 1417 | C | VAL | 199 | 176.147 | 149.618 | 176.107 | 1.00 | 19.36 |
| ATOM | 1418 | O | VAL | 199 | 176.826 | 148.654 | 175.752 | 1.00 | 19.28 |
| ATOM | 1419 | N | LEU | 200 | 175.122 | 149.515 | 176.950 | 1.00 | 19.45 |
| ATOM | 1420 | CA | LEU | 200 | 174.735 | 148.245 | 177.551 | 1.00 | 18.58 |

*FIG. 4A - 25*

| | | | | | | | | | |
|---|---|---|---|---|---|---|---|---|---|
| ATOM | 1421 | CB | LEU | 200 | 174.587 | 148.405 | 179.063 | 1.00 | 19.18 |
| ATOM | 1422 | CG | LEU | 200 | 175.818 | 148.718 | 179.909 | 1.00 | 21.41 |
| ATOM | 1423 | CD1 | LEU | 200 | 175.384 | 148.926 | 181.353 | 1.00 | 20.34 |
| ATOM | 1424 | CD2 | LEU | 200 | 176.819 | 147.583 | 179.803 | 1.00 | 19.47 |
| ATOM | 1425 | C | LEU | 200 | 173.418 | 147.713 | 177.011 | 1.00 | 19.06 |
| ATOM | 1426 | O | LEU | 200 | 173.205 | 146.504 | 176.950 | 1.00 | 19.49 |
| ATOM | 1427 | N | GLU | 201 | 172.527 | 148.617 | 176.626 | 1.00 | 19.00 |
| ATOM | 1428 | CA | GLU | 201 | 171.221 | 148.209 | 176.142 | 1.00 | 19.34 |
| ATOM | 1429 | CB | GLU | 201 | 170.380 | 147.751 | 177.336 | 1.00 | 18.32 |
| ATOM | 1430 | CG | GLU | 201 | 168.928 | 147.428 | 177.041 | 1.00 | 21.67 |
| ATOM | 1431 | CD | GLU | 201 | 168.176 | 147.041 | 178.298 | 1.00 | 22.86 |
| ATOM | 1432 | OE1 | GLU | 201 | 167.546 | 145.965 | 178.324 | 1.00 | 24.61 |
| ATOM | 1433 | OE2 | GLU | 201 | 168.223 | 147.818 | 179.268 | 1.00 | 25.81 |
| ATOM | 1434 | C | GLU | 201 | 170.525 | 149.357 | 175.426 | 1.00 | 20.01 |
| ATOM | 1435 | O | GLU | 201 | 170.799 | 150.524 | 175.701 | 1.00 | 20.51 |
| ATOM | 1436 | N | ALA | 202 | 169.623 | 149.020 | 174.508 | 1.00 | 19.24 |
| ATOM | 1437 | CA | ALA | 202 | 168.879 | 150.032 | 173.774 | 1.00 | 19.51 |
| ATOM | 1438 | CB | ALA | 202 | 169.413 | 150.157 | 172.361 | 1.00 | 18.80 |
| ATOM | 1439 | C | ALA | 202 | 167.408 | 149.656 | 173.746 | 1.00 | 19.05 |
| ATOM | 1440 | O | ALA | 202 | 167.067 | 148.478 | 173.680 | 1.00 | 19.93 |
| ATOM | 1441 | N | ALA | 203 | 166.541 | 150.661 | 173.804 | 1.00 | 18.63 |
| ATOM | 1442 | CA | ALA | 203 | 165.102 | 150.438 | 173.781 | 1.00 | 18.46 |
| ATOM | 1443 | CB | ALA | 203 | 164.472 | 150.974 | 175.055 | 1.00 | 17.86 |
| ATOM | 1444 | C | ALA | 203 | 164.496 | 151.128 | 172.570 | 1.00 | 18.35 |
| ATOM | 1445 | O | ALA | 203 | 164.854 | 152.263 | 172.253 | 1.00 | 18.96 |
| ATOM | 1446 | N | PHE | 204 | 163.581 | 150.437 | 171.897 | 1.00 | 18.48 |
| ATOM | 1447 | CA | PHE | 204 | 162.914 | 150.976 | 170.716 | 1.00 | 19.03 |
| ATOM | 1448 | CB | PHE | 204 | 163.324 | 150.207 | 169.449 | 1.00 | 18.58 |
| ATOM | 1449 | CG | PHE | 204 | 164.807 | 150.139 | 169.214 | 1.00 | 18.99 |
| ATOM | 1450 | CD1 | PHE | 204 | 165.562 | 149.103 | 169.755 | 1.00 | 19.20 |
| ATOM | 1451 | CD2 | PHE | 204 | 165.447 | 151.095 | 168.432 | 1.00 | 17.32 |
| ATOM | 1452 | CE1 | PHE | 204 | 166.931 | 149.018 | 169.517 | 1.00 | 18.79 |
| ATOM | 1453 | CE2 | PHE | 204 | 166.816 | 151.016 | 168.189 | 1.00 | 16.54 |
| ATOM | 1454 | CZ | PHE | 204 | 167.556 | 149.977 | 168.734 | 1.00 | 16.31 |
| ATOM | 1455 | C | PHE | 204 | 161.399 | 150.876 | 170.835 | 1.00 | 19.26 |
| ATOM | 1456 | O | PHE | 204 | 160.871 | 150.117 | 171.648 | 1.00 | 20.51 |
| ATOM | 1457 | N | THR | 205 | 160.711 | 151.659 | 170.014 | 1.00 | 19.86 |
| ATOM | 1458 | CA | THR | 205 | 159.258 | 151.639 | 169.947 | 1.00 | 19.26 |
| ATOM | 1459 | CB | THR | 205 | 158.617 | 152.901 | 170.545 | 1.00 | 18.74 |
| ATOM | 1460 | OG1 | THR | 205 | 158.790 | 152.903 | 171.968 | 1.00 | 18.85 |
| ATOM | 1461 | CG2 | THR | 205 | 157.124 | 152.927 | 170.234 | 1.00 | 16.82 |
| ATOM | 1462 | C | THR | 205 | 158.982 | 151.606 | 168.454 | 1.00 | 19.83 |
| ATOM | 1463 | O | THR | 205 | 159.430 | 152.484 | 167.716 | 1.00 | 20.18 |
| ATOM | 1464 | N | LEU | 206 | 158.272 | 150.581 | 168.000 | 1.00 | 20.00 |
| ATOM | 1465 | CA | LEU | 206 | 157.971 | 150.457 | 166.581 | 1.00 | 20.18 |
| ATOM | 1466 | CB | LEU | 206 | 158.520 | 149.134 | 166.038 | 1.00 | 19.60 |
| ATOM | 1467 | CG | LEU | 206 | 159.964 | 149.146 | 165.525 | 1.00 | 19.34 |
| ATOM | 1468 | CD1 | LEU | 206 | 160.922 | 149.380 | 166.671 | 1.00 | 18.82 |
| ATOM | 1469 | CD2 | LEU | 206 | 160.275 | 147.827 | 164.854 | 1.00 | 17.75 |
| ATOM | 1470 | C | LEU | 206 | 156.475 | 150.533 | 166.351 | 1.00 | 19.83 |
| ATOM | 1471 | O | LEU | 206 | 155.697 | 150.542 | 167.299 | 1.00 | 20.66 |
| ATOM | 1472 | N | ALA | 207 | 156.078 | 150.586 | 165.087 | 1.00 | 19.44 |
| ATOM | 1473 | CA | ALA | 207 | 154.671 | 150.672 | 164.737 | 1.00 | 19.07 |
| ATOM | 1474 | CB | ALA | 207 | 154.462 | 151.759 | 163.689 | 1.00 | 15.16 |
| ATOM | 1475 | C | ALA | 207 | 154.143 | 149.355 | 164.206 | 1.00 | 19.35 |
| ATOM | 1476 | O | ALA | 207 | 154.794 | 148.694 | 163.396 | 1.00 | 21.42 |
| ATOM | 1477 | N | PRO | 208 | 152.955 | 148.946 | 164.668 | 1.00 | 19.30 |

*FIG. 4A - 26*

| | | | | | | | | |
|---|---|---|---|---|---|---|---|---|
| ATOM | 1478 | CD | PRO | 208 | 152.057 | 149.572 | 165.647 | 1.00 18.16 |
| ATOM | 1479 | CA | PRO | 208 | 152.416 | 147.688 | 164.169 | 1.00 19.09 |
| ATOM | 1480 | CB | PRO | 208 | 151.006 | 147.649 | 164.733 | 1.00 18.36 |
| ATOM | 1481 | CG | PRO | 208 | 151.071 | 148.486 | 165.947 | 1.00 17.26 |
| ATOM | 1482 | C | PRO | 208 | 152.416 | 147.742 | 162.656 | 1.00 19.33 |
| ATOM | 1483 | O | PRO | 208 | 152.182 | 148.796 | 162.057 | 1.00 18.22 |
| ATOM | 1484 | N | GLY | 209 | 152.692 | 146.617 | 162.026 | 1.00 20.39 |
| ATOM | 1485 | CA | GLY | 209 | 152.703 | 146.595 | 160.579 | 1.00 20.19 |
| ATOM | 1486 | C | GLY | 209 | 152.121 | 145.277 | 160.083 | 1.00 21.92 |
| ATOM | 1487 | O | GLY | 209 | 151.702 | 144.430 | 160.879 | 1.00 20.62 |
| ATOM | 1488 | N | LYS | 210 | 152.115 | 145.132 | 158.775 | 1.00 23.93 |
| ATOM | 1489 | CA | LYS | 210 | 151.615 | 143.952 | 158.091 | 1.00 26.68 |
| ATOM | 1490 | CB | LYS | 210 | 150.843 | 144.371 | 156.840 | 1.00 30.12 |
| ATOM | 1491 | CG | LYS | 210 | 149.823 | 143.368 | 156.345 | 1.00 37.09 |
| ATOM | 1492 | CD | LYS | 210 | 148.888 | 144.047 | 155.392 | 1.00 43.08 |
| ATOM | 1493 | CE | LYS | 210 | 148.089 | 143.023 | 154.654 | 1.00 47.12 |
| ATOM | 1494 | NZ | LYS | 210 | 147.099 | 143.588 | 153.710 | 1.00 51.93 |
| ATOM | 1495 | C | LYS | 210 | 152.828 | 143.099 | 157.705 | 1.00 25.86 |
| ATOM | 1496 | O | LYS | 210 | 153.570 | 143.415 | 156.777 | 1.00 26.70 |
| ATOM | 1497 | N | MET | 211 | 153.043 | 142.001 | 158.423 | 1.00 24.05 |
| ATOM | 1498 | CA | MET | 211 | 154.199 | 141.139 | 158.187 | 1.00 22.50 |
| ATOM | 1499 | CB | MET | 211 | 154.025 | 139.838 | 158.980 | 1.00 19.70 |
| ATOM | 1500 | CG | MET | 211 | 155.332 | 139.158 | 159.333 | 1.00 11.08 |
| ATOM | 1501 | SD | MET | 211 | 155.229 | 137.813 | 160.583 | 1.00 18.15 |
| ATOM | 1502 | CE | MET | 211 | 155.023 | 136.379 | 159.643 | 1.00 12.30 |
| ATOM | 1503 | C | MET | 211 | 154.594 | 140.806 | 156.744 | 1.00 24.00 |
| ATOM | 1504 | O | MET | 211 | 155.785 | 140.747 | 156.432 | 1.00 26.01 |
| ATOM | 1505 | N | THR | 212 | 153.627 | 140.580 | 155.859 | 1.00 23.79 |
| ATOM | 1506 | CA | THR | 212 | 153.972 | 140.237 | 154.482 | 1.00 23.03 |
| ATOM | 1507 | CB | THR | 212 | 152.730 | 139.871 | 153.657 | 1.00 23.05 |
| ATOM | 1508 | OG1 | THR | 212 | 151.714 | 140.852 | 153.879 | 1.00 26.29 |
| ATOM | 1509 | CG2 | THR | 212 | 152.191 | 138.502 | 154.064 | 1.00 20.69 |
| ATOM | 1510 | C | THR | 212 | 154.641 | 141.445 | 153.864 | 1.00 23.17 |
| ATOM | 1511 | O | THR | 212 | 155.556 | 141.325 | 153.046 | 1.00 24.32 |
| ATOM | 1512 | N | GLU | 213 | 154.191 | 142.619 | 154.281 | 1.00 22.00 |
| ATOM | 1513 | CA | GLU | 213 | 154.751 | 143.856 | 153.771 | 1.00 22.26 |
| ATOM | 1514 | CB | GLU | 213 | 153.826 | 145.026 | 154.090 | 1.00 23.52 |
| ATOM | 1515 | CG | GLU | 213 | 152.456 | 144.902 | 153.465 | 1.00 29.10 |
| ATOM | 1516 | CD | GLU | 213 | 151.623 | 146.154 | 153.635 | 1.00 33.52 |
| ATOM | 1517 | OE1 | GLU | 213 | 152.031 | 147.039 | 154.416 | 1.00 35.20 |
| ATOM | 1518 | OE2 | GLU | 213 | 150.558 | 146.251 | 152.986 | 1.00 37.49 |
| ATOM | 1519 | C | GLU | 213 | 156.118 | 144.099 | 154.384 | 1.00 22.28 |
| ATOM | 1520 | O | GLU | 213 | 157.033 | 144.575 | 153.710 | 1.00 22.79 |
| ATOM | 1521 | N | ILE | 214 | 156.250 | 143.777 | 155.667 | 1.00 20.88 |
| ATOM | 1522 | CA | ILE | 214 | 157.512 | 143.949 | 156.364 | 1.00 18.91 |
| ATOM | 1523 | CB | ILE | 214 | 157.360 | 143.613 | 157.865 | 1.00 18.07 |
| ATOM | 1524 | CG2 | ILE | 214 | 158.721 | 143.503 | 158.527 | 1.00 17.21 |
| ATOM | 1525 | CG1 | ILE | 214 | 156.542 | 144.703 | 158.557 | 1.00 16.02 |
| ATOM | 1526 | CD1 | ILE | 214 | 155.928 | 144.263 | 159.872 | 1.00 15.93 |
| ATOM | 1527 | C | ILE | 214 | 158.527 | 143.009 | 155.722 | 1.00 18.62 |
| ATOM | 1528 | O | ILE | 214 | 159.668 | 143.386 | 155.463 | 1.00 16.80 |
| ATOM | 1529 | N | GLN | 215 | 158.090 | 141.787 | 155.445 | 1.00 19.03 |
| ATOM | 1530 | CA | GLN | 215 | 158.944 | 140.781 | 154.831 | 1.00 18.91 |
| ATOM | 1531 | CB | GLN | 215 | 158.209 | 139.443 | 154.778 | 1.00 18.86 |
| ATOM | 1532 | CG | GLN | 215 | 159.076 | 138.276 | 154.363 | 1.00 19.71 |
| ATOM | 1533 | CD | GLN | 215 | 160.145 | 137.962 | 155.379 | 1.00 20.84 |
| ATOM | 1534 | OE1 | GLN | 215 | 159.852 | 137.707 | 156.546 | 1.00 22.90 |

*FIG. 4A - 27*

| ATOM | 1535 | NE2 | GLN | 215 | 161.398 | 137.975 | 154.942 | 1.00 | 21.72 |
|------|------|-----|-----|-----|---------|---------|---------|------|-------|
| ATOM | 1536 | C   | GLN | 215 | 159.358 | 141.192 | 153.425 | 1.00 | 19.11 |
| ATOM | 1537 | O   | GLN | 215 | 160.510 | 141.021 | 153.029 | 1.00 | 19.50 |
| ATOM | 1538 | N   | ALA | 216 | 158.416 | 141.736 | 152.668 | 1.00 | 19.51 |
| ATOM | 1539 | CA  | ALA | 216 | 158.699 | 142.164 | 151.309 | 1.00 | 18.72 |
| ATOM | 1540 | CB  | ALA | 216 | 157.429 | 142.649 | 150.645 | 1.00 | 15.16 |
| ATOM | 1541 | C   | ALA | 216 | 159.754 | 143.263 | 151.285 | 1.00 | 19.13 |
| ATOM | 1542 | O   | ALA | 216 | 160.593 | 143.304 | 150.389 | 1.00 | 20.90 |
| ATOM | 1543 | N   | LYS | 217 | 159.722 | 144.159 | 152.261 | 1.00 | 19.20 |
| ATOM | 1544 | CA  | LYS | 217 | 160.704 | 145.236 | 152.283 | 1.00 | 19.25 |
| ATOM | 1545 | CB  | LYS | 217 | 160.320 | 146.298 | 153.316 | 1.00 | 18.52 |
| ATOM | 1546 | CG  | LYS | 217 | 161.135 | 147.571 | 153.195 | 1.00 | 18.39 |
| ATOM | 1547 | CD  | LYS | 217 | 160.783 | 148.564 | 154.277 | 1.00 | 20.03 |
| ATOM | 1548 | CE  | LYS | 217 | 161.607 | 149.829 | 154.126 | 1.00 | 22.91 |
| ATOM | 1549 | NZ  | LYS | 217 | 160.988 | 151.003 | 154.807 | 1.00 | 28.08 |
| ATOM | 1550 | C   | LYS | 217 | 162.084 | 144.673 | 152.598 | 1.00 | 19.89 |
| ATOM | 1551 | O   | LYS | 217 | 163.069 | 145.021 | 151.945 | 1.00 | 19.48 |
| ATOM | 1552 | N   | MET | 218 | 162.147 | 143.801 | 153.600 | 1.00 | 17.73 |
| ATOM | 1553 | CA  | MET | 218 | 163.397 | 143.171 | 153.994 | 1.00 | 17.14 |
| ATOM | 1554 | CB  | MET | 218 | 163.163 | 142.230 | 155.190 | 1.00 | 14.25 |
| ATOM | 1555 | CG  | MET | 218 | 162.845 | 142.937 | 156.519 | 1.00 | 10.46 |
| ATOM | 1556 | SD  | MET | 218 | 162.586 | 141.816 | 157.896 | 1.00 | 2.00  |
| ATOM | 1557 | CE  | MET | 218 | 161.128 | 141.341 | 157.598 | 1.00 | 2.68  |
| ATOM | 1558 | C   | MET | 218 | 163.952 | 142.385 | 152.802 | 1.00 | 18.69 |
| ATOM | 1559 | O   | MET | 218 | 165.135 | 142.488 | 152.474 | 1.00 | 19.98 |
| ATOM | 1560 | N   | ASP | 219 | 163.091 | 141.609 | 152.148 | 1.00 | 19.15 |
| ATOM | 1561 | CA  | ASP | 219 | 163.495 | 140.811 | 150.993 | 1.00 | 19.86 |
| ATOM | 1562 | CB  | ASP | 219 | 162.294 | 140.052 | 150.431 | 1.00 | 19.61 |
| ATOM | 1563 | CG  | ASP | 219 | 161.853 | 138.917 | 151.325 | 1.00 | 20.67 |
| ATOM | 1564 | OD1 | ASP | 219 | 162.588 | 138.594 | 152.279 | 1.00 | 20.64 |
| ATOM | 1565 | OD2 | ASP | 219 | 160.769 | 138.347 | 151.077 | 1.00 | 21.52 |
| ATOM | 1566 | C   | ASP | 219 | 164.105 | 141.666 | 149.885 | 1.00 | 21.24 |
| ATOM | 1567 | O   | ASP | 219 | 165.115 | 141.297 | 149.285 | 1.00 | 21.14 |
| ATOM | 1568 | N   | ASP | 220 | 163.482 | 142.806 | 149.610 | 1.00 | 21.69 |
| ATOM | 1569 | CA  | ASP | 220 | 163.968 | 143.699 | 148.569 | 1.00 | 22.00 |
| ATOM | 1570 | CB  | ASP | 220 | 162.938 | 144.799 | 148.306 | 1.00 | 23.29 |
| ATOM | 1571 | CG  | ASP | 220 | 163.409 | 145.801 | 147.278 | 1.00 | 25.59 |
| ATOM | 1572 | OD1 | ASP | 220 | 163.525 | 145.426 | 146.094 | 1.00 | 27.74 |
| ATOM | 1573 | OD2 | ASP | 220 | 163.664 | 146.964 | 147.655 | 1.00 | 28.37 |
| ATOM | 1574 | C   | ASP | 220 | 165.310 | 144.321 | 148.950 | 1.00 | 22.36 |
| ATOM | 1575 | O   | ASP | 220 | 166.217 | 144.411 | 148.120 | 1.00 | 22.52 |
| ATOM | 1576 | N   | LEU | 221 | 165.434 | 144.746 | 150.206 | 1.00 | 21.65 |
| ATOM | 1577 | CA  | LEU | 221 | 166.666 | 145.358 | 150.692 | 1.00 | 21.02 |
| ATOM | 1578 | CB  | LEU | 221 | 166.444 | 145.974 | 152.074 | 1.00 | 18.91 |
| ATOM | 1579 | CG  | LEU | 221 | 165.543 | 147.206 | 152.133 | 1.00 | 18.44 |
| ATOM | 1580 | CD1 | LEU | 221 | 165.616 | 147.810 | 153.528 | 1.00 | 14.81 |
| ATOM | 1581 | CD2 | LEU | 221 | 165.971 | 148.219 | 151.074 | 1.00 | 17.41 |
| ATOM | 1582 | C   | LEU | 221 | 167.799 | 144.340 | 150.763 | 1.00 | 21.87 |
| ATOM | 1583 | O   | LEU | 221 | 168.967 | 144.690 | 150.603 | 1.00 | 22.87 |
| ATOM | 1584 | N   | THR | 222 | 167.455 | 143.082 | 151.012 | 1.00 | 21.49 |
| ATOM | 1585 | CA  | THR | 222 | 168.461 | 142.026 | 151.081 | 1.00 | 21.89 |
| ATOM | 1586 | CB  | THR | 222 | 167.851 | 140.726 | 151.624 | 1.00 | 19.67 |
| ATOM | 1587 | OG1 | THR | 222 | 167.446 | 140.931 | 152.982 | 1.00 | 20.77 |
| ATOM | 1588 | CG2 | THR | 222 | 168.861 | 139.592 | 151.562 | 1.00 | 14.60 |
| ATOM | 1589 | C   | THR | 222 | 169.000 | 141.773 | 149.677 | 1.00 | 22.72 |
| ATOM | 1590 | O   | THR | 222 | 170.204 | 141.681 | 149.454 | 1.00 | 21.76 |
| ATOM | 1591 | N   | GLU | 223 | 168.076 | 141.666 | 148.735 | 1.00 | 25.22 |

*FIG. 4A - 28*

```
ATOM   1592  CA   GLU   223     168.392 141.439 147.337  1.00 27.18
ATOM   1593  CB   GLU   223     167.089 141.373 146.556  1.00 29.86
ATOM   1594  CG   GLU   223     167.215 141.020 145.107  1.00 37.65
ATOM   1595  CD   GLU   223     165.861 140.751 144.497  1.00 44.28
ATOM   1596  OE1  GLU   223     165.090 139.970 145.098  1.00 48.58
ATOM   1597  OE2  GLU   223     165.565 141.323 143.426  1.00 47.78
ATOM   1598  C    GLU   223     169.260 142.580 146.819  1.00 26.88
ATOM   1599  O    GLU   223     170.311 142.357 146.219  1.00 28.25
ATOM   1600  N    ARG   224     168.808 143.805 147.059  1.00 24.94
ATOM   1601  CA   ARG   224     169.526 144.996 146.629  1.00 24.22
ATOM   1602  CB   ARG   224     168.797 146.248 147.135  1.00 23.27
ATOM   1603  CG   ARG   224     169.281 147.566 146.536  1.00 22.79
ATOM   1604  CD   ARG   224     168.547 148.744 147.162  1.00 20.40
ATOM   1605  NE   ARG   224     168.982 150.026 146.617  1.00 19.46
ATOM   1606  CZ   ARG   224     168.313 150.712 145.694  1.00 18.88
ATOM   1607  NH1  ARG   224     167.172 150.240 145.211  1.00 17.28
ATOM   1608  NH2  ARG   224     168.771 151.881 145.268  1.00 16.26
ATOM   1609  C    ARG   224     170.968 145.000 147.131  1.00 24.55
ATOM   1610  O    ARG   224     171.905 145.143 146.346  1.00 25.32
ATOM   1611  N    ARG   225     171.146 144.835 148.438  1.00 24.47
ATOM   1612  CA   ARG   225     172.480 144.842 149.031  1.00 24.94
ATOM   1613  CB   ARG   225     172.391 144.738 150.556  1.00 24.09
ATOM   1614  CG   ARG   225     173.723 144.937 151.257  1.00 23.96
ATOM   1615  CD   ARG   225     173.668 144.488 152.705  1.00 23.50
ATOM   1616  NE   ARG   225     172.946 145.442 153.544  1.00 23.54
ATOM   1617  CZ   ARG   225     173.492 146.516 154.105  1.00 21.24
ATOM   1618  NH1  ARG   225     172.750 147.321 154.851  1.00 18.94
ATOM   1619  NH2  ARG   225     174.778 146.785 153.921  1.00 20.65
ATOM   1620  C    ARG   225     173.367 143.723 148.508  1.00 25.01
ATOM   1621  O    ARG   225     174.538 143.939 148.207  1.00 25.16
ATOM   1622  N    GLU   226     172.811 142.524 148.408  1.00 24.81
ATOM   1623  CA   GLU   226     173.577 141.388 147.929  1.00 25.28
ATOM   1624  CB   GLU   226     172.712 140.131 147.922  1.00 24.47
ATOM   1625  CG   GLU   226     172.591 139.463 149.279  1.00 29.00
ATOM   1626  CD   GLU   226     171.539 138.372 149.303  1.00 31.25
ATOM   1627  OE1  GLU   226     170.748 138.279 148.340  1.00 33.42
ATOM   1628  OE2  GLU   226     171.503 137.605 150.288  1.00 34.36
ATOM   1629  C    GLU   226     174.118 141.644 146.533  1.00 26.67
ATOM   1630  O    GLU   226     175.231 141.240 146.210  1.00 27.88
ATOM   1631  N    SER   227     173.335 142.330 145.708  1.00 26.33
ATOM   1632  CA   SER   227     173.753 142.616 144.340  1.00 26.55
ATOM   1633  CB   SER   227     172.542 143.008 143.493  1.00 25.54
ATOM   1634  OG   SER   227     172.085 144.305 143.829  1.00 28.02
ATOM   1635  C    SER   227     174.808 143.706 144.232  1.00 26.62
ATOM   1636  O    SER   227     175.455 143.836 143.200  1.00 27.87
ATOM   1637  N    LYS   228     174.993 144.477 145.299  1.00 27.70
ATOM   1638  CA   LYS   228     175.960 145.572 145.282  1.00 28.39
ATOM   1639  CB   LYS   228     175.276 146.889 145.657  1.00 28.72
ATOM   1640  CG   LYS   228     174.101 147.297 144.793  1.00 29.69
ATOM   1641  CD   LYS   228     173.602 148.671 145.228  1.00 31.23
ATOM   1642  CE   LYS   228     172.182 148.926 144.763  1.00 30.72
ATOM   1643  NZ   LYS   228     172.155 149.274 143.321  1.00 31.10
ATOM   1644  C    LYS   228     177.176 145.428 146.189  1.00 28.77
ATOM   1645  O    LYS   228     178.196 146.075 145.953  1.00 28.59
ATOM   1646  N    GLN   229     177.082 144.602 147.225  1.00 28.95
ATOM   1647  CA   GLN   229     178.199 144.477 148.148  1.00 28.96
ATOM   1648  CB   GLN   229     177.760 144.968 149.529  1.00 28.91
```

*FIG. 4A - 29*

| ATOM | 1649 | CG  | GLN | 229 | 177.153 | 146.367 | 149.483 | 1.00 | 28.94 |
| ATOM | 1650 | CD  | GLN | 229 | 176.787 | 146.919 | 150.849 | 1.00 | 29.83 |
| ATOM | 1651 | OE1 | GLN | 229 | 176.822 | 146.210 | 151.855 | 1.00 | 31.07 |
| ATOM | 1652 | NE2 | GLN | 229 | 176.430 | 148.196 | 150.888 | 1.00 | 29.56 |
| ATOM | 1653 | C   | GLN | 229 | 178.844 | 143.108 | 148.261 | 1.00 | 29.17 |
| ATOM | 1654 | O   | GLN | 229 | 178.187 | 142.077 | 148.124 | 1.00 | 29.48 |
| ATOM | 1655 | N   | PRO | 230 | 180.164 | 143.089 | 148.505 | 1.00 | 30.33 |
| ATOM | 1656 | CD  | PRO | 230 | 181.003 | 144.289 | 148.665 | 1.00 | 29.73 |
| ATOM | 1657 | CA  | PRO | 230 | 180.940 | 141.855 | 148.647 | 1.00 | 31.54 |
| ATOM | 1658 | CB  | PRO | 230 | 182.379 | 142.321 | 148.456 | 1.00 | 31.07 |
| ATOM | 1659 | CG  | PRO | 230 | 182.373 | 143.727 | 148.949 | 1.00 | 29.78 |
| ATOM | 1660 | C   | PRO | 230 | 180.693 | 141.275 | 150.037 | 1.00 | 32.87 |
| ATOM | 1661 | O   | PRO | 230 | 181.594 | 141.204 | 150.873 | 1.00 | 33.41 |
| ATOM | 1662 | N   | LEU | 231 | 179.452 | 140.869 | 150.272 | 1.00 | 33.14 |
| ATOM | 1663 | CA  | LEU | 231 | 179.040 | 140.319 | 151.555 | 1.00 | 33.92 |
| ATOM | 1664 | CB  | LEU | 231 | 177.522 | 140.133 | 151.576 | 1.00 | 33.33 |
| ATOM | 1665 | CG  | LEU | 231 | 176.635 | 141.376 | 151.651 | 1.00 | 34.07 |
| ATOM | 1666 | CD1 | LEU | 231 | 175.190 | 140.934 | 151.796 | 1.00 | 32.46 |
| ATOM | 1667 | CD2 | LEU | 231 | 177.056 | 142.259 | 152.822 | 1.00 | 32.20 |
| ATOM | 1668 | C   | LEU | 231 | 179.694 | 138.992 | 151.895 | 1.00 | 35.29 |
| ATOM | 1669 | O   | LEU | 231 | 179.605 | 138.536 | 153.031 | 1.00 | 37.38 |
| ATOM | 1670 | N   | GLU | 232 | 180.353 | 138.371 | 150.925 | 1.00 | 36.02 |
| ATOM | 1671 | CA  | GLU | 232 | 180.970 | 137.072 | 151.165 | 1.00 | 37.27 |
| ATOM | 1672 | CB  | GLU | 232 | 180.886 | 136.221 | 149.895 | 1.00 | 38.78 |
| ATOM | 1673 | CG  | GLU | 232 | 181.992 | 136.493 | 148.892 | 1.00 | 42.97 |
| ATOM | 1674 | CD  | GLU | 232 | 181.691 | 137.680 | 148.003 | 1.00 | 45.43 |
| ATOM | 1675 | OE1 | GLU | 232 | 182.453 | 137.911 | 147.043 | 1.00 | 47.83 |
| ATOM | 1676 | OE2 | GLU | 232 | 180.692 | 138.383 | 148.262 | 1.00 | 47.47 |
| ATOM | 1677 | C   | GLU | 232 | 182.410 | 137.077 | 151.675 | 1.00 | 37.52 |
| ATOM | 1678 | O   | GLU | 232 | 182.984 | 136.016 | 151.905 | 1.00 | 39.17 |
| ATOM | 1679 | N   | TYR | 233 | 182.995 | 138.254 | 151.856 | 1.00 | 36.84 |
| ATOM | 1680 | CA  | TYR | 233 | 184.370 | 138.340 | 152.340 | 1.00 | 36.11 |
| ATOM | 1681 | CB  | TYR | 233 | 185.274 | 139.033 | 151.323 | 1.00 | 37.81 |
| ATOM | 1682 | CG  | TYR | 233 | 185.542 | 138.283 | 150.053 | 1.00 | 40.94 |
| ATOM | 1683 | CD1 | TYR | 233 | 185.066 | 138.765 | 148.836 | 1.00 | 42.32 |
| ATOM | 1684 | CE1 | TYR | 233 | 185.357 | 138.119 | 147.646 | 1.00 | 43.41 |
| ATOM | 1685 | CD2 | TYR | 233 | 186.318 | 137.127 | 150.050 | 1.00 | 41.05 |
| ATOM | 1686 | CE2 | TYR | 233 | 186.616 | 136.470 | 148.862 | 1.00 | 43.26 |
| ATOM | 1687 | CZ  | TYR | 233 | 186.132 | 136.974 | 147.664 | 1.00 | 44.01 |
| ATOM | 1688 | OH  | TYR | 233 | 186.429 | 136.342 | 146.482 | 1.00 | 45.98 |
| ATOM | 1689 | C   | TYR | 233 | 184.462 | 139.168 | 153.602 | 1.00 | 35.23 |
| ATOM | 1690 | O   | TYR | 233 | 183.711 | 140.128 | 153.776 | 1.00 | 34.28 |
| ATOM | 1691 | N   | PRO | 234 | 185.383 | 138.809 | 154.509 | 1.00 | 34.52 |
| ATOM | 1692 | CD  | PRO | 234 | 186.359 | 137.708 | 154.532 | 1.00 | 33.72 |
| ATOM | 1693 | CA  | PRO | 234 | 185.453 | 139.648 | 155.698 | 1.00 | 34.09 |
| ATOM | 1694 | CB  | PRO | 234 | 186.632 | 139.080 | 156.484 | 1.00 | 32.94 |
| ATOM | 1695 | CG  | PRO | 234 | 186.837 | 137.712 | 155.951 | 1.00 | 32.23 |
| ATOM | 1696 | C   | PRO | 234 | 185.775 | 141.003 | 155.114 | 1.00 | 35.12 |
| ATOM | 1697 | O   | PRO | 234 | 186.542 | 141.107 | 154.158 | 1.00 | 35.21 |
| ATOM | 1698 | N   | SER | 235 | 185.174 | 142.054 | 155.649 | 1.00 | 36.57 |
| ATOM | 1699 | CA  | SER | 235 | 185.449 | 143.370 | 155.097 | 1.00 | 38.16 |
| ATOM | 1700 | CB  | SER | 235 | 184.623 | 143.596 | 153.825 | 1.00 | 36.82 |
| ATOM | 1701 | OG  | SER | 235 | 183.357 | 144.113 | 154.134 | 1.00 | 37.60 |
| ATOM | 1702 | C   | SER | 235 | 185.212 | 144.507 | 156.055 | 1.00 | 39.77 |
| ATOM | 1703 | O   | SER | 235 | 184.629 | 144.341 | 157.120 | 1.00 | 38.66 |
| ATOM | 1704 | N   | CYS | 236 | 185.721 | 145.661 | 155.680 | 1.00 | 41.95 |
| ATOM | 1705 | CA  | CYS | 236 | 185.552 | 146.852 | 156.444 | 1.00 | 43.66 |

*FIG. 4A - 30*

```
ATOM   1706  CB   CYS   236     186.889 147.485 156.659  1.00 43.12
ATOM   1707  SG   CYS   236     186.762 149.144 157.302  1.00 44.24
ATOM   1708  C    CYS   236     184.728 147.650 155.428  1.00 44.53
ATOM   1709  O    CYS   236     185.088 147.738 154.222  1.00 45.52
ATOM   1710  N    GLY   237     183.633 148.236 155.897  1.00 47.94
ATOM   1711  CA   GLY   237     182.775 148.991 155.001  1.00 45.98
ATOM   1712  C    GLY   237     183.096 150.471 154.855  1.00 48.02
ATOM   1713  O    GLY   237     183.526 151.109 155.812  1.00 50.53
ATOM   1714  N    SER   238     182.836 151.044 153.683  1.00 46.89
ATOM   1715  CA   SER   238     183.127 152.460 153.424  1.00 46.91
ATOM   1716  CB   SER   238     181.832 153.273 153.259  1.00 50.41
ATOM   1717  OG   SER   238     180.732 152.719 153.961  1.00 54.60
ATOM   1718  C    SER   238     184.115 153.189 154.365  1.00 45.67
ATOM   1719  O    SER   238     183.800 153.844 155.377  1.00 45.61
ATOM   1720  N    VAL   239     185.343 153.067 153.912  1.00 39.36
ATOM   1721  CA   VAL   239     186.553 153.597 154.492  1.00 35.97
ATOM   1722  CB   VAL   239     187.690 153.008 153.701  1.00 34.53
ATOM   1723  CG1  VAL   239     189.011 153.252 154.383  1.00 30.87
ATOM   1724  CG2  VAL   239     187.389 151.533 153.469  1.00 28.60
ATOM   1725  C    VAL   239     186.736 155.107 154.492  1.00 35.07
ATOM   1726  O    VAL   239     187.320 155.673 155.422  1.00 35.65
ATOM   1727  N    PHE   240     186.259 155.760 153.439  1.00 33.80
ATOM   1728  CA   PHE   240     186.440 157.196 153.294  1.00 31.77
ATOM   1729  CB   PHE   240     187.072 157.495 151.933  1.00 28.62
ATOM   1730  CG   PHE   240     188.335 156.728 151.655  1.00 28.50
ATOM   1731  CD1  PHE   240     188.328 155.657 150.770  1.00 28.28
ATOM   1732  CD2  PHE   240     189.538 157.095 152.252  1.00 28.52
ATOM   1733  CE1  PHE   240     189.494 154.965 150.478  1.00 28.80
ATOM   1734  CE2  PHE   240     190.714 156.402 151.962  1.00 28.42
ATOM   1735  CZ   PHE   240     190.688 155.337 151.074  1.00 29.85
ATOM   1736  C    PHE   240     185.221 158.080 153.431  1.00 31.57
ATOM   1737  O    PHE   240     184.082 157.635 153.306  1.00 31.32
ATOM   1738  N    GLN   241     185.499 159.357 153.671  1.00 32.52
ATOM   1739  CA   GLN   241     184.473 160.376 153.781  1.00 32.72
ATOM   1740  CB   GLN   241     185.034 161.640 154.431  1.00 36.33
ATOM   1741  CG   GLN   241     185.437 161.532 155.891  1.00 41.47
ATOM   1742  CD   GLN   241     186.133 162.796 156.374  1.00 46.32
ATOM   1743  OE1  GLN   241     186.714 162.824 157.458  1.00 48.90
ATOM   1744  NE2  GLN   241     186.076 163.852 155.562  1.00 49.99
ATOM   1745  C    GLN   241     184.150 160.701 152.334  1.00 31.45
ATOM   1746  O    GLN   241     184.956 160.430 151.441  1.00 30.29
ATOM   1747  N    ARG   242     182.986 161.282 152.083  1.00 28.98
ATOM   1748  CA   ARG   242     182.664 161.636 150.713  1.00 27.46
ATOM   1749  CB   ARG   242     181.157 161.587 150.463  1.00 24.72
ATOM   1750  CG   ARG   242     180.813 161.729 148.992  1.00 22.85
ATOM   1751  CD   ARG   242     179.330 161.652 148.744  1.00 22.19
ATOM   1752  NE   ARG   242     178.756 160.397 149.214  1.00 24.49
ATOM   1753  CZ   ARG   242     177.689 160.319 150.001  1.00 24.31
ATOM   1754  NH1  ARG   242     177.081 161.423 150.408  1.00 26.29
ATOM   1755  NH2  ARG   242     177.218 159.140 150.373  1.00 23.87
ATOM   1756  C    ARG   242     183.189 163.039 150.422  1.00 27.68
ATOM   1757  O    ARG   242     182.823 164.004 151.096  1.00 29.92
ATOM   1758  N    PRO   243     184.083 163.163 149.430  1.00 26.86
ATOM   1759  CD   PRO   243     184.630 162.074 148.603  1.00 26.04
ATOM   1760  CA   PRO   243     184.648 164.464 149.063  1.00 26.27
ATOM   1761  CB   PRO   243     185.869 164.098 148.231  1.00 25.29
ATOM   1762  CG   PRO   243     185.512 162.795 147.615  1.00 25.56
```

*FIG. 4A - 31*

| ATOM | 1763 | C | PRO | 243 | 183.641 | 165.288 | 148.268 | 1.00 | 25.50 |
| ATOM | 1764 | O | PRO | 243 | 182.743 | 164.743 | 147.632 | 1.00 | 27.41 |
| ATOM | 1765 | N | PRO | 244 | 183.779 | 166.619 | 148.297 | 1.00 | 23.72 |
| ATOM | 1766 | CD | PRO | 244 | 184.799 | 167.386 | 149.033 | 1.00 | 21.21 |
| ATOM | 1767 | CA | PRO | 244 | 182.862 | 167.495 | 147.568 | 1.00 | 22.44 |
| ATOM | 1768 | CB | PRO | 244 | 183.484 | 168.877 | 147.737 | 1.00 | 22.43 |
| ATOM | 1769 | CG | PRO | 244 | 184.253 | 168.782 | 149.009 | 1.00 | 19.82 |
| ATOM | 1770 | C | PRO | 244 | 182.661 | 167.144 | 146.100 | 1.00 | 23.83 |
| ATOM | 1771 | O | PRO | 244 | 183.617 | 166.849 | 145.384 | 1.00 | 25.16 |
| ATOM | 1772 | N | GLY | 245 | 181.401 | 167.174 | 145.670 | 1.00 | 24.19 |
| ATOM | 1773 | CA | GLY | 245 | 181.054 | 166.908 | 144.285 | 1.00 | 24.75 |
| ATOM | 1774 | C | GLY | 245 | 181.199 | 165.503 | 143.734 | 1.00 | 26.22 |
| ATOM | 1775 | O | GLY | 245 | 180.863 | 165.262 | 142.571 | 1.00 | 26.48 |
| ATOM | 1776 | N | HIS | 246 | 181.688 | 164.570 | 144.542 | 1.00 | 26.47 |
| ATOM | 1777 | CA | HIS | 246 | 181.861 | 163.202 | 144.064 | 1.00 | 27.44 |
| ATOM | 1778 | CB | HIS | 246 | 183.306 | 162.967 | 143.629 | 1.00 | 27.26 |
| ATOM | 1779 | CG | HIS | 246 | 183.853 | 164.030 | 142.732 | 1.00 | 27.14 |
| ATOM | 1780 | CD2 | HIS | 246 | 184.309 | 165.274 | 143.002 | 1.00 | 26.40 |
| ATOM | 1781 | ND1 | HIS | 246 | 183.984 | 163.857 | 141.373 | 1.00 | 26.13 |
| ATOM | 1782 | CE1 | HIS | 246 | 184.501 | 164.951 | 140.842 | 1.00 | 26.16 |
| ATOM | 1783 | NE2 | HIS | 246 | 184.707 | 165.825 | 141.809 | 1.00 | 27.52 |
| ATOM | 1784 | C | HIS | 246 | 181.513 | 162.142 | 145.089 | 1.00 | 28.28 |
| ATOM | 1785 | O | HIS | 246 | 181.157 | 162.443 | 146.227 | 1.00 | 30.64 |
| ATOM | 1786 | N | PHE | 247 | 181.630 | 160.892 | 144.655 | 1.00 | 28.03 |
| ATOM | 1787 | CA | PHE | 247 | 181.389 | 159.733 | 145.501 | 1.00 | 28.32 |
| ATOM | 1788 | CB | PHE | 247 | 180.353 | 158.809 | 144.862 | 1.00 | 27.24 |
| ATOM | 1789 | CG | PHE | 247 | 178.939 | 159.240 | 145.103 | 1.00 | 25.83 |
| ATOM | 1790 | CD1 | PHE | 247 | 178.174 | 159.775 | 144.071 | 1.00 | 25.04 |
| ATOM | 1791 | CD2 | PHE | 247 | 178.373 | 159.121 | 146.367 | 1.00 | 24.73 |
| ATOM | 1792 | CE1 | PHE | 247 | 176.867 | 160.193 | 144.295 | 1.00 | 23.59 |
| ATOM | 1793 | CE2 | PHE | 247 | 177.068 | 159.535 | 146.605 | 1.00 | 24.44 |
| ATOM | 1794 | CZ | PHE | 247 | 176.310 | 160.071 | 145.564 | 1.00 | 24.42 |
| ATOM | 1795 | C | PHE | 247 | 182.738 | 159.027 | 145.597 | 1.00 | 29.00 |
| ATOM | 1796 | O | PHE | 247 | 183.390 | 158.791 | 144.577 | 1.00 | 29.60 |
| ATOM | 1797 | N | ALA | 248 | 183.161 | 158.701 | 146.815 | 1.00 | 27.78 |
| ATOM | 1798 | CA | ALA | 248 | 184.450 | 158.050 | 147.016 | 1.00 | 26.64 |
| ATOM | 1799 | CB | ALA | 248 | 184.651 | 157.731 | 148.485 | 1.00 | 24.22 |
| ATOM | 1800 | C | ALA | 248 | 184.600 | 156.787 | 146.186 | 1.00 | 26.55 |
| ATOM | 1801 | O | ALA | 248 | 185.602 | 156.606 | 145.497 | 1.00 | 27.74 |
| ATOM | 1802 | N | GLY | 249 | 183.601 | 155.917 | 146.251 | 1.00 | 26.01 |
| ATOM | 1803 | CA | GLY | 249 | 183.657 | 154.676 | 145.502 | 1.00 | 26.61 |
| ATOM | 1804 | C | GLY | 249 | 183.760 | 154.871 | 144.003 | 1.00 | 28.03 |
| ATOM | 1805 | O | GLY | 249 | 184.384 | 154.069 | 143.310 | 1.00 | 27.65 |
| ATOM | 1806 | N | LYS | 250 | 183.142 | 155.931 | 143.491 | 1.00 | 29.61 |
| ATOM | 1807 | CA | LYS | 250 | 183.182 | 156.202 | 142.059 | 1.00 | 29.71 |
| ATOM | 1808 | CB | LYS | 250 | 182.124 | 157.237 | 141.679 | 1.00 | 31.15 |
| ATOM | 1809 | CG | LYS | 250 | 180.725 | 156.664 | 141.580 | 1.00 | 36.20 |
| ATOM | 1810 | CD | LYS | 250 | 179.769 | 157.632 | 140.899 | 1.00 | 41.60 |
| ATOM | 1811 | CE | LYS | 250 | 178.316 | 157.170 | 141.023 | 1.00 | 43.21 |
| ATOM | 1812 | NZ | LYS | 250 | 177.372 | 158.059 | 140.282 | 1.00 | 42.62 |
| ATOM | 1813 | C | LYS | 250 | 184.562 | 156.712 | 141.687 | 1.00 | 29.06 |
| ATOM | 1814 | O | LYS | 250 | 185.113 | 156.343 | 140.650 | 1.00 | 28.52 |
| ATOM | 1815 | N | LEU | 251 | 185.121 | 157.561 | 142.544 | 1.00 | 28.18 |
| ATOM | 1816 | CA | LEU | 251 | 186.451 | 158.112 | 142.316 | 1.00 | 27.31 |
| ATOM | 1817 | CB | LEU | 251 | 186.819 | 159.104 | 143.424 | 1.00 | 24.97 |
| ATOM | 1818 | CG | LEU | 251 | 186.230 | 160.516 | 143.370 | 1.00 | 23.99 |
| ATOM | 1819 | CD1 | LEU | 251 | 186.548 | 161.240 | 144.665 | 1.00 | 21.07 |

*FIG. 4A - 32*

```
ATOM  1820  CD2  LEU  251     186.796  161.275  142.184  1.00  22.33
ATOM  1821  C    LEU  251     187.460  156.972  142.312  1.00  29.04
ATOM  1822  O    LEU  251     188.284  156.861  141.407  1.00  30.74
ATOM  1823  N    ILE  252     187.386  156.123  143.332  1.00  30.25
ATOM  1824  CA   ILE  252     188.295  154.987  143.461  1.00  30.71
ATOM  1825  CB   ILE  252     187.965  154.148  144.720  1.00  28.76
ATOM  1826  CG2  ILE  252     188.559  152.757  144.605  1.00  27.37
ATOM  1827  CG1  ILE  252     188.533  154.832  145.961  1.00  27.92
ATOM  1828  CD1  ILE  252     187.739  154.559  147.205  1.00  29.05
ATOM  1829  C    ILE  252     188.206  154.097  142.233  1.00  32.12
ATOM  1830  O    ILE  252     189.220  153.637  141.712  1.00  32.29
ATOM  1831  N    GLN  253     186.986  153.862  141.770  1.00  32.82
ATOM  1832  CA   GLN  253     186.772  153.021  140.604  1.00  34.29
ATOM  1833  CB   GLN  253     185.282  152.753  140.418  1.00  34.07
ATOM  1834  CG   GLN  253     184.963  151.919  139.200  1.00  33.59
ATOM  1835  CD   GLN  253     183.486  151.683  139.049  1.00  34.93
ATOM  1836  OE1  GLN  253     182.730  152.605  138.750  1.00  37.81
ATOM  1837  NE2  GLN  253     183.060  150.445  139.258  1.00  34.44
ATOM  1838  C    GLN  253     187.333  153.659  139.340  1.00  35.14
ATOM  1839  O    GLN  253     187.999  152.996  138.549  1.00  35.91
ATOM  1840  N    ASP  254     187.061  154.945  139.152  1.00  36.27
ATOM  1841  CA   ASP  254     187.544  155.657  137.975  1.00  36.75
ATOM  1842  CB   ASP  254     186.895  157.034  137.891  1.00  36.78
ATOM  1843  CG   ASP  254     185.425  156.955  137.544  1.00  37.21
ATOM  1844  OD1  ASP  254     185.002  155.914  136.997  1.00  37.11
ATOM  1845  OD2  ASP  254     184.696  157.931  137.819  1.00  38.54
ATOM  1846  C    ASP  254     189.060  155.795  137.982  1.00  36.92
ATOM  1847  O    ASP  254     189.664  156.155  136.972  1.00  37.20
ATOM  1848  N    SER  255     189.672  155.516  139.127  1.00  37.15
ATOM  1849  CA   SER  255     191.123  155.579  139.248  1.00  36.40
ATOM  1850  CB   SER  255     191.520  155.997  140.663  1.00  34.60
ATOM  1851  OG   SER  255     191.180  157.348  140.908  1.00  33.87
ATOM  1852  C    SER  255     191.694  154.194  138.936  1.00  37.31
ATOM  1853  O    SER  255     192.890  153.957  139.085  1.00  37.96
ATOM  1854  N    ASN  256     190.821  153.287  138.502  1.00  37.92
ATOM  1855  CA   ASN  256     191.204  151.919  138.163  1.00  39.85
ATOM  1856  CB   ASN  256     192.129  151.917  136.941  1.00  45.15
ATOM  1857  CG   ASN  256     192.543  150.514  136.525  1.00  51.80
ATOM  1858  OD1  ASN  256     191.768  149.560  136.649  1.00  54.82
ATOM  1859  ND2  ASN  256     193.772  150.381  136.034  1.00  54.46
ATOM  1860  C    ASN  256     191.883  151.190  139.323  1.00  37.86
ATOM  1861  O    ASN  256     192.850  150.454  139.129  1.00  37.61
ATOM  1862  N    LEU  257     191.365  151.382  140.530  1.00  34.85
ATOM  1863  CA   LEU  257     191.942  150.744  141.703  1.00  31.81
ATOM  1864  CB   LEU  257     191.871  151.695  142.895  1.00  29.64
ATOM  1865  CG   LEU  257     192.974  152.748  142.951  1.00  27.48
ATOM  1866  CD1  LEU  257     192.520  153.925  143.790  1.00  25.26
ATOM  1867  CD2  LEU  257     194.230  152.129  143.537  1.00  27.82
ATOM  1868  C    LEU  257     191.272  149.422  142.064  1.00  31.52
ATOM  1869  O    LEU  257     191.800  148.650  142.863  1.00  31.86
ATOM  1870  N    GLN  258     190.112  149.155  141.479  1.00  30.52
ATOM  1871  CA   GLN  258     189.410  147.918  141.777  1.00  30.35
ATOM  1872  CB   GLN  258     188.113  147.835  140.972  1.00  30.26
ATOM  1873  CG   GLN  258     186.930  148.531  141.638  1.00  31.84
ATOM  1874  CD   GLN  258     185.612  148.238  140.948  1.00  33.43
ATOM  1875  OE1  GLN  258     185.443  148.520  139.762  1.00  35.10
ATOM  1876  NE2  GLN  258     184.669  147.669  141.689  1.00  33.12
```

*FIG. 4A - 33*

```
ATOM  1877  C    GLN  258    190.300 146.727 141.460  1.00 31.00
ATOM  1878  O    GLN  258    190.904 146.660 140.395  1.00 31.81
ATOM  1879  N    GLY  259    190.387 145.792 142.399  1.00 31.60
ATOM  1880  CA   GLY  259    191.209 144.616 142.194  1.00 30.72
ATOM  1881  C    GLY  259    192.636 144.788 142.681  1.00 30.99
ATOM  1882  O    GLY  259    193.387 143.815 142.737  1.00 32.02
ATOM  1883  N    HIS  260    193.018 146.014 143.029  1.00 29.64
ATOM  1884  CA   HIS  260    194.371 146.268 143.510  1.00 29.15
ATOM  1885  CB   HIS  260    194.651 147.766 143.588  1.00 28.69
ATOM  1886  CG   HIS  260    196.082 148.088 143.883  1.00 28.61
ATOM  1887  CD2  HIS  260    196.763 148.132 145.054  1.00 27.58
ATOM  1888  ND1  HIS  260    196.999 148.377 142.898  1.00 30.44
ATOM  1889  CE1  HIS  260    198.182 148.581 143.443  1.00 30.23
ATOM  1890  NE2  HIS  260    198.066 148.439 144.755  1.00 29.61
ATOM  1891  C    HIS  260    194.554 145.649 144.887  1.00 30.19
ATOM  1892  O    HIS  260    193.828 145.979 145.822  1.00 30.94
ATOM  1893  N    ARG  261    195.535 144.761 145.011  1.00 29.14
ATOM  1894  CA   ARG  261    195.774 144.083 146.274  1.00 27.15
ATOM  1895  CB   ARG  261    195.613 142.572 146.089  1.00 25.72
ATOM  1896  CG   ARG  261    195.863 141.768 147.353  1.00 25.89
ATOM  1897  CD   ARG  261    195.784 140.278 147.086  1.00 26.11
ATOM  1898  NE   ARG  261    194.655 139.943 146.229  1.00 27.38
ATOM  1899  CZ   ARG  261    194.309 138.703 145.906  1.00 28.22
ATOM  1900  NH1  ARG  261    195.006 137.677 146.375  1.00 29.34
ATOM  1901  NH2  ARG  261    193.266 138.488 145.114  1.00 28.31
ATOM  1902  C    ARG  261    197.127 144.361 146.894  1.00 26.86
ATOM  1903  O    ARG  261    198.108 144.622 146.206  1.00 27.39
ATOM  1904  N    ILE  262    197.152 144.309 148.217  1.00 27.57
ATOM  1905  CA   ILE  262    198.361 144.499 148.998  1.00 27.60
ATOM  1906  CB   ILE  262    198.421 145.898 149.628  1.00 29.12
ATOM  1907  CG2  ILE  262    199.562 145.967 150.629  1.00 27.92
ATOM  1908  CG1  ILE  262    198.633 146.948 148.536  1.00 29.07
ATOM  1909  CD1  ILE  262    198.876 148.347 149.066  1.00 27.18
ATOM  1910  C    ILE  262    198.224 143.449 150.088  1.00 27.97
ATOM  1911  O    ILE  262    197.285 143.490 150.886  1.00 27.08
ATOM  1912  N    GLY  263    199.144 142.494 150.108  1.00 27.14
ATOM  1913  CA   GLY  263    199.058 141.439 151.095  1.00 25.70
ATOM  1914  C    GLY  263    197.848 140.595 150.753  1.00 25.62
ATOM  1915  O    GLY  263    197.748 140.067 149.646  1.00 25.28
ATOM  1916  N    GLY  264    196.917 140.481 151.694  1.00 26.53
ATOM  1917  CA   GLY  264    195.722 139.694 151.452  1.00 26.19
ATOM  1918  C    GLY  264    194.472 140.548 151.365  1.00 26.56
ATOM  1919  O    GLY  264    193.358 140.023 151.359  1.00 27.69
ATOM  1920  N    VAL  265    194.655 141.864 151.291  1.00 26.72
ATOM  1921  CA   VAL  265    193.534 142.800 151.208  1.00 26.85
ATOM  1922  CB   VAL  265    193.573 143.815 152.366  1.00 26.61
ATOM  1923  CG1  VAL  265    192.294 144.645 152.367  1.00 25.28
ATOM  1924  CG2  VAL  265    193.749 143.090 153.692  1.00 24.30
ATOM  1925  C    VAL  265    193.535 143.583 149.897  1.00 26.88
ATOM  1926  O    VAL  265    194.565 144.104 149.479  1.00 27.21
ATOM  1927  N    GLU  266    192.373 143.683 149.260  1.00 27.71
ATOM  1928  CA   GLU  266    192.265 144.406 147.998  1.00 28.50
ATOM  1929  CB   GLU  266    192.324 143.422 146.830  1.00 29.04
ATOM  1930  CG   GLU  266    191.152 142.459 146.782  1.00 30.84
ATOM  1931  CD   GLU  266    191.229 141.502 145.608  1.00 34.28
ATOM  1932  OE1  GLU  266    190.173 141.192 145.018  1.00 34.82
ATOM  1933  OE2  GLU  266    192.347 141.060 145.273  1.00 36.34
```

*FIG. 4A - 34*

| | | | | | | | | |
|---|---|---|---|---|---|---|---|---|
| ATOM | 1934 | C | GLU | 266 | 190.993 | 145.235 | 147.872 | 1.00 27.97 |
| ATOM | 1935 | O | GLU | 266 | 190.024 | 145.028 | 148.601 | 1.00 27.45 |
| ATOM | 1936 | N | VAL | 267 | 191.009 | 146.181 | 146.940 | 1.00 27.58 |
| ATOM | 1937 | CA | VAL | 267 | 189.844 | 147.015 | 146.687 | 1.00 27.38 |
| ATOM | 1938 | CB | VAL | 267 | 190.193 | 148.195 | 145.761 | 1.00 25.98 |
| ATOM | 1939 | CG1 | VAL | 267 | 188.926 | 148.833 | 145.224 | 1.00 24.38 |
| ATOM | 1940 | CG2 | VAL | 267 | 191.020 | 149.215 | 146.518 | 1.00 22.93 |
| ATOM | 1941 | C | VAL | 267 | 188.865 | 146.082 | 145.980 | 1.00 28.88 |
| ATOM | 1942 | O | VAL | 267 | 189.188 | 145.510 | 144.944 | 1.00 30.24 |
| ATOM | 1943 | N | SER | 268 | 187.678 | 145.916 | 146.546 | 1.00 29.48 |
| ATOM | 1944 | CA | SER | 268 | 186.681 | 145.021 | 145.971 | 1.00 29.93 |
| ATOM | 1945 | CB | SER | 268 | 185.406 | 145.057 | 146.809 | 1.00 27.76 |
| ATOM | 1946 | OG | SER | 268 | 184.332 | 144.478 | 146.093 | 1.00 26.19 |
| ATOM | 1947 | C | SER | 268 | 186.331 | 145.301 | 144.509 | 1.00 31.59 |
| ATOM | 1948 | O | SER | 268 | 186.135 | 146.449 | 144.110 | 1.00 31.68 |
| ATOM | 1949 | N | THR | 269 | 186.247 | 144.236 | 143.717 | 1.00 32.10 |
| ATOM | 1950 | CA | THR | 269 | 185.903 | 144.350 | 142.306 | 1.00 31.86 |
| ATOM | 1951 | CB | THR | 269 | 186.409 | 143.139 | 141.513 | 1.00 30.91 |
| ATOM | 1952 | OG1 | THR | 269 | 185.939 | 141.936 | 142.131 | 1.00 33.66 |
| ATOM | 1953 | CG2 | THR | 269 | 187.920 | 143.121 | 141.482 | 1.00 31.32 |
| ATOM | 1954 | C | THR | 269 | 184.388 | 144.423 | 142.144 | 1.00 32.28 |
| ATOM | 1955 | O | THR | 269 | 183.879 | 144.556 | 141.034 | 1.00 34.78 |
| ATOM | 1956 | N | LYS | 270 | 183.671 | 144.327 | 143.258 | 1.00 31.21 |
| ATOM | 1957 | CA | LYS | 270 | 182.216 | 144.383 | 143.232 | 1.00 31.00 |
| ATOM | 1958 | CB | LYS | 270 | 181.640 | 143.310 | 144.153 | 1.00 30.84 |
| ATOM | 1959 | CG | LYS | 270 | 180.126 | 143.184 | 144.117 | 1.00 31.73 |
| ATOM | 1960 | CD | LYS | 270 | 179.683 | 142.076 | 145.052 | 1.00 32.76 |
| ATOM | 1961 | CE | LYS | 270 | 178.289 | 141.578 | 144.727 | 1.00 33.30 |
| ATOM | 1962 | NZ | LYS | 270 | 177.787 | 140.719 | 145.837 | 1.00 33.98 |
| ATOM | 1963 | C | LYS | 270 | 181.737 | 145.760 | 143.675 | 1.00 31.18 |
| ATOM | 1964 | O | LYS | 270 | 180.723 | 146.262 | 143.189 | 1.00 32.59 |
| ATOM | 1965 | N | HIS | 271 | 182.475 | 146.356 | 144.608 | 1.00 30.90 |
| ATOM | 1966 | CA | HIS | 271 | 182.168 | 147.679 | 145.141 | 1.00 29.05 |
| ATOM | 1967 | CB | HIS | 271 | 181.245 | 147.565 | 146.357 | 1.00 29.28 |
| ATOM | 1968 | CG | HIS | 271 | 180.656 | 148.870 | 146.790 | 1.00 31.12 |
| ATOM | 1969 | CD2 | HIS | 271 | 179.373 | 149.243 | 147.012 | 1.00 32.38 |
| ATOM | 1970 | ND1 | HIS | 271 | 181.426 | 149.988 | 147.034 | 1.00 32.76 |
| ATOM | 1971 | CE1 | HIS | 271 | 180.642 | 150.992 | 147.388 | 1.00 32.98 |
| ATOM | 1972 | NE2 | HIS | 271 | 179.394 | 150.565 | 147.382 | 1.00 33.22 |
| ATOM | 1973 | C | HIS | 271 | 183.477 | 148.362 | 145.540 | 1.00 28.49 |
| ATOM | 1974 | O | HIS | 271 | 184.044 | 148.079 | 146.597 | 1.00 29.87 |
| ATOM | 1975 | N | ALA | 272 | 183.947 | 149.263 | 144.685 | 1.00 26.31 |
| ATOM | 1976 | CA | ALA | 272 | 185.197 | 149.979 | 144.912 | 1.00 26.03 |
| ATOM | 1977 | CB | ALA | 272 | 185.401 | 151.008 | 143.817 | 1.00 24.06 |
| ATOM | 1978 | C | ALA | 272 | 185.307 | 150.651 | 146.274 | 1.00 26.68 |
| ATOM | 1979 | O | ALA | 272 | 186.408 | 150.976 | 146.721 | 1.00 26.85 |
| ATOM | 1980 | N | GLY | 273 | 184.172 | 150.859 | 146.933 | 1.00 26.94 |
| ATOM | 1981 | CA | GLY | 273 | 184.192 | 151.501 | 148.233 | 1.00 26.43 |
| ATOM | 1982 | C | GLY | 273 | 184.524 | 150.539 | 149.354 | 1.00 28.67 |
| ATOM | 1983 | O | GLY | 273 | 184.695 | 150.952 | 150.502 | 1.00 29.66 |
| ATOM | 1984 | N | PHE | 274 | 184.624 | 149.255 | 149.020 | 1.00 29.20 |
| ATOM | 1985 | CA | PHE | 274 | 184.923 | 148.218 | 150.001 | 1.00 29.51 |
| ATOM | 1986 | CB | PHE | 274 | 183.945 | 147.059 | 149.850 | 1.00 30.84 |
| ATOM | 1987 | CG | PHE | 274 | 182.639 | 147.272 | 150.538 | 1.00 32.43 |
| ATOM | 1988 | CD1 | PHE | 274 | 181.655 | 148.063 | 149.960 | 1.00 32.99 |
| ATOM | 1989 | CD2 | PHE | 274 | 182.378 | 146.661 | 151.755 | 1.00 33.73 |
| ATOM | 1990 | CE1 | PHE | 274 | 180.425 | 148.239 | 150.586 | 1.00 32.87 |

*FIG. 4A - 35*

```
ATOM   1991  CE2  PHE  274      181.154  146.832  152.385  1.00  34.32
ATOM   1992  CZ   PHE  274      180.175  147.621  151.802  1.00  33.04
ATOM   1993  C    PHE  274      186.329  147.659  149.859  1.00  30.03
ATOM   1994  O    PHE  274      186.844  147.529  148.751  1.00  31.27
ATOM   1995  N    MET  275      186.938  147.320  150.991  1.00  29.31
ATOM   1996  CA   MET  275      188.275  146.734  151.013  1.00  27.85
ATOM   1997  CB   MET  275      189.214  147.568  151.895  1.00  22.84
ATOM   1998  CG   MET  275      189.857  148.744  151.160  1.00  17.72
ATOM   1999  SD   MET  275      191.013  149.680  152.142  1.00  13.44
ATOM   2000  CE   MET  275      191.251  151.005  151.118  1.00  11.84
ATOM   2001  C    MET  275      188.079  145.333  151.596  1.00  28.81
ATOM   2002  O    MET  275      187.785  145.183  152.787  1.00  29.35
ATOM   2003  N    VAL  276      188.233  144.313  150.759  1.00  27.58
ATOM   2004  CA   VAL  276      188.022  142.941  151.198  1.00  27.71
ATOM   2005  CB   VAL  276      187.253  142.131  150.125  1.00  28.22
ATOM   2006  CG1  VAL  276      185.793  142.523  150.133  1.00  25.67
ATOM   2007  CG2  VAL  276      187.856  142.375  148.750  1.00  26.93
ATOM   2008  C    VAL  276      189.278  142.164  151.565  1.00  28.57
ATOM   2009  O    VAL  276      190.335  142.315  150.950  1.00  28.50
ATOM   2010  N    ASN  277      189.141  141.330  152.587  1.00  28.63
ATOM   2011  CA   ASN  277      190.228  140.485  153.050  1.00  28.35
ATOM   2012  CB   ASN  277      190.098  140.259  154.552  1.00  27.00
ATOM   2013  CG   ASN  277      191.285  139.540  155.133  1.00  26.43
ATOM   2014  OD1  ASN  277      192.035  138.881  154.415  1.00  26.76
ATOM   2015  ND2  ASN  277      191.466  139.659  156.444  1.00  25.80
ATOM   2016  C    ASN  277      190.055  139.173  152.294  1.00  29.80
ATOM   2017  O    ASN  277      189.404  138.247  152.777  1.00  30.60
ATOM   2018  N    VAL  278      190.630  139.108  151.096  1.00  30.20
ATOM   2019  CA   VAL  278      190.508  137.932  150.242  1.00  30.09
ATOM   2020  CB   VAL  278      190.575  138.322  148.747  1.00  27.73
ATOM   2021  CG1  VAL  278      189.395  139.204  148.384  1.00  27.69
ATOM   2022  CG2  VAL  278      191.884  139.036  148.458  1.00  25.81
ATOM   2023  C    VAL  278      191.540  136.840  150.475  1.00  31.64
ATOM   2024  O    VAL  278      191.295  135.682  150.150  1.00  32.28
ATOM   2025  N    ASP  279      192.689  137.189  151.038  1.00  32.72
ATOM   2026  CA   ASP  279      193.712  136.176  151.241  1.00  33.53
ATOM   2027  CB   ASP  279      194.687  136.202  150.066  1.00  34.74
ATOM   2028  CG   ASP  279      195.659  135.050  150.095  1.00  37.13
ATOM   2029  OD1  ASP  279      195.313  133.993  150.662  1.00  40.49
ATOM   2030  OD2  ASP  279      196.771  135.199  149.552  1.00  37.72
ATOM   2031  C    ASP  279      194.496  136.241  152.546  1.00  33.84
ATOM   2032  O    ASP  279      195.697  136.513  152.541  1.00  33.60
ATOM   2033  N    ASN  280      193.821  135.989  153.663  1.00  34.60
ATOM   2034  CA   ASN  280      194.493  135.988  154.956  1.00  34.64
ATOM   2035  CB   ASN  280      195.428  134.774  155.018  1.00  36.42
ATOM   2036  CG   ASN  280      195.786  134.373  156.431  1.00  38.05
ATOM   2037  OD1  ASN  280      195.039  134.624  157.373  1.00  39.71
ATOM   2038  ND2  ASN  280      196.941  133.740  156.585  1.00  39.52
ATOM   2039  C    ASN  280      195.287  137.280  155.147  1.00  33.29
ATOM   2040  O    ASN  280      196.444  137.251  155.557  1.00  34.36
ATOM   2041  N    GLY  281      194.654  138.410  154.851  1.00  33.29
ATOM   2042  CA   GLY  281      195.317  139.697  154.979  1.00  32.57
ATOM   2043  C    GLY  281      195.447  140.185  156.406  1.00  32.62
ATOM   2044  O    GLY  281      194.952  139.549  157.332  1.00  34.41
ATOM   2045  N    THR  282      196.108  141.324  156.589  1.00  31.67
ATOM   2046  CA   THR  282      196.301  141.876  157.922  1.00  30.82
ATOM   2047  CB   THR  282      197.778  141.840  158.340  1.00  29.91
```

*FIG. 4A - 36*

| | | | | | | | | |
|---|---|---|---|---|---|---|---|---|
| ATOM | 2048 | OG1 | THR | 282 | 198.508 | 142.794 | 157.561 | 1.00 29.67 |
| ATOM | 2049 | CG2 | THR | 282 | 198.365 | 140.457 | 158.131 | 1.00 28.74 |
| ATOM | 2050 | C | THR | 282 | 195.849 | 143.318 | 158.044 | 1.00 31.46 |
| ATOM | 2051 | O | THR | 282 | 195.548 | 143.981 | 157.053 | 1.00 31.87 |
| ATOM | 2052 | N | ALA | 283 | 195.821 | 143.798 | 159.282 | 1.00 31.81 |
| ATOM | 2053 | CA | ALA | 283 | 195.428 | 145.164 | 159.575 | 1.00 31.59 |
| ATOM | 2054 | CB | ALA | 283 | 195.391 | 145.378 | 161.079 | 1.00 31.46 |
| ATOM | 2055 | C | ALA | 283 | 196.447 | 146.091 | 158.939 | 1.00 31.63 |
| ATOM | 2056 | O | ALA | 283 | 196.165 | 147.256 | 158.667 | 1.00 33.07 |
| ATOM | 2057 | N | THR | 284 | 197.639 | 145.557 | 158.703 | 1.00 31.30 |
| ATOM | 2058 | CA | THR | 284 | 198.718 | 146.325 | 158.099 | 1.00 30.50 |
| ATOM | 2059 | CB | THR | 284 | 200.084 | 145.628 | 158.326 | 1.00 30.92 |
| ATOM | 2060 | OG1 | THR | 284 | 200.190 | 145.214 | 159.696 | 1.00 29.40 |
| ATOM | 2061 | CG2 | THR | 284 | 201.230 | 146.576 | 157.999 | 1.00 27.47 |
| ATOM | 2062 | C | THR | 284 | 198.468 | 146.491 | 156.602 | 1.00 29.85 |
| ATOM | 2063 | O | THR | 284 | 198.822 | 147.512 | 156.012 | 1.00 29.04 |
| ATOM | 2064 | N | ASP | 285 | 197.854 | 145.484 | 155.992 | 1.00 29.73 |
| ATOM | 2065 | CA | ASP | 285 | 197.550 | 145.537 | 154.568 | 1.00 29.96 |
| ATOM | 2066 | CB | ASP | 285 | 197.045 | 144.173 | 154.078 | 1.00 30.03 |
| ATOM | 2067 | CG | ASP | 285 | 198.132 | 143.104 | 154.086 | 1.00 30.48 |
| ATOM | 2068 | OD1 | ASP | 285 | 199.331 | 143.458 | 154.046 | 1.00 30.98 |
| ATOM | 2069 | OD2 | ASP | 285 | 197.786 | 141.903 | 154.127 | 1.00 29.93 |
| ATOM | 2070 | C | ASP | 285 | 196.476 | 146.600 | 154.350 | 1.00 29.40 |
| ATOM | 2071 | O | ASP | 285 | 196.576 | 147.416 | 153.439 | 1.00 29.10 |
| ATOM | 2072 | N | TYR | 286 | 195.455 | 146.579 | 155.204 | 1.00 29.85 |
| ATOM | 2073 | CA | TYR | 286 | 194.352 | 147.534 | 155.137 | 1.00 29.67 |
| ATOM | 2074 | CB | TYR | 286 | 193.413 | 147.345 | 156.333 | 1.00 27.64 |
| ATOM | 2075 | CG | TYR | 286 | 192.253 | 146.415 | 156.057 | 1.00 27.67 |
| ATOM | 2076 | CD1 | TYR | 286 | 192.291 | 145.079 | 156.460 | 1.00 25.85 |
| ATOM | 2077 | CE1 | TYR | 286 | 191.236 | 144.214 | 156.179 | 1.00 23.29 |
| ATOM | 2078 | CD2 | TYR | 286 | 191.126 | 146.863 | 155.369 | 1.00 26.76 |
| ATOM | 2079 | CE2 | TYR | 286 | 190.068 | 146.004 | 155.086 | 1.00 24.12 |
| ATOM | 2080 | CZ | TYR | 286 | 190.134 | 144.685 | 155.494 | 1.00 22.76 |
| ATOM | 2081 | OH | TYR | 286 | 189.096 | 143.832 | 155.215 | 1.00 24.14 |
| ATOM | 2082 | C | TYR | 286 | 194.892 | 148.952 | 155.150 | 1.00 30.82 |
| ATOM | 2083 | O | TYR | 286 | 194.623 | 149.744 | 154.251 | 1.00 31.89 |
| ATOM | 2084 | N | GLU | 287 | 195.663 | 149.265 | 156.181 | 1.00 31.87 |
| ATOM | 2085 | CA | GLU | 287 | 196.237 | 150.591 | 156.322 | 1.00 33.28 |
| ATOM | 2086 | CB | GLU | 287 | 197.066 | 150.657 | 157.601 | 1.00 33.30 |
| ATOM | 2087 | CG | GLU | 287 | 197.630 | 152.028 | 157.891 | 1.00 36.22 |
| ATOM | 2088 | CD | GLU | 287 | 197.894 | 152.248 | 159.365 | 1.00 38.88 |
| ATOM | 2089 | OE1 | GLU | 287 | 198.192 | 151.267 | 160.078 | 1.00 40.17 |
| ATOM | 2090 | OE2 | GLU | 287 | 197.802 | 153.410 | 159.809 | 1.00 40.14 |
| ATOM | 2091 | C | GLU | 287 | 197.103 | 150.979 | 155.129 | 1.00 33.95 |
| ATOM | 2092 | O | GLU | 287 | 197.065 | 152.120 | 154.668 | 1.00 34.71 |
| ATOM | 2093 | N | ASN | 288 | 197.887 | 150.029 | 154.635 | 1.00 34.50 |
| ATOM | 2094 | CA | ASN | 288 | 198.761 | 150.285 | 153.501 | 1.00 33.74 |
| ATOM | 2095 | CB | ASN | 288 | 199.686 | 149.089 | 153.274 | 1.00 36.54 |
| ATOM | 2096 | CG | ASN | 288 | 200.825 | 149.034 | 154.280 | 1.00 39.75 |
| ATOM | 2097 | OD1 | ASN | 288 | 201.316 | 147.956 | 154.626 | 1.00 41.60 |
| ATOM | 2098 | ND2 | ASN | 288 | 201.251 | 150.201 | 154.756 | 1.00 39.30 |
| ATOM | 2099 | C | ASN | 288 | 197.939 | 150.553 | 152.250 | 1.00 32.74 |
| ATOM | 2100 | O | ASN | 288 | 198.247 | 151.455 | 151.473 | 1.00 32.74 |
| ATOM | 2101 | N | LEU | 289 | 196.884 | 149.768 | 152.065 | 1.00 31.47 |
| ATOM | 2102 | CA | LEU | 289 | 196.017 | 149.916 | 150.905 | 1.00 30.00 |
| ATOM | 2103 | CB | LEU | 289 | 195.019 | 148.755 | 150.839 | 1.00 28.72 |
| ATOM | 2104 | CG | LEU | 289 | 194.206 | 148.584 | 149.552 | 1.00 28.80 |

*FIG. 4A - 37*

| | | | | | | | | |
|---|---|---|---|---|---|---|---|---|
| ATOM | 2105 | CD1 | LEU | 289 | 195.124 | 148.544 | 148.334 | 1.00 28.25 |
| ATOM | 2106 | CD2 | LEU | 289 | 193.397 | 147.303 | 149.651 | 1.00 26.82 |
| ATOM | 2107 | C | LEU | 289 | 195.268 | 151.240 | 150.956 | 1.00 30.08 |
| ATOM | 2108 | O | LEU | 289 | 195.020 | 151.856 | 149.921 | 1.00 29.90 |
| ATOM | 2109 | N | ILE | 290 | 194.904 | 151.672 | 152.160 | 1.00 29.54 |
| ATOM | 2110 | CA | ILE | 290 | 194.194 | 152.935 | 152.321 | 1.00 30.98 |
| ATOM | 2111 | CB | ILE | 290 | 193.809 | 153.183 | 153.802 | 1.00 29.90 |
| ATOM | 2112 | CG2 | ILE | 290 | 193.629 | 154.670 | 154.060 | 1.00 29.21 |
| ATOM | 2113 | CG1 | ILE | 290 | 192.511 | 152.443 | 154.133 | 1.00 29.16 |
| ATOM | 2114 | CD1 | ILE | 290 | 192.370 | 152.078 | 155.597 | 1.00 28.20 |
| ATOM | 2115 | C | ILE | 290 | 195.121 | 154.048 | 151.848 | 1.00 33.27 |
| ATOM | 2116 | O | ILE | 290 | 194.742 | 154.888 | 151.028 | 1.00 33.84 |
| ATOM | 2117 | N | HIS | 291 | 196.344 | 154.043 | 152.371 | 1.00 33.95 |
| ATOM | 2118 | CA | HIS | 291 | 197.340 | 155.039 | 152.001 | 1.00 33.23 |
| ATOM | 2119 | CB | HIS | 291 | 198.675 | 154.721 | 152.676 | 1.00 34.91 |
| ATOM | 2120 | CG | HIS | 291 | 198.663 | 154.911 | 154.159 | 1.00 37.51 |
| ATOM | 2121 | CD2 | HIS | 291 | 199.487 | 154.439 | 155.125 | 1.00 39.37 |
| ATOM | 2122 | ND1 | HIS | 291 | 197.718 | 155.678 | 154.803 | 1.00 39.28 |
| ATOM | 2123 | CE1 | HIS | 291 | 197.959 | 155.672 | 156.103 | 1.00 40.30 |
| ATOM | 2124 | NE2 | HIS | 291 | 199.027 | 154.927 | 156.323 | 1.00 41.59 |
| ATOM | 2125 | C | HIS | 291 | 197.527 | 155.047 | 150.487 | 1.00 32.35 |
| ATOM | 2126 | O | HIS | 291 | 197.598 | 156.103 | 149.864 | 1.00 32.87 |
| ATOM | 2127 | N | TYR | 292 | 197.595 | 153.859 | 149.898 | 1.00 31.95 |
| ATOM | 2128 | CA | TYR | 292 | 197.792 | 153.731 | 148.460 | 1.00 32.35 |
| ATOM | 2129 | CB | TYR | 292 | 198.090 | 152.278 | 148.092 | 1.00 32.04 |
| ATOM | 2130 | CG | TYR | 292 | 198.309 | 152.084 | 146.615 | 1.00 32.64 |
| ATOM | 2131 | CD1 | TYR | 292 | 199.545 | 152.355 | 146.032 | 1.00 33.35 |
| ATOM | 2132 | CE1 | TYR | 292 | 199.739 | 152.211 | 144.658 | 1.00 32.19 |
| ATOM | 2133 | CD2 | TYR | 292 | 197.270 | 151.663 | 145.790 | 1.00 33.99 |
| ATOM | 2134 | CE2 | TYR | 292 | 197.451 | 151.516 | 144.421 | 1.00 32.38 |
| ATOM | 2135 | CZ | TYR | 292 | 198.685 | 151.791 | 143.862 | 1.00 31.54 |
| ATOM | 2136 | OH | TYR | 292 | 198.853 | 151.630 | 142.508 | 1.00 29.80 |
| ATOM | 2137 | C | TYR | 292 | 196.605 | 154.222 | 147.643 | 1.00 33.22 |
| ATOM | 2138 | O | TYR | 292 | 196.776 | 154.762 | 146.546 | 1.00 33.63 |
| ATOM | 2139 | N | VAL | 293 | 195.400 | 154.021 | 148.166 | 1.00 33.13 |
| ATOM | 2140 | CA | VAL | 293 | 194.200 | 154.461 | 147.467 | 1.00 31.92 |
| ATOM | 2141 | CB | VAL | 293 | 192.928 | 153.852 | 148.108 | 1.00 32.32 |
| ATOM | 2142 | CG1 | VAL | 293 | 191.688 | 154.646 | 147.700 | 1.00 31.58 |
| ATOM | 2143 | CG2 | VAL | 293 | 192.788 | 152.402 | 147.681 | 1.00 30.62 |
| ATOM | 2144 | C | VAL | 293 | 194.134 | 155.983 | 147.517 | 1.00 31.08 |
| ATOM | 2145 | O | VAL | 293 | 193.808 | 156.634 | 146.529 | 1.00 29.34 |
| ATOM | 2146 | N | GLN | 294 | 194.461 | 156.543 | 148.675 | 1.00 30.97 |
| ATOM | 2147 | CA | GLN | 294 | 194.449 | 157.987 | 148.854 | 1.00 32.24 |
| ATOM | 2148 | CB | GLN | 294 | 194.821 | 158.343 | 150.290 | 1.00 29.82 |
| ATOM | 2149 | CG | GLN | 294 | 193.725 | 158.093 | 151.294 | 1.00 30.16 |
| ATOM | 2150 | CD | GLN | 294 | 194.221 | 158.224 | 152.714 | 1.00 31.27 |
| ATOM | 2151 | OE1 | GLN | 294 | 195.314 | 157.769 | 153.039 | 1.00 34.66 |
| ATOM | 2152 | NE2 | GLN | 294 | 193.420 | 158.850 | 153.570 | 1.00 32.25 |
| ATOM | 2153 | C | GLN | 294 | 195.450 | 158.637 | 147.915 | 1.00 34.35 |
| ATOM | 2154 | O | GLN | 294 | 195.187 | 159.691 | 147.336 | 1.00 34.69 |
| ATOM | 2155 | N | LYS | 295 | 196.606 | 157.999 | 147.774 | 1.00 35.96 |
| ATOM | 2156 | CA | LYS | 295 | 197.663 | 158.515 | 146.917 | 1.00 37.25 |
| ATOM | 2157 | CB | LYS | 295 | 198.964 | 157.744 | 147.169 | 1.00 40.57 |
| ATOM | 2158 | CG | LYS | 295 | 200.017 | 157.911 | 146.077 | 1.00 43.85 |
| ATOM | 2159 | CD | LYS | 295 | 201.282 | 157.128 | 146.397 | 1.00 47.02 |
| ATOM | 2160 | CE | LYS | 295 | 202.206 | 157.056 | 145.192 | 1.00 50.19 |
| ATOM | 2161 | NZ | LYS | 295 | 203.244 | 158.124 | 145.230 | 1.00 52.77 |

*FIG. 4A - 38*

```
ATOM   2162  C    LYS  295     197.297 158.435 145.442  1.00 35.73
ATOM   2163  O    LYS  295     197.489 159.390 144.695  1.00 34.90
ATOM   2164  N    THR  296     196.768 157.294 145.023  1.00 34.66
ATOM   2165  CA   THR  296     196.402 157.110 143.628  1.00 34.58
ATOM   2166  CB   THR  296     195.976 155.670 143.366  1.00 33.81
ATOM   2167  OG1  THR  296     196.961 154.785 143.910  1.00 33.20
ATOM   2168  CG2  THR  296     195.832 155.423 141.875  1.00 31.99
ATOM   2169  C    THR  296     195.282 158.037 143.179  1.00 35.95
ATOM   2170  O    THR  296     195.324 158.577 142.076  1.00 36.45
ATOM   2171  N    VAL  297     194.280 158.217 144.032  1.00 36.43
ATOM   2172  CA   VAL  297     193.152 159.077 143.697  1.00 36.41
ATOM   2173  CB   VAL  297     192.022 158.967 144.748  1.00 35.23
ATOM   2174  CG1  VAL  297     191.013 160.087 144.544  1.00 32.54
ATOM   2175  CG2  VAL  297     191.338 157.609 144.641  1.00 32.42
ATOM   2176  C    VAL  297     193.604 160.523 143.610  1.00 37.60
ATOM   2177  O    VAL  297     193.243 161.240 142.681  1.00 37.46
ATOM   2178  N    LYS  298     194.400 160.945 144.586  1.00 39.63
ATOM   2179  CA   LYS  298     194.907 162.310 144.623  1.00 41.88
ATOM   2180  CB   LYS  298     195.812 162.499 145.837  1.00 42.21
ATOM   2181  CG   LYS  298     196.249 163.928 146.053  1.00 43.88
ATOM   2182  CD   LYS  298     197.047 164.054 147.327  1.00 46.54
ATOM   2183  CE   LYS  298     197.471 165.486 147.561  1.00 48.25
ATOM   2184  NZ   LYS  298     198.278 165.590 148.802  1.00 52.18
ATOM   2185  C    LYS  298     195.680 162.638 143.353  1.00 42.87
ATOM   2186  O    LYS  298     195.636 163.761 142.861  1.00 43.61
ATOM   2187  N    GLU  299     196.390 161.651 142.823  1.00 43.86
ATOM   2188  CA   GLU  299     197.166 161.852 141.613  1.00 44.99
ATOM   2189  CB   GLU  299     198.177 160.715 141.443  1.00 46.84
ATOM   2190  CG   GLU  299     199.317 160.749 142.452  1.00 50.50
ATOM   2191  CD   GLU  299     200.213 159.519 142.380  1.00 53.35
ATOM   2192  OE1  GLU  299     199.859 158.555 141.662  1.00 52.98
ATOM   2193  OE2  GLU  299     201.274 159.519 143.046  1.00 53.38
ATOM   2194  C    GLU  299     196.269 161.929 140.386  1.00 45.07
ATOM   2195  O    GLU  299     196.520 162.713 139.478  1.00 46.36
ATOM   2196  N    LYS  300     195.213 161.125 140.367  1.00 45.88
ATOM   2197  CA   LYS  300     194.301 161.098 139.230  1.00 46.96
ATOM   2198  CB   LYS  300     193.506 159.793 139.215  1.00 48.55
ATOM   2199  CG   LYS  300     194.349 158.549 139.370  1.00 52.60
ATOM   2200  CD   LYS  300     194.843 158.052 138.029  1.00 54.60
ATOM   2201  CE   LYS  300     195.765 156.857 138.196  1.00 56.00
ATOM   2202  NZ   LYS  300     195.192 155.648 137.543  1.00 55.96
ATOM   2203  C    LYS  300     193.319 162.255 139.174  1.00 46.85
ATOM   2204  O    LYS  300     193.020 162.760 138.094  1.00 49.16
ATOM   2205  N    PHE  301     192.814 162.673 140.329  1.00 45.28
ATOM   2206  CA   PHE  301     191.835 163.751 140.370  1.00 43.57
ATOM   2207  CB   PHE  301     190.503 163.215 140.889  1.00 45.24
ATOM   2208  CG   PHE  301     189.957 162.076 140.087  1.00 46.10
ATOM   2209  CD1  PHE  301     190.302 160.767 140.391  1.00 46.50
ATOM   2210  CD2  PHE  301     189.094 162.313 139.028  1.00 47.55
ATOM   2211  CE1  PHE  301     189.792 159.708 139.651  1.00 47.98
ATOM   2212  CE2  PHE  301     188.578 161.263 138.281  1.00 48.94
ATOM   2213  CZ   PHE  301     188.928 159.956 138.593  1.00 48.49
ATOM   2214  C    PHE  301     192.235 164.952 141.210  1.00 41.83
ATOM   2215  O    PHE  301     191.547 165.968 141.206  1.00 43.27
ATOM   2216  N    GLY  302     193.339 164.844 141.933  1.00 39.26
ATOM   2217  CA   GLY  302     193.752 165.957 142.761  1.00 37.23
ATOM   2218  C    GLY  302     192.813 166.099 143.940  1.00 36.91
```

*FIG. 4A - 39*

| | | | | | | | | | |
|---|---|---|---|---|---|---|---|---|---|
| ATOM | 2219 | O | GLY | 302 | 192.750 | 167.149 | 144.576 | 1.00 | 37.96 |
| ATOM | 2220 | N | ILE | 303 | 192.071 | 165.036 | 144.229 | 1.00 | 36.55 |
| ATOM | 2221 | CA | ILE | 303 | 191.141 | 165.046 | 145.345 | 1.00 | 35.65 |
| ATOM | 2222 | CB | ILE | 303 | 189.756 | 164.538 | 144.916 | 1.00 | 34.46 |
| ATOM | 2223 | CG2 | ILE | 303 | 188.915 | 164.220 | 146.142 | 1.00 | 33.99 |
| ATOM | 2224 | CG1 | ILE | 303 | 189.059 | 165.601 | 144.068 | 1.00 | 32.08 |
| ATOM | 2225 | CD1 | ILE | 303 | 188.182 | 165.034 | 142.979 | 1.00 | 29.09 |
| ATOM | 2226 | C | ILE | 303 | 191.678 | 164.156 | 146.454 | 1.00 | 36.97 |
| ATOM | 2227 | O | ILE | 303 | 192.140 | 163.046 | 146.202 | 1.00 | 36.79 |
| ATOM | 2228 | N | GLU | 304 | 191.614 | 164.648 | 147.685 | 1.00 | 38.69 |
| ATOM | 2229 | CA | GLU | 304 | 192.108 | 163.901 | 148.837 | 1.00 | 42.13 |
| ATOM | 2230 | CB | GLU | 304 | 192.858 | 164.836 | 149.784 | 1.00 | 45.89 |
| ATOM | 2231 | CG | GLU | 304 | 193.907 | 165.706 | 149.122 | 1.00 | 54.41 |
| ATOM | 2232 | CD | GLU | 304 | 195.137 | 165.890 | 149.992 | 1.00 | 59.06 |
| ATOM | 2233 | OE1 | GLU | 304 | 195.283 | 166.974 | 150.597 | 1.00 | 61.28 |
| ATOM | 2234 | OE2 | GLU | 304 | 195.958 | 164.950 | 150.070 | 1.00 | 61.94 |
| ATOM | 2235 | C | GLU | 304 | 191.001 | 163.208 | 149.618 | 1.00 | 41.47 |
| ATOM | 2236 | O | GLU | 304 | 190.149 | 163.866 | 150.209 | 1.00 | 43.14 |
| ATOM | 2237 | N | LEU | 305 | 191.026 | 161.881 | 149.631 | 1.00 | 39.59 |
| ATOM | 2238 | CA | LEU | 305 | 190.033 | 161.125 | 150.357 | 1.00 | 36.58 |
| ATOM | 2239 | CB | LEU | 305 | 189.939 | 159.702 | 149.814 | 1.00 | 32.97 |
| ATOM | 2240 | CG | LEU | 305 | 189.397 | 159.586 | 148.392 | 1.00 | 30.06 |
| ATOM | 2241 | CD1 | LEU | 305 | 189.663 | 158.196 | 147.838 | 1.00 | 30.29 |
| ATOM | 2242 | CD2 | LEU | 305 | 187.905 | 159.869 | 148.404 | 1.00 | 28.59 |
| ATOM | 2243 | C | LEU | 305 | 190.458 | 161.091 | 151.807 | 1.00 | 36.98 |
| ATOM | 2244 | O | LEU | 305 | 191.609 | 160.835 | 152.147 | 1.00 | 36.42 |
| ATOM | 2245 | N | ASN | 306 | 189.516 | 161.394 | 152.671 | 1.00 | 37.32 |
| ATOM | 2246 | CA | ASN | 306 | 189.814 | 161.349 | 154.070 | 1.00 | 37.00 |
| ATOM | 2247 | CB | ASN | 306 | 189.171 | 162.550 | 154.780 | 1.00 | 38.24 |
| ATOM | 2248 | CG | ASN | 306 | 189.778 | 163.889 | 154.354 | 1.00 | 39.92 |
| ATOM | 2249 | OD1 | ASN | 306 | 189.081 | 164.857 | 153.990 | 1.00 | 41.88 |
| ATOM | 2250 | ND2 | ASN | 306 | 191.085 | 163.952 | 154.423 | 1.00 | 40.93 |
| ATOM | 2251 | C | ASN | 306 | 189.220 | 160.053 | 154.601 | 1.00 | 37.10 |
| ATOM | 2252 | O | ASN | 306 | 188.110 | 159.670 | 154.198 | 1.00 | 37.29 |
| ATOM | 2253 | N | ARG | 307 | 189.944 | 159.376 | 155.495 | 1.00 | 37.28 |
| ATOM | 2254 | CA | ARG | 307 | 189.490 | 158.126 | 156.119 | 1.00 | 37.98 |
| ATOM | 2255 | CB | ARG | 307 | 190.663 | 157.477 | 156.913 | 1.00 | 38.64 |
| ATOM | 2256 | CG | ARG | 307 | 190.647 | 155.956 | 156.901 | 1.00 | 39.08 |
| ATOM | 2257 | CD | ARG | 307 | 191.529 | 155.453 | 158.036 | 1.00 | 40.11 |
| ATOM | 2258 | NE | ARG | 307 | 192.696 | 156.308 | 158.273 | 1.00 | 41.28 |
| ATOM | 2259 | CZ | ARG | 307 | 193.043 | 156.788 | 159.461 | 1.00 | 42.17 |
| ATOM | 2260 | NH1 | ARG | 307 | 192.304 | 156.507 | 160.528 | 1.00 | 42.47 |
| ATOM | 2261 | NH2 | ARG | 307 | 194.129 | 157.547 | 159.600 | 1.00 | 43.97 |
| ATOM | 2262 | C | ARG | 307 | 188.268 | 158.307 | 157.040 | 1.00 | 37.06 |
| ATOM | 2263 | O | ARG | 307 | 188.202 | 159.234 | 157.844 | 1.00 | 37.53 |
| ATOM | 2264 | N | GLU | 308 | 187.280 | 157.436 | 156.935 | 1.00 | 36.87 |
| ATOM | 2265 | CA | GLU | 308 | 186.119 | 157.510 | 157.783 | 1.00 | 38.77 |
| ATOM | 2266 | CB | GLU | 308 | 184.860 | 157.180 | 157.027 | 1.00 | 40.97 |
| ATOM | 2267 | CG | GLU | 308 | 183.719 | 156.687 | 157.922 | 1.00 | 47.07 |
| ATOM | 2268 | CD | GLU | 308 | 183.063 | 157.778 | 158.792 | 1.00 | 51.54 |
| ATOM | 2269 | OE1 | GLU | 308 | 182.126 | 157.437 | 159.561 | 1.00 | 54.63 |
| ATOM | 2270 | OE2 | GLU | 308 | 183.471 | 158.960 | 158.714 | 1.00 | 53.01 |
| ATOM | 2271 | C | GLU | 308 | 186.321 | 156.462 | 158.880 | 1.00 | 38.78 |
| ATOM | 2272 | O | GLU | 308 | 186.072 | 156.745 | 160.034 | 1.00 | 39.09 |
| ATOM | 2273 | N | VAL | 309 | 186.763 | 155.250 | 158.535 | 1.00 | 37.71 |
| ATOM | 2274 | CA | VAL | 309 | 186.960 | 154.170 | 159.516 | 1.00 | 36.70 |
| ATOM | 2275 | CB | VAL | 309 | 187.161 | 152.825 | 158.812 | 1.00 | 36.59 |

*FIG. 4A - 40*

| | | | | | | | |
|---|---|---|---|---|---|---|---|
| ATOM | 2276 | CG1 | VAL | 309 | 188.450 152.855 158.006 | 1.00 | 36.44 |
| ATOM | 2277 | CG2 | VAL | 309 | 187.158 151.703 159.819 | 1.00 | 35.54 |
| ATOM | 2278 | C | VAL | 309 | 188.141 154.405 160.466 | 1.00 | 36.46 |
| ATOM | 2279 | O | VAL | 309 | 189.245 154.758 160.044 | 1.00 | 36.49 |
| ATOM | 2280 | N | ARG | 310 | 187.878 154.214 161.755 | 1.00 | 36.18 |
| ATOM | 2281 | CA | ARG | 310 | 188.868 154.389 162.798 | 1.00 | 36.22 |
| ATOM | 2282 | CB | ARG | 310 | 188.168 154.426 164.165 | 1.00 | 40.27 |
| ATOM | 2283 | CG | ARG | 310 | 188.877 155.245 165.238 | 1.00 | 47.82 |
| ATOM | 2284 | CD | ARG | 310 | 188.059 155.359 166.533 | 1.00 | 52.17 |
| ATOM | 2285 | NE | ARG | 310 | 187.698 154.062 167.107 | 1.00 | 58.10 |
| ATOM | 2286 | CZ | ARG | 310 | 187.717 153.783 168.410 | 1.00 | 60.88 |
| ATOM | 2287 | NH1 | ARG | 310 | 188.078 154.711 169.288 | 1.00 | 63.01 |
| ATOM | 2288 | NH2 | ARG | 310 | 187.362 152.577 168.841 | 1.00 | 60.46 |
| ATOM | 2289 | C | ARG | 310 | 189.853 153.222 162.752 | 1.00 | 33.96 |
| ATOM | 2290 | O | ARG | 310 | 189.468 152.087 162.467 | 1.00 | 33.49 |
| ATOM | 2291 | N | ILE | 311 | 191.125 153.511 163.005 | 1.00 | 31.84 |
| ATOM | 2292 | CA | ILE | 311 | 192.161 152.483 163.037 | 1.00 | 30.77 |
| ATOM | 2293 | CB | ILE | 311 | 193.277 152.739 161.996 | 1.00 | 30.28 |
| ATOM | 2294 | CG2 | ILE | 311 | 194.417 151.746 162.200 | 1.00 | 28.38 |
| ATOM | 2295 | CG1 | ILE | 311 | 192.714 152.593 160.579 | 1.00 | 30.49 |
| ATOM | 2296 | CD1 | ILE | 311 | 193.761 152.674 159.488 | 1.00 | 26.78 |
| ATOM | 2297 | C | ILE | 311 | 192.760 152.582 164.427 | 1.00 | 29.72 |
| ATOM | 2298 | O | ILE | 311 | 193.257 153.635 164.807 | 1.00 | 31.17 |
| ATOM | 2299 | N | ILE | 312 | 192.703 151.498 165.193 | 1.00 | 28.82 |
| ATOM | 2300 | CA | ILE | 312 | 193.236 151.518 166.551 | 1.00 | 27.85 |
| ATOM | 2301 | CB | ILE | 312 | 192.093 151.406 167.586 | 1.00 | 26.31 |
| ATOM | 2302 | CG2 | ILE | 312 | 191.206 152.633 167.504 | 1.00 | 25.22 |
| ATOM | 2303 | CG1 | ILE | 312 | 191.256 150.154 167.315 | 1.00 | 24.57 |
| ATOM | 2304 | CD1 | ILE | 312 | 190.268 149.817 168.421 | 1.00 | 23.56 |
| ATOM | 2305 | C | ILE | 312 | 194.251 150.409 166.799 | 1.00 | 28.22 |
| ATOM | 2306 | O | ILE | 312 | 194.491 149.571 165.936 | 1.00 | 28.80 |
| ATOM | 2307 | N | GLY | 313 | 194.854 150.409 167.980 | 1.00 | 28.37 |
| ATOM | 2308 | CA | GLY | 313 | 195.828 149.382 168.288 | 1.00 | 30.55 |
| ATOM | 2309 | C | GLY | 313 | 197.245 149.844 168.030 | 1.00 | 32.09 |
| ATOM | 2310 | O | GLY | 313 | 197.465 150.953 167.545 | 1.00 | 32.64 |
| ATOM | 2311 | N | GLU | 314 | 198.208 148.984 168.342 | 1.00 | 33.12 |
| ATOM | 2312 | CA | GLU | 314 | 199.618 149.303 168.168 | 1.00 | 34.21 |
| ATOM | 2313 | CB | GLU | 314 | 200.400 148.868 169.405 | 1.00 | 34.20 |
| ATOM | 2314 | CG | GLU | 314 | 199.815 149.352 170.705 | 1.00 | 38.23 |
| ATOM | 2315 | CD | GLU | 314 | 199.846 150.860 170.812 | 1.00 | 42.74 |
| ATOM | 2316 | OE1 | GLU | 314 | 200.725 151.486 170.179 | 1.00 | 44.45 |
| ATOM | 2317 | OE2 | GLU | 314 | 198.989 151.419 171.528 | 1.00 | 44.13 |
| ATOM | 2318 | C | GLU | 314 | 200.251 148.647 166.953 | 1.00 | 35.38 |
| ATOM | 2319 | O | GLU | 314 | 199.843 147.567 166.532 | 1.00 | 35.52 |
| ATOM | 2320 | N | HIS | 315 | 201.258 149.315 166.395 | 1.00 | 36.51 |
| ATOM | 2321 | CA | HIS | 315 | 201.990 148.780 165.255 | 1.00 | 37.34 |
| ATOM | 2322 | CB | HIS | 315 | 202.920 149.840 164.669 | 1.00 | 36.27 |
| ATOM | 2323 | CG | HIS | 315 | 202.217 150.974 163.982 | 1.00 | 35.04 |
| ATOM | 2324 | CD2 | HIS | 315 | 201.959 152.241 164.390 | 1.00 | 34.37 |
| ATOM | 2325 | ND1 | HIS | 315 | 201.722 150.878 162.699 | 1.00 | 35.28 |
| ATOM | 2326 | CE1 | HIS | 315 | 201.192 152.033 162.346 | 1.00 | 34.94 |
| ATOM | 2327 | NE2 | HIS | 315 | 201.321 152.879 163.351 | 1.00 | 34.35 |
| ATOM | 2328 | C | HIS | 315 | 202.805 147.636 165.858 | 1.00 | 38.99 |
| ATOM | 2329 | O | HIS | 315 | 203.248 147.722 167.003 | 1.00 | 39.19 |
| ATOM | 2330 | N | PRO | 316 | 202.990 146.538 165.103 | 1.00 | 41.36 |
| ATOM | 2331 | CD | PRO | 316 | 202.431 146.318 163.771 | 1.00 | 41.52 |
| ATOM | 2332 | CA | PRO | 316 | 203.751 145.373 165.577 | 1.00 | 43.97 |

*FIG. 4A - 41*

```
ATOM   2333  CB   PRO  316      203.637 144.369 164.419  1.00 42.74
ATOM   2334  CG   PRO  316      203.229 145.164 163.254  1.00 42.33
ATOM   2335  C    PRO  316      205.199 145.639 165.940  1.00 46.96
ATOM   2336  O    PRO  316      205.804 146.592 165.437  1.00 47.04
ATOM   2337  N    LYS  317      205.734 144.794 166.842  1.00 50.74
ATOM   2338  CA   LYS  317      207.126 144.839 167.304  1.00 54.77
ATOM   2339  CB   LYS  317      208.046 145.196 166.135  1.00 57.74
ATOM   2340  CG   LYS  317      208.149 144.150 165.057  1.00 62.70
ATOM   2341  CD   LYS  317      209.053 144.611 163.919  1.00 66.95
ATOM   2342  CE   LYS  317      209.057 143.582 162.788  1.00 70.31
ATOM   2343  NZ   LYS  317      209.927 143.979 161.642  1.00 70.87
ATOM   2344  C    LYS  317      207.340 145.819 168.443  1.00 56.09
ATOM   2345  O    LYS  317      207.184 145.485 169.622  1.00 58.24
ATOM   2346  AP   FAD  401      182.636 147.495 166.101  1.00 24.52
ATOM   2347  AO1  FAD  401      182.979 146.348 167.027  1.00 24.47
ATOM   2348  AO2  FAD  401      183.245 147.390 164.719  1.00 25.30
ATOM   2349  AO5* FAD  401      183.047 148.875 166.777  1.00 24.92
ATOM   2350  AC5* FAD  401      182.725 150.102 166.123  1.00 23.41
ATOM   2351  AC1* FAD  401      182.446 151.147 169.364  1.00 24.12
ATOM   2352  AO4* FAD  401      181.922 151.326 168.046  1.00 24.97
ATOM   2353  AC2* FAD  401      183.892 150.727 169.178  1.00 25.08
ATOM   2354  AO2* FAD  401      184.699 151.169 170.269  1.00 25.23
ATOM   2355  AC3* FAD  401      184.254 151.331 167.809  1.00 25.53
ATOM   2356  AO3* FAD  401      184.671 152.732 167.891  1.00 26.72
ATOM   2357  AC4* FAD  401      182.963 151.305 167.026  1.00 25.17
ATOM   2358  AN9  FAD  401      181.517 150.248 170.025  1.00 23.79
ATOM   2359  AC8  FAD  401      181.352 148.988 169.513  1.00 24.28
ATOM   2360  AN7  FAD  401      180.428 148.405 170.475  1.00 22.93
ATOM   2361  AC5  FAD  401      180.186 149.437 171.527  1.00 22.76
ATOM   2362  AC6  FAD  401      179.449 149.625 172.808  1.00 22.97
ATOM   2363  AN6  FAD  401      178.666 148.676 173.318  1.00 22.70
ATOM   2364  AN1  FAD  401      179.569 150.818 173.512  1.00 24.01
ATOM   2365  AC2  FAD  401      180.382 151.791 173.015  1.00 23.88
ATOM   2366  AN3  FAD  401      181.053 151.750 171.896  1.00 25.65
ATOM   2367  AC4  FAD  401      180.910 150.530 171.214  1.00 23.76
ATOM   2368  O3P  FAD  401      181.090 147.612 165.991  1.00 23.11
ATOM   2369  N1   FAD  401      176.858 150.792 158.754  1.00 23.35
ATOM   2370  C2   FAD  401      175.691 151.496 158.557  1.00 22.63
ATOM   2371  O2   FAD  401      175.374 152.413 159.260  1.00 25.16
ATOM   2372  N3   FAD  401      174.889 151.144 157.517  1.00 22.71
ATOM   2373  C4   FAD  401      175.118 150.103 156.691  1.00 22.68
ATOM   2374  O4   FAD  401      174.347 149.768 155.802  1.00 24.70
ATOM   2375  C4A  FAD  401      176.402 149.307 156.860  1.00 21.88
ATOM   2376  N5   FAD  401      176.737 148.251 156.031  1.00 20.90
ATOM   2377  C5A  FAD  401      177.911 147.556 156.176  1.00 21.42
ATOM   2378  C6   FAD  401      178.226 146.516 155.278  1.00 19.27
ATOM   2379  C7   FAD  401      179.409 145.747 155.450  1.00 20.88
ATOM   2380  C7M  FAD  401      179.701 144.659 154.443  1.00 20.59
ATOM   2381  C8   FAD  401      180.270 146.046 156.569  1.00 21.32
ATOM   2382  C8M  FAD  401      181.478 145.142 156.694  1.00 19.07
ATOM   2383  C9   FAD  401      179.930 147.099 157.424  1.00 20.73
ATOM   2384  C9A  FAD  401      178.754 147.888 157.240  1.00 21.78
ATOM   2385  N10  FAD  401      178.403 148.978 158.109  1.00 22.68
ATOM   2386  C10  FAD  401      177.242 149.736 157.968  1.00 23.48
ATOM   2387  C1*  FAD  401      179.274 149.419 159.255  1.00 23.78
ATOM   2388  C2*  FAD  401      179.038 148.602 160.561  1.00 25.38
ATOM   2389  O2*  FAD  401      178.327 147.389 160.373  1.00 23.95
```

*FIG. 4A - 42*

| | | | | | | | |
|---|---|---|---|---|---|---|---|
| ATOM | 2390 | C3* FAD | 401 | 178.355 | 149.494 | 161.637 | 1.00 26.09 |
| ATOM | 2391 | O3* FAD | 401 | 179.108 | 150.649 | 161.959 | 1.00 29.51 |
| ATOM | 2392 | C4* FAD | 401 | 177.985 | 148.690 | 162.915 | 1.00 26.22 |
| ATOM | 2393 | O4* FAD | 401 | 177.020 | 149.359 | 163.705 | 1.00 29.64 |
| ATOM | 2394 | C5* FAD | 401 | 179.210 | 148.302 | 163.764 | 1.00 24.21 |
| ATOM | 2395 | O5* FAD | 401 | 178.796 | 147.363 | 164.769 | 1.00 24.40 |
| ATOM | 2396 | P   FAD | 401 | 179.974 | 146.580 | 165.397 | 1.00 22.09 |
| ATOM | 2397 | O1P FAD | 401 | 179.384 | 145.753 | 166.522 | 1.00 21.03 |
| ATOM | 2398 | O2P FAD | 401 | 180.603 | 145.733 | 164.304 | 1.00 21.01 |
| ATOM | 2399 | OH2 TIP3 | 501 | 164.718 | 135.631 | 159.010 | 1.00 40.48 |
| ATOM | 2400 | OH2 TIP3 | 502 | 155.694 | 136.831 | 153.194 | 1.00 36.75 |
| ATOM | 2401 | OH2 TIP3 | 503 | 162.775 | 150.346 | 151.241 | 1.00 30.51 |
| ATOM | 2402 | OH2 TIP3 | 504 | 181.850 | 158.959 | 161.722 | 1.00 66.31 |
| ATOM | 2403 | OH2 TIP3 | 505 | 178.974 | 134.227 | 177.921 | 1.00 17.95 |
| ATOM | 2404 | OH2 TIP3 | 506 | 176.285 | 138.612 | 170.349 | 1.00 21.57 |
| ATOM | 2405 | OH2 TIP3 | 507 | 162.813 | 137.237 | 171.345 | 1.00 22.11 |
| ATOM | 2406 | OH2 TIP3 | 508 | 160.719 | 146.161 | 161.250 | 1.00 19.48 |
| ATOM | 2407 | OH2 TIP3 | 509 | 178.606 | 146.237 | 171.341 | 1.00 15.91 |
| ATOM | 2408 | OH2 TIP3 | 510 | 195.405 | 158.630 | 157.390 | 1.00 21.33 |
| ATOM | 2409 | OH2 TIP3 | 511 | 193.436 | 131.043 | 156.577 | 1.00 15.64 |
| ATOM | 2410 | OH2 TIP3 | 512 | 177.918 | 140.856 | 162.393 | 1.00 27.30 |
| ATOM | 2411 | OH2 TIP3 | 513 | 166.124 | 166.124 | 166.124 | 1.00 33.40 |
| ATOM | 2412 | OH2 TIP3 | 514 | 170.571 | 145.963 | 180.503 | 1.00 25.24 |
| ATOM | 2413 | OH2 TIP3 | 515 | 182.430 | 136.948 | 155.786 | 1.00 21.00 |
| ATOM | 2414 | OH2 TIP3 | 516 | 175.611 | 153.313 | 189.312 | 1.00 32.77 |
| ATOM | 2415 | OH2 TIP3 | 517 | 162.705 | 150.094 | 157.994 | 1.00 26.25 |
| ATOM | 2416 | OH2 TIP3 | 518 | 162.244 | 144.156 | 160.377 | 1.00 19.26 |
| ATOM | 2417 | OH2 TIP3 | 519 | 176.934 | 134.595 | 173.808 | 1.00 23.67 |
| ATOM | 2418 | OH2 TIP3 | 520 | 176.277 | 141.072 | 167.354 | 1.00 18.25 |
| ATOM | 2419 | OH2 TIP3 | 521 | 162.496 | 148.001 | 149.834 | 1.00 31.27 |
| ATOM | 2420 | OH2 TIP3 | 522 | 197.691 | 144.141 | 142.645 | 1.00 24.00 |
| ATOM | 2421 | OH2 TIP3 | 523 | 165.089 | 149.250 | 180.265 | 1.00 31.17 |
| ATOM | 2422 | OH2 TIP3 | 524 | 170.628 | 161.816 | 161.515 | 1.00 29.20 |
| ATOM | 2423 | OH2 TIP3 | 525 | 184.220 | 141.824 | 170.925 | 1.00 24.43 |
| ATOM | 2424 | OH2 TIP3 | 526 | 192.056 | 157.235 | 163.596 | 1.00 36.12 |
| ATOM | 2425 | OH2 TIP3 | 527 | 172.009 | 147.193 | 185.478 | 1.00 26.98 |
| ATOM | 2426 | OH2 TIP3 | 528 | 152.972 | 138.333 | 165.234 | 1.00 39.09 |
| ATOM | 2427 | OH2 TIP3 | 529 | 170.361 | 163.399 | 163.392 | 1.00 29.14 |
| ATOM | 2428 | OH2 TIP3 | 530 | 169.966 | 142.519 | 153.894 | 1.00 24.95 |
| ATOM | 2429 | OH2 TIP3 | 531 | 186.366 | 152.070 | 173.000 | 1.00 21.92 |
| ATOM | 2430 | OH2 TIP3 | 532 | 165.070 | 159.221 | 154.605 | 1.00 36.56 |
| ATOM | 2431 | OH2 TIP3 | 533 | 169.694 | 155.603 | 155.831 | 1.00 23.04 |
| ATOM | 2432 | OH2 TIP3 | 534 | 172.568 | 135.104 | 166.061 | 1.00 32.28 |
| ATOM | 2433 | OH2 TIP3 | 535 | 190.714 | 131.661 | 174.130 | 1.00 28.29 |
| ATOM | 2434 | OH2 TIP3 | 536 | 191.844 | 134.782 | 169.868 | 1.00 25.25 |
| ATOM | 2435 | OH2 TIP3 | 537 | 169.954 | 144.899 | 153.244 | 1.00 14.59 |
| ATOM | 2436 | OH2 TIP3 | 538 | 178.402 | 137.750 | 168.115 | 1.00 39.68 |
| ATOM | 2437 | OH2 TIP3 | 539 | 186.394 | 133.232 | 189.530 | 1.00 38.93 |
| ATOM | 2438 | OH2 TIP3 | 540 | 174.125 | 136.938 | 170.045 | 1.00 25.19 |
| ATOM | 2439 | OH2 TIP3 | 541 | 180.468 | 136.315 | 173.453 | 1.00 33.42 |
| ATOM | 2440 | OH2 TIP3 | 542 | 189.544 | 154.240 | 178.908 | 1.00 30.86 |
| ATOM | 2441 | OH2 TIP3 | 543 | 170.271 | 165.503 | 170.008 | 1.00 42.72 |
| ATOM | 2442 | OH2 TIP3 | 544 | 157.497 | 136.738 | 157.081 | 1.00 34.31 |
| ATOM | 2443 | OH2 TIP3 | 545 | 172.502 | 144.875 | 179.109 | 1.00 18.73 |
| ATOM | 2444 | OH2 TIP3 | 546 | 186.598 | 136.892 | 177.331 | 1.00 20.39 |
| ATOM | 2445 | OH2 TIP3 | 547 | 151.860 | 143.858 | 165.263 | 1.00 25.28 |
| ATOM | 2446 | OH2 TIP3 | 548 | 172.612 | 138.352 | 168.348 | 1.00 15.94 |

*FIG. 4A - 43*

```
ATOM   2447  OH2  TIP3   549     179.698 138.420 188.484  1.00 32.65
ATOM   2448  OH2  TIP3   550     187.966 148.723 191.840  1.00 47.09
ATOM   2449  OH2  TIP3   551     176.304 162.014 179.188  1.00 35.77
ATOM   2450  OH2  TIP3   552     187.297 153.719 182.668  1.00 26.21
ATOM   2451  OH2  TIP3   553     163.053 153.278 155.870  1.00 46.04
ATOM   2452  OH2  TIP3   554     175.030 147.291 163.950  1.00 27.71
ATOM   2453  OH2  TIP3   555     150.693 144.342 163.141  1.00 44.55
ATOM   2454  OH2  TIP3   556     186.054 134.501 178.472  1.00 26.89
ATOM   2455  OH2  TIP3   557     155.967 139.092 151.536  1.00 23.04
ATOM   2456  OH2  TIP3   558     181.663 141.859 153.739  1.00 36.09
ATOM   2457  OH2  TIP3   559     166.447 137.098 165.886  1.00 22.53
ATOM   2458  OH2  TIP3   560     167.948 153.122 142.920  1.00 33.53
ATOM   2459  OH2  TIP3   561     155.298 137.067 155.622  1.00 26.94
ATOM   2460  OH2  TIP3   562     162.899 140.880 146.567  1.00 37.48
ATOM   2461  OH2  TIP3   563     160.751 141.682 181.568  1.00 41.89
ATOM   2462  OH2  TIP3   564     191.843 133.331 164.195  1.00 49.06
ATOM   2463  OH2  TIP3   565     150.146 140.844 159.949  1.00 37.63
ATOM   2464  OH2  TIP3   566     191.630 150.128 192.173  1.00 48.50
ATOM   2465  OH2  TIP3   567     181.228 135.149 179.298  1.00 26.45
ATOM   2466  OH2  TIP3   568     198.671 137.247 151.296  1.00 54.72
ATOM   2467  OH2  TIP3   569     174.604 134.975 178.845  1.00 18.39
ATOM   2468  OH2  TIP3   570     156.663 146.091 151.436  1.00 33.15
ATOM   2469  OH2  TIP3   571     155.261 148.403 175.845  1.00 43.52
ATOM   2470  OH2  TIP3   572     186.404 167.245 145.384  1.00 39.32
ATOM   2471  OH2  TIP3   573     184.194 137.144 171.633  1.00 34.57
ATOM   2472  OH2  TIP3   574     172.949 137.866 157.835  1.00 47.33
ATOM   2473  OH2  TIP3   575     172.112 139.823 178.560  1.00 43.61
ATOM   2474  OH2  TIP3   576     170.996 139.769 156.564  1.00 30.84
ATOM   2475  OH2  TIP3   577     159.789 138.911 174.005  1.00 35.18
ATOM   2476  OH2  TIP3   578     184.996 141.818 146.356  1.00 29.10
ATOM   2477  OH2  TIP3   579     174.484 141.851 155.036  1.00 34.86
ATOM   2478  OH2  TIP3   580     160.525 135.833 152.088  1.00 41.16
ATOM   2479  OH2  TIP3   581     185.356 148.219 190.444  1.00 31.30
ATOM   2480  OH2  TIP3   582     168.691 157.898 156.506  1.00 33.68
ATOM   2481  OH2  TIP3   583     182.523 139.480 164.738  1.00 46.11
ATOM   2482  OH2  TIP3   584     188.116 150.849 148.860  1.00 29.82
ATOM   2483  OH2  TIP3   585     172.614 142.642 182.766  1.00 30.62
ATOM   2484  OH2  TIP3   586     187.340 141.551 144.941  1.00 29.45
ATOM   2485  OH2  TIP3   587     179.851 140.402 176.675  1.00 21.57
ATOM   2486  OH2  TIP3   588     170.053 146.541 155.532  1.00 18.51
ATOM   2487  OH2  TIP3   589     170.297 158.425 184.156  1.00 50.46
ATOM   2488  OH2  TIP3   590     177.647 135.349 185.923  1.00 21.00
ATOM   2489  OH2  TIP3   591     186.369 164.606 152.768  1.00 45.16
ATOM   2490  OH2  TIP3   592     151.936 142.300 174.417  1.00 38.37
ATOM   2491  OH2  TIP3   593     187.024 162.111 151.698  1.00 27.09
ATOM   2492  OH2  TIP3   594     177.652 138.931 148.044  1.00 35.72
ATOM   2493  OH2  TIP3   595     165.700 147.789 145.637  1.00 30.30
ATOM   2494  OH2  TIP3   596     161.539 136.081 167.334  1.00 31.50
ATOM   2495  OH2  TIP3   597     191.618 168.569 148.085  1.00 40.48
ATOM   2496  OH2  TIP3   598     201.825 142.708 148.241  1.00 34.94
ATOM   2497  OH2  TIP3   599     176.967 165.901 165.917  1.00 53.34
ATOM   2498  OH2  TIP3   600     177.820 153.065 160.930  1.00 34.65
ATOM   2499  OH2  TIP3   601     160.827 156.090 169.229  1.00 50.47
ATOM   2500  OH2  TIP3   602     161.783 158.386 171.397  1.00 35.06
ATOM   2501  OH2  TIP3   603     185.466 155.078 170.377  1.00 54.06
ATOM   2502  OH2  TIP3   604     192.317 149.279 176.059  1.00 29.65
ATOM   2503  OH2  TIP3   605     167.830 139.843 157.780  1.00 29.76
```

*FIG. 4A - 44*

```
ATOM   2504  OH2  TIP3   606    167.002  165.330  168.876  1.00  54.33
ATOM   2505  OH2  TIP3   607    173.781  142.700  162.477  1.00  18.76
ATOM   2506  OH2  TIP3   608    150.214  139.759  156.842  1.00  40.88
ATOM   2507  OH2  TIP3   609    172.766  140.603  181.451  1.00  33.86
ATOM   2508  OH2  TIP3   610    196.655  151.257  140.248  1.00  52.47
ATOM   2509  OH2  TIP3   611    176.641  140.265  156.003  1.00  53.27
ATOM   2510  OH2  TIP3   612    201.279  142.430  156.849  1.00  52.41
ATOM   2511  OH2  TIP3   613    174.505  141.358  190.418  1.00  54.03
ATOM   2512  OH2  TIP3   614    174.880  135.259  176.038  1.00  36.45
ATOM   2513  OH2  TIP3   615    198.414  140.596  179.432  1.00  33.71
ATOM   2514  OH2  TIP3   616    177.721  148.012  143.452  1.00  42.18
ATOM   2515  OH2  TIP3   617    189.140  152.903  171.242  1.00  32.58
ATOM   2516  OH2  TIP3   618    186.566  130.937  178.351  1.00  32.56
ATOM   2517  OH2  TIP3   619    159.446  134.284  159.176  1.00  46.33
ATOM   2518  OH2  TIP3   620    181.172  148.760  190.185  1.00  35.06
ATOM   2519  OH2  TIP3   621    169.663  162.107  168.799  1.00  34.54
ATOM   2520  OH2  TIP3   622    182.810  137.814  166.903  1.00  39.65
ATOM   2521  OH2  TIP3   623    176.539  147.900  190.157  1.00  39.85
ATOM   2522  OH2  TIP3   624    158.151  152.729  162.853  1.00  44.66
ATOM   2523  OH2  TIP3   625    172.567  141.930  185.756  1.00  50.03
ATOM   2524  OH2  TIP3   626    163.184  135.862  163.140  1.00  43.22
ATOM   2525  OH2  TIP3   627    176.615  163.741  167.642  1.00  27.38
ATOM   2526  OH2  TIP3   628    194.401  133.688  175.780  1.00  28.22
ATOM   2527  OH2  TIP3   629    201.412  142.166  170.890  1.00  33.89
ATOM   2528  OH2  TIP3   630    184.927  141.393  167.559  1.00  53.87
ATOM   2529  OH2  TIP3   631    172.703  137.593  162.528  1.00  38.40
ATOM   2530  OH2  TIP3   632    183.072  140.067  145.636  1.00  35.80
ATOM   2531  OH2  TIP3   633    199.140  146.347  161.917  1.00  37.49
ATOM   2532  OH2  TIP3   634    183.919  155.383  161.781  1.00  49.62
ATOM   2533  OH2  TIP3   635    200.016  141.299  168.839  1.00  36.54
ATOM   2534  OH2  TIP3   636    171.244  144.715  186.281  1.00  50.60
ATOM   2535  OH2  TIP3   637    194.629  153.075  169.948  1.00  55.55
ATOM   2536  OH2  TIP3   638    165.880  138.409  149.126  1.00  37.48
ATOM   2537  OH2  TIP3   639    196.827  134.714  161.949  1.00  50.02
ATOM   2538  OH2  TIP3   640    193.031  161.138  147.865  1.00  29.61
ATOM   2539  OH2  TIP3   641    197.255  137.624  148.232  1.00  42.68
ATOM   2540  OH2  TIP3   642    153.314  147.428  157.160  1.00  38.28
ATOM   2541  OH2  TIP3   643    166.350  144.533  144.341  1.00  41.05
ATOM   2542  OH2  TIP3   644    179.534  146.740  189.775  1.00  37.08
ATOM   2543  OH2  TIP3   645    189.807  154.227  181.761  1.00  45.23
ATOM   2544  OH2  TIP3   646    192.668  160.423  156.446  1.00  43.34
ATOM   2545  OH2  TIP3   647    195.196  166.356  138.956  1.00  49.84
ATOM   2546  OH2  TIP3   648    182.632  154.450  179.524  1.00  23.49
ATOM   2547  OH2  TIP3   649    152.229  150.713  159.799  1.00  40.91
ATOM   2548  OH2  TIP3   650    158.329  138.747  150.255  1.00  30.36
ATOM   2549  OH2  TIP3   651    186.866  153.563  180.116  1.00  36.79
ATOM   2550  OH2  TIP3   652    203.868  143.167  168.063  1.00  56.55
ATOM   2551  OH2  TIP3   653    195.219  162.407  149.826  1.00  43.25
ATOM   2552  OH2  TIP3   654    196.473  155.653  158.699  1.00  40.01
ATOM   2553  OH2  TIP3   655    189.381  155.085  173.397  1.00  57.42
ATOM   2554  OH2  TIP3   656    168.274  137.445  148.249  1.00  34.95
ATOM   2555  OH2  TIP3   657    200.848  140.760  173.087  1.00  37.69
ATOM   2556  OH2  TIP3   658    154.311  141.310  172.896  1.00  37.60
ATOM   2557  OH2  TIP3   659    158.855  146.394  149.431  1.00  57.00
ATOM   2558  OH2  TIP3   660    158.521  140.189  147.901  1.00  39.08
ATOM   2559  OH2  TIP3   661    160.018  142.288  147.957  1.00  33.04
ATOM   2560  OH2  TIP3   662    172.368  138.581  152.522  1.00  44.29
```

*FIG. 4A - 45*

| | | | | | | | |
|---|---|---|---|---|---|---|---|
| ATOM | 2561 | OH2 | TIP3 | 663 | 184.228 | 154.080 | 150.884 | 1.00 | 37.23 |
| ATOM | 2562 | OH2 | TIP3 | 664 | 181.206 | 168.306 | 140.323 | 1.00 | 31.45 |
| ATOM | 2563 | OH2 | TIP3 | 665 | 160.409 | 140.163 | 178.444 | 1.00 | 32.96 |
| ATOM | 2564 | OH2 | TIP3 | 666 | 199.568 | 139.377 | 181.925 | 1.00 | 52.62 |
| ATOM | 2565 | OH2 | TIP3 | 667 | 191.382 | 134.028 | 183.572 | 1.00 | 41.66 |
| ATOM | 2566 | OH2 | TIP3 | 668 | 184.436 | 137.519 | 191.447 | 1.00 | 43.79 |
| ATOM | 2567 | OH2 | TIP3 | 669 | 178.374 | 135.898 | 188.671 | 1.00 | 43.20 |
| ATOM | 2568 | OH2 | TIP3 | 670 | 183.806 | 131.563 | 188.317 | 1.00 | 43.72 |
| ATOM | 2569 | OH2 | TIP3 | 671 | 193.770 | 133.162 | 179.393 | 1.00 | 36.96 |
| ATOM | 2570 | OH2 | TIP3 | 672 | 184.023 | 130.982 | 179.135 | 1.00 | 39.13 |
| ATOM | 2571 | OH2 | TIP3 | 673 | 198.610 | 134.833 | 166.943 | 1.00 | 53.06 |
| ATOM | 2572 | OH2 | TIP3 | 674 | 193.276 | 132.962 | 167.829 | 1.00 | 34.69 |
| ATOM | 2573 | OH2 | TIP3 | 675 | 182.845 | 136.338 | 169.404 | 1.00 | 33.69 |
| ATOM | 2574 | OH2 | TIP3 | 676 | 183.678 | 133.867 | 168.291 | 1.00 | 30.26 |
| ATOM | 2575 | OH2 | TIP3 | 677 | 187.924 | 145.137 | 161.762 | 1.00 | 32.55 |
| ATOM | 2576 | OH2 | TIP3 | 678 | 185.527 | 133.082 | 159.873 | 1.00 | 53.76 |
| ATOM | 2577 | OH2 | TIP3 | 679 | 200.295 | 135.102 | 171.318 | 1.00 | 48.87 |
| ATOM | 2578 | OH2 | TIP3 | 680 | 183.015 | 137.826 | 173.645 | 1.00 | 38.41 |
| ATOM | 2579 | OH2 | TIP3 | 681 | 191.371 | 157.642 | 185.202 | 1.00 | 50.04 |
| ATOM | 2580 | OH2 | TIP3 | 682 | 190.346 | 155.074 | 176.819 | 1.00 | 48.94 |
| ATOM | 2581 | OH2 | TIP3 | 683 | 191.387 | 151.626 | 171.800 | 1.00 | 46.21 |
| ATOM | 2582 | OH2 | TIP3 | 684 | 184.160 | 153.292 | 172.301 | 1.00 | 36.14 |
| ATOM | 2583 | OH2 | TIP3 | 685 | 176.335 | 138.341 | 166.131 | 1.00 | 47.48 |
| ATOM | 2584 | OH2 | TIP3 | 686 | 185.544 | 153.295 | 163.102 | 1.00 | 39.20 |
| ATOM | 2585 | OH2 | TIP3 | 687 | 185.378 | 153.868 | 165.475 | 1.00 | 33.75 |
| ATOM | 2586 | OH2 | TIP3 | 688 | 196.470 | 149.905 | 172.674 | 1.00 | 40.26 |
| ATOM | 2587 | OH2 | TIP3 | 689 | 197.519 | 148.877 | 180.225 | 1.00 | 45.10 |
| ATOM | 2588 | OH2 | TIP3 | 690 | 157.663 | 137.764 | 177.084 | 1.00 | 44.66 |
| ATOM | 2589 | OH2 | TIP3 | 691 | 154.161 | 142.574 | 170.171 | 1.00 | 39.92 |
| ATOM | 2590 | OH2 | TIP3 | 692 | 155.780 | 135.284 | 163.896 | 1.00 | 40.11 |
| ATOM | 2591 | OH2 | TIP3 | 693 | 162.873 | 153.888 | 160.325 | 1.00 | 35.74 |
| ATOM | 2592 | OH2 | TIP3 | 694 | 156.945 | 148.220 | 155.837 | 1.00 | 44.01 |
| ATOM | 2593 | OH2 | TIP3 | 695 | 173.592 | 157.866 | 160.331 | 1.00 | 22.66 |
| ATOM | 2594 | OH2 | TIP3 | 696 | 165.378 | 159.504 | 162.474 | 1.00 | 48.64 |
| ATOM | 2595 | OH2 | TIP3 | 697 | 165.717 | 157.839 | 158.982 | 1.00 | 34.76 |
| ATOM | 2596 | OH2 | TIP3 | 698 | 160.959 | 151.556 | 174.170 | 1.00 | 29.58 |
| ATOM | 2597 | OH2 | TIP3 | 699 | 171.949 | 158.554 | 156.600 | 1.00 | 37.64 |
| ATOM | 2598 | OH2 | TIP3 | 700 | 172.489 | 156.172 | 155.827 | 1.00 | 36.55 |
| ATOM | 2599 | OH2 | TIP3 | 701 | 168.421 | 150.212 | 180.499 | 1.00 | 40.71 |
| ATOM | 2600 | OH2 | TIP3 | 702 | 179.757 | 159.519 | 187.348 | 1.00 | 47.90 |
| ATOM | 2601 | OH2 | TIP3 | 703 | 170.245 | 149.061 | 187.445 | 1.00 | 42.46 |
| ATOM | 2602 | OH2 | TIP3 | 704 | 162.039 | 154.412 | 180.938 | 1.00 | 37.52 |
| ATOM | 2603 | OH2 | TIP3 | 705 | 167.213 | 159.759 | 181.231 | 1.00 | 43.00 |
| ATOM | 2604 | OH2 | TIP3 | 706 | 163.330 | 157.489 | 181.439 | 1.00 | 54.58 |
| ATOM | 2605 | OH2 | TIP3 | 707 | 177.897 | 164.518 | 170.176 | 1.00 | 40.57 |
| ATOM | 2606 | OH2 | TIP3 | 708 | 163.891 | 151.565 | 154.190 | 1.00 | 42.37 |
| ATOM | 2607 | OH2 | TIP3 | 709 | 178.067 | 145.290 | 141.361 | 1.00 | 55.87 |
| ATOM | 2608 | OH2 | TIP3 | 710 | 180.452 | 157.464 | 148.802 | 1.00 | 15.02 |
| ATOM | 2609 | OH2 | TIP3 | 711 | 180.772 | 155.328 | 147.088 | 1.00 | 40.23 |
| ATOM | 2610 | OH2 | TIP3 | 712 | 180.197 | 155.404 | 144.710 | 1.00 | 27.00 |
| ATOM | 2611 | OH2 | TIP3 | 713 | 200.689 | 148.777 | 146.209 | 1.00 | 45.42 |
| END | | | | | | | | |

```
INDE  0  1  25 FOBS=    24.4 SIGMA=   2.6 PHAS=   -90.0 FOM=  0.10 TEST= 0
INDE  0  1  27 FOBS=    75.8 SIGMA=   0.9 PHAS=   -90.0 FOM=  0.97 TEST= 1
INDE  0  1  29 FOBS=    77.8 SIGMA=   1.0 PHAS=   -90.0 FOM=  0.83 TEST= 0
INDE  0  1  31 FOBS=   194.8 SIGMA=   0.6 PHAS=    90.0 FOM=  1.00 TEST= 1
INDE  0  1  33 FOBS=    80.1 SIGMA=   0.9 PHAS=    90.0 FOM=  1.00 TEST= 0
INDE  0  1  35 FOBS=   122.6 SIGMA=   0.7 PHAS=    90.0 FOM=  0.09 TEST= 0
INDE  0  1  37 FOBS=    38.6 SIGMA=   2.1 PHAS=   -90.0 FOM=  1.00 TEST= 0
INDE  0  1  39 FOBS=    35.5 SIGMA=   2.6 PHAS=    90.0 FOM=  0.13 TEST= 0
INDE  0  1  41 FOBS=   158.2 SIGMA=   0.8 PHAS=    90.0 FOM=  1.00 TEST= 0
INDE  0  1  43 FOBS=   235.9 SIGMA=   0.6 PHAS=    90.0 FOM=  0.99 TEST= 0
INDE  0  1  45 FOBS=   149.9 SIGMA=   0.9 PHAS=    90.0 FOM=  0.99 TEST= 0
INDE  0  1  47 FOBS=   327.5 SIGMA=   0.8 PHAS=    90.0 FOM=  1.00 TEST= 0
INDE  0  1  49 FOBS=   364.0 SIGMA=   0.6 PHAS=    90.0 FOM=  1.00 TEST= 0
INDE  0  1  51 FOBS=   321.1 SIGMA=   0.8 PHAS=    90.0 FOM=  1.00 TEST= 0
INDE  0  1  53 FOBS=   139.3 SIGMA=   1.7 PHAS=    90.0 FOM=  0.99 TEST= 0
INDE  0  1  55 FOBS=    74.6 SIGMA=   3.0 PHAS=   -90.0 FOM=  1.00 TEST= 0
INDE  0  1  57 FOBS=    44.2 SIGMA=   4.9 PHAS=   -90.0 FOM=  0.55 TEST= 0
INDE  0  1  59 FOBS=   139.2 SIGMA=   2.3 PHAS=    90.0 FOM=  0.99 TEST= 0
INDE  0  2  28 FOBS=     0.0 SIGMA=   8.1 PHAS=     0.0 FOM=  0.00 TEST= 0
INDE  0  2  30 FOBS=     0.0 SIGMA=   9.1 PHAS=     0.0 FOM=  0.00 TEST= 0
INDE  0  2  32 FOBS=    36.8 SIGMA=   1.4 PHAS=     0.0 FOM=  0.77 TEST= 0
INDE  0  2  34 FOBS=    65.7 SIGMA=   1.3 PHAS=  -180.0 FOM=  1.00 TEST= 0
INDE  0  2  36 FOBS=     0.0 SIGMA=  11.1 PHAS=     0.0 FOM=  0.00 TEST= 1
INDE  0  2  38 FOBS=     0.0 SIGMA=  14.3 PHAS=     0.0 FOM=  0.00 TEST= 0
INDE  0  2  40 FOBS=   329.4 SIGMA=   0.6 PHAS=  -180.0 FOM=  1.00 TEST= 0
INDE  0  2  42 FOBS=   184.6 SIGMA=   0.8 PHAS=     0.0 FOM=  0.92 TEST= 0
INDE  0  2  44 FOBS=    40.4 SIGMA=   3.5 PHAS=     0.0 FOM=  1.00 TEST= 0
INDE  0  2  46 FOBS=   177.9 SIGMA=   1.3 PHAS=     0.0 FOM=  1.00 TEST= 0
INDE  0  2  48 FOBS=   194.1 SIGMA=   1.2 PHAS=     0.0 FOM=  1.00 TEST= 0
INDE  0  2  50 FOBS=     0.0 SIGMA=  21.3 PHAS=     0.0 FOM=  0.00 TEST= 1
INDE  0  2  52 FOBS=   351.0 SIGMA=   0.8 PHAS=     0.0 FOM=  1.00 TEST= 0
INDE  0  2  54 FOBS=   177.2 SIGMA=   1.4 PHAS=  -180.0 FOM=  0.99 TEST= 0
INDE  0  2  56 FOBS=   128.8 SIGMA=   1.8 PHAS=  -180.0 FOM=  1.00 TEST= 0
INDE  0  2  58 FOBS=   120.1 SIGMA=   2.0 PHAS=     0.0 FOM=  1.00 TEST= 0
INDE  0  2  60 FOBS=    72.1 SIGMA=   3.1 PHAS=     0.0 FOM=  0.97 TEST= 1
INDE  0  2  62 FOBS=   115.2 SIGMA=   2.8 PHAS=     0.0 FOM=  1.00 TEST= 0
INDE  0  3  37 FOBS=   119.6 SIGMA=   1.3 PHAS=    90.0 FOM=  1.00 TEST= 1
INDE  0  3  39 FOBS=   281.8 SIGMA=   0.8 PHAS=    90.0 FOM=  1.00 TEST= 0
INDE  0  3  41 FOBS=     0.0 SIGMA=  18.5 PHAS=     0.0 FOM=  0.00 TEST= 0
INDE  0  3  43 FOBS=    65.1 SIGMA=   2.9 PHAS=    90.0 FOM=  0.93 TEST= 0
INDE  0  3  45 FOBS=     0.0 SIGMA=  20.7 PHAS=     0.0 FOM=  0.00 TEST= 0
INDE  0  3  47 FOBS=    36.2 SIGMA=   6.4 PHAS=   -90.0 FOM=  0.06 TEST= 1
INDE  0  3  49 FOBS=    39.8 SIGMA=   6.1 PHAS=    90.0 FOM=  0.89 TEST= 0
INDE  0  3  51 FOBS=    63.0 SIGMA=   3.8 PHAS=   -90.0 FOM=  1.00 TEST= 0
INDE  0  3  53 FOBS=     0.0 SIGMA=  21.5 PHAS=     0.0 FOM=  0.00 TEST= 0
INDE  0  3  55 FOBS=    43.3 SIGMA=   5.2 PHAS=   -90.0 FOM=  0.04 TEST= 0
INDE  0  3  57 FOBS=   117.1 SIGMA=   2.0 PHAS=   -90.0 FOM=  0.99 TEST= 1
INDE  0  3  59 FOBS=    74.1 SIGMA=   3.1 PHAS=    90.0 FOM=  1.00 TEST= 0
INDE  0  3  61 FOBS=     0.0 SIGMA=  21.5 PHAS=     0.0 FOM=  0.00 TEST= 0
INDE  0  3  63 FOBS=    27.3 SIGMA=  11.9 PHAS=   -90.0 FOM=  0.45 TEST= 0
INDE  0  3  65 FOBS=    84.5 SIGMA=   4.0 PHAS=    90.0 FOM=  0.97 TEST= 0
INDE  0  4  18 FOBS=    22.2 SIGMA=   5.0 PHAS=     0.0 FOM=  0.28 TEST= 0
INDE  0  4  20 FOBS=   277.5 SIGMA=   0.8 PHAS=  -180.0 FOM=  0.73 TEST= 0
INDE  0  4  22 FOBS=   155.2 SIGMA=   1.6 PHAS=     0.0 FOM=  0.27 TEST= 0
INDE  0  4  38 FOBS=   319.1 SIGMA=   0.7 PHAS=  -180.0 FOM=  0.99 TEST= 0
INDE  0  4  40 FOBS=    14.7 SIGMA=  11.7 PHAS=  -180.0 FOM=  0.04 TEST= 1
INDE  0  4  42 FOBS=   234.4 SIGMA=   1.0 PHAS=     0.0 FOM=  0.12 TEST= 0
INDE  0  4  44 FOBS=   105.6 SIGMA=   2.0 PHAS=     0.0 FOM=  1.00 TEST= 0
INDE  0  4  46 FOBS=    71.8 SIGMA=   3.3 PHAS=     0.0 FOM=  0.99 TEST= 0
INDE  0  4  48 FOBS=    46.8 SIGMA=   5.4 PHAS=     0.0 FOM=  0.33 TEST= 0
INDE  0  4  50 FOBS=    25.5 SIGMA=   9.8 PHAS=  -180.0 FOM=  0.93 TEST= 0
INDE  0  4  52 FOBS=    55.1 SIGMA=   4.4 PHAS=     0.0 FOM=  0.66 TEST= 0
INDE  0  4  54 FOBS=    87.1 SIGMA=   2.7 PHAS=  -180.0 FOM=  0.88 TEST= 0
INDE  0  4  56 FOBS=   203.1 SIGMA=   1.3 PHAS=  -180.0 FOM=  0.00 TEST= 1
INDE  0  4  58 FOBS=   136.1 SIGMA=   1.8 PHAS=     0.0 FOM=  0.99 TEST= 1
INDE  0  4  60 FOBS=   121.1 SIGMA=   2.0 PHAS=     0.0 FOM=  0.62 TEST= 0
INDE  0  4  62 FOBS=    39.5 SIGMA=   7.1 PHAS=     0.0 FOM=  0.49 TEST= 0
INDE  0  4  64 FOBS=     0.0 SIGMA=  22.2 PHAS=     0.0 FOM=  0.00 TEST= 0
INDE  0  4  66 FOBS=    39.0 SIGMA=   8.9 PHAS=     0.0 FOM=  0.37 TEST= 0
INDE  0  4  68 FOBS=     0.0 SIGMA=  25.8 PHAS=     0.0 FOM=  0.00 TEST= 0
```

*FIG. 12A - 1*

| | | | | | | | | | | | |
|---|---|---|---|---|---|---|---|---|---|---|---|
| INDE | 0 | 5 | 19 | FOBS= | 102.4 | SIGMA= | 1.3 | PHAS= | 90.0 | FOM= 0.98 | TEST= 0 |
| INDE | 0 | 5 | 21 | FOBS= | 78.8 | SIGMA= | 1.8 | PHAS= | 90.0 | FOM= 0.58 | TEST= 0 |
| INDE | 0 | 5 | 23 | FOBS= | 280.6 | SIGMA= | 0.9 | PHAS= | 90.0 | FOM= 1.00 | TEST= 0 |
| INDE | 0 | 5 | 25 | FOBS= | 0.0 | SIGMA= | 17.1 | PHAS= | 0.0 | FOM= 0.00 | TEST= 0 |
| INDE | 0 | 5 | 27 | FOBS= | 61.3 | SIGMA= | 2.7 | PHAS= | 90.0 | FOM= 1.00 | TEST= 0 |
| INDE | 0 | 5 | 29 | FOBS= | 17.0 | SIGMA= | 10.0 | PHAS= | -90.0 | FOM= 0.22 | TEST= 0 |
| INDE | 0 | 5 | 31 | FOBS= | 74.7 | SIGMA= | 2.5 | PHAS= | 90.0 | FOM= 1.00 | TEST= 0 |
| INDE | 0 | 5 | 33 | FOBS= | 349.3 | SIGMA= | 1.4 | PHAS= | -90.0 | FOM= 1.00 | TEST= 0 |
| INDE | 0 | 5 | 35 | FOBS= | 64.5 | SIGMA= | 4.7 | PHAS= | 90.0 | FOM= 0.50 | TEST= 0 |
| INDE | 0 | 5 | 39 | FOBS= | 167.6 | SIGMA= | 1.2 | PHAS= | 90.0 | FOM= 0.87 | TEST= 0 |
| INDE | 0 | 5 | 41 | FOBS= | 248.2 | SIGMA= | 0.9 | PHAS= | 90.0 | FOM= 1.00 | TEST= 0 |
| INDE | 0 | 5 | 43 | FOBS= | 231.2 | SIGMA= | 1.0 | PHAS= | -90.0 | FOM= 1.00 | TEST= 0 |
| INDE | 0 | 5 | 45 | FOBS= | 72.6 | SIGMA= | 3.1 | PHAS= | -90.0 | FOM= 0.99 | TEST= 0 |
| INDE | 0 | 5 | 47 | FOBS= | 94.1 | SIGMA= | 2.5 | PHAS= | 90.0 | FOM= 1.00 | TEST= 0 |
| INDE | 0 | 5 | 49 | FOBS= | 213.9 | SIGMA= | 1.2 | PHAS= | 90.0 | FOM= 0.90 | TEST= 0 |
| INDE | 0 | 5 | 51 | FOBS= | 169.2 | SIGMA= | 1.5 | PHAS= | -90.0 | FOM= 1.00 | TEST= 0 |
| INDE | 0 | 5 | 53 | FOBS= | 41.7 | SIGMA= | 5.4 | PHAS= | 90.0 | FOM= 0.09 | TEST= 0 |
| INDE | 0 | 5 | 55 | FOBS= | 0.0 | SIGMA= | 20.3 | PHAS= | 0.0 | FOM= 0.00 | TEST= 0 |
| INDE | 0 | 5 | 57 | FOBS= | 0.0 | SIGMA= | 20.9 | PHAS= | 0.0 | FOM= 0.00 | TEST= 0 |
| INDE | 0 | 5 | 59 | FOBS= | 158.0 | SIGMA= | 1.4 | PHAS= | -90.0 | FOM= 0.98 | TEST= 0 |
| INDE | 0 | 5 | 61 | FOBS= | 107.2 | SIGMA= | 1.9 | PHAS= | -90.0 | FOM= 0.99 | TEST= 1 |
| INDE | 0 | 5 | 63 | FOBS= | 0.0 | SIGMA= | 21.9 | PHAS= | 0.0 | FOM= 0.00 | TEST= 0 |
| INDE | 0 | 5 | 65 | FOBS= | 0.0 | SIGMA= | 21.9 | PHAS= | 0.0 | FOM= 0.00 | TEST= 0 |
| INDE | 0 | 5 | 67 | FOBS= | 0.0 | SIGMA= | 26.7 | PHAS= | 0.0 | FOM= 0.00 | TEST= 0 |
| INDE | 0 | 5 | 69 | FOBS= | 90.7 | SIGMA= | 4.0 | PHAS= | -90.0 | FOM= 1.00 | TEST= 0 |
| INDE | 0 | 5 | 71 | FOBS= | 16.4 | SIGMA= | 21.1 | PHAS= | 90.0 | FOM= 0.15 | TEST= 0 |
| INDE | 0 | 6 | 18 | FOBS= | 0.0 | SIGMA= | 13.7 | PHAS= | 0.0 | FOM= 0.00 | TEST= 0 |
| INDE | 0 | 6 | 20 | FOBS= | 41.4 | SIGMA= | 3.2 | PHAS= | 0.0 | FOM= 0.83 | TEST= 0 |
| INDE | 0 | 6 | 22 | FOBS= | 320.3 | SIGMA= | 1.2 | PHAS= | 0.0 | FOM= 1.00 | TEST= 0 |
| INDE | 0 | 6 | 24 | FOBS= | 144.7 | SIGMA= | 1.2 | PHAS= | -180.0 | FOM= 1.00 | TEST= 1 |
| INDE | 0 | 6 | 26 | FOBS= | 44.2 | SIGMA= | 3.6 | PHAS= | 0.0 | FOM= 1.00 | TEST= 0 |
| INDE | 0 | 6 | 28 | FOBS= | 61.4 | SIGMA= | 2.8 | PHAS= | -180.0 | FOM= 0.81 | TEST= 1 |
| INDE | 0 | 6 | 30 | FOBS= | 28.3 | SIGMA= | 6.4 | PHAS= | -180.0 | FOM= 0.20 | TEST= 0 |
| INDE | 0 | 6 | 32 | FOBS= | 331.3 | SIGMA= | 1.0 | PHAS= | 0.0 | FOM= 1.00 | TEST= 0 |
| INDE | 0 | 6 | 34 | FOBS= | 64.5 | SIGMA= | 3.3 | PHAS= | 0.0 | FOM= 0.63 | TEST= 0 |
| INDE | 0 | 6 | 36 | FOBS= | 150.9 | SIGMA= | 1.7 | PHAS= | 0.0 | FOM= 0.80 | TEST= 0 |
| INDE | 0 | 6 | 38 | FOBS= | 110.9 | SIGMA= | 3.3 | PHAS= | -180.0 | FOM= 0.45 | TEST= 0 |
| INDE | 0 | 6 | 40 | FOBS= | 200.9 | SIGMA= | 1.1 | PHAS= | 0.0 | FOM= 1.00 | TEST= 0 |
| INDE | 0 | 6 | 42 | FOBS= | 0.0 | SIGMA= | 19.2 | PHAS= | 0.0 | FOM= 0.00 | TEST= 0 |
| INDE | 0 | 6 | 44 | FOBS= | 43.4 | SIGMA= | 4.3 | PHAS= | 0.0 | FOM= 0.08 | TEST= 0 |
| INDE | 0 | 6 | 46 | FOBS= | 62.0 | SIGMA= | 3.3 | PHAS= | 0.0 | FOM= 1.00 | TEST= 0 |
| INDE | 0 | 6 | 48 | FOBS= | 14.0 | SIGMA= | 19.2 | PHAS= | -180.0 | FOM= 0.17 | TEST= 0 |
| INDE | 0 | 6 | 50 | FOBS= | 31.1 | SIGMA= | 7.8 | PHAS= | 0.0 | FOM= 0.04 | TEST= 0 |
| INDE | 0 | 6 | 52 | FOBS= | 149.7 | SIGMA= | 1.7 | PHAS= | -180.0 | FOM= 0.97 | TEST= 0 |
| INDE | 0 | 6 | 54 | FOBS= | 0.0 | SIGMA= | 20.5 | PHAS= | 0.0 | FOM= 0.00 | TEST= 0 |
| INDE | 0 | 6 | 56 | FOBS= | 118.0 | SIGMA= | 1.9 | PHAS= | -180.0 | FOM= 0.61 | TEST= 0 |
| INDE | 0 | 6 | 58 | FOBS= | 56.7 | SIGMA= | 3.6 | PHAS= | 0.0 | FOM= 0.70 | TEST= 0 |
| INDE | 0 | 6 | 60 | FOBS= | 70.3 | SIGMA= | 2.9 | PHAS= | -180.0 | FOM= 1.00 | TEST= 0 |
| INDE | 0 | 6 | 62 | FOBS= | 29.4 | SIGMA= | 6.8 | PHAS= | -180.0 | FOM= 0.35 | TEST= 0 |
| INDE | 0 | 6 | 64 | FOBS= | 0.0 | SIGMA= | 22.3 | PHAS= | 0.0 | FOM= 0.00 | TEST= 0 |
| INDE | 0 | 6 | 66 | FOBS= | 36.6 | SIGMA= | 9.8 | PHAS= | 0.0 | FOM= 0.65 | TEST= 0 |
| INDE | 0 | 6 | 68 | FOBS= | 18.6 | SIGMA= | 19.4 | PHAS= | 0.0 | FOM= 0.33 | TEST= 1 |
| INDE | 0 | 6 | 70 | FOBS= | 36.0 | SIGMA= | 10.3 | PHAS= | 0.0 | FOM= 0.28 | TEST= 0 |
| INDE | 0 | 6 | 72 | FOBS= | 57.0 | SIGMA= | 6.4 | PHAS= | 0.0 | FOM= 0.75 | TEST= 0 |
| INDE | 0 | 7 | 17 | FOBS= | 390.2 | SIGMA= | 0.7 | PHAS= | 90.0 | FOM= 1.00 | TEST= 1 |
| INDE | 0 | 7 | 19 | FOBS= | 158.9 | SIGMA= | 0.7 | PHAS= | 90.0 | FOM= 0.93 | TEST= 0 |
| INDE | 0 | 7 | 21 | FOBS= | 323.8 | SIGMA= | 0.7 | PHAS= | -90.0 | FOM= 0.99 | TEST= 0 |
| INDE | 0 | 7 | 23 | FOBS= | 350.5 | SIGMA= | 0.8 | PHAS= | 90.0 | FOM= 1.00 | TEST= 0 |
| INDE | 0 | 7 | 25 | FOBS= | 50.9 | SIGMA= | 3.0 | PHAS= | 90.0 | FOM= 0.54 | TEST= 0 |
| INDE | 0 | 7 | 27 | FOBS= | 104.0 | SIGMA= | 1.8 | PHAS= | -90.0 | FOM= 1.00 | TEST= 0 |
| INDE | 0 | 7 | 29 | FOBS= | 24.2 | SIGMA= | 7.0 | PHAS= | -90.0 | FOM= 0.12 | TEST= 0 |
| INDE | 0 | 7 | 31 | FOBS= | 111.5 | SIGMA= | 1.8 | PHAS= | 90.0 | FOM= 1.00 | TEST= 0 |
| INDE | 0 | 7 | 33 | FOBS= | 121.4 | SIGMA= | 1.8 | PHAS= | -90.0 | FOM= 1.00 | TEST= 0 |
| INDE | 0 | 7 | 35 | FOBS= | 160.6 | SIGMA= | 1.6 | PHAS= | -90.0 | FOM= 0.88 | TEST= 1 |
| INDE | 0 | 7 | 37 | FOBS= | 39.6 | SIGMA= | 6.0 | PHAS= | -90.0 | FOM= 0.96 | TEST= 0 |
| INDE | 0 | 7 | 39 | FOBS= | 0.0 | SIGMA= | 22.8 | PHAS= | 0.0 | FOM= 0.00 | TEST= 0 |
| INDE | 0 | 7 | 41 | FOBS= | 101.1 | SIGMA= | 3.0 | PHAS= | -90.0 | FOM= 1.00 | TEST= 0 |
| INDE | 0 | 7 | 43 | FOBS= | 240.7 | SIGMA= | 1.1 | PHAS= | -90.0 | FOM= 0.97 | TEST= 0 |
| INDE | 0 | 7 | 45 | FOBS= | 128.5 | SIGMA= | 1.6 | PHAS= | -90.0 | FOM= 0.88 | TEST= 0 |
| INDE | 0 | 7 | 47 | FOBS= | 280.0 | SIGMA= | 0.9 | PHAS= | 90.0 | FOM= 1.00 | TEST= 0 |

*FIG. 12A - 2*

| | | | | | | | | | | | |
|---|---|---|---|---|---|---|---|---|---|---|---|
| INDE | 0 | 7 | 49 | FOBS= | 201.9 | SIGMA= | 1.3 | PHAS= | 90.0 | FOM= | 0.93 | TEST= 1
| INDE | 0 | 7 | 51 | FOBS= | 42.5 | SIGMA= | 6.5 | PHAS= | -90.0 | FOM= | 0.19 | TEST= 0
| INDE | 0 | 7 | 53 | FOBS= | 90.8 | SIGMA= | 2.5 | PHAS= | 90.0 | FOM= | 0.98 | TEST= 0
| INDE | 0 | 7 | 55 | FOBS= | 81.5 | SIGMA= | 2.7 | PHAS= | 90.0 | FOM= | 0.17 | TEST= 0
| INDE | 0 | 7 | 57 | FOBS= | 159.1 | SIGMA= | 1.4 | PHAS= | 90.0 | FOM= | 1.00 | TEST= 0
| INDE | 0 | 7 | 59 | FOBS= | 13.1 | SIGMA= | 17.4 | PHAS= | -90.0 | FOM= | 0.11 | TEST= 0
| INDE | 0 | 7 | 61 | FOBS= | 132.2 | SIGMA= | 1.6 | PHAS= | -90.0 | FOM= | 1.00 | TEST= 0
| INDE | 0 | 7 | 63 | FOBS= | 41.1 | SIGMA= | 6.2 | PHAS= | 90.0 | FOM= | 0.25 | TEST= 1
| INDE | 0 | 7 | 65 | FOBS= | 13.0 | SIGMA= | 22.5 | PHAS= | 90.0 | FOM= | 0.21 | TEST= 0
| INDE | 0 | 7 | 67 | FOBS= | 0.0 | SIGMA= | 26.6 | PHAS= | 0.0 | FOM= | 0.00 | TEST= 0
| INDE | 0 | 7 | 69 | FOBS= | 63.6 | SIGMA= | 5.7 | PHAS= | -90.0 | FOM= | 0.90 | TEST= 0
| INDE | 0 | 7 | 71 | FOBS= | 89.9 | SIGMA= | 4.2 | PHAS= | -90.0 | FOM= | 0.74 | TEST= 0
| INDE | 0 | 7 | 73 | FOBS= | 42.3 | SIGMA= | 9.0 | PHAS= | -90.0 | FOM= | 0.71 | TEST= 0
| INDE | 0 | 7 | 75 | FOBS= | 0.0 | SIGMA= | 27.5 | PHAS= | 0.0 | FOM= | 0.00 | TEST= 0
| INDE | 0 | 8 | 18 | FOBS= | 437.1 | SIGMA= | 0.4 | PHAS= | 0.0 | FOM= | 1.00 | TEST= 0
| INDE | 0 | 8 | 20 | FOBS= | 429.7 | SIGMA= | 0.8 | PHAS= | 0.0 | FOM= | 1.00 | TEST= 0
| INDE | 0 | 8 | 22 | FOBS= | 206.4 | SIGMA= | 0.8 | PHAS= | 0.0 | FOM= | 1.00 | TEST= 0
| INDE | 0 | 8 | 24 | FOBS= | 196.7 | SIGMA= | 0.8 | PHAS= | -180.0 | FOM= | 0.91 | TEST= 1
| INDE | 0 | 8 | 26 | FOBS= | 19.5 | SIGMA= | 8.1 | PHAS= | 0.0 | FOM= | 0.94 | TEST= 0
| INDE | 0 | 8 | 28 | FOBS= | 159.3 | SIGMA= | 1.3 | PHAS= | -180.0 | FOM= | 1.00 | TEST= 0
| INDE | 0 | 8 | 30 | FOBS= | 81.1 | SIGMA= | 2.4 | PHAS= | 0.0 | FOM= | 1.00 | TEST= 0
| INDE | 0 | 8 | 32 | FOBS= | 63.0 | SIGMA= | 3.2 | PHAS= | -180.0 | FOM= | 0.20 | TEST= 0
| INDE | 0 | 8 | 34 | FOBS= | 135.7 | SIGMA= | 1.7 | PHAS= | -180.0 | FOM= | 0.98 | TEST= 0
| INDE | 0 | 8 | 36 | FOBS= | 25.8 | SIGMA= | 8.8 | PHAS= | -180.0 | FOM= | 0.17 | TEST= 0
| INDE | 0 | 8 | 38 | FOBS= | 126.0 | SIGMA= | 2.2 | PHAS= | -180.0 | FOM= | 0.99 | TEST= 1
| INDE | 0 | 8 | 40 | FOBS= | 80.5 | SIGMA= | 3.6 | PHAS= | -180.0 | FOM= | 1.00 | TEST= 0
| INDE | 0 | 8 | 42 | FOBS= | 129.3 | SIGMA= | 2.5 | PHAS= | -180.0 | FOM= | 0.99 | TEST= 0
| INDE | 0 | 8 | 44 | FOBS= | 162.6 | SIGMA= | 1.3 | PHAS= | 0.0 | FOM= | 1.00 | TEST= 0
| INDE | 0 | 8 | 46 | FOBS= | 122.7 | SIGMA= | 1.9 | PHAS= | 0.0 | FOM= | 1.00 | TEST= 0
| INDE | 0 | 8 | 48 | FOBS= | 282.1 | SIGMA= | 1.4 | PHAS= | 0.0 | FOM= | 1.00 | TEST= 0
| INDE | 0 | 8 | 50 | FOBS= | 3.4 | SIGMA= | 79.6 | PHAS= | 0.0 | FOM= | 0.03 | TEST= 0
| INDE | 0 | 8 | 52 | FOBS= | 111.4 | SIGMA= | 2.3 | PHAS= | 0.0 | FOM= | 1.00 | TEST= 0
| INDE | 0 | 8 | 54 | FOBS= | 324.0 | SIGMA= | 1.2 | PHAS= | 0.0 | FOM= | 1.00 | TEST= 0
| INDE | 0 | 8 | 56 | FOBS= | 100.9 | SIGMA= | 2.2 | PHAS= | 0.0 | FOM= | 0.98 | TEST= 0
| INDE | 0 | 8 | 58 | FOBS= | 117.5 | SIGMA= | 1.9 | PHAS= | 0.0 | FOM= | 1.00 | TEST= 0
| INDE | 0 | 8 | 60 | FOBS= | 72.6 | SIGMA= | 2.9 | PHAS= | -180.0 | FOM= | 0.80 | TEST= 0
| INDE | 0 | 8 | 62 | FOBS= | 20.7 | SIGMA= | 12.4 | PHAS= | -180.0 | FOM= | 0.31 | TEST= 0
| INDE | 0 | 8 | 64 | FOBS= | 58.5 | SIGMA= | 4.5 | PHAS= | 0.0 | FOM= | 0.13 | TEST= 0
| INDE | 0 | 8 | 66 | FOBS= | 75.0 | SIGMA= | 5.0 | PHAS= | -180.0 | FOM= | 0.80 | TEST= 0
| INDE | 0 | 8 | 68 | FOBS= | 0.0 | SIGMA= | 27.3 | PHAS= | 0.0 | FOM= | 0.00 | TEST= 0
| INDE | 0 | 8 | 70 | FOBS= | 0.0 | SIGMA= | 27.2 | PHAS= | 0.0 | FOM= | 0.00 | TEST= 0
| INDE | 0 | 8 | 72 | FOBS= | 37.2 | SIGMA= | 9.9 | PHAS= | 0.0 | FOM= | 0.19 | TEST= 0
| INDE | 0 | 8 | 74 | FOBS= | 0.0 | SIGMA= | 27.8 | PHAS= | 0.0 | FOM= | 0.00 | TEST= 0
| INDE | 0 | 8 | 76 | FOBS= | 0.0 | SIGMA= | 28.4 | PHAS= | 0.0 | FOM= | 0.00 | TEST= 0
| INDE | 0 | 9 | 17 | FOBS= | 62.8 | SIGMA= | 1.4 | PHAS= | 90.0 | FOM= | 0.14 | TEST= 0
| INDE | 0 | 9 | 19 | FOBS= | 475.5 | SIGMA= | 0.5 | PHAS= | -90.0 | FOM= | 1.00 | TEST= 0
| INDE | 0 | 9 | 21 | FOBS= | 521.8 | SIGMA= | 0.6 | PHAS= | 90.0 | FOM= | 1.00 | TEST= 0
| INDE | 0 | 9 | 23 | FOBS= | 270.4 | SIGMA= | 0.8 | PHAS= | 90.0 | FOM= | 1.00 | TEST= 0
| INDE | 0 | 9 | 25 | FOBS= | 353.2 | SIGMA= | 0.9 | PHAS= | 90.0 | FOM= | 1.00 | TEST= 0
| INDE | 0 | 9 | 27 | FOBS= | 11.4 | SIGMA= | 14.3 | PHAS= | -90.0 | FOM= | 0.03 | TEST= 0
| INDE | 0 | 9 | 29 | FOBS= | 69.5 | SIGMA= | 2.6 | PHAS= | -90.0 | FOM= | 0.98 | TEST= 0
| INDE | 0 | 9 | 31 | FOBS= | 118.8 | SIGMA= | 1.8 | PHAS= | 90.0 | FOM= | 1.00 | TEST= 0
| INDE | 0 | 9 | 33 | FOBS= | 76.9 | SIGMA= | 2.7 | PHAS= | -90.0 | FOM= | 0.91 | TEST= 0
| INDE | 0 | 9 | 35 | FOBS= | 190.7 | SIGMA= | 1.4 | PHAS= | -90.0 | FOM= | 1.00 | TEST= 0
| INDE | 0 | 9 | 37 | FOBS= | 120.7 | SIGMA= | 2.1 | PHAS= | 90.0 | FOM= | 0.22 | TEST= 0
| INDE | 0 | 9 | 39 | FOBS= | 186.3 | SIGMA= | 1.7 | PHAS= | 90.0 | FOM= | 0.98 | TEST= 0
| INDE | 0 | 9 | 41 | FOBS= | 40.8 | SIGMA= | 7.4 | PHAS= | 90.0 | FOM= | 0.29 | TEST= 0
| INDE | 0 | 9 | 43 | FOBS= | 0.0 | SIGMA= | 25.6 | PHAS= | 0.0 | FOM= | 0.00 | TEST= 0
| INDE | 0 | 9 | 45 | FOBS= | 28.6 | SIGMA= | 7.5 | PHAS= | -90.0 | FOM= | 0.20 | TEST= 0
| INDE | 0 | 9 | 47 | FOBS= | 40.7 | SIGMA= | 6.2 | PHAS= | -90.0 | FOM= | 0.99 | TEST= 0
| INDE | 0 | 9 | 49 | FOBS= | 164.9 | SIGMA= | 1.7 | PHAS= | -90.0 | FOM= | 0.92 | TEST= 0
| INDE | 0 | 9 | 51 | FOBS= | 85.4 | SIGMA= | 3.0 | PHAS= | 90.0 | FOM= | 0.76 | TEST= 0
| INDE | 0 | 9 | 53 | FOBS= | 207.0 | SIGMA= | 1.2 | PHAS= | -90.0 | FOM= | 1.00 | TEST= 1
| INDE | 0 | 9 | 55 | FOBS= | 315.5 | SIGMA= | 0.9 | PHAS= | -90.0 | FOM= | 1.00 | TEST= 0
| INDE | 0 | 9 | 57 | FOBS= | 110.7 | SIGMA= | 2.1 | PHAS= | -90.0 | FOM= | 1.00 | TEST= 0
| INDE | 0 | 9 | 59 | FOBS= | 29.4 | SIGMA= | 9.1 | PHAS= | -90.0 | FOM= | 0.04 | TEST= 0
| INDE | 0 | 9 | 61 | FOBS= | 173.2 | SIGMA= | 1.4 | PHAS= | 90.0 | FOM= | 0.99 | TEST= 0
| INDE | 0 | 9 | 63 | FOBS= | 162.2 | SIGMA= | 1.7 | PHAS= | 90.0 | FOM= | 1.00 | TEST= 0
| INDE | 0 | 9 | 65 | FOBS= | 0.0 | SIGMA= | 24.6 | PHAS= | 0.0 | FOM= | 0.00 | TEST= 0
| INDE | 0 | 9 | 67 | FOBS= | 0.0 | SIGMA= | 27.4 | PHAS= | 0.0 | FOM= | 0.00 | TEST= 0

*FIG. 12A - 3*

| | | | | | | | | | | | |
|---|---|---|---|---|---|---|---|---|---|---|---|
| INDE | 0 | 9 | 69 | FOBS= | 30.4 | SIGMA= | 12.4 | PHAS= | 90.0 | FOM= | 0.32 | TEST= 0
| INDE | 0 | 9 | 71 | FOBS= | 19.2 | SIGMA= | 20.0 | PHAS= | -90.0 | FOM= | 0.22 | TEST= 0
| INDE | 0 | 9 | 73 | FOBS= | 57.0 | SIGMA= | 6.7 | PHAS= | -90.0 | FOM= | 0.92 | TEST= 0
| INDE | 0 | 9 | 75 | FOBS= | 34.0 | SIGMA= | 11.7 | PHAS= | 90.0 | FOM= | 0.71 | TEST= 0
| INDE | 0 | 9 | 77 | FOBS= | 66.5 | SIGMA= | 6.4 | PHAS= | 90.0 | FOM= | 0.92 | TEST= 0
| INDE | 0 | 10 | 16 | FOBS= | 68.6 | SIGMA= | 1.2 | PHAS= | -180.0 | FOM= | 1.00 | TEST= 0
| INDE | 0 | 10 | 18 | FOBS= | 101.6 | SIGMA= | 0.6 | PHAS= | -180.0 | FOM= | 0.87 | TEST= 0
| INDE | 0 | 10 | 20 | FOBS= | 225.8 | SIGMA= | 0.7 | PHAS= | 0.0 | FOM= | 0.93 | TEST= 0
| INDE | 0 | 10 | 22 | FOBS= | 201.2 | SIGMA= | 0.5 | PHAS= | -180.0 | FOM= | 0.99 | TEST= 0
| INDE | 0 | 10 | 24 | FOBS= | 75.8 | SIGMA= | 1.0 | PHAS= | 0.0 | FOM= | 1.00 | TEST= 0
| INDE | 0 | 10 | 26 | FOBS= | 174.4 | SIGMA= | 1.0 | PHAS= | 0.0 | FOM= | 1.00 | TEST= 0
| INDE | 0 | 10 | 28 | FOBS= | 59.9 | SIGMA= | 2.1 | PHAS= | -180.0 | FOM= | 0.54 | TEST= 0
| INDE | 0 | 10 | 30 | FOBS= | 0.0 | SIGMA= | 18.7 | PHAS= | 0.0 | FOM= | 0.00 | TEST= 0
| INDE | 0 | 10 | 32 | FOBS= | 123.5 | SIGMA= | 1.8 | PHAS= | -180.0 | FOM= | 1.00 | TEST= 0
| INDE | 0 | 10 | 34 | FOBS= | 104.4 | SIGMA= | 2.2 | PHAS= | -180.0 | FOM= | 0.99 | TEST= 0
| INDE | 0 | 10 | 36 | FOBS= | 211.0 | SIGMA= | 1.4 | PHAS= | -180.0 | FOM= | 0.99 | TEST= 0
| INDE | 0 | 10 | 38 | FOBS= | 312.5 | SIGMA= | 1.2 | PHAS= | 0.0 | FOM= | 0.25 | TEST= 0
| INDE | 0 | 10 | 40 | FOBS= | 255.9 | SIGMA= | 1.4 | PHAS= | 0.0 | FOM= | 1.00 | TEST= 0
| INDE | 0 | 10 | 42 | FOBS= | 36.6 | SIGMA= | 8.5 | PHAS= | -180.0 | FOM= | 0.01 | TEST= 0
| INDE | 0 | 10 | 44 | FOBS= | 0.0 | SIGMA= | 26.4 | PHAS= | 0.0 | FOM= | 0.00 | TEST= 0
| INDE | 0 | 10 | 46 | FOBS= | 170.7 | SIGMA= | 1.4 | PHAS= | -180.0 | FOM= | 1.00 | TEST= 0
| INDE | 0 | 10 | 48 | FOBS= | 116.8 | SIGMA= | 2.3 | PHAS= | -180.0 | FOM= | 1.00 | TEST= 0
| INDE | 0 | 10 | 50 | FOBS= | 36.1 | SIGMA= | 8.9 | PHAS= | -180.0 | FOM= | 0.10 | TEST= 0
| INDE | 0 | 10 | 52 | FOBS= | 0.0 | SIGMA= | 25.5 | PHAS= | 0.0 | FOM= | 0.00 | TEST= 0
| INDE | 0 | 10 | 54 | FOBS= | 35.5 | SIGMA= | 6.4 | PHAS= | 0.0 | FOM= | 0.13 | TEST= 0
| INDE | 0 | 10 | 56 | FOBS= | 164.4 | SIGMA= | 1.5 | PHAS= | -180.0 | FOM= | 1.00 | TEST= 0
| INDE | 0 | 10 | 58 | FOBS= | 209.4 | SIGMA= | 1.2 | PHAS= | -180.0 | FOM= | 1.00 | TEST= 0
| INDE | 0 | 10 | 60 | FOBS= | 147.7 | SIGMA= | 1.6 | PHAS= | -180.0 | FOM= | 1.00 | TEST= 0
| INDE | 0 | 10 | 62 | FOBS= | 173.4 | SIGMA= | 1.4 | PHAS= | 0.0 | FOM= | 0.77 | TEST= 1
| INDE | 0 | 10 | 64 | FOBS= | 49.1 | SIGMA= | 5.4 | PHAS= | -180.0 | FOM= | 0.14 | TEST= 0
| INDE | 0 | 10 | 66 | FOBS= | 132.6 | SIGMA= | 3.0 | PHAS= | 0.0 | FOM= | 0.36 | TEST= 0
| INDE | 0 | 10 | 68 | FOBS= | 51.6 | SIGMA= | 7.4 | PHAS= | -180.0 | FOM= | 0.01 | TEST= 0
| INDE | 0 | 10 | 70 | FOBS= | 147.4 | SIGMA= | 2.9 | PHAS= | 0.0 | FOM= | 1.00 | TEST= 0
| INDE | 0 | 10 | 72 | FOBS= | 31.3 | SIGMA= | 12.4 | PHAS= | 0.0 | FOM= | 0.63 | TEST= 0
| INDE | 0 | 10 | 74 | FOBS= | 0.0 | SIGMA= | 28.3 | PHAS= | 0.0 | FOM= | 0.00 | TEST= 1
| INDE | 0 | 10 | 76 | FOBS= | 96.8 | SIGMA= | 4.3 | PHAS= | 0.0 | FOM= | 1.00 | TEST= 0
| INDE | 0 | 11 | 15 | FOBS= | 260.2 | SIGMA= | 0.8 | PHAS= | 90.0 | FOM= | 0.96 | TEST= 0
| INDE | 0 | 11 | 17 | FOBS= | 262.7 | SIGMA= | 0.8 | PHAS= | 90.0 | FOM= | 1.00 | TEST= 0
| INDE | 0 | 11 | 19 | FOBS= | 97.4 | SIGMA= | 0.7 | PHAS= | -90.0 | FOM= | 0.04 | TEST= 0
| INDE | 0 | 11 | 21 | FOBS= | 27.2 | SIGMA= | 2.5 | PHAS= | -90.0 | FOM= | 0.74 | TEST= 0
| INDE | 0 | 11 | 23 | FOBS= | 185.9 | SIGMA= | 0.8 | PHAS= | 90.0 | FOM= | 1.00 | TEST= 0
| INDE | 0 | 11 | 25 | FOBS= | 166.4 | SIGMA= | 0.9 | PHAS= | 90.0 | FOM= | 1.00 | TEST= 0
| INDE | 0 | 11 | 27 | FOBS= | 41.1 | SIGMA= | 1.7 | PHAS= | -90.0 | FOM= | 1.00 | TEST= 0
| INDE | 0 | 11 | 29 | FOBS= | 18.2 | SIGMA= | 6.9 | PHAS= | -90.0 | FOM= | 0.97 | TEST= 0
| INDE | 0 | 11 | 31 | FOBS= | 90.3 | SIGMA= | 1.9 | PHAS= | 90.0 | FOM= | 1.00 | TEST= 1
| INDE | 0 | 11 | 33 | FOBS= | 56.1 | SIGMA= | 3.7 | PHAS= | 90.0 | FOM= | 0.54 | TEST= 0
| INDE | 0 | 11 | 35 | FOBS= | 75.2 | SIGMA= | 3.1 | PHAS= | -90.0 | FOM= | 0.53 | TEST= 0
| INDE | 0 | 11 | 37 | FOBS= | 65.6 | SIGMA= | 3.8 | PHAS= | 90.0 | FOM= | 0.88 | TEST= 0
| INDE | 0 | 11 | 39 | FOBS= | 72.4 | SIGMA= | 3.8 | PHAS= | -90.0 | FOM= | 1.00 | TEST= 0
| INDE | 0 | 11 | 41 | FOBS= | 213.4 | SIGMA= | 1.7 | PHAS= | 90.0 | FOM= | 0.19 | TEST= 1
| INDE | 0 | 11 | 43 | FOBS= | 0.0 | SIGMA= | 25.4 | PHAS= | 0.0 | FOM= | 0.00 | TEST= 0
| INDE | 0 | 11 | 45 | FOBS= | 361.9 | SIGMA= | 1.4 | PHAS= | 90.0 | FOM= | 1.00 | TEST= 0
| INDE | 0 | 11 | 47 | FOBS= | 247.7 | SIGMA= | 1.1 | PHAS= | 90.0 | FOM= | 1.00 | TEST= 1
| INDE | 0 | 11 | 49 | FOBS= | 222.4 | SIGMA= | 1.8 | PHAS= | 90.0 | FOM= | 1.00 | TEST= 0
| INDE | 0 | 11 | 51 | FOBS= | 143.3 | SIGMA= | 1.9 | PHAS= | 90.0 | FOM= | 1.00 | TEST= 0
| INDE | 0 | 11 | 53 | FOBS= | 124.0 | SIGMA= | 1.9 | PHAS= | -90.0 | FOM= | 0.95 | TEST= 0
| INDE | 0 | 11 | 55 | FOBS= | 143.5 | SIGMA= | 1.7 | PHAS= | -90.0 | FOM= | 1.00 | TEST= 0
| INDE | 0 | 11 | 57 | FOBS= | 133.2 | SIGMA= | 1.8 | PHAS= | 90.0 | FOM= | 0.90 | TEST= 0
| INDE | 0 | 11 | 59 | FOBS= | 237.0 | SIGMA= | 1.1 | PHAS= | 90.0 | FOM= | 1.00 | TEST= 0
| INDE | 0 | 11 | 61 | FOBS= | 70.1 | SIGMA= | 3.2 | PHAS= | 90.0 | FOM= | 0.60 | TEST= 0
| INDE | 0 | 11 | 63 | FOBS= | 37.0 | SIGMA= | 7.3 | PHAS= | -90.0 | FOM= | 0.14 | TEST= 0
| INDE | 0 | 11 | 65 | FOBS= | 76.6 | SIGMA= | 5.2 | PHAS= | -90.0 | FOM= | 0.63 | TEST= 0
| INDE | 0 | 11 | 67 | FOBS= | 44.7 | SIGMA= | 8.6 | PHAS= | 90.0 | FOM= | 0.46 | TEST= 0
| INDE | 0 | 11 | 69 | FOBS= | 79.6 | SIGMA= | 5.0 | PHAS= | 90.0 | FOM= | 0.76 | TEST= 1
| INDE | 0 | 11 | 71 | FOBS= | 79.8 | SIGMA= | 5.0 | PHAS= | -90.0 | FOM= | 1.00 | TEST= 0
| INDE | 0 | 11 | 73 | FOBS= | 6.2 | SIGMA= | 64.9 | PHAS= | -90.0 | FOM= | 0.08 | TEST= 0
| INDE | 0 | 11 | 75 | FOBS= | 94.9 | SIGMA= | 4.4 | PHAS= | -90.0 | FOM= | 1.00 | TEST= 0
| INDE | 0 | 12 | 14 | FOBS= | 152.1 | SIGMA= | 1.0 | PHAS= | 0.0 | FOM= | 1.00 | TEST= 0
| INDE | 0 | 12 | 16 | FOBS= | 108.4 | SIGMA= | 0.9 | PHAS= | 0.0 | FOM= | 0.66 | TEST= 0
| INDE | 0 | 12 | 18 | FOBS= | 340.1 | SIGMA= | 0.9 | PHAS= | 0.0 | FOM= | 1.00 | TEST= 0

*FIG. 12A - 4*

```
INDE    0   12   20  FOBS=    161.8  SIGMA=    0.8  PHAS=      0.0  FOM=  1.00  TEST=  0
INDE    0   12   22  FOBS=    104.2  SIGMA=    1.1  PHAS=      0.0  FOM=  0.80  TEST=  0
INDE    0   12   24  FOBS=     68.5  SIGMA=    1.0  PHAS=   -180.0  FOM=  0.52  TEST=  0
INDE    0   12   26  FOBS=     42.8  SIGMA=    1.6  PHAS=   -180.0  FOM=  0.96  TEST=  0
INDE    0   12   28  FOBS=    191.6  SIGMA=    0.9  PHAS=      0.0  FOM=  1.00  TEST=  1
INDE    0   12   30  FOBS=     48.2  SIGMA=    2.8  PHAS=      0.0  FOM=  1.00  TEST=  0
INDE    0   12   32  FOBS=     95.4  SIGMA=    1.6  PHAS=   -180.0  FOM=  0.94  TEST=  0
INDE    0   12   34  FOBS=    111.2  SIGMA=    2.1  PHAS=   -180.0  FOM=  1.00  TEST=  0
INDE    0   12   36  FOBS=     56.4  SIGMA=    4.3  PHAS=   -180.0  FOM=  0.88  TEST=  0
INDE    0   12   38  FOBS=    676.9  SIGMA=    1.0  PHAS=      0.0  FOM=  1.00  TEST=  0
INDE    0   12   40  FOBS=    203.6  SIGMA=    1.7  PHAS=      0.0  FOM=  0.96  TEST=  0
INDE    0   12   42  FOBS=    144.6  SIGMA=    2.3  PHAS=   -180.0  FOM=  1.00  TEST=  1
INDE    0   12   44  FOBS=    194.9  SIGMA=    2.1  PHAS=      0.0  FOM=  0.99  TEST=  0
INDE    0   12   46  FOBS=    304.2  SIGMA=    1.6  PHAS=      0.0  FOM=  1.00  TEST=  0
INDE    0   12   48  FOBS=     93.1  SIGMA=    3.0  PHAS=   -180.0  FOM=  0.92  TEST=  0
INDE    0   12   50  FOBS=    181.3  SIGMA=    1.6  PHAS=      0.0  FOM=  1.00  TEST=  0
INDE    0   12   52  FOBS=    238.3  SIGMA=    1.3  PHAS=   -180.0  FOM=  1.00  TEST=  0
INDE    0   12   54  FOBS=      0.0  SIGMA=   27.0  PHAS=      0.0  FOM=  0.00  TEST=  0
INDE    0   12   56  FOBS=     22.0  SIGMA=   10.1  PHAS=   -180.0  FOM=  0.10  TEST=  0
INDE    0   12   58  FOBS=      0.0  SIGMA=   23.1  PHAS=      0.0  FOM=  0.00  TEST=  0
INDE    0   12   60  FOBS=     95.9  SIGMA=    2.4  PHAS=      0.0  FOM=  0.95  TEST=  0
INDE    0   12   62  FOBS=      0.0  SIGMA=   20.9  PHAS=      0.0  FOM=  0.00  TEST=  0
INDE    0   12   64  FOBS=    144.0  SIGMA=    2.3  PHAS=   -180.0  FOM=  1.00  TEST=  0
INDE    0   12   66  FOBS=     90.4  SIGMA=    4.5  PHAS=      0.0  FOM=  0.79  TEST=  0
INDE    0   12   68  FOBS=     59.3  SIGMA=    6.7  PHAS=      0.0  FOM=  0.38  TEST=  1
INDE    0   12   70  FOBS=      0.0  SIGMA=   28.3  PHAS=      0.0  FOM=  0.00  TEST=  0
INDE    0   12   72  FOBS=      0.0  SIGMA=   28.5  PHAS=      0.0  FOM=  0.00  TEST=  0
INDE    0   12   76  FOBS=     90.7  SIGMA=    4.7  PHAS=   -180.0  FOM=  1.00  TEST=  0
INDE    0   13   13  FOBS=     49.4  SIGMA=    2.4  PHAS=     90.0  FOM=  0.20  TEST=  0
INDE    0   13   15  FOBS=     47.4  SIGMA=    2.7  PHAS=     90.0  FOM=  0.41  TEST=  0
INDE    0   13   17  FOBS=     79.3  SIGMA=    1.3  PHAS=    -90.0  FOM=  0.98  TEST=  0
INDE    0   13   19  FOBS=    257.6  SIGMA=    0.8  PHAS=    -90.0  FOM=  1.00  TEST=  0
INDE    0   13   21  FOBS=    147.6  SIGMA=    0.7  PHAS=    -90.0  FOM=  0.94  TEST=  0
INDE    0   13   23  FOBS=    116.5  SIGMA=    0.7  PHAS=    -90.0  FOM=  0.69  TEST=  0
INDE    0   13   25  FOBS=    132.3  SIGMA=    0.6  PHAS=    -90.0  FOM=  0.90  TEST=  1
INDE    0   13   27  FOBS=     57.8  SIGMA=    1.3  PHAS=    -90.0  FOM=  1.00  TEST=  0
INDE    0   13   29  FOBS=      0.0  SIGMA=   13.4  PHAS=      0.0  FOM=  0.00  TEST=  0
INDE    0   13   31  FOBS=    136.4  SIGMA=    0.8  PHAS=    -90.0  FOM=  0.68  TEST=  0
INDE    0   13   33  FOBS=     71.7  SIGMA=    2.2  PHAS=     90.0  FOM=  0.79  TEST=  0
INDE    0   13   35  FOBS=     35.3  SIGMA=    5.5  PHAS=      0.0  FOM=  0.00  TEST=  1
INDE    0   13   37  FOBS=    596.8  SIGMA=    1.0  PHAS=    -90.0  FOM=  1.00  TEST=  0
INDE    0   13   39  FOBS=    441.4  SIGMA=    1.1  PHAS=    -90.0  FOM=  1.00  TEST=  0
INDE    0   13   41  FOBS=    255.4  SIGMA=    1.5  PHAS=    -90.0  FOM=  1.00  TEST=  0
INDE    0   13   43  FOBS=     91.2  SIGMA=    3.9  PHAS=     90.0  FOM=  1.00  TEST=  0
INDE    0   13   45  FOBS=     82.9  SIGMA=    4.6  PHAS=     90.0  FOM=  0.48  TEST=  0
INDE    0   13   47  FOBS=     93.3  SIGMA=    6.3  PHAS=    -90.0  FOM=  0.17  TEST=  0
INDE    0   13   49  FOBS=    255.1  SIGMA=    1.6  PHAS=    -90.0  FOM=  1.00  TEST=  0
INDE    0   13   51  FOBS=    199.0  SIGMA=    1.5  PHAS=     90.0  FOM=  1.00  TEST=  0
INDE    0   13   53  FOBS=     93.9  SIGMA=    2.6  PHAS=     90.0  FOM=  0.99  TEST=  0
INDE    0   13   55  FOBS=      0.0  SIGMA=   23.5  PHAS=      0.0  FOM=  0.00  TEST=  0
INDE    0   13   57  FOBS=     68.0  SIGMA=    3.4  PHAS=     90.0  FOM=  0.95  TEST=  0
INDE    0   13   59  FOBS=      0.0  SIGMA=   21.1  PHAS=      0.0  FOM=  0.00  TEST=  1
INDE    0   13   61  FOBS=     89.4  SIGMA=    2.5  PHAS=    -90.0  FOM=  0.87  TEST=  0
INDE    0   13   63  FOBS=      0.0  SIGMA=   23.3  PHAS=      0.0  FOM=  0.00  TEST=  0
INDE    0   13   65  FOBS=     15.6  SIGMA=   26.3  PHAS=     90.0  FOM=  0.04  TEST=  0
INDE    0   13   67  FOBS=    109.5  SIGMA=    3.8  PHAS=    -90.0  FOM=  0.98  TEST=  0
INDE    0   13   69  FOBS=     47.7  SIGMA=    8.5  PHAS=    -90.0  FOM=  0.99  TEST=  0
INDE    0   13   71  FOBS=     53.2  SIGMA=    7.5  PHAS=    -90.0  FOM=  0.20  TEST=  0
INDE    0   13   73  FOBS=     60.3  SIGMA=    6.9  PHAS=    -90.0  FOM=  0.98  TEST=  0
INDE    0   13   75  FOBS=    104.6  SIGMA=    4.2  PHAS=    -90.0  FOM=  1.00  TEST=  0
INDE    0   14   14  FOBS=    371.1  SIGMA=    0.8  PHAS=      0.0  FOM=  1.00  TEST=  0
INDE    0   14   16  FOBS=     37.1  SIGMA=    3.5  PHAS=      0.0  FOM=  0.48  TEST=  0
INDE    0   14   18  FOBS=    174.1  SIGMA=    0.8  PHAS=      0.0  FOM=  0.96  TEST=  0
INDE    0   14   20  FOBS=     80.7  SIGMA=    1.4  PHAS=   -180.0  FOM=  0.65  TEST=  0
INDE    0   14   22  FOBS=     41.8  SIGMA=    1.8  PHAS=      0.0  FOM=  1.00  TEST=  0
INDE    0   14   24  FOBS=    137.1  SIGMA=    0.8  PHAS=   -180.0  FOM=  0.84  TEST=  0
INDE    0   14   26  FOBS=    212.3  SIGMA=    0.8  PHAS=   -180.0  FOM=  1.00  TEST=  0
INDE    0   14   28  FOBS=    246.4  SIGMA=    0.8  PHAS=      0.0  FOM=  1.00  TEST=  0
INDE    0   14   30  FOBS=      0.0  SIGMA=   13.0  PHAS=      0.0  FOM=  0.00  TEST=  0
INDE    0   14   32  FOBS=    206.2  SIGMA=    0.9  PHAS=   -180.0  FOM=  0.87  TEST=  0
```

*FIG. 12A - 5*

| | | | | | | | | | | | | |
|---|---|---|---|---|---|---|---|---|---|---|---|---|
| INDE | 0 | 14 | 34 | FOBS= | 252.6 | SIGMA= | 0.9 | PHAS= | -180.0 | FOM= | 0.90 | TEST= 0 |
| INDE | 0 | 14 | 36 | FOBS= | 52.4 | SIGMA= | 3.5 | PHAS= | 0.0 | FOM= | 0.59 | TEST= 0 |
| INDE | 0 | 14 | 38 | FOBS= | 106.9 | SIGMA= | 2.8 | PHAS= | 0.0 | FOM= | 1.00 | TEST= 0 |
| INDE | 0 | 14 | 40 | FOBS= | 50.5 | SIGMA= | 6.1 | PHAS= | -180.0 | FOM= | 0.86 | TEST= 0 |
| INDE | 0 | 14 | 42 | FOBS= | 173.5 | SIGMA= | 2.1 | PHAS= | -180.0 | FOM= | 1.00 | TEST= 0 |
| INDE | 0 | 14 | 44 | FOBS= | 167.6 | SIGMA= | 2.4 | PHAS= | 0.0 | FOM= | 1.00 | TEST= 0 |
| INDE | 0 | 14 | 46 | FOBS= | 236.8 | SIGMA= | 2.7 | PHAS= | 0.0 | FOM= | 1.00 | TEST= 0 |
| INDE | 0 | 14 | 48 | FOBS= | 41.7 | SIGMA= | 9.9 | PHAS= | -180.0 | FOM= | 0.33 | TEST= 0 |
| INDE | 0 | 14 | 50 | FOBS= | 154.0 | SIGMA= | 1.9 | PHAS= | 0.0 | FOM= | 1.00 | TEST= 1 |
| INDE | 0 | 14 | 52 | FOBS= | 139.2 | SIGMA= | 2.0 | PHAS= | -180.0 | FOM= | 1.00 | TEST= 0 |
| INDE | 0 | 14 | 54 | FOBS= | 37.0 | SIGMA= | 6.3 | PHAS= | 0.0 | FOM= | 1.00 | TEST= 0 |
| INDE | 0 | 14 | 56 | FOBS= | 0.0 | SIGMA= | 21.2 | PHAS= | 0.0 | FOM= | 0.00 | TEST= 0 |
| INDE | 0 | 14 | 58 | FOBS= | 0.0 | SIGMA= | 21.2 | PHAS= | 0.0 | FOM= | 0.00 | TEST= 0 |
| INDE | 0 | 14 | 60 | FOBS= | 0.0 | SIGMA= | 21.1 | PHAS= | 0.0 | FOM= | 0.00 | TEST= 0 |
| INDE | 0 | 14 | 62 | FOBS= | 48.9 | SIGMA= | 4.6 | PHAS= | -180.0 | FOM= | 0.33 | TEST= 0 |
| INDE | 0 | 14 | 64 | FOBS= | 45.4 | SIGMA= | 7.2 | PHAS= | 0.0 | FOM= | 0.84 | TEST= 0 |
| INDE | 0 | 14 | 66 | FOBS= | 88.7 | SIGMA= | 4.8 | PHAS= | 0.0 | FOM= | 1.00 | TEST= 0 |
| INDE | 0 | 14 | 68 | FOBS= | 23.1 | SIGMA= | 17.6 | PHAS= | -180.0 | FOM= | 0.63 | TEST= 0 |
| INDE | 0 | 14 | 70 | FOBS= | 101.6 | SIGMA= | 4.2 | PHAS= | -180.0 | FOM= | 1.00 | TEST= 0 |
| INDE | 0 | 14 | 72 | FOBS= | 106.7 | SIGMA= | 4.0 | PHAS= | -180.0 | FOM= | 0.97 | TEST= 0 |
| INDE | 0 | 14 | 74 | FOBS= | 157.5 | SIGMA= | 2.9 | PHAS= | -180.0 | FOM= | 1.00 | TEST= 0 |
| INDE | 0 | 14 | 76 | FOBS= | 13.6 | SIGMA= | 32.3 | PHAS= | -180.0 | FOM= | 0.29 | TEST= 0 |
| INDE | 0 | 15 | 15 | FOBS= | 396.6 | SIGMA= | 0.8 | PHAS= | -90.0 | FOM= | 1.00 | TEST= 0 |
| INDE | 0 | 15 | 17 | FOBS= | 233.9 | SIGMA= | 1.5 | PHAS= | -90.0 | FOM= | 1.00 | TEST= 0 |
| INDE | 0 | 15 | 19 | FOBS= | 309.6 | SIGMA= | 0.7 | PHAS= | -90.0 | FOM= | 1.00 | TEST= 0 |
| INDE | 0 | 15 | 21 | FOBS= | 213.1 | SIGMA= | 0.7 | PHAS= | -90.0 | FOM= | 1.00 | TEST= 0 |
| INDE | 0 | 15 | 23 | FOBS= | 36.9 | SIGMA= | 2.1 | PHAS= | -90.0 | FOM= | 1.00 | TEST= 0 |
| INDE | 0 | 15 | 25 | FOBS= | 303.6 | SIGMA= | 0.8 | PHAS= | 90.0 | FOM= | 1.00 | TEST= 0 |
| INDE | 0 | 15 | 27 | FOBS= | 0.0 | SIGMA= | 12.7 | PHAS= | 0.0 | FOM= | 0.00 | TEST= 0 |
| INDE | 0 | 15 | 29 | FOBS= | 60.5 | SIGMA= | 1.4 | PHAS= | -90.0 | FOM= | 0.17 | TEST= 0 |
| INDE | 0 | 15 | 31 | FOBS= | 285.7 | SIGMA= | 0.8 | PHAS= | -90.0 | FOM= | 1.00 | TEST= 0 |
| INDE | 0 | 15 | 33 | FOBS= | 184.0 | SIGMA= | 0.8 | PHAS= | 90.0 | FOM= | 1.00 | TEST= 0 |
| INDE | 0 | 15 | 35 | FOBS= | 20.9 | SIGMA= | 8.4 | PHAS= | 90.0 | FOM= | 0.19 | TEST= 0 |
| INDE | 0 | 15 | 37 | FOBS= | 628.5 | SIGMA= | 1.0 | PHAS= | -90.0 | FOM= | 1.00 | TEST= 0 |
| INDE | 0 | 15 | 39 | FOBS= | 97.7 | SIGMA= | 2.6 | PHAS= | -90.0 | FOM= | 0.09 | TEST= 1 |
| INDE | 0 | 15 | 41 | FOBS= | 165.3 | SIGMA= | 2.2 | PHAS= | -90.0 | FOM= | 0.43 | TEST= 0 |
| INDE | 0 | 15 | 43 | FOBS= | 64.2 | SIGMA= | 5.7 | PHAS= | 90.0 | FOM= | 0.55 | TEST= 0 |
| INDE | 0 | 15 | 45 | FOBS= | 247.9 | SIGMA= | 1.8 | PHAS= | 90.0 | FOM= | 0.98 | TEST= 0 |
| INDE | 0 | 15 | 47 | FOBS= | 157.4 | SIGMA= | 2.7 | PHAS= | -90.0 | FOM= | 1.00 | TEST= 0 |
| INDE | 0 | 15 | 49 | FOBS= | 112.8 | SIGMA= | 3.1 | PHAS= | -90.0 | FOM= | 1.00 | TEST= 0 |
| INDE | 0 | 15 | 51 | FOBS= | 43.7 | SIGMA= | 6.2 | PHAS= | 90.0 | FOM= | 0.15 | TEST= 0 |
| INDE | 0 | 15 | 53 | FOBS= | 0.0 | SIGMA= | 21.6 | PHAS= | 0.0 | FOM= | 0.00 | TEST= 0 |
| INDE | 0 | 15 | 55 | FOBS= | 145.9 | SIGMA= | 1.7 | PHAS= | 90.0 | FOM= | 1.00 | TEST= 1 |
| INDE | 0 | 15 | 57 | FOBS= | 16.7 | SIGMA= | 13.6 | PHAS= | 90.0 | FOM= | 0.17 | TEST= 0 |
| INDE | 0 | 15 | 59 | FOBS= | 44.3 | SIGMA= | 5.0 | PHAS= | -90.0 | FOM= | 0.89 | TEST= 0 |
| INDE | 0 | 15 | 61 | FOBS= | 28.6 | SIGMA= | 8.9 | PHAS= | -90.0 | FOM= | 0.73 | TEST= 0 |
| INDE | 0 | 15 | 63 | FOBS= | 27.6 | SIGMA= | 8.2 | PHAS= | -90.0 | FOM= | 0.73 | TEST= 0 |
| INDE | 0 | 15 | 65 | FOBS= | 46.5 | SIGMA= | 9.3 | PHAS= | -90.0 | FOM= | 0.88 | TEST= 0 |
| INDE | 0 | 15 | 67 | FOBS= | 49.7 | SIGMA= | 8.4 | PHAS= | -90.0 | FOM= | 0.83 | TEST= 0 |
| INDE | 0 | 15 | 69 | FOBS= | 60.7 | SIGMA= | 6.9 | PHAS= | -90.0 | FOM= | 0.40 | TEST= 0 |
| INDE | 0 | 15 | 71 | FOBS= | 82.5 | SIGMA= | 5.2 | PHAS= | 90.0 | FOM= | 1.00 | TEST= 0 |
| INDE | 0 | 15 | 73 | FOBS= | 144.1 | SIGMA= | 3.1 | PHAS= | 90.0 | FOM= | 1.00 | TEST= 0 |
| INDE | 0 | 15 | 75 | FOBS= | 36.0 | SIGMA= | 12.2 | PHAS= | -90.0 | FOM= | 0.19 | TEST= 0 |
| INDE | 0 | 16 | 16 | FOBS= | 301.5 | SIGMA= | 0.9 | PHAS= | -180.0 | FOM= | 1.00 | TEST= 1 |
| INDE | 0 | 16 | 18 | FOBS= | 214.7 | SIGMA= | 1.1 | PHAS= | -180.0 | FOM= | 0.98 | TEST= 0 |
| INDE | 0 | 16 | 20 | FOBS= | 443.7 | SIGMA= | 0.9 | PHAS= | -180.0 | FOM= | 1.00 | TEST= 0 |
| INDE | 0 | 16 | 22 | FOBS= | 167.0 | SIGMA= | 0.9 | PHAS= | -180.0 | FOM= | 1.00 | TEST= 0 |
| INDE | 0 | 16 | 24 | FOBS= | 74.6 | SIGMA= | 1.2 | PHAS= | 0.0 | FOM= | 0.95 | TEST= 0 |
| INDE | 0 | 16 | 26 | FOBS= | 122.0 | SIGMA= | 0.8 | PHAS= | -180.0 | FOM= | 0.99 | TEST= 0 |
| INDE | 0 | 16 | 28 | FOBS= | 17.4 | SIGMA= | 5.0 | PHAS= | 0.0 | FOM= | 1.00 | TEST= 0 |
| INDE | 0 | 16 | 30 | FOBS= | 28.8 | SIGMA= | 3.1 | PHAS= | 0.0 | FOM= | 1.00 | TEST= 0 |
| INDE | 0 | 16 | 32 | FOBS= | 180.2 | SIGMA= | 0.8 | PHAS= | -180.0 | FOM= | 0.91 | TEST= 1 |
| INDE | 0 | 16 | 34 | FOBS= | 495.6 | SIGMA= | 0.8 | PHAS= | 0.0 | FOM= | 1.00 | TEST= 0 |
| INDE | 0 | 16 | 36 | FOBS= | 143.3 | SIGMA= | 1.5 | PHAS= | 0.0 | FOM= | 1.00 | TEST= 0 |
| INDE | 0 | 16 | 38 | FOBS= | 187.6 | SIGMA= | 1.3 | PHAS= | 0.0 | FOM= | 0.97 | TEST= 0 |
| INDE | 0 | 16 | 40 | FOBS= | 127.4 | SIGMA= | 1.9 | PHAS= | -180.0 | FOM= | 0.99 | TEST= 1 |
| INDE | 0 | 16 | 42 | FOBS= | 91.0 | SIGMA= | 3.9 | PHAS= | -180.0 | FOM= | 0.86 | TEST= 0 |
| INDE | 0 | 16 | 44 | FOBS= | 110.6 | SIGMA= | 3.6 | PHAS= | 0.0 | FOM= | 0.77 | TEST= 0 |
| INDE | 0 | 16 | 46 | FOBS= | 80.8 | SIGMA= | 5.3 | PHAS= | 0.0 | FOM= | 0.38 | TEST= 0 |
| INDE | 0 | 16 | 48 | FOBS= | 245.4 | SIGMA= | 1.9 | PHAS= | -180.0 | FOM= | 1.00 | TEST= 0 |

*FIG. 12A - 6*

| | | | | | | | | | | | |
|---|---|---|---|---|---|---|---|---|---|---|---|
| INDE | 0 | 16 | 50 | FOBS= | 113.1 | SIGMA= | 2.5 | PHAS= | 0.0 | FOM= | 1.00 | TEST= 0
| INDE | 0 | 16 | 52 | FOBS= | 141.4 | SIGMA= | 2.0 | PHAS= | -180.0 | FOM= | 0.98 | TEST= 0
| INDE | 0 | 16 | 54 | FOBS= | 50.8 | SIGMA= | 4.6 | PHAS= | 0.0 | FOM= | 0.35 | TEST= 1
| INDE | 0 | 16 | 56 | FOBS= | 110.6 | SIGMA= | 2.2 | PHAS= | 0.0 | FOM= | 1.00 | TEST= 0
| INDE | 0 | 16 | 58 | FOBS= | 98.3 | SIGMA= | 2.4 | PHAS= | -180.0 | FOM= | 1.00 | TEST= 0
| INDE | 0 | 16 | 60 | FOBS= | 26.5 | SIGMA= | 8.6 | PHAS= | -180.0 | FOM= | 0.04 | TEST= 1
| INDE | 0 | 16 | 62 | FOBS= | 176.6 | SIGMA= | 1.8 | PHAS= | -180.0 | FOM= | 1.00 | TEST= 0
| INDE | 0 | 16 | 64 | FOBS= | 56.9 | SIGMA= | 7.7 | PHAS= | 0.0 | FOM= | 0.64 | TEST= 1
| INDE | 0 | 16 | 66 | FOBS= | 56.2 | SIGMA= | 7.7 | PHAS= | 0.0 | FOM= | 0.88 | TEST= 0
| INDE | 0 | 16 | 68 | FOBS= | 16.4 | SIGMA= | 26.0 | PHAS= | -180.0 | FOM= | 0.06 | TEST= 0
| INDE | 0 | 16 | 70 | FOBS= | 27.1 | SIGMA= | 15.5 | PHAS= | -180.0 | FOM= | 0.26 | TEST= 0
| INDE | 0 | 16 | 72 | FOBS= | 42.7 | SIGMA= | 10.0 | PHAS= | 0.0 | FOM= | 0.44 | TEST= 0
| INDE | 0 | 16 | 74 | FOBS= | 59.6 | SIGMA= | 7.4 | PHAS= | -180.0 | FOM= | 0.99 | TEST= 0
| INDE | 0 | 16 | 76 | FOBS= | 0.0 | SIGMA= | 30.0 | PHAS= | 0.0 | FOM= | 0.00 | TEST= 0
| INDE | 0 | 17 | 17 | FOBS= | 86.7 | SIGMA= | 1.9 | PHAS= | 90.0 | FOM= | 0.64 | TEST= 0
| INDE | 0 | 17 | 19 | FOBS= | 291.2 | SIGMA= | 1.0 | PHAS= | 90.0 | FOM= | 1.00 | TEST= 0
| INDE | 0 | 17 | 21 | FOBS= | 185.9 | SIGMA= | 1.2 | PHAS= | 90.0 | FOM= | 1.00 | TEST= 0
| INDE | 0 | 17 | 23 | FOBS= | 12.7 | SIGMA= | 10.8 | PHAS= | 0.0 | FOM= | 0.00 | TEST= 1
| INDE | 0 | 17 | 25 | FOBS= | 97.6 | SIGMA= | 1.0 | PHAS= | 90.0 | FOM= | 0.99 | TEST= 0
| INDE | 0 | 17 | 27 | FOBS= | 231.4 | SIGMA= | 0.9 | PHAS= | 90.0 | FOM= | 1.00 | TEST= 0
| INDE | 0 | 17 | 29 | FOBS= | 0.0 | SIGMA= | 13.6 | PHAS= | 0.0 | FOM= | 0.00 | TEST= 0
| INDE | 0 | 17 | 31 | FOBS= | 287.3 | SIGMA= | 0.8 | PHAS= | -90.0 | FOM= | 1.00 | TEST= 0
| INDE | 0 | 17 | 33 | FOBS= | 268.6 | SIGMA= | 0.7 | PHAS= | -90.0 | FOM= | 0.75 | TEST= 0
| INDE | 0 | 17 | 35 | FOBS= | 8.9 | SIGMA= | 12.3 | PHAS= | -90.0 | FOM= | 0.04 | TEST= 0
| INDE | 0 | 17 | 37 | FOBS= | 324.9 | SIGMA= | 0.9 | PHAS= | -90.0 | FOM= | 1.00 | TEST= 0
| INDE | 0 | 17 | 39 | FOBS= | 159.4 | SIGMA= | 1.8 | PHAS= | 90.0 | FOM= | 0.74 | TEST= 0
| INDE | 0 | 17 | 41 | FOBS= | 0.0 | SIGMA= | 21.6 | PHAS= | 0.0 | FOM= | 0.00 | TEST= 0
| INDE | 0 | 17 | 43 | FOBS= | 85.3 | SIGMA= | 4.5 | PHAS= | 90.0 | FOM= | 0.28 | TEST= 0
| INDE | 0 | 17 | 45 | FOBS= | 0.0 | SIGMA= | 28.6 | PHAS= | 0.0 | FOM= | 0.00 | TEST= 0
| INDE | 0 | 17 | 47 | FOBS= | 360.8 | SIGMA= | 1.5 | PHAS= | -90.0 | FOM= | 0.93 | TEST= 1
| INDE | 0 | 17 | 49 | FOBS= | 140.7 | SIGMA= | 4.2 | PHAS= | -90.0 | FOM= | 0.06 | TEST= 1
| INDE | 0 | 17 | 51 | FOBS= | 0.0 | SIGMA= | 23.3 | PHAS= | 0.0 | FOM= | 0.00 | TEST= 0
| INDE | 0 | 17 | 53 | FOBS= | 165.6 | SIGMA= | 1.6 | PHAS= | 90.0 | FOM= | 1.00 | TEST= 1
| INDE | 0 | 17 | 55 | FOBS= | 42.4 | SIGMA= | 5.7 | PHAS= | 90.0 | FOM= | 0.56 | TEST= 0
| INDE | 0 | 17 | 57 | FOBS= | 32.7 | SIGMA= | 7.1 | PHAS= | -90.0 | FOM= | 0.26 | TEST= 0
| INDE | 0 | 17 | 59 | FOBS= | 130.4 | SIGMA= | 1.9 | PHAS= | 90.0 | FOM= | 0.99 | TEST= 0
| INDE | 0 | 17 | 61 | FOBS= | 91.0 | SIGMA= | 2.6 | PHAS= | 90.0 | FOM= | 0.99 | TEST= 0
| INDE | 0 | 17 | 63 | FOBS= | 76.9 | SIGMA= | 3.0 | PHAS= | 90.0 | FOM= | 1.00 | TEST= 0
| INDE | 0 | 17 | 65 | FOBS= | 30.8 | SIGMA= | 14.2 | PHAS= | 90.0 | FOM= | 0.07 | TEST= 0
| INDE | 0 | 17 | 67 | FOBS= | 94.3 | SIGMA= | 4.8 | PHAS= | -90.0 | FOM= | 0.67 | TEST= 0
| INDE | 0 | 17 | 69 | FOBS= | 0.0 | SIGMA= | 29.5 | PHAS= | 0.0 | FOM= | 0.00 | TEST= 0
| INDE | 0 | 17 | 71 | FOBS= | 35.6 | SIGMA= | 12.1 | PHAS= | 90.0 | FOM= | 0.73 | TEST= 0
| INDE | 0 | 17 | 73 | FOBS= | 87.5 | SIGMA= | 5.1 | PHAS= | 90.0 | FOM= | 0.98 | TEST= 0
| INDE | 0 | 17 | 75 | FOBS= | 33.3 | SIGMA= | 13.5 | PHAS= | -90.0 | FOM= | 0.32 | TEST= 0
| INDE | 0 | 18 | 2 | FOBS= | 36.3 | SIGMA= | 2.2 | PHAS= | -180.0 | FOM= | 0.75 | TEST= 1
| INDE | 0 | 18 | 4 | FOBS= | 69.4 | SIGMA= | 1.0 | PHAS= | 0.0 | FOM= | 1.00 | TEST= 0
| INDE | 0 | 18 | 18 | FOBS= | 158.5 | SIGMA= | 1.3 | PHAS= | -180.0 | FOM= | 0.50 | TEST= 0
| INDE | 0 | 18 | 20 | FOBS= | 93.4 | SIGMA= | 2.0 | PHAS= | 0.0 | FOM= | 1.00 | TEST= 0
| INDE | 0 | 18 | 22 | FOBS= | 22.5 | SIGMA= | 7.7 | PHAS= | -180.0 | FOM= | 0.20 | TEST= 0
| INDE | 0 | 18 | 24 | FOBS= | 108.6 | SIGMA= | 1.0 | PHAS= | -180.0 | FOM= | 1.00 | TEST= 0
| INDE | 0 | 18 | 26 | FOBS= | 0.0 | SIGMA= | 14.6 | PHAS= | 0.0 | FOM= | 0.00 | TEST= 0
| INDE | 0 | 18 | 28 | FOBS= | 158.9 | SIGMA= | 0.7 | PHAS= | 0.0 | FOM= | 0.68 | TEST= 0
| INDE | 0 | 18 | 30 | FOBS= | 102.8 | SIGMA= | 1.3 | PHAS= | 0.0 | FOM= | 0.96 | TEST= 0
| INDE | 0 | 18 | 32 | FOBS= | 35.3 | SIGMA= | 3.0 | PHAS= | 0.0 | FOM= | 1.00 | TEST= 0
| INDE | 0 | 18 | 34 | FOBS= | 539.9 | SIGMA= | 0.5 | PHAS= | -180.0 | FOM= | 1.00 | TEST= 0
| INDE | 0 | 18 | 36 | FOBS= | 98.1 | SIGMA= | 2.2 | PHAS= | 0.0 | FOM= | 0.46 | TEST= 0
| INDE | 0 | 18 | 38 | FOBS= | 112.4 | SIGMA= | 1.2 | PHAS= | 0.0 | FOM= | 0.31 | TEST= 0
| INDE | 0 | 18 | 40 | FOBS= | 83.9 | SIGMA= | 2.9 | PHAS= | -180.0 | FOM= | 1.00 | TEST= 0
| INDE | 0 | 18 | 42 | FOBS= | 166.3 | SIGMA= | 1.7 | PHAS= | 0.0 | FOM= | 0.97 | TEST= 0
| INDE | 0 | 18 | 44 | FOBS= | 35.2 | SIGMA= | 8.1 | PHAS= | 0.0 | FOM= | 0.34 | TEST= 0
| INDE | 0 | 18 | 46 | FOBS= | 204.1 | SIGMA= | 2.2 | PHAS= | -180.0 | FOM= | 1.00 | TEST= 0
| INDE | 0 | 18 | 48 | FOBS= | 0.0 | SIGMA= | 28.0 | PHAS= | 0.0 | FOM= | 0.00 | TEST= 0
| INDE | 0 | 18 | 50 | FOBS= | 88.4 | SIGMA= | 6.3 | PHAS= | -180.0 | FOM= | 0.98 | TEST= 0
| INDE | 0 | 18 | 52 | FOBS= | 88.1 | SIGMA= | 3.2 | PHAS= | 0.0 | FOM= | 0.99 | TEST= 0
| INDE | 0 | 18 | 54 | FOBS= | 96.0 | SIGMA= | 2.6 | PHAS= | 0.0 | FOM= | 1.00 | TEST= 1
| INDE | 0 | 18 | 56 | FOBS= | 41.2 | SIGMA= | 5.7 | PHAS= | 0.0 | FOM= | 0.79 | TEST= 0
| INDE | 0 | 18 | 58 | FOBS= | 66.6 | SIGMA= | 3.5 | PHAS= | 0.0 | FOM= | 1.00 | TEST= 0
| INDE | 0 | 18 | 60 | FOBS= | 141.4 | SIGMA= | 1.7 | PHAS= | 0.0 | FOM= | 1.00 | TEST= 0
| INDE | 0 | 18 | 62 | FOBS= | 0.0 | SIGMA= | 23.6 | PHAS= | 0.0 | FOM= | 0.00 | TEST= 0
| INDE | 0 | 18 | 64 | FOBS= | 134.4 | SIGMA= | 3.5 | PHAS= | 0.0 | FOM= | 0.99 | TEST= 0

*FIG. 12A - 7*

```
INDE  0  18  66  FOBS=  169.9  SIGMA=   2.8  PHAS=     0.0  FOM=  1.00  TEST=  0
INDE  0  18  68  FOBS=    0.0  SIGMA=  29.9  PHAS=     0.0  FOM=  0.00  TEST=  0
INDE  0  18  70  FOBS=   32.1  SIGMA=  13.7  PHAS=     0.0  FOM=  0.32  TEST=  0
INDE  0  18  72  FOBS=    0.0  SIGMA=  29.4  PHAS=     0.0  FOM=  0.00  TEST=  1
INDE  0  18  74  FOBS=   14.8  SIGMA=  30.1  PHAS=  -180.0  FOM=  0.22  TEST=  0
INDE  0  19   1  FOBS=   11.5  SIGMA=   4.2  PHAS=   -90.0  FOM=  0.28  TEST=  1
INDE  0  19   3  FOBS=  109.1  SIGMA=   1.0  PHAS=   -90.0  FOM=  0.05  TEST=  0
INDE  0  19   5  FOBS=  114.6  SIGMA=   0.7  PHAS=   -90.0  FOM=  1.00  TEST=  0
INDE  0  19  19  FOBS=  179.5  SIGMA=   1.2  PHAS=   -90.0  FOM=  0.97  TEST=  0
INDE  0  19  21  FOBS=   85.6  SIGMA=   2.2  PHAS=   -90.0  FOM=  1.00  TEST=  0
INDE  0  19  23  FOBS=    0.0  SIGMA=  19.1  PHAS=     0.0  FOM=  0.00  TEST=  1
INDE  0  19  25  FOBS=   78.9  SIGMA=   1.5  PHAS=    90.0  FOM=  1.00  TEST=  0
INDE  0  19  27  FOBS=   91.3  SIGMA=   1.1  PHAS=    90.0  FOM=  1.00  TEST=  0
INDE  0  19  29  FOBS=   82.2  SIGMA=   1.3  PHAS=    90.0  FOM=  1.00  TEST=  0
INDE  0  19  31  FOBS=  139.3  SIGMA=   0.9  PHAS=    90.0  FOM=  0.88  TEST=  0
INDE  0  19  33  FOBS=   78.8  SIGMA=   2.5  PHAS=    90.0  FOM=  1.00  TEST=  0
INDE  0  19  35  FOBS=  363.7  SIGMA=   1.0  PHAS=    90.0  FOM=  1.00  TEST=  0
INDE  0  19  37  FOBS=   30.7  SIGMA=   5.1  PHAS=    90.0  FOM=  0.70  TEST=  0
INDE  0  19  39  FOBS=   48.9  SIGMA=   2.8  PHAS=    90.0  FOM=  1.00  TEST=  0
INDE  0  19  41  FOBS=   59.9  SIGMA=   4.2  PHAS=   -90.0  FOM=  1.00  TEST=  0
INDE  0  19  43  FOBS=    0.0  SIGMA=  23.6  PHAS=     0.0  FOM=  0.00  TEST=  0
INDE  0  19  45  FOBS=   54.1  SIGMA=   5.6  PHAS=    90.0  FOM=  0.37  TEST=  0
INDE  0  19  47  FOBS=  175.8  SIGMA=   2.5  PHAS=   -90.0  FOM=  0.59  TEST=  1
INDE  0  19  49  FOBS=  370.5  SIGMA=   2.0  PHAS=    90.0  FOM=  1.00  TEST=  0
INDE  0  19  51  FOBS=   32.9  SIGMA=  16.6  PHAS=    90.0  FOM=  0.32  TEST=  0
INDE  0  19  53  FOBS=    0.0  SIGMA=  22.0  PHAS=     0.0  FOM=  0.00  TEST=  0
INDE  0  19  55  FOBS=  158.7  SIGMA=   1.7  PHAS=   -90.0  FOM=  1.00  TEST=  0
INDE  0  19  57  FOBS=  151.8  SIGMA=   1.7  PHAS=   -90.0  FOM=  1.00  TEST=  0
INDE  0  19  59  FOBS=    0.0  SIGMA=  21.6  PHAS=     0.0  FOM=  0.00  TEST=  0
INDE  0  19  61  FOBS=    0.0  SIGMA=  21.5  PHAS=     0.0  FOM=  0.00  TEST=  0
INDE  0  19  63  FOBS=    0.0  SIGMA=  24.5  PHAS=     0.0  FOM=  0.00  TEST=  1
INDE  0  19  65  FOBS=  102.8  SIGMA=   4.5  PHAS=   -90.0  FOM=  1.00  TEST=  0
INDE  0  19  67  FOBS=   32.9  SIGMA=  13.6  PHAS=   -90.0  FOM=  0.50  TEST=  0
INDE  0  19  69  FOBS=   56.2  SIGMA=   8.1  PHAS=    90.0  FOM=  0.54  TEST=  0
INDE  0  19  71  FOBS=   28.8  SIGMA=  15.2  PHAS=    90.0  FOM=  0.00  TEST=  1
INDE  0  19  73  FOBS=   22.4  SIGMA=  19.8  PHAS=   -90.0  FOM=  0.43  TEST=  0
INDE  0  19  75  FOBS=   20.2  SIGMA=  22.7  PHAS=    90.0  FOM=  0.62  TEST=  0
INDE  0  20   2  FOBS=  104.5  SIGMA=   0.6  PHAS=     0.0  FOM=  0.77  TEST=  0
INDE  0  20   4  FOBS=   39.5  SIGMA=   1.8  PHAS=     0.0  FOM=  0.46  TEST=  0
INDE  0  20   6  FOBS=  168.6  SIGMA=   0.6  PHAS=  -180.0  FOM=  0.12  TEST=  0
INDE  0  20  20  FOBS=  183.5  SIGMA=   1.3  PHAS=  -180.0  FOM=  1.00  TEST=  0
INDE  0  20  22  FOBS=  198.4  SIGMA=   1.3  PHAS=  -180.0  FOM=  1.00  TEST=  0
INDE  0  20  24  FOBS=  219.4  SIGMA=   1.2  PHAS=  -180.0  FOM=  0.92  TEST=  1
INDE  0  20  26  FOBS=  214.1  SIGMA=   0.9  PHAS=  -180.0  FOM=  0.87  TEST=  1
INDE  0  20  28  FOBS=  226.0  SIGMA=   0.7  PHAS=     0.0  FOM=  1.00  TEST=  1
INDE  0  20  30  FOBS=   53.0  SIGMA=   2.1  PHAS=     0.0  FOM=  0.57  TEST=  0
INDE  0  20  32  FOBS=    0.0  SIGMA=  18.5  PHAS=     0.0  FOM=  0.00  TEST=  0
INDE  0  20  34  FOBS=  116.8  SIGMA=   1.8  PHAS=     0.0  FOM=  0.84  TEST=  0
INDE  0  20  36  FOBS=  360.3  SIGMA=   1.0  PHAS=     0.0  FOM=  1.00  TEST=  0
INDE  0  20  38  FOBS=  210.6  SIGMA=   0.8  PHAS=     0.0  FOM=  0.67  TEST=  0
INDE  0  20  40  FOBS=  136.0  SIGMA=   1.2  PHAS=     0.0  FOM=  0.96  TEST=  0
INDE  0  20  42  FOBS=  232.8  SIGMA=   1.4  PHAS=     0.0  FOM=  1.00  TEST=  0
INDE  0  20  44  FOBS=   89.2  SIGMA=   3.4  PHAS=     0.0  FOM=  0.53  TEST=  0
INDE  0  20  46  FOBS=   84.0  SIGMA=   3.5  PHAS=  -180.0  FOM=  0.33  TEST=  0
INDE  0  20  48  FOBS=   88.4  SIGMA=   3.8  PHAS=     0.0  FOM=  0.63  TEST=  0
INDE  0  20  50  FOBS=  165.6  SIGMA=   3.6  PHAS=  -180.0  FOM=  0.30  TEST=  1
INDE  0  20  52  FOBS=    0.0  SIGMA=  32.4  PHAS=     0.0  FOM=  0.00  TEST=  0
INDE  0  20  54  FOBS=   74.5  SIGMA=   3.4  PHAS=  -180.0  FOM=  0.94  TEST=  0
INDE  0  20  56  FOBS=  133.4  SIGMA=   1.9  PHAS=  -180.0  FOM=  1.00  TEST=  0
INDE  0  20  58  FOBS=   38.6  SIGMA=   6.2  PHAS=  -180.0  FOM=  1.00  TEST=  0
INDE  0  20  60  FOBS=   27.3  SIGMA=   8.7  PHAS=     0.0  FOM=  0.23  TEST=  0
INDE  0  20  62  FOBS=   70.0  SIGMA=   3.3  PHAS=  -180.0  FOM=  0.34  TEST=  0
INDE  0  20  64  FOBS=    0.0  SIGMA=  30.2  PHAS=     0.0  FOM=  0.00  TEST=  0
INDE  0  20  66  FOBS=   97.8  SIGMA=   4.8  PHAS=     0.0  FOM=  0.23  TEST=  1
INDE  0  20  68  FOBS=   60.5  SIGMA=   7.6  PHAS=     0.0  FOM=  0.92  TEST=  0
INDE  0  20  70  FOBS=   61.3  SIGMA=   7.5  PHAS=     0.0  FOM=  0.01  TEST=  1
INDE  0  20  72  FOBS=   21.1  SIGMA=  21.6  PHAS=  -180.0  FOM=  0.66  TEST=  0
INDE  0  20  74  FOBS=    0.0  SIGMA=  30.1  PHAS=     0.0  FOM=  0.00  TEST=  0
INDE  0  21   1  FOBS=   78.9  SIGMA=   0.8  PHAS=    90.0  FOM=  0.53  TEST=  0
INDE  0  21   5  FOBS=  128.2  SIGMA=   0.7  PHAS=   -90.0  FOM=  1.00  TEST=  0
```

*FIG. 12A - 8*

```
INDE  0  21  21  FOBS=  154.9  SIGMA=   1.5  PHAS=   90.0  FOM=  1.00  TEST= 1
INDE  0  21  23  FOBS=  275.6  SIGMA=   1.1  PHAS=   90.0  FOM=  1.00  TEST= 0
INDE  0  21  25  FOBS=  354.9  SIGMA=   1.1  PHAS=   90.0  FOM=  1.00  TEST= 0
INDE  0  21  27  FOBS=  301.0  SIGMA=   0.9  PHAS=  -90.0  FOM=  1.00  TEST= 0
INDE  0  21  29  FOBS=   78.6  SIGMA=   1.4  PHAS=   90.0  FOM=  0.93  TEST= 0
INDE  0  21  31  FOBS=    0.0  SIGMA=  15.0  PHAS=    0.0  FOM=  0.00  TEST= 0
INDE  0  21  33  FOBS=  118.9  SIGMA=   1.1  PHAS=  -90.0  FOM=  1.00  TEST= 0
INDE  0  21  35  FOBS=   51.5  SIGMA=   4.2  PHAS=  -90.0  FOM=  0.09  TEST= 0
INDE  0  21  37  FOBS=  218.7  SIGMA=   0.9  PHAS=   90.0  FOM=  1.00  TEST= 1
INDE  0  21  39  FOBS=  221.9  SIGMA=   0.9  PHAS=  -90.0  FOM=  0.94  TEST= 0
INDE  0  21  41  FOBS=  224.6  SIGMA=   1.0  PHAS=  -90.0  FOM=  1.00  TEST= 1
INDE  0  21  43  FOBS=   62.7  SIGMA=   2.8  PHAS=  -90.0  FOM=  0.49  TEST= 0
INDE  0  21  45  FOBS=  122.6  SIGMA=   2.6  PHAS=  -90.0  FOM=  1.00  TEST= 0
INDE  0  21  47  FOBS=   42.6  SIGMA=   7.8  PHAS=  -90.0  FOM=  0.02  TEST= 1
INDE  0  21  49  FOBS=    0.0  SIGMA=  25.3  PHAS=    0.0  FOM=  0.00  TEST= 0
INDE  0  21  51  FOBS=   60.2  SIGMA=   8.8  PHAS=   90.0  FOM=  0.91  TEST= 0
INDE  0  21  53  FOBS=   45.4  SIGMA=   5.5  PHAS=   90.0  FOM=  0.92  TEST= 0
INDE  0  21  55  FOBS=    0.0  SIGMA=  24.4  PHAS=    0.0  FOM=  0.00  TEST= 1
INDE  0  21  57  FOBS=   48.5  SIGMA=   5.0  PHAS=  -90.0  FOM=  0.04  TEST= 0
INDE  0  21  59  FOBS=  154.0  SIGMA=   1.7  PHAS=   90.0  FOM=  1.00  TEST= 0
INDE  0  21  61  FOBS=  133.7  SIGMA=   1.9  PHAS=   90.0  FOM=  1.00  TEST= 1
INDE  0  21  63  FOBS=   63.4  SIGMA=   4.8  PHAS=   90.0  FOM=  0.06  TEST= 0
INDE  0  21  65  FOBS=   21.5  SIGMA=  21.2  PHAS=    0.0  FOM=  0.00  TEST= 1
INDE  0  21  67  FOBS=  109.8  SIGMA=   4.3  PHAS=  -90.0  FOM=  0.86  TEST= 0
INDE  0  21  69  FOBS=   12.6  SIGMA=  36.3  PHAS=   90.0  FOM=  0.02  TEST= 0
INDE  0  21  71  FOBS=   28.2  SIGMA=  16.1  PHAS=   90.0  FOM=  0.41  TEST= 0
INDE  0  21  73  FOBS=   49.2  SIGMA=   9.5  PHAS=   90.0  FOM=  0.16  TEST= 0
INDE  0  22   2  FOBS=   30.9  SIGMA=   2.1  PHAS= -180.0  FOM=  0.08  TEST= 0
INDE  0  22   4  FOBS=  223.0  SIGMA=   0.5  PHAS=    0.0  FOM=  1.00  TEST= 0
INDE  0  22   6  FOBS=  306.3  SIGMA=   0.5  PHAS= -180.0  FOM=  1.00  TEST= 0
INDE  0  22  20  FOBS=  199.2  SIGMA=   1.8  PHAS= -180.0  FOM=  0.95  TEST= 0
INDE  0  22  22  FOBS=   34.5  SIGMA=   5.8  PHAS= -180.0  FOM=  0.99  TEST= 0
INDE  0  22  24  FOBS=  159.4  SIGMA=   1.6  PHAS=    0.0  FOM=  0.97  TEST= 0
INDE  0  22  26  FOBS=  118.0  SIGMA=   2.1  PHAS= -180.0  FOM=  0.91  TEST= 0
INDE  0  22  28  FOBS=  382.5  SIGMA=   0.6  PHAS=    0.0  FOM=  1.00  TEST= 0
INDE  0  22  30  FOBS=   11.5  SIGMA=  11.9  PHAS= -180.0  FOM=  0.45  TEST= 0
INDE  0  22  32  FOBS=   58.8  SIGMA=   2.2  PHAS= -180.0  FOM=  1.00  TEST= 0
INDE  0  22  34  FOBS=  223.2  SIGMA=   0.7  PHAS=    0.0  FOM=  0.99  TEST= 0
INDE  0  22  36  FOBS=  196.2  SIGMA=   1.0  PHAS=    0.0  FOM=  0.53  TEST= 0
INDE  0  22  38  FOBS=  262.4  SIGMA=   0.8  PHAS=    0.0  FOM=  1.00  TEST= 0
INDE  0  22  40  FOBS=   50.4  SIGMA=   3.2  PHAS= -180.0  FOM=  0.95  TEST= 1
INDE  0  22  42  FOBS=    0.0  SIGMA=  19.2  PHAS=    0.0  FOM=  0.00  TEST= 0
INDE  0  22  44  FOBS=  141.4  SIGMA=   1.4  PHAS= -180.0  FOM=  1.00  TEST= 0
INDE  0  22  46  FOBS=  110.9  SIGMA=   2.7  PHAS= -180.0  FOM=  0.46  TEST= 0
INDE  0  22  48  FOBS=    0.0  SIGMA=  25.5  PHAS=    0.0  FOM=  0.00  TEST= 0
INDE  0  22  50  FOBS=    0.0  SIGMA=  24.9  PHAS=    0.0  FOM=  0.00  TEST= 0
INDE  0  22  52  FOBS=   67.2  SIGMA=   7.8  PHAS= -180.0  FOM=  0.70  TEST= 0
INDE  0  22  54  FOBS=    0.0  SIGMA=  24.6  PHAS=    0.0  FOM=  0.00  TEST= 1
INDE  0  22  56  FOBS=    0.0  SIGMA=  22.1  PHAS=    0.0  FOM=  0.00  TEST= 0
INDE  0  22  58  FOBS=  115.5  SIGMA=   2.2  PHAS=    0.0  FOM=  1.00  TEST= 0
INDE  0  22  60  FOBS=   58.1  SIGMA=   4.2  PHAS=    0.0  FOM=  0.98  TEST= 1
INDE  0  22  62  FOBS=   25.1  SIGMA=  12.4  PHAS= -180.0  FOM=  0.07  TEST= 1
INDE  0  22  64  FOBS=   25.5  SIGMA=  17.8  PHAS= -180.0  FOM=  0.03  TEST= 0
INDE  0  22  66  FOBS=   41.8  SIGMA=  11.1  PHAS=    0.0  FOM=  0.19  TEST= 1
INDE  0  22  68  FOBS=   37.0  SIGMA=  12.5  PHAS= -180.0  FOM=  0.32  TEST= 0
INDE  0  22  70  FOBS=   68.1  SIGMA=   6.9  PHAS=    0.0  FOM=  0.37  TEST= 0
INDE  0  22  72  FOBS=   69.6  SIGMA=   6.7  PHAS= -180.0  FOM=  0.78  TEST= 0
INDE  0  22  74  FOBS=    0.0  SIGMA=  30.9  PHAS=    0.0  FOM=  0.00  TEST= 0
INDE  0  23   1  FOBS=    0.0  SIGMA=  11.5  PHAS=    0.0  FOM=  0.00  TEST= 0
INDE  0  23   5  FOBS=  281.1  SIGMA=   0.5  PHAS=  -90.0  FOM=  0.99  TEST= 0
INDE  0  23   7  FOBS=  143.2  SIGMA=   0.8  PHAS=  -90.0  FOM=  1.00  TEST= 0
INDE  0  23  21  FOBS=  149.4  SIGMA=   1.5  PHAS=   90.0  FOM=  1.00  TEST= 0
INDE  0  23  23  FOBS=  235.9  SIGMA=   1.2  PHAS=  -90.0  FOM=  0.93  TEST= 0
INDE  0  23  25  FOBS=   49.0  SIGMA=   4.6  PHAS=  -90.0  FOM=  0.29  TEST= 0
INDE  0  23  27  FOBS=   41.1  SIGMA=   4.0  PHAS=   90.0  FOM=  0.89  TEST= 0
INDE  0  23  29  FOBS=   71.8  SIGMA=   2.0  PHAS=   90.0  FOM=  1.00  TEST= 0
INDE  0  23  31  FOBS=  121.4  SIGMA=   1.3  PHAS=  -90.0  FOM=  0.87  TEST= 0
INDE  0  23  33  FOBS=    0.0  SIGMA=  16.4  PHAS=    0.0  FOM=  0.00  TEST= 0
INDE  0  23  35  FOBS=  168.8  SIGMA=   1.1  PHAS=  -90.0  FOM=  0.89  TEST= 0
INDE  0  23  37  FOBS=  255.4  SIGMA=   0.9  PHAS=  -90.0  FOM=  1.00  TEST= 0
```

*FIG. 12A - 9*

```
INDE   0  23  39  FOBS=   174.9  SIGMA=   1.0  PHAS=   -90.0  FOM=  1.00  TEST= 0
INDE   0  23  41  FOBS=     0.0  SIGMA=  19.9  PHAS=     0.0  FOM=  0.00  TEST= 0
INDE   0  23  43  FOBS=   303.6  SIGMA=   0.8  PHAS=    90.0  FOM=  0.94  TEST= 1
INDE   0  23  45  FOBS=    75.8  SIGMA=   2.6  PHAS=   -90.0  FOM=  0.91  TEST= 0
INDE   0  23  47  FOBS=    42.9  SIGMA=   6.7  PHAS=   -90.0  FOM=  0.81  TEST= 0
INDE   0  23  49  FOBS=    64.3  SIGMA=   4.4  PHAS=   -90.0  FOM=  0.98  TEST= 0
INDE   0  23  51  FOBS=   241.1  SIGMA=   1.9  PHAS=    90.0  FOM=  1.00  TEST= 0
INDE   0  23  53  FOBS=    31.9  SIGMA=  12.0  PHAS=    90.0  FOM=  0.24  TEST= 0
INDE   0  23  55  FOBS=     0.0  SIGMA=  22.3  PHAS=     0.0  FOM=  0.00  TEST= 0
INDE   0  23  57  FOBS=    38.4  SIGMA=   7.4  PHAS=   -90.0  FOM=  0.61  TEST= 0
INDE   0  23  59  FOBS=     0.0  SIGMA=  23.7  PHAS=     0.0  FOM=  0.00  TEST= 0
INDE   0  23  61  FOBS=    84.7  SIGMA=   3.3  PHAS=    90.0  FOM=  0.75  TEST= 0
INDE   0  23  63  FOBS=    78.9  SIGMA=   4.1  PHAS=    90.0  FOM=  1.00  TEST= 0
INDE   0  23  65  FOBS=   100.9  SIGMA=   4.7  PHAS=    90.0  FOM=  0.20  TEST= 1
INDE   0  23  67  FOBS=     0.0  SIGMA=  30.5  PHAS=     0.0  FOM=  0.00  TEST= 0
INDE   0  23  69  FOBS=    31.7  SIGMA=  14.6  PHAS=    90.0  FOM=  0.09  TEST= 1
INDE   0  23  71  FOBS=    71.9  SIGMA=   6.6  PHAS=    90.0  FOM=  0.46  TEST= 1
INDE   0  23  73  FOBS=    45.6  SIGMA=  10.5  PHAS=   -90.0  FOM=  0.02  TEST= 0
INDE   0  24   2  FOBS=    43.4  SIGMA=   1.6  PHAS=     0.0  FOM=  0.16  TEST= 0
INDE   0  24   4  FOBS=    46.3  SIGMA=   2.6  PHAS=  -180.0  FOM=  0.27  TEST= 0
INDE   0  24   6  FOBS=   359.8  SIGMA=   0.5  PHAS=  -180.0  FOM=  1.00  TEST= 0
INDE   0  24  22  FOBS=    54.9  SIGMA=   3.8  PHAS=     0.0  FOM=  0.57  TEST= 0
INDE   0  24  24  FOBS=   235.1  SIGMA=   1.3  PHAS=     0.0  FOM=  0.50  TEST= 1
INDE   0  24  26  FOBS=   270.0  SIGMA=   1.3  PHAS=     0.0  FOM=  1.00  TEST= 0
INDE   0  24  28  FOBS=   238.1  SIGMA=   0.8  PHAS=     0.0  FOM=  0.94  TEST= 0
INDE   0  24  30  FOBS=   276.1  SIGMA=   0.7  PHAS=  -180.0  FOM=  1.00  TEST= 0
INDE   0  24  32  FOBS=   110.2  SIGMA=   1.5  PHAS=     0.0  FOM=  0.51  TEST= 0
INDE   0  24  34  FOBS=   226.4  SIGMA=   0.9  PHAS=     0.0  FOM=  1.00  TEST= 0
INDE   0  24  36  FOBS=   236.8  SIGMA=   0.9  PHAS=  -180.0  FOM=  1.00  TEST= 0
INDE   0  24  38  FOBS=   207.6  SIGMA=   0.9  PHAS=  -180.0  FOM=  1.00  TEST= 0
INDE   0  24  40  FOBS=     0.0  SIGMA=  23.7  PHAS=     0.0  FOM=  0.00  TEST= 0
INDE   0  24  42  FOBS=   292.2  SIGMA=   0.9  PHAS=     0.0  FOM=  1.00  TEST= 0
INDE   0  24  44  FOBS=     0.0  SIGMA=  19.4  PHAS=     0.0  FOM=  0.00  TEST= 0
INDE   0  24  46  FOBS=   161.1  SIGMA=   1.2  PHAS=  -180.0  FOM=  1.00  TEST= 0
INDE   0  24  48  FOBS=    27.0  SIGMA=  10.6  PHAS=     0.0  FOM=  0.48  TEST= 0
INDE   0  24  50  FOBS=    39.7  SIGMA=   9.9  PHAS=  -180.0  FOM=  0.34  TEST= 0
INDE   0  24  52  FOBS=     0.0  SIGMA=  27.1  PHAS=     0.0  FOM=  0.00  TEST= 0
INDE   0  24  54  FOBS=     0.0  SIGMA=  27.3  PHAS=     0.0  FOM=  0.00  TEST= 0
INDE   0  24  56  FOBS=    44.6  SIGMA=   5.6  PHAS=  -180.0  FOM=  0.48  TEST= 0
INDE   0  24  58  FOBS=    10.2  SIGMA=  24.2  PHAS=     0.0  FOM=  0.00  TEST= 0
INDE   0  24  60  FOBS=     0.0  SIGMA=  21.9  PHAS=     0.0  FOM=  0.00  TEST= 0
INDE   0  24  62  FOBS=     0.0  SIGMA=  25.1  PHAS=     0.0  FOM=  0.00  TEST= 0
INDE   0  24  64  FOBS=    80.6  SIGMA=   4.0  PHAS=     0.0  FOM=  1.00  TEST= 0
INDE   0  24  66  FOBS=     0.0  SIGMA=  30.7  PHAS=     0.0  FOM=  0.00  TEST= 0
INDE   0  24  68  FOBS=    30.7  SIGMA=  15.3  PHAS=  -180.0  FOM=  0.09  TEST= 0
INDE   0  24  70  FOBS=    16.8  SIGMA=  28.5  PHAS=     0.0  FOM=  0.09  TEST= 1
INDE   0  24  72  FOBS=     6.2  SIGMA=  78.7  PHAS=  -180.0  FOM=  0.18  TEST= 0
INDE   0  25   1  FOBS=     0.0  SIGMA=  11.9  PHAS=     0.0  FOM=  0.00  TEST= 0
INDE   0  25   5  FOBS=    33.9  SIGMA=   2.5  PHAS=   -90.0  FOM=  1.00  TEST= 0
INDE   0  25   7  FOBS=    38.7  SIGMA=   2.4  PHAS=   -90.0  FOM=  0.90  TEST= 0
INDE   0  25  23  FOBS=     9.8  SIGMA=  21.6  PHAS=   -90.0  FOM=  0.02  TEST= 0
INDE   0  25  25  FOBS=   376.4  SIGMA=   1.1  PHAS=   -90.0  FOM=  1.00  TEST= 0
INDE   0  25  27  FOBS=   315.3  SIGMA=   1.2  PHAS=   -90.0  FOM=  1.00  TEST= 0
INDE   0  25  29  FOBS=   242.3  SIGMA=   0.7  PHAS=   -90.0  FOM=  1.00  TEST= 0
INDE   0  25  31  FOBS=   210.8  SIGMA=   1.1  PHAS=   -90.0  FOM=  1.00  TEST= 0
INDE   0  25  33  FOBS=    89.9  SIGMA=   1.9  PHAS=   -90.0  FOM=  1.00  TEST= 0
INDE   0  25  35  FOBS=   147.1  SIGMA=   1.2  PHAS=    90.0  FOM=  1.00  TEST= 0
INDE   0  25  37  FOBS=    67.8  SIGMA=   2.5  PHAS=   -90.0  FOM=  1.00  TEST= 0
INDE   0  25  39  FOBS=    48.3  SIGMA=   3.7  PHAS=   -90.0  FOM=  0.37  TEST= 0
INDE   0  25  41  FOBS=    28.5  SIGMA=   7.0  PHAS=   -90.0  FOM=  0.50  TEST= 0
INDE   0  25  43  FOBS=    54.3  SIGMA=   3.6  PHAS=   -90.0  FOM=  0.80  TEST= 0
INDE   0  25  45  FOBS=   228.4  SIGMA=   1.1  PHAS=    90.0  FOM=  1.00  TEST= 0
INDE   0  25  47  FOBS=   160.9  SIGMA=   1.2  PHAS=    90.0  FOM=  0.98  TEST= 0
INDE   0  25  49  FOBS=    78.8  SIGMA=   3.7  PHAS=    90.0  FOM=  1.00  TEST= 0
INDE   0  25  51  FOBS=   125.7  SIGMA=   3.1  PHAS=    90.0  FOM=  0.87  TEST= 0
INDE   0  25  53  FOBS=    85.8  SIGMA=   3.8  PHAS=    90.0  FOM=  0.03  TEST= 1
INDE   0  25  55  FOBS=    31.6  SIGMA=   8.1  PHAS=   -90.0  FOM=  0.08  TEST= 0
INDE   0  25  57  FOBS=   100.5  SIGMA=   2.5  PHAS=    90.0  FOM=  0.88  TEST= 1
INDE   0  25  59  FOBS=   116.4  SIGMA=   2.2  PHAS=    90.0  FOM=  0.99  TEST= 0
INDE   0  25  61  FOBS=    90.5  SIGMA=   3.7  PHAS=    90.0  FOM=  0.97  TEST= 0
```

*FIG. 12A - 10*

```
INDE  0  25  63  FOBS=   17.9  SIGMA=  17.8  PHAS=   -90.0  FOM=  0.27  TEST= 0
INDE  0  25  65  FOBS=   63.0  SIGMA=   7.6  PHAS=   -90.0  FOM=  0.23  TEST= 0
INDE  0  25  67  FOBS=   54.4  SIGMA=   8.6  PHAS=   -90.0  FOM=  0.94  TEST= 0
INDE  0  25  69  FOBS=   28.5  SIGMA=  16.8  PHAS=    90.0  FOM=  0.05  TEST= 0
INDE  0  25  71  FOBS=   67.7  SIGMA=   7.2  PHAS=    90.0  FOM=  0.98  TEST= 0
INDE  0  25  73  FOBS=   81.4  SIGMA=   6.2  PHAS=    90.0  FOM=  0.94  TEST= 0
INDE  0  26   2  FOBS=   69.8  SIGMA=   1.1  PHAS=     0.0  FOM=  1.00  TEST= 0
INDE  0  26   6  FOBS=   73.2  SIGMA=   1.3  PHAS=     0.0  FOM=  0.53  TEST= 0
INDE  0  26   8  FOBS=    0.0  SIGMA=  14.1  PHAS=     0.0  FOM=  0.00  TEST= 0
INDE  0  26  24  FOBS=  217.0  SIGMA=   1.4  PHAS=  -180.0  FOM=  1.00  TEST= 0
INDE  0  26  26  FOBS=  196.2  SIGMA=   1.6  PHAS=  -180.0  FOM=  1.00  TEST= 0
INDE  0  26  28  FOBS=    0.0  SIGMA=  19.4  PHAS=     0.0  FOM=  0.00  TEST= 0
INDE  0  26  30  FOBS=  239.7  SIGMA=   0.9  PHAS=  -180.0  FOM=  1.00  TEST= 0
INDE  0  26  32  FOBS=   54.5  SIGMA=   3.2  PHAS=  -180.0  FOM=  1.00  TEST= 0
INDE  0  26  34  FOBS=  141.8  SIGMA=   1.4  PHAS=     0.0  FOM=  1.00  TEST= 0
INDE  0  26  36  FOBS=   47.3  SIGMA=   4.1  PHAS=     0.0  FOM=  0.61  TEST= 0
INDE  0  26  38  FOBS=  239.7  SIGMA=   1.0  PHAS=  -180.0  FOM=  1.00  TEST= 0
INDE  0  26  40  FOBS=  383.6  SIGMA=   0.7  PHAS=  -180.0  FOM=  0.97  TEST= 0
INDE  0  26  42  FOBS=  171.6  SIGMA=   1.2  PHAS=  -180.0  FOM=  0.99  TEST= 0
INDE  0  26  44  FOBS=   93.7  SIGMA=   2.1  PHAS=  -180.0  FOM=  0.71  TEST= 0
INDE  0  26  46  FOBS=  139.9  SIGMA=   1.4  PHAS=     0.0  FOM=  0.98  TEST= 1
INDE  0  26  48  FOBS=  285.3  SIGMA=   0.8  PHAS=     0.0  FOM=  1.00  TEST= 0
INDE  0  26  50  FOBS=   43.1  SIGMA=   7.3  PHAS=     0.0  FOM=  0.19  TEST= 0
INDE  0  26  52  FOBS=    0.0  SIGMA=  27.1  PHAS=     0.0  FOM=  0.00  TEST= 0
INDE  0  26  54  FOBS=  137.9  SIGMA=   2.4  PHAS=     0.0  FOM=  1.00  TEST= 0
INDE  0  26  56  FOBS=  122.7  SIGMA=   2.0  PHAS=  -180.0  FOM=  0.92  TEST= 0
INDE  0  26  58  FOBS=   34.1  SIGMA=   8.2  PHAS=     0.0  FOM=  0.38  TEST= 0
INDE  0  26  60  FOBS=   72.0  SIGMA=   4.7  PHAS=     0.0  FOM=  0.24  TEST= 0
INDE  0  26  62  FOBS=   32.3  SIGMA=  10.0  PHAS=     0.0  FOM=  0.61  TEST= 0
INDE  0  26  64  FOBS=    0.0  SIGMA=  25.5  PHAS=     0.0  FOM=  0.00  TEST= 0
INDE  0  26  66  FOBS=    0.0  SIGMA=  30.9  PHAS=     0.0  FOM=  0.00  TEST= 1
INDE  0  26  68  FOBS=   78.5  SIGMA=   6.2  PHAS=  -180.0  FOM=  0.84  TEST= 0
INDE  0  26  70  FOBS=    0.0  SIGMA=  31.3  PHAS=     0.0  FOM=  0.00  TEST= 0
INDE  0  26  72  FOBS=   56.9  SIGMA=   8.8  PHAS=     0.0  FOM=  0.82  TEST= 0
INDE  0  27   1  FOBS=   73.8  SIGMA=   1.1  PHAS=   -90.0  FOM=  1.00  TEST= 0
INDE  0  27   5  FOBS=  126.8  SIGMA=   0.8  PHAS=   -90.0  FOM=  1.00  TEST= 1
INDE  0  27   7  FOBS=   69.6  SIGMA=   1.4  PHAS=   -90.0  FOM=  0.23  TEST= 0
INDE  0  27   9  FOBS=  104.9  SIGMA=   1.1  PHAS=    90.0  FOM=  1.00  TEST= 0
INDE  0  27  25  FOBS=   84.0  SIGMA=   3.1  PHAS=   -90.0  FOM=  0.06  TEST= 1
INDE  0  27  27  FOBS=   94.3  SIGMA=   3.0  PHAS=   -90.0  FOM=  0.11  TEST= 1
INDE  0  27  29  FOBS=  235.5  SIGMA=   1.6  PHAS=    90.0  FOM=  1.00  TEST= 0
INDE  0  27  31  FOBS=    0.0  SIGMA=  18.5  PHAS=     0.0  FOM=  0.00  TEST= 0
INDE  0  27  33  FOBS=  205.1  SIGMA=   1.1  PHAS=    90.0  FOM=  0.85  TEST= 0
INDE  0  27  35  FOBS=   61.4  SIGMA=   3.2  PHAS=   -90.0  FOM=  1.00  TEST= 0
INDE  0  27  37  FOBS=   19.9  SIGMA=  10.5  PHAS=   -90.0  FOM=  0.99  TEST= 0
INDE  0  27  39  FOBS=    0.0  SIGMA=  20.2  PHAS=     0.0  FOM=  0.00  TEST= 0
INDE  0  27  41  FOBS=   23.6  SIGMA=   8.4  PHAS=    90.0  FOM=  0.90  TEST= 0
INDE  0  27  43  FOBS=  317.2  SIGMA=   0.8  PHAS=   -90.0  FOM=  1.00  TEST= 0
INDE  0  27  45  FOBS=   39.5  SIGMA=   4.8  PHAS=   -90.0  FOM=  0.70  TEST= 0
INDE  0  27  47  FOBS=   41.6  SIGMA=   4.5  PHAS=   -90.0  FOM=  0.20  TEST= 0
INDE  0  27  49  FOBS=   89.4  SIGMA=   2.1  PHAS=    90.0  FOM=  0.79  TEST= 0
INDE  0  27  51  FOBS=  166.2  SIGMA=   2.5  PHAS=    90.0  FOM=  1.00  TEST= 0
INDE  0  27  53  FOBS=   77.1  SIGMA=   4.2  PHAS=    90.0  FOM=  0.80  TEST= 0
INDE  0  27  55  FOBS=   22.4  SIGMA=  14.1  PHAS=    90.0  FOM=  0.44  TEST= 1
INDE  0  27  57  FOBS=   77.9  SIGMA=   2.7  PHAS=    90.0  FOM=  0.36  TEST= 0
INDE  0  27  59  FOBS=   90.3  SIGMA=   2.9  PHAS=    90.0  FOM=  1.00  TEST= 0
INDE  0  27  61  FOBS=    0.0  SIGMA=  25.6  PHAS=     0.0  FOM=  0.00  TEST= 0
INDE  0  27  63  FOBS=   40.7  SIGMA=   8.1  PHAS=   -90.0  FOM=  0.31  TEST= 0
INDE  0  27  65  FOBS=    0.0  SIGMA=  31.3  PHAS=     0.0  FOM=  0.00  TEST= 0
INDE  0  27  67  FOBS=    0.0  SIGMA=  31.2  PHAS=     0.0  FOM=  0.00  TEST= 0
INDE  0  27  69  FOBS=    0.0  SIGMA=  31.6  PHAS=     0.0  FOM=  0.00  TEST= 0
INDE  0  27  71  FOBS=    0.0  SIGMA=  31.5  PHAS=     0.0  FOM=  0.00  TEST= 0
INDE  0  28   2  FOBS=  145.7  SIGMA=   0.7  PHAS=     0.0  FOM=  0.99  TEST= 0
INDE  0  28   6  FOBS=   40.8  SIGMA=   2.4  PHAS=     0.0  FOM=  0.40  TEST= 0
INDE  0  28   8  FOBS=   83.7  SIGMA=   1.3  PHAS=  -180.0  FOM=  0.94  TEST= 0
INDE  0  28  26  FOBS=  127.5  SIGMA=   2.3  PHAS=     0.0  FOM=  0.95  TEST= 0
INDE  0  28  28  FOBS=    0.0  SIGMA=  24.2  PHAS=     0.0  FOM=  0.00  TEST= 0
INDE  0  28  30  FOBS=   73.3  SIGMA=   2.5  PHAS=  -180.0  FOM=  0.61  TEST= 0
INDE  0  28  32  FOBS=  356.5  SIGMA=   0.8  PHAS=     0.0  FOM=  0.99  TEST= 0
INDE  0  28  34  FOBS=   28.7  SIGMA=   6.9  PHAS=     0.0  FOM=  0.34  TEST= 0
```

*FIG. 12A - 11*

```
INDE  0  28  36 FOBS=   44.4 SIGMA=   4.8 PHAS= -180.0 FOM= 1.00 TEST= 0
INDE  0  28  38 FOBS=   82.4 SIGMA=   2.8 PHAS= -180.0 FOM= 0.33 TEST= 0
INDE  0  28  40 FOBS=  202.2 SIGMA=   1.3 PHAS=    0.0 FOM= 1.00 TEST= 0
INDE  0  28  42 FOBS=    0.0 SIGMA=  19.8 PHAS=    0.0 FOM= 0.00 TEST= 0
INDE  0  28  44 FOBS=   16.0 SIGMA=  12.0 PHAS= -180.0 FOM= 0.23 TEST= 0
INDE  0  28  46 FOBS=    0.0 SIGMA=  19.3 PHAS=    0.0 FOM= 0.00 TEST= 0
INDE  0  28  48 FOBS=  132.6 SIGMA=   1.5 PHAS=    0.0 FOM= 1.00 TEST= 0
INDE  0  28  50 FOBS=   57.3 SIGMA=   3.5 PHAS=    0.0 FOM= 1.00 TEST= 1
INDE  0  28  52 FOBS=  168.7 SIGMA=   2.5 PHAS=    0.0 FOM= 1.00 TEST= 0
INDE  0  28  54 FOBS=  121.3 SIGMA=   2.7 PHAS=    0.0 FOM= 1.00 TEST= 0
INDE  0  28  56 FOBS=   12.6 SIGMA=  23.6 PHAS=    0.0 FOM= 0.00 TEST= 1
INDE  0  28  58 FOBS=   36.6 SIGMA=   5.8 PHAS=    0.0 FOM= 0.05 TEST= 0
INDE  0  28  60 FOBS=   40.7 SIGMA=   6.8 PHAS= -180.0 FOM= 0.45 TEST= 0
INDE  0  28  62 FOBS=   43.0 SIGMA=   7.7 PHAS= -180.0 FOM= 0.51 TEST= 0
INDE  0  28  64 FOBS=   47.1 SIGMA=   7.1 PHAS=    0.0 FOM= 0.12 TEST= 0
INDE  0  28  66 FOBS=    0.0 SIGMA=  31.4 PHAS=    0.0 FOM= 0.00 TEST= 0
INDE  0  28  68 FOBS=  136.6 SIGMA=   3.9 PHAS= -180.0 FOM= 1.00 TEST= 0
INDE  0  28  70 FOBS=   95.6 SIGMA=   5.4 PHAS= -180.0 FOM= 0.69 TEST= 1
INDE  0  28  72 FOBS=   41.7 SIGMA=  12.2 PHAS=    0.0 FOM= 0.19 TEST= 0
INDE  0  29   1 FOBS=  127.8 SIGMA=   0.8 PHAS=  -90.0 FOM= 1.00 TEST= 0
INDE  0  29   7 FOBS=   68.2 SIGMA=   1.5 PHAS=  -90.0 FOM= 0.85 TEST= 0
INDE  0  29   9 FOBS=   83.1 SIGMA=   1.5 PHAS=  -90.0 FOM= 1.00 TEST= 0
INDE  0  29  25 FOBS=   20.4 SIGMA=  18.7 PHAS=   90.0 FOM= 0.03 TEST= 0
INDE  0  29  27 FOBS=    0.0 SIGMA=  23.5 PHAS=    0.0 FOM= 0.00 TEST= 0
INDE  0  29  29 FOBS=   83.5 SIGMA=   2.7 PHAS=  -90.0 FOM= 1.00 TEST= 0
INDE  0  29  31 FOBS=  304.9 SIGMA=   0.9 PHAS=  -90.0 FOM= 1.00 TEST= 0
INDE  0  29  33 FOBS=   55.7 SIGMA=   3.7 PHAS=   90.0 FOM= 0.04 TEST= 0
INDE  0  29  35 FOBS=  117.4 SIGMA=   1.9 PHAS=   90.0 FOM= 0.07 TEST= 0
INDE  0  29  37 FOBS=    0.0 SIGMA=  22.2 PHAS=    0.0 FOM= 0.00 TEST= 0
INDE  0  29  39 FOBS=   21.0 SIGMA=  11.2 PHAS=  -90.0 FOM= 0.11 TEST= 0
INDE  0  29  41 FOBS=   32.0 SIGMA=   7.2 PHAS=  -90.0 FOM= 0.24 TEST= 0
INDE  0  29  43 FOBS=    0.0 SIGMA=  22.5 PHAS=    0.0 FOM= 0.00 TEST= 0
INDE  0  29  45 FOBS=  158.7 SIGMA=   1.3 PHAS=  -90.0 FOM= 1.00 TEST= 0
INDE  0  29  47 FOBS=    0.0 SIGMA=  19.2 PHAS=    0.0 FOM= 0.00 TEST= 0
INDE  0  29  49 FOBS=  166.2 SIGMA=   1.2 PHAS=  -90.0 FOM= 1.00 TEST= 0
INDE  0  29  51 FOBS=   70.7 SIGMA=   2.8 PHAS=   90.0 FOM= 0.66 TEST= 0
INDE  0  29  53 FOBS=  104.1 SIGMA=   3.1 PHAS=  -90.0 FOM= 0.95 TEST= 0
INDE  0  29  55 FOBS=   76.8 SIGMA=   4.2 PHAS=  -90.0 FOM= 0.98 TEST= 0
INDE  0  29  57 FOBS=    0.0 SIGMA=  22.7 PHAS=    0.0 FOM= 0.00 TEST= 0
INDE  0  29  59 FOBS=   92.3 SIGMA=   2.8 PHAS=   90.0 FOM= 1.00 TEST= 0
INDE  0  29  61 FOBS=    0.0 SIGMA=  25.8 PHAS=    0.0 FOM= 0.00 TEST= 0
INDE  0  29  63 FOBS=   10.5 SIGMA=  31.3 PHAS=  -90.0 FOM= 0.04 TEST= 0
INDE  0  29  65 FOBS=   41.0 SIGMA=  12.4 PHAS=  -90.0 FOM= 0.21 TEST= 0
INDE  0  29  67 FOBS=  125.3 SIGMA=   4.2 PHAS=   90.0 FOM= 0.94 TEST= 0
INDE  0  29  69 FOBS=   91.8 SIGMA=   5.7 PHAS=   90.0 FOM= 1.00 TEST= 0
INDE  0  29  71 FOBS=   74.5 SIGMA=   7.0 PHAS=  -90.0 FOM= 0.17 TEST= 0
INDE  0  30   0 FOBS=  187.5 SIGMA=   0.6 PHAS=    0.0 FOM= 1.00 TEST= 0
INDE  0  30   2 FOBS=  180.0 SIGMA=   0.6 PHAS= -180.0 FOM= 1.00 TEST= 0
INDE  0  30   6 FOBS=   81.2 SIGMA=   1.3 PHAS=    0.0 FOM= 1.00 TEST= 0
INDE  0  30   8 FOBS=  109.6 SIGMA=   1.1 PHAS= -180.0 FOM= 1.00 TEST= 0
INDE  0  30  10 FOBS=   63.9 SIGMA=   2.0 PHAS= -180.0 FOM= 1.00 TEST= 0
INDE  0  30  26 FOBS=  115.3 SIGMA=   2.6 PHAS= -180.0 FOM= 0.83 TEST= 0
INDE  0  30  28 FOBS=  252.5 SIGMA=   1.6 PHAS= -180.0 FOM= 1.00 TEST= 0
INDE  0  30  30 FOBS=  231.0 SIGMA=   1.6 PHAS= -180.0 FOM= 1.00 TEST= 0
INDE  0  30  32 FOBS=    0.0 SIGMA=  20.3 PHAS=    0.0 FOM= 0.00 TEST= 0
INDE  0  30  34 FOBS=  302.4 SIGMA=   0.9 PHAS= -180.0 FOM= 1.00 TEST= 0
INDE  0  30  36 FOBS=   61.7 SIGMA=   3.8 PHAS= -180.0 FOM= 1.00 TEST= 0
INDE  0  30  38 FOBS=  124.9 SIGMA=   2.0 PHAS=    0.0 FOM= 1.00 TEST= 0
INDE  0  30  40 FOBS=  167.7 SIGMA=   1.5 PHAS= -180.0 FOM= 0.95 TEST= 0
INDE  0  30  42 FOBS=   64.3 SIGMA=   3.5 PHAS= -180.0 FOM= 0.99 TEST= 0
INDE  0  30  44 FOBS=  257.0 SIGMA=   1.0 PHAS= -180.0 FOM= 1.00 TEST= 0
INDE  0  30  46 FOBS=    0.0 SIGMA=  19.9 PHAS=    0.0 FOM= 0.00 TEST= 0
INDE  0  30  48 FOBS=    5.2 SIGMA=  35.6 PHAS= -180.0 FOM= 0.06 TEST= 0
INDE  0  30  50 FOBS=   25.0 SIGMA=   8.2 PHAS=    0.0 FOM= 0.05 TEST= 0
INDE  0  30  52 FOBS=    9.2 SIGMA=  23.2 PHAS=    0.0 FOM= 0.06 TEST= 0
INDE  0  30  54 FOBS=  109.0 SIGMA=   3.0 PHAS= -180.0 FOM= 1.00 TEST= 0
INDE  0  30  56 FOBS=   26.9 SIGMA=  14.2 PHAS=    0.0 FOM= 0.24 TEST= 0
INDE  0  30  58 FOBS=    0.0 SIGMA=  27.3 PHAS=    0.0 FOM= 0.00 TEST= 0
INDE  0  30  60 FOBS=    0.0 SIGMA=  22.1 PHAS=    0.0 FOM= 0.00 TEST= 0
INDE  0  30  62 FOBS=   20.8 SIGMA=  14.0 PHAS=    0.0 FOM= 0.20 TEST= 0
```

*FIG. 12A - 12*

| | | | | | | | | | | | |
|---|---|---|---|---|---|---|---|---|---|---|---|
| INDE | 0 | 30 | 64 | FOBS= | 0.0 | SIGMA= | 25.9 | PHAS= | 0.0 | FOM= 0.00 | TEST= 0 |
| INDE | 0 | 30 | 66 | FOBS= | 0.0 | SIGMA= | 31.9 | PHAS= | 0.0 | FOM= 0.00 | TEST= 0 |
| INDE | 0 | 30 | 68 | FOBS= | 32.3 | SIGMA= | 16.1 | PHAS= | -180.0 | FOM= 0.24 | TEST= 1 |
| INDE | 0 | 30 | 70 | FOBS= | 51.7 | SIGMA= | 9.8 | PHAS= | 0.0 | FOM= 0.90 | TEST= 0 |
| INDE | 0 | 31 | 1 | FOBS= | 90.7 | SIGMA= | 1.1 | PHAS= | 90.0 | FOM= 1.00 | TEST= 0 |
| INDE | 0 | 31 | 7 | FOBS= | 0.0 | SIGMA= | 14.7 | PHAS= | 0.0 | FOM= 0.00 | TEST= 0 |
| INDE | 0 | 31 | 9 | FOBS= | 121.6 | SIGMA= | 1.1 | PHAS= | -90.0 | FOM= 1.00 | TEST= 0 |
| INDE | 0 | 31 | 11 | FOBS= | 107.4 | SIGMA= | 1.3 | PHAS= | 90.0 | FOM= 0.74 | TEST= 0 |
| INDE | 0 | 31 | 27 | FOBS= | 103.0 | SIGMA= | 3.2 | PHAS= | 90.0 | FOM= 0.77 | TEST= 0 |
| INDE | 0 | 31 | 29 | FOBS= | 0.0 | SIGMA= | 25.9 | PHAS= | 0.0 | FOM= 0.00 | TEST= 0 |
| INDE | 0 | 31 | 31 | FOBS= | 38.1 | SIGMA= | 6.0 | PHAS= | -90.0 | FOM= 0.96 | TEST= 0 |
| INDE | 0 | 31 | 33 | FOBS= | 380.6 | SIGMA= | 0.8 | PHAS= | 90.0 | FOM= 1.00 | TEST= 0 |
| INDE | 0 | 31 | 35 | FOBS= | 7.6 | SIGMA= | 30.9 | PHAS= | 90.0 | FOM= 0.08 | TEST= 1 |
| INDE | 0 | 31 | 37 | FOBS= | 175.4 | SIGMA= | 1.5 | PHAS= | -90.0 | FOM= 1.00 | TEST= 0 |
| INDE | 0 | 31 | 39 | FOBS= | 0.0 | SIGMA= | 22.0 | PHAS= | 0.0 | FOM= 0.00 | TEST= 1 |
| INDE | 0 | 31 | 41 | FOBS= | 104.9 | SIGMA= | 2.3 | PHAS= | 90.0 | FOM= 0.09 | TEST= 0 |
| INDE | 0 | 31 | 43 | FOBS= | 77.1 | SIGMA= | 3.0 | PHAS= | 90.0 | FOM= 1.00 | TEST= 0 |
| INDE | 0 | 31 | 45 | FOBS= | 0.0 | SIGMA= | 21.0 | PHAS= | 0.0 | FOM= 0.00 | TEST= 0 |
| INDE | 0 | 31 | 47 | FOBS= | 146.5 | SIGMA= | 1.7 | PHAS= | -90.0 | FOM= 1.00 | TEST= 0 |
| INDE | 0 | 31 | 49 | FOBS= | 21.5 | SIGMA= | 8.6 | PHAS= | -90.0 | FOM= 0.19 | TEST= 0 |
| INDE | 0 | 31 | 51 | FOBS= | 43.2 | SIGMA= | 4.5 | PHAS= | 90.0 | FOM= 0.99 | TEST= 0 |
| INDE | 0 | 31 | 53 | FOBS= | 0.0 | SIGMA= | 20.5 | PHAS= | 0.0 | FOM= 0.00 | TEST= 0 |
| INDE | 0 | 31 | 55 | FOBS= | 58.4 | SIGMA= | 5.3 | PHAS= | 90.0 | FOM= 0.87 | TEST= 0 |
| INDE | 0 | 31 | 57 | FOBS= | 0.0 | SIGMA= | 20.5 | PHAS= | 0.0 | FOM= 0.00 | TEST= 0 |
| INDE | 0 | 31 | 59 | FOBS= | 61.7 | SIGMA= | 4.1 | PHAS= | -90.0 | FOM= 0.43 | TEST= 0 |
| INDE | 0 | 31 | 61 | FOBS= | 0.0 | SIGMA= | 26.0 | PHAS= | 0.0 | FOM= 0.00 | TEST= 0 |
| INDE | 0 | 31 | 63 | FOBS= | 45.9 | SIGMA= | 5.4 | PHAS= | -90.0 | FOM= 0.13 | TEST= 0 |
| INDE | 0 | 31 | 65 | FOBS= | 18.9 | SIGMA= | 27.4 | PHAS= | -90.0 | FOM= 0.16 | TEST= 0 |
| INDE | 0 | 31 | 67 | FOBS= | 89.5 | SIGMA= | 5.9 | PHAS= | 90.0 | FOM= 0.97 | TEST= 0 |
| INDE | 0 | 31 | 69 | FOBS= | 0.0 | SIGMA= | 32.2 | PHAS= | 0.0 | FOM= 0.00 | TEST= 0 |
| INDE | 0 | 31 | 71 | FOBS= | 28.1 | SIGMA= | 18.7 | PHAS= | -90.0 | FOM= 0.20 | TEST= 0 |
| INDE | 0 | 32 | 0 | FOBS= | 260.6 | SIGMA= | 0.5 | PHAS= | -180.0 | FOM= 0.97 | TEST= 0 |
| INDE | 0 | 32 | 2 | FOBS= | 42.6 | SIGMA= | 2.3 | PHAS= | -180.0 | FOM= 0.94 | TEST= 0 |
| INDE | 0 | 32 | 6 | FOBS= | 31.1 | SIGMA= | 3.5 | PHAS= | -180.0 | FOM= 0.92 | TEST= 0 |
| INDE | 0 | 32 | 8 | FOBS= | 155.1 | SIGMA= | 0.9 | PHAS= | -180.0 | FOM= 1.00 | TEST= 0 |
| INDE | 0 | 32 | 10 | FOBS= | 78.2 | SIGMA= | 1.7 | PHAS= | -180.0 | FOM= 0.91 | TEST= 0 |
| INDE | 0 | 32 | 28 | FOBS= | 125.8 | SIGMA= | 2.8 | PHAS= | 0.0 | FOM= 0.80 | TEST= 0 |
| INDE | 0 | 32 | 30 | FOBS= | 79.7 | SIGMA= | 3.2 | PHAS= | -180.0 | FOM= 0.91 | TEST= 1 |
| INDE | 0 | 32 | 32 | FOBS= | 289.2 | SIGMA= | 1.0 | PHAS= | 0.0 | FOM= 1.00 | TEST= 0 |
| INDE | 0 | 32 | 34 | FOBS= | 23.2 | SIGMA= | 10.4 | PHAS= | -180.0 | FOM= 0.48 | TEST= 0 |
| INDE | 0 | 32 | 36 | FOBS= | 118.5 | SIGMA= | 2.2 | PHAS= | -180.0 | FOM= 0.99 | TEST= 0 |
| INDE | 0 | 32 | 38 | FOBS= | 0.0 | SIGMA= | 22.2 | PHAS= | 0.0 | FOM= 0.00 | TEST= 0 |
| INDE | 0 | 32 | 40 | FOBS= | 270.7 | SIGMA= | 1.3 | PHAS= | -180.0 | FOM= 1.00 | TEST= 0 |
| INDE | 0 | 32 | 42 | FOBS= | 150.9 | SIGMA= | 1.6 | PHAS= | -180.0 | FOM= 0.08 | TEST= 1 |
| INDE | 0 | 32 | 44 | FOBS= | 0.0 | SIGMA= | 21.1 | PHAS= | 0.0 | FOM= 0.00 | TEST= 0 |
| INDE | 0 | 32 | 46 | FOBS= | 46.1 | SIGMA= | 4.8 | PHAS= | 0.0 | FOM= 0.96 | TEST= 0 |
| INDE | 0 | 32 | 48 | FOBS= | 41.2 | SIGMA= | 5.2 | PHAS= | -180.0 | FOM= 0.47 | TEST= 0 |
| INDE | 0 | 32 | 50 | FOBS= | 35.2 | SIGMA= | 6.4 | PHAS= | 0.0 | FOM= 0.45 | TEST= 0 |
| INDE | 0 | 32 | 52 | FOBS= | 22.0 | SIGMA= | 9.5 | PHAS= | 0.0 | FOM= 0.11 | TEST= 0 |
| INDE | 0 | 32 | 54 | FOBS= | 84.7 | SIGMA= | 3.0 | PHAS= | 0.0 | FOM= 0.97 | TEST= 0 |
| INDE | 0 | 32 | 56 | FOBS= | 87.1 | SIGMA= | 3.5 | PHAS= | 0.0 | FOM= 0.69 | TEST= 0 |
| INDE | 0 | 32 | 58 | FOBS= | 28.8 | SIGMA= | 8.7 | PHAS= | -180.0 | FOM= 0.52 | TEST= 0 |
| INDE | 0 | 32 | 60 | FOBS= | 19.0 | SIGMA= | 13.2 | PHAS= | 0.0 | FOM= 0.44 | TEST= 0 |
| INDE | 0 | 32 | 62 | FOBS= | 73.3 | SIGMA= | 3.5 | PHAS= | 0.0 | FOM= 0.61 | TEST= 0 |
| INDE | 0 | 32 | 64 | FOBS= | 58.8 | SIGMA= | 4.3 | PHAS= | 0.0 | FOM= 0.10 | TEST= 0 |
| INDE | 0 | 32 | 66 | FOBS= | 0.0 | SIGMA= | 32.3 | PHAS= | 0.0 | FOM= 0.00 | TEST= 0 |
| INDE | 0 | 32 | 68 | FOBS= | 0.0 | SIGMA= | 32.3 | PHAS= | 0.0 | FOM= 0.00 | TEST= 0 |
| INDE | 0 | 32 | 70 | FOBS= | 0.0 | SIGMA= | 32.4 | PHAS= | 0.0 | FOM= 0.00 | TEST= 0 |
| INDE | 0 | 33 | 1 | FOBS= | 30.2 | SIGMA= | 3.2 | PHAS= | -90.0 | FOM= 1.00 | TEST= 0 |
| INDE | 0 | 33 | 7 | FOBS= | 67.1 | SIGMA= | 1.8 | PHAS= | 90.0 | FOM= 1.00 | TEST= 0 |
| INDE | 0 | 33 | 9 | FOBS= | 55.5 | SIGMA= | 2.3 | PHAS= | -90.0 | FOM= 0.46 | TEST= 0 |
| INDE | 0 | 33 | 11 | FOBS= | 13.0 | SIGMA= | 10.5 | PHAS= | -90.0 | FOM= 0.46 | TEST= 0 |
| INDE | 0 | 33 | 29 | FOBS= | 111.8 | SIGMA= | 3.4 | PHAS= | -90.0 | FOM= 0.06 | TEST= 0 |
| INDE | 0 | 33 | 31 | FOBS= | 223.8 | SIGMA= | 1.2 | PHAS= | -90.0 | FOM= 1.00 | TEST= 0 |
| INDE | 0 | 33 | 33 | FOBS= | 88.9 | SIGMA= | 2.8 | PHAS= | 90.0 | FOM= 1.00 | TEST= 1 |
| INDE | 0 | 33 | 35 | FOBS= | 78.4 | SIGMA= | 3.3 | PHAS= | 90.0 | FOM= 0.29 | TEST= 0 |
| INDE | 0 | 33 | 37 | FOBS= | 0.0 | SIGMA= | 22.5 | PHAS= | 0.0 | FOM= 0.00 | TEST= 0 |
| INDE | 0 | 33 | 39 | FOBS= | 76.9 | SIGMA= | 3.2 | PHAS= | 90.0 | FOM= 1.00 | TEST= 0 |
| INDE | 0 | 33 | 41 | FOBS= | 0.0 | SIGMA= | 21.6 | PHAS= | 0.0 | FOM= 0.00 | TEST= 0 |
| INDE | 0 | 33 | 43 | FOBS= | 142.9 | SIGMA= | 1.7 | PHAS= | -90.0 | FOM= 1.00 | TEST= 0 |

*FIG. 12A - 13*

```
INDE  0  33  45  FOBS=   192.6  SIGMA=   1.3  PHAS=   -90.0  FOM=  1.00  TEST= 0
INDE  0  33  47  FOBS=   263.1  SIGMA=   1.0  PHAS=   -90.0  FOM=  1.00  TEST= 0
INDE  0  33  49  FOBS=   160.5  SIGMA=   1.4  PHAS=   -90.0  FOM=  0.84  TEST= 1
INDE  0  33  51  FOBS=     0.0  SIGMA=  21.4  PHAS=     0.0  FOM=  0.00  TEST= 0
INDE  0  33  53  FOBS=    67.0  SIGMA=   2.9  PHAS=   -90.0  FOM=  1.00  TEST= 0
INDE  0  33  55  FOBS=    74.6  SIGMA=   3.4  PHAS=   -90.0  FOM=  0.97  TEST= 0
INDE  0  33  57  FOBS=     0.0  SIGMA=  26.8  PHAS=     0.0  FOM=  0.00  TEST= 0
INDE  0  33  59  FOBS=    65.5  SIGMA=   3.9  PHAS=   -90.0  FOM=  0.33  TEST= 0
INDE  0  33  61  FOBS=    42.0  SIGMA=   6.0  PHAS=   -90.0  FOM=  0.19  TEST= 0
INDE  0  33  63  FOBS=     0.0  SIGMA=  22.4  PHAS=     0.0  FOM=  0.00  TEST= 0
INDE  0  33  65  FOBS=    24.2  SIGMA=  10.5  PHAS=    90.0  FOM=  0.42  TEST= 0
INDE  0  33  67  FOBS=    82.4  SIGMA=   6.7  PHAS=   -90.0  FOM=  0.92  TEST= 0
INDE  0  33  69  FOBS=     0.0  SIGMA=  32.5  PHAS=     0.0  FOM=  0.00  TEST= 0
INDE  0  34   0  FOBS=    30.5  SIGMA=   3.4  PHAS=     0.0  FOM=  0.33  TEST= 0
INDE  0  34   2  FOBS=   194.9  SIGMA=   0.7  PHAS=  -180.0  FOM=  1.00  TEST= 0
INDE  0  34   8  FOBS=    47.3  SIGMA=   2.7  PHAS=     0.0  FOM=  0.98  TEST= 0
INDE  0  34  10  FOBS=    81.1  SIGMA=   1.7  PHAS=     0.0  FOM=  1.00  TEST= 0
INDE  0  34  12  FOBS=    94.0  SIGMA=   1.6  PHAS=     0.0  FOM=  0.11  TEST= 0
INDE  0  34  30  FOBS=   211.1  SIGMA=   1.5  PHAS=     0.0  FOM=  0.27  TEST= 0
INDE  0  34  32  FOBS=    73.0  SIGMA=   3.4  PHAS=     0.0  FOM=  0.63  TEST= 0
INDE  0  34  34  FOBS=     0.0  SIGMA=  27.3  PHAS=     0.0  FOM=  0.00  TEST= 0
INDE  0  34  36  FOBS=     0.0  SIGMA=  25.4  PHAS=     0.0  FOM=  0.00  TEST= 0
INDE  0  34  38  FOBS=   186.9  SIGMA=   1.5  PHAS=     0.0  FOM=  1.00  TEST= 0
INDE  0  34  40  FOBS=    87.3  SIGMA=   2.8  PHAS=  -180.0  FOM=  0.08  TEST= 0
INDE  0  34  42  FOBS=     0.0  SIGMA=  21.6  PHAS=     0.0  FOM=  0.00  TEST= 0
INDE  0  34  44  FOBS=   141.1  SIGMA=   1.7  PHAS=  -180.0  FOM=  0.95  TEST= 0
INDE  0  34  46  FOBS=   173.7  SIGMA=   1.4  PHAS=  -180.0  FOM=  1.00  TEST= 0
INDE  0  34  48  FOBS=    55.2  SIGMA=   4.0  PHAS=     0.0  FOM=  0.32  TEST= 0
INDE  0  34  50  FOBS=    13.0  SIGMA=  19.7  PHAS=  -180.0  FOM=  0.20  TEST= 0
INDE  0  34  52  FOBS=    85.6  SIGMA=   2.7  PHAS=  -180.0  FOM=  0.51  TEST= 0
INDE  0  34  54  FOBS=     0.0  SIGMA=  25.0  PHAS=     0.0  FOM=  0.00  TEST= 0
INDE  0  34  56  FOBS=     0.0  SIGMA=  25.3  PHAS=     0.0  FOM=  0.00  TEST= 0
INDE  0  34  58  FOBS=    47.9  SIGMA=   5.3  PHAS=  -180.0  FOM=  0.76  TEST= 0
INDE  0  34  60  FOBS=     0.0  SIGMA=  23.7  PHAS=     0.0  FOM=  0.00  TEST= 0
INDE  0  34  62  FOBS=    27.8  SIGMA=   9.2  PHAS=     0.0  FOM=  0.40  TEST= 0
INDE  0  34  64  FOBS=     0.0  SIGMA=  22.3  PHAS=     0.0  FOM=  0.00  TEST= 0
INDE  0  34  66  FOBS=    30.4  SIGMA=  12.4  PHAS=  -180.0  FOM=  0.03  TEST= 0
INDE  0  34  68  FOBS=     0.0  SIGMA=  32.8  PHAS=     0.0  FOM=  0.00  TEST= 0
INDE  0  35   1  FOBS=    47.9  SIGMA=   2.2  PHAS=   -90.0  FOM=  0.08  TEST= 0
INDE  0  35   7  FOBS=   154.1  SIGMA=   0.9  PHAS=   -90.0  FOM=  1.00  TEST= 1
INDE  0  35   9  FOBS=   134.2  SIGMA=   1.1  PHAS=   -90.0  FOM=  1.00  TEST= 0
INDE  0  35  11  FOBS=   189.9  SIGMA=   0.9  PHAS=   -90.0  FOM=  1.00  TEST= 0
INDE  0  35  13  FOBS=   145.7  SIGMA=   1.2  PHAS=    90.0  FOM=  0.49  TEST= 0
INDE  0  35  29  FOBS=    87.4  SIGMA=   6.4  PHAS=    90.0  FOM=  0.14  TEST= 0
INDE  0  35  31  FOBS=   121.0  SIGMA=   2.5  PHAS=   -90.0  FOM=  0.99  TEST= 0
INDE  0  35  33  FOBS=     0.0  SIGMA=  24.1  PHAS=     0.0  FOM=  0.00  TEST= 0
INDE  0  35  35  FOBS=   190.7  SIGMA=   1.5  PHAS=   -90.0  FOM=  1.00  TEST= 0
INDE  0  35  37  FOBS=   205.0  SIGMA=   1.4  PHAS=   -90.0  FOM=  1.00  TEST= 0
INDE  0  35  39  FOBS=   179.0  SIGMA=   1.5  PHAS=   -90.0  FOM=  1.00  TEST= 0
INDE  0  35  41  FOBS=    56.3  SIGMA=   4.3  PHAS=   -90.0  FOM=  0.36  TEST= 0
INDE  0  35  43  FOBS=   150.1  SIGMA=   1.7  PHAS=   -90.0  FOM=  1.00  TEST= 0
INDE  0  35  45  FOBS=    21.1  SIGMA=  11.9  PHAS=   -90.0  FOM=  0.24  TEST= 0
INDE  0  35  47  FOBS=   142.9  SIGMA=   1.7  PHAS=   -90.0  FOM=  1.00  TEST= 0
INDE  0  35  49  FOBS=    99.9  SIGMA=   2.3  PHAS=    90.0  FOM=  0.99  TEST= 0
INDE  0  35  51  FOBS=     0.0  SIGMA=  22.7  PHAS=     0.0  FOM=  0.00  TEST= 1
INDE  0  35  53  FOBS=    32.8  SIGMA=   9.5  PHAS=   -90.0  FOM=  0.09  TEST= 0
INDE  0  35  55  FOBS=    43.1  SIGMA=   7.3  PHAS=    90.0  FOM=  0.71  TEST= 0
INDE  0  35  57  FOBS=    15.9  SIGMA=  17.5  PHAS=    90.0  FOM=  0.01  TEST= 0
INDE  0  35  59  FOBS=    11.6  SIGMA=  21.7  PHAS=    90.0  FOM=  0.11  TEST= 0
INDE  0  35  61  FOBS=    98.9  SIGMA=   2.6  PHAS=   -90.0  FOM=  1.00  TEST= 0
INDE  0  35  63  FOBS=    83.0  SIGMA=   3.2  PHAS=   -90.0  FOM=  0.17  TEST= 0
INDE  0  35  65  FOBS=     6.3  SIGMA=  40.8  PHAS=    90.0  FOM=  0.10  TEST= 0
INDE  0  35  67  FOBS=    81.6  SIGMA=   3.9  PHAS=   -90.0  FOM=  1.00  TEST= 0
INDE  0  35  69  FOBS=     0.0  SIGMA=  33.2  PHAS=     0.0  FOM=  0.00  TEST= 0
INDE  0  36   0  FOBS=   133.3  SIGMA=   0.9  PHAS=  -180.0  FOM=  1.00  TEST= 0
INDE  0  36   2  FOBS=   149.7  SIGMA=   0.9  PHAS=  -180.0  FOM=  0.99  TEST= 0
INDE  0  36   8  FOBS=   111.2  SIGMA=   1.3  PHAS=  -180.0  FOM=  0.99  TEST= 0
INDE  0  36  10  FOBS=   236.4  SIGMA=   0.8  PHAS=  -180.0  FOM=  0.97  TEST= 0
INDE  0  36  12  FOBS=    96.0  SIGMA=   1.8  PHAS=  -180.0  FOM=  1.00  TEST= 0
INDE  0  36  30  FOBS=     0.0  SIGMA=  34.1  PHAS=     0.0  FOM=  0.00  TEST= 0
```

*FIG. 12A - 14*

```
INDE  0  36  32 FOBS=  201.7 SIGMA=  1.4 PHAS= -180.0 FOM= 0.13 TEST= 1
INDE  0  36  34 FOBS=    0.0 SIGMA= 23.1 PHAS=    0.0 FOM= 0.00 TEST= 0
INDE  0  36  36 FOBS=  101.4 SIGMA=  2.7 PHAS=    0.0 FOM= 0.02 TEST= 1
INDE  0  36  38 FOBS=   54.1 SIGMA=  4.6 PHAS= -180.0 FOM= 0.31 TEST= 0
INDE  0  36  40 FOBS=    0.0 SIGMA= 22.1 PHAS=    0.0 FOM= 0.00 TEST= 0
INDE  0  36  42 FOBS=  303.5 SIGMA=  1.0 PHAS= -180.0 FOM= 1.00 TEST= 0
INDE  0  36  44 FOBS=  140.3 SIGMA=  1.7 PHAS= -180.0 FOM= 1.00 TEST= 0
INDE  0  36  46 FOBS=    0.0 SIGMA= 21.2 PHAS=    0.0 FOM= 0.00 TEST= 0
INDE  0  36  48 FOBS=    0.0 SIGMA= 21.1 PHAS=    0.0 FOM= 0.00 TEST= 0
INDE  0  36  50 FOBS=   13.0 SIGMA= 18.0 PHAS=    0.0 FOM= 0.56 TEST= 0
INDE  0  36  52 FOBS=    0.0 SIGMA= 21.4 PHAS=    0.0 FOM= 0.00 TEST= 0
INDE  0  36  54 FOBS=   22.9 SIGMA= 13.7 PHAS= -180.0 FOM= 0.44 TEST= 0
INDE  0  36  56 FOBS=   56.4 SIGMA=  5.7 PHAS= -180.0 FOM= 0.51 TEST= 0
INDE  0  36  58 FOBS=    0.0 SIGMA= 20.9 PHAS=    0.0 FOM= 0.00 TEST= 0
INDE  0  36  60 FOBS=   25.7 SIGMA= 11.2 PHAS= -180.0 FOM= 0.10 TEST= 0
INDE  0  36  62 FOBS=   91.1 SIGMA=  2.9 PHAS= -180.0 FOM= 1.00 TEST= 0
INDE  0  36  64 FOBS=    0.0 SIGMA= 22.6 PHAS=    0.0 FOM= 0.00 TEST= 0
INDE  0  36  66 FOBS=    0.0 SIGMA= 27.1 PHAS=    0.0 FOM= 0.00 TEST= 0
INDE  0  36  68 FOBS=   69.8 SIGMA=  8.2 PHAS= -180.0 FOM= 0.24 TEST= 0
INDE  0  37   1 FOBS=  137.0 SIGMA=  0.9 PHAS=   90.0 FOM= 1.00 TEST= 0
INDE  0  37   9 FOBS=   46.2 SIGMA=  3.2 PHAS=  -90.0 FOM= 0.53 TEST= 0
INDE  0  37  11 FOBS=  108.7 SIGMA=  1.5 PHAS=  -90.0 FOM= 1.00 TEST= 1
INDE  0  37  13 FOBS=   94.1 SIGMA=  1.9 PHAS=   90.0 FOM= 0.43 TEST= 1
INDE  0  37  31 FOBS=   42.5 SIGMA=  7.5 PHAS=  -90.0 FOM= 0.32 TEST= 0
INDE  0  37  33 FOBS=    0.0 SIGMA= 23.0 PHAS=    0.0 FOM= 0.00 TEST= 0
INDE  0  37  35 FOBS=  370.2 SIGMA=  1.0 PHAS=  -90.0 FOM= 1.00 TEST= 0
INDE  0  37  37 FOBS=   76.6 SIGMA=  3.4 PHAS=  -90.0 FOM= 1.00 TEST= 0
INDE  0  37  39 FOBS=  267.4 SIGMA=  1.1 PHAS=  -90.0 FOM= 1.00 TEST= 0
INDE  0  37  41 FOBS=  150.0 SIGMA=  1.7 PHAS=  -90.0 FOM= 0.03 TEST= 1
INDE  0  37  43 FOBS=  146.3 SIGMA=  1.7 PHAS=   90.0 FOM= 0.99 TEST= 0
INDE  0  37  45 FOBS=    0.0 SIGMA= 21.3 PHAS=    0.0 FOM= 0.00 TEST= 0
INDE  0  37  47 FOBS=   59.1 SIGMA=  3.8 PHAS=   90.0 FOM= 0.28 TEST= 0
INDE  0  37  49 FOBS=   87.6 SIGMA=  2.6 PHAS=  -90.0 FOM= 0.99 TEST= 0
INDE  0  37  51 FOBS=    0.0 SIGMA= 27.5 PHAS=    0.0 FOM= 0.00 TEST= 0
INDE  0  37  53 FOBS=    0.0 SIGMA= 24.8 PHAS=    0.0 FOM= 0.00 TEST= 0
INDE  0  37  55 FOBS=   52.9 SIGMA=  5.9 PHAS=   90.0 FOM= 0.89 TEST= 0
INDE  0  37  57 FOBS=    0.0 SIGMA= 27.0 PHAS=    0.0 FOM= 0.00 TEST= 0
INDE  0  37  59 FOBS=   12.9 SIGMA= 18.7 PHAS=  -90.0 FOM= 0.12 TEST= 0
INDE  0  37  61 FOBS=   43.5 SIGMA=  5.9 PHAS=   90.0 FOM= 0.25 TEST= 0
INDE  0  37  63 FOBS=   66.4 SIGMA=  3.9 PHAS=   90.0 FOM= 0.07 TEST= 0
INDE  0  37  65 FOBS=    0.0 SIGMA= 22.8 PHAS=    0.0 FOM= 0.00 TEST= 0
INDE  0  37  67 FOBS=   38.8 SIGMA= 10.1 PHAS=  -90.0 FOM= 0.30 TEST= 0
INDE  0  38   0 FOBS=  228.0 SIGMA=  0.7 PHAS=    0.0 FOM= 1.00 TEST= 0
INDE  0  38   2 FOBS=  396.9 SIGMA=  0.5 PHAS=    0.0 FOM= 1.00 TEST= 0
INDE  0  38   8 FOBS=  201.2 SIGMA=  0.9 PHAS= -180.0 FOM= 1.00 TEST= 0
INDE  0  38  10 FOBS=  512.9 SIGMA=  0.6 PHAS= -180.0 FOM= 1.00 TEST= 0
INDE  0  38  12 FOBS=    0.0 SIGMA= 18.5 PHAS=    0.0 FOM= 0.00 TEST= 0
INDE  0  38  14 FOBS=  148.5 SIGMA=  1.4 PHAS= -180.0 FOM= 0.86 TEST= 0
INDE  0  38  32 FOBS=  110.6 SIGMA=  2.5 PHAS= -180.0 FOM= 0.99 TEST= 0
INDE  0  38  34 FOBS=   95.2 SIGMA=  2.9 PHAS= -180.0 FOM= 0.94 TEST= 0
INDE  0  38  36 FOBS=  255.3 SIGMA=  1.5 PHAS= -180.0 FOM= 0.99 TEST= 0
INDE  0  38  38 FOBS=    0.0 SIGMA= 22.5 PHAS=    0.0 FOM= 0.00 TEST= 0
INDE  0  38  40 FOBS=  103.3 SIGMA=  2.5 PHAS=    0.0 FOM= 0.74 TEST= 0
INDE  0  38  42 FOBS=    0.0 SIGMA= 21.9 PHAS=    0.0 FOM= 0.00 TEST= 0
INDE  0  38  44 FOBS=   93.3 SIGMA=  2.6 PHAS=    0.0 FOM= 1.00 TEST= 0
INDE  0  38  46 FOBS=  132.5 SIGMA=  1.8 PHAS=    0.0 FOM= 1.00 TEST= 0
INDE  0  38  48 FOBS=  195.0 SIGMA=  1.3 PHAS= -180.0 FOM= 1.00 TEST= 0
INDE  0  38  50 FOBS=  101.8 SIGMA=  2.2 PHAS= -180.0 FOM= 1.00 TEST= 0
INDE  0  38  52 FOBS=   70.4 SIGMA=  4.4 PHAS= -180.0 FOM= 0.80 TEST= 0
INDE  0  38  54 FOBS=    8.8 SIGMA= 35.0 PHAS=    0.0 FOM= 0.09 TEST= 0
INDE  0  38  56 FOBS=   20.3 SIGMA= 15.7 PHAS=    0.0 FOM= 0.20 TEST= 0
INDE  0  38  58 FOBS=   89.6 SIGMA=  2.5 PHAS= -180.0 FOM= 0.40 TEST= 0
INDE  0  38  60 FOBS=   27.4 SIGMA=  9.0 PHAS=    0.0 FOM= 0.00 TEST= 0
INDE  0  38  62 FOBS=    0.0 SIGMA= 24.5 PHAS=    0.0 FOM= 0.00 TEST= 0
INDE  0  38  64 FOBS=  108.2 SIGMA=  2.5 PHAS= -180.0 FOM= 1.00 TEST= 0
INDE  0  38  66 FOBS=   49.7 SIGMA=  8.1 PHAS=    0.0 FOM= 0.86 TEST= 0
INDE  0  39   1 FOBS=  533.5 SIGMA=  0.4 PHAS=  -90.0 FOM= 1.00 TEST= 0
INDE  0  39   9 FOBS=  151.7 SIGMA=  1.2 PHAS=   90.0 FOM= 0.24 TEST= 0
INDE  0  39  11 FOBS=   60.8 SIGMA=  2.8 PHAS=   90.0 FOM= 0.35 TEST= 0
INDE  0  39  13 FOBS=  182.4 SIGMA=  1.2 PHAS=   90.0 FOM= 1.00 TEST= 0
```

*FIG. 12A - 15*

```
INDE  0  39  15 FOBS=   58.2 SIGMA=  3.4 PHAS=  -90.0 FOM= 0.99 TEST= 1
INDE  0  39  31 FOBS=  180.0 SIGMA=  2.8 PHAS=   90.0 FOM= 0.94 TEST= 0
INDE  0  39  33 FOBS=  243.7 SIGMA=  1.3 PHAS=   90.0 FOM= 0.27 TEST= 1
INDE  0  39  35 FOBS=   94.8 SIGMA=  2.9 PHAS=   90.0 FOM= 0.65 TEST= 0
INDE  0  39  37 FOBS=    0.0 SIGMA= 22.7 PHAS=    0.0 FOM= 0.00 TEST= 0
INDE  0  39  39 FOBS=  122.2 SIGMA=  2.1 PHAS=  -90.0 FOM= 0.20 TEST= 0
INDE  0  39  41 FOBS=   83.8 SIGMA=  3.0 PHAS=   90.0 FOM= 0.85 TEST= 0
INDE  0  39  43 FOBS=   87.5 SIGMA=  2.7 PHAS=  -90.0 FOM= 1.00 TEST= 0
INDE  0  39  45 FOBS=  146.1 SIGMA=  1.7 PHAS=  -90.0 FOM= 1.00 TEST= 0
INDE  0  39  47 FOBS=   66.3 SIGMA=  3.5 PHAS=   90.0 FOM= 0.86 TEST= 0
INDE  0  39  49 FOBS=  119.8 SIGMA=  1.9 PHAS=   90.0 FOM= 0.97 TEST= 0
INDE  0  39  51 FOBS=  108.0 SIGMA=  2.1 PHAS=   90.0 FOM= 0.99 TEST= 0
INDE  0  39  53 FOBS=    0.0 SIGMA= 24.7 PHAS=    0.0 FOM= 0.00 TEST= 0
INDE  0  39  55 FOBS=    0.0 SIGMA= 24.8 PHAS=    0.0 FOM= 0.00 TEST= 0
INDE  0  39  57 FOBS=   96.9 SIGMA=  2.9 PHAS=   90.0 FOM= 0.96 TEST= 0
INDE  0  39  59 FOBS=   48.6 SIGMA=  5.4 PHAS=  -90.0 FOM= 0.01 TEST= 0
INDE  0  39  61 FOBS=    0.0 SIGMA= 22.6 PHAS=    0.0 FOM= 0.00 TEST= 0
INDE  0  39  63 FOBS=    0.0 SIGMA= 22.9 PHAS=    0.0 FOM= 0.00 TEST= 0
INDE  0  39  65 FOBS=  126.3 SIGMA=  2.2 PHAS=   90.0 FOM= 1.00 TEST= 0
INDE  0  39  67 FOBS=    0.0 SIGMA= 34.1 PHAS=    0.0 FOM= 0.00 TEST= 0
INDE  0  40   0 FOBS=  450.9 SIGMA=  0.5 PHAS= -180.0 FOM= 1.00 TEST= 0
INDE  0  40   2 FOBS=  125.9 SIGMA=  1.2 PHAS=    0.0 FOM= 0.81 TEST= 0
INDE  0  40  10 FOBS=  227.9 SIGMA=  0.9 PHAS= -180.0 FOM= 1.00 TEST= 0
INDE  0  40  12 FOBS=  185.2 SIGMA=  1.1 PHAS=    0.0 FOM= 1.00 TEST= 1
INDE  0  40  14 FOBS=  134.1 SIGMA=  1.7 PHAS= -180.0 FOM= 0.19 TEST= 0
INDE  0  40  16 FOBS=   11.8 SIGMA= 17.4 PHAS= -180.0 FOM= 0.03 TEST= 0
INDE  0  40  32 FOBS=  286.5 SIGMA=  1.2 PHAS= -180.0 FOM= 1.00 TEST= 0
INDE  0  40  34 FOBS=  145.6 SIGMA=  1.9 PHAS= -180.0 FOM= 1.00 TEST= 0
INDE  0  40  36 FOBS=   62.3 SIGMA=  4.2 PHAS= -180.0 FOM= 0.53 TEST= 0
INDE  0  40  38 FOBS=   62.9 SIGMA=  4.1 PHAS=    0.0 FOM= 0.50 TEST= 0
INDE  0  40  40 FOBS=  177.2 SIGMA=  1.6 PHAS=    0.0 FOM= 0.97 TEST= 0
INDE  0  40  42 FOBS=   57.9 SIGMA=  4.3 PHAS=    0.0 FOM= 0.06 TEST= 0
INDE  0  40  44 FOBS=    0.0 SIGMA= 25.8 PHAS=    0.0 FOM= 0.00 TEST= 0
INDE  0  40  46 FOBS=   67.7 SIGMA=  3.5 PHAS= -180.0 FOM= 0.88 TEST= 0
INDE  0  40  48 FOBS=   58.3 SIGMA=  3.9 PHAS= -180.0 FOM= 0.54 TEST= 0
INDE  0  40  50 FOBS=   33.5 SIGMA=  6.5 PHAS=    0.0 FOM= 0.31 TEST= 0
INDE  0  40  52 FOBS=    0.0 SIGMA= 24.8 PHAS=    0.0 FOM= 0.00 TEST= 0
INDE  0  40  54 FOBS=    0.0 SIGMA= 27.4 PHAS=    0.0 FOM= 0.00 TEST= 0
INDE  0  40  56 FOBS=   60.1 SIGMA=  5.2 PHAS=    0.0 FOM= 0.69 TEST= 0
INDE  0  40  58 FOBS=    0.0 SIGMA= 20.8 PHAS=    0.0 FOM= 0.00 TEST= 0
INDE  0  40  60 FOBS=   41.3 SIGMA=  6.4 PHAS=    0.0 FOM= 0.38 TEST= 0
INDE  0  40  62 FOBS=   86.8 SIGMA=  2.6 PHAS=    0.0 FOM= 0.89 TEST= 0
INDE  0  40  64 FOBS=   27.9 SIGMA=  9.7 PHAS=    0.0 FOM= 0.63 TEST= 0
INDE  0  40  66 FOBS=   76.1 SIGMA=  7.7 PHAS=    0.0 FOM= 0.36 TEST= 0
INDE  0  41   1 FOBS=   58.5 SIGMA=  1.7 PHAS=   90.0 FOM= 0.33 TEST= 0
INDE  0  41   9 FOBS=   54.6 SIGMA=  3.2 PHAS=  -90.0 FOM= 1.00 TEST= 1
INDE  0  41  11 FOBS=   82.4 SIGMA=  2.3 PHAS=  -90.0 FOM= 1.00 TEST= 0
INDE  0  41  13 FOBS=    0.0 SIGMA= 19.7 PHAS=    0.0 FOM= 0.00 TEST= 0
INDE  0  41  15 FOBS=   66.3 SIGMA=  3.4 PHAS=   90.0 FOM= 0.61 TEST= 0
INDE  0  41  31 FOBS=   60.0 SIGMA=  7.8 PHAS=   90.0 FOM= 0.34 TEST= 0
INDE  0  41  33 FOBS=   90.3 SIGMA=  3.0 PHAS=   90.0 FOM= 0.77 TEST= 0
INDE  0  41  35 FOBS=  188.7 SIGMA=  1.5 PHAS=   90.0 FOM= 1.00 TEST= 0
INDE  0  41  37 FOBS=   24.9 SIGMA= 10.2 PHAS=   90.0 FOM= 0.38 TEST= 0
INDE  0  41  39 FOBS=  168.6 SIGMA=  1.6 PHAS=  -90.0 FOM= 1.00 TEST= 0
INDE  0  41  41 FOBS=    0.0 SIGMA= 23.2 PHAS=    0.0 FOM= 0.00 TEST= 0
INDE  0  41  43 FOBS=   61.2 SIGMA=  4.0 PHAS=  -90.0 FOM= 0.27 TEST= 0
INDE  0  41  45 FOBS=  146.7 SIGMA=  1.7 PHAS=  -90.0 FOM= 1.00 TEST= 0
INDE  0  41  47 FOBS=  114.1 SIGMA=  2.1 PHAS=   90.0 FOM= 0.03 TEST= 1
INDE  0  41  49 FOBS=   21.3 SIGMA= 14.7 PHAS=   90.0 FOM= 0.01 TEST= 0
INDE  0  41  51 FOBS=   50.1 SIGMA=  7.8 PHAS=  -90.0 FOM= 0.01 TEST= 0
INDE  0  41  53 FOBS=    0.0 SIGMA= 24.9 PHAS=    0.0 FOM= 0.00 TEST= 0
INDE  0  41  55 FOBS=   53.9 SIGMA=  5.9 PHAS=   90.0 FOM= 0.92 TEST= 0
INDE  0  41  57 FOBS=   24.7 SIGMA= 12.8 PHAS=   90.0 FOM= 0.48 TEST= 0
INDE  0  41  59 FOBS=    0.0 SIGMA= 20.9 PHAS=    0.0 FOM= 0.00 TEST= 0
INDE  0  41  61 FOBS=   45.3 SIGMA=  5.9 PHAS=  -90.0 FOM= 0.25 TEST= 0
INDE  0  41  63 FOBS=    0.0 SIGMA= 21.3 PHAS=    0.0 FOM= 0.00 TEST= 0
INDE  0  41  65 FOBS=   55.9 SIGMA=  7.1 PHAS=   90.0 FOM= 0.94 TEST= 0
INDE  0  42   0 FOBS=  198.0 SIGMA=  0.9 PHAS= -180.0 FOM= 0.57 TEST= 0
INDE  0  42   2 FOBS=  116.7 SIGMA=  1.4 PHAS=    0.0 FOM= 0.44 TEST= 0
INDE  0  42  10 FOBS=    0.0 SIGMA= 19.1 PHAS=    0.0 FOM= 0.00 TEST= 0
```

*FIG. 12A - 16*

| | | | | | | | | | | |
|---|---|---|---|---|---|---|---|---|---|---|
| INDE | 0 | 42 | 12 | FOBS= | 45.2 | SIGMA= | 4.4 | PHAS= | 0.0 | FOM= 0.30 | TEST= 0 |
| INDE | 0 | 42 | 14 | FOBS= | 56.5 | SIGMA= | 3.9 | PHAS= | -180.0 | FOM= 0.61 | TEST= 0 |
| INDE | 0 | 42 | 16 | FOBS= | 95.1 | SIGMA= | 2.6 | PHAS= | -180.0 | FOM= 1.00 | TEST= 0 |
| INDE | 0 | 42 | 32 | FOBS= | 95.9 | SIGMA= | 3.6 | PHAS= | -180.0 | FOM= 0.51 | TEST= 0 |
| INDE | 0 | 42 | 34 | FOBS= | 326.7 | SIGMA= | 1.0 | PHAS= | 0.0 | FOM= 1.00 | TEST= 0 |
| INDE | 0 | 42 | 36 | FOBS= | 63.0 | SIGMA= | 4.1 | PHAS= | 0.0 | FOM= 0.97 | TEST= 0 |
| INDE | 0 | 42 | 38 | FOBS= | 112.1 | SIGMA= | 2.4 | PHAS= | 0.0 | FOM= 0.76 | TEST= 0 |
| INDE | 0 | 42 | 40 | FOBS= | 29.9 | SIGMA= | 9.4 | PHAS= | -180.0 | FOM= 0.09 | TEST= 0 |
| INDE | 0 | 42 | 42 | FOBS= | 62.3 | SIGMA= | 4.0 | PHAS= | -180.0 | FOM= 1.00 | TEST= 0 |
| INDE | 0 | 42 | 44 | FOBS= | 64.8 | SIGMA= | 3.8 | PHAS= | 0.0 | FOM= 0.17 | TEST= 0 |
| INDE | 0 | 42 | 46 | FOBS= | 224.4 | SIGMA= | 1.2 | PHAS= | -180.0 | FOM= 1.00 | TEST= 0 |
| INDE | 0 | 42 | 48 | FOBS= | 47.8 | SIGMA= | 4.8 | PHAS= | -180.0 | FOM= 0.58 | TEST= 0 |
| INDE | 0 | 42 | 50 | FOBS= | 28.5 | SIGMA= | 7.9 | PHAS= | 0.0 | FOM= 0.59 | TEST= 0 |
| INDE | 0 | 42 | 52 | FOBS= | 101.0 | SIGMA= | 3.2 | PHAS= | -180.0 | FOM= 0.26 | TEST= 1 |
| INDE | 0 | 42 | 54 | FOBS= | 100.1 | SIGMA= | 3.2 | PHAS= | 0.0 | FOM= 0.94 | TEST= 0 |
| INDE | 0 | 42 | 56 | FOBS= | 0.0 | SIGMA= | 25.0 | PHAS= | 0.0 | FOM= 0.00 | TEST= 0 |
| INDE | 0 | 42 | 58 | FOBS= | 0.0 | SIGMA= | 20.9 | PHAS= | 0.0 | FOM= 0.00 | TEST= 0 |
| INDE | 0 | 42 | 60 | FOBS= | 63.8 | SIGMA= | 3.6 | PHAS= | 0.0 | FOM= 0.95 | TEST= 0 |
| INDE | 0 | 42 | 62 | FOBS= | 58.0 | SIGMA= | 4.6 | PHAS= | 0.0 | FOM= 0.97 | TEST= 0 |
| INDE | 0 | 42 | 64 | FOBS= | 104.9 | SIGMA= | 2.9 | PHAS= | 0.0 | FOM= 1.00 | TEST= 0 |
| INDE | 0 | 43 | 1 | FOBS= | 212.7 | SIGMA= | 0.7 | PHAS= | -90.0 | FOM= 0.40 | TEST= 1 |
| INDE | 0 | 43 | 11 | FOBS= | 142.0 | SIGMA= | 1.5 | PHAS= | -90.0 | FOM= 0.96 | TEST= 1 |
| INDE | 0 | 43 | 13 | FOBS= | 65.1 | SIGMA= | 3.3 | PHAS= | -90.0 | FOM= 0.90 | TEST= 0 |
| INDE | 0 | 43 | 15 | FOBS= | 212.8 | SIGMA= | 1.3 | PHAS= | 90.0 | FOM= 1.00 | TEST= 0 |
| INDE | 0 | 43 | 17 | FOBS= | 65.5 | SIGMA= | 3.9 | PHAS= | 90.0 | FOM= 0.91 | TEST= 0 |
| INDE | 0 | 43 | 31 | FOBS= | 0.0 | SIGMA= | 30.3 | PHAS= | 0.0 | FOM= 0.00 | TEST= 0 |
| INDE | 0 | 43 | 33 | FOBS= | 151.2 | SIGMA= | 2.4 | PHAS= | -90.0 | FOM= 1.00 | TEST= 0 |
| INDE | 0 | 43 | 35 | FOBS= | 43.2 | SIGMA= | 7.3 | PHAS= | 90.0 | FOM= 0.35 | TEST= 1 |
| INDE | 0 | 43 | 37 | FOBS= | 178.2 | SIGMA= | 1.6 | PHAS= | 90.0 | FOM= 1.00 | TEST= 0 |
| INDE | 0 | 43 | 39 | FOBS= | 142.0 | SIGMA= | 1.9 | PHAS= | -90.0 | FOM= 0.99 | TEST= 0 |
| INDE | 0 | 43 | 41 | FOBS= | 99.1 | SIGMA= | 2.6 | PHAS= | -90.0 | FOM= 0.92 | TEST= 0 |
| INDE | 0 | 43 | 43 | FOBS= | 0.0 | SIGMA= | 22.1 | PHAS= | 0.0 | FOM= 0.00 | TEST= 0 |
| INDE | 0 | 43 | 45 | FOBS= | 132.7 | SIGMA= | 1.9 | PHAS= | 90.0 | FOM= 1.00 | TEST= 0 |
| INDE | 0 | 43 | 47 | FOBS= | 0.0 | SIGMA= | 22.6 | PHAS= | 0.0 | FOM= 0.00 | TEST= 0 |
| INDE | 0 | 43 | 49 | FOBS= | 15.6 | SIGMA= | 17.6 | PHAS= | 90.0 | FOM= 0.07 | TEST= 0 |
| INDE | 0 | 43 | 51 | FOBS= | 66.0 | SIGMA= | 4.8 | PHAS= | 90.0 | FOM= 0.46 | TEST= 0 |
| INDE | 0 | 43 | 53 | FOBS= | 12.4 | SIGMA= | 25.2 | PHAS= | -90.0 | FOM= 0.22 | TEST= 0 |
| INDE | 0 | 43 | 55 | FOBS= | 0.0 | SIGMA= | 25.1 | PHAS= | 0.0 | FOM= 0.00 | TEST= 0 |
| INDE | 0 | 43 | 57 | FOBS= | 0.0 | SIGMA= | 23.5 | PHAS= | 0.0 | FOM= 0.00 | TEST= 0 |
| INDE | 0 | 43 | 59 | FOBS= | 131.4 | SIGMA= | 1.8 | PHAS= | -90.0 | FOM= 1.00 | TEST= 0 |
| INDE | 0 | 43 | 61 | FOBS= | 77.4 | SIGMA= | 3.0 | PHAS= | -90.0 | FOM= 0.97 | TEST= 0 |
| INDE | 0 | 43 | 63 | FOBS= | 111.2 | SIGMA= | 2.5 | PHAS= | -90.0 | FOM= 1.00 | TEST= 0 |
| INDE | 0 | 44 | 0 | FOBS= | 224.3 | SIGMA= | 0.8 | PHAS= | -180.0 | FOM= 1.00 | TEST= 0 |
| INDE | 0 | 44 | 2 | FOBS= | 27.7 | SIGMA= | 8.6 | PHAS= | 0.0 | FOM= 0.12 | TEST= 0 |
| INDE | 0 | 44 | 10 | FOBS= | 170.6 | SIGMA= | 1.3 | PHAS= | -180.0 | FOM= 1.00 | TEST= 0 |
| INDE | 0 | 44 | 12 | FOBS= | 250.2 | SIGMA= | 1.0 | PHAS= | -180.0 | FOM= 1.00 | TEST= 0 |
| INDE | 0 | 44 | 14 | FOBS= | 186.7 | SIGMA= | 1.4 | PHAS= | -180.0 | FOM= 1.00 | TEST= 0 |
| INDE | 0 | 44 | 16 | FOBS= | 91.2 | SIGMA= | 3.0 | PHAS= | 0.0 | FOM= 1.00 | TEST= 0 |
| INDE | 0 | 44 | 18 | FOBS= | 115.7 | SIGMA= | 2.4 | PHAS= | 0.0 | FOM= 1.00 | TEST= 0 |
| INDE | 0 | 44 | 32 | FOBS= | 0.0 | SIGMA= | 26.0 | PHAS= | 0.0 | FOM= 0.00 | TEST= 1 |
| INDE | 0 | 44 | 34 | FOBS= | 185.6 | SIGMA= | 2.0 | PHAS= | 0.0 | FOM= 1.00 | TEST= 0 |
| INDE | 0 | 44 | 36 | FOBS= | 137.9 | SIGMA= | 2.0 | PHAS= | 0.0 | FOM= 0.99 | TEST= 0 |
| INDE | 0 | 44 | 38 | FOBS= | 77.9 | SIGMA= | 3.3 | PHAS= | 0.0 | FOM= 0.66 | TEST= 0 |
| INDE | 0 | 44 | 40 | FOBS= | 158.5 | SIGMA= | 1.7 | PHAS= | -180.0 | FOM= 0.92 | TEST= 0 |
| INDE | 0 | 44 | 42 | FOBS= | 56.3 | SIGMA= | 4.4 | PHAS= | -180.0 | FOM= 0.55 | TEST= 0 |
| INDE | 0 | 44 | 44 | FOBS= | 29.4 | SIGMA= | 8.4 | PHAS= | 0.0 | FOM= 0.47 | TEST= 0 |
| INDE | 0 | 44 | 46 | FOBS= | 0.0 | SIGMA= | 21.8 | PHAS= | 0.0 | FOM= 0.00 | TEST= 0 |
| INDE | 0 | 44 | 48 | FOBS= | 37.0 | SIGMA= | 6.2 | PHAS= | -180.0 | FOM= 0.72 | TEST= 0 |
| INDE | 0 | 44 | 50 | FOBS= | 56.4 | SIGMA= | 4.9 | PHAS= | 0.0 | FOM= 0.96 | TEST= 0 |
| INDE | 0 | 44 | 52 | FOBS= | 0.0 | SIGMA= | 25.0 | PHAS= | 0.0 | FOM= 0.00 | TEST= 0 |
| INDE | 0 | 44 | 54 | FOBS= | 0.0 | SIGMA= | 24.9 | PHAS= | 0.0 | FOM= 0.00 | TEST= 0 |
| INDE | 0 | 44 | 56 | FOBS= | 70.3 | SIGMA= | 4.6 | PHAS= | -180.0 | FOM= 0.49 | TEST= 0 |
| INDE | 0 | 44 | 58 | FOBS= | 89.1 | SIGMA= | 2.6 | PHAS= | -180.0 | FOM= 0.61 | TEST= 0 |
| INDE | 0 | 44 | 60 | FOBS= | 0.0 | SIGMA= | 21.4 | PHAS= | 0.0 | FOM= 0.00 | TEST= 0 |
| INDE | 0 | 44 | 62 | FOBS= | 104.2 | SIGMA= | 2.8 | PHAS= | -180.0 | FOM= 1.00 | TEST= 0 |
| INDE | 0 | 44 | 64 | FOBS= | 21.6 | SIGMA= | 16.6 | PHAS= | 0.0 | FOM= 0.00 | TEST= 1 |
| INDE | 0 | 45 | 1 | FOBS= | 241.8 | SIGMA= | 0.7 | PHAS= | -90.0 | FOM= 0.98 | TEST= 0 |
| INDE | 0 | 45 | 11 | FOBS= | 148.5 | SIGMA= | 1.6 | PHAS= | 90.0 | FOM= 1.00 | TEST= 0 |
| INDE | 0 | 45 | 13 | FOBS= | 45.1 | SIGMA= | 5.3 | PHAS= | 90.0 | FOM= 0.24 | TEST= 0 |
| INDE | 0 | 45 | 15 | FOBS= | 138.4 | SIGMA= | 1.9 | PHAS= | 90.0 | FOM= 1.00 | TEST= 0 |

*FIG. 12A - 17*

```
INDE  0  45  17 FOBS=    0.0 SIGMA=  23.8 PHAS=    0.0 FOM=  0.00 TEST= 0
INDE  0  45  19 FOBS=   54.4 SIGMA=   5.2 PHAS=  -90.0 FOM=  0.56 TEST= 0
INDE  0  45  31 FOBS=    0.0 SIGMA=  30.4 PHAS=    0.0 FOM=  0.00 TEST= 0
INDE  0  45  33 FOBS=  257.9 SIGMA=   1.6 PHAS=  -90.0 FOM=  1.00 TEST= 0
INDE  0  45  35 FOBS=  122.8 SIGMA=   2.2 PHAS=  -90.0 FOM=  1.00 TEST= 0
INDE  0  45  37 FOBS=  260.6 SIGMA=   1.2 PHAS=  -90.0 FOM=  0.94 TEST= 1
INDE  0  45  39 FOBS=   65.4 SIGMA=   4.0 PHAS=   90.0 FOM=  0.65 TEST= 0
INDE  0  45  41 FOBS=   85.5 SIGMA=   3.0 PHAS=  -90.0 FOM=  1.00 TEST= 0
INDE  0  45  43 FOBS=  103.5 SIGMA=   2.5 PHAS=  -90.0 FOM=  0.95 TEST= 0
INDE  0  45  45 FOBS=    0.0 SIGMA=  22.0 PHAS=    0.0 FOM=  0.00 TEST= 0
INDE  0  45  47 FOBS=    0.0 SIGMA=  23.9 PHAS=    0.0 FOM=  0.00 TEST= 0
INDE  0  45  49 FOBS=  109.8 SIGMA=   2.2 PHAS=  -90.0 FOM=  0.99 TEST= 0
INDE  0  45  51 FOBS=    0.0 SIGMA=  25.3 PHAS=    0.0 FOM=  0.00 TEST= 1
INDE  0  45  53 FOBS=    0.0 SIGMA=  25.2 PHAS=    0.0 FOM=  0.00 TEST= 0
INDE  0  45  55 FOBS=   71.5 SIGMA=   4.5 PHAS=   90.0 FOM=  0.23 TEST= 1
INDE  0  45  57 FOBS=  126.7 SIGMA=   2.3 PHAS=  -90.0 FOM=  0.65 TEST= 0
INDE  0  45  59 FOBS=   86.5 SIGMA=   2.7 PHAS=  -90.0 FOM=  0.96 TEST= 0
INDE  0  45  61 FOBS=   47.2 SIGMA=   5.0 PHAS=   90.0 FOM=  0.97 TEST= 0
INDE  0  45  63 FOBS=    0.0 SIGMA=  28.2 PHAS=    0.0 FOM=  0.00 TEST= 0
INDE  0  46   0 FOBS=  247.9 SIGMA=   0.9 PHAS= -180.0 FOM=  1.00 TEST= 0
INDE  0  46   2 FOBS=  345.9 SIGMA=   0.7 PHAS= -180.0 FOM=  1.00 TEST= 0
INDE  0  46  12 FOBS=   38.6 SIGMA=   6.1 PHAS= -180.0 FOM=  0.06 TEST= 0
INDE  0  46  14 FOBS=   80.7 SIGMA=   3.1 PHAS= -180.0 FOM=  0.68 TEST= 0
INDE  0  46  16 FOBS=   33.8 SIGMA=   8.0 PHAS=    0.0 FOM=  0.39 TEST= 0
INDE  0  46  18 FOBS=   49.4 SIGMA=   5.9 PHAS= -180.0 FOM=  0.39 TEST= 0
INDE  0  46  20 FOBS=  234.2 SIGMA=   1.4 PHAS= -180.0 FOM=  1.00 TEST= 0
INDE  0  46  32 FOBS=   44.7 SIGMA=   7.6 PHAS= -180.0 FOM=  0.48 TEST= 0
INDE  0  46  34 FOBS=  164.1 SIGMA=   2.2 PHAS= -180.0 FOM=  1.00 TEST= 0
INDE  0  46  36 FOBS=   29.4 SIGMA=   8.7 PHAS= -180.0 FOM=  0.53 TEST= 0
INDE  0  46  38 FOBS=  211.9 SIGMA=   1.4 PHAS=    0.0 FOM=  1.00 TEST= 0
INDE  0  46  40 FOBS=  130.6 SIGMA=   2.1 PHAS= -180.0 FOM=  1.00 TEST= 0
INDE  0  46  42 FOBS=  254.9 SIGMA=   1.3 PHAS= -180.0 FOM=  1.00 TEST= 0
INDE  0  46  44 FOBS=  111.4 SIGMA=   2.3 PHAS=    0.0 FOM=  0.01 TEST= 1
INDE  0  46  46 FOBS=    0.0 SIGMA=  21.9 PHAS=    0.0 FOM=  0.00 TEST= 0
INDE  0  46  48 FOBS=  118.9 SIGMA=   2.1 PHAS= -180.0 FOM=  1.00 TEST= 0
INDE  0  46  50 FOBS=    0.0 SIGMA=  25.3 PHAS=    0.0 FOM=  0.00 TEST= 0
INDE  0  46  52 FOBS=    0.0 SIGMA=  25.2 PHAS=    0.0 FOM=  0.00 TEST= 0
INDE  0  46  54 FOBS=    0.0 SIGMA=  25.2 PHAS=    0.0 FOM=  0.00 TEST= 0
INDE  0  46  56 FOBS=  110.8 SIGMA=   3.1 PHAS= -180.0 FOM=  1.00 TEST= 0
INDE  0  46  58 FOBS=   22.1 SIGMA=  10.3 PHAS=    0.0 FOM=  0.12 TEST= 0
INDE  0  46  60 FOBS=   10.7 SIGMA=  22.0 PHAS=    0.0 FOM=  0.22 TEST= 0
INDE  0  46  62 FOBS=    0.0 SIGMA=  24.5 PHAS=    0.0 FOM=  0.00 TEST= 0
INDE  0  47   1 FOBS=   50.3 SIGMA=   2.9 PHAS=  -90.0 FOM=  0.98 TEST= 0
INDE  0  47  11 FOBS=   33.7 SIGMA=   9.3 PHAS=  -90.0 FOM=  0.08 TEST= 0
INDE  0  47  13 FOBS=   21.6 SIGMA=  11.6 PHAS=    0.0 FOM=  0.00 TEST= 1
INDE  0  47  15 FOBS=  125.2 SIGMA=   2.1 PHAS=  -90.0 FOM=  0.98 TEST= 0
INDE  0  47  17 FOBS=   71.1 SIGMA=   3.9 PHAS=  -90.0 FOM=  0.55 TEST= 0
INDE  0  47  19 FOBS=  119.7 SIGMA=   2.5 PHAS=   90.0 FOM=  0.94 TEST= 0
INDE  0  47  31 FOBS=  217.1 SIGMA=   2.5 PHAS=  -90.0 FOM=  1.00 TEST= 0
INDE  0  47  33 FOBS=   85.4 SIGMA=   4.1 PHAS=   90.0 FOM=  0.06 TEST= 0
INDE  0  47  35 FOBS=    0.0 SIGMA=  25.4 PHAS=    0.0 FOM=  0.00 TEST= 1
INDE  0  47  37 FOBS=   53.7 SIGMA=   4.9 PHAS=   90.0 FOM=  0.68 TEST= 0
INDE  0  47  39 FOBS=    0.0 SIGMA=  22.6 PHAS=    0.0 FOM=  0.00 TEST= 0
INDE  0  47  41 FOBS=  136.7 SIGMA=   2.2 PHAS=   90.0 FOM=  1.00 TEST= 0
INDE  0  47  43 FOBS=  101.4 SIGMA=   2.6 PHAS=   90.0 FOM=  1.00 TEST= 0
INDE  0  47  45 FOBS=   11.8 SIGMA=  20.9 PHAS=  -90.0 FOM=  0.13 TEST= 0
INDE  0  47  47 FOBS=   14.8 SIGMA=  17.8 PHAS=   90.0 FOM=  0.69 TEST= 0
INDE  0  47  49 FOBS=  119.3 SIGMA=   2.5 PHAS=  -90.0 FOM=  0.98 TEST= 0
INDE  0  47  51 FOBS=   83.5 SIGMA=   4.0 PHAS=  -90.0 FOM=  0.99 TEST= 0
INDE  0  47  53 FOBS=    0.0 SIGMA=  25.2 PHAS=    0.0 FOM=  0.00 TEST= 0
INDE  0  47  55 FOBS=    0.0 SIGMA=  25.3 PHAS=    0.0 FOM=  0.00 TEST= 0
INDE  0  47  57 FOBS=    0.0 SIGMA=  23.7 PHAS=    0.0 FOM=  0.00 TEST= 0
INDE  0  47  59 FOBS=   10.3 SIGMA=  22.4 PHAS=  -90.0 FOM=  0.11 TEST= 0
INDE  0  47  61 FOBS=    0.0 SIGMA=  24.4 PHAS=    0.0 FOM=  0.00 TEST= 0
INDE  0  48   0 FOBS=  445.6 SIGMA=   0.6 PHAS= -180.0 FOM=  1.00 TEST= 0
INDE  0  48   2 FOBS=  111.2 SIGMA=   2.0 PHAS= -180.0 FOM=  1.00 TEST= 0
INDE  0  48  12 FOBS=   73.5 SIGMA=   3.3 PHAS= -180.0 FOM=  0.43 TEST= 0
INDE  0  48  14 FOBS=  179.2 SIGMA=   1.5 PHAS= -180.0 FOM=  1.00 TEST= 0
INDE  0  48  16 FOBS=  148.2 SIGMA=   1.9 PHAS= -180.0 FOM=  1.00 TEST= 0
INDE  0  48  18 FOBS=   62.6 SIGMA=   4.5 PHAS= -180.0 FOM=  1.00 TEST= 0
```

*FIG. 12A - 18*

| | | | | | | | | | | | |
|---|---|---|---|---|---|---|---|---|---|---|---|
| INDE | 0 | 48 | 20 | FOBS= | 187.3 | SIGMA= | 1.7 | PHAS= | -180.0 | FOM= | 1.00 | TEST= 0 |
| INDE | 0 | 48 | 32 | FOBS= | 0.0 | SIGMA= | 26.0 | PHAS= | 0.0 | FOM= | 0.00 | TEST= 0 |
| INDE | 0 | 48 | 34 | FOBS= | 0.0 | SIGMA= | 25.5 | PHAS= | 0.0 | FOM= | 0.00 | TEST= 1 |
| INDE | 0 | 48 | 36 | FOBS= | 5.4 | SIGMA= | 60.3 | PHAS= | 0.0 | FOM= | 0.00 | TEST= 0 |
| INDE | 0 | 48 | 38 | FOBS= | 115.7 | SIGMA= | 2.3 | PHAS= | 0.0 | FOM= | 0.78 | TEST= 0 |
| INDE | 0 | 48 | 40 | FOBS= | 0.0 | SIGMA= | 22.4 | PHAS= | 0.0 | FOM= | 0.00 | TEST= 0 |
| INDE | 0 | 48 | 42 | FOBS= | 0.0 | SIGMA= | 22.4 | PHAS= | 0.0 | FOM= | 0.00 | TEST= 0 |
| INDE | 0 | 48 | 44 | FOBS= | 0.0 | SIGMA= | 22.2 | PHAS= | 0.0 | FOM= | 0.00 | TEST= 0 |
| INDE | 0 | 48 | 46 | FOBS= | 44.0 | SIGMA= | 5.6 | PHAS= | 0.0 | FOM= | 0.15 | TEST= 0 |
| INDE | 0 | 48 | 48 | FOBS= | 135.1 | SIGMA= | 1.9 | PHAS= | -180.0 | FOM= | 1.00 | TEST= 0 |
| INDE | 0 | 48 | 50 | FOBS= | 179.9 | SIGMA= | 1.8 | PHAS= | -180.0 | FOM= | 1.00 | TEST= 0 |
| INDE | 0 | 48 | 52 | FOBS= | 38.5 | SIGMA= | 8.4 | PHAS= | -180.0 | FOM= | 0.22 | TEST= 0 |
| INDE | 0 | 48 | 54 | FOBS= | 0.0 | SIGMA= | 25.6 | PHAS= | 0.0 | FOM= | 0.00 | TEST= 0 |
| INDE | 0 | 48 | 56 | FOBS= | 0.0 | SIGMA= | 25.5 | PHAS= | 0.0 | FOM= | 0.00 | TEST= 0 |
| INDE | 0 | 48 | 58 | FOBS= | 0.0 | SIGMA= | 21.3 | PHAS= | 0.0 | FOM= | 0.00 | TEST= 0 |
| INDE | 0 | 48 | 60 | FOBS= | 34.5 | SIGMA= | 8.6 | PHAS= | 0.0 | FOM= | 0.02 | TEST= 0 |
| INDE | 0 | 49 | 1 | FOBS= | 0.0 | SIGMA= | 25.1 | PHAS= | 0.0 | FOM= | 0.00 | TEST= 0 |
| INDE | 0 | 49 | 3 | FOBS= | 237.9 | SIGMA= | 1.4 | PHAS= | -90.0 | FOM= | 0.99 | TEST= 0 |
| INDE | 0 | 49 | 13 | FOBS= | 121.1 | SIGMA= | 2.1 | PHAS= | 90.0 | FOM= | 0.90 | TEST= 0 |
| INDE | 0 | 49 | 15 | FOBS= | 138.7 | SIGMA= | 1.9 | PHAS= | -90.0 | FOM= | 1.00 | TEST= 1 |
| INDE | 0 | 49 | 17 | FOBS= | 72.0 | SIGMA= | 3.7 | PHAS= | -90.0 | FOM= | 1.00 | TEST= 0 |
| INDE | 0 | 49 | 19 | FOBS= | 302.4 | SIGMA= | 1.2 | PHAS= | 90.0 | FOM= | 1.00 | TEST= 0 |
| INDE | 0 | 49 | 21 | FOBS= | 131.5 | SIGMA= | 2.3 | PHAS= | -90.0 | FOM= | 0.75 | TEST= 0 |
| INDE | 0 | 49 | 31 | FOBS= | 17.8 | SIGMA= | 26.3 | PHAS= | -90.0 | FOM= | 0.26 | TEST= 0 |
| INDE | 0 | 49 | 33 | FOBS= | 29.8 | SIGMA= | 11.3 | PHAS= | -90.0 | FOM= | 0.13 | TEST= 0 |
| INDE | 0 | 49 | 35 | FOBS= | 0.0 | SIGMA= | 25.6 | PHAS= | 0.0 | FOM= | 0.00 | TEST= 0 |
| INDE | 0 | 49 | 37 | FOBS= | 0.0 | SIGMA= | 23.8 | PHAS= | 0.0 | FOM= | 0.00 | TEST= 0 |
| INDE | 0 | 49 | 39 | FOBS= | 0.0 | SIGMA= | 22.4 | PHAS= | 0.0 | FOM= | 0.00 | TEST= 0 |
| INDE | 0 | 49 | 41 | FOBS= | 3.1 | SIGMA= | 80.1 | PHAS= | 90.0 | FOM= | 0.07 | TEST= 0 |
| INDE | 0 | 49 | 43 | FOBS= | 36.1 | SIGMA= | 6.9 | PHAS= | -90.0 | FOM= | 0.69 | TEST= 0 |
| INDE | 0 | 49 | 45 | FOBS= | 84.1 | SIGMA= | 3.0 | PHAS= | -90.0 | FOM= | 0.78 | TEST= 0 |
| INDE | 0 | 49 | 47 | FOBS= | 97.5 | SIGMA= | 2.6 | PHAS= | 90.0 | FOM= | 0.95 | TEST= 0 |
| INDE | 0 | 49 | 49 | FOBS= | 75.7 | SIGMA= | 4.0 | PHAS= | 90.0 | FOM= | 0.98 | TEST= 0 |
| INDE | 0 | 49 | 51 | FOBS= | 48.2 | SIGMA= | 6.9 | PHAS= | 90.0 | FOM= | 0.87 | TEST= 0 |
| INDE | 0 | 49 | 53 | FOBS= | 53.0 | SIGMA= | 6.2 | PHAS= | 90.0 | FOM= | 0.38 | TEST= 1 |
| INDE | 0 | 49 | 55 | FOBS= | 58.2 | SIGMA= | 5.8 | PHAS= | -90.0 | FOM= | 0.16 | TEST= 0 |
| INDE | 0 | 49 | 57 | FOBS= | 0.0 | SIGMA= | 23.8 | PHAS= | 0.0 | FOM= | 0.00 | TEST= 0 |
| INDE | 0 | 49 | 59 | FOBS= | 0.0 | SIGMA= | 24.0 | PHAS= | 0.0 | FOM= | 0.00 | TEST= 0 |
| INDE | 0 | 50 | 0 | FOBS= | 702.8 | SIGMA= | 0.6 | PHAS= | -180.0 | FOM= | 1.00 | TEST= 0 |
| INDE | 0 | 50 | 2 | FOBS= | 155.3 | SIGMA= | 1.4 | PHAS= | 0.0 | FOM= | 0.85 | TEST= 0 |
| INDE | 0 | 50 | 14 | FOBS= | 175.9 | SIGMA= | 1.5 | PHAS= | -180.0 | FOM= | 1.00 | TEST= 0 |
| INDE | 0 | 50 | 16 | FOBS= | 252.7 | SIGMA= | 1.2 | PHAS= | -180.0 | FOM= | 1.00 | TEST= 0 |
| INDE | 0 | 50 | 18 | FOBS= | 115.4 | SIGMA= | 2.4 | PHAS= | -180.0 | FOM= | 1.00 | TEST= 0 |
| INDE | 0 | 50 | 20 | FOBS= | 0.0 | SIGMA= | 23.9 | PHAS= | 0.0 | FOM= | 0.00 | TEST= 0 |
| INDE | 0 | 50 | 22 | FOBS= | 71.8 | SIGMA= | 4.0 | PHAS= | 0.0 | FOM= | 1.00 | TEST= 0 |
| INDE | 0 | 50 | 30 | FOBS= | 47.5 | SIGMA= | 9.8 | PHAS= | 0.0 | FOM= | 0.33 | TEST= 0 |
| INDE | 0 | 50 | 32 | FOBS= | 47.3 | SIGMA= | 7.1 | PHAS= | -180.0 | FOM= | 0.61 | TEST= 1 |
| INDE | 0 | 50 | 34 | FOBS= | 0.0 | SIGMA= | 25.8 | PHAS= | 0.0 | FOM= | 0.00 | TEST= 0 |
| INDE | 0 | 50 | 36 | FOBS= | 0.0 | SIGMA= | 25.4 | PHAS= | 0.0 | FOM= | 0.00 | TEST= 0 |
| INDE | 0 | 50 | 38 | FOBS= | 0.0 | SIGMA= | 23.7 | PHAS= | 0.0 | FOM= | 0.00 | TEST= 0 |
| INDE | 0 | 50 | 40 | FOBS= | 95.1 | SIGMA= | 2.7 | PHAS= | 0.0 | FOM= | 1.00 | TEST= 0 |
| INDE | 0 | 50 | 42 | FOBS= | 40.5 | SIGMA= | 6.2 | PHAS= | -180.0 | FOM= | 0.54 | TEST= 0 |
| INDE | 0 | 50 | 44 | FOBS= | 125.8 | SIGMA= | 2.1 | PHAS= | -180.0 | FOM= | 0.15 | TEST= 1 |
| INDE | 0 | 50 | 46 | FOBS= | 0.0 | SIGMA= | 22.3 | PHAS= | 0.0 | FOM= | 0.00 | TEST= 0 |
| INDE | 0 | 50 | 48 | FOBS= | 0.0 | SIGMA= | 26.4 | PHAS= | 0.0 | FOM= | 0.00 | TEST= 0 |
| INDE | 0 | 50 | 50 | FOBS= | 0.0 | SIGMA= | 26.1 | PHAS= | 0.0 | FOM= | 0.00 | TEST= 0 |
| INDE | 0 | 50 | 52 | FOBS= | 99.6 | SIGMA= | 3.5 | PHAS= | 0.0 | FOM= | 0.96 | TEST= 0 |
| INDE | 0 | 50 | 54 | FOBS= | 63.9 | SIGMA= | 5.3 | PHAS= | 0.0 | FOM= | 0.18 | TEST= 0 |
| INDE | 0 | 50 | 56 | FOBS= | 0.0 | SIGMA= | 25.7 | PHAS= | 0.0 | FOM= | 0.00 | TEST= 0 |
| INDE | 0 | 50 | 58 | FOBS= | 0.0 | SIGMA= | 26.2 | PHAS= | 0.0 | FOM= | 0.00 | TEST= 0 |
| INDE | 0 | 51 | 1 | FOBS= | 315.9 | SIGMA= | 0.8 | PHAS= | 90.0 | FOM= | 1.00 | TEST= 0 |
| INDE | 0 | 51 | 3 | FOBS= | 16.9 | SIGMA= | 12.2 | PHAS= | 0.0 | FOM= | 0.00 | TEST= 1 |
| INDE | 0 | 51 | 13 | FOBS= | 0.0 | SIGMA= | 21.9 | PHAS= | 0.0 | FOM= | 0.00 | TEST= 0 |
| INDE | 0 | 51 | 15 | FOBS= | 0.0 | SIGMA= | 22.5 | PHAS= | 0.0 | FOM= | 0.00 | TEST= 0 |
| INDE | 0 | 51 | 17 | FOBS= | 286.6 | SIGMA= | 1.1 | PHAS= | 90.0 | FOM= | 1.00 | TEST= 0 |
| INDE | 0 | 51 | 19 | FOBS= | 54.7 | SIGMA= | 5.0 | PHAS= | 90.0 | FOM= | 0.19 | TEST= 0 |
| INDE | 0 | 51 | 21 | FOBS= | 55.4 | SIGMA= | 5.2 | PHAS= | 90.0 | FOM= | 1.00 | TEST= 0 |
| INDE | 0 | 51 | 23 | FOBS= | 27.0 | SIGMA= | 10.6 | PHAS= | -90.0 | FOM= | 0.32 | TEST= 0 |
| INDE | 0 | 51 | 31 | FOBS= | 164.3 | SIGMA= | 2.2 | PHAS= | 90.0 | FOM= | 1.00 | TEST= 0 |
| INDE | 0 | 51 | 33 | FOBS= | 47.3 | SIGMA= | 7.1 | PHAS= | -90.0 | FOM= | 0.57 | TEST= 0 |

*FIG. 12A - 19*

```
INDE  0  51  35  FOBS=   81.4  SIGMA=   4.1  PHAS=   90.0  FOM=  0.09  TEST= 0
INDE  0  51  37  FOBS=   42.3  SIGMA=   7.8  PHAS=   90.0  FOM=  0.34  TEST= 0
INDE  0  51  39  FOBS=  212.1  SIGMA=   1.4  PHAS=  -90.0  FOM=  1.00  TEST= 0
INDE  0  51  41  FOBS=   99.6  SIGMA=   2.6  PHAS=  -90.0  FOM=  0.36  TEST= 1
INDE  0  51  43  FOBS=  159.5  SIGMA=   1.7  PHAS=   90.0  FOM=  1.00  TEST= 0
INDE  0  51  45  FOBS=    0.0  SIGMA=  22.3  PHAS=    0.0  FOM=  0.00  TEST= 0
INDE  0  51  47  FOBS=   74.7  SIGMA=   3.4  PHAS=   90.0  FOM=  0.20  TEST= 0
INDE  0  51  49  FOBS=   45.1  SIGMA=   6.6  PHAS=  -90.0  FOM=  0.43  TEST= 0
INDE  0  51  51  FOBS=  124.4  SIGMA=   2.9  PHAS=  -90.0  FOM=  1.00  TEST= 0
INDE  0  51  53  FOBS=   79.4  SIGMA=   4.3  PHAS=  -90.0  FOM=  0.72  TEST= 0
INDE  0  51  55  FOBS=   25.4  SIGMA=  13.2  PHAS=   90.0  FOM=  0.46  TEST= 0
INDE  0  51  57  FOBS=   42.6  SIGMA=   8.2  PHAS=   90.0  FOM=  0.03  TEST= 1
INDE  0  52   0  FOBS=   95.3  SIGMA=   2.2  PHAS=    0.0  FOM=  0.93  TEST= 0
INDE  0  52   2  FOBS=    0.0  SIGMA=  20.2  PHAS=    0.0  FOM=  0.00  TEST= 0
INDE  0  52  14  FOBS=  309.9  SIGMA=   1.0  PHAS=    0.0  FOM=  1.00  TEST= 0
INDE  0  52  16  FOBS=   20.9  SIGMA=  12.1  PHAS=    0.0  FOM=  0.33  TEST= 0
INDE  0  52  18  FOBS=  275.5  SIGMA=   1.2  PHAS=    0.0  FOM=  1.00  TEST= 0
INDE  0  52  20  FOBS=  117.9  SIGMA=   2.4  PHAS=    0.0  FOM=  0.99  TEST= 0
INDE  0  52  22  FOBS=    0.0  SIGMA=  24.2  PHAS=    0.0  FOM=  0.00  TEST= 0
INDE  0  52  24  FOBS=  135.6  SIGMA=   2.3  PHAS= -180.0  FOM=  1.00  TEST= 0
INDE  0  52  30  FOBS=  104.7  SIGMA=   4.6  PHAS=    0.0  FOM=  0.95  TEST= 0
INDE  0  52  32  FOBS=   42.8  SIGMA=   7.8  PHAS=    0.0  FOM=  0.15  TEST= 0
INDE  0  52  34  FOBS=  163.9  SIGMA=   2.2  PHAS=    0.0  FOM=  1.00  TEST= 0
INDE  0  52  36  FOBS=   23.8  SIGMA=  13.8  PHAS= -180.0  FOM=  0.04  TEST= 0
INDE  0  52  38  FOBS=  226.6  SIGMA=   1.7  PHAS= -180.0  FOM=  1.00  TEST= 0
INDE  0  52  40  FOBS=   66.8  SIGMA=   3.8  PHAS=    0.0  FOM=  0.06  TEST= 0
INDE  0  52  42  FOBS=   27.4  SIGMA=  10.1  PHAS=    0.0  FOM=  0.08  TEST= 0
INDE  0  52  44  FOBS=   74.3  SIGMA=   3.5  PHAS=    0.0  FOM=  0.89  TEST= 0
INDE  0  52  46  FOBS=   41.8  SIGMA=   6.0  PHAS= -180.0  FOM=  0.25  TEST= 0
INDE  0  52  48  FOBS=    0.0  SIGMA=  24.3  PHAS=    0.0  FOM=  0.00  TEST= 0
INDE  0  52  50  FOBS=   52.1  SIGMA=   5.8  PHAS= -180.0  FOM=  0.91  TEST= 0
INDE  0  52  52  FOBS=   90.4  SIGMA=   3.9  PHAS= -180.0  FOM=  0.98  TEST= 0
INDE  0  52  54  FOBS=   72.1  SIGMA=   4.8  PHAS= -180.0  FOM=  0.97  TEST= 0
INDE  0  52  56  FOBS=    0.0  SIGMA=  29.4  PHAS=    0.0  FOM=  0.00  TEST= 0
INDE  0  53   1  FOBS=  284.3  SIGMA=   0.8  PHAS=  -90.0  FOM=  1.00  TEST= 0
INDE  0  53   3  FOBS=  228.0  SIGMA=   1.1  PHAS=   90.0  FOM=  1.00  TEST= 0
INDE  0  53  15  FOBS=  128.3  SIGMA=   2.0  PHAS=  -90.0  FOM=  0.68  TEST= 0
INDE  0  53  17  FOBS=   94.2  SIGMA=   2.8  PHAS=  -90.0  FOM=  0.82  TEST= 0
INDE  0  53  19  FOBS=  406.1  SIGMA=   0.9  PHAS=  -90.0  FOM=  1.00  TEST= 0
INDE  0  53  21  FOBS=    0.0  SIGMA=  23.9  PHAS=    0.0  FOM=  0.00  TEST= 0
INDE  0  53  23  FOBS=  159.6  SIGMA=   2.0  PHAS=  -90.0  FOM=  0.23  TEST= 0
INDE  0  53  25  FOBS=  124.2  SIGMA=   2.5  PHAS=   90.0  FOM=  0.47  TEST= 0
INDE  0  53  31  FOBS=    0.0  SIGMA=  26.0  PHAS=    0.0  FOM=  0.00  TEST= 0
INDE  0  53  33  FOBS=  130.4  SIGMA=   2.7  PHAS=  -90.0  FOM=  1.00  TEST= 0
INDE  0  53  35  FOBS=   31.6  SIGMA=  10.7  PHAS=   90.0  FOM=  0.37  TEST= 0
INDE  0  53  37  FOBS=   29.1  SIGMA=  11.4  PHAS=   90.0  FOM=  0.32  TEST= 0
INDE  0  53  39  FOBS=   78.0  SIGMA=   3.3  PHAS=   90.0  FOM=  0.16  TEST= 0
INDE  0  53  41  FOBS=   26.4  SIGMA=   9.5  PHAS=  -90.0  FOM=  0.20  TEST= 0
INDE  0  53  43  FOBS=   56.7  SIGMA=   4.5  PHAS=   90.0  FOM=  0.59  TEST= 0
INDE  0  53  45  FOBS=    0.0  SIGMA=  22.3  PHAS=    0.0  FOM=  0.00  TEST= 0
INDE  0  53  47  FOBS=    0.0  SIGMA=  28.9  PHAS=    0.0  FOM=  0.00  TEST= 0
INDE  0  53  49  FOBS=    0.0  SIGMA=  24.4  PHAS=    0.0  FOM=  0.00  TEST= 0
INDE  0  53  51  FOBS=    0.0  SIGMA=  26.5  PHAS=    0.0  FOM=  0.00  TEST= 0
INDE  0  53  53  FOBS=   36.3  SIGMA=   9.6  PHAS=   90.0  FOM=  0.55  TEST= 0
INDE  0  53  55  FOBS=    0.0  SIGMA=  29.4  PHAS=    0.0  FOM=  0.00  TEST= 0
INDE  0  54   0  FOBS=  426.2  SIGMA=   1.0  PHAS= -180.0  FOM=  1.00  TEST= 0
INDE  0  54   2  FOBS=    0.0  SIGMA=  20.1  PHAS=    0.0  FOM=  0.00  TEST= 0
INDE  0  54   4  FOBS=  404.0  SIGMA=   0.7  PHAS=    0.0  FOM=  1.00  TEST= 0
INDE  0  54  14  FOBS=   20.6  SIGMA=  11.2  PHAS=    0.0  FOM=  0.26  TEST= 0
INDE  0  54  16  FOBS=  243.2  SIGMA=   1.2  PHAS= -180.0  FOM=  0.99  TEST= 0
INDE  0  54  18  FOBS=   64.9  SIGMA=   3.9  PHAS= -180.0  FOM=  0.78  TEST= 0
INDE  0  54  20  FOBS=   56.8  SIGMA=   4.7  PHAS=    0.0  FOM=  0.33  TEST= 0
INDE  0  54  22  FOBS=   36.3  SIGMA=   7.8  PHAS= -180.0  FOM=  0.92  TEST= 0
INDE  0  54  24  FOBS=   28.5  SIGMA=  10.5  PHAS= -180.0  FOM=  0.01  TEST= 1
INDE  0  54  26  FOBS=   76.1  SIGMA=   3.9  PHAS= -180.0  FOM=  0.00  TEST= 1
INDE  0  54  30  FOBS=   73.6  SIGMA=   6.4  PHAS= -180.0  FOM=  0.96  TEST= 0
INDE  0  54  32  FOBS=   56.8  SIGMA=   6.0  PHAS=    0.0  FOM=  0.01  TEST= 0
INDE  0  54  34  FOBS=    0.0  SIGMA=  25.8  PHAS=    0.0  FOM=  0.00  TEST= 0
INDE  0  54  36  FOBS=   43.1  SIGMA=   7.7  PHAS=    0.0  FOM=  0.99  TEST= 0
INDE  0  54  38  FOBS=  149.8  SIGMA=   2.4  PHAS= -180.0  FOM=  0.96  TEST= 0
```

*FIG. 12A - 20*

| | | | | | | | | | | | |
|---|---|---|---|---|---|---|---|---|---|---|---|
| INDE | 0 | 54 | 40 | FOBS= | 41.3 | SIGMA= | 6.1 | PHAS= | -180.0 | FOM= | 0.99 | TEST= 0
| INDE | 0 | 54 | 42 | FOBS= | 0.0 | SIGMA= | 23.5 | PHAS= | 0.0 | FOM= | 0.00 | TEST= 0
| INDE | 0 | 54 | 44 | FOBS= | 57.2 | SIGMA= | 4.5 | PHAS= | 0.0 | FOM= | 0.58 | TEST= 0
| INDE | 0 | 54 | 46 | FOBS= | 0.0 | SIGMA= | 25.0 | PHAS= | 0.0 | FOM= | 0.00 | TEST= 0
| INDE | 0 | 54 | 48 | FOBS= | 0.0 | SIGMA= | 24.5 | PHAS= | 0.0 | FOM= | 0.00 | TEST= 1
| INDE | 0 | 54 | 50 | FOBS= | 0.0 | SIGMA= | 24.6 | PHAS= | 0.0 | FOM= | 0.00 | TEST= 0
| INDE | 0 | 54 | 52 | FOBS= | 0.0 | SIGMA= | 26.6 | PHAS= | 0.0 | FOM= | 0.00 | TEST= 0
| INDE | 0 | 54 | 54 | FOBS= | 0.0 | SIGMA= | 29.4 | PHAS= | 0.0 | FOM= | 0.00 | TEST= 0
| INDE | 0 | 55 | 1 | FOBS= | 48.7 | SIGMA= | 5.7 | PHAS= | 90.0 | FOM= | 0.28 | TEST= 0
| INDE | 0 | 55 | 3 | FOBS= | 0.0 | SIGMA= | 20.2 | PHAS= | 0.0 | FOM= | 0.00 | TEST= 0
| INDE | 0 | 55 | 15 | FOBS= | 136.0 | SIGMA= | 1.8 | PHAS= | -90.0 | FOM= | 0.85 | TEST= 1
| INDE | 0 | 55 | 17 | FOBS= | 55.8 | SIGMA= | 4.5 | PHAS= | -90.0 | FOM= | 0.51 | TEST= 0
| INDE | 0 | 55 | 19 | FOBS= | 93.6 | SIGMA= | 2.8 | PHAS= | -90.0 | FOM= | 0.93 | TEST= 0
| INDE | 0 | 55 | 21 | FOBS= | 27.3 | SIGMA= | 9.8 | PHAS= | 90.0 | FOM= | 0.16 | TEST= 0
| INDE | 0 | 55 | 23 | FOBS= | 206.4 | SIGMA= | 1.6 | PHAS= | 90.0 | FOM= | 1.00 | TEST= 0
| INDE | 0 | 55 | 25 | FOBS= | 172.2 | SIGMA= | 1.9 | PHAS= | -90.0 | FOM= | 1.00 | TEST= 0
| INDE | 0 | 55 | 27 | FOBS= | 0.0 | SIGMA= | 27.7 | PHAS= | 0.0 | FOM= | 0.00 | TEST= 0
| INDE | 0 | 55 | 29 | FOBS= | 110.9 | SIGMA= | 4.4 | PHAS= | 90.0 | FOM= | 0.78 | TEST= 0
| INDE | 0 | 55 | 31 | FOBS= | 16.5 | SIGMA= | 20.4 | PHAS= | 90.0 | FOM= | 0.11 | TEST= 0
| INDE | 0 | 55 | 33 | FOBS= | 173.8 | SIGMA= | 2.1 | PHAS= | -90.0 | FOM= | 1.00 | TEST= 0
| INDE | 0 | 55 | 35 | FOBS= | 164.8 | SIGMA= | 2.2 | PHAS= | -90.0 | FOM= | 1.00 | TEST= 0
| INDE | 0 | 55 | 37 | FOBS= | 41.1 | SIGMA= | 8.0 | PHAS= | 90.0 | FOM= | 0.40 | TEST= 0
| INDE | 0 | 55 | 39 | FOBS= | 59.8 | SIGMA= | 5.5 | PHAS= | -90.0 | FOM= | 0.19 | TEST= 0
| INDE | 0 | 55 | 41 | FOBS= | 0.0 | SIGMA= | 22.4 | PHAS= | 0.0 | FOM= | 0.00 | TEST= 0
| INDE | 0 | 55 | 43 | FOBS= | 0.0 | SIGMA= | 26.6 | PHAS= | 0.0 | FOM= | 0.00 | TEST= 0
| INDE | 0 | 55 | 45 | FOBS= | 53.4 | SIGMA= | 4.8 | PHAS= | 90.0 | FOM= | 0.49 | TEST= 0
| INDE | 0 | 55 | 47 | FOBS= | 13.9 | SIGMA= | 26.6 | PHAS= | -90.0 | FOM= | 0.03 | TEST= 0
| INDE | 0 | 55 | 49 | FOBS= | 0.0 | SIGMA= | 28.8 | PHAS= | 0.0 | FOM= | 0.00 | TEST= 1
| INDE | 0 | 55 | 51 | FOBS= | 36.1 | SIGMA= | 10.1 | PHAS= | 90.0 | FOM= | 0.62 | TEST= 0
| INDE | 0 | 55 | 53 | FOBS= | 0.0 | SIGMA= | 29.7 | PHAS= | 0.0 | FOM= | 0.00 | TEST= 0
| INDE | 0 | 56 | 2 | FOBS= | 68.1 | SIGMA= | 2.9 | PHAS= | 0.0 | FOM= | 0.75 | TEST= 0
| INDE | 0 | 56 | 4 | FOBS= | 142.3 | SIGMA= | 1.5 | PHAS= | 0.0 | FOM= | 1.00 | TEST= 0
| INDE | 0 | 56 | 16 | FOBS= | 56.4 | SIGMA= | 4.2 | PHAS= | -180.0 | FOM= | 0.96 | TEST= 0
| INDE | 0 | 56 | 18 | FOBS= | 0.0 | SIGMA= | 22.4 | PHAS= | 0.0 | FOM= | 0.00 | TEST= 0
| INDE | 0 | 56 | 20 | FOBS= | 45.9 | SIGMA= | 5.6 | PHAS= | -180.0 | FOM= | 0.17 | TEST= 1
| INDE | 0 | 56 | 22 | FOBS= | 0.0 | SIGMA= | 23.4 | PHAS= | 0.0 | FOM= | 0.00 | TEST= 0
| INDE | 0 | 56 | 24 | FOBS= | 124.5 | SIGMA= | 2.4 | PHAS= | 0.0 | FOM= | 1.00 | TEST= 0
| INDE | 0 | 56 | 26 | FOBS= | 53.2 | SIGMA= | 5.6 | PHAS= | 0.0 | FOM= | 0.25 | TEST= 0
| INDE | 0 | 56 | 30 | FOBS= | 0.0 | SIGMA= | 26.1 | PHAS= | 0.0 | FOM= | 0.00 | TEST= 0
| INDE | 0 | 56 | 32 | FOBS= | 60.1 | SIGMA= | 5.7 | PHAS= | -180.0 | FOM= | 0.54 | TEST= 0
| INDE | 0 | 56 | 34 | FOBS= | 219.8 | SIGMA= | 1.8 | PHAS= | -180.0 | FOM= | 1.00 | TEST= 0
| INDE | 0 | 56 | 36 | FOBS= | 0.0 | SIGMA= | 25.9 | PHAS= | 0.0 | FOM= | 0.00 | TEST= 0
| INDE | 0 | 56 | 38 | FOBS= | 34.8 | SIGMA= | 9.6 | PHAS= | -180.0 | FOM= | 0.51 | TEST= 0
| INDE | 0 | 56 | 40 | FOBS= | 0.0 | SIGMA= | 23.6 | PHAS= | 0.0 | FOM= | 0.00 | TEST= 0
| INDE | 0 | 56 | 42 | FOBS= | 30.2 | SIGMA= | 8.3 | PHAS= | -180.0 | FOM= | 0.35 | TEST= 0
| INDE | 0 | 56 | 44 | FOBS= | 10.0 | SIGMA= | 27.8 | PHAS= | 0.0 | FOM= | 0.15 | TEST= 0
| INDE | 0 | 56 | 46 | FOBS= | 42.1 | SIGMA= | 7.2 | PHAS= | -180.0 | FOM= | 0.02 | TEST= 0
| INDE | 0 | 56 | 48 | FOBS= | 12.0 | SIGMA= | 25.8 | PHAS= | 0.0 | FOM= | 0.02 | TEST= 0
| INDE | 0 | 56 | 50 | FOBS= | 57.0 | SIGMA= | 5.5 | PHAS= | 0.0 | FOM= | 0.46 | TEST= 0
| INDE | 0 | 56 | 52 | FOBS= | 0.0 | SIGMA= | 29.9 | PHAS= | 0.0 | FOM= | 0.00 | TEST= 0
| INDE | 0 | 57 | 1 | FOBS= | 105.9 | SIGMA= | 1.9 | PHAS= | -90.0 | FOM= | 0.71 | TEST= 0
| INDE | 0 | 57 | 3 | FOBS= | 0.0 | SIGMA= | 19.9 | PHAS= | 0.0 | FOM= | 0.00 | TEST= 0
| INDE | 0 | 57 | 17 | FOBS= | 0.0 | SIGMA= | 21.8 | PHAS= | 0.0 | FOM= | 0.00 | TEST= 0
| INDE | 0 | 57 | 19 | FOBS= | 120.8 | SIGMA= | 2.3 | PHAS= | 90.0 | FOM= | 1.00 | TEST= 0
| INDE | 0 | 57 | 21 | FOBS= | 0.0 | SIGMA= | 22.9 | PHAS= | 0.0 | FOM= | 0.00 | TEST= 0
| INDE | 0 | 57 | 23 | FOBS= | 20.5 | SIGMA= | 13.7 | PHAS= | -90.0 | FOM= | 0.47 | TEST= 0
| INDE | 0 | 57 | 25 | FOBS= | 147.6 | SIGMA= | 2.1 | PHAS= | -90.0 | FOM= | 1.00 | TEST= 0
| INDE | 0 | 57 | 27 | FOBS= | 82.6 | SIGMA= | 3.7 | PHAS= | -90.0 | FOM= | 0.96 | TEST= 0
| INDE | 0 | 57 | 29 | FOBS= | 54.4 | SIGMA= | 8.5 | PHAS= | -90.0 | FOM= | 0.28 | TEST= 0
| INDE | 0 | 57 | 31 | FOBS= | 38.4 | SIGMA= | 8.8 | PHAS= | -90.0 | FOM= | 0.10 | TEST= 0
| INDE | 0 | 57 | 33 | FOBS= | 35.3 | SIGMA= | 9.6 | PHAS= | -90.0 | FOM= | 0.05 | TEST= 0
| INDE | 0 | 57 | 35 | FOBS= | 73.2 | SIGMA= | 4.6 | PHAS= | -90.0 | FOM= | 0.99 | TEST= 0
| INDE | 0 | 57 | 37 | FOBS= | 0.0 | SIGMA= | 25.6 | PHAS= | 0.0 | FOM= | 0.00 | TEST= 0
| INDE | 0 | 57 | 39 | FOBS= | 0.0 | SIGMA= | 25.7 | PHAS= | 0.0 | FOM= | 0.00 | TEST= 0
| INDE | 0 | 57 | 41 | FOBS= | 0.0 | SIGMA= | 23.7 | PHAS= | 0.0 | FOM= | 0.00 | TEST= 0
| INDE | 0 | 57 | 43 | FOBS= | 63.7 | SIGMA= | 4.0 | PHAS= | 90.0 | FOM= | 0.66 | TEST= 0
| INDE | 0 | 57 | 45 | FOBS= | 48.6 | SIGMA= | 5.3 | PHAS= | 90.0 | FOM= | 0.67 | TEST= 0
| INDE | 0 | 57 | 47 | FOBS= | 52.1 | SIGMA= | 6.1 | PHAS= | 90.0 | FOM= | 0.90 | TEST= 0
| INDE | 0 | 57 | 49 | FOBS= | 42.9 | SIGMA= | 7.2 | PHAS= | -90.0 | FOM= | 0.97 | TEST= 0
| INDE | 0 | 57 | 51 | FOBS= | 44.3 | SIGMA= | 10.3 | PHAS= | -90.0 | FOM= | 0.38 | TEST= 0

*FIG. 12A - 21*

```
INDE   0   58    2 FOBS=    0.0 SIGMA=  19.7 PHAS=    0.0 FOM= 0.00 TEST= 0
INDE   0   58    4 FOBS=   92.8 SIGMA=   2.3 PHAS=    0.0 FOM= 0.41 TEST= 1
INDE   0   58   16 FOBS=   26.8 SIGMA=   8.5 PHAS= -180.0 FOM= 0.01 TEST= 0
INDE   0   58   18 FOBS=   54.8 SIGMA=   4.5 PHAS= -180.0 FOM= 0.87 TEST= 0
INDE   0   58   20 FOBS=   45.8 SIGMA=   5.7 PHAS=    0.0 FOM= 0.75 TEST= 0
INDE   0   58   22 FOBS=   56.1 SIGMA=   4.7 PHAS= -180.0 FOM= 0.24 TEST= 0
INDE   0   58   24 FOBS=    0.0 SIGMA=  23.8 PHAS=    0.0 FOM= 0.00 TEST= 0
INDE   0   58   26 FOBS=   16.1 SIGMA=  18.4 PHAS= -180.0 FOM= 0.04 TEST= 0
INDE   0   58   28 FOBS=    7.6 SIGMA=  32.6 PHAS= -180.0 FOM= 0.18 TEST= 0
INDE   0   58   30 FOBS=    0.0 SIGMA=  25.9 PHAS=    0.0 FOM= 0.00 TEST= 1
INDE   0   58   32 FOBS=   21.8 SIGMA=  15.5 PHAS= -180.0 FOM= 0.29 TEST= 0
INDE   0   58   34 FOBS=  140.6 SIGMA=   2.6 PHAS= -180.0 FOM= 0.73 TEST= 0
INDE   0   58   36 FOBS=    0.0 SIGMA=  25.7 PHAS=    0.0 FOM= 0.00 TEST= 0
INDE   0   58   38 FOBS=   22.5 SIGMA=  14.7 PHAS=    0.0 FOM= 0.66 TEST= 0
INDE   0   58   40 FOBS=    0.0 SIGMA=  25.7 PHAS=    0.0 FOM= 0.00 TEST= 0
INDE   0   58   42 FOBS=   80.3 SIGMA=   3.3 PHAS=    0.0 FOM= 0.94 TEST= 0
INDE   0   58   44 FOBS=   22.0 SIGMA=  16.1 PHAS=    0.0 FOM= 0.27 TEST= 0
INDE   0   58   46 FOBS=   69.6 SIGMA=   4.5 PHAS=    0.0 FOM= 0.97 TEST= 0
INDE   0   58   48 FOBS=   24.2 SIGMA=  12.9 PHAS= -180.0 FOM= 0.43 TEST= 0
INDE   0   58   50 FOBS=   28.2 SIGMA=  16.3 PHAS= -180.0 FOM= 0.54 TEST= 0
INDE   0   59    1 FOBS=  101.5 SIGMA=   2.8 PHAS=  -90.0 FOM= 0.94 TEST= 0
INDE   0   59    3 FOBS=   39.3 SIGMA=   4.8 PHAS=   90.0 FOM= 0.21 TEST= 0
INDE   0   59    5 FOBS=   47.4 SIGMA=   4.2 PHAS=  -90.0 FOM= 0.59 TEST= 0
INDE   0   59   17 FOBS=   44.4 SIGMA=   5.3 PHAS=   90.0 FOM= 0.09 TEST= 0
INDE   0   59   19 FOBS=    0.0 SIGMA=  22.4 PHAS=    0.0 FOM= 0.00 TEST= 0
INDE   0   59   21 FOBS=   77.0 SIGMA=   3.4 PHAS=  -90.0 FOM= 0.99 TEST= 0
INDE   0   59   23 FOBS=   29.5 SIGMA=   9.1 PHAS=   90.0 FOM= 0.09 TEST= 0
INDE   0   59   25 FOBS=   78.8 SIGMA=   3.7 PHAS=  -90.0 FOM= 0.99 TEST= 0
INDE   0   59   27 FOBS=   42.1 SIGMA=   6.1 PHAS=  -90.0 FOM= 0.05 TEST= 0
INDE   0   59   29 FOBS=   71.5 SIGMA=   3.2 PHAS=  -90.0 FOM= 0.99 TEST= 0
INDE   0   59   31 FOBS=  102.4 SIGMA=   3.4 PHAS=   90.0 FOM= 0.70 TEST= 0
INDE   0   59   33 FOBS=    0.0 SIGMA=  26.0 PHAS=    0.0 FOM= 0.00 TEST= 1
INDE   0   59   35 FOBS=   96.3 SIGMA=   3.6 PHAS=  -90.0 FOM= 0.96 TEST= 0
INDE   0   59   37 FOBS=    0.0 SIGMA=  25.9 PHAS=    0.0 FOM= 0.00 TEST= 0
INDE   0   59   39 FOBS=    0.0 SIGMA=  26.0 PHAS=    0.0 FOM= 0.00 TEST= 0
INDE   0   59   41 FOBS=   36.1 SIGMA=   9.1 PHAS=  -90.0 FOM= 0.22 TEST= 0
INDE   0   59   43 FOBS=    0.0 SIGMA=  24.5 PHAS=    0.0 FOM= 0.00 TEST= 1
INDE   0   59   45 FOBS=   41.0 SIGMA=   9.0 PHAS=  -90.0 FOM= 0.53 TEST= 0
INDE   0   59   47 FOBS=   34.2 SIGMA=   9.2 PHAS=  -90.0 FOM= 0.16 TEST= 0
INDE   0   59   49 FOBS=   41.5 SIGMA=  11.3 PHAS=  -90.0 FOM= 0.58 TEST= 0
INDE   0   60    2 FOBS=   34.7 SIGMA=   5.7 PHAS=    0.0 FOM= 0.64 TEST= 1
INDE   0   60    4 FOBS=   93.8 SIGMA=   2.2 PHAS= -180.0 FOM= 0.98 TEST= 0
INDE   0   60   18 FOBS=    0.0 SIGMA=  25.4 PHAS=    0.0 FOM= 0.00 TEST= 0
INDE   0   60   20 FOBS=   86.1 SIGMA=   4.5 PHAS= -180.0 FOM= 0.19 TEST= 0
INDE   0   60   22 FOBS=   36.2 SIGMA=  10.1 PHAS= -180.0 FOM= 0.11 TEST= 0
INDE   0   60   24 FOBS=    0.0 SIGMA=  27.9 PHAS=    0.0 FOM= 0.00 TEST= 0
INDE   0   60   26 FOBS=   63.3 SIGMA=   6.8 PHAS=    0.0 FOM= 0.34 TEST= 1
INDE   0   60   28 FOBS=  129.9 SIGMA=   2.3 PHAS= -180.0 FOM= 1.00 TEST= 0
INDE   0   60   30 FOBS=    8.8 SIGMA=  30.8 PHAS= -180.0 FOM= 0.05 TEST= 0
INDE   0   60   32 FOBS=    0.0 SIGMA=  26.0 PHAS=    0.0 FOM= 0.00 TEST= 0
INDE   0   60   34 FOBS=  127.8 SIGMA=   2.8 PHAS= -180.0 FOM= 1.00 TEST= 0
INDE   0   60   36 FOBS=  115.4 SIGMA=   3.1 PHAS= -180.0 FOM= 1.00 TEST= 0
INDE   0   60   38 FOBS=   69.2 SIGMA=   5.0 PHAS=    0.0 FOM= 0.97 TEST= 0
INDE   0   60   40 FOBS=   35.2 SIGMA=   9.6 PHAS=    0.0 FOM= 0.44 TEST= 0
INDE   0   60   42 FOBS=    0.0 SIGMA=  24.0 PHAS=    0.0 FOM= 0.00 TEST= 0
INDE   0   60   44 FOBS=    0.0 SIGMA=  24.8 PHAS=    0.0 FOM= 0.00 TEST= 0
INDE   0   60   46 FOBS=   29.0 SIGMA=  12.7 PHAS= -180.0 FOM= 0.60 TEST= 0
INDE   0   60   48 FOBS=   38.4 SIGMA=  12.2 PHAS=    0.0 FOM= 0.00 TEST= 1
INDE   0   61    3 FOBS=  203.6 SIGMA=   1.0 PHAS=   90.0 FOM= 0.97 TEST= 1
INDE   0   61    5 FOBS=   78.0 SIGMA=   2.7 PHAS=   90.0 FOM= 0.05 TEST= 1
INDE   0   61   19 FOBS=   58.1 SIGMA=   5.7 PHAS=   90.0 FOM= 0.28 TEST= 0
INDE   0   61   21 FOBS=   12.4 SIGMA=  30.3 PHAS=   90.0 FOM= 0.04 TEST= 0
INDE   0   61   23 FOBS=    0.0 SIGMA=  27.2 PHAS=    0.0 FOM= 0.00 TEST= 0
INDE   0   61   27 FOBS=  110.5 SIGMA=   3.0 PHAS=   90.0 FOM= 1.00 TEST= 0
INDE   0   61   29 FOBS=    0.0 SIGMA=  23.6 PHAS=    0.0 FOM= 0.00 TEST= 0
INDE   0   61   31 FOBS=    0.0 SIGMA=  23.4 PHAS=    0.0 FOM= 0.00 TEST= 0
INDE   0   61   33 FOBS=   56.9 SIGMA=   6.1 PHAS=   90.0 FOM= 0.83 TEST= 0
INDE   0   61   35 FOBS=   47.2 SIGMA=   7.4 PHAS=   90.0 FOM= 0.84 TEST= 0
INDE   0   61   37 FOBS=    0.0 SIGMA=  26.1 PHAS=    0.0 FOM= 0.00 TEST= 0
INDE   0   61   39 FOBS=   97.6 SIGMA=   3.6 PHAS=  -90.0 FOM= 1.00 TEST= 0
```

*FIG. 12A - 22*

```
INDE  0  61  41  FOBS=    0.0  SIGMA=  25.9  PHAS=    0.0  FOM=  0.00  TEST= 0
INDE  0  61  43  FOBS=   16.8  SIGMA=  17.5  PHAS=  -90.0  FOM=  0.32  TEST= 0
INDE  0  61  45  FOBS=  101.1  SIGMA=   5.0  PHAS=   90.0  FOM=  0.97  TEST= 0
INDE  0  61  47  FOBS=    0.0  SIGMA=  31.0  PHAS=    0.0  FOM=  0.00  TEST= 0
INDE  0  62   2  FOBS=  101.1  SIGMA=   2.9  PHAS= -180.0  FOM=  0.82  TEST= 1
INDE  0  62   4  FOBS=  101.4  SIGMA=   2.8  PHAS= -180.0  FOM=  0.99  TEST= 0
INDE  0  62   6  FOBS=   33.1  SIGMA=   8.9  PHAS=    0.0  FOM=  0.04  TEST= 0
INDE  0  62  18  FOBS=   17.9  SIGMA=  17.6  PHAS= -180.0  FOM=  0.06  TEST= 0
INDE  0  62  20  FOBS=    0.0  SIGMA=  26.0  PHAS=    0.0  FOM=  0.00  TEST= 0
INDE  0  62  22  FOBS=   32.8  SIGMA=  11.8  PHAS=    0.0  FOM=  0.96  TEST= 0
INDE  0  62  24  FOBS=    0.0  SIGMA=  27.7  PHAS=    0.0  FOM=  0.00  TEST= 0
INDE  0  62  26  FOBS=    0.0  SIGMA=  25.1  PHAS=    0.0  FOM=  0.00  TEST= 0
INDE  0  62  28  FOBS=   77.6  SIGMA=   3.6  PHAS= -180.0  FOM=  0.24  TEST= 0
INDE  0  62  30  FOBS=   25.4  SIGMA=  11.0  PHAS= -180.0  FOM=  0.38  TEST= 0
INDE  0  62  32  FOBS=   54.5  SIGMA=   5.2  PHAS= -180.0  FOM=  0.94  TEST= 0
INDE  0  62  34  FOBS=   29.0  SIGMA=  11.9  PHAS=    0.0  FOM=  0.18  TEST= 0
INDE  0  62  36  FOBS=   89.6  SIGMA=   4.0  PHAS= -180.0  FOM=  1.00  TEST= 0
INDE  0  62  38  FOBS=   75.0  SIGMA=   4.7  PHAS= -180.0  FOM=  0.98  TEST= 0
INDE  0  62  40  FOBS=    0.0  SIGMA=  26.1  PHAS=    0.0  FOM=  0.00  TEST= 0
INDE  0  62  42  FOBS=   15.0  SIGMA=  22.9  PHAS= -180.0  FOM=  0.19  TEST= 0
INDE  0  62  44  FOBS=    0.0  SIGMA=  31.2  PHAS=    0.0  FOM=  0.00  TEST= 0
INDE  0  62  46  FOBS=    0.0  SIGMA=  31.2  PHAS=    0.0  FOM=  0.00  TEST= 0
INDE  0  63   3  FOBS=   80.4  SIGMA=   3.5  PHAS=   90.0  FOM=  0.25  TEST= 0
INDE  0  63   5  FOBS=   77.8  SIGMA=   3.9  PHAS=   90.0  FOM=  0.77  TEST= 0
INDE  0  63  19  FOBS=   93.2  SIGMA=   3.6  PHAS=  -90.0  FOM=  0.93  TEST= 0
INDE  0  63  21  FOBS=  134.5  SIGMA=   2.8  PHAS=  -90.0  FOM=  0.99  TEST= 0
INDE  0  63  23  FOBS=  100.9  SIGMA=   4.1  PHAS=  -90.0  FOM=  0.97  TEST= 0
INDE  0  63  25  FOBS=    0.0  SIGMA=  24.7  PHAS=    0.0  FOM=  0.00  TEST= 0
INDE  0  63  27  FOBS=   44.3  SIGMA=   6.2  PHAS=  -90.0  FOM=  0.68  TEST= 0
INDE  0  63  29  FOBS=    0.0  SIGMA=  26.1  PHAS=    0.0  FOM=  0.00  TEST= 0
INDE  0  63  31  FOBS=   66.7  SIGMA=   4.3  PHAS=   90.0  FOM=  0.98  TEST= 0
INDE  0  63  33  FOBS=   71.6  SIGMA=   4.0  PHAS=   90.0  FOM=  1.00  TEST= 0
INDE  0  63  35  FOBS=   45.7  SIGMA=   7.6  PHAS=  -90.0  FOM=  0.47  TEST= 0
INDE  0  63  37  FOBS=  117.7  SIGMA=   3.1  PHAS=   90.0  FOM=  1.00  TEST= 0
INDE  0  63  39  FOBS=    0.0  SIGMA=  26.4  PHAS=    0.0  FOM=  0.00  TEST= 0
INDE  0  63  41  FOBS=   60.3  SIGMA=   5.9  PHAS=   90.0  FOM=  0.37  TEST= 0
INDE  0  63  43  FOBS=    0.0  SIGMA=  26.8  PHAS=    0.0  FOM=  0.00  TEST= 0
INDE  0  63  45  FOBS=    0.0  SIGMA=  31.2  PHAS=    0.0  FOM=  0.00  TEST= 0
INDE  0  64   4  FOBS=   66.5  SIGMA=   4.1  PHAS= -180.0  FOM=  0.45  TEST= 0
INDE  0  64   6  FOBS=   31.1  SIGMA=  10.0  PHAS=    0.0  FOM=  0.39  TEST= 0
INDE  0  64  20  FOBS=   88.4  SIGMA=   3.9  PHAS= -180.0  FOM=  0.93  TEST= 0
INDE  0  64  22  FOBS=  119.6  SIGMA=   3.2  PHAS= -180.0  FOM=  0.94  TEST= 1
INDE  0  64  24  FOBS=   20.9  SIGMA=  18.7  PHAS= -180.0  FOM=  0.54  TEST= 0
INDE  0  64  26  FOBS=   40.2  SIGMA=   6.6  PHAS= -180.0  FOM=  0.18  TEST= 0
INDE  0  64  28  FOBS=   30.0  SIGMA=  11.6  PHAS= -180.0  FOM=  0.55  TEST= 0
INDE  0  64  30  FOBS=  110.8  SIGMA=   2.6  PHAS= -180.0  FOM=  0.99  TEST= 0
INDE  0  64  32  FOBS=    7.4  SIGMA=  38.6  PHAS= -180.0  FOM=  0.10  TEST= 0
INDE  0  64  34  FOBS=    0.0  SIGMA=  23.8  PHAS=    0.0  FOM=  0.00  TEST= 0
INDE  0  64  36  FOBS=   34.5  SIGMA=  10.1  PHAS= -180.0  FOM=  0.35  TEST= 0
INDE  0  64  38  FOBS=   33.2  SIGMA=  10.6  PHAS=    0.0  FOM=  0.48  TEST= 0
INDE  0  64  40  FOBS=   59.4  SIGMA=   6.0  PHAS= -180.0  FOM=  0.46  TEST= 0
INDE  0  64  42  FOBS=   57.2  SIGMA=   6.3  PHAS=    0.0  FOM=  0.91  TEST= 0
INDE  0  64  44  FOBS=    0.0  SIGMA=  31.5  PHAS=    0.0  FOM=  0.00  TEST= 0
INDE  0  65   5  FOBS=   17.2  SIGMA=  15.3  PHAS=   90.0  FOM=  0.60  TEST= 0
INDE  0  65   7  FOBS=    0.0  SIGMA=  24.2  PHAS=    0.0  FOM=  0.00  TEST= 0
INDE  0  65  21  FOBS=   64.9  SIGMA=   5.4  PHAS=   90.0  FOM=  0.78  TEST= 0
INDE  0  65  23  FOBS=   31.2  SIGMA=  12.8  PHAS=    0.0  FOM=  0.00  TEST= 1
INDE  0  65  25  FOBS=   25.7  SIGMA=  11.8  PHAS=   90.0  FOM=  0.21  TEST= 0
INDE  0  65  27  FOBS=   59.2  SIGMA=   4.5  PHAS=   90.0  FOM=  0.58  TEST= 0
INDE  0  65  29  FOBS=   79.6  SIGMA=   3.6  PHAS=   90.0  FOM=  0.97  TEST= 0
INDE  0  65  31  FOBS=   73.5  SIGMA=   3.9  PHAS=   90.0  FOM=  1.00  TEST= 0
INDE  0  65  33  FOBS=   60.4  SIGMA=   4.9  PHAS=   90.0  FOM=  0.65  TEST= 0
INDE  0  65  35  FOBS=   59.1  SIGMA=   4.9  PHAS=   90.0  FOM=  0.82  TEST= 0
INDE  0  65  37  FOBS=   54.5  SIGMA=   6.6  PHAS=   90.0  FOM=  0.74  TEST= 0
INDE  0  65  39  FOBS=   10.2  SIGMA=  34.9  PHAS=   90.0  FOM=  0.05  TEST= 0
INDE  0  65  41  FOBS=    7.4  SIGMA=  48.9  PHAS=  -90.0  FOM=  0.06  TEST= 0
INDE  0  66   4  FOBS=   19.7  SIGMA=  13.7  PHAS=    0.0  FOM=  0.35  TEST= 0
INDE  0  66   6  FOBS=    0.0  SIGMA=  24.3  PHAS=    0.0  FOM=  0.00  TEST= 0
INDE  0  66  20  FOBS=    0.0  SIGMA=  25.2  PHAS=    0.0  FOM=  0.00  TEST= 0
INDE  0  66  22  FOBS=    0.0  SIGMA=  26.3  PHAS=    0.0  FOM=  0.00  TEST= 1
```

*FIG. 12A - 23*

| | | | | | | | | | | | |
|---|---|---|---|---|---|---|---|---|---|---|---|
| INDE | 0 | 66 | 24 | FOBS= | 0.0 | SIGMA= | 25.1 | PHAS= | 0.0 | FOM= | 0.00 | TEST= 1
| INDE | 0 | 66 | 26 | FOBS= | 35.1 | SIGMA= | 7.5 | PHAS= | 0.0 | FOM= | 0.00 | TEST= 1
| INDE | 0 | 66 | 28 | FOBS= | 41.2 | SIGMA= | 8.5 | PHAS= | -180.0 | FOM= | 0.00 | TEST= 1
| INDE | 0 | 66 | 30 | FOBS= | 0.0 | SIGMA= | 23.8 | PHAS= | 0.0 | FOM= | 0.00 | TEST= 0
| INDE | 0 | 66 | 32 | FOBS= | 0.0 | SIGMA= | 26.7 | PHAS= | 0.0 | FOM= | 0.00 | TEST= 0
| INDE | 0 | 66 | 34 | FOBS= | 103.1 | SIGMA= | 3.0 | PHAS= | 0.0 | FOM= | 1.00 | TEST= 0
| INDE | 0 | 66 | 36 | FOBS= | 98.5 | SIGMA= | 3.1 | PHAS= | 0.0 | FOM= | 1.00 | TEST= 0
| INDE | 0 | 66 | 38 | FOBS= | 0.0 | SIGMA= | 26.7 | PHAS= | 0.0 | FOM= | 0.00 | TEST= 0
| INDE | 0 | 66 | 40 | FOBS= | 0.0 | SIGMA= | 27.0 | PHAS= | 0.0 | FOM= | 0.00 | TEST= 0
| INDE | 0 | 67 | 5 | FOBS= | 48.0 | SIGMA= | 5.5 | PHAS= | 90.0 | FOM= | 0.76 | TEST= 0
| INDE | 0 | 67 | 7 | FOBS= | 45.5 | SIGMA= | 6.5 | PHAS= | 90.0 | FOM= | 0.70 | TEST= 0
| INDE | 0 | 67 | 21 | FOBS= | 38.2 | SIGMA= | 8.7 | PHAS= | -90.0 | FOM= | 0.48 | TEST= 0
| INDE | 0 | 67 | 23 | FOBS= | 110.7 | SIGMA= | 2.8 | PHAS= | -90.0 | FOM= | 0.99 | TEST= 0
| INDE | 0 | 67 | 25 | FOBS= | 74.5 | SIGMA= | 3.7 | PHAS= | -90.0 | FOM= | 0.98 | TEST= 0
| INDE | 0 | 67 | 27 | FOBS= | 76.0 | SIGMA= | 3.6 | PHAS= | 90.0 | FOM= | 0.98 | TEST= 0
| INDE | 0 | 67 | 29 | FOBS= | 53.9 | SIGMA= | 5.2 | PHAS= | 90.0 | FOM= | 0.62 | TEST= 0
| INDE | 0 | 67 | 31 | FOBS= | 0.0 | SIGMA= | 23.9 | PHAS= | 0.0 | FOM= | 0.00 | TEST= 0
| INDE | 0 | 67 | 33 | FOBS= | 31.4 | SIGMA= | 11.5 | PHAS= | 90.0 | FOM= | 0.01 | TEST= 1
| INDE | 0 | 67 | 35 | FOBS= | 88.1 | SIGMA= | 3.5 | PHAS= | -90.0 | FOM= | 1.00 | TEST= 0
| INDE | 0 | 67 | 37 | FOBS= | 0.0 | SIGMA= | 27.0 | PHAS= | 0.0 | FOM= | 0.00 | TEST= 0
| INDE | 0 | 67 | 39 | FOBS= | 0.0 | SIGMA= | 27.2 | PHAS= | 0.0 | FOM= | 0.00 | TEST= 0
| INDE | 0 | 68 | 4 | FOBS= | 78.7 | SIGMA= | 3.6 | PHAS= | -180.0 | FOM= | 0.28 | TEST= 1
| INDE | 0 | 68 | 6 | FOBS= | 27.5 | SIGMA= | 9.5 | PHAS= | 0.0 | FOM= | 0.42 | TEST= 0
| INDE | 0 | 68 | 8 | FOBS= | 18.6 | SIGMA= | 16.0 | PHAS= | 0.0 | FOM= | 0.37 | TEST= 0
| INDE | 0 | 68 | 22 | FOBS= | 77.8 | SIGMA= | 3.8 | PHAS= | -180.0 | FOM= | 0.41 | TEST= 0
| INDE | 0 | 68 | 24 | FOBS= | 0.0 | SIGMA= | 24.6 | PHAS= | 0.0 | FOM= | 0.00 | TEST= 0
| INDE | 0 | 68 | 26 | FOBS= | 113.3 | SIGMA= | 2.6 | PHAS= | 0.0 | FOM= | 1.00 | TEST= 0
| INDE | 0 | 68 | 28 | FOBS= | 86.2 | SIGMA= | 3.3 | PHAS= | 0.0 | FOM= | 0.52 | TEST= 0
| INDE | 0 | 68 | 30 | FOBS= | 70.1 | SIGMA= | 4.1 | PHAS= | -180.0 | FOM= | 0.32 | TEST= 0
| INDE | 0 | 68 | 32 | FOBS= | 28.9 | SIGMA= | 10.1 | PHAS= | 0.0 | FOM= | 0.26 | TEST= 0
| INDE | 0 | 68 | 34 | FOBS= | 76.0 | SIGMA= | 4.0 | PHAS= | 0.0 | FOM= | 0.96 | TEST= 0
| INDE | 0 | 68 | 36 | FOBS= | 0.0 | SIGMA= | 27.5 | PHAS= | 0.0 | FOM= | 0.00 | TEST= 0
| INDE | 0 | 69 | 5 | FOBS= | 33.5 | SIGMA= | 8.1 | PHAS= | 90.0 | FOM= | 0.65 | TEST= 0
| INDE | 0 | 69 | 7 | FOBS= | 118.0 | SIGMA= | 2.6 | PHAS= | 90.0 | FOM= | 1.00 | TEST= 0
| INDE | 0 | 69 | 21 | FOBS= | 129.4 | SIGMA= | 4.1 | PHAS= | -90.0 | FOM= | 0.83 | TEST= 0
| INDE | 0 | 69 | 23 | FOBS= | 114.6 | SIGMA= | 2.4 | PHAS= | -90.0 | FOM= | 1.00 | TEST= 0
| INDE | 0 | 69 | 25 | FOBS= | 114.9 | SIGMA= | 2.4 | PHAS= | -90.0 | FOM= | 0.99 | TEST= 0
| INDE | 0 | 69 | 27 | FOBS= | 0.0 | SIGMA= | 23.6 | PHAS= | 0.0 | FOM= | 0.00 | TEST= 0
| INDE | 0 | 69 | 29 | FOBS= | 164.6 | SIGMA= | 1.9 | PHAS= | -90.0 | FOM= | 0.05 | TEST= 1
| INDE | 0 | 69 | 31 | FOBS= | 0.0 | SIGMA= | 24.1 | PHAS= | 0.0 | FOM= | 0.00 | TEST= 0
| INDE | 0 | 69 | 33 | FOBS= | 46.7 | SIGMA= | 6.4 | PHAS= | -90.0 | FOM= | 0.90 | TEST= 0
| INDE | 0 | 69 | 35 | FOBS= | 128.1 | SIGMA= | 2.6 | PHAS= | -90.0 | FOM= | 0.97 | TEST= 0
| INDE | 0 | 70 | 6 | FOBS= | 0.0 | SIGMA= | 22.9 | PHAS= | 0.0 | FOM= | 0.00 | TEST= 0
| INDE | 0 | 70 | 8 | FOBS= | 86.7 | SIGMA= | 3.6 | PHAS= | 0.0 | FOM= | 1.00 | TEST= 0
| INDE | 0 | 70 | 22 | FOBS= | 117.8 | SIGMA= | 4.8 | PHAS= | -180.0 | FOM= | 1.00 | TEST= 0
| INDE | 0 | 70 | 24 | FOBS= | 64.0 | SIGMA= | 4.1 | PHAS= | -180.0 | FOM= | 0.95 | TEST= 0
| INDE | 0 | 70 | 26 | FOBS= | 0.0 | SIGMA= | 25.3 | PHAS= | 0.0 | FOM= | 0.00 | TEST= 0
| INDE | 0 | 70 | 28 | FOBS= | 111.2 | SIGMA= | 2.7 | PHAS= | -180.0 | FOM= | 1.00 | TEST= 0
| INDE | 0 | 70 | 30 | FOBS= | 0.0 | SIGMA= | 23.9 | PHAS= | 0.0 | FOM= | 0.00 | TEST= 0
| INDE | 0 | 70 | 32 | FOBS= | 18.6 | SIGMA= | 19.7 | PHAS= | -180.0 | FOM= | 0.28 | TEST= 0
| INDE | 0 | 71 | 5 | FOBS= | 0.0 | SIGMA= | 23.4 | PHAS= | 0.0 | FOM= | 0.00 | TEST= 0
| INDE | 0 | 71 | 7 | FOBS= | 96.9 | SIGMA= | 2.8 | PHAS= | 90.0 | FOM= | 1.00 | TEST= 0
| INDE | 0 | 71 | 9 | FOBS= | 0.0 | SIGMA= | 24.4 | PHAS= | 0.0 | FOM= | 0.00 | TEST= 0
| INDE | 0 | 71 | 23 | FOBS= | 32.1 | SIGMA= | 9.1 | PHAS= | 90.0 | FOM= | 0.93 | TEST= 0
| INDE | 0 | 71 | 25 | FOBS= | 0.0 | SIGMA= | 27.4 | PHAS= | 0.0 | FOM= | 0.00 | TEST= 0
| INDE | 0 | 71 | 27 | FOBS= | 21.3 | SIGMA= | 16.0 | PHAS= | 90.0 | FOM= | 0.13 | TEST= 0
| INDE | 0 | 71 | 29 | FOBS= | 44.1 | SIGMA= | 6.6 | PHAS= | -90.0 | FOM= | 0.88 | TEST= 0
| INDE | 0 | 71 | 31 | FOBS= | 0.0 | SIGMA= | 24.4 | PHAS= | 0.0 | FOM= | 0.00 | TEST= 1
| INDE | 0 | 72 | 6 | FOBS= | 0.0 | SIGMA= | 23.3 | PHAS= | 0.0 | FOM= | 0.00 | TEST= 0
| INDE | 0 | 72 | 8 | FOBS= | 26.6 | SIGMA= | 11.2 | PHAS= | 0.0 | FOM= | 0.63 | TEST= 0
| INDE | 0 | 72 | 24 | FOBS= | 40.9 | SIGMA= | 8.9 | PHAS= | 0.0 | FOM= | 0.39 | TEST= 0
| INDE | 0 | 72 | 26 | FOBS= | 31.3 | SIGMA= | 12.5 | PHAS= | 0.0 | FOM= | 0.17 | TEST= 0
| INDE | 0 | 72 | 28 | FOBS= | 95.9 | SIGMA= | 3.8 | PHAS= | -180.0 | FOM= | 0.95 | TEST= 0
| INDE | 0 | 73 | 7 | FOBS= | 0.0 | SIGMA= | 23.0 | PHAS= | 0.0 | FOM= | 0.00 | TEST= 0
| INDE | 0 | 73 | 9 | FOBS= | 47.0 | SIGMA= | 6.8 | PHAS= | -90.0 | FOM= | 0.77 | TEST= 0
| INDE | 0 | 73 | 25 | FOBS= | 13.7 | SIGMA= | 27.9 | PHAS= | 90.0 | FOM= | 0.14 | TEST= 0
| INDE | 0 | 74 | 6 | FOBS= | 63.5 | SIGMA= | 4.4 | PHAS= | 0.0 | FOM= | 0.58 | TEST= 0
| INDE | 0 | 74 | 8 | FOBS= | 0.0 | SIGMA= | 23.3 | PHAS= | 0.0 | FOM= | 0.00 | TEST= 0
| INDE | 0 | 74 | 10 | FOBS= | 20.7 | SIGMA= | 14.7 | PHAS= | -180.0 | FOM= | 0.02 | TEST= 0
| INDE | 0 | 75 | 9 | FOBS= | 36.4 | SIGMA= | 8.4 | PHAS= | -90.0 | FOM= | 0.37 | TEST= 0

*FIG. 12A - 24*

| | | | | | | | | | | | |
|---|---|---|---|---|---|---|---|---|---|---|---|
| INDE | 0 | 76 | 8 | FOBS= | 43.7 | SIGMA= | 6.2 | PHAS= | 0.0 | FOM= | 0.74 | TEST= 0 |
| INDE | 0 | 76 | 10 | FOBS= | 0.0 | SIGMA= | 25.8 | PHAS= | 0.0 | FOM= | 0.00 | TEST= 0 |
| INDE | 0 | 77 | 7 | FOBS= | 49.3 | SIGMA= | 5.7 | PHAS= | 90.0 | FOM= | 0.72 | TEST= 0 |
| INDE | 0 | 77 | 9 | FOBS= | 0.0 | SIGMA= | 23.5 | PHAS= | 0.0 | FOM= | 0.00 | TEST= 0 |
| INDE | 1 | 2 | 21 | FOBS= | 85.8 | SIGMA= | 1.0 | PHAS= | -97.6 | FOM= | 0.34 | TEST= 0 |
| INDE | 1 | 2 | 23 | FOBS= | 293.8 | SIGMA= | 0.5 | PHAS= | -96.0 | FOM= | 0.92 | TEST= 0 |
| INDE | 1 | 2 | 25 | FOBS= | 196.3 | SIGMA= | 0.6 | PHAS= | 6.8 | FOM= | 0.95 | TEST= 0 |
| INDE | 1 | 2 | 27 | FOBS= | 354.0 | SIGMA= | 0.5 | PHAS= | 44.8 | FOM= | 0.99 | TEST= 0 |
| INDE | 1 | 2 | 29 | FOBS= | 187.6 | SIGMA= | 0.5 | PHAS= | 178.1 | FOM= | 0.99 | TEST= 0 |
| INDE | 1 | 2 | 31 | FOBS= | 123.9 | SIGMA= | 0.7 | PHAS= | -107.7 | FOM= | 0.98 | TEST= 0 |
| INDE | 1 | 2 | 33 | FOBS= | 125.2 | SIGMA= | 0.7 | PHAS= | -55.4 | FOM= | 0.94 | TEST= 0 |
| INDE | 1 | 2 | 35 | FOBS= | 80.4 | SIGMA= | 1.2 | PHAS= | 24.7 | FOM= | 0.98 | TEST= 0 |
| INDE | 1 | 2 | 37 | FOBS= | 120.1 | SIGMA= | 0.9 | PHAS= | 79.7 | FOM= | 0.99 | TEST= 0 |
| INDE | 1 | 2 | 39 | FOBS= | 93.9 | SIGMA= | 1.6 | PHAS= | -21.0 | FOM= | 0.94 | TEST= 0 |
| INDE | 1 | 2 | 41 | FOBS= | 373.5 | SIGMA= | 0.5 | PHAS= | 45.7 | FOM= | 0.97 | TEST= 0 |
| INDE | 1 | 2 | 43 | FOBS= | 112.6 | SIGMA= | 1.0 | PHAS= | 38.0 | FOM= | 0.98 | TEST= 0 |
| INDE | 1 | 2 | 45 | FOBS= | 196.1 | SIGMA= | 0.7 | PHAS= | 46.1 | FOM= | 0.95 | TEST= 0 |
| INDE | 1 | 2 | 47 | FOBS= | 149.8 | SIGMA= | 0.8 | PHAS= | 100.8 | FOM= | 0.85 | TEST= 0 |
| INDE | 1 | 2 | 49 | FOBS= | 184.4 | SIGMA= | 0.9 | PHAS= | 13.8 | FOM= | 0.97 | TEST= 0 |
| INDE | 1 | 2 | 51 | FOBS= | 251.0 | SIGMA= | 1.1 | PHAS= | 27.2 | FOM= | 0.81 | TEST= 1 |
| INDE | 1 | 2 | 53 | FOBS= | 174.0 | SIGMA= | 1.0 | PHAS= | -8.2 | FOM= | 0.93 | TEST= 0 |
| INDE | 1 | 2 | 55 | FOBS= | 78.5 | SIGMA= | 2.0 | PHAS= | -150.9 | FOM= | 0.62 | TEST= 0 |
| INDE | 1 | 2 | 57 | FOBS= | 174.1 | SIGMA= | 1.0 | PHAS= | 106.7 | FOM= | 0.90 | TEST= 0 |
| INDE | 1 | 2 | 59 | FOBS= | 158.1 | SIGMA= | 1.4 | PHAS= | 22.6 | FOM= | 0.94 | TEST= 0 |
| INDE | 1 | 2 | 61 | FOBS= | 23.4 | SIGMA= | 9.3 | PHAS= | -89.7 | FOM= | 0.65 | TEST= 0 |
| INDE | 1 | 2 | 63 | FOBS= | 131.7 | SIGMA= | 2.5 | PHAS= | -102.2 | FOM= | 0.94 | TEST= 0 |
| INDE | 1 | 2 | 65 | FOBS= | 159.2 | SIGMA= | 2.0 | PHAS= | -63.2 | FOM= | 0.95 | TEST= 0 |
| INDE | 1 | 3 | 26 | FOBS= | 19.8 | SIGMA= | 4.9 | PHAS= | -50.2 | FOM= | 0.32 | TEST= 0 |
| INDE | 1 | 3 | 28 | FOBS= | 217.9 | SIGMA= | 0.7 | PHAS= | 60.3 | FOM= | 0.98 | TEST= 0 |
| INDE | 1 | 3 | 30 | FOBS= | 77.9 | SIGMA= | 1.5 | PHAS= | 51.8 | FOM= | 0.92 | TEST= 0 |
| INDE | 1 | 3 | 32 | FOBS= | 201.2 | SIGMA= | 0.8 | PHAS= | 151.2 | FOM= | 0.98 | TEST= 0 |
| INDE | 1 | 3 | 34 | FOBS= | 57.6 | SIGMA= | 1.5 | PHAS= | 147.0 | FOM= | 0.81 | TEST= 0 |
| INDE | 1 | 3 | 36 | FOBS= | 284.0 | SIGMA= | 0.7 | PHAS= | 176.9 | FOM= | 0.97 | TEST= 0 |
| INDE | 1 | 3 | 38 | FOBS= | 294.5 | SIGMA= | 0.7 | PHAS= | 136.3 | FOM= | 0.97 | TEST= 0 |
| INDE | 1 | 3 | 40 | FOBS= | 161.7 | SIGMA= | 0.7 | PHAS= | 48.4 | FOM= | 0.94 | TEST= 0 |
| INDE | 1 | 3 | 42 | FOBS= | 33.9 | SIGMA= | 3.3 | PHAS= | -100.3 | FOM= | 0.66 | TEST= 0 |
| INDE | 1 | 3 | 44 | FOBS= | 188.9 | SIGMA= | 0.7 | PHAS= | -59.5 | FOM= | 0.95 | TEST= 0 |
| INDE | 1 | 3 | 46 | FOBS= | 63.3 | SIGMA= | 2.5 | PHAS= | 26.8 | FOM= | 0.41 | TEST= 0 |
| INDE | 1 | 3 | 48 | FOBS= | 66.7 | SIGMA= | 2.5 | PHAS= | -51.1 | FOM= | 0.86 | TEST= 0 |
| INDE | 1 | 3 | 50 | FOBS= | 152.9 | SIGMA= | 1.2 | PHAS= | -58.8 | FOM= | 0.87 | TEST= 0 |
| INDE | 1 | 3 | 52 | FOBS= | 176.3 | SIGMA= | 1.0 | PHAS= | -96.9 | FOM= | 0.93 | TEST= 0 |
| INDE | 1 | 3 | 54 | FOBS= | 109.4 | SIGMA= | 1.5 | PHAS= | 72.4 | FOM= | 0.65 | TEST= 0 |
| INDE | 1 | 3 | 56 | FOBS= | 150.7 | SIGMA= | 1.1 | PHAS= | 87.8 | FOM= | 0.62 | TEST= 0 |
| INDE | 1 | 3 | 58 | FOBS= | 93.7 | SIGMA= | 1.8 | PHAS= | -108.6 | FOM= | 0.90 | TEST= 0 |
| INDE | 1 | 3 | 60 | FOBS= | 91.8 | SIGMA= | 1.8 | PHAS= | -2.4 | FOM= | 0.73 | TEST= 0 |
| INDE | 1 | 3 | 62 | FOBS= | 102.9 | SIGMA= | 2.3 | PHAS= | -87.3 | FOM= | 0.91 | TEST= 0 |
| INDE | 1 | 3 | 64 | FOBS= | 68.1 | SIGMA= | 4.8 | PHAS= | -169.3 | FOM= | 0.90 | TEST= 0 |
| INDE | 1 | 3 | 66 | FOBS= | 107.6 | SIGMA= | 3.2 | PHAS= | -157.5 | FOM= | 0.91 | TEST= 0 |
| INDE | 1 | 3 | 68 | FOBS= | 86.8 | SIGMA= | 3.8 | PHAS= | -82.2 | FOM= | 0.85 | TEST= 0 |
| INDE | 1 | 4 | 19 | FOBS= | 188.1 | SIGMA= | 0.7 | PHAS= | 105.0 | FOM= | 0.93 | TEST= 0 |
| INDE | 1 | 4 | 21 | FOBS= | 244.7 | SIGMA= | 0.7 | PHAS= | 109.9 | FOM= | 0.95 | TEST= 0 |
| INDE | 1 | 4 | 23 | FOBS= | 150.4 | SIGMA= | 1.7 | PHAS= | -72.4 | FOM= | 0.68 | TEST= 0 |
| INDE | 1 | 4 | 29 | FOBS= | 42.5 | SIGMA= | 2.7 | PHAS= | 170.3 | FOM= | 0.04 | TEST= 0 |
| INDE | 1 | 4 | 31 | FOBS= | 121.5 | SIGMA= | 1.1 | PHAS= | -29.7 | FOM= | 0.99 | TEST= 0 |
| INDE | 1 | 4 | 33 | FOBS= | 208.3 | SIGMA= | 0.8 | PHAS= | -21.6 | FOM= | 0.99 | TEST= 0 |
| INDE | 1 | 4 | 35 | FOBS= | 353.5 | SIGMA= | 0.7 | PHAS= | 72.2 | FOM= | 0.99 | TEST= 0 |
| INDE | 1 | 4 | 37 | FOBS= | 311.5 | SIGMA= | 0.7 | PHAS= | 68.6 | FOM= | 0.98 | TEST= 0 |
| INDE | 1 | 4 | 39 | FOBS= | 219.4 | SIGMA= | 0.9 | PHAS= | 142.8 | FOM= | 0.92 | TEST= 0 |
| INDE | 1 | 4 | 41 | FOBS= | 93.1 | SIGMA= | 2.0 | PHAS= | -1.7 | FOM= | 0.53 | TEST= 0 |
| INDE | 1 | 4 | 43 | FOBS= | 166.5 | SIGMA= | 1.3 | PHAS= | -119.4 | FOM= | 0.97 | TEST= 0 |
| INDE | 1 | 4 | 45 | FOBS= | 124.3 | SIGMA= | 1.3 | PHAS= | -156.2 | FOM= | 0.51 | TEST= 0 |
| INDE | 1 | 4 | 47 | FOBS= | 126.4 | SIGMA= | 1.4 | PHAS= | -1.2 | FOM= | 0.47 | TEST= 1 |
| INDE | 1 | 4 | 49 | FOBS= | 93.3 | SIGMA= | 1.9 | PHAS= | -44.0 | FOM= | 0.94 | TEST= 0 |
| INDE | 1 | 4 | 51 | FOBS= | 125.1 | SIGMA= | 1.4 | PHAS= | 151.6 | FOM= | 0.89 | TEST= 0 |
| INDE | 1 | 4 | 53 | FOBS= | 48.5 | SIGMA= | 3.5 | PHAS= | 133.6 | FOM= | 0.91 | TEST= 0 |
| INDE | 1 | 4 | 55 | FOBS= | 44.2 | SIGMA= | 3.8 | PHAS= | 33.6 | FOM= | 0.48 | TEST= 0 |
| INDE | 1 | 4 | 57 | FOBS= | 141.4 | SIGMA= | 1.2 | PHAS= | 132.9 | FOM= | 0.89 | TEST= 0 |
| INDE | 1 | 4 | 59 | FOBS= | 66.0 | SIGMA= | 2.6 | PHAS= | -96.4 | FOM= | 0.69 | TEST= 0 |
| INDE | 1 | 4 | 61 | FOBS= | 84.6 | SIGMA= | 1.9 | PHAS= | -130.3 | FOM= | 0.88 | TEST= 0 |
| INDE | 1 | 4 | 63 | FOBS= | 0.0 | SIGMA= | 19.2 | PHAS= | 0.0 | FOM= | 0.00 | TEST= 0 |

*FIG. 12A - 25*

```
INDE  1  4  65  FOBS=    40.0  SIGMA=   4.6  PHAS=   154.7  FOM=  0.06  TEST= 0
INDE  1  4  67  FOBS=    66.0  SIGMA=   5.2  PHAS=  -119.4  FOM=  0.87  TEST= 0
INDE  1  4  69  FOBS=    59.5  SIGMA=   5.8  PHAS=  -147.0  FOM=  0.77  TEST= 0
INDE  1  4  71  FOBS=    62.0  SIGMA=   5.4  PHAS=  -157.9  FOM=  0.12  TEST= 1
INDE  1  5  18  FOBS=   274.6  SIGMA=   0.6  PHAS=    22.5  FOM=  0.82  TEST= 0
INDE  1  5  20  FOBS=   379.9  SIGMA=   0.6  PHAS=   -23.0  FOM=  0.97  TEST= 0
INDE  1  5  22  FOBS=    87.2  SIGMA=   1.2  PHAS=   137.4  FOM=  0.80  TEST= 0
INDE  1  5  24  FOBS=    91.7  SIGMA=   1.2  PHAS=   -18.2  FOM=  0.94  TEST= 0
INDE  1  5  26  FOBS=    90.6  SIGMA=   1.3  PHAS=   -54.4  FOM=  0.99  TEST= 0
INDE  1  5  28  FOBS=   117.6  SIGMA=   1.1  PHAS=    18.1  FOM=  0.98  TEST= 0
INDE  1  5  30  FOBS=    89.9  SIGMA=   1.2  PHAS=   155.5  FOM=  0.98  TEST= 0
INDE  1  5  32  FOBS=   256.1  SIGMA=   0.9  PHAS=   -34.6  FOM=  0.96  TEST= 0
INDE  1  5  34  FOBS=   151.2  SIGMA=   0.8  PHAS=  -176.0  FOM=  0.78  TEST= 0
INDE  1  5  36  FOBS=   120.4  SIGMA=   1.2  PHAS=  -113.4  FOM=  0.98  TEST= 0
INDE  1  5  38  FOBS=   191.1  SIGMA=   1.0  PHAS=    70.1  FOM=  0.89  TEST= 0
INDE  1  5  40  FOBS=   128.2  SIGMA=   1.4  PHAS=    62.1  FOM=  0.92  TEST= 0
INDE  1  5  42  FOBS=    47.3  SIGMA=   3.8  PHAS=   -95.7  FOM=  0.30  TEST= 0
INDE  1  5  44  FOBS=   118.1  SIGMA=   1.7  PHAS=   -77.3  FOM=  0.47  TEST= 0
INDE  1  5  46  FOBS=    75.0  SIGMA=   2.2  PHAS=   -57.4  FOM=  0.85  TEST= 0
INDE  1  5  48  FOBS=   194.1  SIGMA=   1.0  PHAS=  -170.3  FOM=  0.94  TEST= 0
INDE  1  5  50  FOBS=    32.0  SIGMA=   5.4  PHAS=   -58.0  FOM=  0.73  TEST= 0
INDE  1  5  52  FOBS=    62.9  SIGMA=   2.8  PHAS=    10.7  FOM=  0.19  TEST= 0
INDE  1  5  54  FOBS=   156.9  SIGMA=   1.0  PHAS=    34.9  FOM=  0.93  TEST= 0
INDE  1  5  56  FOBS=     0.0  SIGMA=  19.1  PHAS=     0.0  FOM=  0.00  TEST= 0
INDE  1  5  58  FOBS=    29.1  SIGMA=   5.1  PHAS=     1.1  FOM=  0.77  TEST= 0
INDE  1  5  60  FOBS=    30.6  SIGMA=   4.8  PHAS=    91.3  FOM=  0.42  TEST= 0
INDE  1  5  62  FOBS=    66.7  SIGMA=   2.2  PHAS=   -45.7  FOM=  0.82  TEST= 0
INDE  1  5  64  FOBS=    16.4  SIGMA=  10.6  PHAS=    81.7  FOM=  0.13  TEST= 1
INDE  1  5  66  FOBS=    84.0  SIGMA=   2.9  PHAS=   168.5  FOM=  0.91  TEST= 0
INDE  1  5  68  FOBS=    57.2  SIGMA=   4.3  PHAS=  -175.0  FOM=  0.30  TEST= 0
INDE  1  5  70  FOBS=    79.1  SIGMA=   4.6  PHAS=  -122.5  FOM=  0.87  TEST= 0
INDE  1  5  72  FOBS=    94.9  SIGMA=   3.8  PHAS=  -101.9  FOM=  0.87  TEST= 0
INDE  1  6  17  FOBS=   361.4  SIGMA=   0.5  PHAS=  -128.9  FOM=  0.93  TEST= 0
INDE  1  6  19  FOBS=   267.1  SIGMA=   0.6  PHAS=   -39.7  FOM=  0.93  TEST= 0
INDE  1  6  21  FOBS=    17.5  SIGMA=   5.3  PHAS=   -99.7  FOM=  0.66  TEST= 0
INDE  1  6  23  FOBS=   331.0  SIGMA=   0.6  PHAS=   -38.2  FOM=  0.98  TEST= 0
INDE  1  6  25  FOBS=    94.2  SIGMA=   1.2  PHAS=   117.8  FOM=  0.94  TEST= 0
INDE  1  6  27  FOBS=    99.9  SIGMA=   1.3  PHAS=  -136.1  FOM=  0.99  TEST= 1
INDE  1  6  29  FOBS=   103.0  SIGMA=   1.3  PHAS=     2.0  FOM=  0.96  TEST= 0
INDE  1  6  31  FOBS=   204.9  SIGMA=   1.0  PHAS=    68.1  FOM=  0.99  TEST= 0
INDE  1  6  33  FOBS=    71.1  SIGMA=   1.4  PHAS=  -167.5  FOM=  0.57  TEST= 0
INDE  1  6  35  FOBS=   231.8  SIGMA=   0.9  PHAS=    65.9  FOM=  0.96  TEST= 0
INDE  1  6  37  FOBS=   157.8  SIGMA=   0.9  PHAS=   166.0  FOM=  0.90  TEST= 0
INDE  1  6  39  FOBS=   205.0  SIGMA=   0.9  PHAS=    13.6  FOM=  0.31  TEST= 1
INDE  1  6  41  FOBS=   162.6  SIGMA=   1.0  PHAS=   142.2  FOM=  0.95  TEST= 0
INDE  1  6  43  FOBS=   228.2  SIGMA=   1.1  PHAS=  -122.7  FOM=  0.97  TEST= 0
INDE  1  6  45  FOBS=   172.8  SIGMA=   1.1  PHAS=  -127.0  FOM=  0.86  TEST= 0
INDE  1  6  47  FOBS=   101.3  SIGMA=   1.6  PHAS=   -32.3  FOM=  0.95  TEST= 0
INDE  1  6  49  FOBS=   179.4  SIGMA=   1.0  PHAS=    81.6  FOM=  0.95  TEST= 0
INDE  1  6  51  FOBS=   150.3  SIGMA=   1.1  PHAS=   166.8  FOM=  0.93  TEST= 0
INDE  1  6  53  FOBS=    33.3  SIGMA=   5.1  PHAS=   -55.0  FOM=  0.40  TEST= 0
INDE  1  6  55  FOBS=   164.6  SIGMA=   1.0  PHAS=   -47.7  FOM=  0.90  TEST= 0
INDE  1  6  57  FOBS=   119.0  SIGMA=   1.3  PHAS=    39.3  FOM=  0.85  TEST= 0
INDE  1  6  59  FOBS=    96.2  SIGMA=   1.5  PHAS=  -141.7  FOM=  0.82  TEST= 0
INDE  1  6  61  FOBS=   127.1  SIGMA=   1.2  PHAS=  -161.1  FOM=  0.96  TEST= 0
INDE  1  6  63  FOBS=   120.0  SIGMA=   1.5  PHAS=  -102.5  FOM=  0.77  TEST= 1
INDE  1  6  65  FOBS=    19.9  SIGMA=   9.4  PHAS=  -118.4  FOM=  0.23  TEST= 0
INDE  1  6  67  FOBS=    88.7  SIGMA=   2.9  PHAS=  -163.3  FOM=  0.89  TEST= 0
INDE  1  6  69  FOBS=   142.4  SIGMA=   1.9  PHAS=   164.5  FOM=  0.96  TEST= 0
INDE  1  6  71  FOBS=    53.2  SIGMA=   6.7  PHAS=  -176.7  FOM=  0.71  TEST= 0
INDE  1  6  73  FOBS=    10.3  SIGMA=  35.8  PHAS=  -121.9  FOM=  0.22  TEST= 0
INDE  1  6  75  FOBS=    13.9  SIGMA=  26.5  PHAS=   101.1  FOM=  0.20  TEST= 0
INDE  1  7  18  FOBS=   371.3  SIGMA=   0.5  PHAS=   -74.9  FOM=  0.97  TEST= 0
INDE  1  7  20  FOBS=   355.5  SIGMA=   0.5  PHAS=   -77.2  FOM=  0.97  TEST= 0
INDE  1  7  22  FOBS=   267.8  SIGMA=   0.6  PHAS=  -149.5  FOM=  0.97  TEST= 0
INDE  1  7  24  FOBS=   122.0  SIGMA=   1.0  PHAS=     9.1  FOM=  0.95  TEST= 1
INDE  1  7  26  FOBS=    64.2  SIGMA=   1.8  PHAS=    22.7  FOM=  0.86  TEST= 0
INDE  1  7  28  FOBS=   109.5  SIGMA=   1.2  PHAS=   151.4  FOM=  0.98  TEST= 0
INDE  1  7  30  FOBS=   135.8  SIGMA=   1.1  PHAS=  -154.6  FOM=  0.98  TEST= 0
INDE  1  7  32  FOBS=   196.1  SIGMA=   0.9  PHAS=   -33.8  FOM=  0.91  TEST= 0
```

*FIG. 12A - 26*

| | | | | | | | | | | | | |
|---|---|---|---|---|---|---|---|---|---|---|---|---|
| INDE | 1 | 7 | 34 | FOBS= | 42.0 | SIGMA= | 2.9 | PHAS= | -53.2 | FOM= | 0.39 | TEST= 0 |
| INDE | 1 | 7 | 36 | FOBS= | 99.9 | SIGMA= | 1.2 | PHAS= | -163.6 | FOM= | 0.93 | TEST= 0 |
| INDE | 1 | 7 | 38 | FOBS= | 91.4 | SIGMA= | 1.4 | PHAS= | 68.1 | FOM= | 0.82 | TEST= 0 |
| INDE | 1 | 7 | 40 | FOBS= | 243.0 | SIGMA= | 0.8 | PHAS= | 78.9 | FOM= | 0.92 | TEST= 0 |
| INDE | 1 | 7 | 42 | FOBS= | 129.0 | SIGMA= | 1.2 | PHAS= | 83.5 | FOM= | 0.95 | TEST= 1 |
| INDE | 1 | 7 | 44 | FOBS= | 148.2 | SIGMA= | 1.4 | PHAS= | 172.6 | FOM= | 0.95 | TEST= 0 |
| INDE | 1 | 7 | 46 | FOBS= | 219.5 | SIGMA= | 1.1 | PHAS= | -165.8 | FOM= | 0.97 | TEST= 0 |
| INDE | 1 | 7 | 48 | FOBS= | 97.2 | SIGMA= | 1.8 | PHAS= | 20.8 | FOM= | 0.80 | TEST= 0 |
| INDE | 1 | 7 | 50 | FOBS= | 59.6 | SIGMA= | 2.7 | PHAS= | 78.8 | FOM= | 0.68 | TEST= 0 |
| INDE | 1 | 7 | 52 | FOBS= | 86.7 | SIGMA= | 1.9 | PHAS= | 179.1 | FOM= | 0.42 | TEST= 0 |
| INDE | 1 | 7 | 54 | FOBS= | 106.3 | SIGMA= | 1.5 | PHAS= | -44.3 | FOM= | 0.71 | TEST= 0 |
| INDE | 1 | 7 | 56 | FOBS= | 99.0 | SIGMA= | 1.6 | PHAS= | -111.2 | FOM= | 0.73 | TEST= 0 |
| INDE | 1 | 7 | 58 | FOBS= | 34.2 | SIGMA= | 4.3 | PHAS= | -33.6 | FOM= | 0.33 | TEST= 0 |
| INDE | 1 | 7 | 60 | FOBS= | 51.3 | SIGMA= | 2.9 | PHAS= | -179.1 | FOM= | 0.47 | TEST= 0 |
| INDE | 1 | 7 | 62 | FOBS= | 111.8 | SIGMA= | 1.4 | PHAS= | 125.8 | FOM= | 0.91 | TEST= 0 |
| INDE | 1 | 7 | 64 | FOBS= | 103.1 | SIGMA= | 1.8 | PHAS= | 177.9 | FOM= | 0.90 | TEST= 1 |
| INDE | 1 | 7 | 66 | FOBS= | 76.8 | SIGMA= | 3.4 | PHAS= | 116.4 | FOM= | 0.42 | TEST= 0 |
| INDE | 1 | 7 | 68 | FOBS= | 66.5 | SIGMA= | 3.9 | PHAS= | 82.0 | FOM= | 0.93 | TEST= 0 |
| INDE | 1 | 7 | 70 | FOBS= | 28.2 | SIGMA= | 9.2 | PHAS= | 172.3 | FOM= | 0.14 | TEST= 1 |
| INDE | 1 | 7 | 72 | FOBS= | 34.4 | SIGMA= | 7.5 | PHAS= | -104.9 | FOM= | 0.56 | TEST= 0 |
| INDE | 1 | 7 | 74 | FOBS= | 36.6 | SIGMA= | 10.3 | PHAS= | -149.6 | FOM= | 0.64 | TEST= 0 |
| INDE | 1 | 7 | 76 | FOBS= | 0.0 | SIGMA= | 27.9 | PHAS= | 0.0 | FOM= | 0.00 | TEST= 0 |
| INDE | 1 | 8 | 17 | FOBS= | 131.8 | SIGMA= | 0.5 | PHAS= | 84.7 | FOM= | 0.81 | TEST= 0 |
| INDE | 1 | 8 | 19 | FOBS= | 276.1 | SIGMA= | 0.5 | PHAS= | -172.6 | FOM= | 0.76 | TEST= 1 |
| INDE | 1 | 8 | 21 | FOBS= | 384.0 | SIGMA= | 0.6 | PHAS= | 103.7 | FOM= | 0.96 | TEST= 0 |
| INDE | 1 | 8 | 23 | FOBS= | 291.7 | SIGMA= | 0.6 | PHAS= | -44.8 | FOM= | 0.99 | TEST= 0 |
| INDE | 1 | 8 | 25 | FOBS= | 136.4 | SIGMA= | 1.0 | PHAS= | 17.5 | FOM= | 0.96 | TEST= 0 |
| INDE | 1 | 8 | 27 | FOBS= | 68.0 | SIGMA= | 1.8 | PHAS= | -114.3 | FOM= | 0.89 | TEST= 0 |
| INDE | 1 | 8 | 29 | FOBS= | 142.6 | SIGMA= | 1.2 | PHAS= | 77.4 | FOM= | 0.94 | TEST= 0 |
| INDE | 1 | 8 | 31 | FOBS= | 28.6 | SIGMA= | 4.6 | PHAS= | 170.3 | FOM= | 0.83 | TEST= 0 |
| INDE | 1 | 8 | 33 | FOBS= | 119.9 | SIGMA= | 1.3 | PHAS= | -160.4 | FOM= | 0.90 | TEST= 0 |
| INDE | 1 | 8 | 35 | FOBS= | 144.7 | SIGMA= | 1.2 | PHAS= | 79.3 | FOM= | 0.72 | TEST= 0 |
| INDE | 1 | 8 | 37 | FOBS= | 154.9 | SIGMA= | 0.9 | PHAS= | 88.7 | FOM= | 0.64 | TEST= 0 |
| INDE | 1 | 8 | 39 | FOBS= | 182.6 | SIGMA= | 1.0 | PHAS= | -1.8 | FOM= | 0.97 | TEST= 0 |
| INDE | 1 | 8 | 41 | FOBS= | 64.0 | SIGMA= | 2.3 | PHAS= | -43.8 | FOM= | 0.84 | TEST= 0 |
| INDE | 1 | 8 | 43 | FOBS= | 49.4 | SIGMA= | 3.5 | PHAS= | -144.0 | FOM= | 0.82 | TEST= 1 |
| INDE | 1 | 8 | 45 | FOBS= | 148.4 | SIGMA= | 1.4 | PHAS= | 13.7 | FOM= | 0.85 | TEST= 0 |
| INDE | 1 | 8 | 47 | FOBS= | 105.4 | SIGMA= | 2.1 | PHAS= | -13.3 | FOM= | 0.90 | TEST= 1 |
| INDE | 1 | 8 | 49 | FOBS= | 128.8 | SIGMA= | 1.3 | PHAS= | -22.1 | FOM= | 0.86 | TEST= 0 |
| INDE | 1 | 8 | 51 | FOBS= | 100.8 | SIGMA= | 1.6 | PHAS= | 42.7 | FOM= | 0.79 | TEST= 0 |
| INDE | 1 | 8 | 53 | FOBS= | 63.9 | SIGMA= | 2.6 | PHAS= | 103.1 | FOM= | 0.88 | TEST= 0 |
| INDE | 1 | 8 | 55 | FOBS= | 117.2 | SIGMA= | 1.4 | PHAS= | -131.2 | FOM= | 0.94 | TEST= 0 |
| INDE | 1 | 8 | 57 | FOBS= | 134.9 | SIGMA= | 1.2 | PHAS= | 77.8 | FOM= | 0.92 | TEST= 0 |
| INDE | 1 | 8 | 59 | FOBS= | 88.7 | SIGMA= | 1.7 | PHAS= | 162.2 | FOM= | 0.81 | TEST= 0 |
| INDE | 1 | 8 | 61 | FOBS= | 89.1 | SIGMA= | 1.7 | PHAS= | 144.3 | FOM= | 0.83 | TEST= 0 |
| INDE | 1 | 8 | 63 | FOBS= | 67.7 | SIGMA= | 2.7 | PHAS= | -38.0 | FOM= | 0.94 | TEST= 0 |
| INDE | 1 | 8 | 65 | FOBS= | 55.7 | SIGMA= | 3.8 | PHAS= | -158.4 | FOM= | 0.49 | TEST= 0 |
| INDE | 1 | 8 | 67 | FOBS= | 0.0 | SIGMA= | 22.8 | PHAS= | 0.0 | FOM= | 0.00 | TEST= 0 |
| INDE | 1 | 8 | 69 | FOBS= | 29.7 | SIGMA= | 8.8 | PHAS= | -71.1 | FOM= | 0.35 | TEST= 0 |
| INDE | 1 | 8 | 71 | FOBS= | 85.7 | SIGMA= | 3.2 | PHAS= | -138.0 | FOM= | 0.84 | TEST= 0 |
| INDE | 1 | 8 | 73 | FOBS= | 53.3 | SIGMA= | 5.1 | PHAS= | 147.0 | FOM= | 0.55 | TEST= 0 |
| INDE | 1 | 8 | 75 | FOBS= | 66.7 | SIGMA= | 4.1 | PHAS= | 114.0 | FOM= | 0.88 | TEST= 0 |
| INDE | 1 | 8 | 77 | FOBS= | 78.0 | SIGMA= | 5.3 | PHAS= | 16.7 | FOM= | 0.90 | TEST= 0 |
| INDE | 1 | 9 | 16 | FOBS= | 109.3 | SIGMA= | 0.5 | PHAS= | 142.5 | FOM= | 0.68 | TEST= 0 |
| INDE | 1 | 9 | 18 | FOBS= | 202.2 | SIGMA= | 0.5 | PHAS= | -11.8 | FOM= | 0.59 | TEST= 1 |
| INDE | 1 | 9 | 20 | FOBS= | 42.5 | SIGMA= | 1.1 | PHAS= | -118.8 | FOM= | 0.89 | TEST= 0 |
| INDE | 1 | 9 | 22 | FOBS= | 449.2 | SIGMA= | 0.6 | PHAS= | 64.3 | FOM= | 0.99 | TEST= 0 |
| INDE | 1 | 9 | 24 | FOBS= | 115.8 | SIGMA= | 0.8 | PHAS= | 136.9 | FOM= | 0.89 | TEST= 0 |
| INDE | 1 | 9 | 26 | FOBS= | 129.6 | SIGMA= | 0.8 | PHAS= | 9.5 | FOM= | 0.98 | TEST= 0 |
| INDE | 1 | 9 | 28 | FOBS= | 36.1 | SIGMA= | 3.3 | PHAS= | 39.8 | FOM= | 0.78 | TEST= 1 |
| INDE | 1 | 9 | 30 | FOBS= | 171.1 | SIGMA= | 1.1 | PHAS= | -160.1 | FOM= | 0.94 | TEST= 0 |
| INDE | 1 | 9 | 32 | FOBS= | 85.0 | SIGMA= | 1.7 | PHAS= | -12.8 | FOM= | 0.93 | TEST= 0 |
| INDE | 1 | 9 | 34 | FOBS= | 71.8 | SIGMA= | 2.1 | PHAS= | 37.8 | FOM= | 0.91 | TEST= 1 |
| INDE | 1 | 9 | 36 | FOBS= | 155.5 | SIGMA= | 1.2 | PHAS= | -169.1 | FOM= | 0.94 | TEST= 0 |
| INDE | 1 | 9 | 38 | FOBS= | 198.2 | SIGMA= | 0.9 | PHAS= | -88.0 | FOM= | 0.93 | TEST= 0 |
| INDE | 1 | 9 | 40 | FOBS= | 156.6 | SIGMA= | 1.0 | PHAS= | -102.9 | FOM= | 0.95 | TEST= 0 |
| INDE | 1 | 9 | 42 | FOBS= | 63.2 | SIGMA= | 2.5 | PHAS= | -76.6 | FOM= | 0.78 | TEST= 0 |
| INDE | 1 | 9 | 44 | FOBS= | 86.3 | SIGMA= | 2.2 | PHAS= | -112.7 | FOM= | 0.88 | TEST= 0 |
| INDE | 1 | 9 | 46 | FOBS= | 68.5 | SIGMA= | 3.0 | PHAS= | -75.4 | FOM= | 0.73 | TEST= 0 |
| INDE | 1 | 9 | 48 | FOBS= | 64.9 | SIGMA= | 3.4 | PHAS= | -108.6 | FOM= | 0.85 | TEST= 0 |

*FIG. 12A - 27*

```
INDE  1  9  50 FOBS=  109.4 SIGMA=  1.5 PHAS= -154.5 FOM= 0.85 TEST= 0
INDE  1  9  52 FOBS=  188.5 SIGMA=  0.9 PHAS=  -40.1 FOM= 0.97 TEST= 0
INDE  1  9  54 FOBS=  183.0 SIGMA=  1.0 PHAS=  -33.1 FOM= 0.96 TEST= 0
INDE  1  9  56 FOBS=   82.8 SIGMA=  1.9 PHAS= -135.1 FOM= 0.90 TEST= 0
INDE  1  9  58 FOBS=  150.0 SIGMA=  1.1 PHAS=   81.2 FOM= 0.93 TEST= 0
INDE  1  9  60 FOBS=   82.5 SIGMA=  1.9 PHAS=   74.8 FOM= 0.06 TEST= 1
INDE  1  9  62 FOBS=  110.8 SIGMA=  1.5 PHAS=  174.5 FOM= 0.93 TEST= 0
INDE  1  9  64 FOBS=  153.4 SIGMA=  1.3 PHAS= -176.3 FOM= 0.95 TEST= 0
INDE  1  9  66 FOBS=  106.9 SIGMA=  2.6 PHAS=   53.1 FOM= 0.82 TEST= 0
INDE  1  9  68 FOBS=   16.5 SIGMA= 16.0 PHAS= -112.4 FOM= 0.15 TEST= 0
INDE  1  9  70 FOBS=   52.7 SIGMA=  5.1 PHAS= -122.2 FOM= 0.90 TEST= 0
INDE  1  9  72 FOBS=   38.0 SIGMA=  7.2 PHAS=   13.3 FOM= 0.77 TEST= 0
INDE  1  9  74 FOBS=   35.9 SIGMA=  7.7 PHAS=   32.1 FOM= 0.49 TEST= 0
INDE  1  9  76 FOBS=  115.5 SIGMA=  2.6 PHAS=  -17.4 FOM= 0.96 TEST= 0
INDE  1 10  15 FOBS=  143.4 SIGMA=  0.5 PHAS=   23.0 FOM= 0.90 TEST= 0
INDE  1 10  17 FOBS=   91.6 SIGMA=  0.6 PHAS=  -11.0 FOM= 0.92 TEST= 1
INDE  1 10  19 FOBS=   39.7 SIGMA=  1.2 PHAS=  140.9 FOM= 0.79 TEST= 0
INDE  1 10  21 FOBS=  204.4 SIGMA=  0.6 PHAS=   40.6 FOM= 0.50 TEST= 1
INDE  1 10  23 FOBS=  274.6 SIGMA=  0.4 PHAS=   43.4 FOM= 0.96 TEST= 0
INDE  1 10  25 FOBS=  227.2 SIGMA=  0.5 PHAS=   40.3 FOM= 0.68 TEST= 0
INDE  1 10  27 FOBS=  118.4 SIGMA=  0.9 PHAS=  -43.7 FOM= 0.99 TEST= 0
INDE  1 10  29 FOBS=   95.7 SIGMA=  1.3 PHAS=  166.6 FOM= 0.70 TEST= 1
INDE  1 10  31 FOBS=  115.2 SIGMA=  1.3 PHAS=  166.1 FOM= 0.96 TEST= 0
INDE  1 10  33 FOBS=   63.6 SIGMA=  2.3 PHAS= -173.9 FOM= 0.44 TEST= 1
INDE  1 10  35 FOBS=   39.4 SIGMA=  4.0 PHAS= -168.5 FOM= 0.41 TEST= 0
INDE  1 10  37 FOBS=  232.0 SIGMA=  1.0 PHAS=  141.8 FOM= 0.82 TEST= 0
INDE  1 10  39 FOBS=  145.8 SIGMA=  1.1 PHAS=   67.4 FOM= 0.84 TEST= 0
INDE  1 10  41 FOBS=  220.2 SIGMA=  0.8 PHAS= -171.9 FOM= 0.97 TEST= 0
INDE  1 10  43 FOBS=   97.8 SIGMA=  1.9 PHAS=  148.0 FOM= 0.85 TEST= 0
INDE  1 10  45 FOBS=  126.6 SIGMA=  1.7 PHAS=  -18.6 FOM= 0.96 TEST= 0
INDE  1 10  47 FOBS=   61.9 SIGMA=  3.5 PHAS=  165.0 FOM= 0.43 TEST= 0
INDE  1 10  49 FOBS=   85.5 SIGMA=  2.4 PHAS= -163.2 FOM= 0.92 TEST= 0
INDE  1 10  51 FOBS=   87.1 SIGMA=  1.9 PHAS=  -70.8 FOM= 0.78 TEST= 0
INDE  1 10  53 FOBS=  183.8 SIGMA=  1.0 PHAS= -167.5 FOM= 0.95 TEST= 0
INDE  1 10  55 FOBS=  219.6 SIGMA=  0.9 PHAS= -142.7 FOM= 0.96 TEST= 0
INDE  1 10  57 FOBS=  103.2 SIGMA=  1.5 PHAS=   35.2 FOM= 0.85 TEST= 0
INDE  1 10  59 FOBS=  127.3 SIGMA=  1.3 PHAS=   33.1 FOM= 0.93 TEST= 0
INDE  1 10  61 FOBS=   86.2 SIGMA=  1.8 PHAS=   80.7 FOM= 0.77 TEST= 0
INDE  1 10  63 FOBS=  124.3 SIGMA=  1.6 PHAS=  -28.1 FOM= 0.82 TEST= 0
INDE  1 10  65 FOBS=  138.9 SIGMA=  1.8 PHAS=   99.6 FOM= 0.24 TEST= 1
INDE  1 10  67 FOBS=   47.4 SIGMA=  5.7 PHAS=  -96.3 FOM= 0.62 TEST= 0
INDE  1 10  69 FOBS=   53.8 SIGMA=  5.1 PHAS=   14.3 FOM= 0.81 TEST= 0
INDE  1 10  71 FOBS=  109.0 SIGMA=  2.6 PHAS= -140.8 FOM= 0.95 TEST= 0
INDE  1 10  73 FOBS=   89.3 SIGMA=  3.2 PHAS=  -89.8 FOM= 0.91 TEST= 0
INDE  1 10  75 FOBS=   55.7 SIGMA=  5.2 PHAS= -176.1 FOM= 0.89 TEST= 0
INDE  1 10  77 FOBS=   59.1 SIGMA=  7.4 PHAS=  -78.2 FOM= 0.78 TEST= 0
INDE  1 11  16 FOBS=  187.9 SIGMA=  0.5 PHAS= -170.5 FOM= 0.91 TEST= 0
INDE  1 11  18 FOBS=  237.2 SIGMA=  0.6 PHAS=  -59.8 FOM= 0.96 TEST= 0
INDE  1 11  20 FOBS=  157.9 SIGMA=  0.5 PHAS=  -58.2 FOM= 0.93 TEST= 0
INDE  1 11  22 FOBS=   47.0 SIGMA=  1.2 PHAS=   49.8 FOM= 0.87 TEST= 0
INDE  1 11  24 FOBS=  129.0 SIGMA=  0.6 PHAS=  -22.4 FOM= 0.99 TEST= 0
INDE  1 11  26 FOBS=   79.4 SIGMA=  0.7 PHAS=  -56.1 FOM= 0.98 TEST= 0
INDE  1 11  28 FOBS=  106.0 SIGMA=  0.7 PHAS=  131.4 FOM= 0.82 TEST= 0
INDE  1 11  30 FOBS=  211.4 SIGMA=  0.7 PHAS=   98.8 FOM= 0.95 TEST= 0
INDE  1 11  32 FOBS=  123.3 SIGMA=  1.3 PHAS=   19.8 FOM= 0.91 TEST= 0
INDE  1 11  34 FOBS=  135.4 SIGMA=  1.3 PHAS= -130.0 FOM= 0.24 TEST= 1
INDE  1 11  36 FOBS=  143.5 SIGMA=  1.3 PHAS=  130.1 FOM= 0.94 TEST= 0
INDE  1 11  38 FOBS=  224.1 SIGMA=  1.0 PHAS=  -86.4 FOM= 0.96 TEST= 0
INDE  1 11  40 FOBS=  187.0 SIGMA=  1.1 PHAS=  -67.2 FOM= 0.95 TEST= 0
INDE  1 11  42 FOBS=  159.2 SIGMA=  1.1 PHAS=   94.7 FOM= 0.97 TEST= 0
INDE  1 11  44 FOBS=  125.4 SIGMA=  1.6 PHAS= -128.3 FOM= 0.98 TEST= 0
INDE  1 11  46 FOBS=  188.4 SIGMA=  1.2 PHAS=    8.5 FOM= 0.93 TEST= 0
INDE  1 11  48 FOBS=   97.0 SIGMA=  2.3 PHAS=  123.1 FOM= 0.88 TEST= 0
INDE  1 11  50 FOBS=  279.1 SIGMA=  0.9 PHAS=  155.1 FOM= 0.94 TEST= 0
INDE  1 11  52 FOBS=   73.7 SIGMA=  2.3 PHAS=  -51.7 FOM= 0.64 TEST= 0
INDE  1 11  54 FOBS=   56.6 SIGMA=  3.0 PHAS=  -44.7 FOM= 0.33 TEST= 0
INDE  1 11  56 FOBS=    0.0 SIGMA= 18.2 PHAS=    0.0 FOM= 0.00 TEST= 0
INDE  1 11  58 FOBS=   74.6 SIGMA=  2.1 PHAS=  128.5 FOM= 0.65 TEST= 0
INDE  1 11  60 FOBS=   46.4 SIGMA=  3.4 PHAS=   42.3 FOM= 0.52 TEST= 0
INDE  1 11  62 FOBS=   33.0 SIGMA=  4.7 PHAS=  -36.1 FOM= 0.47 TEST= 0
```

*FIG. 12A - 28*

| | | | | | | | | | | | | |
|---|---|---|---|---|---|---|---|---|---|---|---|---|
| INDE | 1 | 11 | 64 | FOBS= | 124.3 | SIGMA= | 1.6 | PHAS= | 19.8 | FOM= | 0.84 | TEST= 0 |
| INDE | 1 | 11 | 66 | FOBS= | 87.1 | SIGMA= | 3.3 | PHAS= | -20.1 | FOM= | 0.27 | TEST= 1 |
| INDE | 1 | 11 | 68 | FOBS= | 94.5 | SIGMA= | 3.0 | PHAS= | -129.2 | FOM= | 0.92 | TEST= 0 |
| INDE | 1 | 11 | 70 | FOBS= | 118.7 | SIGMA= | 2.4 | PHAS= | -100.5 | FOM= | 0.95 | TEST= 0 |
| INDE | 1 | 11 | 72 | FOBS= | 111.1 | SIGMA= | 2.6 | PHAS= | -172.4 | FOM= | 0.92 | TEST= 0 |
| INDE | 1 | 11 | 74 | FOBS= | 40.2 | SIGMA= | 10.0 | PHAS= | 94.2 | FOM= | 0.58 | TEST= 0 |
| INDE | 1 | 11 | 76 | FOBS= | 92.5 | SIGMA= | 3.3 | PHAS= | -103.7 | FOM= | 0.86 | TEST= 0 |
| INDE | 1 | 12 | 15 | FOBS= | 237.6 | SIGMA= | 0.6 | PHAS= | 116.2 | FOM= | 0.79 | TEST= 0 |
| INDE | 1 | 12 | 17 | FOBS= | 286.5 | SIGMA= | 0.5 | PHAS= | 146.5 | FOM= | 0.94 | TEST= 0 |
| INDE | 1 | 12 | 19 | FOBS= | 144.3 | SIGMA= | 0.5 | PHAS= | 157.6 | FOM= | 0.93 | TEST= 0 |
| INDE | 1 | 12 | 21 | FOBS= | 156.5 | SIGMA= | 0.5 | PHAS= | -165.6 | FOM= | 0.88 | TEST= 0 |
| INDE | 1 | 12 | 23 | FOBS= | 90.8 | SIGMA= | 0.8 | PHAS= | -133.2 | FOM= | 0.99 | TEST= 0 |
| INDE | 1 | 12 | 25 | FOBS= | 218.8 | SIGMA= | 0.6 | PHAS= | -27.4 | FOM= | 0.95 | TEST= 0 |
| INDE | 1 | 12 | 27 | FOBS= | 116.7 | SIGMA= | 0.5 | PHAS= | 50.3 | FOM= | 0.99 | TEST= 0 |
| INDE | 1 | 12 | 29 | FOBS= | 60.4 | SIGMA= | 1.0 | PHAS= | -80.6 | FOM= | 0.91 | TEST= 0 |
| INDE | 1 | 12 | 31 | FOBS= | 64.9 | SIGMA= | 1.2 | PHAS= | -6.8 | FOM= | 0.75 | TEST= 0 |
| INDE | 1 | 12 | 33 | FOBS= | 140.6 | SIGMA= | 0.9 | PHAS= | -90.0 | FOM= | 0.75 | TEST= 0 |
| INDE | 1 | 12 | 35 | FOBS= | 178.4 | SIGMA= | 1.1 | PHAS= | -126.7 | FOM= | 0.91 | TEST= 0 |
| INDE | 1 | 12 | 37 | FOBS= | 351.8 | SIGMA= | 0.9 | PHAS= | 112.5 | FOM= | 0.99 | TEST= 0 |
| INDE | 1 | 12 | 39 | FOBS= | 258.8 | SIGMA= | 1.0 | PHAS= | -139.5 | FOM= | 0.91 | TEST= 0 |
| INDE | 1 | 12 | 41 | FOBS= | 163.1 | SIGMA= | 1.2 | PHAS= | -130.4 | FOM= | 0.89 | TEST= 0 |
| INDE | 1 | 12 | 43 | FOBS= | 197.5 | SIGMA= | 1.2 | PHAS= | 58.6 | FOM= | 0.81 | TEST= 0 |
| INDE | 1 | 12 | 45 | FOBS= | 74.1 | SIGMA= | 2.9 | PHAS= | 159.3 | FOM= | 0.49 | TEST= 0 |
| INDE | 1 | 12 | 47 | FOBS= | 66.3 | SIGMA= | 3.4 | PHAS= | 72.1 | FOM= | 0.90 | TEST= 0 |
| INDE | 1 | 12 | 49 | FOBS= | 392.9 | SIGMA= | 0.8 | PHAS= | 72.7 | FOM= | 0.98 | TEST= 0 |
| INDE | 1 | 12 | 51 | FOBS= | 155.5 | SIGMA= | 1.4 | PHAS= | -79.0 | FOM= | 0.91 | TEST= 0 |
| INDE | 1 | 12 | 53 | FOBS= | 111.4 | SIGMA= | 1.6 | PHAS= | 138.0 | FOM= | 0.93 | TEST= 1 |
| INDE | 1 | 12 | 55 | FOBS= | 92.6 | SIGMA= | 1.9 | PHAS= | 174.5 | FOM= | 0.90 | TEST= 0 |
| INDE | 1 | 12 | 57 | FOBS= | 76.7 | SIGMA= | 2.1 | PHAS= | 83.7 | FOM= | 0.77 | TEST= 0 |
| INDE | 1 | 12 | 59 | FOBS= | 123.6 | SIGMA= | 1.3 | PHAS= | 73.5 | FOM= | 0.94 | TEST= 0 |
| INDE | 1 | 12 | 61 | FOBS= | 0.0 | SIGMA= | 18.5 | PHAS= | 0.0 | FOM= | 0.00 | TEST= 0 |
| INDE | 1 | 12 | 63 | FOBS= | 117.9 | SIGMA= | 1.7 | PHAS= | -108.3 | FOM= | 0.90 | TEST= 0 |
| INDE | 1 | 12 | 65 | FOBS= | 0.0 | SIGMA= | 23.6 | PHAS= | 0.0 | FOM= | 0.00 | TEST= 0 |
| INDE | 1 | 12 | 67 | FOBS= | 107.8 | SIGMA= | 2.7 | PHAS= | -164.4 | FOM= | 0.92 | TEST= 0 |
| INDE | 1 | 12 | 69 | FOBS= | 50.3 | SIGMA= | 5.6 | PHAS= | 104.3 | FOM= | 0.74 | TEST= 0 |
| INDE | 1 | 12 | 71 | FOBS= | 87.6 | SIGMA= | 3.2 | PHAS= | 162.1 | FOM= | 0.96 | TEST= 0 |
| INDE | 1 | 12 | 73 | FOBS= | 52.3 | SIGMA= | 7.8 | PHAS= | 66.7 | FOM= | 0.54 | TEST= 0 |
| INDE | 1 | 12 | 75 | FOBS= | 133.9 | SIGMA= | 2.3 | PHAS= | -140.4 | FOM= | 0.98 | TEST= 0 |
| INDE | 1 | 13 | 14 | FOBS= | 94.6 | SIGMA= | 1.0 | PHAS= | 31.1 | FOM= | 0.83 | TEST= 0 |
| INDE | 1 | 13 | 16 | FOBS= | 288.9 | SIGMA= | 0.5 | PHAS= | 46.6 | FOM= | 0.94 | TEST= 0 |
| INDE | 1 | 13 | 18 | FOBS= | 275.3 | SIGMA= | 0.6 | PHAS= | -40.8 | FOM= | 0.99 | TEST= 0 |
| INDE | 1 | 13 | 20 | FOBS= | 90.5 | SIGMA= | 0.7 | PHAS= | 86.2 | FOM= | 0.94 | TEST= 0 |
| INDE | 1 | 13 | 22 | FOBS= | 52.1 | SIGMA= | 1.1 | PHAS= | 58.9 | FOM= | 0.98 | TEST= 0 |
| INDE | 1 | 13 | 24 | FOBS= | 67.1 | SIGMA= | 0.9 | PHAS= | -137.2 | FOM= | 0.94 | TEST= 0 |
| INDE | 1 | 13 | 26 | FOBS= | 11.8 | SIGMA= | 5.1 | PHAS= | 155.2 | FOM= | 0.57 | TEST= 0 |
| INDE | 1 | 13 | 28 | FOBS= | 171.0 | SIGMA= | 0.7 | PHAS= | -131.9 | FOM= | 0.99 | TEST= 0 |
| INDE | 1 | 13 | 30 | FOBS= | 90.8 | SIGMA= | 0.8 | PHAS= | 131.8 | FOM= | 0.97 | TEST= 0 |
| INDE | 1 | 13 | 32 | FOBS= | 276.9 | SIGMA= | 0.6 | PHAS= | 166.3 | FOM= | 0.95 | TEST= 0 |
| INDE | 1 | 13 | 34 | FOBS= | 270.3 | SIGMA= | 0.6 | PHAS= | 127.7 | FOM= | 0.97 | TEST= 1 |
| INDE | 1 | 13 | 36 | FOBS= | 164.1 | SIGMA= | 1.2 | PHAS= | 5.9 | FOM= | 0.98 | TEST= 0 |
| INDE | 1 | 13 | 38 | FOBS= | 314.3 | SIGMA= | 1.0 | PHAS= | -105.2 | FOM= | 0.95 | TEST= 0 |
| INDE | 1 | 13 | 40 | FOBS= | 88.0 | SIGMA= | 2.5 | PHAS= | -51.2 | FOM= | 0.86 | TEST= 0 |
| INDE | 1 | 13 | 42 | FOBS= | 184.1 | SIGMA= | 1.2 | PHAS= | 147.0 | FOM= | 0.94 | TEST= 0 |
| INDE | 1 | 13 | 44 | FOBS= | 123.6 | SIGMA= | 1.7 | PHAS= | 68.3 | FOM= | 0.87 | TEST= 0 |
| INDE | 1 | 13 | 46 | FOBS= | 322.9 | SIGMA= | 1.3 | PHAS= | -18.0 | FOM= | 0.97 | TEST= 0 |
| INDE | 1 | 13 | 48 | FOBS= | 359.0 | SIGMA= | 1.2 | PHAS= | -20.6 | FOM= | 0.98 | TEST= 0 |
| INDE | 1 | 13 | 50 | FOBS= | 31.1 | SIGMA= | 7.2 | PHAS= | -53.1 | FOM= | 0.15 | TEST= 0 |
| INDE | 1 | 13 | 52 | FOBS= | 151.1 | SIGMA= | 1.4 | PHAS= | 92.9 | FOM= | 0.98 | TEST= 0 |
| INDE | 1 | 13 | 54 | FOBS= | 43.7 | SIGMA= | 3.9 | PHAS= | 42.5 | FOM= | 0.86 | TEST= 0 |
| INDE | 1 | 13 | 56 | FOBS= | 0.0 | SIGMA= | 17.8 | PHAS= | 0.0 | FOM= | 0.00 | TEST= 0 |
| INDE | 1 | 13 | 58 | FOBS= | 55.7 | SIGMA= | 2.9 | PHAS= | 45.6 | FOM= | 0.90 | TEST= 0 |
| INDE | 1 | 13 | 60 | FOBS= | 63.2 | SIGMA= | 2.5 | PHAS= | -8.4 | FOM= | 0.54 | TEST= 1 |
| INDE | 1 | 13 | 62 | FOBS= | 107.8 | SIGMA= | 1.5 | PHAS= | 151.7 | FOM= | 0.33 | TEST= 1 |
| INDE | 1 | 13 | 64 | FOBS= | 97.4 | SIGMA= | 2.1 | PHAS= | -143.4 | FOM= | 0.52 | TEST= 1 |
| INDE | 1 | 13 | 66 | FOBS= | 58.6 | SIGMA= | 5.0 | PHAS= | -87.6 | FOM= | 0.89 | TEST= 0 |
| INDE | 1 | 13 | 68 | FOBS= | 0.0 | SIGMA= | 23.8 | PHAS= | 0.0 | FOM= | 0.00 | TEST= 0 |
| INDE | 1 | 13 | 70 | FOBS= | 40.0 | SIGMA= | 7.3 | PHAS= | 103.9 | FOM= | 0.54 | TEST= 0 |
| INDE | 1 | 13 | 72 | FOBS= | 57.1 | SIGMA= | 5.1 | PHAS= | 60.6 | FOM= | 0.71 | TEST= 0 |
| INDE | 1 | 13 | 74 | FOBS= | 99.1 | SIGMA= | 3.1 | PHAS= | 119.5 | FOM= | 0.93 | TEST= 0 |
| INDE | 1 | 13 | 76 | FOBS= | 123.9 | SIGMA= | 2.6 | PHAS= | 130.6 | FOM= | 0.95 | TEST= 0 |

*FIG. 12A - 29*

| | | | | | | | | | | | | |
|---|---|---|---|---|---|---|---|---|---|---|---|---|
| INDE | 1 | 14 | 15 | FOBS= | 305.3 | SIGMA= | 0.7 | PHAS= | -80.3 | FOM= | 0.94 | TEST= 0 |
| INDE | 1 | 14 | 17 | FOBS= | 336.6 | SIGMA= | 0.7 | PHAS= | -158.8 | FOM= | 0.95 | TEST= 0 |
| INDE | 1 | 14 | 19 | FOBS= | 164.0 | SIGMA= | 0.6 | PHAS= | -177.8 | FOM= | 0.93 | TEST= 0 |
| INDE | 1 | 14 | 21 | FOBS= | 85.2 | SIGMA= | 0.8 | PHAS= | 146.9 | FOM= | 0.91 | TEST= 0 |
| INDE | 1 | 14 | 23 | FOBS= | 199.9 | SIGMA= | 0.6 | PHAS= | -133.2 | FOM= | 0.94 | TEST= 0 |
| INDE | 1 | 14 | 25 | FOBS= | 168.4 | SIGMA= | 0.5 | PHAS= | -75.1 | FOM= | 0.84 | TEST= 0 |
| INDE | 1 | 14 | 27 | FOBS= | 268.3 | SIGMA= | 0.6 | PHAS= | 95.6 | FOM= | 0.98 | TEST= 0 |
| INDE | 1 | 14 | 29 | FOBS= | 93.8 | SIGMA= | 0.7 | PHAS= | 157.8 | FOM= | 0.97 | TEST= 0 |
| INDE | 1 | 14 | 31 | FOBS= | 47.1 | SIGMA= | 1.4 | PHAS= | -58.0 | FOM= | 0.60 | TEST= 0 |
| INDE | 1 | 14 | 33 | FOBS= | 143.6 | SIGMA= | 0.7 | PHAS= | 34.4 | FOM= | 0.96 | TEST= 1 |
| INDE | 1 | 14 | 35 | FOBS= | 236.7 | SIGMA= | 0.8 | PHAS= | 125.8 | FOM= | 0.97 | TEST= 0 |
| INDE | 1 | 14 | 37 | FOBS= | 371.7 | SIGMA= | 0.9 | PHAS= | -168.4 | FOM= | 0.99 | TEST= 0 |
| INDE | 1 | 14 | 39 | FOBS= | 360.6 | SIGMA= | 0.9 | PHAS= | -141.1 | FOM= | 0.98 | TEST= 0 |
| INDE | 1 | 14 | 41 | FOBS= | 80.5 | SIGMA= | 2.8 | PHAS= | -51.7 | FOM= | 0.95 | TEST= 0 |
| INDE | 1 | 14 | 43 | FOBS= | 229.1 | SIGMA= | 1.4 | PHAS= | 31.2 | FOM= | 0.94 | TEST= 0 |
| INDE | 1 | 14 | 45 | FOBS= | 177.1 | SIGMA= | 1.3 | PHAS= | -52.4 | FOM= | 0.95 | TEST= 0 |
| INDE | 1 | 14 | 47 | FOBS= | 384.6 | SIGMA= | 1.1 | PHAS= | -121.1 | FOM= | 0.96 | TEST= 0 |
| INDE | 1 | 14 | 49 | FOBS= | 63.6 | SIGMA= | 3.3 | PHAS= | 122.3 | FOM= | 0.91 | TEST= 0 |
| INDE | 1 | 14 | 51 | FOBS= | 231.8 | SIGMA= | 1.0 | PHAS= | -66.0 | FOM= | 0.93 | TEST= 1 |
| INDE | 1 | 14 | 53 | FOBS= | 81.2 | SIGMA= | 2.4 | PHAS= | 10.8 | FOM= | 0.91 | TEST= 0 |
| INDE | 1 | 14 | 55 | FOBS= | 20.8 | SIGMA= | 8.2 | PHAS= | 11.9 | FOM= | 0.13 | TEST= 0 |
| INDE | 1 | 14 | 57 | FOBS= | 61.4 | SIGMA= | 2.6 | PHAS= | -150.3 | FOM= | 0.19 | TEST= 1 |
| INDE | 1 | 14 | 59 | FOBS= | 72.9 | SIGMA= | 2.2 | PHAS= | -55.9 | FOM= | 0.54 | TEST= 0 |
| INDE | 1 | 14 | 61 | FOBS= | 0.0 | SIGMA= | 17.7 | PHAS= | 0.0 | FOM= | 0.00 | TEST= 0 |
| INDE | 1 | 14 | 63 | FOBS= | 134.5 | SIGMA= | 1.2 | PHAS= | 104.7 | FOM= | 0.94 | TEST= 0 |
| INDE | 1 | 14 | 65 | FOBS= | 83.0 | SIGMA= | 3.6 | PHAS= | 102.9 | FOM= | 0.95 | TEST= 0 |
| INDE | 1 | 14 | 67 | FOBS= | 35.7 | SIGMA= | 8.3 | PHAS= | -156.6 | FOM= | 0.63 | TEST= 0 |
| INDE | 1 | 14 | 69 | FOBS= | 68.7 | SIGMA= | 4.3 | PHAS= | 138.6 | FOM= | 0.76 | TEST= 0 |
| INDE | 1 | 14 | 71 | FOBS= | 61.4 | SIGMA= | 4.8 | PHAS= | 16.0 | FOM= | 0.88 | TEST= 0 |
| INDE | 1 | 14 | 73 | FOBS= | 31.9 | SIGMA= | 13.0 | PHAS= | 148.3 | FOM= | 0.08 | TEST= 1 |
| INDE | 1 | 14 | 75 | FOBS= | 63.3 | SIGMA= | 6.9 | PHAS= | 110.0 | FOM= | 0.89 | TEST= 0 |
| INDE | 1 | 15 | 16 | FOBS= | 209.1 | SIGMA= | 0.7 | PHAS= | 124.7 | FOM= | 0.92 | TEST= 0 |
| INDE | 1 | 15 | 18 | FOBS= | 193.8 | SIGMA= | 0.8 | PHAS= | 79.2 | FOM= | 0.89 | TEST= 0 |
| INDE | 1 | 15 | 20 | FOBS= | 273.1 | SIGMA= | 0.5 | PHAS= | 28.1 | FOM= | 0.47 | TEST= 1 |
| INDE | 1 | 15 | 22 | FOBS= | 171.6 | SIGMA= | 0.5 | PHAS= | 78.7 | FOM= | 0.92 | TEST= 1 |
| INDE | 1 | 15 | 24 | FOBS= | 136.6 | SIGMA= | 0.6 | PHAS= | 174.7 | FOM= | 0.98 | TEST= 0 |
| INDE | 1 | 15 | 26 | FOBS= | 144.6 | SIGMA= | 0.6 | PHAS= | 23.4 | FOM= | 0.99 | TEST= 0 |
| INDE | 1 | 15 | 28 | FOBS= | 58.2 | SIGMA= | 1.0 | PHAS= | -26.0 | FOM= | 0.98 | TEST= 1 |
| INDE | 1 | 15 | 30 | FOBS= | 154.2 | SIGMA= | 0.6 | PHAS= | -13.4 | FOM= | 0.89 | TEST= 0 |
| INDE | 1 | 15 | 32 | FOBS= | 232.1 | SIGMA= | 0.5 | PHAS= | 174.9 | FOM= | 0.98 | TEST= 0 |
| INDE | 1 | 15 | 34 | FOBS= | 293.5 | SIGMA= | 0.6 | PHAS= | 73.7 | FOM= | 0.93 | TEST= 0 |
| INDE | 1 | 15 | 36 | FOBS= | 341.0 | SIGMA= | 0.7 | PHAS= | 14.0 | FOM= | 0.95 | TEST= 0 |
| INDE | 1 | 15 | 38 | FOBS= | 178.4 | SIGMA= | 0.9 | PHAS= | -171.3 | FOM= | 0.96 | TEST= 0 |
| INDE | 1 | 15 | 40 | FOBS= | 173.3 | SIGMA= | 1.4 | PHAS= | 2.9 | FOM= | 0.83 | TEST= 0 |
| INDE | 1 | 15 | 42 | FOBS= | 173.1 | SIGMA= | 1.5 | PHAS= | -155.3 | FOM= | 0.96 | TEST= 0 |
| INDE | 1 | 15 | 44 | FOBS= | 0.0 | SIGMA= | 20.6 | PHAS= | 0.0 | FOM= | 0.00 | TEST= 0 |
| INDE | 1 | 15 | 46 | FOBS= | 217.9 | SIGMA= | 1.7 | PHAS= | 10.7 | FOM= | 0.88 | TEST= 0 |
| INDE | 1 | 15 | 48 | FOBS= | 163.6 | SIGMA= | 1.8 | PHAS= | 26.8 | FOM= | 0.72 | TEST= 0 |
| INDE | 1 | 15 | 50 | FOBS= | 63.1 | SIGMA= | 3.3 | PHAS= | -153.0 | FOM= | 0.56 | TEST= 0 |
| INDE | 1 | 15 | 52 | FOBS= | 106.7 | SIGMA= | 2.0 | PHAS= | 129.9 | FOM= | 0.83 | TEST= 0 |
| INDE | 1 | 15 | 54 | FOBS= | 83.1 | SIGMA= | 2.1 | PHAS= | -129.1 | FOM= | 0.79 | TEST= 0 |
| INDE | 1 | 15 | 56 | FOBS= | 103.6 | SIGMA= | 1.6 | PHAS= | -35.9 | FOM= | 0.90 | TEST= 0 |
| INDE | 1 | 15 | 58 | FOBS= | 82.7 | SIGMA= | 2.0 | PHAS= | 120.2 | FOM= | 0.69 | TEST= 1 |
| INDE | 1 | 15 | 60 | FOBS= | 0.0 | SIGMA= | 18.6 | PHAS= | 0.0 | FOM= | 0.00 | TEST= 0 |
| INDE | 1 | 15 | 62 | FOBS= | 93.8 | SIGMA= | 1.8 | PHAS= | -46.7 | FOM= | 0.73 | TEST= 0 |
| INDE | 1 | 15 | 64 | FOBS= | 127.5 | SIGMA= | 2.1 | PHAS= | 2.2 | FOM= | 0.96 | TEST= 0 |
| INDE | 1 | 15 | 66 | FOBS= | 93.7 | SIGMA= | 3.3 | PHAS= | -40.9 | FOM= | 0.94 | TEST= 0 |
| INDE | 1 | 15 | 68 | FOBS= | 64.0 | SIGMA= | 4.7 | PHAS= | 40.7 | FOM= | 0.82 | TEST= 0 |
| INDE | 1 | 15 | 70 | FOBS= | 57.3 | SIGMA= | 5.2 | PHAS= | -94.7 | FOM= | 0.82 | TEST= 0 |
| INDE | 1 | 15 | 72 | FOBS= | 85.3 | SIGMA= | 3.6 | PHAS= | -177.9 | FOM= | 0.78 | TEST= 0 |
| INDE | 1 | 15 | 74 | FOBS= | 51.8 | SIGMA= | 8.6 | PHAS= | 50.4 | FOM= | 0.93 | TEST= 0 |
| INDE | 1 | 15 | 76 | FOBS= | 29.5 | SIGMA= | 10.6 | PHAS= | -129.8 | FOM= | 0.59 | TEST= 0 |
| INDE | 1 | 16 | 15 | FOBS= | 308.2 | SIGMA= | 1.3 | PHAS= | 137.5 | FOM= | 0.90 | TEST= 0 |
| INDE | 1 | 16 | 17 | FOBS= | 30.0 | SIGMA= | 3.4 | PHAS= | 38.1 | FOM= | 0.76 | TEST= 0 |
| INDE | 1 | 16 | 19 | FOBS= | 271.4 | SIGMA= | 0.7 | PHAS= | -40.9 | FOM= | 0.96 | TEST= 0 |
| INDE | 1 | 16 | 21 | FOBS= | 116.2 | SIGMA= | 0.6 | PHAS= | 42.2 | FOM= | 0.97 | TEST= 0 |
| INDE | 1 | 16 | 23 | FOBS= | 32.8 | SIGMA= | 2.1 | PHAS= | 116.6 | FOM= | 0.98 | TEST= 0 |
| INDE | 1 | 16 | 25 | FOBS= | 214.3 | SIGMA= | 0.5 | PHAS= | -88.0 | FOM= | 0.98 | TEST= 0 |
| INDE | 1 | 16 | 27 | FOBS= | 110.0 | SIGMA= | 0.7 | PHAS= | -34.9 | FOM= | 0.99 | TEST= 0 |
| INDE | 1 | 16 | 29 | FOBS= | 49.0 | SIGMA= | 1.3 | PHAS= | -175.7 | FOM= | 0.98 | TEST= 0 |

*FIG. 12A - 30*

```
INDE   1   16   31  FOBS=   147.5  SIGMA=   0.5  PHAS=  -141.5  FOM=  0.99  TEST=  0
INDE   1   16   33  FOBS=    75.7  SIGMA=   1.1  PHAS=   -48.7  FOM=  0.98  TEST=  0
INDE   1   16   35  FOBS=   356.7  SIGMA=   0.7  PHAS=    65.6  FOM=  0.97  TEST=  0
INDE   1   16   37  FOBS=   407.5  SIGMA=   0.7  PHAS=  -163.1  FOM=  0.99  TEST=  0
INDE   1   16   39  FOBS=   183.0  SIGMA=   1.0  PHAS=  -132.6  FOM=  0.94  TEST=  0
INDE   1   16   41  FOBS=   136.4  SIGMA=   1.6  PHAS=  -173.7  FOM=  0.91  TEST=  0
INDE   1   16   43  FOBS=    85.1  SIGMA=   3.0  PHAS=   143.9  FOM=  0.77  TEST=  0
INDE   1   16   45  FOBS=   187.8  SIGMA=   1.3  PHAS=   -35.3  FOM=  0.92  TEST=  0
INDE   1   16   47  FOBS=   231.8  SIGMA=   1.2  PHAS=  -122.6  FOM=  0.96  TEST=  0
INDE   1   16   49  FOBS=   140.2  SIGMA=   1.6  PHAS=    29.8  FOM=  0.81  TEST=  0
INDE   1   16   51  FOBS=   106.8  SIGMA=   2.0  PHAS=   -40.9  FOM=  0.73  TEST=  0
INDE   1   16   53  FOBS=   122.0  SIGMA=   1.7  PHAS=    48.9  FOM=  0.89  TEST=  0
INDE   1   16   55  FOBS=   131.8  SIGMA=   1.4  PHAS=    63.5  FOM=  0.94  TEST=  0
INDE   1   16   57  FOBS=    37.8  SIGMA=   4.5  PHAS=  -111.0  FOM=  0.43  TEST=  0
INDE   1   16   59  FOBS=     0.0  SIGMA=  19.7  PHAS=     0.0  FOM=  0.00  TEST=  0
INDE   1   16   61  FOBS=   166.1  SIGMA=   1.1  PHAS=  -150.0  FOM=  0.93  TEST=  0
INDE   1   16   63  FOBS=     2.9  SIGMA=  63.1  PHAS=   -45.1  FOM=  0.01  TEST=  0
INDE   1   16   65  FOBS=    77.3  SIGMA=   4.0  PHAS=   -75.5  FOM=  0.89  TEST=  0
INDE   1   16   67  FOBS=    53.2  SIGMA=   5.7  PHAS=   -95.6  FOM=  0.73  TEST=  0
INDE   1   16   69  FOBS=    80.2  SIGMA=   3.9  PHAS=   -96.4  FOM=  0.82  TEST=  0
INDE   1   16   71  FOBS=    49.1  SIGMA=   6.1  PHAS=    -2.9  FOM=  0.16  TEST=  1
INDE   1   16   73  FOBS=    32.0  SIGMA=   9.6  PHAS=   -27.1  FOM=  0.41  TEST=  0
INDE   1   16   75  FOBS=    60.2  SIGMA=   5.3  PHAS=   105.6  FOM=  0.84  TEST=  0
INDE   1   17   16  FOBS=   210.4  SIGMA=   1.5  PHAS=    81.9  FOM=  0.99  TEST=  0
INDE   1   17   18  FOBS=   238.5  SIGMA=   0.7  PHAS=  -139.3  FOM=  0.93  TEST=  0
INDE   1   17   20  FOBS=    97.9  SIGMA=   0.9  PHAS=  -136.2  FOM=  0.98  TEST=  0
INDE   1   17   22  FOBS=    54.1  SIGMA=   1.4  PHAS=    34.9  FOM=  0.99  TEST=  1
INDE   1   17   24  FOBS=   140.7  SIGMA=   0.6  PHAS=    75.2  FOM=  0.34  TEST=  1
INDE   1   17   26  FOBS=   192.9  SIGMA=   0.6  PHAS=   157.6  FOM=  0.98  TEST=  0
INDE   1   17   28  FOBS=    72.2  SIGMA=   1.0  PHAS=  -119.7  FOM=  0.96  TEST=  0
INDE   1   17   30  FOBS=   104.5  SIGMA=   0.7  PHAS=   -30.1  FOM=  0.98  TEST=  0
INDE   1   17   32  FOBS=   205.6  SIGMA=   0.7  PHAS=   108.2  FOM=  0.87  TEST=  0
INDE   1   17   34  FOBS=   394.9  SIGMA=   0.5  PHAS=    -9.3  FOM=  0.97  TEST=  0
INDE   1   17   36  FOBS=   205.4  SIGMA=   0.9  PHAS=    16.3  FOM=  0.97  TEST=  0
INDE   1   17   38  FOBS=   296.6  SIGMA=   0.7  PHAS=  -162.1  FOM=  0.92  TEST=  0
INDE   1   17   40  FOBS=   133.6  SIGMA=   1.3  PHAS=    77.1  FOM=  0.80  TEST=  0
INDE   1   17   42  FOBS=    44.2  SIGMA=   4.1  PHAS=   150.0  FOM=  0.59  TEST=  0
INDE   1   17   44  FOBS=    96.8  SIGMA=   3.3  PHAS=     8.3  FOM=  0.07  TEST=  1
INDE   1   17   46  FOBS=   185.7  SIGMA=   1.4  PHAS=     4.6  FOM=  0.89  TEST=  0
INDE   1   17   48  FOBS=   230.0  SIGMA=   1.1  PHAS=  -137.7  FOM=  0.93  TEST=  0
INDE   1   17   50  FOBS=   116.5  SIGMA=   1.9  PHAS=   -93.3  FOM=  0.84  TEST=  0
INDE   1   17   52  FOBS=    48.7  SIGMA=   4.2  PHAS=   115.6  FOM=  0.52  TEST=  0
INDE   1   17   54  FOBS=   202.9  SIGMA=   1.2  PHAS=   -42.2  FOM=  0.96  TEST=  0
INDE   1   17   56  FOBS=   121.7  SIGMA=   1.4  PHAS=   -14.9  FOM=  0.96  TEST=  0
INDE   1   17   58  FOBS=    45.6  SIGMA=   3.7  PHAS=   155.2  FOM=  0.70  TEST=  0
INDE   1   17   60  FOBS=    34.1  SIGMA=   5.6  PHAS=    20.9  FOM=  0.46  TEST=  0
INDE   1   17   62  FOBS=    72.4  SIGMA=   2.3  PHAS=    54.6  FOM=  0.29  TEST=  0
INDE   1   17   64  FOBS=   113.8  SIGMA=   2.8  PHAS=   -52.5  FOM=  0.92  TEST=  0
INDE   1   17   66  FOBS=   149.6  SIGMA=   2.2  PHAS=  -112.1  FOM=  0.95  TEST=  0
INDE   1   17   68  FOBS=     0.0  SIGMA=  24.8  PHAS=     0.0  FOM=  0.00  TEST=  0
INDE   1   17   70  FOBS=    27.7  SIGMA=  11.1  PHAS=  -138.7  FOM=  0.56  TEST=  0
INDE   1   17   72  FOBS=    38.5  SIGMA=   7.9  PHAS=   -24.1  FOM=  0.44  TEST=  0
INDE   1   17   74  FOBS=   114.4  SIGMA=   2.8  PHAS=    50.5  FOM=  0.95  TEST=  0
INDE   1   18    1  FOBS=   372.3  SIGMA=   0.4  PHAS=   -93.9  FOM=  0.98  TEST=  0
INDE   1   18    3  FOBS=   153.0  SIGMA=   0.4  PHAS=  -142.0  FOM=  0.93  TEST=  0
INDE   1   18    5  FOBS=   256.9  SIGMA=   0.5  PHAS=  -172.2  FOM=  0.96  TEST=  0
INDE   1   18   17  FOBS=   144.4  SIGMA=   1.1  PHAS=    56.0  FOM=  0.92  TEST=  0
INDE   1   18   19  FOBS=   187.3  SIGMA=   0.8  PHAS=   119.2  FOM=  0.90  TEST=  0
INDE   1   18   21  FOBS=   142.3  SIGMA=   0.8  PHAS=  -152.3  FOM=  0.98  TEST=  0
INDE   1   18   23  FOBS=    22.3  SIGMA=   3.9  PHAS=   -64.4  FOM=  0.49  TEST=  1
INDE   1   18   25  FOBS=   180.1  SIGMA=   0.6  PHAS=    11.2  FOM=  0.97  TEST=  0
INDE   1   18   27  FOBS=   182.0  SIGMA=   0.7  PHAS=     7.7  FOM=  0.96  TEST=  0
INDE   1   18   29  FOBS=   121.7  SIGMA=   0.7  PHAS=   -93.8  FOM=  0.98  TEST=  0
INDE   1   18   31  FOBS=   198.1  SIGMA=   0.8  PHAS=  -161.4  FOM=  0.91  TEST=  0
INDE   1   18   33  FOBS=   362.1  SIGMA=   0.7  PHAS=   -99.8  FOM=  0.97  TEST=  0
INDE   1   18   35  FOBS=   271.6  SIGMA=   0.5  PHAS=    95.8  FOM=  0.93  TEST=  0
INDE   1   18   37  FOBS=   174.3  SIGMA=   1.1  PHAS=   171.8  FOM=  0.12  TEST=  1
INDE   1   18   39  FOBS=   110.0  SIGMA=   1.1  PHAS=    23.5  FOM=  0.91  TEST=  1
INDE   1   18   41  FOBS=   155.9  SIGMA=   1.3  PHAS=    79.1  FOM=  0.96  TEST=  0
INDE   1   18   43  FOBS=   101.2  SIGMA=   2.0  PHAS=   -99.5  FOM=  0.95  TEST=  0
```

*FIG. 12A - 31*

| | | | | | | | | | | | |
|---|---|---|---|---|---|---|---|---|---|---|---|
| INDE | 1 | 18 | 45 | FOBS= | 177.1 | SIGMA= | 2.1 | PHAS= | -115.6 | FOM= 0.12 | TEST= 1 |
| INDE | 1 | 18 | 47 | FOBS= | 195.4 | SIGMA= | 1.3 | PHAS= | 162.4 | FOM= 0.96 | TEST= 0 |
| INDE | 1 | 18 | 49 | FOBS= | 98.6 | SIGMA= | 2.2 | PHAS= | -80.2 | FOM= 0.64 | TEST= 0 |
| INDE | 1 | 18 | 51 | FOBS= | 151.9 | SIGMA= | 1.5 | PHAS= | 121.5 | FOM= 0.90 | TEST= 0 |
| INDE | 1 | 18 | 53 | FOBS= | 54.3 | SIGMA= | 3.8 | PHAS= | -124.6 | FOM= 0.50 | TEST= 0 |
| INDE | 1 | 18 | 55 | FOBS= | 109.8 | SIGMA= | 2.0 | PHAS= | -99.2 | FOM= 0.91 | TEST= 0 |
| INDE | 1 | 18 | 57 | FOBS= | 118.3 | SIGMA= | 1.5 | PHAS= | 124.1 | FOM= 0.56 | TEST= 0 |
| INDE | 1 | 18 | 59 | FOBS= | 58.5 | SIGMA= | 2.8 | PHAS= | -6.2 | FOM= 0.78 | TEST= 0 |
| INDE | 1 | 18 | 61 | FOBS= | 157.1 | SIGMA= | 1.2 | PHAS= | -73.8 | FOM= 0.60 | TEST= 1 |
| INDE | 1 | 18 | 63 | FOBS= | 9.3 | SIGMA= | 22.8 | PHAS= | 76.0 | FOM= 0.06 | TEST= 0 |
| INDE | 1 | 18 | 65 | FOBS= | 88.1 | SIGMA= | 3.6 | PHAS= | 107.9 | FOM= 0.94 | TEST= 0 |
| INDE | 1 | 18 | 67 | FOBS= | 41.5 | SIGMA= | 7.5 | PHAS= | -139.1 | FOM= 0.52 | TEST= 0 |
| INDE | 1 | 18 | 69 | FOBS= | 87.3 | SIGMA= | 3.6 | PHAS= | 166.1 | FOM= 0.64 | TEST= 0 |
| INDE | 1 | 18 | 71 | FOBS= | 37.3 | SIGMA= | 8.4 | PHAS= | -89.0 | FOM= 0.67 | TEST= 0 |
| INDE | 1 | 18 | 73 | FOBS= | 39.7 | SIGMA= | 7.9 | PHAS= | -104.2 | FOM= 0.71 | TEST= 1 |
| INDE | 1 | 18 | 75 | FOBS= | 74.6 | SIGMA= | 4.4 | PHAS= | 10.6 | FOM= 0.90 | TEST= 0 |
| INDE | 1 | 19 | 2 | FOBS= | 235.9 | SIGMA= | 0.5 | PHAS= | -126.7 | FOM= 0.63 | TEST= 0 |
| INDE | 1 | 19 | 4 | FOBS= | 34.9 | SIGMA= | 2.1 | PHAS= | 176.3 | FOM= 0.87 | TEST= 0 |
| INDE | 1 | 19 | 6 | FOBS= | 92.4 | SIGMA= | 1.0 | PHAS= | 168.0 | FOM= 0.72 | TEST= 0 |
| INDE | 1 | 19 | 18 | FOBS= | 137.7 | SIGMA= | 1.0 | PHAS= | 44.2 | FOM= 0.97 | TEST= 0 |
| INDE | 1 | 19 | 20 | FOBS= | 203.4 | SIGMA= | 0.8 | PHAS= | 62.6 | FOM= 0.98 | TEST= 0 |
| INDE | 1 | 19 | 22 | FOBS= | 168.2 | SIGMA= | 0.7 | PHAS= | 77.2 | FOM= 0.99 | TEST= 0 |
| INDE | 1 | 19 | 24 | FOBS= | 99.1 | SIGMA= | 1.0 | PHAS= | 47.2 | FOM= 0.90 | TEST= 0 |
| INDE | 1 | 19 | 26 | FOBS= | 49.6 | SIGMA= | 1.6 | PHAS= | 77.0 | FOM= 0.97 | TEST= 0 |
| INDE | 1 | 19 | 28 | FOBS= | 192.8 | SIGMA= | 0.5 | PHAS= | -156.2 | FOM= 0.95 | TEST= 0 |
| INDE | 1 | 19 | 30 | FOBS= | 88.0 | SIGMA= | 0.9 | PHAS= | -142.8 | FOM= 0.80 | TEST= 0 |
| INDE | 1 | 19 | 32 | FOBS= | 253.9 | SIGMA= | 0.7 | PHAS= | 117.9 | FOM= 0.97 | TEST= 0 |
| INDE | 1 | 19 | 34 | FOBS= | 72.0 | SIGMA= | 1.9 | PHAS= | 73.1 | FOM= 0.88 | TEST= 1 |
| INDE | 1 | 19 | 36 | FOBS= | 263.7 | SIGMA= | 0.6 | PHAS= | 21.3 | FOM= 0.94 | TEST= 0 |
| INDE | 1 | 19 | 38 | FOBS= | 67.3 | SIGMA= | 1.4 | PHAS= | -70.9 | FOM= 0.91 | TEST= 0 |
| INDE | 1 | 19 | 40 | FOBS= | 119.2 | SIGMA= | 1.0 | PHAS= | 140.1 | FOM= 0.87 | TEST= 0 |
| INDE | 1 | 19 | 42 | FOBS= | 61.9 | SIGMA= | 3.1 | PHAS= | 164.5 | FOM= 0.89 | TEST= 0 |
| INDE | 1 | 19 | 44 | FOBS= | 79.7 | SIGMA= | 2.6 | PHAS= | -4.2 | FOM= 0.96 | TEST= 0 |
| INDE | 1 | 19 | 46 | FOBS= | 367.0 | SIGMA= | 1.2 | PHAS= | 11.9 | FOM= 0.97 | TEST= 0 |
| INDE | 1 | 19 | 48 | FOBS= | 100.7 | SIGMA= | 2.4 | PHAS= | 173.9 | FOM= 0.91 | TEST= 0 |
| INDE | 1 | 19 | 50 | FOBS= | 190.6 | SIGMA= | 1.5 | PHAS= | 49.3 | FOM= 0.94 | TEST= 0 |
| INDE | 1 | 19 | 52 | FOBS= | 68.4 | SIGMA= | 3.0 | PHAS= | -61.5 | FOM= 0.84 | TEST= 0 |
| INDE | 1 | 19 | 54 | FOBS= | 58.0 | SIGMA= | 3.8 | PHAS= | -39.3 | FOM= 0.71 | TEST= 0 |
| INDE | 1 | 19 | 56 | FOBS= | 49.5 | SIGMA= | 3.7 | PHAS= | 129.2 | FOM= 0.65 | TEST= 0 |
| INDE | 1 | 19 | 58 | FOBS= | 74.9 | SIGMA= | 2.3 | PHAS= | 125.2 | FOM= 0.79 | TEST= 0 |
| INDE | 1 | 19 | 60 | FOBS= | 42.1 | SIGMA= | 4.0 | PHAS= | 141.8 | FOM= 0.51 | TEST= 0 |
| INDE | 1 | 19 | 62 | FOBS= | 45.2 | SIGMA= | 3.7 | PHAS= | 164.6 | FOM= 0.26 | TEST= 0 |
| INDE | 1 | 19 | 64 | FOBS= | 87.1 | SIGMA= | 3.7 | PHAS= | -30.5 | FOM= 0.86 | TEST= 0 |
| INDE | 1 | 19 | 66 | FOBS= | 80.7 | SIGMA= | 4.0 | PHAS= | -122.0 | FOM= 0.91 | TEST= 0 |
| INDE | 1 | 19 | 68 | FOBS= | 96.7 | SIGMA= | 3.3 | PHAS= | 177.5 | FOM= 0.87 | TEST= 0 |
| INDE | 1 | 19 | 70 | FOBS= | 87.7 | SIGMA= | 3.7 | PHAS= | 123.7 | FOM= 0.87 | TEST= 0 |
| INDE | 1 | 19 | 72 | FOBS= | 50.2 | SIGMA= | 6.4 | PHAS= | 49.9 | FOM= 0.51 | TEST= 0 |
| INDE | 1 | 19 | 74 | FOBS= | 43.9 | SIGMA= | 7.2 | PHAS= | -130.4 | FOM= 0.73 | TEST= 0 |
| INDE | 1 | 20 | 1 | FOBS= | 66.0 | SIGMA= | 1.1 | PHAS= | 90.0 | FOM= 0.83 | TEST= 0 |
| INDE | 1 | 20 | 3 | FOBS= | 226.4 | SIGMA= | 0.5 | PHAS= | 159.1 | FOM= 0.90 | TEST= 0 |
| INDE | 1 | 20 | 5 | FOBS= | 123.6 | SIGMA= | 0.5 | PHAS= | 169.0 | FOM= 0.84 | TEST= 0 |
| INDE | 1 | 20 | 7 | FOBS= | 142.8 | SIGMA= | 0.8 | PHAS= | 175.2 | FOM= 0.66 | TEST= 0 |
| INDE | 1 | 20 | 19 | FOBS= | 118.6 | SIGMA= | 1.2 | PHAS= | -102.6 | FOM= 0.98 | TEST= 0 |
| INDE | 1 | 20 | 21 | FOBS= | 98.5 | SIGMA= | 1.0 | PHAS= | -22.5 | FOM= 0.80 | TEST= 0 |
| INDE | 1 | 20 | 23 | FOBS= | 127.4 | SIGMA= | 0.9 | PHAS= | -75.5 | FOM= 0.95 | TEST= 0 |
| INDE | 1 | 20 | 25 | FOBS= | 137.4 | SIGMA= | 0.8 | PHAS= | -31.9 | FOM= 0.96 | TEST= 0 |
| INDE | 1 | 20 | 27 | FOBS= | 272.5 | SIGMA= | 0.5 | PHAS= | 21.7 | FOM= 0.85 | TEST= 0 |
| INDE | 1 | 20 | 29 | FOBS= | 80.7 | SIGMA= | 1.1 | PHAS= | -17.1 | FOM= 0.96 | TEST= 0 |
| INDE | 1 | 20 | 31 | FOBS= | 89.6 | SIGMA= | 0.9 | PHAS= | -92.0 | FOM= 0.56 | TEST= 1 |
| INDE | 1 | 20 | 33 | FOBS= | 0.0 | SIGMA= | 15.3 | PHAS= | 0.0 | FOM= 0.00 | TEST= 0 |
| INDE | 1 | 20 | 35 | FOBS= | 71.3 | SIGMA= | 2.1 | PHAS= | 22.4 | FOM= 0.89 | TEST= 1 |
| INDE | 1 | 20 | 37 | FOBS= | 426.5 | SIGMA= | 0.5 | PHAS= | -26.4 | FOM= 0.95 | TEST= 0 |
| INDE | 1 | 20 | 39 | FOBS= | 149.6 | SIGMA= | 0.7 | PHAS= | 39.1 | FOM= 0.87 | TEST= 0 |
| INDE | 1 | 20 | 41 | FOBS= | 215.9 | SIGMA= | 0.7 | PHAS= | 113.8 | FOM= 0.95 | TEST= 0 |
| INDE | 1 | 20 | 43 | FOBS= | 227.6 | SIGMA= | 0.8 | PHAS= | -123.1 | FOM= 0.93 | TEST= 0 |
| INDE | 1 | 20 | 45 | FOBS= | 324.7 | SIGMA= | 0.9 | PHAS= | -122.6 | FOM= 0.97 | TEST= 0 |
| INDE | 1 | 20 | 47 | FOBS= | 121.1 | SIGMA= | 2.0 | PHAS= | -102.8 | FOM= 0.69 | TEST= 1 |
| INDE | 1 | 20 | 49 | FOBS= | 144.8 | SIGMA= | 1.6 | PHAS= | 4.8 | FOM= 0.93 | TEST= 0 |
| INDE | 1 | 20 | 51 | FOBS= | 75.4 | SIGMA= | 2.8 | PHAS= | -130.7 | FOM= 0.62 | TEST= 0 |
| INDE | 1 | 20 | 53 | FOBS= | 0.0 | SIGMA= | 21.1 | PHAS= | 0.0 | FOM= 0.00 | TEST= 0 |

*FIG. 12A - 32*

| | | | | | | | | | | | | |
|---|---|---|---|---|---|---|---|---|---|---|---|---|
| INDE | 1 | 20 | 55 | FOBS= | 67.9 | SIGMA= | 3.2 | PHAS= | -38.9 | FOM= | 0.49 | TEST= | 0 |
| INDE | 1 | 20 | 57 | FOBS= | 13.8 | SIGMA= | 12.3 | PHAS= | -146.1 | FOM= | 0.28 | TEST= | 0 |
| INDE | 1 | 20 | 59 | FOBS= | 117.3 | SIGMA= | 1.5 | PHAS= | 6.2 | FOM= | 0.94 | TEST= | 0 |
| INDE | 1 | 20 | 61 | FOBS= | 51.1 | SIGMA= | 3.3 | PHAS= | -67.8 | FOM= | 0.66 | TEST= | 0 |
| INDE | 1 | 20 | 63 | FOBS= | 0.0 | SIGMA= | 20.7 | PHAS= | 0.0 | FOM= | 0.00 | TEST= | 0 |
| INDE | 1 | 20 | 65 | FOBS= | 77.2 | SIGMA= | 4.2 | PHAS= | 117.1 | FOM= | 0.91 | TEST= | 0 |
| INDE | 1 | 20 | 67 | FOBS= | 83.9 | SIGMA= | 3.8 | PHAS= | 88.4 | FOM= | 0.89 | TEST= | 0 |
| INDE | 1 | 20 | 69 | FOBS= | 47.2 | SIGMA= | 6.8 | PHAS= | 47.7 | FOM= | 0.72 | TEST= | 0 |
| INDE | 1 | 20 | 71 | FOBS= | 77.8 | SIGMA= | 4.1 | PHAS= | -40.5 | FOM= | 0.88 | TEST= | 0 |
| INDE | 1 | 20 | 73 | FOBS= | 21.0 | SIGMA= | 15.5 | PHAS= | -167.3 | FOM= | 0.43 | TEST= | 0 |
| INDE | 1 | 20 | 75 | FOBS= | 29.8 | SIGMA= | 11.0 | PHAS= | 67.7 | FOM= | 0.43 | TEST= | 0 |
| INDE | 1 | 21 | 2 | FOBS= | 136.9 | SIGMA= | 0.6 | PHAS= | 1.3 | FOM= | 0.51 | TEST= | 0 |
| INDE | 1 | 21 | 4 | FOBS= | 108.2 | SIGMA= | 0.6 | PHAS= | 4.7 | FOM= | 0.92 | TEST= | 0 |
| INDE | 1 | 21 | 6 | FOBS= | 104.7 | SIGMA= | 0.9 | PHAS= | 64.3 | FOM= | 0.85 | TEST= | 0 |
| INDE | 1 | 21 | 20 | FOBS= | 245.7 | SIGMA= | 0.8 | PHAS= | 127.5 | FOM= | 0.98 | TEST= | 0 |
| INDE | 1 | 21 | 22 | FOBS= | 164.6 | SIGMA= | 0.7 | PHAS= | 121.2 | FOM= | 0.95 | TEST= | 0 |
| INDE | 1 | 21 | 24 | FOBS= | 128.0 | SIGMA= | 0.9 | PHAS= | 75.8 | FOM= | 0.94 | TEST= | 0 |
| INDE | 1 | 21 | 26 | FOBS= | 126.4 | SIGMA= | 0.9 | PHAS= | 0.1 | FOM= | 0.83 | TEST= | 0 |
| INDE | 1 | 21 | 28 | FOBS= | 235.8 | SIGMA= | 0.6 | PHAS= | -103.1 | FOM= | 0.99 | TEST= | 0 |
| INDE | 1 | 21 | 30 | FOBS= | 119.6 | SIGMA= | 0.8 | PHAS= | -143.1 | FOM= | 0.86 | TEST= | 0 |
| INDE | 1 | 21 | 32 | FOBS= | 96.9 | SIGMA= | 0.9 | PHAS= | 118.7 | FOM= | 0.98 | TEST= | 0 |
| INDE | 1 | 21 | 34 | FOBS= | 217.4 | SIGMA= | 0.7 | PHAS= | -86.7 | FOM= | 0.93 | TEST= | 0 |
| INDE | 1 | 21 | 36 | FOBS= | 163.5 | SIGMA= | 1.1 | PHAS= | -110.8 | FOM= | 0.94 | TEST= | 0 |
| INDE | 1 | 21 | 38 | FOBS= | 115.8 | SIGMA= | 1.0 | PHAS= | -85.1 | FOM= | 0.94 | TEST= | 0 |
| INDE | 1 | 21 | 40 | FOBS= | 111.1 | SIGMA= | 1.0 | PHAS= | 30.7 | FOM= | 0.82 | TEST= | 0 |
| INDE | 1 | 21 | 42 | FOBS= | 266.6 | SIGMA= | 0.7 | PHAS= | -178.9 | FOM= | 0.99 | TEST= | 0 |
| INDE | 1 | 21 | 44 | FOBS= | 91.0 | SIGMA= | 2.4 | PHAS= | 118.0 | FOM= | 0.87 | TEST= | 0 |
| INDE | 1 | 21 | 46 | FOBS= | 49.8 | SIGMA= | 4.8 | PHAS= | 2.1 | FOM= | 0.71 | TEST= | 0 |
| INDE | 1 | 21 | 48 | FOBS= | 186.4 | SIGMA= | 1.4 | PHAS= | -97.1 | FOM= | 0.96 | TEST= | 0 |
| INDE | 1 | 21 | 50 | FOBS= | 63.2 | SIGMA= | 3.4 | PHAS= | 144.1 | FOM= | 0.34 | TEST= | 0 |
| INDE | 1 | 21 | 52 | FOBS= | 66.4 | SIGMA= | 3.2 | PHAS= | -1.3 | FOM= | 0.27 | TEST= | 0 |
| INDE | 1 | 21 | 54 | FOBS= | 76.1 | SIGMA= | 3.0 | PHAS= | -7.0 | FOM= | 0.82 | TEST= | 0 |
| INDE | 1 | 21 | 56 | FOBS= | 62.4 | SIGMA= | 3.6 | PHAS= | -127.7 | FOM= | 0.81 | TEST= | 0 |
| INDE | 1 | 21 | 58 | FOBS= | 115.1 | SIGMA= | 1.5 | PHAS= | -134.3 | FOM= | 0.95 | TEST= | 0 |
| INDE | 1 | 21 | 60 | FOBS= | 25.3 | SIGMA= | 6.6 | PHAS= | -157.1 | FOM= | 0.27 | TEST= | 0 |
| INDE | 1 | 21 | 62 | FOBS= | 47.5 | SIGMA= | 4.2 | PHAS= | 54.1 | FOM= | 0.68 | TEST= | 0 |
| INDE | 1 | 21 | 64 | FOBS= | 0.0 | SIGMA= | 30.3 | PHAS= | 0.0 | FOM= | 0.00 | TEST= | 0 |
| INDE | 1 | 21 | 66 | FOBS= | 36.2 | SIGMA= | 8.8 | PHAS= | -7.9 | FOM= | 0.54 | TEST= | 0 |
| INDE | 1 | 21 | 68 | FOBS= | 77.4 | SIGMA= | 4.2 | PHAS= | -59.4 | FOM= | 0.05 | TEST= | 1 |
| INDE | 1 | 21 | 70 | FOBS= | 50.5 | SIGMA= | 6.5 | PHAS= | -130.4 | FOM= | 0.55 | TEST= | 0 |
| INDE | 1 | 21 | 72 | FOBS= | 43.0 | SIGMA= | 7.6 | PHAS= | 94.6 | FOM= | 0.72 | TEST= | 0 |
| INDE | 1 | 21 | 74 | FOBS= | 27.3 | SIGMA= | 12.1 | PHAS= | -94.3 | FOM= | 0.42 | TEST= | 0 |
| INDE | 1 | 22 | 1 | FOBS= | 127.5 | SIGMA= | 0.7 | PHAS= | -13.8 | FOM= | 0.82 | TEST= | 0 |
| INDE | 1 | 22 | 3 | FOBS= | 233.0 | SIGMA= | 0.5 | PHAS= | 156.0 | FOM= | 0.92 | TEST= | 0 |
| INDE | 1 | 22 | 5 | FOBS= | 218.4 | SIGMA= | 0.5 | PHAS= | -95.8 | FOM= | 0.92 | TEST= | 0 |
| INDE | 1 | 22 | 7 | FOBS= | 331.8 | SIGMA= | 0.6 | PHAS= | 113.4 | FOM= | 0.95 | TEST= | 0 |
| INDE | 1 | 22 | 21 | FOBS= | 232.5 | SIGMA= | 0.8 | PHAS= | 24.4 | FOM= | 0.98 | TEST= | 0 |
| INDE | 1 | 22 | 23 | FOBS= | 300.7 | SIGMA= | 0.8 | PHAS= | 45.8 | FOM= | 0.97 | TEST= | 0 |
| INDE | 1 | 22 | 25 | FOBS= | 207.0 | SIGMA= | 0.8 | PHAS= | -38.3 | FOM= | 0.96 | TEST= | 0 |
| INDE | 1 | 22 | 27 | FOBS= | 182.7 | SIGMA= | 0.7 | PHAS= | 44.1 | FOM= | 0.98 | TEST= | 0 |
| INDE | 1 | 22 | 29 | FOBS= | 221.7 | SIGMA= | 0.7 | PHAS= | -25.0 | FOM= | 0.98 | TEST= | 0 |
| INDE | 1 | 22 | 31 | FOBS= | 118.3 | SIGMA= | 0.8 | PHAS= | 121.9 | FOM= | 0.95 | TEST= | 1 |
| INDE | 1 | 22 | 33 | FOBS= | 234.2 | SIGMA= | 0.5 | PHAS= | 121.3 | FOM= | 0.94 | TEST= | 0 |
| INDE | 1 | 22 | 35 | FOBS= | 75.4 | SIGMA= | 1.3 | PHAS= | 123.6 | FOM= | 0.88 | TEST= | 0 |
| INDE | 1 | 22 | 37 | FOBS= | 44.2 | SIGMA= | 2.4 | PHAS= | 62.0 | FOM= | 0.70 | TEST= | 0 |
| INDE | 1 | 22 | 39 | FOBS= | 166.3 | SIGMA= | 0.7 | PHAS= | -85.1 | FOM= | 0.97 | TEST= | 0 |
| INDE | 1 | 22 | 41 | FOBS= | 78.9 | SIGMA= | 2.0 | PHAS= | 133.1 | FOM= | 0.78 | TEST= | 0 |
| INDE | 1 | 22 | 43 | FOBS= | 65.8 | SIGMA= | 2.4 | PHAS= | -51.6 | FOM= | 0.94 | TEST= | 0 |
| INDE | 1 | 22 | 45 | FOBS= | 0.0 | SIGMA= | 20.2 | PHAS= | 0.0 | FOM= | 0.00 | TEST= | 0 |
| INDE | 1 | 22 | 47 | FOBS= | 125.9 | SIGMA= | 1.9 | PHAS= | -156.7 | FOM= | 0.95 | TEST= | 0 |
| INDE | 1 | 22 | 49 | FOBS= | 76.6 | SIGMA= | 2.4 | PHAS= | -177.3 | FOM= | 0.83 | TEST= | 1 |
| INDE | 1 | 22 | 51 | FOBS= | 117.1 | SIGMA= | 1.8 | PHAS= | -60.8 | FOM= | 0.92 | TEST= | 0 |
| INDE | 1 | 22 | 53 | FOBS= | 80.6 | SIGMA= | 2.7 | PHAS= | -33.6 | FOM= | 0.65 | TEST= | 0 |
| INDE | 1 | 22 | 55 | FOBS= | 0.0 | SIGMA= | 22.6 | PHAS= | 0.0 | FOM= | 0.00 | TEST= | 0 |
| INDE | 1 | 22 | 57 | FOBS= | 99.9 | SIGMA= | 2.1 | PHAS= | 116.8 | FOM= | 0.92 | TEST= | 0 |
| INDE | 1 | 22 | 59 | FOBS= | 80.9 | SIGMA= | 2.1 | PHAS= | 45.4 | FOM= | 0.90 | TEST= | 0 |
| INDE | 1 | 22 | 61 | FOBS= | 90.4 | SIGMA= | 1.9 | PHAS= | 30.0 | FOM= | 0.93 | TEST= | 0 |
| INDE | 1 | 22 | 63 | FOBS= | 110.8 | SIGMA= | 2.0 | PHAS= | 3.9 | FOM= | 0.93 | TEST= | 0 |
| INDE | 1 | 22 | 65 | FOBS= | 50.5 | SIGMA= | 6.5 | PHAS= | 6.0 | FOM= | 0.57 | TEST= | 1 |
| INDE | 1 | 22 | 67 | FOBS= | 38.8 | SIGMA= | 8.4 | PHAS= | -152.6 | FOM= | 0.35 | TEST= | 0 |

*FIG. 12A - 33*

```
INDE  1  22  69  FOBS=   49.6  SIGMA=   6.6  PHAS=    65.7  FOM=  0.57  TEST= 0
INDE  1  22  71  FOBS=    0.0  SIGMA=  25.6  PHAS=     0.0  FOM=  0.00  TEST= 0
INDE  1  22  73  FOBS=   18.7  SIGMA=  17.8  PHAS=    18.3  FOM=  0.46  TEST= 0
INDE  1  23   2  FOBS=   86.5  SIGMA=   0.7  PHAS=   173.7  FOM=  0.41  TEST= 0
INDE  1  23   4  FOBS=   34.1  SIGMA=   1.6  PHAS=   132.4  FOM=  0.96  TEST= 0
INDE  1  23   6  FOBS=  180.1  SIGMA=   0.5  PHAS=    47.1  FOM=  0.83  TEST= 0
INDE  1  23   8  FOBS=  196.0  SIGMA=   0.7  PHAS=  -101.9  FOM=  0.97  TEST= 0
INDE  1  23  22  FOBS=  137.3  SIGMA=   1.0  PHAS=   -18.6  FOM=  0.89  TEST= 0
INDE  1  23  24  FOBS=  165.1  SIGMA=   0.8  PHAS=   -51.9  FOM=  0.80  TEST= 0
INDE  1  23  26  FOBS=  151.9  SIGMA=   0.9  PHAS=   -89.4  FOM=  0.96  TEST= 0
INDE  1  23  28  FOBS=  308.4  SIGMA=   0.7  PHAS=   -56.2  FOM=  0.97  TEST= 0
INDE  1  23  30  FOBS=  104.0  SIGMA=   1.2  PHAS=  -102.8  FOM=  0.96  TEST= 0
INDE  1  23  32  FOBS=  127.6  SIGMA=   1.0  PHAS=  -154.9  FOM=  0.92  TEST= 0
INDE  1  23  34  FOBS=  203.9  SIGMA=   0.6  PHAS=   -24.8  FOM=  0.97  TEST= 0
INDE  1  23  36  FOBS=  159.0  SIGMA=   0.7  PHAS=   -13.3  FOM=  0.96  TEST= 0
INDE  1  23  38  FOBS=   85.9  SIGMA=   1.3  PHAS=   126.1  FOM=  0.76  TEST= 0
INDE  1  23  40  FOBS=  205.4  SIGMA=   0.7  PHAS=   174.5  FOM=  0.97  TEST= 0
INDE  1  23  42  FOBS=  254.8  SIGMA=   0.7  PHAS=  -155.1  FOM=  0.70  TEST= 1
INDE  1  23  44  FOBS=  113.3  SIGMA=   1.5  PHAS=   -21.2  FOM=  0.90  TEST= 0
INDE  1  23  46  FOBS=  185.7  SIGMA=   1.0  PHAS=   105.9  FOM=  0.96  TEST= 0
INDE  1  23  48  FOBS=   81.3  SIGMA=   2.9  PHAS=   173.3  FOM=  0.39  TEST= 0
INDE  1  23  50  FOBS=  243.3  SIGMA=   0.9  PHAS=   166.0  FOM=  0.95  TEST= 0
INDE  1  23  52  FOBS=   98.0  SIGMA=   1.9  PHAS=    27.5  FOM=  0.37  TEST= 1
INDE  1  23  54  FOBS=   27.7  SIGMA=   9.1  PHAS=     2.8  FOM=  0.17  TEST= 0
INDE  1  23  56  FOBS=   19.6  SIGMA=  12.3  PHAS=  -111.1  FOM=  0.14  TEST= 0
INDE  1  23  58  FOBS=   72.4  SIGMA=   2.4  PHAS=   -59.6  FOM=  0.90  TEST= 0
INDE  1  23  60  FOBS=   94.8  SIGMA=   1.8  PHAS=    -4.7  FOM=  0.91  TEST= 0
INDE  1  23  62  FOBS=   74.5  SIGMA=   3.0  PHAS=   -29.9  FOM=  0.90  TEST= 0
INDE  1  23  64  FOBS=   87.5  SIGMA=   2.6  PHAS=   -64.7  FOM=  0.91  TEST= 0
INDE  1  23  66  FOBS=   65.4  SIGMA=   5.1  PHAS=     9.5  FOM=  0.05  TEST= 1
INDE  1  23  68  FOBS=   26.3  SIGMA=  12.4  PHAS=  -105.9  FOM=  0.27  TEST= 0
INDE  1  23  70  FOBS=   49.5  SIGMA=   6.7  PHAS=   164.2  FOM=  0.34  TEST= 0
INDE  1  23  72  FOBS=   41.0  SIGMA=   8.2  PHAS=    14.0  FOM=  0.29  TEST= 1
INDE  1  23  74  FOBS=   52.9  SIGMA=   6.6  PHAS=   -82.8  FOM=  0.64  TEST= 0
INDE  1  24   1  FOBS=  144.7  SIGMA=   0.5  PHAS=    70.3  FOM=  0.64  TEST= 0
INDE  1  24   3  FOBS=  171.4  SIGMA=   0.6  PHAS=   134.6  FOM=  0.72  TEST= 0
INDE  1  24   5  FOBS=  206.9  SIGMA=   0.4  PHAS=  -172.7  FOM=  0.94  TEST= 0
INDE  1  24   7  FOBS=  256.8  SIGMA=   0.6  PHAS=   153.6  FOM=  0.95  TEST= 0
INDE  1  24  23  FOBS=  198.1  SIGMA=   0.8  PHAS=    44.3  FOM=  0.96  TEST= 0
INDE  1  24  25  FOBS=   91.5  SIGMA=   1.3  PHAS=   165.4  FOM=  0.98  TEST= 0
INDE  1  24  27  FOBS=  129.0  SIGMA=   1.0  PHAS=  -116.0  FOM=  0.82  TEST= 0
INDE  1  24  29  FOBS=  194.8  SIGMA=   0.8  PHAS=   -70.0  FOM=  0.88  TEST= 0
INDE  1  24  31  FOBS=  411.3  SIGMA=   0.6  PHAS=   164.5  FOM=  0.99  TEST= 0
INDE  1  24  33  FOBS=  231.5  SIGMA=   0.6  PHAS=   118.8  FOM=  0.90  TEST= 0
INDE  1  24  35  FOBS=  236.2  SIGMA=   0.6  PHAS=   -99.6  FOM=  0.95  TEST= 0
INDE  1  24  37  FOBS=   88.4  SIGMA=   1.3  PHAS=   130.1  FOM=  0.56  TEST= 0
INDE  1  24  39  FOBS=  182.7  SIGMA=   0.7  PHAS=    59.3  FOM=  0.98  TEST= 0
INDE  1  24  41  FOBS=  202.7  SIGMA=   0.8  PHAS=    79.2  FOM=  0.96  TEST= 0
INDE  1  24  43  FOBS=  123.2  SIGMA=   1.8  PHAS=   -52.7  FOM=  0.78  TEST= 0
INDE  1  24  45  FOBS=  213.2  SIGMA=   0.7  PHAS=    -4.9  FOM=  0.91  TEST= 0
INDE  1  24  47  FOBS=  167.4  SIGMA=   1.2  PHAS=    49.8  FOM=  0.92  TEST= 0
INDE  1  24  49  FOBS=  141.7  SIGMA=   1.6  PHAS=    38.8  FOM=  0.92  TEST= 0
INDE  1  24  51  FOBS=  159.4  SIGMA=   1.2  PHAS=    17.1  FOM=  0.93  TEST= 0
INDE  1  24  53  FOBS=   56.9  SIGMA=   3.0  PHAS=   -65.8  FOM=  0.72  TEST= 0
INDE  1  24  55  FOBS=   48.0  SIGMA=   4.7  PHAS=    27.7  FOM=  0.54  TEST= 0
INDE  1  24  57  FOBS=   41.4  SIGMA=   5.0  PHAS=   156.0  FOM=  0.70  TEST= 0
INDE  1  24  59  FOBS=   18.6  SIGMA=   9.3  PHAS=   -89.4  FOM=  0.31  TEST= 0
INDE  1  24  61  FOBS=  103.2  SIGMA=   2.1  PHAS=   -53.0  FOM=  0.92  TEST= 0
INDE  1  24  63  FOBS=   20.6  SIGMA=  10.8  PHAS=     0.1  FOM=  0.50  TEST= 0
INDE  1  24  65  FOBS=   28.8  SIGMA=  11.7  PHAS=   -99.7  FOM=  0.57  TEST= 0
INDE  1  24  67  FOBS=   28.6  SIGMA=  11.6  PHAS=  -159.6  FOM=  0.61  TEST= 0
INDE  1  24  69  FOBS=   12.4  SIGMA=  26.7  PHAS=   -94.1  FOM=  0.08  TEST= 0
INDE  1  24  71  FOBS=   47.6  SIGMA=   7.1  PHAS=   -21.9  FOM=  0.85  TEST= 0
INDE  1  24  73  FOBS=   60.8  SIGMA=   5.7  PHAS=   -44.7  FOM=  0.05  TEST= 1
INDE  1  25   2  FOBS=  130.1  SIGMA=   0.6  PHAS=   -91.5  FOM=  0.59  TEST= 0
INDE  1  25   4  FOBS=  128.3  SIGMA=   0.7  PHAS=    96.1  FOM=  0.88  TEST= 0
INDE  1  25   6  FOBS=  258.3  SIGMA=   0.6  PHAS=    89.6  FOM=  0.99  TEST= 0
INDE  1  25   8  FOBS=   99.9  SIGMA=   1.1  PHAS=    -2.8  FOM=  0.96  TEST= 0
INDE  1  25  22  FOBS=  258.3  SIGMA=   1.8  PHAS=   -53.3  FOM=  0.94  TEST= 0
INDE  1  25  24  FOBS=  239.2  SIGMA=   0.8  PHAS=   -24.5  FOM=  0.99  TEST= 0
```

*FIG. 12A - 34*

```
INDE  1  25  26 FOBS=    86.8 SIGMA=   1.5 PHAS=   -90.4 FOM=  0.94 TEST= 0
INDE  1  25  28 FOBS=   295.8 SIGMA=   0.7 PHAS=  -155.5 FOM=  0.95 TEST= 0
INDE  1  25  30 FOBS=   404.4 SIGMA=   0.7 PHAS=   -12.2 FOM=  0.97 TEST= 0
INDE  1  25  32 FOBS=   219.2 SIGMA=   0.8 PHAS=    18.7 FOM=  0.98 TEST= 1
INDE  1  25  34 FOBS=   138.5 SIGMA=   1.0 PHAS=    28.9 FOM=  0.88 TEST= 0
INDE  1  25  36 FOBS=   279.0 SIGMA=   0.5 PHAS=    -7.9 FOM=  0.98 TEST= 0
INDE  1  25  38 FOBS=   153.5 SIGMA=   0.9 PHAS=    59.4 FOM=  0.97 TEST= 0
INDE  1  25  40 FOBS=   139.0 SIGMA=   1.0 PHAS=   -72.1 FOM=  0.68 TEST= 0
INDE  1  25  42 FOBS=    39.8 SIGMA=   3.8 PHAS=   -88.9 FOM=  0.87 TEST= 0
INDE  1  25  44 FOBS=   183.8 SIGMA=   0.9 PHAS=    48.7 FOM=  0.38 TEST= 0
INDE  1  25  46 FOBS=    53.0 SIGMA=   2.5 PHAS=  -134.6 FOM=  0.88 TEST= 0
INDE  1  25  48 FOBS=   117.4 SIGMA=   1.7 PHAS=   -72.0 FOM=  0.96 TEST= 0
INDE  1  25  50 FOBS=    91.0 SIGMA=   2.0 PHAS=   -44.8 FOM=  0.84 TEST= 0
INDE  1  25  52 FOBS=    17.8 SIGMA=  10.4 PHAS=  -179.8 FOM=  0.08 TEST= 1
INDE  1  25  54 FOBS=     0.0 SIGMA=  19.2 PHAS=     0.0 FOM=  0.00 TEST= 0
INDE  1  25  56 FOBS=   102.5 SIGMA=   2.3 PHAS=    49.4 FOM=  0.79 TEST= 0
INDE  1  25  58 FOBS=    64.9 SIGMA=   3.2 PHAS=   108.3 FOM=  0.09 TEST= 1
INDE  1  25  60 FOBS=    35.6 SIGMA=   4.9 PHAS=   -19.2 FOM=  0.26 TEST= 0
INDE  1  25  62 FOBS=     5.5 SIGMA=  41.0 PHAS=  -123.7 FOM=  0.00 TEST= 1
INDE  1  25  64 FOBS=    93.5 SIGMA=   2.5 PHAS=  -146.2 FOM=  0.91 TEST= 0
INDE  1  25  66 FOBS=    53.9 SIGMA=   6.4 PHAS=    34.9 FOM=  0.30 TEST= 0
INDE  1  25  68 FOBS=    36.1 SIGMA=   9.3 PHAS=   140.6 FOM=  0.42 TEST= 0
INDE  1  25  70 FOBS=     0.0 SIGMA=  26.0 PHAS=     0.0 FOM=  0.00 TEST= 0
INDE  1  25  72 FOBS=    36.1 SIGMA=   9.6 PHAS=   150.1 FOM=  0.54 TEST= 0
INDE  1  26   1 FOBS=   165.2 SIGMA=   0.5 PHAS=   124.4 FOM=  0.98 TEST= 0
INDE  1  26   3 FOBS=   158.1 SIGMA=   0.7 PHAS=    29.4 FOM=  0.51 TEST= 1
INDE  1  26   5 FOBS=    65.7 SIGMA=   1.0 PHAS=    52.0 FOM=  0.98 TEST= 0
INDE  1  26   7 FOBS=   148.4 SIGMA=   0.6 PHAS=   -98.4 FOM=  0.96 TEST= 0
INDE  1  26   9 FOBS=   110.8 SIGMA=   1.1 PHAS=   -87.8 FOM=  0.97 TEST= 0
INDE  1  26  23 FOBS=   187.1 SIGMA=   1.5 PHAS=   170.9 FOM=  0.85 TEST= 0
INDE  1  26  25 FOBS=   220.0 SIGMA=   0.7 PHAS=   142.5 FOM=  0.96 TEST= 0
INDE  1  26  27 FOBS=   232.2 SIGMA=   0.8 PHAS=   117.0 FOM=  0.98 TEST= 0
INDE  1  26  29 FOBS=   198.1 SIGMA=   1.0 PHAS=   -88.7 FOM=  0.94 TEST= 0
INDE  1  26  31 FOBS=    43.6 SIGMA=   3.3 PHAS=   -75.3 FOM=  0.11 TEST= 0
INDE  1  26  33 FOBS=   203.1 SIGMA=   0.7 PHAS=     6.9 FOM=  0.97 TEST= 0
INDE  1  26  35 FOBS=   263.6 SIGMA=   0.8 PHAS=   -83.8 FOM=  0.98 TEST= 0
INDE  1  26  37 FOBS=   277.9 SIGMA=   0.6 PHAS=  -110.0 FOM=  0.95 TEST= 0
INDE  1  26  39 FOBS=   266.4 SIGMA=   0.6 PHAS=    62.1 FOM=  0.93 TEST= 0
INDE  1  26  41 FOBS=   280.6 SIGMA=   0.6 PHAS=  -124.7 FOM=  0.88 TEST= 0
INDE  1  26  43 FOBS=   112.0 SIGMA=   1.3 PHAS=   107.0 FOM=  0.65 TEST= 0
INDE  1  26  45 FOBS=   247.1 SIGMA=   0.6 PHAS=   116.9 FOM=  0.96 TEST= 0
INDE  1  26  47 FOBS=   161.8 SIGMA=   0.9 PHAS=   103.7 FOM=  0.96 TEST= 0
INDE  1  26  49 FOBS=    93.8 SIGMA=   1.7 PHAS=   -45.6 FOM=  0.96 TEST= 0
INDE  1  26  51 FOBS=    92.8 SIGMA=   1.8 PHAS=    51.1 FOM=  0.89 TEST= 0
INDE  1  26  53 FOBS=    99.2 SIGMA=   1.7 PHAS=    81.5 FOM=  0.68 TEST= 0
INDE  1  26  55 FOBS=   137.9 SIGMA=   1.4 PHAS=  -106.6 FOM=  0.92 TEST= 0
INDE  1  26  57 FOBS=    30.9 SIGMA=   6.8 PHAS=    79.8 FOM=  0.47 TEST= 0
INDE  1  26  59 FOBS=    78.4 SIGMA=   2.5 PHAS=    11.1 FOM=  0.91 TEST= 0
INDE  1  26  61 FOBS=   105.4 SIGMA=   2.3 PHAS=     6.4 FOM=  0.86 TEST= 0
INDE  1  26  63 FOBS=    39.4 SIGMA=   8.1 PHAS=   -79.7 FOM=  0.04 TEST= 0
INDE  1  26  65 FOBS=    39.1 SIGMA=   8.7 PHAS=    97.4 FOM=  0.32 TEST= 0
INDE  1  26  67 FOBS=    31.3 SIGMA=  11.0 PHAS=  -142.9 FOM=  0.73 TEST= 0
INDE  1  26  69 FOBS=    32.5 SIGMA=  10.6 PHAS=  -107.2 FOM=  0.36 TEST= 0
INDE  1  26  71 FOBS=    25.5 SIGMA=  13.7 PHAS=    22.1 FOM=  0.46 TEST= 0
INDE  1  26  73 FOBS=    39.9 SIGMA=   8.9 PHAS=   -73.6 FOM=  0.10 TEST= 0
INDE  1  27   2 FOBS=    78.5 SIGMA=   0.9 PHAS=   -71.4 FOM=  0.98 TEST= 0
INDE  1  27   6 FOBS=   108.3 SIGMA=   0.7 PHAS=  -170.6 FOM=  0.66 TEST= 0
INDE  1  27   8 FOBS=   212.9 SIGMA=   0.5 PHAS=   147.7 FOM=  0.96 TEST= 0
INDE  1  27  10 FOBS=   180.4 SIGMA=   0.8 PHAS=    63.4 FOM=  0.91 TEST= 1
INDE  1  27  24 FOBS=   249.1 SIGMA=   0.9 PHAS=    54.7 FOM=  0.95 TEST= 0
INDE  1  27  26 FOBS=   212.1 SIGMA=   0.8 PHAS=    36.7 FOM=  0.96 TEST= 0
INDE  1  27  28 FOBS=   167.7 SIGMA=   1.0 PHAS=    96.4 FOM=  0.89 TEST= 0
INDE  1  27  30 FOBS=   176.1 SIGMA=   1.0 PHAS=    43.5 FOM=  0.94 TEST= 0
INDE  1  27  32 FOBS=   169.8 SIGMA=   1.0 PHAS=  -107.4 FOM=  0.91 TEST= 0
INDE  1  27  34 FOBS=   166.4 SIGMA=   0.9 PHAS=     7.7 FOM=  0.96 TEST= 0
INDE  1  27  36 FOBS=   135.5 SIGMA=   1.1 PHAS=  -148.7 FOM=  0.95 TEST= 0
INDE  1  27  38 FOBS=    41.3 SIGMA=   4.0 PHAS=   101.9 FOM=  0.92 TEST= 0
INDE  1  27  40 FOBS=   131.4 SIGMA=   1.1 PHAS=   162.8 FOM=  0.84 TEST= 0
INDE  1  27  42 FOBS=   160.6 SIGMA=   0.9 PHAS=    53.2 FOM=  0.84 TEST= 0
INDE  1  27  44 FOBS=   195.6 SIGMA=   0.8 PHAS=    86.9 FOM=  0.87 TEST= 0
```

*FIG. 12A - 35*

```
INDE  1  27  46 FOBS=   67.3 SIGMA=  2.0 PHAS=   29.0 FOM= 0.95 TEST= 0
INDE  1  27  48 FOBS=  156.6 SIGMA=  1.0 PHAS=  -64.0 FOM= 0.88 TEST= 0
INDE  1  27  50 FOBS=  167.6 SIGMA=  1.0 PHAS=  -58.4 FOM= 0.69 TEST= 1
INDE  1  27  52 FOBS=   93.7 SIGMA=  1.7 PHAS=  -95.5 FOM= 0.91 TEST= 0
INDE  1  27  54 FOBS=   61.6 SIGMA=  2.9 PHAS= -134.2 FOM= 0.17 TEST= 0
INDE  1  27  56 FOBS=   17.4 SIGMA= 13.8 PHAS=  147.0 FOM= 0.27 TEST= 0
INDE  1  27  58 FOBS=   91.6 SIGMA=  1.9 PHAS= -132.0 FOM= 0.77 TEST= 0
INDE  1  27  60 FOBS=   36.1 SIGMA=  6.6 PHAS=    6.3 FOM= 0.66 TEST= 0
INDE  1  27  62 FOBS=   20.0 SIGMA= 16.4 PHAS=   31.0 FOM= 0.17 TEST= 0
INDE  1  27  64 FOBS=   66.6 SIGMA=  3.5 PHAS= -163.6 FOM= 0.59 TEST= 0
INDE  1  27  66 FOBS=    0.0 SIGMA= 26.3 PHAS=    0.0 FOM= 0.00 TEST= 0
INDE  1  27  68 FOBS=   98.2 SIGMA=  3.7 PHAS=  119.0 FOM= 0.91 TEST= 0
INDE  1  27  70 FOBS=    0.0 SIGMA= 26.5 PHAS=    0.0 FOM= 0.00 TEST= 0
INDE  1  27  72 FOBS=    0.0 SIGMA= 26.7 PHAS=    0.0 FOM= 0.00 TEST= 0
INDE  1  28   1 FOBS=  192.1 SIGMA=  0.5 PHAS=  138.9 FOM= 0.98 TEST= 0
INDE  1  28   3 FOBS=  178.0 SIGMA=  0.7 PHAS=  -95.4 FOM= 0.97 TEST= 0
INDE  1  28   5 FOBS=  102.0 SIGMA=  1.0 PHAS=  -12.7 FOM= 0.86 TEST= 0
INDE  1  28   7 FOBS=  157.8 SIGMA=  0.6 PHAS=   64.7 FOM= 0.80 TEST= 0
INDE  1  28   9 FOBS=  140.3 SIGMA=  1.0 PHAS=   47.6 FOM= 0.99 TEST= 0
INDE  1  28  25 FOBS=  236.0 SIGMA=  0.8 PHAS=   33.2 FOM= 0.95 TEST= 1
INDE  1  28  27 FOBS=  198.4 SIGMA=  0.9 PHAS=  -43.6 FOM= 0.97 TEST= 0
INDE  1  28  29 FOBS=  182.4 SIGMA=  1.1 PHAS=  -21.6 FOM= 0.61 TEST= 0
INDE  1  28  31 FOBS=  113.1 SIGMA=  1.5 PHAS=  102.7 FOM= 0.96 TEST= 0
INDE  1  28  33 FOBS=  196.2 SIGMA=  0.9 PHAS=  -82.4 FOM= 0.94 TEST= 0
INDE  1  28  35 FOBS=   90.3 SIGMA=  1.6 PHAS=  -67.0 FOM= 0.92 TEST= 0
INDE  1  28  37 FOBS=  152.0 SIGMA=  1.1 PHAS=  171.0 FOM= 0.98 TEST= 0
INDE  1  28  39 FOBS=  102.8 SIGMA=  1.6 PHAS=   81.3 FOM= 0.94 TEST= 0
INDE  1  28  41 FOBS=    0.0 SIGMA= 17.6 PHAS=    0.0 FOM= 0.00 TEST= 0
INDE  1  28  43 FOBS=  118.9 SIGMA=  1.2 PHAS=  112.7 FOM= 0.51 TEST= 0
INDE  1  28  45 FOBS=   61.8 SIGMA=  2.2 PHAS= -133.2 FOM= 0.89 TEST= 0
INDE  1  28  47 FOBS=   43.7 SIGMA=  3.4 PHAS=  100.4 FOM= 0.24 TEST= 0
INDE  1  28  49 FOBS=  105.4 SIGMA=  1.3 PHAS= -102.5 FOM= 0.92 TEST= 0
INDE  1  28  51 FOBS=   63.9 SIGMA=  2.5 PHAS=   67.5 FOM= 0.93 TEST= 0
INDE  1  28  53 FOBS=   79.7 SIGMA=  2.0 PHAS=  113.2 FOM= 0.76 TEST= 0
INDE  1  28  55 FOBS=   26.3 SIGMA=  7.4 PHAS= -108.8 FOM= 0.44 TEST= 0
INDE  1  28  57 FOBS=    0.0 SIGMA= 19.8 PHAS=    0.0 FOM= 0.00 TEST= 0
INDE  1  28  59 FOBS=   56.6 SIGMA=  3.7 PHAS=   24.3 FOM= 0.80 TEST= 0
INDE  1  28  61 FOBS=    0.0 SIGMA= 21.6 PHAS=    0.0 FOM= 0.00 TEST= 0
INDE  1  28  63 FOBS=   24.7 SIGMA=  9.4 PHAS=  164.3 FOM= 0.16 TEST= 0
INDE  1  28  65 FOBS=   46.5 SIGMA=  7.5 PHAS=   -6.4 FOM= 0.39 TEST= 0
INDE  1  28  67 FOBS=   72.9 SIGMA=  4.9 PHAS=  -35.7 FOM= 0.75 TEST= 0
INDE  1  28  69 FOBS=    0.0 SIGMA= 26.6 PHAS=    0.0 FOM= 0.00 TEST= 0
INDE  1  28  71 FOBS=    0.0 SIGMA= 26.7 PHAS=    0.0 FOM= 0.00 TEST= 1
INDE  1  29   2 FOBS=  140.1 SIGMA=  0.6 PHAS=   83.9 FOM= 0.91 TEST= 0
INDE  1  29   6 FOBS=  157.8 SIGMA=  0.6 PHAS=  -86.8 FOM= 0.96 TEST= 0
INDE  1  29   8 FOBS=   86.2 SIGMA=  0.9 PHAS=   -0.6 FOM= 0.97 TEST= 0
INDE  1  29  10 FOBS=   74.3 SIGMA=  1.7 PHAS=  168.7 FOM= 0.99 TEST= 0
INDE  1  29  26 FOBS=  130.4 SIGMA=  1.2 PHAS=  -45.0 FOM= 0.95 TEST= 0
INDE  1  29  28 FOBS=   30.9 SIGMA=  5.3 PHAS=   84.3 FOM= 0.71 TEST= 0
INDE  1  29  30 FOBS=   61.9 SIGMA=  2.7 PHAS=   73.2 FOM= 0.77 TEST= 0
INDE  1  29  32 FOBS=  111.6 SIGMA=  1.6 PHAS= -115.5 FOM= 0.85 TEST= 0
INDE  1  29  34 FOBS=   42.3 SIGMA=  3.6 PHAS=   25.0 FOM= 0.59 TEST= 0
INDE  1  29  36 FOBS=  125.0 SIGMA=  1.3 PHAS= -170.1 FOM= 0.96 TEST= 0
INDE  1  29  38 FOBS=   98.6 SIGMA=  1.7 PHAS=  117.2 FOM= 0.95 TEST= 0
INDE  1  29  40 FOBS=   48.2 SIGMA=  3.4 PHAS=  -32.5 FOM= 0.82 TEST= 0
INDE  1  29  42 FOBS=   79.5 SIGMA=  2.0 PHAS=  -10.1 FOM= 0.72 TEST= 0
INDE  1  29  44 FOBS=  146.3 SIGMA=  1.0 PHAS=   89.2 FOM= 0.89 TEST= 0
INDE  1  29  46 FOBS=   95.6 SIGMA=  1.5 PHAS=  167.2 FOM= 0.88 TEST= 0
INDE  1  29  48 FOBS=   92.4 SIGMA=  1.6 PHAS=   43.9 FOM= 0.34 TEST= 0
INDE  1  29  50 FOBS=  123.3 SIGMA=  1.1 PHAS= -172.9 FOM= 0.96 TEST= 0
INDE  1  29  52 FOBS=  147.3 SIGMA=  1.1 PHAS=  -22.0 FOM= 0.81 TEST= 0
INDE  1  29  54 FOBS=    0.0 SIGMA= 18.5 PHAS=    0.0 FOM= 0.00 TEST= 0
INDE  1  29  56 FOBS=   78.0 SIGMA=  2.4 PHAS= -137.2 FOM= 0.88 TEST= 0
INDE  1  29  58 FOBS=  114.1 SIGMA=  1.7 PHAS= -178.3 FOM= 0.85 TEST= 0
INDE  1  29  60 FOBS=   50.4 SIGMA=  3.7 PHAS=  -76.9 FOM= 0.74 TEST= 1
INDE  1  29  62 FOBS=   15.6 SIGMA= 15.0 PHAS=   91.8 FOM= 0.11 TEST= 0
INDE  1  29  64 FOBS=   38.6 SIGMA=  6.1 PHAS=  142.6 FOM= 0.34 TEST= 0
INDE  1  29  66 FOBS=   45.7 SIGMA=  7.8 PHAS= -169.3 FOM= 0.80 TEST= 0
INDE  1  29  68 FOBS=  112.4 SIGMA=  3.3 PHAS=  152.8 FOM= 0.95 TEST= 0
INDE  1  29  70 FOBS=   52.6 SIGMA=  6.9 PHAS=   -5.0 FOM= 0.61 TEST= 0
```

*FIG. 12A - 36*

```
INDE  1  29  72 FOBS=   16.6 SIGMA= 22.0 PHAS=  130.7 FOM= 0.28 TEST= 0
INDE  1  30   1 FOBS=  179.3 SIGMA=  0.5 PHAS=  -81.5 FOM= 0.80 TEST= 0
INDE  1  30   3 FOBS=   96.1 SIGMA=  1.1 PHAS=  -56.1 FOM= 0.91 TEST= 0
INDE  1  30   7 FOBS=   23.4 SIGMA=  3.1 PHAS=  117.9 FOM= 0.73 TEST= 0
INDE  1  30   9 FOBS=  139.8 SIGMA=  0.7 PHAS=  100.9 FOM= 0.85 TEST= 0
INDE  1  30  11 FOBS=  123.2 SIGMA=  1.2 PHAS=  111.2 FOM= 0.97 TEST= 0
INDE  1  30  25 FOBS=   70.7 SIGMA=  4.3 PHAS= -158.5 FOM= 0.29 TEST= 0
INDE  1  30  27 FOBS=  103.2 SIGMA=  1.5 PHAS=  -51.5 FOM= 0.86 TEST= 0
INDE  1  30  29 FOBS=  152.5 SIGMA=  1.2 PHAS=  164.6 FOM= 0.94 TEST= 1
INDE  1  30  31 FOBS=  132.2 SIGMA=  1.4 PHAS=   95.6 FOM= 0.90 TEST= 0
INDE  1  30  33 FOBS=  133.0 SIGMA=  1.3 PHAS=  -77.3 FOM= 0.73 TEST= 0
INDE  1  30  35 FOBS=  166.5 SIGMA=  1.0 PHAS=  104.6 FOM= 0.93 TEST= 0
INDE  1  30  37 FOBS=  259.5 SIGMA=  0.8 PHAS=  110.7 FOM= 0.93 TEST= 0
INDE  1  30  39 FOBS=  103.2 SIGMA=  1.7 PHAS=  -92.9 FOM= 0.87 TEST= 0
INDE  1  30  41 FOBS=   50.6 SIGMA=  3.2 PHAS=  103.0 FOM= 0.72 TEST= 0
INDE  1  30  43 FOBS=  113.9 SIGMA=  1.4 PHAS= -121.7 FOM= 0.28 TEST= 0
INDE  1  30  45 FOBS=  120.8 SIGMA=  1.3 PHAS=  128.7 FOM= 0.93 TEST= 0
INDE  1  30  47 FOBS=  139.3 SIGMA=  1.1 PHAS=  135.5 FOM= 0.90 TEST= 0
INDE  1  30  49 FOBS=   68.8 SIGMA=  2.0 PHAS=  140.8 FOM= 0.94 TEST= 1
INDE  1  30  51 FOBS=   29.5 SIGMA=  4.7 PHAS=   48.6 FOM= 0.81 TEST= 0
INDE  1  30  53 FOBS=   59.5 SIGMA=  2.3 PHAS= -131.3 FOM= 0.45 TEST= 0
INDE  1  30  55 FOBS=  114.6 SIGMA=  1.5 PHAS=  121.9 FOM= 0.89 TEST= 0
INDE  1  30  57 FOBS=   73.0 SIGMA=  2.4 PHAS=   56.3 FOM= 0.91 TEST= 0
INDE  1  30  59 FOBS=   52.0 SIGMA=  4.3 PHAS=  105.8 FOM= 0.30 TEST= 0
INDE  1  30  61 FOBS=   43.3 SIGMA=  4.1 PHAS=  128.3 FOM= 0.41 TEST= 0
INDE  1  30  63 FOBS=   50.1 SIGMA=  4.8 PHAS=   -0.8 FOM= 0.67 TEST= 0
INDE  1  30  65 FOBS=   13.7 SIGMA= 26.1 PHAS=  178.4 FOM= 0.27 TEST= 0
INDE  1  30  67 FOBS=  111.4 SIGMA=  3.4 PHAS=   37.2 FOM= 0.93 TEST= 0
INDE  1  30  69 FOBS=   66.5 SIGMA=  5.5 PHAS=   83.8 FOM= 0.89 TEST= 0
INDE  1  30  71 FOBS=   17.1 SIGMA= 21.7 PHAS=  -38.1 FOM= 0.12 TEST= 0
INDE  1  31   2 FOBS=   97.8 SIGMA=  0.8 PHAS= -104.4 FOM= 0.88 TEST= 0
INDE  1  31   6 FOBS=  260.0 SIGMA=  0.6 PHAS=   11.0 FOM= 0.86 TEST= 0
INDE  1  31   8 FOBS=  194.6 SIGMA=  0.6 PHAS=   34.2 FOM= 0.95 TEST= 0
INDE  1  31  10 FOBS=  114.9 SIGMA=  0.8 PHAS= -130.2 FOM= 0.82 TEST= 0
INDE  1  31  12 FOBS=  188.7 SIGMA=  0.9 PHAS=  -92.9 FOM= 0.80 TEST= 0
INDE  1  31  26 FOBS=  258.5 SIGMA=  1.6 PHAS=  -67.1 FOM= 0.54 TEST= 0
INDE  1  31  28 FOBS=  131.8 SIGMA=  1.3 PHAS=   17.6 FOM= 0.96 TEST= 0
INDE  1  31  30 FOBS=  189.2 SIGMA=  1.1 PHAS=   47.3 FOM= 0.91 TEST= 1
INDE  1  31  32 FOBS=  167.9 SIGMA=  1.2 PHAS=  172.3 FOM= 0.92 TEST= 0
INDE  1  31  34 FOBS=  274.4 SIGMA=  0.8 PHAS=   28.8 FOM= 0.96 TEST= 0
INDE  1  31  36 FOBS=  196.1 SIGMA=  1.0 PHAS=  -17.3 FOM= 0.96 TEST= 0
INDE  1  31  38 FOBS=   71.3 SIGMA=  2.5 PHAS=   60.2 FOM= 0.94 TEST= 0
INDE  1  31  40 FOBS=  217.2 SIGMA=  1.0 PHAS=   58.2 FOM= 0.92 TEST= 0
INDE  1  31  42 FOBS=  196.3 SIGMA=  0.9 PHAS=  -25.2 FOM= 0.82 TEST= 1
INDE  1  31  44 FOBS=   59.2 SIGMA=  2.7 PHAS=   31.7 FOM= 0.85 TEST= 0
INDE  1  31  46 FOBS=   70.1 SIGMA=  2.2 PHAS=   43.2 FOM= 0.89 TEST= 0
INDE  1  31  48 FOBS=   27.4 SIGMA=  5.4 PHAS=  107.5 FOM= 0.34 TEST= 0
INDE  1  31  50 FOBS=    0.0 SIGMA= 16.9 PHAS=    0.0 FOM= 0.00 TEST= 0
INDE  1  31  52 FOBS=  103.5 SIGMA=  1.3 PHAS=    5.7 FOM= 0.89 TEST= 0
INDE  1  31  54 FOBS=  101.2 SIGMA=  1.4 PHAS=  126.6 FOM= 0.91 TEST= 0
INDE  1  31  56 FOBS=  100.8 SIGMA=  1.7 PHAS=  -50.0 FOM= 0.91 TEST= 0
INDE  1  31  58 FOBS=   46.6 SIGMA=  4.9 PHAS=  -61.4 FOM= 0.34 TEST= 0
INDE  1  31  60 FOBS=   66.6 SIGMA=  3.4 PHAS=  -60.5 FOM= 0.23 TEST= 1
INDE  1  31  62 FOBS=    0.0 SIGMA= 19.3 PHAS=    0.0 FOM= 0.00 TEST= 0
INDE  1  31  64 FOBS=   24.8 SIGMA=  9.7 PHAS= -144.0 FOM= 0.05 TEST= 0
INDE  1  31  66 FOBS=    0.0 SIGMA= 26.9 PHAS=    0.0 FOM= 0.00 TEST= 0
INDE  1  31  68 FOBS=   79.9 SIGMA=  4.7 PHAS=   36.1 FOM= 0.91 TEST= 0
INDE  1  31  70 FOBS=   31.4 SIGMA= 11.8 PHAS=   -1.3 FOM= 0.56 TEST= 0
INDE  1  32   1 FOBS=   93.0 SIGMA=  0.7 PHAS=  -55.3 FOM= 0.99 TEST= 0
INDE  1  32   3 FOBS=  200.4 SIGMA=  0.7 PHAS=  144.7 FOM= 0.99 TEST= 0
INDE  1  32   7 FOBS=  157.9 SIGMA=  0.7 PHAS=  -42.2 FOM= 0.94 TEST= 0
INDE  1  32   9 FOBS=  183.9 SIGMA=  0.6 PHAS= -125.2 FOM= 0.88 TEST= 0
INDE  1  32  11 FOBS=  136.2 SIGMA=  1.2 PHAS= -173.2 FOM= 0.95 TEST= 0
INDE  1  32  27 FOBS=  217.9 SIGMA=  1.1 PHAS=  123.3 FOM= 0.91 TEST= 0
INDE  1  32  29 FOBS=  118.0 SIGMA=  1.6 PHAS= -119.6 FOM= 0.78 TEST= 0
INDE  1  32  31 FOBS=  166.1 SIGMA=  1.2 PHAS=   65.3 FOM= 0.92 TEST= 0
INDE  1  32  33 FOBS=  225.2 SIGMA=  1.1 PHAS=  -56.5 FOM= 0.95 TEST= 0
INDE  1  32  35 FOBS=  111.7 SIGMA=  1.6 PHAS=   95.4 FOM= 0.48 TEST= 1
INDE  1  32  37 FOBS=  134.7 SIGMA=  1.4 PHAS=  134.3 FOM= 0.90 TEST= 0
INDE  1  32  39 FOBS=  259.8 SIGMA=  0.8 PHAS=  -76.1 FOM= 0.99 TEST= 0
```

*FIG. 12A - 37*

```
INDE  1  32  41  FOBS=    0.0  SIGMA=  19.1  PHAS=    0.0  FOM=  0.00  TEST=  0
INDE  1  32  43  FOBS=  149.9  SIGMA=   1.2  PHAS= -124.2  FOM=  0.95  TEST=  0
INDE  1  32  45  FOBS=   90.4  SIGMA=   1.8  PHAS=  138.4  FOM=  0.66  TEST=  0
INDE  1  32  47  FOBS=  175.3  SIGMA=   1.0  PHAS= -129.4  FOM=  0.96  TEST=  0
INDE  1  32  49  FOBS=   32.1  SIGMA=   4.9  PHAS=  -79.9  FOM=  0.37  TEST=  0
INDE  1  32  51  FOBS=   88.5  SIGMA=   1.6  PHAS= -103.5  FOM=  0.81  TEST=  0
INDE  1  32  53  FOBS=   55.9  SIGMA=   2.2  PHAS=   -4.5  FOM=  0.51  TEST=  0
INDE  1  32  55  FOBS=   98.2  SIGMA=   1.8  PHAS= -121.3  FOM=  0.91  TEST=  0
INDE  1  32  57  FOBS=   91.8  SIGMA=   2.2  PHAS= -125.1  FOM=  0.87  TEST=  0
INDE  1  32  59  FOBS=   95.8  SIGMA=   2.4  PHAS=   99.5  FOM=  0.76  TEST=  0
INDE  1  32  61  FOBS=   42.2  SIGMA=   4.2  PHAS=  135.1  FOM=  0.29  TEST=  1
INDE  1  32  63  FOBS=   23.1  SIGMA=   8.7  PHAS=  -17.4  FOM=  0.42  TEST=  0
INDE  1  32  65  FOBS=   64.1  SIGMA=   4.1  PHAS=  -96.2  FOM=  0.82  TEST=  0
INDE  1  32  67  FOBS=  102.9  SIGMA=   3.8  PHAS=  -22.1  FOM=  0.92  TEST=  0
INDE  1  32  69  FOBS=    0.0  SIGMA=  27.2  PHAS=    0.0  FOM=  0.00  TEST=  0
INDE  1  33   2  FOBS=   99.9  SIGMA=   1.1  PHAS=    0.0  FOM=  0.98  TEST=  0
INDE  1  33   6  FOBS=  125.0  SIGMA=   1.0  PHAS=   98.1  FOM=  0.99  TEST=  0
INDE  1  33   8  FOBS=  234.4  SIGMA=   0.6  PHAS=  114.5  FOM=  0.95  TEST=  0
INDE  1  33  10  FOBS=  149.3  SIGMA=   0.7  PHAS= -157.1  FOM=  0.95  TEST=  0
INDE  1  33  12  FOBS=  150.6  SIGMA=   1.1  PHAS=  -46.7  FOM=  0.94  TEST=  1
INDE  1  33  26  FOBS=  248.4  SIGMA=   1.7  PHAS=   44.8  FOM=  0.85  TEST=  0
INDE  1  33  28  FOBS=  106.6  SIGMA=   1.9  PHAS=   10.8  FOM=  0.86  TEST=  0
INDE  1  33  30  FOBS=  125.3  SIGMA=   1.6  PHAS=  -36.6  FOM=  0.67  TEST=  1
INDE  1  33  32  FOBS=  253.5  SIGMA=   1.0  PHAS= -170.0  FOM=  0.97  TEST=  0
INDE  1  33  34  FOBS=   59.0  SIGMA=   3.3  PHAS=  -43.1  FOM=  0.92  TEST=  0
INDE  1  33  36  FOBS=   51.7  SIGMA=   3.7  PHAS= -113.3  FOM=  0.89  TEST=  0
INDE  1  33  38  FOBS=  196.7  SIGMA=   1.0  PHAS=   99.4  FOM=  0.97  TEST=  0
INDE  1  33  40  FOBS=  151.3  SIGMA=   1.2  PHAS=  120.3  FOM=  0.93  TEST=  0
INDE  1  33  42  FOBS=   82.5  SIGMA=   2.0  PHAS= -129.0  FOM=  0.87  TEST=  0
INDE  1  33  44  FOBS=   45.3  SIGMA=   3.6  PHAS= -164.5  FOM=  0.52  TEST=  0
INDE  1  33  46  FOBS=   99.2  SIGMA=   1.6  PHAS=  106.2  FOM=  0.76  TEST=  1
INDE  1  33  48  FOBS=  204.5  SIGMA=   0.9  PHAS= -157.7  FOM=  0.97  TEST=  0
INDE  1  33  50  FOBS=   42.1  SIGMA=   3.9  PHAS=   26.0  FOM=  0.48  TEST=  0
INDE  1  33  52  FOBS=   46.7  SIGMA=   3.2  PHAS=   46.0  FOM=  0.72  TEST=  0
INDE  1  33  54  FOBS=  117.3  SIGMA=   1.3  PHAS=  128.2  FOM=  0.07  TEST=  1
INDE  1  33  56  FOBS=  116.1  SIGMA=   1.9  PHAS=  121.8  FOM=  0.86  TEST=  0
INDE  1  33  58  FOBS=    0.0  SIGMA=  20.3  PHAS=    0.0  FOM=  0.00  TEST=  0
INDE  1  33  60  FOBS=   34.1  SIGMA=   6.6  PHAS= -172.1  FOM=  0.01  TEST=  1
INDE  1  33  62  FOBS=   31.2  SIGMA=   7.1  PHAS=  -51.2  FOM=  0.43  TEST=  0
INDE  1  33  64  FOBS=    0.0  SIGMA=  20.4  PHAS=    0.0  FOM=  0.00  TEST=  1
INDE  1  33  66  FOBS=   87.6  SIGMA=   2.8  PHAS=  -54.1  FOM=  0.75  TEST=  0
INDE  1  33  68  FOBS=    0.0  SIGMA=  27.6  PHAS=    0.0  FOM=  0.00  TEST=  0
INDE  1  33  70  FOBS=   17.6  SIGMA=  21.7  PHAS=  -36.7  FOM=  0.13  TEST=  0
INDE  1  34   1  FOBS=  109.5  SIGMA=   0.7  PHAS=  -76.7  FOM=  0.71  TEST=  0
INDE  1  34   3  FOBS=  109.5  SIGMA=   1.2  PHAS=  115.4  FOM=  0.83  TEST=  0
INDE  1  34   7  FOBS=  156.0  SIGMA=   0.6  PHAS=   57.5  FOM=  0.98  TEST=  0
INDE  1  34   9  FOBS=  147.8  SIGMA=   0.7  PHAS=  -24.7  FOM=  0.95  TEST=  0
INDE  1  34  11  FOBS=  129.8  SIGMA=   0.9  PHAS=  178.7  FOM=  0.99  TEST=  0
INDE  1  34  13  FOBS=   28.8  SIGMA=   5.4  PHAS=  170.5  FOM=  0.58  TEST=  0
INDE  1  34  27  FOBS=  118.6  SIGMA=   2.3  PHAS=  -96.7  FOM=  0.68  TEST=  0
INDE  1  34  29  FOBS=  301.5  SIGMA=   0.8  PHAS=  -27.1  FOM=  0.89  TEST=  0
INDE  1  34  31  FOBS=  147.2  SIGMA=   1.5  PHAS=   94.6  FOM=  0.95  TEST=  0
INDE  1  34  33  FOBS=   88.5  SIGMA=   2.5  PHAS=  117.4  FOM=  0.94  TEST=  0
INDE  1  34  35  FOBS=  221.0  SIGMA=   0.9  PHAS= -156.8  FOM=  0.41  TEST=  1
INDE  1  34  37  FOBS=  109.6  SIGMA=   1.7  PHAS=   83.0  FOM=  0.96  TEST=  0
INDE  1  34  39  FOBS=  196.6  SIGMA=   1.0  PHAS=  -27.3  FOM=  0.94  TEST=  0
INDE  1  34  41  FOBS=  109.0  SIGMA=   1.6  PHAS=  113.2  FOM=  0.66  TEST=  1
INDE  1  34  43  FOBS=  147.9  SIGMA=   1.2  PHAS=  171.6  FOM=  0.92  TEST=  0
INDE  1  34  45  FOBS=  151.2  SIGMA=   1.1  PHAS= -179.3  FOM=  0.93  TEST=  0
INDE  1  34  47  FOBS=  142.7  SIGMA=   1.2  PHAS=  153.8  FOM=  0.92  TEST=  0
INDE  1  34  49  FOBS=   81.5  SIGMA=   2.0  PHAS=  -39.9  FOM=  0.88  TEST=  1
INDE  1  34  51  FOBS=   28.7  SIGMA=   5.6  PHAS=  -80.7  FOM=  0.28  TEST=  0
INDE  1  34  53  FOBS=   38.2  SIGMA=   3.9  PHAS= -126.1  FOM=  0.54  TEST=  0
INDE  1  34  55  FOBS=   45.0  SIGMA=   3.4  PHAS= -119.2  FOM=  0.71  TEST=  0
INDE  1  34  57  FOBS=   62.4  SIGMA=   3.2  PHAS=  -97.4  FOM=  0.79  TEST=  0
INDE  1  34  59  FOBS=    0.0  SIGMA=  19.6  PHAS=    0.0  FOM=  0.00  TEST=  0
INDE  1  34  61  FOBS=   14.2  SIGMA=  12.4  PHAS=  -71.7  FOM=  0.36  TEST=  0
INDE  1  34  63  FOBS=   36.4  SIGMA=   6.2  PHAS=    8.7  FOM=  0.03  TEST=  0
INDE  1  34  65  FOBS=   35.6  SIGMA=   5.1  PHAS= -166.5  FOM=  0.50  TEST=  0
INDE  1  34  67  FOBS=   94.3  SIGMA=   2.4  PHAS= -152.8  FOM=  0.91  TEST=  0
```

*FIG. 12A - 38*

```
INDE  1  34  69 FOBS=   15.2 SIGMA=  25.4 PHAS=  152.3 FOM= 0.06 TEST= 0
INDE  1  35   2 FOBS=   81.8 SIGMA=   1.5 PHAS=   58.8 FOM= 0.98 TEST= 0
INDE  1  35   8 FOBS=   58.8 SIGMA=   1.6 PHAS=   10.7 FOM= 0.90 TEST= 0
INDE  1  35  10 FOBS=   73.5 SIGMA=   1.4 PHAS= -148.1 FOM= 0.99 TEST= 0
INDE  1  35  12 FOBS=  107.7 SIGMA=   1.1 PHAS=  124.1 FOM= 0.99 TEST= 0
INDE  1  35  14 FOBS=   20.4 SIGMA=   8.0 PHAS=  175.7 FOM= 0.45 TEST= 0
INDE  1  35  28 FOBS=  362.3 SIGMA=   1.1 PHAS=   68.3 FOM= 0.87 TEST= 0
INDE  1  35  30 FOBS=  182.8 SIGMA=   1.2 PHAS=   46.3 FOM= 0.15 TEST= 0
INDE  1  35  32 FOBS=  240.5 SIGMA=   1.1 PHAS=  141.3 FOM= 0.92 TEST= 1
INDE  1  35  34 FOBS=  120.6 SIGMA=   1.8 PHAS=   28.8 FOM= 0.71 TEST= 0
INDE  1  35  36 FOBS=   90.9 SIGMA=   2.1 PHAS=  -26.7 FOM= 0.76 TEST= 1
INDE  1  35  38 FOBS=  139.1 SIGMA=   1.3 PHAS=  -80.8 FOM= 0.95 TEST= 0
INDE  1  35  40 FOBS=  139.8 SIGMA=   1.3 PHAS= -156.2 FOM= 0.88 TEST= 0
INDE  1  35  42 FOBS=  180.0 SIGMA=   1.0 PHAS=   81.1 FOM= 0.92 TEST= 0
INDE  1  35  44 FOBS=  149.9 SIGMA=   1.2 PHAS=  111.4 FOM= 0.96 TEST= 0
INDE  1  35  46 FOBS=  128.2 SIGMA=   1.3 PHAS=   29.3 FOM= 0.85 TEST= 0
INDE  1  35  48 FOBS=   88.2 SIGMA=   1.9 PHAS=  161.7 FOM= 0.95 TEST= 0
INDE  1  35  50 FOBS=   29.4 SIGMA=   6.3 PHAS=   -9.6 FOM= 0.32 TEST= 0
INDE  1  35  52 FOBS=    0.0 SIGMA=  18.5 PHAS=    0.0 FOM= 0.00 TEST= 0
INDE  1  35  54 FOBS=   42.9 SIGMA=   4.7 PHAS=  171.3 FOM= 0.67 TEST= 0
INDE  1  35  56 FOBS=   74.3 SIGMA=   2.4 PHAS=   81.2 FOM= 0.75 TEST= 0
INDE  1  35  58 FOBS=    0.0 SIGMA=  22.2 PHAS=    0.0 FOM= 0.00 TEST= 1
INDE  1  35  60 FOBS=   50.9 SIGMA=   3.8 PHAS=  -50.8 FOM= 0.82 TEST= 0
INDE  1  35  62 FOBS=   22.0 SIGMA=   8.7 PHAS= -169.6 FOM= 0.59 TEST= 0
INDE  1  35  64 FOBS=   13.9 SIGMA=  14.9 PHAS=   36.7 FOM= 0.08 TEST= 0
INDE  1  35  66 FOBS=   32.2 SIGMA=   7.3 PHAS=   25.9 FOM= 0.73 TEST= 0
INDE  1  35  68 FOBS=   69.5 SIGMA=   3.9 PHAS=  113.5 FOM= 0.53 TEST= 0
INDE  1  36   1 FOBS=   33.8 SIGMA=   2.0 PHAS=  156.4 FOM= 0.86 TEST= 0
INDE  1  36   3 FOBS=  202.5 SIGMA=   0.8 PHAS=   24.6 FOM= 0.94 TEST= 0
INDE  1  36   7 FOBS=  136.6 SIGMA=   1.0 PHAS= -119.8 FOM= 0.99 TEST= 0
INDE  1  36   9 FOBS=  194.4 SIGMA=   0.6 PHAS=  -66.1 FOM= 0.95 TEST= 1
INDE  1  36  11 FOBS=   37.0 SIGMA=   2.9 PHAS=   68.3 FOM= 0.99 TEST= 0
INDE  1  36  13 FOBS=   70.1 SIGMA=   2.5 PHAS=  149.9 FOM= 0.08 TEST= 1
INDE  1  36  27 FOBS=  272.9 SIGMA=   1.9 PHAS= -139.8 FOM= 0.94 TEST= 0
INDE  1  36  29 FOBS=  262.0 SIGMA=   1.4 PHAS= -175.9 FOM= 0.86 TEST= 0
INDE  1  36  31 FOBS=  177.4 SIGMA=   1.4 PHAS=  135.4 FOM= 0.93 TEST= 0
INDE  1  36  33 FOBS=  170.1 SIGMA=   1.5 PHAS=   79.1 FOM= 0.98 TEST= 0
INDE  1  36  35 FOBS=  229.2 SIGMA=   0.9 PHAS=  168.6 FOM= 0.95 TEST= 0
INDE  1  36  37 FOBS=  157.1 SIGMA=   1.2 PHAS= -171.1 FOM= 0.98 TEST= 0
INDE  1  36  39 FOBS=  140.6 SIGMA=   1.3 PHAS=  168.7 FOM= 0.92 TEST= 0
INDE  1  36  41 FOBS=   54.9 SIGMA=   3.1 PHAS=  -81.4 FOM= 0.70 TEST= 0
INDE  1  36  43 FOBS=  100.5 SIGMA=   1.7 PHAS=   23.6 FOM= 0.84 TEST= 0
INDE  1  36  45 FOBS=   77.6 SIGMA=   2.1 PHAS= -159.7 FOM= 0.95 TEST= 0
INDE  1  36  47 FOBS=    0.0 SIGMA=  18.6 PHAS=    0.0 FOM= 0.00 TEST= 0
INDE  1  36  49 FOBS=   54.1 SIGMA=   3.1 PHAS=   99.7 FOM= 0.70 TEST= 1
INDE  1  36  51 FOBS=   27.1 SIGMA=   5.8 PHAS=  -73.3 FOM= 0.47 TEST= 0
INDE  1  36  53 FOBS=   17.8 SIGMA=  15.4 PHAS=   10.7 FOM= 0.31 TEST= 0
INDE  1  36  55 FOBS=    0.0 SIGMA=  19.6 PHAS=    0.0 FOM= 0.00 TEST= 0
INDE  1  36  57 FOBS=    9.2 SIGMA=  21.7 PHAS=    6.4 FOM= 0.16 TEST= 0
INDE  1  36  59 FOBS=   51.1 SIGMA=   3.9 PHAS= -122.3 FOM= 0.72 TEST= 0
INDE  1  36  61 FOBS=   59.1 SIGMA=   3.1 PHAS= -132.6 FOM= 0.79 TEST= 0
INDE  1  36  63 FOBS=   84.5 SIGMA=   2.2 PHAS=  -22.6 FOM= 0.12 TEST= 1
INDE  1  36  65 FOBS=   39.7 SIGMA=   5.3 PHAS=  -36.0 FOM= 0.75 TEST= 0
INDE  1  36  67 FOBS=   52.3 SIGMA=   4.7 PHAS= -104.1 FOM= 0.83 TEST= 0
INDE  1  37   2 FOBS=  149.5 SIGMA=   1.0 PHAS=  -24.2 FOM= 0.96 TEST= 0
INDE  1  37   8 FOBS=   98.2 SIGMA=   1.1 PHAS=  135.1 FOM= 0.94 TEST= 0
INDE  1  37  10 FOBS=  119.3 SIGMA=   1.0 PHAS=  124.3 FOM= 0.98 TEST= 0
INDE  1  37  12 FOBS=  270.5 SIGMA=   0.6 PHAS=  112.2 FOM= 0.94 TEST= 0
INDE  1  37  14 FOBS=  176.2 SIGMA=   1.2 PHAS= -143.8 FOM= 0.91 TEST= 0
INDE  1  37  28 FOBS=  373.7 SIGMA=   1.2 PHAS= -110.4 FOM= 0.96 TEST= 0
INDE  1  37  30 FOBS=   73.8 SIGMA=   4.0 PHAS=  122.4 FOM= 0.27 TEST= 0
INDE  1  37  32 FOBS=  217.8 SIGMA=   1.2 PHAS=  135.8 FOM= 0.69 TEST= 1
INDE  1  37  34 FOBS=  166.8 SIGMA=   1.5 PHAS=   13.9 FOM= 0.92 TEST= 0
INDE  1  37  36 FOBS=  177.2 SIGMA=   1.1 PHAS=  135.7 FOM= 0.97 TEST= 0
INDE  1  37  38 FOBS=  131.6 SIGMA=   1.4 PHAS=   44.7 FOM= 0.36 TEST= 1
INDE  1  37  40 FOBS=  166.0 SIGMA=   1.1 PHAS= -170.5 FOM= 0.93 TEST= 0
INDE  1  37  42 FOBS=   73.7 SIGMA=   2.3 PHAS=   93.3 FOM= 0.85 TEST= 0
INDE  1  37  44 FOBS=   85.3 SIGMA=   2.0 PHAS=  -18.8 FOM= 0.63 TEST= 0
INDE  1  37  46 FOBS=  105.8 SIGMA=   1.6 PHAS=  -38.9 FOM= 0.80 TEST= 0
INDE  1  37  48 FOBS=   68.7 SIGMA=   2.4 PHAS=   45.7 FOM= 0.87 TEST= 0
```

*FIG. 12A - 39*

| | | | | | | | | | | | | |
|---|---|---|---|---|---|---|---|---|---|---|---|---|
| INDE | 1 | 37 | 50 | FOBS= | 42.5 | SIGMA= | 3.8 | PHAS= | 32.6 | FOM= | 0.50 | TEST= 0 |
| INDE | 1 | 37 | 52 | FOBS= | 0.0 | SIGMA= | 19.8 | PHAS= | 0.0 | FOM= | 0.00 | TEST= 0 |
| INDE | 1 | 37 | 54 | FOBS= | 0.0 | SIGMA= | 18.7 | PHAS= | 0.0 | FOM= | 0.00 | TEST= 1 |
| INDE | 1 | 37 | 56 | FOBS= | 56.6 | SIGMA= | 3.2 | PHAS= | -146.9 | FOM= | 0.32 | TEST= 0 |
| INDE | 1 | 37 | 58 | FOBS= | 54.5 | SIGMA= | 3.3 | PHAS= | -161.7 | FOM= | 0.82 | TEST= 0 |
| INDE | 1 | 37 | 60 | FOBS= | 84.8 | SIGMA= | 2.4 | PHAS= | -170.9 | FOM= | 0.90 | TEST= 0 |
| INDE | 1 | 37 | 62 | FOBS= | 46.0 | SIGMA= | 3.6 | PHAS= | 151.6 | FOM= | 0.65 | TEST= 0 |
| INDE | 1 | 37 | 64 | FOBS= | 48.7 | SIGMA= | 3.8 | PHAS= | 103.2 | FOM= | 0.79 | TEST= 0 |
| INDE | 1 | 37 | 66 | FOBS= | 0.0 | SIGMA= | 20.9 | PHAS= | 0.0 | FOM= | 0.00 | TEST= 0 |
| INDE | 1 | 37 | 68 | FOBS= | 23.7 | SIGMA= | 16.9 | PHAS= | -119.2 | FOM= | 0.34 | TEST= 0 |
| INDE | 1 | 38 | 1 | FOBS= | 201.4 | SIGMA= | 0.4 | PHAS= | -179.1 | FOM= | 0.95 | TEST= 0 |
| INDE | 1 | 38 | 3 | FOBS= | 325.9 | SIGMA= | 0.6 | PHAS= | -69.4 | FOM= | 0.98 | TEST= 0 |
| INDE | 1 | 38 | 9 | FOBS= | 193.9 | SIGMA= | 0.7 | PHAS= | 173.7 | FOM= | 0.86 | TEST= 0 |
| INDE | 1 | 38 | 11 | FOBS= | 356.4 | SIGMA= | 0.7 | PHAS= | 29.8 | FOM= | 0.97 | TEST= 0 |
| INDE | 1 | 38 | 13 | FOBS= | 146.0 | SIGMA= | 0.9 | PHAS= | 122.8 | FOM= | 0.61 | TEST= 0 |
| INDE | 1 | 38 | 15 | FOBS= | 121.6 | SIGMA= | 1.7 | PHAS= | 100.5 | FOM= | 0.95 | TEST= 1 |
| INDE | 1 | 38 | 27 | FOBS= | 298.4 | SIGMA= | 1.9 | PHAS= | -166.9 | FOM= | 0.84 | TEST= 0 |
| INDE | 1 | 38 | 29 | FOBS= | 236.6 | SIGMA= | 1.6 | PHAS= | 140.9 | FOM= | 0.48 | TEST= 1 |
| INDE | 1 | 38 | 31 | FOBS= | 134.2 | SIGMA= | 1.9 | PHAS= | -111.1 | FOM= | 0.70 | TEST= 0 |
| INDE | 1 | 38 | 33 | FOBS= | 146.9 | SIGMA= | 1.6 | PHAS= | -110.1 | FOM= | 0.66 | TEST= 0 |
| INDE | 1 | 38 | 35 | FOBS= | 308.5 | SIGMA= | 0.9 | PHAS= | 154.4 | FOM= | 0.92 | TEST= 0 |
| INDE | 1 | 38 | 37 | FOBS= | 142.9 | SIGMA= | 1.4 | PHAS= | 96.5 | FOM= | 0.92 | TEST= 0 |
| INDE | 1 | 38 | 39 | FOBS= | 91.6 | SIGMA= | 2.0 | PHAS= | 113.5 | FOM= | 0.88 | TEST= 0 |
| INDE | 1 | 38 | 41 | FOBS= | 94.0 | SIGMA= | 1.9 | PHAS= | 152.6 | FOM= | 0.34 | TEST= 1 |
| INDE | 1 | 38 | 43 | FOBS= | 0.0 | SIGMA= | 18.2 | PHAS= | 0.0 | FOM= | 0.00 | TEST= 0 |
| INDE | 1 | 38 | 45 | FOBS= | 49.6 | SIGMA= | 3.3 | PHAS= | -158.8 | FOM= | 0.84 | TEST= 1 |
| INDE | 1 | 38 | 47 | FOBS= | 152.0 | SIGMA= | 1.1 | PHAS= | -72.8 | FOM= | 0.96 | TEST= 0 |
| INDE | 1 | 38 | 49 | FOBS= | 29.6 | SIGMA= | 5.5 | PHAS= | 138.6 | FOM= | 0.23 | TEST= 0 |
| INDE | 1 | 38 | 51 | FOBS= | 24.2 | SIGMA= | 6.6 | PHAS= | 76.2 | FOM= | 0.48 | TEST= 0 |
| INDE | 1 | 38 | 53 | FOBS= | 59.3 | SIGMA= | 3.2 | PHAS= | 37.8 | FOM= | 0.64 | TEST= 0 |
| INDE | 1 | 38 | 55 | FOBS= | 29.5 | SIGMA= | 5.7 | PHAS= | 6.0 | FOM= | 0.27 | TEST= 0 |
| INDE | 1 | 38 | 57 | FOBS= | 43.8 | SIGMA= | 4.7 | PHAS= | 57.5 | FOM= | 0.54 | TEST= 0 |
| INDE | 1 | 38 | 59 | FOBS= | 103.1 | SIGMA= | 2.0 | PHAS= | 120.5 | FOM= | 0.95 | TEST= 0 |
| INDE | 1 | 38 | 61 | FOBS= | 39.5 | SIGMA= | 4.8 | PHAS= | 81.6 | FOM= | 0.80 | TEST= 0 |
| INDE | 1 | 38 | 63 | FOBS= | 44.2 | SIGMA= | 4.2 | PHAS= | -124.9 | FOM= | 0.69 | TEST= 0 |
| INDE | 1 | 38 | 65 | FOBS= | 68.6 | SIGMA= | 2.7 | PHAS= | 36.4 | FOM= | 0.89 | TEST= 0 |
| INDE | 1 | 38 | 67 | FOBS= | 68.4 | SIGMA= | 6.0 | PHAS= | -123.7 | FOM= | 0.46 | TEST= 0 |
| INDE | 1 | 39 | 2 | FOBS= | 140.4 | SIGMA= | 1.1 | PHAS= | -154.3 | FOM= | 0.92 | TEST= 1 |
| INDE | 1 | 39 | 8 | FOBS= | 279.3 | SIGMA= | 0.7 | PHAS= | 70.7 | FOM= | 0.94 | TEST= 0 |
| INDE | 1 | 39 | 10 | FOBS= | 289.6 | SIGMA= | 0.6 | PHAS= | 62.9 | FOM= | 0.96 | TEST= 0 |
| INDE | 1 | 39 | 12 | FOBS= | 55.5 | SIGMA= | 2.3 | PHAS= | -164.8 | FOM= | 0.87 | TEST= 0 |
| INDE | 1 | 39 | 14 | FOBS= | 127.4 | SIGMA= | 1.1 | PHAS= | -77.1 | FOM= | 0.92 | TEST= 0 |
| INDE | 1 | 39 | 16 | FOBS= | 123.3 | SIGMA= | 1.8 | PHAS= | -22.8 | FOM= | 0.98 | TEST= 1 |
| INDE | 1 | 39 | 28 | FOBS= | 130.9 | SIGMA= | 2.7 | PHAS= | 58.5 | FOM= | 0.90 | TEST= 0 |
| INDE | 1 | 39 | 30 | FOBS= | 157.0 | SIGMA= | 2.3 | PHAS= | -177.9 | FOM= | 0.80 | TEST= 1 |
| INDE | 1 | 39 | 32 | FOBS= | 229.3 | SIGMA= | 1.1 | PHAS= | 75.2 | FOM= | 0.91 | TEST= 0 |
| INDE | 1 | 39 | 34 | FOBS= | 201.8 | SIGMA= | 1.3 | PHAS= | -160.6 | FOM= | 0.19 | TEST= 1 |
| INDE | 1 | 39 | 36 | FOBS= | 187.1 | SIGMA= | 1.1 | PHAS= | 34.6 | FOM= | 0.93 | TEST= 0 |
| INDE | 1 | 39 | 38 | FOBS= | 120.1 | SIGMA= | 1.6 | PHAS= | -27.0 | FOM= | 0.84 | TEST= 0 |
| INDE | 1 | 39 | 40 | FOBS= | 136.2 | SIGMA= | 1.4 | PHAS= | -127.3 | FOM= | 0.87 | TEST= 0 |
| INDE | 1 | 39 | 42 | FOBS= | 100.3 | SIGMA= | 1.8 | PHAS= | -56.4 | FOM= | 0.83 | TEST= 0 |
| INDE | 1 | 39 | 44 | FOBS= | 33.8 | SIGMA= | 4.9 | PHAS= | -130.9 | FOM= | 0.46 | TEST= 0 |
| INDE | 1 | 39 | 46 | FOBS= | 152.7 | SIGMA= | 1.1 | PHAS= | 176.0 | FOM= | 0.94 | TEST= 1 |
| INDE | 1 | 39 | 48 | FOBS= | 87.3 | SIGMA= | 2.0 | PHAS= | 89.6 | FOM= | 0.91 | TEST= 0 |
| INDE | 1 | 39 | 50 | FOBS= | 59.9 | SIGMA= | 2.7 | PHAS= | 60.8 | FOM= | 0.84 | TEST= 0 |
| INDE | 1 | 39 | 52 | FOBS= | 79.5 | SIGMA= | 2.6 | PHAS= | 26.1 | FOM= | 0.86 | TEST= 0 |
| INDE | 1 | 39 | 54 | FOBS= | 0.0 | SIGMA= | 18.3 | PHAS= | 0.0 | FOM= | 0.00 | TEST= 0 |
| INDE | 1 | 39 | 56 | FOBS= | 59.8 | SIGMA= | 3.0 | PHAS= | -36.6 | FOM= | 0.51 | TEST= 0 |
| INDE | 1 | 39 | 58 | FOBS= | 35.5 | SIGMA= | 5.5 | PHAS= | 35.3 | FOM= | 0.79 | TEST= 0 |
| INDE | 1 | 39 | 60 | FOBS= | 56.1 | SIGMA= | 3.6 | PHAS= | 34.4 | FOM= | 0.84 | TEST= 0 |
| INDE | 1 | 39 | 62 | FOBS= | 25.4 | SIGMA= | 7.0 | PHAS= | 115.8 | FOM= | 0.36 | TEST= 0 |
| INDE | 1 | 39 | 64 | FOBS= | 61.8 | SIGMA= | 3.1 | PHAS= | 132.2 | FOM= | 0.06 | TEST= 1 |
| INDE | 1 | 39 | 66 | FOBS= | 100.8 | SIGMA= | 3.4 | PHAS= | -17.7 | FOM= | 0.90 | TEST= 0 |
| INDE | 1 | 40 | 1 | FOBS= | 290.7 | SIGMA= | 0.5 | PHAS= | 115.3 | FOM= | 0.99 | TEST= 0 |
| INDE | 1 | 40 | 3 | FOBS= | 49.2 | SIGMA= | 3.1 | PHAS= | 78.1 | FOM= | 0.89 | TEST= 0 |
| INDE | 1 | 40 | 9 | FOBS= | 188.9 | SIGMA= | 1.0 | PHAS= | -36.3 | FOM= | 0.85 | TEST= 0 |
| INDE | 1 | 40 | 11 | FOBS= | 146.8 | SIGMA= | 0.9 | PHAS= | 34.2 | FOM= | 0.94 | TEST= 0 |
| INDE | 1 | 40 | 13 | FOBS= | 65.5 | SIGMA= | 2.1 | PHAS= | -56.7 | FOM= | 0.38 | TEST= 0 |
| INDE | 1 | 40 | 15 | FOBS= | 105.9 | SIGMA= | 1.4 | PHAS= | 35.1 | FOM= | 0.82 | TEST= 0 |
| INDE | 1 | 40 | 17 | FOBS= | 130.1 | SIGMA= | 1.8 | PHAS= | 164.7 | FOM= | 0.46 | TEST= 0 |

*FIG. 12A - 40*

| | | | | | | | | | | | |
|---|---|---|---|---|---|---|---|---|---|---|---|
| INDE | 1 | 40 | 27 | FOBS= | 205.2 | SIGMA= | 2.6 | PHAS= | -55.4 | FOM= | 0.61 | TEST= 0
| INDE | 1 | 40 | 29 | FOBS= | 87.1 | SIGMA= | 4.1 | PHAS= | 32.6 | FOM= | 0.68 | TEST= 0
| INDE | 1 | 40 | 31 | FOBS= | 214.6 | SIGMA= | 1.8 | PHAS= | -72.8 | FOM= | 0.91 | TEST= 0
| INDE | 1 | 40 | 33 | FOBS= | 65.8 | SIGMA= | 3.7 | PHAS= | -123.5 | FOM= | 0.93 | TEST= 0
| INDE | 1 | 40 | 35 | FOBS= | 124.5 | SIGMA= | 1.7 | PHAS= | -78.6 | FOM= | 0.91 | TEST= 0
| INDE | 1 | 40 | 37 | FOBS= | 46.9 | SIGMA= | 4.0 | PHAS= | -31.9 | FOM= | 0.67 | TEST= 1
| INDE | 1 | 40 | 39 | FOBS= | 65.4 | SIGMA= | 2.9 | PHAS= | -148.1 | FOM= | 0.43 | TEST= 0
| INDE | 1 | 40 | 41 | FOBS= | 230.8 | SIGMA= | 1.1 | PHAS= | -150.2 | FOM= | 0.97 | TEST= 0
| INDE | 1 | 40 | 43 | FOBS= | 104.4 | SIGMA= | 1.7 | PHAS= | 123.9 | FOM= | 0.91 | TEST= 0
| INDE | 1 | 40 | 45 | FOBS= | 111.5 | SIGMA= | 1.5 | PHAS= | 129.8 | FOM= | 0.87 | TEST= 0
| INDE | 1 | 40 | 47 | FOBS= | 126.0 | SIGMA= | 1.3 | PHAS= | 91.1 | FOM= | 0.87 | TEST= 0
| INDE | 1 | 40 | 49 | FOBS= | 29.1 | SIGMA= | 6.3 | PHAS= | -47.4 | FOM= | 0.60 | TEST= 0
| INDE | 1 | 40 | 51 | FOBS= | 87.5 | SIGMA= | 1.9 | PHAS= | -33.2 | FOM= | 0.91 | TEST= 0
| INDE | 1 | 40 | 53 | FOBS= | 42.3 | SIGMA= | 5.3 | PHAS= | 155.6 | FOM= | 0.80 | TEST= 0
| INDE | 1 | 40 | 55 | FOBS= | 30.1 | SIGMA= | 6.7 | PHAS= | 128.5 | FOM= | 0.27 | TEST= 0
| INDE | 1 | 40 | 57 | FOBS= | 63.8 | SIGMA= | 2.8 | PHAS= | -31.5 | FOM= | 0.85 | TEST= 0
| INDE | 1 | 40 | 59 | FOBS= | 20.8 | SIGMA= | 10.6 | PHAS= | -43.1 | FOM= | 0.21 | TEST= 0
| INDE | 1 | 40 | 61 | FOBS= | 0.0 | SIGMA= | 20.2 | PHAS= | 0.0 | FOM= | 0.00 | TEST= 0
| INDE | 1 | 40 | 63 | FOBS= | 43.0 | SIGMA= | 4.7 | PHAS= | -13.4 | FOM= | 0.76 | TEST= 0
| INDE | 1 | 40 | 65 | FOBS= | 58.3 | SIGMA= | 3.9 | PHAS= | -36.3 | FOM= | 0.80 | TEST= 0
| INDE | 1 | 41 | 2 | FOBS= | 116.2 | SIGMA= | 1.4 | PHAS= | -63.7 | FOM= | 0.88 | TEST= 0
| INDE | 1 | 41 | 10 | FOBS= | 167.5 | SIGMA= | 0.8 | PHAS= | 121.6 | FOM= | 0.68 | TEST= 0
| INDE | 1 | 41 | 12 | FOBS= | 282.3 | SIGMA= | 0.6 | PHAS= | -112.4 | FOM= | 0.95 | TEST= 0
| INDE | 1 | 41 | 14 | FOBS= | 127.9 | SIGMA= | 1.2 | PHAS= | -92.4 | FOM= | 0.68 | TEST= 0
| INDE | 1 | 41 | 16 | FOBS= | 128.7 | SIGMA= | 1.9 | PHAS= | 11.8 | FOM= | 0.97 | TEST= 0
| INDE | 1 | 41 | 28 | FOBS= | 137.2 | SIGMA= | 2.7 | PHAS= | -104.1 | FOM= | 0.71 | TEST= 0
| INDE | 1 | 41 | 30 | FOBS= | 171.6 | SIGMA= | 2.1 | PHAS= | 86.4 | FOM= | 0.37 | TEST= 1
| INDE | 1 | 41 | 32 | FOBS= | 195.6 | SIGMA= | 1.9 | PHAS= | 123.9 | FOM= | 0.97 | TEST= 0
| INDE | 1 | 41 | 34 | FOBS= | 157.3 | SIGMA= | 1.5 | PHAS= | -168.9 | FOM= | 0.92 | TEST= 0
| INDE | 1 | 41 | 36 | FOBS= | 45.3 | SIGMA= | 4.0 | PHAS= | -113.7 | FOM= | 0.25 | TEST= 1
| INDE | 1 | 41 | 38 | FOBS= | 63.1 | SIGMA= | 2.9 | PHAS= | -98.9 | FOM= | 0.79 | TEST= 0
| INDE | 1 | 41 | 40 | FOBS= | 155.2 | SIGMA= | 1.2 | PHAS= | -176.7 | FOM= | 0.88 | TEST= 0
| INDE | 1 | 41 | 42 | FOBS= | 67.1 | SIGMA= | 2.6 | PHAS= | 39.4 | FOM= | 0.81 | TEST= 0
| INDE | 1 | 41 | 44 | FOBS= | 87.6 | SIGMA= | 2.0 | PHAS= | -14.1 | FOM= | 0.91 | TEST= 0
| INDE | 1 | 41 | 46 | FOBS= | 81.7 | SIGMA= | 2.1 | PHAS= | 54.8 | FOM= | 0.91 | TEST= 0
| INDE | 1 | 41 | 48 | FOBS= | 43.6 | SIGMA= | 3.9 | PHAS= | 106.8 | FOM= | 0.83 | TEST= 0
| INDE | 1 | 41 | 50 | FOBS= | 43.7 | SIGMA= | 3.8 | PHAS= | -82.1 | FOM= | 0.70 | TEST= 0
| INDE | 1 | 41 | 52 | FOBS= | 14.1 | SIGMA= | 19.1 | PHAS= | -38.7 | FOM= | 0.14 | TEST= 0
| INDE | 1 | 41 | 54 | FOBS= | 45.7 | SIGMA= | 4.7 | PHAS= | 141.7 | FOM= | 0.71 | TEST= 0
| INDE | 1 | 41 | 56 | FOBS= | 20.7 | SIGMA= | 8.6 | PHAS= | 35.0 | FOM= | 0.32 | TEST= 0
| INDE | 1 | 41 | 58 | FOBS= | 0.0 | SIGMA= | 19.9 | PHAS= | 0.0 | FOM= | 0.00 | TEST= 0
| INDE | 1 | 41 | 60 | FOBS= | 34.9 | SIGMA= | 6.0 | PHAS= | 164.5 | FOM= | 0.33 | TEST= 0
| INDE | 1 | 41 | 62 | FOBS= | 85.9 | SIGMA= | 2.1 | PHAS= | -115.8 | FOM= | 0.92 | TEST= 0
| INDE | 1 | 41 | 64 | FOBS= | 64.7 | SIGMA= | 2.9 | PHAS= | -114.1 | FOM= | 0.93 | TEST= 0
| INDE | 1 | 41 | 66 | FOBS= | 0.0 | SIGMA= | 29.0 | PHAS= | 0.0 | FOM= | 0.00 | TEST= 0
| INDE | 1 | 42 | 1 | FOBS= | 225.1 | SIGMA= | 0.4 | PHAS= | -172.6 | FOM= | 0.82 | TEST= 0
| INDE | 1 | 42 | 3 | FOBS= | 206.2 | SIGMA= | 1.3 | PHAS= | -145.7 | FOM= | 0.89 | TEST= 0
| INDE | 1 | 42 | 9 | FOBS= | 160.1 | SIGMA= | 1.2 | PHAS= | 55.4 | FOM= | 0.99 | TEST= 0
| INDE | 1 | 42 | 11 | FOBS= | 210.8 | SIGMA= | 0.8 | PHAS= | 165.2 | FOM= | 0.92 | TEST= 0
| INDE | 1 | 42 | 13 | FOBS= | 132.6 | SIGMA= | 1.2 | PHAS= | 169.5 | FOM= | 0.90 | TEST= 0
| INDE | 1 | 42 | 15 | FOBS= | 76.2 | SIGMA= | 2.1 | PHAS= | -0.1 | FOM= | 0.81 | TEST= 0
| INDE | 1 | 42 | 17 | FOBS= | 143.2 | SIGMA= | 1.9 | PHAS= | 157.2 | FOM= | 0.85 | TEST= 0
| INDE | 1 | 42 | 27 | FOBS= | 0.0 | SIGMA= | 31.2 | PHAS= | 0.0 | FOM= | 0.00 | TEST= 0
| INDE | 1 | 42 | 29 | FOBS= | 23.0 | SIGMA= | 14.8 | PHAS= | 82.9 | FOM= | 0.31 | TEST= 0
| INDE | 1 | 42 | 31 | FOBS= | 49.0 | SIGMA= | 7.0 | PHAS= | 153.9 | FOM= | 0.48 | TEST= 0
| INDE | 1 | 42 | 33 | FOBS= | 297.4 | SIGMA= | 1.2 | PHAS= | 153.8 | FOM= | 0.67 | TEST= 1
| INDE | 1 | 42 | 35 | FOBS= | 75.2 | SIGMA= | 2.7 | PHAS= | -34.4 | FOM= | 0.82 | TEST= 0
| INDE | 1 | 42 | 37 | FOBS= | 35.5 | SIGMA= | 5.1 | PHAS= | -58.8 | FOM= | 0.34 | TEST= 0
| INDE | 1 | 42 | 39 | FOBS= | 109.2 | SIGMA= | 1.7 | PHAS= | -160.4 | FOM= | 0.83 | TEST= 0
| INDE | 1 | 42 | 41 | FOBS= | 108.9 | SIGMA= | 1.7 | PHAS= | 169.5 | FOM= | 0.83 | TEST= 0
| INDE | 1 | 42 | 43 | FOBS= | 0.0 | SIGMA= | 18.5 | PHAS= | 0.0 | FOM= | 0.00 | TEST= 0
| INDE | 1 | 42 | 45 | FOBS= | 99.3 | SIGMA= | 1.8 | PHAS= | -131.1 | FOM= | 0.61 | TEST= 1
| INDE | 1 | 42 | 47 | FOBS= | 137.9 | SIGMA= | 1.3 | PHAS= | 69.6 | FOM= | 0.94 | TEST= 0
| INDE | 1 | 42 | 49 | FOBS= | 88.0 | SIGMA= | 1.9 | PHAS= | -71.9 | FOM= | 0.26 | TEST= 1
| INDE | 1 | 42 | 51 | FOBS= | 51.5 | SIGMA= | 4.1 | PHAS= | -90.3 | FOM= | 0.48 | TEST= 0
| INDE | 1 | 42 | 53 | FOBS= | 119.2 | SIGMA= | 1.7 | PHAS= | 160.2 | FOM= | 0.91 | TEST= 0
| INDE | 1 | 42 | 55 | FOBS= | 54.2 | SIGMA= | 3.3 | PHAS= | -41.3 | FOM= | 0.72 | TEST= 0
| INDE | 1 | 42 | 57 | FOBS= | 45.1 | SIGMA= | 4.5 | PHAS= | 24.5 | FOM= | 0.46 | TEST= 0
| INDE | 1 | 42 | 59 | FOBS= | 41.8 | SIGMA= | 5.3 | PHAS= | 117.7 | FOM= | 0.60 | TEST= 0
| INDE | 1 | 42 | 61 | FOBS= | 47.5 | SIGMA= | 3.7 | PHAS= | -64.1 | FOM= | 0.30 | TEST= 1

*FIG. 12A - 41*

| | | | | | | | | | | | |
|---|---|---|---|---|---|---|---|---|---|---|---|
| INDE | 1 | 42 | 63 | FOBS= | 62.1 | SIGMA= | 2.9 | PHAS= | 157.9 | FOM= | 0.90 | TEST= 0 |
| INDE | 1 | 42 | 65 | FOBS= | 59.3 | SIGMA= | 4.1 | PHAS= | 16.1 | FOM= | 0.20 | TEST= 1 |
| INDE | 1 | 43 | 2 | FOBS= | 166.6 | SIGMA= | 0.8 | PHAS= | 147.5 | FOM= | 0.92 | TEST= 0 |
| INDE | 1 | 43 | 10 | FOBS= | 141.8 | SIGMA= | 1.0 | PHAS= | 108.1 | FOM= | 0.93 | TEST= 0 |
| INDE | 1 | 43 | 12 | FOBS= | 177.9 | SIGMA= | 0.9 | PHAS= | 102.8 | FOM= | 0.91 | TEST= 0 |
| INDE | 1 | 43 | 14 | FOBS= | 151.6 | SIGMA= | 1.1 | PHAS= | 121.3 | FOM= | 0.91 | TEST= 1 |
| INDE | 1 | 43 | 16 | FOBS= | 209.5 | SIGMA= | 1.1 | PHAS= | 46.5 | FOM= | 0.98 | TEST= 0 |
| INDE | 1 | 43 | 18 | FOBS= | 124.2 | SIGMA= | 2.3 | PHAS= | 7.9 | FOM= | 0.92 | TEST= 0 |
| INDE | 1 | 43 | 28 | FOBS= | 88.2 | SIGMA= | 4.0 | PHAS= | -53.7 | FOM= | 0.42 | TEST= 0 |
| INDE | 1 | 43 | 30 | FOBS= | 65.6 | SIGMA= | 5.3 | PHAS= | 105.9 | FOM= | 0.68 | TEST= 0 |
| INDE | 1 | 43 | 32 | FOBS= | 127.6 | SIGMA= | 2.8 | PHAS= | 34.7 | FOM= | 0.79 | TEST= 0 |
| INDE | 1 | 43 | 34 | FOBS= | 91.8 | SIGMA= | 2.6 | PHAS= | -150.6 | FOM= | 0.72 | TEST= 0 |
| INDE | 1 | 43 | 36 | FOBS= | 42.2 | SIGMA= | 4.3 | PHAS= | 113.9 | FOM= | 0.14 | TEST= 0 |
| INDE | 1 | 43 | 38 | FOBS= | 127.7 | SIGMA= | 1.5 | PHAS= | 38.1 | FOM= | 0.11 | TEST= 1 |
| INDE | 1 | 43 | 40 | FOBS= | 76.5 | SIGMA= | 2.4 | PHAS= | 170.7 | FOM= | 0.86 | TEST= 0 |
| INDE | 1 | 43 | 42 | FOBS= | 6.0 | SIGMA= | 31.6 | PHAS= | 133.8 | FOM= | 0.56 | TEST= 0 |
| INDE | 1 | 43 | 44 | FOBS= | 0.0 | SIGMA= | 22.8 | PHAS= | 0.0 | FOM= | 0.00 | TEST= 0 |
| INDE | 1 | 43 | 46 | FOBS= | 150.6 | SIGMA= | 1.2 | PHAS= | 40.9 | FOM= | 0.97 | TEST= 0 |
| INDE | 1 | 43 | 48 | FOBS= | 50.2 | SIGMA= | 3.4 | PHAS= | 133.8 | FOM= | 0.43 | TEST= 0 |
| INDE | 1 | 43 | 50 | FOBS= | 76.6 | SIGMA= | 2.2 | PHAS= | -126.7 | FOM= | 0.78 | TEST= 0 |
| INDE | 1 | 43 | 52 | FOBS= | 31.7 | SIGMA= | 7.6 | PHAS= | 119.5 | FOM= | 0.62 | TEST= 0 |
| INDE | 1 | 43 | 54 | FOBS= | 0.0 | SIGMA= | 18.5 | PHAS= | 0.0 | FOM= | 0.00 | TEST= 0 |
| INDE | 1 | 43 | 56 | FOBS= | 11.1 | SIGMA= | 23.8 | PHAS= | 145.0 | FOM= | 0.09 | TEST= 0 |
| INDE | 1 | 43 | 58 | FOBS= | 38.8 | SIGMA= | 4.8 | PHAS= | -15.5 | FOM= | 0.73 | TEST= 0 |
| INDE | 1 | 43 | 60 | FOBS= | 68.1 | SIGMA= | 3.1 | PHAS= | -139.4 | FOM= | 0.93 | TEST= 0 |
| INDE | 1 | 43 | 62 | FOBS= | 11.7 | SIGMA= | 16.2 | PHAS= | -120.0 | FOM= | 0.06 | TEST= 0 |
| INDE | 1 | 43 | 64 | FOBS= | 56.9 | SIGMA= | 3.8 | PHAS= | -88.9 | FOM= | 0.89 | TEST= 0 |
| INDE | 1 | 44 | 1 | FOBS= | 198.6 | SIGMA= | 0.5 | PHAS= | 145.3 | FOM= | 0.96 | TEST= 0 |
| INDE | 1 | 44 | 11 | FOBS= | 77.9 | SIGMA= | 1.9 | PHAS= | 111.5 | FOM= | 0.95 | TEST= 0 |
| INDE | 1 | 44 | 13 | FOBS= | 81.1 | SIGMA= | 2.0 | PHAS= | 8.3 | FOM= | 0.94 | TEST= 0 |
| INDE | 1 | 44 | 15 | FOBS= | 165.3 | SIGMA= | 1.3 | PHAS= | 14.0 | FOM= | 0.98 | TEST= 0 |
| INDE | 1 | 44 | 17 | FOBS= | 160.5 | SIGMA= | 1.4 | PHAS= | -73.3 | FOM= | 0.93 | TEST= 0 |
| INDE | 1 | 44 | 19 | FOBS= | 227.3 | SIGMA= | 1.4 | PHAS= | -92.2 | FOM= | 0.97 | TEST= 0 |
| INDE | 1 | 44 | 27 | FOBS= | 146.4 | SIGMA= | 3.5 | PHAS= | -142.8 | FOM= | 0.58 | TEST= 0 |
| INDE | 1 | 44 | 29 | FOBS= | 116.9 | SIGMA= | 3.0 | PHAS= | -173.6 | FOM= | 0.78 | TEST= 0 |
| INDE | 1 | 44 | 31 | FOBS= | 102.5 | SIGMA= | 3.4 | PHAS= | -62.0 | FOM= | 0.78 | TEST= 0 |
| INDE | 1 | 44 | 33 | FOBS= | 92.0 | SIGMA= | 3.7 | PHAS= | -168.1 | FOM= | 0.87 | TEST= 0 |
| INDE | 1 | 44 | 35 | FOBS= | 48.2 | SIGMA= | 4.1 | PHAS= | 87.8 | FOM= | 0.78 | TEST= 0 |
| INDE | 1 | 44 | 37 | FOBS= | 207.2 | SIGMA= | 1.0 | PHAS= | -8.4 | FOM= | 0.91 | TEST= 0 |
| INDE | 1 | 44 | 39 | FOBS= | 30.7 | SIGMA= | 6.2 | PHAS= | -171.7 | FOM= | 0.09 | TEST= 1 |
| INDE | 1 | 44 | 41 | FOBS= | 182.2 | SIGMA= | 1.1 | PHAS= | 157.5 | FOM= | 0.96 | TEST= 0 |
| INDE | 1 | 44 | 43 | FOBS= | 67.3 | SIGMA= | 2.6 | PHAS= | 32.7 | FOM= | 0.88 | TEST= 0 |
| INDE | 1 | 44 | 45 | FOBS= | 67.2 | SIGMA= | 2.6 | PHAS= | -41.2 | FOM= | 0.84 | TEST= 0 |
| INDE | 1 | 44 | 47 | FOBS= | 79.7 | SIGMA= | 2.2 | PHAS= | -30.0 | FOM= | 0.78 | TEST= 0 |
| INDE | 1 | 44 | 49 | FOBS= | 61.6 | SIGMA= | 2.8 | PHAS= | 117.7 | FOM= | 0.89 | TEST= 0 |
| INDE | 1 | 44 | 51 | FOBS= | 0.0 | SIGMA= | 22.1 | PHAS= | 0.0 | FOM= | 0.00 | TEST= 0 |
| INDE | 1 | 44 | 53 | FOBS= | 63.4 | SIGMA= | 3.1 | PHAS= | 12.4 | FOM= | 0.75 | TEST= 0 |
| INDE | 1 | 44 | 55 | FOBS= | 40.0 | SIGMA= | 4.8 | PHAS= | -0.2 | FOM= | 0.45 | TEST= 0 |
| INDE | 1 | 44 | 57 | FOBS= | 63.4 | SIGMA= | 2.9 | PHAS= | -101.9 | FOM= | 0.14 | TEST= 0 |
| INDE | 1 | 44 | 59 | FOBS= | 78.1 | SIGMA= | 2.8 | PHAS= | 165.1 | FOM= | 0.91 | TEST= 0 |
| INDE | 1 | 44 | 61 | FOBS= | 0.0 | SIGMA= | 20.4 | PHAS= | 0.0 | FOM= | 0.00 | TEST= 1 |
| INDE | 1 | 44 | 63 | FOBS= | 85.5 | SIGMA= | 2.5 | PHAS= | 155.5 | FOM= | 0.95 | TEST= 0 |
| INDE | 1 | 45 | 2 | FOBS= | 149.8 | SIGMA= | 1.0 | PHAS= | 37.8 | FOM= | 0.90 | TEST= 0 |
| INDE | 1 | 45 | 10 | FOBS= | 85.0 | SIGMA= | 3.3 | PHAS= | -48.2 | FOM= | 0.87 | TEST= 0 |
| INDE | 1 | 45 | 12 | FOBS= | 220.8 | SIGMA= | 0.8 | PHAS= | 55.1 | FOM= | 0.95 | TEST= 0 |
| INDE | 1 | 45 | 14 | FOBS= | 127.4 | SIGMA= | 1.4 | PHAS= | 155.5 | FOM= | 0.84 | TEST= 0 |
| INDE | 1 | 45 | 16 | FOBS= | 52.3 | SIGMA= | 3.7 | PHAS= | 4.8 | FOM= | 0.86 | TEST= 0 |
| INDE | 1 | 45 | 18 | FOBS= | 22.3 | SIGMA= | 10.0 | PHAS= | -73.9 | FOM= | 0.07 | TEST= 0 |
| INDE | 1 | 45 | 20 | FOBS= | 135.1 | SIGMA= | 2.2 | PHAS= | -170.7 | FOM= | 0.90 | TEST= 0 |
| INDE | 1 | 45 | 28 | FOBS= | 173.3 | SIGMA= | 2.2 | PHAS= | 113.5 | FOM= | 0.90 | TEST= 0 |
| INDE | 1 | 45 | 30 | FOBS= | 50.4 | SIGMA= | 6.8 | PHAS= | -174.3 | FOM= | 0.14 | TEST= 0 |
| INDE | 1 | 45 | 32 | FOBS= | 54.3 | SIGMA= | 6.2 | PHAS= | -66.1 | FOM= | 0.82 | TEST= 0 |
| INDE | 1 | 45 | 34 | FOBS= | 120.2 | SIGMA= | 2.9 | PHAS= | -47.5 | FOM= | 0.86 | TEST= 0 |
| INDE | 1 | 45 | 36 | FOBS= | 90.4 | SIGMA= | 2.1 | PHAS= | -141.1 | FOM= | 0.89 | TEST= 0 |
| INDE | 1 | 45 | 38 | FOBS= | 109.8 | SIGMA= | 1.7 | PHAS= | -14.3 | FOM= | 0.81 | TEST= 0 |
| INDE | 1 | 45 | 40 | FOBS= | 195.4 | SIGMA= | 1.1 | PHAS= | 44.1 | FOM= | 0.96 | TEST= 0 |
| INDE | 1 | 45 | 42 | FOBS= | 185.0 | SIGMA= | 1.1 | PHAS= | 59.2 | FOM= | 0.95 | TEST= 0 |
| INDE | 1 | 45 | 44 | FOBS= | 28.4 | SIGMA= | 6.1 | PHAS= | 59.5 | FOM= | 0.21 | TEST= 0 |
| INDE | 1 | 45 | 46 | FOBS= | 24.1 | SIGMA= | 7.6 | PHAS= | 152.9 | FOM= | 0.30 | TEST= 0 |
| INDE | 1 | 45 | 48 | FOBS= | 23.1 | SIGMA= | 8.3 | PHAS= | 22.9 | FOM= | 0.43 | TEST= 0 |

*FIG. 12A - 42*

| | | | | | | | | | | | | |
|---|---|---|---|---|---|---|---|---|---|---|---|---|
| INDE | 1 | 45 | 50 | FOBS= | 0.0 | SIGMA= | 21.3 | PHAS= | 0.0 | FOM= | 0.00 | TEST= 0 |
| INDE | 1 | 45 | 52 | FOBS= | 38.3 | SIGMA= | 5.4 | PHAS= | -81.7 | FOM= | 0.72 | TEST= 0 |
| INDE | 1 | 45 | 54 | FOBS= | 0.0 | SIGMA= | 18.4 | PHAS= | 0.0 | FOM= | 0.00 | TEST= 0 |
| INDE | 1 | 45 | 56 | FOBS= | 34.2 | SIGMA= | 5.8 | PHAS= | 143.0 | FOM= | 0.26 | TEST= 0 |
| INDE | 1 | 45 | 58 | FOBS= | 100.7 | SIGMA= | 1.9 | PHAS= | -105.7 | FOM= | 0.81 | TEST= 0 |
| INDE | 1 | 45 | 60 | FOBS= | 57.7 | SIGMA= | 3.3 | PHAS= | -154.6 | FOM= | 0.84 | TEST= 0 |
| INDE | 1 | 45 | 62 | FOBS= | 0.0 | SIGMA= | 22.7 | PHAS= | 0.0 | FOM= | 0.00 | TEST= 0 |
| INDE | 1 | 46 | 1 | FOBS= | 203.1 | SIGMA= | 0.9 | PHAS= | -157.4 | FOM= | 0.96 | TEST= 0 |
| INDE | 1 | 46 | 11 | FOBS= | 53.3 | SIGMA= | 3.0 | PHAS= | -98.8 | FOM= | 0.61 | TEST= 0 |
| INDE | 1 | 46 | 13 | FOBS= | 113.4 | SIGMA= | 1.6 | PHAS= | -63.3 | FOM= | 0.80 | TEST= 1 |
| INDE | 1 | 46 | 15 | FOBS= | 0.0 | SIGMA= | 20.5 | PHAS= | 0.0 | FOM= | 0.00 | TEST= 0 |
| INDE | 1 | 46 | 17 | FOBS= | 70.3 | SIGMA= | 2.9 | PHAS= | -38.9 | FOM= | 0.81 | TEST= 0 |
| INDE | 1 | 46 | 19 | FOBS= | 114.7 | SIGMA= | 2.1 | PHAS= | -138.7 | FOM= | 0.85 | TEST= 0 |
| INDE | 1 | 46 | 21 | FOBS= | 107.3 | SIGMA= | 2.7 | PHAS= | 120.2 | FOM= | 0.61 | TEST= 0 |
| INDE | 1 | 46 | 27 | FOBS= | 95.3 | SIGMA= | 5.1 | PHAS= | 81.2 | FOM= | 0.39 | TEST= 0 |
| INDE | 1 | 46 | 29 | FOBS= | 0.0 | SIGMA= | 25.9 | PHAS= | 0.0 | FOM= | 0.00 | TEST= 0 |
| INDE | 1 | 46 | 31 | FOBS= | 94.1 | SIGMA= | 3.7 | PHAS= | -171.0 | FOM= | 0.86 | TEST= 0 |
| INDE | 1 | 46 | 33 | FOBS= | 224.1 | SIGMA= | 1.7 | PHAS= | -173.0 | FOM= | 0.97 | TEST= 0 |
| INDE | 1 | 46 | 35 | FOBS= | 89.2 | SIGMA= | 2.8 | PHAS= | 157.5 | FOM= | 0.91 | TEST= 0 |
| INDE | 1 | 46 | 37 | FOBS= | 177.2 | SIGMA= | 1.1 | PHAS= | 29.6 | FOM= | 0.90 | TEST= 0 |
| INDE | 1 | 46 | 39 | FOBS= | 232.1 | SIGMA= | 0.9 | PHAS= | -47.5 | FOM= | 0.97 | TEST= 0 |
| INDE | 1 | 46 | 41 | FOBS= | 147.5 | SIGMA= | 1.3 | PHAS= | -81.9 | FOM= | 0.96 | TEST= 0 |
| INDE | 1 | 46 | 43 | FOBS= | 46.1 | SIGMA= | 4.0 | PHAS= | -8.2 | FOM= | 0.27 | TEST= 0 |
| INDE | 1 | 46 | 45 | FOBS= | 110.3 | SIGMA= | 1.6 | PHAS= | -0.4 | FOM= | 0.86 | TEST= 0 |
| INDE | 1 | 46 | 47 | FOBS= | 32.1 | SIGMA= | 5.5 | PHAS= | -140.5 | FOM= | 0.51 | TEST= 0 |
| INDE | 1 | 46 | 49 | FOBS= | 101.5 | SIGMA= | 1.8 | PHAS= | 155.1 | FOM= | 0.93 | TEST= 0 |
| INDE | 1 | 46 | 51 | FOBS= | 0.0 | SIGMA= | 21.3 | PHAS= | 0.0 | FOM= | 0.00 | TEST= 0 |
| INDE | 1 | 46 | 53 | FOBS= | 14.8 | SIGMA= | 14.1 | PHAS= | 50.8 | FOM= | 0.09 | TEST= 0 |
| INDE | 1 | 46 | 55 | FOBS= | 0.0 | SIGMA= | 19.0 | PHAS= | 0.0 | FOM= | 0.00 | TEST= 0 |
| INDE | 1 | 46 | 57 | FOBS= | 75.5 | SIGMA= | 2.5 | PHAS= | 150.2 | FOM= | 0.82 | TEST= 0 |
| INDE | 1 | 46 | 59 | FOBS= | 43.1 | SIGMA= | 4.4 | PHAS= | 169.1 | FOM= | 0.81 | TEST= 0 |
| INDE | 1 | 46 | 61 | FOBS= | 0.0 | SIGMA= | 22.5 | PHAS= | 0.0 | FOM= | 0.00 | TEST= 0 |
| INDE | 1 | 47 | 2 | FOBS= | 324.2 | SIGMA= | 0.5 | PHAS= | 40.3 | FOM= | 0.94 | TEST= 0 |
| INDE | 1 | 47 | 12 | FOBS= | 67.6 | SIGMA= | 2.6 | PHAS= | -23.9 | FOM= | 0.16 | TEST= 1 |
| INDE | 1 | 47 | 14 | FOBS= | 79.7 | SIGMA= | 2.3 | PHAS= | 143.6 | FOM= | 0.63 | TEST= 0 |
| INDE | 1 | 47 | 16 | FOBS= | 89.2 | SIGMA= | 2.2 | PHAS= | 177.0 | FOM= | 0.92 | TEST= 0 |
| INDE | 1 | 47 | 18 | FOBS= | 130.1 | SIGMA= | 1.6 | PHAS= | -155.3 | FOM= | 0.92 | TEST= 0 |
| INDE | 1 | 47 | 20 | FOBS= | 206.4 | SIGMA= | 1.6 | PHAS= | 92.3 | FOM= | 0.96 | TEST= 0 |
| INDE | 1 | 47 | 22 | FOBS= | 23.2 | SIGMA= | 17.0 | PHAS= | 160.4 | FOM= | 0.04 | TEST= 0 |
| INDE | 1 | 47 | 28 | FOBS= | 57.3 | SIGMA= | 6.2 | PHAS= | -125.3 | FOM= | 0.06 | TEST= 1 |
| INDE | 1 | 47 | 30 | FOBS= | 58.3 | SIGMA= | 5.9 | PHAS= | 146.6 | FOM= | 0.55 | TEST= 0 |
| INDE | 1 | 47 | 32 | FOBS= | 248.6 | SIGMA= | 1.6 | PHAS= | 153.6 | FOM= | 0.94 | TEST= 0 |
| INDE | 1 | 47 | 34 | FOBS= | 100.5 | SIGMA= | 2.7 | PHAS= | 74.0 | FOM= | 0.75 | TEST= 0 |
| INDE | 1 | 47 | 36 | FOBS= | 0.0 | SIGMA= | 20.4 | PHAS= | 0.0 | FOM= | 0.00 | TEST= 0 |
| INDE | 1 | 47 | 38 | FOBS= | 151.1 | SIGMA= | 1.3 | PHAS= | -97.9 | FOM= | 0.12 | TEST= 1 |
| INDE | 1 | 47 | 40 | FOBS= | 129.9 | SIGMA= | 1.5 | PHAS= | -159.9 | FOM= | 0.95 | TEST= 0 |
| INDE | 1 | 47 | 42 | FOBS= | 68.7 | SIGMA= | 2.6 | PHAS= | 104.0 | FOM= | 0.84 | TEST= 0 |
| INDE | 1 | 47 | 44 | FOBS= | 97.4 | SIGMA= | 1.8 | PHAS= | 26.7 | FOM= | 0.86 | TEST= 0 |
| INDE | 1 | 47 | 46 | FOBS= | 43.3 | SIGMA= | 4.0 | PHAS= | -140.1 | FOM= | 0.29 | TEST= 0 |
| INDE | 1 | 47 | 48 | FOBS= | 104.0 | SIGMA= | 1.8 | PHAS= | 41.9 | FOM= | 0.95 | TEST= 0 |
| INDE | 1 | 47 | 50 | FOBS= | 37.3 | SIGMA= | 5.8 | PHAS= | 45.1 | FOM= | 0.50 | TEST= 0 |
| INDE | 1 | 47 | 52 | FOBS= | 40.2 | SIGMA= | 5.2 | PHAS= | -106.3 | FOM= | 0.70 | TEST= 0 |
| INDE | 1 | 47 | 54 | FOBS= | 0.0 | SIGMA= | 19.5 | PHAS= | 0.0 | FOM= | 0.00 | TEST= 0 |
| INDE | 1 | 47 | 56 | FOBS= | 27.2 | SIGMA= | 6.8 | PHAS= | 96.9 | FOM= | 0.28 | TEST= 0 |
| INDE | 1 | 47 | 58 | FOBS= | 35.5 | SIGMA= | 6.1 | PHAS= | 122.7 | FOM= | 0.35 | TEST= 0 |
| INDE | 1 | 47 | 60 | FOBS= | 0.0 | SIGMA= | 22.2 | PHAS= | 0.0 | FOM= | 0.00 | TEST= 0 |
| INDE | 1 | 48 | 1 | FOBS= | 102.2 | SIGMA= | 1.6 | PHAS= | 112.0 | FOM= | 0.92 | TEST= 0 |
| INDE | 1 | 48 | 3 | FOBS= | 101.2 | SIGMA= | 2.7 | PHAS= | 147.0 | FOM= | 0.38 | TEST= 0 |
| INDE | 1 | 48 | 13 | FOBS= | 67.6 | SIGMA= | 2.6 | PHAS= | -119.7 | FOM= | 0.66 | TEST= 0 |
| INDE | 1 | 48 | 15 | FOBS= | 174.7 | SIGMA= | 1.1 | PHAS= | 142.2 | FOM= | 0.96 | TEST= 0 |
| INDE | 1 | 48 | 17 | FOBS= | 176.7 | SIGMA= | 1.2 | PHAS= | 84.1 | FOM= | 0.95 | TEST= 0 |
| INDE | 1 | 48 | 19 | FOBS= | 56.5 | SIGMA= | 3.6 | PHAS= | 48.0 | FOM= | 0.80 | TEST= 0 |
| INDE | 1 | 48 | 21 | FOBS= | 151.8 | SIGMA= | 2.1 | PHAS= | 59.4 | FOM= | 0.84 | TEST= 0 |
| INDE | 1 | 48 | 27 | FOBS= | 182.1 | SIGMA= | 2.9 | PHAS= | 180.0 | FOM= | 0.00 | TEST= 1 |
| INDE | 1 | 48 | 29 | FOBS= | 250.5 | SIGMA= | 1.6 | PHAS= | 164.3 | FOM= | 0.89 | TEST= 0 |
| INDE | 1 | 48 | 31 | FOBS= | 160.5 | SIGMA= | 2.3 | PHAS= | 109.5 | FOM= | 0.95 | TEST= 0 |
| INDE | 1 | 48 | 33 | FOBS= | 81.3 | SIGMA= | 4.2 | PHAS= | 94.0 | FOM= | 0.68 | TEST= 0 |
| INDE | 1 | 48 | 35 | FOBS= | 0.0 | SIGMA= | 21.4 | PHAS= | 0.0 | FOM= | 0.00 | TEST= 0 |
| INDE | 1 | 48 | 37 | FOBS= | 21.0 | SIGMA= | 8.6 | PHAS= | 31.2 | FOM= | 0.05 | TEST= 1 |
| INDE | 1 | 48 | 39 | FOBS= | 34.5 | SIGMA= | 5.4 | PHAS= | -134.6 | FOM= | 0.80 | TEST= 0 |

*FIG. 12A - 43*

```
INDE  1  48  41 FOBS=   44.6 SIGMA=   4.0 PHAS=   48.8 FOM=  0.67 TEST= 0
INDE  1  48  43 FOBS=   41.9 SIGMA=   4.2 PHAS=  -96.5 FOM=  0.79 TEST= 0
INDE  1  48  45 FOBS=    0.0 SIGMA=  19.4 PHAS=    0.0 FOM=  0.00 TEST= 0
INDE  1  48  47 FOBS=  101.4 SIGMA=   1.8 PHAS=  -78.0 FOM=  0.92 TEST= 0
INDE  1  48  49 FOBS=   76.2 SIGMA=   3.0 PHAS= -105.2 FOM=  0.86 TEST= 0
INDE  1  48  51 FOBS=   54.0 SIGMA=   4.0 PHAS= -168.7 FOM=  0.63 TEST= 0
INDE  1  48  53 FOBS=    0.0 SIGMA=  20.6 PHAS=    0.0 FOM=  0.00 TEST= 0
INDE  1  48  55 FOBS=    0.0 SIGMA=  20.3 PHAS=    0.0 FOM=  0.00 TEST= 1
INDE  1  48  57 FOBS=   33.0 SIGMA=   5.7 PHAS= -153.6 FOM=  0.04 TEST= 1
INDE  1  48  59 FOBS=   22.4 SIGMA=  11.3 PHAS=   34.9 FOM=  0.25 TEST= 0
INDE  1  48  61 FOBS=    0.0 SIGMA=  21.5 PHAS=    0.0 FOM=  0.00 TEST= 0
INDE  1  49   2 FOBS=  143.9 SIGMA=   1.0 PHAS=    2.4 FOM=  0.94 TEST= 0
INDE  1  49  12 FOBS=  242.8 SIGMA=   0.9 PHAS=   63.0 FOM=  0.89 TEST= 0
INDE  1  49  14 FOBS=  114.4 SIGMA=   1.6 PHAS=   54.2 FOM=  0.94 TEST= 0
INDE  1  49  16 FOBS=  193.8 SIGMA=   1.0 PHAS=   40.4 FOM=  0.95 TEST= 0
INDE  1  49  18 FOBS=  108.8 SIGMA=   1.9 PHAS= -165.8 FOM=  0.50 TEST= 0
INDE  1  49  20 FOBS=  249.6 SIGMA=   1.0 PHAS=   -7.5 FOM=  0.95 TEST= 0
INDE  1  49  22 FOBS=   95.7 SIGMA=   3.1 PHAS= -117.9 FOM=  0.80 TEST= 0
INDE  1  49  26 FOBS=   79.4 SIGMA=   6.1 PHAS= -167.5 FOM=  0.35 TEST= 0
INDE  1  49  28 FOBS=   43.6 SIGMA=   7.9 PHAS=  -51.6 FOM=  0.28 TEST= 0
INDE  1  49  30 FOBS=   91.5 SIGMA=   3.8 PHAS=   55.3 FOM=  0.85 TEST= 0
INDE  1  49  32 FOBS=   64.6 SIGMA=   5.2 PHAS=   17.5 FOM=  0.78 TEST= 0
INDE  1  49  34 FOBS=   89.0 SIGMA=   3.1 PHAS=  -24.9 FOM=  0.58 TEST= 0
INDE  1  49  36 FOBS=   32.1 SIGMA=   7.2 PHAS=   63.9 FOM=  0.32 TEST= 0
INDE  1  49  38 FOBS=   63.1 SIGMA=   2.9 PHAS=  -72.9 FOM=  0.85 TEST= 0
INDE  1  49  40 FOBS=   58.1 SIGMA=   3.1 PHAS= -148.2 FOM=  0.86 TEST= 0
INDE  1  49  42 FOBS=    0.0 SIGMA=  19.5 PHAS=    0.0 FOM=  0.00 TEST= 0
INDE  1  49  44 FOBS=   41.7 SIGMA=   4.2 PHAS=  170.4 FOM=  0.34 TEST= 0
INDE  1  49  46 FOBS=  106.2 SIGMA=   1.7 PHAS=  164.2 FOM=  0.91 TEST= 0
INDE  1  49  48 FOBS=  111.9 SIGMA=   1.7 PHAS=  118.2 FOM=  0.93 TEST= 0
INDE  1  49  50 FOBS=   80.7 SIGMA=   2.8 PHAS=  100.6 FOM=  0.92 TEST= 0
INDE  1  49  52 FOBS=    0.0 SIGMA=  23.7 PHAS=    0.0 FOM=  0.00 TEST= 0
INDE  1  49  54 FOBS=    0.0 SIGMA=  18.8 PHAS=    0.0 FOM=  0.00 TEST= 0
INDE  1  49  56 FOBS=    0.0 SIGMA=  19.8 PHAS=    0.0 FOM=  0.00 TEST= 0
INDE  1  49  58 FOBS=    0.0 SIGMA=  20.1 PHAS=    0.0 FOM=  0.00 TEST= 1
INDE  1  49  60 FOBS=   47.1 SIGMA=   5.3 PHAS=   49.1 FOM=  0.47 TEST= 0
INDE  1  50   1 FOBS=  291.0 SIGMA=   0.6 PHAS=   80.5 FOM=  0.95 TEST= 0
INDE  1  50   3 FOBS=  108.1 SIGMA=   1.6 PHAS=  -95.3 FOM=  0.33 TEST= 0
INDE  1  50  13 FOBS=  156.0 SIGMA=   1.2 PHAS=  -18.1 FOM=  0.85 TEST= 0
INDE  1  50  15 FOBS=  167.1 SIGMA=   1.2 PHAS= -167.7 FOM=  0.96 TEST= 0
INDE  1  50  17 FOBS=  119.4 SIGMA=   1.6 PHAS=    9.8 FOM=  0.92 TEST= 0
INDE  1  50  19 FOBS=    0.0 SIGMA=  19.9 PHAS=    0.0 FOM=  0.00 TEST= 0
INDE  1  50  21 FOBS=   64.2 SIGMA=   3.2 PHAS= -169.7 FOM=  0.52 TEST= 0
INDE  1  50  23 FOBS=   43.2 SIGMA=   6.8 PHAS=  140.4 FOM=  0.17 TEST= 0
INDE  1  50  27 FOBS=  136.2 SIGMA=   2.7 PHAS=   83.0 FOM=  0.65 TEST= 0
INDE  1  50  29 FOBS=  103.3 SIGMA=   3.4 PHAS= -133.7 FOM=  0.58 TEST= 0
INDE  1  50  31 FOBS=  102.7 SIGMA=   3.4 PHAS=  -21.9 FOM=  0.86 TEST= 0
INDE  1  50  33 FOBS=   38.9 SIGMA=   8.6 PHAS=  -87.0 FOM=  0.45 TEST= 0
INDE  1  50  35 FOBS=    0.0 SIGMA=  21.6 PHAS=    0.0 FOM=  0.00 TEST= 0
INDE  1  50  37 FOBS=   70.9 SIGMA=   3.0 PHAS= -112.3 FOM=  0.17 TEST= 0
INDE  1  50  39 FOBS=  143.7 SIGMA=   1.3 PHAS=  153.6 FOM=  0.96 TEST= 0
INDE  1  50  41 FOBS=   74.6 SIGMA=   2.4 PHAS=  -65.3 FOM=  0.19 TEST= 0
INDE  1  50  43 FOBS=    9.2 SIGMA=  22.1 PHAS=  155.0 FOM=  0.02 TEST= 1
INDE  1  50  45 FOBS=  120.8 SIGMA=   1.5 PHAS=  103.9 FOM=  0.95 TEST= 0
INDE  1  50  47 FOBS=  110.8 SIGMA=   1.7 PHAS=   39.0 FOM=  0.60 TEST= 1
INDE  1  50  49 FOBS=   75.7 SIGMA=   3.0 PHAS=   66.7 FOM=  0.48 TEST= 1
INDE  1  50  51 FOBS=   44.3 SIGMA=   4.9 PHAS=   57.9 FOM=  0.36 TEST= 0
INDE  1  50  53 FOBS=   54.0 SIGMA=   3.6 PHAS=  -90.7 FOM=  0.66 TEST= 0
INDE  1  50  55 FOBS=   51.5 SIGMA=   3.7 PHAS=   55.6 FOM=  0.18 TEST= 1
INDE  1  50  57 FOBS=    0.0 SIGMA=  21.5 PHAS=    0.0 FOM=  0.00 TEST= 0
INDE  1  50  59 FOBS=   46.0 SIGMA=   5.3 PHAS= -116.0 FOM=  0.16 TEST= 1
INDE  1  51   2 FOBS=  271.5 SIGMA=   0.7 PHAS=   16.7 FOM=  0.47 TEST= 1
INDE  1  51  14 FOBS=  249.5 SIGMA=   0.8 PHAS=   55.4 FOM=  0.94 TEST= 0
INDE  1  51  16 FOBS=  191.2 SIGMA=   1.0 PHAS=  146.9 FOM=  0.96 TEST= 0
INDE  1  51  18 FOBS=   97.7 SIGMA=   2.0 PHAS=  -20.4 FOM=  0.53 TEST= 1
INDE  1  51  20 FOBS=    0.0 SIGMA=  21.4 PHAS=    0.0 FOM=  0.00 TEST= 0
INDE  1  51  22 FOBS=  103.5 SIGMA=   2.0 PHAS=  -15.0 FOM=  0.90 TEST= 0
INDE  1  51  24 FOBS=  116.7 SIGMA=   2.7 PHAS=   48.8 FOM=  0.48 TEST= 0
INDE  1  51  26 FOBS=   78.2 SIGMA=   6.3 PHAS= -147.9 FOM=  0.39 TEST= 0
INDE  1  51  28 FOBS=  108.3 SIGMA=   3.3 PHAS=   18.2 FOM=  0.67 TEST= 0
```

*FIG. 12A - 44*

```
INDE  1  51  30  FOBS=   71.2  SIGMA=   4.8  PHAS=  -118.0  FOM=  0.73  TEST= 0
INDE  1  51  32  FOBS=   76.1  SIGMA=   4.5  PHAS=    -7.7  FOM=  0.81  TEST= 0
INDE  1  51  34  FOBS=   80.8  SIGMA=   3.4  PHAS=  -113.8  FOM=  0.81  TEST= 0
INDE  1  51  36  FOBS=   76.2  SIGMA=   3.1  PHAS=    85.5  FOM=  0.89  TEST= 0
INDE  1  51  38  FOBS=  138.7  SIGMA=   1.5  PHAS=    51.7  FOM=  0.96  TEST= 0
INDE  1  51  40  FOBS=   69.8  SIGMA=   2.6  PHAS=   144.4  FOM=  0.83  TEST= 0
INDE  1  51  42  FOBS=  109.5  SIGMA=   1.7  PHAS=   179.6  FOM=  0.91  TEST= 0
INDE  1  51  44  FOBS=  104.2  SIGMA=   1.8  PHAS=    15.9  FOM=  0.92  TEST= 0
INDE  1  51  46  FOBS=    0.0  SIGMA=  18.7  PHAS=     0.0  FOM=  0.00  TEST= 0
INDE  1  51  48  FOBS=   23.7  SIGMA=   9.7  PHAS=   -31.7  FOM=  0.50  TEST= 0
INDE  1  51  50  FOBS=   60.1  SIGMA=   3.8  PHAS=    37.9  FOM=  0.65  TEST= 0
INDE  1  51  52  FOBS=   44.8  SIGMA=   5.9  PHAS=  -139.7  FOM=  0.14  TEST= 1
INDE  1  51  54  FOBS=   94.0  SIGMA=   2.0  PHAS=   132.4  FOM=  0.89  TEST= 0
INDE  1  51  56  FOBS=    0.0  SIGMA=  20.1  PHAS=     0.0  FOM=  0.00  TEST= 0
INDE  1  51  58  FOBS=   39.5  SIGMA=   6.2  PHAS=  -125.4  FOM=  0.12  TEST= 0
INDE  1  52   1  FOBS=  103.0  SIGMA=   1.2  PHAS=  -116.9  FOM=  0.80  TEST= 0
INDE  1  52   3  FOBS=  157.1  SIGMA=   1.0  PHAS=    36.1  FOM=  0.92  TEST= 0
INDE  1  52  13  FOBS=  272.0  SIGMA=   1.0  PHAS=    14.9  FOM=  0.94  TEST= 0
INDE  1  52  15  FOBS=  113.0  SIGMA=   1.6  PHAS=   -36.8  FOM=  0.62  TEST= 1
INDE  1  52  17  FOBS=  110.4  SIGMA=   1.7  PHAS=    31.1  FOM=  0.86  TEST= 0
INDE  1  52  19  FOBS=  148.1  SIGMA=   1.4  PHAS=  -120.5  FOM=  0.95  TEST= 0
INDE  1  52  21  FOBS=   58.2  SIGMA=   3.6  PHAS=   -73.5  FOM=  0.89  TEST= 0
INDE  1  52  23  FOBS=   90.1  SIGMA=   2.3  PHAS=   -96.5  FOM=  0.86  TEST= 0
INDE  1  52  25  FOBS=   80.5  SIGMA=   3.7  PHAS=    55.7  FOM=  0.44  TEST= 0
INDE  1  52  27  FOBS=   49.8  SIGMA=   7.0  PHAS=  -120.9  FOM=  0.25  TEST= 0
INDE  1  52  29  FOBS=   62.1  SIGMA=   5.5  PHAS=  -134.6  FOM=  0.67  TEST= 0
INDE  1  52  31  FOBS=  101.2  SIGMA=   3.4  PHAS=   -93.6  FOM=  0.87  TEST= 0
INDE  1  52  33  FOBS=    0.0  SIGMA=  25.7  PHAS=     0.0  FOM=  0.00  TEST= 0
INDE  1  52  35  FOBS=   53.3  SIGMA=   4.5  PHAS=   -94.2  FOM=  0.82  TEST= 0
INDE  1  52  37  FOBS=  136.6  SIGMA=   1.8  PHAS=   -73.3  FOM=  0.95  TEST= 0
INDE  1  52  39  FOBS=   74.0  SIGMA=   2.5  PHAS=    87.3  FOM=  0.84  TEST= 0
INDE  1  52  41  FOBS=   26.8  SIGMA=   7.3  PHAS=    55.5  FOM=  0.26  TEST= 0
INDE  1  52  43  FOBS=   83.3  SIGMA=   2.2  PHAS=    97.6  FOM=  0.85  TEST= 0
INDE  1  52  45  FOBS=   64.6  SIGMA=   2.8  PHAS=    82.4  FOM=  0.04  TEST= 1
INDE  1  52  47  FOBS=   33.1  SIGMA=   6.2  PHAS=    32.4  FOM=  0.34  TEST= 0
INDE  1  52  49  FOBS=    0.0  SIGMA=  21.4  PHAS=     0.0  FOM=  0.00  TEST= 0
INDE  1  52  51  FOBS=   34.5  SIGMA=   7.1  PHAS=  -163.4  FOM=  0.68  TEST= 0
INDE  1  52  53  FOBS=   11.8  SIGMA=  15.3  PHAS=   -22.2  FOM=  0.23  TEST= 0
INDE  1  52  55  FOBS=   44.6  SIGMA=   4.3  PHAS=    14.7  FOM=  0.75  TEST= 0
INDE  1  52  57  FOBS=    0.0  SIGMA=  25.8  PHAS=     0.0  FOM=  0.00  TEST= 0
INDE  1  53   2  FOBS=  220.9  SIGMA=   1.0  PHAS=   168.6  FOM=  0.96  TEST= 0
INDE  1  53   4  FOBS=  225.3  SIGMA=   1.0  PHAS=   -78.4  FOM=  0.91  TEST= 0
INDE  1  53  14  FOBS=  129.0  SIGMA=   1.4  PHAS=  -131.0  FOM=  0.77  TEST= 0
INDE  1  53  16  FOBS=  162.4  SIGMA=   1.2  PHAS=  -166.5  FOM=  0.91  TEST= 0
INDE  1  53  18  FOBS=  142.6  SIGMA=   1.4  PHAS=   -56.2  FOM=  0.89  TEST= 0
INDE  1  53  20  FOBS=  270.4  SIGMA=   0.9  PHAS=  -160.8  FOM=  0.97  TEST= 0
INDE  1  53  22  FOBS=   90.9  SIGMA=   2.3  PHAS=   154.9  FOM=  0.91  TEST= 0
INDE  1  53  24  FOBS=   90.2  SIGMA=   2.3  PHAS=   100.5  FOM=  0.83  TEST= 0
INDE  1  53  26  FOBS=  119.9  SIGMA=   2.2  PHAS=  -165.5  FOM=  0.85  TEST= 0
INDE  1  53  28  FOBS=   21.7  SIGMA=  15.7  PHAS=   -88.4  FOM=  0.05  TEST= 0
INDE  1  53  30  FOBS=  140.9  SIGMA=   2.6  PHAS=   133.2  FOM=  0.94  TEST= 0
INDE  1  53  32  FOBS=   28.3  SIGMA=  11.8  PHAS=   -28.6  FOM=  0.33  TEST= 0
INDE  1  53  34  FOBS=  150.1  SIGMA=   1.9  PHAS=  -133.3  FOM=  0.97  TEST= 0
INDE  1  53  36  FOBS=   63.2  SIGMA=   3.7  PHAS=   -69.3  FOM=  0.76  TEST= 0
INDE  1  53  38  FOBS=  107.4  SIGMA=   2.2  PHAS=   106.9  FOM=  0.90  TEST= 0
INDE  1  53  40  FOBS=   51.5  SIGMA=   3.5  PHAS=   160.0  FOM=  0.14  TEST= 0
INDE  1  53  42  FOBS=   23.7  SIGMA=   7.5  PHAS=    91.0  FOM=  0.35  TEST= 0
INDE  1  53  44  FOBS=   95.2  SIGMA=   1.9  PHAS=   -34.9  FOM=  0.89  TEST= 0
INDE  1  53  46  FOBS=   42.0  SIGMA=   4.2  PHAS=  -110.4  FOM=  0.51  TEST= 0
INDE  1  53  48  FOBS=    0.0  SIGMA=  21.4  PHAS=     0.0  FOM=  0.00  TEST= 0
INDE  1  53  50  FOBS=   44.1  SIGMA=   5.6  PHAS=   104.7  FOM=  0.52  TEST= 0
INDE  1  53  52  FOBS=   14.8  SIGMA=  14.3  PHAS=   105.2  FOM=  0.23  TEST= 0
INDE  1  53  54  FOBS=    0.0  SIGMA=  19.6  PHAS=     0.0  FOM=  0.00  TEST= 1
INDE  1  53  56  FOBS=   23.0  SIGMA=  15.6  PHAS=   177.8  FOM=  0.19  TEST= 0
INDE  1  54   1  FOBS=  220.0  SIGMA=   0.8  PHAS=    95.4  FOM=  0.96  TEST= 0
INDE  1  54   3  FOBS=  171.9  SIGMA=   1.4  PHAS=    92.4  FOM=  0.92  TEST= 0
INDE  1  54  15  FOBS=  102.1  SIGMA=   1.7  PHAS=  -156.1  FOM=  0.77  TEST= 0
INDE  1  54  17  FOBS=   68.1  SIGMA=   2.7  PHAS=   172.9  FOM=  0.61  TEST= 0
INDE  1  54  19  FOBS=  171.5  SIGMA=   1.2  PHAS=   179.4  FOM=  0.96  TEST= 0
INDE  1  54  21  FOBS=   68.0  SIGMA=   2.9  PHAS=    63.9  FOM=  0.60  TEST= 0
```

*FIG. 12A - 45*

```
INDE  1  54  23  FOBS=  112.2  SIGMA=   1.9  PHAS=   37.0  FOM=  0.94  TEST=  0
INDE  1  54  25  FOBS=   76.1  SIGMA=   2.8  PHAS=   94.9  FOM=  0.77  TEST=  0
INDE  1  54  27  FOBS=   45.6  SIGMA=   4.9  PHAS= -166.1  FOM=  0.12  TEST=  0
INDE  1  54  29  FOBS=   70.2  SIGMA=   4.9  PHAS=  -22.1  FOM=  0.87  TEST=  0
INDE  1  54  31  FOBS=   46.3  SIGMA=   7.2  PHAS=  -34.0  FOM=  0.45  TEST=  0
INDE  1  54  33  FOBS=  121.7  SIGMA=   2.3  PHAS= -178.0  FOM=  0.94  TEST=  0
INDE  1  54  35  FOBS=  135.0  SIGMA=   1.9  PHAS= -162.3  FOM=  0.79  TEST=  1
INDE  1  54  37  FOBS=   70.1  SIGMA=   3.4  PHAS= -109.0  FOM=  0.90  TEST=  0
INDE  1  54  39  FOBS=   46.3  SIGMA=   4.6  PHAS=   85.1  FOM=  0.49  TEST=  0
INDE  1  54  41  FOBS=   19.6  SIGMA=   9.0  PHAS=   65.1  FOM=  0.27  TEST=  1
INDE  1  54  43  FOBS=   49.2  SIGMA=   3.7  PHAS=  -38.9  FOM=  0.20  TEST=  0
INDE  1  54  45  FOBS=   13.5  SIGMA=  14.4  PHAS= -106.1  FOM=  0.11  TEST=  0
INDE  1  54  47  FOBS=    3.9  SIGMA=  66.2  PHAS=  172.3  FOM=  0.02  TEST=  1
INDE  1  54  49  FOBS=    0.0  SIGMA=  21.6  PHAS=    0.0  FOM=  0.00  TEST=  0
INDE  1  54  51  FOBS=   29.8  SIGMA=   7.8  PHAS=    9.8  FOM=  0.33  TEST=  0
INDE  1  54  53  FOBS=    0.0  SIGMA=  21.3  PHAS=    0.0  FOM=  0.00  TEST=  0
INDE  1  54  55  FOBS=   57.4  SIGMA=   4.9  PHAS=   56.4  FOM=  0.42  TEST=  1
INDE  1  55   2  FOBS=  134.8  SIGMA=   1.1  PHAS=  -20.6  FOM=  0.72  TEST=  0
INDE  1  55   4  FOBS=  122.4  SIGMA=   1.2  PHAS= -144.1  FOM=  0.97  TEST=  0
INDE  1  55  16  FOBS=  113.1  SIGMA=   1.6  PHAS=   99.7  FOM=  0.92  TEST=  0
INDE  1  55  18  FOBS=   99.5  SIGMA=   1.8  PHAS=  133.5  FOM=  0.70  TEST=  0
INDE  1  55  20  FOBS=   66.9  SIGMA=   2.8  PHAS=  171.4  FOM=  0.47  TEST=  1
INDE  1  55  22  FOBS=  121.4  SIGMA=   1.7  PHAS=  149.7  FOM=  0.63  TEST=  0
INDE  1  55  24  FOBS=  151.0  SIGMA=   1.5  PHAS=  -15.8  FOM=  0.94  TEST=  0
INDE  1  55  26  FOBS=  152.6  SIGMA=   1.6  PHAS= -129.9  FOM=  0.94  TEST=  0
INDE  1  55  28  FOBS=   43.3  SIGMA=   5.2  PHAS=   14.6  FOM=  0.26  TEST=  0
INDE  1  55  30  FOBS=   25.5  SIGMA=  13.2  PHAS=  -89.4  FOM=  0.00  TEST=  1
INDE  1  55  32  FOBS=    5.6  SIGMA=  60.0  PHAS=    2.3  FOM=  0.06  TEST=  0
INDE  1  55  34  FOBS=   81.4  SIGMA=   3.0  PHAS=   93.4  FOM=  0.81  TEST=  0
INDE  1  55  36  FOBS=   71.0  SIGMA=   3.3  PHAS=  140.9  FOM=  0.09  TEST=  1
INDE  1  55  38  FOBS=   64.7  SIGMA=   3.7  PHAS=   30.3  FOM=  0.82  TEST=  0
INDE  1  55  40  FOBS=   87.9  SIGMA=   2.2  PHAS=   95.2  FOM=  0.88  TEST=  0
INDE  1  55  42  FOBS=   63.8  SIGMA=   2.8  PHAS=   45.1  FOM=  0.59  TEST=  0
INDE  1  55  44  FOBS=    0.0  SIGMA=  20.3  PHAS=    0.0  FOM=  0.00  TEST=  0
INDE  1  55  46  FOBS=   18.7  SIGMA=  10.4  PHAS=   64.0  FOM=  0.06  TEST=  0
INDE  1  55  48  FOBS=    0.0  SIGMA=  23.5  PHAS=    0.0  FOM=  0.00  TEST=  0
INDE  1  55  50  FOBS=    0.0  SIGMA=  21.7  PHAS=    0.0  FOM=  0.00  TEST=  0
INDE  1  55  52  FOBS=    0.0  SIGMA=  22.3  PHAS=    0.0  FOM=  0.00  TEST=  0
INDE  1  55  54  FOBS=   43.7  SIGMA=   7.3  PHAS=  104.9  FOM=  0.29  TEST=  0
INDE  1  56   1  FOBS=  130.8  SIGMA=   1.6  PHAS=  107.1  FOM=  0.88  TEST=  0
INDE  1  56   3  FOBS=   91.0  SIGMA=   1.6  PHAS=  111.1  FOM=  0.75  TEST=  0
INDE  1  56  15  FOBS=  149.1  SIGMA=   1.6  PHAS=  -18.5  FOM=  0.86  TEST=  0
INDE  1  56  17  FOBS=   24.5  SIGMA=   7.0  PHAS=   37.1  FOM=  0.30  TEST=  0
INDE  1  56  19  FOBS=   69.7  SIGMA=   2.6  PHAS=  -95.3  FOM=  0.68  TEST=  0
INDE  1  56  21  FOBS=   54.1  SIGMA=   3.5  PHAS=  -24.6  FOM=  0.87  TEST=  0
INDE  1  56  23  FOBS=   69.5  SIGMA=   2.9  PHAS=   67.1  FOM=  0.76  TEST=  0
INDE  1  56  25  FOBS=  129.6  SIGMA=   1.6  PHAS= -172.7  FOM=  0.94  TEST=  0
INDE  1  56  27  FOBS=   93.4  SIGMA=   2.5  PHAS=  133.6  FOM=  0.91  TEST=  0
INDE  1  56  29  FOBS=   46.1  SIGMA=   4.8  PHAS=  -54.3  FOM=  0.52  TEST=  0
INDE  1  56  31  FOBS=   33.2  SIGMA=  10.1  PHAS=  139.6  FOM=  0.47  TEST=  0
INDE  1  56  33  FOBS=   91.5  SIGMA=   3.1  PHAS= -136.8  FOM=  0.92  TEST=  0
INDE  1  56  35  FOBS=  110.2  SIGMA=   2.2  PHAS= -160.1  FOM=  0.91  TEST=  0
INDE  1  56  37  FOBS=   60.8  SIGMA=   3.9  PHAS=  -90.2  FOM=  0.86  TEST=  0
INDE  1  56  39  FOBS=  111.2  SIGMA=   2.2  PHAS=  -38.0  FOM=  0.86  TEST=  0
INDE  1  56  41  FOBS=   72.0  SIGMA=   2.5  PHAS=  -98.0  FOM=  0.15  TEST=  0
INDE  1  56  43  FOBS=   16.5  SIGMA=  11.3  PHAS=    3.2  FOM=  0.28  TEST=  1
INDE  1  56  45  FOBS=   82.9  SIGMA=   2.2  PHAS=    2.6  FOM=  0.74  TEST=  0
INDE  1  56  47  FOBS=   20.0  SIGMA=  11.8  PHAS=  -27.9  FOM=  0.15  TEST=  0
INDE  1  56  49  FOBS=   21.1  SIGMA=  12.4  PHAS=  -95.3  FOM=  0.12  TEST=  0
INDE  1  56  51  FOBS=   36.4  SIGMA=   7.1  PHAS=  -42.4  FOM=  0.23  TEST=  0
INDE  1  56  53  FOBS=    0.0  SIGMA=  25.1  PHAS=    0.0  FOM=  0.00  TEST=  0
INDE  1  57   2  FOBS=  116.7  SIGMA=   1.2  PHAS=    0.9  FOM=  0.86  TEST=  0
INDE  1  57   4  FOBS=  145.5  SIGMA=   1.2  PHAS=  174.0  FOM=  0.91  TEST=  0
INDE  1  57  16  FOBS=   26.2  SIGMA=   6.3  PHAS=  -69.4  FOM=  0.31  TEST=  0
INDE  1  57  18  FOBS=   87.1  SIGMA=   2.1  PHAS=  130.1  FOM=  0.89  TEST=  0
INDE  1  57  20  FOBS=   45.0  SIGMA=   4.1  PHAS=  -93.8  FOM=  0.21  TEST=  0
INDE  1  57  22  FOBS=   65.5  SIGMA=   2.9  PHAS=  127.3  FOM=  0.49  TEST=  0
INDE  1  57  24  FOBS=    0.0  SIGMA=  21.5  PHAS=    0.0  FOM=  0.00  TEST=  0
INDE  1  57  26  FOBS=   68.7  SIGMA=   2.6  PHAS=  -51.4  FOM=  0.82  TEST=  0
INDE  1  57  28  FOBS=   36.1  SIGMA=   6.3  PHAS=   33.3  FOM=  0.77  TEST=  0
```

*FIG. 12A - 46*

```
INDE   1   57   30 FOBS=    40.0 SIGMA=   6.4 PHAS=    40.9 FOM=  0.47  TEST= 0
INDE   1   57   32 FOBS=    57.1 SIGMA=   4.8 PHAS=    62.7 FOM=  0.25  TEST= 1
INDE   1   57   34 FOBS=   145.9 SIGMA=   1.8 PHAS=    60.0 FOM=  0.21  TEST= 1
INDE   1   57   36 FOBS=    71.1 SIGMA=   3.4 PHAS=  -152.7 FOM=  0.81  TEST= 0
INDE   1   57   38 FOBS=    46.8 SIGMA=   5.0 PHAS=    54.0 FOM=  0.17  TEST= 1
INDE   1   57   40 FOBS=    54.3 SIGMA=   4.3 PHAS=   137.7 FOM=  0.72  TEST= 0
INDE   1   57   42 FOBS=    71.1 SIGMA=   2.6 PHAS=   -84.4 FOM=  0.15  TEST= 1
INDE   1   57   44 FOBS=     0.0 SIGMA=  19.5 PHAS=     0.0 FOM=  0.00  TEST= 1
INDE   1   57   46 FOBS=    34.1 SIGMA=   7.2 PHAS=   -86.4 FOM=  0.45  TEST= 0
INDE   1   57   48 FOBS=    64.3 SIGMA=   3.8 PHAS=     3.1 FOM=  0.78  TEST= 0
INDE   1   57   50 FOBS=    28.1 SIGMA=  11.2 PHAS=   -70.7 FOM=  0.23  TEST= 0
INDE   1   57   52 FOBS=    28.1 SIGMA=  11.5 PHAS=   155.7 FOM=  0.28  TEST= 0
INDE   1   58    1 FOBS=   107.6 SIGMA=   2.0 PHAS=  -175.0 FOM=  0.94  TEST= 0
INDE   1   58    3 FOBS=   143.1 SIGMA=   1.0 PHAS=    28.5 FOM=  0.95  TEST= 0
INDE   1   58    5 FOBS=    66.8 SIGMA=   2.9 PHAS=  -107.3 FOM=  0.83  TEST= 0
INDE   1   58   17 FOBS=    40.6 SIGMA=   4.1 PHAS=    66.8 FOM=  0.15  TEST= 0
INDE   1   58   19 FOBS=    58.1 SIGMA=   3.1 PHAS=    12.8 FOM=  0.67  TEST= 1
INDE   1   58   21 FOBS=    35.0 SIGMA=   5.2 PHAS=  -116.7 FOM=  0.64  TEST= 0
INDE   1   58   23 FOBS=    58.5 SIGMA=   3.1 PHAS=   148.3 FOM=  0.73  TEST= 0
INDE   1   58   25 FOBS=    92.0 SIGMA=   2.0 PHAS=  -139.9 FOM=  0.89  TEST= 0
INDE   1   58   27 FOBS=    88.1 SIGMA=   2.1 PHAS=  -121.5 FOM=  0.67  TEST= 1
INDE   1   58   29 FOBS=    12.2 SIGMA=  24.7 PHAS=  -142.6 FOM=  0.15  TEST= 0
INDE   1   58   31 FOBS=    24.3 SIGMA=  13.8 PHAS=    30.5 FOM=  0.24  TEST= 0
INDE   1   58   33 FOBS=    32.0 SIGMA=   7.5 PHAS=   131.8 FOM=  0.50  TEST= 0
INDE   1   58   35 FOBS=    69.1 SIGMA=   3.5 PHAS=   129.1 FOM=  0.84  TEST= 0
INDE   1   58   37 FOBS=    13.3 SIGMA=  20.1 PHAS=   109.4 FOM=  0.22  TEST= 0
INDE   1   58   39 FOBS=     0.0 SIGMA=  21.7 PHAS=     0.0 FOM=  0.00  TEST= 1
INDE   1   58   41 FOBS=    96.8 SIGMA=   2.3 PHAS=   159.9 FOM=  0.84  TEST= 0
INDE   1   58   43 FOBS=     0.0 SIGMA=  20.0 PHAS=     0.0 FOM=  0.00  TEST= 0
INDE   1   58   45 FOBS=    10.1 SIGMA=  20.7 PHAS=    76.0 FOM=  0.09  TEST= 0
INDE   1   58   47 FOBS=    60.8 SIGMA=   4.0 PHAS=   -97.1 FOM=  0.85  TEST= 0
INDE   1   58   49 FOBS=    68.0 SIGMA=   4.9 PHAS=  -131.8 FOM=  0.90  TEST= 0
INDE   1   58   51 FOBS=     0.0 SIGMA=  25.6 PHAS=     0.0 FOM=  0.00  TEST= 0
INDE   1   59    2 FOBS=    52.5 SIGMA=   3.1 PHAS=   -41.2 FOM=  0.67  TEST= 0
INDE   1   59    4 FOBS=    88.3 SIGMA=   1.6 PHAS=   -80.7 FOM=  0.32  TEST= 0
INDE   1   59   16 FOBS=     5.9 SIGMA=  51.2 PHAS=    -7.8 FOM=  0.13  TEST= 0
INDE   1   59   18 FOBS=    44.4 SIGMA=   3.8 PHAS=    60.3 FOM=  0.82  TEST= 0
INDE   1   59   20 FOBS=    32.5 SIGMA=   5.6 PHAS=    19.9 FOM=  0.57  TEST= 0
INDE   1   59   22 FOBS=    68.0 SIGMA=   2.8 PHAS=   117.3 FOM=  0.62  TEST= 1
INDE   1   59   24 FOBS=     5.0 SIGMA=  36.8 PHAS=   145.5 FOM=  0.12  TEST= 0
INDE   1   59   26 FOBS=    43.5 SIGMA=   4.1 PHAS=  -167.6 FOM=  0.51  TEST= 0
INDE   1   59   28 FOBS=    77.9 SIGMA=   2.7 PHAS=    88.9 FOM=  0.86  TEST= 0
INDE   1   59   30 FOBS=    71.0 SIGMA=   3.3 PHAS=   145.1 FOM=  0.39  TEST= 0
INDE   1   59   32 FOBS=    68.3 SIGMA=   4.1 PHAS=    16.9 FOM=  0.87  TEST= 0
INDE   1   59   34 FOBS=   105.8 SIGMA=   2.4 PHAS=    35.1 FOM=  0.94  TEST= 0
INDE   1   59   36 FOBS=     0.0 SIGMA=  25.8 PHAS=     0.0 FOM=  0.00  TEST= 0
INDE   1   59   38 FOBS=    72.5 SIGMA=   3.4 PHAS=  -126.2 FOM=  0.74  TEST= 0
INDE   1   59   40 FOBS=    64.6 SIGMA=   3.7 PHAS=   139.1 FOM=  0.55  TEST= 0
INDE   1   59   42 FOBS=     0.0 SIGMA=  21.0 PHAS=     0.0 FOM=  0.00  TEST= 0
INDE   1   59   44 FOBS=    35.9 SIGMA=   5.1 PHAS=   158.3 FOM=  0.30  TEST= 0
INDE   1   59   46 FOBS=    74.2 SIGMA=   3.1 PHAS=   157.5 FOM=  0.70  TEST= 0
INDE   1   59   48 FOBS=    36.4 SIGMA=   8.9 PHAS=   139.7 FOM=  0.67  TEST= 0
INDE   1   59   50 FOBS=    25.3 SIGMA=  12.9 PHAS=   166.8 FOM=  0.53  TEST= 0
INDE   1   60    1 FOBS=    98.2 SIGMA=   2.2 PHAS=   126.1 FOM=  0.76  TEST= 0
INDE   1   60    3 FOBS=    73.8 SIGMA=   1.8 PHAS=   -29.8 FOM=  0.77  TEST= 0
INDE   1   60    5 FOBS=    32.2 SIGMA=   4.4 PHAS=   157.3 FOM=  0.21  TEST= 0
INDE   1   60   17 FOBS=    80.0 SIGMA=   2.8 PHAS=   -75.8 FOM=  0.86  TEST= 0
INDE   1   60   19 FOBS=    82.7 SIGMA=   3.0 PHAS=   -19.1 FOM=  0.81  TEST= 0
INDE   1   60   21 FOBS=    38.2 SIGMA=   6.8 PHAS=  -171.9 FOM=  0.09  TEST= 0
INDE   1   60   23 FOBS=    38.5 SIGMA=   6.1 PHAS=  -172.7 FOM=  0.43  TEST= 0
INDE   1   60   25 FOBS=    66.9 SIGMA=   3.4 PHAS=    70.1 FOM=  0.12  TEST= 1
INDE   1   60   27 FOBS=    81.3 SIGMA=   2.9 PHAS=   -64.5 FOM=  0.87  TEST= 0
INDE   1   60   29 FOBS=    23.1 SIGMA=  10.2 PHAS=   178.3 FOM=  0.26  TEST= 0
INDE   1   60   31 FOBS=    65.7 SIGMA=   3.7 PHAS=   -86.8 FOM=  0.23  TEST= 1
INDE   1   60   33 FOBS=    91.6 SIGMA=   2.7 PHAS=   -26.9 FOM=  0.82  TEST= 0
INDE   1   60   35 FOBS=    61.0 SIGMA=   4.0 PHAS=  -109.7 FOM=  0.75  TEST= 0
INDE   1   60   37 FOBS=    48.7 SIGMA=   5.0 PHAS=   116.8 FOM=  0.86  TEST= 0
INDE   1   60   39 FOBS=    48.6 SIGMA=   5.0 PHAS=  -168.3 FOM=  0.51  TEST= 0
INDE   1   60   41 FOBS=    24.3 SIGMA=  11.5 PHAS=  -157.3 FOM=  0.28  TEST= 0
INDE   1   60   43 FOBS=    10.5 SIGMA=  18.2 PHAS=  -160.9 FOM=  0.15  TEST= 0
```

*FIG. 12A - 47*

```
INDE  1  60  45  FOBS=   24.2  SIGMA=   9.0  PHAS=  -37.7  FOM=  0.60  TEST= 0
INDE  1  60  47  FOBS=    0.0  SIGMA=  25.7  PHAS=    0.0  FOM=  0.00  TEST= 0
INDE  1  60  49  FOBS=   56.9  SIGMA=   6.0  PHAS=  120.4  FOM=  0.71  TEST= 0
INDE  1  61   2  FOBS=  183.4  SIGMA=   1.2  PHAS=  131.2  FOM=  0.90  TEST= 0
INDE  1  61   4  FOBS=   90.5  SIGMA=   1.5  PHAS=  119.0  FOM=  0.63  TEST= 0
INDE  1  61   6  FOBS=   49.4  SIGMA=   3.9  PHAS= -116.1  FOM=  0.38  TEST= 0
INDE  1  61  18  FOBS=   52.5  SIGMA=   4.4  PHAS=  131.6  FOM=  0.59  TEST= 0
INDE  1  61  20  FOBS=   45.4  SIGMA=   5.6  PHAS=  138.5  FOM=  0.83  TEST= 0
INDE  1  61  22  FOBS=   65.0  SIGMA=   3.6  PHAS=  175.4  FOM=  0.58  TEST= 0
INDE  1  61  24  FOBS=    0.0  SIGMA=  21.9  PHAS=    0.0  FOM=  0.00  TEST= 0
INDE  1  61  26  FOBS=  127.2  SIGMA=   1.9  PHAS=  -32.2  FOM=  0.32  TEST= 1
INDE  1  61  28  FOBS=   41.1  SIGMA=   5.8  PHAS=   13.7  FOM=  0.44  TEST= 0
INDE  1  61  30  FOBS=   24.3  SIGMA=   9.8  PHAS= -174.9  FOM=  0.12  TEST= 0
INDE  1  61  32  FOBS=   52.8  SIGMA=   4.1  PHAS=   72.6  FOM=  0.68  TEST= 0
INDE  1  61  34  FOBS=   90.4  SIGMA=   2.8  PHAS=   39.1  FOM=  0.17  TEST= 1
INDE  1  61  36  FOBS=  108.9  SIGMA=   2.3  PHAS=   64.6  FOM=  0.93  TEST= 0
INDE  1  61  38  FOBS=   43.0  SIGMA=   5.6  PHAS=  -17.3  FOM=  0.52  TEST= 0
INDE  1  61  40  FOBS=   51.1  SIGMA=   4.7  PHAS= -140.2  FOM=  0.85  TEST= 0
INDE  1  61  42  FOBS=    0.0  SIGMA=  24.0  PHAS=    0.0  FOM=  0.00  TEST= 0
INDE  1  61  44  FOBS=   37.2  SIGMA=   5.4  PHAS= -158.7  FOM=  0.66  TEST= 0
INDE  1  61  46  FOBS=   44.7  SIGMA=   7.6  PHAS=  -52.8  FOM=  0.54  TEST= 0
INDE  1  61  48  FOBS=   80.9  SIGMA=   4.3  PHAS=   18.2  FOM=  0.88  TEST= 0
INDE  1  62   1  FOBS=  176.5  SIGMA=   1.8  PHAS=  -60.0  FOM=  0.95  TEST= 0
INDE  1  62   3  FOBS=    0.0  SIGMA=  19.8  PHAS=    0.0  FOM=  0.00  TEST= 0
INDE  1  62   5  FOBS=   93.6  SIGMA=   2.3  PHAS=   75.7  FOM=  0.93  TEST= 0
INDE  1  62  19  FOBS=   15.6  SIGMA=  14.9  PHAS=   93.9  FOM=  0.25  TEST= 0
INDE  1  62  21  FOBS=   75.5  SIGMA=   3.1  PHAS=  113.4  FOM=  0.79  TEST= 1
INDE  1  62  23  FOBS=  110.2  SIGMA=   2.0  PHAS= -145.9  FOM=  0.88  TEST= 0
INDE  1  62  25  FOBS=    0.0  SIGMA=  20.9  PHAS=    0.0  FOM=  0.00  TEST= 0
INDE  1  62  27  FOBS=    0.0  SIGMA=  23.3  PHAS=    0.0  FOM=  0.00  TEST= 0
INDE  1  62  29  FOBS=   45.0  SIGMA=   6.2  PHAS= -109.6  FOM=  0.27  TEST= 0
INDE  1  62  31  FOBS=   44.6  SIGMA=   4.5  PHAS=   -2.4  FOM=  0.81  TEST= 0
INDE  1  62  33  FOBS=   91.2  SIGMA=   2.5  PHAS=    7.3  FOM=  0.91  TEST= 0
INDE  1  62  35  FOBS=   81.0  SIGMA=   3.1  PHAS=  -61.7  FOM=  0.87  TEST= 0
INDE  1  62  37  FOBS=   34.0  SIGMA=   7.2  PHAS=  -48.4  FOM=  0.33  TEST= 0
INDE  1  62  39  FOBS=   36.9  SIGMA=   6.6  PHAS=  131.7  FOM=  0.62  TEST= 0
INDE  1  62  41  FOBS=    0.0  SIGMA=  22.0  PHAS=    0.0  FOM=  0.00  TEST= 0
INDE  1  62  43  FOBS=   16.3  SIGMA=  13.1  PHAS=  123.8  FOM=  0.46  TEST= 0
INDE  1  62  45  FOBS=   34.3  SIGMA=  10.0  PHAS=    4.1  FOM=  0.59  TEST= 0
INDE  1  63   4  FOBS=    2.0  SIGMA=  96.1  PHAS= -166.5  FOM=  0.05  TEST= 0
INDE  1  63   6  FOBS=  105.2  SIGMA=   2.1  PHAS=  -15.6  FOM=  0.87  TEST= 0
INDE  1  63  18  FOBS=   25.4  SIGMA=  11.9  PHAS=  -19.9  FOM=  0.15  TEST= 0
INDE  1  63  20  FOBS=    0.0  SIGMA=  21.8  PHAS=    0.0  FOM=  0.00  TEST= 0
INDE  1  63  22  FOBS=  105.8  SIGMA=   2.1  PHAS=  106.9  FOM=  0.91  TEST= 0
INDE  1  63  24  FOBS=   76.0  SIGMA=   2.9  PHAS=  171.4  FOM=  0.89  TEST= 0
INDE  1  63  26  FOBS=   41.2  SIGMA=   5.4  PHAS=  138.5  FOM=  0.61  TEST= 0
INDE  1  63  28  FOBS=   35.6  SIGMA=   9.8  PHAS=  146.6  FOM=  0.53  TEST= 0
INDE  1  63  30  FOBS=   71.1  SIGMA=   3.0  PHAS=   46.0  FOM=  0.83  TEST= 0
INDE  1  63  32  FOBS=   25.5  SIGMA=   8.5  PHAS=  137.4  FOM=  0.48  TEST= 0
INDE  1  63  34  FOBS=    0.0  SIGMA=  22.2  PHAS=    0.0  FOM=  0.00  TEST= 0
INDE  1  63  36  FOBS=   62.2  SIGMA=   4.0  PHAS=  158.3  FOM=  0.90  TEST= 0
INDE  1  63  38  FOBS=   29.8  SIGMA=   9.6  PHAS= -158.5  FOM=  0.09  TEST= 1
INDE  1  63  40  FOBS=   35.2  SIGMA=   7.0  PHAS=  -16.2  FOM=  0.26  TEST= 0
INDE  1  63  42  FOBS=   20.3  SIGMA=  14.1  PHAS=  115.3  FOM=  0.05  TEST= 0
INDE  1  63  44  FOBS=    0.0  SIGMA=  26.5  PHAS=    0.0  FOM=  0.00  TEST= 0
INDE  1  64   5  FOBS=   42.7  SIGMA=   4.6  PHAS= -170.5  FOM=  0.50  TEST= 0
INDE  1  64   7  FOBS=   33.4  SIGMA=   8.5  PHAS=  -58.7  FOM=  0.32  TEST= 0
INDE  1  64  19  FOBS=   68.1  SIGMA=   3.4  PHAS= -159.9  FOM=  0.78  TEST= 0
INDE  1  64  21  FOBS=   31.3  SIGMA=   6.9  PHAS= -175.2  FOM=  0.58  TEST= 0
INDE  1  64  23  FOBS=   33.1  SIGMA=   6.7  PHAS=   76.2  FOM=  0.26  TEST= 0
INDE  1  64  25  FOBS=   63.3  SIGMA=   3.5  PHAS=   43.9  FOM=  0.56  TEST= 0
INDE  1  64  27  FOBS=   55.9  SIGMA=   4.1  PHAS= -164.7  FOM=  0.56  TEST= 0
INDE  1  64  29  FOBS=   23.3  SIGMA=  10.4  PHAS=  -32.1  FOM=  0.44  TEST= 0
INDE  1  64  31  FOBS=   97.2  SIGMA=   2.1  PHAS=   10.0  FOM=  0.95  TEST= 0
INDE  1  64  33  FOBS=   55.7  SIGMA=   3.7  PHAS=   34.5  FOM=  0.72  TEST= 0
INDE  1  64  35  FOBS=   55.1  SIGMA=   4.5  PHAS=   25.4  FOM=  0.55  TEST= 0
INDE  1  64  37  FOBS=   42.3  SIGMA=   5.9  PHAS=   81.0  FOM=  0.58  TEST= 0
INDE  1  64  39  FOBS=   58.7  SIGMA=   4.3  PHAS=   -8.5  FOM=  0.57  TEST= 0
INDE  1  64  41  FOBS=   48.2  SIGMA=   5.3  PHAS=   55.7  FOM=  0.75  TEST= 0
INDE  1  64  43  FOBS=    0.0  SIGMA=  26.7  PHAS=    0.0  FOM=  0.00  TEST= 0
```

*FIG. 12A - 48*

| | | | | | | | | | | | |
|---|---|---|---|---|---|---|---|---|---|---|---|
| INDE | 1 | 65 | 2 | FOBS= | 115.8 | SIGMA= | 2.7 | PHAS= | -147.2 | FOM= | 0.87 | TEST= 0
| INDE | 1 | 65 | 4 | FOBS= | 50.8 | SIGMA= | 3.8 | PHAS= | -108.8 | FOM= | 0.76 | TEST= 0
| INDE | 1 | 65 | 6 | FOBS= | 32.5 | SIGMA= | 6.3 | PHAS= | 30.4 | FOM= | 0.37 | TEST= 0
| INDE | 1 | 65 | 20 | FOBS= | 50.9 | SIGMA= | 4.1 | PHAS= | 147.7 | FOM= | 0.76 | TEST= 0
| INDE | 1 | 65 | 22 | FOBS= | 71.3 | SIGMA= | 2.9 | PHAS= | 31.9 | FOM= | 0.83 | TEST= 0
| INDE | 1 | 65 | 24 | FOBS= | 0.0 | SIGMA= | 20.9 | PHAS= | 0.0 | FOM= | 0.00 | TEST= 0
| INDE | 1 | 65 | 26 | FOBS= | 43.9 | SIGMA= | 5.0 | PHAS= | -68.0 | FOM= | 0.18 | TEST= 0
| INDE | 1 | 65 | 28 | FOBS= | 66.3 | SIGMA= | 3.2 | PHAS= | 151.8 | FOM= | 0.74 | TEST= 0
| INDE | 1 | 65 | 30 | FOBS= | 26.0 | SIGMA= | 10.8 | PHAS= | 96.7 | FOM= | 0.64 | TEST= 0
| INDE | 1 | 65 | 32 | FOBS= | 23.0 | SIGMA= | 9.7 | PHAS= | 113.6 | FOM= | 0.49 | TEST= 0
| INDE | 1 | 65 | 34 | FOBS= | 55.1 | SIGMA= | 3.8 | PHAS= | -107.8 | FOM= | 0.84 | TEST= 0
| INDE | 1 | 65 | 36 | FOBS= | 52.6 | SIGMA= | 4.3 | PHAS= | -47.7 | FOM= | 0.04 | TEST= 1
| INDE | 1 | 65 | 38 | FOBS= | 71.7 | SIGMA= | 3.6 | PHAS= | -37.1 | FOM= | 0.84 | TEST= 0
| INDE | 1 | 65 | 40 | FOBS= | 41.6 | SIGMA= | 6.2 | PHAS= | 13.0 | FOM= | 0.77 | TEST= 0
| INDE | 1 | 65 | 42 | FOBS= | 59.2 | SIGMA= | 4.4 | PHAS= | -38.2 | FOM= | 0.85 | TEST= 0
| INDE | 1 | 66 | 5 | FOBS= | 20.3 | SIGMA= | 9.3 | PHAS= | -5.0 | FOM= | 0.47 | TEST= 0
| INDE | 1 | 66 | 7 | FOBS= | 46.9 | SIGMA= | 4.6 | PHAS= | -3.4 | FOM= | 0.19 | TEST= 0
| INDE | 1 | 66 | 19 | FOBS= | 71.5 | SIGMA= | 6.9 | PHAS= | 103.4 | FOM= | 0.29 | TEST= 0
| INDE | 1 | 66 | 21 | FOBS= | 65.0 | SIGMA= | 3.1 | PHAS= | -83.2 | FOM= | 0.07 | TEST= 1
| INDE | 1 | 66 | 23 | FOBS= | 68.1 | SIGMA= | 3.2 | PHAS= | -169.6 | FOM= | 0.82 | TEST= 0
| INDE | 1 | 66 | 25 | FOBS= | 40.0 | SIGMA= | 5.6 | PHAS= | 110.9 | FOM= | 0.55 | TEST= 0
| INDE | 1 | 66 | 27 | FOBS= | 25.9 | SIGMA= | 9.6 | PHAS= | 160.5 | FOM= | 0.18 | TEST= 0
| INDE | 1 | 66 | 29 | FOBS= | 53.4 | SIGMA= | 3.7 | PHAS= | 61.0 | FOM= | 0.79 | TEST= 0
| INDE | 1 | 66 | 31 | FOBS= | 88.7 | SIGMA= | 2.6 | PHAS= | 17.9 | FOM= | 0.94 | TEST= 0
| INDE | 1 | 66 | 33 | FOBS= | 103.1 | SIGMA= | 2.1 | PHAS= | 74.4 | FOM= | 0.91 | TEST= 0
| INDE | 1 | 66 | 35 | FOBS= | 35.3 | SIGMA= | 6.5 | PHAS= | 134.2 | FOM= | 0.45 | TEST= 0
| INDE | 1 | 66 | 37 | FOBS= | 38.4 | SIGMA= | 6.0 | PHAS= | -124.5 | FOM= | 0.66 | TEST= 0
| INDE | 1 | 66 | 39 | FOBS= | 37.8 | SIGMA= | 6.8 | PHAS= | -81.6 | FOM= | 0.70 | TEST= 0
| INDE | 1 | 66 | 41 | FOBS= | 31.2 | SIGMA= | 12.0 | PHAS= | -137.8 | FOM= | 0.52 | TEST= 0
| INDE | 1 | 67 | 4 | FOBS= | 86.2 | SIGMA= | 3.3 | PHAS= | -133.2 | FOM= | 0.77 | TEST= 0
| INDE | 1 | 67 | 6 | FOBS= | 4.6 | SIGMA= | 41.6 | PHAS= | -0.5 | FOM= | 0.10 | TEST= 1
| INDE | 1 | 67 | 18 | FOBS= | 43.4 | SIGMA= | 11.1 | PHAS= | -134.9 | FOM= | 0.50 | TEST= 0
| INDE | 1 | 67 | 20 | FOBS= | 0.0 | SIGMA= | 26.5 | PHAS= | 0.0 | FOM= | 0.00 | TEST= 0
| INDE | 1 | 67 | 22 | FOBS= | 32.7 | SIGMA= | 6.8 | PHAS= | 52.2 | FOM= | 0.29 | TEST= 0
| INDE | 1 | 67 | 24 | FOBS= | 31.3 | SIGMA= | 7.0 | PHAS= | 38.0 | FOM= | 0.10 | TEST= 1
| INDE | 1 | 67 | 26 | FOBS= | 77.3 | SIGMA= | 3.0 | PHAS= | -164.0 | FOM= | 0.83 | TEST= 0
| INDE | 1 | 67 | 28 | FOBS= | 57.2 | SIGMA= | 3.7 | PHAS= | -24.3 | FOM= | 0.25 | TEST= 1
| INDE | 1 | 67 | 30 | FOBS= | 62.0 | SIGMA= | 3.3 | PHAS= | 56.2 | FOM= | 0.85 | TEST= 0
| INDE | 1 | 67 | 32 | FOBS= | 45.4 | SIGMA= | 5.0 | PHAS= | -136.7 | FOM= | 0.56 | TEST= 0
| INDE | 1 | 67 | 34 | FOBS= | 87.7 | SIGMA= | 2.7 | PHAS= | -52.7 | FOM= | 0.92 | TEST= 0
| INDE | 1 | 67 | 36 | FOBS= | 60.3 | SIGMA= | 3.5 | PHAS= | -178.4 | FOM= | 0.83 | TEST= 0
| INDE | 1 | 67 | 38 | FOBS= | 20.9 | SIGMA= | 11.2 | PHAS= | -64.4 | FOM= | 0.14 | TEST= 0
| INDE | 1 | 68 | 3 | FOBS= | 129.2 | SIGMA= | 2.4 | PHAS= | -31.2 | FOM= | 0.92 | TEST= 0
| INDE | 1 | 68 | 5 | FOBS= | 34.3 | SIGMA= | 5.6 | PHAS= | 57.2 | FOM= | 0.59 | TEST= 0
| INDE | 1 | 68 | 7 | FOBS= | 63.4 | SIGMA= | 3.3 | PHAS= | 11.2 | FOM= | 0.88 | TEST= 0
| INDE | 1 | 68 | 17 | FOBS= | 97.9 | SIGMA= | 5.1 | PHAS= | 106.0 | FOM= | 0.75 | TEST= 0
| INDE | 1 | 68 | 19 | FOBS= | 73.4 | SIGMA= | 4.9 | PHAS= | -21.3 | FOM= | 0.39 | TEST= 0
| INDE | 1 | 68 | 21 | FOBS= | 14.9 | SIGMA= | 16.2 | PHAS= | -170.4 | FOM= | 0.58 | TEST= 0
| INDE | 1 | 68 | 23 | FOBS= | 124.1 | SIGMA= | 1.8 | PHAS= | -163.1 | FOM= | 0.94 | TEST= 0
| INDE | 1 | 68 | 25 | FOBS= | 102.6 | SIGMA= | 2.3 | PHAS= | 56.2 | FOM= | 0.48 | TEST= 1
| INDE | 1 | 68 | 27 | FOBS= | 0.0 | SIGMA= | 21.5 | PHAS= | 0.0 | FOM= | 0.00 | TEST= 0
| INDE | 1 | 68 | 29 | FOBS= | 0.0 | SIGMA= | 19.8 | PHAS= | 0.0 | FOM= | 0.00 | TEST= 0
| INDE | 1 | 68 | 31 | FOBS= | 26.7 | SIGMA= | 8.5 | PHAS= | 50.9 | FOM= | 0.15 | TEST= 1
| INDE | 1 | 68 | 33 | FOBS= | 14.9 | SIGMA= | 15.3 | PHAS= | 135.2 | FOM= | 0.36 | TEST= 0
| INDE | 1 | 68 | 35 | FOBS= | 64.2 | SIGMA= | 3.7 | PHAS= | 164.0 | FOM= | 0.91 | TEST= 0
| INDE | 1 | 68 | 37 | FOBS= | 0.0 | SIGMA= | 24.8 | PHAS= | 0.0 | FOM= | 0.00 | TEST= 0
| INDE | 1 | 69 | 4 | FOBS= | 55.7 | SIGMA= | 5.3 | PHAS= | 170.9 | FOM= | 0.34 | TEST= 0
| INDE | 1 | 69 | 6 | FOBS= | 55.9 | SIGMA= | 3.4 | PHAS= | -147.0 | FOM= | 0.84 | TEST= 0
| INDE | 1 | 69 | 8 | FOBS= | 22.0 | SIGMA= | 9.8 | PHAS= | -124.6 | FOM= | 0.30 | TEST= 0
| INDE | 1 | 69 | 18 | FOBS= | 57.6 | SIGMA= | 6.2 | PHAS= | -40.2 | FOM= | 0.58 | TEST= 0
| INDE | 1 | 69 | 20 | FOBS= | 42.3 | SIGMA= | 8.6 | PHAS= | 121.9 | FOM= | 0.55 | TEST= 0
| INDE | 1 | 69 | 22 | FOBS= | 141.6 | SIGMA= | 1.6 | PHAS= | 49.9 | FOM= | 0.95 | TEST= 0
| INDE | 1 | 69 | 24 | FOBS= | 51.2 | SIGMA= | 5.2 | PHAS= | 37.5 | FOM= | 0.74 | TEST= 0
| INDE | 1 | 69 | 26 | FOBS= | 0.0 | SIGMA= | 21.4 | PHAS= | 0.0 | FOM= | 0.00 | TEST= 0
| INDE | 1 | 69 | 28 | FOBS= | 63.3 | SIGMA= | 3.2 | PHAS= | 39.6 | FOM= | 0.75 | TEST= 0
| INDE | 1 | 69 | 30 | FOBS= | 91.6 | SIGMA= | 2.3 | PHAS= | -62.4 | FOM= | 0.83 | TEST= 0
| INDE | 1 | 69 | 32 | FOBS= | 45.2 | SIGMA= | 4.6 | PHAS= | -29.1 | FOM= | 0.66 | TEST= 0
| INDE | 1 | 69 | 34 | FOBS= | 13.5 | SIGMA= | 19.5 | PHAS= | -46.7 | FOM= | 0.36 | TEST= 0
| INDE | 1 | 70 | 5 | FOBS= | 53.7 | SIGMA= | 5.1 | PHAS= | 16.4 | FOM= | 0.79 | TEST= 0
| INDE | 1 | 70 | 7 | FOBS= | 95.5 | SIGMA= | 2.1 | PHAS= | 21.3 | FOM= | 0.92 | TEST= 0

*FIG. 12A - 49*

```
INDE    1   70   19  FOBS=     0.0  SIGMA=   32.1  PHAS=     0.0  FOM=  0.00  TEST=  0
INDE    1   70   21  FOBS=   101.6  SIGMA=    5.5  PHAS=   -96.5  FOM=  0.94  TEST=  0
INDE    1   70   23  FOBS=     0.0  SIGMA=   21.3  PHAS=     0.0  FOM=  0.00  TEST=  0
INDE    1   70   25  FOBS=     0.0  SIGMA=   20.7  PHAS=     0.0  FOM=  0.00  TEST=  0
INDE    1   70   27  FOBS=    70.6  SIGMA=    2.9  PHAS=  -101.4  FOM=  0.92  TEST=  0
INDE    1   70   29  FOBS=    96.8  SIGMA=    2.1  PHAS=   139.4  FOM=  0.92  TEST=  0
INDE    1   70   31  FOBS=    41.3  SIGMA=    5.1  PHAS=  -154.6  FOM=  0.61  TEST=  0
INDE    1   70   33  FOBS=    42.4  SIGMA=    5.1  PHAS=   162.4  FOM=  0.68  TEST=  0
INDE    1   71    4  FOBS=    48.6  SIGMA=    6.1  PHAS=   -89.0  FOM=  0.75  TEST=  0
INDE    1   71    6  FOBS=    58.2  SIGMA=    3.3  PHAS=  -148.4  FOM=  0.71  TEST=  0
INDE    1   71    8  FOBS=    44.2  SIGMA=    4.8  PHAS=   -67.6  FOM=  0.82  TEST=  0
INDE    1   71   24  FOBS=     4.4  SIGMA=   52.1  PHAS=   144.4  FOM=  0.02  TEST=  0
INDE    1   71   26  FOBS=    28.0  SIGMA=    8.1  PHAS=   137.9  FOM=  0.48  TEST=  0
INDE    1   71   28  FOBS=    34.4  SIGMA=    6.0  PHAS=    99.0  FOM=  0.80  TEST=  0
INDE    1   71   30  FOBS=    37.3  SIGMA=    8.4  PHAS=    96.4  FOM=  0.21  TEST=  1
INDE    1   72    5  FOBS=    23.1  SIGMA=   12.6  PHAS=  -172.0  FOM=  0.58  TEST=  0
INDE    1   72    7  FOBS=    21.4  SIGMA=    8.9  PHAS=     9.6  FOM=  0.83  TEST=  0
INDE    1   72    9  FOBS=    71.9  SIGMA=    3.1  PHAS=   169.9  FOM=  0.79  TEST=  0
INDE    1   72   23  FOBS=    20.7  SIGMA=   16.1  PHAS=    52.3  FOM=  0.16  TEST=  0
INDE    1   72   25  FOBS=     0.0  SIGMA=   23.3  PHAS=     0.0  FOM=  0.00  TEST=  0
INDE    1   72   27  FOBS=    39.3  SIGMA=    7.7  PHAS=   119.1  FOM=  0.33  TEST=  0
INDE    1   72   29  FOBS=    70.4  SIGMA=    3.7  PHAS=   141.6  FOM=  0.62  TEST=  0
INDE    1   73    6  FOBS=    35.1  SIGMA=    7.8  PHAS=    11.4  FOM=  0.54  TEST=  0
INDE    1   73    8  FOBS=    37.6  SIGMA=    5.1  PHAS=   -45.8  FOM=  0.61  TEST=  0
INDE    1   73   10  FOBS=    49.8  SIGMA=    5.8  PHAS=   180.0  FOM=  0.00  TEST=  1
INDE    1   73   24  FOBS=    13.4  SIGMA=   26.0  PHAS=   108.2  FOM=  0.03  TEST=  1
INDE    1   73   26  FOBS=    35.8  SIGMA=    7.8  PHAS=   -16.6  FOM=  0.52  TEST=  0
INDE    1   74    5  FOBS=    35.8  SIGMA=    8.1  PHAS=   -62.3  FOM=  0.36  TEST=  0
INDE    1   74    7  FOBS=    64.6  SIGMA=    2.9  PHAS=   -45.0  FOM=  0.82  TEST=  0
INDE    1   74    9  FOBS=     0.0  SIGMA=   20.9  PHAS=     0.0  FOM=  0.00  TEST=  0
INDE    1   75    6  FOBS=    97.0  SIGMA=    3.1  PHAS=   -53.0  FOM=  0.81  TEST=  0
INDE    1   75    8  FOBS=    49.8  SIGMA=    3.8  PHAS=  -116.0  FOM=  0.82  TEST=  0
INDE    1   75   10  FOBS=    20.8  SIGMA=   10.8  PHAS=   139.6  FOM=  0.06  TEST=  0
INDE    1   76    7  FOBS=    81.1  SIGMA=    3.7  PHAS=   109.5  FOM=  0.29  TEST=  0
INDE    1   76    9  FOBS=     0.0  SIGMA=   20.0  PHAS=     0.0  FOM=  0.00  TEST=  0
INDE    1   76   11  FOBS=     8.7  SIGMA=   34.5  PHAS=   110.7  FOM=  0.17  TEST=  0
INDE    1   77    6  FOBS=    55.1  SIGMA=    5.4  PHAS=   -93.9  FOM=  0.62  TEST=  0
INDE    1   77    8  FOBS=    44.4  SIGMA=    4.4  PHAS=    -9.0  FOM=  0.56  TEST=  0
INDE    1   77   10  FOBS=    60.6  SIGMA=    3.8  PHAS=   110.6  FOM=  0.67  TEST=  0
INDE    2    3   19  FOBS=    85.9  SIGMA=    1.0  PHAS=    64.5  FOM=  0.74  TEST=  0
INDE    2    3   21  FOBS=   243.1  SIGMA=    0.6  PHAS=   151.1  FOM=  0.92  TEST=  0
INDE    2    3   23  FOBS=   325.6  SIGMA=    0.5  PHAS=  -145.4  FOM=  0.89  TEST=  0
INDE    2    3   25  FOBS=    68.8  SIGMA=    1.4  PHAS=    22.9  FOM=  0.70  TEST=  0
INDE    2    3   27  FOBS=   189.2  SIGMA=    0.7  PHAS=   -38.9  FOM=  0.98  TEST=  0
INDE    2    3   29  FOBS=   146.8  SIGMA=    0.9  PHAS=    15.0  FOM=  0.94  TEST=  0
INDE    2    3   31  FOBS=   265.1  SIGMA=    0.6  PHAS=  -154.9  FOM=  0.97  TEST=  0
INDE    2    3   33  FOBS=   141.3  SIGMA=    1.0  PHAS=   102.7  FOM=  0.91  TEST=  0
INDE    2    3   35  FOBS=   232.9  SIGMA=    0.7  PHAS=     0.5  FOM=  0.96  TEST=  0
INDE    2    3   37  FOBS=   274.6  SIGMA=    0.7  PHAS=    -9.1  FOM=  0.96  TEST=  0
INDE    2    3   39  FOBS=   443.0  SIGMA=    0.6  PHAS=    55.3  FOM=  0.97  TEST=  0
INDE    2    3   41  FOBS=    92.3  SIGMA=    1.4  PHAS=    22.0  FOM=  0.13  TEST=  0
INDE    2    3   43  FOBS=   317.5  SIGMA=    0.6  PHAS=    83.1  FOM=  0.96  TEST=  0
INDE    2    3   45  FOBS=   114.9  SIGMA=    1.9  PHAS=    80.2  FOM=  0.96  TEST=  0
INDE    2    3   47  FOBS=    52.8  SIGMA=    4.4  PHAS=    23.2  FOM=  0.42  TEST=  1
INDE    2    3   49  FOBS=   174.7  SIGMA=    0.9  PHAS=  -154.6  FOM=  0.95  TEST=  0
INDE    2    3   51  FOBS=   193.1  SIGMA=    1.0  PHAS=   -97.0  FOM=  0.91  TEST=  0
INDE    2    3   53  FOBS=     0.0  SIGMA=   18.6  PHAS=     0.0  FOM=  0.00  TEST=  0
INDE    2    3   55  FOBS=    32.0  SIGMA=    5.2  PHAS=    51.4  FOM=  0.31  TEST=  0
INDE    2    3   57  FOBS=   159.4  SIGMA=    1.1  PHAS=    15.5  FOM=  0.93  TEST=  0
INDE    2    3   59  FOBS=     0.0  SIGMA=   21.4  PHAS=     0.0  FOM=  0.00  TEST=  0
INDE    2    3   61  FOBS=     0.0  SIGMA=   21.1  PHAS=     0.0  FOM=  0.00  TEST=  0
INDE    2    3   63  FOBS=    85.3  SIGMA=    3.8  PHAS=  -156.0  FOM=  0.83  TEST=  0
INDE    2    3   65  FOBS=    96.2  SIGMA=    3.3  PHAS=   123.9  FOM=  0.84  TEST=  0
INDE    2    3   67  FOBS=    77.2  SIGMA=    4.1  PHAS=    47.5  FOM=  0.90  TEST=  0
INDE    2    3   69  FOBS=    70.3  SIGMA=    4.8  PHAS=   130.1  FOM=  0.64  TEST=  0
INDE    2    3   71  FOBS=   101.0  SIGMA=    3.2  PHAS=   -85.7  FOM=  0.85  TEST=  0
INDE    2    4   18  FOBS=    89.7  SIGMA=    0.7  PHAS=   -11.2  FOM=  0.90  TEST=  0
INDE    2    4   20  FOBS=    73.7  SIGMA=    0.9  PHAS=    38.9  FOM=  0.78  TEST=  0
INDE    2    4   22  FOBS=   278.0  SIGMA=    0.6  PHAS=   -55.9  FOM=  0.44  TEST=  1
INDE    2    4   24  FOBS=   148.1  SIGMA=    0.8  PHAS=   151.3  FOM=  0.74  TEST=  0
```

*FIG. 12A - 50*

```
INDE  2  4  26  FOBS=  150.4  SIGMA=   0.8  PHAS=   158.8  FOM=  0.99  TEST= 0
INDE  2  4  28  FOBS=  245.7  SIGMA=   0.7  PHAS=   -66.2  FOM=  0.97  TEST= 0
INDE  2  4  30  FOBS=  139.4  SIGMA=   1.0  PHAS=    53.6  FOM=  0.99  TEST= 0
INDE  2  4  32  FOBS=  234.4  SIGMA=   0.7  PHAS=    51.5  FOM=  0.98  TEST= 0
INDE  2  4  34  FOBS=  263.0  SIGMA=   0.7  PHAS=   141.6  FOM=  0.96  TEST= 0
INDE  2  4  36  FOBS=   88.0  SIGMA=   1.7  PHAS=    44.0  FOM=  0.85  TEST= 0
INDE  2  4  38  FOBS=  202.1  SIGMA=   0.9  PHAS=    13.9  FOM=  0.99  TEST= 0
INDE  2  4  40  FOBS=  268.4  SIGMA=   0.8  PHAS=    31.8  FOM=  0.91  TEST= 0
INDE  2  4  42  FOBS=  281.6  SIGMA=   0.8  PHAS=   -66.9  FOM=  0.96  TEST= 0
INDE  2  4  44  FOBS=  227.4  SIGMA=   1.1  PHAS=   -24.5  FOM=  0.92  TEST= 0
INDE  2  4  46  FOBS=  148.8  SIGMA=   1.6  PHAS=    33.5  FOM=  0.85  TEST= 0
INDE  2  4  48  FOBS=  207.6  SIGMA=   1.3  PHAS=   103.6  FOM=  0.97  TEST= 0
INDE  2  4  50  FOBS=  199.4  SIGMA=   1.0  PHAS=   171.7  FOM=  0.93  TEST= 0
INDE  2  4  52  FOBS=   58.2  SIGMA=   3.0  PHAS=    97.8  FOM=  0.93  TEST= 0
INDE  2  4  54  FOBS=  126.8  SIGMA=   1.4  PHAS=   -15.5  FOM=  0.92  TEST= 0
INDE  2  4  56  FOBS=   28.5  SIGMA=   6.1  PHAS=   -78.2  FOM=  0.34  TEST= 0
INDE  2  4  58  FOBS=   51.6  SIGMA=   3.3  PHAS=    72.3  FOM=  0.49  TEST= 0
INDE  2  4  60  FOBS=   33.6  SIGMA=   5.0  PHAS=   -13.4  FOM=  0.58  TEST= 0
INDE  2  4  62  FOBS=   80.1  SIGMA=   3.8  PHAS=   141.1  FOM=  0.94  TEST= 0
INDE  2  4  64  FOBS=    0.0  SIGMA=  20.8  PHAS=     0.0  FOM=  0.00  TEST= 0
INDE  2  4  66  FOBS=   73.0  SIGMA=   3.9  PHAS=    42.4  FOM=  0.87  TEST= 0
INDE  2  4  68  FOBS=   84.1  SIGMA=   4.0  PHAS=  -171.6  FOM=  0.77  TEST= 0
INDE  2  4  70  FOBS=   75.0  SIGMA=   4.5  PHAS=  -177.0  FOM=  0.91  TEST= 0
INDE  2  4  74  FOBS=   56.4  SIGMA=   6.0  PHAS=    21.6  FOM=  0.47  TEST= 0
INDE  2  5  19  FOBS=  177.8  SIGMA=   0.6  PHAS=    21.7  FOM=  0.96  TEST= 0
INDE  2  5  21  FOBS=  230.4  SIGMA=   0.6  PHAS=  -103.1  FOM=  0.81  TEST= 0
INDE  2  5  23  FOBS=  133.1  SIGMA=   0.7  PHAS=   -72.6  FOM=  0.79  TEST= 0
INDE  2  5  25  FOBS=  193.7  SIGMA=   0.6  PHAS=    24.0  FOM=  0.95  TEST= 0
INDE  2  5  27  FOBS=   88.7  SIGMA=   1.0  PHAS=   -21.2  FOM=  0.92  TEST= 0
INDE  2  5  29  FOBS=  234.2  SIGMA=   0.8  PHAS=  -119.9  FOM=  0.97  TEST= 0
INDE  2  5  31  FOBS=  195.2  SIGMA=   0.8  PHAS=   -87.3  FOM=  0.98  TEST= 0
INDE  2  5  33  FOBS=  173.4  SIGMA=   0.7  PHAS=    48.1  FOM=  0.89  TEST= 0
INDE  2  5  35  FOBS=  253.6  SIGMA=   1.2  PHAS=   -46.1  FOM=  0.96  TEST= 0
INDE  2  5  37  FOBS=   71.7  SIGMA=   2.0  PHAS=     7.4  FOM=  0.98  TEST= 1
INDE  2  5  39  FOBS=  304.6  SIGMA=   0.8  PHAS=    10.6  FOM=  0.96  TEST= 0
INDE  2  5  41  FOBS=   80.5  SIGMA=   2.1  PHAS=     0.4  FOM=  0.78  TEST= 0
INDE  2  5  43  FOBS=  183.1  SIGMA=   1.1  PHAS=   125.3  FOM=  0.98  TEST= 1
INDE  2  5  45  FOBS=   65.0  SIGMA=   3.1  PHAS=   -17.9  FOM=  0.33  TEST= 0
INDE  2  5  47  FOBS=  163.0  SIGMA=   1.5  PHAS=   -84.7  FOM=  0.97  TEST= 0
INDE  2  5  49  FOBS=  132.6  SIGMA=   1.7  PHAS=    49.9  FOM=  0.93  TEST= 0
INDE  2  5  51  FOBS=  119.8  SIGMA=   1.4  PHAS=   142.7  FOM=  0.74  TEST= 0
INDE  2  5  53  FOBS=   47.8  SIGMA=   3.4  PHAS=    90.5  FOM=  0.75  TEST= 0
INDE  2  5  55  FOBS=  209.6  SIGMA=   0.8  PHAS=   -52.5  FOM=  0.90  TEST= 0
INDE  2  5  57  FOBS=   27.1  SIGMA=   5.9  PHAS=   -74.2  FOM=  0.33  TEST= 0
INDE  2  5  59  FOBS=    0.0  SIGMA=  16.9  PHAS=     0.0  FOM=  0.00  TEST= 1
INDE  2  5  61  FOBS=  109.0  SIGMA=   1.4  PHAS=    44.5  FOM=  0.91  TEST= 1
INDE  2  5  63  FOBS=   76.2  SIGMA=   2.4  PHAS=  -174.0  FOM=  0.82  TEST= 0
INDE  2  5  65  FOBS=   44.3  SIGMA=   5.6  PHAS=  -158.2  FOM=  0.56  TEST= 0
INDE  2  5  67  FOBS=   85.9  SIGMA=   4.0  PHAS=    88.3  FOM=  0.93  TEST= 0
INDE  2  5  69  FOBS=  128.7  SIGMA=   2.8  PHAS=   124.0  FOM=  0.95  TEST= 0
INDE  2  5  71  FOBS=   68.7  SIGMA=   5.0  PHAS=   171.2  FOM=  0.75  TEST= 0
INDE  2  5  73  FOBS=   55.4  SIGMA=   6.3  PHAS=   152.7  FOM=  0.76  TEST= 0
INDE  2  5  75  FOBS=   64.9  SIGMA=   5.6  PHAS=     4.6  FOM=  0.82  TEST= 0
INDE  2  6  18  FOBS=  284.3  SIGMA=   0.5  PHAS=  -135.7  FOM=  0.71  TEST= 0
INDE  2  6  20  FOBS=  333.6  SIGMA=   0.7  PHAS=  -112.8  FOM=  0.98  TEST= 0
INDE  2  6  22  FOBS=   88.7  SIGMA=   0.9  PHAS=    72.9  FOM=  0.92  TEST= 0
INDE  2  6  24  FOBS=  256.6  SIGMA=   0.5  PHAS=  -119.1  FOM=  0.95  TEST= 0
INDE  2  6  26  FOBS=  122.1  SIGMA=   0.8  PHAS=  -109.8  FOM=  0.98  TEST= 0
INDE  2  6  28  FOBS=  117.3  SIGMA=   0.8  PHAS=   126.3  FOM=  0.98  TEST= 0
INDE  2  6  30  FOBS=  124.4  SIGMA=   0.8  PHAS=  -145.8  FOM=  0.89  TEST= 0
INDE  2  6  32  FOBS=  148.7  SIGMA=   0.8  PHAS=   -66.6  FOM=  0.92  TEST= 0
INDE  2  6  34  FOBS=  177.3  SIGMA=   1.2  PHAS=   120.8  FOM=  0.94  TEST= 0
INDE  2  6  36  FOBS=  216.7  SIGMA=   0.9  PHAS=    87.8  FOM=  0.82  TEST= 1
INDE  2  6  38  FOBS=  186.9  SIGMA=   1.1  PHAS=    15.3  FOM=  0.87  TEST= 0
INDE  2  6  40  FOBS=  305.8  SIGMA=   1.0  PHAS=   -24.3  FOM=  0.98  TEST= 0
INDE  2  6  42  FOBS=  236.4  SIGMA=   1.3  PHAS=   -28.4  FOM=  0.95  TEST= 0
INDE  2  6  44  FOBS=  145.5  SIGMA=   1.5  PHAS=  -121.8  FOM=  0.87  TEST= 0
INDE  2  6  46  FOBS=   75.8  SIGMA=   2.4  PHAS=   165.2  FOM=  0.64  TEST= 0
INDE  2  6  48  FOBS=  150.5  SIGMA=   1.4  PHAS=   -78.5  FOM=  0.40  TEST= 1
INDE  2  6  50  FOBS=   85.3  SIGMA=   2.3  PHAS=   173.2  FOM=  0.15  TEST= 1
```

*FIG. 12A - 51*

```
INDE  2  6  52  FOBS=   116.6  SIGMA=   1.4  PHAS=    71.4  FOM=  0.92  TEST= 1
INDE  2  6  54  FOBS=    85.8  SIGMA=   1.8  PHAS=  -160.4  FOM=  0.35  TEST= 1
INDE  2  6  56  FOBS=   225.6  SIGMA=   0.8  PHAS=  -125.3  FOM=  0.97  TEST= 0
INDE  2  6  58  FOBS=    23.5  SIGMA=   6.4  PHAS=   -81.0  FOM=  0.18  TEST= 1
INDE  2  6  60  FOBS=    53.8  SIGMA=   2.7  PHAS=   -82.3  FOM=  0.82  TEST= 0
INDE  2  6  62  FOBS=    43.4  SIGMA=   3.4  PHAS=    71.5  FOM=  0.82  TEST= 0
INDE  2  6  64  FOBS=    44.7  SIGMA=   4.0  PHAS=   171.3  FOM=  0.46  TEST= 0
INDE  2  6  66  FOBS=   113.7  SIGMA=   2.3  PHAS=    52.4  FOM=  0.92  TEST= 0
INDE  2  6  68  FOBS=    93.0  SIGMA=   3.9  PHAS=    62.0  FOM=  0.24  TEST= 1
INDE  2  6  70  FOBS=   109.6  SIGMA=   3.4  PHAS=    97.3  FOM=  0.93  TEST= 0
INDE  2  6  72  FOBS=    20.9  SIGMA=  16.8  PHAS=  -161.1  FOM=  0.14  TEST= 0
INDE  2  6  74  FOBS=    50.4  SIGMA=   7.2  PHAS=   -65.7  FOM=  0.10  TEST= 1
INDE  2  6  76  FOBS=     5.9  SIGMA=  63.6  PHAS=   -71.6  FOM=  0.12  TEST= 0
INDE  2  7  17  FOBS=   170.6  SIGMA=   0.5  PHAS=   -19.1  FOM=  0.97  TEST= 0
INDE  2  7  19  FOBS=   243.2  SIGMA=   0.5  PHAS=   140.2  FOM=  0.56  TEST= 1
INDE  2  7  21  FOBS=   228.0  SIGMA=   0.6  PHAS=   166.8  FOM=  0.99  TEST= 0
INDE  2  7  23  FOBS=    48.3  SIGMA=   1.6  PHAS=   130.1  FOM=  0.96  TEST= 0
INDE  2  7  25  FOBS=    81.7  SIGMA=   1.0  PHAS=    73.4  FOM=  0.98  TEST= 0
INDE  2  7  27  FOBS=    53.1  SIGMA=   1.6  PHAS=   124.8  FOM=  0.91  TEST= 0
INDE  2  7  29  FOBS=   107.9  SIGMA=   0.9  PHAS=  -146.6  FOM=  0.90  TEST= 0
INDE  2  7  31  FOBS=    88.9  SIGMA=   1.1  PHAS=   139.8  FOM=  0.98  TEST= 0
INDE  2  7  33  FOBS=   182.2  SIGMA=   0.7  PHAS=   -95.7  FOM=  0.88  TEST= 0
INDE  2  7  35  FOBS=   318.4  SIGMA=   0.8  PHAS=   -46.2  FOM=  0.97  TEST= 0
INDE  2  7  37  FOBS=   512.2  SIGMA=   0.8  PHAS=    14.9  FOM=  0.98  TEST= 0
INDE  2  7  39  FOBS=   225.2  SIGMA=   0.9  PHAS=  -144.1  FOM=  0.87  TEST= 1
INDE  2  7  41  FOBS=   129.9  SIGMA=   1.3  PHAS=   -58.0  FOM=  0.94  TEST= 1
INDE  2  7  43  FOBS=   191.6  SIGMA=   1.0  PHAS=  -127.2  FOM=  0.81  TEST= 0
INDE  2  7  45  FOBS=   178.3  SIGMA=   1.3  PHAS=   155.1  FOM=  0.91  TEST= 0
INDE  2  7  47  FOBS=   111.5  SIGMA=   1.8  PHAS=    94.0  FOM=  0.84  TEST= 0
INDE  2  7  49  FOBS=   143.9  SIGMA=   1.5  PHAS=   -18.7  FOM=  0.93  TEST= 0
INDE  2  7  51  FOBS=   131.4  SIGMA=   1.5  PHAS=    21.2  FOM=  0.85  TEST= 0
INDE  2  7  53  FOBS=    92.1  SIGMA=   1.7  PHAS=   145.1  FOM=  0.93  TEST= 0
INDE  2  7  55  FOBS=   100.3  SIGMA=   1.6  PHAS=  -157.7  FOM=  0.77  TEST= 0
INDE  2  7  57  FOBS=    57.4  SIGMA=   2.7  PHAS=    82.7  FOM=  0.83  TEST= 0
INDE  2  7  59  FOBS=   154.7  SIGMA=   1.1  PHAS=    47.4  FOM=  0.94  TEST= 0
INDE  2  7  61  FOBS=   147.0  SIGMA=   1.1  PHAS=   126.5  FOM=  0.93  TEST= 0
INDE  2  7  63  FOBS=   125.6  SIGMA=   1.5  PHAS=  -157.1  FOM=  0.97  TEST= 0
INDE  2  7  65  FOBS=    70.3  SIGMA=   3.0  PHAS=   130.5  FOM=  0.91  TEST= 0
INDE  2  7  67  FOBS=    78.4  SIGMA=   3.3  PHAS=    45.0  FOM=  0.78  TEST= 0
INDE  2  7  69  FOBS=   129.3  SIGMA=   2.1  PHAS=    61.5  FOM=  0.96  TEST= 0
INDE  2  7  71  FOBS=    17.3  SIGMA=  21.0  PHAS=   130.5  FOM=  0.34  TEST= 0
INDE  2  7  73  FOBS=    32.5  SIGMA=  10.9  PHAS=   -53.9  FOM=  0.23  TEST= 0
INDE  2  7  75  FOBS=    74.5  SIGMA=   5.0  PHAS=    98.4  FOM=  0.04  TEST= 1
INDE  2  7  77  FOBS=    85.4  SIGMA=   4.7  PHAS=   -64.4  FOM=  0.94  TEST= 0
INDE  2  8  16  FOBS=   235.6  SIGMA=   0.4  PHAS=    60.2  FOM=  0.56  TEST= 0
INDE  2  8  18  FOBS=    95.2  SIGMA=   0.7  PHAS=  -156.8  FOM=  0.84  TEST= 1
INDE  2  8  20  FOBS=    81.6  SIGMA=   0.9  PHAS=   174.7  FOM=  0.92  TEST= 0
INDE  2  8  22  FOBS=   281.5  SIGMA=   0.4  PHAS=    22.1  FOM=  0.94  TEST= 0
INDE  2  8  24  FOBS=   103.1  SIGMA=   0.9  PHAS=  -106.5  FOM=  0.93  TEST= 0
INDE  2  8  26  FOBS=   130.8  SIGMA=   0.7  PHAS=     9.6  FOM=  0.99  TEST= 0
INDE  2  8  28  FOBS=   265.3  SIGMA=   0.8  PHAS=    97.4  FOM=  0.97  TEST= 0
INDE  2  8  30  FOBS=   184.6  SIGMA=   0.7  PHAS=    85.9  FOM=  0.92  TEST= 0
INDE  2  8  32  FOBS=   201.4  SIGMA=   0.7  PHAS=   135.9  FOM=  0.99  TEST= 0
INDE  2  8  34  FOBS=   243.0  SIGMA=   1.0  PHAS=  -179.8  FOM=  0.95  TEST= 0
INDE  2  8  36  FOBS=   238.0  SIGMA=   0.9  PHAS=  -129.5  FOM=  0.95  TEST= 1
INDE  2  8  38  FOBS=   156.9  SIGMA=   0.9  PHAS=  -137.8  FOM=  0.97  TEST= 0
INDE  2  8  40  FOBS=   174.6  SIGMA=   1.0  PHAS=  -127.8  FOM=  0.88  TEST= 0
INDE  2  8  42  FOBS=   127.4  SIGMA=   1.4  PHAS=  -175.3  FOM=  0.92  TEST= 0
INDE  2  8  44  FOBS=   327.6  SIGMA=   1.0  PHAS=   122.6  FOM=  0.96  TEST= 0
INDE  2  8  46  FOBS=    84.6  SIGMA=   2.3  PHAS=    99.8  FOM=  0.26  TEST= 0
INDE  2  8  48  FOBS=   140.3  SIGMA=   1.5  PHAS=   -21.4  FOM=  0.88  TEST= 0
INDE  2  8  50  FOBS=   109.9  SIGMA=   1.8  PHAS=   -78.5  FOM=  0.79  TEST= 0
INDE  2  8  52  FOBS=   128.3  SIGMA=   1.6  PHAS=   -67.1  FOM=  0.92  TEST= 0
INDE  2  8  54  FOBS=    34.0  SIGMA=   4.9  PHAS=    61.6  FOM=  0.82  TEST= 0
INDE  2  8  56  FOBS=    99.6  SIGMA=   1.6  PHAS=   173.1  FOM=  0.95  TEST= 0
INDE  2  8  58  FOBS=   202.6  SIGMA=   0.9  PHAS=   -45.7  FOM=  0.96  TEST= 0
INDE  2  8  60  FOBS=    91.8  SIGMA=   1.7  PHAS=   -15.3  FOM=  0.63  TEST= 0
INDE  2  8  62  FOBS=   216.6  SIGMA=   0.9  PHAS=    68.0  FOM=  0.98  TEST= 0
INDE  2  8  64  FOBS=   135.9  SIGMA=   1.4  PHAS=    97.3  FOM=  0.93  TEST= 0
INDE  2  8  66  FOBS=    71.7  SIGMA=   3.8  PHAS=    82.8  FOM=  0.88  TEST= 0
```

*FIG. 12A - 52*

```
INDE  2   8  68 FOBS=   82.4 SIGMA=  3.3 PHAS=  -51.3 FOM= 0.95 TEST= 0
INDE  2   8  70 FOBS=   64.0 SIGMA=  4.2 PHAS=  -52.9 FOM= 0.23 TEST= 0
INDE  2   8  72 FOBS=   63.1 SIGMA=  4.2 PHAS=  132.4 FOM= 0.61 TEST= 0
INDE  2   8  74 FOBS=  115.6 SIGMA=  3.4 PHAS= -135.9 FOM= 0.95 TEST= 0
INDE  2   8  76 FOBS=   99.8 SIGMA=  4.0 PHAS= -143.2 FOM= 0.93 TEST= 0
INDE  2   9  17 FOBS=   71.0 SIGMA=  0.7 PHAS= -135.2 FOM= 0.80 TEST= 0
INDE  2   9  19 FOBS=  192.7 SIGMA=  0.4 PHAS=  155.5 FOM= 0.46 TEST= 1
INDE  2   9  21 FOBS=  108.1 SIGMA=  0.8 PHAS=  171.0 FOM= 0.85 TEST= 0
INDE  2   9  23 FOBS=  107.8 SIGMA=  0.8 PHAS=  -36.8 FOM= 0.90 TEST= 1
INDE  2   9  25 FOBS=   23.7 SIGMA=  3.3 PHAS= -172.5 FOM= 0.77 TEST= 0
INDE  2   9  27 FOBS=   86.3 SIGMA=  1.3 PHAS=  -64.3 FOM= 0.98 TEST= 0
INDE  2   9  29 FOBS=  137.4 SIGMA=  0.8 PHAS=   16.7 FOM= 0.96 TEST= 0
INDE  2   9  31 FOBS=  338.2 SIGMA=  0.7 PHAS=   73.1 FOM= 0.95 TEST= 0
INDE  2   9  33 FOBS=  118.7 SIGMA=  1.0 PHAS=   59.7 FOM= 0.89 TEST= 0
INDE  2   9  35 FOBS=   36.1 SIGMA=  3.4 PHAS=  -23.8 FOM= 0.89 TEST= 0
INDE  2   9  37 FOBS=  502.4 SIGMA=  1.0 PHAS=  104.6 FOM= 0.98 TEST= 0
INDE  2   9  39 FOBS=   82.7 SIGMA=  1.8 PHAS= -145.8 FOM= 0.86 TEST= 0
INDE  2   9  41 FOBS=  190.6 SIGMA=  1.0 PHAS=  100.6 FOM= 0.94 TEST= 0
INDE  2   9  43 FOBS=  235.8 SIGMA=  1.3 PHAS=   -2.0 FOM= 0.94 TEST= 0
INDE  2   9  45 FOBS=  110.3 SIGMA=  1.7 PHAS=  -55.5 FOM= 0.57 TEST= 0
INDE  2   9  47 FOBS=   61.2 SIGMA=  3.3 PHAS= -133.8 FOM= 0.82 TEST= 0
INDE  2   9  49 FOBS=  216.8 SIGMA=  1.1 PHAS= -139.0 FOM= 0.92 TEST= 0
INDE  2   9  51 FOBS=   47.2 SIGMA=  4.2 PHAS=   71.0 FOM= 0.82 TEST= 0
INDE  2   9  53 FOBS=   55.4 SIGMA=  4.0 PHAS=  177.1 FOM= 0.76 TEST= 0
INDE  2   9  55 FOBS=    9.2 SIGMA= 17.1 PHAS=  -59.8 FOM= 0.09 TEST= 0
INDE  2   9  57 FOBS=   92.8 SIGMA=  1.8 PHAS=  -89.9 FOM= 0.94 TEST= 0
INDE  2   9  59 FOBS=  123.1 SIGMA=  1.4 PHAS=    1.1 FOM= 0.92 TEST= 0
INDE  2   9  61 FOBS=   48.8 SIGMA=  3.1 PHAS= -109.4 FOM= 0.83 TEST= 0
INDE  2   9  63 FOBS=   56.0 SIGMA=  3.4 PHAS= -112.6 FOM= 0.83 TEST= 0
INDE  2   9  65 FOBS=  173.4 SIGMA=  1.3 PHAS=  100.6 FOM= 0.94 TEST= 0
INDE  2   9  67 FOBS=    0.0 SIGMA= 23.2 PHAS=    0.0 FOM= 0.00 TEST= 0
INDE  2   9  69 FOBS=   90.4 SIGMA=  3.0 PHAS= -118.1 FOM= 0.94 TEST= 0
INDE  2   9  71 FOBS=  143.4 SIGMA=  2.0 PHAS=  125.0 FOM= 0.96 TEST= 0
INDE  2   9  73 FOBS=   66.6 SIGMA=  4.2 PHAS=  134.6 FOM= 0.72 TEST= 0
INDE  2   9  75 FOBS=   93.6 SIGMA=  3.1 PHAS=   92.1 FOM= 0.96 TEST= 0
INDE  2   9  77 FOBS=   41.9 SIGMA=  9.6 PHAS= -137.9 FOM= 0.69 TEST= 0
INDE  2  10  16 FOBS=  269.7 SIGMA=  0.5 PHAS=  124.6 FOM= 0.98 TEST= 0
INDE  2  10  18 FOBS=  334.8 SIGMA=  0.5 PHAS=  175.3 FOM= 0.95 TEST= 0
INDE  2  10  20 FOBS=  208.8 SIGMA=  0.6 PHAS= -165.9 FOM= 0.81 TEST= 0
INDE  2  10  22 FOBS=   69.7 SIGMA=  1.1 PHAS=  108.5 FOM= 0.97 TEST= 0
INDE  2  10  24 FOBS=   60.8 SIGMA=  1.3 PHAS=   33.2 FOM= 0.89 TEST= 0
INDE  2  10  26 FOBS=   76.6 SIGMA=  1.1 PHAS=   -9.8 FOM= 0.91 TEST= 0
INDE  2  10  28 FOBS=   19.8 SIGMA=  4.4 PHAS= -150.7 FOM= 0.88 TEST= 1
INDE  2  10  30 FOBS=  160.5 SIGMA=  1.0 PHAS=   51.2 FOM= 0.94 TEST= 0
INDE  2  10  32 FOBS=  109.2 SIGMA=  1.0 PHAS=  104.7 FOM= 0.94 TEST= 1
INDE  2  10  34 FOBS=   57.1 SIGMA=  2.0 PHAS=  -49.7 FOM= 0.84 TEST= 0
INDE  2  10  36 FOBS=  241.2 SIGMA=  0.9 PHAS=    3.0 FOM= 0.84 TEST= 0
INDE  2  10  38 FOBS=  180.3 SIGMA=  1.0 PHAS=   67.6 FOM= 0.83 TEST= 0
INDE  2  10  40 FOBS=  136.9 SIGMA=  1.5 PHAS=  -47.0 FOM= 0.55 TEST= 0
INDE  2  10  42 FOBS=   46.2 SIGMA=  3.7 PHAS=   88.8 FOM= 0.54 TEST= 0
INDE  2  10  44 FOBS=  106.4 SIGMA=  1.8 PHAS=  161.4 FOM= 0.94 TEST= 0
INDE  2  10  46 FOBS=  261.9 SIGMA=  0.9 PHAS= -121.0 FOM= 0.97 TEST= 0
INDE  2  10  48 FOBS=  108.9 SIGMA=  1.9 PHAS=  103.3 FOM= 0.74 TEST= 0
INDE  2  10  50 FOBS=  207.8 SIGMA=  1.1 PHAS=   79.4 FOM= 0.96 TEST= 0
INDE  2  10  52 FOBS=  221.6 SIGMA=  1.1 PHAS= -134.0 FOM= 0.91 TEST= 0
INDE  2  10  54 FOBS=  119.7 SIGMA=  1.7 PHAS= -147.3 FOM= 0.92 TEST= 0
INDE  2  10  56 FOBS=  217.5 SIGMA=  0.8 PHAS=  149.0 FOM= 0.95 TEST= 0
INDE  2  10  58 FOBS=    0.0 SIGMA= 18.4 PHAS=    0.0 FOM= 0.00 TEST= 0
INDE  2  10  60 FOBS=   29.8 SIGMA=  6.0 PHAS= -172.8 FOM= 0.47 TEST= 0
INDE  2  10  62 FOBS=  206.4 SIGMA=  0.9 PHAS=  118.0 FOM= 0.98 TEST= 0
INDE  2  10  64 FOBS=   11.2 SIGMA= 22.1 PHAS=   79.3 FOM= 0.19 TEST= 0
INDE  2  10  66 FOBS=    0.0 SIGMA= 23.4 PHAS=    0.0 FOM= 0.00 TEST= 1
INDE  2  10  68 FOBS=   78.6 SIGMA=  3.6 PHAS=  124.3 FOM= 0.93 TEST= 0
INDE  2  10  70 FOBS=   95.4 SIGMA=  3.0 PHAS= -172.9 FOM= 0.92 TEST= 0
INDE  2  10  72 FOBS=   25.1 SIGMA= 11.2 PHAS=   39.6 FOM= 0.78 TEST= 0
INDE  2  10  74 FOBS=   49.0 SIGMA=  5.9 PHAS=  -44.1 FOM= 0.84 TEST= 0
INDE  2  10  76 FOBS=   74.2 SIGMA=  4.0 PHAS=  -27.5 FOM= 0.66 TEST= 0
INDE  2  11  15 FOBS=  254.6 SIGMA=  0.5 PHAS=   12.8 FOM= 0.83 TEST= 0
INDE  2  11  17 FOBS=  439.8 SIGMA=  0.5 PHAS=   43.8 FOM= 0.99 TEST= 0
INDE  2  11  19 FOBS=  151.7 SIGMA=  0.6 PHAS=  105.2 FOM= 0.82 TEST= 0
```

*FIG. 12A - 53*

```
INDE  2 11 21 FOBS=  118.1 SIGMA= 0.7  PHAS=  115.1 FOM= 0.78 TEST= 0
INDE  2 11 23 FOBS=  121.7 SIGMA= 0.5  PHAS=   53.1 FOM= 0.99 TEST= 0
INDE  2 11 25 FOBS=  151.5 SIGMA= 0.7  PHAS=  -75.5 FOM= 0.99 TEST= 0
INDE  2 11 27 FOBS=   73.6 SIGMA= 1.2  PHAS= -103.2 FOM= 0.99 TEST= 0
INDE  2 11 29 FOBS=  132.5 SIGMA= 0.8  PHAS=   94.4 FOM= 0.91 TEST= 0
INDE  2 11 31 FOBS=  278.7 SIGMA= 0.7  PHAS=   52.0 FOM= 0.98 TEST= 0
INDE  2 11 33 FOBS=  133.7 SIGMA= 0.9  PHAS=   33.2 FOM= 0.92 TEST= 0
INDE  2 11 35 FOBS=  354.5 SIGMA= 0.7  PHAS=  171.7 FOM= 0.96 TEST= 0
INDE  2 11 37 FOBS=  283.3 SIGMA= 1.0  PHAS=   85.4 FOM= 0.96 TEST= 0
INDE  2 11 39 FOBS=  159.9 SIGMA= 1.1  PHAS=  147.9 FOM= 0.60 TEST= 0
INDE  2 11 41 FOBS=  177.6 SIGMA= 1.1  PHAS=  119.7 FOM= 0.95 TEST= 0
INDE  2 11 43 FOBS=  328.0 SIGMA= 1.1  PHAS=   40.0 FOM= 0.97 TEST= 0
INDE  2 11 45 FOBS=  222.3 SIGMA= 1.0  PHAS=   89.3 FOM= 0.96 TEST= 0
INDE  2 11 47 FOBS=   24.0 SIGMA= 8.5  PHAS= -140.9 FOM= 0.06 TEST= 0
INDE  2 11 49 FOBS=  143.1 SIGMA= 1.5  PHAS=  -40.3 FOM= 0.92 TEST= 0
INDE  2 11 51 FOBS=   68.4 SIGMA= 3.0  PHAS=   17.2 FOM= 0.39 TEST= 1
INDE  2 11 53 FOBS=   65.9 SIGMA= 3.0  PHAS=  123.0 FOM= 0.94 TEST= 0
INDE  2 11 55 FOBS=  169.0 SIGMA= 1.2  PHAS=   70.1 FOM= 0.76 TEST= 1
INDE  2 11 57 FOBS=   92.2 SIGMA= 1.8  PHAS=   34.9 FOM= 0.95 TEST= 1
INDE  2 11 59 FOBS=   61.6 SIGMA= 2.7  PHAS=    3.4 FOM= 0.88 TEST= 0
INDE  2 11 61 FOBS=   80.9 SIGMA= 1.9  PHAS=   86.6 FOM= 0.91 TEST= 0
INDE  2 11 63 FOBS=  113.5 SIGMA= 1.7  PHAS=   85.3 FOM= 0.90 TEST= 0
INDE  2 11 65 FOBS=   88.2 SIGMA= 2.9  PHAS=   92.5 FOM= 0.52 TEST= 0
INDE  2 11 67 FOBS=    0.0 SIGMA=23.7  PHAS=    0.0 FOM= 0.00 TEST= 0
INDE  2 11 69 FOBS=   58.9 SIGMA= 4.8  PHAS=   59.9 FOM= 0.76 TEST= 0
INDE  2 11 71 FOBS=   84.1 SIGMA= 3.4  PHAS=  107.8 FOM= 0.92 TEST= 0
INDE  2 11 73 FOBS=  105.7 SIGMA= 2.7  PHAS= -124.2 FOM= 0.95 TEST= 0
INDE  2 11 75 FOBS=   79.1 SIGMA= 3.8  PHAS= -130.0 FOM= 0.84 TEST= 0
INDE  2 12 14 FOBS=  170.1 SIGMA= 0.7  PHAS=  -69.5 FOM= 0.10 TEST= 0
INDE  2 12 16 FOBS=  254.4 SIGMA= 0.5  PHAS=  -73.3 FOM= 0.96 TEST= 0
INDE  2 12 18 FOBS=  142.0 SIGMA= 0.6  PHAS=  -67.2 FOM= 0.48 TEST= 1
INDE  2 12 20 FOBS=   82.0 SIGMA= 0.7  PHAS=  -30.5 FOM= 0.96 TEST= 0
INDE  2 12 22 FOBS=   76.7 SIGMA= 0.8  PHAS=    2.9 FOM= 0.88 TEST= 1
INDE  2 12 24 FOBS=   94.5 SIGMA= 0.8  PHAS=   83.1 FOM= 0.95 TEST= 0
INDE  2 12 26 FOBS=  120.2 SIGMA= 0.8  PHAS=  -94.4 FOM= 0.98 TEST= 0
INDE  2 12 28 FOBS=  138.3 SIGMA= 0.8  PHAS=   40.3 FOM= 0.96 TEST= 1
INDE  2 12 30 FOBS=  184.6 SIGMA= 0.7  PHAS=    1.1 FOM= 0.95 TEST= 0
INDE  2 12 32 FOBS=  179.6 SIGMA= 0.7  PHAS=  -48.5 FOM= 0.94 TEST= 0
INDE  2 12 34 FOBS=  171.8 SIGMA= 1.1  PHAS=    8.7 FOM= 0.98 TEST= 0
INDE  2 12 36 FOBS=  270.8 SIGMA= 0.9  PHAS=  111.0 FOM= 0.95 TEST= 0
INDE  2 12 38 FOBS=  268.5 SIGMA= 0.8  PHAS=   60.5 FOM= 0.90 TEST= 0
INDE  2 12 40 FOBS=   54.8 SIGMA= 3.0  PHAS=   12.9 FOM= 0.85 TEST= 0
INDE  2 12 42 FOBS=  136.0 SIGMA= 1.4  PHAS=   11.8 FOM= 0.96 TEST= 1
INDE  2 12 44 FOBS=  365.8 SIGMA= 1.1  PHAS=  -36.6 FOM= 0.98 TEST= 0
INDE  2 12 46 FOBS=  228.1 SIGMA= 1.0  PHAS=  -78.7 FOM= 0.91 TEST= 0
INDE  2 12 48 FOBS=  153.3 SIGMA= 1.5  PHAS= -147.8 FOM= 0.94 TEST= 0
INDE  2 12 50 FOBS=  313.8 SIGMA= 0.9  PHAS=    9.4 FOM= 0.86 TEST= 1
INDE  2 12 52 FOBS=  120.6 SIGMA= 1.7  PHAS= -108.8 FOM= 0.94 TEST= 0
INDE  2 12 54 FOBS=   67.0 SIGMA= 2.9  PHAS=  -17.9 FOM= 0.81 TEST= 0
INDE  2 12 56 FOBS=    0.0 SIGMA=18.6  PHAS=    0.0 FOM= 0.00 TEST= 0
INDE  2 12 58 FOBS=  101.3 SIGMA= 1.7  PHAS=   -4.1 FOM= 0.75 TEST= 0
INDE  2 12 60 FOBS=   61.0 SIGMA= 2.6  PHAS=   -7.7 FOM= 0.88 TEST= 0
INDE  2 12 62 FOBS=   87.8 SIGMA= 1.8  PHAS=   81.7 FOM= 0.83 TEST= 0
INDE  2 12 64 FOBS=   45.5 SIGMA= 4.5  PHAS=   58.1 FOM= 0.33 TEST= 0
INDE  2 12 66 FOBS=   98.3 SIGMA= 3.0  PHAS=  -99.1 FOM= 0.93 TEST= 0
INDE  2 12 68 FOBS=   57.5 SIGMA= 5.0  PHAS=  105.5 FOM= 0.91 TEST= 0
INDE  2 12 70 FOBS=  119.9 SIGMA= 2.4  PHAS=   -1.5 FOM= 0.31 TEST= 1
INDE  2 12 72 FOBS=  122.6 SIGMA= 2.4  PHAS=  105.8 FOM= 0.95 TEST= 0
INDE  2 12 74 FOBS=   79.5 SIGMA= 3.6  PHAS=  -74.9 FOM= 0.27 TEST= 0
INDE  2 12 76 FOBS=  101.3 SIGMA= 3.1  PHAS=  146.2 FOM= 0.96 TEST= 0
INDE  2 13 13 FOBS=  172.6 SIGMA= 1.0  PHAS=  113.8 FOM= 0.05 TEST= 0
INDE  2 13 15 FOBS=  304.1 SIGMA= 0.7  PHAS=  112.6 FOM= 0.90 TEST= 0
INDE  2 13 17 FOBS=  193.2 SIGMA= 0.5  PHAS=   52.4 FOM= 0.89 TEST= 0
INDE  2 13 19 FOBS=   98.6 SIGMA= 0.6  PHAS=  179.6 FOM= 0.90 TEST= 0
INDE  2 13 21 FOBS=   67.4 SIGMA= 0.9  PHAS=   58.9 FOM= 0.71 TEST= 0
INDE  2 13 23 FOBS=   81.2 SIGMA= 0.8  PHAS=  101.4 FOM= 0.99 TEST= 0
INDE  2 13 25 FOBS=  219.5 SIGMA= 0.6  PHAS= -145.4 FOM= 0.94 TEST= 0
INDE  2 13 27 FOBS=   65.9 SIGMA= 1.2  PHAS= -112.6 FOM= 0.98 TEST= 0
INDE  2 13 29 FOBS=  106.3 SIGMA= 1.0  PHAS= -176.2 FOM= 0.90 TEST= 0
INDE  2 13 31 FOBS=  132.6 SIGMA= 0.9  PHAS=  -91.2 FOM= 0.96 TEST= 0
```

*FIG. 12A - 54*

| | | | | | | | | | | | |
|---|---|---|---|---|---|---|---|---|---|---|---|
| INDE | 2 | 13 | 33 | FOBS= | 20.8 | SIGMA= | 3.2 | PHAS= | 72.1 | FOM= | 0.43 | TEST= 0
| INDE | 2 | 13 | 35 | FOBS= | 288.4 | SIGMA= | 0.8 | PHAS= | 92.7 | FOM= | 0.99 | TEST= 0
| INDE | 2 | 13 | 37 | FOBS= | 407.2 | SIGMA= | 0.8 | PHAS= | 30.3 | FOM= | 0.98 | TEST= 1
| INDE | 2 | 13 | 39 | FOBS= | 122.3 | SIGMA= | 1.3 | PHAS= | 51.9 | FOM= | 0.96 | TEST= 0
| INDE | 2 | 13 | 41 | FOBS= | 234.1 | SIGMA= | 1.3 | PHAS= | -105.2 | FOM= | 0.94 | TEST= 0
| INDE | 2 | 13 | 43 | FOBS= | 185.6 | SIGMA= | 1.2 | PHAS= | -110.3 | FOM= | 0.93 | TEST= 0
| INDE | 2 | 13 | 45 | FOBS= | 90.5 | SIGMA= | 2.4 | PHAS= | -32.5 | FOM= | 0.22 | TEST= 0
| INDE | 2 | 13 | 47 | FOBS= | 82.4 | SIGMA= | 2.6 | PHAS= | -33.7 | FOM= | 0.81 | TEST= 0
| INDE | 2 | 13 | 49 | FOBS= | 121.0 | SIGMA= | 1.8 | PHAS= | -70.3 | FOM= | 0.88 | TEST= 0
| INDE | 2 | 13 | 51 | FOBS= | 85.5 | SIGMA= | 2.4 | PHAS= | -153.5 | FOM= | 0.89 | TEST= 0
| INDE | 2 | 13 | 53 | FOBS= | 94.2 | SIGMA= | 2.2 | PHAS= | 37.2 | FOM= | 0.82 | TEST= 0
| INDE | 2 | 13 | 55 | FOBS= | 58.7 | SIGMA= | 3.3 | PHAS= | 45.0 | FOM= | 0.72 | TEST= 0
| INDE | 2 | 13 | 57 | FOBS= | 0.0 | SIGMA= | 17.9 | PHAS= | 0.0 | FOM= | 0.00 | TEST= 0
| INDE | 2 | 13 | 59 | FOBS= | 72.7 | SIGMA= | 2.3 | PHAS= | -44.0 | FOM= | 0.87 | TEST= 0
| INDE | 2 | 13 | 61 | FOBS= | 54.7 | SIGMA= | 3.1 | PHAS= | -159.0 | FOM= | 0.20 | TEST= 1
| INDE | 2 | 13 | 63 | FOBS= | 0.0 | SIGMA= | 19.4 | PHAS= | 0.0 | FOM= | 0.00 | TEST= 0
| INDE | 2 | 13 | 65 | FOBS= | 53.0 | SIGMA= | 5.5 | PHAS= | 139.8 | FOM= | 0.60 | TEST= 0
| INDE | 2 | 13 | 67 | FOBS= | 53.9 | SIGMA= | 5.4 | PHAS= | 135.3 | FOM= | 0.69 | TEST= 0
| INDE | 2 | 13 | 69 | FOBS= | 71.9 | SIGMA= | 4.1 | PHAS= | -16.4 | FOM= | 0.92 | TEST= 0
| INDE | 2 | 13 | 71 | FOBS= | 84.1 | SIGMA= | 3.5 | PHAS= | -12.5 | FOM= | 0.93 | TEST= 0
| INDE | 2 | 13 | 73 | FOBS= | 60.1 | SIGMA= | 4.9 | PHAS= | -111.4 | FOM= | 0.87 | TEST= 0
| INDE | 2 | 13 | 75 | FOBS= | 17.6 | SIGMA= | 16.9 | PHAS= | 135.5 | FOM= | 0.50 | TEST= 0
| INDE | 2 | 14 | 12 | FOBS= | 343.0 | SIGMA= | 0.6 | PHAS= | 19.8 | FOM= | 0.98 | TEST= 0
| INDE | 2 | 14 | 14 | FOBS= | 325.0 | SIGMA= | 0.8 | PHAS= | 11.1 | FOM= | 0.95 | TEST= 0
| INDE | 2 | 14 | 16 | FOBS= | 257.0 | SIGMA= | 0.6 | PHAS= | -36.3 | FOM= | 0.93 | TEST= 0
| INDE | 2 | 14 | 18 | FOBS= | 100.8 | SIGMA= | 0.7 | PHAS= | -8.5 | FOM= | 0.96 | TEST= 0
| INDE | 2 | 14 | 20 | FOBS= | 170.7 | SIGMA= | 0.5 | PHAS= | -16.0 | FOM= | 0.92 | TEST= 0
| INDE | 2 | 14 | 22 | FOBS= | 165.0 | SIGMA= | 0.5 | PHAS= | -6.7 | FOM= | 0.99 | TEST= 0
| INDE | 2 | 14 | 24 | FOBS= | 244.6 | SIGMA= | 0.5 | PHAS= | 123.6 | FOM= | 0.93 | TEST= 1
| INDE | 2 | 14 | 26 | FOBS= | 144.6 | SIGMA= | 0.6 | PHAS= | 122.2 | FOM= | 0.95 | TEST= 0
| INDE | 2 | 14 | 28 | FOBS= | 149.7 | SIGMA= | 0.6 | PHAS= | 67.9 | FOM= | 0.99 | TEST= 0
| INDE | 2 | 14 | 30 | FOBS= | 225.7 | SIGMA= | 0.6 | PHAS= | 46.1 | FOM= | 0.95 | TEST= 0
| INDE | 2 | 14 | 32 | FOBS= | 69.0 | SIGMA= | 1.1 | PHAS= | 50.2 | FOM= | 0.67 | TEST= 0
| INDE | 2 | 14 | 34 | FOBS= | 186.5 | SIGMA= | 0.8 | PHAS= | -51.2 | FOM= | 0.88 | TEST= 1
| INDE | 2 | 14 | 36 | FOBS= | 345.4 | SIGMA= | 0.6 | PHAS= | -53.6 | FOM= | 0.99 | TEST= 0
| INDE | 2 | 14 | 38 | FOBS= | 258.8 | SIGMA= | 1.0 | PHAS= | -78.0 | FOM= | 0.91 | TEST= 0
| INDE | 2 | 14 | 40 | FOBS= | 129.9 | SIGMA= | 1.4 | PHAS= | 147.8 | FOM= | 0.96 | TEST= 0
| INDE | 2 | 14 | 42 | FOBS= | 196.9 | SIGMA= | 1.3 | PHAS= | 151.2 | FOM= | 0.92 | TEST= 0
| INDE | 2 | 14 | 44 | FOBS= | 77.1 | SIGMA= | 2.8 | PHAS= | -39.2 | FOM= | 0.85 | TEST= 0
| INDE | 2 | 14 | 46 | FOBS= | 127.2 | SIGMA= | 1.7 | PHAS= | -77.7 | FOM= | 0.96 | TEST= 0
| INDE | 2 | 14 | 48 | FOBS= | 345.0 | SIGMA= | 1.1 | PHAS= | -130.1 | FOM= | 0.98 | TEST= 0
| INDE | 2 | 14 | 50 | FOBS= | 73.1 | SIGMA= | 2.9 | PHAS= | 90.9 | FOM= | 0.90 | TEST= 1
| INDE | 2 | 14 | 52 | FOBS= | 109.9 | SIGMA= | 1.9 | PHAS= | 8.4 | FOM= | 0.87 | TEST= 0
| INDE | 2 | 14 | 54 | FOBS= | 77.6 | SIGMA= | 2.6 | PHAS= | -76.3 | FOM= | 0.70 | TEST= 0
| INDE | 2 | 14 | 56 | FOBS= | 57.5 | SIGMA= | 3.4 | PHAS= | -78.6 | FOM= | 0.64 | TEST= 0
| INDE | 2 | 14 | 58 | FOBS= | 124.8 | SIGMA= | 1.4 | PHAS= | 33.6 | FOM= | 0.92 | TEST= 0
| INDE | 2 | 14 | 60 | FOBS= | 41.0 | SIGMA= | 3.9 | PHAS= | -173.5 | FOM= | 0.29 | TEST= 0
| INDE | 2 | 14 | 62 | FOBS= | 95.7 | SIGMA= | 1.7 | PHAS= | -176.7 | FOM= | 0.91 | TEST= 0
| INDE | 2 | 14 | 64 | FOBS= | 35.8 | SIGMA= | 6.2 | PHAS= | -36.6 | FOM= | 0.54 | TEST= 0
| INDE | 2 | 14 | 66 | FOBS= | 32.1 | SIGMA= | 9.2 | PHAS= | -137.4 | FOM= | 0.56 | TEST= 0
| INDE | 2 | 14 | 68 | FOBS= | 9.7 | SIGMA= | 29.9 | PHAS= | -98.5 | FOM= | 0.09 | TEST= 0
| INDE | 2 | 14 | 70 | FOBS= | 76.8 | SIGMA= | 3.9 | PHAS= | -167.3 | FOM= | 0.89 | TEST= 0
| INDE | 2 | 14 | 72 | FOBS= | 22.2 | SIGMA= | 13.5 | PHAS= | -144.8 | FOM= | 0.66 | TEST= 0
| INDE | 2 | 14 | 74 | FOBS= | 33.0 | SIGMA= | 9.1 | PHAS= | 110.5 | FOM= | 0.30 | TEST= 0
| INDE | 2 | 14 | 76 | FOBS= | 63.3 | SIGMA= | 5.0 | PHAS= | 106.7 | FOM= | 0.88 | TEST= 0
| INDE | 2 | 15 | 11 | FOBS= | 51.2 | SIGMA= | 2.0 | PHAS= | -80.2 | FOM= | 0.96 | TEST= 0
| INDE | 2 | 15 | 13 | FOBS= | 420.7 | SIGMA= | 0.6 | PHAS= | -69.2 | FOM= | 0.96 | TEST= 0
| INDE | 2 | 15 | 15 | FOBS= | 162.0 | SIGMA= | 0.8 | PHAS= | 170.9 | FOM= | 0.65 | TEST= 1
| INDE | 2 | 15 | 17 | FOBS= | 84.3 | SIGMA= | 0.9 | PHAS= | -175.4 | FOM= | 0.88 | TEST= 0
| INDE | 2 | 15 | 19 | FOBS= | 209.5 | SIGMA= | 0.5 | PHAS= | -100.8 | FOM= | 0.88 | TEST= 1
| INDE | 2 | 15 | 21 | FOBS= | 184.4 | SIGMA= | 0.6 | PHAS= | -49.7 | FOM= | 0.87 | TEST= 0
| INDE | 2 | 15 | 23 | FOBS= | 103.5 | SIGMA= | 0.8 | PHAS= | -26.0 | FOM= | 0.95 | TEST= 0
| INDE | 2 | 15 | 25 | FOBS= | 91.8 | SIGMA= | 0.8 | PHAS= | 173.4 | FOM= | 0.88 | TEST= 1
| INDE | 2 | 15 | 27 | FOBS= | 131.0 | SIGMA= | 0.7 | PHAS= | -21.7 | FOM= | 0.99 | TEST= 0
| INDE | 2 | 15 | 29 | FOBS= | 173.3 | SIGMA= | 0.7 | PHAS= | 3.9 | FOM= | 0.97 | TEST= 0
| INDE | 2 | 15 | 31 | FOBS= | 288.9 | SIGMA= | 0.6 | PHAS= | -91.8 | FOM= | 0.97 | TEST= 0
| INDE | 2 | 15 | 33 | FOBS= | 218.2 | SIGMA= | 0.7 | PHAS= | 174.1 | FOM= | 0.97 | TEST= 0
| INDE | 2 | 15 | 35 | FOBS= | 101.8 | SIGMA= | 1.3 | PHAS= | 50.3 | FOM= | 0.91 | TEST= 0
| INDE | 2 | 15 | 37 | FOBS= | 108.8 | SIGMA= | 1.4 | PHAS= | -170.0 | FOM= | 0.97 | TEST= 0
| INDE | 2 | 15 | 39 | FOBS= | 357.2 | SIGMA= | 0.8 | PHAS= | 71.5 | FOM= | 0.65 | TEST= 1

*FIG. 12A - 55*

```
INDE   2   15   41  FOBS=    191.0  SIGMA=    1.1  PHAS=   -67.4  FOM=  0.95  TEST= 0
INDE   2   15   43  FOBS=     65.8  SIGMA=    3.1  PHAS=  -178.3  FOM=  0.69  TEST= 0
INDE   2   15   45  FOBS=    102.0  SIGMA=    2.2  PHAS=   -42.8  FOM=  0.88  TEST= 0
INDE   2   15   47  FOBS=    224.3  SIGMA=    1.2  PHAS=  -175.6  FOM=  0.94  TEST= 0
INDE   2   15   49  FOBS=     93.5  SIGMA=    2.3  PHAS=   152.5  FOM=  0.72  TEST= 0
INDE   2   15   51  FOBS=    144.3  SIGMA=    1.5  PHAS=  -119.9  FOM=  0.82  TEST= 0
INDE   2   15   53  FOBS=    167.2  SIGMA=    1.3  PHAS=   -57.9  FOM=  0.91  TEST= 0
INDE   2   15   55  FOBS=     16.2  SIGMA=   12.2  PHAS=     0.0  FOM=  0.00  TEST= 1
INDE   2   15   57  FOBS=    115.5  SIGMA=    1.7  PHAS=  -137.6  FOM=  0.86  TEST= 0
INDE   2   15   59  FOBS=     31.7  SIGMA=    5.3  PHAS=    87.6  FOM=  0.70  TEST= 0
INDE   2   15   61  FOBS=    101.0  SIGMA=    1.7  PHAS=   113.7  FOM=  0.82  TEST= 0
INDE   2   15   63  FOBS=     35.4  SIGMA=    4.5  PHAS=    21.6  FOM=  0.40  TEST= 0
INDE   2   15   65  FOBS=     66.2  SIGMA=    4.6  PHAS=   -26.0  FOM=  0.83  TEST= 0
INDE   2   15   67  FOBS=     77.8  SIGMA=    3.8  PHAS=   157.2  FOM=  0.83  TEST= 0
INDE   2   15   69  FOBS=     72.4  SIGMA=    4.1  PHAS=    61.8  FOM=  0.71  TEST= 0
INDE   2   15   71  FOBS=     36.2  SIGMA=    8.4  PHAS=  -143.3  FOM=  0.56  TEST= 0
INDE   2   15   73  FOBS=     60.3  SIGMA=    5.1  PHAS=   122.7  FOM=  0.93  TEST= 0
INDE   2   15   75  FOBS=     65.5  SIGMA=    4.8  PHAS=   -19.3  FOM=  0.90  TEST= 0
INDE   2   16   12  FOBS=    151.2  SIGMA=    0.9  PHAS=  -112.0  FOM=  0.67  TEST= 0
INDE   2   16   14  FOBS=    358.3  SIGMA=    0.6  PHAS=  -149.1  FOM=  0.96  TEST= 1
INDE   2   16   16  FOBS=    278.5  SIGMA=    0.6  PHAS=    45.3  FOM=  0.96  TEST= 0
INDE   2   16   18  FOBS=    232.9  SIGMA=    0.6  PHAS=    70.2  FOM=  0.91  TEST= 0
INDE   2   16   20  FOBS=    152.5  SIGMA=    0.6  PHAS=  -137.5  FOM=  0.96  TEST= 0
INDE   2   16   22  FOBS=    112.6  SIGMA=    0.7  PHAS=   -95.4  FOM=  0.92  TEST= 0
INDE   2   16   24  FOBS=    123.8  SIGMA=    0.7  PHAS=    -1.6  FOM=  0.99  TEST= 0
INDE   2   16   26  FOBS=    103.0  SIGMA=    0.8  PHAS=    99.2  FOM=  0.88  TEST= 0
INDE   2   16   28  FOBS=    124.2  SIGMA=    0.7  PHAS=  -130.0  FOM=  0.98  TEST= 0
INDE   2   16   30  FOBS=    123.6  SIGMA=    0.9  PHAS=  -120.8  FOM=  0.95  TEST= 0
INDE   2   16   32  FOBS=    145.4  SIGMA=    0.6  PHAS=   128.6  FOM=  0.99  TEST= 0
INDE   2   16   34  FOBS=    166.1  SIGMA=    0.7  PHAS=   143.2  FOM=  0.90  TEST= 0
INDE   2   16   36  FOBS=    430.1  SIGMA=    0.7  PHAS=    15.6  FOM=  0.98  TEST= 1
INDE   2   16   38  FOBS=    154.7  SIGMA=    0.8  PHAS=  -179.7  FOM=  0.95  TEST= 0
INDE   2   16   40  FOBS=    107.2  SIGMA=    1.1  PHAS=   -91.0  FOM=  0.88  TEST= 0
INDE   2   16   42  FOBS=    222.3  SIGMA=    1.0  PHAS=   138.8  FOM=  0.94  TEST= 0
INDE   2   16   44  FOBS=    103.4  SIGMA=    2.2  PHAS=   149.3  FOM=  0.86  TEST= 0
INDE   2   16   46  FOBS=     54.3  SIGMA=    4.0  PHAS=   114.7  FOM=  0.68  TEST= 0
INDE   2   16   48  FOBS=    190.4  SIGMA=    1.2  PHAS=   148.2  FOM=  0.93  TEST= 0
INDE   2   16   50  FOBS=     28.9  SIGMA=    7.2  PHAS=  -153.7  FOM=  0.24  TEST= 0
INDE   2   16   52  FOBS=     19.8  SIGMA=   10.1  PHAS=   170.2  FOM=  0.12  TEST= 0
INDE   2   16   54  FOBS=    145.8  SIGMA=    1.4  PHAS=   178.7  FOM=  0.94  TEST= 0
INDE   2   16   56  FOBS=     76.8  SIGMA=    2.6  PHAS=  -120.9  FOM=  0.81  TEST= 0
INDE   2   16   58  FOBS=     24.3  SIGMA=    9.5  PHAS=    73.8  FOM=  0.56  TEST= 0
INDE   2   16   60  FOBS=     57.5  SIGMA=    2.9  PHAS=  -102.7  FOM=  0.76  TEST= 0
INDE   2   16   62  FOBS=    135.2  SIGMA=    1.3  PHAS=  -160.1  FOM=  0.95  TEST= 0
INDE   2   16   64  FOBS=     93.3  SIGMA=    2.9  PHAS=  -103.7  FOM=  0.90  TEST= 0
INDE   2   16   66  FOBS=     88.9  SIGMA=    3.5  PHAS=  -158.4  FOM=  0.93  TEST= 0
INDE   2   16   68  FOBS=      0.0  SIGMA=   24.4  PHAS=     0.0  FOM=  0.00  TEST= 0
INDE   2   16   70  FOBS=     94.1  SIGMA=    3.3  PHAS=   145.6  FOM=  0.89  TEST= 0
INDE   2   16   72  FOBS=     21.4  SIGMA=   14.5  PHAS=    76.2  FOM=  0.13  TEST= 0
INDE   2   16   74  FOBS=     40.2  SIGMA=    7.8  PHAS=    10.6  FOM=  0.68  TEST= 0
INDE   2   16   76  FOBS=     19.8  SIGMA=   16.1  PHAS=    70.7  FOM=  0.26  TEST= 0
INDE   2   17   13  FOBS=    196.6  SIGMA=    0.8  PHAS=   104.9  FOM=  0.50  TEST= 0
INDE   2   17   15  FOBS=     90.2  SIGMA=    1.4  PHAS=    85.1  FOM=  0.93  TEST= 0
INDE   2   17   17  FOBS=    387.5  SIGMA=    0.5  PHAS=   -20.5  FOM=  0.96  TEST= 0
INDE   2   17   19  FOBS=    104.4  SIGMA=    0.9  PHAS=    65.1  FOM=  0.97  TEST= 0
INDE   2   17   21  FOBS=    149.8  SIGMA=    0.6  PHAS=   120.4  FOM=  0.88  TEST= 0
INDE   2   17   23  FOBS=    162.7  SIGMA=    0.6  PHAS=  -173.1  FOM=  0.99  TEST= 0
INDE   2   17   25  FOBS=    128.4  SIGMA=    0.6  PHAS=  -144.4  FOM=  0.91  TEST= 0
INDE   2   17   27  FOBS=     62.0  SIGMA=    1.3  PHAS=     3.1  FOM=  0.98  TEST= 0
INDE   2   17   29  FOBS=    110.9  SIGMA=    0.8  PHAS=   118.9  FOM=  0.96  TEST= 0
INDE   2   17   31  FOBS=     83.9  SIGMA=    1.0  PHAS=  -174.1  FOM=  0.99  TEST= 0
INDE   2   17   33  FOBS=    366.4  SIGMA=    0.6  PHAS=   101.2  FOM=  0.99  TEST= 0
INDE   2   17   35  FOBS=    180.7  SIGMA=    0.9  PHAS=    -7.2  FOM=  0.96  TEST= 0
INDE   2   17   37  FOBS=    219.7  SIGMA=    0.8  PHAS=  -118.2  FOM=  0.93  TEST= 0
INDE   2   17   39  FOBS=    274.0  SIGMA=    0.6  PHAS=   137.3  FOM=  0.95  TEST= 0
INDE   2   17   41  FOBS=    176.8  SIGMA=    0.7  PHAS=    78.0  FOM=  0.96  TEST= 0
INDE   2   17   43  FOBS=    220.2  SIGMA=    1.1  PHAS=    71.8  FOM=  0.93  TEST= 0
INDE   2   17   45  FOBS=    251.6  SIGMA=    1.1  PHAS=    41.2  FOM=  0.94  TEST= 0
INDE   2   17   47  FOBS=     63.3  SIGMA=    3.5  PHAS=   -19.3  FOM=  0.93  TEST= 0
INDE   2   17   49  FOBS=     59.6  SIGMA=    3.6  PHAS=   -43.4  FOM=  0.80  TEST= 0
```

*FIG. 12A - 56*

| | | | | | | | | | | | | |
|---|---|---|---|---|---|---|---|---|---|---|---|---|
| INDE | 2 | 17 | 51 | FOBS= | 95.6 | SIGMA= | 2.2 | PHAS= | -154.8 | FOM= | 0.27 | TEST= 0 |
| INDE | 2 | 17 | 53 | FOBS= | 75.2 | SIGMA= | 2.7 | PHAS= | -9.0 | FOM= | 0.89 | TEST= 0 |
| INDE | 2 | 17 | 55 | FOBS= | 62.1 | SIGMA= | 3.3 | PHAS= | 171.0 | FOM= | 0.60 | TEST= 0 |
| INDE | 2 | 17 | 57 | FOBS= | 0.0 | SIGMA= | 22.0 | PHAS= | 0.0 | FOM= | 0.00 | TEST= 0 |
| INDE | 2 | 17 | 59 | FOBS= | 73.9 | SIGMA= | 2.4 | PHAS= | 74.0 | FOM= | 0.77 | TEST= 0 |
| INDE | 2 | 17 | 61 | FOBS= | 159.4 | SIGMA= | 1.1 | PHAS= | 144.2 | FOM= | 0.96 | TEST= 0 |
| INDE | 2 | 17 | 63 | FOBS= | 135.0 | SIGMA= | 1.4 | PHAS= | 109.1 | FOM= | 0.94 | TEST= 0 |
| INDE | 2 | 17 | 65 | FOBS= | 40.5 | SIGMA= | 7.6 | PHAS= | -76.0 | FOM= | 0.43 | TEST= 0 |
| INDE | 2 | 17 | 67 | FOBS= | 39.5 | SIGMA= | 7.8 | PHAS= | 7.9 | FOM= | 0.58 | TEST= 0 |
| INDE | 2 | 17 | 69 | FOBS= | 110.8 | SIGMA= | 2.8 | PHAS= | 58.5 | FOM= | 0.88 | TEST= 0 |
| INDE | 2 | 17 | 71 | FOBS= | 54.7 | SIGMA= | 5.7 | PHAS= | 106.4 | FOM= | 0.53 | TEST= 0 |
| INDE | 2 | 17 | 73 | FOBS= | 57.2 | SIGMA= | 5.6 | PHAS= | 153.5 | FOM= | 0.71 | TEST= 1 |
| INDE | 2 | 17 | 75 | FOBS= | 84.6 | SIGMA= | 3.8 | PHAS= | -55.4 | FOM= | 0.93 | TEST= 0 |
| INDE | 2 | 18 | 2 | FOBS= | 312.2 | SIGMA= | 0.5 | PHAS= | -177.4 | FOM= | 0.91 | TEST= 0 |
| INDE | 2 | 18 | 4 | FOBS= | 185.2 | SIGMA= | 0.4 | PHAS= | -106.4 | FOM= | 0.99 | TEST= 0 |
| INDE | 2 | 18 | 6 | FOBS= | 201.3 | SIGMA= | 0.6 | PHAS= | -107.9 | FOM= | 0.95 | TEST= 0 |
| INDE | 2 | 18 | 14 | FOBS= | 174.6 | SIGMA= | 0.9 | PHAS= | -91.6 | FOM= | 0.86 | TEST= 0 |
| INDE | 2 | 18 | 16 | FOBS= | 162.6 | SIGMA= | 0.9 | PHAS= | -85.1 | FOM= | 0.77 | TEST= 0 |
| INDE | 2 | 18 | 18 | FOBS= | 153.0 | SIGMA= | 0.9 | PHAS= | -97.3 | FOM= | 0.95 | TEST= 0 |
| INDE | 2 | 18 | 20 | FOBS= | 126.3 | SIGMA= | 0.8 | PHAS= | -13.1 | FOM= | 0.96 | TEST= 0 |
| INDE | 2 | 18 | 22 | FOBS= | 141.8 | SIGMA= | 0.7 | PHAS= | 53.0 | FOM= | 0.99 | TEST= 1 |
| INDE | 2 | 18 | 24 | FOBS= | 91.4 | SIGMA= | 0.9 | PHAS= | 51.0 | FOM= | 0.98 | TEST= 0 |
| INDE | 2 | 18 | 26 | FOBS= | 122.8 | SIGMA= | 0.7 | PHAS= | 25.6 | FOM= | 0.99 | TEST= 0 |
| INDE | 2 | 18 | 28 | FOBS= | 25.5 | SIGMA= | 3.1 | PHAS= | 37.6 | FOM= | 0.76 | TEST= 1 |
| INDE | 2 | 18 | 30 | FOBS= | 106.3 | SIGMA= | 0.9 | PHAS= | 176.2 | FOM= | 0.89 | TEST= 0 |
| INDE | 2 | 18 | 32 | FOBS= | 190.9 | SIGMA= | 0.7 | PHAS= | 32.9 | FOM= | 0.98 | TEST= 0 |
| INDE | 2 | 18 | 34 | FOBS= | 237.2 | SIGMA= | 0.5 | PHAS= | -170.1 | FOM= | 0.96 | TEST= 0 |
| INDE | 2 | 18 | 36 | FOBS= | 340.1 | SIGMA= | 0.7 | PHAS= | -44.4 | FOM= | 0.95 | TEST= 0 |
| INDE | 2 | 18 | 38 | FOBS= | 190.0 | SIGMA= | 0.9 | PHAS= | 97.0 | FOM= | 0.93 | TEST= 0 |
| INDE | 2 | 18 | 40 | FOBS= | 77.4 | SIGMA= | 1.5 | PHAS= | -35.2 | FOM= | 0.94 | TEST= 0 |
| INDE | 2 | 18 | 42 | FOBS= | 237.0 | SIGMA= | 0.7 | PHAS= | 0.5 | FOM= | 0.96 | TEST= 0 |
| INDE | 2 | 18 | 44 | FOBS= | 313.3 | SIGMA= | 0.9 | PHAS= | -108.4 | FOM= | 0.98 | TEST= 0 |
| INDE | 2 | 18 | 46 | FOBS= | 133.8 | SIGMA= | 1.7 | PHAS= | -104.0 | FOM= | 0.76 | TEST= 0 |
| INDE | 2 | 18 | 48 | FOBS= | 95.6 | SIGMA= | 2.3 | PHAS= | -175.1 | FOM= | 0.97 | TEST= 0 |
| INDE | 2 | 18 | 50 | FOBS= | 171.7 | SIGMA= | 1.3 | PHAS= | -120.1 | FOM= | 0.60 | TEST= 1 |
| INDE | 2 | 18 | 52 | FOBS= | 75.1 | SIGMA= | 2.8 | PHAS= | -161.9 | FOM= | 0.37 | TEST= 0 |
| INDE | 2 | 18 | 54 | FOBS= | 111.0 | SIGMA= | 1.9 | PHAS= | -150.2 | FOM= | 0.93 | TEST= 0 |
| INDE | 2 | 18 | 56 | FOBS= | 155.2 | SIGMA= | 1.4 | PHAS= | -63.9 | FOM= | 0.90 | TEST= 0 |
| INDE | 2 | 18 | 58 | FOBS= | 138.4 | SIGMA= | 1.6 | PHAS= | 9.9 | FOM= | 0.95 | TEST= 0 |
| INDE | 2 | 18 | 60 | FOBS= | 168.1 | SIGMA= | 1.1 | PHAS= | -20.6 | FOM= | 0.96 | TEST= 0 |
| INDE | 2 | 18 | 62 | FOBS= | 29.2 | SIGMA= | 6.8 | PHAS= | -3.9 | FOM= | 0.57 | TEST= 0 |
| INDE | 2 | 18 | 64 | FOBS= | 0.0 | SIGMA= | 25.2 | PHAS= | 0.0 | FOM= | 0.00 | TEST= 0 |
| INDE | 2 | 18 | 66 | FOBS= | 14.0 | SIGMA= | 22.1 | PHAS= | 175.3 | FOM= | 0.55 | TEST= 1 |
| INDE | 2 | 18 | 68 | FOBS= | 0.0 | SIGMA= | 24.8 | PHAS= | 0.0 | FOM= | 0.00 | TEST= 0 |
| INDE | 2 | 18 | 70 | FOBS= | 62.2 | SIGMA= | 5.1 | PHAS= | 6.8 | FOM= | 0.85 | TEST= 0 |
| INDE | 2 | 18 | 72 | FOBS= | 66.4 | SIGMA= | 4.8 | PHAS= | -118.0 | FOM= | 0.70 | TEST= 0 |
| INDE | 2 | 18 | 74 | FOBS= | 43.1 | SIGMA= | 7.6 | PHAS= | 113.2 | FOM= | 0.56 | TEST= 0 |
| INDE | 2 | 19 | 3 | FOBS= | 232.2 | SIGMA= | 0.5 | PHAS= | 87.0 | FOM= | 0.82 | TEST= 0 |
| INDE | 2 | 19 | 5 | FOBS= | 143.6 | SIGMA= | 0.7 | PHAS= | 37.1 | FOM= | 0.95 | TEST= 0 |
| INDE | 2 | 19 | 7 | FOBS= | 215.2 | SIGMA= | 0.6 | PHAS= | 143.1 | FOM= | 0.91 | TEST= 0 |
| INDE | 2 | 19 | 15 | FOBS= | 93.2 | SIGMA= | 1.4 | PHAS= | 102.6 | FOM= | 0.69 | TEST= 0 |
| INDE | 2 | 19 | 17 | FOBS= | 129.5 | SIGMA= | 1.1 | PHAS= | 139.5 | FOM= | 0.99 | TEST= 0 |
| INDE | 2 | 19 | 19 | FOBS= | 28.4 | SIGMA= | 3.0 | PHAS= | -158.3 | FOM= | 0.66 | TEST= 0 |
| INDE | 2 | 19 | 21 | FOBS= | 155.4 | SIGMA= | 0.7 | PHAS= | 28.1 | FOM= | 0.98 | TEST= 0 |
| INDE | 2 | 19 | 23 | FOBS= | 45.3 | SIGMA= | 2.0 | PHAS= | -140.4 | FOM= | 0.95 | TEST= 0 |
| INDE | 2 | 19 | 25 | FOBS= | 151.4 | SIGMA= | 0.7 | PHAS= | -138.9 | FOM= | 0.99 | TEST= 0 |
| INDE | 2 | 19 | 27 | FOBS= | 208.3 | SIGMA= | 0.6 | PHAS= | -97.6 | FOM= | 0.99 | TEST= 0 |
| INDE | 2 | 19 | 29 | FOBS= | 113.0 | SIGMA= | 0.8 | PHAS= | 164.5 | FOM= | 0.95 | TEST= 0 |
| INDE | 2 | 19 | 31 | FOBS= | 225.3 | SIGMA= | 0.6 | PHAS= | 119.7 | FOM= | 0.93 | TEST= 0 |
| INDE | 2 | 19 | 33 | FOBS= | 256.6 | SIGMA= | 0.7 | PHAS= | 76.8 | FOM= | 0.92 | TEST= 0 |
| INDE | 2 | 19 | 35 | FOBS= | 112.2 | SIGMA= | 1.0 | PHAS= | 88.9 | FOM= | 0.88 | TEST= 0 |
| INDE | 2 | 19 | 37 | FOBS= | 137.4 | SIGMA= | 0.8 | PHAS= | -75.1 | FOM= | 0.97 | TEST= 0 |
| INDE | 2 | 19 | 39 | FOBS= | 241.1 | SIGMA= | 0.6 | PHAS= | -121.2 | FOM= | 0.93 | TEST= 0 |
| INDE | 2 | 19 | 41 | FOBS= | 89.8 | SIGMA= | 1.4 | PHAS= | 33.9 | FOM= | 0.77 | TEST= 0 |
| INDE | 2 | 19 | 43 | FOBS= | 151.0 | SIGMA= | 1.0 | PHAS= | 129.9 | FOM= | 0.92 | TEST= 0 |
| INDE | 2 | 19 | 45 | FOBS= | 339.4 | SIGMA= | 0.8 | PHAS= | 121.9 | FOM= | 0.97 | TEST= 0 |
| INDE | 2 | 19 | 47 | FOBS= | 166.5 | SIGMA= | 1.4 | PHAS= | -141.3 | FOM= | 0.87 | TEST= 0 |
| INDE | 2 | 19 | 49 | FOBS= | 95.6 | SIGMA= | 2.3 | PHAS= | 110.7 | FOM= | 0.95 | TEST= 0 |
| INDE | 2 | 19 | 51 | FOBS= | 154.9 | SIGMA= | 1.4 | PHAS= | 56.4 | FOM= | 0.93 | TEST= 0 |
| INDE | 2 | 19 | 53 | FOBS= | 0.0 | SIGMA= | 20.8 | PHAS= | 0.0 | FOM= | 0.00 | TEST= 0 |

*FIG. 12A - 57*

```
INDE  2  19  55  FOBS=  118.8  SIGMA=   1.8  PHAS=  -166.2  FOM=  0.92  TEST= 0
INDE  2  19  57  FOBS=  111.1  SIGMA=   1.9  PHAS=   -96.3  FOM=  0.87  TEST= 0
INDE  2  19  59  FOBS=  179.7  SIGMA=   1.3  PHAS=   -77.1  FOM=  0.97  TEST= 0
INDE  2  19  61  FOBS=  112.5  SIGMA=   1.6  PHAS=  -136.1  FOM=  0.94  TEST= 0
INDE  2  19  63  FOBS=   84.1  SIGMA=   2.4  PHAS=   -16.6  FOM=  0.45  TEST= 0
INDE  2  19  65  FOBS=   64.8  SIGMA=   4.9  PHAS=   -33.7  FOM=  0.88  TEST= 0
INDE  2  19  67  FOBS=   44.6  SIGMA=   7.0  PHAS=   -71.1  FOM=  0.67  TEST= 0
INDE  2  19  69  FOBS=   32.6  SIGMA=   9.6  PHAS=    17.6  FOM=  0.23  TEST= 0
INDE  2  19  71  FOBS=   35.5  SIGMA=   8.8  PHAS=   128.1  FOM=  0.74  TEST= 0
INDE  2  19  73  FOBS=    0.0  SIGMA=  25.4  PHAS=     0.0  FOM=  0.00  TEST= 0
INDE  2  19  75  FOBS=   14.2  SIGMA=  23.1  PHAS=   -92.6  FOM=  0.24  TEST= 0
INDE  2  20   2  FOBS=  182.1  SIGMA=   0.6  PHAS=   -37.8  FOM=  0.93  TEST= 0
INDE  2  20   4  FOBS=  181.0  SIGMA=   0.5  PHAS=   137.9  FOM=  0.47  TEST= 0
INDE  2  20   6  FOBS=   28.4  SIGMA=   3.0  PHAS=   142.9  FOM=  0.46  TEST= 0
INDE  2  20   8  FOBS=  130.6  SIGMA=   0.9  PHAS=    49.9  FOM=  0.72  TEST= 0
INDE  2  20  16  FOBS=   43.9  SIGMA=   2.9  PHAS=   145.7  FOM=  0.35  TEST= 0
INDE  2  20  18  FOBS=  219.7  SIGMA=   0.9  PHAS=    11.6  FOM=  0.99  TEST= 0
INDE  2  20  20  FOBS=  166.7  SIGMA=   0.8  PHAS=    20.3  FOM=  0.94  TEST= 0
INDE  2  20  22  FOBS=  243.0  SIGMA=   0.6  PHAS=   -44.7  FOM=  0.97  TEST= 0
INDE  2  20  24  FOBS=   52.4  SIGMA=   1.9  PHAS=    16.8  FOM=  0.94  TEST= 0
INDE  2  20  26  FOBS=  120.3  SIGMA=   0.8  PHAS=   109.5  FOM=  0.95  TEST= 0
INDE  2  20  28  FOBS=   92.2  SIGMA=   1.0  PHAS=    75.4  FOM=  0.98  TEST= 0
INDE  2  20  30  FOBS=  136.7  SIGMA=   0.7  PHAS=   108.5  FOM=  0.93  TEST= 0
INDE  2  20  32  FOBS=  231.9  SIGMA=   0.8  PHAS=    36.6  FOM=  0.92  TEST= 0
INDE  2  20  34  FOBS=  145.2  SIGMA=   0.9  PHAS=   -71.8  FOM=  0.96  TEST= 0
INDE  2  20  36  FOBS=  298.1  SIGMA=   0.7  PHAS=   -76.4  FOM=  0.96  TEST= 0
INDE  2  20  38  FOBS=  237.9  SIGMA=   0.6  PHAS=   166.6  FOM=  0.96  TEST= 0
INDE  2  20  40  FOBS=    0.0  SIGMA=  16.3  PHAS=     0.0  FOM=  0.00  TEST= 0
INDE  2  20  42  FOBS=  394.9  SIGMA=   0.6  PHAS=    28.7  FOM=  0.99  TEST= 0
INDE  2  20  44  FOBS=  103.8  SIGMA=   1.4  PHAS=   -30.4  FOM=  0.72  TEST= 0
INDE  2  20  46  FOBS=   95.5  SIGMA=   2.0  PHAS=    68.3  FOM=  0.93  TEST= 0
INDE  2  20  48  FOBS=   65.5  SIGMA=   3.3  PHAS=   173.8  FOM=  0.60  TEST= 0
INDE  2  20  50  FOBS=  171.2  SIGMA=   1.3  PHAS=   -44.9  FOM=  0.95  TEST= 0
INDE  2  20  52  FOBS=   92.2  SIGMA=   2.3  PHAS=  -115.7  FOM=  0.63  TEST= 0
INDE  2  20  54  FOBS=   79.7  SIGMA=   2.6  PHAS=   179.5  FOM=  0.86  TEST= 0
INDE  2  20  56  FOBS=   74.2  SIGMA=   2.7  PHAS=  -159.2  FOM=  0.66  TEST= 0
INDE  2  20  58  FOBS=  116.9  SIGMA=   1.9  PHAS=   155.2  FOM=  0.89  TEST= 0
INDE  2  20  60  FOBS=   85.6  SIGMA=   2.6  PHAS=  -104.8  FOM=  0.87  TEST= 0
INDE  2  20  62  FOBS=    0.0  SIGMA=  20.2  PHAS=     0.0  FOM=  0.00  TEST= 0
INDE  2  20  64  FOBS=   83.7  SIGMA=   3.9  PHAS=  -143.3  FOM=  0.88  TEST= 0
INDE  2  20  66  FOBS=   69.1  SIGMA=   4.7  PHAS=  -155.1  FOM=  0.74  TEST= 0
INDE  2  20  68  FOBS=   72.1  SIGMA=   4.4  PHAS=    89.2  FOM=  0.76  TEST= 0
INDE  2  20  70  FOBS=   75.0  SIGMA=   4.3  PHAS=     7.0  FOM=  0.88  TEST= 0
INDE  2  20  72  FOBS=   45.7  SIGMA=   7.0  PHAS=   -29.6  FOM=  0.75  TEST= 0
INDE  2  20  74  FOBS=   70.0  SIGMA=   4.8  PHAS=   167.8  FOM=  0.92  TEST= 0
INDE  2  21   3  FOBS=  305.7  SIGMA=   0.5  PHAS=    51.9  FOM=  0.97  TEST= 0
INDE  2  21   5  FOBS=  283.2  SIGMA=   0.6  PHAS=    14.0  FOM=  0.94  TEST= 0
INDE  2  21   7  FOBS=  157.2  SIGMA=   0.8  PHAS=    23.0  FOM=  0.82  TEST= 0
INDE  2  21  17  FOBS=   32.7  SIGMA=   4.1  PHAS=    45.2  FOM=  0.41  TEST= 0
INDE  2  21  19  FOBS=  105.5  SIGMA=   1.1  PHAS=  -111.8  FOM=  0.99  TEST= 0
INDE  2  21  21  FOBS=   78.2  SIGMA=   1.3  PHAS=   -60.7  FOM=  0.90  TEST= 0
INDE  2  21  23  FOBS=  154.2  SIGMA=   0.8  PHAS=  -130.9  FOM=  0.97  TEST= 0
INDE  2  21  25  FOBS=    0.0  SIGMA=  14.8  PHAS=     0.0  FOM=  0.00  TEST= 0
INDE  2  21  27  FOBS=  301.3  SIGMA=   0.6  PHAS=   -37.7  FOM=  0.99  TEST= 0
INDE  2  21  29  FOBS=  284.5  SIGMA=   0.6  PHAS=  -119.2  FOM=  0.97  TEST= 0
INDE  2  21  31  FOBS=    0.0  SIGMA=  13.8  PHAS=     0.0  FOM=  0.00  TEST= 0
INDE  2  21  33  FOBS=  205.7  SIGMA=   0.8  PHAS=    44.6  FOM=  0.98  TEST= 0
INDE  2  21  35  FOBS=  302.5  SIGMA=   0.8  PHAS=  -174.4  FOM=  0.93  TEST= 0
INDE  2  21  37  FOBS=   86.2  SIGMA=   1.5  PHAS=  -179.6  FOM=  0.97  TEST= 1
INDE  2  21  39  FOBS=  218.8  SIGMA=   0.6  PHAS=   -48.6  FOM=  0.50  TEST= 1
INDE  2  21  41  FOBS=  270.0  SIGMA=   0.9  PHAS=   -49.5  FOM=  0.99  TEST= 0
INDE  2  21  43  FOBS=   32.7  SIGMA=   4.7  PHAS=  -159.4  FOM=  0.28  TEST= 0
INDE  2  21  45  FOBS=   86.5  SIGMA=   1.7  PHAS=  -161.1  FOM=  0.90  TEST= 0
INDE  2  21  47  FOBS=   88.0  SIGMA=   2.1  PHAS=  -100.7  FOM=  0.77  TEST= 0
INDE  2  21  49  FOBS=  152.2  SIGMA=   1.3  PHAS=  -179.0  FOM=  0.96  TEST= 0
INDE  2  21  51  FOBS=  106.2  SIGMA=   2.0  PHAS=   130.2  FOM=  0.84  TEST= 0
INDE  2  21  53  FOBS=   90.8  SIGMA=   2.3  PHAS=   106.0  FOM=  0.66  TEST= 0
INDE  2  21  55  FOBS=   29.6  SIGMA=   9.2  PHAS=   141.5  FOM=  0.05  TEST= 0
INDE  2  21  57  FOBS=   82.8  SIGMA=   2.4  PHAS=   101.6  FOM=  0.78  TEST= 0
INDE  2  21  59  FOBS=    0.0  SIGMA=  22.5  PHAS=     0.0  FOM=  0.00  TEST= 1
```

*FIG. 12A - 58*

```
INDE  2  21  61  FOBS=    34.7  SIGMA=   4.9  PHAS=  -108.2  FOM=  0.33  TEST=  0
INDE  2  21  63  FOBS=    75.5  SIGMA=   3.0  PHAS=  -105.3  FOM=  0.54  TEST=  0
INDE  2  21  65  FOBS=    40.6  SIGMA=   7.9  PHAS=   153.7  FOM=  0.50  TEST=  0
INDE  2  21  67  FOBS=     0.0  SIGMA=  25.4  PHAS=     0.0  FOM=  0.00  TEST=  0
INDE  2  21  69  FOBS=    46.3  SIGMA=   6.8  PHAS=   -39.5  FOM=  0.66  TEST=  0
INDE  2  21  71  FOBS=    58.3  SIGMA=   5.6  PHAS=  -108.8  FOM=  0.89  TEST=  0
INDE  2  21  73  FOBS=     0.0  SIGMA=  25.7  PHAS=     0.0  FOM=  0.00  TEST=  0
INDE  2  22   2  FOBS=   252.5  SIGMA=   0.5  PHAS=  -129.1  FOM=  0.87  TEST=  1
INDE  2  22   4  FOBS=   316.1  SIGMA=   0.5  PHAS=     0.3  FOM=  0.92  TEST=  0
INDE  2  22   6  FOBS=   113.7  SIGMA=   0.9  PHAS=  -111.1  FOM=  0.96  TEST=  0
INDE  2  22   8  FOBS=   102.2  SIGMA=   1.1  PHAS=   -20.1  FOM=  0.49  TEST=  0
INDE  2  22  18  FOBS=   180.7  SIGMA=   1.0  PHAS=    -9.7  FOM=  0.98  TEST=  0
INDE  2  22  20  FOBS=   189.9  SIGMA=   1.0  PHAS=    79.2  FOM=  0.92  TEST=  0
INDE  2  22  22  FOBS=    94.5  SIGMA=   1.1  PHAS=   -66.7  FOM=  0.99  TEST=  0
INDE  2  22  24  FOBS=   221.0  SIGMA=   0.6  PHAS=   -44.1  FOM=  0.97  TEST=  0
INDE  2  22  26  FOBS=   121.8  SIGMA=   1.0  PHAS=  -118.4  FOM=  0.97  TEST=  0
INDE  2  22  28  FOBS=   166.9  SIGMA=   0.8  PHAS=   174.7  FOM=  0.98  TEST=  0
INDE  2  22  30  FOBS=   223.8  SIGMA=   0.6  PHAS=   177.2  FOM=  0.97  TEST=  0
INDE  2  22  32  FOBS=   115.3  SIGMA=   1.0  PHAS=   130.6  FOM=  0.92  TEST=  0
INDE  2  22  34  FOBS=    50.4  SIGMA=   2.1  PHAS=   -61.4  FOM=  0.33  TEST=  0
INDE  2  22  36  FOBS=   107.2  SIGMA=   1.0  PHAS=   149.8  FOM=  0.86  TEST=  0
INDE  2  22  38  FOBS=   118.2  SIGMA=   1.0  PHAS=    83.9  FOM=  0.78  TEST=  0
INDE  2  22  40  FOBS=   252.1  SIGMA=   0.9  PHAS=   141.3  FOM=  0.96  TEST=  0
INDE  2  22  42  FOBS=   230.2  SIGMA=   1.1  PHAS=    95.2  FOM=  0.95  TEST=  0
INDE  2  22  44  FOBS=    79.1  SIGMA=   2.2  PHAS=   168.3  FOM=  0.90  TEST=  0
INDE  2  22  46  FOBS=   111.3  SIGMA=   1.3  PHAS=   -90.8  FOM=  0.83  TEST=  0
INDE  2  22  48  FOBS=   182.7  SIGMA=   0.9  PHAS=   153.0  FOM=  0.91  TEST=  0
INDE  2  22  50  FOBS=   207.6  SIGMA=   0.9  PHAS=    37.9  FOM=  0.94  TEST=  0
INDE  2  22  52  FOBS=    60.7  SIGMA=   3.5  PHAS=    25.7  FOM=  0.71  TEST=  0
INDE  2  22  54  FOBS=    68.7  SIGMA=   3.0  PHAS=  -115.1  FOM=  0.59  TEST=  0
INDE  2  22  56  FOBS=     0.0  SIGMA=  20.2  PHAS=     0.0  FOM=  0.00  TEST=  0
INDE  2  22  58  FOBS=     0.0  SIGMA=  19.8  PHAS=     0.0  FOM=  0.00  TEST=  0
INDE  2  22  60  FOBS=    11.3  SIGMA=  19.2  PHAS=   -22.8  FOM=  0.05  TEST=  0
INDE  2  22  62  FOBS=    58.0  SIGMA=   3.6  PHAS=    64.3  FOM=  0.44  TEST=  0
INDE  2  22  64  FOBS=    50.2  SIGMA=   6.6  PHAS=   -73.4  FOM=  0.58  TEST=  0
INDE  2  22  66  FOBS=    15.7  SIGMA=  28.5  PHAS=    62.5  FOM=  0.23  TEST=  0
INDE  2  22  68  FOBS=    72.5  SIGMA=   4.6  PHAS=    99.8  FOM=  0.72  TEST=  0
INDE  2  22  70  FOBS=    27.1  SIGMA=  11.9  PHAS=  -114.3  FOM=  0.00  TEST=  1
INDE  2  22  72  FOBS=    21.2  SIGMA=  15.4  PHAS=    15.6  FOM=  0.15  TEST=  0
INDE  2  22  74  FOBS=    39.3  SIGMA=   8.6  PHAS=  -144.2  FOM=  0.64  TEST=  0
INDE  2  23   3  FOBS=    84.4  SIGMA=   1.1  PHAS=    22.0  FOM=  0.95  TEST=  0
INDE  2  23   5  FOBS=   109.4  SIGMA=   0.6  PHAS=   100.3  FOM=  0.82  TEST=  0
INDE  2  23   7  FOBS=   259.9  SIGMA=   0.6  PHAS=    -6.4  FOM=  0.98  TEST=  0
INDE  2  23   9  FOBS=   127.5  SIGMA=   1.0  PHAS=  -179.1  FOM=  0.85  TEST=  0
INDE  2  23  17  FOBS=   128.3  SIGMA=   1.8  PHAS=   -27.2  FOM=  0.86  TEST=  0
INDE  2  23  19  FOBS=   125.7  SIGMA=   1.3  PHAS=   -83.4  FOM=  0.70  TEST=  0
INDE  2  23  21  FOBS=   195.1  SIGMA=   0.8  PHAS=   -43.5  FOM=  0.97  TEST=  0
INDE  2  23  23  FOBS=   203.5  SIGMA=   0.8  PHAS=   -73.2  FOM=  0.96  TEST=  0
INDE  2  23  25  FOBS=   172.9  SIGMA=   0.8  PHAS=  -162.5  FOM=  0.97  TEST=  0
INDE  2  23  27  FOBS=    53.3  SIGMA=   2.2  PHAS=   -95.2  FOM=  0.96  TEST=  0
INDE  2  23  29  FOBS=   171.7  SIGMA=   0.8  PHAS=   176.1  FOM=  0.93  TEST=  0
INDE  2  23  31  FOBS=    52.8  SIGMA=   2.2  PHAS=    74.8  FOM=  0.49  TEST=  0
INDE  2  23  33  FOBS=   434.3  SIGMA=   0.6  PHAS=    67.1  FOM=  0.97  TEST=  0
INDE  2  23  35  FOBS=    91.5  SIGMA=   1.3  PHAS=    86.4  FOM=  0.96  TEST=  0
INDE  2  23  37  FOBS=    46.0  SIGMA=   2.4  PHAS=  -101.1  FOM=  0.78  TEST=  0
INDE  2  23  39  FOBS=   161.4  SIGMA=   0.8  PHAS=   -55.3  FOM=  0.90  TEST=  0
INDE  2  23  41  FOBS=   193.9  SIGMA=   1.1  PHAS=   -31.4  FOM=  0.92  TEST=  0
INDE  2  23  43  FOBS=   142.7  SIGMA=   1.2  PHAS=    51.2  FOM=  0.92  TEST=  0
INDE  2  23  45  FOBS=   226.3  SIGMA=   0.7  PHAS=  -143.6  FOM=  0.91  TEST=  0
INDE  2  23  47  FOBS=   153.2  SIGMA=   1.0  PHAS=    73.9  FOM=  0.90  TEST=  0
INDE  2  23  49  FOBS=   159.2  SIGMA=   1.0  PHAS=    24.4  FOM=  0.61  TEST=  1
INDE  2  23  51  FOBS=    61.2  SIGMA=   2.8  PHAS=  -158.2  FOM=  0.64  TEST=  1
INDE  2  23  53  FOBS=     0.0  SIGMA=  21.7  PHAS=     0.0  FOM=  0.00  TEST=  0
INDE  2  23  55  FOBS=     0.0  SIGMA=  21.2  PHAS=     0.0  FOM=  0.00  TEST=  0
INDE  2  23  57  FOBS=    39.7  SIGMA=   5.6  PHAS=    45.3  FOM=  0.40  TEST=  0
INDE  2  23  59  FOBS=     7.5  SIGMA=  28.9  PHAS=     0.2  FOM=  0.06  TEST=  0
INDE  2  23  61  FOBS=    99.1  SIGMA=   2.5  PHAS=   -44.1  FOM=  0.80  TEST=  0
INDE  2  23  63  FOBS=    93.8  SIGMA=   2.5  PHAS=   -45.0  FOM=  0.90  TEST=  0
INDE  2  23  65  FOBS=    14.4  SIGMA=  23.0  PHAS=   107.0  FOM=  0.29  TEST=  0
INDE  2  23  67  FOBS=    66.9  SIGMA=   5.0  PHAS=     0.1  FOM=  0.74  TEST=  0
```

*FIG. 12A - 59*

```
INDE  2  23  69  FOBS=   33.1  SIGMA=   9.9  PHAS=   -13.4  FOM=  0.29  TEST= 0
INDE  2  23  71  FOBS=   39.3  SIGMA=   8.5  PHAS=  -141.4  FOM=  0.46  TEST= 0
INDE  2  23  73  FOBS=    0.0  SIGMA=  26.1  PHAS=     0.0  FOM=  0.00  TEST= 0
INDE  2  24   2  FOBS=   94.4  SIGMA=   1.0  PHAS=     9.3  FOM=  0.24  TEST= 0
INDE  2  24   4  FOBS=  190.3  SIGMA=   0.7  PHAS=   -28.2  FOM=  0.95  TEST= 0
INDE  2  24   6  FOBS=   26.4  SIGMA=   3.6  PHAS=  -121.0  FOM=  0.92  TEST= 0
INDE  2  24   8  FOBS=   69.6  SIGMA=   1.5  PHAS=   -95.1  FOM=  0.81  TEST= 0
INDE  2  24  18  FOBS=  177.7  SIGMA=   1.5  PHAS=   -59.8  FOM=  0.71  TEST= 0
INDE  2  24  20  FOBS=  131.4  SIGMA=   1.3  PHAS=  -174.2  FOM=  0.99  TEST= 0
INDE  2  24  22  FOBS=  198.4  SIGMA=   1.1  PHAS=   157.6  FOM=  0.94  TEST= 0
INDE  2  24  24  FOBS=   86.3  SIGMA=   1.4  PHAS=  -127.5  FOM=  0.99  TEST= 0
INDE  2  24  26  FOBS=   88.1  SIGMA=   1.4  PHAS=   177.2  FOM=  0.78  TEST= 0
INDE  2  24  28  FOBS=  261.6  SIGMA=   0.8  PHAS=   165.5  FOM=  0.91  TEST= 0
INDE  2  24  30  FOBS=  295.6  SIGMA=   0.6  PHAS=  -148.0  FOM=  0.94  TEST= 0
INDE  2  24  32  FOBS=  216.9  SIGMA=   0.9  PHAS=    84.9  FOM=  0.86  TEST= 0
INDE  2  24  34  FOBS=  417.5  SIGMA=   0.5  PHAS=   -48.2  FOM=  0.97  TEST= 0
INDE  2  24  36  FOBS=  212.8  SIGMA=   0.6  PHAS=  -112.7  FOM=  0.94  TEST= 0
INDE  2  24  38  FOBS=   40.4  SIGMA=   2.9  PHAS=    -5.7  FOM=  0.87  TEST= 0
INDE  2  24  40  FOBS=   46.4  SIGMA=   3.0  PHAS=    11.6  FOM=  0.56  TEST= 0
INDE  2  24  42  FOBS=   60.2  SIGMA=   2.3  PHAS=    60.4  FOM=  0.92  TEST= 0
INDE  2  24  44  FOBS=  215.9  SIGMA=   1.4  PHAS=  -126.0  FOM=  0.94  TEST= 0
INDE  2  24  46  FOBS=    0.0  SIGMA=  17.2  PHAS=     0.0  FOM=  0.00  TEST= 1
INDE  2  24  48  FOBS=   27.8  SIGMA=   5.2  PHAS=  -131.6  FOM=  0.44  TEST= 0
INDE  2  24  50  FOBS=  140.7  SIGMA=   1.3  PHAS=  -156.1  FOM=  0.84  TEST= 0
INDE  2  24  52  FOBS=   45.9  SIGMA=   3.8  PHAS=   -51.8  FOM=  0.64  TEST= 0
INDE  2  24  54  FOBS=   64.4  SIGMA=   2.7  PHAS=   -36.7  FOM=  0.36  TEST= 0
INDE  2  24  56  FOBS=   33.3  SIGMA=   6.2  PHAS=  -155.7  FOM=  0.43  TEST= 0
INDE  2  24  58  FOBS=    0.0  SIGMA=  20.9  PHAS=     0.0  FOM=  0.00  TEST= 0
INDE  2  24  60  FOBS=   91.9  SIGMA=   2.4  PHAS=   -98.5  FOM=  0.82  TEST= 0
INDE  2  24  62  FOBS=   55.7  SIGMA=   4.1  PHAS=  -166.9  FOM=  0.58  TEST= 0
INDE  2  24  64  FOBS=   37.8  SIGMA=   6.0  PHAS=   -87.0  FOM=  0.27  TEST= 0
INDE  2  24  66  FOBS=   88.7  SIGMA=   3.8  PHAS=   -71.7  FOM=  0.87  TEST= 0
INDE  2  24  68  FOBS=   23.3  SIGMA=  20.6  PHAS=   176.6  FOM=  0.37  TEST= 0
INDE  2  24  70  FOBS=    0.0  SIGMA=  25.7  PHAS=     0.0  FOM=  0.00  TEST= 0
INDE  2  24  72  FOBS=   18.5  SIGMA=  18.2  PHAS=   -26.1  FOM=  0.17  TEST= 0
INDE  2  25   3  FOBS=  120.9  SIGMA=   0.9  PHAS=   -86.0  FOM=  0.88  TEST= 0
INDE  2  25   5  FOBS=   73.1  SIGMA=   0.9  PHAS=    59.2  FOM=  0.98  TEST= 0
INDE  2  25   7  FOBS=  178.9  SIGMA=   0.7  PHAS=    74.7  FOM=  0.99  TEST= 0
INDE  2  25   9  FOBS=   85.1  SIGMA=   1.3  PHAS=    71.5  FOM=  0.84  TEST= 1
INDE  2  25  19  FOBS=  115.9  SIGMA=   1.5  PHAS=  -147.3  FOM=  0.87  TEST= 0
INDE  2  25  21  FOBS=  270.9  SIGMA=   0.9  PHAS=    28.8  FOM=  0.95  TEST= 0
INDE  2  25  23  FOBS=   72.2  SIGMA=   1.6  PHAS=    24.8  FOM=  0.56  TEST= 1
INDE  2  25  25  FOBS=  130.3  SIGMA=   1.0  PHAS=    59.0  FOM=  0.68  TEST= 0
INDE  2  25  27  FOBS=  126.9  SIGMA=   1.1  PHAS=    12.8  FOM=  0.95  TEST= 0
INDE  2  25  29  FOBS=  268.9  SIGMA=   0.7  PHAS=    94.9  FOM=  0.94  TEST= 0
INDE  2  25  31  FOBS=  137.9  SIGMA=   1.1  PHAS=   -67.8  FOM=  0.92  TEST= 0
INDE  2  25  33  FOBS=  216.4  SIGMA=   1.0  PHAS=   -44.3  FOM=  0.90  TEST= 0
INDE  2  25  35  FOBS=   36.1  SIGMA=   3.9  PHAS=   -87.5  FOM=  0.68  TEST= 0
INDE  2  25  37  FOBS=  204.5  SIGMA=   0.7  PHAS=  -145.1  FOM=  0.95  TEST= 0
INDE  2  25  39  FOBS=  298.3  SIGMA=   0.6  PHAS=   -33.2  FOM=  0.93  TEST= 0
INDE  2  25  41  FOBS=    0.0  SIGMA=  17.8  PHAS=     0.0  FOM=  0.00  TEST= 0
INDE  2  25  43  FOBS=    0.0  SIGMA=  17.0  PHAS=     0.0  FOM=  0.00  TEST= 0
INDE  2  25  45  FOBS=  130.5  SIGMA=   1.2  PHAS=    45.3  FOM=  0.77  TEST= 0
INDE  2  25  47  FOBS=  153.0  SIGMA=   1.1  PHAS=     8.8  FOM=  0.85  TEST= 1
INDE  2  25  49  FOBS=  109.2  SIGMA=   1.3  PHAS=   -46.8  FOM=  0.90  TEST= 0
INDE  2  25  51  FOBS=   69.7  SIGMA=   1.9  PHAS=  -102.3  FOM=  0.79  TEST= 0
INDE  2  25  53  FOBS=   32.2  SIGMA=   5.2  PHAS=    75.0  FOM=  0.30  TEST= 0
INDE  2  25  55  FOBS=  100.6  SIGMA=   1.7  PHAS=   174.8  FOM=  0.76  TEST= 0
INDE  2  25  57  FOBS=   69.9  SIGMA=   3.0  PHAS=    -9.8  FOM=  0.22  TEST= 0
INDE  2  25  59  FOBS=   40.1  SIGMA=   6.1  PHAS=    64.8  FOM=  0.60  TEST= 0
INDE  2  25  61  FOBS=   59.8  SIGMA=   5.4  PHAS=  -125.8  FOM=  0.76  TEST= 0
INDE  2  25  63  FOBS=   86.1  SIGMA=   2.7  PHAS=   -92.2  FOM=  0.83  TEST= 0
INDE  2  25  65  FOBS=   45.0  SIGMA=   7.7  PHAS=   178.5  FOM=  0.73  TEST= 0
INDE  2  25  67  FOBS=   40.2  SIGMA=   8.4  PHAS=  -136.8  FOM=  0.68  TEST= 0
INDE  2  25  69  FOBS=   72.4  SIGMA=   4.7  PHAS=   177.4  FOM=  0.19  TEST= 1
INDE  2  25  71  FOBS=   32.7  SIGMA=  10.5  PHAS=  -124.1  FOM=  0.16  TEST= 0
INDE  2  25  73  FOBS=    0.0  SIGMA=  26.4  PHAS=     0.0  FOM=  0.00  TEST= 0
INDE  2  26   2  FOBS=  219.9  SIGMA=   0.6  PHAS=   100.6  FOM=  0.96  TEST= 0
INDE  2  26   4  FOBS=  187.7  SIGMA=   0.7  PHAS=   -56.1  FOM=  0.98  TEST= 0
INDE  2  26   6  FOBS=  278.9  SIGMA=   0.5  PHAS=     7.2  FOM=  0.98  TEST= 1
```

*FIG. 12A - 60*

| | | | | | | | | | | | |
|---|---|---|---|---|---|---|---|---|---|---|---|
| INDE | 2 | 26 | 8 | FOBS= | 151.0 | SIGMA= | 0.9 | PHAS= | 3.9 | FOM= | 0.99 | TEST= 0
| INDE | 2 | 26 | 10 | FOBS= | 204.9 | SIGMA= | 0.8 | PHAS= | -108.3 | FOM= | 0.98 | TEST= 0
| INDE | 2 | 26 | 20 | FOBS= | 115.2 | SIGMA= | 1.6 | PHAS= | -86.5 | FOM= | 0.87 | TEST= 0
| INDE | 2 | 26 | 22 | FOBS= | 256.7 | SIGMA= | 0.9 | PHAS= | -153.8 | FOM= | 0.96 | TEST= 0
| INDE | 2 | 26 | 24 | FOBS= | 149.1 | SIGMA= | 0.9 | PHAS= | -76.1 | FOM= | 0.93 | TEST= 0
| INDE | 2 | 26 | 26 | FOBS= | 73.4 | SIGMA= | 1.8 | PHAS= | -107.6 | FOM= | 0.82 | TEST= 0
| INDE | 2 | 26 | 28 | FOBS= | 198.7 | SIGMA= | 1.0 | PHAS= | 25.2 | FOM= | 0.98 | TEST= 0
| INDE | 2 | 26 | 30 | FOBS= | 225.2 | SIGMA= | 0.8 | PHAS= | -116.9 | FOM= | 0.94 | TEST= 0
| INDE | 2 | 26 | 32 | FOBS= | 77.1 | SIGMA= | 2.0 | PHAS= | -96.6 | FOM= | 0.74 | TEST= 0
| INDE | 2 | 26 | 34 | FOBS= | 338.7 | SIGMA= | 0.8 | PHAS= | -77.8 | FOM= | 0.95 | TEST= 1
| INDE | 2 | 26 | 36 | FOBS= | 210.5 | SIGMA= | 0.8 | PHAS= | -132.9 | FOM= | 0.93 | TEST= 0
| INDE | 2 | 26 | 38 | FOBS= | 212.4 | SIGMA= | 0.7 | PHAS= | 150.5 | FOM= | 0.97 | TEST= 0
| INDE | 2 | 26 | 40 | FOBS= | 268.9 | SIGMA= | 0.6 | PHAS= | -26.0 | FOM= | 0.97 | TEST= 0
| INDE | 2 | 26 | 42 | FOBS= | 124.6 | SIGMA= | 1.2 | PHAS= | 123.1 | FOM= | 0.96 | TEST= 0
| INDE | 2 | 26 | 44 | FOBS= | 107.6 | SIGMA= | 1.5 | PHAS= | -136.1 | FOM= | 0.96 | TEST= 0
| INDE | 2 | 26 | 46 | FOBS= | 102.5 | SIGMA= | 1.4 | PHAS= | -161.4 | FOM= | 0.22 | TEST= 1
| INDE | 2 | 26 | 48 | FOBS= | 0.0 | SIGMA= | 18.2 | PHAS= | 0.0 | FOM= | 0.00 | TEST= 0
| INDE | 2 | 26 | 50 | FOBS= | 141.8 | SIGMA= | 1.0 | PHAS= | -165.2 | FOM= | 0.94 | TEST= 0
| INDE | 2 | 26 | 52 | FOBS= | 95.5 | SIGMA= | 1.4 | PHAS= | 139.8 | FOM= | 0.88 | TEST= 0
| INDE | 2 | 26 | 54 | FOBS= | 152.4 | SIGMA= | 1.2 | PHAS= | 20.8 | FOM= | 0.62 | TEST= 1
| INDE | 2 | 26 | 56 | FOBS= | 0.0 | SIGMA= | 19.7 | PHAS= | 0.0 | FOM= | 0.00 | TEST= 0
| INDE | 2 | 26 | 58 | FOBS= | 29.5 | SIGMA= | 7.6 | PHAS= | -136.4 | FOM= | 0.33 | TEST= 0
| INDE | 2 | 26 | 60 | FOBS= | 106.0 | SIGMA= | 2.4 | PHAS= | -30.2 | FOM= | 0.79 | TEST= 0
| INDE | 2 | 26 | 62 | FOBS= | 27.0 | SIGMA= | 11.6 | PHAS= | 42.1 | FOM= | 0.58 | TEST= 0
| INDE | 2 | 26 | 64 | FOBS= | 103.1 | SIGMA= | 2.3 | PHAS= | 95.0 | FOM= | 0.93 | TEST= 0
| INDE | 2 | 26 | 66 | FOBS= | 58.6 | SIGMA= | 6.0 | PHAS= | 104.2 | FOM= | 0.72 | TEST= 0
| INDE | 2 | 26 | 68 | FOBS= | 80.0 | SIGMA= | 4.4 | PHAS= | 93.9 | FOM= | 0.87 | TEST= 0
| INDE | 2 | 26 | 70 | FOBS= | 0.0 | SIGMA= | 26.2 | PHAS= | 0.0 | FOM= | 0.00 | TEST= 0
| INDE | 2 | 26 | 72 | FOBS= | 0.0 | SIGMA= | 26.3 | PHAS= | 0.0 | FOM= | 0.00 | TEST= 0
| INDE | 2 | 27 | 3 | FOBS= | 42.5 | SIGMA= | 2.2 | PHAS= | 38.3 | FOM= | 0.66 | TEST= 0
| INDE | 2 | 27 | 5 | FOBS= | 338.4 | SIGMA= | 0.5 | PHAS= | -120.6 | FOM= | 0.99 | TEST= 0
| INDE | 2 | 27 | 7 | FOBS= | 242.8 | SIGMA= | 0.6 | PHAS= | -127.0 | FOM= | 0.98 | TEST= 1
| INDE | 2 | 27 | 9 | FOBS= | 57.6 | SIGMA= | 2.0 | PHAS= | 127.3 | FOM= | 0.93 | TEST= 0
| INDE | 2 | 27 | 11 | FOBS= | 40.3 | SIGMA= | 3.0 | PHAS= | -145.1 | FOM= | 0.71 | TEST= 0
| INDE | 2 | 27 | 19 | FOBS= | 110.8 | SIGMA= | 2.4 | PHAS= | 0.0 | FOM= | 0.00 | TEST= 1
| INDE | 2 | 27 | 21 | FOBS= | 279.0 | SIGMA= | 0.9 | PHAS= | 18.4 | FOM= | 0.86 | TEST= 0
| INDE | 2 | 27 | 23 | FOBS= | 216.0 | SIGMA= | 1.1 | PHAS= | 149.7 | FOM= | 0.95 | TEST= 1
| INDE | 2 | 27 | 25 | FOBS= | 215.8 | SIGMA= | 0.8 | PHAS= | -36.0 | FOM= | 0.80 | TEST= 1
| INDE | 2 | 27 | 27 | FOBS= | 154.5 | SIGMA= | 1.0 | PHAS= | -20.2 | FOM= | 0.96 | TEST= 0
| INDE | 2 | 27 | 29 | FOBS= | 89.8 | SIGMA= | 1.7 | PHAS= | 165.5 | FOM= | 0.86 | TEST= 0
| INDE | 2 | 27 | 31 | FOBS= | 161.1 | SIGMA= | 1.1 | PHAS= | -67.3 | FOM= | 0.85 | TEST= 0
| INDE | 2 | 27 | 33 | FOBS= | 179.2 | SIGMA= | 1.2 | PHAS= | -148.3 | FOM= | 0.95 | TEST= 0
| INDE | 2 | 27 | 35 | FOBS= | 241.3 | SIGMA= | 0.8 | PHAS= | -107.6 | FOM= | 0.97 | TEST= 1
| INDE | 2 | 27 | 37 | FOBS= | 237.8 | SIGMA= | 0.9 | PHAS= | 75.9 | FOM= | 0.56 | TEST= 1
| INDE | 2 | 27 | 39 | FOBS= | 149.8 | SIGMA= | 1.0 | PHAS= | -33.2 | FOM= | 0.96 | TEST= 0
| INDE | 2 | 27 | 41 | FOBS= | 189.3 | SIGMA= | 0.8 | PHAS= | -111.1 | FOM= | 0.92 | TEST= 0
| INDE | 2 | 27 | 43 | FOBS= | 169.8 | SIGMA= | 0.9 | PHAS= | 86.0 | FOM= | 0.94 | TEST= 0
| INDE | 2 | 27 | 45 | FOBS= | 0.0 | SIGMA= | 17.5 | PHAS= | 0.0 | FOM= | 0.00 | TEST= 0
| INDE | 2 | 27 | 47 | FOBS= | 140.9 | SIGMA= | 1.0 | PHAS= | 22.6 | FOM= | 0.91 | TEST= 1
| INDE | 2 | 27 | 49 | FOBS= | 6.5 | SIGMA= | 23.9 | PHAS= | 141.6 | FOM= | 0.15 | TEST= 0
| INDE | 2 | 27 | 51 | FOBS= | 37.6 | SIGMA= | 3.8 | PHAS= | -143.7 | FOM= | 0.11 | TEST= 0
| INDE | 2 | 27 | 53 | FOBS= | 126.3 | SIGMA= | 1.1 | PHAS= | 9.7 | FOM= | 0.91 | TEST= 0
| INDE | 2 | 27 | 55 | FOBS= | 0.0 | SIGMA= | 19.8 | PHAS= | 0.0 | FOM= | 0.00 | TEST= 1
| INDE | 2 | 27 | 57 | FOBS= | 13.8 | SIGMA= | 14.3 | PHAS= | -138.1 | FOM= | 0.27 | TEST= 0
| INDE | 2 | 27 | 59 | FOBS= | 14.1 | SIGMA= | 25.2 | PHAS= | -143.4 | FOM= | 0.27 | TEST= 0
| INDE | 2 | 27 | 61 | FOBS= | 115.7 | SIGMA= | 2.9 | PHAS= | -85.1 | FOM= | 0.95 | TEST= 0
| INDE | 2 | 27 | 63 | FOBS= | 73.1 | SIGMA= | 3.2 | PHAS= | -50.4 | FOM= | 0.92 | TEST= 0
| INDE | 2 | 27 | 65 | FOBS= | 0.0 | SIGMA= | 26.3 | PHAS= | 0.0 | FOM= | 0.00 | TEST= 0
| INDE | 2 | 27 | 67 | FOBS= | 99.2 | SIGMA= | 3.7 | PHAS= | 53.5 | FOM= | 0.90 | TEST= 0
| INDE | 2 | 27 | 69 | FOBS= | 0.0 | SIGMA= | 26.4 | PHAS= | 0.0 | FOM= | 0.00 | TEST= 0
| INDE | 2 | 27 | 71 | FOBS= | 41.9 | SIGMA= | 8.5 | PHAS= | 104.2 | FOM= | 0.16 | TEST= 0
| INDE | 2 | 28 | 2 | FOBS= | 265.0 | SIGMA= | 0.6 | PHAS= | 0.1 | FOM= | 0.99 | TEST= 0
| INDE | 2 | 28 | 4 | FOBS= | 163.5 | SIGMA= | 0.8 | PHAS= | -102.1 | FOM= | 0.94 | TEST= 0
| INDE | 2 | 28 | 6 | FOBS= | 236.8 | SIGMA= | 0.6 | PHAS= | -175.4 | FOM= | 0.99 | TEST= 0
| INDE | 2 | 28 | 8 | FOBS= | 123.3 | SIGMA= | 1.0 | PHAS= | 50.8 | FOM= | 0.96 | TEST= 0
| INDE | 2 | 28 | 10 | FOBS= | 119.7 | SIGMA= | 1.2 | PHAS= | -25.9 | FOM= | 0.99 | TEST= 0
| INDE | 2 | 28 | 20 | FOBS= | 347.5 | SIGMA= | 1.3 | PHAS= | 48.1 | FOM= | 0.95 | TEST= 0
| INDE | 2 | 28 | 22 | FOBS= | 187.3 | SIGMA= | 1.2 | PHAS= | -173.5 | FOM= | 0.84 | TEST= 0
| INDE | 2 | 28 | 24 | FOBS= | 183.5 | SIGMA= | 1.4 | PHAS= | -128.0 | FOM= | 0.96 | TEST= 0
| INDE | 2 | 28 | 26 | FOBS= | 335.8 | SIGMA= | 0.7 | PHAS= | -85.0 | FOM= | 0.96 | TEST= 0

*FIG. 12A - 61*

```
INDE  2  28  28  FOBS=  238.8  SIGMA=   0.8  PHAS=  -38.0  FOM=  0.93  TEST= 0
INDE  2  28  30  FOBS=  162.8  SIGMA=   1.1  PHAS= -118.2  FOM=  0.95  TEST= 0
INDE  2  28  32  FOBS=   48.4  SIGMA=   3.4  PHAS=  -86.4  FOM=  0.43  TEST= 0
INDE  2  28  34  FOBS=  157.5  SIGMA=   1.2  PHAS= -104.0  FOM=  0.88  TEST= 0
INDE  2  28  36  FOBS=  202.5  SIGMA=   1.0  PHAS= -141.2  FOM=  0.95  TEST= 1
INDE  2  28  38  FOBS=  161.8  SIGMA=   1.1  PHAS=   71.7  FOM=  0.84  TEST= 0
INDE  2  28  40  FOBS=   92.3  SIGMA=   1.8  PHAS=  -17.8  FOM=  0.42  TEST= 0
INDE  2  28  42  FOBS=   30.4  SIGMA=   5.2  PHAS= -102.8  FOM=  0.22  TEST= 0
INDE  2  28  44  FOBS=  198.5  SIGMA=   0.9  PHAS=   -8.7  FOM=  0.94  TEST= 0
INDE  2  28  46  FOBS=   42.2  SIGMA=   3.3  PHAS=   65.0  FOM=  0.29  TEST= 0
INDE  2  28  48  FOBS=   64.7  SIGMA=   2.0  PHAS=  -14.8  FOM=  0.76  TEST= 0
INDE  2  28  50  FOBS=   66.2  SIGMA=   2.1  PHAS=  114.1  FOM=  0.36  TEST= 1
INDE  2  28  52  FOBS=  132.8  SIGMA=   1.1  PHAS= -175.3  FOM=  0.88  TEST= 0
INDE  2  28  54  FOBS=   61.8  SIGMA=   2.2  PHAS=  -62.6  FOM=  0.87  TEST= 0
INDE  2  28  56  FOBS=   53.7  SIGMA=   3.1  PHAS=  132.0  FOM=  0.92  TEST= 0
INDE  2  28  58  FOBS=  126.9  SIGMA=   1.4  PHAS=  132.2  FOM=  0.93  TEST= 0
INDE  2  28  60  FOBS=   37.7  SIGMA=   7.2  PHAS=  157.0  FOM=  0.55  TEST= 0
INDE  2  28  62  FOBS=   62.0  SIGMA=   5.3  PHAS= -153.2  FOM=  0.85  TEST= 0
INDE  2  28  64  FOBS=   24.6  SIGMA=  10.7  PHAS=  109.4  FOM=  0.31  TEST= 0
INDE  2  28  66  FOBS=   65.2  SIGMA=   5.5  PHAS=   34.2  FOM=  0.61  TEST= 0
INDE  2  28  68  FOBS=   66.7  SIGMA=   5.5  PHAS=   35.4  FOM=  0.92  TEST= 0
INDE  2  28  70  FOBS=   61.7  SIGMA=   5.9  PHAS= -142.2  FOM=  0.88  TEST= 0
INDE  2  28  72  FOBS=    0.0  SIGMA=  26.8  PHAS=    0.0  FOM=  0.00  TEST= 0
INDE  2  29   3  FOBS=  181.4  SIGMA=   0.7  PHAS= -125.6  FOM=  0.97  TEST= 0
INDE  2  29   5  FOBS=   70.9  SIGMA=   1.3  PHAS=  -76.5  FOM=  0.91  TEST= 0
INDE  2  29   7  FOBS=  119.8  SIGMA=   0.7  PHAS=  -41.4  FOM=  0.67  TEST= 0
INDE  2  29   9  FOBS=  228.3  SIGMA=   0.7  PHAS=  -38.3  FOM=  0.99  TEST= 0
INDE  2  29  11  FOBS=   32.7  SIGMA=   3.9  PHAS=    8.4  FOM=  0.35  TEST= 0
INDE  2  29  21  FOBS=  135.1  SIGMA=   1.5  PHAS=  -43.2  FOM=  0.90  TEST= 0
INDE  2  29  23  FOBS=  198.0  SIGMA=   1.2  PHAS=   93.0  FOM=  0.94  TEST= 0
INDE  2  29  25  FOBS=  370.4  SIGMA=   0.9  PHAS=  179.2  FOM=  0.97  TEST= 0
INDE  2  29  27  FOBS=  305.1  SIGMA=   0.8  PHAS= -126.9  FOM=  0.98  TEST= 0
INDE  2  29  29  FOBS=  139.0  SIGMA=   1.2  PHAS= -131.4  FOM=  0.81  TEST= 0
INDE  2  29  31  FOBS=  104.4  SIGMA=   1.7  PHAS=  -93.6  FOM=  0.91  TEST= 0
INDE  2  29  33  FOBS=  120.2  SIGMA=   1.5  PHAS=  173.4  FOM=  0.89  TEST= 0
INDE  2  29  35  FOBS=   20.8  SIGMA=   8.8  PHAS= -169.6  FOM=  0.18  TEST= 0
INDE  2  29  37  FOBS=  196.2  SIGMA=   1.0  PHAS=  120.4  FOM=  0.97  TEST= 0
INDE  2  29  39  FOBS=   38.0  SIGMA=   4.4  PHAS=   40.6  FOM=  0.29  TEST= 0
INDE  2  29  41  FOBS=   61.9  SIGMA=   2.7  PHAS=  140.2  FOM=  0.87  TEST= 0
INDE  2  29  43  FOBS=  127.2  SIGMA=   1.3  PHAS= -101.3  FOM=  0.71  TEST= 0
INDE  2  29  45  FOBS=  127.2  SIGMA=   1.2  PHAS=  -50.6  FOM=  0.65  TEST= 1
INDE  2  29  47  FOBS=   99.9  SIGMA=   1.4  PHAS=   54.9  FOM=  0.28  TEST= 0
INDE  2  29  49  FOBS=  125.9  SIGMA=   1.0  PHAS= -130.2  FOM=  0.84  TEST= 0
INDE  2  29  51  FOBS=    0.0  SIGMA=  16.7  PHAS=    0.0  FOM=  0.00  TEST= 1
INDE  2  29  53  FOBS=   63.6  SIGMA=   2.2  PHAS= -115.5  FOM=  0.31  TEST= 1
INDE  2  29  55  FOBS=   57.1  SIGMA=   2.7  PHAS=  -46.5  FOM=  0.49  TEST= 0
INDE  2  29  57  FOBS=    0.0  SIGMA=  19.2  PHAS=    0.0  FOM=  0.00  TEST= 0
INDE  2  29  59  FOBS=   91.9  SIGMA=   2.5  PHAS=   48.8  FOM=  0.92  TEST= 0
INDE  2  29  61  FOBS=   72.9  SIGMA=   3.4  PHAS=  164.3  FOM=  0.88  TEST= 0
INDE  2  29  63  FOBS=   33.1  SIGMA=   9.7  PHAS= -158.1  FOM=  0.32  TEST= 0
INDE  2  29  65  FOBS=   47.8  SIGMA=   7.5  PHAS=  -67.7  FOM=  0.54  TEST= 0
INDE  2  29  67  FOBS=   70.8  SIGMA=   5.2  PHAS= -102.2  FOM=  0.88  TEST= 0
INDE  2  29  69  FOBS=   70.1  SIGMA=   5.2  PHAS=   46.8  FOM=  0.85  TEST= 0
INDE  2  29  71  FOBS=   50.3  SIGMA=   7.3  PHAS= -128.9  FOM=  0.04  TEST= 1
INDE  2  30   2  FOBS=   68.7  SIGMA=   1.6  PHAS=  169.6  FOM=  0.79  TEST= 0
INDE  2  30   4  FOBS=  235.1  SIGMA=   0.7  PHAS=  167.0  FOM=  0.94  TEST= 1
INDE  2  30   6  FOBS=  158.7  SIGMA=   0.8  PHAS= -150.8  FOM=  0.99  TEST= 0
INDE  2  30   8  FOBS=  188.4  SIGMA=   0.5  PHAS= -157.8  FOM=  0.94  TEST= 0
INDE  2  30  10  FOBS=   40.5  SIGMA=   3.1  PHAS= -175.8  FOM=  0.86  TEST= 0
INDE  2  30  12  FOBS=   52.4  SIGMA=   2.6  PHAS=   93.2  FOM=  0.96  TEST= 0
INDE  2  30  22  FOBS=  131.7  SIGMA=   1.7  PHAS=  132.1  FOM=  0.04  TEST= 1
INDE  2  30  24  FOBS=  200.3  SIGMA=   1.2  PHAS=   91.1  FOM=  0.89  TEST= 0
INDE  2  30  26  FOBS=  241.0  SIGMA=   1.1  PHAS=  116.2  FOM=  0.91  TEST= 0
INDE  2  30  28  FOBS=  154.8  SIGMA=   1.1  PHAS= -137.4  FOM=  0.99  TEST= 0
INDE  2  30  30  FOBS=  151.9  SIGMA=   1.2  PHAS=  178.3  FOM=  0.93  TEST= 0
INDE  2  30  32  FOBS=  129.4  SIGMA=   1.5  PHAS=  -89.0  FOM=  0.66  TEST= 0
INDE  2  30  34  FOBS=  109.6  SIGMA=   1.8  PHAS=  -43.7  FOM=  0.98  TEST= 0
INDE  2  30  36  FOBS=  191.9  SIGMA=   1.2  PHAS=   94.9  FOM=  0.97  TEST= 0
INDE  2  30  38  FOBS=  244.1  SIGMA=   0.8  PHAS=   23.6  FOM=  0.97  TEST= 0
INDE  2  30  40  FOBS=  124.9  SIGMA=   1.4  PHAS= -123.9  FOM=  0.90  TEST= 0
```

*FIG. 12A - 62*

| | | | | | | | | | | | |
|---|---|---|---|---|---|---|---|---|---|---|---|
| INDE | 2 | 30 | 42 | FOBS= | 116.1 | SIGMA= | 1.4 | PHAS= | -94.1 | FOM= | 0.96 | TEST= 0 |
| INDE | 2 | 30 | 44 | FOBS= | 165.8 | SIGMA= | 1.1 | PHAS= | -130.9 | FOM= | 0.90 | TEST= 0 |
| INDE | 2 | 30 | 46 | FOBS= | 84.5 | SIGMA= | 1.8 | PHAS= | -165.7 | FOM= | 0.71 | TEST= 0 |
| INDE | 2 | 30 | 48 | FOBS= | 81.7 | SIGMA= | 1.6 | PHAS= | 177.8 | FOM= | 0.25 | TEST= 0 |
| INDE | 2 | 30 | 50 | FOBS= | 111.5 | SIGMA= | 1.1 | PHAS= | 80.9 | FOM= | 0.89 | TEST= 0 |
| INDE | 2 | 30 | 52 | FOBS= | 155.2 | SIGMA= | 1.0 | PHAS= | -58.4 | FOM= | 0.92 | TEST= 0 |
| INDE | 2 | 30 | 54 | FOBS= | 16.8 | SIGMA= | 8.5 | PHAS= | -97.8 | FOM= | 0.21 | TEST= 0 |
| INDE | 2 | 30 | 56 | FOBS= | 124.9 | SIGMA= | 1.3 | PHAS= | 121.0 | FOM= | 0.93 | TEST= 0 |
| INDE | 2 | 30 | 58 | FOBS= | 52.3 | SIGMA= | 3.5 | PHAS= | -105.5 | FOM= | 0.83 | TEST= 0 |
| INDE | 2 | 30 | 60 | FOBS= | 59.9 | SIGMA= | 3.7 | PHAS= | -67.2 | FOM= | 0.29 | TEST= 0 |
| INDE | 2 | 30 | 62 | FOBS= | 100.3 | SIGMA= | 2.5 | PHAS= | 86.7 | FOM= | 0.94 | TEST= 0 |
| INDE | 2 | 30 | 64 | FOBS= | 71.8 | SIGMA= | 3.4 | PHAS= | -108.8 | FOM= | 0.83 | TEST= 0 |
| INDE | 2 | 30 | 66 | FOBS= | 64.8 | SIGMA= | 5.7 | PHAS= | 116.9 | FOM= | 0.86 | TEST= 0 |
| INDE | 2 | 30 | 68 | FOBS= | 62.8 | SIGMA= | 5.9 | PHAS= | -111.6 | FOM= | 0.21 | TEST= 1 |
| INDE | 2 | 30 | 70 | FOBS= | 51.3 | SIGMA= | 7.2 | PHAS= | 3.0 | FOM= | 0.69 | TEST= 0 |
| INDE | 2 | 31 | 3 | FOBS= | 156.3 | SIGMA= | 0.8 | PHAS= | 77.1 | FOM= | 0.99 | TEST= 0 |
| INDE | 2 | 31 | 7 | FOBS= | 173.8 | SIGMA= | 0.5 | PHAS= | 64.5 | FOM= | 0.83 | TEST= 0 |
| INDE | 2 | 31 | 9 | FOBS= | 150.5 | SIGMA= | 0.7 | PHAS= | 27.4 | FOM= | 0.90 | TEST= 0 |
| INDE | 2 | 31 | 11 | FOBS= | 54.9 | SIGMA= | 2.5 | PHAS= | -135.2 | FOM= | 0.98 | TEST= 0 |
| INDE | 2 | 31 | 13 | FOBS= | 202.4 | SIGMA= | 0.9 | PHAS= | -163.8 | FOM= | 0.91 | TEST= 0 |
| INDE | 2 | 31 | 21 | FOBS= | 102.1 | SIGMA= | 2.9 | PHAS= | -3.9 | FOM= | 0.36 | TEST= 0 |
| INDE | 2 | 31 | 23 | FOBS= | 265.9 | SIGMA= | 1.1 | PHAS= | 80.3 | FOM= | 0.81 | TEST= 0 |
| INDE | 2 | 31 | 25 | FOBS= | 267.2 | SIGMA= | 1.1 | PHAS= | 110.1 | FOM= | 0.94 | TEST= 0 |
| INDE | 2 | 31 | 27 | FOBS= | 232.5 | SIGMA= | 0.9 | PHAS= | 58.8 | FOM= | 0.89 | TEST= 0 |
| INDE | 2 | 31 | 29 | FOBS= | 228.7 | SIGMA= | 0.9 | PHAS= | 83.9 | FOM= | 0.97 | TEST= 0 |
| INDE | 2 | 31 | 31 | FOBS= | 107.9 | SIGMA= | 1.8 | PHAS= | -79.9 | FOM= | 0.99 | TEST= 0 |
| INDE | 2 | 31 | 33 | FOBS= | 189.5 | SIGMA= | 1.1 | PHAS= | 121.6 | FOM= | 0.98 | TEST= 0 |
| INDE | 2 | 31 | 35 | FOBS= | 276.8 | SIGMA= | 0.9 | PHAS= | -0.4 | FOM= | 0.96 | TEST= 0 |
| INDE | 2 | 31 | 37 | FOBS= | 41.3 | SIGMA= | 4.8 | PHAS= | -34.2 | FOM= | 0.26 | TEST= 0 |
| INDE | 2 | 31 | 39 | FOBS= | 172.8 | SIGMA= | 1.1 | PHAS= | 167.9 | FOM= | 0.95 | TEST= 0 |
| INDE | 2 | 31 | 41 | FOBS= | 158.7 | SIGMA= | 1.1 | PHAS= | 75.8 | FOM= | 0.90 | TEST= 0 |
| INDE | 2 | 31 | 43 | FOBS= | 229.1 | SIGMA= | 0.8 | PHAS= | 157.7 | FOM= | 0.97 | TEST= 0 |
| INDE | 2 | 31 | 45 | FOBS= | 124.7 | SIGMA= | 1.4 | PHAS= | 55.0 | FOM= | 0.86 | TEST= 0 |
| INDE | 2 | 31 | 47 | FOBS= | 130.0 | SIGMA= | 1.2 | PHAS= | 121.1 | FOM= | 0.94 | TEST= 0 |
| INDE | 2 | 31 | 49 | FOBS= | 82.4 | SIGMA= | 1.6 | PHAS= | 136.8 | FOM= | 0.92 | TEST= 0 |
| INDE | 2 | 31 | 51 | FOBS= | 95.5 | SIGMA= | 1.3 | PHAS= | 70.0 | FOM= | 0.77 | TEST= 1 |
| INDE | 2 | 31 | 53 | FOBS= | 115.2 | SIGMA= | 1.2 | PHAS= | -152.1 | FOM= | 0.94 | TEST= 0 |
| INDE | 2 | 31 | 55 | FOBS= | 143.4 | SIGMA= | 1.1 | PHAS= | 57.7 | FOM= | 0.95 | TEST= 0 |
| INDE | 2 | 31 | 57 | FOBS= | 0.0 | SIGMA= | 18.1 | PHAS= | 0.0 | FOM= | 0.00 | TEST= 0 |
| INDE | 2 | 31 | 59 | FOBS= | 89.5 | SIGMA= | 2.6 | PHAS= | 153.8 | FOM= | 0.87 | TEST= 0 |
| INDE | 2 | 31 | 61 | FOBS= | 105.5 | SIGMA= | 2.2 | PHAS= | 45.1 | FOM= | 0.94 | TEST= 0 |
| INDE | 2 | 31 | 63 | FOBS= | 8.8 | SIGMA= | 27.5 | PHAS= | -43.8 | FOM= | 0.07 | TEST= 0 |
| INDE | 2 | 31 | 65 | FOBS= | 9.3 | SIGMA= | 39.2 | PHAS= | 168.4 | FOM= | 0.09 | TEST= 0 |
| INDE | 2 | 31 | 67 | FOBS= | 51.4 | SIGMA= | 7.3 | PHAS= | -86.2 | FOM= | 0.80 | TEST= 0 |
| INDE | 2 | 31 | 69 | FOBS= | 48.8 | SIGMA= | 7.7 | PHAS= | -3.6 | FOM= | 0.87 | TEST= 0 |
| INDE | 2 | 31 | 71 | FOBS= | 18.1 | SIGMA= | 20.7 | PHAS= | -84.7 | FOM= | 0.14 | TEST= 0 |
| INDE | 2 | 32 | 2 | FOBS= | 111.8 | SIGMA= | 1.1 | PHAS= | -123.4 | FOM= | 0.98 | TEST= 0 |
| INDE | 2 | 32 | 4 | FOBS= | 242.1 | SIGMA= | 0.7 | PHAS= | 15.6 | FOM= | 0.98 | TEST= 0 |
| INDE | 2 | 32 | 6 | FOBS= | 329.2 | SIGMA= | 0.5 | PHAS= | -24.4 | FOM= | 0.99 | TEST= 0 |
| INDE | 2 | 32 | 8 | FOBS= | 291.7 | SIGMA= | 0.6 | PHAS= | -52.0 | FOM= | 0.97 | TEST= 0 |
| INDE | 2 | 32 | 10 | FOBS= | 58.6 | SIGMA= | 2.3 | PHAS= | -177.3 | FOM= | 0.68 | TEST= 0 |
| INDE | 2 | 32 | 12 | FOBS= | 292.2 | SIGMA= | 0.8 | PHAS= | 162.5 | FOM= | 0.95 | TEST= 0 |
| INDE | 2 | 32 | 22 | FOBS= | 113.0 | SIGMA= | 2.1 | PHAS= | 84.6 | FOM= | 0.84 | TEST= 0 |
| INDE | 2 | 32 | 24 | FOBS= | 302.1 | SIGMA= | 1.1 | PHAS= | -61.9 | FOM= | 0.89 | TEST= 0 |
| INDE | 2 | 32 | 26 | FOBS= | 102.4 | SIGMA= | 2.4 | PHAS= | -139.2 | FOM= | 0.90 | TEST= 0 |
| INDE | 2 | 32 | 28 | FOBS= | 229.1 | SIGMA= | 0.9 | PHAS= | -7.4 | FOM= | 0.95 | TEST= 0 |
| INDE | 2 | 32 | 30 | FOBS= | 30.8 | SIGMA= | 6.8 | PHAS= | -172.8 | FOM= | 0.07 | TEST= 0 |
| INDE | 2 | 32 | 32 | FOBS= | 223.0 | SIGMA= | 1.0 | PHAS= | 2.2 | FOM= | 0.98 | TEST= 0 |
| INDE | 2 | 32 | 34 | FOBS= | 64.3 | SIGMA= | 5.5 | PHAS= | -48.6 | FOM= | 0.91 | TEST= 1 |
| INDE | 2 | 32 | 36 | FOBS= | 204.2 | SIGMA= | 1.2 | PHAS= | -81.9 | FOM= | 0.73 | TEST= 0 |
| INDE | 2 | 32 | 38 | FOBS= | 302.9 | SIGMA= | 0.7 | PHAS= | 5.0 | FOM= | 0.97 | TEST= 0 |
| INDE | 2 | 32 | 40 | FOBS= | 68.8 | SIGMA= | 2.5 | PHAS= | -17.9 | FOM= | 0.93 | TEST= 0 |
| INDE | 2 | 32 | 42 | FOBS= | 21.7 | SIGMA= | 7.5 | PHAS= | -99.2 | FOM= | 0.31 | TEST= 1 |
| INDE | 2 | 32 | 44 | FOBS= | 113.2 | SIGMA= | 1.5 | PHAS= | 112.3 | FOM= | 0.64 | TEST= 1 |
| INDE | 2 | 32 | 46 | FOBS= | 159.9 | SIGMA= | 1.1 | PHAS= | 15.2 | FOM= | 0.94 | TEST= 0 |
| INDE | 2 | 32 | 48 | FOBS= | 163.6 | SIGMA= | 1.0 | PHAS= | 118.1 | FOM= | 0.96 | TEST= 0 |
| INDE | 2 | 32 | 50 | FOBS= | 76.9 | SIGMA= | 1.7 | PHAS= | -71.8 | FOM= | 0.90 | TEST= 0 |
| INDE | 2 | 32 | 52 | FOBS= | 90.6 | SIGMA= | 1.4 | PHAS= | -54.4 | FOM= | 0.78 | TEST= 0 |
| INDE | 2 | 32 | 54 | FOBS= | 83.0 | SIGMA= | 1.9 | PHAS= | 9.7 | FOM= | 0.94 | TEST= 0 |
| INDE | 2 | 32 | 56 | FOBS= | 0.0 | SIGMA= | 18.5 | PHAS= | 0.0 | FOM= | 0.00 | TEST= 1 |

*FIG. 12A - 63*

```
INDE  2  32  58  FOBS=   59.0  SIGMA=   3.1  PHAS=   153.4  FOM=  0.83  TEST= 0
INDE  2  32  60  FOBS=   97.3  SIGMA=   2.4  PHAS=    -0.7  FOM=  0.91  TEST= 0
INDE  2  32  62  FOBS=   53.0  SIGMA=   4.2  PHAS=     9.6  FOM=  0.77  TEST= 0
INDE  2  32  64  FOBS=   64.6  SIGMA=   3.9  PHAS=   -60.3  FOM=  0.76  TEST= 0
INDE  2  32  66  FOBS=   65.7  SIGMA=   5.7  PHAS=   120.8  FOM=  0.89  TEST= 0
INDE  2  32  68  FOBS=   94.2  SIGMA=   4.1  PHAS=   -92.0  FOM=  0.95  TEST= 0
INDE  2  32  70  FOBS=   55.0  SIGMA=   7.0  PHAS=  -115.2  FOM=  0.78  TEST= 0
INDE  2  33   3  FOBS=  115.7  SIGMA=   1.1  PHAS=  -101.9  FOM=  0.74  TEST= 0
INDE  2  33   7  FOBS=  193.4  SIGMA=   0.8  PHAS=  -102.3  FOM=  0.95  TEST= 0
INDE  2  33   9  FOBS=   89.0  SIGMA=   1.1  PHAS=  -138.1  FOM=  0.73  TEST= 1
INDE  2  33  11  FOBS=  151.1  SIGMA=   1.1  PHAS=   109.1  FOM=  0.89  TEST= 0
INDE  2  33  13  FOBS=  210.4  SIGMA=   1.0  PHAS=   132.3  FOM=  0.95  TEST= 0
INDE  2  33  21  FOBS=  178.9  SIGMA=   2.0  PHAS=  -140.5  FOM=  0.78  TEST= 0
INDE  2  33  23  FOBS=  167.0  SIGMA=   1.6  PHAS=   168.9  FOM=  0.88  TEST= 0
INDE  2  33  25  FOBS=  227.8  SIGMA=   1.3  PHAS=  -144.4  FOM=  0.92  TEST= 0
INDE  2  33  27  FOBS=  132.0  SIGMA=   2.1  PHAS=    42.9  FOM=  0.78  TEST= 0
INDE  2  33  29  FOBS=   87.5  SIGMA=   2.2  PHAS=   125.6  FOM=  0.14  TEST= 0
INDE  2  33  31  FOBS=  252.1  SIGMA=   0.9  PHAS=   -87.9  FOM=  0.98  TEST= 0
INDE  2  33  33  FOBS=  176.2  SIGMA=   1.3  PHAS=    78.4  FOM=  0.93  TEST= 0
INDE  2  33  35  FOBS=  211.1  SIGMA=   1.2  PHAS=    -7.0  FOM=  0.94  TEST= 0
INDE  2  33  37  FOBS=  167.7  SIGMA=   1.4  PHAS=  -136.9  FOM=  0.90  TEST= 0
INDE  2  33  39  FOBS=  139.3  SIGMA=   1.3  PHAS=  -125.0  FOM=  0.91  TEST= 0
INDE  2  33  41  FOBS=   88.5  SIGMA=   1.9  PHAS=    52.7  FOM=  0.62  TEST= 0
INDE  2  33  43  FOBS=  173.1  SIGMA=   1.1  PHAS=    74.1  FOM=  0.17  TEST= 1
INDE  2  33  45  FOBS=  115.1  SIGMA=   1.5  PHAS=    39.4  FOM=  0.89  TEST= 0
INDE  2  33  47  FOBS=  117.2  SIGMA=   1.5  PHAS=   -19.1  FOM=  0.91  TEST= 0
INDE  2  33  49  FOBS=   46.1  SIGMA=   3.1  PHAS=    93.2  FOM=  0.55  TEST= 0
INDE  2  33  51  FOBS=   37.1  SIGMA=   3.9  PHAS=  -143.6  FOM=  0.54  TEST= 0
INDE  2  33  53  FOBS=  129.6  SIGMA=   1.0  PHAS=  -120.7  FOM=  0.94  TEST= 0
INDE  2  33  55  FOBS=   53.8  SIGMA=   2.8  PHAS=   179.5  FOM=  0.84  TEST= 0
INDE  2  33  57  FOBS=   75.3  SIGMA=   2.4  PHAS=    82.9  FOM=  0.71  TEST= 0
INDE  2  33  59  FOBS=    0.0  SIGMA=  19.5  PHAS=     0.0  FOM=  0.00  TEST= 0
INDE  2  33  61  FOBS=   37.4  SIGMA=   6.0  PHAS=   -52.0  FOM=  0.63  TEST= 0
INDE  2  33  63  FOBS=   89.0  SIGMA=   2.6  PHAS=   -88.2  FOM=  0.93  TEST= 0
INDE  2  33  65  FOBS=   73.3  SIGMA=   2.7  PHAS=   116.5  FOM=  0.84  TEST= 0
INDE  2  33  67  FOBS=   34.1  SIGMA=  11.1  PHAS=  -124.6  FOM=  0.65  TEST= 0
INDE  2  33  69  FOBS=   67.8  SIGMA=   5.7  PHAS=   135.8  FOM=  0.88  TEST= 0
INDE  2  34   2  FOBS=  137.2  SIGMA=   1.0  PHAS=   147.6  FOM=  0.97  TEST= 0
INDE  2  34   4  FOBS=   72.9  SIGMA=   1.8  PHAS=   -75.4  FOM=  0.74  TEST= 0
INDE  2  34   6  FOBS=  119.1  SIGMA=   1.3  PHAS=   -36.4  FOM=  0.98  TEST= 0
INDE  2  34   8  FOBS=  236.6  SIGMA=   0.5  PHAS=    44.7  FOM=  0.96  TEST= 0
INDE  2  34  10  FOBS=   23.6  SIGMA=   4.0  PHAS=   152.7  FOM=  0.76  TEST= 1
INDE  2  34  12  FOBS=  265.1  SIGMA=   0.8  PHAS=   107.8  FOM=  0.97  TEST= 0
INDE  2  34  14  FOBS=  166.4  SIGMA=   1.2  PHAS=   -34.9  FOM=  0.94  TEST= 0
INDE  2  34  22  FOBS=  294.1  SIGMA=   1.6  PHAS=   129.5  FOM=  0.92  TEST= 0
INDE  2  34  24  FOBS=   54.7  SIGMA=   4.6  PHAS=   173.0  FOM=  0.77  TEST= 0
INDE  2  34  26  FOBS=  107.4  SIGMA=   2.5  PHAS=   -98.9  FOM=  0.74  TEST= 0
INDE  2  34  28  FOBS=   41.7  SIGMA=   5.8  PHAS=    92.8  FOM=  0.53  TEST= 0
INDE  2  34  30  FOBS=  167.7  SIGMA=   1.3  PHAS=   151.3  FOM=  0.94  TEST= 0
INDE  2  34  32  FOBS=   43.6  SIGMA=   4.9  PHAS=   113.6  FOM=  0.95  TEST= 0
INDE  2  34  34  FOBS=  281.0  SIGMA=   1.0  PHAS=  -120.8  FOM=  0.96  TEST= 0
INDE  2  34  36  FOBS=    0.0  SIGMA=  21.1  PHAS=     0.0  FOM=  0.00  TEST= 0
INDE  2  34  38  FOBS=  212.0  SIGMA=   1.0  PHAS=     0.2  FOM=  0.97  TEST= 0
INDE  2  34  40  FOBS=   90.2  SIGMA=   1.9  PHAS=   -21.1  FOM=  0.32  TEST= 0
INDE  2  34  42  FOBS=  164.9  SIGMA=   1.1  PHAS=   -21.1  FOM=  0.93  TEST= 0
INDE  2  34  44  FOBS=   97.1  SIGMA=   1.8  PHAS=   -40.1  FOM=  0.62  TEST= 0
INDE  2  34  46  FOBS=  100.5  SIGMA=   1.7  PHAS=   -90.7  FOM=  0.80  TEST= 0
INDE  2  34  48  FOBS=  106.1  SIGMA=   1.6  PHAS=   110.5  FOM=  0.78  TEST= 0
INDE  2  34  50  FOBS=   88.3  SIGMA=   1.6  PHAS=  -103.3  FOM=  0.83  TEST= 0
INDE  2  34  52  FOBS=   26.7  SIGMA=   6.3  PHAS=   -91.5  FOM=  0.17  TEST= 1
INDE  2  34  54  FOBS=   78.1  SIGMA=   2.1  PHAS=   129.4  FOM=  0.77  TEST= 0
INDE  2  34  56  FOBS=   51.8  SIGMA=   3.3  PHAS=     8.0  FOM=  0.69  TEST= 0
INDE  2  34  58  FOBS=   67.9  SIGMA=   2.7  PHAS=    99.3  FOM=  0.77  TEST= 0
INDE  2  34  60  FOBS=    0.0  SIGMA=  19.6  PHAS=     0.0  FOM=  0.00  TEST= 1
INDE  2  34  62  FOBS=  109.8  SIGMA=   2.1  PHAS=  -165.8  FOM=  0.88  TEST= 0
INDE  2  34  64  FOBS=   40.2  SIGMA=   5.6  PHAS=  -178.6  FOM=  0.23  TEST= 0
INDE  2  34  66  FOBS=    0.0  SIGMA=  20.7  PHAS=     0.0  FOM=  0.00  TEST= 0
INDE  2  34  68  FOBS=   45.2  SIGMA=   7.0  PHAS=   -53.3  FOM=  0.31  TEST= 0
INDE  2  35   3  FOBS=  201.6  SIGMA=   0.8  PHAS=   -67.6  FOM=  0.92  TEST= 0
INDE  2  35   7  FOBS=  211.9  SIGMA=   0.7  PHAS=  -125.6  FOM=  0.99  TEST= 0
```

*FIG. 12A - 64*

| | | | | | | | | | | | |
|---|---|---|---|---|---|---|---|---|---|---|---|
| INDE | 2 | 35 | 9 | FOBS= | 257.5 | SIGMA= | 0.5 | PHAS= | -128.4 | FOM= | 0.97 | TEST= 0
| INDE | 2 | 35 | 11 | FOBS= | 72.4 | SIGMA= | 1.4 | PHAS= | -127.8 | FOM= | 0.87 | TEST= 0
| INDE | 2 | 35 | 13 | FOBS= | 118.0 | SIGMA= | 1.6 | PHAS= | -89.2 | FOM= | 0.85 | TEST= 0
| INDE | 2 | 35 | 15 | FOBS= | 158.4 | SIGMA= | 1.3 | PHAS= | 113.3 | FOM= | 0.83 | TEST= 0
| INDE | 2 | 35 | 23 | FOBS= | 0.0 | SIGMA= | 22.4 | PHAS= | 0.0 | FOM= | 0.00 | TEST= 0
| INDE | 2 | 35 | 25 | FOBS= | 142.2 | SIGMA= | 2.0 | PHAS= | 128.3 | FOM= | 0.92 | TEST= 0
| INDE | 2 | 35 | 27 | FOBS= | 97.0 | SIGMA= | 3.0 | PHAS= | -59.0 | FOM= | 0.79 | TEST= 0
| INDE | 2 | 35 | 29 | FOBS= | 56.4 | SIGMA= | 4.2 | PHAS= | -119.1 | FOM= | 0.09 | TEST= 0
| INDE | 2 | 35 | 31 | FOBS= | 79.9 | SIGMA= | 2.7 | PHAS= | 10.2 | FOM= | 0.91 | TEST= 0
| INDE | 2 | 35 | 33 | FOBS= | 279.1 | SIGMA= | 1.0 | PHAS= | 69.3 | FOM= | 0.94 | TEST= 0
| INDE | 2 | 35 | 35 | FOBS= | 169.2 | SIGMA= | 1.5 | PHAS= | 92.3 | FOM= | 0.79 | TEST= 0
| INDE | 2 | 35 | 37 | FOBS= | 124.2 | SIGMA= | 1.9 | PHAS= | -147.6 | FOM= | 0.89 | TEST= 0
| INDE | 2 | 35 | 39 | FOBS= | 233.5 | SIGMA= | 0.9 | PHAS= | -126.9 | FOM= | 0.97 | TEST= 0
| INDE | 2 | 35 | 41 | FOBS= | 37.0 | SIGMA= | 4.6 | PHAS= | -82.5 | FOM= | 0.41 | TEST= 0
| INDE | 2 | 35 | 43 | FOBS= | 22.1 | SIGMA= | 7.7 | PHAS= | 69.5 | FOM= | 0.01 | TEST= 0
| INDE | 2 | 35 | 45 | FOBS= | 92.9 | SIGMA= | 1.9 | PHAS= | 160.1 | FOM= | 0.92 | TEST= 0
| INDE | 2 | 35 | 47 | FOBS= | 176.3 | SIGMA= | 1.0 | PHAS= | -103.3 | FOM= | 0.94 | TEST= 0
| INDE | 2 | 35 | 49 | FOBS= | 57.9 | SIGMA= | 2.5 | PHAS= | 36.7 | FOM= | 0.73 | TEST= 0
| INDE | 2 | 35 | 51 | FOBS= | 0.0 | SIGMA= | 16.7 | PHAS= | 0.0 | FOM= | 0.00 | TEST= 0
| INDE | 2 | 35 | 53 | FOBS= | 26.7 | SIGMA= | 6.3 | PHAS= | -100.7 | FOM= | 0.36 | TEST= 0
| INDE | 2 | 35 | 55 | FOBS= | 45.3 | SIGMA= | 3.7 | PHAS= | -165.0 | FOM= | 0.46 | TEST= 0
| INDE | 2 | 35 | 57 | FOBS= | 84.8 | SIGMA= | 2.2 | PHAS= | -79.6 | FOM= | 0.73 | TEST= 0
| INDE | 2 | 35 | 59 | FOBS= | 53.5 | SIGMA= | 4.9 | PHAS= | 155.6 | FOM= | 0.24 | TEST= 1
| INDE | 2 | 35 | 61 | FOBS= | 119.7 | SIGMA= | 1.7 | PHAS= | 175.1 | FOM= | 0.76 | TEST= 0
| INDE | 2 | 35 | 63 | FOBS= | 46.4 | SIGMA= | 4.9 | PHAS= | 105.9 | FOM= | 0.63 | TEST= 0
| INDE | 2 | 35 | 65 | FOBS= | 49.6 | SIGMA= | 3.9 | PHAS= | 127.4 | FOM= | 0.56 | TEST= 0
| INDE | 2 | 35 | 67 | FOBS= | 2.0 | SIGMA= | 118.9 | PHAS= | -153.3 | FOM= | 0.05 | TEST= 0
| INDE | 2 | 35 | 69 | FOBS= | 47.0 | SIGMA= | 8.5 | PHAS= | -136.1 | FOM= | 0.67 | TEST= 0
| INDE | 2 | 36 | 2 | FOBS= | 223.8 | SIGMA= | 0.7 | PHAS= | 97.0 | FOM= | 0.86 | TEST= 0
| INDE | 2 | 36 | 4 | FOBS= | 223.8 | SIGMA= | 0.8 | PHAS= | -123.3 | FOM= | 0.88 | TEST= 0
| INDE | 2 | 36 | 8 | FOBS= | 55.0 | SIGMA= | 1.7 | PHAS= | 138.1 | FOM= | 0.98 | TEST= 0
| INDE | 2 | 36 | 10 | FOBS= | 166.7 | SIGMA= | 0.7 | PHAS= | 91.2 | FOM= | 0.87 | TEST= 0
| INDE | 2 | 36 | 12 | FOBS= | 105.5 | SIGMA= | 1.6 | PHAS= | -14.1 | FOM= | 0.98 | TEST= 0
| INDE | 2 | 36 | 14 | FOBS= | 75.5 | SIGMA= | 2.4 | PHAS= | -159.5 | FOM= | 0.09 | TEST= 1
| INDE | 2 | 36 | 16 | FOBS= | 267.9 | SIGMA= | 1.3 | PHAS= | 102.9 | FOM= | 0.92 | TEST= 0
| INDE | 2 | 36 | 22 | FOBS= | 259.5 | SIGMA= | 1.8 | PHAS= | 94.6 | FOM= | 0.35 | TEST= 0
| INDE | 2 | 36 | 24 | FOBS= | 63.5 | SIGMA= | 4.3 | PHAS= | -109.3 | FOM= | 0.09 | TEST= 0
| INDE | 2 | 36 | 26 | FOBS= | 116.1 | SIGMA= | 2.6 | PHAS= | -23.8 | FOM= | 0.32 | TEST= 1
| INDE | 2 | 36 | 28 | FOBS= | 299.1 | SIGMA= | 1.3 | PHAS= | 123.5 | FOM= | 0.94 | TEST= 0
| INDE | 2 | 36 | 30 | FOBS= | 155.0 | SIGMA= | 1.6 | PHAS= | 42.9 | FOM= | 0.49 | TEST= 0
| INDE | 2 | 36 | 32 | FOBS= | 279.3 | SIGMA= | 1.0 | PHAS= | 16.5 | FOM= | 0.99 | TEST= 0
| INDE | 2 | 36 | 34 | FOBS= | 262.8 | SIGMA= | 1.2 | PHAS= | -23.3 | FOM= | 0.96 | TEST= 0
| INDE | 2 | 36 | 36 | FOBS= | 120.9 | SIGMA= | 2.0 | PHAS= | 80.0 | FOM= | 0.54 | TEST= 0
| INDE | 2 | 36 | 38 | FOBS= | 226.9 | SIGMA= | 1.0 | PHAS= | 147.6 | FOM= | 0.96 | TEST= 0
| INDE | 2 | 36 | 40 | FOBS= | 179.5 | SIGMA= | 1.0 | PHAS= | 135.6 | FOM= | 0.94 | TEST= 0
| INDE | 2 | 36 | 42 | FOBS= | 0.0 | SIGMA= | 18.6 | PHAS= | 0.0 | FOM= | 0.00 | TEST= 0
| INDE | 2 | 36 | 44 | FOBS= | 132.6 | SIGMA= | 1.4 | PHAS= | 86.1 | FOM= | 0.25 | TEST= 1
| INDE | 2 | 36 | 46 | FOBS= | 104.5 | SIGMA= | 1.7 | PHAS= | 113.8 | FOM= | 0.91 | TEST= 0
| INDE | 2 | 36 | 48 | FOBS= | 50.2 | SIGMA= | 3.3 | PHAS= | -88.2 | FOM= | 0.68 | TEST= 0
| INDE | 2 | 36 | 50 | FOBS= | 52.6 | SIGMA= | 2.7 | PHAS= | -60.0 | FOM= | 0.68 | TEST= 0
| INDE | 2 | 36 | 52 | FOBS= | 17.9 | SIGMA= | 8.1 | PHAS= | 128.0 | FOM= | 0.62 | TEST= 0
| INDE | 2 | 36 | 54 | FOBS= | 0.0 | SIGMA= | 18.3 | PHAS= | 0.0 | FOM= | 0.00 | TEST= 1
| INDE | 2 | 36 | 56 | FOBS= | 32.2 | SIGMA= | 5.2 | PHAS= | 169.4 | FOM= | 0.37 | TEST= 0
| INDE | 2 | 36 | 58 | FOBS= | 22.5 | SIGMA= | 8.0 | PHAS= | 49.9 | FOM= | 0.20 | TEST= 0
| INDE | 2 | 36 | 60 | FOBS= | 85.7 | SIGMA= | 2.7 | PHAS= | 157.7 | FOM= | 0.86 | TEST= 0
| INDE | 2 | 36 | 62 | FOBS= | 0.0 | SIGMA= | 20.5 | PHAS= | 0.0 | FOM= | 0.00 | TEST= 0
| INDE | 2 | 36 | 64 | FOBS= | 54.7 | SIGMA= | 4.2 | PHAS= | -0.4 | FOM= | 0.74 | TEST= 0
| INDE | 2 | 36 | 66 | FOBS= | 0.0 | SIGMA= | 22.9 | PHAS= | 0.0 | FOM= | 0.00 | TEST= 0
| INDE | 2 | 36 | 68 | FOBS= | 58.6 | SIGMA= | 6.8 | PHAS= | 172.0 | FOM= | 0.72 | TEST= 0
| INDE | 2 | 37 | 3 | FOBS= | 187.2 | SIGMA= | 0.9 | PHAS= | -84.4 | FOM= | 0.94 | TEST= 0
| INDE | 2 | 37 | 7 | FOBS= | 223.3 | SIGMA= | 0.7 | PHAS= | -171.2 | FOM= | 0.83 | TEST= 0
| INDE | 2 | 37 | 9 | FOBS= | 148.2 | SIGMA= | 0.8 | PHAS= | -162.3 | FOM= | 0.89 | TEST= 0
| INDE | 2 | 37 | 11 | FOBS= | 143.7 | SIGMA= | 0.9 | PHAS= | -102.9 | FOM= | 0.96 | TEST= 0
| INDE | 2 | 37 | 13 | FOBS= | 77.5 | SIGMA= | 2.4 | PHAS= | 19.4 | FOM= | 0.82 | TEST= 0
| INDE | 2 | 37 | 15 | FOBS= | 197.5 | SIGMA= | 1.2 | PHAS= | 100.8 | FOM= | 0.97 | TEST= 0
| INDE | 2 | 37 | 23 | FOBS= | 212.7 | SIGMA= | 1.5 | PHAS= | -82.1 | FOM= | 0.84 | TEST= 0
| INDE | 2 | 37 | 25 | FOBS= | 37.1 | SIGMA= | 7.8 | PHAS= | 51.2 | FOM= | 0.03 | TEST= 0
| INDE | 2 | 37 | 27 | FOBS= | 268.2 | SIGMA= | 1.4 | PHAS= | 120.2 | FOM= | 0.95 | TEST= 0
| INDE | 2 | 37 | 29 | FOBS= | 35.3 | SIGMA= | 9.3 | PHAS= | -147.6 | FOM= | 0.35 | TEST= 0
| INDE | 2 | 37 | 31 | FOBS= | 98.8 | SIGMA= | 2.4 | PHAS= | -144.2 | FOM= | 0.53 | TEST= 0

*FIG. 12A - 65*

| | | | | | | | | | | | | |
|---|---|---|---|---|---|---|---|---|---|---|---|---|
| INDE | 2 | 37 | 33 | FOBS= | 159.1 | SIGMA= | 1.5 | PHAS= | -82.6 | FOM= | 0.65 | TEST= 0 |
| INDE | 2 | 37 | 35 | FOBS= | 213.0 | SIGMA= | 1.2 | PHAS= | -142.5 | FOM= | 0.94 | TEST= 0 |
| INDE | 2 | 37 | 37 | FOBS= | 301.8 | SIGMA= | 0.9 | PHAS= | 55.9 | FOM= | 0.98 | TEST= 0 |
| INDE | 2 | 37 | 39 | FOBS= | 71.4 | SIGMA= | 2.5 | PHAS= | -67.0 | FOM= | 0.73 | TEST= 0 |
| INDE | 2 | 37 | 41 | FOBS= | 69.2 | SIGMA= | 2.5 | PHAS= | 69.8 | FOM= | 0.21 | TEST= 0 |
| INDE | 2 | 37 | 43 | FOBS= | 27.5 | SIGMA= | 6.6 | PHAS= | -47.4 | FOM= | 0.27 | TEST= 0 |
| INDE | 2 | 37 | 45 | FOBS= | 36.6 | SIGMA= | 4.7 | PHAS= | 56.0 | FOM= | 0.80 | TEST= 0 |
| INDE | 2 | 37 | 47 | FOBS= | 111.4 | SIGMA= | 1.5 | PHAS= | -171.1 | FOM= | 0.80 | TEST= 1 |
| INDE | 2 | 37 | 49 | FOBS= | 15.6 | SIGMA= | 13.2 | PHAS= | 141.1 | FOM= | 0.27 | TEST= 0 |
| INDE | 2 | 37 | 51 | FOBS= | 55.4 | SIGMA= | 2.6 | PHAS= | -88.4 | FOM= | 0.36 | TEST= 0 |
| INDE | 2 | 37 | 53 | FOBS= | 30.7 | SIGMA= | 5.8 | PHAS= | 79.3 | FOM= | 0.32 | TEST= 0 |
| INDE | 2 | 37 | 55 | FOBS= | 55.6 | SIGMA= | 3.0 | PHAS= | -30.4 | FOM= | 0.53 | TEST= 0 |
| INDE | 2 | 37 | 57 | FOBS= | 45.3 | SIGMA= | 3.7 | PHAS= | -9.7 | FOM= | 0.35 | TEST= 0 |
| INDE | 2 | 37 | 59 | FOBS= | 0.0 | SIGMA= | 23.0 | PHAS= | 0.0 | FOM= | 0.00 | TEST= 0 |
| INDE | 2 | 37 | 61 | FOBS= | 46.7 | SIGMA= | 4.9 | PHAS= | 109.3 | FOM= | 0.74 | TEST= 0 |
| INDE | 2 | 37 | 63 | FOBS= | 21.5 | SIGMA= | 9.9 | PHAS= | 129.1 | FOM= | 0.61 | TEST= 0 |
| INDE | 2 | 37 | 65 | FOBS= | 20.6 | SIGMA= | 9.5 | PHAS= | 162.6 | FOM= | 0.15 | TEST= 0 |
| INDE | 2 | 37 | 67 | FOBS= | 52.6 | SIGMA= | 6.2 | PHAS= | 103.8 | FOM= | 0.74 | TEST= 0 |
| INDE | 2 | 38 | 2 | FOBS= | 167.1 | SIGMA= | 1.0 | PHAS= | 61.9 | FOM= | 0.98 | TEST= 0 |
| INDE | 2 | 38 | 4 | FOBS= | 83.9 | SIGMA= | 1.8 | PHAS= | -120.2 | FOM= | 0.87 | TEST= 0 |
| INDE | 2 | 38 | 8 | FOBS= | 106.0 | SIGMA= | 1.4 | PHAS= | 54.3 | FOM= | 0.85 | TEST= 0 |
| INDE | 2 | 38 | 10 | FOBS= | 180.4 | SIGMA= | 0.7 | PHAS= | 114.7 | FOM= | 0.98 | TEST= 0 |
| INDE | 2 | 38 | 12 | FOBS= | 213.9 | SIGMA= | 0.7 | PHAS= | -73.4 | FOM= | 0.97 | TEST= 0 |
| INDE | 2 | 38 | 14 | FOBS= | 216.6 | SIGMA= | 1.1 | PHAS= | 126.3 | FOM= | 0.88 | TEST= 0 |
| INDE | 2 | 38 | 16 | FOBS= | 243.4 | SIGMA= | 1.1 | PHAS= | 43.0 | FOM= | 0.94 | TEST= 0 |
| INDE | 2 | 38 | 22 | FOBS= | 86.7 | SIGMA= | 4.8 | PHAS= | 46.8 | FOM= | 0.20 | TEST= 0 |
| INDE | 2 | 38 | 24 | FOBS= | 141.7 | SIGMA= | 2.2 | PHAS= | -103.7 | FOM= | 0.78 | TEST= 0 |
| INDE | 2 | 38 | 26 | FOBS= | 94.6 | SIGMA= | 3.4 | PHAS= | 117.9 | FOM= | 0.77 | TEST= 1 |
| INDE | 2 | 38 | 28 | FOBS= | 136.6 | SIGMA= | 2.6 | PHAS= | 162.3 | FOM= | 0.86 | TEST= 0 |
| INDE | 2 | 38 | 30 | FOBS= | 290.1 | SIGMA= | 1.4 | PHAS= | 87.7 | FOM= | 0.97 | TEST= 0 |
| INDE | 2 | 38 | 32 | FOBS= | 184.7 | SIGMA= | 1.3 | PHAS= | -25.4 | FOM= | 0.91 | TEST= 0 |
| INDE | 2 | 38 | 34 | FOBS= | 101.2 | SIGMA= | 2.3 | PHAS= | 30.1 | FOM= | 0.91 | TEST= 0 |
| INDE | 2 | 38 | 36 | FOBS= | 125.1 | SIGMA= | 1.9 | PHAS= | 97.1 | FOM= | 0.91 | TEST= 0 |
| INDE | 2 | 38 | 38 | FOBS= | 70.1 | SIGMA= | 2.9 | PHAS= | -170.8 | FOM= | 0.86 | TEST= 0 |
| INDE | 2 | 38 | 40 | FOBS= | 78.1 | SIGMA= | 2.3 | PHAS= | 178.1 | FOM= | 0.85 | TEST= 0 |
| INDE | 2 | 38 | 42 | FOBS= | 107.7 | SIGMA= | 1.6 | PHAS= | -153.1 | FOM= | 0.93 | TEST= 0 |
| INDE | 2 | 38 | 44 | FOBS= | 18.7 | SIGMA= | 10.2 | PHAS= | 62.9 | FOM= | 0.05 | TEST= 1 |
| INDE | 2 | 38 | 46 | FOBS= | 84.4 | SIGMA= | 2.1 | PHAS= | 65.0 | FOM= | 0.83 | TEST= 0 |
| INDE | 2 | 38 | 48 | FOBS= | 39.7 | SIGMA= | 4.2 | PHAS= | 60.2 | FOM= | 0.20 | TEST= 0 |
| INDE | 2 | 38 | 50 | FOBS= | 0.0 | SIGMA= | 16.9 | PHAS= | 0.0 | FOM= | 0.00 | TEST= 0 |
| INDE | 2 | 38 | 52 | FOBS= | 44.4 | SIGMA= | 3.9 | PHAS= | 39.0 | FOM= | 0.11 | TEST= 1 |
| INDE | 2 | 38 | 54 | FOBS= | 0.0 | SIGMA= | 20.5 | PHAS= | 0.0 | FOM= | 0.00 | TEST= 0 |
| INDE | 2 | 38 | 56 | FOBS= | 41.0 | SIGMA= | 4.1 | PHAS= | -170.4 | FOM= | 0.31 | TEST= 1 |
| INDE | 2 | 38 | 58 | FOBS= | 18.5 | SIGMA= | 10.5 | PHAS= | -111.5 | FOM= | 0.28 | TEST= 0 |
| INDE | 2 | 38 | 60 | FOBS= | 59.0 | SIGMA= | 3.3 | PHAS= | 66.7 | FOM= | 0.73 | TEST= 0 |
| INDE | 2 | 38 | 62 | FOBS= | 61.6 | SIGMA= | 3.3 | PHAS= | 46.2 | FOM= | 0.78 | TEST= 0 |
| INDE | 2 | 38 | 64 | FOBS= | 82.5 | SIGMA= | 2.5 | PHAS= | 70.3 | FOM= | 0.89 | TEST= 0 |
| INDE | 2 | 38 | 66 | FOBS= | 0.0 | SIGMA= | 23.5 | PHAS= | 0.0 | FOM= | 0.00 | TEST= 0 |
| INDE | 2 | 39 | 3 | FOBS= | 252.6 | SIGMA= | 0.8 | PHAS= | -92.9 | FOM= | 0.96 | TEST= 0 |
| INDE | 2 | 39 | 9 | FOBS= | 121.6 | SIGMA= | 1.0 | PHAS= | -141.4 | FOM= | 0.96 | TEST= 0 |
| INDE | 2 | 39 | 11 | FOBS= | 252.1 | SIGMA= | 0.7 | PHAS= | -95.8 | FOM= | 0.97 | TEST= 0 |
| INDE | 2 | 39 | 13 | FOBS= | 94.6 | SIGMA= | 1.4 | PHAS= | 87.6 | FOM= | 0.92 | TEST= 0 |
| INDE | 2 | 39 | 15 | FOBS= | 108.1 | SIGMA= | 2.1 | PHAS= | 56.3 | FOM= | 0.86 | TEST= 1 |
| INDE | 2 | 39 | 17 | FOBS= | 255.5 | SIGMA= | 1.1 | PHAS= | -147.8 | FOM= | 0.93 | TEST= 0 |
| INDE | 2 | 39 | 23 | FOBS= | 135.2 | SIGMA= | 3.4 | PHAS= | 0.0 | FOM= | 0.00 | TEST= 1 |
| INDE | 2 | 39 | 25 | FOBS= | 189.8 | SIGMA= | 1.9 | PHAS= | 139.5 | FOM= | 0.95 | TEST= 0 |
| INDE | 2 | 39 | 27 | FOBS= | 193.4 | SIGMA= | 1.9 | PHAS= | 120.2 | FOM= | 0.97 | TEST= 0 |
| INDE | 2 | 39 | 29 | FOBS= | 106.5 | SIGMA= | 3.3 | PHAS= | 8.7 | FOM= | 0.87 | TEST= 0 |
| INDE | 2 | 39 | 31 | FOBS= | 71.9 | SIGMA= | 4.2 | PHAS= | 140.7 | FOM= | 0.47 | TEST= 0 |
| INDE | 2 | 39 | 33 | FOBS= | 50.2 | SIGMA= | 4.6 | PHAS= | -116.8 | FOM= | 0.83 | TEST= 0 |
| INDE | 2 | 39 | 35 | FOBS= | 257.8 | SIGMA= | 1.1 | PHAS= | 115.0 | FOM= | 0.97 | TEST= 0 |
| INDE | 2 | 39 | 37 | FOBS= | 177.1 | SIGMA= | 1.4 | PHAS= | 22.9 | FOM= | 0.96 | TEST= 0 |
| INDE | 2 | 39 | 39 | FOBS= | 0.0 | SIGMA= | 20.7 | PHAS= | 0.0 | FOM= | 0.00 | TEST= 0 |
| INDE | 2 | 39 | 41 | FOBS= | 238.1 | SIGMA= | 0.9 | PHAS= | 130.8 | FOM= | 0.97 | TEST= 0 |
| INDE | 2 | 39 | 43 | FOBS= | 59.0 | SIGMA= | 2.9 | PHAS= | 155.8 | FOM= | 0.80 | TEST= 0 |
| INDE | 2 | 39 | 45 | FOBS= | 100.3 | SIGMA= | 1.8 | PHAS= | -28.4 | FOM= | 0.84 | TEST= 0 |
| INDE | 2 | 39 | 47 | FOBS= | 94.0 | SIGMA= | 1.8 | PHAS= | 50.4 | FOM= | 0.60 | TEST= 0 |
| INDE | 2 | 39 | 49 | FOBS= | 70.2 | SIGMA= | 2.3 | PHAS= | 90.3 | FOM= | 0.77 | TEST= 0 |
| INDE | 2 | 39 | 51 | FOBS= | 48.8 | SIGMA= | 3.0 | PHAS= | 111.8 | FOM= | 0.32 | TEST= 0 |
| INDE | 2 | 39 | 53 | FOBS= | 25.3 | SIGMA= | 7.1 | PHAS= | 19.6 | FOM= | 0.43 | TEST= 0 |

*FIG. 12A - 66*

| | | | | | | | | | | | |
|---|---|---|---|---|---|---|---|---|---|---|---|
| INDE | 2 | 39 | 55 | FOBS= | 15.8 | SIGMA= | 12.2 | PHAS= | 171.3 | FOM= | 0.02 | TEST= 1
| INDE | 2 | 39 | 57 | FOBS= | 0.0 | SIGMA= | 18.8 | PHAS= | 0.0 | FOM= | 0.00 | TEST= 0
| INDE | 2 | 39 | 59 | FOBS= | 0.0 | SIGMA= | 19.3 | PHAS= | 0.0 | FOM= | 0.00 | TEST= 0
| INDE | 2 | 39 | 61 | FOBS= | 53.6 | SIGMA= | 3.7 | PHAS= | 8.9 | FOM= | 0.75 | TEST= 0
| INDE | 2 | 39 | 63 | FOBS= | 35.5 | SIGMA= | 6.9 | PHAS= | 37.7 | FOM= | 0.37 | TEST= 0
| INDE | 2 | 39 | 65 | FOBS= | 54.8 | SIGMA= | 3.1 | PHAS= | 126.8 | FOM= | 0.72 | TEST= 0
| INDE | 2 | 39 | 67 | FOBS= | 49.9 | SIGMA= | 8.4 | PHAS= | -135.2 | FOM= | 0.83 | TEST= 0
| INDE | 2 | 40 | 2 | FOBS= | 289.0 | SIGMA= | 0.7 | PHAS= | 164.2 | FOM= | 0.97 | TEST= 0
| INDE | 2 | 40 | 4 | FOBS= | 267.4 | SIGMA= | 0.8 | PHAS= | -166.9 | FOM= | 0.92 | TEST= 0
| INDE | 2 | 40 | 8 | FOBS= | 191.1 | SIGMA= | 0.9 | PHAS= | 6.3 | FOM= | 0.92 | TEST= 0
| INDE | 2 | 40 | 10 | FOBS= | 164.4 | SIGMA= | 0.8 | PHAS= | 50.4 | FOM= | 0.88 | TEST= 0
| INDE | 2 | 40 | 12 | FOBS= | 106.0 | SIGMA= | 1.3 | PHAS= | 118.3 | FOM= | 0.57 | TEST= 0
| INDE | 2 | 40 | 14 | FOBS= | 126.1 | SIGMA= | 1.2 | PHAS= | 119.0 | FOM= | 0.94 | TEST= 0
| INDE | 2 | 40 | 16 | FOBS= | 175.7 | SIGMA= | 1.5 | PHAS= | -92.6 | FOM= | 0.99 | TEST= 0
| INDE | 2 | 40 | 18 | FOBS= | 108.1 | SIGMA= | 2.2 | PHAS= | 157.3 | FOM= | 0.45 | TEST= 0
| INDE | 2 | 40 | 22 | FOBS= | 0.0 | SIGMA= | 29.9 | PHAS= | 0.0 | FOM= | 0.00 | TEST= 0
| INDE | 2 | 40 | 24 | FOBS= | 219.9 | SIGMA= | 1.7 | PHAS= | 75.3 | FOM= | 0.97 | TEST= 0
| INDE | 2 | 40 | 26 | FOBS= | 276.5 | SIGMA= | 1.5 | PHAS= | -164.9 | FOM= | 0.06 | TEST= 1
| INDE | 2 | 40 | 28 | FOBS= | 91.8 | SIGMA= | 3.9 | PHAS= | 12.7 | FOM= | 0.69 | TEST= 0
| INDE | 2 | 40 | 30 | FOBS= | 130.9 | SIGMA= | 2.7 | PHAS= | 55.7 | FOM= | 0.86 | TEST= 0
| INDE | 2 | 40 | 32 | FOBS= | 47.3 | SIGMA= | 5.6 | PHAS= | 165.4 | FOM= | 0.09 | TEST= 0
| INDE | 2 | 40 | 34 | FOBS= | 248.6 | SIGMA= | 1.1 | PHAS= | 38.1 | FOM= | 0.97 | TEST= 0
| INDE | 2 | 40 | 36 | FOBS= | 43.2 | SIGMA= | 5.5 | PHAS= | -22.7 | FOM= | 0.10 | TEST= 1
| INDE | 2 | 40 | 38 | FOBS= | 77.9 | SIGMA= | 2.6 | PHAS= | -146.9 | FOM= | 0.49 | TEST= 0
| INDE | 2 | 40 | 40 | FOBS= | 0.0 | SIGMA= | 20.8 | PHAS= | 0.0 | FOM= | 0.00 | TEST= 0
| INDE | 2 | 40 | 42 | FOBS= | 98.0 | SIGMA= | 1.8 | PHAS= | 100.2 | FOM= | 0.92 | TEST= 0
| INDE | 2 | 40 | 44 | FOBS= | 59.0 | SIGMA= | 3.0 | PHAS= | -120.8 | FOM= | 0.19 | TEST= 1
| INDE | 2 | 40 | 46 | FOBS= | 80.7 | SIGMA= | 2.2 | PHAS= | -90.4 | FOM= | 0.91 | TEST= 0
| INDE | 2 | 40 | 48 | FOBS= | 186.0 | SIGMA= | 1.0 | PHAS= | -0.4 | FOM= | 0.96 | TEST= 0
| INDE | 2 | 40 | 50 | FOBS= | 100.0 | SIGMA= | 1.5 | PHAS= | -6.3 | FOM= | 0.73 | TEST= 0
| INDE | 2 | 40 | 52 | FOBS= | 96.6 | SIGMA= | 1.8 | PHAS= | -83.6 | FOM= | 0.93 | TEST= 0
| INDE | 2 | 40 | 54 | FOBS= | 50.0 | SIGMA= | 3.4 | PHAS= | 53.5 | FOM= | 0.84 | TEST= 0
| INDE | 2 | 40 | 56 | FOBS= | 60.8 | SIGMA= | 2.8 | PHAS= | 107.7 | FOM= | 0.64 | TEST= 0
| INDE | 2 | 40 | 58 | FOBS= | 0.0 | SIGMA= | 18.4 | PHAS= | 0.0 | FOM= | 0.00 | TEST= 0
| INDE | 2 | 40 | 60 | FOBS= | 76.1 | SIGMA= | 2.4 | PHAS= | -10.0 | FOM= | 0.87 | TEST= 0
| INDE | 2 | 40 | 62 | FOBS= | 0.0 | SIGMA= | 21.4 | PHAS= | 0.0 | FOM= | 0.00 | TEST= 1
| INDE | 2 | 40 | 64 | FOBS= | 0.0 | SIGMA= | 21.3 | PHAS= | 0.0 | FOM= | 0.00 | TEST= 0
| INDE | 2 | 40 | 66 | FOBS= | 62.6 | SIGMA= | 6.7 | PHAS= | 106.0 | FOM= | 0.84 | TEST= 0
| INDE | 2 | 41 | 3 | FOBS= | 209.6 | SIGMA= | 1.0 | PHAS= | 105.6 | FOM= | 0.95 | TEST= 0
| INDE | 2 | 41 | 9 | FOBS= | 275.7 | SIGMA= | 0.8 | PHAS= | -73.9 | FOM= | 0.96 | TEST= 0
| INDE | 2 | 41 | 11 | FOBS= | 375.4 | SIGMA= | 0.8 | PHAS= | -2.5 | FOM= | 0.98 | TEST= 0
| INDE | 2 | 41 | 13 | FOBS= | 48.3 | SIGMA= | 3.0 | PHAS= | 170.1 | FOM= | 0.40 | TEST= 0
| INDE | 2 | 41 | 15 | FOBS= | 52.6 | SIGMA= | 4.3 | PHAS= | -111.8 | FOM= | 0.70 | TEST= 0
| INDE | 2 | 41 | 17 | FOBS= | 125.5 | SIGMA= | 2.1 | PHAS= | 113.7 | FOM= | 0.85 | TEST= 0
| INDE | 2 | 41 | 19 | FOBS= | 77.3 | SIGMA= | 4.7 | PHAS= | 101.8 | FOM= | 0.52 | TEST= 0
| INDE | 2 | 41 | 23 | FOBS= | 39.8 | SIGMA= | 12.1 | PHAS= | 109.2 | FOM= | 0.06 | TEST= 0
| INDE | 2 | 41 | 25 | FOBS= | 114.2 | SIGMA= | 3.1 | PHAS= | -78.0 | FOM= | 0.96 | TEST= 0
| INDE | 2 | 41 | 27 | FOBS= | 0.0 | SIGMA= | 26.7 | PHAS= | 0.0 | FOM= | 0.00 | TEST= 0
| INDE | 2 | 41 | 29 | FOBS= | 107.4 | SIGMA= | 3.3 | PHAS= | -105.2 | FOM= | 0.87 | TEST= 0
| INDE | 2 | 41 | 31 | FOBS= | 30.5 | SIGMA= | 11.2 | PHAS= | 143.5 | FOM= | 0.06 | TEST= 1
| INDE | 2 | 41 | 33 | FOBS= | 103.4 | SIGMA= | 2.4 | PHAS= | 87.9 | FOM= | 0.84 | TEST= 0
| INDE | 2 | 41 | 35 | FOBS= | 89.8 | SIGMA= | 2.5 | PHAS= | 123.2 | FOM= | 0.70 | TEST= 0
| INDE | 2 | 41 | 37 | FOBS= | 113.9 | SIGMA= | 2.0 | PHAS= | -145.7 | FOM= | 0.71 | TEST= 0
| INDE | 2 | 41 | 39 | FOBS= | 134.8 | SIGMA= | 1.4 | PHAS= | 164.8 | FOM= | 0.75 | TEST= 0
| INDE | 2 | 41 | 41 | FOBS= | 173.8 | SIGMA= | 1.1 | PHAS= | 100.8 | FOM= | 0.97 | TEST= 0
| INDE | 2 | 41 | 43 | FOBS= | 106.1 | SIGMA= | 1.7 | PHAS= | 16.8 | FOM= | 0.90 | TEST= 0
| INDE | 2 | 41 | 45 | FOBS= | 67.9 | SIGMA= | 2.6 | PHAS= | -124.9 | FOM= | 0.32 | TEST= 0
| INDE | 2 | 41 | 47 | FOBS= | 106.4 | SIGMA= | 1.7 | PHAS= | -75.0 | FOM= | 0.93 | TEST= 0
| INDE | 2 | 41 | 49 | FOBS= | 44.8 | SIGMA= | 3.5 | PHAS= | -83.7 | FOM= | 0.80 | TEST= 0
| INDE | 2 | 41 | 51 | FOBS= | 131.2 | SIGMA= | 1.4 | PHAS= | -155.3 | FOM= | 0.93 | TEST= 0
| INDE | 2 | 41 | 53 | FOBS= | 33.6 | SIGMA= | 5.4 | PHAS= | 110.7 | FOM= | 0.37 | TEST= 1
| INDE | 2 | 41 | 55 | FOBS= | 91.0 | SIGMA= | 1.9 | PHAS= | 46.9 | FOM= | 0.93 | TEST= 0
| INDE | 2 | 41 | 57 | FOBS= | 88.9 | SIGMA= | 2.1 | PHAS= | -32.8 | FOM= | 0.89 | TEST= 0
| INDE | 2 | 41 | 59 | FOBS= | 41.9 | SIGMA= | 4.3 | PHAS= | -86.7 | FOM= | 0.77 | TEST= 0
| INDE | 2 | 41 | 61 | FOBS= | 52.5 | SIGMA= | 3.5 | PHAS= | -13.0 | FOM= | 0.52 | TEST= 1
| INDE | 2 | 41 | 63 | FOBS= | 0.0 | SIGMA= | 23.0 | PHAS= | 0.0 | FOM= | 0.00 | TEST= 0
| INDE | 2 | 41 | 65 | FOBS= | 64.4 | SIGMA= | 3.7 | PHAS= | -106.1 | FOM= | 0.20 | TEST= 1
| INDE | 2 | 42 | 2 | FOBS= | 147.8 | SIGMA= | 0.8 | PHAS= | -44.3 | FOM= | 0.60 | TEST= 0
| INDE | 2 | 42 | 10 | FOBS= | 254.8 | SIGMA= | 0.9 | PHAS= | -46.3 | FOM= | 0.95 | TEST= 0
| INDE | 2 | 42 | 12 | FOBS= | 82.2 | SIGMA= | 2.7 | PHAS= | 138.6 | FOM= | 0.39 | TEST= 0

*FIG. 12A - 67*

```
INDE  2  42  14 FOBS=    57.3 SIGMA=   2.7 PHAS=  -179.2 FOM=  0.96 TEST= 0
INDE  2  42  16 FOBS=   347.1 SIGMA=   1.0 PHAS=   -56.9 FOM=  0.91 TEST= 1
INDE  2  42  18 FOBS=   272.4 SIGMA=   1.2 PHAS=    -5.7 FOM=  0.97 TEST= 0
INDE  2  42  22 FOBS=   102.5 SIGMA=   4.9 PHAS=   123.1 FOM=  0.43 TEST= 0
INDE  2  42  24 FOBS=   113.3 SIGMA=   3.2 PHAS=   -69.7 FOM=  0.60 TEST= 0
INDE  2  42  26 FOBS=    37.3 SIGMA=   9.5 PHAS=    25.4 FOM=  0.13 TEST= 0
INDE  2  42  28 FOBS=     0.0 SIGMA=  26.3 PHAS=     0.0 FOM=  0.00 TEST= 0
INDE  2  42  30 FOBS=   133.0 SIGMA=   2.7 PHAS=   -57.2 FOM=  0.31 TEST= 1
INDE  2  42  32 FOBS=   127.6 SIGMA=   2.8 PHAS=     2.9 FOM=  0.60 TEST= 0
INDE  2  42  34 FOBS=   196.6 SIGMA=   1.4 PHAS=    14.5 FOM=  0.95 TEST= 0
INDE  2  42  36 FOBS=    68.2 SIGMA=   3.3 PHAS=    63.7 FOM=  0.50 TEST= 0
INDE  2  42  38 FOBS=    72.5 SIGMA=   2.8 PHAS=   104.2 FOM=  0.70 TEST= 0
INDE  2  42  40 FOBS=    75.3 SIGMA=   2.4 PHAS=   102.4 FOM=  0.82 TEST= 0
INDE  2  42  42 FOBS=   132.4 SIGMA=   1.4 PHAS=    63.7 FOM=  0.91 TEST= 0
INDE  2  42  44 FOBS=   135.7 SIGMA=   1.4 PHAS=  -109.9 FOM=  0.89 TEST= 0
INDE  2  42  46 FOBS=   135.3 SIGMA=   1.4 PHAS=  -175.2 FOM=  0.95 TEST= 0
INDE  2  42  48 FOBS=   101.4 SIGMA=   1.7 PHAS=   156.4 FOM=  0.75 TEST= 0
INDE  2  42  50 FOBS=    72.9 SIGMA=   2.0 PHAS=   158.4 FOM=  0.82 TEST= 0
INDE  2  42  52 FOBS=    69.2 SIGMA=   2.8 PHAS=   169.8 FOM=  0.66 TEST= 0
INDE  2  42  54 FOBS=   129.0 SIGMA=   1.4 PHAS=    45.9 FOM=  0.95 TEST= 0
INDE  2  42  56 FOBS=    15.8 SIGMA=  12.2 PHAS=   -58.2 FOM=  0.74 TEST= 0
INDE  2  42  58 FOBS=     0.0 SIGMA=  20.0 PHAS=     0.0 FOM=  0.00 TEST= 0
INDE  2  42  60 FOBS=    14.0 SIGMA=  15.5 PHAS=  -157.8 FOM=  0.01 TEST= 1
INDE  2  42  62 FOBS=     0.0 SIGMA=  19.8 PHAS=     0.0 FOM=  0.00 TEST= 0
INDE  2  42  64 FOBS=    83.5 SIGMA=   3.2 PHAS=   166.7 FOM=  0.87 TEST= 0
INDE  2  43   3 FOBS=   211.0 SIGMA=   1.0 PHAS=    85.8 FOM=  0.94 TEST= 0
INDE  2  43   9 FOBS=   357.7 SIGMA=   1.0 PHAS=   -83.9 FOM=  0.99 TEST= 0
INDE  2  43  11 FOBS=   167.6 SIGMA=   0.9 PHAS=    68.2 FOM=  0.94 TEST= 0
INDE  2  43  13 FOBS=    76.5 SIGMA=   2.0 PHAS=  -125.4 FOM=  0.56 TEST= 1
INDE  2  43  15 FOBS=   192.0 SIGMA=   1.0 PHAS=  -145.5 FOM=  0.92 TEST= 0
INDE  2  43  17 FOBS=   122.8 SIGMA=   2.3 PHAS=   160.4 FOM=  0.93 TEST= 0
INDE  2  43  19 FOBS=   113.3 SIGMA=   2.6 PHAS=  -108.0 FOM=  0.95 TEST= 1
INDE  2  43  23 FOBS=    15.3 SIGMA=  33.1 PHAS=    85.0 FOM=  0.07 TEST= 0
INDE  2  43  25 FOBS=   158.1 SIGMA=   2.4 PHAS=  -119.1 FOM=  0.63 TEST= 0
INDE  2  43  27 FOBS=   139.8 SIGMA=   2.7 PHAS=     3.5 FOM=  0.80 TEST= 0
INDE  2  43  29 FOBS=    51.7 SIGMA=   6.7 PHAS=   128.2 FOM=  0.42 TEST= 0
INDE  2  43  31 FOBS=   248.8 SIGMA=   1.6 PHAS=    18.0 FOM=  0.40 TEST= 1
INDE  2  43  33 FOBS=    89.0 SIGMA=   3.8 PHAS=   143.9 FOM=  0.53 TEST= 0
INDE  2  43  35 FOBS=    99.1 SIGMA=   2.3 PHAS=   -98.6 FOM=  0.93 TEST= 0
INDE  2  43  37 FOBS=    44.3 SIGMA=   4.9 PHAS=  -174.7 FOM=  0.19 TEST= 0
INDE  2  43  39 FOBS=    11.9 SIGMA=  15.0 PHAS=    81.5 FOM=  0.27 TEST= 0
INDE  2  43  41 FOBS=   175.4 SIGMA=   1.1 PHAS=    79.6 FOM=  0.97 TEST= 0
INDE  2  43  43 FOBS=    56.8 SIGMA=   3.1 PHAS=   -33.2 FOM=  0.69 TEST= 0
INDE  2  43  45 FOBS=   137.8 SIGMA=   1.4 PHAS=   111.0 FOM=  0.97 TEST= 0
INDE  2  43  47 FOBS=    36.7 SIGMA=   4.7 PHAS=    18.8 FOM=  0.71 TEST= 0
INDE  2  43  49 FOBS=    62.2 SIGMA=   2.6 PHAS=    51.6 FOM=  0.85 TEST= 0
INDE  2  43  51 FOBS=    30.5 SIGMA=   6.9 PHAS=  -165.4 FOM=  0.28 TEST= 0
INDE  2  43  53 FOBS=    63.7 SIGMA=   2.7 PHAS=     6.5 FOM=  0.69 TEST= 0
INDE  2  43  55 FOBS=     0.0 SIGMA=  18.6 PHAS=     0.0 FOM=  0.00 TEST= 0
INDE  2  43  57 FOBS=    70.2 SIGMA=   2.7 PHAS=   -91.9 FOM=  0.83 TEST= 0
INDE  2  43  59 FOBS=   112.5 SIGMA=   1.7 PHAS=   -55.5 FOM=  0.49 TEST= 1
INDE  2  43  61 FOBS=    31.9 SIGMA=   6.8 PHAS=  -162.4 FOM=  0.60 TEST= 0
INDE  2  43  63 FOBS=    59.7 SIGMA=   4.3 PHAS=    43.1 FOM=  0.91 TEST= 0
INDE  2  44   2 FOBS=   154.7 SIGMA=   1.1 PHAS=    91.3 FOM=  0.97 TEST= 0
INDE  2  44  10 FOBS=   134.6 SIGMA=   1.5 PHAS=   -85.6 FOM=  0.82 TEST= 0
INDE  2  44  12 FOBS=   169.3 SIGMA=   1.0 PHAS=    38.9 FOM=  0.98 TEST= 0
INDE  2  44  14 FOBS=   162.8 SIGMA=   1.1 PHAS=   156.5 FOM=  0.72 TEST= 1
INDE  2  44  16 FOBS=   292.8 SIGMA=   0.8 PHAS=    15.7 FOM=  0.44 TEST= 1
INDE  2  44  18 FOBS=     0.0 SIGMA=  24.3 PHAS=     0.0 FOM=  0.00 TEST= 0
INDE  2  44  20 FOBS=    95.9 SIGMA=   3.1 PHAS=   145.4 FOM=  0.93 TEST= 0
INDE  2  44  22 FOBS=    45.7 SIGMA=  11.3 PHAS=    50.9 FOM=  0.26 TEST= 0
INDE  2  44  24 FOBS=   200.6 SIGMA=   2.0 PHAS=  -109.9 FOM=  0.85 TEST= 0
INDE  2  44  26 FOBS=    69.2 SIGMA=   5.1 PHAS=   -84.2 FOM=  0.77 TEST= 0
INDE  2  44  28 FOBS=    80.1 SIGMA=   4.4 PHAS=   -81.5 FOM=  0.46 TEST= 0
INDE  2  44  30 FOBS=   231.5 SIGMA=   1.7 PHAS=    41.7 FOM=  0.92 TEST= 0
INDE  2  44  32 FOBS=   127.2 SIGMA=   2.7 PHAS=   -49.8 FOM=  0.71 TEST= 0
INDE  2  44  34 FOBS=    33.2 SIGMA=   7.8 PHAS=  -164.4 FOM=  0.35 TEST= 0
INDE  2  44  36 FOBS=     0.0 SIGMA=  22.3 PHAS=     0.0 FOM=  0.00 TEST= 0
INDE  2  44  38 FOBS=   195.2 SIGMA=   1.1 PHAS=   -51.5 FOM=  0.51 TEST= 1
INDE  2  44  40 FOBS=   160.4 SIGMA=   1.2 PHAS=   -84.8 FOM=  0.26 TEST= 1
```

*FIG. 12A - 68*

```
INDE   2  44  42 FOBS=    82.5 SIGMA=   2.2 PHAS=   34.9 FOM=  0.91 TEST= 0
INDE   2  44  44 FOBS=   105.9 SIGMA=   1.8 PHAS=   -8.1 FOM=  0.94 TEST= 0
INDE   2  44  46 FOBS=    92.0 SIGMA=   2.0 PHAS=    0.7 FOM=  0.88 TEST= 0
INDE   2  44  48 FOBS=    57.7 SIGMA=   3.0 PHAS=  -44.7 FOM=  0.81 TEST= 0
INDE   2  44  50 FOBS=    53.2 SIGMA=   3.3 PHAS= -114.6 FOM=  0.30 TEST= 1
INDE   2  44  52 FOBS=    24.9 SIGMA=   7.7 PHAS=   16.2 FOM=  0.11 TEST= 1
INDE   2  44  54 FOBS=    88.7 SIGMA=   2.0 PHAS=   88.3 FOM=  0.69 TEST= 0
INDE   2  44  56 FOBS=    29.0 SIGMA=   6.0 PHAS=   92.9 FOM=  0.76 TEST= 0
INDE   2  44  58 FOBS=   130.1 SIGMA=   1.4 PHAS= -164.8 FOM=  0.97 TEST= 0
INDE   2  44  60 FOBS=   107.2 SIGMA=   1.8 PHAS=  146.2 FOM=  0.94 TEST= 0
INDE   2  44  62 FOBS=    76.6 SIGMA=   2.7 PHAS= -134.4 FOM=  0.87 TEST= 0
INDE   2  44  64 FOBS=    34.2 SIGMA=  11.2 PHAS= -154.2 FOM=  0.23 TEST= 0
INDE   2  45   3 FOBS=   381.4 SIGMA=   0.8 PHAS=  -35.3 FOM=  0.99 TEST= 0
INDE   2  45  11 FOBS=    68.1 SIGMA=   2.3 PHAS=  172.6 FOM=  0.92 TEST= 0
INDE   2  45  13 FOBS=   242.5 SIGMA=   0.9 PHAS=  -68.1 FOM=  0.94 TEST= 0
INDE   2  45  15 FOBS=    35.0 SIGMA=   5.2 PHAS=   30.4 FOM=  0.94 TEST= 0
INDE   2  45  17 FOBS=   118.0 SIGMA=   1.7 PHAS=  -16.7 FOM=  0.96 TEST= 0
INDE   2  45  19 FOBS=    60.8 SIGMA=   5.2 PHAS= -119.8 FOM=  0.55 TEST= 1
INDE   2  45  21 FOBS=    59.5 SIGMA=   5.0 PHAS=   60.8 FOM=  0.66 TEST= 0
INDE   2  45  23 FOBS=   106.3 SIGMA=   5.0 PHAS=   90.0 FOM=  0.32 TEST= 0
INDE   2  45  25 FOBS=   182.1 SIGMA=   2.1 PHAS=  125.0 FOM=  0.82 TEST= 0
INDE   2  45  27 FOBS=    98.2 SIGMA=   3.6 PHAS= -177.6 FOM=  0.77 TEST= 0
INDE   2  45  29 FOBS=   132.7 SIGMA=   2.7 PHAS=   49.5 FOM=  0.91 TEST= 0
INDE   2  45  31 FOBS=    75.6 SIGMA=   4.5 PHAS=  -64.7 FOM=  0.66 TEST= 0
INDE   2  45  33 FOBS=    72.1 SIGMA=   4.7 PHAS= -166.4 FOM=  0.34 TEST= 0
INDE   2  45  35 FOBS=   125.8 SIGMA=   2.0 PHAS= -179.1 FOM=  0.86 TEST= 0
INDE   2  45  37 FOBS=   121.9 SIGMA=   1.9 PHAS= -123.3 FOM=  0.93 TEST= 0
INDE   2  45  39 FOBS=   204.7 SIGMA=   1.0 PHAS= -101.9 FOM=  0.85 TEST= 0
INDE   2  45  41 FOBS=    65.0 SIGMA=   2.8 PHAS=   44.3 FOM=  0.33 TEST= 0
INDE   2  45  43 FOBS=   119.1 SIGMA=   1.6 PHAS=  -60.8 FOM=  0.91 TEST= 0
INDE   2  45  45 FOBS=    95.2 SIGMA=   1.9 PHAS=  -63.5 FOM=  0.85 TEST= 0
INDE   2  45  47 FOBS=    48.7 SIGMA=   3.6 PHAS=  -61.7 FOM=  0.37 TEST= 0
INDE   2  45  49 FOBS=     0.0 SIGMA=  17.7 PHAS=    0.0 FOM=  0.00 TEST= 0
INDE   2  45  51 FOBS=    15.4 SIGMA=  11.9 PHAS=  -67.9 FOM=  0.26 TEST= 0
INDE   2  45  53 FOBS=    64.4 SIGMA=   2.7 PHAS=  -83.9 FOM=  0.82 TEST= 0
INDE   2  45  55 FOBS=     0.0 SIGMA=  21.1 PHAS=    0.0 FOM=  0.00 TEST= 0
INDE   2  45  57 FOBS=   102.9 SIGMA=   1.8 PHAS=   52.2 FOM=  0.90 TEST= 0
INDE   2  45  59 FOBS=     7.0 SIGMA=  31.4 PHAS=   61.4 FOM=  0.34 TEST= 0
INDE   2  45  61 FOBS=    69.2 SIGMA=   3.0 PHAS=  123.5 FOM=  0.90 TEST= 0
INDE   2  45  63 FOBS=    78.5 SIGMA=   3.3 PHAS=   96.3 FOM=  0.91 TEST= 0
INDE   2  46   2 FOBS=    76.4 SIGMA=   1.7 PHAS=  -70.5 FOM=  0.80 TEST= 0
INDE   2  46  12 FOBS=   100.0 SIGMA=   1.7 PHAS=   -4.1 FOM=  0.86 TEST= 0
INDE   2  46  14 FOBS=    52.0 SIGMA=   3.4 PHAS= -155.4 FOM=  0.81 TEST= 0
INDE   2  46  16 FOBS=    58.6 SIGMA=   3.4 PHAS=  -68.8 FOM=  0.86 TEST= 0
INDE   2  46  18 FOBS=   169.4 SIGMA=   1.5 PHAS=  -92.1 FOM=  0.92 TEST= 0
INDE   2  46  20 FOBS=    88.2 SIGMA=   3.5 PHAS=  102.7 FOM=  0.26 TEST= 0
INDE   2  46  22 FOBS=   164.2 SIGMA=   1.7 PHAS=  103.7 FOM=  0.05 TEST= 1
INDE   2  46  24 FOBS=    58.0 SIGMA=   6.2 PHAS=  -64.2 FOM=  0.28 TEST= 0
INDE   2  46  26 FOBS=   123.2 SIGMA=   3.0 PHAS= -146.1 FOM=  0.58 TEST= 0
INDE   2  46  28 FOBS=    92.8 SIGMA=   3.8 PHAS=   26.6 FOM=  0.85 TEST= 0
INDE   2  46  30 FOBS=    58.5 SIGMA=   5.9 PHAS=  -94.1 FOM=  0.58 TEST= 0
INDE   2  46  32 FOBS=    79.5 SIGMA=   4.3 PHAS= -124.6 FOM=  0.75 TEST= 0
INDE   2  46  34 FOBS=   110.1 SIGMA=   3.1 PHAS= -134.3 FOM=  0.76 TEST= 1
INDE   2  46  36 FOBS=   149.0 SIGMA=   1.6 PHAS=  102.3 FOM=  0.93 TEST= 0
INDE   2  46  38 FOBS=     0.0 SIGMA=  19.9 PHAS=    0.0 FOM=  0.00 TEST= 0
INDE   2  46  40 FOBS=    51.2 SIGMA=   3.5 PHAS=  -92.9 FOM=  0.60 TEST= 0
INDE   2  46  42 FOBS=    90.2 SIGMA=   2.0 PHAS= -131.5 FOM=  0.81 TEST= 0
INDE   2  46  44 FOBS=    13.1 SIGMA=  14.0 PHAS= -101.7 FOM=  0.25 TEST= 1
INDE   2  46  46 FOBS=    88.3 SIGMA=   2.1 PHAS=  -79.5 FOM=  0.84 TEST= 0
INDE   2  46  48 FOBS=    72.6 SIGMA=   2.4 PHAS= -124.7 FOM=  0.78 TEST= 0
INDE   2  46  50 FOBS=    34.2 SIGMA=   5.4 PHAS=   59.4 FOM=  0.48 TEST= 0
INDE   2  46  52 FOBS=    81.2 SIGMA=   2.2 PHAS= -113.5 FOM=  0.85 TEST= 0
INDE   2  46  54 FOBS=    12.9 SIGMA=  14.0 PHAS=  177.4 FOM=  0.13 TEST= 0
INDE   2  46  56 FOBS=    28.2 SIGMA=   6.5 PHAS=  100.3 FOM=  0.44 TEST= 0
INDE   2  46  58 FOBS=     0.0 SIGMA=  18.8 PHAS=    0.0 FOM=  0.00 TEST= 0
INDE   2  46  60 FOBS=    42.7 SIGMA=   4.9 PHAS=   93.4 FOM=  0.76 TEST= 0
INDE   2  46  62 FOBS=    71.7 SIGMA=   3.6 PHAS=   -4.7 FOM=  0.78 TEST= 0
INDE   2  47   3 FOBS=   150.7 SIGMA=   1.0 PHAS=  -48.2 FOM=  0.90 TEST= 0
INDE   2  47  11 FOBS=    21.9 SIGMA=  10.2 PHAS=   63.5 FOM=  0.21 TEST= 0
INDE   2  47  13 FOBS=   121.9 SIGMA=   1.5 PHAS= -154.5 FOM=  0.94 TEST= 0
```

*FIG. 12A - 69*

| | | | | | | | | | | | |
|---|---|---|---|---|---|---|---|---|---|---|---|
| INDE | 2 | 47 | 15 | FOBS= | 86.6 | SIGMA= | 2.2 | PHAS= | 66.5 | FOM= | 0.76 | TEST= 0
| INDE | 2 | 47 | 17 | FOBS= | 235.7 | SIGMA= | 1.0 | PHAS= | -1.1 | FOM= | 0.98 | TEST= 0
| INDE | 2 | 47 | 19 | FOBS= | 132.9 | SIGMA= | 2.4 | PHAS= | 166.6 | FOM= | 0.85 | TEST= 0
| INDE | 2 | 47 | 21 | FOBS= | 172.8 | SIGMA= | 1.9 | PHAS= | -45.9 | FOM= | 0.75 | TEST= 0
| INDE | 2 | 47 | 23 | FOBS= | 102.3 | SIGMA= | 2.3 | PHAS= | -23.4 | FOM= | 0.50 | TEST= 0
| INDE | 2 | 47 | 25 | FOBS= | 162.8 | SIGMA= | 2.3 | PHAS= | 153.5 | FOM= | 0.88 | TEST= 0
| INDE | 2 | 47 | 27 | FOBS= | 80.0 | SIGMA= | 4.4 | PHAS= | 133.2 | FOM= | 0.83 | TEST= 0
| INDE | 2 | 47 | 29 | FOBS= | 190.4 | SIGMA= | 2.0 | PHAS= | 142.9 | FOM= | 0.79 | TEST= 0
| INDE | 2 | 47 | 31 | FOBS= | 100.3 | SIGMA= | 3.5 | PHAS= | 169.8 | FOM= | 0.88 | TEST= 0
| INDE | 2 | 47 | 33 | FOBS= | 238.4 | SIGMA= | 1.6 | PHAS= | 91.0 | FOM= | 0.97 | TEST= 0
| INDE | 2 | 47 | 35 | FOBS= | 52.2 | SIGMA= | 6.3 | PHAS= | -0.6 | FOM= | 0.66 | TEST= 0
| INDE | 2 | 47 | 37 | FOBS= | 190.2 | SIGMA= | 1.3 | PHAS= | -16.2 | FOM= | 0.94 | TEST= 0
| INDE | 2 | 47 | 39 | FOBS= | 151.3 | SIGMA= | 1.3 | PHAS= | -89.8 | FOM= | 0.93 | TEST= 0
| INDE | 2 | 47 | 41 | FOBS= | 134.9 | SIGMA= | 1.4 | PHAS= | -175.9 | FOM= | 0.93 | TEST= 0
| INDE | 2 | 47 | 43 | FOBS= | 93.2 | SIGMA= | 2.1 | PHAS= | 103.7 | FOM= | 0.84 | TEST= 0
| INDE | 2 | 47 | 45 | FOBS= | 45.3 | SIGMA= | 4.0 | PHAS= | -55.1 | FOM= | 0.75 | TEST= 0
| INDE | 2 | 47 | 47 | FOBS= | 99.0 | SIGMA= | 1.9 | PHAS= | 161.8 | FOM= | 0.92 | TEST= 0
| INDE | 2 | 47 | 49 | FOBS= | 38.9 | SIGMA= | 5.5 | PHAS= | 120.2 | FOM= | 0.60 | TEST= 0
| INDE | 2 | 47 | 51 | FOBS= | 46.2 | SIGMA= | 3.8 | PHAS= | -173.7 | FOM= | 0.81 | TEST= 0
| INDE | 2 | 47 | 53 | FOBS= | 31.5 | SIGMA= | 5.8 | PHAS= | -133.3 | FOM= | 0.53 | TEST= 0
| INDE | 2 | 47 | 55 | FOBS= | 0.0 | SIGMA= | 19.7 | PHAS= | 0.0 | FOM= | 0.00 | TEST= 1
| INDE | 2 | 47 | 57 | FOBS= | 32.3 | SIGMA= | 5.5 | PHAS= | 38.3 | FOM= | 0.67 | TE6T= 0
| INDE | 2 | 47 | 59 | FOBS= | 24.8 | SIGMA= | 8.8 | PHAS= | -104.8 | FOM= | 0.21 | TEST= 0
| INDE | 2 | 47 | 61 | FOBS= | 3.8 | SIGMA= | 73.3 | PHAS= | 105.1 | FOM= | 0.06 | TEST= 0
| INDE | 2 | 48 | 2 | FOBS= | 150.5 | SIGMA= | 0.9 | PHAS= | -93.0 | FOM= | 0.91 | TEST= 0
| INDE | 2 | 48 | 12 | FOBS= | 98.8 | SIGMA= | 1.8 | PHAS= | 47.1 | FOM= | 0.75 | TEST= 0
| INDE | 2 | 48 | 14 | FOBS= | 47.7 | SIGMA= | 3.7 | PHAS= | -151.6 | FOM= | 0.54 | TEST= 0
| INDE | 2 | 48 | 16 | FOBS= | 48.0 | SIGMA= | 3.9 | PHAS= | -149.6 | FOM= | 0.13 | TEST= 0
| INDE | 2 | 48 | 18 | FOBS= | 124.7 | SIGMA= | 1.7 | PHAS= | -70.8 | FOM= | 0.90 | TEST= 0
| INDE | 2 | 48 | 20 | FOBS= | 106.7 | SIGMA= | 2.9 | PHAS= | 162.3 | FOM= | 0.88 | TEST= 1
| INDE | 2 | 48 | 22 | FOBS= | 167.1 | SIGMA= | 1.7 | PHAS= | -114.7 | FOM= | 0.53 | TEST= 0
| INDE | 2 | 48 | 24 | FOBS= | 35.1 | SIGMA= | 10.1 | PHAS= | 37.8 | FOM= | 0.23 | TEST= 0
| INDE | 2 | 48 | 26 | FOBS= | 67.2 | SIGMA= | 5.2 | PHAS= | -155.1 | FOM= | 0.64 | TEST= 0
| INDE | 2 | 48 | 28 | FOBS= | 201.4 | SIGMA= | 2.0 | PHAS= | 37.0 | FOM= | 0.94 | TEST= 0
| INDE | 2 | 48 | 30 | FOBS= | 238.2 | SIGMA= | 1.7 | PHAS= | 88.9 | FOM= | 0.94 | TEST= 0
| INDE | 2 | 48 | 32 | FOBS= | 106.4 | SIGMA= | 3.3 | PHAS= | 40.9 | FOM= | 0.95 | TEST= 0
| INDE | 2 | 48 | 34 | FOBS= | 161.5 | SIGMA= | 2.2 | PHAS= | -94.0 | FOM= | 0.91 | TEST= 0
| INDE | 2 | 48 | 36 | FOBS= | 63.9 | SIGMA= | 4.4 | PHAS= | -110.9 | FOM= | 0.82 | TEST= 0
| INDE | 2 | 48 | 38 | FOBS= | 149.0 | SIGMA= | 1.4 | PHAS= | -148.3 | FOM= | 0.96 | TEST= 0
| INDE | 2 | 48 | 40 | FOBS= | 131.7 | SIGMA= | 1.4 | PHAS= | 152.3 | FOM= | 0.97 | TEST= 0
| INDE | 2 | 48 | 42 | FOBS= | 51.3 | SIGMA= | 3.6 | PHAS= | 48.1 | FOM= | 0.79 | TEST= 0
| INDE | 2 | 48 | 44 | FOBS= | 27.9 | SIGMA= | 7.6 | PHAS= | 48.9 | FOM= | 0.30 | TEST= 1
| INDE | 2 | 48 | 46 | FOBS= | 89.4 | SIGMA= | 2.1 | PHAS= | -18.8 | FOM= | 0.78 | TEST= 1
| INDE | 2 | 48 | 48 | FOBS= | 40.4 | SIGMA= | 4.9 | PHAS= | -41.1 | FOM= | 0.51 | TEST= 0
| INDE | 2 | 48 | 50 | FOBS= | 42.6 | SIGMA= | 4.2 | PHAS= | 64.2 | FOM= | 0.65 | TEST= 0
| INDE | 2 | 48 | 52 | FOBS= | 9.6 | SIGMA= | 20.1 | PHAS= | 106.1 | FOM= | 0.22 | TEST= 0
| INDE | 2 | 48 | 54 | FOBS= | 0.0 | SIGMA= | 19.1 | PHAS= | 0.0 | FOM= | 0.00 | TEST= 0
| INDE | 2 | 48 | 56 | FOBS= | 50.6 | SIGMA= | 3.7 | PHAS= | -130.7 | FOM= | 0.68 | TEST= 0
| INDE | 2 | 48 | 58 | FOBS= | 29.8 | SIGMA= | 6.9 | PHAS= | 118.4 | FOM= | 0.48 | TEST= 0
| INDE | 2 | 48 | 60 | FOBS= | 35.1 | SIGMA= | 6.9 | PHAS= | 58.5 | FOM= | 0.19 | TEST= 0
| INDE | 2 | 49 | 3 | FOBS= | 78.7 | SIGMA= | 2.2 | PHAS= | -15.2 | FOM= | 0.86 | TEST= 0
| INDE | 2 | 49 | 13 | FOBS= | 85.8 | SIGMA= | 2.1 | PHAS= | 116.7 | FOM= | 0.76 | TEST= 0
| INDE | 2 | 49 | 15 | FOBS= | 148.2 | SIGMA= | 1.3 | PHAS= | 77.8 | FOM= | 0.97 | TEST= 0
| INDE | 2 | 49 | 17 | FOBS= | 153.3 | SIGMA= | 1.3 | PHAS= | -31.4 | FOM= | 0.90 | TEST= 0
| INDE | 2 | 49 | 19 | FOBS= | 139.5 | SIGMA= | 1.5 | PHAS= | 115.2 | FOM= | 0.95 | TEST= 0
| INDE | 2 | 49 | 21 | FOBS= | 42.1 | SIGMA= | 7.2 | PHAS= | -166.8 | FOM= | 0.57 | TEST= 0
| INDE | 2 | 49 | 23 | FOBS= | 117.8 | SIGMA= | 2.0 | PHAS= | -131.2 | FOM= | 0.65 | TEST= 0
| INDE | 2 | 49 | 25 | FOBS= | 147.2 | SIGMA= | 2.5 | PHAS= | 93.5 | FOM= | 0.69 | TEST= 0
| INDE | 2 | 49 | 27 | FOBS= | 44.1 | SIGMA= | 7.8 | PHAS= | -52.0 | FOM= | 0.62 | TEST= 0
| INDE | 2 | 49 | 29 | FOBS= | 50.4 | SIGMA= | 6.8 | PHAS= | 71.3 | FOM= | 0.03 | TEST= 1
| INDE | 2 | 49 | 31 | FOBS= | 104.9 | SIGMA= | 3.3 | PHAS= | 6.2 | FOM= | 0.90 | TEST= 0
| INDE | 2 | 49 | 33 | FOBS= | 33.9 | SIGMA= | 9.7 | PHAS= | 25.0 | FOM= | 0.29 | TEST= 0
| INDE | 2 | 49 | 35 | FOBS= | 118.2 | SIGMA= | 2.9 | PHAS= | 166.1 | FOM= | 0.93 | TEST= 0
| INDE | 2 | 49 | 37 | FOBS= | 57.9 | SIGMA= | 4.9 | PHAS= | 139.8 | FOM= | 0.70 | TEST= 1
| INDE | 2 | 49 | 39 | FOBS= | 95.3 | SIGMA= | 1.9 | PHAS= | 102.8 | FOM= | 0.93 | TEST= 0
| INDE | 2 | 49 | 41 | FOBS= | 62.0 | SIGMA= | 2.9 | PHAS= | 123.2 | FOM= | 0.24 | TEST= 0
| INDE | 2 | 49 | 43 | FOBS= | 0.0 | SIGMA= | 26.1 | PHAS= | 0.0 | FOM= | 0.00 | TEST= 0
| INDE | 2 | 49 | 45 | FOBS= | 51.3 | SIGMA= | 3.6 | PHAS= | -108.5 | FOM= | 0.03 | TEST= 1
| INDE | 2 | 49 | 47 | FOBS= | 48.0 | SIGMA= | 5.2 | PHAS= | -179.7 | FOM= | 0.79 | TEST= 0
| INDE | 2 | 49 | 49 | FOBS= | 15.2 | SIGMA= | 13.3 | PHAS= | 129.5 | FOM= | 0.49 | TEST= 0

*FIG. 12A - 70*

```
INDE  2  49  51 FOBS=   55.5 SIGMA=  3.2 PHAS=  103.8 FOM= 0.75 TEST= 0
INDE  2  49  53 FOBS=   10.1 SIGMA= 18.8 PHAS=  -37.5 FOM= 0.13 TEST= 0
INDE  2  49  55 FOBS=   87.4 SIGMA=  2.1 PHAS=  126.7 FOM= 0.88 TEST= 0
INDE  2  49  57 FOBS=    0.0 SIGMA= 20.0 PHAS=    0.0 FOM= 0.00 TEST= 0
INDE  2  49  59 FOBS=    5.1 SIGMA= 59.1 PHAS=  165.3 FOM= 0.00 TEST= 1
INDE  2  50   2 FOBS=  165.6 SIGMA=  0.8 PHAS=  -44.3 FOM= 0.93 TEST= 0
INDE  2  50  12 FOBS=  112.7 SIGMA=  2.0 PHAS=    9.3 FOM= 0.86 TEST= 0
INDE  2  50  14 FOBS=  119.6 SIGMA=  1.5 PHAS=  -38.7 FOM= 0.95 TEST= 0
INDE  2  50  16 FOBS=  247.6 SIGMA=  0.9 PHAS=   46.0 FOM= 0.96 TEST= 0
INDE  2  50  18 FOBS=  135.8 SIGMA=  1.5 PHAS= -119.3 FOM= 0.90 TEST= 0
INDE  2  50  20 FOBS=  102.8 SIGMA=  2.0 PHAS=  -90.0 FOM= 0.76 TEST= 0
INDE  2  50  22 FOBS=   19.7 SIGMA= 13.1 PHAS=  126.2 FOM= 0.40 TEST= 0
INDE  2  50  24 FOBS=   84.5 SIGMA=  2.8 PHAS=    6.6 FOM= 0.54 TEST= 0
INDE  2  50  26 FOBS=  128.0 SIGMA=  2.8 PHAS=  175.7 FOM= 0.90 TEST= 0
INDE  2  50  28 FOBS=    0.0 SIGMA= 26.1 PHAS=    0.0 FOM= 0.00 TEST= 0
INDE  2  50  30 FOBS=    0.0 SIGMA= 25.9 PHAS=    0.0 FOM= 0.00 TEST= 0
INDE  2  50  32 FOBS=  102.8 SIGMA=  3.3 PHAS=  -79.2 FOM= 0.67 TEST= 0
INDE  2  50  34 FOBS=   84.9 SIGMA=  4.0 PHAS= -176.2 FOM= 0.62 TEST= 0
INDE  2  50  36 FOBS=  109.5 SIGMA=  3.1 PHAS=   16.1 FOM= 0.89 TEST= 0
INDE  2  50  38 FOBS=   81.4 SIGMA=  2.4 PHAS=  -56.7 FOM= 0.82 TEST= 0
INDE  2  50  40 FOBS=   89.2 SIGMA=  2.0 PHAS=   45.4 FOM= 0.89 TEST= 0
INDE  2  50  42 FOBS=   62.3 SIGMA=  2.9 PHAS=  153.5 FOM= 0.58 TEST= 0
INDE  2  50  44 FOBS=   35.5 SIGMA=  5.5 PHAS= -166.2 FOM= 0.66 TEST= 0
INDE  2  50  46 FOBS=  112.2 SIGMA=  1.7 PHAS=   60.9 FOM= 0.94 TEST= 0
INDE  2  50  48 FOBS=   41.4 SIGMA=  5.6 PHAS=  100.3 FOM= 0.45 TEST= 0
INDE  2  50  50 FOBS=   81.8 SIGMA=  2.2 PHAS=   -1.9 FOM= 0.91 TEST= 0
INDE  2  50  52 FOBS=   92.6 SIGMA=  2.0 PHAS=   -8.8 FOM= 0.94 TEST= 0
INDE  2  50  54 FOBS=   68.3 SIGMA=  2.6 PHAS=   12.8 FOM= 0.64 TEST= 0
INDE  2  50  56 FOBS=    8.7 SIGMA= 27.3 PHAS=  -11.4 FOM= 0.00 TEST= 1
INDE  2  50  58 FOBS=   39.3 SIGMA=  6.7 PHAS=  -30.0 FOM= 0.10 TEST= 1
INDE  2  51   3 FOBS=  179.0 SIGMA=  1.0 PHAS=  -53.2 FOM= 0.75 TEST= 0
INDE  2  51  13 FOBS=   39.1 SIGMA=  5.9 PHAS=  -62.7 FOM= 0.78 TEST= 0
INDE  2  51  15 FOBS=  181.8 SIGMA=  1.3 PHAS=  -28.0 FOM= 0.61 TEST= 1
INDE  2  51  17 FOBS=   57.1 SIGMA=  3.3 PHAS=  -93.1 FOM= 0.65 TEST= 0
INDE  2  51  19 FOBS=  103.9 SIGMA=  1.9 PHAS=  166.4 FOM= 0.88 TEST= 0
INDE  2  51  21 FOBS=  130.6 SIGMA=  1.5 PHAS=   89.7 FOM= 0.83 TEST= 0
INDE  2  51  23 FOBS=   71.5 SIGMA=  3.3 PHAS= -152.9 FOM= 0.93 TEST= 0
INDE  2  51  25 FOBS=   62.4 SIGMA=  3.7 PHAS=  109.0 FOM= 0.17 TEST= 1
INDE  2  51  27 FOBS=  102.8 SIGMA=  3.4 PHAS=  104.4 FOM= 0.81 TEST= 0
INDE  2  51  29 FOBS=  102.9 SIGMA=  3.4 PHAS=  -56.5 FOM= 0.59 TEST= 0
INDE  2  51  31 FOBS=   53.7 SIGMA=  6.3 PHAS= -156.9 FOM= 0.73 TEST= 0
INDE  2  51  33 FOBS=   30.1 SIGMA= 10.9 PHAS=  -66.4 FOM= 0.30 TEST= 0
INDE  2  51  35 FOBS=  133.1 SIGMA=  2.6 PHAS=  165.5 FOM= 0.94 TEST= 0
INDE  2  51  37 FOBS=   90.2 SIGMA=  3.0 PHAS= -121.8 FOM= 0.54 TEST= 0
INDE  2  51  39 FOBS=    0.0 SIGMA= 19.2 PHAS=    0.0 FOM= 0.00 TEST= 0
INDE  2  51  41 FOBS=    0.0 SIGMA= 20.1 PHAS=    0.0 FOM= 0.00 TEST= 0
INDE  2  51  43 FOBS=   75.9 SIGMA=  2.5 PHAS=   92.2 FOM= 0.74 TEST= 0
INDE  2  51  45 FOBS=  105.9 SIGMA=  1.8 PHAS=  -18.4 FOM= 0.93 TEST= 0
INDE  2  51  47 FOBS=  105.3 SIGMA=  1.8 PHAS=  -25.9 FOM= 0.96 TEST= 0
INDE  2  51  49 FOBS=   48.6 SIGMA=  3.8 PHAS=  -11.1 FOM= 0.41 TEST= 1
INDE  2  51  51 FOBS=   12.3 SIGMA= 14.8 PHAS=  -96.1 FOM= 0.41 TEST= 0
INDE  2  51  53 FOBS=   92.9 SIGMA=  2.0 PHAS= -126.3 FOM= 0.93 TEST= 0
INDE  2  51  55 FOBS=    0.0 SIGMA= 19.9 PHAS=    0.0 FOM= 0.00 TEST= 0
INDE  2  51  57 FOBS=    0.0 SIGMA= 23.2 PHAS=    0.0 FOM= 0.00 TEST= 0
INDE  2  52   2 FOBS=   84.8 SIGMA=  1.7 PHAS=   66.2 FOM= 0.86 TEST= 0
INDE  2  52   4 FOBS=  209.0 SIGMA=  1.0 PHAS=  -98.2 FOM= 0.51 TEST= 0
INDE  2  52  14 FOBS=  140.2 SIGMA=  1.3 PHAS=  -77.5 FOM= 0.94 TEST= 0
INDE  2  52  16 FOBS=  236.5 SIGMA=  0.9 PHAS=   95.6 FOM= 0.91 TEST= 0
INDE  2  52  18 FOBS=  148.0 SIGMA=  1.3 PHAS=   40.8 FOM= 0.81 TEST= 0
INDE  2  52  20 FOBS=  106.2 SIGMA=  2.2 PHAS=   21.7 FOM= 0.89 TEST= 0
INDE  2  52  22 FOBS=  133.9 SIGMA=  1.4 PHAS=  110.4 FOM= 0.20 TEST= 1
INDE  2  52  24 FOBS=   26.7 SIGMA= 12.5 PHAS=  -66.9 FOM= 0.13 TEST= 0
INDE  2  52  26 FOBS=   71.0 SIGMA=  3.3 PHAS=   98.2 FOM= 0.84 TEST= 0
INDE  2  52  28 FOBS=   20.8 SIGMA= 16.3 PHAS=   12.7 FOM= 0.00 TEST= 1
INDE  2  52  30 FOBS=   39.6 SIGMA=  8.6 PHAS=   90.9 FOM= 0.23 TEST= 0
INDE  2  52  32 FOBS=   92.7 SIGMA=  3.7 PHAS=  141.6 FOM= 0.73 TEST= 0
INDE  2  52  34 FOBS=   79.0 SIGMA=  4.2 PHAS= -147.1 FOM= 0.80 TEST= 0
INDE  2  52  36 FOBS=   53.2 SIGMA=  6.3 PHAS=  -23.6 FOM= 0.73 TEST= 0
INDE  2  52  38 FOBS=    0.0 SIGMA= 20.6 PHAS=    0.0 FOM= 0.00 TEST= 0
INDE  2  52  40 FOBS=    0.0 SIGMA= 19.8 PHAS=    0.0 FOM= 0.00 TEST= 0
```

*FIG. 12A - 71*

| | | | | | | | | | | | |
|---|---|---|---|---|---|---|---|---|---|---|---|
| INDE | 2 | 52 | 42 | FOBS= | 41.0 | SIGMA= | 4.6 | PHAS= | 119.4 | FOM= | 0.37 | TEST= 0
| INDE | 2 | 52 | 44 | FOBS= | 36.2 | SIGMA= | 5.2 | PHAS= | -48.0 | FOM= | 0.61 | TEST= 0
| INDE | 2 | 52 | 46 | FOBS= | 36.5 | SIGMA= | 5.1 | PHAS= | -107.2 | FOM= | 0.72 | TEST= 0
| INDE | 2 | 52 | 48 | FOBS= | 30.1 | SIGMA= | 7.1 | PHAS= | -123.1 | FOM= | 0.56 | TEST= 1
| INDE | 2 | 52 | 50 | FOBS= | 55.3 | SIGMA= | 3.3 | PHAS= | -68.2 | FOM= | 0.79 | TEST= 0
| INDE | 2 | 52 | 52 | FOBS= | 61.2 | SIGMA= | 3.0 | PHAS= | 69.7 | FOM= | 0.81 | TEST= 0
| INDE | 2 | 52 | 54 | FOBS= | 37.0 | SIGMA= | 5.6 | PHAS= | 88.2 | FOM= | 0.74 | TEST= 0
| INDE | 2 | 52 | 56 | FOBS= | 0.0 | SIGMA= | 21.9 | PHAS= | 0.0 | FOM= | 0.00 | TEST= 0
| INDE | 2 | 53 | 3 | FOBS= | 249.4 | SIGMA= | 0.6 | PHAS= | 2.7 | FOM= | 0.96 | TEST= 0
| INDE | 2 | 53 | 13 | FOBS= | 87.6 | SIGMA= | 3.4 | PHAS= | -125.0 | FOM= | 0.77 | TEST= 0
| INDE | 2 | 53 | 15 | FOBS= | 82.4 | SIGMA= | 2.1 | PHAS= | -156.4 | FOM= | 0.73 | TEST= 0
| INDE | 2 | 53 | 17 | FOBS= | 156.3 | SIGMA= | 1.2 | PHAS= | 8.2 | FOM= | 0.92 | TEST= 0
| INDE | 2 | 53 | 19 | FOBS= | 153.8 | SIGMA= | 1.3 | PHAS= | -97.6 | FOM= | 0.94 | TEST= 0
| INDE | 2 | 53 | 21 | FOBS= | 89.4 | SIGMA= | 2.4 | PHAS= | 148.1 | FOM= | 0.86 | TEST= 0
| INDE | 2 | 53 | 23 | FOBS= | 96.0 | SIGMA= | 1.9 | PHAS= | 33.5 | FOM= | 0.85 | TEST= 0
| INDE | 2 | 53 | 25 | FOBS= | 127.4 | SIGMA= | 1.9 | PHAS= | -55.6 | FOM= | 0.79 | TEST= 0
| INDE | 2 | 53 | 27 | FOBS= | 43.6 | SIGMA= | 5.2 | PHAS= | 33.9 | FOM= | 0.57 | TEST= 0
| INDE | 2 | 53 | 29 | FOBS= | 151.1 | SIGMA= | 2.4 | PHAS= | -148.6 | FOM= | 0.95 | TEST= 0
| INDE | 2 | 53 | 31 | FOBS= | 71.5 | SIGMA= | 4.7 | PHAS= | 50.2 | FOM= | 0.73 | TEST= 0
| INDE | 2 | 53 | 33 | FOBS= | 76.6 | SIGMA= | 4.4 | PHAS= | 88.8 | FOM= | 0.84 | TEST= 0
| INDE | 2 | 53 | 35 | FOBS= | 133.6 | SIGMA= | 2.6 | PHAS= | 139.1 | FOM= | 0.83 | TEST= 1
| INDE | 2 | 53 | 37 | FOBS= | 117.6 | SIGMA= | 2.4 | PHAS= | -160.0 | FOM= | 0.95 | TEST= 0
| INDE | 2 | 53 | 39 | FOBS= | 11.7 | SIGMA= | 17.6 | PHAS= | -118.6 | FOM= | 0.02 | TEST= 0
| INDE | 2 | 53 | 41 | FOBS= | 30.3 | SIGMA= | 5.8 | PHAS= | 96.0 | FOM= | 0.50 | TEST= 0
| INDE | 2 | 53 | 43 | FOBS= | 112.5 | SIGMA= | 1.7 | PHAS= | 22.6 | FOM= | 0.61 | TEST= 1
| INDE | 2 | 53 | 45 | FOBS= | 84.8 | SIGMA= | 2.3 | PHAS= | -126.4 | FOM= | 0.85 | TEST= 0
| INDE | 2 | 53 | 47 | FOBS= | 32.2 | SIGMA= | 7.2 | PHAS= | -108.4 | FOM= | 0.45 | TEST= 0
| INDE | 2 | 53 | 49 | FOBS= | 49.6 | SIGMA= | 4.0 | PHAS= | -104.8 | FOM= | 0.34 | TEST= 0
| INDE | 2 | 53 | 51 | FOBS= | 0.0 | SIGMA= | 20.9 | PHAS= | 0.0 | FOM= | 0.00 | TEST= 0
| INDE | 2 | 53 | 53 | FOBS= | 0.0 | SIGMA= | 19.6 | PHAS= | 0.0 | FOM= | 0.00 | TEST= 0
| INDE | 2 | 53 | 55 | FOBS= | 0.0 | SIGMA= | 21.1 | PHAS= | 0.0 | FOM= | 0.00 | TEST= 1
| INDE | 2 | 54 | 2 | FOBS= | 67.8 | SIGMA= | 1.8 | PHAS= | -37.0 | FOM= | 0.88 | TEST= 0
| INDE | 2 | 54 | 4 | FOBS= | 113.7 | SIGMA= | 1.7 | PHAS= | 6.2 | FOM= | 0.89 | TEST= 0
| INDE | 2 | 54 | 14 | FOBS= | 184.9 | SIGMA= | 1.3 | PHAS= | 65.9 | FOM= | 0.91 | TEST= 0
| INDE | 2 | 54 | 16 | FOBS= | 56.7 | SIGMA= | 3.0 | PHAS= | 28.9 | FOM= | 0.85 | TEST= 0
| INDE | 2 | 54 | 18 | FOBS= | 108.1 | SIGMA= | 1.7 | PHAS= | -82.8 | FOM= | 0.17 | TEST= 1
| INDE | 2 | 54 | 20 | FOBS= | 145.4 | SIGMA= | 1.3 | PHAS= | 97.9 | FOM= | 0.95 | TEST= 0
| INDE | 2 | 54 | 22 | FOBS= | 54.5 | SIGMA= | 3.2 | PHAS= | 98.4 | FOM= | 0.39 | TEST= 0
| INDE | 2 | 54 | 24 | FOBS= | 129.1 | SIGMA= | 1.9 | PHAS= | -47.6 | FOM= | 0.92 | TEST= 0
| INDE | 2 | 54 | 26 | FOBS= | 89.2 | SIGMA= | 2.6 | PHAS= | -168.0 | FOM= | 0.92 | TEST= 0
| INDE | 2 | 54 | 28 | FOBS= | 111.5 | SIGMA= | 2.1 | PHAS= | 116.4 | FOM= | 0.82 | TEST= 1
| INDE | 2 | 54 | 30 | FOBS= | 0.0 | SIGMA= | 25.9 | PHAS= | 0.0 | FOM= | 0.00 | TEST= 0
| INDE | 2 | 54 | 32 | FOBS= | 56.8 | SIGMA= | 5.9 | PHAS= | -27.3 | FOM= | 0.54 | TEST= 0
| INDE | 2 | 54 | 34 | FOBS= | 42.3 | SIGMA= | 7.8 | PHAS= | -46.4 | FOM= | 0.38 | TEST= 0
| INDE | 2 | 54 | 36 | FOBS= | 87.4 | SIGMA= | 3.8 | PHAS= | -48.2 | FOM= | 0.39 | TEST= 0
| INDE | 2 | 54 | 38 | FOBS= | 74.9 | SIGMA= | 3.2 | PHAS= | 130.7 | FOM= | 0.82 | TEST= 0
| INDE | 2 | 54 | 40 | FOBS= | 46.4 | SIGMA= | 3.8 | PHAS= | 40.0 | FOM= | 0.81 | TEST= 0
| INDE | 2 | 54 | 42 | FOBS= | 90.0 | SIGMA= | 2.0 | PHAS= | -21.3 | FOM= | 0.76 | TEST= 0
| INDE | 2 | 54 | 44 | FOBS= | 0.0 | SIGMA= | 19.4 | PHAS= | 0.0 | FOM= | 0.00 | TEST= 0
| INDE | 2 | 54 | 46 | FOBS= | 63.7 | SIGMA= | 3.0 | PHAS= | 126.6 | FOM= | 0.69 | TEST= 0
| INDE | 2 | 54 | 48 | FOBS= | 0.0 | SIGMA= | 20.2 | PHAS= | 0.0 | FOM= | 0.00 | TEST= 0
| INDE | 2 | 54 | 50 | FOBS= | 0.0 | SIGMA= | 20.8 | PHAS= | 0.0 | FOM= | 0.00 | TEST= 0
| INDE | 2 | 54 | 52 | FOBS= | 0.0 | SIGMA= | 20.5 | PHAS= | 0.0 | FOM= | 0.00 | TEST= 0
| INDE | 2 | 54 | 54 | FOBS= | 48.2 | SIGMA= | 5.2 | PHAS= | 123.4 | FOM= | 0.16 | TEST= 0
| INDE | 2 | 55 | 3 | FOBS= | 127.1 | SIGMA= | 1.1 | PHAS= | -70.9 | FOM= | 0.89 | TEST= 0
| INDE | 2 | 55 | 15 | FOBS= | 40.7 | SIGMA= | 4.1 | PHAS= | -137.9 | FOM= | 0.23 | TEST= 0
| INDE | 2 | 55 | 17 | FOBS= | 0.0 | SIGMA= | 18.6 | PHAS= | 0.0 | FOM= | 0.00 | TEST= 0
| INDE | 2 | 55 | 19 | FOBS= | 26.5 | SIGMA= | 8.0 | PHAS= | -130.9 | FOM= | 0.26 | TEST= 0
| INDE | 2 | 55 | 21 | FOBS= | 86.9 | SIGMA= | 2.0 | PHAS= | -116.0 | FOM= | 0.84 | TEST= 0
| INDE | 2 | 55 | 23 | FOBS= | 74.8 | SIGMA= | 2.4 | PHAS= | -10.6 | FOM= | 0.64 | TEST= 0
| INDE | 2 | 55 | 25 | FOBS= | 0.0 | SIGMA= | 22.9 | PHAS= | 0.0 | FOM= | 0.00 | TEST= 0
| INDE | 2 | 55 | 27 | FOBS= | 127.9 | SIGMA= | 1.9 | PHAS= | 115.7 | FOM= | 0.95 | TEST= 0
| INDE | 2 | 55 | 29 | FOBS= | 40.3 | SIGMA= | 5.6 | PHAS= | -93.3 | FOM= | 0.55 | TEST= 0
| INDE | 2 | 55 | 31 | FOBS= | 27.6 | SIGMA= | 12.0 | PHAS= | 12.5 | FOM= | 0.14 | TEST= 0
| INDE | 2 | 55 | 33 | FOBS= | 86.8 | SIGMA= | 4.0 | PHAS= | 169.9 | FOM= | 0.49 | TEST= 0
| INDE | 2 | 55 | 35 | FOBS= | 65.3 | SIGMA= | 5.1 | PHAS= | 121.0 | FOM= | 0.78 | TEST= 0
| INDE | 2 | 55 | 37 | FOBS= | 117.7 | SIGMA= | 2.4 | PHAS= | 164.8 | FOM= | 0.91 | TEST= 0
| INDE | 2 | 55 | 39 | FOBS= | 31.7 | SIGMA= | 7.3 | PHAS= | -79.1 | FOM= | 0.51 | TEST= 0
| INDE | 2 | 55 | 41 | FOBS= | 97.4 | SIGMA= | 1.9 | PHAS= | 64.9 | FOM= | 0.51 | TEST= 0
| INDE | 2 | 55 | 43 | FOBS= | 0.0 | SIGMA= | 20.2 | PHAS= | 0.0 | FOM= | 0.00 | TEST= 0

*FIG. 12A - 72*

```
INDE 2 55 45 FOBS=   33.5 SIGMA=  5.6 PHAS= -100.0 FOM= 0.66 TEST= 0
INDE 2 55 47 FOBS=   29.5 SIGMA=  7.4 PHAS= -173.5 FOM= 0.17 TEST= 1
INDE 2 55 49 FOBS=   27.5 SIGMA=  7.9 PHAS=  175.1 FOM= 0.08 TEST= 0
INDE 2 55 51 FOBS=   47.8 SIGMA=  4.3 PHAS=  122.2 FOM= 0.63 TEST= 0
INDE 2 55 53 FOBS=    0.0 SIGMA= 25.1 PHAS=    0.0 FOM= 0.00 TEST= 0
INDE 2 56  2 FOBS=   73.3 SIGMA=  3.1 PHAS= -142.4 FOM= 0.32 TEST= 0
INDE 2 56  4 FOBS=   84.1 SIGMA=  2.0 PHAS=  -34.3 FOM= 0.95 TEST= 0
INDE 2 56 16 FOBS=   78.1 SIGMA=  2.2 PHAS=  -98.4 FOM= 0.72 TEST= 0
INDE 2 56 18 FOBS=   50.3 SIGMA=  3.5 PHAS=  -47.2 FOM= 0.10 TEST= 0
INDE 2 56 20 FOBS=  129.2 SIGMA=  1.4 PHAS=   96.0 FOM= 0.94 TEST= 0
INDE 2 56 22 FOBS=   94.7 SIGMA=  1.8 PHAS=  134.8 FOM= 0.65 TEST= 0
INDE 2 56 24 FOBS=   34.3 SIGMA=  5.5 PHAS=  151.5 FOM= 0.26 TEST= 0
INDE 2 56 26 FOBS=  149.6 SIGMA=  1.7 PHAS=  131.4 FOM= 0.95 TEST= 0
INDE 2 56 28 FOBS=   70.8 SIGMA=  3.3 PHAS=  -20.0 FOM= 0.66 TEST= 0
INDE 2 56 30 FOBS=   55.8 SIGMA=  4.1 PHAS=  -81.6 FOM= 0.54 TEST= 1
INDE 2 56 32 FOBS=   74.5 SIGMA=  4.6 PHAS=   27.4 FOM= 0.67 TEST= 0
INDE 2 56 34 FOBS=    0.0 SIGMA= 25.7 PHAS=    0.0 FOM= 0.00 TEST= 0
INDE 2 56 36 FOBS=   68.8 SIGMA=  3.9 PHAS=  132.6 FOM= 0.32 TEST= 0
INDE 2 56 38 FOBS=   45.1 SIGMA=  5.2 PHAS=  166.2 FOM= 0.49 TEST= 0
INDE 2 56 40 FOBS=   15.7 SIGMA= 12.7 PHAS=  -80.8 FOM= 0.71 TEST= 0
INDE 2 56 42 FOBS=   55.9 SIGMA=  3.2 PHAS=   66.4 FOM= 0.48 TEST= 0
INDE 2 56 44 FOBS=   66.1 SIGMA=  2.9 PHAS=  168.6 FOM= 0.81 TEST= 0
INDE 2 56 46 FOBS=   23.4 SIGMA= 10.2 PHAS=    1.3 FOM= 0.21 TEST= 0
INDE 2 56 48 FOBS=   30.0 SIGMA=  7.9 PHAS=   98.3 FOM= 0.14 TEST= 1
INDE 2 56 50 FOBS=    0.0 SIGMA= 21.0 PHAS=    0.0 FOM= 0.00 TEST= 0
INDE 2 56 52 FOBS=    0.0 SIGMA= 25.2 PHAS=    0.0 FOM= 0.00 TEST= 0
INDE 2 57  3 FOBS=  137.7 SIGMA=  1.0 PHAS=  -96.9 FOM= 0.85 TEST= 0
INDE 2 57  5 FOBS=  253.3 SIGMA=  0.9 PHAS=   52.5 FOM= 0.94 TEST= 0
INDE 2 57 15 FOBS=  170.7 SIGMA=  1.4 PHAS= -114.0 FOM= 0.86 TEST= 1
INDE 2 57 17 FOBS=   92.6 SIGMA=  1.9 PHAS=  136.9 FOM= 0.76 TEST= 0
INDE 2 57 19 FOBS=   81.8 SIGMA=  2.1 PHAS=   13.7 FOM= 0.55 TEST= 1
INDE 2 57 21 FOBS=    0.0 SIGMA= 18.1 PHAS=    0.0 FOM= 0.00 TEST= 1
INDE 2 57 23 FOBS=  126.4 SIGMA=  1.4 PHAS=   60.0 FOM= 0.95 TEST= 0
INDE 2 57 25 FOBS=  144.0 SIGMA=  1.3 PHAS=   36.5 FOM= 0.95 TEST= 0
INDE 2 57 27 FOBS=   86.8 SIGMA=  2.7 PHAS=  143.7 FOM= 0.57 TEST= 0
INDE 2 57 29 FOBS=   56.8 SIGMA=  4.1 PHAS=  109.3 FOM= 0.40 TEST= 0
INDE 2 57 31 FOBS=   23.4 SIGMA=  9.7 PHAS= -104.5 FOM= 0.16 TEST= 0
INDE 2 57 33 FOBS=   75.0 SIGMA=  4.5 PHAS=  134.5 FOM= 0.81 TEST= 0
INDE 2 57 35 FOBS=   35.7 SIGMA=  9.3 PHAS=  130.6 FOM= 0.30 TEST= 0
INDE 2 57 37 FOBS=   42.8 SIGMA=  5.5 PHAS=  140.0 FOM= 0.37 TEST= 0
INDE 2 57 39 FOBS=   95.4 SIGMA=  2.5 PHAS= -169.9 FOM= 0.89 TEST= 0
INDE 2 57 41 FOBS=   35.3 SIGMA=  5.6 PHAS=  124.7 FOM= 0.61 TEST= 1
INDE 2 57 43 FOBS=   15.3 SIGMA= 14.0 PHAS=  163.0 FOM= 0.19 TEST= 0
INDE 2 57 45 FOBS=   47.8 SIGMA=  4.0 PHAS=  -67.1 FOM= 0.41 TEST= 0
INDE 2 57 47 FOBS=   37.3 SIGMA=  6.5 PHAS= -166.9 FOM= 0.63 TEST= 0
INDE 2 57 49 FOBS=   43.6 SIGMA=  5.0 PHAS=  -36.8 FOM= 0.22 TEST= 0
INDE 2 57 51 FOBS=   59.0 SIGMA=  5.5 PHAS= -132.7 FOM= 0.77 TEST= 0
INDE 2 58  2 FOBS=  116.8 SIGMA=  1.9 PHAS=  136.8 FOM= 0.83 TEST= 0
INDE 2 58  4 FOBS=   97.1 SIGMA=  1.4 PHAS=  -51.2 FOM= 0.91 TEST= 0
INDE 2 58 16 FOBS=   40.8 SIGMA=  5.4 PHAS= -162.1 FOM= 0.48 TEST= 0
INDE 2 58 18 FOBS=  117.3 SIGMA=  1.4 PHAS=  -25.7 FOM= 0.92 TEST= 0
INDE 2 58 20 FOBS=   23.5 SIGMA=  6.8 PHAS=  -49.5 FOM= 0.78 TEST= 0
INDE 2 58 22 FOBS=   93.5 SIGMA=  1.8 PHAS=   56.8 FOM= 0.87 TEST= 0
INDE 2 58 24 FOBS=   91.6 SIGMA=  2.0 PHAS=  -20.2 FOM= 0.94 TEST= 0
INDE 2 58 26 FOBS=   44.1 SIGMA=  4.0 PHAS= -103.6 FOM= 0.75 TEST= 0
INDE 2 58 28 FOBS=   37.2 SIGMA=  7.4 PHAS=  -66.0 FOM= 0.27 TEST= 0
INDE 2 58 30 FOBS=    0.0 SIGMA= 21.3 PHAS=    0.0 FOM= 0.00 TEST= 0
INDE 2 58 32 FOBS=   72.2 SIGMA=  3.2 PHAS=  -51.4 FOM= 0.59 TEST= 0
INDE 2 58 34 FOBS=   47.9 SIGMA=  7.0 PHAS=  -13.1 FOM= 0.49 TEST= 0
INDE 2 58 36 FOBS=   34.4 SIGMA=  7.8 PHAS=  151.1 FOM= 0.68 TEST= 0
INDE 2 58 38 FOBS=   43.7 SIGMA=  5.5 PHAS=  106.6 FOM= 0.22 TEST= 0
INDE 2 58 40 FOBS=   65.3 SIGMA=  3.7 PHAS=  -20.3 FOM= 0.61 TEST= 0
INDE 2 58 42 FOBS=   67.6 SIGMA=  2.7 PHAS=   79.9 FOM= 0.88 TEST= 0
INDE 2 58 44 FOBS=   18.6 SIGMA= 10.9 PHAS=  135.3 FOM= 0.42 TEST= 0
INDE 2 58 46 FOBS=    0.0 SIGMA= 21.8 PHAS=    0.0 FOM= 0.00 TEST= 0
INDE 2 58 48 FOBS=    0.0 SIGMA= 22.6 PHAS=    0.0 FOM= 0.00 TEST= 0
INDE 2 58 50 FOBS=    6.9 SIGMA= 47.6 PHAS=  144.2 FOM= 0.44 TEST= 0
INDE 2 59  3 FOBS=  158.9 SIGMA=  1.1 PHAS=  -91.4 FOM= 0.57 TEST= 1
INDE 2 59  5 FOBS=    0.0 SIGMA= 18.9 PHAS=    0.0 FOM= 0.00 TEST= 0
INDE 2 59 17 FOBS=   30.3 SIGMA=  5.4 PHAS= -116.1 FOM= 0.62 TEST= 1
```

*FIG. 12A - 73*

| | | | | | | | | | | | |
|---|---|---|---|---|---|---|---|---|---|---|---|
| INDE | 2 | 59 | 19 | FOBS= | 66.2 | SIGMA= | 2.4 | PHAS= | -102.9 | FOM= | 0.87 | TEST= 0
| INDE | 2 | 59 | 21 | FOBS= | 20.2 | SIGMA= | 8.9 | PHAS= | 152.0 | FOM= | 0.23 | TEST= 1
| INDE | 2 | 59 | 23 | FOBS= | 45.9 | SIGMA= | 3.7 | PHAS= | 65.9 | FOM= | 0.74 | TEST= 0
| INDE | 2 | 59 | 25 | FOBS= | 66.7 | SIGMA= | 3.0 | PHAS= | 121.3 | FOM= | 0.46 | TEST= 1
| INDE | 2 | 59 | 27 | FOBS= | 54.3 | SIGMA= | 3.7 | PHAS= | 160.3 | FOM= | 0.71 | TEST= 0
| INDE | 2 | 59 | 29 | FOBS= | 59.7 | SIGMA= | 3.9 | PHAS= | -50.7 | FOM= | 0.59 | TEST= 0
| INDE | 2 | 59 | 31 | FOBS= | 21.9 | SIGMA= | 11.9 | PHAS= | 77.4 | FOM= | 0.18 | TEST= 0
| INDE | 2 | 59 | 33 | FOBS= | 42.7 | SIGMA= | 7.3 | PHAS= | 10.9 | FOM= | 0.46 | TEST= 0
| INDE | 2 | 59 | 35 | FOBS= | 19.3 | SIGMA= | 13.9 | PHAS= | -6.4 | FOM= | 0.12 | TEST= 0
| INDE | 2 | 59 | 37 | FOBS= | 72.8 | SIGMA= | 3.3 | PHAS= | 24.0 | FOM= | 0.77 | TEST= 0
| INDE | 2 | 59 | 39 | FOBS= | 108.7 | SIGMA= | 2.3 | PHAS= | -173.2 | FOM= | 0.92 | TEST= 0
| INDE | 2 | 59 | 41 | FOBS= | 40.7 | SIGMA= | 5.8 | PHAS= | 46.5 | FOM= | 0.76 | TEST= 0
| INDE | 2 | 59 | 43 | FOBS= | 0.0 | SIGMA= | 20.1 | PHAS= | 0.0 | FOM= | 0.00 | TEST= 0
| INDE | 2 | 59 | 45 | FOBS= | 49.9 | SIGMA= | 4.8 | PHAS= | 91.6 | FOM= | 0.35 | TEST= 0
| INDE | 2 | 59 | 47 | FOBS= | 36.3 | SIGMA= | 7.9 | PHAS= | 63.6 | FOM= | 0.52 | TEST= 0
| INDE | 2 | 59 | 49 | FOBS= | 0.0 | SIGMA= | 25.5 | PHAS= | 0.0 | FOM= | 0.00 | TEST= 0
| INDE | 2 | 60 | 2 | FOBS= | 129.7 | SIGMA= | 1.7 | PHAS= | -36.4 | FOM= | 0.90 | TEST= 0
| INDE | 2 | 60 | 4 | FOBS= | 70.2 | SIGMA= | 1.8 | PHAS= | -34.8 | FOM= | 0.50 | TEST= 1
| INDE | 2 | 60 | 6 | FOBS= | 90.3 | SIGMA= | 2.1 | PHAS= | 145.3 | FOM= | 0.42 | TEST= 0
| INDE | 2 | 60 | 18 | FOBS= | 21.6 | SIGMA= | 12.4 | PHAS= | 30.3 | FOM= | 0.35 | TEST= 0
| INDE | 2 | 60 | 20 | FOBS= | 0.0 | SIGMA= | 22.4 | PHAS= | 0.0 | FOM= | 0.00 | TEST= 0
| INDE | 2 | 60 | 22 | FOBS= | 111.7 | SIGMA= | 2.0 | PHAS= | -47.6 | FOM= | 0.83 | TEST= 0
| INDE | 2 | 60 | 24 | FOBS= | 25.0 | SIGMA= | 9.7 | PHAS= | -52.2 | FOM= | 0.12 | TEST= 0
| INDE | 2 | 60 | 26 | FOBS= | 62.1 | SIGMA= | 3.7 | PHAS= | -30.5 | FOM= | 0.87 | TEST= 0
| INDE | 2 | 60 | 28 | FOBS= | 0.0 | SIGMA= | 23.2 | PHAS= | 0.0 | FOM= | 0.00 | TEST= 0
| INDE | 2 | 60 | 30 | FOBS= | 45.7 | SIGMA= | 6.1 | PHAS= | -122.9 | FOM= | 0.10 | TEST= 1
| INDE | 2 | 60 | 32 | FOBS= | 76.3 | SIGMA= | 3.7 | PHAS= | -78.5 | FOM= | 0.83 | TEST= 0
| INDE | 2 | 60 | 34 | FOBS= | 31.9 | SIGMA= | 10.6 | PHAS= | -52.5 | FOM= | 0.65 | TEST= 0
| INDE | 2 | 60 | 36 | FOBS= | 46.8 | SIGMA= | 5.2 | PHAS= | 166.5 | FOM= | 0.60 | TEST= 0
| INDE | 2 | 60 | 38 | FOBS= | 38.8 | SIGMA= | 6.2 | PHAS= | 104.2 | FOM= | 0.69 | TEST= 0
| INDE | 2 | 60 | 40 | FOBS= | 0.0 | SIGMA= | 21.7 | PHAS= | 0.0 | FOM= | 0.00 | TEST= 0
| INDE | 2 | 60 | 42 | FOBS= | 13.4 | SIGMA= | 17.7 | PHAS= | -107.0 | FOM= | 0.12 | TEST= 0
| INDE | 2 | 60 | 44 | FOBS= | 64.3 | SIGMA= | 3.0 | PHAS= | 52.8 | FOM= | 0.85 | TEST= 0
| INDE | 2 | 60 | 46 | FOBS= | 102.0 | SIGMA= | 3.0 | PHAS= | -72.6 | FOM= | 0.89 | TEST= 0
| INDE | 2 | 60 | 48 | FOBS= | 45.6 | SIGMA= | 7.4 | PHAS= | -56.8 | FOM= | 0.48 | TEST= 0
| INDE | 2 | 61 | 3 | FOBS= | 192.9 | SIGMA= | 1.2 | PHAS= | -92.5 | FOM= | 0.93 | TEST= 0
| INDE | 2 | 61 | 5 | FOBS= | 32.5 | SIGMA= | 4.0 | PHAS= | 70.1 | FOM= | 0.53 | TEST= 0
| INDE | 2 | 61 | 17 | FOBS= | 21.0 | SIGMA= | 12.3 | PHAS= | -133.6 | FOM= | 0.53 | TEST= 0
| INDE | 2 | 61 | 19 | FOBS= | 30.1 | SIGMA= | 6.6 | PHAS= | 154.6 | FOM= | 0.45 | TEST= 0
| INDE | 2 | 61 | 21 | FOBS= | 68.0 | SIGMA= | 3.1 | PHAS= | 10.9 | FOM= | 0.12 | TEST= 1
| INDE | 2 | 61 | 23 | FOBS= | 106.3 | SIGMA= | 2.1 | PHAS= | 166.2 | FOM= | 0.94 | TEST= 0
| INDE | 2 | 61 | 25 | FOBS= | 142.8 | SIGMA= | 1.7 | PHAS= | 174.3 | FOM= | 0.95 | TEST= 0
| INDE | 2 | 61 | 27 | FOBS= | 51.6 | SIGMA= | 4.5 | PHAS= | -179.8 | FOM= | 0.77 | TEST= 0
| INDE | 2 | 61 | 29 | FOBS= | 17.1 | SIGMA= | 15.3 | PHAS= | -61.2 | FOM= | 0.26 | TEST= 0
| INDE | 2 | 61 | 31 | FOBS= | 83.1 | SIGMA= | 3.5 | PHAS= | 157.3 | FOM= | 0.90 | TEST= 0
| INDE | 2 | 61 | 33 | FOBS= | 79.6 | SIGMA= | 3.6 | PHAS= | -80.5 | FOM= | 0.86 | TEST= 0
| INDE | 2 | 61 | 35 | FOBS= | 0.0 | SIGMA= | 26.0 | PHAS= | 0.0 | FOM= | 0.00 | TEST= 1
| INDE | 2 | 61 | 37 | FOBS= | 95.2 | SIGMA= | 2.6 | PHAS= | 37.3 | FOM= | 0.91 | TEST= 0
| INDE | 2 | 61 | 39 | FOBS= | 19.1 | SIGMA= | 12.5 | PHAS= | -108.9 | FOM= | 0.16 | TEST= 0
| INDE | 2 | 61 | 41 | FOBS= | 36.5 | SIGMA= | 7.6 | PHAS= | -157.5 | FOM= | 0.69 | TEST= 0
| INDE | 2 | 61 | 43 | FOBS= | 37.8 | SIGMA= | 5.5 | PHAS= | -31.7 | FOM= | 0.14 | TEST= 1
| INDE | 2 | 61 | 45 | FOBS= | 32.5 | SIGMA= | 10.7 | PHAS= | -126.1 | FOM= | 0.53 | TEST= 0
| INDE | 2 | 61 | 47 | FOBS= | 60.4 | SIGMA= | 5.7 | PHAS= | 127.5 | FOM= | 0.83 | TEST= 0
| INDE | 2 | 62 | 2 | FOBS= | 126.0 | SIGMA= | 2.6 | PHAS= | -146.3 | FOM= | 0.87 | TEST= 0
| INDE | 2 | 62 | 4 | FOBS= | 133.8 | SIGMA= | 1.5 | PHAS= | 171.4 | FOM= | 0.95 | TEST= 0
| INDE | 2 | 62 | 6 | FOBS= | 39.3 | SIGMA= | 7.0 | PHAS= | -173.4 | FOM= | 0.51 | TEST= 0
| INDE | 2 | 62 | 16 | FOBS= | 90.7 | SIGMA= | 5.4 | PHAS= | -62.3 | FOM= | 0.77 | TEST= 0
| INDE | 2 | 62 | 18 | FOBS= | 88.7 | SIGMA= | 2.7 | PHAS= | 41.8 | FOM= | 0.92 | TEST= 0
| INDE | 2 | 62 | 20 | FOBS= | 38.2 | SIGMA= | 5.3 | PHAS= | 48.7 | FOM= | 0.91 | TEST= 0
| INDE | 2 | 62 | 22 | FOBS= | 115.4 | SIGMA= | 1.9 | PHAS= | 54.1 | FOM= | 0.91 | TEST= 0
| INDE | 2 | 62 | 24 | FOBS= | 154.4 | SIGMA= | 1.5 | PHAS= | 104.0 | FOM= | 0.97 | TEST= 0
| INDE | 2 | 62 | 26 | FOBS= | 117.2 | SIGMA= | 2.0 | PHAS= | 38.9 | FOM= | 0.94 | TEST= 0
| INDE | 2 | 62 | 28 | FOBS= | 63.1 | SIGMA= | 3.8 | PHAS= | -91.6 | FOM= | 0.39 | TEST= 0
| INDE | 2 | 62 | 30 | FOBS= | 110.8 | SIGMA= | 2.2 | PHAS= | -78.5 | FOM= | 0.11 | TEST= 1
| INDE | 2 | 62 | 32 | FOBS= | 73.8 | SIGMA= | 3.9 | PHAS= | 14.3 | FOM= | 0.31 | TEST= 1
| INDE | 2 | 62 | 34 | FOBS= | 30.9 | SIGMA= | 7.8 | PHAS= | -26.4 | FOM= | 0.63 | TEST= 0
| INDE | 2 | 62 | 36 | FOBS= | 0.0 | SIGMA= | 23.8 | PHAS= | 0.0 | FOM= | 0.00 | TEST= 0
| INDE | 2 | 62 | 38 | FOBS= | 48.2 | SIGMA= | 5.1 | PHAS= | -45.9 | FOM= | 0.23 | TEST= 0
| INDE | 2 | 62 | 40 | FOBS= | 62.4 | SIGMA= | 4.0 | PHAS= | 136.1 | FOM= | 0.82 | TEST= 0
| INDE | 2 | 62 | 42 | FOBS= | 0.0 | SIGMA= | 26.4 | PHAS= | 0.0 | FOM= | 0.00 | TEST= 0

*FIG. 12A - 74*

```
INDE  2  62  44  FOBS=   95.8  SIGMA=   3.8  PHAS=   76.8  FOM=  0.45  TEST= 1
INDE  2  62  46  FOBS=    0.0  SIGMA=  26.3  PHAS=    0.0  FOM=  0.00  TEST= 0
INDE  2  63   3  FOBS=   70.9  SIGMA=   4.3  PHAS=   58.8  FOM=  0.77  TEST= 0
INDE  2  63   5  FOBS=   99.9  SIGMA=   1.9  PHAS=   73.5  FOM=  0.93  TEST= 0
INDE  2  63  15  FOBS=    0.0  SIGMA=  30.8  PHAS=    0.0  FOM=  0.00  TEST= 0
INDE  2  63  17  FOBS=  113.6  SIGMA=   3.2  PHAS=  -41.3  FOM=  0.86  TEST= 0
INDE  2  63  19  FOBS=   18.9  SIGMA=  10.1  PHAS=   -6.0  FOM=  0.54  TEST= 0
INDE  2  63  21  FOBS=   78.9  SIGMA=   2.7  PHAS=  156.5  FOM=  0.63  TEST= 0
INDE  2  63  23  FOBS=   31.0  SIGMA=   6.9  PHAS=  -89.8  FOM=  0.49  TEST= 0
INDE  2  63  25  FOBS=   55.3  SIGMA=   4.0  PHAS=   -8.4  FOM=  0.81  TEST= 0
INDE  2  63  27  FOBS=    0.0  SIGMA=  25.2  PHAS=    0.0  FOM=  0.00  TEST= 0
INDE  2  63  29  FOBS=   52.5  SIGMA=   4.6  PHAS=   -7.6  FOM=  0.63  TEST= 0
INDE  2  63  31  FOBS=  106.1  SIGMA=   2.3  PHAS=  -74.6  FOM=  0.89  TEST= 0
INDE  2  63  33  FOBS=   27.8  SIGMA=   8.8  PHAS=   73.2  FOM=  0.11  TEST= 0
INDE  2  63  35  FOBS=   67.2  SIGMA=   3.3  PHAS=  -88.8  FOM=  0.73  TEST= 0
INDE  2  63  37  FOBS=    0.0  SIGMA=  22.1  PHAS=    0.0  FOM=  0.00  TEST= 0
INDE  2  63  39  FOBS=   69.2  SIGMA=   3.6  PHAS=   -9.5  FOM=  0.86  TEST= 0
INDE  2  63  41  FOBS=   14.0  SIGMA=  17.6  PHAS= -113.8  FOM=  0.08  TEST= 0
INDE  2  63  43  FOBS=   83.8  SIGMA=   3.1  PHAS=   39.9  FOM=  0.89  TEST= 0
INDE  2  63  45  FOBS=   66.4  SIGMA=   5.4  PHAS=  -16.1  FOM=  0.81  TEST= 0
INDE  2  64   2  FOBS=   69.3  SIGMA=   4.4  PHAS= -178.7  FOM=  0.38  TEST= 0
INDE  2  64   4  FOBS=   67.3  SIGMA=   4.7  PHAS=   83.8  FOM=  0.45  TEST= 0
INDE  2  64   6  FOBS=    0.0  SIGMA=  19.6  PHAS=    0.0  FOM=  0.00  TEST= 1
INDE  2  64  14  FOBS=   15.7  SIGMA=  31.0  PHAS= -123.2  FOM=  0.13  TEST= 0
INDE  2  64  16  FOBS=  134.2  SIGMA=   2.8  PHAS=  154.9  FOM=  0.01  TEST= 1
INDE  2  64  18  FOBS=   67.1  SIGMA=   5.3  PHAS=   84.6  FOM=  0.27  TEST= 1
INDE  2  64  20  FOBS=   50.5  SIGMA=   3.9  PHAS=   65.7  FOM=  0.70  TEST= 0
INDE  2  64  22  FOBS=   24.1  SIGMA=   8.7  PHAS=   25.2  FOM=  0.50  TEST= 0
INDE  2  64  24  FOBS=   45.9  SIGMA=   4.8  PHAS=  178.9  FOM=  0.56  TEST= 0
INDE  2  64  26  FOBS=   31.1  SIGMA=   7.1  PHAS=  -59.4  FOM=  0.37  TEST= 0
INDE  2  64  28  FOBS=   75.7  SIGMA=   3.7  PHAS=  107.9  FOM=  0.47  TEST= 1
INDE  2  64  30  FOBS=   27.8  SIGMA=   8.7  PHAS=  106.3  FOM=  0.47  TEST= 0
INDE  2  64  32  FOBS=   51.2  SIGMA=   4.7  PHAS=   -4.5  FOM=  0.78  TEST= 0
INDE  2  64  34  FOBS=   53.5  SIGMA=   4.2  PHAS=  -89.5  FOM=  0.02  TEST= 1
INDE  2  64  36  FOBS=   34.3  SIGMA=   6.5  PHAS=  124.5  FOM=  0.47  TEST= 0
INDE  2  64  38  FOBS=   30.8  SIGMA=   9.2  PHAS= -122.2  FOM=  0.51  TEST= 0
INDE  2  64  40  FOBS=    0.0  SIGMA=  22.3  PHAS=    0.0  FOM=  0.00  TEST= 1
INDE  2  64  42  FOBS=   88.8  SIGMA=   2.9  PHAS=  -80.5  FOM=  0.89  TEST= 0
INDE  2  64  44  FOBS=   61.1  SIGMA=   5.9  PHAS=  -59.3  FOM=  0.72  TEST= 0
INDE  2  65   5  FOBS=    0.0  SIGMA=  19.8  PHAS=    0.0  FOM=  0.00  TEST= 0
INDE  2  65   7  FOBS=   39.4  SIGMA=   7.1  PHAS=   33.9  FOM=  0.25  TEST= 0
INDE  2  65  13  FOBS=   35.1  SIGMA=  14.0  PHAS= -178.4  FOM=  0.05  TEST= 0
INDE  2  65  15  FOBS=  119.9  SIGMA=   3.1  PHAS=  104.2  FOM=  0.10  TEST= 1
INDE  2  65  17  FOBS=   57.3  SIGMA=   6.2  PHAS= -119.2  FOM=  0.43  TEST= 0
INDE  2  65  19  FOBS=    0.0  SIGMA=  22.7  PHAS=    0.0  FOM=  0.00  TEST= 0
INDE  2  65  21  FOBS=   31.4  SIGMA=   6.4  PHAS=   48.0  FOM=  0.29  TEST= 0
INDE  2  65  23  FOBS=   31.0  SIGMA=   6.9  PHAS=  138.5  FOM=  0.24  TEST= 1
INDE  2  65  25  FOBS=   59.2  SIGMA=   3.8  PHAS=  102.8  FOM=  0.30  TEST= 0
INDE  2  65  27  FOBS=   44.5  SIGMA=   5.1  PHAS=   44.5  FOM=  0.72  TEST= 0
INDE  2  65  29  FOBS=   47.0  SIGMA=   5.8  PHAS= -159.2  FOM=  0.21  TEST= 1
INDE  2  65  31  FOBS=   93.8  SIGMA=   2.7  PHAS=  -41.1  FOM=  0.93  TEST= 0
INDE  2  65  33  FOBS=   87.0  SIGMA=   2.6  PHAS=   16.4  FOM=  0.87  TEST= 0
INDE  2  65  35  FOBS=    3.9  SIGMA=  57.6  PHAS=   -8.0  FOM=  0.03  TEST= 0
INDE  2  65  37  FOBS=   53.7  SIGMA=   4.2  PHAS=   89.5  FOM=  0.85  TEST= 0
INDE  2  65  39  FOBS=   70.3  SIGMA=   3.3  PHAS= -178.7  FOM=  0.75  TEST= 0
INDE  2  65  41  FOBS=    0.0  SIGMA=  22.6  PHAS=    0.0  FOM=  0.00  TEST= 0
INDE  2  66   2  FOBS=  117.1  SIGMA=   2.7  PHAS=  141.2  FOM=  0.92  TEST= 0
INDE  2  66   4  FOBS=   29.1  SIGMA=  10.1  PHAS=  151.4  FOM=  0.57  TEST= 0
INDE  2  66   6  FOBS=    0.0  SIGMA=  19.2  PHAS=    0.0  FOM=  0.00  TEST= 0
INDE  2  66  12  FOBS=  111.7  SIGMA=   4.6  PHAS= -120.4  FOM=  0.86  TEST= 0
INDE  2  66  14  FOBS=   70.0  SIGMA=   7.1  PHAS=  -33.2  FOM=  0.54  TEST= 0
INDE  2  66  16  FOBS=   74.1  SIGMA=   4.8  PHAS=   76.8  FOM=  0.73  TEST= 0
INDE  2  66  18  FOBS=  104.6  SIGMA=   3.5  PHAS=  106.8  FOM=  0.28  TEST= 1
INDE  2  66  20  FOBS=   17.5  SIGMA=  13.2  PHAS=  172.9  FOM=  0.11  TEST= 0
INDE  2  66  22  FOBS=   66.3  SIGMA=   3.1  PHAS= -119.4  FOM=  0.63  TEST= 1
INDE  2  66  24  FOBS=   46.9  SIGMA=   4.6  PHAS=  135.7  FOM=  0.55  TEST= 0
INDE  2  66  26  FOBS=   17.9  SIGMA=  12.6  PHAS= -131.1  FOM=  0.29  TEST= 0
INDE  2  66  28  FOBS=    0.0  SIGMA=  22.7  PHAS=    0.0  FOM=  0.00  TEST= 0
INDE  2  66  30  FOBS=   50.0  SIGMA=   5.6  PHAS=    1.3  FOM=  0.84  TEST= 0
INDE  2  66  32  FOBS=   21.7  SIGMA=  10.2  PHAS=  -79.0  FOM=  0.49  TEST= 0
```

*FIG. 12A - 75*

```
INDE  2  66  34  FOBS=    0.0  SIGMA=  22.2  PHAS=    0.0  FOM=  0.00  TEST=  0
INDE  2  66  36  FOBS=   25.6  SIGMA=  10.1  PHAS= -136.3  FOM=  0.01  TEST=  1
INDE  2  66  38  FOBS=   59.1  SIGMA=   3.9  PHAS=   94.5  FOM=  0.66  TEST=  0
INDE  2  66  40  FOBS=   36.3  SIGMA=   6.5  PHAS=  -78.7  FOM=  0.36  TEST=  1
INDE  2  67   3  FOBS=   73.6  SIGMA=   4.2  PHAS=    1.7  FOM=  0.12  TEST=  1
INDE  2  67   5  FOBS=   39.0  SIGMA=   8.1  PHAS=   46.7  FOM=  0.36  TEST=  0
INDE  2  67   7  FOBS=   83.9  SIGMA=   2.5  PHAS=  -21.0  FOM=  0.43  TEST=  0
INDE  2  67  11  FOBS=    0.0  SIGMA=  31.2  PHAS=    0.0  FOM=  0.00  TEST=  0
INDE  2  67  13  FOBS=   98.6  SIGMA=   5.2  PHAS= -179.5  FOM=  0.90  TEST=  0
INDE  2  67  15  FOBS=   50.9  SIGMA=   7.0  PHAS=  137.7  FOM=  0.34  TEST=  0
INDE  2  67  17  FOBS=   34.8  SIGMA=  10.1  PHAS=   28.0  FOM=  0.40  TEST=  0
INDE  2  67  19  FOBS=   30.8  SIGMA=  11.4  PHAS=   92.4  FOM=  0.12  TEST=  0
INDE  2  67  21  FOBS=   29.9  SIGMA=   6.6  PHAS=   88.7  FOM=  0.53  TEST=  1
INDE  2  67  23  FOBS=   29.2  SIGMA=   7.2  PHAS=   78.6  FOM=  0.77  TEST=  0
INDE  2  67  25  FOBS=   61.4  SIGMA=   3.7  PHAS=   76.2  FOM=  0.28  TEST=  0
INDE  2  67  27  FOBS=   62.5  SIGMA=   3.7  PHAS=   95.7  FOM=  0.89  TEST=  0
INDE  2  67  29  FOBS=    0.0  SIGMA=  21.7  PHAS=    0.0  FOM=  0.00  TEST=  0
INDE  2  67  31  FOBS=   80.2  SIGMA=   3.1  PHAS=  -59.1  FOM=  0.94  TEST=  0
INDE  2  67  33  FOBS=   51.1  SIGMA=   4.1  PHAS=   13.3  FOM=  0.74  TEST=  0
INDE  2  67  35  FOBS=   43.5  SIGMA=   6.0  PHAS= -130.2  FOM=  0.70  TEST=  0
INDE  2  67  37  FOBS=   71.7  SIGMA=   3.3  PHAS=   75.7  FOM=  0.88  TEST=  0
INDE  2  67  39  FOBS=   18.0  SIGMA=  14.8  PHAS= -163.1  FOM=  0.23  TEST=  0
INDE  2  68   4  FOBS=   95.8  SIGMA=   3.2  PHAS= -155.8  FOM=  0.74  TEST=  0
INDE  2  68   6  FOBS=  102.3  SIGMA=   2.0  PHAS=  -58.3  FOM=  0.95  TEST=  0
INDE  2  68   8  FOBS=   59.9  SIGMA=   4.8  PHAS=  -53.4  FOM=  0.75  TEST=  0
INDE  2  68  14  FOBS=   44.1  SIGMA=   8.0  PHAS=   51.6  FOM=  0.17  TEST=  0
INDE  2  68  16  FOBS=   66.8  SIGMA=   5.3  PHAS=  131.1  FOM=  0.49  TEST=  0
INDE  2  68  18  FOBS=   59.0  SIGMA=   6.1  PHAS=   81.2  FOM=  0.62  TEST=  0
INDE  2  68  20  FOBS=    0.0  SIGMA=  26.5  PHAS=    0.0  FOM=  0.00  TEST=  0
INDE  2  68  22  FOBS=  128.0  SIGMA=   1.7  PHAS=   41.6  FOM=  0.21  TEST=  1
INDE  2  68  24  FOBS=    0.0  SIGMA=  20.9  PHAS=    0.0  FOM=  0.00  TEST=  0
INDE  2  68  26  FOBS=   52.9  SIGMA=   4.3  PHAS=   -3.8  FOM=  0.85  TEST=  0
INDE  2  68  28  FOBS=    0.0  SIGMA=  22.8  PHAS=    0.0  FOM=  0.00  TEST=  0
INDE  2  68  30  FOBS=   18.4  SIGMA=  13.2  PHAS=   94.3  FOM=  0.02  TEST=  1
INDE  2  68  32  FOBS=   47.8  SIGMA=   4.8  PHAS=  -99.3  FOM=  0.10  TEST=  1
INDE  2  68  34  FOBS=   46.4  SIGMA=   5.0  PHAS= -164.6  FOM=  0.80  TEST=  0
INDE  2  68  36  FOBS=   71.6  SIGMA=   3.1  PHAS=   42.1  FOM=  0.88  TEST=  0
INDE  2  69   3  FOBS=  141.3  SIGMA=   2.3  PHAS= -131.2  FOM=  0.94  TEST=  0
INDE  2  69   5  FOBS=   92.3  SIGMA=   3.2  PHAS= -132.3  FOM=  0.92  TEST=  0
INDE  2  69   7  FOBS=   65.4  SIGMA=   2.8  PHAS= -127.4  FOM=  0.93  TEST=  0
INDE  2  69  15  FOBS=   29.5  SIGMA=  17.9  PHAS=   92.3  FOM=  0.06  TEST=  0
INDE  2  69  17  FOBS=   49.9  SIGMA=  10.3  PHAS=   56.3  FOM=  0.58  TEST=  0
INDE  2  69  19  FOBS=   27.8  SIGMA=  12.7  PHAS= -149.9  FOM=  0.19  TEST=  0
INDE  2  69  21  FOBS=   89.8  SIGMA=   2.7  PHAS=  115.3  FOM=  0.94  TEST=  0
INDE  2  69  23  FOBS=    0.0  SIGMA=  20.4  PHAS=    0.0  FOM=  0.00  TEST=  0
INDE  2  69  25  FOBS=    0.0  SIGMA=  21.1  PHAS=    0.0  FOM=  0.00  TEST=  0
INDE  2  69  27  FOBS=    0.0  SIGMA=  22.7  PHAS=    0.0  FOM=  0.00  TEST=  0
INDE  2  69  29  FOBS=   45.0  SIGMA=   5.4  PHAS=  -21.1  FOM=  0.80  TEST=  0
INDE  2  69  31  FOBS=   20.1  SIGMA=  11.0  PHAS=  -73.5  FOM=  0.49  TEST=  0
INDE  2  69  33  FOBS=   45.1  SIGMA=   5.8  PHAS=   46.8  FOM=  0.70  TEST=  0
INDE  2  69  35  FOBS=   31.0  SIGMA=   7.7  PHAS=   -2.8  FOM=  0.33  TEST=  0
INDE  2  70   4  FOBS=   52.1  SIGMA=   6.0  PHAS= -175.7  FOM=  0.84  TEST=  0
INDE  2  70   6  FOBS=   98.0  SIGMA=   3.3  PHAS=  144.7  FOM=  0.92  TEST=  0
INDE  2  70   8  FOBS=   33.1  SIGMA=   6.2  PHAS=   44.4  FOM=  0.14  TEST=  1
INDE  2  70  20  FOBS=  107.8  SIGMA=   5.1  PHAS=   14.9  FOM=  0.95  TEST=  0
INDE  2  70  22  FOBS=   52.7  SIGMA=   5.4  PHAS= -123.9  FOM=  0.13  TEST=  0
INDE  2  70  24  FOBS=    0.0  SIGMA=  21.6  PHAS=    0.0  FOM=  0.00  TEST=  0
INDE  2  70  26  FOBS=   26.8  SIGMA=   8.4  PHAS=   73.3  FOM=  0.37  TEST=  0
INDE  2  70  28  FOBS=   91.3  SIGMA=   2.7  PHAS= -171.7  FOM=  0.93  TEST=  0
INDE  2  70  30  FOBS=   75.0  SIGMA=   3.0  PHAS= -168.0  FOM=  0.90  TEST=  0
INDE  2  70  32  FOBS=   27.4  SIGMA=   8.4  PHAS= -124.9  FOM=  0.74  TEST=  0
INDE  2  71   3  FOBS=   84.5  SIGMA=   3.6  PHAS=  159.7  FOM=  0.85  TEST=  0
INDE  2  71   5  FOBS=   26.0  SIGMA=  11.3  PHAS=  143.3  FOM=  0.28  TEST=  0
INDE  2  71   7  FOBS=   52.3  SIGMA=   3.8  PHAS=   25.0  FOM=  0.83  TEST=  0
INDE  2  71   9  FOBS=   87.4  SIGMA=   3.4  PHAS=   70.3  FOM=  0.56  TEST=  0
INDE  2  71  23  FOBS=   25.8  SIGMA=  13.4  PHAS= -113.6  FOM=  0.14  TEST=  0
INDE  2  71  25  FOBS=    0.0  SIGMA=  24.7  PHAS=    0.0  FOM=  0.00  TEST=  0
INDE  2  71  27  FOBS=   70.7  SIGMA=   3.8  PHAS=   58.3  FOM=  0.12  TEST=  1
INDE  2  71  29  FOBS=   86.3  SIGMA=   2.6  PHAS=   67.7  FOM=  0.90  TEST=  0
INDE  2  71  31  FOBS=   68.9  SIGMA=   3.1  PHAS=  132.2  FOM=  0.85  TEST=  0
```

*FIG. 12A - 76*

```
INDE  2  72   6  FOBS=   52.4  SIGMA=   5.6  PHAS=  -117.1  FOM=  0.49  TEST=  0
INDE  2  72   8  FOBS=   53.6  SIGMA=   3.5  PHAS=   -56.6  FOM=  0.88  TEST=  0
INDE  2  72  24  FOBS=   22.3  SIGMA=  11.5  PHAS=   139.8  FOM=  0.32  TEST=  0
INDE  2  72  26  FOBS=   48.0  SIGMA=   5.9  PHAS=   -97.6  FOM=  0.77  TEST=  0
INDE  2  72  28  FOBS=    0.0  SIGMA=  23.4  PHAS=     0.0  FOM=  0.00  TEST=  0
INDE  2  73   7  FOBS=   34.9  SIGMA=   9.0  PHAS=  -116.1  FOM=  0.77  TEST=  0
INDE  2  73   9  FOBS=   20.7  SIGMA=   9.4  PHAS=   178.7  FOM=  0.31  TEST=  0
INDE  2  73  25  FOBS=   22.4  SIGMA=  11.9  PHAS=    49.6  FOM=  0.20  TEST=  0
INDE  2  74   4  FOBS=   25.9  SIGMA=  11.7  PHAS=  -130.7  FOM=  0.45  TEST=  0
INDE  2  74   6  FOBS=   66.7  SIGMA=   4.5  PHAS=  -143.4  FOM=  0.76  TEST=  0
INDE  2  74   8  FOBS=   38.5  SIGMA=   6.3  PHAS=   150.4  FOM=  0.71  TEST=  0
INDE  2  74  10  FOBS=   29.2  SIGMA=   9.8  PHAS=   129.0  FOM=  0.62  TEST=  0
INDE  2  75   7  FOBS=   76.8  SIGMA=   3.9  PHAS=  -108.9  FOM=  0.92  TEST=  0
INDE  2  75   9  FOBS=   27.1  SIGMA=   6.9  PHAS=    66.8  FOM=  0.57  TEST=  0
INDE  2  75  11  FOBS=   37.1  SIGMA=   7.6  PHAS=     6.2  FOM=  0.56  TEST=  0
INDE  2  76   6  FOBS=   39.1  SIGMA=   8.0  PHAS=  -151.1  FOM=  0.87  TEST=  0
INDE  2  76   8  FOBS=   36.9  SIGMA=   8.8  PHAS=   136.9  FOM=  0.61  TEST=  0
INDE  2  76  10  FOBS=   27.9  SIGMA=   7.3  PHAS=  -107.7  FOM=  0.47  TEST=  0
INDE  2  77   7  FOBS=  104.5  SIGMA=   3.1  PHAS=   127.1  FOM=  0.85  TEST=  0
INDE  2  77   9  FOBS=    0.0  SIGMA=  20.0  PHAS=     0.0  FOM=  0.00  TEST=  1
INDE  3   4  19  FOBS=  187.0  SIGMA=   0.5  PHAS=  -175.0  FOM=  0.92  TEST=  0
INDE  3   4  21  FOBS=  348.1  SIGMA=   0.6  PHAS=   128.6  FOM=  0.93  TEST=  0
INDE  3   4  23  FOBS=  170.0  SIGMA=   0.7  PHAS=   121.4  FOM=  0.29  TEST=  1
INDE  3   4  25  FOBS=   69.3  SIGMA=   1.5  PHAS=  -103.5  FOM=  0.92  TEST=  0
INDE  3   4  27  FOBS=   18.3  SIGMA=   5.7  PHAS=    18.0  FOM=  0.48  TEST=  0
INDE  3   4  29  FOBS=  231.3  SIGMA=   0.7  PHAS=  -171.0  FOM=  0.98  TEST=  0
INDE  3   4  31  FOBS=   90.0  SIGMA=   1.4  PHAS=   144.4  FOM=  0.98  TEST=  0
INDE  3   4  33  FOBS=  148.0  SIGMA=   1.0  PHAS=   -62.5  FOM=  0.96  TEST=  0
INDE  3   4  35  FOBS=  179.7  SIGMA=   0.9  PHAS=    48.3  FOM=  0.45  TEST=  0
INDE  3   4  37  FOBS=  237.6  SIGMA=   0.8  PHAS=   -72.8  FOM=  0.98  TEST=  0
INDE  3   4  39  FOBS=   71.6  SIGMA=   2.4  PHAS=    27.1  FOM=  0.89  TEST=  0
INDE  3   4  41  FOBS=  360.4  SIGMA=   0.7  PHAS=    -7.7  FOM=  0.97  TEST=  0
INDE  3   4  43  FOBS=  217.7  SIGMA=   1.1  PHAS=    32.3  FOM=  0.96  TEST=  0
INDE  3   4  45  FOBS=  227.4  SIGMA=   0.7  PHAS=  -104.3  FOM=  0.97  TEST=  0
INDE  3   4  47  FOBS=  259.0  SIGMA=   0.7  PHAS=   -74.9  FOM=  0.96  TEST=  0
INDE  3   4  49  FOBS=   43.5  SIGMA=   3.7  PHAS=  -124.3  FOM=  0.91  TEST=  0
INDE  3   4  51  FOBS=  188.9  SIGMA=   1.5  PHAS=   148.2  FOM=  0.98  TEST=  0
INDE  3   4  53  FOBS=  104.1  SIGMA=   2.5  PHAS=   152.9  FOM=  0.84  TEST=  0
INDE  3   4  55  FOBS=  129.2  SIGMA=   1.4  PHAS=  -113.3  FOM=  0.91  TEST=  1
INDE  3   4  57  FOBS=   58.0  SIGMA=   3.4  PHAS=   143.4  FOM=  0.23  TEST=  0
INDE  3   4  59  FOBS=    0.0  SIGMA=  20.6  PHAS=     0.0  FOM=  0.00  TEST=  0
INDE  3   4  61  FOBS=  150.7  SIGMA=   1.5  PHAS=   -79.5  FOM=  0.95  TEST=  0
INDE  3   4  63  FOBS=   98.0  SIGMA=   2.3  PHAS=   -12.4  FOM=  0.36  TEST=  0
INDE  3   4  65  FOBS=   48.7  SIGMA=   4.9  PHAS=    92.4  FOM=  0.23  TEST=  0
INDE  3   4  67  FOBS=  182.8  SIGMA=   1.9  PHAS=   -15.1  FOM=  0.95  TEST=  0
INDE  3   4  69  FOBS=  114.8  SIGMA=   3.0  PHAS=     8.9  FOM=  0.95  TEST=  0
INDE  3   4  73  FOBS=   42.4  SIGMA=   7.9  PHAS=   111.3  FOM=  0.47  TEST=  0
INDE  3   4  75  FOBS=    0.0  SIGMA=  26.2  PHAS=     0.0  FOM=  0.00  TEST=  0
INDE  3   5  18  FOBS=  188.2  SIGMA=   0.5  PHAS=    42.1  FOM=  0.66  TEST=  0
INDE  3   5  20  FOBS=  175.2  SIGMA=   0.6  PHAS=    37.8  FOM=  0.92  TEST=  0
INDE  3   5  22  FOBS=  308.4  SIGMA=   0.6  PHAS=    25.1  FOM=  0.92  TEST=  0
INDE  3   5  24  FOBS=  205.5  SIGMA=   0.5  PHAS=  -172.1  FOM=  0.32  TEST=  1
INDE  3   5  26  FOBS=  128.1  SIGMA=   0.7  PHAS=    33.9  FOM=  0.99  TEST=  0
INDE  3   5  28  FOBS=  121.5  SIGMA=   0.8  PHAS=   -73.4  FOM=  0.81  TEST=  0
INDE  3   5  30  FOBS=  119.2  SIGMA=   0.9  PHAS=   133.4  FOM=  0.93  TEST=  0
INDE  3   5  32  FOBS=  158.5  SIGMA=   0.8  PHAS=  -176.2  FOM=  0.98  TEST=  0
INDE  3   5  34  FOBS=  157.7  SIGMA=   1.5  PHAS=   -61.1  FOM=  0.95  TEST=  0
INDE  3   5  36  FOBS=   99.3  SIGMA=   1.4  PHAS=   -32.6  FOM=  0.95  TEST=  0
INDE  3   5  38  FOBS=  194.4  SIGMA=   1.0  PHAS=    90.2  FOM=  0.92  TEST=  0
INDE  3   5  40  FOBS=  431.0  SIGMA=   0.6  PHAS=   -76.3  FOM=  0.89  TEST=  1
INDE  3   5  42  FOBS=  312.0  SIGMA=   1.0  PHAS=  -122.7  FOM=  0.96  TEST=  0
INDE  3   5  44  FOBS=  106.9  SIGMA=   1.9  PHAS=   -97.4  FOM=  0.98  TEST=  0
INDE  3   5  46  FOBS=  123.2  SIGMA=   1.7  PHAS=   166.0  FOM=  0.75  TEST=  0
INDE  3   5  48  FOBS=  148.7  SIGMA=   1.6  PHAS=   121.3  FOM=  0.98  TEST=  0
INDE  3   5  50  FOBS=  190.0  SIGMA=   1.2  PHAS=    25.5  FOM=  0.95  TEST=  0
INDE  3   5  52  FOBS=   59.9  SIGMA=   3.4  PHAS=   -43.9  FOM=  0.47  TEST=  0
INDE  3   5  54  FOBS=  103.0  SIGMA=   1.7  PHAS=    64.1  FOM=  0.74  TEST=  0
INDE  3   5  56  FOBS=   78.0  SIGMA=   1.9  PHAS=  -157.5  FOM=  0.96  TEST=  0
INDE  3   5  58  FOBS=   16.3  SIGMA=   9.9  PHAS=    13.4  FOM=  0.46  TEST=  0
INDE  3   5  60  FOBS=   79.3  SIGMA=   1.9  PHAS=  -179.8  FOM=  0.92  TEST=  0
```

*FIG. 12A - 77*

| | | | | | | | | | | | |
|---|---|---|---|---|---|---|---|---|---|---|---|
| INDE | 3 | 5 | 62 | FOBS= | 59.3 | SIGMA= | 3.2 | PHAS= | -104.7 | FOM= 0.83 | TEST= 0 |
| INDE | 3 | 5 | 64 | FOBS= | 43.8 | SIGMA= | 4.7 | PHAS= | -108.4 | FOM= 0.17 | TEST= 1 |
| INDE | 3 | 5 | 66 | FOBS= | 80.2 | SIGMA= | 3.6 | PHAS= | -55.6 | FOM= 0.93 | TEST= 0 |
| INDE | 3 | 5 | 68 | FOBS= | 95.8 | SIGMA= | 3.6 | PHAS= | -59.6 | FOM= 0.94 | TEST= 0 |
| INDE | 3 | 5 | 70 | FOBS= | 0.0 | SIGMA= | 25.9 | PHAS= | 0.0 | FOM= 0.00 | TEST= 0 |
| INDE | 3 | 5 | 72 | FOBS= | 67.1 | SIGMA= | 5.0 | PHAS= | -169.5 | FOM= 0.84 | TEST= 0 |
| INDE | 3 | 5 | 74 | FOBS= | 34.4 | SIGMA= | 9.9 | PHAS= | 53.4 | FOM= 0.57 | TEST= 0 |
| INDE | 3 | 5 | 76 | FOBS= | 71.5 | SIGMA= | 5.1 | PHAS= | -69.4 | FOM= 0.82 | TEST= 0 |
| INDE | 3 | 6 | 17 | FOBS= | 436.3 | SIGMA= | 0.4 | PHAS= | 56.6 | FOM= 0.93 | TEST= 0 |
| INDE | 3 | 6 | 19 | FOBS= | 341.5 | SIGMA= | 0.5 | PHAS= | -54.9 | FOM= 0.95 | TEST= 0 |
| INDE | 3 | 6 | 21 | FOBS= | 207.3 | SIGMA= | 0.6 | PHAS= | -105.9 | FOM= 0.83 | TEST= 0 |
| INDE | 3 | 6 | 23 | FOBS= | 308.0 | SIGMA= | 0.6 | PHAS= | -75.6 | FOM= 0.97 | TEST= 0 |
| INDE | 3 | 6 | 25 | FOBS= | 179.8 | SIGMA= | 0.6 | PHAS= | -106.9 | FOM= 0.92 | TEST= 0 |
| INDE | 3 | 6 | 27 | FOBS= | 132.7 | SIGMA= | 0.7 | PHAS= | -141.5 | FOM= 0.97 | TEST= 0 |
| INDE | 3 | 6 | 29 | FOBS= | 70.7 | SIGMA= | 1.3 | PHAS= | 76.9 | FOM= 0.98 | TEST= 0 |
| INDE | 3 | 6 | 31 | FOBS= | 189.9 | SIGMA= | 0.6 | PHAS= | 86.5 | FOM= 0.92 | TEST= 0 |
| INDE | 3 | 6 | 33 | FOBS= | 122.9 | SIGMA= | 0.9 | PHAS= | 155.6 | FOM= 0.93 | TEST= 1 |
| INDE | 3 | 6 | 35 | FOBS= | 138.2 | SIGMA= | 0.9 | PHAS= | -109.1 | FOM= 0.83 | TEST= 0 |
| INDE | 3 | 6 | 37 | FOBS= | 408.6 | SIGMA= | 0.8 | PHAS= | -61.0 | FOM= 0.97 | TEST= 0 |
| INDE | 3 | 6 | 39 | FOBS= | 178.9 | SIGMA= | 0.9 | PHAS= | -50.2 | FOM= 0.96 | TEST= 0 |
| INDE | 3 | 6 | 41 | FOBS= | 209.4 | SIGMA= | 1.0 | PHAS= | -127.5 | FOM= 0.86 | TEST= 0 |
| INDE | 3 | 6 | 43 | FOBS= | 26.0 | SIGMA= | 5.9 | PHAS= | 166.0 | FOM= 0.31 | TEST= 0 |
| INDE | 3 | 6 | 45 | FOBS= | 112.0 | SIGMA= | 1.6 | PHAS= | 175.4 | FOM= 0.88 | TEST= 0 |
| INDE | 3 | 6 | 47 | FOBS= | 81.6 | SIGMA= | 2.3 | PHAS= | 150.6 | FOM= 0.86 | TEST= 0 |
| INDE | 3 | 6 | 49 | FOBS= | 97.0 | SIGMA= | 2.1 | PHAS= | -59.3 | FOM= 0.94 | TEST= 0 |
| INDE | 3 | 6 | 51 | FOBS= | 55.8 | SIGMA= | 3.4 | PHAS= | -89.7 | FOM= 0.30 | TEST= 0 |
| INDE | 3 | 6 | 53 | FOBS= | 52.5 | SIGMA= | 3.5 | PHAS= | 90.2 | FOM= 0.79 | TEST= 0 |
| INDE | 3 | 6 | 55 | FOBS= | 42.8 | SIGMA= | 3.9 | PHAS= | -133.8 | FOM= 0.59 | TEST= 0 |
| INDE | 3 | 6 | 57 | FOBS= | 135.9 | SIGMA= | 1.3 | PHAS= | 95.9 | FOM= 0.76 | TEST= 0 |
| INDE | 3 | 6 | 59 | FOBS= | 97.0 | SIGMA= | 1.6 | PHAS= | -16.2 | FOM= 0.84 | TEST= 0 |
| INDE | 3 | 6 | 61 | FOBS= | 85.1 | SIGMA= | 1.8 | PHAS= | 146.1 | FOM= 0.78 | TEST= 0 |
| INDE | 3 | 6 | 63 | FOBS= | 55.1 | SIGMA= | 3.5 | PHAS= | 93.4 | FOM= 0.85 | TEST= 0 |
| INDE | 3 | 6 | 65 | FOBS= | 78.9 | SIGMA= | 3.3 | PHAS= | 175.0 | FOM= 0.68 | TEST= 0 |
| INDE | 3 | 6 | 67 | FOBS= | 57.0 | SIGMA= | 6.3 | PHAS= | -129.4 | FOM= 0.86 | TEST= 0 |
| INDE | 3 | 6 | 69 | FOBS= | 77.0 | SIGMA= | 4.6 | PHAS= | -25.8 | FOM= 0.83 | TEST= 0 |
| INDE | 3 | 6 | 71 | FOBS= | 68.5 | SIGMA= | 5.1 | PHAS= | 63.8 | FOM= 0.89 | TEST= 0 |
| INDE | 3 | 6 | 73 | FOBS= | 20.0 | SIGMA= | 17.5 | PHAS= | 145.2 | FOM= 0.24 | TEST= 0 |
| INDE | 3 | 6 | 75 | FOBS= | 107.3 | SIGMA= | 3.5 | PHAS= | -67.2 | FOM= 0.90 | TEST= 0 |
| INDE | 3 | 6 | 77 | FOBS= | 108.4 | SIGMA= | 3.5 | PHAS= | -167.3 | FOM= 0.94 | TEST= 0 |
| INDE | 3 | 7 | 18 | FOBS= | 415.3 | SIGMA= | 0.4 | PHAS= | -147.4 | FOM= 0.93 | TEST= 1 |
| INDE | 3 | 7 | 20 | FOBS= | 348.5 | SIGMA= | 0.5 | PHAS= | -148.0 | FOM= 0.97 | TEST= 0 |
| INDE | 3 | 7 | 22 | FOBS= | 153.8 | SIGMA= | 0.5 | PHAS= | -178.3 | FOM= 0.96 | TEST= 0 |
| INDE | 3 | 7 | 24 | FOBS= | 311.4 | SIGMA= | 0.5 | PHAS= | 164.6 | FOM= 0.97 | TEST= 0 |
| INDE | 3 | 7 | 26 | FOBS= | 37.6 | SIGMA= | 2.2 | PHAS= | -128.9 | FOM= 0.90 | TEST= 0 |
| INDE | 3 | 7 | 28 | FOBS= | 200.1 | SIGMA= | 0.6 | PHAS= | -12.8 | FOM= 0.99 | TEST= 0 |
| INDE | 3 | 7 | 30 | FOBS= | 56.1 | SIGMA= | 1.7 | PHAS= | 16.6 | FOM= 0.99 | TEST= 0 |
| INDE | 3 | 7 | 32 | FOBS= | 149.7 | SIGMA= | 0.8 | PHAS= | 27.8 | FOM= 0.96 | TEST= 0 |
| INDE | 3 | 7 | 34 | FOBS= | 337.7 | SIGMA= | 0.8 | PHAS= | 28.1 | FOM= 0.97 | TEST= 0 |
| INDE | 3 | 7 | 36 | FOBS= | 200.0 | SIGMA= | 0.8 | PHAS= | 144.8 | FOM= 0.90 | TEST= 0 |
| INDE | 3 | 7 | 38 | FOBS= | 334.9 | SIGMA= | 0.9 | PHAS= | -47.4 | FOM= 0.99 | TEST= 0 |
| INDE | 3 | 7 | 40 | FOBS= | 124.9 | SIGMA= | 1.3 | PHAS= | 63.0 | FOM= 0.66 | TEST= 0 |
| INDE | 3 | 7 | 42 | FOBS= | 69.8 | SIGMA= | 2.2 | PHAS= | -106.9 | FOM= 0.90 | TEST= 0 |
| INDE | 3 | 7 | 44 | FOBS= | 111.9 | SIGMA= | 1.5 | PHAS= | 137.4 | FOM= 0.67 | TEST= 0 |
| INDE | 3 | 7 | 46 | FOBS= | 224.6 | SIGMA= | 0.9 | PHAS= | 73.8 | FOM= 0.92 | TEST= 0 |
| INDE | 3 | 7 | 48 | FOBS= | 86.3 | SIGMA= | 2.3 | PHAS= | -178.4 | FOM= 0.07 | TEST= 0 |
| INDE | 3 | 7 | 50 | FOBS= | 91.9 | SIGMA= | 2.2 | PHAS= | 163.0 | FOM= 0.55 | TEST= 0 |
| INDE | 3 | 7 | 52 | FOBS= | 82.2 | SIGMA= | 2.3 | PHAS= | -73.9 | FOM= 0.77 | TEST= 1 |
| INDE | 3 | 7 | 54 | FOBS= | 60.9 | SIGMA= | 3.1 | PHAS= | -4.5 | FOM= 0.34 | TEST= 0 |
| INDE | 3 | 7 | 56 | FOBS= | 38.3 | SIGMA= | 4.3 | PHAS= | 79.1 | FOM= 0.67 | TEST= 0 |
| INDE | 3 | 7 | 58 | FOBS= | 39.2 | SIGMA= | 3.8 | PHAS= | -178.0 | FOM= 0.61 | TEST= 0 |
| INDE | 3 | 7 | 60 | FOBS= | 144.8 | SIGMA= | 1.1 | PHAS= | -32.7 | FOM= 0.87 | TEST= 0 |
| INDE | 3 | 7 | 62 | FOBS= | 92.9 | SIGMA= | 1.7 | PHAS= | -1.2 | FOM= 0.91 | TEST= 0 |
| INDE | 3 | 7 | 64 | FOBS= | 65.5 | SIGMA= | 2.8 | PHAS= | 75.6 | FOM= 0.82 | TEST= 0 |
| INDE | 3 | 7 | 66 | FOBS= | 168.4 | SIGMA= | 1.5 | PHAS= | 79.3 | FOM= 0.96 | TEST= 0 |
| INDE | 3 | 7 | 68 | FOBS= | 72.6 | SIGMA= | 5.1 | PHAS= | 158.6 | FOM= 0.92 | TEST= 0 |
| INDE | 3 | 7 | 70 | FOBS= | 115.2 | SIGMA= | 3.2 | PHAS= | -7.9 | FOM= 0.95 | TEST= 0 |
| INDE | 3 | 7 | 72 | FOBS= | 0.0 | SIGMA= | 26.5 | PHAS= | 0.0 | FOM= 0.00 | TEST= 1 |
| INDE | 3 | 7 | 74 | FOBS= | 65.9 | SIGMA= | 5.6 | PHAS= | 161.9 | FOM= 0.87 | TEST= 0 |
| INDE | 3 | 7 | 76 | FOBS= | 84.3 | SIGMA= | 4.5 | PHAS= | 136.6 | FOM= 0.91 | TEST= 0 |
| INDE | 3 | 8 | 17 | FOBS= | 438.4 | SIGMA= | 0.4 | PHAS= | -63.0 | FOM= 0.87 | TEST= 1 |

*FIG. 12A - 78*

```
INDE    3   8   19  FOBS=   335.4   SIGMA=   0.3  PHAS=   138.7  FOM=  0.96  TEST= 0
INDE    3   8   21  FOBS=   329.0   SIGMA=   0.5  PHAS=   115.7  FOM=  0.96  TEST= 0
INDE    3   8   23  FOBS=   121.3   SIGMA=   0.6  PHAS=   -11.9  FOM=  0.97  TEST= 0
INDE    3   8   25  FOBS=    33.7   SIGMA=   2.6  PHAS=    77.2  FOM=  0.89  TEST= 0
INDE    3   8   27  FOBS=   130.8   SIGMA=   0.8  PHAS=  -133.2  FOM=  0.97  TEST= 0
INDE    3   8   29  FOBS=    60.0   SIGMA=   1.6  PHAS=    41.1  FOM=  0.52  TEST= 0
INDE    3   8   31  FOBS=    77.2   SIGMA=   1.3  PHAS=   -46.0  FOM=  0.98  TEST= 0
INDE    3   8   33  FOBS=    97.2   SIGMA=   1.1  PHAS=   -27.2  FOM=  0.97  TEST= 0
INDE    3   8   35  FOBS=   238.2   SIGMA=   1.0  PHAS=   -43.8  FOM=  0.95  TEST= 0
INDE    3   8   37  FOBS=   369.9   SIGMA=   1.1  PHAS=   -16.8  FOM=  0.98  TEST= 0
INDE    3   8   39  FOBS=    88.3   SIGMA=   1.7  PHAS=   -25.0  FOM=  0.89  TEST= 0
INDE    3   8   41  FOBS=   153.9   SIGMA=   1.3  PHAS=   -43.6  FOM=  0.92  TEST= 0
INDE    3   8   43  FOBS=   161.5   SIGMA=   1.1  PHAS=   -83.7  FOM=  0.89  TEST= 0
INDE    3   8   45  FOBS=   299.0   SIGMA=   1.1  PHAS=    -2.5  FOM=  0.97  TEST= 0
INDE    3   8   47  FOBS=   147.3   SIGMA=   1.4  PHAS=    65.2  FOM=  0.89  TEST= 0
INDE    3   8   49  FOBS=    60.8   SIGMA=   3.3  PHAS=  -161.0  FOM=  0.38  TEST= 0
INDE    3   8   51  FOBS=    74.3   SIGMA=   2.6  PHAS=     4.5  FOM=  0.94  TEST= 0
INDE    3   8   53  FOBS=    56.7   SIGMA=   3.4  PHAS=   145.1  FOM=  0.53  TEST= 0
INDE    3   8   55  FOBS=    50.6   SIGMA=   3.7  PHAS=   -57.0  FOM=  0.92  TEST= 0
INDE    3   8   57  FOBS=    78.1   SIGMA=   2.0  PHAS=  -160.8  FOM=  0.54  TEST= 0
INDE    3   8   59  FOBS=   147.3   SIGMA=   1.1  PHAS=   -86.7  FOM=  0.96  TEST= 0
INDE    3   8   61  FOBS=    94.3   SIGMA=   1.6  PHAS=   163.5  FOM=  0.91  TEST= 0
INDE    3   8   63  FOBS=    72.0   SIGMA=   2.8  PHAS=    58.9  FOM=  0.78  TEST= 1
INDE    3   8   65  FOBS=   140.2   SIGMA=   1.6  PHAS=     8.1  FOM=  0.94  TEST= 0
INDE    3   8   67  FOBS=   159.9   SIGMA=   1.8  PHAS=    22.4  FOM=  0.98  TEST= 0
INDE    3   8   69  FOBS=    54.3   SIGMA=   7.0  PHAS=   -88.1  FOM=  0.65  TEST= 0
INDE    3   8   71  FOBS=    10.0   SIGMA=  37.8  PHAS=   144.0  FOM=  0.04  TEST= 0
INDE    3   8   73  FOBS=    67.9   SIGMA=   5.5  PHAS=    11.4  FOM=  0.87  TEST= 0
INDE    3   8   75  FOBS=    19.2   SIGMA=  20.0  PHAS=    12.2  FOM=  0.63  TEST= 0
INDE    3   8   77  FOBS=    65.4   SIGMA=   6.0  PHAS=    70.9  FOM=  0.37  TEST= 0
INDE    3   9   16  FOBS=   247.9   SIGMA=   0.3  PHAS=   165.8  FOM=  0.91  TEST= 0
INDE    3   9   18  FOBS=   175.4   SIGMA=   0.4  PHAS=   112.4  FOM=  0.82  TEST= 0
INDE    3   9   20  FOBS=   263.1   SIGMA=   0.4  PHAS=    63.9  FOM=  0.88  TEST= 0
INDE    3   9   22  FOBS=    88.8   SIGMA=   0.6  PHAS=    96.2  FOM=  0.95  TEST= 1
INDE    3   9   24  FOBS=   211.6   SIGMA=   0.4  PHAS=  -122.2  FOM=  0.96  TEST= 0
INDE    3   9   26  FOBS=     5.5   SIGMA=  13.6  PHAS=  -169.6  FOM=  0.51  TEST= 0
INDE    3   9   28  FOBS=   135.4   SIGMA=   0.8  PHAS=   -18.0  FOM=  0.99  TEST= 0
INDE    3   9   30  FOBS=    28.7   SIGMA=   3.3  PHAS=   -92.1  FOM=  0.48  TEST= 0
INDE    3   9   32  FOBS=   327.0   SIGMA=   0.7  PHAS=    26.6  FOM=  0.98  TEST= 1
INDE    3   9   34  FOBS=   136.7   SIGMA=   1.0  PHAS=    62.1  FOM=  0.96  TEST= 0
INDE    3   9   36  FOBS=   535.0   SIGMA=   1.0  PHAS=  -153.6  FOM=  0.99  TEST= 0
INDE    3   9   38  FOBS=   311.6   SIGMA=   0.8  PHAS=   -41.1  FOM=  0.96  TEST= 0
INDE    3   9   40  FOBS=   287.9   SIGMA=   0.9  PHAS=  -153.2  FOM=  0.95  TEST= 0
INDE    3   9   42  FOBS=    18.6   SIGMA=   9.0  PHAS=   130.8  FOM=  0.15  TEST= 0
INDE    3   9   44  FOBS=   110.7   SIGMA=   1.6  PHAS=  -114.9  FOM=  0.95  TEST= 0
INDE    3   9   46  FOBS=    95.0   SIGMA=   2.1  PHAS=  -154.1  FOM=  0.69  TEST= 0
INDE    3   9   48  FOBS=   193.3   SIGMA=   1.2  PHAS=   -69.0  FOM=  0.94  TEST= 0
INDE    3   9   50  FOBS=    97.1   SIGMA=   2.1  PHAS=  -129.2  FOM=  0.71  TEST= 0
INDE    3   9   52  FOBS=    52.8   SIGMA=   4.2  PHAS=   -67.0  FOM=  0.61  TEST= 0
INDE    3   9   54  FOBS=    53.2   SIGMA=   3.6  PHAS=   -61.5  FOM=  0.75  TEST= 0
INDE    3   9   56  FOBS=    50.6   SIGMA=   3.8  PHAS=   120.4  FOM=  0.93  TEST= 0
INDE    3   9   58  FOBS=   137.0   SIGMA=   1.2  PHAS=   133.2  FOM=  0.96  TEST= 0
INDE    3   9   60  FOBS=    45.5   SIGMA=   3.8  PHAS=    28.6  FOM=  0.80  TEST= 0
INDE    3   9   62  FOBS=   160.2   SIGMA=   1.2  PHAS=     2.4  FOM=  0.96  TEST= 0
INDE    3   9   64  FOBS=    24.9   SIGMA=   7.9  PHAS=  -114.6  FOM=  0.52  TEST= 0
INDE    3   9   66  FOBS=   100.7   SIGMA=   2.8  PHAS=   -23.6  FOM=  0.94  TEST= 0
INDE    3   9   68  FOBS=   113.9   SIGMA=   2.5  PHAS=   -65.6  FOM=  0.90  TEST= 0
INDE    3   9   70  FOBS=    77.7   SIGMA=   3.6  PHAS=   135.7  FOM=  0.88  TEST= 0
INDE    3   9   72  FOBS=    84.4   SIGMA=   3.3  PHAS=   -31.8  FOM=  0.90  TEST= 0
INDE    3   9   74  FOBS=    86.2   SIGMA=   4.5  PHAS=  -167.1  FOM=  0.86  TEST= 0
INDE    3   9   76  FOBS=    42.6   SIGMA=   9.3  PHAS=  -128.6  FOM=  0.45  TEST= 0
INDE    3  10   15  FOBS=    51.2   SIGMA=   0.7  PHAS=   -57.2  FOM=  0.95  TEST= 0
INDE    3  10   17  FOBS=    99.3   SIGMA=   0.4  PHAS=  -156.5  FOM=  0.92  TEST= 0
INDE    3  10   19  FOBS=   171.0   SIGMA=   0.4  PHAS=    44.9  FOM=  0.87  TEST= 0
INDE    3  10   21  FOBS=   198.9   SIGMA=   0.4  PHAS=    56.9  FOM=  0.88  TEST= 0
INDE    3  10   23  FOBS=    58.5   SIGMA=   0.9  PHAS=   150.3  FOM=  0.98  TEST= 0
INDE    3  10   25  FOBS=    92.9   SIGMA=   0.6  PHAS=   114.5  FOM=  0.95  TEST= 0
INDE    3  10   27  FOBS=    62.0   SIGMA=   1.0  PHAS=    16.5  FOM=  0.99  TEST= 0
INDE    3  10   29  FOBS=    82.0   SIGMA=   1.1  PHAS=    14.1  FOM=  0.96  TEST= 0
INDE    3  10   31  FOBS=   311.6   SIGMA=   0.8  PHAS=   -55.3  FOM=  0.97  TEST= 0
```

*FIG. 12A - 79*

```
INDE  3  10  33  FOBS=   241.1  SIGMA=   0.8  PHAS=   -48.4  FOM=  0.94  TEST=  0
INDE  3  10  35  FOBS=   352.4  SIGMA=   0.9  PHAS=    93.6  FOM=  0.96  TEST=  0
INDE  3  10  37  FOBS=   294.4  SIGMA=   1.0  PHAS=    37.9  FOM=  0.94  TEST=  0
INDE  3  10  39  FOBS=    42.1  SIGMA=   3.6  PHAS=    28.5  FOM=  0.74  TEST=  1
INDE  3  10  41  FOBS=    60.7  SIGMA=   2.8  PHAS=  -173.0  FOM=  0.91  TEST=  1
INDE  3  10  43  FOBS=   230.1  SIGMA=   0.9  PHAS=   -40.0  FOM=  0.97  TEST=  0
INDE  3  10  45  FOBS=   286.3  SIGMA=   0.9  PHAS=     6.2  FOM=  0.96  TEST=  0
INDE  3  10  47  FOBS=   228.4  SIGMA=   1.2  PHAS=   174.1  FOM=  0.94  TEST=  0
INDE  3  10  49  FOBS=   161.4  SIGMA=   1.3  PHAS=  -167.6  FOM=  0.96  TEST=  0
INDE  3  10  51  FOBS=   133.7  SIGMA=   1.5  PHAS=   -55.7  FOM=  0.90  TEST=  0
INDE  3  10  53  FOBS=   167.3  SIGMA=   1.2  PHAS=  -152.0  FOM=  0.87  TEST=  0
INDE  3  10  55  FOBS=    70.8  SIGMA=   3.1  PHAS=  -135.8  FOM=  0.29  TEST=  1
INDE  3  10  57  FOBS=   159.8  SIGMA=   1.3  PHAS=    26.1  FOM=  0.95  TEST=  0
INDE  3  10  59  FOBS=   138.9  SIGMA=   1.2  PHAS=   -28.3  FOM=  0.94  TEST=  0
INDE  3  10  61  FOBS=    97.5  SIGMA=   1.6  PHAS=   150.3  FOM=  0.87  TEST=  0
INDE  3  10  63  FOBS=   123.9  SIGMA=   1.7  PHAS=    85.2  FOM=  0.94  TEST=  0
INDE  3  10  65  FOBS=    36.9  SIGMA=   7.0  PHAS=   -27.8  FOM=  0.27  TEST=  0
INDE  3  10  67  FOBS=    73.7  SIGMA=   3.8  PHAS=  -129.4  FOM=  0.86  TEST=  0
INDE  3  10  69  FOBS=    66.9  SIGMA=   4.2  PHAS=   -53.0  FOM=  0.81  TEST=  0
INDE  3  10  71  FOBS=    69.7  SIGMA=   4.1  PHAS=    82.8  FOM=  0.78  TEST=  0
INDE  3  10  73  FOBS=    17.2  SIGMA=  16.6  PHAS=  -150.8  FOM=  0.28  TEST=  0
INDE  3  10  75  FOBS=    60.7  SIGMA=   6.5  PHAS=    38.7  FOM=  0.07  TEST=  1
INDE  3  11  14  FOBS=   220.6  SIGMA=   0.4  PHAS=   116.0  FOM=  0.89  TEST=  0
INDE  3  11  16  FOBS=   173.8  SIGMA=   0.4  PHAS=   153.7  FOM=  0.68  TEST=  0
INDE  3  11  18  FOBS=   338.5  SIGMA=   0.4  PHAS=   -39.5  FOM=  0.96  TEST=  0
INDE  3  11  20  FOBS=   164.2  SIGMA=   0.4  PHAS=    18.1  FOM=  0.85  TEST=  0
INDE  3  11  22  FOBS=    58.8  SIGMA=   1.0  PHAS=   -11.6  FOM=  0.30  TEST=  0
INDE  3  11  24  FOBS=   151.1  SIGMA=   0.6  PHAS=   -39.0  FOM=  0.99  TEST=  1
INDE  3  11  26  FOBS=    92.4  SIGMA=   0.8  PHAS=   -74.8  FOM=  0.98  TEST=  1
INDE  3  11  28  FOBS=   168.7  SIGMA=   0.6  PHAS=   -88.9  FOM=  0.97  TEST=  0
INDE  3  11  30  FOBS=   146.4  SIGMA=   0.7  PHAS=   161.4  FOM=  0.95  TEST=  0
INDE  3  11  32  FOBS=   130.9  SIGMA=   0.9  PHAS=  -112.8  FOM=  0.95  TEST=  0
INDE  3  11  34  FOBS=   233.5  SIGMA=   0.9  PHAS=   -73.2  FOM=  0.94  TEST=  1
INDE  3  11  36  FOBS=    72.4  SIGMA=   1.9  PHAS=    -2.6  FOM=  0.69  TEST=  0
INDE  3  11  38  FOBS=   314.0  SIGMA=   0.7  PHAS=   -26.1  FOM=  0.94  TEST=  0
INDE  3  11  40  FOBS=    54.8  SIGMA=   3.0  PHAS=  -125.5  FOM=  0.95  TEST=  0
INDE  3  11  42  FOBS=   105.8  SIGMA=   1.6  PHAS=    64.1  FOM=  0.91  TEST=  0
INDE  3  11  44  FOBS=   269.6  SIGMA=   1.3  PHAS=  -122.2  FOM=  0.97  TEST=  0
INDE  3  11  46  FOBS=    38.8  SIGMA=   8.0  PHAS=   117.2  FOM=  0.32  TEST=  0
INDE  3  11  48  FOBS=    39.9  SIGMA=   5.6  PHAS=    55.3  FOM=  0.03  TEST=  0
INDE  3  11  50  FOBS=    63.5  SIGMA=   3.2  PHAS=   -38.7  FOM=  0.24  TEST=  0
INDE  3  11  52  FOBS=   124.1  SIGMA=   1.6  PHAS=   167.6  FOM=  0.87  TEST=  0
INDE  3  11  54  FOBS=   185.8  SIGMA=   1.3  PHAS=   130.0  FOM=  0.77  TEST=  0
INDE  3  11  56  FOBS=     0.0  SIGMA=  19.5  PHAS=     0.0  FOM=  0.00  TEST=  0
INDE  3  11  58  FOBS=   100.0  SIGMA=   2.0  PHAS=   -44.1  FOM=  0.92  TEST=  0
INDE  3  11  60  FOBS=    27.6  SIGMA=   7.1  PHAS=   -16.9  FOM=  0.81  TEST=  0
INDE  3  11  62  FOBS=   165.2  SIGMA=   1.1  PHAS=    31.6  FOM=  0.97  TEST=  0
INDE  3  11  64  FOBS=    56.8  SIGMA=   3.9  PHAS=    92.5  FOM=  0.67  TEST=  0
INDE  3  11  66  FOBS=    57.1  SIGMA=   4.9  PHAS=   148.6  FOM=  0.80  TEST=  0
INDE  3  11  68  FOBS=    53.3  SIGMA=   5.3  PHAS=    98.0  FOM=  0.53  TEST=  0
INDE  3  11  70  FOBS=    96.2  SIGMA=   3.0  PHAS=  -169.1  FOM=  0.79  TEST=  0
INDE  3  11  72  FOBS=    18.6  SIGMA=  15.3  PHAS=   -15.1  FOM=  0.54  TEST=  0
INDE  3  11  74  FOBS=     0.0  SIGMA=  24.1  PHAS=     0.0  FOM=  0.00  TEST=  0
INDE  3  11  76  FOBS=     0.0  SIGMA=  29.8  PHAS=     0.0  FOM=  0.00  TEST=  0
INDE  3  12  13  FOBS=   371.3  SIGMA=   0.5  PHAS=   162.7  FOM=  0.32  TEST=  0
INDE  3  12  15  FOBS=   339.3  SIGMA=   0.4  PHAS=   -47.7  FOM=  0.91  TEST=  0
INDE  3  12  17  FOBS=   293.7  SIGMA=   0.5  PHAS=  -149.9  FOM=  0.93  TEST=  0
INDE  3  12  19  FOBS=   258.7  SIGMA=   0.5  PHAS=  -130.8  FOM=  0.93  TEST=  0
INDE  3  12  21  FOBS=   161.6  SIGMA=   0.4  PHAS=   -60.5  FOM=  0.94  TEST=  0
INDE  3  12  23  FOBS=    61.8  SIGMA=   1.0  PHAS=   -55.1  FOM=  0.97  TEST=  0
INDE  3  12  25  FOBS=    91.1  SIGMA=   0.8  PHAS=    48.9  FOM=  0.98  TEST=  0
INDE  3  12  27  FOBS=   174.2  SIGMA=   0.5  PHAS=   132.9  FOM=  0.95  TEST=  0
INDE  3  12  29  FOBS=   152.2  SIGMA=   0.6  PHAS=    73.1  FOM=  0.96  TEST=  0
INDE  3  12  31  FOBS=    84.9  SIGMA=   1.1  PHAS=    10.1  FOM=  0.98  TEST=  0
INDE  3  12  33  FOBS=    30.0  SIGMA=   2.6  PHAS=   106.9  FOM=  0.95  TEST=  0
INDE  3  12  35  FOBS=    86.5  SIGMA=   1.6  PHAS=   -57.6  FOM=  0.96  TEST=  0
INDE  3  12  37  FOBS=   256.3  SIGMA=   0.7  PHAS=    55.1  FOM=  0.93  TEST=  0
INDE  3  12  39  FOBS=   147.9  SIGMA=   1.3  PHAS=   -73.1  FOM=  0.95  TEST=  0
INDE  3  12  41  FOBS=   178.3  SIGMA=   1.1  PHAS=  -175.5  FOM=  0.93  TEST=  0
INDE  3  12  43  FOBS=    63.2  SIGMA=   2.8  PHAS=    -1.0  FOM=  0.92  TEST=  0
```

*FIG. 12A - 80*

```
INDE  3  12  45  FOBS=   110.0  SIGMA=   1.9  PHAS=  -103.2  FOM=  0.90  TEST=  0
INDE  3  12  47  FOBS=   134.4  SIGMA=   1.6  PHAS=  -149.9  FOM=  0.93  TEST=  0
INDE  3  12  49  FOBS=   147.6  SIGMA=   1.7  PHAS=   133.7  FOM=  0.95  TEST=  0
INDE  3  12  51  FOBS=    80.0  SIGMA=   2.5  PHAS=    -7.7  FOM=  0.81  TEST=  0
INDE  3  12  53  FOBS=   101.2  SIGMA=   2.0  PHAS=  -111.8  FOM=  0.11  TEST=  1
INDE  3  12  55  FOBS=    18.7  SIGMA=  10.4  PHAS=   -56.2  FOM=  0.14  TEST=  0
INDE  3  12  57  FOBS=     0.0  SIGMA=  20.9  PHAS=     0.0  FOM=  0.00  TEST=  0
INDE  3  12  59  FOBS=   128.8  SIGMA=   1.6  PHAS=   -91.2  FOM=  0.60  TEST=  1
INDE  3  12  61  FOBS=    72.6  SIGMA=   2.2  PHAS=   -65.4  FOM=  0.69  TEST=  0
INDE  3  12  63  FOBS=    69.8  SIGMA=   3.0  PHAS=    36.8  FOM=  0.87  TEST=  0
INDE  3  12  65  FOBS=   124.9  SIGMA=   2.1  PHAS=    34.2  FOM=  0.94  TEST=  0
INDE  3  12  67  FOBS=    75.1  SIGMA=   3.8  PHAS=   123.4  FOM=  0.87  TEST=  0
INDE  3  12  69  FOBS=    96.4  SIGMA=   3.0  PHAS=    35.6  FOM=  0.84  TEST=  0
INDE  3  12  71  FOBS=    72.6  SIGMA=   3.9  PHAS=  -147.8  FOM=  0.92  TEST=  0
INDE  3  12  73  FOBS=    68.9  SIGMA=   4.3  PHAS=   171.3  FOM=  0.84  TEST=  0
INDE  3  12  75  FOBS=    37.7  SIGMA=   8.0  PHAS=   167.5  FOM=  0.89  TEST=  0
INDE  3  13  12  FOBS=   327.9  SIGMA=   0.6  PHAS=    -2.0  FOM=  0.37  TEST=  0
INDE  3  13  14  FOBS=   201.9  SIGMA=   0.7  PHAS=    11.7  FOM=  0.11  TEST=  0
INDE  3  13  16  FOBS=   215.1  SIGMA=   0.6  PHAS=  -144.2  FOM=  0.87  TEST=  0
INDE  3  13  18  FOBS=    76.3  SIGMA=   0.8  PHAS=  -115.8  FOM=  0.93  TEST=  0
INDE  3  13  20  FOBS=   143.8  SIGMA=   0.5  PHAS=   178.5  FOM=  0.68  TEST=  0
INDE  3  13  22  FOBS=   118.2  SIGMA=   0.6  PHAS=  -173.7  FOM=  0.99  TEST=  0
INDE  3  13  24  FOBS=   258.2  SIGMA=   0.5  PHAS=  -108.7  FOM=  0.90  TEST=  1
INDE  3  13  26  FOBS=    73.7  SIGMA=   1.1  PHAS=    25.3  FOM=  0.99  TEST=  0
INDE  3  13  28  FOBS=   136.0  SIGMA=   0.7  PHAS=   -14.7  FOM=  0.96  TEST=  0
INDE  3  13  30  FOBS=   214.6  SIGMA=   0.6  PHAS=   -49.8  FOM=  0.99  TEST=  0
INDE  3  13  32  FOBS=    85.6  SIGMA=   1.1  PHAS=  -160.7  FOM=  0.86  TEST=  0
INDE  3  13  34  FOBS=   170.4  SIGMA=   0.7  PHAS=  -163.5  FOM=  0.98  TEST=  0
INDE  3  13  36  FOBS=    69.2  SIGMA=   1.4  PHAS=    -9.7  FOM=  0.86  TEST=  0
INDE  3  13  38  FOBS=   167.9  SIGMA=   1.1  PHAS=   -79.9  FOM=  0.97  TEST=  0
INDE  3  13  40  FOBS=    19.9  SIGMA=   9.0  PHAS=    -6.2  FOM=  0.07  TEST=  0
INDE  3  13  42  FOBS=   158.5  SIGMA=   1.3  PHAS=    98.1  FOM=  0.98  TEST=  1
INDE  3  13  44  FOBS=   163.0  SIGMA=   1.3  PHAS=  -174.2  FOM=  0.95  TEST=  0
INDE  3  13  46  FOBS=   166.6  SIGMA=   1.3  PHAS=  -165.8  FOM=  0.86  TEST=  0
INDE  3  13  48  FOBS=    79.3  SIGMA=   3.6  PHAS=    80.8  FOM=  0.90  TEST=  0
INDE  3  13  50  FOBS=   178.8  SIGMA=   1.2  PHAS=    13.1  FOM=  0.93  TEST=  0
INDE  3  13  52  FOBS=    32.3  SIGMA=   6.7  PHAS=    71.7  FOM=  0.17  TEST=  0
INDE  3  13  54  FOBS=     0.0  SIGMA=  19.7  PHAS=     0.0  FOM=  0.00  TEST=  0
INDE  3  13  56  FOBS=    50.7  SIGMA=   3.8  PHAS=  -100.7  FOM=  0.73  TEST=  0
INDE  3  13  58  FOBS=    26.9  SIGMA=   7.2  PHAS=  -129.2  FOM=  0.10  TEST=  0
INDE  3  13  60  FOBS=    14.3  SIGMA=  12.5  PHAS=  -134.4  FOM=  0.20  TEST=  0
INDE  3  13  62  FOBS=    66.5  SIGMA=   2.5  PHAS=    19.7  FOM=  0.16  TEST=  1
INDE  3  13  64  FOBS=    54.5  SIGMA=   4.1  PHAS=   -66.6  FOM=  0.88  TEST=  0
INDE  3  13  66  FOBS=     0.0  SIGMA=  24.1  PHAS=     0.0  FOM=  0.00  TEST=  0
INDE  3  13  68  FOBS=    87.1  SIGMA=   3.4  PHAS=    24.9  FOM=  0.88  TEST=  0
INDE  3  13  70  FOBS=   111.7  SIGMA=   2.7  PHAS=    98.2  FOM=  0.76  TEST=  0
INDE  3  13  72  FOBS=    58.1  SIGMA=   5.0  PHAS=    72.7  FOM=  0.84  TEST=  0
INDE  3  13  74  FOBS=    62.0  SIGMA=   4.8  PHAS=    97.6  FOM=  0.93  TEST=  0
INDE  3  13  76  FOBS=    98.3  SIGMA=   3.2  PHAS=    62.2  FOM=  0.96  TEST=  0
INDE  3  14  11  FOBS=   187.9  SIGMA=   0.7  PHAS=    99.7  FOM=  0.99  TEST=  0
INDE  3  14  13  FOBS=   235.6  SIGMA=   0.9  PHAS=   163.0  FOM=  0.34  TEST=  0
INDE  3  14  15  FOBS=   188.9  SIGMA=   0.7  PHAS=   -69.2  FOM=  0.86  TEST=  0
INDE  3  14  17  FOBS=   275.3  SIGMA=   0.6  PHAS=   159.7  FOM=  0.97  TEST=  0
INDE  3  14  19  FOBS=   104.1  SIGMA=   0.6  PHAS=   157.9  FOM=  0.96  TEST=  0
INDE  3  14  21  FOBS=    40.9  SIGMA=   1.5  PHAS=  -178.7  FOM=  0.45  TEST=  0
INDE  3  14  23  FOBS=    52.3  SIGMA=   1.2  PHAS=   156.5  FOM=  0.98  TEST=  0
INDE  3  14  25  FOBS=    96.6  SIGMA=   0.8  PHAS=    54.3  FOM=  0.93  TEST=  0
INDE  3  14  27  FOBS=    95.1  SIGMA=   0.9  PHAS=    63.2  FOM=  0.98  TEST=  0
INDE  3  14  29  FOBS=    84.9  SIGMA=   1.0  PHAS=  -165.4  FOM=  0.96  TEST=  0
INDE  3  14  31  FOBS=   105.7  SIGMA=   0.9  PHAS=   -39.2  FOM=  0.39  TEST=  0
INDE  3  14  33  FOBS=   138.8  SIGMA=   0.8  PHAS=    69.8  FOM=  0.90  TEST=  0
INDE  3  14  35  FOBS=   111.0  SIGMA=   0.8  PHAS=    41.7  FOM=  0.98  TEST=  0
INDE  3  14  37  FOBS=   160.5  SIGMA=   1.1  PHAS=    -9.0  FOM=  0.83  TEST=  0
INDE  3  14  39  FOBS=    18.2  SIGMA=   9.0  PHAS=  -172.5  FOM=  0.37  TEST=  0
INDE  3  14  41  FOBS=     8.6  SIGMA=  21.1  PHAS=   126.7  FOM=  0.28  TEST=  0
INDE  3  14  43  FOBS=   161.5  SIGMA=   1.2  PHAS=    54.0  FOM=  0.95  TEST=  0
INDE  3  14  45  FOBS=   119.9  SIGMA=   1.7  PHAS=  -167.3  FOM=  0.83  TEST=  0
INDE  3  14  47  FOBS=   184.8  SIGMA=   1.3  PHAS=  -117.2  FOM=  0.95  TEST=  0
INDE  3  14  49  FOBS=   124.5  SIGMA=   1.7  PHAS=  -133.2  FOM=  0.91  TEST=  0
INDE  3  14  51  FOBS=     0.0  SIGMA=  20.2  PHAS=     0.0  FOM=  0.00  TEST=  0
```

*FIG. 12A - 81*

| | | | | | | | | | | | | |
|---|---|---|---|---|---|---|---|---|---|---|---|---|
| INDE | 3 | 14 | 53 | FOBS= | 47.7 | SIGMA= | 4.2 | PHAS= | -26.2 | FOM= | 0.46 | TEST= 0 |
| INDE | 3 | 14 | 55 | FOBS= | 56.4 | SIGMA= | 3.5 | PHAS= | -158.2 | FOM= | 0.51 | TEST= 0 |
| INDE | 3 | 14 | 57 | FOBS= | 78.3 | SIGMA= | 2.5 | PHAS= | 143.9 | FOM= | 0.91 | TEST= 0 |
| INDE | 3 | 14 | 59 | FOBS= | 33.7 | SIGMA= | 5.7 | PHAS= | -49.4 | FOM= | 0.58 | TEST= 0 |
| INDE | 3 | 14 | 61 | FOBS= | 40.3 | SIGMA= | 3.9 | PHAS= | -48.5 | FOM= | 0.72 | TEST= 0 |
| INDE | 3 | 14 | 63 | FOBS= | 18.2 | SIGMA= | 4.7 | PHAS= | -33.5 | FOM= | 0.33 | TEST= 0 |
| INDE | 3 | 14 | 65 | FOBS= | 35.6 | SIGMA= | 8.4 | PHAS= | -176.2 | FOM= | 0.62 | TEST= 0 |
| INDE | 3 | 14 | 67 | FOBS= | 40.0 | SIGMA= | 7.3 | PHAS= | 1.1 | FOM= | 0.37 | TEST= 0 |
| INDE | 3 | 14 | 69 | FOBS= | 89.5 | SIGMA= | 3.3 | PHAS= | -75.2 | FOM= | 0.92 | TEST= 0 |
| INDE | 3 | 14 | 71 | FOBS= | 36.5 | SIGMA= | 8.2 | PHAS= | -30.9 | FOM= | 0.64 | TEST= 0 |
| INDE | 3 | 14 | 73 | FOBS= | 21.6 | SIGMA= | 13.8 | PHAS= | 147.1 | FOM= | 0.12 | TEST= 0 |
| INDE | 3 | 14 | 75 | FOBS= | 0.0 | SIGMA= | 24.6 | PHAS= | 0.0 | FOM= | 0.00 | TEST= 0 |
| INDE | 3 | 15 | 10 | FOBS= | 123.1 | SIGMA= | 1.0 | PHAS= | 70.9 | FOM= | 0.91 | TEST= 0 |
| INDE | 3 | 15 | 12 | FOBS= | 166.9 | SIGMA= | 0.8 | PHAS= | -16.1 | FOM= | 0.68 | TEST= 0 |
| INDE | 3 | 15 | 14 | FOBS= | 335.7 | SIGMA= | 0.7 | PHAS= | 174.8 | FOM= | 0.96 | TEST= 0 |
| INDE | 3 | 15 | 16 | FOBS= | 76.9 | SIGMA= | 1.0 | PHAS= | 164.6 | FOM= | 0.80 | TEST= 0 |
| INDE | 3 | 15 | 18 | FOBS= | 82.9 | SIGMA= | 0.8 | PHAS= | 61.2 | FOM= | 0.89 | TEST= 0 |
| INDE | 3 | 15 | 20 | FOBS= | 169.1 | SIGMA= | 0.5 | PHAS= | 119.3 | FOM= | 0.75 | TEST= 0 |
| INDE | 3 | 15 | 22 | FOBS= | 22.8 | SIGMA= | 2.9 | PHAS= | -106.5 | FOM= | 0.55 | TEST= 0 |
| INDE | 3 | 15 | 24 | FOBS= | 304.6 | SIGMA= | 0.6 | PHAS= | -43.0 | FOM= | 0.98 | TEST= 0 |
| INDE | 3 | 15 | 26 | FOBS= | 198.3 | SIGMA= | 0.5 | PHAS= | -14.2 | FOM= | 0.98 | TEST= 0 |
| INDE | 3 | 15 | 28 | FOBS= | 183.1 | SIGMA= | 0.7 | PHAS= | 17.7 | FOM= | 0.97 | TEST= 0 |
| INDE | 3 | 15 | 30 | FOBS= | 175.5 | SIGMA= | 0.6 | PHAS= | -15.3 | FOM= | 0.92 | TEST= 0 |
| INDE | 3 | 15 | 32 | FOBS= | 155.3 | SIGMA= | 0.7 | PHAS= | -161.6 | FOM= | 0.98 | TEST= 0 |
| INDE | 3 | 15 | 34 | FOBS= | 254.5 | SIGMA= | 0.6 | PHAS= | 110.8 | FOM= | 0.99 | TEST= 0 |
| INDE | 3 | 15 | 36 | FOBS= | 180.8 | SIGMA= | 0.8 | PHAS= | -101.9 | FOM= | 0.97 | TEST= 0 |
| INDE | 3 | 15 | 38 | FOBS= | 222.5 | SIGMA= | 0.7 | PHAS= | 160.1 | FOM= | 0.91 | TEST= 0 |
| INDE | 3 | 15 | 40 | FOBS= | 241.1 | SIGMA= | 0.9 | PHAS= | -34.2 | FOM= | 0.93 | TEST= 0 |
| INDE | 3 | 15 | 42 | FOBS= | 39.3 | SIGMA= | 5.0 | PHAS= | -173.2 | FOM= | 0.45 | TEST= 0 |
| INDE | 3 | 15 | 44 | FOBS= | 232.2 | SIGMA= | 1.1 | PHAS= | 71.0 | FOM= | 0.94 | TEST= 0 |
| INDE | 3 | 15 | 46 | FOBS= | 163.8 | SIGMA= | 1.4 | PHAS= | -151.4 | FOM= | 0.94 | TEST= 0 |
| INDE | 3 | 15 | 48 | FOBS= | 390.5 | SIGMA= | 1.1 | PHAS= | 130.1 | FOM= | 0.99 | TEST= 0 |
| INDE | 3 | 15 | 50 | FOBS= | 109.1 | SIGMA= | 2.0 | PHAS= | 84.0 | FOM= | 0.67 | TEST= 0 |
| INDE | 3 | 15 | 52 | FOBS= | 86.2 | SIGMA= | 2.4 | PHAS= | -6.7 | FOM= | 0.91 | TEST= 0 |
| INDE | 3 | 15 | 54 | FOBS= | 66.1 | SIGMA= | 3.1 | PHAS= | -10.2 | FOM= | 0.50 | TEST= 0 |
| INDE | 3 | 15 | 56 | FOBS= | 46.1 | SIGMA= | 4.3 | PHAS= | 67.0 | FOM= | 0.49 | TEST= 1 |
| INDE | 3 | 15 | 58 | FOBS= | 56.3 | SIGMA= | 3.5 | PHAS= | 117.5 | FOM= | 0.55 | TEST= 0 |
| INDE | 3 | 15 | 60 | FOBS= | 71.9 | SIGMA= | 2.7 | PHAS= | -124.3 | FOM= | 0.85 | TEST= 0 |
| INDE | 3 | 15 | 62 | FOBS= | 134.1 | SIGMA= | 1.3 | PHAS= | 79.2 | FOM= | 0.92 | TEST= 0 |
| INDE | 3 | 15 | 64 | FOBS= | 68.1 | SIGMA= | 3.4 | PHAS= | 143.7 | FOM= | 0.68 | TEST= 0 |
| INDE | 3 | 15 | 66 | FOBS= | 68.3 | SIGMA= | 4.5 | PHAS= | 156.5 | FOM= | 0.84 | TEST= 0 |
| INDE | 3 | 15 | 68 | FOBS= | 43.6 | SIGMA= | 6.9 | PHAS= | 158.8 | FOM= | 0.73 | TEST= 0 |
| INDE | 3 | 15 | 70 | FOBS= | 30.2 | SIGMA= | 9.8 | PHAS= | 135.4 | FOM= | 0.30 | TEST= 0 |
| INDE | 3 | 15 | 72 | FOBS= | 60.4 | SIGMA= | 5.1 | PHAS= | 177.6 | FOM= | 0.85 | TEST= 0 |
| INDE | 3 | 15 | 74 | FOBS= | 54.5 | SIGMA= | 5.8 | PHAS= | 67.9 | FOM= | 0.85 | TEST= 0 |
| INDE | 3 | 15 | 76 | FOBS= | 14.4 | SIGMA= | 21.6 | PHAS= | 26.6 | FOM= | 0.35 | TEST= 0 |
| INDE | 3 | 16 | 9 | FOBS= | 453.4 | SIGMA= | 0.9 | PHAS= | 18.1 | FOM= | 0.79 | TEST= 0 |
| INDE | 3 | 16 | 11 | FOBS= | 182.8 | SIGMA= | 0.8 | PHAS= | 54.2 | FOM= | 0.94 | TEST= 0 |
| INDE | 3 | 16 | 13 | FOBS= | 143.1 | SIGMA= | 0.9 | PHAS= | 172.8 | FOM= | 0.87 | TEST= 0 |
| INDE | 3 | 16 | 15 | FOBS= | 301.5 | SIGMA= | 0.9 | PHAS= | 151.5 | FOM= | 0.48 | TEST= 1 |
| INDE | 3 | 16 | 17 | FOBS= | 94.1 | SIGMA= | 0.9 | PHAS= | -84.8 | FOM= | 0.88 | TEST= 0 |
| INDE | 3 | 16 | 19 | FOBS= | 224.2 | SIGMA= | 0.7 | PHAS= | -47.2 | FOM= | 0.93 | TEST= 0 |
| INDE | 3 | 16 | 21 | FOBS= | 47.6 | SIGMA= | 1.5 | PHAS= | -26.9 | FOM= | 0.88 | TEST= 1 |
| INDE | 3 | 16 | 23 | FOBS= | 158.0 | SIGMA= | 0.6 | PHAS= | 147.5 | FOM= | 0.90 | TEST= 0 |
| INDE | 3 | 16 | 25 | FOBS= | 186.1 | SIGMA= | 0.6 | PHAS= | -170.3 | FOM= | 0.98 | TEST= 0 |
| INDE | 3 | 16 | 27 | FOBS= | 203.2 | SIGMA= | 0.7 | PHAS= | -41.9 | FOM= | 0.90 | TEST= 0 |
| INDE | 3 | 16 | 29 | FOBS= | 132.5 | SIGMA= | 0.7 | PHAS= | -65.8 | FOM= | 0.99 | TEST= 0 |
| INDE | 3 | 16 | 31 | FOBS= | 175.7 | SIGMA= | 0.6 | PHAS= | 150.1 | FOM= | 0.93 | TEST= 0 |
| INDE | 3 | 16 | 33 | FOBS= | 149.4 | SIGMA= | 0.9 | PHAS= | 17.2 | FOM= | 0.99 | TEST= 0 |
| INDE | 3 | 16 | 35 | FOBS= | 263.9 | SIGMA= | 0.6 | PHAS= | 53.3 | FOM= | 0.95 | TEST= 0 |
| INDE | 3 | 16 | 37 | FOBS= | 179.6 | SIGMA= | 0.7 | PHAS= | -154.3 | FOM= | 0.99 | TEST= 0 |
| INDE | 3 | 16 | 39 | FOBS= | 26.6 | SIGMA= | 3.7 | PHAS= | -102.0 | FOM= | 0.36 | TEST= 0 |
| INDE | 3 | 16 | 41 | FOBS= | 208.2 | SIGMA= | 1.0 | PHAS= | -156.4 | FOM= | 0.95 | TEST= 0 |
| INDE | 3 | 16 | 43 | FOBS= | 90.1 | SIGMA= | 2.2 | PHAS= | 55.2 | FOM= | 0.77 | TEST= 0 |
| INDE | 3 | 16 | 45 | FOBS= | 40.5 | SIGMA= | 5.3 | PHAS= | -157.6 | FOM= | 0.71 | TEST= 0 |
| INDE | 3 | 16 | 47 | FOBS= | 124.4 | SIGMA= | 1.8 | PHAS= | 54.0 | FOM= | 0.92 | TEST= 0 |
| INDE | 3 | 16 | 49 | FOBS= | 230.7 | SIGMA= | 1.2 | PHAS= | 49.6 | FOM= | 0.96 | TEST= 0 |
| INDE | 3 | 16 | 51 | FOBS= | 48.0 | SIGMA= | 4.2 | PHAS= | -49.2 | FOM= | 0.51 | TEST= 0 |
| INDE | 3 | 16 | 53 | FOBS= | 190.4 | SIGMA= | 1.2 | PHAS= | -83.6 | FOM= | 0.94 | TEST= 0 |
| INDE | 3 | 16 | 55 | FOBS= | 26.9 | SIGMA= | 7.4 | PHAS= | -97.0 | FOM= | 0.14 | TEST= 0 |

*FIG. 12A - 82*

| | | | | | | | | | | | | |
|---|---|---|---|---|---|---|---|---|---|---|---|---|
| INDE | 3 | 16 | 57 | FOBS= | 0.0 | SIGMA= | 19.8 | PHAS= | 0.0 | FOM= | 0.00 | TEST= 1 |
| INDE | 3 | 16 | 59 | FOBS= | 101.5 | SIGMA= | 2.0 | PHAS= | -23.4 | FOM= | 0.92 | TEST= 0 |
| INDE | 3 | 16 | 61 | FOBS= | 0.0 | SIGMA= | 21.5 | PHAS= | 0.0 | FOM= | 0.00 | TEST= 0 |
| INDE | 3 | 16 | 63 | FOBS= | 104.8 | SIGMA= | 1.8 | PHAS= | 66.6 | FOM= | 0.85 | TEST= 0 |
| INDE | 3 | 16 | 65 | FOBS= | 20.5 | SIGMA= | 14.9 | PHAS= | -62.7 | FOM= | 0.09 | TEST= 0 |
| INDE | 3 | 16 | 67 | FOBS= | 92.9 | SIGMA= | 3.3 | PHAS= | 112.9 | FOM= | 0.76 | TEST= 0 |
| INDE | 3 | 16 | 69 | FOBS= | 44.9 | SIGMA= | 6.8 | PHAS= | -59.9 | FOM= | 0.84 | TEST= 0 |
| INDE | 3 | 16 | 71 | FOBS= | 62.8 | SIGMA= | 4.9 | PHAS= | 67.1 | FOM= | 0.65 | TEST= 0 |
| INDE | 3 | 16 | 73 | FOBS= | 23.7 | SIGMA= | 13.1 | PHAS= | 69.2 | FOM= | 0.68 | TEST= 0 |
| INDE | 3 | 16 | 75 | FOBS= | 22.0 | SIGMA= | 14.3 | PHAS= | -114.0 | FOM= | 0.33 | TEST= 1 |
| INDE | 3 | 17 | 6 | FOBS= | 188.1 | SIGMA= | 0.5 | PHAS= | 72.5 | FOM= | 0.56 | TEST= 0 |
| INDE | 3 | 17 | 8 | FOBS= | 491.2 | SIGMA= | 0.9 | PHAS= | -110.2 | FOM= | 0.91 | TEST= 0 |
| INDE | 3 | 17 | 10 | FOBS= | 390.0 | SIGMA= | 0.7 | PHAS= | -51.1 | FOM= | 0.96 | TEST= 0 |
| INDE | 3 | 17 | 12 | FOBS= | 35.5 | SIGMA= | 3.1 | PHAS= | -19.4 | FOM= | 0.66 | TEST= 0 |
| INDE | 3 | 17 | 14 | FOBS= | 314.5 | SIGMA= | 0.7 | PHAS= | -168.9 | FOM= | 0.93 | TEST= 0 |
| INDE | 3 | 17 | 16 | FOBS= | 104.6 | SIGMA= | 1.0 | PHAS= | 68.3 | FOM= | 0.65 | TEST= 0 |
| INDE | 3 | 17 | 18 | FOBS= | 327.8 | SIGMA= | 0.7 | PHAS= | -109.5 | FOM= | 0.96 | TEST= 0 |
| INDE | 3 | 17 | 20 | FOBS= | 148.0 | SIGMA= | 0.7 | PHAS= | 170.2 | FOM= | 0.56 | TEST= 0 |
| INDE | 3 | 17 | 22 | FOBS= | 54.6 | SIGMA= | 1.4 | PHAS= | 31.1 | FOM= | 0.96 | TEST= 0 |
| INDE | 3 | 17 | 24 | FOBS= | 93.3 | SIGMA= | 0.8 | PHAS= | 98.5 | FOM= | 0.98 | TEST= 0 |
| INDE | 3 | 17 | 26 | FOBS= | 0.0 | SIGMA= | 12.2 | PHAS= | 0.0 | FOM= | 0.00 | TEST= 0 |
| INDE | 3 | 17 | 28 | FOBS= | 61.7 | SIGMA= | 1.3 | PHAS= | -99.3 | FOM= | 0.93 | TEST= 0 |
| INDE | 3 | 17 | 30 | FOBS= | 67.8 | SIGMA= | 1.3 | PHAS= | 58.5 | FOM= | 0.95 | TEST= 0 |
| INDE | 3 | 17 | 32 | FOBS= | 201.6 | SIGMA= | 0.6 | PHAS= | 137.8 | FOM= | 0.95 | TEST= 0 |
| INDE | 3 | 17 | 34 | FOBS= | 283.2 | SIGMA= | 0.6 | PHAS= | 58.0 | FOM= | 0.99 | TEST= 0 |
| INDE | 3 | 17 | 36 | FOBS= | 325.2 | SIGMA= | 0.5 | PHAS= | -81.2 | FOM= | 0.99 | TEST= 0 |
| INDE | 3 | 17 | 38 | FOBS= | 244.6 | SIGMA= | 0.7 | PHAS= | -176.2 | FOM= | 0.98 | TEST= 0 |
| INDE | 3 | 17 | 40 | FOBS= | 207.6 | SIGMA= | 0.9 | PHAS= | 98.4 | FOM= | 0.92 | TEST= 0 |
| INDE | 3 | 17 | 42 | FOBS= | 119.2 | SIGMA= | 1.1 | PHAS= | 141.4 | FOM= | 0.96 | TEST= 0 |
| INDE | 3 | 17 | 44 | FOBS= | 102.5 | SIGMA= | 2.1 | PHAS= | 125.4 | FOM= | 0.90 | TEST= 0 |
| INDE | 3 | 17 | 46 | FOBS= | 213.0 | SIGMA= | 1.1 | PHAS= | -34.5 | FOM= | 0.92 | TEST= 1 |
| INDE | 3 | 17 | 48 | FOBS= | 86.7 | SIGMA= | 2.5 | PHAS= | 55.7 | FOM= | 0.84 | TEST= 0 |
| INDE | 3 | 17 | 50 | FOBS= | 119.4 | SIGMA= | 1.8 | PHAS= | -131.1 | FOM= | 0.90 | TEST= 0 |
| INDE | 3 | 17 | 52 | FOBS= | 80.1 | SIGMA= | 2.6 | PHAS= | 103.9 | FOM= | 0.52 | TEST= 0 |
| INDE | 3 | 17 | 54 | FOBS= | 177.1 | SIGMA= | 1.3 | PHAS= | -171.7 | FOM= | 0.81 | TEST= 0 |
| INDE | 3 | 17 | 56 | FOBS= | 120.3 | SIGMA= | 1.7 | PHAS= | 174.8 | FOM= | 0.94 | TEST= 0 |
| INDE | 3 | 17 | 58 | FOBS= | 97.5 | SIGMA= | 2.1 | PHAS= | -121.0 | FOM= | 0.72 | TEST= 0 |
| INDE | 3 | 17 | 60 | FOBS= | 105.9 | SIGMA= | 1.9 | PHAS= | -155.1 | FOM= | 0.89 | TEST= 0 |
| INDE | 3 | 17 | 62 | FOBS= | 118.9 | SIGMA= | 1.9 | PHAS= | 116.6 | FOM= | 0.92 | TEST= 0 |
| INDE | 3 | 17 | 64 | FOBS= | 67.5 | SIGMA= | 4.7 | PHAS= | -6.3 | FOM= | 0.77 | TEST= 0 |
| INDE | 3 | 17 | 66 | FOBS= | 0.0 | SIGMA= | 24.6 | PHAS= | 0.0 | FOM= | 0.00 | TEST= 0 |
| INDE | 3 | 17 | 68 | FOBS= | 130.5 | SIGMA= | 2.5 | PHAS= | -43.7 | FOM= | 0.42 | TEST= 1 |
| INDE | 3 | 17 | 70 | FOBS= | 0.0 | SIGMA= | 24.7 | PHAS= | 0.0 | FOM= | 0.00 | TEST= 1 |
| INDE | 3 | 17 | 72 | FOBS= | 0.0 | SIGMA= | 24.9 | PHAS= | 0.0 | FOM= | 0.00 | TEST= 0 |
| INDE | 3 | 17 | 74 | FOBS= | 68.1 | SIGMA= | 4.8 | PHAS= | 24.9 | FOM= | 0.92 | TEST= 0 |
| INDE | 3 | 18 | 3 | FOBS= | 180.8 | SIGMA= | 0.6 | PHAS= | -76.8 | FOM= | 0.98 | TEST= 0 |
| INDE | 3 | 18 | 5 | FOBS= | 124.3 | SIGMA= | 0.5 | PHAS= | 35.2 | FOM= | 0.23 | TEST= 0 |
| INDE | 3 | 18 | 7 | FOBS= | 191.3 | SIGMA= | 0.6 | PHAS= | 78.9 | FOM= | 0.80 | TEST= 0 |
| INDE | 3 | 18 | 9 | FOBS= | 89.3 | SIGMA= | 1.4 | PHAS= | 131.8 | FOM= | 0.35 | TEST= 0 |
| INDE | 3 | 18 | 11 | FOBS= | 88.2 | SIGMA= | 1.4 | PHAS= | -129.4 | FOM= | 0.31 | TEST= 0 |
| INDE | 3 | 18 | 13 | FOBS= | 66.0 | SIGMA= | 1.9 | PHAS= | 169.9 | FOM= | 0.90 | TEST= 0 |
| INDE | 3 | 18 | 15 | FOBS= | 94.5 | SIGMA= | 1.4 | PHAS= | 67.6 | FOM= | 0.84 | TEST= 0 |
| INDE | 3 | 18 | 17 | FOBS= | 100.9 | SIGMA= | 1.3 | PHAS= | -176.2 | FOM= | 0.84 | TEST= 0 |
| INDE | 3 | 18 | 19 | FOBS= | 264.0 | SIGMA= | 0.7 | PHAS= | 166.6 | FOM= | 0.93 | TEST= 0 |
| INDE | 3 | 18 | 21 | FOBS= | 33.1 | SIGMA= | 2.6 | PHAS= | -123.5 | FOM= | 0.94 | TEST= 0 |
| INDE | 3 | 18 | 23 | FOBS= | 107.0 | SIGMA= | 0.8 | PHAS= | 65.3 | FOM= | 0.95 | TEST= 0 |
| INDE | 3 | 18 | 25 | FOBS= | 180.3 | SIGMA= | 0.5 | PHAS= | 75.0 | FOM= | 0.98 | TEST= 0 |
| INDE | 3 | 18 | 27 | FOBS= | 16.5 | SIGMA= | 4.7 | PHAS= | -172.6 | FOM= | 0.13 | TEST= 0 |
| INDE | 3 | 18 | 29 | FOBS= | 33.6 | SIGMA= | 2.5 | PHAS= | 45.7 | FOM= | 0.30 | TEST= 0 |
| INDE | 3 | 18 | 31 | FOBS= | 109.4 | SIGMA= | 0.9 | PHAS= | 101.5 | FOM= | 0.90 | TEST= 0 |
| INDE | 3 | 18 | 33 | FOBS= | 371.1 | SIGMA= | 0.6 | PHAS= | -30.2 | FOM= | 0.97 | TEST= 1 |
| INDE | 3 | 18 | 35 | FOBS= | 211.5 | SIGMA= | 0.7 | PHAS= | 32.2 | FOM= | 0.91 | TEST= 0 |
| INDE | 3 | 18 | 37 | FOBS= | 281.0 | SIGMA= | 0.7 | PHAS= | -156.1 | FOM= | 0.97 | TEST= 0 |
| INDE | 3 | 18 | 39 | FOBS= | 259.2 | SIGMA= | 0.7 | PHAS= | 77.8 | FOM= | 0.98 | TEST= 0 |
| INDE | 3 | 18 | 41 | FOBS= | 157.5 | SIGMA= | 0.8 | PHAS= | 38.8 | FOM= | 0.87 | TEST= 0 |
| INDE | 3 | 18 | 43 | FOBS= | 322.5 | SIGMA= | 0.6 | PHAS= | -16.4 | FOM= | 0.96 | TEST= 1 |
| INDE | 3 | 18 | 45 | FOBS= | 81.8 | SIGMA= | 2.6 | PHAS= | -150.3 | FOM= | 0.55 | TEST= 0 |
| INDE | 3 | 18 | 47 | FOBS= | 0.0 | SIGMA= | 20.7 | PHAS= | 0.0 | FOM= | 0.00 | TEST= 0 |
| INDE | 3 | 18 | 49 | FOBS= | 109.2 | SIGMA= | 2.2 | PHAS= | -167.1 | FOM= | 0.66 | TEST= 0 |
| INDE | 3 | 18 | 51 | FOBS= | 86.6 | SIGMA= | 2.4 | PHAS= | -108.1 | FOM= | 0.71 | TEST= 1 |

*FIG. 12A - 83*

| | | | | | | | | | | | | |
|---|---|---|---|---|---|---|---|---|---|---|---|---|
| INDE | 3 | 18 | 53 | FOBS= | 114.7 | SIGMA= | 1.9 | PHAS= | -54.6 | FOM= | 0.46 | TEST= 1 |
| INDE | 3 | 18 | 55 | FOBS= | 210.1 | SIGMA= | 1.1 | PHAS= | 89.9 | FOM= | 0.96 | TEST= 0 |
| INDE | 3 | 18 | 57 | FOBS= | 152.6 | SIGMA= | 1.4 | PHAS= | 139.7 | FOM= | 0.89 | TEST= 0 |
| INDE | 3 | 18 | 59 | FOBS= | 50.4 | SIGMA= | 3.9 | PHAS= | -92.1 | FOM= | 0.48 | TEST= 0 |
| INDE | 3 | 18 | 61 | FOBS= | 79.2 | SIGMA= | 2.5 | PHAS= | 75.0 | FOM= | 0.89 | TEST= 0 |
| INDE | 3 | 18 | 63 | FOBS= | 113.4 | SIGMA= | 1.7 | PHAS= | -84.3 | FOM= | 0.88 | TEST= 0 |
| INDE | 3 | 18 | 65 | FOBS= | 0.0 | SIGMA= | 24.9 | PHAS= | 0.0 | FOM= | 0.00 | TEST= 0 |
| INDE | 3 | 18 | 67 | FOBS= | 50.5 | SIGMA= | 6.2 | PHAS= | -134.2 | FOM= | 0.69 | TEST= 0 |
| INDE | 3 | 18 | 69 | FOBS= | 84.6 | SIGMA= | 3.8 | PHAS= | -40.1 | FOM= | 0.88 | TEST= 0 |
| INDE | 3 | 18 | 71 | FOBS= | 48.1 | SIGMA= | 6.5 | PHAS= | -34.8 | FOM= | 0.80 | TEST= 0 |
| INDE | 3 | 18 | 73 | FOBS= | 56.6 | SIGMA= | 5.7 | PHAS= | 135.7 | FOM= | 0.59 | TEST= 0 |
| INDE | 3 | 18 | 75 | FOBS= | 0.0 | SIGMA= | 25.6 | PHAS= | 0.0 | FOM= | 0.00 | TEST= 0 |
| INDE | 3 | 19 | 4 | FOBS= | 150.8 | SIGMA= | 0.7 | PHAS= | 6.3 | FOM= | 0.96 | TEST= 0 |
| INDE | 3 | 19 | 6 | FOBS= | 103.2 | SIGMA= | 1.0 | PHAS= | 10.9 | FOM= | 0.62 | TEST= 1 |
| INDE | 3 | 19 | 8 | FOBS= | 193.1 | SIGMA= | 0.7 | PHAS= | -31.8 | FOM= | 0.94 | TEST= 0 |
| INDE | 3 | 19 | 10 | FOBS= | 91.7 | SIGMA= | 1.4 | PHAS= | -124.5 | FOM= | 0.49 | TEST= 0 |
| INDE | 3 | 19 | 12 | FOBS= | 62.8 | SIGMA= | 2.0 | PHAS= | 116.4 | FOM= | 0.87 | TEST= 0 |
| INDE | 3 | 19 | 14 | FOBS= | 178.0 | SIGMA= | 0.9 | PHAS= | -147.8 | FOM= | 0.85 | TEST= 0 |
| INDE | 3 | 19 | 16 | FOBS= | 77.9 | SIGMA= | 1.7 | PHAS= | -99.6 | FOM= | 0.78 | TEST= 1 |
| INDE | 3 | 19 | 18 | FOBS= | 134.2 | SIGMA= | 0.9 | PHAS= | 29.2 | FOM= | 0.97 | TEST= 0 |
| INDE | 3 | 19 | 20 | FOBS= | 108.5 | SIGMA= | 0.9 | PHAS= | 63.4 | FOM= | 0.96 | TEST= 0 |
| INDE | 3 | 19 | 22 | FOBS= | 120.5 | SIGMA= | 0.9 | PHAS= | -33.6 | FOM= | 0.99 | TEST= 0 |
| INDE | 3 | 19 | 24 | FOBS= | 118.4 | SIGMA= | 0.8 | PHAS= | -94.3 | FOM= | 0.99 | TEST= 0 |
| INDE | 3 | 19 | 26 | FOBS= | 188.9 | SIGMA= | 0.5 | PHAS= | -30.7 | FOM= | 0.92 | TEST= 0 |
| INDE | 3 | 19 | 28 | FOBS= | 105.2 | SIGMA= | 0.9 | PHAS= | -11.0 | FOM= | 0.75 | TEST= 0 |
| INDE | 3 | 19 | 30 | FOBS= | 28.5 | SIGMA= | 3.1 | PHAS= | 104.2 | FOM= | 0.68 | TEST= 0 |
| INDE | 3 | 19 | 32 | FOBS= | 118.2 | SIGMA= | 0.9 | PHAS= | 32.2 | FOM= | 0.80 | TEST= 0 |
| INDE | 3 | 19 | 34 | FOBS= | 71.5 | SIGMA= | 1.7 | PHAS= | -147.7 | FOM= | 0.97 | TEST= 1 |
| INDE | 3 | 19 | 36 | FOBS= | 172.1 | SIGMA= | 0.9 | PHAS= | -114.0 | FOM= | 0.98 | TEST= 0 |
| INDE | 3 | 19 | 38 | FOBS= | 80.9 | SIGMA= | 1.4 | PHAS= | -72.2 | FOM= | 0.91 | TEST= 0 |
| INDE | 3 | 19 | 40 | FOBS= | 115.7 | SIGMA= | 1.1 | PHAS= | 151.8 | FOM= | 0.94 | TEST= 0 |
| INDE | 3 | 19 | 42 | FOBS= | 312.7 | SIGMA= | 0.7 | PHAS= | -60.0 | FOM= | 0.97 | TEST= 0 |
| INDE | 3 | 19 | 44 | FOBS= | 167.3 | SIGMA= | 1.0 | PHAS= | -93.6 | FOM= | 0.96 | TEST= 0 |
| INDE | 3 | 19 | 46 | FOBS= | 171.0 | SIGMA= | 1.2 | PHAS= | -22.1 | FOM= | 0.91 | TEST= 1 |
| INDE | 3 | 19 | 48 | FOBS= | 154.6 | SIGMA= | 1.5 | PHAS= | 118.0 | FOM= | 0.96 | TEST= 0 |
| INDE | 3 | 19 | 50 | FOBS= | 187.8 | SIGMA= | 1.2 | PHAS= | 118.1 | FOM= | 0.97 | TEST= 0 |
| INDE | 3 | 19 | 52 | FOBS= | 193.3 | SIGMA= | 1.2 | PHAS= | 71.4 | FOM= | 0.91 | TEST= 0 |
| INDE | 3 | 19 | 54 | FOBS= | 86.6 | SIGMA= | 2.4 | PHAS= | 112.6 | FOM= | 0.88 | TEST= 0 |
| INDE | 3 | 19 | 56 | FOBS= | 0.0 | SIGMA= | 21.2 | PHAS= | 0.0 | FOM= | 0.00 | TEST= 0 |
| INDE | 3 | 19 | 58 | FOBS= | 105.5 | SIGMA= | 2.0 | PHAS= | 56.8 | FOM= | 0.93 | TEST= 0 |
| INDE | 3 | 19 | 60 | FOBS= | 61.5 | SIGMA= | 3.3 | PHAS= | -114.8 | FOM= | 0.76 | TEST= 0 |
| INDE | 3 | 19 | 62 | FOBS= | 22.9 | SIGMA= | 11.9 | PHAS= | -166.4 | FOM= | 0.27 | TEST= 0 |
| INDE | 3 | 19 | 64 | FOBS= | 36.8 | SIGMA= | 8.6 | PHAS= | 51.0 | FOM= | 0.46 | TEST= 0 |
| INDE | 3 | 19 | 66 | FOBS= | 33.9 | SIGMA= | 9.2 | PHAS= | 135.3 | FOM= | 0.23 | TEST= 0 |
| INDE | 3 | 19 | 68 | FOBS= | 44.1 | SIGMA= | 7.2 | PHAS= | 107.8 | FOM= | 0.66 | TEST= 0 |
| INDE | 3 | 19 | 70 | FOBS= | 62.7 | SIGMA= | 5.0 | PHAS= | -135.4 | FOM= | 0.88 | TEST= 0 |
| INDE | 3 | 19 | 72 | FOBS= | 17.1 | SIGMA= | 18.8 | PHAS= | -58.0 | FOM= | 0.35 | TEST= 0 |
| INDE | 3 | 19 | 74 | FOBS= | 35.9 | SIGMA= | 9.1 | PHAS= | 1.8 | FOM= | 0.45 | TEST= 0 |
| INDE | 3 | 20 | 3 | FOBS= | 413.6 | SIGMA= | 0.5 | PHAS= | -74.2 | FOM= | 0.98 | TEST= 0 |
| INDE | 3 | 20 | 5 | FOBS= | 517.0 | SIGMA= | 0.5 | PHAS= | -109.9 | FOM= | 0.98 | TEST= 0 |
| INDE | 3 | 20 | 7 | FOBS= | 64.7 | SIGMA= | 1.5 | PHAS= | -80.4 | FOM= | 0.85 | TEST= 0 |
| INDE | 3 | 20 | 9 | FOBS= | 53.6 | SIGMA= | 1.5 | PHAS= | 122.3 | FOM= | 0.75 | TEST= 1 |
| INDE | 3 | 20 | 11 | FOBS= | 203.7 | SIGMA= | 0.9 | PHAS= | 72.0 | FOM= | 0.90 | TEST= 0 |
| INDE | 3 | 20 | 13 | FOBS= | 90.8 | SIGMA= | 1.5 | PHAS= | -131.9 | FOM= | 0.96 | TEST= 0 |
| INDE | 3 | 20 | 15 | FOBS= | 104.0 | SIGMA= | 1.4 | PHAS= | -38.3 | FOM= | 0.11 | TEST= 0 |
| INDE | 3 | 20 | 17 | FOBS= | 81.8 | SIGMA= | 1.7 | PHAS= | 40.1 | FOM= | 0.99 | TEST= 0 |
| INDE | 3 | 20 | 19 | FOBS= | 147.5 | SIGMA= | 0.8 | PHAS= | -48.7 | FOM= | 0.91 | TEST= 0 |
| INDE | 3 | 20 | 21 | FOBS= | 159.5 | SIGMA= | 0.7 | PHAS= | -0.7 | FOM= | 0.99 | TEST= 0 |
| INDE | 3 | 20 | 23 | FOBS= | 141.0 | SIGMA= | 0.8 | PHAS= | 162.6 | FOM= | 0.83 | TEST= 0 |
| INDE | 3 | 20 | 25 | FOBS= | 68.1 | SIGMA= | 1.5 | PHAS= | -166.8 | FOM= | 0.98 | TEST= 0 |
| INDE | 3 | 20 | 27 | FOBS= | 115.6 | SIGMA= | 0.9 | PHAS= | -122.5 | FOM= | 0.98 | TEST= 0 |
| INDE | 3 | 20 | 29 | FOBS= | 43.4 | SIGMA= | 2.0 | PHAS= | 140.9 | FOM= | 0.98 | TEST= 0 |
| INDE | 3 | 20 | 31 | FOBS= | 91.8 | SIGMA= | 1.1 | PHAS= | -13.5 | FOM= | 0.94 | TEST= 0 |
| INDE | 3 | 20 | 33 | FOBS= | 313.4 | SIGMA= | 0.5 | PHAS= | -1.7 | FOM= | 0.98 | TEST= 0 |
| INDE | 3 | 20 | 35 | FOBS= | 245.2 | SIGMA= | 0.7 | PHAS= | 109.5 | FOM= | 0.94 | TEST= 0 |
| INDE | 3 | 20 | 37 | FOBS= | 203.2 | SIGMA= | 0.8 | PHAS= | -175.6 | FOM= | 0.92 | TEST= 0 |
| INDE | 3 | 20 | 39 | FOBS= | 265.9 | SIGMA= | 0.6 | PHAS= | 131.4 | FOM= | 0.97 | TEST= 0 |
| INDE | 3 | 20 | 41 | FOBS= | 143.9 | SIGMA= | 0.9 | PHAS= | 164.9 | FOM= | 0.98 | TEST= 0 |
| INDE | 3 | 20 | 43 | FOBS= | 187.1 | SIGMA= | 0.9 | PHAS= | -114.0 | FOM= | 0.90 | TEST= 0 |
| INDE | 3 | 20 | 45 | FOBS= | 148.3 | SIGMA= | 0.9 | PHAS= | 135.2 | FOM= | 0.37 | TEST= 0 |

*FIG. 12A - 84*

| | | | | | | | | | | | | | |
|---|---|---|---|---|---|---|---|---|---|---|---|---|---|
| INDE | 3 | 20 | 47 | FOBS= | 0.0 | SIGMA= | 17.2 | PHAS= | 0.0 | FOM= | 0.00 | TEST= | 0 |
| INDE | 3 | 20 | 49 | FOBS= | 231.9 | SIGMA= | 1.1 | PHAS= | 43.1 | FOM= | 0.97 | TEST= | 0 |
| INDE | 3 | 20 | 51 | FOBS= | 208.5 | SIGMA= | 1.1 | PHAS= | -44.1 | FOM= | 0.54 | TEST= | 1 |
| INDE | 3 | 20 | 53 | FOBS= | 65.9 | SIGMA= | 3.1 | PHAS= | 22.6 | FOM= | 0.78 | TEST= | 0 |
| INDE | 3 | 20 | 55 | FOBS= | 44.8 | SIGMA= | 4.6 | PHAS= | 46.9 | FOM= | 0.17 | TEST= | 0 |
| INDE | 3 | 20 | 57 | FOBS= | 20.6 | SIGMA= | 10.7 | PHAS= | 90.2 | FOM= | 0.23 | TEST= | 0 |
| INDE | 3 | 20 | 59 | FOBS= | 37.8 | SIGMA= | 5.3 | PHAS= | -53.4 | FOM= | 0.67 | TEST= | 0 |
| INDE | 3 | 20 | 61 | FOBS= | 0.0 | SIGMA= | 19.8 | PHAS= | 0.0 | FOM= | 0.00 | TEST= | 0 |
| INDE | 3 | 20 | 63 | FOBS= | 167.2 | SIGMA= | 1.7 | PHAS= | -175.2 | FOM= | 0.23 | TEST= | 1 |
| INDE | 3 | 20 | 65 | FOBS= | 0.0 | SIGMA= | 25.3 | PHAS= | 0.0 | FOM= | 0.00 | TEST= | 0 |
| INDE | 3 | 20 | 67 | FOBS= | 24.1 | SIGMA= | 13.2 | PHAS= | -154.4 | FOM= | 0.20 | TEST= | 0 |
| INDE | 3 | 20 | 69 | FOBS= | 28.7 | SIGMA= | 11.2 | PHAS= | 52.1 | FOM= | 0.53 | TEST= | 0 |
| INDE | 3 | 20 | 71 | FOBS= | 0.0 | SIGMA= | 25.2 | PHAS= | 0.0 | FOM= | 0.00 | TEST= | 0 |
| INDE | 3 | 20 | 73 | FOBS= | 103.1 | SIGMA= | 3.3 | PHAS= | -129.8 | FOM= | 0.93 | TEST= | 0 |
| INDE | 3 | 20 | 75 | FOBS= | 27.7 | SIGMA= | 12.1 | PHAS= | 120.3 | FOM= | 0.53 | TEST= | 0 |
| INDE | 3 | 21 | 4 | FOBS= | 277.3 | SIGMA= | 0.6 | PHAS= | -158.1 | FOM= | 0.91 | TEST= | 0 |
| INDE | 3 | 21 | 6 | FOBS= | 186.0 | SIGMA= | 0.7 | PHAS= | 162.7 | FOM= | 0.85 | TEST= | 0 |
| INDE | 3 | 21 | 8 | FOBS= | 156.8 | SIGMA= | 0.8 | PHAS= | -26.0 | FOM= | 0.55 | TEST= | 0 |
| INDE | 3 | 21 | 10 | FOBS= | 146.2 | SIGMA= | 1.1 | PHAS= | 106.1 | FOM= | 0.72 | TEST= | 0 |
| INDE | 3 | 21 | 12 | FOBS= | 153.1 | SIGMA= | 1.1 | PHAS= | 80.4 | FOM= | 0.96 | TEST= | 0 |
| INDE | 3 | 21 | 14 | FOBS= | 5.1 | SIGMA= | 25.2 | PHAS= | 108.3 | FOM= | 0.02 | TEST= | 0 |
| INDE | 3 | 21 | 16 | FOBS= | 212.4 | SIGMA= | 0.9 | PHAS= | -40.5 | FOM= | 0.99 | TEST= | 0 |
| INDE | 3 | 21 | 18 | FOBS= | 244.0 | SIGMA= | 0.8 | PHAS= | -53.8 | FOM= | 0.97 | TEST= | 0 |
| INDE | 3 | 21 | 20 | FOBS= | 136.2 | SIGMA= | 0.8 | PHAS= | -95.4 | FOM= | 0.99 | TEST= | 0 |
| INDE | 3 | 21 | 22 | FOBS= | 183.7 | SIGMA= | 0.8 | PHAS= | -134.9 | FOM= | 0.90 | TEST= | 1 |
| INDE | 3 | 21 | 24 | FOBS= | 240.7 | SIGMA= | 0.6 | PHAS= | -165.3 | FOM= | 0.97 | TEST= | 0 |
| INDE | 3 | 21 | 26 | FOBS= | 59.0 | SIGMA= | 1.8 | PHAS= | 39.9 | FOM= | 0.97 | TEST= | 0 |
| INDE | 3 | 21 | 28 | FOBS= | 191.3 | SIGMA= | 0.6 | PHAS= | -51.9 | FOM= | 0.98 | TEST= | 0 |
| INDE | 3 | 21 | 30 | FOBS= | 166.5 | SIGMA= | 0.7 | PHAS= | 143.3 | FOM= | 0.90 | TEST= | 0 |
| INDE | 3 | 21 | 32 | FOBS= | 60.9 | SIGMA= | 1.9 | PHAS= | 156.9 | FOM= | 0.86 | TEST= | 0 |
| INDE | 3 | 21 | 34 | FOBS= | 331.6 | SIGMA= | 0.7 | PHAS= | -106.7 | FOM= | 0.88 | TEST= | 1 |
| INDE | 3 | 21 | 36 | FOBS= | 154.2 | SIGMA= | 1.0 | PHAS= | 99.0 | FOM= | 0.97 | TEST= | 0 |
| INDE | 3 | 21 | 38 | FOBS= | 173.0 | SIGMA= | 1.0 | PHAS= | 19.0 | FOM= | 0.92 | TEST= | 0 |
| INDE | 3 | 21 | 40 | FOBS= | 255.2 | SIGMA= | 0.8 | PHAS= | 93.8 | FOM= | 0.93 | TEST= | 0 |
| INDE | 3 | 21 | 42 | FOBS= | 60.9 | SIGMA= | 2.3 | PHAS= | 48.8 | FOM= | 0.85 | TEST= | 0 |
| INDE | 3 | 21 | 44 | FOBS= | 94.0 | SIGMA= | 1.5 | PHAS= | 127.7 | FOM= | 0.69 | TEST= | 0 |
| INDE | 3 | 21 | 46 | FOBS= | 79.3 | SIGMA= | 1.7 | PHAS= | 33.6 | FOM= | 0.66 | TEST= | 0 |
| INDE | 3 | 21 | 48 | FOBS= | 147.3 | SIGMA= | 1.1 | PHAS= | -113.4 | FOM= | 0.44 | TEST= | 0 |
| INDE | 3 | 21 | 50 | FOBS= | 60.4 | SIGMA= | 3.3 | PHAS= | -109.7 | FOM= | 0.94 | TEST= | 0 |
| INDE | 3 | 21 | 52 | FOBS= | 73.3 | SIGMA= | 2.9 | PHAS= | 32.0 | FOM= | 0.11 | TEST= | 0 |
| INDE | 3 | 21 | 54 | FOBS= | 121.7 | SIGMA= | 1.8 | PHAS= | 65.9 | FOM= | 0.88 | TEST= | 0 |
| INDE | 3 | 21 | 56 | FOBS= | 31.4 | SIGMA= | 7.0 | PHAS= | 159.2 | FOM= | 0.36 | TEST= | 0 |
| INDE | 3 | 21 | 58 | FOBS= | 23.3 | SIGMA= | 10.2 | PHAS= | 65.2 | FOM= | 0.04 | TEST= | 0 |
| INDE | 3 | 21 | 60 | FOBS= | 0.0 | SIGMA= | 19.9 | PHAS= | 0.0 | FOM= | 0.00 | TEST= | 0 |
| INDE | 3 | 21 | 62 | FOBS= | 77.0 | SIGMA= | 3.1 | PHAS= | 119.8 | FOM= | 0.17 | TEST= | 1 |
| INDE | 3 | 21 | 64 | FOBS= | 56.8 | SIGMA= | 8.0 | PHAS= | 117.7 | FOM= | 0.70 | TEST= | 0 |
| INDE | 3 | 21 | 66 | FOBS= | 40.3 | SIGMA= | 8.1 | PHAS= | 65.2 | FOM= | 0.67 | TEST= | 0 |
| INDE | 3 | 21 | 68 | FOBS= | 14.5 | SIGMA= | 22.2 | PHAS= | 32.6 | FOM= | 0.08 | TEST= | 0 |
| INDE | 3 | 21 | 70 | FOBS= | 0.0 | SIGMA= | 25.4 | PHAS= | 0.0 | FOM= | 0.00 | TEST= | 0 |
| INDE | 3 | 21 | 72 | FOBS= | 54.6 | SIGMA= | 6.0 | PHAS= | -158.1 | FOM= | 0.83 | TEST= | 0 |
| INDE | 3 | 21 | 74 | FOBS= | 59.2 | SIGMA= | 5.7 | PHAS= | 131.0 | FOM= | 0.79 | TEST= | 0 |
| INDE | 3 | 22 | 3 | FOBS= | 173.9 | SIGMA= | 0.7 | PHAS= | -36.8 | FOM= | 0.91 | TEST= | 0 |
| INDE | 3 | 22 | 5 | FOBS= | 280.2 | SIGMA= | 0.6 | PHAS= | -67.4 | FOM= | 0.53 | TEST= | 1 |
| INDE | 3 | 22 | 7 | FOBS= | 87.0 | SIGMA= | 1.2 | PHAS= | 114.2 | FOM= | 0.91 | TEST= | 1 |
| INDE | 3 | 22 | 9 | FOBS= | 206.2 | SIGMA= | 0.7 | PHAS= | 103.8 | FOM= | 0.95 | TEST= | 0 |
| INDE | 3 | 22 | 11 | FOBS= | 387.5 | SIGMA= | 0.8 | PHAS= | 31.2 | FOM= | 0.95 | TEST= | 0 |
| INDE | 3 | 22 | 13 | FOBS= | 107.8 | SIGMA= | 1.4 | PHAS= | 51.8 | FOM= | 0.98 | TEST= | 1 |
| INDE | 3 | 22 | 15 | FOBS= | 227.1 | SIGMA= | 0.9 | PHAS= | -77.3 | FOM= | 0.99 | TEST= | 0 |
| INDE | 3 | 22 | 17 | FOBS= | 144.8 | SIGMA= | 1.2 | PHAS= | -130.6 | FOM= | 0.98 | TEST= | 0 |
| INDE | 3 | 22 | 19 | FOBS= | 159.2 | SIGMA= | 1.1 | PHAS= | -129.7 | FOM= | 0.99 | TEST= | 0 |
| INDE | 3 | 22 | 21 | FOBS= | 88.3 | SIGMA= | 1.2 | PHAS= | 38.3 | FOM= | 0.92 | TEST= | 0 |
| INDE | 3 | 22 | 23 | FOBS= | 216.7 | SIGMA= | 0.7 | PHAS= | 68.3 | FOM= | 0.93 | TEST= | 0 |
| INDE | 3 | 22 | 25 | FOBS= | 165.4 | SIGMA= | 0.8 | PHAS= | 117.6 | FOM= | 0.99 | TEST= | 0 |
| INDE | 3 | 22 | 27 | FOBS= | 169.2 | SIGMA= | 0.9 | PHAS= | -126.7 | FOM= | 0.99 | TEST= | 0 |
| INDE | 3 | 22 | 29 | FOBS= | 186.0 | SIGMA= | 0.8 | PHAS= | 96.6 | FOM= | 0.94 | TEST= | 1 |
| INDE | 3 | 22 | 31 | FOBS= | 223.0 | SIGMA= | 0.6 | PHAS= | 99.0 | FOM= | 0.96 | TEST= | 0 |
| INDE | 3 | 22 | 33 | FOBS= | 147.5 | SIGMA= | 0.8 | PHAS= | -64.8 | FOM= | 0.98 | TEST= | 0 |
| INDE | 3 | 22 | 35 | FOBS= | 89.5 | SIGMA= | 1.5 | PHAS= | -99.4 | FOM= | 0.81 | TEST= | 1 |
| INDE | 3 | 22 | 37 | FOBS= | 38.0 | SIGMA= | 3.3 | PHAS= | 53.4 | FOM= | 0.96 | TEST= | 0 |
| INDE | 3 | 22 | 39 | FOBS= | 92.9 | SIGMA= | 1.6 | PHAS= | 76.0 | FOM= | 0.81 | TEST= | 0 |

*FIG. 12A - 85*

```
INDE  3  22  41  FOBS=    0.0  SIGMA=  18.4  PHAS=    0.0  FOM=  0.00  TEST= 0
INDE  3  22  43  FOBS=   54.4  SIGMA=   2.6  PHAS=   67.9  FOM=  0.66  TEST= 0
INDE  3  22  45  FOBS=  126.5  SIGMA=   1.1  PHAS=   55.0  FOM=  0.92  TEST= 0
INDE  3  22  47  FOBS=  242.3  SIGMA=   0.6  PHAS= -152.1  FOM=  0.93  TEST= 0
INDE  3  22  49  FOBS=  138.4  SIGMA=   1.0  PHAS=  136.9  FOM=  0.86  TEST= 0
INDE  3  22  51  FOBS=   88.9  SIGMA=   2.1  PHAS=  -70.0  FOM=  0.92  TEST= 0
INDE  3  22  53  FOBS=  165.6  SIGMA=   1.4  PHAS=  -26.0  FOM=  0.93  TEST= 0
INDE  3  22  55  FOBS=   41.2  SIGMA=   5.4  PHAS=  -43.2  FOM=  0.42  TEST= 0
INDE  3  22  57  FOBS=    0.0  SIGMA=  20.1  PHAS=    0.0  FOM=  0.00  TEST= 0
INDE  3  22  59  FOBS=    0.0  SIGMA=  19.9  PHAS=    0.0  FOM=  0.00  TEST= 0
INDE  3  22  61  FOBS=    0.0  SIGMA=  23.2  PHAS=    0.0  FOM=  0.00  TEST= 0
INDE  3  22  63  FOBS=   71.8  SIGMA=   4.4  PHAS=  -46.7  FOM=  0.77  TEST= 0
INDE  3  22  65  FOBS=   58.2  SIGMA=   5.7  PHAS=  -28.7  FOM=  0.22  TEST= 0
INDE  3  22  67  FOBS=   41.0  SIGMA=   8.0  PHAS=   -7.6  FOM=  0.02  TEST= 1
INDE  3  22  69  FOBS=   12.4  SIGMA=  35.9  PHAS=  -48.6  FOM=  0.20  TEST= 0
INDE  3  22  71  FOBS=   77.3  SIGMA=   4.3  PHAS=  145.3  FOM=  0.84  TEST= 0
INDE  3  22  73  FOBS=   46.2  SIGMA=   7.3  PHAS=  -99.4  FOM=  0.39  TEST= 0
INDE  3  23   4  FOBS=  317.6  SIGMA=   0.5  PHAS=  -99.2  FOM=  0.97  TEST= 0
INDE  3  23   6  FOBS=   70.6  SIGMA=   1.5  PHAS=   82.3  FOM=  0.61  TEST= 0
INDE  3  23   8  FOBS=  110.8  SIGMA=   1.0  PHAS= -129.6  FOM=  0.95  TEST= 1
INDE  3  23  10  FOBS=   53.5  SIGMA=   2.1  PHAS=   45.5  FOM=  0.74  TEST= 1
INDE  3  23  12  FOBS=  252.6  SIGMA=   0.9  PHAS=  -64.7  FOM=  0.77  TEST= 0
INDE  3  23  14  FOBS=  185.7  SIGMA=   1.0  PHAS=  -59.7  FOM=  0.98  TEST= 0
INDE  3  23  16  FOBS=   91.4  SIGMA=   1.7  PHAS= -142.9  FOM=  0.79  TEST= 0
INDE  3  23  18  FOBS=  140.5  SIGMA=   1.2  PHAS= -100.4  FOM=  0.83  TEST= 0
INDE  3  23  20  FOBS=   88.3  SIGMA=   1.8  PHAS=  -12.5  FOM=  0.92  TEST= 1
INDE  3  23  22  FOBS=  131.8  SIGMA=   0.9  PHAS=  -75.7  FOM=  0.96  TEST= 0
INDE  3  23  24  FOBS=   10.0  SIGMA=  12.2  PHAS=  -10.5  FOM=  0.45  TEST= 0
INDE  3  23  26  FOBS=  155.0  SIGMA=   0.8  PHAS=   82.1  FOM=  0.94  TEST= 0
INDE  3  23  28  FOBS=  124.2  SIGMA=   1.0  PHAS=  136.2  FOM=  0.69  TEST= 0
INDE  3  23  30  FOBS=  210.1  SIGMA=   0.7  PHAS=   22.0  FOM=  0.98  TEST= 0
INDE  3  23  32  FOBS=   57.5  SIGMA=   2.1  PHAS=   49.8  FOM=  0.79  TEST= 0
INDE  3  23  34  FOBS=  322.7  SIGMA=   0.6  PHAS= -145.6  FOM=  0.92  TEST= 0
INDE  3  23  36  FOBS=   26.8  SIGMA=   6.1  PHAS=   -9.3  FOM=  0.05  TEST= 0
INDE  3  23  38  FOBS=   72.9  SIGMA=   1.7  PHAS=   -6.9  FOM=  0.80  TEST= 0
INDE  3  23  40  FOBS=  149.3  SIGMA=   0.9  PHAS=   -2.5  FOM=  0.96  TEST= 0
INDE  3  23  42  FOBS=  133.3  SIGMA=   1.2  PHAS=  -26.4  FOM=  0.74  TEST= 0
INDE  3  23  44  FOBS=  159.4  SIGMA=   1.0  PHAS=   61.5  FOM=  0.88  TEST= 0
INDE  3  23  46  FOBS=  291.1  SIGMA=   0.7  PHAS=  132.4  FOM=  0.97  TEST= 0
INDE  3  23  48  FOBS=  229.1  SIGMA=   0.7  PHAS=   74.3  FOM=  0.95  TEST= 0
INDE  3  23  50  FOBS=    0.0  SIGMA=  16.2  PHAS=    0.0  FOM=  0.00  TEST= 0
INDE  3  23  52  FOBS=   78.2  SIGMA=   2.3  PHAS= -159.3  FOM=  0.86  TEST= 0
INDE  3  23  54  FOBS=  102.0  SIGMA=   2.1  PHAS= -100.4  FOM=  0.73  TEST= 0
INDE  3  23  56  FOBS=   50.3  SIGMA=   4.1  PHAS=  -93.6  FOM=  0.73  TEST= 0
INDE  3  23  58  FOBS=   62.4  SIGMA=   3.3  PHAS=  114.4  FOM=  0.08  TEST= 1
INDE  3  23  60  FOBS=   37.2  SIGMA=   5.4  PHAS=   23.9  FOM=  0.08  TEST= 0
INDE  3  23  62  FOBS=  113.3  SIGMA=   2.9  PHAS=    0.5  FOM=  0.90  TEST= 0
INDE  3  23  64  FOBS=   69.8  SIGMA=   6.7  PHAS= -127.7  FOM=  0.83  TEST= 0
INDE  3  23  66  FOBS=    0.0  SIGMA=  25.7  PHAS=    0.0  FOM=  0.00  TEST= 0
INDE  3  23  68  FOBS=   46.4  SIGMA=   7.2  PHAS=  -92.8  FOM=  0.29  TEST= 0
INDE  3  23  70  FOBS=   36.1  SIGMA=   9.2  PHAS=  171.7  FOM=  0.36  TEST= 0
INDE  3  23  72  FOBS=   34.3  SIGMA=   9.8  PHAS=   81.4  FOM=  0.50  TEST= 0
INDE  3  23  74  FOBS=   45.8  SIGMA=   7.5  PHAS= -129.8  FOM=  0.35  TEST= 0
INDE  3  24   3  FOBS=  196.5  SIGMA=   0.6  PHAS= -156.2  FOM=  0.93  TEST= 0
INDE  3  24   5  FOBS=  172.3  SIGMA=   0.5  PHAS= -121.3  FOM=  0.89  TEST= 0
INDE  3  24   7  FOBS=   65.3  SIGMA=   1.6  PHAS=  -95.9  FOM=  0.81  TEST= 0
INDE  3  24   9  FOBS=   57.7  SIGMA=   1.9  PHAS= -174.9  FOM=  0.96  TEST= 0
INDE  3  24  11  FOBS=   86.1  SIGMA=   2.5  PHAS= -146.6  FOM=  0.36  TEST= 0
INDE  3  24  13  FOBS=  287.3  SIGMA=   0.9  PHAS=  -86.5  FOM=  0.99  TEST= 0
INDE  3  24  15  FOBS=  180.7  SIGMA=   1.1  PHAS= -102.5  FOM=  0.96  TEST= 0
INDE  3  24  17  FOBS=   97.5  SIGMA=   1.7  PHAS=  118.7  FOM=  0.96  TEST= 0
INDE  3  24  19  FOBS=  155.8  SIGMA=   1.2  PHAS= -153.6  FOM=  0.97  TEST= 0
INDE  3  24  21  FOBS=   99.5  SIGMA=   1.3  PHAS= -146.9  FOM=  0.94  TEST= 0
INDE  3  24  23  FOBS=  160.9  SIGMA=   0.8  PHAS=    0.5  FOM=  0.91  TEST= 0
INDE  3  24  25  FOBS=   67.5  SIGMA=   1.7  PHAS=   -3.4  FOM=  0.91  TEST= 1
INDE  3  24  27  FOBS=  114.4  SIGMA=   1.1  PHAS=  -74.9  FOM=  0.96  TEST= 0
INDE  3  24  29  FOBS=   98.0  SIGMA=   1.3  PHAS=  -52.6  FOM=  0.65  TEST= 0
INDE  3  24  31  FOBS=  102.5  SIGMA=   1.4  PHAS=  166.0  FOM=  0.90  TEST= 0
INDE  3  24  33  FOBS=  115.2  SIGMA=   1.2  PHAS=  -77.8  FOM=  0.97  TEST= 0
INDE  3  24  35  FOBS=  242.7  SIGMA=   0.6  PHAS= -126.9  FOM=  0.97  TEST= 0
```

*FIG. 12A - 86*

```
INDE  3  24  37  FOBS=  127.4  SIGMA=   1.2  PHAS=    73.9  FOM=  0.98  TEST= 0
INDE  3  24  39  FOBS=  136.6  SIGMA=   1.0  PHAS=   -45.4  FOM=  0.94  TEST= 0
INDE  3  24  41  FOBS=  191.8  SIGMA=   0.7  PHAS=  -112.8  FOM=  0.95  TEST= 0
INDE  3  24  43  FOBS=   95.7  SIGMA=   1.6  PHAS=   -83.7  FOM=  0.90  TEST= 0
INDE  3  24  45  FOBS=  275.7  SIGMA=   0.7  PHAS=    48.3  FOM=  0.96  TEST= 0
INDE  3  24  47  FOBS=  247.6  SIGMA=   0.8  PHAS=   -15.7  FOM=  0.95  TEST= 0
INDE  3  24  49  FOBS=  147.6  SIGMA=   1.0  PHAS=   -63.2  FOM=  0.91  TEST= 0
INDE  3  24  51  FOBS=  192.1  SIGMA=   0.8  PHAS=    86.8  FOM=  0.95  TEST= 0
INDE  3  24  53  FOBS=   98.6  SIGMA=   1.7  PHAS=    63.4  FOM=  0.92  TEST= 0
INDE  3  24  55  FOBS=  128.5  SIGMA=   1.7  PHAS=   145.6  FOM=  0.56  TEST= 1
INDE  3  24  57  FOBS=   49.0  SIGMA=   4.2  PHAS=   140.2  FOM=  0.43  TEST= 0
INDE  3  24  59  FOBS=   75.9  SIGMA=   2.7  PHAS=   -18.4  FOM=  0.75  TEST= 0
INDE  3  24  61  FOBS=   72.1  SIGMA=   3.4  PHAS=   -52.2  FOM=  0.06  TEST= 1
INDE  3  24  63  FOBS=  126.0  SIGMA=   2.7  PHAS=   174.4  FOM=  0.26  TEST= 1
INDE  3  24  65  FOBS=    0.0  SIGMA=  30.4  PHAS=     0.0  FOM=  0.00  TEST= 0
INDE  3  24  67  FOBS=   96.3  SIGMA=   3.6  PHAS=  -152.1  FOM=  0.85  TEST= 0
INDE  3  24  69  FOBS=   60.5  SIGMA=   5.5  PHAS=    96.3  FOM=  0.38  TEST= 0
INDE  3  24  71  FOBS=   52.9  SIGMA=   6.4  PHAS=   113.4  FOM=  0.16  TEST= 0
INDE  3  24  73  FOBS=   36.0  SIGMA=   9.7  PHAS=   130.7  FOM=  0.34  TEST= 0
INDE  3  25   4  FOBS=  182.1  SIGMA=   0.7  PHAS=   150.2  FOM=  0.96  TEST= 0
INDE  3  25   6  FOBS=   39.1  SIGMA=   2.6  PHAS=   123.6  FOM=  0.97  TEST= 0
INDE  3  25   8  FOBS=   85.2  SIGMA=   1.3  PHAS=   -11.6  FOM=  0.95  TEST= 0
INDE  3  25  10  FOBS=  100.8  SIGMA=   1.3  PHAS=   151.5  FOM=  0.93  TEST= 0
INDE  3  25  12  FOBS=  196.3  SIGMA=   1.5  PHAS=   134.7  FOM=  0.86  TEST= 0
INDE  3  25  14  FOBS=  103.8  SIGMA=   1.6  PHAS=  -157.6  FOM=  0.96  TEST= 0
INDE  3  25  16  FOBS=   97.6  SIGMA=   1.7  PHAS=   -13.8  FOM=  0.99  TEST= 1
INDE  3  25  18  FOBS=  149.8  SIGMA=   1.2  PHAS=   177.7  FOM=  0.87  TEST= 0
INDE  3  25  20  FOBS=  263.5  SIGMA=   0.9  PHAS=   103.1  FOM=  0.99  TEST= 0
INDE  3  25  22  FOBS=  256.2  SIGMA=   0.8  PHAS=  -102.3  FOM=  0.97  TEST= 0
INDE  3  25  24  FOBS=  110.3  SIGMA=   1.1  PHAS=   -81.8  FOM=  0.99  TEST= 0
INDE  3  25  26  FOBS=   38.0  SIGMA=   3.2  PHAS=   118.1  FOM=  0.18  TEST= 0
INDE  3  25  28  FOBS=   54.2  SIGMA=   2.4  PHAS=   159.3  FOM=  0.91  TEST= 0
INDE  3  25  30  FOBS=  107.6  SIGMA=   1.3  PHAS=   -44.6  FOM=  0.70  TEST= 0
INDE  3  25  32  FOBS=  104.3  SIGMA=   1.4  PHAS=   -88.2  FOM=  0.86  TEST= 0
INDE  3  25  34  FOBS=  294.3  SIGMA=   0.8  PHAS=   155.3  FOM=  0.97  TEST= 0
INDE  3  25  36  FOBS=  169.3  SIGMA=   1.0  PHAS=  -131.6  FOM=  0.94  TEST= 0
INDE  3  25  38  FOBS=  178.0  SIGMA=   0.9  PHAS=    22.2  FOM=  0.83  TEST= 0
INDE  3  25  40  FOBS=  289.4  SIGMA=   0.6  PHAS=   -73.0  FOM=  0.97  TEST= 0
INDE  3  25  42  FOBS=   55.7  SIGMA=   2.4  PHAS=   -95.8  FOM=  0.95  TEST= 0
INDE  3  25  44  FOBS=    0.0  SIGMA=  17.2  PHAS=     0.0  FOM=  0.00  TEST= 0
INDE  3  25  46  FOBS=  168.6  SIGMA=   1.0  PHAS=   -71.7  FOM=  0.80  TEST= 0
INDE  3  25  48  FOBS=   21.2  SIGMA=   6.6  PHAS=  -106.5  FOM=  0.37  TEST= 0
INDE  3  25  50  FOBS=   26.0  SIGMA=   5.5  PHAS=   124.2  FOM=  0.41  TEST= 0
INDE  3  25  52  FOBS=   81.5  SIGMA=   1.7  PHAS=    12.3  FOM=  0.68  TEST= 0
INDE  3  25  54  FOBS=   91.5  SIGMA=   1.9  PHAS=   -29.0  FOM=  0.87  TEST= 0
INDE  3  25  56  FOBS=  129.5  SIGMA=   1.6  PHAS=    34.4  FOM=  0.90  TEST= 0
INDE  3  25  58  FOBS=   32.1  SIGMA=   6.3  PHAS=   115.6  FOM=  0.70  TEST= 0
INDE  3  25  60  FOBS=   82.6  SIGMA=   3.0  PHAS=   -94.4  FOM=  0.75  TEST= 0
INDE  3  25  62  FOBS=   83.0  SIGMA=   3.9  PHAS=   -14.4  FOM=  0.91  TEST= 0
INDE  3  25  64  FOBS=    0.0  SIGMA=  25.2  PHAS=     0.0  FOM=  0.00  TEST= 0
INDE  3  25  66  FOBS=   67.1  SIGMA=   5.2  PHAS=    -7.8  FOM=  0.72  TEST= 0
INDE  3  25  68  FOBS=   52.9  SIGMA=   6.5  PHAS=   115.3  FOM=  0.85  TEST= 0
INDE  3  25  70  FOBS=   27.6  SIGMA=  12.4  PHAS=   106.8  FOM=  0.44  TEST= 1
INDE  3  25  72  FOBS=   38.3  SIGMA=   9.0  PHAS=    60.1  FOM=  0.61  TEST= 0
INDE  3  26   3  FOBS=  149.8  SIGMA=   0.8  PHAS=    31.9  FOM=  0.99  TEST= 0
INDE  3  26   5  FOBS=  122.7  SIGMA=   0.7  PHAS=   147.0  FOM=  0.66  TEST= 0
INDE  3  26   7  FOBS=  100.7  SIGMA=   1.2  PHAS=   -39.4  FOM=  0.98  TEST= 0
INDE  3  26   9  FOBS=  185.5  SIGMA=   0.8  PHAS=   -71.9  FOM=  0.99  TEST= 0
INDE  3  26  11  FOBS=   88.0  SIGMA=   1.5  PHAS=   104.0  FOM=  0.39  TEST= 0
INDE  3  26  13  FOBS=   92.6  SIGMA=   2.5  PHAS=   -98.4  FOM=  0.14  TEST= 0
INDE  3  26  15  FOBS=   53.6  SIGMA=   3.0  PHAS=   176.6  FOM=  0.65  TEST= 0
INDE  3  26  17  FOBS=   64.3  SIGMA=   2.6  PHAS=   172.6  FOM=  0.94  TEST= 0
INDE  3  26  19  FOBS=  157.8  SIGMA=   1.2  PHAS=     1.5  FOM=  0.99  TEST= 0
INDE  3  26  21  FOBS=   18.9  SIGMA=   8.8  PHAS=  -129.0  FOM=  0.39  TEST= 0
INDE  3  26  23  FOBS=  133.2  SIGMA=   1.1  PHAS=   179.4  FOM=  0.98  TEST= 0
INDE  3  26  25  FOBS=  184.0  SIGMA=   0.8  PHAS=   -71.1  FOM=  0.98  TEST= 0
INDE  3  26  27  FOBS=  122.1  SIGMA=   1.2  PHAS=  -157.7  FOM=  0.91  TEST= 0
INDE  3  26  29  FOBS=   57.5  SIGMA=   2.4  PHAS=   -20.7  FOM=  0.12  TEST= 1
INDE  3  26  31  FOBS=  234.7  SIGMA=   0.8  PHAS=   165.3  FOM=  0.95  TEST= 0
INDE  3  26  33  FOBS=    0.0  SIGMA=  17.5  PHAS=     0.0  FOM=  0.00  TEST= 1
```

*FIG. 12A - 87*

| | | | | | | | | | | | |
|---|---|---|---|---|---|---|---|---|---|---|---|
| INDE | 3 | 26 | 35 | FOBS= | 257.0 | SIGMA= | 0.8 | PHAS= | -148.5 | FOM= | 0.94 | TEST= 0
| INDE | 3 | 26 | 37 | FOBS= | 204.5 | SIGMA= | 0.9 | PHAS= | -134.1 | FOM= | 0.91 | TEST= 0
| INDE | 3 | 26 | 39 | FOBS= | 91.0 | SIGMA= | 1.8 | PHAS= | 123.2 | FOM= | 0.48 | TEST= 0
| INDE | 3 | 26 | 41 | FOBS= | 279.5 | SIGMA= | 0.7 | PHAS= | -145.0 | FOM= | 0.97 | TEST= 0
| INDE | 3 | 26 | 43 | FOBS= | 197.8 | SIGMA= | 0.7 | PHAS= | -12.5 | FOM= | 0.94 | TEST= 0
| INDE | 3 | 26 | 45 | FOBS= | 0.0 | SIGMA= | 17.2 | PHAS= | 0.0 | FOM= | 0.00 | TEST= 0
| INDE | 3 | 26 | 47 | FOBS= | 111.2 | SIGMA= | 1.3 | PHAS= | -126.9 | FOM= | 0.88 | TEST= 0
| INDE | 3 | 26 | 49 | FOBS= | 67.4 | SIGMA= | 2.0 | PHAS= | -18.1 | FOM= | 0.84 | TEST= 0
| INDE | 3 | 26 | 51 | FOBS= | 126.1 | SIGMA= | 1.1 | PHAS= | 80.6 | FOM= | 0.73 | TEST= 0
| INDE | 3 | 26 | 53 | FOBS= | 0.0 | SIGMA= | 16.8 | PHAS= | 0.0 | FOM= | 0.00 | TEST= 0
| INDE | 3 | 26 | 55 | FOBS= | 130.9 | SIGMA= | 1.3 | PHAS= | -138.1 | FOM= | 0.90 | TEST= 0
| INDE | 3 | 26 | 57 | FOBS= | 39.6 | SIGMA= | 4.8 | PHAS= | 58.7 | FOM= | 0.35 | TEST= 0
| INDE | 3 | 26 | 59 | FOBS= | 67.7 | SIGMA= | 3.1 | PHAS= | 47.1 | FOM= | 0.73 | TEST= 0
| INDE | 3 | 26 | 61 | FOBS= | 105.6 | SIGMA= | 3.2 | PHAS= | -173.3 | FOM= | 0.89 | TEST= 0
| INDE | 3 | 26 | 63 | FOBS= | 129.7 | SIGMA= | 2.6 | PHAS= | -152.6 | FOM= | 0.96 | TEST= 0
| INDE | 3 | 26 | 65 | FOBS= | 75.3 | SIGMA= | 6.3 | PHAS= | -79.8 | FOM= | 0.80 | TEST= 0
| INDE | 3 | 26 | 67 | FOBS= | 55.6 | SIGMA= | 6.4 | PHAS= | -149.7 | FOM= | 0.81 | TEST= 0
| INDE | 3 | 26 | 69 | FOBS= | 67.0 | SIGMA= | 5.2 | PHAS= | -8.6 | FOM= | 0.79 | TEST= 0
| INDE | 3 | 26 | 71 | FOBS= | 59.4 | SIGMA= | 5.9 | PHAS= | -30.9 | FOM= | 0.78 | TEST= 0
| INDE | 3 | 26 | 73 | FOBS= | 0.0 | SIGMA= | 26.6 | PHAS= | 0.0 | FOM= | 0.00 | TEST= 0
| INDE | 3 | 27 | 4 | FOBS= | 64.4 | SIGMA= | 1.6 | PHAS= | -86.3 | FOM= | 0.89 | TEST= 0
| INDE | 3 | 27 | 6 | FOBS= | 113.3 | SIGMA= | 0.7 | PHAS= | -133.5 | FOM= | 0.93 | TEST= 0
| INDE | 3 | 27 | 8 | FOBS= | 131.6 | SIGMA= | 1.0 | PHAS= | -129.7 | FOM= | 0.99 | TEST= 0
| INDE | 3 | 27 | 10 | FOBS= | 127.7 | SIGMA= | 1.1 | PHAS= | 173.3 | FOM= | 0.99 | TEST= 0
| INDE | 3 | 27 | 12 | FOBS= | 114.7 | SIGMA= | 1.2 | PHAS= | 100.6 | FOM= | 0.98 | TEST= 0
| INDE | 3 | 27 | 14 | FOBS= | 17.6 | SIGMA= | 9.3 | PHAS= | -157.0 | FOM= | 0.05 | TEST= 1
| INDE | 3 | 27 | 16 | FOBS= | 126.4 | SIGMA= | 1.5 | PHAS= | 57.0 | FOM= | 0.97 | TEST= 0
| INDE | 3 | 27 | 18 | FOBS= | 273.4 | SIGMA= | 0.9 | PHAS= | -92.4 | FOM= | 0.99 | TEST= 0
| INDE | 3 | 27 | 20 | FOBS= | 31.2 | SIGMA= | 5.5 | PHAS= | 111.9 | FOM= | 0.66 | TEST= 1
| INDE | 3 | 27 | 22 | FOBS= | 71.6 | SIGMA= | 2.5 | PHAS= | -131.2 | FOM= | 0.43 | TEST= 0
| INDE | 3 | 27 | 24 | FOBS= | 186.2 | SIGMA= | 1.0 | PHAS= | 105.7 | FOM= | 0.95 | TEST= 0
| INDE | 3 | 27 | 26 | FOBS= | 170.8 | SIGMA= | 0.9 | PHAS= | 133.3 | FOM= | 0.92 | TEST= 0
| INDE | 3 | 27 | 28 | FOBS= | 131.0 | SIGMA= | 1.2 | PHAS= | -99.3 | FOM= | 0.91 | TEST= 0
| INDE | 3 | 27 | 30 | FOBS= | 83.4 | SIGMA= | 1.8 | PHAS= | 115.7 | FOM= | 0.87 | TEST= 0
| INDE | 3 | 27 | 32 | FOBS= | 193.3 | SIGMA= | 0.9 | PHAS= | -152.5 | FOM= | 0.89 | TEST= 0
| INDE | 3 | 27 | 34 | FOBS= | 159.9 | SIGMA= | 1.1 | PHAS= | -152.8 | FOM= | 0.96 | TEST= 0
| INDE | 3 | 27 | 36 | FOBS= | 431.0 | SIGMA= | 0.9 | PHAS= | 149.5 | FOM= | 0.98 | TEST= 0
| INDE | 3 | 27 | 38 | FOBS= | 257.7 | SIGMA= | 0.9 | PHAS= | 76.5 | FOM= | 0.96 | TEST= 0
| INDE | 3 | 27 | 40 | FOBS= | 119.4 | SIGMA= | 1.4 | PHAS= | -153.0 | FOM= | 0.92 | TEST= 0
| INDE | 3 | 27 | 42 | FOBS= | 266.8 | SIGMA= | 0.7 | PHAS= | 171.6 | FOM= | 0.95 | TEST= 0
| INDE | 3 | 27 | 44 | FOBS= | 57.7 | SIGMA= | 2.3 | PHAS= | -65.0 | FOM= | 0.43 | TEST= 0
| INDE | 3 | 27 | 46 | FOBS= | 94.0 | SIGMA= | 1.5 | PHAS= | 94.7 | FOM= | 0.95 | TEST= 0
| INDE | 3 | 27 | 48 | FOBS= | 88.1 | SIGMA= | 1.6 | PHAS= | -61.4 | FOM= | 0.79 | TEST= 0
| INDE | 3 | 27 | 50 | FOBS= | 93.2 | SIGMA= | 1.5 | PHAS= | -74.3 | FOM= | 0.77 | TEST= 0
| INDE | 3 | 27 | 52 | FOBS= | 71.4 | SIGMA= | 1.9 | PHAS= | 89.1 | FOM= | 0.78 | TEST= 0
| INDE | 3 | 27 | 54 | FOBS= | 61.6 | SIGMA= | 2.2 | PHAS= | 109.4 | FOM= | 0.54 | TEST= 0
| INDE | 3 | 27 | 56 | FOBS= | 0.0 | SIGMA= | 19.2 | PHAS= | 0.0 | FOM= | 0.00 | TEST= 0
| INDE | 3 | 27 | 58 | FOBS= | 19.7 | SIGMA= | 9.3 | PHAS= | 48.2 | FOM= | 0.37 | TEST= 0
| INDE | 3 | 27 | 60 | FOBS= | 96.8 | SIGMA= | 3.0 | PHAS= | 11.6 | FOM= | 0.84 | TEST= 0
| INDE | 3 | 27 | 62 | FOBS= | 63.9 | SIGMA= | 5.1 | PHAS= | 68.6 | FOM= | 0.70 | TEST= 0
| INDE | 3 | 27 | 64 | FOBS= | 28.4 | SIGMA= | 11.4 | PHAS= | 66.2 | FOM= | 0.54 | TEST= 0
| INDE | 3 | 27 | 66 | FOBS= | 89.0 | SIGMA= | 5.5 | PHAS= | 123.4 | FOM= | 0.90 | TEST= 0
| INDE | 3 | 27 | 68 | FOBS= | 0.0 | SIGMA= | 26.7 | PHAS= | 0.0 | FOM= | 0.00 | TEST= 0
| INDE | 3 | 27 | 70 | FOBS= | 62.7 | SIGMA= | 5.7 | PHAS= | 166.0 | FOM= | 0.80 | TEST= 0
| INDE | 3 | 27 | 72 | FOBS= | 0.0 | SIGMA= | 26.7 | PHAS= | 0.0 | FOM= | 0.00 | TEST= 1
| INDE | 3 | 28 | 3 | FOBS= | 128.0 | SIGMA= | 0.9 | PHAS= | -79.8 | FOM= | 0.98 | TEST= 0
| INDE | 3 | 28 | 5 | FOBS= | 278.1 | SIGMA= | 0.4 | PHAS= | 176.3 | FOM= | 0.99 | TEST= 0
| INDE | 3 | 28 | 7 | FOBS= | 169.7 | SIGMA= | 0.8 | PHAS= | 176.4 | FOM= | 0.99 | TEST= 0
| INDE | 3 | 28 | 9 | FOBS= | 115.2 | SIGMA= | 1.1 | PHAS= | -46.8 | FOM= | 0.99 | TEST= 0
| INDE | 3 | 28 | 11 | FOBS= | 32.9 | SIGMA= | 3.9 | PHAS= | -167.9 | FOM= | 0.84 | TEST= 0
| INDE | 3 | 28 | 15 | FOBS= | 162.9 | SIGMA= | 1.3 | PHAS= | -28.6 | FOM= | 0.27 | TEST= 1
| INDE | 3 | 28 | 17 | FOBS= | 170.7 | SIGMA= | 1.2 | PHAS= | -78.1 | FOM= | 0.90 | TEST= 0
| INDE | 3 | 28 | 19 | FOBS= | 275.9 | SIGMA= | 1.0 | PHAS= | 152.3 | FOM= | 0.97 | TEST= 0
| INDE | 3 | 28 | 21 | FOBS= | 239.0 | SIGMA= | 1.0 | PHAS= | -74.7 | FOM= | 0.93 | TEST= 0
| INDE | 3 | 28 | 23 | FOBS= | 185.1 | SIGMA= | 1.2 | PHAS= | -1.1 | FOM= | 0.89 | TEST= 0
| INDE | 3 | 28 | 25 | FOBS= | 55.7 | SIGMA= | 2.5 | PHAS= | 83.6 | FOM= | 0.58 | TEST= 0
| INDE | 3 | 28 | 27 | FOBS= | 191.0 | SIGMA= | 0.9 | PHAS= | -158.4 | FOM= | 0.98 | TEST= 0
| INDE | 3 | 28 | 29 | FOBS= | 134.9 | SIGMA= | 1.2 | PHAS= | -163.0 | FOM= | 0.70 | TEST= 0
| INDE | 3 | 28 | 31 | FOBS= | 216.3 | SIGMA= | 1.0 | PHAS= | 137.1 | FOM= | 0.89 | TEST= 0
| INDE | 3 | 28 | 33 | FOBS= | 4.7 | SIGMA= | 45.5 | PHAS= | -32.5 | FOM= | 0.01 | TEST= 0

*FIG. 12A - 88*

```
INDE  3  28  35  FOBS=   26.0  SIGMA=   8.1  PHAS=  134.8  FOM= 0.72  TEST= 0
INDE  3  28  37  FOBS=  269.2  SIGMA=   0.9  PHAS=   61.2  FOM= 0.97  TEST= 0
INDE  3  28  39  FOBS=   64.2  SIGMA=   3.4  PHAS=   12.7  FOM= 0.62  TEST= 0
INDE  3  28  41  FOBS=  214.2  SIGMA=   1.0  PHAS=  111.6  FOM= 0.91  TEST= 0
INDE  3  28  43  FOBS=  139.0  SIGMA=   1.0  PHAS=  -18.8  FOM= 0.95  TEST= 0
INDE  3  28  45  FOBS=  158.1  SIGMA=   0.9  PHAS=  -96.3  FOM= 0.93  TEST= 0
INDE  3  28  47  FOBS=    0.0  SIGMA=  17.1  PHAS=    0.0  FOM= 0.00  TEST= 0
INDE  3  28  49  FOBS=   90.1  SIGMA=   1.6  PHAS= -170.3  FOM= 0.59  TEST= 0
INDE  3  28  51  FOBS=   92.9  SIGMA=   1.5  PHAS=  -63.0  FOM= 0.92  TEST= 0
INDE  3  28  53  FOBS=   85.0  SIGMA=   1.6  PHAS=  -22.3  FOM= 0.81  TEST= 0
INDE  3  28  55  FOBS=   66.0  SIGMA=   2.0  PHAS=  -95.3  FOM= 0.62  TEST= 1
INDE  3  28  57  FOBS=   47.6  SIGMA=   3.5  PHAS=   36.0  FOM= 0.46  TEST= 0
INDE  3  28  59  FOBS=   49.3  SIGMA=   3.7  PHAS=   72.2  FOM= 0.46  TEST= 0
INDE  3  28  61  FOBS=   35.7  SIGMA=   9.0  PHAS= -133.8  FOM= 0.62  TEST= 0
INDE  3  28  63  FOBS=   34.4  SIGMA=   9.4  PHAS=   35.4  FOM= 0.04  TEST= 1
INDE  3  28  65  FOBS=   20.3  SIGMA=  24.0  PHAS=  -46.2  FOM= 0.39  TEST= 0
INDE  3  28  67  FOBS=   35.7  SIGMA=  10.2  PHAS=  143.6  FOM= 0.28  TEST= 1
INDE  3  28  69  FOBS=   96.8  SIGMA=   3.8  PHAS=  -74.0  FOM= 0.94  TEST= 0
INDE  3  28  71  FOBS=   45.1  SIGMA=   8.1  PHAS=   93.2  FOM= 0.77  TEST= 0
INDE  3  29   4  FOBS=  143.8  SIGMA=   0.9  PHAS=   40.5  FOM= 0.97  TEST= 0
INDE  3  29   6  FOBS=  172.7  SIGMA=   0.6  PHAS=   76.2  FOM= 0.98  TEST= 0
INDE  3  29   8  FOBS=   38.7  SIGMA=   3.0  PHAS=  -84.8  FOM= 0.83  TEST= 0
INDE  3  29  10  FOBS=  179.2  SIGMA=   0.9  PHAS= -117.8  FOM= 0.63  TEST= 1
INDE  3  29  12  FOBS=  205.0  SIGMA=   0.9  PHAS=   28.1  FOM= 0.96  TEST= 0
INDE  3  29  14  FOBS=   90.2  SIGMA=   2.8  PHAS=  -16.7  FOM= 0.53  TEST= 0
INDE  3  29  16  FOBS=  194.6  SIGMA=   1.2  PHAS= -120.3  FOM= 0.90  TEST= 0
INDE  3  29  18  FOBS=  139.1  SIGMA=   1.5  PHAS=  -78.4  FOM= 0.79  TEST= 0
INDE  3  29  20  FOBS=  132.4  SIGMA=   1.6  PHAS=    1.1  FOM= 0.92  TEST= 0
INDE  3  29  22  FOBS=  149.8  SIGMA=   1.5  PHAS= -163.8  FOM= 0.92  TEST= 0
INDE  3  29  24  FOBS=  152.8  SIGMA=   1.5  PHAS=  -73.6  FOM= 0.86  TEST= 0
INDE  3  29  26  FOBS=  160.7  SIGMA=   1.1  PHAS=   72.0  FOM= 0.98  TEST= 0
INDE  3  29  28  FOBS=  180.0  SIGMA=   1.0  PHAS= -158.7  FOM= 0.96  TEST= 0
INDE  3  29  30  FOBS=   44.6  SIGMA=   3.6  PHAS=   13.6  FOM= 0.79  TEST= 0
INDE  3  29  32  FOBS=  193.1  SIGMA=   1.0  PHAS=  156.5  FOM= 0.93  TEST= 0
INDE  3  29  34  FOBS=  221.6  SIGMA=   0.9  PHAS= -146.5  FOM= 0.98  TEST= 0
INDE  3  29  36  FOBS=    0.0  SIGMA=  21.4  PHAS=    0.0  FOM= 0.00  TEST= 0
INDE  3  29  38  FOBS=  270.5  SIGMA=   0.9  PHAS=   34.7  FOM= 0.97  TEST= 0
INDE  3  29  40  FOBS=  122.2  SIGMA=   1.7  PHAS= -138.3  FOM= 0.83  TEST= 0
INDE  3  29  42  FOBS=  179.3  SIGMA=   1.0  PHAS= -167.3  FOM= 0.90  TEST= 0
INDE  3  29  44  FOBS=  131.7  SIGMA=   1.2  PHAS=  172.4  FOM= 0.87  TEST= 0
INDE  3  29  46  FOBS=  151.5  SIGMA=   0.9  PHAS= -162.2  FOM= 0.84  TEST= 1
INDE  3  29  48  FOBS=   64.2  SIGMA=   2.1  PHAS=  -56.9  FOM= 0.63  TEST= 0
INDE  3  29  50  FOBS=   44.1  SIGMA=   3.1  PHAS=   90.6  FOM= 0.66  TEST= 0
INDE  3  29  52  FOBS=   89.6  SIGMA=   1.6  PHAS=  101.4  FOM= 0.82  TEST= 0
INDE  3  29  54  FOBS=   22.8  SIGMA=   6.5  PHAS=  174.0  FOM= 0.35  TEST= 0
INDE  3  29  56  FOBS=  104.9  SIGMA=   1.5  PHAS=  -54.5  FOM= 0.87  TEST= 0
INDE  3  29  58  FOBS=  103.2  SIGMA=   1.8  PHAS=  115.9  FOM= 0.62  TEST= 0
INDE  3  29  60  FOBS=   72.2  SIGMA=   2.8  PHAS=   -1.7  FOM= 0.25  TEST= 0
INDE  3  29  62  FOBS=   48.9  SIGMA=   6.7  PHAS=   70.2  FOM= 0.80  TEST= 0
INDE  3  29  64  FOBS=   60.9  SIGMA=   5.4  PHAS=  135.2  FOM= 0.90  TEST= 0
INDE  3  29  66  FOBS=   46.8  SIGMA=  10.6  PHAS= -113.8  FOM= 0.67  TEST= 0
INDE  3  29  68  FOBS=    0.0  SIGMA=  27.0  PHAS=    0.0  FOM= 0.00  TEST= 0
INDE  3  29  70  FOBS=   40.9  SIGMA=   8.9  PHAS= -146.9  FOM= 0.43  TEST= 0
INDE  3  29  72  FOBS=   31.4  SIGMA=  11.9  PHAS=   49.6  FOM= 0.53  TEST= 0
INDE  3  30   3  FOBS=  205.1  SIGMA=   0.7  PHAS=  -61.0  FOM= 0.93  TEST= 0
INDE  3  30   5  FOBS=  179.4  SIGMA=   0.8  PHAS=  -79.4  FOM= 0.98  TEST= 0
INDE  3  30   7  FOBS=  207.6  SIGMA=   0.5  PHAS=  -92.6  FOM= 0.91  TEST= 0
INDE  3  30   9  FOBS=  113.5  SIGMA=   1.2  PHAS=  153.6  FOM= 0.95  TEST= 1
INDE  3  30  11  FOBS=  184.5  SIGMA=   0.9  PHAS= -124.7  FOM= 0.94  TEST= 1
INDE  3  30  13  FOBS=  154.1  SIGMA=   1.1  PHAS=  -32.8  FOM= 0.94  TEST= 0
INDE  3  30  15  FOBS=  124.6  SIGMA=   2.3  PHAS= -125.9  FOM= 0.34  TEST= 0
INDE  3  30  17  FOBS=  171.0  SIGMA=   1.3  PHAS=  -21.0  FOM= 0.87  TEST= 0
INDE  3  30  19  FOBS=  125.7  SIGMA=   1.7  PHAS= -169.1  FOM= 0.99  TEST= 0
INDE  3  30  21  FOBS=  200.7  SIGMA=   1.2  PHAS=    7.7  FOM= 0.99  TEST= 0
INDE  3  30  23  FOBS=  158.9  SIGMA=   1.5  PHAS=   11.3  FOM= 0.96  TEST= 0
INDE  3  30  25  FOBS=  323.8  SIGMA=   0.9  PHAS=  139.6  FOM= 0.99  TEST= 0
INDE  3  30  27  FOBS=  137.2  SIGMA=   1.2  PHAS=  153.9  FOM= 0.97  TEST= 0
INDE  3  30  29  FOBS=  218.9  SIGMA=   0.9  PHAS= -144.9  FOM= 0.99  TEST= 0
INDE  3  30  31  FOBS=  192.3  SIGMA=   1.0  PHAS=  107.4  FOM= 0.98  TEST= 0
INDE  3  30  33  FOBS=  160.8  SIGMA=   1.2  PHAS=  119.5  FOM= 0.98  TEST= 0
```

*FIG. 12A - 89*

| | | | | | | | | | | | |
|---|---|---|---|---|---|---|---|---|---|---|---|
| INDE | 3 | 30 | 35 | FOBS= | 214.5 | SIGMA= | 1.0 | PHAS= | -179.3 | FOM= | 0.95 | TEST= 0 |
| INDE | 3 | 30 | 37 | FOBS= | 311.9 | SIGMA= | 0.8 | PHAS= | 54.4 | FOM= | 0.98 | TEST= 0 |
| INDE | 3 | 30 | 39 | FOBS= | 98.0 | SIGMA= | 2.3 | PHAS= | -20.4 | FOM= | 0.92 | TEST= 0 |
| INDE | 3 | 30 | 41 | FOBS= | 68.5 | SIGMA= | 2.6 | PHAS= | 114.2 | FOM= | 0.94 | TEST= 0 |
| INDE | 3 | 30 | 43 | FOBS= | 72.3 | SIGMA= | 2.1 | PHAS= | 85.6 | FOM= | 0.42 | TEST= 0 |
| INDE | 3 | 30 | 45 | FOBS= | 38.3 | SIGMA= | 3.5 | PHAS= | -117.1 | FOM= | 0.61 | TEST= 1 |
| INDE | 3 | 30 | 47 | FOBS= | 47.3 | SIGMA= | 2.7 | PHAS= | 100.4 | FOM= | 0.41 | TEST= 0 |
| INDE | 3 | 30 | 49 | FOBS= | 144.0 | SIGMA= | 1.0 | PHAS= | 166.6 | FOM= | 0.42 | TEST= 1 |
| INDE | 3 | 30 | 51 | FOBS= | 67.2 | SIGMA= | 2.1 | PHAS= | -7.0 | FOM= | 0.92 | TEST= 0 |
| INDE | 3 | 30 | 53 | FOBS= | 121.1 | SIGMA= | 1.2 | PHAS= | 89.0 | FOM= | 0.43 | TEST= 0 |
| INDE | 3 | 30 | 55 | FOBS= | 104.8 | SIGMA= | 1.5 | PHAS= | -164.2 | FOM= | 0.84 | TEST= 0 |
| INDE | 3 | 30 | 57 | FOBS= | 128.3 | SIGMA= | 1.3 | PHAS= | -15.5 | FOM= | 0.32 | TEST= 1 |
| INDE | 3 | 30 | 59 | FOBS= | 42.0 | SIGMA= | 4.8 | PHAS= | 63.4 | FOM= | 0.08 | TEST= 1 |
| INDE | 3 | 30 | 61 | FOBS= | 44.7 | SIGMA= | 4.5 | PHAS= | 84.2 | FOM= | 0.37 | TEST= 0 |
| INDE | 3 | 30 | 63 | FOBS= | 136.1 | SIGMA= | 2.2 | PHAS= | 27.0 | FOM= | 0.97 | TEST= 0 |
| INDE | 3 | 30 | 65 | FOBS= | 81.4 | SIGMA= | 6.2 | PHAS= | 138.1 | FOM= | 0.91 | TEST= 0 |
| INDE | 3 | 30 | 67 | FOBS= | 51.2 | SIGMA= | 7.3 | PHAS= | 104.9 | FOM= | 0.52 | TEST= 0 |
| INDE | 3 | 30 | 69 | FOBS= | 42.7 | SIGMA= | 8.7 | PHAS= | -39.7 | FOM= | 0.76 | TEST= 0 |
| INDE | 3 | 30 | 71 | FOBS= | 0.0 | SIGMA= | 27.2 | PHAS= | 0.0 | FOM= | 0.00 | TEST= 0 |
| INDE | 3 | 31 | 4 | FOBS= | 87.8 | SIGMA= | 1.4 | PHAS= | -163.3 | FOM= | 0.99 | TEST= 0 |
| INDE | 3 | 31 | 6 | FOBS= | 144.6 | SIGMA= | 0.7 | PHAS= | -103.8 | FOM= | 0.91 | TEST= 0 |
| INDE | 3 | 31 | 8 | FOBS= | 57.4 | SIGMA= | 1.4 | PHAS= | 143.6 | FOM= | 0.98 | TEST= 0 |
| INDE | 3 | 31 | 10 | FOBS= | 100.3 | SIGMA= | 1.4 | PHAS= | 33.9 | FOM= | 0.94 | TEST= 0 |
| INDE | 3 | 31 | 12 | FOBS= | 109.1 | SIGMA= | 1.4 | PHAS= | -8.3 | FOM= | 0.35 | TEST= 0 |
| INDE | 3 | 31 | 14 | FOBS= | 170.6 | SIGMA= | 1.1 | PHAS= | 172.7 | FOM= | 0.93 | TEST= 0 |
| INDE | 3 | 31 | 16 | FOBS= | 244.8 | SIGMA= | 1.1 | PHAS= | -104.0 | FOM= | 0.94 | TEST= 0 |
| INDE | 3 | 31 | 18 | FOBS= | 76.6 | SIGMA= | 2.6 | PHAS= | -48.0 | FOM= | 0.98 | TEST= 0 |
| INDE | 3 | 31 | 20 | FOBS= | 287.6 | SIGMA= | 1.0 | PHAS= | -109.1 | FOM= | 0.97 | TEST= 1 |
| INDE | 3 | 31 | 22 | FOBS= | 185.9 | SIGMA= | 1.3 | PHAS= | -87.4 | FOM= | 0.96 | TEST= 0 |
| INDE | 3 | 31 | 24 | FOBS= | 198.3 | SIGMA= | 1.3 | PHAS= | -17.9 | FOM= | 0.92 | TEST= 0 |
| INDE | 3 | 31 | 26 | FOBS= | 394.2 | SIGMA= | 0.7 | PHAS= | 166.3 | FOM= | 0.97 | TEST= 0 |
| INDE | 3 | 31 | 28 | FOBS= | 199.2 | SIGMA= | 1.0 | PHAS= | -164.5 | FOM= | 0.87 | TEST= 0 |
| INDE | 3 | 31 | 30 | FOBS= | 127.1 | SIGMA= | 1.5 | PHAS= | 49.8 | FOM= | 0.99 | TEST= 0 |
| INDE | 3 | 31 | 32 | FOBS= | 21.8 | SIGMA= | 8.6 | PHAS= | -167.4 | FOM= | 0.92 | TEST= 0 |
| INDE | 3 | 31 | 34 | FOBS= | 109.6 | SIGMA= | 1.9 | PHAS= | 74.2 | FOM= | 0.86 | TEST= 0 |
| INDE | 3 | 31 | 36 | FOBS= | 225.6 | SIGMA= | 1.1 | PHAS= | -26.1 | FOM= | 0.33 | TEST= 1 |
| INDE | 3 | 31 | 38 | FOBS= | 227.2 | SIGMA= | 1.1 | PHAS= | -56.5 | FOM= | 0.94 | TEST= 0 |
| INDE | 3 | 31 | 40 | FOBS= | 146.8 | SIGMA= | 1.4 | PHAS= | 153.0 | FOM= | 0.90 | TEST= 0 |
| INDE | 3 | 31 | 42 | FOBS= | 108.8 | SIGMA= | 1.6 | PHAS= | -121.1 | FOM= | 0.90 | TEST= 0 |
| INDE | 3 | 31 | 44 | FOBS= | 181.1 | SIGMA= | 0.9 | PHAS= | 85.3 | FOM= | 0.96 | TEST= 0 |
| INDE | 3 | 31 | 46 | FOBS= | 70.0 | SIGMA= | 2.0 | PHAS= | -178.7 | FOM= | 0.19 | TEST= 0 |
| INDE | 3 | 31 | 48 | FOBS= | 49.9 | SIGMA= | 2.7 | PHAS= | 73.6 | FOM= | 0.84 | TEST= 0 |
| INDE | 3 | 31 | 50 | FOBS= | 46.6 | SIGMA= | 2.9 | PHAS= | 121.1 | FOM= | 0.45 | TEST= 0 |
| INDE | 3 | 31 | 52 | FOBS= | 99.2 | SIGMA= | 1.4 | PHAS= | -60.6 | FOM= | 0.90 | TEST= 0 |
| INDE | 3 | 31 | 54 | FOBS= | 122.6 | SIGMA= | 1.2 | PHAS= | 45.4 | FOM= | 0.89 | TEST= 0 |
| INDE | 3 | 31 | 56 | FOBS= | 86.7 | SIGMA= | 1.8 | PHAS= | -5.1 | FOM= | 0.91 | TEST= 0 |
| INDE | 3 | 31 | 58 | FOBS= | 0.0 | SIGMA= | 21.1 | PHAS= | 0.0 | FOM= | 0.00 | TEST= 0 |
| INDE | 3 | 31 | 60 | FOBS= | 76.4 | SIGMA= | 2.7 | PHAS= | 33.0 | FOM= | 0.86 | TEST= 1 |
| INDE | 3 | 31 | 62 | FOBS= | 160.3 | SIGMA= | 1.4 | PHAS= | -21.6 | FOM= | 0.97 | TEST= 0 |
| INDE | 3 | 31 | 64 | FOBS= | 46.7 | SIGMA= | 6.0 | PHAS= | -85.7 | FOM= | 0.43 | TEST= 1 |
| INDE | 3 | 31 | 66 | FOBS= | 110.0 | SIGMA= | 4.8 | PHAS= | 5.5 | FOM= | 0.93 | TEST= 0 |
| INDE | 3 | 31 | 68 | FOBS= | 0.0 | SIGMA= | 27.3 | PHAS= | 0.0 | FOM= | 0.00 | TEST= 0 |
| INDE | 3 | 31 | 70 | FOBS= | 45.2 | SIGMA= | 12.3 | PHAS= | -79.9 | FOM= | 0.60 | TEST= 0 |
| INDE | 3 | 32 | 3 | FOBS= | 113.2 | SIGMA= | 1.1 | PHAS= | 114.2 | FOM= | 0.99 | TEST= 0 |
| INDE | 3 | 32 | 5 | FOBS= | 123.4 | SIGMA= | 1.1 | PHAS= | -41.9 | FOM= | 0.80 | TEST= 0 |
| INDE | 3 | 32 | 7 | FOBS= | 143.7 | SIGMA= | 0.6 | PHAS= | -154.9 | FOM= | 0.93 | TEST= 0 |
| INDE | 3 | 32 | 9 | FOBS= | 208.8 | SIGMA= | 0.9 | PHAS= | -128.4 | FOM= | 0.92 | TEST= 0 |
| INDE | 3 | 32 | 11 | FOBS= | 205.2 | SIGMA= | 0.9 | PHAS= | 171.2 | FOM= | 0.93 | TEST= 0 |
| INDE | 3 | 32 | 13 | FOBS= | 130.0 | SIGMA= | 1.3 | PHAS= | 114.4 | FOM= | 0.81 | TEST= 0 |
| INDE | 3 | 32 | 17 | FOBS= | 101.1 | SIGMA= | 2.1 | PHAS= | -104.8 | FOM= | 0.77 | TEST= 0 |
| INDE | 3 | 32 | 19 | FOBS= | 238.6 | SIGMA= | 1.1 | PHAS= | -3.4 | FOM= | 0.84 | TEST= 0 |
| INDE | 3 | 32 | 21 | FOBS= | 311.7 | SIGMA= | 1.0 | PHAS= | -155.3 | FOM= | 0.90 | TEST= 0 |
| INDE | 3 | 32 | 23 | FOBS= | 104.2 | SIGMA= | 2.2 | PHAS= | -12.7 | FOM= | 0.85 | TEST= 0 |
| INDE | 3 | 32 | 25 | FOBS= | 378.4 | SIGMA= | 1.0 | PHAS= | 172.2 | FOM= | 0.98 | TEST= 0 |
| INDE | 3 | 32 | 27 | FOBS= | 248.1 | SIGMA= | 1.0 | PHAS= | 102.6 | FOM= | 0.95 | TEST= 0 |
| INDE | 3 | 32 | 29 | FOBS= | 95.7 | SIGMA= | 1.9 | PHAS= | -30.1 | FOM= | 0.74 | TEST= 0 |
| INDE | 3 | 32 | 31 | FOBS= | 48.8 | SIGMA= | 3.9 | PHAS= | 54.0 | FOM= | 0.81 | TEST= 0 |
| INDE | 3 | 32 | 33 | FOBS= | 93.6 | SIGMA= | 2.2 | PHAS= | 30.8 | FOM= | 0.80 | TEST= 0 |
| INDE | 3 | 32 | 35 | FOBS= | 398.7 | SIGMA= | 1.1 | PHAS= | -107.4 | FOM= | 0.97 | TEST= 0 |
| INDE | 3 | 32 | 37 | FOBS= | 240.3 | SIGMA= | 1.0 | PHAS= | 141.8 | FOM= | 0.94 | TEST= 0 |

*FIG. 12A - 90*

```
INDE  3  32  39  FOBS=   89.3  SIGMA=   2.6  PHAS=  -120.1  FOM=  0.65  TEST=  0
INDE  3  32  41  FOBS=   81.2  SIGMA=   2.2  PHAS=   -38.5  FOM=  0.84  TEST=  0
INDE  3  32  43  FOBS=   66.5  SIGMA=   2.4  PHAS=   -84.5  FOM=  0.37  TEST=  0
INDE  3  32  45  FOBS=  207.0  SIGMA=   0.8  PHAS=    17.2  FOM=  0.89  TEST=  0
INDE  3  32  47  FOBS=   75.7  SIGMA=   2.1  PHAS=   -59.5  FOM=  0.83  TEST=  0
INDE  3  32  49  FOBS=  135.0  SIGMA=   1.0  PHAS=    34.2  FOM=  0.92  TEST=  0
INDE  3  32  51  FOBS=   35.7  SIGMA=   4.4  PHAS=  -155.2  FOM=  0.35  TEST=  0
INDE  3  32  53  FOBS=   81.7  SIGMA=   1.7  PHAS=  -164.5  FOM=  0.72  TEST=  0
INDE  3  32  55  FOBS=   92.4  SIGMA=   1.6  PHAS=   -44.0  FOM=  0.95  TEST=  0
INDE  3  32  57  FOBS=   32.7  SIGMA=   5.2  PHAS=   -40.9  FOM=  0.46  TEST=  0
INDE  3  32  59  FOBS=  100.1  SIGMA=   1.9  PHAS=    55.9  FOM=  0.95  TEST=  0
INDE  3  32  61  FOBS=   64.6  SIGMA=   3.2  PHAS=   -85.6  FOM=  0.91  TEST=  0
INDE  3  32  63  FOBS=   66.0  SIGMA=   3.4  PHAS=   -86.1  FOM=  0.89  TEST=  0
INDE  3  32  65  FOBS=  141.3  SIGMA=   2.3  PHAS=   -93.6  FOM=  0.15  TEST=  1
INDE  3  32  67  FOBS=   72.4  SIGMA=   7.2  PHAS=   -17.7  FOM=  0.80  TEST=  0
INDE  3  32  69  FOBS=   30.3  SIGMA=  12.6  PHAS=   -63.9  FOM=  0.68  TEST=  0
INDE  3  33   4  FOBS=  128.0  SIGMA=   1.1  PHAS=  -167.4  FOM=  0.96  TEST=  0
INDE  3  33   6  FOBS=  257.5  SIGMA=   0.6  PHAS=  -130.7  FOM=  0.99  TEST=  0
INDE  3  33   8  FOBS=   91.0  SIGMA=   1.0  PHAS=  -173.4  FOM=  0.73  TEST=  1
INDE  3  33  10  FOBS=  178.8  SIGMA=   1.0  PHAS=   108.9  FOM=  0.96  TEST=  0
INDE  3  33  12  FOBS=   91.3  SIGMA=   1.7  PHAS=    70.3  FOM=  0.95  TEST=  0
INDE  3  33  14  FOBS=  200.1  SIGMA=   1.0  PHAS=   119.6  FOM=  0.98  TEST=  1
INDE  3  33  16  FOBS=  147.2  SIGMA=   2.3  PHAS=     0.0  FOM=  0.00  TEST=  1
INDE  3  33  18  FOBS=  143.7  SIGMA=   1.7  PHAS=    62.5  FOM=  0.98  TEST=  0
INDE  3  33  20  FOBS=   96.2  SIGMA=   2.4  PHAS=  -171.3  FOM=  0.67  TEST=  0
INDE  3  33  22  FOBS=  177.5  SIGMA=   1.5  PHAS=    93.5  FOM=  0.95  TEST=  1
INDE  3  33  24  FOBS=  338.5  SIGMA=   1.0  PHAS=    48.5  FOM=  0.98  TEST=  0
INDE  3  33  26  FOBS=  300.9  SIGMA=   1.1  PHAS=   111.3  FOM=  0.96  TEST=  0
INDE  3  33  28  FOBS=  229.8  SIGMA=   1.1  PHAS=   -52.1  FOM=  0.92  TEST=  0
INDE  3  33  30  FOBS=  319.9  SIGMA=   0.8  PHAS=   -40.0  FOM=  0.97  TEST=  0
INDE  3  33  32  FOBS=   13.1  SIGMA=  16.6  PHAS=   -33.0  FOM=  0.11  TEST=  0
INDE  3  33  34  FOBS=   43.9  SIGMA=   7.5  PHAS=   144.4  FOM=  0.93  TEST=  0
INDE  3  33  36  FOBS=  141.2  SIGMA=   1.7  PHAS=  -121.2  FOM=  0.93  TEST=  0
INDE  3  33  38  FOBS=  100.0  SIGMA=   2.2  PHAS=   147.1  FOM=  0.41  TEST=  0
INDE  3  33  40  FOBS=  135.1  SIGMA=   1.7  PHAS=   178.5  FOM=  0.89  TEST=  0
INDE  3  33  42  FOBS=  171.6  SIGMA=   1.1  PHAS=  -108.0  FOM=  0.93  TEST=  0
INDE  3  33  44  FOBS=   20.8  SIGMA=   9.6  PHAS=   -58.4  FOM=  0.05  TEST=  0
INDE  3  33  46  FOBS=  104.3  SIGMA=   1.4  PHAS=   -80.7  FOM=  0.17  TEST=  1
INDE  3  33  48  FOBS=   97.1  SIGMA=   1.5  PHAS=   -48.8  FOM=  0.89  TEST=  0
INDE  3  33  50  FOBS=   55.4  SIGMA=   2.6  PHAS=  -171.4  FOM=  0.66  TEST=  0
INDE  3  33  52  FOBS=   52.7  SIGMA=   2.7  PHAS=  -108.7  FOM=  0.77  TEST=  0
INDE  3  33  54  FOBS=   81.3  SIGMA=   1.9  PHAS=  -155.0  FOM=  0.89  TEST=  0
INDE  3  33  56  FOBS=    0.0  SIGMA=  17.5  PHAS=     0.0  FOM=  0.00  TEST=  0
INDE  3  33  58  FOBS=   54.5  SIGMA=   3.5  PHAS=   -55.4  FOM=  0.73  TEST=  0
INDE  3  33  60  FOBS=   23.6  SIGMA=   7.6  PHAS=   162.2  FOM=  0.07  TEST=  0
INDE  3  33  62  FOBS=   48.4  SIGMA=   4.3  PHAS=   169.6  FOM=  0.71  TEST=  0
INDE  3  33  64  FOBS=  136.0  SIGMA=   1.8  PHAS=  -170.9  FOM=  0.97  TEST=  0
INDE  3  33  66  FOBS=   98.1  SIGMA=   3.1  PHAS=   -41.6  FOM=  0.84  TEST=  0
INDE  3  33  68  FOBS=  125.3  SIGMA=   3.2  PHAS=  -141.3  FOM=  0.96  TEST=  0
INDE  3  33  70  FOBS=   41.9  SIGMA=   9.2  PHAS=  -155.4  FOM=  0.52  TEST=  0
INDE  3  34   3  FOBS=  190.0  SIGMA=   0.8  PHAS=    44.9  FOM=  0.86  TEST=  0
INDE  3  34   5  FOBS=  207.5  SIGMA=   0.8  PHAS=   119.2  FOM=  0.95  TEST=  0
INDE  3  34   7  FOBS=  123.0  SIGMA=   1.0  PHAS=   168.3  FOM=  0.98  TEST=  0
INDE  3  34   9  FOBS=   44.0  SIGMA=   2.1  PHAS=    11.4  FOM=  0.95  TEST=  0
INDE  3  34  11  FOBS=  230.9  SIGMA=   0.9  PHAS=   130.3  FOM=  0.93  TEST=  0
INDE  3  34  13  FOBS=  280.1  SIGMA=   0.9  PHAS=    46.4  FOM=  0.96  TEST=  0
INDE  3  34  15  FOBS=   93.4  SIGMA=   2.0  PHAS=  -103.0  FOM=  0.87  TEST=  1
INDE  3  34  17  FOBS=  130.5  SIGMA=   1.9  PHAS=  -124.7  FOM=  0.27  TEST=  0
INDE  3  34  19  FOBS=   30.2  SIGMA=   7.4  PHAS=   114.3  FOM=  0.82  TEST=  0
INDE  3  34  21  FOBS=  143.6  SIGMA=   1.8  PHAS=   111.4  FOM=  0.96  TEST=  0
INDE  3  34  23  FOBS=  233.0  SIGMA=   1.3  PHAS=     6.4  FOM=  0.89  TEST=  0
INDE  3  34  25  FOBS=  158.3  SIGMA=   1.8  PHAS=    34.1  FOM=  0.87  TEST=  0
INDE  3  34  27  FOBS=  147.2  SIGMA=   2.0  PHAS=  -114.3  FOM=  0.80  TEST=  0
INDE  3  34  29  FOBS=  167.8  SIGMA=   1.4  PHAS=  -112.4  FOM=  0.86  TEST=  0
INDE  3  34  31  FOBS=  257.0  SIGMA=   1.0  PHAS=  -106.2  FOM=  0.98  TEST=  0
INDE  3  34  33  FOBS=  225.8  SIGMA=   1.1  PHAS=   -20.1  FOM=  0.97  TEST=  0
INDE  3  34  35  FOBS=  165.8  SIGMA=   1.5  PHAS=  -163.1  FOM=  0.92  TEST=  0
INDE  3  34  37  FOBS=  288.6  SIGMA=   0.9  PHAS=   109.5  FOM=  0.96  TEST=  0
INDE  3  34  39  FOBS=   80.9  SIGMA=   2.8  PHAS=  -132.7  FOM=  0.71  TEST=  0
INDE  3  34  41  FOBS=   68.5  SIGMA=   2.9  PHAS=  -157.1  FOM=  0.30  TEST=  0
```

*FIG. 12A - 91*

| | | | | | | | | | | | | |
|---|---|---|---|---|---|---|---|---|---|---|---|---|
| INDE | 3 | 34 | 43 | FOBS= | 74.0 | SIGMA= | 2.3 | PHAS= | -171.6 | FOM= | 0.36 | TEST= 0 |
| INDE | 3 | 34 | 45 | FOBS= | 113.4 | SIGMA= | 1.4 | PHAS= | 149.1 | FOM= | 0.88 | TEST= 0 |
| INDE | 3 | 34 | 47 | FOBS= | 126.2 | SIGMA= | 1.2 | PHAS= | 172.5 | FOM= | 0.92 | TEST= 0 |
| INDE | 3 | 34 | 49 | FOBS= | 78.4 | SIGMA= | 1.9 | PHAS= | -29.7 | FOM= | 0.61 | TEST= 0 |
| INDE | 3 | 34 | 51 | FOBS= | 91.2 | SIGMA= | 1.6 | PHAS= | 133.6 | FOM= | 0.92 | TEST= 0 |
| INDE | 3 | 34 | 53 | FOBS= | 71.2 | SIGMA= | 2.1 | PHAS= | 169.4 | FOM= | 0.91 | TEST= 0 |
| INDE | 3 | 34 | 55 | FOBS= | 91.7 | SIGMA= | 2.0 | PHAS= | 47.5 | FOM= | 0.40 | TEST= 1 |
| INDE | 3 | 34 | 57 | FOBS= | 0.0 | SIGMA= | 19.6 | PHAS= | 0.0 | FOM= | 0.00 | TEST= 0 |
| INDE | 3 | 34 | 59 | FOBS= | 41.5 | SIGMA= | 4.3 | PHAS= | 67.4 | FOM= | 0.72 | TEST= 0 |
| INDE | 3 | 34 | 61 | FOBS= | 43.1 | SIGMA= | 4.3 | PHAS= | 47.4 | FOM= | 0.71 | TEST= 0 |
| INDE | 3 | 34 | 63 | FOBS= | 90.1 | SIGMA= | 2.6 | PHAS= | 94.0 | FOM= | 0.25 | TEST= 1 |
| INDE | 3 | 34 | 65 | FOBS= | 54.8 | SIGMA= | 4.2 | PHAS= | 129.6 | FOM= | 0.13 | TEST= 0 |
| INDE | 3 | 34 | 67 | FOBS= | 41.0 | SIGMA= | 7.5 | PHAS= | 118.2 | FOM= | 0.71 | TEST= 0 |
| INDE | 3 | 34 | 69 | FOBS= | 72.5 | SIGMA= | 7.4 | PHAS= | 110.3 | FOM= | 0.71 | TEST= 0 |
| INDE | 3 | 35 | 4 | FOBS= | 194.9 | SIGMA= | 0.9 | PHAS= | 77.0 | FOM= | 0.63 | TEST= 1 |
| INDE | 3 | 35 | 8 | FOBS= | 174.0 | SIGMA= | 0.7 | PHAS= | -25.3 | FOM= | 0.98 | TEST= 0 |
| INDE | 3 | 35 | 10 | FOBS= | 52.6 | SIGMA= | 1.9 | PHAS= | -156.4 | FOM= | 0.15 | TEST= 0 |
| INDE | 3 | 35 | 12 | FOBS= | 333.0 | SIGMA= | 0.8 | PHAS= | 36.7 | FOM= | 0.99 | TEST= 0 |
| INDE | 3 | 35 | 14 | FOBS= | 72.8 | SIGMA= | 2.5 | PHAS= | 165.8 | FOM= | 0.42 | TEST= 0 |
| INDE | 3 | 35 | 16 | FOBS= | 303.7 | SIGMA= | 0.8 | PHAS= | 11.0 | FOM= | 0.97 | TEST= 0 |
| INDE | 3 | 35 | 18 | FOBS= | 83.1 | SIGMA= | 2.9 | PHAS= | -163.0 | FOM= | 0.61 | TEST= 0 |
| INDE | 3 | 35 | 20 | FOBS= | 247.8 | SIGMA= | 1.3 | PHAS= | 161.1 | FOM= | 0.93 | TEST= 0 |
| INDE | 3 | 35 | 22 | FOBS= | 251.5 | SIGMA= | 1.3 | PHAS= | -0.4 | FOM= | 0.85 | TEST= 0 |
| INDE | 3 | 35 | 24 | FOBS= | 205.9 | SIGMA= | 1.5 | PHAS= | -73.7 | FOM= | 0.95 | TEST= 0 |
| INDE | 3 | 35 | 26 | FOBS= | 91.8 | SIGMA= | 3.0 | PHAS= | -21.3 | FOM= | 0.70 | TEST= 1 |
| INDE | 3 | 35 | 28 | FOBS= | 29.8 | SIGMA= | 9.6 | PHAS= | -9.0 | FOM= | 0.14 | TEST= 0 |
| INDE | 3 | 35 | 30 | FOBS= | 59.8 | SIGMA= | 3.5 | PHAS= | 50.1 | FOM= | 0.21 | TEST= 0 |
| INDE | 3 | 35 | 32 | FOBS= | 202.3 | SIGMA= | 1.2 | PHAS= | -154.8 | FOM= | 0.97 | TEST= 0 |
| INDE | 3 | 35 | 34 | FOBS= | 16.1 | SIGMA= | 14.4 | PHAS= | -35.8 | FOM= | 0.56 | TEST= 1 |
| INDE | 3 | 35 | 36 | FOBS= | 0.0 | SIGMA= | 25.6 | PHAS= | 0.0 | FOM= | 0.00 | TEST= 1 |
| INDE | 3 | 35 | 38 | FOBS= | 119.7 | SIGMA= | 2.0 | PHAS= | 18.1 | FOM= | 0.68 | TEST= 0 |
| INDE | 3 | 35 | 40 | FOBS= | 110.3 | SIGMA= | 2.1 | PHAS= | 157.1 | FOM= | 0.63 | TEST= 1 |
| INDE | 3 | 35 | 42 | FOBS= | 66.8 | SIGMA= | 2.6 | PHAS= | -114.9 | FOM= | 0.90 | TEST= 0 |
| INDE | 3 | 35 | 44 | FOBS= | 150.4 | SIGMA= | 1.1 | PHAS= | -101.4 | FOM= | 0.80 | TEST= 1 |
| INDE | 3 | 35 | 46 | FOBS= | 92.7 | SIGMA= | 1.6 | PHAS= | 20.9 | FOM= | 0.90 | TEST= 0 |
| INDE | 3 | 35 | 48 | FOBS= | 99.7 | SIGMA= | 1.5 | PHAS= | 157.0 | FOM= | 0.89 | TEST= 0 |
| INDE | 3 | 35 | 50 | FOBS= | 26.8 | SIGMA= | 5.5 | PHAS= | -122.7 | FOM= | 0.27 | TEST= 0 |
| INDE | 3 | 35 | 52 | FOBS= | 80.0 | SIGMA= | 1.8 | PHAS= | 26.7 | FOM= | 0.88 | TEST= 0 |
| INDE | 3 | 35 | 54 | FOBS= | 0.0 | SIGMA= | 18.1 | PHAS= | 0.0 | FOM= | 0.00 | TEST= 0 |
| INDE | 3 | 35 | 56 | FOBS= | 57.0 | SIGMA= | 3.1 | PHAS= | 75.0 | FOM= | 0.40 | TEST= 1 |
| INDE | 3 | 35 | 58 | FOBS= | 91.3 | SIGMA= | 2.0 | PHAS= | -21.7 | FOM= | 0.77 | TEST= 0 |
| INDE | 3 | 35 | 60 | FOBS= | 113.9 | SIGMA= | 1.9 | PHAS= | -11.8 | FOM= | 0.91 | TEST= 0 |
| INDE | 3 | 35 | 62 | FOBS= | 0.0 | SIGMA= | 23.8 | PHAS= | 0.0 | FOM= | 0.00 | TEST= 0 |
| INDE | 3 | 35 | 64 | FOBS= | 12.2 | SIGMA= | 18.5 | PHAS= | -151.1 | FOM= | 0.25 | TEST= 0 |
| INDE | 3 | 35 | 66 | FOBS= | 26.2 | SIGMA= | 10.0 | PHAS= | 107.3 | FOM= | 0.26 | TEST= 0 |
| INDE | 3 | 35 | 68 | FOBS= | 48.4 | SIGMA= | 5.7 | PHAS= | -154.0 | FOM= | 0.56 | TEST= 0 |
| INDE | 3 | 36 | 3 | FOBS= | 157.2 | SIGMA= | 1.0 | PHAS= | -115.9 | FOM= | 0.64 | TEST= 0 |
| INDE | 3 | 36 | 5 | FOBS= | 85.5 | SIGMA= | 1.8 | PHAS= | 80.5 | FOM= | 0.88 | TEST= 0 |
| INDE | 3 | 36 | 7 | FOBS= | 130.0 | SIGMA= | 1.0 | PHAS= | 121.6 | FOM= | 0.94 | TEST= 0 |
| INDE | 3 | 36 | 9 | FOBS= | 155.6 | SIGMA= | 0.7 | PHAS= | 146.0 | FOM= | 0.89 | TEST= 0 |
| INDE | 3 | 36 | 11 | FOBS= | 57.2 | SIGMA= | 2.8 | PHAS= | -3.2 | FOM= | 0.79 | TEST= 0 |
| INDE | 3 | 36 | 13 | FOBS= | 234.5 | SIGMA= | 1.0 | PHAS= | -69.9 | FOM= | 0.97 | TEST= 0 |
| INDE | 3 | 36 | 15 | FOBS= | 140.1 | SIGMA= | 1.5 | PHAS= | -113.3 | FOM= | 0.98 | TEST= 0 |
| INDE | 3 | 36 | 17 | FOBS= | 74.6 | SIGMA= | 2.3 | PHAS= | 31.8 | FOM= | 0.43 | TEST= 0 |
| INDE | 3 | 36 | 19 | FOBS= | 168.5 | SIGMA= | 1.7 | PHAS= | 89.3 | FOM= | 0.77 | TEST= 0 |
| INDE | 3 | 36 | 21 | FOBS= | 219.5 | SIGMA= | 1.4 | PHAS= | 145.3 | FOM= | 0.95 | TEST= 0 |
| INDE | 3 | 36 | 23 | FOBS= | 222.8 | SIGMA= | 1.4 | PHAS= | -155.0 | FOM= | 0.95 | TEST= 0 |
| INDE | 3 | 36 | 25 | FOBS= | 190.3 | SIGMA= | 1.7 | PHAS= | -159.0 | FOM= | 0.96 | TEST= 0 |
| INDE | 3 | 36 | 27 | FOBS= | 271.2 | SIGMA= | 1.3 | PHAS= | -93.3 | FOM= | 0.96 | TEST= 0 |
| INDE | 3 | 36 | 29 | FOBS= | 127.6 | SIGMA= | 2.2 | PHAS= | 133.7 | FOM= | 0.85 | TEST= 0 |
| INDE | 3 | 36 | 31 | FOBS= | 181.3 | SIGMA= | 1.3 | PHAS= | 105.9 | FOM= | 0.94 | TEST= 0 |
| INDE | 3 | 36 | 33 | FOBS= | 144.5 | SIGMA= | 1.7 | PHAS= | 35.6 | FOM= | 0.88 | TEST= 0 |
| INDE | 3 | 36 | 35 | FOBS= | 100.2 | SIGMA= | 2.4 | PHAS= | -146.6 | FOM= | 0.88 | TEST= 0 |
| INDE | 3 | 36 | 37 | FOBS= | 90.3 | SIGMA= | 2.5 | PHAS= | -56.6 | FOM= | 0.63 | TEST= 0 |
| INDE | 3 | 36 | 39 | FOBS= | 233.2 | SIGMA= | 1.8 | PHAS= | 177.9 | FOM= | 0.96 | TEST= 0 |
| INDE | 3 | 36 | 41 | FOBS= | 154.9 | SIGMA= | 1.4 | PHAS= | 135.1 | FOM= | 0.85 | TEST= 0 |
| INDE | 3 | 36 | 43 | FOBS= | 61.3 | SIGMA= | 2.8 | PHAS= | 150.6 | FOM= | 0.88 | TEST= 0 |
| INDE | 3 | 36 | 45 | FOBS= | 207.0 | SIGMA= | 0.8 | PHAS= | 168.7 | FOM= | 0.95 | TEST= 0 |
| INDE | 3 | 36 | 47 | FOBS= | 146.5 | SIGMA= | 1.1 | PHAS= | 74.9 | FOM= | 0.95 | TEST= 0 |
| INDE | 3 | 36 | 49 | FOBS= | 55.2 | SIGMA= | 2.6 | PHAS= | 15.5 | FOM= | 0.58 | TEST= 0 |

*FIG. 12A - 92*

| | | | | | | | | | | | | |
|---|---|---|---|---|---|---|---|---|---|---|---|---|
| INDE | 3 | 36 | 51 | FOBS= | 69.4 | SIGMA= | 2.1 | PHAS= | -98.2 | FOM= | 0.77 | TEST= 1 |
| INDE | 3 | 36 | 53 | FOBS= | 0.0 | SIGMA= | 18.3 | PHAS= | 0.0 | FOM= | 0.00 | TEST= 0 |
| INDE | 3 | 36 | 55 | FOBS= | 0.0 | SIGMA= | 18.9 | PHAS= | 0.0 | FOM= | 0.00 | TEST= 0 |
| INDE | 3 | 36 | 57 | FOBS= | 80.0 | SIGMA= | 2.3 | PHAS= | -114.0 | FOM= | 0.65 | TEST= 0 |
| INDE | 3 | 36 | 59 | FOBS= | 117.1 | SIGMA= | 1.6 | PHAS= | -103.6 | FOM= | 0.94 | TEST= 0 |
| INDE | 3 | 36 | 61 | FOBS= | 0.0 | SIGMA= | 20.2 | PHAS= | 0.0 | FOM= | 0.00 | TEST= 1 |
| INDE | 3 | 36 | 63 | FOBS= | 22.3 | SIGMA= | 8.8 | PHAS= | 78.0 | FOM= | 0.42 | TEST= 0 |
| INDE | 3 | 36 | 65 | FOBS= | 43.3 | SIGMA= | 5.3 | PHAS= | 5.5 | FOM= | 0.73 | TEST= 0 |
| INDE | 3 | 36 | 67 | FOBS= | 83.2 | SIGMA= | 3.9 | PHAS= | 68.0 | FOM= | 0.84 | TEST= 0 |
| INDE | 3 | 37 | 4 | FOBS= | 315.7 | SIGMA= | 0.7 | PHAS= | -157.1 | FOM= | 0.99 | TEST= 0 |
| INDE | 3 | 37 | 8 | FOBS= | 174.5 | SIGMA= | 0.8 | PHAS= | -29.4 | FOM= | 0.92 | TEST= 0 |
| INDE | 3 | 37 | 10 | FOBS= | 84.7 | SIGMA= | 1.3 | PHAS= | 167.4 | FOM= | 0.91 | TEST= 0 |
| INDE | 3 | 37 | 12 | FOBS= | 236.6 | SIGMA= | 0.9 | PHAS= | -165.4 | FOM= | 0.97 | TEST= 0 |
| INDE | 3 | 37 | 14 | FOBS= | 116.5 | SIGMA= | 1.7 | PHAS= | -175.9 | FOM= | 0.98 | TEST= 0 |
| INDE | 3 | 37 | 16 | FOBS= | 320.6 | SIGMA= | 0.9 | PHAS= | -1.7 | FOM= | 0.95 | TEST= 0 |
| INDE | 3 | 37 | 18 | FOBS= | 182.0 | SIGMA= | 1.6 | PHAS= | -111.2 | FOM= | 0.76 | TEST= 0 |
| INDE | 3 | 37 | 20 | FOBS= | 126.1 | SIGMA= | 2.2 | PHAS= | 149.2 | FOM= | 0.87 | TEST= 0 |
| INDE | 3 | 37 | 22 | FOBS= | 99.4 | SIGMA= | 2.9 | PHAS= | 76.0 | FOM= | 0.95 | TEST= 0 |
| INDE | 3 | 37 | 24 | FOBS= | 151.8 | SIGMA= | 2.0 | PHAS= | 140.0 | FOM= | 0.92 | TEST= 0 |
| INDE | 3 | 37 | 26 | FOBS= | 189.2 | SIGMA= | 1.8 | PHAS= | 154.2 | FOM= | 0.91 | TEST= 0 |
| INDE | 3 | 37 | 28 | FOBS= | 160.8 | SIGMA= | 2.1 | PHAS= | 46.0 | FOM= | 0.97 | TEST= 0 |
| INDE | 3 | 37 | 30 | FOBS= | 268.4 | SIGMA= | 1.2 | PHAS= | 19.7 | FOM= | 0.97 | TEST= 0 |
| INDE | 3 | 37 | 32 | FOBS= | 162.4 | SIGMA= | 1.5 | PHAS= | -45.2 | FOM= | 0.90 | TEST= 0 |
| INDE | 3 | 37 | 34 | FOBS= | 368.2 | SIGMA= | 0.8 | PHAS= | -81.0 | FOM= | 0.97 | TEST= 0 |
| INDE | 3 | 37 | 36 | FOBS= | 180.0 | SIGMA= | 1.4 | PHAS= | 139.1 | FOM= | 0.90 | TEST= 0 |
| INDE | 3 | 37 | 38 | FOBS= | 261.9 | SIGMA= | 1.0 | PHAS= | -12.7 | FOM= | 0.97 | TEST= 0 |
| INDE | 3 | 37 | 40 | FOBS= | 110.7 | SIGMA= | 2.1 | PHAS= | 98.5 | FOM= | 0.48 | TEST= 1 |
| INDE | 3 | 37 | 42 | FOBS= | 136.9 | SIGMA= | 1.4 | PHAS= | 89.1 | FOM= | 0.93 | TEST= 0 |
| INDE | 3 | 37 | 44 | FOBS= | 112.1 | SIGMA= | 1.4 | PHAS= | 99.0 | FOM= | 0.75 | TEST= 0 |
| INDE | 3 | 37 | 46 | FOBS= | 170.0 | SIGMA= | 1.0 | PHAS= | -48.3 | FOM= | 0.94 | TEST= 0 |
| INDE | 3 | 37 | 48 | FOBS= | 20.0 | SIGMA= | 8.6 | PHAS= | -129.3 | FOM= | 0.15 | TEST= 1 |
| INDE | 3 | 37 | 50 | FOBS= | 74.2 | SIGMA= | 2.0 | PHAS= | 36.5 | FOM= | 0.65 | TEST= 0 |
| INDE | 3 | 37 | 52 | FOBS= | 12.9 | SIGMA= | 12.2 | PHAS= | 107.7 | FOM= | 0.21 | TEST= 0 |
| INDE | 3 | 37 | 54 | FOBS= | 80.0 | SIGMA= | 2.1 | PHAS= | 124.8 | FOM= | 0.55 | TEST= 0 |
| INDE | 3 | 37 | 56 | FOBS= | 29.0 | SIGMA= | 5.7 | PHAS= | -176.8 | FOM= | 0.39 | TEST= 0 |
| INDE | 3 | 37 | 58 | FOBS= | 68.8 | SIGMA= | 2.6 | PHAS= | -155.0 | FOM= | 0.84 | TEST= 0 |
| INDE | 3 | 37 | 60 | FOBS= | 0.0 | SIGMA= | 18.9 | PHAS= | 0.0 | FOM= | 0.00 | TEST= 0 |
| INDE | 3 | 37 | 62 | FOBS= | 0.0 | SIGMA= | 20.3 | PHAS= | 0.0 | FOM= | 0.00 | TEST= 0 |
| INDE | 3 | 37 | 64 | FOBS= | 48.5 | SIGMA= | 4.1 | PHAS= | -39.5 | FOM= | 0.54 | TEST= 0 |
| INDE | 3 | 37 | 66 | FOBS= | 0.0 | SIGMA= | 22.9 | PHAS= | 0.0 | FOM= | 0.00 | TEST= 0 |
| INDE | 3 | 37 | 68 | FOBS= | 0.0 | SIGMA= | 28.4 | PHAS= | 0.0 | FOM= | 0.00 | TEST= 0 |
| INDE | 3 | 38 | 3 | FOBS= | 167.8 | SIGMA= | 1.0 | PHAS= | -121.3 | FOM= | 0.99 | TEST= 0 |
| INDE | 3 | 38 | 5 | FOBS= | 309.0 | SIGMA= | 0.7 | PHAS= | 156.4 | FOM= | 0.95 | TEST= 1 |
| INDE | 3 | 38 | 7 | FOBS= | 138.5 | SIGMA= | 1.4 | PHAS= | 161.9 | FOM= | 0.92 | TEST= 0 |
| INDE | 3 | 38 | 9 | FOBS= | 246.9 | SIGMA= | 0.6 | PHAS= | 129.6 | FOM= | 0.96 | TEST= 0 |
| INDE | 3 | 38 | 11 | FOBS= | 167.5 | SIGMA= | 0.9 | PHAS= | 57.5 | FOM= | 0.94 | TEST= 0 |
| INDE | 3 | 38 | 13 | FOBS= | 372.7 | SIGMA= | 0.8 | PHAS= | -125.1 | FOM= | 0.96 | TEST= 0 |
| INDE | 3 | 38 | 15 | FOBS= | 44.7 | SIGMA= | 4.6 | PHAS= | 144.1 | FOM= | 0.90 | TEST= 0 |
| INDE | 3 | 38 | 17 | FOBS= | 168.7 | SIGMA= | 1.3 | PHAS= | 95.8 | FOM= | 0.97 | TEST= 0 |
| INDE | 3 | 38 | 19 | FOBS= | 387.9 | SIGMA= | 1.1 | PHAS= | -134.6 | FOM= | 0.94 | TEST= 0 |
| INDE | 3 | 38 | 21 | FOBS= | 135.6 | SIGMA= | 2.2 | PHAS= | 118.6 | FOM= | 0.73 | TEST= 0 |
| INDE | 3 | 38 | 23 | FOBS= | 40.4 | SIGMA= | 7.3 | PHAS= | 53.1 | FOM= | 0.39 | TEST= 0 |
| INDE | 3 | 38 | 25 | FOBS= | 118.4 | SIGMA= | 2.7 | PHAS= | 50.4 | FOM= | 0.96 | TEST= 0 |
| INDE | 3 | 38 | 27 | FOBS= | 161.6 | SIGMA= | 2.2 | PHAS= | 17.5 | FOM= | 0.82 | TEST= 0 |
| INDE | 3 | 38 | 29 | FOBS= | 133.6 | SIGMA= | 2.6 | PHAS= | -121.3 | FOM= | 0.78 | TEST= 0 |
| INDE | 3 | 38 | 31 | FOBS= | 89.4 | SIGMA= | 3.0 | PHAS= | 48.4 | FOM= | 0.90 | TEST= 0 |
| INDE | 3 | 38 | 33 | FOBS= | 201.1 | SIGMA= | 1.5 | PHAS= | -174.9 | FOM= | 0.95 | TEST= 0 |
| INDE | 3 | 38 | 35 | FOBS= | 117.0 | SIGMA= | 2.0 | PHAS= | 66.7 | FOM= | 0.81 | TEST= 0 |
| INDE | 3 | 38 | 37 | FOBS= | 172.7 | SIGMA= | 1.7 | PHAS= | -26.3 | FOM= | 0.93 | TEST= 0 |
| INDE | 3 | 38 | 39 | FOBS= | 48.5 | SIGMA= | 5.2 | PHAS= | 163.3 | FOM= | 0.24 | TEST= 1 |
| INDE | 3 | 38 | 41 | FOBS= | 176.4 | SIGMA= | 1.2 | PHAS= | 84.0 | FOM= | 0.74 | TEST= 1 |
| INDE | 3 | 38 | 43 | FOBS= | 173.9 | SIGMA= | 1.1 | PHAS= | 4.8 | FOM= | 0.83 | TEST= 0 |
| INDE | 3 | 38 | 45 | FOBS= | 119.1 | SIGMA= | 1.3 | PHAS= | -116.6 | FOM= | 0.95 | TEST= 0 |
| INDE | 3 | 38 | 47 | FOBS= | 0.0 | SIGMA= | 18.2 | PHAS= | 0.0 | FOM= | 0.00 | TEST= 0 |
| INDE | 3 | 38 | 49 | FOBS= | 15.5 | SIGMA= | 12.1 | PHAS= | -21.8 | FOM= | 0.10 | TEST= 0 |
| INDE | 3 | 38 | 51 | FOBS= | 89.9 | SIGMA= | 1.6 | PHAS= | -49.3 | FOM= | 0.82 | TEST= 0 |
| INDE | 3 | 38 | 53 | FOBS= | 72.8 | SIGMA= | 2.4 | PHAS= | 17.7 | FOM= | 0.92 | TEST= 0 |
| INDE | 3 | 38 | 55 | FOBS= | 43.9 | SIGMA= | 3.9 | PHAS= | 12.8 | FOM= | 0.69 | TEST= 0 |
| INDE | 3 | 38 | 57 | FOBS= | 40.2 | SIGMA= | 4.1 | PHAS= | 175.0 | FOM= | 0.56 | TEST= 0 |
| INDE | 3 | 38 | 59 | FOBS= | 0.0 | SIGMA= | 19.5 | PHAS= | 0.0 | FOM= | 0.00 | TEST= 0 |

*FIG. 12A - 93*

```
INDE  3  38  61  FOBS=   21.6  SIGMA=   8.5  PHAS=  -117.6  FOM=  0.47  TEST= 0
INDE  3  38  63  FOBS=   36.3  SIGMA=   6.3  PHAS=    -7.3  FOM=  0.20  TEST= 1
INDE  3  38  65  FOBS=    0.0  SIGMA=  21.0  PHAS=     0.0  FOM=  0.00  TEST= 0
INDE  3  38  67  FOBS=   35.7  SIGMA=  10.9  PHAS=  -117.5  FOM=  0.08  TEST= 0
INDE  3  39   4  FOBS=  296.2  SIGMA=   0.8  PHAS=   127.1  FOM=  0.96  TEST= 0
INDE  3  39   8  FOBS=  282.7  SIGMA=   0.7  PHAS=   -88.5  FOM=  0.95  TEST= 1
INDE  3  39  10  FOBS=  219.6  SIGMA=   0.6  PHAS=    73.2  FOM=  0.85  TEST= 0
INDE  3  39  12  FOBS=  204.5  SIGMA=   0.7  PHAS=   169.1  FOM=  0.94  TEST= 0
INDE  3  39  14  FOBS=  277.6  SIGMA=   1.0  PHAS=   125.9  FOM=  0.86  TEST= 0
INDE  3  39  16  FOBS=  271.7  SIGMA=   1.1  PHAS=    13.5  FOM=  0.97  TEST= 0
INDE  3  39  18  FOBS=  120.4  SIGMA=   1.6  PHAS=    94.9  FOM=  0.96  TEST= 0
INDE  3  39  20  FOBS=  179.2  SIGMA=   1.8  PHAS=    73.1  FOM=  0.93  TEST= 0
INDE  3  39  22  FOBS=  255.3  SIGMA=   1.5  PHAS=   -80.4  FOM=  0.89  TEST= 0
INDE  3  39  24  FOBS=  140.9  SIGMA=   2.4  PHAS=  -101.5  FOM=  0.94  TEST= 0
INDE  3  39  26  FOBS=   86.1  SIGMA=   4.0  PHAS=   -55.8  FOM=  0.95  TEST= 0
INDE  3  39  28  FOBS=   84.0  SIGMA=   4.1  PHAS=   -37.6  FOM=  0.76  TEST= 0
INDE  3  39  30  FOBS=  168.4  SIGMA=   2.2  PHAS=   -17.3  FOM=  0.92  TEST= 0
INDE  3  39  32  FOBS=   70.6  SIGMA=   3.5  PHAS=    43.5  FOM=  0.87  TEST= 0
INDE  3  39  34  FOBS=  191.5  SIGMA=   1.3  PHAS=   -95.2  FOM=  0.97  TEST= 0
INDE  3  39  36  FOBS=  194.5  SIGMA=   1.3  PHAS=    38.8  FOM=  0.90  TEST= 1
INDE  3  39  38  FOBS=   64.6  SIGMA=   3.4  PHAS=   -51.8  FOM=  0.93  TEST= 0
INDE  3  39  40  FOBS=   43.8  SIGMA=   5.7  PHAS=  -160.6  FOM=  0.46  TEST= 0
INDE  3  39  42  FOBS=  131.5  SIGMA=   1.4  PHAS=    -5.6  FOM=  0.94  TEST= 0
INDE  3  39  44  FOBS=   86.3  SIGMA=   2.0  PHAS=   123.9  FOM=  0.62  TEST= 0
INDE  3  39  46  FOBS=   95.1  SIGMA=   1.6  PHAS=  -145.0  FOM=  0.83  TEST= 0
INDE  3  39  48  FOBS=   84.3  SIGMA=   1.8  PHAS=   -85.9  FOM=  0.84  TEST= 0
INDE  3  39  50  FOBS=   72.5  SIGMA=   2.0  PHAS=  -109.3  FOM=  0.79  TEST= 0
INDE  3  39  52  FOBS=   56.7  SIGMA=   3.1  PHAS=  -109.0  FOM=  0.65  TEST= 0
INDE  3  39  54  FOBS=   74.1  SIGMA=   2.4  PHAS=   -75.6  FOM=  0.85  TEST= 0
INDE  3  39  56  FOBS=   38.4  SIGMA=   4.4  PHAS=   -37.2  FOM=  0.08  TEST= 0
INDE  3  39  58  FOBS=    0.0  SIGMA=  18.1  PHAS=     0.0  FOM=  0.00  TEST= 1
INDE  3  39  60  FOBS=    0.0  SIGMA=  18.9  PHAS=     0.0  FOM=  0.00  TEST= 0
INDE  3  39  62  FOBS=    0.0  SIGMA=  19.2  PHAS=     0.0  FOM=  0.00  TEST= 0
INDE  3  39  64  FOBS=   14.0  SIGMA=  16.4  PHAS=   160.5  FOM=  0.17  TEST= 0
INDE  3  39  66  FOBS=   57.1  SIGMA=   5.9  PHAS=     0.2  FOM=  0.88  TEST= 0
INDE  3  40   3  FOBS=  231.1  SIGMA=   0.9  PHAS=    43.1  FOM=  0.90  TEST= 0
INDE  3  40   5  FOBS=  136.8  SIGMA=   1.8  PHAS=   115.6  FOM=  0.97  TEST= 0
INDE  3  40   9  FOBS=  175.5  SIGMA=   1.0  PHAS=   178.8  FOM=  0.87  TEST= 0
INDE  3  40  11  FOBS=  136.9  SIGMA=   1.0  PHAS=   -14.3  FOM=  0.81  TEST= 1
INDE  3  40  13  FOBS=   99.7  SIGMA=   1.6  PHAS=    57.1  FOM=  0.89  TEST= 0
INDE  3  40  15  FOBS=  317.9  SIGMA=   1.0  PHAS=   -43.3  FOM=  0.99  TEST= 1
INDE  3  40  17  FOBS=   49.3  SIGMA=   4.3  PHAS=  -177.2  FOM=  0.76  TEST= 0
INDE  3  40  19  FOBS=   84.3  SIGMA=   2.3  PHAS=     8.5  FOM=  0.48  TEST= 0
INDE  3  40  21  FOBS=   48.6  SIGMA=   6.5  PHAS=   -59.3  FOM=  0.41  TEST= 0
INDE  3  40  23  FOBS=  220.3  SIGMA=   1.7  PHAS=   131.0  FOM=  0.98  TEST= 0
INDE  3  40  25  FOBS=   57.1  SIGMA=   6.0  PHAS=    63.8  FOM=  0.71  TEST= 0
INDE  3  40  27  FOBS=    0.0  SIGMA=  26.4  PHAS=     0.0  FOM=  0.00  TEST= 0
INDE  3  40  29  FOBS=  161.8  SIGMA=   2.3  PHAS=  -143.1  FOM=  0.93  TEST= 0
INDE  3  40  31  FOBS=  109.0  SIGMA=   3.2  PHAS=   -70.4  FOM=  0.86  TEST= 0
INDE  3  40  33  FOBS=  149.2  SIGMA=   1.6  PHAS=   116.4  FOM=  0.95  TEST= 0
INDE  3  40  35  FOBS=  131.8  SIGMA=   1.8  PHAS=   -13.1  FOM=  0.89  TEST= 0
INDE  3  40  37  FOBS=  105.6  SIGMA=   2.2  PHAS=   -57.5  FOM=  0.94  TEST= 0
INDE  3  40  39  FOBS=  102.2  SIGMA=   2.4  PHAS=    76.2  FOM=  0.78  TEST= 0
INDE  3  40  41  FOBS=  111.7  SIGMA=   1.9  PHAS=   143.3  FOM=  0.95  TEST= 0
INDE  3  40  43  FOBS=   58.9  SIGMA=   3.0  PHAS=   107.3  FOM=  0.50  TEST= 0
INDE  3  40  45  FOBS=   76.6  SIGMA=   2.0  PHAS=   -58.1  FOM=  0.76  TEST= 0
INDE  3  40  47  FOBS=    0.0  SIGMA=  17.2  PHAS=     0.0  FOM=  0.00  TEST= 0
INDE  3  40  49  FOBS=   70.6  SIGMA=   2.1  PHAS=  -170.5  FOM=  0.08  TEST= 1
INDE  3  40  51  FOBS=    0.0  SIGMA=  17.0  PHAS=     0.0  FOM=  0.00  TEST= 0
INDE  3  40  53  FOBS=   97.5  SIGMA=   1.8  PHAS=  -138.1  FOM=  0.90  TEST= 0
INDE  3  40  55  FOBS=   81.9  SIGMA=   2.1  PHAS=   -60.9  FOM=  0.81  TEST= 0
INDE  3  40  57  FOBS=   22.5  SIGMA=   9.2  PHAS=  -164.1  FOM=  0.20  TEST= 0
INDE  3  40  59  FOBS=   32.2  SIGMA=   5.8  PHAS=    43.5  FOM=  0.20  TEST= 0
INDE  3  40  61  FOBS=   75.6  SIGMA=   2.5  PHAS=   -76.6  FOM=  0.89  TEST= 0
INDE  3  40  63  FOBS=   39.4  SIGMA=   5.1  PHAS=  -102.3  FOM=  0.06  TEST= 1
INDE  3  40  65  FOBS=   26.9  SIGMA=   9.8  PHAS=    50.9  FOM=  0.36  TEST= 0
INDE  3  41   4  FOBS=  147.9  SIGMA=   1.3  PHAS=    88.4  FOM=  0.92  TEST= 0
INDE  3  41   8  FOBS=  302.0  SIGMA=   1.0  PHAS=     0.9  FOM=  0.91  TEST= 1
INDE  3  41  10  FOBS=   25.3  SIGMA=   4.9  PHAS=  -154.8  FOM=  0.42  TEST= 0
INDE  3  41  12  FOBS=  376.3  SIGMA=   0.8  PHAS=   -59.5  FOM=  0.97  TEST= 0
```

*FIG. 12A - 94*

| | | | | | | | | | | | | |
|---|---|---|---|---|---|---|---|---|---|---|---|---|
| INDE | 3 | 41 | 14 | FOBS= | 26.9 | SIGMA= | 8.1 | PHAS= | -106.0 | FOM= | 0.40 | TEST= 0 |
| INDE | 3 | 41 | 16 | FOBS= | 415.3 | SIGMA= | 0.9 | PHAS= | -172.1 | FOM= | 0.98 | TEST= 0 |
| INDE | 3 | 41 | 18 | FOBS= | 92.8 | SIGMA= | 2.2 | PHAS= | -111.8 | FOM= | 0.60 | TEST= 0 |
| INDE | 3 | 41 | 20 | FOBS= | 91.6 | SIGMA= | 2.3 | PHAS= | -23.1 | FOM= | 0.88 | TEST= 0 |
| INDE | 3 | 41 | 22 | FOBS= | 148.0 | SIGMA= | 2.4 | PHAS= | -101.3 | FOM= | 0.70 | TEST= 0 |
| INDE | 3 | 41 | 24 | FOBS= | 81.2 | SIGMA= | 4.3 | PHAS= | -66.8 | FOM= | 0.74 | TEST= 0 |
| INDE | 3 | 41 | 26 | FOBS= | 36.3 | SIGMA= | 9.8 | PHAS= | -69.4 | FOM= | 0.63 | TEST= 0 |
| INDE | 3 | 41 | 28 | FOBS= | 0.0 | SIGMA= | 26.3 | PHAS= | 0.0 | FOM= | 0.00 | TEST= 0 |
| INDE | 3 | 41 | 30 | FOBS= | 164.3 | SIGMA= | 2.3 | PHAS= | 140.0 | FOM= | 0.84 | TEST= 0 |
| INDE | 3 | 41 | 32 | FOBS= | 116.5 | SIGMA= | 2.6 | PHAS= | -147.1 | FOM= | 0.48 | TEST= 1 |
| INDE | 3 | 41 | 34 | FOBS= | 238.4 | SIGMA= | 1.1 | PHAS= | -62.8 | FOM= | 0.97 | TEST= 0 |
| INDE | 3 | 41 | 36 | FOBS= | 119.9 | SIGMA= | 1.9 | PHAS= | -68.0 | FOM= | 0.86 | TEST= 0 |
| INDE | 3 | 41 | 38 | FOBS= | 86.4 | SIGMA= | 2.6 | PHAS= | -136.3 | FOM= | 0.87 | TEST= 0 |
| INDE | 3 | 41 | 40 | FOBS= | 52.0 | SIGMA= | 4.8 | PHAS= | 64.5 | FOM= | 0.83 | TEST= 0 |
| INDE | 3 | 41 | 42 | FOBS= | 200.9 | SIGMA= | 1.0 | PHAS= | 15.9 | FOM= | 0.93 | TEST= 0 |
| INDE | 3 | 41 | 44 | FOBS= | 0.0 | SIGMA= | 18.4 | PHAS= | 0.0 | FOM= | 0.00 | TEST= 0 |
| INDE | 3 | 41 | 46 | FOBS= | 70.8 | SIGMA= | 2.2 | PHAS= | 156.3 | FOM= | 0.78 | TEST= 0 |
| INDE | 3 | 41 | 48 | FOBS= | 84.0 | SIGMA= | 1.8 | PHAS= | -155.6 | FOM= | 0.92 | TEST= 0 |
| INDE | 3 | 41 | 50 | FOBS= | 81.3 | SIGMA= | 1.8 | PHAS= | -104.3 | FOM= | 0.84 | TEST= 0 |
| INDE | 3 | 41 | 52 | FOBS= | 69.3 | SIGMA= | 2.5 | PHAS= | 157.4 | FOM= | 0.87 | TEST= 0 |
| INDE | 3 | 41 | 54 | FOBS= | 26.3 | SIGMA= | 7.7 | PHAS= | -178.8 | FOM= | 0.18 | TEST= 0 |
| INDE | 3 | 41 | 56 | FOBS= | 80.0 | SIGMA= | 2.2 | PHAS= | 13.1 | FOM= | 0.91 | TEST= 0 |
| INDE | 3 | 41 | 58 | FOBS= | 32.7 | SIGMA= | 5.2 | PHAS= | -107.9 | FOM= | 0.16 | TEST= 0 |
| INDE | 3 | 41 | 60 | FOBS= | 0.0 | SIGMA= | 20.8 | PHAS= | 0.0 | FOM= | 0.00 | TEST= 0 |
| INDE | 3 | 41 | 62 | FOBS= | 63.2 | SIGMA= | 3.0 | PHAS= | -94.8 | FOM= | 0.57 | TEST= 1 |
| INDE | 3 | 41 | 64 | FOBS= | 36.9 | SIGMA= | 6.1 | PHAS= | -133.5 | FOM= | 0.45 | TEST= 0 |
| INDE | 3 | 41 | 66 | FOBS= | 123.8 | SIGMA= | 4.8 | PHAS= | -52.3 | FOM= | 0.91 | TEST= 0 |
| INDE | 3 | 42 | 3 | FOBS= | 53.8 | SIGMA= | 3.4 | PHAS= | -171.3 | FOM= | 0.84 | TEST= 0 |
| INDE | 3 | 42 | 9 | FOBS= | 251.6 | SIGMA= | 0.8 | PHAS= | -95.0 | FOM= | 0.99 | TEST= 1 |
| INDE | 3 | 42 | 11 | FOBS= | 476.0 | SIGMA= | 0.7 | PHAS= | -114.8 | FOM= | 0.98 | TEST= 0 |
| INDE | 3 | 42 | 13 | FOBS= | 155.1 | SIGMA= | 1.2 | PHAS= | 179.6 | FOM= | 0.98 | TEST= 0 |
| INDE | 3 | 42 | 15 | FOBS= | 237.4 | SIGMA= | 1.2 | PHAS= | 106.7 | FOM= | 0.99 | TEST= 0 |
| INDE | 3 | 42 | 17 | FOBS= | 354.0 | SIGMA= | 1.1 | PHAS= | 44.6 | FOM= | 0.99 | TEST= 0 |
| INDE | 3 | 42 | 19 | FOBS= | 160.4 | SIGMA= | 1.5 | PHAS= | -27.9 | FOM= | 0.73 | TEST= 0 |
| INDE | 3 | 42 | 21 | FOBS= | 163.2 | SIGMA= | 2.3 | PHAS= | -149.6 | FOM= | 0.94 | TEST= 0 |
| INDE | 3 | 42 | 23 | FOBS= | 129.6 | SIGMA= | 2.9 | PHAS= | 149.6 | FOM= | 0.50 | TEST= 0 |
| INDE | 3 | 42 | 25 | FOBS= | 97.0 | SIGMA= | 3.8 | PHAS= | 124.3 | FOM= | 0.82 | TEST= 1 |
| INDE | 3 | 42 | 27 | FOBS= | 109.6 | SIGMA= | 3.3 | PHAS= | -78.3 | FOM= | 0.72 | TEST= 0 |
| INDE | 3 | 42 | 29 | FOBS= | 179.7 | SIGMA= | 2.1 | PHAS= | -13.0 | FOM= | 0.93 | TEST= 0 |
| INDE | 3 | 42 | 31 | FOBS= | 92.5 | SIGMA= | 3.7 | PHAS= | -3.3 | FOM= | 0.58 | TEST= 0 |
| INDE | 3 | 42 | 33 | FOBS= | 288.3 | SIGMA= | 1.1 | PHAS= | 84.2 | FOM= | 0.96 | TEST= 0 |
| INDE | 3 | 42 | 35 | FOBS= | 194.4 | SIGMA= | 1.3 | PHAS= | -170.1 | FOM= | 0.96 | TEST= 0 |
| INDE | 3 | 42 | 37 | FOBS= | 240.8 | SIGMA= | 1.1 | PHAS= | -160.5 | FOM= | 0.30 | TEST= 1 |
| INDE | 3 | 42 | 39 | FOBS= | 85.0 | SIGMA= | 2.8 | PHAS= | -55.8 | FOM= | 0.74 | TEST= 0 |
| INDE | 3 | 42 | 41 | FOBS= | 65.8 | SIGMA= | 3.3 | PHAS= | 28.8 | FOM= | 0.77 | TEST= 1 |
| INDE | 3 | 42 | 43 | FOBS= | 154.9 | SIGMA= | 1.3 | PHAS= | -82.9 | FOM= | 0.92 | TEST= 0 |
| INDE | 3 | 42 | 45 | FOBS= | 112.3 | SIGMA= | 1.4 | PHAS= | -153.7 | FOM= | 0.85 | TEST= 1 |
| INDE | 3 | 42 | 47 | FOBS= | 130.3 | SIGMA= | 1.2 | PHAS= | 125.7 | FOM= | 0.92 | TEST= 0 |
| INDE | 3 | 42 | 49 | FOBS= | 109.8 | SIGMA= | 1.4 | PHAS= | 123.0 | FOM= | 0.77 | TEST= 0 |
| INDE | 3 | 42 | 51 | FOBS= | 62.5 | SIGMA= | 2.8 | PHAS= | 169.4 | FOM= | 0.86 | TEST= 0 |
| INDE | 3 | 42 | 53 | FOBS= | 0.0 | SIGMA= | 18.5 | PHAS= | 0.0 | FOM= | 0.00 | TEST= 0 |
| INDE | 3 | 42 | 55 | FOBS= | 96.3 | SIGMA= | 1.9 | PHAS= | -41.9 | FOM= | 0.89 | TEST= 0 |
| INDE | 3 | 42 | 57 | FOBS= | 64.0 | SIGMA= | 2.7 | PHAS= | -129.3 | FOM= | 0.77 | TEST= 0 |
| INDE | 3 | 42 | 59 | FOBS= | 0.0 | SIGMA= | 19.0 | PHAS= | 0.0 | FOM= | 0.00 | TEST= 1 |
| INDE | 3 | 42 | 61 | FOBS= | 51.7 | SIGMA= | 3.7 | PHAS= | 112.0 | FOM= | 0.58 | TEST= 0 |
| INDE | 3 | 42 | 63 | FOBS= | 94.2 | SIGMA= | 2.4 | PHAS= | -42.7 | FOM= | 0.90 | TEST= 0 |
| INDE | 3 | 42 | 65 | FOBS= | 37.3 | SIGMA= | 9.9 | PHAS= | 121.2 | FOM= | 0.78 | TEST= 0 |
| INDE | 3 | 43 | 4 | FOBS= | 128.4 | SIGMA= | 1.7 | PHAS= | 9.8 | FOM= | 0.76 | TEST= 0 |
| INDE | 3 | 43 | 10 | FOBS= | 370.4 | SIGMA= | 0.7 | PHAS= | -156.8 | FOM= | 0.99 | TEST= 0 |
| INDE | 3 | 43 | 12 | FOBS= | 112.2 | SIGMA= | 2.1 | PHAS= | -63.5 | FOM= | 0.94 | TEST= 0 |
| INDE | 3 | 43 | 14 | FOBS= | 90.4 | SIGMA= | 1.8 | PHAS= | 57.1 | FOM= | 0.90 | TEST= 1 |
| INDE | 3 | 43 | 16 | FOBS= | 103.6 | SIGMA= | 2.6 | PHAS= | -158.9 | FOM= | 0.94 | TEST= 0 |
| INDE | 3 | 43 | 18 | FOBS= | 295.0 | SIGMA= | 1.1 | PHAS= | -79.1 | FOM= | 0.99 | TEST= 0 |
| INDE | 3 | 43 | 20 | FOBS= | 42.9 | SIGMA= | 6.4 | PHAS= | 82.8 | FOM= | 0.48 | TEST= 0 |
| INDE | 3 | 43 | 22 | FOBS= | 150.7 | SIGMA= | 2.5 | PHAS= | 89.5 | FOM= | 0.78 | TEST= 0 |
| INDE | 3 | 43 | 24 | FOBS= | 59.8 | SIGMA= | 6.1 | PHAS= | -125.0 | FOM= | 0.75 | TEST= 0 |
| INDE | 3 | 43 | 26 | FOBS= | 282.4 | SIGMA= | 1.5 | PHAS= | -169.9 | FOM= | 0.96 | TEST= 0 |
| INDE | 3 | 43 | 28 | FOBS= | 115.8 | SIGMA= | 3.1 | PHAS= | -163.3 | FOM= | 0.88 | TEST= 0 |
| INDE | 3 | 43 | 30 | FOBS= | 217.4 | SIGMA= | 1.8 | PHAS= | -110.1 | FOM= | 0.89 | TEST= 0 |
| INDE | 3 | 43 | 32 | FOBS= | 72.0 | SIGMA= | 4.7 | PHAS= | -88.7 | FOM= | 0.38 | TEST= 0 |

*FIG. 12A - 95*

```
INDE  3  43  34  FOBS=   99.4  SIGMA=   2.6  PHAS=  136.0  FOM=  0.13  TEST= 1
INDE  3  43  36  FOBS=  133.0  SIGMA=   1.7  PHAS=  111.0  FOM=  0.91  TEST= 0
INDE  3  43  38  FOBS=    0.0  SIGMA=  22.4  PHAS=    0.0  FOM=  0.00  TEST= 0
INDE  3  43  40  FOBS=    0.0  SIGMA=  23.7  PHAS=    0.0  FOM=  0.00  TEST= 0
INDE  3  43  42  FOBS=  123.0  SIGMA=   1.6  PHAS=  -11.8  FOM=  0.88  TEST= 0
INDE  3  43  44  FOBS=   69.8  SIGMA=   2.5  PHAS=  148.2  FOM=  0.87  TEST= 0
INDE  3  43  46  FOBS=  115.9  SIGMA=   1.4  PHAS=   71.0  FOM=  0.95  TEST= 0
INDE  3  43  48  FOBS=   52.4  SIGMA=   2.8  PHAS=   52.0  FOM=  0.70  TEST= 0
INDE  3  43  50  FOBS=   28.3  SIGMA=   5.8  PHAS=   27.8  FOM=  0.62  TEST= 0
INDE  3  43  52  FOBS=   99.3  SIGMA=   1.8  PHAS=  101.3  FOM=  0.88  TEST= 0
INDE  3  43  54  FOBS=  119.7  SIGMA=   1.5  PHAS=  -66.4  FOM=  0.90  TEST= 0
INDE  3  43  56  FOBS=   62.0  SIGMA=   2.9  PHAS=  -31.2  FOM=  0.79  TEST= 0
INDE  3  43  58  FOBS=   77.6  SIGMA=   2.3  PHAS=   86.5  FOM=  0.93  TEST= 0
INDE  3  43  60  FOBS=    0.0  SIGMA=  18.6  PHAS=    0.0  FOM=  0.00  TEST= 1
INDE  3  43  62  FOBS=   69.1  SIGMA=   2.8  PHAS=   95.3  FOM=  0.29  TEST= 1
INDE  3  43  64  FOBS=    0.0  SIGMA=  23.8  PHAS=    0.0  FOM=  0.00  TEST= 0
INDE  3  44   3  FOBS=  307.4  SIGMA=   0.9  PHAS=  -68.2  FOM=  0.94  TEST= 0
INDE  3  44  11  FOBS=   55.8  SIGMA=   2.7  PHAS=    5.1  FOM=  0.29  TEST= 0
INDE  3  44  13  FOBS=  133.7  SIGMA=   1.3  PHAS= -104.2  FOM=  0.98  TEST= 0
INDE  3  44  15  FOBS=  147.4  SIGMA=   1.2  PHAS=   97.3  FOM=  0.77  TEST= 0
INDE  3  44  17  FOBS=  218.9  SIGMA=   1.3  PHAS=  -68.3  FOM=  0.96  TEST= 0
INDE  3  44  19  FOBS=  111.6  SIGMA=   2.2  PHAS= -108.3  FOM=  0.90  TEST= 1
INDE  3  44  21  FOBS=  132.6  SIGMA=   1.9  PHAS=   31.7  FOM=  0.96  TEST= 0
INDE  3  44  23  FOBS=  159.6  SIGMA=   2.5  PHAS=  -12.6  FOM=  0.89  TEST= 0
INDE  3  44  25  FOBS=  278.8  SIGMA=   1.6  PHAS=  104.6  FOM=  0.95  TEST= 0
INDE  3  44  27  FOBS=  165.3  SIGMA=   2.3  PHAS=  103.5  FOM=  0.89  TEST= 0
INDE  3  44  29  FOBS=   24.0  SIGMA=  14.3  PHAS=  133.3  FOM=  0.31  TEST= 0
INDE  3  44  31  FOBS=   18.2  SIGMA=  18.4  PHAS=  -70.0  FOM=  0.05  TEST= 0
INDE  3  44  33  FOBS=  143.6  SIGMA=   2.4  PHAS=   55.5  FOM=  0.82  TEST= 0
INDE  3  44  35  FOBS=   76.6  SIGMA=   2.9  PHAS=   49.5  FOM=  0.79  TEST= 0
INDE  3  44  37  FOBS=   55.9  SIGMA=   3.9  PHAS=   75.0  FOM=  0.82  TEST= 0
INDE  3  44  39  FOBS=    0.0  SIGMA=  23.6  PHAS=    0.0  FOM=  0.00  TEST= 0
INDE  3  44  41  FOBS=   49.8  SIGMA=   4.2  PHAS=   40.1  FOM=  0.44  TEST= 0
INDE  3  44  43  FOBS=   51.5  SIGMA=   3.5  PHAS=   -3.7  FOM=  0.37  TEST= 1
INDE  3  44  45  FOBS=   51.3  SIGMA=   3.1  PHAS=   52.6  FOM=  0.77  TEST= 0
INDE  3  44  47  FOBS=   77.4  SIGMA=   2.0  PHAS=  -12.6  FOM=  0.83  TEST= 0
INDE  3  44  49  FOBS=   77.1  SIGMA=   2.0  PHAS= -104.2  FOM=  0.91  TEST= 0
INDE  3  44  51  FOBS=   21.2  SIGMA=   8.6  PHAS=   44.0  FOM=  0.39  TEST= 0
INDE  3  44  53  FOBS=   55.8  SIGMA=   3.1  PHAS=  178.9  FOM=  0.52  TEST= 0
INDE  3  44  55  FOBS=  118.8  SIGMA=   1.6  PHAS= -178.8  FOM=  0.94  TEST= 0
INDE  3  44  57  FOBS=   57.3  SIGMA=   3.1  PHAS=  -70.9  FOM=  0.89  TEST= 0
INDE  3  44  59  FOBS=   14.2  SIGMA=  12.5  PHAS=  -63.3  FOM=  0.05  TEST= 0
INDE  3  44  61  FOBS=   55.5  SIGMA=   3.5  PHAS=   93.1  FOM=  0.66  TEST= 0
INDE  3  44  63  FOBS=    0.0  SIGMA=  25.7  PHAS=    0.0  FOM=  0.00  TEST= 0
INDE  3  45   4  FOBS=  314.6  SIGMA=   0.9  PHAS= -130.9  FOM=  0.98  TEST= 0
INDE  3  45  10  FOBS=  119.9  SIGMA=   1.7  PHAS= -103.3  FOM=  0.57  TEST= 0
INDE  3  45  12  FOBS=  113.7  SIGMA=   1.4  PHAS=  -86.3  FOM=  0.90  TEST= 0
INDE  3  45  14  FOBS=   74.8  SIGMA=   2.4  PHAS=  113.3  FOM=  0.74  TEST= 0
INDE  3  45  16  FOBS=  129.3  SIGMA=   1.5  PHAS=   91.3  FOM=  0.93  TEST= 0
INDE  3  45  18  FOBS=  224.5  SIGMA=   1.2  PHAS= -133.8  FOM=  0.90  TEST= 0
INDE  3  45  20  FOBS=    0.0  SIGMA=  24.1  PHAS=    0.0  FOM=  0.00  TEST= 0
INDE  3  45  22  FOBS=   57.2  SIGMA=   4.1  PHAS=  -10.9  FOM=  0.73  TEST= 0
INDE  3  45  24  FOBS=   37.6  SIGMA=   9.5  PHAS= -134.5  FOM=  0.09  TEST= 0
INDE  3  45  26  FOBS=   76.2  SIGMA=   4.7  PHAS=  104.5  FOM=  0.49  TEST= 0
INDE  3  45  28  FOBS=  109.3  SIGMA=   3.3  PHAS=   92.6  FOM=  0.92  TEST= 0
INDE  3  45  30  FOBS=  113.6  SIGMA=   3.1  PHAS=  -15.8  FOM=  0.53  TEST= 0
INDE  3  45  32  FOBS=   79.7  SIGMA=   4.2  PHAS=  -51.2  FOM=  0.46  TEST= 0
INDE  3  45  34  FOBS=  191.1  SIGMA=   1.9  PHAS= -110.1  FOM=  0.94  TEST= 0
INDE  3  45  36  FOBS=   32.3  SIGMA=   7.2  PHAS= -117.3  FOM=  0.10  TEST= 0
INDE  3  45  38  FOBS=   13.5  SIGMA=  15.9  PHAS=  -38.5  FOM=  0.11  TEST= 0
INDE  3  45  40  FOBS=    0.0  SIGMA=  22.7  PHAS=    0.0  FOM=  0.00  TEST= 1
INDE  3  45  42  FOBS=  102.5  SIGMA=   1.9  PHAS=   -6.5  FOM=  0.87  TEST= 0
INDE  3  45  44  FOBS=   40.1  SIGMA=   4.3  PHAS=  148.8  FOM=  0.47  TEST= 0
INDE  3  45  46  FOBS=   87.7  SIGMA=   1.8  PHAS=  -75.2  FOM=  0.83  TEST= 0
INDE  3  45  48  FOBS=   24.7  SIGMA=   6.6  PHAS=  -97.7  FOM=  0.15  TEST= 0
INDE  3  45  50  FOBS=   61.1  SIGMA=   2.9  PHAS=  106.2  FOM=  0.39  TEST= 0
INDE  3  45  52  FOBS=    0.0  SIGMA=  21.1  PHAS=    0.0  FOM=  0.00  TEST= 0
INDE  3  45  54  FOBS=   46.2  SIGMA=   3.8  PHAS=  169.7  FOM=  0.41  TEST= 0
INDE  3  45  56  FOBS=   18.7  SIGMA=  10.6  PHAS=   85.5  FOM=  0.35  TEST= 0
INDE  3  45  58  FOBS=   58.7  SIGMA=   3.1  PHAS=   56.2  FOM=  0.78  TEST= 0
```

*FIG. 12A - 96*

| | | | | | | | | | | | | |
|---|---|---|---|---|---|---|---|---|---|---|---|---|
| INDE | 3 | 45 | 60 | FOBS= | 70.7 | SIGMA= | 2.6 | PHAS= | 85.4 | FOM= | 0.41 | TEST= 0 |
| INDE | 3 | 45 | 62 | FOBS= | 68.6 | SIGMA= | 3.3 | PHAS= | 102.8 | FOM= | 0.70 | TEST= 0 |
| INDE | 3 | 46 | 3 | FOBS= | 161.9 | SIGMA= | 1.1 | PHAS= | -123.9 | FOM= | 0.85 | TEST= 0 |
| INDE | 3 | 46 | 11 | FOBS= | 207.9 | SIGMA= | 1.2 | PHAS= | 159.2 | FOM= | 0.92 | TEST= 0 |
| INDE | 3 | 46 | 13 | FOBS= | 167.9 | SIGMA= | 1.1 | PHAS= | -153.8 | FOM= | 0.89 | TEST= 0 |
| INDE | 3 | 46 | 15 | FOBS= | 152.0 | SIGMA= | 1.3 | PHAS= | -41.2 | FOM= | 0.87 | TEST= 0 |
| INDE | 3 | 46 | 17 | FOBS= | 333.8 | SIGMA= | 1.0 | PHAS= | -38.0 | FOM= | 0.98 | TEST= 0 |
| INDE | 3 | 46 | 19 | FOBS= | 41.3 | SIGMA= | 5.7 | PHAS= | 121.0 | FOM= | 0.28 | TEST= 0 |
| INDE | 3 | 46 | 21 | FOBS= | 74.1 | SIGMA= | 3.2 | PHAS= | -83.2 | FOM= | 0.51 | TEST= 0 |
| INDE | 3 | 46 | 23 | FOBS= | 199.3 | SIGMA= | 1.3 | PHAS= | -61.7 | FOM= | 0.75 | TEST= 1 |
| INDE | 3 | 46 | 25 | FOBS= | 177.7 | SIGMA= | 2.2 | PHAS= | -46.3 | FOM= | 0.17 | TEST= 1 |
| INDE | 3 | 46 | 27 | FOBS= | 165.7 | SIGMA= | 2.3 | PHAS= | 56.1 | FOM= | 0.87 | TEST= 0 |
| INDE | 3 | 46 | 29 | FOBS= | 163.4 | SIGMA= | 2.2 | PHAS= | 3.2 | FOM= | 0.95 | TEST= 0 |
| INDE | 3 | 46 | 31 | FOBS= | 58.8 | SIGMA= | 5.7 | PHAS= | -80.6 | FOM= | 0.42 | TEST= 0 |
| INDE | 3 | 46 | 33 | FOBS= | 122.6 | SIGMA= | 2.9 | PHAS= | -126.1 | FOM= | 0.73 | TEST= 0 |
| INDE | 3 | 46 | 35 | FOBS= | 137.9 | SIGMA= | 2.0 | PHAS= | 157.4 | FOM= | 0.97 | TEST= 0 |
| INDE | 3 | 46 | 37 | FOBS= | 34.3 | SIGMA= | 6.3 | PHAS= | -66.5 | FOM= | 0.20 | TEST= 0 |
| INDE | 3 | 46 | 39 | FOBS= | 0.0 | SIGMA= | 21.6 | PHAS= | 0.0 | FOM= | 0.00 | TEST= 0 |
| INDE | 3 | 46 | 41 | FOBS= | 90.9 | SIGMA= | 2.3 | PHAS= | -126.1 | FOM= | 0.81 | TEST= 0 |
| INDE | 3 | 46 | 43 | FOBS= | 0.0 | SIGMA= | 20.2 | PHAS= | 0.0 | FOM= | 0.00 | TEST= 0 |
| INDE | 3 | 46 | 45 | FOBS= | 58.5 | SIGMA= | 2.7 | PHAS= | 1.1 | FOM= | 0.50 | TEST= 0 |
| INDE | 3 | 46 | 47 | FOBS= | 39.8 | SIGMA= | 3.9 | PHAS= | -118.7 | FOM= | 0.50 | TEST= 0 |
| INDE | 3 | 46 | 49 | FOBS= | 0.0 | SIGMA= | 17.3 | PHAS= | 0.0 | FOM= | 0.00 | TEST= 1 |
| INDE | 3 | 46 | 51 | FOBS= | 95.4 | SIGMA= | 1.9 | PHAS= | 59.4 | FOM= | 0.92 | TEST= 0 |
| INDE | 3 | 46 | 53 | FOBS= | 58.8 | SIGMA= | 3.0 | PHAS= | 170.7 | FOM= | 0.76 | TEST= 0 |
| INDE | 3 | 46 | 55 | FOBS= | 0.0 | SIGMA= | 20.4 | PHAS= | 0.0 | FOM= | 0.00 | TEST= 0 |
| INDE | 3 | 46 | 57 | FOBS= | 52.6 | SIGMA= | 3.4 | PHAS= | -58.8 | FOM= | 0.82 | TEST= 0 |
| INDE | 3 | 46 | 59 | FOBS= | 13.7 | SIGMA= | 16.5 | PHAS= | 175.0 | FOM= | 0.18 | TEST= 0 |
| INDE | 3 | 46 | 61 | FOBS= | 80.5 | SIGMA= | 2.8 | PHAS= | 65.2 | FOM= | 0.92 | TEST= 0 |
| INDE | 3 | 47 | 4 | FOBS= | 231.1 | SIGMA= | 1.2 | PHAS= | 165.1 | FOM= | 0.93 | TEST= 0 |
| INDE | 3 | 47 | 12 | FOBS= | 106.6 | SIGMA= | 1.7 | PHAS= | -73.6 | FOM= | 0.97 | TEST= 0 |
| INDE | 3 | 47 | 14 | FOBS= | 238.4 | SIGMA= | 0.9 | PHAS= | 169.7 | FOM= | 0.94 | TEST= 0 |
| INDE | 3 | 47 | 16 | FOBS= | 197.8 | SIGMA= | 1.1 | PHAS= | 121.5 | FOM= | 0.93 | TEST= 0 |
| INDE | 3 | 47 | 18 | FOBS= | 288.8 | SIGMA= | 1.2 | PHAS= | -112.1 | FOM= | 0.98 | TEST= 0 |
| INDE | 3 | 47 | 20 | FOBS= | 0.0 | SIGMA= | 21.7 | PHAS= | 0.0 | FOM= | 0.00 | TEST= 0 |
| INDE | 3 | 47 | 22 | FOBS= | 153.2 | SIGMA= | 1.6 | PHAS= | 115.3 | FOM= | 0.91 | TEST= 0 |
| INDE | 3 | 47 | 24 | FOBS= | 116.4 | SIGMA= | 2.0 | PHAS= | -133.4 | FOM= | 0.69 | TEST= 0 |
| INDE | 3 | 47 | 26 | FOBS= | 71.4 | SIGMA= | 5.0 | PHAS= | -151.2 | FOM= | 0.72 | TEST= 0 |
| INDE | 3 | 47 | 28 | FOBS= | 209.1 | SIGMA= | 1.9 | PHAS= | -67.9 | FOM= | 0.96 | TEST= 0 |
| INDE | 3 | 47 | 30 | FOBS= | 0.0 | SIGMA= | 26.0 | PHAS= | 0.0 | FOM= | 0.00 | TEST= 0 |
| INDE | 3 | 47 | 32 | FOBS= | 149.0 | SIGMA= | 2.5 | PHAS= | 135.5 | FOM= | 0.95 | TEST= 0 |
| INDE | 3 | 47 | 34 | FOBS= | 29.9 | SIGMA= | 10.9 | PHAS= | -178.3 | FOM= | 0.10 | TEST= 1 |
| INDE | 3 | 47 | 36 | FOBS= | 84.5 | SIGMA= | 3.1 | PHAS= | 99.5 | FOM= | 0.76 | TEST= 0 |
| INDE | 3 | 47 | 38 | FOBS= | 22.5 | SIGMA= | 10.2 | PHAS= | -123.0 | FOM= | 0.78 | TEST= 0 |
| INDE | 3 | 47 | 40 | FOBS= | 109.6 | SIGMA= | 2.2 | PHAS= | -153.1 | FOM= | 0.92 | TEST= 0 |
| INDE | 3 | 47 | 42 | FOBS= | 62.6 | SIGMA= | 3.0 | PHAS= | 151.1 | FOM= | 0.85 | TEST= 0 |
| INDE | 3 | 47 | 44 | FOBS= | 0.0 | SIGMA= | 18.1 | PHAS= | 0.0 | FOM= | 0.00 | TEST= 0 |
| INDE | 3 | 47 | 46 | FOBS= | 103.2 | SIGMA= | 1.6 | PHAS= | -109.2 | FOM= | 0.90 | TEST= 0 |
| INDE | 3 | 47 | 48 | FOBS= | 58.5 | SIGMA= | 2.7 | PHAS= | 141.0 | FOM= | 0.80 | TEST= 0 |
| INDE | 3 | 47 | 50 | FOBS= | 99.1 | SIGMA= | 1.8 | PHAS= | -47.9 | FOM= | 0.89 | TEST= 0 |
| INDE | 3 | 47 | 52 | FOBS= | 0.0 | SIGMA= | 19.9 | PHAS= | 0.0 | FOM= | 0.00 | TEST= 0 |
| INDE | 3 | 47 | 54 | FOBS= | 59.9 | SIGMA= | 2.9 | PHAS= | -134.8 | FOM= | 0.71 | TEST= 0 |
| INDE | 3 | 47 | 56 | FOBS= | 0.0 | SIGMA= | 18.8 | PHAS= | 0.0 | FOM= | 0.00 | TEST= 0 |
| INDE | 3 | 47 | 58 | FOBS= | 58.7 | SIGMA= | 3.3 | PHAS= | 62.7 | FOM= | 0.54 | TEST= 0 |
| INDE | 3 | 47 | 60 | FOBS= | 0.0 | SIGMA= | 21.3 | PHAS= | 0.0 | FOM= | 0.00 | TEST= 0 |
| INDE | 3 | 48 | 3 | FOBS= | 135.3 | SIGMA= | 1.4 | PHAS= | -86.0 | FOM= | 0.89 | TEST= 0 |
| INDE | 3 | 48 | 11 | FOBS= | 95.4 | SIGMA= | 2.4 | PHAS= | -133.2 | FOM= | 0.72 | TEST= 0 |
| INDE | 3 | 48 | 13 | FOBS= | 114.2 | SIGMA= | 1.6 | PHAS= | 89.6 | FOM= | 0.92 | TEST= 0 |
| INDE | 3 | 48 | 15 | FOBS= | 78.6 | SIGMA= | 2.4 | PHAS= | -0.7 | FOM= | 0.86 | TEST= 0 |
| INDE | 3 | 48 | 17 | FOBS= | 277.2 | SIGMA= | 0.8 | PHAS= | -41.4 | FOM= | 0.96 | TEST= 0 |
| INDE | 3 | 48 | 19 | FOBS= | 0.0 | SIGMA= | 23.6 | PHAS= | 0.0 | FOM= | 0.00 | TEST= 0 |
| INDE | 3 | 48 | 21 | FOBS= | 119.9 | SIGMA= | 2.0 | PHAS= | 21.8 | FOM= | 0.88 | TEST= 1 |
| INDE | 3 | 48 | 23 | FOBS= | 32.1 | SIGMA= | 8.2 | PHAS= | -28.1 | FOM= | 0.13 | TEST= 1 |
| INDE | 3 | 48 | 25 | FOBS= | 102.4 | SIGMA= | 2.3 | PHAS= | 34.3 | FOM= | 0.73 | TEST= 0 |
| INDE | 3 | 48 | 27 | FOBS= | 236.4 | SIGMA= | 1.7 | PHAS= | 150.0 | FOM= | 0.93 | TEST= 0 |
| INDE | 3 | 48 | 29 | FOBS= | 58.8 | SIGMA= | 5.9 | PHAS= | -173.2 | FOM= | 0.71 | TEST= 0 |
| INDE | 3 | 48 | 31 | FOBS= | 181.6 | SIGMA= | 2.1 | PHAS= | 32.7 | FOM= | 0.91 | TEST= 0 |
| INDE | 3 | 48 | 33 | FOBS= | 196.3 | SIGMA= | 1.9 | PHAS= | -8.9 | FOM= | 0.97 | TEST= 0 |
| INDE | 3 | 48 | 35 | FOBS= | 30.8 | SIGMA= | 10.5 | PHAS= | -125.2 | FOM= | 0.12 | TEST= 0 |
| INDE | 3 | 48 | 37 | FOBS= | 104.9 | SIGMA= | 2.3 | PHAS= | -66.4 | FOM= | 0.94 | TEST= 0 |

*FIG. 12A - 97*

```
INDE  3  48  39 FOBS=   70.9 SIGMA=  3.3 PHAS= -159.3 FOM= 0.67 TEST= 0
INDE  3  48  41 FOBS=  111.9 SIGMA=  1.9 PHAS=  115.2 FOM= 0.93 TEST= 0
INDE  3  48  43 FOBS=    0.0 SIGMA= 19.1 PHAS=    0.0 FOM= 0.00 TEST= 0
INDE  3  48  45 FOBS=    0.0 SIGMA= 17.6 PHAS=    0.0 FOM= 0.00 TEST= 0
INDE  3  48  47 FOBS=   77.8 SIGMA=  2.0 PHAS=  166.2 FOM= 0.73 TEST= 0
INDE  3  48  49 FOBS=   93.9 SIGMA=  2.0 PHAS= -153.9 FOM= 0.53 TEST= 1
INDE  3  48  51 FOBS=    0.0 SIGMA= 19.8 PHAS=    0.0 FOM= 0.00 TEST= 1
INDE  3  48  53 FOBS=   67.3 SIGMA=  2.7 PHAS= -176.3 FOM= 0.83 TEST= 0
INDE  3  48  55 FOBS=   46.9 SIGMA=  3.8 PHAS=  157.4 FOM= 0.09 TEST= 0
INDE  3  48  57 FOBS=   35.1 SIGMA=  6.0 PHAS=  105.8 FOM= 0.39 TEST= 0
INDE  3  48  59 FOBS=    0.0 SIGMA= 23.9 PHAS=    0.0 FOM= 0.00 TEST= 1
INDE  3  48  61 FOBS=   78.0 SIGMA=  3.3 PHAS=   84.2 FOM= 0.76 TEST= 0
INDE  3  49  12 FOBS=   49.5 SIGMA=  4.5 PHAS=  -34.0 FOM= 0.59 TEST= 0
INDE  3  49  14 FOBS=    0.0 SIGMA= 18.5 PHAS=    0.0 FOM= 0.00 TEST= 0
INDE  3  49  16 FOBS=  184.9 SIGMA=  1.0 PHAS=  -28.8 FOM= 0.94 TEST= 0
INDE  3  49  18 FOBS=  197.1 SIGMA=  1.1 PHAS= -135.5 FOM= 0.95 TEST= 0
INDE  3  49  20 FOBS=    0.0 SIGMA= 25.2 PHAS=    0.0 FOM= 0.00 TEST= 0
INDE  3  49  22 FOBS=   47.7 SIGMA=  4.9 PHAS=  -64.8 FOM= 0.34 TEST= 0
INDE  3  49  24 FOBS=   88.8 SIGMA=  2.7 PHAS= -174.5 FOM= 0.75 TEST= 0
INDE  3  49  26 FOBS=  109.8 SIGMA=  3.3 PHAS=   37.7 FOM= 0.87 TEST= 0
INDE  3  49  28 FOBS=   70.1 SIGMA=  4.9 PHAS=   18.8 FOM= 0.43 TEST= 0
INDE  3  49  30 FOBS=  158.6 SIGMA=  2.3 PHAS=   43.4 FOM= 0.81 TEST= 1
INDE  3  49  32 FOBS=  104.7 SIGMA=  3.3 PHAS=  -64.0 FOM= 0.94 TEST= 0
INDE  3  49  34 FOBS=  180.4 SIGMA=  2.0 PHAS= -140.0 FOM= 0.93 TEST= 0
INDE  3  49  36 FOBS=  115.0 SIGMA=  2.9 PHAS=  172.5 FOM= 0.89 TEST= 0
INDE  3  49  38 FOBS=   62.8 SIGMA=  3.4 PHAS=  -73.0 FOM= 0.47 TEST= 1
INDE  3  49  40 FOBS=   39.1 SIGMA=  6.4 PHAS=   22.5 FOM= 0.74 TEST= 0
INDE  3  49  42 FOBS=   63.6 SIGMA=  2.9 PHAS=   70.1 FOM= 0.60 TEST= 1
INDE  3  49  44 FOBS=   39.9 SIGMA=  4.1 PHAS=   80.1 FOM= 0.33 TEST= 0
INDE  3  49  46 FOBS=   37.9 SIGMA=  4.1 PHAS=  -90.2 FOM= 0.54 TEST= 0
INDE  3  49  48 FOBS=   27.8 SIGMA=  5.6 PHAS=  168.1 FOM= 0.47 TEST= 0
INDE  3  49  50 FOBS=   30.6 SIGMA=  5.9 PHAS= -115.0 FOM= 0.53 TEST= 0
INDE  3  49  52 FOBS=   60.1 SIGMA=  3.0 PHAS=   31.7 FOM= 0.67 TEST= 0
INDE  3  49  54 FOBS=   48.6 SIGMA=  3.7 PHAS= -127.1 FOM= 0.83 TEST= 0
INDE  3  49  56 FOBS=   36.4 SIGMA=  4.9 PHAS=   26.5 FOM= 0.49 TEST= 0
INDE  3  49  58 FOBS=   64.3 SIGMA=  3.3 PHAS=   10.9 FOM= 0.72 TEST= 0
INDE  3  49  60 FOBS=   29.6 SIGMA= 11.2 PHAS=  -84.5 FOM= 0.18 TEST= 1
INDE  3  50   3 FOBS=   70.2 SIGMA=  1.6 PHAS=  -58.8 FOM= 0.94 TEST= 0
INDE  3  50  13 FOBS=   78.3 SIGMA=  2.4 PHAS=  -30.2 FOM= 0.85 TEST= 0
INDE  3  50  15 FOBS=  114.1 SIGMA=  1.6 PHAS= -117.4 FOM= 0.86 TEST= 0
INDE  3  50  17 FOBS=  247.9 SIGMA=  0.9 PHAS= -112.1 FOM= 0.94 TEST= 0
INDE  3  50  19 FOBS=   27.6 SIGMA=  6.2 PHAS=  123.7 FOM= 0.15 TEST= 0
INDE  3  50  21 FOBS=  115.0 SIGMA=  2.1 PHAS=    6.6 FOM= 0.64 TEST= 0
INDE  3  50  23 FOBS=  206.2 SIGMA=  1.3 PHAS=  115.6 FOM= 0.92 TEST= 0
INDE  3  50  25 FOBS=   70.4 SIGMA=  3.3 PHAS=   68.0 FOM= 0.60 TEST= 0
INDE  3  50  27 FOBS=   93.5 SIGMA=  3.8 PHAS=   52.6 FOM= 0.72 TEST= 0
INDE  3  50  29 FOBS=   73.3 SIGMA=  4.7 PHAS=  -63.0 FOM= 0.48 TEST= 0
INDE  3  50  31 FOBS=   75.3 SIGMA=  4.5 PHAS=   66.0 FOM= 0.05 TEST= 1
INDE  3  50  33 FOBS=   50.2 SIGMA=  9.2 PHAS=   96.7 FOM= 0.59 TEST= 0
INDE  3  50  35 FOBS=  213.8 SIGMA=  1.8 PHAS=   95.5 FOM= 0.97 TEST= 0
INDE  3  50  37 FOBS=   51.1 SIGMA=  4.9 PHAS=   76.5 FOM= 0.24 TEST= 0
INDE  3  50  39 FOBS=    0.0 SIGMA= 23.3 PHAS=    0.0 FOM= 0.00 TEST= 0
INDE  3  50  41 FOBS=   28.2 SIGMA=  7.2 PHAS=  -74.3 FOM= 0.48 TEST= 0
INDE  3  50  43 FOBS=   53.2 SIGMA=  3.3 PHAS=  -45.5 FOM= 0.68 TEST= 0
INDE  3  50  45 FOBS=   48.3 SIGMA=  3.3 PHAS= -175.4 FOM= 0.72 TEST= 0
INDE  3  50  47 FOBS=   91.0 SIGMA=  1.8 PHAS=  -82.2 FOM= 0.88 TEST= 1
INDE  3  50  49 FOBS=   59.6 SIGMA=  3.1 PHAS=   76.2 FOM= 0.64 TEST= 0
INDE  3  50  51 FOBS=   28.0 SIGMA=  6.4 PHAS=  117.9 FOM= 0.42 TEST= 0
INDE  3  50  53 FOBS=   62.1 SIGMA=  2.9 PHAS= -175.0 FOM= 0.79 TEST= 0
INDE  3  50  55 FOBS=    0.0 SIGMA= 18.9 PHAS=    0.0 FOM= 0.00 TEST= 0
INDE  3  50  57 FOBS=    0.0 SIGMA= 21.4 PHAS=    0.0 FOM= 0.00 TEST= 0
INDE  3  50  59 FOBS=   46.2 SIGMA=  5.4 PHAS= -152.3 FOM= 0.44 TEST= 0
INDE  3  51   4 FOBS=   46.0 SIGMA=  3.7 PHAS=  149.7 FOM= 0.08 TEST= 0
INDE  3  51  12 FOBS=   84.1 SIGMA=  2.6 PHAS= -162.1 FOM= 0.16 TEST= 0
INDE  3  51  14 FOBS=  136.8 SIGMA=  1.3 PHAS=  115.4 FOM= 0.88 TEST= 0
INDE  3  51  16 FOBS=  170.5 SIGMA=  1.1 PHAS=  -68.4 FOM= 0.91 TEST= 0
INDE  3  51  18 FOBS=   65.4 SIGMA=  2.6 PHAS=  167.4 FOM= 0.80 TEST= 0
INDE  3  51  20 FOBS=  127.1 SIGMA=  1.4 PHAS=   56.4 FOM= 0.80 TEST= 0
INDE  3  51  22 FOBS=  243.1 SIGMA=  1.1 PHAS=   62.2 FOM= 0.15 TEST= 1
INDE  3  51  24 FOBS=  201.4 SIGMA=  1.3 PHAS=   19.5 FOM= 0.94 TEST= 0
```

*FIG. 12A - 98*

| | | | | | | | | | | | |
|---|---|---|---|---|---|---|---|---|---|---|---|
| INDE | 3 | 51 | 26 | FOBS= | 69.2 | SIGMA= | 3.4 | PHAS= | 22.5 | FOM= | 0.93 | TEST= 0
| INDE | 3 | 51 | 28 | FOBS= | 87.8 | SIGMA= | 4.0 | PHAS= | 13.9 | FOM= | 0.44 | TEST= 1
| INDE | 3 | 51 | 30 | FOBS= | 0.0 | SIGMA= | 25.8 | PHAS= | 0.0 | FOM= | 0.00 | TEST= 0
| INDE | 3 | 51 | 32 | FOBS= | 39.5 | SIGMA= | 8.5 | PHAS= | -117.7 | FOM= | 0.06 | TEST= 1
| INDE | 3 | 51 | 34 | FOBS= | 44.2 | SIGMA= | 7.5 | PHAS= | -23.8 | FOM= | 0.56 | TEST= 0
| INDE | 3 | 51 | 36 | FOBS= | 0.0 | SIGMA= | 25.4 | PHAS= | 0.0 | FOM= | 0.00 | TEST= 0
| INDE | 3 | 51 | 38 | FOBS= | 7.9 | SIGMA= | 31.7 | PHAS= | -33.3 | FOM= | 0.04 | TEST= 0
| INDE | 3 | 51 | 40 | FOBS= | 0.0 | SIGMA= | 21.2 | PHAS= | 0.0 | FOM= | 0.00 | TEST= 0
| INDE | 3 | 51 | 42 | FOBS= | 36.0 | SIGMA= | 5.2 | PHAS= | 154.2 | FOM= | 0.68 | TEST= 0
| INDE | 3 | 51 | 44 | FOBS= | 74.3 | SIGMA= | 2.3 | PHAS= | 102.5 | FOM= | 0.89 | TEST= 0
| INDE | 3 | 51 | 46 | FOBS= | 38.2 | SIGMA= | 5.1 | PHAS= | -124.8 | FOM= | 0.43 | TEST= 0
| INDE | 3 | 51 | 48 | FOBS= | 120.7 | SIGMA= | 1.6 | PHAS= | -128.8 | FOM= | 0.62 | TEST= 1
| INDE | 3 | 51 | 50 | FOBS= | 73.5 | SIGMA= | 2.5 | PHAS= | -144.5 | FOM= | 0.53 | TEST= 0
| INDE | 3 | 51 | 52 | FOBS= | 82.5 | SIGMA= | 2.2 | PHAS= | -127.8 | FOM= | 0.26 | TEST= 1
| INDE | 3 | 51 | 54 | FOBS= | 0.0 | SIGMA= | 20.0 | PHAS= | 0.0 | FOM= | 0.00 | TEST= 1
| INDE | 3 | 51 | 56 | FOBS= | 57.0 | SIGMA= | 3.4 | PHAS= | -127.8 | FOM= | 0.24 | TEST= 0
| INDE | 3 | 51 | 58 | FOBS= | 0.0 | SIGMA= | 22.2 | PHAS= | 0.0 | FOM= | 0.00 | TEST= 0
| INDE | 3 | 52 | 3 | FOBS= | 133.0 | SIGMA= | 1.9 | PHAS= | -133.8 | FOM= | 0.96 | TEST= 0
| INDE | 3 | 52 | 13 | FOBS= | 136.6 | SIGMA= | 1.7 | PHAS= | 34.4 | FOM= | 0.93 | TEST= 0
| INDE | 3 | 52 | 15 | FOBS= | 156.0 | SIGMA= | 1.1 | PHAS= | -132.4 | FOM= | 0.91 | TEST= 0
| INDE | 3 | 52 | 17 | FOBS= | 54.9 | SIGMA= | 3.0 | PHAS= | 10.2 | FOM= | 0.26 | TEST= 0
| INDE | 3 | 52 | 19 | FOBS= | 54.7 | SIGMA= | 3.1 | PHAS= | 19.5 | FOM= | 0.58 | TEST= 0
| INDE | 3 | 52 | 21 | FOBS= | 182.2 | SIGMA= | 1.2 | PHAS= | -112.9 | FOM= | 0.89 | TEST= 1
| INDE | 3 | 52 | 23 | FOBS= | 146.2 | SIGMA= | 1.7 | PHAS= | -61.6 | FOM= | 0.88 | TEST= 0
| INDE | 3 | 52 | 25 | FOBS= | 154.4 | SIGMA= | 1.6 | PHAS= | -113.5 | FOM= | 0.91 | TEST= 0
| INDE | 3 | 52 | 27 | FOBS= | 17.5 | SIGMA= | 13.2 | PHAS= | -31.7 | FOM= | 0.17 | TEST= 0
| INDE | 3 | 52 | 29 | FOBS= | 69.0 | SIGMA= | 4.9 | PHAS= | 172.0 | FOM= | 0.64 | TEST= 0
| INDE | 3 | 52 | 31 | FOBS= | 46.3 | SIGMA= | 7.3 | PHAS= | -172.2 | FOM= | 0.35 | TEST= 0
| INDE | 3 | 52 | 33 | FOBS= | 105.3 | SIGMA= | 3.3 | PHAS= | -15.2 | FOM= | 0.80 | TEST= 0
| INDE | 3 | 52 | 35 | FOBS= | 144.8 | SIGMA= | 2.4 | PHAS= | 91.8 | FOM= | 0.93 | TEST= 0
| INDE | 3 | 52 | 37 | FOBS= | 61.0 | SIGMA= | 5.4 | PHAS= | 40.2 | FOM= | 0.28 | TEST= 0
| INDE | 3 | 52 | 39 | FOBS= | 27.2 | SIGMA= | 8.3 | PHAS= | 24.5 | FOM= | 0.55 | TEST= 0
| INDE | 3 | 52 | 41 | FOBS= | 27.7 | SIGMA= | 6.7 | PHAS= | -56.6 | FOM= | 0.27 | TEST= 0
| INDE | 3 | 52 | 43 | FOBS= | 72.7 | SIGMA= | 2.3 | PHAS= | 34.6 | FOM= | 0.88 | TEST= 0
| INDE | 3 | 52 | 45 | FOBS= | 68.8 | SIGMA= | 2.3 | PHAS= | 143.5 | FOM= | 0.41 | TEST= 0
| INDE | 3 | 52 | 47 | FOBS= | 77.1 | SIGMA= | 2.1 | PHAS= | -168.4 | FOM= | 0.85 | TEST= 0
| INDE | 3 | 52 | 49 | FOBS= | 58.2 | SIGMA= | 3.2 | PHAS= | 25.6 | FOM= | 0.77 | TEST= 0
| INDE | 3 | 52 | 51 | FOBS= | 80.5 | SIGMA= | 2.3 | PHAS= | 156.3 | FOM= | 0.90 | TEST= 0
| INDE | 3 | 52 | 53 | FOBS= | 42.3 | SIGMA= | 4.3 | PHAS= | 136.3 | FOM= | 0.15 | TEST= 1
| INDE | 3 | 52 | 55 | FOBS= | 14.4 | SIGMA= | 14.2 | PHAS= | 38.7 | FOM= | 0.08 | TEST= 1
| INDE | 3 | 52 | 57 | FOBS= | 0.0 | SIGMA= | 24.0 | PHAS= | 0.0 | FOM= | 0.00 | TEST= 0
| INDE | 3 | 53 | 4 | FOBS= | 44.3 | SIGMA= | 3.6 | PHAS= | -76.3 | FOM= | 0.27 | TEST= 0
| INDE | 3 | 53 | 14 | FOBS= | 16.7 | SIGMA= | 13.1 | PHAS= | 74.7 | FOM= | 0.01 | TEST= 1
| INDE | 3 | 53 | 16 | FOBS= | 90.7 | SIGMA= | 1.8 | PHAS= | -10.1 | FOM= | 0.70 | TEST= 0
| INDE | 3 | 53 | 18 | FOBS= | 176.5 | SIGMA= | 1.0 | PHAS= | -51.4 | FOM= | 0.94 | TEST= 0
| INDE | 3 | 53 | 20 | FOBS= | 67.6 | SIGMA= | 2.6 | PHAS= | -169.9 | FOM= | 0.88 | TEST= 0
| INDE | 3 | 53 | 22 | FOBS= | 0.0 | SIGMA= | 20.6 | PHAS= | 0.0 | FOM= | 0.00 | TEST= 1
| INDE | 3 | 53 | 24 | FOBS= | 47.1 | SIGMA= | 4.9 | PHAS= | -122.7 | FOM= | 0.71 | TEST= 0
| INDE | 3 | 53 | 26 | FOBS= | 99.5 | SIGMA= | 2.4 | PHAS= | 171.4 | FOM= | 0.92 | TEST= 0
| INDE | 3 | 53 | 28 | FOBS= | 32.2 | SIGMA= | 7.1 | PHAS= | 22.4 | FOM= | 0.26 | TEST= 0
| INDE | 3 | 53 | 30 | FOBS= | 112.4 | SIGMA= | 3.1 | PHAS= | 112.1 | FOM= | 0.94 | TEST= 0
| INDE | 3 | 53 | 32 | FOBS= | 46.1 | SIGMA= | 7.2 | PHAS= | 72.9 | FOM= | 0.44 | TEST= 0
| INDE | 3 | 53 | 34 | FOBS= | 29.3 | SIGMA= | 11.4 | PHAS= | 64.7 | FOM= | 0.50 | TEST= 1
| INDE | 3 | 53 | 36 | FOBS= | 40.1 | SIGMA= | 8.2 | PHAS= | -107.2 | FOM= | 0.24 | TEST= 0
| INDE | 3 | 53 | 38 | FOBS= | 28.8 | SIGMA= | 11.1 | PHAS= | -129.9 | FOM= | 0.51 | TEST= 0
| INDE | 3 | 53 | 40 | FOBS= | 51.9 | SIGMA= | 3.9 | PHAS= | -84.7 | FOM= | 0.41 | TEST= 0
| INDE | 3 | 53 | 42 | FOBS= | 0.0 | SIGMA= | 19.5 | PHAS= | 0.0 | FOM= | 0.00 | TEST= 1
| INDE | 3 | 53 | 44 | FOBS= | 82.4 | SIGMA= | 2.1 | PHAS= | -51.7 | FOM= | 0.88 | TEST= 0
| INDE | 3 | 53 | 46 | FOBS= | 56.6 | SIGMA= | 2.9 | PHAS= | 66.6 | FOM= | 0.63 | TEST= 0
| INDE | 3 | 53 | 48 | FOBS= | 12.4 | SIGMA= | 15.4 | PHAS= | -56.8 | FOM= | 0.09 | TEST= 0
| INDE | 3 | 53 | 50 | FOBS= | 31.3 | SIGMA= | 6.2 | PHAS= | -126.9 | FOM= | 0.29 | TEST= 0
| INDE | 3 | 53 | 52 | FOBS= | 38.3 | SIGMA= | 5.1 | PHAS= | 69.5 | FOM= | 0.41 | TEST= 0
| INDE | 3 | 53 | 54 | FOBS= | 62.1 | SIGMA= | 3.2 | PHAS= | -55.3 | FOM= | 0.85 | TEST= 0
| INDE | 3 | 53 | 56 | FOBS= | 55.9 | SIGMA= | 5.1 | PHAS= | 50.5 | FOM= | 0.84 | TEST= 0
| INDE | 3 | 54 | 3 | FOBS= | 109.7 | SIGMA= | 1.5 | PHAS= | -130.4 | FOM= | 0.98 | TEST= 0
| INDE | 3 | 54 | 15 | FOBS= | 43.2 | SIGMA= | 3.7 | PHAS= | -153.5 | FOM= | 0.23 | TEST= 1
| INDE | 3 | 54 | 17 | FOBS= | 76.7 | SIGMA= | 2.1 | PHAS= | -70.8 | FOM= | 0.77 | TEST= 0
| INDE | 3 | 54 | 19 | FOBS= | 176.2 | SIGMA= | 1.0 | PHAS= | 152.6 | FOM= | 0.96 | TEST= 0
| INDE | 3 | 54 | 21 | FOBS= | 0.0 | SIGMA= | 18.4 | PHAS= | 0.0 | FOM= | 0.00 | TEST= 0
| INDE | 3 | 54 | 23 | FOBS= | 119.1 | SIGMA= | 2.0 | PHAS= | 8.2 | FOM= | 0.69 | TEST= 0

*FIG. 12A - 99*

| | | | | | | | | | | | |
|---|---|---|---|---|---|---|---|---|---|---|---|
| INDE | 3 | 54 | 25 | FOBS= | 65.4 | SIGMA= | 3.6 | PHAS= | -170.8 | FOM= | 0.74 | TEST= 1
| INDE | 3 | 54 | 27 | FOBS= | 94.7 | SIGMA= | 2.5 | PHAS= | 96.1 | FOM= | 0.90 | TEST= 0
| INDE | 3 | 54 | 29 | FOBS= | 119.2 | SIGMA= | 2.0 | PHAS= | 88.1 | FOM= | 0.94 | TEST= 0
| INDE | 3 | 54 | 31 | FOBS= | 33.4 | SIGMA= | 10.0 | PHAS= | -128.4 | FOM= | 0.07 | TEST= 1
| INDE | 3 | 54 | 33 | FOBS= | 80.7 | SIGMA= | 4.2 | PHAS= | -4.4 | FOM= | 0.91 | TEST= 0
| INDE | 3 | 54 | 35 | FOBS= | 74.5 | SIGMA= | 4.5 | PHAS= | 76.1 | FOM= | 0.85 | TEST= 0
| INDE | 3 | 54 | 37 | FOBS= | 52.1 | SIGMA= | 6.2 | PHAS= | 117.9 | FOM= | 0.85 | TEST= 0
| INDE | 3 | 54 | 39 | FOBS= | 130.3 | SIGMA= | 2.0 | PHAS= | 85.3 | FOM= | 0.92 | TEST= 0
| INDE | 3 | 54 | 41 | FOBS= | 75.6 | SIGMA= | 2.4 | PHAS= | 19.8 | FOM= | 0.82 | TEST= 0
| INDE | 3 | 54 | 43 | FOBS= | 118.0 | SIGMA= | 1.5 | PHAS= | -108.2 | FOM= | 0.02 | TEST= 1
| INDE | 3 | 54 | 45 | FOBS= | 57.3 | SIGMA= | 2.8 | PHAS= | -161.4 | FOM= | 0.88 | TEST= 0
| INDE | 3 | 54 | 47 | FOBS= | 31.5 | SIGMA= | 5.9 | PHAS= | -77.2 | FOM= | 0.58 | TEST= 0
| INDE | 3 | 54 | 49 | FOBS= | 26.3 | SIGMA= | 7.1 | PHAS= | -134.1 | FOM= | 0.21 | TEST= 0
| INDE | 3 | 54 | 51 | FOBS= | 41.2 | SIGMA= | 5.2 | PHAS= | 69.2 | FOM= | 0.81 | TEST= 0
| INDE | 3 | 54 | 53 | FOBS= | 45.2 | SIGMA= | 5.1 | PHAS= | 108.3 | FOM= | 0.45 | TEST= 0
| INDE | 3 | 54 | 55 | FOBS= | 61.6 | SIGMA= | 4.6 | PHAS= | -108.9 | FOM= | 0.83 | TEST= 0
| INDE | 3 | 55 | 4 | FOBS= | 64.3 | SIGMA= | 2.1 | PHAS= | 104.2 | FOM= | 0.84 | TEST= 0
| INDE | 3 | 55 | 14 | FOBS= | 137.7 | SIGMA= | 1.5 | PHAS= | -53.8 | FOM= | 0.96 | TEST= 0
| INDE | 3 | 55 | 16 | FOBS= | 73.0 | SIGMA= | 2.1 | PHAS= | -104.0 | FOM= | 0.90 | TEST= 0
| INDE | 3 | 55 | 18 | FOBS= | 23.3 | SIGMA= | 6.8 | PHAS= | 12.3 | FOM= | 0.28 | TEST= 0
| INDE | 3 | 55 | 20 | FOBS= | 131.3 | SIGMA= | 1.4 | PHAS= | -38.7 | FOM= | 0.92 | TEST= 0
| INDE | 3 | 55 | 22 | FOBS= | 59.2 | SIGMA= | 2.9 | PHAS= | -23.4 | FOM= | 0.50 | TEST= 0
| INDE | 3 | 55 | 24 | FOBS= | 26.2 | SIGMA= | 8.6 | PHAS= | 57.4 | FOM= | 0.10 | TEST= 0
| INDE | 3 | 55 | 26 | FOBS= | 59.5 | SIGMA= | 3.9 | PHAS= | 61.9 | FOM= | 0.91 | TEST= 0
| INDE | 3 | 55 | 28 | FOBS= | 130.2 | SIGMA= | 1.9 | PHAS= | 42.8 | FOM= | 0.60 | TEST= 1
| INDE | 3 | 55 | 30 | FOBS= | 48.2 | SIGMA= | 4.7 | PHAS= | -172.0 | FOM= | 0.71 | TEST= 0
| INDE | 3 | 55 | 32 | FOBS= | 99.3 | SIGMA= | 3.5 | PHAS= | -80.0 | FOM= | 0.88 | TEST= 0
| INDE | 3 | 55 | 34 | FOBS= | 0.0 | SIGMA= | 25.6 | PHAS= | 0.0 | FOM= | 0.00 | TEST= 0
| INDE | 3 | 55 | 36 | FOBS= | 0.0 | SIGMA= | 25.4 | PHAS= | 0.0 | FOM= | 0.00 | TEST= 1
| INDE | 3 | 55 | 38 | FOBS= | 107.8 | SIGMA= | 3.1 | PHAS= | 32.6 | FOM= | 0.84 | TEST= 0
| INDE | 3 | 55 | 40 | FOBS= | 83.5 | SIGMA= | 2.7 | PHAS= | -106.3 | FOM= | 0.78 | TEST= 0
| INDE | 3 | 55 | 42 | FOBS= | 45.5 | SIGMA= | 3.7 | PHAS= | -25.9 | FOM= | 0.40 | TEST= 0
| INDE | 3 | 55 | 44 | FOBS= | 30.7 | SIGMA= | 5.9 | PHAS= | 98.1 | FOM= | 0.68 | TEST= 0
| INDE | 3 | 55 | 46 | FOBS= | 35.8 | SIGMA= | 4.5 | PHAS= | 178.2 | FOM= | 0.46 | TEST= 0
| INDE | 3 | 55 | 48 | FOBS= | 0.0 | SIGMA= | 22.1 | PHAS= | 0.0 | FOM= | 0.00 | TEST= 0
| INDE | 3 | 55 | 50 | FOBS= | 33.4 | SIGMA= | 6.6 | PHAS= | 90.3 | FOM= | 0.18 | TEST= 0
| INDE | 3 | 55 | 52 | FOBS= | 0.0 | SIGMA= | 22.4 | PHAS= | 0.0 | FOM= | 0.00 | TEST= 0
| INDE | 3 | 55 | 54 | FOBS= | 0.0 | SIGMA= | 25.3 | PHAS= | 0.0 | FOM= | 0.00 | TEST= 0
| INDE | 3 | 56 | 3 | FOBS= | 67.7 | SIGMA= | 3.4 | PHAS= | 133.4 | FOM= | 0.85 | TEST= 0
| INDE | 3 | 56 | 5 | FOBS= | 245.7 | SIGMA= | 0.8 | PHAS= | -78.5 | FOM= | 0.93 | TEST= 0
| INDE | 3 | 56 | 13 | FOBS= | 47.3 | SIGMA= | 10.7 | PHAS= | 141.3 | FOM= | 0.30 | TEST= 0
| INDE | 3 | 56 | 15 | FOBS= | 50.3 | SIGMA= | 3.8 | PHAS= | 174.8 | FOM= | 0.53 | TEST= 0
| INDE | 3 | 56 | 17 | FOBS= | 44.2 | SIGMA= | 3.5 | PHAS= | 89.5 | FOM= | 0.57 | TEST= 0
| INDE | 3 | 56 | 19 | FOBS= | 75.7 | SIGMA= | 2.1 | PHAS= | 146.7 | FOM= | 0.78 | TEST= 0
| INDE | 3 | 56 | 21 | FOBS= | 9.2 | SIGMA= | 18.1 | PHAS= | -103.4 | FOM= | 0.04 | TEST= 0
| INDE | 3 | 56 | 23 | FOBS= | 60.3 | SIGMA= | 2.9 | PHAS= | -5.8 | FOM= | 0.73 | TEST= 0
| INDE | 3 | 56 | 25 | FOBS= | 40.2 | SIGMA= | 5.6 | PHAS= | -89.9 | FOM= | 0.64 | TEST= 0
| INDE | 3 | 56 | 27 | FOBS= | 92.4 | SIGMA= | 2.6 | PHAS= | 28.6 | FOM= | 0.92 | TEST= 0
| INDE | 3 | 56 | 29 | FOBS= | 49.2 | SIGMA= | 4.7 | PHAS= | 136.0 | FOM= | 0.81 | TEST= 0
| INDE | 3 | 56 | 31 | FOBS= | 134.6 | SIGMA= | 1.8 | PHAS= | 178.3 | FOM= | 0.92 | TEST= 0
| INDE | 3 | 56 | 33 | FOBS= | 0.0 | SIGMA= | 25.9 | PHAS= | 0.0 | FOM= | 0.00 | TEST= 0
| INDE | 3 | 56 | 35 | FOBS= | 0.0 | SIGMA= | 25.8 | PHAS= | 0.0 | FOM= | 0.00 | TEST= 0
| INDE | 3 | 56 | 37 | FOBS= | 0.0 | SIGMA= | 25.6 | PHAS= | 0.0 | FOM= | 0.00 | TEST= 0
| INDE | 3 | 56 | 39 | FOBS= | 0.0 | SIGMA= | 22.9 | PHAS= | 0.0 | FOM= | 0.00 | TEST= 0
| INDE | 3 | 56 | 41 | FOBS= | 46.0 | SIGMA= | 3.6 | PHAS= | 98.5 | FOM= | 0.62 | TEST= 0
| INDE | 3 | 56 | 43 | FOBS= | 22.1 | SIGMA= | 8.4 | PHAS= | -33.3 | FOM= | 0.63 | TEST= 0
| INDE | 3 | 56 | 45 | FOBS= | 0.0 | SIGMA= | 18.8 | PHAS= | 0.0 | FOM= | 0.00 | TEST= 0
| INDE | 3 | 56 | 47 | FOBS= | 0.0 | SIGMA= | 22.4 | PHAS= | 0.0 | FOM= | 0.00 | TEST= 0
| INDE | 3 | 56 | 49 | FOBS= | 0.0 | SIGMA= | 23.3 | PHAS= | 0.0 | FOM= | 0.00 | TEST= 0
| INDE | 3 | 56 | 51 | FOBS= | 50.6 | SIGMA= | 5.2 | PHAS= | 85.0 | FOM= | 0.84 | TEST= 0
| INDE | 3 | 56 | 53 | FOBS= | 53.0 | SIGMA= | 6.2 | PHAS= | -122.8 | FOM= | 0.71 | TEST= 0
| INDE | 3 | 57 | 4 | FOBS= | 74.8 | SIGMA= | 2.1 | PHAS= | 176.6 | FOM= | 0.64 | TEST= 1
| INDE | 3 | 57 | 14 | FOBS= | 88.7 | SIGMA= | 5.8 | PHAS= | -97.0 | FOM= | 0.87 | TEST= 0
| INDE | 3 | 57 | 16 | FOBS= | 88.6 | SIGMA= | 2.2 | PHAS= | -173.9 | FOM= | 0.88 | TEST= 0
| INDE | 3 | 57 | 18 | FOBS= | 27.7 | SIGMA= | 6.6 | PHAS= | 10.4 | FOM= | 0.41 | TEST= 0
| INDE | 3 | 57 | 20 | FOBS= | 146.7 | SIGMA= | 1.2 | PHAS= | -56.0 | FOM= | 0.96 | TEST= 0
| INDE | 3 | 57 | 22 | FOBS= | 44.8 | SIGMA= | 3.8 | PHAS= | 132.8 | FOM= | 0.64 | TEST= 0
| INDE | 3 | 57 | 24 | FOBS= | 54.9 | SIGMA= | 3.2 | PHAS= | 28.9 | FOM= | 0.67 | TEST= 0
| INDE | 3 | 57 | 26 | FOBS= | 56.5 | SIGMA= | 4.1 | PHAS= | 9.2 | FOM= | 0.82 | TEST= 0
| INDE | 3 | 57 | 28 | FOBS= | 64.7 | SIGMA= | 3.6 | PHAS= | 117.5 | FOM= | 0.75 | TEST= 0

*FIG. 12A - 100*

```
INDE  3  57  30 FOBS=   77.1 SIGMA=  3.1 PHAS=  134.1 FOM= 0.92 TEST= 0
INDE  3  57  32 FOBS=   46.4 SIGMA=  5.0 PHAS=  -87.9 FOM= 0.35 TEST= 0
INDE  3  57  34 FOBS=    0.0 SIGMA= 25.6 PHAS=    0.0 FOM= 0.00 TEST= 0
INDE  3  57  36 FOBS=   69.8 SIGMA=  4.8 PHAS=  143.7 FOM= 0.85 TEST= 0
INDE  3  57  38 FOBS=   16.0 SIGMA= 20.2 PHAS= -156.5 FOM= 0.42 TEST= 0
INDE  3  57  40 FOBS=  104.7 SIGMA=  2.0 PHAS=  170.7 FOM= 0.91 TEST= 0
INDE  3  57  42 FOBS=   61.9 SIGMA=  3.1 PHAS=  -35.8 FOM= 0.84 TEST= 0
INDE  3  57  44 FOBS=   78.2 SIGMA=  2.5 PHAS=   43.4 FOM= 0.70 TEST= 0
INDE  3  57  46 FOBS=   49.6 SIGMA=  4.4 PHAS=  -92.2 FOM= 0.78 TEST= 0
INDE  3  57  48 FOBS=    0.0 SIGMA= 21.1 PHAS=    0.0 FOM= 0.00 TEST= 1
INDE  3  57  50 FOBS=   43.6 SIGMA=  6.0 PHAS=   -8.1 FOM= 0.69 TEST= 0
INDE  3  57  52 FOBS=    0.0 SIGMA= 25.5 PHAS=    0.0 FOM= 0.00 TEST= 0
INDE  3  58   3 FOBS=   59.7 SIGMA=  3.9 PHAS=  -45.5 FOM= 0.45 TEST= 0
INDE  3  58   5 FOBS=  148.4 SIGMA=  1.1 PHAS=  -32.9 FOM= 0.89 TEST= 0
INDE  3  58  13 FOBS=   83.8 SIGMA=  6.2 PHAS=  180.0 FOM= 0.00 TEST= 1
INDE  3  58  15 FOBS=  109.8 SIGMA=  2.1 PHAS=  133.5 FOM= 0.87 TEST= 0
INDE  3  58  17 FOBS=  104.8 SIGMA=  1.5 PHAS=  125.5 FOM= 0.92 TEST= 0
INDE  3  58  19 FOBS=  148.5 SIGMA=  1.1 PHAS= -138.1 FOM= 0.94 TEST= 0
INDE  3  58  21 FOBS=   19.4 SIGMA=  9.0 PHAS=  150.5 FOM= 0.09 TEST= 0
INDE  3  58  23 FOBS=  132.1 SIGMA=  1.4 PHAS=   23.2 FOM= 0.93 TEST= 0
INDE  3  58  25 FOBS=  113.0 SIGMA=  1.6 PHAS=  -68.5 FOM= 0.95 TEST= 0
INDE  3  58  27 FOBS=    0.0 SIGMA= 21.3 PHAS=    0.0 FOM= 0.00 TEST= 0
INDE  3  58  29 FOBS=   29.9 SIGMA=  9.1 PHAS=   67.1 FOM= 0.53 TEST= 0
INDE  3  58  31 FOBS=   51.7 SIGMA=  4.5 PHAS=  164.2 FOM= 0.64 TEST= 0
INDE  3  58  33 FOBS=   68.2 SIGMA=  3.4 PHAS=  105.9 FOM= 0.69 TEST= 0
INDE  3  58  35 FOBS=   47.2 SIGMA=  7.1 PHAS=   98.0 FOM= 0.59 TEST= 0
INDE  3  58  37 FOBS=  120.9 SIGMA=  2.9 PHAS=   83.1 FOM= 0.93 TEST= 0
INDE  3  58  39 FOBS=  147.6 SIGMA=  2.0 PHAS=   73.8 FOM= 0.96 TEST= 0
INDE  3  58  41 FOBS=   26.1 SIGMA= 12.9 PHAS=   76.0 FOM= 0.17 TEST= 1
INDE  3  58  43 FOBS=   42.9 SIGMA=  4.4 PHAS=  -62.1 FOM= 0.79 TEST= 0
INDE  3  58  45 FOBS=   23.9 SIGMA=  7.9 PHAS= -115.2 FOM= 0.16 TEST= 0
INDE  3  58  47 FOBS=   49.8 SIGMA=  4.5 PHAS=  171.5 FOM= 0.77 TEST= 0
INDE  3  58  49 FOBS=    0.0 SIGMA= 22.9 PHAS=    0.0 FOM= 0.00 TEST= 0
INDE  3  58  51 FOBS=   37.5 SIGMA=  8.8 PHAS=  176.7 FOM= 0.31 TEST= 0
INDE  3  59   4 FOBS=  122.6 SIGMA=  1.4 PHAS= -123.0 FOM= 0.86 TEST= 0
INDE  3  59   6 FOBS=   67.2 SIGMA=  2.5 PHAS=   54.2 FOM= 0.29 TEST= 0
INDE  3  59  12 FOBS=   50.9 SIGMA=  9.5 PHAS=   82.5 FOM= 0.22 TEST= 0
INDE  3  59  14 FOBS=   45.8 SIGMA=  7.8 PHAS= -154.7 FOM= 0.19 TEST= 0
INDE  3  59  16 FOBS=   25.4 SIGMA=  8.9 PHAS=  -73.5 FOM= 0.22 TEST= 0
INDE  3  59  18 FOBS=   75.9 SIGMA=  2.3 PHAS= -119.5 FOM= 0.86 TEST= 0
INDE  3  59  20 FOBS=    0.0 SIGMA= 20.5 PHAS=    0.0 FOM= 0.00 TEST= 1
INDE  3  59  22 FOBS=  109.8 SIGMA=  1.8 PHAS=  -65.0 FOM= 0.92 TEST= 0
INDE  3  59  24 FOBS=   96.6 SIGMA=  2.1 PHAS=  -99.4 FOM= 0.84 TEST= 0
INDE  3  59  26 FOBS=   41.0 SIGMA=  4.8 PHAS= -140.0 FOM= 0.45 TEST= 0
INDE  3  59  28 FOBS=    0.0 SIGMA= 21.4 PHAS=    0.0 FOM= 0.00 TEST= 0
INDE  3  59  30 FOBS=    0.0 SIGMA= 21.4 PHAS=    0.0 FOM= 0.00 TEST= 0
INDE  3  59  32 FOBS=   66.2 SIGMA=  3.6 PHAS=   76.3 FOM= 0.73 TEST= 0
INDE  3  59  34 FOBS=   51.8 SIGMA=  4.5 PHAS=    3.5 FOM= 0.74 TEST= 0
INDE  3  59  36 FOBS=   70.4 SIGMA=  4.8 PHAS=   55.6 FOM= 0.85 TEST= 0
INDE  3  59  38 FOBS=  123.6 SIGMA=  2.3 PHAS=  -29.5 FOM= 0.96 TEST= 0
INDE  3  59  40 FOBS=   61.6 SIGMA=  3.9 PHAS=   71.8 FOM= 0.87 TEST= 0
INDE  3  59  42 FOBS=   73.6 SIGMA=  2.6 PHAS=   -4.6 FOM= 0.88 TEST= 0
INDE  3  59  44 FOBS=   42.0 SIGMA=  4.5 PHAS= -127.4 FOM= 0.58 TEST= 0
INDE  3  59  46 FOBS=   24.1 SIGMA= 12.0 PHAS=  141.7 FOM= 0.19 TEST= 0
INDE  3  59  48 FOBS=    0.0 SIGMA= 23.8 PHAS=    0.0 FOM= 0.00 TEST= 0
INDE  3  59  50 FOBS=   38.9 SIGMA=  8.7 PHAS=  161.6 FOM= 0.06 TEST= 0
INDE  3  60   3 FOBS=  124.5 SIGMA=  1.9 PHAS= -134.4 FOM= 0.90 TEST= 0
INDE  3  60   5 FOBS=   62.0 SIGMA=  1.9 PHAS=   61.1 FOM= 0.92 TEST= 1
INDE  3  60  11 FOBS=    0.0 SIGMA= 31.0 PHAS=    0.0 FOM= 0.00 TEST= 0
INDE  3  60  13 FOBS=   69.3 SIGMA=  5.2 PHAS=   60.2 FOM= 0.55 TEST= 0
INDE  3  60  15 FOBS=   48.9 SIGMA=  7.2 PHAS=  -52.3 FOM= 0.28 TEST= 0
INDE  3  60  17 FOBS=   99.7 SIGMA=  2.4 PHAS= -165.9 FOM= 0.95 TEST= 0
INDE  3  60  19 FOBS=   54.1 SIGMA=  3.8 PHAS=  -98.8 FOM= 0.73 TEST= 0
INDE  3  60  21 FOBS=   22.4 SIGMA=  8.2 PHAS=  100.1 FOM= 0.12 TEST= 0
INDE  3  60  23 FOBS=   51.3 SIGMA=  3.8 PHAS=  107.6 FOM= 0.39 TEST= 0
INDE  3  60  25 FOBS=   90.2 SIGMA=  2.6 PHAS=   44.6 FOM= 0.83 TEST= 0
INDE  3  60  27 FOBS=    0.0 SIGMA= 21.3 PHAS=    0.0 FOM= 0.00 TEST= 0
INDE  3  60  29 FOBS=   41.2 SIGMA=  8.2 PHAS=  -13.6 FOM= 0.48 TEST= 0
INDE  3  60  31 FOBS=   72.3 SIGMA=  3.9 PHAS=    0.5 FOM= 0.88 TEST= 0
INDE  3  60  33 FOBS=   18.9 SIGMA= 18.5 PHAS= -146.6 FOM= 0.35 TEST= 0
```

*FIG. 12A - 101*

```
INDE  3  60  35  FOBS=   76.9  SIGMA=   3.7  PHAS=  -115.6  FOM=  0.88  TEST= 0
INDE  3  60  37  FOBS=   94.4  SIGMA=   3.6  PHAS=   -95.2  FOM=  0.92  TEST= 0
INDE  3  60  39  FOBS=   47.9  SIGMA=   5.0  PHAS=  -135.4  FOM=  0.08  TEST= 1
INDE  3  60  41  FOBS=   46.7  SIGMA=   5.1  PHAS=   -48.0  FOM=  0.77  TEST= 0
INDE  3  60  43  FOBS=   56.4  SIGMA=   3.4  PHAS=  -142.0  FOM=  0.72  TEST= 0
INDE  3  60  45  FOBS=   77.7  SIGMA=   3.2  PHAS=    84.5  FOM=  0.09  TEST= 1
INDE  3  60  47  FOBS=   24.6  SIGMA=  14.4  PHAS=    64.0  FOM=  0.12  TEST= 1
INDE  3  60  49  FOBS=   18.8  SIGMA=  17.9  PHAS=    63.0  FOM=  0.14  TEST= 0
INDE  3  61   4  FOBS=  167.6  SIGMA=   1.5  PHAS=   166.9  FOM=  0.95  TEST= 0
INDE  3  61   6  FOBS=    0.0  SIGMA=  18.2  PHAS=     0.0  FOM=  0.00  TEST= 1
INDE  3  61  10  FOBS=   84.4  SIGMA=   6.0  PHAS=  -139.1  FOM=  0.74  TEST= 0
INDE  3  61  12  FOBS=   70.7  SIGMA=   5.2  PHAS=    -4.9  FOM=  0.82  TEST= 0
INDE  3  61  14  FOBS=   52.3  SIGMA=   6.7  PHAS=  -148.7  FOM=  0.61  TEST= 0
INDE  3  61  16  FOBS=  187.7  SIGMA=   2.1  PHAS=   178.8  FOM=  0.56  TEST= 1
INDE  3  61  18  FOBS=  109.0  SIGMA=   2.2  PHAS=  -116.1  FOM=  0.91  TEST= 0
INDE  3  61  20  FOBS=    0.0  SIGMA=  20.1  PHAS=     0.0  FOM=  0.00  TEST= 0
INDE  3  61  22  FOBS=   82.4  SIGMA=   2.6  PHAS=   -72.1  FOM=  0.72  TEST= 0
INDE  3  61  24  FOBS=   96.5  SIGMA=   2.4  PHAS=    50.6  FOM=  0.68  TEST= 0
INDE  3  61  26  FOBS=   39.0  SIGMA=   5.9  PHAS=  -121.6  FOM=  0.43  TEST= 0
INDE  3  61  28  FOBS=    0.0  SIGMA=  21.5  PHAS=     0.0  FOM=  0.00  TEST= 0
INDE  3  61  30  FOBS=  129.0  SIGMA=   2.3  PHAS=  -101.9  FOM=  0.96  TEST= 0
INDE  3  61  32  FOBS=   54.7  SIGMA=   5.2  PHAS=    48.3  FOM=  0.64  TEST= 0
INDE  3  61  34  FOBS=   67.4  SIGMA=   4.2  PHAS=  -174.2  FOM=  0.73  TEST= 0
INDE  3  61  36  FOBS=   84.2  SIGMA=   3.4  PHAS=   125.9  FOM=  0.92  TEST= 0
INDE  3  61  38  FOBS=   49.9  SIGMA=   5.5  PHAS=   -59.7  FOM=  0.82  TEST= 0
INDE  3  61  40  FOBS=   35.1  SIGMA=   6.9  PHAS=   -36.9  FOM=  0.69  TEST= 0
INDE  3  61  42  FOBS=   47.4  SIGMA=   4.3  PHAS=  -164.3  FOM=  0.40  TEST= 1
INDE  3  61  44  FOBS=   87.9  SIGMA=   2.5  PHAS=   -47.9  FOM=  0.89  TEST= 0
INDE  3  61  46  FOBS=   50.8  SIGMA=   6.8  PHAS=  -139.5  FOM=  0.76  TEST= 0
INDE  3  61  48  FOBS=   25.6  SIGMA=  13.6  PHAS=   -17.9  FOM=  0.13  TEST= 0
INDE  3  62   3  FOBS=    0.0  SIGMA=  26.0  PHAS=     0.0  FOM=  0.00  TEST= 0
INDE  3  62   5  FOBS=  102.2  SIGMA=   1.8  PHAS=    56.7  FOM=  0.89  TEST= 0
INDE  3  62   9  FOBS=   58.7  SIGMA=   8.7  PHAS=   135.3  FOM=  0.85  TEST= 0
INDE  3  62  11  FOBS=    0.0  SIGMA=  26.8  PHAS=     0.0  FOM=  0.00  TEST= 0
INDE  3  62  13  FOBS=   77.0  SIGMA=   4.7  PHAS=   136.2  FOM=  0.75  TEST= 0
INDE  3  62  15  FOBS=   96.6  SIGMA=   3.7  PHAS=     2.1  FOM=  0.63  TEST= 0
INDE  3  62  17  FOBS=  172.9  SIGMA=   2.3  PHAS=   158.7  FOM=  0.95  TEST= 0
INDE  3  62  19  FOBS=   79.0  SIGMA=   2.5  PHAS=    21.7  FOM=  0.92  TEST= 0
INDE  3  62  21  FOBS=   91.9  SIGMA=   2.3  PHAS=    49.1  FOM=  0.46  TEST= 1
INDE  3  62  23  FOBS=   45.9  SIGMA=   4.8  PHAS=   141.9  FOM=  0.61  TEST= 0
INDE  3  62  25  FOBS=  127.2  SIGMA=   1.8  PHAS=    85.1  FOM=  0.94  TEST= 0
INDE  3  62  27  FOBS=   47.1  SIGMA=   4.9  PHAS=   -63.5  FOM=  0.32  TEST= 0
INDE  3  62  29  FOBS=  112.8  SIGMA=   2.2  PHAS=  -159.5  FOM=  0.92  TEST= 0
INDE  3  62  31  FOBS=   48.3  SIGMA=   5.8  PHAS=  -119.1  FOM=  0.20  TEST= 0
INDE  3  62  33  FOBS=   29.6  SIGMA=  11.5  PHAS=   -13.3  FOM=  0.44  TEST= 0
INDE  3  62  35  FOBS=   54.9  SIGMA=   5.2  PHAS=   -99.0  FOM=  0.66  TEST= 0
INDE  3  62  37  FOBS=   44.4  SIGMA=   5.5  PHAS=    -2.9  FOM=  0.29  TEST= 0
INDE  3  62  39  FOBS=   83.3  SIGMA=   3.0  PHAS=  -116.3  FOM=  0.90  TEST= 0
INDE  3  62  41  FOBS=   34.4  SIGMA=   8.1  PHAS=   134.1  FOM=  0.52  TEST= 0
INDE  3  62  43  FOBS=  111.9  SIGMA=   2.0  PHAS=  -163.2  FOM=  0.87  TEST= 0
INDE  3  62  45  FOBS=    0.0  SIGMA=  26.3  PHAS=     0.0  FOM=  0.00  TEST= 0
INDE  3  63   4  FOBS=   80.3  SIGMA=   4.2  PHAS=    98.1  FOM=  0.64  TEST= 0
INDE  3  63   6  FOBS=    0.0  SIGMA=  20.6  PHAS=     0.0  FOM=  0.00  TEST= 0
INDE  3  63   8  FOBS=  125.4  SIGMA=   4.2  PHAS=   180.0  FOM=  0.00  TEST= 1
INDE  3  63  10  FOBS=    0.0  SIGMA=  26.7  PHAS=     0.0  FOM=  0.00  TEST= 0
INDE  3  63  12  FOBS=   79.7  SIGMA=   4.6  PHAS=    23.1  FOM=  0.36  TEST= 0
INDE  3  63  14  FOBS=   50.5  SIGMA=   7.0  PHAS=   122.9  FOM=  0.33  TEST= 0
INDE  3  63  16  FOBS=   58.7  SIGMA=   6.0  PHAS=  -177.9  FOM=  0.10  TEST= 1
INDE  3  63  18  FOBS=   64.4  SIGMA=   3.6  PHAS=   -56.0  FOM=  0.79  TEST= 0
INDE  3  63  20  FOBS=  130.9  SIGMA=   1.6  PHAS=   -43.1  FOM=  0.96  TEST= 0
INDE  3  63  22  FOBS=   85.0  SIGMA=   2.5  PHAS=     9.1  FOM=  0.91  TEST= 0
INDE  3  63  24  FOBS=   94.2  SIGMA=   2.4  PHAS=    94.9  FOM=  0.67  TEST= 1
INDE  3  63  26  FOBS=   92.0  SIGMA=   2.5  PHAS=   -75.1  FOM=  0.88  TEST= 0
INDE  3  63  28  FOBS=   74.4  SIGMA=   3.2  PHAS=    85.4  FOM=  0.86  TEST= 0
INDE  3  63  30  FOBS=   60.6  SIGMA=   4.0  PHAS=   -19.1  FOM=  0.80  TEST= 0
INDE  3  63  32  FOBS=   92.0  SIGMA=   3.1  PHAS=  -153.0  FOM=  0.94  TEST= 0
INDE  3  63  34  FOBS=   60.4  SIGMA=   4.8  PHAS=  -105.8  FOM=  0.75  TEST= 0
INDE  3  63  36  FOBS=    0.0  SIGMA=  23.8  PHAS=     0.0  FOM=  0.00  TEST= 0
INDE  3  63  38  FOBS=   59.4  SIGMA=   3.8  PHAS=    86.6  FOM=  0.78  TEST= 0
INDE  3  63  40  FOBS=   28.4  SIGMA=  12.5  PHAS=   -95.6  FOM=  0.32  TEST= 0
```

*FIG. 12A - 102*

| | | | | | | | | | | | | |
|---|---|---|---|---|---|---|---|---|---|---|---|---|
| INDE | 3 | 63 | 42 | FOBS= | 55.4 | SIGMA= | 4.5 | PHAS= | 128.1 | FOM= | 0.88 | TEST= 0 |
| INDE | 3 | 63 | 44 | FOBS= | 29.1 | SIGMA= | 12.1 | PHAS= | 48.9 | FOM= | 0.77 | TEST= 0 |
| INDE | 3 | 64 | 3 | FOBS= | 34.9 | SIGMA= | 9.0 | PHAS= | 178.9 | FOM= | 0.44 | TEST= 0 |
| INDE | 3 | 64 | 5 | FOBS= | 23.8 | SIGMA= | 13.7 | PHAS= | -34.2 | FOM= | 0.28 | TEST= 0 |
| INDE | 3 | 64 | 7 | FOBS= | 0.0 | SIGMA= | 21.5 | PHAS= | 0.0 | FOM= | 0.00 | TEST= 1 |
| INDE | 3 | 64 | 9 | FOBS= | 81.8 | SIGMA= | 4.4 | PHAS= | 169.7 | FOM= | 0.73 | TEST= 0 |
| INDE | 3 | 64 | 11 | FOBS= | 73.1 | SIGMA= | 5.0 | PHAS= | 140.6 | FOM= | 0.03 | TEST= 1 |
| INDE | 3 | 64 | 13 | FOBS= | 30.7 | SIGMA= | 11.4 | PHAS= | -92.7 | FOM= | 0.16 | TEST= 0 |
| INDE | 3 | 64 | 15 | FOBS= | 73.5 | SIGMA= | 4.8 | PHAS= | 20.8 | FOM= | 0.80 | TEST= 0 |
| INDE | 3 | 64 | 17 | FOBS= | 40.4 | SIGMA= | 8.8 | PHAS= | -148.8 | FOM= | 0.39 | TEST= 0 |
| INDE | 3 | 64 | 19 | FOBS= | 18.8 | SIGMA= | 12.2 | PHAS= | 179.0 | FOM= | 0.46 | TEST= 0 |
| INDE | 3 | 64 | 21 | FOBS= | 60.0 | SIGMA= | 3.4 | PHAS= | 50.3 | FOM= | 0.48 | TEST= 0 |
| INDE | 3 | 64 | 23 | FOBS= | 65.7 | SIGMA= | 3.2 | PHAS= | -79.2 | FOM= | 0.74 | TEST= 0 |
| INDE | 3 | 64 | 25 | FOBS= | 34.0 | SIGMA= | 6.5 | PHAS= | 97.6 | FOM= | 0.60 | TEST= 0 |
| INDE | 3 | 64 | 27 | FOBS= | 43.8 | SIGMA= | 6.2 | PHAS= | -124.7 | FOM= | 0.61 | TEST= 0 |
| INDE | 3 | 64 | 29 | FOBS= | 73.2 | SIGMA= | 3.3 | PHAS= | -64.9 | FOM= | 0.86 | TEST= 0 |
| INDE | 3 | 64 | 31 | FOBS= | 19.5 | SIGMA= | 12.3 | PHAS= | -131.8 | FOM= | 0.15 | TEST= 0 |
| INDE | 3 | 64 | 33 | FOBS= | 48.2 | SIGMA= | 6.0 | PHAS= | 24.4 | FOM= | 0.76 | TEST= 0 |
| INDE | 3 | 64 | 35 | FOBS= | 0.0 | SIGMA= | 26.1 | PHAS= | 0.0 | FOM= | 0.00 | TEST= 0 |
| INDE | 3 | 64 | 37 | FOBS= | 49.3 | SIGMA= | 5.1 | PHAS= | 67.2 | FOM= | 0.05 | TEST= 1 |
| INDE | 3 | 64 | 39 | FOBS= | 33.6 | SIGMA= | 7.4 | PHAS= | -112.9 | FOM= | 0.61 | TEST= 0 |
| INDE | 3 | 64 | 41 | FOBS= | 61.1 | SIGMA= | 4.2 | PHAS= | -22.0 | FOM= | 0.67 | TEST= 0 |
| INDE | 3 | 64 | 43 | FOBS= | 47.2 | SIGMA= | 6.3 | PHAS= | 4.3 | FOM= | 0.73 | TEST= 0 |
| INDE | 3 | 65 | 4 | FOBS= | 78.6 | SIGMA= | 4.2 | PHAS= | 77.5 | FOM= | 0.81 | TEST= 0 |
| INDE | 3 | 65 | 6 | FOBS= | 46.2 | SIGMA= | 3.6 | PHAS= | 116.1 | FOM= | 0.44 | TEST= 0 |
| INDE | 3 | 65 | 8 | FOBS= | 38.3 | SIGMA= | 9.2 | PHAS= | 33.9 | FOM= | 0.56 | TEST= 0 |
| INDE | 3 | 65 | 10 | FOBS= | 65.7 | SIGMA= | 5.5 | PHAS= | 35.3 | FOM= | 0.79 | TEST= 0 |
| INDE | 3 | 65 | 12 | FOBS= | 55.1 | SIGMA= | 6.5 | PHAS= | 146.4 | FOM= | 0.65 | TEST= 0 |
| INDE | 3 | 65 | 14 | FOBS= | 83.8 | SIGMA= | 4.3 | PHAS= | 177.2 | FOM= | 0.44 | TEST= 1 |
| INDE | 3 | 65 | 16 | FOBS= | 22.6 | SIGMA= | 15.5 | PHAS= | -46.3 | FOM= | 0.46 | TEST= 0 |
| INDE | 3 | 65 | 18 | FOBS= | 0.0 | SIGMA= | 26.5 | PHAS= | 0.0 | FOM= | 0.00 | TEST= 0 |
| INDE | 3 | 65 | 20 | FOBS= | 81.6 | SIGMA= | 3.0 | PHAS= | -4.7 | FOM= | 0.89 | TEST= 0 |
| INDE | 3 | 65 | 22 | FOBS= | 56.3 | SIGMA= | 3.7 | PHAS= | -43.7 | FOM= | 0.54 | TEST= 0 |
| INDE | 3 | 65 | 24 | FOBS= | 24.5 | SIGMA= | 9.7 | PHAS= | 96.5 | FOM= | 0.09 | TEST= 0 |
| INDE | 3 | 65 | 26 | FOBS= | 0.0 | SIGMA= | 23.0 | PHAS= | 0.0 | FOM= | 0.00 | TEST= 0 |
| INDE | 3 | 65 | 28 | FOBS= | 4.9 | SIGMA= | 55.0 | PHAS= | -116.6 | FOM= | 0.04 | TEST= 0 |
| INDE | 3 | 65 | 30 | FOBS= | 30.4 | SIGMA= | 7.8 | PHAS= | 156.7 | FOM= | 0.05 | TEST= 1 |
| INDE | 3 | 65 | 32 | FOBS= | 88.1 | SIGMA= | 2.8 | PHAS= | -118.7 | FOM= | 0.93 | TEST= 0 |
| INDE | 3 | 65 | 34 | FOBS= | 66.5 | SIGMA= | 4.4 | PHAS= | -48.7 | FOM= | 0.90 | TEST= 0 |
| INDE | 3 | 65 | 36 | FOBS= | 0.0 | SIGMA= | 23.7 | PHAS= | 0.0 | FOM= | 0.00 | TEST= 0 |
| INDE | 3 | 65 | 38 | FOBS= | 40.7 | SIGMA= | 6.3 | PHAS= | 53.3 | FOM= | 0.28 | TEST= 0 |
| INDE | 3 | 65 | 40 | FOBS= | 91.3 | SIGMA= | 2.6 | PHAS= | 151.4 | FOM= | 0.87 | TEST= 0 |
| INDE | 3 | 65 | 42 | FOBS= | 0.0 | SIGMA= | 22.7 | PHAS= | 0.0 | FOM= | 0.00 | TEST= 0 |
| INDE | 3 | 66 | 5 | FOBS= | 75.1 | SIGMA= | 3.7 | PHAS= | 24.9 | FOM= | 0.76 | TEST= 0 |
| INDE | 3 | 66 | 7 | FOBS= | 110.6 | SIGMA= | 1.7 | PHAS= | -88.5 | FOM= | 0.86 | TEST= 0 |
| INDE | 3 | 66 | 9 | FOBS= | 9.7 | SIGMA= | 36.3 | PHAS= | -129.6 | FOM= | 0.09 | TEST= 0 |
| INDE | 3 | 66 | 11 | FOBS= | 70.6 | SIGMA= | 5.2 | PHAS= | -52.2 | FOM= | 0.82 | TEST= 0 |
| INDE | 3 | 66 | 13 | FOBS= | 52.1 | SIGMA= | 6.9 | PHAS= | 96.0 | FOM= | 0.73 | TEST= 0 |
| INDE | 3 | 66 | 15 | FOBS= | 0.0 | SIGMA= | 26.5 | PHAS= | 0.0 | FOM= | 0.00 | TEST= 0 |
| INDE | 3 | 66 | 17 | FOBS= | 33.4 | SIGMA= | 10.5 | PHAS= | -107.7 | FOM= | 0.24 | TEST= 0 |
| INDE | 3 | 66 | 19 | FOBS= | 92.1 | SIGMA= | 2.5 | PHAS= | -111.5 | FOM= | 0.83 | TEST= 0 |
| INDE | 3 | 66 | 21 | FOBS= | 37.3 | SIGMA= | 5.3 | PHAS= | -163.5 | FOM= | 0.24 | TEST= 0 |
| INDE | 3 | 66 | 23 | FOBS= | 97.9 | SIGMA= | 2.3 | PHAS= | -171.0 | FOM= | 0.87 | TEST= 0 |
| INDE | 3 | 66 | 25 | FOBS= | 56.3 | SIGMA= | 3.9 | PHAS= | -47.6 | FOM= | 0.87 | TEST= 0 |
| INDE | 3 | 66 | 27 | FOBS= | 0.0 | SIGMA= | 21.5 | PHAS= | 0.0 | FOM= | 0.00 | TEST= 0 |
| INDE | 3 | 66 | 29 | FOBS= | 0.0 | SIGMA= | 23.3 | PHAS= | 0.0 | FOM= | 0.00 | TEST= 0 |
| INDE | 3 | 66 | 31 | FOBS= | 87.0 | SIGMA= | 2.9 | PHAS= | -154.1 | FOM= | 0.89 | TEST= 0 |
| INDE | 3 | 66 | 33 | FOBS= | 44.4 | SIGMA= | 5.6 | PHAS= | 179.8 | FOM= | 0.70 | TEST= 0 |
| INDE | 3 | 66 | 35 | FOBS= | 0.0 | SIGMA= | 23.9 | PHAS= | 0.0 | FOM= | 0.00 | TEST= 0 |
| INDE | 3 | 66 | 37 | FOBS= | 43.9 | SIGMA= | 5.3 | PHAS= | -21.7 | FOM= | 0.67 | TEST= 0 |
| INDE | 3 | 66 | 39 | FOBS= | 36.6 | SIGMA= | 7.2 | PHAS= | 31.7 | FOM= | 0.75 | TEST= 0 |
| INDE | 3 | 66 | 41 | FOBS= | 7.7 | SIGMA= | 47.5 | PHAS= | -96.0 | FOM= | 0.12 | TEST= 0 |
| INDE | 3 | 67 | 4 | FOBS= | 53.9 | SIGMA= | 5.8 | PHAS= | -178.0 | FOM= | 0.58 | TEST= 0 |
| INDE | 3 | 67 | 6 | FOBS= | 111.5 | SIGMA= | 2.6 | PHAS= | -150.9 | FOM= | 0.95 | TEST= 0 |
| INDE | 3 | 67 | 8 | FOBS= | 0.0 | SIGMA= | 21.6 | PHAS= | 0.0 | FOM= | 0.00 | TEST= 0 |
| INDE | 3 | 67 | 10 | FOBS= | 36.2 | SIGMA= | 9.9 | PHAS= | -88.7 | FOM= | 0.26 | TEST= 0 |
| INDE | 3 | 67 | 12 | FOBS= | 47.0 | SIGMA= | 7.6 | PHAS= | 110.4 | FOM= | 0.68 | TEST= 0 |
| INDE | 3 | 67 | 14 | FOBS= | 39.1 | SIGMA= | 9.0 | PHAS= | 86.5 | FOM= | 0.64 | TEST= 0 |
| INDE | 3 | 67 | 16 | FOBS= | 23.1 | SIGMA= | 15.1 | PHAS= | -82.1 | FOM= | 0.29 | TEST= 0 |
| INDE | 3 | 67 | 18 | FOBS= | 84.1 | SIGMA= | 4.3 | PHAS= | 82.0 | FOM= | 0.50 | TEST= 0 |

*FIG. 12A - 103*

| | | | | | | | | | | | |
|---|---|---|---|---|---|---|---|---|---|---|---|
| INDE | 3 | 67 | 20 | FOBS= | 47.0 | SIGMA= | 4.9 | PHAS= | 132.5 | FOM= | 0.74 | TEST= 0
| INDE | 3 | 67 | 22 | FOBS= | 147.1 | SIGMA= | 1.5 | PHAS= | 160.7 | FOM= | 0.94 | TEST= 0
| INDE | 3 | 67 | 24 | FOBS= | 0.0 | SIGMA= | 21.8 | PHAS= | 0.0 | FOM= | 0.00 | TEST= 0
| INDE | 3 | 67 | 26 | FOBS= | 0.0 | SIGMA= | 21.3 | PHAS= | 0.0 | FOM= | 0.00 | TEST= 0
| INDE | 3 | 67 | 28 | FOBS= | 0.0 | SIGMA= | 23.4 | PHAS= | 0.0 | FOM= | 0.00 | TEST= 0
| INDE | 3 | 67 | 30 | FOBS= | 53.6 | SIGMA= | 5.3 | PHAS= | -20.4 | FOM= | 0.84 | TEST= 0
| INDE | 3 | 67 | 32 | FOBS= | 0.0 | SIGMA= | 24.0 | PHAS= | 0.0 | FOM= | 0.00 | TEST= 0
| INDE | 3 | 67 | 34 | FOBS= | 0.0 | SIGMA= | 22.3 | PHAS= | 0.0 | FOM= | 0.00 | TEST= 0
| INDE | 3 | 67 | 36 | FOBS= | 49.2 | SIGMA= | 4.7 | PHAS= | -135.6 | FOM= | 0.47 | TEST= 0
| INDE | 3 | 67 | 38 | FOBS= | 46.4 | SIGMA= | 5.1 | PHAS= | -50.7 | FOM= | 0.81 | TEST= 0
| INDE | 3 | 68 | 3 | FOBS= | 141.7 | SIGMA= | 2.3 | PHAS= | -148.6 | FOM= | 0.33 | TEST= 1
| INDE | 3 | 68 | 5 | FOBS= | 56.0 | SIGMA= | 5.9 | PHAS= | 95.8 | FOM= | 0.86 | TEST= 0
| INDE | 3 | 68 | 7 | FOBS= | 66.2 | SIGMA= | 2.7 | PHAS= | 159.8 | FOM= | 0.88 | TEST= 0
| INDE | 3 | 68 | 11 | FOBS= | 63.7 | SIGMA= | 8.1 | PHAS= | -137.6 | FOM= | 0.09 | TEST= 1
| INDE | 3 | 68 | 13 | FOBS= | 84.0 | SIGMA= | 6.3 | PHAS= | 22.9 | FOM= | 0.82 | TEST= 0
| INDE | 3 | 68 | 15 | FOBS= | 15.7 | SIGMA= | 22.4 | PHAS= | -143.4 | FOM= | 0.06 | TEST= 0
| INDE | 3 | 68 | 17 | FOBS= | 33.1 | SIGMA= | 10.7 | PHAS= | 24.0 | FOM= | 0.26 | TEST= 0
| INDE | 3 | 68 | 19 | FOBS= | 0.0 | SIGMA= | 26.5 | PHAS= | 0.0 | FOM= | 0.00 | TEST= 0
| INDE | 3 | 68 | 21 | FOBS= | 89.8 | SIGMA= | 2.8 | PHAS= | 25.5 | FOM= | 0.92 | TEST= 0
| INDE | 3 | 68 | 23 | FOBS= | 0.0 | SIGMA= | 20.5 | PHAS= | 0.0 | FOM= | 0.00 | TEST= 0
| INDE | 3 | 68 | 25 | FOBS= | 46.9 | SIGMA= | 4.7 | PHAS= | 66.7 | FOM= | 0.82 | TEST= 0
| INDE | 3 | 68 | 27 | FOBS= | 22.5 | SIGMA= | 10.3 | PHAS= | 172.7 | FOM= | 0.29 | TEST= 0
| INDE | 3 | 68 | 29 | FOBS= | 52.1 | SIGMA= | 4.6 | PHAS= | -43.9 | FOM= | 0.71 | TEST= 0
| INDE | 3 | 68 | 31 | FOBS= | 100.3 | SIGMA= | 2.6 | PHAS= | -113.1 | FOM= | 0.96 | TEST= 0
| INDE | 3 | 68 | 33 | FOBS= | 33.8 | SIGMA= | 7.5 | PHAS= | -82.5 | FOM= | 0.60 | TEST= 0
| INDE | 3 | 68 | 35 | FOBS= | 47.2 | SIGMA= | 4.9 | PHAS= | 140.9 | FOM= | 0.73 | TEST= 0
| INDE | 3 | 68 | 37 | FOBS= | 54.7 | SIGMA= | 4.4 | PHAS= | -65.3 | FOM= | 0.66 | TEST= 0
| INDE | 3 | 69 | 4 | FOBS= | 59.1 | SIGMA= | 5.3 | PHAS= | 110.5 | FOM= | 0.80 | TEST= 0
| INDE | 3 | 69 | 6 | FOBS= | 103.5 | SIGMA= | 3.4 | PHAS= | -154.4 | FOM= | 0.22 | TEST= 1
| INDE | 3 | 69 | 8 | FOBS= | 45.7 | SIGMA= | 4.7 | PHAS= | 168.0 | FOM= | 0.39 | TEST= 0
| INDE | 3 | 69 | 16 | FOBS= | 36.1 | SIGMA= | 14.4 | PHAS= | 155.9 | FOM= | 0.31 | TEST= 0
| INDE | 3 | 69 | 18 | FOBS= | 41.9 | SIGMA= | 12.1 | PHAS= | -28.7 | FOM= | 0.60 | TEST= 0
| INDE | 3 | 69 | 20 | FOBS= | 25.3 | SIGMA= | 14.2 | PHAS= | -147.8 | FOM= | 0.50 | TEST= 0
| INDE | 3 | 69 | 22 | FOBS= | 34.7 | SIGMA= | 7.1 | PHAS= | 57.0 | FOM= | 0.33 | TEST= 0
| INDE | 3 | 69 | 24 | FOBS= | 56.8 | SIGMA= | 3.9 | PHAS= | -14.4 | FOM= | 0.89 | TEST= 0
| INDE | 3 | 69 | 26 | FOBS= | 50.3 | SIGMA= | 4.4 | PHAS= | 61.4 | FOM= | 0.67 | TEST= 0
| INDE | 3 | 69 | 28 | FOBS= | 0.0 | SIGMA= | 21.7 | PHAS= | 0.0 | FOM= | 0.00 | TEST= 0
| INDE | 3 | 69 | 30 | FOBS= | 0.0 | SIGMA= | 22.0 | PHAS= | 0.0 | FOM= | 0.00 | TEST= 0
| INDE | 3 | 69 | 32 | FOBS= | 93.9 | SIGMA= | 2.8 | PHAS= | 163.4 | FOM= | 0.91 | TEST= 0
| INDE | 3 | 69 | 34 | FOBS= | 58.0 | SIGMA= | 4.0 | PHAS= | 155.8 | FOM= | 0.20 | TEST= 1
| INDE | 3 | 70 | 3 | FOBS= | 120.4 | SIGMA= | 2.7 | PHAS= | 65.6 | FOM= | 0.94 | TEST= 0
| INDE | 3 | 70 | 5 | FOBS= | 89.3 | SIGMA= | 3.5 | PHAS= | 96.0 | FOM= | 0.88 | TEST= 0
| INDE | 3 | 70 | 9 | FOBS= | 44.3 | SIGMA= | 5.9 | PHAS= | 20.9 | FOM= | 0.55 | TEST= 0
| INDE | 3 | 70 | 19 | FOBS= | 100.5 | SIGMA= | 5.3 | PHAS= | 140.0 | FOM= | 0.66 | TEST= 0
| INDE | 3 | 70 | 21 | FOBS= | 86.6 | SIGMA= | 6.1 | PHAS= | -44.8 | FOM= | 0.90 | TEST= 0
| INDE | 3 | 70 | 23 | FOBS= | 40.1 | SIGMA= | 5.6 | PHAS= | -53.0 | FOM= | 0.47 | TEST= 0
| INDE | 3 | 70 | 25 | FOBS= | 0.0 | SIGMA= | 21.0 | PHAS= | 0.0 | FOM= | 0.00 | TEST= 1
| INDE | 3 | 70 | 27 | FOBS= | 62.6 | SIGMA= | 3.7 | PHAS= | -84.2 | FOM= | 0.51 | TEST= 0
| INDE | 3 | 70 | 29 | FOBS= | 0.0 | SIGMA= | 22.0 | PHAS= | 0.0 | FOM= | 0.00 | TEST= 0
| INDE | 3 | 70 | 31 | FOBS= | 53.7 | SIGMA= | 4.6 | PHAS= | 114.7 | FOM= | 0.82 | TEST= 0
| INDE | 3 | 70 | 33 | FOBS= | 65.5 | SIGMA= | 4.0 | PHAS= | 101.3 | FOM= | 0.68 | TEST= 0
| INDE | 3 | 71 | 4 | FOBS= | 59.1 | SIGMA= | 5.3 | PHAS= | 6.2 | FOM= | 0.78 | TEST= 0
| INDE | 3 | 71 | 6 | FOBS= | 46.7 | SIGMA= | 7.1 | PHAS= | 54.7 | FOM= | 0.54 | TEST= 0
| INDE | 3 | 71 | 8 | FOBS= | 71.1 | SIGMA= | 2.5 | PHAS= | -116.6 | FOM= | 0.66 | TEST= 0
| INDE | 3 | 71 | 22 | FOBS= | 9.1 | SIGMA= | 35.2 | PHAS= | -19.4 | FOM= | 0.25 | TEST= 0
| INDE | 3 | 71 | 24 | FOBS= | 0.0 | SIGMA= | 24.4 | PHAS= | 0.0 | FOM= | 0.00 | TEST= 0
| INDE | 3 | 71 | 26 | FOBS= | 0.0 | SIGMA= | 24.0 | PHAS= | 0.0 | FOM= | 0.00 | TEST= 0
| INDE | 3 | 71 | 28 | FOBS= | 39.0 | SIGMA= | 6.7 | PHAS= | 87.4 | FOM= | 0.51 | TEST= 0
| INDE | 3 | 71 | 30 | FOBS= | 47.1 | SIGMA= | 6.3 | PHAS= | 56.3 | FOM= | 0.84 | TEST= 0
| INDE | 3 | 72 | 3 | FOBS= | 31.0 | SIGMA= | 10.4 | PHAS= | 168.0 | FOM= | 0.39 | TEST= 0
| INDE | 3 | 72 | 5 | FOBS= | 0.0 | SIGMA= | 24.6 | PHAS= | 0.0 | FOM= | 0.00 | TEST= 0
| INDE | 3 | 72 | 7 | FOBS= | 70.7 | SIGMA= | 4.9 | PHAS= | 124.3 | FOM= | 0.82 | TEST= 0
| INDE | 3 | 72 | 9 | FOBS= | 0.0 | SIGMA= | 20.7 | PHAS= | 0.0 | FOM= | 0.00 | TEST= 0
| INDE | 3 | 72 | 23 | FOBS= | 17.7 | SIGMA= | 19.3 | PHAS= | 76.9 | FOM= | 0.06 | TEST= 0
| INDE | 3 | 72 | 25 | FOBS= | 22.0 | SIGMA= | 12.3 | PHAS= | 59.0 | FOM= | 0.12 | TEST= 0
| INDE | 3 | 72 | 27 | FOBS= | 39.3 | SIGMA= | 7.6 | PHAS= | -124.0 | FOM= | 0.65 | TEST= 0
| INDE | 3 | 72 | 29 | FOBS= | 93.6 | SIGMA= | 3.0 | PHAS= | -31.5 | FOM= | 0.90 | TEST= 0
| INDE | 3 | 73 | 4 | FOBS= | 56.4 | SIGMA= | 5.5 | PHAS= | 55.2 | FOM= | 0.20 | TEST= 0
| INDE | 3 | 73 | 6 | FOBS= | 44.8 | SIGMA= | 6.9 | PHAS= | -98.7 | FOM= | 0.23 | TEST= 0
| INDE | 3 | 73 | 8 | FOBS= | 0.0 | SIGMA= | 26.0 | PHAS= | 0.0 | FOM= | 0.00 | TEST= 0

*FIG. 12A - 104*

```
INDE  3  73  10  FOBS=    0.0  SIGMA= 23.1  PHAS=    0.0  FOM= 0.00  TEST= 0
INDE  3  73  24  FOBS=   36.2  SIGMA= 10.0  PHAS=    4.1  FOM= 0.60  TEST= 0
INDE  3  73  26  FOBS=   51.0  SIGMA=  5.6  PHAS= -160.6  FOM= 0.17  TEST= 1
INDE  3  74   3  FOBS=   53.3  SIGMA=  6.1  PHAS=  146.0  FOM= 0.00  TEST= 1
INDE  3  74   5  FOBS=   46.9  SIGMA=  6.8  PHAS=  147.2  FOM= 0.74  TEST= 0
INDE  3  74   7  FOBS=   89.2  SIGMA=  3.8  PHAS=  157.8  FOM= 0.93  TEST= 0
INDE  3  74   9  FOBS=   12.0  SIGMA= 14.8  PHAS= -127.8  FOM= 0.07  TEST= 0
INDE  3  75   4  FOBS=   48.7  SIGMA=  6.8  PHAS= -122.8  FOM= 0.17  TEST= 1
INDE  3  75   6  FOBS=   84.5  SIGMA=  3.8  PHAS=   81.0  FOM= 0.69  TEST= 0
INDE  3  75   8  FOBS=   72.1  SIGMA=  4.8  PHAS=   96.8  FOM= 0.88  TEST= 0
INDE  3  75  10  FOBS=   61.6  SIGMA=  3.4  PHAS=  125.3  FOM= 0.84  TEST= 0
INDE  3  76   5  FOBS=   11.7  SIGMA= 28.4  PHAS=  145.2  FOM= 0.08  TEST= 0
INDE  3  76   7  FOBS=   72.3  SIGMA=  4.5  PHAS=  125.7  FOM= 0.82  TEST= 0
INDE  3  76   9  FOBS=   88.7  SIGMA=  4.1  PHAS=    5.4  FOM= 0.90  TEST= 0
INDE  3  76  11  FOBS=   72.6  SIGMA=  3.8  PHAS=  180.0  FOM= 0.00  TEST= 1
INDE  3  77   6  FOBS=    0.0  SIGMA= 25.7  PHAS=    0.0  FOM= 0.00  TEST= 1
INDE  3  77   8  FOBS=   85.9  SIGMA=  4.1  PHAS=   17.4  FOM= 0.40  TEST= 1
INDE  3  77  10  FOBS=    0.0  SIGMA= 26.9  PHAS=    0.0  FOM= 0.00  TEST= 0
INDE  4   5  17  FOBS=  160.1  SIGMA=  0.4  PHAS=   -7.3  FOM= 0.27  TEST= 0
INDE  4   5  19  FOBS=  252.9  SIGMA=  0.4  PHAS= -170.4  FOM= 0.80  TEST= 0
INDE  4   5  21  FOBS=  215.8  SIGMA=  0.5  PHAS=   31.2  FOM= 0.13  TEST= 1
INDE  4   5  23  FOBS=  204.4  SIGMA=  0.6  PHAS=  -73.2  FOM= 0.93  TEST= 0
INDE  4   5  25  FOBS=   90.1  SIGMA=  0.9  PHAS=   71.5  FOM= 0.98  TEST= 0
INDE  4   5  27  FOBS=   18.2  SIGMA=  5.0  PHAS=    1.8  FOM= 0.06  TEST= 1
INDE  4   5  29  FOBS=  122.1  SIGMA=  0.8  PHAS=  -97.8  FOM= 0.98  TEST= 0
INDE  4   5  31  FOBS=   64.9  SIGMA=  1.8  PHAS=   -7.2  FOM= 0.96  TEST= 0
INDE  4   5  33  FOBS=   76.1  SIGMA=  1.6  PHAS=   78.0  FOM= 0.83  TEST= 0
INDE  4   5  35  FOBS=  314.0  SIGMA=  0.6  PHAS= -118.4  FOM= 0.96  TEST= 0
INDE  4   5  37  FOBS=  544.2  SIGMA=  0.6  PHAS= -162.5  FOM= 0.99  TEST= 0
INDE  4   5  39  FOBS=   92.3  SIGMA=  1.6  PHAS=  -23.9  FOM= 0.69  TEST= 0
INDE  4   5  41  FOBS=  365.3  SIGMA=  0.8  PHAS=  -70.6  FOM= 0.99  TEST= 0
INDE  4   5  43  FOBS=  185.8  SIGMA=  1.0  PHAS= -121.2  FOM= 0.96  TEST= 1
INDE  4   5  45  FOBS=  131.5  SIGMA=  1.6  PHAS= -124.2  FOM= 0.96  TEST= 0
INDE  4   5  47  FOBS=  172.7  SIGMA=  1.4  PHAS=  -71.7  FOM= 0.44  TEST= 0
INDE  4   5  49  FOBS=   70.4  SIGMA=  3.3  PHAS=  152.2  FOM= 0.95  TEST= 0
INDE  4   5  51  FOBS=  154.7  SIGMA=  1.5  PHAS=   78.5  FOM= 0.77  TEST= 0
INDE  4   5  53  FOBS=  108.1  SIGMA=  1.9  PHAS=  105.1  FOM= 0.82  TEST= 0
INDE  4   5  55  FOBS=  160.9  SIGMA=  1.3  PHAS=  -33.2  FOM= 0.94  TEST= 0
INDE  4   5  57  FOBS=  199.7  SIGMA=  1.5  PHAS=  -49.2  FOM= 0.96  TEST= 0
INDE  4   5  59  FOBS=  162.6  SIGMA=  1.7  PHAS=  -72.8  FOM= 0.53  TEST= 0
INDE  4   5  61  FOBS=    0.0  SIGMA= 20.3  PHAS=    0.0  FOM= 0.00  TEST= 0
INDE  4   5  63  FOBS=   33.6  SIGMA=  6.0  PHAS=  130.8  FOM= 0.49  TEST= 0
INDE  4   5  65  FOBS=   60.6  SIGMA=  4.2  PHAS=  -95.4  FOM= 0.28  TEST= 0
INDE  4   5  67  FOBS=   79.9  SIGMA=  4.4  PHAS= -174.6  FOM= 0.89  TEST= 0
INDE  4   5  69  FOBS=   88.1  SIGMA=  4.0  PHAS= -149.5  FOM= 0.93  TEST= 0
INDE  4   5  71  FOBS=   49.6  SIGMA=  6.7  PHAS= -112.9  FOM= 0.12  TEST= 0
INDE  4   5  73  FOBS=   38.7  SIGMA=  8.7  PHAS=  132.8  FOM= 0.73  TEST= 0
INDE  4   5  75  FOBS=   48.2  SIGMA=  7.2  PHAS= -111.3  FOM= 0.78  TEST= 0
INDE  4   5  77  FOBS=   79.1  SIGMA=  4.6  PHAS=   10.5  FOM= 0.23  TEST= 0
INDE  4   6  18  FOBS=   51.5  SIGMA=  1.0  PHAS=   44.0  FOM= 0.95  TEST= 1
INDE  4   6  20  FOBS=  133.9  SIGMA=  0.6  PHAS= -145.3  FOM= 0.94  TEST= 0
INDE  4   6  22  FOBS=  128.1  SIGMA=  0.8  PHAS=  160.8  FOM= 0.95  TEST= 0
INDE  4   6  24  FOBS=   97.3  SIGMA=  0.9  PHAS=   93.4  FOM= 0.95  TEST= 0
INDE  4   6  26  FOBS=  193.4  SIGMA=  0.6  PHAS=  -99.4  FOM= 0.95  TEST= 0
INDE  4   6  28  FOBS=  138.8  SIGMA=  0.7  PHAS= -160.2  FOM= 0.89  TEST= 0
INDE  4   6  30  FOBS=   87.5  SIGMA=  1.1  PHAS= -169.3  FOM= 0.96  TEST= 0
INDE  4   6  32  FOBS=  104.4  SIGMA=  1.1  PHAS=  -64.9  FOM= 0.98  TEST= 0
INDE  4   6  34  FOBS=   74.6  SIGMA=  1.5  PHAS=   23.2  FOM= 0.49  TEST= 0
INDE  4   6  36  FOBS=  324.7  SIGMA=  0.9  PHAS=  104.7  FOM= 0.98  TEST= 0
INDE  4   6  38  FOBS=  179.5  SIGMA=  0.8  PHAS= -136.6  FOM= 0.84  TEST= 0
INDE  4   6  40  FOBS=   79.4  SIGMA=  1.8  PHAS=  -41.0  FOM= 0.98  TEST= 0
INDE  4   6  42  FOBS=  180.0  SIGMA=  1.1  PHAS=  148.3  FOM= 0.91  TEST= 0
INDE  4   6  44  FOBS=   21.2  SIGMA=  7.7  PHAS=  -26.4  FOM= 0.65  TEST= 0
INDE  4   6  46  FOBS=  127.7  SIGMA=  1.5  PHAS=  115.3  FOM= 0.98  TEST= 0
INDE  4   6  48  FOBS=   40.0  SIGMA=  5.6  PHAS=   22.2  FOM= 0.65  TEST= 0
INDE  4   6  50  FOBS=  123.6  SIGMA=  1.7  PHAS=  -26.5  FOM= 0.75  TEST= 0
INDE  4   6  52  FOBS=    0.0  SIGMA= 22.1  PHAS=    0.0  FOM= 0.00  TEST= 0
INDE  4   6  54  FOBS=  168.9  SIGMA=  1.2  PHAS=  -75.3  FOM= 0.88  TEST= 0
INDE  4   6  56  FOBS=  214.9  SIGMA=  1.1  PHAS= -119.7  FOM= 0.97  TEST= 0
INDE  4   6  58  FOBS=   59.9  SIGMA=  3.1  PHAS=  144.8  FOM= 0.33  TEST= 0
```

*FIG. 12A - 105*

```
INDE  4  6  60  FOBS=  147.5  SIGMA=   1.2  PHAS=  -129.2  FOM=  0.97  TEST= 0
INDE  4  6  62  FOBS=   32.8  SIGMA=   5.4  PHAS=   110.8  FOM=  0.31  TEST= 0
INDE  4  6  64  FOBS=   80.2  SIGMA=   2.5  PHAS=     8.2  FOM=  0.69  TEST= 1
INDE  4  6  66  FOBS=   50.0  SIGMA=   9.8  PHAS=    19.4  FOM=  0.14  TEST= 1
INDE  4  6  68  FOBS=   84.3  SIGMA=   4.4  PHAS=    88.4  FOM=  0.83  TEST= 0
INDE  4  6  70  FOBS=   38.4  SIGMA=   9.3  PHAS=  -173.1  FOM=  0.44  TEST= 0
INDE  4  6  72  FOBS=   28.7  SIGMA=  12.0  PHAS=   150.0  FOM=  0.07  TEST= 0
INDE  4  6  74  FOBS=   75.8  SIGMA=   4.7  PHAS=    75.0  FOM=  0.89  TEST= 0
INDE  4  6  76  FOBS=    0.0  SIGMA=  26.9  PHAS=     0.0  FOM=  0.00  TEST= 1
INDE  4  7  17  FOBS=  157.7  SIGMA=   0.5  PHAS=   -60.6  FOM=  0.67  TEST= 0
INDE  4  7  19  FOBS=  206.3  SIGMA=   0.5  PHAS=   -37.6  FOM=  0.91  TEST= 0
INDE  4  7  21  FOBS=  251.2  SIGMA=   0.6  PHAS=   119.6  FOM=  0.94  TEST= 0
INDE  4  7  23  FOBS=  155.1  SIGMA=   0.6  PHAS=  -151.3  FOM=  0.91  TEST= 0
INDE  4  7  25  FOBS=  161.1  SIGMA=   0.6  PHAS=   147.2  FOM=  0.57  TEST= 1
INDE  4  7  27  FOBS=  141.6  SIGMA=   0.7  PHAS=   133.2  FOM=  0.98  TEST= 1
INDE  4  7  29  FOBS=  132.6  SIGMA=   0.8  PHAS=  -104.8  FOM=  0.99  TEST= 0
INDE  4  7  31  FOBS=   61.9  SIGMA=   1.7  PHAS=   139.5  FOM=  0.99  TEST= 0
INDE  4  7  33  FOBS=   87.1  SIGMA=   1.3  PHAS=  -119.1  FOM=  0.98  TEST= 0
INDE  4  7  35  FOBS=  360.5  SIGMA=   0.7  PHAS=   -15.3  FOM=  0.99  TEST= 0
INDE  4  7  37  FOBS=    0.0  SIGMA=  16.1  PHAS=     0.0  FOM=  0.00  TEST= 0
INDE  4  7  39  FOBS=  328.9  SIGMA=   0.6  PHAS=  -132.7  FOM=  0.98  TEST= 0
INDE  4  7  41  FOBS=  268.3  SIGMA=   0.8  PHAS=  -126.7  FOM=  0.40  TEST= 1
INDE  4  7  43  FOBS=  178.6  SIGMA=   1.0  PHAS=  -161.8  FOM=  0.93  TEST= 0
INDE  4  7  45  FOBS=  238.1  SIGMA=   1.1  PHAS=  -152.9  FOM=  0.97  TEST= 0
INDE  4  7  47  FOBS=  197.3  SIGMA=   1.1  PHAS=   -46.4  FOM=  0.92  TEST= 0
INDE  4  7  49  FOBS=   72.6  SIGMA=   2.8  PHAS=   -90.1  FOM=  0.75  TEST= 0
INDE  4  7  51  FOBS=   98.6  SIGMA=   2.0  PHAS=    26.2  FOM=  0.89  TEST= 0
INDE  4  7  53  FOBS=   25.7  SIGMA=   8.0  PHAS=  -128.7  FOM=  0.61  TEST= 0
INDE  4  7  55  FOBS=   34.3  SIGMA=   6.0  PHAS=   175.9  FOM=  0.86  TEST= 0
INDE  4  7  57  FOBS=   30.6  SIGMA=   6.6  PHAS=  -169.6  FOM=  0.38  TEST= 0
INDE  4  7  59  FOBS=  111.7  SIGMA=   1.7  PHAS=   113.3  FOM=  0.88  TEST= 0
INDE  4  7  61  FOBS=   82.5  SIGMA=   1.9  PHAS=    83.4  FOM=  0.92  TEST= 0
INDE  4  7  63  FOBS=    0.0  SIGMA=  18.9  PHAS=     0.0  FOM=  0.00  TEST= 0
INDE  4  7  65  FOBS=   69.6  SIGMA=   3.7  PHAS=  -146.4  FOM=  0.86  TEST= 0
INDE  4  7  67  FOBS=  118.2  SIGMA=   3.3  PHAS=   -86.3  FOM=  0.93  TEST= 0
INDE  4  7  69  FOBS=  116.7  SIGMA=   3.3  PHAS=    82.4  FOM=  0.90  TEST= 0
INDE  4  7  71  FOBS=   25.1  SIGMA=  14.6  PHAS=  -125.3  FOM=  0.11  TEST= 0
INDE  4  7  73  FOBS=   20.8  SIGMA=  17.1  PHAS=    -1.5  FOM=  0.37  TEST= 0
INDE  4  7  75  FOBS=   76.6  SIGMA=   4.9  PHAS=   -68.5  FOM=  0.86  TEST= 0
INDE  4  7  77  FOBS=   44.0  SIGMA=   8.8  PHAS=    88.8  FOM=  0.77  TEST= 0
INDE  4  8  16  FOBS=  304.8  SIGMA=   0.4  PHAS=   -37.7  FOM=  0.61  TEST= 0
INDE  4  8  18  FOBS=  249.4  SIGMA=   0.4  PHAS=   177.5  FOM=  0.94  TEST= 0
INDE  4  8  20  FOBS=  101.1  SIGMA=   0.5  PHAS=  -170.2  FOM=  0.30  TEST= 0
INDE  4  8  22  FOBS=  197.6  SIGMA=   0.4  PHAS=    64.3  FOM=  0.87  TEST= 0
INDE  4  8  24  FOBS=  153.9  SIGMA=   0.5  PHAS=    68.2  FOM=  0.99  TEST= 0
INDE  4  8  26  FOBS=   43.9  SIGMA=   2.0  PHAS=   114.6  FOM=  0.94  TEST= 0
INDE  4  8  28  FOBS=  107.9  SIGMA=   0.9  PHAS=   159.1  FOM=  0.99  TEST= 0
INDE  4  8  30  FOBS=   51.9  SIGMA=   1.8  PHAS=   145.0  FOM=  0.92  TEST= 0
INDE  4  8  32  FOBS=  117.2  SIGMA=   1.0  PHAS=  -155.3  FOM=  0.99  TEST= 0
INDE  4  8  34  FOBS=   95.7  SIGMA=   1.3  PHAS=    -8.3  FOM=  0.43  TEST= 0
INDE  4  8  36  FOBS=   83.4  SIGMA=   1.6  PHAS=    83.1  FOM=  0.94  TEST= 0
INDE  4  8  38  FOBS=  441.7  SIGMA=   1.1  PHAS=   -95.2  FOM=  0.97  TEST= 0
INDE  4  8  40  FOBS=  343.6  SIGMA=   0.9  PHAS=   123.6  FOM=  0.95  TEST= 0
INDE  4  8  42  FOBS=  233.4  SIGMA=   1.1  PHAS=   126.4  FOM=  0.97  TEST= 0
INDE  4  8  44  FOBS=  246.6  SIGMA=   0.8  PHAS=   112.3  FOM=  0.95  TEST= 0
INDE  4  8  46  FOBS=  195.3  SIGMA=   1.1  PHAS=  -154.7  FOM=  0.94  TEST= 0
INDE  4  8  48  FOBS=  177.9  SIGMA=   1.4  PHAS=  -135.2  FOM=  0.92  TEST= 0
INDE  4  8  50  FOBS=  115.7  SIGMA=   1.8  PHAS=   140.4  FOM=  0.41  TEST= 0
INDE  4  8  52  FOBS=  116.7  SIGMA=   1.7  PHAS=  -106.7  FOM=  0.72  TEST= 0
INDE  4  8  54  FOBS=   56.0  SIGMA=   3.4  PHAS=   132.5  FOM=  0.76  TEST= 0
INDE  4  8  56  FOBS=  146.2  SIGMA=   1.9  PHAS=  -108.9  FOM=  0.86  TEST= 0
INDE  4  8  58  FOBS=  188.9  SIGMA=   1.1  PHAS=    13.8  FOM=  0.97  TEST= 0
INDE  4  8  60  FOBS=  161.8  SIGMA=   1.3  PHAS=   -71.0  FOM=  0.96  TEST= 0
INDE  4  8  62  FOBS=   20.5  SIGMA=   8.9  PHAS=    45.6  FOM=  0.13  TEST= 0
INDE  4  8  64  FOBS=   41.4  SIGMA=   5.5  PHAS=    43.8  FOM=  0.16  TEST= 0
INDE  4  8  66  FOBS=   43.5  SIGMA=   5.5  PHAS=   158.3  FOM=  0.81  TEST= 0
INDE  4  8  68  FOBS=  114.5  SIGMA=   3.4  PHAS=   -44.7  FOM=  0.92  TEST= 0
INDE  4  8  70  FOBS=   52.6  SIGMA=   7.1  PHAS=   -84.4  FOM=  0.76  TEST= 0
INDE  4  8  72  FOBS=    0.0  SIGMA=  27.4  PHAS=     0.0  FOM=  0.00  TEST= 0
INDE  4  8  74  FOBS=    0.0  SIGMA=  27.0  PHAS=     0.0  FOM=  0.00  TEST= 0
```

*FIG. 12A - 106*

```
INDE  4   8  76 FOBS=   31.0 SIGMA= 12.3 PHAS=  107.5 FOM= 0.67 TEST= 0
INDE  4   9  15 FOBS=  139.1 SIGMA=  0.4 PHAS= -137.0 FOM= 0.95 TEST= 0
INDE  4   9  17 FOBS=  267.4 SIGMA=  0.4 PHAS=   68.3 FOM= 0.98 TEST= 0
INDE  4   9  19 FOBS=  185.7 SIGMA=  0.4 PHAS=   46.9 FOM= 0.89 TEST= 0
INDE  4   9  21 FOBS=  162.9 SIGMA=  0.4 PHAS=  -77.6 FOM= 0.64 TEST= 0
INDE  4   9  23 FOBS=  155.7 SIGMA=  0.4 PHAS=  -48.4 FOM= 0.98 TEST= 0
INDE  4   9  25 FOBS=  101.3 SIGMA=  0.6 PHAS=  179.1 FOM= 0.96 TEST= 0
INDE  4   9  27 FOBS=  165.1 SIGMA=  0.5 PHAS=   75.1 FOM= 0.98 TEST= 0
INDE  4   9  29 FOBS=  143.5 SIGMA=  0.6 PHAS=  -41.7 FOM= 0.95 TEST= 0
INDE  4   9  31 FOBS=  238.7 SIGMA=  0.7 PHAS=   97.9 FOM= 0.94 TEST= 1
INDE  4   9  33 FOBS=  254.4 SIGMA=  0.6 PHAS=  -52.8 FOM= 0.99 TEST= 1
INDE  4   9  35 FOBS=  345.4 SIGMA=  1.1 PHAS=  -55.0 FOM= 0.97 TEST= 0
INDE  4   9  37 FOBS=  419.4 SIGMA=  0.8 PHAS=   98.7 FOM= 0.94 TEST= 0
INDE  4   9  39 FOBS=   67.0 SIGMA=  2.1 PHAS= -101.6 FOM= 0.86 TEST= 0
INDE  4   9  41 FOBS=  188.9 SIGMA=  1.3 PHAS=   29.8 FOM= 0.88 TEST= 0
INDE  4   9  43 FOBS=   91.7 SIGMA=  1.9 PHAS=  -74.7 FOM= 0.76 TEST= 0
INDE  4   9  45 FOBS=  100.4 SIGMA=  1.9 PHAS=  164.9 FOM= 0.73 TEST= 0
INDE  4   9  47 FOBS=  263.4 SIGMA=  0.9 PHAS=  100.6 FOM= 0.93 TEST= 0
INDE  4   9  49 FOBS=   99.1 SIGMA=  2.1 PHAS=  161.2 FOM= 0.79 TEST= 0
INDE  4   9  51 FOBS=   99.1 SIGMA=  2.3 PHAS=   74.6 FOM= 0.81 TEST= 0
INDE  4   9  53 FOBS=   94.2 SIGMA=  2.1 PHAS=    4.1 FOM= 0.83 TEST= 0
INDE  4   9  55 FOBS=   45.7 SIGMA=  4.2 PHAS= -158.7 FOM= 0.84 TEST= 0
INDE  4   9  57 FOBS=   72.3 SIGMA=  2.6 PHAS= -152.5 FOM= 0.85 TEST= 0
INDE  4   9  59 FOBS=  124.8 SIGMA=  1.6 PHAS= -136.1 FOM= 0.94 TEST= 0
INDE  4   9  61 FOBS=   95.0 SIGMA=  1.8 PHAS=    3.0 FOM= 0.92 TEST= 0
INDE  4   9  63 FOBS=   77.9 SIGMA=  2.4 PHAS=  -27.8 FOM= 0.87 TEST= 0
INDE  4   9  65 FOBS=    0.0 SIGMA= 20.8 PHAS=    0.0 FOM= 0.00 TEST= 0
INDE  4   9  67 FOBS=   58.5 SIGMA=  4.7 PHAS=  -61.3 FOM= 0.83 TEST= 0
INDE  4   9  69 FOBS=   71.9 SIGMA=  4.0 PHAS= -145.3 FOM= 0.91 TEST= 0
INDE  4   9  71 FOBS=   52.2 SIGMA=  7.4 PHAS=   44.6 FOM= 0.47 TEST= 0
INDE  4   9  73 FOBS=   59.4 SIGMA=  6.6 PHAS=  -83.4 FOM= 0.73 TEST= 0
INDE  4   9  75 FOBS=   55.1 SIGMA=  7.2 PHAS=   22.0 FOM= 0.89 TEST= 0
INDE  4   9  77 FOBS=   36.5 SIGMA= 10.8 PHAS=   81.6 FOM= 0.30 TEST= 0
INDE  4  10  16 FOBS=  128.7 SIGMA=  0.4 PHAS= -179.8 FOM= 0.46 TEST= 0
INDE  4  10  18 FOBS=   33.3 SIGMA=  1.4 PHAS=  163.4 FOM= 0.84 TEST= 0
INDE  4  10  20 FOBS=  102.9 SIGMA=  0.5 PHAS=  -45.2 FOM= 0.71 TEST= 0
INDE  4  10  22 FOBS=  139.5 SIGMA=  0.4 PHAS=  -59.5 FOM= 0.76 TEST= 0
INDE  4  10  24 FOBS=  209.0 SIGMA=  0.5 PHAS=  164.1 FOM= 0.94 TEST= 0
INDE  4  10  26 FOBS=  128.9 SIGMA=  0.5 PHAS=  115.0 FOM= 0.91 TEST= 0
INDE  4  10  28 FOBS=  158.6 SIGMA=  0.4 PHAS=  -92.5 FOM= 0.97 TEST= 0
INDE  4  10  30 FOBS=  228.5 SIGMA=  0.7 PHAS=    1.2 FOM= 0.99 TEST= 0
INDE  4  10  32 FOBS=   43.8 SIGMA=  2.0 PHAS=   64.6 FOM= 0.83 TEST= 0
INDE  4  10  34 FOBS=  163.7 SIGMA=  0.9 PHAS=  147.4 FOM= 0.98 TEST= 0
INDE  4  10  36 FOBS=   69.6 SIGMA=  2.0 PHAS=   39.9 FOM= 0.95 TEST= 1
INDE  4  10  38 FOBS=  358.3 SIGMA=  0.8 PHAS= -128.4 FOM= 0.97 TEST= 1
INDE  4  10  40 FOBS=   74.4 SIGMA=  2.0 PHAS=  -17.7 FOM= 0.70 TEST= 1
INDE  4  10  42 FOBS=   54.6 SIGMA=  3.0 PHAS=   87.5 FOM= 0.80 TEST= 0
INDE  4  10  44 FOBS=  259.4 SIGMA=  1.0 PHAS=  140.4 FOM= 0.95 TEST= 0
INDE  4  10  46 FOBS=  189.2 SIGMA=  1.1 PHAS=  -70.4 FOM= 0.97 TEST= 0
INDE  4  10  48 FOBS=   74.8 SIGMA=  2.7 PHAS=  113.8 FOM= 0.67 TEST= 0
INDE  4  10  50 FOBS=  146.4 SIGMA=  1.4 PHAS=  102.1 FOM= 0.80 TEST= 0
INDE  4  10  52 FOBS=  178.4 SIGMA=  1.2 PHAS=  -53.8 FOM= 0.93 TEST= 0
INDE  4  10  54 FOBS=  124.1 SIGMA=  1.6 PHAS=  161.5 FOM= 0.89 TEST= 0
INDE  4  10  56 FOBS=  135.5 SIGMA=  1.5 PHAS=  109.2 FOM= 0.82 TEST= 1
INDE  4  10  58 FOBS=  109.3 SIGMA=  1.8 PHAS=   29.5 FOM= 0.91 TEST= 0
INDE  4  10  60 FOBS=  149.9 SIGMA=  1.3 PHAS= -117.9 FOM= 0.96 TEST= 0
INDE  4  10  62 FOBS=   45.8 SIGMA=  3.4 PHAS= -122.6 FOM= 0.65 TEST= 1
INDE  4  10  64 FOBS=   50.8 SIGMA=  4.3 PHAS=    5.1 FOM= 0.75 TEST= 0
INDE  4  10  66 FOBS=   25.8 SIGMA= 10.8 PHAS=   -5.3 FOM= 0.36 TEST= 0
INDE  4  10  68 FOBS=  107.5 SIGMA=  2.7 PHAS= -157.3 FOM= 0.50 TEST= 1
INDE  4  10  70 FOBS=   55.7 SIGMA=  5.1 PHAS= -164.6 FOM= 0.36 TEST= 1
INDE  4  10  72 FOBS=   18.3 SIGMA= 21.4 PHAS=  -35.7 FOM= 0.31 TEST= 0
INDE  4  10  74 FOBS=    0.0 SIGMA= 28.3 PHAS=    0.0 FOM= 0.00 TEST= 0
INDE  4  10  76 FOBS=   64.3 SIGMA=  6.4 PHAS=   31.1 FOM= 0.91 TEST= 0
INDE  4  11  15 FOBS=  157.3 SIGMA=  0.4 PHAS=   -1.2 FOM= 0.83 TEST= 0
INDE  4  11  17 FOBS=  322.3 SIGMA=  0.4 PHAS=   55.8 FOM= 0.95 TEST= 0
INDE  4  11  19 FOBS=  227.9 SIGMA=  0.5 PHAS= -176.4 FOM= 0.95 TEST= 0
INDE  4  11  21 FOBS=  144.4 SIGMA=  0.4 PHAS= -126.1 FOM= 0.94 TEST= 0
INDE  4  11  23 FOBS=  119.5 SIGMA=  0.5 PHAS=   42.8 FOM= 0.91 TEST= 0
INDE  4  11  25 FOBS=  163.8 SIGMA=  0.4 PHAS=   15.1 FOM= 0.99 TEST= 0
```

*FIG. 12A - 107*

| | | | | | | | | | | | | |
|---|---|---|---|---|---|---|---|---|---|---|---|---|
| INDE | 4 | 11 | 27 | FOBS= | 169.1 | SIGMA= | 0.6 | PHAS= | -5.7 | FOM= | 0.91 | TEST= 0 |
| INDE | 4 | 11 | 29 | FOBS= | 201.6 | SIGMA= | 0.5 | PHAS= | -87.2 | FOM= | 0.97 | TEST= 0 |
| INDE | 4 | 11 | 31 | FOBS= | 67.8 | SIGMA= | 1.0 | PHAS= | 13.8 | FOM= | 0.92 | TEST= 0 |
| INDE | 4 | 11 | 33 | FOBS= | 174.9 | SIGMA= | 0.7 | PHAS= | -37.3 | FOM= | 0.88 | TEST= 0 |
| INDE | 4 | 11 | 35 | FOBS= | 260.2 | SIGMA= | 0.8 | PHAS= | -49.5 | FOM= | 0.96 | TEST= 0 |
| INDE | 4 | 11 | 37 | FOBS= | 163.9 | SIGMA= | 1.0 | PHAS= | 60.4 | FOM= | 0.20 | TEST= 1 |
| INDE | 4 | 11 | 39 | FOBS= | 302.1 | SIGMA= | 1.0 | PHAS= | 174.3 | FOM= | 0.95 | TEST= 0 |
| INDE | 4 | 11 | 41 | FOBS= | 276.1 | SIGMA= | 1.0 | PHAS= | 150.0 | FOM= | 0.90 | TEST= 0 |
| INDE | 4 | 11 | 43 | FOBS= | 135.1 | SIGMA= | 1.4 | PHAS= | -55.7 | FOM= | 0.75 | TEST= 0 |
| INDE | 4 | 11 | 45 | FOBS= | 48.7 | SIGMA= | 3.9 | PHAS= | -141.0 | FOM= | 0.80 | TEST= 0 |
| INDE | 4 | 11 | 47 | FOBS= | 0.0 | SIGMA= | 20.3 | PHAS= | 0.0 | FOM= | 0.00 | TEST= 0 |
| INDE | 4 | 11 | 49 | FOBS= | 67.1 | SIGMA= | 3.1 | PHAS= | 132.6 | FOM= | 0.95 | TEST= 0 |
| INDE | 4 | 11 | 51 | FOBS= | 82.1 | SIGMA= | 2.4 | PHAS= | 146.0 | FOM= | 0.74 | TEST= 0 |
| INDE | 4 | 11 | 53 | FOBS= | 57.6 | SIGMA= | 3.4 | PHAS= | 136.1 | FOM= | 0.14 | TEST= 0 |
| INDE | 4 | 11 | 55 | FOBS= | 131.0 | SIGMA= | 1.6 | PHAS= | 54.1 | FOM= | 0.72 | TEST= 0 |
| INDE | 4 | 11 | 57 | FOBS= | 62.2 | SIGMA= | 3.1 | PHAS= | 37.3 | FOM= | 0.61 | TEST= 0 |
| INDE | 4 | 11 | 59 | FOBS= | 125.7 | SIGMA= | 1.7 | PHAS= | -123.0 | FOM= | 0.91 | TEST= 0 |
| INDE | 4 | 11 | 61 | FOBS= | 90.4 | SIGMA= | 2.1 | PHAS= | 64.4 | FOM= | 0.81 | TEST= 0 |
| INDE | 4 | 11 | 63 | FOBS= | 81.4 | SIGMA= | 2.3 | PHAS= | 5.6 | FOM= | 0.91 | TEST= 0 |
| INDE | 4 | 11 | 65 | FOBS= | 98.5 | SIGMA= | 2.3 | PHAS= | -83.7 | FOM= | 0.22 | TEST= 1 |
| INDE | 4 | 11 | 67 | FOBS= | 67.7 | SIGMA= | 4.2 | PHAS= | -10.0 | FOM= | 0.58 | TEST= 0 |
| INDE | 4 | 11 | 69 | FOBS= | 97.1 | SIGMA= | 3.0 | PHAS= | -64.5 | FOM= | 0.58 | TEST= 0 |
| INDE | 4 | 11 | 71 | FOBS= | 19.2 | SIGMA= | 15.0 | PHAS= | 144.4 | FOM= | 0.15 | TEST= 0 |
| INDE | 4 | 11 | 73 | FOBS= | 44.2 | SIGMA= | 6.6 | PHAS= | 128.2 | FOM= | 0.58 | TEST= 0 |
| INDE | 4 | 11 | 75 | FOBS= | 0.0 | SIGMA= | 28.7 | PHAS= | 0.0 | FOM= | 0.00 | TEST= 1 |
| INDE | 4 | 12 | 14 | FOBS= | 186.6 | SIGMA= | 0.4 | PHAS= | 5.1 | FOM= | 0.96 | TEST= 0 |
| INDE | 4 | 12 | 16 | FOBS= | 312.5 | SIGMA= | 0.4 | PHAS= | -121.9 | FOM= | 0.93 | TEST= 0 |
| INDE | 4 | 12 | 18 | FOBS= | 135.6 | SIGMA= | 0.4 | PHAS= | -94.7 | FOM= | 0.90 | TEST= 0 |
| INDE | 4 | 12 | 20 | FOBS= | 134.9 | SIGMA= | 0.4 | PHAS= | 73.4 | FOM= | 0.89 | TEST= 0 |
| INDE | 4 | 12 | 22 | FOBS= | 55.3 | SIGMA= | 1.0 | PHAS= | -118.8 | FOM= | 0.74 | TEST= 0 |
| INDE | 4 | 12 | 24 | FOBS= | 130.7 | SIGMA= | 0.5 | PHAS= | -129.5 | FOM= | 0.97 | TEST= 0 |
| INDE | 4 | 12 | 26 | FOBS= | 245.2 | SIGMA= | 0.5 | PHAS= | -66.1 | FOM= | 0.99 | TEST= 0 |
| INDE | 4 | 12 | 28 | FOBS= | 153.5 | SIGMA= | 0.6 | PHAS= | -120.2 | FOM= | 0.98 | TEST= 0 |
| INDE | 4 | 12 | 30 | FOBS= | 52.3 | SIGMA= | 1.4 | PHAS= | -103.0 | FOM= | 0.93 | TEST= 0 |
| INDE | 4 | 12 | 32 | FOBS= | 61.3 | SIGMA= | 1.5 | PHAS= | -154.8 | FOM= | 0.98 | TEST= 0 |
| INDE | 4 | 12 | 34 | FOBS= | 204.3 | SIGMA= | 1.1 | PHAS= | 172.1 | FOM= | 0.93 | TEST= 0 |
| INDE | 4 | 12 | 36 | FOBS= | 333.7 | SIGMA= | 0.9 | PHAS= | 153.0 | FOM= | 0.95 | TEST= 0 |
| INDE | 4 | 12 | 38 | FOBS= | 14.5 | SIGMA= | 10.5 | PHAS= | -161.6 | FOM= | 0.03 | TEST= 0 |
| INDE | 4 | 12 | 40 | FOBS= | 91.8 | SIGMA= | 1.7 | PHAS= | 75.9 | FOM= | 0.93 | TEST= 0 |
| INDE | 4 | 12 | 42 | FOBS= | 217.9 | SIGMA= | 1.0 | PHAS= | 86.9 | FOM= | 0.98 | TEST= 0 |
| INDE | 4 | 12 | 44 | FOBS= | 111.4 | SIGMA= | 1.7 | PHAS= | -45.6 | FOM= | 0.89 | TEST= 0 |
| INDE | 4 | 12 | 46 | FOBS= | 78.3 | SIGMA= | 2.7 | PHAS= | -115.4 | FOM= | 0.83 | TEST= 1 |
| INDE | 4 | 12 | 48 | FOBS= | 125.9 | SIGMA= | 1.7 | PHAS= | 173.2 | FOM= | 0.77 | TEST= 0 |
| INDE | 4 | 12 | 50 | FOBS= | 91.2 | SIGMA= | 2.3 | PHAS= | 30.3 | FOM= | 0.95 | TEST= 0 |
| INDE | 4 | 12 | 52 | FOBS= | 78.2 | SIGMA= | 2.6 | PHAS= | -37.1 | FOM= | 0.81 | TEST= 1 |
| INDE | 4 | 12 | 54 | FOBS= | 12.1 | SIGMA= | 21.0 | PHAS= | -94.2 | FOM= | 0.02 | TEST= 0 |
| INDE | 4 | 12 | 56 | FOBS= | 12.6 | SIGMA= | 15.3 | PHAS= | -170.0 | FOM= | 0.10 | TEST= 0 |
| INDE | 4 | 12 | 58 | FOBS= | 0.0 | SIGMA= | 19.5 | PHAS= | 0.0 | FOM= | 0.00 | TEST= 1 |
| INDE | 4 | 12 | 60 | FOBS= | 114.1 | SIGMA= | 1.7 | PHAS= | -96.9 | FOM= | 0.95 | TEST= 0 |
| INDE | 4 | 12 | 62 | FOBS= | 117.5 | SIGMA= | 1.7 | PHAS= | -64.1 | FOM= | 0.90 | TEST= 0 |
| INDE | 4 | 12 | 64 | FOBS= | 0.0 | SIGMA= | 21.1 | PHAS= | 0.0 | FOM= | 0.00 | TEST= 0 |
| INDE | 4 | 12 | 66 | FOBS= | 6.3 | SIGMA= | 46.3 | PHAS= | -52.8 | FOM= | 0.08 | TEST= 0 |
| INDE | 4 | 12 | 68 | FOBS= | 87.1 | SIGMA= | 3.3 | PHAS= | 48.9 | FOM= | 0.30 | TEST= 0 |
| INDE | 4 | 12 | 70 | FOBS= | 27.0 | SIGMA= | 10.7 | PHAS= | 92.3 | FOM= | 0.25 | TEST= 0 |
| INDE | 4 | 12 | 72 | FOBS= | 16.1 | SIGMA= | 18.5 | PHAS= | -97.0 | FOM= | 0.13 | TEST= 0 |
| INDE | 4 | 12 | 74 | FOBS= | 23.9 | SIGMA= | 12.5 | PHAS= | 42.0 | FOM= | 0.08 | TEST= 0 |
| INDE | 4 | 12 | 76 | FOBS= | 0.0 | SIGMA= | 24.9 | PHAS= | 0.0 | FOM= | 0.00 | TEST= 0 |
| INDE | 4 | 13 | 13 | FOBS= | 146.9 | SIGMA= | 0.5 | PHAS= | 33.3 | FOM= | 0.81 | TEST= 0 |
| INDE | 4 | 13 | 15 | FOBS= | 198.9 | SIGMA= | 0.4 | PHAS= | 47.1 | FOM= | 0.06 | TEST= 1 |
| INDE | 4 | 13 | 17 | FOBS= | 323.0 | SIGMA= | 0.5 | PHAS= | 88.7 | FOM= | 0.97 | TEST= 0 |
| INDE | 4 | 13 | 19 | FOBS= | 274.7 | SIGMA= | 0.4 | PHAS= | 140.0 | FOM= | 0.97 | TEST= 0 |
| INDE | 4 | 13 | 21 | FOBS= | 127.0 | SIGMA= | 0.5 | PHAS= | 168.9 | FOM= | 0.90 | TEST= 0 |
| INDE | 4 | 13 | 23 | FOBS= | 117.6 | SIGMA= | 0.6 | PHAS= | 85.2 | FOM= | 0.98 | TEST= 0 |
| INDE | 4 | 13 | 25 | FOBS= | 176.5 | SIGMA= | 0.4 | PHAS= | -134.3 | FOM= | 0.98 | TEST= 0 |
| INDE | 4 | 13 | 27 | FOBS= | 53.8 | SIGMA= | 1.3 | PHAS= | -157.3 | FOM= | 0.99 | TEST= 0 |
| INDE | 4 | 13 | 29 | FOBS= | 100.6 | SIGMA= | 0.9 | PHAS= | 37.0 | FOM= | 0.98 | TEST= 0 |
| INDE | 4 | 13 | 31 | FOBS= | 59.0 | SIGMA= | 1.6 | PHAS= | 11.2 | FOM= | 0.96 | TEST= 0 |
| INDE | 4 | 13 | 33 | FOBS= | 146.0 | SIGMA= | 0.8 | PHAS= | -5.6 | FOM= | 0.96 | TEST= 0 |
| INDE | 4 | 13 | 35 | FOBS= | 219.9 | SIGMA= | 0.9 | PHAS= | 100.3 | FOM= | 0.77 | TEST= 0 |
| INDE | 4 | 13 | 37 | FOBS= | 283.7 | SIGMA= | 0.7 | PHAS= | -0.8 | FOM= | 0.95 | TEST= 0 |

*FIG. 12A - 108*

| | | | | | | | | | | | |
|---|---|---|---|---|---|---|---|---|---|---|---|
| INDE | 4 | 13 | 39 | FOBS= | 45.9 | SIGMA= | 3.3 | PHAS= | -29.7 | FOM= | 0.09 | TEST= 0
| INDE | 4 | 13 | 41 | FOBS= | 0.0 | SIGMA= | 20.2 | PHAS= | 0.0 | FOM= | 0.00 | TEST= 0
| INDE | 4 | 13 | 43 | FOBS= | 163.1 | SIGMA= | 1.2 | PHAS= | -84.6 | FOM= | 0.64 | TEST= 0
| INDE | 4 | 13 | 45 | FOBS= | 110.4 | SIGMA= | 1.9 | PHAS= | -142.5 | FOM= | 0.96 | TEST= 0
| INDE | 4 | 13 | 47 | FOBS= | 237.4 | SIGMA= | 1.0 | PHAS= | 118.7 | FOM= | 0.95 | TEST= 0
| INDE | 4 | 13 | 49 | FOBS= | 91.8 | SIGMA= | 2.3 | PHAS= | 131.8 | FOM= | 0.90 | TEST= 0
| INDE | 4 | 13 | 51 | FOBS= | 130.5 | SIGMA= | 1.6 | PHAS= | -24.0 | FOM= | 0.99 | TEST= 0
| INDE | 4 | 13 | 53 | FOBS= | 59.3 | SIGMA= | 3.3 | PHAS= | -90.5 | FOM= | 0.21 | TEST= 0
| INDE | 4 | 13 | 55 | FOBS= | 86.3 | SIGMA= | 2.3 | PHAS= | 50.5 | FOM= | 0.43 | TEST= 0
| INDE | 4 | 13 | 57 | FOBS= | 9.5 | SIGMA= | 20.1 | PHAS= | 27.6 | FOM= | 0.08 | TEST= 0
| INDE | 4 | 13 | 59 | FOBS= | 0.0 | SIGMA= | 20.9 | PHAS= | 0.0 | FOM= | 0.00 | TEST= 0
| INDE | 4 | 13 | 61 | FOBS= | 165.2 | SIGMA= | 1.3 | PHAS= | 164.5 | FOM= | 0.96 | TEST= 0
| INDE | 4 | 13 | 63 | FOBS= | 16.7 | SIGMA= | 12.6 | PHAS= | -157.8 | FOM= | 0.06 | TEST= 0
| INDE | 4 | 13 | 65 | FOBS= | 67.2 | SIGMA= | 3.8 | PHAS= | -109.2 | FOM= | 0.89 | TEST= 0
| INDE | 4 | 13 | 67 | FOBS= | 20.5 | SIGMA= | 14.1 | PHAS= | -106.1 | FOM= | 0.41 | TEST= 0
| INDE | 4 | 13 | 69 | FOBS= | 0.0 | SIGMA= | 23.9 | PHAS= | 0.0 | FOM= | 0.00 | TEST= 0
| INDE | 4 | 13 | 71 | FOBS= | 35.5 | SIGMA= | 8.2 | PHAS= | 41.7 | FOM= | 0.46 | TEST= 0
| INDE | 4 | 13 | 73 | FOBS= | 69.7 | SIGMA= | 4.4 | PHAS= | 115.5 | FOM= | 0.88 | TEST= 0
| INDE | 4 | 13 | 75 | FOBS= | 85.5 | SIGMA= | 3.7 | PHAS= | 64.6 | FOM= | 0.95 | TEST= 0
| INDE | 4 | 14 | 12 | FOBS= | 178.0 | SIGMA= | 0.5 | PHAS= | -37.8 | FOM= | 0.86 | TEST= 0
| INDE | 4 | 14 | 14 | FOBS= | 261.2 | SIGMA= | 0.5 | PHAS= | 9.4 | FOM= | 0.90 | TEST= 0
| INDE | 4 | 14 | 16 | FOBS= | 162.4 | SIGMA= | 0.4 | PHAS= | -77.4 | FOM= | 0.79 | TEST= 0
| INDE | 4 | 14 | 18 | FOBS= | 130.5 | SIGMA= | 0.5 | PHAS= | 80.9 | FOM= | 0.91 | TEST= 0
| INDE | 4 | 14 | 20 | FOBS= | 212.8 | SIGMA= | 0.4 | PHAS= | 45.9 | FOM= | 0.91 | TEST= 0
| INDE | 4 | 14 | 22 | FOBS= | 104.0 | SIGMA= | 0.6 | PHAS= | 80.9 | FOM= | 0.91 | TEST= 0
| INDE | 4 | 14 | 24 | FOBS= | 112.6 | SIGMA= | 0.6 | PHAS= | 147.3 | FOM= | 0.98 | TEST= 0
| INDE | 4 | 14 | 26 | FOBS= | 33.7 | SIGMA= | 2.3 | PHAS= | 132.2 | FOM= | 0.54 | TEST= 1
| INDE | 4 | 14 | 28 | FOBS= | 251.1 | SIGMA= | 0.6 | PHAS= | -61.5 | FOM= | 0.97 | TEST= 0
| INDE | 4 | 14 | 30 | FOBS= | 114.2 | SIGMA= | 0.8 | PHAS= | -54.1 | FOM= | 0.99 | TEST= 0
| INDE | 4 | 14 | 32 | FOBS= | 56.2 | SIGMA= | 1.7 | PHAS= | -60.4 | FOM= | 0.21 | TEST= 0
| INDE | 4 | 14 | 34 | FOBS= | 126.9 | SIGMA= | 1.0 | PHAS= | -40.0 | FOM= | 0.99 | TEST= 0
| INDE | 4 | 14 | 36 | FOBS= | 0.0 | SIGMA= | 17.0 | PHAS= | 0.0 | FOM= | 0.00 | TEST= 0
| INDE | 4 | 14 | 38 | FOBS= | 142.4 | SIGMA= | 1.1 | PHAS= | -88.8 | FOM= | 0.53 | TEST= 0
| INDE | 4 | 14 | 40 | FOBS= | 117.1 | SIGMA= | 1.5 | PHAS= | -145.7 | FOM= | 0.83 | TEST= 0
| INDE | 4 | 14 | 42 | FOBS= | 143.9 | SIGMA= | 1.3 | PHAS= | 104.6 | FOM= | 0.93 | TEST= 0
| INDE | 4 | 14 | 44 | FOBS= | 18.0 | SIGMA= | 12.7 | PHAS= | -104.1 | FOM= | 0.02 | TEST= 1
| INDE | 4 | 14 | 46 | FOBS= | 146.8 | SIGMA= | 1.5 | PHAS= | 111.9 | FOM= | 0.92 | TEST= 1
| INDE | 4 | 14 | 48 | FOBS= | 220.1 | SIGMA= | 1.1 | PHAS= | 35.5 | FOM= | 0.96 | TEST= 0
| INDE | 4 | 14 | 50 | FOBS= | 140.9 | SIGMA= | 1.5 | PHAS= | -70.9 | FOM= | 0.87 | TEST= 0
| INDE | 4 | 14 | 52 | FOBS= | 165.0 | SIGMA= | 1.3 | PHAS= | -67.9 | FOM= | 0.88 | TEST= 0
| INDE | 4 | 14 | 54 | FOBS= | 125.2 | SIGMA= | 1.6 | PHAS= | -72.0 | FOM= | 0.83 | TEST= 0
| INDE | 4 | 14 | 56 | FOBS= | 42.2 | SIGMA= | 4.9 | PHAS= | -116.7 | FOM= | 0.37 | TEST= 0
| INDE | 4 | 14 | 58 | FOBS= | 75.4 | SIGMA= | 2.6 | PHAS= | -19.0 | FOM= | 0.90 | TEST= 0
| INDE | 4 | 14 | 60 | FOBS= | 62.3 | SIGMA= | 3.1 | PHAS= | -51.1 | FOM= | 0.85 | TEST= 0
| INDE | 4 | 14 | 62 | FOBS= | 75.6 | SIGMA= | 2.6 | PHAS= | 66.4 | FOM= | 0.93 | TEST= 0
| INDE | 4 | 14 | 64 | FOBS= | 105.1 | SIGMA= | 2.6 | PHAS= | 122.9 | FOM= | 0.89 | TEST= 0
| INDE | 4 | 14 | 66 | FOBS= | 103.6 | SIGMA= | 3.0 | PHAS= | 125.8 | FOM= | 0.92 | TEST= 0
| INDE | 4 | 14 | 68 | FOBS= | 30.8 | SIGMA= | 9.7 | PHAS= | -24.3 | FOM= | 0.27 | TEST= 0
| INDE | 4 | 14 | 70 | FOBS= | 64.6 | SIGMA= | 4.6 | PHAS= | -40.8 | FOM= | 0.73 | TEST= 0
| INDE | 4 | 14 | 72 | FOBS= | 92.5 | SIGMA= | 3.3 | PHAS= | -33.9 | FOM= | 0.94 | TEST= 0
| INDE | 4 | 14 | 74 | FOBS= | 66.2 | SIGMA= | 4.7 | PHAS= | 4.8 | FOM= | 0.87 | TEST= 0
| INDE | 4 | 14 | 76 | FOBS= | 91.9 | SIGMA= | 3.5 | PHAS= | -11.5 | FOM= | 0.92 | TEST= 0
| INDE | 4 | 15 | 9 | FOBS= | 251.7 | SIGMA= | 0.6 | PHAS= | -65.0 | FOM= | 0.84 | TEST= 0
| INDE | 4 | 15 | 11 | FOBS= | 365.5 | SIGMA= | 0.6 | PHAS= | -42.1 | FOM= | 0.91 | TEST= 0
| INDE | 4 | 15 | 13 | FOBS= | 193.3 | SIGMA= | 0.5 | PHAS= | -113.4 | FOM= | 0.88 | TEST= 0
| INDE | 4 | 15 | 15 | FOBS= | 216.9 | SIGMA= | 0.7 | PHAS= | 156.4 | FOM= | 0.60 | TEST= 0
| INDE | 4 | 15 | 17 | FOBS= | 168.8 | SIGMA= | 0.6 | PHAS= | 114.8 | FOM= | 0.84 | TEST= 0
| INDE | 4 | 15 | 19 | FOBS= | 81.4 | SIGMA= | 0.8 | PHAS= | 157.5 | FOM= | 0.88 | TEST= 1
| INDE | 4 | 15 | 21 | FOBS= | 154.4 | SIGMA= | 0.5 | PHAS= | 50.4 | FOM= | 0.93 | TEST= 0
| INDE | 4 | 15 | 23 | FOBS= | 319.8 | SIGMA= | 0.5 | PHAS= | 9.1 | FOM= | 0.97 | TEST= 0
| INDE | 4 | 15 | 25 | FOBS= | 31.9 | SIGMA= | 2.0 | PHAS= | -82.3 | FOM= | 0.95 | TEST= 0
| INDE | 4 | 15 | 27 | FOBS= | 192.1 | SIGMA= | 0.5 | PHAS= | -61.3 | FOM= | 0.57 | TEST= 1
| INDE | 4 | 15 | 29 | FOBS= | 95.8 | SIGMA= | 0.9 | PHAS= | -64.7 | FOM= | 0.91 | TEST= 0
| INDE | 4 | 15 | 31 | FOBS= | 65.1 | SIGMA= | 1.5 | PHAS= | -95.7 | FOM= | 0.60 | TEST= 0
| INDE | 4 | 15 | 33 | FOBS= | 217.7 | SIGMA= | 0.6 | PHAS= | 126.7 | FOM= | 0.97 | TEST= 0
| INDE | 4 | 15 | 35 | FOBS= | 174.9 | SIGMA= | 0.8 | PHAS= | -67.1 | FOM= | 0.92 | TEST= 0
| INDE | 4 | 15 | 37 | FOBS= | 171.8 | SIGMA= | 0.9 | PHAS= | -135.5 | FOM= | 0.98 | TEST= 0
| INDE | 4 | 15 | 39 | FOBS= | 192.4 | SIGMA= | 0.9 | PHAS= | 59.9 | FOM= | 0.91 | TEST= 0
| INDE | 4 | 15 | 41 | FOBS= | 66.2 | SIGMA= | 1.8 | PHAS= | -61.6 | FOM= | 0.79 | TEST= 0
| INDE | 4 | 15 | 43 | FOBS= | 82.1 | SIGMA= | 2.4 | PHAS= | 142.3 | FOM= | 0.90 | TEST= 0

*FIG. 12A - 109*

```
INDE  4  15  45  FOBS=   275.5  SIGMA=   0.9  PHAS=    80.1  FOM=  0.95  TEST= 0
INDE  4  15  47  FOBS=   194.1  SIGMA=   1.2  PHAS=  -114.8  FOM=  0.93  TEST= 0
INDE  4  15  49  FOBS=   113.1  SIGMA=   1.9  PHAS=   -33.8  FOM=  0.72  TEST= 0
INDE  4  15  51  FOBS=    27.7  SIGMA=   7.4  PHAS=  -119.9  FOM=  0.10  TEST= 0
INDE  4  15  53  FOBS=   176.7  SIGMA=   1.2  PHAS=  -121.6  FOM=  0.93  TEST= 0
INDE  4  15  55  FOBS=    60.8  SIGMA=   3.3  PHAS=  -148.1  FOM=  0.18  TEST= 1
INDE  4  15  57  FOBS=   124.8  SIGMA=   1.6  PHAS=  -131.5  FOM=  0.95  TEST= 0
INDE  4  15  59  FOBS=    92.9  SIGMA=   2.1  PHAS=  -136.2  FOM=  0.79  TEST= 0
INDE  4  15  61  FOBS=   114.2  SIGMA=   1.7  PHAS=   177.6  FOM=  0.82  TEST= 0
INDE  4  15  63  FOBS=   112.4  SIGMA=   2.1  PHAS=   -16.5  FOM=  0.92  TEST= 0
INDE  4  15  65  FOBS=    85.3  SIGMA=   3.6  PHAS=    21.8  FOM=  0.88  TEST= 0
INDE  4  15  67  FOBS=    55.2  SIGMA=   5.5  PHAS=    74.6  FOM=  0.75  TEST= 0
INDE  4  15  69  FOBS=    56.8  SIGMA=   5.3  PHAS=  -154.6  FOM=  0.79  TEST= 0
INDE  4  15  71  FOBS=    94.2  SIGMA=   3.3  PHAS=  -117.3  FOM=  0.94  TEST= 0
INDE  4  15  73  FOBS=    35.1  SIGMA=   8.6  PHAS=  -169.2  FOM=  0.70  TEST= 0
INDE  4  15  75  FOBS=     0.0  SIGMA=  25.1  PHAS=     0.0  FOM=  0.00  TEST= 0
INDE  4  16   8  FOBS=   335.9  SIGMA=   0.7  PHAS=   136.2  FOM=  0.82  TEST= 0
INDE  4  16  10  FOBS=   354.4  SIGMA=   0.5  PHAS=  -163.1  FOM=  0.23  TEST= 1
INDE  4  16  12  FOBS=   157.3  SIGMA=   0.7  PHAS=   -96.7  FOM=  0.89  TEST= 0
INDE  4  16  14  FOBS=   232.9  SIGMA=   0.6  PHAS=    67.3  FOM=  0.94  TEST= 0
INDE  4  16  16  FOBS=   201.6  SIGMA=   0.5  PHAS=    30.1  FOM=  0.86  TEST= 0
INDE  4  16  18  FOBS=   188.8  SIGMA=   0.5  PHAS=    89.2  FOM=  0.88  TEST= 0
INDE  4  16  20  FOBS=   173.8  SIGMA=   0.5  PHAS=   -98.0  FOM=  0.84  TEST= 0
INDE  4  16  22  FOBS=   262.9  SIGMA=   0.5  PHAS=   -47.0  FOM=  0.95  TEST= 1
INDE  4  16  24  FOBS=   209.0  SIGMA=   0.6  PHAS=  -131.8  FOM=  0.97  TEST= 0
INDE  4  16  26  FOBS=   134.0  SIGMA=   0.6  PHAS=  -159.5  FOM=  0.93  TEST= 0
INDE  4  16  28  FOBS=   233.6  SIGMA=   0.5  PHAS=   -84.1  FOM=  0.97  TEST= 0
INDE  4  16  30  FOBS=   162.6  SIGMA=   0.7  PHAS=  -113.0  FOM=  0.98  TEST= 0
INDE  4  16  32  FOBS=   342.0  SIGMA=   0.6  PHAS=    60.5  FOM=  0.96  TEST= 0
INDE  4  16  34  FOBS=   211.7  SIGMA=   0.7  PHAS=    45.5  FOM=  0.99  TEST= 0
INDE  4  16  36  FOBS=    98.9  SIGMA=   1.3  PHAS=    63.0  FOM=  0.99  TEST= 1
INDE  4  16  38  FOBS=   232.5  SIGMA=   0.7  PHAS=   113.5  FOM=  0.96  TEST= 1
INDE  4  16  40  FOBS=   101.6  SIGMA=   1.0  PHAS=  -155.6  FOM=  0.74  TEST= 0
INDE  4  16  42  FOBS=   184.5  SIGMA=   0.8  PHAS=   118.7  FOM=  0.74  TEST= 0
INDE  4  16  44  FOBS=   183.0  SIGMA=   1.2  PHAS=    -7.8  FOM=  0.92  TEST= 0
INDE  4  16  46  FOBS=   112.8  SIGMA=   2.0  PHAS=    67.4  FOM=  0.57  TEST= 0
INDE  4  16  48  FOBS=   210.0  SIGMA=   1.1  PHAS=    66.8  FOM=  0.93  TEST= 0
INDE  4  16  50  FOBS=   166.3  SIGMA=   1.3  PHAS=     7.1  FOM=  0.94  TEST= 0
INDE  4  16  52  FOBS=    60.8  SIGMA=   3.4  PHAS=   -80.3  FOM=  0.65  TEST= 0
INDE  4  16  54  FOBS=   133.8  SIGMA=   1.6  PHAS=    96.1  FOM=  0.28  TEST= 0
INDE  4  16  56  FOBS=   155.6  SIGMA=   1.4  PHAS=   107.9  FOM=  0.95  TEST= 0
INDE  4  16  58  FOBS=   131.6  SIGMA=   1.6  PHAS=   110.8  FOM=  0.95  TEST= 0
INDE  4  16  60  FOBS=    23.9  SIGMA=   8.1  PHAS=   102.4  FOM=  0.11  TEST= 0
INDE  4  16  62  FOBS=    21.4  SIGMA=   9.0  PHAS=    45.9  FOM=  0.15  TEST= 0
INDE  4  16  64  FOBS=    59.3  SIGMA=   4.7  PHAS=   -39.5  FOM=  0.65  TEST= 0
INDE  4  16  66  FOBS=     0.0  SIGMA=  24.8  PHAS=     0.0  FOM=  0.00  TEST= 0
INDE  4  16  68  FOBS=   112.6  SIGMA=   2.9  PHAS=    35.7  FOM=  0.92  TEST= 0
INDE  4  16  70  FOBS=    58.1  SIGMA=   5.4  PHAS=   139.7  FOM=  0.80  TEST= 0
INDE  4  16  72  FOBS=    37.3  SIGMA=   8.3  PHAS=  -179.4  FOM=  0.52  TEST= 0
INDE  4  16  74  FOBS=    25.3  SIGMA=  12.4  PHAS=     4.0  FOM=  0.55  TEST= 0
INDE  4  16  76  FOBS=    30.3  SIGMA=   9.7  PHAS=   -15.9  FOM=  0.32  TEST= 0
INDE  4  17   5  FOBS=   189.2  SIGMA=   0.4  PHAS=    13.0  FOM=  0.56  TEST= 1
INDE  4  17   7  FOBS=   530.6  SIGMA=   0.6  PHAS=   -76.8  FOM=  0.97  TEST= 0
INDE  4  17   9  FOBS=    38.9  SIGMA=   1.9  PHAS=  -104.9  FOM=  0.83  TEST= 1
INDE  4  17  11  FOBS=    97.6  SIGMA=   1.0  PHAS=  -134.3  FOM=  0.85  TEST= 0
INDE  4  17  13  FOBS=   213.3  SIGMA=   0.6  PHAS=  -101.7  FOM=  0.79  TEST= 1
INDE  4  17  15  FOBS=    65.1  SIGMA=   1.5  PHAS=    84.8  FOM=  0.17  TEST= 0
INDE  4  17  17  FOBS=   185.0  SIGMA=   0.5  PHAS=     3.2  FOM=  0.84  TEST= 0
INDE  4  17  19  FOBS=   192.0  SIGMA=   0.6  PHAS=   141.3  FOM=  0.98  TEST= 1
INDE  4  17  21  FOBS=   124.5  SIGMA=   0.6  PHAS=   164.7  FOM=  0.98  TEST= 0
INDE  4  17  23  FOBS=    56.0  SIGMA=   1.2  PHAS=   179.5  FOM=  0.92  TEST= 0
INDE  4  17  25  FOBS=   176.9  SIGMA=   0.6  PHAS=    64.4  FOM=  0.92  TEST= 0
INDE  4  17  27  FOBS=    77.4  SIGMA=   1.0  PHAS=   110.0  FOM=  0.60  TEST= 0
INDE  4  17  29  FOBS=   109.2  SIGMA=   0.7  PHAS=   152.4  FOM=  0.88  TEST= 0
INDE  4  17  31  FOBS=   100.8  SIGMA=   1.0  PHAS=   -67.5  FOM=  0.94  TEST= 0
INDE  4  17  33  FOBS=   129.5  SIGMA=   0.9  PHAS=   -89.2  FOM=  0.95  TEST= 0
INDE  4  17  35  FOBS=   480.5  SIGMA=   0.7  PHAS=   -69.9  FOM=  0.98  TEST= 0
INDE  4  17  37  FOBS=   128.5  SIGMA=   1.1  PHAS=   170.9  FOM=  0.90  TEST= 0
INDE  4  17  39  FOBS=   164.4  SIGMA=   0.9  PHAS=    87.0  FOM=  0.97  TEST= 0
INDE  4  17  41  FOBS=    61.6  SIGMA=   1.7  PHAS=    14.5  FOM=  0.96  TEST= 0
```

*FIG. 12A - 110*

| | | | | | | | | | | | | |
|---|---|---|---|---|---|---|---|---|---|---|---|---|
| INDE | 4 | 17 | 43 | FOBS= | 124.4 | SIGMA= | 1.2 | PHAS= | -58.1 | FOM= | 0.93 | TEST= 0 |
| INDE | 4 | 17 | 45 | FOBS= | 211.6 | SIGMA= | 1.1 | PHAS= | 52.0 | FOM= | 0.97 | TEST= 0 |
| INDE | 4 | 17 | 47 | FOBS= | 218.3 | SIGMA= | 1.5 | PHAS= | -91.8 | FOM= | 0.94 | TEST= 0 |
| INDE | 4 | 17 | 49 | FOBS= | 286.1 | SIGMA= | 1.2 | PHAS= | -30.5 | FOM= | 0.97 | TEST= 0 |
| INDE | 4 | 17 | 51 | FOBS= | 60.8 | SIGMA= | 3.6 | PHAS= | -145.8 | FOM= | 0.25 | TEST= 0 |
| INDE | 4 | 17 | 53 | FOBS= | 118.7 | SIGMA= | 1.8 | PHAS= | -76.5 | FOM= | 0.88 | TEST= 0 |
| INDE | 4 | 17 | 55 | FOBS= | 157.6 | SIGMA= | 1.4 | PHAS= | 0.7 | FOM= | 0.94 | TEST= 0 |
| INDE | 4 | 17 | 57 | FOBS= | 107.9 | SIGMA= | 1.9 | PHAS= | 59.8 | FOM= | 0.87 | TEST= 0 |
| INDE | 4 | 17 | 59 | FOBS= | 0.0 | SIGMA= | 19.6 | PHAS= | 0.0 | FOM= | 0.00 | TEST= 0 |
| INDE | 4 | 17 | 61 | FOBS= | 18.4 | SIGMA= | 10.5 | PHAS= | 112.2 | FOM= | 0.09 | TEST= 0 |
| INDE | 4 | 17 | 63 | FOBS= | 67.2 | SIGMA= | 3.5 | PHAS= | 31.6 | FOM= | 0.80 | TEST= 0 |
| INDE | 4 | 17 | 65 | FOBS= | 62.5 | SIGMA= | 7.0 | PHAS= | -131.1 | FOM= | 0.55 | TEST= 0 |
| INDE | 4 | 17 | 67 | FOBS= | 69.5 | SIGMA= | 4.6 | PHAS= | 144.5 | FOM= | 0.78 | TEST= 0 |
| INDE | 4 | 17 | 69 | FOBS= | 31.2 | SIGMA= | 10.0 | PHAS= | -67.2 | FOM= | 0.17 | TEST= 1 |
| INDE | 4 | 17 | 71 | FOBS= | 43.4 | SIGMA= | 7.2 | PHAS= | -92.6 | FOM= | 0.08 | TEST= 1 |
| INDE | 4 | 17 | 73 | FOBS= | 0.0 | SIGMA= | 25.1 | PHAS= | 0.0 | FOM= | 0.00 | TEST= 0 |
| INDE | 4 | 17 | 75 | FOBS= | 38.8 | SIGMA= | 8.3 | PHAS= | -63.0 | FOM= | 0.59 | TEST= 0 |
| INDE | 4 | 18 | 4 | FOBS= | 48.1 | SIGMA= | 1.0 | PHAS= | 17.1 | FOM= | 0.98 | TEST= 0 |
| INDE | 4 | 18 | 6 | FOBS= | 376.0 | SIGMA= | 0.5 | PHAS= | -59.6 | FOM= | 0.74 | TEST= 1 |
| INDE | 4 | 18 | 8 | FOBS= | 380.3 | SIGMA= | 0.6 | PHAS= | -124.2 | FOM= | 0.97 | TEST= 0 |
| INDE | 4 | 18 | 10 | FOBS= | 224.3 | SIGMA= | 0.7 | PHAS= | 178.4 | FOM= | 0.76 | TEST= 0 |
| INDE | 4 | 18 | 12 | FOBS= | 75.6 | SIGMA= | 1.4 | PHAS= | 117.7 | FOM= | 0.64 | TEST= 0 |
| INDE | 4 | 18 | 14 | FOBS= | 285.8 | SIGMA= | 0.7 | PHAS= | 119.1 | FOM= | 0.95 | TEST= 0 |
| INDE | 4 | 18 | 16 | FOBS= | 117.6 | SIGMA= | 1.0 | PHAS= | -150.0 | FOM= | 0.87 | TEST= 0 |
| INDE | 4 | 18 | 18 | FOBS= | 131.9 | SIGMA= | 0.7 | PHAS= | -96.8 | FOM= | 0.94 | TEST= 0 |
| INDE | 4 | 18 | 20 | FOBS= | 60.4 | SIGMA= | 1.3 | PHAS= | -59.6 | FOM= | 0.39 | TEST= 0 |
| INDE | 4 | 18 | 22 | FOBS= | 73.8 | SIGMA= | 1.0 | PHAS= | -0.2 | FOM= | 0.65 | TEST= 0 |
| INDE | 4 | 18 | 24 | FOBS= | 71.1 | SIGMA= | 1.1 | PHAS= | -105.3 | FOM= | 0.73 | TEST= 1 |
| INDE | 4 | 18 | 26 | FOBS= | 161.8 | SIGMA= | 0.5 | PHAS= | -70.9 | FOM= | 0.43 | TEST= 0 |
| INDE | 4 | 18 | 28 | FOBS= | 89.1 | SIGMA= | 0.9 | PHAS= | -121.3 | FOM= | 0.87 | TEST= 0 |
| INDE | 4 | 18 | 30 | FOBS= | 47.0 | SIGMA= | 1.7 | PHAS= | -114.4 | FOM= | 0.92 | TEST= 0 |
| INDE | 4 | 18 | 32 | FOBS= | 233.3 | SIGMA= | 0.6 | PHAS= | 99.7 | FOM= | 0.48 | TEST= 1 |
| INDE | 4 | 18 | 34 | FOBS= | 112.1 | SIGMA= | 1.2 | PHAS= | -116.3 | FOM= | 0.95 | TEST= 1 |
| INDE | 4 | 18 | 36 | FOBS= | 63.6 | SIGMA= | 2.2 | PHAS= | -150.7 | FOM= | 0.97 | TEST= 0 |
| INDE | 4 | 18 | 38 | FOBS= | 324.4 | SIGMA= | 0.6 | PHAS= | 87.0 | FOM= | 0.94 | TEST= 0 |
| INDE | 4 | 18 | 40 | FOBS= | 120.7 | SIGMA= | 1.0 | PHAS= | 49.3 | FOM= | 0.96 | TEST= 0 |
| INDE | 4 | 18 | 42 | FOBS= | 29.4 | SIGMA= | 3.9 | PHAS= | -61.0 | FOM= | 0.35 | TEST= 0 |
| INDE | 4 | 18 | 44 | FOBS= | 273.1 | SIGMA= | 0.7 | PHAS= | -59.6 | FOM= | 0.95 | TEST= 0 |
| INDE | 4 | 18 | 46 | FOBS= | 123.4 | SIGMA= | 1.9 | PHAS= | -158.0 | FOM= | 0.89 | TEST= 0 |
| INDE | 4 | 18 | 48 | FOBS= | 154.1 | SIGMA= | 1.5 | PHAS= | -93.3 | FOM= | 0.88 | TEST= 0 |
| INDE | 4 | 18 | 50 | FOBS= | 70.9 | SIGMA= | 3.0 | PHAS= | 132.7 | FOM= | 0.87 | TEST= 0 |
| INDE | 4 | 18 | 52 | FOBS= | 119.3 | SIGMA= | 1.8 | PHAS= | -80.0 | FOM= | 0.57 | TEST= 0 |
| INDE | 4 | 18 | 54 | FOBS= | 57.0 | SIGMA= | 3.6 | PHAS= | 127.0 | FOM= | 0.41 | TEST= 0 |
| INDE | 4 | 18 | 56 | FOBS= | 89.7 | SIGMA= | 2.3 | PHAS= | -26.1 | FOM= | 0.85 | TEST= 0 |
| INDE | 4 | 18 | 58 | FOBS= | 82.9 | SIGMA= | 2.5 | PHAS= | 64.3 | FOM= | 0.92 | TEST= 0 |
| INDE | 4 | 18 | 60 | FOBS= | 0.0 | SIGMA= | 19.7 | PHAS= | 0.0 | FOM= | 0.00 | TEST= 0 |
| INDE | 4 | 18 | 62 | FOBS= | 86.0 | SIGMA= | 2.7 | PHAS= | -22.8 | FOM= | 0.89 | TEST= 0 |
| INDE | 4 | 18 | 64 | FOBS= | 79.7 | SIGMA= | 5.5 | PHAS= | -136.5 | FOM= | 0.82 | TEST= 0 |
| INDE | 4 | 18 | 66 | FOBS= | 25.1 | SIGMA= | 17.5 | PHAS= | -121.4 | FOM= | 0.03 | TEST= 0 |
| INDE | 4 | 18 | 68 | FOBS= | 134.0 | SIGMA= | 2.5 | PHAS= | 23.5 | FOM= | 0.97 | TEST= 0 |
| INDE | 4 | 18 | 70 | FOBS= | 58.5 | SIGMA= | 5.4 | PHAS= | 58.0 | FOM= | 0.89 | TEST= 0 |
| INDE | 4 | 18 | 72 | FOBS= | 58.8 | SIGMA= | 5.5 | PHAS= | -119.9 | FOM= | 0.82 | TEST= 0 |
| INDE | 4 | 18 | 74 | FOBS= | 0.0 | SIGMA= | 25.1 | PHAS= | 0.0 | FOM= | 0.00 | TEST= 0 |
| INDE | 4 | 19 | 5 | FOBS= | 384.0 | SIGMA= | 0.4 | PHAS= | 178.0 | FOM= | 0.96 | TEST= 0 |
| INDE | 4 | 19 | 7 | FOBS= | 69.3 | SIGMA= | 1.1 | PHAS= | 120.1 | FOM= | 0.82 | TEST= 0 |
| INDE | 4 | 19 | 9 | FOBS= | 76.5 | SIGMA= | 1.1 | PHAS= | -92.3 | FOM= | 0.67 | TEST= 0 |
| INDE | 4 | 19 | 11 | FOBS= | 191.9 | SIGMA= | 0.9 | PHAS= | 42.6 | FOM= | 0.67 | TEST= 0 |
| INDE | 4 | 19 | 13 | FOBS= | 163.9 | SIGMA= | 1.0 | PHAS= | 10.8 | FOM= | 0.95 | TEST= 0 |
| INDE | 4 | 19 | 15 | FOBS= | 157.7 | SIGMA= | 1.0 | PHAS= | 48.3 | FOM= | 0.97 | TEST= 0 |
| INDE | 4 | 19 | 17 | FOBS= | 165.8 | SIGMA= | 0.8 | PHAS= | 112.2 | FOM= | 0.91 | TEST= 0 |
| INDE | 4 | 19 | 19 | FOBS= | 141.3 | SIGMA= | 0.7 | PHAS= | 177.8 | FOM= | 0.97 | TEST= 0 |
| INDE | 4 | 19 | 21 | FOBS= | 27.0 | SIGMA= | 3.3 | PHAS= | 166.1 | FOM= | 0.23 | TEST= 0 |
| INDE | 4 | 19 | 23 | FOBS= | 125.7 | SIGMA= | 0.7 | PHAS= | -75.9 | FOM= | 0.97 | TEST= 1 |
| INDE | 4 | 19 | 25 | FOBS= | 76.8 | SIGMA= | 1.0 | PHAS= | 78.0 | FOM= | 0.71 | TEST= 0 |
| INDE | 4 | 19 | 27 | FOBS= | 117.5 | SIGMA= | 0.7 | PHAS= | 151.9 | FOM= | 0.98 | TEST= 0 |
| INDE | 4 | 19 | 29 | FOBS= | 89.1 | SIGMA= | 0.9 | PHAS= | -141.3 | FOM= | 0.95 | TEST= 0 |
| INDE | 4 | 19 | 31 | FOBS= | 123.2 | SIGMA= | 0.7 | PHAS= | 124.0 | FOM= | 0.85 | TEST= 0 |
| INDE | 4 | 19 | 33 | FOBS= | 166.6 | SIGMA= | 0.7 | PHAS= | -27.4 | FOM= | 0.87 | TEST= 0 |
| INDE | 4 | 19 | 35 | FOBS= | 180.3 | SIGMA= | 0.9 | PHAS= | -37.5 | FOM= | 0.91 | TEST= 0 |
| INDE | 4 | 19 | 37 | FOBS= | 304.9 | SIGMA= | 0.6 | PHAS= | 94.8 | FOM= | 0.95 | TEST= 1 |

*FIG. 12A - 111*

```
INDE  4  19  39  FOBS=   65.2  SIGMA=   2.3  PHAS=   -6.6  FOM= 0.37  TEST= 0
INDE  4  19  41  FOBS=  219.6  SIGMA=   0.6  PHAS=   62.2  FOM= 0.97  TEST= 0
INDE  4  19  43  FOBS=  147.9  SIGMA=   1.0  PHAS= -139.0  FOM= 0.99  TEST= 0
INDE  4  19  45  FOBS=  275.3  SIGMA=   0.6  PHAS=   76.6  FOM= 0.97  TEST= 0
INDE  4  19  47  FOBS=   29.7  SIGMA=   5.8  PHAS= -129.8  FOM= 0.83  TEST= 0
INDE  4  19  49  FOBS=   94.9  SIGMA=   2.3  PHAS=  -25.0  FOM= 0.87  TEST= 0
INDE  4  19  51  FOBS=  177.2  SIGMA=   1.3  PHAS=   90.0  FOM= 0.94  TEST= 0
INDE  4  19  53  FOBS=   73.9  SIGMA=   2.8  PHAS=   19.4  FOM= 0.70  TEST= 0
INDE  4  19  55  FOBS=  116.5  SIGMA=   1.8  PHAS=  -25.7  FOM= 0.89  TEST= 0
INDE  4  19  57  FOBS=    0.0  SIGMA=  20.0  PHAS=    0.0  FOM= 0.00  TEST= 0
INDE  4  19  59  FOBS=   81.4  SIGMA=   2.5  PHAS=  -55.4  FOM= 0.93  TEST= 0
INDE  4  19  61  FOBS=  164.4  SIGMA=   1.3  PHAS= -104.7  FOM= 0.95  TEST= 0
INDE  4  19  63  FOBS=  172.8  SIGMA=   1.5  PHAS=  176.4  FOM= 0.96  TEST= 0
INDE  4  19  65  FOBS=    0.0  SIGMA=  29.3  PHAS=    0.0  FOM= 0.00  TEST= 0
INDE  4  19  67  FOBS=   24.3  SIGMA=  13.3  PHAS= -128.9  FOM= 0.47  TEST= 0
INDE  4  19  69  FOBS=   95.3  SIGMA=   3.5  PHAS=  -71.0  FOM= 0.96  TEST= 0
INDE  4  19  71  FOBS=   39.1  SIGMA=   8.2  PHAS=   78.6  FOM= 0.30  TEST= 0
INDE  4  19  73  FOBS=   58.4  SIGMA=   5.7  PHAS=  109.8  FOM= 0.83  TEST= 0
INDE  4  19  75  FOBS=   38.0  SIGMA=   8.8  PHAS=  174.8  FOM= 0.14  TEST= 1
INDE  4  20   4  FOBS=   84.0  SIGMA=   0.7  PHAS= -162.2  FOM= 0.69  TEST= 0
INDE  4  20   6  FOBS=  352.7  SIGMA=   0.5  PHAS=  171.1  FOM= 0.94  TEST= 0
INDE  4  20   8  FOBS=   96.3  SIGMA=   1.0  PHAS=  -96.5  FOM= 0.90  TEST= 0
INDE  4  20  10  FOBS=   90.1  SIGMA=   1.0  PHAS=  -65.4  FOM= 0.78  TEST= 0
INDE  4  20  12  FOBS=  230.8  SIGMA=   0.8  PHAS=  -26.3  FOM= 0.96  TEST= 0
INDE  4  20  14  FOBS=  117.0  SIGMA=   1.3  PHAS= -122.7  FOM= 0.82  TEST= 0
INDE  4  20  16  FOBS=   86.6  SIGMA=   1.6  PHAS=  -38.3  FOM= 0.98  TEST= 0
INDE  4  20  18  FOBS=   39.4  SIGMA=   2.6  PHAS=  -26.4  FOM= 0.87  TEST= 0
INDE  4  20  20  FOBS=  138.8  SIGMA=   0.8  PHAS=  144.7  FOM= 0.99  TEST= 0
INDE  4  20  22  FOBS=   65.6  SIGMA=   1.5  PHAS=   42.6  FOM= 0.99  TEST= 0
INDE  4  20  24  FOBS=  182.2  SIGMA=   0.6  PHAS=  110.2  FOM= 0.99  TEST= 0
INDE  4  20  26  FOBS=    8.8  SIGMA=  10.5  PHAS=  -47.5  FOM= 0.22  TEST= 0
INDE  4  20  28  FOBS=   51.5  SIGMA=   1.6  PHAS= -131.1  FOM= 0.89  TEST= 0
INDE  4  20  30  FOBS=  232.0  SIGMA=   0.5  PHAS=    9.2  FOM= 0.95  TEST= 0
INDE  4  20  32  FOBS=  218.2  SIGMA=   0.5  PHAS=   74.6  FOM= 0.80  TEST= 0
INDE  4  20  34  FOBS=  259.7  SIGMA=   0.6  PHAS= -133.1  FOM= 0.99  TEST= 0
INDE  4  20  36  FOBS=  231.3  SIGMA=   0.8  PHAS=  -94.0  FOM= 0.92  TEST= 1
INDE  4  20  38  FOBS=  144.9  SIGMA=   1.1  PHAS=  -91.8  FOM= 0.96  TEST= 0
INDE  4  20  40  FOBS=  251.2  SIGMA=   0.9  PHAS=   22.5  FOM= 0.95  TEST= 0
INDE  4  20  42  FOBS=  161.4  SIGMA=   0.8  PHAS=  -50.8  FOM= 0.93  TEST= 0
INDE  4  20  44  FOBS=   79.6  SIGMA=   1.7  PHAS= -167.6  FOM= 0.95  TEST= 0
INDE  4  20  46  FOBS=   79.2  SIGMA=   1.6  PHAS=   -0.8  FOM= 0.51  TEST= 0
INDE  4  20  48  FOBS=   19.6  SIGMA=   6.5  PHAS=  158.9  FOM= 0.78  TEST= 1
INDE  4  20  50  FOBS=  285.9  SIGMA=   1.0  PHAS=  -14.5  FOM= 0.97  TEST= 0
INDE  4  20  52  FOBS=  165.0  SIGMA=   1.4  PHAS=  -32.7  FOM= 0.94  TEST= 0
INDE  4  20  54  FOBS=   94.6  SIGMA=   2.3  PHAS=   23.6  FOM= 0.88  TEST= 0
INDE  4  20  56  FOBS=   21.0  SIGMA=   9.5  PHAS= -147.0  FOM= 0.37  TEST= 0
INDE  4  20  58  FOBS=   36.6  SIGMA=   5.9  PHAS= -119.3  FOM= 0.76  TEST= 0
INDE  4  20  60  FOBS=   88.3  SIGMA=   2.3  PHAS= -148.8  FOM= 0.92  TEST= 0
INDE  4  20  62  FOBS=  103.9  SIGMA=   2.3  PHAS=  134.1  FOM= 0.81  TEST= 0
INDE  4  20  64  FOBS=  123.7  SIGMA=   3.7  PHAS= -138.1  FOM= 0.91  TEST= 0
INDE  4  20  66  FOBS=    0.0  SIGMA=  29.6  PHAS=    0.0  FOM= 0.00  TEST= 0
INDE  4  20  68  FOBS=    0.0  SIGMA=  25.4  PHAS=    0.0  FOM= 0.00  TEST= 0
INDE  4  20  70  FOBS=    0.0  SIGMA=  25.4  PHAS=    0.0  FOM= 0.00  TEST= 0
INDE  4  20  72  FOBS=   32.2  SIGMA=  14.8  PHAS=  -28.6  FOM= 0.54  TEST= 0
INDE  4  20  74  FOBS=   47.7  SIGMA=   7.1  PHAS=  122.1  FOM= 0.45  TEST= 0
INDE  4  21   5  FOBS=  404.8  SIGMA=   0.5  PHAS=  155.0  FOM= 0.98  TEST= 0
INDE  4  21   7  FOBS=  197.1  SIGMA=   0.8  PHAS=   59.7  FOM= 0.94  TEST= 0
INDE  4  21   9  FOBS=   86.0  SIGMA=   1.0  PHAS=  -24.8  FOM= 0.92  TEST= 0
INDE  4  21  11  FOBS=  168.8  SIGMA=   1.0  PHAS=  -74.1  FOM= 0.96  TEST= 0
INDE  4  21  13  FOBS=  118.1  SIGMA=   1.3  PHAS= -178.6  FOM= 0.49  TEST= 1
INDE  4  21  15  FOBS=   76.3  SIGMA=   1.8  PHAS= -116.7  FOM= 0.99  TEST= 0
INDE  4  21  17  FOBS=  125.9  SIGMA=   1.2  PHAS= -123.6  FOM= 0.94  TEST= 0
INDE  4  21  19  FOBS=  133.4  SIGMA=   0.9  PHAS= -177.8  FOM= 0.95  TEST= 0
INDE  4  21  21  FOBS=  146.6  SIGMA=   0.8  PHAS=  -34.4  FOM= 0.98  TEST= 0
INDE  4  21  23  FOBS=  164.4  SIGMA=   0.7  PHAS=  -16.3  FOM= 0.96  TEST= 0
INDE  4  21  25  FOBS=  173.2  SIGMA=   0.7  PHAS=   45.0  FOM= 0.92  TEST= 0
INDE  4  21  27  FOBS=   79.5  SIGMA=   1.1  PHAS=  -43.2  FOM= 0.97  TEST= 0
INDE  4  21  29  FOBS=  309.2  SIGMA=   0.5  PHAS=  -87.8  FOM= 0.96  TEST= 1
INDE  4  21  31  FOBS=   83.7  SIGMA=   1.1  PHAS=  -98.3  FOM= 0.92  TEST= 0
INDE  4  21  33  FOBS=  162.0  SIGMA=   0.7  PHAS=    3.0  FOM= 0.99  TEST= 0
```

*FIG. 12A - 112*

| | | | | | | | | | | | | |
|---|---|---|---|---|---|---|---|---|---|---|---|---|
| INDE | 4 | 21 | 35 | FOBS= | 285.3 | SIGMA= | 0.6 | PHAS= | -151.0 | FOM= | 0.98 | TEST= 0 |
| INDE | 4 | 21 | 37 | FOBS= | 0.0 | SIGMA= | 17.9 | PHAS= | 0.0 | FOM= | 0.00 | TEST= 0 |
| INDE | 4 | 21 | 39 | FOBS= | 295.8 | SIGMA= | 0.7 | PHAS= | -117.9 | FOM= | 0.97 | TEST= 0 |
| INDE | 4 | 21 | 41 | FOBS= | 0.0 | SIGMA= | 16.3 | PHAS= | 0.0 | FOM= | 0.00 | TEST= 0 |
| INDE | 4 | 21 | 43 | FOBS= | 162.5 | SIGMA= | 0.9 | PHAS= | 26.8 | FOM= | 0.20 | TEST= 1 |
| INDE | 4 | 21 | 45 | FOBS= | 214.9 | SIGMA= | 0.7 | PHAS= | 74.9 | FOM= | 0.94 | TEST= 0 |
| INDE | 4 | 21 | 47 | FOBS= | 70.0 | SIGMA= | 1.8 | PHAS= | -101.4 | FOM= | 0.72 | TEST= 1 |
| INDE | 4 | 21 | 49 | FOBS= | 120.8 | SIGMA= | 1.1 | PHAS= | -69.9 | FOM= | 0.92 | TEST= 0 |
| INDE | 4 | 21 | 51 | FOBS= | 145.8 | SIGMA= | 1.5 | PHAS= | -170.6 | FOM= | 0.90 | TEST= 0 |
| INDE | 4 | 21 | 53 | FOBS= | 167.8 | SIGMA= | 1.5 | PHAS= | -91.9 | FOM= | 0.93 | TEST= 0 |
| INDE | 4 | 21 | 55 | FOBS= | 141.1 | SIGMA= | 1.5 | PHAS= | -168.3 | FOM= | 0.40 | TEST= 1 |
| INDE | 4 | 21 | 57 | FOBS= | 49.1 | SIGMA= | 4.2 | PHAS= | 179.2 | FOM= | 0.80 | TEST= 0 |
| INDE | 4 | 21 | 59 | FOBS= | 102.9 | SIGMA= | 2.0 | PHAS= | 177.9 | FOM= | 0.94 | TEST= 0 |
| INDE | 4 | 21 | 61 | FOBS= | 0.0 | SIGMA= | 19.6 | PHAS= | 0.0 | FOM= | 0.00 | TEST= 0 |
| INDE | 4 | 21 | 63 | FOBS= | 124.3 | SIGMA= | 2.6 | PHAS= | -177.5 | FOM= | 0.93 | TEST= 0 |
| INDE | 4 | 21 | 65 | FOBS= | 90.1 | SIGMA= | 5.0 | PHAS= | 142.5 | FOM= | 0.89 | TEST= 0 |
| INDE | 4 | 21 | 67 | FOBS= | 0.0 | SIGMA= | 29.4 | PHAS= | 0.0 | FOM= | 0.00 | TEST= 1 |
| INDE | 4 | 21 | 69 | FOBS= | 16.2 | SIGMA= | 20.0 | PHAS= | -103.2 | FOM= | 0.06 | TEST= 0 |
| INDE | 4 | 21 | 71 | FOBS= | 20.2 | SIGMA= | 16.2 | PHAS= | 58.3 | FOM= | 0.13 | TEST= 0 |
| INDE | 4 | 21 | 73 | FOBS= | 101.3 | SIGMA= | 3.4 | PHAS= | 125.8 | FOM= | 0.91 | TEST= 0 |
| INDE | 4 | 22 | 4 | FOBS= | 150.6 | SIGMA= | 0.6 | PHAS= | 130.3 | FOM= | 0.97 | TEST= 0 |
| INDE | 4 | 22 | 6 | FOBS= | 140.5 | SIGMA= | 0.7 | PHAS= | -114.3 | FOM= | 0.83 | TEST= 0 |
| INDE | 4 | 22 | 8 | FOBS= | 73.8 | SIGMA= | 1.2 | PHAS= | 21.6 | FOM= | 0.61 | TEST= 0 |
| INDE | 4 | 22 | 10 | FOBS= | 100.7 | SIGMA= | 0.9 | PHAS= | 58.6 | FOM= | 0.91 | TEST= 0 |
| INDE | 4 | 22 | 12 | FOBS= | 116.5 | SIGMA= | 1.3 | PHAS= | 24.2 | FOM= | 0.70 | TEST= 0 |
| INDE | 4 | 22 | 14 | FOBS= | 119.0 | SIGMA= | 1.3 | PHAS= | -24.2 | FOM= | 0.98 | TEST= 0 |
| INDE | 4 | 22 | 16 | FOBS= | 149.5 | SIGMA= | 1.1 | PHAS= | 175.4 | FOM= | 0.18 | TEST= 1 |
| INDE | 4 | 22 | 18 | FOBS= | 160.2 | SIGMA= | 1.1 | PHAS= | -170.6 | FOM= | 0.97 | TEST= 0 |
| INDE | 4 | 22 | 20 | FOBS= | 131.8 | SIGMA= | 1.0 | PHAS= | 134.4 | FOM= | 0.94 | TEST= 1 |
| INDE | 4 | 22 | 22 | FOBS= | 76.0 | SIGMA= | 1.4 | PHAS= | 158.8 | FOM= | 0.95 | TEST= 0 |
| INDE | 4 | 22 | 24 | FOBS= | 32.7 | SIGMA= | 3.2 | PHAS= | -146.8 | FOM= | 0.92 | TEST= 0 |
| INDE | 4 | 22 | 26 | FOBS= | 126.2 | SIGMA= | 1.0 | PHAS= | -42.3 | FOM= | 0.98 | TEST= 0 |
| INDE | 4 | 22 | 28 | FOBS= | 342.0 | SIGMA= | 0.5 | PHAS= | -172.9 | FOM= | 0.98 | TEST= 0 |
| INDE | 4 | 22 | 30 | FOBS= | 128.4 | SIGMA= | 0.8 | PHAS= | 156.5 | FOM= | 0.99 | TEST= 0 |
| INDE | 4 | 22 | 32 | FOBS= | 140.8 | SIGMA= | 0.8 | PHAS= | 20.9 | FOM= | 0.96 | TEST= 0 |
| INDE | 4 | 22 | 34 | FOBS= | 108.1 | SIGMA= | 1.1 | PHAS= | 173.3 | FOM= | 0.98 | TEST= 0 |
| INDE | 4 | 22 | 36 | FOBS= | 96.6 | SIGMA= | 1.3 | PHAS= | 123.2 | FOM= | 0.98 | TEST= 0 |
| INDE | 4 | 22 | 38 | FOBS= | 124.2 | SIGMA= | 1.4 | PHAS= | 143.4 | FOM= | 0.96 | TEST= 0 |
| INDE | 4 | 22 | 40 | FOBS= | 37.1 | SIGMA= | 4.7 | PHAS= | 96.7 | FOM= | 0.90 | TEST= 1 |
| INDE | 4 | 22 | 42 | FOBS= | 139.8 | SIGMA= | 1.1 | PHAS= | -24.6 | FOM= | 0.87 | TEST= 1 |
| INDE | 4 | 22 | 44 | FOBS= | 253.9 | SIGMA= | 0.7 | PHAS= | 13.4 | FOM= | 0.94 | TEST= 0 |
| INDE | 4 | 22 | 46 | FOBS= | 202.9 | SIGMA= | 0.7 | PHAS= | -16.3 | FOM= | 0.91 | TEST= 0 |
| INDE | 4 | 22 | 48 | FOBS= | 97.8 | SIGMA= | 1.3 | PHAS= | 153.6 | FOM= | 0.73 | TEST= 1 |
| INDE | 4 | 22 | 50 | FOBS= | 104.3 | SIGMA= | 1.2 | PHAS= | 27.5 | FOM= | 0.92 | TEST= 0 |
| INDE | 4 | 22 | 52 | FOBS= | 99.3 | SIGMA= | 2.2 | PHAS= | 29.4 | FOM= | 0.95 | TEST= 0 |
| INDE | 4 | 22 | 54 | FOBS= | 78.1 | SIGMA= | 2.7 | PHAS= | 133.1 | FOM= | 0.86 | TEST= 0 |
| INDE | 4 | 22 | 56 | FOBS= | 78.4 | SIGMA= | 2.6 | PHAS= | 85.9 | FOM= | 0.74 | TEST= 0 |
| INDE | 4 | 22 | 58 | FOBS= | 70.2 | SIGMA= | 2.9 | PHAS= | 71.1 | FOM= | 0.78 | TEST= 0 |
| INDE | 4 | 22 | 60 | FOBS= | 46.9 | SIGMA= | 4.2 | PHAS= | 84.6 | FOM= | 0.86 | TEST= 0 |
| INDE | 4 | 22 | 62 | FOBS= | 38.6 | SIGMA= | 6.1 | PHAS= | 69.4 | FOM= | 0.15 | TEST= 0 |
| INDE | 4 | 22 | 64 | FOBS= | 69.6 | SIGMA= | 6.5 | PHAS= | 78.9 | FOM= | 0.83 | TEST= 0 |
| INDE | 4 | 22 | 66 | FOBS= | 58.0 | SIGMA= | 7.8 | PHAS= | 14.4 | FOM= | 0.28 | TEST= 0 |
| INDE | 4 | 22 | 68 | FOBS= | 0.0 | SIGMA= | 25.6 | PHAS= | 0.0 | FOM= | 0.00 | TEST= 0 |
| INDE | 4 | 22 | 70 | FOBS= | 13.2 | SIGMA= | 24.8 | PHAS= | -78.0 | FOM= | 0.02 | TEST= 0 |
| INDE | 4 | 22 | 72 | FOBS= | 64.5 | SIGMA= | 5.3 | PHAS= | 81.9 | FOM= | 0.71 | TEST= 0 |
| INDE | 4 | 22 | 74 | FOBS= | 50.4 | SIGMA= | 6.9 | PHAS= | 126.8 | FOM= | 0.71 | TEST= 0 |
| INDE | 4 | 23 | 5 | FOBS= | 461.0 | SIGMA= | 0.5 | PHAS= | 138.1 | FOM= | 0.97 | TEST= 0 |
| INDE | 4 | 23 | 7 | FOBS= | 94.5 | SIGMA= | 1.1 | PHAS= | -155.1 | FOM= | 0.92 | TEST= 0 |
| INDE | 4 | 23 | 9 | FOBS= | 81.7 | SIGMA= | 1.1 | PHAS= | 71.5 | FOM= | 0.90 | TEST= 0 |
| INDE | 4 | 23 | 11 | FOBS= | 75.8 | SIGMA= | 1.3 | PHAS= | -12.3 | FOM= | 0.93 | TEST= 0 |
| INDE | 4 | 23 | 13 | FOBS= | 204.1 | SIGMA= | 1.0 | PHAS= | -86.2 | FOM= | 0.92 | TEST= 0 |
| INDE | 4 | 23 | 15 | FOBS= | 239.6 | SIGMA= | 0.9 | PHAS= | -119.4 | FOM= | 0.98 | TEST= 0 |
| INDE | 4 | 23 | 17 | FOBS= | 48.9 | SIGMA= | 3.0 | PHAS= | 83.8 | FOM= | 0.90 | TEST= 0 |
| INDE | 4 | 23 | 19 | FOBS= | 149.6 | SIGMA= | 1.2 | PHAS= | 151.6 | FOM= | 0.99 | TEST= 0 |
| INDE | 4 | 23 | 21 | FOBS= | 242.3 | SIGMA= | 0.7 | PHAS= | -50.6 | FOM= | 0.96 | TEST= 0 |
| INDE | 4 | 23 | 23 | FOBS= | 72.2 | SIGMA= | 1.5 | PHAS= | -47.4 | FOM= | 0.96 | TEST= 0 |
| INDE | 4 | 23 | 25 | FOBS= | 91.9 | SIGMA= | 1.3 | PHAS= | -81.4 | FOM= | 0.97 | TEST= 0 |
| INDE | 4 | 23 | 27 | FOBS= | 57.5 | SIGMA= | 2.1 | PHAS= | 5.6 | FOM= | 0.86 | TEST= 0 |
| INDE | 4 | 23 | 29 | FOBS= | 190.0 | SIGMA= | 0.8 | PHAS= | 97.9 | FOM= | 0.97 | TEST= 0 |
| INDE | 4 | 23 | 31 | FOBS= | 50.8 | SIGMA= | 2.0 | PHAS= | -123.1 | FOM= | 0.75 | TEST= 0 |

*FIG. 12A - 113*

```
INDE  4  23  33  FOBS=   120.1  SIGMA=   1.0  PHAS=  -102.6  FOM=  0.62  TEST=  0
INDE  4  23  35  FOBS=   235.9  SIGMA=   0.7  PHAS=   117.5  FOM=  0.91  TEST=  1
INDE  4  23  37  FOBS=    41.2  SIGMA=   3.3  PHAS=   -24.0  FOM=  0.37  TEST=  0
INDE  4  23  39  FOBS=    19.9  SIGMA=   8.3  PHAS=    38.0  FOM=  0.85  TEST=  0
INDE  4  23  41  FOBS=    97.9  SIGMA=   1.7  PHAS=  -109.2  FOM=  0.72  TEST=  0
INDE  4  23  43  FOBS=   190.4  SIGMA=   1.0  PHAS=  -113.1  FOM=  0.89  TEST=  0
INDE  4  23  45  FOBS=   188.4  SIGMA=   0.9  PHAS=   -76.3  FOM=  0.96  TEST=  0
INDE  4  23  47  FOBS=    89.3  SIGMA=   1.8  PHAS=   145.2  FOM=  0.85  TEST=  0
INDE  4  23  49  FOBS=     0.0  SIGMA=  16.6  PHAS=     0.0  FOM=  0.00  TEST=  0
INDE  4  23  51  FOBS=   119.3  SIGMA=   1.1  PHAS=   -15.3  FOM=  0.86  TEST=  0
INDE  4  23  53  FOBS=   193.2  SIGMA=   1.2  PHAS=   -30.4  FOM=  0.95  TEST=  0
INDE  4  23  55  FOBS=    84.3  SIGMA=   2.5  PHAS=    10.3  FOM=  0.78  TEST=  0
INDE  4  23  57  FOBS=     0.0  SIGMA=  20.9  PHAS=     0.0  FOM=  0.00  TEST=  0
INDE  4  23  59  FOBS=     9.0  SIGMA=  24.1  PHAS=   161.3  FOM=  0.30  TEST=  0
INDE  4  23  61  FOBS=    58.2  SIGMA=   3.7  PHAS=    50.0  FOM=  0.68  TEST=  0
INDE  4  23  63  FOBS=    30.5  SIGMA=  10.3  PHAS=  -113.9  FOM=  0.77  TEST=  0
INDE  4  23  65  FOBS=     0.0  SIGMA=  30.0  PHAS=     0.0  FOM=  0.00  TEST=  0
INDE  4  23  67  FOBS=    39.6  SIGMA=  11.4  PHAS=   -66.2  FOM=  0.30  TEST=  0
INDE  4  23  69  FOBS=     0.0  SIGMA=  25.9  PHAS=     0.0  FOM=  0.00  TEST=  0
INDE  4  23  71  FOBS=    14.0  SIGMA=  24.1  PHAS=    66.9  FOM=  0.20  TEST=  0
INDE  4  23  73  FOBS=    52.6  SIGMA=   6.6  PHAS=    22.6  FOM=  0.78  TEST=  0
INDE  4  24   4  FOBS=   269.0  SIGMA=   0.5  PHAS=   103.1  FOM=  0.94  TEST=  0
INDE  4  24   6  FOBS=   128.2  SIGMA=   0.6  PHAS=    78.4  FOM=  0.83  TEST=  0
INDE  4  24   8  FOBS=    27.9  SIGMA=   3.1  PHAS=    40.0  FOM=  0.95  TEST=  0
INDE  4  24  10  FOBS=    70.5  SIGMA=   1.3  PHAS=    90.1  FOM=  0.87  TEST=  0
INDE  4  24  12  FOBS=    38.9  SIGMA=   3.8  PHAS=    87.4  FOM=  0.94  TEST=  1
INDE  4  24  14  FOBS=   193.5  SIGMA=   1.0  PHAS=  -152.8  FOM=  0.99  TEST=  0
INDE  4  24  16  FOBS=   188.5  SIGMA=   1.0  PHAS=  -157.7  FOM=  0.98  TEST=  1
INDE  4  24  18  FOBS=   100.0  SIGMA=   1.6  PHAS=    65.2  FOM=  0.97  TEST=  0
INDE  4  24  20  FOBS=    86.1  SIGMA=   1.9  PHAS=  -164.7  FOM=  0.96  TEST=  0
INDE  4  24  22  FOBS=   202.7  SIGMA=   0.8  PHAS=   149.7  FOM=  0.99  TEST=  0
INDE  4  24  24  FOBS=   113.3  SIGMA=   1.1  PHAS=  -136.7  FOM=  0.96  TEST=  0
INDE  4  24  26  FOBS=   135.5  SIGMA=   1.0  PHAS=   -36.5  FOM=  0.92  TEST=  0
INDE  4  24  28  FOBS=    66.4  SIGMA=   1.9  PHAS=   116.7  FOM=  0.65  TEST=  0
INDE  4  24  30  FOBS=   169.6  SIGMA=   0.8  PHAS=  -130.7  FOM=  0.96  TEST=  0
INDE  4  24  32  FOBS=    81.1  SIGMA=   1.5  PHAS=   158.6  FOM=  0.96  TEST=  0
INDE  4  24  34  FOBS=    39.6  SIGMA=   3.0  PHAS=   129.9  FOM=  0.83  TEST=  0
INDE  4  24  36  FOBS=    91.8  SIGMA=   1.4  PHAS=   141.9  FOM=  0.94  TEST=  0
INDE  4  24  38  FOBS=   168.8  SIGMA=   0.9  PHAS=   -93.3  FOM=  0.90  TEST=  1
INDE  4  24  40  FOBS=   214.6  SIGMA=   0.9  PHAS=  -124.5  FOM=  0.95  TEST=  0
INDE  4  24  42  FOBS=   130.5  SIGMA=   1.2  PHAS=   160.4  FOM=  0.89  TEST=  0
INDE  4  24  44  FOBS=    84.2  SIGMA=   1.7  PHAS=  -169.1  FOM=  0.71  TEST=  0
INDE  4  24  46  FOBS=   134.2  SIGMA=   1.2  PHAS=    64.2  FOM=  0.84  TEST=  0
INDE  4  24  48  FOBS=   177.0  SIGMA=   0.9  PHAS=   -15.1  FOM=  0.96  TEST=  0
INDE  4  24  50  FOBS=    18.4  SIGMA=   7.2  PHAS=    93.2  FOM=  0.73  TEST=  0
INDE  4  24  52  FOBS=    65.8  SIGMA=   2.0  PHAS=   -70.0  FOM=  0.94  TEST=  0
INDE  4  24  54  FOBS=   186.7  SIGMA=   1.1  PHAS=  -119.7  FOM=  0.95  TEST=  0
INDE  4  24  56  FOBS=    46.1  SIGMA=   4.5  PHAS=  -161.1  FOM=  0.91  TEST=  0
INDE  4  24  58  FOBS=   119.7  SIGMA=   1.8  PHAS=    56.3  FOM=  0.92  TEST=  0
INDE  4  24  60  FOBS=   105.0  SIGMA=   2.4  PHAS=   -46.3  FOM=  0.83  TEST=  0
INDE  4  24  62  FOBS=   151.5  SIGMA=   2.3  PHAS=   -76.3  FOM=  0.96  TEST=  0
INDE  4  24  64  FOBS=     0.0  SIGMA=  25.0  PHAS=     0.0  FOM=  0.00  TEST=  0
INDE  4  24  66  FOBS=     0.0  SIGMA=  30.2  PHAS=     0.0  FOM=  0.00  TEST=  0
INDE  4  24  68  FOBS=    37.6  SIGMA=  12.2  PHAS=   -47.6  FOM=  0.11  TEST=  1
INDE  4  24  70  FOBS=    67.8  SIGMA=   5.1  PHAS=    24.9  FOM=  0.84  TEST=  0
INDE  4  24  72  FOBS=    16.2  SIGMA=  21.3  PHAS=   -21.9  FOM=  0.18  TEST=  0
INDE  4  25   5  FOBS=   119.6  SIGMA=   0.9  PHAS=    48.9  FOM=  0.99  TEST=  0
INDE  4  25   7  FOBS=    50.9  SIGMA=   1.9  PHAS=   -46.3  FOM=  0.88  TEST=  0
INDE  4  25   9  FOBS=    86.3  SIGMA=   1.1  PHAS=  -166.6  FOM=  0.97  TEST=  0
INDE  4  25  11  FOBS=    99.7  SIGMA=   1.1  PHAS=  -178.3  FOM=  0.92  TEST=  0
INDE  4  25  13  FOBS=   109.4  SIGMA=   1.6  PHAS=    89.0  FOM=  0.92  TEST=  0
INDE  4  25  15  FOBS=   178.1  SIGMA=   1.1  PHAS=    98.6  FOM=  0.98  TEST=  0
INDE  4  25  17  FOBS=   131.4  SIGMA=   1.3  PHAS=   -47.9  FOM=  0.95  TEST=  0
INDE  4  25  19  FOBS=   175.0  SIGMA=   1.1  PHAS=   149.2  FOM=  0.98  TEST=  0
INDE  4  25  21  FOBS=   325.2  SIGMA=   0.8  PHAS=    46.7  FOM=  0.98  TEST=  0
INDE  4  25  23  FOBS=    50.0  SIGMA=   2.4  PHAS=   140.3  FOM=  0.96  TEST=  0
INDE  4  25  25  FOBS=   156.3  SIGMA=   0.9  PHAS=  -170.5  FOM=  0.99  TEST=  0
INDE  4  25  27  FOBS=    14.9  SIGMA=   8.3  PHAS=  -179.9  FOM=  0.60  TEST=  0
INDE  4  25  29  FOBS=   250.8  SIGMA=   0.7  PHAS=    66.8  FOM=  0.92  TEST=  0
INDE  4  25  31  FOBS=   168.0  SIGMA=   0.9  PHAS=    92.8  FOM=  0.97  TEST=  0
```

*FIG. 12A - 114*

```
INDE  4  25  33 FOBS=  158.1 SIGMA=  0.9 PHAS= -163.7 FOM= 0.87 TEST= 0
INDE  4  25  35 FOBS=  111.2 SIGMA=  1.3 PHAS=  103.6 FOM= 0.97 TEST= 0
INDE  4  25  37 FOBS=  226.7 SIGMA=  0.7 PHAS=  160.2 FOM= 0.94 TEST= 0
INDE  4  25  39 FOBS=   74.7 SIGMA=  2.0 PHAS=  118.8 FOM= 0.92 TEST= 0
INDE  4  25  41 FOBS=  222.3 SIGMA=  0.8 PHAS=  143.3 FOM= 0.93 TEST= 0
INDE  4  25  43 FOBS=   45.6 SIGMA=  3.5 PHAS=  -84.0 FOM= 0.88 TEST= 0
INDE  4  25  45 FOBS=  224.5 SIGMA=  0.9 PHAS=   -9.5 FOM= 0.97 TEST= 0
INDE  4  25  47 FOBS=  151.9 SIGMA=  1.1 PHAS= -115.6 FOM= 0.94 TEST= 0
INDE  4  25  49 FOBS=  169.6 SIGMA=  0.9 PHAS=  140.1 FOM= 0.32 TEST= 1
INDE  4  25  51 FOBS=   84.2 SIGMA=  1.6 PHAS=  -46.8 FOM= 0.94 TEST= 0
INDE  4  25  53 FOBS=    0.0 SIGMA= 16.2 PHAS=    0.0 FOM= 0.00 TEST= 0
INDE  4  25  55 FOBS=  153.6 SIGMA=  1.2 PHAS=  115.5 FOM= 0.75 TEST= 1
INDE  4  25  57 FOBS=   60.8 SIGMA=  3.4 PHAS=  -77.9 FOM= 0.87 TEST= 0
INDE  4  25  59 FOBS=   39.6 SIGMA=  5.2 PHAS= -109.8 FOM= 0.66 TEST= 0
INDE  4  25  61 FOBS=   67.7 SIGMA=  4.1 PHAS= -166.8 FOM= 0.66 TEST= 0
INDE  4  25  63 FOBS=   79.7 SIGMA=  4.1 PHAS= -172.0 FOM= 0.88 TEST= 0
INDE  4  25  65 FOBS=   56.3 SIGMA=  8.3 PHAS= -157.8 FOM= 0.56 TEST= 0
INDE  4  25  67 FOBS=   49.5 SIGMA=  9.2 PHAS= -127.7 FOM= 0.87 TEST= 0
INDE  4  25  69 FOBS=   25.1 SIGMA= 13.8 PHAS=  145.1 FOM= 0.65 TEST= 0
INDE  4  25  71 FOBS=   38.0 SIGMA=  9.2 PHAS=   74.2 FOM= 0.52 TEST= 0
INDE  4  25  73 FOBS=   44.3 SIGMA=  8.1 PHAS=    3.9 FOM= 0.76 TEST= 0
INDE  4  26   4 FOBS=   59.3 SIGMA=  1.8 PHAS=  -82.2 FOM= 0.96 TEST= 0
INDE  4  26   6 FOBS=   57.3 SIGMA=  1.3 PHAS=   73.8 FOM= 0.50 TEST= 0
INDE  4  26   8 FOBS=  108.9 SIGMA=  0.9 PHAS=  -15.8 FOM= 0.97 TEST= 0
INDE  4  26  10 FOBS=   65.1 SIGMA=  1.5 PHAS=  155.6 FOM= 0.98 TEST= 0
INDE  4  26  12 FOBS=  161.1 SIGMA=  0.8 PHAS=   50.6 FOM= 0.99 TEST= 0
INDE  4  26  14 FOBS=  120.2 SIGMA=  1.5 PHAS=  -56.3 FOM= 0.93 TEST= 0
INDE  4  26  16 FOBS=   91.9 SIGMA=  1.8 PHAS= -171.6 FOM= 0.91 TEST= 0
INDE  4  26  18 FOBS=   59.4 SIGMA=  2.8 PHAS=  161.2 FOM= 0.96 TEST= 0
INDE  4  26  20 FOBS=  179.6 SIGMA=  1.1 PHAS= -148.3 FOM= 0.30 TEST= 1
INDE  4  26  22 FOBS=  173.6 SIGMA=  1.0 PHAS=  157.7 FOM= 0.96 TEST= 0
INDE  4  26  24 FOBS=   85.2 SIGMA=  1.5 PHAS=  103.6 FOM= 0.95 TEST= 0
INDE  4  26  26 FOBS=  136.4 SIGMA=  1.0 PHAS=  -55.8 FOM= 0.94 TEST= 0
INDE  4  26  28 FOBS=   45.4 SIGMA=  3.2 PHAS=   57.6 FOM= 0.87 TEST= 0
INDE  4  26  30 FOBS=   30.5 SIGMA=  4.6 PHAS= -146.2 FOM= 0.44 TEST= 0
INDE  4  26  32 FOBS=  233.9 SIGMA=  0.7 PHAS=   66.7 FOM= 0.89 TEST= 0
INDE  4  26  34 FOBS=   99.0 SIGMA=  1.5 PHAS=   55.6 FOM= 0.98 TEST= 0
INDE  4  26  36 FOBS=  113.2 SIGMA=  1.5 PHAS=  147.1 FOM= 0.93 TEST= 0
INDE  4  26  38 FOBS=   18.1 SIGMA=  9.0 PHAS=   16.5 FOM= 0.11 TEST= 0
INDE  4  26  40 FOBS=   85.8 SIGMA=  2.0 PHAS=  -42.8 FOM= 0.72 TEST= 0
INDE  4  26  42 FOBS=  283.9 SIGMA=  0.7 PHAS=   61.6 FOM= 0.97 TEST= 0
INDE  4  26  44 FOBS=  201.0 SIGMA=  0.9 PHAS=  -91.0 FOM= 0.93 TEST= 0
INDE  4  26  46 FOBS=  136.4 SIGMA=  1.1 PHAS= -102.6 FOM= 0.98 TEST= 0
INDE  4  26  48 FOBS=  120.1 SIGMA=  1.2 PHAS=   85.0 FOM= 0.79 TEST= 0
INDE  4  26  50 FOBS=   86.9 SIGMA=  1.6 PHAS= -132.7 FOM= 0.47 TEST= 0
INDE  4  26  52 FOBS=  100.8 SIGMA=  1.3 PHAS=  -55.3 FOM= 0.96 TEST= 0
INDE  4  26  54 FOBS=  109.1 SIGMA=  1.2 PHAS=  -22.2 FOM= 0.26 TEST= 1
INDE  4  26  56 FOBS=   44.9 SIGMA=  3.7 PHAS=   21.5 FOM= 0.54 TEST= 0
INDE  4  26  58 FOBS=   24.8 SIGMA=  8.3 PHAS=   65.4 FOM= 0.46 TEST= 0
INDE  4  26  60 FOBS=   58.6 SIGMA=  3.9 PHAS=  -30.1 FOM= 0.53 TEST= 0
INDE  4  26  62 FOBS=   66.3 SIGMA=  4.9 PHAS= -136.9 FOM= 0.68 TEST= 0
INDE  4  26  64 FOBS=   45.9 SIGMA=  7.0 PHAS=   74.2 FOM= 0.63 TEST= 0
INDE  4  26  66 FOBS=   28.4 SIGMA= 16.6 PHAS= -150.9 FOM= 0.08 TEST= 1
INDE  4  26  68 FOBS=   60.5 SIGMA=  7.7 PHAS=  105.8 FOM= 0.89 TEST= 0
INDE  4  26  70 FOBS=  117.7 SIGMA=  3.1 PHAS=   46.1 FOM= 0.94 TEST= 0
INDE  4  26  72 FOBS=   79.4 SIGMA=  4.6 PHAS=  -85.6 FOM= 0.91 TEST= 0
INDE  4  27   5 FOBS=   67.0 SIGMA=  1.5 PHAS=  149.3 FOM= 0.19 TEST= 0
INDE  4  27   7 FOBS=    0.0 SIGMA= 14.8 PHAS=    0.0 FOM= 0.00 TEST= 0
INDE  4  27   9 FOBS=  202.0 SIGMA=  0.8 PHAS= -139.0 FOM= 0.87 TEST= 0
INDE  4  27  11 FOBS=   82.5 SIGMA=  1.3 PHAS=  140.9 FOM= 0.99 TEST= 0
INDE  4  27  13 FOBS=   40.6 SIGMA=  2.6 PHAS=  -91.4 FOM= 0.78 TEST= 0
INDE  4  27  15 FOBS=  135.0 SIGMA=  1.4 PHAS=  176.5 FOM= 0.88 TEST= 0
INDE  4  27  17 FOBS=  159.9 SIGMA=  1.3 PHAS=   31.0 FOM= 0.81 TEST= 0
INDE  4  27  19 FOBS=  150.3 SIGMA=  1.3 PHAS= -180.0 FOM= 0.97 TEST= 1
INDE  4  27  21 FOBS=   70.4 SIGMA=  2.5 PHAS=    9.5 FOM= 0.92 TEST= 0
INDE  4  27  23 FOBS=   69.5 SIGMA=  2.1 PHAS= -110.0 FOM= 0.47 TEST= 0
INDE  4  27  25 FOBS=   80.3 SIGMA=  1.6 PHAS= -147.2 FOM= 0.96 TEST= 0
INDE  4  27  27 FOBS=  114.0 SIGMA=  1.3 PHAS=  108.5 FOM= 0.92 TEST= 0
INDE  4  27  29 FOBS=  202.4 SIGMA=  0.8 PHAS=   82.5 FOM= 0.64 TEST= 1
INDE  4  27  31 FOBS=  193.8 SIGMA=  1.1 PHAS=   57.7 FOM= 0.92 TEST= 0
```

*FIG. 12A - 115*

```
INDE  4  27  33  FOBS=   53.9  SIGMA=   2.8  PHAS=   -1.0  FOM= 0.92  TEST= 0
INDE  4  27  35  FOBS=  232.5  SIGMA=   0.9  PHAS= -150.6  FOM= 0.95  TEST= 0
INDE  4  27  37  FOBS=  278.9  SIGMA=   0.8  PHAS=  167.8  FOM= 0.97  TEST= 0
INDE  4  27  39  FOBS=   47.5  SIGMA=   3.6  PHAS=   -9.3  FOM= 0.38  TEST= 0
INDE  4  27  41  FOBS=  212.3  SIGMA=   0.8  PHAS=  -78.9  FOM= 0.94  TEST= 0
INDE  4  27  43  FOBS=  211.9  SIGMA=   0.7  PHAS= -133.8  FOM= 0.97  TEST= 0
INDE  4  27  45  FOBS=  278.9  SIGMA=   0.7  PHAS= -172.7  FOM= 0.98  TEST= 0
INDE  4  27  47  FOBS=   94.6  SIGMA=   1.5  PHAS=   72.7  FOM= 0.85  TEST= 0
INDE  4  27  49  FOBS=    0.0  SIGMA=  17.3  PHAS=    0.0  FOM= 0.00  TEST= 1
INDE  4  27  51  FOBS=  154.8  SIGMA=   0.9  PHAS= -134.8  FOM= 0.97  TEST= 0
INDE  4  27  53  FOBS=   97.6  SIGMA=   1.4  PHAS=  -84.4  FOM= 0.60  TEST= 1
INDE  4  27  55  FOBS=   73.1  SIGMA=   1.8  PHAS=  126.0  FOM= 0.15  TEST= 0
INDE  4  27  57  FOBS=   87.5  SIGMA=   1.9  PHAS=  -36.6  FOM= 0.89  TEST= 0
INDE  4  27  59  FOBS=   71.2  SIGMA=   3.0  PHAS=   12.0  FOM= 0.79  TEST= 0
INDE  4  27  61  FOBS=   64.1  SIGMA=   5.1  PHAS=  107.4  FOM= 0.60  TEST= 0
INDE  4  27  63  FOBS=   43.5  SIGMA=   7.4  PHAS=  102.2  FOM= 0.75  TEST= 0
INDE  4  27  65  FOBS=   33.8  SIGMA=  14.1  PHAS=  172.4  FOM= 0.66  TEST= 0
INDE  4  27  67  FOBS=   87.3  SIGMA=   5.6  PHAS=   83.7  FOM= 0.91  TEST= 0
INDE  4  27  69  FOBS=  128.7  SIGMA=   3.8  PHAS=  165.0  FOM= 0.93  TEST= 0
INDE  4  27  71  FOBS=    0.0  SIGMA=  33.1  PHAS=    0.0  FOM= 0.00  TEST= 0
INDE  4  28   4  FOBS=  180.6  SIGMA=   0.8  PHAS= -136.8  FOM= 0.95  TEST= 0
INDE  4  28   6  FOBS=   52.0  SIGMA=   1.5  PHAS=   76.9  FOM= 0.95  TEST= 0
INDE  4  28   8  FOBS=  101.6  SIGMA=   1.0  PHAS=   72.8  FOM= 0.95  TEST= 0
INDE  4  28  10  FOBS=   87.3  SIGMA=   1.2  PHAS= -151.4  FOM= 0.99  TEST= 0
INDE  4  28  12  FOBS=   69.0  SIGMA=   1.6  PHAS=   12.4  FOM= 0.93  TEST= 1
INDE  4  28  14  FOBS=   87.6  SIGMA=   2.0  PHAS=   52.2  FOM= 0.94  TEST= 0
INDE  4  28  16  FOBS=  126.7  SIGMA=   1.5  PHAS=  -42.8  FOM= 0.92  TEST= 0
INDE  4  28  18  FOBS=  264.8  SIGMA=   1.0  PHAS= -138.6  FOM= 0.94  TEST= 0
INDE  4  28  20  FOBS=  206.4  SIGMA=   1.1  PHAS=   18.4  FOM= 0.96  TEST= 0
INDE  4  28  22  FOBS=  119.1  SIGMA=   1.7  PHAS= -179.0  FOM= 0.89  TEST= 0
INDE  4  28  24  FOBS=  242.3  SIGMA=   0.8  PHAS= -151.5  FOM= 0.95  TEST= 0
INDE  4  28  26  FOBS=  187.5  SIGMA=   1.0  PHAS=  -43.7  FOM= 0.99  TEST= 0
INDE  4  28  28  FOBS=  111.0  SIGMA=   1.4  PHAS=   84.0  FOM= 0.90  TEST= 0
INDE  4  28  30  FOBS=   79.4  SIGMA=   2.0  PHAS= -154.1  FOM= 0.85  TEST= 0
INDE  4  28  32  FOBS=   93.9  SIGMA=   1.8  PHAS=  -55.3  FOM= 0.90  TEST= 0
INDE  4  28  34  FOBS=  176.2  SIGMA=   0.9  PHAS=  161.5  FOM= 0.94  TEST= 0
INDE  4  28  36  FOBS=  246.6  SIGMA=   0.8  PHAS=  131.2  FOM= 0.97  TEST= 0
INDE  4  28  38  FOBS=  231.7  SIGMA=   0.9  PHAS=   37.7  FOM= 0.97  TEST= 0
INDE  4  28  40  FOBS=  307.5  SIGMA=   0.7  PHAS=  178.3  FOM= 0.97  TEST= 0
INDE  4  28  42  FOBS=  363.8  SIGMA=   0.6  PHAS=   94.4  FOM= 0.99  TEST= 0
INDE  4  28  44  FOBS=  184.7  SIGMA=   0.8  PHAS=   97.9  FOM= 0.97  TEST= 0
INDE  4  28  46  FOBS=  105.4  SIGMA=   1.4  PHAS=   82.1  FOM= 0.90  TEST= 0
INDE  4  28  48  FOBS=  102.6  SIGMA=   1.4  PHAS=   71.4  FOM= 0.83  TEST= 0
INDE  4  28  50  FOBS=  105.1  SIGMA=   1.3  PHAS= -178.6  FOM= 0.95  TEST= 0
INDE  4  28  52  FOBS=  125.5  SIGMA=   1.1  PHAS=  147.6  FOM= 0.59  TEST= 0
INDE  4  28  54  FOBS=   37.1  SIGMA=   3.6  PHAS=   59.1  FOM= 0.51  TEST= 0
INDE  4  28  56  FOBS=   94.7  SIGMA=   1.6  PHAS=  177.1  FOM= 0.92  TEST= 0
INDE  4  28  58  FOBS=  105.9  SIGMA=   1.8  PHAS=  -92.1  FOM= 0.90  TEST= 0
INDE  4  28  60  FOBS=   95.9  SIGMA=   2.9  PHAS=  -60.3  FOM= 0.89  TEST= 0
INDE  4  28  62  FOBS=   39.9  SIGMA=   8.1  PHAS=  -51.4  FOM= 0.37  TEST= 0
INDE  4  28  64  FOBS=  108.3  SIGMA=   3.1  PHAS=   11.8  FOM= 0.94  TEST= 0
INDE  4  28  66  FOBS=   71.7  SIGMA=   6.9  PHAS=   -8.4  FOM= 0.91  TEST= 0
INDE  4  28  68  FOBS=  106.4  SIGMA=   4.7  PHAS=   25.6  FOM= 0.94  TEST= 0
INDE  4  28  70  FOBS=   61.1  SIGMA=   5.9  PHAS=  115.9  FOM= 0.82  TEST= 0
INDE  4  28  72  FOBS=   35.7  SIGMA=  15.5  PHAS=  -66.2  FOM= 0.71  TEST= 0
INDE  4  29   5  FOBS=  206.3  SIGMA=   0.8  PHAS= -162.4  FOM= 0.95  TEST= 0
INDE  4  29   7  FOBS=  130.6  SIGMA=   1.0  PHAS= -114.9  FOM= 0.98  TEST= 0
INDE  4  29   9  FOBS=  125.6  SIGMA=   0.9  PHAS= -132.9  FOM= 0.99  TEST= 0
INDE  4  29  11  FOBS=  210.9  SIGMA=   0.7  PHAS=  131.5  FOM= 0.97  TEST= 0
INDE  4  29  13  FOBS=  182.1  SIGMA=   0.8  PHAS=  -30.7  FOM= 0.97  TEST= 0
INDE  4  29  15  FOBS=  197.6  SIGMA=   1.2  PHAS=  -45.7  FOM= 0.86  TEST= 0
INDE  4  29  17  FOBS=  236.8  SIGMA=   1.1  PHAS=  157.5  FOM= 0.97  TEST= 0
INDE  4  29  19  FOBS=  183.8  SIGMA=   1.2  PHAS= -148.9  FOM= 0.96  TEST= 0
INDE  4  29  21  FOBS=  297.2  SIGMA=   1.0  PHAS= -126.1  FOM= 0.97  TEST= 0
INDE  4  29  23  FOBS=  184.7  SIGMA=   1.3  PHAS=   -6.0  FOM= 0.87  TEST= 0
INDE  4  29  25  FOBS=  347.0  SIGMA=   0.7  PHAS=  139.4  FOM= 0.92  TEST= 0
INDE  4  29  27  FOBS=  144.9  SIGMA=   1.1  PHAS=   77.6  FOM= 0.85  TEST= 1
INDE  4  29  29  FOBS=  306.0  SIGMA=   0.7  PHAS=  121.5  FOM= 0.98  TEST= 0
INDE  4  29  31  FOBS=   71.7  SIGMA=   2.4  PHAS= -137.0  FOM= 0.93  TEST= 0
INDE  4  29  33  FOBS=   49.9  SIGMA=   3.5  PHAS=   38.9  FOM= 0.84  TEST= 0
```

*FIG. 12A - 116*

| | | | | | | | | | | | |
|---|---|---|---|---|---|---|---|---|---|---|---|
| INDE | 4 | 29 | 35 | FOBS= | 272.4 | SIGMA= | 0.8 | PHAS= | 105.2 | FOM= | 0.97 | TEST= 0
| INDE | 4 | 29 | 37 | FOBS= | 21.9 | SIGMA= | 10.0 | PHAS= | -6.5 | FOM= | 0.15 | TEST= 0
| INDE | 4 | 29 | 39 | FOBS= | 314.6 | SIGMA= | 0.8 | PHAS= | -2.4 | FOM= | 0.98 | TEST= 0
| INDE | 4 | 29 | 41 | FOBS= | 452.5 | SIGMA= | 0.6 | PHAS= | 38.3 | FOM= | 0.98 | TEST= 0
| INDE | 4 | 29 | 43 | FOBS= | 0.0 | SIGMA= | 18.4 | PHAS= | 0.0 | FOM= | 0.00 | TEST= 0
| INDE | 4 | 29 | 45 | FOBS= | 53.4 | SIGMA= | 2.5 | PHAS= | 137.2 | FOM= | 0.67 | TEST= 0
| INDE | 4 | 29 | 47 | FOBS= | 199.8 | SIGMA= | 0.8 | PHAS= | 47.0 | FOM= | 0.92 | TEST= 0
| INDE | 4 | 29 | 49 | FOBS= | 106.4 | SIGMA= | 1.4 | PHAS= | 122.2 | FOM= | 0.92 | TEST= 0
| INDE | 4 | 29 | 51 | FOBS= | 133.9 | SIGMA= | 1.1 | PHAS= | 125.3 | FOM= | 0.80 | TEST= 1
| INDE | 4 | 29 | 53 | FOBS= | 60.3 | SIGMA= | 2.2 | PHAS= | -19.2 | FOM= | 0.88 | TEST= 0
| INDE | 4 | 29 | 55 | FOBS= | 34.0 | SIGMA= | 4.5 | PHAS= | 62.7 | FOM= | 0.57 | TEST= 0
| INDE | 4 | 29 | 57 | FOBS= | 102.9 | SIGMA= | 1.7 | PHAS= | 160.5 | FOM= | 0.88 | TEST= 0
| INDE | 4 | 29 | 59 | FOBS= | 42.6 | SIGMA= | 4.5 | PHAS= | 99.0 | FOM= | 0.65 | TEST= 0
| INDE | 4 | 29 | 61 | FOBS= | 28.4 | SIGMA= | 8.5 | PHAS= | 129.1 | FOM= | 0.62 | TEST= 0
| INDE | 4 | 29 | 63 | FOBS= | 115.4 | SIGMA= | 3.0 | PHAS= | -76.3 | FOM= | 0.50 | TEST= 1
| INDE | 4 | 29 | 65 | FOBS= | 74.3 | SIGMA= | 6.7 | PHAS= | -80.4 | FOM= | 0.77 | TEST= 0
| INDE | 4 | 29 | 67 | FOBS= | 20.5 | SIGMA= | 24.2 | PHAS= | -137.6 | FOM= | 0.56 | TEST= 0
| INDE | 4 | 29 | 69 | FOBS= | 0.0 | SIGMA= | 31.3 | PHAS= | 0.0 | FOM= | 0.00 | TEST= 0
| INDE | 4 | 29 | 71 | FOBS= | 42.2 | SIGMA= | 8.8 | PHAS= | 24.7 | FOM= | 0.61 | TEST= 0
| INDE | 4 | 30 | 4 | FOBS= | 92.3 | SIGMA= | 1.4 | PHAS= | -61.1 | FOM= | 0.58 | TEST= 0
| INDE | 4 | 30 | 6 | FOBS= | 137.9 | SIGMA= | 0.6 | PHAS= | 129.4 | FOM= | 0.95 | TEST= 0
| INDE | 4 | 30 | 8 | FOBS= | 307.4 | SIGMA= | 0.6 | PHAS= | 149.0 | FOM= | 0.97 | TEST= 0
| INDE | 4 | 30 | 10 | FOBS= | 153.4 | SIGMA= | 0.8 | PHAS= | -115.8 | FOM= | 0.73 | TEST= 0
| INDE | 4 | 30 | 12 | FOBS= | 99.0 | SIGMA= | 1.2 | PHAS= | -69.3 | FOM= | 0.73 | TEST= 1
| INDE | 4 | 30 | 14 | FOBS= | 230.5 | SIGMA= | 1.1 | PHAS= | -132.5 | FOM= | 0.97 | TEST= 0
| INDE | 4 | 30 | 16 | FOBS= | 238.1 | SIGMA= | 1.1 | PHAS= | 52.0 | FOM= | 0.99 | TEST= 0
| INDE | 4 | 30 | 18 | FOBS= | 152.6 | SIGMA= | 1.4 | PHAS= | 116.8 | FOM= | 0.96 | TEST= 0
| INDE | 4 | 30 | 20 | FOBS= | 412.2 | SIGMA= | 0.9 | PHAS= | 108.7 | FOM= | 0.98 | TEST= 0
| INDE | 4 | 30 | 22 | FOBS= | 208.5 | SIGMA= | 1.2 | PHAS= | -129.4 | FOM= | 0.82 | TEST= 0
| INDE | 4 | 30 | 24 | FOBS= | 116.7 | SIGMA= | 1.9 | PHAS= | -108.1 | FOM= | 0.96 | TEST= 0
| INDE | 4 | 30 | 26 | FOBS= | 382.1 | SIGMA= | 1.0 | PHAS= | 39.4 | FOM= | 0.95 | TEST= 0
| INDE | 4 | 30 | 28 | FOBS= | 251.9 | SIGMA= | 0.9 | PHAS= | 58.2 | FOM= | 0.96 | TEST= 0
| INDE | 4 | 30 | 30 | FOBS= | 208.2 | SIGMA= | 0.9 | PHAS= | 72.2 | FOM= | 0.94 | TEST= 0
| INDE | 4 | 30 | 32 | FOBS= | 46.1 | SIGMA= | 4.2 | PHAS= | 125.2 | FOM= | 0.88 | TEST= 0
| INDE | 4 | 30 | 34 | FOBS= | 115.8 | SIGMA= | 1.7 | PHAS= | 96.1 | FOM= | 0.85 | TEST= 0
| INDE | 4 | 30 | 36 | FOBS= | 327.3 | SIGMA= | 0.7 | PHAS= | 134.4 | FOM= | 0.96 | TEST= 0
| INDE | 4 | 30 | 38 | FOBS= | 277.7 | SIGMA= | 0.8 | PHAS= | -58.8 | FOM= | 0.97 | TEST= 0
| INDE | 4 | 30 | 40 | FOBS= | 65.2 | SIGMA= | 3.0 | PHAS= | -163.6 | FOM= | 0.88 | TEST= 0
| INDE | 4 | 30 | 42 | FOBS= | 71.6 | SIGMA= | 2.6 | PHAS= | -23.1 | FOM= | 0.87 | TEST= 0
| INDE | 4 | 30 | 44 | FOBS= | 95.4 | SIGMA= | 1.6 | PHAS= | 75.4 | FOM= | 0.57 | TEST= 0
| INDE | 4 | 30 | 46 | FOBS= | 111.3 | SIGMA= | 1.3 | PHAS= | 48.5 | FOM= | 0.88 | TEST= 0
| INDE | 4 | 30 | 48 | FOBS= | 54.3 | SIGMA= | 2.6 | PHAS= | 54.6 | FOM= | 0.36 | TEST= 0
| INDE | 4 | 30 | 50 | FOBS= | 129.2 | SIGMA= | 1.1 | PHAS= | 13.8 | FOM= | 0.74 | TEST= 1
| INDE | 4 | 30 | 52 | FOBS= | 62.5 | SIGMA= | 2.2 | PHAS= | -83.1 | FOM= | 0.77 | TEST= 0
| INDE | 4 | 30 | 54 | FOBS= | 83.3 | SIGMA= | 1.6 | PHAS= | -26.8 | FOM= | 0.92 | TEST= 0
| INDE | 4 | 30 | 56 | FOBS= | 89.0 | SIGMA= | 1.7 | PHAS= | 103.2 | FOM= | 0.91 | TEST= 0
| INDE | 4 | 30 | 58 | FOBS= | 107.1 | SIGMA= | 1.9 | PHAS= | 20.2 | FOM= | 0.85 | TEST= 0
| INDE | 4 | 30 | 60 | FOBS= | 93.9 | SIGMA= | 2.2 | PHAS= | -31.0 | FOM= | 0.89 | TEST= 0
| INDE | 4 | 30 | 62 | FOBS= | 68.9 | SIGMA= | 3.3 | PHAS= | 121.2 | FOM= | 0.75 | TEST= 0
| INDE | 4 | 30 | 64 | FOBS= | 84.2 | SIGMA= | 4.1 | PHAS= | 143.5 | FOM= | 0.59 | TEST= 0
| INDE | 4 | 30 | 66 | FOBS= | 87.4 | SIGMA= | 5.8 | PHAS= | 120.4 | FOM= | 0.88 | TEST= 0
| INDE | 4 | 30 | 68 | FOBS= | 21.7 | SIGMA= | 22.7 | PHAS= | 58.8 | FOM= | 0.26 | TEST= 0
| INDE | 4 | 30 | 70 | FOBS= | 80.3 | SIGMA= | 4.7 | PHAS= | -135.3 | FOM= | 0.88 | TEST= 0
| INDE | 4 | 31 | 5 | FOBS= | 117.6 | SIGMA= | 1.2 | PHAS= | 170.5 | FOM= | 0.99 | TEST= 0
| INDE | 4 | 31 | 7 | FOBS= | 219.7 | SIGMA= | 0.5 | PHAS= | 109.5 | FOM= | 0.97 | TEST= 0
| INDE | 4 | 31 | 9 | FOBS= | 274.0 | SIGMA= | 0.7 | PHAS= | 99.6 | FOM= | 0.98 | TEST= 0
| INDE | 4 | 31 | 11 | FOBS= | 226.8 | SIGMA= | 0.8 | PHAS= | 138.0 | FOM= | 0.92 | TEST= 0
| INDE | 4 | 31 | 13 | FOBS= | 124.8 | SIGMA= | 1.1 | PHAS= | 178.1 | FOM= | 0.96 | TEST= 0
| INDE | 4 | 31 | 15 | FOBS= | 125.1 | SIGMA= | 1.1 | PHAS= | -59.9 | FOM= | 0.99 | TEST= 0
| INDE | 4 | 31 | 17 | FOBS= | 70.1 | SIGMA= | 2.8 | PHAS= | -30.9 | FOM= | 0.81 | TEST= 0
| INDE | 4 | 31 | 19 | FOBS= | 404.0 | SIGMA= | 0.9 | PHAS= | -57.2 | FOM= | 0.99 | TEST= 0
| INDE | 4 | 31 | 21 | FOBS= | 167.9 | SIGMA= | 1.4 | PHAS= | -27.6 | FOM= | 0.96 | TEST= 0
| INDE | 4 | 31 | 23 | FOBS= | 148.2 | SIGMA= | 1.6 | PHAS= | 92.0 | FOM= | 0.99 | TEST= 0
| INDE | 4 | 31 | 25 | FOBS= | 128.7 | SIGMA= | 1.9 | PHAS= | 111.0 | FOM= | 0.95 | TEST= 0
| INDE | 4 | 31 | 27 | FOBS= | 246.3 | SIGMA= | 1.0 | PHAS= | 55.1 | FOM= | 0.97 | TEST= 0
| INDE | 4 | 31 | 29 | FOBS= | 76.2 | SIGMA= | 2.3 | PHAS= | 93.0 | FOM= | 0.82 | TEST= 0
| INDE | 4 | 31 | 31 | FOBS= | 161.7 | SIGMA= | 1.2 | PHAS= | -55.9 | FOM= | 0.87 | TEST= 0
| INDE | 4 | 31 | 33 | FOBS= | 25.9 | SIGMA= | 8.6 | PHAS= | 23.1 | FOM= | 0.14 | TEST= 0
| INDE | 4 | 31 | 35 | FOBS= | 284.4 | SIGMA= | 1.0 | PHAS= | 103.2 | FOM= | 0.95 | TEST= 0
| INDE | 4 | 31 | 37 | FOBS= | 78.2 | SIGMA= | 2.6 | PHAS= | -11.3 | FOM= | 0.80 | TEST= 0

*FIG. 12A - 117*

| | | | | | | | | | | | | |
|---|---|---|---|---|---|---|---|---|---|---|---|---|
| INDE | 4 | 31 | 39 | FOBS= | 149.0 | SIGMA= | 1.4 | PHAS= | -135.3 | FOM= | 0.77 | TEST= 0 |
| INDE | 4 | 31 | 41 | FOBS= | 146.1 | SIGMA= | 1.3 | PHAS= | 29.2 | FOM= | 0.97 | TEST= 0 |
| INDE | 4 | 31 | 43 | FOBS= | 155.7 | SIGMA= | 1.2 | PHAS= | 161.5 | FOM= | 0.90 | TEST= 0 |
| INDE | 4 | 31 | 45 | FOBS= | 153.2 | SIGMA= | 1.0 | PHAS= | -81.7 | FOM= | 0.44 | TEST= 1 |
| INDE | 4 | 31 | 47 | FOBS= | 136.1 | SIGMA= | 1.0 | PHAS= | -47.7 | FOM= | 0.26 | TEST= 0 |
| INDE | 4 | 31 | 49 | FOBS= | 103.8 | SIGMA= | 1.5 | PHAS= | -70.4 | FOM= | 0.79 | TEST= 0 |
| INDE | 4 | 31 | 51 | FOBS= | 101.6 | SIGMA= | 1.4 | PHAS= | 130.3 | FOM= | 0.89 | TEST= 0 |
| INDE | 4 | 31 | 53 | FOBS= | 91.4 | SIGMA= | 1.5 | PHAS= | 171.1 | FOM= | 0.82 | TEST= 0 |
| INDE | 4 | 31 | 55 | FOBS= | 0.0 | SIGMA= | 17.4 | PHAS= | 0.0 | FOM= | 0.00 | TEST= 1 |
| INDE | 4 | 31 | 57 | FOBS= | 92.5 | SIGMA= | 1.8 | PHAS= | -64.2 | FOM= | 0.87 | TEST= 0 |
| INDE | 4 | 31 | 59 | FOBS= | 43.6 | SIGMA= | 4.7 | PHAS= | -124.3 | FOM= | 0.84 | TEST= 0 |
| INDE | 4 | 31 | 61 | FOBS= | 74.3 | SIGMA= | 2.8 | PHAS= | 110.4 | FOM= | 0.89 | TEST= 0 |
| INDE | 4 | 31 | 63 | FOBS= | 39.2 | SIGMA= | 5.7 | PHAS= | -75.9 | FOM= | 0.58 | TEST= 0 |
| INDE | 4 | 31 | 65 | FOBS= | 145.9 | SIGMA= | 3.6 | PHAS= | 59.2 | FOM= | 0.97 | TEST= 0 |
| INDE | 4 | 31 | 67 | FOBS= | 22.5 | SIGMA= | 22.0 | PHAS= | -69.6 | FOM= | 0.16 | TEST= 0 |
| INDE | 4 | 31 | 69 | FOBS= | 0.0 | SIGMA= | 31.6 | PHAS= | 0.0 | FOM= | 0.00 | TEST= 0 |
| INDE | 4 | 31 | 71 | FOBS= | 24.0 | SIGMA= | 15.8 | PHAS= | 89.1 | FOM= | 0.48 | TEST= 0 |
| INDE | 4 | 32 | 4 | FOBS= | 169.8 | SIGMA= | 0.9 | PHAS= | 45.8 | FOM= | 0.94 | TEST= 0 |
| INDE | 4 | 32 | 6 | FOBS= | 147.5 | SIGMA= | 0.7 | PHAS= | -52.7 | FOM= | 0.88 | TEST= 1 |
| INDE | 4 | 32 | 8 | FOBS= | 133.6 | SIGMA= | 1.2 | PHAS= | -6.6 | FOM= | 0.98 | TEST= 1 |
| INDE | 4 | 32 | 10 | FOBS= | 168.6 | SIGMA= | 0.8 | PHAS= | 23.9 | FOM= | 0.88 | TEST= 0 |
| INDE | 4 | 32 | 12 | FOBS= | 118.0 | SIGMA= | 1.1 | PHAS= | 98.8 | FOM= | 0.95 | TEST= 0 |
| INDE | 4 | 32 | 14 | FOBS= | 87.4 | SIGMA= | 1.5 | PHAS= | -134.4 | FOM= | 0.99 | TEST= 0 |
| INDE | 4 | 32 | 16 | FOBS= | 55.0 | SIGMA= | 3.7 | PHAS= | 154.2 | FOM= | 0.93 | TEST= 0 |
| INDE | 4 | 32 | 18 | FOBS= | 236.7 | SIGMA= | 1.2 | PHAS= | -125.4 | FOM= | 0.96 | TEST= 0 |
| INDE | 4 | 32 | 20 | FOBS= | 168.6 | SIGMA= | 1.5 | PHAS= | 167.6 | FOM= | 0.75 | TEST= 1 |
| INDE | 4 | 32 | 22 | FOBS= | 113.4 | SIGMA= | 2.1 | PHAS= | -169.5 | FOM= | 0.26 | TEST= 1 |
| INDE | 4 | 32 | 24 | FOBS= | 345.4 | SIGMA= | 1.0 | PHAS= | -68.7 | FOM= | 0.99 | TEST= 0 |
| INDE | 4 | 32 | 26 | FOBS= | 283.9 | SIGMA= | 1.1 | PHAS= | 80.8 | FOM= | 0.97 | TEST= 0 |
| INDE | 4 | 32 | 28 | FOBS= | 155.0 | SIGMA= | 1.2 | PHAS= | -14.9 | FOM= | 0.96 | TEST= 1 |
| INDE | 4 | 32 | 30 | FOBS= | 108.6 | SIGMA= | 1.8 | PHAS= | -127.6 | FOM= | 0.93 | TEST= 0 |
| INDE | 4 | 32 | 32 | FOBS= | 104.8 | SIGMA= | 1.9 | PHAS= | 176.3 | FOM= | 0.30 | TEST= 1 |
| INDE | 4 | 32 | 34 | FOBS= | 120.2 | SIGMA= | 2.7 | PHAS= | 31.4 | FOM= | 0.93 | TEST= 0 |
| INDE | 4 | 32 | 36 | FOBS= | 268.9 | SIGMA= | 0.9 | PHAS= | -166.0 | FOM= | 0.94 | TEST= 0 |
| INDE | 4 | 32 | 38 | FOBS= | 185.3 | SIGMA= | 1.2 | PHAS= | 20.5 | FOM= | 0.93 | TEST= 0 |
| INDE | 4 | 32 | 40 | FOBS= | 173.9 | SIGMA= | 1.2 | PHAS= | 79.9 | FOM= | 0.93 | TEST= 0 |
| INDE | 4 | 32 | 42 | FOBS= | 0.0 | SIGMA= | 19.4 | PHAS= | 0.0 | FOM= | 0.00 | TEST= 0 |
| INDE | 4 | 32 | 44 | FOBS= | 80.7 | SIGMA= | 1.9 | PHAS= | 112.6 | FOM= | 0.83 | TEST= 0 |
| INDE | 4 | 32 | 46 | FOBS= | 32.0 | SIGMA= | 4.8 | PHAS= | 110.2 | FOM= | 0.37 | TEST= 0 |
| INDE | 4 | 32 | 48 | FOBS= | 32.6 | SIGMA= | 4.6 | PHAS= | 124.7 | FOM= | 0.70 | TEST= 0 |
| INDE | 4 | 32 | 50 | FOBS= | 114.2 | SIGMA= | 1.4 | PHAS= | 70.4 | FOM= | 0.46 | TEST= 1 |
| INDE | 4 | 32 | 52 | FOBS= | 32.2 | SIGMA= | 4.8 | PHAS= | 75.0 | FOM= | 0.52 | TEST= 0 |
| INDE | 4 | 32 | 54 | FOBS= | 51.1 | SIGMA= | 2.9 | PHAS= | 19.2 | FOM= | 0.86 | TEST= 0 |
| INDE | 4 | 32 | 56 | FOBS= | 0.0 | SIGMA= | 17.8 | PHAS= | 0.0 | FOM= | 0.00 | TEST= 0 |
| INDE | 4 | 32 | 58 | FOBS= | 91.7 | SIGMA= | 2.0 | PHAS= | 133.2 | FOM= | 0.93 | TEST= 0 |
| INDE | 4 | 32 | 60 | FOBS= | 78.5 | SIGMA= | 2.7 | PHAS= | -8.2 | FOM= | 0.74 | TEST= 0 |
| INDE | 4 | 32 | 62 | FOBS= | 42.7 | SIGMA= | 4.8 | PHAS= | 14.8 | FOM= | 0.87 | TEST= 0 |
| INDE | 4 | 32 | 64 | FOBS= | 102.2 | SIGMA= | 2.1 | PHAS= | 25.2 | FOM= | 0.93 | TEST= 0 |
| INDE | 4 | 32 | 66 | FOBS= | 0.0 | SIGMA= | 31.9 | PHAS= | 0.0 | FOM= | 0.00 | TEST= 0 |
| INDE | 4 | 32 | 68 | FOBS= | 0.0 | SIGMA= | 32.0 | PHAS= | 0.0 | FOM= | 0.00 | TEST= 0 |
| INDE | 4 | 32 | 70 | FOBS= | 0.0 | SIGMA= | 31.9 | PHAS= | 0.0 | FOM= | 0.00 | TEST= 1 |
| INDE | 4 | 33 | 5 | FOBS= | 50.0 | SIGMA= | 2.7 | PHAS= | 97.7 | FOM= | 0.89 | TEST= 0 |
| INDE | 4 | 33 | 7 | FOBS= | 233.9 | SIGMA= | 0.6 | PHAS= | 165.0 | FOM= | 0.99 | TEST= 0 |
| INDE | 4 | 33 | 9 | FOBS= | 30.7 | SIGMA= | 4.1 | PHAS= | -49.4 | FOM= | 0.75 | TEST= 0 |
| INDE | 4 | 33 | 11 | FOBS= | 169.2 | SIGMA= | 0.8 | PHAS= | 39.5 | FOM= | 0.91 | TEST= 0 |
| INDE | 4 | 33 | 13 | FOBS= | 108.3 | SIGMA= | 1.2 | PHAS= | 115.9 | FOM= | 0.97 | TEST= 0 |
| INDE | 4 | 33 | 15 | FOBS= | 266.9 | SIGMA= | 0.8 | PHAS= | 86.3 | FOM= | 0.95 | TEST= 0 |
| INDE | 4 | 33 | 17 | FOBS= | 210.6 | SIGMA= | 1.3 | PHAS= | 116.1 | FOM= | 0.96 | TEST= 0 |
| INDE | 4 | 33 | 19 | FOBS= | 248.9 | SIGMA= | 1.2 | PHAS= | -32.8 | FOM= | 0.97 | TEST= 0 |
| INDE | 4 | 33 | 21 | FOBS= | 160.2 | SIGMA= | 1.6 | PHAS= | 51.4 | FOM= | 0.96 | TEST= 0 |
| INDE | 4 | 33 | 23 | FOBS= | 116.1 | SIGMA= | 2.1 | PHAS= | 162.0 | FOM= | 0.85 | TEST= 1 |
| INDE | 4 | 33 | 25 | FOBS= | 68.2 | SIGMA= | 3.6 | PHAS= | -50.3 | FOM= | 0.83 | TEST= 0 |
| INDE | 4 | 33 | 27 | FOBS= | 221.6 | SIGMA= | 1.1 | PHAS= | 22.6 | FOM= | 0.93 | TEST= 0 |
| INDE | 4 | 33 | 29 | FOBS= | 60.9 | SIGMA= | 3.0 | PHAS= | -173.9 | FOM= | 0.78 | TEST= 0 |
| INDE | 4 | 33 | 31 | FOBS= | 98.1 | SIGMA= | 2.1 | PHAS= | -128.7 | FOM= | 0.78 | TEST= 0 |
| INDE | 4 | 33 | 33 | FOBS= | 39.7 | SIGMA= | 5.4 | PHAS= | -47.4 | FOM= | 0.89 | TEST= 0 |
| INDE | 4 | 33 | 35 | FOBS= | 196.1 | SIGMA= | 1.3 | PHAS= | 86.2 | FOM= | 0.94 | TEST= 0 |
| INDE | 4 | 33 | 37 | FOBS= | 182.4 | SIGMA= | 1.2 | PHAS= | 88.1 | FOM= | 0.94 | TEST= 0 |
| INDE | 4 | 33 | 39 | FOBS= | 57.9 | SIGMA= | 3.4 | PHAS= | -35.2 | FOM= | 0.69 | TEST= 0 |
| INDE | 4 | 33 | 41 | FOBS= | 117.2 | SIGMA= | 1.6 | PHAS= | -39.4 | FOM= | 0.86 | TEST= 0 |

*FIG. 12A - 118*

| | | | | | | | | | | | | |
|---|---|---|---|---|---|---|---|---|---|---|---|---|
| INDE | 4 | 33 | 43 | FOBS= | 113.2 | SIGMA= | 1.6 | PHAS= | 133.0 | FOM= | 0.66 | TEST= 0 |
| INDE | 4 | 33 | 45 | FOBS= | 118.0 | SIGMA= | 1.3 | PHAS= | 14.9 | FOM= | 0.77 | TEST= 0 |
| INDE | 4 | 33 | 47 | FOBS= | 94.3 | SIGMA= | 1.6 | PHAS= | 6.9 | FOM= | 0.90 | TEST= 0 |
| INDE | 4 | 33 | 49 | FOBS= | 78.2 | SIGMA= | 1.9 | PHAS= | -80.1 | FOM= | 0.89 | TEST= 0 |
| INDE | 4 | 33 | 51 | FOBS= | 21.6 | SIGMA= | 6.9 | PHAS= | 12.0 | FOM= | 0.34 | TEST= 0 |
| INDE | 4 | 33 | 53 | FOBS= | 69.2 | SIGMA= | 2.1 | PHAS= | -142.4 | FOM= | 0.86 | TEST= 0 |
| INDE | 4 | 33 | 55 | FOBS= | 38.3 | SIGMA= | 3.8 | PHAS= | -96.1 | FOM= | 0.33 | TEST= 0 |
| INDE | 4 | 33 | 57 | FOBS= | 82.5 | SIGMA= | 2.1 | PHAS= | 1.9 | FOM= | 0.87 | TEST= 1 |
| INDE | 4 | 33 | 59 | FOBS= | 50.2 | SIGMA= | 3.5 | PHAS= | -8.8 | FOM= | 0.49 | TEST= 0 |
| INDE | 4 | 33 | 61 | FOBS= | 48.9 | SIGMA= | 4.2 | PHAS= | -85.2 | FOM= | 0.83 | TEST= 0 |
| INDE | 4 | 33 | 63 | FOBS= | 96.1 | SIGMA= | 2.2 | PHAS= | -68.7 | FOM= | 0.96 | TEST= 0 |
| INDE | 4 | 33 | 65 | FOBS= | 29.8 | SIGMA= | 7.8 | PHAS= | 87.8 | FOM= | 0.55 | TEST= 0 |
| INDE | 4 | 33 | 67 | FOBS= | 0.0 | SIGMA= | 27.0 | PHAS= | 0.0 | FOM= | 0.00 | TEST= 0 |
| INDE | 4 | 33 | 69 | FOBS= | 26.9 | SIGMA= | 19.1 | PHAS= | 166.0 | FOM= | 0.36 | TEST= 0 |
| INDE | 4 | 34 | 4 | FOBS= | 2.0 | SIGMA= | 66.5 | PHAS= | -119.6 | FOM= | 0.05 | TEST= 0 |
| INDE | 4 | 34 | 6 | FOBS= | 235.0 | SIGMA= | 0.8 | PHAS= | 69.4 | FOM= | 0.93 | TEST= 0 |
| INDE | 4 | 34 | 8 | FOBS= | 75.4 | SIGMA= | 1.2 | PHAS= | 152.5 | FOM= | 0.28 | TEST= 0 |
| INDE | 4 | 34 | 10 | FOBS= | 69.0 | SIGMA= | 2.0 | PHAS= | -78.2 | FOM= | 0.98 | TEST= 0 |
| INDE | 4 | 34 | 12 | FOBS= | 191.5 | SIGMA= | 0.8 | PHAS= | 36.9 | FOM= | 0.95 | TEST= 0 |
| INDE | 4 | 34 | 14 | FOBS= | 386.8 | SIGMA= | 0.7 | PHAS= | 9.3 | FOM= | 0.98 | TEST= 0 |
| INDE | 4 | 34 | 16 | FOBS= | 198.5 | SIGMA= | 1.0 | PHAS= | -23.5 | FOM= | 0.95 | TEST= 0 |
| INDE | 4 | 34 | 18 | FOBS= | 298.9 | SIGMA= | 1.1 | PHAS= | -126.7 | FOM= | 0.88 | TEST= 0 |
| INDE | 4 | 34 | 20 | FOBS= | 68.1 | SIGMA= | 3.5 | PHAS= | -141.9 | FOM= | 0.93 | TEST= 0 |
| INDE | 4 | 34 | 22 | FOBS= | 163.8 | SIGMA= | 1.7 | PHAS= | -85.3 | FOM= | 0.93 | TEST= 0 |
| INDE | 4 | 34 | 24 | FOBS= | 232.9 | SIGMA= | 1.3 | PHAS= | -110.5 | FOM= | 0.96 | TEST= 0 |
| INDE | 4 | 34 | 26 | FOBS= | 95.1 | SIGMA= | 2.8 | PHAS= | -69.5 | FOM= | 0.30 | TEST= 0 |
| INDE | 4 | 34 | 28 | FOBS= | 267.7 | SIGMA= | 1.0 | PHAS= | -135.8 | FOM= | 0.93 | TEST= 0 |
| INDE | 4 | 34 | 30 | FOBS= | 243.5 | SIGMA= | 1.1 | PHAS= | -84.7 | FOM= | 0.95 | TEST= 0 |
| INDE | 4 | 34 | 32 | FOBS= | 59.5 | SIGMA= | 3.6 | PHAS= | -100.7 | FOM= | 0.66 | TEST= 0 |
| INDE | 4 | 34 | 34 | FOBS= | 226.1 | SIGMA= | 1.1 | PHAS= | -100.7 | FOM= | 0.96 | TEST= 0 |
| INDE | 4 | 34 | 36 | FOBS= | 93.5 | SIGMA= | 2.6 | PHAS= | 110.9 | FOM= | 0.73 | TEST= 0 |
| INDE | 4 | 34 | 38 | FOBS= | 335.8 | SIGMA= | 0.8 | PHAS= | 3.5 | FOM= | 0.97 | TEST= 0 |
| INDE | 4 | 34 | 40 | FOBS= | 0.0 | SIGMA= | 19.5 | PHAS= | 0.0 | FOM= | 0.00 | TEST= 1 |
| INDE | 4 | 34 | 42 | FOBS= | 110.2 | SIGMA= | 1.7 | PHAS= | 162.6 | FOM= | 0.80 | TEST= 1 |
| INDE | 4 | 34 | 44 | FOBS= | 152.7 | SIGMA= | 1.1 | PHAS= | -155.4 | FOM= | 0.89 | TEST= 0 |
| INDE | 4 | 34 | 46 | FOBS= | 0.0 | SIGMA= | 17.8 | PHAS= | 0.0 | FOM= | 0.00 | TEST= 0 |
| INDE | 4 | 34 | 48 | FOBS= | 72.3 | SIGMA= | 2.0 | PHAS= | 28.3 | FOM= | 0.62 | TEST= 0 |
| INDE | 4 | 34 | 50 | FOBS= | 111.9 | SIGMA= | 1.3 | PHAS= | -143.2 | FOM= | 0.94 | TEST= 0 |
| INDE | 4 | 34 | 52 | FOBS= | 0.0 | SIGMA= | 18.3 | PHAS= | 0.0 | FOM= | 0.00 | TEST= 0 |
| INDE | 4 | 34 | 54 | FOBS= | 88.6 | SIGMA= | 1.9 | PHAS= | 120.0 | FOM= | 0.93 | TEST= 0 |
| INDE | 4 | 34 | 56 | FOBS= | 48.0 | SIGMA= | 3.7 | PHAS= | -101.2 | FOM= | 0.82 | TEST= 0 |
| INDE | 4 | 34 | 58 | FOBS= | 61.5 | SIGMA= | 2.9 | PHAS= | -152.8 | FOM= | 0.74 | TEST= 1 |
| INDE | 4 | 34 | 60 | FOBS= | 40.9 | SIGMA= | 4.4 | PHAS= | -161.1 | FOM= | 0.43 | TEST= 0 |
| INDE | 4 | 34 | 62 | FOBS= | 53.6 | SIGMA= | 3.4 | PHAS= | -127.2 | FOM= | 0.73 | TEST= 0 |
| INDE | 4 | 34 | 64 | FOBS= | 53.0 | SIGMA= | 3.9 | PHAS= | 124.0 | FOM= | 0.90 | TEST= 0 |
| INDE | 4 | 34 | 66 | FOBS= | 50.1 | SIGMA= | 4.7 | PHAS= | -147.3 | FOM= | 0.07 | TEST= 1 |
| INDE | 4 | 34 | 68 | FOBS= | 69.9 | SIGMA= | 5.4 | PHAS= | 137.0 | FOM= | 0.14 | TEST= 1 |
| INDE | 4 | 35 | 5 | FOBS= | 229.8 | SIGMA= | 0.8 | PHAS= | 36.1 | FOM= | 0.98 | TEST= 0 |
| INDE | 4 | 35 | 7 | FOBS= | 190.3 | SIGMA= | 0.7 | PHAS= | 80.9 | FOM= | 0.98 | TEST= 0 |
| INDE | 4 | 35 | 9 | FOBS= | 136.8 | SIGMA= | 0.8 | PHAS= | -45.1 | FOM= | 0.98 | TEST= 0 |
| INDE | 4 | 35 | 11 | FOBS= | 94.6 | SIGMA= | 1.4 | PHAS= | 67.7 | FOM= | 0.69 | TEST= 0 |
| INDE | 4 | 35 | 13 | FOBS= | 334.3 | SIGMA= | 0.8 | PHAS= | -55.9 | FOM= | 0.98 | TEST= 0 |
| INDE | 4 | 35 | 15 | FOBS= | 110.7 | SIGMA= | 1.4 | PHAS= | 72.8 | FOM= | 0.98 | TEST= 0 |
| INDE | 4 | 35 | 17 | FOBS= | 184.1 | SIGMA= | 1.0 | PHAS= | -57.5 | FOM= | 0.88 | TEST= 0 |
| INDE | 4 | 35 | 19 | FOBS= | 133.1 | SIGMA= | 2.0 | PHAS= | -77.7 | FOM= | 0.90 | TEST= 0 |
| INDE | 4 | 35 | 21 | FOBS= | 280.1 | SIGMA= | 1.2 | PHAS= | 96.2 | FOM= | 0.99 | TEST= 0 |
| INDE | 4 | 35 | 23 | FOBS= | 313.8 | SIGMA= | 1.1 | PHAS= | 118.7 | FOM= | 0.97 | TEST= 0 |
| INDE | 4 | 35 | 25 | FOBS= | 320.2 | SIGMA= | 1.1 | PHAS= | 119.2 | FOM= | 0.96 | TEST= 0 |
| INDE | 4 | 35 | 27 | FOBS= | 159.3 | SIGMA= | 1.9 | PHAS= | 154.7 | FOM= | 0.86 | TEST= 0 |
| INDE | 4 | 35 | 29 | FOBS= | 129.2 | SIGMA= | 1.9 | PHAS= | 144.0 | FOM= | 0.84 | TEST= 1 |
| INDE | 4 | 35 | 31 | FOBS= | 259.2 | SIGMA= | 1.0 | PHAS= | -165.6 | FOM= | 0.97 | TEST= 0 |
| INDE | 4 | 35 | 33 | FOBS= | 171.4 | SIGMA= | 1.4 | PHAS= | 178.8 | FOM= | 0.94 | TEST= 0 |
| INDE | 4 | 35 | 35 | FOBS= | 37.1 | SIGMA= | 6.6 | PHAS= | 165.3 | FOM= | 0.53 | TEST= 0 |
| INDE | 4 | 35 | 37 | FOBS= | 103.3 | SIGMA= | 2.2 | PHAS= | -92.0 | FOM= | 0.70 | TEST= 0 |
| INDE | 4 | 35 | 39 | FOBS= | 132.1 | SIGMA= | 1.6 | PHAS= | -81.3 | FOM= | 0.88 | TEST= 0 |
| INDE | 4 | 35 | 41 | FOBS= | 146.9 | SIGMA= | 1.3 | PHAS= | 55.8 | FOM= | 0.93 | TEST= 0 |
| INDE | 4 | 35 | 43 | FOBS= | 51.0 | SIGMA= | 3.5 | PHAS= | 114.0 | FOM= | 0.17 | TEST= 1 |
| INDE | 4 | 35 | 45 | FOBS= | 229.7 | SIGMA= | 0.8 | PHAS= | 105.3 | FOM= | 0.95 | TEST= 0 |
| INDE | 4 | 35 | 47 | FOBS= | 66.4 | SIGMA= | 2.3 | PHAS= | -32.8 | FOM= | 0.80 | TEST= 0 |
| INDE | 4 | 35 | 49 | FOBS= | 68.5 | SIGMA= | 2.1 | PHAS= | 172.6 | FOM= | 0.78 | TEST= 0 |

*FIG. 12A - 119*

```
INDE  4  35  51  FOBS=   82.0  SIGMA=   1.8  PHAS=  148.8  FOM=  0.85  TEST= 0
INDE  4  35  53  FOBS=   53.7  SIGMA=   3.4  PHAS=   94.5  FOM=  0.55  TEST= 0
INDE  4  35  55  FOBS=   58.4  SIGMA=   3.1  PHAS=    8.1  FOM=  0.89  TEST= 0
INDE  4  35  57  FOBS=   18.1  SIGMA=   9.7  PHAS=   22.2  FOM=  0.41  TEST= 0
INDE  4  35  59  FOBS=   42.4  SIGMA=   4.1  PHAS=   96.8  FOM=  0.52  TEST= 0
INDE  4  35  61  FOBS=   17.0  SIGMA=  10.4  PHAS= -122.1  FOM=  0.16  TEST= 0
INDE  4  35  63  FOBS=   57.1  SIGMA=   3.2  PHAS=  -39.7  FOM=  0.24  TEST= 0
INDE  4  35  65  FOBS=   43.4  SIGMA=   4.8  PHAS= -164.2  FOM=  0.71  TEST= 0
INDE  4  35  67  FOBS=   58.7  SIGMA=   4.5  PHAS=  -31.0  FOM=  0.85  TEST= 0
INDE  4  35  69  FOBS=   85.9  SIGMA=   6.4  PHAS= -173.4  FOM=  0.61  TEST= 0
INDE  4  36   4  FOBS=  205.8  SIGMA=   0.9  PHAS=  -67.8  FOM=  0.99  TEST= 0
INDE  4  36   6  FOBS=  131.3  SIGMA=   1.3  PHAS=  -53.4  FOM=  0.92  TEST= 0
INDE  4  36   8  FOBS=  213.6  SIGMA=   0.7  PHAS=  -20.4  FOM=  0.96  TEST= 0
INDE  4  36  10  FOBS=   60.8  SIGMA=   2.4  PHAS=   95.1  FOM=  0.90  TEST= 0
INDE  4  36  12  FOBS=  201.1  SIGMA=   0.8  PHAS=  -61.0  FOM=  0.96  TEST= 0
INDE  4  36  14  FOBS=   16.7  SIGMA=   8.5  PHAS=  148.4  FOM=  0.26  TEST= 1
INDE  4  36  16  FOBS=   96.5  SIGMA=   1.7  PHAS= -117.1  FOM=  0.87  TEST= 0
INDE  4  36  18  FOBS=  138.9  SIGMA=   1.2  PHAS=  178.6  FOM=  0.12  TEST= 0
INDE  4  36  20  FOBS=  216.3  SIGMA=   1.4  PHAS=   47.1  FOM=  0.95  TEST= 0
INDE  4  36  22  FOBS=  210.6  SIGMA=   1.5  PHAS=  -34.3  FOM=  0.95  TEST= 0
INDE  4  36  24  FOBS=  203.7  SIGMA=   1.6  PHAS=   31.9  FOM=  0.99  TEST= 0
INDE  4  36  26  FOBS=  296.3  SIGMA=   1.2  PHAS=   34.1  FOM=  0.93  TEST= 0
INDE  4  36  28  FOBS=   68.9  SIGMA=   4.4  PHAS=  141.2  FOM=  0.70  TEST= 0
INDE  4  36  30  FOBS=   94.2  SIGMA=   2.7  PHAS=  -48.6  FOM=  0.82  TEST= 0
INDE  4  36  32  FOBS=  246.2  SIGMA=   1.2  PHAS=   79.7  FOM=  0.87  TEST= 0
INDE  4  36  34  FOBS=   25.8  SIGMA=   8.9  PHAS=  -80.6  FOM=  0.41  TEST= 0
INDE  4  36  36  FOBS=  162.5  SIGMA=   1.6  PHAS=  156.8  FOM=  0.91  TEST= 0
INDE  4  36  38  FOBS=  247.1  SIGMA=   0.9  PHAS= -132.4  FOM=  0.94  TEST= 0
INDE  4  36  40  FOBS=   16.4  SIGMA=  13.3  PHAS= -115.9  FOM=  0.10  TEST= 0
INDE  4  36  42  FOBS=  121.9  SIGMA=   1.5  PHAS=   83.1  FOM=  0.83  TEST= 0
INDE  4  36  44  FOBS=   44.1  SIGMA=   3.7  PHAS= -127.2  FOM=  0.76  TEST= 0
INDE  4  36  46  FOBS=   49.5  SIGMA=   3.7  PHAS= -166.9  FOM=  0.77  TEST= 0
INDE  4  36  48  FOBS=   53.2  SIGMA=   2.8  PHAS=   45.3  FOM=  0.86  TEST= 0
INDE  4  36  50  FOBS=   83.1  SIGMA=   1.8  PHAS=  102.9  FOM=  0.84  TEST= 0
INDE  4  36  52  FOBS=   53.9  SIGMA=   2.6  PHAS=  -56.5  FOM=  0.49  TEST= 0
INDE  4  36  54  FOBS=   75.2  SIGMA=   2.4  PHAS=   26.8  FOM=  0.19  TEST= 1
INDE  4  36  56  FOBS=   75.0  SIGMA=   2.4  PHAS=   92.0  FOM=  0.22  TEST= 1
INDE  4  36  58  FOBS=   91.1  SIGMA=   2.0  PHAS=  -93.5  FOM=  0.91  TEST= 0
INDE  4  36  60  FOBS=   59.5  SIGMA=   3.0  PHAS= -174.2  FOM=  0.90  TEST= 0
INDE  4  36  62  FOBS=    0.0  SIGMA=  19.5  PHAS=    0.0  FOM=  0.00  TEST= 0
INDE  4  36  64  FOBS=   64.9  SIGMA=   2.9  PHAS=   55.6  FOM=  0.25  TEST= 0
INDE  4  36  66  FOBS=   69.0  SIGMA=   3.5  PHAS=  157.9  FOM=  0.90  TEST= 0
INDE  4  36  68  FOBS=    0.0  SIGMA=  27.8  PHAS=    0.0  FOM=  0.00  TEST= 0
INDE  4  37   5  FOBS=  241.7  SIGMA=   0.9  PHAS=   83.4  FOM=  0.96  TEST= 0
INDE  4  37   7  FOBS=  195.1  SIGMA=   0.7  PHAS=   50.6  FOM=  0.88  TEST= 0
INDE  4  37   9  FOBS=  101.7  SIGMA=   1.2  PHAS=  -97.7  FOM=  0.93  TEST= 0
INDE  4  37  11  FOBS=  109.1  SIGMA=   1.5  PHAS=  -32.1  FOM=  0.25  TEST= 0
INDE  4  37  13  FOBS=  272.7  SIGMA=   0.9  PHAS=  162.3  FOM=  0.99  TEST= 0
INDE  4  37  15  FOBS=  212.8  SIGMA=   0.9  PHAS=  138.2  FOM=  0.97  TEST= 0
INDE  4  37  17  FOBS=  275.3  SIGMA=   0.8  PHAS=  -17.4  FOM=  0.95  TEST= 0
INDE  4  37  19  FOBS=  107.9  SIGMA=   2.6  PHAS=  -96.6  FOM=  0.54  TEST= 0
INDE  4  37  21  FOBS=  144.4  SIGMA=   2.1  PHAS=   30.1  FOM=  0.86  TEST= 0
INDE  4  37  23  FOBS=  117.3  SIGMA=   2.5  PHAS=   38.8  FOM=  0.43  TEST= 0
INDE  4  37  25  FOBS=  100.6  SIGMA=   3.0  PHAS=  -77.9  FOM=  0.86  TEST= 0
INDE  4  37  27  FOBS=  142.3  SIGMA=   2.3  PHAS= -123.6  FOM=  0.91  TEST= 0
INDE  4  37  29  FOBS=   38.6  SIGMA=   8.3  PHAS=  -45.6  FOM=  0.75  TEST= 0
INDE  4  37  31  FOBS=  160.2  SIGMA=   1.6  PHAS=  -50.5  FOM=  0.89  TEST= 0
INDE  4  37  33  FOBS=  252.0  SIGMA=   1.2  PHAS=   -7.3  FOM=  0.95  TEST= 0
INDE  4  37  35  FOBS=  212.0  SIGMA=   1.3  PHAS= -142.6  FOM=  0.95  TEST= 0
INDE  4  37  37  FOBS=  138.5  SIGMA=   1.8  PHAS=   80.8  FOM=  0.87  TEST= 0
INDE  4  37  39  FOBS=   65.9  SIGMA=   3.0  PHAS=  129.4  FOM=  0.65  TEST= 0
INDE  4  37  41  FOBS=  107.8  SIGMA=   1.7  PHAS=   69.5  FOM=  0.92  TEST= 0
INDE  4  37  43  FOBS=  140.2  SIGMA=   1.3  PHAS=   42.1  FOM=  0.94  TEST= 0
INDE  4  37  45  FOBS=  198.3  SIGMA=   0.9  PHAS=   59.2  FOM=  0.97  TEST= 0
INDE  4  37  47  FOBS=   84.6  SIGMA=   1.8  PHAS=   81.6  FOM=  0.72  TEST= 0
INDE  4  37  49  FOBS=    0.0  SIGMA=  17.0  PHAS=    0.0  FOM=  0.00  TEST= 0
INDE  4  37  51  FOBS=  115.5  SIGMA=   1.3  PHAS= -114.2  FOM=  0.95  TEST= 0
INDE  4  37  53  FOBS=   77.1  SIGMA=   2.2  PHAS= -120.0  FOM=  0.78  TEST= 0
INDE  4  37  55  FOBS=   54.3  SIGMA=   3.4  PHAS=  -23.6  FOM=  0.50  TEST= 0
INDE  4  37  57  FOBS=   96.3  SIGMA=   1.9  PHAS=  152.1  FOM=  0.77  TEST= 1
```

*FIG. 12A - 120*

| | | | | | | | | | | | |
|---|---|---|---|---|---|---|---|---|---|---|---|
| INDE | 4 | 37 | 59 | FOBS= | 132.5 | SIGMA= | 1.4 | PHAS= | 133.1 | FOM= 0.96 | TEST= 0 |
| INDE | 4 | 37 | 61 | FOBS= | 0.0 | SIGMA= | 19.7 | PHAS= | 0.0 | FOM= 0.00 | TEST= 0 |
| INDE | 4 | 37 | 63 | FOBS= | 59.3 | SIGMA= | 3.1 | PHAS= | 57.8 | FOM= 0.31 | TEST= 0 |
| INDE | 4 | 37 | 65 | FOBS= | 0.0 | SIGMA= | 19.4 | PHAS= | 0.0 | FOM= 0.00 | TEST= 0 |
| INDE | 4 | 37 | 67 | FOBS= | 56.4 | SIGMA= | 5.6 | PHAS= | 8.5 | FOM= 0.78 | TEST= 0 |
| INDE | 4 | 38 | 4 | FOBS= | 89.6 | SIGMA= | 1.8 | PHAS= | -56.0 | FOM= 0.65 | TEST= 0 |
| INDE | 4 | 38 | 6 | FOBS= | 12.4 | SIGMA= | 18.8 | PHAS= | -81.5 | FOM= 0.06 | TEST= 1 |
| INDE | 4 | 38 | 8 | FOBS= | 64.4 | SIGMA= | 2.0 | PHAS= | 167.4 | FOM= 0.92 | TEST= 0 |
| INDE | 4 | 38 | 10 | FOBS= | 163.3 | SIGMA= | 0.7 | PHAS= | 78.7 | FOM= 0.86 | TEST= 0 |
| INDE | 4 | 38 | 12 | FOBS= | 195.9 | SIGMA= | 0.9 | PHAS= | -103.4 | FOM= 0.95 | TEST= 0 |
| INDE | 4 | 38 | 14 | FOBS= | 224.5 | SIGMA= | 1.0 | PHAS= | 117.1 | FOM= 0.98 | TEST= 0 |
| INDE | 4 | 38 | 16 | FOBS= | 292.0 | SIGMA= | 0.9 | PHAS= | -124.8 | FOM= 0.95 | TEST= 0 |
| INDE | 4 | 38 | 18 | FOBS= | 255.6 | SIGMA= | 1.0 | PHAS= | 5.5 | FOM= 0.60 | TEST= 1 |
| INDE | 4 | 38 | 20 | FOBS= | 151.1 | SIGMA= | 2.1 | PHAS= | 151.4 | FOM= 0.86 | TEST= 0 |
| INDE | 4 | 38 | 22 | FOBS= | 120.8 | SIGMA= | 2.5 | PHAS= | -63.1 | FOM= 0.94 | TEST= 0 |
| INDE | 4 | 38 | 24 | FOBS= | 82.3 | SIGMA= | 3.8 | PHAS= | -109.7 | FOM= 0.95 | TEST= 0 |
| INDE | 4 | 38 | 26 | FOBS= | 136.6 | SIGMA= | 2.4 | PHAS= | -177.4 | FOM= 0.95 | TEST= 0 |
| INDE | 4 | 38 | 28 | FOBS= | 142.8 | SIGMA= | 2.4 | PHAS= | -137.8 | FOM= 0.82 | TEST= 0 |
| INDE | 4 | 38 | 30 | FOBS= | 242.4 | SIGMA= | 1.4 | PHAS= | -118.2 | FOM= 0.95 | TEST= 0 |
| INDE | 4 | 38 | 32 | FOBS= | 204.5 | SIGMA= | 1.2 | PHAS= | -91.9 | FOM= 0.95 | TEST= 0 |
| INDE | 4 | 38 | 34 | FOBS= | 376.5 | SIGMA= | 0.9 | PHAS= | -179.6 | FOM= 0.98 | TEST= 0 |
| INDE | 4 | 38 | 36 | FOBS= | 147.8 | SIGMA= | 1.7 | PHAS= | 7.5 | FOM= 0.82 | TEST= 0 |
| INDE | 4 | 38 | 38 | FOBS= | 211.2 | SIGMA= | 1.1 | PHAS= | -98.8 | FOM= 0.95 | TEST= 0 |
| INDE | 4 | 38 | 40 | FOBS= | 22.8 | SIGMA= | 12.0 | PHAS= | 53.0 | FOM= 0.22 | TEST= 1 |
| INDE | 4 | 38 | 42 | FOBS= | 70.2 | SIGMA= | 2.6 | PHAS= | -4.9 | FOM= 0.87 | TEST= 0 |
| INDE | 4 | 38 | 44 | FOBS= | 233.3 | SIGMA= | 0.8 | PHAS= | -41.7 | FOM= 0.96 | TEST= 0 |
| INDE | 4 | 38 | 46 | FOBS= | 76.1 | SIGMA= | 2.0 | PHAS= | -95.6 | FOM= 0.32 | TEST= 0 |
| INDE | 4 | 38 | 48 | FOBS= | 69.4 | SIGMA= | 2.2 | PHAS= | -176.4 | FOM= 0.83 | TEST= 0 |
| INDE | 4 | 38 | 50 | FOBS= | 95.2 | SIGMA= | 1.6 | PHAS= | 136.8 | FOM= 0.86 | TEST= 0 |
| INDE | 4 | 38 | 52 | FOBS= | 101.5 | SIGMA= | 1.8 | PHAS= | 164.4 | FOM= 0.89 | TEST= 0 |
| INDE | 4 | 38 | 54 | FOBS= | 35.0 | SIGMA= | 4.8 | PHAS= | -69.4 | FOM= 0.49 | TEST= 0 |
| INDE | 4 | 38 | 56 | FOBS= | 0.0 | SIGMA= | 20.6 | PHAS= | 0.0 | FOM= 0.00 | TEST= 0 |
| INDE | 4 | 38 | 58 | FOBS= | 102.7 | SIGMA= | 1.8 | PHAS= | 62.8 | FOM= 0.92 | TEST= 0 |
| INDE | 4 | 38 | 60 | FOBS= | 40.4 | SIGMA= | 4.4 | PHAS= | 18.0 | FOM= 0.72 | TEST= 0 |
| INDE | 4 | 38 | 62 | FOBS= | 23.8 | SIGMA= | 7.6 | PHAS= | -178.9 | FOM= 0.27 | TEST= 0 |
| INDE | 4 | 38 | 64 | FOBS= | 36.3 | SIGMA= | 5.8 | PHAS= | -33.3 | FOM= 0.56 | TEST= 0 |
| INDE | 4 | 38 | 66 | FOBS= | 89.6 | SIGMA= | 2.9 | PHAS= | -83.4 | FOM= 0.92 | TEST= 0 |
| INDE | 4 | 39 | 5 | FOBS= | 263.2 | SIGMA= | 0.9 | PHAS= | 89.0 | FOM= 0.90 | TEST= 0 |
| INDE | 4 | 39 | 9 | FOBS= | 81.6 | SIGMA= | 1.7 | PHAS= | 42.3 | FOM= 0.79 | TEST= 0 |
| INDE | 4 | 39 | 11 | FOBS= | 145.4 | SIGMA= | 0.9 | PHAS= | -77.5 | FOM= 0.86 | TEST= 0 |
| INDE | 4 | 39 | 13 | FOBS= | 280.6 | SIGMA= | 0.8 | PHAS= | 172.8 | FOM= 0.89 | TEST= 0 |
| INDE | 4 | 39 | 15 | FOBS= | 159.6 | SIGMA= | 1.2 | PHAS= | 146.5 | FOM= 0.98 | TEST= 0 |
| INDE | 4 | 39 | 17 | FOBS= | 64.1 | SIGMA= | 2.9 | PHAS= | 143.1 | FOM= 0.98 | TEST= 0 |
| INDE | 4 | 39 | 19 | FOBS= | 236.7 | SIGMA= | 1.0 | PHAS= | 131.5 | FOM= 0.93 | TEST= 0 |
| INDE | 4 | 39 | 21 | FOBS= | 186.2 | SIGMA= | 1.8 | PHAS= | 2.7 | FOM= 0.91 | TEST= 0 |
| INDE | 4 | 39 | 23 | FOBS= | 136.0 | SIGMA= | 2.5 | PHAS= | 63.0 | FOM= 0.81 | TEST= 0 |
| INDE | 4 | 39 | 25 | FOBS= | 210.7 | SIGMA= | 1.8 | PHAS= | 131.5 | FOM= 0.94 | TEST= 0 |
| INDE | 4 | 39 | 27 | FOBS= | 126.9 | SIGMA= | 2.7 | PHAS= | 64.5 | FOM= 0.93 | TEST= 0 |
| INDE | 4 | 39 | 29 | FOBS= | 253.4 | SIGMA= | 1.6 | PHAS= | 114.8 | FOM= 0.96 | TEST= 0 |
| INDE | 4 | 39 | 31 | FOBS= | 150.4 | SIGMA= | 1.9 | PHAS= | -164.0 | FOM= 0.61 | TEST= 0 |
| INDE | 4 | 39 | 33 | FOBS= | 179.6 | SIGMA= | 1.4 | PHAS= | 34.6 | FOM= 0.92 | TEST= 0 |
| INDE | 4 | 39 | 35 | FOBS= | 203.5 | SIGMA= | 1.3 | PHAS= | 145.2 | FOM= 0.97 | TEST= 0 |
| INDE | 4 | 39 | 37 | FOBS= | 106.4 | SIGMA= | 2.3 | PHAS= | -54.0 | FOM= 0.82 | TEST= 0 |
| INDE | 4 | 39 | 39 | FOBS= | 84.8 | SIGMA= | 2.4 | PHAS= | 179.8 | FOM= 0.71 | TEST= 0 |
| INDE | 4 | 39 | 41 | FOBS= | 176.5 | SIGMA= | 1.1 | PHAS= | 43.7 | FOM= 0.95 | TEST= 0 |
| INDE | 4 | 39 | 43 | FOBS= | 13.7 | SIGMA= | 13.2 | PHAS= | -171.0 | FOM= 0.22 | TEST= 0 |
| INDE | 4 | 39 | 45 | FOBS= | 151.4 | SIGMA= | 1.1 | PHAS= | -147.0 | FOM= 0.96 | TEST= 0 |
| INDE | 4 | 39 | 47 | FOBS= | 114.9 | SIGMA= | 1.4 | PHAS= | 101.6 | FOM= 0.92 | TEST= 0 |
| INDE | 4 | 39 | 49 | FOBS= | 89.5 | SIGMA= | 1.7 | PHAS= | 134.0 | FOM= 0.70 | TEST= 0 |
| INDE | 4 | 39 | 51 | FOBS= | 50.6 | SIGMA= | 3.0 | PHAS= | 63.0 | FOM= 0.71 | TEST= 0 |
| INDE | 4 | 39 | 53 | FOBS= | 40.5 | SIGMA= | 4.3 | PHAS= | 178.3 | FOM= 0.58 | TEST= 0 |
| INDE | 4 | 39 | 55 | FOBS= | 62.4 | SIGMA= | 2.7 | PHAS= | -127.9 | FOM= 0.79 | TEST= 0 |
| INDE | 4 | 39 | 57 | FOBS= | 20.5 | SIGMA= | 8.9 | PHAS= | 31.6 | FOM= 0.67 | TEST= 0 |
| INDE | 4 | 39 | 59 | FOBS= | 0.0 | SIGMA= | 20.4 | PHAS= | 0.0 | FOM= 0.00 | TEST= 0 |
| INDE | 4 | 39 | 61 | FOBS= | 0.0 | SIGMA= | 20.3 | PHAS= | 0.0 | FOM= 0.00 | TEST= 1 |
| INDE | 4 | 39 | 63 | FOBS= | 0.0 | SIGMA= | 19.9 | PHAS= | 0.0 | FOM= 0.00 | TEST= 0 |
| INDE | 4 | 39 | 65 | FOBS= | 37.9 | SIGMA= | 6.9 | PHAS= | 152.3 | FOM= 0.73 | TEST= 0 |
| INDE | 4 | 39 | 67 | FOBS= | 105.6 | SIGMA= | 3.3 | PHAS= | -107.8 | FOM= 0.84 | TEST= 0 |
| INDE | 4 | 40 | 4 | FOBS= | 120.3 | SIGMA= | 1.6 | PHAS= | 4.5 | FOM= 0.96 | TEST= 0 |
| INDE | 4 | 40 | 8 | FOBS= | 320.4 | SIGMA= | 0.6 | PHAS= | -40.2 | FOM= 0.96 | TEST= 0 |

*FIG. 12A - 121*

```
INDE  4  40  10 FOBS=  175.3 SIGMA=  0.8 PHAS=   77.2 FOM= 0.90 TEST= 0
INDE  4  40  12 FOBS=  170.5 SIGMA=  0.9 PHAS= -156.8 FOM= 0.95 TEST= 0
INDE  4  40  14 FOBS=  274.2 SIGMA=  1.0 PHAS=   21.0 FOM= 0.94 TEST= 0
INDE  4  40  16 FOBS=   38.5 SIGMA=  4.7 PHAS= -155.0 FOM= 0.54 TEST= 0
INDE  4  40  18 FOBS=  121.9 SIGMA=  1.7 PHAS=   60.4 FOM= 0.87 TEST= 0
INDE  4  40  20 FOBS=  135.2 SIGMA=  1.6 PHAS=  -31.9 FOM= 0.46 TEST= 1
INDE  4  40  22 FOBS=  188.9 SIGMA=  1.9 PHAS= -145.4 FOM= 0.95 TEST= 0
INDE  4  40  24 FOBS=  186.3 SIGMA=  2.0 PHAS=   72.4 FOM= 0.84 TEST= 0
INDE  4  40  26 FOBS=    0.0 SIGMA= 26.1 PHAS=    0.0 FOM= 0.00 TEST= 0
INDE  4  40  28 FOBS=  203.6 SIGMA=  1.9 PHAS=  -10.2 FOM= 0.96 TEST= 0
INDE  4  40  30 FOBS=  236.0 SIGMA=  1.6 PHAS=   -6.2 FOM= 0.70 TEST= 1
INDE  4  40  32 FOBS=   33.2 SIGMA=  7.9 PHAS=   78.4 FOM= 0.70 TEST= 1
INDE  4  40  34 FOBS=  107.7 SIGMA=  2.2 PHAS=  106.6 FOM= 0.82 TEST= 0
INDE  4  40  36 FOBS=   37.2 SIGMA=  6.4 PHAS=  -15.3 FOM= 0.45 TEST= 0
INDE  4  40  38 FOBS=  115.7 SIGMA=  2.0 PHAS= -148.0 FOM= 0.62 TEST= 1
INDE  4  40  40 FOBS=  258.6 SIGMA=  0.9 PHAS=  -66.0 FOM= 0.94 TEST= 0
INDE  4  40  42 FOBS=   24.8 SIGMA=  9.5 PHAS=  -96.5 FOM= 0.22 TEST= 0
INDE  4  40  44 FOBS=   95.0 SIGMA=  1.8 PHAS=   88.1 FOM= 0.88 TEST= 0
INDE  4  40  46 FOBS=   58.4 SIGMA=  2.6 PHAS=   84.8 FOM= 0.91 TEST= 0
INDE  4  40  48 FOBS=   30.5 SIGMA=  4.9 PHAS=  -39.5 FOM= 0.36 TEST= 0
INDE  4  40  50 FOBS=    0.0 SIGMA= 18.6 PHAS=    0.0 FOM= 0.00 TEST= 0
INDE  4  40  52 FOBS=   49.0 SIGMA=  3.5 PHAS=  -21.9 FOM= 0.69 TEST= 0
INDE  4  40  54 FOBS=   74.5 SIGMA=  2.4 PHAS=  124.9 FOM= 0.84 TEST= 0
INDE  4  40  56 FOBS=   22.4 SIGMA=  7.6 PHAS= -102.4 FOM= 0.67 TEST= 0
INDE  4  40  58 FOBS=   22.2 SIGMA=  9.4 PHAS=   50.0 FOM= 0.42 TEST= 0
INDE  4  40  60 FOBS=   35.3 SIGMA=  6.0 PHAS=   36.1 FOM= 0.70 TEST= 0
INDE  4  40  62 FOBS=   32.4 SIGMA=  5.7 PHAS=  107.6 FOM= 0.47 TEST= 0
INDE  4  40  64 FOBS=   82.7 SIGMA=  2.3 PHAS=   30.6 FOM= 0.90 TEST= 0
INDE  4  40  66 FOBS=   30.1 SIGMA= 13.2 PHAS= -148.2 FOM= 0.74 TEST= 0
INDE  4  41   5 FOBS=  115.2 SIGMA=  1.7 PHAS=   -4.1 FOM= 0.94 TEST= 0
INDE  4  41   9 FOBS=  147.5 SIGMA=  1.1 PHAS=  -43.3 FOM= 0.95 TEST= 0
INDE  4  41  11 FOBS=  237.8 SIGMA=  0.8 PHAS=   36.5 FOM= 0.97 TEST= 0
INDE  4  41  13 FOBS=  115.2 SIGMA=  1.6 PHAS= -169.7 FOM= 0.95 TEST= 0
INDE  4  41  15 FOBS=  196.4 SIGMA=  1.1 PHAS=  -94.9 FOM= 0.96 TEST= 0
INDE  4  41  17 FOBS=  203.5 SIGMA=  1.1 PHAS=  158.3 FOM= 0.71 TEST= 0
INDE  4  41  19 FOBS=  142.2 SIGMA=  1.6 PHAS=   70.8 FOM= 0.35 TEST= 0
INDE  4  41  21 FOBS=    0.0 SIGMA= 22.0 PHAS=    0.0 FOM= 0.00 TEST= 0
INDE  4  41  23 FOBS=  194.6 SIGMA=  2.0 PHAS=   71.7 FOM= 0.95 TEST= 0
INDE  4  41  25 FOBS=   71.2 SIGMA=  5.0 PHAS=   19.6 FOM= 0.37 TEST= 0
INDE  4  41  27 FOBS=   64.1 SIGMA=  5.5 PHAS=  131.3 FOM= 0.13 TEST= 0
INDE  4  41  29 FOBS=  200.3 SIGMA=  1.9 PHAS=  -99.3 FOM= 0.87 TEST= 0
INDE  4  41  31 FOBS=   93.1 SIGMA=  3.7 PHAS=  -49.7 FOM= 0.80 TEST= 0
INDE  4  41  33 FOBS=  228.6 SIGMA=  1.3 PHAS=    9.6 FOM= 0.95 TEST= 0
INDE  4  41  35 FOBS=   71.3 SIGMA=  3.4 PHAS=   75.8 FOM= 0.63 TEST= 0
INDE  4  41  37 FOBS=  176.5 SIGMA=  1.5 PHAS=   68.2 FOM= 0.91 TEST= 0
INDE  4  41  39 FOBS=  102.7 SIGMA=  2.0 PHAS=  166.3 FOM= 0.90 TEST= 0
INDE  4  41  41 FOBS=  102.0 SIGMA=  1.9 PHAS=  -26.3 FOM= 0.86 TEST= 0
INDE  4  41  43 FOBS=  113.9 SIGMA=  1.7 PHAS=  135.4 FOM= 0.84 TEST= 0
INDE  4  41  45 FOBS=    0.0 SIGMA= 17.7 PHAS=    0.0 FOM= 0.00 TEST= 0
INDE  4  41  47 FOBS=   22.1 SIGMA=  7.2 PHAS=    9.3 FOM= 0.25 TEST= 0
INDE  4  41  49 FOBS=   54.7 SIGMA=  2.7 PHAS=   36.8 FOM= 0.64 TEST= 0
INDE  4  41  51 FOBS=   40.8 SIGMA=  4.6 PHAS= -150.3 FOM= 0.42 TEST= 0
INDE  4  41  53 FOBS=    0.0 SIGMA= 21.7 PHAS=    0.0 FOM= 0.00 TEST= 0
INDE  4  41  55 FOBS=    0.0 SIGMA= 18.6 PHAS=    0.0 FOM= 0.00 TEST= 0
INDE  4  41  57 FOBS=    0.0 SIGMA= 19.0 PHAS=    0.0 FOM= 0.00 TEST= 0
INDE  4  41  59 FOBS=   50.5 SIGMA=  3.7 PHAS=  -82.8 FOM= 0.66 TEST= 0
INDE  4  41  61 FOBS=    9.5 SIGMA= 20.3 PHAS= -158.1 FOM= 0.05 TEST= 0
INDE  4  41  63 FOBS=   94.2 SIGMA=  2.1 PHAS=  -75.9 FOM= 0.91 TEST= 0
INDE  4  41  65 FOBS=   98.7 SIGMA=  2.6 PHAS=   10.2 FOM= 0.93 TEST= 0
INDE  4  42   4 FOBS=  109.0 SIGMA=  1.9 PHAS=  -37.2 FOM= 0.95 TEST= 0
INDE  4  42  10 FOBS=  134.5 SIGMA=  1.3 PHAS=  -72.2 FOM= 0.93 TEST= 0
INDE  4  42  12 FOBS=  310.7 SIGMA=  0.6 PHAS= -159.3 FOM= 0.98 TEST= 0
INDE  4  42  14 FOBS=   73.8 SIGMA=  2.6 PHAS=   97.0 FOM= 0.81 TEST= 0
INDE  4  42  16 FOBS=  215.8 SIGMA=  1.1 PHAS=   82.6 FOM= 0.94 TEST= 0
INDE  4  42  18 FOBS=  248.7 SIGMA=  1.2 PHAS=  130.3 FOM= 0.94 TEST= 0
INDE  4  42  20 FOBS=  158.4 SIGMA=  1.5 PHAS=  -90.5 FOM= 0.86 TEST= 0
INDE  4  42  22 FOBS=   54.4 SIGMA=  5.0 PHAS=  -61.7 FOM= 0.84 TEST= 0
INDE  4  42  24 FOBS=  135.5 SIGMA=  2.8 PHAS=   24.2 FOM= 0.86 TEST= 0
INDE  4  42  26 FOBS=  153.1 SIGMA=  2.5 PHAS=   50.8 FOM= 0.92 TEST= 0
INDE  4  42  28 FOBS=  203.3 SIGMA=  1.9 PHAS=   76.4 FOM= 0.89 TEST= 0
```

*FIG. 12A - 122*

| | | | | | | | | | | | |
|---|---|---|---|---|---|---|---|---|---|---|---|
| INDE | 4 | 42 | 30 | FOBS= | 121.8 | SIGMA= | 2.9 | PHAS= | -141.5 | FOM= | 0.78 | TEST= 0 |
| INDE | 4 | 42 | 32 | FOBS= | 164.4 | SIGMA= | 2.2 | PHAS= | 154.9 | FOM= | 0.91 | TEST= 0 |
| INDE | 4 | 42 | 34 | FOBS= | 71.5 | SIGMA= | 3.1 | PHAS= | -73.7 | FOM= | 0.73 | TEST= 0 |
| INDE | 4 | 42 | 36 | FOBS= | 83.0 | SIGMA= | 2.9 | PHAS= | 38.4 | FOM= | 0.72 | TEST= 0 |
| INDE | 4 | 42 | 38 | FOBS= | 173.1 | SIGMA= | 1.4 | PHAS= | 37.0 | FOM= | 0.97 | TEST= 0 |
| INDE | 4 | 42 | 40 | FOBS= | 75.3 | SIGMA= | 2.7 | PHAS= | -122.8 | FOM= | 0.66 | TEST= 0 |
| INDE | 4 | 42 | 42 | FOBS= | 98.3 | SIGMA= | 1.9 | PHAS= | -43.9 | FOM= | 0.55 | TEST= 1 |
| INDE | 4 | 42 | 44 | FOBS= | 88.5 | SIGMA= | 1.9 | PHAS= | -37.2 | FOM= | 0.91 | TEST= 0 |
| INDE | 4 | 42 | 46 | FOBS= | 68.8 | SIGMA= | 2.2 | PHAS= | 2.2 | FOM= | 0.13 | TEST= 1 |
| INDE | 4 | 42 | 48 | FOBS= | 58.4 | SIGMA= | 2.6 | PHAS= | -89.0 | FOM= | 0.92 | TEST= 0 |
| INDE | 4 | 42 | 50 | FOBS= | 22.5 | SIGMA= | 7.5 | PHAS= | -77.2 | FOM= | 0.15 | TEST= 0 |
| INDE | 4 | 42 | 52 | FOBS= | 56.1 | SIGMA= | 3.1 | PHAS= | 74.5 | FOM= | 0.86 | TEST= 0 |
| INDE | 4 | 42 | 54 | FOBS= | 39.6 | SIGMA= | 4.6 | PHAS= | 165.9 | FOM= | 0.73 | TEST= 0 |
| INDE | 4 | 42 | 56 | FOBS= | 87.1 | SIGMA= | 2.0 | PHAS= | -117.4 | FOM= | 0.92 | TEST= 0 |
| INDE | 4 | 42 | 58 | FOBS= | 0.0 | SIGMA= | 19.0 | PHAS= | 0.0 | FOM= | 0.00 | TEST= 0 |
| INDE | 4 | 42 | 60 | FOBS= | 0.0 | SIGMA= | 21.7 | PHAS= | 0.0 | FOM= | 0.00 | TEST= 0 |
| INDE | 4 | 42 | 62 | FOBS= | 43.2 | SIGMA= | 4.4 | PHAS= | 69.5 | FOM= | 0.80 | TEST= 0 |
| INDE | 4 | 42 | 64 | FOBS= | 99.4 | SIGMA= | 2.5 | PHAS= | -169.1 | FOM= | 0.93 | TEST= 0 |
| INDE | 4 | 43 | 5 | FOBS= | 162.8 | SIGMA= | 1.4 | PHAS= | 102.1 | FOM= | 0.79 | TEST= 0 |
| INDE | 4 | 43 | 9 | FOBS= | 177.2 | SIGMA= | 1.0 | PHAS= | -131.6 | FOM= | 0.96 | TEST= 0 |
| INDE | 4 | 43 | 11 | FOBS= | 445.7 | SIGMA= | 0.9 | PHAS= | 151.3 | FOM= | 0.98 | TEST= 0 |
| INDE | 4 | 43 | 13 | FOBS= | 193.2 | SIGMA= | 0.8 | PHAS= | 105.8 | FOM= | 0.91 | TEST= 0 |
| INDE | 4 | 43 | 15 | FOBS= | 140.6 | SIGMA= | 1.5 | PHAS= | 29.1 | FOM= | 0.97 | TEST= 0 |
| INDE | 4 | 43 | 17 | FOBS= | 291.2 | SIGMA= | 1.1 | PHAS= | -43.8 | FOM= | 0.93 | TEST= 0 |
| INDE | 4 | 43 | 19 | FOBS= | 141.4 | SIGMA= | 2.0 | PHAS= | -123.6 | FOM= | 0.93 | TEST= 0 |
| INDE | 4 | 43 | 21 | FOBS= | 95.7 | SIGMA= | 2.5 | PHAS= | -87.7 | FOM= | 0.82 | TEST= 0 |
| INDE | 4 | 43 | 23 | FOBS= | 171.4 | SIGMA= | 2.3 | PHAS= | -105.6 | FOM= | 0.89 | TEST= 0 |
| INDE | 4 | 43 | 25 | FOBS= | 157.7 | SIGMA= | 2.4 | PHAS= | -48.8 | FOM= | 0.91 | TEST= 0 |
| INDE | 4 | 43 | 27 | FOBS= | 96.9 | SIGMA= | 3.7 | PHAS= | -39.9 | FOM= | 0.79 | TEST= 0 |
| INDE | 4 | 43 | 29 | FOBS= | 62.8 | SIGMA= | 5.5 | PHAS= | 111.0 | FOM= | 0.49 | TEST= 0 |
| INDE | 4 | 43 | 31 | FOBS= | 99.6 | SIGMA= | 3.5 | PHAS= | 80.8 | FOM= | 0.76 | TEST= 0 |
| INDE | 4 | 43 | 33 | FOBS= | 175.7 | SIGMA= | 1.8 | PHAS= | 18.0 | FOM= | 0.93 | TEST= 0 |
| INDE | 4 | 43 | 35 | FOBS= | 148.9 | SIGMA= | 1.7 | PHAS= | 51.2 | FOM= | 0.89 | TEST= 0 |
| INDE | 4 | 43 | 37 | FOBS= | 154.5 | SIGMA= | 1.6 | PHAS= | -7.0 | FOM= | 0.89 | TEST= 0 |
| INDE | 4 | 43 | 39 | FOBS= | 72.3 | SIGMA= | 2.8 | PHAS= | 9.2 | FOM= | 0.39 | TEST= 0 |
| INDE | 4 | 43 | 41 | FOBS= | 33.7 | SIGMA= | 6.5 | PHAS= | -9.4 | FOM= | 0.57 | TEST= 0 |
| INDE | 4 | 43 | 43 | FOBS= | 73.7 | SIGMA= | 2.5 | PHAS= | -154.6 | FOM= | 0.80 | TEST= 0 |
| INDE | 4 | 43 | 45 | FOBS= | 75.7 | SIGMA= | 2.1 | PHAS= | 142.8 | FOM= | 0.72 | TEST= 0 |
| INDE | 4 | 43 | 47 | FOBS= | 60.1 | SIGMA= | 2.5 | PHAS= | 45.5 | FOM= | 0.77 | TEST= 0 |
| INDE | 4 | 43 | 49 | FOBS= | 0.0 | SIGMA= | 18.3 | PHAS= | 0.0 | FOM= | 0.00 | TEST= 0 |
| INDE | 4 | 43 | 51 | FOBS= | 0.0 | SIGMA= | 19.0 | PHAS= | 0.0 | FOM= | 0.00 | TEST= 1 |
| INDE | 4 | 43 | 53 | FOBS= | 46.9 | SIGMA= | 3.7 | PHAS= | 63.5 | FOM= | 0.78 | TEST= 0 |
| INDE | 4 | 43 | 55 | FOBS= | 149.9 | SIGMA= | 1.3 | PHAS= | 86.5 | FOM= | 0.94 | TEST= 0 |
| INDE | 4 | 43 | 57 | FOBS= | 105.7 | SIGMA= | 1.7 | PHAS= | 178.6 | FOM= | 0.94 | TEST= 0 |
| INDE | 4 | 43 | 59 | FOBS= | 42.9 | SIGMA= | 4.4 | PHAS= | -76.2 | FOM= | 0.79 | TEST= 0 |
| INDE | 4 | 43 | 61 | FOBS= | 8.5 | SIGMA= | 30.7 | PHAS= | 1.0 | FOM= | 0.21 | TEST= 0 |
| INDE | 4 | 43 | 63 | FOBS= | 85.4 | SIGMA= | 2.7 | PHAS= | -11.9 | FOM= | 0.81 | TEST= 0 |
| INDE | 4 | 44 | 4 | FOBS= | 42.1 | SIGMA= | 5.4 | PHAS= | -14.5 | FOM= | 0.67 | TEST= 0 |
| INDE | 4 | 44 | 10 | FOBS= | 164.6 | SIGMA= | 1.1 | PHAS= | -1.6 | FOM= | 0.94 | TEST= 0 |
| INDE | 4 | 44 | 12 | FOBS= | 178.0 | SIGMA= | 0.9 | PHAS= | -24.8 | FOM= | 0.95 | TEST= 1 |
| INDE | 4 | 44 | 14 | FOBS= | 49.9 | SIGMA= | 3.0 | PHAS= | 28.6 | FOM= | 0.92 | TEST= 0 |
| INDE | 4 | 44 | 16 | FOBS= | 207.8 | SIGMA= | 1.2 | PHAS= | 20.4 | FOM= | 0.90 | TEST= 0 |
| INDE | 4 | 44 | 18 | FOBS= | 126.9 | SIGMA= | 1.9 | PHAS= | -170.7 | FOM= | 0.97 | TEST= 0 |
| INDE | 4 | 44 | 20 | FOBS= | 186.0 | SIGMA= | 1.4 | PHAS= | 111.2 | FOM= | 0.68 | TEST= 0 |
| INDE | 4 | 44 | 22 | FOBS= | 85.2 | SIGMA= | 2.9 | PHAS= | -82.0 | FOM= | 0.87 | TEST= 0 |
| INDE | 4 | 44 | 24 | FOBS= | 299.9 | SIGMA= | 1.5 | PHAS= | 169.7 | FOM= | 0.97 | TEST= 0 |
| INDE | 4 | 44 | 26 | FOBS= | 150.9 | SIGMA= | 2.5 | PHAS= | 80.8 | FOM= | 0.79 | TEST= 0 |
| INDE | 4 | 44 | 28 | FOBS= | 265.0 | SIGMA= | 1.6 | PHAS= | 30.6 | FOM= | 0.96 | TEST= 0 |
| INDE | 4 | 44 | 30 | FOBS= | 0.0 | SIGMA= | 25.8 | PHAS= | 0.0 | FOM= | 0.00 | TEST= 0 |
| INDE | 4 | 44 | 32 | FOBS= | 113.3 | SIGMA= | 3.0 | PHAS= | -141.6 | FOM= | 0.91 | TEST= 0 |
| INDE | 4 | 44 | 34 | FOBS= | 129.5 | SIGMA= | 2.1 | PHAS= | -48.3 | FOM= | 0.91 | TEST= 0 |
| INDE | 4 | 44 | 36 | FOBS= | 103.3 | SIGMA= | 2.4 | PHAS= | 28.7 | FOM= | 0.73 | TEST= 0 |
| INDE | 4 | 44 | 38 | FOBS= | 50.2 | SIGMA= | 4.3 | PHAS= | -55.7 | FOM= | 0.51 | TEST= 0 |
| INDE | 4 | 44 | 40 | FOBS= | 71.4 | SIGMA= | 2.8 | PHAS= | 174.5 | FOM= | 0.75 | TEST= 0 |
| INDE | 4 | 44 | 42 | FOBS= | 40.5 | SIGMA= | 4.5 | PHAS= | -78.8 | FOM= | 0.57 | TEST= 0 |
| INDE | 4 | 44 | 44 | FOBS= | 101.0 | SIGMA= | 1.7 | PHAS= | 43.3 | FOM= | 0.79 | TEST= 0 |
| INDE | 4 | 44 | 46 | FOBS= | 71.3 | SIGMA= | 2.2 | PHAS= | 50.8 | FOM= | 0.91 | TEST= 0 |
| INDE | 4 | 44 | 48 | FOBS= | 88.5 | SIGMA= | 1.7 | PHAS= | -20.7 | FOM= | 0.92 | TEST= 0 |
| INDE | 4 | 44 | 50 | FOBS= | 44.6 | SIGMA= | 4.1 | PHAS= | 144.3 | FOM= | 0.69 | TEST= 0 |
| INDE | 4 | 44 | 52 | FOBS= | 72.9 | SIGMA= | 2.4 | PHAS= | 9.8 | FOM= | 0.77 | TEST= 0 |

*FIG. 12A - 123*

| | | | | | | | | | | |
|---|---|---|---|---|---|---|---|---|---|---|
| INDE | 4 | 44 | 54 | FOBS= | 59.3 | SIGMA= | 3.0 | PHAS= | -64.9 | FOM= 0.83 | TEST= 0 |
| INDE | 4 | 44 | 56 | FOBS= | 105.2 | SIGMA= | 1.7 | PHAS= | 60.6 | FOM= 0.93 | TEST= 0 |
| INDE | 4 | 44 | 58 | FOBS= | 0.0 | SIGMA= | 19.3 | PHAS= | 0.0 | FOM= 0.00 | TEST= 0 |
| INDE | 4 | 44 | 60 | FOBS= | 54.3 | SIGMA= | 3.3 | PHAS= | -138.2 | FOM= 0.73 | TEST= 0 |
| INDE | 4 | 44 | 62 | FOBS= | 18.4 | SIGMA= | 15.0 | PHAS= | -85.2 | FOM= 0.25 | TEST= 0 |
| INDE | 4 | 44 | 64 | FOBS= | 12.3 | SIGMA= | 45.2 | PHAS= | 131.1 | FOM= 0.28 | TEST= 0 |
| INDE | 4 | 45 | 5 | FOBS= | 209.0 | SIGMA= | 1.3 | PHAS= | 155.1 | FOM= 0.95 | TEST= 0 |
| INDE | 4 | 45 | 11 | FOBS= | 146.0 | SIGMA= | 1.3 | PHAS= | -122.9 | FOM= 0.95 | TEST= 0 |
| INDE | 4 | 45 | 13 | FOBS= | 170.2 | SIGMA= | 1.0 | PHAS= | -178.3 | FOM= 0.98 | TEST= 0 |
| INDE | 4 | 45 | 15 | FOBS= | 222.1 | SIGMA= | 0.8 | PHAS= | -148.6 | FOM= 0.94 | TEST= 0 |
| INDE | 4 | 45 | 17 | FOBS= | 265.3 | SIGMA= | 1.1 | PHAS= | -98.7 | FOM= 0.95 | TEST= 0 |
| INDE | 4 | 45 | 19 | FOBS= | 142.0 | SIGMA= | 1.8 | PHAS= | 85.6 | FOM= 0.79 | TEST= 0 |
| INDE | 4 | 45 | 21 | FOBS= | 207.7 | SIGMA= | 1.3 | PHAS= | -49.0 | FOM= 0.38 | TEST= 1 |
| INDE | 4 | 45 | 23 | FOBS= | 85.6 | SIGMA= | 2.8 | PHAS= | 69.4 | FOM= 0.62 | TEST= 0 |
| INDE | 4 | 45 | 25 | FOBS= | 140.1 | SIGMA= | 2.7 | PHAS= | 39.3 | FOM= 0.92 | TEST= 0 |
| INDE | 4 | 45 | 27 | FOBS= | 146.0 | SIGMA= | 2.5 | PHAS= | 40.5 | FOM= 0.18 | TEST= 1 |
| INDE | 4 | 45 | 29 | FOBS= | 89.6 | SIGMA= | 3.8 | PHAS= | -84.9 | FOM= 0.84 | TEST= 0 |
| INDE | 4 | 45 | 31 | FOBS= | 30.2 | SIGMA= | 11.0 | PHAS= | 150.4 | FOM= 0.27 | TEST= 0 |
| INDE | 4 | 45 | 33 | FOBS= | 148.4 | SIGMA= | 2.4 | PHAS= | 12.5 | FOM= 0.91 | TEST= 0 |
| INDE | 4 | 45 | 35 | FOBS= | 80.1 | SIGMA= | 3.2 | PHAS= | -108.4 | FOM= 0.77 | TEST= 0 |
| INDE | 4 | 45 | 37 | FOBS= | 60.1 | SIGMA= | 3.9 | PHAS= | -7.7 | FOM= 0.30 | TEST= 0 |
| INDE | 4 | 45 | 39 | FOBS= | 0.0 | SIGMA= | 20.4 | PHAS= | 0.0 | FOM= 0.00 | TEST= 0 |
| INDE | 4 | 45 | 41 | FOBS= | 120.4 | SIGMA= | 1.6 | PHAS= | 116.1 | FOM= 0.92 | TEST= 0 |
| INDE | 4 | 45 | 43 | FOBS= | 53.4 | SIGMA= | 3.5 | PHAS= | -51.6 | FOM= 0.20 | TEST= 1 |
| INDE | 4 | 45 | 45 | FOBS= | 95.3 | SIGMA= | 1.7 | PHAS= | 4.0 | FOM= 0.86 | TEST= 0 |
| INDE | 4 | 45 | 47 | FOBS= | 41.1 | SIGMA= | 3.9 | PHAS= | -128.9 | FOM= 0.65 | TEST= 0 |
| INDE | 4 | 45 | 49 | FOBS= | 39.6 | SIGMA= | 4.0 | PHAS= | -173.2 | FOM= 0.46 | TEST= 0 |
| INDE | 4 | 45 | 51 | FOBS= | 101.8 | SIGMA= | 1.8 | PHAS= | 10.4 | FOM= 0.91 | TEST= 0 |
| INDE | 4 | 45 | 53 | FOBS= | 18.2 | SIGMA= | 10.8 | PHAS= | -58.5 | FOM= 0.03 | TEST= 0 |
| INDE | 4 | 45 | 55 | FOBS= | 39.8 | SIGMA= | 5.0 | PHAS= | 47.4 | FOM= 0.67 | TEST= 0 |
| INDE | 4 | 45 | 57 | FOBS= | 0.0 | SIGMA= | 20.7 | PHAS= | 0.0 | FOM= 0.00 | TEST= 0 |
| INDE | 4 | 45 | 59 | FOBS= | 53.2 | SIGMA= | 3.4 | PHAS= | 156.0 | FOM= 0.15 | TEST= 1 |
| INDE | 4 | 45 | 61 | FOBS= | 37.0 | SIGMA= | 5.9 | PHAS= | 69.6 | FOM= 0.75 | TEST= 0 |
| INDE | 4 | 45 | 63 | FOBS= | 85.3 | SIGMA= | 3.3 | PHAS= | 23.1 | FOM= 0.87 | TEST= 0 |
| INDE | 4 | 46 | 4 | FOBS= | 242.6 | SIGMA= | 1.2 | PHAS= | 87.4 | FOM= 0.98 | TEST= 0 |
| INDE | 4 | 46 | 10 | FOBS= | 83.7 | SIGMA= | 2.3 | PHAS= | -156.7 | FOM= 0.45 | TEST= 0 |
| INDE | 4 | 46 | 12 | FOBS= | 126.6 | SIGMA= | 1.2 | PHAS= | 173.7 | FOM= 0.98 | TEST= 0 |
| INDE | 4 | 46 | 14 | FOBS= | 316.8 | SIGMA= | 0.9 | PHAS= | 116.0 | FOM= 0.97 | TEST= 0 |
| INDE | 4 | 46 | 16 | FOBS= | 254.0 | SIGMA= | 1.1 | PHAS= | 75.5 | FOM= 0.95 | TEST= 0 |
| INDE | 4 | 46 | 18 | FOBS= | 134.0 | SIGMA= | 1.8 | PHAS= | -130.6 | FOM= 0.93 | TEST= 0 |
| INDE | 4 | 46 | 20 | FOBS= | 49.5 | SIGMA= | 4.9 | PHAS= | 30.7 | FOM= 0.33 | TEST= 0 |
| INDE | 4 | 46 | 22 | FOBS= | 0.0 | SIGMA= | 23.4 | PHAS= | 0.0 | FOM= 0.00 | TEST= 0 |
| INDE | 4 | 46 | 24 | FOBS= | 194.1 | SIGMA= | 1.3 | PHAS= | -125.8 | FOM= 0.90 | TEST= 0 |
| INDE | 4 | 46 | 26 | FOBS= | 32.4 | SIGMA= | 10.8 | PHAS= | 100.9 | FOM= 0.30 | TEST= 0 |
| INDE | 4 | 46 | 28 | FOBS= | 84.3 | SIGMA= | 4.1 | PHAS= | 119.8 | FOM= 0.60 | TEST= 0 |
| INDE | 4 | 46 | 30 | FOBS= | 77.2 | SIGMA= | 4.4 | PHAS= | -143.3 | FOM= 0.79 | TEST= 0 |
| INDE | 4 | 46 | 32 | FOBS= | 92.7 | SIGMA= | 3.7 | PHAS= | -76.4 | FOM= 0.57 | TEST= 0 |
| INDE | 4 | 46 | 34 | FOBS= | 90.4 | SIGMA= | 3.7 | PHAS= | -157.2 | FOM= 0.90 | TEST= 0 |
| INDE | 4 | 46 | 36 | FOBS= | 177.3 | SIGMA= | 1.4 | PHAS= | 85.5 | FOM= 0.96 | TEST= 0 |
| INDE | 4 | 46 | 38 | FOBS= | 59.5 | SIGMA= | 3.4 | PHAS= | 49.1 | FOM= 0.68 | TEST= 0 |
| INDE | 4 | 46 | 40 | FOBS= | 65.5 | SIGMA= | 3.0 | PHAS= | 117.5 | FOM= 0.62 | TEST= 1 |
| INDE | 4 | 46 | 42 | FOBS= | 31.8 | SIGMA= | 5.8 | PHAS= | -74.1 | FOM= 0.76 | TEST= 0 |
| INDE | 4 | 46 | 44 | FOBS= | 90.5 | SIGMA= | 1.9 | PHAS= | -4.5 | FOM= 0.63 | TEST= 0 |
| INDE | 4 | 46 | 46 | FOBS= | 59.4 | SIGMA= | 2.6 | PHAS= | -141.9 | FOM= 0.76 | TEST= 0 |
| INDE | 4 | 46 | 48 | FOBS= | 0.0 | SIGMA= | 19.1 | PHAS= | 0.0 | FOM= 0.00 | TEST= 0 |
| INDE | 4 | 46 | 50 | FOBS= | 39.6 | SIGMA= | 4.4 | PHAS= | 179.9 | FOM= 0.64 | TEST= 0 |
| INDE | 4 | 46 | 52 | FOBS= | 97.1 | SIGMA= | 1.9 | PHAS= | -117.0 | FOM= 0.72 | TEST= 1 |
| INDE | 4 | 46 | 54 | FOBS= | 24.0 | SIGMA= | 9.9 | PHAS= | 58.2 | FOM= 0.02 | TEST= 1 |
| INDE | 4 | 46 | 56 | FOBS= | 56.8 | SIGMA= | 3.2 | PHAS= | 37.7 | FOM= 0.76 | TEST= 0 |
| INDE | 4 | 46 | 58 | FOBS= | 18.2 | SIGMA= | 10.5 | PHAS= | -32.0 | FOM= 0.03 | TEST= 1 |
| INDE | 4 | 46 | 60 | FOBS= | 39.5 | SIGMA= | 4.9 | PHAS= | 108.8 | FOM= 0.70 | TEST= 0 |
| INDE | 4 | 46 | 62 | FOBS= | 34.9 | SIGMA= | 6.9 | PHAS= | -45.9 | FOM= 0.72 | TEST= 0 |
| INDE | 4 | 47 | 5 | FOBS= | 157.4 | SIGMA= | 2.5 | PHAS= | 36.0 | FOM= 0.95 | TEST= 0 |
| INDE | 4 | 47 | 11 | FOBS= | 366.8 | SIGMA= | 0.9 | PHAS= | 135.6 | FOM= 0.95 | TEST= 0 |
| INDE | 4 | 47 | 13 | FOBS= | 117.2 | SIGMA= | 1.4 | PHAS= | 103.5 | FOM= 0.93 | TEST= 0 |
| INDE | 4 | 47 | 15 | FOBS= | 160.4 | SIGMA= | 1.1 | PHAS= | 88.7 | FOM= 0.90 | TEST= 0 |
| INDE | 4 | 47 | 17 | FOBS= | 292.1 | SIGMA= | 1.1 | PHAS= | -70.0 | FOM= 0.96 | TEST= 0 |
| INDE | 4 | 47 | 19 | FOBS= | 79.1 | SIGMA= | 3.0 | PHAS= | -54.5 | FOM= 0.21 | TEST= 0 |
| INDE | 4 | 47 | 21 | FOBS= | 165.6 | SIGMA= | 1.8 | PHAS= | -121.4 | FOM= 0.91 | TEST= 0 |
| INDE | 4 | 47 | 23 | FOBS= | 69.6 | SIGMA= | 3.4 | PHAS= | 35.3 | FOM= 0.28 | TEST= 0 |

*FIG. 12A - 124*

```
INDE  4  47  25 FOBS=   62.2 SIGMA=  3.8 PHAS= -125.5 FOM= 0.25 TEST= 0
INDE  4  47  27 FOBS=  117.1 SIGMA=  3.1 PHAS=   41.0 FOM= 0.86 TEST= 0
INDE  4  47  29 FOBS=   55.1 SIGMA=  6.3 PHAS= -169.4 FOM= 0.72 TEST= 0
INDE  4  47  31 FOBS=    0.0 SIGMA= 26.0 PHAS=    0.0 FOM= 0.00 TEST= 0
INDE  4  47  33 FOBS=    0.0 SIGMA= 25.7 PHAS=    0.0 FOM= 0.00 TEST= 0
INDE  4  47  35 FOBS=   63.3 SIGMA=  4.5 PHAS=  -90.8 FOM= 0.73 TEST= 0
INDE  4  47  37 FOBS=  143.3 SIGMA=  1.6 PHAS=  -18.6 FOM= 0.93 TEST= 0
INDE  4  47  39 FOBS=   85.6 SIGMA=  2.3 PHAS=  -44.6 FOM= 0.96 TEST= 0
INDE  4  47  41 FOBS=   87.0 SIGMA=  2.2 PHAS=  138.2 FOM= 0.94 TEST= 0
INDE  4  47  43 FOBS=   83.5 SIGMA=  2.3 PHAS=  134.4 FOM= 0.76 TEST= 0
INDE  4  47  45 FOBS=    0.0 SIGMA= 17.6 PHAS=    0.0 FOM= 0.00 TEST= 0
INDE  4  47  47 FOBS=  106.4 SIGMA=  1.5 PHAS=  172.4 FOM= 0.92 TEST= 0
INDE  4  47  49 FOBS=   48.9 SIGMA=  3.7 PHAS=   89.7 FOM= 0.82 TEST= 0
INDE  4  47  51 FOBS=    0.0 SIGMA= 20.3 PHAS=    0.0 FOM= 0.00 TEST= 0
INDE  4  47  53 FOBS=   19.8 SIGMA=  8.9 PHAS=  -66.7 FOM= 0.13 TEST= 1
INDE  4  47  55 FOBS=    0.0 SIGMA= 24.3 PHAS=    0.0 FOM= 0.00 TEST= 0
INDE  4  47  57 FOBS=   15.6 SIGMA= 13.3 PHAS=  154.1 FOM= 0.11 TEST= 0
INDE  4  47  59 FOBS=    0.0 SIGMA= 20.4 PHAS=    0.0 FOM= 0.00 TEST= 0
INDE  4  47  61 FOBS=   59.9 SIGMA=  4.1 PHAS=   -9.0 FOM= 0.81 TEST= 0
INDE  4  48   4 FOBS=   52.8 SIGMA=  5.0 PHAS=  166.8 FOM= 0.82 TEST= 0
INDE  4  48  10 FOBS=  201.2 SIGMA=  2.9 PHAS=  -19.4 FOM= 0.89 TEST= 0
INDE  4  48  12 FOBS=  293.6 SIGMA=  1.0 PHAS=  145.9 FOM= 0.94 TEST= 0
INDE  4  48  14 FOBS=   93.6 SIGMA=  1.8 PHAS=   20.0 FOM= 0.96 TEST= 0
INDE  4  48  16 FOBS=  151.6 SIGMA=  1.2 PHAS=    7.2 FOM= 0.91 TEST= 0
INDE  4  48  18 FOBS=  162.1 SIGMA=  1.5 PHAS= -114.4 FOM= 0.95 TEST= 0
INDE  4  48  20 FOBS=    0.0 SIGMA= 24.5 PHAS=    0.0 FOM= 0.00 TEST= 0
INDE  4  48  22 FOBS=   59.5 SIGMA=  4.0 PHAS=  -32.8 FOM= 0.84 TEST= 0
INDE  4  48  24 FOBS=  107.9 SIGMA=  2.2 PHAS=   91.1 FOM= 0.89 TEST= 0
INDE  4  48  26 FOBS=  105.9 SIGMA=  2.3 PHAS= -120.6 FOM= 0.86 TEST= 0
INDE  4  48  28 FOBS=    0.0 SIGMA= 26.4 PHAS=    0.0 FOM= 0.00 TEST= 0
INDE  4  48  30 FOBS=   54.6 SIGMA=  6.4 PHAS=   84.8 FOM= 0.80 TEST= 0
INDE  4  48  32 FOBS=  101.9 SIGMA=  3.4 PHAS=   62.2 FOM= 0.94 TEST= 0
INDE  4  48  34 FOBS=  144.5 SIGMA=  2.4 PHAS= -150.6 FOM= 0.94 TEST= 0
INDE  4  48  36 FOBS=   35.2 SIGMA=  7.1 PHAS= -142.4 FOM= 0.27 TEST= 0
INDE  4  48  38 FOBS=   81.8 SIGMA=  2.4 PHAS= -140.9 FOM= 0.95 TEST= 0
INDE  4  48  40 FOBS=   55.3 SIGMA=  3.6 PHAS=  166.3 FOM= 0.75 TEST= 0
INDE  4  48  42 FOBS=   89.6 SIGMA=  2.1 PHAS=   43.9 FOM= 0.93 TEST= 0
INDE  4  48  44 FOBS=   52.3 SIGMA=  3.2 PHAS=   46.9 FOM= 0.80 TEST= 0
INDE  4  48  46 FOBS=   44.9 SIGMA=  3.7 PHAS=  117.2 FOM= 0.23 TEST= 0
INDE  4  48  48 FOBS=   53.1 SIGMA=  3.0 PHAS=   77.2 FOM= 0.83 TEST= 0
INDE  4  48  50 FOBS=    0.0 SIGMA= 19.3 PHAS=    0.0 FOM= 0.00 TEST= 0
INDE  4  48  52 FOBS=   48.2 SIGMA=  3.7 PHAS= -157.4 FOM= 0.72 TEST= 0
INDE  4  48  54 FOBS=   63.4 SIGMA=  2.8 PHAS=  148.6 FOM= 0.90 TEST= 0
INDE  4  48  56 FOBS=    0.0 SIGMA= 21.2 PHAS=    0.0 FOM= 0.00 TEST= 0
INDE  4  48  58 FOBS=   54.4 SIGMA=  3.6 PHAS= -148.9 FOM= 0.05 TEST= 1
INDE  4  48  60 FOBS=   49.5 SIGMA=  4.6 PHAS= -158.2 FOM= 0.52 TEST= 0
INDE  4  49   9 FOBS=   52.3 SIGMA= 10.4 PHAS=   17.8 FOM= 0.31 TEST= 0
INDE  4  49  11 FOBS=  149.0 SIGMA=  1.6 PHAS= -107.3 FOM= 0.88 TEST= 0
INDE  4  49  13 FOBS=  140.8 SIGMA=  1.2 PHAS= -126.9 FOM= 0.93 TEST= 0
INDE  4  49  15 FOBS=   90.4 SIGMA=  1.8 PHAS= -130.4 FOM= 0.84 TEST= 0
INDE  4  49  17 FOBS=  311.7 SIGMA=  0.8 PHAS= -142.0 FOM= 0.97 TEST= 0
INDE  4  49  19 FOBS=  145.3 SIGMA=  1.7 PHAS= -148.5 FOM= 0.94 TEST= 0
INDE  4  49  21 FOBS=  135.3 SIGMA=  1.8 PHAS=  -86.3 FOM= 0.89 TEST= 0
INDE  4  49  23 FOBS=  211.1 SIGMA=  1.3 PHAS=  -31.7 FOM= 0.94 TEST= 0
INDE  4  49  25 FOBS=    0.0 SIGMA= 21.6 PHAS=    0.0 FOM= 0.00 TEST= 0
INDE  4  49  27 FOBS=   52.0 SIGMA=  4.4 PHAS= -108.3 FOM= 0.49 TEST= 0
INDE  4  49  29 FOBS=   77.1 SIGMA=  4.5 PHAS=   45.5 FOM= 0.81 TEST= 0
INDE  4  49  31 FOBS=  201.2 SIGMA=  1.9 PHAS=  -17.9 FOM= 0.96 TEST= 0
INDE  4  49  33 FOBS=  132.1 SIGMA=  2.6 PHAS=  -64.3 FOM= 0.93 TEST= 0
INDE  4  49  35 FOBS=   76.9 SIGMA=  4.3 PHAS=  140.2 FOM= 0.76 TEST= 0
INDE  4  49  37 FOBS=   35.8 SIGMA=  7.0 PHAS=  130.0 FOM= 0.78 TEST= 0
INDE  4  49  39 FOBS=   26.2 SIGMA= 10.1 PHAS=  166.4 FOM= 0.59 TEST= 0
INDE  4  49  41 FOBS=   18.7 SIGMA= 10.2 PHAS=  177.8 FOM= 0.13 TEST= 0
INDE  4  49  43 FOBS=    0.0 SIGMA= 21.7 PHAS=    0.0 FOM= 0.00 TEST= 1
INDE  4  49  45 FOBS=    0.0 SIGMA= 18.3 PHAS=    0.0 FOM= 0.00 TEST= 0
INDE  4  49  47 FOBS=   20.7 SIGMA=  8.9 PHAS=  144.4 FOM= 0.06 TEST= 0
INDE  4  49  49 FOBS=   87.8 SIGMA=  2.1 PHAS=   53.4 FOM= 0.76 TEST= 0
INDE  4  49  51 FOBS=   63.2 SIGMA=  2.8 PHAS=  120.5 FOM= 0.84 TEST= 0
INDE  4  49  53 FOBS=   91.1 SIGMA=  2.0 PHAS=   51.2 FOM= 0.89 TEST= 0
INDE  4  49  55 FOBS=   33.5 SIGMA=  5.4 PHAS=   87.5 FOM= 0.80 TEST= 0
```

*FIG. 12A - 125*

```
INDE  4  49  57  FOBS=   49.0  SIGMA=   3.8  PHAS=   95.7  FOM= 0.31  TEST= 0
INDE  4  49  59  FOBS=   27.6  SIGMA=   9.2  PHAS=   34.4  FOM= 0.33  TEST= 0
INDE  4  50   4  FOBS=  172.3  SIGMA=   1.1  PHAS= -153.0  FOM= 0.58  TEST= 1
INDE  4  50  10  FOBS=   55.1  SIGMA=   9.8  PHAS= -129.4  FOM= 0.26  TEST= 0
INDE  4  50  12  FOBS=  145.1  SIGMA=   1.3  PHAS=  129.9  FOM= 0.78  TEST= 1
INDE  4  50  14  FOBS=    0.0  SIGMA=  17.4  PHAS=    0.0  FOM= 0.00  TEST= 0
INDE  4  50  16  FOBS=  106.7  SIGMA=   1.6  PHAS=  119.9  FOM= 0.84  TEST= 0
INDE  4  50  18  FOBS=  120.1  SIGMA=   1.5  PHAS=  118.3  FOM= 0.90  TEST= 0
INDE  4  50  20  FOBS=   52.4  SIGMA=   4.3  PHAS=  104.5  FOM= 0.73  TEST= 0
INDE  4  50  22  FOBS=  197.4  SIGMA=   1.3  PHAS= -125.0  FOM= 0.94  TEST= 0
INDE  4  50  24  FOBS=    0.0  SIGMA=  23.1  PHAS=    0.0  FOM= 0.00  TEST= 1
INDE  4  50  26  FOBS=   70.3  SIGMA=   3.4  PHAS=  -82.7  FOM= 0.90  TEST= 0
INDE  4  50  28  FOBS=   63.2  SIGMA=   5.4  PHAS=  -58.4  FOM= 0.28  TEST= 0
INDE  4  50  30  FOBS=  129.8  SIGMA=   2.7  PHAS=  -63.2  FOM= 0.84  TEST= 0
INDE  4  50  32  FOBS=   53.1  SIGMA=   6.2  PHAS= -119.0  FOM= 0.39  TEST= 0
INDE  4  50  34  FOBS=   94.2  SIGMA=   3.6  PHAS= -170.6  FOM= 0.89  TEST= 0
INDE  4  50  36  FOBS=  114.1  SIGMA=   2.6  PHAS=   32.1  FOM= 0.85  TEST= 0
INDE  4  50  38  FOBS=   47.1  SIGMA=   4.1  PHAS= -165.3  FOM= 0.67  TEST= 0
INDE  4  50  40  FOBS=   27.7  SIGMA=   7.4  PHAS=   48.7  FOM= 0.50  TEST= 0
INDE  4  50  42  FOBS=   19.3  SIGMA=  10.5  PHAS=   45.5  FOM= 0.30  TEST= 0
INDE  4  50  44  FOBS=   70.7  SIGMA=   2.4  PHAS=  -81.0  FOM= 0.78  TEST= 0
INDE  4  50  46  FOBS=   49.1  SIGMA=   3.2  PHAS=   54.3  FOM= 0.50  TEST= 0
INDE  4  50  48  FOBS=   45.6  SIGMA=   4.5  PHAS=  126.6  FOM= 0.61  TEST= 0
INDE  4  50  50  FOBS=    9.5  SIGMA=  22.4  PHAS= -131.9  FOM= 0.01  TEST= 1
INDE  4  50  52  FOBS=   29.0  SIGMA=   6.7  PHAS= -149.9  FOM= 0.22  TEST= 0
INDE  4  50  54  FOBS=   10.6  SIGMA=  17.8  PHAS=  -46.3  FOM= 0.16  TEST= 0
INDE  4  50  56  FOBS=   56.5  SIGMA=   3.3  PHAS=  -80.9  FOM= 0.79  TEST= 0
INDE  4  50  58  FOBS=   73.4  SIGMA=   3.1  PHAS=   14.4  FOM= 0.11  TEST= 1
INDE  4  51   9  FOBS=   89.9  SIGMA=   5.9  PHAS=   93.7  FOM= 0.46  TEST= 0
INDE  4  51  11  FOBS=  201.5  SIGMA=   2.1  PHAS=  168.2  FOM= 0.86  TEST= 0
INDE  4  51  13  FOBS=  121.9  SIGMA=   1.6  PHAS= -134.0  FOM= 0.85  TEST= 0
INDE  4  51  15  FOBS=  134.9  SIGMA=   1.2  PHAS=    5.7  FOM= 0.77  TEST= 0
INDE  4  51  17  FOBS=  112.2  SIGMA=   1.5  PHAS=  155.8  FOM= 0.46  TEST= 1
INDE  4  51  19  FOBS=   97.6  SIGMA=   1.8  PHAS=   12.4  FOM= 0.10  TEST= 0
INDE  4  51  21  FOBS=   59.1  SIGMA=   3.8  PHAS= -150.6  FOM= 0.65  TEST= 0
INDE  4  51  23  FOBS=    0.0  SIGMA=  21.6  PHAS=    0.0  FOM= 0.00  TEST= 0
INDE  4  51  25  FOBS=   47.7  SIGMA=   4.9  PHAS=  161.7  FOM= 0.20  TEST= 0
INDE  4  51  27  FOBS=   77.0  SIGMA=   3.1  PHAS=   37.2  FOM= 0.71  TEST= 0
INDE  4  51  29  FOBS=   46.0  SIGMA=   7.4  PHAS=  141.4  FOM= 0.62  TEST= 0
INDE  4  51  31  FOBS=   30.9  SIGMA=  10.8  PHAS=   39.9  FOM= 0.48  TEST= 0
INDE  4  51  33  FOBS=   51.3  SIGMA=   6.4  PHAS=   79.0  FOM= 0.62  TEST= 0
INDE  4  51  35  FOBS=   68.5  SIGMA=   4.9  PHAS=   21.4  FOM= 0.60  TEST= 0
INDE  4  51  37  FOBS=   86.0  SIGMA=   2.6  PHAS=  -16.9  FOM= 0.79  TEST= 0
INDE  4  51  39  FOBS=    0.0  SIGMA=  20.9  PHAS=    0.0  FOM= 0.00  TEST= 0
INDE  4  51  41  FOBS=    0.0  SIGMA=  18.9  PHAS=    0.0  FOM= 0.00  TEST= 0
INDE  4  51  43  FOBS=    0.0  SIGMA=  19.6  PHAS=    0.0  FOM= 0.00  TEST= 0
INDE  4  51  45  FOBS=    0.0  SIGMA=  18.0  PHAS=    0.0  FOM= 0.00  TEST= 0
INDE  4  51  47  FOBS=   43.5  SIGMA=   3.7  PHAS= -155.8  FOM= 0.50  TEST= 0
INDE  4  51  49  FOBS=   74.1  SIGMA=   2.5  PHAS=  -88.0  FOM= 0.68  TEST= 0
INDE  4  51  51  FOBS=  102.2  SIGMA=   1.9  PHAS=   61.7  FOM= 0.90  TEST= 0
INDE  4  51  53  FOBS=   72.8  SIGMA=   2.5  PHAS=  151.6  FOM= 0.04  TEST= 0
INDE  4  51  55  FOBS=   48.8  SIGMA=   4.0  PHAS=  159.9  FOM= 0.77  TEST= 0
INDE  4  51  57  FOBS=   50.2  SIGMA=   4.6  PHAS=  132.4  FOM= 0.83  TEST= 0
INDE  4  52   4  FOBS=  174.9  SIGMA=   1.6  PHAS= -174.5  FOM= 0.65  TEST= 0
INDE  4  52   8  FOBS=   53.5  SIGMA=  10.0  PHAS=    5.5  FOM= 0.12  TEST= 0
INDE  4  52  10  FOBS=   96.4  SIGMA=   4.0  PHAS=   77.1  FOM= 0.49  TEST= 0
INDE  4  52  12  FOBS=  291.9  SIGMA=   0.9  PHAS=  129.4  FOM= 0.98  TEST= 0
INDE  4  52  14  FOBS=   36.2  SIGMA=   5.7  PHAS=   17.3  FOM= 0.49  TEST= 0
INDE  4  52  16  FOBS=   67.8  SIGMA=   2.4  PHAS=  177.0  FOM= 0.76  TEST= 0
INDE  4  52  18  FOBS=    0.0  SIGMA=  18.4  PHAS=    0.0  FOM= 0.00  TEST= 0
INDE  4  52  20  FOBS=   58.2  SIGMA=   2.9  PHAS=  -33.8  FOM= 0.49  TEST= 0
INDE  4  52  22  FOBS=   77.1  SIGMA=   3.0  PHAS=  -62.4  FOM= 0.59  TEST= 1
INDE  4  52  24  FOBS=  114.1  SIGMA=   2.1  PHAS=  -61.7  FOM= 0.94  TEST= 0
INDE  4  52  26  FOBS=  108.5  SIGMA=   2.2  PHAS=  -14.9  FOM= 0.15  TEST= 1
INDE  4  52  28  FOBS=   86.6  SIGMA=   2.7  PHAS=    7.7  FOM= 0.85  TEST= 0
INDE  4  52  30  FOBS=   88.7  SIGMA=   3.9  PHAS=   19.7  FOM= 0.82  TEST= 0
INDE  4  52  32  FOBS=  111.5  SIGMA=   3.1  PHAS=   -1.8  FOM= 0.74  TEST= 0
INDE  4  52  34  FOBS=  111.2  SIGMA=   3.1  PHAS= -107.7  FOM= 0.93  TEST= 0
INDE  4  52  36  FOBS=   35.7  SIGMA=   9.9  PHAS=   66.8  FOM= 0.47  TEST= 0
INDE  4  52  38  FOBS=   77.5  SIGMA=   2.7  PHAS=   85.6  FOM= 0.83  TEST= 0
```

*FIG. 12A - 126*

```
INDE  4  52  40  FOBS=   47.1  SIGMA=   4.1  PHAS=   -86.9  FOM=  0.39  TEST= 0
INDE  4  52  42  FOBS=    0.0  SIGMA=  19.4  PHAS=     0.0  FOM=  0.00  TEST= 1
INDE  4  52  44  FOBS=   62.8  SIGMA=   2.6  PHAS=  -122.7  FOM=  0.40  TEST= 0
INDE  4  52  46  FOBS=   37.6  SIGMA=   5.0  PHAS=   -43.2  FOM=  0.28  TEST= 0
INDE  4  52  48  FOBS=  116.5  SIGMA=   1.7  PHAS=   123.5  FOM=  0.92  TEST= 0
INDE  4  52  50  FOBS=   20.7  SIGMA=   8.8  PHAS=  -107.7  FOM=  0.50  TEST= 0
INDE  4  52  52  FOBS=    0.0  SIGMA=  21.2  PHAS=     0.0  FOM=  0.00  TEST= 0
INDE  4  52  54  FOBS=    0.0  SIGMA=  20.2  PHAS=     0.0  FOM=  0.00  TEST= 1
INDE  4  52  56  FOBS=   75.7  SIGMA=   3.1  PHAS=   -43.2  FOM=  0.83  TEST= 0
INDE  4  53   5  FOBS=  121.8  SIGMA=   1.4  PHAS=     0.0  FOM=  0.00  TEST= 1
INDE  4  53   9  FOBS=    0.0  SIGMA=  32.3  PHAS=     0.0  FOM=  0.00  TEST= 0
INDE  4  53  11  FOBS=   82.0  SIGMA=   4.6  PHAS=    73.1  FOM=  0.56  TEST= 0
INDE  4  53  13  FOBS=  210.2  SIGMA=   1.2  PHAS=    -2.6  FOM=  0.95  TEST= 0
INDE  4  53  15  FOBS=  225.0  SIGMA=   0.9  PHAS=   -20.6  FOM=  0.85  TEST= 0
INDE  4  53  17  FOBS=    0.0  SIGMA=  19.0  PHAS=     0.0  FOM=  0.00  TEST= 0
INDE  4  53  19  FOBS=   67.3  SIGMA=   2.6  PHAS=  -172.4  FOM=  0.75  TEST= 0
INDE  4  53  21  FOBS=  127.0  SIGMA=   1.8  PHAS=   138.0  FOM=  0.86  TEST= 0
INDE  4  53  23  FOBS=   74.6  SIGMA=   3.1  PHAS=   127.5  FOM=  0.50  TEST= 0
INDE  4  53  25  FOBS=  189.2  SIGMA=   1.4  PHAS=  -148.9  FOM=  0.94  TEST= 0
INDE  4  53  27  FOBS=  137.4  SIGMA=   1.8  PHAS=    20.3  FOM=  0.83  TEST= 0
INDE  4  53  29  FOBS=   99.5  SIGMA=   2.4  PHAS=   -28.8  FOM=  0.12  TEST= 1
INDE  4  53  31  FOBS=   75.6  SIGMA=   4.5  PHAS=   -48.2  FOM=  0.15  TEST= 0
INDE  4  53  33  FOBS=   35.7  SIGMA=   9.2  PHAS=   169.9  FOM=  0.60  TEST= 0
INDE  4  53  35  FOBS=   26.0  SIGMA=  13.6  PHAS=   -26.8  FOM=  0.53  TEST= 0
INDE  4  53  37  FOBS=  137.2  SIGMA=   1.9  PHAS=   -31.0  FOM=  0.94  TEST= 0
INDE  4  53  39  FOBS=   46.2  SIGMA=   4.4  PHAS=   -66.0  FOM=  0.74  TEST= 0
INDE  4  53  41  FOBS=    0.0  SIGMA=  18.9  PHAS=     0.0  FOM=  0.00  TEST= 0
INDE  4  53  43  FOBS=    0.0  SIGMA=  18.3  PHAS=     0.0  FOM=  0.00  TEST= 0
INDE  4  53  45  FOBS=   81.4  SIGMA=   2.0  PHAS=   138.7  FOM=  0.84  TEST= 0
INDE  4  53  47  FOBS=   74.4  SIGMA=   2.6  PHAS=   111.2  FOM=  0.62  TEST= 0
INDE  4  53  49  FOBS=   20.9  SIGMA=   9.4  PHAS=   164.7  FOM=  0.25  TEST= 0
INDE  4  53  51  FOBS=   45.8  SIGMA=   4.1  PHAS=    18.4  FOM=  0.51  TEST= 0
INDE  4  53  53  FOBS=   52.3  SIGMA=   3.6  PHAS=     7.8  FOM=  0.82  TEST= 0
INDE  4  53  55  FOBS=  110.0  SIGMA=   2.4  PHAS=   174.2  FOM=  0.94  TEST= 0
INDE  4  54   8  FOBS=  140.6  SIGMA=   3.9  PHAS=    76.7  FOM=  0.60  TEST= 0
INDE  4  54  10  FOBS=  129.3  SIGMA=   3.0  PHAS=   -16.2  FOM=  0.79  TEST= 0
INDE  4  54  12  FOBS=  108.6  SIGMA=   3.6  PHAS=  -113.1  FOM=  0.87  TEST= 0
INDE  4  54  14  FOBS=  129.6  SIGMA=   1.5  PHAS=  -111.3  FOM=  0.91  TEST= 0
INDE  4  54  16  FOBS=   61.9  SIGMA=   2.5  PHAS=  -140.2  FOM=  0.32  TEST= 0
INDE  4  54  18  FOBS=  154.0  SIGMA=   1.1  PHAS=  -148.3  FOM=  0.91  TEST= 0
INDE  4  54  20  FOBS=   49.9  SIGMA=   3.5  PHAS=    52.3  FOM=  0.53  TEST= 0
INDE  4  54  22  FOBS=   48.4  SIGMA=   4.6  PHAS=    26.7  FOM=  0.58  TEST= 0
INDE  4  54  24  FOBS=   19.7  SIGMA=  11.5  PHAS=    33.3  FOM=  0.45  TEST= 0
INDE  4  54  26  FOBS=   64.7  SIGMA=   3.6  PHAS=   -68.3  FOM=  0.52  TEST= 1
INDE  4  54  28  FOBS=   63.5  SIGMA=   3.7  PHAS=  -116.3  FOM=  0.78  TEST= 0
INDE  4  54  30  FOBS=   95.5  SIGMA=   2.5  PHAS=    47.8  FOM=  0.85  TEST= 0
INDE  4  54  32  FOBS=   60.8  SIGMA=   5.5  PHAS=   104.2  FOM=  0.83  TEST= 0
INDE  4  54  34  FOBS=   95.7  SIGMA=   3.0  PHAS=  -124.2  FOM=  0.90  TEST= 0
INDE  4  54  36  FOBS=    0.0  SIGMA=  21.9  PHAS=     0.0  FOM=  0.00  TEST= 0
INDE  4  54  38  FOBS=   93.5  SIGMA=   2.7  PHAS=   120.1  FOM=  0.94  TEST= 0
INDE  4  54  40  FOBS=    0.0  SIGMA=  20.8  PHAS=     0.0  FOM=  0.00  TEST= 1
INDE  4  54  42  FOBS=   61.9  SIGMA=   3.0  PHAS=   -86.6  FOM=  0.85  TEST= 0
INDE  4  54  44  FOBS=  103.6  SIGMA=   1.6  PHAS=  -136.5  FOM=  0.81  TEST= 0
INDE  4  54  46  FOBS=    0.0  SIGMA=  18.5  PHAS=     0.0  FOM=  0.00  TEST= 0
INDE  4  54  48  FOBS=   36.3  SIGMA=   5.1  PHAS=   100.2  FOM=  0.45  TEST= 0
INDE  4  54  50  FOBS=   13.4  SIGMA=  15.5  PHAS=  -141.2  FOM=  0.26  TEST= 0
INDE  4  54  52  FOBS=   41.9  SIGMA=   4.8  PHAS=   -35.7  FOM=  0.76  TEST= 0
INDE  4  54  54  FOBS=   32.4  SIGMA=   8.6  PHAS=   -39.2  FOM=  0.23  TEST= 0
INDE  4  55   5  FOBS=  189.2  SIGMA=   1.4  PHAS=   174.5  FOM=  0.99  TEST= 0
INDE  4  55   7  FOBS=  131.2  SIGMA=   4.1  PHAS=    10.8  FOM=  0.71  TEST= 0
INDE  4  55   9  FOBS=  158.3  SIGMA=   2.5  PHAS=  -152.1  FOM=  0.83  TEST= 0
INDE  4  55  11  FOBS=  143.3  SIGMA=   2.7  PHAS=  -109.4  FOM=  0.91  TEST= 0
INDE  4  55  13  FOBS=  171.2  SIGMA=   2.3  PHAS=    88.1  FOM=  0.96  TEST= 0
INDE  4  55  15  FOBS=    0.0  SIGMA=  20.1  PHAS=     0.0  FOM=  0.00  TEST= 0
INDE  4  55  17  FOBS=   70.6  SIGMA=   2.2  PHAS=   176.4  FOM=  0.86  TEST= 0
INDE  4  55  19  FOBS=  181.8  SIGMA=   1.0  PHAS=    31.8  FOM=  0.96  TEST= 0
INDE  4  55  21  FOBS=    0.0  SIGMA=  19.7  PHAS=     0.0  FOM=  0.00  TEST= 0
INDE  4  55  23  FOBS=   87.5  SIGMA=   2.6  PHAS=  -117.1  FOM=  0.82  TEST= 0
INDE  4  55  25  FOBS=    0.0  SIGMA=  21.4  PHAS=     0.0  FOM=  0.00  TEST= 0
INDE  4  55  27  FOBS=   48.5  SIGMA=   4.8  PHAS=   -93.2  FOM=  0.49  TEST= 0
```

*FIG. 12A - 127*

```
INDE  4  55  29 FOBS=   93.6 SIGMA=   2.5 PHAS=   -6.8 FOM=  0.85 TEST= 0
INDE  4  55  31 FOBS=   66.5 SIGMA=   3.5 PHAS=    7.2 FOM=  0.78 TEST= 0
INDE  4  55  33 FOBS=    0.0 SIGMA=  23.7 PHAS=    0.0 FOM=  0.00 TEST= 0
INDE  4  55  35 FOBS=    0.0 SIGMA=  23.9 PHAS=    0.0 FOM=  0.00 TEST= 0
INDE  4  55  37 FOBS=  124.9 SIGMA=   2.1 PHAS=   28.0 FOM=  0.95 TEST= 0
INDE  4  55  39 FOBS=   68.4 SIGMA=   3.3 PHAS=  -22.1 FOM=  0.89 TEST= 0
INDE  4  55  41 FOBS=   58.8 SIGMA=   3.1 PHAS= -157.7 FOM=  0.63 TEST= 0
INDE  4  55  43 FOBS=  112.3 SIGMA=   1.6 PHAS=  166.8 FOM=  0.60 TEST= 1
INDE  4  55  45 FOBS=   41.3 SIGMA=   3.9 PHAS=  134.2 FOM=  0.49 TEST= 0
INDE  4  55  47 FOBS=   42.4 SIGMA=   4.9 PHAS= -147.5 FOM=  0.07 TEST= 1
INDE  4  55  49 FOBS=   24.8 SIGMA=   8.2 PHAS=  -89.4 FOM=  0.02 TEST= 1
INDE  4  55  51 FOBS=   75.9 SIGMA=   3.0 PHAS=  -36.6 FOM=  0.87 TEST= 0
INDE  4  55  53 FOBS=    0.0 SIGMA=  23.7 PHAS=    0.0 FOM=  0.00 TEST= 0
INDE  4  56   6 FOBS=   99.3 SIGMA=   5.4 PHAS= -167.4 FOM=  0.49 TEST= 0
INDE  4  56   8 FOBS=  109.0 SIGMA=   3.5 PHAS=  148.5 FOM=  0.70 TEST= 0
INDE  4  56  10 FOBS=   73.2 SIGMA=   5.1 PHAS=   15.0 FOM=  0.71 TEST= 0
INDE  4  56  12 FOBS=   30.8 SIGMA=  11.7 PHAS= -179.0 FOM=  0.18 TEST= 0
INDE  4  56  14 FOBS=   46.8 SIGMA=   3.9 PHAS=   43.1 FOM=  0.16 TEST= 0
INDE  4  56  16 FOBS=  122.5 SIGMA=   1.3 PHAS=  111.7 FOM=  0.93 TEST= 0
INDE  4  56  18 FOBS=   76.4 SIGMA=   2.1 PHAS= -140.4 FOM=  0.80 TEST= 0
INDE  4  56  20 FOBS=  168.3 SIGMA=   1.1 PHAS= -119.7 FOM=  0.95 TEST= 0
INDE  4  56  22 FOBS=   81.1 SIGMA=   2.1 PHAS= -166.4 FOM=  0.68 TEST= 0
INDE  4  56  24 FOBS=   10.5 SIGMA=  21.2 PHAS=  -96.6 FOM=  0.25 TEST= 0
INDE  4  56  26 FOBS=    0.0 SIGMA=  21.4 PHAS=    0.0 FOM=  0.00 TEST= 0
INDE  4  56  28 FOBS=   40.6 SIGMA=   5.7 PHAS=  -55.7 FOM=  0.68 TEST= 0
INDE  4  56  30 FOBS=   36.9 SIGMA=   7.2 PHAS=   69.0 FOM=  0.72 TEST= 0
INDE  4  56  32 FOBS=    0.0 SIGMA=  21.4 PHAS=    0.0 FOM=  0.00 TEST= 0
INDE  4  56  34 FOBS=   37.1 SIGMA=   6.6 PHAS= -171.1 FOM=  0.21 TEST= 0
INDE  4  56  36 FOBS=   27.5 SIGMA=   8.8 PHAS= -173.0 FOM=  0.00 TEST= 1
INDE  4  56  38 FOBS=   35.5 SIGMA=   6.7 PHAS=   29.5 FOM=  0.57 TEST= 0
INDE  4  56  40 FOBS=   79.8 SIGMA=   2.6 PHAS=  109.3 FOM=  0.75 TEST= 0
INDE  4  56  42 FOBS=   33.9 SIGMA=   5.6 PHAS=  110.1 FOM=  0.44 TEST= 0
INDE  4  56  44 FOBS=   26.7 SIGMA=   6.4 PHAS=   92.8 FOM=  0.06 TEST= 0
INDE  4  56  46 FOBS=    0.0 SIGMA=  22.3 PHAS=    0.0 FOM=  0.00 TEST= 0
INDE  4  56  48 FOBS=   15.3 SIGMA=  14.4 PHAS=  -51.7 FOM=  0.07 TEST= 0
INDE  4  56  50 FOBS=   59.1 SIGMA=   3.8 PHAS= -162.9 FOM=  0.85 TEST= 0
INDE  4  56  52 FOBS=   47.3 SIGMA=   6.0 PHAS=  -36.2 FOM=  0.84 TEST= 0
INDE  4  57   5 FOBS=  122.6 SIGMA=   1.5 PHAS= -111.9 FOM=  0.95 TEST= 0
INDE  4  57   7 FOBS=  122.3 SIGMA=   3.2 PHAS=   79.6 FOM=  0.89 TEST= 0
INDE  4  57   9 FOBS=    0.0 SIGMA=  27.0 PHAS=    0.0 FOM=  0.00 TEST= 0
INDE  4  57  11 FOBS=   91.7 SIGMA=   4.1 PHAS= -110.5 FOM=  0.76 TEST= 0
INDE  4  57  13 FOBS=   39.4 SIGMA=   9.1 PHAS=    0.9 FOM=  0.10 TEST= 1
INDE  4  57  15 FOBS=   51.6 SIGMA=   3.5 PHAS=  -70.4 FOM=  0.23 TEST= 0
INDE  4  57  17 FOBS=   99.7 SIGMA=   1.6 PHAS=   60.1 FOM=  0.97 TEST= 0
INDE  4  57  19 FOBS=  136.9 SIGMA=   1.2 PHAS=   95.4 FOM=  0.94 TEST= 0
INDE  4  57  21 FOBS=  111.7 SIGMA=   1.6 PHAS=  178.5 FOM=  0.70 TEST= 1
INDE  4  57  23 FOBS=    0.0 SIGMA=  19.6 PHAS=    0.0 FOM=  0.00 TEST= 0
INDE  4  57  25 FOBS=   32.8 SIGMA=   7.7 PHAS=  105.6 FOM=  0.16 TEST= 0
INDE  4  57  27 FOBS=   35.6 SIGMA=   6.5 PHAS=   -6.7 FOM=  0.76 TEST= 0
INDE  4  57  29 FOBS=   32.2 SIGMA=   7.2 PHAS=  175.6 FOM=  0.23 TEST= 0
INDE  4  57  31 FOBS=  122.7 SIGMA=   2.0 PHAS=   55.3 FOM=  0.93 TEST= 0
INDE  4  57  33 FOBS=    0.0 SIGMA=  20.5 PHAS=    0.0 FOM=  0.00 TEST= 0
INDE  4  57  35 FOBS=   37.2 SIGMA=   6.5 PHAS=  -89.9 FOM=  0.54 TEST= 0
INDE  4  57  37 FOBS=   49.1 SIGMA=   4.9 PHAS=  -11.1 FOM=  0.85 TEST= 0
INDE  4  57  39 FOBS=   98.1 SIGMA=   2.9 PHAS=  -37.8 FOM=  0.93 TEST= 0
INDE  4  57  41 FOBS=  134.9 SIGMA=   1.8 PHAS=   31.5 FOM=  0.97 TEST= 0
INDE  4  57  43 FOBS=   63.0 SIGMA=   2.9 PHAS= -143.5 FOM=  0.62 TEST= 0
INDE  4  57  45 FOBS=   26.1 SIGMA=   9.0 PHAS=  -32.3 FOM=  0.36 TEST= 0
INDE  4  57  47 FOBS=   47.5 SIGMA=   4.7 PHAS=  153.7 FOM=  0.81 TEST= 0
INDE  4  57  49 FOBS=    0.0 SIGMA=  21.1 PHAS=    0.0 FOM=  0.00 TEST= 0
INDE  4  57  51 FOBS=    0.0 SIGMA=  25.5 PHAS=    0.0 FOM=  0.00 TEST= 0
INDE  4  58   4 FOBS=  109.9 SIGMA=   2.1 PHAS=  105.2 FOM=  0.87 TEST= 0
INDE  4  58   6 FOBS=   61.6 SIGMA=   2.2 PHAS=  150.9 FOM=  0.53 TEST= 0
INDE  4  58   8 FOBS=  109.4 SIGMA=   3.5 PHAS=   55.1 FOM=  0.80 TEST= 0
INDE  4  58  10 FOBS=   42.2 SIGMA=   8.7 PHAS=  115.3 FOM=  0.30 TEST= 0
INDE  4  58  12 FOBS=   77.9 SIGMA=   4.7 PHAS=  145.6 FOM=  0.77 TEST= 1
INDE  4  58  14 FOBS=   49.2 SIGMA=   7.3 PHAS= -173.1 FOM=  0.59 TEST= 0
INDE  4  58  16 FOBS=   60.1 SIGMA=   3.1 PHAS=  -63.1 FOM=  0.50 TEST= 1
INDE  4  58  18 FOBS=   66.9 SIGMA=   2.3 PHAS=  -17.6 FOM=  0.91 TEST= 0
INDE  4  58  20 FOBS=  118.7 SIGMA=   1.4 PHAS=  175.5 FOM=  0.90 TEST= 0
```

*FIG. 12A - 128*

```
INDE  4  58  22  FOBS=   12.3  SIGMA=  17.1  PHAS=  -143.5  FOM=  0.31  TEST=  0
INDE  4  58  24  FOBS=   82.2  SIGMA=   2.1  PHAS=   -40.4  FOM=  0.92  TEST=  0
INDE  4  58  26  FOBS=   67.8  SIGMA=   3.4  PHAS=  -100.0  FOM=  0.93  TEST=  0
INDE  4  58  28  FOBS=   73.7  SIGMA=   3.2  PHAS=    82.8  FOM=  0.30  TEST=  1
INDE  4  58  30  FOBS=   77.8  SIGMA=   3.0  PHAS=    13.1  FOM=  0.82  TEST=  0
INDE  4  58  32  FOBS=   34.0  SIGMA=   7.8  PHAS=   -69.3  FOM=  0.47  TEST=  0
INDE  4  58  34  FOBS=   33.2  SIGMA=   7.0  PHAS=   -33.3  FOM=  0.41  TEST=  0
INDE  4  58  36  FOBS=    0.0  SIGMA=  26.6  PHAS=     0.0  FOM=  0.00  TEST=  0
INDE  4  58  38  FOBS=   51.2  SIGMA=   6.5  PHAS=  -144.6  FOM=  0.74  TEST=  0
INDE  4  58  40  FOBS=  120.6  SIGMA=   2.8  PHAS=   -50.9  FOM=  0.96  TEST=  0
INDE  4  58  42  FOBS=   69.5  SIGMA=   2.8  PHAS=   -70.4  FOM=  0.35  TEST=  1
INDE  4  58  44  FOBS=   68.3  SIGMA=   2.7  PHAS=  -165.6  FOM=  0.68  TEST=  0
INDE  4  58  46  FOBS=   19.3  SIGMA=  12.3  PHAS=   175.9  FOM=  0.29  TEST=  1
INDE  4  58  48  FOBS=   41.9  SIGMA=   5.9  PHAS=   109.0  FOM=  0.66  TEST=  0
INDE  4  58  50  FOBS=   28.0  SIGMA=  11.8  PHAS=   107.1  FOM=  0.39  TEST=  0
INDE  4  59   5  FOBS=  107.8  SIGMA=   1.7  PHAS=   117.1  FOM=  0.98  TEST=  0
INDE  4  59   7  FOBS=   11.4  SIGMA=  31.1  PHAS=    12.1  FOM=  0.13  TEST=  0
INDE  4  59   9  FOBS=   92.2  SIGMA=   4.0  PHAS=    -4.8  FOM=  0.81  TEST=  0
INDE  4  59  11  FOBS=   82.4  SIGMA=   4.5  PHAS=    44.0  FOM=  0.85  TEST=  0
INDE  4  59  13  FOBS=   84.6  SIGMA=   4.3  PHAS=    47.4  FOM=  0.74  TEST=  0
INDE  4  59  15  FOBS=   22.4  SIGMA=  15.8  PHAS=   142.5  FOM=  0.31  TEST=  0
INDE  4  59  17  FOBS=   41.0  SIGMA=   6.4  PHAS=  -113.5  FOM=  0.48  TEST=  0
INDE  4  59  19  FOBS=  140.8  SIGMA=   1.3  PHAS=   161.5  FOM=  0.92  TEST=  0
INDE  4  59  21  FOBS=    0.0  SIGMA=  19.4  PHAS=     0.0  FOM=  0.00  TEST=  0
INDE  4  59  23  FOBS=   88.1  SIGMA=   2.3  PHAS=  -153.3  FOM=  0.80  TEST=  0
INDE  4  59  25  FOBS=   61.4  SIGMA=   3.2  PHAS=  -123.8  FOM=  0.86  TEST=  0
INDE  4  59  27  FOBS=   29.8  SIGMA=   7.6  PHAS=  -136.0  FOM=  0.28  TEST=  0
INDE  4  59  29  FOBS=   76.4  SIGMA=   3.1  PHAS=  -102.3  FOM=  0.91  TEST=  0
INDE  4  59  31  FOBS=   64.1  SIGMA=   3.4  PHAS=   -94.0  FOM=  0.36  TEST=  0
INDE  4  59  33  FOBS=   43.8  SIGMA=   5.4  PHAS=    -2.1  FOM=  0.78  TEST=  0
INDE  4  59  35  FOBS=    0.0  SIGMA=  21.6  PHAS=     0.0  FOM=  0.00  TEST=  0
INDE  4  59  37  FOBS=   64.3  SIGMA=   5.2  PHAS=    92.7  FOM=  0.76  TEST=  0
INDE  4  59  39  FOBS=  150.6  SIGMA=   2.4  PHAS=  -119.8  FOM=  0.97  TEST=  0
INDE  4  59  41  FOBS=    0.0  SIGMA=  22.2  PHAS=     0.0  FOM=  0.00  TEST=  0
INDE  4  59  43  FOBS=   69.5  SIGMA=   2.6  PHAS=  -138.2  FOM=  0.76  TEST=  0
INDE  4  59  45  FOBS=    0.0  SIGMA=  20.9  PHAS=     0.0  FOM=  0.00  TEST=  0
INDE  4  59  47  FOBS=   37.0  SIGMA=   8.4  PHAS=    88.7  FOM=  0.74  TEST=  0
INDE  4  59  49  FOBS=    0.0  SIGMA=  25.7  PHAS=     0.0  FOM=  0.00  TEST=  0
INDE  4  60   4  FOBS=  113.6  SIGMA=   2.0  PHAS=    39.4  FOM=  0.80  TEST=  1
INDE  4  60   6  FOBS=    0.0  SIGMA=  13.6  PHAS=     0.0  FOM=  0.00  TEST=  0
INDE  4  60   8  FOBS=   69.1  SIGMA=   5.2  PHAS=   -23.5  FOM=  0.46  TEST=  0
INDE  4  60  10  FOBS=   65.2  SIGMA=   5.5  PHAS=    48.6  FOM=  0.50  TEST=  1
INDE  4  60  12  FOBS=   18.4  SIGMA=  19.6  PHAS=   -51.8  FOM=  0.12  TEST=  0
INDE  4  60  14  FOBS=    8.8  SIGMA=  40.3  PHAS=    66.6  FOM=  0.12  TEST=  0
INDE  4  60  16  FOBS=  119.1  SIGMA=   2.0  PHAS=   150.9  FOM=  0.85  TEST=  0
INDE  4  60  18  FOBS=  168.2  SIGMA=   1.2  PHAS=   139.0  FOM=  0.97  TEST=  0
INDE  4  60  20  FOBS=   87.9  SIGMA=   2.1  PHAS=  -146.7  FOM=  0.25  TEST=  1
INDE  4  60  22  FOBS=   39.7  SIGMA=   4.8  PHAS=  -166.3  FOM=  0.65  TEST=  0
INDE  4  60  24  FOBS=  119.5  SIGMA=   1.7  PHAS=    -1.4  FOM=  0.86  TEST=  0
INDE  4  60  26  FOBS=   36.3  SIGMA=   5.5  PHAS=   -79.3  FOM=  0.68  TEST=  0
INDE  4  60  28  FOBS=   83.7  SIGMA=   2.8  PHAS=   133.9  FOM=  0.88  TEST=  0
INDE  4  60  30  FOBS=  136.8  SIGMA=   2.2  PHAS=   160.3  FOM=  0.96  TEST=  0
INDE  4  60  32  FOBS=  118.5  SIGMA=   2.5  PHAS=   -84.9  FOM=  0.91  TEST=  0
INDE  4  60  34  FOBS=  111.0  SIGMA=   2.6  PHAS=   -50.5  FOM=  0.96  TEST=  0
INDE  4  60  36  FOBS=   78.8  SIGMA=   3.6  PHAS=     5.1  FOM=  0.91  TEST=  0
INDE  4  60  38  FOBS=  120.8  SIGMA=   2.9  PHAS=   171.7  FOM=  0.95  TEST=  0
INDE  4  60  40  FOBS=   64.8  SIGMA=   5.1  PHAS=   -32.7  FOM=  0.88  TEST=  0
INDE  4  60  42  FOBS=   28.0  SIGMA=   7.9  PHAS=   -74.9  FOM=  0.29  TEST=  0
INDE  4  60  44  FOBS=    0.0  SIGMA=  20.4  PHAS=     0.0  FOM=  0.00  TEST=  0
INDE  4  60  46  FOBS=   55.8  SIGMA=   4.8  PHAS=    26.2  FOM=  0.83  TEST=  0
INDE  4  60  48  FOBS=    0.0  SIGMA=  26.2  PHAS=     0.0  FOM=  0.00  TEST=  0
INDE  4  61   5  FOBS=   18.5  SIGMA=  12.9  PHAS=    70.3  FOM=  0.03  TEST=  1
INDE  4  61   7  FOBS=  113.6  SIGMA=   3.2  PHAS=  -162.1  FOM=  0.90  TEST=  0
INDE  4  61   9  FOBS=  112.5  SIGMA=   3.3  PHAS=    38.4  FOM=  0.86  TEST=  0
INDE  4  61  11  FOBS=  101.9  SIGMA=   3.6  PHAS=    58.8  FOM=  0.92  TEST=  0
INDE  4  61  13  FOBS=   46.0  SIGMA=   7.8  PHAS=   -30.4  FOM=  0.53  TEST=  0
INDE  4  61  15  FOBS=    0.0  SIGMA=  26.6  PHAS=     0.0  FOM=  0.00  TEST=  0
INDE  4  61  17  FOBS=  168.6  SIGMA=   2.3  PHAS=    75.2  FOM=  0.98  TEST=  0
INDE  4  61  19  FOBS=   46.0  SIGMA=   4.4  PHAS=   143.6  FOM=  0.69  TEST=  0
INDE  4  61  21  FOBS=  102.9  SIGMA=   2.1  PHAS=     3.1  FOM=  0.90  TEST=  0
```

*FIG. 12A - 129*

```
INDE  4  61  23  FOBS=   42.5  SIGMA=   5.2  PHAS=   52.2  FOM=  0.59  TEST= 1
INDE  4  61  25  FOBS=    0.0  SIGMA=  21.2  PHAS=    0.0  FOM=  0.00  TEST= 0
INDE  4  61  27  FOBS=   59.9  SIGMA=   3.8  PHAS= -162.2  FOM=  0.71  TEST= 0
INDE  4  61  29  FOBS=   94.0  SIGMA=   3.0  PHAS=   76.1  FOM=  0.87  TEST= 0
INDE  4  61  31  FOBS=   67.5  SIGMA=   4.2  PHAS=  170.4  FOM=  0.91  TEST= 0
INDE  4  61  33  FOBS=   66.6  SIGMA=   4.3  PHAS=  -80.1  FOM=  0.84  TEST= 0
INDE  4  61  35  FOBS=  112.7  SIGMA=   2.6  PHAS= -156.5  FOM=  0.93  TEST= 0
INDE  4  61  37  FOBS=   51.0  SIGMA=   5.6  PHAS=   48.6  FOM=  0.79  TEST= 0
INDE  4  61  39  FOBS=   67.6  SIGMA=   5.0  PHAS=  148.3  FOM=  0.86  TEST= 0
INDE  4  61  41  FOBS=   76.8  SIGMA=   3.6  PHAS= -139.7  FOM=  0.92  TEST= 0
INDE  4  61  43  FOBS=   24.9  SIGMA=   7.7  PHAS=   40.2  FOM=  0.23  TEST= 1
INDE  4  61  45  FOBS=   81.5  SIGMA=   3.4  PHAS=  -98.0  FOM=  0.89  TEST= 0
INDE  4  61  47  FOBS=   77.2  SIGMA=   4.6  PHAS=  -49.8  FOM=  0.74  TEST= 0
INDE  4  62   4  FOBS=  147.0  SIGMA=   1.8  PHAS=  127.1  FOM=  0.78  TEST= 0
INDE  4  62   6  FOBS=   52.2  SIGMA=   6.7  PHAS=   85.4  FOM=  0.49  TEST= 0
INDE  4  62   8  FOBS=   31.3  SIGMA=  11.2  PHAS= -122.7  FOM=  0.36  TEST= 0
INDE  4  62  10  FOBS=   94.1  SIGMA=   3.8  PHAS=    2.5  FOM=  0.92  TEST= 0
INDE  4  62  12  FOBS=   60.9  SIGMA=   5.8  PHAS=  -55.2  FOM=  0.88  TEST= 0
INDE  4  62  14  FOBS=   58.9  SIGMA=   6.1  PHAS=   70.7  FOM=  0.87  TEST= 0
INDE  4  62  16  FOBS=   60.5  SIGMA=   5.9  PHAS=   45.6  FOM=  0.68  TEST= 0
INDE  4  62  18  FOBS=  168.8  SIGMA=   1.5  PHAS=   47.0  FOM=  0.87  TEST= 0
INDE  4  62  20  FOBS=   98.6  SIGMA=   2.1  PHAS= -128.4  FOM=  0.93  TEST= 0
INDE  4  62  22  FOBS=  126.5  SIGMA=   1.7  PHAS=  145.7  FOM=  0.04  TEST= 1
INDE  4  62  24  FOBS=   24.7  SIGMA=   8.9  PHAS=  104.6  FOM=  0.49  TEST= 0
INDE  4  62  26  FOBS=   92.8  SIGMA=   2.5  PHAS=  124.8  FOM=  0.87  TEST= 0
INDE  4  62  28  FOBS=   60.4  SIGMA=   3.8  PHAS=  -15.2  FOM=  0.45  TEST= 1
INDE  4  62  30  FOBS=    0.0  SIGMA=  26.2  PHAS=    0.0  FOM=  0.00  TEST= 0
INDE  4  62  32  FOBS=   48.4  SIGMA=   7.1  PHAS=  132.0  FOM=  0.65  TEST= 0
INDE  4  62  34  FOBS=   42.4  SIGMA=   6.7  PHAS=   96.0  FOM=  0.23  TEST= 0
INDE  4  62  36  FOBS=   18.5  SIGMA=  19.2  PHAS=   71.4  FOM=  0.40  TEST= 0
INDE  4  62  38  FOBS=   43.8  SIGMA=   6.5  PHAS=    1.6  FOM=  0.83  TEST= 0
INDE  4  62  40  FOBS=   35.8  SIGMA=   9.3  PHAS= -168.5  FOM=  0.31  TEST= 1
INDE  4  62  42  FOBS=    8.7  SIGMA=  28.5  PHAS=  -42.9  FOM=  0.04  TEST= 0
INDE  4  62  44  FOBS=  114.9  SIGMA=   2.7  PHAS=  -81.6  FOM=  0.87  TEST= 0
INDE  4  62  46  FOBS=   33.8  SIGMA=  10.5  PHAS=  140.6  FOM=  0.70  TEST= 0
INDE  4  63   5  FOBS=   35.7  SIGMA=   6.8  PHAS=    4.4  FOM=  0.45  TEST= 0
INDE  4  63   7  FOBS=   49.6  SIGMA=   4.0  PHAS= -175.4  FOM=  0.87  TEST= 0
INDE  4  63   9  FOBS=  137.7  SIGMA=   2.7  PHAS=  162.2  FOM=  0.95  TEST= 0
INDE  4  63  11  FOBS=   46.2  SIGMA=   7.6  PHAS=  -91.3  FOM=  0.67  TEST= 0
INDE  4  63  13  FOBS=   93.1  SIGMA=   3.9  PHAS=  -24.4  FOM=  0.88  TEST= 0
INDE  4  63  15  FOBS=   92.0  SIGMA=   3.9  PHAS=  -27.9  FOM=  0.88  TEST= 0
INDE  4  63  17  FOBS=   63.3  SIGMA=   5.6  PHAS=  -44.3  FOM=  0.58  TEST= 0
INDE  4  63  19  FOBS=   79.3  SIGMA=   3.0  PHAS=    4.1  FOM=  0.92  TEST= 0
INDE  4  63  21  FOBS=    9.6  SIGMA=  23.3  PHAS=  155.2  FOM=  0.12  TEST= 0
INDE  4  63  23  FOBS=   38.2  SIGMA=   5.6  PHAS= -132.5  FOM=  0.19  TEST= 0
INDE  4  63  25  FOBS=  132.6  SIGMA=   1.8  PHAS=   20.7  FOM=  0.96  TEST= 0
INDE  4  63  27  FOBS=   61.5  SIGMA=   3.8  PHAS=  160.6  FOM=  0.90  TEST= 0
INDE  4  63  29  FOBS=   26.4  SIGMA=   8.8  PHAS= -122.7  FOM=  0.16  TEST= 0
INDE  4  63  31  FOBS=   62.1  SIGMA=   4.6  PHAS= -112.1  FOM=  0.83  TEST= 0
INDE  4  63  33  FOBS=   34.5  SIGMA=   9.9  PHAS= -126.0  FOM=  0.05  TEST= 0
INDE  4  63  35  FOBS=   32.0  SIGMA=  11.0  PHAS= -136.4  FOM=  0.27  TEST= 0
INDE  4  63  37  FOBS=   34.3  SIGMA=   8.3  PHAS=  -83.0  FOM=  0.57  TEST= 0
INDE  4  63  39  FOBS=   31.8  SIGMA=   9.0  PHAS=  138.3  FOM=  0.42  TEST= 0
INDE  4  63  41  FOBS=   59.0  SIGMA=   4.2  PHAS= -153.4  FOM=  0.90  TEST= 0
INDE  4  63  43  FOBS=   70.0  SIGMA=   3.6  PHAS=  154.6  FOM=  0.87  TEST= 0
INDE  4  63  45  FOBS=    0.0  SIGMA=  26.5  PHAS=    0.0  FOM=  0.00  TEST= 0
INDE  4  64   4  FOBS=   63.2  SIGMA=   3.5  PHAS=  -30.7  FOM=  0.72  TEST= 0
INDE  4  64   6  FOBS=   60.7  SIGMA=   4.7  PHAS=   12.7  FOM=  0.66  TEST= 0
INDE  4  64   8  FOBS=  108.2  SIGMA=   3.4  PHAS=   44.6  FOM=  0.87  TEST= 0
INDE  4  64  10  FOBS=  139.5  SIGMA=   2.7  PHAS=   93.6  FOM=  0.94  TEST= 0
INDE  4  64  12  FOBS=   64.5  SIGMA=   5.4  PHAS=  -32.4  FOM=  0.77  TEST= 0
INDE  4  64  14  FOBS=   42.8  SIGMA=   8.2  PHAS= -135.4  FOM=  0.67  TEST= 0
INDE  4  64  16  FOBS=   57.5  SIGMA=   6.2  PHAS=  -94.8  FOM=  0.85  TEST= 0
INDE  4  64  18  FOBS=   43.3  SIGMA=   5.2  PHAS= -148.1  FOM=  0.34  TEST= 0
INDE  4  64  20  FOBS=   75.1  SIGMA=   2.7  PHAS=  -95.2  FOM=  0.63  TEST= 0
INDE  4  64  22  FOBS=  108.0  SIGMA=   2.0  PHAS=  -82.1  FOM=  0.86  TEST= 0
INDE  4  64  24  FOBS=   35.9  SIGMA=   6.1  PHAS= -138.3  FOM=  0.52  TEST= 0
INDE  4  64  26  FOBS=   90.2  SIGMA=   2.6  PHAS=  -12.1  FOM=  0.93  TEST= 0
INDE  4  64  28  FOBS=   47.9  SIGMA=   4.9  PHAS=    9.5  FOM=  0.35  TEST= 0
INDE  4  64  30  FOBS=   90.5  SIGMA=   2.7  PHAS= -176.6  FOM=  0.91  TEST= 0
```

*FIG. 12A - 130*

```
INDE   4   64   32  FOBS=   121.0  SIGMA=   2.5  PHAS=   131.7  FOM=  0.96  TEST=  0
INDE   4   64   34  FOBS=    49.7  SIGMA=   5.8  PHAS=  -136.8  FOM=  0.82  TEST=  0
INDE   4   64   36  FOBS=     0.0  SIGMA=  24.0  PHAS=     0.0  FOM=  0.00  TEST=  0
INDE   4   64   38  FOBS=    40.9  SIGMA=   7.1  PHAS=   -46.2  FOM=  0.74  TEST=  0
INDE   4   64   40  FOBS=    54.8  SIGMA=   4.6  PHAS=   126.2  FOM=  0.74  TEST=  0
INDE   4   64   42  FOBS=    42.6  SIGMA=   5.9  PHAS=    83.1  FOM=  0.76  TEST=  0
INDE   4   65    5  FOBS=   102.3  SIGMA=   2.4  PHAS=   -78.1  FOM=  0.88  TEST=  0
INDE   4   65    7  FOBS=   135.7  SIGMA=   1.2  PHAS=    73.5  FOM=  0.33  TEST=  1
INDE   4   65    9  FOBS=    26.7  SIGMA=  13.0  PHAS=    63.4  FOM=  0.39  TEST=  0
INDE   4   65   11  FOBS=    98.5  SIGMA=   3.7  PHAS=   -91.2  FOM=  0.85  TEST=  0
INDE   4   65   13  FOBS=    72.0  SIGMA=   4.9  PHAS=    30.0  FOM=  0.41  TEST=  0
INDE   4   65   15  FOBS=     0.0  SIGMA=  26.3  PHAS=     0.0  FOM=  0.00  TEST=  0
INDE   4   65   17  FOBS=    23.4  SIGMA=  15.0  PHAS=   176.8  FOM=  0.40  TEST=  0
INDE   4   65   19  FOBS=     0.0  SIGMA=  21.3  PHAS=     0.0  FOM=  0.00  TEST=  0
INDE   4   65   21  FOBS=    41.0  SIGMA=   6.0  PHAS=   -75.0  FOM=  0.47  TEST=  0
INDE   4   65   23  FOBS=    45.4  SIGMA=   4.6  PHAS=   147.5  FOM=  0.67  TEST=  0
INDE   4   65   25  FOBS=    52.3  SIGMA=   4.2  PHAS=  -165.0  FOM=  0.60  TEST=  0
INDE   4   65   27  FOBS=    94.3  SIGMA=   2.5  PHAS=  -122.7  FOM=  0.92  TEST=  0
INDE   4   65   29  FOBS=    36.9  SIGMA=   6.3  PHAS=  -142.0  FOM=  0.17  TEST=  0
INDE   4   65   31  FOBS=    62.7  SIGMA=   3.8  PHAS=    32.5  FOM=  0.90  TEST=  0
INDE   4   65   33  FOBS=     0.0  SIGMA=  24.1  PHAS=     0.0  FOM=  0.00  TEST=  0
INDE   4   65   35  FOBS=    23.1  SIGMA=  12.4  PHAS=    71.6  FOM=  0.10  TEST=  0
INDE   4   65   37  FOBS=     8.9  SIGMA=  33.0  PHAS=   -46.1  FOM=  0.00  TEST=  1
INDE   4   65   39  FOBS=    37.2  SIGMA=   6.9  PHAS=   165.2  FOM=  0.84  TEST=  0
INDE   4   65   41  FOBS=    44.7  SIGMA=   5.2  PHAS=    24.1  FOM=  0.19  TEST=  1
INDE   4   66    4  FOBS=     0.0  SIGMA=  22.0  PHAS=     0.0  FOM=  0.00  TEST=  0
INDE   4   66    6  FOBS=    81.3  SIGMA=   3.0  PHAS=   170.2  FOM=  0.68  TEST=  0
INDE   4   66    8  FOBS=   116.3  SIGMA=   1.8  PHAS=  -122.0  FOM=  0.93  TEST=  0
INDE   4   66   10  FOBS=     4.9  SIGMA=  71.2  PHAS=   -36.6  FOM=  0.08  TEST=  0
INDE   4   66   12  FOBS=    29.8  SIGMA=  11.8  PHAS=  -126.1  FOM=  0.53  TEST=  0
INDE   4   66   14  FOBS=     0.0  SIGMA=  26.3  PHAS=     0.0  FOM=  0.00  TEST=  0
INDE   4   66   16  FOBS=    47.5  SIGMA=   7.4  PHAS=  -141.4  FOM=  0.57  TEST=  0
INDE   4   66   18  FOBS=     0.0  SIGMA=  26.4  PHAS=     0.0  FOM=  0.00  TEST=  1
INDE   4   66   20  FOBS=    46.6  SIGMA=   7.5  PHAS=  -120.1  FOM=  0.54  TEST=  0
INDE   4   66   22  FOBS=     7.7  SIGMA=  29.8  PHAS=   -57.1  FOM=  0.01  TEST=  1
INDE   4   66   24  FOBS=    86.0  SIGMA=   2.5  PHAS=    48.6  FOM=  0.88  TEST=  0
INDE   4   66   26  FOBS=     0.0  SIGMA=  22.7  PHAS=     0.0  FOM=  0.00  TEST=  0
INDE   4   66   28  FOBS=     0.0  SIGMA=  23.4  PHAS=     0.0  FOM=  0.00  TEST=  0
INDE   4   66   30  FOBS=    58.1  SIGMA=   4.9  PHAS=    -1.3  FOM=  0.73  TEST=  0
INDE   4   66   32  FOBS=    92.9  SIGMA=   2.7  PHAS=     1.9  FOM=  0.06  TEST=  1
INDE   4   66   34  FOBS=     0.0  SIGMA=  24.0  PHAS=     0.0  FOM=  0.00  TEST=  0
INDE   4   66   36  FOBS=    40.5  SIGMA=   8.7  PHAS=    81.5  FOM=  0.32  TEST=  0
INDE   4   66   38  FOBS=    17.5  SIGMA=  19.9  PHAS=   116.6  FOM=  0.23  TEST=  0
INDE   4   66   40  FOBS=   107.5  SIGMA=   2.3  PHAS=    38.6  FOM=  0.94  TEST=  0
INDE   4   67    5  FOBS=     0.0  SIGMA=  26.6  PHAS=     0.0  FOM=  0.00  TEST=  0
INDE   4   67    7  FOBS=   110.2  SIGMA=   4.8  PHAS=   153.3  FOM=  0.94  TEST=  0
INDE   4   67    9  FOBS=    52.8  SIGMA=   6.8  PHAS=   136.9  FOM=  0.76  TEST=  0
INDE   4   67   11  FOBS=    61.4  SIGMA=   5.8  PHAS=  -144.9  FOM=  0.80  TEST=  0
INDE   4   67   13  FOBS=    22.9  SIGMA=  15.3  PHAS=  -147.4  FOM=  0.30  TEST=  0
INDE   4   67   15  FOBS=    51.7  SIGMA=   6.8  PHAS=    -5.6  FOM=  0.81  TEST=  0
INDE   4   67   17  FOBS=     0.0  SIGMA=  26.5  PHAS=     0.0  FOM=  0.00  TEST=  0
INDE   4   67   19  FOBS=    91.6  SIGMA=   4.0  PHAS=   155.4  FOM=  0.93  TEST=  0
INDE   4   67   21  FOBS=    38.7  SIGMA=   6.1  PHAS=  -132.3  FOM=  0.40  TEST=  0
INDE   4   67   23  FOBS=    94.0  SIGMA=   2.3  PHAS=    86.4  FOM=  0.89  TEST=  0
INDE   4   67   25  FOBS=    35.7  SIGMA=   7.3  PHAS=  -116.5  FOM=  0.58  TEST=  0
INDE   4   67   27  FOBS=     0.0  SIGMA=  21.6  PHAS=     0.0  FOM=  0.00  TEST=  1
INDE   4   67   29  FOBS=     0.0  SIGMA=  26.0  PHAS=     0.0  FOM=  0.00  TEST=  0
INDE   4   67   31  FOBS=    40.9  SIGMA=   7.0  PHAS=   131.3  FOM=  0.26  TEST=  0
INDE   4   67   33  FOBS=    44.5  SIGMA=   7.9  PHAS=    48.8  FOM=  0.52  TEST=  0
INDE   4   67   35  FOBS=     0.0  SIGMA=  24.2  PHAS=     0.0  FOM=  0.00  TEST=  1
INDE   4   67   37  FOBS=     3.5  SIGMA=  99.7  PHAS=   -24.4  FOM=  0.05  TEST=  0
INDE   4   67   39  FOBS=    78.1  SIGMA=   3.5  PHAS=   -55.4  FOM=  0.84  TEST=  0
INDE   4   68    6  FOBS=    81.2  SIGMA=   4.1  PHAS=    91.9  FOM=  0.86  TEST=  0
INDE   4   68    8  FOBS=    44.3  SIGMA=   4.0  PHAS=    71.5  FOM=  0.74  TEST=  0
INDE   4   68   12  FOBS=     0.0  SIGMA=  31.9  PHAS=     0.0  FOM=  0.00  TEST=  0
INDE   4   68   14  FOBS=    46.2  SIGMA=   7.6  PHAS=   -88.6  FOM=  0.75  TEST=  0
INDE   4   68   16  FOBS=    58.0  SIGMA=   6.1  PHAS=  -143.0  FOM=  0.72  TEST=  0
INDE   4   68   18  FOBS=    26.6  SIGMA=  13.3  PHAS=   -48.0  FOM=  0.52  TEST=  0
INDE   4   68   20  FOBS=    81.9  SIGMA=   2.8  PHAS=    70.0  FOM=  0.86  TEST=  0
INDE   4   68   22  FOBS=    65.3  SIGMA=   3.8  PHAS=    49.3  FOM=  0.84  TEST=  0
```

*FIG. 12A - 131*

| | | | | | | | | | | | | | |
|---|---|---|---|---|---|---|---|---|---|---|---|---|---|
| INDE | 4 | 68 | 24 | FOBS= | 48.1 | SIGMA= | 4.5 | PHAS= | 51.5 | FOM= | 0.08 | TEST= | 0 |
| INDE | 4 | 68 | 26 | FOBS= | 60.1 | SIGMA= | 3.8 | PHAS= | -55.7 | FOM= | 0.90 | TEST= | 0 |
| INDE | 4 | 68 | 28 | FOBS= | 60.1 | SIGMA= | 4.0 | PHAS= | -14.2 | FOM= | 0.20 | TEST= | 1 |
| INDE | 4 | 68 | 30 | FOBS= | 26.1 | SIGMA= | 13.3 | PHAS= | -64.1 | FOM= | 0.36 | TEST= | 0 |
| INDE | 4 | 68 | 32 | FOBS= | 47.4 | SIGMA= | 5.3 | PHAS= | 154.6 | FOM= | 0.82 | TEST= | 0 |
| INDE | 4 | 68 | 34 | FOBS= | 0.0 | SIGMA= | 26.8 | PHAS= | 0.0 | FOM= | 0.00 | TEST= | 0 |
| INDE | 4 | 68 | 36 | FOBS= | 7.5 | SIGMA= | 40.2 | PHAS= | 108.1 | FOM= | 0.11 | TEST= | 0 |
| INDE | 4 | 69 | 5 | FOBS= | 63.0 | SIGMA= | 5.5 | PHAS= | 3.6 | FOM= | 0.84 | TEST= | 0 |
| INDE | 4 | 69 | 7 | FOBS= | 35.3 | SIGMA= | 9.7 | PHAS= | 169.3 | FOM= | 0.39 | TEST= | 0 |
| INDE | 4 | 69 | 9 | FOBS= | 0.0 | SIGMA= | 21.8 | PHAS= | 0.0 | FOM= | 0.00 | TEST= | 0 |
| INDE | 4 | 69 | 15 | FOBS= | 36.5 | SIGMA= | 14.0 | PHAS= | -70.6 | FOM= | 0.15 | TEST= | 0 |
| INDE | 4 | 69 | 17 | FOBS= | 53.5 | SIGMA= | 9.4 | PHAS= | 115.0 | FOM= | 0.76 | TEST= | 0 |
| INDE | 4 | 69 | 19 | FOBS= | 47.4 | SIGMA= | 7.4 | PHAS= | -66.1 | FOM= | 0.49 | TEST= | 0 |
| INDE | 4 | 69 | 21 | FOBS= | 43.4 | SIGMA= | 5.6 | PHAS= | -60.4 | FOM= | 0.77 | TEST= | 0 |
| INDE | 4 | 69 | 23 | FOBS= | 36.1 | SIGMA= | 5.8 | PHAS= | 47.0 | FOM= | 0.73 | TEST= | 0 |
| INDE | 4 | 69 | 25 | FOBS= | 76.4 | SIGMA= | 2.9 | PHAS= | -105.3 | FOM= | 0.89 | TEST= | 0 |
| INDE | 4 | 69 | 27 | FOBS= | 88.6 | SIGMA= | 2.6 | PHAS= | -131.8 | FOM= | 0.84 | TEST= | 0 |
| INDE | 4 | 69 | 29 | FOBS= | 0.0 | SIGMA= | 22.0 | PHAS= | 0.0 | FOM= | 0.00 | TEST= | 0 |
| INDE | 4 | 69 | 31 | FOBS= | 64.7 | SIGMA= | 3.9 | PHAS= | 117.1 | FOM= | 0.81 | TEST= | 0 |
| INDE | 4 | 69 | 33 | FOBS= | 57.1 | SIGMA= | 4.5 | PHAS= | 17.8 | FOM= | 0.23 | TEST= | 0 |
| INDE | 4 | 69 | 35 | FOBS= | 47.0 | SIGMA= | 5.6 | PHAS= | 41.1 | FOM= | 0.70 | TEST= | 0 |
| INDE | 4 | 70 | 4 | FOBS= | 103.9 | SIGMA= | 3.2 | PHAS= | -81.5 | FOM= | 0.94 | TEST= | 0 |
| INDE | 4 | 70 | 6 | FOBS= | 22.5 | SIGMA= | 15.7 | PHAS= | 27.5 | FOM= | 0.06 | TEST= | 0 |
| INDE | 4 | 70 | 20 | FOBS= | 73.1 | SIGMA= | 7.2 | PHAS= | 47.6 | FOM= | 0.81 | TEST= | 0 |
| INDE | 4 | 70 | 22 | FOBS= | 36.6 | SIGMA= | 7.6 | PHAS= | -62.2 | FOM= | 0.74 | TEST= | 0 |
| INDE | 4 | 70 | 24 | FOBS= | 62.8 | SIGMA= | 3.4 | PHAS= | -123.3 | FOM= | 0.62 | TEST= | 0 |
| INDE | 4 | 70 | 26 | FOBS= | 38.8 | SIGMA= | 5.7 | PHAS= | -76.7 | FOM= | 0.46 | TEST= | 0 |
| INDE | 4 | 70 | 28 | FOBS= | 0.0 | SIGMA= | 21.6 | PHAS= | 0.0 | FOM= | 0.00 | TEST= | 0 |
| INDE | 4 | 70 | 30 | FOBS= | 0.0 | SIGMA= | 22.2 | PHAS= | 0.0 | FOM= | 0.00 | TEST= | 0 |
| INDE | 4 | 70 | 32 | FOBS= | 0.0 | SIGMA= | 27.1 | PHAS= | 0.0 | FOM= | 0.00 | TEST= | 0 |
| INDE | 4 | 71 | 5 | FOBS= | 0.0 | SIGMA= | 25.2 | PHAS= | 0.0 | FOM= | 0.00 | TEST= | 0 |
| INDE | 4 | 71 | 7 | FOBS= | 73.8 | SIGMA= | 4.6 | PHAS= | 35.1 | FOM= | 0.80 | TEST= | 0 |
| INDE | 4 | 71 | 9 | FOBS= | 30.4 | SIGMA= | 5.6 | PHAS= | 132.0 | FOM= | 0.35 | TEST= | 0 |
| INDE | 4 | 71 | 23 | FOBS= | 29.0 | SIGMA= | 11.7 | PHAS= | -133.3 | FOM= | 0.39 | TEST= | 0 |
| INDE | 4 | 71 | 25 | FOBS= | 0.0 | SIGMA= | 22.0 | PHAS= | 0.0 | FOM= | 0.00 | TEST= | 0 |
| INDE | 4 | 71 | 27 | FOBS= | 26.4 | SIGMA= | 9.6 | PHAS= | 97.1 | FOM= | 0.32 | TEST= | 0 |
| INDE | 4 | 71 | 29 | FOBS= | 0.0 | SIGMA= | 23.7 | PHAS= | 0.0 | FOM= | 0.00 | TEST= | 0 |
| INDE | 4 | 71 | 31 | FOBS= | 29.8 | SIGMA= | 8.6 | PHAS= | 18.5 | FOM= | 0.32 | TEST= | 0 |
| INDE | 4 | 72 | 4 | FOBS= | 0.0 | SIGMA= | 25.7 | PHAS= | 0.0 | FOM= | 0.00 | TEST= | 0 |
| INDE | 4 | 72 | 6 | FOBS= | 41.7 | SIGMA= | 8.2 | PHAS= | 67.8 | FOM= | 0.60 | TEST= | 0 |
| INDE | 4 | 72 | 8 | FOBS= | 45.0 | SIGMA= | 7.7 | PHAS= | -112.5 | FOM= | 0.14 | TEST= | 0 |
| INDE | 4 | 72 | 10 | FOBS= | 0.0 | SIGMA= | 22.3 | PHAS= | 0.0 | FOM= | 0.00 | TEST= | 0 |
| INDE | 4 | 72 | 24 | FOBS= | 0.0 | SIGMA= | 26.3 | PHAS= | 0.0 | FOM= | 0.00 | TEST= | 0 |
| INDE | 4 | 72 | 26 | FOBS= | 66.4 | SIGMA= | 4.4 | PHAS= | -27.5 | FOM= | 0.75 | TEST= | 0 |
| INDE | 4 | 72 | 28 | FOBS= | 21.9 | SIGMA= | 13.8 | PHAS= | 52.2 | FOM= | 0.27 | TEST= | 0 |
| INDE | 4 | 73 | 5 | FOBS= | 28.4 | SIGMA= | 11.4 | PHAS= | 31.2 | FOM= | 0.36 | TEST= | 0 |
| INDE | 4 | 73 | 7 | FOBS= | 41.8 | SIGMA= | 8.6 | PHAS= | 32.5 | FOM= | 0.84 | TEST= | 0 |
| INDE | 4 | 73 | 23 | FOBS= | 0.0 | SIGMA= | 25.6 | PHAS= | 0.0 | FOM= | 0.00 | TEST= | 0 |
| INDE | 4 | 73 | 25 | FOBS= | 55.2 | SIGMA= | 4.9 | PHAS= | -175.1 | FOM= | 0.34 | TEST= | 0 |
| INDE | 4 | 74 | 4 | FOBS= | 29.1 | SIGMA= | 11.6 | PHAS= | -71.6 | FOM= | 0.43 | TEST= | 0 |
| INDE | 4 | 74 | 6 | FOBS= | 22.5 | SIGMA= | 14.2 | PHAS= | -80.5 | FOM= | 0.61 | TEST= | 0 |
| INDE | 4 | 74 | 8 | FOBS= | 47.2 | SIGMA= | 7.6 | PHAS= | 32.7 | FOM= | 0.72 | TEST= | 0 |
| INDE | 4 | 74 | 10 | FOBS= | 48.6 | SIGMA= | 3.8 | PHAS= | 46.4 | FOM= | 0.43 | TEST= | 0 |
| INDE | 4 | 75 | 5 | FOBS= | 0.0 | SIGMA= | 26.0 | PHAS= | 0.0 | FOM= | 0.00 | TEST= | 0 |
| INDE | 4 | 75 | 7 | FOBS= | 21.9 | SIGMA= | 15.9 | PHAS= | 12.7 | FOM= | 0.50 | TEST= | 0 |
| INDE | 4 | 75 | 9 | FOBS= | 65.9 | SIGMA= | 5.4 | PHAS= | -92.2 | FOM= | 0.85 | TEST= | 0 |
| INDE | 4 | 75 | 11 | FOBS= | 0.0 | SIGMA= | 22.4 | PHAS= | 0.0 | FOM= | 0.00 | TEST= | 0 |
| INDE | 4 | 76 | 4 | FOBS= | 54.8 | SIGMA= | 6.3 | PHAS= | 147.3 | FOM= | 0.50 | TEST= | 0 |
| INDE | 4 | 76 | 6 | FOBS= | 16.9 | SIGMA= | 19.9 | PHAS= | -108.1 | FOM= | 0.35 | TEST= | 0 |
| INDE | 4 | 76 | 12 | FOBS= | 65.1 | SIGMA= | 4.2 | PHAS= | -34.9 | FOM= | 0.30 | TEST= | 0 |
| INDE | 4 | 77 | 5 | FOBS= | 0.0 | SIGMA= | 26.3 | PHAS= | 0.0 | FOM= | 0.00 | TEST= | 0 |
| INDE | 4 | 77 | 7 | FOBS= | 0.0 | SIGMA= | 25.9 | PHAS= | 0.0 | FOM= | 0.00 | TEST= | 0 |
| INDE | 4 | 77 | 9 | FOBS= | 124.7 | SIGMA= | 3.1 | PHAS= | -166.6 | FOM= | 0.94 | TEST= | 0 |
| INDE | 5 | 6 | 17 | FOBS= | 236.0 | SIGMA= | 0.4 | PHAS= | -73.0 | FOM= | 0.90 | TEST= | 0 |
| INDE | 5 | 6 | 19 | FOBS= | 393.2 | SIGMA= | 0.4 | PHAS= | -34.2 | FOM= | 0.94 | TEST= | 0 |
| INDE | 5 | 6 | 21 | FOBS= | 248.0 | SIGMA= | 0.5 | PHAS= | -36.7 | FOM= | 0.96 | TEST= | 0 |
| INDE | 5 | 6 | 23 | FOBS= | 111.2 | SIGMA= | 0.8 | PHAS= | 150.4 | FOM= | 0.94 | TEST= | 0 |
| INDE | 5 | 6 | 25 | FOBS= | 138.8 | SIGMA= | 0.7 | PHAS= | -44.8 | FOM= | 0.98 | TEST= | 0 |
| INDE | 5 | 6 | 27 | FOBS= | 78.9 | SIGMA= | 1.2 | PHAS= | -179.8 | FOM= | 0.63 | TEST= | 0 |
| INDE | 5 | 6 | 29 | FOBS= | 149.5 | SIGMA= | 0.8 | PHAS= | 93.9 | FOM= | 0.88 | TEST= | 0 |

*FIG. 12A - 132*

| | | | | | | | | | | | |
|---|---|---|---|---|---|---|---|---|---|---|---|
| INDE | 5 | 6 | 31 | FOBS= | 167.0 | SIGMA= | 0.9 | PHAS= | 79.2 | FOM= | 0.93 | TEST= 0
| INDE | 5 | 6 | 33 | FOBS= | 174.8 | SIGMA= | 0.7 | PHAS= | 158.6 | FOM= | 0.97 | TEST= 0
| INDE | 5 | 6 | 35 | FOBS= | 212.7 | SIGMA= | 0.8 | PHAS= | 169.2 | FOM= | 0.90 | TEST= 0
| INDE | 5 | 6 | 37 | FOBS= | 256.7 | SIGMA= | 0.8 | PHAS= | 61.5 | FOM= | 0.98 | TEST= 0
| INDE | 5 | 6 | 39 | FOBS= | 118.6 | SIGMA= | 1.2 | PHAS= | 93.8 | FOM= | 0.94 | TEST= 0
| INDE | 5 | 6 | 41 | FOBS= | 314.7 | SIGMA= | 0.7 | PHAS= | -153.2 | FOM= | 0.94 | TEST= 0
| INDE | 5 | 6 | 43 | FOBS= | 195.6 | SIGMA= | 0.9 | PHAS= | 121.5 | FOM= | 0.90 | TEST= 1
| INDE | 5 | 6 | 45 | FOBS= | 153.3 | SIGMA= | 1.2 | PHAS= | 171.9 | FOM= | 0.90 | TEST= 0
| INDE | 5 | 6 | 47 | FOBS= | 139.7 | SIGMA= | 1.5 | PHAS= | -150.9 | FOM= | 0.96 | TEST= 0
| INDE | 5 | 6 | 49 | FOBS= | 130.3 | SIGMA= | 1.6 | PHAS= | 131.6 | FOM= | 0.93 | TEST= 0
| INDE | 5 | 6 | 51 | FOBS= | 212.7 | SIGMA= | 1.4 | PHAS= | 161.8 | FOM= | 0.89 | TEST= 0
| INDE | 5 | 6 | 53 | FOBS= | 128.5 | SIGMA= | 1.5 | PHAS= | 26.6 | FOM= | 0.89 | TEST= 0
| INDE | 5 | 6 | 55 | FOBS= | 111.4 | SIGMA= | 1.7 | PHAS= | 26.4 | FOM= | 0.20 | TEST= 1
| INDE | 5 | 6 | 57 | FOBS= | 252.2 | SIGMA= | 1.3 | PHAS= | -152.5 | FOM= | 0.96 | TEST= 0
| INDE | 5 | 6 | 59 | FOBS= | 68.4 | SIGMA= | 3.8 | PHAS= | -51.5 | FOM= | 0.92 | TEST= 0
| INDE | 5 | 6 | 61 | FOBS= | 53.0 | SIGMA= | 4.8 | PHAS= | 48.9 | FOM= | 0.10 | TEST= 0
| INDE | 5 | 6 | 63 | FOBS= | 50.6 | SIGMA= | 4.1 | PHAS= | 71.5 | FOM= | 0.51 | TEST= 0
| INDE | 5 | 6 | 65 | FOBS= | 122.9 | SIGMA= | 2.1 | PHAS= | 171.5 | FOM= | 0.92 | TEST= 0
| INDE | 5 | 6 | 67 | FOBS= | 129.1 | SIGMA= | 2.8 | PHAS= | 116.2 | FOM= | 0.95 | TEST= 0
| INDE | 5 | 6 | 69 | FOBS= | 93.7 | SIGMA= | 4.1 | PHAS= | 78.3 | FOM= | 0.84 | TEST= 0
| INDE | 5 | 6 | 71 | FOBS= | 46.2 | SIGMA= | 7.8 | PHAS= | 41.6 | FOM= | 0.71 | TEST= 0
| INDE | 5 | 6 | 73 | FOBS= | 0.0 | SIGMA= | 26.7 | PHAS= | 0.0 | FOM= | 0.00 | TEST= 0
| INDE | 5 | 6 | 75 | FOBS= | 48.8 | SIGMA= | 7.2 | PHAS= | -132.4 | FOM= | 0.57 | TEST= 0
| INDE | 5 | 6 | 77 | FOBS= | 45.3 | SIGMA= | 8.0 | PHAS= | -151.3 | FOM= | 0.67 | TEST= 0
| INDE | 5 | 7 | 16 | FOBS= | 313.4 | SIGMA= | 0.4 | PHAS= | -96.3 | FOM= | 0.77 | TEST= 0
| INDE | 5 | 7 | 18 | FOBS= | 118.3 | SIGMA= | 0.5 | PHAS= | -175.9 | FOM= | 0.92 | TEST= 0
| INDE | 5 | 7 | 20 | FOBS= | 320.3 | SIGMA= | 0.4 | PHAS= | -145.0 | FOM= | 0.97 | TEST= 0
| INDE | 5 | 7 | 22 | FOBS= | 205.6 | SIGMA= | 0.5 | PHAS= | 71.9 | FOM= | 0.80 | TEST= 0
| INDE | 5 | 7 | 24 | FOBS= | 122.5 | SIGMA= | 0.7 | PHAS= | 141.2 | FOM= | 0.98 | TEST= 0
| INDE | 5 | 7 | 26 | FOBS= | 48.8 | SIGMA= | 1.6 | PHAS= | -17.9 | FOM= | 0.92 | TEST= 0
| INDE | 5 | 7 | 28 | FOBS= | 200.5 | SIGMA= | 0.6 | PHAS= | 17.8 | FOM= | 0.96 | TEST= 0
| INDE | 5 | 7 | 30 | FOBS= | 50.4 | SIGMA= | 2.0 | PHAS= | 69.8 | FOM= | 0.98 | TEST= 0
| INDE | 5 | 7 | 32 | FOBS= | 226.2 | SIGMA= | 0.6 | PHAS= | 48.6 | FOM= | 0.96 | TEST= 0
| INDE | 5 | 7 | 34 | FOBS= | 249.9 | SIGMA= | 0.6 | PHAS= | 30.1 | FOM= | 0.98 | TEST= 1
| INDE | 5 | 7 | 36 | FOBS= | 110.6 | SIGMA= | 1.1 | PHAS= | -52.2 | FOM= | 0.97 | TEST= 0
| INDE | 5 | 7 | 38 | FOBS= | 74.5 | SIGMA= | 1.8 | PHAS= | 37.2 | FOM= | 0.98 | TEST= 0
| INDE | 5 | 7 | 40 | FOBS= | 174.0 | SIGMA= | 0.9 | PHAS= | 35.5 | FOM= | 0.96 | TEST= 0
| INDE | 5 | 7 | 42 | FOBS= | 284.0 | SIGMA= | 0.8 | PHAS= | 94.0 | FOM= | 0.93 | TEST= 0
| INDE | 5 | 7 | 44 | FOBS= | 91.4 | SIGMA= | 1.9 | PHAS= | -41.3 | FOM= | 0.72 | TEST= 0
| INDE | 5 | 7 | 46 | FOBS= | 228.4 | SIGMA= | 1.1 | PHAS= | 94.2 | FOM= | 0.99 | TEST= 0
| INDE | 5 | 7 | 48 | FOBS= | 121.9 | SIGMA= | 1.7 | PHAS= | 173.4 | FOM= | 0.78 | TEST= 0
| INDE | 5 | 7 | 50 | FOBS= | 70.8 | SIGMA= | 3.3 | PHAS= | 68.9 | FOM= | 0.83 | TEST= 0
| INDE | 5 | 7 | 52 | FOBS= | 99.3 | SIGMA= | 2.0 | PHAS= | -39.2 | FOM= | 0.92 | TEST= 0
| INDE | 5 | 7 | 54 | FOBS= | 75.7 | SIGMA= | 2.5 | PHAS= | 109.8 | FOM= | 0.66 | TEST= 0
| INDE | 5 | 7 | 56 | FOBS= | 208.6 | SIGMA= | 1.0 | PHAS= | 127.4 | FOM= | 0.96 | TEST= 0
| INDE | 5 | 7 | 58 | FOBS= | 120.8 | SIGMA= | 1.6 | PHAS= | -155.0 | FOM= | 0.94 | TEST= 0
| INDE | 5 | 7 | 60 | FOBS= | 158.5 | SIGMA= | 1.5 | PHAS= | -156.6 | FOM= | 0.97 | TEST= 0
| INDE | 5 | 7 | 62 | FOBS= | 0.0 | SIGMA= | 22.2 | PHAS= | 0.0 | FOM= | 0.00 | TEST= 0
| INDE | 5 | 7 | 64 | FOBS= | 107.5 | SIGMA= | 2.2 | PHAS= | 100.9 | FOM= | 0.82 | TEST= 0
| INDE | 5 | 7 | 66 | FOBS= | 121.1 | SIGMA= | 2.2 | PHAS= | 62.9 | FOM= | 0.95 | TEST= 0
| INDE | 5 | 7 | 68 | FOBS= | 28.6 | SIGMA= | 12.6 | PHAS= | -71.3 | FOM= | 0.52 | TEST= 0
| INDE | 5 | 7 | 70 | FOBS= | 34.8 | SIGMA= | 11.0 | PHAS= | 30.1 | FOM= | 0.43 | TEST= 0
| INDE | 5 | 7 | 72 | FOBS= | 36.7 | SIGMA= | 10.2 | PHAS= | 111.0 | FOM= | 0.59 | TEST= 0
| INDE | 5 | 7 | 74 | FOBS= | 15.7 | SIGMA= | 23.3 | PHAS= | 41.9 | FOM= | 0.38 | TEST= 0
| INDE | 5 | 7 | 76 | FOBS= | 0.0 | SIGMA= | 27.0 | PHAS= | 0.0 | FOM= | 0.00 | TEST= 0
| INDE | 5 | 8 | 17 | FOBS= | 359.8 | SIGMA= | 0.4 | PHAS= | -104.0 | FOM= | 0.90 | TEST= 0
| INDE | 5 | 8 | 19 | FOBS= | 82.2 | SIGMA= | 0.6 | PHAS= | -155.9 | FOM= | 0.95 | TEST= 0
| INDE | 5 | 8 | 21 | FOBS= | 101.8 | SIGMA= | 0.6 | PHAS= | 81.4 | FOM= | 0.64 | TEST= 0
| INDE | 5 | 8 | 23 | FOBS= | 145.1 | SIGMA= | 0.5 | PHAS= | 85.5 | FOM= | 0.79 | TEST= 0
| INDE | 5 | 8 | 25 | FOBS= | 73.5 | SIGMA= | 1.1 | PHAS= | -0.5 | FOM= | 0.98 | TEST= 0
| INDE | 5 | 8 | 27 | FOBS= | 92.7 | SIGMA= | 1.1 | PHAS= | -90.3 | FOM= | 0.96 | TEST= 0
| INDE | 5 | 8 | 29 | FOBS= | 166.6 | SIGMA= | 0.7 | PHAS= | -121.4 | FOM= | 0.91 | TEST= 0
| INDE | 5 | 8 | 31 | FOBS= | 114.2 | SIGMA= | 1.0 | PHAS= | -19.7 | FOM= | 0.72 | TEST= 0
| INDE | 5 | 8 | 33 | FOBS= | 83.9 | SIGMA= | 1.4 | PHAS= | 114.5 | FOM= | 0.89 | TEST= 0
| INDE | 5 | 8 | 35 | FOBS= | 369.0 | SIGMA= | 0.5 | PHAS= | -79.1 | FOM= | 0.98 | TEST= 0
| INDE | 5 | 8 | 37 | FOBS= | 421.2 | SIGMA= | 0.7 | PHAS= | -51.7 | FOM= | 0.98 | TEST= 0
| INDE | 5 | 8 | 39 | FOBS= | 267.7 | SIGMA= | 0.8 | PHAS= | -165.5 | FOM= | 0.96 | TEST= 0
| INDE | 5 | 8 | 41 | FOBS= | 131.7 | SIGMA= | 1.2 | PHAS= | -17.1 | FOM= | 0.88 | TEST= 0
| INDE | 5 | 8 | 43 | FOBS= | 91.8 | SIGMA= | 1.8 | PHAS= | 99.7 | FOM= | 0.84 | TEST= 0
| INDE | 5 | 8 | 45 | FOBS= | 130.7 | SIGMA= | 1.5 | PHAS= | 16.7 | FOM= | 0.96 | TEST= 0

*FIG. 12A - 133*

| | | | | | | | | | | | |
|---|---|---|---|---|---|---|---|---|---|---|---|
| INDE | 5 | 8 | 47 | FOBS= | 83.1 | SIGMA= | 2.4 | PHAS= | 121.2 | FOM= 0.84 | TEST= 0 |
| INDE | 5 | 8 | 49 | FOBS= | 135.9 | SIGMA= | 1.5 | PHAS= | 146.0 | FOM= 0.86 | TEST= 0 |
| INDE | 5 | 8 | 51 | FOBS= | 157.4 | SIGMA= | 1.3 | PHAS= | -35.0 | FOM= 0.84 | TEST= 0 |
| INDE | 5 | 8 | 53 | FOBS= | 91.5 | SIGMA= | 2.2 | PHAS= | -125.3 | FOM= 0.84 | TEST= 0 |
| INDE | 5 | 8 | 55 | FOBS= | 150.8 | SIGMA= | 1.4 | PHAS= | -26.6 | FOM= 0.93 | TEST= 0 |
| INDE | 5 | 8 | 57 | FOBS= | 201.7 | SIGMA= | 1.2 | PHAS= | 130.3 | FOM= 0.96 | TEST= 0 |
| INDE | 5 | 8 | 59 | FOBS= | 127.4 | SIGMA= | 1.5 | PHAS= | 34.4 | FOM= 0.96 | TEST= 0 |
| INDE | 5 | 8 | 61 | FOBS= | 53.4 | SIGMA= | 3.5 | PHAS= | -90.5 | FOM= 0.94 | TEST= 0 |
| INDE | 5 | 8 | 63 | FOBS= | 43.9 | SIGMA= | 4.8 | PHAS= | 28.4 | FOM= 0.72 | TEST= 0 |
| INDE | 5 | 8 | 65 | FOBS= | 37.2 | SIGMA= | 6.1 | PHAS= | -110.4 | FOM= 0.12 | TEST= 1 |
| INDE | 5 | 8 | 67 | FOBS= | 0.0 | SIGMA= | 27.5 | PHAS= | 0.0 | FOM= 0.00 | TEST= 0 |
| INDE | 5 | 8 | 69 | FOBS= | 20.8 | SIGMA= | 17.4 | PHAS= | 0.0 | FOM= 0.00 | TEST= 1 |
| INDE | 5 | 8 | 71 | FOBS= | 14.4 | SIGMA= | 27.0 | PHAS= | 65.2 | FOM= 0.27 | TEST= 0 |
| INDE | 5 | 8 | 73 | FOBS= | 29.2 | SIGMA= | 13.3 | PHAS= | 139.9 | FOM= 0.04 | TEST= 0 |
| INDE | 5 | 8 | 75 | FOBS= | 66.5 | SIGMA= | 5.9 | PHAS= | -105.5 | FOM= 0.83 | TEST= 0 |
| INDE | 5 | 8 | 77 | FOBS= | 87.7 | SIGMA= | 4.4 | PHAS= | 27.8 | FOM= 0.75 | TEST= 0 |
| INDE | 5 | 9 | 16 | FOBS= | 427.3 | SIGMA= | 0.3 | PHAS= | 13.5 | FOM= 0.94 | TEST= 0 |
| INDE | 5 | 9 | 18 | FOBS= | 244.7 | SIGMA= | 0.4 | PHAS= | 135.7 | FOM= 0.90 | TEST= 0 |
| INDE | 5 | 9 | 20 | FOBS= | 134.4 | SIGMA= | 0.4 | PHAS= | 165.4 | FOM= 0.62 | TEST= 0 |
| INDE | 5 | 9 | 22 | FOBS= | 142.5 | SIGMA= | 0.4 | PHAS= | -10.1 | FOM= 0.95 | TEST= 0 |
| INDE | 5 | 9 | 24 | FOBS= | 103.1 | SIGMA= | 0.6 | PHAS= | -114.7 | FOM= 0.91 | TEST= 0 |
| INDE | 5 | 9 | 26 | FOBS= | 226.7 | SIGMA= | 0.4 | PHAS= | 135.7 | FOM= 0.97 | TEST= 0 |
| INDE | 5 | 9 | 28 | FOBS= | 143.8 | SIGMA= | 0.5 | PHAS= | 72.4 | FOM= 0.96 | TEST= 0 |
| INDE | 5 | 9 | 30 | FOBS= | 170.6 | SIGMA= | 0.6 | PHAS= | 131.4 | FOM= 0.93 | TEST= 1 |
| INDE | 5 | 9 | 32 | FOBS= | 294.1 | SIGMA= | 0.6 | PHAS= | -13.3 | FOM= 0.99 | TEST= 0 |
| INDE | 5 | 9 | 34 | FOBS= | 109.0 | SIGMA= | 0.7 | PHAS= | 34.1 | FOM= 0.72 | TEST= 0 |
| INDE | 5 | 9 | 36 | FOBS= | 432.1 | SIGMA= | 0.7 | PHAS= | -158.9 | FOM= 0.98 | TEST= 0 |
| INDE | 5 | 9 | 38 | FOBS= | 181.6 | SIGMA= | 1.0 | PHAS= | -163.6 | FOM= 0.97 | TEST= 0 |
| INDE | 5 | 9 | 40 | FOBS= | 133.4 | SIGMA= | 1.4 | PHAS= | 129.4 | FOM= 0.90 | TEST= 0 |
| INDE | 5 | 9 | 42 | FOBS= | 197.2 | SIGMA= | 1.1 | PHAS= | 40.7 | FOM= 0.90 | TEST= 0 |
| INDE | 5 | 9 | 44 | FOBS= | 0.0 | SIGMA= | 18.7 | PHAS= | 0.0 | FOM= 0.00 | TEST= 0 |
| INDE | 5 | 9 | 46 | FOBS= | 180.7 | SIGMA= | 1.2 | PHAS= | 97.6 | FOM= 0.91 | TEST= 0 |
| INDE | 5 | 9 | 48 | FOBS= | 102.1 | SIGMA= | 2.0 | PHAS= | 36.8 | FOM= 0.90 | TEST= 0 |
| INDE | 5 | 9 | 50 | FOBS= | 82.4 | SIGMA= | 2.5 | PHAS= | 116.5 | FOM= 0.78 | TEST= 0 |
| INDE | 5 | 9 | 52 | FOBS= | 0.0 | SIGMA= | 19.7 | PHAS= | 0.0 | FOM= 0.00 | TEST= 0 |
| INDE | 5 | 9 | 54 | FOBS= | 63.6 | SIGMA= | 3.1 | PHAS= | 51.6 | FOM= 0.85 | TEST= 0 |
| INDE | 5 | 9 | 56 | FOBS= | 120.3 | SIGMA= | 1.7 | PHAS= | 108.3 | FOM= 0.90 | TEST= 0 |
| INDE | 5 | 9 | 58 | FOBS= | 138.1 | SIGMA= | 1.5 | PHAS= | -27.6 | FOM= 0.94 | TEST= 0 |
| INDE | 5 | 9 | 60 | FOBS= | 140.5 | SIGMA= | 1.7 | PHAS= | -170.0 | FOM= 0.97 | TEST= 0 |
| INDE | 5 | 9 | 62 | FOBS= | 42.4 | SIGMA= | 4.4 | PHAS= | -109.5 | FOM= 0.70 | TEST= 0 |
| INDE | 5 | 9 | 64 | FOBS= | 35.5 | SIGMA= | 6.4 | PHAS= | -80.5 | FOM= 0.81 | TEST= 0 |
| INDE | 5 | 9 | 66 | FOBS= | 36.3 | SIGMA= | 6.7 | PHAS= | -54.2 | FOM= 0.36 | TEST= 0 |
| INDE | 5 | 9 | 68 | FOBS= | 0.0 | SIGMA= | 27.6 | PHAS= | 0.0 | FOM= 0.00 | TEST= 0 |
| INDE | 5 | 9 | 70 | FOBS= | 34.5 | SIGMA= | 10.8 | PHAS= | 139.4 | FOM= 0.43 | TEST= 0 |
| INDE | 5 | 9 | 72 | FOBS= | 62.9 | SIGMA= | 6.4 | PHAS= | -15.4 | FOM= 0.55 | TEST= 0 |
| INDE | 5 | 9 | 74 | FOBS= | 0.0 | SIGMA= | 28.3 | PHAS= | 0.0 | FOM= 0.00 | TEST= 0 |
| INDE | 5 | 9 | 76 | FOBS= | 95.5 | SIGMA= | 4.3 | PHAS= | -71.8 | FOM= 0.94 | TEST= 0 |
| INDE | 5 | 10 | 15 | FOBS= | 377.4 | SIGMA= | 0.4 | PHAS= | 27.9 | FOM= 0.96 | TEST= 0 |
| INDE | 5 | 10 | 17 | FOBS= | 339.7 | SIGMA= | 0.4 | PHAS= | -3.4 | FOM= 0.48 | TEST= 1 |
| INDE | 5 | 10 | 19 | FOBS= | 397.2 | SIGMA= | 0.4 | PHAS= | 55.9 | FOM= 0.94 | TEST= 0 |
| INDE | 5 | 10 | 21 | FOBS= | 88.4 | SIGMA= | 0.6 | PHAS= | 91.4 | FOM= 0.64 | TEST= 0 |
| INDE | 5 | 10 | 23 | FOBS= | 269.6 | SIGMA= | 0.4 | PHAS= | 176.9 | FOM= 0.99 | TEST= 0 |
| INDE | 5 | 10 | 25 | FOBS= | 58.2 | SIGMA= | 1.0 | PHAS= | 13.9 | FOM= 0.98 | TEST= 0 |
| INDE | 5 | 10 | 27 | FOBS= | 271.6 | SIGMA= | 0.5 | PHAS= | -6.7 | FOM= 0.96 | TEST= 0 |
| INDE | 5 | 10 | 29 | FOBS= | 171.7 | SIGMA= | 0.5 | PHAS= | -60.6 | FOM= 0.96 | TEST= 0 |
| INDE | 5 | 10 | 31 | FOBS= | 293.2 | SIGMA= | 0.5 | PHAS= | -56.3 | FOM= 0.97 | TEST= 0 |
| INDE | 5 | 10 | 33 | FOBS= | 185.8 | SIGMA= | 0.5 | PHAS= | -144.1 | FOM= 0.99 | TEST= 0 |
| INDE | 5 | 10 | 35 | FOBS= | 0.0 | SIGMA= | 15.4 | PHAS= | 0.0 | FOM= 0.00 | TEST= 0 |
| INDE | 5 | 10 | 37 | FOBS= | 164.2 | SIGMA= | 1.0 | PHAS= | 31.3 | FOM= 0.92 | TEST= 0 |
| INDE | 5 | 10 | 39 | FOBS= | 242.8 | SIGMA= | 0.7 | PHAS= | 116.9 | FOM= 0.92 | TEST= 0 |
| INDE | 5 | 10 | 41 | FOBS= | 105.1 | SIGMA= | 1.5 | PHAS= | -14.9 | FOM= 0.93 | TEST= 0 |
| INDE | 5 | 10 | 43 | FOBS= | 43.4 | SIGMA= | 3.9 | PHAS= | -149.1 | FOM= 0.49 | TEST= 0 |
| INDE | 5 | 10 | 45 | FOBS= | 288.1 | SIGMA= | 0.8 | PHAS= | 38.3 | FOM= 0.98 | TEST= 0 |
| INDE | 5 | 10 | 47 | FOBS= | 52.6 | SIGMA= | 3.9 | PHAS= | -64.1 | FOM= 0.66 | TEST= 0 |
| INDE | 5 | 10 | 49 | FOBS= | 60.0 | SIGMA= | 3.4 | PHAS= | 10.5 | FOM= 0.89 | TEST= 0 |
| INDE | 5 | 10 | 51 | FOBS= | 247.0 | SIGMA= | 0.9 | PHAS= | 29.1 | FOM= 0.95 | TEST= 0 |
| INDE | 5 | 10 | 53 | FOBS= | 284.5 | SIGMA= | 0.9 | PHAS= | -86.6 | FOM= 0.98 | TEST= 0 |
| INDE | 5 | 10 | 55 | FOBS= | 190.1 | SIGMA= | 1.1 | PHAS= | -14.2 | FOM= 0.95 | TEST= 0 |
| INDE | 5 | 10 | 57 | FOBS= | 47.1 | SIGMA= | 4.1 | PHAS= | 60.7 | FOM= 0.92 | TEST= 0 |
| INDE | 5 | 10 | 59 | FOBS= | 43.3 | SIGMA= | 4.4 | PHAS= | 87.7 | FOM= 0.58 | TEST= 0 |

*FIG. 12A - 134*

| | | | | | | | | | | | |
|---|---|---|---|---|---|---|---|---|---|---|---|
| INDE | 5 | 10 | 61 | FOBS= | 58.5 | SIGMA= | 3.3 | PHAS= | -160.4 | FOM= 0.69 | TEST= 0 |
| INDE | 5 | 10 | 63 | FOBS= | 51.2 | SIGMA= | 4.1 | PHAS= | -139.4 | FOM= 0.68 | TEST= 0 |
| INDE | 5 | 10 | 65 | FOBS= | 0.0 | SIGMA= | 22.9 | PHAS= | 0.0 | FOM= 0.00 | TEST= 0 |
| INDE | 5 | 10 | 67 | FOBS= | 78.3 | SIGMA= | 3.6 | PHAS= | -168.3 | FOM= 0.87 | TEST= 0 |
| INDE | 5 | 10 | 69 | FOBS= | 50.2 | SIGMA= | 7.8 | PHAS= | 88.7 | FOM= 0.09 | TEST= 1 |
| INDE | 5 | 10 | 71 | FOBS= | 83.8 | SIGMA= | 4.7 | PHAS= | 139.3 | FOM= 0.79 | TEST= 0 |
| INDE | 5 | 10 | 73 | FOBS= | 45.6 | SIGMA= | 9.0 | PHAS= | -20.9 | FOM= 0.78 | TEST= 0 |
| INDE | 5 | 10 | 75 | FOBS= | 35.9 | SIGMA= | 11.2 | PHAS= | -137.0 | FOM= 0.41 | TEST= 0 |
| INDE | 5 | 11 | 14 | FOBS= | 59.6 | SIGMA= | 0.7 | PHAS= | 22.0 | FOM= 0.77 | TEST= 0 |
| INDE | 5 | 11 | 16 | FOBS= | 154.0 | SIGMA= | 0.4 | PHAS= | -108.5 | FOM= 0.88 | TEST= 1 |
| INDE | 5 | 11 | 18 | FOBS= | 308.6 | SIGMA= | 0.4 | PHAS= | -36.1 | FOM= 0.96 | TEST= 0 |
| INDE | 5 | 11 | 20 | FOBS= | 178.0 | SIGMA= | 0.4 | PHAS= | -14.6 | FOM= 0.95 | TEST= 0 |
| INDE | 5 | 11 | 22 | FOBS= | 253.1 | SIGMA= | 0.4 | PHAS= | 63.0 | FOM= 0.92 | TEST= 0 |
| INDE | 5 | 11 | 24 | FOBS= | 161.3 | SIGMA= | 0.5 | PHAS= | 86.1 | FOM= 0.99 | TEST= 0 |
| INDE | 5 | 11 | 26 | FOBS= | 72.8 | SIGMA= | 0.9 | PHAS= | -139.9 | FOM= 0.87 | TEST= 0 |
| INDE | 5 | 11 | 28 | FOBS= | 184.7 | SIGMA= | 0.4 | PHAS= | -70.7 | FOM= 0.97 | TEST= 0 |
| INDE | 5 | 11 | 30 | FOBS= | 371.3 | SIGMA= | 0.6 | PHAS= | -161.6 | FOM= 0.98 | TEST= 0 |
| INDE | 5 | 11 | 32 | FOBS= | 102.9 | SIGMA= | 0.8 | PHAS= | -95.9 | FOM= 0.96 | TEST= 0 |
| INDE | 5 | 11 | 34 | FOBS= | 97.7 | SIGMA= | 1.0 | PHAS= | -7.6 | FOM= 0.92 | TEST= 0 |
| INDE | 5 | 11 | 36 | FOBS= | 121.1 | SIGMA= | 0.9 | PHAS= | 75.9 | FOM= 0.96 | TEST= 0 |
| INDE | 5 | 11 | 38 | FOBS= | 109.1 | SIGMA= | 1.3 | PHAS= | -35.0 | FOM= 0.77 | TEST= 0 |
| INDE | 5 | 11 | 40 | FOBS= | 96.6 | SIGMA= | 1.6 | PHAS= | 67.9 | FOM= 0.07 | TEST= 0 |
| INDE | 5 | 11 | 42 | FOBS= | 291.9 | SIGMA= | 0.8 | PHAS= | 52.2 | FOM= 0.88 | TEST= 0 |
| INDE | 5 | 11 | 44 | FOBS= | 159.4 | SIGMA= | 1.2 | PHAS= | -78.1 | FOM= 0.93 | TEST= 1 |
| INDE | 5 | 11 | 46 | FOBS= | 66.6 | SIGMA= | 3.1 | PHAS= | -83.2 | FOM= 0.95 | TEST= 0 |
| INDE | 5 | 11 | 48 | FOBS= | 66.6 | SIGMA= | 3.1 | PHAS= | -77.8 | FOM= 0.93 | TEST= 0 |
| INDE | 5 | 11 | 50 | FOBS= | 91.6 | SIGMA= | 2.2 | PHAS= | -115.5 | FOM= 0.71 | TEST= 0 |
| INDE | 5 | 11 | 52 | FOBS= | 150.0 | SIGMA= | 1.4 | PHAS= | -135.1 | FOM= 0.95 | TEST= 0 |
| INDE | 5 | 11 | 54 | FOBS= | 171.9 | SIGMA= | 1.3 | PHAS= | 176.3 | FOM= 0.94 | TEST= 0 |
| INDE | 5 | 11 | 56 | FOBS= | 34.0 | SIGMA= | 6.7 | PHAS= | -71.4 | FOM= 0.74 | TEST= 0 |
| INDE | 5 | 11 | 58 | FOBS= | 192.1 | SIGMA= | 1.1 | PHAS= | -27.2 | FOM= 0.95 | TEST= 0 |
| INDE | 5 | 11 | 60 | FOBS= | 101.4 | SIGMA= | 2.0 | PHAS= | 147.4 | FOM= 0.94 | TEST= 0 |
| INDE | 5 | 11 | 62 | FOBS= | 71.4 | SIGMA= | 2.7 | PHAS= | 160.4 | FOM= 0.87 | TEST= 0 |
| INDE | 5 | 11 | 64 | FOBS= | 47.2 | SIGMA= | 4.9 | PHAS= | -144.1 | FOM= 0.47 | TEST= 0 |
| INDE | 5 | 11 | 66 | FOBS= | 78.2 | SIGMA= | 3.8 | PHAS= | 107.4 | FOM= 0.90 | TEST= 0 |
| INDE | 5 | 11 | 68 | FOBS= | 32.9 | SIGMA= | 12.3 | PHAS= | 134.6 | FOM= 0.62 | TEST= 0 |
| INDE | 5 | 11 | 70 | FOBS= | 61.5 | SIGMA= | 4.7 | PHAS= | 31.2 | FOM= 0.75 | TEST= 0 |
| INDE | 5 | 11 | 72 | FOBS= | 32.2 | SIGMA= | 12.2 | PHAS= | -145.7 | FOM= 0.65 | TEST= 0 |
| INDE | 5 | 11 | 74 | FOBS= | 60.0 | SIGMA= | 7.1 | PHAS= | 73.5 | FOM= 0.26 | TEST= 0 |
| INDE | 5 | 11 | 76 | FOBS= | 90.2 | SIGMA= | 4.7 | PHAS= | -56.1 | FOM= 0.88 | TEST= 0 |
| INDE | 5 | 12 | 13 | FOBS= | 207.0 | SIGMA= | 0.5 | PHAS= | 93.8 | FOM= 0.10 | TEST= 1 |
| INDE | 5 | 12 | 15 | FOBS= | 332.3 | SIGMA= | 0.5 | PHAS= | -80.6 | FOM= 0.99 | TEST= 0 |
| INDE | 5 | 12 | 17 | FOBS= | 34.2 | SIGMA= | 1.3 | PHAS= | -49.0 | FOM= 0.57 | TEST= 0 |
| INDE | 5 | 12 | 19 | FOBS= | 137.0 | SIGMA= | 0.5 | PHAS= | 92.3 | FOM= 0.92 | TEST= 0 |
| INDE | 5 | 12 | 21 | FOBS= | 183.2 | SIGMA= | 0.5 | PHAS= | -13.7 | FOM= 0.64 | TEST= 1 |
| INDE | 5 | 12 | 23 | FOBS= | 73.4 | SIGMA= | 0.8 | PHAS= | -21.8 | FOM= 0.97 | TEST= 0 |
| INDE | 5 | 12 | 25 | FOBS= | 99.3 | SIGMA= | 0.6 | PHAS= | 31.6 | FOM= 0.99 | TEST= 0 |
| INDE | 5 | 12 | 27 | FOBS= | 125.1 | SIGMA= | 0.6 | PHAS= | -141.8 | FOM= 0.99 | TEST= 0 |
| INDE | 5 | 12 | 29 | FOBS= | 164.7 | SIGMA= | 0.6 | PHAS= | -167.6 | FOM= 0.97 | TEST= 0 |
| INDE | 5 | 12 | 31 | FOBS= | 85.5 | SIGMA= | 0.9 | PHAS= | 63.8 | FOM= 0.86 | TEST= 0 |
| INDE | 5 | 12 | 33 | FOBS= | 104.4 | SIGMA= | 0.8 | PHAS= | -131.3 | FOM= 0.56 | TEST= 1 |
| INDE | 5 | 12 | 35 | FOBS= | 193.9 | SIGMA= | 0.7 | PHAS= | 150.6 | FOM= 0.77 | TEST= 1 |
| INDE | 5 | 12 | 37 | FOBS= | 61.1 | SIGMA= | 1.5 | PHAS= | 72.4 | FOM= 0.95 | TEST= 0 |
| INDE | 5 | 12 | 39 | FOBS= | 91.8 | SIGMA= | 1.7 | PHAS= | -128.9 | FOM= 0.75 | TEST= 0 |
| INDE | 5 | 12 | 41 | FOBS= | 184.2 | SIGMA= | 1.0 | PHAS= | 166.8 | FOM= 0.34 | TEST= 1 |
| INDE | 5 | 12 | 43 | FOBS= | 83.8 | SIGMA= | 2.2 | PHAS= | -47.7 | FOM= 0.93 | TEST= 1 |
| INDE | 5 | 12 | 45 | FOBS= | 155.8 | SIGMA= | 1.3 | PHAS= | -135.2 | FOM= 0.95 | TEST= 1 |
| INDE | 5 | 12 | 47 | FOBS= | 21.3 | SIGMA= | 10.7 | PHAS= | -61.5 | FOM= 0.13 | TEST= 0 |
| INDE | 5 | 12 | 49 | FOBS= | 143.8 | SIGMA= | 1.5 | PHAS= | 68.1 | FOM= 0.93 | TEST= 0 |
| INDE | 5 | 12 | 51 | FOBS= | 99.9 | SIGMA= | 2.0 | PHAS= | 14.4 | FOM= 0.86 | TEST= 0 |
| INDE | 5 | 12 | 53 | FOBS= | 45.7 | SIGMA= | 4.4 | PHAS= | -40.1 | FOM= 0.73 | TEST= 0 |
| INDE | 5 | 12 | 55 | FOBS= | 0.0 | SIGMA= | 19.6 | PHAS= | 0.0 | FOM= 0.00 | TEST= 1 |
| INDE | 5 | 12 | 57 | FOBS= | 98.3 | SIGMA= | 2.0 | PHAS= | -71.7 | FOM= 0.73 | TEST= 0 |
| INDE | 5 | 12 | 59 | FOBS= | 53.0 | SIGMA= | 3.7 | PHAS= | -102.0 | FOM= 0.83 | TEST= 0 |
| INDE | 5 | 12 | 61 | FOBS= | 28.4 | SIGMA= | 8.4 | PHAS= | -158.2 | FOM= 0.28 | TEST= 0 |
| INDE | 5 | 12 | 63 | FOBS= | 33.0 | SIGMA= | 7.0 | PHAS= | 74.8 | FOM= 0.49 | TEST= 0 |
| INDE | 5 | 12 | 65 | FOBS= | 77.6 | SIGMA= | 3.5 | PHAS= | 43.6 | FOM= 0.90 | TEST= 0 |
| INDE | 5 | 12 | 67 | FOBS= | 77.5 | SIGMA= | 3.9 | PHAS= | 64.4 | FOM= 0.84 | TEST= 0 |
| INDE | 5 | 12 | 69 | FOBS= | 9.9 | SIGMA= | 29.9 | PHAS= | -5.5 | FOM= 0.11 | TEST= 0 |
| INDE | 5 | 12 | 71 | FOBS= | 13.0 | SIGMA= | 22.5 | PHAS= | 10.4 | FOM= 0.07 | TEST= 0 |

*FIG. 12A - 135*

```
INDE  5 12 73 FOBS=    0.0 SIGMA= 24.3 PHAS=    0.0 FOM= 0.00 TEST= 0
INDE  5 12 75 FOBS=    0.0 SIGMA= 29.6 PHAS=    0.0 FOM= 0.00 TEST= 0
INDE  5 13 12 FOBS=  162.9 SIGMA=  0.5 PHAS=  104.7 FOM= 0.87 TEST= 0
INDE  5 13 14 FOBS=  245.8 SIGMA=  0.5 PHAS= -146.9 FOM= 0.93 TEST= 0
INDE  5 13 16 FOBS=  313.2 SIGMA=  0.4 PHAS=  172.4 FOM= 0.94 TEST= 0
INDE  5 13 18 FOBS=  124.2 SIGMA=  0.4 PHAS= -163.6 FOM= 0.99 TEST= 0
INDE  5 13 20 FOBS=  136.3 SIGMA=  0.4 PHAS=  -31.2 FOM= 0.86 TEST= 0
INDE  5 13 22 FOBS=  146.8 SIGMA=  0.5 PHAS=  102.0 FOM= 0.97 TEST= 0
INDE  5 13 24 FOBS=   60.5 SIGMA=  1.0 PHAS=   -3.0 FOM= 0.72 TEST= 0
INDE  5 13 26 FOBS=   68.4 SIGMA=  0.9 PHAS= -145.5 FOM= 0.46 TEST= 0
INDE  5 13 28 FOBS=  239.9 SIGMA=  0.4 PHAS=  150.5 FOM= 0.95 TEST= 0
INDE  5 13 30 FOBS=   86.5 SIGMA=  0.9 PHAS=  168.2 FOM= 0.96 TEST= 0
INDE  5 13 32 FOBS=  180.7 SIGMA=  0.6 PHAS=  -62.3 FOM= 0.98 TEST= 0
INDE  5 13 34 FOBS=   57.3 SIGMA=  1.4 PHAS= -109.8 FOM= 0.95 TEST= 0
INDE  5 13 36 FOBS=  217.2 SIGMA=  0.6 PHAS=   62.6 FOM= 0.98 TEST= 0
INDE  5 13 38 FOBS=    0.0 SIGMA= 17.6 PHAS=    0.0 FOM= 0.00 TEST= 0
INDE  5 13 40 FOBS=  183.1 SIGMA=  1.3 PHAS=  141.4 FOM= 0.93 TEST= 0
INDE  5 13 42 FOBS=   56.7 SIGMA=  3.1 PHAS=   27.9 FOM= 0.36 TEST= 0
INDE  5 13 44 FOBS=  116.5 SIGMA=  1.7 PHAS= -139.1 FOM= 0.95 TEST= 0
INDE  5 13 46 FOBS=  134.2 SIGMA=  1.6 PHAS=  172.0 FOM= 0.94 TEST= 0
INDE  5 13 48 FOBS=  275.4 SIGMA=  0.9 PHAS=  -34.7 FOM= 0.95 TEST= 0
INDE  5 13 50 FOBS=  129.6 SIGMA=  1.6 PHAS=  -87.6 FOM= 0.96 TEST= 0
INDE  5 13 52 FOBS=  274.5 SIGMA=  0.9 PHAS=  -93.8 FOM= 0.98 TEST= 0
INDE  5 13 54 FOBS=   67.7 SIGMA=  2.9 PHAS=  165.5 FOM= 0.64 TEST= 0
INDE  5 13 56 FOBS=    0.0 SIGMA= 19.6 PHAS=    0.0 FOM= 0.00 TEST= 0
INDE  5 13 58 FOBS=   90.6 SIGMA=  2.2 PHAS=  151.0 FOM= 0.92 TEST= 0
INDE  5 13 60 FOBS=  195.9 SIGMA=  1.1 PHAS= -159.0 FOM= 0.96 TEST= 0
INDE  5 13 62 FOBS=   53.0 SIGMA=  3.6 PHAS=  127.1 FOM= 0.51 TEST= 1
INDE  5 13 64 FOBS=  126.3 SIGMA=  2.2 PHAS=  -12.1 FOM= 0.92 TEST= 0
INDE  5 13 66 FOBS=  132.5 SIGMA=  3.2 PHAS=  -37.8 FOM= 0.94 TEST= 0
INDE  5 13 68 FOBS=   61.3 SIGMA=  4.9 PHAS=  -88.0 FOM= 0.57 TEST= 0
INDE  5 13 70 FOBS=   53.3 SIGMA=  5.7 PHAS=  -65.4 FOM= 0.76 TEST= 0
INDE  5 13 72 FOBS=   68.2 SIGMA=  4.4 PHAS= -138.8 FOM= 0.87 TEST= 0
INDE  5 13 74 FOBS=   49.6 SIGMA=  6.3 PHAS=   88.1 FOM= 0.80 TEST= 0
INDE  5 13 76 FOBS=   53.6 SIGMA=  8.4 PHAS=  -26.4 FOM= 0.87 TEST= 0
INDE  5 14 11 FOBS=  283.2 SIGMA=  0.4 PHAS=  -68.2 FOM= 0.75 TEST= 0
INDE  5 14 13 FOBS=  161.3 SIGMA=  0.5 PHAS=   12.1 FOM= 0.72 TEST= 0
INDE  5 14 15 FOBS=  152.1 SIGMA=  0.7 PHAS=   68.6 FOM= 0.89 TEST= 0
INDE  5 14 17 FOBS=  152.5 SIGMA=  0.4 PHAS=   37.5 FOM= 0.86 TEST= 0
INDE  5 14 19 FOBS=  251.0 SIGMA=  0.4 PHAS=   26.4 FOM= 0.99 TEST= 0
INDE  5 14 21 FOBS=  117.6 SIGMA=  0.5 PHAS=  -21.7 FOM= 0.94 TEST= 0
INDE  5 14 23 FOBS=  152.2 SIGMA=  0.5 PHAS=  -11.7 FOM= 0.98 TEST= 0
INDE  5 14 25 FOBS=   48.2 SIGMA=  1.3 PHAS=  -19.9 FOM= 0.82 TEST= 0
INDE  5 14 27 FOBS=   83.8 SIGMA=  0.8 PHAS=   76.4 FOM= 0.79 TEST= 0
INDE  5 14 29 FOBS=  131.8 SIGMA=  0.6 PHAS= -128.0 FOM= 0.98 TEST= 0
INDE  5 14 31 FOBS=   26.0 SIGMA=  3.0 PHAS= -139.7 FOM= 0.28 TEST= 0
INDE  5 14 33 FOBS=   80.6 SIGMA=  1.1 PHAS=   17.8 FOM= 0.48 TEST= 0
INDE  5 14 35 FOBS=  117.2 SIGMA=  1.0 PHAS= -144.5 FOM= 0.92 TEST= 0
INDE  5 14 37 FOBS=  140.1 SIGMA=  1.0 PHAS=    3.2 FOM= 0.90 TEST= 0
INDE  5 14 39 FOBS=   85.6 SIGMA=  1.8 PHAS=   14.1 FOM= 0.70 TEST= 0
INDE  5 14 41 FOBS=  126.9 SIGMA=  1.4 PHAS=  171.8 FOM= 0.95 TEST= 1
INDE  5 14 43 FOBS=    0.0 SIGMA= 21.9 PHAS=    0.0 FOM= 0.00 TEST= 0
INDE  5 14 45 FOBS=   68.5 SIGMA=  3.0 PHAS=  159.7 FOM= 0.94 TEST= 0
INDE  5 14 47 FOBS=  185.5 SIGMA=  1.2 PHAS=  140.5 FOM= 0.91 TEST= 0
INDE  5 14 49 FOBS=   89.5 SIGMA=  2.3 PHAS=  -81.9 FOM= 0.87 TEST= 1
INDE  5 14 51 FOBS=  114.2 SIGMA=  1.8 PHAS= -149.1 FOM= 0.94 TEST= 0
INDE  5 14 53 FOBS=  203.6 SIGMA=  1.1 PHAS=  144.9 FOM= 0.89 TEST= 0
INDE  5 14 55 FOBS=   49.9 SIGMA=  4.2 PHAS=   71.8 FOM= 0.23 TEST= 0
INDE  5 14 57 FOBS=   88.7 SIGMA=  2.2 PHAS=   87.6 FOM= 0.72 TEST= 0
INDE  5 14 59 FOBS=  148.9 SIGMA=  1.4 PHAS=   92.3 FOM= 0.89 TEST= 0
INDE  5 14 61 FOBS=  124.5 SIGMA=  1.6 PHAS=  110.0 FOM= 0.53 TEST= 1
INDE  5 14 63 FOBS=   41.7 SIGMA=  5.6 PHAS= -156.3 FOM= 0.26 TEST= 1
INDE  5 14 65 FOBS=  142.7 SIGMA=  2.4 PHAS= -105.0 FOM= 0.93 TEST= 0
INDE  5 14 67 FOBS=   34.4 SIGMA= 12.2 PHAS= -156.6 FOM= 0.50 TEST= 0
INDE  5 14 69 FOBS=   46.3 SIGMA=  6.4 PHAS=  161.7 FOM= 0.18 TEST= 0
INDE  5 14 71 FOBS=   49.1 SIGMA=  6.2 PHAS= -141.6 FOM= 0.18 TEST= 1
INDE  5 14 73 FOBS=   22.0 SIGMA= 14.0 PHAS= -139.6 FOM= 0.25 TEST= 0
INDE  5 14 75 FOBS=   77.6 SIGMA=  6.0 PHAS=   -6.5 FOM= 0.90 TEST= 0
INDE  5 15 10 FOBS=  345.3 SIGMA=  0.5 PHAS=   93.9 FOM= 0.89 TEST= 0
INDE  5 15 12 FOBS=  317.3 SIGMA=  0.5 PHAS= -125.5 FOM= 0.95 TEST= 0
```

*FIG. 12A - 136*

```
INDE  5  15  14  FOBS=  158.4  SIGMA=  0.5  PHAS=   -62.4  FOM=  0.71  TEST=  0
INDE  5  15  16  FOBS=  117.9  SIGMA=  0.5  PHAS=  -108.1  FOM=  0.79  TEST=  0
INDE  5  15  18  FOBS=  111.3  SIGMA=  0.5  PHAS=   -99.3  FOM=  0.85  TEST=  0
INDE  5  15  20  FOBS=   58.9  SIGMA=  0.9  PHAS=   -10.9  FOM=  0.99  TEST=  0
INDE  5  15  22  FOBS=   41.8  SIGMA=  1.3  PHAS=   -96.3  FOM=  0.90  TEST=  0
INDE  5  15  24  FOBS=  255.5  SIGMA=  0.5  PHAS=   -93.8  FOM=  0.99  TEST=  0
INDE  5  15  26  FOBS=   33.4  SIGMA=  1.9  PHAS=   151.1  FOM=  0.41  TEST=  0
INDE  5  15  28  FOBS=  219.6  SIGMA=  0.5  PHAS=  -135.3  FOM=  0.99  TEST=  0
INDE  5  15  30  FOBS=   93.6  SIGMA=  0.9  PHAS=  -151.3  FOM=  0.98  TEST=  0
INDE  5  15  32  FOBS=  197.5  SIGMA=  0.7  PHAS=   -43.6  FOM=  0.98  TEST=  0
INDE  5  15  34  FOBS=  150.6  SIGMA=  0.8  PHAS=    37.5  FOM=  0.99  TEST=  0
INDE  5  15  36  FOBS=  137.4  SIGMA=  0.9  PHAS=   -33.7  FOM=  0.99  TEST=  0
INDE  5  15  38  FOBS=  116.7  SIGMA=  1.2  PHAS=    11.3  FOM=  0.96  TEST=  0
INDE  5  15  40  FOBS=  131.1  SIGMA=  1.3  PHAS=    19.4  FOM=  0.96  TEST=  0
INDE  5  15  42  FOBS=   74.1  SIGMA=  1.7  PHAS=    10.7  FOM=  0.68  TEST=  0
INDE  5  15  44  FOBS=  119.1  SIGMA=  1.7  PHAS=   121.5  FOM=  0.96  TEST=  0
INDE  5  15  46  FOBS=  114.0  SIGMA=  1.9  PHAS=   -19.9  FOM=  0.88  TEST=  0
INDE  5  15  48  FOBS=   84.4  SIGMA=  2.5  PHAS=   -64.7  FOM=  0.58  TEST=  0
INDE  5  15  50  FOBS=  102.4  SIGMA=  2.1  PHAS=  -158.8  FOM=  0.90  TEST=  0
INDE  5  15  52  FOBS=  101.0  SIGMA=  2.1  PHAS=   -37.6  FOM=  0.84  TEST=  0
INDE  5  15  54  FOBS=  106.5  SIGMA=  1.9  PHAS=  -160.3  FOM=  0.36  TEST=  0
INDE  5  15  56  FOBS=  196.0  SIGMA=  1.3  PHAS=   -10.8  FOM=  0.96  TEST=  0
INDE  5  15  58  FOBS=   87.5  SIGMA=  2.3  PHAS=     7.1  FOM=  0.77  TEST=  0
INDE  5  15  60  FOBS=   41.3  SIGMA=  5.0  PHAS=   -33.3  FOM=  0.24  TEST=  1
INDE  5  15  62  FOBS=   70.6  SIGMA=  2.8  PHAS=    49.6  FOM=  0.89  TEST=  0
INDE  5  15  64  FOBS=   68.1  SIGMA=  4.1  PHAS=   130.0  FOM=  0.66  TEST=  0
INDE  5  15  66  FOBS=   90.8  SIGMA=  4.7  PHAS=  -178.9  FOM=  0.91  TEST=  0
INDE  5  15  68  FOBS=   51.6  SIGMA=  5.9  PHAS=   -24.2  FOM=  0.76  TEST=  0
INDE  5  15  70  FOBS=   33.4  SIGMA=  9.1  PHAS=   -97.0  FOM=  0.70  TEST=  0
INDE  5  15  72  FOBS=   70.7  SIGMA=  4.5  PHAS=  -155.3  FOM=  0.90  TEST=  0
INDE  5  15  74  FOBS=   63.9  SIGMA=  4.9  PHAS=   115.0  FOM=  0.67  TEST=  0
INDE  5  15  76  FOBS=   46.5  SIGMA=  7.1  PHAS=   -85.6  FOM=  0.65  TEST=  0
INDE  5  16   7  FOBS=   81.0  SIGMA=  0.7  PHAS=  -151.6  FOM=  0.73  TEST=  0
INDE  5  16   9  FOBS=  180.7  SIGMA=  0.5  PHAS=    73.8  FOM=  0.99  TEST=  0
INDE  5  16  11  FOBS=  244.2  SIGMA=  0.4  PHAS=   140.9  FOM=  0.91  TEST=  0
INDE  5  16  13  FOBS=  283.3  SIGMA=  0.5  PHAS=   143.9  FOM=  0.93  TEST=  0
INDE  5  16  15  FOBS=  170.7  SIGMA=  0.5  PHAS=   -35.2  FOM=  0.99  TEST=  0
INDE  5  16  17  FOBS=   77.2  SIGMA=  0.8  PHAS=    10.8  FOM=  0.85  TEST=  0
INDE  5  16  19  FOBS=  269.8  SIGMA=  0.4  PHAS=    12.2  FOM=  0.96  TEST=  0
INDE  5  16  21  FOBS=  104.1  SIGMA=  0.6  PHAS=   -76.2  FOM=  0.98  TEST=  0
INDE  5  16  23  FOBS=  210.2  SIGMA=  0.4  PHAS=  -147.5  FOM=  0.99  TEST=  0
INDE  5  16  25  FOBS=  170.2  SIGMA=  0.4  PHAS=   174.9  FOM=  0.84  TEST=  1
INDE  5  16  27  FOBS=  129.0  SIGMA=  0.7  PHAS=   101.8  FOM=  0.96  TEST=  0
INDE  5  16  29  FOBS=  103.4  SIGMA=  1.0  PHAS=  -153.1  FOM=  0.77  TEST=  0
INDE  5  16  31  FOBS=  196.6  SIGMA=  0.7  PHAS=   171.6  FOM=  0.99  TEST=  0
INDE  5  16  33  FOBS=  143.1  SIGMA=  0.9  PHAS=   -48.8  FOM=  0.91  TEST=  0
INDE  5  16  35  FOBS=  181.0  SIGMA=  0.7  PHAS=   -96.3  FOM=  0.99  TEST=  0
INDE  5  16  37  FOBS=   43.9  SIGMA=  2.8  PHAS=  -168.9  FOM=  0.26  TEST=  0
INDE  5  16  39  FOBS=  205.3  SIGMA=  0.7  PHAS=   -27.7  FOM=  0.96  TEST=  0
INDE  5  16  41  FOBS=  277.2  SIGMA=  0.8  PHAS=  -127.9  FOM=  0.93  TEST=  1
INDE  5  16  43  FOBS=  104.9  SIGMA=  1.4  PHAS=   -12.6  FOM=  0.79  TEST=  0
INDE  5  16  45  FOBS=  167.8  SIGMA=  1.4  PHAS=    -1.9  FOM=  0.82  TEST=  1
INDE  5  16  47  FOBS=  156.1  SIGMA=  1.7  PHAS=   176.6  FOM=  0.89  TEST=  0
INDE  5  16  49  FOBS=  109.0  SIGMA=  2.0  PHAS=  -120.2  FOM=  0.86  TEST=  0
INDE  5  16  51  FOBS=  152.0  SIGMA=  1.4  PHAS=   -73.1  FOM=  0.93  TEST=  0
INDE  5  16  53  FOBS=  137.2  SIGMA=  1.6  PHAS=  -161.2  FOM=  0.93  TEST=  0
INDE  5  16  55  FOBS=  186.7  SIGMA=  1.2  PHAS=  -100.7  FOM=  0.96  TEST=  0
INDE  5  16  57  FOBS=   52.6  SIGMA=  4.0  PHAS=  -172.5  FOM=  0.30  TEST=  0
INDE  5  16  59  FOBS=    0.0  SIGMA= 22.0  PHAS=     0.0  FOM=  0.00  TEST=  0
INDE  5  16  61  FOBS=   10.9  SIGMA= 17.7  PHAS=    23.9  FOM=  0.13  TEST=  0
INDE  5  16  63  FOBS=   11.8  SIGMA= 17.4  PHAS=     4.1  FOM=  0.11  TEST=  0
INDE  5  16  65  FOBS=   82.0  SIGMA=  5.4  PHAS=    61.6  FOM=  0.63  TEST=  0
INDE  5  16  67  FOBS=  118.6  SIGMA=  3.8  PHAS=   101.6  FOM=  0.95  TEST=  0
INDE  5  16  69  FOBS=    0.0  SIGMA= 24.7  PHAS=     0.0  FOM=  0.00  TEST=  0
INDE  5  16  71  FOBS=   38.5  SIGMA=  8.1  PHAS=    54.5  FOM=  0.03  TEST=  1
INDE  5  16  73  FOBS=   45.3  SIGMA=  7.0  PHAS=    81.6  FOM=  0.68  TEST=  0
INDE  5  16  75  FOBS=    0.0  SIGMA= 25.3  PHAS=     0.0  FOM=  0.00  TEST=  0
INDE  5  17   6  FOBS=  215.0  SIGMA=  0.4  PHAS=  -163.7  FOM=  0.31  TEST=  0
INDE  5  17   8  FOBS=  213.4  SIGMA=  0.5  PHAS=   -18.8  FOM=  0.64  TEST=  0
INDE  5  17  10  FOBS=  281.4  SIGMA=  0.5  PHAS=    50.0  FOM=  0.94  TEST=  0
```

*FIG. 12A - 137*

```
INDE   5  17  12 FOBS=   204.6 SIGMA=   0.5 PHAS=    23.8 FOM=  0.88 TEST= 0
INDE   5  17  14 FOBS=   158.0 SIGMA=   0.7 PHAS=  -125.0 FOM=  0.38 TEST= 0
INDE   5  17  16 FOBS=    91.4 SIGMA=   0.8 PHAS=  -114.2 FOM=  0.96 TEST= 0
INDE   5  17  18 FOBS=   148.1 SIGMA=   0.5 PHAS=   -89.6 FOM=  0.90 TEST= 0
INDE   5  17  20 FOBS=    63.5 SIGMA=   1.0 PHAS=   154.8 FOM=  0.31 TEST= 0
INDE   5  17  22 FOBS=   154.6 SIGMA=   0.5 PHAS=  -167.6 FOM=  0.91 TEST= 0
INDE   5  17  24 FOBS=   269.4 SIGMA=   0.5 PHAS=    94.0 FOM=  0.93 TEST= 0
INDE   5  17  26 FOBS=    93.6 SIGMA=   0.8 PHAS=    94.7 FOM=  0.93 TEST= 0
INDE   5  17  28 FOBS=   144.4 SIGMA=   0.7 PHAS=   173.1 FOM=  0.94 TEST= 0
INDE   5  17  30 FOBS=    96.8 SIGMA=   1.1 PHAS=  -179.0 FOM=  0.85 TEST= 1
INDE   5  17  32 FOBS=   103.5 SIGMA=   1.1 PHAS=   -52.5 FOM=  0.96 TEST= 0
INDE   5  17  34 FOBS=    83.1 SIGMA=   1.4 PHAS=    -5.7 FOM=  0.87 TEST= 0
INDE   5  17  36 FOBS=   324.0 SIGMA=   0.6 PHAS=   -74.2 FOM=  0.98 TEST= 0
INDE   5  17  38 FOBS=   137.4 SIGMA=   1.0 PHAS=     9.9 FOM=  0.93 TEST= 0
INDE   5  17  40 FOBS=   148.9 SIGMA=   1.0 PHAS=    85.8 FOM=  0.81 TEST= 0
INDE   5  17  42 FOBS=    44.7 SIGMA=   3.0 PHAS=   179.6 FOM=  0.39 TEST= 0
INDE   5  17  44 FOBS=   183.2 SIGMA=   0.9 PHAS=   112.8 FOM=  0.62 TEST= 1
INDE   5  17  46 FOBS=   259.0 SIGMA=   1.1 PHAS=   -15.3 FOM=  0.96 TEST= 0
INDE   5  17  48 FOBS=    80.1 SIGMA=   2.7 PHAS=   122.9 FOM=  0.81 TEST= 0
INDE   5  17  50 FOBS=   166.3 SIGMA=   1.3 PHAS=   -97.5 FOM=  0.96 TEST= 0
INDE   5  17  52 FOBS=   115.9 SIGMA=   1.8 PHAS=   -47.1 FOM=  0.11 TEST= 1
INDE   5  17  54 FOBS=   182.6 SIGMA=   1.2 PHAS=   147.7 FOM=  0.93 TEST= 0
INDE   5  17  56 FOBS=    31.9 SIGMA=   6.8 PHAS=   -61.4 FOM=  0.70 TEST= 0
INDE   5  17  58 FOBS=   103.8 SIGMA=   1.9 PHAS=     2.0 FOM=  0.82 TEST= 0
INDE   5  17  60 FOBS=    32.2 SIGMA=   6.0 PHAS=   -65.2 FOM=  0.43 TEST= 0
INDE   5  17  62 FOBS=    12.0 SIGMA=  15.8 PHAS=  -166.6 FOM=  0.13 TEST= 0
INDE   5  17  64 FOBS=    47.3 SIGMA=   7.1 PHAS=    31.4 FOM=  0.58 TEST= 0
INDE   5  17  66 FOBS=    74.9 SIGMA=   5.8 PHAS=    35.8 FOM=  0.89 TEST= 0
INDE   5  17  68 FOBS=   109.9 SIGMA=   4.1 PHAS=   -36.0 FOM=  0.96 TEST= 0
INDE   5  17  70 FOBS=   109.9 SIGMA=   3.0 PHAS=  -128.9 FOM=  0.27 TEST= 1
INDE   5  17  72 FOBS=    72.4 SIGMA=   4.4 PHAS=  -124.3 FOM=  0.76 TEST= 0
INDE   5  17  74 FOBS=     0.0 SIGMA=  25.3 PHAS=     0.0 FOM=  0.00 TEST= 1
INDE   5  18   5 FOBS=   293.5 SIGMA=   0.4 PHAS=    42.6 FOM=  0.85 TEST= 0
INDE   5  18   7 FOBS=   339.4 SIGMA=   0.6 PHAS=   -75.6 FOM=  0.94 TEST= 0
INDE   5  18   9 FOBS=   194.6 SIGMA=   0.6 PHAS=   -91.6 FOM=  0.92 TEST= 0
INDE   5  18  11 FOBS=    45.0 SIGMA=   2.0 PHAS=    48.8 FOM=  0.59 TEST= 0
INDE   5  18  13 FOBS=   194.4 SIGMA=   0.6 PHAS=  -157.8 FOM=  0.77 TEST= 0
INDE   5  18  15 FOBS=    30.5 SIGMA=   3.3 PHAS=  -170.1 FOM=  0.63 TEST= 0
INDE   5  18  17 FOBS=   185.9 SIGMA=   0.6 PHAS=    78.0 FOM=  0.91 TEST= 0
INDE   5  18  19 FOBS=    36.0 SIGMA=   2.0 PHAS=    32.4 FOM=  0.95 TEST= 0
INDE   5  18  21 FOBS=   115.1 SIGMA=   0.7 PHAS=    34.3 FOM=  0.98 TEST= 0
INDE   5  18  23 FOBS=    42.8 SIGMA=   1.7 PHAS=    54.4 FOM=  0.86 TEST= 0
INDE   5  18  25 FOBS=   100.7 SIGMA=   0.8 PHAS=    -3.1 FOM=  0.89 TEST= 0
INDE   5  18  27 FOBS=   167.4 SIGMA=   0.6 PHAS=    66.3 FOM=  0.95 TEST= 0
INDE   5  18  29 FOBS=   123.9 SIGMA=   0.8 PHAS=   132.9 FOM=  0.99 TEST= 0
INDE   5  18  31 FOBS=   208.5 SIGMA=   0.7 PHAS=   137.3 FOM=  0.95 TEST= 0
INDE   5  18  33 FOBS=   100.3 SIGMA=   1.2 PHAS=   -58.9 FOM=  0.89 TEST= 0
INDE   5  18  35 FOBS=   298.1 SIGMA=   0.6 PHAS=  -130.2 FOM=  0.96 TEST= 0
INDE   5  18  37 FOBS=   238.4 SIGMA=   0.7 PHAS=  -150.7 FOM=  0.96 TEST= 0
INDE   5  18  39 FOBS=   145.0 SIGMA=   1.0 PHAS=   -35.1 FOM=  0.95 TEST= 0
INDE   5  18  41 FOBS=   100.3 SIGMA=   1.5 PHAS=   -69.8 FOM=  0.85 TEST= 0
INDE   5  18  43 FOBS=   178.5 SIGMA=   0.7 PHAS=     0.1 FOM=  0.96 TEST= 0
INDE   5  18  45 FOBS=   111.4 SIGMA=   1.5 PHAS=   -41.7 FOM=  0.95 TEST= 0
INDE   5  18  47 FOBS=    38.9 SIGMA=   4.0 PHAS=   121.7 FOM=  0.32 TEST= 0
INDE   5  18  49 FOBS=   219.2 SIGMA=   1.1 PHAS=  -129.8 FOM=  0.94 TEST= 0
INDE   5  18  51 FOBS=   116.1 SIGMA=   1.9 PHAS=   -66.0 FOM=  0.96 TEST= 0
INDE   5  18  53 FOBS=   182.4 SIGMA=   1.2 PHAS=   -22.9 FOM=  0.07 TEST= 1
INDE   5  18  55 FOBS=    33.0 SIGMA=   6.2 PHAS=   -15.4 FOM=  0.52 TEST= 0
INDE   5  18  57 FOBS=   167.7 SIGMA=   1.3 PHAS=  -136.4 FOM=  0.95 TEST= 0
INDE   5  18  59 FOBS=     0.0 SIGMA=  21.0 PHAS=     0.0 FOM=  0.00 TEST= 0
INDE   5  18  61 FOBS=   128.0 SIGMA=   1.6 PHAS=   151.3 FOM=  0.95 TEST= 0
INDE   5  18  63 FOBS=   105.3 SIGMA=   2.3 PHAS=    25.0 FOM=  0.46 TEST= 0
INDE   5  18  65 FOBS=    38.1 SIGMA=  11.5 PHAS=   -53.0 FOM=  0.01 TEST= 1
INDE   5  18  67 FOBS=    56.4 SIGMA=   7.8 PHAS=   100.4 FOM=  0.77 TEST= 0
INDE   5  18  69 FOBS=   106.1 SIGMA=   4.3 PHAS=  -141.7 FOM=  0.91 TEST= 0
INDE   5  18  71 FOBS=    37.1 SIGMA=   8.6 PHAS=  -128.5 FOM=  0.16 TEST= 0
INDE   5  18  73 FOBS=     0.0 SIGMA=  25.7 PHAS=     0.0 FOM=  0.00 TEST= 0
INDE   5  18  75 FOBS=    47.7 SIGMA=   7.0 PHAS=   -66.5 FOM=  0.54 TEST= 0
INDE   5  19   6 FOBS=   309.7 SIGMA=   0.4 PHAS=  -155.3 FOM=  0.91 TEST= 0
INDE   5  19   8 FOBS=   241.7 SIGMA=   0.7 PHAS=  -133.2 FOM=  0.85 TEST= 0
```

*FIG. 12A - 138*

```
INDE   5  19  10 FOBS=   14.7 SIGMA=   6.4 PHAS=  -20.5 FOM= 0.43 TEST= 0
INDE   5  19  12 FOBS=  144.4 SIGMA=   0.8 PHAS=  -80.2 FOM= 0.74 TEST= 0
INDE   5  19  14 FOBS=  117.7 SIGMA=   0.9 PHAS=   83.7 FOM= 0.83 TEST= 0
INDE   5  19  16 FOBS=   28.5 SIGMA=   3.7 PHAS=  106.9 FOM= 0.50 TEST= 0
INDE   5  19  18 FOBS=   49.2 SIGMA=   1.7 PHAS=   14.8 FOM= 0.91 TEST= 0
INDE   5  19  20 FOBS=  106.5 SIGMA=   0.8 PHAS=   52.4 FOM= 0.41 TEST= 0
INDE   5  19  22 FOBS=  241.8 SIGMA=   0.5 PHAS=  -58.5 FOM= 0.99 TEST= 0
INDE   5  19  24 FOBS=  109.7 SIGMA=   0.8 PHAS= -164.1 FOM= 0.93 TEST= 1
INDE   5  19  26 FOBS=   53.2 SIGMA=   1.5 PHAS=  117.6 FOM= 0.94 TEST= 0
INDE   5  19  28 FOBS=  128.0 SIGMA=   0.7 PHAS=   49.4 FOM= 0.99 TEST= 0
INDE   5  19  30 FOBS=  123.2 SIGMA=   0.8 PHAS= -126.9 FOM= 0.91 TEST= 0
INDE   5  19  32 FOBS=  211.1 SIGMA=   0.7 PHAS=   21.7 FOM= 0.95 TEST= 0
INDE   5  19  34 FOBS=   25.8 SIGMA=   5.0 PHAS=   56.8 FOM= 0.61 TEST= 0
INDE   5  19  36 FOBS=  319.2 SIGMA=   0.6 PHAS= -172.5 FOM= 0.96 TEST= 0
INDE   5  19  38 FOBS=   55.7 SIGMA=   2.5 PHAS= -101.0 FOM= 0.85 TEST= 0
INDE   5  19  40 FOBS=  171.3 SIGMA=   1.0 PHAS= -129.4 FOM= 0.94 TEST= 0
INDE   5  19  42 FOBS=  194.5 SIGMA=   0.9 PHAS=  -97.5 FOM= 0.99 TEST= 0
INDE   5  19  44 FOBS=  186.5 SIGMA=   0.9 PHAS=  169.1 FOM= 0.96 TEST= 0
INDE   5  19  46 FOBS=   76.1 SIGMA=   1.7 PHAS=  -49.8 FOM= 0.87 TEST= 0
INDE   5  19  48 FOBS=   53.7 SIGMA=   2.0 PHAS=  111.7 FOM= 0.88 TEST= 0
INDE   5  19  50 FOBS=  182.6 SIGMA=   1.3 PHAS= -148.5 FOM= 0.96 TEST= 0
INDE   5  19  52 FOBS=   63.6 SIGMA=   3.3 PHAS=    7.1 FOM= 0.74 TEST= 0
INDE   5  19  54 FOBS=  146.2 SIGMA=   1.5 PHAS=  -33.9 FOM= 0.94 TEST= 0
INDE   5  19  56 FOBS=    0.0 SIGMA=  20.0 PHAS=    0.0 FOM= 0.00 TEST= 0
INDE   5  19  58 FOBS=   38.2 SIGMA=   5.2 PHAS=   91.8 FOM= 0.32 TEST= 0
INDE   5  19  60 FOBS=   30.0 SIGMA=   6.6 PHAS=   25.0 FOM= 0.38 TEST= 0
INDE   5  19  62 FOBS=   72.5 SIGMA=   3.2 PHAS=  135.0 FOM= 0.84 TEST= 0
INDE   5  19  64 FOBS=  171.2 SIGMA=   2.8 PHAS=  103.2 FOM= 0.97 TEST= 0
INDE   5  19  66 FOBS=   38.3 SIGMA=  11.5 PHAS=  -25.9 FOM= 0.16 TEST= 0
INDE   5  19  68 FOBS=   53.7 SIGMA=   8.3 PHAS=   -1.4 FOM= 0.90 TEST= 0
INDE   5  19  70 FOBS=   34.8 SIGMA=   9.4 PHAS=  -50.5 FOM= 0.01 TEST= 1
INDE   5  19  72 FOBS=   92.7 SIGMA=   3.6 PHAS= -120.7 FOM= 0.84 TEST= 0
INDE   5  19  74 FOBS=   15.3 SIGMA=  21.6 PHAS=  -81.6 FOM= 0.26 TEST= 0
INDE   5  20   5 FOBS=   71.3 SIGMA=   0.8 PHAS=  102.4 FOM= 0.72 TEST= 0
INDE   5  20   7 FOBS=  133.9 SIGMA=   0.6 PHAS=   36.4 FOM= 0.72 TEST= 0
INDE   5  20   9 FOBS=  144.3 SIGMA=   0.6 PHAS= -135.9 FOM= 0.96 TEST= 0
INDE   5  20  11 FOBS=  290.7 SIGMA=   0.6 PHAS=  157.5 FOM= 0.89 TEST= 0
INDE   5  20  13 FOBS=  193.8 SIGMA=   0.7 PHAS= -120.2 FOM= 0.76 TEST= 0
INDE   5  20  15 FOBS=   99.5 SIGMA=   1.2 PHAS=  122.1 FOM= 0.95 TEST= 0
INDE   5  20  17 FOBS=  125.7 SIGMA=   0.9 PHAS=   71.0 FOM= 0.96 TEST= 0
INDE   5  20  19 FOBS=    0.0 SIGMA=  14.2 PHAS=    0.0 FOM= 0.00 TEST= 0
INDE   5  20  21 FOBS=   70.6 SIGMA=   1.2 PHAS=  121.6 FOM= 0.88 TEST= 0
INDE   5  20  23 FOBS=  166.0 SIGMA=   0.7 PHAS= -139.7 FOM= 0.97 TEST= 0
INDE   5  20  25 FOBS=   74.3 SIGMA=   1.2 PHAS=    8.6 FOM= 0.96 TEST= 0
INDE   5  20  27 FOBS=   99.7 SIGMA=   0.9 PHAS=   23.0 FOM= 0.98 TEST= 0
INDE   5  20  29 FOBS=  165.9 SIGMA=   0.6 PHAS=  123.9 FOM= 0.89 TEST= 0
INDE   5  20  31 FOBS=   85.0 SIGMA=   1.2 PHAS= -172.9 FOM= 0.94 TEST= 0
INDE   5  20  33 FOBS=  260.8 SIGMA=   0.6 PHAS=  -51.8 FOM= 0.96 TEST= 1
INDE   5  20  35 FOBS=   89.5 SIGMA=   1.5 PHAS=   48.8 FOM= 0.95 TEST= 0
INDE   5  20  37 FOBS=    0.0 SIGMA=  17.3 PHAS=    0.0 FOM= 0.00 TEST= 0
INDE   5  20  39 FOBS=  396.5 SIGMA=   0.6 PHAS=  140.1 FOM= 0.98 TEST= 0
INDE   5  20  41 FOBS=   83.6 SIGMA=   2.0 PHAS=    1.6 FOM= 0.98 TEST= 0
INDE   5  20  43 FOBS=   48.8 SIGMA=   3.1 PHAS=  -46.9 FOM= 0.04 TEST= 0
INDE   5  20  45 FOBS=  195.0 SIGMA=   0.8 PHAS=   29.7 FOM= 0.97 TEST= 0
INDE   5  20  47 FOBS=   83.2 SIGMA=   1.6 PHAS=   -4.3 FOM= 0.71 TEST= 0
INDE   5  20  49 FOBS=   89.9 SIGMA=   1.6 PHAS=  -57.7 FOM= 0.53 TEST= 0
INDE   5  20  51 FOBS=   85.8 SIGMA=   2.5 PHAS=  -47.6 FOM= 0.88 TEST= 0
INDE   5  20  53 FOBS=  106.0 SIGMA=   2.0 PHAS= -151.8 FOM= 0.81 TEST= 1
INDE   5  20  55 FOBS=   66.8 SIGMA=   3.1 PHAS= -144.5 FOM= 0.67 TEST= 0
INDE   5  20  57 FOBS=   52.6 SIGMA=   3.8 PHAS=  113.2 FOM= 0.76 TEST= 0
INDE   5  20  59 FOBS=    0.0 SIGMA=  20.7 PHAS=    0.0 FOM= 0.00 TEST= 0
INDE   5  20  61 FOBS=   79.0 SIGMA=   2.7 PHAS=  158.1 FOM= 0.88 TEST= 0
INDE   5  20  63 FOBS=  114.5 SIGMA=   2.1 PHAS=   51.5 FOM= 0.90 TEST= 0
INDE   5  20  65 FOBS=   86.9 SIGMA=   5.2 PHAS=   15.0 FOM= 0.89 TEST= 0
INDE   5  20  67 FOBS=    0.0 SIGMA=  29.6 PHAS=    0.0 FOM= 0.00 TEST= 0
INDE   5  20  69 FOBS=   46.4 SIGMA=   9.8 PHAS=  -74.3 FOM= 0.76 TEST= 0
INDE   5  20  71 FOBS=   51.1 SIGMA=   6.5 PHAS=   26.2 FOM= 0.53 TEST= 0
INDE   5  20  73 FOBS=   42.1 SIGMA=   8.1 PHAS=  167.9 FOM= 0.63 TEST= 0
INDE   5  21   6 FOBS=  440.0 SIGMA=   0.5 PHAS=  121.9 FOM= 0.99 TEST= 0
INDE   5  21   8 FOBS=   84.2 SIGMA=   1.0 PHAS= -145.5 FOM= 0.57 TEST= 0
```

*FIG. 12A - 139*

```
INDE  5  21  10 FOBS=  156.7 SIGMA=  0.7 PHAS=  -93.8 FOM= 0.78 TEST= 0
INDE  5  21  12 FOBS=  415.0 SIGMA=  0.7 PHAS= -155.8 FOM= 0.98 TEST= 0
INDE  5  21  14 FOBS=  152.9 SIGMA=  0.8 PHAS=  125.5 FOM= 0.84 TEST= 0
INDE  5  21  16 FOBS=   47.4 SIGMA=  2.5 PHAS=  -88.8 FOM= 0.87 TEST= 0
INDE  5  21  18 FOBS=   46.9 SIGMA=  2.2 PHAS= -157.6 FOM= 0.22 TEST= 0
INDE  5  21  20 FOBS=  195.8 SIGMA=  0.6 PHAS=   52.9 FOM= 0.99 TEST= 0
INDE  5  21  22 FOBS=  157.1 SIGMA=  0.7 PHAS=  -18.8 FOM= 0.89 TEST= 0
INDE  5  21  24 FOBS=   74.0 SIGMA=  1.2 PHAS= -132.6 FOM= 0.92 TEST= 0
INDE  5  21  26 FOBS=   94.8 SIGMA=  1.0 PHAS=  -95.6 FOM= 0.95 TEST= 0
INDE  5  21  28 FOBS=  110.3 SIGMA=  0.9 PHAS=  -39.3 FOM= 0.99 TEST= 0
INDE  5  21  30 FOBS=  173.6 SIGMA=  0.7 PHAS= -118.3 FOM= 0.94 TEST= 0
INDE  5  21  32 FOBS=  112.8 SIGMA=  1.0 PHAS=  121.4 FOM= 0.99 TEST= 1
INDE  5  21  34 FOBS=  196.2 SIGMA=  0.7 PHAS= -122.4 FOM= 0.96 TEST= 0
INDE  5  21  36 FOBS=  136.9 SIGMA=  1.1 PHAS= -178.6 FOM= 0.97 TEST= 0
INDE  5  21  38 FOBS=  162.2 SIGMA=  1.0 PHAS=    3.3 FOM= 0.90 TEST= 0
INDE  5  21  40 FOBS=   94.1 SIGMA=  1.7 PHAS=  116.2 FOM= 0.96 TEST= 0
INDE  5  21  42 FOBS=  160.3 SIGMA=  1.1 PHAS= -171.4 FOM= 0.67 TEST= 1
INDE  5  21  44 FOBS=  120.6 SIGMA=  1.2 PHAS= -163.4 FOM= 0.61 TEST= 0
INDE  5  21  46 FOBS=  142.7 SIGMA=  1.0 PHAS=  -52.6 FOM= 0.82 TEST= 0
INDE  5  21  48 FOBS=   75.5 SIGMA=  1.7 PHAS= -138.9 FOM= 0.70 TEST= 0
INDE  5  21  50 FOBS=  230.0 SIGMA=  0.7 PHAS= -142.5 FOM= 0.95 TEST= 0
INDE  5  21  52 FOBS=   93.1 SIGMA=  2.3 PHAS=   -2.4 FOM= 0.83 TEST= 0
INDE  5  21  54 FOBS=  145.9 SIGMA=  1.5 PHAS=  -11.3 FOM= 0.95 TEST= 0
INDE  5  21  56 FOBS=    0.0 SIGMA= 20.2 PHAS=    0.0 FOM= 0.00 TEST= 0
INDE  5  21  58 FOBS=   50.2 SIGMA=  4.0 PHAS=   45.8 FOM= 0.53 TEST= 0
INDE  5  21  60 FOBS=  103.7 SIGMA=  2.0 PHAS=   81.1 FOM= 0.32 TEST= 1
INDE  5  21  62 FOBS=    0.0 SIGMA= 23.6 PHAS=    0.0 FOM= 0.00 TEST= 0
INDE  5  21  64 FOBS=   32.7 SIGMA= 13.6 PHAS=  144.1 FOM= 0.56 TEST= 0
INDE  5  21  66 FOBS=   38.3 SIGMA= 11.7 PHAS=  155.4 FOM= 0.46 TEST= 0
INDE  5  21  68 FOBS=    0.0 SIGMA= 29.8 PHAS=    0.0 FOM= 0.00 TEST= 1
INDE  5  21  70 FOBS=   18.3 SIGMA= 24.9 PHAS= -119.6 FOM= 0.27 TEST= 0
INDE  5  21  72 FOBS=   26.7 SIGMA= 12.7 PHAS= -140.6 FOM= 0.64 TEST= 0
INDE  5  21  74 FOBS=   43.3 SIGMA=  8.0 PHAS=   52.8 FOM= 0.82 TEST= 0
INDE  5  22   5 FOBS=  510.4 SIGMA=  0.5 PHAS=   36.6 FOM= 0.98 TEST= 0
INDE  5  22   7 FOBS=  346.4 SIGMA=  0.5 PHAS=   83.5 FOM= 0.94 TEST= 0
INDE  5  22   9 FOBS=   64.5 SIGMA=  1.2 PHAS= -151.4 FOM= 0.41 TEST= 1
INDE  5  22  11 FOBS=  227.5 SIGMA=  0.6 PHAS=  143.9 FOM= 0.80 TEST= 0
INDE  5  22  13 FOBS=  278.6 SIGMA=  0.6 PHAS=   87.9 FOM= 0.96 TEST= 0
INDE  5  22  15 FOBS=  124.3 SIGMA=  1.1 PHAS=  147.2 FOM= 0.92 TEST= 0
INDE  5  22  17 FOBS=   79.8 SIGMA=  1.6 PHAS= -147.5 FOM= 0.95 TEST= 0
INDE  5  22  19 FOBS=   35.4 SIGMA=  2.6 PHAS=   -9.7 FOM= 0.93 TEST= 0
INDE  5  22  21 FOBS=  200.7 SIGMA=  0.6 PHAS= -114.4 FOM= 0.93 TEST= 0
INDE  5  22  23 FOBS=  203.4 SIGMA=  0.6 PHAS= -109.8 FOM= 0.98 TEST= 0
INDE  5  22  25 FOBS=  232.2 SIGMA=  0.6 PHAS=  153.6 FOM= 0.94 TEST= 0
INDE  5  22  27 FOBS=  278.4 SIGMA=  0.6 PHAS= -119.2 FOM= 0.99 TEST= 0
INDE  5  22  29 FOBS=  276.6 SIGMA=  0.5 PHAS=  175.7 FOM= 0.98 TEST= 1
INDE  5  22  31 FOBS=  235.4 SIGMA=  0.6 PHAS=  119.2 FOM= 0.98 TEST= 0
INDE  5  22  33 FOBS=   44.8 SIGMA=  2.5 PHAS=   35.6 FOM= 0.32 TEST= 0
INDE  5  22  35 FOBS=  202.9 SIGMA=  0.7 PHAS=  116.1 FOM= 0.84 TEST= 0
INDE  5  22  37 FOBS=   74.1 SIGMA=  2.0 PHAS= -166.2 FOM= 0.98 TEST= 0
INDE  5  22  39 FOBS=  218.6 SIGMA=  0.8 PHAS=  133.0 FOM= 0.88 TEST= 0
INDE  5  22  41 FOBS=  162.9 SIGMA=  1.1 PHAS=   37.0 FOM= 0.91 TEST= 0
INDE  5  22  43 FOBS=  177.6 SIGMA=  1.1 PHAS=  132.9 FOM= 0.95 TEST= 0
INDE  5  22  45 FOBS=   63.0 SIGMA=  2.2 PHAS=  -62.9 FOM= 0.74 TEST= 0
INDE  5  22  47 FOBS=  143.2 SIGMA=  1.0 PHAS= -178.5 FOM= 0.86 TEST= 0
INDE  5  22  49 FOBS=  145.4 SIGMA=  0.9 PHAS=  107.7 FOM= 0.80 TEST= 0
INDE  5  22  51 FOBS=  112.2 SIGMA=  1.2 PHAS= -143.4 FOM= 0.93 TEST= 0
INDE  5  22  53 FOBS=  281.7 SIGMA=  0.9 PHAS= -110.6 FOM= 0.98 TEST= 0
INDE  5  22  55 FOBS=  137.2 SIGMA=  1.6 PHAS=  -66.7 FOM= 0.87 TEST= 0
INDE  5  22  57 FOBS=   72.3 SIGMA=  2.9 PHAS=   80.7 FOM= 0.90 TEST= 0
INDE  5  22  59 FOBS=   76.4 SIGMA=  2.7 PHAS=   77.4 FOM= 0.83 TEST= 0
INDE  5  22  61 FOBS=    0.0 SIGMA= 20.4 PHAS=    0.0 FOM= 0.00 TEST= 0
INDE  5  22  63 FOBS=   84.4 SIGMA=  3.8 PHAS=  126.9 FOM= 0.92 TEST= 0
INDE  5  22  65 FOBS=   53.1 SIGMA=  8.4 PHAS=   81.2 FOM= 0.84 TEST= 0
INDE  5  22  67 FOBS=   35.0 SIGMA= 12.7 PHAS=  113.1 FOM= 0.15 TEST= 0
INDE  5  22  71 FOBS=   17.1 SIGMA= 19.9 PHAS= -179.6 FOM= 0.10 TEST= 0
INDE  5  22  73 FOBS=   39.4 SIGMA=  8.9 PHAS=  -80.5 FOM= 0.70 TEST= 0
INDE  5  23   6 FOBS=  246.2 SIGMA=  0.5 PHAS=   13.7 FOM= 0.99 TEST= 0
INDE  5  23   8 FOBS=   71.9 SIGMA=  1.1 PHAS=  -75.4 FOM= 0.97 TEST= 0
INDE  5  23  10 FOBS=  188.9 SIGMA=  0.7 PHAS=  -21.5 FOM= 0.98 TEST= 0
```

*FIG. 12A - 140*

```
INDE  5  23  12  FOBS=   87.2  SIGMA=   1.0  PHAS=  -43.5  FOM= 0.98  TEST= 0
INDE  5  23  14  FOBS=  128.2  SIGMA=   1.0  PHAS= -171.0  FOM= 0.98  TEST= 0
INDE  5  23  16  FOBS=  122.5  SIGMA=   1.1  PHAS=  158.8  FOM= 0.90  TEST= 0
INDE  5  23  18  FOBS=   35.0  SIGMA=   3.2  PHAS=  -48.7  FOM= 0.98  TEST= 0
INDE  5  23  20  FOBS=  263.0  SIGMA=   0.6  PHAS=   51.2  FOM= 0.95  TEST= 0
INDE  5  23  22  FOBS=   21.1  SIGMA=   4.2  PHAS=  123.1  FOM= 0.91  TEST= 0
INDE  5  23  24  FOBS=  226.1  SIGMA=   0.6  PHAS=   50.9  FOM= 0.95  TEST= 0
INDE  5  23  26  FOBS=  232.6  SIGMA=   0.6  PHAS=  114.4  FOM= 0.90  TEST= 0
INDE  5  23  28  FOBS=  276.0  SIGMA=   0.5  PHAS=  126.0  FOM= 0.99  TEST= 0
INDE  5  23  30  FOBS=  279.5  SIGMA=   0.6  PHAS=   44.3  FOM= 0.96  TEST= 0
INDE  5  23  32  FOBS=  247.8  SIGMA=   0.7  PHAS=   88.6  FOM= 0.94  TEST= 0
INDE  5  23  34  FOBS=   73.1  SIGMA=   1.6  PHAS= -174.6  FOM= 0.94  TEST= 0
INDE  5  23  36  FOBS=   75.7  SIGMA=   1.6  PHAS=   33.8  FOM= 0.74  TEST= 0
INDE  5  23  38  FOBS=   95.8  SIGMA=   1.7  PHAS=  131.4  FOM= 0.92  TEST= 0
INDE  5  23  40  FOBS=    0.0  SIGMA=  19.4  PHAS=    0.0  FOM= 0.00  TEST= 0
INDE  5  23  42  FOBS=  111.4  SIGMA=   1.7  PHAS=   -1.6  FOM= 0.94  TEST= 0
INDE  5  23  44  FOBS=  141.4  SIGMA=   1.4  PHAS=  -75.1  FOM= 0.64  TEST= 0
INDE  5  23  46  FOBS=   31.2  SIGMA=   4.5  PHAS=  -71.8  FOM= 0.29  TEST= 0
INDE  5  23  48  FOBS=  148.1  SIGMA=   0.9  PHAS=   18.9  FOM= 0.78  TEST= 0
INDE  5  23  50  FOBS=   85.0  SIGMA=   1.5  PHAS= -145.2  FOM= 0.90  TEST= 0
INDE  5  23  52  FOBS=   91.9  SIGMA=   1.4  PHAS=  126.7  FOM= 0.93  TEST= 0
INDE  5  23  54  FOBS=  134.9  SIGMA=   1.6  PHAS=  178.9  FOM= 0.93  TEST= 0
INDE  5  23  56  FOBS=   27.0  SIGMA=   8.3  PHAS= -115.0  FOM= 0.28  TEST= 0
INDE  5  23  58  FOBS=   75.1  SIGMA=   2.8  PHAS=  -34.8  FOM= 0.91  TEST= 0
INDE  5  23  60  FOBS=   23.5  SIGMA=   9.3  PHAS= -129.4  FOM= 0.25  TEST= 0
INDE  5  23  62  FOBS=   76.1  SIGMA=   3.6  PHAS= -127.6  FOM= 0.94  TEST= 0
INDE  5  23  64  FOBS=   47.6  SIGMA=   9.5  PHAS=  -35.9  FOM= 0.76  TEST= 0
INDE  5  23  66  FOBS=   77.1  SIGMA=   5.9  PHAS=   42.7  FOM= 0.79  TEST= 0
INDE  5  23  68  FOBS=   11.6  SIGMA=  38.7  PHAS= -170.1  FOM= 0.10  TEST= 0
INDE  5  23  70  FOBS=   41.4  SIGMA=  11.1  PHAS= -139.5  FOM= 0.06  TEST= 0
INDE  5  23  72  FOBS=   43.5  SIGMA=   8.0  PHAS=  116.2  FOM= 0.76  TEST= 0
INDE  5  23  74  FOBS=   36.9  SIGMA=   9.7  PHAS=  148.1  FOM= 0.42  TEST= 0
INDE  5  24   5  FOBS=   91.1  SIGMA=   0.9  PHAS=   28.6  FOM= 0.93  TEST= 1
INDE  5  24   7  FOBS=  104.2  SIGMA=   0.7  PHAS=  164.8  FOM= 0.80  TEST= 0
INDE  5  24   9  FOBS=  106.2  SIGMA=   0.8  PHAS= -139.2  FOM= 0.98  TEST= 0
INDE  5  24  11  FOBS=   71.0  SIGMA=   1.2  PHAS=  129.8  FOM= 0.83  TEST= 1
INDE  5  24  13  FOBS=  225.3  SIGMA=   0.7  PHAS=   68.0  FOM= 0.98  TEST= 0
INDE  5  24  15  FOBS=  260.6  SIGMA=   0.7  PHAS=  136.6  FOM= 0.94  TEST= 0
INDE  5  24  17  FOBS=  155.4  SIGMA=   1.0  PHAS=  141.7  FOM= 0.95  TEST= 0
INDE  5  24  19  FOBS=  165.8  SIGMA=   0.9  PHAS=  -16.0  FOM= 0.93  TEST= 0
INDE  5  24  21  FOBS=  185.8  SIGMA=   0.7  PHAS= -103.9  FOM= 0.95  TEST= 0
INDE  5  24  23  FOBS=  229.4  SIGMA=   0.6  PHAS=  -62.4  FOM= 0.99  TEST= 0
INDE  5  24  25  FOBS=   86.5  SIGMA=   1.2  PHAS=  -46.6  FOM= 0.86  TEST= 0
INDE  5  24  27  FOBS=  147.4  SIGMA=   0.8  PHAS=  -84.7  FOM= 0.99  TEST= 0
INDE  5  24  29  FOBS=  293.7  SIGMA=   0.5  PHAS=  -39.1  FOM= 0.92  TEST= 0
INDE  5  24  31  FOBS=  178.5  SIGMA=   0.8  PHAS=   29.6  FOM= 0.93  TEST= 0
INDE  5  24  33  FOBS=  201.6  SIGMA=   0.7  PHAS=   63.2  FOM= 0.96  TEST= 0
INDE  5  24  35  FOBS=  158.7  SIGMA=   0.9  PHAS=  167.9  FOM= 0.79  TEST= 0
INDE  5  24  37  FOBS=   15.0  SIGMA=  10.1  PHAS=   94.2  FOM= 0.01  TEST= 1
INDE  5  24  39  FOBS=  101.1  SIGMA=   1.7  PHAS=   14.4  FOM= 0.28  TEST= 1
INDE  5  24  41  FOBS=  107.4  SIGMA=   1.7  PHAS=  133.2  FOM= 0.80  TEST= 0
INDE  5  24  43  FOBS=  106.1  SIGMA=   1.8  PHAS=  149.7  FOM= 0.89  TEST= 0
INDE  5  24  45  FOBS=  111.2  SIGMA=   1.3  PHAS= -133.6  FOM= 0.91  TEST= 0
INDE  5  24  47  FOBS=   67.0  SIGMA=   2.1  PHAS=   68.4  FOM= 0.34  TEST= 0
INDE  5  24  49  FOBS=   25.3  SIGMA=   5.6  PHAS=  -30.2  FOM= 0.31  TEST= 0
INDE  5  24  51  FOBS=   20.3  SIGMA=   6.5  PHAS=   75.7  FOM= 0.56  TEST= 0
INDE  5  24  53  FOBS=   87.6  SIGMA=   1.4  PHAS= -144.5  FOM= 0.86  TEST= 0
INDE  5  24  55  FOBS=   29.4  SIGMA=   7.2  PHAS=  -79.5  FOM= 0.14  TEST= 0
INDE  5  24  57  FOBS=  119.2  SIGMA=   1.8  PHAS=  162.4  FOM= 0.94  TEST= 0
INDE  5  24  59  FOBS=    0.0  SIGMA=  21.0  PHAS=    0.0  FOM= 0.00  TEST= 0
INDE  5  24  61  FOBS=   25.0  SIGMA=   9.7  PHAS=  175.6  FOM= 0.55  TEST= 0
INDE  5  24  63  FOBS=  110.4  SIGMA=   3.0  PHAS=  156.2  FOM= 0.87  TEST= 0
INDE  5  24  65  FOBS=   34.3  SIGMA=  13.4  PHAS=  -59.3  FOM= 0.10  TEST= 1
INDE  5  24  67  FOBS=   41.0  SIGMA=  11.2  PHAS=  160.7  FOM= 0.60  TEST= 0
INDE  5  24  69  FOBS=   32.8  SIGMA=  14.1  PHAS=   10.2  FOM= 0.62  TEST= 0
INDE  5  24  71  FOBS=   58.9  SIGMA=   8.1  PHAS=    6.9  FOM= 0.84  TEST= 0
INDE  5  24  73  FOBS=   75.9  SIGMA=   4.8  PHAS=  -12.8  FOM= 0.80  TEST= 0
INDE  5  25   6  FOBS=  124.9  SIGMA=   0.6  PHAS=   61.6  FOM= 0.91  TEST= 0
INDE  5  25   8  FOBS=  120.6  SIGMA=   0.8  PHAS= -162.4  FOM= 0.98  TEST= 0
INDE  5  25  10  FOBS=  136.7  SIGMA=   0.7  PHAS=   31.0  FOM= 0.99  TEST= 0
```

*FIG. 12A - 141*

```
INDE  5 25 12 FOBS=  86.8 SIGMA=  1.0 PHAS=   78.4 FOM= 0.63 TEST= 1
INDE  5 25 14 FOBS=  21.9 SIGMA=  5.1 PHAS=  -83.8 FOM= 0.74 TEST= 0
INDE  5 25 16 FOBS= 205.8 SIGMA=  0.9 PHAS=   63.3 FOM= 0.98 TEST= 0
INDE  5 25 18 FOBS= 190.6 SIGMA=  0.8 PHAS=  -57.4 FOM= 0.90 TEST= 0
INDE  5 25 20 FOBS= 167.6 SIGMA=  0.9 PHAS=  119.8 FOM= 0.95 TEST= 0
INDE  5 25 22 FOBS=  91.0 SIGMA=  1.3 PHAS= -165.0 FOM= 0.91 TEST= 0
INDE  5 25 24 FOBS= 154.5 SIGMA=  0.8 PHAS=  157.4 FOM= 0.99 TEST= 0
INDE  5 25 26 FOBS= 297.7 SIGMA=  0.5 PHAS= -152.0 FOM= 0.70 TEST= 1
INDE  5 25 28 FOBS= 285.4 SIGMA=  0.6 PHAS=  178.6 FOM= 0.93 TEST= 0
INDE  5 25 30 FOBS= 102.8 SIGMA=  1.2 PHAS=   12.5 FOM= 0.86 TEST= 0
INDE  5 25 32 FOBS= 251.7 SIGMA=  0.8 PHAS=   -9.4 FOM= 0.98 TEST= 0
INDE  5 25 34 FOBS= 183.0 SIGMA=  0.8 PHAS=   44.4 FOM= 0.91 TEST= 0
INDE  5 25 36 FOBS= 130.2 SIGMA=  1.2 PHAS=  -49.9 FOM= 0.93 TEST= 0
INDE  5 25 38 FOBS= 171.7 SIGMA=  0.9 PHAS=  135.1 FOM= 0.94 TEST= 1
INDE  5 25 40 FOBS=  44.1 SIGMA=  4.4 PHAS=  106.5 FOM= 0.58 TEST= 0
INDE  5 25 42 FOBS=  82.1 SIGMA=  2.3 PHAS=    0.4 FOM= 0.90 TEST= 0
INDE  5 25 44 FOBS=   0.0 SIGMA= 20.3 PHAS=    0.0 FOM= 0.00 TEST= 0
INDE  5 25 46 FOBS=  85.4 SIGMA=  1.7 PHAS= -176.7 FOM= 0.39 TEST= 0
INDE  5 25 48 FOBS= 129.0 SIGMA=  1.1 PHAS= -123.4 FOM= 0.89 TEST= 0
INDE  5 25 50 FOBS=  59.9 SIGMA=  2.2 PHAS= -115.7 FOM= 0.86 TEST= 0
INDE  5 25 52 FOBS=  60.6 SIGMA=  2.2 PHAS= -139.6 FOM= 0.83 TEST= 0
INDE  5 25 54 FOBS=  88.6 SIGMA=  1.4 PHAS=  133.4 FOM= 0.93 TEST= 0
INDE  5 25 56 FOBS= 119.1 SIGMA=  1.7 PHAS=   -7.0 FOM= 0.89 TEST= 0
INDE  5 25 58 FOBS=  44.4 SIGMA=  4.7 PHAS=  -23.1 FOM= 0.70 TEST= 0
INDE  5 25 60 FOBS=   0.0 SIGMA= 21.0 PHAS=    0.0 FOM= 0.00 TEST= 0
INDE  5 25 62 FOBS=  37.4 SIGMA=  8.5 PHAS= -156.1 FOM= 0.30 TEST= 0
INDE  5 25 64 FOBS=  68.7 SIGMA=  4.7 PHAS=  -40.0 FOM= 0.60 TEST= 0
INDE  5 25 66 FOBS=  29.8 SIGMA= 15.5 PHAS=   22.9 FOM= 0.25 TEST= 0
INDE  5 25 68 FOBS= 112.7 SIGMA=  4.4 PHAS= -139.2 FOM= 0.88 TEST= 0
INDE  5 25 70 FOBS=  59.0 SIGMA=  8.0 PHAS=  -50.5 FOM= 0.81 TEST= 0
INDE  5 25 72 FOBS=  36.9 SIGMA=  9.7 PHAS=   75.4 FOM= 0.28 TEST= 0
INDE  5 26  5 FOBS=  70.2 SIGMA=  1.2 PHAS=  -27.6 FOM= 0.94 TEST= 1
INDE  5 26  7 FOBS= 122.1 SIGMA=  0.6 PHAS=   49.2 FOM= 0.99 TEST= 0
INDE  5 26  9 FOBS=  56.2 SIGMA=  1.5 PHAS=  -93.3 FOM= 0.35 TEST= 0
INDE  5 26 11 FOBS=  49.2 SIGMA=  1.8 PHAS=   60.7 FOM= 0.96 TEST= 0
INDE  5 26 13 FOBS=  77.7 SIGMA=  1.2 PHAS=   38.7 FOM= 0.95 TEST= 1
INDE  5 26 15 FOBS= 123.2 SIGMA=  1.1 PHAS=  -89.2 FOM= 0.89 TEST= 0
INDE  5 26 17 FOBS= 180.0 SIGMA=  1.0 PHAS= -103.9 FOM= 0.96 TEST= 0
INDE  5 26 19 FOBS= 151.9 SIGMA=  1.0 PHAS=   75.0 FOM= 0.98 TEST= 0
INDE  5 26 21 FOBS= 206.4 SIGMA=  0.8 PHAS=  -54.8 FOM= 0.88 TEST= 0
INDE  5 26 23 FOBS=   0.0 SIGMA= 16.4 PHAS=    0.0 FOM= 0.00 TEST= 1
INDE  5 26 25 FOBS= 305.5 SIGMA=  0.5 PHAS=   30.6 FOM= 0.95 TEST= 0
INDE  5 26 27 FOBS= 121.9 SIGMA=  1.0 PHAS=  123.2 FOM= 0.95 TEST= 0
INDE  5 26 29 FOBS= 220.4 SIGMA=  0.7 PHAS=  -14.0 FOM= 0.94 TEST= 0
INDE  5 26 31 FOBS=   0.0 SIGMA= 16.3 PHAS=    0.0 FOM= 0.00 TEST= 0
INDE  5 26 33 FOBS= 154.8 SIGMA=  1.0 PHAS=  -78.5 FOM= 0.95 TEST= 0
INDE  5 26 35 FOBS= 186.0 SIGMA=  0.9 PHAS= -139.4 FOM= 0.98 TEST= 0
INDE  5 26 37 FOBS=  83.1 SIGMA=  2.0 PHAS=  118.6 FOM= 0.90 TEST= 0
INDE  5 26 39 FOBS= 127.5 SIGMA=  1.3 PHAS=   16.8 FOM= 0.88 TEST= 0
INDE  5 26 41 FOBS= 308.7 SIGMA=  0.7 PHAS=  161.7 FOM= 0.97 TEST= 0
INDE  5 26 43 FOBS=  77.2 SIGMA=  2.4 PHAS=  126.6 FOM= 0.81 TEST= 0
INDE  5 26 45 FOBS= 116.3 SIGMA=  1.4 PHAS=  133.4 FOM= 0.97 TEST= 0
INDE  5 26 47 FOBS= 125.3 SIGMA=  1.2 PHAS=  150.8 FOM= 0.91 TEST= 0
INDE  5 26 49 FOBS= 130.7 SIGMA=  1.1 PHAS=  106.2 FOM= 0.57 TEST= 0
INDE  5 26 51 FOBS= 183.1 SIGMA=  0.8 PHAS=  145.5 FOM= 0.96 TEST= 0
INDE  5 26 53 FOBS=  80.0 SIGMA=  1.6 PHAS=  151.6 FOM= 0.78 TEST= 0
INDE  5 26 55 FOBS=  54.3 SIGMA=  2.3 PHAS=  -67.4 FOM= 0.79 TEST= 0
INDE  5 26 57 FOBS= 117.5 SIGMA=  1.6 PHAS= -153.5 FOM= 0.94 TEST= 0
INDE  5 26 59 FOBS=  66.4 SIGMA=  3.7 PHAS=  -34.0 FOM= 0.40 TEST= 0
INDE  5 26 61 FOBS=   0.0 SIGMA= 23.8 PHAS=    0.0 FOM= 0.00 TEST= 0
INDE  5 26 63 FOBS=   0.0 SIGMA= 25.4 PHAS=    0.0 FOM= 0.00 TEST= 0
INDE  5 26 65 FOBS=   0.0 SIGMA= 30.3 PHAS=    0.0 FOM= 0.00 TEST= 0
INDE  5 26 67 FOBS= 125.0 SIGMA=  3.9 PHAS=  159.8 FOM= 0.91 TEST= 0
INDE  5 26 69 FOBS=  62.3 SIGMA=  7.8 PHAS=   94.0 FOM= 0.93 TEST= 0
INDE  5 26 71 FOBS=  97.3 SIGMA=  5.0 PHAS=  -22.7 FOM= 0.64 TEST= 1
INDE  5 26 73 FOBS=  59.4 SIGMA=  6.2 PHAS= -122.7 FOM= 0.88 TEST= 0
INDE  5 27  6 FOBS=  71.7 SIGMA=  1.0 PHAS=   -1.1 FOM= 0.94 TEST= 1
INDE  5 27  8 FOBS= 207.7 SIGMA=  0.6 PHAS= -100.4 FOM= 0.97 TEST= 0
INDE  5 27 10 FOBS=  92.0 SIGMA=  1.1 PHAS=  140.5 FOM= 0.95 TEST= 0
INDE  5 27 12 FOBS=  28.0 SIGMA=  3.5 PHAS=  -33.6 FOM= 0.54 TEST= 0
```

*FIG. 12A - 142*

| | | | | | | | | | | | |
|---|---|---|---|---|---|---|---|---|---|---|---|
| INDE | 5 | 27 | 14 | FOBS= | 140.2 | SIGMA= | 0.8 | PHAS= | -133.0 | FOM= | 0.93 | TEST= 0
| INDE | 5 | 27 | 16 | FOBS= | 254.7 | SIGMA= | 1.0 | PHAS= | 179.9 | FOM= | 0.95 | TEST= 0
| INDE | 5 | 27 | 18 | FOBS= | 236.5 | SIGMA= | 0.9 | PHAS= | -99.4 | FOM= | 0.96 | TEST= 0
| INDE | 5 | 27 | 20 | FOBS= | 43.8 | SIGMA= | 3.0 | PHAS= | 98.7 | FOM= | 0.90 | TEST= 0
| INDE | 5 | 27 | 22 | FOBS= | 166.4 | SIGMA= | 1.0 | PHAS= | 99.2 | FOM= | 0.96 | TEST= 0
| INDE | 5 | 27 | 24 | FOBS= | 29.0 | SIGMA= | 4.8 | PHAS= | 173.5 | FOM= | 0.18 | TEST= 0
| INDE | 5 | 27 | 26 | FOBS= | 195.5 | SIGMA= | 0.7 | PHAS= | -151.6 | FOM= | 0.92 | TEST= 1
| INDE | 5 | 27 | 28 | FOBS= | 92.3 | SIGMA= | 1.4 | PHAS= | 175.8 | FOM= | 0.22 | TEST= 1
| INDE | 5 | 27 | 30 | FOBS= | 143.2 | SIGMA= | 1.0 | PHAS= | -4.5 | FOM= | 0.90 | TEST= 0
| INDE | 5 | 27 | 32 | FOBS= | 57.7 | SIGMA= | 2.5 | PHAS= | 130.8 | FOM= | 0.44 | TEST= 0
| INDE | 5 | 27 | 34 | FOBS= | 119.5 | SIGMA= | 1.4 | PHAS= | 156.0 | FOM= | 0.93 | TEST= 0
| INDE | 5 | 27 | 36 | FOBS= | 338.1 | SIGMA= | 0.8 | PHAS= | 146.6 | FOM= | 0.97 | TEST= 0
| INDE | 5 | 27 | 38 | FOBS= | 103.1 | SIGMA= | 1.7 | PHAS= | 96.0 | FOM= | 0.85 | TEST= 0
| INDE | 5 | 27 | 40 | FOBS= | 284.5 | SIGMA= | 0.7 | PHAS= | 49.5 | FOM= | 0.97 | TEST= 0
| INDE | 5 | 27 | 42 | FOBS= | 199.6 | SIGMA= | 0.9 | PHAS= | -25.4 | FOM= | 0.97 | TEST= 0
| INDE | 5 | 27 | 44 | FOBS= | 74.8 | SIGMA= | 2.4 | PHAS= | 65.3 | FOM= | 0.95 | TEST= 0
| INDE | 5 | 27 | 46 | FOBS= | 115.2 | SIGMA= | 1.3 | PHAS= | 136.5 | FOM= | 0.89 | TEST= 1
| INDE | 5 | 27 | 48 | FOBS= | 189.1 | SIGMA= | 0.9 | PHAS= | -47.1 | FOM= | 0.65 | TEST= 1
| INDE | 5 | 27 | 50 | FOBS= | 211.9 | SIGMA= | 0.7 | PHAS= | 26.7 | FOM= | 0.94 | TEST= 0
| INDE | 5 | 27 | 52 | FOBS= | 44.6 | SIGMA= | 3.0 | PHAS= | 99.0 | FOM= | 0.75 | TEST= 0
| INDE | 5 | 27 | 54 | FOBS= | 36.8 | SIGMA= | 3.6 | PHAS= | -83.3 | FOM= | 0.71 | TEST= 0
| INDE | 5 | 27 | 56 | FOBS= | 12.3 | SIGMA= | 11.8 | PHAS= | 71.6 | FOM= | 0.30 | TEST= 0
| INDE | 5 | 27 | 58 | FOBS= | 126.9 | SIGMA= | 1.4 | PHAS= | 110.1 | FOM= | 0.07 | TEST= 1
| INDE | 5 | 27 | 60 | FOBS= | 54.0 | SIGMA= | 4.7 | PHAS= | -133.8 | FOM= | 0.75 | TEST= 0
| INDE | 5 | 27 | 62 | FOBS= | 45.7 | SIGMA= | 7.1 | PHAS= | -90.3 | FOM= | 0.20 | TEST= 1
| INDE | 5 | 27 | 64 | FOBS= | 90.3 | SIGMA= | 3.7 | PHAS= | -94.7 | FOM= | 0.90 | TEST= 0
| INDE | 5 | 27 | 66 | FOBS= | 77.7 | SIGMA= | 6.2 | PHAS= | -174.3 | FOM= | 0.38 | TEST= 0
| INDE | 5 | 27 | 68 | FOBS= | 39.4 | SIGMA= | 12.1 | PHAS= | -32.1 | FOM= | 0.79 | TEST= 0
| INDE | 5 | 27 | 70 | FOBS= | 77.2 | SIGMA= | 6.4 | PHAS= | 25.3 | FOM= | 0.93 | TEST= 0
| INDE | 5 | 27 | 72 | FOBS= | 87.5 | SIGMA= | 5.6 | PHAS= | 174.1 | FOM= | 0.93 | TEST= 0
| INDE | 5 | 28 | 5 | FOBS= | 90.1 | SIGMA= | 1.1 | PHAS= | 125.5 | FOM= | 0.72 | TEST= 1
| INDE | 5 | 28 | 7 | FOBS= | 118.0 | SIGMA= | 0.7 | PHAS= | 131.1 | FOM= | 0.96 | TEST= 0
| INDE | 5 | 28 | 9 | FOBS= | 83.2 | SIGMA= | 1.3 | PHAS= | -160.1 | FOM= | 0.92 | TEST= 0
| INDE | 5 | 28 | 11 | FOBS= | 181.8 | SIGMA= | 0.7 | PHAS= | 135.7 | FOM= | 0.90 | TEST= 0
| INDE | 5 | 28 | 13 | FOBS= | 68.3 | SIGMA= | 1.7 | PHAS= | 108.7 | FOM= | 0.93 | TEST= 1
| INDE | 5 | 28 | 15 | FOBS= | 84.9 | SIGMA= | 2.1 | PHAS= | 85.1 | FOM= | 0.94 | TEST= 0
| INDE | 5 | 28 | 17 | FOBS= | 138.6 | SIGMA= | 1.4 | PHAS= | 100.8 | FOM= | 0.99 | TEST= 0
| INDE | 5 | 28 | 19 | FOBS= | 285.3 | SIGMA= | 0.8 | PHAS= | 152.4 | FOM= | 0.97 | TEST= 0
| INDE | 5 | 28 | 21 | FOBS= | 196.5 | SIGMA= | 1.0 | PHAS= | -38.2 | FOM= | 0.97 | TEST= 0
| INDE | 5 | 28 | 23 | FOBS= | 92.4 | SIGMA= | 1.6 | PHAS= | -5.3 | FOM= | 0.67 | TEST= 1
| INDE | 5 | 28 | 25 | FOBS= | 336.9 | SIGMA= | 0.7 | PHAS= | 77.3 | FOM= | 0.96 | TEST= 0
| INDE | 5 | 28 | 27 | FOBS= | 85.2 | SIGMA= | 1.5 | PHAS= | 134.6 | FOM= | 0.90 | TEST= 0
| INDE | 5 | 28 | 29 | FOBS= | 270.6 | SIGMA= | 0.6 | PHAS= | -42.9 | FOM= | 0.94 | TEST= 0
| INDE | 5 | 28 | 31 | FOBS= | 180.7 | SIGMA= | 0.9 | PHAS= | 25.2 | FOM= | 0.95 | TEST= 0
| INDE | 5 | 28 | 33 | FOBS= | 138.8 | SIGMA= | 1.2 | PHAS= | -139.0 | FOM= | 0.96 | TEST= 0
| INDE | 5 | 28 | 35 | FOBS= | 372.5 | SIGMA= | 0.7 | PHAS= | 99.7 | FOM= | 0.97 | TEST= 0
| INDE | 5 | 28 | 37 | FOBS= | 402.4 | SIGMA= | 0.8 | PHAS= | 94.3 | FOM= | 0.98 | TEST= 0
| INDE | 5 | 28 | 39 | FOBS= | 322.2 | SIGMA= | 0.8 | PHAS= | -70.3 | FOM= | 0.97 | TEST= 0
| INDE | 5 | 28 | 41 | FOBS= | 128.1 | SIGMA= | 1.5 | PHAS= | -100.1 | FOM= | 0.90 | TEST= 0
| INDE | 5 | 28 | 43 | FOBS= | 74.4 | SIGMA= | 2.1 | PHAS= | 66.6 | FOM= | 0.84 | TEST= 0
| INDE | 5 | 28 | 45 | FOBS= | 222.7 | SIGMA= | 0.9 | PHAS= | 86.1 | FOM= | 0.96 | TEST= 0
| INDE | 5 | 28 | 47 | FOBS= | 181.9 | SIGMA= | 0.9 | PHAS= | -64.8 | FOM= | 0.16 | TEST= 1
| INDE | 5 | 28 | 49 | FOBS= | 103.7 | SIGMA= | 1.4 | PHAS= | -79.3 | FOM= | 0.88 | TEST= 0
| INDE | 5 | 28 | 51 | FOBS= | 75.5 | SIGMA= | 1.8 | PHAS= | 111.0 | FOM= | 0.86 | TEST= 0
| INDE | 5 | 28 | 53 | FOBS= | 143.0 | SIGMA= | 1.0 | PHAS= | 154.3 | FOM= | 0.83 | TEST= 0
| INDE | 5 | 28 | 55 | FOBS= | 26.9 | SIGMA= | 5.4 | PHAS= | -146.5 | FOM= | 0.27 | TEST= 0
| INDE | 5 | 28 | 57 | FOBS= | 110.3 | SIGMA= | 1.4 | PHAS= | 9.2 | FOM= | 0.79 | TEST= 0
| INDE | 5 | 28 | 59 | FOBS= | 45.1 | SIGMA= | 3.6 | PHAS= | -5.4 | FOM= | 0.04 | TEST= 1
| INDE | 5 | 28 | 61 | FOBS= | 88.5 | SIGMA= | 3.8 | PHAS= | -88.8 | FOM= | 0.46 | TEST= 0
| INDE | 5 | 28 | 63 | FOBS= | 107.2 | SIGMA= | 3.2 | PHAS= | 100.6 | FOM= | 0.89 | TEST= 0
| INDE | 5 | 28 | 65 | FOBS= | 0.0 | SIGMA= | 30.9 | PHAS= | 0.0 | FOM= | 0.00 | TEST= 0
| INDE | 5 | 28 | 67 | FOBS= | 0.0 | SIGMA= | 30.8 | PHAS= | 0.0 | FOM= | 0.00 | TEST= 0
| INDE | 5 | 28 | 69 | FOBS= | 0.0 | SIGMA= | 31.0 | PHAS= | 0.0 | FOM= | 0.00 | TEST= 0
| INDE | 5 | 28 | 71 | FOBS= | 67.4 | SIGMA= | 7.4 | PHAS= | 8.0 | FOM= | 0.90 | TEST= 0
| INDE | 5 | 29 | 6 | FOBS= | 230.0 | SIGMA= | 0.6 | PHAS= | -20.9 | FOM= | 0.94 | TEST= 0
| INDE | 5 | 29 | 8 | FOBS= | 47.0 | SIGMA= | 2.2 | PHAS= | 128.6 | FOM= | 0.92 | TEST= 0
| INDE | 5 | 29 | 10 | FOBS= | 255.3 | SIGMA= | 0.7 | PHAS= | 150.6 | FOM= | 0.98 | TEST= 0
| INDE | 5 | 29 | 12 | FOBS= | 186.9 | SIGMA= | 0.8 | PHAS= | 55.0 | FOM= | 0.96 | TEST= 1
| INDE | 5 | 29 | 14 | FOBS= | 112.9 | SIGMA= | 1.1 | PHAS= | -138.4 | FOM= | 0.96 | TEST= 1
| INDE | 5 | 29 | 16 | FOBS= | 188.0 | SIGMA= | 1.2 | PHAS= | -143.5 | FOM= | 0.99 | TEST= 0

*FIG. 12A - 143*

```
INDE  5  29  18  FOBS=   110.9  SIGMA=   1.8  PHAS=     3.8  FOM=  0.94  TEST= 0
INDE  5  29  20  FOBS=   156.6  SIGMA=   1.4  PHAS=   -91.4  FOM=  0.96  TEST= 0
INDE  5  29  22  FOBS=   200.6  SIGMA=   1.0  PHAS=    89.7  FOM=  0.78  TEST= 0
INDE  5  29  24  FOBS=   143.2  SIGMA=   1.1  PHAS=   -77.9  FOM=  0.61  TEST= 0
INDE  5  29  26  FOBS=   108.4  SIGMA=   1.3  PHAS=   -23.7  FOM=  0.48  TEST= 0
INDE  5  29  28  FOBS=   215.2  SIGMA=   0.7  PHAS=  -111.6  FOM=  0.98  TEST= 1
INDE  5  29  30  FOBS=   184.1  SIGMA=   0.9  PHAS=   -76.8  FOM=  0.91  TEST= 0
INDE  5  29  32  FOBS=   150.6  SIGMA=   1.1  PHAS=   124.6  FOM=  0.58  TEST= 0
INDE  5  29  34  FOBS=     0.0  SIGMA=  18.3  PHAS=     0.0  FOM=  0.00  TEST= 0
INDE  5  29  36  FOBS=   363.5  SIGMA=   0.7  PHAS=    22.5  FOM=  0.98  TEST= 0
INDE  5  29  38  FOBS=   159.0  SIGMA=   1.2  PHAS=   119.3  FOM=  0.72  TEST= 1
INDE  5  29  40  FOBS=   135.2  SIGMA=   1.6  PHAS=    90.6  FOM=  0.89  TEST= 1
INDE  5  29  42  FOBS=   323.1  SIGMA=   0.7  PHAS=   -55.3  FOM=  0.98  TEST= 0
INDE  5  29  44  FOBS=   222.9  SIGMA=   0.8  PHAS=    -9.1  FOM=  0.95  TEST= 0
INDE  5  29  46  FOBS=   124.1  SIGMA=   1.3  PHAS=   -17.3  FOM=  0.85  TEST= 0
INDE  5  29  48  FOBS=     0.0  SIGMA=  17.0  PHAS=     0.0  FOM=  0.00  TEST= 0
INDE  5  29  50  FOBS=   119.5  SIGMA=   1.2  PHAS=   -17.0  FOM=  0.52  TEST= 0
INDE  5  29  52  FOBS=   153.0  SIGMA=   1.0  PHAS=    94.7  FOM=  0.94  TEST= 0
INDE  5  29  54  FOBS=    46.8  SIGMA=   2.8  PHAS=   -61.2  FOM=  0.88  TEST= 0
INDE  5  29  56  FOBS=    57.1  SIGMA=   2.6  PHAS=   -13.4  FOM=  0.88  TEST= 1
INDE  5  29  58  FOBS=    79.0  SIGMA=   2.0  PHAS=   115.4  FOM=  0.17  TEST= 1
INDE  5  29  60  FOBS=   149.0  SIGMA=   1.2  PHAS=  -135.0  FOM=  0.92  TEST= 0
INDE  5  29  62  FOBS=    67.2  SIGMA=   5.0  PHAS=    50.2  FOM=  0.79  TEST= 0
INDE  5  29  64  FOBS=    18.9  SIGMA=  17.4  PHAS=   -66.1  FOM=  0.18  TEST= 0
INDE  5  29  66  FOBS=     0.0  SIGMA=  31.0  PHAS=     0.0  FOM=  0.00  TEST= 0
INDE  5  29  68  FOBS=     0.0  SIGMA=  31.2  PHAS=     0.0  FOM=  0.00  TEST= 0
INDE  5  29  70  FOBS=    66.2  SIGMA=   7.5  PHAS=   119.0  FOM=  0.34  TEST= 0
INDE  5  30   5  FOBS=   134.1  SIGMA=   0.9  PHAS=   144.0  FOM=  0.91  TEST= 0
INDE  5  30   7  FOBS=    80.1  SIGMA=   1.1  PHAS=  -174.0  FOM=  0.95  TEST= 0
INDE  5  30   9  FOBS=   288.0  SIGMA=   0.9  PHAS=    36.3  FOM=  0.97  TEST= 0
INDE  5  30  11  FOBS=    80.9  SIGMA=   1.4  PHAS=   106.8  FOM=  0.92  TEST= 0
INDE  5  30  13  FOBS=   115.7  SIGMA=   1.1  PHAS=   -42.2  FOM=  0.94  TEST= 0
INDE  5  30  15  FOBS=   316.4  SIGMA=   0.8  PHAS=   -20.6  FOM=  0.86  TEST= 0
INDE  5  30  17  FOBS=   191.2  SIGMA=   1.2  PHAS=  -151.2  FOM=  0.98  TEST= 0
INDE  5  30  19  FOBS=   258.8  SIGMA=   1.1  PHAS=  -174.1  FOM=  0.97  TEST= 0
INDE  5  30  21  FOBS=   115.4  SIGMA=   1.9  PHAS=    49.3  FOM=  0.79  TEST= 0
INDE  5  30  23  FOBS=   292.9  SIGMA=   1.1  PHAS=   -73.3  FOM=  0.97  TEST= 0
INDE  5  30  25  FOBS=   196.4  SIGMA=   0.9  PHAS=    66.2  FOM=  0.90  TEST= 0
INDE  5  30  27  FOBS=   160.8  SIGMA=   0.9  PHAS=   -62.9  FOM=  0.85  TEST= 0
INDE  5  30  29  FOBS=    76.7  SIGMA=   1.9  PHAS=   171.2  FOM=  0.72  TEST= 0
INDE  5  30  31  FOBS=   139.2  SIGMA=   1.2  PHAS=    81.7  FOM=  0.27  TEST= 0
INDE  5  30  33  FOBS=   112.9  SIGMA=   1.6  PHAS=   159.8  FOM=  0.78  TEST= 0
INDE  5  30  35  FOBS=     0.0  SIGMA=  19.9  PHAS=     0.0  FOM=  0.00  TEST= 1
INDE  5  30  37  FOBS=   210.6  SIGMA=   1.0  PHAS=   -26.6  FOM=  0.92  TEST= 0
INDE  5  30  39  FOBS=   192.6  SIGMA=   1.1  PHAS=  -107.1  FOM=  0.93  TEST= 0
INDE  5  30  41  FOBS=    95.2  SIGMA=   2.3  PHAS=   -26.2  FOM=  0.60  TEST= 0
INDE  5  30  43  FOBS=   178.6  SIGMA=   1.1  PHAS=  -134.7  FOM=  0.96  TEST= 0
INDE  5  30  45  FOBS=   105.2  SIGMA=   1.6  PHAS=  -164.6  FOM=  0.87  TEST= 0
INDE  5  30  47  FOBS=   180.8  SIGMA=   0.9  PHAS=   -85.7  FOM=  0.90  TEST= 0
INDE  5  30  49  FOBS=   155.2  SIGMA=   1.0  PHAS=    48.8  FOM=  0.90  TEST= 0
INDE  5  30  51  FOBS=   175.9  SIGMA=   0.9  PHAS=    57.8  FOM=  0.96  TEST= 0
INDE  5  30  53  FOBS=    99.5  SIGMA=   1.4  PHAS=    61.8  FOM=  0.61  TEST= 0
INDE  5  30  55  FOBS=   103.7  SIGMA=   1.5  PHAS=  -130.0  FOM=  0.94  TEST= 0
INDE  5  30  57  FOBS=    45.7  SIGMA=   3.3  PHAS=   -22.5  FOM=  0.59  TEST= 0
INDE  5  30  59  FOBS=    59.4  SIGMA=   3.0  PHAS=   108.2  FOM=  0.58  TEST= 0
INDE  5  30  61  FOBS=    16.6  SIGMA=  12.2  PHAS=   157.7  FOM=  0.19  TEST= 1
INDE  5  30  63  FOBS=    63.9  SIGMA=   4.4  PHAS=    42.7  FOM=  0.88  TEST= 0
INDE  5  30  65  FOBS=    37.0  SIGMA=  13.3  PHAS=   -23.3  FOM=  0.68  TEST= 0
INDE  5  30  67  FOBS=    78.3  SIGMA=   6.4  PHAS=     9.5  FOM=  0.20  TEST= 1
INDE  5  30  69  FOBS=    40.8  SIGMA=  12.0  PHAS=   -66.2  FOM=  0.77  TEST= 0
INDE  5  30  71  FOBS=    43.6  SIGMA=  11.6  PHAS=   142.2  FOM=  0.29  TEST= 0
INDE  5  31   6  FOBS=   115.4  SIGMA=   0.8  PHAS=    48.3  FOM=  0.93  TEST= 0
INDE  5  31   8  FOBS=   187.2  SIGMA=   0.7  PHAS=    88.2  FOM=  0.94  TEST= 0
INDE  5  31  10  FOBS=    31.5  SIGMA=   3.6  PHAS=  -153.5  FOM=  0.81  TEST= 0
INDE  5  31  12  FOBS=    69.1  SIGMA=   1.7  PHAS=   140.6  FOM=  0.95  TEST= 0
INDE  5  31  14  FOBS=    25.9  SIGMA=   4.8  PHAS=  -116.3  FOM=  0.11  TEST= 0
INDE  5  31  16  FOBS=    89.1  SIGMA=   1.5  PHAS=   -70.6  FOM=  0.99  TEST= 0
INDE  5  31  18  FOBS=   163.1  SIGMA=   1.4  PHAS=   124.4  FOM=  0.84  TEST= 0
INDE  5  31  20  FOBS=   227.7  SIGMA=   1.2  PHAS=   -56.4  FOM=  0.95  TEST= 0
INDE  5  31  22  FOBS=   120.5  SIGMA=   1.9  PHAS=   -95.7  FOM=  0.96  TEST= 0
```

*FIG. 12A - 144*

| | | | | | | | | | | | |
|---|---|---|---|---|---|---|---|---|---|---|---|
| INDE | 5 | 31 | 24 | FOBS= | 325.5 | SIGMA= | 1.1 | PHAS= | -95.6 | FOM= 0.98 | TEST= 0 |
| INDE | 5 | 31 | 26 | FOBS= | 149.2 | SIGMA= | 1.1 | PHAS= | 4.9 | FOM= 0.33 | TEST= 1 |
| INDE | 5 | 31 | 28 | FOBS= | 209.5 | SIGMA= | 0.9 | PHAS= | -106.6 | FOM= 0.94 | TEST= 0 |
| INDE | 5 | 31 | 30 | FOBS= | 148.9 | SIGMA= | 1.1 | PHAS= | 31.8 | FOM= 0.93 | TEST= 0 |
| INDE | 5 | 31 | 32 | FOBS= | 215.5 | SIGMA= | 0.9 | PHAS= | 78.2 | FOM= 0.85 | TEST= 0 |
| INDE | 5 | 31 | 34 | FOBS= | 99.7 | SIGMA= | 1.9 | PHAS= | -167.6 | FOM= 0.85 | TEST= 0 |
| INDE | 5 | 31 | 36 | FOBS= | 282.8 | SIGMA= | 0.8 | PHAS= | 79.5 | FOM= 0.97 | TEST= 0 |
| INDE | 5 | 31 | 38 | FOBS= | 119.4 | SIGMA= | 1.6 | PHAS= | -122.1 | FOM= 0.91 | TEST= 0 |
| INDE | 5 | 31 | 40 | FOBS= | 102.7 | SIGMA= | 1.9 | PHAS= | 58.7 | FOM= 0.90 | TEST= 0 |
| INDE | 5 | 31 | 42 | FOBS= | 124.4 | SIGMA= | 1.5 | PHAS= | -127.7 | FOM= 0.93 | TEST= 0 |
| INDE | 5 | 31 | 44 | FOBS= | 184.4 | SIGMA= | 1.1 | PHAS= | 80.4 | FOM= 0.95 | TEST= 0 |
| INDE | 5 | 31 | 46 | FOBS= | 135.1 | SIGMA= | 1.2 | PHAS= | 86.5 | FOM= 0.91 | TEST= 0 |
| INDE | 5 | 31 | 48 | FOBS= | 54.5 | SIGMA= | 2.8 | PHAS= | -47.0 | FOM= 0.84 | TEST= 0 |
| INDE | 5 | 31 | 50 | FOBS= | 107.7 | SIGMA= | 1.4 | PHAS= | -51.2 | FOM= 0.90 | TEST= 0 |
| INDE | 5 | 31 | 52 | FOBS= | 102.0 | SIGMA= | 1.4 | PHAS= | -1.7 | FOM= 0.88 | TEST= 0 |
| INDE | 5 | 31 | 54 | FOBS= | 46.9 | SIGMA= | 3.2 | PHAS= | 169.1 | FOM= 0.52 | TEST= 0 |
| INDE | 5 | 31 | 56 | FOBS= | 44.2 | SIGMA= | 3.3 | PHAS= | 129.7 | FOM= 0.63 | TEST= 0 |
| INDE | 5 | 31 | 58 | FOBS= | 23.8 | SIGMA= | 7.3 | PHAS= | -10.9 | FOM= 0.31 | TEST= 0 |
| INDE | 5 | 31 | 60 | FOBS= | 46.4 | SIGMA= | 3.7 | PHAS= | -157.5 | FOM= 0.60 | TEST= 0 |
| INDE | 5 | 31 | 62 | FOBS= | 95.9 | SIGMA= | 2.2 | PHAS= | -11.4 | FOM= 0.94 | TEST= 0 |
| INDE | 5 | 31 | 64 | FOBS= | 55.0 | SIGMA= | 5.2 | PHAS= | -75.2 | FOM= 0.69 | TEST= 0 |
| INDE | 5 | 31 | 66 | FOBS= | 61.0 | SIGMA= | 8.2 | PHAS= | -23.0 | FOM= 0.78 | TEST= 0 |
| INDE | 5 | 31 | 68 | FOBS= | 0.0 | SIGMA= | 31.4 | PHAS= | 0.0 | FOM= 0.00 | TEST= 0 |
| INDE | 5 | 31 | 70 | FOBS= | 73.9 | SIGMA= | 6.9 | PHAS= | 159.4 | FOM= 0.92 | TEST= 0 |
| INDE | 5 | 32 | 5 | FOBS= | 146.3 | SIGMA= | 0.6 | PHAS= | 106.4 | FOM= 0.98 | TEST= 0 |
| INDE | 5 | 32 | 7 | FOBS= | 291.2 | SIGMA= | 0.6 | PHAS= | 62.5 | FOM= 0.97 | TEST= 0 |
| INDE | 5 | 32 | 9 | FOBS= | 223.3 | SIGMA= | 0.7 | PHAS= | 37.7 | FOM= 0.91 | TEST= 0 |
| INDE | 5 | 32 | 11 | FOBS= | 119.5 | SIGMA= | 1.1 | PHAS= | 100.9 | FOM= 0.50 | TEST= 0 |
| INDE | 5 | 32 | 13 | FOBS= | 211.1 | SIGMA= | 0.9 | PHAS= | 1.2 | FOM= 0.97 | TEST= 0 |
| INDE | 5 | 32 | 15 | FOBS= | 165.8 | SIGMA= | 0.9 | PHAS= | 176.3 | FOM= 0.96 | TEST= 1 |
| INDE | 5 | 32 | 17 | FOBS= | 159.5 | SIGMA= | 1.1 | PHAS= | -166.2 | FOM= 0.94 | TEST= 0 |
| INDE | 5 | 32 | 19 | FOBS= | 363.0 | SIGMA= | 1.0 | PHAS= | -178.2 | FOM= 0.98 | TEST= 0 |
| INDE | 5 | 32 | 21 | FOBS= | 47.2 | SIGMA= | 4.6 | PHAS= | -141.1 | FOM= 0.85 | TEST= 0 |
| INDE | 5 | 32 | 23 | FOBS= | 166.2 | SIGMA= | 1.5 | PHAS= | 103.4 | FOM= 0.92 | TEST= 0 |
| INDE | 5 | 32 | 25 | FOBS= | 166.3 | SIGMA= | 1.4 | PHAS= | 162.1 | FOM= 0.96 | TEST= 0 |
| INDE | 5 | 32 | 27 | FOBS= | 105.6 | SIGMA= | 1.6 | PHAS= | 20.5 | FOM= 0.89 | TEST= 0 |
| INDE | 5 | 32 | 29 | FOBS= | 99.8 | SIGMA= | 1.6 | PHAS= | 164.7 | FOM= 0.76 | TEST= 0 |
| INDE | 5 | 32 | 31 | FOBS= | 68.3 | SIGMA= | 2.6 | PHAS= | -128.5 | FOM= 0.84 | TEST= 0 |
| INDE | 5 | 32 | 33 | FOBS= | 91.2 | SIGMA= | 2.1 | PHAS= | 87.9 | FOM= 0.91 | TEST= 0 |
| INDE | 5 | 32 | 35 | FOBS= | 389.0 | SIGMA= | 0.9 | PHAS= | -0.4 | FOM= 0.98 | TEST= 0 |
| INDE | 5 | 32 | 37 | FOBS= | 224.4 | SIGMA= | 1.0 | PHAS= | 25.9 | FOM= 0.93 | TEST= 0 |
| INDE | 5 | 32 | 39 | FOBS= | 63.5 | SIGMA= | 3.0 | PHAS= | -70.5 | FOM= 0.90 | TEST= 1 |
| INDE | 5 | 32 | 41 | FOBS= | 72.0 | SIGMA= | 2.6 | PHAS= | -10.7 | FOM= 0.84 | TEST= 0 |
| INDE | 5 | 32 | 43 | FOBS= | 0.0 | SIGMA= | 20.3 | PHAS= | 0.0 | FOM= 0.00 | TEST= 0 |
| INDE | 5 | 32 | 45 | FOBS= | 104.8 | SIGMA= | 1.8 | PHAS= | 21.6 | FOM= 0.82 | TEST= 0 |
| INDE | 5 | 32 | 47 | FOBS= | 106.0 | SIGMA= | 1.4 | PHAS= | -42.2 | FOM= 0.89 | TEST= 0 |
| INDE | 5 | 32 | 49 | FOBS= | 57.3 | SIGMA= | 2.7 | PHAS= | -56.7 | FOM= 0.68 | TEST= 0 |
| INDE | 5 | 32 | 51 | FOBS= | 68.7 | SIGMA= | 2.2 | PHAS= | -137.3 | FOM= 0.88 | TEST= 0 |
| INDE | 5 | 32 | 53 | FOBS= | 39.2 | SIGMA= | 3.5 | PHAS= | 94.5 | FOM= 0.84 | TEST= 0 |
| INDE | 5 | 32 | 55 | FOBS= | 48.9 | SIGMA= | 3.0 | PHAS= | -64.0 | FOM= 0.53 | TEST= 0 |
| INDE | 5 | 32 | 57 | FOBS= | 37.8 | SIGMA= | 4.3 | PHAS= | -160.8 | FOM= 0.47 | TEST= 0 |
| INDE | 5 | 32 | 59 | FOBS= | 42.6 | SIGMA= | 4.0 | PHAS= | 55.0 | FOM= 0.58 | TEST= 0 |
| INDE | 5 | 32 | 61 | FOBS= | 0.0 | SIGMA= | 21.4 | PHAS= | 0.0 | FOM= 0.00 | TEST= 0 |
| INDE | 5 | 32 | 63 | FOBS= | 59.7 | SIGMA= | 3.4 | PHAS= | -137.0 | FOM= 0.75 | TEST= 0 |
| INDE | 5 | 32 | 65 | FOBS= | 71.1 | SIGMA= | 4.2 | PHAS= | -42.0 | FOM= 0.94 | TEST= 0 |
| INDE | 5 | 32 | 67 | FOBS= | 0.0 | SIGMA= | 31.6 | PHAS= | 0.0 | FOM= 0.00 | TEST= 0 |
| INDE | 5 | 32 | 69 | FOBS= | 33.6 | SIGMA= | 14.9 | PHAS= | 128.5 | FOM= 0.66 | TEST= 0 |
| INDE | 5 | 33 | 6 | FOBS= | 221.4 | SIGMA= | 0.7 | PHAS= | -2.9 | FOM= 0.99 | TEST= 0 |
| INDE | 5 | 33 | 8 | FOBS= | 143.6 | SIGMA= | 0.9 | PHAS= | -15.4 | FOM= 0.94 | TEST= 0 |
| INDE | 5 | 33 | 10 | FOBS= | 253.6 | SIGMA= | 0.7 | PHAS= | -122.0 | FOM= 0.88 | TEST= 0 |
| INDE | 5 | 33 | 12 | FOBS= | 244.9 | SIGMA= | 0.8 | PHAS= | -125.2 | FOM= 0.85 | TEST= 1 |
| INDE | 5 | 33 | 14 | FOBS= | 146.9 | SIGMA= | 1.0 | PHAS= | 173.2 | FOM= 0.99 | TEST= 0 |
| INDE | 5 | 33 | 16 | FOBS= | 148.5 | SIGMA= | 1.1 | PHAS= | 103.7 | FOM= 0.98 | TEST= 0 |
| INDE | 5 | 33 | 18 | FOBS= | 312.8 | SIGMA= | 1.0 | PHAS= | 99.2 | FOM= 0.97 | TEST= 0 |
| INDE | 5 | 33 | 20 | FOBS= | 89.2 | SIGMA= | 2.6 | PHAS= | 85.7 | FOM= 0.90 | TEST= 0 |
| INDE | 5 | 33 | 22 | FOBS= | 111.0 | SIGMA= | 2.2 | PHAS= | -133.1 | FOM= 0.87 | TEST= 1 |
| INDE | 5 | 33 | 24 | FOBS= | 49.1 | SIGMA= | 4.9 | PHAS= | 153.5 | FOM= 0.50 | TEST= 0 |
| INDE | 5 | 33 | 26 | FOBS= | 271.7 | SIGMA= | 1.2 | PHAS= | 101.2 | FOM= 0.93 | TEST= 1 |
| INDE | 5 | 33 | 28 | FOBS= | 55.7 | SIGMA= | 3.2 | PHAS= | -123.6 | FOM= 0.67 | TEST= 0 |
| INDE | 5 | 33 | 30 | FOBS= | 62.0 | SIGMA= | 2.7 | PHAS= | 146.1 | FOM= 0.88 | TEST= 0 |

*FIG. 12A - 145*

```
INDE  5  33  32  FOBS=   151.6  SIGMA=   1.3  PHAS=    65.5  FOM=  0.80  TEST= 0
INDE  5  33  34  FOBS=   131.2  SIGMA=   2.0  PHAS=  -177.4  FOM=  0.95  TEST= 0
INDE  5  33  36  FOBS=    62.8  SIGMA=   3.3  PHAS=   -70.9  FOM=  0.71  TEST= 0
INDE  5  33  38  FOBS=   283.4  SIGMA=   1.0  PHAS=   -41.1  FOM=  0.97  TEST= 0
INDE  5  33  40  FOBS=   126.5  SIGMA=   1.5  PHAS=    24.3  FOM=  0.82  TEST= 0
INDE  5  33  42  FOBS=   101.8  SIGMA=   1.8  PHAS=  -113.1  FOM=  0.33  TEST= 0
INDE  5  33  44  FOBS=    73.5  SIGMA=   2.5  PHAS=    38.2  FOM=  0.48  TEST= 0
INDE  5  33  46  FOBS=    52.6  SIGMA=   3.4  PHAS=    -5.9  FOM=  0.79  TEST= 0
INDE  5  33  48  FOBS=   123.1  SIGMA=   1.2  PHAS=  -110.6  FOM=  0.87  TEST= 0
INDE  5  33  50  FOBS=   119.6  SIGMA=   1.4  PHAS=  -178.7  FOM=  0.91  TEST= 0
INDE  5  33  52  FOBS=    65.8  SIGMA=   2.3  PHAS=   -96.8  FOM=  0.87  TEST= 0
INDE  5  33  54  FOBS=    25.8  SIGMA=   7.0  PHAS=    58.4  FOM=  0.25  TEST= 0
INDE  5  33  56  FOBS=    55.4  SIGMA=   2.9  PHAS=   162.2  FOM=  0.72  TEST= 0
INDE  5  33  58  FOBS=     1.8  SIGMA=  96.9  PHAS=   -95.2  FOM=  0.01  TEST= 0
INDE  5  33  60  FOBS=    37.4  SIGMA=   4.7  PHAS=   -50.2  FOM=  0.51  TEST= 0
INDE  5  33  62  FOBS=    25.9  SIGMA=   8.6  PHAS=    66.3  FOM=  0.18  TEST= 1
INDE  5  33  64  FOBS=    51.4  SIGMA=   4.1  PHAS=  -115.3  FOM=  0.83  TEST= 0
INDE  5  33  66  FOBS=     0.0  SIGMA=  24.6  PHAS=     0.0  FOM=  0.00  TEST= 0
INDE  5  33  68  FOBS=     0.0  SIGMA=  31.8  PHAS=     0.0  FOM=  0.00  TEST= 0
INDE  5  33  70  FOBS=    54.2  SIGMA=   9.6  PHAS=  -165.2  FOM=  0.37  TEST= 0
INDE  5  34   5  FOBS=   130.3  SIGMA=   1.0  PHAS=   -50.8  FOM=  0.71  TEST= 0
INDE  5  34   7  FOBS=   266.8  SIGMA=   0.5  PHAS=    11.6  FOM=  0.96  TEST= 0
INDE  5  34   9  FOBS=   184.1  SIGMA=   1.0  PHAS=  -103.1  FOM=  0.88  TEST= 0
INDE  5  34  11  FOBS=    65.6  SIGMA=   2.0  PHAS=   128.2  FOM=  0.95  TEST= 0
INDE  5  34  13  FOBS=   183.6  SIGMA=   0.9  PHAS=    82.0  FOM=  0.98  TEST= 0
INDE  5  34  15  FOBS=   305.5  SIGMA=   0.7  PHAS=     7.8  FOM=  0.91  TEST= 1
INDE  5  34  17  FOBS=   266.5  SIGMA=   0.8  PHAS=   -13.2  FOM=  0.93  TEST= 0
INDE  5  34  19  FOBS=   144.4  SIGMA=   1.8  PHAS=  -145.6  FOM=  0.98  TEST= 0
INDE  5  34  21  FOBS=   220.2  SIGMA=   1.3  PHAS=   -28.0  FOM=  0.94  TEST= 0
INDE  5  34  23  FOBS=    55.7  SIGMA=   4.5  PHAS=   -10.0  FOM=  0.84  TEST= 0
INDE  5  34  25  FOBS=    77.4  SIGMA=   3.4  PHAS=    18.9  FOM=  0.79  TEST= 0
INDE  5  34  27  FOBS=    92.2  SIGMA=   2.6  PHAS=     1.6  FOM=  0.13  TEST= 0
INDE  5  34  29  FOBS=   101.6  SIGMA=   1.9  PHAS=    91.1  FOM=  0.96  TEST= 0
INDE  5  34  31  FOBS=   113.4  SIGMA=   1.7  PHAS=  -177.6  FOM=  0.73  TEST= 0
INDE  5  34  33  FOBS=   120.0  SIGMA=   1.7  PHAS=    52.5  FOM=  0.64  TEST= 0
INDE  5  34  35  FOBS=   103.8  SIGMA=   2.1  PHAS=    35.0  FOM=  0.65  TEST= 0
INDE  5  34  37  FOBS=    65.1  SIGMA=   3.0  PHAS=    54.7  FOM=  0.77  TEST= 0
INDE  5  34  39  FOBS=   271.3  SIGMA=   0.9  PHAS=   -98.2  FOM=  0.82  TEST= 1
INDE  5  34  41  FOBS=   113.6  SIGMA=   1.7  PHAS=  -114.8  FOM=  0.41  TEST= 0
INDE  5  34  43  FOBS=    43.6  SIGMA=   4.1  PHAS=    34.2  FOM=  0.51  TEST= 0
INDE  5  34  45  FOBS=     0.0  SIGMA=  18.8  PHAS=     0.0  FOM=  0.00  TEST= 1
INDE  5  34  47  FOBS=    24.9  SIGMA=   6.4  PHAS=     0.0  FOM=  0.00  TEST= 1
INDE  5  34  49  FOBS=    78.3  SIGMA=   1.9  PHAS=   164.0  FOM=  0.55  TEST= 0
INDE  5  34  51  FOBS=   186.4  SIGMA=   1.0  PHAS=   131.0  FOM=  0.97  TEST= 0
INDE  5  34  53  FOBS=    50.6  SIGMA=   3.0  PHAS=   120.8  FOM=  0.73  TEST= 0
INDE  5  34  55  FOBS=    87.7  SIGMA=   2.1  PHAS=   -10.4  FOM=  0.78  TEST= 1
INDE  5  34  57  FOBS=    45.5  SIGMA=   3.8  PHAS=  -115.9  FOM=  0.90  TEST= 0
INDE  5  34  59  FOBS=    19.8  SIGMA=   8.7  PHAS=  -130.9  FOM=  0.20  TEST= 0
INDE  5  34  61  FOBS=     0.0  SIGMA=  19.2  PHAS=     0.0  FOM=  0.00  TEST= 0
INDE  5  34  63  FOBS=    59.4  SIGMA=   3.5  PHAS=  -146.8  FOM=  0.92  TEST= 0
INDE  5  34  65  FOBS=     0.0  SIGMA=  21.3  PHAS=     0.0  FOM=  0.00  TEST= 0
INDE  5  34  67  FOBS=     0.0  SIGMA=  24.6  PHAS=     0.0  FOM=  0.00  TEST= 0
INDE  5  34  69  FOBS=    22.9  SIGMA=  23.0  PHAS=   169.5  FOM=  0.32  TEST= 0
INDE  5  35   6  FOBS=   163.0  SIGMA=   0.9  PHAS=   -86.9  FOM=  0.92  TEST= 0
INDE  5  35   8  FOBS=    84.7  SIGMA=   1.2  PHAS=   -34.6  FOM=  0.96  TEST= 0
INDE  5  35  10  FOBS=   139.6  SIGMA=   1.0  PHAS=  -166.5  FOM=  0.93  TEST= 0
INDE  5  35  12  FOBS=   184.8  SIGMA=   0.9  PHAS=   -12.5  FOM=  0.91  TEST= 0
INDE  5  35  14  FOBS=   217.5  SIGMA=   0.8  PHAS=   -74.3  FOM=  0.87  TEST= 0
INDE  5  35  16  FOBS=   292.2  SIGMA=   0.9  PHAS=   -86.2  FOM=  0.98  TEST= 0
INDE  5  35  18  FOBS=    88.3  SIGMA=   1.8  PHAS=   -72.5  FOM=  0.57  TEST= 0
INDE  5  35  20  FOBS=   266.6  SIGMA=   1.2  PHAS=  -176.7  FOM=  0.98  TEST= 1
INDE  5  35  22  FOBS=   361.0  SIGMA=   1.1  PHAS=  -123.6  FOM=  0.92  TEST= 0
INDE  5  35  24  FOBS=   177.6  SIGMA=   1.7  PHAS=   148.6  FOM=  0.96  TEST= 0
INDE  5  35  26  FOBS=   117.7  SIGMA=   2.5  PHAS=    30.7  FOM=  0.87  TEST= 0
INDE  5  35  28  FOBS=    92.3  SIGMA=   2.5  PHAS=    96.4  FOM=  0.88  TEST= 0
INDE  5  35  30  FOBS=   137.6  SIGMA=   1.5  PHAS=  -122.7  FOM=  0.93  TEST= 0
INDE  5  35  32  FOBS=   157.4  SIGMA=   1.4  PHAS=   130.9  FOM=  0.94  TEST= 0
INDE  5  35  34  FOBS=    75.2  SIGMA=   2.9  PHAS=  -129.9  FOM=  0.61  TEST= 0
INDE  5  35  36  FOBS=    97.2  SIGMA=   2.3  PHAS=    -6.4  FOM=  0.74  TEST= 0
INDE  5  35  38  FOBS=   108.4  SIGMA=   1.8  PHAS=  -115.7  FOM=  0.88  TEST= 0
```

*FIG. 12A - 146*

| | | | | | | | | | | | |
|---|---|---|---|---|---|---|---|---|---|---|---|
| INDE | 5 | 35 | 40 | FOBS= | 204.9 | SIGMA= | 1.0 | PHAS= | 168.6 | FOM= | 0.04 | TEST= | 1 |
| INDE | 5 | 35 | 42 | FOBS= | 108.5 | SIGMA= | 1.7 | PHAS= | -18.6 | FOM= | 0.92 | TEST= | 0 |
| INDE | 5 | 35 | 44 | FOBS= | 84.0 | SIGMA= | 2.2 | PHAS= | 125.7 | FOM= | 0.83 | TEST= | 0 |
| INDE | 5 | 35 | 46 | FOBS= | 90.5 | SIGMA= | 2.0 | PHAS= | 40.6 | FOM= | 0.91 | TEST= | 0 |
| INDE | 5 | 35 | 48 | FOBS= | 87.2 | SIGMA= | 1.7 | PHAS= | -76.1 | FOM= | 0.72 | TEST= | 0 |
| INDE | 5 | 35 | 50 | FOBS= | 72.9 | SIGMA= | 2.0 | PHAS= | 20.4 | FOM= | 0.93 | TEST= | 0 |
| INDE | 5 | 35 | 52 | FOBS= | 45.6 | SIGMA= | 3.6 | PHAS= | 152.3 | FOM= | 0.47 | TEST= | 0 |
| INDE | 5 | 35 | 54 | FOBS= | 74.4 | SIGMA= | 2.4 | PHAS= | -137.7 | FOM= | 0.08 | TEST= | 1 |
| INDE | 5 | 35 | 56 | FOBS= | 76.0 | SIGMA= | 2.4 | PHAS= | -153.3 | FOM= | 0.87 | TEST= | 0 |
| INDE | 5 | 35 | 58 | FOBS= | 51.2 | SIGMA= | 3.4 | PHAS= | 130.8 | FOM= | 0.57 | TEST= | 0 |
| INDE | 5 | 35 | 60 | FOBS= | 0.0 | SIGMA= | 18.7 | PHAS= | 0.0 | FOM= | 0.00 | TEST= | 0 |
| INDE | 5 | 35 | 62 | FOBS= | 68.2 | SIGMA= | 2.6 | PHAS= | 149.2 | FOM= | 0.66 | TEST= | 0 |
| INDE | 5 | 35 | 64 | FOBS= | 64.5 | SIGMA= | 3.2 | PHAS= | -143.2 | FOM= | 0.82 | TEST= | 0 |
| INDE | 5 | 35 | 66 | FOBS= | 72.3 | SIGMA= | 3.3 | PHAS= | 82.2 | FOM= | 0.69 | TEST= | 1 |
| INDE | 5 | 35 | 68 | FOBS= | 0.0 | SIGMA= | 24.9 | PHAS= | 0.0 | FOM= | 0.00 | TEST= | 0 |
| INDE | 5 | 36 | 5 | FOBS= | 115.9 | SIGMA= | 1.2 | PHAS= | -137.6 | FOM= | 0.87 | TEST= | 0 |
| INDE | 5 | 36 | 7 | FOBS= | 126.7 | SIGMA= | 0.8 | PHAS= | 94.0 | FOM= | 0.83 | TEST= | 0 |
| INDE | 5 | 36 | 9 | FOBS= | 262.9 | SIGMA= | 0.7 | PHAS= | -178.9 | FOM= | 0.98 | TEST= | 0 |
| INDE | 5 | 36 | 11 | FOBS= | 161.5 | SIGMA= | 1.0 | PHAS= | 16.5 | FOM= | 0.97 | TEST= | 1 |
| INDE | 5 | 36 | 13 | FOBS= | 187.7 | SIGMA= | 0.9 | PHAS= | -175.5 | FOM= | 0.94 | TEST= | 0 |
| INDE | 5 | 36 | 15 | FOBS= | 108.8 | SIGMA= | 1.5 | PHAS= | -6.2 | FOM= | 0.98 | TEST= | 0 |
| INDE | 5 | 36 | 17 | FOBS= | 95.1 | SIGMA= | 1.8 | PHAS= | 176.2 | FOM= | 0.82 | TEST= | 0 |
| INDE | 5 | 36 | 19 | FOBS= | 126.2 | SIGMA= | 1.4 | PHAS= | 122.8 | FOM= | 0.91 | TEST= | 0 |
| INDE | 5 | 36 | 21 | FOBS= | 106.5 | SIGMA= | 2.6 | PHAS= | 46.0 | FOM= | 0.63 | TEST= | 0 |
| INDE | 5 | 36 | 23 | FOBS= | 138.2 | SIGMA= | 2.1 | PHAS= | 74.5 | FOM= | 0.93 | TEST= | 0 |
| INDE | 5 | 36 | 25 | FOBS= | 207.0 | SIGMA= | 1.6 | PHAS= | 20.9 | FOM= | 0.95 | TEST= | 1 |
| INDE | 5 | 36 | 27 | FOBS= | 172.9 | SIGMA= | 1.9 | PHAS= | -83.3 | FOM= | 0.85 | TEST= | 0 |
| INDE | 5 | 36 | 29 | FOBS= | 101.4 | SIGMA= | 2.1 | PHAS= | 15.4 | FOM= | 0.95 | TEST= | 0 |
| INDE | 5 | 36 | 31 | FOBS= | 297.5 | SIGMA= | 0.8 | PHAS= | 142.8 | FOM= | 0.95 | TEST= | 0 |
| INDE | 5 | 36 | 33 | FOBS= | 149.6 | SIGMA= | 1.5 | PHAS= | -41.6 | FOM= | 0.93 | TEST= | 0 |
| INDE | 5 | 36 | 35 | FOBS= | 135.0 | SIGMA= | 1.6 | PHAS= | -160.9 | FOM= | 0.90 | TEST= | 0 |
| INDE | 5 | 36 | 37 | FOBS= | 285.3 | SIGMA= | 0.9 | PHAS= | 129.7 | FOM= | 0.40 | TEST= | 1 |
| INDE | 5 | 36 | 39 | FOBS= | 38.2 | SIGMA= | 5.5 | PHAS= | -149.0 | FOM= | 0.18 | TEST= | 0 |
| INDE | 5 | 36 | 41 | FOBS= | 119.8 | SIGMA= | 1.6 | PHAS= | -152.7 | FOM= | 0.89 | TEST= | 0 |
| INDE | 5 | 36 | 43 | FOBS= | 171.4 | SIGMA= | 1.1 | PHAS= | -67.5 | FOM= | 0.93 | TEST= | 0 |
| INDE | 5 | 36 | 45 | FOBS= | 136.0 | SIGMA= | 1.4 | PHAS= | -24.9 | FOM= | 0.95 | TEST= | 0 |
| INDE | 5 | 36 | 47 | FOBS= | 52.1 | SIGMA= | 3.3 | PHAS= | 14.5 | FOM= | 0.45 | TEST= | 0 |
| INDE | 5 | 36 | 49 | FOBS= | 88.1 | SIGMA= | 1.7 | PHAS= | -147.9 | FOM= | 0.63 | TEST= | 0 |
| INDE | 5 | 36 | 51 | FOBS= | 71.3 | SIGMA= | 2.0 | PHAS= | 130.2 | FOM= | 0.67 | TEST= | 0 |
| INDE | 5 | 36 | 53 | FOBS= | 40.2 | SIGMA= | 4.5 | PHAS= | 111.8 | FOM= | 0.79 | TEST= | 0 |
| INDE | 5 | 36 | 55 | FOBS= | 58.7 | SIGMA= | 3.1 | PHAS= | -84.0 | FOM= | 0.78 | TEST= | 0 |
| INDE | 5 | 36 | 57 | FOBS= | 18.1 | SIGMA= | 9.7 | PHAS= | -84.3 | FOM= | 0.08 | TEST= | 0 |
| INDE | 5 | 36 | 59 | FOBS= | 29.5 | SIGMA= | 6.3 | PHAS= | -18.6 | FOM= | 0.28 | TEST= | 0 |
| INDE | 5 | 36 | 61 | FOBS= | 63.3 | SIGMA= | 2.8 | PHAS= | 29.8 | FOM= | 0.78 | TEST= | 0 |
| INDE | 5 | 36 | 63 | FOBS= | 92.4 | SIGMA= | 2.0 | PHAS= | 125.8 | FOM= | 0.85 | TEST= | 0 |
| INDE | 5 | 36 | 65 | FOBS= | 70.7 | SIGMA= | 2.7 | PHAS= | 177.2 | FOM= | 0.86 | TEST= | 0 |
| INDE | 5 | 36 | 67 | FOBS= | 27.6 | SIGMA= | 11.3 | PHAS= | -73.5 | FOM= | 0.18 | TEST= | 0 |
| INDE | 5 | 37 | 6 | FOBS= | 296.0 | SIGMA= | 0.8 | PHAS= | -155.5 | FOM= | 0.96 | TEST= | 0 |
| INDE | 5 | 37 | 8 | FOBS= | 150.6 | SIGMA= | 0.8 | PHAS= | 46.4 | FOM= | 0.98 | TEST= | 0 |
| INDE | 5 | 37 | 10 | FOBS= | 158.0 | SIGMA= | 1.0 | PHAS= | 80.5 | FOM= | 0.94 | TEST= | 0 |
| INDE | 5 | 37 | 12 | FOBS= | 160.6 | SIGMA= | 1.0 | PHAS= | -111.5 | FOM= | 0.90 | TEST= | 1 |
| INDE | 5 | 37 | 14 | FOBS= | 10.9 | SIGMA= | 13.7 | PHAS= | 88.2 | FOM= | 0.00 | TEST= | 1 |
| INDE | 5 | 37 | 16 | FOBS= | 87.2 | SIGMA= | 1.9 | PHAS= | -168.9 | FOM= | 0.79 | TEST= | 0 |
| INDE | 5 | 37 | 18 | FOBS= | 122.2 | SIGMA= | 1.5 | PHAS= | -100.7 | FOM= | 0.96 | TEST= | 0 |
| INDE | 5 | 37 | 20 | FOBS= | 115.1 | SIGMA= | 2.5 | PHAS= | 23.7 | FOM= | 0.89 | TEST= | 0 |
| INDE | 5 | 37 | 22 | FOBS= | 126.5 | SIGMA= | 2.3 | PHAS= | -154.1 | FOM= | 0.93 | TEST= | 0 |
| INDE | 5 | 37 | 24 | FOBS= | 98.3 | SIGMA= | 3.0 | PHAS= | -58.8 | FOM= | 0.63 | TEST= | 0 |
| INDE | 5 | 37 | 26 | FOBS= | 82.2 | SIGMA= | 3.8 | PHAS= | 57.8 | FOM= | 0.87 | TEST= | 0 |
| INDE | 5 | 37 | 28 | FOBS= | 74.1 | SIGMA= | 3.8 | PHAS= | -162.1 | FOM= | 0.60 | TEST= | 0 |
| INDE | 5 | 37 | 30 | FOBS= | 0.0 | SIGMA= | 21.4 | PHAS= | 0.0 | FOM= | 0.00 | TEST= | 0 |
| INDE | 5 | 37 | 32 | FOBS= | 64.9 | SIGMA= | 3.2 | PHAS= | 75.2 | FOM= | 0.46 | TEST= | 0 |
| INDE | 5 | 37 | 34 | FOBS= | 45.0 | SIGMA= | 5.8 | PHAS= | -102.8 | FOM= | 0.86 | TEST= | 0 |
| INDE | 5 | 37 | 36 | FOBS= | 268.4 | SIGMA= | 0.9 | PHAS= | 153.4 | FOM= | 0.97 | TEST= | 0 |
| INDE | 5 | 37 | 38 | FOBS= | 206.2 | SIGMA= | 1.1 | PHAS= | 136.1 | FOM= | 0.93 | TEST= | 0 |
| INDE | 5 | 37 | 40 | FOBS= | 102.4 | SIGMA= | 1.9 | PHAS= | 143.1 | FOM= | 0.92 | TEST= | 0 |
| INDE | 5 | 37 | 42 | FOBS= | 45.4 | SIGMA= | 4.0 | PHAS= | 118.6 | FOM= | 0.45 | TEST= | 1 |
| INDE | 5 | 37 | 44 | FOBS= | 119.7 | SIGMA= | 1.6 | PHAS= | -160.5 | FOM= | 0.95 | TEST= | 0 |
| INDE | 5 | 37 | 46 | FOBS= | 62.4 | SIGMA= | 2.9 | PHAS= | 51.0 | FOM= | 0.77 | TEST= | 0 |
| INDE | 5 | 37 | 48 | FOBS= | 55.1 | SIGMA= | 2.7 | PHAS= | 116.4 | FOM= | 0.70 | TEST= | 0 |
| INDE | 5 | 37 | 50 | FOBS= | 125.8 | SIGMA= | 1.2 | PHAS= | 53.2 | FOM= | 0.94 | TEST= | 0 |

*FIG. 12A - 147*

| | | | | | | | | | | | |
|---|---|---|---|---|---|---|---|---|---|---|---|
| INDE | 5 | 37 | 52 | FOBS= | 77.7 | SIGMA= | 1.9 | PHAS= | 143.7 | FOM= 0.90 | TEST= 0 |
| INDE | 5 | 37 | 54 | FOBS= | 18.7 | SIGMA= | 12.2 | PHAS= | 85.5 | FOM= 0.40 | TEST= 0 |
| INDE | 5 | 37 | 56 | FOBS= | 93.1 | SIGMA= | 2.0 | PHAS= | -145.2 | FOM= 0.79 | TEST= 0 |
| INDE | 5 | 37 | 58 | FOBS= | 16.7 | SIGMA= | 10.5 | PHAS= | 164.6 | FOM= 0.36 | TEST= 0 |
| INDE | 5 | 37 | 60 | FOBS= | 47.6 | SIGMA= | 3.7 | PHAS= | 89.9 | FOM= 0.76 | TEST= 0 |
| INDE | 5 | 37 | 62 | FOBS= | 31.0 | SIGMA= | 5.7 | PHAS= | 80.9 | FOM= 0.43 | TEST= 0 |
| INDE | 5 | 37 | 64 | FOBS= | 0.0 | SIGMA= | 20.5 | PHAS= | 0.0 | FOM= 0.00 | TEST= 0 |
| INDE | 5 | 37 | 66 | FOBS= | 86.8 | SIGMA= | 3.0 | PHAS= | 109.1 | FOM= 0.93 | TEST= 0 |
| INDE | 5 | 37 | 68 | FOBS= | 16.0 | SIGMA= | 24.4 | PHAS= | -35.8 | FOM= 0.19 | TEST= 0 |
| INDE | 5 | 38 | 5 | FOBS= | 340.5 | SIGMA= | 0.8 | PHAS= | 128.8 | FOM= 0.96 | TEST= 0 |
| INDE | 5 | 38 | 7 | FOBS= | 104.7 | SIGMA= | 1.3 | PHAS= | 69.5 | FOM= 0.99 | TEST= 0 |
| INDE | 5 | 38 | 9 | FOBS= | 77.6 | SIGMA= | 1.6 | PHAS= | 13.3 | FOM= 0.37 | TEST= 0 |
| INDE | 5 | 38 | 11 | FOBS= | 308.5 | SIGMA= | 0.7 | PHAS= | -4.4 | FOM= 0.95 | TEST= 0 |
| INDE | 5 | 38 | 13 | FOBS= | 213.8 | SIGMA= | 0.9 | PHAS= | -157.7 | FOM= 0.95 | TEST= 0 |
| INDE | 5 | 38 | 15 | FOBS= | 234.6 | SIGMA= | 0.9 | PHAS= | 53.8 | FOM= 0.95 | TEST= 0 |
| INDE | 5 | 38 | 17 | FOBS= | 22.5 | SIGMA= | 7.8 | PHAS= | 51.5 | FOM= 0.19 | TEST= 0 |
| INDE | 5 | 38 | 19 | FOBS= | 81.8 | SIGMA= | 2.3 | PHAS= | -166.7 | FOM= 0.16 | TEST= 0 |
| INDE | 5 | 38 | 21 | FOBS= | 222.1 | SIGMA= | 1.5 | PHAS= | -3.5 | FOM= 0.80 | TEST= 0 |
| INDE | 5 | 38 | 23 | FOBS= | 131.9 | SIGMA= | 2.4 | PHAS= | -15.3 | FOM= 0.95 | TEST= 1 |
| INDE | 5 | 38 | 25 | FOBS= | 74.9 | SIGMA= | 4.2 | PHAS= | -59.8 | FOM= 0.72 | TEST= 0 |
| INDE | 5 | 38 | 27 | FOBS= | 0.0 | SIGMA= | 25.4 | PHAS= | 0.0 | FOM= 0.00 | TEST= 0 |
| INDE | 5 | 38 | 29 | FOBS= | 90.1 | SIGMA= | 3.3 | PHAS= | 15.4 | FOM= 0.74 | TEST= 1 |
| INDE | 5 | 38 | 31 | FOBS= | 96.7 | SIGMA= | 2.3 | PHAS= | 157.1 | FOM= 0.90 | TEST= 0 |
| INDE | 5 | 38 | 33 | FOBS= | 274.2 | SIGMA= | 0.9 | PHAS= | -96.2 | FOM= 0.96 | TEST= 0 |
| INDE | 5 | 38 | 35 | FOBS= | 337.2 | SIGMA= | 1.0 | PHAS= | 86.3 | FOM= 0.98 | TEST= 0 |
| INDE | 5 | 38 | 37 | FOBS= | 59.3 | SIGMA= | 3.4 | PHAS= | -11.0 | FOM= 0.69 | TEST= 0 |
| INDE | 5 | 38 | 39 | FOBS= | 21.3 | SIGMA= | 9.3 | PHAS= | 41.0 | FOM= 0.67 | TEST= 0 |
| INDE | 5 | 38 | 41 | FOBS= | 138.2 | SIGMA= | 1.4 | PHAS= | 14.8 | FOM= 0.94 | TEST= 0 |
| INDE | 5 | 38 | 43 | FOBS= | 134.5 | SIGMA= | 1.4 | PHAS= | 5.4 | FOM= 0.96 | TEST= 0 |
| INDE | 5 | 38 | 45 | FOBS= | 64.7 | SIGMA= | 2.8 | PHAS= | -30.4 | FOM= 0.88 | TEST= 0 |
| INDE | 5 | 38 | 47 | FOBS= | 94.7 | SIGMA= | 1.7 | PHAS= | -14.3 | FOM= 0.93 | TEST= 0 |
| INDE | 5 | 38 | 49 | FOBS= | 52.0 | SIGMA= | 2.8 | PHAS= | -7.8 | FOM= 0.36 | TEST= 0 |
| INDE | 5 | 38 | 51 | FOBS= | 37.6 | SIGMA= | 4.2 | PHAS= | 54.9 | FOM= 0.23 | TEST= 0 |
| INDE | 5 | 38 | 53 | FOBS= | 68.9 | SIGMA= | 2.5 | PHAS= | 82.2 | FOM= 0.81 | TEST= 0 |
| INDE | 5 | 38 | 55 | FOBS= | 64.1 | SIGMA= | 2.8 | PHAS= | -114.9 | FOM= 0.64 | TEST= 0 |
| INDE | 5 | 38 | 57 | FOBS= | 56.3 | SIGMA= | 3.2 | PHAS= | 84.2 | FOM= 0.74 | TEST= 0 |
| INDE | 5 | 38 | 59 | FOBS= | 62.8 | SIGMA= | 2.9 | PHAS= | 45.0 | FOM= 0.86 | TEST= 0 |
| INDE | 5 | 38 | 61 | FOBS= | 0.0 | SIGMA= | 19.6 | PHAS= | 0.0 | FOM= 0.00 | TEST= 0 |
| INDE | 5 | 38 | 63 | FOBS= | 33.0 | SIGMA= | 5.8 | PHAS= | 29.7 | FOM= 0.66 | TEST= 0 |
| INDE | 5 | 38 | 65 | FOBS= | 0.0 | SIGMA= | 21.5 | PHAS= | 0.0 | FOM= 0.00 | TEST= 0 |
| INDE | 5 | 38 | 67 | FOBS= | 27.6 | SIGMA= | 10.6 | PHAS= | -130.5 | FOM= 0.54 | TEST= 0 |
| INDE | 5 | 39 | 6 | FOBS= | 55.3 | SIGMA= | 2.7 | PHAS= | -23.6 | FOM= 0.98 | TEST= 0 |
| INDE | 5 | 39 | 8 | FOBS= | 272.2 | SIGMA= | 0.7 | PHAS= | -35.1 | FOM= 0.94 | TEST= 0 |
| INDE | 5 | 39 | 10 | FOBS= | 246.2 | SIGMA= | 0.7 | PHAS= | -110.4 | FOM= 0.91 | TEST= 0 |
| INDE | 5 | 39 | 12 | FOBS= | 212.8 | SIGMA= | 0.9 | PHAS= | 158.1 | FOM= 0.45 | TEST= 1 |
| INDE | 5 | 39 | 14 | FOBS= | 103.6 | SIGMA= | 1.7 | PHAS= | 34.0 | FOM= 0.95 | TEST= 1 |
| INDE | 5 | 39 | 16 | FOBS= | 163.0 | SIGMA= | 1.2 | PHAS= | 43.3 | FOM= 0.91 | TEST= 0 |
| INDE | 5 | 39 | 18 | FOBS= | 162.7 | SIGMA= | 1.3 | PHAS= | -152.3 | FOM= 0.83 | TEST= 0 |
| INDE | 5 | 39 | 20 | FOBS= | 44.9 | SIGMA= | 4.3 | PHAS= | 60.0 | FOM= 0.29 | TEST= 0 |
| INDE | 5 | 39 | 22 | FOBS= | 373.2 | SIGMA= | 1.2 | PHAS= | 168.9 | FOM= 0.98 | TEST= 0 |
| INDE | 5 | 39 | 24 | FOBS= | 230.3 | SIGMA= | 1.6 | PHAS= | -141.3 | FOM= 0.98 | TEST= 0 |
| INDE | 5 | 39 | 26 | FOBS= | 145.9 | SIGMA= | 2.4 | PHAS= | 90.2 | FOM= 0.78 | TEST= 0 |
| INDE | 5 | 39 | 28 | FOBS= | 176.9 | SIGMA= | 1.8 | PHAS= | -70.4 | FOM= 0.95 | TEST= 0 |
| INDE | 5 | 39 | 30 | FOBS= | 92.5 | SIGMA= | 2.9 | PHAS= | 129.6 | FOM= 0.80 | TEST= 0 |
| INDE | 5 | 39 | 32 | FOBS= | 90.9 | SIGMA= | 2.4 | PHAS= | 151.6 | FOM= 0.70 | TEST= 0 |
| INDE | 5 | 39 | 34 | FOBS= | 0.0 | SIGMA= | 20.3 | PHAS= | 0.0 | FOM= 0.00 | TEST= 0 |
| INDE | 5 | 39 | 36 | FOBS= | 174.3 | SIGMA= | 1.3 | PHAS= | 60.8 | FOM= 0.82 | TEST= 0 |
| INDE | 5 | 39 | 38 | FOBS= | 82.5 | SIGMA= | 2.4 | PHAS= | 170.1 | FOM= 0.91 | TEST= 0 |
| INDE | 5 | 39 | 40 | FOBS= | 181.6 | SIGMA= | 1.1 | PHAS= | -163.5 | FOM= 0.94 | TEST= 0 |
| INDE | 5 | 39 | 42 | FOBS= | 159.9 | SIGMA= | 1.2 | PHAS= | -84.4 | FOM= 0.94 | TEST= 0 |
| INDE | 5 | 39 | 44 | FOBS= | 121.1 | SIGMA= | 1.6 | PHAS= | -68.4 | FOM= 0.90 | TEST= 0 |
| INDE | 5 | 39 | 46 | FOBS= | 55.3 | SIGMA= | 3.2 | PHAS= | 161.9 | FOM= 0.63 | TEST= 0 |
| INDE | 5 | 39 | 48 | FOBS= | 0.0 | SIGMA= | 18.3 | PHAS= | 0.0 | FOM= 0.00 | TEST= 0 |
| INDE | 5 | 39 | 50 | FOBS= | 23.2 | SIGMA= | 6.9 | PHAS= | 58.0 | FOM= 0.45 | TEST= 0 |
| INDE | 5 | 39 | 52 | FOBS= | 27.0 | SIGMA= | 6.4 | PHAS= | 6.7 | FOM= 0.16 | TEST= 0 |
| INDE | 5 | 39 | 54 | FOBS= | 113.2 | SIGMA= | 1.6 | PHAS= | 126.9 | FOM= 0.60 | TEST= 0 |
| INDE | 5 | 39 | 56 | FOBS= | 19.2 | SIGMA= | 11.8 | PHAS= | 179.1 | FOM= 0.36 | TEST= 0 |
| INDE | 5 | 39 | 58 | FOBS= | 72.5 | SIGMA= | 2.5 | PHAS= | -78.9 | FOM= 0.72 | TEST= 1 |
| INDE | 5 | 39 | 60 | FOBS= | 0.0 | SIGMA= | 19.8 | PHAS= | 0.0 | FOM= 0.00 | TEST= 0 |
| INDE | 5 | 39 | 62 | FOBS= | 0.0 | SIGMA= | 20.5 | PHAS= | 0.0 | FOM= 0.00 | TEST= 0 |

*FIG. 12A - 148*

| | | | | | | | | | | | |
|---|---|---|---|---|---|---|---|---|---|---|---|
| INDE | 5 | 39 | 64 | FOBS= | 69.1 | SIGMA= | 2.7 | PHAS= | -124.2 | FOM= 0.70 | TEST= 0 |
| INDE | 5 | 39 | 66 | FOBS= | 48.1 | SIGMA= | 6.6 | PHAS= | 120.9 | FOM= 0.56 | TEST= 0 |
| INDE | 5 | 40 | 5 | FOBS= | 343.6 | SIGMA= | 0.9 | PHAS= | -68.8 | FOM= 0.98 | TEST= 0 |
| INDE | 5 | 40 | 7 | FOBS= | 87.0 | SIGMA= | 3.2 | PHAS= | 118.0 | FOM= 0.65 | TEST= 0 |
| INDE | 5 | 40 | 9 | FOBS= | 298.6 | SIGMA= | 1.3 | PHAS= | -138.7 | FOM= 0.97 | TEST= 0 |
| INDE | 5 | 40 | 11 | FOBS= | 181.9 | SIGMA= | 0.8 | PHAS= | -16.1 | FOM= 0.96 | TEST= 0 |
| INDE | 5 | 40 | 13 | FOBS= | 356.2 | SIGMA= | 0.7 | PHAS= | 82.7 | FOM= 0.97 | TEST= 0 |
| INDE | 5 | 40 | 15 | FOBS= | 179.0 | SIGMA= | 1.1 | PHAS= | -44.6 | FOM= 0.95 | TEST= 0 |
| INDE | 5 | 40 | 17 | FOBS= | 323.2 | SIGMA= | 0.8 | PHAS= | -56.9 | FOM= 0.70 | TEST= 0 |
| INDE | 5 | 40 | 19 | FOBS= | 189.0 | SIGMA= | 1.2 | PHAS= | 24.8 | FOM= 0.90 | TEST= 0 |
| INDE | 5 | 40 | 21 | FOBS= | 105.8 | SIGMA= | 2.1 | PHAS= | 34.1 | FOM= 0.84 | TEST= 0 |
| INDE | 5 | 40 | 23 | FOBS= | 276.0 | SIGMA= | 1.5 | PHAS= | 87.3 | FOM= 0.90 | TEST= 0 |
| INDE | 5 | 40 | 25 | FOBS= | 108.0 | SIGMA= | 3.3 | PHAS= | 29.3 | FOM= 0.85 | TEST= 0 |
| INDE | 5 | 40 | 27 | FOBS= | 32.5 | SIGMA= | 10.6 | PHAS= | -14.6 | FOM= 0.21 | TEST= 0 |
| INDE | 5 | 40 | 29 | FOBS= | 72.5 | SIGMA= | 4.2 | PHAS= | -175.1 | FOM= 0.12 | TEST= 0 |
| INDE | 5 | 40 | 31 | FOBS= | 78.3 | SIGMA= | 3.0 | PHAS= | -85.0 | FOM= 0.79 | TEST= 0 |
| INDE | 5 | 40 | 33 | FOBS= | 57.7 | SIGMA= | 3.6 | PHAS= | -130.0 | FOM= 0.70 | TEST= 1 |
| INDE | 5 | 40 | 35 | FOBS= | 161.7 | SIGMA= | 1.3 | PHAS= | 15.3 | FOM= 0.92 | TEST= 0 |
| INDE | 5 | 40 | 37 | FOBS= | 185.3 | SIGMA= | 1.1 | PHAS= | -77.5 | FOM= 0.96 | TEST= 0 |
| INDE | 5 | 40 | 39 | FOBS= | 145.6 | SIGMA= | 1.4 | PHAS= | 21.3 | FOM= 0.94 | TEST= 0 |
| INDE | 5 | 40 | 41 | FOBS= | 67.6 | SIGMA= | 2.8 | PHAS= | 162.2 | FOM= 0.51 | TEST= 0 |
| INDE | 5 | 40 | 43 | FOBS= | 54.2 | SIGMA= | 3.4 | PHAS= | 105.2 | FOM= 0.61 | TEST= 0 |
| INDE | 5 | 40 | 45 | FOBS= | 45.2 | SIGMA= | 4.1 | PHAS= | 139.9 | FOM= 0.22 | TEST= 0 |
| INDE | 5 | 40 | 47 | FOBS= | 164.2 | SIGMA= | 1.1 | PHAS= | -22.7 | FOM= 0.95 | TEST= 0 |
| INDE | 5 | 40 | 49 | FOBS= | 43.1 | SIGMA= | 3.4 | PHAS= | -67.1 | FOM= 0.48 | TEST= 0 |
| INDE | 5 | 40 | 51 | FOBS= | 62.3 | SIGMA= | 2.4 | PHAS= | -80.8 | FOM= 0.88 | TEST= 0 |
| INDE | 5 | 40 | 53 | FOBS= | 124.2 | SIGMA= | 1.5 | PHAS= | 163.0 | FOM= 0.62 | TEST= 1 |
| INDE | 5 | 40 | 55 | FOBS= | 27.3 | SIGMA= | 6.7 | PHAS= | 168.3 | FOM= 0.11 | TEST= 1 |
| INDE | 5 | 40 | 57 | FOBS= | 42.1 | SIGMA= | 4.3 | PHAS= | 120.4 | FOM= 0.45 | TEST= 0 |
| INDE | 5 | 40 | 59 | FOBS= | 0.0 | SIGMA= | 19.0 | PHAS= | 0.0 | FOM= 0.00 | TEST= 1 |
| INDE | 5 | 40 | 61 | FOBS= | 0.0 | SIGMA= | 19.0 | PHAS= | 0.0 | FOM= 0.00 | TEST= 0 |
| INDE | 5 | 40 | 63 | FOBS= | 73.3 | SIGMA= | 2.6 | PHAS= | 104.8 | FOM= 0.80 | TEST= 0 |
| INDE | 5 | 40 | 65 | FOBS= | 89.3 | SIGMA= | 2.6 | PHAS= | -57.1 | FOM= 0.91 | TEST= 0 |
| INDE | 5 | 41 | 6 | FOBS= | 225.6 | SIGMA= | 0.9 | PHAS= | -148.8 | FOM= 0.88 | TEST= 0 |
| INDE | 5 | 41 | 8 | FOBS= | 139.7 | SIGMA= | 1.2 | PHAS= | 146.3 | FOM= 0.96 | TEST= 0 |
| INDE | 5 | 41 | 10 | FOBS= | 53.3 | SIGMA= | 2.6 | PHAS= | -117.3 | FOM= 0.94 | TEST= 1 |
| INDE | 5 | 41 | 12 | FOBS= | 152.7 | SIGMA= | 1.2 | PHAS= | 5.2 | FOM= 0.92 | TEST= 0 |
| INDE | 5 | 41 | 14 | FOBS= | 156.2 | SIGMA= | 1.3 | PHAS= | -43.5 | FOM= 0.95 | TEST= 1 |
| INDE | 5 | 41 | 16 | FOBS= | 47.1 | SIGMA= | 4.1 | PHAS= | -81.0 | FOM= 0.88 | TEST= 1 |
| INDE | 5 | 41 | 18 | FOBS= | 302.9 | SIGMA= | 1.0 | PHAS= | 95.4 | FOM= 0.80 | TEST= 1 |
| INDE | 5 | 41 | 20 | FOBS= | 88.8 | SIGMA= | 2.5 | PHAS= | -86.9 | FOM= 0.92 | TEST= 0 |
| INDE | 5 | 41 | 22 | FOBS= | 207.3 | SIGMA= | 1.2 | PHAS= | -160.9 | FOM= 0.94 | TEST= 0 |
| INDE | 5 | 41 | 24 | FOBS= | 174.5 | SIGMA= | 2.2 | PHAS= | -79.6 | FOM= 0.82 | TEST= 0 |
| INDE | 5 | 41 | 26 | FOBS= | 176.9 | SIGMA= | 2.2 | PHAS= | -92.5 | FOM= 0.73 | TEST= 0 |
| INDE | 5 | 41 | 28 | FOBS= | 146.5 | SIGMA= | 2.5 | PHAS= | -15.2 | FOM= 0.76 | TEST= 0 |
| INDE | 5 | 41 | 30 | FOBS= | 20.9 | SIGMA= | 12.3 | PHAS= | -115.0 | FOM= 0.13 | TEST= 0 |
| INDE | 5 | 41 | 32 | FOBS= | 182.6 | SIGMA= | 1.3 | PHAS= | -6.6 | FOM= 0.89 | TEST= 0 |
| INDE | 5 | 41 | 34 | FOBS= | 0.0 | SIGMA= | 20.0 | PHAS= | 0.0 | FOM= 0.00 | TEST= 0 |
| INDE | 5 | 41 | 36 | FOBS= | 129.7 | SIGMA= | 1.6 | PHAS= | -177.9 | FOM= 0.89 | TEST= 0 |
| INDE | 5 | 41 | 38 | FOBS= | 207.0 | SIGMA= | 1.0 | PHAS= | -89.9 | FOM= 0.93 | TEST= 0 |
| INDE | 5 | 41 | 40 | FOBS= | 218.7 | SIGMA= | 1.0 | PHAS= | 67.2 | FOM= 0.91 | TEST= 0 |
| INDE | 5 | 41 | 42 | FOBS= | 120.6 | SIGMA= | 1.6 | PHAS= | -139.1 | FOM= 0.75 | TEST= 0 |
| INDE | 5 | 41 | 44 | FOBS= | 113.9 | SIGMA= | 1.6 | PHAS= | 18.9 | FOM= 0.93 | TEST= 0 |
| INDE | 5 | 41 | 46 | FOBS= | 53.6 | SIGMA= | 3.3 | PHAS= | -99.9 | FOM= 0.37 | TEST= 1 |
| INDE | 5 | 41 | 48 | FOBS= | 101.9 | SIGMA= | 1.5 | PHAS= | -139.8 | FOM= 0.93 | TEST= 0 |
| INDE | 5 | 41 | 50 | FOBS= | 130.8 | SIGMA= | 1.2 | PHAS= | -142.6 | FOM= 0.91 | TEST= 0 |
| INDE | 5 | 41 | 52 | FOBS= | 33.0 | SIGMA= | 5.6 | PHAS= | 61.2 | FOM= 0.08 | TEST= 1 |
| INDE | 5 | 41 | 54 | FOBS= | 101.6 | SIGMA= | 1.8 | PHAS= | 88.1 | FOM= 0.92 | TEST= 0 |
| INDE | 5 | 41 | 56 | FOBS= | 2.8 | SIGMA= | 80.5 | PHAS= | 82.3 | FOM= 0.26 | TEST= 1 |
| INDE | 5 | 41 | 58 | FOBS= | 31.0 | SIGMA= | 5.9 | PHAS= | -44.4 | FOM= 0.34 | TEST= 0 |
| INDE | 5 | 41 | 60 | FOBS= | 0.0 | SIGMA= | 19.6 | PHAS= | 0.0 | FOM= 0.00 | TEST= 1 |
| INDE | 5 | 41 | 62 | FOBS= | 51.6 | SIGMA= | 3.6 | PHAS= | -6.8 | FOM= 0.87 | TEST= 0 |
| INDE | 5 | 41 | 64 | FOBS= | 36.8 | SIGMA= | 6.6 | PHAS= | 50.0 | FOM= 0.03 | TEST= 1 |
| INDE | 5 | 42 | 5 | FOBS= | 108.9 | SIGMA= | 1.7 | PHAS= | -25.6 | FOM= 0.83 | TEST= 0 |
| INDE | 5 | 42 | 7 | FOBS= | 350.3 | SIGMA= | 1.2 | PHAS= | 110.1 | FOM= 0.97 | TEST= 0 |
| INDE | 5 | 42 | 9 | FOBS= | 173.8 | SIGMA= | 0.9 | PHAS= | -133.2 | FOM= 0.95 | TEST= 0 |
| INDE | 5 | 42 | 11 | FOBS= | 205.6 | SIGMA= | 0.8 | PHAS= | -107.6 | FOM= 0.29 | TEST= 1 |
| INDE | 5 | 42 | 13 | FOBS= | 233.2 | SIGMA= | 1.0 | PHAS= | 86.9 | FOM= 0.94 | TEST= 0 |
| INDE | 5 | 42 | 15 | FOBS= | 88.2 | SIGMA= | 2.3 | PHAS= | 137.4 | FOM= 0.53 | TEST= 0 |
| INDE | 5 | 42 | 17 | FOBS= | 78.6 | SIGMA= | 2.7 | PHAS= | 161.5 | FOM= 0.31 | TEST= 0 |

*FIG. 12A - 149*

```
INDE  5  42  19  FOBS=   43.4  SIGMA=   5.2  PHAS=  -30.7  FOM= 0.77  TEST= 1
INDE  5  42  21  FOBS=  202.1  SIGMA=   1.3  PHAS=  156.8  FOM= 0.96  TEST= 0
INDE  5  42  23  FOBS=   93.8  SIGMA=   2.6  PHAS=  116.9  FOM= 0.93  TEST= 0
INDE  5  42  25  FOBS=  102.5  SIGMA=   3.6  PHAS=  168.8  FOM= 0.78  TEST= 0
INDE  5  42  27  FOBS=   74.8  SIGMA=   4.8  PHAS= -102.7  FOM= 0.40  TEST= 0
INDE  5  42  29  FOBS=  174.3  SIGMA=   1.8  PHAS=  -22.9  FOM= 0.97  TEST= 0
INDE  5  42  31  FOBS=  194.1  SIGMA=   1.4  PHAS= -122.1  FOM= 0.96  TEST= 0
INDE  5  42  33  FOBS=  158.1  SIGMA=   1.5  PHAS= -100.0  FOM= 0.93  TEST= 0
INDE  5  42  35  FOBS=  116.4  SIGMA=   1.8  PHAS= -111.1  FOM= 0.05  TEST= 1
INDE  5  42  37  FOBS=    0.0  SIGMA=  20.0  PHAS=    0.0  FOM= 0.00  TEST= 1
INDE  5  42  39  FOBS=   50.1  SIGMA=   3.9  PHAS=  -27.7  FOM= 0.94  TEST= 0
INDE  5  42  41  FOBS=  175.3  SIGMA=   1.2  PHAS= -149.3  FOM= 0.94  TEST= 0
INDE  5  42  43  FOBS=  179.7  SIGMA=   1.1  PHAS=   52.9  FOM= 0.96  TEST= 0
INDE  5  42  45  FOBS=   25.4  SIGMA=   7.4  PHAS= -144.3  FOM= 0.19  TEST= 0
INDE  5  42  47  FOBS=    0.0  SIGMA=  17.9  PHAS=    0.0  FOM= 0.00  TEST= 0
INDE  5  42  49  FOBS=  120.3  SIGMA=   1.3  PHAS= -177.0  FOM= 0.94  TEST= 0
INDE  5  42  51  FOBS=   13.7  SIGMA=  15.1  PHAS=  102.2  FOM= 0.20  TEST= 0
INDE  5  42  53  FOBS=   93.7  SIGMA=   1.9  PHAS=    1.3  FOM= 0.87  TEST= 0
INDE  5  42  55  FOBS=   82.5  SIGMA=   2.2  PHAS=   17.7  FOM= 0.86  TEST= 0
INDE  5  42  57  FOBS=   62.4  SIGMA=   2.9  PHAS=   75.0  FOM= 0.65  TEST= 0
INDE  5  42  59  FOBS=   52.0  SIGMA=   3.6  PHAS=    0.3  FOM= 0.23  TEST= 0
INDE  5  42  61  FOBS=   68.0  SIGMA=   2.8  PHAS=  172.6  FOM= 0.63  TEST= 1
INDE  5  42  63  FOBS=   55.9  SIGMA=   4.3  PHAS= -100.6  FOM= 0.90  TEST= 0
INDE  5  42  65  FOBS=   78.9  SIGMA=   3.6  PHAS=   -0.1  FOM= 0.87  TEST= 0
INDE  5  43   6  FOBS=  165.6  SIGMA=   1.2  PHAS=   16.7  FOM= 0.96  TEST= 0
INDE  5  43   8  FOBS=  265.1  SIGMA=   1.5  PHAS=  120.9  FOM= 0.85  TEST= 1
INDE  5  43  10  FOBS=  298.2  SIGMA=   0.8  PHAS= -154.5  FOM= 0.97  TEST= 0
INDE  5  43  12  FOBS=   92.9  SIGMA=   1.7  PHAS=   25.1  FOM= 0.91  TEST= 0
INDE  5  43  14  FOBS=  124.3  SIGMA=   1.7  PHAS=  -62.4  FOM= 0.80  TEST= 0
INDE  5  43  16  FOBS=  240.9  SIGMA=   1.0  PHAS=   10.7  FOM= 0.98  TEST= 0
INDE  5  43  18  FOBS=  296.8  SIGMA=   0.9  PHAS=   43.3  FOM= 0.94  TEST= 0
INDE  5  43  20  FOBS=  150.4  SIGMA=   2.0  PHAS=   -7.2  FOM= 0.93  TEST= 0
INDE  5  43  22  FOBS=  102.1  SIGMA=   2.4  PHAS= -164.6  FOM= 0.56  TEST= 0
INDE  5  43  24  FOBS=  162.0  SIGMA=   2.4  PHAS=   49.9  FOM= 0.95  TEST= 0
INDE  5  43  26  FOBS=  143.0  SIGMA=   2.6  PHAS=   -1.5  FOM= 0.65  TEST= 0
INDE  5  43  28  FOBS=  259.9  SIGMA=   1.6  PHAS=  -82.6  FOM= 0.96  TEST= 0
INDE  5  43  30  FOBS=  128.8  SIGMA=   2.1  PHAS= -179.5  FOM= 0.87  TEST= 0
INDE  5  43  32  FOBS=  251.2  SIGMA=   1.2  PHAS=  106.6  FOM= 0.96  TEST= 0
INDE  5  43  34  FOBS=  181.0  SIGMA=   1.3  PHAS=  161.7  FOM= 0.91  TEST= 0
INDE  5  43  36  FOBS=   31.2  SIGMA=   6.8  PHAS=   59.7  FOM= 0.34  TEST= 0
INDE  5  43  38  FOBS=  170.6  SIGMA=   1.2  PHAS=  -84.2  FOM= 0.91  TEST= 1
INDE  5  43  40  FOBS=  128.8  SIGMA=   1.5  PHAS=   66.1  FOM= 0.75  TEST= 0
INDE  5  43  42  FOBS=   80.3  SIGMA=   2.4  PHAS=   70.3  FOM= 0.87  TEST= 0
INDE  5  43  44  FOBS=   43.1  SIGMA=   4.2  PHAS=  -50.5  FOM= 0.59  TEST= 0
INDE  5  43  46  FOBS=   65.8  SIGMA=   2.7  PHAS=  -35.4  FOM= 0.20  TEST= 0
INDE  5  43  48  FOBS=   25.2  SIGMA=   6.2  PHAS= -159.5  FOM= 0.18  TEST= 0
INDE  5  43  50  FOBS=   36.6  SIGMA=   4.4  PHAS=  133.7  FOM= 0.79  TEST= 0
INDE  5  43  52  FOBS=    0.0  SIGMA=  19.8  PHAS=    0.0  FOM= 0.00  TEST= 0
INDE  5  43  54  FOBS=    0.0  SIGMA=  20.4  PHAS=    0.0  FOM= 0.00  TEST= 0
INDE  5  43  56  FOBS=  120.1  SIGMA=   1.5  PHAS=  -42.2  FOM= 0.95  TEST= 0
INDE  5  43  58  FOBS=   79.5  SIGMA=   2.2  PHAS=  -23.3  FOM= 0.80  TEST= 0
INDE  5  43  60  FOBS=   91.2  SIGMA=   2.1  PHAS=  161.5  FOM= 0.92  TEST= 0
INDE  5  43  62  FOBS=   25.2  SIGMA=   8.7  PHAS=   47.4  FOM= 0.10  TEST= 0
INDE  5  43  64  FOBS=   13.7  SIGMA=  17.7  PHAS= -125.5  FOM= 0.33  TEST= 0
INDE  5  44   5  FOBS=  178.1  SIGMA=   1.2  PHAS=  -26.3  FOM= 0.80  TEST= 0
INDE  5  44   7  FOBS=  181.2  SIGMA=   2.0  PHAS=   -4.1  FOM= 0.91  TEST= 0
INDE  5  44   9  FOBS=  204.5  SIGMA=   1.0  PHAS=   17.5  FOM= 0.91  TEST= 0
INDE  5  44  11  FOBS=  190.9  SIGMA=   0.9  PHAS=  -16.0  FOM= 0.97  TEST= 0
INDE  5  44  13  FOBS=   53.4  SIGMA=   2.7  PHAS= -176.0  FOM= 0.83  TEST= 0
INDE  5  44  15  FOBS=   81.5  SIGMA=   2.7  PHAS=  115.5  FOM= 0.88  TEST= 0
INDE  5  44  17  FOBS=  349.1  SIGMA=   1.4  PHAS= -114.2  FOM= 0.98  TEST= 0
INDE  5  44  19  FOBS=  223.5  SIGMA=   1.2  PHAS= -118.1  FOM= 0.75  TEST= 0
INDE  5  44  21  FOBS=  143.2  SIGMA=   1.8  PHAS= -121.2  FOM= 0.88  TEST= 0
INDE  5  44  23  FOBS=  358.3  SIGMA=   1.0  PHAS=  -83.6  FOM= 0.97  TEST= 0
INDE  5  44  25  FOBS=   68.9  SIGMA=   5.2  PHAS= -110.5  FOM= 0.64  TEST= 0
INDE  5  44  27  FOBS=  200.3  SIGMA=   1.9  PHAS=  164.6  FOM= 0.91  TEST= 0
INDE  5  44  29  FOBS=    0.0  SIGMA=  24.3  PHAS=    0.0  FOM= 0.00  TEST= 0
INDE  5  44  31  FOBS=  108.5  SIGMA=   2.4  PHAS=   17.5  FOM= 0.82  TEST= 0
INDE  5  44  33  FOBS=  198.5  SIGMA=   1.4  PHAS=    4.2  FOM= 0.92  TEST= 0
INDE  5  44  35  FOBS=   94.5  SIGMA=   2.2  PHAS=    3.3  FOM= 0.65  TEST= 1
```

*FIG. 12A - 150*

```
INDE   5  44  37  FOBS=    0.0  SIGMA=  20.0  PHAS=    0.0  FOM= 0.00  TEST= 0
INDE   5  44  39  FOBS=    7.6  SIGMA=  26.6  PHAS=  -49.0  FOM= 0.02  TEST= 0
INDE   5  44  41  FOBS=  160.9  SIGMA=   1.3  PHAS=  -24.2  FOM= 0.93  TEST= 0
INDE   5  44  43  FOBS=   94.9  SIGMA=   2.0  PHAS=  -76.8  FOM= 0.89  TEST= 0
INDE   5  44  45  FOBS=   10.6  SIGMA=  19.2  PHAS=  -54.3  FOM= 0.20  TEST= 0
INDE   5  44  47  FOBS=   72.3  SIGMA=   2.3  PHAS=   48.8  FOM= 0.87  TEST= 0
INDE   5  44  49  FOBS=   33.2  SIGMA=   4.7  PHAS= -119.1  FOM= 0.49  TEST= 0
INDE   5  44  51  FOBS=   29.6  SIGMA=   6.7  PHAS=  102.0  FOM= 0.44  TEST= 0
INDE   5  44  53  FOBS=   59.7  SIGMA=   3.0  PHAS=  -16.7  FOM= 0.90  TEST= 0
INDE   5  44  55  FOBS=   62.8  SIGMA=   2.8  PHAS=  -96.2  FOM= 0.75  TEST= 0
INDE   5  44  57  FOBS=    0.0  SIGMA=  19.9  PHAS=    0.0  FOM= 0.00  TEST= 0
INDE   5  44  59  FOBS=    0.0  SIGMA=  18.6  PHAS=    0.0  FOM= 0.00  TEST= 0
INDE   5  44  61  FOBS=    0.0  SIGMA=  20.3  PHAS=    0.0  FOM= 0.00  TEST= 0
INDE   5  44  63  FOBS=   73.6  SIGMA=   3.4  PHAS= -157.4  FOM= 0.88  TEST= 0
INDE   5  45   6  FOBS=  151.4  SIGMA=   1.4  PHAS=  129.2  FOM= 0.54  TEST= 1
INDE   5  45   8  FOBS=   65.2  SIGMA=   5.5  PHAS=    9.7  FOM= 0.42  TEST= 0
INDE   5  45  10  FOBS=  316.2  SIGMA=   0.8  PHAS=  -78.8  FOM= 0.98  TEST= 0
INDE   5  45  12  FOBS=  104.2  SIGMA=   1.5  PHAS= -179.2  FOM= 0.40  TEST= 1
INDE   5  45  14  FOBS=  194.4  SIGMA=   0.9  PHAS=   -9.4  FOM= 0.87  TEST= 1
INDE   5  45  16  FOBS=  233.1  SIGMA=   1.1  PHAS=   -0.2  FOM= 0.94  TEST= 0
INDE   5  45  18  FOBS=  265.4  SIGMA=   1.3  PHAS=  141.2  FOM= 0.95  TEST= 0
INDE   5  45  20  FOBS=  127.8  SIGMA=   2.0  PHAS=   -2.6  FOM= 0.94  TEST= 0
INDE   5  45  22  FOBS=  157.2  SIGMA=   1.7  PHAS= -173.9  FOM= 0.91  TEST= 0
INDE   5  45  24  FOBS=  255.2  SIGMA=   1.1  PHAS=  127.3  FOM= 0.95  TEST= 0
INDE   5  45  26  FOBS=  192.5  SIGMA=   2.0  PHAS=   -8.4  FOM= 0.80  TEST= 0
INDE   5  45  28  FOBS=  134.7  SIGMA=   2.3  PHAS=  -66.5  FOM= 0.72  TEST= 0
INDE   5  45  30  FOBS=   49.8  SIGMA=   5.1  PHAS=   98.7  FOM= 0.26  TEST= 0
INDE   5  45  32  FOBS=   88.7  SIGMA=   2.9  PHAS=   84.1  FOM= 0.84  TEST= 0
INDE   5  45  34  FOBS=  136.8  SIGMA=   1.6  PHAS=  -61.3  FOM= 0.89  TEST= 0
INDE   5  45  36  FOBS=   69.5  SIGMA=   2.9  PHAS=    5.6  FOM= 0.64  TEST= 0
INDE   5  45  38  FOBS=    0.0  SIGMA=  19.7  PHAS=    0.0  FOM= 0.00  TEST= 0
INDE   5  45  40  FOBS=    0.0  SIGMA=  19.2  PHAS=    0.0  FOM= 0.00  TEST= 0
INDE   5  45  42  FOBS=  141.5  SIGMA=   1.4  PHAS=  154.0  FOM= 0.92  TEST= 0
INDE   5  45  44  FOBS=  112.6  SIGMA=   1.7  PHAS=  -19.9  FOM= 0.17  TEST= 0
INDE   5  45  46  FOBS=   72.4  SIGMA=   2.5  PHAS=  -32.0  FOM= 0.91  TEST= 0
INDE   5  45  48  FOBS=   41.0  SIGMA=   3.7  PHAS=  -48.1  FOM= 0.58  TEST= 0
INDE   5  45  50  FOBS=  124.1  SIGMA=   1.5  PHAS=   94.0  FOM= 0.92  TEST= 0
INDE   5  45  52  FOBS=   31.5  SIGMA=   5.6  PHAS=  -69.2  FOM= 0.04  TEST= 1
INDE   5  45  54  FOBS=    0.0  SIGMA=  19.5  PHAS=    0.0  FOM= 0.00  TEST= 0
INDE   5  45  56  FOBS=    0.0  SIGMA=  19.5  PHAS=    0.0  FOM= 0.00  TEST= 0
INDE   5  45  58  FOBS=    0.0  SIGMA=  19.9  PHAS=    0.0  FOM= 0.00  TEST= 0
INDE   5  45  60  FOBS=   80.2  SIGMA=   2.3  PHAS=  137.1  FOM= 0.90  TEST= 0
INDE   5  45  62  FOBS=    4.5  SIGMA=  72.9  PHAS=  124.3  FOM= 0.16  TEST= 0
INDE   5  46   5  FOBS=  134.3  SIGMA=   1.6  PHAS=   -9.7  FOM= 0.97  TEST= 0
INDE   5  46   7  FOBS=  101.8  SIGMA=   3.7  PHAS=   96.0  FOM= 0.55  TEST= 0
INDE   5  46   9  FOBS=  133.4  SIGMA=   2.9  PHAS=  178.0  FOM= 0.95  TEST= 0
INDE   5  46  11  FOBS=  199.1  SIGMA=   1.2  PHAS= -110.3  FOM= 0.92  TEST= 0
INDE   5  46  13  FOBS=   81.1  SIGMA=   2.0  PHAS=  171.3  FOM= 0.82  TEST= 0
INDE   5  46  15  FOBS=  201.0  SIGMA=   1.3  PHAS=   47.5  FOM= 0.94  TEST= 0
INDE   5  46  17  FOBS=  129.9  SIGMA=   1.9  PHAS= -124.5  FOM= 0.91  TEST= 0
INDE   5  46  19  FOBS=  168.6  SIGMA=   1.5  PHAS= -142.8  FOM= 0.94  TEST= 0
INDE   5  46  21  FOBS=  148.1  SIGMA=   1.7  PHAS=  179.2  FOM= 0.86  TEST= 0
INDE   5  46  23  FOBS=  134.5  SIGMA=   1.9  PHAS=  -58.8  FOM= 0.95  TEST= 0
INDE   5  46  25  FOBS=  169.0  SIGMA=   1.5  PHAS=  126.0  FOM= 0.80  TEST= 0
INDE   5  46  27  FOBS=   55.1  SIGMA=   6.3  PHAS=  148.8  FOM= 0.52  TEST= 0
INDE   5  46  29  FOBS=   78.6  SIGMA=   3.8  PHAS= -105.3  FOM= 0.86  TEST= 0
INDE   5  46  31  FOBS=  104.6  SIGMA=   2.5  PHAS=   10.9  FOM= 0.90  TEST= 0
INDE   5  46  33  FOBS=  126.7  SIGMA=   2.0  PHAS=  -61.1  FOM= 0.90  TEST= 0
INDE   5  46  35  FOBS=  137.8  SIGMA=   1.6  PHAS=  164.6  FOM= 0.92  TEST= 0
INDE   5  46  37  FOBS=    0.0  SIGMA=  19.1  PHAS=    0.0  FOM= 0.00  TEST= 0
INDE   5  46  39  FOBS=   48.9  SIGMA=   3.8  PHAS=   -3.7  FOM= 0.52  TEST= 0
INDE   5  46  41  FOBS=  159.6  SIGMA=   1.3  PHAS=   55.1  FOM= 0.96  TEST= 0
INDE   5  46  43  FOBS=   65.5  SIGMA=   2.8  PHAS= -133.2  FOM= 0.40  TEST= 0
INDE   5  46  45  FOBS=   70.4  SIGMA=   2.6  PHAS=  -52.5  FOM= 0.83  TEST= 0
INDE   5  46  47  FOBS=   29.5  SIGMA=   5.6  PHAS=   15.7  FOM= 0.26  TEST= 0
INDE   5  46  49  FOBS=  126.1  SIGMA=   1.3  PHAS=  -47.3  FOM= 0.96  TEST= 0
INDE   5  46  51  FOBS=  105.6  SIGMA=   1.7  PHAS=   -5.3  FOM= 0.85  TEST= 0
INDE   5  46  53  FOBS=    0.0  SIGMA=  19.5  PHAS=    0.0  FOM= 0.00  TEST= 0
INDE   5  46  55  FOBS=    0.0  SIGMA=  21.4  PHAS=    0.0  FOM= 0.00  TEST= 0
INDE   5  46  57  FOBS=   30.8  SIGMA=   5.9  PHAS=   -1.0  FOM= 0.42  TEST= 0
```

*FIG. 12A - 151*

```
INDE  5  46  59  FOBS=    0.0  SIGMA=  19.0  PHAS=    0.0  FOM=  0.00  TEST= 0
INDE  5  46  61  FOBS=   79.0  SIGMA=   2.6  PHAS=   13.7  FOM=  0.93  TEST= 0
INDE  5  47   6  FOBS=   41.5  SIGMA=   9.1  PHAS= -136.2  FOM=  0.70  TEST= 0
INDE  5  47   8  FOBS=  183.5  SIGMA=   2.3  PHAS=   41.3  FOM=  0.93  TEST= 0
INDE  5  47  10  FOBS=  177.1  SIGMA=   1.1  PHAS=  -86.9  FOM=  0.89  TEST= 0
INDE  5  47  12  FOBS=  189.2  SIGMA=   1.4  PHAS=  145.6  FOM=  0.97  TEST= 0
INDE  5  47  14  FOBS=  204.9  SIGMA=   1.2  PHAS=   -4.0  FOM=  0.94  TEST= 0
INDE  5  47  16  FOBS=  230.0  SIGMA=   1.1  PHAS=    8.5  FOM=  0.94  TEST= 0
INDE  5  47  18  FOBS=  372.2  SIGMA=   1.0  PHAS=  178.7  FOM=  0.98  TEST= 0
INDE  5  47  20  FOBS=   79.5  SIGMA=   4.7  PHAS=  172.8  FOM=  0.59  TEST= 0
INDE  5  47  22  FOBS=   30.5  SIGMA=   7.8  PHAS=  104.8  FOM=  0.67  TEST= 0
INDE  5  47  24  FOBS=    0.0  SIGMA=  23.3  PHAS=    0.0  FOM=  0.00  TEST= 0
INDE  5  47  26  FOBS=   27.9  SIGMA=   8.4  PHAS=   40.8  FOM=  0.24  TEST= 0
INDE  5  47  28  FOBS=   28.8  SIGMA=  10.2  PHAS=   60.1  FOM=  0.16  TEST= 0
INDE  5  47  30  FOBS=    0.0  SIGMA=  22.3  PHAS=    0.0  FOM=  0.00  TEST= 0
INDE  5  47  32  FOBS=   76.6  SIGMA=   3.3  PHAS=  -24.6  FOM=  0.88  TEST= 0
INDE  5  47  34  FOBS=   50.2  SIGMA=   4.9  PHAS=   96.3  FOM=  0.62  TEST= 0
INDE  5  47  36  FOBS=   45.8  SIGMA=   4.6  PHAS=   40.4  FOM=  0.68  TEST= 0
INDE  5  47  38  FOBS=   83.9  SIGMA=   2.2  PHAS=  -81.4  FOM=  0.90  TEST= 0
INDE  5  47  40  FOBS=  162.3  SIGMA=   1.2  PHAS= -141.7  FOM=  0.96  TEST= 0
INDE  5  47  42  FOBS=    0.0  SIGMA=  19.2  PHAS=    0.0  FOM=  0.00  TEST= 0
INDE  5  47  44  FOBS=   82.9  SIGMA=   2.2  PHAS=  -94.5  FOM=  0.81  TEST= 0
INDE  5  47  46  FOBS=   68.1  SIGMA=   2.7  PHAS=  -43.4  FOM=  0.85  TEST= 0
INDE  5  47  48  FOBS=   65.9  SIGMA=   2.4  PHAS= -133.4  FOM=  0.90  TEST= 0
INDE  5  47  50  FOBS=   66.6  SIGMA=   2.7  PHAS= -117.3  FOM=  0.06  TEST= 1
INDE  5  47  52  FOBS=   39.7  SIGMA=   4.8  PHAS= -131.8  FOM=  0.43  TEST= 0
INDE  5  47  54  FOBS=   29.9  SIGMA=   6.7  PHAS=   67.5  FOM=  0.40  TEST= 0
INDE  5  47  56  FOBS=   11.6  SIGMA=  16.6  PHAS= -139.9  FOM=  0.22  TEST= 0
INDE  5  47  58  FOBS=   19.8  SIGMA=   9.7  PHAS=   73.4  FOM=  0.06  TEST= 0
INDE  5  47  60  FOBS=    0.0  SIGMA=  21.1  PHAS=    0.0  FOM=  0.00  TEST= 0
INDE  5  48   5  FOBS=   57.0  SIGMA=   4.0  PHAS=  -90.0  FOM=  0.51  TEST= 1
INDE  5  48   7  FOBS=  136.4  SIGMA=   3.0  PHAS= -172.7  FOM=  0.93  TEST= 0
INDE  5  48   9  FOBS=  189.0  SIGMA=   2.3  PHAS=  -53.5  FOM=  0.90  TEST= 1
INDE  5  48  11  FOBS=  288.0  SIGMA=   1.0  PHAS= -101.0  FOM=  0.97  TEST= 0
INDE  5  48  13  FOBS=  112.0  SIGMA=   1.4  PHAS=   91.7  FOM=  0.94  TEST= 0
INDE  5  48  15  FOBS=   75.3  SIGMA=   2.3  PHAS=   67.7  FOM=  0.86  TEST= 0
INDE  5  48  17  FOBS=    0.0  SIGMA=  21.5  PHAS=    0.0  FOM=  0.00  TEST= 0
INDE  5  48  19  FOBS=  135.6  SIGMA=   1.8  PHAS=  170.2  FOM=  0.90  TEST= 0
INDE  5  48  21  FOBS=    0.0  SIGMA=  21.6  PHAS=    0.0  FOM=  0.00  TEST= 1
INDE  5  48  23  FOBS=  147.1  SIGMA=   1.7  PHAS= -152.6  FOM=  0.91  TEST= 0
INDE  5  48  25  FOBS=    0.0  SIGMA=  23.0  PHAS=    0.0  FOM=  0.00  TEST= 0
INDE  5  48  27  FOBS=  101.9  SIGMA=   2.2  PHAS=  115.8  FOM=  0.80  TEST= 0
INDE  5  48  29  FOBS=    0.0  SIGMA=  27.5  PHAS=    0.0  FOM=  0.00  TEST= 0
INDE  5  48  31  FOBS=  170.3  SIGMA=   1.6  PHAS=  -71.7  FOM=  0.97  TEST= 0
INDE  5  48  33  FOBS=  200.6  SIGMA=   1.4  PHAS=  -65.5  FOM=  0.95  TEST= 0
INDE  5  48  35  FOBS=   82.6  SIGMA=   3.0  PHAS=  136.1  FOM=  0.64  TEST= 0
INDE  5  48  37  FOBS=  110.7  SIGMA=   1.9  PHAS= -160.5  FOM=  0.95  TEST= 0
INDE  5  48  39  FOBS=  175.1  SIGMA=   1.2  PHAS=  160.7  FOM=  0.95  TEST= 1
INDE  5  48  41  FOBS=   95.8  SIGMA=   2.0  PHAS=   82.2  FOM=  0.92  TEST= 0
INDE  5  48  43  FOBS=   51.4  SIGMA=   3.6  PHAS=  -40.9  FOM=  0.38  TEST= 0
INDE  5  48  45  FOBS=   25.1  SIGMA=   7.2  PHAS=  -20.9  FOM=  0.14  TEST= 0
INDE  5  48  47  FOBS=   17.5  SIGMA=  10.9  PHAS= -155.3  FOM=  0.32  TEST= 0
INDE  5  48  49  FOBS=   41.6  SIGMA=   4.3  PHAS=   61.8  FOM=  0.60  TEST= 0
INDE  5  48  51  FOBS=   27.1  SIGMA=   7.7  PHAS= -122.0  FOM=  0.14  TEST= 0
INDE  5  48  53  FOBS=   90.5  SIGMA=   2.0  PHAS=   63.9  FOM=  0.05  TEST= 1
INDE  5  48  55  FOBS=   35.2  SIGMA=   5.7  PHAS=  -31.9  FOM=  0.07  TEST= 1
INDE  5  48  57  FOBS=   65.5  SIGMA=   3.0  PHAS=  151.6  FOM=  0.18  TEST= 1
INDE  5  48  59  FOBS=    0.0  SIGMA=  20.3  PHAS=    0.0  FOM=  0.00  TEST= 0
INDE  5  49   6  FOBS=   88.1  SIGMA=   4.6  PHAS=   17.1  FOM=  0.91  TEST= 0
INDE  5  49   8  FOBS=   68.9  SIGMA=   5.7  PHAS=  177.0  FOM=  0.79  TEST= 1
INDE  5  49  10  FOBS=  151.1  SIGMA=   2.7  PHAS= -125.9  FOM=  0.90  TEST= 0
INDE  5  49  12  FOBS=  148.9  SIGMA=   1.3  PHAS=   70.8  FOM=  0.90  TEST= 0
INDE  5  49  14  FOBS=  107.7  SIGMA=   1.7  PHAS=  167.9  FOM=  0.88  TEST= 0
INDE  5  49  16  FOBS=  113.2  SIGMA=   1.5  PHAS=  -37.7  FOM=  0.63  TEST= 1
INDE  5  49  18  FOBS=  206.3  SIGMA=   1.3  PHAS= -119.0  FOM=  0.92  TEST= 0
INDE  5  49  20  FOBS=   39.8  SIGMA=   5.7  PHAS=  -82.2  FOM=  0.18  TEST= 0
INDE  5  49  22  FOBS=   33.2  SIGMA=   7.9  PHAS=  104.5  FOM=  0.53  TEST= 0
INDE  5  49  24  FOBS=   68.9  SIGMA=   3.6  PHAS=   -0.6  FOM=  0.44  TEST= 0
INDE  5  49  26  FOBS=   82.6  SIGMA=   2.7  PHAS=  167.2  FOM=  0.64  TEST= 0
INDE  5  49  28  FOBS=  142.1  SIGMA=   1.6  PHAS=  125.3  FOM=  0.88  TEST= 0
```

*FIG. 12A - 152*

```
INDE   5  49  30  FOBS=    44.1  SIGMA=   5.7  PHAS=  -171.0  FOM=  0.52  TEST=  0
INDE   5  49  32  FOBS=   189.7  SIGMA=   1.5  PHAS=   -88.7  FOM=  0.95  TEST=  0
INDE   5  49  34  FOBS=   145.8  SIGMA=   1.8  PHAS=  -175.0  FOM=  0.93  TEST=  0
INDE   5  49  36  FOBS=    71.1  SIGMA=   3.0  PHAS=   140.0  FOM=  0.89  TEST=  0
INDE   5  49  38  FOBS=   129.0  SIGMA=   1.5  PHAS=   109.5  FOM=  0.95  TEST=  0
INDE   5  49  40  FOBS=    86.9  SIGMA=   2.2  PHAS=    89.8  FOM=  0.91  TEST=  1
INDE   5  49  42  FOBS=    43.2  SIGMA=   4.4  PHAS=   -21.9  FOM=  0.65  TEST=  0
INDE   5  49  44  FOBS=    24.2  SIGMA=   8.8  PHAS=    -8.7  FOM=  0.36  TEST=  0
INDE   5  49  46  FOBS=     0.0  SIGMA=  19.0  PHAS=     0.0  FOM=  0.00  TEST=  0
INDE   5  49  48  FOBS=     0.0  SIGMA=  17.5  PHAS=     0.0  FOM=  0.00  TEST=  0
INDE   5  49  50  FOBS=    81.4  SIGMA=   2.3  PHAS=     3.3  FOM=  0.05  TEST=  1
INDE   5  49  52  FOBS=   108.9  SIGMA=   1.7  PHAS=    66.6  FOM=  0.93  TEST=  0
INDE   5  49  54  FOBS=    28.6  SIGMA=   6.8  PHAS=    43.8  FOM=  0.18  TEST=  0
INDE   5  49  56  FOBS=    46.4  SIGMA=   3.9  PHAS=   -61.9  FOM=  0.74  TEST=  0
INDE   5  49  58  FOBS=    13.2  SIGMA=  17.3  PHAS=    43.2  FOM=  0.07  TEST=  0
INDE   5  49  60  FOBS=    40.3  SIGMA=   6.3  PHAS=   -82.6  FOM=  0.02  TEST=  1
INDE   5  50   5  FOBS=   151.3  SIGMA=   1.6  PHAS=   -94.4  FOM=  0.87  TEST=  0
INDE   5  50   7  FOBS=   166.4  SIGMA=   2.5  PHAS=  -135.8  FOM=  0.84  TEST=  1
INDE   5  50   9  FOBS=     0.0  SIGMA=  27.7  PHAS=     0.0  FOM=  0.00  TEST=  0
INDE   5  50  11  FOBS=    83.4  SIGMA=   2.6  PHAS=   113.6  FOM=  0.89  TEST=  0
INDE   5  50  13  FOBS=   264.4  SIGMA=   0.8  PHAS=    71.1  FOM=  0.96  TEST=  0
INDE   5  50  15  FOBS=   176.8  SIGMA=   1.0  PHAS=   119.7  FOM=  0.89  TEST=  0
INDE   5  50  17  FOBS=   109.8  SIGMA=   1.6  PHAS=   129.9  FOM=  0.78  TEST=  0
INDE   5  50  19  FOBS=   171.6  SIGMA=   1.4  PHAS=   144.7  FOM=  0.87  TEST=  0
INDE   5  50  21  FOBS=     0.0  SIGMA=  21.2  PHAS=     0.0  FOM=  0.00  TEST=  0
INDE   5  50  23  FOBS=   239.8  SIGMA=   1.1  PHAS=  -164.5  FOM=  0.94  TEST=  0
INDE   5  50  25  FOBS=    13.8  SIGMA=  17.1  PHAS=    92.5  FOM=  0.06  TEST=  0
INDE   5  50  27  FOBS=    51.3  SIGMA=   4.2  PHAS=   115.7  FOM=  0.51  TEST=  0
INDE   5  50  29  FOBS=   129.9  SIGMA=   1.6  PHAS=    20.7  FOM=  0.90  TEST=  0
INDE   5  50  31  FOBS=   126.5  SIGMA=   2.1  PHAS=  -112.0  FOM=  0.89  TEST=  0
INDE   5  50  33  FOBS=    85.9  SIGMA=   2.9  PHAS=   148.7  FOM=  0.84  TEST=  0
INDE   5  50  35  FOBS=   141.5  SIGMA=   1.8  PHAS=   110.2  FOM=  0.96  TEST=  0
INDE   5  50  37  FOBS=    42.0  SIGMA=   4.9  PHAS=    20.3  FOM=  0.84  TEST=  0
INDE   5  50  39  FOBS=    60.8  SIGMA=   3.0  PHAS=    84.2  FOM=  0.74  TEST=  0
INDE   5  50  41  FOBS=    66.6  SIGMA=   2.8  PHAS=    34.5  FOM=  0.85  TEST=  0
INDE   5  50  43  FOBS=    60.1  SIGMA=   3.1  PHAS=   -20.1  FOM=  0.91  TEST=  0
INDE   5  50  45  FOBS=    12.6  SIGMA=  17.5  PHAS=    78.1  FOM=  0.12  TEST=  0
INDE   5  50  47  FOBS=     0.0  SIGMA=  18.2  PHAS=     0.0  FOM=  0.00  TEST=  0
INDE   5  50  49  FOBS=    85.6  SIGMA=   2.2  PHAS=    95.4  FOM=  0.75  TEST=  0
INDE   5  50  51  FOBS=    88.7  SIGMA=   2.1  PHAS=    19.0  FOM=  0.88  TEST=  0
INDE   5  50  53  FOBS=     0.0  SIGMA=  19.5  PHAS=     0.0  FOM=  0.00  TEST=  0
INDE   5  50  55  FOBS=     0.0  SIGMA=  20.8  PHAS=     0.0  FOM=  0.00  TEST=  0
INDE   5  50  57  FOBS=    31.9  SIGMA=   7.9  PHAS=  -154.8  FOM=  0.43  TEST=  0
INDE   5  50  59  FOBS=    62.9  SIGMA=   4.0  PHAS=  -177.3  FOM=  0.77  TEST=  0
INDE   5  51   6  FOBS=   139.3  SIGMA=   2.9  PHAS=  -124.6  FOM=  0.88  TEST=  0
INDE   5  51   8  FOBS=   142.2  SIGMA=   2.8  PHAS=   124.7  FOM=  0.95  TEST=  0
INDE   5  51  10  FOBS=   111.7  SIGMA=   3.5  PHAS=   -40.8  FOM=  0.71  TEST=  0
INDE   5  51  12  FOBS=   359.0  SIGMA=   1.4  PHAS=    18.3  FOM=  0.98  TEST=  0
INDE   5  51  14  FOBS=   213.5  SIGMA=   0.9  PHAS=    47.8  FOM=  0.92  TEST=  0
INDE   5  51  16  FOBS=   127.3  SIGMA=   1.3  PHAS=   -59.5  FOM=  0.81  TEST=  0
INDE   5  51  18  FOBS=    31.6  SIGMA=   5.3  PHAS=    -8.7  FOM=  0.68  TEST=  0
INDE   5  51  20  FOBS=    59.5  SIGMA=   3.8  PHAS=   -28.4  FOM=  0.49  TEST=  0
INDE   5  51  22  FOBS=   182.6  SIGMA=   1.4  PHAS=   124.4  FOM=  0.97  TEST=  0
INDE   5  51  24  FOBS=    80.2  SIGMA=   3.0  PHAS=    24.8  FOM=  0.65  TEST=  0
INDE   5  51  26  FOBS=   130.4  SIGMA=   1.8  PHAS=    29.1  FOM=  0.64  TEST=  0
INDE   5  51  28  FOBS=    45.9  SIGMA=   4.3  PHAS=   -57.3  FOM=  0.56  TEST=  0
INDE   5  51  30  FOBS=    68.8  SIGMA=   3.6  PHAS=    15.5  FOM=  0.66  TEST=  1
INDE   5  51  32  FOBS=    77.0  SIGMA=   3.3  PHAS=  -134.4  FOM=  0.77  TEST=  0
INDE   5  51  34  FOBS=   103.4  SIGMA=   2.4  PHAS=    -6.2  FOM=  0.20  TEST=  1
INDE   5  51  36  FOBS=    99.0  SIGMA=   2.5  PHAS=    16.5  FOM=  0.91  TEST=  0
INDE   5  51  38  FOBS=   131.5  SIGMA=   1.7  PHAS=   -11.0  FOM=  0.88  TEST=  0
INDE   5  51  40  FOBS=    87.4  SIGMA=   2.1  PHAS=    -9.0  FOM=  0.76  TEST=  0
INDE   5  51  42  FOBS=     0.0  SIGMA=  18.9  PHAS=     0.0  FOM=  0.00  TEST=  1
INDE   5  51  44  FOBS=    85.3  SIGMA=   2.2  PHAS=  -138.6  FOM=  0.63  TEST=  0
INDE   5  51  46  FOBS=     0.0  SIGMA=  19.1  PHAS=     0.0  FOM=  0.00  TEST=  0
INDE   5  51  48  FOBS=     0.0  SIGMA=  19.8  PHAS=     0.0  FOM=  0.00  TEST=  0
INDE   5  51  50  FOBS=    36.7  SIGMA=   5.3  PHAS=   107.2  FOM=  0.02  TEST=  1
INDE   5  51  52  FOBS=    55.2  SIGMA=   3.5  PHAS=    34.3  FOM=  0.79  TEST=  0
INDE   5  51  54  FOBS=    49.8  SIGMA=   3.7  PHAS=  -150.3  FOM=  0.77  TEST=  0
INDE   5  51  56  FOBS=    59.1  SIGMA=   3.6  PHAS=   176.8  FOM=  0.70  TEST=  0
```

*FIG. 12A - 153*

| | | | | | | | | | | | | | |
|---|---|---|---|---|---|---|---|---|---|---|---|---|---|
| INDE | 5 | 51 | 58 | FOBS= | 78.6 | SIGMA= | 3.2 | PHAS= | 93.6 | FOM= | 0.91 | TEST= | 0 |
| INDE | 5 | 52 | 5 | FOBS= | 75.9 | SIGMA= | 3.6 | PHAS= | -108.8 | FOM= | 0.73 | TEST= | 0 |
| INDE | 5 | 52 | 7 | FOBS= | 86.2 | SIGMA= | 4.5 | PHAS= | 68.5 | FOM= | 0.83 | TEST= | 0 |
| INDE | 5 | 52 | 9 | FOBS= | 45.9 | SIGMA= | 8.1 | PHAS= | 47.9 | FOM= | 0.36 | TEST= | 0 |
| INDE | 5 | 52 | 11 | FOBS= | 44.9 | SIGMA= | 8.3 | PHAS= | -121.3 | FOM= | 0.34 | TEST= | 0 |
| INDE | 5 | 52 | 13 | FOBS= | 129.7 | SIGMA= | 1.9 | PHAS= | -108.5 | FOM= | 0.88 | TEST= | 0 |
| INDE | 5 | 52 | 15 | FOBS= | 167.5 | SIGMA= | 1.0 | PHAS= | -96.8 | FOM= | 0.95 | TEST= | 0 |
| INDE | 5 | 52 | 17 | FOBS= | 50.8 | SIGMA= | 3.3 | PHAS= | 95.4 | FOM= | 0.36 | TEST= | 0 |
| INDE | 5 | 52 | 19 | FOBS= | 0.0 | SIGMA= | 20.5 | PHAS= | 0.0 | FOM= | 0.00 | TEST= | 0 |
| INDE | 5 | 52 | 21 | FOBS= | 44.9 | SIGMA= | 5.0 | PHAS= | 58.6 | FOM= | 0.30 | TEST= | 0 |
| INDE | 5 | 52 | 23 | FOBS= | 60.2 | SIGMA= | 3.9 | PHAS= | -27.1 | FOM= | 0.57 | TEST= | 0 |
| INDE | 5 | 52 | 25 | FOBS= | 47.4 | SIGMA= | 4.6 | PHAS= | 6.6 | FOM= | 0.18 | TEST= | 0 |
| INDE | 5 | 52 | 27 | FOBS= | 70.1 | SIGMA= | 2.9 | PHAS= | -139.7 | FOM= | 0.58 | TEST= | 1 |
| INDE | 5 | 52 | 29 | FOBS= | 123.4 | SIGMA= | 1.7 | PHAS= | -56.8 | FOM= | 0.47 | TEST= | 1 |
| INDE | 5 | 52 | 31 | FOBS= | 34.4 | SIGMA= | 7.1 | PHAS= | -71.6 | FOM= | 0.25 | TEST= | 0 |
| INDE | 5 | 52 | 33 | FOBS= | 104.9 | SIGMA= | 2.4 | PHAS= | -1.7 | FOM= | 0.85 | TEST= | 0 |
| INDE | 5 | 52 | 35 | FOBS= | 82.0 | SIGMA= | 3.0 | PHAS= | -159.7 | FOM= | 0.88 | TEST= | 0 |
| INDE | 5 | 52 | 37 | FOBS= | 91.6 | SIGMA= | 2.7 | PHAS= | -112.3 | FOM= | 0.88 | TEST= | 0 |
| INDE | 5 | 52 | 39 | FOBS= | 72.4 | SIGMA= | 2.7 | PHAS= | -95.3 | FOM= | 0.53 | TEST= | 0 |
| INDE | 5 | 52 | 41 | FOBS= | 19.3 | SIGMA= | 10.4 | PHAS= | -176.7 | FOM= | 0.08 | TEST= | 1 |
| INDE | 5 | 52 | 43 | FOBS= | 14.8 | SIGMA= | 13.3 | PHAS= | -0.9 | FOM= | 0.13 | TEST= | 0 |
| INDE | 5 | 52 | 45 | FOBS= | 51.0 | SIGMA= | 3.6 | PHAS= | 109.2 | FOM= | 0.73 | TEST= | 0 |
| INDE | 5 | 52 | 47 | FOBS= | 70.1 | SIGMA= | 2.3 | PHAS= | 177.4 | FOM= | 0.70 | TEST= | 0 |
| INDE | 5 | 52 | 49 | FOBS= | 71.9 | SIGMA= | 2.6 | PHAS= | -121.9 | FOM= | 0.05 | TEST= | 1 |
| INDE | 5 | 52 | 51 | FOBS= | 0.0 | SIGMA= | 19.7 | PHAS= | 0.0 | FOM= | 0.00 | TEST= | 0 |
| INDE | 5 | 52 | 53 | FOBS= | 26.8 | SIGMA= | 8.6 | PHAS= | -7.2 | FOM= | 0.38 | TEST= | 0 |
| INDE | 5 | 52 | 55 | FOBS= | 133.5 | SIGMA= | 1.7 | PHAS= | 79.2 | FOM= | 0.97 | TEST= | 0 |
| INDE | 5 | 52 | 57 | FOBS= | 105.5 | SIGMA= | 2.5 | PHAS= | 29.2 | FOM= | 0.90 | TEST= | 0 |
| INDE | 5 | 53 | 6 | FOBS= | 198.5 | SIGMA= | 2.1 | PHAS= | -109.5 | FOM= | 0.95 | TEST= | 0 |
| INDE | 5 | 53 | 8 | FOBS= | 64.0 | SIGMA= | 5.9 | PHAS= | -144.2 | FOM= | 0.45 | TEST= | 1 |
| INDE | 5 | 53 | 10 | FOBS= | 76.0 | SIGMA= | 5.0 | PHAS= | -54.8 | FOM= | 0.66 | TEST= | 0 |
| INDE | 5 | 53 | 12 | FOBS= | 176.2 | SIGMA= | 2.3 | PHAS= | 66.9 | FOM= | 0.97 | TEST= | 0 |
| INDE | 5 | 53 | 14 | FOBS= | 0.0 | SIGMA= | 20.0 | PHAS= | 0.0 | FOM= | 0.00 | TEST= | 0 |
| INDE | 5 | 53 | 16 | FOBS= | 180.9 | SIGMA= | 1.0 | PHAS= | -92.0 | FOM= | 0.89 | TEST= | 1 |
| INDE | 5 | 53 | 18 | FOBS= | 0.0 | SIGMA= | 19.2 | PHAS= | 0.0 | FOM= | 0.00 | TEST= | 0 |
| INDE | 5 | 53 | 20 | FOBS= | 38.1 | SIGMA= | 5.9 | PHAS= | 174.2 | FOM= | 0.83 | TEST= | 0 |
| INDE | 5 | 53 | 22 | FOBS= | 65.1 | SIGMA= | 3.5 | PHAS= | 65.2 | FOM= | 0.37 | TEST= | 0 |
| INDE | 5 | 53 | 24 | FOBS= | 100.9 | SIGMA= | 2.2 | PHAS= | -73.2 | FOM= | 0.91 | TEST= | 0 |
| INDE | 5 | 53 | 26 | FOBS= | 76.5 | SIGMA= | 2.6 | PHAS= | 168.5 | FOM= | 0.39 | TEST= | 0 |
| INDE | 5 | 53 | 28 | FOBS= | 95.4 | SIGMA= | 2.1 | PHAS= | -137.4 | FOM= | 0.75 | TEST= | 0 |
| INDE | 5 | 53 | 30 | FOBS= | 92.8 | SIGMA= | 2.2 | PHAS= | -56.0 | FOM= | 0.91 | TEST= | 0 |
| INDE | 5 | 53 | 32 | FOBS= | 88.5 | SIGMA= | 2.9 | PHAS= | -53.5 | FOM= | 0.82 | TEST= | 0 |
| INDE | 5 | 53 | 34 | FOBS= | 104.6 | SIGMA= | 2.4 | PHAS= | 114.2 | FOM= | 0.90 | TEST= | 0 |
| INDE | 5 | 53 | 36 | FOBS= | 131.8 | SIGMA= | 2.0 | PHAS= | 53.4 | FOM= | 0.95 | TEST= | 0 |
| INDE | 5 | 53 | 38 | FOBS= | 74.2 | SIGMA= | 2.8 | PHAS= | 9.5 | FOM= | 0.68 | TEST= | 0 |
| INDE | 5 | 53 | 40 | FOBS= | 0.0 | SIGMA= | 21.2 | PHAS= | 0.0 | FOM= | 0.00 | TEST= | 0 |
| INDE | 5 | 53 | 42 | FOBS= | 0.0 | SIGMA= | 19.5 | PHAS= | 0.0 | FOM= | 0.00 | TEST= | 1 |
| INDE | 5 | 53 | 44 | FOBS= | 26.1 | SIGMA= | 7.6 | PHAS= | 134.2 | FOM= | 0.61 | TEST= | 0 |
| INDE | 5 | 53 | 46 | FOBS= | 57.3 | SIGMA= | 3.0 | PHAS= | 88.3 | FOM= | 0.39 | TEST= | 1 |
| INDE | 5 | 53 | 48 | FOBS= | 61.2 | SIGMA= | 3.1 | PHAS= | 40.4 | FOM= | 0.88 | TEST= | 0 |
| INDE | 5 | 53 | 50 | FOBS= | 0.0 | SIGMA= | 20.4 | PHAS= | 0.0 | FOM= | 0.00 | TEST= | 0 |
| INDE | 5 | 53 | 52 | FOBS= | 0.0 | SIGMA= | 21.0 | PHAS= | 0.0 | FOM= | 0.00 | TEST= | 0 |
| INDE | 5 | 53 | 54 | FOBS= | 102.8 | SIGMA= | 2.1 | PHAS= | -66.2 | FOM= | 0.96 | TEST= | 0 |
| INDE | 5 | 53 | 56 | FOBS= | 112.2 | SIGMA= | 2.7 | PHAS= | 20.1 | FOM= | 0.94 | TEST= | 0 |
| INDE | 5 | 54 | 5 | FOBS= | 73.4 | SIGMA= | 4.2 | PHAS= | 179.6 | FOM= | 0.81 | TEST= | 0 |
| INDE | 5 | 54 | 7 | FOBS= | 147.3 | SIGMA= | 2.6 | PHAS= | -165.4 | FOM= | 0.87 | TEST= | 0 |
| INDE | 5 | 54 | 9 | FOBS= | 61.0 | SIGMA= | 6.1 | PHAS= | 75.5 | FOM= | 0.35 | TEST= | 0 |
| INDE | 5 | 54 | 11 | FOBS= | 183.7 | SIGMA= | 2.2 | PHAS= | -113.2 | FOM= | 0.32 | TEST= | 1 |
| INDE | 5 | 54 | 13 | FOBS= | 145.5 | SIGMA= | 1.3 | PHAS= | -29.1 | FOM= | 0.94 | TEST= | 0 |
| INDE | 5 | 54 | 15 | FOBS= | 78.0 | SIGMA= | 2.4 | PHAS= | -163.4 | FOM= | 0.85 | TEST= | 0 |
| INDE | 5 | 54 | 17 | FOBS= | 36.6 | SIGMA= | 4.3 | PHAS= | -176.3 | FOM= | 0.34 | TEST= | 0 |
| INDE | 5 | 54 | 19 | FOBS= | 0.0 | SIGMA= | 18.3 | PHAS= | 0.0 | FOM= | 0.00 | TEST= | 0 |
| INDE | 5 | 54 | 21 | FOBS= | 45.7 | SIGMA= | 4.6 | PHAS= | 155.3 | FOM= | 0.14 | TEST= | 1 |
| INDE | 5 | 54 | 23 | FOBS= | 28.2 | SIGMA= | 8.1 | PHAS= | 96.9 | FOM= | 0.17 | TEST= | 1 |
| INDE | 5 | 54 | 25 | FOBS= | 132.0 | SIGMA= | 1.6 | PHAS= | -132.7 | FOM= | 0.93 | TEST= | 0 |
| INDE | 5 | 54 | 27 | FOBS= | 99.8 | SIGMA= | 2.0 | PHAS= | -106.7 | FOM= | 0.80 | TEST= | 0 |
| INDE | 5 | 54 | 29 | FOBS= | 85.9 | SIGMA= | 2.3 | PHAS= | 161.0 | FOM= | 0.30 | TEST= | 1 |
| INDE | 5 | 54 | 31 | FOBS= | 79.9 | SIGMA= | 2.5 | PHAS= | -139.7 | FOM= | 0.85 | TEST= | 0 |
| INDE | 5 | 54 | 33 | FOBS= | 103.4 | SIGMA= | 2.5 | PHAS= | -9.7 | FOM= | 0.93 | TEST= | 0 |
| INDE | 5 | 54 | 35 | FOBS= | 42.3 | SIGMA= | 5.7 | PHAS= | -17.6 | FOM= | 0.55 | TEST= | 1 |

*FIG. 12A - 154*

```
INDE   5   54   37  FOBS=    139.1  SIGMA=   1.8  PHAS=   -81.4  FOM=  0.94  TEST= 0
INDE   5   54   39  FOBS=     40.9  SIGMA=   5.0  PHAS=    -6.4  FOM=  0.54  TEST= 0
INDE   5   54   41  FOBS=      0.0  SIGMA=  19.5  PHAS=     0.0  FOM=  0.00  TEST= 0
INDE   5   54   43  FOBS=     70.4  SIGMA=   2.6  PHAS=  -122.4  FOM=  0.67  TEST= 0
INDE   5   54   45  FOBS=    124.2  SIGMA=   1.6  PHAS=    67.3  FOM=  0.94  TEST= 0
INDE   5   54   47  FOBS=     61.0  SIGMA=   3.1  PHAS=    14.5  FOM=  0.01  TEST= 1
INDE   5   54   49  FOBS=     57.7  SIGMA=   3.3  PHAS=   -53.3  FOM=  0.66  TEST= 0
INDE   5   54   51  FOBS=     58.7  SIGMA=   3.5  PHAS=  -157.3  FOM=  0.59  TEST= 0
INDE   5   54   53  FOBS=     61.4  SIGMA=   3.9  PHAS=  -138.1  FOM=  0.89  TEST= 0
INDE   5   54   55  FOBS=      0.0  SIGMA=  25.8  PHAS=     0.0  FOM=  0.00  TEST= 0
INDE   5   55    6  FOBS=    151.0  SIGMA=   2.2  PHAS=    97.9  FOM=  0.91  TEST= 0
INDE   5   55    8  FOBS=     22.2  SIGMA=  13.6  PHAS=   -65.1  FOM=  0.37  TEST= 0
INDE   5   55   10  FOBS=     83.3  SIGMA=   4.5  PHAS=  -153.5  FOM=  0.74  TEST= 0
INDE   5   55   12  FOBS=    163.1  SIGMA=   2.4  PHAS=  -169.1  FOM=  0.89  TEST= 0
INDE   5   55   14  FOBS=    114.4  SIGMA=   1.6  PHAS=   -41.9  FOM=  0.85  TEST= 0
INDE   5   55   16  FOBS=     79.9  SIGMA=   1.9  PHAS=   -40.7  FOM=  0.74  TEST= 0
INDE   5   55   18  FOBS=    184.3  SIGMA=   1.0  PHAS=   116.7  FOM=  0.96  TEST= 0
INDE   5   55   20  FOBS=     74.8  SIGMA=   2.2  PHAS=   174.2  FOM=  0.90  TEST= 0
INDE   5   55   22  FOBS=     43.3  SIGMA=   5.1  PHAS=   140.8  FOM=  0.49  TEST= 0
INDE   5   55   24  FOBS=    102.8  SIGMA=   1.9  PHAS=   159.4  FOM=  0.79  TEST= 0
INDE   5   55   26  FOBS=     64.3  SIGMA=   3.1  PHAS=   118.1  FOM=  0.44  TEST= 0
INDE   5   55   28  FOBS=     47.8  SIGMA=   4.2  PHAS=   175.9  FOM=  0.68  TEST= 0
INDE   5   55   30  FOBS=    108.5  SIGMA=   1.9  PHAS=    -5.3  FOM=  0.83  TEST= 0
INDE   5   55   32  FOBS=     33.5  SIGMA=   5.9  PHAS=   -70.6  FOM=  0.39  TEST= 0
INDE   5   55   34  FOBS=     47.7  SIGMA=   5.1  PHAS=   -76.3  FOM=  0.33  TEST= 0
INDE   5   55   36  FOBS=     66.1  SIGMA=   3.7  PHAS=   157.4  FOM=  0.87  TEST= 0
INDE   5   55   38  FOBS=    105.4  SIGMA=   2.3  PHAS=   -46.5  FOM=  0.91  TEST= 0
INDE   5   55   40  FOBS=     69.0  SIGMA=   3.0  PHAS=   -75.6  FOM=  0.87  TEST= 0
INDE   5   55   42  FOBS=     85.1  SIGMA=   2.2  PHAS=    45.4  FOM=  0.24  TEST= 1
INDE   5   55   44  FOBS=     36.8  SIGMA=   5.0  PHAS=   125.2  FOM=  0.68  TEST= 0
INDE   5   55   46  FOBS=     35.9  SIGMA=   5.1  PHAS=    17.5  FOM=  0.35  TEST= 0
INDE   5   55   48  FOBS=     27.0  SIGMA=   7.9  PHAS=    51.5  FOM=  0.37  TEST= 0
INDE   5   55   50  FOBS=     39.9  SIGMA=   5.2  PHAS=    86.6  FOM=  0.24  TEST= 0
INDE   5   55   52  FOBS=     57.7  SIGMA=   4.5  PHAS=  -158.8  FOM=  0.87  TEST= 0
INDE   5   55   54  FOBS=      0.0  SIGMA=  25.7  PHAS=     0.0  FOM=  0.00  TEST= 0
INDE   5   56    5  FOBS=      0.0  SIGMA=  24.6  PHAS=     0.0  FOM=  0.00  TEST= 0
INDE   5   56    7  FOBS=     50.1  SIGMA=   6.1  PHAS=   -60.0  FOM=  0.43  TEST= 0
INDE   5   56    9  FOBS=    128.6  SIGMA=   2.5  PHAS=   104.5  FOM=  0.91  TEST= 0
INDE   5   56   11  FOBS=     28.9  SIGMA=  10.4  PHAS=   146.4  FOM=  0.16  TEST= 0
INDE   5   56   13  FOBS=     55.3  SIGMA=   5.4  PHAS=   -18.9  FOM=  0.78  TEST= 0
INDE   5   56   15  FOBS=    146.8  SIGMA=   1.3  PHAS=  -128.6  FOM=  0.89  TEST= 0
INDE   5   56   17  FOBS=    141.6  SIGMA=   1.1  PHAS=   -35.7  FOM=  0.94  TEST= 0
INDE   5   56   19  FOBS=    172.4  SIGMA=   1.0  PHAS=    14.4  FOM=  0.98  TEST= 0
INDE   5   56   21  FOBS=     58.4  SIGMA=   2.8  PHAS=   116.2  FOM=  0.84  TEST= 0
INDE   5   56   23  FOBS=     96.7  SIGMA=   2.0  PHAS=   110.5  FOM=  0.88  TEST= 0
INDE   5   56   25  FOBS=     52.3  SIGMA=   3.7  PHAS=   158.7  FOM=  0.52  TEST= 0
INDE   5   56   27  FOBS=      7.9  SIGMA=  24.6  PHAS=    -0.6  FOM=  0.06  TEST= 0
INDE   5   56   29  FOBS=     68.6  SIGMA=   2.9  PHAS=   139.8  FOM=  0.86  TEST= 0
INDE   5   56   31  FOBS=     45.0  SIGMA=   4.4  PHAS=   -68.2  FOM=  0.64  TEST= 0
INDE   5   56   33  FOBS=      0.0  SIGMA=  19.7  PHAS=     0.0  FOM=  0.00  TEST= 0
INDE   5   56   35  FOBS=     75.7  SIGMA=   3.2  PHAS=   133.6  FOM=  0.51  TEST= 0
INDE   5   56   37  FOBS=     61.6  SIGMA=   3.9  PHAS=  -141.5  FOM=  0.64  TEST= 0
INDE   5   56   39  FOBS=    129.1  SIGMA=   1.8  PHAS=  -128.8  FOM=  0.95  TEST= 0
INDE   5   56   41  FOBS=     65.9  SIGMA=   2.9  PHAS=   -90.3  FOM=  0.84  TEST= 0
INDE   5   56   43  FOBS=     51.7  SIGMA=   3.8  PHAS=    77.8  FOM=  0.65  TEST= 0
INDE   5   56   45  FOBS=     59.0  SIGMA=   3.1  PHAS=    35.5  FOM=  0.89  TEST= 0
INDE   5   56   47  FOBS=     50.3  SIGMA=   4.5  PHAS=    47.1  FOM=  0.51  TEST= 0
INDE   5   56   49  FOBS=     27.1  SIGMA=   8.2  PHAS=   -72.1  FOM=  0.38  TEST= 0
INDE   5   56   51  FOBS=      0.0  SIGMA=  22.9  PHAS=     0.0  FOM=  0.00  TEST= 1
INDE   5   56   53  FOBS=      0.0  SIGMA=  25.7  PHAS=     0.0  FOM=  0.00  TEST= 1
INDE   5   57    6  FOBS=     65.6  SIGMA=   4.0  PHAS=   139.5  FOM=  0.81  TEST= 0
INDE   5   57    8  FOBS=     42.7  SIGMA=   6.9  PHAS=    13.2  FOM=  0.71  TEST= 0
INDE   5   57   10  FOBS=    125.8  SIGMA=   2.5  PHAS=   -94.9  FOM=  0.58  TEST= 1
INDE   5   57   12  FOBS=     87.3  SIGMA=   3.5  PHAS=  -141.0  FOM=  0.68  TEST= 0
INDE   5   57   14  FOBS=      0.0  SIGMA=  19.8  PHAS=     0.0  FOM=  0.00  TEST= 0
INDE   5   57   16  FOBS=     53.0  SIGMA=   3.4  PHAS=   143.7  FOM=  0.70  TEST= 1
INDE   5   57   18  FOBS=    151.6  SIGMA=   1.1  PHAS=  -133.6  FOM=  0.95  TEST= 1
INDE   5   57   20  FOBS=      4.5  SIGMA=  34.5  PHAS=  -168.2  FOM=  0.03  TEST= 0
INDE   5   57   22  FOBS=     84.6  SIGMA=   1.9  PHAS=    94.4  FOM=  0.72  TEST= 1
INDE   5   57   24  FOBS=     35.1  SIGMA=   5.4  PHAS=   134.4  FOM=  0.68  TEST= 1
```

*FIG. 12A - 155*

```
INDE   5   57   26  FOBS=   66.0  SIGMA=   2.9  PHAS=    44.0  FOM=  0.82  TEST= 0
INDE   5   57   28  FOBS=   82.3  SIGMA=   2.4  PHAS=   -54.0  FOM=  0.79  TEST= 0
INDE   5   57   30  FOBS=   73.3  SIGMA=   2.7  PHAS=    95.4  FOM=  0.72  TEST= 0
INDE   5   57   32  FOBS=   46.9  SIGMA=   4.6  PHAS=   -94.2  FOM=  0.34  TEST= 0
INDE   5   57   34  FOBS=    0.0  SIGMA=  19.7  PHAS=     0.0  FOM=  0.00  TEST= 0
INDE   5   57   36  FOBS=   48.9  SIGMA=   4.9  PHAS=  -175.8  FOM=  0.62  TEST= 0
INDE   5   57   38  FOBS=   32.6  SIGMA=   8.5  PHAS=     9.2  FOM=  0.35  TEST= 0
INDE   5   57   40  FOBS=   71.1  SIGMA=   3.2  PHAS=   180.0  FOM=  0.89  TEST= 0
INDE   5   57   42  FOBS=   61.1  SIGMA=   3.5  PHAS=   -45.4  FOM=  0.59  TEST= 0
INDE   5   57   44  FOBS=   14.3  SIGMA=  17.2  PHAS=   -34.0  FOM=  0.11  TEST= 0
INDE   5   57   46  FOBS=   84.3  SIGMA=   2.7  PHAS=   -93.8  FOM=  0.84  TEST= 0
INDE   5   57   48  FOBS=   13.8  SIGMA=  16.2  PHAS=    26.1  FOM=  0.26  TEST= 0
INDE   5   57   50  FOBS=    0.0  SIGMA=  24.1  PHAS=     0.0  FOM=  0.00  TEST= 1
INDE   5   57   52  FOBS=   65.3  SIGMA=   5.2  PHAS=  -152.0  FOM=  0.62  TEST= 0
INDE   5   58    5  FOBS=    0.0  SIGMA=  22.5  PHAS=     0.0  FOM=  0.00  TEST= 0
INDE   5   58    7  FOBS=   72.7  SIGMA=   3.6  PHAS=    -0.2  FOM=  0.69  TEST= 0
INDE   5   58    9  FOBS=   76.1  SIGMA=   3.5  PHAS=   -91.2  FOM=  0.69  TEST= 0
INDE   5   58   11  FOBS=  101.5  SIGMA=   3.0  PHAS=   -90.9  FOM=  0.89  TEST= 0
INDE   5   58   13  FOBS=    3.3  SIGMA=  89.2  PHAS=   106.6  FOM=  0.04  TEST= 0
INDE   5   58   15  FOBS=   41.4  SIGMA=   4.0  PHAS=    61.7  FOM=  0.87  TEST= 0
INDE   5   58   17  FOBS=   87.6  SIGMA=   2.1  PHAS=   169.9  FOM=  0.89  TEST= 0
INDE   5   58   19  FOBS=    0.0  SIGMA=  17.6  PHAS=     0.0  FOM=  0.00  TEST= 0
INDE   5   58   21  FOBS=  112.4  SIGMA=   1.4  PHAS=   109.1  FOM=  0.80  TEST= 0
INDE   5   58   23  FOBS=   64.2  SIGMA=   2.5  PHAS=    86.3  FOM=  0.88  TEST= 0
INDE   5   58   25  FOBS=  102.8  SIGMA=   1.9  PHAS=   -26.9  FOM=  0.95  TEST= 0
INDE   5   58   27  FOBS=   92.7  SIGMA=   2.1  PHAS=   164.9  FOM=  0.88  TEST= 0
INDE   5   58   29  FOBS=   35.3  SIGMA=   5.6  PHAS=    45.4  FOM=  0.13  TEST= 0
INDE   5   58   31  FOBS=   32.9  SIGMA=   5.9  PHAS=   -47.1  FOM=  0.45  TEST= 0
INDE   5   58   33  FOBS=   10.9  SIGMA=  24.3  PHAS=  -100.7  FOM=  0.17  TEST= 0
INDE   5   58   35  FOBS=    2.7  SIGMA=  78.7  PHAS=    -0.1  FOM=  0.04  TEST= 0
INDE   5   58   37  FOBS=   60.5  SIGMA=   5.4  PHAS=    20.2  FOM=  0.21  TEST= 0
INDE   5   58   39  FOBS=   47.7  SIGMA=   6.8  PHAS=   122.6  FOM=  0.64  TEST= 1
INDE   5   58   41  FOBS=   36.7  SIGMA=   6.7  PHAS=   -86.9  FOM=  0.61  TEST= 0
INDE   5   58   43  FOBS=   85.7  SIGMA=   2.5  PHAS=  -172.1  FOM=  0.80  TEST= 0
INDE   5   58   45  FOBS=   41.4  SIGMA=   6.1  PHAS=     6.8  FOM=  0.01  TEST= 0
INDE   5   58   47  FOBS=   60.6  SIGMA=   3.7  PHAS=    76.2  FOM=  0.09  TEST= 1
INDE   5   58   49  FOBS=    0.0  SIGMA=  23.2  PHAS=     0.0  FOM=  0.00  TEST= 0
INDE   5   58   51  FOBS=   72.6  SIGMA=   4.8  PHAS=    16.9  FOM=  0.66  TEST= 0
INDE   5   59    6  FOBS=   35.4  SIGMA=   4.0  PHAS=    17.1  FOM=  0.32  TEST= 0
INDE   5   59    8  FOBS=   36.9  SIGMA=   8.0  PHAS=    29.0  FOM=  0.07  TEST= 0
INDE   5   59   10  FOBS=    0.0  SIGMA=  22.7  PHAS=     0.0  FOM=  0.00  TEST= 0
INDE   5   59   12  FOBS=   32.6  SIGMA=   7.9  PHAS=  -159.3  FOM=  0.61  TEST= 1
INDE   5   59   14  FOBS=   21.4  SIGMA=  11.9  PHAS=    33.6  FOM=  0.44  TEST= 0
INDE   5   59   16  FOBS=  107.8  SIGMA=   1.8  PHAS=    48.7  FOM=  0.90  TEST= 0
INDE   5   59   18  FOBS=    0.0  SIGMA=  17.6  PHAS=     0.0  FOM=  0.00  TEST= 0
INDE   5   59   20  FOBS=  120.5  SIGMA=   1.5  PHAS=    60.5  FOM=  0.93  TEST= 0
INDE   5   59   22  FOBS=   80.0  SIGMA=   2.2  PHAS=   -29.0  FOM=  0.84  TEST= 0
INDE   5   59   24  FOBS=   22.1  SIGMA=   9.2  PHAS=    -8.5  FOM=  0.03  TEST= 1
INDE   5   59   26  FOBS=   41.6  SIGMA=   4.6  PHAS=   -93.2  FOM=  0.53  TEST= 0
INDE   5   59   28  FOBS=  117.5  SIGMA=   1.7  PHAS=     6.6  FOM=  0.82  TEST= 0
INDE   5   59   30  FOBS=   46.8  SIGMA=   4.6  PHAS=   111.5  FOM=  0.69  TEST= 0
INDE   5   59   32  FOBS=   54.8  SIGMA=   4.3  PHAS=   179.0  FOM=  0.78  TEST= 0
INDE   5   59   34  FOBS=   77.6  SIGMA=   3.1  PHAS=  -114.7  FOM=  0.91  TEST= 0
INDE   5   59   36  FOBS=   89.7  SIGMA=   2.7  PHAS=   -81.5  FOM=  0.89  TEST= 0
INDE   5   59   38  FOBS=   96.2  SIGMA=   3.5  PHAS=    -5.8  FOM=  0.93  TEST= 0
INDE   5   59   40  FOBS=   92.7  SIGMA=   3.5  PHAS=   176.0  FOM=  0.94  TEST= 0
INDE   5   59   42  FOBS=   35.8  SIGMA=   6.9  PHAS=  -118.4  FOM=  0.22  TEST= 0
INDE   5   59   44  FOBS=   39.6  SIGMA=   5.4  PHAS=  -147.6  FOM=  0.29  TEST= 1
INDE   5   59   46  FOBS=   40.3  SIGMA=   6.3  PHAS=  -102.7  FOM=  0.81  TEST= 0
INDE   5   59   48  FOBS=   29.0  SIGMA=   9.4  PHAS=    -2.6  FOM=  0.75  TEST= 0
INDE   5   59   50  FOBS=   37.4  SIGMA=   9.2  PHAS=     2.2  FOM=  0.61  TEST= 0
INDE   5   60    5  FOBS=   94.6  SIGMA=   2.8  PHAS=   161.6  FOM=  0.52  TEST= 0
INDE   5   60    7  FOBS=   50.9  SIGMA=   5.0  PHAS=   -16.9  FOM=  0.55  TEST= 0
INDE   5   60    9  FOBS=  118.6  SIGMA=   2.2  PHAS=    15.3  FOM=  0.88  TEST= 0
INDE   5   60   11  FOBS=  128.6  SIGMA=   2.1  PHAS=   -19.3  FOM=  0.96  TEST= 0
INDE   5   60   13  FOBS=  105.6  SIGMA=   2.5  PHAS=    36.1  FOM=  0.87  TEST= 0
INDE   5   60   15  FOBS=   76.7  SIGMA=   3.3  PHAS=   -52.3  FOM=  0.53  TEST= 0
INDE   5   60   17  FOBS=   71.9  SIGMA=   2.7  PHAS=   -69.6  FOM=  0.35  TEST= 0
INDE   5   60   19  FOBS=   44.1  SIGMA=   4.1  PHAS=    20.6  FOM=  0.82  TEST= 0
INDE   5   60   21  FOBS=  102.0  SIGMA=   1.7  PHAS=  -124.9  FOM=  0.92  TEST= 0
```

*FIG. 12A - 156*

```
INDE  5  60  23 FOBS=   92.3 SIGMA=  2.0 PHAS=   93.6 FOM= 0.57 TEST= 0
INDE  5  60  25 FOBS=   56.7 SIGMA=  3.3 PHAS=  -29.4 FOM= 0.35 TEST= 1
INDE  5  60  27 FOBS=   92.0 SIGMA=  2.5 PHAS=  168.9 FOM= 0.89 TEST= 0
INDE  5  60  29 FOBS=   36.0 SIGMA=  6.4 PHAS=    0.2 FOM= 0.32 TEST= 0
INDE  5  60  31 FOBS=   57.7 SIGMA=  4.1 PHAS=   76.1 FOM= 0.84 TEST= 0
INDE  5  60  33 FOBS=   32.7 SIGMA=  8.5 PHAS= -101.5 FOM= 0.14 TEST= 1
INDE  5  60  35 FOBS=  125.2 SIGMA=  2.4 PHAS= -173.5 FOM= 0.94 TEST= 0
INDE  5  60  37 FOBS=  132.7 SIGMA=  2.2 PHAS=  -91.3 FOM= 0.96 TEST= 0
INDE  5  60  39 FOBS=  108.0 SIGMA=  3.1 PHAS=   83.7 FOM= 0.96 TEST= 0
INDE  5  60  41 FOBS=   52.5 SIGMA=  5.3 PHAS=  131.4 FOM= 0.57 TEST= 0
INDE  5  60  43 FOBS=   44.2 SIGMA=  4.9 PHAS=    0.8 FOM= 0.49 TEST= 0
INDE  5  60  45 FOBS=   55.9 SIGMA=  4.1 PHAS=  149.9 FOM= 0.87 TEST= 0
INDE  5  60  47 FOBS=   27.4 SIGMA= 12.5 PHAS= -169.5 FOM= 0.37 TEST= 0
INDE  5  60  49 FOBS=   41.0 SIGMA=  8.6 PHAS=  -76.9 FOM= 0.72 TEST= 0
INDE  5  61   6 FOBS=  155.1 SIGMA=  1.8 PHAS= -111.0 FOM= 0.96 TEST= 0
INDE  5  61   8 FOBS=  114.3 SIGMA=  2.4 PHAS=  158.0 FOM= 0.90 TEST= 0
INDE  5  61  10 FOBS=   90.8 SIGMA=  2.9 PHAS=  -86.2 FOM= 0.91 TEST= 0
INDE  5  61  12 FOBS=   70.8 SIGMA=  3.6 PHAS=  -54.3 FOM= 0.91 TEST= 0
INDE  5  61  14 FOBS=   79.8 SIGMA=  3.2 PHAS=  -53.0 FOM= 0.87 TEST= 0
INDE  5  61  16 FOBS=    0.0 SIGMA= 19.9 PHAS=    0.0 FOM= 0.00 TEST= 1
INDE  5  61  18 FOBS=  153.9 SIGMA=  1.4 PHAS=  -28.8 FOM= 0.93 TEST= 0
INDE  5  61  20 FOBS=  146.9 SIGMA=  1.4 PHAS=  126.1 FOM= 0.93 TEST= 0
INDE  5  61  22 FOBS=  116.1 SIGMA=  1.9 PHAS= -128.2 FOM= 0.88 TEST= 0
INDE  5  61  24 FOBS=   48.6 SIGMA=  4.7 PHAS= -142.1 FOM= 0.38 TEST= 0
INDE  5  61  26 FOBS=    0.0 SIGMA= 24.8 PHAS=    0.0 FOM= 0.00 TEST= 0
INDE  5  61  28 FOBS=   71.3 SIGMA=  3.9 PHAS=   71.3 FOM= 0.85 TEST= 0
INDE  5  61  30 FOBS=   48.0 SIGMA=  5.8 PHAS=   22.3 FOM= 0.77 TEST= 0
INDE  5  61  32 FOBS=   73.5 SIGMA=  3.8 PHAS=   73.5 FOM= 0.81 TEST= 0
INDE  5  61  34 FOBS=   46.9 SIGMA=  6.0 PHAS= -129.0 FOM= 0.83 TEST= 0
INDE  5  61  36 FOBS=  119.0 SIGMA=  2.5 PHAS=  178.3 FOM= 0.94 TEST= 0
INDE  5  61  38 FOBS=   67.2 SIGMA=  4.2 PHAS= -103.8 FOM= 0.90 TEST= 0
INDE  5  61  40 FOBS=   77.7 SIGMA=  4.3 PHAS=  -68.0 FOM= 0.87 TEST= 0
INDE  5  61  42 FOBS=   42.1 SIGMA=  6.0 PHAS=  157.4 FOM= 0.60 TEST= 0
INDE  5  61  44 FOBS=   62.9 SIGMA=  3.8 PHAS=  -94.1 FOM= 0.89 TEST= 0
INDE  5  61  46 FOBS=   18.9 SIGMA= 19.4 PHAS=   -7.4 FOM= 0.28 TEST= 0
INDE  5  62   5 FOBS=   88.2 SIGMA=  2.0 PHAS= -158.7 FOM= 0.91 TEST= 0
INDE  5  62   7 FOBS=  152.3 SIGMA=  1.1 PHAS=   77.5 FOM= 0.96 TEST= 0
INDE  5  62   9 FOBS=  212.7 SIGMA=  1.4 PHAS=   79.6 FOM= 0.98 TEST= 0
INDE  5  62  11 FOBS=   45.3 SIGMA=  5.7 PHAS=  -85.1 FOM= 0.06 TEST= 1
INDE  5  62  13 FOBS=  125.0 SIGMA=  2.1 PHAS= -132.5 FOM= 0.93 TEST= 0
INDE  5  62  15 FOBS=   30.5 SIGMA=  8.0 PHAS= -109.5 FOM= 0.18 TEST= 0
INDE  5  62  17 FOBS=   22.1 SIGMA=  9.1 PHAS= -154.9 FOM= 0.39 TEST= 0
INDE  5  62  19 FOBS=   73.5 SIGMA=  3.4 PHAS=  -56.8 FOM= 0.79 TEST= 0
INDE  5  62  21 FOBS=   42.2 SIGMA=  4.9 PHAS=  145.6 FOM= 0.65 TEST= 0
INDE  5  62  23 FOBS=   41.4 SIGMA=  5.2 PHAS=  132.4 FOM= 0.71 TEST= 0
INDE  5  62  25 FOBS=    0.0 SIGMA= 21.3 PHAS=    0.0 FOM= 0.00 TEST= 1
INDE  5  62  27 FOBS=  128.1 SIGMA=  1.9 PHAS=   37.5 FOM= 0.95 TEST= 0
INDE  5  62  29 FOBS=   33.7 SIGMA=  8.1 PHAS=  -79.0 FOM= 0.40 TEST= 0
INDE  5  62  31 FOBS=   74.0 SIGMA=  3.9 PHAS=   16.6 FOM= 0.67 TEST= 0
INDE  5  62  33 FOBS=    0.0 SIGMA= 25.8 PHAS=    0.0 FOM= 0.00 TEST= 0
INDE  5  62  35 FOBS=   73.3 SIGMA=  3.9 PHAS=  118.7 FOM= 0.36 TEST= 1
INDE  5  62  37 FOBS=  106.6 SIGMA=  2.7 PHAS=   98.2 FOM= 0.96 TEST= 0
INDE  5  62  39 FOBS=   62.8 SIGMA=  4.5 PHAS=   98.6 FOM= 0.90 TEST= 0
INDE  5  62  41 FOBS=   42.8 SIGMA=  7.6 PHAS=  115.4 FOM= 0.85 TEST= 0
INDE  5  62  43 FOBS=    0.0 SIGMA= 25.6 PHAS=    0.0 FOM= 0.00 TEST= 0
INDE  5  62  45 FOBS=   83.0 SIGMA=  4.4 PHAS= -172.7 FOM= 0.96 TEST= 0
INDE  5  63   6 FOBS=   44.3 SIGMA=  5.7 PHAS=  145.7 FOM= 0.25 TEST= 1
INDE  5  63   8 FOBS=  157.8 SIGMA=  1.7 PHAS=  -48.9 FOM= 0.96 TEST= 0
INDE  5  63  10 FOBS=  109.7 SIGMA=  3.4 PHAS=   20.7 FOM= 0.94 TEST= 0
INDE  5  63  12 FOBS=  133.0 SIGMA=  2.9 PHAS=  138.1 FOM= 0.95 TEST= 0
INDE  5  63  14 FOBS=   36.3 SIGMA=  9.7 PHAS=  154.8 FOM= 0.32 TEST= 0
INDE  5  63  16 FOBS=   11.7 SIGMA= 29.9 PHAS=  176.3 FOM= 0.29 TEST= 0
INDE  5  63  18 FOBS=   63.5 SIGMA=  3.6 PHAS=  117.6 FOM= 0.66 TEST= 0
INDE  5  63  20 FOBS=   32.5 SIGMA=  6.1 PHAS=  172.1 FOM= 0.39 TEST= 0
INDE  5  63  22 FOBS=   67.1 SIGMA=  3.1 PHAS= -176.3 FOM= 0.41 TEST= 0
INDE  5  63  24 FOBS=   97.7 SIGMA=  2.3 PHAS=   97.9 FOM= 0.90 TEST= 0
INDE  5  63  26 FOBS=   92.2 SIGMA=  2.6 PHAS=  -61.1 FOM= 0.94 TEST= 0
INDE  5  63  28 FOBS=    0.0 SIGMA= 21.2 PHAS=    0.0 FOM= 0.00 TEST= 0
INDE  5  63  30 FOBS=    0.0 SIGMA= 23.4 PHAS=    0.0 FOM= 0.00 TEST= 0
INDE  5  63  32 FOBS=    0.0 SIGMA= 23.8 PHAS=    0.0 FOM= 0.00 TEST= 0
```

*FIG. 12A - 157*

```
INDE  5  63  34 FOBS=  48.7 SIGMA=  5.8 PHAS=  -29.1 FOM= 0.46 TEST= 0
INDE  5  63  36 FOBS=  80.2 SIGMA=  3.6 PHAS=    5.0 FOM= 0.94 TEST= 0
INDE  5  63  38 FOBS=   0.0 SIGMA= 23.7 PHAS=    0.0 FOM= 0.00 TEST= 0
INDE  5  63  40 FOBS=  49.9 SIGMA=  5.7 PHAS=  -25.5 FOM= 0.85 TEST= 0
INDE  5  63  42 FOBS=   0.0 SIGMA= 25.8 PHAS=    0.0 FOM= 0.00 TEST= 0
INDE  5  63  44 FOBS=  91.3 SIGMA=  4.0 PHAS=   96.7 FOM= 0.87 TEST= 0
INDE  5  64   5 FOBS= 102.0 SIGMA=  2.2 PHAS=  168.1 FOM= 0.68 TEST= 0
INDE  5  64   7 FOBS=  47.9 SIGMA=  5.9 PHAS= -145.8 FOM= 0.75 TEST= 0
INDE  5  64   9 FOBS=   0.0 SIGMA= 23.8 PHAS=    0.0 FOM= 0.00 TEST= 0
INDE  5  64  11 FOBS=  72.8 SIGMA=  4.9 PHAS=   25.9 FOM= 0.89 TEST= 0
INDE  5  64  13 FOBS=  64.0 SIGMA=  5.6 PHAS=  -75.5 FOM= 0.74 TEST= 0
INDE  5  64  15 FOBS=  51.2 SIGMA=  6.9 PHAS=  175.3 FOM= 0.25 TEST= 0
INDE  5  64  17 FOBS=  62.2 SIGMA=  5.7 PHAS=  141.8 FOM= 0.74 TEST= 0
INDE  5  64  19 FOBS=  34.4 SIGMA=  6.7 PHAS=  126.1 FOM= 0.27 TEST= 0
INDE  5  64  21 FOBS=  48.9 SIGMA=  4.1 PHAS=    2.5 FOM= 0.66 TEST= 0
INDE  5  64  23 FOBS=  45.3 SIGMA=  4.7 PHAS=  -87.7 FOM= 0.57 TEST= 0
INDE  5  64  25 FOBS=  78.0 SIGMA=  2.9 PHAS=  124.9 FOM= 0.67 TEST= 0
INDE  5  64  27 FOBS=  86.6 SIGMA=  2.7 PHAS=  167.8 FOM= 0.85 TEST= 0
INDE  5  64  29 FOBS=  88.8 SIGMA=  2.6 PHAS=  173.9 FOM= 0.86 TEST= 0
INDE  5  64  31 FOBS=  81.8 SIGMA=  3.5 PHAS=  111.2 FOM= 0.87 TEST= 0
INDE  5  64  33 FOBS=  90.0 SIGMA=  3.3 PHAS=  -16.7 FOM= 0.88 TEST= 0
INDE  5  64  35 FOBS=  62.5 SIGMA=  4.6 PHAS=  -99.6 FOM= 0.72 TEST= 0
INDE  5  64  37 FOBS=  13.4 SIGMA= 21.3 PHAS=   14.9 FOM= 0.09 TEST= 0
INDE  5  64  39 FOBS=   0.0 SIGMA= 23.9 PHAS=    0.0 FOM= 0.00 TEST= 0
INDE  5  64  41 FOBS=  58.7 SIGMA=  5.0 PHAS=  105.4 FOM= 0.87 TEST= 0
INDE  5  64  43 FOBS=  55.7 SIGMA=  6.2 PHAS=   62.7 FOM= 0.88 TEST= 0
INDE  5  65   6 FOBS=  82.8 SIGMA=  3.5 PHAS=   76.9 FOM= 0.93 TEST= 0
INDE  5  65   8 FOBS=  85.0 SIGMA=  1.9 PHAS= -158.8 FOM= 0.72 TEST= 0
INDE  5  65  10 FOBS=  83.0 SIGMA=  4.3 PHAS=    7.3 FOM= 0.86 TEST= 0
INDE  5  65  12 FOBS=  64.8 SIGMA=  5.5 PHAS= -160.7 FOM= 0.74 TEST= 0
INDE  5  65  14 FOBS=  52.8 SIGMA=  6.7 PHAS=  136.2 FOM= 0.51 TEST= 0
INDE  5  65  16 FOBS=  49.4 SIGMA=  7.1 PHAS=    1.2 FOM= 0.26 TEST= 0
INDE  5  65  18 FOBS=  32.2 SIGMA=  6.7 PHAS=  -17.4 FOM= 0.72 TEST= 0
INDE  5  65  20 FOBS=   0.0 SIGMA= 23.3 PHAS=    0.0 FOM= 0.00 TEST= 0
INDE  5  65  22 FOBS=  55.2 SIGMA=  3.7 PHAS=  172.9 FOM= 0.63 TEST= 0
INDE  5  65  24 FOBS=  26.3 SIGMA= 11.7 PHAS=   36.2 FOM= 0.41 TEST= 0
INDE  5  65  26 FOBS=  48.8 SIGMA=  5.6 PHAS= -127.6 FOM= 0.23 TEST= 1
INDE  5  65  28 FOBS=  99.8 SIGMA=  2.4 PHAS=   98.4 FOM= 0.92 TEST= 0
INDE  5  65  30 FOBS= 104.7 SIGMA=  2.3 PHAS=   44.0 FOM= 0.94 TEST= 0
INDE  5  65  32 FOBS= 112.8 SIGMA=  2.6 PHAS=  -13.0 FOM= 0.92 TEST= 0
INDE  5  65  34 FOBS=  14.9 SIGMA= 19.4 PHAS= -143.1 FOM= 0.18 TEST= 0
INDE  5  65  36 FOBS=   0.0 SIGMA= 26.1 PHAS=    0.0 FOM= 0.00 TEST= 0
INDE  5  65  38 FOBS=  34.0 SIGMA=  8.5 PHAS= -163.8 FOM= 0.63 TEST= 0
INDE  5  65  40 FOBS=  84.9 SIGMA=  3.5 PHAS=   33.2 FOM= 0.79 TEST= 0
INDE  5  65  42 FOBS= 100.2 SIGMA=  2.7 PHAS=    3.2 FOM= 0.93 TEST= 0
INDE  5  66   5 FOBS=  91.0 SIGMA=  2.7 PHAS= -143.7 FOM= 0.88 TEST= 0
INDE  5  66   7 FOBS=   0.0 SIGMA= 26.3 PHAS=    0.0 FOM= 0.00 TEST= 0
INDE  5  66   9 FOBS=  97.1 SIGMA=  3.7 PHAS=   75.4 FOM= 0.86 TEST= 0
INDE  5  66  11 FOBS=   9.5 SIGMA= 36.4 PHAS= -157.2 FOM= 0.15 TEST= 0
INDE  5  66  13 FOBS=  75.9 SIGMA=  4.7 PHAS=  164.6 FOM= 0.81 TEST= 0
INDE  5  66  15 FOBS= 134.3 SIGMA=  2.8 PHAS= -119.6 FOM= 0.91 TEST= 0
INDE  5  66  17 FOBS=  53.3 SIGMA=  6.6 PHAS= -108.8 FOM= 0.82 TEST= 0
INDE  5  66  19 FOBS=   0.0 SIGMA= 22.5 PHAS=    0.0 FOM= 0.00 TEST= 0
INDE  5  66  21 FOBS=   0.0 SIGMA= 22.0 PHAS=    0.0 FOM= 0.00 TEST= 0
INDE  5  66  23 FOBS=   0.0 SIGMA= 20.3 PHAS=    0.0 FOM= 0.00 TEST= 1
INDE  5  66  25 FOBS=  36.7 SIGMA=  7.2 PHAS=  -97.3 FOM= 0.11 TEST= 0
INDE  5  66  27 FOBS=  52.3 SIGMA=  5.3 PHAS=  -20.7 FOM= 0.29 TEST= 0
INDE  5  66  29 FOBS=  54.7 SIGMA=  4.3 PHAS= -109.4 FOM= 0.78 TEST= 0
INDE  5  66  31 FOBS=  90.9 SIGMA=  2.7 PHAS=  -84.4 FOM= 0.95 TEST= 0
INDE  5  66  33 FOBS=   0.0 SIGMA= 26.5 PHAS=    0.0 FOM= 0.00 TEST= 0
INDE  5  66  35 FOBS=  29.4 SIGMA= 12.3 PHAS=  155.6 FOM= 0.34 TEST= 0
INDE  5  66  37 FOBS=  63.2 SIGMA=  4.7 PHAS=  100.4 FOM= 0.52 TEST= 0
INDE  5  66  39 FOBS=  71.9 SIGMA=  4.2 PHAS=   81.1 FOM= 0.80 TEST= 0
INDE  5  67   6 FOBS=  26.7 SIGMA= 13.1 PHAS=   56.7 FOM= 0.65 TEST= 0
INDE  5  67   8 FOBS= 109.9 SIGMA=  4.9 PHAS=  140.7 FOM= 0.93 TEST= 0
INDE  5  67  10 FOBS=  40.9 SIGMA=  8.4 PHAS= -150.4 FOM= 0.50 TEST= 0
INDE  5  67  12 FOBS=   0.0 SIGMA= 26.4 PHAS=    0.0 FOM= 0.00 TEST= 0
INDE  5  67  14 FOBS= 135.5 SIGMA=  2.8 PHAS=  121.4 FOM= 0.94 TEST= 0
INDE  5  67  16 FOBS=  92.4 SIGMA=  3.9 PHAS= -178.4 FOM= 0.93 TEST= 0
INDE  5  67  18 FOBS=  82.2 SIGMA=  4.4 PHAS= -158.6 FOM= 0.90 TEST= 0
```

*FIG. 12A - 158*

```
INDE  5  67  20  FOBS=    0.0  SIGMA=  21.3  PHAS=     0.0  FOM=  0.00  TEST= 0
INDE  5  67  22  FOBS=    0.0  SIGMA=  20.3  PHAS=     0.0  FOM=  0.00  TEST= 0
INDE  5  67  24  FOBS=   99.3  SIGMA=   2.2  PHAS=   -28.4  FOM=  0.92  TEST= 0
INDE  5  67  26  FOBS=   83.5  SIGMA=   2.8  PHAS=   135.2  FOM=  0.93  TEST= 0
INDE  5  67  28  FOBS=   54.4  SIGMA=   5.2  PHAS=   177.8  FOM=  0.85  TEST= 0
INDE  5  67  30  FOBS=    0.0  SIGMA=  21.9  PHAS=     0.0  FOM=  0.00  TEST= 0
INDE  5  67  32  FOBS=   33.9  SIGMA=   7.1  PHAS=   106.0  FOM=  0.74  TEST= 0
INDE  5  67  34  FOBS=   21.2  SIGMA=  13.6  PHAS=   -51.5  FOM=  0.09  TEST= 0
INDE  5  67  36  FOBS=   23.2  SIGMA=  12.8  PHAS=    50.5  FOM=  0.25  TEST= 0
INDE  5  67  38  FOBS=    0.0  SIGMA=  26.4  PHAS=     0.0  FOM=  0.00  TEST= 0
INDE  5  68   5  FOBS=   59.6  SIGMA=   6.2  PHAS=  -114.8  FOM=  0.73  TEST= 0
INDE  5  68   9  FOBS=   93.8  SIGMA=   2.0  PHAS=    61.6  FOM=  0.91  TEST= 0
INDE  5  68  11  FOBS=    0.0  SIGMA=  31.8  PHAS=     0.0  FOM=  0.00  TEST= 0
INDE  5  68  13  FOBS=    0.0  SIGMA=  31.7  PHAS=     0.0  FOM=  0.00  TEST= 0
INDE  5  68  15  FOBS=   44.2  SIGMA=   7.9  PHAS=  -138.6  FOM=  0.42  TEST= 0
INDE  5  68  17  FOBS=   79.2  SIGMA=   4.6  PHAS=    71.6  FOM=  0.86  TEST= 0
INDE  5  68  19  FOBS=   55.9  SIGMA=   6.3  PHAS=    85.4  FOM=  0.72  TEST= 0
INDE  5  68  21  FOBS=    0.0  SIGMA=  21.5  PHAS=     0.0  FOM=  0.00  TEST= 0
INDE  5  68  23  FOBS=   55.2  SIGMA=   3.9  PHAS=   -59.3  FOM=  0.84  TEST= 0
INDE  5  68  25  FOBS=   65.1  SIGMA=   3.4  PHAS=    48.6  FOM=  0.84  TEST= 0
INDE  5  68  27  FOBS=   54.6  SIGMA=   4.3  PHAS=    92.9  FOM=  0.81  TEST= 0
INDE  5  68  29  FOBS=    0.0  SIGMA=  23.8  PHAS=     0.0  FOM=  0.00  TEST= 0
INDE  5  68  31  FOBS=   69.5  SIGMA=   3.6  PHAS=  -141.5  FOM=  0.08  TEST= 1
INDE  5  68  33  FOBS=   41.7  SIGMA=   5.9  PHAS=    56.9  FOM=  0.50  TEST= 0
INDE  5  68  35  FOBS=    0.0  SIGMA=  24.3  PHAS=     0.0  FOM=  0.00  TEST= 0
INDE  5  68  37  FOBS=   21.7  SIGMA=  17.3  PHAS=  -174.7  FOM=  0.00  TEST= 1
INDE  5  69   6  FOBS=   50.2  SIGMA=   6.8  PHAS=   -54.8  FOM=  0.69  TEST= 0
INDE  5  69  16  FOBS=   45.6  SIGMA=  10.8  PHAS=   167.5  FOM=  0.72  TEST= 0
INDE  5  69  18  FOBS=   23.4  SIGMA=  21.0  PHAS=  -106.7  FOM=  0.06  TEST= 0
INDE  5  69  20  FOBS=   67.9  SIGMA=   5.2  PHAS=   -20.4  FOM=  0.13  TEST= 1
INDE  5  69  22  FOBS=   65.6  SIGMA=   3.7  PHAS=  -157.4  FOM=  0.69  TEST= 0
INDE  5  69  24  FOBS=   50.3  SIGMA=   4.3  PHAS=   -28.2  FOM=  0.78  TEST= 0
INDE  5  69  26  FOBS=   75.8  SIGMA=   3.0  PHAS=  -139.8  FOM=  0.86  TEST= 0
INDE  5  69  28  FOBS=   43.9  SIGMA=   5.4  PHAS=  -156.2  FOM=  0.67  TEST= 0
INDE  5  69  30  FOBS=    0.0  SIGMA=  24.2  PHAS=     0.0  FOM=  0.00  TEST= 0
INDE  5  69  32  FOBS=   70.8  SIGMA=   3.5  PHAS=    53.3  FOM=  0.85  TEST= 0
INDE  5  69  34  FOBS=    0.0  SIGMA=  24.0  PHAS=     0.0  FOM=  0.00  TEST= 1
INDE  5  70   5  FOBS=   61.4  SIGMA=   5.7  PHAS=   152.1  FOM=  0.87  TEST= 0
INDE  5  70   7  FOBS=   54.6  SIGMA=   6.5  PHAS=  -160.7  FOM=  0.25  TEST= 0
INDE  5  70  21  FOBS=   45.4  SIGMA=   5.8  PHAS=  -142.5  FOM=  0.34  TEST= 0
INDE  5  70  23  FOBS=    0.0  SIGMA=  24.0  PHAS=     0.0  FOM=  0.00  TEST= 1
INDE  5  70  25  FOBS=   54.2  SIGMA=   4.0  PHAS=    88.9  FOM=  0.59  TEST= 0
INDE  5  70  27  FOBS=   76.1  SIGMA=   3.0  PHAS=   125.7  FOM=  0.91  TEST= 0
INDE  5  70  29  FOBS=    0.0  SIGMA=  21.9  PHAS=     0.0  FOM=  0.00  TEST= 0
INDE  5  70  31  FOBS=   40.9  SIGMA=   7.2  PHAS=   -29.5  FOM=  0.83  TEST= 0
INDE  5  70  33  FOBS=   25.6  SIGMA=  10.0  PHAS=    29.9  FOM=  0.18  TEST= 0
INDE  5  71   6  FOBS=   34.3  SIGMA=  10.8  PHAS=    59.5  FOM=  0.52  TEST= 0
INDE  5  71  10  FOBS=   36.6  SIGMA=   5.0  PHAS=   125.2  FOM=  0.25  TEST= 0
INDE  5  71  22  FOBS=   47.0  SIGMA=   6.7  PHAS=   -80.8  FOM=  0.41  TEST= 0
INDE  5  71  24  FOBS=   23.5  SIGMA=  15.3  PHAS=  -103.3  FOM=  0.39  TEST= 0
INDE  5  71  26  FOBS=   26.6  SIGMA=  12.1  PHAS=   146.8  FOM=  0.09  TEST= 1
INDE  5  71  28  FOBS=    0.0  SIGMA=  22.7  PHAS=     0.0  FOM=  0.00  TEST= 0
INDE  5  71  30  FOBS=   26.7  SIGMA=   9.4  PHAS=   -93.4  FOM=  0.54  TEST= 0
INDE  5  72   5  FOBS=    0.0  SIGMA=  26.3  PHAS=     0.0  FOM=  0.00  TEST= 0
INDE  5  72   7  FOBS=   85.8  SIGMA=   4.1  PHAS=   -52.5  FOM=  0.94  TEST= 0
INDE  5  72  23  FOBS=   15.8  SIGMA=  20.8  PHAS=   146.9  FOM=  0.15  TEST= 0
INDE  5  72  25  FOBS=   48.4  SIGMA=   5.8  PHAS=   161.1  FOM=  0.22  TEST= 1
INDE  5  72  27  FOBS=    0.0  SIGMA=  24.2  PHAS=     0.0  FOM=  0.00  TEST= 0
INDE  5  73   6  FOBS=    0.0  SIGMA=  26.4  PHAS=     0.0  FOM=  0.00  TEST= 0
INDE  5  73   8  FOBS=   52.0  SIGMA=   6.9  PHAS=  -137.4  FOM=  0.70  TEST= 0
INDE  5  73  24  FOBS=    0.0  SIGMA=  26.3  PHAS=     0.0  FOM=  0.00  TEST= 0
INDE  5  73  26  FOBS=   36.6  SIGMA=   7.9  PHAS=   -38.1  FOM=  0.25  TEST= 0
INDE  5  74   5  FOBS=   54.6  SIGMA=   6.1  PHAS=     7.0  FOM=  0.78  TEST= 0
INDE  5  74   7  FOBS=   29.4  SIGMA=  12.7  PHAS=  -105.9  FOM=  0.39  TEST= 0
INDE  5  74  11  FOBS=    0.0  SIGMA=  18.7  PHAS=     0.0  FOM=  0.00  TEST= 0
INDE  5  75   6  FOBS=   79.4  SIGMA=   4.5  PHAS=   122.3  FOM=  0.80  TEST= 0
INDE  5  75   8  FOBS=    0.0  SIGMA=  27.1  PHAS=     0.0  FOM=  0.00  TEST= 0
INDE  5  76   5  FOBS=    0.0  SIGMA=  26.2  PHAS=     0.0  FOM=  0.00  TEST= 0
INDE  5  76   7  FOBS=    0.0  SIGMA=  26.9  PHAS=     0.0  FOM=  0.00  TEST= 1
INDE  5  76   9  FOBS=  102.8  SIGMA=   3.8  PHAS=   124.4  FOM=  0.91  TEST= 0
```

*FIG. 12A - 159*

| | | | | | | | | | | | | |
|---|---|---|---|---|---|---|---|---|---|---|---|---|
| INDE | 5 | 77 | 6 | FOBS= | 54.0 | SIGMA= | 6.5 | PHAS= | 108.7 | FOM= | 0.38 | TEST= 0 |
| INDE | 5 | 77 | 8 | FOBS= | 73.6 | SIGMA= | 5.4 | PHAS= | -105.0 | FOM= | 0.02 | TEST= 1 |
| INDE | 6 | 7 | 17 | FOBS= | 143.5 | SIGMA= | 0.5 | PHAS= | 149.0 | FOM= | 0.91 | TEST= 0 |
| INDE | 6 | 7 | 19 | FOBS= | 125.9 | SIGMA= | 0.5 | PHAS= | 16.6 | FOM= | 0.92 | TEST= 0 |
| INDE | 6 | 7 | 21 | FOBS= | 183.9 | SIGMA= | 0.5 | PHAS= | 119.0 | FOM= | 0.73 | TEST= 1 |
| INDE | 6 | 7 | 23 | FOBS= | 194.3 | SIGMA= | 0.5 | PHAS= | -31.3 | FOM= | 0.97 | TEST= 0 |
| INDE | 6 | 7 | 25 | FOBS= | 100.5 | SIGMA= | 0.8 | PHAS= | 72.6 | FOM= | 0.94 | TEST= 0 |
| INDE | 6 | 7 | 27 | FOBS= | 93.8 | SIGMA= | 1.1 | PHAS= | 97.0 | FOM= | 0.99 | TEST= 0 |
| INDE | 6 | 7 | 29 | FOBS= | 74.9 | SIGMA= | 1.4 | PHAS= | -151.8 | FOM= | 0.99 | TEST= 0 |
| INDE | 6 | 7 | 31 | FOBS= | 168.6 | SIGMA= | 0.8 | PHAS= | 108.8 | FOM= | 0.95 | TEST= 1 |
| INDE | 6 | 7 | 33 | FOBS= | 304.7 | SIGMA= | 0.9 | PHAS= | 31.9 | FOM= | 0.97 | TEST= 0 |
| INDE | 6 | 7 | 35 | FOBS= | 103.7 | SIGMA= | 1.2 | PHAS= | -58.9 | FOM= | 0.92 | TEST= 0 |
| INDE | 6 | 7 | 37 | FOBS= | 281.7 | SIGMA= | 0.7 | PHAS= | -113.7 | FOM= | 0.94 | TEST= 0 |
| INDE | 6 | 7 | 39 | FOBS= | 124.5 | SIGMA= | 1.2 | PHAS= | 103.9 | FOM= | 0.76 | TEST= 0 |
| INDE | 6 | 7 | 41 | FOBS= | 261.2 | SIGMA= | 0.8 | PHAS= | -153.5 | FOM= | 0.96 | TEST= 0 |
| INDE | 6 | 7 | 43 | FOBS= | 249.5 | SIGMA= | 0.9 | PHAS= | 38.5 | FOM= | 0.94 | TEST= 0 |
| INDE | 6 | 7 | 45 | FOBS= | 86.3 | SIGMA= | 2.5 | PHAS= | -87.8 | FOM= | 0.88 | TEST= 0 |
| INDE | 6 | 7 | 47 | FOBS= | 57.7 | SIGMA= | 4.0 | PHAS= | -157.3 | FOM= | 0.77 | TEST= 0 |
| INDE | 6 | 7 | 49 | FOBS= | 269.0 | SIGMA= | 0.9 | PHAS= | 97.1 | FOM= | 0.95 | TEST= 0 |
| INDE | 6 | 7 | 51 | FOBS= | 167.9 | SIGMA= | 1.5 | PHAS= | 95.8 | FOM= | 0.82 | TEST= 0 |
| INDE | 6 | 7 | 53 | FOBS= | 130.9 | SIGMA= | 1.5 | PHAS= | -150.2 | FOM= | 0.40 | TEST= 1 |
| INDE | 6 | 7 | 55 | FOBS= | 149.0 | SIGMA= | 1.4 | PHAS= | 142.5 | FOM= | 0.91 | TEST= 0 |
| INDE | 6 | 7 | 57 | FOBS= | 107.4 | SIGMA= | 2.5 | PHAS= | 36.1 | FOM= | 0.85 | TEST= 0 |
| INDE | 6 | 7 | 59 | FOBS= | 53.3 | SIGMA= | 4.8 | PHAS= | -129.4 | FOM= | 0.33 | TEST= 0 |
| INDE | 6 | 7 | 61 | FOBS= | 61.3 | SIGMA= | 4.3 | PHAS= | 151.8 | FOM= | 0.83 | TEST= 0 |
| INDE | 6 | 7 | 63 | FOBS= | 37.3 | SIGMA= | 6.6 | PHAS= | 84.4 | FOM= | 0.46 | TEST= 0 |
| INDE | 6 | 7 | 65 | FOBS= | 46.2 | SIGMA= | 7.7 | PHAS= | 13.4 | FOM= | 0.03 | TEST= 1 |
| INDE | 6 | 7 | 67 | FOBS= | 88.7 | SIGMA= | 4.3 | PHAS= | 30.0 | FOM= | 0.83 | TEST= 0 |
| INDE | 6 | 7 | 69 | FOBS= | 84.2 | SIGMA= | 4.5 | PHAS= | 150.0 | FOM= | 0.63 | TEST= 0 |
| INDE | 6 | 7 | 71 | FOBS= | 41.9 | SIGMA= | 8.7 | PHAS= | -38.2 | FOM= | 0.58 | TEST= 0 |
| INDE | 6 | 7 | 73 | FOBS= | 97.3 | SIGMA= | 4.1 | PHAS= | 32.6 | FOM= | 0.86 | TEST= 0 |
| INDE | 6 | 7 | 75 | FOBS= | 27.7 | SIGMA= | 13.8 | PHAS= | -164.6 | FOM= | 0.26 | TEST= 0 |
| INDE | 6 | 7 | 77 | FOBS= | 0.0 | SIGMA= | 27.8 | PHAS= | 0.0 | FOM= | 0.00 | TEST= 0 |
| INDE | 6 | 8 | 16 | FOBS= | 90.0 | SIGMA= | 0.5 | PHAS= | -177.3 | FOM= | 0.68 | TEST= 0 |
| INDE | 6 | 8 | 18 | FOBS= | 167.9 | SIGMA= | 0.4 | PHAS= | -0.4 | FOM= | 0.84 | TEST= 0 |
| INDE | 6 | 8 | 20 | FOBS= | 49.5 | SIGMA= | 1.0 | PHAS= | 2.0 | FOM= | 0.95 | TEST= 0 |
| INDE | 6 | 8 | 22 | FOBS= | 106.2 | SIGMA= | 0.6 | PHAS= | -76.0 | FOM= | 0.88 | TEST= 0 |
| INDE | 6 | 8 | 24 | FOBS= | 145.8 | SIGMA= | 0.6 | PHAS= | 32.2 | FOM= | 0.97 | TEST= 0 |
| INDE | 6 | 8 | 26 | FOBS= | 92.3 | SIGMA= | 1.1 | PHAS= | -54.9 | FOM= | 0.94 | TEST= 0 |
| INDE | 6 | 8 | 28 | FOBS= | 149.5 | SIGMA= | 0.8 | PHAS= | -39.7 | FOM= | 0.96 | TEST= 0 |
| INDE | 6 | 8 | 30 | FOBS= | 64.0 | SIGMA= | 1.5 | PHAS= | 65.7 | FOM= | 0.99 | TEST= 0 |
| INDE | 6 | 8 | 32 | FOBS= | 250.8 | SIGMA= | 0.6 | PHAS= | -76.8 | FOM= | 0.99 | TEST= 0 |
| INDE | 6 | 8 | 34 | FOBS= | 341.9 | SIGMA= | 0.8 | PHAS= | -27.1 | FOM= | 0.99 | TEST= 0 |
| INDE | 6 | 8 | 36 | FOBS= | 360.7 | SIGMA= | 0.6 | PHAS= | 97.7 | FOM= | 0.96 | TEST= 0 |
| INDE | 6 | 8 | 38 | FOBS= | 203.0 | SIGMA= | 0.8 | PHAS= | 127.3 | FOM= | 0.97 | TEST= 0 |
| INDE | 6 | 8 | 40 | FOBS= | 253.9 | SIGMA= | 0.8 | PHAS= | 65.7 | FOM= | 0.95 | TEST= 0 |
| INDE | 6 | 8 | 42 | FOBS= | 52.4 | SIGMA= | 3.1 | PHAS= | -81.0 | FOM= | 0.79 | TEST= 0 |
| INDE | 6 | 8 | 44 | FOBS= | 56.3 | SIGMA= | 3.1 | PHAS= | 154.5 | FOM= | 0.65 | TEST= 0 |
| INDE | 6 | 8 | 46 | FOBS= | 0.0 | SIGMA= | 21.3 | PHAS= | 0.0 | FOM= | 0.00 | TEST= 0 |
| INDE | 6 | 8 | 48 | FOBS= | 90.5 | SIGMA= | 2.3 | PHAS= | 113.0 | FOM= | 0.95 | TEST= 0 |
| INDE | 6 | 8 | 50 | FOBS= | 148.7 | SIGMA= | 1.4 | PHAS= | 12.8 | FOM= | 0.60 | TEST= 1 |
| INDE | 6 | 8 | 52 | FOBS= | 116.5 | SIGMA= | 1.7 | PHAS= | -79.8 | FOM= | 0.79 | TEST= 0 |
| INDE | 6 | 8 | 54 | FOBS= | 125.2 | SIGMA= | 1.6 | PHAS= | 5.7 | FOM= | 0.80 | TEST= 0 |
| INDE | 6 | 8 | 56 | FOBS= | 148.6 | SIGMA= | 1.4 | PHAS= | -103.5 | FOM= | 0.93 | TEST= 0 |
| INDE | 6 | 8 | 58 | FOBS= | 133.9 | SIGMA= | 1.5 | PHAS= | 98.0 | FOM= | 0.96 | TEST= 0 |
| INDE | 6 | 8 | 60 | FOBS= | 88.8 | SIGMA= | 2.9 | PHAS= | 60.1 | FOM= | 0.93 | TEST= 0 |
| INDE | 6 | 8 | 62 | FOBS= | 23.2 | SIGMA= | 12.4 | PHAS= | 106.1 | FOM= | 0.34 | TEST= 0 |
| INDE | 6 | 8 | 64 | FOBS= | 111.7 | SIGMA= | 3.3 | PHAS= | 7.1 | FOM= | 0.87 | TEST= 0 |
| INDE | 6 | 8 | 66 | FOBS= | 59.0 | SIGMA= | 8.3 | PHAS= | 72.8 | FOM= | 0.54 | TEST= 0 |
| INDE | 6 | 8 | 68 | FOBS= | 12.4 | SIGMA= | 31.3 | PHAS= | -144.3 | FOM= | 0.04 | TEST= 1 |
| INDE | 6 | 8 | 70 | FOBS= | 0.0 | SIGMA= | 27.4 | PHAS= | 0.0 | FOM= | 0.00 | TEST= 0 |
| INDE | 6 | 8 | 72 | FOBS= | 50.3 | SIGMA= | 7.4 | PHAS= | -30.0 | FOM= | 0.83 | TEST= 0 |
| INDE | 6 | 8 | 74 | FOBS= | 0.0 | SIGMA= | 28.4 | PHAS= | 0.0 | FOM= | 0.00 | TEST= 0 |
| INDE | 6 | 8 | 76 | FOBS= | 52.7 | SIGMA= | 7.5 | PHAS= | -177.3 | FOM= | 0.88 | TEST= 0 |
| INDE | 6 | 9 | 15 | FOBS= | 44.6 | SIGMA= | 0.9 | PHAS= | -170.8 | FOM= | 0.83 | TEST= 0 |
| INDE | 6 | 9 | 17 | FOBS= | 97.2 | SIGMA= | 0.5 | PHAS= | -71.1 | FOM= | 0.68 | TEST= 0 |
| INDE | 6 | 9 | 19 | FOBS= | 110.8 | SIGMA= | 0.5 | PHAS= | -115.4 | FOM= | 0.76 | TEST= 1 |
| INDE | 6 | 9 | 21 | FOBS= | 41.5 | SIGMA= | 1.3 | PHAS= | -179.4 | FOM= | 0.92 | TEST= 0 |
| INDE | 6 | 9 | 23 | FOBS= | 56.5 | SIGMA= | 1.2 | PHAS= | -52.4 | FOM= | 0.96 | TEST= 0 |
| INDE | 6 | 9 | 25 | FOBS= | 140.1 | SIGMA= | 0.7 | PHAS= | -142.8 | FOM= | 0.96 | TEST= 0 |

*FIG. 12A - 160*

| | | | | | | | | | | |
|---|---|---|---|---|---|---|---|---|---|---|
| INDE | 6 | 9 | 27 | FOBS= | 146.9 | SIGMA= | 0.7 | PHAS= | 131.1 | FOM= | 0.96 | TEST= 0
| INDE | 6 | 9 | 29 | FOBS= | 200.6 | SIGMA= | 0.7 | PHAS= | -168.4 | FOM= | 0.97 | TEST= 0
| INDE | 6 | 9 | 31 | FOBS= | 132.8 | SIGMA= | 0.9 | PHAS= | 113.2 | FOM= | 0.96 | TEST= 0
| INDE | 6 | 9 | 33 | FOBS= | 216.5 | SIGMA= | 0.7 | PHAS= | -163.5 | FOM= | 0.98 | TEST= 0
| INDE | 6 | 9 | 35 | FOBS= | 148.7 | SIGMA= | 1.0 | PHAS= | -36.1 | FOM= | 0.46 | TEST= 1
| INDE | 6 | 9 | 37 | FOBS= | 130.1 | SIGMA= | 1.1 | PHAS= | 74.4 | FOM= | 0.88 | TEST= 0
| INDE | 6 | 9 | 39 | FOBS= | 245.7 | SIGMA= | 0.7 | PHAS= | 21.6 | FOM= | 0.97 | TEST= 0
| INDE | 6 | 9 | 41 | FOBS= | 0.0 | SIGMA= | 17.5 | PHAS= | 0.0 | FOM= | 0.00 | TEST= 1
| INDE | 6 | 9 | 43 | FOBS= | 95.6 | SIGMA= | 1.8 | PHAS= | 0.0 | FOM= | 0.95 | TEST= 0
| INDE | 6 | 9 | 45 | FOBS= | 39.5 | SIGMA= | 4.8 | PHAS= | -44.8 | FOM= | 0.60 | TEST= 0
| INDE | 6 | 9 | 47 | FOBS= | 100.6 | SIGMA= | 2.1 | PHAS= | 98.1 | FOM= | 0.47 | TEST= 0
| INDE | 6 | 9 | 49 | FOBS= | 60.4 | SIGMA= | 3.4 | PHAS= | 52.6 | FOM= | 0.60 | TEST= 0
| INDE | 6 | 9 | 51 | FOBS= | 0.0 | SIGMA= | 20.9 | PHAS= | 0.0 | FOM= | 0.00 | TEST= 0
| INDE | 6 | 9 | 53 | FOBS= | 187.4 | SIGMA= | 1.2 | PHAS= | -160.9 | FOM= | 0.96 | TEST= 0
| INDE | 6 | 9 | 55 | FOBS= | 179.4 | SIGMA= | 1.2 | PHAS= | -144.2 | FOM= | 0.95 | TEST= 0
| INDE | 6 | 9 | 57 | FOBS= | 139.5 | SIGMA= | 1.7 | PHAS= | 55.6 | FOM= | 0.97 | TEST= 0
| INDE | 6 | 9 | 59 | FOBS= | 182.0 | SIGMA= | 1.2 | PHAS= | -89.7 | FOM= | 0.98 | TEST= 0
| INDE | 6 | 9 | 61 | FOBS= | 55.2 | SIGMA= | 3.4 | PHAS= | -44.4 | FOM= | 0.83 | TEST= 0
| INDE | 6 | 9 | 63 | FOBS= | 56.5 | SIGMA= | 4.4 | PHAS= | 52.1 | FOM= | 0.55 | TEST= 0
| INDE | 6 | 9 | 65 | FOBS= | 37.2 | SIGMA= | 9.3 | PHAS= | -69.5 | FOM= | 0.56 | TEST= 0
| INDE | 6 | 9 | 69 | FOBS= | 43.6 | SIGMA= | 9.0 | PHAS= | 0.1 | FOM= | 0.32 | TEST= 0
| INDE | 6 | 9 | 71 | FOBS= | 19.1 | SIGMA= | 19.9 | PHAS= | -87.0 | FOM= | 0.29 | TEST= 0
| INDE | 6 | 9 | 73 | FOBS= | 81.1 | SIGMA= | 4.8 | PHAS= | -97.8 | FOM= | 0.88 | TEST= 0
| INDE | 6 | 9 | 75 | FOBS= | 52.2 | SIGMA= | 8.0 | PHAS= | 94.4 | FOM= | 0.78 | TEST= 0
| INDE | 6 | 9 | 77 | FOBS= | 34.0 | SIGMA= | 12.2 | PHAS= | 74.1 | FOM= | 0.16 | TEST= 0
| INDE | 6 | 10 | 14 | FOBS= | 272.8 | SIGMA= | 0.3 | PHAS= | 63.6 | FOM= | 0.87 | TEST= 0
| INDE | 6 | 10 | 16 | FOBS= | 115.4 | SIGMA= | 0.4 | PHAS= | -99.5 | FOM= | 0.96 | TEST= 0
| INDE | 6 | 10 | 18 | FOBS= | 100.0 | SIGMA= | 0.5 | PHAS= | 82.2 | FOM= | 0.94 | TEST= 0
| INDE | 6 | 10 | 20 | FOBS= | 109.8 | SIGMA= | 0.5 | PHAS= | -74.9 | FOM= | 0.95 | TEST= 0
| INDE | 6 | 10 | 22 | FOBS= | 154.9 | SIGMA= | 0.4 | PHAS= | -89.3 | FOM= | 0.79 | TEST= 0
| INDE | 6 | 10 | 24 | FOBS= | 169.9 | SIGMA= | 0.4 | PHAS= | 97.9 | FOM= | 0.99 | TEST= 0
| INDE | 6 | 10 | 26 | FOBS= | 177.9 | SIGMA= | 0.4 | PHAS= | 37.0 | FOM= | 0.97 | TEST= 0
| INDE | 6 | 10 | 28 | FOBS= | 189.5 | SIGMA= | 0.5 | PHAS= | 6.4 | FOM= | 0.91 | TEST= 0
| INDE | 6 | 10 | 30 | FOBS= | 248.6 | SIGMA= | 0.5 | PHAS= | 41.1 | FOM= | 0.99 | TEST= 0
| INDE | 6 | 10 | 32 | FOBS= | 142.4 | SIGMA= | 0.7 | PHAS= | -71.7 | FOM= | 0.92 | TEST= 0
| INDE | 6 | 10 | 34 | FOBS= | 247.0 | SIGMA= | 0.5 | PHAS= | 50.5 | FOM= | 0.94 | TEST= 0
| INDE | 6 | 10 | 36 | FOBS= | 183.6 | SIGMA= | 0.6 | PHAS= | -137.2 | FOM= | 0.91 | TEST= 0
| INDE | 6 | 10 | 38 | FOBS= | 311.5 | SIGMA= | 0.5 | PHAS= | -82.0 | FOM= | 0.96 | TEST= 0
| INDE | 6 | 10 | 40 | FOBS= | 266.1 | SIGMA= | 0.7 | PHAS= | -35.1 | FOM= | 0.98 | TEST= 0
| INDE | 6 | 10 | 42 | FOBS= | 253.4 | SIGMA= | 0.9 | PHAS= | -52.2 | FOM= | 0.93 | TEST= 0
| INDE | 6 | 10 | 44 | FOBS= | 128.2 | SIGMA= | 1.5 | PHAS= | 131.7 | FOM= | 0.98 | TEST= 0
| INDE | 6 | 10 | 46 | FOBS= | 173.4 | SIGMA= | 1.2 | PHAS= | 48.0 | FOM= | 0.88 | TEST= 0
| INDE | 6 | 10 | 48 | FOBS= | 93.7 | SIGMA= | 2.3 | PHAS= | 5.8 | FOM= | 0.50 | TEST= 1
| INDE | 6 | 10 | 50 | FOBS= | 117.7 | SIGMA= | 1.8 | PHAS= | 119.7 | FOM= | 0.88 | TEST= 0
| INDE | 6 | 10 | 52 | FOBS= | 121.4 | SIGMA= | 1.7 | PHAS= | 5.3 | FOM= | 0.97 | TEST= 0
| INDE | 6 | 10 | 54 | FOBS= | 195.1 | SIGMA= | 1.1 | PHAS= | 118.2 | FOM= | 0.95 | TEST= 0
| INDE | 6 | 10 | 56 | FOBS= | 47.6 | SIGMA= | 4.5 | PHAS= | 5.5 | FOM= | 0.74 | TEST= 0
| INDE | 6 | 10 | 58 | FOBS= | 71.5 | SIGMA= | 2.8 | PHAS= | -177.6 | FOM= | 0.94 | TEST= 0
| INDE | 6 | 10 | 60 | FOBS= | 69.2 | SIGMA= | 2.8 | PHAS= | 173.0 | FOM= | 0.90 | TEST= 0
| INDE | 6 | 10 | 62 | FOBS= | 55.3 | SIGMA= | 3.4 | PHAS= | -156.4 | FOM= | 0.63 | TEST= 0
| INDE | 6 | 10 | 64 | FOBS= | 19.8 | SIGMA= | 11.5 | PHAS= | -107.4 | FOM= | 0.13 | TEST= 0
| INDE | 6 | 10 | 66 | FOBS= | 53.6 | SIGMA= | 9.4 | PHAS= | 36.6 | FOM= | 0.24 | TEST= 1
| INDE | 6 | 10 | 70 | FOBS= | 0.0 | SIGMA= | 28.1 | PHAS= | 0.0 | FOM= | 0.00 | TEST= 0
| INDE | 6 | 10 | 72 | FOBS= | 39.9 | SIGMA= | 9.8 | PHAS= | 113.0 | FOM= | 0.83 | TEST= 0
| INDE | 6 | 10 | 74 | FOBS= | 55.7 | SIGMA= | 7.2 | PHAS= | -77.3 | FOM= | 0.70 | TEST= 0
| INDE | 6 | 11 | 13 | FOBS= | 183.8 | SIGMA= | 0.5 | PHAS= | 25.7 | FOM= | 0.90 | TEST= 0
| INDE | 6 | 11 | 15 | FOBS= | 110.2 | SIGMA= | 0.5 | PHAS= | -175.3 | FOM= | 0.91 | TEST= 0
| INDE | 6 | 11 | 17 | FOBS= | 102.4 | SIGMA= | 0.5 | PHAS= | -75.9 | FOM= | 0.98 | TEST= 0
| INDE | 6 | 11 | 19 | FOBS= | 119.7 | SIGMA= | 0.5 | PHAS= | -117.3 | FOM= | 0.93 | TEST= 0
| INDE | 6 | 11 | 21 | FOBS= | 186.3 | SIGMA= | 0.4 | PHAS= | -161.7 | FOM= | 0.89 | TEST= 0
| INDE | 6 | 11 | 23 | FOBS= | 128.1 | SIGMA= | 0.5 | PHAS= | 43.1 | FOM= | 0.99 | TEST= 0
| INDE | 6 | 11 | 25 | FOBS= | 143.2 | SIGMA= | 0.5 | PHAS= | -24.2 | FOM= | 0.84 | TEST= 1
| INDE | 6 | 11 | 27 | FOBS= | 80.2 | SIGMA= | 0.8 | PHAS= | -80.8 | FOM= | 0.98 | TEST= 1
| INDE | 6 | 11 | 29 | FOBS= | 297.6 | SIGMA= | 0.4 | PHAS= | -101.3 | FOM= | 0.97 | TEST= 0
| INDE | 6 | 11 | 31 | FOBS= | 105.7 | SIGMA= | 0.7 | PHAS= | -94.0 | FOM= | 0.97 | TEST= 0
| INDE | 6 | 11 | 33 | FOBS= | 178.3 | SIGMA= | 0.7 | PHAS= | -96.8 | FOM= | 0.96 | TEST= 0
| INDE | 6 | 11 | 35 | FOBS= | 188.6 | SIGMA= | 1.1 | PHAS= | -130.0 | FOM= | 0.93 | TEST= 0
| INDE | 6 | 11 | 37 | FOBS= | 177.5 | SIGMA= | 0.7 | PHAS= | -95.8 | FOM= | 0.98 | TEST= 0
| INDE | 6 | 11 | 39 | FOBS= | 374.5 | SIGMA= | 0.5 | PHAS= | -158.4 | FOM= | 0.98 | TEST= 0
| INDE | 6 | 11 | 41 | FOBS= | 406.0 | SIGMA= | 0.5 | PHAS= | -166.5 | FOM= | 0.98 | TEST= 0

*FIG. 12A - 161*

| | | | | | | | | | | | | |
|---|---|---|---|---|---|---|---|---|---|---|---|---|
| INDE | 6 | 11 | 43 | FOBS= | 89.9 | SIGMA= | 2.0 | PHAS= | 9.3 | FOM= | 0.83 | TEST= 0 |
| INDE | 6 | 11 | 45 | FOBS= | 136.6 | SIGMA= | 1.5 | PHAS= | 18.1 | FOM= | 0.88 | TEST= 0 |
| INDE | 6 | 11 | 47 | FOBS= | 74.9 | SIGMA= | 2.8 | PHAS= | -89.6 | FOM= | 0.79 | TEST= 0 |
| INDE | 6 | 11 | 49 | FOBS= | 147.6 | SIGMA= | 1.5 | PHAS= | -91.5 | FOM= | 0.78 | TEST= 0 |
| INDE | 6 | 11 | 51 | FOBS= | 95.6 | SIGMA= | 2.1 | PHAS= | -61.0 | FOM= | 0.88 | TEST= 0 |
| INDE | 6 | 11 | 53 | FOBS= | 187.9 | SIGMA= | 1.3 | PHAS= | -131.0 | FOM= | 0.89 | TEST= 0 |
| INDE | 6 | 11 | 55 | FOBS= | 49.3 | SIGMA= | 5.2 | PHAS= | -59.1 | FOM= | 0.59 | TEST= 0 |
| INDE | 6 | 11 | 57 | FOBS= | 0.0 | SIGMA= | 19.8 | PHAS= | 0.0 | FOM= | 0.00 | TEST= 0 |
| INDE | 6 | 11 | 59 | FOBS= | 35.7 | SIGMA= | 6.6 | PHAS= | -177.8 | FOM= | 0.44 | TEST= 0 |
| INDE | 6 | 11 | 61 | FOBS= | 85.3 | SIGMA= | 2.3 | PHAS= | 138.7 | FOM= | 0.80 | TEST= 0 |
| INDE | 6 | 11 | 63 | FOBS= | 6.7 | SIGMA= | 39.8 | PHAS= | -164.7 | FOM= | 0.02 | TEST= 0 |
| INDE | 6 | 11 | 65 | FOBS= | 57.5 | SIGMA= | 4.7 | PHAS= | -74.8 | FOM= | 0.19 | TEST= 1 |
| INDE | 6 | 11 | 67 | FOBS= | 84.7 | SIGMA= | 5.0 | PHAS= | -32.6 | FOM= | 0.87 | TEST= 0 |
| INDE | 6 | 11 | 69 | FOBS= | 124.5 | SIGMA= | 3.4 | PHAS= | 87.0 | FOM= | 0.40 | TEST= 1 |
| INDE | 6 | 11 | 71 | FOBS= | 74.9 | SIGMA= | 5.4 | PHAS= | 172.7 | FOM= | 0.04 | TEST= 1 |
| INDE | 6 | 11 | 73 | FOBS= | 19.6 | SIGMA= | 20.8 | PHAS= | 172.1 | FOM= | 0.35 | TEST= 0 |
| INDE | 6 | 11 | 75 | FOBS= | 30.4 | SIGMA= | 13.5 | PHAS= | -76.5 | FOM= | 0.25 | TEST= 0 |
| INDE | 6 | 12 | 12 | FOBS= | 137.2 | SIGMA= | 0.4 | PHAS= | 23.1 | FOM= | 0.39 | TEST= 0 |
| INDE | 6 | 12 | 14 | FOBS= | 245.7 | SIGMA= | 0.4 | PHAS= | -11.6 | FOM= | 0.96 | TEST= 0 |
| INDE | 6 | 12 | 16 | FOBS= | 125.0 | SIGMA= | 0.5 | PHAS= | 172.6 | FOM= | 0.95 | TEST= 0 |
| INDE | 6 | 12 | 18 | FOBS= | 218.4 | SIGMA= | 0.4 | PHAS= | 153.4 | FOM= | 0.81 | TEST= 0 |
| INDE | 6 | 12 | 20 | FOBS= | 58.2 | SIGMA= | 0.9 | PHAS= | 2.9 | FOM= | 0.96 | TEST= 0 |
| INDE | 6 | 12 | 22 | FOBS= | 170.7 | SIGMA= | 0.4 | PHAS= | -40.8 | FOM= | 0.96 | TEST= 0 |
| INDE | 6 | 12 | 24 | FOBS= | 117.7 | SIGMA= | 0.6 | PHAS= | 8.8 | FOM= | 0.96 | TEST= 0 |
| INDE | 6 | 12 | 26 | FOBS= | 146.2 | SIGMA= | 0.5 | PHAS= | -57.8 | FOM= | 0.97 | TEST= 0 |
| INDE | 6 | 12 | 28 | FOBS= | 157.9 | SIGMA= | 0.5 | PHAS= | -160.5 | FOM= | 0.91 | TEST= 0 |
| INDE | 6 | 12 | 30 | FOBS= | 382.3 | SIGMA= | 0.5 | PHAS= | 142.6 | FOM= | 0.97 | TEST= 0 |
| INDE | 6 | 12 | 32 | FOBS= | 310.3 | SIGMA= | 0.5 | PHAS= | -118.6 | FOM= | 0.98 | TEST= 0 |
| INDE | 6 | 12 | 34 | FOBS= | 63.4 | SIGMA= | 1.3 | PHAS= | -133.0 | FOM= | 0.47 | TEST= 0 |
| INDE | 6 | 12 | 36 | FOBS= | 120.1 | SIGMA= | 0.8 | PHAS= | 168.6 | FOM= | 0.75 | TEST= 1 |
| INDE | 6 | 12 | 38 | FOBS= | 205.6 | SIGMA= | 1.1 | PHAS= | -0.1 | FOM= | 0.93 | TEST= 0 |
| INDE | 6 | 12 | 40 | FOBS= | 380.7 | SIGMA= | 0.5 | PHAS= | 91.3 | FOM= | 0.95 | TEST= 0 |
| INDE | 6 | 12 | 42 | FOBS= | 180.4 | SIGMA= | 0.8 | PHAS= | 86.1 | FOM= | 0.95 | TEST= 0 |
| INDE | 6 | 12 | 44 | FOBS= | 125.0 | SIGMA= | 1.6 | PHAS= | -108.2 | FOM= | 0.91 | TEST= 0 |
| INDE | 6 | 12 | 46 | FOBS= | 91.0 | SIGMA= | 2.3 | PHAS= | 138.4 | FOM= | 0.95 | TEST= 0 |
| INDE | 6 | 12 | 48 | FOBS= | 154.4 | SIGMA= | 1.4 | PHAS= | -171.4 | FOM= | 0.94 | TEST= 0 |
| INDE | 6 | 12 | 50 | FOBS= | 227.1 | SIGMA= | 1.1 | PHAS= | 143.5 | FOM= | 0.96 | TEST= 0 |
| INDE | 6 | 12 | 52 | FOBS= | 200.5 | SIGMA= | 1.1 | PHAS= | 161.7 | FOM= | 0.91 | TEST= 0 |
| INDE | 6 | 12 | 54 | FOBS= | 110.1 | SIGMA= | 1.8 | PHAS= | 130.9 | FOM= | 0.91 | TEST= 0 |
| INDE | 6 | 12 | 56 | FOBS= | 82.0 | SIGMA= | 2.4 | PHAS= | 135.2 | FOM= | 0.79 | TEST= 0 |
| INDE | 6 | 12 | 58 | FOBS= | 98.5 | SIGMA= | 2.0 | PHAS= | -107.0 | FOM= | 0.60 | TEST= 0 |
| INDE | 6 | 12 | 60 | FOBS= | 86.6 | SIGMA= | 2.3 | PHAS= | 34.9 | FOM= | 0.77 | TEST= 0 |
| INDE | 6 | 12 | 62 | FOBS= | 44.2 | SIGMA= | 4.8 | PHAS= | 112.3 | FOM= | 0.75 | TEST= 0 |
| INDE | 6 | 12 | 64 | FOBS= | 51.1 | SIGMA= | 4.6 | PHAS= | 154.6 | FOM= | 0.48 | TEST= 0 |
| INDE | 6 | 12 | 66 | FOBS= | 70.5 | SIGMA= | 6.0 | PHAS= | -41.9 | FOM= | 0.65 | TEST= 0 |
| INDE | 6 | 12 | 68 | FOBS= | 67.1 | SIGMA= | 6.3 | PHAS= | 0.0 | FOM= | 0.72 | TEST= 0 |
| INDE | 6 | 12 | 70 | FOBS= | 0.0 | SIGMA= | 24.4 | PHAS= | 0.0 | FOM= | 0.00 | TEST= 0 |
| INDE | 6 | 12 | 72 | FOBS= | 58.4 | SIGMA= | 7.2 | PHAS= | 66.8 | FOM= | 0.68 | TEST= 0 |
| INDE | 6 | 12 | 74 | FOBS= | 27.0 | SIGMA= | 15.5 | PHAS= | 1.7 | FOM= | 0.05 | TEST= 0 |
| INDE | 6 | 12 | 76 | FOBS= | 43.3 | SIGMA= | 10.0 | PHAS= | -148.3 | FOM= | 0.80 | TEST= 0 |
| INDE | 6 | 13 | 11 | FOBS= | 103.6 | SIGMA= | 0.6 | PHAS= | -163.6 | FOM= | 0.78 | TEST= 0 |
| INDE | 6 | 13 | 13 | FOBS= | 110.2 | SIGMA= | 0.5 | PHAS= | -24.8 | FOM= | 0.86 | TEST= 0 |
| INDE | 6 | 13 | 15 | FOBS= | 70.5 | SIGMA= | 0.7 | PHAS= | -81.5 | FOM= | 0.45 | TEST= 0 |
| INDE | 6 | 13 | 17 | FOBS= | 65.1 | SIGMA= | 0.8 | PHAS= | -128.4 | FOM= | 0.99 | TEST= 0 |
| INDE | 6 | 13 | 19 | FOBS= | 136.5 | SIGMA= | 0.5 | PHAS= | -28.8 | FOM= | 0.92 | TEST= 0 |
| INDE | 6 | 13 | 21 | FOBS= | 325.5 | SIGMA= | 0.4 | PHAS= | -174.7 | FOM= | 0.88 | TEST= 1 |
| INDE | 6 | 13 | 23 | FOBS= | 154.0 | SIGMA= | 0.5 | PHAS= | -45.1 | FOM= | 0.90 | TEST= 0 |
| INDE | 6 | 13 | 25 | FOBS= | 180.8 | SIGMA= | 0.5 | PHAS= | -96.3 | FOM= | 0.98 | TEST= 0 |
| INDE | 6 | 13 | 27 | FOBS= | 133.6 | SIGMA= | 0.6 | PHAS= | -142.1 | FOM= | 0.97 | TEST= 0 |
| INDE | 6 | 13 | 29 | FOBS= | 255.6 | SIGMA= | 0.7 | PHAS= | 129.5 | FOM= | 0.98 | TEST= 0 |
| INDE | 6 | 13 | 31 | FOBS= | 220.0 | SIGMA= | 0.5 | PHAS= | 30.0 | FOM= | 0.92 | TEST= 0 |
| INDE | 6 | 13 | 33 | FOBS= | 113.9 | SIGMA= | 0.7 | PHAS= | 165.6 | FOM= | 0.96 | TEST= 0 |
| INDE | 6 | 13 | 35 | FOBS= | 113.8 | SIGMA= | 0.8 | PHAS= | 147.5 | FOM= | 0.51 | TEST= 0 |
| INDE | 6 | 13 | 37 | FOBS= | 296.7 | SIGMA= | 0.6 | PHAS= | -59.3 | FOM= | 0.96 | TEST= 0 |
| INDE | 6 | 13 | 39 | FOBS= | 102.4 | SIGMA= | 1.1 | PHAS= | -50.8 | FOM= | 0.89 | TEST= 0 |
| INDE | 6 | 13 | 41 | FOBS= | 192.6 | SIGMA= | 0.9 | PHAS= | 83.5 | FOM= | 0.83 | TEST= 0 |
| INDE | 6 | 13 | 43 | FOBS= | 90.9 | SIGMA= | 2.1 | PHAS= | 5.8 | FOM= | 0.93 | TEST= 0 |
| INDE | 6 | 13 | 45 | FOBS= | 28.4 | SIGMA= | 7.0 | PHAS= | 178.7 | FOM= | 0.50 | TEST= 0 |
| INDE | 6 | 13 | 47 | FOBS= | 254.3 | SIGMA= | 1.0 | PHAS= | 59.7 | FOM= | 0.97 | TEST= 0 |
| INDE | 6 | 13 | 49 | FOBS= | 70.6 | SIGMA= | 2.9 | PHAS= | -60.2 | FOM= | 0.65 | TEST= 0 |

*FIG. 12A - 162*

| | | | | | | | | | | | |
|---|---|---|---|---|---|---|---|---|---|---|---|
| INDE | 6 | 13 | 51 | FOBS= | 161.8 | SIGMA= | 1.3 | PHAS= | 43.1 | FOM= | 0.96 | TEST= 0
| INDE | 6 | 13 | 53 | FOBS= | 27.6 | SIGMA= | 7.2 | PHAS= | -76.6 | FOM= | 0.68 | TEST= 0
| INDE | 6 | 13 | 55 | FOBS= | 150.4 | SIGMA= | 1.4 | PHAS= | 71.7 | FOM= | 0.87 | TEST= 0
| INDE | 6 | 13 | 57 | FOBS= | 62.1 | SIGMA= | 3.2 | PHAS= | -164.9 | FOM= | 0.47 | TEST= 1
| INDE | 6 | 13 | 59 | FOBS= | 87.9 | SIGMA= | 2.2 | PHAS= | 46.2 | FOM= | 0.12 | TEST= 1
| INDE | 6 | 13 | 61 | FOBS= | 84.4 | SIGMA= | 2.3 | PHAS= | 135.3 | FOM= | 0.83 | TEST= 0
| INDE | 6 | 13 | 63 | FOBS= | 54.1 | SIGMA= | 4.3 | PHAS= | 26.0 | FOM= | 0.59 | TEST= 0
| INDE | 6 | 13 | 65 | FOBS= | 67.4 | SIGMA= | 4.1 | PHAS= | -56.7 | FOM= | 0.83 | TEST= 0
| INDE | 6 | 13 | 67 | FOBS= | 89.8 | SIGMA= | 4.8 | PHAS= | -57.1 | FOM= | 0.58 | TEST= 1
| INDE | 6 | 13 | 69 | FOBS= | 25.6 | SIGMA= | 16.7 | PHAS= | -25.3 | FOM= | 0.29 | TEST= 0
| INDE | 6 | 13 | 71 | FOBS= | 0.0 | SIGMA= | 24.7 | PHAS= | 0.0 | FOM= | 0.00 | TEST= 0
| INDE | 6 | 13 | 73 | FOBS= | 44.1 | SIGMA= | 7.1 | PHAS= | 126.0 | FOM= | 0.71 | TEST= 0
| INDE | 6 | 13 | 75 | FOBS= | 60.0 | SIGMA= | 7.2 | PHAS= | 6.5 | FOM= | 0.76 | TEST= 0
| INDE | 6 | 14 | 10 | FOBS= | 428.4 | SIGMA= | 0.5 | PHAS= | -136.3 | FOM= | 0.42 | TEST= 0
| INDE | 6 | 14 | 12 | FOBS= | 153.0 | SIGMA= | 0.5 | PHAS= | 156.8 | FOM= | 0.78 | TEST= 0
| INDE | 6 | 14 | 14 | FOBS= | 147.3 | SIGMA= | 0.5 | PHAS= | -83.9 | FOM= | 0.84 | TEST= 0
| INDE | 6 | 14 | 16 | FOBS= | 124.6 | SIGMA= | 0.5 | PHAS= | 75.7 | FOM= | 0.89 | TEST= 0
| INDE | 6 | 14 | 18 | FOBS= | 163.2 | SIGMA= | 0.5 | PHAS= | 117.8 | FOM= | 0.99 | TEST= 0
| INDE | 6 | 14 | 20 | FOBS= | 71.5 | SIGMA= | 0.8 | PHAS= | -146.3 | FOM= | 0.80 | TEST= 0
| INDE | 6 | 14 | 22 | FOBS= | 182.5 | SIGMA= | 0.5 | PHAS= | 66.8 | FOM= | 0.90 | TEST= 0
| INDE | 6 | 14 | 24 | FOBS= | 121.1 | SIGMA= | 0.6 | PHAS= | 97.4 | FOM= | 0.92 | TEST= 0
| INDE | 6 | 14 | 26 | FOBS= | 108.2 | SIGMA= | 0.7 | PHAS= | 98.3 | FOM= | 0.96 | TEST= 0
| INDE | 6 | 14 | 28 | FOBS= | 133.5 | SIGMA= | 0.6 | PHAS= | 78.2 | FOM= | 0.99 | TEST= 0
| INDE | 6 | 14 | 30 | FOBS= | 104.4 | SIGMA= | 0.8 | PHAS= | 119.2 | FOM= | 0.96 | TEST= 0
| INDE | 6 | 14 | 32 | FOBS= | 210.6 | SIGMA= | 0.5 | PHAS= | -124.9 | FOM= | 0.97 | TEST= 0
| INDE | 6 | 14 | 34 | FOBS= | 73.3 | SIGMA= | 1.1 | PHAS= | -99.7 | FOM= | 0.96 | TEST= 0
| INDE | 6 | 14 | 36 | FOBS= | 158.9 | SIGMA= | 0.6 | PHAS= | 158.8 | FOM= | 0.88 | TEST= 0
| INDE | 6 | 14 | 38 | FOBS= | 182.1 | SIGMA= | 0.8 | PHAS= | -87.3 | FOM= | 0.93 | TEST= 0
| INDE | 6 | 14 | 40 | FOBS= | 144.2 | SIGMA= | 1.0 | PHAS= | -64.8 | FOM= | 0.32 | TEST= 0
| INDE | 6 | 14 | 42 | FOBS= | 66.8 | SIGMA= | 2.7 | PHAS= | 16.0 | FOM= | 0.89 | TEST= 0
| INDE | 6 | 14 | 44 | FOBS= | 102.8 | SIGMA= | 2.0 | PHAS= | 152.2 | FOM= | 0.54 | TEST= 0
| INDE | 6 | 14 | 46 | FOBS= | 150.3 | SIGMA= | 1.5 | PHAS= | -100.3 | FOM= | 0.94 | TEST= 0
| INDE | 6 | 14 | 48 | FOBS= | 0.0 | SIGMA= | 20.3 | PHAS= | 0.0 | FOM= | 0.00 | TEST= 1
| INDE | 6 | 14 | 50 | FOBS= | 100.3 | SIGMA= | 2.1 | PHAS= | 146.1 | FOM= | 0.81 | TEST= 1
| INDE | 6 | 14 | 52 | FOBS= | 243.1 | SIGMA= | 1.1 | PHAS= | -169.0 | FOM= | 0.98 | TEST= 0
| INDE | 6 | 14 | 54 | FOBS= | 47.1 | SIGMA= | 4.2 | PHAS= | 27.7 | FOM= | 0.41 | TEST= 0
| INDE | 6 | 14 | 56 | FOBS= | 41.4 | SIGMA= | 4.7 | PHAS= | -114.4 | FOM= | 0.62 | TEST= 0
| INDE | 6 | 14 | 58 | FOBS= | 50.6 | SIGMA= | 4.2 | PHAS= | 30.9 | FOM= | 0.34 | TEST= 0
| INDE | 6 | 14 | 60 | FOBS= | 59.1 | SIGMA= | 3.6 | PHAS= | 15.9 | FOM= | 0.66 | TEST= 0
| INDE | 6 | 14 | 62 | FOBS= | 107.4 | SIGMA= | 1.8 | PHAS= | 21.6 | FOM= | 0.90 | TEST= 0
| INDE | 6 | 14 | 64 | FOBS= | 65.8 | SIGMA= | 4.1 | PHAS= | -88.9 | FOM= | 0.86 | TEST= 0
| INDE | 6 | 14 | 66 | FOBS= | 177.5 | SIGMA= | 2.6 | PHAS= | 170.1 | FOM= | 0.96 | TEST= 0
| INDE | 6 | 14 | 68 | FOBS= | 45.0 | SIGMA= | 9.5 | PHAS= | -147.5 | FOM= | 0.70 | TEST= 0
| INDE | 6 | 14 | 70 | FOBS= | 30.7 | SIGMA= | 14.2 | PHAS= | -133.4 | FOM= | 0.56 | TEST= 0
| INDE | 6 | 14 | 72 | FOBS= | 0.0 | SIGMA= | 25.0 | PHAS= | 0.0 | FOM= | 0.00 | TEST= 0
| INDE | 6 | 14 | 74 | FOBS= | 0.0 | SIGMA= | 30.1 | PHAS= | 0.0 | FOM= | 0.00 | TEST= 0
| INDE | 6 | 14 | 76 | FOBS= | 66.6 | SIGMA= | 6.8 | PHAS= | -85.7 | FOM= | 0.82 | TEST= 0
| INDE | 6 | 15 | 9 | FOBS= | 148.2 | SIGMA= | 0.5 | PHAS= | 47.2 | FOM= | 0.94 | TEST= 0
| INDE | 6 | 15 | 11 | FOBS= | 347.6 | SIGMA= | 0.5 | PHAS= | 17.2 | FOM= | 0.92 | TEST= 0
| INDE | 6 | 15 | 13 | FOBS= | 163.0 | SIGMA= | 0.5 | PHAS= | 130.9 | FOM= | 0.91 | TEST= 0
| INDE | 6 | 15 | 15 | FOBS= | 227.4 | SIGMA= | 0.6 | PHAS= | -68.0 | FOM= | 0.93 | TEST= 0
| INDE | 6 | 15 | 17 | FOBS= | 255.0 | SIGMA= | 0.5 | PHAS= | -43.5 | FOM= | 0.93 | TEST= 0
| INDE | 6 | 15 | 19 | FOBS= | 21.9 | SIGMA= | 2.5 | PHAS= | -125.7 | FOM= | 0.85 | TEST= 0
| INDE | 6 | 15 | 21 | FOBS= | 107.2 | SIGMA= | 0.5 | PHAS= | -99.1 | FOM= | 0.99 | TEST= 0
| INDE | 6 | 15 | 23 | FOBS= | 247.9 | SIGMA= | 0.4 | PHAS= | -52.6 | FOM= | 0.91 | TEST= 0
| INDE | 6 | 15 | 25 | FOBS= | 58.6 | SIGMA= | 1.2 | PHAS= | 141.8 | FOM= | 0.98 | TEST= 0
| INDE | 6 | 15 | 27 | FOBS= | 155.1 | SIGMA= | 0.6 | PHAS= | -24.2 | FOM= | 0.99 | TEST= 0
| INDE | 6 | 15 | 29 | FOBS= | 165.1 | SIGMA= | 0.6 | PHAS= | 145.0 | FOM= | 0.99 | TEST= 0
| INDE | 6 | 15 | 31 | FOBS= | 229.1 | SIGMA= | 0.6 | PHAS= | 89.0 | FOM= | 0.97 | TEST= 0
| INDE | 6 | 15 | 33 | FOBS= | 282.3 | SIGMA= | 0.5 | PHAS= | -152.6 | FOM= | 0.97 | TEST= 0
| INDE | 6 | 15 | 35 | FOBS= | 118.2 | SIGMA= | 0.8 | PHAS= | 112.0 | FOM= | 0.92 | TEST= 0
| INDE | 6 | 15 | 37 | FOBS= | 134.7 | SIGMA= | 0.8 | PHAS= | 6.9 | FOM= | 0.94 | TEST= 0
| INDE | 6 | 15 | 39 | FOBS= | 172.2 | SIGMA= | 0.9 | PHAS= | -73.0 | FOM= | 0.91 | TEST= 0
| INDE | 6 | 15 | 41 | FOBS= | 197.4 | SIGMA= | 1.0 | PHAS= | 117.7 | FOM= | 0.93 | TEST= 0
| INDE | 6 | 15 | 43 | FOBS= | 191.4 | SIGMA= | 1.1 | PHAS= | -72.2 | FOM= | 0.13 | TEST= 1
| INDE | 6 | 15 | 45 | FOBS= | 49.9 | SIGMA= | 4.2 | PHAS= | -58.0 | FOM= | 0.66 | TEST= 0
| INDE | 6 | 15 | 47 | FOBS= | 114.7 | SIGMA= | 1.9 | PHAS= | 94.2 | FOM= | 0.86 | TEST= 0
| INDE | 6 | 15 | 49 | FOBS= | 92.6 | SIGMA= | 2.3 | PHAS= | 71.5 | FOM= | 0.64 | TEST= 0
| INDE | 6 | 15 | 51 | FOBS= | 149.6 | SIGMA= | 1.4 | PHAS= | 125.1 | FOM= | 0.93 | TEST= 0
| INDE | 6 | 15 | 53 | FOBS= | 0.0 | SIGMA= | 20.0 | PHAS= | 0.0 | FOM= | 0.00 | TEST= 0

*FIG. 12A - 163*

```
INDE   6  15  55  FOBS=    51.2  SIGMA=   3.8  PHAS=  160.0  FOM=  0.75  TEST= 0
INDE   6  15  57  FOBS=   113.4  SIGMA=   1.8  PHAS= -149.0  FOM=  0.89  TEST= 0
INDE   6  15  59  FOBS=    76.7  SIGMA=   2.6  PHAS=  -21.0  FOM=  0.63  TEST= 1
INDE   6  15  61  FOBS=    40.4  SIGMA=   4.8  PHAS= -120.4  FOM=  0.47  TEST= 0
INDE   6  15  63  FOBS=    28.3  SIGMA=   7.1  PHAS= -116.1  FOM=  0.17  TEST= 0
INDE   6  15  65  FOBS=    56.7  SIGMA=   5.8  PHAS=   56.5  FOM=  0.16  TEST= 1
INDE   6  15  67  FOBS=   100.5  SIGMA=   4.2  PHAS=   69.5  FOM=  0.93  TEST= 0
INDE   6  15  69  FOBS=    56.6  SIGMA=   7.6  PHAS=  -69.3  FOM=  0.07  TEST= 1
INDE   6  15  71  FOBS=    69.8  SIGMA=   4.5  PHAS= -139.9  FOM=  0.90  TEST= 0
INDE   6  15  73  FOBS=     6.9  SIGMA=  45.8  PHAS=  170.0  FOM=  0.09  TEST= 0
INDE   6  15  75  FOBS=    50.6  SIGMA=   6.4  PHAS=  -71.4  FOM=  0.81  TEST= 0
INDE   6  16   6  FOBS=   353.2  SIGMA=   0.4  PHAS= -152.6  FOM=  0.75  TEST= 0
INDE   6  16   8  FOBS=   181.9  SIGMA=   0.4  PHAS= -160.2  FOM=  0.79  TEST= 0
INDE   6  16  10  FOBS=   217.7  SIGMA=   0.5  PHAS=  -46.2  FOM=  0.91  TEST= 0
INDE   6  16  12  FOBS=   138.5  SIGMA=   0.6  PHAS=   -1.2  FOM=  0.57  TEST= 0
INDE   6  16  14  FOBS=    29.8  SIGMA=   2.2  PHAS= -101.3  FOM=  0.58  TEST= 0
INDE   6  16  16  FOBS=   329.8  SIGMA=   0.5  PHAS= -156.8  FOM=  0.98  TEST= 0
INDE   6  16  18  FOBS=   210.6  SIGMA=   0.5  PHAS=  106.0  FOM=  0.89  TEST= 0
INDE   6  16  20  FOBS=   137.1  SIGMA=   0.5  PHAS=  -62.2  FOM=  0.99  TEST= 0
INDE   6  16  22  FOBS=   176.7  SIGMA=   0.5  PHAS=  178.6  FOM=  0.98  TEST= 0
INDE   6  16  24  FOBS=   235.8  SIGMA=   0.5  PHAS=  164.1  FOM=  0.96  TEST= 1
INDE   6  16  26  FOBS=    96.1  SIGMA=   0.8  PHAS=  171.9  FOM=  0.96  TEST= 0
INDE   6  16  28  FOBS=   135.9  SIGMA=   0.6  PHAS=   54.7  FOM=  0.98  TEST= 0
INDE   6  16  30  FOBS=   113.9  SIGMA=   0.7  PHAS=   91.6  FOM=  0.99  TEST= 0
INDE   6  16  32  FOBS=   238.4  SIGMA=   0.5  PHAS=   52.0  FOM=  0.96  TEST= 0
INDE   6  16  34  FOBS=   146.6  SIGMA=   0.7  PHAS=  103.8  FOM=  0.92  TEST= 0
INDE   6  16  36  FOBS=   182.8  SIGMA=   0.7  PHAS=  -94.9  FOM=  0.95  TEST= 0
INDE   6  16  38  FOBS=   282.2  SIGMA=   0.7  PHAS=  -76.7  FOM=  0.94  TEST= 0
INDE   6  16  40  FOBS=   261.2  SIGMA=   0.8  PHAS=  -93.6  FOM=  0.96  TEST= 0
INDE   6  16  42  FOBS=   227.7  SIGMA=   1.0  PHAS=   52.9  FOM=  0.92  TEST= 1
INDE   6  16  44  FOBS=   134.3  SIGMA=   1.6  PHAS=  136.0  FOM=  0.61  TEST= 0
INDE   6  16  46  FOBS=   151.1  SIGMA=   1.5  PHAS=  -69.7  FOM=  0.86  TEST= 1
INDE   6  16  48  FOBS=   176.6  SIGMA=   1.4  PHAS=  113.7  FOM=  0.41  TEST= 1
INDE   6  16  50  FOBS=   118.4  SIGMA=   1.8  PHAS=   40.5  FOM=  0.88  TEST= 1
INDE   6  16  52  FOBS=   160.6  SIGMA=   1.4  PHAS= -136.6  FOM=  0.90  TEST= 0
INDE   6  16  54  FOBS=    60.3  SIGMA=   3.4  PHAS=   74.2  FOM=  0.87  TEST= 0
INDE   6  16  56  FOBS=   115.3  SIGMA=   1.8  PHAS= -179.7  FOM=  0.90  TEST= 0
INDE   6  16  58  FOBS=   102.6  SIGMA=   2.0  PHAS=  173.6  FOM=  0.82  TEST= 0
INDE   6  16  60  FOBS=   108.0  SIGMA=   1.9  PHAS=  158.7  FOM=  0.91  TEST= 0
INDE   6  16  62  FOBS=     0.0  SIGMA=  20.1  PHAS=    0.0  FOM=  0.00  TEST= 0
INDE   6  16  64  FOBS=    57.4  SIGMA=   4.8  PHAS=   35.1  FOM=  0.77  TEST= 0
INDE   6  16  68  FOBS=     0.0  SIGMA=  29.1  PHAS=    0.0  FOM=  0.00  TEST= 0
INDE   6  16  70  FOBS=   116.0  SIGMA=   3.9  PHAS=  160.9  FOM=  0.95  TEST= 0
INDE   6  16  72  FOBS=    97.7  SIGMA=   3.4  PHAS=  171.4  FOM=  0.93  TEST= 0
INDE   6  16  74  FOBS=    52.0  SIGMA=   6.3  PHAS= -166.3  FOM=  0.35  TEST= 0
INDE   6  17   7  FOBS=    36.4  SIGMA=   1.3  PHAS= -131.3  FOM=  0.96  TEST= 0
INDE   6  17   9  FOBS=   332.7  SIGMA=   0.5  PHAS=  162.4  FOM=  0.98  TEST= 0
INDE   6  17  11  FOBS=   110.3  SIGMA=   0.6  PHAS=   36.4  FOM=  0.85  TEST= 0
INDE   6  17  13  FOBS=    82.2  SIGMA=   0.9  PHAS=    7.6  FOM=  0.40  TEST= 0
INDE   6  17  15  FOBS=    67.6  SIGMA=   1.0  PHAS= -172.0  FOM=  0.85  TEST= 0
INDE   6  17  17  FOBS=   106.3  SIGMA=   0.7  PHAS=   23.8  FOM=  0.96  TEST= 1
INDE   6  17  19  FOBS=    50.9  SIGMA=   1.2  PHAS=  118.3  FOM=  0.99  TEST= 0
INDE   6  17  21  FOBS=   114.2  SIGMA=   0.6  PHAS= -101.0  FOM=  0.99  TEST= 0
INDE   6  17  23  FOBS=    45.3  SIGMA=   1.4  PHAS=  125.9  FOM=  0.95  TEST= 0
INDE   6  17  25  FOBS=   273.5  SIGMA=   0.5  PHAS=   89.6  FOM=  0.98  TEST= 0
INDE   6  17  27  FOBS=   146.7  SIGMA=   0.6  PHAS=  -14.8  FOM=  0.82  TEST= 0
INDE   6  17  29  FOBS=    92.8  SIGMA=   0.9  PHAS=  -33.3  FOM=  0.94  TEST= 0
INDE   6  17  31  FOBS=   140.9  SIGMA=   0.7  PHAS=   23.2  FOM=  0.98  TEST= 0
INDE   6  17  33  FOBS=   190.0  SIGMA=   0.7  PHAS=  -30.6  FOM=  0.97  TEST= 0
INDE   6  17  35  FOBS=   196.1  SIGMA=   0.7  PHAS=    5.2  FOM=  0.97  TEST= 1
INDE   6  17  37  FOBS=   240.9  SIGMA=   0.7  PHAS=  136.6  FOM=  0.94  TEST= 0
INDE   6  17  39  FOBS=   333.9  SIGMA=   0.6  PHAS= -146.2  FOM=  0.97  TEST= 0
INDE   6  17  41  FOBS=   148.5  SIGMA=   1.1  PHAS=  134.3  FOM=  0.97  TEST= 1
INDE   6  17  43  FOBS=   149.9  SIGMA=   1.3  PHAS= -127.8  FOM=  0.95  TEST= 0
INDE   6  17  45  FOBS=   149.6  SIGMA=   1.5  PHAS=  -28.7  FOM=  0.97  TEST= 0
INDE   6  17  47  FOBS=   170.2  SIGMA=   1.4  PHAS=  -59.7  FOM=  0.89  TEST= 0
INDE   6  17  49  FOBS=    31.7  SIGMA=   7.6  PHAS=  117.2  FOM=  0.32  TEST= 0
INDE   6  17  51  FOBS=   175.8  SIGMA=   1.5  PHAS= -168.4  FOM=  0.97  TEST= 0
INDE   6  17  53  FOBS=    37.5  SIGMA=   5.4  PHAS=  146.6  FOM=  0.72  TEST= 0
INDE   6  17  55  FOBS=    78.8  SIGMA=   2.6  PHAS=   26.2  FOM=  0.94  TEST= 0
```

*FIG. 12A - 164*

```
INDE  6  17  57  FOBS=  162.5  SIGMA=   1.3  PHAS=   125.2  FOM=  0.90  TEST= 0
INDE  6  17  59  FOBS=   96.9  SIGMA=   2.1  PHAS=    30.7  FOM=  0.85  TEST= 0
INDE  6  17  61  FOBS=  132.8  SIGMA=   1.5  PHAS=    45.0  FOM=  0.95  TEST= 0
INDE  6  17  63  FOBS=   97.3  SIGMA=   2.4  PHAS=    28.1  FOM=  0.82  TEST= 0
INDE  6  17  65  FOBS=   97.5  SIGMA=   4.5  PHAS=  -178.5  FOM=  0.80  TEST= 0
INDE  6  17  67  FOBS=   58.6  SIGMA=   7.5  PHAS=    24.2  FOM=  0.89  TEST= 0
INDE  6  17  69  FOBS=   26.7  SIGMA=  16.6  PHAS=    15.5  FOM=  0.49  TEST= 0
INDE  6  17  71  FOBS=   66.6  SIGMA=   6.6  PHAS=    67.1  FOM=  0.60  TEST= 0
INDE  6  17  73  FOBS=   70.2  SIGMA=   4.7  PHAS=   136.3  FOM=  0.90  TEST= 0
INDE  6  17  75  FOBS=   23.6  SIGMA=  14.1  PHAS=   156.0  FOM=  0.30  TEST= 0
INDE  6  18   6  FOBS=  169.1  SIGMA=   0.5  PHAS=    20.4  FOM=  0.55  TEST= 1
INDE  6  18   8  FOBS=  208.2  SIGMA=   0.6  PHAS=   137.6  FOM=  0.41  TEST= 1
INDE  6  18  10  FOBS=  237.9  SIGMA=   0.5  PHAS=  -168.8  FOM=  0.35  TEST= 1
INDE  6  18  12  FOBS=   66.8  SIGMA=   1.1  PHAS=   -56.5  FOM=  0.62  TEST= 0
INDE  6  18  14  FOBS=  117.3  SIGMA=   0.7  PHAS=  -127.4  FOM=  0.91  TEST= 0
INDE  6  18  16  FOBS=   98.9  SIGMA=   0.8  PHAS=   179.9  FOM=  0.85  TEST= 0
INDE  6  18  18  FOBS=  119.5  SIGMA=   0.6  PHAS=    26.3  FOM=  0.99  TEST= 0
INDE  6  18  20  FOBS=  100.0  SIGMA=   0.7  PHAS=  -118.2  FOM=  0.93  TEST= 0
INDE  6  18  22  FOBS=  101.5  SIGMA=   0.7  PHAS=  -112.5  FOM=  0.98  TEST= 1
INDE  6  18  24  FOBS=  142.8  SIGMA=   0.5  PHAS=    25.8  FOM=  0.76  TEST= 0
INDE  6  18  26  FOBS=   65.1  SIGMA=   1.1  PHAS=    16.2  FOM=  0.98  TEST= 0
INDE  6  18  28  FOBS=   85.1  SIGMA=   1.0  PHAS=   -36.2  FOM=  0.88  TEST= 0
INDE  6  18  30  FOBS=  161.1  SIGMA=   0.7  PHAS=  -171.2  FOM=  0.95  TEST= 0
INDE  6  18  32  FOBS=   34.0  SIGMA=   3.1  PHAS=   -72.5  FOM=  0.87  TEST= 0
INDE  6  18  34  FOBS=  293.5  SIGMA=   0.6  PHAS=   -87.5  FOM=  0.95  TEST= 1
INDE  6  18  36  FOBS=  276.0  SIGMA=   0.6  PHAS=  -108.4  FOM=  0.94  TEST= 0
INDE  6  18  38  FOBS=  186.8  SIGMA=   0.8  PHAS=   144.4  FOM=  0.78  TEST= 0
INDE  6  18  40  FOBS=  165.9  SIGMA=   1.1  PHAS=    85.2  FOM=  0.95  TEST= 0
INDE  6  18  42  FOBS=  224.7  SIGMA=   0.8  PHAS=   140.5  FOM=  0.96  TEST= 0
INDE  6  18  44  FOBS=   20.7  SIGMA=   9.8  PHAS=  -124.9  FOM=  0.43  TEST= 0
INDE  6  18  46  FOBS=  206.7  SIGMA=   0.8  PHAS=  -153.8  FOM=  0.97  TEST= 0
INDE  6  18  48  FOBS=   79.8  SIGMA=   1.9  PHAS=   -45.1  FOM=  0.86  TEST= 0
INDE  6  18  50  FOBS=  205.8  SIGMA=   1.1  PHAS=   129.5  FOM=  0.69  TEST= 1
INDE  6  18  52  FOBS=  245.7  SIGMA=   1.0  PHAS=  -174.0  FOM=  0.95  TEST= 0
INDE  6  18  54  FOBS=   58.8  SIGMA=   3.5  PHAS=   125.0  FOM=  0.86  TEST= 0
INDE  6  18  56  FOBS=  202.5  SIGMA=   1.1  PHAS=   -56.2  FOM=  0.95  TEST= 0
INDE  6  18  58  FOBS=    0.0  SIGMA=  19.9  PHAS=     0.0  FOM=  0.00  TEST= 0
INDE  6  18  60  FOBS=  114.2  SIGMA=   1.8  PHAS=   -91.3  FOM=  0.93  TEST= 0
INDE  6  18  62  FOBS=  148.6  SIGMA=   1.7  PHAS=   -11.9  FOM=  0.94  TEST= 0
INDE  6  18  64  FOBS=  199.5  SIGMA=   1.9  PHAS=    25.0  FOM=  0.96  TEST= 0
INDE  6  18  66  FOBS=   63.3  SIGMA=   7.0  PHAS=  -100.1  FOM=  0.78  TEST= 0
INDE  6  18  68  FOBS=  101.7  SIGMA=   4.4  PHAS=   -64.4  FOM=  0.95  TEST= 0
INDE  6  18  70  FOBS=   54.2  SIGMA=   8.4  PHAS=   147.9  FOM=  0.69  TEST= 0
INDE  6  18  72  FOBS=   98.4  SIGMA=   4.7  PHAS=   103.4  FOM=  0.93  TEST= 0
INDE  6  18  74  FOBS=   42.3  SIGMA=   7.8  PHAS=   102.7  FOM=  0.85  TEST= 0
INDE  6  19   7  FOBS=  238.5  SIGMA=   0.5  PHAS=   -85.3  FOM=  0.93  TEST= 0
INDE  6  19   9  FOBS=  104.7  SIGMA=   0.6  PHAS=    77.5  FOM=  0.95  TEST= 0
INDE  6  19  11  FOBS=  155.5  SIGMA=   0.5  PHAS=    11.8  FOM=  0.82  TEST= 0
INDE  6  19  13  FOBS=   60.8  SIGMA=   1.3  PHAS=    31.7  FOM=  0.96  TEST= 1
INDE  6  19  15  FOBS=  143.2  SIGMA=   0.7  PHAS=    13.7  FOM=  0.92  TEST= 0
INDE  6  19  17  FOBS=  113.9  SIGMA=   0.7  PHAS=   -44.0  FOM=  0.75  TEST= 0
INDE  6  19  19  FOBS=   40.2  SIGMA=   1.6  PHAS=  -135.0  FOM=  0.92  TEST= 0
INDE  6  19  21  FOBS=   52.4  SIGMA=   1.3  PHAS=  -134.7  FOM=  0.98  TEST= 0
INDE  6  19  23  FOBS=  211.4  SIGMA=   0.5  PHAS=  -134.3  FOM=  0.97  TEST= 0
INDE  6  19  25  FOBS=   28.7  SIGMA=   2.6  PHAS=    47.9  FOM=  0.14  TEST= 0
INDE  6  19  27  FOBS=   99.8  SIGMA=   0.9  PHAS=    26.8  FOM=  0.89  TEST= 0
INDE  6  19  29  FOBS=  251.2  SIGMA=   0.6  PHAS=   -29.6  FOM=  0.98  TEST= 0
INDE  6  19  31  FOBS=  252.3  SIGMA=   0.6  PHAS=    92.2  FOM=  0.98  TEST= 0
INDE  6  19  33  FOBS=  101.3  SIGMA=   1.1  PHAS=   156.3  FOM=  0.77  TEST= 0
INDE  6  19  35  FOBS=  289.3  SIGMA=   0.6  PHAS=   166.8  FOM=  0.98  TEST= 1
INDE  6  19  37  FOBS=  312.6  SIGMA=   0.6  PHAS=   130.2  FOM=  0.96  TEST= 0
INDE  6  19  39  FOBS=  198.2  SIGMA=   0.8  PHAS=    32.9  FOM=  0.94  TEST= 0
INDE  6  19  41  FOBS=  196.1  SIGMA=   0.9  PHAS=    15.8  FOM=  0.89  TEST= 0
INDE  6  19  43  FOBS=   89.7  SIGMA=   1.9  PHAS=  -117.4  FOM=  0.46  TEST= 0
INDE  6  19  45  FOBS=  148.0  SIGMA=   1.3  PHAS=     4.0  FOM=  0.92  TEST= 0
INDE  6  19  47  FOBS=   66.1  SIGMA=   2.0  PHAS=     4.9  FOM=  0.33  TEST= 0
INDE  6  19  49  FOBS=   80.8  SIGMA=   1.9  PHAS=  -121.7  FOM=  0.37  TEST= 0
INDE  6  19  51  FOBS=  207.0  SIGMA=   1.1  PHAS=   132.3  FOM=  0.96  TEST= 0
INDE  6  19  53  FOBS=  146.7  SIGMA=   1.5  PHAS=    43.1  FOM=  0.93  TEST= 0
INDE  6  19  55  FOBS=   56.3  SIGMA=   3.6  PHAS=   -92.4  FOM=  0.82  TEST= 0
```

*FIG. 12A - 165*

| | | | | | | | | | | | | |
|---|---|---|---|---|---|---|---|---|---|---|---|---|
| INDE | 6 | 19 | 57 | FOBS= | 94.4 | SIGMA= | 2.2 | PHAS= | 142.5 | FOM= | 0.80 | TEST= 0 |
| INDE | 6 | 19 | 59 | FOBS= | 28.7 | SIGMA= | 6.9 | PHAS= | 142.7 | FOM= | 0.16 | TEST= 0 |
| INDE | 6 | 19 | 61 | FOBS= | 0.0 | SIGMA= | 20.3 | PHAS= | 0.0 | FOM= | 0.00 | TEST= 0 |
| INDE | 6 | 19 | 63 | FOBS= | 158.9 | SIGMA= | 1.6 | PHAS= | 168.1 | FOM= | 0.13 | TEST= 1 |
| INDE | 6 | 19 | 65 | FOBS= | 92.0 | SIGMA= | 4.8 | PHAS= | -66.4 | FOM= | 0.92 | TEST= 0 |
| INDE | 6 | 19 | 67 | FOBS= | 53.0 | SIGMA= | 8.4 | PHAS= | -163.9 | FOM= | 0.35 | TEST= 0 |
| INDE | 6 | 19 | 69 | FOBS= | 55.7 | SIGMA= | 8.1 | PHAS= | -168.0 | FOM= | 0.80 | TEST= 0 |
| INDE | 6 | 19 | 71 | FOBS= | 72.1 | SIGMA= | 6.4 | PHAS= | 15.4 | FOM= | 0.91 | TEST= 0 |
| INDE | 6 | 19 | 73 | FOBS= | 46.2 | SIGMA= | 7.3 | PHAS= | 65.8 | FOM= | 0.86 | TEST= 0 |
| INDE | 6 | 19 | 75 | FOBS= | 0.0 | SIGMA= | 31.7 | PHAS= | 0.0 | FOM= | 0.00 | TEST= 0 |
| INDE | 6 | 20 | 6 | FOBS= | 410.0 | SIGMA= | 0.5 | PHAS= | 108.9 | FOM= | 0.96 | TEST= 0 |
| INDE | 6 | 20 | 8 | FOBS= | 137.5 | SIGMA= | 0.7 | PHAS= | -125.7 | FOM= | 0.83 | TEST= 1 |
| INDE | 6 | 20 | 10 | FOBS= | 131.7 | SIGMA= | 0.6 | PHAS= | -94.6 | FOM= | 0.74 | TEST= 0 |
| INDE | 6 | 20 | 12 | FOBS= | 166.2 | SIGMA= | 0.5 | PHAS= | -167.8 | FOM= | 0.58 | TEST= 1 |
| INDE | 6 | 20 | 14 | FOBS= | 139.3 | SIGMA= | 0.7 | PHAS= | -63.2 | FOM= | 0.78 | TEST= 0 |
| INDE | 6 | 20 | 16 | FOBS= | 50.8 | SIGMA= | 1.7 | PHAS= | 33.4 | FOM= | 0.91 | TEST= 0 |
| INDE | 6 | 20 | 18 | FOBS= | 103.4 | SIGMA= | 0.8 | PHAS= | -55.1 | FOM= | 0.98 | TEST= 0 |
| INDE | 6 | 20 | 20 | FOBS= | 124.0 | SIGMA= | 0.7 | PHAS= | -125.7 | FOM= | 0.94 | TEST= 1 |
| INDE | 6 | 20 | 22 | FOBS= | 229.8 | SIGMA= | 0.5 | PHAS= | -152.8 | FOM= | 0.97 | TEST= 0 |
| INDE | 6 | 20 | 24 | FOBS= | 150.7 | SIGMA= | 0.7 | PHAS= | 139.1 | FOM= | 0.99 | TEST= 0 |
| INDE | 6 | 20 | 26 | FOBS= | 112.2 | SIGMA= | 0.9 | PHAS= | 98.8 | FOM= | 0.88 | TEST= 0 |
| INDE | 6 | 20 | 28 | FOBS= | 139.5 | SIGMA= | 0.8 | PHAS= | -92.2 | FOM= | 0.99 | TEST= 0 |
| INDE | 6 | 20 | 30 | FOBS= | 120.9 | SIGMA= | 0.8 | PHAS= | -73.1 | FOM= | 0.92 | TEST= 0 |
| INDE | 6 | 20 | 32 | FOBS= | 238.2 | SIGMA= | 0.6 | PHAS= | 9.2 | FOM= | 0.94 | TEST= 0 |
| INDE | 6 | 20 | 34 | FOBS= | 130.8 | SIGMA= | 1.0 | PHAS= | 111.7 | FOM= | 0.91 | TEST= 0 |
| INDE | 6 | 20 | 36 | FOBS= | 198.6 | SIGMA= | 0.8 | PHAS= | 84.3 | FOM= | 0.96 | TEST= 0 |
| INDE | 6 | 20 | 38 | FOBS= | 212.0 | SIGMA= | 0.8 | PHAS= | -81.0 | FOM= | 0.94 | TEST= 0 |
| INDE | 6 | 20 | 40 | FOBS= | 232.1 | SIGMA= | 0.8 | PHAS= | 55.2 | FOM= | 0.94 | TEST= 0 |
| INDE | 6 | 20 | 42 | FOBS= | 218.8 | SIGMA= | 0.9 | PHAS= | -129.2 | FOM= | 0.99 | TEST= 0 |
| INDE | 6 | 20 | 44 | FOBS= | 120.8 | SIGMA= | 1.5 | PHAS= | -149.1 | FOM= | 0.78 | TEST= 0 |
| INDE | 6 | 20 | 46 | FOBS= | 258.6 | SIGMA= | 0.8 | PHAS= | -76.9 | FOM= | 0.91 | TEST= 1 |
| INDE | 6 | 20 | 48 | FOBS= | 139.4 | SIGMA= | 1.0 | PHAS= | -79.0 | FOM= | 0.86 | TEST= 0 |
| INDE | 6 | 20 | 50 | FOBS= | 115.9 | SIGMA= | 1.3 | PHAS= | 88.8 | FOM= | 0.86 | TEST= 0 |
| INDE | 6 | 20 | 52 | FOBS= | 106.7 | SIGMA= | 2.0 | PHAS= | -7.7 | FOM= | 0.92 | TEST= 0 |
| INDE | 6 | 20 | 54 | FOBS= | 131.5 | SIGMA= | 1.7 | PHAS= | -120.8 | FOM= | 0.90 | TEST= 0 |
| INDE | 6 | 20 | 56 | FOBS= | 130.2 | SIGMA= | 1.7 | PHAS= | -97.4 | FOM= | 0.89 | TEST= 0 |
| INDE | 6 | 20 | 58 | FOBS= | 114.8 | SIGMA= | 1.8 | PHAS= | 30.9 | FOM= | 0.78 | TEST= 0 |
| INDE | 6 | 20 | 60 | FOBS= | 59.7 | SIGMA= | 3.3 | PHAS= | -74.8 | FOM= | 0.79 | TEST= 0 |
| INDE | 6 | 20 | 62 | FOBS= | 75.0 | SIGMA= | 3.2 | PHAS= | 143.5 | FOM= | 0.76 | TEST= 0 |
| INDE | 6 | 20 | 64 | FOBS= | 0.0 | SIGMA= | 30.1 | PHAS= | 0.0 | FOM= | 0.00 | TEST= 0 |
| INDE | 6 | 20 | 66 | FOBS= | 80.3 | SIGMA= | 5.6 | PHAS= | -151.0 | FOM= | 0.85 | TEST= 0 |
| INDE | 6 | 20 | 68 | FOBS= | 54.8 | SIGMA= | 8.3 | PHAS= | 10.0 | FOM= | 0.63 | TEST= 0 |
| INDE | 6 | 20 | 70 | FOBS= | 12.8 | SIGMA= | 35.2 | PHAS= | -128.5 | FOM= | 0.19 | TEST= 0 |
| INDE | 6 | 20 | 72 | FOBS= | 27.2 | SIGMA= | 17.1 | PHAS= | -144.7 | FOM= | 0.38 | TEST= 0 |
| INDE | 6 | 20 | 74 | FOBS= | 54.1 | SIGMA= | 6.4 | PHAS= | -129.0 | FOM= | 0.08 | TEST= 1 |
| INDE | 6 | 21 | 7 | FOBS= | 344.0 | SIGMA= | 0.5 | PHAS= | 45.1 | FOM= | 0.92 | TEST= 0 |
| INDE | 6 | 21 | 9 | FOBS= | 48.3 | SIGMA= | 1.5 | PHAS= | 144.4 | FOM= | 0.96 | TEST= 0 |
| INDE | 6 | 21 | 11 | FOBS= | 156.2 | SIGMA= | 0.6 | PHAS= | -155.5 | FOM= | 0.98 | TEST= 0 |
| INDE | 6 | 21 | 13 | FOBS= | 264.6 | SIGMA= | 0.6 | PHAS= | 140.5 | FOM= | 0.96 | TEST= 0 |
| INDE | 6 | 21 | 15 | FOBS= | 152.8 | SIGMA= | 0.9 | PHAS= | 15.5 | FOM= | 0.96 | TEST= 0 |
| INDE | 6 | 21 | 17 | FOBS= | 75.5 | SIGMA= | 1.4 | PHAS= | -51.7 | FOM= | 0.95 | TEST= 0 |
| INDE | 6 | 21 | 19 | FOBS= | 174.4 | SIGMA= | 0.7 | PHAS= | -169.8 | FOM= | 0.99 | TEST= 0 |
| INDE | 6 | 21 | 21 | FOBS= | 196.1 | SIGMA= | 0.6 | PHAS= | 96.9 | FOM= | 0.93 | TEST= 0 |
| INDE | 6 | 21 | 23 | FOBS= | 220.9 | SIGMA= | 0.5 | PHAS= | 150.7 | FOM= | 0.96 | TEST= 1 |
| INDE | 6 | 21 | 25 | FOBS= | 135.5 | SIGMA= | 0.8 | PHAS= | 75.6 | FOM= | 0.99 | TEST= 0 |
| INDE | 6 | 21 | 27 | FOBS= | 83.1 | SIGMA= | 1.2 | PHAS= | 25.1 | FOM= | 0.96 | TEST= 0 |
| INDE | 6 | 21 | 29 | FOBS= | 143.2 | SIGMA= | 0.8 | PHAS= | -48.9 | FOM= | 0.99 | TEST= 0 |
| INDE | 6 | 21 | 31 | FOBS= | 158.1 | SIGMA= | 0.7 | PHAS= | 162.7 | FOM= | 0.92 | TEST= 0 |
| INDE | 6 | 21 | 33 | FOBS= | 159.0 | SIGMA= | 0.8 | PHAS= | -43.1 | FOM= | 0.96 | TEST= 0 |
| INDE | 6 | 21 | 35 | FOBS= | 112.1 | SIGMA= | 1.2 | PHAS= | -57.3 | FOM= | 0.95 | TEST= 0 |
| INDE | 6 | 21 | 37 | FOBS= | 248.6 | SIGMA= | 0.9 | PHAS= | 108.1 | FOM= | 0.95 | TEST= 0 |
| INDE | 6 | 21 | 39 | FOBS= | 62.8 | SIGMA= | 2.5 | PHAS= | 69.3 | FOM= | 0.68 | TEST= 0 |
| INDE | 6 | 21 | 41 | FOBS= | 124.4 | SIGMA= | 1.4 | PHAS= | -35.2 | FOM= | 0.86 | TEST= 0 |
| INDE | 6 | 21 | 43 | FOBS= | 72.6 | SIGMA= | 2.5 | PHAS= | 105.1 | FOM= | 0.67 | TEST= 0 |
| INDE | 6 | 21 | 45 | FOBS= | 151.1 | SIGMA= | 1.3 | PHAS= | 162.3 | FOM= | 0.90 | TEST= 0 |
| INDE | 6 | 21 | 47 | FOBS= | 103.6 | SIGMA= | 1.3 | PHAS= | -155.3 | FOM= | 0.92 | TEST= 0 |
| INDE | 6 | 21 | 49 | FOBS= | 109.7 | SIGMA= | 1.4 | PHAS= | -139.4 | FOM= | 0.89 | TEST= 0 |
| INDE | 6 | 21 | 51 | FOBS= | 223.4 | SIGMA= | 1.1 | PHAS= | 162.0 | FOM= | 0.95 | TEST= 0 |
| INDE | 6 | 21 | 53 | FOBS= | 90.2 | SIGMA= | 2.4 | PHAS= | 124.0 | FOM= | 0.83 | TEST= 0 |
| INDE | 6 | 21 | 55 | FOBS= | 169.9 | SIGMA= | 1.3 | PHAS= | -178.6 | FOM= | 0.95 | TEST= 0 |

*FIG. 12A - 166*

```
INDE  6  21  57  FOBS=   41.8  SIGMA=   4.9  PHAS=   76.1  FOM= 0.19  TEST= 1
INDE  6  21  59  FOBS=   59.2  SIGMA=   3.4  PHAS= -159.8  FOM= 0.78  TEST= 0
INDE  6  21  61  FOBS=    0.0  SIGMA=  20.4  PHAS=    0.0  FOM= 0.00  TEST= 0
INDE  6  21  63  FOBS=   35.7  SIGMA=   7.5  PHAS= -106.4  FOM= 0.14  TEST= 1
INDE  6  21  65  FOBS=    0.0  SIGMA=  30.0  PHAS=    0.0  FOM= 0.00  TEST= 0
INDE  6  21  67  FOBS=   35.0  SIGMA=  12.7  PHAS=  -50.0  FOM= 0.16  TEST= 1
INDE  6  21  69  FOBS=   44.3  SIGMA=  10.2  PHAS= -118.7  FOM= 0.51  TEST= 0
INDE  6  21  71  FOBS=   10.0  SIGMA=  46.3  PHAS= -174.4  FOM= 0.21  TEST= 0
INDE  6  21  73  FOBS=   80.8  SIGMA=   5.9  PHAS=  118.8  FOM= 0.92  TEST= 0
INDE  6  22   6  FOBS=  179.1  SIGMA=   0.5  PHAS=  -61.2  FOM= 0.40  TEST= 1
INDE  6  22   8  FOBS=  132.1  SIGMA=   0.6  PHAS=  -12.9  FOM= 0.92  TEST= 0
INDE  6  22  10  FOBS=  157.2  SIGMA=   0.7  PHAS=  173.2  FOM= 0.93  TEST= 0
INDE  6  22  12  FOBS=  341.1  SIGMA=   0.6  PHAS=  117.1  FOM= 0.99  TEST= 0
INDE  6  22  14  FOBS=  193.5  SIGMA=   0.7  PHAS=   53.5  FOM= 0.96  TEST= 0
INDE  6  22  16  FOBS=   64.7  SIGMA=   1.9  PHAS=  171.1  FOM= 0.29  TEST= 1
INDE  6  22  18  FOBS=   71.0  SIGMA=   1.6  PHAS= -171.6  FOM= 0.97  TEST= 0
INDE  6  22  20  FOBS=  195.7  SIGMA=   0.7  PHAS=  -29.2  FOM= 0.94  TEST= 0
INDE  6  22  22  FOBS=   40.8  SIGMA=   2.2  PHAS= -137.0  FOM= 0.88  TEST= 0
INDE  6  22  24  FOBS=  152.0  SIGMA=   0.7  PHAS=  -93.2  FOM= 0.94  TEST= 0
INDE  6  22  26  FOBS=  135.9  SIGMA=   0.9  PHAS=   23.5  FOM= 0.95  TEST= 0
INDE  6  22  28  FOBS=  178.1  SIGMA=   0.7  PHAS=  168.8  FOM= 0.85  TEST= 0
INDE  6  22  30  FOBS=  103.3  SIGMA=   1.1  PHAS=   70.2  FOM= 0.99  TEST= 0
INDE  6  22  32  FOBS=  259.2  SIGMA=   0.6  PHAS=   23.8  FOM= 0.92  TEST= 0
INDE  6  22  34  FOBS=   75.2  SIGMA=   1.8  PHAS=  144.2  FOM= 0.91  TEST= 1
INDE  6  22  36  FOBS=   93.6  SIGMA=   1.5  PHAS=  147.4  FOM= 0.62  TEST= 0
INDE  6  22  38  FOBS=  154.9  SIGMA=   1.0  PHAS= -145.8  FOM= 0.94  TEST= 0
INDE  6  22  40  FOBS=  140.4  SIGMA=   1.3  PHAS=   30.2  FOM= 0.91  TEST= 0
INDE  6  22  42  FOBS=  215.3  SIGMA=   0.9  PHAS=  -99.2  FOM= 0.92  TEST= 0
INDE  6  22  44  FOBS=  119.4  SIGMA=   1.6  PHAS=   78.2  FOM= 0.72  TEST= 1
INDE  6  22  46  FOBS=  119.3  SIGMA=   1.5  PHAS= -180.0  FOM= 0.75  TEST= 0
INDE  6  22  48  FOBS=  119.5  SIGMA=   1.1  PHAS=   75.3  FOM= 0.86  TEST= 0
INDE  6  22  50  FOBS=  137.4  SIGMA=   1.1  PHAS=   83.4  FOM= 0.91  TEST= 0
INDE  6  22  52  FOBS=   59.6  SIGMA=   2.2  PHAS=  -12.7  FOM= 0.30  TEST= 0
INDE  6  22  54  FOBS=  146.7  SIGMA=   1.2  PHAS=  169.6  FOM= 0.39  TEST= 1
INDE  6  22  56  FOBS=  109.3  SIGMA=   2.0  PHAS=  178.1  FOM= 0.72  TEST= 1
INDE  6  22  58  FOBS=   69.7  SIGMA=   3.0  PHAS=   91.4  FOM= 0.82  TEST= 0
INDE  6  22  60  FOBS=    0.0  SIGMA=  20.6  PHAS=    0.0  FOM= 0.00  TEST= 0
INDE  6  22  62  FOBS=   45.4  SIGMA=   5.9  PHAS=  157.9  FOM= 0.80  TEST= 0
INDE  6  22  64  FOBS=   47.2  SIGMA=   9.5  PHAS=   79.0  FOM= 0.55  TEST= 0
INDE  6  22  66  FOBS=    0.0  SIGMA=  30.0  PHAS=    0.0  FOM= 0.00  TEST= 0
INDE  6  22  68  FOBS=   21.8  SIGMA=  20.9  PHAS= -126.1  FOM= 0.31  TEST= 0
INDE  6  22  70  FOBS=   43.7  SIGMA=  10.5  PHAS=  133.6  FOM= 0.28  TEST= 0
INDE  6  22  72  FOBS=   35.2  SIGMA=  13.5  PHAS=   60.4  FOM= 0.74  TEST= 0
INDE  6  22  74  FOBS=    0.0  SIGMA=  26.6  PHAS=    0.0  FOM= 0.00  TEST= 0
INDE  6  23   7  FOBS=   50.7  SIGMA=   1.3  PHAS=  149.5  FOM= 0.91  TEST= 0
INDE  6  23   9  FOBS=  246.1  SIGMA=   0.7  PHAS=  160.4  FOM= 0.95  TEST= 0
INDE  6  23  11  FOBS=  139.0  SIGMA=   0.7  PHAS=   37.4  FOM= 0.91  TEST= 0
INDE  6  23  13  FOBS=  319.3  SIGMA=   0.7  PHAS=   18.0  FOM= 0.99  TEST= 0
INDE  6  23  15  FOBS=  287.8  SIGMA=   0.7  PHAS=   35.4  FOM= 0.96  TEST= 0
INDE  6  23  17  FOBS=  136.0  SIGMA=   1.1  PHAS=   92.1  FOM= 0.89  TEST= 0
INDE  6  23  19  FOBS=  269.6  SIGMA=   0.7  PHAS= -133.4  FOM= 0.97  TEST= 0
INDE  6  23  21  FOBS=   84.6  SIGMA=   1.2  PHAS=   87.1  FOM= 0.98  TEST= 0
INDE  6  23  23  FOBS=  405.9  SIGMA=   0.5  PHAS=  171.9  FOM= 0.96  TEST= 0
INDE  6  23  25  FOBS=  184.5  SIGMA=   0.7  PHAS= -163.5  FOM= 0.65  TEST= 1
INDE  6  23  27  FOBS=   70.4  SIGMA=   1.6  PHAS=  169.9  FOM= 0.95  TEST= 0
INDE  6  23  29  FOBS=  175.7  SIGMA=   0.8  PHAS=   50.7  FOM= 0.98  TEST= 0
INDE  6  23  31  FOBS=  204.9  SIGMA=   0.7  PHAS=   -4.5  FOM= 0.86  TEST= 1
INDE  6  23  33  FOBS=  429.2  SIGMA=   0.5  PHAS=  -65.2  FOM= 0.97  TEST= 0
INDE  6  23  35  FOBS=  329.0  SIGMA=   0.6  PHAS=   90.4  FOM= 0.90  TEST= 1
INDE  6  23  37  FOBS=  236.7  SIGMA=   0.7  PHAS=   57.8  FOM= 0.96  TEST= 0
INDE  6  23  39  FOBS=   60.7  SIGMA=   2.9  PHAS=  140.6  FOM= 0.72  TEST= 0
INDE  6  23  41  FOBS=   47.6  SIGMA=   3.7  PHAS= -151.3  FOM= 0.52  TEST= 0
INDE  6  23  43  FOBS=   93.4  SIGMA=   2.0  PHAS=  -16.2  FOM= 0.91  TEST= 0
INDE  6  23  45  FOBS=  173.2  SIGMA=   1.1  PHAS=   96.6  FOM= 0.93  TEST= 0
INDE  6  23  47  FOBS=  180.3  SIGMA=   0.9  PHAS=   21.7  FOM= 0.91  TEST= 0
INDE  6  23  49  FOBS=  189.8  SIGMA=   0.9  PHAS=  -72.0  FOM= 0.95  TEST= 0
INDE  6  23  51  FOBS=  140.4  SIGMA=   1.0  PHAS=  122.7  FOM= 0.95  TEST= 0
INDE  6  23  53  FOBS=  172.3  SIGMA=   1.2  PHAS=  122.1  FOM= 0.93  TEST= 0
INDE  6  23  55  FOBS=   86.5  SIGMA=   1.9  PHAS=  138.6  FOM= 0.91  TEST= 0
INDE  6  23  57  FOBS=  102.0  SIGMA=   2.1  PHAS=   79.5  FOM= 0.91  TEST= 0
```

*FIG. 12A - 167*

```
INDE  6  23  59  FOBS=    0.0  SIGMA=  20.1  PHAS=    0.0  FOM= 0.00  TEST= 0
INDE  6  23  61  FOBS=    0.0  SIGMA=  21.8  PHAS=    0.0  FOM= 0.00  TEST= 0
INDE  6  23  63  FOBS=  103.2  SIGMA=   3.2  PHAS=   48.9  FOM= 0.89  TEST= 0
INDE  6  23  65  FOBS=   36.4  SIGMA=  12.4  PHAS= -174.0  FOM= 0.05  TEST= 1
INDE  6  23  67  FOBS=   36.9  SIGMA=  12.3  PHAS=   85.1  FOM= 0.11  TEST= 0
INDE  6  23  69  FOBS=   52.7  SIGMA=   8.8  PHAS= -105.1  FOM= 0.23  TEST= 0
INDE  6  23  71  FOBS=    0.0  SIGMA=  30.6  PHAS=    0.0  FOM= 0.00  TEST= 0
INDE  6  23  73  FOBS=   29.3  SIGMA=  16.7  PHAS= -111.4  FOM= 0.29  TEST= 0
INDE  6  24   6  FOBS=  147.9  SIGMA=   0.6  PHAS=   70.7  FOM= 0.98  TEST= 0
INDE  6  24   8  FOBS=  322.3  SIGMA=   0.5  PHAS=   75.2  FOM= 0.99  TEST= 1
INDE  6  24  10  FOBS=   94.8  SIGMA=   0.9  PHAS=  165.9  FOM= 0.92  TEST= 0
INDE  6  24  12  FOBS=   83.0  SIGMA=   1.1  PHAS=  166.8  FOM= 0.69  TEST= 0
INDE  6  24  14  FOBS=  122.5  SIGMA=   0.8  PHAS=  -24.4  FOM= 0.95  TEST= 0
INDE  6  24  16  FOBS=  186.5  SIGMA=   0.9  PHAS=  -23.8  FOM= 0.94  TEST= 0
INDE  6  24  18  FOBS=  351.9  SIGMA=   0.7  PHAS=  108.8  FOM= 0.99  TEST= 0
INDE  6  24  20  FOBS=  103.5  SIGMA=   1.2  PHAS=  -41.4  FOM= 0.64  TEST= 0
INDE  6  24  22  FOBS=  278.2  SIGMA=   0.6  PHAS=   43.1  FOM= 0.99  TEST= 0
INDE  6  24  24  FOBS=  173.7  SIGMA=   0.7  PHAS=   90.5  FOM= 0.89  TEST= 0
INDE  6  24  26  FOBS=  221.6  SIGMA=   0.6  PHAS=   80.8  FOM= 0.99  TEST= 1
INDE  6  24  28  FOBS=  303.5  SIGMA=   0.6  PHAS=   59.5  FOM= 0.98  TEST= 0
INDE  6  24  30  FOBS=  174.6  SIGMA=   0.8  PHAS=  -50.2  FOM= 0.92  TEST= 0
INDE  6  24  32  FOBS=  321.6  SIGMA=   0.6  PHAS=  -81.6  FOM= 0.95  TEST= 0
INDE  6  24  34  FOBS=  378.6  SIGMA=   0.6  PHAS=  -81.7  FOM= 0.96  TEST= 0
INDE  6  24  36  FOBS=  167.4  SIGMA=   0.9  PHAS=  -52.9  FOM= 0.83  TEST= 0
INDE  6  24  38  FOBS=  176.7  SIGMA=   1.0  PHAS=  121.9  FOM= 0.96  TEST= 1
INDE  6  24  40  FOBS=    0.0  SIGMA=  18.6  PHAS=    0.0  FOM= 0.00  TEST= 0
INDE  6  24  42  FOBS=  195.5  SIGMA=   1.1  PHAS=  163.9  FOM= 0.98  TEST= 0
INDE  6  24  44  FOBS=   29.7  SIGMA=   6.7  PHAS= -155.6  FOM= 0.30  TEST= 0
INDE  6  24  46  FOBS=  184.6  SIGMA=   1.1  PHAS=  -32.8  FOM= 0.85  TEST= 0
INDE  6  24  48  FOBS=   36.7  SIGMA=   3.8  PHAS=   64.9  FOM= 0.37  TEST= 0
INDE  6  24  50  FOBS=  113.8  SIGMA=   1.2  PHAS=  119.7  FOM= 0.81  TEST= 0
INDE  6  24  52  FOBS=  119.1  SIGMA=   1.3  PHAS=   -5.0  FOM= 0.93  TEST= 0
INDE  6  24  54  FOBS=  100.8  SIGMA=   1.3  PHAS=   46.3  FOM= 0.92  TEST= 0
INDE  6  24  56  FOBS=   43.9  SIGMA=   3.9  PHAS= -131.0  FOM= 0.70  TEST= 0
INDE  6  24  58  FOBS=   61.4  SIGMA=   3.4  PHAS=   41.5  FOM= 0.75  TEST= 0
INDE  6  24  60  FOBS=   46.3  SIGMA=   4.8  PHAS=  -79.7  FOM= 0.60  TEST= 0
INDE  6  24  62  FOBS=    0.0  SIGMA=  23.5  PHAS=    0.0  FOM= 0.00  TEST= 0
INDE  6  24  64  FOBS=   83.0  SIGMA=   5.6  PHAS=  -82.7  FOM= 0.89  TEST= 0
INDE  6  24  66  FOBS=   43.1  SIGMA=  10.5  PHAS=  -97.1  FOM= 0.37  TEST= 0
INDE  6  24  68  FOBS=   67.2  SIGMA=   6.9  PHAS=   57.5  FOM= 0.83  TEST= 0
INDE  6  24  70  FOBS=   19.7  SIGMA=  23.7  PHAS= -155.9  FOM= 0.43  TEST= 0
INDE  6  24  72  FOBS=   76.4  SIGMA=   6.5  PHAS=   99.4  FOM= 0.02  TEST= 1
INDE  6  25   7  FOBS=  267.2  SIGMA=   0.5  PHAS=  -16.2  FOM= 0.94  TEST= 0
INDE  6  25   9  FOBS=  182.1  SIGMA=   0.7  PHAS=   55.0  FOM= 0.99  TEST= 0
INDE  6  25  11  FOBS=  169.2  SIGMA=   0.6  PHAS=   10.9  FOM= 0.90  TEST= 1
INDE  6  25  13  FOBS=  289.7  SIGMA=   0.7  PHAS=   -8.6  FOM= 0.96  TEST= 1
INDE  6  25  15  FOBS=   76.7  SIGMA=   1.6  PHAS=   77.9  FOM= 0.94  TEST= 0
INDE  6  25  17  FOBS=  191.7  SIGMA=   0.9  PHAS=   15.3  FOM= 0.99  TEST= 0
INDE  6  25  19  FOBS=   69.3  SIGMA=   1.8  PHAS= -171.4  FOM= 0.44  TEST= 0
INDE  6  25  21  FOBS=  109.0  SIGMA=   1.1  PHAS=  -95.6  FOM= 0.95  TEST= 0
INDE  6  25  23  FOBS=  267.1  SIGMA=   0.6  PHAS= -121.2  FOM= 0.99  TEST= 0
INDE  6  25  25  FOBS=  218.3  SIGMA=   0.7  PHAS=  -68.0  FOM= 0.98  TEST= 0
INDE  6  25  27  FOBS=   81.6  SIGMA=   1.5  PHAS=   -2.3  FOM= 0.98  TEST= 1
INDE  6  25  29  FOBS=  106.8  SIGMA=   1.2  PHAS=  -52.7  FOM= 0.53  TEST= 0
INDE  6  25  31  FOBS=  125.9  SIGMA=   1.1  PHAS= -100.8  FOM= 0.89  TEST= 0
INDE  6  25  33  FOBS=  192.9  SIGMA=   0.9  PHAS= -169.6  FOM= 0.96  TEST= 1
INDE  6  25  35  FOBS=   89.9  SIGMA=   1.5  PHAS=  142.7  FOM= 0.95  TEST= 0
INDE  6  25  37  FOBS=   58.2  SIGMA=   2.5  PHAS=  151.8  FOM= 0.99  TEST= 0
INDE  6  25  39  FOBS=  181.5  SIGMA=   1.0  PHAS=   59.2  FOM= 0.89  TEST= 0
INDE  6  25  41  FOBS=  247.5  SIGMA=   0.9  PHAS=   35.4  FOM= 0.96  TEST= 0
INDE  6  25  43  FOBS=  206.9  SIGMA=   1.0  PHAS=   40.5  FOM= 0.95  TEST= 0
INDE  6  25  45  FOBS=   21.3  SIGMA=   8.8  PHAS=  -42.1  FOM= 0.49  TEST= 0
INDE  6  25  47  FOBS=  138.8  SIGMA=   1.3  PHAS=  -33.4  FOM= 0.92  TEST= 0
INDE  6  25  49  FOBS=   97.6  SIGMA=   1.4  PHAS=  -52.4  FOM= 0.79  TEST= 0
INDE  6  25  51  FOBS=  143.9  SIGMA=   1.1  PHAS=  -56.2  FOM= 0.60  TEST= 0
INDE  6  25  53  FOBS=   73.9  SIGMA=   1.8  PHAS=  100.0  FOM= 0.75  TEST= 0
INDE  6  25  55  FOBS=   92.9  SIGMA=   1.4  PHAS=   50.5  FOM= 0.86  TEST= 0
INDE  6  25  57  FOBS=   53.6  SIGMA=   3.2  PHAS=  119.6  FOM= 0.87  TEST= 0
INDE  6  25  59  FOBS=  117.5  SIGMA=   2.2  PHAS= -136.2  FOM= 0.88  TEST= 0
INDE  6  25  61  FOBS=   54.7  SIGMA=   4.5  PHAS=  172.7  FOM= 0.74  TEST= 0
```

*FIG. 12A - 168*

| | | | | | | | | | | | |
|---|---|---|---|---|---|---|---|---|---|---|---|
| INDE | 6 | 25 | 63 | FOBS= | 25.5 | SIGMA= | 12.3 | PHAS= | -37.7 | FOM= | 0.44 | TEST= 0 |
| INDE | 6 | 25 | 65 | FOBS= | 49.1 | SIGMA= | 9.3 | PHAS= | -176.5 | FOM= | 0.73 | TEST= 0 |
| INDE | 6 | 25 | 67 | FOBS= | 43.3 | SIGMA= | 10.7 | PHAS= | 37.3 | FOM= | 0.58 | TEST= 0 |
| INDE | 6 | 25 | 69 | FOBS= | 25.5 | SIGMA= | 18.2 | PHAS= | 53.6 | FOM= | 0.27 | TEST= 0 |
| INDE | 6 | 25 | 71 | FOBS= | 59.0 | SIGMA= | 8.1 | PHAS= | -6.0 | FOM= | 0.04 | TEST= 1 |
| INDE | 6 | 25 | 73 | FOBS= | 30.7 | SIGMA= | 16.4 | PHAS= | 148.8 | FOM= | 0.01 | TEST= 1 |
| INDE | 6 | 26 | 6 | FOBS= | 138.3 | SIGMA= | 0.6 | PHAS= | -114.1 | FOM= | 0.94 | TEST= 0 |
| INDE | 6 | 26 | 8 | FOBS= | 58.5 | SIGMA= | 1.2 | PHAS= | 90.0 | FOM= | 0.92 | TEST= 0 |
| INDE | 6 | 26 | 10 | FOBS= | 103.5 | SIGMA= | 0.9 | PHAS= | -110.4 | FOM= | 0.84 | TEST= 0 |
| INDE | 6 | 26 | 12 | FOBS= | 171.9 | SIGMA= | 0.7 | PHAS= | -103.9 | FOM= | 0.98 | TEST= 1 |
| INDE | 6 | 26 | 14 | FOBS= | 86.6 | SIGMA= | 1.1 | PHAS= | -117.6 | FOM= | 0.90 | TEST= 0 |
| INDE | 6 | 26 | 16 | FOBS= | 41.2 | SIGMA= | 2.7 | PHAS= | 93.3 | FOM= | 0.95 | TEST= 0 |
| INDE | 6 | 26 | 18 | FOBS= | 299.0 | SIGMA= | 0.7 | PHAS= | -151.5 | FOM= | 0.98 | TEST= 1 |
| INDE | 6 | 26 | 20 | FOBS= | 117.2 | SIGMA= | 1.2 | PHAS= | -3.6 | FOM= | 0.90 | TEST= 1 |
| INDE | 6 | 26 | 22 | FOBS= | 111.5 | SIGMA= | 1.1 | PHAS= | 83.6 | FOM= | 0.98 | TEST= 0 |
| INDE | 6 | 26 | 24 | FOBS= | 290.9 | SIGMA= | 0.7 | PHAS= | 147.6 | FOM= | 0.97 | TEST= 0 |
| INDE | 6 | 26 | 26 | FOBS= | 59.6 | SIGMA= | 1.9 | PHAS= | 127.0 | FOM= | 0.87 | TEST= 0 |
| INDE | 6 | 26 | 28 | FOBS= | 221.9 | SIGMA= | 0.7 | PHAS= | 91.9 | FOM= | 0.95 | TEST= 0 |
| INDE | 6 | 26 | 30 | FOBS= | 292.6 | SIGMA= | 0.6 | PHAS= | -169.6 | FOM= | 0.94 | TEST= 1 |
| INDE | 6 | 26 | 32 | FOBS= | 49.7 | SIGMA= | 2.9 | PHAS= | 58.1 | FOM= | 0.17 | TEST= 0 |
| INDE | 6 | 26 | 34 | FOBS= | 37.8 | SIGMA= | 3.8 | PHAS= | -171.8 | FOM= | 0.38 | TEST= 0 |
| INDE | 6 | 26 | 36 | FOBS= | 178.8 | SIGMA= | 0.9 | PHAS= | 89.8 | FOM= | 0.96 | TEST= 0 |
| INDE | 6 | 26 | 38 | FOBS= | 169.6 | SIGMA= | 1.0 | PHAS= | 72.6 | FOM= | 0.92 | TEST= 0 |
| INDE | 6 | 26 | 40 | FOBS= | 274.0 | SIGMA= | 0.8 | PHAS= | -71.3 | FOM= | 0.96 | TEST= 0 |
| INDE | 6 | 26 | 42 | FOBS= | 161.7 | SIGMA= | 1.2 | PHAS= | -101.1 | FOM= | 0.94 | TEST= 0 |
| INDE | 6 | 26 | 44 | FOBS= | 114.0 | SIGMA= | 1.6 | PHAS= | -124.0 | FOM= | 0.83 | TEST= 0 |
| INDE | 6 | 26 | 46 | FOBS= | 94.9 | SIGMA= | 1.9 | PHAS= | -90.6 | FOM= | 0.89 | TEST= 0 |
| INDE | 6 | 26 | 48 | FOBS= | 196.4 | SIGMA= | 0.9 | PHAS= | -165.8 | FOM= | 0.88 | TEST= 0 |
| INDE | 6 | 26 | 50 | FOBS= | 133.3 | SIGMA= | 1.4 | PHAS= | -121.8 | FOM= | 0.84 | TEST= 0 |
| INDE | 6 | 26 | 52 | FOBS= | 128.0 | SIGMA= | 1.1 | PHAS= | 4.3 | FOM= | 0.81 | TEST= 0 |
| INDE | 6 | 26 | 54 | FOBS= | 99.1 | SIGMA= | 1.3 | PHAS= | -14.9 | FOM= | 0.89 | TEST= 0 |
| INDE | 6 | 26 | 56 | FOBS= | 84.1 | SIGMA= | 1.8 | PHAS= | -82.5 | FOM= | 0.85 | TEST= 0 |
| INDE | 6 | 26 | 58 | FOBS= | 140.4 | SIGMA= | 1.3 | PHAS= | 90.2 | FOM= | 0.89 | TEST= 0 |
| INDE | 6 | 26 | 60 | FOBS= | 72.0 | SIGMA= | 3.5 | PHAS= | 108.0 | FOM= | 0.81 | TEST= 0 |
| INDE | 6 | 26 | 62 | FOBS= | 96.3 | SIGMA= | 3.4 | PHAS= | 174.5 | FOM= | 0.88 | TEST= 0 |
| INDE | 6 | 26 | 64 | FOBS= | 82.9 | SIGMA= | 4.0 | PHAS= | 177.5 | FOM= | 0.82 | TEST= 0 |
| INDE | 6 | 26 | 66 | FOBS= | 45.8 | SIGMA= | 10.1 | PHAS= | -13.3 | FOM= | 0.30 | TEST= 0 |
| INDE | 6 | 26 | 68 | FOBS= | 0.0 | SIGMA= | 30.6 | PHAS= | 0.0 | FOM= | 0.00 | TEST= 0 |
| INDE | 6 | 26 | 70 | FOBS= | 52.6 | SIGMA= | 9.1 | PHAS= | 21.2 | FOM= | 0.71 | TEST= 0 |
| INDE | 6 | 26 | 72 | FOBS= | 65.5 | SIGMA= | 7.5 | PHAS= | -5.1 | FOM= | 0.84 | TEST= 0 |
| INDE | 6 | 27 | 7 | FOBS= | 178.0 | SIGMA= | 0.5 | PHAS= | 25.4 | FOM= | 0.93 | TEST= 0 |
| INDE | 6 | 27 | 9 | FOBS= | 31.5 | SIGMA= | 2.7 | PHAS= | 112.6 | FOM= | 0.86 | TEST= 0 |
| INDE | 6 | 27 | 11 | FOBS= | 124.4 | SIGMA= | 0.8 | PHAS= | 133.1 | FOM= | 0.97 | TEST= 0 |
| INDE | 6 | 27 | 13 | FOBS= | 45.7 | SIGMA= | 2.0 | PHAS= | 42.7 | FOM= | 0.94 | TEST= 0 |
| INDE | 6 | 27 | 15 | FOBS= | 149.3 | SIGMA= | 0.8 | PHAS= | 67.1 | FOM= | 0.96 | TEST= 0 |
| INDE | 6 | 27 | 17 | FOBS= | 319.3 | SIGMA= | 1.0 | PHAS= | 87.9 | FOM= | 0.99 | TEST= 0 |
| INDE | 6 | 27 | 19 | FOBS= | 95.3 | SIGMA= | 1.4 | PHAS= | 90.4 | FOM= | 0.95 | TEST= 0 |
| INDE | 6 | 27 | 21 | FOBS= | 207.1 | SIGMA= | 0.8 | PHAS= | -126.3 | FOM= | 0.95 | TEST= 0 |
| INDE | 6 | 27 | 23 | FOBS= | 168.7 | SIGMA= | 0.8 | PHAS= | 31.2 | FOM= | 0.84 | TEST= 0 |
| INDE | 6 | 27 | 25 | FOBS= | 335.2 | SIGMA= | 0.6 | PHAS= | -33.2 | FOM= | 0.95 | TEST= 0 |
| INDE | 6 | 27 | 27 | FOBS= | 100.5 | SIGMA= | 1.3 | PHAS= | -20.7 | FOM= | 0.94 | TEST= 0 |
| INDE | 6 | 27 | 29 | FOBS= | 0.0 | SIGMA= | 17.2 | PHAS= | 0.0 | FOM= | 0.00 | TEST= 0 |
| INDE | 6 | 27 | 31 | FOBS= | 70.7 | SIGMA= | 2.1 | PHAS= | -179.8 | FOM= | 0.95 | TEST= 1 |
| INDE | 6 | 27 | 33 | FOBS= | 151.4 | SIGMA= | 1.0 | PHAS= | 87.6 | FOM= | 0.98 | TEST= 0 |
| INDE | 6 | 27 | 35 | FOBS= | 86.7 | SIGMA= | 2.0 | PHAS= | 100.6 | FOM= | 0.92 | TEST= 0 |
| INDE | 6 | 27 | 37 | FOBS= | 160.3 | SIGMA= | 1.2 | PHAS= | 48.9 | FOM= | 0.95 | TEST= 0 |
| INDE | 6 | 27 | 39 | FOBS= | 221.3 | SIGMA= | 0.8 | PHAS= | 145.6 | FOM= | 0.93 | TEST= 0 |
| INDE | 6 | 27 | 41 | FOBS= | 106.3 | SIGMA= | 2.0 | PHAS= | 100.5 | FOM= | 0.86 | TEST= 0 |
| INDE | 6 | 27 | 43 | FOBS= | 93.7 | SIGMA= | 2.0 | PHAS= | 177.0 | FOM= | 0.94 | TEST= 0 |
| INDE | 6 | 27 | 45 | FOBS= | 64.0 | SIGMA= | 2.8 | PHAS= | -78.6 | FOM= | 0.59 | TEST= 0 |
| INDE | 6 | 27 | 47 | FOBS= | 223.9 | SIGMA= | 0.9 | PHAS= | 84.3 | FOM= | 0.97 | TEST= 0 |
| INDE | 6 | 27 | 49 | FOBS= | 143.5 | SIGMA= | 1.0 | PHAS= | 148.0 | FOM= | 0.91 | TEST= 0 |
| INDE | 6 | 27 | 51 | FOBS= | 134.2 | SIGMA= | 1.1 | PHAS= | -27.5 | FOM= | 0.93 | TEST= 0 |
| INDE | 6 | 27 | 53 | FOBS= | 0.0 | SIGMA= | 17.2 | PHAS= | 0.0 | FOM= | 0.00 | TEST= 0 |
| INDE | 6 | 27 | 55 | FOBS= | 48.1 | SIGMA= | 2.7 | PHAS= | 161.2 | FOM= | 0.71 | TEST= 0 |
| INDE | 6 | 27 | 57 | FOBS= | 35.6 | SIGMA= | 4.3 | PHAS= | -47.3 | FOM= | 0.82 | TEST= 0 |
| INDE | 6 | 27 | 59 | FOBS= | 29.5 | SIGMA= | 7.6 | PHAS= | -83.2 | FOM= | 0.08 | TEST= 0 |
| INDE | 6 | 27 | 61 | FOBS= | 26.5 | SIGMA= | 12.2 | PHAS= | -178.9 | FOM= | 0.16 | TEST= 0 |
| INDE | 6 | 27 | 63 | FOBS= | 62.0 | SIGMA= | 5.3 | PHAS= | 9.8 | FOM= | 0.87 | TEST= 0 |
| INDE | 6 | 27 | 65 | FOBS= | 26.8 | SIGMA= | 17.4 | PHAS= | 142.0 | FOM= | 0.51 | TEST= 0 |

*FIG. 12A - 169*

```
INDE  6  27  67 FOBS=    0.0 SIGMA= 30.8 PHAS=    0.0 FOM= 0.00 TEST= 0
INDE  6  27  69 FOBS=   49.3 SIGMA=  9.7 PHAS=   76.0 FOM= 0.57 TEST= 0
INDE  6  27  71 FOBS=  168.7 SIGMA=  3.1 PHAS=  -70.1 FOM= 0.97 TEST= 0
INDE  6  28   6 FOBS=  166.2 SIGMA=  0.7 PHAS=  -92.0 FOM= 0.95 TEST= 0
INDE  6  28   8 FOBS=   54.7 SIGMA=  1.4 PHAS=  -11.8 FOM= 0.99 TEST= 0
INDE  6  28  10 FOBS=  148.6 SIGMA=  0.7 PHAS=   95.9 FOM= 0.95 TEST= 0
INDE  6  28  12 FOBS=  153.7 SIGMA=  0.7 PHAS=   85.6 FOM= 0.98 TEST= 0
INDE  6  28  14 FOBS=  134.1 SIGMA=  0.8 PHAS=   53.7 FOM= 0.95 TEST= 0
INDE  6  28  16 FOBS=   27.2 SIGMA=  4.0 PHAS=  -15.4 FOM= 0.92 TEST= 0
INDE  6  28  18 FOBS=   60.5 SIGMA=  2.5 PHAS= -146.7 FOM= 0.43 TEST= 0
INDE  6  28  20 FOBS=   51.6 SIGMA=  2.7 PHAS=   25.8 FOM= 0.84 TEST= 1
INDE  6  28  22 FOBS=  142.2 SIGMA=  1.1 PHAS=  -69.4 FOM= 0.97 TEST= 0
INDE  6  28  24 FOBS=  237.1 SIGMA=  0.7 PHAS= -161.8 FOM= 0.95 TEST= 0
INDE  6  28  26 FOBS=  135.1 SIGMA=  1.0 PHAS=  -76.8 FOM= 0.91 TEST= 0
INDE  6  28  28 FOBS=   15.1 SIGMA=  9.6 PHAS=  162.2 FOM= 0.08 TEST= 0
INDE  6  28  30 FOBS=  192.4 SIGMA=  0.9 PHAS= -136.7 FOM= 0.84 TEST= 0
INDE  6  28  32 FOBS=  343.7 SIGMA=  0.7 PHAS=  -24.2 FOM= 0.95 TEST= 0
INDE  6  28  34 FOBS=  176.6 SIGMA=  1.0 PHAS= -129.3 FOM= 0.83 TEST= 0
INDE  6  28  36 FOBS=   97.7 SIGMA=  2.0 PHAS=   48.4 FOM= 0.96 TEST= 1
INDE  6  28  38 FOBS=  315.9 SIGMA=  0.9 PHAS=   28.9 FOM= 0.96 TEST= 0
INDE  6  28  40 FOBS=  156.5 SIGMA=  1.2 PHAS=    2.4 FOM= 0.81 TEST= 0
INDE  6  28  42 FOBS=  144.0 SIGMA=  1.8 PHAS= -124.7 FOM= 0.94 TEST= 0
INDE  6  28  44 FOBS=  172.7 SIGMA=  1.1 PHAS= -172.2 FOM= 0.94 TEST= 0
INDE  6  28  46 FOBS=  176.0 SIGMA=  1.1 PHAS=  -28.9 FOM= 0.93 TEST= 0
INDE  6  28  48 FOBS=   61.4 SIGMA=  2.8 PHAS=   49.1 FOM= 0.84 TEST= 0
INDE  6  28  50 FOBS=  105.1 SIGMA=  1.5 PHAS=  -72.6 FOM= 0.46 TEST= 1
INDE  6  28  52 FOBS=  103.5 SIGMA=  1.3 PHAS=  -51.6 FOM= 0.82 TEST= 0
INDE  6  28  54 FOBS=   42.8 SIGMA=  3.1 PHAS= -166.4 FOM= 0.48 TEST= 0
INDE  6  28  56 FOBS=   54.4 SIGMA=  2.7 PHAS=   82.2 FOM= 0.14 TEST= 0
INDE  6  28  58 FOBS=   17.5 SIGMA=  9.0 PHAS= -122.1 FOM= 0.49 TEST= 0
INDE  6  28  60 FOBS=   83.0 SIGMA=  2.3 PHAS=  172.3 FOM= 0.60 TEST= 0
INDE  6  28  62 FOBS=   51.9 SIGMA=  6.3 PHAS=  -65.7 FOM= 0.22 TEST= 0
INDE  6  28  64 FOBS=   26.1 SIGMA= 12.5 PHAS=   -7.6 FOM= 0.24 TEST= 0
INDE  6  28  66 FOBS=    0.0 SIGMA= 30.9 PHAS=    0.0 FOM= 0.00 TEST= 0
INDE  6  28  68 FOBS=    0.0 SIGMA= 31.3 PHAS=    0.0 FOM= 0.00 TEST= 0
INDE  6  29   7 FOBS=  110.0 SIGMA=  0.7 PHAS= -113.2 FOM= 0.92 TEST= 0
INDE  6  29   9 FOBS=   83.2 SIGMA=  1.2 PHAS=  -66.9 FOM= 0.95 TEST= 0
INDE  6  29  11 FOBS=  245.3 SIGMA=  0.6 PHAS=   69.4 FOM= 0.99 TEST= 0
INDE  6  29  13 FOBS=  234.3 SIGMA=  0.7 PHAS=  -86.4 FOM= 0.99 TEST= 0
INDE  6  29  15 FOBS=  119.0 SIGMA=  1.0 PHAS=   30.2 FOM= 0.98 TEST= 0
INDE  6  29  17 FOBS=  194.4 SIGMA=  1.0 PHAS=  143.3 FOM= 0.95 TEST= 0
INDE  6  29  19 FOBS=   14.7 SIGMA=  9.3 PHAS=  149.4 FOM= 0.52 TEST= 0
INDE  6  29  21 FOBS=  420.1 SIGMA=  0.8 PHAS= -173.5 FOM= 0.97 TEST= 0
INDE  6  29  23 FOBS=   73.9 SIGMA=  2.1 PHAS= -138.9 FOM= 0.89 TEST= 0
INDE  6  29  25 FOBS=  158.3 SIGMA=  1.0 PHAS= -174.5 FOM= 0.92 TEST= 0
INDE  6  29  27 FOBS=   37.8 SIGMA=  3.6 PHAS= -148.5 FOM= 0.91 TEST= 0
INDE  6  29  29 FOBS=  129.0 SIGMA=  1.2 PHAS=  140.3 FOM= 0.95 TEST= 0
INDE  6  29  31 FOBS=  271.4 SIGMA=  0.7 PHAS=  178.6 FOM= 0.86 TEST= 0
INDE  6  29  33 FOBS=   85.2 SIGMA=  1.9 PHAS=  -88.5 FOM= 0.27 TEST= 0
INDE  6  29  35 FOBS=  196.7 SIGMA=  1.0 PHAS=  119.9 FOM= 0.95 TEST= 0
INDE  6  29  37 FOBS=  117.2 SIGMA=  1.8 PHAS=  -96.9 FOM= 0.94 TEST= 0
INDE  6  29  39 FOBS=   49.2 SIGMA=  4.2 PHAS= -147.7 FOM= 0.33 TEST= 0
INDE  6  29  41 FOBS=  237.9 SIGMA=  0.9 PHAS=   15.0 FOM= 0.96 TEST= 0
INDE  6  29  43 FOBS=  168.1 SIGMA=  1.2 PHAS=  103.7 FOM= 0.94 TEST= 0
INDE  6  29  45 FOBS=   92.8 SIGMA=  2.2 PHAS=   57.7 FOM= 0.92 TEST= 0
INDE  6  29  47 FOBS=   81.4 SIGMA=  2.2 PHAS=  161.5 FOM= 0.70 TEST= 0
INDE  6  29  49 FOBS=   56.8 SIGMA=  2.5 PHAS=  131.8 FOM= 0.61 TEST= 0
INDE  6  29  51 FOBS=   76.6 SIGMA=  1.8 PHAS=   -3.5 FOM= 0.83 TEST= 0
INDE  6  29  53 FOBS=   99.2 SIGMA=  1.4 PHAS=   31.8 FOM= 0.93 TEST= 0
INDE  6  29  55 FOBS=  124.0 SIGMA=  1.2 PHAS=  124.4 FOM= 0.87 TEST= 0
INDE  6  29  57 FOBS=   22.2 SIGMA=  7.2 PHAS= -127.0 FOM= 0.31 TEST= 0
INDE  6  29  59 FOBS=   79.4 SIGMA=  2.0 PHAS=  167.0 FOM= 0.81 TEST= 0
INDE  6  29  61 FOBS=   62.6 SIGMA=  3.1 PHAS= -119.4 FOM= 0.51 TEST= 1
INDE  6  29  63 FOBS=   94.8 SIGMA=  3.6 PHAS=  -50.3 FOM= 0.91 TEST= 0
INDE  6  29  65 FOBS=    6.1 SIGMA= 77.8 PHAS= -131.7 FOM= 0.07 TEST= 0
INDE  6  29  67 FOBS=    0.0 SIGMA= 31.2 PHAS=    0.0 FOM= 0.00 TEST= 0
INDE  6  29  69 FOBS=   62.9 SIGMA=  7.9 PHAS= -110.4 FOM= 0.75 TEST= 0
INDE  6  29  71 FOBS=   74.0 SIGMA=  6.7 PHAS=  -58.1 FOM= 0.37 TEST= 1
INDE  6  30   6 FOBS=   93.2 SIGMA=  1.1 PHAS= -141.8 FOM= 0.83 TEST= 0
INDE  6  30   8 FOBS=  161.3 SIGMA=  0.6 PHAS=  115.6 FOM= 0.95 TEST= 0
```

*FIG. 12A - 170*

```
INDE   6   30   10  FOBS=    204.5  SIGMA=   0.6  PHAS=    19.3  FOM=  0.97  TEST= 0
INDE   6   30   12  FOBS=    230.5  SIGMA=   0.6  PHAS=   117.4  FOM=  0.98  TEST= 1
INDE   6   30   14  FOBS=    153.9  SIGMA=   0.8  PHAS=   175.2  FOM=  0.98  TEST= 1
INDE   6   30   16  FOBS=    171.4  SIGMA=   0.8  PHAS=    82.0  FOM=  0.98  TEST= 0
INDE   6   30   18  FOBS=    185.2  SIGMA=   1.1  PHAS=   138.8  FOM=  0.98  TEST= 0
INDE   6   30   20  FOBS=    355.3  SIGMA=   0.7  PHAS=   145.3  FOM=  0.97  TEST= 0
INDE   6   30   22  FOBS=    254.6  SIGMA=   0.8  PHAS=    65.0  FOM=  0.89  TEST= 0
INDE   6   30   24  FOBS=    359.3  SIGMA=   0.8  PHAS=   166.9  FOM=  0.99  TEST= 0
INDE   6   30   26  FOBS=    274.3  SIGMA=   0.7  PHAS=    44.5  FOM=  0.96  TEST= 0
INDE   6   30   28  FOBS=    156.2  SIGMA=   1.0  PHAS=    90.8  FOM=  0.98  TEST= 0
INDE   6   30   30  FOBS=    213.7  SIGMA=   0.9  PHAS=   115.3  FOM=  0.90  TEST= 0
INDE   6   30   32  FOBS=    180.4  SIGMA=   1.0  PHAS=    51.7  FOM=  0.30  TEST= 0
INDE   6   30   34  FOBS=     84.3  SIGMA=   2.1  PHAS=    54.5  FOM=  0.81  TEST= 0
INDE   6   30   36  FOBS=    214.7  SIGMA=   1.0  PHAS=     2.0  FOM=  0.97  TEST= 0
INDE   6   30   38  FOBS=    131.4  SIGMA=   1.5  PHAS=   -48.8  FOM=  0.80  TEST= 0
INDE   6   30   40  FOBS=     80.8  SIGMA=   2.4  PHAS=    13.2  FOM=  0.90  TEST= 1
INDE   6   30   42  FOBS=    159.1  SIGMA=   1.2  PHAS=   -95.8  FOM=  0.92  TEST= 0
INDE   6   30   44  FOBS=    131.6  SIGMA=   1.4  PHAS=  -102.4  FOM=  0.23  TEST= 0
INDE   6   30   46  FOBS=    251.9  SIGMA=   0.9  PHAS=    -3.3  FOM=  0.96  TEST= 0
INDE   6   30   48  FOBS=    108.2  SIGMA=   1.7  PHAS=    11.6  FOM=  0.67  TEST= 0
INDE   6   30   50  FOBS=     86.5  SIGMA=   1.6  PHAS=   -67.1  FOM=  0.95  TEST= 0
INDE   6   30   52  FOBS=    206.2  SIGMA=   0.9  PHAS=   -39.8  FOM=  0.95  TEST= 0
INDE   6   30   54  FOBS=     74.1  SIGMA=   1.8  PHAS=   -16.1  FOM=  0.77  TEST= 0
INDE   6   30   56  FOBS=      0.0  SIGMA=  17.6  PHAS=     0.0  FOM=  0.00  TEST= 0
INDE   6   30   58  FOBS=     24.5  SIGMA=   6.6  PHAS=  -173.9  FOM=  0.07  TEST= 0
INDE   6   30   60  FOBS=     69.5  SIGMA=   2.5  PHAS=   146.3  FOM=  0.82  TEST= 0
INDE   6   30   62  FOBS=    103.0  SIGMA=   2.0  PHAS=  -147.5  FOM=  0.03  TEST= 1
INDE   6   30   64  FOBS=     36.3  SIGMA=   9.1  PHAS=  -112.4  FOM=  0.30  TEST= 0
INDE   6   30   66  FOBS=     43.1  SIGMA=  11.5  PHAS=   134.2  FOM=  0.54  TEST= 0
INDE   6   30   68  FOBS=     59.8  SIGMA=   8.2  PHAS=  -141.2  FOM=  0.05  TEST= 1
INDE   6   30   70  FOBS=     57.9  SIGMA=   8.8  PHAS=   -82.7  FOM=  0.42  TEST= 0
INDE   6   31    7  FOBS=     88.7  SIGMA=   1.2  PHAS=   -70.0  FOM=  0.82  TEST= 0
INDE   6   31    9  FOBS=    242.6  SIGMA=   0.7  PHAS=   -40.3  FOM=  0.96  TEST= 0
INDE   6   31   11  FOBS=    145.5  SIGMA=   0.8  PHAS=   -61.8  FOM=  0.62  TEST= 0
INDE   6   31   13  FOBS=    206.3  SIGMA=   0.7  PHAS=   -40.7  FOM=  0.87  TEST= 0
INDE   6   31   15  FOBS=    183.7  SIGMA=   0.8  PHAS=    41.0  FOM=  0.99  TEST= 0
INDE   6   31   17  FOBS=    122.9  SIGMA=   1.1  PHAS=    64.2  FOM=  0.99  TEST= 0
INDE   6   31   19  FOBS=    365.4  SIGMA=   0.7  PHAS=    82.5  FOM=  0.97  TEST= 0
INDE   6   31   21  FOBS=     57.5  SIGMA=   2.7  PHAS=   -21.9  FOM=  0.92  TEST= 0
INDE   6   31   23  FOBS=    511.3  SIGMA=   0.7  PHAS=    73.6  FOM=  0.99  TEST= 0
INDE   6   31   25  FOBS=    154.4  SIGMA=   1.1  PHAS=   -72.5  FOM=  0.73  TEST= 0
INDE   6   31   27  FOBS=    423.4  SIGMA=   0.7  PHAS=   -25.8  FOM=  0.97  TEST= 0
INDE   6   31   29  FOBS=    234.1  SIGMA=   0.8  PHAS=    34.0  FOM=  0.94  TEST= 0
INDE   6   31   31  FOBS=     48.5  SIGMA=   3.5  PHAS=   -51.2  FOM=  0.77  TEST= 0
INDE   6   31   33  FOBS=    105.1  SIGMA=   1.7  PHAS=   -11.6  FOM=  0.69  TEST= 0
INDE   6   31   35  FOBS=    124.2  SIGMA=   1.6  PHAS=  -171.8  FOM=  0.96  TEST= 0
INDE   6   31   37  FOBS=    109.9  SIGMA=   1.8  PHAS=  -109.5  FOM=  0.91  TEST= 0
INDE   6   31   39  FOBS=     98.6  SIGMA=   2.0  PHAS=   158.1  FOM=  0.89  TEST= 0
INDE   6   31   41  FOBS=    213.6  SIGMA=   1.0  PHAS=   -46.8  FOM=  0.95  TEST= 0
INDE   6   31   43  FOBS=    163.0  SIGMA=   1.2  PHAS=   132.7  FOM=  0.92  TEST= 0
INDE   6   31   45  FOBS=     63.3  SIGMA=   3.0  PHAS=  -157.3  FOM=  0.48  TEST= 1
INDE   6   31   47  FOBS=    231.1  SIGMA=   1.0  PHAS=   -58.2  FOM=  0.94  TEST= 0
INDE   6   31   49  FOBS=     53.5  SIGMA=   3.2  PHAS=   -73.6  FOM=  0.91  TEST= 0
INDE   6   31   51  FOBS=     16.0  SIGMA=  10.0  PHAS=    39.6  FOM=  0.09  TEST= 0
INDE   6   31   53  FOBS=      9.0  SIGMA=  15.0  PHAS=   -18.5  FOM=  0.22  TEST= 0
INDE   6   31   55  FOBS=      0.0  SIGMA=  18.3  PHAS=     0.0  FOM=  0.00  TEST= 0
INDE   6   31   57  FOBS=      0.0  SIGMA=  18.1  PHAS=     0.0  FOM=  0.00  TEST= 0
INDE   6   31   59  FOBS=      0.0  SIGMA=  18.4  PHAS=     0.0  FOM=  0.00  TEST= 0
INDE   6   31   61  FOBS=     56.8  SIGMA=   3.1  PHAS=   120.9  FOM=  0.85  TEST= 0
INDE   6   31   63  FOBS=      0.0  SIGMA=  19.8  PHAS=     0.0  FOM=  0.00  TEST= 0
INDE   6   31   65  FOBS=     33.4  SIGMA=  14.9  PHAS=  -119.0  FOM=  0.52  TEST= 0
INDE   6   31   67  FOBS=     69.0  SIGMA=   7.2  PHAS=    13.1  FOM=  0.62  TEST= 0
INDE   6   31   69  FOBS=     25.0  SIGMA=  20.0  PHAS=  -150.2  FOM=  0.72  TEST= 0
INDE   6   31   71  FOBS=     76.5  SIGMA=   6.8  PHAS=    90.4  FOM=  0.80  TEST= 0
INDE   6   32    6  FOBS=     91.5  SIGMA=   1.1  PHAS=   -79.4  FOM=  0.79  TEST= 0
INDE   6   32    8  FOBS=     61.4  SIGMA=   1.4  PHAS=  -116.7  FOM=  0.97  TEST= 0
INDE   6   32   10  FOBS=     62.0  SIGMA=   1.7  PHAS=   158.3  FOM=  0.80  TEST= 0
INDE   6   32   12  FOBS=    250.7  SIGMA=   0.6  PHAS=    98.4  FOM=  0.96  TEST= 0
INDE   6   32   14  FOBS=    247.0  SIGMA=   0.7  PHAS=  -143.6  FOM=  0.99  TEST= 0
INDE   6   32   16  FOBS=      0.0  SIGMA=  15.0  PHAS=     0.0  FOM=  0.00  TEST= 1
```

*FIG. 12A - 171*

```
INDE  6  32  18  FOBS=  141.1  SIGMA=   1.0  PHAS=   15.4  FOM=  0.84  TEST= 0
INDE  6  32  20  FOBS=   98.5  SIGMA=   1.7  PHAS=  137.1  FOM=  0.81  TEST= 0
INDE  6  32  22  FOBS=  314.7  SIGMA=   0.8  PHAS= -167.7  FOM=  0.99  TEST= 0
INDE  6  32  24  FOBS=  113.7  SIGMA=   1.6  PHAS= -117.0  FOM=  0.92  TEST= 0
INDE  6  32  26  FOBS=  200.2  SIGMA=   0.9  PHAS=  150.1  FOM=  0.47  TEST= 1
INDE  6  32  28  FOBS=  112.8  SIGMA=   1.6  PHAS=  -80.2  FOM=  0.88  TEST= 0
INDE  6  32  30  FOBS=    0.0  SIGMA=  19.5  PHAS=    0.0  FOM=  0.00  TEST= 0
INDE  6  32  32  FOBS=   90.9  SIGMA=   2.0  PHAS=   -9.6  FOM=  0.28  TEST= 0
INDE  6  32  34  FOBS=  242.4  SIGMA=   0.9  PHAS=   69.1  FOM=  0.98  TEST= 0
INDE  6  32  36  FOBS=  134.6  SIGMA=   1.5  PHAS=  -16.5  FOM=  0.96  TEST= 0
INDE  6  32  38  FOBS=  102.6  SIGMA=   1.9  PHAS= -109.3  FOM=  0.89  TEST= 0
INDE  6  32  40  FOBS=  124.3  SIGMA=   1.6  PHAS=  -63.6  FOM=  0.84  TEST= 0
INDE  6  32  42  FOBS=    0.0  SIGMA=  20.2  PHAS=    0.0  FOM=  0.00  TEST= 0
INDE  6  32  44  FOBS=   81.1  SIGMA=   2.2  PHAS=  -95.2  FOM=  0.71  TEST= 0
INDE  6  32  46  FOBS=  168.9  SIGMA=   1.3  PHAS=  -52.3  FOM=  0.84  TEST= 0
INDE  6  32  48  FOBS=  119.3  SIGMA=   1.7  PHAS= -165.8  FOM=  0.94  TEST= 0
INDE  6  32  50  FOBS=   25.3  SIGMA=   6.2  PHAS= -152.8  FOM=  0.31  TEST= 0
INDE  6  32  52  FOBS=   32.0  SIGMA=   4.6  PHAS= -124.9  FOM=  0.33  TEST= 0
INDE  6  32  54  FOBS=   89.9  SIGMA=   1.7  PHAS=   34.7  FOM=  0.85  TEST= 0
INDE  6  32  56  FOBS=   38.2  SIGMA=   4.5  PHAS=   34.3  FOM=  0.10  TEST= 0
INDE  6  32  58  FOBS=    0.0  SIGMA=  18.0  PHAS=    0.0  FOM=  0.00  TEST= 0
INDE  6  32  60  FOBS=    0.0  SIGMA=  19.0  PHAS=    0.0  FOM=  0.00  TEST= 0
INDE  6  32  62  FOBS=   56.8  SIGMA=   3.1  PHAS= -100.8  FOM=  0.38  TEST= 0
INDE  6  32  64  FOBS=   38.0  SIGMA=   5.2  PHAS=  163.5  FOM=  0.34  TEST= 0
INDE  6  32  66  FOBS=    0.0  SIGMA=  31.6  PHAS=    0.0  FOM=  0.00  TEST= 0
INDE  6  32  68  FOBS=    0.0  SIGMA=  31.5  PHAS=    0.0  FOM=  0.00  TEST= 0
INDE  6  32  70  FOBS=   88.6  SIGMA=   5.9  PHAS=   83.8  FOM=  0.83  TEST= 0
INDE  6  33   7  FOBS=  151.1  SIGMA=   0.8  PHAS=  -68.2  FOM=  0.92  TEST= 1
INDE  6  33   9  FOBS=  192.4  SIGMA=   0.7  PHAS=  -35.2  FOM=  0.95  TEST= 0
INDE  6  33  11  FOBS=   38.6  SIGMA=   2.8  PHAS=  157.4  FOM=  0.81  TEST= 0
INDE  6  33  13  FOBS=  113.0  SIGMA=   1.1  PHAS=   53.7  FOM=  0.99  TEST= 0
INDE  6  33  15  FOBS=  199.1  SIGMA=   0.7  PHAS=   77.3  FOM=  0.96  TEST= 0
INDE  6  33  17  FOBS=  130.3  SIGMA=   1.0  PHAS=   47.5  FOM=  0.82  TEST= 0
INDE  6  33  19  FOBS=  168.2  SIGMA=   1.1  PHAS=   79.4  FOM=  0.92  TEST= 1
INDE  6  33  21  FOBS=   92.4  SIGMA=   1.9  PHAS= -154.5  FOM=  0.31  TEST= 0
INDE  6  33  23  FOBS=  129.6  SIGMA=   1.5  PHAS= -109.8  FOM=  0.98  TEST= 0
INDE  6  33  25  FOBS=  159.2  SIGMA=   1.3  PHAS= -173.6  FOM=  0.92  TEST= 0
INDE  6  33  27  FOBS=  253.4  SIGMA=   0.8  PHAS=  -16.5  FOM=  0.94  TEST= 0
INDE  6  33  29  FOBS=  154.2  SIGMA=   1.2  PHAS=   48.7  FOM=  0.82  TEST= 0
INDE  6  33  31  FOBS=  111.4  SIGMA=   1.7  PHAS=   94.7  FOM=  0.68  TEST= 0
INDE  6  33  33  FOBS=  183.3  SIGMA=   1.1  PHAS=  -25.3  FOM=  0.79  TEST= 1
INDE  6  33  35  FOBS=  321.5  SIGMA=   0.8  PHAS=  -68.2  FOM=  0.96  TEST= 0
INDE  6  33  37  FOBS=   54.2  SIGMA=   3.6  PHAS=  -11.6  FOM=  0.76  TEST= 0
INDE  6  33  39  FOBS=  250.5  SIGMA=   0.9  PHAS= -154.6  FOM=  0.97  TEST= 0
INDE  6  33  41  FOBS=  123.0  SIGMA=   1.6  PHAS=   -7.9  FOM=  0.85  TEST= 0
INDE  6  33  43  FOBS=   41.5  SIGMA=   4.4  PHAS=   64.5  FOM=  0.28  TEST= 0
INDE  6  33  45  FOBS=   45.7  SIGMA=   3.9  PHAS= -169.3  FOM=  0.48  TEST= 0
INDE  6  33  47  FOBS=   50.0  SIGMA=   4.0  PHAS= -117.7  FOM=  0.89  TEST= 0
INDE  6  33  49  FOBS=   39.5  SIGMA=   5.0  PHAS=   68.0  FOM=  0.18  TEST= 0
INDE  6  33  51  FOBS=   51.3  SIGMA=   2.9  PHAS=   28.8  FOM=  0.85  TEST= 0
INDE  6  33  53  FOBS=   94.6  SIGMA=   1.6  PHAS=  -71.2  FOM=  0.86  TEST= 0
INDE  6  33  55  FOBS=  153.4  SIGMA=   1.2  PHAS= -109.5  FOM=  0.96  TEST= 0
INDE  6  33  57  FOBS=   30.9  SIGMA=   5.4  PHAS=  103.6  FOM=  0.48  TEST= 0
INDE  6  33  59  FOBS=   62.6  SIGMA=   2.8  PHAS=    2.8  FOM=  0.78  TEST= 0
INDE  6  33  61  FOBS=   40.3  SIGMA=   4.3  PHAS= -158.9  FOM=  0.48  TEST= 0
INDE  6  33  63  FOBS=   66.0  SIGMA=   2.7  PHAS=  -61.5  FOM=  0.42  TEST= 0
INDE  6  33  65  FOBS=   16.3  SIGMA=  12.4  PHAS=  147.8  FOM=  0.24  TEST= 0
INDE  6  33  67  FOBS=   70.0  SIGMA=   5.3  PHAS=   44.8  FOM=  0.77  TEST= 0
INDE  6  33  69  FOBS=   89.1  SIGMA=   5.9  PHAS=   33.5  FOM=  0.89  TEST= 0
INDE  6  34   6  FOBS=   91.5  SIGMA=   1.2  PHAS=  127.3  FOM=  0.92  TEST= 0
INDE  6  34   8  FOBS=  374.5  SIGMA=   0.7  PHAS= -124.7  FOM=  0.97  TEST= 0
INDE  6  34  10  FOBS=  240.5  SIGMA=   0.6  PHAS=  152.7  FOM=  0.99  TEST= 0
INDE  6  34  12  FOBS=  102.9  SIGMA=   1.2  PHAS=  131.3  FOM=  0.77  TEST= 1
INDE  6  34  14  FOBS=  206.4  SIGMA=   0.8  PHAS=   27.5  FOM=  0.98  TEST= 0
INDE  6  34  16  FOBS=   95.1  SIGMA=   1.4  PHAS=    4.0  FOM=  0.96  TEST= 0
INDE  6  34  18  FOBS=  277.1  SIGMA=   0.8  PHAS=  -84.0  FOM=  0.90  TEST= 0
INDE  6  34  20  FOBS=  220.9  SIGMA=   1.0  PHAS=  119.8  FOM=  0.93  TEST= 0
INDE  6  34  22  FOBS=  479.0  SIGMA=   0.7  PHAS=  170.7  FOM=  0.98  TEST= 0
INDE  6  34  24  FOBS=  228.8  SIGMA=   1.0  PHAS=  155.8  FOM=  0.98  TEST= 0
INDE  6  34  26  FOBS=  232.1  SIGMA=   1.0  PHAS=  -52.8  FOM=  0.92  TEST= 0
```

*FIG. 12A - 172*

```
INDE   6   34   28 FOBS=    47.2 SIGMA=    3.8 PHAS=   -94.0 FOM=   0.47 TEST= 0
INDE   6   34   30 FOBS=   126.1 SIGMA=    1.5 PHAS=   -68.0 FOM=   0.97 TEST= 0
INDE   6   34   32 FOBS=   142.4 SIGMA=    1.5 PHAS=    -8.2 FOM=   0.91 TEST= 0
INDE   6   34   34 FOBS=   130.2 SIGMA=    1.6 PHAS=    53.2 FOM=   0.68 TEST= 0
INDE   6   34   36 FOBS=   223.1 SIGMA=    1.0 PHAS=   -92.8 FOM=   0.91 TEST= 0
INDE   6   34   38 FOBS=    14.2 SIGMA=   14.8 PHAS=   171.6 FOM=   0.28 TEST= 0
INDE   6   34   40 FOBS=   129.2 SIGMA=    1.5 PHAS=  -135.4 FOM=   0.86 TEST= 0
INDE   6   34   42 FOBS=   123.6 SIGMA=    1.5 PHAS=  -133.5 FOM=   0.61 TEST= 0
INDE   6   34   44 FOBS=    32.4 SIGMA=    6.0 PHAS=    39.8 FOM=   0.45 TEST= 0
INDE   6   34   46 FOBS=     0.0 SIGMA=   19.6 PHAS=     0.0 FOM=   0.00 TEST= 0
INDE   6   34   48 FOBS=    43.8 SIGMA=    4.0 PHAS=   155.1 FOM=   0.62 TEST= 0
INDE   6   34   50 FOBS=   163.8 SIGMA=    1.2 PHAS=  -131.1 FOM=   0.96 TEST= 0
INDE   6   34   52 FOBS=    80.4 SIGMA=    2.0 PHAS=   148.1 FOM=   0.72 TEST= 0
INDE   6   34   54 FOBS=    32.8 SIGMA=    5.4 PHAS=   164.8 FOM=   0.83 TEST= 0
INDE   6   34   56 FOBS=    95.3 SIGMA=    2.2 PHAS=   177.1 FOM=   0.92 TEST= 0
INDE   6   34   58 FOBS=     0.0 SIGMA=   20.0 PHAS=     0.0 FOM=   0.00 TEST= 0
INDE   6   34   60 FOBS=    53.2 SIGMA=    3.3 PHAS=  -155.9 FOM=   0.22 TEST= 1
INDE   6   34   62 FOBS=    62.9 SIGMA=    2.8 PHAS=   -96.0 FOM=   0.61 TEST= 0
INDE   6   34   64 FOBS=     0.0 SIGMA=   21.2 PHAS=     0.0 FOM=   0.00 TEST= 0
INDE   6   34   66 FOBS=    54.3 SIGMA=    4.3 PHAS=     3.9 FOM=   0.08 TEST= 1
INDE   6   34   68 FOBS=    48.9 SIGMA=    7.7 PHAS=    47.7 FOM=   0.08 TEST= 1
INDE   6   35    7 FOBS=   194.6 SIGMA=    0.6 PHAS=    75.2 FOM=   0.92 TEST= 0
INDE   6   35    9 FOBS=   159.5 SIGMA=    0.9 PHAS=    91.9 FOM=   0.89 TEST= 0
INDE   6   35   11 FOBS=   118.5 SIGMA=    1.1 PHAS=    36.5 FOM=   0.99 TEST= 0
INDE   6   35   13 FOBS=   132.8 SIGMA=    1.0 PHAS=   -72.2 FOM=   0.98 TEST= 0
INDE   6   35   15 FOBS=   262.6 SIGMA=    0.7 PHAS=   -40.9 FOM=   0.99 TEST= 0
INDE   6   35   17 FOBS=    92.3 SIGMA=    1.5 PHAS=   170.9 FOM=   0.67 TEST= 0
INDE   6   35   19 FOBS=    76.2 SIGMA=    2.0 PHAS=   -34.4 FOM=   0.92 TEST= 0
INDE   6   35   21 FOBS=   236.6 SIGMA=    1.0 PHAS=    80.5 FOM=   0.96 TEST= 0
INDE   6   35   23 FOBS=   446.9 SIGMA=    0.7 PHAS=   -13.3 FOM=   0.80 TEST= 1
INDE   6   35   25 FOBS=   370.9 SIGMA=    1.1 PHAS=   126.2 FOM=   0.98 TEST= 0
INDE   6   35   27 FOBS=   120.1 SIGMA=    1.9 PHAS=   151.1 FOM=   0.96 TEST= 0
INDE   6   35   29 FOBS=    69.0 SIGMA=    2.9 PHAS=  -125.2 FOM=   0.96 TEST= 0
INDE   6   35   31 FOBS=    88.3 SIGMA=    2.3 PHAS=  -145.4 FOM=   0.91 TEST= 0
INDE   6   35   33 FOBS=   111.7 SIGMA=    2.0 PHAS=   -86.6 FOM=   0.93 TEST= 0
INDE   6   35   35 FOBS=   305.1 SIGMA=    0.8 PHAS=  -123.0 FOM=   0.96 TEST= 1
INDE   6   35   37 FOBS=   247.6 SIGMA=    0.9 PHAS=   -54.4 FOM=   0.82 TEST= 1
INDE   6   35   39 FOBS=   101.2 SIGMA=    1.9 PHAS=  -161.1 FOM=   0.91 TEST= 0
INDE   6   35   41 FOBS=   105.7 SIGMA=    1.8 PHAS=    86.0 FOM=   0.41 TEST= 1
INDE   6   35   43 FOBS=   163.7 SIGMA=    1.2 PHAS=  -124.5 FOM=   0.93 TEST= 0
INDE   6   35   45 FOBS=    38.0 SIGMA=    5.8 PHAS=   -80.8 FOM=   0.14 TEST= 1
INDE   6   35   47 FOBS=    79.9 SIGMA=    2.2 PHAS=   -31.6 FOM=   0.87 TEST= 0
INDE   6   35   49 FOBS=   220.0 SIGMA=    0.9 PHAS=   127.3 FOM=   0.96 TEST= 0
INDE   6   35   51 FOBS=   140.7 SIGMA=    1.3 PHAS=   -76.8 FOM=   0.20 TEST= 1
INDE   6   35   53 FOBS=    95.9 SIGMA=    1.9 PHAS=    89.7 FOM=   0.86 TEST= 0
INDE   6   35   55 FOBS=    34.8 SIGMA=    5.1 PHAS=    79.4 FOM=   0.16 TEST= 0
INDE   6   35   57 FOBS=    40.7 SIGMA=    4.3 PHAS=   121.3 FOM=   0.74 TEST= 0
INDE   6   35   59 FOBS=    39.5 SIGMA=    4.5 PHAS=    48.4 FOM=   0.51 TEST= 0
INDE   6   35   61 FOBS=     0.0 SIGMA=   19.1 PHAS=     0.0 FOM=   0.00 TEST= 0
INDE   6   35   63 FOBS=    15.4 SIGMA=   12.3 PHAS=  -118.8 FOM=   0.04 TEST= 0
INDE   6   35   65 FOBS=    89.1 SIGMA=    2.4 PHAS=   131.9 FOM=   0.94 TEST= 0
INDE   6   35   67 FOBS=    49.1 SIGMA=    6.3 PHAS=    49.2 FOM=   0.41 TEST= 0
INDE   6   35   69 FOBS=     0.0 SIGMA=   27.6 PHAS=     0.0 FOM=   0.00 TEST= 0
INDE   6   36    6 FOBS=   352.4 SIGMA=    0.8 PHAS=   123.8 FOM=   0.96 TEST= 0
INDE   6   36    8 FOBS=   343.3 SIGMA=    0.9 PHAS=  -115.5 FOM=   0.98 TEST= 0
INDE   6   36   10 FOBS=   245.1 SIGMA=    0.8 PHAS=    31.2 FOM=   0.97 TEST= 0
INDE   6   36   12 FOBS=   191.4 SIGMA=    0.8 PHAS=  -119.2 FOM=   0.97 TEST= 0
INDE   6   36   14 FOBS=   196.5 SIGMA=    0.9 PHAS=   134.3 FOM=   0.99 TEST= 0
INDE   6   36   16 FOBS=   175.1 SIGMA=    0.9 PHAS=   -29.6 FOM=   0.41 TEST= 0
INDE   6   36   18 FOBS=    84.4 SIGMA=    1.9 PHAS=  -160.0 FOM=   0.46 TEST= 0
INDE   6   36   20 FOBS=   225.8 SIGMA=    0.9 PHAS=    63.6 FOM=   0.97 TEST= 0
INDE   6   36   22 FOBS=   378.6 SIGMA=    0.8 PHAS=    99.1 FOM=   0.97 TEST= 0
INDE   6   36   24 FOBS=   475.1 SIGMA=    1.0 PHAS=    31.7 FOM=   0.98 TEST= 0
INDE   6   36   26 FOBS=   425.1 SIGMA=    0.8 PHAS=    18.3 FOM=   0.98 TEST= 0
INDE   6   36   28 FOBS=   165.9 SIGMA=    1.5 PHAS=    76.6 FOM=   0.94 TEST= 0
INDE   6   36   30 FOBS=   227.2 SIGMA=    1.0 PHAS=  -167.3 FOM=   0.99 TEST= 0
INDE   6   36   32 FOBS=   188.5 SIGMA=    1.2 PHAS=    34.0 FOM=   0.94 TEST= 0
INDE   6   36   34 FOBS=    85.4 SIGMA=    2.4 PHAS=   178.3 FOM=   0.94 TEST= 0
INDE   6   36   36 FOBS=   355.0 SIGMA=    0.9 PHAS=   104.0 FOM=   0.97 TEST= 0
INDE   6   36   38 FOBS=   236.6 SIGMA=    1.1 PHAS=    95.3 FOM=   0.94 TEST= 0
```

*FIG. 12A - 173*

| | | | | | | | | | | | |
|---|---|---|---|---|---|---|---|---|---|---|---|
|INDE|6|36|40|FOBS=|80.4|SIGMA=|2.3|PHAS=|-160.6|FOM=|0.86|TEST=|0|
|INDE|6|36|42|FOBS=|107.7|SIGMA=|1.8|PHAS=|126.0|FOM=|0.58|TEST=|0|
|INDE|6|36|44|FOBS=|65.0|SIGMA=|2.8|PHAS=|112.9|FOM=|0.83|TEST=|0|
|INDE|6|36|46|FOBS=|76.8|SIGMA=|2.4|PHAS=|-5.4|FOM=|0.82|TEST=|0|
|INDE|6|36|48|FOBS=|81.6|SIGMA=|2.2|PHAS=|0.9|FOM=|0.90|TEST=|0|
|INDE|6|36|50|FOBS=|59.2|SIGMA=|2.7|PHAS=|-9.4|FOM=|0.75|TEST=|0|
|INDE|6|36|52|FOBS=|0.0|SIGMA=|19.0|PHAS=|0.0|FOM=|0.00|TEST=|1|
|INDE|6|36|54|FOBS=|66.9|SIGMA=|2.7|PHAS=|-4.3|FOM=|0.78|TEST=|0|
|INDE|6|36|56|FOBS=|10.8|SIGMA=|18.7|PHAS=|88.1|FOM=|0.11|TEST=|0|
|INDE|6|36|58|FOBS=|0.0|SIGMA=|18.7|PHAS=|0.0|FOM=|0.00|TEST=|0|
|INDE|6|36|60|FOBS=|52.5|SIGMA=|3.4|PHAS=|46.3|FOM=|0.39|TEST=|0|
|INDE|6|36|62|FOBS=|48.9|SIGMA=|3.6|PHAS=|-116.7|FOM=|0.39|TEST=|0|
|INDE|6|36|64|FOBS=|25.3|SIGMA=|7.2|PHAS=|93.8|FOM=|0.41|TEST=|0|
|INDE|6|36|66|FOBS=|112.2|SIGMA=|2.2|PHAS=|50.8|FOM=|0.95|TEST=|0|
|INDE|6|36|68|FOBS=|0.0|SIGMA=|27.8|PHAS=|0.0|FOM=|0.00|TEST=|1|
|INDE|6|37|7|FOBS=|271.9|SIGMA=|0.6|PHAS=|125.4|FOM=|0.97|TEST=|0|
|INDE|6|37|9|FOBS=|354.3|SIGMA=|1.1|PHAS=|-128.2|FOM=|0.97|TEST=|0|
|INDE|6|37|11|FOBS=|219.7|SIGMA=|0.7|PHAS=|-60.7|FOM=|0.98|TEST=|0|
|INDE|6|37|13|FOBS=|83.8|SIGMA=|1.6|PHAS=|104.6|FOM=|0.94|TEST=|0|
|INDE|6|37|15|FOBS=|151.1|SIGMA=|1.0|PHAS=|-26.6|FOM=|0.73|TEST=|1|
|INDE|6|37|17|FOBS=|174.6|SIGMA=|1.0|PHAS=|-1.2|FOM=|0.86|TEST=|1|
|INDE|6|37|19|FOBS=|174.1|SIGMA=|1.1|PHAS=|-67.2|FOM=|0.94|TEST=|0|
|INDE|6|37|21|FOBS=|290.3|SIGMA=|1.1|PHAS=|-65.4|FOM=|0.97|TEST=|0|
|INDE|6|37|23|FOBS=|286.1|SIGMA=|1.0|PHAS=|-42.8|FOM=|0.97|TEST=|1|
|INDE|6|37|25|FOBS=|186.9|SIGMA=|1.3|PHAS=|-103.9|FOM=|0.94|TEST=|0|
|INDE|6|37|27|FOBS=|198.8|SIGMA=|1.3|PHAS=|-56.3|FOM=|0.94|TEST=|0|
|INDE|6|37|29|FOBS=|22.4|SIGMA=|10.0|PHAS=|-108.1|FOM=|0.07|TEST=|0|
|INDE|6|37|31|FOBS=|49.0|SIGMA=|4.5|PHAS=|96.2|FOM=|0.87|TEST=|0|
|INDE|6|37|33|FOBS=|23.0|SIGMA=|9.1|PHAS=|-127.6|FOM=|0.22|TEST=|0|
|INDE|6|37|35|FOBS=|78.0|SIGMA=|2.6|PHAS=|-87.2|FOM=|0.89|TEST=|0|
|INDE|6|37|37|FOBS=|104.5|SIGMA=|1.9|PHAS=|24.4|FOM=|0.79|TEST=|0|
|INDE|6|37|39|FOBS=|46.6|SIGMA=|4.0|PHAS=|77.2|FOM=|0.57|TEST=|0|
|INDE|6|37|41|FOBS=|80.2|SIGMA=|2.3|PHAS=|167.8|FOM=|0.65|TEST=|0|
|INDE|6|37|43|FOBS=|46.9|SIGMA=|3.9|PHAS=|-105.6|FOM=|0.36|TEST=|1|
|INDE|6|37|45|FOBS=|47.8|SIGMA=|3.8|PHAS=|-84.2|FOM=|0.65|TEST=|0|
|INDE|6|37|47|FOBS=|145.0|SIGMA=|1.3|PHAS=|-87.9|FOM=|0.96|TEST=|0|
|INDE|6|37|49|FOBS=|55.9|SIGMA=|3.3|PHAS=|108.9|FOM=|0.67|TEST=|0|
|INDE|6|37|51|FOBS=|33.4|SIGMA=|4.3|PHAS=|177.6|FOM=|0.07|TEST=|1|
|INDE|6|37|53|FOBS=|95.1|SIGMA=|2.0|PHAS=|110.8|FOM=|0.73|TEST=|0|
|INDE|6|37|55|FOBS=|81.2|SIGMA=|2.3|PHAS=|-95.8|FOM=|0.64|TEST=|0|
|INDE|6|37|57|FOBS=|0.0|SIGMA=|18.8|PHAS=|0.0|FOM=|0.00|TEST=|0|
|INDE|6|37|59|FOBS=|0.0|SIGMA=|20.5|PHAS=|0.0|FOM=|0.00|TEST=|0|
|INDE|6|37|61|FOBS=|0.0|SIGMA=|19.6|PHAS=|0.0|FOM=|0.00|TEST=|0|
|INDE|6|37|63|FOBS=|78.2|SIGMA=|2.3|PHAS=|-5.2|FOM=|0.65|TEST=|0|
|INDE|6|37|65|FOBS=|0.0|SIGMA=|20.7|PHAS=|0.0|FOM=|0.00|TEST=|1|
|INDE|6|37|67|FOBS=|27.0|SIGMA=|11.6|PHAS=|-4.7|FOM=|0.48|TEST=|0|
|INDE|6|38|6|FOBS=|53.3|SIGMA=|2.4|PHAS=|135.9|FOM=|0.77|TEST=|0|
|INDE|6|38|8|FOBS=|270.7|SIGMA=|0.6|PHAS=|152.0|FOM=|0.93|TEST=|1|
|INDE|6|38|10|FOBS=|275.0|SIGMA=|1.0|PHAS=|99.2|FOM=|0.96|TEST=|0|
|INDE|6|38|12|FOBS=|228.2|SIGMA=|0.7|PHAS=|-125.7|FOM=|0.98|TEST=|0|
|INDE|6|38|14|FOBS=|153.0|SIGMA=|1.0|PHAS=|56.7|FOM=|0.69|TEST=|0|
|INDE|6|38|16|FOBS=|50.3|SIGMA=|3.0|PHAS=|-139.6|FOM=|0.77|TEST=|0|
|INDE|6|38|18|FOBS=|204.9|SIGMA=|1.0|PHAS=|-169.1|FOM=|0.96|TEST=|0|
|INDE|6|38|20|FOBS=|187.5|SIGMA=|1.0|PHAS=|-165.0|FOM=|0.93|TEST=|0|
|INDE|6|38|22|FOBS=|165.8|SIGMA=|1.4|PHAS=|115.4|FOM=|0.95|TEST=|0|
|INDE|6|38|24|FOBS=|136.4|SIGMA=|1.8|PHAS=|158.6|FOM=|0.91|TEST=|0|
|INDE|6|38|26|FOBS=|107.1|SIGMA=|2.3|PHAS=|-133.0|FOM=|0.90|TEST=|0|
|INDE|6|38|28|FOBS=|143.1|SIGMA=|1.8|PHAS=|-142.7|FOM=|0.83|TEST=|0|
|INDE|6|38|30|FOBS=|83.3|SIGMA=|2.7|PHAS=|163.1|FOM=|0.73|TEST=|0|
|INDE|6|38|32|FOBS=|0.0|SIGMA=|20.4|PHAS=|0.0|FOM=|0.00|TEST=|0|
|INDE|6|38|34|FOBS=|233.8|SIGMA=|1.0|PHAS=|-168.4|FOM=|0.87|TEST=|0|
|INDE|6|38|36|FOBS=|201.5|SIGMA=|1.1|PHAS=|-110.0|FOM=|0.12|TEST=|1|
|INDE|6|38|38|FOBS=|123.2|SIGMA=|1.6|PHAS=|67.4|FOM=|0.85|TEST=|0|
|INDE|6|38|40|FOBS=|135.6|SIGMA=|1.4|PHAS=|102.8|FOM=|0.84|TEST=|0|
|INDE|6|38|42|FOBS=|60.8|SIGMA=|3.0|PHAS=|98.9|FOM=|0.76|TEST=|0|
|INDE|6|38|44|FOBS=|40.9|SIGMA=|4.8|PHAS=|-105.5|FOM=|0.58|TEST=|0|
|INDE|6|38|46|FOBS=|13.3|SIGMA=|13.3|PHAS=|-167.8|FOM=|0.24|TEST=|0|
|INDE|6|38|48|FOBS=|81.4|SIGMA=|2.2|PHAS=|-92.2|FOM=|0.85|TEST=|0|
|INDE|6|38|50|FOBS=|0.0|SIGMA=|20.5|PHAS=|0.0|FOM=|0.00|TEST=|1|
|INDE|6|38|52|FOBS=|122.3|SIGMA=|1.5|PHAS=|122.0|FOM=|0.87|TEST=|0|

*FIG. 12A - 174*

| | | | | | | | | | | | |
|---|---|---|---|---|---|---|---|---|---|---|---|
| INDE | 6 | 38 | 54 | FOBS= | 69.9 | SIGMA= | 2.7 | PHAS= | 24.2 | FOM= | 0.82 | TEST= 0
| INDE | 6 | 38 | 56 | FOBS= | 46.4 | SIGMA= | 3.9 | PHAS= | 137.3 | FOM= | 0.59 | TEST= 0
| INDE | 6 | 38 | 58 | FOBS= | 15.8 | SIGMA= | 12.0 | PHAS= | 40.8 | FOM= | 0.16 | TEST= 0
| INDE | 6 | 38 | 60 | FOBS= | 0.0 | SIGMA= | 21.7 | PHAS= | 0.0 | FOM= | 0.00 | TEST= 0
| INDE | 6 | 38 | 62 | FOBS= | 0.0 | SIGMA= | 18.8 | PHAS= | 0.0 | FOM= | 0.00 | TEST= 1
| INDE | 6 | 38 | 64 | FOBS= | 17.6 | SIGMA= | 14.8 | PHAS= | -113.5 | FOM= | 0.40 | TEST= 0
| INDE | 6 | 38 | 66 | FOBS= | 15.1 | SIGMA= | 18.1 | PHAS= | 64.8 | FOM= | 0.25 | TEST= 0
| INDE | 6 | 39 | 7 | FOBS= | 361.8 | SIGMA= | 0.9 | PHAS= | 28.6 | FOM= | 0.99 | TEST= 0
| INDE | 6 | 39 | 9 | FOBS= | 32.2 | SIGMA= | 4.1 | PHAS= | 82.6 | FOM= | 0.27 | TEST= 0
| INDE | 6 | 39 | 11 | FOBS= | 186.7 | SIGMA= | 0.9 | PHAS= | -127.2 | FOM= | 0.97 | TEST= 0
| INDE | 6 | 39 | 13 | FOBS= | 162.0 | SIGMA= | 1.0 | PHAS= | 44.0 | FOM= | 0.97 | TEST= 0
| INDE | 6 | 39 | 15 | FOBS= | 48.4 | SIGMA= | 3.1 | PHAS= | 16.9 | FOM= | 0.59 | TEST= 0
| INDE | 6 | 39 | 17 | FOBS= | 122.3 | SIGMA= | 1.4 | PHAS= | -13.5 | FOM= | 0.90 | TEST= 0
| INDE | 6 | 39 | 19 | FOBS= | 174.5 | SIGMA= | 1.1 | PHAS= | 0.9 | FOM= | 0.84 | TEST= 0
| INDE | 6 | 39 | 21 | FOBS= | 221.5 | SIGMA= | 0.9 | PHAS= | -36.1 | FOM= | 0.89 | TEST= 0
| INDE | 6 | 39 | 23 | FOBS= | 39.6 | SIGMA= | 6.0 | PHAS= | 83.9 | FOM= | 0.91 | TEST= 1
| INDE | 6 | 39 | 25 | FOBS= | 314.4 | SIGMA= | 1.0 | PHAS= | 161.1 | FOM= | 0.96 | TEST= 0
| INDE | 6 | 39 | 27 | FOBS= | 126.2 | SIGMA= | 2.1 | PHAS= | 39.1 | FOM= | 0.96 | TEST= 1
| INDE | 6 | 39 | 29 | FOBS= | 143.6 | SIGMA= | 1.9 | PHAS= | -173.1 | FOM= | 0.76 | TEST= 0
| INDE | 6 | 39 | 31 | FOBS= | 109.3 | SIGMA= | 2.1 | PHAS= | 52.0 | FOM= | 0.55 | TEST= 0
| INDE | 6 | 39 | 33 | FOBS= | 83.9 | SIGMA= | 2.4 | PHAS= | -91.4 | FOM= | 0.91 | TEST= 1
| INDE | 6 | 39 | 35 | FOBS= | 0.0 | SIGMA= | 19.6 | PHAS= | 0.0 | FOM= | 0.00 | TEST= 0
| INDE | 6 | 39 | 37 | FOBS= | 116.1 | SIGMA= | 1.7 | PHAS= | -144.5 | FOM= | 0.93 | TEST= 0
| INDE | 6 | 39 | 39 | FOBS= | 113.2 | SIGMA= | 1.7 | PHAS= | -44.2 | FOM= | 0.92 | TEST= 0
| INDE | 6 | 39 | 41 | FOBS= | 150.5 | SIGMA= | 1.3 | PHAS= | -8.4 | FOM= | 0.95 | TEST= 0
| INDE | 6 | 39 | 43 | FOBS= | 59.5 | SIGMA= | 3.1 | PHAS= | -42.9 | FOM= | 0.59 | TEST= 0
| INDE | 6 | 39 | 45 | FOBS= | 97.6 | SIGMA= | 1.9 | PHAS= | -163.2 | FOM= | 0.86 | TEST= 0
| INDE | 6 | 39 | 47 | FOBS= | 136.4 | SIGMA= | 1.4 | PHAS= | -143.5 | FOM= | 0.96 | TEST= 0
| INDE | 6 | 39 | 49 | FOBS= | 69.4 | SIGMA= | 2.6 | PHAS= | -179.1 | FOM= | 0.66 | TEST= 0
| INDE | 6 | 39 | 51 | FOBS= | 41.1 | SIGMA= | 3.6 | PHAS= | -69.4 | FOM= | 0.14 | TEST= 1
| INDE | 6 | 39 | 53 | FOBS= | 137.4 | SIGMA= | 1.3 | PHAS= | 14.2 | FOM= | 0.80 | TEST= 0
| INDE | 6 | 39 | 55 | FOBS= | 27.9 | SIGMA= | 6.5 | PHAS= | -106.9 | FOM= | 0.31 | TEST= 0
| INDE | 6 | 39 | 57 | FOBS= | 39.4 | SIGMA= | 4.6 | PHAS= | -31.8 | FOM= | 0.38 | TEST= 0
| INDE | 6 | 39 | 59 | FOBS= | 0.0 | SIGMA= | 18.8 | PHAS= | 0.0 | FOM= | 0.00 | TEST= 0
| INDE | 6 | 39 | 61 | FOBS= | 0.0 | SIGMA= | 20.3 | PHAS= | 0.0 | FOM= | 0.00 | TEST= 0
| INDE | 6 | 39 | 63 | FOBS= | 41.3 | SIGMA= | 4.4 | PHAS= | -33.6 | FOM= | 0.68 | TEST= 0
| INDE | 6 | 39 | 65 | FOBS= | 21.7 | SIGMA= | 10.7 | PHAS= | 179.0 | FOM= | 0.60 | TEST= 0
| INDE | 6 | 39 | 67 | FOBS= | 0.0 | SIGMA= | 28.2 | PHAS= | 0.0 | FOM= | 0.00 | TEST= 0
| INDE | 6 | 40 | 6 | FOBS= | 162.8 | SIGMA= | 1.0 | PHAS= | -112.4 | FOM= | 0.91 | TEST= 0
| INDE | 6 | 40 | 8 | FOBS= | 27.4 | SIGMA= | 5.2 | PHAS= | -80.8 | FOM= | 0.43 | TEST= 0
| INDE | 6 | 40 | 10 | FOBS= | 332.6 | SIGMA= | 0.6 | PHAS= | 105.8 | FOM= | 0.97 | TEST= 0
| INDE | 6 | 40 | 12 | FOBS= | 40.5 | SIGMA= | 3.9 | PHAS= | 87.8 | FOM= | 0.83 | TEST= 0
| INDE | 6 | 40 | 14 | FOBS= | 304.5 | SIGMA= | 0.7 | PHAS= | -41.3 | FOM= | 0.99 | TEST= 0
| INDE | 6 | 40 | 16 | FOBS= | 57.4 | SIGMA= | 2.8 | PHAS= | -23.4 | FOM= | 0.98 | TEST= 0
| INDE | 6 | 40 | 18 | FOBS= | 182.4 | SIGMA= | 1.0 | PHAS= | 155.9 | FOM= | 0.66 | TEST= 0
| INDE | 6 | 40 | 20 | FOBS= | 199.9 | SIGMA= | 1.1 | PHAS= | -124.2 | FOM= | 0.73 | TEST= 0
| INDE | 6 | 40 | 22 | FOBS= | 304.7 | SIGMA= | 0.9 | PHAS= | 81.6 | FOM= | 0.97 | TEST= 0
| INDE | 6 | 40 | 24 | FOBS= | 237.9 | SIGMA= | 1.2 | PHAS= | 92.0 | FOM= | 0.97 | TEST= 1
| INDE | 6 | 40 | 26 | FOBS= | 64.5 | SIGMA= | 4.0 | PHAS= | 24.0 | FOM= | 0.39 | TEST= 0
| INDE | 6 | 40 | 28 | FOBS= | 91.6 | SIGMA= | 2.9 | PHAS= | -87.0 | FOM= | 0.90 | TEST= 0
| INDE | 6 | 40 | 30 | FOBS= | 81.5 | SIGMA= | 3.2 | PHAS= | 47.9 | FOM= | 0.93 | TEST= 0
| INDE | 6 | 40 | 32 | FOBS= | 115.4 | SIGMA= | 2.0 | PHAS= | -115.5 | FOM= | 0.92 | TEST= 0
| INDE | 6 | 40 | 34 | FOBS= | 149.9 | SIGMA= | 1.4 | PHAS= | 147.6 | FOM= | 0.92 | TEST= 0
| INDE | 6 | 40 | 36 | FOBS= | 130.1 | SIGMA= | 1.5 | PHAS= | 4.9 | FOM= | 0.95 | TEST= 0
| INDE | 6 | 40 | 38 | FOBS= | 191.3 | SIGMA= | 1.1 | PHAS= | 146.2 | FOM= | 0.96 | TEST= 0
| INDE | 6 | 40 | 40 | FOBS= | 0.0 | SIGMA= | 19.3 | PHAS= | 0.0 | FOM= | 0.00 | TEST= 1
| INDE | 6 | 40 | 42 | FOBS= | 46.6 | SIGMA= | 3.9 | PHAS= | -91.1 | FOM= | 0.47 | TEST= 0
| INDE | 6 | 40 | 44 | FOBS= | 56.4 | SIGMA= | 3.2 | PHAS= | 10.1 | FOM= | 0.55 | TEST= 0
| INDE | 6 | 40 | 46 | FOBS= | 150.3 | SIGMA= | 1.3 | PHAS= | 83.5 | FOM= | 0.95 | TEST= 0
| INDE | 6 | 40 | 48 | FOBS= | 55.9 | SIGMA= | 3.2 | PHAS= | 150.9 | FOM= | 0.70 | TEST= 0
| INDE | 6 | 40 | 50 | FOBS= | 103.3 | SIGMA= | 1.6 | PHAS= | 22.3 | FOM= | 0.88 | TEST= 0
| INDE | 6 | 40 | 52 | FOBS= | 80.1 | SIGMA= | 2.3 | PHAS= | -102.6 | FOM= | 0.40 | TEST= 1
| INDE | 6 | 40 | 54 | FOBS= | 28.2 | SIGMA= | 7.0 | PHAS= | 45.7 | FOM= | 0.62 | TEST= 1
| INDE | 6 | 40 | 56 | FOBS= | 68.1 | SIGMA= | 2.7 | PHAS= | 91.3 | FOM= | 0.62 | TEST= 1
| INDE | 6 | 40 | 58 | FOBS= | 0.0 | SIGMA= | 19.0 | PHAS= | 0.0 | FOM= | 0.00 | TEST= 0
| INDE | 6 | 40 | 60 | FOBS= | 0.0 | SIGMA= | 19.6 | PHAS= | 0.0 | FOM= | 0.00 | TEST= 0
| INDE | 6 | 40 | 62 | FOBS= | 29.1 | SIGMA= | 8.0 | PHAS= | -96.0 | FOM= | 0.63 | TEST= 0
| INDE | 6 | 40 | 64 | FOBS= | 0.0 | SIGMA= | 20.6 | PHAS= | 0.0 | FOM= | 0.00 | TEST= 0
| INDE | 6 | 40 | 66 | FOBS= | 72.6 | SIGMA= | 4.5 | PHAS= | -31.1 | FOM= | 0.60 | TEST= 0
| INDE | 6 | 41 | 7 | FOBS= | 165.9 | SIGMA= | 1.0 | PHAS= | 74.6 | FOM= | 0.98 | TEST= 0

*FIG. 12A - 175*

```
INDE  6  41   9 FOBS=  239.2 SIGMA=  0.6 PHAS=   41.1 FOM= 0.96 TEST= 0
INDE  6  41  11 FOBS=  179.9 SIGMA=  1.1 PHAS=   -7.1 FOM= 0.71 TEST= 0
INDE  6  41  13 FOBS=  396.5 SIGMA=  0.7 PHAS=   -0.9 FOM= 0.77 TEST= 1
INDE  6  41  15 FOBS=  201.3 SIGMA=  0.9 PHAS=  -24.1 FOM= 0.56 TEST= 1
INDE  6  41  17 FOBS=   93.0 SIGMA=  1.9 PHAS=  -46.0 FOM= 0.79 TEST= 0
INDE  6  41  19 FOBS=  179.4 SIGMA=  1.2 PHAS=    3.1 FOM= 0.91 TEST= 0
INDE  6  41  21 FOBS=  295.5 SIGMA=  0.9 PHAS=  -11.7 FOM= 0.95 TEST= 0
INDE  6  41  23 FOBS=  283.6 SIGMA=  1.0 PHAS=  -24.0 FOM= 0.92 TEST= 1
INDE  6  41  25 FOBS=   34.6 SIGMA=  7.6 PHAS=   57.7 FOM= 0.29 TEST= 0
INDE  6  41  27 FOBS=  127.0 SIGMA=  2.2 PHAS=  175.1 FOM= 0.61 TEST= 0
INDE  6  41  29 FOBS=   82.9 SIGMA=  3.1 PHAS=  -80.1 FOM= 0.92 TEST= 0
INDE  6  41  31 FOBS=  182.6 SIGMA=  1.5 PHAS=  167.2 FOM= 0.69 TEST= 1
INDE  6  41  33 FOBS=  178.3 SIGMA=  1.3 PHAS= -166.1 FOM= 0.93 TEST= 0
INDE  6  41  35 FOBS=  149.9 SIGMA=  1.4 PHAS=  -98.9 FOM= 0.91 TEST= 0
INDE  6  41  37 FOBS=   79.0 SIGMA=  2.5 PHAS=   80.3 FOM= 0.76 TEST= 0
INDE  6  41  39 FOBS=  124.9 SIGMA=  1.6 PHAS= -141.2 FOM= 0.93 TEST= 0
INDE  6  41  41 FOBS=   10.9 SIGMA= 19.0 PHAS=   84.3 FOM= 0.10 TEST= 0
INDE  6  41  43 FOBS=   35.7 SIGMA=  5.1 PHAS=  -51.0 FOM= 0.52 TEST= 0
INDE  6  41  45 FOBS=  126.2 SIGMA=  1.5 PHAS=  -18.3 FOM= 0.92 TEST= 0
INDE  6  41  47 FOBS=   82.8 SIGMA=  2.2 PHAS=   42.9 FOM= 0.03 TEST= 1
INDE  6  41  49 FOBS=   64.1 SIGMA=  2.8 PHAS=   88.5 FOM= 0.17 TEST= 0
INDE  6  41  51 FOBS=  144.1 SIGMA=  1.3 PHAS= -141.7 FOM= 0.90 TEST= 0
INDE  6  41  53 FOBS=   76.8 SIGMA=  2.3 PHAS=  -75.7 FOM= 0.80 TEST= 0
INDE  6  41  55 FOBS=  103.1 SIGMA=  1.7 PHAS=   -4.9 FOM= 0.91 TEST= 0
INDE  6  41  57 FOBS=   45.2 SIGMA=  4.1 PHAS=  -53.5 FOM= 0.76 TEST= 0
INDE  6  41  59 FOBS=   49.1 SIGMA=  4.4 PHAS=  -89.2 FOM= 0.74 TEST= 0
INDE  6  41  61 FOBS=   62.0 SIGMA=  3.0 PHAS=  112.3 FOM= 0.90 TEST= 0
INDE  6  41  63 FOBS=   66.1 SIGMA=  2.9 PHAS= -154.1 FOM= 0.84 TEST= 0
INDE  6  41  65 FOBS=   83.0 SIGMA=  3.0 PHAS= -100.6 FOM= 0.93 TEST= 0
INDE  6  42   6 FOBS=  141.7 SIGMA=  1.2 PHAS= -126.7 FOM= 0.71 TEST= 0
INDE  6  42   8 FOBS=  495.3 SIGMA=  0.5 PHAS=   17.8 FOM= 0.57 TEST= 1
INDE  6  42  10 FOBS=    0.0 SIGMA= 16.2 PHAS=    0.0 FOM= 0.00 TEST= 0
INDE  6  42  12 FOBS=  248.5 SIGMA=  0.9 PHAS=    3.8 FOM= 0.77 TEST= 0
INDE  6  42  14 FOBS=  172.4 SIGMA=  1.1 PHAS= -126.7 FOM= 0.57 TEST= 1
INDE  6  42  16 FOBS=  142.0 SIGMA=  1.3 PHAS=  -85.0 FOM= 0.85 TEST= 0
INDE  6  42  18 FOBS=  243.5 SIGMA=  1.0 PHAS=  -28.5 FOM= 0.96 TEST= 0
INDE  6  42  20 FOBS=  165.2 SIGMA=  1.6 PHAS= -154.1 FOM= 0.92 TEST= 0
INDE  6  42  22 FOBS=   60.9 SIGMA=  3.3 PHAS=  -95.8 FOM= 0.76 TEST= 0
INDE  6  42  24 FOBS=  200.7 SIGMA=  1.1 PHAS=  -39.1 FOM= 0.92 TEST= 0
INDE  6  42  26 FOBS=  194.1 SIGMA=  1.5 PHAS= -127.2 FOM= 0.93 TEST= 0
INDE  6  42  28 FOBS=  143.9 SIGMA=  1.9 PHAS= -157.3 FOM= 0.90 TEST= 0
INDE  6  42  30 FOBS=    0.0 SIGMA= 27.9 PHAS=    0.0 FOM= 0.00 TEST= 0
INDE  6  42  32 FOBS=  110.4 SIGMA=  2.0 PHAS=   39.6 FOM= 0.90 TEST= 0
INDE  6  42  34 FOBS=  176.9 SIGMA=  1.2 PHAS=  105.6 FOM= 0.94 TEST= 0
INDE  6  42  36 FOBS=    0.0 SIGMA= 21.2 PHAS=    0.0 FOM= 0.00 TEST= 0
INDE  6  42  38 FOBS=   38.9 SIGMA=  5.7 PHAS=  167.7 FOM= 0.73 TEST= 1
INDE  6  42  40 FOBS=  204.2 SIGMA=  1.0 PHAS=  -34.9 FOM= 0.80 TEST= 1
INDE  6  42  42 FOBS=  131.8 SIGMA=  1.5 PHAS=  130.8 FOM= 0.82 TEST= 0
INDE  6  42  44 FOBS=  149.7 SIGMA=  1.3 PHAS=  -72.2 FOM= 0.94 TEST= 0
INDE  6  42  46 FOBS=    0.0 SIGMA= 19.3 PHAS=    0.0 FOM= 0.00 TEST= 0
INDE  6  42  48 FOBS=   47.8 SIGMA=  3.7 PHAS= -108.1 FOM= 0.61 TEST= 0
INDE  6  42  50 FOBS=  138.6 SIGMA=  1.2 PHAS=  108.9 FOM= 0.96 TEST= 0
INDE  6  42  52 FOBS=   67.8 SIGMA=  2.6 PHAS=  154.8 FOM= 0.82 TEST= 0
INDE  6  42  54 FOBS=   17.3 SIGMA= 10.6 PHAS=  -94.6 FOM= 0.04 TEST= 1
INDE  6  42  56 FOBS=   58.5 SIGMA=  3.0 PHAS= -126.6 FOM= 0.81 TEST= 0
INDE  6  42  58 FOBS=   96.3 SIGMA=  2.0 PHAS= -139.7 FOM= 0.93 TEST= 0
INDE  6  42  60 FOBS=   40.9 SIGMA=  4.6 PHAS=  -57.4 FOM= 0.61 TEST= 0
INDE  6  42  62 FOBS=   42.1 SIGMA=  4.8 PHAS=    9.9 FOM= 0.49 TEST= 0
INDE  6  42  64 FOBS=   74.1 SIGMA=  3.0 PHAS=  145.4 FOM= 0.91 TEST= 0
INDE  6  43   7 FOBS=  304.6 SIGMA=  1.1 PHAS= -130.1 FOM= 0.94 TEST= 0
INDE  6  43   9 FOBS=  354.2 SIGMA=  0.6 PHAS=  -76.8 FOM= 0.94 TEST= 0
INDE  6  43  11 FOBS=   60.9 SIGMA=  2.5 PHAS=  -90.9 FOM= 0.91 TEST= 0
INDE  6  43  13 FOBS=  141.1 SIGMA=  1.3 PHAS=   -9.8 FOM= 0.95 TEST= 0
INDE  6  43  15 FOBS=  186.7 SIGMA=  1.1 PHAS=  108.7 FOM= 0.89 TEST= 0
INDE  6  43  17 FOBS=   75.7 SIGMA=  2.9 PHAS=  -42.4 FOM= 0.63 TEST= 0
INDE  6  43  19 FOBS=  120.5 SIGMA=  1.7 PHAS=   87.8 FOM= 0.87 TEST= 0
INDE  6  43  21 FOBS=   99.5 SIGMA=  2.3 PHAS= -156.2 FOM= 0.93 TEST= 0
INDE  6  43  23 FOBS=  271.0 SIGMA=  0.9 PHAS= -172.7 FOM= 0.97 TEST= 0
INDE  6  43  25 FOBS=  150.4 SIGMA=  1.5 PHAS= -148.7 FOM= 0.83 TEST= 0
INDE  6  43  27 FOBS=   47.7 SIGMA=  5.4 PHAS=   83.1 FOM= 0.64 TEST= 0
```

*FIG. 12A - 176*

```
INDE  6  43  29  FOBS=   164.7  SIGMA=   1.7  PHAS=  -153.5  FOM=  0.92  TEST=  0
INDE  6  43  31  FOBS=    52.9  SIGMA=   4.8  PHAS=    49.6  FOM=  0.50  TEST=  0
INDE  6  43  33  FOBS=   178.3  SIGMA=   1.3  PHAS=   -34.7  FOM=  0.93  TEST=  0
INDE  6  43  35  FOBS=    49.1  SIGMA=   3.8  PHAS=   -57.3  FOM=  0.59  TEST=  0
INDE  6  43  37  FOBS=    79.4  SIGMA=   2.4  PHAS=   -22.8  FOM=  0.83  TEST=  0
INDE  6  43  39  FOBS=    71.2  SIGMA=   2.7  PHAS=  -158.2  FOM=  0.87  TEST=  0
INDE  6  43  41  FOBS=   189.3  SIGMA=   1.1  PHAS=   170.5  FOM=  0.93  TEST=  0
INDE  6  43  43  FOBS=    40.8  SIGMA=   4.5  PHAS=   -42.6  FOM=  0.33  TEST=  0
INDE  6  43  45  FOBS=     0.0  SIGMA=  19.0  PHAS=     0.0  FOM=  0.00  TEST=  0
INDE  6  43  47  FOBS=    34.4  SIGMA=   5.4  PHAS=   -69.8  FOM=  0.49  TEST=  0
INDE  6  43  49  FOBS=     0.0  SIGMA=  19.4  PHAS=     0.0  FOM=  0.00  TEST=  0
INDE  6  43  51  FOBS=    54.0  SIGMA=   3.5  PHAS=    47.0  FOM=  0.79  TEST=  0
INDE  6  43  53  FOBS=    82.3  SIGMA=   2.2  PHAS=  -119.7  FOM=  0.85  TEST=  0
INDE  6  43  55  FOBS=    29.7  SIGMA=   6.0  PHAS=    72.6  FOM=  0.23  TEST=  0
INDE  6  43  57  FOBS=    75.3  SIGMA=   2.4  PHAS=   161.5  FOM=  0.88  TEST=  0
INDE  6  43  59  FOBS=     8.4  SIGMA=  23.6  PHAS=  -165.1  FOM=  0.30  TEST=  0
INDE  6  43  61  FOBS=     0.0  SIGMA=  19.4  PHAS=     0.0  FOM=  0.00  TEST=  0
INDE  6  43  63  FOBS=    37.4  SIGMA=   6.0  PHAS=   113.8  FOM=  0.31  TEST=  0
INDE  6  44   6  FOBS=    95.2  SIGMA=   1.8  PHAS=   163.0  FOM=  0.83  TEST=  0
INDE  6  44   8  FOBS=     0.0  SIGMA=  21.8  PHAS=     0.0  FOM=  0.00  TEST=  0
INDE  6  44  10  FOBS=   104.3  SIGMA=   1.4  PHAS=  -162.9  FOM=  0.90  TEST=  0
INDE  6  44  12  FOBS=   143.8  SIGMA=   1.0  PHAS=  -116.4  FOM=  0.86  TEST=  0
INDE  6  44  14  FOBS=   170.0  SIGMA=   1.2  PHAS=   -63.3  FOM=  0.76  TEST=  0
INDE  6  44  16  FOBS=   409.5  SIGMA=   0.8  PHAS=   -70.2  FOM=  0.98  TEST=  0
INDE  6  44  18  FOBS=    89.8  SIGMA=   2.3  PHAS=  -112.9  FOM=  0.80  TEST=  0
INDE  6  44  20  FOBS=    52.0  SIGMA=   4.3  PHAS=    67.6  FOM=  0.90  TEST=  0
INDE  6  44  22  FOBS=   151.6  SIGMA=   1.5  PHAS=    90.7  FOM=  0.97  TEST=  0
INDE  6  44  24  FOBS=   114.5  SIGMA=   1.9  PHAS=   154.6  FOM=  0.93  TEST=  0
INDE  6  44  26  FOBS=   173.1  SIGMA=   1.6  PHAS=  -106.6  FOM=  0.90  TEST=  0
INDE  6  44  28  FOBS=   110.4  SIGMA=   2.4  PHAS=   111.6  FOM=  0.84  TEST=  0
INDE  6  44  30  FOBS=    78.6  SIGMA=   3.2  PHAS=    43.0  FOM=  0.90  TEST=  0
INDE  6  44  32  FOBS=    67.5  SIGMA=   3.7  PHAS=   -51.5  FOM=  0.64  TEST=  0
INDE  6  44  34  FOBS=    73.1  SIGMA=   2.9  PHAS=  -104.4  FOM=  0.79  TEST=  1
INDE  6  44  36  FOBS=     0.0  SIGMA=  20.4  PHAS=     0.0  FOM=  0.00  TEST=  0
INDE  6  44  38  FOBS=    39.7  SIGMA=   5.0  PHAS=    98.2  FOM=  0.76  TEST=  0
INDE  6  44  40  FOBS=    69.5  SIGMA=   2.7  PHAS=   117.8  FOM=  0.94  TEST=  0
INDE  6  44  42  FOBS=   136.1  SIGMA=   1.4  PHAS=    27.6  FOM=  0.96  TEST=  0
INDE  6  44  44  FOBS=     0.0  SIGMA=  19.0  PHAS=     0.0  FOM=  0.00  TEST=  0
INDE  6  44  46  FOBS=    51.3  SIGMA=   3.5  PHAS=  -110.4  FOM=  0.81  TEST=  0
INDE  6  44  48  FOBS=    85.7  SIGMA=   2.1  PHAS=     7.2  FOM=  0.10  TEST=  1
INDE  6  44  50  FOBS=     0.0  SIGMA=  23.0  PHAS=     0.0  FOM=  0.00  TEST=  0
INDE  6  44  52  FOBS=    63.4  SIGMA=   2.8  PHAS=   103.1  FOM=  0.81  TEST=  0
INDE  6  44  54  FOBS=     0.0  SIGMA=  20.0  PHAS=     0.0  FOM=  0.00  TEST=  0
INDE  6  44  56  FOBS=    18.1  SIGMA=  10.8  PHAS=  -168.3  FOM=  0.21  TEST=  0
INDE  6  44  58  FOBS=     0.0  SIGMA=  20.4  PHAS=     0.0  FOM=  0.00  TEST=  0
INDE  6  44  60  FOBS=    62.7  SIGMA=   3.0  PHAS=    78.1  FOM=  0.90  TEST=  0
INDE  6  44  62  FOBS=     0.0  SIGMA=  21.0  PHAS=     0.0  FOM=  0.00  TEST=  1
INDE  6  45   7  FOBS=    98.7  SIGMA=   2.1  PHAS=    77.0  FOM=  0.51  TEST=  0
INDE  6  45   9  FOBS=   143.2  SIGMA=   1.2  PHAS=   -73.3  FOM=  0.86  TEST=  0
INDE  6  45  11  FOBS=   352.0  SIGMA=   0.7  PHAS=  -166.1  FOM=  0.98  TEST=  0
INDE  6  45  13  FOBS=   149.0  SIGMA=   1.0  PHAS=   108.6  FOM=  0.90  TEST=  0
INDE  6  45  15  FOBS=   114.7  SIGMA=   1.8  PHAS=   -74.4  FOM=  0.81  TEST=  0
INDE  6  45  17  FOBS=   230.4  SIGMA=   1.0  PHAS=  -170.7  FOM=  0.90  TEST=  1
INDE  6  45  19  FOBS=   228.5  SIGMA=   1.0  PHAS=   119.5  FOM=  0.96  TEST=  0
INDE  6  45  21  FOBS=    28.7  SIGMA=   8.1  PHAS=   102.5  FOM=  0.82  TEST=  1
INDE  6  45  23  FOBS=   194.3  SIGMA=   1.2  PHAS=   165.8  FOM=  0.98  TEST=  0
INDE  6  45  25  FOBS=   109.2  SIGMA=   1.9  PHAS=    59.6  FOM=  0.34  TEST=  1
INDE  6  45  27  FOBS=   106.3  SIGMA=   2.5  PHAS=    36.7  FOM=  0.79  TEST=  1
INDE  6  45  29  FOBS=    99.8  SIGMA=   2.6  PHAS=  -151.7  FOM=  0.88  TEST=  0
INDE  6  45  31  FOBS=    37.6  SIGMA=   6.6  PHAS=   -68.0  FOM=  0.34  TEST=  0
INDE  6  45  33  FOBS=     0.0  SIGMA=  23.6  PHAS=     0.0  FOM=  0.00  TEST=  0
INDE  6  45  35  FOBS=   101.0  SIGMA=   2.1  PHAS=  -135.5  FOM=  0.86  TEST=  0
INDE  6  45  37  FOBS=    55.9  SIGMA=   3.4  PHAS=   -25.0  FOM=  0.95  TEST=  1
INDE  6  45  39  FOBS=     0.0  SIGMA=  19.2  PHAS=     0.0  FOM=  0.00  TEST=  0
INDE  6  45  41  FOBS=    60.2  SIGMA=   3.1  PHAS=   -50.9  FOM=  0.91  TEST=  0
INDE  6  45  43  FOBS=    47.3  SIGMA=   3.9  PHAS=    22.8  FOM=  0.61  TEST=  0
INDE  6  45  45  FOBS=    75.3  SIGMA=   2.4  PHAS=   131.1  FOM=  0.42  TEST=  0
INDE  6  45  47  FOBS=    76.4  SIGMA=   2.4  PHAS=   -80.6  FOM=  0.71  TEST=  0
INDE  6  45  49  FOBS=   138.8  SIGMA=   1.4  PHAS=  -157.6  FOM=  0.96  TEST=  0
INDE  6  45  51  FOBS=    87.0  SIGMA=   2.1  PHAS=    12.2  FOM=  0.89  TEST=  0
```

*FIG. 12A - 177*

```
INDE  6  45  53  FOBS=   40.6  SIGMA=   4.3  PHAS=  -109.6  FOM=  0.54  TEST= 0
INDE  6  45  55  FOBS=   61.7  SIGMA=   2.9  PHAS=   151.8  FOM=  0.73  TEST= 0
INDE  6  45  57  FOBS=    0.0  SIGMA=  20.7  PHAS=     0.0  FOM=  0.00  TEST= 0
INDE  6  45  59  FOBS=    0.0  SIGMA=  20.4  PHAS=     0.0  FOM=  0.00  TEST= 0
INDE  6  45  61  FOBS=   68.6  SIGMA=   3.3  PHAS=   -31.0  FOM=  0.90  TEST= 0
INDE  6  45  63  FOBS=   44.6  SIGMA=   6.2  PHAS=    88.0  FOM=  0.55  TEST= 0
INDE  6  46   6  FOBS=   39.7  SIGMA=   5.4  PHAS=    -2.7  FOM=  0.85  TEST= 0
INDE  6  46   8  FOBS=  129.3  SIGMA=   2.1  PHAS=   -57.4  FOM=  0.91  TEST= 0
INDE  6  46  10  FOBS=  140.6  SIGMA=   1.4  PHAS=   122.0  FOM=  0.93  TEST= 0
INDE  6  46  12  FOBS=  129.1  SIGMA=   1.4  PHAS=   172.0  FOM=  0.89  TEST= 0
INDE  6  46  14  FOBS=  156.6  SIGMA=   1.4  PHAS=   -80.5  FOM=  0.94  TEST= 0
INDE  6  46  16  FOBS=  208.8  SIGMA=   1.1  PHAS=   -67.4  FOM=  0.96  TEST= 0
INDE  6  46  18  FOBS=  157.8  SIGMA=   1.4  PHAS=   108.7  FOM=  0.93  TEST= 0
INDE  6  46  20  FOBS=   48.6  SIGMA=   4.5  PHAS=  -114.6  FOM=  0.25  TEST= 0
INDE  6  46  22  FOBS=   84.1  SIGMA=   2.5  PHAS=    44.7  FOM=  0.93  TEST= 0
INDE  6  46  24  FOBS=  242.5  SIGMA=   1.0  PHAS=  -111.0  FOM=  0.88  TEST= 0
INDE  6  46  26  FOBS=  137.4  SIGMA=   1.6  PHAS=   -44.6  FOM=  0.81  TEST= 0
INDE  6  46  28  FOBS=  111.0  SIGMA=   2.4  PHAS=    46.0  FOM=  0.80  TEST= 0
INDE  6  46  30  FOBS=   67.2  SIGMA=   3.8  PHAS=    88.2  FOM=  0.83  TEST= 0
INDE  6  46  32  FOBS=  120.3  SIGMA=   2.1  PHAS=   -40.8  FOM=  0.90  TEST= 0
INDE  6  46  34  FOBS=   64.1  SIGMA=   3.5  PHAS=  -129.9  FOM=  0.77  TEST= 0
INDE  6  46  36  FOBS=   63.2  SIGMA=   3.3  PHAS=    33.1  FOM=  0.58  TEST= 0
INDE  6  46  38  FOBS=    0.0  SIGMA=  19.1  PHAS=     0.0  FOM=  0.00  TEST= 0
INDE  6  46  40  FOBS=   97.8  SIGMA=   2.0  PHAS=   139.3  FOM=  0.92  TEST= 0
INDE  6  46  42  FOBS=  134.8  SIGMA=   1.5  PHAS=   -27.2  FOM=  0.83  TEST= 1
INDE  6  46  44  FOBS=  101.7  SIGMA=   1.8  PHAS=  -138.2  FOM=  0.85  TEST= 0
INDE  6  46  46  FOBS=  145.0  SIGMA=   1.3  PHAS=  -125.6  FOM=  0.96  TEST= 0
INDE  6  46  48  FOBS=   39.2  SIGMA=   4.6  PHAS=   138.8  FOM=  0.53  TEST= 0
INDE  6  46  50  FOBS=   55.9  SIGMA=   3.5  PHAS=   175.9  FOM=  0.67  TEST= 0
INDE  6  46  52  FOBS=    4.1  SIGMA=  46.0  PHAS=  -126.7  FOM=  0.08  TEST= 0
INDE  6  46  54  FOBS=    0.0  SIGMA=  21.0  PHAS=     0.0  FOM=  0.00  TEST= 0
INDE  6  46  56  FOBS=   18.1  SIGMA=  11.9  PHAS=    60.0  FOM=  0.30  TEST= 0
INDE  6  46  58  FOBS=   53.8  SIGMA=   3.4  PHAS=   -22.2  FOM=  0.58  TEST= 0
INDE  6  46  60  FOBS=   44.8  SIGMA=   5.0  PHAS=   140.8  FOM=  0.32  TEST= 1
INDE  6  46  62  FOBS=   23.0  SIGMA=  12.5  PHAS=  -109.1  FOM=  0.40  TEST= 0
INDE  6  47   7  FOBS=   71.1  SIGMA=   3.8  PHAS=   144.7  FOM=  0.87  TEST= 0
INDE  6  47   9  FOBS=  176.7  SIGMA=   1.7  PHAS=   -60.2  FOM=  0.77  TEST= 1
INDE  6  47  11  FOBS=  290.6  SIGMA=   0.8  PHAS=   167.5  FOM=  0.96  TEST= 0
INDE  6  47  13  FOBS=  204.9  SIGMA=   0.9  PHAS=    95.4  FOM=  0.97  TEST= 0
INDE  6  47  15  FOBS=  104.4  SIGMA=   2.0  PHAS=   -65.9  FOM=  0.78  TEST= 0
INDE  6  47  17  FOBS=  125.7  SIGMA=   1.7  PHAS=  -106.5  FOM=  0.96  TEST= 0
INDE  6  47  19  FOBS=  413.6  SIGMA=   0.7  PHAS=   124.9  FOM=  0.98  TEST= 0
INDE  6  47  21  FOBS=  129.3  SIGMA=   1.8  PHAS=   159.8  FOM=  0.90  TEST= 0
INDE  6  47  23  FOBS=   68.7  SIGMA=   3.0  PHAS=   155.2  FOM=  0.55  TEST= 0
INDE  6  47  25  FOBS=  176.4  SIGMA=   1.3  PHAS=    55.3  FOM=  0.90  TEST= 0
INDE  6  47  27  FOBS=   55.1  SIGMA=   3.6  PHAS=   -36.5  FOM=  0.72  TEST= 0
INDE  6  47  29  FOBS=   40.5  SIGMA=   7.3  PHAS=    -0.2  FOM=  0.15  TEST= 0
INDE  6  47  31  FOBS=   75.3  SIGMA=   3.4  PHAS=  -166.5  FOM=  0.81  TEST= 0
INDE  6  47  33  FOBS=  250.4  SIGMA=   1.2  PHAS=  -134.1  FOM=  0.97  TEST= 0
INDE  6  47  35  FOBS=   36.4  SIGMA=   5.7  PHAS=    35.9  FOM=  0.31  TEST= 0
INDE  6  47  37  FOBS=  126.4  SIGMA=   1.6  PHAS=     9.5  FOM=  0.89  TEST= 0
INDE  6  47  39  FOBS=   27.6  SIGMA=   8.5  PHAS=    83.8  FOM=  0.20  TEST= 0
INDE  6  47  41  FOBS=   68.0  SIGMA=   2.8  PHAS=    69.3  FOM=  0.80  TEST= 0
INDE  6  47  43  FOBS=   45.3  SIGMA=   4.2  PHAS=   -79.7  FOM=  0.33  TEST= 0
INDE  6  47  45  FOBS=   70.9  SIGMA=   2.6  PHAS=   150.4  FOM=  0.87  TEST= 0
INDE  6  47  47  FOBS=  127.4  SIGMA=   1.5  PHAS=  -123.5  FOM=  0.79  TEST= 0
INDE  6  47  49  FOBS=   83.0  SIGMA=   2.4  PHAS=   168.2  FOM=  0.88  TEST= 0
INDE  6  47  51  FOBS=    0.0  SIGMA=  21.6  PHAS=     0.0  FOM=  0.00  TEST= 1
INDE  6  47  53  FOBS=   44.7  SIGMA=   4.0  PHAS=    48.5  FOM=  0.22  TEST= 1
INDE  6  47  55  FOBS=   55.5  SIGMA=   3.2  PHAS=    44.2  FOM=  0.65  TEST= 0
INDE  6  47  57  FOBS=   52.5  SIGMA=   3.5  PHAS=  -100.6  FOM=  0.84  TEST= 0
INDE  6  47  59  FOBS=   74.3  SIGMA=   2.8  PHAS=   -62.0  FOM=  0.75  TEST= 0
INDE  6  47  61  FOBS=   80.0  SIGMA=   3.2  PHAS=   -33.1  FOM=  0.85  TEST= 0
INDE  6  48   6  FOBS=  107.3  SIGMA=   1.9  PHAS=  -166.8  FOM=  0.70  TEST= 0
INDE  6  48   8  FOBS=   54.1  SIGMA=   5.1  PHAS=   -29.4  FOM=  0.92  TEST= 0
INDE  6  48  10  FOBS=  139.4  SIGMA=   1.4  PHAS=   -86.9  FOM=  0.79  TEST= 0
INDE  6  48  12  FOBS=   98.4  SIGMA=   1.7  PHAS=   170.5  FOM=  0.90  TEST= 0
INDE  6  48  14  FOBS=  273.1  SIGMA=   0.7  PHAS=    17.6  FOM=  0.96  TEST= 0
INDE  6  48  16  FOBS=  189.4  SIGMA=   1.3  PHAS=     5.9  FOM=  0.91  TEST= 0
INDE  6  48  18  FOBS=  206.1  SIGMA=   1.1  PHAS=    58.5  FOM=  0.93  TEST= 0
```

*FIG. 12A - 178*

| | | | | | | | | | | | | |
|---|---|---|---|---|---|---|---|---|---|---|---|---|
| INDE | 6 | 48 | 20 | FOBS= | 185.1 | SIGMA= | 1.2 | PHAS= | 69.7 | FOM= | 0.94 | TEST= 0 |
| INDE | 6 | 48 | 22 | FOBS= | 162.8 | SIGMA= | 1.3 | PHAS= | -95.7 | FOM= | 0.70 | TEST= 0 |
| INDE | 6 | 48 | 24 | FOBS= | 81.6 | SIGMA= | 2.5 | PHAS= | 3.8 | FOM= | 0.35 | TEST= 0 |
| INDE | 6 | 48 | 26 | FOBS= | 106.4 | SIGMA= | 2.0 | PHAS= | -70.1 | FOM= | 0.79 | TEST= 0 |
| INDE | 6 | 48 | 28 | FOBS= | 123.5 | SIGMA= | 1.7 | PHAS= | 49.4 | FOM= | 0.90 | TEST= 0 |
| INDE | 6 | 48 | 30 | FOBS= | 141.3 | SIGMA= | 1.9 | PHAS= | 7.5 | FOM= | 0.95 | TEST= 0 |
| INDE | 6 | 48 | 32 | FOBS= | 136.8 | SIGMA= | 1.9 | PHAS= | 160.5 | FOM= | 0.90 | TEST= 0 |
| INDE | 6 | 48 | 34 | FOBS= | 219.0 | SIGMA= | 1.3 | PHAS= | 168.6 | FOM= | 0.97 | TEST= 0 |
| INDE | 6 | 48 | 36 | FOBS= | 59.0 | SIGMA= | 3.5 | PHAS= | 51.5 | FOM= | 0.15 | TEST= 1 |
| INDE | 6 | 48 | 38 | FOBS= | 34.3 | SIGMA= | 5.7 | PHAS= | -117.3 | FOM= | 0.63 | TEST= 1 |
| INDE | 6 | 48 | 40 | FOBS= | 84.3 | SIGMA= | 2.2 | PHAS= | 43.8 | FOM= | 0.87 | TEST= 0 |
| INDE | 6 | 48 | 42 | FOBS= | 96.0 | SIGMA= | 2.0 | PHAS= | -40.9 | FOM= | 0.85 | TEST= 0 |
| INDE | 6 | 48 | 44 | FOBS= | 65.2 | SIGMA= | 2.8 | PHAS= | -147.9 | FOM= | 0.49 | TEST= 0 |
| INDE | 6 | 48 | 46 | FOBS= | 0.0 | SIGMA= | 19.9 | PHAS= | 0.0 | FOM= | 0.00 | TEST= 0 |
| INDE | 6 | 48 | 48 | FOBS= | 69.6 | SIGMA= | 2.6 | PHAS= | 126.6 | FOM= | 0.88 | TEST= 0 |
| INDE | 6 | 48 | 50 | FOBS= | 100.4 | SIGMA= | 2.0 | PHAS= | 27.8 | FOM= | 0.83 | TEST= 0 |
| INDE | 6 | 48 | 52 | FOBS= | 0.0 | SIGMA= | 20.4 | PHAS= | 0.0 | FOM= | 0.00 | TEST= 0 |
| INDE | 6 | 48 | 54 | FOBS= | 15.7 | SIGMA= | 15.7 | PHAS= | -71.1 | FOM= | 0.16 | TEST= 0 |
| INDE | 6 | 48 | 56 | FOBS= | 22.0 | SIGMA= | 10.0 | PHAS= | -166.6 | FOM= | 0.31 | TEST= 0 |
| INDE | 6 | 48 | 58 | FOBS= | 72.5 | SIGMA= | 2.7 | PHAS= | -160.7 | FOM= | 0.77 | TEST= 0 |
| INDE | 6 | 48 | 60 | FOBS= | 48.3 | SIGMA= | 4.8 | PHAS= | -95.8 | FOM= | 0.68 | TEST= 0 |
| INDE | 6 | 49 | 7 | FOBS= | 187.3 | SIGMA= | 1.6 | PHAS= | 112.3 | FOM= | 0.86 | TEST= 0 |
| INDE | 6 | 49 | 9 | FOBS= | 117.2 | SIGMA= | 2.4 | PHAS= | 143.1 | FOM= | 0.69 | TEST= 0 |
| INDE | 6 | 49 | 11 | FOBS= | 289.4 | SIGMA= | 0.9 | PHAS= | 174.7 | FOM= | 0.97 | TEST= 0 |
| INDE | 6 | 49 | 13 | FOBS= | 183.1 | SIGMA= | 1.0 | PHAS= | -54.0 | FOM= | 0.93 | TEST= 0 |
| INDE | 6 | 49 | 15 | FOBS= | 291.7 | SIGMA= | 0.6 | PHAS= | -28.6 | FOM= | 0.97 | TEST= 0 |
| INDE | 6 | 49 | 17 | FOBS= | 243.5 | SIGMA= | 0.9 | PHAS= | -63.1 | FOM= | 0.95 | TEST= 0 |
| INDE | 6 | 49 | 19 | FOBS= | 0.0 | SIGMA= | 22.3 | PHAS= | 0.0 | FOM= | 0.00 | TEST= 0 |
| INDE | 6 | 49 | 21 | FOBS= | 0.0 | SIGMA= | 21.5 | PHAS= | 0.0 | FOM= | 0.00 | TEST= 0 |
| INDE | 6 | 49 | 23 | FOBS= | 276.5 | SIGMA= | 0.9 | PHAS= | 94.9 | FOM= | 0.97 | TEST= 0 |
| INDE | 6 | 49 | 25 | FOBS= | 39.2 | SIGMA= | 5.2 | PHAS= | -3.7 | FOM= | 0.41 | TEST= 0 |
| INDE | 6 | 49 | 27 | FOBS= | 31.2 | SIGMA= | 6.4 | PHAS= | -133.3 | FOM= | 0.28 | TEST= 0 |
| INDE | 6 | 49 | 29 | FOBS= | 62.8 | SIGMA= | 3.2 | PHAS= | -13.6 | FOM= | 0.73 | TEST= 1 |
| INDE | 6 | 49 | 31 | FOBS= | 17.3 | SIGMA= | 17.2 | PHAS= | 139.2 | FOM= | 0.03 | TEST= 0 |
| INDE | 6 | 49 | 33 | FOBS= | 129.6 | SIGMA= | 2.0 | PHAS= | -166.1 | FOM= | 0.89 | TEST= 0 |
| INDE | 6 | 49 | 35 | FOBS= | 114.7 | SIGMA= | 2.2 | PHAS= | 41.9 | FOM= | 0.89 | TEST= 0 |
| INDE | 6 | 49 | 37 | FOBS= | 105.6 | SIGMA= | 2.0 | PHAS= | 104.4 | FOM= | 0.87 | TEST= 0 |
| INDE | 6 | 49 | 39 | FOBS= | 84.1 | SIGMA= | 2.2 | PHAS= | 48.0 | FOM= | 0.91 | TEST= 0 |
| INDE | 6 | 49 | 41 | FOBS= | 64.6 | SIGMA= | 2.8 | PHAS= | -62.4 | FOM= | 0.80 | TEST= 0 |
| INDE | 6 | 49 | 43 | FOBS= | 89.8 | SIGMA= | 2.1 | PHAS= | -116.1 | FOM= | 0.55 | TEST= 1 |
| INDE | 6 | 49 | 45 | FOBS= | 67.3 | SIGMA= | 2.7 | PHAS= | 168.7 | FOM= | 0.47 | TEST= 0 |
| INDE | 6 | 49 | 47 | FOBS= | 0.0 | SIGMA= | 19.7 | PHAS= | 0.0 | FOM= | 0.00 | TEST= 0 |
| INDE | 6 | 49 | 49 | FOBS= | 67.2 | SIGMA= | 3.0 | PHAS= | -22.7 | FOM= | 0.90 | TEST= 0 |
| INDE | 6 | 49 | 51 | FOBS= | 31.0 | SIGMA= | 6.2 | PHAS= | 165.0 | FOM= | 0.08 | TEST= 1 |
| INDE | 6 | 49 | 53 | FOBS= | 94.5 | SIGMA= | 2.0 | PHAS= | -27.1 | FOM= | 0.13 | TEST= 1 |
| INDE | 6 | 49 | 55 | FOBS= | 59.8 | SIGMA= | 3.1 | PHAS= | 61.1 | FOM= | 0.83 | TEST= 0 |
| INDE | 6 | 49 | 57 | FOBS= | 54.3 | SIGMA= | 4.1 | PHAS= | -109.8 | FOM= | 0.06 | TEST= 1 |
| INDE | 6 | 49 | 59 | FOBS= | 0.0 | SIGMA= | 22.5 | PHAS= | 0.0 | FOM= | 0.00 | TEST= 0 |
| INDE | 6 | 50 | 6 | FOBS= | 133.6 | SIGMA= | 1.5 | PHAS= | -130.1 | FOM= | 0.91 | TEST= 0 |
| INDE | 6 | 50 | 8 | FOBS= | 216.8 | SIGMA= | 1.4 | PHAS= | 38.6 | FOM= | 0.95 | TEST= 0 |
| INDE | 6 | 50 | 10 | FOBS= | 42.0 | SIGMA= | 6.5 | PHAS= | 16.4 | FOM= | 0.34 | TEST= 1 |
| INDE | 6 | 50 | 12 | FOBS= | 111.8 | SIGMA= | 1.5 | PHAS= | -155.4 | FOM= | 0.88 | TEST= 0 |
| INDE | 6 | 50 | 14 | FOBS= | 105.3 | SIGMA= | 1.5 | PHAS= | -82.2 | FOM= | 0.84 | TEST= 0 |
| INDE | 6 | 50 | 16 | FOBS= | 156.1 | SIGMA= | 1.1 | PHAS= | -174.2 | FOM= | 0.89 | TEST= 0 |
| INDE | 6 | 50 | 18 | FOBS= | 145.6 | SIGMA= | 1.4 | PHAS= | 151.2 | FOM= | 0.60 | TEST= 1 |
| INDE | 6 | 50 | 20 | FOBS= | 0.0 | SIGMA= | 20.4 | PHAS= | 0.0 | FOM= | 0.00 | TEST= 0 |
| INDE | 6 | 50 | 22 | FOBS= | 122.1 | SIGMA= | 1.7 | PHAS= | -19.5 | FOM= | 0.93 | TEST= 0 |
| INDE | 6 | 50 | 24 | FOBS= | 155.1 | SIGMA= | 1.4 | PHAS= | 9.6 | FOM= | 0.94 | TEST= 0 |
| INDE | 6 | 50 | 26 | FOBS= | 85.8 | SIGMA= | 2.4 | PHAS= | 44.9 | FOM= | 0.83 | TEST= 0 |
| INDE | 6 | 50 | 28 | FOBS= | 58.7 | SIGMA= | 3.4 | PHAS= | 29.8 | FOM= | 0.38 | TEST= 0 |
| INDE | 6 | 50 | 30 | FOBS= | 78.5 | SIGMA= | 2.6 | PHAS= | -5.9 | FOM= | 0.83 | TEST= 1 |
| INDE | 6 | 50 | 32 | FOBS= | 152.7 | SIGMA= | 1.7 | PHAS= | 140.6 | FOM= | 0.79 | TEST= 1 |
| INDE | 6 | 50 | 34 | FOBS= | 109.0 | SIGMA= | 2.3 | PHAS= | -137.5 | FOM= | 0.94 | TEST= 0 |
| INDE | 6 | 50 | 36 | FOBS= | 143.7 | SIGMA= | 1.6 | PHAS= | -1.1 | FOM= | 0.93 | TEST= 0 |
| INDE | 6 | 50 | 38 | FOBS= | 136.6 | SIGMA= | 1.6 | PHAS= | -25.1 | FOM= | 0.91 | TEST= 0 |
| INDE | 6 | 50 | 40 | FOBS= | 63.0 | SIGMA= | 2.9 | PHAS= | -26.1 | FOM= | 0.86 | TEST= 0 |
| INDE | 6 | 50 | 42 | FOBS= | 41.7 | SIGMA= | 4.4 | PHAS= | -177.3 | FOM= | 0.42 | TEST= 0 |
| INDE | 6 | 50 | 44 | FOBS= | 31.2 | SIGMA= | 5.8 | PHAS= | -159.1 | FOM= | 0.29 | TEST= 0 |
| INDE | 6 | 50 | 46 | FOBS= | 0.0 | SIGMA= | 19.0 | PHAS= | 0.0 | FOM= | 0.00 | TEST= 0 |
| INDE | 6 | 50 | 48 | FOBS= | 0.0 | SIGMA= | 21.9 | PHAS= | 0.0 | FOM= | 0.00 | TEST= 0 |

*FIG. 12A - 179*

```
INDE  6  50  50  FOBS=   49.9 SIGMA=  3.7 PHAS= -116.7 FOM= 0.58 TEST= 0
INDE  6  50  52  FOBS=   89.2 SIGMA=  2.1 PHAS=  -47.6 FOM= 0.91 TEST= 0
INDE  6  50  54  FOBS=    0.0 SIGMA= 19.1 PHAS=    0.0 FOM= 0.00 TEST= 0
INDE  6  50  56  FOBS=   46.5 SIGMA=  4.3 PHAS=  -98.2 FOM= 0.45 TEST= 0
INDE  6  50  58  FOBS=    0.0 SIGMA= 21.3 PHAS=    0.0 FOM= 0.00 TEST= 0
INDE  6  51   7  FOBS=  180.2 SIGMA=  1.7 PHAS=  172.4 FOM= 0.88 TEST= 0
INDE  6  51   9  FOBS=   64.7 SIGMA=  4.2 PHAS=   -5.8 FOM= 0.89 TEST= 0
INDE  6  51  11  FOBS=  122.6 SIGMA=  2.3 PHAS=  179.0 FOM= 0.64 TEST= 0
INDE  6  51  13  FOBS=    0.0 SIGMA= 17.9 PHAS=    0.0 FOM= 0.00 TEST= 0
INDE  6  51  15  FOBS=   86.1 SIGMA=  1.7 PHAS=   15.1 FOM= 0.55 TEST= 0
INDE  6  51  17  FOBS=   47.2 SIGMA=  3.2 PHAS=   28.5 FOM= 0.82 TEST= 0
INDE  6  51  19  FOBS=  149.4 SIGMA=  1.4 PHAS=   41.7 FOM= 0.92 TEST= 0
INDE  6  51  21  FOBS=   80.7 SIGMA=  2.4 PHAS= -158.4 FOM= 0.71 TEST= 0
INDE  6  51  23  FOBS=  157.1 SIGMA=  1.4 PHAS=  153.3 FOM= 0.07 TEST= 1
INDE  6  51  25  FOBS=  108.2 SIGMA=  1.9 PHAS=  -96.2 FOM= 0.76 TEST= 0
INDE  6  51  27  FOBS=   60.3 SIGMA=  3.4 PHAS=   22.0 FOM= 0.21 TEST= 0
INDE  6  51  29  FOBS=   40.3 SIGMA=  5.4 PHAS=  171.8 FOM= 0.47 TEST= 0
INDE  6  51  31  FOBS=   76.1 SIGMA=  2.6 PHAS=  -19.7 FOM= 0.86 TEST= 0
INDE  6  51  33  FOBS=  202.9 SIGMA=  1.4 PHAS=  111.9 FOM= 0.95 TEST= 0
INDE  6  51  35  FOBS=   22.3 SIGMA= 10.8 PHAS=  125.4 FOM= 0.49 TEST= 0
INDE  6  51  37  FOBS=   29.1 SIGMA=  7.0 PHAS=  -39.4 FOM= 0.01 TEST= 1
INDE  6  51  39  FOBS=   25.9 SIGMA=  8.0 PHAS=  -31.8 FOM= 0.30 TEST= 0
INDE  6  51  41  FOBS=  102.5 SIGMA=  1.8 PHAS=  -80.0 FOM= 0.89 TEST= 0
INDE  6  51  43  FOBS=  113.2 SIGMA=  1.7 PHAS= -141.4 FOM= 0.30 TEST= 1
INDE  6  51  45  FOBS=   24.0 SIGMA=  8.3 PHAS=   50.1 FOM= 0.32 TEST= 0
INDE  6  51  47  FOBS=   53.3 SIGMA=  3.4 PHAS=  100.3 FOM= 0.35 TEST= 1
INDE  6  51  49  FOBS=   73.2 SIGMA=  2.8 PHAS=  -20.1 FOM= 0.63 TEST= 0
INDE  6  51  51  FOBS=    0.0 SIGMA= 19.6 PHAS=    0.0 FOM= 0.00 TEST= 0
INDE  6  51  53  FOBS=   35.8 SIGMA=  5.2 PHAS=  -28.5 FOM= 0.17 TEST= 0
INDE  6  51  55  FOBS=   40.2 SIGMA=  4.7 PHAS=  -40.0 FOM= 0.16 TEST= 0
INDE  6  51  57  FOBS=   65.3 SIGMA=  3.9 PHAS=  164.9 FOM= 0.78 TEST= 0
INDE  6  52   6  FOBS=  240.4 SIGMA=  1.3 PHAS=  169.2 FOM= 0.93 TEST= 0
INDE  6  52   8  FOBS=  159.1 SIGMA=  1.8 PHAS=   15.4 FOM= 0.89 TEST= 0
INDE  6  52  10  FOBS=    0.0 SIGMA= 24.7 PHAS=    0.0 FOM= 0.00 TEST= 0
INDE  6  52  12  FOBS=  129.5 SIGMA=  1.3 PHAS=   10.3 FOM= 0.19 TEST= 1
INDE  6  52  14  FOBS=  125.5 SIGMA=  1.4 PHAS=  -31.1 FOM= 0.95 TEST= 0
INDE  6  52  16  FOBS=  152.6 SIGMA=  1.0 PHAS= -172.3 FOM= 0.90 TEST= 0
INDE  6  52  18  FOBS=  110.3 SIGMA=  1.5 PHAS=  -87.3 FOM= 0.98 TEST= 0
INDE  6  52  20  FOBS=  101.6 SIGMA=  2.0 PHAS=  -81.5 FOM= 0.82 TEST= 0
INDE  6  52  22  FOBS=  192.2 SIGMA=  1.1 PHAS=   39.3 FOM= 0.94 TEST= 0
INDE  6  52  24  FOBS=   63.3 SIGMA=  3.1 PHAS= -156.7 FOM= 0.68 TEST= 0
INDE  6  52  26  FOBS=   97.0 SIGMA=  2.1 PHAS=   66.4 FOM= 0.83 TEST= 0
INDE  6  52  28  FOBS=   61.3 SIGMA=  3.3 PHAS=   65.3 FOM= 0.86 TEST= 0
INDE  6  52  30  FOBS=   83.7 SIGMA=  2.4 PHAS= -133.1 FOM= 0.87 TEST= 0
INDE  6  52  32  FOBS=   42.4 SIGMA=  5.1 PHAS=  -15.9 FOM= 0.19 TEST= 0
INDE  6  52  34  FOBS=   59.9 SIGMA=  4.1 PHAS=  -47.4 FOM= 0.79 TEST= 0
INDE  6  52  36  FOBS=   66.3 SIGMA=  3.6 PHAS=  -54.0 FOM= 0.80 TEST= 0
INDE  6  52  38  FOBS=   69.7 SIGMA=  3.0 PHAS= -117.6 FOM= 0.54 TEST= 0
INDE  6  52  40  FOBS=   29.7 SIGMA=  6.4 PHAS= -162.4 FOM= 0.30 TEST= 0
INDE  6  52  42  FOBS=   49.6 SIGMA=  3.7 PHAS= -167.9 FOM= 0.37 TEST= 0
INDE  6  52  44  FOBS=   21.4 SIGMA=  9.2 PHAS=  178.9 FOM= 0.09 TEST= 0
INDE  6  52  46  FOBS=   62.0 SIGMA=  3.0 PHAS=    3.4 FOM= 0.87 TEST= 0
INDE  6  52  48  FOBS=    0.0 SIGMA= 20.8 PHAS=    0.0 FOM= 0.00 TEST= 0
INDE  6  52  50  FOBS=   39.4 SIGMA=  5.0 PHAS=  -93.5 FOM= 0.67 TEST= 0
INDE  6  52  52  FOBS=   36.8 SIGMA=  5.0 PHAS=   52.1 FOM= 0.32 TEST= 0
INDE  6  52  54  FOBS=  118.8 SIGMA=  1.7 PHAS= -170.7 FOM= 0.96 TEST= 0
INDE  6  52  56  FOBS=   94.4 SIGMA=  2.3 PHAS=  -51.8 FOM= 0.90 TEST= 0
INDE  6  53   7  FOBS=  110.7 SIGMA=  2.5 PHAS=  153.0 FOM= 0.75 TEST= 0
INDE  6  53   9  FOBS=  102.7 SIGMA=  2.7 PHAS=    0.0 FOM= 0.79 TEST= 0
INDE  6  53  11  FOBS=   65.5 SIGMA=  4.1 PHAS=  130.6 FOM= 0.84 TEST= 0
INDE  6  53  13  FOBS=  173.4 SIGMA=  1.2 PHAS=  -83.2 FOM= 0.90 TEST= 0
INDE  6  53  15  FOBS=  130.6 SIGMA=  1.3 PHAS=   13.6 FOM= 0.85 TEST= 0
INDE  6  53  17  FOBS=  107.9 SIGMA=  1.4 PHAS=  144.0 FOM= 0.94 TEST= 0
INDE  6  53  19  FOBS=  114.4 SIGMA=  1.7 PHAS=  -93.1 FOM= 0.56 TEST= 0
INDE  6  53  21  FOBS=  215.1 SIGMA=  1.0 PHAS= -151.2 FOM= 0.82 TEST= 0
INDE  6  53  23  FOBS=   65.4 SIGMA=  3.0 PHAS=  -46.7 FOM= 0.49 TEST= 0
INDE  6  53  25  FOBS=    0.0 SIGMA= 19.8 PHAS=    0.0 FOM= 0.00 TEST= 0
INDE  6  53  27  FOBS=    0.0 SIGMA= 23.8 PHAS=    0.0 FOM= 0.00 TEST= 0
INDE  6  53  29  FOBS=   44.0 SIGMA=  4.5 PHAS=   41.3 FOM= 0.57 TEST= 0
INDE  6  53  31  FOBS=   56.2 SIGMA=  3.5 PHAS=  -61.8 FOM= 0.29 TEST= 1
```

*FIG. 12A - 180*

```
INDE  6  53  33  FOBS=   189.3  SIGMA=   1.4  PHAS=  -131.4  FOM=  0.96  TEST=  0
INDE  6  53  35  FOBS=    54.2  SIGMA=   4.5  PHAS=   144.3  FOM=  0.84  TEST=  0
INDE  6  53  37  FOBS=     0.0  SIGMA=  21.7  PHAS=     0.0  FOM=  0.00  TEST=  0
INDE  6  53  39  FOBS=    65.5  SIGMA=   3.1  PHAS=   -86.0  FOM=  0.36  TEST=  0
INDE  6  53  41  FOBS=     0.0  SIGMA=  19.4  PHAS=     0.0  FOM=  0.00  TEST=  0
INDE  6  53  43  FOBS=    68.5  SIGMA=   2.7  PHAS=  -172.5  FOM=  0.88  TEST=  0
INDE  6  53  45  FOBS=    42.9  SIGMA=   4.3  PHAS=   -15.0  FOM=  0.73  TEST=  0
INDE  6  53  47  FOBS=    31.8  SIGMA=   6.8  PHAS=  -134.8  FOM=  0.01  TEST=  1
INDE  6  53  49  FOBS=     0.0  SIGMA=  22.8  PHAS=     0.0  FOM=  0.00  TEST=  0
INDE  6  53  51  FOBS=    52.9  SIGMA=   3.6  PHAS=    84.3  FOM=  0.72  TEST=  0
INDE  6  53  53  FOBS=    83.3  SIGMA=   2.3  PHAS=    57.9  FOM=  0.94  TEST=  0
INDE  6  53  55  FOBS=    39.9  SIGMA=   7.6  PHAS=   143.4  FOM=  0.83  TEST=  0
INDE  6  54   6  FOBS=     0.0  SIGMA=  22.9  PHAS=     0.0  FOM=  0.00  TEST=  0
INDE  6  54   8  FOBS=    78.3  SIGMA=   3.4  PHAS=   133.9  FOM=  0.09  TEST=  1
INDE  6  54  10  FOBS=    58.9  SIGMA=   4.4  PHAS=    24.0  FOM=  0.63  TEST=  0
INDE  6  54  12  FOBS=   103.9  SIGMA=   2.6  PHAS=   102.6  FOM=  0.47  TEST=  0
INDE  6  54  14  FOBS=   232.5  SIGMA=   1.0  PHAS=  -109.1  FOM=  0.97  TEST=  0
INDE  6  54  16  FOBS=    88.5  SIGMA=   1.6  PHAS=  -152.9  FOM=  0.92  TEST=  0
INDE  6  54  18  FOBS=    91.8  SIGMA=   1.7  PHAS=    74.4  FOM=  0.83  TEST=  1
INDE  6  54  20  FOBS=   167.8  SIGMA=   1.3  PHAS=    93.0  FOM=  0.92  TEST=  0
INDE  6  54  22  FOBS=   111.7  SIGMA=   1.9  PHAS=    94.2  FOM=  0.91  TEST=  0
INDE  6  54  24  FOBS=    63.2  SIGMA=   3.1  PHAS=   -70.9  FOM=  0.68  TEST=  0
INDE  6  54  26  FOBS=    21.8  SIGMA=   9.1  PHAS=   106.1  FOM=  0.67  TEST=  0
INDE  6  54  28  FOBS=    70.2  SIGMA=   2.9  PHAS=  -173.1  FOM=  0.76  TEST=  0
INDE  6  54  30  FOBS=   112.0  SIGMA=   1.8  PHAS=   -88.0  FOM=  0.74  TEST=  0
INDE  6  54  32  FOBS=   140.4  SIGMA=   1.5  PHAS=   154.7  FOM=  0.90  TEST=  0
INDE  6  54  34  FOBS=    75.8  SIGMA=   3.2  PHAS=   178.1  FOM=  0.63  TEST=  0
INDE  6  54  36  FOBS=   103.2  SIGMA=   2.4  PHAS=   -25.0  FOM=  0.86  TEST=  0
INDE  6  54  38  FOBS=    83.8  SIGMA=   2.7  PHAS=  -125.1  FOM=  0.88  TEST=  0
INDE  6  54  40  FOBS=    60.2  SIGMA=   3.4  PHAS=  -132.1  FOM=  0.59  TEST=  0
INDE  6  54  42  FOBS=    23.3  SIGMA=   8.9  PHAS=   -85.4  FOM=  0.26  TEST=  0
INDE  6  54  44  FOBS=    59.6  SIGMA=   3.1  PHAS=   119.6  FOM=  0.88  TEST=  0
INDE  6  54  46  FOBS=    48.9  SIGMA=   4.0  PHAS=    15.0  FOM=  0.77  TEST=  0
INDE  6  54  48  FOBS=    79.1  SIGMA=   2.6  PHAS=    19.4  FOM=  0.89  TEST=  0
INDE  6  54  50  FOBS=    39.9  SIGMA=   5.1  PHAS=   -65.8  FOM=  0.56  TEST=  0
INDE  6  54  52  FOBS=    34.1  SIGMA=   8.2  PHAS=   -36.2  FOM=  0.40  TEST=  0
INDE  6  54  54  FOBS=    28.8  SIGMA=   9.1  PHAS=   174.9  FOM=  0.47  TEST=  0
INDE  6  55   7  FOBS=   101.6  SIGMA=   2.7  PHAS=    54.3  FOM=  0.85  TEST=  0
INDE  6  55   9  FOBS=     0.0  SIGMA=  22.8  PHAS=     0.0  FOM=  0.00  TEST=  0
INDE  6  55  11  FOBS=     0.0  SIGMA=  27.1  PHAS=     0.0  FOM=  0.00  TEST=  0
INDE  6  55  13  FOBS=    63.1  SIGMA=   2.4  PHAS=    30.2  FOM=  0.02  TEST=  0
INDE  6  55  15  FOBS=   105.8  SIGMA=   1.7  PHAS=   165.3  FOM=  0.93  TEST=  0
INDE  6  55  17  FOBS=   109.6  SIGMA=   1.4  PHAS=  -162.0  FOM=  0.94  TEST=  0
INDE  6  55  19  FOBS=   178.7  SIGMA=   0.9  PHAS=   -32.0  FOM=  0.95  TEST=  0
INDE  6  55  21  FOBS=    63.6  SIGMA=   3.0  PHAS=    40.9  FOM=  0.75  TEST=  0
INDE  6  55  23  FOBS=    69.2  SIGMA=   2.8  PHAS=   -11.1  FOM=  0.45  TEST=  1
INDE  6  55  25  FOBS=    73.3  SIGMA=   2.7  PHAS=    75.2  FOM=  0.72  TEST=  0
INDE  6  55  27  FOBS=    54.8  SIGMA=   3.6  PHAS=   178.8  FOM=  0.73  TEST=  0
INDE  6  55  29  FOBS=    53.8  SIGMA=   3.7  PHAS=    66.0  FOM=  0.82  TEST=  0
INDE  6  55  31  FOBS=    52.9  SIGMA=   3.8  PHAS=   -72.3  FOM=  0.50  TEST=  0
INDE  6  55  33  FOBS=    69.6  SIGMA=   2.9  PHAS=    50.9  FOM=  0.69  TEST=  0
INDE  6  55  35  FOBS=    53.0  SIGMA=   4.5  PHAS=     6.5  FOM=  0.66  TEST=  0
INDE  6  55  37  FOBS=    28.8  SIGMA=   9.1  PHAS=    79.5  FOM=  0.07  TEST=  1
INDE  6  55  39  FOBS=    81.1  SIGMA=   2.6  PHAS=  -176.7  FOM=  0.88  TEST=  0
INDE  6  55  41  FOBS=    93.0  SIGMA=   2.0  PHAS=   168.1  FOM=  0.89  TEST=  0
INDE  6  55  43  FOBS=     0.0  SIGMA=  19.6  PHAS=     0.0  FOM=  0.00  TEST=  0
INDE  6  55  45  FOBS=   119.7  SIGMA=   1.6  PHAS=   -19.4  FOM=  0.94  TEST=  0
INDE  6  55  47  FOBS=    80.2  SIGMA=   2.9  PHAS=   -36.8  FOM=  0.83  TEST=  0
INDE  6  55  49  FOBS=    24.7  SIGMA=   8.9  PHAS=   -51.8  FOM=  0.23  TEST=  0
INDE  6  55  51  FOBS=     0.0  SIGMA=  23.7  PHAS=     0.0  FOM=  0.00  TEST=  1
INDE  6  55  53  FOBS=    50.0  SIGMA=   6.0  PHAS=   137.5  FOM=  0.71  TEST=  0
INDE  6  56   6  FOBS=   149.5  SIGMA=   1.8  PHAS=   -47.5  FOM=  0.84  TEST=  0
INDE  6  56   8  FOBS=   114.2  SIGMA=   2.4  PHAS=  -111.6  FOM=  0.77  TEST=  1
INDE  6  56  10  FOBS=    40.9  SIGMA=   6.5  PHAS=    22.0  FOM=  0.47  TEST=  0
INDE  6  56  12  FOBS=    53.5  SIGMA=   4.8  PHAS=   158.3  FOM=  0.72  TEST=  0
INDE  6  56  14  FOBS=   135.9  SIGMA=   1.2  PHAS=  -108.5  FOM=  0.95  TEST=  0
INDE  6  56  16  FOBS=    75.5  SIGMA=   2.2  PHAS=    54.7  FOM=  0.81  TEST=  0
INDE  6  56  18  FOBS=   131.2  SIGMA=   1.2  PHAS=   135.2  FOM=  0.94  TEST=  0
INDE  6  56  20  FOBS=    62.7  SIGMA=   2.4  PHAS=   125.5  FOM=  0.29  TEST=  0
INDE  6  56  22  FOBS=     2.8  SIGMA=  71.2  PHAS=     0.0  FOM=  0.00  TEST=  1
```

*FIG. 12A - 181*

```
INDE  6  56  24 FOBS=   48.3 SIGMA=   4.0 PHAS=  -11.3 FOM= 0.71 TEST= 0
INDE  6  56  26 FOBS=   75.8 SIGMA=   2.6 PHAS=  -28.0 FOM= 0.73 TEST= 0
INDE  6  56  28 FOBS=   91.5 SIGMA=   2.2 PHAS= -179.9 FOM= 0.87 TEST= 0
INDE  6  56  30 FOBS=   45.1 SIGMA=   4.8 PHAS=  -58.0 FOM= 0.33 TEST= 0
INDE  6  56  32 FOBS=   57.7 SIGMA=   3.4 PHAS=  -46.3 FOM= 0.47 TEST= 0
INDE  6  56  34 FOBS=   46.1 SIGMA=   4.2 PHAS= -129.5 FOM= 0.41 TEST= 0
INDE  6  56  36 FOBS=   30.4 SIGMA=   8.7 PHAS=   33.0 FOM= 0.19 TEST= 0
INDE  6  56  38 FOBS=   23.4 SIGMA=  10.1 PHAS= -173.5 FOM= 0.23 TEST= 0
INDE  6  56  40 FOBS=   77.1 SIGMA=   2.7 PHAS=  125.4 FOM= 0.87 TEST= 0
INDE  6  56  42 FOBS=   64.5 SIGMA=   3.1 PHAS=  176.9 FOM= 0.74 TEST= 0
INDE  6  56  44 FOBS=   34.8 SIGMA=   6.5 PHAS= -173.4 FOM= 0.53 TEST= 0
INDE  6  56  46 FOBS=   87.9 SIGMA=   2.9 PHAS=  -85.3 FOM= 0.27 TEST= 1
INDE  6  56  48 FOBS=   20.3 SIGMA=  12.4 PHAS=  -60.4 FOM= 0.28 TEST= 0
INDE  6  56  50 FOBS=   43.5 SIGMA=   5.2 PHAS=  -80.7 FOM= 0.57 TEST= 0
INDE  6  56  52 FOBS=   61.0 SIGMA=   4.9 PHAS=  117.9 FOM= 0.86 TEST= 0
INDE  6  57   7 FOBS=  133.1 SIGMA=   2.0 PHAS= -119.9 FOM= 0.65 TEST= 1
INDE  6  57   9 FOBS=   56.7 SIGMA=   4.6 PHAS=   89.2 FOM= 0.24 TEST= 0
INDE  6  57  11 FOBS=  143.1 SIGMA=   1.9 PHAS= -131.5 FOM= 0.89 TEST= 0
INDE  6  57  13 FOBS=   52.7 SIGMA=   4.9 PHAS= -142.3 FOM= 0.57 TEST= 0
INDE  6  57  15 FOBS=   34.9 SIGMA=   4.5 PHAS=  -70.0 FOM= 0.32 TEST= 0
INDE  6  57  17 FOBS=   61.6 SIGMA=   2.5 PHAS=   10.8 FOM= 0.91 TEST= 0
INDE  6  57  19 FOBS=   47.7 SIGMA=   3.1 PHAS=  -49.1 FOM= 0.16 TEST= 0
INDE  6  57  21 FOBS=    0.0 SIGMA=  17.7 PHAS=    0.0 FOM= 0.00 TEST= 0
INDE  6  57  23 FOBS=    0.0 SIGMA=  20.6 PHAS=    0.0 FOM= 0.00 TEST= 0
INDE  6  57  25 FOBS=    0.0 SIGMA=  20.6 PHAS=    0.0 FOM= 0.00 TEST= 1
INDE  6  57  27 FOBS=   48.8 SIGMA=   4.0 PHAS=   43.3 FOM= 0.75 TEST= 0
INDE  6  57  29 FOBS=   87.6 SIGMA=   2.3 PHAS=  122.3 FOM= 0.77 TEST= 0
INDE  6  57  31 FOBS=   22.8 SIGMA=   8.6 PHAS=  -15.4 FOM= 0.29 TEST= 0
INDE  6  57  33 FOBS=    0.0 SIGMA=  20.6 PHAS=    0.0 FOM= 0.00 TEST= 0
INDE  6  57  35 FOBS=    0.0 SIGMA=  21.4 PHAS=    0.0 FOM= 0.00 TEST= 0
INDE  6  57  37 FOBS=  102.3 SIGMA=   2.8 PHAS=   39.3 FOM= 0.92 TEST= 0
INDE  6  57  39 FOBS=   60.7 SIGMA=   4.5 PHAS=  -26.0 FOM= 0.46 TEST= 0
INDE  6  57  41 FOBS=   28.6 SIGMA=  10.4 PHAS=   80.6 FOM= 0.48 TEST= 0
INDE  6  57  43 FOBS=   20.0 SIGMA=  12.1 PHAS=   51.7 FOM= 0.68 TEST= 0
INDE  6  57  45 FOBS=   21.4 SIGMA=  10.0 PHAS=   10.2 FOM= 0.21 TEST= 0
INDE  6  57  47 FOBS=   50.4 SIGMA=   5.0 PHAS=  106.1 FOM= 0.21 TEST= 1
INDE  6  57  49 FOBS=   43.0 SIGMA=   5.7 PHAS=  -97.3 FOM= 0.51 TEST= 0
INDE  6  57  51 FOBS=   28.0 SIGMA=  10.6 PHAS=   84.6 FOM= 0.17 TEST= 0
INDE  6  58   6 FOBS=  142.7 SIGMA=   2.0 PHAS=  102.9 FOM= 0.93 TEST= 0
INDE  6  58   8 FOBS=   14.8 SIGMA=  20.0 PHAS=  -78.2 FOM= 0.09 TEST= 0
INDE  6  58  10 FOBS=  107.1 SIGMA=   2.5 PHAS=  -75.9 FOM= 0.42 TEST= 1
INDE  6  58  12 FOBS=  145.5 SIGMA=   1.9 PHAS=  155.6 FOM= 0.95 TEST= 0
INDE  6  58  14 FOBS=   46.9 SIGMA=   6.2 PHAS=   13.9 FOM= 0.52 TEST= 1
INDE  6  58  16 FOBS=  122.5 SIGMA=   1.4 PHAS=  -26.4 FOM= 0.92 TEST= 0
INDE  6  58  18 FOBS=  106.1 SIGMA=   1.4 PHAS=  144.8 FOM= 0.93 TEST= 0
INDE  6  58  20 FOBS=   40.6 SIGMA=   4.0 PHAS=  -93.8 FOM= 0.60 TEST= 0
INDE  6  58  22 FOBS=   33.3 SIGMA=   4.5 PHAS=   26.7 FOM= 0.31 TEST= 0
INDE  6  58  24 FOBS=  107.6 SIGMA=   1.8 PHAS=   27.7 FOM= 0.89 TEST= 0
INDE  6  58  26 FOBS=  167.9 SIGMA=   1.3 PHAS=  -99.9 FOM= 0.43 TEST= 1
INDE  6  58  28 FOBS=   60.0 SIGMA=   3.3 PHAS=  -81.6 FOM= 0.53 TEST= 0
INDE  6  58  30 FOBS=   43.3 SIGMA=   4.6 PHAS= -151.6 FOM= 0.07 TEST= 1
INDE  6  58  32 FOBS=    0.0 SIGMA=  23.3 PHAS=    0.0 FOM= 0.00 TEST= 0
INDE  6  58  34 FOBS=   71.0 SIGMA=   3.1 PHAS=  171.6 FOM= 0.77 TEST= 0
INDE  6  58  36 FOBS=   49.9 SIGMA=   4.7 PHAS= -103.9 FOM= 0.61 TEST= 0
INDE  6  58  38 FOBS=   70.4 SIGMA=   4.6 PHAS=  -92.8 FOM= 0.89 TEST= 0
INDE  6  58  40 FOBS=   79.2 SIGMA=   3.2 PHAS=   74.6 FOM= 0.68 TEST= 0
INDE  6  58  42 FOBS=   50.5 SIGMA=   4.5 PHAS= -113.8 FOM= 0.75 TEST= 0
INDE  6  58  44 FOBS=    0.0 SIGMA=  20.5 PHAS=    0.0 FOM= 0.00 TEST= 0
INDE  6  58  46 FOBS=   65.5 SIGMA=   3.9 PHAS=  161.8 FOM= 0.78 TEST= 0
INDE  6  58  48 FOBS=   58.6 SIGMA=   5.5 PHAS= -145.3 FOM= 0.74 TEST= 0
INDE  6  58  50 FOBS=   42.8 SIGMA=   7.0 PHAS=   88.5 FOM= 0.46 TEST= 0
INDE  6  59   7 FOBS=  100.3 SIGMA=   2.7 PHAS=   24.6 FOM= 0.10 TEST= 1
INDE  6  59   9 FOBS=   57.0 SIGMA=   4.6 PHAS=  -82.1 FOM= 0.39 TEST= 0
INDE  6  59  11 FOBS=  106.3 SIGMA=   2.5 PHAS= -110.1 FOM= 0.92 TEST= 0
INDE  6  59  13 FOBS=    0.0 SIGMA=  24.1 PHAS=    0.0 FOM= 0.00 TEST= 0
INDE  6  59  15 FOBS=   49.7 SIGMA=   3.9 PHAS=   59.0 FOM= 0.28 TEST= 0
INDE  6  59  17 FOBS=   62.2 SIGMA=   3.2 PHAS=  -20.9 FOM= 0.69 TEST= 0
INDE  6  59  19 FOBS=   91.6 SIGMA=   1.8 PHAS=   81.0 FOM= 0.86 TEST= 0
INDE  6  59  21 FOBS=   90.4 SIGMA=   1.9 PHAS=   51.7 FOM= 0.91 TEST= 0
INDE  6  59  23 FOBS=   88.4 SIGMA=   2.1 PHAS= -103.4 FOM= 0.91 TEST= 0
```

*FIG. 12A - 182*

```
INDE  6  59  25  FOBS=   77.5  SIGMA=   2.5  PHAS=  -104.1  FOM=  0.75  TEST=  1
INDE  6  59  27  FOBS=   71.6  SIGMA=   2.7  PHAS=    62.0  FOM=  0.19  TEST=  1
INDE  6  59  29  FOBS=   41.3  SIGMA=   5.1  PHAS=  -109.3  FOM=  0.23  TEST=  0
INDE  6  59  31  FOBS=   18.0  SIGMA=  18.3  PHAS=   157.4  FOM=  0.10  TEST=  0
INDE  6  59  33  FOBS=   39.4  SIGMA=   6.0  PHAS=  -153.1  FOM=  0.61  TEST=  0
INDE  6  59  35  FOBS=   91.3  SIGMA=   2.6  PHAS=   156.7  FOM=  0.89  TEST=  0
INDE  6  59  37  FOBS=   40.4  SIGMA=   5.9  PHAS=   176.1  FOM=  0.53  TEST=  0
INDE  6  59  39  FOBS=  102.2  SIGMA=   3.3  PHAS=    98.4  FOM=  0.11  TEST=  1
INDE  6  59  41  FOBS=   53.1  SIGMA=   4.7  PHAS=    44.3  FOM=  0.84  TEST=  0
INDE  6  59  43  FOBS=   47.3  SIGMA=   4.5  PHAS=  -111.8  FOM=  0.62  TEST=  0
INDE  6  59  45  FOBS=   90.5  SIGMA=   2.8  PHAS=   -10.7  FOM=  0.30  TEST=  1
INDE  6  59  47  FOBS=   86.9  SIGMA=   3.7  PHAS=   122.5  FOM=  0.90  TEST=  0
INDE  6  59  49  FOBS=   41.8  SIGMA=   8.4  PHAS=   110.7  FOM=  0.79  TEST=  0
INDE  6  60   6  FOBS=  148.5  SIGMA=   1.9  PHAS=   147.0  FOM=  0.88  TEST=  0
INDE  6  60   8  FOBS=   99.7  SIGMA=   2.6  PHAS=   104.5  FOM=  0.54  TEST=  0
INDE  6  60  10  FOBS=   65.4  SIGMA=   4.0  PHAS=   111.6  FOM=  0.55  TEST=  0
INDE  6  60  12  FOBS=  131.2  SIGMA=   2.1  PHAS=    30.9  FOM=  0.11  TEST=  1
INDE  6  60  14  FOBS=   80.2  SIGMA=   3.2  PHAS=   -53.8  FOM=  0.88  TEST=  0
INDE  6  60  16  FOBS=   54.6  SIGMA=   3.4  PHAS=  -114.0  FOM=  0.90  TEST=  0
INDE  6  60  18  FOBS=   51.6  SIGMA=   3.8  PHAS=  -173.0  FOM=  0.54  TEST=  0
INDE  6  60  20  FOBS=  101.6  SIGMA=   1.8  PHAS=   -38.7  FOM=  0.93  TEST=  0
INDE  6  60  22  FOBS=   77.7  SIGMA=   2.2  PHAS=   139.1  FOM=  0.92  TEST=  0
INDE  6  60  24  FOBS=    0.0  SIGMA=  19.7  PHAS=     0.0  FOM=  0.00  TEST=  0
INDE  6  60  26  FOBS=  135.5  SIGMA=   1.8  PHAS=  -118.4  FOM=  0.93  TEST=  0
INDE  6  60  28  FOBS=    0.0  SIGMA=  21.3  PHAS=     0.0  FOM=  0.00  TEST=  0
INDE  6  60  30  FOBS=    0.0  SIGMA=  23.4  PHAS=     0.0  FOM=  0.00  TEST=  0
INDE  6  60  32  FOBS=   89.2  SIGMA=   2.7  PHAS=    67.5  FOM=  0.90  TEST=  0
INDE  6  60  34  FOBS=   69.8  SIGMA=   3.5  PHAS=   159.3  FOM=  0.86  TEST=  0
INDE  6  60  36  FOBS=   44.6  SIGMA=   6.3  PHAS=   116.1  FOM=  0.87  TEST=  0
INDE  6  60  38  FOBS=  111.2  SIGMA=   2.6  PHAS=   179.1  FOM=  0.95  TEST=  0
INDE  6  60  40  FOBS=   64.1  SIGMA=   5.1  PHAS=   -51.3  FOM=  0.81  TEST=  0
INDE  6  60  42  FOBS=   36.6  SIGMA=   6.9  PHAS=   130.4  FOM=  0.26  TEST=  0
INDE  6  60  44  FOBS=   68.1  SIGMA=   3.2  PHAS=  -169.8  FOM=  0.92  TEST=  0
INDE  6  60  46  FOBS=   48.0  SIGMA=   6.6  PHAS=   121.4  FOM=  0.83  TEST=  0
INDE  6  60  48  FOBS=   90.2  SIGMA=   4.0  PHAS=    43.1  FOM=  0.94  TEST=  0
INDE  6  61   7  FOBS=   61.3  SIGMA=   4.2  PHAS=   -16.2  FOM=  0.57  TEST=  0
INDE  6  61   9  FOBS=  190.5  SIGMA=   1.5  PHAS=    -8.6  FOM=  0.97  TEST=  0
INDE  6  61  11  FOBS=   77.2  SIGMA=   3.3  PHAS=   -40.5  FOM=  0.87  TEST=  0
INDE  6  61  13  FOBS=   62.2  SIGMA=   4.1  PHAS=   -72.1  FOM=  0.76  TEST=  0
INDE  6  61  15  FOBS=  115.5  SIGMA=   2.3  PHAS=   156.9  FOM=  0.90  TEST=  0
INDE  6  61  17  FOBS=   56.2  SIGMA=   3.4  PHAS=    98.8  FOM=  0.81  TEST=  0
INDE  6  61  19  FOBS=   38.7  SIGMA=   4.7  PHAS=  -171.0  FOM=  0.83  TEST=  0
INDE  6  61  21  FOBS=    0.0  SIGMA=  19.7  PHAS=     0.0  FOM=  0.00  TEST=  0
INDE  6  61  23  FOBS=   46.8  SIGMA=   4.8  PHAS=    97.1  FOM=  0.25  TEST=  1
INDE  6  61  25  FOBS=   91.8  SIGMA=   2.5  PHAS=   118.8  FOM=  0.85  TEST=  0
INDE  6  61  27  FOBS=   50.3  SIGMA=   5.4  PHAS=    75.3  FOM=  0.52  TEST=  0
INDE  6  61  29  FOBS=    8.9  SIGMA=  30.2  PHAS=    76.0  FOM=  0.05  TEST=  0
INDE  6  61  31  FOBS=   81.3  SIGMA=   3.5  PHAS=   -74.1  FOM=  0.66  TEST=  0
INDE  6  61  33  FOBS=   10.9  SIGMA=  30.4  PHAS=    -4.2  FOM=  0.15  TEST=  0
INDE  6  61  35  FOBS=   67.2  SIGMA=   4.2  PHAS=    -1.0  FOM=  0.47  TEST=  0
INDE  6  61  37  FOBS=  114.9  SIGMA=   2.5  PHAS=    -0.1  FOM=  0.96  TEST=  0
INDE  6  61  39  FOBS=  122.0  SIGMA=   2.4  PHAS=    18.2  FOM=  0.97  TEST=  0
INDE  6  61  41  FOBS=   46.5  SIGMA=   6.1  PHAS=    56.4  FOM=  0.33  TEST=  0
INDE  6  61  43  FOBS=   80.3  SIGMA=   3.2  PHAS=    28.7  FOM=  0.92  TEST=  0
INDE  6  61  45  FOBS=   78.2  SIGMA=   4.1  PHAS=    95.4  FOM=  0.94  TEST=  0
INDE  6  61  47  FOBS=   89.0  SIGMA=   5.5  PHAS=   -28.8  FOM=  0.93  TEST=  0
INDE  6  62   6  FOBS=  121.3  SIGMA=   2.2  PHAS=   144.9  FOM=  0.95  TEST=  0
INDE  6  62   8  FOBS=  132.4  SIGMA=   2.0  PHAS=  -118.4  FOM=  0.94  TEST=  0
INDE  6  62  10  FOBS=  141.9  SIGMA=   1.9  PHAS=   -57.5  FOM=  0.97  TEST=  0
INDE  6  62  12  FOBS=   22.2  SIGMA=  12.9  PHAS=     0.3  FOM=  0.41  TEST=  0
INDE  6  62  14  FOBS=   81.0  SIGMA=   4.5  PHAS=   150.5  FOM=  0.82  TEST=  0
INDE  6  62  16  FOBS=   29.7  SIGMA=   9.4  PHAS=    48.2  FOM=  0.38  TEST=  0
INDE  6  62  18  FOBS=  108.3  SIGMA=   2.3  PHAS=    46.2  FOM=  0.91  TEST=  0
INDE  6  62  20  FOBS=   34.7  SIGMA=   5.7  PHAS=    49.5  FOM=  0.66  TEST=  0
INDE  6  62  22  FOBS=   35.0  SIGMA=   6.1  PHAS=   126.8  FOM=  0.66  TEST=  0
INDE  6  62  24  FOBS=   60.9  SIGMA=   3.7  PHAS=     2.8  FOM=  0.85  TEST=  0
INDE  6  62  26  FOBS=   44.5  SIGMA=   5.1  PHAS=     0.1  FOM=  0.65  TEST=  0
INDE  6  62  28  FOBS=   82.4  SIGMA=   3.3  PHAS=    -7.9  FOM=  0.89  TEST=  0
INDE  6  62  30  FOBS=    0.0  SIGMA=  23.3  PHAS=     0.0  FOM=  0.00  TEST=  0
INDE  6  62  32  FOBS=   22.2  SIGMA=  12.7  PHAS=   -43.5  FOM=  0.11  TEST=  1
```

*FIG. 12A - 183*

```
INDE  6  62  34  FOBS=   69.8  SIGMA=   4.1  PHAS=  -157.0  FOM=  0.88  TEST= 0
INDE  6  62  36  FOBS=   85.7  SIGMA=   3.3  PHAS=  -132.0  FOM=  0.95  TEST= 0
INDE  6  62  38  FOBS=   42.6  SIGMA=   6.6  PHAS=  -127.6  FOM=  0.82  TEST= 0
INDE  6  62  40  FOBS=   84.4  SIGMA=   3.4  PHAS=   -70.8  FOM=  0.91  TEST= 0
INDE  6  62  42  FOBS=   25.2  SIGMA=  10.0  PHAS=   -79.8  FOM=  0.23  TEST= 0
INDE  6  62  44  FOBS=   63.9  SIGMA=   5.8  PHAS=   -75.8  FOM=  0.90  TEST= 0
INDE  6  62  46  FOBS=   49.5  SIGMA=   9.8  PHAS=   136.2  FOM=  0.12  TEST= 1
INDE  6  63   7  FOBS=  105.0  SIGMA=   2.5  PHAS=    38.2  FOM=  0.91  TEST= 0
INDE  6  63   9  FOBS=   47.2  SIGMA=   5.3  PHAS=  -178.2  FOM=  0.11  TEST= 1
INDE  6  63  11  FOBS=  141.3  SIGMA=   2.7  PHAS=  -100.0  FOM=  0.94  TEST= 0
INDE  6  63  13  FOBS=   42.4  SIGMA=   8.3  PHAS=    62.9  FOM=  0.53  TEST= 0
INDE  6  63  15  FOBS=   72.5  SIGMA=   4.9  PHAS=   104.1  FOM=  0.85  TEST= 0
INDE  6  63  17  FOBS=    0.0  SIGMA=  21.8  PHAS=     0.0  FOM=  0.00  TEST= 0
INDE  6  63  19  FOBS=   37.2  SIGMA=   6.3  PHAS=    95.0  FOM=  0.41  TEST= 0
INDE  6  63  21  FOBS=    0.0  SIGMA=  21.0  PHAS=     0.0  FOM=  0.00  TEST= 1
INDE  6  63  23  FOBS=   65.7  SIGMA=   3.3  PHAS=  -151.2  FOM=  0.11  TEST= 1
INDE  6  63  25  FOBS=   70.9  SIGMA=   3.2  PHAS=    20.2  FOM=  0.89  TEST= 0
INDE  6  63  27  FOBS=  101.9  SIGMA=   2.3  PHAS=  -113.5  FOM=  0.09  TEST= 1
INDE  6  63  29  FOBS=   36.3  SIGMA=   7.5  PHAS=   -12.8  FOM=  0.70  TEST= 0
INDE  6  63  31  FOBS=   25.5  SIGMA=  13.1  PHAS=    -7.3  FOM=  0.37  TEST= 0
INDE  6  63  33  FOBS=    0.0  SIGMA=  23.7  PHAS=     0.0  FOM=  0.00  TEST= 0
INDE  6  63  35  FOBS=   82.2  SIGMA=   3.5  PHAS=   120.2  FOM=  0.89  TEST= 0
INDE  6  63  37  FOBS=   14.4  SIGMA=  22.7  PHAS=    70.0  FOM=  0.14  TEST= 0
INDE  6  63  39  FOBS=   28.5  SIGMA=   9.8  PHAS=    -6.8  FOM=  0.55  TEST= 0
INDE  6  63  41  FOBS=    0.0  SIGMA=  23.9  PHAS=     0.0  FOM=  0.00  TEST= 0
INDE  6  63  43  FOBS=   28.8  SIGMA=  11.6  PHAS=  -155.6  FOM=  0.29  TEST= 0
INDE  6  63  45  FOBS=   60.7  SIGMA=   7.9  PHAS=   100.0  FOM=  0.79  TEST= 0
INDE  6  64   6  FOBS=  117.3  SIGMA=   3.2  PHAS=    10.0  FOM=  0.65  TEST= 1
INDE  6  64   8  FOBS=   74.9  SIGMA=   3.9  PHAS=   179.4  FOM=  0.93  TEST= 0
INDE  6  64  10  FOBS=   55.7  SIGMA=   6.4  PHAS=     2.6  FOM=  0.59  TEST= 0
INDE  6  64  12  FOBS=  120.9  SIGMA=   3.1  PHAS=    26.8  FOM=  0.90  TEST= 0
INDE  6  64  14  FOBS=   42.0  SIGMA=   8.3  PHAS=   120.3  FOM=  0.48  TEST= 0
INDE  6  64  16  FOBS=   37.1  SIGMA=   9.3  PHAS=   -64.0  FOM=  0.43  TEST= 0
INDE  6  64  18  FOBS=   69.7  SIGMA=   3.5  PHAS=    80.3  FOM=  0.70  TEST= 0
INDE  6  64  20  FOBS=   52.9  SIGMA=   4.5  PHAS=    76.9  FOM=  0.40  TEST= 1
INDE  6  64  22  FOBS=   76.0  SIGMA=   2.8  PHAS=    11.6  FOM=  0.64  TEST= 0
INDE  6  64  24  FOBS=   76.5  SIGMA=   2.9  PHAS=  -126.4  FOM=  0.68  TEST= 0
INDE  6  64  26  FOBS=  100.1  SIGMA=   2.4  PHAS=     3.0  FOM=  0.18  TEST= 1
INDE  6  64  28  FOBS=   72.9  SIGMA=   3.8  PHAS=   -38.2  FOM=  0.87  TEST= 0
INDE  6  64  30  FOBS=    0.0  SIGMA=  23.4  PHAS=     0.0  FOM=  0.00  TEST= 0
INDE  6  64  32  FOBS=    0.0  SIGMA=  23.6  PHAS=     0.0  FOM=  0.00  TEST= 1
INDE  6  64  34  FOBS=   84.2  SIGMA=   3.5  PHAS=   -96.1  FOM=  0.72  TEST= 0
INDE  6  64  36  FOBS=   57.8  SIGMA=   5.0  PHAS=  -129.3  FOM=  0.70  TEST= 0
INDE  6  64  38  FOBS=   36.8  SIGMA=   7.7  PHAS=    22.0  FOM=  0.10  TEST= 0
INDE  6  64  40  FOBS=   41.9  SIGMA=   6.8  PHAS=  -113.2  FOM=  0.74  TEST= 0
INDE  6  64  42  FOBS=    0.0  SIGMA=  24.2  PHAS=     0.0  FOM=  0.00  TEST= 0
INDE  6  65   7  FOBS=   82.7  SIGMA=   4.3  PHAS=   -73.6  FOM=  0.58  TEST= 0
INDE  6  65   9  FOBS=   61.4  SIGMA=   5.7  PHAS=   -48.3  FOM=  0.80  TEST= 0
INDE  6  65  11  FOBS=  132.5  SIGMA=   2.8  PHAS=   -49.3  FOM=  0.94  TEST= 0
INDE  6  65  13  FOBS=   40.3  SIGMA=   8.8  PHAS=  -178.8  FOM=  0.42  TEST= 0
INDE  6  65  15  FOBS=  130.7  SIGMA=   2.8  PHAS=    21.0  FOM=  0.22  TEST= 1
INDE  6  65  17  FOBS=   40.0  SIGMA=   8.6  PHAS=    86.1  FOM=  0.58  TEST= 0
INDE  6  65  19  FOBS=   42.2  SIGMA=   5.3  PHAS=    42.0  FOM=  0.57  TEST= 0
INDE  6  65  21  FOBS=   64.4  SIGMA=   3.7  PHAS=   -62.8  FOM=  0.86  TEST= 0
INDE  6  65  23  FOBS=   24.1  SIGMA=   8.7  PHAS=   176.9  FOM=  0.31  TEST= 0
INDE  6  65  25  FOBS=    0.0  SIGMA=  26.0  PHAS=     0.0  FOM=  0.00  TEST= 1
INDE  6  65  27  FOBS=   60.1  SIGMA=   3.9  PHAS=   154.3  FOM=  0.80  TEST= 0
INDE  6  65  29  FOBS=   76.7  SIGMA=   4.4  PHAS=   105.2  FOM=  0.90  TEST= 0
INDE  6  65  31  FOBS=   65.0  SIGMA=   4.4  PHAS=    40.6  FOM=  0.74  TEST= 0
INDE  6  65  33  FOBS=   41.0  SIGMA=   7.0  PHAS=  -155.2  FOM=  0.59  TEST= 0
INDE  6  65  35  FOBS=   44.5  SIGMA=   6.5  PHAS=   118.6  FOM=  0.77  TEST= 0
INDE  6  65  37  FOBS=   36.5  SIGMA=   9.3  PHAS=   -76.3  FOM=  0.54  TEST= 0
INDE  6  65  39  FOBS=    0.0  SIGMA=  24.0  PHAS=     0.0  FOM=  0.00  TEST= 0
INDE  6  65  41  FOBS=   13.4  SIGMA=  22.0  PHAS=    26.1  FOM=  0.29  TEST= 0
INDE  6  66   6  FOBS=   24.7  SIGMA=  10.1  PHAS=    20.5  FOM=  0.74  TEST= 0
INDE  6  66   8  FOBS=   84.0  SIGMA=   4.3  PHAS=   112.1  FOM=  0.84  TEST= 0
INDE  6  66  10  FOBS=   68.1  SIGMA=   5.1  PHAS=   -64.3  FOM=  0.55  TEST= 0
INDE  6  66  12  FOBS=   21.3  SIGMA=  16.3  PHAS=   -35.5  FOM=  0.06  TEST= 0
INDE  6  66  14  FOBS=  133.0  SIGMA=   2.8  PHAS=    51.7  FOM=  0.94  TEST= 0
INDE  6  66  16  FOBS=   12.6  SIGMA=  27.4  PHAS=    49.9  FOM=  0.17  TEST= 0
```

*FIG. 12A - 184*

```
INDE  6  66  18 FOBS=   13.9 SIGMA=  24.7 PHAS=  -176.8 FOM=  0.20 TEST= 0
INDE  6  66  20 FOBS=    0.0 SIGMA=  21.5 PHAS=     0.0 FOM=  0.00 TEST= 1
INDE  6  66  22 FOBS=   29.6 SIGMA=   9.9 PHAS=  -157.8 FOM=  0.18 TEST= 0
INDE  6  66  24 FOBS=   15.5 SIGMA=  13.7 PHAS=  -159.3 FOM=  0.12 TEST= 0
INDE  6  66  26 FOBS=   69.5 SIGMA=   3.9 PHAS=    45.2 FOM=  0.89 TEST= 0
INDE  6  66  28 FOBS=  108.7 SIGMA=   2.2 PHAS=    21.6 FOM=  0.95 TEST= 0
INDE  6  66  30 FOBS=   40.0 SIGMA=   8.6 PHAS=    -5.8 FOM=  0.75 TEST= 0
INDE  6  66  32 FOBS=   92.2 SIGMA=   3.2 PHAS=  -131.6 FOM=  0.91 TEST= 0
INDE  6  66  34 FOBS=   56.2 SIGMA=   5.2 PHAS=    71.1 FOM=  0.53 TEST= 0
INDE  6  66  36 FOBS=   31.5 SIGMA=  10.8 PHAS=  -158.6 FOM=  0.32 TEST= 0
INDE  6  66  38 FOBS=   55.5 SIGMA=   5.3 PHAS=  -151.9 FOM=  0.15 TEST= 1
INDE  6  66  40 FOBS=   67.4 SIGMA=   4.5 PHAS=   -44.1 FOM=  0.76 TEST= 0
INDE  6  67   7 FOBS=   28.0 SIGMA=  18.0 PHAS=   -61.6 FOM=  0.33 TEST= 0
INDE  6  67   9 FOBS=  152.2 SIGMA=   3.6 PHAS=   -25.3 FOM=  0.95 TEST= 0
INDE  6  67  11 FOBS=   64.9 SIGMA=   5.4 PHAS=  -109.5 FOM=  0.13 TEST= 0
INDE  6  67  13 FOBS=   27.4 SIGMA=  12.8 PHAS=  -141.9 FOM=  0.54 TEST= 0
INDE  6  67  15 FOBS=   46.8 SIGMA=   7.5 PHAS=   -76.9 FOM=  0.54 TEST= 0
INDE  6  67  17 FOBS=   29.3 SIGMA=  11.9 PHAS=   126.4 FOM=  0.34 TEST= 0
INDE  6  67  19 FOBS=   74.2 SIGMA=   3.0 PHAS=   138.9 FOM=  0.81 TEST= 0
INDE  6  67  21 FOBS=   56.2 SIGMA=   4.3 PHAS=   146.7 FOM=  0.35 TEST= 0
INDE  6  67  23 FOBS=   31.1 SIGMA=   6.7 PHAS=   167.5 FOM=  0.38 TEST= 0
INDE  6  67  25 FOBS=  112.3 SIGMA=   2.0 PHAS=  -127.0 FOM=  0.95 TEST= 0
INDE  6  67  27 FOBS=   97.6 SIGMA=   2.9 PHAS=   -32.9 FOM=  0.94 TEST= 0
INDE  6  67  29 FOBS=   80.8 SIGMA=   3.0 PHAS=   120.9 FOM=  0.91 TEST= 0
INDE  6  67  31 FOBS=  108.7 SIGMA=   2.7 PHAS=   170.1 FOM=  0.90 TEST= 0
INDE  6  67  33 FOBS=   26.2 SIGMA=  11.0 PHAS=     2.4 FOM=  0.39 TEST= 0
INDE  6  67  35 FOBS=    0.0 SIGMA=  26.6 PHAS=     0.0 FOM=  0.00 TEST= 0
INDE  6  67  37 FOBS=   24.5 SIGMA=  12.1 PHAS=    46.2 FOM=  0.41 TEST= 0
INDE  6  67  39 FOBS=   73.0 SIGMA=   7.1 PHAS=  -177.6 FOM=  0.74 TEST= 0
INDE  6  68   6 FOBS=   92.8 SIGMA=   4.0 PHAS=  -157.2 FOM=  0.87 TEST= 0
INDE  6  68  12 FOBS=   17.5 SIGMA=  28.7 PHAS=    13.9 FOM=  0.02 TEST= 1
INDE  6  68  14 FOBS=   60.8 SIGMA=   8.1 PHAS=   -40.9 FOM=  0.67 TEST= 0
INDE  6  68  16 FOBS=   78.5 SIGMA=   4.5 PHAS=    98.9 FOM=  0.90 TEST= 0
INDE  6  68  18 FOBS=   83.0 SIGMA=   4.3 PHAS=    65.4 FOM=  0.90 TEST= 0
INDE  6  68  20 FOBS=   69.5 SIGMA=   3.3 PHAS=   123.5 FOM=  0.40 TEST= 1
INDE  6  68  22 FOBS=   19.9 SIGMA=  14.5 PHAS=    95.7 FOM=  0.07 TEST= 0
INDE  6  68  24 FOBS=   81.8 SIGMA=   2.6 PHAS=   151.3 FOM=  0.81 TEST= 0
INDE  6  68  26 FOBS=    0.0 SIGMA=  21.3 PHAS=     0.0 FOM=  0.00 TEST= 0
INDE  6  68  28 FOBS=   81.6 SIGMA=   3.5 PHAS=     1.9 FOM=  0.88 TEST= 0
INDE  6  68  30 FOBS=   45.4 SIGMA=   5.4 PHAS=    64.6 FOM=  0.23 TEST= 1
INDE  6  68  32 FOBS=   42.3 SIGMA=   6.8 PHAS=    42.9 FOM=  0.31 TEST= 0
INDE  6  68  34 FOBS=    0.0 SIGMA=  24.1 PHAS=     0.0 FOM=  0.00 TEST= 0
INDE  6  68  36 FOBS=    9.2 SIGMA=  32.4 PHAS=  -100.3 FOM=  0.10 TEST= 0
INDE  6  69  17 FOBS=   69.3 SIGMA=   7.1 PHAS=   -17.7 FOM=  0.87 TEST= 0
INDE  6  69  19 FOBS=   79.7 SIGMA=   6.4 PHAS=    -2.5 FOM=  0.91 TEST= 0
INDE  6  69  21 FOBS=    0.0 SIGMA=  21.4 PHAS=     0.0 FOM=  0.00 TEST= 1
INDE  6  69  23 FOBS=   59.2 SIGMA=   4.3 PHAS=    91.4 FOM=  0.65 TEST= 0
INDE  6  69  25 FOBS=   92.1 SIGMA=   2.4 PHAS=   -37.8 FOM=  0.95 TEST= 0
INDE  6  69  27 FOBS=   61.7 SIGMA=   3.8 PHAS=   -21.2 FOM=  0.70 TEST= 0
INDE  6  69  29 FOBS=    0.0 SIGMA=  24.0 PHAS=     0.0 FOM=  0.00 TEST= 0
INDE  6  69  31 FOBS=    0.0 SIGMA=  22.3 PHAS=     0.0 FOM=  0.00 TEST= 0
INDE  6  69  33 FOBS=   34.7 SIGMA=   8.5 PHAS=   -61.1 FOM=  0.72 TEST= 0
INDE  6  69  35 FOBS=    0.0 SIGMA=  24.5 PHAS=     0.0 FOM=  0.00 TEST= 1
INDE  6  70   6 FOBS=   56.2 SIGMA=   6.3 PHAS=    52.3 FOM=  0.28 TEST= 0
INDE  6  70  20 FOBS=   74.5 SIGMA=   6.9 PHAS=   -94.3 FOM=  0.85 TEST= 0
INDE  6  70  22 FOBS=   33.9 SIGMA=   8.0 PHAS=    19.4 FOM=  0.18 TEST= 0
INDE  6  70  24 FOBS=   44.9 SIGMA=   5.3 PHAS=  -118.9 FOM=  0.73 TEST= 0
INDE  6  70  26 FOBS=   86.4 SIGMA=   2.7 PHAS=  -133.8 FOM=  0.93 TEST= 0
INDE  6  70  28 FOBS=    0.0 SIGMA=  23.6 PHAS=     0.0 FOM=  0.00 TEST= 1
INDE  6  70  30 FOBS=    0.0 SIGMA=  24.2 PHAS=     0.0 FOM=  0.00 TEST= 0
INDE  6  70  32 FOBS=   90.8 SIGMA=   2.9 PHAS=  -134.6 FOM=  0.89 TEST= 0
INDE  6  71   7 FOBS=   48.6 SIGMA=   7.6 PHAS=   -94.7 FOM=  0.45 TEST= 0
INDE  6  71  23 FOBS=   30.4 SIGMA=  11.1 PHAS=   -76.1 FOM=  0.07 TEST= 1
INDE  6  71  25 FOBS=   23.9 SIGMA=  10.1 PHAS=   113.1 FOM=  0.34 TEST= 1
INDE  6  71  27 FOBS=    0.0 SIGMA=  22.5 PHAS=     0.0 FOM=  0.00 TEST= 0
INDE  6  71  29 FOBS=    0.0 SIGMA=  23.5 PHAS=     0.0 FOM=  0.00 TEST= 0
INDE  6  71  31 FOBS=   49.2 SIGMA=  10.9 PHAS=  -173.8 FOM=  0.78 TEST= 0
INDE  6  72   6 FOBS=  102.0 SIGMA=   3.8 PHAS=   -12.1 FOM=  0.93 TEST= 0
INDE  6  72   8 FOBS=   28.5 SIGMA=  13.0 PHAS=   -64.0 FOM=  0.16 TEST= 0
INDE  6  72  22 FOBS=   13.1 SIGMA=  23.5 PHAS=     0.0 FOM=  0.00 TEST= 1
```

*FIG. 12A - 185*

| | | | | | | | | | | | | |
|---|---|---|---|---|---|---|---|---|---|---|---|---|
| INDE | 6 | 72 | 24 | FOBS= | 38.3 | SIGMA= | 9.3 | PHAS= | -112.5 | FOM= | 0.61 | TEST= 0 |
| INDE | 6 | 72 | 26 | FOBS= | 0.0 | SIGMA= | 23.8 | PHAS= | 0.0 | FOM= | 0.00 | TEST= 0 |
| INDE | 6 | 72 | 28 | FOBS= | 0.0 | SIGMA= | 24.7 | PHAS= | 0.0 | FOM= | 0.00 | TEST= 0 |
| INDE | 6 | 73 | 7 | FOBS= | 96.5 | SIGMA= | 3.7 | PHAS= | -116.7 | FOM= | 0.95 | TEST= 0 |
| INDE | 6 | 73 | 23 | FOBS= | 65.1 | SIGMA= | 5.1 | PHAS= | -116.7 | FOM= | 0.67 | TEST= 0 |
| INDE | 6 | 73 | 25 | FOBS= | 8.5 | SIGMA= | 44.5 | PHAS= | 173.9 | FOM= | 0.14 | TEST= 0 |
| INDE | 6 | 74 | 6 | FOBS= | 40.3 | SIGMA= | 9.1 | PHAS= | 85.2 | FOM= | 0.52 | TEST= 0 |
| INDE | 6 | 74 | 8 | FOBS= | 40.3 | SIGMA= | 9.2 | PHAS= | 134.2 | FOM= | 0.66 | TEST= 0 |
| INDE | 6 | 75 | 7 | FOBS= | 60.0 | SIGMA= | 6.5 | PHAS= | 18.1 | FOM= | 0.76 | TEST= 0 |
| INDE | 6 | 75 | 9 | FOBS= | 63.9 | SIGMA= | 6.0 | PHAS= | 44.1 | FOM= | 0.60 | TEST= 0 |
| INDE | 6 | 76 | 6 | FOBS= | 0.0 | SIGMA= | 27.1 | PHAS= | 0.0 | FOM= | 0.00 | TEST= 0 |
| INDE | 6 | 77 | 7 | FOBS= | 0.0 | SIGMA= | 27.7 | PHAS= | 0.0 | FOM= | 0.00 | TEST= 1 |
| INDE | 6 | 77 | 9 | FOBS= | 67.1 | SIGMA= | 6.0 | PHAS= | 96.1 | FOM= | 0.79 | TEST= 0 |
| INDE | 7 | 8 | 15 | FOBS= | 100.9 | SIGMA= | 0.5 | PHAS= | -47.4 | FOM= | 0.96 | TEST= 0 |
| INDE | 7 | 8 | 17 | FOBS= | 229.6 | SIGMA= | 0.5 | PHAS= | 129.3 | FOM= | 0.86 | TEST= 0 |
| INDE | 7 | 8 | 19 | FOBS= | 63.9 | SIGMA= | 0.8 | PHAS= | 118.9 | FOM= | 0.47 | TEST= 0 |
| INDE | 7 | 8 | 21 | FOBS= | 69.9 | SIGMA= | 0.9 | PHAS= | 47.5 | FOM= | 0.96 | TEST= 0 |
| INDE | 7 | 8 | 23 | FOBS= | 106.0 | SIGMA= | 0.7 | PHAS= | 106.1 | FOM= | 0.41 | TEST= 0 |
| INDE | 7 | 8 | 25 | FOBS= | 151.4 | SIGMA= | 0.6 | PHAS= | -45.5 | FOM= | 0.98 | TEST= 0 |
| INDE | 7 | 8 | 27 | FOBS= | 142.3 | SIGMA= | 0.6 | PHAS= | 20.1 | FOM= | 0.98 | TEST= 0 |
| INDE | 7 | 8 | 29 | FOBS= | 109.9 | SIGMA= | 0.9 | PHAS= | 173.1 | FOM= | 0.99 | TEST= 0 |
| INDE | 7 | 8 | 31 | FOBS= | 211.9 | SIGMA= | 0.7 | PHAS= | 15.4 | FOM= | 0.96 | TEST= 0 |
| INDE | 7 | 8 | 33 | FOBS= | 47.7 | SIGMA= | 2.3 | PHAS= | -65.9 | FOM= | 0.93 | TEST= 0 |
| INDE | 7 | 8 | 35 | FOBS= | 501.8 | SIGMA= | 0.8 | PHAS= | -166.1 | FOM= | 0.99 | TEST= 0 |
| INDE | 7 | 8 | 37 | FOBS= | 264.0 | SIGMA= | 0.7 | PHAS= | -130.9 | FOM= | 0.91 | TEST= 0 |
| INDE | 7 | 8 | 39 | FOBS= | 120.8 | SIGMA= | 1.2 | PHAS= | -145.2 | FOM= | 0.20 | TEST= 1 |
| INDE | 7 | 8 | 41 | FOBS= | 156.6 | SIGMA= | 1.1 | PHAS= | -59.6 | FOM= | 0.96 | TEST= 0 |
| INDE | 7 | 8 | 43 | FOBS= | 84.1 | SIGMA= | 2.1 | PHAS= | -40.1 | FOM= | 0.93 | TEST= 1 |
| INDE | 7 | 8 | 45 | FOBS= | 24.9 | SIGMA= | 8.5 | PHAS= | -151.0 | FOM= | 0.75 | TEST= 0 |
| INDE | 7 | 8 | 47 | FOBS= | 115.5 | SIGMA= | 1.8 | PHAS= | 149.8 | FOM= | 0.87 | TEST= 0 |
| INDE | 7 | 8 | 49 | FOBS= | 186.7 | SIGMA= | 1.2 | PHAS= | 31.4 | FOM= | 0.93 | TEST= 0 |
| INDE | 7 | 8 | 51 | FOBS= | 139.7 | SIGMA= | 1.5 | PHAS= | 14.5 | FOM= | 0.92 | TEST= 0 |
| INDE | 7 | 8 | 53 | FOBS= | 148.7 | SIGMA= | 1.4 | PHAS= | 64.1 | FOM= | 0.92 | TEST= 0 |
| INDE | 7 | 8 | 55 | FOBS= | 237.9 | SIGMA= | 1.3 | PHAS= | 37.3 | FOM= | 0.97 | TEST= 0 |
| INDE | 7 | 8 | 57 | FOBS= | 40.2 | SIGMA= | 6.5 | PHAS= | 134.1 | FOM= | 0.77 | TEST= 0 |
| INDE | 7 | 8 | 59 | FOBS= | 53.5 | SIGMA= | 4.9 | PHAS= | 79.8 | FOM= | 0.79 | TEST= 0 |
| INDE | 7 | 8 | 61 | FOBS= | 50.9 | SIGMA= | 4.9 | PHAS= | -41.6 | FOM= | 0.39 | TEST= 1 |
| INDE | 7 | 8 | 63 | FOBS= | 0.0 | SIGMA= | 24.0 | PHAS= | 0.0 | FOM= | 0.00 | TEST= 0 |
| INDE | 7 | 8 | 65 | FOBS= | 80.5 | SIGMA= | 4.4 | PHAS= | 177.9 | FOM= | 0.92 | TEST= 0 |
| INDE | 7 | 8 | 71 | FOBS= | 0.0 | SIGMA= | 27.8 | PHAS= | 0.0 | FOM= | 0.00 | TEST= 0 |
| INDE | 7 | 8 | 73 | FOBS= | 91.3 | SIGMA= | 4.4 | PHAS= | -96.0 | FOM= | 0.91 | TEST= 0 |
| INDE | 7 | 8 | 75 | FOBS= | 51.8 | SIGMA= | 7.5 | PHAS= | -46.7 | FOM= | 0.77 | TEST= 0 |
| INDE | 7 | 8 | 77 | FOBS= | 0.0 | SIGMA= | 29.1 | PHAS= | 0.0 | FOM= | 0.00 | TEST= 0 |
| INDE | 7 | 9 | 14 | FOBS= | 181.4 | SIGMA= | 0.5 | PHAS= | 91.0 | FOM= | 0.82 | TEST= 0 |
| INDE | 7 | 9 | 16 | FOBS= | 159.4 | SIGMA= | 0.4 | PHAS= | 104.5 | FOM= | 0.70 | TEST= 0 |
| INDE | 7 | 9 | 18 | FOBS= | 125.9 | SIGMA= | 0.5 | PHAS= | -144.4 | FOM= | 0.85 | TEST= 0 |
| INDE | 7 | 9 | 20 | FOBS= | 101.9 | SIGMA= | 0.6 | PHAS= | 167.1 | FOM= | 0.87 | TEST= 0 |
| INDE | 7 | 9 | 22 | FOBS= | 29.4 | SIGMA= | 2.0 | PHAS= | 18.2 | FOM= | 0.56 | TEST= 1 |
| INDE | 7 | 9 | 24 | FOBS= | 167.0 | SIGMA= | 0.5 | PHAS= | -90.4 | FOM= | 0.96 | TEST= 0 |
| INDE | 7 | 9 | 26 | FOBS= | 193.0 | SIGMA= | 0.5 | PHAS= | 172.3 | FOM= | 0.99 | TEST= 0 |
| INDE | 7 | 9 | 28 | FOBS= | 118.6 | SIGMA= | 0.9 | PHAS= | -70.1 | FOM= | 0.98 | TEST= 0 |
| INDE | 7 | 9 | 30 | FOBS= | 66.4 | SIGMA= | 1.5 | PHAS= | 3.6 | FOM= | 0.96 | TEST= 0 |
| INDE | 7 | 9 | 32 | FOBS= | 210.9 | SIGMA= | 0.6 | PHAS= | -95.7 | FOM= | 0.97 | TEST= 0 |
| INDE | 7 | 9 | 34 | FOBS= | 181.3 | SIGMA= | 0.9 | PHAS= | -154.8 | FOM= | 0.95 | TEST= 0 |
| INDE | 7 | 9 | 36 | FOBS= | 302.7 | SIGMA= | 0.6 | PHAS= | -145.8 | FOM= | 0.74 | TEST= 0 |
| INDE | 7 | 9 | 38 | FOBS= | 164.5 | SIGMA= | 0.9 | PHAS= | 106.9 | FOM= | 0.98 | TEST= 1 |
| INDE | 7 | 9 | 40 | FOBS= | 316.2 | SIGMA= | 0.9 | PHAS= | -131.9 | FOM= | 0.96 | TEST= 1 |
| INDE | 7 | 9 | 42 | FOBS= | 173.7 | SIGMA= | 1.1 | PHAS= | -120.6 | FOM= | 0.76 | TEST= 0 |
| INDE | 7 | 9 | 44 | FOBS= | 185.9 | SIGMA= | 1.1 | PHAS= | 3.6 | FOM= | 0.94 | TEST= 0 |
| INDE | 7 | 9 | 46 | FOBS= | 152.8 | SIGMA= | 1.6 | PHAS= | 69.9 | FOM= | 0.77 | TEST= 0 |
| INDE | 7 | 9 | 48 | FOBS= | 73.5 | SIGMA= | 2.9 | PHAS= | 175.2 | FOM= | 0.76 | TEST= 0 |
| INDE | 7 | 9 | 50 | FOBS= | 136.0 | SIGMA= | 1.6 | PHAS= | 26.0 | FOM= | 0.79 | TEST= 0 |
| INDE | 7 | 9 | 52 | FOBS= | 71.6 | SIGMA= | 2.8 | PHAS= | -37.0 | FOM= | 0.84 | TEST= 0 |
| INDE | 7 | 9 | 54 | FOBS= | 160.1 | SIGMA= | 1.3 | PHAS= | -6.2 | FOM= | 0.89 | TEST= 0 |
| INDE | 7 | 9 | 56 | FOBS= | 21.7 | SIGMA= | 9.6 | PHAS= | -108.2 | FOM= | 0.18 | TEST= 0 |
| INDE | 7 | 9 | 58 | FOBS= | 228.4 | SIGMA= | 1.1 | PHAS= | 10.0 | FOM= | 0.98 | TEST= 0 |
| INDE | 7 | 9 | 60 | FOBS= | 41.5 | SIGMA= | 6.2 | PHAS= | 115.2 | FOM= | 0.54 | TEST= 0 |
| INDE | 7 | 9 | 62 | FOBS= | 103.9 | SIGMA= | 2.5 | PHAS= | -143.1 | FOM= | 0.88 | TEST= 0 |
| INDE | 7 | 9 | 64 | FOBS= | 0.0 | SIGMA= | 26.3 | PHAS= | 0.0 | FOM= | 0.00 | TEST= 0 |
| INDE | 7 | 9 | 66 | FOBS= | 35.2 | SIGMA= | 9.9 | PHAS= | -47.2 | FOM= | 0.09 | TEST= 0 |

*FIG. 12A - 186*

| | | | | | | | | | | | |
|---|---|---|---|---|---|---|---|---|---|---|---|
| INDE | 7 | 9 | 72 | FOBS= | 2.8 | SIGMA= | 142.6 | PHAS= | 0.0 | FOM= | 0.00 | TEST= 1
| INDE | 7 | 9 | 74 | FOBS= | 88.9 | SIGMA= | 4.6 | PHAS= | -160.7 | FOM= | 0.91 | TEST= 0
| INDE | 7 | 9 | 76 | FOBS= | 0.0 | SIGMA= | 28.4 | PHAS= | 0.0 | FOM= | 0.00 | TEST= 0
| INDE | 7 | 10 | 15 | FOBS= | 416.1 | SIGMA= | 0.4 | PHAS= | -10.0 | FOM= | 0.92 | TEST= 0
| INDE | 7 | 10 | 17 | FOBS= | 77.9 | SIGMA= | 0.7 | PHAS= | 104.1 | FOM= | 0.94 | TEST= 0
| INDE | 7 | 10 | 19 | FOBS= | 119.4 | SIGMA= | 0.5 | PHAS= | 59.4 | FOM= | 0.83 | TEST= 0
| INDE | 7 | 10 | 21 | FOBS= | 132.5 | SIGMA= | 0.5 | PHAS= | 108.2 | FOM= | 0.93 | TEST= 0
| INDE | 7 | 10 | 23 | FOBS= | 187.5 | SIGMA= | 0.5 | PHAS= | 175.5 | FOM= | 0.96 | TEST= 0
| INDE | 7 | 10 | 25 | FOBS= | 51.3 | SIGMA= | 1.3 | PHAS= | 28.6 | FOM= | 0.99 | TEST= 0
| INDE | 7 | 10 | 27 | FOBS= | 143.9 | SIGMA= | 0.6 | PHAS= | 39.4 | FOM= | 0.97 | TEST= 0
| INDE | 7 | 10 | 29 | FOBS= | 153.1 | SIGMA= | 0.7 | PHAS= | 164.1 | FOM= | 0.97 | TEST= 0
| INDE | 7 | 10 | 31 | FOBS= | 114.4 | SIGMA= | 1.0 | PHAS= | -102.1 | FOM= | 0.92 | TEST= 0
| INDE | 7 | 10 | 33 | FOBS= | 373.3 | SIGMA= | 0.7 | PHAS= | 172.0 | FOM= | 0.96 | TEST= 0
| INDE | 7 | 10 | 35 | FOBS= | 188.0 | SIGMA= | 1.1 | PHAS= | -13.8 | FOM= | 0.70 | TEST= 0
| INDE | 7 | 10 | 37 | FOBS= | 166.1 | SIGMA= | 0.9 | PHAS= | -18.3 | FOM= | 0.97 | TEST= 0
| INDE | 7 | 10 | 39 | FOBS= | 241.0 | SIGMA= | 0.8 | PHAS= | 119.7 | FOM= | 0.97 | TEST= 0
| INDE | 7 | 10 | 41 | FOBS= | 290.7 | SIGMA= | 0.8 | PHAS= | 132.9 | FOM= | 0.95 | TEST= 0
| INDE | 7 | 10 | 43 | FOBS= | 127.5 | SIGMA= | 1.2 | PHAS= | -89.1 | FOM= | 0.83 | TEST= 0
| INDE | 7 | 10 | 45 | FOBS= | 65.1 | SIGMA= | 1.9 | PHAS= | -65.3 | FOM= | 0.87 | TEST= 1
| INDE | 7 | 10 | 47 | FOBS= | 210.0 | SIGMA= | 1.2 | PHAS= | 71.0 | FOM= | 0.94 | TEST= 0
| INDE | 7 | 10 | 49 | FOBS= | 61.2 | SIGMA= | 3.8 | PHAS= | 124.2 | FOM= | 0.72 | TEST= 0
| INDE | 7 | 10 | 51 | FOBS= | 70.9 | SIGMA= | 2.9 | PHAS= | -86.5 | FOM= | 0.38 | TEST= 0
| INDE | 7 | 10 | 53 | FOBS= | 0.0 | SIGMA= | 20.8 | PHAS= | 0.0 | FOM= | 0.00 | TEST= 0
| INDE | 7 | 10 | 55 | FOBS= | 59.7 | SIGMA= | 3.3 | PHAS= | 56.0 | FOM= | 0.57 | TEST= 0
| INDE | 7 | 10 | 57 | FOBS= | 98.1 | SIGMA= | 2.0 | PHAS= | -115.3 | FOM= | 0.88 | TEST= 0
| INDE | 7 | 10 | 59 | FOBS= | 24.1 | SIGMA= | 7.9 | PHAS= | 100.3 | FOM= | 0.21 | TEST= 0
| INDE | 7 | 10 | 61 | FOBS= | 56.9 | SIGMA= | 3.3 | PHAS= | -168.1 | FOM= | 0.09 | TEST= 0
| INDE | 7 | 10 | 63 | FOBS= | 76.1 | SIGMA= | 3.2 | PHAS= | 158.0 | FOM= | 0.60 | TEST= 0
| INDE | 7 | 10 | 65 | FOBS= | 58.5 | SIGMA= | 6.0 | PHAS= | -126.9 | FOM= | 0.83 | TEST= 0
| INDE | 7 | 10 | 73 | FOBS= | 60.7 | SIGMA= | 6.8 | PHAS= | 41.6 | FOM= | 0.86 | TEST= 0
| INDE | 7 | 10 | 75 | FOBS= | 20.6 | SIGMA= | 20.0 | PHAS= | 151.6 | FOM= | 0.26 | TEST= 0
| INDE | 7 | 11 | 14 | FOBS= | 327.6 | SIGMA= | 0.5 | PHAS= | -51.0 | FOM= | 0.98 | TEST= 0
| INDE | 7 | 11 | 16 | FOBS= | 224.4 | SIGMA= | 0.4 | PHAS= | -68.2 | FOM= | 0.86 | TEST= 0
| INDE | 7 | 11 | 18 | FOBS= | 102.7 | SIGMA= | 0.5 | PHAS= | -11.7 | FOM= | 0.78 | TEST= 0
| INDE | 7 | 11 | 20 | FOBS= | 60.7 | SIGMA= | 0.8 | PHAS= | -76.3 | FOM= | 0.90 | TEST= 0
| INDE | 7 | 11 | 22 | FOBS= | 53.1 | SIGMA= | 1.0 | PHAS= | 45.9 | FOM= | 0.95 | TEST= 0
| INDE | 7 | 11 | 24 | FOBS= | 173.7 | SIGMA= | 0.4 | PHAS= | 5.1 | FOM= | 0.99 | TEST= 0
| INDE | 7 | 11 | 26 | FOBS= | 170.1 | SIGMA= | 0.5 | PHAS= | -99.6 | FOM= | 0.99 | TEST= 0
| INDE | 7 | 11 | 28 | FOBS= | 119.2 | SIGMA= | 0.6 | PHAS= | -76.7 | FOM= | 0.96 | TEST= 0
| INDE | 7 | 11 | 30 | FOBS= | 168.5 | SIGMA= | 0.5 | PHAS= | 59.2 | FOM= | 0.94 | TEST= 0
| INDE | 7 | 11 | 32 | FOBS= | 178.3 | SIGMA= | 0.5 | PHAS= | 127.2 | FOM= | 0.94 | TEST= 0
| INDE | 7 | 11 | 34 | FOBS= | 81.7 | SIGMA= | 1.2 | PHAS= | -157.4 | FOM= | 0.70 | TEST= 0
| INDE | 7 | 11 | 36 | FOBS= | 193.6 | SIGMA= | 0.6 | PHAS= | -129.9 | FOM= | 0.86 | TEST= 0
| INDE | 7 | 11 | 38 | FOBS= | 222.4 | SIGMA= | 0.7 | PHAS= | -128.4 | FOM= | 0.79 | TEST= 1
| INDE | 7 | 11 | 40 | FOBS= | 166.9 | SIGMA= | 0.7 | PHAS= | 16.4 | FOM= | 0.90 | TEST= 0
| INDE | 7 | 11 | 42 | FOBS= | 282.9 | SIGMA= | 0.6 | PHAS= | 109.7 | FOM= | 0.89 | TEST= 0
| INDE | 7 | 11 | 44 | FOBS= | 196.8 | SIGMA= | 1.2 | PHAS= | -98.6 | FOM= | 0.77 | TEST= 1
| INDE | 7 | 11 | 46 | FOBS= | 313.5 | SIGMA= | 0.9 | PHAS= | -4.1 | FOM= | 0.95 | TEST= 0
| INDE | 7 | 11 | 48 | FOBS= | 32.5 | SIGMA= | 6.9 | PHAS= | -51.2 | FOM= | 0.32 | TEST= 0
| INDE | 7 | 11 | 50 | FOBS= | 151.4 | SIGMA= | 1.4 | PHAS= | 78.4 | FOM= | 0.96 | TEST= 0
| INDE | 7 | 11 | 52 | FOBS= | 64.5 | SIGMA= | 3.2 | PHAS= | -128.4 | FOM= | 0.07 | TEST= 0
| INDE | 7 | 11 | 54 | FOBS= | 0.0 | SIGMA= | 20.0 | PHAS= | 0.0 | FOM= | 0.00 | TEST= 0
| INDE | 7 | 11 | 56 | FOBS= | 69.2 | SIGMA= | 2.9 | PHAS= | -63.9 | FOM= | 0.80 | TEST= 0
| INDE | 7 | 11 | 58 | FOBS= | 102.4 | SIGMA= | 2.0 | PHAS= | 88.9 | FOM= | 0.88 | TEST= 0
| INDE | 7 | 11 | 60 | FOBS= | 0.0 | SIGMA= | 20.3 | PHAS= | 0.0 | FOM= | 0.00 | TEST= 0
| INDE | 7 | 11 | 62 | FOBS= | 12.3 | SIGMA= | 16.7 | PHAS= | 32.7 | FOM= | 0.19 | TEST= 0
| INDE | 7 | 11 | 64 | FOBS= | 43.0 | SIGMA= | 7.4 | PHAS= | -140.2 | FOM= | 0.37 | TEST= 0
| INDE | 7 | 11 | 66 | FOBS= | 0.0 | SIGMA= | 31.9 | PHAS= | 0.0 | FOM= | 0.00 | TEST= 0
| INDE | 7 | 11 | 72 | FOBS= | 48.8 | SIGMA= | 8.5 | PHAS= | -37.0 | FOM= | 0.58 | TEST= 0
| INDE | 7 | 11 | 74 | FOBS= | 0.0 | SIGMA= | 29.2 | PHAS= | 0.0 | FOM= | 0.00 | TEST= 0
| INDE | 7 | 11 | 76 | FOBS= | 45.4 | SIGMA= | 9.3 | PHAS= | 123.3 | FOM= | 0.60 | TEST= 0
| INDE | 7 | 12 | 13 | FOBS= | 155.9 | SIGMA= | 0.4 | PHAS= | -23.8 | FOM= | 0.68 | TEST= 0
| INDE | 7 | 12 | 15 | FOBS= | 124.4 | SIGMA= | 0.5 | PHAS= | -119.9 | FOM= | 0.99 | TEST= 0
| INDE | 7 | 12 | 17 | FOBS= | 289.4 | SIGMA= | 0.4 | PHAS= | 173.9 | FOM= | 0.81 | TEST= 0
| INDE | 7 | 12 | 19 | FOBS= | 88.1 | SIGMA= | 0.6 | PHAS= | 174.5 | FOM= | 0.22 | TEST= 0
| INDE | 7 | 12 | 21 | FOBS= | 128.8 | SIGMA= | 0.5 | PHAS= | -177.9 | FOM= | 0.66 | TEST= 0
| INDE | 7 | 12 | 23 | FOBS= | 170.9 | SIGMA= | 0.5 | PHAS= | -98.2 | FOM= | 0.92 | TEST= 0
| INDE | 7 | 12 | 25 | FOBS= | 99.9 | SIGMA= | 0.7 | PHAS= | 165.1 | FOM= | 0.88 | TEST= 1
| INDE | 7 | 12 | 27 | FOBS= | 131.2 | SIGMA= | 0.6 | PHAS= | -171.8 | FOM= | 0.92 | TEST= 0
| INDE | 7 | 12 | 29 | FOBS= | 71.7 | SIGMA= | 1.0 | PHAS= | 143.9 | FOM= | 0.99 | TEST= 0

*FIG. 12A - 187*

```
INDE  7  12  31 FOBS=  123.6 SIGMA=  0.6 PHAS=    3.0 FOM= 0.94 TEST= 0
INDE  7  12  33 FOBS=  246.9 SIGMA=  0.5 PHAS=  151.7 FOM= 0.95 TEST= 0
INDE  7  12  35 FOBS=  220.9 SIGMA=  0.6 PHAS=  171.6 FOM= 0.82 TEST= 0
INDE  7  12  37 FOBS=  264.0 SIGMA=  0.6 PHAS=  158.9 FOM= 0.96 TEST= 0
INDE  7  12  39 FOBS=  242.8 SIGMA=  0.7 PHAS=  125.2 FOM= 0.93 TEST= 0
INDE  7  12  41 FOBS=  227.9 SIGMA=  0.9 PHAS=   42.8 FOM= 0.97 TEST= 0
INDE  7  12  43 FOBS=  276.1 SIGMA=  0.6 PHAS=  -35.8 FOM= 0.96 TEST= 0
INDE  7  12  45 FOBS=  153.6 SIGMA=  1.1 PHAS= -133.2 FOM= 0.94 TEST= 0
INDE  7  12  47 FOBS=  108.4 SIGMA=  2.0 PHAS=  -95.9 FOM= 0.85 TEST= 0
INDE  7  12  49 FOBS=   94.7 SIGMA=  2.2 PHAS=  179.5 FOM= 0.93 TEST= 0
INDE  7  12  51 FOBS=  140.6 SIGMA=  1.5 PHAS=    7.5 FOM= 0.93 TEST= 0
INDE  7  12  53 FOBS=   33.5 SIGMA=  5.9 PHAS=  125.0 FOM= 0.43 TEST= 0
INDE  7  12  55 FOBS=   47.8 SIGMA=  4.2 PHAS=  -70.2 FOM= 0.39 TEST= 0
INDE  7  12  57 FOBS=   26.3 SIGMA=  8.1 PHAS=   44.6 FOM= 0.30 TEST= 0
INDE  7  12  59 FOBS=   69.7 SIGMA=  2.8 PHAS=   14.7 FOM= 0.53 TEST= 0
INDE  7  12  61 FOBS=   65.0 SIGMA=  3.0 PHAS=  -11.7 FOM= 0.59 TEST= 0
INDE  7  12  63 FOBS=   37.4 SIGMA=  5.6 PHAS=  -75.2 FOM= 0.66 TEST= 0
INDE  7  12  65 FOBS=   66.0 SIGMA=  4.1 PHAS=  -93.8 FOM= 0.69 TEST= 0
INDE  7  12  67 FOBS=   25.5 SIGMA= 16.8 PHAS=   88.6 FOM= 0.18 TEST= 0
INDE  7  12  73 FOBS=    0.0 SIGMA= 29.3 PHAS=    0.0 FOM= 0.00 TEST= 0
INDE  7  12  75 FOBS=    0.0 SIGMA= 29.6 PHAS=    0.0 FOM= 0.00 TEST= 0
INDE  7  13  12 FOBS=  159.7 SIGMA=  0.5 PHAS=  150.0 FOM= 0.34 TEST= 0
INDE  7  13  14 FOBS=  235.6 SIGMA=  0.6 PHAS= -124.7 FOM= 0.92 TEST= 0
INDE  7  13  16 FOBS=   53.3 SIGMA=  1.0 PHAS=   70.8 FOM= 0.94 TEST= 0
INDE  7  13  18 FOBS=  223.2 SIGMA=  0.4 PHAS=   67.9 FOM= 0.86 TEST= 0
INDE  7  13  20 FOBS=   93.2 SIGMA=  0.6 PHAS=   22.3 FOM= 0.94 TEST= 0
INDE  7  13  22 FOBS=  175.0 SIGMA=  0.5 PHAS=   90.2 FOM= 0.97 TEST= 1
INDE  7  13  24 FOBS=  161.4 SIGMA=  0.5 PHAS=  -29.4 FOM= 0.97 TEST= 0
INDE  7  13  26 FOBS=   71.1 SIGMA=  1.0 PHAS=  -33.2 FOM= 0.82 TEST= 0
INDE  7  13  28 FOBS=  117.9 SIGMA=  0.6 PHAS=  126.3 FOM= 0.99 TEST= 0
INDE  7  13  30 FOBS=  279.4 SIGMA=  0.4 PHAS=   77.1 FOM= 0.93 TEST= 0
INDE  7  13  32 FOBS=  165.2 SIGMA=  0.5 PHAS=  140.2 FOM= 0.93 TEST= 0
INDE  7  13  34 FOBS=  194.2 SIGMA=  0.5 PHAS=  163.4 FOM= 0.91 TEST= 0
INDE  7  13  36 FOBS=  204.3 SIGMA=  0.6 PHAS=   41.7 FOM= 0.85 TEST= 1
INDE  7  13  38 FOBS=  429.8 SIGMA=  0.6 PHAS= -169.7 FOM= 0.61 TEST= 0
INDE  7  13  40 FOBS=  150.0 SIGMA=  1.2 PHAS=   -8.5 FOM= 0.93 TEST= 0
INDE  7  13  42 FOBS=  127.0 SIGMA=  1.0 PHAS=  -48.0 FOM= 0.96 TEST= 0
INDE  7  13  44 FOBS=  107.6 SIGMA=  1.4 PHAS= -127.5 FOM= 0.98 TEST= 0
INDE  7  13  46 FOBS=  199.1 SIGMA=  1.2 PHAS= -171.6 FOM= 0.93 TEST= 0
INDE  7  13  48 FOBS=  110.2 SIGMA=  1.9 PHAS=   20.3 FOM= 0.90 TEST= 0
INDE  7  13  50 FOBS=  118.4 SIGMA=  1.8 PHAS=   44.3 FOM= 0.85 TEST= 0
INDE  7  13  52 FOBS=  145.3 SIGMA=  1.5 PHAS=   12.9 FOM= 0.91 TEST= 0
INDE  7  13  54 FOBS=   81.1 SIGMA=  2.5 PHAS=  156.9 FOM= 0.42 TEST= 1
INDE  7  13  56 FOBS=   78.6 SIGMA=  2.5 PHAS=  -73.3 FOM= 0.81 TEST= 0
INDE  7  13  58 FOBS=   75.5 SIGMA=  2.6 PHAS=  138.9 FOM= 0.86 TEST= 0
INDE  7  13  60 FOBS=  161.2 SIGMA=  1.3 PHAS=  -90.3 FOM= 0.75 TEST= 1
INDE  7  13  62 FOBS=   57.7 SIGMA=  3.4 PHAS= -156.0 FOM= 0.54 TEST= 0
INDE  7  13  64 FOBS=   46.9 SIGMA=  5.8 PHAS= -159.7 FOM= 0.65 TEST= 0
INDE  7  13  66 FOBS=   43.8 SIGMA= 10.0 PHAS=  -67.1 FOM= 0.46 TEST= 0
INDE  7  13  68 FOBS=   43.4 SIGMA=  9.9 PHAS= -102.3 FOM= 0.53 TEST= 0
INDE  7  13  70 FOBS=   19.7 SIGMA= 22.1 PHAS= -117.6 FOM= 0.07 TEST= 0
INDE  7  13  74 FOBS=    0.0 SIGMA= 29.5 PHAS=    0.0 FOM= 0.00 TEST= 0
INDE  7  13  76 FOBS=    0.0 SIGMA= 30.1 PHAS=    0.0 FOM= 0.00 TEST= 0
INDE  7  14   9 FOBS=  265.6 SIGMA=  0.5 PHAS=  -76.2 FOM= 0.69 TEST= 0
INDE  7  14  11 FOBS=  290.8 SIGMA=  0.5 PHAS=  -14.3 FOM= 0.89 TEST= 0
INDE  7  14  13 FOBS=   66.3 SIGMA=  0.8 PHAS=  129.3 FOM= 0.95 TEST= 0
INDE  7  14  15 FOBS=  256.1 SIGMA=  0.5 PHAS=  144.9 FOM= 0.79 TEST= 1
INDE  7  14  17 FOBS=   50.8 SIGMA=  1.1 PHAS=   57.3 FOM= 0.96 TEST= 0
INDE  7  14  19 FOBS=  100.2 SIGMA=  0.6 PHAS=   -5.5 FOM= 0.96 TEST= 0
INDE  7  14  21 FOBS=  176.3 SIGMA=  0.5 PHAS= -134.5 FOM= 0.96 TEST= 0
INDE  7  14  23 FOBS=   73.2 SIGMA=  0.9 PHAS=  142.6 FOM= 0.57 TEST= 0
INDE  7  14  25 FOBS=   49.4 SIGMA=  1.4 PHAS=  -46.9 FOM= 0.97 TEST= 1
INDE  7  14  27 FOBS=   52.0 SIGMA=  1.3 PHAS= -136.2 FOM= 0.91 TEST= 0
INDE  7  14  29 FOBS=  264.7 SIGMA=  0.4 PHAS=   35.9 FOM= 0.98 TEST= 1
INDE  7  14  31 FOBS=  330.9 SIGMA=  0.4 PHAS=   28.3 FOM= 0.96 TEST= 0
INDE  7  14  33 FOBS=  194.7 SIGMA=  0.5 PHAS=  108.3 FOM= 0.95 TEST= 0
INDE  7  14  35 FOBS=   99.1 SIGMA=  0.9 PHAS=  -90.5 FOM= 0.95 TEST= 0
INDE  7  14  37 FOBS=  174.6 SIGMA=  0.7 PHAS=   91.6 FOM= 0.41 TEST= 0
INDE  7  14  39 FOBS=  175.9 SIGMA=  0.8 PHAS=  173.0 FOM= 0.88 TEST= 0
INDE  7  14  41 FOBS=   89.5 SIGMA=  1.4 PHAS=  -13.9 FOM= 0.74 TEST= 0
```

*FIG. 12A - 188*

```
INDE  7  14  43  FOBS=   55.7  SIGMA=   2.8  PHAS=  -98.9  FOM=  0.87  TEST= 0
INDE  7  14  45  FOBS=  245.9  SIGMA=   0.7  PHAS=  117.0  FOM=  0.95  TEST= 0
INDE  7  14  47  FOBS=  143.2  SIGMA=   1.5  PHAS=   19.1  FOM=  0.05  TEST= 1
INDE  7  14  49  FOBS=   56.7  SIGMA=   3.6  PHAS=  -77.9  FOM=  0.44  TEST= 0
INDE  7  14  51  FOBS=  209.1  SIGMA=   1.1  PHAS=  -37.7  FOM=  0.95  TEST= 0
INDE  7  14  53  FOBS=  150.7  SIGMA=   1.4  PHAS=  169.1  FOM=  0.96  TEST= 0
INDE  7  14  55  FOBS=   45.8  SIGMA=   4.3  PHAS=  -71.4  FOM=  0.13  TEST= 0
INDE  7  14  57  FOBS=  137.1  SIGMA=   1.5  PHAS=   81.1  FOM=  0.96  TEST= 0
INDE  7  14  59  FOBS=  137.0  SIGMA=   1.5  PHAS=  113.3  FOM=  0.92  TEST= 0
INDE  7  14  61  FOBS=  159.9  SIGMA=   1.3  PHAS=  162.0  FOM=  0.96  TEST= 0
INDE  7  14  63  FOBS=   62.1  SIGMA=   4.3  PHAS=    5.3  FOM=  0.54  TEST= 0
INDE  7  14  65  FOBS=  103.1  SIGMA=   2.7  PHAS= -135.8  FOM=  0.93  TEST= 0
INDE  7  14  67  FOBS=   83.9  SIGMA=   5.3  PHAS= -103.6  FOM=  0.80  TEST= 0
INDE  7  14  69  FOBS=   81.7  SIGMA=   5.5  PHAS= -122.9  FOM=  0.88  TEST= 0
INDE  7  14  71  FOBS=   38.8  SIGMA=  11.4  PHAS=  108.0  FOM=  0.49  TEST= 0
INDE  7  14  75  FOBS=   48.5  SIGMA=   9.5  PHAS=  -88.0  FOM=  0.58  TEST= 0
INDE  7  15   8  FOBS=  226.0  SIGMA=   0.4  PHAS= -155.0  FOM=  0.97  TEST= 0
INDE  7  15  10  FOBS=   56.0  SIGMA=   0.9  PHAS= -151.5  FOM=  0.70  TEST= 0
INDE  7  15  12  FOBS=  322.4  SIGMA=   0.5  PHAS=  116.0  FOM=  0.17  TEST= 1
INDE  7  15  14  FOBS=  283.9  SIGMA=   0.5  PHAS=   52.5  FOM=  0.91  TEST= 0
INDE  7  15  16  FOBS=  108.5  SIGMA=   0.5  PHAS=   91.8  FOM=  0.39  TEST= 0
INDE  7  15  18  FOBS=   85.1  SIGMA=   0.7  PHAS=  -94.4  FOM=  0.96  TEST= 0
INDE  7  15  20  FOBS=   36.2  SIGMA=   1.7  PHAS=   65.5  FOM=  0.99  TEST= 0
INDE  7  15  22  FOBS=  176.5  SIGMA=   0.5  PHAS=   44.7  FOM=  0.97  TEST= 0
INDE  7  15  24  FOBS=  122.3  SIGMA=   0.6  PHAS=  -46.5  FOM=  0.99  TEST= 0
INDE  7  15  26  FOBS=  129.7  SIGMA=   0.7  PHAS=   62.3  FOM=  0.89  TEST= 0
INDE  7  15  28  FOBS=  196.0  SIGMA=   0.5  PHAS=  -26.9  FOM=  0.89  TEST= 1
INDE  7  15  30  FOBS=  128.4  SIGMA=   0.6  PHAS=   20.9  FOM=  0.97  TEST= 0
INDE  7  15  32  FOBS=  299.4  SIGMA=   0.5  PHAS=  -30.5  FOM=  0.95  TEST= 0
INDE  7  15  34  FOBS=  241.2  SIGMA=   0.5  PHAS=   84.5  FOM=  0.97  TEST= 0
INDE  7  15  36  FOBS=  190.4  SIGMA=   0.6  PHAS=   67.9  FOM=  0.96  TEST= 0
INDE  7  15  38  FOBS=  206.3  SIGMA=   0.8  PHAS=  -66.6  FOM=  0.95  TEST= 0
INDE  7  15  40  FOBS=  280.4  SIGMA=   0.7  PHAS= -123.0  FOM=  0.91  TEST= 0
INDE  7  15  42  FOBS=  173.3  SIGMA=   0.8  PHAS=  -53.3  FOM=  0.90  TEST= 0
INDE  7  15  44  FOBS=  145.0  SIGMA=   1.5  PHAS=   64.5  FOM=  0.89  TEST= 0
INDE  7  15  46  FOBS=  276.3  SIGMA=   0.9  PHAS=  166.1  FOM=  0.84  TEST= 1
INDE  7  15  48  FOBS=   97.5  SIGMA=   2.2  PHAS=   31.9  FOM=  0.55  TEST= 0
INDE  7  15  50  FOBS=   67.4  SIGMA=   3.1  PHAS= -104.9  FOM=  0.45  TEST= 0
INDE  7  15  52  FOBS=  257.9  SIGMA=   0.9  PHAS=  121.3  FOM=  0.97  TEST= 0
INDE  7  15  54  FOBS=   52.8  SIGMA=   3.8  PHAS=    8.5  FOM=  0.72  TEST= 0
INDE  7  15  56  FOBS=  169.6  SIGMA=   1.3  PHAS=  -44.6  FOM=  0.96  TEST= 0
INDE  7  15  58  FOBS=  156.7  SIGMA=   1.3  PHAS=   24.2  FOM=  0.95  TEST= 0
INDE  7  15  60  FOBS=  136.0  SIGMA=   1.5  PHAS=   35.0  FOM=  0.88  TEST= 1
INDE  7  15  62  FOBS=   26.4  SIGMA=   7.1  PHAS=   76.1  FOM=  0.66  TEST= 0
INDE  7  15  64  FOBS=  102.3  SIGMA=   2.8  PHAS=   88.3  FOM=  0.04  TEST= 1
INDE  7  15  66  FOBS=  155.9  SIGMA=   3.0  PHAS=  146.4  FOM=  0.97  TEST= 0
INDE  7  15  68  FOBS=   66.1  SIGMA=   6.8  PHAS=  165.2  FOM=  0.76  TEST= 0
INDE  7  15  70  FOBS=   68.3  SIGMA=   6.6  PHAS=  146.5  FOM=  0.56  TEST= 0
INDE  7  15  72  FOBS=   44.7  SIGMA=  10.2  PHAS=  111.2  FOM=  0.72  TEST= 0
INDE  7  15  74  FOBS=    0.0  SIGMA=  25.6  PHAS=    0.0  FOM=  0.00  TEST= 0
INDE  7  16   7  FOBS=  176.2  SIGMA=   0.4  PHAS=  143.6  FOM=  0.89  TEST= 0
INDE  7  16   9  FOBS=  280.7  SIGMA=   0.5  PHAS=   96.3  FOM=  0.93  TEST= 0
INDE  7  16  11  FOBS=   43.4  SIGMA=   1.2  PHAS=  -40.2  FOM=  0.92  TEST= 0
INDE  7  16  13  FOBS=  129.1  SIGMA=   0.6  PHAS=  -71.8  FOM=  0.60  TEST= 0
INDE  7  16  15  FOBS=  226.4  SIGMA=   0.6  PHAS=  -67.3  FOM=  0.92  TEST= 0
INDE  7  16  17  FOBS=  147.8  SIGMA=   0.5  PHAS= -148.1  FOM=  0.86  TEST= 0
INDE  7  16  19  FOBS=  121.2  SIGMA=   0.5  PHAS=   28.6  FOM=  0.99  TEST= 0
INDE  7  16  21  FOBS=  150.0  SIGMA=   0.5  PHAS= -158.0  FOM=  0.97  TEST= 0
INDE  7  16  23  FOBS=  268.6  SIGMA=   0.5  PHAS= -132.6  FOM=  0.96  TEST= 0
INDE  7  16  25  FOBS=   65.7  SIGMA=   1.1  PHAS=    2.8  FOM=  0.99  TEST= 0
INDE  7  16  27  FOBS=  161.4  SIGMA=   0.5  PHAS= -105.7  FOM=  0.92  TEST= 0
INDE  7  16  29  FOBS=  105.9  SIGMA=   0.8  PHAS=  -61.4  FOM=  0.99  TEST= 0
INDE  7  16  31  FOBS=  157.8  SIGMA=   0.6  PHAS=  -18.5  FOM=  0.87  TEST= 1
INDE  7  16  33  FOBS=  257.2  SIGMA=   0.5  PHAS=  -89.4  FOM=  0.98  TEST= 0
INDE  7  16  35  FOBS=  415.9  SIGMA=   0.5  PHAS=  -16.7  FOM=  0.99  TEST= 0
INDE  7  16  37  FOBS=   76.0  SIGMA=   1.3  PHAS=  -80.5  FOM=  0.98  TEST= 0
INDE  7  16  39  FOBS=  144.1  SIGMA=   0.8  PHAS=  171.4  FOM=  0.93  TEST= 0
INDE  7  16  41  FOBS=  208.8  SIGMA=   0.7  PHAS=   92.6  FOM=  0.88  TEST= 0
INDE  7  16  43  FOBS=   65.3  SIGMA=   3.1  PHAS=   62.2  FOM=  0.88  TEST= 0
INDE  7  16  45  FOBS=  170.3  SIGMA=   1.4  PHAS=   81.7  FOM=  0.96  TEST= 0
```

*FIG. 12A - 189*

| | | | | | | | | | | | |
|---|---|---|---|---|---|---|---|---|---|---|---|
| INDE | 7 | 16 | 47 | FOBS= | 73.2 | SIGMA= | 3.0 | PHAS= | -86.1 | FOM= | 0.18 | TEST= 1
| INDE | 7 | 16 | 49 | FOBS= | 30.0 | SIGMA= | 6.9 | PHAS= | 82.2 | FOM= | 0.22 | TEST= 0
| INDE | 7 | 16 | 51 | FOBS= | 92.7 | SIGMA= | 2.3 | PHAS= | 0.9 | FOM= | 0.92 | TEST= 0
| INDE | 7 | 16 | 53 | FOBS= | 70.4 | SIGMA= | 2.9 | PHAS= | 124.7 | FOM= | 0.81 | TEST= 0
| INDE | 7 | 16 | 55 | FOBS= | 173.7 | SIGMA= | 1.3 | PHAS= | -106.0 | FOM= | 0.96 | TEST= 0
| INDE | 7 | 16 | 57 | FOBS= | 135.9 | SIGMA= | 1.5 | PHAS= | -117.1 | FOM= | 0.91 | TEST= 0
| INDE | 7 | 16 | 59 | FOBS= | 105.7 | SIGMA= | 1.9 | PHAS= | -78.4 | FOM= | 0.93 | TEST= 0
| INDE | 7 | 16 | 61 | FOBS= | 31.5 | SIGMA= | 6.1 | PHAS= | 34.5 | FOM= | 0.80 | TEST= 0
| INDE | 7 | 16 | 63 | FOBS= | 64.2 | SIGMA= | 3.6 | PHAS= | 57.8 | FOM= | 0.87 | TEST= 0
| INDE | 7 | 16 | 65 | FOBS= | 98.1 | SIGMA= | 3.4 | PHAS= | 47.1 | FOM= | 0.93 | TEST= 0
| INDE | 7 | 16 | 67 | FOBS= | 52.5 | SIGMA= | 8.2 | PHAS= | 98.3 | FOM= | 0.69 | TEST= 0
| INDE | 7 | 16 | 69 | FOBS= | 65.1 | SIGMA= | 6.8 | PHAS= | -153.9 | FOM= | 0.72 | TEST= 0
| INDE | 7 | 16 | 71 | FOBS= | 45.5 | SIGMA= | 9.9 | PHAS= | 58.7 | FOM= | 0.62 | TEST= 0
| INDE | 7 | 16 | 73 | FOBS= | 67.0 | SIGMA= | 7.0 | PHAS= | 55.0 | FOM= | 0.81 | TEST= 0
| INDE | 7 | 16 | 75 | FOBS= | 16.6 | SIGMA= | 20.3 | PHAS= | 83.0 | FOM= | 0.06 | TEST= 0
| INDE | 7 | 17 | 8 | FOBS= | 108.4 | SIGMA= | 0.5 | PHAS= | -27.1 | FOM= | 0.83 | TEST= 0
| INDE | 7 | 17 | 10 | FOBS= | 192.4 | SIGMA= | 0.4 | PHAS= | 56.5 | FOM= | 0.90 | TEST= 0
| INDE | 7 | 17 | 12 | FOBS= | 57.2 | SIGMA= | 1.0 | PHAS= | -62.0 | FOM= | 0.91 | TEST= 0
| INDE | 7 | 17 | 14 | FOBS= | 186.4 | SIGMA= | 0.7 | PHAS= | 179.1 | FOM= | 0.84 | TEST= 0
| INDE | 7 | 17 | 16 | FOBS= | 187.3 | SIGMA= | 0.6 | PHAS= | 158.0 | FOM= | 0.98 | TEST= 0
| INDE | 7 | 17 | 18 | FOBS= | 42.5 | SIGMA= | 1.5 | PHAS= | -168.5 | FOM= | 0.85 | TEST= 1
| INDE | 7 | 17 | 20 | FOBS= | 18.6 | SIGMA= | 3.4 | PHAS= | 148.3 | FOM= | 0.95 | TEST= 0
| INDE | 7 | 17 | 22 | FOBS= | 294.1 | SIGMA= | 0.4 | PHAS= | 104.1 | FOM= | 0.98 | TEST= 0
| INDE | 7 | 17 | 24 | FOBS= | 110.3 | SIGMA= | 0.8 | PHAS= | 156.3 | FOM= | 0.99 | TEST= 0
| INDE | 7 | 17 | 26 | FOBS= | 163.7 | SIGMA= | 0.6 | PHAS= | 2.6 | FOM= | 0.92 | TEST= 0
| INDE | 7 | 17 | 28 | FOBS= | 95.4 | SIGMA= | 0.8 | PHAS= | -70.6 | FOM= | 0.93 | TEST= 0
| INDE | 7 | 17 | 30 | FOBS= | 110.2 | SIGMA= | 0.8 | PHAS= | -130.8 | FOM= | 0.96 | TEST= 0
| INDE | 7 | 17 | 32 | FOBS= | 195.8 | SIGMA= | 0.5 | PHAS= | -37.1 | FOM= | 0.97 | TEST= 0
| INDE | 7 | 17 | 34 | FOBS= | 131.1 | SIGMA= | 0.9 | PHAS= | -122.1 | FOM= | 0.98 | TEST= 0
| INDE | 7 | 17 | 36 | FOBS= | 420.5 | SIGMA= | 0.5 | PHAS= | -133.1 | FOM= | 0.97 | TEST= 0
| INDE | 7 | 17 | 38 | FOBS= | 171.9 | SIGMA= | 0.7 | PHAS= | -91.5 | FOM= | 0.81 | TEST= 0
| INDE | 7 | 17 | 40 | FOBS= | 141.0 | SIGMA= | 1.1 | PHAS= | 133.9 | FOM= | 0.85 | TEST= 0
| INDE | 7 | 17 | 42 | FOBS= | 266.5 | SIGMA= | 0.9 | PHAS= | 18.6 | FOM= | 0.96 | TEST= 0
| INDE | 7 | 17 | 44 | FOBS= | 265.5 | SIGMA= | 1.1 | PHAS= | 70.9 | FOM= | 0.98 | TEST= 0
| INDE | 7 | 17 | 46 | FOBS= | 22.8 | SIGMA= | 9.6 | PHAS= | 123.6 | FOM= | 0.15 | TEST= 0
| INDE | 7 | 17 | 48 | FOBS= | 129.8 | SIGMA= | 1.2 | PHAS= | -108.7 | FOM= | 0.95 | TEST= 0
| INDE | 7 | 17 | 50 | FOBS= | 105.3 | SIGMA= | 2.0 | PHAS= | 48.8 | FOM= | 0.84 | TEST= 0
| INDE | 7 | 17 | 52 | FOBS= | 221.5 | SIGMA= | 1.1 | PHAS= | 112.8 | FOM= | 0.89 | TEST= 0
| INDE | 7 | 17 | 54 | FOBS= | 92.9 | SIGMA= | 2.2 | PHAS= | 103.8 | FOM= | 0.75 | TEST= 0
| INDE | 7 | 17 | 56 | FOBS= | 170.9 | SIGMA= | 1.3 | PHAS= | -152.3 | FOM= | 0.96 | TEST= 0
| INDE | 7 | 17 | 58 | FOBS= | 47.1 | SIGMA= | 4.2 | PHAS= | 89.4 | FOM= | 0.73 | TEST= 0
| INDE | 7 | 17 | 60 | FOBS= | 64.8 | SIGMA= | 3.0 | PHAS= | 153.1 | FOM= | 0.88 | TEST= 0
| INDE | 7 | 17 | 62 | FOBS= | 157.1 | SIGMA= | 1.6 | PHAS= | -53.8 | FOM= | 0.96 | TEST= 0
| INDE | 7 | 17 | 64 | FOBS= | 123.3 | SIGMA= | 2.3 | PHAS= | -47.1 | FOM= | 0.97 | TEST= 0
| INDE | 7 | 17 | 66 | FOBS= | 34.2 | SIGMA= | 13.0 | PHAS= | 47.4 | FOM= | 0.47 | TEST= 0
| INDE | 7 | 17 | 68 | FOBS= | 80.1 | SIGMA= | 5.5 | PHAS= | 143.8 | FOM= | 0.53 | TEST= 0
| INDE | 7 | 17 | 70 | FOBS= | 0.0 | SIGMA= | 29.6 | PHAS= | 0.0 | FOM= | 0.00 | TEST= 0
| INDE | 7 | 17 | 72 | FOBS= | 34.6 | SIGMA= | 13.3 | PHAS= | 30.6 | FOM= | 0.61 | TEST= 0
| INDE | 7 | 17 | 74 | FOBS= | 65.6 | SIGMA= | 7.4 | PHAS= | 97.6 | FOM= | 0.82 | TEST= 0
| INDE | 7 | 18 | 7 | FOBS= | 311.6 | SIGMA= | 0.4 | PHAS= | -149.3 | FOM= | 0.95 | TEST= 0
| INDE | 7 | 18 | 9 | FOBS= | 106.1 | SIGMA= | 0.6 | PHAS= | 118.0 | FOM= | 0.94 | TEST= 0
| INDE | 7 | 18 | 11 | FOBS= | 232.3 | SIGMA= | 0.5 | PHAS= | 13.3 | FOM= | 0.88 | TEST= 0
| INDE | 7 | 18 | 13 | FOBS= | 111.7 | SIGMA= | 0.7 | PHAS= | -73.2 | FOM= | 0.95 | TEST= 1
| INDE | 7 | 18 | 15 | FOBS= | 100.5 | SIGMA= | 0.9 | PHAS= | -176.1 | FOM= | 0.92 | TEST= 0
| INDE | 7 | 18 | 17 | FOBS= | 75.9 | SIGMA= | 1.0 | PHAS= | 151.8 | FOM= | 0.97 | TEST= 0
| INDE | 7 | 18 | 19 | FOBS= | 81.1 | SIGMA= | 0.9 | PHAS= | -10.4 | FOM= | 0.99 | TEST= 0
| INDE | 7 | 18 | 21 | FOBS= | 92.8 | SIGMA= | 0.8 | PHAS= | 96.6 | FOM= | 0.96 | TEST= 0
| INDE | 7 | 18 | 23 | FOBS= | 112.2 | SIGMA= | 0.7 | PHAS= | 132.4 | FOM= | 0.98 | TEST= 0
| INDE | 7 | 18 | 25 | FOBS= | 72.4 | SIGMA= | 1.1 | PHAS= | -4.1 | FOM= | 0.95 | TEST= 0
| INDE | 7 | 18 | 27 | FOBS= | 98.1 | SIGMA= | 0.8 | PHAS= | -102.7 | FOM= | 0.94 | TEST= 0
| INDE | 7 | 18 | 29 | FOBS= | 301.0 | SIGMA= | 0.4 | PHAS= | -111.8 | FOM= | 0.96 | TEST= 0
| INDE | 7 | 18 | 31 | FOBS= | 84.6 | SIGMA= | 1.0 | PHAS= | -110.0 | FOM= | 0.99 | TEST= 1
| INDE | 7 | 18 | 33 | FOBS= | 209.2 | SIGMA= | 0.6 | PHAS= | -86.0 | FOM= | 0.98 | TEST= 0
| INDE | 7 | 18 | 35 | FOBS= | 260.5 | SIGMA= | 0.5 | PHAS= | 147.8 | FOM= | 0.91 | TEST= 0
| INDE | 7 | 18 | 37 | FOBS= | 360.9 | SIGMA= | 0.6 | PHAS= | 171.2 | FOM= | 0.95 | TEST= 0
| INDE | 7 | 18 | 39 | FOBS= | 128.7 | SIGMA= | 1.2 | PHAS= | 118.0 | FOM= | 0.74 | TEST= 0
| INDE | 7 | 18 | 41 | FOBS= | 227.6 | SIGMA= | 0.8 | PHAS= | -52.0 | FOM= | 0.94 | TEST= 0
| INDE | 7 | 18 | 43 | FOBS= | 165.5 | SIGMA= | 1.1 | PHAS= | 19.1 | FOM= | 0.92 | TEST= 1
| INDE | 7 | 18 | 45 | FOBS= | 200.2 | SIGMA= | 1.2 | PHAS= | -95.5 | FOM= | 0.92 | TEST= 0
| INDE | 7 | 18 | 47 | FOBS= | 173.4 | SIGMA= | 1.3 | PHAS= | -96.1 | FOM= | 0.95 | TEST= 0

*FIG. 12A - 190*

```
INDE    7  18  49 FOBS=    0.0 SIGMA= 13.1 PHAS=    0.0 FOM= 0.00  TEST= 1
INDE    7  18  51 FOBS=  136.9 SIGMA=  1.6 PHAS=   30.8 FOM= 0.95  TEST= 0
INDE    7  18  53 FOBS=  205.8 SIGMA=  1.1 PHAS=   87.6 FOM= 0.97  TEST= 0
INDE    7  18  55 FOBS=  109.4 SIGMA=  1.9 PHAS=   59.2 FOM= 0.93  TEST= 0
INDE    7  18  57 FOBS=   73.7 SIGMA=  2.8 PHAS= -135.5 FOM= 0.83  TEST= 0
INDE    7  18  59 FOBS=  105.0 SIGMA=  2.0 PHAS=   37.5 FOM= 0.87  TEST= 0
INDE    7  18  61 FOBS=   35.9 SIGMA=  5.4 PHAS= -153.9 FOM= 0.49  TEST= 0
INDE    7  18  63 FOBS=  163.1 SIGMA=  1.6 PHAS= -140.7 FOM= 0.96  TEST= 0
INDE    7  18  65 FOBS=  141.4 SIGMA=  3.3 PHAS=  -87.2 FOM= 0.95  TEST= 0
INDE    7  18  67 FOBS=   34.1 SIGMA= 12.9 PHAS=   70.6 FOM= 0.29  TEST= 0
INDE    7  18  69 FOBS=   21.0 SIGMA= 21.2 PHAS= -104.8 FOM= 0.01  TEST= 1
INDE    7  18  71 FOBS=   28.3 SIGMA= 15.6 PHAS=   99.4 FOM= 0.34  TEST= 0
INDE    7  18  73 FOBS=   78.4 SIGMA=  6.0 PHAS=   45.4 FOM= 0.92  TEST= 0
INDE    7  18  75 FOBS=  124.7 SIGMA=  2.9 PHAS=   45.7 FOM= 0.94  TEST= 0
INDE    7  19   8 FOBS=  189.4 SIGMA=  0.5 PHAS=  120.9 FOM= 0.93  TEST= 0
INDE    7  19  10 FOBS=   64.4 SIGMA=  1.0 PHAS=  -32.2 FOM= 0.93  TEST= 0
INDE    7  19  12 FOBS=   52.4 SIGMA=  1.2 PHAS= -160.3 FOM= 0.95  TEST= 0
INDE    7  19  14 FOBS=  117.9 SIGMA=  0.7 PHAS=  152.0 FOM= 0.97  TEST= 0
INDE    7  19  16 FOBS=   16.5 SIGMA=  4.7 PHAS=   37.0 FOM= 0.53  TEST= 0
INDE    7  19  18 FOBS=  118.5 SIGMA=  0.7 PHAS=  -97.7 FOM= 0.99  TEST= 0
INDE    7  19  20 FOBS=   71.0 SIGMA=  1.0 PHAS= -144.2 FOM= 0.85  TEST= 0
INDE    7  19  22 FOBS=  156.0 SIGMA=  0.6 PHAS=  103.0 FOM= 0.97  TEST= 0
INDE    7  19  24 FOBS=  179.0 SIGMA=  0.5 PHAS=  123.7 FOM= 0.95  TEST= 1
INDE    7  19  26 FOBS=   72.5 SIGMA=  1.0 PHAS=   15.3 FOM= 0.98  TEST= 0
INDE    7  19  28 FOBS=  110.4 SIGMA=  0.8 PHAS=   78.0 FOM= 0.84  TEST= 0
INDE    7  19  30 FOBS=  324.4 SIGMA=  0.5 PHAS= -175.8 FOM= 0.99  TEST= 0
INDE    7  19  32 FOBS=  110.8 SIGMA=  0.9 PHAS= -117.4 FOM= 0.98  TEST= 0
INDE    7  19  34 FOBS=  187.8 SIGMA=  0.7 PHAS=   97.1 FOM= 0.88  TEST= 0
INDE    7  19  36 FOBS=  494.6 SIGMA=  0.5 PHAS=  160.1 FOM= 0.97  TEST= 0
INDE    7  19  38 FOBS=  241.9 SIGMA=  0.7 PHAS=  110.7 FOM= 0.93  TEST= 0
INDE    7  19  40 FOBS=   85.6 SIGMA=  1.8 PHAS=  -29.8 FOM= 0.73  TEST= 0
INDE    7  19  42 FOBS=  137.0 SIGMA=  1.3 PHAS=  118.4 FOM= 0.92  TEST= 0
INDE    7  19  44 FOBS=  187.2 SIGMA=  1.0 PHAS=  111.7 FOM= 0.93  TEST= 0
INDE    7  19  46 FOBS=  283.0 SIGMA=  0.8 PHAS= -179.7 FOM= 0.96  TEST= 0
INDE    7  19  48 FOBS=  162.5 SIGMA=  1.4 PHAS= -140.1 FOM= 0.90  TEST= 0
INDE    7  19  50 FOBS=   28.3 SIGMA=  4.0 PHAS=  -48.3 FOM= 0.65  TEST= 0
INDE    7  19  52 FOBS=  188.3 SIGMA=  1.2 PHAS=   43.6 FOM= 0.97  TEST= 0
INDE    7  19  54 FOBS=  109.8 SIGMA=  1.9 PHAS=    6.8 FOM= 0.89  TEST= 0
INDE    7  19  56 FOBS=  165.6 SIGMA=  1.3 PHAS=  178.2 FOM= 0.97  TEST= 0
INDE    7  19  58 FOBS=   78.8 SIGMA=  2.6 PHAS=  157.3 FOM= 0.60  TEST= 0
INDE    7  19  60 FOBS=   70.9 SIGMA=  2.8 PHAS= -170.2 FOM= 0.84  TEST= 0
INDE    7  19  62 FOBS=    0.0 SIGMA= 23.2 PHAS=    0.0 FOM= 0.00  TEST= 0
INDE    7  19  64 FOBS=   39.9 SIGMA=  8.5 PHAS= -140.8 FOM= 0.70  TEST= 0
INDE    7  19  66 FOBS=   82.4 SIGMA=  5.4 PHAS= -155.9 FOM= 0.87  TEST= 0
INDE    7  19  68 FOBS=   66.6 SIGMA=  6.8 PHAS= -125.6 FOM= 0.84  TEST= 0
INDE    7  19  70 FOBS=   49.5 SIGMA=  9.1 PHAS=   53.7 FOM= 0.82  TEST= 0
INDE    7  19  72 FOBS=   70.1 SIGMA=  6.7 PHAS=   -8.1 FOM= 0.88  TEST= 0
INDE    7  19  74 FOBS=  133.1 SIGMA=  3.7 PHAS=   -8.2 FOM= 0.96  TEST= 0
INDE    7  20   7 FOBS=  193.1 SIGMA=  0.5 PHAS=  -28.3 FOM= 0.89  TEST= 0
INDE    7  20   9 FOBS=   63.5 SIGMA=  1.0 PHAS=   68.7 FOM= 0.95  TEST= 0
INDE    7  20  11 FOBS=  231.6 SIGMA=  0.5 PHAS=  -61.5 FOM= 0.53  TEST= 1
INDE    7  20  13 FOBS=   51.7 SIGMA=  1.3 PHAS=  114.7 FOM= 0.89  TEST= 0
INDE    7  20  15 FOBS=  169.7 SIGMA=  0.7 PHAS= -119.7 FOM= 0.94  TEST= 0
INDE    7  20  17 FOBS=   87.2 SIGMA=  0.9 PHAS= -159.6 FOM= 0.96  TEST= 0
INDE    7  20  19 FOBS=   65.5 SIGMA=  1.2 PHAS=  166.1 FOM= 0.98  TEST= 0
INDE    7  20  21 FOBS=  106.9 SIGMA=  0.7 PHAS=   53.2 FOM= 0.98  TEST= 0
INDE    7  20  23 FOBS=  311.5 SIGMA=  0.5 PHAS=   92.1 FOM= 0.98  TEST= 0
INDE    7  20  25 FOBS=   24.6 SIGMA=  3.0 PHAS=   85.2 FOM= 0.89  TEST= 0
INDE    7  20  27 FOBS=  201.5 SIGMA=  0.5 PHAS=  -22.8 FOM= 0.93  TEST= 0
INDE    7  20  29 FOBS=  114.3 SIGMA=  0.8 PHAS=  -86.5 FOM= 0.98  TEST= 0
INDE    7  20  31 FOBS=  177.8 SIGMA=  0.6 PHAS=   19.0 FOM= 0.95  TEST= 0
INDE    7  20  33 FOBS=  126.7 SIGMA=  1.0 PHAS=  -61.3 FOM= 0.83  TEST= 0
INDE    7  20  35 FOBS=  168.7 SIGMA=  0.9 PHAS=  -14.0 FOM= 0.97  TEST= 0
INDE    7  20  37 FOBS=  523.9 SIGMA=  0.6 PHAS=   45.0 FOM= 0.98  TEST= 0
INDE    7  20  39 FOBS=   47.1 SIGMA=  3.2 PHAS=  -87.3 FOM= 0.88  TEST= 1
INDE    7  20  41 FOBS=  403.3 SIGMA=  0.6 PHAS=  -16.5 FOM= 0.99  TEST= 0
INDE    7  20  43 FOBS=  167.4 SIGMA=  1.1 PHAS=  -17.3 FOM= 0.89  TEST= 0
INDE    7  20  45 FOBS=   46.3 SIGMA=  4.6 PHAS=   28.4 FOM= 0.61  TEST= 0
INDE    7  20  47 FOBS=  133.0 SIGMA=  1.5 PHAS= -120.3 FOM= 0.83  TEST= 0
INDE    7  20  49 FOBS=  125.5 SIGMA=  1.3 PHAS= -158.9 FOM= 0.62  TEST= 0
```

*FIG. 12A - 191*

| | | | | | | | | | | | |
|---|---|---|---|---|---|---|---|---|---|---|---|
| INDE | 7 | 20 | 51 | FOBS= | 121.4 | SIGMA= | 1.3 | PHAS= | 24.6 | FOM= | 0.92 | TEST= 0
| INDE | 7 | 20 | 53 | FOBS= | 143.2 | SIGMA= | 1.5 | PHAS= | -64.0 | FOM= | 0.91 | TEST= 0
| INDE | 7 | 20 | 55 | FOBS= | 113.3 | SIGMA= | 1.9 | PHAS= | 89.4 | FOM= | 0.90 | TEST= 0
| INDE | 7 | 20 | 57 | FOBS= | 113.1 | SIGMA= | 1.9 | PHAS= | 121.9 | FOM= | 0.91 | TEST= 0
| INDE | 7 | 20 | 59 | FOBS= | 0.0 | SIGMA= | 19.9 | PHAS= | 0.0 | FOM= | 0.00 | TEST= 0
| INDE | 7 | 20 | 61 | FOBS= | 43.5 | SIGMA= | 4.8 | PHAS= | -170.0 | FOM= | 0.75 | TEST= 0
| INDE | 7 | 20 | 63 | FOBS= | 81.1 | SIGMA= | 2.9 | PHAS= | 165.8 | FOM= | 0.85 | TEST= 0
| INDE | 7 | 20 | 65 | FOBS= | 27.8 | SIGMA= | 16.2 | PHAS= | -105.9 | FOM= | 0.30 | TEST= 0
| INDE | 7 | 20 | 67 | FOBS= | 95.3 | SIGMA= | 4.9 | PHAS= | 151.2 | FOM= | 0.92 | TEST= 0
| INDE | 7 | 20 | 69 | FOBS= | 0.0 | SIGMA= | 29.9 | PHAS= | 0.0 | FOM= | 0.00 | TEST= 1
| INDE | 7 | 20 | 71 | FOBS= | 70.2 | SIGMA= | 6.6 | PHAS= | -93.6 | FOM= | 0.88 | TEST= 0
| INDE | 7 | 20 | 73 | FOBS= | 75.8 | SIGMA= | 6.3 | PHAS= | 52.5 | FOM= | 0.01 | TEST= 1
| INDE | 7 | 21 | 8 | FOBS= | 118.0 | SIGMA= | 0.6 | PHAS= | 176.9 | FOM= | 0.62 | TEST= 1
| INDE | 7 | 21 | 10 | FOBS= | 143.1 | SIGMA= | 0.6 | PHAS= | -164.5 | FOM= | 0.94 | TEST= 0
| INDE | 7 | 21 | 12 | FOBS= | 149.9 | SIGMA= | 0.6 | PHAS= | 130.6 | FOM= | 0.86 | TEST= 0
| INDE | 7 | 21 | 14 | FOBS= | 290.6 | SIGMA= | 0.5 | PHAS= | 34.3 | FOM= | 0.94 | TEST= 0
| INDE | 7 | 21 | 16 | FOBS= | 77.4 | SIGMA= | 1.2 | PHAS= | 133.2 | FOM= | 0.98 | TEST= 0
| INDE | 7 | 21 | 18 | FOBS= | 138.6 | SIGMA= | 0.7 | PHAS= | 174.1 | FOM= | 0.96 | TEST= 0
| INDE | 7 | 21 | 20 | FOBS= | 196.8 | SIGMA= | 0.6 | PHAS= | 130.0 | FOM= | 0.96 | TEST= 0
| INDE | 7 | 21 | 22 | FOBS= | 133.2 | SIGMA= | 0.7 | PHAS= | -36.8 | FOM= | 0.96 | TEST= 0
| INDE | 7 | 21 | 24 | FOBS= | 85.0 | SIGMA= | 1.0 | PHAS= | 106.0 | FOM= | 0.99 | TEST= 0
| INDE | 7 | 21 | 26 | FOBS= | 93.4 | SIGMA= | 0.9 | PHAS= | -44.9 | FOM= | 0.98 | TEST= 1
| INDE | 7 | 21 | 28 | FOBS= | 154.6 | SIGMA= | 0.7 | PHAS= | 11.1 | FOM= | 0.82 | TEST= 1
| INDE | 7 | 21 | 30 | FOBS= | 343.8 | SIGMA= | 0.6 | PHAS= | -118.8 | FOM= | 0.98 | TEST= 0
| INDE | 7 | 21 | 32 | FOBS= | 196.3 | SIGMA= | 0.7 | PHAS= | -85.6 | FOM= | 0.95 | TEST= 0
| INDE | 7 | 21 | 34 | FOBS= | 160.0 | SIGMA= | 0.9 | PHAS= | -50.4 | FOM= | 0.72 | TEST= 0
| INDE | 7 | 21 | 36 | FOBS= | 90.0 | SIGMA= | 1.9 | PHAS= | -113.9 | FOM= | 0.44 | TEST= 1
| INDE | 7 | 21 | 38 | FOBS= | 31.5 | SIGMA= | 5.0 | PHAS= | -10.6 | FOM= | 0.70 | TEST= 0
| INDE | 7 | 21 | 40 | FOBS= | 64.3 | SIGMA= | 2.8 | PHAS= | -134.1 | FOM= | 0.84 | TEST= 0
| INDE | 7 | 21 | 42 | FOBS= | 273.1 | SIGMA= | 0.9 | PHAS= | -159.0 | FOM= | 0.93 | TEST= 1
| INDE | 7 | 21 | 44 | FOBS= | 116.8 | SIGMA= | 1.6 | PHAS= | -158.0 | FOM= | 0.82 | TEST= 0
| INDE | 7 | 21 | 46 | FOBS= | 289.2 | SIGMA= | 0.7 | PHAS= | -155.3 | FOM= | 0.63 | TEST= 1
| INDE | 7 | 21 | 48 | FOBS= | 142.5 | SIGMA= | 1.3 | PHAS= | 155.3 | FOM= | 0.89 | TEST= 0
| INDE | 7 | 21 | 50 | FOBS= | 160.0 | SIGMA= | 1.0 | PHAS= | -82.1 | FOM= | 0.94 | TEST= 0
| INDE | 7 | 21 | 52 | FOBS= | 74.1 | SIGMA= | 1.7 | PHAS= | 163.6 | FOM= | 0.81 | TEST= 0
| INDE | 7 | 21 | 54 | FOBS= | 60.6 | SIGMA= | 2.6 | PHAS= | -170.7 | FOM= | 0.82 | TEST= 0
| INDE | 7 | 21 | 56 | FOBS= | 65.6 | SIGMA= | 3.1 | PHAS= | 129.4 | FOM= | 0.20 | TEST= 1
| INDE | 7 | 21 | 58 | FOBS= | 68.6 | SIGMA= | 3.0 | PHAS= | 35.1 | FOM= | 0.59 | TEST= 0
| INDE | 7 | 21 | 60 | FOBS= | 96.7 | SIGMA= | 2.1 | PHAS= | 119.8 | FOM= | 0.90 | TEST= 0
| INDE | 7 | 21 | 62 | FOBS= | 103.8 | SIGMA= | 2.3 | PHAS= | 117.2 | FOM= | 0.91 | TEST= 0
| INDE | 7 | 21 | 64 | FOBS= | 47.9 | SIGMA= | 9.5 | PHAS= | 39.6 | FOM= | 0.10 | TEST= 1
| INDE | 7 | 21 | 66 | FOBS= | 45.9 | SIGMA= | 10.0 | PHAS= | 162.7 | FOM= | 0.15 | TEST= 1
| INDE | 7 | 21 | 68 | FOBS= | 54.8 | SIGMA= | 8.3 | PHAS= | 66.4 | FOM= | 0.30 | TEST= 0
| INDE | 7 | 21 | 70 | FOBS= | 49.1 | SIGMA= | 9.4 | PHAS= | -161.9 | FOM= | 0.59 | TEST= 0
| INDE | 7 | 21 | 72 | FOBS= | 1.6 | SIGMA= | 297.0 | PHAS= | 135.3 | FOM= | 0.06 | TEST= 0
| INDE | 7 | 21 | 74 | FOBS= | 71.4 | SIGMA= | 6.9 | PHAS= | 36.5 | FOM= | 0.70 | TEST= 0
| INDE | 7 | 22 | 7 | FOBS= | 180.1 | SIGMA= | 0.5 | PHAS= | 83.4 | FOM= | 0.93 | TEST= 0
| INDE | 7 | 22 | 9 | FOBS= | 221.9 | SIGMA= | 0.5 | PHAS= | 76.8 | FOM= | 0.97 | TEST= 0
| INDE | 7 | 22 | 11 | FOBS= | 227.3 | SIGMA= | 0.5 | PHAS= | 121.8 | FOM= | 0.98 | TEST= 0
| INDE | 7 | 22 | 13 | FOBS= | 110.9 | SIGMA= | 0.7 | PHAS= | -1.5 | FOM= | 0.86 | TEST= 0
| INDE | 7 | 22 | 15 | FOBS= | 275.8 | SIGMA= | 0.6 | PHAS= | -43.2 | FOM= | 0.96 | TEST= 0
| INDE | 7 | 22 | 17 | FOBS= | 106.9 | SIGMA= | 0.9 | PHAS= | 124.1 | FOM= | 0.96 | TEST= 0
| INDE | 7 | 22 | 19 | FOBS= | 295.4 | SIGMA= | 0.5 | PHAS= | 105.3 | FOM= | 0.99 | TEST= 0
| INDE | 7 | 22 | 21 | FOBS= | 112.2 | SIGMA= | 0.8 | PHAS= | -0.1 | FOM= | 0.76 | TEST= 0
| INDE | 7 | 22 | 23 | FOBS= | 324.5 | SIGMA= | 0.7 | PHAS= | 69.0 | FOM= | 0.98 | TEST= 0
| INDE | 7 | 22 | 25 | FOBS= | 126.6 | SIGMA= | 0.9 | PHAS= | 153.1 | FOM= | 0.76 | TEST= 1
| INDE | 7 | 22 | 27 | FOBS= | 259.3 | SIGMA= | 0.7 | PHAS= | -113.2 | FOM= | 0.92 | TEST= 1
| INDE | 7 | 22 | 29 | FOBS= | 259.6 | SIGMA= | 0.5 | PHAS= | 143.8 | FOM= | 0.95 | TEST= 0
| INDE | 7 | 22 | 31 | FOBS= | 245.7 | SIGMA= | 0.6 | PHAS= | 131.7 | FOM= | 0.99 | TEST= 0
| INDE | 7 | 22 | 33 | FOBS= | 309.6 | SIGMA= | 0.6 | PHAS= | -135.5 | FOM= | 0.97 | TEST= 0
| INDE | 7 | 22 | 35 | FOBS= | 253.5 | SIGMA= | 0.7 | PHAS= | -95.8 | FOM= | 0.97 | TEST= 0
| INDE | 7 | 22 | 37 | FOBS= | 293.0 | SIGMA= | 0.6 | PHAS= | -12.2 | FOM= | 0.97 | TEST= 0
| INDE | 7 | 22 | 39 | FOBS= | 159.2 | SIGMA= | 1.1 | PHAS= | 112.3 | FOM= | 0.97 | TEST= 0
| INDE | 7 | 22 | 41 | FOBS= | 160.6 | SIGMA= | 1.2 | PHAS= | -5.6 | FOM= | 0.89 | TEST= 0
| INDE | 7 | 22 | 43 | FOBS= | 81.0 | SIGMA= | 2.4 | PHAS= | 167.3 | FOM= | 0.88 | TEST= 0
| INDE | 7 | 22 | 45 | FOBS= | 288.7 | SIGMA= | 0.9 | PHAS= | 50.2 | FOM= | 0.96 | TEST= 0
| INDE | 7 | 22 | 47 | FOBS= | 172.6 | SIGMA= | 1.1 | PHAS= | 72.9 | FOM= | 0.89 | TEST= 0
| INDE | 7 | 22 | 49 | FOBS= | 234.1 | SIGMA= | 0.9 | PHAS= | 149.0 | FOM= | 0.96 | TEST= 0
| INDE | 7 | 22 | 51 | FOBS= | 181.2 | SIGMA= | 0.8 | PHAS= | 59.9 | FOM= | 0.95 | TEST= 0
| INDE | 7 | 22 | 53 | FOBS= | 38.9 | SIGMA= | 3.3 | PHAS= | 17.7 | FOM= | 0.72 | TEST= 0

*FIG. 12A - 192*

```
INDE  7  22  55  FOBS=   77.6  SIGMA=   2.7  PHAS=  114.8  FOM=  0.92  TEST= 0
INDE  7  22  57  FOBS=   76.1  SIGMA=   2.7  PHAS=   84.6  FOM=  0.89  TEST= 0
INDE  7  22  59  FOBS=   80.8  SIGMA=   2.6  PHAS=   30.8  FOM=  0.90  TEST= 0
INDE  7  22  61  FOBS=   66.8  SIGMA=   3.6  PHAS=   42.5  FOM=  0.84  TEST= 0
INDE  7  22  63  FOBS=    0.0  SIGMA=  23.0  PHAS=    0.0  FOM=  0.00  TEST= 0
INDE  7  22  65  FOBS=   41.2  SIGMA=  11.1  PHAS=   25.1  FOM=  0.37  TEST= 0
INDE  7  22  67  FOBS=   79.4  SIGMA=   5.9  PHAS=   59.8  FOM=  0.81  TEST= 0
INDE  7  22  69  FOBS=   92.7  SIGMA=   5.1  PHAS= -169.3  FOM=  0.72  TEST= 0
INDE  7  22  71  FOBS=    0.0  SIGMA=  30.4  PHAS=    0.0  FOM=  0.00  TEST= 0
INDE  7  22  73  FOBS=   63.2  SIGMA=   7.7  PHAS=   35.6  FOM=  0.87  TEST= 0
INDE  7  23   8  FOBS=  331.7  SIGMA=   0.5  PHAS=  -24.3  FOM=  0.98  TEST= 0
INDE  7  23  10  FOBS=  395.2  SIGMA=   0.7  PHAS=   46.1  FOM=  0.97  TEST= 0
INDE  7  23  12  FOBS=  236.9  SIGMA=   0.5  PHAS=   69.4  FOM=  0.96  TEST= 0
INDE  7  23  14  FOBS=   55.1  SIGMA=   1.4  PHAS= -131.7  FOM=  0.99  TEST= 0
INDE  7  23  16  FOBS=  129.5  SIGMA=   1.0  PHAS=  -91.7  FOM=  0.95  TEST= 0
INDE  7  23  18  FOBS=  240.0  SIGMA=   0.8  PHAS=   33.2  FOM=  0.99  TEST= 0
INDE  7  23  20  FOBS=   92.8  SIGMA=   1.1  PHAS=  137.6  FOM=  0.83  TEST= 0
INDE  7  23  22  FOBS=  355.1  SIGMA=   0.5  PHAS=  -81.2  FOM=  0.97  TEST= 0
INDE  7  23  24  FOBS=  112.1  SIGMA=   1.0  PHAS=   50.2  FOM=  0.57  TEST= 0
INDE  7  23  26  FOBS=  210.1  SIGMA=   0.7  PHAS=   75.1  FOM=  0.95  TEST= 0
INDE  7  23  28  FOBS=  255.7  SIGMA=   0.6  PHAS=   49.8  FOM=  0.94  TEST= 0
INDE  7  23  30  FOBS=  221.9  SIGMA=   0.7  PHAS=  -11.1  FOM=  0.93  TEST= 0
INDE  7  23  32  FOBS=  122.9  SIGMA=   1.0  PHAS=   84.0  FOM=  0.97  TEST= 1
INDE  7  23  34  FOBS=  371.7  SIGMA=   0.6  PHAS=  162.5  FOM=  0.97  TEST= 0
INDE  7  23  36  FOBS=  178.2  SIGMA=   0.9  PHAS=  147.2  FOM=  0.96  TEST= 0
INDE  7  23  38  FOBS=   79.9  SIGMA=   2.0  PHAS=  -35.8  FOM=  0.81  TEST= 0
INDE  7  23  40  FOBS=   66.7  SIGMA=   2.7  PHAS=  -51.4  FOM=  0.90  TEST= 0
INDE  7  23  42  FOBS=  117.6  SIGMA=   1.6  PHAS=  129.8  FOM=  0.90  TEST= 0
INDE  7  23  44  FOBS=   49.7  SIGMA=   3.7  PHAS= -156.7  FOM=  0.89  TEST= 0
INDE  7  23  46  FOBS=  135.7  SIGMA=   1.4  PHAS=  -60.3  FOM=  0.92  TEST= 0
INDE  7  23  48  FOBS=  308.7  SIGMA=   0.7  PHAS=  -21.9  FOM=  0.98  TEST= 0
INDE  7  23  50  FOBS=   56.8  SIGMA=   2.7  PHAS=  -71.4  FOM=  0.26  TEST= 1
INDE  7  23  52  FOBS=   39.5  SIGMA=   3.5  PHAS=   -5.2  FOM=  0.55  TEST= 0
INDE  7  23  54  FOBS=   83.3  SIGMA=   1.9  PHAS=   97.9  FOM=  0.84  TEST= 0
INDE  7  23  56  FOBS=  102.2  SIGMA=   1.6  PHAS=   96.2  FOM=  0.89  TEST= 0
INDE  7  23  58  FOBS=  139.5  SIGMA=   1.6  PHAS=  -26.1  FOM=  0.93  TEST= 0
INDE  7  23  60  FOBS=    0.0  SIGMA=  20.7  PHAS=    0.0  FOM=  0.00  TEST= 0
INDE  7  23  62  FOBS=   69.9  SIGMA=   3.4  PHAS=    1.0  FOM=  0.54  TEST= 0
INDE  7  23  64  FOBS=   43.7  SIGMA=  10.5  PHAS=   17.9  FOM=  0.49  TEST= 0
INDE  7  23  66  FOBS=    9.0  SIGMA=  50.2  PHAS=  -98.0  FOM=  0.15  TEST= 0
INDE  7  23  70  FOBS=   45.6  SIGMA=  10.3  PHAS= -122.9  FOM=  0.06  TEST= 1
INDE  7  23  72  FOBS=   22.8  SIGMA=  21.1  PHAS=  -41.7  FOM=  0.52  TEST= 0
INDE  7  24   7  FOBS=  175.5  SIGMA=   0.6  PHAS=  150.7  FOM=  0.49  TEST= 0
INDE  7  24   9  FOBS=  366.0  SIGMA=   0.6  PHAS=  -58.6  FOM=  0.98  TEST= 0
INDE  7  24  11  FOBS=  169.5  SIGMA=   0.6  PHAS=  -65.7  FOM=  0.82  TEST= 0
INDE  7  24  13  FOBS=  176.0  SIGMA=   0.6  PHAS=  -41.6  FOM=  0.99  TEST= 1
INDE  7  24  15  FOBS=   60.5  SIGMA=   1.5  PHAS=  -67.5  FOM=  0.87  TEST= 0
INDE  7  24  17  FOBS=  233.8  SIGMA=   0.8  PHAS= -117.4  FOM=  0.98  TEST= 0
INDE  7  24  19  FOBS=  262.7  SIGMA=   0.7  PHAS=   30.0  FOM=  0.95  TEST= 0
INDE  7  24  21  FOBS=  206.6  SIGMA=   0.7  PHAS=  111.3  FOM=  0.98  TEST= 0
INDE  7  24  23  FOBS=  123.8  SIGMA=   0.9  PHAS=  166.4  FOM=  0.85  TEST= 0
INDE  7  24  25  FOBS=   92.0  SIGMA=   1.2  PHAS=   -0.9  FOM=  0.74  TEST= 0
INDE  7  24  27  FOBS=  117.2  SIGMA=   1.1  PHAS=  -43.0  FOM=  0.96  TEST= 0
INDE  7  24  29  FOBS=  211.4  SIGMA=   0.7  PHAS=  -46.7  FOM=  0.94  TEST= 0
INDE  7  24  31  FOBS=  274.0  SIGMA=   0.6  PHAS=  -50.5  FOM=  0.45  TEST= 1
INDE  7  24  33  FOBS=  123.6  SIGMA=   1.1  PHAS=   33.0  FOM=  0.78  TEST= 0
INDE  7  24  35  FOBS=  142.2  SIGMA=   1.2  PHAS=    7.2  FOM=  0.91  TEST= 0
INDE  7  24  37  FOBS=  124.3  SIGMA=   1.3  PHAS=  -38.3  FOM=  0.93  TEST= 0
INDE  7  24  39  FOBS=  235.4  SIGMA=   0.8  PHAS=  101.2  FOM=  0.95  TEST= 0
INDE  7  24  41  FOBS=  102.7  SIGMA=   1.8  PHAS=  -89.0  FOM=  0.72  TEST= 0
INDE  7  24  43  FOBS=  108.4  SIGMA=   1.8  PHAS=  -31.9  FOM=  0.94  TEST= 0
INDE  7  24  45  FOBS=   73.4  SIGMA=   2.5  PHAS=   73.4  FOM=  0.66  TEST= 0
INDE  7  24  47  FOBS=  237.3  SIGMA=   0.9  PHAS= -121.5  FOM=  0.98  TEST= 0
INDE  7  24  49  FOBS=  137.1  SIGMA=   1.3  PHAS= -137.8  FOM=  0.89  TEST= 0
INDE  7  24  51  FOBS=   99.8  SIGMA=   1.3  PHAS=   24.9  FOM=  0.88  TEST= 0
INDE  7  24  53  FOBS=  105.5  SIGMA=   1.3  PHAS=  -25.0  FOM=  0.89  TEST= 0
INDE  7  24  55  FOBS=  131.8  SIGMA=   1.0  PHAS=  -23.6  FOM=  0.93  TEST= 0
INDE  7  24  57  FOBS=   87.3  SIGMA=   2.4  PHAS=   36.5  FOM=  0.93  TEST= 0
INDE  7  24  59  FOBS=   26.9  SIGMA=   7.4  PHAS=   88.9  FOM=  0.32  TEST= 0
INDE  7  24  61  FOBS=   48.1  SIGMA=   5.0  PHAS=  137.7  FOM=  0.60  TEST= 0
```

*FIG. 12A - 193*

```
INDE   7   24   63  FOBS=    40.1  SIGMA=   7.9  PHAS=   -91.8  FOM=  0.64  TEST= 0
INDE   7   24   65  FOBS=    73.8  SIGMA=   6.3  PHAS=  -155.2  FOM=  0.55  TEST= 1
INDE   7   24   67  FOBS=    71.5  SIGMA=   6.5  PHAS=    69.5  FOM=  0.88  TEST= 0
INDE   7   24   69  FOBS=    57.2  SIGMA=   8.3  PHAS=   -40.8  FOM=  0.79  TEST= 0
INDE   7   24   71  FOBS=    33.8  SIGMA=  14.0  PHAS=   162.0  FOM=  0.36  TEST= 0
INDE   7   24   73  FOBS=    45.0  SIGMA=  11.0  PHAS=  -116.9  FOM=  0.23  TEST= 0
INDE   7   25    8  FOBS=   134.9  SIGMA=   0.6  PHAS=   -76.6  FOM=  0.89  TEST= 0
INDE   7   25   10  FOBS=   101.6  SIGMA=   0.9  PHAS=    53.6  FOM=  0.95  TEST= 0
INDE   7   25   12  FOBS=    74.0  SIGMA=   1.2  PHAS=    -8.1  FOM=  0.93  TEST= 0
INDE   7   25   14  FOBS=   163.5  SIGMA=   0.7  PHAS=  -114.6  FOM=  0.92  TEST= 0
INDE   7   25   16  FOBS=    98.0  SIGMA=   1.4  PHAS=    26.3  FOM=  0.96  TEST= 0
INDE   7   25   18  FOBS=   166.8  SIGMA=   0.9  PHAS=    -0.6  FOM=  0.95  TEST= 0
INDE   7   25   20  FOBS=   107.7  SIGMA=   1.2  PHAS=   -31.2  FOM=  0.88  TEST= 0
INDE   7   25   22  FOBS=   193.9  SIGMA=   0.7  PHAS=   -68.1  FOM=  0.99  TEST= 0
INDE   7   25   24  FOBS=   161.9  SIGMA=   0.8  PHAS=    95.6  FOM=  0.94  TEST= 0
INDE   7   25   26  FOBS=   151.9  SIGMA=   0.9  PHAS=   -57.8  FOM=  0.96  TEST= 0
INDE   7   25   28  FOBS=   206.6  SIGMA=   0.7  PHAS=   -28.5  FOM=  0.99  TEST= 0
INDE   7   25   30  FOBS=   163.9  SIGMA=   0.8  PHAS=  -145.7  FOM=  0.96  TEST= 1
INDE   7   25   32  FOBS=   334.0  SIGMA=   0.7  PHAS=  -174.5  FOM=  0.97  TEST= 0
INDE   7   25   34  FOBS=   163.9  SIGMA=   0.9  PHAS=   131.1  FOM=  0.81  TEST= 0
INDE   7   25   36  FOBS=    46.5  SIGMA=   3.6  PHAS=  -120.3  FOM=  0.38  TEST= 0
INDE   7   25   38  FOBS=   166.0  SIGMA=   1.1  PHAS=     6.5  FOM=  0.95  TEST= 0
INDE   7   25   40  FOBS=   169.6  SIGMA=   1.2  PHAS=    76.0  FOM=  0.90  TEST= 0
INDE   7   25   42  FOBS=   246.8  SIGMA=   0.9  PHAS=   117.0  FOM=  0.99  TEST= 0
INDE   7   25   44  FOBS=    19.4  SIGMA=   9.3  PHAS=    99.7  FOM=  0.11  TEST= 0
INDE   7   25   46  FOBS=   120.6  SIGMA=   1.5  PHAS=   143.1  FOM=  0.89  TEST= 0
INDE   7   25   48  FOBS=     0.0  SIGMA=  19.2  PHAS=     0.0  FOM=  0.00  TEST= 0
INDE   7   25   50  FOBS=    77.3  SIGMA=   2.3  PHAS=  -154.1  FOM=  0.81  TEST= 0
INDE   7   25   52  FOBS=   185.1  SIGMA=   0.9  PHAS=  -134.0  FOM=  0.96  TEST= 0
INDE   7   25   54  FOBS=    72.2  SIGMA=   1.8  PHAS=  -117.4  FOM=  0.79  TEST= 0
INDE   7   25   56  FOBS=    55.7  SIGMA=   2.9  PHAS=  -131.0  FOM=  0.86  TEST= 0
INDE   7   25   58  FOBS=   173.8  SIGMA=   1.4  PHAS=   -33.2  FOM=  0.96  TEST= 0
INDE   7   25   60  FOBS=    89.3  SIGMA=   2.8  PHAS=    64.3  FOM=  0.87  TEST= 0
INDE   7   25   62  FOBS=   155.9  SIGMA=   1.9  PHAS=    86.0  FOM=  0.95  TEST= 0
INDE   7   25   64  FOBS=    90.7  SIGMA=   3.6  PHAS=  -171.1  FOM=  0.40  TEST= 1
INDE   7   25   66  FOBS=     0.0  SIGMA=  30.3  PHAS=     0.0  FOM=  0.00  TEST= 0
INDE   7   25   68  FOBS=     0.0  SIGMA=  30.6  PHAS=     0.0  FOM=  0.00  TEST= 0
INDE   7   25   70  FOBS=    40.3  SIGMA=  12.1  PHAS=   168.9  FOM=  0.47  TEST= 0
INDE   7   25   72  FOBS=    68.7  SIGMA=   7.3  PHAS=   175.7  FOM=  0.53  TEST= 0
INDE   7   26    7  FOBS=    52.0  SIGMA=   1.4  PHAS=  -105.4  FOM=  0.96  TEST= 0
INDE   7   26    9  FOBS=   257.4  SIGMA=   0.6  PHAS=   -38.2  FOM=  0.98  TEST= 0
INDE   7   26   11  FOBS=   221.8  SIGMA=   0.6  PHAS=   -49.1  FOM=  0.96  TEST= 0
INDE   7   26   13  FOBS=   286.8  SIGMA=   0.5  PHAS=   -82.9  FOM=  0.96  TEST= 0
INDE   7   26   15  FOBS=   110.7  SIGMA=   0.9  PHAS=  -109.8  FOM=  0.99  TEST= 0
INDE   7   26   17  FOBS=   242.6  SIGMA=   0.8  PHAS=   -83.6  FOM=  0.93  TEST= 0
INDE   7   26   19  FOBS=   207.9  SIGMA=   0.8  PHAS=   -24.9  FOM=  0.92  TEST= 0
INDE   7   26   21  FOBS=   237.6  SIGMA=   0.8  PHAS=   174.2  FOM=  0.96  TEST= 0
INDE   7   26   23  FOBS=   239.3  SIGMA=   0.7  PHAS=   -41.1  FOM=  0.94  TEST= 1
INDE   7   26   25  FOBS=    71.6  SIGMA=   1.7  PHAS=  -119.5  FOM=  0.97  TEST= 0
INDE   7   26   27  FOBS=   282.0  SIGMA=   0.6  PHAS=  -131.2  FOM=  0.97  TEST= 0
INDE   7   26   29  FOBS=   247.4  SIGMA=   0.6  PHAS=   -36.9  FOM=  0.95  TEST= 0
INDE   7   26   31  FOBS=   237.9  SIGMA=   0.8  PHAS=   122.4  FOM=  0.91  TEST= 1
INDE   7   26   33  FOBS=   222.9  SIGMA=   0.9  PHAS=    35.4  FOM=  0.88  TEST= 1
INDE   7   26   35  FOBS=    99.0  SIGMA=   1.4  PHAS=    -0.6  FOM=  0.95  TEST= 0
INDE   7   26   37  FOBS=    98.4  SIGMA=   1.7  PHAS=  -119.4  FOM=  0.98  TEST= 0
INDE   7   26   39  FOBS=   246.7  SIGMA=   0.9  PHAS=   -14.7  FOM=  0.94  TEST= 0
INDE   7   26   41  FOBS=   238.0  SIGMA=   1.0  PHAS=     8.2  FOM=  0.96  TEST= 0
INDE   7   26   43  FOBS=   132.9  SIGMA=   1.4  PHAS=    -3.1  FOM=  0.92  TEST= 0
INDE   7   26   45  FOBS=    66.0  SIGMA=   2.7  PHAS=   159.9  FOM=  0.52  TEST= 0
INDE   7   26   47  FOBS=    69.2  SIGMA=   2.6  PHAS=   -71.5  FOM=  0.67  TEST= 0
INDE   7   26   49  FOBS=    51.5  SIGMA=   3.4  PHAS=    70.0  FOM=  0.57  TEST= 0
INDE   7   26   51  FOBS=    58.1  SIGMA=   2.3  PHAS=  -147.5  FOM=  0.88  TEST= 0
INDE   7   26   53  FOBS=     0.0  SIGMA=  16.3  PHAS=     0.0  FOM=  0.00  TEST= 0
INDE   7   26   55  FOBS=     0.0  SIGMA=  15.9  PHAS=     0.0  FOM=  0.00  TEST= 0
INDE   7   26   57  FOBS=   101.2  SIGMA=   1.5  PHAS=  -156.9  FOM=  0.86  TEST= 0
INDE   7   26   59  FOBS=    22.4  SIGMA=   8.3  PHAS=  -137.0  FOM=  0.05  TEST= 0
INDE   7   26   61  FOBS=    89.5  SIGMA=   3.2  PHAS=   -10.4  FOM=  0.92  TEST= 0
INDE   7   26   63  FOBS=    48.0  SIGMA=   6.6  PHAS=   -51.4  FOM=  0.46  TEST= 0
INDE   7   26   65  FOBS=    44.0  SIGMA=  10.5  PHAS=    88.4  FOM=  0.47  TEST= 0
INDE   7   26   67  FOBS=     0.0  SIGMA=  30.8  PHAS=     0.0  FOM=  0.00  TEST= 1
```

*FIG. 12A - 194*

```
INDE  7  26  69  FOBS=   58.1  SIGMA=   8.2  PHAS=   34.6  FOM=  0.42  TEST= 0
INDE  7  26  71  FOBS=   47.6  SIGMA=  10.4  PHAS=  130.1  FOM=  0.69  TEST= 0
INDE  7  27   8  FOBS=  222.4  SIGMA=   0.5  PHAS=  -49.2  FOM=  0.98  TEST= 0
INDE  7  27  10  FOBS=  181.3  SIGMA=   0.6  PHAS= -113.4  FOM=  0.98  TEST= 1
INDE  7  27  12  FOBS=  162.3  SIGMA=   0.8  PHAS=  152.6  FOM=  0.93  TEST= 0
INDE  7  27  14  FOBS=  186.7  SIGMA=   0.7  PHAS=  166.8  FOM=  0.99  TEST= 0
INDE  7  27  16  FOBS=  181.2  SIGMA=   0.7  PHAS=   88.4  FOM=  0.98  TEST= 0
INDE  7  27  18  FOBS=  157.1  SIGMA=   1.0  PHAS=   11.7  FOM=  0.97  TEST= 0
INDE  7  27  20  FOBS=  114.2  SIGMA=   1.2  PHAS=    9.6  FOM=  0.77  TEST= 0
INDE  7  27  22  FOBS=  144.2  SIGMA=   1.0  PHAS=  145.5  FOM=  0.99  TEST= 0
INDE  7  27  24  FOBS=  185.6  SIGMA=   0.8  PHAS=   68.8  FOM=  0.96  TEST= 0
INDE  7  27  26  FOBS=  109.4  SIGMA=   1.2  PHAS= -127.6  FOM=  0.93  TEST= 0
INDE  7  27  28  FOBS=  173.1  SIGMA=   0.8  PHAS=  143.2  FOM=  0.98  TEST= 0
INDE  7  27  30  FOBS=  223.1  SIGMA=   0.7  PHAS=   90.0  FOM=  0.80  TEST= 0
INDE  7  27  32  FOBS=   75.7  SIGMA=   1.9  PHAS= -137.8  FOM=  0.94  TEST= 0
INDE  7  27  34  FOBS=   90.0  SIGMA=   1.8  PHAS=  -13.7  FOM=  0.96  TEST= 0
INDE  7  27  36  FOBS=   58.0  SIGMA=   2.9  PHAS= -178.7  FOM=  0.99  TEST= 0
INDE  7  27  38  FOBS=   94.4  SIGMA=   1.7  PHAS= -165.3  FOM=  0.90  TEST= 0
INDE  7  27  40  FOBS=   61.4  SIGMA=   3.4  PHAS=  -84.1  FOM=  0.66  TEST= 0
INDE  7  27  42  FOBS=   40.9  SIGMA=   4.8  PHAS= -127.5  FOM=  0.41  TEST= 0
INDE  7  27  44  FOBS=  130.6  SIGMA=   1.4  PHAS=   52.0  FOM=  0.93  TEST= 0
INDE  7  27  46  FOBS=  173.5  SIGMA=   1.1  PHAS= -171.1  FOM=  0.95  TEST= 0
INDE  7  27  48  FOBS=  117.7  SIGMA=   1.5  PHAS=  -72.8  FOM=  0.93  TEST= 0
INDE  7  27  50  FOBS=   41.2  SIGMA=   4.2  PHAS=  138.4  FOM=  0.61  TEST= 0
INDE  7  27  52  FOBS=  170.1  SIGMA=   0.9  PHAS= -133.6  FOM=  0.95  TEST= 0
INDE  7  27  54  FOBS=   20.7  SIGMA=   8.5  PHAS= -145.0  FOM=  0.32  TEST= 0
INDE  7  27  56  FOBS=   74.3  SIGMA=   2.0  PHAS= -167.7  FOM=  0.74  TEST= 0
INDE  7  27  58  FOBS=   87.3  SIGMA=   1.9  PHAS= -121.9  FOM=  0.85  TEST= 0
INDE  7  27  60  FOBS=   40.4  SIGMA=   5.2  PHAS= -128.8  FOM=  0.11  TEST= 0
INDE  7  27  62  FOBS=   33.8  SIGMA=   9.6  PHAS=   65.5  FOM=  0.35  TEST= 0
INDE  7  27  64  FOBS=    0.0  SIGMA=  25.2  PHAS=    0.0  FOM=  0.00  TEST= 0
INDE  7  27  66  FOBS=    0.0  SIGMA=  30.7  PHAS=    0.0  FOM=  0.00  TEST= 0
INDE  7  27  68  FOBS=   23.3  SIGMA=  20.3  PHAS= -174.7  FOM=  0.32  TEST= 0
INDE  7  27  70  FOBS=   58.4  SIGMA=   8.5  PHAS=    5.6  FOM=  0.94  TEST= 0
INDE  7  27  72  FOBS=   59.4  SIGMA=   8.7  PHAS=  -50.0  FOM=  0.56  TEST= 0
INDE  7  28   7  FOBS=  108.8  SIGMA=   0.7  PHAS= -135.6  FOM=  0.99  TEST= 0
INDE  7  28   9  FOBS=  143.0  SIGMA=   0.7  PHAS= -109.9  FOM=  0.97  TEST= 0
INDE  7  28  11  FOBS=  197.4  SIGMA=   0.7  PHAS=   40.2  FOM=  0.96  TEST= 0
INDE  7  28  13  FOBS=  104.1  SIGMA=   1.0  PHAS=    6.8  FOM=  0.98  TEST= 0
INDE  7  28  15  FOBS=  207.8  SIGMA=   0.6  PHAS=   44.1  FOM=  0.98  TEST= 0
INDE  7  28  17  FOBS=  146.4  SIGMA=   0.9  PHAS=   -6.7  FOM=  0.87  TEST= 1
INDE  7  28  19  FOBS=   69.5  SIGMA=   2.0  PHAS=  161.7  FOM=  0.75  TEST= 0
INDE  7  28  21  FOBS=  232.4  SIGMA=   0.8  PHAS=  101.6  FOM=  0.96  TEST= 0
INDE  7  28  23  FOBS=  258.3  SIGMA=   0.7  PHAS=  -73.6  FOM=  0.84  TEST= 0
INDE  7  28  25  FOBS=  135.7  SIGMA=   1.1  PHAS=  119.7  FOM=  0.86  TEST= 0
INDE  7  28  27  FOBS=  138.1  SIGMA=   1.0  PHAS=  154.4  FOM=  0.98  TEST= 0
INDE  7  28  29  FOBS=  108.9  SIGMA=   1.3  PHAS=   11.9  FOM=  0.88  TEST= 0
INDE  7  28  31  FOBS=  404.7  SIGMA=   0.7  PHAS=  -31.5  FOM=  0.81  TEST= 1
INDE  7  28  33  FOBS=  176.5  SIGMA=   1.0  PHAS=  -41.1  FOM=  0.92  TEST= 0
INDE  7  28  35  FOBS=  225.4  SIGMA=   1.1  PHAS=   83.4  FOM=  0.97  TEST= 0
INDE  7  28  37  FOBS=  176.1  SIGMA=   1.1  PHAS=  112.0  FOM=  0.97  TEST= 0
INDE  7  28  39  FOBS=  115.0  SIGMA=   1.5  PHAS=  -53.0  FOM=  0.75  TEST= 0
INDE  7  28  41  FOBS=  299.7  SIGMA=   0.8  PHAS=  -46.6  FOM=  0.96  TEST= 0
INDE  7  28  43  FOBS=  123.1  SIGMA=   1.7  PHAS=  -76.4  FOM=  0.98  TEST= 0
INDE  7  28  45  FOBS=   98.3  SIGMA=   1.9  PHAS=   10.2  FOM=  0.77  TEST= 0
INDE  7  28  47  FOBS=   43.2  SIGMA=   4.0  PHAS=  -46.0  FOM=  0.37  TEST= 0
INDE  7  28  49  FOBS=   19.5  SIGMA=  10.5  PHAS=   52.1  FOM=  0.08  TEST= 1
INDE  7  28  51  FOBS=   82.2  SIGMA=   1.9  PHAS= -110.4  FOM=  0.46  TEST= 0
INDE  7  28  53  FOBS=   45.2  SIGMA=   2.9  PHAS= -160.6  FOM=  0.65  TEST= 0
INDE  7  28  55  FOBS=  109.5  SIGMA=   1.4  PHAS=  106.1  FOM=  0.84  TEST= 0
INDE  7  28  57  FOBS=    0.0  SIGMA=  17.7  PHAS=    0.0  FOM=  0.00  TEST= 0
INDE  7  28  59  FOBS=   92.0  SIGMA=   1.9  PHAS=  138.4  FOM=  0.87  TEST= 0
INDE  7  28  61  FOBS=   80.0  SIGMA=   2.9  PHAS= -176.2  FOM=  0.92  TEST= 0
INDE  7  28  63  FOBS=   47.4  SIGMA=   6.9  PHAS= -153.7  FOM=  0.70  TEST= 0
INDE  7  28  65  FOBS=   22.5  SIGMA=  21.0  PHAS=  -36.0  FOM=  0.18  TEST= 0
INDE  7  28  67  FOBS=    0.0  SIGMA=  31.1  PHAS=    0.0  FOM=  0.00  TEST= 1
INDE  7  28  69  FOBS=    0.0  SIGMA=  31.2  PHAS=    0.0  FOM=  0.00  TEST= 0
INDE  7  28  71  FOBS=  118.8  SIGMA=   4.3  PHAS= -106.9  FOM=  0.97  TEST= 0
INDE  7  29   8  FOBS=   26.4  SIGMA=   3.0  PHAS=  152.1  FOM=  0.92  TEST= 0
INDE  7  29  10  FOBS=  115.2  SIGMA=   0.9  PHAS=  -52.5  FOM=  0.85  TEST= 0
```

*FIG. 12A - 195*

```
INDE  7 29 12 FOBS=   343.2 SIGMA=  0.8 PHAS=   -8.3 FOM= 0.99 TEST= 0
INDE  7 29 14 FOBS=   200.3 SIGMA=  0.7 PHAS=  -26.9 FOM= 0.87 TEST= 0
INDE  7 29 16 FOBS=   155.9 SIGMA=  0.8 PHAS=  -47.8 FOM= 0.93 TEST= 1
INDE  7 29 18 FOBS=   266.8 SIGMA=  0.8 PHAS=   20.1 FOM= 0.95 TEST= 0
INDE  7 29 20 FOBS=    66.5 SIGMA=  2.2 PHAS=  -27.3 FOM= 0.95 TEST= 0
INDE  7 29 22 FOBS=   241.0 SIGMA=  1.2 PHAS=  -64.4 FOM= 0.78 TEST= 1
INDE  7 29 24 FOBS=   237.3 SIGMA=  0.7 PHAS=   27.3 FOM= 0.80 TEST= 0
INDE  7 29 26 FOBS=   221.7 SIGMA=  0.8 PHAS=   45.0 FOM= 0.94 TEST= 0
INDE  7 29 28 FOBS=   120.5 SIGMA=  1.2 PHAS=  118.7 FOM= 0.94 TEST= 0
INDE  7 29 30 FOBS=   168.1 SIGMA=  1.0 PHAS= -112.0 FOM= 0.85 TEST= 0
INDE  7 29 32 FOBS=   185.3 SIGMA=  0.9 PHAS=  -73.8 FOM= 0.89 TEST= 0
INDE  7 29 34 FOBS=    69.8 SIGMA=  2.4 PHAS=  -45.3 FOM= 0.89 TEST= 0
INDE  7 29 36 FOBS=   200.8 SIGMA=  1.2 PHAS=   -9.9 FOM= 0.92 TEST= 0
INDE  7 29 38 FOBS=     0.0 SIGMA= 19.4 PHAS=    0.0 FOM= 0.00 TEST= 0
INDE  7 29 40 FOBS=   155.3 SIGMA=  1.3 PHAS= -111.8 FOM= 0.90 TEST= 0
INDE  7 29 42 FOBS=   149.7 SIGMA=  1.4 PHAS= -116.9 FOM= 0.94 TEST= 0
INDE  7 29 44 FOBS=    72.9 SIGMA=  2.7 PHAS=   99.6 FOM= 0.66 TEST= 0
INDE  7 29 46 FOBS=   212.2 SIGMA=  1.0 PHAS= -127.7 FOM= 0.96 TEST= 0
INDE  7 29 48 FOBS=    55.5 SIGMA=  3.1 PHAS=  -48.4 FOM= 0.65 TEST= 0
INDE  7 29 50 FOBS=    54.0 SIGMA=  3.2 PHAS=  173.1 FOM= 0.25 TEST= 0
INDE  7 29 52 FOBS=    29.1 SIGMA=  4.7 PHAS= -139.9 FOM= 0.64 TEST= 0
INDE  7 29 54 FOBS=    63.5 SIGMA=  2.1 PHAS=  -20.4 FOM= 0.32 TEST= 0
INDE  7 29 56 FOBS=    27.4 SIGMA=  5.3 PHAS=   -8.4 FOM= 0.67 TEST= 1
INDE  7 29 58 FOBS=    58.6 SIGMA=  2.7 PHAS= -131.6 FOM= 0.86 TEST= 0
INDE  7 29 60 FOBS=    82.7 SIGMA=  2.2 PHAS=  120.9 FOM= 0.93 TEST= 0
INDE  7 29 62 FOBS=    97.8 SIGMA=  3.0 PHAS=  102.5 FOM= 0.92 TEST= 0
INDE  7 29 64 FOBS=     0.0 SIGMA= 25.5 PHAS=    0.0 FOM= 0.00 TEST= 0
INDE  7 29 66 FOBS=    48.6 SIGMA= 10.1 PHAS=   88.4 FOM= 0.51 TEST= 0
INDE  7 29 68 FOBS=     0.0 SIGMA= 31.1 PHAS=    0.0 FOM= 0.00 TEST= 0
INDE  7 29 70 FOBS=    66.9 SIGMA=  7.4 PHAS=  178.5 FOM= 0.75 TEST= 0
INDE  7 30  7 FOBS=   165.5 SIGMA=  0.8 PHAS= -177.4 FOM= 0.97 TEST= 0
INDE  7 30  9 FOBS=    29.0 SIGMA=  3.0 PHAS=  135.0 FOM= 0.98 TEST= 0
INDE  7 30 11 FOBS=   128.7 SIGMA=  0.9 PHAS= -123.8 FOM= 0.82 TEST= 0
INDE  7 30 13 FOBS=   195.9 SIGMA=  0.7 PHAS=  -97.9 FOM= 0.99 TEST= 1
INDE  7 30 15 FOBS=    75.9 SIGMA=  1.4 PHAS=  124.8 FOM= 0.92 TEST= 0
INDE  7 30 17 FOBS=   237.9 SIGMA=  0.8 PHAS= -136.1 FOM= 0.96 TEST= 0
INDE  7 30 19 FOBS=    58.0 SIGMA=  2.6 PHAS=  -44.2 FOM= 0.92 TEST= 0
INDE  7 30 21 FOBS=   219.9 SIGMA=  0.9 PHAS=  125.0 FOM= 0.96 TEST= 0
INDE  7 30 23 FOBS=   311.1 SIGMA=  0.7 PHAS=  -68.7 FOM= 0.96 TEST= 0
INDE  7 30 25 FOBS=   262.0 SIGMA=  0.8 PHAS=   44.3 FOM= 0.99 TEST= 0
INDE  7 30 27 FOBS=   187.0 SIGMA=  1.0 PHAS=    6.4 FOM= 0.87 TEST= 1
INDE  7 30 29 FOBS=    77.9 SIGMA=  1.9 PHAS=    6.6 FOM= 0.96 TEST= 0
INDE  7 30 31 FOBS=    43.8 SIGMA=  3.6 PHAS=  115.8 FOM= 0.85 TEST= 0
INDE  7 30 33 FOBS=   224.1 SIGMA=  0.9 PHAS= -125.5 FOM= 0.97 TEST= 0
INDE  7 30 35 FOBS=   157.1 SIGMA=  1.2 PHAS=  131.6 FOM= 0.74 TEST= 1
INDE  7 30 37 FOBS=    93.1 SIGMA=  2.3 PHAS=  -41.2 FOM= 0.83 TEST= 0
INDE  7 30 39 FOBS=   152.4 SIGMA=  1.3 PHAS=  135.8 FOM= 0.92 TEST= 0
INDE  7 30 41 FOBS=   160.8 SIGMA=  1.2 PHAS= -103.4 FOM= 0.95 TEST= 0
INDE  7 30 43 FOBS=   125.9 SIGMA=  1.8 PHAS= -125.0 FOM= 0.79 TEST= 0
INDE  7 30 45 FOBS=   127.5 SIGMA=  1.6 PHAS=  101.0 FOM= 0.93 TEST= 0
INDE  7 30 47 FOBS=   157.2 SIGMA=  1.3 PHAS= -179.4 FOM= 0.88 TEST= 0
INDE  7 30 49 FOBS=     0.0 SIGMA= 18.4 PHAS=    0.0 FOM= 0.00 TEST= 0
INDE  7 30 51 FOBS=   180.1 SIGMA=  1.0 PHAS= -112.9 FOM= 0.54 TEST= 1
INDE  7 30 53 FOBS=    77.8 SIGMA=  1.8 PHAS= -104.3 FOM= 0.91 TEST= 0
INDE  7 30 55 FOBS=    35.4 SIGMA=  4.3 PHAS=   -0.6 FOM= 0.80 TEST= 0
INDE  7 30 57 FOBS=    31.4 SIGMA=  4.8 PHAS=   89.6 FOM= 0.31 TEST= 0
INDE  7 30 59 FOBS=   120.1 SIGMA=  1.4 PHAS=  126.1 FOM= 0.76 TEST= 0
INDE  7 30 61 FOBS=   110.6 SIGMA=  1.6 PHAS=   54.1 FOM= 0.94 TEST= 0
INDE  7 30 63 FOBS=     0.0 SIGMA= 23.5 PHAS=    0.0 FOM= 0.00 TEST= 0
INDE  7 30 65 FOBS=    23.5 SIGMA= 20.7 PHAS=   37.2 FOM= 0.27 TEST= 0
INDE  7 30 67 FOBS=     0.0 SIGMA= 31.3 PHAS=    0.0 FOM= 0.00 TEST= 0
INDE  7 30 71 FOBS=    67.6 SIGMA=  7.6 PHAS= -104.3 FOM= 0.81 TEST= 0
INDE  7 31  8 FOBS=    86.3 SIGMA=  1.0 PHAS=   81.0 FOM= 0.99 TEST= 0
INDE  7 31 10 FOBS=    62.6 SIGMA=  1.6 PHAS= -103.0 FOM= 0.85 TEST= 0
INDE  7 31 12 FOBS=   255.5 SIGMA=  0.6 PHAS=    8.7 FOM= 0.98 TEST= 0
INDE  7 31 14 FOBS=   117.0 SIGMA=  1.0 PHAS=   93.2 FOM= 0.99 TEST= 0
INDE  7 31 16 FOBS=   111.5 SIGMA=  1.1 PHAS=   31.8 FOM= 0.96 TEST= 0
INDE  7 31 18 FOBS=    42.0 SIGMA=  2.9 PHAS=   68.1 FOM= 0.56 TEST= 0
INDE  7 31 20 FOBS=   194.3 SIGMA=  1.0 PHAS=   82.2 FOM= 0.95 TEST= 0
INDE  7 31 22 FOBS=   386.3 SIGMA=  0.7 PHAS=  142.3 FOM= 0.98 TEST= 0
```

*FIG. 12A - 196*

```
INDE  7  31  24  FOBS=   226.2  SIGMA=   0.9  PHAS=   -40.6  FOM=  0.99  TEST= 0
INDE  7  31  26  FOBS=   202.7  SIGMA=   0.9  PHAS=    -5.7  FOM=  0.79  TEST= 0
INDE  7  31  28  FOBS=   139.5  SIGMA=   1.2  PHAS=   -95.4  FOM=  0.86  TEST= 0
INDE  7  31  30  FOBS=   231.7  SIGMA=   0.8  PHAS=   -10.3  FOM=  0.95  TEST= 0
INDE  7  31  32  FOBS=    16.5  SIGMA=  10.2  PHAS=     4.7  FOM=  0.73  TEST= 0
INDE  7  31  34  FOBS=    94.8  SIGMA=   1.9  PHAS=  -107.8  FOM=  0.82  TEST= 0
INDE  7  31  36  FOBS=   171.5  SIGMA=   1.2  PHAS=  -156.6  FOM=  0.96  TEST= 0
INDE  7  31  38  FOBS=   123.3  SIGMA=   1.8  PHAS=    99.0  FOM=  0.90  TEST= 0
INDE  7  31  40  FOBS=   173.2  SIGMA=   1.2  PHAS=    74.1  FOM=  0.89  TEST= 0
INDE  7  31  42  FOBS=   266.5  SIGMA=   0.9  PHAS=   174.6  FOM=  0.69  TEST= 1
INDE  7  31  44  FOBS=     0.0  SIGMA=  21.2  PHAS=     0.0  FOM=  0.00  TEST= 0
INDE  7  31  46  FOBS=    42.1  SIGMA=   4.6  PHAS=   -58.0  FOM=  0.36  TEST= 0
INDE  7  31  48  FOBS=    71.2  SIGMA=   2.7  PHAS=  -128.9  FOM=  0.88  TEST= 0
INDE  7  31  50  FOBS=    86.1  SIGMA=   2.3  PHAS=  -130.5  FOM=  0.81  TEST= 1
INDE  7  31  52  FOBS=    97.1  SIGMA=   1.5  PHAS=  -152.5  FOM=  0.74  TEST= 0
INDE  7  31  54  FOBS=   149.1  SIGMA=   1.1  PHAS=  -102.6  FOM=  0.97  TEST= 0
INDE  7  31  56  FOBS=     0.0  SIGMA=  17.4  PHAS=     0.0  FOM=  0.00  TEST= 0
INDE  7  31  58  FOBS=    18.4  SIGMA=   8.9  PHAS=  -148.8  FOM=  0.08  TEST= 0
INDE  7  31  60  FOBS=    26.3  SIGMA=   6.4  PHAS=    77.6  FOM=  0.55  TEST= 0
INDE  7  31  62  FOBS=    48.3  SIGMA=   3.5  PHAS=    40.7  FOM=  0.46  TEST= 0
INDE  7  31  64  FOBS=    65.9  SIGMA=   3.8  PHAS=   -75.5  FOM=  0.68  TEST= 0
INDE  7  31  66  FOBS=    68.5  SIGMA=   7.3  PHAS=   171.1  FOM=  0.22  TEST= 1
INDE  7  31  68  FOBS=    57.3  SIGMA=   8.8  PHAS=   -37.8  FOM=  0.70  TEST= 0
INDE  7  31  70  FOBS=    37.8  SIGMA=  13.2  PHAS=   166.1  FOM=  0.61  TEST= 0
INDE  7  32   7  FOBS=    70.7  SIGMA=   1.5  PHAS=   156.1  FOM=  0.97  TEST= 0
INDE  7  32   9  FOBS=    59.0  SIGMA=   1.8  PHAS=   122.9  FOM=  0.95  TEST= 0
INDE  7  32  11  FOBS=   125.8  SIGMA=   0.9  PHAS=   179.5  FOM=  0.84  TEST= 0
INDE  7  32  13  FOBS=   283.0  SIGMA=   0.7  PHAS=   -24.0  FOM=  0.99  TEST= 0
INDE  7  32  15  FOBS=   181.5  SIGMA=   0.8  PHAS=   -10.8  FOM=  0.94  TEST= 0
INDE  7  32  17  FOBS=    73.3  SIGMA=   1.7  PHAS=   -62.2  FOM=  0.69  TEST= 0
INDE  7  32  19  FOBS=   196.4  SIGMA=   0.8  PHAS=     9.1  FOM=  0.97  TEST= 0
INDE  7  32  21  FOBS=   261.7  SIGMA=   0.8  PHAS=    33.4  FOM=  0.95  TEST= 0
INDE  7  32  23  FOBS=   143.6  SIGMA=   1.3  PHAS=   170.4  FOM=  0.97  TEST= 0
INDE  7  32  25  FOBS=    69.4  SIGMA=   2.6  PHAS=    93.6  FOM=  0.83  TEST= 0
INDE  7  32  27  FOBS=   341.9  SIGMA=   0.7  PHAS=   -48.0  FOM=  0.93  TEST= 0
INDE  7  32  29  FOBS=   258.3  SIGMA=   0.7  PHAS=   -68.5  FOM=  0.95  TEST= 0
INDE  7  32  31  FOBS=   182.6  SIGMA=   1.0  PHAS=   -38.7  FOM=  0.92  TEST= 0
INDE  7  32  33  FOBS=    88.9  SIGMA=   2.1  PHAS=    70.2  FOM=  0.27  TEST= 0
INDE  7  32  35  FOBS=   167.1  SIGMA=   1.2  PHAS=    49.0  FOM=  0.86  TEST= 0
INDE  7  32  37  FOBS=    68.8  SIGMA=   2.8  PHAS=   -96.8  FOM=  0.21  TEST= 0
INDE  7  32  39  FOBS=    72.3  SIGMA=   2.9  PHAS=    40.4  FOM=  0.74  TEST= 0
INDE  7  32  41  FOBS=   165.4  SIGMA=   1.2  PHAS=  -108.5  FOM=  0.91  TEST= 0
INDE  7  32  43  FOBS=    63.9  SIGMA=   2.8  PHAS=   -34.5  FOM=  0.68  TEST= 0
INDE  7  32  45  FOBS=   117.1  SIGMA=   2.0  PHAS=   177.1  FOM=  0.94  TEST= 0
INDE  7  32  47  FOBS=   192.3  SIGMA=   1.2  PHAS=  -147.6  FOM=  0.97  TEST= 0
INDE  7  32  49  FOBS=    70.6  SIGMA=   2.7  PHAS=  -109.3  FOM=  0.29  TEST= 1
INDE  7  32  51  FOBS=     0.0  SIGMA=  19.4  PHAS=     0.0  FOM=  0.00  TEST= 0
INDE  7  32  53  FOBS=   172.9  SIGMA=   0.9  PHAS=   169.7  FOM=  0.93  TEST= 0
INDE  7  32  55  FOBS=   103.7  SIGMA=   1.5  PHAS=  -168.7  FOM=  0.95  TEST= 0
INDE  7  32  57  FOBS=     0.0  SIGMA=  18.1  PHAS=     0.0  FOM=  0.00  TEST= 0
INDE  7  32  59  FOBS=     0.0  SIGMA=  23.9  PHAS=     0.0  FOM=  0.00  TEST= 0
INDE  7  32  61  FOBS=    31.6  SIGMA=   5.4  PHAS=    48.5  FOM=  0.36  TEST= 0
INDE  7  32  63  FOBS=    33.0  SIGMA=   5.2  PHAS=   156.3  FOM=  0.40  TEST= 0
INDE  7  32  65  FOBS=    39.3  SIGMA=   9.5  PHAS=   -64.8  FOM=  0.39  TEST= 0
INDE  7  32  67  FOBS=     0.0  SIGMA=  31.5  PHAS=     0.0  FOM=  0.00  TEST= 0
INDE  7  32  69  FOBS=    21.3  SIGMA=  24.1  PHAS=   136.5  FOM=  0.39  TEST= 0
INDE  7  33   8  FOBS=   221.1  SIGMA=   0.6  PHAS=    85.3  FOM=  0.94  TEST= 0
INDE  7  33  10  FOBS=    83.5  SIGMA=   1.3  PHAS=    15.3  FOM=  0.98  TEST= 0
INDE  7  33  12  FOBS=   162.6  SIGMA=   0.8  PHAS=    66.8  FOM=  0.97  TEST= 0
INDE  7  33  14  FOBS=   101.2  SIGMA=   1.2  PHAS=  -135.4  FOM=  0.91  TEST= 0
INDE  7  33  16  FOBS=    82.5  SIGMA=   1.5  PHAS=   -57.6  FOM=  0.95  TEST= 0
INDE  7  33  18  FOBS=   181.9  SIGMA=   0.9  PHAS=   -75.0  FOM=  0.98  TEST= 0
INDE  7  33  20  FOBS=   232.8  SIGMA=   0.9  PHAS=   -71.3  FOM=  0.91  TEST= 1
INDE  7  33  22  FOBS=   250.2  SIGMA=   0.9  PHAS=    55.7  FOM=  0.96  TEST= 1
INDE  7  33  24  FOBS=    80.7  SIGMA=   2.3  PHAS=   140.0  FOM=  0.95  TEST= 1
INDE  7  33  26  FOBS=   216.6  SIGMA=   1.1  PHAS=   120.9  FOM=  0.94  TEST= 0
INDE  7  33  28  FOBS=   274.6  SIGMA=   0.8  PHAS=  -148.7  FOM=  0.94  TEST= 0
INDE  7  33  30  FOBS=   112.6  SIGMA=   1.6  PHAS=  -158.7  FOM=  0.95  TEST= 0
INDE  7  33  32  FOBS=   132.2  SIGMA=   1.4  PHAS=  -124.0  FOM=  0.87  TEST= 0
INDE  7  33  34  FOBS=   206.4  SIGMA=   1.0  PHAS=   -49.7  FOM=  0.95  TEST= 0
```

*FIG. 12A - 197*

```
INDE  7  33  36  FOBS=  325.2  SIGMA=   0.8  PHAS=  -172.6  FOM=  0.98  TEST= 0
INDE  7  33  38  FOBS=   36.0  SIGMA=   5.8  PHAS=  -142.0  FOM=  0.35  TEST= 0
INDE  7  33  40  FOBS=  226.2  SIGMA=   1.0  PHAS=   134.6  FOM=  0.95  TEST= 0
INDE  7  33  42  FOBS=   22.2  SIGMA=   8.6  PHAS=  -174.0  FOM=  0.61  TEST= 0
INDE  7  33  44  FOBS=   73.3  SIGMA=   2.5  PHAS=  -148.2  FOM=  0.21  TEST= 0
INDE  7  33  46  FOBS=  135.3  SIGMA=   1.7  PHAS=    84.7  FOM=  0.98  TEST= 0
INDE  7  33  48  FOBS=  118.4  SIGMA=   1.9  PHAS=   132.1  FOM=  0.90  TEST= 0
INDE  7  33  50  FOBS=  138.3  SIGMA=   1.5  PHAS=   127.8  FOM=  0.94  TEST= 0
INDE  7  33  52  FOBS=  118.2  SIGMA=   1.5  PHAS=    82.2  FOM=  0.86  TEST= 0
INDE  7  33  54  FOBS=   27.2  SIGMA=   7.0  PHAS=   -72.9  FOM=  0.52  TEST= 0
INDE  7  33  56  FOBS=  139.3  SIGMA=   1.3  PHAS=   140.0  FOM=  0.96  TEST= 0
INDE  7  33  58  FOBS=   40.8  SIGMA=   4.8  PHAS=    99.2  FOM=  0.48  TEST= 0
INDE  7  33  60  FOBS=   34.9  SIGMA=   5.3  PHAS=   -61.5  FOM=  0.47  TEST= 0
INDE  7  33  62  FOBS=    0.0  SIGMA=  19.1  PHAS=     0.0  FOM=  0.00  TEST= 0
INDE  7  33  64  FOBS=   67.7  SIGMA=   2.6  PHAS=  -171.9  FOM=  0.74  TEST= 0
INDE  7  33  66  FOBS=   48.8  SIGMA=   4.6  PHAS=    78.0  FOM=  0.41  TEST= 0
INDE  7  33  68  FOBS=   10.3  SIGMA=  49.4  PHAS=     7.5  FOM=  0.19  TEST= 0
INDE  7  33  70  FOBS=   77.5  SIGMA=   6.9  PHAS=   -23.9  FOM=  0.87  TEST= 0
INDE  7  34   7  FOBS=  420.2  SIGMA=   0.7  PHAS=   -47.8  FOM=  0.98  TEST= 0
INDE  7  34   9  FOBS=  181.1  SIGMA=   0.7  PHAS=  -137.7  FOM=  0.99  TEST= 0
INDE  7  34  11  FOBS=  195.8  SIGMA=   0.7  PHAS=   -54.3  FOM=  0.91  TEST= 0
INDE  7  34  13  FOBS=   96.9  SIGMA=   1.3  PHAS=   -20.8  FOM=  0.98  TEST= 0
INDE  7  34  15  FOBS=   13.4  SIGMA=   9.1  PHAS=   -38.2  FOM=  0.06  TEST= 0
INDE  7  34  17  FOBS=   50.5  SIGMA=   2.6  PHAS=   -80.6  FOM=  0.25  TEST= 0
INDE  7  34  19  FOBS=  181.0  SIGMA=   0.9  PHAS=   -97.6  FOM=  0.97  TEST= 0
INDE  7  34  21  FOBS=  300.0  SIGMA=   0.8  PHAS=   -49.3  FOM=  0.97  TEST= 0
INDE  7  34  23  FOBS=  242.9  SIGMA=   1.0  PHAS=    63.6  FOM=  0.83  TEST= 0
INDE  7  34  25  FOBS=  489.2  SIGMA=   0.8  PHAS=    60.4  FOM=  0.99  TEST= 0
INDE  7  34  27  FOBS=   53.1  SIGMA=   3.4  PHAS=   166.9  FOM=  0.92  TEST= 0
INDE  7  34  29  FOBS=   82.7  SIGMA=   2.3  PHAS=    95.3  FOM=  0.70  TEST= 0
INDE  7  34  31  FOBS=  181.9  SIGMA=   1.1  PHAS=   135.7  FOM=  0.96  TEST= 0
INDE  7  34  33  FOBS=  195.6  SIGMA=   1.1  PHAS=  -161.7  FOM=  0.95  TEST= 0
INDE  7  34  35  FOBS=  274.3  SIGMA=   0.9  PHAS=   116.8  FOM=  0.97  TEST= 0
INDE  7  34  37  FOBS=  248.2  SIGMA=   0.9  PHAS=   124.0  FOM=  0.97  TEST= 0
INDE  7  34  39  FOBS=  136.5  SIGMA=   1.4  PHAS=    64.7  FOM=  0.91  TEST= 0
INDE  7  34  41  FOBS=    0.0  SIGMA=  19.2  PHAS=     0.0  FOM=  0.00  TEST= 0
INDE  7  34  43  FOBS=   60.9  SIGMA=   3.0  PHAS=  -101.4  FOM=  0.18  TEST= 0
INDE  7  34  45  FOBS=  100.2  SIGMA=   1.8  PHAS=   157.3  FOM=  0.84  TEST= 1
INDE  7  34  47  FOBS=   27.0  SIGMA=   9.3  PHAS=   169.0  FOM=  0.14  TEST= 0
INDE  7  34  49  FOBS=  146.9  SIGMA=   1.6  PHAS=    12.8  FOM=  0.96  TEST= 0
INDE  7  34  51  FOBS=   42.5  SIGMA=   5.1  PHAS=    69.9  FOM=  0.72  TEST= 0
INDE  7  34  53  FOBS=   69.0  SIGMA=   2.4  PHAS=  -171.1  FOM=  0.33  TEST= 0
INDE  7  34  55  FOBS=   37.1  SIGMA=   6.8  PHAS=  -144.7  FOM=  0.60  TEST= 0
INDE  7  34  57  FOBS=  106.9  SIGMA=   1.8  PHAS=    39.5  FOM=  0.90  TEST= 0
INDE  7  34  59  FOBS=  103.7  SIGMA=   1.8  PHAS=   -62.3  FOM=  0.91  TEST= 0
INDE  7  34  61  FOBS=   99.0  SIGMA=   1.8  PHAS=   178.3  FOM=  0.76  TEST= 0
INDE  7  34  63  FOBS=   76.9  SIGMA=   2.3  PHAS=   121.7  FOM=  0.84  TEST= 0
INDE  7  34  65  FOBS=   84.0  SIGMA=   2.3  PHAS=    15.6  FOM=  0.88  TEST= 0
INDE  7  34  67  FOBS=   82.0  SIGMA=   2.8  PHAS=   -41.2  FOM=  0.91  TEST= 0
INDE  7  34  69  FOBS=   61.8  SIGMA=   8.4  PHAS=  -101.1  FOM=  0.89  TEST= 0
INDE  7  35   8  FOBS=  279.4  SIGMA=   0.7  PHAS=   153.6  FOM=  0.98  TEST= 0
INDE  7  35  10  FOBS=  183.9  SIGMA=   0.8  PHAS=  -130.7  FOM=  0.98  TEST= 0
INDE  7  35  12  FOBS=  117.3  SIGMA=   1.1  PHAS=  -158.2  FOM=  0.95  TEST= 1
INDE  7  35  14  FOBS=  138.3  SIGMA=   1.0  PHAS=   -50.3  FOM=  0.96  TEST= 0
INDE  7  35  16  FOBS=  117.7  SIGMA=   1.2  PHAS=   -59.1  FOM=  0.94  TEST= 1
INDE  7  35  18  FOBS=  189.0  SIGMA=   0.9  PHAS=    81.5  FOM=  0.85  TEST= 0
INDE  7  35  20  FOBS=  209.9  SIGMA=   0.8  PHAS=  -145.4  FOM=  0.92  TEST= 0
INDE  7  35  22  FOBS=  159.2  SIGMA=   1.4  PHAS=   -15.8  FOM=  0.97  TEST= 0
INDE  7  35  24  FOBS=  272.5  SIGMA=   1.0  PHAS=   -63.2  FOM=  0.92  TEST= 0
INDE  7  35  26  FOBS=  114.1  SIGMA=   2.0  PHAS=    -2.1  FOM=  0.95  TEST= 0
INDE  7  35  28  FOBS=   38.4  SIGMA=   5.0  PHAS=   -49.4  FOM=  0.48  TEST= 0
INDE  7  35  30  FOBS=  181.4  SIGMA=   1.2  PHAS=   122.9  FOM=  0.98  TEST= 0
INDE  7  35  32  FOBS=  106.0  SIGMA=   1.9  PHAS=   108.0  FOM=  0.67  TEST= 0
INDE  7  35  34  FOBS=   39.6  SIGMA=   5.3  PHAS=   -41.3  FOM=  0.66  TEST= 0
INDE  7  35  36  FOBS=   97.1  SIGMA=   2.1  PHAS=    49.0  FOM=  0.89  TEST= 0
INDE  7  35  38  FOBS=  293.5  SIGMA=   0.9  PHAS=    -1.6  FOM=  0.97  TEST= 0
INDE  7  35  40  FOBS=   46.2  SIGMA=   6.0  PHAS=  -156.5  FOM=  0.85  TEST= 0
INDE  7  35  42  FOBS=   48.9  SIGMA=   4.1  PHAS=   -42.2  FOM=  0.73  TEST= 0
INDE  7  35  44  FOBS=  101.3  SIGMA=   1.8  PHAS=    66.8  FOM=  0.93  TEST= 0
INDE  7  35  46  FOBS=   91.1  SIGMA=   2.0  PHAS=    52.7  FOM=  0.88  TEST= 0
```

*FIG. 12A - 198*

```
INDE  7  35  48  FOBS=  131.2  SIGMA=   1.6  PHAS=   -92.6  FOM=  0.86  TEST= 0
INDE  7  35  50  FOBS=   90.4  SIGMA=   2.5  PHAS=    26.4  FOM=  0.86  TEST= 0
INDE  7  35  52  FOBS=   77.5  SIGMA=   2.4  PHAS=    86.3  FOM=  0.44  TEST= 1
INDE  7  35  54  FOBS=   66.6  SIGMA=   2.7  PHAS=  -131.7  FOM=  0.71  TEST= 0
INDE  7  35  56  FOBS=   41.7  SIGMA=   4.3  PHAS=  -118.6  FOM=  0.61  TEST= 0
INDE  7  35  58  FOBS=    0.0  SIGMA=  21.0  PHAS=     0.0  FOM=  0.00  TEST= 0
INDE  7  35  60  FOBS=   61.7  SIGMA=   2.9  PHAS=  -111.4  FOM=  0.52  TEST= 0
INDE  7  35  62  FOBS=   49.6  SIGMA=   3.6  PHAS=    85.6  FOM=  0.63  TEST= 0
INDE  7  35  64  FOBS=   51.4  SIGMA=   3.4  PHAS=  -157.4  FOM=  0.83  TEST= 0
INDE  7  35  66  FOBS=   36.0  SIGMA=   5.9  PHAS=   -84.0  FOM=  0.55  TEST= 0
INDE  7  35  68  FOBS=   40.1  SIGMA=   7.8  PHAS=   177.7  FOM=  0.08  TEST= 1
INDE  7  36   7  FOBS=  545.2  SIGMA=   0.8  PHAS=   -50.6  FOM=  0.99  TEST= 0
INDE  7  36   9  FOBS=  470.9  SIGMA=   0.8  PHAS=   125.8  FOM=  0.97  TEST= 0
INDE  7  36  11  FOBS=  141.5  SIGMA=   1.0  PHAS=   172.8  FOM=  0.96  TEST= 0
INDE  7  36  13  FOBS=  195.5  SIGMA=   0.8  PHAS=   138.9  FOM=  0.95  TEST= 0
INDE  7  36  15  FOBS=  258.7  SIGMA=   0.7  PHAS=  -130.0  FOM=  0.97  TEST= 0
INDE  7  36  17  FOBS=  181.4  SIGMA=   0.9  PHAS=  -104.2  FOM=  0.96  TEST= 0
INDE  7  36  19  FOBS=  260.7  SIGMA=   1.0  PHAS=  -101.3  FOM=  0.93  TEST= 0
INDE  7  36  21  FOBS=  367.2  SIGMA=   0.8  PHAS=  -144.5  FOM=  0.99  TEST= 0
INDE  7  36  23  FOBS=  186.4  SIGMA=   1.3  PHAS=    25.7  FOM=  0.26  TEST= 0
INDE  7  36  25  FOBS=  382.6  SIGMA=   0.8  PHAS=    17.6  FOM=  0.95  TEST= 0
INDE  7  36  27  FOBS=  104.6  SIGMA=   2.2  PHAS=   -30.7  FOM=  0.72  TEST= 0
INDE  7  36  29  FOBS=  182.4  SIGMA=   1.2  PHAS=    24.7  FOM=  0.86  TEST= 0
INDE  7  36  31  FOBS=  241.2  SIGMA=   0.9  PHAS=    88.1  FOM=  0.91  TEST= 1
INDE  7  36  33  FOBS=  126.3  SIGMA=   1.6  PHAS=   -52.2  FOM=  0.88  TEST= 0
INDE  7  36  35  FOBS=  200.8  SIGMA=   1.1  PHAS=   171.6  FOM=  0.94  TEST= 0
INDE  7  36  37  FOBS=  151.0  SIGMA=   1.4  PHAS=  -126.9  FOM=  0.89  TEST= 0
INDE  7  36  39  FOBS=   82.1  SIGMA=   2.3  PHAS=   -69.5  FOM=  0.90  TEST= 0
INDE  7  36  41  FOBS=  151.4  SIGMA=   1.3  PHAS=  -167.4  FOM=  0.92  TEST= 0
INDE  7  36  43  FOBS=   32.4  SIGMA=   6.0  PHAS=   -67.2  FOM=  0.34  TEST= 0
INDE  7  36  45  FOBS=   52.2  SIGMA=   3.5  PHAS=    65.2  FOM=  0.77  TEST= 0
INDE  7  36  47  FOBS=   29.3  SIGMA=   6.8  PHAS=  -128.4  FOM=  0.24  TEST= 0
INDE  7  36  49  FOBS=   99.6  SIGMA=   2.0  PHAS=   -63.7  FOM=  0.90  TEST= 0
INDE  7  36  51  FOBS=    0.0  SIGMA=  20.6  PHAS=     0.0  FOM=  0.00  TEST= 0
INDE  7  36  53  FOBS=   87.7  SIGMA=   2.1  PHAS=    50.7  FOM=  0.37  TEST= 1
INDE  7  36  55  FOBS=   63.8  SIGMA=   2.8  PHAS=  -161.7  FOM=  0.70  TEST= 0
INDE  7  36  57  FOBS=    0.0  SIGMA=  18.8  PHAS=     0.0  FOM=  0.00  TEST= 0
INDE  7  36  59  FOBS=    0.0  SIGMA=  20.1  PHAS=     0.0  FOM=  0.00  TEST= 0
INDE  7  36  61  FOBS=   18.4  SIGMA=  12.0  PHAS=    96.7  FOM=  0.15  TEST= 0
INDE  7  36  63  FOBS=   39.3  SIGMA=   4.5  PHAS=   111.4  FOM=  0.66  TEST= 0
INDE  7  36  65  FOBS=   78.5  SIGMA=   2.4  PHAS=   106.4  FOM=  0.90  TEST= 0
INDE  7  36  67  FOBS=   96.8  SIGMA=   2.6  PHAS=   -10.6  FOM=  0.94  TEST= 0
INDE  7  37   8  FOBS=  319.2  SIGMA=   0.6  PHAS=   164.7  FOM=  0.88  TEST= 0
INDE  7  37  10  FOBS=  281.6  SIGMA=   0.7  PHAS=    66.9  FOM=  0.97  TEST= 0
INDE  7  37  12  FOBS=  284.3  SIGMA=   0.7  PHAS=   150.8  FOM=  0.99  TEST= 0
INDE  7  37  14  FOBS=  263.5  SIGMA=   0.7  PHAS=    74.9  FOM=  0.99  TEST= 0
INDE  7  37  16  FOBS=  208.1  SIGMA=   0.8  PHAS=   131.1  FOM=  0.88  TEST= 0
INDE  7  37  18  FOBS=  192.4  SIGMA=   1.2  PHAS=   161.2  FOM=  0.91  TEST= 0
INDE  7  37  20  FOBS=   92.4  SIGMA=   1.8  PHAS=    66.2  FOM=  0.83  TEST= 0
INDE  7  37  22  FOBS=  149.3  SIGMA=   1.2  PHAS=    97.0  FOM=  0.97  TEST= 0
INDE  7  37  24  FOBS=  267.5  SIGMA=   1.0  PHAS=   -25.0  FOM=  0.96  TEST= 0
INDE  7  37  26  FOBS=  120.4  SIGMA=   2.0  PHAS=    -2.3  FOM=  0.85  TEST= 1
INDE  7  37  28  FOBS=  111.8  SIGMA=   2.2  PHAS=  -138.7  FOM=  0.91  TEST= 0
INDE  7  37  30  FOBS=  101.6  SIGMA=   2.2  PHAS=    56.1  FOM=  0.87  TEST= 0
INDE  7  37  32  FOBS=  167.5  SIGMA=   1.3  PHAS=   -97.3  FOM=  0.89  TEST= 0
INDE  7  37  34  FOBS=  109.5  SIGMA=   1.8  PHAS=   105.8  FOM=  0.76  TEST= 0
INDE  7  37  36  FOBS=   88.8  SIGMA=   2.2  PHAS=   132.6  FOM=  0.78  TEST= 0
INDE  7  37  38  FOBS=    0.0  SIGMA=  19.4  PHAS=     0.0  FOM=  0.00  TEST= 0
INDE  7  37  40  FOBS=  130.8  SIGMA=   1.5  PHAS=   129.9  FOM=  0.84  TEST= 0
INDE  7  37  42  FOBS=   88.4  SIGMA=   2.1  PHAS=    81.8  FOM=  0.90  TEST= 0
INDE  7  37  44  FOBS=   69.8  SIGMA=   2.6  PHAS=    56.5  FOM=  0.71  TEST= 0
INDE  7  37  46  FOBS=   40.4  SIGMA=   4.5  PHAS=    67.8  FOM=  0.67  TEST= 0
INDE  7  37  48  FOBS=  143.0  SIGMA=   1.3  PHAS=  -146.5  FOM=  0.93  TEST= 0
INDE  7  37  50  FOBS=   28.9  SIGMA=   7.8  PHAS=    24.2  FOM=  0.46  TEST= 0
INDE  7  37  52  FOBS=    0.0  SIGMA=  23.1  PHAS=     0.0  FOM=  0.00  TEST= 0
INDE  7  37  54  FOBS=   66.7  SIGMA=   2.7  PHAS=    23.1  FOM=  0.57  TEST= 0
INDE  7  37  56  FOBS=    0.0  SIGMA=  18.8  PHAS=     0.0  FOM=  0.00  TEST= 0
INDE  7  37  58  FOBS=    0.0  SIGMA=  19.6  PHAS=     0.0  FOM=  0.00  TEST= 0
INDE  7  37  60  FOBS=   40.4  SIGMA=   4.4  PHAS=    -1.9  FOM=  0.56  TEST= 0
INDE  7  37  62  FOBS=    0.0  SIGMA=  18.8  PHAS=     0.0  FOM=  0.00  TEST= 0
```

*FIG. 12A - 199*

| | | | | | | | | | | | |
|---|---|---|---|---|---|---|---|---|---|---|---|
| INDE | 7 | 37 | 64 | FOBS= | 36.8 | SIGMA= | 4.9 | PHAS= | 41.1 | FOM= | 0.50 | TEST= 0
| INDE | 7 | 37 | 66 | FOBS= | 50.2 | SIGMA= | 4.7 | PHAS= | 10.5 | FOM= | 0.73 | TEST= 0
| INDE | 7 | 37 | 68 | FOBS= | 0.0 | SIGMA= | 28.0 | PHAS= | 0.0 | FOM= | 0.00 | TEST= 0
| INDE | 7 | 38 | 7 | FOBS= | 206.0 | SIGMA= | 0.8 | PHAS= | 45.3 | FOM= | 0.98 | TEST= 0
| INDE | 7 | 38 | 9 | FOBS= | 160.2 | SIGMA= | 1.8 | PHAS= | 95.3 | FOM= | 0.97 | TEST= 0
| INDE | 7 | 38 | 11 | FOBS= | 187.5 | SIGMA= | 0.8 | PHAS= | 29.4 | FOM= | 0.93 | TEST= 0
| INDE | 7 | 38 | 13 | FOBS= | 149.1 | SIGMA= | 1.0 | PHAS= | 55.8 | FOM= | 0.98 | TEST= 1
| INDE | 7 | 38 | 15 | FOBS= | 311.9 | SIGMA= | 0.7 | PHAS= | -46.8 | FOM= | 0.94 | TEST= 0
| INDE | 7 | 38 | 17 | FOBS= | 284.4 | SIGMA= | 0.8 | PHAS= | 79.6 | FOM= | 0.31 | TEST= 1
| INDE | 7 | 38 | 19 | FOBS= | 141.4 | SIGMA= | 1.3 | PHAS= | -95.9 | FOM= | 0.91 | TEST= 1
| INDE | 7 | 38 | 21 | FOBS= | 44.3 | SIGMA= | 3.8 | PHAS= | -140.7 | FOM= | 0.33 | TEST= 0
| INDE | 7 | 38 | 23 | FOBS= | 210.3 | SIGMA= | 1.2 | PHAS= | -12.0 | FOM= | 0.98 | TEST= 1
| INDE | 7 | 38 | 25 | FOBS= | 65.9 | SIGMA= | 3.6 | PHAS= | 144.2 | FOM= | 0.23 | TEST= 0
| INDE | 7 | 38 | 27 | FOBS= | 186.8 | SIGMA= | 1.4 | PHAS= | -31.4 | FOM= | 0.95 | TEST= 0
| INDE | 7 | 38 | 29 | FOBS= | 137.8 | SIGMA= | 1.9 | PHAS= | 30.9 | FOM= | 0.56 | TEST= 0
| INDE | 7 | 38 | 31 | FOBS= | 0.0 | SIGMA= | 22.0 | PHAS= | 0.0 | FOM= | 0.00 | TEST= 0
| INDE | 7 | 38 | 33 | FOBS= | 147.2 | SIGMA= | 1.4 | PHAS= | 151.4 | FOM= | 0.89 | TEST= 0
| INDE | 7 | 38 | 35 | FOBS= | 48.2 | SIGMA= | 4.3 | PHAS= | 84.7 | FOM= | 0.52 | TEST= 1
| INDE | 7 | 38 | 37 | FOBS= | 176.7 | SIGMA= | 1.2 | PHAS= | 100.3 | FOM= | 0.92 | TEST= 0
| INDE | 7 | 38 | 39 | FOBS= | 115.7 | SIGMA= | 1.7 | PHAS= | 14.8 | FOM= | 0.77 | TEST= 0
| INDE | 7 | 38 | 41 | FOBS= | 81.9 | SIGMA= | 2.3 | PHAS= | 52.4 | FOM= | 0.31 | TEST= 0
| INDE | 7 | 38 | 43 | FOBS= | 91.5 | SIGMA= | 2.0 | PHAS= | -37.8 | FOM= | 0.85 | TEST= 0
| INDE | 7 | 38 | 45 | FOBS= | 14.8 | SIGMA= | 12.2 | PHAS= | 28.4 | FOM= | 0.20 | TEST= 0
| INDE | 7 | 38 | 47 | FOBS= | 51.1 | SIGMA= | 3.5 | PHAS= | 106.7 | FOM= | 0.74 | TEST= 1
| INDE | 7 | 38 | 49 | FOBS= | 80.0 | SIGMA= | 2.3 | PHAS= | 148.7 | FOM= | 0.84 | TEST= 0
| INDE | 7 | 38 | 51 | FOBS= | 0.0 | SIGMA= | 19.7 | PHAS= | 0.0 | FOM= | 0.00 | TEST= 0
| INDE | 7 | 38 | 53 | FOBS= | 101.2 | SIGMA= | 1.9 | PHAS= | 55.5 | FOM= | 0.88 | TEST= 0
| INDE | 7 | 38 | 55 | FOBS= | 15.6 | SIGMA= | 13.6 | PHAS= | 150.4 | FOM= | 0.05 | TEST= 1
| INDE | 7 | 38 | 57 | FOBS= | 27.4 | SIGMA= | 6.6 | PHAS= | 139.2 | FOM= | 0.58 | TEST= 0
| INDE | 7 | 38 | 59 | FOBS= | 20.6 | SIGMA= | 8.7 | PHAS= | -26.2 | FOM= | 0.06 | TEST= 0
| INDE | 7 | 38 | 61 | FOBS= | 0.0 | SIGMA= | 18.9 | PHAS= | 0.0 | FOM= | 0.00 | TEST= 0
| INDE | 7 | 38 | 63 | FOBS= | 39.2 | SIGMA= | 4.7 | PHAS= | -117.2 | FOM= | 0.38 | TEST= 1
| INDE | 7 | 38 | 65 | FOBS= | 0.0 | SIGMA= | 19.6 | PHAS= | 0.0 | FOM= | 0.00 | TEST= 0
| INDE | 7 | 38 | 67 | FOBS= | 16.7 | SIGMA= | 14.5 | PHAS= | 31.4 | FOM= | 0.67 | TEST= 0
| INDE | 7 | 39 | 8 | FOBS= | 327.2 | SIGMA= | 0.6 | PHAS= | 22.7 | FOM= | 0.92 | TEST= 1
| INDE | 7 | 39 | 10 | FOBS= | 271.5 | SIGMA= | 0.9 | PHAS= | -19.9 | FOM= | 0.94 | TEST= 1
| INDE | 7 | 39 | 12 | FOBS= | 156.2 | SIGMA= | 1.0 | PHAS= | 10.9 | FOM= | 0.68 | TEST= 0
| INDE | 7 | 39 | 14 | FOBS= | 341.8 | SIGMA= | 0.6 | PHAS= | -61.2 | FOM= | 0.98 | TEST= 0
| INDE | 7 | 39 | 16 | FOBS= | 234.3 | SIGMA= | 0.9 | PHAS= | -90.3 | FOM= | 0.58 | TEST= 0
| INDE | 7 | 39 | 18 | FOBS= | 202.7 | SIGMA= | 0.9 | PHAS= | 100.5 | FOM= | 0.95 | TEST= 0
| INDE | 7 | 39 | 20 | FOBS= | 173.8 | SIGMA= | 1.1 | PHAS= | -135.9 | FOM= | 0.82 | TEST= 0
| INDE | 7 | 39 | 22 | FOBS= | 114.7 | SIGMA= | 1.6 | PHAS= | -49.7 | FOM= | 0.90 | TEST= 0
| INDE | 7 | 39 | 24 | FOBS= | 86.1 | SIGMA= | 2.9 | PHAS= | -31.0 | FOM= | 0.72 | TEST= 0
| INDE | 7 | 39 | 26 | FOBS= | 159.7 | SIGMA= | 1.7 | PHAS= | 101.4 | FOM= | 0.82 | TEST= 1
| INDE | 7 | 39 | 28 | FOBS= | 322.4 | SIGMA= | 1.0 | PHAS= | -146.8 | FOM= | 0.98 | TEST= 0
| INDE | 7 | 39 | 30 | FOBS= | 168.5 | SIGMA= | 1.5 | PHAS= | -113.0 | FOM= | 0.94 | TEST= 0
| INDE | 7 | 39 | 32 | FOBS= | 17.4 | SIGMA= | 15.4 | PHAS= | 28.2 | FOM= | 0.15 | TEST= 0
| INDE | 7 | 39 | 34 | FOBS= | 95.7 | SIGMA= | 2.1 | PHAS= | 99.4 | FOM= | 0.77 | TEST= 0
| INDE | 7 | 39 | 36 | FOBS= | 54.4 | SIGMA= | 3.5 | PHAS= | -89.6 | FOM= | 0.77 | TEST= 0
| INDE | 7 | 39 | 38 | FOBS= | 168.6 | SIGMA= | 1.2 | PHAS= | 2.3 | FOM= | 0.96 | TEST= 0
| INDE | 7 | 39 | 40 | FOBS= | 96.7 | SIGMA= | 2.0 | PHAS= | 60.3 | FOM= | 0.74 | TEST= 0
| INDE | 7 | 39 | 42 | FOBS= | 116.2 | SIGMA= | 1.7 | PHAS= | -66.4 | FOM= | 0.95 | TEST= 0
| INDE | 7 | 39 | 44 | FOBS= | 145.0 | SIGMA= | 1.3 | PHAS= | -128.9 | FOM= | 0.92 | TEST= 0
| INDE | 7 | 39 | 46 | FOBS= | 82.9 | SIGMA= | 2.2 | PHAS= | -70.1 | FOM= | 0.84 | TEST= 0
| INDE | 7 | 39 | 48 | FOBS= | 73.7 | SIGMA= | 2.4 | PHAS= | 120.9 | FOM= | 0.82 | TEST= 0
| INDE | 7 | 39 | 50 | FOBS= | 45.3 | SIGMA= | 3.9 | PHAS= | -12.7 | FOM= | 0.47 | TEST= 0
| INDE | 7 | 39 | 52 | FOBS= | 59.0 | SIGMA= | 3.3 | PHAS= | 17.0 | FOM= | 0.88 | TEST= 0
| INDE | 7 | 39 | 54 | FOBS= | 93.3 | SIGMA= | 2.0 | PHAS= | -13.5 | FOM= | 0.81 | TEST= 0
| INDE | 7 | 39 | 56 | FOBS= | 65.4 | SIGMA= | 2.8 | PHAS= | 68.5 | FOM= | 0.86 | TEST= 0
| INDE | 7 | 39 | 58 | FOBS= | 35.0 | SIGMA= | 5.2 | PHAS= | 117.5 | FOM= | 0.50 | TEST= 0
| INDE | 7 | 39 | 60 | FOBS= | 0.0 | SIGMA= | 22.6 | PHAS= | 0.0 | FOM= | 0.00 | TEST= 0
| INDE | 7 | 39 | 62 | FOBS= | 31.8 | SIGMA= | 5.8 | PHAS= | 56.7 | FOM= | 0.47 | TEST= 0
| INDE | 7 | 39 | 64 | FOBS= | 35.4 | SIGMA= | 6.1 | PHAS= | 148.2 | FOM= | 0.56 | TEST= 0
| INDE | 7 | 39 | 66 | FOBS= | 0.0 | SIGMA= | 27.9 | PHAS= | 0.0 | FOM= | 0.00 | TEST= 0
| INDE | 7 | 40 | 7 | FOBS= | 324.4 | SIGMA= | 0.9 | PHAS= | -52.7 | FOM= | 0.92 | TEST= 0
| INDE | 7 | 40 | 9 | FOBS= | 186.0 | SIGMA= | 0.9 | PHAS= | -121.7 | FOM= | 0.98 | TEST= 1
| INDE | 7 | 40 | 11 | FOBS= | 62.3 | SIGMA= | 2.4 | PHAS= | -57.4 | FOM= | 0.63 | TEST= 1
| INDE | 7 | 40 | 13 | FOBS= | 206.9 | SIGMA= | 0.9 | PHAS= | -107.4 | FOM= | 0.93 | TEST= 0
| INDE | 7 | 40 | 15 | FOBS= | 205.0 | SIGMA= | 1.0 | PHAS= | -150.0 | FOM= | 0.95 | TEST= 0
| INDE | 7 | 40 | 17 | FOBS= | 119.3 | SIGMA= | 1.5 | PHAS= | 2.9 | FOM= | 0.96 | TEST= 0

*FIG. 12A - 200*

```
INDE  7  40  19  FOBS=  145.6  SIGMA=   1.4  PHAS=  -178.6  FOM=  0.92  TEST= 0
INDE  7  40  21  FOBS=  180.5  SIGMA=   1.2  PHAS=  -165.0  FOM=  0.95  TEST= 0
INDE  7  40  23  FOBS=   80.6  SIGMA=   2.4  PHAS=  -129.1  FOM=  0.79  TEST= 0
INDE  7  40  25  FOBS=  251.7  SIGMA=   1.2  PHAS=    31.6  FOM=  0.40  TEST= 1
INDE  7  40  27  FOBS=   49.9  SIGMA=   5.8  PHAS=   -70.0  FOM=  0.46  TEST= 0
INDE  7  40  29  FOBS=  248.5  SIGMA=   1.2  PHAS=   157.0  FOM=  0.96  TEST= 1
INDE  7  40  31  FOBS=  147.7  SIGMA=   1.5  PHAS=    32.2  FOM=  0.86  TEST= 0
INDE  7  40  33  FOBS=  299.6  SIGMA=   0.9  PHAS=  -177.8  FOM=  0.96  TEST= 0
INDE  7  40  35  FOBS=  112.1  SIGMA=   1.8  PHAS=    96.4  FOM=  0.94  TEST= 0
INDE  7  40  37  FOBS=  159.3  SIGMA=   1.3  PHAS=   -90.3  FOM=  0.89  TEST= 0
INDE  7  40  39  FOBS=    0.0  SIGMA=  19.8  PHAS=     0.0  FOM=  0.00  TEST= 0
INDE  7  40  41  FOBS=   88.9  SIGMA=   2.2  PHAS=     5.1  FOM=  0.50  TEST= 1
INDE  7  40  43  FOBS=  139.5  SIGMA=   1.4  PHAS=  -176.9  FOM=  0.94  TEST= 0
INDE  7  40  45  FOBS=   86.5  SIGMA=   2.1  PHAS=   166.7  FOM=  0.76  TEST= 0
INDE  7  40  47  FOBS=   69.3  SIGMA=   2.6  PHAS=    66.6  FOM=  0.85  TEST= 0
INDE  7  40  49  FOBS=   24.8  SIGMA=   7.1  PHAS=   116.8  FOM=  0.21  TEST= 0
INDE  7  40  51  FOBS=  166.1  SIGMA=   1.2  PHAS=   -65.5  FOM=  0.97  TEST= 0
INDE  7  40  53  FOBS=   29.2  SIGMA=   6.5  PHAS=     0.3  FOM=  0.67  TEST= 0
INDE  7  40  55  FOBS=   89.1  SIGMA=   2.1  PHAS=   -81.8  FOM=  0.89  TEST= 0
INDE  7  40  57  FOBS=   48.7  SIGMA=   4.4  PHAS=    71.5  FOM=  0.75  TEST= 0
INDE  7  40  59  FOBS=   58.4  SIGMA=   3.2  PHAS=   -97.6  FOM=  0.25  TEST= 1
INDE  7  40  61  FOBS=   65.0  SIGMA=   2.9  PHAS=    -6.2  FOM=  0.86  TEST= 0
INDE  7  40  63  FOBS=   33.6  SIGMA=   5.9  PHAS=    -4.6  FOM=  0.56  TEST= 0
INDE  7  40  65  FOBS=   60.6  SIGMA=   3.6  PHAS=    99.5  FOM=  0.78  TEST= 0
INDE  7  41   8  FOBS=  202.4  SIGMA=   0.9  PHAS=  -163.1  FOM=  0.97  TEST= 0
INDE  7  41  10  FOBS=  115.7  SIGMA=   1.9  PHAS=   -56.3  FOM=  0.77  TEST= 0
INDE  7  41  12  FOBS=  103.8  SIGMA=   1.6  PHAS=  -119.7  FOM=  0.67  TEST= 0
INDE  7  41  14  FOBS=  227.6  SIGMA=   0.9  PHAS=  -162.9  FOM=  0.97  TEST= 0
INDE  7  41  16  FOBS=   72.6  SIGMA=   2.4  PHAS=    66.9  FOM=  0.20  TEST= 0
INDE  7  41  18  FOBS=    0.0  SIGMA=  18.9  PHAS=     0.0  FOM=  0.00  TEST= 1
INDE  7  41  20  FOBS=  388.1  SIGMA=   1.0  PHAS=   106.4  FOM=  0.89  TEST= 1
INDE  7  41  22  FOBS=  155.7  SIGMA=   1.4  PHAS=     8.2  FOM=  0.91  TEST= 0
INDE  7  41  24  FOBS=  195.2  SIGMA=   1.2  PHAS=   -79.7  FOM=  0.91  TEST= 0
INDE  7  41  26  FOBS=   52.5  SIGMA=   5.0  PHAS=   124.9  FOM=  0.87  TEST= 0
INDE  7  41  28  FOBS=  225.6  SIGMA=   1.3  PHAS=   133.4  FOM=  0.94  TEST= 0
INDE  7  41  30  FOBS=   94.2  SIGMA=   2.7  PHAS=   -17.8  FOM=  0.91  TEST= 0
INDE  7  41  32  FOBS=  284.8  SIGMA=   0.9  PHAS=   -60.4  FOM=  0.12  TEST= 1
INDE  7  41  34  FOBS=  192.6  SIGMA=   1.1  PHAS=    53.3  FOM=  0.95  TEST= 0
INDE  7  41  36  FOBS=   81.0  SIGMA=   2.4  PHAS=   159.2  FOM=  0.66  TEST= 0
INDE  7  41  38  FOBS=  104.7  SIGMA=   1.9  PHAS=   -53.4  FOM=  0.90  TEST= 0
INDE  7  41  40  FOBS=   62.8  SIGMA=   3.0  PHAS=   -51.2  FOM=  0.73  TEST= 0
INDE  7  41  42  FOBS=    0.0  SIGMA=  19.3  PHAS=     0.0  FOM=  0.00  TEST= 0
INDE  7  41  44  FOBS=   61.9  SIGMA=   3.0  PHAS=   138.2  FOM=  0.84  TEST= 0
INDE  7  41  46  FOBS=  113.6  SIGMA=   1.6  PHAS=   -54.1  FOM=  0.94  TEST= 0
INDE  7  41  48  FOBS=   57.0  SIGMA=   3.1  PHAS=   -28.8  FOM=  0.24  TEST= 0
INDE  7  41  50  FOBS=   76.2  SIGMA=   2.4  PHAS=  -126.6  FOM=  0.88  TEST= 0
INDE  7  41  52  FOBS=   41.9  SIGMA=   5.1  PHAS=  -160.8  FOM=  0.58  TEST= 0
INDE  7  41  54  FOBS=   75.5  SIGMA=   2.5  PHAS=  -167.7  FOM=  0.86  TEST= 0
INDE  7  41  56  FOBS=   26.0  SIGMA=   7.2  PHAS=    -6.5  FOM=  0.86  TEST= 0
INDE  7  41  58  FOBS=   36.4  SIGMA=   5.1  PHAS=   124.5  FOM=  0.69  TEST= 0
INDE  7  41  60  FOBS=   83.5  SIGMA=   2.3  PHAS=  -140.0  FOM=  0.93  TEST= 0
INDE  7  41  62  FOBS=   67.2  SIGMA=   2.8  PHAS=   -38.6  FOM=  0.29  TEST= 1
INDE  7  41  64  FOBS=   55.9  SIGMA=   4.3  PHAS=    19.0  FOM=  0.82  TEST= 0
INDE  7  42   7  FOBS=  349.5  SIGMA=   0.9  PHAS=   120.9  FOM=  0.96  TEST= 0
INDE  7  42   9  FOBS=  249.8  SIGMA=   1.3  PHAS=  -154.7  FOM=  0.95  TEST= 0
INDE  7  42  11  FOBS=  234.0  SIGMA=   1.2  PHAS=   152.4  FOM=  0.93  TEST= 0
INDE  7  42  13  FOBS=  139.4  SIGMA=   1.3  PHAS=  -176.9  FOM=  0.96  TEST= 0
INDE  7  42  15  FOBS=  105.7  SIGMA=   1.7  PHAS=   105.1  FOM=  0.70  TEST= 0
INDE  7  42  17  FOBS=   56.6  SIGMA=   3.7  PHAS=     0.9  FOM=  0.92  TEST= 0
INDE  7  42  19  FOBS=  372.1  SIGMA=   0.9  PHAS=   -83.3  FOM=  0.98  TEST= 0
INDE  7  42  21  FOBS=  210.4  SIGMA=   1.2  PHAS=    16.6  FOM=  0.91  TEST= 0
INDE  7  42  23  FOBS=   78.3  SIGMA=   2.7  PHAS=   146.2  FOM=  0.76  TEST= 0
INDE  7  42  25  FOBS=  112.5  SIGMA=   1.9  PHAS=   162.1  FOM=  0.87  TEST= 0
INDE  7  42  27  FOBS=  163.5  SIGMA=   1.7  PHAS=    67.2  FOM=  0.91  TEST= 0
INDE  7  42  29  FOBS=  159.3  SIGMA=   2.0  PHAS=   -98.7  FOM=  0.10  TEST= 1
INDE  7  42  31  FOBS=  137.8  SIGMA=   1.9  PHAS=  -106.3  FOM=  0.95  TEST= 0
INDE  7  42  33  FOBS=  189.1  SIGMA=   1.3  PHAS=  -112.1  FOM=  0.91  TEST= 0
INDE  7  42  35  FOBS=  115.2  SIGMA=   1.7  PHAS=    33.4  FOM=  0.88  TEST= 0
INDE  7  42  37  FOBS=   38.8  SIGMA=   5.2  PHAS=   120.3  FOM=  0.14  TEST= 0
INDE  7  42  39  FOBS=  147.7  SIGMA=   1.4  PHAS=  -150.1  FOM=  0.96  TEST= 0
```

*FIG. 12A - 201*

```
INDE  7  42  41  FOBS=    0.0  SIGMA=  19.4  PHAS=    0.0  FOM=  0.00  TEST= 1
INDE  7  42  43  FOBS=   58.7  SIGMA=   3.2  PHAS=    1.7  FOM=  0.78  TEST= 1
INDE  7  42  45  FOBS=   49.3  SIGMA=   3.7  PHAS= -159.4  FOM=  0.54  TEST= 0
INDE  7  42  47  FOBS=   12.9  SIGMA=  14.5  PHAS= -126.6  FOM=  0.09  TEST= 1
INDE  7  42  49  FOBS=   72.3  SIGMA=   2.5  PHAS= -168.0  FOM=  0.77  TEST= 0
INDE  7  42  51  FOBS=   89.2  SIGMA=   2.3  PHAS=   30.1  FOM=  0.79  TEST= 0
INDE  7  42  53  FOBS=  109.1  SIGMA=   1.7  PHAS=  108.2  FOM=  0.64  TEST= 1
INDE  7  42  55  FOBS=   33.3  SIGMA=   5.6  PHAS=   35.1  FOM=  0.24  TEST= 0
INDE  7  42  57  FOBS=   35.4  SIGMA=   5.3  PHAS=  -21.6  FOM=  0.24  TEST= 0
INDE  7  42  59  FOBS=   56.6  SIGMA=   3.3  PHAS=   97.8  FOM=  0.58  TEST= 0
INDE  7  42  61  FOBS=    0.0  SIGMA=  19.3  PHAS=    0.0  FOM=  0.00  TEST= 0
INDE  7  42  63  FOBS=    0.0  SIGMA=  21.9  PHAS=    0.0  FOM=  0.00  TEST= 0
INDE  7  42  65  FOBS=   56.3  SIGMA=   7.2  PHAS=   23.3  FOM=  0.76  TEST= 0
INDE  7  43   8  FOBS=  107.4  SIGMA=   1.6  PHAS=   64.8  FOM=  0.93  TEST= 0
INDE  7  43  10  FOBS=  188.2  SIGMA=   1.4  PHAS=  117.7  FOM=  0.95  TEST= 0
INDE  7  43  12  FOBS=   96.2  SIGMA=   1.8  PHAS=   25.1  FOM=  0.88  TEST= 0
INDE  7  43  14  FOBS=   31.0  SIGMA=   5.7  PHAS= -141.5  FOM=  0.19  TEST= 0
INDE  7  43  16  FOBS=   57.0  SIGMA=   3.3  PHAS=  108.9  FOM=  0.24  TEST= 0
INDE  7  43  18  FOBS=  270.4  SIGMA=   0.9  PHAS= -152.7  FOM=  0.97  TEST= 0
INDE  7  43  20  FOBS=   43.7  SIGMA=   5.0  PHAS=  132.7  FOM=  0.63  TEST= 0
INDE  7  43  22  FOBS=  113.5  SIGMA=   2.1  PHAS=   -2.6  FOM=  0.98  TEST= 0
INDE  7  43  24  FOBS=  148.1  SIGMA=   1.5  PHAS=  125.1  FOM=  0.65  TEST= 0
INDE  7  43  26  FOBS=  137.1  SIGMA=   1.6  PHAS=   81.1  FOM=  0.88  TEST= 0
INDE  7  43  28  FOBS=  162.1  SIGMA=   1.7  PHAS=  -42.4  FOM=  0.93  TEST= 0
INDE  7  43  30  FOBS=   25.7  SIGMA=  10.7  PHAS=  141.5  FOM=  0.37  TEST= 0
INDE  7  43  32  FOBS=    0.0  SIGMA=  22.1  PHAS=    0.0  FOM=  0.00  TEST= 0
INDE  7  43  34  FOBS=  101.8  SIGMA=   2.1  PHAS= -100.3  FOM=  0.93  TEST= 0
INDE  7  43  36  FOBS=   49.8  SIGMA=   3.8  PHAS=   37.2  FOM=  0.84  TEST= 1
INDE  7  43  38  FOBS=  117.2  SIGMA=   1.7  PHAS=  -46.4  FOM=  0.67  TEST= 1
INDE  7  43  40  FOBS=  140.8  SIGMA=   1.4  PHAS=  -69.0  FOM=  0.89  TEST= 0
INDE  7  43  42  FOBS=   83.7  SIGMA=   2.3  PHAS=  -53.9  FOM=  0.77  TEST= 0
INDE  7  43  44  FOBS=   64.8  SIGMA=   2.9  PHAS= -100.5  FOM=  0.88  TEST= 0
INDE  7  43  46  FOBS=   47.4  SIGMA=   3.8  PHAS= -179.9  FOM=  0.67  TEST= 0
INDE  7  43  48  FOBS=   59.1  SIGMA=   3.0  PHAS= -179.8  FOM=  0.84  TEST= 0
INDE  7  43  50  FOBS=   32.0  SIGMA=   6.0  PHAS=   30.1  FOM=  0.35  TEST= 0
INDE  7  43  52  FOBS=  161.7  SIGMA=   1.3  PHAS=   16.7  FOM=  0.96  TEST= 0
INDE  7  43  54  FOBS=   46.5  SIGMA=   3.8  PHAS=   34.0  FOM=  0.67  TEST= 0
INDE  7  43  56  FOBS=   41.7  SIGMA=   4.5  PHAS=  -35.7  FOM=  0.55  TEST= 0
INDE  7  43  58  FOBS=   57.3  SIGMA=   3.3  PHAS=  127.6  FOM=  0.81  TEST= 0
INDE  7  43  60  FOBS=   45.8  SIGMA=   4.1  PHAS=  163.2  FOM=  0.20  TEST= 0
INDE  7  43  62  FOBS=    0.0  SIGMA=  21.7  PHAS=    0.0  FOM=  0.00  TEST= 0
INDE  7  43  64  FOBS=   36.5  SIGMA=   8.7  PHAS= -110.5  FOM=  0.42  TEST= 0
INDE  7  44   7  FOBS=  164.3  SIGMA=   1.3  PHAS=   25.0  FOM=  0.92  TEST= 0
INDE  7  44   9  FOBS=  119.5  SIGMA=   1.4  PHAS=  163.3  FOM=  0.46  TEST= 0
INDE  7  44  11  FOBS=   90.0  SIGMA=   1.7  PHAS=   72.7  FOM=  0.91  TEST= 0
INDE  7  44  13  FOBS=   90.0  SIGMA=   2.1  PHAS=  -13.3  FOM=  0.85  TEST= 0
INDE  7  44  15  FOBS=  172.2  SIGMA=   1.2  PHAS=  -38.9  FOM=  0.95  TEST= 0
INDE  7  44  17  FOBS=   71.5  SIGMA=   2.8  PHAS=   69.7  FOM=  0.48  TEST= 0
INDE  7  44  19  FOBS=  118.8  SIGMA=   1.8  PHAS=   81.8  FOM=  0.91  TEST= 1
INDE  7  44  21  FOBS=   57.8  SIGMA=   3.6  PHAS=  139.9  FOM=  0.83  TEST= 0
INDE  7  44  23  FOBS=    0.0  SIGMA=  20.6  PHAS=    0.0  FOM=  0.00  TEST= 0
INDE  7  44  25  FOBS=  133.6  SIGMA=   1.6  PHAS=   21.5  FOM=  0.89  TEST= 0
INDE  7  44  27  FOBS=  148.7  SIGMA=   1.6  PHAS= -177.9  FOM=  0.84  TEST= 0
INDE  7  44  29  FOBS=   58.2  SIGMA=   4.4  PHAS=   61.2  FOM=  0.77  TEST= 0
INDE  7  44  31  FOBS=   97.0  SIGMA=   2.6  PHAS=  -95.5  FOM=  0.81  TEST= 0
INDE  7  44  33  FOBS=   56.5  SIGMA=   3.7  PHAS= -145.7  FOM=  0.52  TEST= 1
INDE  7  44  35  FOBS=  171.0  SIGMA=   1.3  PHAS=  174.9  FOM=  0.96  TEST= 0
INDE  7  44  37  FOBS=  115.4  SIGMA=   1.7  PHAS= -117.8  FOM=  0.87  TEST= 0
INDE  7  44  39  FOBS=   78.3  SIGMA=   2.5  PHAS= -176.1  FOM=  0.86  TEST= 1
INDE  7  44  41  FOBS=    0.0  SIGMA=  22.2  PHAS=    0.0  FOM=  0.00  TEST= 0
INDE  7  44  43  FOBS=   53.4  SIGMA=   3.5  PHAS=  -87.0  FOM=  0.81  TEST= 0
INDE  7  44  45  FOBS=    7.3  SIGMA=  27.6  PHAS=   58.0  FOM=  0.06  TEST= 0
INDE  7  44  47  FOBS=   35.0  SIGMA=   5.4  PHAS=  145.0  FOM=  0.49  TEST= 0
INDE  7  44  49  FOBS=   39.0  SIGMA=   4.5  PHAS=  154.2  FOM=  0.68  TEST= 0
INDE  7  44  51  FOBS=   49.4  SIGMA=   4.0  PHAS=  -53.1  FOM=  0.73  TEST= 0
INDE  7  44  53  FOBS=   78.0  SIGMA=   2.3  PHAS=  -75.8  FOM=  0.69  TEST= 0
INDE  7  44  55  FOBS=   54.6  SIGMA=   3.3  PHAS=  -90.9  FOM=  0.87  TEST= 0
INDE  7  44  57  FOBS=   51.5  SIGMA=   3.7  PHAS=   55.8  FOM=  0.85  TEST= 0
INDE  7  44  59  FOBS=   50.1  SIGMA=   3.8  PHAS=  126.1  FOM=  0.31  TEST= 1
INDE  7  44  61  FOBS=    0.0  SIGMA=  21.8  PHAS=    0.0  FOM=  0.00  TEST= 0
```

*FIG. 12A - 202*

```
INDE  7 44 63 FOBS=  63.2 SIGMA=  3.6 PHAS=  125.5 FOM= 0.88 TEST= 0
INDE  7 45  8 FOBS=  95.1 SIGMA=  2.7 PHAS=   28.6 FOM= 0.73 TEST= 0
INDE  7 45 10 FOBS= 221.8 SIGMA=  1.6 PHAS=  -80.8 FOM= 0.94 TEST= 0
INDE  7 45 12 FOBS= 230.1 SIGMA=  0.8 PHAS=  143.8 FOM= 0.95 TEST= 0
INDE  7 45 14 FOBS= 167.7 SIGMA=  1.2 PHAS=  -73.7 FOM= 0.91 TEST= 0
INDE  7 45 16 FOBS= 291.9 SIGMA=  0.9 PHAS= -148.0 FOM= 0.86 TEST= 1
INDE  7 45 18 FOBS=  13.8 SIGMA= 14.8 PHAS=   61.8 FOM= 0.27 TEST= 0
INDE  7 45 20 FOBS= 160.6 SIGMA=  1.5 PHAS=  175.3 FOM= 0.42 TEST= 1
INDE  7 45 22 FOBS= 103.1 SIGMA=  2.1 PHAS=  -19.3 FOM= 0.63 TEST= 0
INDE  7 45 24 FOBS=  56.0 SIGMA=  3.8 PHAS=  161.1 FOM= 0.68 TEST= 0
INDE  7 45 26 FOBS=  91.7 SIGMA=  2.3 PHAS=   26.6 FOM= 0.40 TEST= 0
INDE  7 45 28 FOBS= 245.5 SIGMA=  1.2 PHAS=  -43.4 FOM= 0.95 TEST= 0
INDE  7 45 30 FOBS=  37.5 SIGMA=  7.9 PHAS=  -73.3 FOM= 0.10 TEST= 0
INDE  7 45 32 FOBS=  40.4 SIGMA=  6.1 PHAS= -147.3 FOM= 0.38 TEST= 0
INDE  7 45 34 FOBS=  30.3 SIGMA=  7.8 PHAS=  -94.9 FOM= 0.38 TEST= 0
INDE  7 45 36 FOBS= 206.6 SIGMA=  1.1 PHAS=   82.3 FOM= 0.96 TEST= 0
INDE  7 45 38 FOBS=   0.0 SIGMA= 20.1 PHAS=    0.0 FOM= 0.00 TEST= 0
INDE  7 45 40 FOBS= 128.1 SIGMA=  1.5 PHAS=   76.0 FOM= 0.93 TEST= 1
INDE  7 45 42 FOBS=   0.0 SIGMA= 19.8 PHAS=    0.0 FOM= 0.00 TEST= 0
INDE  7 45 44 FOBS=  57.4 SIGMA=  3.2 PHAS=  146.7 FOM= 0.41 TEST= 0
INDE  7 45 46 FOBS=  80.9 SIGMA=  2.3 PHAS=  143.1 FOM= 0.83 TEST= 0
INDE  7 45 48 FOBS= 133.4 SIGMA=  1.4 PHAS=  -61.4 FOM= 0.15 TEST= 1
INDE  7 45 50 FOBS=  91.1 SIGMA=  2.2 PHAS=  102.2 FOM= 0.93 TEST= 0
INDE  7 45 52 FOBS=   0.0 SIGMA= 21.5 PHAS=    0.0 FOM= 0.00 TEST= 0
INDE  7 45 54 FOBS=  68.9 SIGMA=  2.6 PHAS=  158.4 FOM= 0.82 TEST= 0
INDE  7 45 56 FOBS=   0.0 SIGMA= 19.9 PHAS=    0.0 FOM= 0.00 TEST= 0
INDE  7 45 58 FOBS=  11.1 SIGMA= 17.1 PHAS=   16.6 FOM= 0.15 TEST= 0
INDE  7 45 60 FOBS=  44.1 SIGMA=  4.7 PHAS=   27.7 FOM= 0.82 TEST= 0
INDE  7 45 62 FOBS=  14.3 SIGMA= 19.1 PHAS=  -11.7 FOM= 0.17 TEST= 0
INDE  7 46  7 FOBS=  64.8 SIGMA=  3.0 PHAS=   75.9 FOM= 0.95 TEST= 0
INDE  7 46  9 FOBS= 238.7 SIGMA=  0.8 PHAS= -154.8 FOM= 0.96 TEST= 0
INDE  7 46 11 FOBS= 194.5 SIGMA=  0.9 PHAS=   55.8 FOM= 0.94 TEST= 0
INDE  7 46 13 FOBS= 318.4 SIGMA=  0.9 PHAS=   64.5 FOM= 0.96 TEST= 0
INDE  7 46 15 FOBS= 191.2 SIGMA=  1.2 PHAS=  168.7 FOM= 0.88 TEST= 0
INDE  7 46 17 FOBS= 171.3 SIGMA=  1.3 PHAS= -152.4 FOM= 0.96 TEST= 0
INDE  7 46 19 FOBS= 226.0 SIGMA=  1.0 PHAS=   54.1 FOM= 0.95 TEST= 0
INDE  7 46 21 FOBS=  81.9 SIGMA=  2.7 PHAS=   86.7 FOM= 0.34 TEST= 0
INDE  7 46 23 FOBS=  50.4 SIGMA=  4.1 PHAS=   52.8 FOM= 0.26 TEST= 0
INDE  7 46 25 FOBS= 173.8 SIGMA=  1.3 PHAS=    7.5 FOM= 0.89 TEST= 0
INDE  7 46 27 FOBS= 164.5 SIGMA=  1.3 PHAS= -116.8 FOM= 0.89 TEST= 0
INDE  7 46 29 FOBS=   0.0 SIGMA= 22.4 PHAS=    0.0 FOM= 0.00 TEST= 0
INDE  7 46 31 FOBS=  77.9 SIGMA=  3.2 PHAS=   58.9 FOM= 0.77 TEST= 0
INDE  7 46 33 FOBS=  81.9 SIGMA=  3.0 PHAS=   43.5 FOM= 0.30 TEST= 0
INDE  7 46 35 FOBS=  76.1 SIGMA=  2.8 PHAS=  139.5 FOM= 0.74 TEST= 0
INDE  7 46 37 FOBS=  94.9 SIGMA=  2.0 PHAS=  -50.2 FOM= 0.89 TEST= 0
INDE  7 46 39 FOBS= 107.5 SIGMA=  1.8 PHAS=  -15.3 FOM= 0.92 TEST= 0
INDE  7 46 41 FOBS= 108.4 SIGMA=  1.8 PHAS=   31.2 FOM= 0.90 TEST= 1
INDE  7 46 43 FOBS=  90.6 SIGMA=  2.1 PHAS=  -78.1 FOM= 0.88 TEST= 0
INDE  7 46 45 FOBS=  37.8 SIGMA=  5.1 PHAS=   16.7 FOM= 0.53 TEST= 0
INDE  7 46 47 FOBS=  97.6 SIGMA=  1.9 PHAS=  146.4 FOM= 0.52 TEST= 1
INDE  7 46 49 FOBS=  71.6 SIGMA=  2.5 PHAS=   80.1 FOM= 0.90 TEST= 0
INDE  7 46 51 FOBS=  23.3 SIGMA=  8.4 PHAS=   -5.3 FOM= 0.57 TEST= 0
INDE  7 46 53 FOBS=  44.2 SIGMA=  4.7 PHAS=   39.3 FOM= 0.70 TEST= 0
INDE  7 46 55 FOBS=  69.4 SIGMA=  2.6 PHAS=   54.8 FOM= 0.67 TEST= 0
INDE  7 46 57 FOBS=   0.0 SIGMA= 20.1 PHAS=    0.0 FOM= 0.00 TEST= 0
INDE  7 46 59 FOBS=  75.4 SIGMA=  2.6 PHAS= -101.7 FOM= 0.88 TEST= 0
INDE  7 46 61 FOBS=  42.2 SIGMA=  5.4 PHAS= -110.3 FOM= 0.84 TEST= 0
INDE  7 47  8 FOBS=  38.1 SIGMA=  8.4 PHAS=   11.2 FOM= 0.56 TEST= 0
INDE  7 47 10 FOBS= 213.7 SIGMA=  1.5 PHAS= -103.5 FOM= 0.95 TEST= 0
INDE  7 47 12 FOBS= 130.4 SIGMA=  1.4 PHAS=  135.9 FOM= 0.83 TEST= 0
INDE  7 47 14 FOBS= 247.6 SIGMA=  1.1 PHAS=  -44.7 FOM= 0.97 TEST= 0
INDE  7 47 16 FOBS= 203.6 SIGMA=  1.1 PHAS=   49.4 FOM= 0.26 TEST= 1
INDE  7 47 18 FOBS=   0.0 SIGMA= 20.2 PHAS=    0.0 FOM= 0.00 TEST= 1
INDE  7 47 20 FOBS= 150.9 SIGMA=  1.6 PHAS=   58.6 FOM= 0.89 TEST= 1
INDE  7 47 22 FOBS=  47.2 SIGMA=  4.3 PHAS= -176.7 FOM= 0.54 TEST= 0
INDE  7 47 24 FOBS=  79.7 SIGMA=  2.6 PHAS= -168.6 FOM= 0.69 TEST= 0
INDE  7 47 26 FOBS= 190.1 SIGMA=  1.2 PHAS=  -89.2 FOM= 0.90 TEST= 0
INDE  7 47 28 FOBS=   0.0 SIGMA= 20.6 PHAS=    0.0 FOM= 0.00 TEST= 0
INDE  7 47 30 FOBS= 124.2 SIGMA=  2.1 PHAS=  -99.9 FOM= 0.70 TEST= 0
INDE  7 47 32 FOBS= 136.9 SIGMA=  1.9 PHAS=  -29.7 FOM= 0.97 TEST= 0
```

FIG. 12A - 203

| | | | | | | | | | | | |
|---|---|---|---|---|---|---|---|---|---|---|---|
|INDE|7|47|34|FOBS=|108.8|SIGMA=|2.3|PHAS=|61.9|FOM=|0.70|TEST=|0|
|INDE|7|47|36|FOBS=|51.2|SIGMA=|4.1|PHAS=|62.0|FOM=|0.62|TEST=|0|
|INDE|7|47|38|FOBS=|153.8|SIGMA=|1.3|PHAS=|-107.8|FOM=|0.94|TEST=|0|
|INDE|7|47|40|FOBS=|100.2|SIGMA=|1.9|PHAS=|-85.7|FOM=|0.66|TEST=|1|
|INDE|7|47|42|FOBS=|125.1|SIGMA=|1.6|PHAS=|-99.8|FOM=|0.91|TEST=|0|
|INDE|7|47|44|FOBS=|95.5|SIGMA=|2.0|PHAS=|175.9|FOM=|0.91|TEST=|0|
|INDE|7|47|46|FOBS=|111.0|SIGMA=|1.7|PHAS=|70.3|FOM=|0.77|TEST=|0|
|INDE|7|47|48|FOBS=|0.0|SIGMA=|19.9|PHAS=|0.0|FOM=|0.00|TEST=|1|
|INDE|7|47|50|FOBS=|0.0|SIGMA=|19.8|PHAS=|0.0|FOM=|0.00|TEST=|1|
|INDE|7|47|52|FOBS=|25.0|SIGMA=|9.5|PHAS=|-33.3|FOM=|0.49|TEST=|0|
|INDE|7|47|54|FOBS=|44.2|SIGMA=|4.4|PHAS=|-115.1|FOM=|0.33|TEST=|1|
|INDE|7|47|56|FOBS=|71.8|SIGMA=|2.6|PHAS=|-60.4|FOM=|0.73|TEST=|0|
|INDE|7|47|58|FOBS=|24.4|SIGMA=|7.9|PHAS=|133.2|FOM=|0.74|TEST=|0|
|INDE|7|47|60|FOBS=|8.0|SIGMA=|28.4|PHAS=|163.7|FOM=|0.22|TEST=|0|
|INDE|7|48|7|FOBS=|139.1|SIGMA=|1.5|PHAS=|91.5|FOM=|0.06|TEST=|1|
|INDE|7|48|9|FOBS=|144.3|SIGMA=|2.0|PHAS=|-41.2|FOM=|0.55|TEST=|0|
|INDE|7|48|11|FOBS=|137.9|SIGMA=|1.2|PHAS=|-9.1|FOM=|0.25|TEST=|0|
|INDE|7|48|13|FOBS=|191.5|SIGMA=|1.2|PHAS=|144.1|FOM=|0.94|TEST=|0|
|INDE|7|48|15|FOBS=|308.0|SIGMA=|0.8|PHAS=|-118.3|FOM=|0.98|TEST=|0|
|INDE|7|48|17|FOBS=|140.9|SIGMA=|1.5|PHAS=|-147.2|FOM=|0.85|TEST=|0|
|INDE|7|48|19|FOBS=|136.5|SIGMA=|1.6|PHAS=|52.2|FOM=|0.89|TEST=|0|
|INDE|7|48|21|FOBS=|129.0|SIGMA=|1.7|PHAS=|40.0|FOM=|0.81|TEST=|1|
|INDE|7|48|23|FOBS=|125.6|SIGMA=|1.7|PHAS=|107.3|FOM=|0.84|TEST=|0|
|INDE|7|48|25|FOBS=|54.4|SIGMA=|3.8|PHAS=|121.8|FOM=|0.18|TEST=|0|
|INDE|7|48|27|FOBS=|98.6|SIGMA=|2.1|PHAS=|116.3|FOM=|0.95|TEST=|0|
|INDE|7|48|29|FOBS=|126.4|SIGMA=|1.6|PHAS=|30.3|FOM=|0.94|TEST=|0|
|INDE|7|48|31|FOBS=|72.7|SIGMA=|3.4|PHAS=|-51.5|FOM=|0.55|TEST=|0|
|INDE|7|48|33|FOBS=|111.5|SIGMA=|2.3|PHAS=|-156.7|FOM=|0.93|TEST=|0|
|INDE|7|48|35|FOBS=|74.8|SIGMA=|3.0|PHAS=|140.3|FOM=|0.75|TEST=|0|
|INDE|7|48|37|FOBS=|74.5|SIGMA=|2.8|PHAS=|-94.7|FOM=|0.78|TEST=|0|
|INDE|7|48|39|FOBS=|80.0|SIGMA=|2.4|PHAS=|115.7|FOM=|0.71|TEST=|0|
|INDE|7|48|41|FOBS=|51.0|SIGMA=|3.6|PHAS=|-149.1|FOM=|0.54|TEST=|0|
|INDE|7|48|43|FOBS=|69.3|SIGMA=|2.7|PHAS=|157.6|FOM=|0.56|TEST=|0|
|INDE|7|48|45|FOBS=|158.7|SIGMA=|1.2|PHAS=|51.7|FOM=|0.91|TEST=|0|
|INDE|7|48|47|FOBS=|63.2|SIGMA=|2.9|PHAS=|-166.5|FOM=|0.82|TEST=|0|
|INDE|7|48|49|FOBS=|70.9|SIGMA=|3.1|PHAS=|-138.7|FOM=|0.37|TEST=|1|
|INDE|7|48|51|FOBS=|43.1|SIGMA=|4.6|PHAS=|-95.8|FOM=|0.59|TEST=|0|
|INDE|7|48|53|FOBS=|59.0|SIGMA=|3.1|PHAS=|97.6|FOM=|0.02|TEST=|1|
|INDE|7|48|55|FOBS=|17.9|SIGMA=|11.4|PHAS=|-26.5|FOM=|0.29|TEST=|0|
|INDE|7|48|57|FOBS=|0.0|SIGMA=|20.2|PHAS=|0.0|FOM=|0.00|TEST=|1|
|INDE|7|48|59|FOBS=|55.1|SIGMA=|3.9|PHAS=|103.3|FOM=|0.73|TEST=|0|
|INDE|7|49|8|FOBS=|35.1|SIGMA=|7.9|PHAS=|-158.7|FOM=|0.33|TEST=|0|
|INDE|7|49|10|FOBS=|167.1|SIGMA=|1.8|PHAS=|-132.5|FOM=|0.90|TEST=|0|
|INDE|7|49|12|FOBS=|202.5|SIGMA=|0.9|PHAS=|112.2|FOM=|0.94|TEST=|0|
|INDE|7|49|14|FOBS=|0.0|SIGMA=|19.7|PHAS=|0.0|FOM=|0.00|TEST=|0|
|INDE|7|49|16|FOBS=|92.0|SIGMA=|2.3|PHAS=|-103.7|FOM=|0.89|TEST=|0|
|INDE|7|49|18|FOBS=|61.0|SIGMA=|3.3|PHAS=|74.6|FOM=|0.78|TEST=|0|
|INDE|7|49|20|FOBS=|0.0|SIGMA=|21.8|PHAS=|0.0|FOM=|0.00|TEST=|0|
|INDE|7|49|22|FOBS=|171.0|SIGMA=|1.3|PHAS=|175.7|FOM=|0.94|TEST=|0|
|INDE|7|49|24|FOBS=|157.3|SIGMA=|1.4|PHAS=|9.9|FOM=|0.92|TEST=|0|
|INDE|7|49|26|FOBS=|196.9|SIGMA=|1.2|PHAS=|-5.8|FOM=|0.91|TEST=|0|
|INDE|7|49|28|FOBS=|152.1|SIGMA=|1.4|PHAS=|-24.8|FOM=|0.90|TEST=|0|
|INDE|7|49|30|FOBS=|148.1|SIGMA=|1.4|PHAS=|-116.9|FOM=|0.93|TEST=|0|
|INDE|7|49|32|FOBS=|81.7|SIGMA=|3.1|PHAS=|67.0|FOM=|0.87|TEST=|0|
|INDE|7|49|34|FOBS=|224.2|SIGMA=|1.3|PHAS=|107.4|FOM=|0.98|TEST=|0|
|INDE|7|49|36|FOBS=|67.2|SIGMA=|3.1|PHAS=|119.9|FOM=|0.64|TEST=|0|
|INDE|7|49|38|FOBS=|43.7|SIGMA=|4.7|PHAS=|-107.8|FOM=|0.68|TEST=|0|
|INDE|7|49|40|FOBS=|0.0|SIGMA=|22.3|PHAS=|0.0|FOM=|0.00|TEST=|0|
|INDE|7|49|42|FOBS=|35.3|SIGMA=|5.5|PHAS=|-130.4|FOM=|0.38|TEST=|0|
|INDE|7|49|44|FOBS=|50.4|SIGMA=|4.1|PHAS=|-75.4|FOM=|0.60|TEST=|0|
|INDE|7|49|46|FOBS=|30.0|SIGMA=|6.4|PHAS=|22.4|FOM=|0.35|TEST=|0|
|INDE|7|49|48|FOBS=|112.4|SIGMA=|1.7|PHAS=|63.8|FOM=|0.90|TEST=|0|
|INDE|7|49|50|FOBS=|20.3|SIGMA=|9.8|PHAS=|178.5|FOM=|0.41|TEST=|0|
|INDE|7|49|52|FOBS=|63.0|SIGMA=|3.2|PHAS=|147.6|FOM=|0.84|TEST=|0|
|INDE|7|49|54|FOBS=|35.6|SIGMA=|5.1|PHAS=|-161.5|FOM=|0.61|TEST=|0|
|INDE|7|49|56|FOBS=|69.2|SIGMA=|2.7|PHAS=|-72.7|FOM=|0.78|TEST=|0|
|INDE|7|49|58|FOBS=|52.1|SIGMA=|4.1|PHAS=|93.5|FOM=|0.76|TEST=|0|
|INDE|7|50|7|FOBS=|208.1|SIGMA=|1.2|PHAS=|80.5|FOM=|0.97|TEST=|0|
|INDE|7|50|9|FOBS=|145.0|SIGMA=|2.0|PHAS=|-12.9|FOM=|0.89|TEST=|0|
|INDE|7|50|11|FOBS=|140.0|SIGMA=|1.4|PHAS=|95.3|FOM=|0.84|TEST=|0|

*FIG. 12A - 204*

```
INDE  7  50  13  FOBS=   99.7  SIGMA=   1.7  PHAS=  147.2  FOM=  0.94  TEST= 0
INDE  7  50  15  FOBS=  159.5  SIGMA=   1.0  PHAS= -152.9  FOM=  0.95  TEST= 0
INDE  7  50  17  FOBS=  107.2  SIGMA=   1.9  PHAS=  131.7  FOM=  0.94  TEST= 0
INDE  7  50  19  FOBS=  153.6  SIGMA=   1.4  PHAS=  -18.1  FOM=  0.96  TEST= 0
INDE  7  50  21  FOBS=  138.3  SIGMA=   1.6  PHAS=   75.2  FOM=  0.90  TEST= 0
INDE  7  50  23  FOBS=  121.0  SIGMA=   1.7  PHAS=   33.4  FOM=  0.91  TEST= 0
INDE  7  50  25  FOBS=  116.6  SIGMA=   1.8  PHAS=  176.0  FOM=  0.28  TEST= 1
INDE  7  50  27  FOBS=   61.0  SIGMA=   3.8  PHAS=   94.9  FOM=  0.61  TEST= 0
INDE  7  50  29  FOBS=   71.2  SIGMA=   2.8  PHAS=  107.1  FOM=  0.90  TEST= 0
INDE  7  50  31  FOBS=   68.0  SIGMA=   2.9  PHAS= -107.7  FOM=  0.68  TEST= 0
INDE  7  50  33  FOBS=  172.7  SIGMA=   1.6  PHAS=   11.2  FOM=  0.96  TEST= 0
INDE  7  50  35  FOBS=  127.1  SIGMA=   2.0  PHAS=   54.3  FOM=  0.94  TEST= 0
INDE  7  50  37  FOBS=   36.8  SIGMA=   5.6  PHAS=  -22.5  FOM=  0.59  TEST= 0
INDE  7  50  39  FOBS=   24.4  SIGMA=   8.7  PHAS=  -28.3  FOM=  0.76  TEST= 0
INDE  7  50  41  FOBS=   69.8  SIGMA=   2.6  PHAS= -152.3  FOM=  0.63  TEST= 0
INDE  7  50  43  FOBS=   94.4  SIGMA=   2.0  PHAS=  153.4  FOM=  0.82  TEST= 0
INDE  7  50  45  FOBS=   39.4  SIGMA=   4.9  PHAS=  128.7  FOM=  0.52  TEST= 0
INDE  7  50  47  FOBS=   81.9  SIGMA=   2.3  PHAS=  -49.6  FOM=  0.75  TEST= 0
INDE  7  50  49  FOBS=   90.6  SIGMA=   2.3  PHAS=  -70.8  FOM=  0.81  TEST= 0
INDE  7  50  51  FOBS=   89.1  SIGMA=   2.3  PHAS=   76.4  FOM=  0.83  TEST= 0
INDE  7  50  53  FOBS=   38.0  SIGMA=   4.8  PHAS= -115.8  FOM=  0.11  TEST= 1
INDE  7  50  55  FOBS=    0.0  SIGMA=  20.6  PHAS=    0.0  FOM=  0.00  TEST= 0
INDE  7  50  57  FOBS=    0.0  SIGMA=  20.5  PHAS=    0.0  FOM=  0.00  TEST= 0
INDE  7  50  59  FOBS=   42.9  SIGMA=   7.3  PHAS=  132.2  FOM=  0.68  TEST= 0
INDE  7  51   8  FOBS=   79.7  SIGMA=   3.4  PHAS=  -57.5  FOM=  0.83  TEST= 0
INDE  7  51  10  FOBS=  157.2  SIGMA=   1.8  PHAS=  -58.5  FOM=  0.92  TEST= 0
INDE  7  51  12  FOBS=   82.1  SIGMA=   1.9  PHAS=   60.3  FOM=  0.93  TEST= 0
INDE  7  51  14  FOBS=   91.1  SIGMA=   1.9  PHAS=   88.9  FOM=  0.84  TEST= 0
INDE  7  51  16  FOBS=  161.7  SIGMA=   1.0  PHAS=   41.9  FOM=  0.75  TEST= 1
INDE  7  51  18  FOBS=   87.5  SIGMA=   2.3  PHAS=   58.9  FOM=  0.93  TEST= 0
INDE  7  51  20  FOBS=  172.4  SIGMA=   1.2  PHAS=  -96.3  FOM=  0.90  TEST= 0
INDE  7  51  22  FOBS=  170.9  SIGMA=   1.3  PHAS= -108.0  FOM=  0.94  TEST= 0
INDE  7  51  24  FOBS=  130.5  SIGMA=   1.6  PHAS=  -27.8  FOM=  0.63  TEST= 0
INDE  7  51  26  FOBS=   48.4  SIGMA=   4.2  PHAS=  -36.2  FOM=  0.62  TEST= 0
INDE  7  51  28  FOBS=  113.4  SIGMA=   1.8  PHAS=  -21.1  FOM=  0.84  TEST= 0
INDE  7  51  30  FOBS=   85.6  SIGMA=   2.4  PHAS=   30.7  FOM=  0.78  TEST= 0
INDE  7  51  32  FOBS=  141.2  SIGMA=   1.5  PHAS= -112.5  FOM=  0.86  TEST= 0
INDE  7  51  34  FOBS=   51.8  SIGMA=   4.7  PHAS=  -54.6  FOM=  0.71  TEST= 0
INDE  7  51  36  FOBS=   39.3  SIGMA=   6.0  PHAS= -115.8  FOM=  0.50  TEST= 0
INDE  7  51  38  FOBS=  114.2  SIGMA=   1.9  PHAS= -110.4  FOM=  0.91  TEST= 0
INDE  7  51  40  FOBS=   91.8  SIGMA=   2.0  PHAS= -111.1  FOM=  0.81  TEST= 0
INDE  7  51  42  FOBS=   30.3  SIGMA=   6.0  PHAS=  -88.1  FOM=  0.26  TEST= 0
INDE  7  51  44  FOBS=    0.0  SIGMA=  20.6  PHAS=    0.0  FOM=  0.00  TEST= 0
INDE  7  51  46  FOBS=   98.0  SIGMA=   1.9  PHAS=  -56.1  FOM=  0.91  TEST= 0
INDE  7  51  48  FOBS=   35.9  SIGMA=   6.6  PHAS= -108.2  FOM=  0.09  TEST= 1
INDE  7  51  50  FOBS=   70.5  SIGMA=   2.9  PHAS= -140.3  FOM=  0.88  TEST= 0
INDE  7  51  52  FOBS=    0.0  SIGMA=  21.5  PHAS=    0.0  FOM=  0.00  TEST= 0
INDE  7  51  54  FOBS=   44.5  SIGMA=   4.7  PHAS=  125.7  FOM=  0.74  TEST= 0
INDE  7  51  56  FOBS=   41.1  SIGMA=   5.2  PHAS=  166.8  FOM=  0.80  TEST= 0
INDE  7  51  58  FOBS=   41.7  SIGMA=   6.2  PHAS=  103.9  FOM=  0.73  TEST= 0
INDE  7  52   7  FOBS=  223.5  SIGMA=   1.4  PHAS=  106.1  FOM=  0.95  TEST= 0
INDE  7  52   9  FOBS=  135.0  SIGMA=   2.1  PHAS=  -82.4  FOM=  0.95  TEST= 0
INDE  7  52  11  FOBS=   98.2  SIGMA=   2.8  PHAS=   49.0  FOM=  0.67  TEST= 1
INDE  7  52  13  FOBS=   57.4  SIGMA=   2.7  PHAS=   79.3  FOM=  0.90  TEST= 0
INDE  7  52  15  FOBS=  183.3  SIGMA=   1.0  PHAS= -100.0  FOM=  0.95  TEST= 0
INDE  7  52  17  FOBS=  159.7  SIGMA=   1.1  PHAS=   -6.7  FOM=  0.95  TEST= 0
INDE  7  52  19  FOBS=   21.3  SIGMA=   8.9  PHAS=  -37.6  FOM=  0.19  TEST= 0
INDE  7  52  21  FOBS=  234.2  SIGMA=   1.0  PHAS=  145.6  FOM=  0.95  TEST= 0
INDE  7  52  23  FOBS=   23.9  SIGMA=   8.9  PHAS=  134.9  FOM=  0.13  TEST= 0
INDE  7  52  25  FOBS=   81.5  SIGMA=   2.5  PHAS= -141.2  FOM=  0.32  TEST= 1
INDE  7  52  27  FOBS=   53.6  SIGMA=   3.7  PHAS=  -62.1  FOM=  0.56  TEST= 0
INDE  7  52  29  FOBS=   93.8  SIGMA=   2.2  PHAS=  -56.4  FOM=  0.96  TEST= 0
INDE  7  52  31  FOBS=   53.4  SIGMA=   3.7  PHAS= -139.7  FOM=  0.78  TEST= 0
INDE  7  52  33  FOBS=   82.6  SIGMA=   2.4  PHAS=  136.5  FOM=  0.87  TEST= 0
INDE  7  52  35  FOBS=   99.6  SIGMA=   2.5  PHAS=  111.0  FOM=  0.62  TEST= 0
INDE  7  52  37  FOBS=   58.9  SIGMA=   3.7  PHAS= -158.4  FOM=  0.88  TEST= 0
INDE  7  52  39  FOBS=   86.7  SIGMA=   2.4  PHAS= -124.8  FOM=  0.85  TEST= 0
INDE  7  52  41  FOBS=   80.0  SIGMA=   2.3  PHAS= -170.0  FOM=  0.93  TEST= 0
INDE  7  52  43  FOBS=  107.8  SIGMA=   1.8  PHAS=   95.2  FOM=  0.92  TEST= 0
INDE  7  52  45  FOBS=   48.8  SIGMA=   3.8  PHAS=  165.8  FOM=  0.87  TEST= 0
```

*FIG. 12A - 205*

| | | | | | | | | | | | |
|---|---|---|---|---|---|---|---|---|---|---|---|
| INDE | 7 | 52 | 47 | FOBS= | 52.5 | SIGMA= | 3.5 | PHAS= | 161.4 | FOM= | 0.82 | TEST= 0
| INDE | 7 | 52 | 49 | FOBS= | 37.8 | SIGMA= | 5.4 | PHAS= | -53.6 | FOM= | 0.37 | TEST= 0
| INDE | 7 | 52 | 51 | FOBS= | 0.0 | SIGMA= | 20.9 | PHAS= | 0.0 | FOM= | 0.00 | TEST= 0
| INDE | 7 | 52 | 53 | FOBS= | 68.2 | SIGMA= | 2.8 | PHAS= | -50.1 | FOM= | 0.92 | TEST= 0
| INDE | 7 | 52 | 55 | FOBS= | 73.6 | SIGMA= | 3.0 | PHAS= | 45.9 | FOM= | 0.90 | TEST= 0
| INDE | 7 | 52 | 57 | FOBS= | 39.6 | SIGMA= | 7.6 | PHAS= | 89.6 | FOM= | 0.59 | TEST= 0
| INDE | 7 | 53 | 8 | FOBS= | 122.2 | SIGMA= | 2.3 | PHAS= | 22.2 | FOM= | 0.91 | TEST= 0
| INDE | 7 | 53 | 10 | FOBS= | 195.3 | SIGMA= | 1.7 | PHAS= | -75.2 | FOM= | 0.95 | TEST= 0
| INDE | 7 | 53 | 12 | FOBS= | 139.3 | SIGMA= | 1.1 | PHAS= | -3.5 | FOM= | 0.93 | TEST= 0
| INDE | 7 | 53 | 14 | FOBS= | 153.0 | SIGMA= | 1.1 | PHAS= | 135.9 | FOM= | 0.90 | TEST= 0
| INDE | 7 | 53 | 16 | FOBS= | 125.9 | SIGMA= | 1.2 | PHAS= | -159.6 | FOM= | 0.92 | TEST= 0
| INDE | 7 | 53 | 18 | FOBS= | 72.0 | SIGMA= | 2.6 | PHAS= | 69.1 | FOM= | 0.71 | TEST= 0
| INDE | 7 | 53 | 20 | FOBS= | 116.3 | SIGMA= | 1.7 | PHAS= | 83.9 | FOM= | 0.26 | TEST= 0
| INDE | 7 | 53 | 22 | FOBS= | 47.7 | SIGMA= | 4.4 | PHAS= | 45.4 | FOM= | 0.82 | TEST= 0
| INDE | 7 | 53 | 24 | FOBS= | 0.0 | SIGMA= | 19.7 | PHAS= | 0.0 | FOM= | 0.00 | TEST= 0
| INDE | 7 | 53 | 26 | FOBS= | 61.2 | SIGMA= | 3.3 | PHAS= | -47.5 | FOM= | 0.79 | TEST= 0
| INDE | 7 | 53 | 28 | FOBS= | 0.0 | SIGMA= | 20.6 | PHAS= | 0.0 | FOM= | 0.00 | TEST= 1
| INDE | 7 | 53 | 30 | FOBS= | 60.4 | SIGMA= | 3.3 | PHAS= | -161.4 | FOM= | 0.72 | TEST= 0
| INDE | 7 | 53 | 32 | FOBS= | 62.2 | SIGMA= | 3.2 | PHAS= | -34.5 | FOM= | 0.28 | TEST= 0
| INDE | 7 | 53 | 34 | FOBS= | 114.1 | SIGMA= | 1.8 | PHAS= | 83.4 | FOM= | 0.94 | TEST= 0
| INDE | 7 | 53 | 36 | FOBS= | 103.2 | SIGMA= | 2.4 | PHAS= | 61.9 | FOM= | 0.87 | TEST= 0
| INDE | 7 | 53 | 38 | FOBS= | 41.4 | SIGMA= | 4.9 | PHAS= | 161.4 | FOM= | 0.70 | TEST= 0
| INDE | 7 | 53 | 40 | FOBS= | 115.3 | SIGMA= | 1.7 | PHAS= | 55.1 | FOM= | 0.55 | TEST= 1
| INDE | 7 | 53 | 42 | FOBS= | 43.6 | SIGMA= | 4.2 | PHAS= | -2.2 | FOM= | 0.55 | TEST= 0
| INDE | 7 | 53 | 44 | FOBS= | 80.6 | SIGMA= | 2.3 | PHAS= | 76.4 | FOM= | 0.94 | TEST= 0
| INDE | 7 | 53 | 46 | FOBS= | 28.3 | SIGMA= | 7.2 | PHAS= | 137.5 | FOM= | 0.23 | TEST= 0
| INDE | 7 | 53 | 48 | FOBS= | 9.2 | SIGMA= | 24.6 | PHAS= | -19.0 | FOM= | 0.10 | TEST= 0
| INDE | 7 | 53 | 50 | FOBS= | 61.9 | SIGMA= | 3.3 | PHAS= | -164.5 | FOM= | 0.76 | TEST= 0
| INDE | 7 | 53 | 52 | FOBS= | 21.7 | SIGMA= | 9.1 | PHAS= | 130.3 | FOM= | 0.27 | TEST= 0
| INDE | 7 | 53 | 54 | FOBS= | 7.7 | SIGMA= | 30.7 | PHAS= | -100.3 | FOM= | 0.21 | TEST= 0
| INDE | 7 | 53 | 56 | FOBS= | 34.7 | SIGMA= | 8.7 | PHAS= | 140.5 | FOM= | 0.48 | TEST= 0
| INDE | 7 | 54 | 7 | FOBS= | 0.0 | SIGMA= | 22.9 | PHAS= | 0.0 | FOM= | 0.00 | TEST= 0
| INDE | 7 | 54 | 9 | FOBS= | 104.9 | SIGMA= | 2.6 | PHAS= | -161.7 | FOM= | 0.61 | TEST= 0
| INDE | 7 | 54 | 11 | FOBS= | 196.7 | SIGMA= | 1.5 | PHAS= | -63.3 | FOM= | 0.93 | TEST= 0
| INDE | 7 | 54 | 13 | FOBS= | 95.9 | SIGMA= | 1.6 | PHAS= | -47.9 | FOM= | 0.72 | TEST= 0
| INDE | 7 | 54 | 15 | FOBS= | 27.6 | SIGMA= | 5.8 | PHAS= | 157.6 | FOM= | 0.42 | TEST= 0
| INDE | 7 | 54 | 17 | FOBS= | 126.5 | SIGMA= | 1.2 | PHAS= | 108.6 | FOM= | 0.92 | TEST= 0
| INDE | 7 | 54 | 19 | FOBS= | 170.2 | SIGMA= | 1.2 | PHAS= | 177.4 | FOM= | 0.90 | TEST= 0
| INDE | 7 | 54 | 21 | FOBS= | 55.8 | SIGMA= | 3.5 | PHAS= | -168.1 | FOM= | 0.37 | TEST= 0
| INDE | 7 | 54 | 23 | FOBS= | 88.9 | SIGMA= | 2.2 | PHAS= | -54.9 | FOM= | 0.83 | TEST= 0
| INDE | 7 | 54 | 25 | FOBS= | 102.2 | SIGMA= | 2.0 | PHAS= | -103.2 | FOM= | 0.97 | TEST= 0
| INDE | 7 | 54 | 27 | FOBS= | 27.0 | SIGMA= | 7.2 | PHAS= | -23.1 | FOM= | 0.32 | TEST= 0
| INDE | 7 | 54 | 29 | FOBS= | 42.1 | SIGMA= | 4.7 | PHAS= | 109.8 | FOM= | 0.46 | TEST= 0
| INDE | 7 | 54 | 31 | FOBS= | 101.8 | SIGMA= | 2.0 | PHAS= | 163.7 | FOM= | 0.85 | TEST= 0
| INDE | 7 | 54 | 33 | FOBS= | 16.2 | SIGMA= | 12.0 | PHAS= | -49.6 | FOM= | 0.16 | TEST= 0
| INDE | 7 | 54 | 35 | FOBS= | 111.7 | SIGMA= | 1.8 | PHAS= | -25.5 | FOM= | 0.93 | TEST= 0
| INDE | 7 | 54 | 37 | FOBS= | 105.0 | SIGMA= | 2.4 | PHAS= | -75.6 | FOM= | 0.92 | TEST= 0
| INDE | 7 | 54 | 39 | FOBS= | 51.6 | SIGMA= | 3.9 | PHAS= | -112.8 | FOM= | 0.46 | TEST= 0
| INDE | 7 | 54 | 41 | FOBS= | 67.0 | SIGMA= | 2.7 | PHAS= | -2.4 | FOM= | 0.62 | TEST= 0
| INDE | 7 | 54 | 43 | FOBS= | 0.0 | SIGMA= | 21.0 | PHAS= | 0.0 | FOM= | 0.00 | TEST= 0
| INDE | 7 | 54 | 45 | FOBS= | 2.1 | SIGMA= | 94.2 | PHAS= | -27.4 | FOM= | 0.06 | TEST= 0
| INDE | 7 | 54 | 47 | FOBS= | 47.4 | SIGMA= | 4.3 | PHAS= | 85.8 | FOM= | 0.55 | TEST= 0
| INDE | 7 | 54 | 49 | FOBS= | 60.6 | SIGMA= | 3.4 | PHAS= | -79.1 | FOM= | 0.81 | TEST= 0
| INDE | 7 | 54 | 51 | FOBS= | 0.0 | SIGMA= | 22.4 | PHAS= | 0.0 | FOM= | 0.00 | TEST= 0
| INDE | 7 | 54 | 53 | FOBS= | 53.6 | SIGMA= | 4.5 | PHAS= | -5.8 | FOM= | 0.64 | TEST= 0
| INDE | 7 | 54 | 55 | FOBS= | 75.6 | SIGMA= | 4.7 | PHAS= | 26.6 | FOM= | 0.91 | TEST= 0
| INDE | 7 | 55 | 8 | FOBS= | 48.2 | SIGMA= | 5.5 | PHAS= | -44.3 | FOM= | 0.75 | TEST= 0
| INDE | 7 | 55 | 10 | FOBS= | 31.3 | SIGMA= | 9.7 | PHAS= | 89.8 | FOM= | 0.21 | TEST= 0
| INDE | 7 | 55 | 12 | FOBS= | 41.8 | SIGMA= | 6.2 | PHAS= | 103.5 | FOM= | 0.39 | TEST= 0
| INDE | 7 | 55 | 14 | FOBS= | 129.0 | SIGMA= | 1.3 | PHAS= | 168.3 | FOM= | 0.87 | TEST= 0
| INDE | 7 | 55 | 16 | FOBS= | 61.9 | SIGMA= | 2.7 | PHAS= | 26.5 | FOM= | 0.87 | TEST= 0
| INDE | 7 | 55 | 18 | FOBS= | 209.2 | SIGMA= | 0.8 | PHAS= | 73.5 | FOM= | 0.95 | TEST= 0
| INDE | 7 | 55 | 20 | FOBS= | 0.0 | SIGMA= | 20.3 | PHAS= | 0.0 | FOM= | 0.00 | TEST= 0
| INDE | 7 | 55 | 22 | FOBS= | 0.0 | SIGMA= | 20.3 | PHAS= | 0.0 | FOM= | 0.00 | TEST= 1
| INDE | 7 | 55 | 24 | FOBS= | 157.7 | SIGMA= | 1.3 | PHAS= | 178.1 | FOM= | 0.90 | TEST= 0
| INDE | 7 | 55 | 26 | FOBS= | 106.7 | SIGMA= | 1.9 | PHAS= | -121.5 | FOM= | 0.94 | TEST= 0
| INDE | 7 | 55 | 28 | FOBS= | 133.2 | SIGMA= | 1.6 | PHAS= | 98.3 | FOM= | 0.92 | TEST= 0
| INDE | 7 | 55 | 30 | FOBS= | 154.8 | SIGMA= | 1.4 | PHAS= | 74.2 | FOM= | 0.95 | TEST= 0
| INDE | 7 | 55 | 32 | FOBS= | 82.9 | SIGMA= | 2.4 | PHAS= | 112.5 | FOM= | 0.79 | TEST= 0
| INDE | 7 | 55 | 34 | FOBS= | 15.7 | SIGMA= | 15.2 | PHAS= | 4.6 | FOM= | 0.00 | TEST= 1

*FIG. 12A - 206*

```
INDE  7  55  36  FOBS=   62.6  SIGMA=   3.1  PHAS=  -145.1  FOM=  0.82  TEST= 0
INDE  7  55  38  FOBS=   55.7  SIGMA=   4.3  PHAS=  -155.9  FOM=  0.81  TEST= 0
INDE  7  55  40  FOBS=    0.0  SIGMA=  20.0  PHAS=     0.0  FOM=  0.00  TEST= 0
INDE  7  55  42  FOBS=   27.7  SIGMA=   6.6  PHAS=    23.7  FOM=  0.14  TEST= 0
INDE  7  55  44  FOBS=   85.5  SIGMA=   2.2  PHAS=    87.5  FOM=  0.92  TEST= 0
INDE  7  55  46  FOBS=   37.3  SIGMA=   6.7  PHAS=    89.8  FOM=  0.28  TEST= 0
INDE  7  55  48  FOBS=   31.6  SIGMA=   7.3  PHAS=  -127.5  FOM=  0.35  TEST= 0
INDE  7  55  50  FOBS=   61.2  SIGMA=   4.2  PHAS=   106.7  FOM=  0.88  TEST= 0
INDE  7  55  52  FOBS=    0.0  SIGMA=  23.2  PHAS=     0.0  FOM=  0.00  TEST= 0
INDE  7  55  54  FOBS=   89.3  SIGMA=   4.1  PHAS=  -105.0  FOM=  0.89  TEST= 0
INDE  7  56   7  FOBS=  135.8  SIGMA=   2.0  PHAS=   152.0  FOM=  0.94  TEST= 0
INDE  7  56   9  FOBS=  162.8  SIGMA=   1.7  PHAS=   105.5  FOM=  0.66  TEST= 1
INDE  7  56  11  FOBS=   99.2  SIGMA=   2.7  PHAS=   -48.0  FOM=  0.72  TEST= 0
INDE  7  56  13  FOBS=   48.2  SIGMA=   5.4  PHAS=   -42.6  FOM=  0.59  TEST= 0
INDE  7  56  15  FOBS=   44.3  SIGMA=   3.6  PHAS=  -144.5  FOM=  0.55  TEST= 0
INDE  7  56  17  FOBS=  171.4  SIGMA=   0.9  PHAS=   -50.0  FOM=  0.94  TEST= 0
INDE  7  56  19  FOBS=    0.0  SIGMA=  17.2  PHAS=     0.0  FOM=  0.00  TEST= 0
INDE  7  56  21  FOBS=   10.1  SIGMA=  20.5  PHAS=   163.9  FOM=  0.10  TEST= 0
INDE  7  56  23  FOBS=   45.5  SIGMA=   4.2  PHAS=    78.9  FOM=  0.39  TEST= 0
INDE  7  56  25  FOBS=   54.4  SIGMA=   3.6  PHAS=   143.6  FOM=  0.23  TEST= 0
INDE  7  56  27  FOBS=   37.5  SIGMA=   5.2  PHAS=   -83.3  FOM=  0.37  TEST= 0
INDE  7  56  29  FOBS=  133.2  SIGMA=   1.6  PHAS=    -2.0  FOM=  0.96  TEST= 0
INDE  7  56  31  FOBS=  108.2  SIGMA=   1.9  PHAS=   -23.2  FOM=  0.91  TEST= 0
INDE  7  56  33  FOBS=   86.5  SIGMA=   2.3  PHAS=   -69.4  FOM=  0.61  TEST= 0
INDE  7  56  35  FOBS=    0.0  SIGMA=  19.6  PHAS=     0.0  FOM=  0.00  TEST= 0
INDE  7  56  37  FOBS=   25.9  SIGMA=  10.2  PHAS=   -52.5  FOM=  0.26  TEST= 0
INDE  7  56  39  FOBS=    0.0  SIGMA=  20.0  PHAS=     0.0  FOM=  0.00  TEST= 0
INDE  7  56  41  FOBS=   37.3  SIGMA=   6.0  PHAS=    60.4  FOM=  0.59  TEST= 0
INDE  7  56  43  FOBS=   38.0  SIGMA=   5.2  PHAS=    -7.5  FOM=  0.42  TEST= 0
INDE  7  56  45  FOBS=   68.6  SIGMA=   3.2  PHAS=     4.2  FOM=  0.86  TEST= 0
INDE  7  56  47  FOBS=   33.6  SIGMA=   8.4  PHAS=    11.3  FOM=  0.54  TEST= 0
INDE  7  56  49  FOBS=  116.3  SIGMA=   2.3  PHAS=   -12.1  FOM=  0.94  TEST= 0
INDE  7  56  51  FOBS=   24.7  SIGMA=  13.3  PHAS=    30.8  FOM=  0.44  TEST= 0
INDE  7  56  53  FOBS=   95.1  SIGMA=   3.8  PHAS=    79.1  FOM=  0.91  TEST= 0
INDE  7  57   8  FOBS=  152.7  SIGMA=   2.1  PHAS=    84.2  FOM=  0.95  TEST= 0
INDE  7  57  10  FOBS=  131.1  SIGMA=   2.1  PHAS=    53.5  FOM=  0.90  TEST= 0
INDE  7  57  12  FOBS=   66.4  SIGMA=   4.0  PHAS=   124.5  FOM=  0.78  TEST= 0
INDE  7  57  14  FOBS=  168.0  SIGMA=   1.0  PHAS=  -175.6  FOM=  0.90  TEST= 0
INDE  7  57  16  FOBS=   41.3  SIGMA=   4.1  PHAS=  -103.0  FOM=  0.76  TEST= 0
INDE  7  57  18  FOBS=   27.6  SIGMA=   6.3  PHAS=   129.6  FOM=  0.32  TEST= 0
INDE  7  57  20  FOBS=   76.0  SIGMA=   2.0  PHAS=    90.4  FOM=  0.73  TEST= 1
INDE  7  57  22  FOBS=    0.0  SIGMA=  20.3  PHAS=     0.0  FOM=  0.00  TEST= 0
INDE  7  57  24  FOBS=   44.6  SIGMA=   4.4  PHAS=    40.8  FOM=  0.39  TEST= 0
INDE  7  57  26  FOBS=   48.8  SIGMA=   4.3  PHAS=  -144.6  FOM=  0.78  TEST= 0
INDE  7  57  28  FOBS=   65.4  SIGMA=   3.0  PHAS=  -135.4  FOM=  0.55  TEST= 0
INDE  7  57  30  FOBS=   46.3  SIGMA=   4.3  PHAS=   106.5  FOM=  0.36  TEST= 0
INDE  7  57  32  FOBS=   41.8  SIGMA=   5.2  PHAS=  -120.8  FOM=  0.82  TEST= 0
INDE  7  57  34  FOBS=    0.0  SIGMA=  19.7  PHAS=     0.0  FOM=  0.00  TEST= 0
INDE  7  57  36  FOBS=   34.3  SIGMA=   6.1  PHAS=   112.4  FOM=  0.49  TEST= 0
INDE  7  57  38  FOBS=    0.0  SIGMA=  23.2  PHAS=     0.0  FOM=  0.00  TEST= 0
INDE  7  57  40  FOBS=   19.0  SIGMA=  11.7  PHAS=   -21.0  FOM=  0.16  TEST= 0
INDE  7  57  42  FOBS=    0.0  SIGMA=  20.5  PHAS=     0.0  FOM=  0.00  TEST= 0
INDE  7  57  44  FOBS=    0.0  SIGMA=  22.3  PHAS=     0.0  FOM=  0.00  TEST= 1
INDE  7  57  46  FOBS=   49.7  SIGMA=   5.1  PHAS=   179.0  FOM=  0.46  TEST= 0
INDE  7  57  48  FOBS=   41.3  SIGMA=   6.3  PHAS=   -51.6  FOM=  0.66  TEST= 0
INDE  7  57  50  FOBS=   49.0  SIGMA=   6.6  PHAS=  -125.1  FOM=  0.78  TEST= 0
INDE  7  57  52  FOBS=   63.1  SIGMA=   5.7  PHAS=    -9.1  FOM=  0.76  TEST= 0
INDE  7  58   7  FOBS=  110.3  SIGMA=   2.5  PHAS=    27.8  FOM=  0.92  TEST= 0
INDE  7  58   9  FOBS=  116.9  SIGMA=   2.3  PHAS=    -5.5  FOM=  0.91  TEST= 0
INDE  7  58  11  FOBS=  118.4  SIGMA=   2.3  PHAS=  -134.5  FOM=  0.96  TEST= 0
INDE  7  58  13  FOBS=  133.2  SIGMA=   2.0  PHAS=    65.9  FOM=  0.90  TEST= 0
INDE  7  58  15  FOBS=   66.7  SIGMA=   2.4  PHAS=   -44.5  FOM=  0.59  TEST= 1
INDE  7  58  17  FOBS=  143.8  SIGMA=   1.2  PHAS=  -116.1  FOM=  0.95  TEST= 0
INDE  7  58  19  FOBS=  119.7  SIGMA=   1.3  PHAS=     9.7  FOM=  0.93  TEST= 0
INDE  7  58  21  FOBS=    0.0  SIGMA=  18.3  PHAS=     0.0  FOM=  0.00  TEST= 0
INDE  7  58  23  FOBS=   64.1  SIGMA=   3.2  PHAS=   169.0  FOM=  0.61  TEST= 0
INDE  7  58  25  FOBS=   50.2  SIGMA=   3.8  PHAS=   -18.1  FOM=  0.51  TEST= 1
INDE  7  58  27  FOBS=   55.2  SIGMA=   3.5  PHAS=   174.1  FOM=  0.27  TEST= 0
INDE  7  58  29  FOBS=   77.2  SIGMA=   2.6  PHAS=   -11.9  FOM=  0.82  TEST= 0
INDE  7  58  31  FOBS=   28.4  SIGMA=   7.6  PHAS=   174.2  FOM=  0.33  TEST= 0
```

*FIG. 12A - 207*

| | | | | | | | | | | | |
|---|---|---|---|---|---|---|---|---|---|---|---|
| INDE | 7 | 58 | 33 | FOBS= | 42.0 | SIGMA= | 5.1 | PHAS= | 160.3 | FOM= 0.55 | TEST= 0 |
| INDE | 7 | 58 | 35 | FOBS= | 69.0 | SIGMA= | 3.2 | PHAS= | 90.1 | FOM= 0.70 | TEST= 0 |
| INDE | 7 | 58 | 37 | FOBS= | 13.3 | SIGMA= | 17.6 | PHAS= | -67.7 | FOM= 0.39 | TEST= 0 |
| INDE | 7 | 58 | 39 | FOBS= | 0.0 | SIGMA= | 25.2 | PHAS= | 0.0 | FOM= 0.00 | TEST= 0 |
| INDE | 7 | 58 | 41 | FOBS= | 63.8 | SIGMA= | 3.9 | PHAS= | -73.0 | FOM= 0.58 | TEST= 0 |
| INDE | 7 | 58 | 43 | FOBS= | 0.0 | SIGMA= | 21.3 | PHAS= | 0.0 | FOM= 0.00 | TEST= 0 |
| INDE | 7 | 58 | 45 | FOBS= | 52.6 | SIGMA= | 4.2 | PHAS= | 140.7 | FOM= 0.18 | TEST= 0 |
| INDE | 7 | 58 | 47 | FOBS= | 45.0 | SIGMA= | 7.0 | PHAS= | -5.3 | FOM= 0.68 | TEST= 0 |
| INDE | 7 | 58 | 49 | FOBS= | 69.6 | SIGMA= | 4.8 | PHAS= | -123.5 | FOM= 0.09 | TEST= 1 |
| INDE | 7 | 58 | 51 | FOBS= | 37.3 | SIGMA= | 9.6 | PHAS= | 50.0 | FOM= 0.18 | TEST= 0 |
| INDE | 7 | 59 | 8 | FOBS= | 61.7 | SIGMA= | 4.2 | PHAS= | -82.4 | FOM= 0.41 | TEST= 0 |
| INDE | 7 | 59 | 10 | FOBS= | 78.0 | SIGMA= | 3.3 | PHAS= | -83.7 | FOM= 0.86 | TEST= 0 |
| INDE | 7 | 59 | 12 | FOBS= | 61.6 | SIGMA= | 4.2 | PHAS= | 12.5 | FOM= 0.80 | TEST= 0 |
| INDE | 7 | 59 | 14 | FOBS= | 81.9 | SIGMA= | 3.1 | PHAS= | -163.8 | FOM= 0.91 | TEST= 0 |
| INDE | 7 | 59 | 16 | FOBS= | 53.6 | SIGMA= | 3.6 | PHAS= | -7.8 | FOM= 0.60 | TEST= 0 |
| INDE | 7 | 59 | 18 | FOBS= | 70.0 | SIGMA= | 2.8 | PHAS= | 164.6 | FOM= 0.86 | TEST= 0 |
| INDE | 7 | 59 | 20 | FOBS= | 56.7 | SIGMA= | 3.0 | PHAS= | -62.0 | FOM= 0.29 | TEST= 0 |
| INDE | 7 | 59 | 22 | FOBS= | 113.5 | SIGMA= | 1.5 | PHAS= | -30.2 | FOM= 0.94 | TEST= 0 |
| INDE | 7 | 59 | 24 | FOBS= | 32.3 | SIGMA= | 5.9 | PHAS= | 168.0 | FOM= 0.18 | TEST= 0 |
| INDE | 7 | 59 | 26 | FOBS= | 116.4 | SIGMA= | 1.7 | PHAS= | 175.2 | FOM= 0.72 | TEST= 1 |
| INDE | 7 | 59 | 28 | FOBS= | 0.0 | SIGMA= | 21.8 | PHAS= | 0.0 | FOM= 0.00 | TEST= 0 |
| INDE | 7 | 59 | 30 | FOBS= | 0.0 | SIGMA= | 21.9 | PHAS= | 0.0 | FOM= 0.00 | TEST= 0 |
| INDE | 7 | 59 | 32 | FOBS= | 59.9 | SIGMA= | 4.0 | PHAS= | 24.0 | FOM= 0.19 | TEST= 1 |
| INDE | 7 | 59 | 34 | FOBS= | 98.1 | SIGMA= | 2.5 | PHAS= | 73.2 | FOM= 0.92 | TEST= 0 |
| INDE | 7 | 59 | 36 | FOBS= | 62.2 | SIGMA= | 3.8 | PHAS= | 50.1 | FOM= 0.55 | TEST= 0 |
| INDE | 7 | 59 | 38 | FOBS= | 47.8 | SIGMA= | 5.9 | PHAS= | 110.5 | FOM= 0.67 | TEST= 0 |
| INDE | 7 | 59 | 40 | FOBS= | 26.9 | SIGMA= | 11.7 | PHAS= | 122.6 | FOM= 0.59 | TEST= 0 |
| INDE | 7 | 59 | 42 | FOBS= | 77.6 | SIGMA= | 3.3 | PHAS= | -60.2 | FOM= 0.54 | TEST= 0 |
| INDE | 7 | 59 | 44 | FOBS= | 66.0 | SIGMA= | 3.3 | PHAS= | 78.5 | FOM= 0.87 | TEST= 0 |
| INDE | 7 | 59 | 46 | FOBS= | 31.7 | SIGMA= | 8.0 | PHAS= | 32.9 | FOM= 0.38 | TEST= 0 |
| INDE | 7 | 59 | 48 | FOBS= | 45.9 | SIGMA= | 8.1 | PHAS= | -163.7 | FOM= 0.04 | TEST= 1 |
| INDE | 7 | 59 | 50 | FOBS= | 80.0 | SIGMA= | 6.2 | PHAS= | -33.5 | FOM= 0.88 | TEST= 0 |
| INDE | 7 | 60 | 7 | FOBS= | 60.4 | SIGMA= | 4.2 | PHAS= | -172.8 | FOM= 0.68 | TEST= 1 |
| INDE | 7 | 60 | 9 | FOBS= | 86.4 | SIGMA= | 3.0 | PHAS= | 170.5 | FOM= 0.90 | TEST= 0 |
| INDE | 7 | 60 | 11 | FOBS= | 166.0 | SIGMA= | 1.7 | PHAS= | -154.7 | FOM= 0.95 | TEST= 0 |
| INDE | 7 | 60 | 13 | FOBS= | 81.8 | SIGMA= | 3.2 | PHAS= | 29.0 | FOM= 0.56 | TEST= 0 |
| INDE | 7 | 60 | 15 | FOBS= | 57.2 | SIGMA= | 3.1 | PHAS= | 57.7 | FOM= 0.64 | TEST= 0 |
| INDE | 7 | 60 | 17 | FOBS= | 73.1 | SIGMA= | 2.7 | PHAS= | 68.6 | FOM= 0.25 | TEST= 1 |
| INDE | 7 | 60 | 19 | FOBS= | 134.9 | SIGMA= | 1.3 | PHAS= | 23.7 | FOM= 0.95 | TEST= 0 |
| INDE | 7 | 60 | 21 | FOBS= | 95.1 | SIGMA= | 1.8 | PHAS= | -85.2 | FOM= 0.85 | TEST= 0 |
| INDE | 7 | 60 | 23 | FOBS= | 76.1 | SIGMA= | 2.4 | PHAS= | 157.3 | FOM= 0.81 | TEST= 0 |
| INDE | 7 | 60 | 25 | FOBS= | 56.9 | SIGMA= | 3.7 | PHAS= | -87.7 | FOM= 0.03 | TEST= 1 |
| INDE | 7 | 60 | 27 | FOBS= | 30.9 | SIGMA= | 7.4 | PHAS= | -153.8 | FOM= 0.28 | TEST= 0 |
| INDE | 7 | 60 | 29 | FOBS= | 6.8 | SIGMA= | 33.5 | PHAS= | 29.2 | FOM= 0.06 | TEST= 0 |
| INDE | 7 | 60 | 31 | FOBS= | 0.0 | SIGMA= | 23.4 | PHAS= | 0.0 | FOM= 0.00 | TEST= 0 |
| INDE | 7 | 60 | 33 | FOBS= | 66.8 | SIGMA= | 3.6 | PHAS= | 2.8 | FOM= 0.79 | TEST= 0 |
| INDE | 7 | 60 | 35 | FOBS= | 25.5 | SIGMA= | 10.5 | PHAS= | -156.8 | FOM= 0.28 | TEST= 0 |
| INDE | 7 | 60 | 37 | FOBS= | 167.6 | SIGMA= | 1.6 | PHAS= | -83.9 | FOM= 0.97 | TEST= 0 |
| INDE | 7 | 60 | 39 | FOBS= | 110.7 | SIGMA= | 2.6 | PHAS= | -36.7 | FOM= 0.91 | TEST= 0 |
| INDE | 7 | 60 | 41 | FOBS= | 97.2 | SIGMA= | 2.6 | PHAS= | -78.7 | FOM= 0.91 | TEST= 0 |
| INDE | 7 | 60 | 43 | FOBS= | 99.3 | SIGMA= | 2.4 | PHAS= | -75.3 | FOM= 0.89 | TEST= 0 |
| INDE | 7 | 60 | 45 | FOBS= | 0.0 | SIGMA= | 23.3 | PHAS= | 0.0 | FOM= 0.00 | TEST= 0 |
| INDE | 7 | 60 | 47 | FOBS= | 40.7 | SIGMA= | 9.3 | PHAS= | -155.6 | FOM= 0.24 | TEST= 0 |
| INDE | 7 | 61 | 8 | FOBS= | 90.0 | SIGMA= | 2.9 | PHAS= | 109.0 | FOM= 0.78 | TEST= 0 |
| INDE | 7 | 61 | 10 | FOBS= | 42.9 | SIGMA= | 6.0 | PHAS= | -126.4 | FOM= 0.37 | TEST= 0 |
| INDE | 7 | 61 | 12 | FOBS= | 84.3 | SIGMA= | 3.1 | PHAS= | -15.3 | FOM= 0.78 | TEST= 0 |
| INDE | 7 | 61 | 14 | FOBS= | 105.6 | SIGMA= | 2.5 | PHAS= | -119.3 | FOM= 0.92 | TEST= 0 |
| INDE | 7 | 61 | 16 | FOBS= | 0.0 | SIGMA= | 19.0 | PHAS= | 0.0 | FOM= 0.00 | TEST= 0 |
| INDE | 7 | 61 | 18 | FOBS= | 91.2 | SIGMA= | 2.3 | PHAS= | -61.7 | FOM= 0.92 | TEST= 0 |
| INDE | 7 | 61 | 20 | FOBS= | 0.0 | SIGMA= | 20.2 | PHAS= | 0.0 | FOM= 0.00 | TEST= 0 |
| INDE | 7 | 61 | 22 | FOBS= | 44.1 | SIGMA= | 4.5 | PHAS= | -32.1 | FOM= 0.30 | TEST= 0 |
| INDE | 7 | 61 | 24 | FOBS= | 122.8 | SIGMA= | 1.9 | PHAS= | -131.5 | FOM= 0.93 | TEST= 0 |
| INDE | 7 | 61 | 26 | FOBS= | 67.2 | SIGMA= | 4.1 | PHAS= | 177.9 | FOM= 0.81 | TEST= 0 |
| INDE | 7 | 61 | 28 | FOBS= | 23.6 | SIGMA= | 11.4 | PHAS= | 76.1 | FOM= 0.07 | TEST= 0 |
| INDE | 7 | 61 | 30 | FOBS= | 0.0 | SIGMA= | 23.1 | PHAS= | 0.0 | FOM= 0.00 | TEST= 0 |
| INDE | 7 | 61 | 32 | FOBS= | 69.4 | SIGMA= | 4.1 | PHAS= | -64.0 | FOM= 0.78 | TEST= 0 |
| INDE | 7 | 61 | 34 | FOBS= | 13.4 | SIGMA= | 24.1 | PHAS= | 115.9 | FOM= 0.39 | TEST= 1 |
| INDE | 7 | 61 | 36 | FOBS= | 147.8 | SIGMA= | 2.0 | PHAS= | 150.2 | FOM= 0.96 | TEST= 0 |
| INDE | 7 | 61 | 38 | FOBS= | 112.9 | SIGMA= | 2.6 | PHAS= | 171.5 | FOM= 0.96 | TEST= 0 |
| INDE | 7 | 61 | 40 | FOBS= | 93.7 | SIGMA= | 3.0 | PHAS= | -153.5 | FOM= 0.94 | TEST= 0 |

*FIG. 12A - 208*

```
INDE  7  61  42  FOBS=    97.8  SIGMA=   2.7  PHAS=   135.4  FOM=  0.91  TEST= 0
INDE  7  61  44  FOBS=    56.5  SIGMA=   4.7  PHAS=   170.5  FOM=  0.86  TEST= 0
INDE  7  61  46  FOBS=    98.7  SIGMA=   3.9  PHAS=    78.7  FOM=  0.93  TEST= 0
INDE  7  62   7  FOBS=    65.9  SIGMA=   3.9  PHAS=    17.4  FOM=  0.45  TEST= 0
INDE  7  62   9  FOBS=    42.3  SIGMA=   6.0  PHAS=   161.3  FOM=  0.45  TEST= 0
INDE  7  62  11  FOBS=   178.6  SIGMA=   2.2  PHAS=  -153.9  FOM=  0.97  TEST= 0
INDE  7  62  13  FOBS=    73.7  SIGMA=   3.4  PHAS=  -128.9  FOM=  0.93  TEST= 0
INDE  7  62  15  FOBS=   127.6  SIGMA=   2.9  PHAS=    99.5  FOM=  0.94  TEST= 0
INDE  7  62  17  FOBS=    31.2  SIGMA=   6.4  PHAS=    53.8  FOM=  0.62  TEST= 1
INDE  7  62  19  FOBS=     0.0  SIGMA=  21.4  PHAS=     0.0  FOM=  0.00  TEST= 0
INDE  7  62  21  FOBS=    60.7  SIGMA=   3.5  PHAS=   139.2  FOM=  0.61  TEST= 0
INDE  7  62  23  FOBS=    24.0  SIGMA=  14.1  PHAS=     5.5  FOM=  0.06  TEST= 1
INDE  7  62  25  FOBS=     0.0  SIGMA=  20.9  PHAS=     0.0  FOM=  0.00  TEST= 0
INDE  7  62  27  FOBS=    45.4  SIGMA=   6.1  PHAS=  -158.6  FOM=  0.11  TEST= 1
INDE  7  62  29  FOBS=    86.0  SIGMA=   3.2  PHAS=   -75.8  FOM=  0.89  TEST= 0
INDE  7  62  31  FOBS=    52.2  SIGMA=   5.3  PHAS=     0.8  FOM=  0.80  TEST= 0
INDE  7  62  33  FOBS=    22.9  SIGMA=  12.3  PHAS=   -16.5  FOM=  0.49  TEST= 0
INDE  7  62  35  FOBS=    29.6  SIGMA=  11.1  PHAS=    88.4  FOM=  0.22  TEST= 0
INDE  7  62  37  FOBS=    55.5  SIGMA=   5.1  PHAS=   101.4  FOM=  0.81  TEST= 0
INDE  7  62  39  FOBS=    46.2  SIGMA=   6.1  PHAS=    33.3  FOM=  0.67  TEST= 0
INDE  7  62  41  FOBS=    51.8  SIGMA=   5.5  PHAS=   -29.8  FOM=  0.77  TEST= 0
INDE  7  62  43  FOBS=     0.0  SIGMA=  23.8  PHAS=     0.0  FOM=  0.00  TEST= 1
INDE  7  62  45  FOBS=     0.0  SIGMA=  27.4  PHAS=     0.0  FOM=  0.00  TEST= 0
INDE  7  63   8  FOBS=     0.0  SIGMA=  22.2  PHAS=     0.0  FOM=  0.00  TEST= 0
INDE  7  63  10  FOBS=    27.5  SIGMA=   8.8  PHAS=  -179.4  FOM=  0.45  TEST= 0
INDE  7  63  12  FOBS=    47.3  SIGMA=   6.0  PHAS=    97.0  FOM=  0.42  TEST= 0
INDE  7  63  14  FOBS=    59.5  SIGMA=   6.0  PHAS=    -2.4  FOM=  0.59  TEST= 0
INDE  7  63  16  FOBS=    66.7  SIGMA=   5.2  PHAS=    31.2  FOM=  0.69  TEST= 0
INDE  7  63  18  FOBS=    77.3  SIGMA=   3.0  PHAS=   -50.5  FOM=  0.81  TEST= 0
INDE  7  63  20  FOBS=   103.8  SIGMA=   2.3  PHAS=   -17.4  FOM=  0.92  TEST= 0
INDE  7  63  22  FOBS=     0.0  SIGMA=  20.4  PHAS=     0.0  FOM=  0.00  TEST= 0
INDE  7  63  24  FOBS=     0.0  SIGMA=  22.2  PHAS=     0.0  FOM=  0.00  TEST= 0
INDE  7  63  26  FOBS=     0.0  SIGMA=  23.4  PHAS=     0.0  FOM=  0.00  TEST= 0
INDE  7  63  28  FOBS=    96.8  SIGMA=   2.9  PHAS=   -83.4  FOM=  0.88  TEST= 0
INDE  7  63  30  FOBS=    59.1  SIGMA=   4.6  PHAS=  -101.1  FOM=  0.64  TEST= 0
INDE  7  63  32  FOBS=    54.6  SIGMA=   5.1  PHAS=   -18.5  FOM=  0.12  TEST= 0
INDE  7  63  34  FOBS=    43.8  SIGMA=   6.4  PHAS=   158.7  FOM=  0.73  TEST= 0
INDE  7  63  36  FOBS=    53.6  SIGMA=   5.2  PHAS=   101.2  FOM=  0.67  TEST= 0
INDE  7  63  38  FOBS=    29.6  SIGMA=   9.5  PHAS=    26.8  FOM=  0.55  TEST= 0
INDE  7  63  40  FOBS=    82.4  SIGMA=   3.5  PHAS=  -133.3  FOM=  0.92  TEST= 0
INDE  7  63  42  FOBS=     0.0  SIGMA=  26.7  PHAS=     0.0  FOM=  0.00  TEST= 0
INDE  7  63  44  FOBS=    84.1  SIGMA=   4.5  PHAS=   -41.2  FOM=  0.08  TEST= 1
INDE  7  64   7  FOBS=   103.9  SIGMA=   3.5  PHAS=   -93.2  FOM=  0.94  TEST= 0
INDE  7  64   9  FOBS=   101.1  SIGMA=   3.6  PHAS=    97.8  FOM=  0.90  TEST= 0
INDE  7  64  11  FOBS=     0.0  SIGMA=  26.4  PHAS=     0.0  FOM=  0.00  TEST= 0
INDE  7  64  13  FOBS=    69.9  SIGMA=   5.1  PHAS=   -82.3  FOM=  0.83  TEST= 0
INDE  7  64  15  FOBS=   110.8  SIGMA=   3.3  PHAS=    71.7  FOM=  0.89  TEST= 0
INDE  7  64  17  FOBS=    32.6  SIGMA=   6.4  PHAS=   175.8  FOM=  0.21  TEST= 0
INDE  7  64  19  FOBS=    18.7  SIGMA=  12.3  PHAS=   -23.7  FOM=  0.40  TEST= 0
INDE  7  64  21  FOBS=    10.5  SIGMA=  23.4  PHAS=   -38.9  FOM=  0.01  TEST= 1
INDE  7  64  23  FOBS=    69.1  SIGMA=   3.1  PHAS=   -68.0  FOM=  0.89  TEST= 0
INDE  7  64  25  FOBS=    77.8  SIGMA=   2.9  PHAS=   -14.4  FOM=  0.12  TEST= 1
INDE  7  64  27  FOBS=    20.6  SIGMA=  13.4  PHAS=   152.9  FOM=  0.42  TEST= 0
INDE  7  64  29  FOBS=    45.1  SIGMA=   6.1  PHAS=  -147.0  FOM=  0.81  TEST= 0
INDE  7  64  31  FOBS=     0.0  SIGMA=  23.2  PHAS=     0.0  FOM=  0.00  TEST= 0
INDE  7  64  33  FOBS=     0.0  SIGMA=  23.5  PHAS=     0.0  FOM=  0.00  TEST= 0
INDE  7  64  35  FOBS=     0.0  SIGMA=  25.6  PHAS=     0.0  FOM=  0.00  TEST= 1
INDE  7  64  37  FOBS=    41.0  SIGMA=   8.5  PHAS=  -141.8  FOM=  0.59  TEST= 0
INDE  7  64  39  FOBS=    35.4  SIGMA=   8.1  PHAS=   -71.3  FOM=  0.58  TEST= 0
INDE  7  64  41  FOBS=    43.7  SIGMA=   6.6  PHAS=  -159.4  FOM=  0.49  TEST= 0
INDE  7  64  43  FOBS=    39.3  SIGMA=   7.6  PHAS=  -172.9  FOM=  0.57  TEST= 0
INDE  7  65   8  FOBS=    79.2  SIGMA=   4.5  PHAS=    49.6  FOM=  0.91  TEST= 0
INDE  7  65  10  FOBS=    90.1  SIGMA=   4.1  PHAS=   -88.6  FOM=  0.83  TEST= 0
INDE  7  65  12  FOBS=   125.6  SIGMA=   3.0  PHAS=   -88.1  FOM=  0.96  TEST= 0
INDE  7  65  14  FOBS=    83.6  SIGMA=   4.3  PHAS=   -48.3  FOM=  0.88  TEST= 0
INDE  7  65  16  FOBS=    81.3  SIGMA=   4.4  PHAS=    29.8  FOM=  0.84  TEST= 0
INDE  7  65  18  FOBS=    63.8  SIGMA=   3.3  PHAS=    20.7  FOM=  0.72  TEST= 0
INDE  7  65  20  FOBS=    87.2  SIGMA=   2.7  PHAS=   -20.6  FOM=  0.82  TEST= 0
INDE  7  65  22  FOBS=    39.5  SIGMA=   5.1  PHAS=  -130.4  FOM=  0.75  TEST= 0
INDE  7  65  24  FOBS=    71.1  SIGMA=   3.0  PHAS=   112.5  FOM=  0.89  TEST= 0
```

*FIG. 12A - 209*

| | | | | | | | | | | | |
|---|---|---|---|---|---|---|---|---|---|---|---|
| INDE | 7 | 65 | 26 | FOBS= | 27.6 | SIGMA= | 8.2 | PHAS= | 135.2 | FOM= | 0.33 | TEST= 0 |
| INDE | 7 | 65 | 28 | FOBS= | 29.1 | SIGMA= | 11.8 | PHAS= | -118.7 | FOM= | 0.44 | TEST= 0 |
| INDE | 7 | 65 | 30 | FOBS= | 97.3 | SIGMA= | 3.0 | PHAS= | 52.3 | FOM= | 0.91 | TEST= 0 |
| INDE | 7 | 65 | 32 | FOBS= | 58.4 | SIGMA= | 4.9 | PHAS= | -136.8 | FOM= | 0.68 | TEST= 0 |
| INDE | 7 | 65 | 34 | FOBS= | 44.9 | SIGMA= | 6.3 | PHAS= | -96.1 | FOM= | 0.41 | TEST= 0 |
| INDE | 7 | 65 | 36 | FOBS= | 29.1 | SIGMA= | 9.9 | PHAS= | 66.1 | FOM= | 0.53 | TEST= 0 |
| INDE | 7 | 65 | 38 | FOBS= | 71.8 | SIGMA= | 4.1 | PHAS= | 123.4 | FOM= | 0.87 | TEST= 0 |
| INDE | 7 | 65 | 40 | FOBS= | 0.0 | SIGMA= | 24.2 | PHAS= | 0.0 | FOM= | 0.00 | TEST= 0 |
| INDE | 7 | 65 | 42 | FOBS= | 0.0 | SIGMA= | 31.5 | PHAS= | 0.0 | FOM= | 0.00 | TEST= 0 |
| INDE | 7 | 66 | 7 | FOBS= | 75.8 | SIGMA= | 4.6 | PHAS= | -171.9 | FOM= | 0.48 | TEST= 1 |
| INDE | 7 | 66 | 9 | FOBS= | 96.8 | SIGMA= | 3.7 | PHAS= | -158.7 | FOM= | 0.88 | TEST= 0 |
| INDE | 7 | 66 | 11 | FOBS= | 118.2 | SIGMA= | 3.1 | PHAS= | -146.7 | FOM= | 0.95 | TEST= 0 |
| INDE | 7 | 66 | 13 | FOBS= | 96.7 | SIGMA= | 3.8 | PHAS= | 174.4 | FOM= | 0.95 | TEST= 0 |
| INDE | 7 | 66 | 15 | FOBS= | 106.0 | SIGMA= | 3.4 | PHAS= | -91.8 | FOM= | 0.72 | TEST= 0 |
| INDE | 7 | 66 | 17 | FOBS= | 84.4 | SIGMA= | 4.2 | PHAS= | -47.1 | FOM= | 0.91 | TEST= 0 |
| INDE | 7 | 66 | 19 | FOBS= | 41.9 | SIGMA= | 5.3 | PHAS= | 14.7 | FOM= | 0.75 | TEST= 0 |
| INDE | 7 | 66 | 21 | FOBS= | 15.0 | SIGMA= | 15.7 | PHAS= | -67.2 | FOM= | 0.35 | TEST= 0 |
| INDE | 7 | 66 | 23 | FOBS= | 25.5 | SIGMA= | 10.1 | PHAS= | 52.0 | FOM= | 0.47 | TEST= 0 |
| INDE | 7 | 66 | 25 | FOBS= | 20.8 | SIGMA= | 12.7 | PHAS= | 113.2 | FOM= | 0.17 | TEST= 0 |
| INDE | 7 | 66 | 27 | FOBS= | 97.2 | SIGMA= | 2.5 | PHAS= | 125.2 | FOM= | 0.14 | TEST= 1 |
| INDE | 7 | 66 | 29 | FOBS= | 123.7 | SIGMA= | 2.4 | PHAS= | 174.1 | FOM= | 0.40 | TEST= 1 |
| INDE | 7 | 66 | 31 | FOBS= | 138.3 | SIGMA= | 2.2 | PHAS= | -43.1 | FOM= | 0.05 | TEST= 1 |
| INDE | 7 | 66 | 33 | FOBS= | 34.5 | SIGMA= | 8.3 | PHAS= | 147.1 | FOM= | 0.63 | TEST= 0 |
| INDE | 7 | 66 | 35 | FOBS= | 0.0 | SIGMA= | 23.8 | PHAS= | 0.0 | FOM= | 0.00 | TEST= 0 |
| INDE | 7 | 66 | 37 | FOBS= | 41.3 | SIGMA= | 7.1 | PHAS= | -60.0 | FOM= | 0.11 | TEST= 0 |
| INDE | 7 | 66 | 39 | FOBS= | 31.6 | SIGMA= | 10.9 | PHAS= | 49.3 | FOM= | 0.65 | TEST= 0 |
| INDE | 7 | 67 | 8 | FOBS= | 124.5 | SIGMA= | 4.2 | PHAS= | 82.2 | FOM= | 0.94 | TEST= 0 |
| INDE | 7 | 67 | 10 | FOBS= | 45.3 | SIGMA= | 10.9 | PHAS= | 154.8 | FOM= | 0.83 | TEST= 0 |
| INDE | 7 | 67 | 12 | FOBS= | 0.0 | SIGMA= | 26.1 | PHAS= | 0.0 | FOM= | 0.00 | TEST= 0 |
| INDE | 7 | 67 | 14 | FOBS= | 54.8 | SIGMA= | 6.4 | PHAS= | 124.2 | FOM= | 0.72 | TEST= 0 |
| INDE | 7 | 67 | 16 | FOBS= | 53.5 | SIGMA= | 6.5 | PHAS= | -47.2 | FOM= | 0.11 | TEST= 1 |
| INDE | 7 | 67 | 18 | FOBS= | 0.0 | SIGMA= | 26.3 | PHAS= | 0.0 | FOM= | 0.00 | TEST= 0 |
| INDE | 7 | 67 | 20 | FOBS= | 0.0 | SIGMA= | 22.6 | PHAS= | 0.0 | FOM= | 0.00 | TEST= 0 |
| INDE | 7 | 67 | 22 | FOBS= | 0.0 | SIGMA= | 21.7 | PHAS= | 0.0 | FOM= | 0.00 | TEST= 0 |
| INDE | 7 | 67 | 24 | FOBS= | 82.9 | SIGMA= | 2.6 | PHAS= | 23.9 | FOM= | 0.50 | TEST= 1 |
| INDE | 7 | 67 | 26 | FOBS= | 31.5 | SIGMA= | 8.7 | PHAS= | 98.7 | FOM= | 0.61 | TEST= 0 |
| INDE | 7 | 67 | 28 | FOBS= | 166.7 | SIGMA= | 1.5 | PHAS= | -136.2 | FOM= | 0.96 | TEST= 0 |
| INDE | 7 | 67 | 30 | FOBS= | 90.9 | SIGMA= | 3.2 | PHAS= | -13.0 | FOM= | 0.06 | TEST= 1 |
| INDE | 7 | 67 | 32 | FOBS= | 0.0 | SIGMA= | 26.4 | PHAS= | 0.0 | FOM= | 0.00 | TEST= 0 |
| INDE | 7 | 67 | 34 | FOBS= | 0.0 | SIGMA= | 26.8 | PHAS= | 0.0 | FOM= | 0.00 | TEST= 1 |
| INDE | 7 | 67 | 36 | FOBS= | 34.4 | SIGMA= | 8.4 | PHAS= | 168.6 | FOM= | 0.28 | TEST= 0 |
| INDE | 7 | 67 | 38 | FOBS= | 47.3 | SIGMA= | 8.2 | PHAS= | -64.0 | FOM= | 0.57 | TEST= 0 |
| INDE | 7 | 68 | 13 | FOBS= | 67.8 | SIGMA= | 7.3 | PHAS= | 48.6 | FOM= | 0.78 | TEST= 0 |
| INDE | 7 | 68 | 15 | FOBS= | 41.8 | SIGMA= | 11.6 | PHAS= | 128.8 | FOM= | 0.22 | TEST= 0 |
| INDE | 7 | 68 | 17 | FOBS= | 0.0 | SIGMA= | 26.3 | PHAS= | 0.0 | FOM= | 0.00 | TEST= 0 |
| INDE | 7 | 68 | 19 | FOBS= | 51.9 | SIGMA= | 6.8 | PHAS= | -5.8 | FOM= | 0.57 | TEST= 0 |
| INDE | 7 | 68 | 21 | FOBS= | 59.3 | SIGMA= | 4.0 | PHAS= | 36.5 | FOM= | 0.43 | TEST= 0 |
| INDE | 7 | 68 | 23 | FOBS= | 26.7 | SIGMA= | 9.3 | PHAS= | -107.9 | FOM= | 0.24 | TEST= 0 |
| INDE | 7 | 68 | 25 | FOBS= | 20.3 | SIGMA= | 11.9 | PHAS= | -122.9 | FOM= | 0.55 | TEST= 0 |
| INDE | 7 | 68 | 27 | FOBS= | 27.5 | SIGMA= | 12.0 | PHAS= | 102.1 | FOM= | 0.37 | TEST= 0 |
| INDE | 7 | 68 | 29 | FOBS= | 13.8 | SIGMA= | 17.3 | PHAS= | -57.6 | FOM= | 0.27 | TEST= 0 |
| INDE | 7 | 68 | 31 | FOBS= | 0.0 | SIGMA= | 23.9 | PHAS= | 0.0 | FOM= | 0.00 | TEST= 0 |
| INDE | 7 | 68 | 33 | FOBS= | 60.0 | SIGMA= | 4.9 | PHAS= | 10.3 | FOM= | 0.05 | TEST= 1 |
| INDE | 7 | 68 | 35 | FOBS= | 0.0 | SIGMA= | 24.1 | PHAS= | 0.0 | FOM= | 0.00 | TEST= 1 |
| INDE | 7 | 68 | 37 | FOBS= | 0.0 | SIGMA= | 31.7 | PHAS= | 0.0 | FOM= | 0.00 | TEST= 0 |
| INDE | 7 | 69 | 16 | FOBS= | 69.2 | SIGMA= | 7.1 | PHAS= | 8.4 | FOM= | 0.69 | TEST= 0 |
| INDE | 7 | 69 | 18 | FOBS= | 0.0 | SIGMA= | 31.5 | PHAS= | 0.0 | FOM= | 0.00 | TEST= 0 |
| INDE | 7 | 69 | 20 | FOBS= | 65.8 | SIGMA= | 3.8 | PHAS= | -163.1 | FOM= | 0.59 | TEST= 0 |
| INDE | 7 | 69 | 22 | FOBS= | 13.8 | SIGMA= | 17.7 | PHAS= | 161.3 | FOM= | 0.25 | TEST= 0 |
| INDE | 7 | 69 | 24 | FOBS= | 21.4 | SIGMA= | 10.9 | PHAS= | 57.3 | FOM= | 0.52 | TEST= 0 |
| INDE | 7 | 69 | 26 | FOBS= | 0.0 | SIGMA= | 21.3 | PHAS= | 0.0 | FOM= | 0.00 | TEST= 0 |
| INDE | 7 | 69 | 28 | FOBS= | 103.5 | SIGMA= | 2.8 | PHAS= | -143.6 | FOM= | 0.89 | TEST= 0 |
| INDE | 7 | 69 | 30 | FOBS= | 45.7 | SIGMA= | 5.4 | PHAS= | -70.8 | FOM= | 0.28 | TEST= 1 |
| INDE | 7 | 69 | 32 | FOBS= | 34.1 | SIGMA= | 8.7 | PHAS= | -6.0 | FOM= | 0.46 | TEST= 0 |
| INDE | 7 | 69 | 34 | FOBS= | 60.0 | SIGMA= | 5.0 | PHAS= | 158.3 | FOM= | 0.54 | TEST= 0 |
| INDE | 7 | 70 | 7 | FOBS= | 39.8 | SIGMA= | 9.3 | PHAS= | 100.3 | FOM= | 0.47 | TEST= 0 |
| INDE | 7 | 70 | 21 | FOBS= | 28.3 | SIGMA= | 8.9 | PHAS= | 103.5 | FOM= | 0.44 | TEST= 0 |
| INDE | 7 | 70 | 23 | FOBS= | 57.4 | SIGMA= | 5.1 | PHAS= | 69.6 | FOM= | 0.70 | TEST= 0 |
| INDE | 7 | 70 | 25 | FOBS= | 80.5 | SIGMA= | 3.0 | PHAS= | -126.1 | FOM= | 0.91 | TEST= 0 |
| INDE | 7 | 70 | 27 | FOBS= | 93.1 | SIGMA= | 2.5 | PHAS= | 147.0 | FOM= | 0.87 | TEST= 0 |

*FIG. 12A - 210*

| | | | | | | | | | | | | |
|---|---|---|---|---|---|---|---|---|---|---|---|---|
| INDE | 7 | 70 | 29 | FOBS= | 0.0 | SIGMA= | 23.9 | PHAS= | 0.0 | FOM= | 0.00 | TEST= 0 |
| INDE | 7 | 70 | 31 | FOBS= | 39.0 | SIGMA= | 7.4 | PHAS= | -89.3 | FOM= | 0.55 | TEST= 0 |
| INDE | 7 | 70 | 33 | FOBS= | 47.4 | SIGMA= | 11.1 | PHAS= | -6.3 | FOM= | 0.18 | TEST= 1 |
| INDE | 7 | 71 | 22 | FOBS= | 0.0 | SIGMA= | 24.8 | PHAS= | 0.0 | FOM= | 0.00 | TEST= 0 |
| INDE | 7 | 71 | 24 | FOBS= | 25.0 | SIGMA= | 14.7 | PHAS= | 98.9 | FOM= | 0.37 | TEST= 0 |
| INDE | 7 | 71 | 26 | FOBS= | 61.3 | SIGMA= | 4.1 | PHAS= | 138.1 | FOM= | 0.83 | TEST= 0 |
| INDE | 7 | 71 | 28 | FOBS= | 53.7 | SIGMA= | 5.0 | PHAS= | 119.4 | FOM= | 0.65 | TEST= 0 |
| INDE | 7 | 71 | 30 | FOBS= | 46.1 | SIGMA= | 6.5 | PHAS= | -155.3 | FOM= | 0.41 | TEST= 0 |
| INDE | 7 | 72 | 7 | FOBS= | 34.5 | SIGMA= | 11.0 | PHAS= | -168.3 | FOM= | 0.57 | TEST= 0 |
| INDE | 7 | 72 | 23 | FOBS= | 13.5 | SIGMA= | 24.3 | PHAS= | 0.0 | FOM= | 0.00 | TEST= 1 |
| INDE | 7 | 72 | 25 | FOBS= | 0.0 | SIGMA= | 27.8 | PHAS= | 0.0 | FOM= | 0.00 | TEST= 0 |
| INDE | 7 | 72 | 27 | FOBS= | 17.6 | SIGMA= | 16.7 | PHAS= | 61.1 | FOM= | 0.30 | TEST= 0 |
| INDE | 7 | 73 | 8 | FOBS= | 43.2 | SIGMA= | 8.8 | PHAS= | 139.9 | FOM= | 0.68 | TEST= 0 |
| INDE | 7 | 73 | 22 | FOBS= | 4.5 | SIGMA= | 66.1 | PHAS= | 29.8 | FOM= | 0.06 | TEST= 0 |
| INDE | 7 | 73 | 24 | FOBS= | 86.7 | SIGMA= | 4.1 | PHAS= | 166.0 | FOM= | 0.80 | TEST= 0 |
| INDE | 7 | 74 | 7 | FOBS= | 27.9 | SIGMA= | 13.3 | PHAS= | -14.5 | FOM= | 0.44 | TEST= 0 |
| INDE | 7 | 75 | 8 | FOBS= | 0.0 | SIGMA= | 27.7 | PHAS= | 0.0 | FOM= | 0.00 | TEST= 0 |
| INDE | 7 | 76 | 7 | FOBS= | 0.0 | SIGMA= | 28.5 | PHAS= | 0.0 | FOM= | 0.00 | TEST= 0 |
| INDE | 7 | 76 | 9 | FOBS= | 76.7 | SIGMA= | 5.3 | PHAS= | 31.6 | FOM= | 0.68 | TEST= 0 |
| INDE | 7 | 77 | 8 | FOBS= | 0.0 | SIGMA= | 28.3 | PHAS= | 0.0 | FOM= | 0.00 | TEST= 0 |
| INDE | 8 | 9 | 15 | FOBS= | 224.9 | SIGMA= | 0.5 | PHAS= | -82.3 | FOM= | 0.98 | TEST= 1 |
| INDE | 8 | 9 | 17 | FOBS= | 313.2 | SIGMA= | 0.5 | PHAS= | -164.8 | FOM= | 0.93 | TEST= 0 |
| INDE | 8 | 9 | 19 | FOBS= | 39.8 | SIGMA= | 1.4 | PHAS= | 55.7 | FOM= | 0.86 | TEST= 0 |
| INDE | 8 | 9 | 21 | FOBS= | 166.6 | SIGMA= | 0.5 | PHAS= | 90.4 | FOM= | 0.91 | TEST= 0 |
| INDE | 8 | 9 | 23 | FOBS= | 169.1 | SIGMA= | 0.4 | PHAS= | 26.3 | FOM= | 0.86 | TEST= 0 |
| INDE | 8 | 9 | 25 | FOBS= | 168.9 | SIGMA= | 0.5 | PHAS= | -152.1 | FOM= | 0.98 | TEST= 1 |
| INDE | 8 | 9 | 27 | FOBS= | 44.7 | SIGMA= | 1.6 | PHAS= | 104.9 | FOM= | 0.94 | TEST= 0 |
| INDE | 8 | 9 | 29 | FOBS= | 87.8 | SIGMA= | 1.0 | PHAS= | 81.8 | FOM= | 0.99 | TEST= 0 |
| INDE | 8 | 9 | 31 | FOBS= | 71.4 | SIGMA= | 1.5 | PHAS= | -6.3 | FOM= | 0.73 | TEST= 0 |
| INDE | 8 | 9 | 33 | FOBS= | 66.4 | SIGMA= | 1.7 | PHAS= | 145.6 | FOM= | 0.87 | TEST= 0 |
| INDE | 8 | 9 | 35 | FOBS= | 516.1 | SIGMA= | 0.8 | PHAS= | 80.3 | FOM= | 0.98 | TEST= 0 |
| INDE | 8 | 9 | 37 | FOBS= | 198.0 | SIGMA= | 0.9 | PHAS= | 85.1 | FOM= | 0.98 | TEST= 0 |
| INDE | 8 | 9 | 39 | FOBS= | 252.9 | SIGMA= | 0.7 | PHAS= | 34.9 | FOM= | 0.93 | TEST= 0 |
| INDE | 8 | 9 | 41 | FOBS= | 149.4 | SIGMA= | 1.2 | PHAS= | 118.5 | FOM= | 0.96 | TEST= 0 |
| INDE | 8 | 9 | 43 | FOBS= | 231.4 | SIGMA= | 0.9 | PHAS= | 171.8 | FOM= | 0.90 | TEST= 0 |
| INDE | 8 | 9 | 45 | FOBS= | 51.8 | SIGMA= | 3.7 | PHAS= | -125.1 | FOM= | 0.94 | TEST= 0 |
| INDE | 8 | 9 | 47 | FOBS= | 239.7 | SIGMA= | 1.0 | PHAS= | -53.2 | FOM= | 0.96 | TEST= 0 |
| INDE | 8 | 9 | 49 | FOBS= | 169.8 | SIGMA= | 1.3 | PHAS= | 20.0 | FOM= | 0.95 | TEST= 0 |
| INDE | 8 | 9 | 51 | FOBS= | 110.6 | SIGMA= | 1.9 | PHAS= | -121.4 | FOM= | 0.87 | TEST= 0 |
| INDE | 8 | 9 | 53 | FOBS= | 53.0 | SIGMA= | 3.7 | PHAS= | 154.1 | FOM= | 0.44 | TEST= 0 |
| INDE | 8 | 9 | 55 | FOBS= | 54.8 | SIGMA= | 4.8 | PHAS= | -41.4 | FOM= | 0.74 | TEST= 0 |
| INDE | 8 | 9 | 57 | FOBS= | 117.9 | SIGMA= | 2.3 | PHAS= | 102.3 | FOM= | 0.88 | TEST= 0 |
| INDE | 8 | 9 | 59 | FOBS= | 126.5 | SIGMA= | 2.1 | PHAS= | -86.6 | FOM= | 0.94 | TEST= 0 |
| INDE | 8 | 9 | 61 | FOBS= | 0.0 | SIGMA= | 24.2 | PHAS= | 0.0 | FOM= | 0.00 | TEST= 0 |
| INDE | 8 | 9 | 63 | FOBS= | 81.9 | SIGMA= | 4.4 | PHAS= | 107.7 | FOM= | 0.81 | TEST= 0 |
| INDE | 8 | 9 | 65 | FOBS= | 107.4 | SIGMA= | 3.4 | PHAS= | 98.1 | FOM= | 0.88 | TEST= 0 |
| INDE | 8 | 9 | 75 | FOBS= | 20.1 | SIGMA= | 20.2 | PHAS= | 144.6 | FOM= | 0.44 | TEST= 0 |
| INDE | 8 | 10 | 14 | FOBS= | 186.6 | SIGMA= | 0.5 | PHAS= | 166.2 | FOM= | 0.98 | TEST= 0 |
| INDE | 8 | 10 | 16 | FOBS= | 351.4 | SIGMA= | 0.5 | PHAS= | 122.9 | FOM= | 0.79 | TEST= 0 |
| INDE | 8 | 10 | 18 | FOBS= | 165.6 | SIGMA= | 0.5 | PHAS= | 55.4 | FOM= | 0.82 | TEST= 0 |
| INDE | 8 | 10 | 20 | FOBS= | 68.4 | SIGMA= | 0.9 | PHAS= | 145.7 | FOM= | 0.98 | TEST= 0 |
| INDE | 8 | 10 | 22 | FOBS= | 178.0 | SIGMA= | 0.5 | PHAS= | -3.9 | FOM= | 0.95 | TEST= 1 |
| INDE | 8 | 10 | 24 | FOBS= | 65.5 | SIGMA= | 1.0 | PHAS= | 165.7 | FOM= | 0.75 | TEST= 0 |
| INDE | 8 | 10 | 26 | FOBS= | 172.4 | SIGMA= | 0.5 | PHAS= | 34.8 | FOM= | 0.87 | TEST= 0 |
| INDE | 8 | 10 | 28 | FOBS= | 109.5 | SIGMA= | 0.7 | PHAS= | -47.6 | FOM= | 0.92 | TEST= 0 |
| INDE | 8 | 10 | 30 | FOBS= | 156.1 | SIGMA= | 0.8 | PHAS= | -32.3 | FOM= | 0.97 | TEST= 0 |
| INDE | 8 | 10 | 32 | FOBS= | 107.4 | SIGMA= | 1.1 | PHAS= | -142.0 | FOM= | 0.98 | TEST= 1 |
| INDE | 8 | 10 | 34 | FOBS= | 181.1 | SIGMA= | 0.8 | PHAS= | 97.7 | FOM= | 0.79 | TEST= 0 |
| INDE | 8 | 10 | 36 | FOBS= | 88.6 | SIGMA= | 1.5 | PHAS= | -145.9 | FOM= | 0.99 | TEST= 0 |
| INDE | 8 | 10 | 38 | FOBS= | 218.7 | SIGMA= | 0.8 | PHAS= | -50.6 | FOM= | 0.96 | TEST= 0 |
| INDE | 8 | 10 | 40 | FOBS= | 155.0 | SIGMA= | 1.1 | PHAS= | -20.2 | FOM= | 0.91 | TEST= 0 |
| INDE | 8 | 10 | 42 | FOBS= | 207.8 | SIGMA= | 0.9 | PHAS= | 69.0 | FOM= | 0.91 | TEST= 0 |
| INDE | 8 | 10 | 44 | FOBS= | 335.4 | SIGMA= | 0.7 | PHAS= | -111.4 | FOM= | 0.94 | TEST= 0 |
| INDE | 8 | 10 | 46 | FOBS= | 246.8 | SIGMA= | 1.0 | PHAS= | -168.7 | FOM= | 0.94 | TEST= 0 |
| INDE | 8 | 10 | 48 | FOBS= | 125.0 | SIGMA= | 1.7 | PHAS= | -68.9 | FOM= | 0.77 | TEST= 0 |
| INDE | 8 | 10 | 50 | FOBS= | 108.8 | SIGMA= | 1.5 | PHAS= | 34.2 | FOM= | 0.96 | TEST= 0 |
| INDE | 8 | 10 | 52 | FOBS= | 173.7 | SIGMA= | 1.3 | PHAS= | 43.7 | FOM= | 0.94 | TEST= 0 |
| INDE | 8 | 10 | 54 | FOBS= | 29.1 | SIGMA= | 7.2 | PHAS= | 176.0 | FOM= | 0.47 | TEST= 0 |
| INDE | 8 | 10 | 56 | FOBS= | 145.5 | SIGMA= | 1.4 | PHAS= | -97.5 | FOM= | 0.97 | TEST= 0 |
| INDE | 8 | 10 | 58 | FOBS= | 53.9 | SIGMA= | 4.7 | PHAS= | 37.7 | FOM= | 0.09 | TEST= 0 |

*FIG. 12A - 211*

```
INDE  8 10 60 FOBS=  65.8 SIGMA=  3.9 PHAS=   80.5 FOM= 0.16 TEST= 1
INDE  8 10 62 FOBS=   0.0 SIGMA= 26.8 PHAS=    0.0 FOM= 0.00 TEST= 0
INDE  8 10 64 FOBS=   0.0 SIGMA= 26.6 PHAS=    0.0 FOM= 0.00 TEST= 0
INDE  8 10 66 FOBS=   0.0 SIGMA= 26.4 PHAS=    0.0 FOM= 0.00 TEST= 1
INDE  8 10 76 FOBS=  31.6 SIGMA= 13.6 PHAS=   51.3 FOM= 0.60 TEST= 0
INDE  8 11 13 FOBS= 303.8 SIGMA=  0.5 PHAS=   48.3 FOM= 0.92 TEST= 0
INDE  8 11 15 FOBS=  16.6 SIGMA=  2.9 PHAS=  159.1 FOM= 0.28 TEST= 1
INDE  8 11 17 FOBS=  36.0 SIGMA=  1.4 PHAS=  -95.1 FOM= 0.53 TEST= 0
INDE  8 11 19 FOBS=  88.6 SIGMA=  0.7 PHAS=    5.6 FOM= 0.46 TEST= 0
INDE  8 11 21 FOBS= 193.1 SIGMA=  0.4 PHAS=  110.1 FOM= 0.59 TEST= 1
INDE  8 11 23 FOBS= 198.1 SIGMA=  0.4 PHAS=   37.6 FOM= 0.94 TEST= 0
INDE  8 11 25 FOBS= 170.1 SIGMA=  0.5 PHAS= -111.8 FOM= 0.99 TEST= 0
INDE  8 11 27 FOBS=  29.8 SIGMA=  2.2 PHAS=  -77.5 FOM= 0.94 TEST= 0
INDE  8 11 29 FOBS=  96.2 SIGMA=  0.9 PHAS= -128.1 FOM= 0.93 TEST= 0
INDE  8 11 31 FOBS= 120.4 SIGMA=  0.9 PHAS= -151.0 FOM= 0.95 TEST= 0
INDE  8 11 33 FOBS= 133.2 SIGMA=  1.0 PHAS=   82.3 FOM= 0.93 TEST= 0
INDE  8 11 35 FOBS= 143.0 SIGMA=  1.3 PHAS= -144.1 FOM= 0.96 TEST= 1
INDE  8 11 37 FOBS= 111.8 SIGMA=  1.3 PHAS= -155.5 FOM= 0.86 TEST= 0
INDE  8 11 39 FOBS=  86.3 SIGMA=  1.8 PHAS=  157.4 FOM= 0.94 TEST= 0
INDE  8 11 41 FOBS= 226.4 SIGMA=  0.8 PHAS=  -31.4 FOM= 0.96 TEST= 0
INDE  8 11 43 FOBS= 267.0 SIGMA=  0.6 PHAS= -133.5 FOM= 0.92 TEST= 0
INDE  8 11 45 FOBS=  35.3 SIGMA=  3.9 PHAS=  123.6 FOM= 0.86 TEST= 0
INDE  8 11 47 FOBS=  21.8 SIGMA=  7.9 PHAS=   32.2 FOM= 0.83 TEST= 0
INDE  8 11 49 FOBS= 101.2 SIGMA=  1.6 PHAS=  -34.5 FOM= 0.90 TEST= 0
INDE  8 11 51 FOBS= 197.3 SIGMA=  1.1 PHAS=  -52.8 FOM= 0.94 TEST= 0
INDE  8 11 53 FOBS= 153.0 SIGMA=  1.4 PHAS=  -64.3 FOM= 0.93 TEST= 0
INDE  8 11 55 FOBS=  63.3 SIGMA=  3.1 PHAS= -134.8 FOM= 0.26 TEST= 0
INDE  8 11 57 FOBS= 102.8 SIGMA=  2.0 PHAS= -170.6 FOM= 0.86 TEST= 0
INDE  8 11 59 FOBS= 125.3 SIGMA=  1.6 PHAS=  -41.3 FOM= 0.93 TEST= 0
INDE  8 11 61 FOBS=   0.0 SIGMA= 21.7 PHAS=    0.0 FOM= 0.00 TEST= 0
INDE  8 11 63 FOBS=  57.0 SIGMA=  4.9 PHAS=  -78.2 FOM= 0.77 TEST= 1
INDE  8 11 65 FOBS=  74.7 SIGMA=  4.8 PHAS=  139.6 FOM= 0.84 TEST= 0
INDE  8 11 75 FOBS=   0.0 SIGMA= 29.2 PHAS=    0.0 FOM= 0.00 TEST= 0
INDE  8 12 12 FOBS= 359.5 SIGMA=  0.5 PHAS=   80.9 FOM= 0.98 TEST= 0
INDE  8 12 14 FOBS=  88.2 SIGMA=  0.6 PHAS= -132.2 FOM= 0.70 TEST= 0
INDE  8 12 16 FOBS= 155.4 SIGMA=  0.5 PHAS= -166.9 FOM= 0.80 TEST= 0
INDE  8 12 18 FOBS= 108.3 SIGMA=  0.5 PHAS=   -1.3 FOM= 0.86 TEST= 0
INDE  8 12 20 FOBS= 164.8 SIGMA=  0.4 PHAS=  -45.2 FOM= 0.79 TEST= 1
INDE  8 12 22 FOBS= 206.0 SIGMA=  0.4 PHAS=  -18.1 FOM= 0.93 TEST= 0
INDE  8 12 24 FOBS=  87.5 SIGMA=  0.7 PHAS= -136.9 FOM= 0.99 TEST= 1
INDE  8 12 26 FOBS=  35.5 SIGMA=  1.6 PHAS=  101.5 FOM= 0.96 TEST= 0
INDE  8 12 28 FOBS=  87.4 SIGMA=  0.8 PHAS=   66.1 FOM= 0.04 TEST= 0
INDE  8 12 30 FOBS= 179.0 SIGMA=  0.5 PHAS=   26.4 FOM= 0.95 TEST= 0
INDE  8 12 32 FOBS=  95.8 SIGMA=  0.9 PHAS=  -23.7 FOM= 0.92 TEST= 1
INDE  8 12 34 FOBS= 174.5 SIGMA=  0.6 PHAS=  115.8 FOM= 0.89 TEST= 0
INDE  8 12 36 FOBS= 400.7 SIGMA=  0.7 PHAS=  162.4 FOM= 0.96 TEST= 0
INDE  8 12 38 FOBS= 216.1 SIGMA=  0.7 PHAS=  146.9 FOM= 0.92 TEST= 0
INDE  8 12 40 FOBS=  51.4 SIGMA=  2.2 PHAS=  -38.9 FOM= 0.70 TEST= 0
INDE  8 12 42 FOBS= 132.7 SIGMA=  1.0 PHAS= -157.5 FOM= 0.94 TEST= 0
INDE  8 12 44 FOBS= 311.5 SIGMA=  1.0 PHAS= -149.2 FOM= 0.98 TEST= 0
INDE  8 12 46 FOBS= 129.7 SIGMA=  1.1 PHAS= -164.0 FOM= 0.92 TEST= 0
INDE  8 12 48 FOBS= 125.8 SIGMA=  1.4 PHAS= -101.6 FOM= 0.88 TEST= 0
INDE  8 12 50 FOBS=  14.2 SIGMA= 14.7 PHAS= -136.1 FOM= 0.75 TEST= 0
INDE  8 12 52 FOBS= 183.9 SIGMA=  1.2 PHAS= -111.2 FOM= 0.95 TEST= 0
INDE  8 12 54 FOBS= 102.9 SIGMA=  2.0 PHAS= -178.2 FOM= 0.93 TEST= 0
INDE  8 12 56 FOBS= 189.6 SIGMA=  1.1 PHAS= -170.0 FOM= 0.95 TEST= 0
INDE  8 12 58 FOBS=   0.0 SIGMA= 19.8 PHAS=    0.0 FOM= 0.00 TEST= 0
INDE  8 12 60 FOBS=  67.2 SIGMA=  2.9 PHAS= -157.5 FOM= 0.88 TEST= 1
INDE  8 12 62 FOBS=   0.0 SIGMA= 20.1 PHAS=    0.0 FOM= 0.00 TEST= 0
INDE  8 12 64 FOBS=  62.2 SIGMA=  4.4 PHAS=  138.5 FOM= 0.69 TEST= 0
INDE  8 12 66 FOBS=   0.0 SIGMA= 31.7 PHAS=    0.0 FOM= 0.00 TEST= 0
INDE  8 12 76 FOBS=  49.2 SIGMA=  9.2 PHAS=  151.2 FOM= 0.59 TEST= 0
INDE  8 13 11 FOBS= 231.9 SIGMA=  0.4 PHAS=  -57.0 FOM= 0.58 TEST= 0
INDE  8 13 13 FOBS= 219.6 SIGMA=  0.5 PHAS=  -17.0 FOM= 0.99 TEST= 0
INDE  8 13 15 FOBS=  75.8 SIGMA=  0.7 PHAS= -160.7 FOM= 0.95 TEST= 1
INDE  8 13 17 FOBS=  26.4 SIGMA=  1.8 PHAS=   84.1 FOM= 0.93 TEST= 0
INDE  8 13 19 FOBS=  25.8 SIGMA=  2.2 PHAS=  -74.3 FOM= 0.32 TEST= 0
INDE  8 13 21 FOBS= 225.9 SIGMA=  0.5 PHAS= -126.6 FOM= 0.98 TEST= 0
INDE  8 13 23 FOBS= 165.4 SIGMA=  0.4 PHAS=   21.6 FOM= 0.96 TEST= 0
INDE  8 13 25 FOBS=  29.3 SIGMA=  1.9 PHAS=   90.2 FOM= 0.92 TEST= 0
```

*FIG. 12A - 212*

| | | | | | | | | | | | | | |
|---|---|---|---|---|---|---|---|---|---|---|---|---|---|
| INDE | 8 | 13 | 27 | FOBS= | 44.9 | SIGMA= | 1.5 | PHAS= | -142.0 | FOM= | 0.98 | TEST= | 0 |
| INDE | 8 | 13 | 29 | FOBS= | 136.9 | SIGMA= | 0.6 | PHAS= | -60.2 | FOM= | 0.75 | TEST= | 0 |
| INDE | 8 | 13 | 31 | FOBS= | 243.9 | SIGMA= | 0.5 | PHAS= | -67.2 | FOM= | 0.97 | TEST= | 0 |
| INDE | 8 | 13 | 33 | FOBS= | 218.5 | SIGMA= | 0.5 | PHAS= | 58.9 | FOM= | 0.96 | TEST= | 0 |
| INDE | 8 | 13 | 35 | FOBS= | 336.6 | SIGMA= | 0.7 | PHAS= | 82.0 | FOM= | 0.99 | TEST= | 1 |
| INDE | 8 | 13 | 37 | FOBS= | 390.1 | SIGMA= | 0.6 | PHAS= | -28.9 | FOM= | 0.94 | TEST= | 0 |
| INDE | 8 | 13 | 39 | FOBS= | 41.8 | SIGMA= | 2.7 | PHAS= | 118.0 | FOM= | 0.45 | TEST= | 0 |
| INDE | 8 | 13 | 41 | FOBS= | 169.0 | SIGMA= | 0.9 | PHAS= | -68.8 | FOM= | 0.90 | TEST= | 0 |
| INDE | 8 | 13 | 43 | FOBS= | 38.0 | SIGMA= | 3.5 | PHAS= | 167.4 | FOM= | 0.18 | TEST= | 0 |
| INDE | 8 | 13 | 45 | FOBS= | 129.7 | SIGMA= | 1.2 | PHAS= | 105.0 | FOM= | 0.93 | TEST= | 0 |
| INDE | 8 | 13 | 47 | FOBS= | 182.3 | SIGMA= | 0.9 | PHAS= | 114.0 | FOM= | 0.96 | TEST= | 0 |
| INDE | 8 | 13 | 49 | FOBS= | 131.6 | SIGMA= | 1.2 | PHAS= | 148.0 | FOM= | 0.79 | TEST= | 0 |
| INDE | 8 | 13 | 51 | FOBS= | 117.5 | SIGMA= | 1.8 | PHAS= | -172.9 | FOM= | 0.91 | TEST= | 0 |
| INDE | 8 | 13 | 53 | FOBS= | 97.2 | SIGMA= | 2.1 | PHAS= | 136.2 | FOM= | 0.81 | TEST= | 0 |
| INDE | 8 | 13 | 55 | FOBS= | 207.8 | SIGMA= | 1.1 | PHAS= | 108.2 | FOM= | 0.96 | TEST= | 0 |
| INDE | 8 | 13 | 57 | FOBS= | 32.4 | SIGMA= | 6.1 | PHAS= | -30.0 | FOM= | 0.74 | TEST= | 0 |
| INDE | 8 | 13 | 59 | FOBS= | 148.6 | SIGMA= | 1.4 | PHAS= | 33.8 | FOM= | 0.95 | TEST= | 0 |
| INDE | 8 | 13 | 61 | FOBS= | 19.6 | SIGMA= | 10.8 | PHAS= | -176.5 | FOM= | 0.18 | TEST= | 0 |
| INDE | 8 | 13 | 63 | FOBS= | 52.4 | SIGMA= | 4.6 | PHAS= | 112.6 | FOM= | 0.80 | TEST= | 0 |
| INDE | 8 | 13 | 65 | FOBS= | 95.2 | SIGMA= | 3.0 | PHAS= | 129.0 | FOM= | 0.89 | TEST= | 0 |
| INDE | 8 | 14 | 8 | FOBS= | 315.5 | SIGMA= | 0.4 | PHAS= | -29.6 | FOM= | 0.50 | TEST= | 0 |
| INDE | 8 | 14 | 10 | FOBS= | 243.1 | SIGMA= | 0.5 | PHAS= | -100.5 | FOM= | 0.60 | TEST= | 0 |
| INDE | 8 | 14 | 12 | FOBS= | 40.3 | SIGMA= | 1.2 | PHAS= | 74.8 | FOM= | 0.95 | TEST= | 0 |
| INDE | 8 | 14 | 14 | FOBS= | 91.8 | SIGMA= | 0.8 | PHAS= | -86.1 | FOM= | 0.92 | TEST= | 0 |
| INDE | 8 | 14 | 16 | FOBS= | 195.5 | SIGMA= | 0.4 | PHAS= | 104.7 | FOM= | 0.93 | TEST= | 0 |
| INDE | 8 | 14 | 18 | FOBS= | 88.9 | SIGMA= | 0.7 | PHAS= | 13.9 | FOM= | 0.78 | TEST= | 0 |
| INDE | 8 | 14 | 20 | FOBS= | 63.8 | SIGMA= | 1.0 | PHAS= | 7.9 | FOM= | 0.99 | TEST= | 0 |
| INDE | 8 | 14 | 22 | FOBS= | 41.9 | SIGMA= | 1.3 | PHAS= | -154.3 | FOM= | 0.81 | TEST= | 0 |
| INDE | 8 | 14 | 24 | FOBS= | 61.8 | SIGMA= | 1.0 | PHAS= | -82.2 | FOM= | 0.28 | TEST= | 0 |
| INDE | 8 | 14 | 26 | FOBS= | 119.1 | SIGMA= | 0.6 | PHAS= | -88.1 | FOM= | 0.97 | TEST= | 0 |
| INDE | 8 | 14 | 28 | FOBS= | 286.5 | SIGMA= | 0.4 | PHAS= | 156.8 | FOM= | 0.97 | TEST= | 0 |
| INDE | 8 | 14 | 30 | FOBS= | 125.2 | SIGMA= | 0.7 | PHAS= | -148.1 | FOM= | 0.96 | TEST= | 0 |
| INDE | 8 | 14 | 32 | FOBS= | 274.5 | SIGMA= | 0.4 | PHAS= | -142.1 | FOM= | 0.87 | TEST= | 0 |
| INDE | 8 | 14 | 34 | FOBS= | 342.9 | SIGMA= | 0.4 | PHAS= | 1.5 | FOM= | 0.97 | TEST= | 0 |
| INDE | 8 | 14 | 36 | FOBS= | 343.7 | SIGMA= | 0.4 | PHAS= | -135.5 | FOM= | 0.95 | TEST= | 0 |
| INDE | 8 | 14 | 38 | FOBS= | 312.4 | SIGMA= | 0.5 | PHAS= | 173.9 | FOM= | 0.79 | TEST= | 1 |
| INDE | 8 | 14 | 40 | FOBS= | 101.1 | SIGMA= | 1.2 | PHAS= | 50.2 | FOM= | 0.72 | TEST= | 0 |
| INDE | 8 | 14 | 42 | FOBS= | 91.8 | SIGMA= | 1.5 | PHAS= | -97.1 | FOM= | 0.78 | TEST= | 0 |
| INDE | 8 | 14 | 44 | FOBS= | 62.3 | SIGMA= | 2.3 | PHAS= | -143.9 | FOM= | 0.89 | TEST= | 0 |
| INDE | 8 | 14 | 46 | FOBS= | 300.5 | SIGMA= | 0.9 | PHAS= | 35.8 | FOM= | 0.95 | TEST= | 0 |
| INDE | 8 | 14 | 48 | FOBS= | 158.3 | SIGMA= | 0.9 | PHAS= | 120.8 | FOM= | 0.42 | TEST= | 0 |
| INDE | 8 | 14 | 50 | FOBS= | 75.1 | SIGMA= | 2.8 | PHAS= | 55.8 | FOM= | 0.91 | TEST= | 0 |
| INDE | 8 | 14 | 52 | FOBS= | 161.3 | SIGMA= | 1.4 | PHAS= | -49.0 | FOM= | 0.94 | TEST= | 0 |
| INDE | 8 | 14 | 54 | FOBS= | 154.6 | SIGMA= | 1.6 | PHAS= | -113.9 | FOM= | 0.07 | TEST= | 1 |
| INDE | 8 | 14 | 56 | FOBS= | 102.6 | SIGMA= | 2.0 | PHAS= | -149.5 | FOM= | 0.91 | TEST= | 0 |
| INDE | 8 | 14 | 58 | FOBS= | 102.8 | SIGMA= | 2.0 | PHAS= | -49.9 | FOM= | 0.79 | TEST= | 0 |
| INDE | 8 | 14 | 60 | FOBS= | 129.7 | SIGMA= | 1.6 | PHAS= | -99.9 | FOM= | 0.93 | TEST= | 0 |
| INDE | 8 | 14 | 62 | FOBS= | 115.0 | SIGMA= | 2.1 | PHAS= | 93.6 | FOM= | 0.94 | TEST= | 0 |
| INDE | 8 | 14 | 64 | FOBS= | 89.4 | SIGMA= | 3.1 | PHAS= | 15.1 | FOM= | 0.89 | TEST= | 0 |
| INDE | 8 | 14 | 66 | FOBS= | 0.0 | SIGMA= | 29.8 | PHAS= | 0.0 | FOM= | 0.00 | TEST= | 0 |
| INDE | 8 | 14 | 68 | FOBS= | 42.6 | SIGMA= | 10.3 | PHAS= | 45.7 | FOM= | 0.52 | TEST= | 0 |
| INDE | 8 | 14 | 76 | FOBS= | 67.6 | SIGMA= | 7.0 | PHAS= | 138.8 | FOM= | 0.54 | TEST= | 0 |
| INDE | 8 | 15 | 9 | FOBS= | 102.9 | SIGMA= | 0.5 | PHAS= | 13.2 | FOM= | 0.86 | TEST= | 0 |
| INDE | 8 | 15 | 11 | FOBS= | 148.4 | SIGMA= | 0.4 | PHAS= | -124.3 | FOM= | 0.91 | TEST= | 0 |
| INDE | 8 | 15 | 13 | FOBS= | 265.4 | SIGMA= | 0.4 | PHAS= | -168.6 | FOM= | 0.86 | TEST= | 0 |
| INDE | 8 | 15 | 15 | FOBS= | 176.4 | SIGMA= | 0.5 | PHAS= | -108.5 | FOM= | 0.25 | TEST= | 1 |
| INDE | 8 | 15 | 17 | FOBS= | 167.6 | SIGMA= | 0.5 | PHAS= | -15.3 | FOM= | 0.90 | TEST= | 0 |
| INDE | 8 | 15 | 19 | FOBS= | 38.0 | SIGMA= | 1.6 | PHAS= | -44.9 | FOM= | 0.92 | TEST= | 0 |
| INDE | 8 | 15 | 21 | FOBS= | 126.3 | SIGMA= | 0.6 | PHAS= | 84.0 | FOM= | 0.97 | TEST= | 0 |
| INDE | 8 | 15 | 23 | FOBS= | 160.0 | SIGMA= | 0.5 | PHAS= | 26.6 | FOM= | 0.99 | TEST= | 0 |
| INDE | 8 | 15 | 25 | FOBS= | 134.0 | SIGMA= | 0.6 | PHAS= | 137.8 | FOM= | 0.99 | TEST= | 0 |
| INDE | 8 | 15 | 27 | FOBS= | 73.8 | SIGMA= | 1.0 | PHAS= | 109.9 | FOM= | 0.95 | TEST= | 0 |
| INDE | 8 | 15 | 29 | FOBS= | 82.9 | SIGMA= | 0.9 | PHAS= | 142.5 | FOM= | 0.91 | TEST= | 0 |
| INDE | 8 | 15 | 31 | FOBS= | 61.5 | SIGMA= | 1.3 | PHAS= | -8.9 | FOM= | 0.29 | TEST= | 0 |
| INDE | 8 | 15 | 33 | FOBS= | 309.3 | SIGMA= | 0.4 | PHAS= | -137.0 | FOM= | 0.97 | TEST= | 0 |
| INDE | 8 | 15 | 35 | FOBS= | 175.3 | SIGMA= | 0.6 | PHAS= | -175.1 | FOM= | 0.96 | TEST= | 0 |
| INDE | 8 | 15 | 37 | FOBS= | 311.7 | SIGMA= | 0.5 | PHAS= | 78.2 | FOM= | 0.95 | TEST= | 0 |
| INDE | 8 | 15 | 39 | FOBS= | 0.0 | SIGMA= | 15.3 | PHAS= | 0.0 | FOM= | 0.00 | TEST= | 0 |
| INDE | 8 | 15 | 41 | FOBS= | 196.6 | SIGMA= | 0.8 | PHAS= | -117.6 | FOM= | 0.78 | TEST= | 1 |
| INDE | 8 | 15 | 43 | FOBS= | 102.0 | SIGMA= | 1.4 | PHAS= | 173.1 | FOM= | 0.79 | TEST= | 0 |

*FIG. 12A - 213*

```
INDE  8  15  45 FOBS=  196.6 SIGMA=  0.8 PHAS=  -47.6 FOM= 0.94 TEST= 0
INDE  8  15  47 FOBS=  142.3 SIGMA=  1.1 PHAS=  116.6 FOM= 0.90 TEST= 0
INDE  8  15  49 FOBS=   18.5 SIGMA= 13.8 PHAS= -109.1 FOM= 0.33 TEST= 0
INDE  8  15  51 FOBS=  190.5 SIGMA=  1.2 PHAS= -138.9 FOM= 0.95 TEST= 0
INDE  8  15  53 FOBS=   67.6 SIGMA=  3.0 PHAS=   33.7 FOM= 0.90 TEST= 0
INDE  8  15  55 FOBS=   37.7 SIGMA=  5.3 PHAS=  127.0 FOM= 0.36 TEST= 0
INDE  8  15  57 FOBS=   68.5 SIGMA=  2.9 PHAS=  173.5 FOM= 0.57 TEST= 1
INDE  8  15  59 FOBS=   97.0 SIGMA=  2.1 PHAS=  124.4 FOM= 0.89 TEST= 0
INDE  8  15  61 FOBS=  129.3 SIGMA=  1.6 PHAS=   12.4 FOM= 0.96 TEST= 0
INDE  8  15  63 FOBS=   83.6 SIGMA=  3.3 PHAS=  -32.1 FOM= 0.87 TEST= 0
INDE  8  15  65 FOBS=  111.1 SIGMA=  2.6 PHAS= -120.9 FOM= 0.91 TEST= 0
INDE  8  15  67 FOBS=   24.6 SIGMA= 18.3 PHAS=   -5.4 FOM= 0.44 TEST= 0
INDE  8  15  69 FOBS=    0.0 SIGMA= 29.9 PHAS=    0.0 FOM= 0.00 TEST= 0
INDE  8  15  71 FOBS=   32.5 SIGMA= 14.1 PHAS= -177.7 FOM= 0.15 TEST= 0
INDE  8  16   8 FOBS=   92.0 SIGMA=  0.6 PHAS=   45.1 FOM= 0.56 TEST= 0
INDE  8  16  10 FOBS=  228.7 SIGMA=  0.4 PHAS=   10.5 FOM= 0.91 TEST= 0
INDE  8  16  12 FOBS=  134.7 SIGMA=  0.5 PHAS=   56.7 FOM= 0.87 TEST= 0
INDE  8  16  14 FOBS=   99.0 SIGMA=  0.7 PHAS=  130.6 FOM= 0.56 TEST= 0
INDE  8  16  16 FOBS=  156.2 SIGMA=  0.5 PHAS=  -93.5 FOM= 0.82 TEST= 0
INDE  8  16  18 FOBS=  169.9 SIGMA=  0.5 PHAS= -176.2 FOM= 0.86 TEST= 0
INDE  8  16  20 FOBS=  108.6 SIGMA=  0.6 PHAS=  -60.2 FOM= 0.99 TEST= 0
INDE  8  16  22 FOBS=  214.6 SIGMA=  0.5 PHAS=  -16.8 FOM= 0.93 TEST= 0
INDE  8  16  24 FOBS=   93.8 SIGMA=  0.8 PHAS=  112.4 FOM= 0.99 TEST= 0
INDE  8  16  26 FOBS=  237.9 SIGMA=  0.4 PHAS=  -90.7 FOM= 0.99 TEST= 0
INDE  8  16  28 FOBS=  163.7 SIGMA=  0.5 PHAS=  147.6 FOM= 0.99 TEST= 0
INDE  8  16  30 FOBS=   81.9 SIGMA=  1.0 PHAS= -176.3 FOM= 0.94 TEST= 0
INDE  8  16  32 FOBS=  243.6 SIGMA=  0.5 PHAS=  -84.8 FOM= 0.96 TEST= 0
INDE  8  16  34 FOBS=  292.9 SIGMA=  0.6 PHAS=  119.8 FOM= 0.93 TEST= 0
INDE  8  16  36 FOBS=  139.6 SIGMA=  0.8 PHAS=  -10.0 FOM= 0.98 TEST= 0
INDE  8  16  38 FOBS=   98.2 SIGMA=  1.1 PHAS=  -95.9 FOM= 0.90 TEST= 0
INDE  8  16  40 FOBS=  108.3 SIGMA=  1.1 PHAS=   64.7 FOM= 0.92 TEST= 0
INDE  8  16  42 FOBS=  204.2 SIGMA=  0.7 PHAS=   69.7 FOM= 0.24 TEST= 1
INDE  8  16  44 FOBS=  171.3 SIGMA=  0.9 PHAS=   46.1 FOM= 0.90 TEST= 0
INDE  8  16  46 FOBS=  241.7 SIGMA=  0.8 PHAS=   50.2 FOM= 0.97 TEST= 0
INDE  8  16  48 FOBS=  191.2 SIGMA=  1.4 PHAS=  150.6 FOM= 0.92 TEST= 0
INDE  8  16  50 FOBS=   68.3 SIGMA=  3.0 PHAS=    4.0 FOM= 0.91 TEST= 0
INDE  8  16  52 FOBS=   66.7 SIGMA=  3.1 PHAS=    8.7 FOM= 0.87 TEST= 0
INDE  8  16  54 FOBS=  117.7 SIGMA=  1.8 PHAS=  -16.0 FOM= 0.81 TEST= 0
INDE  8  16  56 FOBS=  107.7 SIGMA=  1.9 PHAS=  137.0 FOM= 0.92 TEST= 0
INDE  8  16  58 FOBS=    0.0 SIGMA= 20.7 PHAS=    0.0 FOM= 0.00 TEST= 0
INDE  8  16  60 FOBS=   46.6 SIGMA=  4.2 PHAS=  -55.0 FOM= 0.78 TEST= 0
INDE  8  16  62 FOBS=   79.5 SIGMA=  3.0 PHAS= -143.3 FOM= 0.92 TEST= 0
INDE  8  16  64 FOBS=   87.9 SIGMA=  3.2 PHAS=  178.2 FOM= 0.89 TEST= 0
INDE  8  16  66 FOBS=   91.8 SIGMA=  4.8 PHAS=  110.4 FOM= 0.88 TEST= 0
INDE  8  16  68 FOBS=    0.0 SIGMA= 30.1 PHAS=    0.0 FOM= 0.00 TEST= 0
INDE  8  16  70 FOBS=    0.0 SIGMA= 29.9 PHAS=    0.0 FOM= 0.00 TEST= 0
INDE  8  16  72 FOBS=   40.0 SIGMA= 11.6 PHAS=  -85.5 FOM= 0.33 TEST= 0
INDE  8  16  74 FOBS=   31.3 SIGMA= 15.3 PHAS=   67.3 FOM= 0.19 TEST= 0
INDE  8  17   9 FOBS=  227.3 SIGMA=  0.4 PHAS=  101.7 FOM= 0.13 TEST= 1
INDE  8  17  11 FOBS=  256.9 SIGMA=  0.5 PHAS=  -93.8 FOM= 0.90 TEST= 0
INDE  8  17  13 FOBS=  129.7 SIGMA=  0.5 PHAS=  -92.0 FOM= 0.91 TEST= 0
INDE  8  17  15 FOBS=  123.2 SIGMA=  0.6 PHAS=  126.5 FOM= 0.90 TEST= 0
INDE  8  17  17 FOBS=  147.1 SIGMA=  0.5 PHAS=  171.3 FOM= 0.77 TEST= 0
INDE  8  17  19 FOBS=  102.1 SIGMA=  0.7 PHAS=  135.7 FOM= 0.99 TEST= 0
INDE  8  17  21 FOBS=  178.8 SIGMA=  0.5 PHAS= -156.0 FOM= 0.97 TEST= 0
INDE  8  17  23 FOBS=  114.1 SIGMA=  0.7 PHAS=   28.8 FOM= 0.99 TEST= 1
INDE  8  17  25 FOBS=  140.0 SIGMA=  0.6 PHAS=  136.3 FOM= 0.97 TEST= 0
INDE  8  17  27 FOBS=   88.7 SIGMA=  0.9 PHAS= -154.8 FOM= 0.95 TEST= 0
INDE  8  17  29 FOBS=   89.0 SIGMA=  0.9 PHAS= -120.5 FOM= 0.99 TEST= 0
INDE  8  17  31 FOBS=  148.9 SIGMA=  0.6 PHAS=  136.4 FOM= 0.92 TEST= 0
INDE  8  17  33 FOBS=  214.4 SIGMA=  0.5 PHAS= -168.2 FOM= 0.93 TEST= 1
INDE  8  17  35 FOBS=  346.2 SIGMA=  0.6 PHAS=  -90.7 FOM= 0.99 TEST= 0
INDE  8  17  37 FOBS=  130.3 SIGMA=  0.9 PHAS=  120.3 FOM= 0.96 TEST= 0
INDE  8  17  39 FOBS=   94.2 SIGMA=  1.2 PHAS= -126.4 FOM= 0.79 TEST= 0
INDE  8  17  41 FOBS=  114.7 SIGMA=  1.1 PHAS=  -12.6 FOM= 0.44 TEST= 0
INDE  8  17  43 FOBS=  146.6 SIGMA=  1.0 PHAS=  -69.6 FOM= 0.91 TEST= 0
INDE  8  17  45 FOBS=  307.4 SIGMA=  0.8 PHAS=    7.1 FOM= 0.97 TEST= 0
INDE  8  17  47 FOBS=  139.6 SIGMA=  1.6 PHAS=    4.9 FOM= 0.95 TEST= 0
INDE  8  17  49 FOBS=  138.6 SIGMA=  1.6 PHAS=  153.6 FOM= 0.93 TEST= 0
INDE  8  17  51 FOBS=   49.2 SIGMA=  4.2 PHAS= -126.5 FOM= 0.85 TEST= 0
```

*FIG. 12A - 214*

```
INDE  8  17  53  FOBS=  207.8  SIGMA=   1.1  PHAS=     6.0  FOM=  0.56  TEST= 1
INDE  8  17  55  FOBS=  104.3  SIGMA=   2.0  PHAS=   -15.8  FOM=  0.89  TEST= 1
INDE  8  17  57  FOBS=  214.2  SIGMA=   1.1  PHAS=   112.7  FOM=  0.98  TEST= 0
INDE  8  17  59  FOBS=   45.2  SIGMA=   4.4  PHAS=   -76.4  FOM=  0.01  TEST= 0
INDE  8  17  61  FOBS=  124.0  SIGMA=   1.7  PHAS=    57.3  FOM=  0.93  TEST= 0
INDE  8  17  63  FOBS=  139.6  SIGMA=   1.8  PHAS=   103.2  FOM=  0.90  TEST= 0
INDE  8  17  65  FOBS=    0.0  SIGMA=  25.7  PHAS=     0.0  FOM=  0.00  TEST= 0
INDE  8  17  67  FOBS=   82.2  SIGMA=   5.4  PHAS=    23.6  FOM=  0.88  TEST= 0
INDE  8  17  69  FOBS=   90.4  SIGMA=   5.2  PHAS=    63.6  FOM=  0.67  TEST= 0
INDE  8  17  71  FOBS=   65.3  SIGMA=   7.2  PHAS=    49.3  FOM=  0.83  TEST= 0
INDE  8  17  73  FOBS=   28.2  SIGMA=  16.9  PHAS=   -74.5  FOM=  0.32  TEST= 0
INDE  8  17  75  FOBS=   33.1  SIGMA=  15.0  PHAS=   -22.4  FOM=  0.14  TEST= 0
INDE  8  18   8  FOBS=  265.7  SIGMA=   0.5  PHAS=   110.9  FOM=  0.87  TEST= 0
INDE  8  18  10  FOBS=   98.1  SIGMA=   0.6  PHAS=    35.6  FOM=  0.95  TEST= 1
INDE  8  18  12  FOBS=  138.8  SIGMA=   0.5  PHAS=   145.7  FOM=  0.87  TEST= 1
INDE  8  18  14  FOBS=  107.2  SIGMA=   0.7  PHAS=   100.9  FOM=  0.99  TEST= 0
INDE  8  18  16  FOBS=  141.6  SIGMA=   0.6  PHAS=    46.1  FOM=  0.97  TEST= 0
INDE  8  18  18  FOBS=  138.4  SIGMA=   0.6  PHAS=   114.4  FOM=  0.99  TEST= 0
INDE  8  18  20  FOBS=   40.3  SIGMA=   1.7  PHAS=   127.8  FOM=  0.97  TEST= 0
INDE  8  18  22  FOBS=  226.7  SIGMA=   0.5  PHAS=    17.5  FOM=  0.97  TEST= 0
INDE  8  18  24  FOBS=  138.3  SIGMA=   0.6  PHAS=    87.4  FOM=  0.92  TEST= 0
INDE  8  18  26  FOBS=   69.9  SIGMA=   1.1  PHAS=   160.8  FOM=  0.98  TEST= 1
INDE  8  18  28  FOBS=   84.0  SIGMA=   1.0  PHAS=  -176.9  FOM=  0.89  TEST= 0
INDE  8  18  30  FOBS=  265.7  SIGMA=   0.5  PHAS=   109.0  FOM=  0.99  TEST= 0
INDE  8  18  32  FOBS=   68.1  SIGMA=   1.3  PHAS=   -23.9  FOM=  0.52  TEST= 0
INDE  8  18  34  FOBS=  255.9  SIGMA=   0.7  PHAS=  -113.9  FOM=  0.99  TEST= 0
INDE  8  18  36  FOBS=  198.1  SIGMA=   0.7  PHAS=   163.7  FOM=  0.93  TEST= 0
INDE  8  18  38  FOBS=  172.6  SIGMA=   0.8  PHAS=   139.5  FOM=  0.92  TEST= 0
INDE  8  18  40  FOBS=  146.7  SIGMA=   0.9  PHAS=    40.8  FOM=  0.90  TEST= 0
INDE  8  18  42  FOBS=   65.1  SIGMA=   2.0  PHAS=  -151.9  FOM=  0.39  TEST= 0
INDE  8  18  44  FOBS=  262.7  SIGMA=   0.9  PHAS=   -22.1  FOM=  0.97  TEST= 0
INDE  8  18  46  FOBS=  161.9  SIGMA=   1.5  PHAS=    49.9  FOM=  0.91  TEST= 0
INDE  8  18  48  FOBS=  209.1  SIGMA=   1.1  PHAS=   147.7  FOM=  0.92  TEST= 0
INDE  8  18  50  FOBS=  170.0  SIGMA=   1.3  PHAS=    11.3  FOM=  0.96  TEST= 0
INDE  8  18  52  FOBS=  132.4  SIGMA=   1.6  PHAS=  -103.5  FOM=  0.88  TEST= 0
INDE  8  18  54  FOBS=  133.1  SIGMA=   1.6  PHAS=   -62.0  FOM=  0.93  TEST= 0
INDE  8  18  56  FOBS=  115.8  SIGMA=   1.8  PHAS=    -7.0  FOM=  0.97  TEST= 0
INDE  8  18  58  FOBS=   21.2  SIGMA=  10.2  PHAS=   100.2  FOM=  0.05  TEST= 0
INDE  8  18  60  FOBS=   79.4  SIGMA=   2.6  PHAS=   -64.5  FOM=  0.90  TEST= 0
INDE  8  18  62  FOBS=    8.1  SIGMA=  28.7  PHAS=  -118.5  FOM=  0.31  TEST= 0
INDE  8  18  64  FOBS=   76.0  SIGMA=   3.7  PHAS=    76.5  FOM=  0.75  TEST= 0
INDE  8  18  66  FOBS=   64.2  SIGMA=   6.9  PHAS=   -93.5  FOM=  0.79  TEST= 0
INDE  8  18  68  FOBS=    0.0  SIGMA=  30.1  PHAS=     0.0  FOM=  0.00  TEST= 0
INDE  8  18  70  FOBS=   47.2  SIGMA=   9.8  PHAS=   -19.3  FOM=  0.73  TEST= 0
INDE  8  18  72  FOBS=   40.9  SIGMA=  11.7  PHAS=   -68.6  FOM=  0.59  TEST= 0
INDE  8  18  74  FOBS=   52.8  SIGMA=   9.3  PHAS=   -86.4  FOM=  0.06  TEST= 1
INDE  8  19   9  FOBS=  160.2  SIGMA=   0.5  PHAS=    74.3  FOM=  0.86  TEST= 0
INDE  8  19  11  FOBS=  128.1  SIGMA=   0.5  PHAS=   164.9  FOM=  0.59  TEST= 0
INDE  8  19  13  FOBS=   45.1  SIGMA=   1.3  PHAS=    33.2  FOM=  0.95  TEST= 0
INDE  8  19  15  FOBS=  101.7  SIGMA=   0.9  PHAS=   115.4  FOM=  0.99  TEST= 0
INDE  8  19  17  FOBS=   49.8  SIGMA=   1.5  PHAS=   167.9  FOM=  0.98  TEST= 0
INDE  8  19  19  FOBS=   95.1  SIGMA=   0.9  PHAS=   116.4  FOM=  0.99  TEST= 0
INDE  8  19  21  FOBS=   57.7  SIGMA=   1.3  PHAS=   -97.8  FOM=  0.73  TEST= 0
INDE  8  19  23  FOBS=  232.7  SIGMA=   0.4  PHAS=    -8.4  FOM=  0.97  TEST= 0
INDE  8  19  25  FOBS=  201.1  SIGMA=   0.5  PHAS=    63.7  FOM=  0.96  TEST= 0
INDE  8  19  27  FOBS=  178.6  SIGMA=   0.6  PHAS=    91.9  FOM=  0.98  TEST= 0
INDE  8  19  29  FOBS=   89.9  SIGMA=   1.0  PHAS=  -101.5  FOM=  0.79  TEST= 0
INDE  8  19  31  FOBS=  134.6  SIGMA=   0.7  PHAS=   165.3  FOM=  0.57  TEST= 0
INDE  8  19  33  FOBS=  498.0  SIGMA=   0.5  PHAS=   174.5  FOM=  0.99  TEST= 0
INDE  8  19  35  FOBS=  198.0  SIGMA=   1.0  PHAS=   -99.8  FOM=  0.83  TEST= 0
INDE  8  19  37  FOBS=  304.8  SIGMA=   0.7  PHAS=    80.0  FOM=  0.95  TEST= 0
INDE  8  19  39  FOBS=  160.3  SIGMA=   0.8  PHAS=    55.3  FOM=  0.77  TEST= 0
INDE  8  19  41  FOBS=  324.7  SIGMA=   0.6  PHAS=  -128.4  FOM=  0.91  TEST= 1
INDE  8  19  43  FOBS=  134.0  SIGMA=   1.4  PHAS=   -81.9  FOM=  0.92  TEST= 0
INDE  8  19  45  FOBS=  201.4  SIGMA=   1.1  PHAS=   -52.0  FOM=  0.96  TEST= 0
INDE  8  19  47  FOBS=   85.3  SIGMA=   2.4  PHAS=    87.6  FOM=  0.68  TEST= 0
INDE  8  19  49  FOBS=  128.8  SIGMA=   1.7  PHAS=   156.5  FOM=  0.90  TEST= 0
INDE  8  19  51  FOBS=   13.1  SIGMA=  10.1  PHAS=  -110.6  FOM=  0.08  TEST= 0
INDE  8  19  53  FOBS=   48.3  SIGMA=   2.8  PHAS=   153.4  FOM=  0.83  TEST= 0
INDE  8  19  55  FOBS=   33.2  SIGMA=   6.6  PHAS=   -47.3  FOM=  0.24  TEST= 0
```

*FIG. 12A - 215*

```
INDE  8  19  57  FOBS=   114.0  SIGMA=   1.8  PHAS=   115.9  FOM=  0.95  TEST= 0
INDE  8  19  59  FOBS=    62.4  SIGMA=   3.2  PHAS=   -64.5  FOM=  0.23  TEST= 1
INDE  8  19  61  FOBS=    47.7  SIGMA=   4.1  PHAS=   103.4  FOM=  0.70  TEST= 0
INDE  8  19  63  FOBS=     0.0  SIGMA=  21.6  PHAS=     0.0  FOM=  0.00  TEST= 0
INDE  8  19  65  FOBS=    51.1  SIGMA=   8.9  PHAS=  -112.7  FOM=  0.79  TEST= 0
INDE  8  19  67  FOBS=    26.2  SIGMA=  16.8  PHAS=   121.0  FOM=  0.03  TEST= 1
INDE  8  19  69  FOBS=    31.2  SIGMA=  14.5  PHAS=   108.6  FOM=  0.34  TEST= 0
INDE  8  19  71  FOBS=    21.6  SIGMA=  21.2  PHAS=   -50.2  FOM=  0.28  TEST= 0
INDE  8  19  73  FOBS=    39.0  SIGMA=  12.5  PHAS=   105.0  FOM=  0.27  TEST= 0
INDE  8  20   8  FOBS=   161.3  SIGMA=   0.5  PHAS=    36.1  FOM=  0.32  TEST= 1
INDE  8  20  10  FOBS=   132.5  SIGMA=   0.5  PHAS=    10.7  FOM=  0.76  TEST= 0
INDE  8  20  12  FOBS=    97.1  SIGMA=   0.7  PHAS=   168.7  FOM=  0.85  TEST= 1
INDE  8  20  14  FOBS=   165.5  SIGMA=   0.5  PHAS=   -14.7  FOM=  0.95  TEST= 0
INDE  8  20  16  FOBS=   174.8  SIGMA=   0.7  PHAS=    58.0  FOM=  0.99  TEST= 0
INDE  8  20  18  FOBS=   230.6  SIGMA=   0.5  PHAS=    90.0  FOM=  0.97  TEST= 0
INDE  8  20  20  FOBS=   196.2  SIGMA=   0.6  PHAS=    86.3  FOM=  0.98  TEST= 0
INDE  8  20  22  FOBS=    84.4  SIGMA=   1.0  PHAS=   166.2  FOM=  0.96  TEST= 0
INDE  8  20  24  FOBS=   261.1  SIGMA=   0.5  PHAS=    -2.2  FOM=  0.98  TEST= 0
INDE  8  20  26  FOBS=    60.4  SIGMA=   1.4  PHAS=    16.1  FOM=  0.93  TEST= 0
INDE  8  20  28  FOBS=    84.8  SIGMA=   1.1  PHAS=   -70.8  FOM=  0.82  TEST= 0
INDE  8  20  30  FOBS=   271.3  SIGMA=   0.5  PHAS=   119.8  FOM=  0.98  TEST= 0
INDE  8  20  32  FOBS=   124.2  SIGMA=   0.8  PHAS=    26.5  FOM=  0.40  TEST= 1
INDE  8  20  34  FOBS=   227.4  SIGMA=   0.6  PHAS=    25.6  FOM=  0.94  TEST= 0
INDE  8  20  36  FOBS=   262.1  SIGMA=   0.7  PHAS=   106.3  FOM=  0.92  TEST= 0
INDE  8  20  38  FOBS=   318.6  SIGMA=   0.6  PHAS=   -24.6  FOM=  0.96  TEST= 0
INDE  8  20  40  FOBS=   328.4  SIGMA=   0.7  PHAS=    78.9  FOM=  0.98  TEST= 0
INDE  8  20  42  FOBS=   260.8  SIGMA=   0.8  PHAS=    90.8  FOM=  0.93  TEST= 0
INDE  8  20  44  FOBS=   137.8  SIGMA=   1.4  PHAS=   -38.8  FOM=  0.95  TEST= 0
INDE  8  20  46  FOBS=   201.1  SIGMA=   1.0  PHAS=   -13.4  FOM=  0.93  TEST= 0
INDE  8  20  48  FOBS=   142.4  SIGMA=   1.4  PHAS=    90.6  FOM=  0.93  TEST= 0
INDE  8  20  50  FOBS=   122.8  SIGMA=   1.8  PHAS=   131.7  FOM=  0.80  TEST= 0
INDE  8  20  52  FOBS=   152.4  SIGMA=   1.0  PHAS=  -106.8  FOM=  0.91  TEST= 0
INDE  8  20  54  FOBS=    81.1  SIGMA=   1.8  PHAS=   165.9  FOM=  0.82  TEST= 0
INDE  8  20  56  FOBS=    60.5  SIGMA=   3.4  PHAS=    27.5  FOM=  0.82  TEST= 0
INDE  8  20  58  FOBS=    23.1  SIGMA=   9.3  PHAS=    14.4  FOM=  0.02  TEST= 1
INDE  8  20  60  FOBS=    35.0  SIGMA=   5.7  PHAS=    12.6  FOM=  0.37  TEST= 0
INDE  8  20  62  FOBS=     0.0  SIGMA=  21.5  PHAS=     0.0  FOM=  0.00  TEST= 1
INDE  8  20  64  FOBS=     0.0  SIGMA=  25.8  PHAS=     0.0  FOM=  0.00  TEST= 0
INDE  8  20  66  FOBS=    94.2  SIGMA=   4.9  PHAS=   167.4  FOM=  0.89  TEST= 0
INDE  8  20  68  FOBS=    42.7  SIGMA=  10.7  PHAS=   -70.1  FOM=  0.06  TEST= 1
INDE  8  20  70  FOBS=    47.1  SIGMA=   9.4  PHAS=   -86.2  FOM=  0.79  TEST= 0
INDE  8  20  72  FOBS=    31.5  SIGMA=  14.9  PHAS=  -144.8  FOM=  0.00  TEST= 1
INDE  8  20  74  FOBS=    68.9  SIGMA=   7.2  PHAS=   -64.2  FOM=  0.84  TEST= 0
INDE  8  21   9  FOBS=   214.4  SIGMA=   0.4  PHAS=   -54.6  FOM=  0.80  TEST= 1
INDE  8  21  11  FOBS=    65.9  SIGMA=   1.0  PHAS=    96.8  FOM=  0.94  TEST= 0
INDE  8  21  13  FOBS=   170.5  SIGMA=   0.5  PHAS=   111.3  FOM=  0.97  TEST= 0
INDE  8  21  15  FOBS=    91.5  SIGMA=   1.1  PHAS=   -65.1  FOM=  0.97  TEST= 0
INDE  8  21  17  FOBS=   173.9  SIGMA=   0.6  PHAS=     3.5  FOM=  0.95  TEST= 0
INDE  8  21  19  FOBS=   144.1  SIGMA=   0.7  PHAS=     2.9  FOM=  0.97  TEST= 0
INDE  8  21  21  FOBS=   350.7  SIGMA=   0.5  PHAS=     8.0  FOM=  0.98  TEST= 0
INDE  8  21  23  FOBS=   185.6  SIGMA=   0.5  PHAS=   -70.0  FOM=  0.97  TEST= 0
INDE  8  21  25  FOBS=   121.7  SIGMA=   0.7  PHAS=    76.3  FOM=  0.45  TEST= 0
INDE  8  21  27  FOBS=   176.4  SIGMA=   0.5  PHAS=   145.4  FOM=  0.91  TEST= 0
INDE  8  21  29  FOBS=    45.8  SIGMA=   2.1  PHAS=  -124.0  FOM=  0.63  TEST= 0
INDE  8  21  31  FOBS=    87.7  SIGMA=   1.2  PHAS=    43.9  FOM=  0.98  TEST= 0
INDE  8  21  33  FOBS=   149.4  SIGMA=   0.8  PHAS=  -120.0  FOM=  0.56  TEST= 0
INDE  8  21  35  FOBS=   362.1  SIGMA=   0.6  PHAS=   -89.5  FOM=  0.95  TEST= 0
INDE  8  21  37  FOBS=   156.8  SIGMA=   1.0  PHAS=   -79.9  FOM=  0.80  TEST= 1
INDE  8  21  39  FOBS=   161.5  SIGMA=   1.0  PHAS=   -37.3  FOM=  0.96  TEST= 0
INDE  8  21  41  FOBS=   336.4  SIGMA=   0.8  PHAS=   -59.1  FOM=  0.97  TEST= 0
INDE  8  21  43  FOBS=   248.3  SIGMA=   1.0  PHAS=   -97.8  FOM=  0.95  TEST= 0
INDE  8  21  45  FOBS=   303.7  SIGMA=   0.7  PHAS=  -106.4  FOM=  0.97  TEST= 0
INDE  8  21  47  FOBS=    21.2  SIGMA=   9.8  PHAS=  -148.3  FOM=  0.40  TEST= 1
INDE  8  21  49  FOBS=   143.2  SIGMA=   1.4  PHAS=    39.4  FOM=  0.95  TEST= 0
INDE  8  21  51  FOBS=    99.3  SIGMA=   2.2  PHAS=  -159.7  FOM=  0.94  TEST= 0
INDE  8  21  53  FOBS=    94.4  SIGMA=   1.3  PHAS=  -141.3  FOM=  0.92  TEST= 0
INDE  8  21  55  FOBS=    35.5  SIGMA=   4.2  PHAS=   -48.3  FOM=  0.80  TEST= 0
INDE  8  21  57  FOBS=    22.4  SIGMA=   9.0  PHAS=    -6.2  FOM=  0.39  TEST= 0
INDE  8  21  59  FOBS=    50.5  SIGMA=   4.0  PHAS=  -142.9  FOM=  0.43  TEST= 0
INDE  8  21  61  FOBS=    65.5  SIGMA=   3.6  PHAS=    91.6  FOM=  0.76  TEST= 0
```

*FIG. 12A - 216*

```
INDE  8 21 63 FOBS=  105.3 SIGMA=  2.3 PHAS=   49.1 FOM= 0.91 TEST= 0
INDE  8 21 65 FOBS=   85.7 SIGMA=  5.4 PHAS= -112.1 FOM= 0.39 TEST= 1
INDE  8 21 67 FOBS=  104.0 SIGMA=  4.5 PHAS=   71.1 FOM= 0.92 TEST= 0
INDE  8 21 69 FOBS=   49.1 SIGMA=  9.4 PHAS=   98.3 FOM= 0.32 TEST= 0
INDE  8 21 71 FOBS=   75.1 SIGMA=  6.3 PHAS= -174.2 FOM= 0.92 TEST= 0
INDE  8 21 73 FOBS=    0.0 SIGMA= 30.9 PHAS=    0.0 FOM= 0.00 TEST= 0
INDE  8 22  8 FOBS=  240.1 SIGMA=  0.5 PHAS= -107.1 FOM= 0.90 TEST= 0
INDE  8 22 10 FOBS=  202.7 SIGMA=  0.5 PHAS=  -33.6 FOM= 0.84 TEST= 0
INDE  8 22 12 FOBS=  177.3 SIGMA=  0.5 PHAS=   -0.7 FOM= 0.99 TEST= 0
INDE  8 22 14 FOBS=  158.8 SIGMA=  0.6 PHAS=   -9.5 FOM= 0.98 TEST= 1
INDE  8 22 16 FOBS=  160.3 SIGMA=  0.7 PHAS= -120.5 FOM= 0.99 TEST= 1
INDE  8 22 18 FOBS=   56.2 SIGMA=  1.6 PHAS= -113.1 FOM= 0.26 TEST= 0
INDE  8 22 20 FOBS=  139.1 SIGMA=  0.7 PHAS=  -27.6 FOM= 0.99 TEST= 0
INDE  8 22 22 FOBS=  275.9 SIGMA=  0.5 PHAS= -155.7 FOM= 0.94 TEST= 0
INDE  8 22 24 FOBS=  319.1 SIGMA=  0.5 PHAS=   26.3 FOM= 0.97 TEST= 0
INDE  8 22 26 FOBS=  277.2 SIGMA=  0.5 PHAS=   -8.8 FOM= 0.95 TEST= 0
INDE  8 22 28 FOBS=   79.4 SIGMA=  1.1 PHAS= -133.4 FOM= 0.91 TEST= 0
INDE  8 22 30 FOBS=  224.0 SIGMA=  0.6 PHAS=  132.5 FOM= 0.88 TEST= 0
INDE  8 22 32 FOBS=   51.1 SIGMA=  2.1 PHAS=  130.0 FOM= 0.59 TEST= 0
INDE  8 22 34 FOBS=  180.9 SIGMA=  0.8 PHAS=   55.0 FOM= 0.98 TEST= 0
INDE  8 22 36 FOBS=  271.5 SIGMA=  0.7 PHAS=  116.1 FOM= 0.97 TEST= 0
INDE  8 22 38 FOBS=  172.4 SIGMA=  1.0 PHAS= -112.0 FOM= 0.91 TEST= 0
INDE  8 22 40 FOBS=  110.3 SIGMA=  1.8 PHAS=   98.8 FOM= 0.79 TEST= 0
INDE  8 22 42 FOBS=   76.1 SIGMA=  2.4 PHAS= -163.7 FOM= 0.59 TEST= 0
INDE  8 22 44 FOBS=  346.0 SIGMA=  0.7 PHAS=  138.9 FOM= 0.98 TEST= 0
INDE  8 22 46 FOBS=  245.6 SIGMA=  0.9 PHAS=  102.7 FOM= 0.95 TEST= 0
INDE  8 22 48 FOBS=  115.8 SIGMA=  1.6 PHAS= -101.3 FOM= 0.87 TEST= 1
INDE  8 22 50 FOBS=  170.1 SIGMA=  1.2 PHAS=  115.8 FOM= 0.98 TEST= 0
INDE  8 22 52 FOBS=   16.8 SIGMA=  9.6 PHAS=  -31.8 FOM= 0.10 TEST= 0
INDE  8 22 54 FOBS=   52.4 SIGMA=  2.4 PHAS= -128.9 FOM= 0.43 TEST= 1
INDE  8 22 56 FOBS=  108.0 SIGMA=  1.4 PHAS= -142.3 FOM= 0.76 TEST= 0
INDE  8 22 58 FOBS=   79.7 SIGMA=  2.6 PHAS=  174.1 FOM= 0.85 TEST= 0
INDE  8 22 60 FOBS=   61.5 SIGMA=  3.3 PHAS=  -36.8 FOM= 0.38 TEST= 1
INDE  8 22 62 FOBS=   86.8 SIGMA=  2.8 PHAS=   -5.4 FOM= 0.89 TEST= 0
INDE  8 22 64 FOBS=   47.6 SIGMA=  9.7 PHAS=  -71.7 FOM= 0.78 TEST= 0
INDE  8 22 66 FOBS=   39.8 SIGMA= 11.8 PHAS=  132.3 FOM= 0.39 TEST= 0
INDE  8 22 68 FOBS=  106.8 SIGMA=  4.3 PHAS=  -15.1 FOM= 0.95 TEST= 0
INDE  8 22 70 FOBS=   83.6 SIGMA=  5.7 PHAS=  103.9 FOM= 0.90 TEST= 0
INDE  8 22 72 FOBS=   18.8 SIGMA= 25.6 PHAS=    0.0 FOM= 0.00 TEST= 1
INDE  8 22 74 FOBS=   58.4 SIGMA=  8.4 PHAS=  -44.9 FOM= 0.82 TEST= 0
INDE  8 23  9 FOBS=  235.6 SIGMA=  0.5 PHAS= -111.9 FOM= 0.97 TEST= 0
INDE  8 23 11 FOBS=  143.4 SIGMA=  0.6 PHAS=  -71.0 FOM= 0.87 TEST= 0
INDE  8 23 13 FOBS=   63.1 SIGMA=  1.2 PHAS= -123.7 FOM= 0.98 TEST= 0
INDE  8 23 15 FOBS=   69.4 SIGMA=  1.1 PHAS=  123.8 FOM= 0.92 TEST= 0
INDE  8 23 17 FOBS=  152.2 SIGMA=  0.8 PHAS=  103.4 FOM= 0.99 TEST= 1
INDE  8 23 19 FOBS=  177.1 SIGMA=  0.6 PHAS=  -59.6 FOM= 0.96 TEST= 0
INDE  8 23 21 FOBS=  262.5 SIGMA=  0.5 PHAS=   -0.5 FOM= 0.88 TEST= 1
INDE  8 23 23 FOBS=  213.4 SIGMA=  0.5 PHAS= -146.7 FOM= 0.87 TEST= 0
INDE  8 23 25 FOBS=  224.7 SIGMA=  0.5 PHAS= -176.2 FOM= 0.93 TEST= 0
INDE  8 23 27 FOBS=  116.9 SIGMA=  0.8 PHAS=  156.8 FOM= 0.99 TEST= 0
INDE  8 23 29 FOBS=  155.1 SIGMA=  0.7 PHAS=   10.7 FOM= 0.75 TEST= 0
INDE  8 23 31 FOBS=  107.4 SIGMA=  1.2 PHAS=  150.3 FOM= 0.90 TEST= 0
INDE  8 23 33 FOBS=  133.9 SIGMA=  1.2 PHAS=  -88.3 FOM= 0.97 TEST= 0
INDE  8 23 35 FOBS=  138.6 SIGMA=  1.1 PHAS= -115.1 FOM= 0.85 TEST= 0
INDE  8 23 37 FOBS=   75.3 SIGMA=  2.0 PHAS=  -92.6 FOM= 0.58 TEST= 0
INDE  8 23 39 FOBS=  152.2 SIGMA=  1.2 PHAS=  -20.0 FOM= 0.95 TEST= 0
INDE  8 23 41 FOBS=    0.0 SIGMA= 18.9 PHAS=    0.0 FOM= 0.00 TEST= 0
INDE  8 23 43 FOBS=   72.6 SIGMA=  2.6 PHAS=   -8.3 FOM= 0.69 TEST= 0
INDE  8 23 45 FOBS=  204.1 SIGMA=  1.0 PHAS=    4.3 FOM= 0.95 TEST= 0
INDE  8 23 47 FOBS=  124.3 SIGMA=  1.5 PHAS=   91.3 FOM= 0.96 TEST= 0
INDE  8 23 49 FOBS=   94.1 SIGMA=  1.9 PHAS= -105.7 FOM= 0.26 TEST= 1
INDE  8 23 51 FOBS=   52.5 SIGMA=  3.4 PHAS=   77.4 FOM= 0.55 TEST= 1
INDE  8 23 53 FOBS=  114.1 SIGMA=  1.2 PHAS= -154.6 FOM= 0.93 TEST= 0
INDE  8 23 55 FOBS=   55.5 SIGMA=  2.4 PHAS=  124.4 FOM= 0.63 TEST= 0
INDE  8 23 57 FOBS=  215.0 SIGMA=  1.1 PHAS=   48.2 FOM= 0.97 TEST= 0
INDE  8 23 59 FOBS=   56.7 SIGMA=  3.6 PHAS= -107.2 FOM= 0.86 TEST= 0
INDE  8 23 61 FOBS=   45.4 SIGMA=  5.3 PHAS=  -25.1 FOM= 0.50 TEST= 0
INDE  8 23 63 FOBS=   72.2 SIGMA=  3.8 PHAS= -140.6 FOM= 0.84 TEST= 0
INDE  8 23 65 FOBS=   24.3 SIGMA= 19.1 PHAS=   74.1 FOM= 0.12 TEST= 0
INDE  8 23 67 FOBS=   20.6 SIGMA= 22.7 PHAS=  131.1 FOM= 0.19 TEST= 1
```

*FIG. 12A - 217*

```
INDE  8 23 69 FOBS=   47.6 SIGMA=  9.9 PHAS=  -75.4 FOM= 0.40 TEST= 0
INDE  8 23 71 FOBS=   49.7 SIGMA=  9.6 PHAS=   41.9 FOM= 0.71 TEST= 0
INDE  8 23 73 FOBS=   48.5 SIGMA= 10.2 PHAS=  -66.5 FOM= 0.76 TEST= 0
INDE  8 24  8 FOBS=   27.6 SIGMA=  2.3 PHAS=  130.2 FOM= 0.78 TEST= 0
INDE  8 24 10 FOBS=  168.9 SIGMA=  0.6 PHAS= -134.8 FOM= 0.97 TEST= 0
INDE  8 24 12 FOBS=   54.9 SIGMA=  1.4 PHAS=    2.3 FOM= 0.30 TEST= 0
INDE  8 24 14 FOBS=   99.2 SIGMA=  0.9 PHAS=  -15.2 FOM= 0.64 TEST= 1
INDE  8 24 16 FOBS=  282.2 SIGMA=  0.6 PHAS=   10.5 FOM= 0.98 TEST= 0
INDE  8 24 18 FOBS=   51.1 SIGMA=  1.9 PHAS= -177.4 FOM= 0.71 TEST= 0
INDE  8 24 20 FOBS=  204.3 SIGMA=  0.6 PHAS=  -95.2 FOM= 0.94 TEST= 0
INDE  8 24 22 FOBS=   57.7 SIGMA=  1.6 PHAS= -124.0 FOM= 0.29 TEST= 0
INDE  8 24 24 FOBS=  311.8 SIGMA=  0.7 PHAS=   58.3 FOM= 0.98 TEST= 0
INDE  8 24 26 FOBS=   24.0 SIGMA=  4.1 PHAS=  117.0 FOM= 0.55 TEST= 0
INDE  8 24 28 FOBS=  166.9 SIGMA=  0.8 PHAS= -111.4 FOM= 0.97 TEST= 0
INDE  8 24 30 FOBS=  102.1 SIGMA=  1.2 PHAS=  -73.2 FOM= 0.91 TEST= 0
INDE  8 24 32 FOBS=  162.8 SIGMA=  0.9 PHAS=  128.0 FOM= 0.94 TEST= 0
INDE  8 24 34 FOBS=  147.6 SIGMA=  1.1 PHAS=   28.3 FOM= 0.57 TEST= 0
INDE  8 24 36 FOBS=   60.7 SIGMA=  2.7 PHAS=  -12.0 FOM= 0.44 TEST= 0
INDE  8 24 38 FOBS=  281.1 SIGMA=  0.7 PHAS= -172.1 FOM= 0.97 TEST= 0
INDE  8 24 40 FOBS=  169.9 SIGMA=  1.1 PHAS=    9.5 FOM= 0.98 TEST= 0
INDE  8 24 42 FOBS=  255.4 SIGMA=  0.9 PHAS=   24.2 FOM= 0.96 TEST= 0
INDE  8 24 44 FOBS=    0.0 SIGMA= 19.0 PHAS=    0.0 FOM= 0.00 TEST= 0
INDE  8 24 46 FOBS=  141.0 SIGMA=  1.3 PHAS=   12.0 FOM= 0.97 TEST= 0
INDE  8 24 48 FOBS=  144.3 SIGMA=  1.3 PHAS= -152.4 FOM= 0.93 TEST= 0
INDE  8 24 50 FOBS=   46.4 SIGMA=  3.7 PHAS=   -7.1 FOM= 0.16 TEST= 1
INDE  8 24 52 FOBS=   37.3 SIGMA=  4.9 PHAS=   -3.7 FOM= 0.38 TEST= 0
INDE  8 24 54 FOBS=  158.5 SIGMA=  0.9 PHAS=   73.6 FOM= 0.95 TEST= 0
INDE  8 24 56 FOBS=   58.3 SIGMA=  2.3 PHAS=   79.5 FOM= 0.64 TEST= 0
INDE  8 24 58 FOBS=  114.7 SIGMA=  1.4 PHAS= -110.5 FOM= 0.95 TEST= 0
INDE  8 24 60 FOBS=   39.3 SIGMA=  6.1 PHAS=  -30.9 FOM= 0.57 TEST= 0
INDE  8 24 62 FOBS=  117.3 SIGMA=  2.5 PHAS=   26.9 FOM= 0.92 TEST= 0
INDE  8 24 64 FOBS=    0.0 SIGMA= 30.2 PHAS=    0.0 FOM= 0.00 TEST= 0
INDE  8 24 66 FOBS=   37.6 SIGMA= 12.6 PHAS= -177.7 FOM= 0.14 TEST= 1
INDE  8 24 68 FOBS=  118.0 SIGMA=  4.2 PHAS=   -0.9 FOM= 0.96 TEST= 0
INDE  8 24 70 FOBS=   27.8 SIGMA= 17.1 PHAS=   36.1 FOM= 0.34 TEST= 0
INDE  8 24 72 FOBS=    0.0 SIGMA= 31.4 PHAS=    0.0 FOM= 0.00 TEST= 0
INDE  8 25  9 FOBS=  196.6 SIGMA=  0.5 PHAS= -145.8 FOM= 0.96 TEST= 0
INDE  8 25 11 FOBS=  152.9 SIGMA=  0.6 PHAS= -144.8 FOM= 0.88 TEST= 0
INDE  8 25 13 FOBS=  191.8 SIGMA=  0.5 PHAS=  -86.1 FOM= 0.98 TEST= 0
INDE  8 25 15 FOBS=  178.8 SIGMA=  0.6 PHAS= -129.1 FOM= 0.96 TEST= 0
INDE  8 25 17 FOBS=   70.3 SIGMA=  1.5 PHAS=  125.7 FOM= 0.29 TEST= 0
INDE  8 25 19 FOBS=  170.9 SIGMA=  0.8 PHAS=  -89.2 FOM= 0.85 TEST= 0
INDE  8 25 21 FOBS=  212.5 SIGMA=  0.6 PHAS=   76.9 FOM= 0.85 TEST= 0
INDE  8 25 23 FOBS=   68.7 SIGMA=  1.7 PHAS=  142.3 FOM= 0.89 TEST= 0
INDE  8 25 25 FOBS=  119.0 SIGMA=  1.0 PHAS=    5.2 FOM= 0.95 TEST= 0
INDE  8 25 27 FOBS=  308.3 SIGMA=  0.6 PHAS=  131.8 FOM= 0.98 TEST= 0
INDE  8 25 29 FOBS=  131.3 SIGMA=  1.0 PHAS= -130.5 FOM= 0.90 TEST= 0
INDE  8 25 31 FOBS=   56.6 SIGMA=  2.3 PHAS= -103.1 FOM= 0.42 TEST= 0
INDE  8 25 33 FOBS=  176.0 SIGMA=  0.8 PHAS= -103.3 FOM= 0.85 TEST= 1
INDE  8 25 35 FOBS=  235.9 SIGMA=  0.8 PHAS= -105.1 FOM= 0.92 TEST= 0
INDE  8 25 37 FOBS=  123.5 SIGMA=  1.5 PHAS=  100.9 FOM= 0.95 TEST= 1
INDE  8 25 39 FOBS=   65.6 SIGMA=  2.7 PHAS=   68.3 FOM= 0.82 TEST= 0
INDE  8 25 41 FOBS=  237.3 SIGMA=  0.9 PHAS=  -83.7 FOM= 0.97 TEST= 0
INDE  8 25 43 FOBS=  170.8 SIGMA=  1.2 PHAS=  -34.7 FOM= 0.96 TEST= 0
INDE  8 25 45 FOBS=  136.1 SIGMA=  1.4 PHAS=   -6.0 FOM= 0.95 TEST= 0
INDE  8 25 47 FOBS=   63.1 SIGMA=  2.8 PHAS= -166.3 FOM= 0.45 TEST= 0
INDE  8 25 49 FOBS=   59.1 SIGMA=  3.0 PHAS=  116.7 FOM= 0.65 TEST= 0
INDE  8 25 51 FOBS=   64.6 SIGMA=  2.7 PHAS= -129.3 FOM= 0.85 TEST= 0
INDE  8 25 53 FOBS=   90.2 SIGMA=  1.6 PHAS= -113.1 FOM= 0.60 TEST= 0
INDE  8 25 55 FOBS=  157.8 SIGMA=  0.9 PHAS=  -87.4 FOM= 0.63 TEST= 1
INDE  8 25 57 FOBS=  119.6 SIGMA=  1.4 PHAS=   87.0 FOM= 0.94 TEST= 0
INDE  8 25 59 FOBS=  109.6 SIGMA=  1.6 PHAS= -171.7 FOM= 0.87 TEST= 0
INDE  8 25 61 FOBS=   81.1 SIGMA=  3.1 PHAS=  -71.6 FOM= 0.91 TEST= 0
INDE  8 25 63 FOBS=    0.0 SIGMA= 25.0 PHAS=    0.0 FOM= 0.00 TEST= 0
INDE  8 25 65 FOBS=   76.5 SIGMA=  6.3 PHAS=  165.8 FOM= 0.59 TEST= 0
INDE  8 25 67 FOBS=   56.2 SIGMA=  8.5 PHAS=  -98.0 FOM= 0.87 TEST= 0
INDE  8 25 69 FOBS=   72.1 SIGMA=  6.8 PHAS=  -91.2 FOM= 0.90 TEST= 0
INDE  8 25 71 FOBS=    0.0 SIGMA= 31.5 PHAS=    0.0 FOM= 0.00 TEST= 0
INDE  8 25 73 FOBS=   23.6 SIGMA= 21.1 PHAS=   32.5 FOM= 0.10 TEST= 1
INDE  8 26  8 FOBS=  110.7 SIGMA=  0.7 PHAS=  170.1 FOM= 0.99 TEST= 0
```

*FIG. 12A - 218*

| | | | | | | | | | | | |
|---|---|---|---|---|---|---|---|---|---|---|---|
| INDE | 8 | 26 | 10 | FOBS= | 139.2 | SIGMA= | 0.7 | PHAS= | -140.1 | FOM= | 0.95 | TEST= 0
| INDE | 8 | 26 | 12 | FOBS= | 89.1 | SIGMA= | 1.1 | PHAS= | -133.3 | FOM= | 0.98 | TEST= 0
| INDE | 8 | 26 | 14 | FOBS= | 209.2 | SIGMA= | 0.6 | PHAS= | 171.1 | FOM= | 0.98 | TEST= 0
| INDE | 8 | 26 | 16 | FOBS= | 85.2 | SIGMA= | 1.3 | PHAS= | -34.8 | FOM= | 0.94 | TEST= 0
| INDE | 8 | 26 | 18 | FOBS= | 183.8 | SIGMA= | 0.9 | PHAS= | -128.4 | FOM= | 0.83 | TEST= 1
| INDE | 8 | 26 | 20 | FOBS= | 188.6 | SIGMA= | 0.9 | PHAS= | -139.8 | FOM= | 0.92 | TEST= 0
| INDE | 8 | 26 | 22 | FOBS= | 131.3 | SIGMA= | 1.0 | PHAS= | 29.7 | FOM= | 0.93 | TEST= 0
| INDE | 8 | 26 | 24 | FOBS= | 63.5 | SIGMA= | 1.9 | PHAS= | 104.9 | FOM= | 0.95 | TEST= 0
| INDE | 8 | 26 | 26 | FOBS= | 14.9 | SIGMA= | 7.7 | PHAS= | -125.7 | FOM= | 0.36 | TEST= 0
| INDE | 8 | 26 | 28 | FOBS= | 179.1 | SIGMA= | 0.8 | PHAS= | 68.6 | FOM= | 0.99 | TEST= 0
| INDE | 8 | 26 | 30 | FOBS= | 251.0 | SIGMA= | 0.7 | PHAS= | 148.4 | FOM= | 0.90 | TEST= 0
| INDE | 8 | 26 | 32 | FOBS= | 293.1 | SIGMA= | 0.6 | PHAS= | 96.7 | FOM= | 0.97 | TEST= 0
| INDE | 8 | 26 | 34 | FOBS= | 55.9 | SIGMA= | 2.7 | PHAS= | 118.9 | FOM= | 0.97 | TEST= 0
| INDE | 8 | 26 | 36 | FOBS= | 0.0 | SIGMA= | 19.9 | PHAS= | 0.0 | FOM= | 0.00 | TEST= 0
| INDE | 8 | 26 | 38 | FOBS= | 0.0 | SIGMA= | 20.2 | PHAS= | 0.0 | FOM= | 0.00 | TEST= 0
| INDE | 8 | 26 | 40 | FOBS= | 110.6 | SIGMA= | 1.9 | PHAS= | -74.0 | FOM= | 0.84 | TEST= 1
| INDE | 8 | 26 | 42 | FOBS= | 219.3 | SIGMA= | 0.9 | PHAS= | -20.6 | FOM= | 0.96 | TEST= 0
| INDE | 8 | 26 | 44 | FOBS= | 193.2 | SIGMA= | 1.0 | PHAS= | -71.6 | FOM= | 0.97 | TEST= 0
| INDE | 8 | 26 | 46 | FOBS= | 0.0 | SIGMA= | 19.2 | PHAS= | 0.0 | FOM= | 0.00 | TEST= 0
| INDE | 8 | 26 | 48 | FOBS= | 178.6 | SIGMA= | 1.1 | PHAS= | -167.3 | FOM= | 0.89 | TEST= 0
| INDE | 8 | 26 | 50 | FOBS= | 108.3 | SIGMA= | 1.6 | PHAS= | 142.1 | FOM= | 0.93 | TEST= 0
| INDE | 8 | 26 | 52 | FOBS= | 206.3 | SIGMA= | 0.9 | PHAS= | 126.8 | FOM= | 0.94 | TEST= 0
| INDE | 8 | 26 | 54 | FOBS= | 77.4 | SIGMA= | 1.7 | PHAS= | -150.9 | FOM= | 0.77 | TEST= 0
| INDE | 8 | 26 | 56 | FOBS= | 38.5 | SIGMA= | 4.3 | PHAS= | 90.2 | FOM= | 0.61 | TEST= 0
| INDE | 8 | 26 | 58 | FOBS= | 87.8 | SIGMA= | 2.0 | PHAS= | -176.0 | FOM= | 0.76 | TEST= 0
| INDE | 8 | 26 | 60 | FOBS= | 88.0 | SIGMA= | 2.0 | PHAS= | 90.4 | FOM= | 0.89 | TEST= 0
| INDE | 8 | 26 | 62 | FOBS= | 75.4 | SIGMA= | 4.3 | PHAS= | -34.8 | FOM= | 0.84 | TEST= 0
| INDE | 8 | 26 | 64 | FOBS= | 75.1 | SIGMA= | 4.4 | PHAS= | 114.4 | FOM= | 0.56 | TEST= 0
| INDE | 8 | 26 | 66 | FOBS= | 38.7 | SIGMA= | 12.3 | PHAS= | 139.4 | FOM= | 0.65 | TEST= 0
| INDE | 8 | 26 | 68 | FOBS= | 51.5 | SIGMA= | 9.5 | PHAS= | 75.1 | FOM= | 0.74 | TEST= 0
| INDE | 8 | 26 | 70 | FOBS= | 0.0 | SIGMA= | 30.9 | PHAS= | 0.0 | FOM= | 0.00 | TEST= 1
| INDE | 8 | 26 | 72 | FOBS= | 43.3 | SIGMA= | 11.6 | PHAS= | 13.4 | FOM= | 0.56 | TEST= 0
| INDE | 8 | 27 | 9 | FOBS= | 86.8 | SIGMA= | 0.9 | PHAS= | -110.4 | FOM= | 0.87 | TEST= 0
| INDE | 8 | 27 | 11 | FOBS= | 251.3 | SIGMA= | 0.6 | PHAS= | -156.0 | FOM= | 0.98 | TEST= 0
| INDE | 8 | 27 | 13 | FOBS= | 74.0 | SIGMA= | 1.3 | PHAS= | -163.5 | FOM= | 0.96 | TEST= 0
| INDE | 8 | 27 | 15 | FOBS= | 26.3 | SIGMA= | 3.7 | PHAS= | 44.5 | FOM= | 0.38 | TEST= 0
| INDE | 8 | 27 | 17 | FOBS= | 77.9 | SIGMA= | 1.5 | PHAS= | 82.2 | FOM= | 0.97 | TEST= 0
| INDE | 8 | 27 | 19 | FOBS= | 94.0 | SIGMA= | 1.5 | PHAS= | -31.5 | FOM= | 0.98 | TEST= 0
| INDE | 8 | 27 | 21 | FOBS= | 193.6 | SIGMA= | 0.9 | PHAS= | 12.6 | FOM= | 0.93 | TEST= 0
| INDE | 8 | 27 | 23 | FOBS= | 289.8 | SIGMA= | 0.7 | PHAS= | 115.0 | FOM= | 0.97 | TEST= 0
| INDE | 8 | 27 | 25 | FOBS= | 133.8 | SIGMA= | 1.0 | PHAS= | 47.1 | FOM= | 0.76 | TEST= 0
| INDE | 8 | 27 | 27 | FOBS= | 166.4 | SIGMA= | 0.8 | PHAS= | 89.9 | FOM= | 0.99 | TEST= 1
| INDE | 8 | 27 | 29 | FOBS= | 131.5 | SIGMA= | 1.1 | PHAS= | 49.5 | FOM= | 0.92 | TEST= 1
| INDE | 8 | 27 | 31 | FOBS= | 211.5 | SIGMA= | 0.9 | PHAS= | -26.0 | FOM= | 0.67 | TEST= 0
| INDE | 8 | 27 | 33 | FOBS= | 275.4 | SIGMA= | 0.7 | PHAS= | -25.6 | FOM= | 0.99 | TEST= 0
| INDE | 8 | 27 | 35 | FOBS= | 239.2 | SIGMA= | 0.8 | PHAS= | -31.7 | FOM= | 0.96 | TEST= 0
| INDE | 8 | 27 | 37 | FOBS= | 140.9 | SIGMA= | 1.4 | PHAS= | 93.9 | FOM= | 0.80 | TEST= 1
| INDE | 8 | 27 | 39 | FOBS= | 185.4 | SIGMA= | 1.2 | PHAS= | 178.2 | FOM= | 0.88 | TEST= 0
| INDE | 8 | 27 | 41 | FOBS= | 366.4 | SIGMA= | 0.7 | PHAS= | -105.9 | FOM= | 0.98 | TEST= 0
| INDE | 8 | 27 | 43 | FOBS= | 216.5 | SIGMA= | 0.9 | PHAS= | -125.9 | FOM= | 0.92 | TEST= 0
| INDE | 8 | 27 | 45 | FOBS= | 128.6 | SIGMA= | 1.4 | PHAS= | -119.5 | FOM= | 0.91 | TEST= 1
| INDE | 8 | 27 | 47 | FOBS= | 135.0 | SIGMA= | 1.4 | PHAS= | 115.6 | FOM= | 0.96 | TEST= 0
| INDE | 8 | 27 | 49 | FOBS= | 114.0 | SIGMA= | 1.6 | PHAS= | 148.8 | FOM= | 0.75 | TEST= 0
| INDE | 8 | 27 | 51 | FOBS= | 0.0 | SIGMA= | 18.8 | PHAS= | 0.0 | FOM= | 0.00 | TEST= 0
| INDE | 8 | 27 | 53 | FOBS= | 100.4 | SIGMA= | 1.7 | PHAS= | 137.5 | FOM= | 0.89 | TEST= 0
| INDE | 8 | 27 | 55 | FOBS= | 26.8 | SIGMA= | 4.8 | PHAS= | -23.7 | FOM= | 0.21 | TEST= 0
| INDE | 8 | 27 | 57 | FOBS= | 123.4 | SIGMA= | 1.3 | PHAS= | 3.9 | FOM= | 0.88 | TEST= 0
| INDE | 8 | 27 | 59 | FOBS= | 29.0 | SIGMA= | 7.8 | PHAS= | 147.1 | FOM= | 0.39 | TEST= 0
| INDE | 8 | 27 | 61 | FOBS= | 60.2 | SIGMA= | 3.2 | PHAS= | 10.7 | FOM= | 0.69 | TEST= 0
| INDE | 8 | 27 | 63 | FOBS= | 64.6 | SIGMA= | 5.0 | PHAS= | 49.4 | FOM= | 0.62 | TEST= 0
| INDE | 8 | 27 | 65 | FOBS= | 0.0 | SIGMA= | 30.7 | PHAS= | 0.0 | FOM= | 0.00 | TEST= 0
| INDE | 8 | 27 | 67 | FOBS= | 84.0 | SIGMA= | 5.7 | PHAS= | -36.9 | FOM= | 0.90 | TEST= 0
| INDE | 8 | 27 | 69 | FOBS= | 21.5 | SIGMA= | 22.4 | PHAS= | 30.9 | FOM= | 0.54 | TEST= 0
| INDE | 8 | 27 | 71 | FOBS= | 0.0 | SIGMA= | 32.1 | PHAS= | 0.0 | FOM= | 0.00 | TEST= 0
| INDE | 8 | 28 | 8 | FOBS= | 132.4 | SIGMA= | 0.7 | PHAS= | -128.9 | FOM= | 0.91 | TEST= 0
| INDE | 8 | 28 | 10 | FOBS= | 255.8 | SIGMA= | 0.7 | PHAS= | 156.1 | FOM= | 0.99 | TEST= 0
| INDE | 8 | 28 | 12 | FOBS= | 90.6 | SIGMA= | 1.1 | PHAS= | -55.3 | FOM= | 0.91 | TEST= 0
| INDE | 8 | 28 | 14 | FOBS= | 115.2 | SIGMA= | 1.0 | PHAS= | -172.5 | FOM= | 0.91 | TEST= 0
| INDE | 8 | 28 | 16 | FOBS= | 61.3 | SIGMA= | 1.7 | PHAS= | -56.6 | FOM= | 0.96 | TEST= 0
| INDE | 8 | 28 | 18 | FOBS= | 144.4 | SIGMA= | 0.8 | PHAS= | -109.8 | FOM= | 0.98 | TEST= 0

*FIG. 12A - 219*

```
INDE   8   28   20  FOBS=    211.7  SIGMA=    0.8  PHAS=   -134.9  FOM=  0.94  TEST= 0
INDE   8   28   22  FOBS=    340.4  SIGMA=    0.7  PHAS=    -33.4  FOM=  0.96  TEST= 1
INDE   8   28   24  FOBS=    191.2  SIGMA=    0.8  PHAS=    -57.7  FOM=  0.94  TEST= 0
INDE   8   28   26  FOBS=    283.4  SIGMA=    0.6  PHAS=    -64.2  FOM=  0.98  TEST= 0
INDE   8   28   28  FOBS=    206.5  SIGMA=    0.8  PHAS=     44.5  FOM=  0.92  TEST= 0
INDE   8   28   30  FOBS=     96.0  SIGMA=    1.5  PHAS=     33.3  FOM=  0.68  TEST= 0
INDE   8   28   32  FOBS=    197.7  SIGMA=    0.9  PHAS=    -94.3  FOM=  0.94  TEST= 0
INDE   8   28   34  FOBS=    286.7  SIGMA=    0.8  PHAS=   -134.7  FOM=  0.99  TEST= 0
INDE   8   28   36  FOBS=    167.4  SIGMA=    1.1  PHAS=     17.3  FOM=  0.72  TEST= 1
INDE   8   28   38  FOBS=    250.7  SIGMA=    0.9  PHAS=      6.4  FOM=  0.97  TEST= 0
INDE   8   28   40  FOBS=    203.8  SIGMA=    1.1  PHAS=    154.3  FOM=  0.94  TEST= 0
INDE   8   28   42  FOBS=    131.9  SIGMA=    1.6  PHAS=   -119.3  FOM=  0.93  TEST= 0
INDE   8   28   44  FOBS=     96.9  SIGMA=    2.1  PHAS=    135.9  FOM=  0.82  TEST= 0
INDE   8   28   46  FOBS=      0.0  SIGMA=   20.3  PHAS=      0.0  FOM=  0.00  TEST= 0
INDE   8   28   48  FOBS=    107.2  SIGMA=    1.7  PHAS=    169.3  FOM=  0.92  TEST= 0
INDE   8   28   50  FOBS=    104.6  SIGMA=    1.7  PHAS=    127.7  FOM=  0.88  TEST= 0
INDE   8   28   52  FOBS=     73.7  SIGMA=    2.3  PHAS=   -163.0  FOM=  0.92  TEST= 0
INDE   8   28   54  FOBS=      0.0  SIGMA=   17.7  PHAS=      0.0  FOM=  0.00  TEST= 0
INDE   8   28   56  FOBS=     27.3  SIGMA=    5.5  PHAS=    117.2  FOM=  0.56  TEST= 0
INDE   8   28   58  FOBS=     90.8  SIGMA=    1.7  PHAS=    164.9  FOM=  0.91  TEST= 0
INDE   8   28   60  FOBS=     82.8  SIGMA=    2.0  PHAS=     19.9  FOM=  0.88  TEST= 0
INDE   8   28   62  FOBS=     33.0  SIGMA=    9.7  PHAS=    -26.4  FOM=  0.39  TEST= 1
INDE   8   28   64  FOBS=     37.1  SIGMA=    8.7  PHAS=     74.6  FOM=  0.58  TEST= 0
INDE   8   28   66  FOBS=     16.6  SIGMA=   28.8  PHAS=   -162.4  FOM=  0.28  TEST= 0
INDE   8   28   68  FOBS=      0.0  SIGMA=   31.1  PHAS=      0.0  FOM=  0.00  TEST= 0
INDE   8   28   70  FOBS=     83.0  SIGMA=    6.1  PHAS=    -65.8  FOM=  0.92  TEST= 0
INDE   8   28   72  FOBS=     44.3  SIGMA=   11.6  PHAS=   -129.3  FOM=  0.55  TEST= 0
INDE   8   29    9  FOBS=     14.1  SIGMA=    6.6  PHAS=    169.1  FOM=  0.84  TEST= 0
INDE   8   29   11  FOBS=    143.5  SIGMA=    0.8  PHAS=    153.5  FOM=  0.99  TEST= 0
INDE   8   29   13  FOBS=    199.1  SIGMA=    0.7  PHAS=   -143.7  FOM=  0.97  TEST= 0
INDE   8   29   15  FOBS=    154.8  SIGMA=    0.8  PHAS=    108.9  FOM=  0.98  TEST= 0
INDE   8   29   17  FOBS=     82.6  SIGMA=    1.5  PHAS=    113.9  FOM=  0.95  TEST= 0
INDE   8   29   19  FOBS=    106.4  SIGMA=    1.4  PHAS=   -112.2  FOM=  0.92  TEST= 1
INDE   8   29   21  FOBS=    179.2  SIGMA=    1.0  PHAS=    152.8  FOM=  0.97  TEST= 1
INDE   8   29   23  FOBS=    445.6  SIGMA=    0.6  PHAS=   -157.3  FOM=  0.97  TEST= 0
INDE   8   29   25  FOBS=    292.7  SIGMA=    0.8  PHAS=   -134.4  FOM=  0.97  TEST= 0
INDE   8   29   27  FOBS=    217.1  SIGMA=    0.7  PHAS=   -119.5  FOM=  0.96  TEST= 0
INDE   8   29   29  FOBS=    116.5  SIGMA=    1.3  PHAS=     33.7  FOM=  0.96  TEST= 0
INDE   8   29   31  FOBS=      0.0  SIGMA=   17.7  PHAS=      0.0  FOM=  0.00  TEST= 0
INDE   8   29   33  FOBS=    280.6  SIGMA=    0.7  PHAS=   -124.9  FOM=  0.98  TEST= 1
INDE   8   29   35  FOBS=     97.6  SIGMA=    1.9  PHAS=     27.9  FOM=  0.56  TEST= 0
INDE   8   29   37  FOBS=    133.4  SIGMA=    1.4  PHAS=    -99.9  FOM=  0.76  TEST= 0
INDE   8   29   39  FOBS=     75.2  SIGMA=    2.9  PHAS=    124.7  FOM=  0.14  TEST= 0
INDE   8   29   41  FOBS=    161.9  SIGMA=    1.3  PHAS=    170.0  FOM=  0.92  TEST= 0
INDE   8   29   43  FOBS=    171.5  SIGMA=    1.3  PHAS=    170.8  FOM=  0.93  TEST= 0
INDE   8   29   45  FOBS=     95.6  SIGMA=    2.1  PHAS=    -91.5  FOM=  0.91  TEST= 0
INDE   8   29   47  FOBS=    219.2  SIGMA=    1.0  PHAS=     95.2  FOM=  0.95  TEST= 0
INDE   8   29   49  FOBS=     55.7  SIGMA=    3.1  PHAS=    111.6  FOM=  0.81  TEST= 0
INDE   8   29   51  FOBS=     92.7  SIGMA=    1.9  PHAS=   -153.7  FOM=  0.86  TEST= 0
INDE   8   29   53  FOBS=     54.4  SIGMA=    3.1  PHAS=    128.7  FOM=  0.91  TEST= 0
INDE   8   29   55  FOBS=     59.7  SIGMA=    2.5  PHAS=    -94.2  FOM=  0.40  TEST= 0
INDE   8   29   57  FOBS=     84.5  SIGMA=    1.9  PHAS=     61.1  FOM=  0.95  TEST= 0
INDE   8   29   59  FOBS=     85.4  SIGMA=    1.9  PHAS=    130.8  FOM=  0.89  TEST= 0
INDE   8   29   61  FOBS=     33.3  SIGMA=    5.5  PHAS=    -65.0  FOM=  0.64  TEST= 0
INDE   8   29   63  FOBS=      0.0  SIGMA=   25.4  PHAS=      0.0  FOM=  0.00  TEST= 0
INDE   8   29   65  FOBS=     58.7  SIGMA=    8.1  PHAS=    -80.4  FOM=  0.74  TEST= 0
INDE   8   29   67  FOBS=      0.0  SIGMA=   30.9  PHAS=      0.0  FOM=  0.00  TEST= 1
INDE   8   29   69  FOBS=     59.0  SIGMA=    8.3  PHAS=   -158.2  FOM=  0.73  TEST= 0
INDE   8   29   71  FOBS=    121.6  SIGMA=    4.4  PHAS=    171.2  FOM=  0.96  TEST= 0
INDE   8   30    8  FOBS=    131.7  SIGMA=    0.7  PHAS=     53.3  FOM=  0.85  TEST= 0
INDE   8   30   10  FOBS=    117.4  SIGMA=    0.9  PHAS=    155.4  FOM=  0.96  TEST= 0
INDE   8   30   12  FOBS=     53.2  SIGMA=    1.9  PHAS=     55.0  FOM=  0.70  TEST= 0
INDE   8   30   14  FOBS=    105.7  SIGMA=    1.1  PHAS=    169.2  FOM=  0.94  TEST= 0
INDE   8   30   16  FOBS=    179.9  SIGMA=    0.8  PHAS=    -37.7  FOM=  0.96  TEST= 0
INDE   8   30   18  FOBS=    104.7  SIGMA=    1.2  PHAS=    -78.2  FOM=  0.81  TEST= 1
INDE   8   30   20  FOBS=     36.9  SIGMA=    4.0  PHAS=   -153.1  FOM=  0.18  TEST= 0
INDE   8   30   22  FOBS=    523.6  SIGMA=    0.7  PHAS=     48.3  FOM=  0.98  TEST= 0
INDE   8   30   24  FOBS=    338.8  SIGMA=    0.6  PHAS=    146.0  FOM=  0.97  TEST= 0
INDE   8   30   26  FOBS=     57.2  SIGMA=    2.6  PHAS=   -117.7  FOM=  0.94  TEST= 0
INDE   8   30   28  FOBS=      0.0  SIGMA=   18.1  PHAS=      0.0  FOM=  0.00  TEST= 0
```

*FIG. 12A - 220*

| | | | | | | | | | | | |
|---|---|---|---|---|---|---|---|---|---|---|---|
| INDE | 8 | 30 | 30 | FOBS= | 71.3 | SIGMA= | 2.2 | PHAS= | -79.3 | FOM= | 0.95 | TEST= 0
| INDE | 8 | 30 | 32 | FOBS= | 93.4 | SIGMA= | 1.8 | PHAS= | -127.2 | FOM= | 0.89 | TEST= 0
| INDE | 8 | 30 | 34 | FOBS= | 264.1 | SIGMA= | 0.8 | PHAS= | 145.4 | FOM= | 0.94 | TEST= 0
| INDE | 8 | 30 | 36 | FOBS= | 139.9 | SIGMA= | 1.4 | PHAS= | 92.7 | FOM= | 0.78 | TEST= 1
| INDE | 8 | 30 | 38 | FOBS= | 0.0 | SIGMA= | 19.5 | PHAS= | 0.0 | FOM= | 0.00 | TEST= 1
| INDE | 8 | 30 | 40 | FOBS= | 93.7 | SIGMA= | 2.3 | PHAS= | 42.6 | FOM= | 0.89 | TEST= 0
| INDE | 8 | 30 | 42 | FOBS= | 145.4 | SIGMA= | 1.7 | PHAS= | 118.4 | FOM= | 0.80 | TEST= 0
| INDE | 8 | 30 | 44 | FOBS= | 145.8 | SIGMA= | 1.4 | PHAS= | 152.1 | FOM= | 0.95 | TEST= 0
| INDE | 8 | 30 | 46 | FOBS= | 56.9 | SIGMA= | 3.5 | PHAS= | 46.3 | FOM= | 0.29 | TEST= 1
| INDE | 8 | 30 | 48 | FOBS= | 53.6 | SIGMA= | 3.6 | PHAS= | 121.5 | FOM= | 0.73 | TEST= 0
| INDE | 8 | 30 | 50 | FOBS= | 71.9 | SIGMA= | 2.4 | PHAS= | 102.9 | FOM= | 0.45 | TEST= 0
| INDE | 8 | 30 | 52 | FOBS= | 38.5 | SIGMA= | 4.6 | PHAS= | 109.6 | FOM= | 0.48 | TEST= 0
| INDE | 8 | 30 | 54 | FOBS= | 102.6 | SIGMA= | 1.5 | PHAS= | 145.6 | FOM= | 0.91 | TEST= 0
| INDE | 8 | 30 | 56 | FOBS= | 55.6 | SIGMA= | 2.6 | PHAS= | -83.9 | FOM= | 0.51 | TEST= 0
| INDE | 8 | 30 | 58 | FOBS= | 14.8 | SIGMA= | 10.4 | PHAS= | 138.5 | FOM= | 0.39 | TEST= 0
| INDE | 8 | 30 | 60 | FOBS= | 116.7 | SIGMA= | 1.5 | PHAS= | 67.3 | FOM= | 0.95 | TEST= 0
| INDE | 8 | 30 | 62 | FOBS= | 50.1 | SIGMA= | 3.7 | PHAS= | 17.6 | FOM= | 0.76 | TEST= 0
| INDE | 8 | 30 | 64 | FOBS= | 67.9 | SIGMA= | 3.4 | PHAS= | -114.4 | FOM= | 0.62 | TEST= 0
| INDE | 8 | 30 | 66 | FOBS= | 27.7 | SIGMA= | 17.6 | PHAS= | -98.1 | FOM= | 0.44 | TEST= 0
| INDE | 8 | 30 | 68 | FOBS= | 25.2 | SIGMA= | 19.6 | PHAS= | -50.0 | FOM= | 0.38 | TEST= 0
| INDE | 8 | 31 | 9 | FOBS= | 174.0 | SIGMA= | 0.6 | PHAS= | 5.8 | FOM= | 0.91 | TEST= 0
| INDE | 8 | 31 | 11 | FOBS= | 163.5 | SIGMA= | 0.8 | PHAS= | 67.8 | FOM= | 0.90 | TEST= 0
| INDE | 8 | 31 | 13 | FOBS= | 208.1 | SIGMA= | 0.7 | PHAS= | -86.3 | FOM= | 0.94 | TEST= 0
| INDE | 8 | 31 | 15 | FOBS= | 23.8 | SIGMA= | 4.6 | PHAS= | 38.9 | FOM= | 0.39 | TEST= 0
| INDE | 8 | 31 | 17 | FOBS= | 58.3 | SIGMA= | 2.2 | PHAS= | -17.4 | FOM= | 0.44 | TEST= 0
| INDE | 8 | 31 | 19 | FOBS= | 44.6 | SIGMA= | 2.7 | PHAS= | -131.8 | FOM= | 0.97 | TEST= 0
| INDE | 8 | 31 | 21 | FOBS= | 174.3 | SIGMA= | 1.1 | PHAS= | -86.8 | FOM= | 0.98 | TEST= 0
| INDE | 8 | 31 | 23 | FOBS= | 258.9 | SIGMA= | 0.9 | PHAS= | 11.1 | FOM= | 0.95 | TEST= 0
| INDE | 8 | 31 | 25 | FOBS= | 107.8 | SIGMA= | 1.5 | PHAS= | -57.8 | FOM= | 0.91 | TEST= 0
| INDE | 8 | 31 | 27 | FOBS= | 151.5 | SIGMA= | 1.2 | PHAS= | -66.0 | FOM= | 0.92 | TEST= 0
| INDE | 8 | 31 | 29 | FOBS= | 37.4 | SIGMA= | 4.1 | PHAS= | 150.4 | FOM= | 0.34 | TEST= 0
| INDE | 8 | 31 | 31 | FOBS= | 52.8 | SIGMA= | 3.2 | PHAS= | 32.7 | FOM= | 0.81 | TEST= 0
| INDE | 8 | 31 | 33 | FOBS= | 59.5 | SIGMA= | 3.3 | PHAS= | 73.5 | FOM= | 0.69 | TEST= 0
| INDE | 8 | 31 | 35 | FOBS= | 137.3 | SIGMA= | 1.6 | PHAS= | -13.5 | FOM= | 0.82 | TEST= 0
| INDE | 8 | 31 | 37 | FOBS= | 167.7 | SIGMA= | 1.2 | PHAS= | 113.1 | FOM= | 0.97 | TEST= 0
| INDE | 8 | 31 | 39 | FOBS= | 53.2 | SIGMA= | 3.6 | PHAS= | 37.2 | FOM= | 0.70 | TEST= 0
| INDE | 8 | 31 | 41 | FOBS= | 122.2 | SIGMA= | 1.6 | PHAS= | -86.1 | FOM= | 0.95 | TEST= 0
| INDE | 8 | 31 | 43 | FOBS= | 146.7 | SIGMA= | 1.6 | PHAS= | 124.6 | FOM= | 0.87 | TEST= 0
| INDE | 8 | 31 | 45 | FOBS= | 50.8 | SIGMA= | 3.9 | PHAS= | 20.7 | FOM= | 0.92 | TEST= 0
| INDE | 8 | 31 | 47 | FOBS= | 70.5 | SIGMA= | 2.8 | PHAS= | 35.6 | FOM= | 0.82 | TEST= 0
| INDE | 8 | 31 | 49 | FOBS= | 0.0 | SIGMA= | 20.1 | PHAS= | 0.0 | FOM= | 0.00 | TEST= 1
| INDE | 8 | 31 | 51 | FOBS= | 108.5 | SIGMA= | 1.7 | PHAS= | 179.4 | FOM= | 0.51 | TEST= 1
| INDE | 8 | 31 | 53 | FOBS= | 147.1 | SIGMA= | 1.2 | PHAS= | 31.3 | FOM= | 0.94 | TEST= 0
| INDE | 8 | 31 | 55 | FOBS= | 73.2 | SIGMA= | 2.1 | PHAS= | -173.1 | FOM= | 0.73 | TEST= 0
| INDE | 8 | 31 | 57 | FOBS= | 47.0 | SIGMA= | 3.3 | PHAS= | 118.5 | FOM= | 0.64 | TEST= 0
| INDE | 8 | 31 | 59 | FOBS= | 54.4 | SIGMA= | 3.2 | PHAS= | 42.6 | FOM= | 0.84 | TEST= 0
| INDE | 8 | 31 | 61 | FOBS= | 96.7 | SIGMA= | 1.8 | PHAS= | -20.7 | FOM= | 0.90 | TEST= 0
| INDE | 8 | 31 | 63 | FOBS= | 0.0 | SIGMA= | 20.0 | PHAS= | 0.0 | FOM= | 0.00 | TEST= 0
| INDE | 8 | 31 | 65 | FOBS= | 0.0 | SIGMA= | 31.1 | PHAS= | 0.0 | FOM= | 0.00 | TEST= 0
| INDE | 8 | 31 | 67 | FOBS= | 0.0 | SIGMA= | 31.4 | PHAS= | 0.0 | FOM= | 0.00 | TEST= 0
| INDE | 8 | 31 | 69 | FOBS= | 82.6 | SIGMA= | 6.2 | PHAS= | -110.7 | FOM= | 0.58 | TEST= 0
| INDE | 8 | 32 | 8 | FOBS= | 72.6 | SIGMA= | 1.5 | PHAS= | -72.2 | FOM= | 0.92 | TEST= 1
| INDE | 8 | 32 | 10 | FOBS= | 141.9 | SIGMA= | 0.8 | PHAS= | -79.6 | FOM= | 0.65 | TEST= 0
| INDE | 8 | 32 | 12 | FOBS= | 141.1 | SIGMA= | 0.9 | PHAS= | 1.4 | FOM= | 0.96 | TEST= 0
| INDE | 8 | 32 | 14 | FOBS= | 217.1 | SIGMA= | 0.7 | PHAS= | -152.5 | FOM= | 0.98 | TEST= 0
| INDE | 8 | 32 | 16 | FOBS= | 326.1 | SIGMA= | 0.6 | PHAS= | -97.4 | FOM= | 0.99 | TEST= 0
| INDE | 8 | 32 | 18 | FOBS= | 72.1 | SIGMA= | 1.9 | PHAS= | -168.8 | FOM= | 0.76 | TEST= 0
| INDE | 8 | 32 | 20 | FOBS= | 76.8 | SIGMA= | 1.7 | PHAS= | 16.5 | FOM= | 0.65 | TEST= 0
| INDE | 8 | 32 | 22 | FOBS= | 236.8 | SIGMA= | 0.9 | PHAS= | -66.0 | FOM= | 0.96 | TEST= 0
| INDE | 8 | 32 | 24 | FOBS= | 151.7 | SIGMA= | 1.3 | PHAS= | 150.3 | FOM= | 0.96 | TEST= 0
| INDE | 8 | 32 | 26 | FOBS= | 259.6 | SIGMA= | 0.8 | PHAS= | 85.0 | FOM= | 0.88 | TEST= 0
| INDE | 8 | 32 | 28 | FOBS= | 156.7 | SIGMA= | 1.2 | PHAS= | 122.5 | FOM= | 0.60 | TEST= 0
| INDE | 8 | 32 | 30 | FOBS= | 120.6 | SIGMA= | 1.4 | PHAS= | -68.9 | FOM= | 0.81 | TEST= 0
| INDE | 8 | 32 | 32 | FOBS= | 107.5 | SIGMA= | 1.7 | PHAS= | 124.3 | FOM= | 0.59 | TEST= 0
| INDE | 8 | 32 | 34 | FOBS= | 248.5 | SIGMA= | 0.9 | PHAS= | 141.6 | FOM= | 0.96 | TEST= 0
| INDE | 8 | 32 | 36 | FOBS= | 324.8 | SIGMA= | 1.2 | PHAS= | 83.2 | FOM= | 0.98 | TEST= 0
| INDE | 8 | 32 | 38 | FOBS= | 8.9 | SIGMA= | 24.2 | PHAS= | 19.3 | FOM= | 0.07 | TEST= 0
| INDE | 8 | 32 | 40 | FOBS= | 174.6 | SIGMA= | 1.2 | PHAS= | -32.4 | FOM= | 0.94 | TEST= 0
| INDE | 8 | 32 | 42 | FOBS= | 184.2 | SIGMA= | 1.1 | PHAS= | 90.9 | FOM= | 0.91 | TEST= 0
| INDE | 8 | 32 | 44 | FOBS= | 86.6 | SIGMA= | 2.6 | PHAS= | -84.9 | FOM= | 0.75 | TEST= 0

*FIG. 12A - 221*

```
INDE  8  32  46 FOBS=   95.0 SIGMA=  2.4 PHAS=  -74.0 FOM= 0.94 TEST= 0
INDE  8  32  48 FOBS=   61.9 SIGMA=  3.1 PHAS= -156.9 FOM= 0.34 TEST= 1
INDE  8  32  50 FOBS=    0.0 SIGMA= 20.4 PHAS=    0.0 FOM= 0.00 TEST= 0
INDE  8  32  52 FOBS=   92.4 SIGMA=  2.1 PHAS= -124.2 FOM= 0.45 TEST= 1
INDE  8  32  54 FOBS=   84.7 SIGMA=  2.1 PHAS= -166.5 FOM= 0.92 TEST= 0
INDE  8  32  56 FOBS=   43.4 SIGMA=  3.7 PHAS=   91.8 FOM= 0.82 TEST= 0
INDE  8  32  58 FOBS=   57.2 SIGMA=  2.9 PHAS=  -14.7 FOM= 0.48 TEST= 0
INDE  8  32  60 FOBS=    0.0 SIGMA= 19.8 PHAS=    0.0 FOM= 0.00 TEST= 0
INDE  8  32  62 FOBS=   55.3 SIGMA=  3.1 PHAS= -119.2 FOM= 0.32 TEST= 0
INDE  8  32  64 FOBS=   75.5 SIGMA=  2.4 PHAS=  101.9 FOM= 0.88 TEST= 0
INDE  8  32  66 FOBS=   40.5 SIGMA=  9.0 PHAS=  144.4 FOM= 0.46 TEST= 0
INDE  8  32  68 FOBS=   25.6 SIGMA= 19.5 PHAS=  -34.8 FOM= 0.21 TEST= 0
INDE  8  32  70 FOBS=   44.6 SIGMA= 11.7 PHAS=  130.9 FOM= 0.50 TEST= 0
INDE  8  33   9 FOBS=  104.8 SIGMA=  0.9 PHAS=  -11.1 FOM= 0.96 TEST= 0
INDE  8  33  11 FOBS=   87.9 SIGMA=  1.3 PHAS=  134.7 FOM= 0.93 TEST= 0
INDE  8  33  13 FOBS=  164.7 SIGMA=  0.8 PHAS=  -88.4 FOM= 0.47 TEST= 1
INDE  8  33  15 FOBS=  230.1 SIGMA=  0.8 PHAS=  -96.5 FOM= 0.33 TEST= 1
INDE  8  33  17 FOBS=  106.9 SIGMA=  1.2 PHAS=  167.5 FOM= 0.87 TEST= 0
INDE  8  33  19 FOBS=  185.9 SIGMA=  0.8 PHAS= -104.2 FOM= 0.92 TEST= 0
INDE  8  33  21 FOBS=  292.6 SIGMA=  0.7 PHAS= -161.9 FOM= 0.98 TEST= 1
INDE  8  33  23 FOBS=  162.8 SIGMA=  1.3 PHAS=  -18.6 FOM= 0.94 TEST= 0
INDE  8  33  25 FOBS=  182.2 SIGMA=  1.2 PHAS=  -24.2 FOM= 0.65 TEST= 1
INDE  8  33  27 FOBS=  222.1 SIGMA=  0.9 PHAS=    0.3 FOM= 0.96 TEST= 0
INDE  8  33  29 FOBS=   99.0 SIGMA=  1.8 PHAS= -130.4 FOM= 0.87 TEST= 0
INDE  8  33  31 FOBS=   79.0 SIGMA=  2.3 PHAS=   40.2 FOM= 0.84 TEST= 1
INDE  8  33  33 FOBS=  261.1 SIGMA=  0.9 PHAS=   86.7 FOM= 0.96 TEST= 0
INDE  8  33  35 FOBS=  278.2 SIGMA=  0.9 PHAS=  -44.8 FOM= 0.98 TEST= 0
INDE  8  33  37 FOBS=  221.7 SIGMA=  1.3 PHAS=   67.6 FOM= 0.95 TEST= 0
INDE  8  33  39 FOBS=    0.0 SIGMA= 20.0 PHAS=    0.0 FOM= 0.00 TEST= 0
INDE  8  33  41 FOBS=   90.9 SIGMA=  2.1 PHAS=    2.9 FOM= 0.71 TEST= 1
INDE  8  33  43 FOBS=   44.1 SIGMA=  4.3 PHAS= -149.5 FOM= 0.84 TEST= 0
INDE  8  33  45 FOBS=  177.2 SIGMA=  1.4 PHAS=  141.6 FOM= 0.97 TEST= 0
INDE  8  33  47 FOBS=  108.8 SIGMA=  2.1 PHAS=  127.2 FOM= 0.85 TEST= 0
INDE  8  33  49 FOBS=   84.5 SIGMA=  2.5 PHAS=  -81.5 FOM= 0.84 TEST= 0
INDE  8  33  51 FOBS=    0.0 SIGMA= 20.2 PHAS=    0.0 FOM= 0.00 TEST= 0
INDE  8  33  53 FOBS=   61.1 SIGMA=  3.1 PHAS=   65.1 FOM= 0.86 TEST= 0
INDE  8  33  55 FOBS=   90.0 SIGMA=  2.0 PHAS=  170.5 FOM= 0.86 TEST= 0
INDE  8  33  57 FOBS=   27.6 SIGMA=  6.3 PHAS=   71.1 FOM= 0.40 TEST= 1
INDE  8  33  59 FOBS=   24.2 SIGMA=  7.6 PHAS= -150.3 FOM= 0.43 TEST= 0
INDE  8  33  61 FOBS=   64.6 SIGMA=  2.7 PHAS=  133.0 FOM= 0.61 TEST= 0
INDE  8  33  63 FOBS=   66.0 SIGMA=  2.6 PHAS=  -27.0 FOM= 0.85 TEST= 0
INDE  8  33  65 FOBS=   34.7 SIGMA=  6.2 PHAS=   11.7 FOM= 0.71 TEST= 0
INDE  8  33  67 FOBS=    0.0 SIGMA= 26.9 PHAS=    0.0 FOM= 0.00 TEST= 0
INDE  8  33  69 FOBS=    7.0 SIGMA= 73.7 PHAS=   47.6 FOM= 0.20 TEST= 0
INDE  8  34   8 FOBS=  329.9 SIGMA=  0.7 PHAS= -112.7 FOM= 0.94 TEST= 0
INDE  8  34  10 FOBS=  237.3 SIGMA=  0.7 PHAS=   34.1 FOM= 0.97 TEST= 0
INDE  8  34  12 FOBS=   31.5 SIGMA=  3.7 PHAS=  164.2 FOM= 0.19 TEST= 0
INDE  8  34  14 FOBS=  330.5 SIGMA=  0.7 PHAS= -126.4 FOM= 0.95 TEST= 0
INDE  8  34  16 FOBS=  135.7 SIGMA=  1.0 PHAS= -127.7 FOM= 0.95 TEST= 0
INDE  8  34  18 FOBS=  284.3 SIGMA=  0.8 PHAS= -145.3 FOM= 0.97 TEST= 0
INDE  8  34  20 FOBS=  280.7 SIGMA=  0.7 PHAS=  142.3 FOM= 0.88 TEST= 0
INDE  8  34  22 FOBS=  248.3 SIGMA=  1.0 PHAS= -139.2 FOM= 0.97 TEST= 0
INDE  8  34  24 FOBS=  104.9 SIGMA=  2.0 PHAS= -145.6 FOM= 0.97 TEST= 0
INDE  8  34  26 FOBS=  344.3 SIGMA=  0.8 PHAS=  -29.4 FOM= 0.96 TEST= 0
INDE  8  34  28 FOBS=   74.3 SIGMA=  2.5 PHAS= -165.1 FOM= 0.92 TEST= 0
INDE  8  34  30 FOBS=   46.8 SIGMA=  3.8 PHAS=  -33.9 FOM= 0.82 TEST= 0
INDE  8  34  32 FOBS=  125.2 SIGMA=  1.6 PHAS=  -11.9 FOM= 0.93 TEST= 0
INDE  8  34  34 FOBS=   63.5 SIGMA=  3.3 PHAS=  165.8 FOM= 0.12 TEST= 0
INDE  8  34  36 FOBS=   82.1 SIGMA=  2.5 PHAS=  -33.8 FOM= 0.83 TEST= 0
INDE  8  34  38 FOBS=  100.5 SIGMA=  2.1 PHAS=   14.2 FOM= 0.43 TEST= 1
INDE  8  34  40 FOBS=   98.4 SIGMA=  2.0 PHAS=  -51.6 FOM= 0.91 TEST= 0
INDE  8  34  42 FOBS=   60.7 SIGMA=  3.0 PHAS=    0.0 FOM= 0.82 TEST= 0
INDE  8  34  44 FOBS=   71.7 SIGMA=  2.5 PHAS=  -14.6 FOM= 0.93 TEST= 0
INDE  8  34  46 FOBS=  210.6 SIGMA=  1.2 PHAS=   16.0 FOM= 0.97 TEST= 0
INDE  8  34  48 FOBS=  182.6 SIGMA=  1.3 PHAS=   70.7 FOM= 0.91 TEST= 0
INDE  8  34  50 FOBS=   89.6 SIGMA=  2.5 PHAS=  -70.1 FOM= 0.86 TEST= 0
INDE  8  34  52 FOBS=  125.3 SIGMA=  1.6 PHAS=  -14.7 FOM= 0.80 TEST= 0
INDE  8  34  54 FOBS=   70.3 SIGMA=  2.8 PHAS=   88.2 FOM= 0.30 TEST= 1
INDE  8  34  56 FOBS=  148.4 SIGMA=  1.3 PHAS=  121.3 FOM= 0.95 TEST= 0
INDE  8  34  58 FOBS=   39.2 SIGMA=  4.4 PHAS=   48.0 FOM= 0.55 TEST= 0
```

*FIG. 12A - 222*

```
INDE  8  34  60  FOBS=    54.6  SIGMA=   3.2  PHAS=  162.8  FOM=  0.81  TEST= 0
INDE  8  34  62  FOBS=    66.7  SIGMA=   2.7  PHAS=  143.6  FOM=  0.21  TEST= 1
INDE  8  34  64  FOBS=    38.5  SIGMA=   4.5  PHAS=   69.6  FOM=  0.84  TEST= 0
INDE  8  34  66  FOBS=    78.5  SIGMA=   2.5  PHAS=  -61.9  FOM=  0.88  TEST= 0
INDE  8  34  68  FOBS=   106.3  SIGMA=   2.5  PHAS=  -54.2  FOM=  0.95  TEST= 0
INDE  8  35   9  FOBS=   250.3  SIGMA=   0.7  PHAS=  -39.0  FOM=  0.94  TEST= 0
INDE  8  35  11  FOBS=    77.5  SIGMA=   2.1  PHAS=  109.1  FOM=  0.96  TEST= 0
INDE  8  35  13  FOBS=   210.9  SIGMA=   0.7  PHAS=  157.6  FOM=  0.98  TEST= 0
INDE  8  35  15  FOBS=   236.9  SIGMA=   0.8  PHAS=  140.1  FOM=  0.96  TEST= 0
INDE  8  35  17  FOBS=   404.7  SIGMA=   0.6  PHAS=  117.5  FOM=  0.96  TEST= 0
INDE  8  35  19  FOBS=   253.4  SIGMA=   0.9  PHAS= -177.5  FOM=  0.97  TEST= 0
INDE  8  35  21  FOBS=   378.4  SIGMA=   0.7  PHAS=  109.1  FOM=  0.97  TEST= 0
INDE  8  35  23  FOBS=     0.0  SIGMA=  19.9  PHAS=    0.0  FOM=  0.00  TEST= 0
INDE  8  35  25  FOBS=   276.5  SIGMA=   1.0  PHAS=  -97.0  FOM=  0.95  TEST= 0
INDE  8  35  27  FOBS=    61.5  SIGMA=   3.6  PHAS=  -92.0  FOM=  0.89  TEST= 0
INDE  8  35  29  FOBS=   113.3  SIGMA=   2.2  PHAS= -142.4  FOM=  0.90  TEST= 0
INDE  8  35  31  FOBS=   182.9  SIGMA=   1.1  PHAS=  -24.7  FOM=  0.96  TEST= 0
INDE  8  35  33  FOBS=    98.7  SIGMA=   2.1  PHAS=  108.2  FOM=  0.63  TEST= 0
INDE  8  35  35  FOBS=   101.4  SIGMA=   2.0  PHAS= -106.8  FOM=  0.74  TEST= 1
INDE  8  35  37  FOBS=   121.5  SIGMA=   1.7  PHAS=  105.8  FOM=  0.82  TEST= 0
INDE  8  35  39  FOBS=   150.0  SIGMA=   1.3  PHAS= -115.2  FOM=  0.92  TEST= 0
INDE  8  35  41  FOBS=     0.0  SIGMA=  20.1  PHAS=    0.0  FOM=  0.00  TEST= 0
INDE  8  35  43  FOBS=   101.2  SIGMA=   1.9  PHAS= -113.4  FOM=  0.89  TEST= 0
INDE  8  35  45  FOBS=    19.6  SIGMA=   9.2  PHAS= -159.3  FOM=  0.41  TEST= 0
INDE  8  35  47  FOBS=   112.8  SIGMA=   2.0  PHAS=  -21.2  FOM=  0.85  TEST= 0
INDE  8  35  49  FOBS=    40.5  SIGMA=   5.9  PHAS=  -99.4  FOM=  0.51  TEST= 0
INDE  8  35  51  FOBS=    40.0  SIGMA=   5.4  PHAS=  -35.8  FOM=  0.54  TEST= 0
INDE  8  35  53  FOBS=    59.0  SIGMA=   3.6  PHAS=  -38.0  FOM=  0.82  TEST= 0
INDE  8  35  55  FOBS=    84.3  SIGMA=   2.2  PHAS=   46.1  FOM=  0.89  TEST= 0
INDE  8  35  57  FOBS=    62.2  SIGMA=   2.9  PHAS=  164.8  FOM=  0.69  TEST= 0
INDE  8  35  59  FOBS=    41.0  SIGMA=   4.5  PHAS=   60.6  FOM=  0.23  TEST= 0
INDE  8  35  61  FOBS=    97.4  SIGMA=   1.9  PHAS=   81.5  FOM=  0.92  TEST= 0
INDE  8  35  63  FOBS=    65.7  SIGMA=   2.7  PHAS=    2.3  FOM=  0.87  TEST= 0
INDE  8  35  65  FOBS=    87.8  SIGMA=   2.2  PHAS=  -32.3  FOM=  0.63  TEST= 0
INDE  8  35  67  FOBS=   107.7  SIGMA=   2.2  PHAS= -148.6  FOM=  0.96  TEST= 0
INDE  8  36   8  FOBS=   462.0  SIGMA=   0.8  PHAS=  141.8  FOM=  0.96  TEST= 0
INDE  8  36  10  FOBS=   293.9  SIGMA=   0.6  PHAS=   32.9  FOM=  0.98  TEST= 0
INDE  8  36  12  FOBS=   290.8  SIGMA=   0.7  PHAS=  117.1  FOM=  0.93  TEST= 0
INDE  8  36  14  FOBS=   194.0  SIGMA=   0.8  PHAS=    4.3  FOM=  0.96  TEST= 0
INDE  8  36  16  FOBS=   237.1  SIGMA=   0.9  PHAS=   22.8  FOM=  0.96  TEST= 0
INDE  8  36  18  FOBS=   343.3  SIGMA=   0.8  PHAS=  -32.7  FOM=  0.94  TEST= 0
INDE  8  36  20  FOBS=   242.9  SIGMA=   1.0  PHAS=   36.0  FOM=  0.97  TEST= 0
INDE  8  36  22  FOBS=   213.9  SIGMA=   0.9  PHAS=   50.5  FOM=  0.96  TEST= 0
INDE  8  36  24  FOBS=     0.0  SIGMA=  20.7  PHAS=    0.0  FOM=  0.00  TEST= 0
INDE  8  36  26  FOBS=   196.8  SIGMA=   1.3  PHAS=  -21.7  FOM=  0.90  TEST= 0
INDE  8  36  28  FOBS=    93.3  SIGMA=   2.2  PHAS=   22.5  FOM=  0.77  TEST= 0
INDE  8  36  30  FOBS=   164.4  SIGMA=   1.4  PHAS= -114.9  FOM=  0.88  TEST= 0
INDE  8  36  32  FOBS=    38.3  SIGMA=   5.2  PHAS=  115.8  FOM=  0.20  TEST= 1
INDE  8  36  34  FOBS=   226.3  SIGMA=   1.0  PHAS= -156.2  FOM=  0.95  TEST= 1
INDE  8  36  36  FOBS=     8.9  SIGMA=  21.8  PHAS=   19.0  FOM=  0.02  TEST= 1
INDE  8  36  38  FOBS=     0.0  SIGMA=  19.6  PHAS=    0.0  FOM=  0.00  TEST= 0
INDE  8  36  40  FOBS=    66.6  SIGMA=   2.8  PHAS= -135.6  FOM=  0.92  TEST= 0
INDE  8  36  42  FOBS=   180.0  SIGMA=   1.1  PHAS=  100.9  FOM=  0.91  TEST= 0
INDE  8  36  44  FOBS=     0.0  SIGMA=  20.5  PHAS=    0.0  FOM=  0.00  TEST= 0
INDE  8  36  46  FOBS=    82.3  SIGMA=   2.2  PHAS=    5.5  FOM=  0.82  TEST= 0
INDE  8  36  48  FOBS=    50.5  SIGMA=   4.4  PHAS=  125.5  FOM=  0.46  TEST= 0
INDE  8  36  50  FOBS=    81.1  SIGMA=   2.7  PHAS= -109.2  FOM=  0.88  TEST= 0
INDE  8  36  52  FOBS=     5.2  SIGMA=  44.3  PHAS=  142.1  FOM=  0.07  TEST= 0
INDE  8  36  54  FOBS=    41.1  SIGMA=   5.6  PHAS= -123.2  FOM=  0.66  TEST= 0
INDE  8  36  56  FOBS=     0.0  SIGMA=  18.9  PHAS=    0.0  FOM=  0.00  TEST= 0
INDE  8  36  58  FOBS=     0.0  SIGMA=  20.2  PHAS=    0.0  FOM=  0.00  TEST= 0
INDE  8  36  60  FOBS=     0.0  SIGMA=  18.8  PHAS=    0.0  FOM=  0.00  TEST= 0
INDE  8  36  62  FOBS=     0.0  SIGMA=  18.7  PHAS=    0.0  FOM=  0.00  TEST= 0
INDE  8  36  64  FOBS=    50.0  SIGMA=   3.6  PHAS=   41.9  FOM=  0.82  TEST= 0
INDE  8  36  66  FOBS=    63.8  SIGMA=   3.3  PHAS=   54.1  FOM=  0.93  TEST= 0
INDE  8  36  68  FOBS=    54.9  SIGMA=   5.8  PHAS=   52.3  FOM=  0.30  TEST= 1
INDE  8  37   9  FOBS=   162.2  SIGMA=   0.9  PHAS=   15.6  FOM=  0.96  TEST= 0
INDE  8  37  11  FOBS=   231.0  SIGMA=   0.8  PHAS=  -96.3  FOM=  0.87  TEST= 0
INDE  8  37  13  FOBS=   185.4  SIGMA=   0.9  PHAS=   26.2  FOM=  0.95  TEST= 0
INDE  8  37  15  FOBS=   205.0  SIGMA=   0.8  PHAS= -136.7  FOM=  0.94  TEST= 0
```

*FIG. 12A - 223*

```
INDE  8  37  17  FOBS=   382.7  SIGMA=   0.6  PHAS=  -142.2  FOM=  0.96  TEST= 0
INDE  8  37  19  FOBS=   417.9  SIGMA=   0.7  PHAS=  -139.6  FOM=  0.95  TEST= 0
INDE  8  37  21  FOBS=   274.8  SIGMA=   0.8  PHAS=   -83.7  FOM=  0.94  TEST= 0
INDE  8  37  23  FOBS=   244.6  SIGMA=   0.8  PHAS=    38.4  FOM=  0.85  TEST= 0
INDE  8  37  25  FOBS=   278.7  SIGMA=   1.0  PHAS=   -89.2  FOM=  0.88  TEST= 0
INDE  8  37  27  FOBS=   295.0  SIGMA=   1.0  PHAS=   -82.4  FOM=  0.94  TEST= 1
INDE  8  37  29  FOBS=    98.7  SIGMA=   2.2  PHAS=  -136.1  FOM=  0.63  TEST= 0
INDE  8  37  31  FOBS=   166.3  SIGMA=   1.4  PHAS=   -60.9  FOM=  0.65  TEST= 0
INDE  8  37  33  FOBS=   104.7  SIGMA=   1.9  PHAS=    73.2  FOM=  0.63  TEST= 0
INDE  8  37  35  FOBS=     0.0  SIGMA=  20.2  PHAS=     0.0  FOM=  0.00  TEST= 0
INDE  8  37  37  FOBS=    40.6  SIGMA=   4.7  PHAS=   -51.8  FOM=  0.30  TEST= 0
INDE  8  37  39  FOBS=   136.7  SIGMA=   1.5  PHAS=   -97.8  FOM=  0.96  TEST= 0
INDE  8  37  41  FOBS=   140.8  SIGMA=   1.4  PHAS=    81.8  FOM=  0.90  TEST= 0
INDE  8  37  43  FOBS=    44.8  SIGMA=   4.1  PHAS=   107.6  FOM=  0.32  TEST= 0
INDE  8  37  45  FOBS=   123.3  SIGMA=   1.5  PHAS=   -29.5  FOM=  0.92  TEST= 0
INDE  8  37  47  FOBS=   112.6  SIGMA=   1.7  PHAS=   -45.0  FOM=  0.86  TEST= 1
INDE  8  37  49  FOBS=   101.0  SIGMA=   2.2  PHAS=   137.7  FOM=  0.88  TEST= 0
INDE  8  37  51  FOBS=     0.0  SIGMA=  23.1  PHAS=     0.0  FOM=  0.00  TEST= 0
INDE  8  37  53  FOBS=    49.7  SIGMA=   4.3  PHAS=   -28.0  FOM=  0.71  TEST= 0
INDE  8  37  55  FOBS=     0.0  SIGMA=  22.5  PHAS=     0.0  FOM=  0.00  TEST= 0
INDE  8  37  57  FOBS=    36.2  SIGMA=   4.9  PHAS=   175.9  FOM=  0.71  TEST= 0
INDE  8  37  59  FOBS=   105.0  SIGMA=   1.8  PHAS=   123.3  FOM=  0.76  TEST= 0
INDE  8  37  61  FOBS=    46.7  SIGMA=   3.8  PHAS=  -100.4  FOM=  0.51  TEST= 0
INDE  8  37  63  FOBS=     0.0  SIGMA=  19.7  PHAS=     0.0  FOM=  0.00  TEST= 0
INDE  8  37  65  FOBS=    88.2  SIGMA=   2.1  PHAS=   -47.1  FOM=  0.89  TEST= 0
INDE  8  37  67  FOBS=    97.5  SIGMA=   2.5  PHAS=   -56.2  FOM=  0.95  TEST= 0
INDE  8  38   8  FOBS=   138.5  SIGMA=   1.1  PHAS=   -71.6  FOM=  0.92  TEST= 1
INDE  8  38  10  FOBS=   114.9  SIGMA=   1.4  PHAS=  -120.4  FOM=  0.43  TEST= 0
INDE  8  38  12  FOBS=   122.6  SIGMA=   1.2  PHAS=  -139.5  FOM=  0.93  TEST= 0
INDE  8  38  14  FOBS=    53.3  SIGMA=   2.7  PHAS=    44.2  FOM=  0.82  TEST= 0
INDE  8  38  16  FOBS=   279.2  SIGMA=   0.9  PHAS=   149.2  FOM=  0.84  TEST= 0
INDE  8  38  18  FOBS=   204.3  SIGMA=   0.9  PHAS=   126.2  FOM=  0.94  TEST= 0
INDE  8  38  20  FOBS=   290.9  SIGMA=   0.8  PHAS=   164.0  FOM=  0.97  TEST= 0
INDE  8  38  22  FOBS=   190.8  SIGMA=   1.0  PHAS=   135.3  FOM=  0.98  TEST= 0
INDE  8  38  24  FOBS=   290.5  SIGMA=   0.8  PHAS=   -77.5  FOM=  0.95  TEST= 0
INDE  8  38  26  FOBS=   144.1  SIGMA=   1.8  PHAS=    51.7  FOM=  0.67  TEST= 0
INDE  8  38  28  FOBS=   176.9  SIGMA=   1.6  PHAS=   174.6  FOM=  0.89  TEST= 0
INDE  8  38  30  FOBS=    44.4  SIGMA=   5.1  PHAS=   -54.1  FOM=  0.30  TEST= 1
INDE  8  38  32  FOBS=   131.8  SIGMA=   1.6  PHAS=  -141.6  FOM=  0.81  TEST= 0
INDE  8  38  34  FOBS=     0.0  SIGMA=  19.7  PHAS=     0.0  FOM=  0.00  TEST= 0
INDE  8  38  36  FOBS=   204.2  SIGMA=   1.1  PHAS=  -154.6  FOM=  0.94  TEST= 0
INDE  8  38  38  FOBS=   157.2  SIGMA=   1.3  PHAS=    63.8  FOM=  0.83  TEST= 0
INDE  8  38  40  FOBS=    37.9  SIGMA=   5.2  PHAS=    99.2  FOM=  0.23  TEST= 0
INDE  8  38  42  FOBS=    63.9  SIGMA=   2.9  PHAS=    22.2  FOM=  0.86  TEST= 0
INDE  8  38  44  FOBS=    60.6  SIGMA=   3.1  PHAS=  -146.3  FOM=  0.78  TEST= 0
INDE  8  38  46  FOBS=   128.8  SIGMA=   1.5  PHAS=  -140.9  FOM=  0.94  TEST= 0
INDE  8  38  48  FOBS=    42.8  SIGMA=   4.4  PHAS=    10.8  FOM=  0.59  TEST= 0
INDE  8  38  50  FOBS=     4.7  SIGMA=  67.1  PHAS=     0.3  FOM=  0.02  TEST= 0
INDE  8  38  52  FOBS=    24.1  SIGMA=   9.0  PHAS=    31.2  FOM=  0.12  TEST= 0
INDE  8  38  54  FOBS=    63.0  SIGMA=   3.4  PHAS=   -87.0  FOM=  0.18  TEST= 1
INDE  8  38  56  FOBS=    20.0  SIGMA=   9.7  PHAS=  -100.0  FOM=  0.23  TEST= 0
INDE  8  38  58  FOBS=    91.2  SIGMA=   2.0  PHAS=    59.1  FOM=  0.92  TEST= 0
INDE  8  38  60  FOBS=    35.5  SIGMA=   5.4  PHAS=   157.0  FOM=  0.61  TEST= 0
INDE  8  38  62  FOBS=    47.3  SIGMA=   3.8  PHAS=   -67.3  FOM=  0.68  TEST= 0
INDE  8  38  64  FOBS=    71.1  SIGMA=   2.6  PHAS=   114.4  FOM=  0.24  TEST= 0
INDE  8  38  66  FOBS=    37.8  SIGMA=   6.2  PHAS=  -159.9  FOM=  0.56  TEST= 0
INDE  8  39   9  FOBS=   176.4  SIGMA=   0.9  PHAS=   -18.9  FOM=  0.95  TEST= 0
INDE  8  39  11  FOBS=   117.0  SIGMA=   1.3  PHAS=   118.1  FOM=  0.95  TEST= 0
INDE  8  39  13  FOBS=   210.5  SIGMA=   0.8  PHAS=   -51.5  FOM=  0.92  TEST= 0
INDE  8  39  15  FOBS=    28.1  SIGMA=   5.6  PHAS=   157.7  FOM=  0.15  TEST= 1
INDE  8  39  17  FOBS=   111.0  SIGMA=   1.5  PHAS=   176.2  FOM=  0.85  TEST= 0
INDE  8  39  19  FOBS=   357.9  SIGMA=   0.7  PHAS=    30.4  FOM=  0.99  TEST= 0
INDE  8  39  21  FOBS=   241.9  SIGMA=   0.9  PHAS=    55.8  FOM=  0.96  TEST= 0
INDE  8  39  23  FOBS=    65.5  SIGMA=   2.9  PHAS=  -140.9  FOM=  0.94  TEST= 0
INDE  8  39  25  FOBS=    57.3  SIGMA=   4.4  PHAS=   -56.4  FOM=  0.84  TEST= 0
INDE  8  39  27  FOBS=   263.5  SIGMA=   1.1  PHAS=   -94.1  FOM=  0.97  TEST= 0
INDE  8  39  29  FOBS=    68.9  SIGMA=   3.8  PHAS=  -164.1  FOM=  0.27  TEST= 0
INDE  8  39  31  FOBS=    26.8  SIGMA=   9.1  PHAS=   150.7  FOM=  0.53  TEST= 0
INDE  8  39  33  FOBS=    52.8  SIGMA=   4.1  PHAS=    89.7  FOM=  0.82  TEST= 0
INDE  8  39  35  FOBS=   110.0  SIGMA=   1.8  PHAS=   103.7  FOM=  0.85  TEST= 0
```

*FIG. 12A - 224*

| | | | | | | | | | | | | |
|---|---|---|---|---|---|---|---|---|---|---|---|---|
| INDE | 8 | 39 | 37 | FOBS= | 232.1 | SIGMA= | 0.9 | PHAS= | 82.6 | FOM= | 0.97 | TEST= 0 |
| INDE | 8 | 39 | 39 | FOBS= | 117.7 | SIGMA= | 1.7 | PHAS= | -114.6 | FOM= | 0.91 | TEST= 1 |
| INDE | 8 | 39 | 41 | FOBS= | 31.5 | SIGMA= | 7.1 | PHAS= | -47.5 | FOM= | 0.59 | TEST= 0 |
| INDE | 8 | 39 | 43 | FOBS= | 45.3 | SIGMA= | 4.4 | PHAS= | -175.5 | FOM= | 0.70 | TEST= 0 |
| INDE | 8 | 39 | 45 | FOBS= | 146.6 | SIGMA= | 1.3 | PHAS= | 112.2 | FOM= | 0.92 | TEST= 0 |
| INDE | 8 | 39 | 47 | FOBS= | 87.2 | SIGMA= | 2.1 | PHAS= | -122.3 | FOM= | 0.51 | TEST= 0 |
| INDE | 8 | 39 | 49 | FOBS= | 10.8 | SIGMA= | 21.3 | PHAS= | -160.8 | FOM= | 0.00 | TEST= 1 |
| INDE | 8 | 39 | 51 | FOBS= | 83.5 | SIGMA= | 2.7 | PHAS= | -138.9 | FOM= | 0.85 | TEST= 0 |
| INDE | 8 | 39 | 53 | FOBS= | 69.8 | SIGMA= | 3.1 | PHAS= | -61.2 | FOM= | 0.90 | TEST= 0 |
| INDE | 8 | 39 | 55 | FOBS= | 7.3 | SIGMA= | 31.6 | PHAS= | -72.9 | FOM= | 0.18 | TEST= 0 |
| INDE | 8 | 39 | 57 | FOBS= | 72.4 | SIGMA= | 2.6 | PHAS= | 0.0 | FOM= | 0.77 | TEST= 0 |
| INDE | 8 | 39 | 59 | FOBS= | 0.0 | SIGMA= | 19.0 | PHAS= | 0.0 | FOM= | 0.00 | TEST= 0 |
| INDE | 8 | 39 | 61 | FOBS= | 33.1 | SIGMA= | 5.4 | PHAS= | -135.9 | FOM= | 0.55 | TEST= 0 |
| INDE | 8 | 39 | 63 | FOBS= | 0.0 | SIGMA= | 19.1 | PHAS= | 0.0 | FOM= | 0.00 | TEST= 0 |
| INDE | 8 | 39 | 65 | FOBS= | 0.0 | SIGMA= | 20.7 | PHAS= | 0.0 | FOM= | 0.00 | TEST= 0 |
| INDE | 8 | 40 | 8 | FOBS= | 116.2 | SIGMA= | 1.4 | PHAS= | -146.5 | FOM= | 0.42 | TEST= 0 |
| INDE | 8 | 40 | 10 | FOBS= | 204.5 | SIGMA= | 1.2 | PHAS= | -110.0 | FOM= | 0.99 | TEST= 0 |
| INDE | 8 | 40 | 12 | FOBS= | 216.6 | SIGMA= | 1.0 | PHAS= | -46.4 | FOM= | 0.94 | TEST= 0 |
| INDE | 8 | 40 | 14 | FOBS= | 178.5 | SIGMA= | 1.0 | PHAS= | -171.2 | FOM= | 0.96 | TEST= 0 |
| INDE | 8 | 40 | 16 | FOBS= | 221.3 | SIGMA= | 0.9 | PHAS= | 146.3 | FOM= | 0.94 | TEST= 0 |
| INDE | 8 | 40 | 18 | FOBS= | 226.6 | SIGMA= | 0.9 | PHAS= | -71.1 | FOM= | 0.99 | TEST= 0 |
| INDE | 8 | 40 | 20 | FOBS= | 355.3 | SIGMA= | 0.8 | PHAS= | -42.0 | FOM= | 0.96 | TEST= 0 |
| INDE | 8 | 40 | 22 | FOBS= | 149.6 | SIGMA= | 1.4 | PHAS= | -94.6 | FOM= | 0.87 | TEST= 0 |
| INDE | 8 | 40 | 24 | FOBS= | 98.1 | SIGMA= | 2.1 | PHAS= | -151.9 | FOM= | 0.90 | TEST= 0 |
| INDE | 8 | 40 | 26 | FOBS= | 143.1 | SIGMA= | 1.9 | PHAS= | 43.1 | FOM= | 0.79 | TEST= 0 |
| INDE | 8 | 40 | 28 | FOBS= | 305.7 | SIGMA= | 1.0 | PHAS= | 136.2 | FOM= | 0.98 | TEST= 0 |
| INDE | 8 | 40 | 30 | FOBS= | 84.8 | SIGMA= | 3.0 | PHAS= | 158.3 | FOM= | 0.78 | TEST= 0 |
| INDE | 8 | 40 | 32 | FOBS= | 231.9 | SIGMA= | 1.2 | PHAS= | -57.0 | FOM= | 0.96 | TEST= 0 |
| INDE | 8 | 40 | 34 | FOBS= | 97.6 | SIGMA= | 2.0 | PHAS= | 72.8 | FOM= | 0.82 | TEST= 0 |
| INDE | 8 | 40 | 36 | FOBS= | 234.5 | SIGMA= | 0.9 | PHAS= | -9.7 | FOM= | 0.95 | TEST= 0 |
| INDE | 8 | 40 | 38 | FOBS= | 0.0 | SIGMA= | 19.5 | PHAS= | 0.0 | FOM= | 0.00 | TEST= 0 |
| INDE | 8 | 40 | 40 | FOBS= | 0.0 | SIGMA= | 19.9 | PHAS= | 0.0 | FOM= | 0.00 | TEST= 0 |
| INDE | 8 | 40 | 42 | FOBS= | 138.7 | SIGMA= | 1.4 | PHAS= | -93.5 | FOM= | 0.94 | TEST= 0 |
| INDE | 8 | 40 | 44 | FOBS= | 177.1 | SIGMA= | 1.1 | PHAS= | 73.7 | FOM= | 0.95 | TEST= 0 |
| INDE | 8 | 40 | 46 | FOBS= | 164.0 | SIGMA= | 1.2 | PHAS= | 145.0 | FOM= | 0.96 | TEST= 0 |
| INDE | 8 | 40 | 48 | FOBS= | 0.0 | SIGMA= | 18.8 | PHAS= | 0.0 | FOM= | 0.00 | TEST= 0 |
| INDE | 8 | 40 | 50 | FOBS= | 58.3 | SIGMA= | 3.0 | PHAS= | 98.4 | FOM= | 0.74 | TEST= 0 |
| INDE | 8 | 40 | 52 | FOBS= | 92.9 | SIGMA= | 2.4 | PHAS= | -171.6 | FOM= | 0.95 | TEST= 0 |
| INDE | 8 | 40 | 54 | FOBS= | 24.9 | SIGMA= | 8.6 | PHAS= | -156.6 | FOM= | 0.48 | TEST= 1 |
| INDE | 8 | 40 | 56 | FOBS= | 61.6 | SIGMA= | 3.1 | PHAS= | -98.4 | FOM= | 0.60 | TEST= 0 |
| INDE | 8 | 40 | 58 | FOBS= | 88.2 | SIGMA= | 2.1 | PHAS= | -29.5 | FOM= | 0.54 | TEST= 1 |
| INDE | 8 | 40 | 60 | FOBS= | 78.7 | SIGMA= | 2.4 | PHAS= | 156.2 | FOM= | 0.93 | TEST= 0 |
| INDE | 8 | 40 | 62 | FOBS= | 0.0 | SIGMA= | 19.1 | PHAS= | 0.0 | FOM= | 0.00 | TEST= 0 |
| INDE | 8 | 40 | 64 | FOBS= | 29.5 | SIGMA= | 8.0 | PHAS= | 10.5 | FOM= | 0.29 | TEST= 0 |
| INDE | 8 | 40 | 66 | FOBS= | 42.7 | SIGMA= | 6.4 | PHAS= | 30.7 | FOM= | 0.78 | TEST= 0 |
| INDE | 8 | 41 | 9 | FOBS= | 33.5 | SIGMA= | 5.2 | PHAS= | -129.1 | FOM= | 0.92 | TEST= 0 |
| INDE | 8 | 41 | 11 | FOBS= | 43.9 | SIGMA= | 4.9 | PHAS= | 23.2 | FOM= | 0.71 | TEST= 0 |
| INDE | 8 | 41 | 13 | FOBS= | 116.2 | SIGMA= | 1.5 | PHAS= | 177.9 | FOM= | 0.81 | TEST= 0 |
| INDE | 8 | 41 | 15 | FOBS= | 196.9 | SIGMA= | 1.1 | PHAS= | 46.9 | FOM= | 0.91 | TEST= 1 |
| INDE | 8 | 41 | 17 | FOBS= | 24.9 | SIGMA= | 9.9 | PHAS= | 108.2 | FOM= | 0.11 | TEST= 0 |
| INDE | 8 | 41 | 19 | FOBS= | 356.5 | SIGMA= | 0.9 | PHAS= | 152.5 | FOM= | 0.96 | TEST= 0 |
| INDE | 8 | 41 | 21 | FOBS= | 142.1 | SIGMA= | 1.5 | PHAS= | 124.4 | FOM= | 0.88 | TEST= 0 |
| INDE | 8 | 41 | 23 | FOBS= | 86.0 | SIGMA= | 2.4 | PHAS= | 92.6 | FOM= | 0.36 | TEST= 0 |
| INDE | 8 | 41 | 25 | FOBS= | 116.8 | SIGMA= | 1.9 | PHAS= | 21.9 | FOM= | 0.35 | TEST= 1 |
| INDE | 8 | 41 | 27 | FOBS= | 130.4 | SIGMA= | 2.1 | PHAS= | -31.8 | FOM= | 0.93 | TEST= 0 |
| INDE | 8 | 41 | 29 | FOBS= | 352.2 | SIGMA= | 0.9 | PHAS= | 45.5 | FOM= | 0.97 | TEST= 0 |
| INDE | 8 | 41 | 31 | FOBS= | 58.7 | SIGMA= | 3.7 | PHAS= | 97.8 | FOM= | 0.82 | TEST= 0 |
| INDE | 8 | 41 | 33 | FOBS= | 88.9 | SIGMA= | 2.5 | PHAS= | 164.1 | FOM= | 0.90 | TEST= 0 |
| INDE | 8 | 41 | 35 | FOBS= | 148.4 | SIGMA= | 1.4 | PHAS= | -96.6 | FOM= | 0.05 | TEST= 1 |
| INDE | 8 | 41 | 37 | FOBS= | 74.2 | SIGMA= | 2.6 | PHAS= | -1.4 | FOM= | 0.85 | TEST= 0 |
| INDE | 8 | 41 | 39 | FOBS= | 40.4 | SIGMA= | 4.7 | PHAS= | 101.9 | FOM= | 0.44 | TEST= 0 |
| INDE | 8 | 41 | 41 | FOBS= | 102.9 | SIGMA= | 1.9 | PHAS= | -145.1 | FOM= | 0.86 | TEST= 0 |
| INDE | 8 | 41 | 43 | FOBS= | 89.1 | SIGMA= | 2.1 | PHAS= | -103.6 | FOM= | 0.88 | TEST= 0 |
| INDE | 8 | 41 | 45 | FOBS= | 136.6 | SIGMA= | 1.4 | PHAS= | 3.2 | FOM= | 0.95 | TEST= 0 |
| INDE | 8 | 41 | 47 | FOBS= | 44.5 | SIGMA= | 4.1 | PHAS= | 39.8 | FOM= | 0.35 | TEST= 0 |
| INDE | 8 | 41 | 49 | FOBS= | 48.3 | SIGMA= | 3.7 | PHAS= | 74.8 | FOM= | 0.63 | TEST= 1 |
| INDE | 8 | 41 | 51 | FOBS= | 52.4 | SIGMA= | 4.2 | PHAS= | -155.9 | FOM= | 0.76 | TEST= 0 |
| INDE | 8 | 41 | 53 | FOBS= | 64.0 | SIGMA= | 3.4 | PHAS= | -103.3 | FOM= | 0.84 | TEST= 0 |
| INDE | 8 | 41 | 55 | FOBS= | 88.4 | SIGMA= | 2.5 | PHAS= | -18.9 | FOM= | 0.75 | TEST= 0 |
| INDE | 8 | 41 | 57 | FOBS= | 52.0 | SIGMA= | 3.8 | PHAS= | -143.0 | FOM= | 0.89 | TEST= 0 |

*FIG. 12A - 225*

```
INDE   8   41   59 FOBS=    41.1 SIGMA=   5.2 PHAS=   175.2 FOM=  0.37 TEST= 0
INDE   8   41   61 FOBS=     0.0 SIGMA=  22.9 PHAS=     0.0 FOM=  0.00 TEST= 0
INDE   8   41   63 FOBS=     0.0 SIGMA=  20.8 PHAS=     0.0 FOM=  0.00 TEST= 1
INDE   8   41   65 FOBS=    93.0 SIGMA=   2.6 PHAS=   -52.6 FOM=  0.89 TEST= 0
INDE   8   42    8 FOBS=     0.0 SIGMA=  21.3 PHAS=     0.0 FOM=  0.00 TEST= 0
INDE   8   42   10 FOBS=   250.8 SIGMA=   1.1 PHAS=  -160.8 FOM=  0.93 TEST= 0
INDE   8   42   12 FOBS=     0.0 SIGMA=  18.2 PHAS=     0.0 FOM=  0.00 TEST= 0
INDE   8   42   14 FOBS=    94.6 SIGMA=   1.9 PHAS=    98.6 FOM=  0.86 TEST= 0
INDE   8   42   16 FOBS=     0.0 SIGMA=  20.7 PHAS=     0.0 FOM=  0.00 TEST= 0
INDE   8   42   18 FOBS=   313.5 SIGMA=   0.8 PHAS=   -14.6 FOM=  0.96 TEST= 0
INDE   8   42   20 FOBS=   180.1 SIGMA=   1.3 PHAS=    -4.6 FOM=  0.86 TEST= 0
INDE   8   42   22 FOBS=   174.9 SIGMA=   1.3 PHAS=   -40.8 FOM=  0.96 TEST= 0
INDE   8   42   24 FOBS=   120.6 SIGMA=   1.8 PHAS=   -75.3 FOM=  0.69 TEST= 0
INDE   8   42   26 FOBS=    44.4 SIGMA=   4.7 PHAS=    62.9 FOM=  0.91 TEST= 0
INDE   8   42   28 FOBS=    91.6 SIGMA=   2.9 PHAS=    14.2 FOM=  0.58 TEST= 1
INDE   8   42   30 FOBS=   268.8 SIGMA=   1.1 PHAS=   -77.5 FOM=  0.94 TEST= 0
INDE   8   42   32 FOBS=    97.3 SIGMA=   2.3 PHAS=   -62.1 FOM=  0.85 TEST= 0
INDE   8   42   34 FOBS=   136.2 SIGMA=   1.6 PHAS=   151.6 FOM=  0.83 TEST= 0
INDE   8   42   36 FOBS=    11.0 SIGMA=  18.3 PHAS=  -105.4 FOM=  0.09 TEST= 0
INDE   8   42   38 FOBS=   143.3 SIGMA=   1.4 PHAS=   -91.4 FOM=  0.97 TEST= 0
INDE   8   42   40 FOBS=    68.6 SIGMA=   2.8 PHAS=   176.6 FOM=  0.84 TEST= 0
INDE   8   42   42 FOBS=   126.3 SIGMA=   1.6 PHAS=   176.0 FOM=  0.92 TEST= 0
INDE   8   42   44 FOBS=    48.2 SIGMA=   3.8 PHAS=   150.7 FOM=  0.91 TEST= 0
INDE   8   42   46 FOBS=    40.7 SIGMA=   4.8 PHAS=   173.5 FOM=  0.71 TEST= 0
INDE   8   42   48 FOBS=    10.9 SIGMA=  17.3 PHAS=   117.9 FOM=  0.44 TEST= 1
INDE   8   42   50 FOBS=    98.7 SIGMA=   1.9 PHAS=   111.9 FOM=  0.46 TEST= 1
INDE   8   42   52 FOBS=    89.0 SIGMA=   2.3 PHAS=  -100.9 FOM=  0.88 TEST= 0
INDE   8   42   54 FOBS=     0.0 SIGMA=  21.7 PHAS=     0.0 FOM=  0.00 TEST= 0
INDE   8   42   56 FOBS=    39.9 SIGMA=   4.7 PHAS=   -18.3 FOM=  0.58 TEST= 0
INDE   8   42   58 FOBS=    95.6 SIGMA=   2.0 PHAS=    32.6 FOM=  0.89 TEST= 0
INDE   8   42   60 FOBS=    32.2 SIGMA=   6.3 PHAS=    34.7 FOM=  0.06 TEST= 1
INDE   8   42   62 FOBS=    40.0 SIGMA=   4.7 PHAS=  -172.2 FOM=  0.50 TEST= 0
INDE   8   42   64 FOBS=    50.1 SIGMA=   4.5 PHAS=   126.6 FOM=  0.51 TEST= 0
INDE   8   43    9 FOBS=    90.6 SIGMA=   1.7 PHAS=    43.7 FOM=  0.96 TEST= 0
INDE   8   43   11 FOBS=   238.1 SIGMA=   1.2 PHAS=    50.4 FOM=  0.98 TEST= 0
INDE   8   43   13 FOBS=   129.4 SIGMA=   1.4 PHAS=   146.5 FOM=  0.94 TEST= 0
INDE   8   43   15 FOBS=    63.2 SIGMA=   3.0 PHAS=   152.2 FOM=  0.61 TEST= 0
INDE   8   43   17 FOBS=   294.7 SIGMA=   0.8 PHAS=   -67.7 FOM=  0.95 TEST= 0
INDE   8   43   19 FOBS=   157.2 SIGMA=   1.4 PHAS=  -156.9 FOM=  0.88 TEST= 0
INDE   8   43   21 FOBS=   250.2 SIGMA=   1.0 PHAS=   -77.0 FOM=  0.88 TEST= 0
INDE   8   43   23 FOBS=   198.6 SIGMA=   1.2 PHAS=  -113.6 FOM=  0.92 TEST= 0
INDE   8   43   25 FOBS=   144.6 SIGMA=   1.5 PHAS=    93.0 FOM=  0.86 TEST= 0
INDE   8   43   27 FOBS=   248.3 SIGMA=   1.0 PHAS=    18.6 FOM=  0.94 TEST= 0
INDE   8   43   29 FOBS=   122.5 SIGMA=   2.1 PHAS=  -106.8 FOM=  0.90 TEST= 0
INDE   8   43   31 FOBS=   164.6 SIGMA=   1.6 PHAS=   146.5 FOM=  0.96 TEST= 0
INDE   8   43   33 FOBS=    73.4 SIGMA=   2.9 PHAS=   162.2 FOM=  0.91 TEST= 1
INDE   8   43   35 FOBS=   111.6 SIGMA=   1.8 PHAS=    99.3 FOM=  0.90 TEST= 1
INDE   8   43   37 FOBS=    59.9 SIGMA=   3.1 PHAS=    92.6 FOM=  0.73 TEST= 0
INDE   8   43   39 FOBS=   285.7 SIGMA=   0.9 PHAS=   134.5 FOM=  0.97 TEST= 0
INDE   8   43   41 FOBS=   105.0 SIGMA=   1.9 PHAS=   113.9 FOM=  0.91 TEST= 0
INDE   8   43   43 FOBS=    46.1 SIGMA=   4.0 PHAS=    86.8 FOM=  0.41 TEST= 0
INDE   8   43   45 FOBS=     0.0 SIGMA=  22.1 PHAS=     0.0 FOM=  0.00 TEST= 0
INDE   8   43   47 FOBS=    34.8 SIGMA=   5.4 PHAS=  -129.9 FOM=  0.70 TEST= 0
INDE   8   43   49 FOBS=    66.1 SIGMA=   2.7 PHAS=  -138.7 FOM=  0.56 TEST= 1
INDE   8   43   51 FOBS=    54.8 SIGMA=   3.6 PHAS=  -130.2 FOM=  0.72 TEST= 0
INDE   8   43   53 FOBS=    35.8 SIGMA=   5.5 PHAS=  -136.1 FOM=  0.47 TEST= 0
INDE   8   43   55 FOBS=     0.0 SIGMA=  21.5 PHAS=     0.0 FOM=  0.00 TEST= 0
INDE   8   43   57 FOBS=    81.3 SIGMA=   2.4 PHAS=   -64.7 FOM=  0.84 TEST= 0
INDE   8   43   59 FOBS=     0.0 SIGMA=  20.0 PHAS=     0.0 FOM=  0.00 TEST= 0
INDE   8   43   61 FOBS=     0.0 SIGMA=  19.4 PHAS=     0.0 FOM=  0.00 TEST= 1
INDE   8   43   63 FOBS=    57.5 SIGMA=   3.9 PHAS=    17.6 FOM=  0.87 TEST= 0
INDE   8   44    8 FOBS=   288.2 SIGMA=   0.8 PHAS=   -60.8 FOM=  0.97 TEST= 0
INDE   8   44   10 FOBS=   126.4 SIGMA=   2.1 PHAS=   159.0 FOM=  0.82 TEST= 1
INDE   8   44   12 FOBS=    37.3 SIGMA=   6.8 PHAS=   -12.7 FOM=  0.85 TEST= 0
INDE   8   44   14 FOBS=    68.3 SIGMA=   2.8 PHAS=   -14.8 FOM=  0.78 TEST= 0
INDE   8   44   16 FOBS=   227.6 SIGMA=   1.0 PHAS=   150.0 FOM=  0.94 TEST= 0
INDE   8   44   18 FOBS=   153.4 SIGMA=   1.4 PHAS=   167.5 FOM=  0.80 TEST= 0
INDE   8   44   20 FOBS=     0.0 SIGMA=  21.0 PHAS=     0.0 FOM=  0.00 TEST= 0
INDE   8   44   22 FOBS=    78.1 SIGMA=   2.7 PHAS=   159.1 FOM=  0.74 TEST= 0
INDE   8   44   24 FOBS=     0.0 SIGMA=  20.5 PHAS=     0.0 FOM=  0.00 TEST= 0
```

*FIG. 12A - 226*

```
INDE  8  44  26  FOBS=  194.6  SIGMA=   1.2  PHAS=   -54.9  FOM=  0.95  TEST= 0
INDE  8  44  28  FOBS=  142.6  SIGMA=   1.5  PHAS=   -84.5  FOM=  0.75  TEST= 0
INDE  8  44  30  FOBS=   71.8  SIGMA=   3.5  PHAS=    25.2  FOM=  0.81  TEST= 0
INDE  8  44  32  FOBS=   66.3  SIGMA=   3.7  PHAS=   106.2  FOM=  0.87  TEST= 0
INDE  8  44  34  FOBS=   82.8  SIGMA=   2.6  PHAS=  -112.4  FOM=  0.83  TEST= 0
INDE  8  44  36  FOBS=   88.4  SIGMA=   2.2  PHAS=    45.3  FOM=  0.88  TEST= 0
INDE  8  44  38  FOBS=  108.1  SIGMA=   1.8  PHAS=    80.2  FOM=  0.63  TEST= 0
INDE  8  44  40  FOBS=   90.7  SIGMA=   2.1  PHAS=    61.0  FOM=  0.96  TEST= 0
INDE  8  44  42  FOBS=   58.1  SIGMA=   3.2  PHAS=   -30.5  FOM=  0.16  TEST= 0
INDE  8  44  44  FOBS=   24.2  SIGMA=   9.6  PHAS=   127.5  FOM=  0.40  TEST= 0
INDE  8  44  46  FOBS=   83.7  SIGMA=   2.2  PHAS=   110.0  FOM=  0.83  TEST= 0
INDE  8  44  48  FOBS=  172.9  SIGMA=   1.2  PHAS=   130.4  FOM=  0.96  TEST= 0
INDE  8  44  50  FOBS=   69.1  SIGMA=   2.9  PHAS=   134.2  FOM=  0.84  TEST= 0
INDE  8  44  52  FOBS=   89.2  SIGMA=   2.3  PHAS=   -67.6  FOM=  0.70  TEST= 0
INDE  8  44  54  FOBS=   41.2  SIGMA=   5.7  PHAS=    54.9  FOM=  0.77  TEST= 0
INDE  8  44  56  FOBS=   42.6  SIGMA=   4.5  PHAS=   179.8  FOM=  0.69  TEST= 0
INDE  8  44  58  FOBS=    0.0  SIGMA=  19.5  PHAS=     0.0  FOM=  0.00  TEST= 0
INDE  8  44  60  FOBS=    0.0  SIGMA=  19.5  PHAS=     0.0  FOM=  0.00  TEST= 0
INDE  8  44  62  FOBS=   65.8  SIGMA=   3.5  PHAS=  -117.8  FOM=  0.82  TEST= 0
INDE  8  45   9  FOBS=   96.7  SIGMA=   1.3  PHAS=  -154.4  FOM=  0.56  TEST= 0
INDE  8  45  11  FOBS=  141.3  SIGMA=   1.1  PHAS=   159.0  FOM=  0.81  TEST= 0
INDE  8  45  13  FOBS=  142.2  SIGMA=   1.4  PHAS=    23.6  FOM=  0.86  TEST= 0
INDE  8  45  15  FOBS=   54.5  SIGMA=   3.7  PHAS=   -81.7  FOM=  0.72  TEST= 0
INDE  8  45  17  FOBS=  142.6  SIGMA=   1.5  PHAS=    91.5  FOM=  0.88  TEST= 0
INDE  8  45  19  FOBS=  145.3  SIGMA=   1.5  PHAS=   -29.8  FOM=  0.76  TEST= 0
INDE  8  45  21  FOBS=  147.9  SIGMA=   1.5  PHAS=    81.9  FOM=  0.90  TEST= 0
INDE  8  45  23  FOBS=   58.6  SIGMA=   3.6  PHAS=  -150.1  FOM=  0.89  TEST= 0
INDE  8  45  25  FOBS=  183.1  SIGMA=   1.2  PHAS=  -161.2  FOM=  0.92  TEST= 0
INDE  8  45  27  FOBS=   92.8  SIGMA=   2.2  PHAS=  -128.6  FOM=  0.65  TEST= 0
INDE  8  45  29  FOBS=  127.7  SIGMA=   1.6  PHAS=  -115.0  FOM=  0.94  TEST= 0
INDE  8  45  31  FOBS=   65.5  SIGMA=   3.8  PHAS=    82.9  FOM=  0.39  TEST= 0
INDE  8  45  33  FOBS=   20.0  SIGMA=  12.7  PHAS=   -39.1  FOM=  0.19  TEST= 0
INDE  8  45  35  FOBS=  154.5  SIGMA=   1.5  PHAS=   123.9  FOM=  0.95  TEST= 0
INDE  8  45  37  FOBS=  135.9  SIGMA=   1.5  PHAS=    59.1  FOM=  0.68  TEST= 1
INDE  8  45  39  FOBS=   51.0  SIGMA=   3.7  PHAS=  -161.9  FOM=  0.62  TEST= 0
INDE  8  45  41  FOBS=   61.9  SIGMA=   3.0  PHAS=   -53.2  FOM=  0.80  TEST= 0
INDE  8  45  43  FOBS=   61.5  SIGMA=   3.0  PHAS=  -100.5  FOM=  0.70  TEST= 0
INDE  8  45  45  FOBS=    0.0  SIGMA=  19.0  PHAS=     0.0  FOM=  0.00  TEST= 0
INDE  8  45  47  FOBS=  113.2  SIGMA=   1.7  PHAS=    25.8  FOM=  0.92  TEST= 0
INDE  8  45  49  FOBS=   41.6  SIGMA=   4.4  PHAS=    11.8  FOM=  0.87  TEST= 0
INDE  8  45  51  FOBS=   30.2  SIGMA=   7.3  PHAS=   -90.5  FOM=  0.21  TEST= 0
INDE  8  45  53  FOBS=   96.7  SIGMA=   2.1  PHAS=   -85.2  FOM=  0.92  TEST= 0
INDE  8  45  55  FOBS=    0.0  SIGMA=  22.1  PHAS=     0.0  FOM=  0.00  TEST= 0
INDE  8  45  57  FOBS=    0.0  SIGMA=  20.2  PHAS=     0.0  FOM=  0.00  TEST= 0
INDE  8  45  59  FOBS=   43.1  SIGMA=   4.5  PHAS=    58.0  FOM=  0.20  TEST= 1
INDE  8  45  61  FOBS=    0.0  SIGMA=  21.1  PHAS=     0.0  FOM=  0.00  TEST= 1
INDE  8  46   8  FOBS=  154.0  SIGMA=   1.4  PHAS=   -47.6  FOM=  0.95  TEST= 1
INDE  8  46  10  FOBS=  230.4  SIGMA=   0.9  PHAS=    99.2  FOM=  0.96  TEST= 0
INDE  8  46  12  FOBS=  166.8  SIGMA=   1.8  PHAS=    80.0  FOM=  0.91  TEST= 1
INDE  8  46  14  FOBS=  165.3  SIGMA=   1.4  PHAS=  -113.8  FOM=  0.95  TEST= 0
INDE  8  46  16  FOBS=  113.9  SIGMA=   1.8  PHAS=   151.0  FOM=  0.74  TEST= 1
INDE  8  46  18  FOBS=  100.3  SIGMA=   2.1  PHAS=  -119.7  FOM=  0.90  TEST= 0
INDE  8  46  20  FOBS=  213.2  SIGMA=   1.2  PHAS=    48.9  FOM=  0.42  TEST= 1
INDE  8  46  22  FOBS=  121.4  SIGMA=   1.8  PHAS=  -125.1  FOM=  0.57  TEST= 0
INDE  8  46  24  FOBS=  225.2  SIGMA=   1.1  PHAS=   117.2  FOM=  0.94  TEST= 0
INDE  8  46  26  FOBS=   42.7  SIGMA=   5.3  PHAS=    96.7  FOM=  0.29  TEST= 0
INDE  8  46  28  FOBS=   52.7  SIGMA=   3.8  PHAS=  -159.4  FOM=  0.67  TEST= 0
INDE  8  46  30  FOBS=   66.4  SIGMA=   3.8  PHAS=   118.2  FOM=  0.21  TEST= 1
INDE  8  46  32  FOBS=    0.0  SIGMA=  23.9  PHAS=     0.0  FOM=  0.00  TEST= 0
INDE  8  46  34  FOBS=   85.4  SIGMA=   2.5  PHAS=   -84.5  FOM=  0.44  TEST= 0
INDE  8  46  36  FOBS=  224.8  SIGMA=   1.1  PHAS=    -3.6  FOM=  0.98  TEST= 0
INDE  8  46  38  FOBS=   64.0  SIGMA=   2.9  PHAS=   152.6  FOM=  0.63  TEST= 0
INDE  8  46  40  FOBS=   23.3  SIGMA=   8.4  PHAS=   150.8  FOM=  0.32  TEST= 0
INDE  8  46  42  FOBS=    0.0  SIGMA=  20.2  PHAS=     0.0  FOM=  0.00  TEST= 0
INDE  8  46  44  FOBS=    0.0  SIGMA=  19.6  PHAS=     0.0  FOM=  0.00  TEST= 0
INDE  8  46  46  FOBS=   54.2  SIGMA=   3.4  PHAS=   -45.5  FOM=  0.46  TEST= 0
INDE  8  46  48  FOBS=    0.0  SIGMA=  19.7  PHAS=     0.0  FOM=  0.00  TEST= 0
INDE  8  46  50  FOBS=    0.0  SIGMA=  22.1  PHAS=     0.0  FOM=  0.00  TEST= 1
INDE  8  46  52  FOBS=   64.4  SIGMA=   3.4  PHAS=   175.7  FOM=  0.83  TEST= 0
INDE  8  46  54  FOBS=   15.4  SIGMA=  13.9  PHAS=    17.2  FOM=  0.07  TEST= 0
```

*FIG. 12A - 227*

```
INDE  8  46  56  FOBS=   37.3  SIGMA=   4.9  PHAS=  -177.7  FOM=  0.69  TEST= 0
INDE  8  46  58  FOBS=   24.0  SIGMA=   9.6  PHAS=    14.7  FOM=  0.69  TEST= 0
INDE  8  46  60  FOBS=   29.0  SIGMA=   7.8  PHAS=   -66.8  FOM=  0.24  TEST= 0
INDE  8  46  62  FOBS=   37.5  SIGMA=   6.8  PHAS=    71.4  FOM=  0.41  TEST= 0
INDE  8  47   9  FOBS=   46.8  SIGMA=   7.0  PHAS=   -75.1  FOM=  0.53  TEST= 0
INDE  8  47  11  FOBS=   54.5  SIGMA=   3.0  PHAS=  -100.4  FOM=  0.72  TEST= 0
INDE  8  47  13  FOBS=  362.4  SIGMA=   1.1  PHAS=    26.9  FOM=  0.98  TEST= 0
INDE  8  47  15  FOBS=  115.4  SIGMA=   1.8  PHAS=   137.6  FOM=  0.90  TEST= 0
INDE  8  47  17  FOBS=  307.8  SIGMA=   0.9  PHAS=   172.2  FOM=  0.98  TEST= 0
INDE  8  47  19  FOBS=   59.4  SIGMA=   3.9  PHAS=   140.6  FOM=  0.93  TEST= 0
INDE  8  47  21  FOBS=   20.0  SIGMA=  10.8  PHAS=    64.9  FOM=  0.23  TEST= 0
INDE  8  47  23  FOBS=  171.3  SIGMA=   1.3  PHAS=    65.5  FOM=  0.86  TEST= 0
INDE  8  47  25  FOBS=   88.5  SIGMA=   2.4  PHAS=   -26.4  FOM=  0.90  TEST= 0
INDE  8  47  27  FOBS=   29.4  SIGMA=   6.9  PHAS=   100.0  FOM=  0.04  TEST= 0
INDE  8  47  29  FOBS=  197.9  SIGMA=   1.1  PHAS=   -23.3  FOM=  0.95  TEST= 0
INDE  8  47  31  FOBS=   63.3  SIGMA=   3.9  PHAS=    96.6  FOM=  0.81  TEST= 0
INDE  8  47  33  FOBS=   31.0  SIGMA=   7.9  PHAS=   -63.9  FOM=  0.22  TEST= 0
INDE  8  47  35  FOBS=   61.3  SIGMA=   3.5  PHAS=   -52.7  FOM=  0.34  TEST= 0
INDE  8  47  37  FOBS=   94.3  SIGMA=   2.1  PHAS=   -36.6  FOM=  0.93  TEST= 0
INDE  8  47  39  FOBS=   59.4  SIGMA=   3.1  PHAS=   -36.6  FOM=  0.80  TEST= 0
INDE  8  47  41  FOBS=    0.0  SIGMA=  19.5  PHAS=     0.0  FOM=  0.00  TEST= 0
INDE  8  47  43  FOBS=   56.1  SIGMA=   3.3  PHAS=  -132.5  FOM=  0.54  TEST= 0
INDE  8  47  45  FOBS=   71.4  SIGMA=   2.6  PHAS=     6.1  FOM=  0.56  TEST= 0
INDE  8  47  47  FOBS=    0.0  SIGMA=  19.0  PHAS=     0.0  FOM=  0.00  TEST= 0
INDE  8  47  49  FOBS=    0.0  SIGMA=  19.9  PHAS=     0.0  FOM=  0.00  TEST= 0
INDE  8  47  51  FOBS=   51.3  SIGMA=   4.2  PHAS=    66.4  FOM=  0.81  TEST= 0
INDE  8  47  53  FOBS=   31.6  SIGMA=   8.5  PHAS=     7.7  FOM=  0.16  TEST= 0
INDE  8  47  55  FOBS=    7.5  SIGMA=  26.6  PHAS=    42.8  FOM=  0.08  TEST= 0
INDE  8  47  57  FOBS=    0.0  SIGMA=  19.8  PHAS=     0.0  FOM=  0.00  TEST= 1
INDE  8  47  59  FOBS=   56.5  SIGMA=   4.1  PHAS=    56.3  FOM=  0.74  TEST= 0
INDE  8  47  61  FOBS=   33.3  SIGMA=   7.6  PHAS=    84.4  FOM=  0.12  TEST= 0
INDE  8  48   8  FOBS=  181.8  SIGMA=   1.2  PHAS=    44.7  FOM=  0.96  TEST= 0
INDE  8  48  10  FOBS=  143.6  SIGMA=   1.3  PHAS=   144.8  FOM=  0.23  TEST= 1
INDE  8  48  12  FOBS=    0.0  SIGMA=  19.9  PHAS=     0.0  FOM=  0.00  TEST= 0
INDE  8  48  14  FOBS=  144.5  SIGMA=   1.6  PHAS=   -48.0  FOM=  0.86  TEST= 1
INDE  8  48  16  FOBS=  152.9  SIGMA=   1.4  PHAS=    76.2  FOM=  0.95  TEST= 0
INDE  8  48  18  FOBS=  237.9  SIGMA=   1.0  PHAS=    57.6  FOM=  0.96  TEST= 0
INDE  8  48  20  FOBS=  221.0  SIGMA=   1.0  PHAS=     0.1  FOM=  0.97  TEST= 0
INDE  8  48  22  FOBS=   68.8  SIGMA=   3.0  PHAS=  -102.1  FOM=  0.69  TEST= 0
INDE  8  48  24  FOBS=    0.0  SIGMA=  20.1  PHAS=     0.0  FOM=  0.00  TEST= 0
INDE  8  48  26  FOBS=  183.9  SIGMA=   1.2  PHAS=  -165.7  FOM=  0.34  TEST= 1
INDE  8  48  28  FOBS=   72.3  SIGMA=   2.8  PHAS=   -80.6  FOM=  0.45  TEST= 0
INDE  8  48  30  FOBS=   98.5  SIGMA=   2.1  PHAS=  -166.6  FOM=  0.84  TEST= 0
INDE  8  48  32  FOBS=  121.0  SIGMA=   2.1  PHAS=   -93.9  FOM=  0.90  TEST= 0
INDE  8  48  34  FOBS=    0.0  SIGMA=  21.9  PHAS=     0.0  FOM=  0.00  TEST= 0
INDE  8  48  36  FOBS=   86.3  SIGMA=   2.4  PHAS=    -2.4  FOM=  0.34  TEST= 1
INDE  8  48  38  FOBS=   81.5  SIGMA=   2.3  PHAS=   176.0  FOM=  0.86  TEST= 0
INDE  8  48  40  FOBS=  103.4  SIGMA=   1.8  PHAS=   112.0  FOM=  0.16  TEST= 1
INDE  8  48  42  FOBS=   86.8  SIGMA=   2.2  PHAS=   174.9  FOM=  0.71  TEST= 0
INDE  8  48  44  FOBS=   21.0  SIGMA=   8.8  PHAS=   111.3  FOM=  0.19  TEST= 0
INDE  8  48  46  FOBS=   52.8  SIGMA=   3.5  PHAS=   -53.9  FOM=  0.84  TEST= 0
INDE  8  48  48  FOBS=   20.5  SIGMA=   8.8  PHAS=    86.0  FOM=  0.07  TEST= 0
INDE  8  48  50  FOBS=   14.5  SIGMA=  13.8  PHAS=    24.2  FOM=  0.05  TEST= 1
INDE  8  48  52  FOBS=   31.4  SIGMA=   8.1  PHAS=    -5.8  FOM=  0.48  TEST= 0
INDE  8  48  54  FOBS=    0.0  SIGMA=  20.0  PHAS=     0.0  FOM=  0.00  TEST= 0
INDE  8  48  56  FOBS=    0.0  SIGMA=  19.7  PHAS=     0.0  FOM=  0.00  TEST= 1
INDE  8  48  58  FOBS=   34.5  SIGMA=   6.1  PHAS=   -20.8  FOM=  0.48  TEST= 0
INDE  8  48  60  FOBS=   31.4  SIGMA=   8.2  PHAS=    50.8  FOM=  0.04  TEST= 0
INDE  8  49   9  FOBS=  135.1  SIGMA=   2.1  PHAS=   -58.9  FOM=  0.90  TEST= 0
INDE  8  49  11  FOBS=   66.2  SIGMA=   2.2  PHAS=  -179.6  FOM=  0.78  TEST= 0
INDE  8  49  13  FOBS=  225.3  SIGMA=   1.2  PHAS=    75.7  FOM=  0.93  TEST= 0
INDE  8  49  15  FOBS=   81.6  SIGMA=   2.4  PHAS=   -26.3  FOM=  0.83  TEST= 0
INDE  8  49  17  FOBS=  124.2  SIGMA=   1.6  PHAS=   -66.0  FOM=  0.91  TEST= 0
INDE  8  49  19  FOBS=  295.8  SIGMA=   0.8  PHAS=   -65.9  FOM=  0.96  TEST= 0
INDE  8  49  21  FOBS=  174.6  SIGMA=   1.3  PHAS=   -79.8  FOM=  0.95  TEST= 0
INDE  8  49  23  FOBS=  167.0  SIGMA=   1.3  PHAS=   100.7  FOM=  0.93  TEST= 0
INDE  8  49  25  FOBS=   66.4  SIGMA=   3.1  PHAS=    18.2  FOM=  0.69  TEST= 0
INDE  8  49  27  FOBS=   95.4  SIGMA=   2.2  PHAS=   -19.7  FOM=  0.86  TEST= 0
INDE  8  49  29  FOBS=  104.8  SIGMA=   2.0  PHAS=   -48.1  FOM=  0.93  TEST= 0
INDE  8  49  31  FOBS=  121.4  SIGMA=   1.7  PHAS=   169.7  FOM=  0.78  TEST= 0
```

*FIG. 12A - 228*

| | | | | | | | | | | | | |
|---|---|---|---|---|---|---|---|---|---|---|---|---|
| INDE | 8 | 49 | 33 | FOBS= | 63.9 | SIGMA= | 3.9 | PHAS= | -176.2 | FOM= | 0.75 | TEST= 0 |
| INDE | 8 | 49 | 35 | FOBS= | 106.5 | SIGMA= | 2.1 | PHAS= | 43.2 | FOM= | 0.07 | TEST= 1 |
| INDE | 8 | 49 | 37 | FOBS= | 39.9 | SIGMA= | 5.1 | PHAS= | -160.9 | FOM= | 0.07 | TEST= 0 |
| INDE | 8 | 49 | 39 | FOBS= | 43.3 | SIGMA= | 4.2 | PHAS= | -152.8 | FOM= | 0.73 | TEST= 0 |
| INDE | 8 | 49 | 41 | FOBS= | 94.1 | SIGMA= | 2.0 | PHAS= | 101.2 | FOM= | 0.88 | TEST= 0 |
| INDE | 8 | 49 | 43 | FOBS= | 100.7 | SIGMA= | 1.9 | PHAS= | 77.1 | FOM= | 0.88 | TEST= 0 |
| INDE | 8 | 49 | 45 | FOBS= | 96.7 | SIGMA= | 2.0 | PHAS= | -137.8 | FOM= | 0.68 | TEST= 0 |
| INDE | 8 | 49 | 47 | FOBS= | 29.5 | SIGMA= | 6.5 | PHAS= | -126.7 | FOM= | 0.11 | TEST= 0 |
| INDE | 8 | 49 | 49 | FOBS= | 0.0 | SIGMA= | 22.0 | PHAS= | 0.0 | FOM= | 0.00 | TEST= 1 |
| INDE | 8 | 49 | 51 | FOBS= | 78.9 | SIGMA= | 2.6 | PHAS= | -167.7 | FOM= | 0.81 | TEST= 0 |
| INDE | 8 | 49 | 53 | FOBS= | 0.0 | SIGMA= | 20.8 | PHAS= | 0.0 | FOM= | 0.00 | TEST= 0 |
| INDE | 8 | 49 | 55 | FOBS= | 13.0 | SIGMA= | 15.0 | PHAS= | 74.7 | FOM= | 0.06 | TEST= 0 |
| INDE | 8 | 49 | 57 | FOBS= | 51.6 | SIGMA= | 4.1 | PHAS= | -161.8 | FOM= | 0.39 | TEST= 0 |
| INDE | 8 | 49 | 59 | FOBS= | 55.3 | SIGMA= | 3.9 | PHAS= | 5.8 | FOM= | 0.79 | TEST= 0 |
| INDE | 8 | 50 | 8 | FOBS= | 167.2 | SIGMA= | 1.8 | PHAS= | 29.2 | FOM= | 0.95 | TEST= 0 |
| INDE | 8 | 50 | 10 | FOBS= | 303.9 | SIGMA= | 1.1 | PHAS= | -139.4 | FOM= | 0.97 | TEST= 0 |
| INDE | 8 | 50 | 12 | FOBS= | 55.8 | SIGMA= | 2.7 | PHAS= | -138.7 | FOM= | 0.07 | TEST= 0 |
| INDE | 8 | 50 | 14 | FOBS= | 115.0 | SIGMA= | 1.5 | PHAS= | -66.2 | FOM= | 0.88 | TEST= 0 |
| INDE | 8 | 50 | 16 | FOBS= | 163.6 | SIGMA= | 1.3 | PHAS= | -148.9 | FOM= | 0.95 | TEST= 0 |
| INDE | 8 | 50 | 18 | FOBS= | 18.6 | SIGMA= | 10.6 | PHAS= | 102.2 | FOM= | 0.26 | TEST= 0 |
| INDE | 8 | 50 | 20 | FOBS= | 200.2 | SIGMA= | 1.1 | PHAS= | -152.6 | FOM= | 0.97 | TEST= 0 |
| INDE | 8 | 50 | 22 | FOBS= | 145.1 | SIGMA= | 1.5 | PHAS= | 81.2 | FOM= | 0.84 | TEST= 0 |
| INDE | 8 | 50 | 24 | FOBS= | 180.7 | SIGMA= | 1.2 | PHAS= | 4.5 | FOM= | 0.94 | TEST= 0 |
| INDE | 8 | 50 | 26 | FOBS= | 208.1 | SIGMA= | 1.1 | PHAS= | -105.8 | FOM= | 0.44 | TEST= 1 |
| INDE | 8 | 50 | 28 | FOBS= | 159.2 | SIGMA= | 1.4 | PHAS= | -132.4 | FOM= | 0.96 | TEST= 0 |
| INDE | 8 | 50 | 30 | FOBS= | 60.0 | SIGMA= | 3.3 | PHAS= | -129.3 | FOM= | 0.64 | TEST= 0 |
| INDE | 8 | 50 | 32 | FOBS= | 102.2 | SIGMA= | 2.0 | PHAS= | 109.4 | FOM= | 0.87 | TEST= 0 |
| INDE | 8 | 50 | 34 | FOBS= | 66.9 | SIGMA= | 3.7 | PHAS= | -37.4 | FOM= | 0.82 | TEST= 0 |
| INDE | 8 | 50 | 36 | FOBS= | 119.1 | SIGMA= | 1.8 | PHAS= | 14.2 | FOM= | 0.91 | TEST= 0 |
| INDE | 8 | 50 | 38 | FOBS= | 67.2 | SIGMA= | 3.1 | PHAS= | 83.0 | FOM= | 0.90 | TEST= 0 |
| INDE | 8 | 50 | 40 | FOBS= | 76.5 | SIGMA= | 2.4 | PHAS= | 47.8 | FOM= | 0.67 | TEST= 0 |
| INDE | 8 | 50 | 42 | FOBS= | 65.4 | SIGMA= | 2.8 | PHAS= | 92.5 | FOM= | 0.10 | TEST= 1 |
| INDE | 8 | 50 | 44 | FOBS= | 34.5 | SIGMA= | 5.6 | PHAS= | 179.8 | FOM= | 0.35 | TEST= 0 |
| INDE | 8 | 50 | 46 | FOBS= | 25.3 | SIGMA= | 12.4 | PHAS= | -40.0 | FOM= | 0.42 | TEST= 0 |
| INDE | 8 | 50 | 48 | FOBS= | 5.7 | SIGMA= | 35.3 | PHAS= | -111.1 | FOM= | 0.17 | TEST= 0 |
| INDE | 8 | 50 | 50 | FOBS= | 78.0 | SIGMA= | 2.6 | PHAS= | 145.9 | FOM= | 0.72 | TEST= 0 |
| INDE | 8 | 50 | 52 | FOBS= | 53.5 | SIGMA= | 3.8 | PHAS= | 5.7 | FOM= | 0.83 | TEST= 0 |
| INDE | 8 | 50 | 54 | FOBS= | 8.5 | SIGMA= | 23.7 | PHAS= | 116.5 | FOM= | 0.07 | TEST= 0 |
| INDE | 8 | 50 | 56 | FOBS= | 36.5 | SIGMA= | 5.9 | PHAS= | 92.1 | FOM= | 0.32 | TEST= 0 |
| INDE | 8 | 50 | 58 | FOBS= | 42.2 | SIGMA= | 5.1 | PHAS= | -53.6 | FOM= | 0.52 | TEST= 0 |
| INDE | 8 | 51 | 9 | FOBS= | 24.0 | SIGMA= | 15.5 | PHAS= | 127.2 | FOM= | 0.21 | TEST= 0 |
| INDE | 8 | 51 | 11 | FOBS= | 141.1 | SIGMA= | 1.3 | PHAS= | 158.3 | FOM= | 0.90 | TEST= 0 |
| INDE | 8 | 51 | 13 | FOBS= | 30.6 | SIGMA= | 5.4 | PHAS= | 97.5 | FOM= | 0.92 | TEST= 0 |
| INDE | 8 | 51 | 15 | FOBS= | 161.8 | SIGMA= | 1.0 | PHAS= | 98.0 | FOM= | 0.96 | TEST= 0 |
| INDE | 8 | 51 | 17 | FOBS= | 47.0 | SIGMA= | 4.1 | PHAS= | -55.6 | FOM= | 0.89 | TEST= 0 |
| INDE | 8 | 51 | 19 | FOBS= | 141.5 | SIGMA= | 1.5 | PHAS= | -36.7 | FOM= | 0.94 | TEST= 0 |
| INDE | 8 | 51 | 21 | FOBS= | 153.5 | SIGMA= | 1.5 | PHAS= | 39.9 | FOM= | 0.82 | TEST= 0 |
| INDE | 8 | 51 | 23 | FOBS= | 34.0 | SIGMA= | 5.9 | PHAS= | 140.6 | FOM= | 0.37 | TEST= 0 |
| INDE | 8 | 51 | 25 | FOBS= | 85.6 | SIGMA= | 2.4 | PHAS= | -8.4 | FOM= | 0.87 | TEST= 0 |
| INDE | 8 | 51 | 27 | FOBS= | 44.8 | SIGMA= | 4.5 | PHAS= | -161.6 | FOM= | 0.70 | TEST= 0 |
| INDE | 8 | 51 | 29 | FOBS= | 107.3 | SIGMA= | 1.9 | PHAS= | 173.9 | FOM= | 0.93 | TEST= 0 |
| INDE | 8 | 51 | 31 | FOBS= | 67.1 | SIGMA= | 3.0 | PHAS= | -109.7 | FOM= | 0.62 | TEST= 0 |
| INDE | 8 | 51 | 33 | FOBS= | 24.7 | SIGMA= | 7.9 | PHAS= | 132.8 | FOM= | 0.42 | TEST= 0 |
| INDE | 8 | 51 | 35 | FOBS= | 76.9 | SIGMA= | 3.1 | PHAS= | -82.7 | FOM= | 0.76 | TEST= 0 |
| INDE | 8 | 51 | 37 | FOBS= | 70.8 | SIGMA= | 2.9 | PHAS= | 65.6 | FOM= | 0.26 | TEST= 0 |
| INDE | 8 | 51 | 39 | FOBS= | 157.1 | SIGMA= | 1.3 | PHAS= | -129.9 | FOM= | 0.95 | TEST= 0 |
| INDE | 8 | 51 | 41 | FOBS= | 20.9 | SIGMA= | 9.0 | PHAS= | -14.7 | FOM= | 0.22 | TEST= 0 |
| INDE | 8 | 51 | 43 | FOBS= | 40.0 | SIGMA= | 4.6 | PHAS= | -66.0 | FOM= | 0.07 | TEST= 1 |
| INDE | 8 | 51 | 45 | FOBS= | 115.0 | SIGMA= | 1.7 | PHAS= | 85.0 | FOM= | 0.91 | TEST= 0 |
| INDE | 8 | 51 | 47 | FOBS= | 25.6 | SIGMA= | 7.3 | PHAS= | -156.7 | FOM= | 0.59 | TEST= 0 |
| INDE | 8 | 51 | 49 | FOBS= | 42.2 | SIGMA= | 4.9 | PHAS= | -131.0 | FOM= | 0.69 | TEST= 0 |
| INDE | 8 | 51 | 51 | FOBS= | 82.3 | SIGMA= | 2.5 | PHAS= | -152.7 | FOM= | 0.83 | TEST= 0 |
| INDE | 8 | 51 | 53 | FOBS= | 67.1 | SIGMA= | 3.1 | PHAS= | -160.0 | FOM= | 0.82 | TEST= 0 |
| INDE | 8 | 51 | 55 | FOBS= | 0.0 | SIGMA= | 22.6 | PHAS= | 0.0 | FOM= | 0.00 | TEST= 0 |
| INDE | 8 | 51 | 57 | FOBS= | 0.0 | SIGMA= | 20.9 | PHAS= | 0.0 | FOM= | 0.00 | TEST= 0 |
| INDE | 8 | 52 | 8 | FOBS= | 181.8 | SIGMA= | 1.6 | PHAS= | 31.0 | FOM= | 0.86 | TEST= 0 |
| INDE | 8 | 52 | 10 | FOBS= | 116.7 | SIGMA= | 2.4 | PHAS= | -158.0 | FOM= | 0.90 | TEST= 0 |
| INDE | 8 | 52 | 12 | FOBS= | 107.6 | SIGMA= | 1.4 | PHAS= | -115.2 | FOM= | 0.91 | TEST= 0 |
| INDE | 8 | 52 | 14 | FOBS= | 255.2 | SIGMA= | 0.8 | PHAS= | -26.1 | FOM= | 0.97 | TEST= 0 |
| INDE | 8 | 52 | 16 | FOBS= | 64.4 | SIGMA= | 2.5 | PHAS= | 81.4 | FOM= | 0.82 | TEST= 0 |

*FIG. 12A - 229*

```
INDE  8  52  18  FOBS=   78.5  SIGMA=   2.5  PHAS=  -123.4  FOM=  0.91  TEST= 0
INDE  8  52  20  FOBS=  161.8  SIGMA=   1.3  PHAS=  -147.8  FOM=  0.93  TEST= 0
INDE  8  52  22  FOBS=   71.1  SIGMA=   2.8  PHAS=   125.5  FOM=  0.56  TEST= 0
INDE  8  52  24  FOBS=   69.3  SIGMA=   2.9  PHAS=   -62.7  FOM=  0.88  TEST= 0
INDE  8  52  26  FOBS=   58.6  SIGMA=   3.4  PHAS=   -54.9  FOM=  0.70  TEST= 0
INDE  8  52  28  FOBS=   37.7  SIGMA=   5.3  PHAS=   -47.3  FOM=  0.42  TEST= 0
INDE  8  52  30  FOBS=    0.0  SIGMA=  21.0  PHAS=     0.0  FOM=  0.00  TEST= 0
INDE  8  52  32  FOBS=  105.8  SIGMA=   1.9  PHAS=    86.9  FOM=  0.46  TEST= 1
INDE  8  52  34  FOBS=   69.3  SIGMA=   2.9  PHAS=    20.9  FOM=  0.84  TEST= 0
INDE  8  52  36  FOBS=    0.0  SIGMA=  21.7  PHAS=     0.0  FOM=  0.00  TEST= 0
INDE  8  52  38  FOBS=  164.9  SIGMA=   1.4  PHAS=   115.7  FOM=  0.94  TEST= 0
INDE  8  52  40  FOBS=   72.6  SIGMA=   2.5  PHAS=   167.6  FOM=  0.85  TEST= 0
INDE  8  52  42  FOBS=   29.6  SIGMA=   6.1  PHAS=   158.6  FOM=  0.61  TEST= 0
INDE  8  52  44  FOBS=   38.9  SIGMA=   4.7  PHAS=     4.3  FOM=  0.85  TEST= 0
INDE  8  52  46  FOBS=   52.7  SIGMA=   3.5  PHAS=    94.4  FOM=  0.44  TEST= 0
INDE  8  52  48  FOBS=   42.3  SIGMA=   4.9  PHAS=    94.1  FOM=  0.81  TEST= 0
INDE  8  52  50  FOBS=   70.2  SIGMA=   3.0  PHAS=   124.2  FOM=  0.92  TEST= 0
INDE  8  52  52  FOBS=   35.3  SIGMA=   5.8  PHAS=    54.1  FOM=  0.59  TEST= 0
INDE  8  52  54  FOBS=   43.4  SIGMA=   5.2  PHAS=   151.6  FOM=  0.74  TEST= 0
INDE  8  52  56  FOBS=    0.0  SIGMA=  20.9  PHAS=     0.0  FOM=  0.00  TEST= 0
INDE  8  53   9  FOBS=   75.3  SIGMA=   3.6  PHAS=    11.2  FOM=  0.83  TEST= 0
INDE  8  53  11  FOBS=  171.1  SIGMA=   1.7  PHAS=   154.5  FOM=  0.94  TEST= 0
INDE  8  53  13  FOBS=  179.2  SIGMA=   1.2  PHAS=  -127.8  FOM=  0.92  TEST= 0
INDE  8  53  15  FOBS=  131.0  SIGMA=   1.3  PHAS=    35.9  FOM=  0.34  TEST= 1
INDE  8  53  17  FOBS=    0.0  SIGMA=  20.6  PHAS=     0.0  FOM=  0.00  TEST= 0
INDE  8  53  19  FOBS=   79.6  SIGMA=   2.4  PHAS=   112.2  FOM=  0.74  TEST= 1
INDE  8  53  21  FOBS=   58.2  SIGMA=   3.4  PHAS=    94.6  FOM=  0.84  TEST= 0
INDE  8  53  23  FOBS=   45.8  SIGMA=   4.2  PHAS=  -125.8  FOM=  0.92  TEST= 0
INDE  8  53  25  FOBS=   32.6  SIGMA=   6.1  PHAS=   137.0  FOM=  0.72  TEST= 0
INDE  8  53  27  FOBS=  127.5  SIGMA=   1.6  PHAS=  -141.3  FOM=  0.94  TEST= 0
INDE  8  53  29  FOBS=   90.6  SIGMA=   2.3  PHAS=   162.9  FOM=  0.75  TEST= 0
INDE  8  53  31  FOBS=   48.3  SIGMA=   4.1  PHAS=    86.3  FOM=  0.73  TEST= 0
INDE  8  53  33  FOBS=   63.1  SIGMA=   3.2  PHAS=   157.0  FOM=  0.61  TEST= 0
INDE  8  53  35  FOBS=   22.2  SIGMA=  10.7  PHAS=   153.9  FOM=  0.11  TEST= 0
INDE  8  53  37  FOBS=   94.1  SIGMA=   2.4  PHAS=   130.5  FOM=  0.86  TEST= 0
INDE  8  53  39  FOBS=   71.1  SIGMA=   2.9  PHAS=   108.4  FOM=  0.75  TEST= 0
INDE  8  53  41  FOBS=   38.2  SIGMA=   5.0  PHAS=   -17.0  FOM=  0.77  TEST= 0
INDE  8  53  43  FOBS=   77.6  SIGMA=   2.4  PHAS=   -68.7  FOM=  0.85  TEST= 0
INDE  8  53  45  FOBS=   52.5  SIGMA=   3.5  PHAS=     6.0  FOM=  0.82  TEST= 0
INDE  8  53  47  FOBS=   66.8  SIGMA=   3.1  PHAS=    55.1  FOM=  0.88  TEST= 0
INDE  8  53  49  FOBS=   24.5  SIGMA=  10.2  PHAS=    17.7  FOM=  0.37  TEST= 0
INDE  8  53  51  FOBS=    0.0  SIGMA=  20.3  PHAS=     0.0  FOM=  0.00  TEST= 0
INDE  8  53  53  FOBS=   25.2  SIGMA=   8.8  PHAS=   -55.1  FOM=  0.40  TEST= 0
INDE  8  53  55  FOBS=    0.0  SIGMA=  23.5  PHAS=     0.0  FOM=  0.00  TEST= 0
INDE  8  54   8  FOBS=   88.5  SIGMA=   3.0  PHAS=  -122.0  FOM=  0.86  TEST= 1
INDE  8  54  10  FOBS=   79.1  SIGMA=   3.4  PHAS=    16.7  FOM=  0.78  TEST= 0
INDE  8  54  12  FOBS=  100.4  SIGMA=   1.8  PHAS=   158.6  FOM=  0.81  TEST= 0
INDE  8  54  14  FOBS=    0.0  SIGMA=  19.9  PHAS=     0.0  FOM=  0.00  TEST= 0
INDE  8  54  16  FOBS=   73.2  SIGMA=   2.4  PHAS=   143.4  FOM=  0.66  TEST= 0
INDE  8  54  18  FOBS=   95.2  SIGMA=   2.0  PHAS=   -36.1  FOM=  0.89  TEST= 0
INDE  8  54  20  FOBS=    0.0  SIGMA=  19.6  PHAS=     0.0  FOM=  0.00  TEST= 0
INDE  8  54  22  FOBS=   64.6  SIGMA=   3.2  PHAS=   161.3  FOM=  0.45  TEST= 0
INDE  8  54  24  FOBS=   32.0  SIGMA=   6.1  PHAS=    29.7  FOM=  0.28  TEST= 0
INDE  8  54  26  FOBS=  140.0  SIGMA=   1.5  PHAS=   133.6  FOM=  0.93  TEST= 0
INDE  8  54  28  FOBS=   93.0  SIGMA=   2.2  PHAS=     7.0  FOM=  0.59  TEST= 0
INDE  8  54  30  FOBS=   92.9  SIGMA=   2.2  PHAS=    46.6  FOM=  0.89  TEST= 0
INDE  8  54  32  FOBS=   77.4  SIGMA=   2.6  PHAS=   106.5  FOM=  0.83  TEST= 0
INDE  8  54  34  FOBS=    7.0  SIGMA=  28.0  PHAS=    74.3  FOM=  0.05  TEST= 1
INDE  8  54  36  FOBS=   71.8  SIGMA=   2.8  PHAS=   -30.8  FOM=  0.89  TEST= 0
INDE  8  54  38  FOBS=   52.7  SIGMA=   3.8  PHAS=    36.8  FOM=  0.73  TEST= 0
INDE  8  54  40  FOBS=    0.0  SIGMA=  20.7  PHAS=     0.0  FOM=  0.00  TEST= 0
INDE  8  54  42  FOBS=   97.9  SIGMA=   1.9  PHAS=  -146.8  FOM=  0.91  TEST= 0
INDE  8  54  44  FOBS=  112.2  SIGMA=   1.7  PHAS=   -14.7  FOM=  0.93  TEST= 0
INDE  8  54  46  FOBS=   28.4  SIGMA=   7.7  PHAS=    37.3  FOM=  0.38  TEST= 0
INDE  8  54  48  FOBS=   78.3  SIGMA=   2.7  PHAS=   -20.2  FOM=  0.91  TEST= 0
INDE  8  54  50  FOBS=   37.4  SIGMA=   6.8  PHAS=   148.1  FOM=  0.36  TEST= 0
INDE  8  54  52  FOBS=   32.2  SIGMA=   9.7  PHAS=    84.8  FOM=  0.11  TEST= 1
INDE  8  54  54  FOBS=   57.2  SIGMA=   5.8  PHAS=   123.1  FOM=  0.87  TEST= 0
INDE  8  55   9  FOBS=   95.8  SIGMA=   2.8  PHAS=    70.3  FOM=  0.45  TEST= 0
INDE  8  55  11  FOBS=   60.5  SIGMA=   4.4  PHAS=  -162.6  FOM=  0.62  TEST= 0
```

*FIG. 12A - 230*

```
INDE  8  55  13  FOBS=   38.0  SIGMA=   3.9  PHAS=  146.7  FOM=  0.23  TEST=  0
INDE  8  55  15  FOBS=  103.2  SIGMA=   1.6  PHAS=   67.8  FOM=  0.83  TEST=  0
INDE  8  55  17  FOBS=   59.8  SIGMA=   2.5  PHAS= -123.5  FOM=  0.55  TEST=  0
INDE  8  55  19  FOBS=   79.2  SIGMA=   2.5  PHAS=   34.2  FOM=  0.27  TEST=  1
INDE  8  55  21  FOBS=    0.0  SIGMA=  21.6  PHAS=    0.0  FOM=  0.00  TEST=  0
INDE  8  55  23  FOBS=   76.0  SIGMA=   2.6  PHAS= -134.5  FOM=  0.34  TEST=  1
INDE  8  55  25  FOBS=   66.4  SIGMA=   2.9  PHAS=   56.3  FOM=  0.83  TEST=  0
INDE  8  55  27  FOBS=   17.1  SIGMA=  11.3  PHAS=  -54.5  FOM=  0.05  TEST=  1
INDE  8  55  29  FOBS=   79.7  SIGMA=   2.5  PHAS= -127.8  FOM=  0.23  TEST=  1
INDE  8  55  31  FOBS=  104.8  SIGMA=   2.0  PHAS=   13.7  FOM=  0.90  TEST=  0
INDE  8  55  33  FOBS=    0.0  SIGMA=  20.6  PHAS=    0.0  FOM=  0.00  TEST=  0
INDE  8  55  35  FOBS=  103.1  SIGMA=   2.0  PHAS= -165.5  FOM=  0.92  TEST=  0
INDE  8  55  37  FOBS=   52.4  SIGMA=   3.7  PHAS= -123.4  FOM=  0.77  TEST=  0
INDE  8  55  39  FOBS=    0.0  SIGMA=  20.9  PHAS=    0.0  FOM=  0.00  TEST=  0
INDE  8  55  41  FOBS=   45.1  SIGMA=   4.3  PHAS= -179.4  FOM=  0.18  TEST=  1
INDE  8  55  43  FOBS=  105.8  SIGMA=   1.8  PHAS= -110.9  FOM=  0.26  TEST=  1
INDE  8  55  45  FOBS=   72.0  SIGMA=   2.8  PHAS=  -48.1  FOM=  0.91  TEST=  0
INDE  8  55  47  FOBS=   66.8  SIGMA=   3.5  PHAS=  -57.8  FOM=  0.85  TEST=  0
INDE  8  55  49  FOBS=   94.0  SIGMA=   2.5  PHAS= -156.8  FOM=  0.93  TEST=  0
INDE  8  55  51  FOBS=   44.3  SIGMA=   7.6  PHAS=  -50.8  FOM=  0.46  TEST=  0
INDE  8  55  53  FOBS=  106.7  SIGMA=   3.2  PHAS=  -10.6  FOM=  0.95  TEST=  0
INDE  8  56   8  FOBS=   56.5  SIGMA=   4.6  PHAS=  154.7  FOM=  0.01  TEST=  0
INDE  8  56  10  FOBS=  164.2  SIGMA=   1.7  PHAS=   25.3  FOM=  0.94  TEST=  0
INDE  8  56  12  FOBS=   24.0  SIGMA=  10.8  PHAS=  -44.3  FOM=  0.38  TEST=  0
INDE  8  56  14  FOBS=   63.7  SIGMA=   2.4  PHAS=  -29.3  FOM=  0.87  TEST=  0
INDE  8  56  16  FOBS=  136.7  SIGMA=   1.3  PHAS=    5.3  FOM=  0.84  TEST=  0
INDE  8  56  18  FOBS=   73.5  SIGMA=   2.0  PHAS=  -30.8  FOM=  0.51  TEST=  0
INDE  8  56  20  FOBS=    0.0  SIGMA=  19.3  PHAS=    0.0  FOM=  0.00  TEST=  0
INDE  8  56  22  FOBS=   57.6  SIGMA=   3.2  PHAS=   42.5  FOM=  0.69  TEST=  0
INDE  8  56  24  FOBS=   78.6  SIGMA=   2.5  PHAS=  148.1  FOM=  0.07  TEST=  1
INDE  8  56  26  FOBS=   56.5  SIGMA=   3.5  PHAS=  162.9  FOM=  0.92  TEST=  0
INDE  8  56  28  FOBS=   89.2  SIGMA=   2.2  PHAS=   66.5  FOM=  0.86  TEST=  0
INDE  8  56  30  FOBS=  158.8  SIGMA=   1.4  PHAS=  -25.8  FOM=  0.96  TEST=  0
INDE  8  56  32  FOBS=  107.0  SIGMA=   1.9  PHAS=  -60.0  FOM=  0.87  TEST=  0
INDE  8  56  34  FOBS=   61.1  SIGMA=   3.2  PHAS=  151.7  FOM=  0.72  TEST=  0
INDE  8  56  36  FOBS=   50.3  SIGMA=   3.9  PHAS=  118.0  FOM=  0.61  TEST=  0
INDE  8  56  38  FOBS=    0.0  SIGMA=  21.5  PHAS=    0.0  FOM=  0.00  TEST=  0
INDE  8  56  40  FOBS=   25.1  SIGMA=   8.1  PHAS=  127.6  FOM=  0.27  TEST=  0
INDE  8  56  42  FOBS=   46.9  SIGMA=   4.2  PHAS=  -81.6  FOM=  0.04  TEST=  1
INDE  8  56  44  FOBS=   33.9  SIGMA=   6.2  PHAS=   24.1  FOM=  0.37  TEST=  0
INDE  8  56  46  FOBS=    0.0  SIGMA=  22.5  PHAS=    0.0  FOM=  0.00  TEST=  0
INDE  8  56  48  FOBS=   28.2  SIGMA=  10.1  PHAS=  119.0  FOM=  0.25  TEST=  1
INDE  8  56  50  FOBS=   31.2  SIGMA=  12.0  PHAS=  -59.5  FOM=  0.41  TEST=  0
INDE  8  56  52  FOBS=   61.4  SIGMA=   6.6  PHAS= -114.4  FOM=  0.81  TEST=  0
INDE  8  57   9  FOBS=  106.2  SIGMA=   2.5  PHAS=   22.0  FOM=  0.89  TEST=  0
INDE  8  57  11  FOBS=   50.7  SIGMA=   5.2  PHAS= -146.0  FOM=  0.67  TEST=  1
INDE  8  57  13  FOBS=  124.0  SIGMA=   2.2  PHAS=  -94.0  FOM=  0.96  TEST=  0
INDE  8  57  15  FOBS=    0.0  SIGMA=  18.6  PHAS=    0.0  FOM=  0.00  TEST=  0
INDE  8  57  17  FOBS=  166.1  SIGMA=   1.1  PHAS= -162.5  FOM=  0.93  TEST=  0
INDE  8  57  19  FOBS=   11.8  SIGMA=  15.9  PHAS=  175.6  FOM=  0.22  TEST=  0
INDE  8  57  21  FOBS=   69.6  SIGMA=   2.7  PHAS=   39.4  FOM=  0.59  TEST=  0
INDE  8  57  23  FOBS=   49.3  SIGMA=   3.9  PHAS=  -59.9  FOM=  0.12  TEST=  1
INDE  8  57  25  FOBS=   43.0  SIGMA=   4.5  PHAS=   11.2  FOM=  0.45  TEST=  0
INDE  8  57  27  FOBS=   24.9  SIGMA=   8.5  PHAS= -146.9  FOM=  0.59  TEST=  0
INDE  8  57  29  FOBS=  166.9  SIGMA=   1.3  PHAS= -102.8  FOM=  0.97  TEST=  0
INDE  8  57  31  FOBS=   96.9  SIGMA=   2.1  PHAS=  -93.9  FOM=  0.44  TEST=  1
INDE  8  57  33  FOBS=   43.6  SIGMA=   4.5  PHAS=  177.7  FOM=  0.69  TEST=  0
INDE  8  57  35  FOBS=    0.0  SIGMA=  20.4  PHAS=    0.0  FOM=  0.00  TEST=  0
INDE  8  57  37  FOBS=   30.9  SIGMA=   9.5  PHAS=   41.0  FOM=  0.18  TEST=  0
INDE  8  57  39  FOBS=    0.0  SIGMA=  21.0  PHAS=    0.0  FOM=  0.00  TEST=  1
INDE  8  57  41  FOBS=    0.0  SIGMA=  22.2  PHAS=    0.0  FOM=  0.00  TEST=  0
INDE  8  57  43  FOBS=   68.7  SIGMA=   3.2  PHAS= -153.3  FOM=  0.89  TEST=  0
INDE  8  57  45  FOBS=   51.7  SIGMA=   4.2  PHAS=  -71.1  FOM=  0.89  TEST=  0
INDE  8  57  47  FOBS=   35.1  SIGMA=   7.9  PHAS=  -71.1  FOM=  0.63  TEST=  0
INDE  8  57  49  FOBS=  123.9  SIGMA=   2.8  PHAS= -104.6  FOM=  0.97  TEST=  0
INDE  8  57  51  FOBS=    0.0  SIGMA=  28.0  PHAS=    0.0  FOM=  0.00  TEST=  0
INDE  8  58   8  FOBS=   56.1  SIGMA=   4.6  PHAS=   23.4  FOM=  0.81  TEST=  0
INDE  8  58  10  FOBS=  146.3  SIGMA=   1.9  PHAS=  -71.0  FOM=  0.97  TEST=  0
INDE  8  58  12  FOBS=  127.4  SIGMA=   2.1  PHAS=  149.8  FOM=  0.90  TEST=  0
INDE  8  58  14  FOBS=   51.4  SIGMA=   3.4  PHAS=   43.0  FOM=  0.74  TEST=  0
```

*FIG. 12A - 231*

```
INDE  8  58  16  FOBS=   72.7  SIGMA=   2.6  PHAS=    7.9  FOM=  0.65  TEST=  0
INDE  8  58  18  FOBS=  139.4  SIGMA=   1.5  PHAS=  101.6  FOM=  0.96  TEST=  0
INDE  8  58  20  FOBS=   71.4  SIGMA=   2.4  PHAS=  -91.7  FOM=  0.68  TEST=  0
INDE  8  58  22  FOBS=   92.0  SIGMA=   2.1  PHAS=  -90.0  FOM=  0.87  TEST=  0
INDE  8  58  24  FOBS=    8.1  SIGMA=  27.8  PHAS=   46.7  FOM=  0.05  TEST=  0
INDE  8  58  26  FOBS=    0.0  SIGMA=  19.4  PHAS=    0.0  FOM=  0.00  TEST=  0
INDE  8  58  28  FOBS=   49.3  SIGMA=   3.9  PHAS=   82.9  FOM=  0.55  TEST=  1
INDE  8  58  30  FOBS=   67.2  SIGMA=   2.9  PHAS= -119.0  FOM=  0.77  TEST=  0
INDE  8  58  32  FOBS=   62.4  SIGMA=   3.5  PHAS=   18.1  FOM=  0.48  TEST=  0
INDE  8  58  34  FOBS=   83.5  SIGMA=   2.6  PHAS=   -7.3  FOM=  0.59  TEST=  0
INDE  8  58  36  FOBS=   67.3  SIGMA=   3.6  PHAS=  -10.9  FOM=  0.85  TEST=  0
INDE  8  58  38  FOBS=    0.0  SIGMA=  21.6  PHAS=    0.0  FOM=  0.00  TEST=  0
INDE  8  58  40  FOBS=    0.0  SIGMA=  21.1  PHAS=    0.0  FOM=  0.00  TEST=  0
INDE  8  58  42  FOBS=   43.2  SIGMA=   5.8  PHAS=  166.5  FOM=  0.20  TEST=  1
INDE  8  58  44  FOBS=   78.1  SIGMA=   2.8  PHAS=  110.0  FOM=  0.90  TEST=  0
INDE  8  58  46  FOBS=    0.0  SIGMA=  22.5  PHAS=    0.0  FOM=  0.00  TEST=  0
INDE  8  58  48  FOBS=   85.7  SIGMA=   3.9  PHAS= -168.7  FOM=  0.90  TEST=  0
INDE  8  58  50  FOBS=  105.1  SIGMA=   3.8  PHAS= -156.7  FOM=  0.91  TEST=  0
INDE  8  59   9  FOBS=   66.9  SIGMA=   3.8  PHAS= -179.9  FOM=  0.33  TEST=  0
INDE  8  59  11  FOBS=  161.4  SIGMA=   2.4  PHAS=  127.6  FOM=  0.92  TEST=  0
INDE  8  59  13  FOBS=   98.8  SIGMA=   2.7  PHAS=  -95.0  FOM=  0.93  TEST=  0
INDE  8  59  15  FOBS=   27.0  SIGMA=   6.6  PHAS=  121.4  FOM=  0.32  TEST=  0
INDE  8  59  17  FOBS=   47.4  SIGMA=   4.0  PHAS=  -72.5  FOM=  0.62  TEST=  0
INDE  8  59  19  FOBS=   46.8  SIGMA=   3.5  PHAS=  -54.7  FOM=  0.22  TEST=  0
INDE  8  59  21  FOBS=   14.9  SIGMA=  11.2  PHAS=   33.8  FOM=  0.13  TEST=  0
INDE  8  59  23  FOBS=   17.3  SIGMA=   6.0  PHAS=  161.1  FOM=  0.43  TEST=  0
INDE  8  59  25  FOBS=   47.4  SIGMA=   4.1  PHAS=  -90.0  FOM=  0.50  TEST=  0
INDE  8  59  27  FOBS=   41.8  SIGMA=   4.6  PHAS= -154.2  FOM=  0.36  TEST=  0
INDE  8  59  29  FOBS=   86.2  SIGMA=   2.5  PHAS= -108.0  FOM=  0.70  TEST=  0
INDE  8  59  31  FOBS=   49.5  SIGMA=   4.7  PHAS= -178.3  FOM=  0.42  TEST=  0
INDE  8  59  33  FOBS=  100.2  SIGMA=   2.4  PHAS= -121.5  FOM=  0.91  TEST=  0
INDE  8  59  35  FOBS=   41.4  SIGMA=   6.5  PHAS= -130.2  FOM=  0.68  TEST=  0
INDE  8  59  37  FOBS=   63.3  SIGMA=   3.8  PHAS= -152.5  FOM=  0.88  TEST=  0
INDE  8  59  39  FOBS=  117.7  SIGMA=   2.1  PHAS= -177.6  FOM=  0.89  TEST=  0
INDE  8  59  41  FOBS=   83.4  SIGMA=   2.5  PHAS= -163.1  FOM=  0.02  TEST=  1
INDE  8  59  43  FOBS=   54.0  SIGMA=   4.0  PHAS=  120.8  FOM=  0.71  TEST=  0
INDE  8  59  45  FOBS=    0.0  SIGMA=  22.4  PHAS=    0.0  FOM=  0.00  TEST=  0
INDE  8  59  47  FOBS=   51.8  SIGMA=   7.5  PHAS=  -24.5  FOM=  0.03  TEST=  1
INDE  8  59  49  FOBS=   56.3  SIGMA=   6.8  PHAS=  149.6  FOM=  0.70  TEST=  0
INDE  8  60   8  FOBS=   81.6  SIGMA=   3.2  PHAS=   -6.0  FOM=  0.76  TEST=  0
INDE  8  60  10  FOBS=    0.0  SIGMA=  24.4  PHAS=    0.0  FOM=  0.00  TEST=  0
INDE  8  60  12  FOBS=  144.9  SIGMA=   1.9  PHAS=  159.0  FOM=  0.96  TEST=  0
INDE  8  60  14  FOBS=  117.5  SIGMA=   2.2  PHAS=  177.9  FOM=  0.93  TEST=  0
INDE  8  60  16  FOBS=    0.0  SIGMA=  20.1  PHAS=    0.0  FOM=  0.00  TEST=  0
INDE  8  60  18  FOBS=    0.0  SIGMA=  19.6  PHAS=    0.0  FOM=  0.00  TEST=  1
INDE  8  60  20  FOBS=   70.2  SIGMA=   2.4  PHAS=  106.5  FOM=  0.26  TEST=  1
INDE  8  60  22  FOBS=   37.2  SIGMA=   4.8  PHAS= -129.5  FOM=  0.48  TEST=  0
INDE  8  60  24  FOBS=  111.4  SIGMA=   2.0  PHAS=  135.0  FOM=  0.77  TEST=  0
INDE  8  60  26  FOBS=    0.0  SIGMA=  21.5  PHAS=    0.0  FOM=  0.00  TEST=  0
INDE  8  60  28  FOBS=   83.7  SIGMA=   2.8  PHAS=  102.4  FOM=  0.84  TEST=  0
INDE  8  60  30  FOBS=   19.1  SIGMA=  12.1  PHAS=  119.9  FOM=  0.28  TEST=  0
INDE  8  60  32  FOBS=   56.0  SIGMA=   4.3  PHAS=  166.5  FOM=  0.66  TEST=  0
INDE  8  60  34  FOBS=    0.0  SIGMA=  21.7  PHAS=    0.0  FOM=  0.00  TEST=  0
INDE  8  60  36  FOBS=  122.7  SIGMA=   2.1  PHAS=   45.2  FOM=  0.92  TEST=  0
INDE  8  60  38  FOBS=   89.0  SIGMA=   2.8  PHAS=   76.3  FOM=  0.91  TEST=  0
INDE  8  60  40  FOBS=   55.1  SIGMA=   4.4  PHAS=  -21.6  FOM=  0.12  TEST=  1
INDE  8  60  42  FOBS=   80.7  SIGMA=   3.2  PHAS=  -20.3  FOM=  0.25  TEST=  1
INDE  8  60  44  FOBS=   36.3  SIGMA=   6.1  PHAS=   22.8  FOM=  0.40  TEST=  0
INDE  8  60  46  FOBS=    0.0  SIGMA=  25.1  PHAS=    0.0  FOM=  0.00  TEST=  0
INDE  8  60  48  FOBS=    0.0  SIGMA=  31.4  PHAS=    0.0  FOM=  0.00  TEST=  0
INDE  8  61   9  FOBS=    0.0  SIGMA=  22.4  PHAS=    0.0  FOM=  0.00  TEST=  0
INDE  8  61  11  FOBS=  172.1  SIGMA=   1.6  PHAS=   91.6  FOM=  0.97  TEST=  0
INDE  8  61  13  FOBS=  116.0  SIGMA=   2.2  PHAS=   97.2  FOM=  0.86  TEST=  0
INDE  8  61  15  FOBS=   82.8  SIGMA=   3.1  PHAS=   55.8  FOM=  0.91  TEST=  0
INDE  8  61  17  FOBS=   76.4  SIGMA=   2.5  PHAS=   13.5  FOM=  0.76  TEST=  0
INDE  8  61  19  FOBS=   69.9  SIGMA=   2.8  PHAS= -104.8  FOM=  0.82  TEST=  0
INDE  8  61  21  FOBS=   64.8  SIGMA=   3.1  PHAS=   19.3  FOM=  0.62  TEST=  0
INDE  8  61  23  FOBS=   15.2  SIGMA=  12.6  PHAS=  111.8  FOM=  0.36  TEST=  0
INDE  8  61  25  FOBS=   91.8  SIGMA=   3.0  PHAS=  113.1  FOM=  0.80  TEST=  0
INDE  8  61  27  FOBS=   41.1  SIGMA=   6.6  PHAS=   84.3  FOM=  0.67  TEST=  0
```

*FIG. 12A - 232*

| | | | | | | | | | | | |
|---|---|---|---|---|---|---|---|---|---|---|---|
| INDE | 8 | 61 | 29 | FOBS= | 42.1 | SIGMA= | 6.4 | PHAS= | -54.6 | FOM= | 0.64 | TEST= 0
| INDE | 8 | 61 | 31 | FOBS= | 0.0 | SIGMA= | 25.8 | PHAS= | 0.0 | FOM= | 0.00 | TEST= 0
| INDE | 8 | 61 | 33 | FOBS= | 0.0 | SIGMA= | 23.4 | PHAS= | 0.0 | FOM= | 0.00 | TEST= 0
| INDE | 8 | 61 | 35 | FOBS= | 41.3 | SIGMA= | 6.7 | PHAS= | -35.9 | FOM= | 0.46 | TEST= 0
| INDE | 8 | 61 | 37 | FOBS= | 0.0 | SIGMA= | 23.5 | PHAS= | 0.0 | FOM= | 0.00 | TEST= 0
| INDE | 8 | 61 | 39 | FOBS= | 52.6 | SIGMA= | 5.4 | PHAS= | -141.2 | FOM= | 0.82 | TEST= 0
| INDE | 8 | 61 | 41 | FOBS= | 83.8 | SIGMA= | 2.8 | PHAS= | -174.6 | FOM= | 0.90 | TEST= 0
| INDE | 8 | 61 | 43 | FOBS= | 0.0 | SIGMA= | 21.6 | PHAS= | 0.0 | FOM= | 0.00 | TEST= 0
| INDE | 8 | 61 | 45 | FOBS= | 80.1 | SIGMA= | 4.1 | PHAS= | -173.0 | FOM= | 0.83 | TEST= 0
| INDE | 8 | 61 | 47 | FOBS= | 71.9 | SIGMA= | 7.0 | PHAS= | -22.6 | FOM= | 0.78 | TEST= 0
| INDE | 8 | 62 | 8 | FOBS= | 0.0 | SIGMA= | 23.8 | PHAS= | 0.0 | FOM= | 0.00 | TEST= 0
| INDE | 8 | 62 | 10 | FOBS= | 95.1 | SIGMA= | 2.8 | PHAS= | -24.0 | FOM= | 0.55 | TEST= 1
| INDE | 8 | 62 | 12 | FOBS= | 83.0 | SIGMA= | 3.1 | PHAS= | -28.1 | FOM= | 0.15 | TEST= 1
| INDE | 8 | 62 | 14 | FOBS= | 123.9 | SIGMA= | 3.0 | PHAS= | -154.8 | FOM= | 0.96 | TEST= 0
| INDE | 8 | 62 | 16 | FOBS= | 62.9 | SIGMA= | 3.0 | PHAS= | 4.8 | FOM= | 0.66 | TEST= 0
| INDE | 8 | 62 | 18 | FOBS= | 66.1 | SIGMA= | 3.4 | PHAS= | -65.8 | FOM= | 0.27 | TEST= 1
| INDE | 8 | 62 | 20 | FOBS= | 125.1 | SIGMA= | 2.0 | PHAS= | -115.2 | FOM= | 0.95 | TEST= 0
| INDE | 8 | 62 | 22 | FOBS= | 73.0 | SIGMA= | 3.0 | PHAS= | -30.6 | FOM= | 0.83 | TEST= 0
| INDE | 8 | 62 | 24 | FOBS= | 71.9 | SIGMA= | 3.8 | PHAS= | 50.2 | FOM= | 0.36 | TEST= 1
| INDE | 8 | 62 | 26 | FOBS= | 106.5 | SIGMA= | 2.7 | PHAS= | 31.4 | FOM= | 0.91 | TEST= 0
| INDE | 8 | 62 | 28 | FOBS= | 67.2 | SIGMA= | 4.1 | PHAS= | 18.0 | FOM= | 0.77 | TEST= 0
| INDE | 8 | 62 | 30 | FOBS= | 74.3 | SIGMA= | 3.7 | PHAS= | 155.0 | FOM= | 0.92 | TEST= 0
| INDE | 8 | 62 | 32 | FOBS= | 116.8 | SIGMA= | 2.5 | PHAS= | -95.6 | FOM= | 0.91 | TEST= 0
| INDE | 8 | 62 | 34 | FOBS= | 0.0 | SIGMA= | 26.4 | PHAS= | 0.0 | FOM= | 0.00 | TEST= 0
| INDE | 8 | 62 | 36 | FOBS= | 51.9 | SIGMA= | 6.8 | PHAS= | 100.9 | FOM= | 0.75 | TEST= 0
| INDE | 8 | 62 | 38 | FOBS= | 77.7 | SIGMA= | 3.7 | PHAS= | 53.1 | FOM= | 0.89 | TEST= 0
| INDE | 8 | 62 | 40 | FOBS= | 123.0 | SIGMA= | 2.4 | PHAS= | 68.2 | FOM= | 0.94 | TEST= 0
| INDE | 8 | 62 | 42 | FOBS= | 50.4 | SIGMA= | 5.7 | PHAS= | 83.4 | FOM= | 0.39 | TEST= 1
| INDE | 8 | 62 | 44 | FOBS= | 0.0 | SIGMA= | 27.1 | PHAS= | 0.0 | FOM= | 0.00 | TEST= 0
| INDE | 8 | 62 | 46 | FOBS= | 63.8 | SIGMA= | 7.9 | PHAS= | 85.1 | FOM= | 0.77 | TEST= 0
| INDE | 8 | 63 | 9 | FOBS= | 0.0 | SIGMA= | 23.3 | PHAS= | 0.0 | FOM= | 0.00 | TEST= 1
| INDE | 8 | 63 | 11 | FOBS= | 131.0 | SIGMA= | 2.9 | PHAS= | 153.1 | FOM= | 0.93 | TEST= 0
| INDE | 8 | 63 | 13 | FOBS= | 66.7 | SIGMA= | 5.2 | PHAS= | 130.8 | FOM= | 0.80 | TEST= 0
| INDE | 8 | 63 | 15 | FOBS= | 60.2 | SIGMA= | 5.8 | PHAS= | 12.6 | FOM= | 0.87 | TEST= 0
| INDE | 8 | 63 | 17 | FOBS= | 37.6 | SIGMA= | 5.5 | PHAS= | 9.1 | FOM= | 0.73 | TEST= 0
| INDE | 8 | 63 | 19 | FOBS= | 55.9 | SIGMA= | 4.1 | PHAS= | 159.4 | FOM= | 0.58 | TEST= 0
| INDE | 8 | 63 | 21 | FOBS= | 64.1 | SIGMA= | 3.2 | PHAS= | 176.2 | FOM= | 0.76 | TEST= 0
| INDE | 8 | 63 | 23 | FOBS= | 0.0 | SIGMA= | 20.8 | PHAS= | 0.0 | FOM= | 0.00 | TEST= 0
| INDE | 8 | 63 | 25 | FOBS= | 42.2 | SIGMA= | 6.4 | PHAS= | -0.3 | FOM= | 0.79 | TEST= 0
| INDE | 8 | 63 | 27 | FOBS= | 106.0 | SIGMA= | 2.7 | PHAS= | 23.1 | FOM= | 0.87 | TEST= 0
| INDE | 8 | 63 | 29 | FOBS= | 32.4 | SIGMA= | 10.2 | PHAS= | 172.8 | FOM= | 0.17 | TEST= 0
| INDE | 8 | 63 | 31 | FOBS= | 50.1 | SIGMA= | 5.5 | PHAS= | -172.1 | FOM= | 0.16 | TEST= 0
| INDE | 8 | 63 | 33 | FOBS= | 50.7 | SIGMA= | 5.4 | PHAS= | -111.1 | FOM= | 0.60 | TEST= 0
| INDE | 8 | 63 | 35 | FOBS= | 34.5 | SIGMA= | 8.2 | PHAS= | 104.1 | FOM= | 0.54 | TEST= 0
| INDE | 8 | 63 | 37 | FOBS= | 41.5 | SIGMA= | 6.8 | PHAS= | 77.4 | FOM= | 0.58 | TEST= 0
| INDE | 8 | 63 | 39 | FOBS= | 103.9 | SIGMA= | 2.8 | PHAS= | -56.4 | FOM= | 0.94 | TEST= 0
| INDE | 8 | 63 | 41 | FOBS= | 39.5 | SIGMA= | 7.3 | PHAS= | 55.5 | FOM= | 0.18 | TEST= 1
| INDE | 8 | 63 | 43 | FOBS= | 55.9 | SIGMA= | 5.3 | PHAS= | -163.4 | FOM= | 0.46 | TEST= 0
| INDE | 8 | 64 | 8 | FOBS= | 37.4 | SIGMA= | 7.5 | PHAS= | 148.2 | FOM= | 0.64 | TEST= 0
| INDE | 8 | 64 | 10 | FOBS= | 103.1 | SIGMA= | 3.5 | PHAS= | 53.2 | FOM= | 0.92 | TEST= 0
| INDE | 8 | 64 | 12 | FOBS= | 16.8 | SIGMA= | 20.6 | PHAS= | -39.6 | FOM= | 0.26 | TEST= 0
| INDE | 8 | 64 | 14 | FOBS= | 77.7 | SIGMA= | 4.5 | PHAS= | -143.6 | FOM= | 0.83 | TEST= 0
| INDE | 8 | 64 | 16 | FOBS= | 122.7 | SIGMA= | 3.0 | PHAS= | -35.7 | FOM= | 0.93 | TEST= 0
| INDE | 8 | 64 | 18 | FOBS= | 12.5 | SIGMA= | 17.4 | PHAS= | 6.9 | FOM= | 0.03 | TEST= 1
| INDE | 8 | 64 | 20 | FOBS= | 73.4 | SIGMA= | 3.2 | PHAS= | -124.9 | FOM= | 0.89 | TEST= 0
| INDE | 8 | 64 | 22 | FOBS= | 57.5 | SIGMA= | 3.6 | PHAS= | 45.7 | FOM= | 0.61 | TEST= 0
| INDE | 8 | 64 | 24 | FOBS= | 29.0 | SIGMA= | 8.4 | PHAS= | -23.9 | FOM= | 0.30 | TEST= 0
| INDE | 8 | 64 | 26 | FOBS= | 16.3 | SIGMA= | 16.4 | PHAS= | -23.4 | FOM= | 0.45 | TEST= 0
| INDE | 8 | 64 | 28 | FOBS= | 52.4 | SIGMA= | 5.3 | PHAS= | -114.2 | FOM= | 0.68 | TEST= 0
| INDE | 8 | 64 | 30 | FOBS= | 31.5 | SIGMA= | 10.6 | PHAS= | -136.8 | FOM= | 0.04 | TEST= 1
| INDE | 8 | 64 | 32 | FOBS= | 0.0 | SIGMA= | 23.5 | PHAS= | 0.0 | FOM= | 0.00 | TEST= 0
| INDE | 8 | 64 | 34 | FOBS= | 51.7 | SIGMA= | 5.4 | PHAS= | 147.1 | FOM= | 0.34 | TEST= 0
| INDE | 8 | 64 | 36 | FOBS= | 39.1 | SIGMA= | 7.2 | PHAS= | -9.4 | FOM= | 0.54 | TEST= 0
| INDE | 8 | 64 | 38 | FOBS= | 30.6 | SIGMA= | 10.8 | PHAS= | -16.6 | FOM= | 0.17 | TEST= 0
| INDE | 8 | 64 | 40 | FOBS= | 53.6 | SIGMA= | 7.0 | PHAS= | 123.9 | FOM= | 0.71 | TEST= 0
| INDE | 8 | 64 | 42 | FOBS= | 0.0 | SIGMA= | 24.3 | PHAS= | 0.0 | FOM= | 0.00 | TEST= 0
| INDE | 8 | 65 | 9 | FOBS= | 89.2 | SIGMA= | 4.0 | PHAS= | 5.4 | FOM= | 0.83 | TEST= 0
| INDE | 8 | 65 | 11 | FOBS= | 0.0 | SIGMA= | 26.4 | PHAS= | 0.0 | FOM= | 0.00 | TEST= 1
| INDE | 8 | 65 | 13 | FOBS= | 55.9 | SIGMA= | 6.3 | PHAS= | -171.8 | FOM= | 0.80 | TEST= 0
| INDE | 8 | 65 | 15 | FOBS= | 46.0 | SIGMA= | 7.6 | PHAS= | -154.4 | FOM= | 0.44 | TEST= 0

*FIG. 12A - 233*

```
INDE  8  65  17  FOBS=   19.2  SIGMA=  17.9  PHAS=  -100.4  FOM=  0.09  TEST= 0
INDE  8  65  19  FOBS=    0.0  SIGMA=  21.2  PHAS=     0.0  FOM=  0.00  TEST= 0
INDE  8  65  21  FOBS=   97.0  SIGMA=   2.5  PHAS=  -121.1  FOM=  0.63  TEST= 0
INDE  8  65  23  FOBS=   75.8  SIGMA=   2.8  PHAS=  -144.7  FOM=  0.84  TEST= 0
INDE  8  65  25  FOBS=   87.6  SIGMA=   2.6  PHAS=   -66.8  FOM=  0.68  TEST= 0
INDE  8  65  27  FOBS=   14.7  SIGMA=  22.8  PHAS=    15.9  FOM=  0.21  TEST= 0
INDE  8  65  29  FOBS=   92.4  SIGMA=   3.1  PHAS=   154.3  FOM=  0.91  TEST= 0
INDE  8  65  31  FOBS=   86.3  SIGMA=   3.3  PHAS=   -44.9  FOM=  0.87  TEST= 0
INDE  8  65  33  FOBS=   45.4  SIGMA=   6.2  PHAS=    37.7  FOM=  0.55  TEST= 0
INDE  8  65  35  FOBS=   36.0  SIGMA=   7.8  PHAS=  -141.8  FOM=  0.35  TEST= 0
INDE  8  65  37  FOBS=    0.0  SIGMA=  26.9  PHAS=     0.0  FOM=  0.00  TEST= 0
INDE  8  65  39  FOBS=   47.4  SIGMA=   6.2  PHAS=     9.7  FOM=  0.58  TEST= 0
INDE  8  65  41  FOBS=   34.5  SIGMA=  11.1  PHAS=   171.0  FOM=  0.45  TEST= 0
INDE  8  66   8  FOBS=   25.8  SIGMA=  13.6  PHAS=    12.3  FOM=  0.14  TEST= 0
INDE  8  66  10  FOBS=   52.5  SIGMA=   6.7  PHAS=   119.8  FOM=  0.74  TEST= 0
INDE  8  66  12  FOBS=   80.0  SIGMA=   4.5  PHAS=  -166.4  FOM=  0.91  TEST= 0
INDE  8  66  14  FOBS=   83.7  SIGMA=   4.2  PHAS=    51.1  FOM=  0.81  TEST= 0
INDE  8  66  16  FOBS=   45.0  SIGMA=   7.7  PHAS=    -1.8  FOM=  0.77  TEST= 0
INDE  8  66  18  FOBS=   34.4  SIGMA=   6.0  PHAS=  -134.5  FOM=  0.74  TEST= 0
INDE  8  66  20  FOBS=   54.6  SIGMA=   4.3  PHAS=   -91.9  FOM=  0.59  TEST= 0
INDE  8  66  22  FOBS=   30.9  SIGMA=   7.8  PHAS=   137.7  FOM=  0.40  TEST= 0
INDE  8  66  24  FOBS=   79.3  SIGMA=   2.7  PHAS=   -37.9  FOM=  0.77  TEST= 0
INDE  8  66  26  FOBS=    9.8  SIGMA=  23.0  PHAS=    92.8  FOM=  0.16  TEST= 0
INDE  8  66  28  FOBS=   71.8  SIGMA=   3.9  PHAS=   139.9  FOM=  0.44  TEST= 0
INDE  8  66  30  FOBS=   38.3  SIGMA=   7.4  PHAS=   -57.1  FOM=  0.46  TEST= 0
INDE  8  66  32  FOBS=   68.1  SIGMA=   4.2  PHAS=   -97.0  FOM=  0.80  TEST= 0
INDE  8  66  34  FOBS=   37.3  SIGMA=   7.6  PHAS=  -158.0  FOM=  0.28  TEST= 1
INDE  8  66  36  FOBS=   58.0  SIGMA=   5.0  PHAS=   137.7  FOM=  0.22  TEST= 1
INDE  8  66  38  FOBS=   29.2  SIGMA=  10.0  PHAS=    96.3  FOM=  0.07  TEST= 1
INDE  8  66  40  FOBS=   67.8  SIGMA=   4.5  PHAS=   -62.8  FOM=  0.29  TEST= 0
INDE  8  67   9  FOBS=   94.0  SIGMA=   5.3  PHAS=    50.9  FOM=  0.77  TEST= 0
INDE  8  67  11  FOBS=   84.9  SIGMA=   4.2  PHAS=    60.3  FOM=  0.88  TEST= 0
INDE  8  67  13  FOBS=   27.8  SIGMA=  12.6  PHAS=   -87.9  FOM=  0.22  TEST= 0
INDE  8  67  15  FOBS=   41.8  SIGMA=   8.3  PHAS=   -35.0  FOM=  0.52  TEST= 0
INDE  8  67  17  FOBS=   49.6  SIGMA=   7.0  PHAS=  -107.1  FOM=  0.66  TEST= 1
INDE  8  67  19  FOBS=   44.7  SIGMA=   4.8  PHAS=   -46.0  FOM=  0.37  TEST= 0
INDE  8  67  21  FOBS=   53.7  SIGMA=   4.4  PHAS=  -105.5  FOM=  0.47  TEST= 0
INDE  8  67  23  FOBS=   55.6  SIGMA=   3.8  PHAS=    45.5  FOM=  0.33  TEST= 0
INDE  8  67  25  FOBS=   84.3  SIGMA=   2.6  PHAS=  -151.3  FOM=  0.91  TEST= 0
INDE  8  67  27  FOBS=   66.7  SIGMA=   3.5  PHAS=   -88.3  FOM=  0.82  TEST= 0
INDE  8  67  29  FOBS=   56.8  SIGMA=   5.0  PHAS=   113.8  FOM=  0.80  TEST= 0
INDE  8  67  31  FOBS=  107.6  SIGMA=   2.7  PHAS=  -128.8  FOM=  0.88  TEST= 0
INDE  8  67  33  FOBS=   32.4  SIGMA=  10.9  PHAS=   171.5  FOM=  0.17  TEST= 0
INDE  8  67  35  FOBS=    0.0  SIGMA=  23.8  PHAS=     0.0  FOM=  0.00  TEST= 1
INDE  8  67  37  FOBS=    0.0  SIGMA=  24.3  PHAS=     0.0  FOM=  0.00  TEST= 0
INDE  8  68  14  FOBS=   19.7  SIGMA=  24.4  PHAS=    -2.8  FOM=  0.16  TEST= 0
INDE  8  68  16  FOBS=   43.7  SIGMA=   7.9  PHAS=   -74.0  FOM=  0.26  TEST= 0
INDE  8  68  18  FOBS=   33.6  SIGMA=  10.3  PHAS=   166.5  FOM=  0.20  TEST= 0
INDE  8  68  20  FOBS=   68.4  SIGMA=   3.3  PHAS=   -81.9  FOM=  0.51  TEST= 0
INDE  8  68  22  FOBS=   47.8  SIGMA=   5.0  PHAS=    38.3  FOM=  0.22  TEST= 0
INDE  8  68  24  FOBS=    0.0  SIGMA=  20.7  PHAS=     0.0  FOM=  0.00  TEST= 0
INDE  8  68  26  FOBS=   99.0  SIGMA=   2.3  PHAS=   138.4  FOM=  0.93  TEST= 0
INDE  8  68  28  FOBS=   58.0  SIGMA=   4.1  PHAS=    81.6  FOM=  0.82  TEST= 0
INDE  8  68  30  FOBS=   56.9  SIGMA=   5.2  PHAS=   142.7  FOM=  0.77  TEST= 0
INDE  8  68  32  FOBS=    0.0  SIGMA=  26.8  PHAS=     0.0  FOM=  0.00  TEST= 0
INDE  8  68  34  FOBS=    0.0  SIGMA=  26.6  PHAS=     0.0  FOM=  0.00  TEST= 0
INDE  8  68  36  FOBS=    0.0  SIGMA=  24.1  PHAS=     0.0  FOM=  0.00  TEST= 0
INDE  8  69  17  FOBS=    0.0  SIGMA=  31.2  PHAS=     0.0  FOM=  0.00  TEST= 0
INDE  8  69  19  FOBS=   54.2  SIGMA=   9.0  PHAS=   -29.7  FOM=  0.39  TEST= 0
INDE  8  69  21  FOBS=   61.8  SIGMA=   8.1  PHAS=   174.2  FOM=  0.12  TEST= 0
INDE  8  69  23  FOBS=   18.8  SIGMA=  18.6  PHAS=    53.0  FOM=  0.55  TEST= 0
INDE  8  69  25  FOBS=   61.9  SIGMA=   3.6  PHAS=    77.1  FOM=  0.84  TEST= 0
INDE  8  69  27  FOBS=   46.3  SIGMA=   6.0  PHAS=   -36.9  FOM=  0.29  TEST= 0
INDE  8  69  29  FOBS=   29.1  SIGMA=   9.8  PHAS=    90.5  FOM=  0.62  TEST= 0
INDE  8  69  31  FOBS=    0.0  SIGMA=  24.0  PHAS=     0.0  FOM=  0.00  TEST= 0
INDE  8  69  33  FOBS=   87.6  SIGMA=   3.5  PHAS=   -94.1  FOM=  0.87  TEST= 0
INDE  8  70  20  FOBS=    0.0  SIGMA=  23.2  PHAS=     0.0  FOM=  0.00  TEST= 1
INDE  8  70  22  FOBS=   17.8  SIGMA=  15.6  PHAS=   149.0  FOM=  0.19  TEST= 0
INDE  8  70  24  FOBS=   55.4  SIGMA=   5.2  PHAS=   -25.2  FOM=  0.92  TEST= 0
INDE  8  70  26  FOBS=   21.1  SIGMA=  12.6  PHAS=   121.7  FOM=  0.07  TEST= 0
```

*FIG. 12A - 234*

| | | | | | | | | | | | |
|---|---|---|---|---|---|---|---|---|---|---|---|
| INDE | 8 | 70 | 28 | FOBS= | 49.3 | SIGMA= | 5.7 | PHAS= | 74.6 | FOM= 0.59 | TEST= 0 |
| INDE | 8 | 70 | 30 | FOBS= | 32.0 | SIGMA= | 7.7 | PHAS= | -14.3 | FOM= 0.16 | TEST= 0 |
| INDE | 8 | 70 | 32 | FOBS= | 62.5 | SIGMA= | 4.8 | PHAS= | -166.9 | FOM= 0.81 | TEST= 0 |
| INDE | 8 | 71 | 21 | FOBS= | 38.8 | SIGMA= | 7.4 | PHAS= | 102.9 | FOM= 0.10 | TEST= 1 |
| INDE | 8 | 71 | 23 | FOBS= | 12.3 | SIGMA= | 27.8 | PHAS= | 7.1 | FOM= 0.22 | TEST= 0 |
| INDE | 8 | 71 | 25 | FOBS= | 61.1 | SIGMA= | 6.0 | PHAS= | -123.5 | FOM= 0.82 | TEST= 0 |
| INDE | 8 | 71 | 27 | FOBS= | 0.0 | SIGMA= | 22.7 | PHAS= | 0.0 | FOM= 0.00 | TEST= 0 |
| INDE | 8 | 71 | 29 | FOBS= | 38.5 | SIGMA= | 9.1 | PHAS= | 97.3 | FOM= 0.39 | TEST= 0 |
| INDE | 8 | 72 | 22 | FOBS= | 21.7 | SIGMA= | 14.1 | PHAS= | -102.4 | FOM= 0.01 | TEST= 0 |
| INDE | 8 | 72 | 24 | FOBS= | 0.0 | SIGMA= | 26.9 | PHAS= | 0.0 | FOM= 0.00 | TEST= 0 |
| INDE | 8 | 72 | 26 | FOBS= | 12.4 | SIGMA= | 23.1 | PHAS= | 106.1 | FOM= 0.11 | TEST= 0 |
| INDE | 8 | 72 | 28 | FOBS= | 60.0 | SIGMA= | 5.4 | PHAS= | -35.1 | FOM= 0.45 | TEST= 0 |
| INDE | 8 | 73 | 23 | FOBS= | 54.6 | SIGMA= | 5.9 | PHAS= | 14.3 | FOM= 0.27 | TEST= 0 |
| INDE | 8 | 73 | 25 | FOBS= | 29.2 | SIGMA= | 13.2 | PHAS= | 46.5 | FOM= 0.51 | TEST= 0 |
| INDE | 8 | 74 | 8 | FOBS= | 68.2 | SIGMA= | 5.9 | PHAS= | 177.8 | FOM= 0.54 | TEST= 0 |
| INDE | 8 | 76 | 8 | FOBS= | 0.0 | SIGMA= | 28.4 | PHAS= | 0.0 | FOM= 0.00 | TEST= 0 |
| INDE | 9 | 10 | 13 | FOBS= | 156.2 | SIGMA= | 0.6 | PHAS= | -69.1 | FOM= 0.85 | TEST= 0 |
| INDE | 9 | 10 | 15 | FOBS= | 105.9 | SIGMA= | 0.6 | PHAS= | -177.4 | FOM= 0.70 | TEST= 0 |
| INDE | 9 | 10 | 17 | FOBS= | 320.2 | SIGMA= | 0.4 | PHAS= | 93.2 | FOM= 0.94 | TEST= 0 |
| INDE | 9 | 10 | 19 | FOBS= | 174.1 | SIGMA= | 0.4 | PHAS= | -59.9 | FOM= 0.87 | TEST= 0 |
| INDE | 9 | 10 | 21 | FOBS= | 319.3 | SIGMA= | 0.5 | PHAS= | -2.5 | FOM= 0.95 | TEST= 0 |
| INDE | 9 | 10 | 23 | FOBS= | 44.2 | SIGMA= | 1.4 | PHAS= | -48.9 | FOM= 0.91 | TEST= 0 |
| INDE | 9 | 10 | 25 | FOBS= | 131.6 | SIGMA= | 0.6 | PHAS= | 123.9 | FOM= 0.99 | TEST= 0 |
| INDE | 9 | 10 | 27 | FOBS= | 77.6 | SIGMA= | 1.0 | PHAS= | 173.2 | FOM= 0.31 | TEST= 0 |
| INDE | 9 | 10 | 29 | FOBS= | 112.4 | SIGMA= | 0.7 | PHAS= | 139.7 | FOM= 0.99 | TEST= 0 |
| INDE | 9 | 10 | 31 | FOBS= | 52.0 | SIGMA= | 1.7 | PHAS= | 133.2 | FOM= 0.88 | TEST= 0 |
| INDE | 9 | 10 | 33 | FOBS= | 96.7 | SIGMA= | 1.3 | PHAS= | 63.5 | FOM= 0.99 | TEST= 0 |
| INDE | 9 | 10 | 35 | FOBS= | 204.2 | SIGMA= | 1.0 | PHAS= | -42.5 | FOM= 0.94 | TEST= 0 |
| INDE | 9 | 10 | 37 | FOBS= | 220.1 | SIGMA= | 0.8 | PHAS= | 79.0 | FOM= 0.99 | TEST= 0 |
| INDE | 9 | 10 | 39 | FOBS= | 15.4 | SIGMA= | 11.1 | PHAS= | -29.2 | FOM= 0.02 | TEST= 0 |
| INDE | 9 | 10 | 41 | FOBS= | 311.2 | SIGMA= | 0.7 | PHAS= | -154.7 | FOM= 0.92 | TEST= 0 |
| INDE | 9 | 10 | 43 | FOBS= | 130.0 | SIGMA= | 1.5 | PHAS= | 60.8 | FOM= 0.66 | TEST= 0 |
| INDE | 9 | 10 | 45 | FOBS= | 250.5 | SIGMA= | 0.9 | PHAS= | -140.5 | FOM= 0.96 | TEST= 0 |
| INDE | 9 | 10 | 47 | FOBS= | 102.8 | SIGMA= | 2.1 | PHAS= | 16.1 | FOM= 0.75 | TEST= 1 |
| INDE | 9 | 10 | 49 | FOBS= | 153.5 | SIGMA= | 1.4 | PHAS= | -73.1 | FOM= 0.88 | TEST= 1 |
| INDE | 9 | 10 | 51 | FOBS= | 234.4 | SIGMA= | 1.0 | PHAS= | -170.9 | FOM= 0.92 | TEST= 1 |
| INDE | 9 | 10 | 53 | FOBS= | 50.9 | SIGMA= | 4.4 | PHAS= | -54.3 | FOM= 0.54 | TEST= 0 |
| INDE | 9 | 10 | 55 | FOBS= | 63.3 | SIGMA= | 2.8 | PHAS= | 57.9 | FOM= 0.98 | TEST= 0 |
| INDE | 9 | 10 | 57 | FOBS= | 177.7 | SIGMA= | 1.6 | PHAS= | 148.1 | FOM= 0.68 | TEST= 1 |
| INDE | 9 | 10 | 59 | FOBS= | 129.6 | SIGMA= | 2.1 | PHAS= | -125.7 | FOM= 0.82 | TEST= 0 |
| INDE | 9 | 10 | 61 | FOBS= | 0.0 | SIGMA= | 22.2 | PHAS= | 0.0 | FOM= 0.00 | TEST= 0 |
| INDE | 9 | 10 | 63 | FOBS= | 101.4 | SIGMA= | 3.6 | PHAS= | 85.5 | FOM= 0.10 | TEST= 1 |
| INDE | 9 | 10 | 65 | FOBS= | 153.5 | SIGMA= | 2.5 | PHAS= | 10.6 | FOM= 0.97 | TEST= 0 |
| INDE | 9 | 11 | 12 | FOBS= | 149.6 | SIGMA= | 0.5 | PHAS= | -9.3 | FOM= 0.74 | TEST= 0 |
| INDE | 9 | 11 | 14 | FOBS= | 40.0 | SIGMA= | 1.6 | PHAS= | -34.2 | FOM= 0.89 | TEST= 0 |
| INDE | 9 | 11 | 16 | FOBS= | 27.0 | SIGMA= | 2.2 | PHAS= | 3.4 | FOM= 0.32 | TEST= 0 |
| INDE | 9 | 11 | 18 | FOBS= | 93.9 | SIGMA= | 0.6 | PHAS= | -135.3 | FOM= 0.73 | TEST= 0 |
| INDE | 9 | 11 | 20 | FOBS= | 204.6 | SIGMA= | 0.4 | PHAS= | -179.6 | FOM= 0.95 | TEST= 0 |
| INDE | 9 | 11 | 22 | FOBS= | 52.6 | SIGMA= | 1.1 | PHAS= | -104.2 | FOM= 0.52 | TEST= 0 |
| INDE | 9 | 11 | 24 | FOBS= | 172.2 | SIGMA= | 0.5 | PHAS= | -84.3 | FOM= 0.98 | TEST= 1 |
| INDE | 9 | 11 | 26 | FOBS= | 22.2 | SIGMA= | 2.9 | PHAS= | -10.9 | FOM= 0.87 | TEST= 0 |
| INDE | 9 | 11 | 28 | FOBS= | 56.3 | SIGMA= | 1.3 | PHAS= | -13.0 | FOM= 0.96 | TEST= 0 |
| INDE | 9 | 11 | 30 | FOBS= | 195.2 | SIGMA= | 0.6 | PHAS= | -98.8 | FOM= 0.97 | TEST= 0 |
| INDE | 9 | 11 | 32 | FOBS= | 32.5 | SIGMA= | 3.2 | PHAS= | -129.9 | FOM= 0.93 | TEST= 0 |
| INDE | 9 | 11 | 34 | FOBS= | 61.7 | SIGMA= | 2.0 | PHAS= | -64.4 | FOM= 0.96 | TEST= 0 |
| INDE | 9 | 11 | 36 | FOBS= | 223.2 | SIGMA= | 0.7 | PHAS= | 130.7 | FOM= 0.98 | TEST= 0 |
| INDE | 9 | 11 | 38 | FOBS= | 232.6 | SIGMA= | 0.8 | PHAS= | -133.5 | FOM= 0.95 | TEST= 0 |
| INDE | 9 | 11 | 40 | FOBS= | 185.1 | SIGMA= | 1.0 | PHAS= | 39.4 | FOM= 0.89 | TEST= 0 |
| INDE | 9 | 11 | 42 | FOBS= | 216.5 | SIGMA= | 1.0 | PHAS= | 121.6 | FOM= 0.40 | TEST= 1 |
| INDE | 9 | 11 | 44 | FOBS= | 284.8 | SIGMA= | 1.0 | PHAS= | 143.7 | FOM= 0.97 | TEST= 0 |
| INDE | 9 | 11 | 46 | FOBS= | 68.9 | SIGMA= | 3.1 | PHAS= | 94.5 | FOM= 0.52 | TEST= 0 |
| INDE | 9 | 11 | 48 | FOBS= | 64.3 | SIGMA= | 2.7 | PHAS= | -170.5 | FOM= 0.85 | TEST= 0 |
| INDE | 9 | 11 | 50 | FOBS= | 115.6 | SIGMA= | 1.3 | PHAS= | -39.3 | FOM= 0.96 | TEST= 0 |
| INDE | 9 | 11 | 52 | FOBS= | 15.0 | SIGMA= | 9.2 | PHAS= | 127.5 | FOM= 0.76 | TEST= 0 |
| INDE | 9 | 11 | 54 | FOBS= | 162.7 | SIGMA= | 1.0 | PHAS= | 120.1 | FOM= 0.92 | TEST= 0 |
| INDE | 9 | 11 | 56 | FOBS= | 134.2 | SIGMA= | 1.5 | PHAS= | 135.8 | FOM= 0.94 | TEST= 0 |
| INDE | 9 | 11 | 58 | FOBS= | 126.9 | SIGMA= | 2.1 | PHAS= | 117.6 | FOM= 0.90 | TEST= 0 |
| INDE | 9 | 11 | 60 | FOBS= | 0.0 | SIGMA= | 24.0 | PHAS= | 0.0 | FOM= 0.00 | TEST= 0 |
| INDE | 9 | 11 | 62 | FOBS= | 0.0 | SIGMA= | 23.7 | PHAS= | 0.0 | FOM= 0.00 | TEST= 0 |
| INDE | 9 | 11 | 64 | FOBS= | 30.9 | SIGMA= | 11.3 | PHAS= | -117.5 | FOM= 0.43 | TEST= 0 |

*FIG. 12A - 235*

```
INDE  9 11 66 FOBS=    0.0 SIGMA= 26.2 PHAS=    0.0 FOM= 0.00 TEST= 0
INDE  9 12 11 FOBS=  150.9 SIGMA=  0.5 PHAS=  140.1 FOM= 0.90 TEST= 0
INDE  9 12 13 FOBS=  270.3 SIGMA=  0.5 PHAS=  -60.3 FOM= 0.99 TEST= 0
INDE  9 12 15 FOBS=  168.9 SIGMA=  0.4 PHAS= -164.6 FOM= 0.89 TEST= 0
INDE  9 12 17 FOBS=  260.5 SIGMA=  0.4 PHAS=  130.1 FOM= 0.51 TEST= 1
INDE  9 12 19 FOBS=   87.8 SIGMA=  0.7 PHAS=   78.2 FOM= 0.88 TEST= 0
INDE  9 12 21 FOBS=   42.1 SIGMA=  1.4 PHAS=   61.0 FOM= 0.95 TEST= 0
INDE  9 12 23 FOBS=  176.0 SIGMA=  0.5 PHAS= -122.7 FOM= 0.99 TEST= 0
INDE  9 12 25 FOBS=  127.5 SIGMA=  0.6 PHAS= -160.7 FOM= 0.94 TEST= 0
INDE  9 12 27 FOBS=   70.6 SIGMA=  1.0 PHAS= -151.8 FOM= 0.98 TEST= 0
INDE  9 12 29 FOBS=  195.0 SIGMA=  0.5 PHAS=  142.1 FOM= 0.32 TEST= 1
INDE  9 12 31 FOBS=  167.1 SIGMA=  0.7 PHAS=  173.0 FOM= 0.98 TEST= 0
INDE  9 12 33 FOBS=   99.6 SIGMA=  1.1 PHAS=  -18.5 FOM= 0.87 TEST= 0
INDE  9 12 35 FOBS=  147.2 SIGMA=  1.0 PHAS=   96.4 FOM= 0.92 TEST= 1
INDE  9 12 37 FOBS=  235.7 SIGMA=  0.8 PHAS=  125.8 FOM= 0.99 TEST= 0
INDE  9 12 39 FOBS=  142.2 SIGMA=  1.0 PHAS=   19.4 FOM= 0.89 TEST= 0
INDE  9 12 41 FOBS=  298.5 SIGMA=  1.0 PHAS=  -92.8 FOM= 0.98 TEST= 0
INDE  9 12 43 FOBS=  230.5 SIGMA=  0.8 PHAS=    9.9 FOM= 0.93 TEST= 0
INDE  9 12 45 FOBS=  190.8 SIGMA=  0.8 PHAS=   78.6 FOM= 0.60 TEST= 1
INDE  9 12 47 FOBS=  150.5 SIGMA=  1.5 PHAS= -144.3 FOM= 0.63 TEST= 0
INDE  9 12 49 FOBS=  220.3 SIGMA=  0.9 PHAS= -130.6 FOM= 0.91 TEST= 0
INDE  9 12 51 FOBS=   59.0 SIGMA=  2.3 PHAS= -122.1 FOM= 0.53 TEST= 0
INDE  9 12 53 FOBS=   43.5 SIGMA=  3.0 PHAS=   98.2 FOM= 0.13 TEST= 0
INDE  9 12 55 FOBS=  265.1 SIGMA=  1.0 PHAS=    6.2 FOM= 0.96 TEST= 0
INDE  9 12 57 FOBS=   75.7 SIGMA=  2.6 PHAS=   61.0 FOM= 0.24 TEST= 1
INDE  9 12 59 FOBS=   66.2 SIGMA=  3.0 PHAS=  -74.0 FOM= 0.78 TEST= 1
INDE  9 12 61 FOBS=   41.0 SIGMA=  6.2 PHAS= -113.5 FOM= 0.74 TEST= 0
INDE  9 12 63 FOBS=   43.6 SIGMA=  6.5 PHAS=   60.7 FOM= 0.34 TEST= 0
INDE  9 12 65 FOBS=   86.5 SIGMA=  4.2 PHAS=   28.2 FOM= 0.58 TEST= 1
INDE  9 13 10 FOBS=  136.2 SIGMA=  0.5 PHAS=  176.6 FOM= 0.35 TEST= 0
INDE  9 13 12 FOBS=   84.7 SIGMA=  0.7 PHAS=  -44.4 FOM= 0.95 TEST= 0
INDE  9 13 14 FOBS=  146.4 SIGMA=  0.6 PHAS=  -41.9 FOM= 0.83 TEST= 0
INDE  9 13 16 FOBS=  228.9 SIGMA=  0.5 PHAS=  109.6 FOM= 0.90 TEST= 0
INDE  9 13 18 FOBS=   73.2 SIGMA=  0.8 PHAS=   30.9 FOM= 0.95 TEST= 0
INDE  9 13 20 FOBS=   13.7 SIGMA=  4.0 PHAS=  138.3 FOM= 0.89 TEST= 0
INDE  9 13 22 FOBS=  320.7 SIGMA=  0.4 PHAS=  105.7 FOM= 0.96 TEST= 0
INDE  9 13 24 FOBS=   76.4 SIGMA=  0.8 PHAS=  175.3 FOM= 0.94 TEST= 0
INDE  9 13 26 FOBS=  105.6 SIGMA=  0.6 PHAS=  101.0 FOM= 0.96 TEST= 0
INDE  9 13 28 FOBS=  193.9 SIGMA=  0.4 PHAS=   79.4 FOM= 0.99 TEST= 0
INDE  9 13 30 FOBS=   35.1 SIGMA=  2.1 PHAS=  108.8 FOM= 0.95 TEST= 0
INDE  9 13 32 FOBS=  258.4 SIGMA=  0.5 PHAS= -166.0 FOM= 0.94 TEST= 0
INDE  9 13 34 FOBS=  114.8 SIGMA=  0.8 PHAS= -111.7 FOM= 0.33 TEST= 0
INDE  9 13 36 FOBS=  328.4 SIGMA=  0.7 PHAS=   62.4 FOM= 0.99 TEST= 0
INDE  9 13 38 FOBS=  139.2 SIGMA=  0.9 PHAS= -153.7 FOM= 0.90 TEST= 0
INDE  9 13 40 FOBS=   56.8 SIGMA=  2.2 PHAS=   19.9 FOM= 0.80 TEST= 0
INDE  9 13 42 FOBS=  183.9 SIGMA=  0.9 PHAS= -123.5 FOM= 0.71 TEST= 0
INDE  9 13 44 FOBS=  220.7 SIGMA=  1.2 PHAS=  147.8 FOM= 0.91 TEST= 0
INDE  9 13 46 FOBS=  157.6 SIGMA=  1.2 PHAS= -138.5 FOM= 0.92 TEST= 0
INDE  9 13 48 FOBS=   65.5 SIGMA=  2.3 PHAS=  115.4 FOM= 0.82 TEST= 0
INDE  9 13 50 FOBS=   86.7 SIGMA=  1.7 PHAS= -178.1 FOM= 0.86 TEST= 0
INDE  9 13 52 FOBS=  150.7 SIGMA=  1.2 PHAS= -170.1 FOM= 0.97 TEST= 0
INDE  9 13 54 FOBS=  142.8 SIGMA=  1.1 PHAS=  -77.3 FOM= 0.94 TEST= 1
INDE  9 13 56 FOBS=   71.5 SIGMA=  2.8 PHAS=  -50.6 FOM= 0.73 TEST= 0
INDE  9 13 58 FOBS=   72.5 SIGMA=  2.8 PHAS=  132.0 FOM= 0.89 TEST= 0
INDE  9 13 60 FOBS=   61.8 SIGMA=  3.2 PHAS=   91.1 FOM= 0.63 TEST= 0
INDE  9 13 62 FOBS=   38.5 SIGMA=  4.9 PHAS=  -84.4 FOM= 0.50 TEST= 0
INDE  9 13 64 FOBS=  128.8 SIGMA=  2.9 PHAS=  -65.1 FOM= 0.93 TEST= 0
INDE  9 13 66 FOBS=   33.0 SIGMA= 15.0 PHAS= -175.7 FOM= 0.32 TEST= 0
INDE  9 14  9 FOBS=  242.8 SIGMA=  0.5 PHAS=  147.4 FOM= 0.96 TEST= 0
INDE  9 14 11 FOBS=  381.2 SIGMA=  0.5 PHAS=  105.0 FOM= 0.97 TEST= 0
INDE  9 14 13 FOBS=   93.3 SIGMA=  0.6 PHAS= -113.9 FOM= 0.83 TEST= 0
INDE  9 14 15 FOBS=  254.4 SIGMA=  0.5 PHAS= -171.6 FOM= 0.90 TEST= 0
INDE  9 14 17 FOBS=   81.3 SIGMA=  0.7 PHAS=   26.3 FOM= 0.64 TEST= 1
INDE  9 14 19 FOBS=   69.6 SIGMA=  0.9 PHAS=  -47.2 FOM= 0.91 TEST= 0
INDE  9 14 21 FOBS=  186.0 SIGMA=  0.4 PHAS=  -18.3 FOM= 0.92 TEST= 1
INDE  9 14 23 FOBS=  110.6 SIGMA=  0.6 PHAS=  -44.3 FOM= 0.06 TEST= 0
INDE  9 14 25 FOBS=  151.4 SIGMA=  0.5 PHAS=  -25.1 FOM= 0.99 TEST= 0
INDE  9 14 27 FOBS=   91.6 SIGMA=  0.7 PHAS=  -77.1 FOM= 0.93 TEST= 0
INDE  9 14 29 FOBS=  115.5 SIGMA=  0.7 PHAS=   61.3 FOM= 0.87 TEST= 0
INDE  9 14 31 FOBS=  303.0 SIGMA=  0.5 PHAS=  135.1 FOM= 0.94 TEST= 0
```

*FIG. 12A - 236*

```
INDE  9  14  33  FOBS=  173.5  SIGMA=   0.6  PHAS=  163.5  FOM=  0.93  TEST= 0
INDE  9  14  35  FOBS=  447.6  SIGMA=   0.6  PHAS=  -45.5  FOM=  0.98  TEST= 0
INDE  9  14  37  FOBS=  140.7  SIGMA=   1.0  PHAS=   53.8  FOM=  0.95  TEST= 0
INDE  9  14  39  FOBS=  147.2  SIGMA=   0.9  PHAS=  106.2  FOM=  0.95  TEST= 0
INDE  9  14  41  FOBS=  188.5  SIGMA=   1.0  PHAS= -116.9  FOM=  0.92  TEST= 0
INDE  9  14  43  FOBS=   80.2  SIGMA=   1.8  PHAS=   39.8  FOM=  0.53  TEST= 0
INDE  9  14  45  FOBS=  138.8  SIGMA=   1.1  PHAS=  116.3  FOM=  0.69  TEST= 1
INDE  9  14  47  FOBS=  266.2  SIGMA=   0.7  PHAS=  -56.1  FOM=  0.37  TEST= 1
INDE  9  14  49  FOBS=   62.1  SIGMA=   2.8  PHAS=  117.3  FOM=  0.85  TEST= 0
INDE  9  14  51  FOBS=  140.4  SIGMA=   1.2  PHAS=   85.2  FOM=  0.95  TEST= 0
INDE  9  14  53  FOBS=  147.2  SIGMA=   1.1  PHAS= -138.2  FOM=  0.81  TEST= 0
INDE  9  14  55  FOBS=   63.4  SIGMA=   3.2  PHAS=  -13.5  FOM=  0.07  TEST= 0
INDE  9  14  57  FOBS=   92.4  SIGMA=   2.2  PHAS=  119.3  FOM=  0.85  TEST= 1
INDE  9  14  59  FOBS=   99.2  SIGMA=   2.0  PHAS=  -52.6  FOM=  0.90  TEST= 0
INDE  9  14  61  FOBS=  117.1  SIGMA=   1.7  PHAS= -148.5  FOM=  0.96  TEST= 0
INDE  9  14  63  FOBS=   18.1  SIGMA=  15.0  PHAS=   50.4  FOM=  0.30  TEST= 0
INDE  9  14  65  FOBS=  130.5  SIGMA=   2.2  PHAS= -167.4  FOM=  0.19  TEST= 1
INDE  9  15  10  FOBS=  182.4  SIGMA=   0.4  PHAS=  -34.5  FOM=  0.91  TEST= 0
INDE  9  15  12  FOBS=  226.2  SIGMA=   0.5  PHAS=  -39.7  FOM=  0.91  TEST= 0
INDE  9  15  14  FOBS=  268.0  SIGMA=   0.5  PHAS=   87.7  FOM=  0.94  TEST= 0
INDE  9  15  16  FOBS=   49.2  SIGMA=   1.3  PHAS=   34.4  FOM=  0.43  TEST= 0
INDE  9  15  18  FOBS=   40.6  SIGMA=   1.4  PHAS=  159.0  FOM=  0.35  TEST= 0
INDE  9  15  20  FOBS=   87.2  SIGMA=   0.7  PHAS= -119.0  FOM=  0.99  TEST= 0
INDE  9  15  22  FOBS=   30.2  SIGMA=   2.1  PHAS=   97.4  FOM=  0.90  TEST= 0
INDE  9  15  24  FOBS=  175.4  SIGMA=   0.4  PHAS= -153.6  FOM=  0.87  TEST= 0
INDE  9  15  26  FOBS=   72.1  SIGMA=   0.9  PHAS= -168.6  FOM=  0.88  TEST= 0
INDE  9  15  28  FOBS=  200.8  SIGMA=   0.5  PHAS=   44.5  FOM=  0.94  TEST= 0
INDE  9  15  30  FOBS=  239.7  SIGMA=   0.4  PHAS=   97.6  FOM=  0.96  TEST= 0
INDE  9  15  32  FOBS=  116.5  SIGMA=   0.8  PHAS=    6.1  FOM=  0.73  TEST= 0
INDE  9  15  34  FOBS=   16.0  SIGMA=   6.1  PHAS= -172.4  FOM=  0.02  TEST= 1
INDE  9  15  36  FOBS=  170.2  SIGMA=   0.6  PHAS= -165.6  FOM=  0.92  TEST= 0
INDE  9  15  38  FOBS=  165.4  SIGMA=   0.7  PHAS=   26.1  FOM=  0.85  TEST= 0
INDE  9  15  40  FOBS=   27.7  SIGMA=   4.4  PHAS=  -56.3  FOM=  0.07  TEST= 0
INDE  9  15  42  FOBS=  330.3  SIGMA=   1.0  PHAS=  -78.7  FOM=  0.92  TEST= 0
INDE  9  15  44  FOBS=  158.8  SIGMA=   1.0  PHAS=  -15.5  FOM=  0.85  TEST= 0
INDE  9  15  46  FOBS=  279.3  SIGMA=   1.0  PHAS= -137.7  FOM=  0.95  TEST= 0
INDE  9  15  48  FOBS=  128.1  SIGMA=   1.2  PHAS=   40.4  FOM=  0.86  TEST= 0
INDE  9  15  50  FOBS=   94.7  SIGMA=   1.5  PHAS=  -51.7  FOM=  0.96  TEST= 0
INDE  9  15  52  FOBS=   88.3  SIGMA=   1.8  PHAS=  179.7  FOM=  0.91  TEST= 0
INDE  9  15  54  FOBS=  105.6  SIGMA=   2.0  PHAS= -125.0  FOM=  0.78  TEST= 0
INDE  9  15  56  FOBS=   58.1  SIGMA=   3.5  PHAS=   17.2  FOM=  0.90  TEST= 1
INDE  9  15  58  FOBS=   78.2  SIGMA=   2.6  PHAS=   87.9  FOM=  0.84  TEST= 0
INDE  9  15  60  FOBS=  164.5  SIGMA=   1.3  PHAS=  117.0  FOM=  0.97  TEST= 0
INDE  9  15  62  FOBS=   36.1  SIGMA=   5.4  PHAS=   82.8  FOM=  0.82  TEST= 0
INDE  9  15  64  FOBS=   49.8  SIGMA=   5.7  PHAS=   58.6  FOM=  0.38  TEST= 0
INDE  9  15  66  FOBS=  132.4  SIGMA=   3.6  PHAS=   93.2  FOM=  0.95  TEST= 0
INDE  9  15  68  FOBS=   47.8  SIGMA=   9.6  PHAS=   61.9  FOM=  0.68  TEST= 0
INDE  9  16   9  FOBS=  263.7  SIGMA=   0.5  PHAS=  -87.5  FOM=  0.85  TEST= 0
INDE  9  16  11  FOBS=  130.6  SIGMA=   0.5  PHAS=  141.6  FOM=  0.81  TEST= 0
INDE  9  16  13  FOBS=  136.8  SIGMA=   0.5  PHAS= -119.6  FOM=  0.74  TEST= 0
INDE  9  16  15  FOBS=  147.1  SIGMA=   0.6  PHAS=    6.1  FOM=  0.84  TEST= 0
INDE  9  16  17  FOBS=  106.7  SIGMA=   0.7  PHAS= -159.2  FOM=  0.80  TEST= 0
INDE  9  16  19  FOBS=  100.5  SIGMA=   0.7  PHAS=  -14.1  FOM=  0.99  TEST= 0
INDE  9  16  21  FOBS=  111.3  SIGMA=   0.6  PHAS=   37.7  FOM=  0.99  TEST= 0
INDE  9  16  23  FOBS=  230.4  SIGMA=   0.4  PHAS= -126.5  FOM=  0.99  TEST= 0
INDE  9  16  25  FOBS=  176.3  SIGMA=   0.5  PHAS=   31.1  FOM=  0.97  TEST= 0
INDE  9  16  27  FOBS=  160.2  SIGMA=   0.5  PHAS=  173.7  FOM=  0.99  TEST= 0
INDE  9  16  29  FOBS=  142.5  SIGMA=   0.6  PHAS=  -25.4  FOM=  0.90  TEST= 0
INDE  9  16  31  FOBS=  157.9  SIGMA=   0.6  PHAS=   22.7  FOM=  0.97  TEST= 0
INDE  9  16  33  FOBS=  205.9  SIGMA=   0.5  PHAS=  174.6  FOM=  0.95  TEST= 0
INDE  9  16  35  FOBS=  285.6  SIGMA=   0.5  PHAS=   34.5  FOM=  0.93  TEST= 0
INDE  9  16  37  FOBS=  317.3  SIGMA=   0.5  PHAS=  -37.9  FOM=  0.96  TEST= 0
INDE  9  16  39  FOBS=  118.5  SIGMA=   1.0  PHAS= -156.5  FOM=  0.93  TEST= 0
INDE  9  16  41  FOBS=  102.2  SIGMA=   1.3  PHAS=  148.5  FOM=  0.82  TEST= 0
INDE  9  16  43  FOBS=  260.5  SIGMA=   0.8  PHAS= -175.5  FOM=  0.92  TEST= 0
INDE  9  16  45  FOBS=  101.8  SIGMA=   1.6  PHAS= -160.0  FOM=  0.93  TEST= 0
INDE  9  16  47  FOBS=  180.9  SIGMA=   0.9  PHAS=  -30.4  FOM=  0.66  TEST= 1
INDE  9  16  49  FOBS=  127.4  SIGMA=   1.2  PHAS=   65.7  FOM=  0.95  TEST= 0
INDE  9  16  51  FOBS=   87.5  SIGMA=   1.9  PHAS=  -95.6  FOM=  0.70  TEST= 0
INDE  9  16  53  FOBS=   61.8  SIGMA=   3.3  PHAS= -115.4  FOM=  0.35  TEST= 0
```

*FIG. 12A - 237*

| | | | | | | | | | | | | |
|---|---|---|---|---|---|---|---|---|---|---|---|---|
| INDE | 9 | 16 | 55 | FOBS= | 141.1 | SIGMA= | 1.5 | PHAS= | -110.9 | FOM= | 0.89 | TEST= 0 |
| INDE | 9 | 16 | 57 | FOBS= | 133.3 | SIGMA= | 1.6 | PHAS= | -11.8 | FOM= | 0.93 | TEST= 0 |
| INDE | 9 | 16 | 59 | FOBS= | 121.9 | SIGMA= | 1.7 | PHAS= | -26.2 | FOM= | 0.95 | TEST= 0 |
| INDE | 9 | 16 | 61 | FOBS= | 150.1 | SIGMA= | 1.4 | PHAS= | -42.6 | FOM= | 0.97 | TEST= 0 |
| INDE | 9 | 16 | 63 | FOBS= | 3.7 | SIGMA= | 74.3 | PHAS= | 40.3 | FOM= | 0.05 | TEST= 0 |
| INDE | 9 | 16 | 65 | FOBS= | 0.0 | SIGMA= | 25.7 | PHAS= | 0.0 | FOM= | 0.00 | TEST= 0 |
| INDE | 9 | 16 | 67 | FOBS= | 110.7 | SIGMA= | 4.3 | PHAS= | -25.0 | FOM= | 0.90 | TEST= 0 |
| INDE | 9 | 16 | 69 | FOBS= | 73.8 | SIGMA= | 6.3 | PHAS= | -171.8 | FOM= | 0.07 | TEST= 1 |
| INDE | 9 | 16 | 71 | FOBS= | 70.6 | SIGMA= | 6.7 | PHAS= | -4.4 | FOM= | 0.67 | TEST= 0 |
| INDE | 9 | 17 | 10 | FOBS= | 181.5 | SIGMA= | 0.4 | PHAS= | -81.5 | FOM= | 0.91 | TEST= 0 |
| INDE | 9 | 17 | 12 | FOBS= | 21.2 | SIGMA= | 2.7 | PHAS= | -158.4 | FOM= | 0.47 | TEST= 1 |
| INDE | 9 | 17 | 14 | FOBS= | 135.7 | SIGMA= | 0.5 | PHAS= | 153.6 | FOM= | 0.93 | TEST= 0 |
| INDE | 9 | 17 | 16 | FOBS= | 59.7 | SIGMA= | 1.1 | PHAS= | -78.3 | FOM= | 0.89 | TEST= 0 |
| INDE | 9 | 17 | 18 | FOBS= | 169.1 | SIGMA= | 0.5 | PHAS= | 124.9 | FOM= | 0.97 | TEST= 0 |
| INDE | 9 | 17 | 20 | FOBS= | 54.2 | SIGMA= | 1.2 | PHAS= | -115.0 | FOM= | 0.93 | TEST= 0 |
| INDE | 9 | 17 | 22 | FOBS= | 147.5 | SIGMA= | 0.5 | PHAS= | 124.7 | FOM= | 0.99 | TEST= 0 |
| INDE | 9 | 17 | 24 | FOBS= | 133.2 | SIGMA= | 0.7 | PHAS= | -104.8 | FOM= | 0.94 | TEST= 1 |
| INDE | 9 | 17 | 26 | FOBS= | 82.3 | SIGMA= | 0.9 | PHAS= | 97.8 | FOM= | 0.98 | TEST= 0 |
| INDE | 9 | 17 | 28 | FOBS= | 209.4 | SIGMA= | 0.5 | PHAS= | 49.6 | FOM= | 0.97 | TEST= 0 |
| INDE | 9 | 17 | 30 | FOBS= | 58.3 | SIGMA= | 1.4 | PHAS= | 170.5 | FOM= | 0.96 | TEST= 0 |
| INDE | 9 | 17 | 32 | FOBS= | 99.2 | SIGMA= | 0.9 | PHAS= | -171.0 | FOM= | 0.93 | TEST= 0 |
| INDE | 9 | 17 | 34 | FOBS= | 200.3 | SIGMA= | 0.7 | PHAS= | 70.5 | FOM= | 0.92 | TEST= 0 |
| INDE | 9 | 17 | 36 | FOBS= | 505.0 | SIGMA= | 0.5 | PHAS= | -134.8 | FOM= | 0.98 | TEST= 0 |
| INDE | 9 | 17 | 38 | FOBS= | 90.7 | SIGMA= | 1.2 | PHAS= | -10.8 | FOM= | 0.43 | TEST= 0 |
| INDE | 9 | 17 | 40 | FOBS= | 74.6 | SIGMA= | 1.6 | PHAS= | -70.8 | FOM= | 0.89 | TEST= 0 |
| INDE | 9 | 17 | 42 | FOBS= | 41.9 | SIGMA= | 3.3 | PHAS= | 5.2 | FOM= | 0.62 | TEST= 0 |
| INDE | 9 | 17 | 44 | FOBS= | 243.3 | SIGMA= | 0.8 | PHAS= | 103.9 | FOM= | 0.90 | TEST= 0 |
| INDE | 9 | 17 | 46 | FOBS= | 205.3 | SIGMA= | 0.8 | PHAS= | -22.8 | FOM= | 0.95 | TEST= 0 |
| INDE | 9 | 17 | 48 | FOBS= | 127.9 | SIGMA= | 1.4 | PHAS= | -59.2 | FOM= | 0.91 | TEST= 0 |
| INDE | 9 | 17 | 50 | FOBS= | 43.2 | SIGMA= | 4.8 | PHAS= | -76.7 | FOM= | 0.79 | TEST= 0 |
| INDE | 9 | 17 | 52 | FOBS= | 91.8 | SIGMA= | 2.3 | PHAS= | 175.1 | FOM= | 0.72 | TEST= 0 |
| INDE | 9 | 17 | 54 | FOBS= | 149.7 | SIGMA= | 1.5 | PHAS= | 164.2 | FOM= | 0.95 | TEST= 0 |
| INDE | 9 | 17 | 56 | FOBS= | 150.9 | SIGMA= | 1.4 | PHAS= | -165.8 | FOM= | 0.95 | TEST= 0 |
| INDE | 9 | 17 | 58 | FOBS= | 0.0 | SIGMA= | 21.1 | PHAS= | 0.0 | FOM= | 0.00 | TEST= 0 |
| INDE | 9 | 17 | 60 | FOBS= | 100.0 | SIGMA= | 2.1 | PHAS= | -144.5 | FOM= | 0.94 | TEST= 0 |
| INDE | 9 | 17 | 62 | FOBS= | 43.9 | SIGMA= | 5.4 | PHAS= | -119.2 | FOM= | 0.53 | TEST= 0 |
| INDE | 9 | 17 | 64 | FOBS= | 114.0 | SIGMA= | 2.5 | PHAS= | 41.8 | FOM= | 0.93 | TEST= 0 |
| INDE | 9 | 17 | 66 | FOBS= | 51.6 | SIGMA= | 9.1 | PHAS= | -41.5 | FOM= | 0.13 | TEST= 1 |
| INDE | 9 | 17 | 68 | FOBS= | 55.4 | SIGMA= | 8.5 | PHAS= | 148.8 | FOM= | 0.59 | TEST= 0 |
| INDE | 9 | 17 | 70 | FOBS= | 23.9 | SIGMA= | 19.5 | PHAS= | 126.8 | FOM= | 0.32 | TEST= 0 |
| INDE | 9 | 17 | 72 | FOBS= | 0.0 | SIGMA= | 30.8 | PHAS= | 0.0 | FOM= | 0.00 | TEST= 0 |
| INDE | 9 | 18 | 9 | FOBS= | 135.2 | SIGMA= | 0.5 | PHAS= | -6.2 | FOM= | 0.83 | TEST= 0 |
| INDE | 9 | 18 | 11 | FOBS= | 136.7 | SIGMA= | 0.5 | PHAS= | 140.6 | FOM= | 0.94 | TEST= 0 |
| INDE | 9 | 18 | 13 | FOBS= | 146.8 | SIGMA= | 0.5 | PHAS= | 38.7 | FOM= | 0.75 | TEST= 0 |
| INDE | 9 | 18 | 15 | FOBS= | 176.9 | SIGMA= | 0.6 | PHAS= | 48.2 | FOM= | 0.94 | TEST= 0 |
| INDE | 9 | 18 | 17 | FOBS= | 116.3 | SIGMA= | 0.6 | PHAS= | 59.7 | FOM= | 0.98 | TEST= 0 |
| INDE | 9 | 18 | 19 | FOBS= | 164.9 | SIGMA= | 0.5 | PHAS= | 60.8 | FOM= | 0.84 | TEST= 0 |
| INDE | 9 | 18 | 21 | FOBS= | 201.6 | SIGMA= | 0.5 | PHAS= | 78.5 | FOM= | 0.94 | TEST= 0 |
| INDE | 9 | 18 | 23 | FOBS= | 221.8 | SIGMA= | 0.5 | PHAS= | -114.5 | FOM= | 0.98 | TEST= 0 |
| INDE | 9 | 18 | 25 | FOBS= | 105.7 | SIGMA= | 0.8 | PHAS= | -54.5 | FOM= | 0.94 | TEST= 0 |
| INDE | 9 | 18 | 27 | FOBS= | 81.0 | SIGMA= | 1.0 | PHAS= | 23.6 | FOM= | 0.99 | TEST= 0 |
| INDE | 9 | 18 | 29 | FOBS= | 114.1 | SIGMA= | 0.8 | PHAS= | -138.0 | FOM= | 0.79 | TEST= 0 |
| INDE | 9 | 18 | 31 | FOBS= | 259.2 | SIGMA= | 0.5 | PHAS= | 41.4 | FOM= | 0.97 | TEST= 0 |
| INDE | 9 | 18 | 33 | FOBS= | 207.6 | SIGMA= | 0.6 | PHAS= | 51.2 | FOM= | 0.98 | TEST= 0 |
| INDE | 9 | 18 | 35 | FOBS= | 329.0 | SIGMA= | 0.5 | PHAS= | -174.7 | FOM= | 0.96 | TEST= 0 |
| INDE | 9 | 18 | 37 | FOBS= | 242.2 | SIGMA= | 0.6 | PHAS= | -144.5 | FOM= | 0.34 | TEST= 1 |
| INDE | 9 | 18 | 39 | FOBS= | 199.3 | SIGMA= | 0.7 | PHAS= | -170.7 | FOM= | 0.03 | TEST= 1 |
| INDE | 9 | 18 | 41 | FOBS= | 130.5 | SIGMA= | 1.0 | PHAS= | 164.6 | FOM= | 0.63 | TEST= 0 |
| INDE | 9 | 18 | 43 | FOBS= | 90.2 | SIGMA= | 1.7 | PHAS= | 70.9 | FOM= | 0.88 | TEST= 0 |
| INDE | 9 | 18 | 45 | FOBS= | 220.0 | SIGMA= | 0.8 | PHAS= | -109.3 | FOM= | 0.49 | TEST= 1 |
| INDE | 9 | 18 | 47 | FOBS= | 342.1 | SIGMA= | 0.7 | PHAS= | -56.4 | FOM= | 0.86 | TEST= 1 |
| INDE | 9 | 18 | 49 | FOBS= | 299.6 | SIGMA= | 0.9 | PHAS= | 92.2 | FOM= | 0.98 | TEST= 0 |
| INDE | 9 | 18 | 51 | FOBS= | 85.0 | SIGMA= | 2.5 | PHAS= | -52.6 | FOM= | 0.94 | TEST= 0 |
| INDE | 9 | 18 | 53 | FOBS= | 36.9 | SIGMA= | 5.6 | PHAS= | -32.2 | FOM= | 0.25 | TEST= 0 |
| INDE | 9 | 18 | 55 | FOBS= | 97.3 | SIGMA= | 2.1 | PHAS= | 70.0 | FOM= | 0.94 | TEST= 0 |
| INDE | 9 | 18 | 57 | FOBS= | 152.7 | SIGMA= | 1.4 | PHAS= | 18.9 | FOM= | 0.95 | TEST= 0 |
| INDE | 9 | 18 | 59 | FOBS= | 0.0 | SIGMA= | 21.0 | PHAS= | 0.0 | FOM= | 0.00 | TEST= 0 |
| INDE | 9 | 18 | 61 | FOBS= | 91.8 | SIGMA= | 2.6 | PHAS= | -67.0 | FOM= | 0.87 | TEST= 0 |
| INDE | 9 | 18 | 63 | FOBS= | 17.7 | SIGMA= | 13.4 | PHAS= | 41.3 | FOM= | 0.29 | TEST= 0 |
| INDE | 9 | 18 | 65 | FOBS= | 108.8 | SIGMA= | 3.2 | PHAS= | -46.1 | FOM= | 0.92 | TEST= 0 |

*FIG. 12A - 238*

| | | | | | | | | | | | |
|---|---|---|---|---|---|---|---|---|---|---|---|
| INDE | 9 | 18 | 67 | FOBS= | 43.7 | SIGMA= | 10.4 | PHAS= | -64.4 | FOM= | 0.14 | TEST= 1
| INDE | 9 | 18 | 69 | FOBS= | 47.9 | SIGMA= | 9.7 | PHAS= | -17.4 | FOM= | 0.04 | TEST= 1
| INDE | 9 | 18 | 71 | FOBS= | 0.0 | SIGMA= | 30.6 | PHAS= | 0.0 | FOM= | 0.00 | TEST= 0
| INDE | 9 | 18 | 73 | FOBS= | 54.1 | SIGMA= | 9.1 | PHAS= | -62.6 | FOM= | 0.54 | TEST= 0
| INDE | 9 | 18 | 75 | FOBS= | 101.7 | SIGMA= | 5.1 | PHAS= | 47.6 | FOM= | 0.79 | TEST= 0
| INDE | 9 | 19 | 10 | FOBS= | 30.7 | SIGMA= | 1.7 | PHAS= | -2.7 | FOM= | 0.94 | TEST= 0
| INDE | 9 | 19 | 12 | FOBS= | 104.2 | SIGMA= | 0.6 | PHAS= | 112.3 | FOM= | 0.95 | TEST= 0
| INDE | 9 | 19 | 14 | FOBS= | 258.5 | SIGMA= | 0.5 | PHAS= | -48.6 | FOM= | 0.96 | TEST= 0
| INDE | 9 | 19 | 16 | FOBS= | 280.1 | SIGMA= | 0.6 | PHAS= | -42.7 | FOM= | 0.99 | TEST= 0
| INDE | 9 | 19 | 18 | FOBS= | 170.2 | SIGMA= | 0.5 | PHAS= | -10.7 | FOM= | 0.99 | TEST= 0
| INDE | 9 | 19 | 20 | FOBS= | 262.9 | SIGMA= | 0.5 | PHAS= | -23.1 | FOM= | 0.96 | TEST= 0
| INDE | 9 | 19 | 22 | FOBS= | 125.2 | SIGMA= | 0.8 | PHAS= | 67.6 | FOM= | 0.95 | TEST= 0
| INDE | 9 | 19 | 24 | FOBS= | 193.8 | SIGMA= | 0.5 | PHAS= | 172.4 | FOM= | 0.95 | TEST= 0
| INDE | 9 | 19 | 26 | FOBS= | 77.2 | SIGMA= | 1.1 | PHAS= | -83.0 | FOM= | 0.53 | TEST= 0
| INDE | 9 | 19 | 28 | FOBS= | 233.4 | SIGMA= | 0.5 | PHAS= | 4.5 | FOM= | 0.87 | TEST= 0
| INDE | 9 | 19 | 30 | FOBS= | 166.4 | SIGMA= | 0.6 | PHAS= | 57.3 | FOM= | 0.98 | TEST= 0
| INDE | 9 | 19 | 32 | FOBS= | 246.8 | SIGMA= | 0.5 | PHAS= | -103.6 | FOM= | 0.97 | TEST= 0
| INDE | 9 | 19 | 34 | FOBS= | 224.1 | SIGMA= | 0.6 | PHAS= | 37.1 | FOM= | 0.90 | TEST= 0
| INDE | 9 | 19 | 36 | FOBS= | 328.3 | SIGMA= | 0.5 | PHAS= | 135.2 | FOM= | 0.96 | TEST= 0
| INDE | 9 | 19 | 38 | FOBS= | 251.4 | SIGMA= | 0.6 | PHAS= | 89.3 | FOM= | 0.95 | TEST= 0
| INDE | 9 | 19 | 40 | FOBS= | 306.5 | SIGMA= | 0.7 | PHAS= | -47.6 | FOM= | 0.96 | TEST= 0
| INDE | 9 | 19 | 42 | FOBS= | 117.6 | SIGMA= | 1.2 | PHAS= | 51.3 | FOM= | 0.88 | TEST= 0
| INDE | 9 | 19 | 44 | FOBS= | 126.7 | SIGMA= | 1.2 | PHAS= | -102.7 | FOM= | 0.86 | TEST= 0
| INDE | 9 | 19 | 46 | FOBS= | 273.4 | SIGMA= | 0.8 | PHAS= | -103.8 | FOM= | 0.98 | TEST= 0
| INDE | 9 | 19 | 48 | FOBS= | 152.3 | SIGMA= | 1.5 | PHAS= | -42.4 | FOM= | 0.96 | TEST= 0
| INDE | 9 | 19 | 50 | FOBS= | 89.8 | SIGMA= | 2.4 | PHAS= | 5.8 | FOM= | 0.68 | TEST= 1
| INDE | 9 | 19 | 52 | FOBS= | 92.8 | SIGMA= | 2.3 | PHAS= | 111.9 | FOM= | 0.51 | TEST= 0
| INDE | 9 | 19 | 54 | FOBS= | 142.1 | SIGMA= | 1.0 | PHAS= | -146.4 | FOM= | 0.91 | TEST= 0
| INDE | 9 | 19 | 56 | FOBS= | 174.5 | SIGMA= | 1.3 | PHAS= | -112.6 | FOM= | 0.97 | TEST= 0
| INDE | 9 | 19 | 58 | FOBS= | 0.0 | SIGMA= | 20.9 | PHAS= | 0.0 | FOM= | 0.00 | TEST= 0
| INDE | 9 | 19 | 60 | FOBS= | 85.2 | SIGMA= | 2.4 | PHAS= | -172.4 | FOM= | 0.90 | TEST= 0
| INDE | 9 | 19 | 62 | FOBS= | 57.4 | SIGMA= | 4.1 | PHAS= | -156.6 | FOM= | 0.19 | TEST= 0
| INDE | 9 | 19 | 64 | FOBS= | 0.0 | SIGMA= | 26.4 | PHAS= | 0.0 | FOM= | 0.00 | TEST= 0
| INDE | 9 | 19 | 68 | FOBS= | 0.0 | SIGMA= | 30.0 | PHAS= | 0.0 | FOM= | 0.00 | TEST= 0
| INDE | 9 | 19 | 70 | FOBS= | 11.3 | SIGMA= | 41.4 | PHAS= | 20.1 | FOM= | 0.05 | TEST= 0
| INDE | 9 | 19 | 72 | FOBS= | 69.0 | SIGMA= | 7.1 | PHAS= | -152.7 | FOM= | 0.84 | TEST= 0
| INDE | 9 | 19 | 74 | FOBS= | 55.6 | SIGMA= | 9.1 | PHAS= | -20.3 | FOM= | 0.05 | TEST= 1
| INDE | 9 | 20 | 9 | FOBS= | 141.9 | SIGMA= | 0.5 | PHAS= | 53.3 | FOM= | 0.93 | TEST= 0
| INDE | 9 | 20 | 11 | FOBS= | 177.3 | SIGMA= | 0.5 | PHAS= | 13.6 | FOM= | 0.99 | TEST= 0
| INDE | 9 | 20 | 13 | FOBS= | 124.7 | SIGMA= | 0.6 | PHAS= | 151.9 | FOM= | 0.99 | TEST= 0
| INDE | 9 | 20 | 15 | FOBS= | 203.0 | SIGMA= | 0.5 | PHAS= | -157.3 | FOM= | 0.97 | TEST= 0
| INDE | 9 | 20 | 17 | FOBS= | 80.4 | SIGMA= | 0.9 | PHAS= | -119.3 | FOM= | 0.99 | TEST= 0
| INDE | 9 | 20 | 19 | FOBS= | 223.0 | SIGMA= | 0.5 | PHAS= | -102.4 | FOM= | 0.99 | TEST= 0
| INDE | 9 | 20 | 21 | FOBS= | 223.1 | SIGMA= | 0.5 | PHAS= | -82.5 | FOM= | 0.99 | TEST= 0
| INDE | 9 | 20 | 23 | FOBS= | 121.0 | SIGMA= | 0.8 | PHAS= | 22.3 | FOM= | 0.99 | TEST= 0
| INDE | 9 | 20 | 25 | FOBS= | 109.2 | SIGMA= | 0.8 | PHAS= | -15.9 | FOM= | 0.95 | TEST= 0
| INDE | 9 | 20 | 27 | FOBS= | 347.8 | SIGMA= | 0.5 | PHAS= | -5.3 | FOM= | 0.98 | TEST= 0
| INDE | 9 | 20 | 29 | FOBS= | 59.3 | SIGMA= | 1.6 | PHAS= | -161.7 | FOM= | 0.55 | TEST= 0
| INDE | 9 | 20 | 31 | FOBS= | 209.9 | SIGMA= | 0.5 | PHAS= | 15.1 | FOM= | 0.93 | TEST= 0
| INDE | 9 | 20 | 33 | FOBS= | 314.9 | SIGMA= | 0.5 | PHAS= | 71.8 | FOM= | 0.96 | TEST= 0
| INDE | 9 | 20 | 35 | FOBS= | 0.0 | SIGMA= | 14.6 | PHAS= | 0.0 | FOM= | 0.00 | TEST= 0
| INDE | 9 | 20 | 37 | FOBS= | 382.6 | SIGMA= | 0.6 | PHAS= | 27.5 | FOM= | 0.97 | TEST= 0
| INDE | 9 | 20 | 39 | FOBS= | 231.0 | SIGMA= | 0.7 | PHAS= | -147.8 | FOM= | 0.96 | TEST= 0
| INDE | 9 | 20 | 41 | FOBS= | 168.8 | SIGMA= | 1.0 | PHAS= | 165.8 | FOM= | 0.94 | TEST= 0
| INDE | 9 | 20 | 43 | FOBS= | 18.5 | SIGMA= | 7.8 | PHAS= | 130.7 | FOM= | 0.15 | TEST= 0
| INDE | 9 | 20 | 45 | FOBS= | 371.4 | SIGMA= | 0.7 | PHAS= | -165.2 | FOM= | 0.98 | TEST= 0
| INDE | 9 | 20 | 47 | FOBS= | 200.3 | SIGMA= | 1.1 | PHAS= | -156.0 | FOM= | 0.97 | TEST= 0
| INDE | 9 | 20 | 49 | FOBS= | 113.7 | SIGMA= | 2.0 | PHAS= | 56.7 | FOM= | 0.84 | TEST= 0
| INDE | 9 | 20 | 51 | FOBS= | 106.3 | SIGMA= | 2.0 | PHAS= | -4.6 | FOM= | 0.80 | TEST= 0
| INDE | 9 | 20 | 53 | FOBS= | 44.8 | SIGMA= | 4.6 | PHAS= | -176.5 | FOM= | 0.32 | TEST= 0
| INDE | 9 | 20 | 55 | FOBS= | 68.7 | SIGMA= | 2.0 | PHAS= | 59.9 | FOM= | 0.71 | TEST= 0
| INDE | 9 | 20 | 57 | FOBS= | 28.1 | SIGMA= | 7.2 | PHAS= | -141.0 | FOM= | 0.42 | TEST= 0
| INDE | 9 | 20 | 59 | FOBS= | 73.3 | SIGMA= | 2.8 | PHAS= | 110.2 | FOM= | 0.84 | TEST= 0
| INDE | 9 | 20 | 61 | FOBS= | 90.7 | SIGMA= | 2.6 | PHAS= | 8.6 | FOM= | 0.91 | TEST= 0
| INDE | 9 | 20 | 63 | FOBS= | 76.8 | SIGMA= | 3.1 | PHAS= | -1.3 | FOM= | 0.88 | TEST= 0
| INDE | 9 | 20 | 65 | FOBS= | 113.8 | SIGMA= | 4.1 | PHAS= | -167.4 | FOM= | 0.87 | TEST= 0
| INDE | 9 | 20 | 67 | FOBS= | 102.6 | SIGMA= | 4.5 | PHAS= | 53.3 | FOM= | 0.94 | TEST= 0
| INDE | 9 | 20 | 69 | FOBS= | 63.0 | SIGMA= | 7.4 | PHAS= | -4.1 | FOM= | 0.84 | TEST= 0
| INDE | 9 | 20 | 71 | FOBS= | 60.2 | SIGMA= | 8.0 | PHAS= | 135.7 | FOM= | 0.87 | TEST= 0
| INDE | 9 | 20 | 73 | FOBS= | 34.1 | SIGMA= | 14.7 | PHAS= | 9.9 | FOM= | 0.54 | TEST= 0

*FIG. 12A - 239*

```
INDE  9 21 10 FOBS=  164.7 SIGMA=   0.5 PHAS= -111.0 FOM= 0.96 TEST= 0
INDE  9 21 12 FOBS=   74.6 SIGMA=   0.9 PHAS= -153.5 FOM= 0.91 TEST= 0
INDE  9 21 14 FOBS=  141.5 SIGMA=   0.6 PHAS=   18.4 FOM= 0.99 TEST= 0
INDE  9 21 16 FOBS=   76.0 SIGMA=   1.0 PHAS= -158.9 FOM= 0.74 TEST= 0
INDE  9 21 18 FOBS=  122.5 SIGMA=   0.7 PHAS=  -48.3 FOM= 0.99 TEST= 0
INDE  9 21 20 FOBS=  146.2 SIGMA=   0.7 PHAS=  112.2 FOM= 0.99 TEST= 0
INDE  9 21 22 FOBS=   72.1 SIGMA=   1.1 PHAS=  -99.1 FOM= 0.93 TEST= 0
INDE  9 21 24 FOBS=  274.5 SIGMA=   0.5 PHAS=  -76.8 FOM= 0.94 TEST= 0
INDE  9 21 26 FOBS=  336.5 SIGMA=   0.5 PHAS= -109.6 FOM= 0.97 TEST= 0
INDE  9 21 28 FOBS=  216.9 SIGMA=   0.6 PHAS=  -71.5 FOM= 0.95 TEST= 0
INDE  9 21 30 FOBS=  130.1 SIGMA=   0.8 PHAS=  -40.5 FOM= 0.54 TEST= 0
INDE  9 21 32 FOBS=  282.0 SIGMA=   0.5 PHAS=  -81.9 FOM= 0.98 TEST= 0
INDE  9 21 34 FOBS=  335.1 SIGMA=   0.5 PHAS=  -68.4 FOM= 0.97 TEST= 0
INDE  9 21 36 FOBS=  209.3 SIGMA=   0.7 PHAS= -102.5 FOM= 0.93 TEST= 0
INDE  9 21 38 FOBS=   71.2 SIGMA=   1.8 PHAS=  144.0 FOM= 0.82 TEST= 0
INDE  9 21 40 FOBS=  155.5 SIGMA=   1.0 PHAS=   69.6 FOM= 0.96 TEST= 0
INDE  9 21 42 FOBS=  119.5 SIGMA=   1.4 PHAS=   72.1 FOM= 0.88 TEST= 1
INDE  9 21 44 FOBS=    0.0 SIGMA=  20.0 PHAS=    0.0 FOM= 0.00 TEST= 0
INDE  9 21 46 FOBS=  122.6 SIGMA=   1.5 PHAS=  102.6 FOM= 0.86 TEST= 1
INDE  9 21 48 FOBS=   97.9 SIGMA=   2.0 PHAS=   31.2 FOM= 0.67 TEST= 0
INDE  9 21 50 FOBS=  142.6 SIGMA=   1.4 PHAS=  -51.3 FOM= 0.88 TEST= 0
INDE  9 21 52 FOBS=   63.7 SIGMA=   3.3 PHAS=  143.0 FOM= 0.78 TEST= 0
INDE  9 21 54 FOBS=   36.5 SIGMA=   4.3 PHAS=  171.2 FOM= 0.41 TEST= 0
INDE  9 21 56 FOBS=   32.8 SIGMA=   4.3 PHAS= -100.0 FOM= 0.38 TEST= 0
INDE  9 21 58 FOBS=  107.6 SIGMA=   1.9 PHAS=  100.4 FOM= 0.85 TEST= 0
INDE  9 21 60 FOBS=   16.5 SIGMA=  14.3 PHAS= -143.4 FOM= 0.48 TEST= 0
INDE  9 21 62 FOBS=   46.4 SIGMA=   5.1 PHAS=  -92.9 FOM= 0.60 TEST= 0
INDE  9 21 64 FOBS=    2.5 SIGMA= 132.8 PHAS= -119.0 FOM= 0.02 TEST= 0
INDE  9 21 66 FOBS=   51.5 SIGMA=   8.9 PHAS=  120.4 FOM= 0.46 TEST= 0
INDE  9 21 68 FOBS=   82.2 SIGMA=   5.6 PHAS=  -70.1 FOM= 0.88 TEST= 0
INDE  9 21 70 FOBS=   41.7 SIGMA=  11.1 PHAS=  -85.3 FOM= 0.70 TEST= 0
INDE  9 21 72 FOBS=   45.6 SIGMA=  10.6 PHAS=   56.1 FOM= 0.05 TEST= 1
INDE  9 21 74 FOBS=   17.0 SIGMA=  29.5 PHAS= -113.8 FOM= 0.28 TEST= 0
INDE  9 22  9 FOBS=  172.7 SIGMA=   0.4 PHAS=  137.0 FOM= 0.97 TEST= 0
INDE  9 22 11 FOBS=   90.3 SIGMA=   0.8 PHAS=  135.9 FOM= 0.97 TEST= 1
INDE  9 22 13 FOBS=   95.7 SIGMA=   0.8 PHAS=   77.2 FOM= 0.94 TEST= 0
INDE  9 22 15 FOBS=  144.1 SIGMA=   0.7 PHAS=   32.5 FOM= 0.98 TEST= 0
INDE  9 22 17 FOBS=   13.3 SIGMA=   6.7 PHAS=  -86.3 FOM= 0.80 TEST= 0
INDE  9 22 19 FOBS=  183.0 SIGMA=   0.6 PHAS=  -29.3 FOM= 0.97 TEST= 0
INDE  9 22 21 FOBS=  245.2 SIGMA=   0.6 PHAS=  -96.9 FOM= 0.95 TEST= 0
INDE  9 22 23 FOBS=  215.1 SIGMA=   0.5 PHAS=  116.9 FOM= 0.97 TEST= 0
INDE  9 22 25 FOBS=  105.0 SIGMA=   0.9 PHAS= -170.3 FOM= 0.89 TEST= 0
INDE  9 22 27 FOBS=  185.3 SIGMA=   0.6 PHAS= -178.3 FOM= 0.97 TEST= 0
INDE  9 22 29 FOBS=  259.1 SIGMA=   0.6 PHAS= -173.3 FOM= 0.92 TEST= 0
INDE  9 22 31 FOBS=   87.1 SIGMA=   1.3 PHAS=  159.5 FOM= 0.88 TEST= 0
INDE  9 22 33 FOBS=  435.8 SIGMA=   0.6 PHAS=  146.3 FOM= 0.97 TEST= 0
INDE  9 22 35 FOBS=  476.8 SIGMA=   0.6 PHAS=  176.2 FOM= 0.97 TEST= 0
INDE  9 22 37 FOBS=   98.5 SIGMA=   1.3 PHAS=  162.8 FOM= 0.93 TEST= 1
INDE  9 22 39 FOBS=  166.6 SIGMA=   0.9 PHAS= -171.3 FOM= 0.97 TEST= 1
INDE  9 22 41 FOBS=   32.7 SIGMA=   5.6 PHAS=   61.5 FOM= 0.18 TEST= 0
INDE  9 22 43 FOBS=  201.2 SIGMA=   1.0 PHAS= -158.0 FOM= 0.96 TEST= 0
INDE  9 22 45 FOBS=  187.5 SIGMA=   1.1 PHAS=  162.1 FOM= 0.81 TEST= 1
INDE  9 22 47 FOBS=  254.1 SIGMA=   0.9 PHAS=   10.7 FOM= 0.97 TEST= 0
INDE  9 22 49 FOBS=   67.9 SIGMA=   2.5 PHAS= -128.3 FOM= 0.91 TEST= 0
INDE  9 22 51 FOBS=  106.1 SIGMA=   1.8 PHAS=   48.7 FOM= 0.84 TEST= 0
INDE  9 22 53 FOBS=   89.8 SIGMA=   2.4 PHAS=  120.2 FOM= 0.91 TEST= 0
INDE  9 22 55 FOBS=   30.7 SIGMA=   4.0 PHAS=  -41.8 FOM= 0.32 TEST= 0
INDE  9 22 57 FOBS=   82.2 SIGMA=   1.8 PHAS=  -63.5 FOM= 0.87 TEST= 0
INDE  9 22 59 FOBS=   64.5 SIGMA=   3.1 PHAS=   84.2 FOM= 0.78 TEST= 0
INDE  9 22 61 FOBS=   62.1 SIGMA=   3.9 PHAS=   14.9 FOM= 0.56 TEST= 0
INDE  9 22 63 FOBS=   68.4 SIGMA=   4.1 PHAS=  117.4 FOM= 0.33 TEST= 1
INDE  9 22 67 FOBS=   87.5 SIGMA=   5.4 PHAS=   42.6 FOM= 0.94 TEST= 0
INDE  9 22 69 FOBS=   81.7 SIGMA=   5.8 PHAS= -138.4 FOM= 0.89 TEST= 0
INDE  9 22 71 FOBS=   57.6 SIGMA=   8.2 PHAS=   71.8 FOM= 0.82 TEST= 0
INDE  9 23 10 FOBS=   92.6 SIGMA=   0.7 PHAS=  100.9 FOM= 0.96 TEST= 0
INDE  9 23 12 FOBS=  106.1 SIGMA=   0.7 PHAS= -147.3 FOM= 0.96 TEST= 1
INDE  9 23 14 FOBS=   88.9 SIGMA=   0.9 PHAS=  -50.3 FOM= 0.90 TEST= 0
INDE  9 23 16 FOBS=  174.0 SIGMA=   0.7 PHAS=  -88.4 FOM= 0.99 TEST= 0
INDE  9 23 18 FOBS=  138.0 SIGMA=   0.8 PHAS=  -34.6 FOM= 0.94 TEST= 0
INDE  9 23 20 FOBS=  249.5 SIGMA=   0.6 PHAS=  162.5 FOM= 0.96 TEST= 0
```

*FIG. 12A - 240*

| | | | | | | | | | | | |
|---|---|---|---|---|---|---|---|---|---|---|---|
| INDE | 9 | 23 | 22 | FOBS= | 140.3 | SIGMA= | 0.7 | PHAS= | -49.0 | FOM= | 0.76 | TEST= 0
| INDE | 9 | 23 | 24 | FOBS= | 76.2 | SIGMA= | 1.2 | PHAS= | -45.1 | FOM= | 0.90 | TEST= 0
| INDE | 9 | 23 | 26 | FOBS= | 164.9 | SIGMA= | 0.6 | PHAS= | 144.5 | FOM= | 0.92 | TEST= 0
| INDE | 9 | 23 | 28 | FOBS= | 357.0 | SIGMA= | 0.6 | PHAS= | 97.0 | FOM= | 0.97 | TEST= 0
| INDE | 9 | 23 | 30 | FOBS= | 348.9 | SIGMA= | 0.6 | PHAS= | 82.9 | FOM= | 0.97 | TEST= 0
| INDE | 9 | 23 | 32 | FOBS= | 383.0 | SIGMA= | 0.6 | PHAS= | 52.9 | FOM= | 0.96 | TEST= 0
| INDE | 9 | 23 | 34 | FOBS= | 186.9 | SIGMA= | 0.8 | PHAS= | 43.8 | FOM= | 0.86 | TEST= 0
| INDE | 9 | 23 | 36 | FOBS= | 108.4 | SIGMA= | 1.2 | PHAS= | 74.7 | FOM= | 0.91 | TEST= 0
| INDE | 9 | 23 | 38 | FOBS= | 248.3 | SIGMA= | 0.8 | PHAS= | 72.0 | FOM= | 0.97 | TEST= 0
| INDE | 9 | 23 | 40 | FOBS= | 83.6 | SIGMA= | 2.1 | PHAS= | -33.1 | FOM= | 0.97 | TEST= 0
| INDE | 9 | 23 | 42 | FOBS= | 144.1 | SIGMA= | 1.3 | PHAS= | -24.6 | FOM= | 0.82 | TEST= 0
| INDE | 9 | 23 | 44 | FOBS= | 172.6 | SIGMA= | 1.1 | PHAS= | 55.4 | FOM= | 0.96 | TEST= 0
| INDE | 9 | 23 | 46 | FOBS= | 296.6 | SIGMA= | 0.8 | PHAS= | -61.4 | FOM= | 0.98 | TEST= 0
| INDE | 9 | 23 | 48 | FOBS= | 47.0 | SIGMA= | 3.7 | PHAS= | 28.8 | FOM= | 0.85 | TEST= 1
| INDE | 9 | 23 | 50 | FOBS= | 0.0 | SIGMA= | 19.5 | PHAS= | 0.0 | FOM= | 0.00 | TEST= 0
| INDE | 9 | 23 | 52 | FOBS= | 102.6 | SIGMA= | 1.9 | PHAS= | -60.3 | FOM= | 0.85 | TEST= 0
| INDE | 9 | 23 | 54 | FOBS= | 111.1 | SIGMA= | 1.9 | PHAS= | 32.2 | FOM= | 0.68 | TEST= 0
| INDE | 9 | 23 | 56 | FOBS= | 85.5 | SIGMA= | 1.5 | PHAS= | 104.5 | FOM= | 0.94 | TEST= 0
| INDE | 9 | 23 | 58 | FOBS= | 36.6 | SIGMA= | 4.8 | PHAS= | -151.0 | FOM= | 0.47 | TEST= 0
| INDE | 9 | 23 | 60 | FOBS= | 46.5 | SIGMA= | 5.2 | PHAS= | -125.4 | FOM= | 0.80 | TEST= 0
| INDE | 9 | 23 | 62 | FOBS= | 100.6 | SIGMA= | 2.5 | PHAS= | -83.7 | FOM= | 0.91 | TEST= 0
| INDE | 9 | 23 | 64 | FOBS= | 30.9 | SIGMA= | 15.3 | PHAS= | -149.6 | FOM= | 0.50 | TEST= 0
| INDE | 9 | 23 | 66 | FOBS= | 48.0 | SIGMA= | 9.7 | PHAS= | -65.5 | FOM= | 0.74 | TEST= 0
| INDE | 9 | 23 | 68 | FOBS= | 99.3 | SIGMA= | 4.9 | PHAS= | -103.0 | FOM= | 0.90 | TEST= 0
| INDE | 9 | 23 | 70 | FOBS= | 33.5 | SIGMA= | 14.1 | PHAS= | -50.5 | FOM= | 0.47 | TEST= 0
| INDE | 9 | 23 | 72 | FOBS= | 67.5 | SIGMA= | 7.1 | PHAS= | -18.8 | FOM= | 0.92 | TEST= 0
| INDE | 9 | 24 | 9 | FOBS= | 47.6 | SIGMA= | 1.3 | PHAS= | -129.4 | FOM= | 0.76 | TEST= 0
| INDE | 9 | 24 | 11 | FOBS= | 173.3 | SIGMA= | 0.6 | PHAS= | 148.5 | FOM= | 0.94 | TEST= 0
| INDE | 9 | 24 | 13 | FOBS= | 198.3 | SIGMA= | 0.5 | PHAS= | 91.7 | FOM= | 0.97 | TEST= 0
| INDE | 9 | 24 | 15 | FOBS= | 85.1 | SIGMA= | 1.0 | PHAS= | 58.3 | FOM= | 0.94 | TEST= 0
| INDE | 9 | 24 | 17 | FOBS= | 217.5 | SIGMA= | 0.6 | PHAS= | -100.7 | FOM= | 0.95 | TEST= 0
| INDE | 9 | 24 | 19 | FOBS= | 24.3 | SIGMA= | 4.7 | PHAS= | 83.0 | FOM= | 0.27 | TEST= 1
| INDE | 9 | 24 | 21 | FOBS= | 113.1 | SIGMA= | 0.9 | PHAS= | -158.1 | FOM= | 0.80 | TEST= 0
| INDE | 9 | 24 | 23 | FOBS= | 287.5 | SIGMA= | 0.6 | PHAS= | 127.4 | FOM= | 0.99 | TEST= 1
| INDE | 9 | 24 | 25 | FOBS= | 264.6 | SIGMA= | 0.6 | PHAS= | 45.7 | FOM= | 0.95 | TEST= 0
| INDE | 9 | 24 | 27 | FOBS= | 303.2 | SIGMA= | 0.5 | PHAS= | 25.0 | FOM= | 0.99 | TEST= 0
| INDE | 9 | 24 | 29 | FOBS= | 183.5 | SIGMA= | 0.6 | PHAS= | -16.6 | FOM= | 0.94 | TEST= 0
| INDE | 9 | 24 | 31 | FOBS= | 284.3 | SIGMA= | 0.6 | PHAS= | -19.6 | FOM= | 0.95 | TEST= 0
| INDE | 9 | 24 | 33 | FOBS= | 82.0 | SIGMA= | 1.5 | PHAS= | 3.8 | FOM= | 0.91 | TEST= 0
| INDE | 9 | 24 | 35 | FOBS= | 122.9 | SIGMA= | 1.2 | PHAS= | 163.0 | FOM= | 0.84 | TEST= 0
| INDE | 9 | 24 | 37 | FOBS= | 156.2 | SIGMA= | 1.1 | PHAS= | -84.8 | FOM= | 0.92 | TEST= 0
| INDE | 9 | 24 | 39 | FOBS= | 0.0 | SIGMA= | 18.4 | PHAS= | 0.0 | FOM= | 0.00 | TEST= 0
| INDE | 9 | 24 | 41 | FOBS= | 62.5 | SIGMA= | 3.1 | PHAS= | -94.2 | FOM= | 0.58 | TEST= 0
| INDE | 9 | 24 | 43 | FOBS= | 239.8 | SIGMA= | 0.9 | PHAS= | -134.2 | FOM= | 0.95 | TEST= 1
| INDE | 9 | 24 | 45 | FOBS= | 176.3 | SIGMA= | 1.2 | PHAS= | -142.0 | FOM= | 0.94 | TEST= 1
| INDE | 9 | 24 | 47 | FOBS= | 95.0 | SIGMA= | 1.9 | PHAS= | -99.3 | FOM= | 0.97 | TEST= 0
| INDE | 9 | 24 | 49 | FOBS= | 43.8 | SIGMA= | 3.9 | PHAS= | 162.5 | FOM= | 0.87 | TEST= 0
| INDE | 9 | 24 | 51 | FOBS= | 32.5 | SIGMA= | 5.5 | PHAS= | 95.5 | FOM= | 0.13 | TEST= 0
| INDE | 9 | 24 | 53 | FOBS= | 114.9 | SIGMA= | 1.7 | PHAS= | 178.8 | FOM= | 0.92 | TEST= 0
| INDE | 9 | 24 | 55 | FOBS= | 114.9 | SIGMA= | 1.4 | PHAS= | 13.3 | FOM= | 0.89 | TEST= 0
| INDE | 9 | 24 | 57 | FOBS= | 176.5 | SIGMA= | 1.3 | PHAS= | 15.0 | FOM= | 0.96 | TEST= 0
| INDE | 9 | 24 | 59 | FOBS= | 114.2 | SIGMA= | 1.5 | PHAS= | 121.2 | FOM= | 0.95 | TEST= 0
| INDE | 9 | 24 | 61 | FOBS= | 121.5 | SIGMA= | 2.1 | PHAS= | -145.0 | FOM= | 0.79 | TEST= 1
| INDE | 9 | 24 | 63 | FOBS= | 56.7 | SIGMA= | 5.7 | PHAS= | 103.8 | FOM= | 0.66 | TEST= 0
| INDE | 9 | 24 | 65 | FOBS= | 27.6 | SIGMA= | 17.2 | PHAS= | 40.4 | FOM= | 0.09 | TEST= 0
| INDE | 9 | 24 | 67 | FOBS= | 123.7 | SIGMA= | 4.1 | PHAS= | 89.3 | FOM= | 0.96 | TEST= 0
| INDE | 9 | 24 | 69 | FOBS= | 34.5 | SIGMA= | 13.7 | PHAS= | -176.9 | FOM= | 0.51 | TEST= 0
| INDE | 9 | 24 | 71 | FOBS= | 46.3 | SIGMA= | 10.5 | PHAS= | -125.5 | FOM= | 0.65 | TEST= 0
| INDE | 9 | 24 | 73 | FOBS= | 88.3 | SIGMA= | 5.8 | PHAS= | -120.7 | FOM= | 0.93 | TEST= 0
| INDE | 9 | 25 | 10 | FOBS= | 75.4 | SIGMA= | 0.9 | PHAS= | 121.6 | FOM= | 0.98 | TEST= 0
| INDE | 9 | 25 | 12 | FOBS= | 123.1 | SIGMA= | 0.7 | PHAS= | -39.4 | FOM= | 0.96 | TEST= 1
| INDE | 9 | 25 | 14 | FOBS= | 101.4 | SIGMA= | 0.9 | PHAS= | 47.5 | FOM= | 0.72 | TEST= 0
| INDE | 9 | 25 | 16 | FOBS= | 127.3 | SIGMA= | 0.8 | PHAS= | -153.3 | FOM= | 0.90 | TEST= 0
| INDE | 9 | 25 | 18 | FOBS= | 67.5 | SIGMA= | 1.5 | PHAS= | -139.5 | FOM= | 0.17 | TEST= 0
| INDE | 9 | 25 | 20 | FOBS= | 213.6 | SIGMA= | 0.6 | PHAS= | 136.9 | FOM= | 0.93 | TEST= 0
| INDE | 9 | 25 | 22 | FOBS= | 177.9 | SIGMA= | 0.7 | PHAS= | -18.6 | FOM= | 0.94 | TEST= 0
| INDE | 9 | 25 | 24 | FOBS= | 325.5 | SIGMA= | 0.5 | PHAS= | -13.2 | FOM= | 0.98 | TEST= 0
| INDE | 9 | 25 | 26 | FOBS= | 188.9 | SIGMA= | 0.6 | PHAS= | -110.9 | FOM= | 0.98 | TEST= 0
| INDE | 9 | 25 | 28 | FOBS= | 100.6 | SIGMA= | 1.1 | PHAS= | 37.2 | FOM= | 0.95 | TEST= 0
| INDE | 9 | 25 | 30 | FOBS= | 9.0 | SIGMA= | 12.8 | PHAS= | -117.9 | FOM= | 0.58 | TEST= 0

*FIG. 12A - 241*

```
INDE  9  25  32  FOBS=  173.3  SIGMA=   1.0  PHAS=   -46.4  FOM=  0.98  TEST= 1
INDE  9  25  34  FOBS=  178.9  SIGMA=   1.0  PHAS=   -61.9  FOM=  0.89  TEST= 0
INDE  9  25  36  FOBS=   96.3  SIGMA=   1.8  PHAS=   170.1  FOM=  0.89  TEST= 0
INDE  9  25  38  FOBS=  147.8  SIGMA=   1.3  PHAS=    18.6  FOM=  0.90  TEST= 0
INDE  9  25  40  FOBS=  147.6  SIGMA=   1.3  PHAS=   -76.0  FOM=  0.89  TEST= 0
INDE  9  25  42  FOBS=  195.6  SIGMA=   1.1  PHAS=  -163.1  FOM=  0.94  TEST= 0
INDE  9  25  44  FOBS=  106.0  SIGMA=   1.8  PHAS=   136.5  FOM=  0.98  TEST= 0
INDE  9  25  46  FOBS=    0.0  SIGMA=  18.6  PHAS=     0.0  FOM=  0.00  TEST= 0
INDE  9  25  48  FOBS=  203.6  SIGMA=   1.0  PHAS=   100.8  FOM=  0.96  TEST= 0
INDE  9  25  50  FOBS=  178.3  SIGMA=   1.1  PHAS=    31.2  FOM=  0.82  TEST= 0
INDE  9  25  52  FOBS=   78.9  SIGMA=   2.2  PHAS=    88.2  FOM=  0.78  TEST= 1
INDE  9  25  54  FOBS=   63.2  SIGMA=   2.8  PHAS=    57.8  FOM=  0.52  TEST= 1
INDE  9  25  56  FOBS=   84.5  SIGMA=   1.8  PHAS=   -41.9  FOM=  0.64  TEST= 1
INDE  9  25  58  FOBS=   59.9  SIGMA=   2.7  PHAS=   -36.0  FOM=  0.86  TEST= 0
INDE  9  25  60  FOBS=   97.0  SIGMA=   1.8  PHAS=    22.0  FOM=  0.94  TEST= 0
INDE  9  25  62  FOBS=    0.0  SIGMA=  23.6  PHAS=     0.0  FOM=  0.00  TEST= 0
INDE  9  25  64  FOBS=    0.0  SIGMA=  31.0  PHAS=     0.0  FOM=  0.00  TEST= 0
INDE  9  25  66  FOBS=  103.4  SIGMA=   4.8  PHAS=   -37.7  FOM=  0.92  TEST= 0
INDE  9  25  68  FOBS=   79.8  SIGMA=   6.2  PHAS=   -47.3  FOM=  0.93  TEST= 0
INDE  9  25  70  FOBS=   18.4  SIGMA=  26.0  PHAS=    24.1  FOM=  0.21  TEST= 0
INDE  9  25  72  FOBS=   53.3  SIGMA=   9.3  PHAS=   164.0  FOM=  0.72  TEST= 0
INDE  9  26   9  FOBS=   99.8  SIGMA=   0.7  PHAS=  -152.3  FOM=  0.87  TEST= 0
INDE  9  26  11  FOBS=  119.6  SIGMA=   0.7  PHAS=   161.7  FOM=  0.97  TEST= 0
INDE  9  26  13  FOBS=  176.9  SIGMA=   0.6  PHAS=  -170.4  FOM=  0.97  TEST= 0
INDE  9  26  15  FOBS=   61.1  SIGMA=   1.4  PHAS=    56.0  FOM=  0.85  TEST= 0
INDE  9  26  17  FOBS=  126.7  SIGMA=   0.8  PHAS=   -44.2  FOM=  0.90  TEST= 0
INDE  9  26  19  FOBS=  130.4  SIGMA=   0.9  PHAS=   134.8  FOM=  0.95  TEST= 0
INDE  9  26  21  FOBS=   75.9  SIGMA=   1.3  PHAS=  -157.7  FOM=  0.81  TEST= 0
INDE  9  26  23  FOBS=  211.4  SIGMA=   0.6  PHAS=   -60.2  FOM=  0.95  TEST= 0
INDE  9  26  25  FOBS=  162.7  SIGMA=   0.7  PHAS=  -107.6  FOM=  0.89  TEST= 0
INDE  9  26  27  FOBS=  141.6  SIGMA=   0.9  PHAS=     4.9  FOM=  0.98  TEST= 0
INDE  9  26  29  FOBS=  203.1  SIGMA=   0.8  PHAS=   -67.4  FOM=  0.90  TEST= 0
INDE  9  26  31  FOBS=   78.4  SIGMA=   1.8  PHAS=   176.7  FOM=  0.74  TEST= 0
INDE  9  26  33  FOBS=  218.4  SIGMA=   0.9  PHAS=   133.4  FOM=  0.92  TEST= 0
INDE  9  26  35  FOBS=  214.6  SIGMA=   0.9  PHAS=  -135.9  FOM=  0.92  TEST= 0
INDE  9  26  37  FOBS=  149.5  SIGMA=   1.3  PHAS=   -35.2  FOM=  0.90  TEST= 1
INDE  9  26  39  FOBS=    0.0  SIGMA=  19.8  PHAS=     0.0  FOM=  0.00  TEST= 1
INDE  9  26  41  FOBS=  265.7  SIGMA=   0.9  PHAS=   106.8  FOM=  0.96  TEST= 0
INDE  9  26  43  FOBS=   56.0  SIGMA=   3.4  PHAS=    81.6  FOM=  0.18  TEST= 0
INDE  9  26  45  FOBS=   41.7  SIGMA=   4.2  PHAS=    52.7  FOM=  0.19  TEST= 0
INDE  9  26  47  FOBS=  146.9  SIGMA=   1.3  PHAS=   -10.4  FOM=  0.94  TEST= 0
INDE  9  26  49  FOBS=   89.2  SIGMA=   2.0  PHAS=   -23.7  FOM=  0.56  TEST= 0
INDE  9  26  51  FOBS=   70.9  SIGMA=   2.4  PHAS=   -42.5  FOM=  0.62  TEST= 0
INDE  9  26  53  FOBS=    0.0  SIGMA=  18.3  PHAS=     0.0  FOM=  0.00  TEST= 0
INDE  9  26  55  FOBS=   96.6  SIGMA=   1.8  PHAS=   166.5  FOM=  0.91  TEST= 0
INDE  9  26  57  FOBS=   73.0  SIGMA=   2.1  PHAS=   -37.6  FOM=  0.86  TEST= 0
INDE  9  26  59  FOBS=   91.6  SIGMA=   2.0  PHAS=   150.6  FOM=  0.85  TEST= 0
INDE  9  26  61  FOBS=    0.0  SIGMA=  18.6  PHAS=     0.0  FOM=  0.00  TEST= 0
INDE  9  26  63  FOBS=   50.1  SIGMA=   6.4  PHAS=    11.4  FOM=  0.76  TEST= 0
INDE  9  26  65  FOBS=   55.5  SIGMA=   8.7  PHAS=   137.0  FOM=  0.52  TEST= 0
INDE  9  26  67  FOBS=   75.0  SIGMA=   6.6  PHAS=   175.3  FOM=  0.91  TEST= 0
INDE  9  26  69  FOBS=   28.1  SIGMA=  17.4  PHAS=  -106.3  FOM=  0.79  TEST= 0
INDE  9  26  71  FOBS=    0.0  SIGMA=  31.0  PHAS=     0.0  FOM=  0.00  TEST= 0
INDE  9  27  10  FOBS=   73.2  SIGMA=   1.0  PHAS=   137.1  FOM=  0.95  TEST= 0
INDE  9  27  12  FOBS=  272.5  SIGMA=   0.5  PHAS=   129.8  FOM=  0.96  TEST= 1
INDE  9  27  14  FOBS=  165.6  SIGMA=   0.6  PHAS=   127.1  FOM=  0.97  TEST= 0
INDE  9  27  16  FOBS=  124.6  SIGMA=   0.8  PHAS=  -120.9  FOM=  0.93  TEST= 0
INDE  9  27  18  FOBS=  151.4  SIGMA=   0.7  PHAS=    77.7  FOM=  0.93  TEST= 0
INDE  9  27  20  FOBS=  273.9  SIGMA=   0.7  PHAS=    95.2  FOM=  0.98  TEST= 0
INDE  9  27  22  FOBS=  292.4  SIGMA=   0.6  PHAS=  -140.1  FOM=  0.96  TEST= 0
INDE  9  27  24  FOBS=   91.2  SIGMA=   1.3  PHAS=    97.5  FOM=  0.22  TEST= 0
INDE  9  27  26  FOBS=  213.6  SIGMA=   0.7  PHAS=  -169.4  FOM=  0.98  TEST= 0
INDE  9  27  28  FOBS=  185.8  SIGMA=   0.8  PHAS=   -95.3  FOM=  0.85  TEST= 0
INDE  9  27  30  FOBS=  103.4  SIGMA=   1.4  PHAS=   -55.4  FOM=  0.52  TEST= 0
INDE  9  27  32  FOBS=  195.6  SIGMA=   0.9  PHAS=    46.6  FOM=  0.80  TEST= 0
INDE  9  27  34  FOBS=  139.6  SIGMA=   1.2  PHAS=   127.5  FOM=  0.85  TEST= 0
INDE  9  27  36  FOBS=  302.0  SIGMA=   0.8  PHAS=  -143.9  FOM=  0.94  TEST= 0
INDE  9  27  38  FOBS=  162.2  SIGMA=   1.3  PHAS=   -89.6  FOM=  0.93  TEST= 0
INDE  9  27  40  FOBS=  280.8  SIGMA=   0.9  PHAS=    16.0  FOM=  0.97  TEST= 0
INDE  9  27  42  FOBS=   95.1  SIGMA=   2.2  PHAS=  -114.2  FOM=  0.75  TEST= 0
```

*FIG. 12A - 242*

```
INDE  9 27 44 FOBS=    0.0 SIGMA= 19.9 PHAS=    0.0 FOM= 0.00 TEST= 0
INDE  9 27 46 FOBS=   97.4 SIGMA=  1.8 PHAS= -158.7 FOM= 0.85 TEST= 0
INDE  9 27 48 FOBS=  120.9 SIGMA=  1.5 PHAS= -175.9 FOM= 0.08 TEST= 1
INDE  9 27 50 FOBS=  160.7 SIGMA=  1.1 PHAS=   77.1 FOM= 0.95 TEST= 0
INDE  9 27 52 FOBS=   67.5 SIGMA=  2.5 PHAS=  168.2 FOM= 0.82 TEST= 0
INDE  9 27 54 FOBS=  130.0 SIGMA=  1.4 PHAS=  108.3 FOM= 0.92 TEST= 0
INDE  9 27 56 FOBS=  111.4 SIGMA=  1.6 PHAS=  125.3 FOM= 0.82 TEST= 0
INDE  9 27 58 FOBS=    0.0 SIGMA= 17.7 PHAS=    0.0 FOM= 0.00 TEST= 0
INDE  9 27 60 FOBS=   96.5 SIGMA=  1.9 PHAS=   28.6 FOM= 0.90 TEST= 0
INDE  9 27 62 FOBS=   77.5 SIGMA=  2.5 PHAS=  -49.3 FOM= 0.91 TEST= 0
INDE  9 27 64 FOBS=   80.4 SIGMA=  4.1 PHAS=  -26.8 FOM= 0.85 TEST= 0
INDE  9 27 66 FOBS=   75.1 SIGMA=  6.5 PHAS=   72.4 FOM= 0.90 TEST= 0
INDE  9 27 68 FOBS=    0.0 SIGMA= 31.2 PHAS=    0.0 FOM= 0.00 TEST= 0
INDE  9 27 70 FOBS=   17.9 SIGMA= 27.5 PHAS=   88.3 FOM= 0.05 TEST= 0
INDE  9 27 72 FOBS=   40.0 SIGMA= 12.8 PHAS=  -73.6 FOM= 0.50 TEST= 0
INDE  9 28  9 FOBS=  161.9 SIGMA=  0.6 PHAS= -119.5 FOM= 0.98 TEST= 0
INDE  9 28 11 FOBS=  385.0 SIGMA=  0.6 PHAS=   74.4 FOM= 0.98 TEST= 0
INDE  9 28 13 FOBS=   82.5 SIGMA=  1.2 PHAS=  122.4 FOM= 0.81 TEST= 0
INDE  9 28 15 FOBS=  174.9 SIGMA=  0.7 PHAS=   48.2 FOM= 0.90 TEST= 0
INDE  9 28 17 FOBS=  107.3 SIGMA=  1.2 PHAS=  -30.1 FOM= 0.99 TEST= 0
INDE  9 28 19 FOBS=   91.5 SIGMA=  1.3 PHAS=  -52.6 FOM= 0.91 TEST= 0
INDE  9 28 21 FOBS=  270.0 SIGMA=  0.8 PHAS=   40.3 FOM= 0.96 TEST= 0
INDE  9 28 23 FOBS=  217.8 SIGMA=  0.8 PHAS=   29.7 FOM= 0.94 TEST= 0
INDE  9 28 25 FOBS=  161.7 SIGMA=  1.0 PHAS=   85.9 FOM= 0.96 TEST= 0
INDE  9 28 27 FOBS=  130.1 SIGMA=  1.1 PHAS=  178.5 FOM= 0.88 TEST= 0
INDE  9 28 29 FOBS=  201.1 SIGMA=  0.8 PHAS= -174.4 FOM= 0.86 TEST= 0
INDE  9 28 31 FOBS=   42.2 SIGMA=  3.6 PHAS= -160.4 FOM= 0.64 TEST= 0
INDE  9 28 33 FOBS=  272.3 SIGMA=  0.9 PHAS= -139.8 FOM= 0.94 TEST= 0
INDE  9 28 35 FOBS=   70.9 SIGMA=  2.4 PHAS=  165.5 FOM= 0.80 TEST= 0
INDE  9 28 37 FOBS=  181.7 SIGMA=  1.5 PHAS=  109.7 FOM= 0.79 TEST= 1
INDE  9 28 39 FOBS=    0.0 SIGMA= 21.8 PHAS=    0.0 FOM= 0.00 TEST= 0
INDE  9 28 41 FOBS=  132.8 SIGMA=  1.6 PHAS=  123.3 FOM= 0.86 TEST= 1
INDE  9 28 43 FOBS=  121.3 SIGMA=  1.7 PHAS= -157.1 FOM= 0.73 TEST= 1
INDE  9 28 45 FOBS=   38.6 SIGMA=  5.1 PHAS=  102.4 FOM= 0.46 TEST= 0
INDE  9 28 47 FOBS=   94.4 SIGMA=  1.9 PHAS=   57.1 FOM= 0.94 TEST= 0
INDE  9 28 49 FOBS=    6.8 SIGMA= 26.6 PHAS=   51.0 FOM= 0.05 TEST= 0
INDE  9 28 51 FOBS=  111.6 SIGMA=  1.6 PHAS=   46.1 FOM= 0.87 TEST= 0
INDE  9 28 53 FOBS=   96.6 SIGMA=  1.8 PHAS=   70.7 FOM= 0.96 TEST= 0
INDE  9 28 55 FOBS=    0.0 SIGMA= 18.3 PHAS=    0.0 FOM= 0.00 TEST= 0
INDE  9 28 57 FOBS=   82.6 SIGMA=  1.8 PHAS=  -34.2 FOM= 0.83 TEST= 0
INDE  9 28 59 FOBS=   54.3 SIGMA=  3.1 PHAS=  101.0 FOM= 0.81 TEST= 0
INDE  9 28 61 FOBS=   30.2 SIGMA=  7.5 PHAS= -147.9 FOM= 0.65 TEST= 0
INDE  9 28 63 FOBS=   27.6 SIGMA=  7.1 PHAS=  -82.1 FOM= 0.53 TEST= 0
INDE  9 28 65 FOBS=    0.0 SIGMA= 31.0 PHAS=    0.0 FOM= 0.00 TEST= 0
INDE  9 28 67 FOBS=    0.0 SIGMA= 31.6 PHAS=    0.0 FOM= 0.00 TEST= 0
INDE  9 28 69 FOBS=   27.4 SIGMA= 18.3 PHAS=  -19.7 FOM= 0.61 TEST= 0
INDE  9 28 71 FOBS=   53.6 SIGMA=  9.7 PHAS=  175.0 FOM= 0.76 TEST= 0
INDE  9 29 10 FOBS=  120.2 SIGMA=  0.8 PHAS=  -30.2 FOM= 0.98 TEST= 0
INDE  9 29 12 FOBS=  100.9 SIGMA=  1.1 PHAS=   64.9 FOM= 0.95 TEST= 0
INDE  9 29 14 FOBS=   66.6 SIGMA=  1.6 PHAS=  106.7 FOM= 0.72 TEST= 0
INDE  9 29 16 FOBS=  143.1 SIGMA=  0.9 PHAS=    1.3 FOM= 0.98 TEST= 0
INDE  9 29 18 FOBS=   61.6 SIGMA=  2.0 PHAS=   16.0 FOM= 0.87 TEST= 0
INDE  9 29 20 FOBS=  126.4 SIGMA=  1.0 PHAS= -166.9 FOM= 0.82 TEST= 0
INDE  9 29 22 FOBS=  436.4 SIGMA=  0.8 PHAS=  -80.3 FOM= 0.98 TEST= 0
INDE  9 29 24 FOBS=  169.4 SIGMA=  0.9 PHAS=  163.3 FOM= 0.40 TEST= 0
INDE  9 29 26 FOBS=  239.5 SIGMA=  0.8 PHAS=  127.1 FOM= 0.99 TEST= 0
INDE  9 29 28 FOBS=  171.5 SIGMA=  0.9 PHAS=  159.8 FOM= 0.90 TEST= 0
INDE  9 29 30 FOBS=  155.1 SIGMA=  1.0 PHAS=   55.9 FOM= 0.98 TEST= 0
INDE  9 29 32 FOBS=   72.8 SIGMA=  2.2 PHAS=   17.5 FOM= 0.83 TEST= 0
INDE  9 29 34 FOBS=  289.8 SIGMA=  0.9 PHAS=  132.0 FOM= 0.99 TEST= 0
INDE  9 29 36 FOBS=  227.0 SIGMA=  0.9 PHAS=  -40.5 FOM= 0.92 TEST= 0
INDE  9 29 38 FOBS=  239.2 SIGMA=  1.1 PHAS=   14.4 FOM= 0.92 TEST= 0
INDE  9 29 40 FOBS=  192.9 SIGMA=  1.2 PHAS=   -1.7 FOM= 0.92 TEST= 0
INDE  9 29 42 FOBS=  166.5 SIGMA=  1.3 PHAS=  144.5 FOM= 0.93 TEST= 0
INDE  9 29 44 FOBS=   97.8 SIGMA=  2.1 PHAS=   94.4 FOM= 0.85 TEST= 0
INDE  9 29 46 FOBS=  154.9 SIGMA=  1.4 PHAS= -177.2 FOM= 0.91 TEST= 0
INDE  9 29 48 FOBS=  167.6 SIGMA=  1.1 PHAS=   82.3 FOM= 0.93 TEST= 0
INDE  9 29 50 FOBS=   91.1 SIGMA=  1.9 PHAS=   18.6 FOM= 0.87 TEST= 0
INDE  9 29 52 FOBS=   49.7 SIGMA=  3.4 PHAS=  109.4 FOM= 0.62 TEST= 0
INDE  9 29 54 FOBS=   75.2 SIGMA=  2.3 PHAS=   77.9 FOM= 0.95 TEST= 0
```

*FIG. 12A - 243*

| | | | | | | | | | | | |
|---|---|---|---|---|---|---|---|---|---|---|---|
| INDE | 9 | 29 | 56 | FOBS= | 143.3 | SIGMA= | 1.2 | PHAS= | 162.8 | FOM= | 0.95 | TEST= 0
| INDE | 9 | 29 | 58 | FOBS= | 42.8 | SIGMA= | 3.6 | PHAS= | 47.0 | FOM= | 0.59 | TEST= 0
| INDE | 9 | 29 | 60 | FOBS= | 73.6 | SIGMA= | 2.5 | PHAS= | 30.1 | FOM= | 0.17 | TEST= 1
| INDE | 9 | 29 | 62 | FOBS= | 54.4 | SIGMA= | 3.9 | PHAS= | -155.5 | FOM= | 0.80 | TEST= 0
| INDE | 9 | 29 | 64 | FOBS= | 59.4 | SIGMA= | 3.5 | PHAS= | -75.5 | FOM= | 0.67 | TEST= 0
| INDE | 9 | 29 | 66 | FOBS= | 71.0 | SIGMA= | 7.0 | PHAS= | 129.3 | FOM= | 0.89 | TEST= 0
| INDE | 9 | 29 | 68 | FOBS= | 26.8 | SIGMA= | 18.5 | PHAS= | -24.1 | FOM= | 0.28 | TEST= 0
| INDE | 9 | 30 | 9 | FOBS= | 165.0 | SIGMA= | 0.6 | PHAS= | -135.3 | FOM= | 0.95 | TEST= 0
| INDE | 9 | 30 | 11 | FOBS= | 117.2 | SIGMA= | 1.0 | PHAS= | 83.2 | FOM= | 0.98 | TEST= 0
| INDE | 9 | 30 | 13 | FOBS= | 147.2 | SIGMA= | 0.8 | PHAS= | -118.4 | FOM= | 0.82 | TEST= 0
| INDE | 9 | 30 | 15 | FOBS= | 28.9 | SIGMA= | 3.7 | PHAS= | 50.1 | FOM= | 0.33 | TEST= 0
| INDE | 9 | 30 | 17 | FOBS= | 254.3 | SIGMA= | 0.7 | PHAS= | -105.8 | FOM= | 0.96 | TEST= 0
| INDE | 9 | 30 | 19 | FOBS= | 145.0 | SIGMA= | 0.9 | PHAS= | -153.2 | FOM= | 0.97 | TEST= 0
| INDE | 9 | 30 | 21 | FOBS= | 382.2 | SIGMA= | 0.8 | PHAS= | 133.1 | FOM= | 0.99 | TEST= 0
| INDE | 9 | 30 | 23 | FOBS= | 174.1 | SIGMA= | 1.1 | PHAS= | 163.9 | FOM= | 0.92 | TEST= 0
| INDE | 9 | 30 | 25 | FOBS= | 185.7 | SIGMA= | 0.9 | PHAS= | 54.3 | FOM= | 0.98 | TEST= 1
| INDE | 9 | 30 | 27 | FOBS= | 35.0 | SIGMA= | 4.5 | PHAS= | 67.6 | FOM= | 0.87 | TEST= 0
| INDE | 9 | 30 | 29 | FOBS= | 210.0 | SIGMA= | 0.8 | PHAS= | -6.6 | FOM= | 0.97 | TEST= 0
| INDE | 9 | 30 | 31 | FOBS= | 263.1 | SIGMA= | 0.8 | PHAS= | -55.5 | FOM= | 0.98 | TEST= 0
| INDE | 9 | 30 | 33 | FOBS= | 176.3 | SIGMA= | 1.1 | PHAS= | 169.5 | FOM= | 0.99 | TEST= 0
| INDE | 9 | 30 | 35 | FOBS= | 156.2 | SIGMA= | 1.3 | PHAS= | 92.6 | FOM= | 0.94 | TEST= 0
| INDE | 9 | 30 | 37 | FOBS= | 158.5 | SIGMA= | 1.3 | PHAS= | -36.9 | FOM= | 0.95 | TEST= 0
| INDE | 9 | 30 | 39 | FOBS= | 41.2 | SIGMA= | 6.2 | PHAS= | 25.6 | FOM= | 0.67 | TEST= 1
| INDE | 9 | 30 | 41 | FOBS= | 36.3 | SIGMA= | 6.9 | PHAS= | 81.4 | FOM= | 0.31 | TEST= 1
| INDE | 9 | 30 | 43 | FOBS= | 127.8 | SIGMA= | 1.6 | PHAS= | 94.3 | FOM= | 0.71 | TEST= 0
| INDE | 9 | 30 | 45 | FOBS= | 184.2 | SIGMA= | 1.2 | PHAS= | 84.1 | FOM= | 0.96 | TEST= 0
| INDE | 9 | 30 | 47 | FOBS= | 154.2 | SIGMA= | 1.3 | PHAS= | 1.5 | FOM= | 0.93 | TEST= 0
| INDE | 9 | 30 | 49 | FOBS= | 43.5 | SIGMA= | 4.4 | PHAS= | 9.8 | FOM= | 0.72 | TEST= 0
| INDE | 9 | 30 | 51 | FOBS= | 71.5 | SIGMA= | 2.4 | PHAS= | 83.8 | FOM= | 0.28 | TEST= 0
| INDE | 9 | 30 | 53 | FOBS= | 97.9 | SIGMA= | 1.8 | PHAS= | -20.1 | FOM= | 0.73 | TEST= 0
| INDE | 9 | 30 | 55 | FOBS= | 121.7 | SIGMA= | 1.5 | PHAS= | 55.4 | FOM= | 0.95 | TEST= 0
| INDE | 9 | 30 | 57 | FOBS= | 51.7 | SIGMA= | 3.0 | PHAS= | 40.3 | FOM= | 0.43 | TEST= 0
| INDE | 9 | 30 | 59 | FOBS= | 63.3 | SIGMA= | 2.4 | PHAS= | 31.6 | FOM= | 0.84 | TEST= 0
| INDE | 9 | 30 | 61 | FOBS= | 49.4 | SIGMA= | 3.6 | PHAS= | -54.3 | FOM= | 0.13 | TEST= 0
| INDE | 9 | 30 | 63 | FOBS= | 57.2 | SIGMA= | 3.5 | PHAS= | 110.3 | FOM= | 0.38 | TEST= 0
| INDE | 9 | 30 | 65 | FOBS= | 13.3 | SIGMA= | 18.3 | PHAS= | -99.3 | FOM= | 0.01 | TEST= 1
| INDE | 9 | 30 | 67 | FOBS= | 41.4 | SIGMA= | 12.1 | PHAS= | -9.1 | FOM= | 0.75 | TEST= 0
| INDE | 9 | 30 | 69 | FOBS= | 50.8 | SIGMA= | 10.1 | PHAS= | -54.4 | FOM= | 0.61 | TEST= 0
| INDE | 9 | 30 | 71 | FOBS= | 127.3 | SIGMA= | 4.3 | PHAS= | 95.8 | FOM= | 0.93 | TEST= 0
| INDE | 9 | 31 | 10 | FOBS= | 75.2 | SIGMA= | 1.2 | PHAS= | -122.8 | FOM= | 0.92 | TEST= 1
| INDE | 9 | 31 | 12 | FOBS= | 190.1 | SIGMA= | 0.7 | PHAS= | -23.8 | FOM= | 0.61 | TEST= 1
| INDE | 9 | 31 | 14 | FOBS= | 298.7 | SIGMA= | 0.6 | PHAS= | 132.7 | FOM= | 0.96 | TEST= 0
| INDE | 9 | 31 | 16 | FOBS= | 310.1 | SIGMA= | 0.6 | PHAS= | 136.1 | FOM= | 0.98 | TEST= 0
| INDE | 9 | 31 | 18 | FOBS= | 176.0 | SIGMA= | 0.9 | PHAS= | 172.1 | FOM= | 0.96 | TEST= 0
| INDE | 9 | 31 | 20 | FOBS= | 143.6 | SIGMA= | 1.0 | PHAS= | 78.9 | FOM= | 0.97 | TEST= 1
| INDE | 9 | 31 | 22 | FOBS= | 106.3 | SIGMA= | 1.6 | PHAS= | 109.0 | FOM= | 0.72 | TEST= 1
| INDE | 9 | 31 | 24 | FOBS= | 136.0 | SIGMA= | 1.4 | PHAS= | 54.2 | FOM= | 0.93 | TEST= 0
| INDE | 9 | 31 | 26 | FOBS= | 108.2 | SIGMA= | 1.5 | PHAS= | -65.6 | FOM= | 0.94 | TEST= 0
| INDE | 9 | 31 | 28 | FOBS= | 198.6 | SIGMA= | 0.9 | PHAS= | -80.3 | FOM= | 0.93 | TEST= 0
| INDE | 9 | 31 | 30 | FOBS= | 91.2 | SIGMA= | 1.8 | PHAS= | -121.6 | FOM= | 0.73 | TEST= 0
| INDE | 9 | 31 | 32 | FOBS= | 0.0 | SIGMA= | 18.6 | PHAS= | 0.0 | FOM= | 0.00 | TEST= 0
| INDE | 9 | 31 | 34 | FOBS= | 285.5 | SIGMA= | 0.9 | PHAS= | 26.5 | FOM= | 0.95 | TEST= 0
| INDE | 9 | 31 | 36 | FOBS= | 129.3 | SIGMA= | 1.6 | PHAS= | -133.8 | FOM= | 0.56 | TEST= 1
| INDE | 9 | 31 | 38 | FOBS= | 75.8 | SIGMA= | 2.6 | PHAS= | -6.2 | FOM= | 0.83 | TEST= 0
| INDE | 9 | 31 | 40 | FOBS= | 202.0 | SIGMA= | 1.3 | PHAS= | -77.8 | FOM= | 0.95 | TEST= 0
| INDE | 9 | 31 | 42 | FOBS= | 96.8 | SIGMA= | 2.4 | PHAS= | -95.5 | FOM= | 0.58 | TEST= 1
| INDE | 9 | 31 | 44 | FOBS= | 173.2 | SIGMA= | 1.4 | PHAS= | 54.2 | FOM= | 0.49 | TEST= 1
| INDE | 9 | 31 | 46 | FOBS= | 22.5 | SIGMA= | 9.3 | PHAS= | -174.8 | FOM= | 0.07 | TEST= 0
| INDE | 9 | 31 | 48 | FOBS= | 0.0 | SIGMA= | 19.6 | PHAS= | 0.0 | FOM= | 0.00 | TEST= 0
| INDE | 9 | 31 | 50 | FOBS= | 60.2 | SIGMA= | 3.2 | PHAS= | -68.6 | FOM= | 0.69 | TEST= 0
| INDE | 9 | 31 | 52 | FOBS= | 63.5 | SIGMA= | 2.9 | PHAS= | 155.1 | FOM= | 0.89 | TEST= 0
| INDE | 9 | 31 | 54 | FOBS= | 93.6 | SIGMA= | 1.9 | PHAS= | -31.7 | FOM= | 0.90 | TEST= 0
| INDE | 9 | 31 | 56 | FOBS= | 0.0 | SIGMA= | 20.4 | PHAS= | 0.0 | FOM= | 0.00 | TEST= 0
| INDE | 9 | 31 | 58 | FOBS= | 0.0 | SIGMA= | 17.6 | PHAS= | 0.0 | FOM= | 0.00 | TEST= 0
| INDE | 9 | 31 | 60 | FOBS= | 125.3 | SIGMA= | 1.4 | PHAS= | -22.8 | FOM= | 0.95 | TEST= 0
| INDE | 9 | 31 | 62 | FOBS= | 0.0 | SIGMA= | 18.8 | PHAS= | 0.0 | FOM= | 0.00 | TEST= 0
| INDE | 9 | 31 | 64 | FOBS= | 0.0 | SIGMA= | 19.2 | PHAS= | 0.0 | FOM= | 0.00 | TEST= 0
| INDE | 9 | 31 | 66 | FOBS= | 0.0 | SIGMA= | 31.4 | PHAS= | 0.0 | FOM= | 0.00 | TEST= 0
| INDE | 9 | 31 | 68 | FOBS= | 70.7 | SIGMA= | 7.1 | PHAS= | -93.5 | FOM= | 0.93 | TEST= 0
| INDE | 9 | 31 | 70 | FOBS= | 94.5 | SIGMA= | 5.6 | PHAS= | -29.3 | FOM= | 0.69 | TEST= 0

*FIG. 12A - 244*

| | | | | | | | | | | | | |
|---|---|---|---|---|---|---|---|---|---|---|---|---|
| INDE | 9 | 32 | 9 | FOBS= | 35.9 | SIGMA= | 2.5 | PHAS= | -120.4 | FOM= | 0.93 | TEST= 0 |
| INDE | 9 | 32 | 11 | FOBS= | 63.6 | SIGMA= | 1.7 | PHAS= | -92.0 | FOM= | 0.96 | TEST= 0 |
| INDE | 9 | 32 | 13 | FOBS= | 177.9 | SIGMA= | 0.8 | PHAS= | -66.4 | FOM= | 0.99 | TEST= 0 |
| INDE | 9 | 32 | 15 | FOBS= | 405.1 | SIGMA= | 0.7 | PHAS= | 44.3 | FOM= | 0.98 | TEST= 0 |
| INDE | 9 | 32 | 17 | FOBS= | 147.4 | SIGMA= | 0.9 | PHAS= | 107.5 | FOM= | 0.96 | TEST= 0 |
| INDE | 9 | 32 | 19 | FOBS= | 173.4 | SIGMA= | 0.9 | PHAS= | 121.5 | FOM= | 0.92 | TEST= 0 |
| INDE | 9 | 32 | 21 | FOBS= | 142.3 | SIGMA= | 1.0 | PHAS= | 57.0 | FOM= | 0.95 | TEST= 0 |
| INDE | 9 | 32 | 23 | FOBS= | 204.5 | SIGMA= | 1.0 | PHAS= | -135.6 | FOM= | 0.81 | TEST= 0 |
| INDE | 9 | 32 | 25 | FOBS= | 16.9 | SIGMA= | 12.0 | PHAS= | 132.2 | FOM= | 0.17 | TEST= 0 |
| INDE | 9 | 32 | 27 | FOBS= | 440.8 | SIGMA= | 0.7 | PHAS= | -94.1 | FOM= | 0.95 | TEST= 1 |
| INDE | 9 | 32 | 29 | FOBS= | 138.2 | SIGMA= | 1.2 | PHAS= | -52.3 | FOM= | 0.87 | TEST= 0 |
| INDE | 9 | 32 | 31 | FOBS= | 212.4 | SIGMA= | 0.9 | PHAS= | -120.5 | FOM= | 0.92 | TEST= 0 |
| INDE | 9 | 32 | 33 | FOBS= | 0.0 | SIGMA= | 19.7 | PHAS= | 0.0 | FOM= | 0.00 | TEST= 0 |
| INDE | 9 | 32 | 35 | FOBS= | 0.0 | SIGMA= | 20.5 | PHAS= | 0.0 | FOM= | 0.00 | TEST= 0 |
| INDE | 9 | 32 | 37 | FOBS= | 207.7 | SIGMA= | 1.0 | PHAS= | -12.8 | FOM= | 0.94 | TEST= 0 |
| INDE | 9 | 32 | 39 | FOBS= | 54.7 | SIGMA= | 3.5 | PHAS= | 142.9 | FOM= | 0.18 | TEST= 0 |
| INDE | 9 | 32 | 41 | FOBS= | 293.4 | SIGMA= | 0.9 | PHAS= | 169.1 | FOM= | 0.94 | TEST= 0 |
| INDE | 9 | 32 | 43 | FOBS= | 99.5 | SIGMA= | 2.3 | PHAS= | 7.7 | FOM= | 0.59 | TEST= 0 |
| INDE | 9 | 32 | 45 | FOBS= | 45.0 | SIGMA= | 5.1 | PHAS= | -10.9 | FOM= | 0.67 | TEST= 0 |
| INDE | 9 | 32 | 47 | FOBS= | 59.0 | SIGMA= | 3.3 | PHAS= | 1.8 | FOM= | 0.65 | TEST= 0 |
| INDE | 9 | 32 | 49 | FOBS= | 119.6 | SIGMA= | 1.7 | PHAS= | 114.2 | FOM= | 0.92 | TEST= 0 |
| INDE | 9 | 32 | 51 | FOBS= | 83.4 | SIGMA= | 2.3 | PHAS= | 120.1 | FOM= | 0.94 | TEST= 0 |
| INDE | 9 | 32 | 53 | FOBS= | 104.3 | SIGMA= | 1.9 | PHAS= | -80.8 | FOM= | 0.97 | TEST= 0 |
| INDE | 9 | 32 | 55 | FOBS= | 40.4 | SIGMA= | 4.1 | PHAS= | -3.2 | FOM= | 0.08 | TEST= 1 |
| INDE | 9 | 32 | 57 | FOBS= | 24.5 | SIGMA= | 7.1 | PHAS= | 16.3 | FOM= | 0.25 | TEST= 0 |
| INDE | 9 | 32 | 59 | FOBS= | 0.0 | SIGMA= | 18.4 | PHAS= | 0.0 | FOM= | 0.00 | TEST= 0 |
| INDE | 9 | 32 | 61 | FOBS= | 70.2 | SIGMA= | 2.4 | PHAS= | -146.0 | FOM= | 0.65 | TEST= 0 |
| INDE | 9 | 32 | 63 | FOBS= | 61.5 | SIGMA= | 2.8 | PHAS= | -176.3 | FOM= | 0.74 | TEST= 0 |
| INDE | 9 | 32 | 65 | FOBS= | 0.0 | SIGMA= | 20.3 | PHAS= | 0.0 | FOM= | 0.00 | TEST= 0 |
| INDE | 9 | 32 | 67 | FOBS= | 36.6 | SIGMA= | 13.7 | PHAS= | 154.0 | FOM= | 0.60 | TEST= 0 |
| INDE | 9 | 32 | 69 | FOBS= | 27.0 | SIGMA= | 19.1 | PHAS= | -171.4 | FOM= | 0.43 | TEST= 0 |
| INDE | 9 | 33 | 10 | FOBS= | 167.9 | SIGMA= | 0.7 | PHAS= | -68.6 | FOM= | 0.91 | TEST= 0 |
| INDE | 9 | 33 | 12 | FOBS= | 186.4 | SIGMA= | 0.8 | PHAS= | -36.7 | FOM= | 0.83 | TEST= 0 |
| INDE | 9 | 33 | 14 | FOBS= | 232.7 | SIGMA= | 0.7 | PHAS= | -179.7 | FOM= | 0.94 | TEST= 0 |
| INDE | 9 | 33 | 16 | FOBS= | 172.3 | SIGMA= | 0.9 | PHAS= | 141.4 | FOM= | 0.54 | TEST= 1 |
| INDE | 9 | 33 | 18 | FOBS= | 273.5 | SIGMA= | 0.7 | PHAS= | 42.6 | FOM= | 0.94 | TEST= 0 |
| INDE | 9 | 33 | 20 | FOBS= | 0.0 | SIGMA= | 16.4 | PHAS= | 0.0 | FOM= | 0.00 | TEST= 0 |
| INDE | 9 | 33 | 22 | FOBS= | 137.2 | SIGMA= | 1.1 | PHAS= | 82.9 | FOM= | 0.84 | TEST= 0 |
| INDE | 9 | 33 | 24 | FOBS= | 135.5 | SIGMA= | 1.5 | PHAS= | 56.8 | FOM= | 0.84 | TEST= 0 |
| INDE | 9 | 33 | 26 | FOBS= | 237.5 | SIGMA= | 0.9 | PHAS= | -166.4 | FOM= | 0.79 | TEST= 0 |
| INDE | 9 | 33 | 28 | FOBS= | 263.0 | SIGMA= | 0.8 | PHAS= | -146.8 | FOM= | 0.94 | TEST= 0 |
| INDE | 9 | 33 | 30 | FOBS= | 178.4 | SIGMA= | 1.1 | PHAS= | -145.8 | FOM= | 0.92 | TEST= 0 |
| INDE | 9 | 33 | 32 | FOBS= | 143.7 | SIGMA= | 1.4 | PHAS= | -127.7 | FOM= | 0.90 | TEST= 1 |
| INDE | 9 | 33 | 34 | FOBS= | 230.8 | SIGMA= | 1.0 | PHAS= | -29.5 | FOM= | 0.90 | TEST= 0 |
| INDE | 9 | 33 | 36 | FOBS= | 157.8 | SIGMA= | 1.5 | PHAS= | -172.6 | FOM= | 0.91 | TEST= 0 |
| INDE | 9 | 33 | 38 | FOBS= | 0.0 | SIGMA= | 20.1 | PHAS= | 0.0 | FOM= | 0.00 | TEST= 0 |
| INDE | 9 | 33 | 40 | FOBS= | 101.3 | SIGMA= | 1.9 | PHAS= | 82.1 | FOM= | 0.92 | TEST= 0 |
| INDE | 9 | 33 | 42 | FOBS= | 73.8 | SIGMA= | 2.8 | PHAS= | -43.8 | FOM= | 0.86 | TEST= 0 |
| INDE | 9 | 33 | 44 | FOBS= | 144.3 | SIGMA= | 1.7 | PHAS= | -173.7 | FOM= | 0.89 | TEST= 0 |
| INDE | 9 | 33 | 46 | FOBS= | 76.5 | SIGMA= | 3.0 | PHAS= | -52.0 | FOM= | 0.37 | TEST= 0 |
| INDE | 9 | 33 | 48 | FOBS= | 132.0 | SIGMA= | 1.8 | PHAS= | -5.7 | FOM= | 0.94 | TEST= 0 |
| INDE | 9 | 33 | 50 | FOBS= | 48.5 | SIGMA= | 3.9 | PHAS= | 104.2 | FOM= | 0.18 | TEST= 0 |
| INDE | 9 | 33 | 52 | FOBS= | 84.6 | SIGMA= | 2.2 | PHAS= | 157.9 | FOM= | 0.92 | TEST= 0 |
| INDE | 9 | 33 | 54 | FOBS= | 56.7 | SIGMA= | 3.2 | PHAS= | 125.2 | FOM= | 0.84 | TEST= 0 |
| INDE | 9 | 33 | 56 | FOBS= | 69.6 | SIGMA= | 3.0 | PHAS= | 87.6 | FOM= | 0.68 | TEST= 0 |
| INDE | 9 | 33 | 58 | FOBS= | 0.0 | SIGMA= | 18.1 | PHAS= | 0.0 | FOM= | 0.00 | TEST= 0 |
| INDE | 9 | 33 | 60 | FOBS= | 17.2 | SIGMA= | 9.8 | PHAS= | 167.9 | FOM= | 0.08 | TEST= 1 |
| INDE | 9 | 33 | 62 | FOBS= | 108.1 | SIGMA= | 1.7 | PHAS= | 49.5 | FOM= | 0.91 | TEST= 0 |
| INDE | 9 | 33 | 64 | FOBS= | 0.0 | SIGMA= | 18.9 | PHAS= | 0.0 | FOM= | 0.00 | TEST= 0 |
| INDE | 9 | 33 | 66 | FOBS= | 48.5 | SIGMA= | 4.4 | PHAS= | -24.8 | FOM= | 0.23 | TEST= 1 |
| INDE | 9 | 33 | 68 | FOBS= | 0.0 | SIGMA= | 31.9 | PHAS= | 0.0 | FOM= | 0.00 | TEST= 1 |
| INDE | 9 | 34 | 9 | FOBS= | 248.1 | SIGMA= | 0.7 | PHAS= | -154.2 | FOM= | 0.94 | TEST= 1 |
| INDE | 9 | 34 | 11 | FOBS= | 240.1 | SIGMA= | 0.7 | PHAS= | -103.4 | FOM= | 0.97 | TEST= 0 |
| INDE | 9 | 34 | 13 | FOBS= | 213.6 | SIGMA= | 0.7 | PHAS= | -65.4 | FOM= | 0.90 | TEST= 0 |
| INDE | 9 | 34 | 15 | FOBS= | 400.0 | SIGMA= | 0.8 | PHAS= | 173.6 | FOM= | 0.99 | TEST= 0 |
| INDE | 9 | 34 | 17 | FOBS= | 146.4 | SIGMA= | 1.0 | PHAS= | 44.7 | FOM= | 0.94 | TEST= 0 |
| INDE | 9 | 34 | 19 | FOBS= | 166.1 | SIGMA= | 1.0 | PHAS= | 15.9 | FOM= | 0.93 | TEST= 0 |
| INDE | 9 | 34 | 21 | FOBS= | 153.2 | SIGMA= | 1.1 | PHAS= | 32.1 | FOM= | 0.96 | TEST= 0 |
| INDE | 9 | 34 | 23 | FOBS= | 99.9 | SIGMA= | 2.0 | PHAS= | -148.5 | FOM= | 0.93 | TEST= 0 |
| INDE | 9 | 34 | 25 | FOBS= | 168.4 | SIGMA= | 1.3 | PHAS= | 117.7 | FOM= | 0.93 | TEST= 0 |

*FIG. 12A - 245*

| | | | | | | | | | | | | |
|---|---|---|---|---|---|---|---|---|---|---|---|---|
| INDE | 9 | 34 | 27 | FOBS= | 237.3 | SIGMA= | 0.9 | PHAS= | -132.3 | FOM= | 0.93 | TEST= 0 |
| INDE | 9 | 34 | 29 | FOBS= | 214.3 | SIGMA= | 1.0 | PHAS= | -178.9 | FOM= | 0.95 | TEST= 0 |
| INDE | 9 | 34 | 31 | FOBS= | 223.1 | SIGMA= | 0.9 | PHAS= | -164.4 | FOM= | 0.95 | TEST= 0 |
| INDE | 9 | 34 | 33 | FOBS= | 127.3 | SIGMA= | 1.6 | PHAS= | -24.0 | FOM= | 0.38 | TEST= 0 |
| INDE | 9 | 34 | 35 | FOBS= | 128.1 | SIGMA= | 1.6 | PHAS= | 172.5 | FOM= | 0.96 | TEST= 0 |
| INDE | 9 | 34 | 37 | FOBS= | 42.1 | SIGMA= | 4.7 | PHAS= | 15.8 | FOM= | 0.61 | TEST= 0 |
| INDE | 9 | 34 | 39 | FOBS= | 61.7 | SIGMA= | 3.2 | PHAS= | 44.4 | FOM= | 0.93 | TEST= 0 |
| INDE | 9 | 34 | 41 | FOBS= | 71.4 | SIGMA= | 2.6 | PHAS= | -133.6 | FOM= | 0.85 | TEST= 1 |
| INDE | 9 | 34 | 43 | FOBS= | 80.2 | SIGMA= | 2.6 | PHAS= | 150.0 | FOM= | 0.45 | TEST= 0 |
| INDE | 9 | 34 | 45 | FOBS= | 181.6 | SIGMA= | 1.4 | PHAS= | 69.3 | FOM= | 0.95 | TEST= 0 |
| INDE | 9 | 34 | 47 | FOBS= | 84.6 | SIGMA= | 2.7 | PHAS= | -83.9 | FOM= | 0.69 | TEST= 0 |
| INDE | 9 | 34 | 49 | FOBS= | 83.9 | SIGMA= | 2.7 | PHAS= | -101.9 | FOM= | 0.73 | TEST= 0 |
| INDE | 9 | 34 | 51 | FOBS= | 0.0 | SIGMA= | 19.9 | PHAS= | 0.0 | FOM= | 0.00 | TEST= 1 |
| INDE | 9 | 34 | 53 | FOBS= | 45.2 | SIGMA= | 4.1 | PHAS= | -70.5 | FOM= | 0.69 | TEST= 0 |
| INDE | 9 | 34 | 55 | FOBS= | 84.2 | SIGMA= | 2.5 | PHAS= | 20.7 | FOM= | 0.86 | TEST= 0 |
| INDE | 9 | 34 | 57 | FOBS= | 96.9 | SIGMA= | 2.2 | PHAS= | 70.6 | FOM= | 0.95 | TEST= 0 |
| INDE | 9 | 34 | 59 | FOBS= | 0.0 | SIGMA= | 18.5 | PHAS= | 0.0 | FOM= | 0.00 | TEST= 0 |
| INDE | 9 | 34 | 61 | FOBS= | 17.4 | SIGMA= | 12.0 | PHAS= | -13.0 | FOM= | 0.11 | TEST= 0 |
| INDE | 9 | 34 | 63 | FOBS= | 24.2 | SIGMA= | 7.2 | PHAS= | -110.4 | FOM= | 0.35 | TEST= 0 |
| INDE | 9 | 34 | 65 | FOBS= | 60.0 | SIGMA= | 3.1 | PHAS= | -54.3 | FOM= | 0.90 | TEST= 0 |
| INDE | 9 | 34 | 67 | FOBS= | 39.7 | SIGMA= | 5.6 | PHAS= | 15.1 | FOM= | 0.64 | TEST= 0 |
| INDE | 9 | 34 | 69 | FOBS= | 64.3 | SIGMA= | 8.3 | PHAS= | -83.2 | FOM= | 0.86 | TEST= 0 |
| INDE | 9 | 35 | 10 | FOBS= | 389.8 | SIGMA= | 0.6 | PHAS= | 147.6 | FOM= | 0.96 | TEST= 1 |
| INDE | 9 | 35 | 12 | FOBS= | 120.4 | SIGMA= | 1.1 | PHAS= | -83.4 | FOM= | 0.27 | TEST= 0 |
| INDE | 9 | 35 | 14 | FOBS= | 152.1 | SIGMA= | 1.0 | PHAS= | 135.4 | FOM= | 0.90 | TEST= 0 |
| INDE | 9 | 35 | 16 | FOBS= | 156.0 | SIGMA= | 1.2 | PHAS= | 90.8 | FOM= | 0.97 | TEST= 0 |
| INDE | 9 | 35 | 18 | FOBS= | 60.0 | SIGMA= | 2.6 | PHAS= | -22.5 | FOM= | 0.93 | TEST= 0 |
| INDE | 9 | 35 | 20 | FOBS= | 183.6 | SIGMA= | 0.9 | PHAS= | -120.7 | FOM= | 0.99 | TEST= 0 |
| INDE | 9 | 35 | 22 | FOBS= | 73.9 | SIGMA= | 2.2 | PHAS= | -36.2 | FOM= | 0.78 | TEST= 0 |
| INDE | 9 | 35 | 24 | FOBS= | 198.5 | SIGMA= | 1.2 | PHAS= | -6.2 | FOM= | 0.95 | TEST= 0 |
| INDE | 9 | 35 | 26 | FOBS= | 171.8 | SIGMA= | 1.4 | PHAS= | -169.8 | FOM= | 0.91 | TEST= 0 |
| INDE | 9 | 35 | 28 | FOBS= | 97.8 | SIGMA= | 2.0 | PHAS= | 122.9 | FOM= | 0.80 | TEST= 0 |
| INDE | 9 | 35 | 30 | FOBS= | 228.6 | SIGMA= | 1.0 | PHAS= | 120.4 | FOM= | 0.91 | TEST= 0 |
| INDE | 9 | 35 | 32 | FOBS= | 104.6 | SIGMA= | 1.9 | PHAS= | -166.4 | FOM= | 0.93 | TEST= 0 |
| INDE | 9 | 35 | 34 | FOBS= | 20.0 | SIGMA= | 9.9 | PHAS= | 37.5 | FOM= | 0.75 | TEST= 0 |
| INDE | 9 | 35 | 36 | FOBS= | 173.6 | SIGMA= | 1.2 | PHAS= | -124.9 | FOM= | 0.91 | TEST= 0 |
| INDE | 9 | 35 | 38 | FOBS= | 125.0 | SIGMA= | 1.6 | PHAS= | -71.4 | FOM= | 0.66 | TEST= 0 |
| INDE | 9 | 35 | 40 | FOBS= | 48.9 | SIGMA= | 3.9 | PHAS= | -68.8 | FOM= | 0.42 | TEST= 0 |
| INDE | 9 | 35 | 42 | FOBS= | 71.4 | SIGMA= | 2.6 | PHAS= | -44.6 | FOM= | 0.76 | TEST= 0 |
| INDE | 9 | 35 | 44 | FOBS= | 12.0 | SIGMA= | 18.0 | PHAS= | -96.6 | FOM= | 0.55 | TEST= 0 |
| INDE | 9 | 35 | 46 | FOBS= | 80.4 | SIGMA= | 2.8 | PHAS= | -43.7 | FOM= | 0.58 | TEST= 0 |
| INDE | 9 | 35 | 48 | FOBS= | 74.1 | SIGMA= | 3.0 | PHAS= | -102.2 | FOM= | 0.69 | TEST= 0 |
| INDE | 9 | 35 | 50 | FOBS= | 64.0 | SIGMA= | 3.4 | PHAS= | 168.6 | FOM= | 0.70 | TEST= 0 |
| INDE | 9 | 35 | 52 | FOBS= | 56.1 | SIGMA= | 3.9 | PHAS= | -114.6 | FOM= | 0.14 | TEST= 0 |
| INDE | 9 | 35 | 54 | FOBS= | 85.2 | SIGMA= | 2.6 | PHAS= | 138.8 | FOM= | 0.90 | TEST= 0 |
| INDE | 9 | 35 | 56 | FOBS= | 46.4 | SIGMA= | 4.5 | PHAS= | -0.4 | FOM= | 0.20 | TEST= 1 |
| INDE | 9 | 35 | 58 | FOBS= | 40.1 | SIGMA= | 4.4 | PHAS= | 43.9 | FOM= | 0.48 | TEST= 0 |
| INDE | 9 | 35 | 60 | FOBS= | 30.1 | SIGMA= | 5.8 | PHAS= | 179.6 | FOM= | 0.51 | TEST= 0 |
| INDE | 9 | 35 | 62 | FOBS= | 62.8 | SIGMA= | 2.8 | PHAS= | 14.9 | FOM= | 0.75 | TEST= 0 |
| INDE | 9 | 35 | 64 | FOBS= | 92.3 | SIGMA= | 2.0 | PHAS= | -86.8 | FOM= | 0.90 | TEST= 0 |
| INDE | 9 | 35 | 66 | FOBS= | 146.1 | SIGMA= | 1.7 | PHAS= | -146.1 | FOM= | 0.59 | TEST= 1 |
| INDE | 9 | 35 | 68 | FOBS= | 63.7 | SIGMA= | 3.6 | PHAS= | -167.9 | FOM= | 0.87 | TEST= 0 |
| INDE | 9 | 36 | 9 | FOBS= | 426.5 | SIGMA= | 0.7 | PHAS= | 12.9 | FOM= | 0.94 | TEST= 0 |
| INDE | 9 | 36 | 11 | FOBS= | 148.3 | SIGMA= | 1.0 | PHAS= | -153.2 | FOM= | 0.92 | TEST= 1 |
| INDE | 9 | 36 | 13 | FOBS= | 164.0 | SIGMA= | 0.9 | PHAS= | -32.9 | FOM= | 0.98 | TEST= 0 |
| INDE | 9 | 36 | 15 | FOBS= | 294.4 | SIGMA= | 0.7 | PHAS= | 92.2 | FOM= | 0.96 | TEST= 0 |
| INDE | 9 | 36 | 17 | FOBS= | 357.1 | SIGMA= | 0.9 | PHAS= | 33.5 | FOM= | 0.97 | TEST= 0 |
| INDE | 9 | 36 | 19 | FOBS= | 149.3 | SIGMA= | 1.2 | PHAS= | 137.2 | FOM= | 0.93 | TEST= 0 |
| INDE | 9 | 36 | 21 | FOBS= | 399.1 | SIGMA= | 0.7 | PHAS= | -149.8 | FOM= | 0.96 | TEST= 0 |
| INDE | 9 | 36 | 23 | FOBS= | 287.4 | SIGMA= | 0.8 | PHAS= | 15.1 | FOM= | 0.56 | TEST= 1 |
| INDE | 9 | 36 | 25 | FOBS= | 200.6 | SIGMA= | 1.3 | PHAS= | 134.4 | FOM= | 0.95 | TEST= 0 |
| INDE | 9 | 36 | 27 | FOBS= | 14.9 | SIGMA= | 18.3 | PHAS= | -147.7 | FOM= | 0.08 | TEST= 0 |
| INDE | 9 | 36 | 29 | FOBS= | 145.3 | SIGMA= | 1.5 | PHAS= | -46.2 | FOM= | 0.94 | TEST= 0 |
| INDE | 9 | 36 | 31 | FOBS= | 96.4 | SIGMA= | 2.2 | PHAS= | 156.6 | FOM= | 0.91 | TEST= 0 |
| INDE | 9 | 36 | 33 | FOBS= | 135.2 | SIGMA= | 1.5 | PHAS= | 64.6 | FOM= | 0.75 | TEST= 0 |
| INDE | 9 | 36 | 35 | FOBS= | 155.7 | SIGMA= | 1.3 | PHAS= | 154.0 | FOM= | 0.97 | TEST= 0 |
| INDE | 9 | 36 | 37 | FOBS= | 129.7 | SIGMA= | 1.6 | PHAS= | -151.9 | FOM= | 0.47 | TEST= 0 |
| INDE | 9 | 36 | 39 | FOBS= | 162.9 | SIGMA= | 1.3 | PHAS= | -134.1 | FOM= | 0.82 | TEST= 0 |
| INDE | 9 | 36 | 41 | FOBS= | 64.8 | SIGMA= | 2.9 | PHAS= | -150.4 | FOM= | 0.66 | TEST= 0 |
| INDE | 9 | 36 | 43 | FOBS= | 58.1 | SIGMA= | 3.2 | PHAS= | 86.8 | FOM= | 0.26 | TEST= 0 |

*FIG. 12A - 246*

```
INDE  9  36  45  FOBS=   61.1  SIGMA=   3.4  PHAS=  -168.3  FOM=  0.51  TEST=  0
INDE  9  36  47  FOBS=   70.2  SIGMA=   3.2  PHAS=   -99.7  FOM=  0.49  TEST=  0
INDE  9  36  49  FOBS=   80.2  SIGMA=   2.8  PHAS=    11.9  FOM=  0.81  TEST=  0
INDE  9  36  51  FOBS=  114.6  SIGMA=   2.0  PHAS=  -178.6  FOM=  0.89  TEST=  0
INDE  9  36  53  FOBS=   28.6  SIGMA=   8.1  PHAS=    72.2  FOM=  0.19  TEST=  1
INDE  9  36  55  FOBS=   39.8  SIGMA=   5.3  PHAS=   -21.2  FOM=  0.30  TEST=  0
INDE  9  36  57  FOBS=   25.1  SIGMA=   9.0  PHAS=    97.7  FOM=  0.76  TEST=  0
INDE  9  36  59  FOBS=   47.2  SIGMA=   3.8  PHAS=    15.3  FOM=  0.69  TEST=  0
INDE  9  36  61  FOBS=   35.8  SIGMA=   5.3  PHAS=  -120.3  FOM=  0.54  TEST=  0
INDE  9  36  63  FOBS=   14.2  SIGMA=  14.7  PHAS=   -87.6  FOM=  0.12  TEST=  0
INDE  9  36  65  FOBS=   63.0  SIGMA=   2.9  PHAS=  -168.3  FOM=  0.89  TEST=  0
INDE  9  36  67  FOBS=   52.8  SIGMA=   4.4  PHAS=   145.6  FOM=  0.80  TEST=  0
INDE  9  37  10  FOBS=  115.1  SIGMA=   1.1  PHAS=   -24.4  FOM=  0.95  TEST=  0
INDE  9  37  12  FOBS=   39.8  SIGMA=   4.0  PHAS=    55.3  FOM=  0.63  TEST=  0
INDE  9  37  14  FOBS=   76.1  SIGMA=   1.9  PHAS=  -132.0  FOM=  0.87  TEST=  0
INDE  9  37  16  FOBS=  219.0  SIGMA=   0.8  PHAS=   -31.4  FOM=  0.94  TEST=  0
INDE  9  37  18  FOBS=  203.4  SIGMA=   1.0  PHAS=    12.2  FOM=  0.96  TEST=  1
INDE  9  37  20  FOBS=  288.8  SIGMA=   0.8  PHAS=    89.8  FOM=  0.96  TEST=  0
INDE  9  37  22  FOBS=  266.8  SIGMA=   0.8  PHAS=   111.2  FOM=  0.96  TEST=  0
INDE  9  37  24  FOBS=  183.7  SIGMA=   1.1  PHAS=  -100.8  FOM=  0.63  TEST=  1
INDE  9  37  26  FOBS=  166.6  SIGMA=   1.5  PHAS=     2.2  FOM=  0.92  TEST=  0
INDE  9  37  28  FOBS=   70.0  SIGMA=   3.6  PHAS=  -120.3  FOM=  0.73  TEST=  0
INDE  9  37  30  FOBS=  126.8  SIGMA=   1.8  PHAS=   161.5  FOM=  0.79  TEST=  0
INDE  9  37  32  FOBS=  134.8  SIGMA=   1.5  PHAS=    64.0  FOM=  0.86  TEST=  0
INDE  9  37  34  FOBS=  188.5  SIGMA=   1.1  PHAS=    39.5  FOM=  0.93  TEST=  0
INDE  9  37  36  FOBS=  222.1  SIGMA=   1.0  PHAS=   115.7  FOM=  0.94  TEST=  0
INDE  9  37  38  FOBS=   84.8  SIGMA=   2.3  PHAS=   152.4  FOM=  0.85  TEST=  0
INDE  9  37  40  FOBS=  173.1  SIGMA=   1.2  PHAS=   151.6  FOM=  0.88  TEST=  0
INDE  9  37  42  FOBS=  105.4  SIGMA=   1.8  PHAS=    -2.6  FOM=  0.35  TEST=  0
INDE  9  37  44  FOBS=  100.2  SIGMA=   1.9  PHAS=    67.6  FOM=  0.84  TEST=  0
INDE  9  37  46  FOBS=   49.3  SIGMA=   3.7  PHAS=  -111.8  FOM=  0.15  TEST=  1
INDE  9  37  48  FOBS=  108.2  SIGMA=   2.1  PHAS=   -96.4  FOM=  0.92  TEST=  0
INDE  9  37  50  FOBS=   44.5  SIGMA=   4.9  PHAS=    70.6  FOM=  0.39  TEST=  0
INDE  9  37  52  FOBS=  110.2  SIGMA=   2.0  PHAS=    23.6  FOM=  0.92  TEST=  0
INDE  9  37  54  FOBS=   26.1  SIGMA=   8.8  PHAS=   -84.8  FOM=  0.22  TEST=  0
INDE  9  37  56  FOBS=    4.4  SIGMA=  52.1  PHAS=   -37.5  FOM=  0.08  TEST=  0
INDE  9  37  58  FOBS=   62.1  SIGMA=   2.9  PHAS=  -131.5  FOM=  0.61  TEST=  0
INDE  9  37  60  FOBS=    0.0  SIGMA=  22.6  PHAS=     0.0  FOM=  0.00  TEST=  0
INDE  9  37  62  FOBS=   43.1  SIGMA=   4.2  PHAS=  -159.8  FOM=  0.69  TEST=  0
INDE  9  37  64  FOBS=   81.5  SIGMA=   2.3  PHAS=   -17.4  FOM=  0.77  TEST=  0
INDE  9  37  66  FOBS=    0.0  SIGMA=  27.8  PHAS=     0.0  FOM=  0.00  TEST=  0
INDE  9  38   9  FOBS=  131.8  SIGMA=   1.1  PHAS=  -123.0  FOM=  0.98  TEST=  0
INDE  9  38  11  FOBS=  129.6  SIGMA=   1.1  PHAS=   -82.1  FOM=  0.83  TEST=  0
INDE  9  38  13  FOBS=   96.3  SIGMA=   1.6  PHAS=   166.7  FOM=  0.78  TEST=  0
INDE  9  38  15  FOBS=  117.0  SIGMA=   1.4  PHAS=  -134.7  FOM=  0.96  TEST=  0
INDE  9  38  17  FOBS=  162.4  SIGMA=   1.1  PHAS=    97.0  FOM=  0.74  TEST=  0
INDE  9  38  19  FOBS=  154.4  SIGMA=   1.2  PHAS=   -43.8  FOM=  0.95  TEST=  0
INDE  9  38  21  FOBS=  142.0  SIGMA=   1.3  PHAS=   -19.6  FOM=  0.93  TEST=  0
INDE  9  38  23  FOBS=  237.1  SIGMA=   0.9  PHAS=     4.5  FOM=  0.93  TEST=  0
INDE  9  38  25  FOBS=  173.0  SIGMA=   1.2  PHAS=  -107.9  FOM=  0.83  TEST=  1
INDE  9  38  27  FOBS=  289.8  SIGMA=   1.1  PHAS=  -144.4  FOM=  0.97  TEST=  0
INDE  9  38  29  FOBS=    0.0  SIGMA=  21.0  PHAS=     0.0  FOM=  0.00  TEST=  0
INDE  9  38  31  FOBS=   37.2  SIGMA=   5.9  PHAS=   -18.6  FOM=  0.19  TEST=  0
INDE  9  38  33  FOBS=  167.6  SIGMA=   1.2  PHAS=   -47.9  FOM=  0.86  TEST=  0
INDE  9  38  35  FOBS=  272.8  SIGMA=   1.0  PHAS=   -47.4  FOM=  0.98  TEST=  0
INDE  9  38  37  FOBS=  111.0  SIGMA=   1.8  PHAS=   172.0  FOM=  0.66  TEST=  0
INDE  9  38  39  FOBS=  153.8  SIGMA=   1.3  PHAS=    96.1  FOM=  0.93  TEST=  0
INDE  9  38  41  FOBS=   81.7  SIGMA=   2.3  PHAS=    85.9  FOM=  0.80  TEST=  0
INDE  9  38  43  FOBS=   71.3  SIGMA=   2.6  PHAS=     1.3  FOM=  0.76  TEST=  0
INDE  9  38  45  FOBS=  141.0  SIGMA=   1.4  PHAS=   -49.6  FOM=  0.91  TEST=  0
INDE  9  38  47  FOBS=   93.3  SIGMA=   2.0  PHAS=   143.2  FOM=  0.88  TEST=  0
INDE  9  38  49  FOBS=    0.0  SIGMA=  22.7  PHAS=     0.0  FOM=  0.00  TEST=  0
INDE  9  38  51  FOBS=   23.0  SIGMA=   9.4  PHAS=   145.2  FOM=  0.39  TEST=  0
INDE  9  38  53  FOBS=  142.2  SIGMA=   1.6  PHAS=  -133.8  FOM=  0.92  TEST=  0
INDE  9  38  55  FOBS=   63.6  SIGMA=   3.4  PHAS=   168.5  FOM=  0.73  TEST=  0
INDE  9  38  57  FOBS=  127.0  SIGMA=   1.8  PHAS=   155.9  FOM=  0.87  TEST=  1
INDE  9  38  59  FOBS=    0.0  SIGMA=  19.5  PHAS=     0.0  FOM=  0.00  TEST=  0
INDE  9  38  61  FOBS=   61.4  SIGMA=   3.0  PHAS=    76.9  FOM=  0.75  TEST=  1
INDE  9  38  63  FOBS=   29.8  SIGMA=   6.4  PHAS=   157.7  FOM=  0.60  TEST=  0
INDE  9  38  65  FOBS=    0.0  SIGMA=  20.5  PHAS=     0.0  FOM=  0.00  TEST=  1
```

*FIG. 12A - 247*

| | | | | | | | | | | | | |
|---|---|---|---|---|---|---|---|---|---|---|---|---|
| INDE | 9 | 38 | 67 | FOBS= | 25.7 | SIGMA= | 11.4 | PHAS= | -152.9 | FOM= | 0.43 | TEST= 0 |
| INDE | 9 | 39 | 10 | FOBS= | 189.0 | SIGMA= | 0.9 | PHAS= | -174.8 | FOM= | 0.96 | TEST= 0 |
| INDE | 9 | 39 | 12 | FOBS= | 170.4 | SIGMA= | 1.0 | PHAS= | 8.6 | FOM= | 0.83 | TEST= 0 |
| INDE | 9 | 39 | 14 | FOBS= | 7.0 | SIGMA= | 21.9 | PHAS= | -29.6 | FOM= | 0.02 | TEST= 0 |
| INDE | 9 | 39 | 16 | FOBS= | 123.1 | SIGMA= | 1.4 | PHAS= | 38.6 | FOM= | 0.93 | TEST= 0 |
| INDE | 9 | 39 | 18 | FOBS= | 240.5 | SIGMA= | 0.9 | PHAS= | 114.8 | FOM= | 0.98 | TEST= 0 |
| INDE | 9 | 39 | 20 | FOBS= | 109.4 | SIGMA= | 1.7 | PHAS= | -169.5 | FOM= | 0.88 | TEST= 0 |
| INDE | 9 | 39 | 22 | FOBS= | 230.7 | SIGMA= | 1.0 | PHAS= | -85.7 | FOM= | 0.98 | TEST= 0 |
| INDE | 9 | 39 | 24 | FOBS= | 287.3 | SIGMA= | 0.8 | PHAS= | 138.1 | FOM= | 0.92 | TEST= 1 |
| INDE | 9 | 39 | 26 | FOBS= | 168.4 | SIGMA= | 1.3 | PHAS= | -80.0 | FOM= | 0.97 | TEST= 0 |
| INDE | 9 | 39 | 28 | FOBS= | 116.3 | SIGMA= | 2.3 | PHAS= | 168.2 | FOM= | 0.68 | TEST= 0 |
| INDE | 9 | 39 | 30 | FOBS= | 55.1 | SIGMA= | 4.0 | PHAS= | 17.5 | FOM= | 0.61 | TEST= 0 |
| INDE | 9 | 39 | 32 | FOBS= | 154.2 | SIGMA= | 1.5 | PHAS= | -94.3 | FOM= | 0.88 | TEST= 0 |
| INDE | 9 | 39 | 34 | FOBS= | 193.6 | SIGMA= | 1.1 | PHAS= | -166.8 | FOM= | 0.97 | TEST= 0 |
| INDE | 9 | 39 | 36 | FOBS= | 317.8 | SIGMA= | 0.8 | PHAS= | 158.7 | FOM= | 0.98 | TEST= 0 |
| INDE | 9 | 39 | 38 | FOBS= | 121.2 | SIGMA= | 1.7 | PHAS= | -1.8 | FOM= | 0.91 | TEST= 0 |
| INDE | 9 | 39 | 40 | FOBS= | 152.6 | SIGMA= | 1.3 | PHAS= | 49.6 | FOM= | 0.93 | TEST= 0 |
| INDE | 9 | 39 | 42 | FOBS= | 80.3 | SIGMA= | 2.4 | PHAS= | -73.9 | FOM= | 0.76 | TEST= 0 |
| INDE | 9 | 39 | 44 | FOBS= | 138.5 | SIGMA= | 1.4 | PHAS= | -154.8 | FOM= | 0.29 | TEST= 1 |
| INDE | 9 | 39 | 46 | FOBS= | 167.9 | SIGMA= | 1.2 | PHAS= | 52.5 | FOM= | 0.97 | TEST= 0 |
| INDE | 9 | 39 | 48 | FOBS= | 0.0 | SIGMA= | 19.9 | PHAS= | 0.0 | FOM= | 0.00 | TEST= 0 |
| INDE | 9 | 39 | 50 | FOBS= | 60.9 | SIGMA= | 3.6 | PHAS= | 82.3 | FOM= | 0.56 | TEST= 0 |
| INDE | 9 | 39 | 52 | FOBS= | 126.1 | SIGMA= | 1.8 | PHAS= | 71.4 | FOM= | 0.80 | TEST= 1 |
| INDE | 9 | 39 | 54 | FOBS= | 103.0 | SIGMA= | 2.1 | PHAS= | 66.6 | FOM= | 0.81 | TEST= 0 |
| INDE | 9 | 39 | 56 | FOBS= | 52.1 | SIGMA= | 4.1 | PHAS= | 118.0 | FOM= | 0.85 | TEST= 0 |
| INDE | 9 | 39 | 58 | FOBS= | 52.4 | SIGMA= | 3.5 | PHAS= | 82.3 | FOM= | 0.43 | TEST= 1 |
| INDE | 9 | 39 | 60 | FOBS= | 59.2 | SIGMA= | 3.1 | PHAS= | 44.7 | FOM= | 0.78 | TEST= 0 |
| INDE | 9 | 39 | 62 | FOBS= | 0.0 | SIGMA= | 20.5 | PHAS= | 0.0 | FOM= | 0.00 | TEST= 0 |
| INDE | 9 | 39 | 64 | FOBS= | 16.3 | SIGMA= | 13.1 | PHAS= | 70.6 | FOM= | 0.20 | TEST= 0 |
| INDE | 9 | 39 | 66 | FOBS= | 0.0 | SIGMA= | 21.8 | PHAS= | 0.0 | FOM= | 0.00 | TEST= 0 |
| INDE | 9 | 40 | 9 | FOBS= | 132.4 | SIGMA= | 1.3 | PHAS= | -80.6 | FOM= | 0.87 | TEST= 0 |
| INDE | 9 | 40 | 11 | FOBS= | 282.1 | SIGMA= | 1.1 | PHAS= | -125.6 | FOM= | 0.96 | TEST= 0 |
| INDE | 9 | 40 | 13 | FOBS= | 353.2 | SIGMA= | 0.7 | PHAS= | -108.1 | FOM= | 0.97 | TEST= 0 |
| INDE | 9 | 40 | 15 | FOBS= | 95.8 | SIGMA= | 1.8 | PHAS= | -70.2 | FOM= | 0.87 | TEST= 0 |
| INDE | 9 | 40 | 17 | FOBS= | 203.3 | SIGMA= | 1.0 | PHAS= | 9.4 | FOM= | 0.95 | TEST= 0 |
| INDE | 9 | 40 | 19 | FOBS= | 279.7 | SIGMA= | 0.9 | PHAS= | -19.6 | FOM= | 0.95 | TEST= 0 |
| INDE | 9 | 40 | 21 | FOBS= | 44.6 | SIGMA= | 4.3 | PHAS= | -142.2 | FOM= | 0.86 | TEST= 0 |
| INDE | 9 | 40 | 23 | FOBS= | 254.7 | SIGMA= | 0.9 | PHAS= | 135.2 | FOM= | 0.95 | TEST= 0 |
| INDE | 9 | 40 | 25 | FOBS= | 178.7 | SIGMA= | 1.2 | PHAS= | 107.3 | FOM= | 0.97 | TEST= 0 |
| INDE | 9 | 40 | 27 | FOBS= | 266.0 | SIGMA= | 1.2 | PHAS= | -161.9 | FOM= | 0.97 | TEST= 0 |
| INDE | 9 | 40 | 29 | FOBS= | 102.8 | SIGMA= | 2.6 | PHAS= | -7.3 | FOM= | 0.89 | TEST= 0 |
| INDE | 9 | 40 | 31 | FOBS= | 56.5 | SIGMA= | 3.8 | PHAS= | -104.8 | FOM= | 0.91 | TEST= 1 |
| INDE | 9 | 40 | 33 | FOBS= | 117.3 | SIGMA= | 1.9 | PHAS= | 161.3 | FOM= | 0.94 | TEST= 0 |
| INDE | 9 | 40 | 35 | FOBS= | 262.3 | SIGMA= | 0.9 | PHAS= | 58.9 | FOM= | 0.98 | TEST= 0 |
| INDE | 9 | 40 | 37 | FOBS= | 96.0 | SIGMA= | 2.0 | PHAS= | -49.9 | FOM= | 0.89 | TEST= 0 |
| INDE | 9 | 40 | 39 | FOBS= | 76.2 | SIGMA= | 2.5 | PHAS= | 46.8 | FOM= | 0.74 | TEST= 0 |
| INDE | 9 | 40 | 41 | FOBS= | 106.8 | SIGMA= | 1.8 | PHAS= | 8.3 | FOM= | 0.77 | TEST= 0 |
| INDE | 9 | 40 | 43 | FOBS= | 233.6 | SIGMA= | 1.0 | PHAS= | 153.8 | FOM= | 0.97 | TEST= 0 |
| INDE | 9 | 40 | 45 | FOBS= | 110.9 | SIGMA= | 1.7 | PHAS= | -70.1 | FOM= | 0.90 | TEST= 0 |
| INDE | 9 | 40 | 47 | FOBS= | 82.5 | SIGMA= | 2.2 | PHAS= | 0.4 | FOM= | 0.87 | TEST= 0 |
| INDE | 9 | 40 | 49 | FOBS= | 45.1 | SIGMA= | 4.7 | PHAS= | -178.3 | FOM= | 0.50 | TEST= 0 |
| INDE | 9 | 40 | 51 | FOBS= | 0.0 | SIGMA= | 20.9 | PHAS= | 0.0 | FOM= | 0.00 | TEST= 0 |
| INDE | 9 | 40 | 53 | FOBS= | 22.3 | SIGMA= | 9.7 | PHAS= | -154.8 | FOM= | 0.34 | TEST= 0 |
| INDE | 9 | 40 | 55 | FOBS= | 81.5 | SIGMA= | 2.7 | PHAS= | -64.1 | FOM= | 0.83 | TEST= 0 |
| INDE | 9 | 40 | 57 | FOBS= | 136.8 | SIGMA= | 1.7 | PHAS= | 74.0 | FOM= | 0.93 | TEST= 0 |
| INDE | 9 | 40 | 59 | FOBS= | 89.0 | SIGMA= | 2.1 | PHAS= | -88.1 | FOM= | 0.95 | TEST= 0 |
| INDE | 9 | 40 | 61 | FOBS= | 63.6 | SIGMA= | 2.9 | PHAS= | 33.8 | FOM= | 0.73 | TEST= 0 |
| INDE | 9 | 40 | 63 | FOBS= | 0.0 | SIGMA= | 20.7 | PHAS= | 0.0 | FOM= | 0.00 | TEST= 0 |
| INDE | 9 | 40 | 65 | FOBS= | 0.0 | SIGMA= | 20.9 | PHAS= | 0.0 | FOM= | 0.00 | TEST= 0 |
| INDE | 9 | 41 | 10 | FOBS= | 421.6 | SIGMA= | 0.8 | PHAS= | 160.6 | FOM= | 0.97 | TEST= 0 |
| INDE | 9 | 41 | 12 | FOBS= | 405.0 | SIGMA= | 0.7 | PHAS= | -169.2 | FOM= | 0.99 | TEST= 0 |
| INDE | 9 | 41 | 14 | FOBS= | 289.4 | SIGMA= | 0.8 | PHAS= | 167.0 | FOM= | 0.94 | TEST= 0 |
| INDE | 9 | 41 | 16 | FOBS= | 109.1 | SIGMA= | 1.7 | PHAS= | -19.2 | FOM= | 0.87 | TEST= 0 |
| INDE | 9 | 41 | 18 | FOBS= | 361.9 | SIGMA= | 0.7 | PHAS= | -156.3 | FOM= | 0.98 | TEST= 0 |
| INDE | 9 | 41 | 20 | FOBS= | 150.7 | SIGMA= | 1.5 | PHAS= | -112.4 | FOM= | 0.95 | TEST= 0 |
| INDE | 9 | 41 | 22 | FOBS= | 140.2 | SIGMA= | 1.5 | PHAS= | 86.9 | FOM= | 0.93 | TEST= 0 |
| INDE | 9 | 41 | 24 | FOBS= | 121.0 | SIGMA= | 1.8 | PHAS= | 66.2 | FOM= | 0.80 | TEST= 0 |
| INDE | 9 | 41 | 26 | FOBS= | 136.9 | SIGMA= | 1.6 | PHAS= | -6.8 | FOM= | 0.95 | TEST= 1 |
| INDE | 9 | 41 | 28 | FOBS= | 219.6 | SIGMA= | 1.3 | PHAS= | 21.8 | FOM= | 0.73 | TEST= 1 |
| INDE | 9 | 41 | 30 | FOBS= | 70.7 | SIGMA= | 3.6 | PHAS= | -59.2 | FOM= | 0.07 | TEST= 0 |

*FIG. 12A - 248*

| | | | | | | | | | | | | |
|---|---|---|---|---|---|---|---|---|---|---|---|---|
| INDE | 9 | 41 | 32 | FOBS= | 201.1 | SIGMA= | 1.2 | PHAS= | -142.1 | FOM= | 0.91 | TEST= 0 |
| INDE | 9 | 41 | 34 | FOBS= | 79.0 | SIGMA= | 2.6 | PHAS= | 55.8 | FOM= | 0.84 | TEST= 0 |
| INDE | 9 | 41 | 36 | FOBS= | 68.3 | SIGMA= | 2.9 | PHAS= | 170.4 | FOM= | 0.48 | TEST= 0 |
| INDE | 9 | 41 | 38 | FOBS= | 66.8 | SIGMA= | 2.9 | PHAS= | -144.5 | FOM= | 0.83 | TEST= 0 |
| INDE | 9 | 41 | 40 | FOBS= | 48.0 | SIGMA= | 4.0 | PHAS= | -3.1 | FOM= | 0.79 | TEST= 0 |
| INDE | 9 | 41 | 42 | FOBS= | 72.7 | SIGMA= | 2.7 | PHAS= | 76.6 | FOM= | 0.85 | TEST= 0 |
| INDE | 9 | 41 | 44 | FOBS= | 125.9 | SIGMA= | 1.6 | PHAS= | 70.2 | FOM= | 0.97 | TEST= 0 |
| INDE | 9 | 41 | 46 | FOBS= | 35.1 | SIGMA= | 5.5 | PHAS= | 20.5 | FOM= | 0.38 | TEST= 0 |
| INDE | 9 | 41 | 48 | FOBS= | 83.1 | SIGMA= | 2.2 | PHAS= | 37.9 | FOM= | 0.69 | TEST= 0 |
| INDE | 9 | 41 | 50 | FOBS= | 0.0 | SIGMA= | 19.8 | PHAS= | 0.0 | FOM= | 0.00 | TEST= 0 |
| INDE | 9 | 41 | 52 | FOBS= | 99.5 | SIGMA= | 2.2 | PHAS= | 103.5 | FOM= | 0.93 | TEST= 0 |
| INDE | 9 | 41 | 54 | FOBS= | 16.3 | SIGMA= | 13.2 | PHAS= | 93.0 | FOM= | 0.32 | TEST= 0 |
| INDE | 9 | 41 | 56 | FOBS= | 125.6 | SIGMA= | 1.8 | PHAS= | -70.2 | FOM= | 0.95 | TEST= 0 |
| INDE | 9 | 41 | 58 | FOBS= | 78.9 | SIGMA= | 2.4 | PHAS= | -88.3 | FOM= | 0.88 | TEST= 0 |
| INDE | 9 | 41 | 60 | FOBS= | 55.5 | SIGMA= | 3.4 | PHAS= | -154.3 | FOM= | 0.48 | TEST= 0 |
| INDE | 9 | 41 | 62 | FOBS= | 0.0 | SIGMA= | 19.9 | PHAS= | 0.0 | FOM= | 0.00 | TEST= 0 |
| INDE | 9 | 41 | 64 | FOBS= | 0.0 | SIGMA= | 20.9 | PHAS= | 0.0 | FOM= | 0.00 | TEST= 0 |
| INDE | 9 | 42 | 9 | FOBS= | 90.0 | SIGMA= | 1.9 | PHAS= | 85.3 | FOM= | 0.95 | TEST= 0 |
| INDE | 9 | 42 | 11 | FOBS= | 242.7 | SIGMA= | 1.1 | PHAS= | 64.9 | FOM= | 0.95 | TEST= 1 |
| INDE | 9 | 42 | 13 | FOBS= | 215.6 | SIGMA= | 1.0 | PHAS= | 138.0 | FOM= | 0.50 | TEST= 1 |
| INDE | 9 | 42 | 15 | FOBS= | 98.5 | SIGMA= | 1.9 | PHAS= | -94.3 | FOM= | 0.26 | TEST= 0 |
| INDE | 9 | 42 | 17 | FOBS= | 254.9 | SIGMA= | 0.9 | PHAS= | 103.1 | FOM= | 0.92 | TEST= 0 |
| INDE | 9 | 42 | 19 | FOBS= | 51.4 | SIGMA= | 4.1 | PHAS= | -27.9 | FOM= | 0.85 | TEST= 0 |
| INDE | 9 | 42 | 21 | FOBS= | 38.4 | SIGMA= | 5.4 | PHAS= | -9.6 | FOM= | 0.38 | TEST= 0 |
| INDE | 9 | 42 | 23 | FOBS= | 50.0 | SIGMA= | 4.7 | PHAS= | 123.7 | FOM= | 0.78 | TEST= 0 |
| INDE | 9 | 42 | 25 | FOBS= | 157.8 | SIGMA= | 1.4 | PHAS= | -86.7 | FOM= | 0.97 | TEST= 0 |
| INDE | 9 | 42 | 27 | FOBS= | 124.2 | SIGMA= | 1.7 | PHAS= | -33.1 | FOM= | 0.93 | TEST= 0 |
| INDE | 9 | 42 | 29 | FOBS= | 161.6 | SIGMA= | 1.7 | PHAS= | -54.7 | FOM= | 0.85 | TEST= 0 |
| INDE | 9 | 42 | 31 | FOBS= | 62.9 | SIGMA= | 3.7 | PHAS= | 105.0 | FOM= | 0.23 | TEST= 0 |
| INDE | 9 | 42 | 33 | FOBS= | 74.2 | SIGMA= | 2.9 | PHAS= | 98.4 | FOM= | 0.23 | TEST= 0 |
| INDE | 9 | 42 | 35 | FOBS= | 61.8 | SIGMA= | 3.1 | PHAS= | 35.6 | FOM= | 0.88 | TEST= 0 |
| INDE | 9 | 42 | 37 | FOBS= | 95.4 | SIGMA= | 2.0 | PHAS= | -2.2 | FOM= | 0.87 | TEST= 0 |
| INDE | 9 | 42 | 39 | FOBS= | 34.1 | SIGMA= | 5.6 | PHAS= | 107.5 | FOM= | 0.86 | TEST= 0 |
| INDE | 9 | 42 | 41 | FOBS= | 0.0 | SIGMA= | 19.4 | PHAS= | 0.0 | FOM= | 0.00 | TEST= 0 |
| INDE | 9 | 42 | 43 | FOBS= | 0.0 | SIGMA= | 19.2 | PHAS= | 0.0 | FOM= | 0.00 | TEST= 0 |
| INDE | 9 | 42 | 45 | FOBS= | 56.1 | SIGMA= | 3.3 | PHAS= | -107.5 | FOM= | 0.54 | TEST= 0 |
| INDE | 9 | 42 | 47 | FOBS= | 44.0 | SIGMA= | 4.1 | PHAS= | 117.7 | FOM= | 0.69 | TEST= 0 |
| INDE | 9 | 42 | 49 | FOBS= | 160.9 | SIGMA= | 1.2 | PHAS= | 168.1 | FOM= | 0.87 | TEST= 0 |
| INDE | 9 | 42 | 51 | FOBS= | 0.0 | SIGMA= | 20.4 | PHAS= | 0.0 | FOM= | 0.00 | TEST= 0 |
| INDE | 9 | 42 | 53 | FOBS= | 28.3 | SIGMA= | 8.4 | PHAS= | 144.0 | FOM= | 0.42 | TEST= 0 |
| INDE | 9 | 42 | 55 | FOBS= | 0.0 | SIGMA= | 20.8 | PHAS= | 0.0 | FOM= | 0.00 | TEST= 0 |
| INDE | 9 | 42 | 57 | FOBS= | 80.7 | SIGMA= | 2.7 | PHAS= | -145.1 | FOM= | 0.80 | TEST= 0 |
| INDE | 9 | 42 | 59 | FOBS= | 57.0 | SIGMA= | 3.3 | PHAS= | 162.8 | FOM= | 0.54 | TEST= 0 |
| INDE | 9 | 42 | 61 | FOBS= | 0.0 | SIGMA= | 20.0 | PHAS= | 0.0 | FOM= | 0.00 | TEST= 0 |
| INDE | 9 | 42 | 63 | FOBS= | 32.4 | SIGMA= | 6.8 | PHAS= | -123.3 | FOM= | 0.76 | TEST= 0 |
| INDE | 9 | 43 | 10 | FOBS= | 297.4 | SIGMA= | 1.2 | PHAS= | 55.4 | FOM= | 0.96 | TEST= 0 |
| INDE | 9 | 43 | 12 | FOBS= | 100.2 | SIGMA= | 2.5 | PHAS= | 174.7 | FOM= | 0.75 | TEST= 0 |
| INDE | 9 | 43 | 14 | FOBS= | 155.8 | SIGMA= | 1.3 | PHAS= | -15.8 | FOM= | 0.87 | TEST= 0 |
| INDE | 9 | 43 | 16 | FOBS= | 247.9 | SIGMA= | 0.9 | PHAS= | 27.3 | FOM= | 0.97 | TEST= 0 |
| INDE | 9 | 43 | 18 | FOBS= | 167.2 | SIGMA= | 1.3 | PHAS= | -141.2 | FOM= | 0.87 | TEST= 0 |
| INDE | 9 | 43 | 20 | FOBS= | 129.4 | SIGMA= | 1.8 | PHAS= | 166.5 | FOM= | 0.90 | TEST= 0 |
| INDE | 9 | 43 | 22 | FOBS= | 157.0 | SIGMA= | 1.4 | PHAS= | 35.7 | FOM= | 0.86 | TEST= 0 |
| INDE | 9 | 43 | 24 | FOBS= | 182.8 | SIGMA= | 1.3 | PHAS= | 167.8 | FOM= | 0.91 | TEST= 0 |
| INDE | 9 | 43 | 26 | FOBS= | 44.1 | SIGMA= | 4.7 | PHAS= | -112.9 | FOM= | 0.23 | TEST= 0 |
| INDE | 9 | 43 | 28 | FOBS= | 124.2 | SIGMA= | 1.7 | PHAS= | -91.9 | FOM= | 0.93 | TEST= 0 |
| INDE | 9 | 43 | 30 | FOBS= | 172.0 | SIGMA= | 1.6 | PHAS= | 172.4 | FOM= | 0.93 | TEST= 0 |
| INDE | 9 | 43 | 32 | FOBS= | 0.0 | SIGMA= | 20.5 | PHAS= | 0.0 | FOM= | 0.00 | TEST= 0 |
| INDE | 9 | 43 | 34 | FOBS= | 9.5 | SIGMA= | 21.6 | PHAS= | -98.2 | FOM= | 0.03 | TEST= 0 |
| INDE | 9 | 43 | 36 | FOBS= | 89.0 | SIGMA= | 2.2 | PHAS= | 6.8 | FOM= | 0.67 | TEST= 0 |
| INDE | 9 | 43 | 38 | FOBS= | 164.7 | SIGMA= | 1.3 | PHAS= | -141.5 | FOM= | 0.96 | TEST= 0 |
| INDE | 9 | 43 | 40 | FOBS= | 70.8 | SIGMA= | 2.7 | PHAS= | 96.8 | FOM= | 0.80 | TEST= 0 |
| INDE | 9 | 43 | 42 | FOBS= | 0.0 | SIGMA= | 20.1 | PHAS= | 0.0 | FOM= | 0.00 | TEST= 0 |
| INDE | 9 | 43 | 44 | FOBS= | 79.1 | SIGMA= | 2.4 | PHAS= | -55.3 | FOM= | 0.85 | TEST= 0 |
| INDE | 9 | 43 | 46 | FOBS= | 118.9 | SIGMA= | 1.6 | PHAS= | -8.1 | FOM= | 0.93 | TEST= 0 |
| INDE | 9 | 43 | 48 | FOBS= | 178.3 | SIGMA= | 1.1 | PHAS= | 59.5 | FOM= | 0.63 | TEST= 1 |
| INDE | 9 | 43 | 50 | FOBS= | 124.3 | SIGMA= | 1.5 | PHAS= | 63.3 | FOM= | 0.87 | TEST= 0 |
| INDE | 9 | 43 | 52 | FOBS= | 40.7 | SIGMA= | 5.3 | PHAS= | 79.9 | FOM= | 0.17 | TEST= 1 |
| INDE | 9 | 43 | 54 | FOBS= | 0.0 | SIGMA= | 22.2 | PHAS= | 0.0 | FOM= | 0.00 | TEST= 0 |
| INDE | 9 | 43 | 56 | FOBS= | 62.4 | SIGMA= | 3.5 | PHAS= | -175.5 | FOM= | 0.77 | TEST= 0 |
| INDE | 9 | 43 | 58 | FOBS= | 0.0 | SIGMA= | 20.1 | PHAS= | 0.0 | FOM= | 0.00 | TEST= 0 |

*FIG. 12A - 249*

```
INDE  9 43 60 FOBS=   0.0 SIGMA= 19.3 PHAS=    0.0 FOM= 0.00 TEST= 0
INDE  9 43 62 FOBS=  55.8 SIGMA=  4.0 PHAS=  123.4 FOM= 0.84 TEST= 0
INDE  9 43 64 FOBS=  39.2 SIGMA=  5.8 PHAS=   -5.9 FOM= 0.46 TEST= 0
INDE  9 44  9 FOBS= 242.1 SIGMA=  0.9 PHAS= -102.0 FOM= 0.94 TEST= 0
INDE  9 44 11 FOBS= 141.0 SIGMA=  1.9 PHAS=  -10.2 FOM= 0.96 TEST= 0
INDE  9 44 13 FOBS= 178.7 SIGMA=  1.1 PHAS=   51.1 FOM= 0.94 TEST= 0
INDE  9 44 15 FOBS= 230.9 SIGMA=  1.0 PHAS= -125.3 FOM= 0.93 TEST= 0
INDE  9 44 17 FOBS= 101.5 SIGMA=  2.1 PHAS=   10.9 FOM= 0.94 TEST= 0
INDE  9 44 19 FOBS= 220.3 SIGMA=  1.1 PHAS=   64.2 FOM= 0.93 TEST= 0
INDE  9 44 21 FOBS= 181.9 SIGMA=  1.2 PHAS=   71.9 FOM= 0.72 TEST= 0
INDE  9 44 23 FOBS= 134.1 SIGMA=  1.6 PHAS=   94.8 FOM= 0.83 TEST= 0
INDE  9 44 25 FOBS=  94.3 SIGMA=  2.3 PHAS=   81.5 FOM= 0.88 TEST= 0
INDE  9 44 27 FOBS=  99.6 SIGMA=  2.1 PHAS=   52.9 FOM= 0.49 TEST= 1
INDE  9 44 29 FOBS= 112.4 SIGMA=  1.9 PHAS=  136.9 FOM= 0.91 TEST= 0
INDE  9 44 31 FOBS=  69.2 SIGMA=  3.6 PHAS=   45.9 FOM= 0.68 TEST= 0
INDE  9 44 33 FOBS=  33.7 SIGMA=  7.7 PHAS=   -6.2 FOM= 0.62 TEST= 0
INDE  9 44 35 FOBS=  41.7 SIGMA=  5.0 PHAS=  -43.5 FOM= 0.21 TEST= 0
INDE  9 44 37 FOBS= 128.5 SIGMA=  1.5 PHAS=  -64.6 FOM= 0.85 TEST= 0
INDE  9 44 39 FOBS= 149.9 SIGMA=  1.4 PHAS=   59.7 FOM= 0.94 TEST= 1
INDE  9 44 41 FOBS=  53.2 SIGMA=  3.5 PHAS=   41.3 FOM= 0.40 TEST= 0
INDE  9 44 43 FOBS=  84.5 SIGMA=  2.2 PHAS=  -74.8 FOM= 0.19 TEST= 1
INDE  9 44 45 FOBS=  99.5 SIGMA=  1.9 PHAS= -170.2 FOM= 0.90 TEST= 0
INDE  9 44 47 FOBS= 165.5 SIGMA=  1.2 PHAS= -121.0 FOM= 0.94 TEST= 0
INDE  9 44 49 FOBS=  99.6 SIGMA=  1.9 PHAS= -106.1 FOM= 0.82 TEST= 0
INDE  9 44 51 FOBS= 100.0 SIGMA=  2.1 PHAS=  -93.8 FOM= 0.29 TEST= 1
INDE  9 44 53 FOBS= 134.3 SIGMA=  1.6 PHAS= -177.6 FOM= 0.96 TEST= 0
INDE  9 44 55 FOBS=  48.5 SIGMA=  4.6 PHAS=  -79.9 FOM= 0.06 TEST= 0
INDE  9 44 57 FOBS=  80.8 SIGMA=  2.8 PHAS=  113.2 FOM= 0.84 TEST= 0
INDE  9 44 59 FOBS=   0.0 SIGMA= 21.0 PHAS=    0.0 FOM= 0.00 TEST= 0
INDE  9 44 61 FOBS=  43.5 SIGMA=  5.1 PHAS=   54.7 FOM= 0.38 TEST= 0
INDE  9 44 63 FOBS=  29.6 SIGMA=  9.7 PHAS= -133.9 FOM= 0.42 TEST= 0
INDE  9 45 10 FOBS= 213.5 SIGMA=  1.0 PHAS= -170.1 FOM= 0.88 TEST= 0
INDE  9 45 12 FOBS=  13.8 SIGMA= 19.2 PHAS=   33.7 FOM= 0.12 TEST= 0
INDE  9 45 14 FOBS= 136.8 SIGMA=  1.5 PHAS=  -90.5 FOM= 0.89 TEST= 0
INDE  9 45 16 FOBS=  66.5 SIGMA=  3.1 PHAS= -158.3 FOM= 0.66 TEST= 0
INDE  9 45 18 FOBS=   0.0 SIGMA= 20.3 PHAS=    0.0 FOM= 0.00 TEST= 0
INDE  9 45 20 FOBS= 107.3 SIGMA=  2.1 PHAS=  -73.5 FOM= 0.73 TEST= 0
INDE  9 45 22 FOBS= 107.0 SIGMA=  2.0 PHAS=   -3.2 FOM= 0.71 TEST= 0
INDE  9 45 24 FOBS=   0.0 SIGMA= 20.3 PHAS=    0.0 FOM= 0.00 TEST= 0
INDE  9 45 26 FOBS=  63.1 SIGMA=  3.3 PHAS=  129.5 FOM= 0.91 TEST= 0
INDE  9 45 28 FOBS=  14.1 SIGMA= 17.8 PHAS=  -20.6 FOM= 0.04 TEST= 0
INDE  9 45 30 FOBS=  26.9 SIGMA=  8.2 PHAS=  141.6 FOM= 0.31 TEST= 0
INDE  9 45 32 FOBS= 135.3 SIGMA=  1.9 PHAS=   16.0 FOM= 0.94 TEST= 0
INDE  9 45 34 FOBS= 146.9 SIGMA=  1.5 PHAS=  173.7 FOM= 0.81 TEST= 0
INDE  9 45 36 FOBS=  12.1 SIGMA= 17.3 PHAS=  161.8 FOM= 0.09 TEST= 0
INDE  9 45 38 FOBS= 107.5 SIGMA=  1.8 PHAS=  -11.3 FOM= 0.77 TEST= 1
INDE  9 45 40 FOBS=  86.1 SIGMA=  2.2 PHAS=  -17.5 FOM= 0.78 TEST= 0
INDE  9 45 42 FOBS=   0.0 SIGMA= 19.1 PHAS=    0.0 FOM= 0.00 TEST= 0
INDE  9 45 44 FOBS=  39.0 SIGMA=  4.7 PHAS= -146.8 FOM= 0.63 TEST= 0
INDE  9 45 46 FOBS= 119.5 SIGMA=  1.6 PHAS=   52.7 FOM= 0.96 TEST= 0
INDE  9 45 48 FOBS=  86.8 SIGMA=  2.2 PHAS=   61.5 FOM= 0.91 TEST= 0
INDE  9 45 50 FOBS=  67.4 SIGMA=  3.0 PHAS=  103.0 FOM= 0.77 TEST= 0
INDE  9 45 52 FOBS= 118.7 SIGMA=  1.8 PHAS=   97.9 FOM= 0.94 TEST= 0
INDE  9 45 54 FOBS= 156.9 SIGMA=  1.4 PHAS=   20.1 FOM= 0.29 TEST= 1
INDE  9 45 56 FOBS=  59.4 SIGMA=  3.7 PHAS=  -83.9 FOM= 0.16 TEST= 1
INDE  9 45 58 FOBS=  54.1 SIGMA=  3.6 PHAS=   32.7 FOM= 0.85 TEST= 0
INDE  9 45 60 FOBS=  52.9 SIGMA=  4.3 PHAS=   -6.3 FOM= 0.47 TEST= 0
INDE  9 45 62 FOBS=   0.0 SIGMA= 21.3 PHAS=    0.0 FOM= 0.00 TEST= 0
INDE  9 46  9 FOBS= 144.0 SIGMA=  1.5 PHAS=  120.3 FOM= 0.88 TEST= 0
INDE  9 46 11 FOBS=  98.5 SIGMA=  2.0 PHAS=   57.1 FOM= 0.95 TEST= 0
INDE  9 46 13 FOBS= 182.2 SIGMA=  1.6 PHAS=  -50.2 FOM= 0.95 TEST= 0
INDE  9 46 15 FOBS= 141.5 SIGMA=  1.5 PHAS= -170.5 FOM= 0.95 TEST= 0
INDE  9 46 17 FOBS= 185.6 SIGMA=  1.2 PHAS=   28.9 FOM= 0.94 TEST= 0
INDE  9 46 19 FOBS= 181.8 SIGMA=  1.2 PHAS=  172.3 FOM= 0.77 TEST= 0
INDE  9 46 21 FOBS= 234.9 SIGMA=  1.0 PHAS=  -28.1 FOM= 0.94 TEST= 0
INDE  9 46 23 FOBS=  94.3 SIGMA=  2.2 PHAS=  158.6 FOM= 0.85 TEST= 0
INDE  9 46 25 FOBS= 133.4 SIGMA=  1.6 PHAS=  102.6 FOM= 0.94 TEST= 0
INDE  9 46 27 FOBS= 124.8 SIGMA=  1.7 PHAS=  -95.3 FOM= 0.81 TEST= 0
INDE  9 46 29 FOBS= 161.2 SIGMA=  1.3 PHAS= -131.1 FOM= 0.79 TEST= 0
INDE  9 46 31 FOBS= 130.3 SIGMA=  1.6 PHAS=  -41.9 FOM= 0.88 TEST= 0
```

*FIG. 12A - 250*

| | | | | | | | | | | | | |
|---|---|---|---|---|---|---|---|---|---|---|---|---|
| INDE | 9 | 46 | 33 | FOBS= | 51.4 | SIGMA= | 4.8 | PHAS= | -87.2 | FOM= | 0.45 | TEST= 0 |
| INDE | 9 | 46 | 35 | FOBS= | 161.0 | SIGMA= | 1.4 | PHAS= | 83.1 | FOM= | 0.63 | TEST= 1 |
| INDE | 9 | 46 | 37 | FOBS= | 207.7 | SIGMA= | 1.0 | PHAS= | -90.0 | FOM= | 0.97 | TEST= 0 |
| INDE | 9 | 46 | 39 | FOBS= | 0.0 | SIGMA= | 19.7 | PHAS= | 0.0 | FOM= | 0.00 | TEST= 0 |
| INDE | 9 | 46 | 41 | FOBS= | 58.7 | SIGMA= | 3.2 | PHAS= | 53.1 | FOM= | 0.40 | TEST= 0 |
| INDE | 9 | 46 | 43 | FOBS= | 0.0 | SIGMA= | 19.2 | PHAS= | 0.0 | FOM= | 0.00 | TEST= 0 |
| INDE | 9 | 46 | 45 | FOBS= | 64.1 | SIGMA= | 2.9 | PHAS= | -85.2 | FOM= | 0.92 | TEST= 0 |
| INDE | 9 | 46 | 47 | FOBS= | 64.7 | SIGMA= | 2.9 | PHAS= | -44.0 | FOM= | 0.81 | TEST= 0 |
| INDE | 9 | 46 | 49 | FOBS= | 0.0 | SIGMA= | 19.5 | PHAS= | 0.0 | FOM= | 0.00 | TEST= 0 |
| INDE | 9 | 46 | 51 | FOBS= | 30.5 | SIGMA= | 7.0 | PHAS= | -6.4 | FOM= | 0.47 | TEST= 0 |
| INDE | 9 | 46 | 53 | FOBS= | 137.4 | SIGMA= | 1.6 | PHAS= | 29.1 | FOM= | 0.96 | TEST= 0 |
| INDE | 9 | 46 | 55 | FOBS= | 54.4 | SIGMA= | 3.7 | PHAS= | -91.8 | FOM= | 0.71 | TEST= 0 |
| INDE | 9 | 46 | 57 | FOBS= | 37.6 | SIGMA= | 9.8 | PHAS= | 0.1 | FOM= | 0.44 | TEST= 0 |
| INDE | 9 | 46 | 59 | FOBS= | 78.1 | SIGMA= | 2.8 | PHAS= | -39.2 | FOM= | 0.92 | TEST= 0 |
| INDE | 9 | 46 | 61 | FOBS= | 0.0 | SIGMA= | 22.2 | PHAS= | 0.0 | FOM= | 0.00 | TEST= 0 |
| INDE | 9 | 47 | 10 | FOBS= | 211.1 | SIGMA= | 0.8 | PHAS= | -58.9 | FOM= | 0.82 | TEST= 1 |
| INDE | 9 | 47 | 12 | FOBS= | 101.2 | SIGMA= | 2.8 | PHAS= | 92.1 | FOM= | 0.91 | TEST= 0 |
| INDE | 9 | 47 | 14 | FOBS= | 132.9 | SIGMA= | 1.6 | PHAS= | -136.3 | FOM= | 0.93 | TEST= 0 |
| INDE | 9 | 47 | 16 | FOBS= | 100.0 | SIGMA= | 2.1 | PHAS= | -59.8 | FOM= | 0.69 | TEST= 0 |
| INDE | 9 | 47 | 18 | FOBS= | 70.0 | SIGMA= | 3.0 | PHAS= | -20.1 | FOM= | 0.72 | TEST= 0 |
| INDE | 9 | 47 | 20 | FOBS= | 209.9 | SIGMA= | 1.1 | PHAS= | -98.9 | FOM= | 0.94 | TEST= 0 |
| INDE | 9 | 47 | 22 | FOBS= | 51.0 | SIGMA= | 4.0 | PHAS= | -148.9 | FOM= | 0.71 | TEST= 0 |
| INDE | 9 | 47 | 24 | FOBS= | 192.6 | SIGMA= | 1.2 | PHAS= | 18.1 | FOM= | 0.95 | TEST= 0 |
| INDE | 9 | 47 | 26 | FOBS= | 91.3 | SIGMA= | 2.3 | PHAS= | 115.2 | FOM= | 0.19 | TEST= 1 |
| INDE | 9 | 47 | 28 | FOBS= | 134.1 | SIGMA= | 1.6 | PHAS= | 144.9 | FOM= | 0.91 | TEST= 0 |
| INDE | 9 | 47 | 30 | FOBS= | 149.2 | SIGMA= | 1.4 | PHAS= | -141.5 | FOM= | 0.94 | TEST= 0 |
| INDE | 9 | 47 | 32 | FOBS= | 0.0 | SIGMA= | 22.1 | PHAS= | 0.0 | FOM= | 0.00 | TEST= 0 |
| INDE | 9 | 47 | 34 | FOBS= | 28.4 | SIGMA= | 7.8 | PHAS= | -119.6 | FOM= | 0.48 | TEST= 0 |
| INDE | 9 | 47 | 36 | FOBS= | 148.7 | SIGMA= | 1.5 | PHAS= | -127.0 | FOM= | 0.92 | TEST= 0 |
| INDE | 9 | 47 | 38 | FOBS= | 46.0 | SIGMA= | 4.0 | PHAS= | 167.0 | FOM= | 0.30 | TEST= 0 |
| INDE | 9 | 47 | 40 | FOBS= | 0.0 | SIGMA= | 19.2 | PHAS= | 0.0 | FOM= | 0.00 | TEST= 0 |
| INDE | 9 | 47 | 42 | FOBS= | 74.6 | SIGMA= | 2.5 | PHAS= | 34.0 | FOM= | 0.63 | TEST= 0 |
| INDE | 9 | 47 | 44 | FOBS= | 45.5 | SIGMA= | 4.1 | PHAS= | 82.8 | FOM= | 0.38 | TEST= 1 |
| INDE | 9 | 47 | 46 | FOBS= | 0.0 | SIGMA= | 19.9 | PHAS= | 0.0 | FOM= | 0.00 | TEST= 0 |
| INDE | 9 | 47 | 48 | FOBS= | 0.0 | SIGMA= | 19.0 | PHAS= | 0.0 | FOM= | 0.00 | TEST= 0 |
| INDE | 9 | 47 | 50 | FOBS= | 0.0 | SIGMA= | 22.2 | PHAS= | 0.0 | FOM= | 0.00 | TEST= 0 |
| INDE | 9 | 47 | 52 | FOBS= | 60.8 | SIGMA= | 3.3 | PHAS= | -76.4 | FOM= | 0.88 | TEST= 0 |
| INDE | 9 | 47 | 54 | FOBS= | 0.0 | SIGMA= | 21.9 | PHAS= | 0.0 | FOM= | 0.00 | TEST= 0 |
| INDE | 9 | 47 | 56 | FOBS= | 36.1 | SIGMA= | 6.7 | PHAS= | 31.7 | FOM= | 0.21 | TEST= 0 |
| INDE | 9 | 47 | 58 | FOBS= | 37.2 | SIGMA= | 5.7 | PHAS= | -127.5 | FOM= | 0.38 | TEST= 0 |
| INDE | 9 | 47 | 60 | FOBS= | 49.9 | SIGMA= | 4.7 | PHAS= | -138.7 | FOM= | 0.04 | TEST= 1 |
| INDE | 9 | 48 | 9 | FOBS= | 198.2 | SIGMA= | 1.3 | PHAS= | -176.6 | FOM= | 0.96 | TEST= 0 |
| INDE | 9 | 48 | 11 | FOBS= | 128.5 | SIGMA= | 1.2 | PHAS= | -138.8 | FOM= | 0.78 | TEST= 0 |
| INDE | 9 | 48 | 13 | FOBS= | 190.9 | SIGMA= | 1.6 | PHAS= | -39.7 | FOM= | 0.74 | TEST= 1 |
| INDE | 9 | 48 | 15 | FOBS= | 84.9 | SIGMA= | 2.4 | PHAS= | 127.2 | FOM= | 0.96 | TEST= 0 |
| INDE | 9 | 48 | 17 | FOBS= | 95.5 | SIGMA= | 2.1 | PHAS= | 139.9 | FOM= | 0.70 | TEST= 0 |
| INDE | 9 | 48 | 19 | FOBS= | 82.2 | SIGMA= | 2.8 | PHAS= | -121.3 | FOM= | 0.90 | TEST= 1 |
| INDE | 9 | 48 | 21 | FOBS= | 64.0 | SIGMA= | 3.4 | PHAS= | -35.3 | FOM= | 0.73 | TEST= 0 |
| INDE | 9 | 48 | 23 | FOBS= | 40.3 | SIGMA= | 5.0 | PHAS= | 96.4 | FOM= | 0.58 | TEST= 0 |
| INDE | 9 | 48 | 25 | FOBS= | 44.3 | SIGMA= | 4.6 | PHAS= | -31.8 | FOM= | 0.80 | TEST= 0 |
| INDE | 9 | 48 | 27 | FOBS= | 91.3 | SIGMA= | 2.3 | PHAS= | 29.6 | FOM= | 0.37 | TEST= 0 |
| INDE | 9 | 48 | 29 | FOBS= | 85.5 | SIGMA= | 2.4 | PHAS= | -104.6 | FOM= | 0.77 | TEST= 0 |
| INDE | 9 | 48 | 31 | FOBS= | 112.9 | SIGMA= | 1.8 | PHAS= | 77.9 | FOM= | 0.83 | TEST= 0 |
| INDE | 9 | 48 | 33 | FOBS= | 0.0 | SIGMA= | 22.0 | PHAS= | 0.0 | FOM= | 0.00 | TEST= 0 |
| INDE | 9 | 48 | 35 | FOBS= | 0.0 | SIGMA= | 21.0 | PHAS= | 0.0 | FOM= | 0.00 | TEST= 0 |
| INDE | 9 | 48 | 37 | FOBS= | 62.5 | SIGMA= | 3.3 | PHAS= | -137.6 | FOM= | 0.72 | TEST= 0 |
| INDE | 9 | 48 | 39 | FOBS= | 27.9 | SIGMA= | 6.6 | PHAS= | -106.2 | FOM= | 0.32 | TEST= 0 |
| INDE | 9 | 48 | 41 | FOBS= | 32.5 | SIGMA= | 5.7 | PHAS= | -81.9 | FOM= | 0.20 | TEST= 0 |
| INDE | 9 | 48 | 43 | FOBS= | 59.8 | SIGMA= | 3.1 | PHAS= | -3.4 | FOM= | 0.74 | TEST= 0 |
| INDE | 9 | 48 | 45 | FOBS= | 57.7 | SIGMA= | 3.2 | PHAS= | -33.0 | FOM= | 0.05 | TEST= 0 |
| INDE | 9 | 48 | 47 | FOBS= | 25.9 | SIGMA= | 7.4 | PHAS= | -93.4 | FOM= | 0.41 | TEST= 0 |
| INDE | 9 | 48 | 49 | FOBS= | 50.9 | SIGMA= | 4.0 | PHAS= | 117.1 | FOM= | 0.29 | TEST= 0 |
| INDE | 9 | 48 | 51 | FOBS= | 0.0 | SIGMA= | 20.1 | PHAS= | 0.0 | FOM= | 0.00 | TEST= 0 |
| INDE | 9 | 48 | 53 | FOBS= | 0.0 | SIGMA= | 20.7 | PHAS= | 0.0 | FOM= | 0.00 | TEST= 0 |
| INDE | 9 | 48 | 55 | FOBS= | 30.0 | SIGMA= | 10.1 | PHAS= | 13.0 | FOM= | 0.29 | TEST= 0 |
| INDE | 9 | 48 | 57 | FOBS= | 24.2 | SIGMA= | 10.2 | PHAS= | -21.7 | FOM= | 0.29 | TEST= 0 |
| INDE | 9 | 48 | 59 | FOBS= | 45.4 | SIGMA= | 5.2 | PHAS= | -53.6 | FOM= | 0.14 | TEST= 1 |
| INDE | 9 | 49 | 10 | FOBS= | 97.8 | SIGMA= | 1.9 | PHAS= | 103.7 | FOM= | 0.96 | TEST= 0 |
| INDE | 9 | 49 | 12 | FOBS= | 199.8 | SIGMA= | 1.5 | PHAS= | 173.5 | FOM= | 0.93 | TEST= 0 |
| INDE | 9 | 49 | 14 | FOBS= | 80.5 | SIGMA= | 3.4 | PHAS= | -98.8 | FOM= | 0.88 | TEST= 0 |

*FIG. 12A - 251*

| | | | | | | | | | | | |
|---|---|---|---|---|---|---|---|---|---|---|---|
| INDE | 9 | 49 | 16 | FOBS= | 83.5 | SIGMA= | 2.4 | PHAS= | -36.8 | FOM= | 0.80 | TEST= 0
| INDE | 9 | 49 | 18 | FOBS= | 32.5 | SIGMA= | 6.1 | PHAS= | 52.6 | FOM= | 0.80 | TEST= 0
| INDE | 9 | 49 | 20 | FOBS= | 110.0 | SIGMA= | 1.9 | PHAS= | -147.9 | FOM= | 0.93 | TEST= 0
| INDE | 9 | 49 | 22 | FOBS= | 17.1 | SIGMA= | 11.6 | PHAS= | -173.3 | FOM= | 0.58 | TEST= 1
| INDE | 9 | 49 | 24 | FOBS= | 129.3 | SIGMA= | 1.6 | PHAS= | -22.2 | FOM= | 0.85 | TEST= 0
| INDE | 9 | 49 | 26 | FOBS= | 72.5 | SIGMA= | 2.8 | PHAS= | 24.3 | FOM= | 0.82 | TEST= 0
| INDE | 9 | 49 | 28 | FOBS= | 59.2 | SIGMA= | 3.5 | PHAS= | -127.4 | FOM= | 0.52 | TEST= 0
| INDE | 9 | 49 | 30 | FOBS= | 142.5 | SIGMA= | 1.5 | PHAS= | -110.8 | FOM= | 0.79 | TEST= 0
| INDE | 9 | 49 | 32 | FOBS= | 0.0 | SIGMA= | 19.9 | PHAS= | 0.0 | FOM= | 0.00 | TEST= 0
| INDE | 9 | 49 | 34 | FOBS= | 67.1 | SIGMA= | 3.7 | PHAS= | 98.0 | FOM= | 0.62 | TEST= 0
| INDE | 9 | 49 | 36 | FOBS= | 50.9 | SIGMA= | 4.0 | PHAS= | -71.0 | FOM= | 0.63 | TEST= 0
| INDE | 9 | 49 | 38 | FOBS= | 49.9 | SIGMA= | 4.0 | PHAS= | 10.8 | FOM= | 0.69 | TEST= 0
| INDE | 9 | 49 | 40 | FOBS= | 112.4 | SIGMA= | 1.7 | PHAS= | 130.3 | FOM= | 0.93 | TEST= 0
| INDE | 9 | 49 | 42 | FOBS= | 0.0 | SIGMA= | 19.1 | PHAS= | 0.0 | FOM= | 0.00 | TEST= 0
| INDE | 9 | 49 | 44 | FOBS= | 42.9 | SIGMA= | 4.3 | PHAS= | -64.6 | FOM= | 0.59 | TEST= 0
| INDE | 9 | 49 | 46 | FOBS= | 69.2 | SIGMA= | 2.7 | PHAS= | -139.6 | FOM= | 0.82 | TEST= 0
| INDE | 9 | 49 | 48 | FOBS= | 27.9 | SIGMA= | 6.9 | PHAS= | -29.8 | FOM= | 0.06 | TEST= 0
| INDE | 9 | 49 | 50 | FOBS= | 16.5 | SIGMA= | 12.3 | PHAS= | -81.8 | FOM= | 0.10 | TEST= 0
| INDE | 9 | 49 | 52 | FOBS= | 52.9 | SIGMA= | 3.9 | PHAS= | -81.9 | FOM= | 0.69 | TEST= 0
| INDE | 9 | 49 | 54 | FOBS= | 28.5 | SIGMA= | 7.7 | PHAS= | -59.5 | FOM= | 0.49 | TEST= 0
| INDE | 9 | 49 | 56 | FOBS= | 33.3 | SIGMA= | 6.2 | PHAS= | -86.3 | FOM= | 0.50 | TEST= 0
| INDE | 9 | 49 | 58 | FOBS= | 16.0 | SIGMA= | 19.6 | PHAS= | -152.9 | FOM= | 0.31 | TEST= 0
| INDE | 9 | 50 | 9 | FOBS= | 286.8 | SIGMA= | 1.2 | PHAS= | -52.8 | FOM= | 0.96 | TEST= 0
| INDE | 9 | 50 | 11 | FOBS= | 158.5 | SIGMA= | 1.2 | PHAS= | 116.3 | FOM= | 0.91 | TEST= 0
| INDE | 9 | 50 | 13 | FOBS= | 85.2 | SIGMA= | 2.0 | PHAS= | -53.1 | FOM= | 0.94 | TEST= 0
| INDE | 9 | 50 | 15 | FOBS= | 66.7 | SIGMA= | 3.0 | PHAS= | -141.1 | FOM= | 0.80 | TEST= 0
| INDE | 9 | 50 | 17 | FOBS= | 236.3 | SIGMA= | 1.0 | PHAS= | 170.4 | FOM= | 0.96 | TEST= 0
| INDE | 9 | 50 | 19 | FOBS= | 117.1 | SIGMA= | 1.8 | PHAS= | -130.1 | FOM= | 0.92 | TEST= 0
| INDE | 9 | 50 | 21 | FOBS= | 0.0 | SIGMA= | 20.6 | PHAS= | 0.0 | FOM= | 0.00 | TEST= 0
| INDE | 9 | 50 | 23 | FOBS= | 204.0 | SIGMA= | 1.1 | PHAS= | 23.7 | FOM= | 0.96 | TEST= 0
| INDE | 9 | 50 | 25 | FOBS= | 211.3 | SIGMA= | 1.1 | PHAS= | -67.7 | FOM= | 0.95 | TEST= 1
| INDE | 9 | 50 | 27 | FOBS= | 157.4 | SIGMA= | 1.4 | PHAS= | -80.5 | FOM= | 0.91 | TEST= 0
| INDE | 9 | 50 | 29 | FOBS= | 95.4 | SIGMA= | 2.2 | PHAS= | 163.8 | FOM= | 0.72 | TEST= 0
| INDE | 9 | 50 | 31 | FOBS= | 74.2 | SIGMA= | 2.7 | PHAS= | 123.1 | FOM= | 0.38 | TEST= 0
| INDE | 9 | 50 | 33 | FOBS= | 165.4 | SIGMA= | 1.3 | PHAS= | -1.0 | FOM= | 0.92 | TEST= 0
| INDE | 9 | 50 | 35 | FOBS= | 0.0 | SIGMA= | 21.7 | PHAS= | 0.0 | FOM= | 0.00 | TEST= 0
| INDE | 9 | 50 | 37 | FOBS= | 67.9 | SIGMA= | 3.0 | PHAS= | -124.3 | FOM= | 0.80 | TEST= 0
| INDE | 9 | 50 | 39 | FOBS= | 165.8 | SIGMA= | 1.2 | PHAS= | 101.9 | FOM= | 0.95 | TEST= 0
| INDE | 9 | 50 | 41 | FOBS= | 66.7 | SIGMA= | 2.8 | PHAS= | 51.8 | FOM= | 0.77 | TEST= 0
| INDE | 9 | 50 | 43 | FOBS= | 72.2 | SIGMA= | 2.6 | PHAS= | -76.0 | FOM= | 0.77 | TEST= 0
| INDE | 9 | 50 | 45 | FOBS= | 114.0 | SIGMA= | 1.7 | PHAS= | 130.4 | FOM= | 0.90 | TEST= 0
| INDE | 9 | 50 | 47 | FOBS= | 0.0 | SIGMA= | 20.3 | PHAS= | 0.0 | FOM= | 0.00 | TEST= 0
| INDE | 9 | 50 | 49 | FOBS= | 0.0 | SIGMA= | 20.2 | PHAS= | 0.0 | FOM= | 0.00 | TEST= 0
| INDE | 9 | 50 | 51 | FOBS= | 113.5 | SIGMA= | 1.9 | PHAS= | -45.4 | FOM= | 0.11 | TEST= 1
| INDE | 9 | 50 | 53 | FOBS= | 52.4 | SIGMA= | 3.9 | PHAS= | -155.1 | FOM= | 0.63 | TEST= 0
| INDE | 9 | 50 | 55 | FOBS= | 25.5 | SIGMA= | 9.4 | PHAS= | 163.7 | FOM= | 0.39 | TEST= 0
| INDE | 9 | 50 | 57 | FOBS= | 0.0 | SIGMA= | 22.0 | PHAS= | 0.0 | FOM= | 0.00 | TEST= 0
| INDE | 9 | 51 | 10 | FOBS= | 125.1 | SIGMA= | 2.2 | PHAS= | 143.7 | FOM= | 0.90 | TEST= 0
| INDE | 9 | 51 | 12 | FOBS= | 134.4 | SIGMA= | 1.1 | PHAS= | 83.3 | FOM= | 0.96 | TEST= 0
| INDE | 9 | 51 | 14 | FOBS= | 202.6 | SIGMA= | 0.9 | PHAS= | -163.8 | FOM= | 0.95 | TEST= 0
| INDE | 9 | 51 | 16 | FOBS= | 78.7 | SIGMA= | 2.5 | PHAS= | 38.3 | FOM= | 0.90 | TEST= 0
| INDE | 9 | 51 | 18 | FOBS= | 156.3 | SIGMA= | 1.3 | PHAS= | 87.8 | FOM= | 0.86 | TEST= 0
| INDE | 9 | 51 | 20 | FOBS= | 102.3 | SIGMA= | 2.0 | PHAS= | 115.3 | FOM= | 0.92 | TEST= 0
| INDE | 9 | 51 | 22 | FOBS= | 207.1 | SIGMA= | 1.1 | PHAS= | -19.0 | FOM= | 0.95 | TEST= 0
| INDE | 9 | 51 | 24 | FOBS= | 162.0 | SIGMA= | 1.3 | PHAS= | -72.7 | FOM= | 0.94 | TEST= 0
| INDE | 9 | 51 | 26 | FOBS= | 122.2 | SIGMA= | 1.7 | PHAS= | -115.3 | FOM= | 0.92 | TEST= 0
| INDE | 9 | 51 | 28 | FOBS= | 152.0 | SIGMA= | 1.4 | PHAS= | 174.4 | FOM= | 0.95 | TEST= 0
| INDE | 9 | 51 | 30 | FOBS= | 29.0 | SIGMA= | 8.5 | PHAS= | 83.3 | FOM= | 0.11 | TEST= 0
| INDE | 9 | 51 | 32 | FOBS= | 32.7 | SIGMA= | 6.0 | PHAS= | -101.0 | FOM= | 0.73 | TEST= 0
| INDE | 9 | 51 | 34 | FOBS= | 0.0 | SIGMA= | 22.1 | PHAS= | 0.0 | FOM= | 0.00 | TEST= 0
| INDE | 9 | 51 | 36 | FOBS= | 38.8 | SIGMA= | 5.6 | PHAS= | 178.1 | FOM= | 0.62 | TEST= 0
| INDE | 9 | 51 | 38 | FOBS= | 183.5 | SIGMA= | 1.2 | PHAS= | -14.2 | FOM= | 0.96 | TEST= 0
| INDE | 9 | 51 | 40 | FOBS= | 122.8 | SIGMA= | 1.6 | PHAS= | 65.7 | FOM= | 0.95 | TEST= 0
| INDE | 9 | 51 | 42 | FOBS= | 44.7 | SIGMA= | 4.3 | PHAS= | 5.8 | FOM= | 0.57 | TEST= 0
| INDE | 9 | 51 | 44 | FOBS= | 65.0 | SIGMA= | 2.9 | PHAS= | 102.0 | FOM= | 0.07 | TEST= 1
| INDE | 9 | 51 | 46 | FOBS= | 24.8 | SIGMA= | 8.0 | PHAS= | 20.3 | FOM= | 0.67 | TEST= 0
| INDE | 9 | 51 | 48 | FOBS= | 45.7 | SIGMA= | 4.5 | PHAS= | 107.9 | FOM= | 0.37 | TEST= 0
| INDE | 9 | 51 | 50 | FOBS= | 76.4 | SIGMA= | 2.7 | PHAS= | -24.0 | FOM= | 0.84 | TEST= 0
| INDE | 9 | 51 | 52 | FOBS= | 28.1 | SIGMA= | 10.3 | PHAS= | -150.7 | FOM= | 0.34 | TEST= 0
| INDE | 9 | 51 | 54 | FOBS= | 49.3 | SIGMA= | 4.2 | PHAS= | 83.9 | FOM= | 0.80 | TEST= 0

*FIG. 12A - 252*

| | | | | | | | | | | | |
|---|---|---|---|---|---|---|---|---|---|---|---|
| INDE | 9 | 51 | 56 | FOBS= | 37.3 | SIGMA= | 6.6 | PHAS= | 1.1 | FOM= | 0.70 | TEST= 0 |
| INDE | 9 | 51 | 58 | FOBS= | 0.0 | SIGMA= | 28.8 | PHAS= | 0.0 | FOM= | 0.00 | TEST= 0 |
| INDE | 9 | 52 | 9 | FOBS= | 210.9 | SIGMA= | 1.4 | PHAS= | -51.3 | FOM= | 0.91 | TEST= 0 |
| INDE | 9 | 52 | 11 | FOBS= | 167.7 | SIGMA= | 1.1 | PHAS= | 28.7 | FOM= | 0.95 | TEST= 0 |
| INDE | 9 | 52 | 13 | FOBS= | 220.9 | SIGMA= | 1.0 | PHAS= | 81.8 | FOM= | 0.97 | TEST= 0 |
| INDE | 9 | 52 | 15 | FOBS= | 51.8 | SIGMA= | 3.8 | PHAS= | -178.3 | FOM= | 0.71 | TEST= 0 |
| INDE | 9 | 52 | 17 | FOBS= | 62.0 | SIGMA= | 3.1 | PHAS= | -91.4 | FOM= | 0.83 | TEST= 0 |
| INDE | 9 | 52 | 19 | FOBS= | 144.0 | SIGMA= | 1.4 | PHAS= | -65.1 | FOM= | 0.83 | TEST= 0 |
| INDE | 9 | 52 | 21 | FOBS= | 104.0 | SIGMA= | 2.0 | PHAS= | -128.1 | FOM= | 0.88 | TEST= 0 |
| INDE | 9 | 52 | 23 | FOBS= | 40.8 | SIGMA= | 4.9 | PHAS= | -116.6 | FOM= | 0.52 | TEST= 0 |
| INDE | 9 | 52 | 25 | FOBS= | 104.4 | SIGMA= | 2.0 | PHAS= | -80.5 | FOM= | 0.85 | TEST= 0 |
| INDE | 9 | 52 | 27 | FOBS= | 119.6 | SIGMA= | 1.7 | PHAS= | 147.0 | FOM= | 0.93 | TEST= 0 |
| INDE | 9 | 52 | 29 | FOBS= | 136.7 | SIGMA= | 1.5 | PHAS= | 101.5 | FOM= | 0.94 | TEST= 0 |
| INDE | 9 | 52 | 31 | FOBS= | 82.9 | SIGMA= | 2.4 | PHAS= | 149.1 | FOM= | 0.76 | TEST= 0 |
| INDE | 9 | 52 | 33 | FOBS= | 38.9 | SIGMA= | 5.6 | PHAS= | 101.6 | FOM= | 0.61 | TEST= 0 |
| INDE | 9 | 52 | 35 | FOBS= | 74.0 | SIGMA= | 2.7 | PHAS= | -121.9 | FOM= | 0.87 | TEST= 1 |
| INDE | 9 | 52 | 37 | FOBS= | 115.8 | SIGMA= | 1.8 | PHAS= | 102.8 | FOM= | 0.90 | TEST= 0 |
| INDE | 9 | 52 | 39 | FOBS= | 35.8 | SIGMA= | 5.6 | PHAS= | -8.7 | FOM= | 0.11 | TEST= 0 |
| INDE | 9 | 52 | 41 | FOBS= | 95.0 | SIGMA= | 2.1 | PHAS= | -85.1 | FOM= | 0.86 | TEST= 0 |
| INDE | 9 | 52 | 43 | FOBS= | 115.9 | SIGMA= | 1.8 | PHAS= | -139.7 | FOM= | 0.92 | TEST= 0 |
| INDE | 9 | 52 | 45 | FOBS= | 102.9 | SIGMA= | 1.9 | PHAS= | -87.9 | FOM= | 0.91 | TEST= 0 |
| INDE | 9 | 52 | 47 | FOBS= | 47.9 | SIGMA= | 3.9 | PHAS= | -144.1 | FOM= | 0.50 | TEST= 0 |
| INDE | 9 | 52 | 49 | FOBS= | 32.7 | SIGMA= | 6.3 | PHAS= | -86.3 | FOM= | 0.59 | TEST= 0 |
| INDE | 9 | 52 | 51 | FOBS= | 28.8 | SIGMA= | 9.4 | PHAS= | 91.7 | FOM= | 0.47 | TEST= 0 |
| INDE | 9 | 52 | 53 | FOBS= | 9.3 | SIGMA= | 30.1 | PHAS= | -141.8 | FOM= | 0.07 | TEST= 0 |
| INDE | 9 | 52 | 55 | FOBS= | 0.0 | SIGMA= | 23.2 | PHAS= | 0.0 | FOM= | 0.00 | TEST= 0 |
| INDE | 9 | 52 | 57 | FOBS= | 0.0 | SIGMA= | 22.0 | PHAS= | 0.0 | FOM= | 0.00 | TEST= 1 |
| INDE | 9 | 53 | 10 | FOBS= | 128.1 | SIGMA= | 2.2 | PHAS= | -134.0 | FOM= | 0.88 | TEST= 0 |
| INDE | 9 | 53 | 12 | FOBS= | 83.5 | SIGMA= | 1.8 | PHAS= | 35.0 | FOM= | 0.89 | TEST= 0 |
| INDE | 9 | 53 | 14 | FOBS= | 49.0 | SIGMA= | 3.3 | PHAS= | 10.5 | FOM= | 0.85 | TEST= 0 |
| INDE | 9 | 53 | 16 | FOBS= | 61.7 | SIGMA= | 4.2 | PHAS= | 2.5 | FOM= | 0.56 | TEST= 0 |
| INDE | 9 | 53 | 18 | FOBS= | 61.0 | SIGMA= | 3.1 | PHAS= | 148.1 | FOM= | 0.91 | TEST= 0 |
| INDE | 9 | 53 | 20 | FOBS= | 99.0 | SIGMA= | 2.0 | PHAS= | -164.2 | FOM= | 0.88 | TEST= 0 |
| INDE | 9 | 53 | 22 | FOBS= | 102.0 | SIGMA= | 2.0 | PHAS= | -179.6 | FOM= | 0.74 | TEST= 0 |
| INDE | 9 | 53 | 24 | FOBS= | 74.5 | SIGMA= | 2.7 | PHAS= | -123.4 | FOM= | 0.70 | TEST= 0 |
| INDE | 9 | 53 | 26 | FOBS= | 125.6 | SIGMA= | 1.7 | PHAS= | 46.0 | FOM= | 0.94 | TEST= 0 |
| INDE | 9 | 53 | 28 | FOBS= | 61.9 | SIGMA= | 3.2 | PHAS= | 65.9 | FOM= | 0.88 | TEST= 0 |
| INDE | 9 | 53 | 30 | FOBS= | 73.7 | SIGMA= | 2.7 | PHAS= | 22.8 | FOM= | 0.86 | TEST= 0 |
| INDE | 9 | 53 | 32 | FOBS= | 95.3 | SIGMA= | 2.1 | PHAS= | 43.5 | FOM= | 0.92 | TEST= 0 |
| INDE | 9 | 53 | 34 | FOBS= | 65.1 | SIGMA= | 3.1 | PHAS= | 111.6 | FOM= | 0.49 | TEST= 0 |
| INDE | 9 | 53 | 36 | FOBS= | 0.0 | SIGMA= | 19.8 | PHAS= | 0.0 | FOM= | 0.00 | TEST= 0 |
| INDE | 9 | 53 | 38 | FOBS= | 131.1 | SIGMA= | 1.6 | PHAS= | 7.7 | FOM= | 0.91 | TEST= 0 |
| INDE | 9 | 53 | 40 | FOBS= | 43.6 | SIGMA= | 4.3 | PHAS= | 100.1 | FOM= | 0.16 | TEST= 0 |
| INDE | 9 | 53 | 42 | FOBS= | 154.6 | SIGMA= | 1.3 | PHAS= | 102.2 | FOM= | 0.96 | TEST= 0 |
| INDE | 9 | 53 | 44 | FOBS= | 67.7 | SIGMA= | 2.8 | PHAS= | -152.3 | FOM= | 0.88 | TEST= 0 |
| INDE | 9 | 53 | 46 | FOBS= | 66.4 | SIGMA= | 2.8 | PHAS= | -95.5 | FOM= | 0.50 | TEST= 0 |
| INDE | 9 | 53 | 48 | FOBS= | 42.3 | SIGMA= | 4.9 | PHAS= | -138.8 | FOM= | 0.39 | TEST= 0 |
| INDE | 9 | 53 | 50 | FOBS= | 38.3 | SIGMA= | 5.4 | PHAS= | 45.4 | FOM= | 0.57 | TEST= 0 |
| INDE | 9 | 53 | 52 | FOBS= | 51.8 | SIGMA= | 4.0 | PHAS= | 148.5 | FOM= | 0.63 | TEST= 0 |
| INDE | 9 | 53 | 54 | FOBS= | 0.0 | SIGMA= | 26.0 | PHAS= | 0.0 | FOM= | 0.00 | TEST= 1 |
| INDE | 9 | 53 | 56 | FOBS= | 0.0 | SIGMA= | 25.7 | PHAS= | 0.0 | FOM= | 0.00 | TEST= 0 |
| INDE | 9 | 54 | 9 | FOBS= | 112.6 | SIGMA= | 2.4 | PHAS= | 131.7 | FOM= | 0.93 | TEST= 0 |
| INDE | 9 | 54 | 11 | FOBS= | 68.2 | SIGMA= | 3.9 | PHAS= | 21.6 | FOM= | 0.77 | TEST= 0 |
| INDE | 9 | 54 | 13 | FOBS= | 50.9 | SIGMA= | 2.9 | PHAS= | 111.0 | FOM= | 0.72 | TEST= 0 |
| INDE | 9 | 54 | 15 | FOBS= | 109.1 | SIGMA= | 1.6 | PHAS= | -50.0 | FOM= | 0.60 | TEST= 0 |
| INDE | 9 | 54 | 17 | FOBS= | 16.2 | SIGMA= | 16.5 | PHAS= | -48.9 | FOM= | 0.13 | TEST= 0 |
| INDE | 9 | 54 | 19 | FOBS= | 67.6 | SIGMA= | 2.9 | PHAS= | 159.7 | FOM= | 0.78 | TEST= 0 |
| INDE | 9 | 54 | 21 | FOBS= | 78.7 | SIGMA= | 2.5 | PHAS= | -168.5 | FOM= | 0.85 | TEST= 0 |
| INDE | 9 | 54 | 23 | FOBS= | 132.1 | SIGMA= | 1.6 | PHAS= | 94.7 | FOM= | 0.92 | TEST= 0 |
| INDE | 9 | 54 | 25 | FOBS= | 66.5 | SIGMA= | 3.0 | PHAS= | -156.8 | FOM= | 0.41 | TEST= 0 |
| INDE | 9 | 54 | 27 | FOBS= | 0.0 | SIGMA= | 20.5 | PHAS= | 0.0 | FOM= | 0.00 | TEST= 0 |
| INDE | 9 | 54 | 29 | FOBS= | 53.1 | SIGMA= | 3.7 | PHAS= | 54.9 | FOM= | 0.46 | TEST= 0 |
| INDE | 9 | 54 | 31 | FOBS= | 93.4 | SIGMA= | 2.2 | PHAS= | -41.8 | FOM= | 0.94 | TEST= 0 |
| INDE | 9 | 54 | 33 | FOBS= | 82.4 | SIGMA= | 2.4 | PHAS= | 40.6 | FOM= | 0.88 | TEST= 0 |
| INDE | 9 | 54 | 35 | FOBS= | 0.0 | SIGMA= | 19.7 | PHAS= | 0.0 | FOM= | 0.00 | TEST= 0 |
| INDE | 9 | 54 | 37 | FOBS= | 89.8 | SIGMA= | 2.3 | PHAS= | 105.7 | FOM= | 0.81 | TEST= 0 |
| INDE | 9 | 54 | 39 | FOBS= | 33.6 | SIGMA= | 7.2 | PHAS= | -97.4 | FOM= | 0.58 | TEST= 0 |
| INDE | 9 | 54 | 41 | FOBS= | 58.5 | SIGMA= | 3.1 | PHAS= | -73.0 | FOM= | 0.80 | TEST= 0 |
| INDE | 9 | 54 | 43 | FOBS= | 83.1 | SIGMA= | 2.3 | PHAS= | 81.1 | FOM= | 0.79 | TEST= 0 |
| INDE | 9 | 54 | 45 | FOBS= | 58.0 | SIGMA= | 3.3 | PHAS= | -145.9 | FOM= | 0.90 | TEST= 0 |

*FIG. 12A - 253*

| | | | | | | | | | | | |
|---|---|---|---|---|---|---|---|---|---|---|---|
| INDE | 9 | 54 | 47 | FOBS= | 0.0 | SIGMA= | 21.2 | PHAS= | 0.0 | FOM= | 0.00 | TEST= 0
| INDE | 9 | 54 | 49 | FOBS= | 0.0 | SIGMA= | 22.6 | PHAS= | 0.0 | FOM= | 0.00 | TEST= 0
| INDE | 9 | 54 | 51 | FOBS= | 49.3 | SIGMA= | 4.8 | PHAS= | 58.9 | FOM= | 0.70 | TEST= 0
| INDE | 9 | 54 | 53 | FOBS= | 67.9 | SIGMA= | 4.3 | PHAS= | -110.7 | FOM= | 0.85 | TEST= 0
| INDE | 9 | 54 | 55 | FOBS= | 36.8 | SIGMA= | 11.4 | PHAS= | 52.7 | FOM= | 0.67 | TEST= 0
| INDE | 9 | 55 | 10 | FOBS= | 124.3 | SIGMA= | 2.2 | PHAS= | -18.7 | FOM= | 0.89 | TEST= 0
| INDE | 9 | 55 | 12 | FOBS= | 110.2 | SIGMA= | 2.4 | PHAS= | 152.8 | FOM= | 0.72 | TEST= 0
| INDE | 9 | 55 | 14 | FOBS= | 75.2 | SIGMA= | 2.0 | PHAS= | 172.8 | FOM= | 0.45 | TEST= 0
| INDE | 9 | 55 | 16 | FOBS= | 73.5 | SIGMA= | 2.3 | PHAS= | -29.7 | FOM= | 0.84 | TEST= 0
| INDE | 9 | 55 | 18 | FOBS= | 70.0 | SIGMA= | 2.8 | PHAS= | -163.3 | FOM= | 0.81 | TEST= 0
| INDE | 9 | 55 | 20 | FOBS= | 0.0 | SIGMA= | 21.3 | PHAS= | 0.0 | FOM= | 0.00 | TEST= 1
| INDE | 9 | 55 | 22 | FOBS= | 54.0 | SIGMA= | 3.8 | PHAS= | 4.6 | FOM= | 0.69 | TEST= 0
| INDE | 9 | 55 | 24 | FOBS= | 94.4 | SIGMA= | 2.1 | PHAS= | 62.5 | FOM= | 0.86 | TEST= 0
| INDE | 9 | 55 | 26 | FOBS= | 82.6 | SIGMA= | 2.4 | PHAS= | 18.9 | FOM= | 0.89 | TEST= 0
| INDE | 9 | 55 | 28 | FOBS= | 0.0 | SIGMA= | 20.6 | PHAS= | 0.0 | FOM= | 0.00 | TEST= 0
| INDE | 9 | 55 | 30 | FOBS= | 63.9 | SIGMA= | 3.1 | PHAS= | -140.5 | FOM= | 0.69 | TEST= 0
| INDE | 9 | 55 | 32 | FOBS= | 91.3 | SIGMA= | 2.2 | PHAS= | -67.3 | FOM= | 0.84 | TEST= 0
| INDE | 9 | 55 | 34 | FOBS= | 49.6 | SIGMA= | 3.9 | PHAS= | -32.0 | FOM= | 0.77 | TEST= 0
| INDE | 9 | 55 | 36 | FOBS= | 97.7 | SIGMA= | 2.1 | PHAS= | 89.6 | FOM= | 0.91 | TEST= 0
| INDE | 9 | 55 | 38 | FOBS= | 53.3 | SIGMA= | 3.3 | PHAS= | -132.5 | FOM= | 0.91 | TEST= 0
| INDE | 9 | 55 | 40 | FOBS= | 65.3 | SIGMA= | 3.1 | PHAS= | 104.4 | FOM= | 0.39 | TEST= 0
| INDE | 9 | 55 | 42 | FOBS= | 48.7 | SIGMA= | 3.8 | PHAS= | -28.9 | FOM= | 0.36 | TEST= 1
| INDE | 9 | 55 | 44 | FOBS= | 33.0 | SIGMA= | 6.0 | PHAS= | -134.5 | FOM= | 0.61 | TEST= 0
| INDE | 9 | 55 | 46 | FOBS= | 0.0 | SIGMA= | 20.9 | PHAS= | 0.0 | FOM= | 0.00 | TEST= 0
| INDE | 9 | 55 | 48 | FOBS= | 66.7 | SIGMA= | 3.6 | PHAS= | -96.7 | FOM= | 0.62 | TEST= 0
| INDE | 9 | 55 | 50 | FOBS= | 55.0 | SIGMA= | 4.8 | PHAS= | 73.4 | FOM= | 0.92 | TEST= 0
| INDE | 9 | 55 | 52 | FOBS= | 0.0 | SIGMA= | 29.8 | PHAS= | 0.0 | FOM= | 0.00 | TEST= 0
| INDE | 9 | 55 | 54 | FOBS= | 45.1 | SIGMA= | 14.0 | PHAS= | -73.5 | FOM= | 0.83 | TEST= 0
| INDE | 9 | 56 | 9 | FOBS= | 44.3 | SIGMA= | 8.2 | PHAS= | -134.7 | FOM= | 0.43 | TEST= 0
| INDE | 9 | 56 | 11 | FOBS= | 140.5 | SIGMA= | 2.0 | PHAS= | -68.8 | FOM= | 0.92 | TEST= 0
| INDE | 9 | 56 | 13 | FOBS= | 38.9 | SIGMA= | 3.7 | PHAS= | -32.4 | FOM= | 0.23 | TEST= 0
| INDE | 9 | 56 | 15 | FOBS= | 25.9 | SIGMA= | 5.9 | PHAS= | 77.0 | FOM= | 0.44 | TEST= 0
| INDE | 9 | 56 | 17 | FOBS= | 0.0 | SIGMA= | 18.6 | PHAS= | 0.0 | FOM= | 0.00 | TEST= 0
| INDE | 9 | 56 | 19 | FOBS= | 83.9 | SIGMA= | 2.3 | PHAS= | -141.5 | FOM= | 0.78 | TEST= 0
| INDE | 9 | 56 | 21 | FOBS= | 0.0 | SIGMA= | 20.0 | PHAS= | 0.0 | FOM= | 0.00 | TEST= 0
| INDE | 9 | 56 | 23 | FOBS= | 54.4 | SIGMA= | 3.5 | PHAS= | -16.1 | FOM= | 0.56 | TEST= 0
| INDE | 9 | 56 | 25 | FOBS= | 105.7 | SIGMA= | 1.9 | PHAS= | -79.7 | FOM= | 0.91 | TEST= 0
| INDE | 9 | 56 | 27 | FOBS= | 57.2 | SIGMA= | 3.4 | PHAS= | 160.0 | FOM= | 0.72 | TEST= 0
| INDE | 9 | 56 | 29 | FOBS= | 27.0 | SIGMA= | 8.0 | PHAS= | 174.3 | FOM= | 0.19 | TEST= 1
| INDE | 9 | 56 | 31 | FOBS= | 61.7 | SIGMA= | 3.2 | PHAS= | -92.8 | FOM= | 0.87 | TEST= 0
| INDE | 9 | 56 | 33 | FOBS= | 70.2 | SIGMA= | 2.8 | PHAS= | -117.5 | FOM= | 0.78 | TEST= 0
| INDE | 9 | 56 | 35 | FOBS= | 62.1 | SIGMA= | 3.4 | PHAS= | 87.2 | FOM= | 0.87 | TEST= 0
| INDE | 9 | 56 | 37 | FOBS= | 85.9 | SIGMA= | 2.3 | PHAS= | 120.7 | FOM= | 0.81 | TEST= 0
| INDE | 9 | 56 | 39 | FOBS= | 0.0 | SIGMA= | 20.3 | PHAS= | 0.0 | FOM= | 0.00 | TEST= 1
| INDE | 9 | 56 | 41 | FOBS= | 0.0 | SIGMA= | 20.9 | PHAS= | 0.0 | FOM= | 0.00 | TEST= 0
| INDE | 9 | 56 | 43 | FOBS= | 100.3 | SIGMA= | 2.1 | PHAS= | 138.0 | FOM= | 0.93 | TEST= 0
| INDE | 9 | 56 | 45 | FOBS= | 98.6 | SIGMA= | 2.3 | PHAS= | -167.3 | FOM= | 0.94 | TEST= 0
| INDE | 9 | 56 | 47 | FOBS= | 36.6 | SIGMA= | 7.0 | PHAS= | 158.1 | FOM= | 0.53 | TEST= 0
| INDE | 9 | 56 | 49 | FOBS= | 65.4 | SIGMA= | 4.8 | PHAS= | 69.1 | FOM= | 0.85 | TEST= 0
| INDE | 9 | 56 | 51 | FOBS= | 31.4 | SIGMA= | 10.9 | PHAS= | -62.1 | FOM= | 0.64 | TEST= 0
| INDE | 9 | 56 | 53 | FOBS= | 69.2 | SIGMA= | 7.9 | PHAS= | 155.9 | FOM= | 0.63 | TEST= 0
| INDE | 9 | 57 | 10 | FOBS= | 0.0 | SIGMA= | 22.7 | PHAS= | 0.0 | FOM= | 0.00 | TEST= 0
| INDE | 9 | 57 | 12 | FOBS= | 50.6 | SIGMA= | 5.1 | PHAS= | -41.2 | FOM= | 0.35 | TEST= 0
| INDE | 9 | 57 | 14 | FOBS= | 86.3 | SIGMA= | 1.8 | PHAS= | -175.7 | FOM= | 0.94 | TEST= 0
| INDE | 9 | 57 | 16 | FOBS= | 117.5 | SIGMA= | 1.4 | PHAS= | -96.4 | FOM= | 0.92 | TEST= 0
| INDE | 9 | 57 | 18 | FOBS= | 114.9 | SIGMA= | 1.4 | PHAS= | -178.6 | FOM= | 0.79 | TEST= 0
| INDE | 9 | 57 | 20 | FOBS= | 25.5 | SIGMA= | 7.4 | PHAS= | 150.8 | FOM= | 0.32 | TEST= 0
| INDE | 9 | 57 | 22 | FOBS= | 43.2 | SIGMA= | 4.4 | PHAS= | -22.4 | FOM= | 0.70 | TEST= 0
| INDE | 9 | 57 | 24 | FOBS= | 48.3 | SIGMA= | 4.0 | PHAS= | 63.8 | FOM= | 0.11 | TEST= 1
| INDE | 9 | 57 | 26 | FOBS= | 0.0 | SIGMA= | 20.5 | PHAS= | 0.0 | FOM= | 0.00 | TEST= 0
| INDE | 9 | 57 | 28 | FOBS= | 24.8 | SIGMA= | 7.8 | PHAS= | -13.8 | FOM= | 0.38 | TEST= 0
| INDE | 9 | 57 | 30 | FOBS= | 165.1 | SIGMA= | 1.3 | PHAS= | -179.6 | FOM= | 0.83 | TEST= 1
| INDE | 9 | 57 | 32 | FOBS= | 131.2 | SIGMA= | 1.6 | PHAS= | -131.1 | FOM= | 0.93 | TEST= 0
| INDE | 9 | 57 | 34 | FOBS= | 1.9 | SIGMA= | 104.3 | PHAS= | -44.0 | FOM= | 0.01 | TEST= 0
| INDE | 9 | 57 | 36 | FOBS= | 48.1 | SIGMA= | 4.5 | PHAS= | 171.7 | FOM= | 0.63 | TEST= 0
| INDE | 9 | 57 | 38 | FOBS= | 34.4 | SIGMA= | 6.3 | PHAS= | 81.7 | FOM= | 0.03 | TEST= 1
| INDE | 9 | 57 | 40 | FOBS= | 0.0 | SIGMA= | 20.2 | PHAS= | 0.0 | FOM= | 0.00 | TEST= 0
| INDE | 9 | 57 | 42 | FOBS= | 76.8 | SIGMA= | 3.0 | PHAS= | -33.4 | FOM= | 0.84 | TEST= 0
| INDE | 9 | 57 | 44 | FOBS= | 79.3 | SIGMA= | 2.8 | PHAS= | 48.1 | FOM= | 0.94 | TEST= 0
| INDE | 9 | 57 | 46 | FOBS= | 0.0 | SIGMA= | 22.5 | PHAS= | 0.0 | FOM= | 0.00 | TEST= 0

*FIG. 12A - 254*

```
INDE  9  57  48  FOBS=  118.9  SIGMA=   2.3  PHAS=   -25.6  FOM=  0.94  TEST= 0
INDE  9  57  50  FOBS=   77.2  SIGMA=   4.6  PHAS=  -176.4  FOM=  0.82  TEST= 0
INDE  9  57  52  FOBS=   46.5  SIGMA=  11.5  PHAS=   102.3  FOM=  0.36  TEST= 0
INDE  9  58   9  FOBS=  148.6  SIGMA=   1.8  PHAS=   -33.1  FOM=  0.94  TEST= 0
INDE  9  58  11  FOBS=   15.2  SIGMA=  19.5  PHAS=   -57.9  FOM=  0.22  TEST= 0
INDE  9  58  13  FOBS=  131.9  SIGMA=   2.1  PHAS=   100.7  FOM=  0.80  TEST= 0
INDE  9  58  15  FOBS=  132.2  SIGMA=   1.4  PHAS=   129.8  FOM=  0.91  TEST= 0
INDE  9  58  17  FOBS=   73.4  SIGMA=   2.7  PHAS=   172.8  FOM=  0.91  TEST= 0
INDE  9  58  19  FOBS=   64.5  SIGMA=   2.6  PHAS=    46.2  FOM=  0.78  TEST= 0
INDE  9  58  21  FOBS=    0.0  SIGMA=  19.3  PHAS=     0.0  FOM=  0.00  TEST= 0
INDE  9  58  23  FOBS=   68.4  SIGMA=   2.8  PHAS=   -82.6  FOM=  0.80  TEST= 0
INDE  9  58  25  FOBS=    0.0  SIGMA=  19.7  PHAS=     0.0  FOM=  0.00  TEST= 0
INDE  9  58  27  FOBS=   56.4  SIGMA=   3.4  PHAS=   133.4  FOM=  0.79  TEST= 0
INDE  9  58  29  FOBS=   82.9  SIGMA=   2.4  PHAS=    54.2  FOM=  0.24  TEST= 0
INDE  9  58  31  FOBS=  162.2  SIGMA=   1.4  PHAS=   129.9  FOM=  0.96  TEST= 0
INDE  9  58  33  FOBS=   43.0  SIGMA=   5.0  PHAS=   145.7  FOM=  0.74  TEST= 0
INDE  9  58  35  FOBS=  107.0  SIGMA=   2.3  PHAS=   142.2  FOM=  0.90  TEST= 0
INDE  9  58  37  FOBS=   21.9  SIGMA=  10.9  PHAS=    73.2  FOM=  0.17  TEST= 0
INDE  9  58  39  FOBS=   34.6  SIGMA=   7.3  PHAS=    99.3  FOM=  0.46  TEST= 0
INDE  9  58  41  FOBS=   42.5  SIGMA=   5.2  PHAS=  -153.1  FOM=  0.19  TEST= 0
INDE  9  58  43  FOBS=   29.5  SIGMA=   7.2  PHAS=   -90.6  FOM=  0.36  TEST= 0
INDE  9  58  45  FOBS=   46.0  SIGMA=   4.8  PHAS=   -65.7  FOM=  0.47  TEST= 0
INDE  9  58  47  FOBS=  106.5  SIGMA=   2.6  PHAS=  -172.4  FOM=  0.94  TEST= 0
INDE  9  58  49  FOBS=   76.0  SIGMA=   4.5  PHAS=   167.5  FOM=  0.90  TEST= 0
INDE  9  59  10  FOBS=  139.3  SIGMA=   1.9  PHAS=  -166.5  FOM=  0.94  TEST= 0
INDE  9  59  12  FOBS=  177.6  SIGMA=   1.6  PHAS=    21.7  FOM=  0.92  TEST= 0
INDE  9  59  14  FOBS=   97.8  SIGMA=   2.7  PHAS=   101.0  FOM=  0.92  TEST= 0
INDE  9  59  16  FOBS=   40.9  SIGMA=   4.5  PHAS=    31.0  FOM=  0.83  TEST= 0
INDE  9  59  18  FOBS=   21.1  SIGMA=   9.4  PHAS=    -5.8  FOM=  0.04  TEST= 0
INDE  9  59  20  FOBS=   63.4  SIGMA=   2.6  PHAS=   -43.5  FOM=  0.54  TEST= 0
INDE  9  59  22  FOBS=   70.9  SIGMA=   2.7  PHAS=  -161.5  FOM=  0.89  TEST= 0
INDE  9  59  24  FOBS=   64.4  SIGMA=   3.0  PHAS=   110.0  FOM=  0.68  TEST= 0
INDE  9  59  26  FOBS=    0.0  SIGMA=  19.5  PHAS=     0.0  FOM=  0.00  TEST= 0
INDE  9  59  28  FOBS=   98.6  SIGMA=   2.2  PHAS=    -0.6  FOM=  0.85  TEST= 0
INDE  9  59  30  FOBS=   14.1  SIGMA=  18.9  PHAS=    64.7  FOM=  0.07  TEST= 0
INDE  9  59  32  FOBS=    0.0  SIGMA=  21.6  PHAS=     0.0  FOM=  0.00  TEST= 0
INDE  9  59  34  FOBS=   45.0  SIGMA=   5.3  PHAS=    87.2  FOM=  0.73  TEST= 0
INDE  9  59  36  FOBS=    0.0  SIGMA=  25.2  PHAS=     0.0  FOM=  0.00  TEST= 1
INDE  9  59  38  FOBS=   16.0  SIGMA=  15.2  PHAS=   -84.1  FOM=  0.18  TEST= 0
INDE  9  59  40  FOBS=   26.8  SIGMA=   7.7  PHAS=    -5.6  FOM=  0.04  TEST= 0
INDE  9  59  42  FOBS=    7.6  SIGMA=  30.8  PHAS=   -26.3  FOM=  0.16  TEST= 0
INDE  9  59  44  FOBS=   39.8  SIGMA=   5.5  PHAS=    36.7  FOM=  0.73  TEST= 0
INDE  9  59  46  FOBS=    0.0  SIGMA=  23.5  PHAS=     0.0  FOM=  0.00  TEST= 0
INDE  9  59  48  FOBS=   51.1  SIGMA=   6.6  PHAS=    80.8  FOM=  0.85  TEST= 0
INDE  9  60   9  FOBS=   28.1  SIGMA=   9.0  PHAS=    56.0  FOM=  0.15  TEST= 0
INDE  9  60  11  FOBS=    0.0  SIGMA=  23.8  PHAS=     0.0  FOM=  0.00  TEST= 0
INDE  9  60  13  FOBS=  139.8  SIGMA=   1.9  PHAS=    19.2  FOM=  0.89  TEST= 0
INDE  9  60  15  FOBS=   20.5  SIGMA=   8.4  PHAS=    67.1  FOM=  0.25  TEST= 1
INDE  9  60  17  FOBS=   62.6  SIGMA=   3.1  PHAS=  -157.6  FOM=  0.56  TEST= 0
INDE  9  60  19  FOBS=   11.8  SIGMA=  17.0  PHAS=  -138.7  FOM=  0.11  TEST= 0
INDE  9  60  21  FOBS=    0.0  SIGMA=  18.9  PHAS=     0.0  FOM=  0.00  TEST= 0
INDE  9  60  23  FOBS=   35.6  SIGMA=   6.3  PHAS=     5.6  FOM=  0.87  TEST= 0
INDE  9  60  25  FOBS=   48.3  SIGMA=   4.8  PHAS=   122.1  FOM=  0.44  TEST= 0
INDE  9  60  27  FOBS=   22.6  SIGMA=  12.0  PHAS=   109.9  FOM=  0.06  TEST= 0
INDE  9  60  29  FOBS=   63.0  SIGMA=   3.7  PHAS=  -122.9  FOM=  0.72  TEST= 0
INDE  9  60  31  FOBS=   27.2  SIGMA=   8.6  PHAS=    65.1  FOM=  0.14  TEST= 0
INDE  9  60  33  FOBS=   24.5  SIGMA=  10.8  PHAS=    88.0  FOM=  0.38  TEST= 0
INDE  9  60  35  FOBS=    0.0  SIGMA=  23.1  PHAS=     0.0  FOM=  0.00  TEST= 0
INDE  9  60  37  FOBS=    0.0  SIGMA=  23.6  PHAS=     0.0  FOM=  0.00  TEST= 0
INDE  9  60  39  FOBS=   82.2  SIGMA=   3.0  PHAS=    90.8  FOM=  0.90  TEST= 0
INDE  9  60  41  FOBS=   95.5  SIGMA=   2.3  PHAS=   -67.5  FOM=  0.12  TEST= 1
INDE  9  60  43  FOBS=   40.5  SIGMA=   6.6  PHAS=   -66.0  FOM=  0.36  TEST= 0
INDE  9  60  45  FOBS=    0.0  SIGMA=  25.2  PHAS=     0.0  FOM=  0.00  TEST= 0
INDE  9  60  47  FOBS=    0.0  SIGMA=  28.0  PHAS=     0.0  FOM=  0.00  TEST= 0
INDE  9  61  10  FOBS=    0.0  SIGMA=  26.7  PHAS=     0.0  FOM=  0.00  TEST= 0
INDE  9  61  12  FOBS=   47.0  SIGMA=   6.1  PHAS=   -15.5  FOM=  0.55  TEST= 0
INDE  9  61  14  FOBS=   54.3  SIGMA=   4.6  PHAS=   101.4  FOM=  0.72  TEST= 0
INDE  9  61  16  FOBS=   56.6  SIGMA=   3.3  PHAS=   -51.8  FOM=  0.80  TEST= 0
INDE  9  61  18  FOBS=   26.5  SIGMA=   7.0  PHAS=    40.0  FOM=  0.13  TEST= 0
INDE  9  61  20  FOBS=   26.8  SIGMA=   8.5  PHAS=   140.5  FOM=  0.64  TEST= 0
```

*FIG. 12A - 255*

```
INDE  9  61  22  FOBS=  158.5  SIGMA=   1.5  PHAS=  -101.1  FOM=  0.96  TEST=  0
INDE  9  61  24  FOBS=    0.0  SIGMA=  21.1  PHAS=     0.0  FOM=  0.00  TEST=  0
INDE  9  61  26  FOBS=    0.0  SIGMA=  23.1  PHAS=     0.0  FOM=  0.00  TEST=  0
INDE  9  61  28  FOBS=  103.7  SIGMA=   2.3  PHAS=     0.5  FOM=  0.91  TEST=  0
INDE  9  61  30  FOBS=    0.0  SIGMA=  23.2  PHAS=     0.0  FOM=  0.00  TEST=  0
INDE  9  61  32  FOBS=   82.9  SIGMA=   3.4  PHAS=   151.2  FOM=  0.69  TEST=  0
INDE  9  61  34  FOBS=    0.0  SIGMA=  23.3  PHAS=     0.0  FOM=  0.00  TEST=  0
INDE  9  61  36  FOBS=   36.3  SIGMA=   7.8  PHAS=   -40.6  FOM=  0.76  TEST=  0
INDE  9  61  38  FOBS=   38.0  SIGMA=   7.4  PHAS=   -14.5  FOM=  0.63  TEST=  0
INDE  9  61  40  FOBS=   87.5  SIGMA=   3.3  PHAS=   -56.0  FOM=  0.88  TEST=  0
INDE  9  61  42  FOBS=   53.7  SIGMA=   4.4  PHAS=  -134.3  FOM=  0.43  TEST=  0
INDE  9  61  44  FOBS=   35.3  SIGMA=   6.8  PHAS=   -47.8  FOM=  0.32  TEST=  0
INDE  9  61  46  FOBS=   16.5  SIGMA=  23.6  PHAS=   -71.7  FOM=  0.10  TEST=  0
INDE  9  62   9  FOBS=   60.5  SIGMA=   4.2  PHAS=   131.4  FOM=  0.50  TEST=  0
INDE  9  62  11  FOBS=   40.6  SIGMA=   6.2  PHAS=    33.1  FOM=  0.46  TEST=  0
INDE  9  62  13  FOBS=   50.1  SIGMA=   4.8  PHAS=   -70.4  FOM=  0.53  TEST=  0
INDE  9  62  15  FOBS=   30.8  SIGMA=   9.2  PHAS=   -58.2  FOM=  0.25  TEST=  0
INDE  9  62  17  FOBS=   93.9  SIGMA=   2.4  PHAS=   -62.6  FOM=  0.91  TEST=  0
INDE  9  62  19  FOBS=    0.0  SIGMA=  21.5  PHAS=     0.0  FOM=  0.00  TEST=  0
INDE  9  62  21  FOBS=  132.8  SIGMA=   1.7  PHAS=   159.8  FOM=  0.91  TEST=  0
INDE  9  62  23  FOBS=   97.1  SIGMA=   2.8  PHAS=  -141.7  FOM=  0.92  TEST=  0
INDE  9  62  25  FOBS=    0.0  SIGMA=  23.1  PHAS=     0.0  FOM=  0.00  TEST=  0
INDE  9  62  27  FOBS=   76.6  SIGMA=   3.7  PHAS=   -40.0  FOM=  0.91  TEST=  0
INDE  9  62  29  FOBS=  144.1  SIGMA=   2.0  PHAS=  -121.2  FOM=  0.96  TEST=  0
INDE  9  62  31  FOBS=   42.8  SIGMA=   6.3  PHAS=    19.9  FOM=  0.62  TEST=  0
INDE  9  62  33  FOBS=   74.1  SIGMA=   3.8  PHAS=   160.7  FOM=  0.15  TEST=  1
INDE  9  62  35  FOBS=    0.0  SIGMA=  23.6  PHAS=     0.0  FOM=  0.00  TEST=  0
INDE  9  62  37  FOBS=   27.2  SIGMA=  10.3  PHAS=    55.5  FOM=  0.53  TEST=  0
INDE  9  62  39  FOBS=   53.2  SIGMA=   5.4  PHAS=   168.9  FOM=  0.71  TEST=  0
INDE  9  62  41  FOBS=    0.0  SIGMA=  21.6  PHAS=     0.0  FOM=  0.00  TEST=  0
INDE  9  62  43  FOBS=   34.9  SIGMA=  10.5  PHAS=    33.8  FOM=  0.13  TEST=  0
INDE  9  62  45  FOBS=  122.9  SIGMA=   2.8  PHAS=  -164.8  FOM=  0.95  TEST=  0
INDE  9  63  10  FOBS=   42.0  SIGMA=   6.9  PHAS=  -154.9  FOM=  0.67  TEST=  0
INDE  9  63  12  FOBS=   52.8  SIGMA=   6.7  PHAS=   140.4  FOM=  0.80  TEST=  0
INDE  9  63  14  FOBS=  106.4  SIGMA=   3.4  PHAS=   133.0  FOM=  0.92  TEST=  0
INDE  9  63  16  FOBS=   81.9  SIGMA=   2.4  PHAS=   -91.1  FOM=  0.92  TEST=  0
INDE  9  63  18  FOBS=   62.2  SIGMA=   3.5  PHAS=   -92.2  FOM=  0.56  TEST=  1
INDE  9  63  20  FOBS=   47.5  SIGMA=   5.1  PHAS=   165.3  FOM=  0.78  TEST=  0
INDE  9  63  22  FOBS=   76.3  SIGMA=   3.2  PHAS=   -81.1  FOM=  0.89  TEST=  0
INDE  9  63  24  FOBS=    0.0  SIGMA=  22.9  PHAS=     0.0  FOM=  0.00  TEST=  1
INDE  9  63  26  FOBS=   31.3  SIGMA=   8.6  PHAS=  -110.4  FOM=  0.82  TEST=  0
INDE  9  63  28  FOBS=   99.2  SIGMA=   2.9  PHAS=  -112.4  FOM=  0.68  TEST=  0
INDE  9  63  30  FOBS=  103.1  SIGMA=   2.7  PHAS=   143.6  FOM=  0.41  TEST=  1
INDE  9  63  32  FOBS=    0.0  SIGMA=  26.0  PHAS=     0.0  FOM=  0.00  TEST=  1
INDE  9  63  34  FOBS=    0.0  SIGMA=  23.4  PHAS=     0.0  FOM=  0.00  TEST=  0
INDE  9  63  36  FOBS=   38.4  SIGMA=   7.4  PHAS=    51.6  FOM=  0.07  TEST=  1
INDE  9  63  38  FOBS=   66.5  SIGMA=   4.3  PHAS=   -30.8  FOM=  0.88  TEST=  0
INDE  9  63  40  FOBS=   66.7  SIGMA=   4.4  PHAS=   -67.7  FOM=  0.65  TEST=  0
INDE  9  63  42  FOBS=   11.6  SIGMA=  25.1  PHAS=   -32.1  FOM=  0.15  TEST=  0
INDE  9  63  44  FOBS=   81.1  SIGMA=   4.8  PHAS=    80.3  FOM=  0.92  TEST=  0
INDE  9  64   9  FOBS=   90.9  SIGMA=   4.0  PHAS=    96.1  FOM=  0.91  TEST=  0
INDE  9  64  11  FOBS=  122.4  SIGMA=   3.0  PHAS=    26.1  FOM=  0.95  TEST=  0
INDE  9  64  13  FOBS=    0.0  SIGMA=  26.2  PHAS=     0.0  FOM=  0.00  TEST=  0
INDE  9  64  15  FOBS=   57.6  SIGMA=   6.1  PHAS=    72.4  FOM=  0.57  TEST=  0
INDE  9  64  17  FOBS=   57.0  SIGMA=   3.6  PHAS=  -109.0  FOM=  0.89  TEST=  0
INDE  9  64  19  FOBS=   41.5  SIGMA=   5.4  PHAS=   175.9  FOM=  0.59  TEST=  0
INDE  9  64  21  FOBS=  137.1  SIGMA=   1.9  PHAS=   114.9  FOM=  0.95  TEST=  0
INDE  9  64  23  FOBS=   72.6  SIGMA=   3.0  PHAS=  -155.6  FOM=  0.91  TEST=  0
INDE  9  64  25  FOBS=   85.6  SIGMA=   3.2  PHAS=  -142.7  FOM=  0.61  TEST=  0
INDE  9  64  27  FOBS=   48.5  SIGMA=   5.6  PHAS=   -91.4  FOM=  0.72  TEST=  0
INDE  9  64  29  FOBS=   73.9  SIGMA=   3.8  PHAS=    96.9  FOM=  0.83  TEST=  0
INDE  9  64  31  FOBS=   10.2  SIGMA=  26.7  PHAS=   141.6  FOM=  0.09  TEST=  0
INDE  9  64  33  FOBS=    0.0  SIGMA=  26.1  PHAS=     0.0  FOM=  0.00  TEST=  0
INDE  9  64  35  FOBS=   34.5  SIGMA=  10.3  PHAS=  -157.8  FOM=  0.02  TEST=  1
INDE  9  64  37  FOBS=    0.0  SIGMA=  26.7  PHAS=     0.0  FOM=  0.00  TEST=  1
INDE  9  64  39  FOBS=   82.1  SIGMA=   3.6  PHAS=  -159.0  FOM=  0.92  TEST=  0
INDE  9  64  41  FOBS=   19.1  SIGMA=  15.4  PHAS=    56.1  FOM=  0.01  TEST=  0
INDE  9  64  43  FOBS=   27.9  SIGMA=  10.9  PHAS=   -49.8  FOM=  0.28  TEST=  0
INDE  9  65  10  FOBS=  108.3  SIGMA=   3.4  PHAS=   -51.5  FOM=  0.91  TEST=  0
INDE  9  65  12  FOBS=    0.0  SIGMA=  26.2  PHAS=     0.0  FOM=  0.00  TEST=  0
```

*FIG. 12A - 256*

| | | | | | | | | | | | | |
|---|---|---|---|---|---|---|---|---|---|---|---|---|
| INDE | 9 | 65 | 14 | FOBS= | 35.6 | SIGMA= | 9.8 | PHAS= | 156.7 | FOM= | 0.55 | TEST= 0 |
| INDE | 9 | 65 | 16 | FOBS= | 62.7 | SIGMA= | 5.5 | PHAS= | -124.1 | FOM= | 0.77 | TEST= 0 |
| INDE | 9 | 65 | 18 | FOBS= | 22.7 | SIGMA= | 9.2 | PHAS= | 146.3 | FOM= | 0.28 | TEST= 0 |
| INDE | 9 | 65 | 20 | FOBS= | 75.0 | SIGMA= | 3.1 | PHAS= | 106.3 | FOM= | 0.67 | TEST= 0 |
| INDE | 9 | 65 | 22 | FOBS= | 22.1 | SIGMA= | 15.3 | PHAS= | 11.8 | FOM= | 0.02 | TEST= 1 |
| INDE | 9 | 65 | 24 | FOBS= | 44.5 | SIGMA= | 4.9 | PHAS= | 138.4 | FOM= | 0.57 | TEST= 0 |
| INDE | 9 | 65 | 26 | FOBS= | 68.6 | SIGMA= | 4.0 | PHAS= | -173.2 | FOM= | 0.11 | TEST= 1 |
| INDE | 9 | 65 | 28 | FOBS= | 0.0 | SIGMA= | 23.4 | PHAS= | 0.0 | FOM= | 0.00 | TEST= 0 |
| INDE | 9 | 65 | 30 | FOBS= | 48.1 | SIGMA= | 5.9 | PHAS= | 61.4 | FOM= | 0.80 | TEST= 0 |
| INDE | 9 | 65 | 32 | FOBS= | 46.0 | SIGMA= | 6.1 | PHAS= | -123.5 | FOM= | 0.01 | TEST= 1 |
| INDE | 9 | 65 | 34 | FOBS= | 68.6 | SIGMA= | 4.1 | PHAS= | 52.7 | FOM= | 0.61 | TEST= 0 |
| INDE | 9 | 65 | 36 | FOBS= | 0.0 | SIGMA= | 23.9 | PHAS= | 0.0 | FOM= | 0.00 | TEST= 0 |
| INDE | 9 | 65 | 38 | FOBS= | 59.9 | SIGMA= | 5.0 | PHAS= | 117.8 | FOM= | 0.47 | TEST= 0 |
| INDE | 9 | 65 | 40 | FOBS= | 35.2 | SIGMA= | 8.5 | PHAS= | 103.7 | FOM= | 0.03 | TEST= 1 |
| INDE | 9 | 66 | 9 | FOBS= | 23.1 | SIGMA= | 15.5 | PHAS= | 51.6 | FOM= | 0.28 | TEST= 0 |
| INDE | 9 | 66 | 11 | FOBS= | 8.4 | SIGMA= | 41.1 | PHAS= | -101.3 | FOM= | 0.19 | TEST= 0 |
| INDE | 9 | 66 | 13 | FOBS= | 51.3 | SIGMA= | 6.8 | PHAS= | 128.4 | FOM= | 0.73 | TEST= 0 |
| INDE | 9 | 66 | 15 | FOBS= | 0.0 | SIGMA= | 26.2 | PHAS= | 0.0 | FOM= | 0.00 | TEST= 0 |
| INDE | 9 | 66 | 17 | FOBS= | 49.4 | SIGMA= | 6.9 | PHAS= | -120.6 | FOM= | 0.60 | TEST= 0 |
| INDE | 9 | 66 | 19 | FOBS= | 58.8 | SIGMA= | 3.8 | PHAS= | -25.0 | FOM= | 0.37 | TEST= 0 |
| INDE | 9 | 66 | 21 | FOBS= | 55.4 | SIGMA= | 4.2 | PHAS= | 95.4 | FOM= | 0.40 | TEST= 0 |
| INDE | 9 | 66 | 23 | FOBS= | 63.2 | SIGMA= | 3.3 | PHAS= | 53.8 | FOM= | 0.75 | TEST= 0 |
| INDE | 9 | 66 | 25 | FOBS= | 51.2 | SIGMA= | 4.4 | PHAS= | -164.8 | FOM= | 0.82 | TEST= 0 |
| INDE | 9 | 66 | 27 | FOBS= | 0.0 | SIGMA= | 23.3 | PHAS= | 0.0 | FOM= | 0.00 | TEST= 1 |
| INDE | 9 | 66 | 29 | FOBS= | 28.0 | SIGMA= | 9.9 | PHAS= | 97.7 | FOM= | 0.31 | TEST= 0 |
| INDE | 9 | 66 | 31 | FOBS= | 0.0 | SIGMA= | 23.7 | PHAS= | 0.0 | FOM= | 0.00 | TEST= 0 |
| INDE | 9 | 66 | 33 | FOBS= | 48.3 | SIGMA= | 5.9 | PHAS= | -73.9 | FOM= | 0.29 | TEST= 1 |
| INDE | 9 | 66 | 35 | FOBS= | 0.0 | SIGMA= | 23.8 | PHAS= | 0.0 | FOM= | 0.00 | TEST= 0 |
| INDE | 9 | 66 | 37 | FOBS= | 49.4 | SIGMA= | 5.9 | PHAS= | 83.1 | FOM= | 0.84 | TEST= 0 |
| INDE | 9 | 66 | 39 | FOBS= | 47.3 | SIGMA= | 6.4 | PHAS= | 83.6 | FOM= | 0.72 | TEST= 0 |
| INDE | 9 | 67 | 10 | FOBS= | 39.9 | SIGMA= | 12.1 | PHAS= | -7.6 | FOM= | 0.10 | TEST= 1 |
| INDE | 9 | 67 | 12 | FOBS= | 59.0 | SIGMA= | 6.0 | PHAS= | 61.7 | FOM= | 0.57 | TEST= 0 |
| INDE | 9 | 67 | 14 | FOBS= | 79.3 | SIGMA= | 4.5 | PHAS= | 134.0 | FOM= | 0.84 | TEST= 0 |
| INDE | 9 | 67 | 16 | FOBS= | 54.6 | SIGMA= | 6.4 | PHAS= | -38.4 | FOM= | 0.31 | TEST= 1 |
| INDE | 9 | 67 | 18 | FOBS= | 33.7 | SIGMA= | 10.2 | PHAS= | 168.5 | FOM= | 0.76 | TEST= 0 |
| INDE | 9 | 67 | 20 | FOBS= | 40.7 | SIGMA= | 5.6 | PHAS= | -107.9 | FOM= | 0.54 | TEST= 0 |
| INDE | 9 | 67 | 22 | FOBS= | 100.6 | SIGMA= | 2.4 | PHAS= | -87.6 | FOM= | 0.04 | TEST= 1 |
| INDE | 9 | 67 | 24 | FOBS= | 0.0 | SIGMA= | 22.8 | PHAS= | 0.0 | FOM= | 0.00 | TEST= 0 |
| INDE | 9 | 67 | 26 | FOBS= | 77.2 | SIGMA= | 3.0 | PHAS= | 78.3 | FOM= | 0.84 | TEST= 0 |
| INDE | 9 | 67 | 28 | FOBS= | 14.8 | SIGMA= | 18.8 | PHAS= | 151.7 | FOM= | 0.28 | TEST= 0 |
| INDE | 9 | 67 | 30 | FOBS= | 94.7 | SIGMA= | 3.1 | PHAS= | 36.6 | FOM= | 0.90 | TEST= 0 |
| INDE | 9 | 67 | 32 | FOBS= | 36.7 | SIGMA= | 7.8 | PHAS= | 171.5 | FOM= | 0.29 | TEST= 1 |
| INDE | 9 | 67 | 34 | FOBS= | 26.1 | SIGMA= | 10.9 | PHAS= | 129.0 | FOM= | 0.10 | TEST= 0 |
| INDE | 9 | 67 | 36 | FOBS= | 35.7 | SIGMA= | 8.1 | PHAS= | -53.9 | FOM= | 0.22 | TEST= 0 |
| INDE | 9 | 67 | 38 | FOBS= | 63.7 | SIGMA= | 4.8 | PHAS= | -39.8 | FOM= | 0.84 | TEST= 0 |
| INDE | 9 | 68 | 13 | FOBS= | 67.6 | SIGMA= | 7.3 | PHAS= | 179.9 | FOM= | 0.72 | TEST= 0 |
| INDE | 9 | 68 | 15 | FOBS= | 34.9 | SIGMA= | 14.1 | PHAS= | -142.0 | FOM= | 0.54 | TEST= 0 |
| INDE | 9 | 68 | 17 | FOBS= | 44.6 | SIGMA= | 7.8 | PHAS= | -149.1 | FOM= | 0.59 | TEST= 0 |
| INDE | 9 | 68 | 19 | FOBS= | 41.4 | SIGMA= | 5.0 | PHAS= | 54.9 | FOM= | 0.44 | TEST= 0 |
| INDE | 9 | 68 | 21 | FOBS= | 103.3 | SIGMA= | 2.4 | PHAS= | 67.1 | FOM= | 0.13 | TEST= 1 |
| INDE | 9 | 68 | 23 | FOBS= | 33.1 | SIGMA= | 7.4 | PHAS= | 17.4 | FOM= | 0.16 | TEST= 0 |
| INDE | 9 | 68 | 25 | FOBS= | 0.0 | SIGMA= | 26.2 | PHAS= | 0.0 | FOM= | 0.00 | TEST= 0 |
| INDE | 9 | 68 | 27 | FOBS= | 31.1 | SIGMA= | 8.5 | PHAS= | 67.0 | FOM= | 0.76 | TEST= 0 |
| INDE | 9 | 68 | 29 | FOBS= | 42.4 | SIGMA= | 6.7 | PHAS= | -71.5 | FOM= | 0.82 | TEST= 0 |
| INDE | 9 | 68 | 31 | FOBS= | 0.0 | SIGMA= | 26.5 | PHAS= | 0.0 | FOM= | 0.00 | TEST= 0 |
| INDE | 9 | 68 | 33 | FOBS= | 26.7 | SIGMA= | 10.8 | PHAS= | -150.8 | FOM= | 0.15 | TEST= 0 |
| INDE | 9 | 68 | 35 | FOBS= | 0.0 | SIGMA= | 24.1 | PHAS= | 0.0 | FOM= | 0.00 | TEST= 0 |
| INDE | 9 | 69 | 18 | FOBS= | 25.7 | SIGMA= | 19.4 | PHAS= | -132.3 | FOM= | 0.09 | TEST= 0 |
| INDE | 9 | 69 | 20 | FOBS= | 26.0 | SIGMA= | 9.4 | PHAS= | -131.7 | FOM= | 0.34 | TEST= 0 |
| INDE | 9 | 69 | 22 | FOBS= | 23.8 | SIGMA= | 11.4 | PHAS= | 48.0 | FOM= | 0.21 | TEST= 0 |
| INDE | 9 | 69 | 24 | FOBS= | 0.0 | SIGMA= | 22.3 | PHAS= | 0.0 | FOM= | 0.00 | TEST= 0 |
| INDE | 9 | 69 | 26 | FOBS= | 93.0 | SIGMA= | 3.0 | PHAS= | -26.1 | FOM= | 0.90 | TEST= 0 |
| INDE | 9 | 69 | 28 | FOBS= | 0.0 | SIGMA= | 23.1 | PHAS= | 0.0 | FOM= | 0.00 | TEST= 0 |
| INDE | 9 | 69 | 30 | FOBS= | 0.0 | SIGMA= | 23.7 | PHAS= | 0.0 | FOM= | 0.00 | TEST= 0 |
| INDE | 9 | 69 | 32 | FOBS= | 46.1 | SIGMA= | 6.5 | PHAS= | -19.1 | FOM= | 0.78 | TEST= 0 |
| INDE | 9 | 69 | 34 | FOBS= | 28.8 | SIGMA= | 10.3 | PHAS= | -141.0 | FOM= | 0.45 | TEST= 0 |
| INDE | 9 | 70 | 21 | FOBS= | 87.3 | SIGMA= | 3.4 | PHAS= | -69.0 | FOM= | 0.72 | TEST= 0 |
| INDE | 9 | 70 | 23 | FOBS= | 0.0 | SIGMA= | 23.5 | PHAS= | 0.0 | FOM= | 0.00 | TEST= 0 |
| INDE | 9 | 70 | 25 | FOBS= | 50.5 | SIGMA= | 4.8 | PHAS= | -58.9 | FOM= | 0.80 | TEST= 0 |
| INDE | 9 | 70 | 27 | FOBS= | 20.4 | SIGMA= | 13.6 | PHAS= | 80.2 | FOM= | 0.27 | TEST= 0 |

*FIG. 12A - 257*

```
INDE   9  70  29  FOBS=   40.4  SIGMA=   8.6  PHAS=   43.2  FOM= 0.57  TEST= 0
INDE   9  70  31  FOBS=   11.7  SIGMA=  30.6  PHAS=  -94.2  FOM= 0.33  TEST= 0
INDE   9  71  22  FOBS=    0.0  SIGMA=  25.0  PHAS=    0.0  FOM= 0.00  TEST= 0
INDE   9  71  24  FOBS=   72.4  SIGMA=   4.8  PHAS=  -75.4  FOM= 0.90  TEST= 0
INDE   9  71  26  FOBS=   51.2  SIGMA=   5.7  PHAS=  -76.5  FOM= 0.60  TEST= 0
INDE   9  71  28  FOBS=   14.1  SIGMA=  24.1  PHAS= -133.5  FOM= 0.14  TEST= 0
INDE   9  71  30  FOBS=   48.7  SIGMA=   5.8  PHAS=   80.6  FOM= 0.39  TEST= 0
INDE   9  72  21  FOBS=   10.0  SIGMA=  27.4  PHAS=  -64.6  FOM= 0.10  TEST= 0
INDE   9  72  23  FOBS=   41.4  SIGMA=   8.3  PHAS= -123.1  FOM= 0.81  TEST= 0
INDE   9  72  25  FOBS=   13.6  SIGMA=  26.7  PHAS= -174.3  FOM= 0.41  TEST= 0
INDE   9  72  27  FOBS=   34.4  SIGMA=   8.9  PHAS=   80.0  FOM= 0.18  TEST= 0
INDE   9  73  22  FOBS=   49.5  SIGMA=   6.0  PHAS=  -49.6  FOM= 0.08  TEST= 1
INDE   9  73  24  FOBS=    0.0  SIGMA=  26.8  PHAS=    0.0  FOM= 0.00  TEST= 0
INDE  10  11  11  FOBS=  158.4  SIGMA=   0.4  PHAS=   -5.4  FOM= 0.73  TEST= 0
INDE  10  11  13  FOBS=  164.6  SIGMA=   0.4  PHAS=  119.4  FOM= 0.80  TEST= 1
INDE  10  11  15  FOBS=  410.0  SIGMA=   0.5  PHAS=   75.3  FOM= 0.96  TEST= 0
INDE  10  11  17  FOBS=  292.6  SIGMA=   0.5  PHAS=   37.8  FOM= 0.89  TEST= 0
INDE  10  11  19  FOBS=  158.1  SIGMA=   0.5  PHAS=  100.2  FOM= 0.91  TEST= 0
INDE  10  11  21  FOBS=   96.4  SIGMA=   0.7  PHAS=   33.2  FOM= 0.94  TEST= 0
INDE  10  11  23  FOBS=  110.5  SIGMA=   0.6  PHAS=  -30.8  FOM= 0.99  TEST= 0
INDE  10  11  25  FOBS=   66.6  SIGMA=   1.0  PHAS= -148.4  FOM= 0.95  TEST= 0
INDE  10  11  27  FOBS=   96.5  SIGMA=   0.8  PHAS=   64.9  FOM= 0.91  TEST= 0
INDE  10  11  29  FOBS=  197.3  SIGMA=   0.5  PHAS=   53.8  FOM= 0.96  TEST= 0
INDE  10  11  31  FOBS=   96.5  SIGMA=   0.9  PHAS=   77.3  FOM= 0.99  TEST= 0
INDE  10  11  33  FOBS=  159.1  SIGMA=   0.7  PHAS=  -93.3  FOM= 0.99  TEST= 0
INDE  10  11  35  FOBS=  287.4  SIGMA=   0.7  PHAS= -153.3  FOM= 0.96  TEST= 0
INDE  10  11  37  FOBS=  271.1  SIGMA=   0.7  PHAS=   23.0  FOM= 0.95  TEST= 0
INDE  10  11  39  FOBS=  275.2  SIGMA=   0.7  PHAS= -148.1  FOM= 0.93  TEST= 0
INDE  10  11  41  FOBS=  290.9  SIGMA=   0.8  PHAS= -103.5  FOM= 0.97  TEST= 0
INDE  10  11  43  FOBS=  384.8  SIGMA=   0.8  PHAS=  -43.7  FOM= 0.97  TEST= 0
INDE  10  11  45  FOBS=  268.1  SIGMA=   1.2  PHAS=   85.0  FOM= 0.34  TEST= 1
INDE  10  11  47  FOBS=  137.3  SIGMA=   1.6  PHAS=  179.3  FOM= 0.90  TEST= 0
INDE  10  11  49  FOBS=  168.5  SIGMA=   1.3  PHAS=  116.1  FOM= 0.95  TEST= 0
INDE  10  11  51  FOBS=   65.2  SIGMA=   3.1  PHAS=   36.6  FOM= 0.73  TEST= 0
INDE  10  11  53  FOBS=  197.5  SIGMA=   1.7  PHAS=  -34.8  FOM= 0.90  TEST= 0
INDE  10  11  55  FOBS=  208.6  SIGMA=   1.4  PHAS=  -60.5  FOM= 0.96  TEST= 0
INDE  10  11  57  FOBS=   66.3  SIGMA=   2.1  PHAS=  104.7  FOM= 0.77  TEST= 0
INDE  10  11  59  FOBS=   50.0  SIGMA=   5.2  PHAS=  -64.7  FOM= 0.20  TEST= 0
INDE  10  11  61  FOBS=    0.0  SIGMA=  22.4  PHAS=    0.0  FOM= 0.00  TEST= 0
INDE  10  11  63  FOBS=   78.5  SIGMA=   4.6  PHAS=  -13.1  FOM= 0.78  TEST= 0
INDE  10  11  65  FOBS=   97.6  SIGMA=   3.7  PHAS=  -63.2  FOM= 0.88  TEST= 0
INDE  10  11  67  FOBS=   30.4  SIGMA=  16.5  PHAS=  162.0  FOM= 0.23  TEST= 0
INDE  10  12  10  FOBS=  127.8  SIGMA=   0.4  PHAS=   53.4  FOM= 0.89  TEST= 0
INDE  10  12  12  FOBS=  142.3  SIGMA=   0.6  PHAS=    8.3  FOM= 0.97  TEST= 0
INDE  10  12  14  FOBS=  250.2  SIGMA=   0.5  PHAS=  -81.3  FOM= 0.85  TEST= 0
INDE  10  12  16  FOBS=  254.1  SIGMA=   0.5  PHAS=  -20.6  FOM= 0.96  TEST= 0
INDE  10  12  18  FOBS=  188.3  SIGMA=   0.4  PHAS=   -5.6  FOM= 0.87  TEST= 0
INDE  10  12  20  FOBS=  106.5  SIGMA=   0.6  PHAS=  -11.6  FOM= 0.94  TEST= 0
INDE  10  12  22  FOBS=  174.6  SIGMA=   0.5  PHAS=  -73.6  FOM= 0.99  TEST= 0
INDE  10  12  24  FOBS=   93.4  SIGMA=   0.7  PHAS=  129.3  FOM= 0.99  TEST= 0
INDE  10  12  26  FOBS=   53.5  SIGMA=   1.3  PHAS=   79.4  FOM= 0.99  TEST= 1
INDE  10  12  28  FOBS=  170.9  SIGMA=   0.5  PHAS=  -32.3  FOM= 0.99  TEST= 0
INDE  10  12  30  FOBS=   88.7  SIGMA=   0.9  PHAS= -149.7  FOM= 0.93  TEST= 0
INDE  10  12  32  FOBS=  243.7  SIGMA=   0.5  PHAS=  151.0  FOM= 0.97  TEST= 0
INDE  10  12  34  FOBS=  157.9  SIGMA=   0.9  PHAS=  111.0  FOM= 0.98  TEST= 0
INDE  10  12  36  FOBS=  191.3  SIGMA=   0.9  PHAS=  113.5  FOM= 0.90  TEST= 0
INDE  10  12  38  FOBS=  243.5  SIGMA=   0.8  PHAS=  102.3  FOM= 0.98  TEST= 1
INDE  10  12  40  FOBS=  194.8  SIGMA=   1.1  PHAS=  -14.1  FOM= 0.93  TEST= 0
INDE  10  12  42  FOBS=  262.3  SIGMA=   1.1  PHAS= -175.0  FOM= 0.96  TEST= 0
INDE  10  12  44  FOBS=   85.4  SIGMA=   2.4  PHAS=    7.2  FOM= 0.26  TEST= 0
INDE  10  12  46  FOBS=  154.9  SIGMA=   1.7  PHAS=  121.5  FOM= 0.91  TEST= 0
INDE  10  12  48  FOBS=   95.0  SIGMA=   1.9  PHAS=   15.7  FOM= 0.83  TEST= 0
INDE  10  12  50  FOBS=  101.0  SIGMA=   1.5  PHAS=  -76.6  FOM= 0.80  TEST= 0
INDE  10  12  52  FOBS=   72.5  SIGMA=   2.0  PHAS=  -94.6  FOM= 0.81  TEST= 0
INDE  10  12  54  FOBS=   54.5  SIGMA=   2.5  PHAS=  179.2  FOM= 0.91  TEST= 1
INDE  10  12  56  FOBS=  143.1  SIGMA=   1.3  PHAS=  -87.6  FOM= 0.95  TEST= 0
INDE  10  12  58  FOBS=   64.7  SIGMA=   4.1  PHAS=   96.9  FOM= 0.90  TEST= 0
INDE  10  12  60  FOBS=  118.2  SIGMA=   2.3  PHAS=  -79.3  FOM= 0.89  TEST= 0
INDE  10  12  62  FOBS=   99.4  SIGMA=   2.5  PHAS=  -56.8  FOM= 0.81  TEST= 0
INDE  10  12  64  FOBS=   42.5  SIGMA=   8.2  PHAS= -173.5  FOM= 0.68  TEST= 0
```

*FIG. 12A - 258*

| | | | | | | | | | | | | |
|---|---|---|---|---|---|---|---|---|---|---|---|---|
| INDE | 10 | 12 | 66 | FOBS= | 6.9 | SIGMA= | 49.1 | PHAS= | -106.5 | FOM= | 0.05 | TEST= 0 |
| INDE | 10 | 13 | 11 | FOBS= | 271.9 | SIGMA= | 0.5 | PHAS= | 20.6 | FOM= | 0.91 | TEST= 0 |
| INDE | 10 | 13 | 13 | FOBS= | 117.8 | SIGMA= | 0.6 | PHAS= | -171.9 | FOM= | 0.89 | TEST= 0 |
| INDE | 10 | 13 | 15 | FOBS= | 188.8 | SIGMA= | 0.4 | PHAS= | -126.9 | FOM= | 0.92 | TEST= 0 |
| INDE | 10 | 13 | 17 | FOBS= | 117.4 | SIGMA= | 0.5 | PHAS= | -43.2 | FOM= | 0.96 | TEST= 0 |
| INDE | 10 | 13 | 19 | FOBS= | 96.1 | SIGMA= | 0.6 | PHAS= | 176.4 | FOM= | 0.85 | TEST= 0 |
| INDE | 10 | 13 | 21 | FOBS= | 143.4 | SIGMA= | 0.5 | PHAS= | 163.5 | FOM= | 0.99 | TEST= 0 |
| INDE | 10 | 13 | 23 | FOBS= | 165.8 | SIGMA= | 0.5 | PHAS= | -10.7 | FOM= | 0.97 | TEST= 1 |
| INDE | 10 | 13 | 25 | FOBS= | 87.6 | SIGMA= | 0.8 | PHAS= | 141.1 | FOM= | 0.99 | TEST= 0 |
| INDE | 10 | 13 | 27 | FOBS= | 128.3 | SIGMA= | 0.6 | PHAS= | 170.9 | FOM= | 0.79 | TEST= 0 |
| INDE | 10 | 13 | 29 | FOBS= | 78.0 | SIGMA= | 1.0 | PHAS= | -18.8 | FOM= | 0.99 | TEST= 0 |
| INDE | 10 | 13 | 31 | FOBS= | 279.6 | SIGMA= | 0.5 | PHAS= | 19.3 | FOM= | 0.77 | TEST= 1 |
| INDE | 10 | 13 | 33 | FOBS= | 208.5 | SIGMA= | 0.7 | PHAS= | 48.0 | FOM= | 0.92 | TEST= 0 |
| INDE | 10 | 13 | 35 | FOBS= | 101.9 | SIGMA= | 1.2 | PHAS= | -25.8 | FOM= | 0.96 | TEST= 0 |
| INDE | 10 | 13 | 37 | FOBS= | 503.5 | SIGMA= | 0.6 | PHAS= | -10.3 | FOM= | 0.87 | TEST= 1 |
| INDE | 10 | 13 | 39 | FOBS= | 0.0 | SIGMA= | 17.3 | PHAS= | 0.0 | FOM= | 0.00 | TEST= 0 |
| INDE | 10 | 13 | 41 | FOBS= | 233.2 | SIGMA= | 0.7 | PHAS= | -121.9 | FOM= | 0.94 | TEST= 0 |
| INDE | 10 | 13 | 43 | FOBS= | 192.4 | SIGMA= | 0.9 | PHAS= | -84.8 | FOM= | 0.95 | TEST= 0 |
| INDE | 10 | 13 | 45 | FOBS= | 175.1 | SIGMA= | 0.9 | PHAS= | 151.8 | FOM= | 0.93 | TEST= 0 |
| INDE | 10 | 13 | 47 | FOBS= | 230.3 | SIGMA= | 0.9 | PHAS= | 143.5 | FOM= | 0.97 | TEST= 0 |
| INDE | 10 | 13 | 49 | FOBS= | 161.2 | SIGMA= | 1.1 | PHAS= | -153.7 | FOM= | 0.91 | TEST= 0 |
| INDE | 10 | 13 | 51 | FOBS= | 144.9 | SIGMA= | 1.0 | PHAS= | 175.8 | FOM= | 0.94 | TEST= 0 |
| INDE | 10 | 13 | 53 | FOBS= | 91.0 | SIGMA= | 1.6 | PHAS= | 128.8 | FOM= | 0.68 | TEST= 0 |
| INDE | 10 | 13 | 55 | FOBS= | 90.1 | SIGMA= | 1.8 | PHAS= | 155.9 | FOM= | 0.74 | TEST= 1 |
| INDE | 10 | 13 | 57 | FOBS= | 138.4 | SIGMA= | 1.0 | PHAS= | 138.4 | FOM= | 0.93 | TEST= 0 |
| INDE | 10 | 13 | 59 | FOBS= | 139.7 | SIGMA= | 1.7 | PHAS= | 141.8 | FOM= | 0.95 | TEST= 0 |
| INDE | 10 | 13 | 61 | FOBS= | 140.4 | SIGMA= | 1.9 | PHAS= | 154.5 | FOM= | 0.87 | TEST= 0 |
| INDE | 10 | 13 | 63 | FOBS= | 0.0 | SIGMA= | 26.2 | PHAS= | 0.0 | FOM= | 0.00 | TEST= 0 |
| INDE | 10 | 13 | 65 | FOBS= | 16.5 | SIGMA= | 20.7 | PHAS= | -150.9 | FOM= | 0.44 | TEST= 0 |
| INDE | 10 | 14 | 10 | FOBS= | 257.5 | SIGMA= | 0.5 | PHAS= | -172.3 | FOM= | 0.91 | TEST= 0 |
| INDE | 10 | 14 | 12 | FOBS= | 232.3 | SIGMA= | 0.5 | PHAS= | 22.8 | FOM= | 0.91 | TEST= 0 |
| INDE | 10 | 14 | 14 | FOBS= | 169.7 | SIGMA= | 0.6 | PHAS= | -146.6 | FOM= | 0.69 | TEST= 0 |
| INDE | 10 | 14 | 16 | FOBS= | 88.3 | SIGMA= | 0.7 | PHAS= | 130.5 | FOM= | 0.91 | TEST= 0 |
| INDE | 10 | 14 | 18 | FOBS= | 104.9 | SIGMA= | 0.6 | PHAS= | 21.4 | FOM= | 0.93 | TEST= 0 |
| INDE | 10 | 14 | 20 | FOBS= | 134.9 | SIGMA= | 0.5 | PHAS= | 54.9 | FOM= | 0.97 | TEST= 0 |
| INDE | 10 | 14 | 22 | FOBS= | 179.3 | SIGMA= | 0.5 | PHAS= | -80.6 | FOM= | 0.98 | TEST= 0 |
| INDE | 10 | 14 | 24 | FOBS= | 56.4 | SIGMA= | 1.1 | PHAS= | 73.6 | FOM= | 0.95 | TEST= 0 |
| INDE | 10 | 14 | 26 | FOBS= | 109.7 | SIGMA= | 0.6 | PHAS= | 29.9 | FOM= | 0.99 | TEST= 0 |
| INDE | 10 | 14 | 28 | FOBS= | 105.9 | SIGMA= | 0.7 | PHAS= | -39.0 | FOM= | 0.96 | TEST= 0 |
| INDE | 10 | 14 | 30 | FOBS= | 121.6 | SIGMA= | 0.6 | PHAS= | -120.1 | FOM= | 0.99 | TEST= 0 |
| INDE | 10 | 14 | 32 | FOBS= | 22.5 | SIGMA= | 3.8 | PHAS= | -61.7 | FOM= | 0.95 | TEST= 0 |
| INDE | 10 | 14 | 34 | FOBS= | 243.1 | SIGMA= | 0.6 | PHAS= | -3.3 | FOM= | 0.98 | TEST= 0 |
| INDE | 10 | 14 | 36 | FOBS= | 346.1 | SIGMA= | 0.6 | PHAS= | -85.6 | FOM= | 0.97 | TEST= 0 |
| INDE | 10 | 14 | 38 | FOBS= | 113.8 | SIGMA= | 1.1 | PHAS= | -49.5 | FOM= | 0.92 | TEST= 0 |
| INDE | 10 | 14 | 40 | FOBS= | 0.0 | SIGMA= | 16.0 | PHAS= | 0.0 | FOM= | 0.00 | TEST= 0 |
| INDE | 10 | 14 | 42 | FOBS= | 479.5 | SIGMA= | 0.7 | PHAS= | -164.7 | FOM= | 0.98 | TEST= 0 |
| INDE | 10 | 14 | 44 | FOBS= | 89.2 | SIGMA= | 1.8 | PHAS= | 61.8 | FOM= | 0.92 | TEST= 0 |
| INDE | 10 | 14 | 46 | FOBS= | 256.3 | SIGMA= | 1.2 | PHAS= | 77.3 | FOM= | 0.89 | TEST= 1 |
| INDE | 10 | 14 | 48 | FOBS= | 55.4 | SIGMA= | 2.8 | PHAS= | 120.6 | FOM= | 0.70 | TEST= 0 |
| INDE | 10 | 14 | 50 | FOBS= | 162.2 | SIGMA= | 1.0 | PHAS= | 87.6 | FOM= | 0.93 | TEST= 0 |
| INDE | 10 | 14 | 52 | FOBS= | 114.5 | SIGMA= | 1.3 | PHAS= | 38.3 | FOM= | 0.94 | TEST= 0 |
| INDE | 10 | 14 | 54 | FOBS= | 175.5 | SIGMA= | 1.0 | PHAS= | 134.7 | FOM= | 0.94 | TEST= 0 |
| INDE | 10 | 14 | 56 | FOBS= | 0.0 | SIGMA= | 17.2 | PHAS= | 0.0 | FOM= | 0.00 | TEST= 0 |
| INDE | 10 | 14 | 58 | FOBS= | 120.0 | SIGMA= | 1.7 | PHAS= | 18.6 | FOM= | 0.93 | TEST= 0 |
| INDE | 10 | 14 | 60 | FOBS= | 84.2 | SIGMA= | 2.4 | PHAS= | 10.7 | FOM= | 0.93 | TEST= 0 |
| INDE | 10 | 14 | 62 | FOBS= | 74.1 | SIGMA= | 3.3 | PHAS= | 70.8 | FOM= | 0.91 | TEST= 0 |
| INDE | 10 | 14 | 64 | FOBS= | 47.9 | SIGMA= | 7.4 | PHAS= | -48.7 | FOM= | 0.70 | TEST= 0 |
| INDE | 10 | 14 | 66 | FOBS= | 90.1 | SIGMA= | 5.6 | PHAS= | 68.1 | FOM= | 0.75 | TEST= 1 |
| INDE | 10 | 15 | 11 | FOBS= | 154.3 | SIGMA= | 0.5 | PHAS= | -8.3 | FOM= | 0.92 | TEST= 0 |
| INDE | 10 | 15 | 13 | FOBS= | 236.6 | SIGMA= | 0.4 | PHAS= | -93.8 | FOM= | 0.94 | TEST= 0 |
| INDE | 10 | 15 | 15 | FOBS= | 44.5 | SIGMA= | 1.7 | PHAS= | -56.2 | FOM= | 0.43 | TEST= 0 |
| INDE | 10 | 15 | 17 | FOBS= | 86.4 | SIGMA= | 0.7 | PHAS= | -127.0 | FOM= | 0.18 | TEST= 1 |
| INDE | 10 | 15 | 19 | FOBS= | 63.7 | SIGMA= | 1.0 | PHAS= | -61.2 | FOM= | 0.95 | TEST= 0 |
| INDE | 10 | 15 | 21 | FOBS= | 72.9 | SIGMA= | 0.9 | PHAS= | 164.6 | FOM= | 0.98 | TEST= 0 |
| INDE | 10 | 15 | 23 | FOBS= | 86.1 | SIGMA= | 0.7 | PHAS= | 120.6 | FOM= | 0.87 | TEST= 0 |
| INDE | 10 | 15 | 25 | FOBS= | 57.1 | SIGMA= | 1.1 | PHAS= | -153.5 | FOM= | 0.98 | TEST= 0 |
| INDE | 10 | 15 | 27 | FOBS= | 134.9 | SIGMA= | 0.6 | PHAS= | 142.1 | FOM= | 0.96 | TEST= 0 |
| INDE | 10 | 15 | 29 | FOBS= | 54.7 | SIGMA= | 1.3 | PHAS= | 102.9 | FOM= | 0.92 | TEST= 1 |
| INDE | 10 | 15 | 31 | FOBS= | 269.5 | SIGMA= | 0.4 | PHAS= | 31.6 | FOM= | 0.97 | TEST= 0 |
| INDE | 10 | 15 | 33 | FOBS= | 105.0 | SIGMA= | 0.9 | PHAS= | -170.0 | FOM= | 0.88 | TEST= 0 |

*FIG. 12A - 259*

```
INDE  10  15  35  FOBS=   290.9  SIGMA=   0.6  PHAS=   -98.8  FOM=  0.92  TEST= 1
INDE  10  15  37  FOBS=   179.0  SIGMA=   0.8  PHAS=  -137.5  FOM=  0.96  TEST= 0
INDE  10  15  39  FOBS=    39.7  SIGMA=   3.0  PHAS=   -18.8  FOM=  0.83  TEST= 0
INDE  10  15  41  FOBS=   125.7  SIGMA=   2.0  PHAS=   153.9  FOM=  0.85  TEST= 0
INDE  10  15  43  FOBS=   198.3  SIGMA=   0.8  PHAS=   145.7  FOM=  0.96  TEST= 0
INDE  10  15  45  FOBS=   292.1  SIGMA=   0.8  PHAS=   -63.5  FOM=  0.97  TEST= 0
INDE  10  15  47  FOBS=   144.0  SIGMA=   1.1  PHAS=    83.4  FOM=  0.44  TEST= 0
INDE  10  15  49  FOBS=    53.0  SIGMA=   2.9  PHAS=   -12.8  FOM=  0.87  TEST= 0
INDE  10  15  51  FOBS=   200.6  SIGMA=   1.2  PHAS=   -76.8  FOM=  0.90  TEST= 0
INDE  10  15  53  FOBS=   161.3  SIGMA=   1.1  PHAS=   111.9  FOM=  0.90  TEST= 0
INDE  10  15  55  FOBS=    94.2  SIGMA=   1.5  PHAS=    99.5  FOM=  0.93  TEST= 0
INDE  10  15  57  FOBS=    75.5  SIGMA=   2.7  PHAS=  -134.1  FOM=  0.91  TEST= 0
INDE  10  15  59  FOBS=   172.3  SIGMA=   1.3  PHAS=  -146.9  FOM=  0.95  TEST= 0
INDE  10  15  61  FOBS=    45.0  SIGMA=   4.4  PHAS=   153.4  FOM=  0.56  TEST= 1
INDE  10  15  63  FOBS=    44.7  SIGMA=   6.2  PHAS=   -56.5  FOM=  0.47  TEST= 0
INDE  10  15  65  FOBS=     0.0  SIGMA=  23.4  PHAS=     0.0  FOM=  0.00  TEST= 0
INDE  10  16  10  FOBS=   401.7  SIGMA=   0.4  PHAS=  -178.6  FOM=  0.96  TEST= 0
INDE  10  16  12  FOBS=    47.8  SIGMA=   1.3  PHAS=    32.7  FOM=  0.92  TEST= 0
INDE  10  16  14  FOBS=   134.9  SIGMA=   0.6  PHAS=   179.7  FOM=  0.89  TEST= 0
INDE  10  16  16  FOBS=   141.5  SIGMA=   0.6  PHAS=  -123.9  FOM=  0.67  TEST= 0
INDE  10  16  18  FOBS=   200.8  SIGMA=   0.4  PHAS=    91.8  FOM=  0.98  TEST= 0
INDE  10  16  20  FOBS=    81.1  SIGMA=   0.8  PHAS=  -154.4  FOM=  0.71  TEST= 0
INDE  10  16  22  FOBS=   260.1  SIGMA=   0.4  PHAS=   -12.4  FOM=  0.99  TEST= 0
INDE  10  16  24  FOBS=   257.6  SIGMA=   0.4  PHAS=    48.6  FOM=  0.98  TEST= 1
INDE  10  16  26  FOBS=   206.4  SIGMA=   0.4  PHAS=   -45.3  FOM=  0.96  TEST= 0
INDE  10  16  28  FOBS=   242.0  SIGMA=   0.4  PHAS=     4.1  FOM=  0.97  TEST= 0
INDE  10  16  30  FOBS=   204.3  SIGMA=   0.5  PHAS=   -58.3  FOM=  0.93  TEST= 0
INDE  10  16  32  FOBS=   110.2  SIGMA=   0.8  PHAS=   -66.4  FOM=  0.83  TEST= 0
INDE  10  16  34  FOBS=   194.9  SIGMA=   0.6  PHAS=    66.5  FOM=  0.93  TEST= 0
INDE  10  16  36  FOBS=    89.4  SIGMA=   1.4  PHAS=   168.8  FOM=  0.95  TEST= 0
INDE  10  16  38  FOBS=   183.5  SIGMA=   0.7  PHAS=   -94.7  FOM=  0.94  TEST= 0
INDE  10  16  40  FOBS=    82.5  SIGMA=   1.5  PHAS=  -135.8  FOM=  0.68  TEST= 1
INDE  10  16  42  FOBS=     0.0  SIGMA=  16.8  PHAS=     0.0  FOM=  0.00  TEST= 0
INDE  10  16  44  FOBS=    89.7  SIGMA=   1.8  PHAS=   176.0  FOM=  0.85  TEST= 0
INDE  10  16  46  FOBS=    87.1  SIGMA=   1.9  PHAS=   108.0  FOM=  0.85  TEST= 0
INDE  10  16  48  FOBS=   193.4  SIGMA=   0.9  PHAS=  -151.0  FOM=  0.96  TEST= 0
INDE  10  16  50  FOBS=    30.2  SIGMA=   5.1  PHAS=   -78.1  FOM=  0.62  TEST= 0
INDE  10  16  52  FOBS=    21.3  SIGMA=   6.9  PHAS=  -178.1  FOM=  0.36  TEST= 1
INDE  10  16  54  FOBS=   102.1  SIGMA=   1.4  PHAS=    37.5  FOM=  0.88  TEST= 0
INDE  10  16  56  FOBS=   108.7  SIGMA=   2.0  PHAS=    64.5  FOM=  0.88  TEST= 0
INDE  10  16  58  FOBS=    80.1  SIGMA=   2.6  PHAS=    75.2  FOM=  0.73  TEST= 0
INDE  10  16  60  FOBS=   130.8  SIGMA=   1.6  PHAS=    61.6  FOM=  0.94  TEST= 0
INDE  10  16  62  FOBS=     0.0  SIGMA=  23.1  PHAS=     0.0  FOM=  0.00  TEST= 0
INDE  10  16  64  FOBS=    96.5  SIGMA=   3.0  PHAS=   -33.1  FOM=  0.83  TEST= 0
INDE  10  16  66  FOBS=    43.8  SIGMA=  10.5  PHAS=   -30.0  FOM=  0.78  TEST= 0
INDE  10  17  11  FOBS=    46.5  SIGMA=   1.2  PHAS=   -76.6  FOM=  0.80  TEST= 0
INDE  10  17  13  FOBS=    79.1  SIGMA=   0.8  PHAS=    13.8  FOM=  0.99  TEST= 0
INDE  10  17  15  FOBS=   165.8  SIGMA=   0.5  PHAS=    68.0  FOM=  0.94  TEST= 0
INDE  10  17  17  FOBS=    34.3  SIGMA=   2.1  PHAS=    49.5  FOM=  0.80  TEST= 0
INDE  10  17  19  FOBS=   187.8  SIGMA=   0.5  PHAS=    87.2  FOM=  0.92  TEST= 0
INDE  10  17  21  FOBS=    76.5  SIGMA=   0.9  PHAS=  -111.1  FOM=  0.84  TEST= 0
INDE  10  17  23  FOBS=   132.3  SIGMA=   0.6  PHAS=   -15.6  FOM=  0.97  TEST= 0
INDE  10  17  25  FOBS=   181.3  SIGMA=   0.5  PHAS=  -163.2  FOM=  0.96  TEST= 0
INDE  10  17  27  FOBS=   160.7  SIGMA=   0.5  PHAS=  -150.9  FOM=  0.99  TEST= 0
INDE  10  17  29  FOBS=   249.2  SIGMA=   0.4  PHAS=   -85.1  FOM=  0.97  TEST= 0
INDE  10  17  31  FOBS=   242.1  SIGMA=   0.5  PHAS=   -86.9  FOM=  0.96  TEST= 0
INDE  10  17  33  FOBS=    30.1  SIGMA=   3.1  PHAS=  -115.9  FOM=  0.42  TEST= 0
INDE  10  17  35  FOBS=   376.2  SIGMA=   0.5  PHAS=   -57.6  FOM=  0.96  TEST= 0
INDE  10  17  37  FOBS=   278.9  SIGMA=   0.5  PHAS=   154.7  FOM=  0.96  TEST= 0
INDE  10  17  39  FOBS=   140.0  SIGMA=   0.9  PHAS=   150.9  FOM=  0.08  TEST= 0
INDE  10  17  41  FOBS=    82.9  SIGMA=   1.7  PHAS=  -100.4  FOM=  0.82  TEST= 0
INDE  10  17  43  FOBS=   112.1  SIGMA=   1.3  PHAS=  -137.5  FOM=  0.47  TEST= 1
INDE  10  17  45  FOBS=    98.9  SIGMA=   1.7  PHAS=    38.2  FOM=  0.73  TEST= 0
INDE  10  17  47  FOBS=   170.3  SIGMA=   1.0  PHAS=   129.6  FOM=  0.76  TEST= 1
INDE  10  17  49  FOBS=    62.0  SIGMA=   3.4  PHAS=    64.9  FOM=  0.53  TEST= 0
INDE  10  17  51  FOBS=   127.1  SIGMA=   1.2  PHAS=  -175.5  FOM=  0.93  TEST= 0
INDE  10  17  53  FOBS=    34.2  SIGMA=   5.1  PHAS=  -146.2  FOM=  0.72  TEST= 0
INDE  10  17  55  FOBS=    49.6  SIGMA=   4.1  PHAS=    14.8  FOM=  0.77  TEST= 0
INDE  10  17  57  FOBS=    22.4  SIGMA=   9.0  PHAS=   167.9  FOM=  0.03  TEST= 0
INDE  10  17  59  FOBS=    71.8  SIGMA=   2.9  PHAS=   -69.4  FOM=  0.35  TEST= 0
```

*FIG. 12A - 260*

```
INDE 10 17 61 FOBS=   64.4 SIGMA=  3.3 PHAS= -128.5 FOM= 0.85 TEST= 0
INDE 10 17 63 FOBS=   40.0 SIGMA=  6.0 PHAS=  159.9 FOM= 0.57 TEST= 0
INDE 10 17 65 FOBS=    6.0 SIGMA= 56.7 PHAS= -158.2 FOM= 0.14 TEST= 0
INDE 10 17 67 FOBS=   64.1 SIGMA=  7.2 PHAS= -127.5 FOM= 0.84 TEST= 0
INDE 10 17 69 FOBS=   56.2 SIGMA=  8.4 PHAS=   93.5 FOM= 0.39 TEST= 0
INDE 10 18 10 FOBS=   83.9 SIGMA=  0.7 PHAS=  133.4 FOM= 0.90 TEST= 0
INDE 10 18 12 FOBS=   62.5 SIGMA=  1.0 PHAS=   41.2 FOM= 0.81 TEST= 0
INDE 10 18 14 FOBS=   25.6 SIGMA=  2.3 PHAS= -173.9 FOM= 0.66 TEST= 0
INDE 10 18 16 FOBS=  176.2 SIGMA=  0.5 PHAS=  -88.0 FOM= 0.99 TEST= 0
INDE 10 18 18 FOBS=  131.4 SIGMA=  0.7 PHAS=  -56.8 FOM= 0.52 TEST= 1
INDE 10 18 20 FOBS=  123.9 SIGMA=  0.7 PHAS= -125.0 FOM= 0.56 TEST= 0
INDE 10 18 22 FOBS=  244.2 SIGMA=  0.4 PHAS=  -17.3 FOM= 0.96 TEST= 0
INDE 10 18 24 FOBS=  223.5 SIGMA=  0.5 PHAS=  137.4 FOM= 0.95 TEST= 0
INDE 10 18 26 FOBS=  118.5 SIGMA=  0.7 PHAS=  128.2 FOM= 0.96 TEST= 0
INDE 10 18 28 FOBS=   88.6 SIGMA=  0.9 PHAS= -104.7 FOM= 0.96 TEST= 0
INDE 10 18 30 FOBS=   68.7 SIGMA=  1.3 PHAS=  142.1 FOM= 0.81 TEST= 0
INDE 10 18 32 FOBS=   99.8 SIGMA=  1.0 PHAS=   85.6 FOM= 0.94 TEST= 0
INDE 10 18 34 FOBS=  207.9 SIGMA=  0.6 PHAS=  -80.4 FOM= 0.96 TEST= 0
INDE 10 18 36 FOBS=  320.5 SIGMA=  0.5 PHAS=  118.4 FOM= 0.95 TEST= 0
INDE 10 18 38 FOBS=    0.0 SIGMA= 15.9 PHAS=    0.0 FOM= 0.00 TEST= 0
INDE 10 18 40 FOBS=  220.2 SIGMA=  0.7 PHAS= -151.7 FOM= 0.94 TEST= 0
INDE 10 18 42 FOBS=   22.8 SIGMA=  6.6 PHAS=  141.1 FOM= 0.86 TEST= 0
INDE 10 18 44 FOBS=  155.6 SIGMA=  1.1 PHAS=  -30.0 FOM= 0.87 TEST= 0
INDE 10 18 46 FOBS=   57.1 SIGMA=  2.9 PHAS=  -63.4 FOM= 0.88 TEST= 0
INDE 10 18 48 FOBS=  325.1 SIGMA=  0.7 PHAS= -175.6 FOM= 0.98 TEST= 0
INDE 10 18 50 FOBS=  170.8 SIGMA=  1.0 PHAS=   32.7 FOM= 0.96 TEST= 0
INDE 10 18 52 FOBS=   33.6 SIGMA=  5.0 PHAS=  149.3 FOM= 0.26 TEST= 0
INDE 10 18 54 FOBS=   49.9 SIGMA=  4.1 PHAS=  -61.2 FOM= 0.12 TEST= 1
INDE 10 18 56 FOBS=   49.9 SIGMA=  4.6 PHAS=   55.0 FOM= 0.61 TEST= 0
INDE 10 18 58 FOBS=   56.4 SIGMA=  3.9 PHAS=   16.4 FOM= 0.77 TEST= 0
INDE 10 18 60 FOBS=  118.8 SIGMA=  1.8 PHAS=   79.6 FOM= 0.93 TEST= 0
INDE 10 18 62 FOBS=   10.0 SIGMA= 23.3 PHAS=  -95.2 FOM= 0.14 TEST= 0
INDE 10 18 64 FOBS=   92.6 SIGMA=  3.1 PHAS=  -23.0 FOM= 0.94 TEST= 0
INDE 10 18 68 FOBS=   52.7 SIGMA=  9.0 PHAS=   57.7 FOM= 0.88 TEST= 0
INDE 10 18 70 FOBS=   46.6 SIGMA= 10.1 PHAS=  -30.4 FOM= 0.78 TEST= 0
INDE 10 18 72 FOBS=   30.0 SIGMA= 16.3 PHAS= -102.9 FOM= 0.16 TEST= 0
INDE 10 19 11 FOBS=  171.2 SIGMA=  0.4 PHAS=  -44.0 FOM= 0.98 TEST= 0
INDE 10 19 13 FOBS=  224.0 SIGMA=  0.5 PHAS=   72.7 FOM= 0.92 TEST= 0
INDE 10 19 15 FOBS=   65.1 SIGMA=  1.1 PHAS= -122.3 FOM= 0.99 TEST= 0
INDE 10 19 17 FOBS=  129.3 SIGMA=  0.6 PHAS= -128.6 FOM= 0.99 TEST= 0
INDE 10 19 19 FOBS=  140.4 SIGMA=  0.7 PHAS= -144.8 FOM= 0.95 TEST= 1
INDE 10 19 21 FOBS=  226.6 SIGMA=  0.5 PHAS= -153.0 FOM= 0.92 TEST= 0
INDE 10 19 23 FOBS=  103.6 SIGMA=  0.8 PHAS=  -51.5 FOM= 0.33 TEST= 1
INDE 10 19 25 FOBS=  114.9 SIGMA=  0.8 PHAS=  142.4 FOM= 0.93 TEST= 0
INDE 10 19 27 FOBS=  119.4 SIGMA=  0.8 PHAS=  154.0 FOM= 0.95 TEST= 0
INDE 10 19 29 FOBS=  145.5 SIGMA=  0.7 PHAS=  -43.3 FOM= 0.66 TEST= 0
INDE 10 19 31 FOBS=  368.8 SIGMA=  0.5 PHAS=  -38.2 FOM= 0.98 TEST= 0
INDE 10 19 33 FOBS=   57.3 SIGMA=  2.7 PHAS= -128.7 FOM= 0.92 TEST= 0
INDE 10 19 35 FOBS=    0.0 SIGMA= 14.5 PHAS=    0.0 FOM= 0.00 TEST= 0
INDE 10 19 37 FOBS=  240.0 SIGMA=  0.7 PHAS=   85.3 FOM= 0.93 TEST= 0
INDE 10 19 39 FOBS=  279.7 SIGMA=  0.7 PHAS=   39.0 FOM= 0.93 TEST= 0
INDE 10 19 41 FOBS=  304.9 SIGMA=  0.6 PHAS=  150.9 FOM= 0.96 TEST= 0
INDE 10 19 43 FOBS=   63.2 SIGMA=  2.3 PHAS=   21.1 FOM= 0.94 TEST= 0
INDE 10 19 45 FOBS=   43.7 SIGMA=  3.9 PHAS=   36.3 FOM= 0.51 TEST= 0
INDE 10 19 47 FOBS=  165.6 SIGMA=  1.0 PHAS=  132.7 FOM= 0.95 TEST= 0
INDE 10 19 49 FOBS=  104.5 SIGMA=  1.5 PHAS=   13.7 FOM= 0.87 TEST= 0
INDE 10 19 51 FOBS=  106.7 SIGMA=  2.0 PHAS=  -95.7 FOM= 0.74 TEST= 0
INDE 10 19 53 FOBS=   52.0 SIGMA=  4.3 PHAS= -123.4 FOM= 0.37 TEST= 0
INDE 10 19 55 FOBS=   68.0 SIGMA=  3.1 PHAS=  -98.5 FOM= 0.91 TEST= 0
INDE 10 19 57 FOBS=  162.9 SIGMA=  1.4 PHAS= -126.4 FOM= 0.96 TEST= 0
INDE 10 19 59 FOBS=   42.0 SIGMA=  4.8 PHAS=  -30.6 FOM= 0.71 TEST= 0
INDE 10 19 61 FOBS=  120.9 SIGMA=  2.1 PHAS= -127.6 FOM= 0.93 TEST= 0
INDE 10 19 63 FOBS=  120.6 SIGMA=  2.1 PHAS= -125.3 FOM= 0.95 TEST= 0
INDE 10 19 65 FOBS=   74.7 SIGMA=  5.2 PHAS= -163.5 FOM= 0.84 TEST= 0
INDE 10 19 67 FOBS=  124.8 SIGMA=  1.0 PHAS=  -67.9 FOM= 0.96 TEST= 0
INDE 10 19 69 FOBS=   67.8 SIGMA=  7.1 PHAS=  -57.3 FOM= 0.86 TEST= 0
INDE 10 19 71 FOBS=   15.5 SIGMA= 30.9 PHAS= -138.4 FOM= 0.24 TEST= 0
INDE 10 19 73 FOBS=   61.9 SIGMA=  3.1 PHAS=  158.8 FOM= 0.71 TEST= 0
INDE 10 20 10 FOBS=  130.1 SIGMA=  0.5 PHAS=  111.7 FOM= 0.85 TEST= 0
INDE 10 20 12 FOBS=   51.4 SIGMA=  1.2 PHAS=  -49.1 FOM= 0.95 TEST= 0
```

*FIG. 12A - 261*

| | | | | | | | | | | | |
|---|---|---|---|---|---|---|---|---|---|---|---|
| INDE | 10 | 20 | 14 | FOBS= | 30.1 | SIGMA= | 2.2 | PHAS= | -150.5 | FOM= 0.96 | TEST= 0 |
| INDE | 10 | 20 | 16 | FOBS= | 226.4 | SIGMA= | 0.5 | PHAS= | -162.6 | FOM= 0.99 | TEST= 0 |
| INDE | 10 | 20 | 18 | FOBS= | 50.6 | SIGMA= | 1.5 | PHAS= | 64.4 | FOM= 0.92 | TEST= 0 |
| INDE | 10 | 20 | 20 | FOBS= | 49.2 | SIGMA= | 1.5 | PHAS= | -39.5 | FOM= 0.97 | TEST= 0 |
| INDE | 10 | 20 | 22 | FOBS= | 65.0 | SIGMA= | 1.2 | PHAS= | 116.4 | FOM= 0.98 | TEST= 0 |
| INDE | 10 | 20 | 24 | FOBS= | 0.0 | SIGMA= | 13.5 | PHAS= | 0.0 | FOM= 0.00 | TEST= 0 |
| INDE | 10 | 20 | 26 | FOBS= | 188.4 | SIGMA= | 0.6 | PHAS= | 135.8 | FOM= 0.95 | TEST= 0 |
| INDE | 10 | 20 | 28 | FOBS= | 216.6 | SIGMA= | 0.6 | PHAS= | -92.8 | FOM= 0.96 | TEST= 0 |
| INDE | 10 | 20 | 30 | FOBS= | 77.5 | SIGMA= | 1.3 | PHAS= | -97.0 | FOM= 0.95 | TEST= 0 |
| INDE | 10 | 20 | 32 | FOBS= | 304.9 | SIGMA= | 0.5 | PHAS= | -174.5 | FOM= 0.95 | TEST= 0 |
| INDE | 10 | 20 | 34 | FOBS= | 130.4 | SIGMA= | 0.9 | PHAS= | -49.9 | FOM= 0.86 | TEST= 0 |
| INDE | 10 | 20 | 36 | FOBS= | 157.3 | SIGMA= | 0.9 | PHAS= | 114.7 | FOM= 0.92 | TEST= 1 |
| INDE | 10 | 20 | 38 | FOBS= | 322.2 | SIGMA= | 0.5 | PHAS= | 1.1 | FOM= 0.97 | TEST= 0 |
| INDE | 10 | 20 | 40 | FOBS= | 170.3 | SIGMA= | 0.8 | PHAS= | 55.7 | FOM= 0.84 | TEST= 0 |
| INDE | 10 | 20 | 42 | FOBS= | 298.5 | SIGMA= | 0.6 | PHAS= | 37.9 | FOM= 0.94 | TEST= 0 |
| INDE | 10 | 20 | 44 | FOBS= | 248.5 | SIGMA= | 0.8 | PHAS= | -70.5 | FOM= 0.97 | TEST= 0 |
| INDE | 10 | 20 | 46 | FOBS= | 81.7 | SIGMA= | 1.9 | PHAS= | 14.5 | FOM= 0.82 | TEST= 0 |
| INDE | 10 | 20 | 48 | FOBS= | 104.4 | SIGMA= | 1.4 | PHAS= | -165.8 | FOM= 0.94 | TEST= 0 |
| INDE | 10 | 20 | 50 | FOBS= | 64.9 | SIGMA= | 3.3 | PHAS= | -84.4 | FOM= 0.87 | TEST= 0 |
| INDE | 10 | 20 | 52 | FOBS= | 0.0 | SIGMA= | 23.7 | PHAS= | 0.0 | FOM= 0.00 | TEST= 0 |
| INDE | 10 | 20 | 54 | FOBS= | 150.8 | SIGMA= | 1.5 | PHAS= | 102.6 | FOM= 0.92 | TEST= 0 |
| INDE | 10 | 20 | 56 | FOBS= | 108.6 | SIGMA= | 1.9 | PHAS= | 154.2 | FOM= 0.80 | TEST= 0 |
| INDE | 10 | 20 | 58 | FOBS= | 0.0 | SIGMA= | 20.9 | PHAS= | 0.0 | FOM= 0.00 | TEST= 0 |
| INDE | 10 | 20 | 60 | FOBS= | 138.6 | SIGMA= | 1.8 | PHAS= | 97.2 | FOM= 0.95 | TEST= 0 |
| INDE | 10 | 20 | 62 | FOBS= | 113.1 | SIGMA= | 2.2 | PHAS= | 107.8 | FOM= 0.45 | TEST= 1 |
| INDE | 10 | 20 | 64 | FOBS= | 60.1 | SIGMA= | 5.7 | PHAS= | 158.8 | FOM= 0.67 | TEST= 0 |
| INDE | 10 | 20 | 66 | FOBS= | 170.1 | SIGMA= | 2.9 | PHAS= | 151.5 | FOM= 0.96 | TEST= 0 |
| INDE | 10 | 20 | 68 | FOBS= | 45.7 | SIGMA= | 10.2 | PHAS= | -100.1 | FOM= 0.61 | TEST= 0 |
| INDE | 10 | 20 | 70 | FOBS= | 22.8 | SIGMA= | 21.0 | PHAS= | -164.1 | FOM= 0.34 | TEST= 0 |
| INDE | 10 | 20 | 72 | FOBS= | 94.0 | SIGMA= | 5.4 | PHAS= | 80.6 | FOM= 0.85 | TEST= 0 |
| INDE | 10 | 20 | 74 | FOBS= | 25.4 | SIGMA= | 20.4 | PHAS= | 167.3 | FOM= 0.01 | TEST= 1 |
| INDE | 10 | 21 | 11 | FOBS= | 179.8 | SIGMA= | 0.5 | PHAS= | -63.4 | FOM= 0.80 | TEST= 0 |
| INDE | 10 | 21 | 13 | FOBS= | 136.3 | SIGMA= | 0.6 | PHAS= | 24.8 | FOM= 0.99 | TEST= 0 |
| INDE | 10 | 21 | 15 | FOBS= | 109.8 | SIGMA= | 0.7 | PHAS= | -31.1 | FOM= 0.98 | TEST= 1 |
| INDE | 10 | 21 | 17 | FOBS= | 121.3 | SIGMA= | 0.6 | PHAS= | 51.0 | FOM= 0.96 | TEST= 0 |
| INDE | 10 | 21 | 19 | FOBS= | 310.5 | SIGMA= | 0.5 | PHAS= | -137.8 | FOM= 0.99 | TEST= 0 |
| INDE | 10 | 21 | 21 | FOBS= | 49.0 | SIGMA= | 1.5 | PHAS= | 27.9 | FOM= 0.98 | TEST= 0 |
| INDE | 10 | 21 | 23 | FOBS= | 89.5 | SIGMA= | 1.1 | PHAS= | 33.8 | FOM= 0.98 | TEST= 0 |
| INDE | 10 | 21 | 25 | FOBS= | 37.6 | SIGMA= | 2.5 | PHAS= | 9.9 | FOM= 0.91 | TEST= 0 |
| INDE | 10 | 21 | 27 | FOBS= | 146.6 | SIGMA= | 0.7 | PHAS= | 92.9 | FOM= 0.97 | TEST= 0 |
| INDE | 10 | 21 | 29 | FOBS= | 81.3 | SIGMA= | 1.2 | PHAS= | -158.9 | FOM= 0.92 | TEST= 0 |
| INDE | 10 | 21 | 31 | FOBS= | 185.0 | SIGMA= | 0.7 | PHAS= | -51.2 | FOM= 0.95 | TEST= 1 |
| INDE | 10 | 21 | 33 | FOBS= | 165.9 | SIGMA= | 0.8 | PHAS= | 33.7 | FOM= 0.67 | TEST= 0 |
| INDE | 10 | 21 | 35 | FOBS= | 127.9 | SIGMA= | 0.9 | PHAS= | -13.5 | FOM= 0.21 | TEST= 0 |
| INDE | 10 | 21 | 37 | FOBS= | 13.1 | SIGMA= | 9.3 | PHAS= | -18.2 | FOM= 0.06 | TEST= 0 |
| INDE | 10 | 21 | 39 | FOBS= | 186.5 | SIGMA= | 0.8 | PHAS= | -28.5 | FOM= 0.95 | TEST= 0 |
| INDE | 10 | 21 | 41 | FOBS= | 184.1 | SIGMA= | 0.8 | PHAS= | -33.7 | FOM= 0.96 | TEST= 0 |
| INDE | 10 | 21 | 43 | FOBS= | 150.7 | SIGMA= | 1.0 | PHAS= | 178.9 | FOM= 0.48 | TEST= 1 |
| INDE | 10 | 21 | 45 | FOBS= | 162.7 | SIGMA= | 1.0 | PHAS= | 135.7 | FOM= 0.95 | TEST= 0 |
| INDE | 10 | 21 | 47 | FOBS= | 39.8 | SIGMA= | 4.4 | PHAS= | -17.7 | FOM= 0.77 | TEST= 0 |
| INDE | 10 | 21 | 49 | FOBS= | 73.5 | SIGMA= | 2.6 | PHAS= | -10.0 | FOM= 0.75 | TEST= 0 |
| INDE | 10 | 21 | 51 | FOBS= | 154.2 | SIGMA= | 1.5 | PHAS= | -154.3 | FOM= 0.92 | TEST= 0 |
| INDE | 10 | 21 | 53 | FOBS= | 70.2 | SIGMA= | 3.0 | PHAS= | 35.7 | FOM= 0.75 | TEST= 0 |
| INDE | 10 | 21 | 55 | FOBS= | 53.9 | SIGMA= | 3.9 | PHAS= | -36.4 | FOM= 0.78 | TEST= 0 |
| INDE | 10 | 21 | 57 | FOBS= | 27.5 | SIGMA= | 5.1 | PHAS= | 119.8 | FOM= 0.60 | TEST= 0 |
| INDE | 10 | 21 | 59 | FOBS= | 109.9 | SIGMA= | 1.9 | PHAS= | 17.9 | FOM= 0.93 | TEST= 0 |
| INDE | 10 | 21 | 61 | FOBS= | 87.8 | SIGMA= | 2.8 | PHAS= | 35.7 | FOM= 0.79 | TEST= 0 |
| INDE | 10 | 21 | 63 | FOBS= | 68.7 | SIGMA= | 3.5 | PHAS= | -22.9 | FOM= 0.34 | TEST= 0 |
| INDE | 10 | 21 | 65 | FOBS= | 89.5 | SIGMA= | 5.2 | PHAS= | 62.6 | FOM= 0.90 | TEST= 0 |
| INDE | 10 | 21 | 67 | FOBS= | 72.8 | SIGMA= | 6.6 | PHAS= | -12.9 | FOM= 0.93 | TEST= 0 |
| INDE | 10 | 21 | 69 | FOBS= | 38.8 | SIGMA= | 12.1 | PHAS= | 172.6 | FOM= 0.47 | TEST= 0 |
| INDE | 10 | 21 | 71 | FOBS= | 55.8 | SIGMA= | 8.9 | PHAS= | 37.6 | FOM= 0.75 | TEST= 0 |
| INDE | 10 | 21 | 73 | FOBS= | 47.2 | SIGMA= | 10.8 | PHAS= | -67.3 | FOM= 0.16 | TEST= 1 |
| INDE | 10 | 22 | 10 | FOBS= | 70.4 | SIGMA= | 0.9 | PHAS= | -88.5 | FOM= 0.99 | TEST= 0 |
| INDE | 10 | 22 | 12 | FOBS= | 83.2 | SIGMA= | 0.8 | PHAS= | -124.2 | FOM= 0.95 | TEST= 0 |
| INDE | 10 | 22 | 14 | FOBS= | 135.1 | SIGMA= | 0.6 | PHAS= | -112.1 | FOM= 0.99 | TEST= 0 |
| INDE | 10 | 22 | 16 | FOBS= | 92.3 | SIGMA= | 0.9 | PHAS= | -130.8 | FOM= 0.99 | TEST= 0 |
| INDE | 10 | 22 | 18 | FOBS= | 176.9 | SIGMA= | 0.6 | PHAS= | 125.5 | FOM= 0.99 | TEST= 0 |
| INDE | 10 | 22 | 20 | FOBS= | 43.8 | SIGMA= | 2.0 | PHAS= | 50.3 | FOM= 0.90 | TEST= 0 |
| INDE | 10 | 22 | 22 | FOBS= | 59.8 | SIGMA= | 1.4 | PHAS= | -170.5 | FOM= 0.33 | TEST= 0 |

*FIG. 12A - 262*

```
INDE 10 22 24 FOBS=    93.1 SIGMA=  1.0 PHAS=  -38.7 FOM= 0.93 TEST= 0
INDE 10 22 26 FOBS=    98.6 SIGMA=  1.1 PHAS=  -95.1 FOM= 0.56 TEST= 0
INDE 10 22 28 FOBS=    68.0 SIGMA=  1.5 PHAS=  -20.0 FOM= 0.98 TEST= 0
INDE 10 22 30 FOBS=   108.8 SIGMA=  1.0 PHAS=   -8.1 FOM= 0.96 TEST= 0
INDE 10 22 32 FOBS=   171.9 SIGMA=  0.9 PHAS= -103.2 FOM= 0.99 TEST= 0
INDE 10 22 34 FOBS=    65.0 SIGMA=  1.8 PHAS= -108.8 FOM= 0.35 TEST= 0
INDE 10 22 36 FOBS=     0.0 SIGMA= 15.8 PHAS=    0.0 FOM= 0.00 TEST= 0
INDE 10 22 38 FOBS=   229.3 SIGMA=  0.7 PHAS=  -67.3 FOM= 0.98 TEST= 0
INDE 10 22 40 FOBS=   185.5 SIGMA=  0.8 PHAS= -122.4 FOM= 0.95 TEST= 0
INDE 10 22 42 FOBS=   258.5 SIGMA=  0.7 PHAS=  -83.8 FOM= 0.88 TEST= 1
INDE 10 22 44 FOBS=    44.6 SIGMA=  3.4 PHAS=  179.2 FOM= 0.23 TEST= 0
INDE 10 22 46 FOBS=    74.3 SIGMA=  2.4 PHAS=  146.7 FOM= 0.91 TEST= 1
INDE 10 22 48 FOBS=   164.7 SIGMA=  1.1 PHAS=  -96.0 FOM= 0.98 TEST= 0
INDE 10 22 50 FOBS=    83.0 SIGMA=  2.3 PHAS=  167.3 FOM= 0.70 TEST= 0
INDE 10 22 52 FOBS=   125.7 SIGMA=  1.6 PHAS=  132.7 FOM= 0.89 TEST= 0
INDE 10 22 54 FOBS=     0.0 SIGMA= 20.2 PHAS=    0.0 FOM= 0.00 TEST= 0
INDE 10 22 56 FOBS=    67.6 SIGMA=  3.1 PHAS=  -84.0 FOM= 0.87 TEST= 0
INDE 10 22 58 FOBS=    22.0 SIGMA=  6.7 PHAS=   29.4 FOM= 0.47 TEST= 0
INDE 10 22 60 FOBS=    64.3 SIGMA=  3.8 PHAS=   20.4 FOM= 0.93 TEST= 0
INDE 10 22 62 FOBS=     3.9 SIGMA= 61.6 PHAS=  112.8 FOM= 0.03 TEST= 0
INDE 10 22 64 FOBS=    48.2 SIGMA=  9.5 PHAS=  -88.6 FOM= 0.51 TEST= 0
INDE 10 22 66 FOBS=    83.4 SIGMA=  5.6 PHAS= -166.6 FOM= 0.92 TEST= 0
INDE 10 22 68 FOBS=    51.4 SIGMA=  9.0 PHAS=  -42.5 FOM= 0.75 TEST= 0
INDE 10 22 70 FOBS=    75.4 SIGMA=  6.4 PHAS=  148.7 FOM= 0.88 TEST= 0
INDE 10 22 72 FOBS=    75.3 SIGMA=  6.6 PHAS=  -79.9 FOM= 0.89 TEST= 0
INDE 10 23 11 FOBS=    20.7 SIGMA=  3.0 PHAS=  170.1 FOM= 0.27 TEST= 0
INDE 10 23 13 FOBS=    91.8 SIGMA=  0.8 PHAS=   54.9 FOM= 0.96 TEST= 0
INDE 10 23 15 FOBS=   121.6 SIGMA=  0.7 PHAS=   -6.7 FOM= 0.86 TEST= 0
INDE 10 23 17 FOBS=   117.9 SIGMA=  0.8 PHAS=  125.3 FOM= 0.99 TEST= 1
INDE 10 23 19 FOBS=   117.5 SIGMA=  0.8 PHAS= -140.1 FOM= 0.92 TEST= 0
INDE 10 23 21 FOBS=   133.8 SIGMA=  0.8 PHAS=   90.6 FOM= 0.90 TEST= 0
INDE 10 23 23 FOBS=    94.5 SIGMA=  1.0 PHAS=  -24.8 FOM= 0.97 TEST= 0
INDE 10 23 25 FOBS=   182.6 SIGMA=  0.6 PHAS= -111.6 FOM= 0.86 TEST= 0
INDE 10 23 27 FOBS=    79.8 SIGMA=  1.4 PHAS=   93.0 FOM= 0.77 TEST= 0
INDE 10 23 29 FOBS=    79.7 SIGMA=  1.4 PHAS=  169.5 FOM= 0.19 TEST= 0
INDE 10 23 31 FOBS=    68.7 SIGMA=  1.7 PHAS=  112.6 FOM= 0.97 TEST= 1
INDE 10 23 33 FOBS=   143.3 SIGMA=  0.9 PHAS=   44.7 FOM= 0.96 TEST= 0
INDE 10 23 35 FOBS=   208.8 SIGMA=  0.7 PHAS=   63.8 FOM= 0.90 TEST= 0
INDE 10 23 37 FOBS=   248.5 SIGMA=  0.6 PHAS=  110.3 FOM= 0.94 TEST= 0
INDE 10 23 39 FOBS=     0.0 SIGMA= 17.0 PHAS=    0.0 FOM= 0.00 TEST= 0
INDE 10 23 41 FOBS=   119.2 SIGMA=  1.3 PHAS= -154.1 FOM= 0.80 TEST= 1
INDE 10 23 43 FOBS=   186.4 SIGMA=  1.0 PHAS=  145.9 FOM= 0.97 TEST= 0
INDE 10 23 45 FOBS=   342.5 SIGMA=  0.8 PHAS=  102.2 FOM= 0.50 TEST= 1
INDE 10 23 47 FOBS=   107.5 SIGMA=  1.7 PHAS= -155.9 FOM= 0.98 TEST= 0
INDE 10 23 49 FOBS=    45.9 SIGMA=  3.7 PHAS=   89.6 FOM= 0.53 TEST= 0
INDE 10 23 51 FOBS=   120.1 SIGMA=  1.6 PHAS=   23.0 FOM= 0.90 TEST= 0
INDE 10 23 53 FOBS=   106.2 SIGMA=  1.8 PHAS=  127.7 FOM= 0.33 TEST= 1
INDE 10 23 55 FOBS=    72.1 SIGMA=  2.9 PHAS= -159.8 FOM= 0.83 TEST= 0
INDE 10 23 57 FOBS=     0.0 SIGMA= 21.1 PHAS=    0.0 FOM= 0.00 TEST= 0
INDE 10 23 59 FOBS=    97.2 SIGMA=  1.7 PHAS=  -38.3 FOM= 0.87 TEST= 0
INDE 10 23 61 FOBS=    65.3 SIGMA=  3.8 PHAS=  -34.2 FOM= 0.59 TEST= 0
INDE 10 23 63 FOBS=    73.7 SIGMA=  3.8 PHAS=  -61.4 FOM= 0.71 TEST= 0
INDE 10 23 65 FOBS=    45.3 SIGMA= 10.3 PHAS=   68.9 FOM= 0.42 TEST= 0
INDE 10 23 67 FOBS=   112.6 SIGMA=  4.3 PHAS=  -57.3 FOM= 0.95 TEST= 0
INDE 10 23 69 FOBS=    45.3 SIGMA= 10.2 PHAS=   30.3 FOM= 0.02 TEST= 1
INDE 10 23 71 FOBS=    42.0 SIGMA= 11.4 PHAS=  108.7 FOM= 0.80 TEST= 1
INDE 10 24 10 FOBS=    51.0 SIGMA=  1.2 PHAS=  143.4 FOM= 0.98 TEST= 0
INDE 10 24 12 FOBS=    54.7 SIGMA=  1.3 PHAS=  143.1 FOM= 0.86 TEST= 0
INDE 10 24 14 FOBS=   184.5 SIGMA=  0.5 PHAS= -108.0 FOM= 0.97 TEST= 0
INDE 10 24 16 FOBS=   155.0 SIGMA=  0.7 PHAS=  -49.5 FOM= 0.91 TEST= 0
INDE 10 24 18 FOBS=    96.3 SIGMA=  0.9 PHAS=   86.7 FOM= 0.95 TEST= 0
INDE 10 24 20 FOBS=   172.0 SIGMA=  0.6 PHAS=   54.6 FOM= 0.96 TEST= 0
INDE 10 24 22 FOBS=   208.6 SIGMA=  0.6 PHAS= -158.9 FOM= 0.96 TEST= 1
INDE 10 24 24 FOBS=   127.0 SIGMA=  0.8 PHAS=  149.2 FOM= 0.61 TEST= 1
INDE 10 24 26 FOBS=    71.4 SIGMA=  1.4 PHAS=  -69.6 FOM= 0.43 TEST= 0
INDE 10 24 28 FOBS=   265.1 SIGMA=  0.7 PHAS=   13.0 FOM= 0.97 TEST= 0
INDE 10 24 30 FOBS=   244.1 SIGMA=  0.7 PHAS=   30.1 FOM= 0.97 TEST= 0
INDE 10 24 32 FOBS=   168.5 SIGMA=  0.8 PHAS=  -66.7 FOM= 0.89 TEST= 0
INDE 10 24 34 FOBS=    71.5 SIGMA=  1.8 PHAS=  -92.5 FOM= 0.86 TEST= 0
INDE 10 24 36 FOBS=   143.2 SIGMA=  1.0 PHAS=  -20.6 FOM= 0.94 TEST= 0
```

*FIG. 12A - 263*

```
INDE  10  24  38  FOBS=   100.9  SIGMA=   1.4  PHAS=   -43.8  FOM=  0.82  TEST= 0
INDE  10  24  40  FOBS=    89.8  SIGMA=   1.7  PHAS=  -169.1  FOM=  0.90  TEST= 0
INDE  10  24  42  FOBS=   186.5  SIGMA=   1.1  PHAS=   -47.7  FOM=  0.97  TEST= 0
INDE  10  24  44  FOBS=   169.7  SIGMA=   1.1  PHAS=    -2.1  FOM=  0.96  TEST= 1
INDE  10  24  46  FOBS=     5.4  SIGMA=  32.3  PHAS=   -59.5  FOM=  0.19  TEST= 0
INDE  10  24  48  FOBS=    97.8  SIGMA=   1.8  PHAS=     9.8  FOM=  0.90  TEST= 0
INDE  10  24  50  FOBS=   155.1  SIGMA=   1.2  PHAS=   -30.2  FOM=  0.90  TEST= 0
INDE  10  24  52  FOBS=    40.7  SIGMA=   4.4  PHAS=  -138.9  FOM=  0.12  TEST= 0
INDE  10  24  54  FOBS=   150.5  SIGMA=   1.3  PHAS=    93.5  FOM=  0.94  TEST= 0
INDE  10  24  56  FOBS=    46.6  SIGMA=   4.5  PHAS=   102.9  FOM=  0.36  TEST= 0
INDE  10  24  58  FOBS=    92.3  SIGMA=   1.7  PHAS=  -116.3  FOM=  0.62  TEST= 0
INDE  10  24  60  FOBS=     0.0  SIGMA=  17.9  PHAS=     0.0  FOM=  0.00  TEST= 0
INDE  10  24  62  FOBS=     0.0  SIGMA=  22.1  PHAS=     0.0  FOM=  0.00  TEST= 0
INDE  10  24  64  FOBS=    75.3  SIGMA=   6.4  PHAS=   107.1  FOM=  0.27  TEST= 1
INDE  10  24  66  FOBS=   109.5  SIGMA=   4.5  PHAS=   179.9  FOM=  0.94  TEST= 0
INDE  10  24  68  FOBS=     0.0  SIGMA=  30.7  PHAS=     0.0  FOM=  0.00  TEST= 0
INDE  10  24  70  FOBS=     0.0  SIGMA=  30.5  PHAS=     0.0  FOM=  0.00  TEST= 0
INDE  10  24  72  FOBS=    45.4  SIGMA=  10.9  PHAS=     2.6  FOM=  0.45  TEST= 0
INDE  10  25  11  FOBS=   128.5  SIGMA=   0.6  PHAS=    89.7  FOM=  0.99  TEST= 0
INDE  10  25  13  FOBS=    51.9  SIGMA=   1.5  PHAS=  -158.9  FOM=  0.98  TEST= 0
INDE  10  25  15  FOBS=   190.6  SIGMA=   0.6  PHAS=   -86.6  FOM=  0.96  TEST= 0
INDE  10  25  17  FOBS=   210.2  SIGMA=   0.6  PHAS=  -104.8  FOM=  0.98  TEST= 0
INDE  10  25  19  FOBS=    83.5  SIGMA=   1.1  PHAS=   -33.3  FOM=  0.98  TEST= 0
INDE  10  25  21  FOBS=   290.9  SIGMA=   0.6  PHAS=    37.9  FOM=  0.95  TEST= 0
INDE  10  25  23  FOBS=   256.0  SIGMA=   0.6  PHAS=    46.8  FOM=  0.97  TEST= 0
INDE  10  25  25  FOBS=   200.4  SIGMA=   0.6  PHAS=   -95.8  FOM=  0.96  TEST= 0
INDE  10  25  27  FOBS=   225.8  SIGMA=   0.6  PHAS=  -133.2  FOM=  0.94  TEST= 0
INDE  10  25  29  FOBS=   241.5  SIGMA=   0.6  PHAS=    61.1  FOM=  0.38  TEST= 1
INDE  10  25  31  FOBS=    96.4  SIGMA=   1.4  PHAS=   -82.6  FOM=  0.96  TEST= 0
INDE  10  25  33  FOBS=   137.2  SIGMA=   1.0  PHAS=   -19.5  FOM=  0.96  TEST= 0
INDE  10  25  35  FOBS=     0.0  SIGMA=  18.1  PHAS=     0.0  FOM=  0.00  TEST= 0
INDE  10  25  37  FOBS=   157.9  SIGMA=   1.0  PHAS=   122.8  FOM=  0.96  TEST= 0
INDE  10  25  39  FOBS=   101.8  SIGMA=   1.8  PHAS=    98.5  FOM=  0.95  TEST= 0
INDE  10  25  41  FOBS=   135.2  SIGMA=   1.4  PHAS=  -163.6  FOM=  0.80  TEST= 0
INDE  10  25  43  FOBS=    56.6  SIGMA=   3.2  PHAS=  -162.2  FOM=  0.52  TEST= 0
INDE  10  25  45  FOBS=   130.5  SIGMA=   1.4  PHAS=    87.7  FOM=  0.91  TEST= 0
INDE  10  25  47  FOBS=   107.7  SIGMA=   1.7  PHAS=  -133.3  FOM=  0.86  TEST= 0
INDE  10  25  49  FOBS=     0.0  SIGMA=  18.5  PHAS=     0.0  FOM=  0.00  TEST= 0
INDE  10  25  51  FOBS=   118.8  SIGMA=   1.5  PHAS=  -122.0  FOM=  0.85  TEST= 0
INDE  10  25  53  FOBS=    83.5  SIGMA=   2.1  PHAS=    11.2  FOM=  0.89  TEST= 0
INDE  10  25  55  FOBS=    94.6  SIGMA=   2.0  PHAS=     5.2  FOM=  0.87  TEST= 0
INDE  10  25  57  FOBS=    81.9  SIGMA=   2.6  PHAS=   -39.4  FOM=  0.92  TEST= 0
INDE  10  25  59  FOBS=    46.3  SIGMA=   3.7  PHAS=    19.7  FOM=  0.87  TEST= 0
INDE  10  25  61  FOBS=   105.2  SIGMA=   1.6  PHAS=   -62.1  FOM=  0.84  TEST= 0
INDE  10  25  63  FOBS=    61.5  SIGMA=   5.4  PHAS=    90.1  FOM=  0.35  TEST= 0
INDE  10  25  65  FOBS=    71.0  SIGMA=   6.9  PHAS=    21.7  FOM=  0.85  TEST= 0
INDE  10  25  67  FOBS=    27.8  SIGMA=  17.6  PHAS=    18.4  FOM=  0.44  TEST= 0
INDE  10  25  69  FOBS=    62.3  SIGMA=   7.8  PHAS=  -172.1  FOM=  0.80  TEST= 0
INDE  10  25  71  FOBS=     0.0  SIGMA=  31.2  PHAS=     0.0  FOM=  0.00  TEST= 0
INDE  10  26  10  FOBS=    54.0  SIGMA=   1.2  PHAS=    39.2  FOM=  0.63  TEST= 0
INDE  10  26  12  FOBS=   104.3  SIGMA=   0.9  PHAS=    40.9  FOM=  0.96  TEST= 0
INDE  10  26  14  FOBS=   129.9  SIGMA=   0.7  PHAS=   110.3  FOM=  0.94  TEST= 0
INDE  10  26  16  FOBS=    88.1  SIGMA=   1.1  PHAS=   165.9  FOM=  0.89  TEST= 0
INDE  10  26  18  FOBS=   143.1  SIGMA=   0.7  PHAS=  -149.9  FOM=  0.99  TEST= 0
INDE  10  26  20  FOBS=   231.6  SIGMA=   0.6  PHAS=     0.3  FOM=  0.97  TEST= 0
INDE  10  26  22  FOBS=   147.8  SIGMA=   0.8  PHAS=   -80.8  FOM=  0.97  TEST= 0
INDE  10  26  24  FOBS=   201.1  SIGMA=   0.7  PHAS=  -115.4  FOM=  0.94  TEST= 0
INDE  10  26  26  FOBS=   191.9  SIGMA=   0.6  PHAS=   100.1  FOM=  0.98  TEST= 0
INDE  10  26  28  FOBS=   112.8  SIGMA=   1.0  PHAS=   -33.7  FOM=  0.12  TEST= 0
INDE  10  26  30  FOBS=   246.1  SIGMA=   0.6  PHAS=  -179.8  FOM=  0.82  TEST= 0
INDE  10  26  32  FOBS=   188.6  SIGMA=   0.8  PHAS=  -148.9  FOM=  0.98  TEST= 0
INDE  10  26  34  FOBS=   151.7  SIGMA=   1.0  PHAS=  -117.5  FOM=  0.95  TEST= 0
INDE  10  26  36  FOBS=   113.6  SIGMA=   1.5  PHAS=  -156.6  FOM=  0.50  TEST= 0
INDE  10  26  38  FOBS=   123.1  SIGMA=   1.6  PHAS=  -125.7  FOM=  0.93  TEST= 0
INDE  10  26  40  FOBS=   124.8  SIGMA=   1.7  PHAS=    82.6  FOM=  0.73  TEST= 0
INDE  10  26  42  FOBS=   185.4  SIGMA=   1.1  PHAS=    -1.2  FOM=  0.90  TEST= 0
INDE  10  26  44  FOBS=   152.9  SIGMA=   1.3  PHAS=    37.1  FOM=  0.77  TEST= 0
INDE  10  26  46  FOBS=    78.9  SIGMA=   2.3  PHAS=    14.4  FOM=  0.71  TEST= 0
INDE  10  26  48  FOBS=   171.3  SIGMA=   1.1  PHAS=    12.2  FOM=  0.92  TEST= 0
INDE  10  26  50  FOBS=    69.7  SIGMA=   2.5  PHAS=    59.5  FOM=  0.62  TEST= 0
```

*FIG. 12A - 264*

```
INDE 10 26 52 FOBS=    61.4 SIGMA=  2.8 PHAS=  -16.5 FOM= 0.47 TEST= 0
INDE 10 26 54 FOBS=    47.9 SIGMA=  3.7 PHAS= -105.7 FOM= 0.44 TEST= 1
INDE 10 26 56 FOBS=   105.4 SIGMA=  1.8 PHAS=   96.9 FOM= 0.73 TEST= 0
INDE 10 26 58 FOBS=   142.9 SIGMA=  1.7 PHAS= -155.8 FOM= 0.95 TEST= 0
INDE 10 26 60 FOBS=    34.2 SIGMA=  5.1 PHAS= -122.3 FOM= 0.66 TEST= 0
INDE 10 26 62 FOBS=     0.0 SIGMA= 19.3 PHAS=    0.0 FOM= 0.00 TEST= 0
INDE 10 26 64 FOBS=     0.0 SIGMA= 25.5 PHAS=    0.0 FOM= 0.00 TEST= 1
INDE 10 26 66 FOBS=    60.3 SIGMA=  8.2 PHAS=  139.1 FOM= 0.71 TEST= 0
INDE 10 26 68 FOBS=     0.0 SIGMA= 31.1 PHAS=    0.0 FOM= 0.00 TEST= 0
INDE 10 26 70 FOBS=     0.0 SIGMA= 31.6 PHAS=    0.0 FOM= 0.00 TEST= 0
INDE 10 26 72 FOBS=    58.4 SIGMA=  8.8 PHAS=   72.4 FOM= 0.05 TEST= 1
INDE 10 27 11 FOBS=    68.1 SIGMA=  1.1 PHAS=    7.7 FOM= 0.70 TEST= 0
INDE 10 27 13 FOBS=   133.8 SIGMA=  0.7 PHAS=   17.0 FOM= 0.98 TEST= 0
INDE 10 27 15 FOBS=   157.7 SIGMA=  0.7 PHAS=   -9.9 FOM= 0.96 TEST= 0
INDE 10 27 17 FOBS=   194.4 SIGMA=  0.6 PHAS= -135.6 FOM= 0.98 TEST= 0
INDE 10 27 19 FOBS=    36.9 SIGMA=  2.5 PHAS= -176.7 FOM= 0.81 TEST= 0
INDE 10 27 21 FOBS=   232.3 SIGMA=  0.7 PHAS=  -22.3 FOM= 0.98 TEST= 0
INDE 10 27 23 FOBS=    89.3 SIGMA=  1.2 PHAS=  132.1 FOM= 0.89 TEST= 0
INDE 10 27 25 FOBS=   108.3 SIGMA=  1.1 PHAS=  171.1 FOM= 0.98 TEST= 0
INDE 10 27 27 FOBS=   178.6 SIGMA=  0.7 PHAS=   -0.9 FOM= 0.77 TEST= 0
INDE 10 27 29 FOBS=   121.7 SIGMA=  1.0 PHAS=   21.0 FOM= 0.78 TEST= 0
INDE 10 27 31 FOBS=   279.0 SIGMA=  0.6 PHAS=  101.9 FOM= 0.94 TEST= 0
INDE 10 27 33 FOBS=   190.9 SIGMA=  1.0 PHAS=  108.4 FOM= 0.97 TEST= 0
INDE 10 27 35 FOBS=    72.0 SIGMA=  2.8 PHAS=   59.8 FOM= 0.76 TEST= 0
INDE 10 27 37 FOBS=   168.3 SIGMA=  1.2 PHAS=   86.3 FOM= 0.98 TEST= 0
INDE 10 27 39 FOBS=   270.3 SIGMA=  0.9 PHAS=   67.3 FOM= 0.94 TEST= 0
INDE 10 27 41 FOBS=   256.0 SIGMA=  0.9 PHAS=  -25.7 FOM= 0.95 TEST= 0
INDE 10 27 43 FOBS=   116.9 SIGMA=  1.8 PHAS=  156.6 FOM= 0.80 TEST= 0
INDE 10 27 45 FOBS=   106.9 SIGMA=  1.7 PHAS=  -35.3 FOM= 0.74 TEST= 0
INDE 10 27 47 FOBS=   193.0 SIGMA=  1.0 PHAS=  -66.7 FOM= 0.95 TEST= 0
INDE 10 27 49 FOBS=    39.5 SIGMA=  4.4 PHAS=  130.2 FOM= 0.56 TEST= 0
INDE 10 27 51 FOBS=    97.1 SIGMA=  1.8 PHAS=   -1.4 FOM= 0.39 TEST= 1
INDE 10 27 53 FOBS=     8.4 SIGMA= 22.2 PHAS= -119.0 FOM= 0.11 TEST= 0
INDE 10 27 55 FOBS=    81.5 SIGMA=  2.1 PHAS=    4.1 FOM= 0.91 TEST= 0
INDE 10 27 57 FOBS=    81.8 SIGMA=  2.6 PHAS=   26.3 FOM= 0.85 TEST= 0
INDE 10 27 59 FOBS=    88.0 SIGMA=  2.0 PHAS=   80.5 FOM= 0.86 TEST= 0
INDE 10 27 61 FOBS=    74.0 SIGMA=  2.5 PHAS=    9.9 FOM= 0.70 TEST= 0
INDE 10 27 63 FOBS=    32.6 SIGMA=  5.8 PHAS=   11.3 FOM= 0.86 TEST= 0
INDE 10 27 67 FOBS=    76.6 SIGMA=  6.5 PHAS=   74.2 FOM= 0.94 TEST= 0
INDE 10 27 69 FOBS=    86.8 SIGMA=  5.8 PHAS= -179.9 FOM= 0.86 TEST= 0
INDE 10 27 71 FOBS=     0.0 SIGMA= 31.7 PHAS=    0.0 FOM= 0.00 TEST= 0
INDE 10 28 10 FOBS=   167.7 SIGMA=  0.6 PHAS=  166.1 FOM= 0.95 TEST= 0
INDE 10 28 12 FOBS=   221.3 SIGMA=  0.5 PHAS=   35.1 FOM= 0.90 TEST= 0
INDE 10 28 14 FOBS=    49.3 SIGMA=  1.8 PHAS=  167.7 FOM= 0.43 TEST= 0
INDE 10 28 16 FOBS=    38.7 SIGMA=  2.4 PHAS=    0.8 FOM= 0.40 TEST= 0
INDE 10 28 18 FOBS=    87.8 SIGMA=  1.1 PHAS= -106.7 FOM= 0.87 TEST= 0
INDE 10 28 20 FOBS=    33.6 SIGMA=  2.9 PHAS=  -46.7 FOM= 0.62 TEST= 0
INDE 10 28 22 FOBS=   122.7 SIGMA=  1.0 PHAS=  156.5 FOM= 0.80 TEST= 0
INDE 10 28 24 FOBS=    42.7 SIGMA=  2.7 PHAS=   55.9 FOM= 0.53 TEST= 0
INDE 10 28 26 FOBS=   242.1 SIGMA=  0.6 PHAS=   32.6 FOM= 0.97 TEST= 0
INDE 10 28 28 FOBS=   158.7 SIGMA=  0.9 PHAS= -136.3 FOM= 0.88 TEST= 0
INDE 10 28 30 FOBS=   119.8 SIGMA=  1.2 PHAS=  -89.9 FOM= 0.98 TEST= 0
INDE 10 28 32 FOBS=   265.6 SIGMA=  0.7 PHAS=  -51.1 FOM= 0.92 TEST= 0
INDE 10 28 34 FOBS=   168.2 SIGMA=  1.5 PHAS=   32.0 FOM= 0.95 TEST= 0
INDE 10 28 36 FOBS=    50.7 SIGMA=  4.8 PHAS=  169.3 FOM= 0.73 TEST= 0
INDE 10 28 38 FOBS=   235.4 SIGMA=  1.1 PHAS=  -76.2 FOM= 0.95 TEST= 0
INDE 10 28 40 FOBS=   265.1 SIGMA=  0.9 PHAS=  -91.7 FOM= 0.98 TEST= 0
INDE 10 28 42 FOBS=   164.6 SIGMA=  1.3 PHAS=  -20.6 FOM= 0.94 TEST= 0
INDE 10 28 44 FOBS=   103.3 SIGMA=  2.0 PHAS=  148.6 FOM= 0.87 TEST= 0
INDE 10 28 46 FOBS=    92.1 SIGMA=  2.0 PHAS=  123.2 FOM= 0.87 TEST= 1
INDE 10 28 48 FOBS=    44.3 SIGMA=  4.1 PHAS=    1.9 FOM= 0.34 TEST= 0
INDE 10 28 50 FOBS=    32.7 SIGMA=  5.5 PHAS=  -44.5 FOM= 0.23 TEST= 0
INDE 10 28 52 FOBS=    52.8 SIGMA=  3.2 PHAS=  -11.8 FOM= 0.56 TEST= 0
INDE 10 28 54 FOBS=   113.5 SIGMA=  1.5 PHAS=   18.8 FOM= 0.88 TEST= 0
INDE 10 28 56 FOBS=   140.8 SIGMA=  1.3 PHAS=   73.6 FOM= 0.95 TEST= 0
INDE 10 28 58 FOBS=    56.2 SIGMA=  3.5 PHAS=  -71.2 FOM= 0.47 TEST= 0
INDE 10 28 60 FOBS=    67.4 SIGMA=  2.5 PHAS=  -82.9 FOM= 0.60 TEST= 0
INDE 10 28 62 FOBS=    54.2 SIGMA=  3.8 PHAS= -130.2 FOM= 0.69 TEST= 0
INDE 10 28 64 FOBS=    31.6 SIGMA=  6.1 PHAS=  -78.4 FOM= 0.53 TEST= 0
INDE 10 28 66 FOBS=   116.9 SIGMA=  4.3 PHAS=  -21.1 FOM= 0.95 TEST= 0
```

*FIG. 12A - 265*

| | | | | | | | | | | | | | |
|---|---|---|---|---|---|---|---|---|---|---|---|---|---|
| INDE | 10 | 28 | 68 | FOBS= | 96.0 | SIGMA= | 5.2 | PHAS= | -27.7 | FOM= | 0.92 | TEST= | 0 |
| INDE | 10 | 28 | 70 | FOBS= | 87.1 | SIGMA= | 5.9 | PHAS= | -82.1 | FOM= | 0.71 | TEST= | 0 |
| INDE | 10 | 29 | 11 | FOBS= | 117.4 | SIGMA= | 0.7 | PHAS= | -86.6 | FOM= | 0.96 | TEST= | 0 |
| INDE | 10 | 29 | 13 | FOBS= | 54.2 | SIGMA= | 1.7 | PHAS= | 147.9 | FOM= | 0.89 | TEST= | 0 |
| INDE | 10 | 29 | 15 | FOBS= | 131.5 | SIGMA= | 0.8 | PHAS= | 97.5 | FOM= | 0.83 | TEST= | 0 |
| INDE | 10 | 29 | 17 | FOBS= | 151.8 | SIGMA= | 0.8 | PHAS= | -172.5 | FOM= | 0.97 | TEST= | 0 |
| INDE | 10 | 29 | 19 | FOBS= | 64.9 | SIGMA= | 1.6 | PHAS= | 149.1 | FOM= | 0.94 | TEST= | 0 |
| INDE | 10 | 29 | 21 | FOBS= | 201.2 | SIGMA= | 0.7 | PHAS= | 18.4 | FOM= | 0.91 | TEST= | 1 |
| INDE | 10 | 29 | 23 | FOBS= | 225.1 | SIGMA= | 0.7 | PHAS= | 59.7 | FOM= | 0.93 | TEST= | 0 |
| INDE | 10 | 29 | 25 | FOBS= | 138.3 | SIGMA= | 1.0 | PHAS= | -172.8 | FOM= | 0.93 | TEST= | 0 |
| INDE | 10 | 29 | 27 | FOBS= | 83.0 | SIGMA= | 1.7 | PHAS= | -91.3 | FOM= | 0.31 | TEST= | 0 |
| INDE | 10 | 29 | 29 | FOBS= | 260.5 | SIGMA= | 0.7 | PHAS= | 117.3 | FOM= | 0.95 | TEST= | 0 |
| INDE | 10 | 29 | 31 | FOBS= | 282.7 | SIGMA= | 0.7 | PHAS= | -164.7 | FOM= | 0.97 | TEST= | 0 |
| INDE | 10 | 29 | 33 | FOBS= | 231.6 | SIGMA= | 0.8 | PHAS= | -178.5 | FOM= | 0.95 | TEST= | 0 |
| INDE | 10 | 29 | 35 | FOBS= | 91.7 | SIGMA= | 2.2 | PHAS= | -15.8 | FOM= | 0.88 | TEST= | 1 |
| INDE | 10 | 29 | 37 | FOBS= | 37.9 | SIGMA= | 6.2 | PHAS= | 178.0 | FOM= | 0.19 | TEST= | 0 |
| INDE | 10 | 29 | 39 | FOBS= | 13.5 | SIGMA= | 17.9 | PHAS= | 61.9 | FOM= | 0.05 | TEST= | 0 |
| INDE | 10 | 29 | 41 | FOBS= | 173.4 | SIGMA= | 1.3 | PHAS= | -82.0 | FOM= | 0.97 | TEST= | 0 |
| INDE | 10 | 29 | 43 | FOBS= | 57.9 | SIGMA= | 3.5 | PHAS= | 51.1 | FOM= | 0.85 | TEST= | 0 |
| INDE | 10 | 29 | 45 | FOBS= | 137.6 | SIGMA= | 1.5 | PHAS= | -40.9 | FOM= | 0.84 | TEST= | 0 |
| INDE | 10 | 29 | 47 | FOBS= | 142.7 | SIGMA= | 1.4 | PHAS= | -143.0 | FOM= | 0.90 | TEST= | 0 |
| INDE | 10 | 29 | 49 | FOBS= | 112.2 | SIGMA= | 1.6 | PHAS= | 104.5 | FOM= | 0.23 | TEST= | 1 |
| INDE | 10 | 29 | 51 | FOBS= | 78.6 | SIGMA= | 2.2 | PHAS= | -102.3 | FOM= | 0.73 | TEST= | 0 |
| INDE | 10 | 29 | 53 | FOBS= | 71.4 | SIGMA= | 2.4 | PHAS= | -85.7 | FOM= | 0.61 | TEST= | 0 |
| INDE | 10 | 29 | 55 | FOBS= | 175.3 | SIGMA= | 1.1 | PHAS= | -20.7 | FOM= | 0.97 | TEST= | 0 |
| INDE | 10 | 29 | 57 | FOBS= | 36.0 | SIGMA= | 5.0 | PHAS= | 28.2 | FOM= | 0.67 | TEST= | 0 |
| INDE | 10 | 29 | 59 | FOBS= | 39.5 | SIGMA= | 4.3 | PHAS= | -129.5 | FOM= | 0.20 | TEST= | 0 |
| INDE | 10 | 29 | 61 | FOBS= | 57.6 | SIGMA= | 3.2 | PHAS= | -77.4 | FOM= | 0.09 | TEST= | 1 |
| INDE | 10 | 29 | 63 | FOBS= | 44.3 | SIGMA= | 4.7 | PHAS= | 34.4 | FOM= | 0.49 | TEST= | 0 |
| INDE | 10 | 29 | 65 | FOBS= | 94.6 | SIGMA= | 2.4 | PHAS= | -146.1 | FOM= | 0.92 | TEST= | 0 |
| INDE | 10 | 29 | 67 | FOBS= | 48.6 | SIGMA= | 10.3 | PHAS= | -90.4 | FOM= | 0.15 | TEST= | 1 |
| INDE | 10 | 29 | 69 | FOBS= | 53.8 | SIGMA= | 9.6 | PHAS= | -151.7 | FOM= | 0.84 | TEST= | 0 |
| INDE | 10 | 29 | 71 | FOBS= | 65.4 | SIGMA= | 8.2 | PHAS= | 23.5 | FOM= | 0.70 | TEST= | 0 |
| INDE | 10 | 30 | 10 | FOBS= | 278.2 | SIGMA= | 0.5 | PHAS= | 147.5 | FOM= | 0.95 | TEST= | 0 |
| INDE | 10 | 30 | 12 | FOBS= | 0.0 | SIGMA= | 16.2 | PHAS= | 0.0 | FOM= | 0.00 | TEST= | 1 |
| INDE | 10 | 30 | 14 | FOBS= | 152.6 | SIGMA= | 0.8 | PHAS= | 51.4 | FOM= | 0.98 | TEST= | 0 |
| INDE | 10 | 30 | 16 | FOBS= | 229.4 | SIGMA= | 0.6 | PHAS= | 5.3 | FOM= | 0.98 | TEST= | 0 |
| INDE | 10 | 30 | 18 | FOBS= | 77.0 | SIGMA= | 1.5 | PHAS= | 22.6 | FOM= | 0.98 | TEST= | 0 |
| INDE | 10 | 30 | 20 | FOBS= | 35.6 | SIGMA= | 3.5 | PHAS= | 164.4 | FOM= | 0.95 | TEST= | 0 |
| INDE | 10 | 30 | 22 | FOBS= | 131.8 | SIGMA= | 1.3 | PHAS= | 115.0 | FOM= | 0.67 | TEST= | 0 |
| INDE | 10 | 30 | 24 | FOBS= | 396.5 | SIGMA= | 0.8 | PHAS= | 86.9 | FOM= | 0.98 | TEST= | 1 |
| INDE | 10 | 30 | 26 | FOBS= | 212.7 | SIGMA= | 0.9 | PHAS= | -7.2 | FOM= | 0.92 | TEST= | 0 |
| INDE | 10 | 30 | 28 | FOBS= | 222.2 | SIGMA= | 0.9 | PHAS= | 29.9 | FOM= | 0.86 | TEST= | 0 |
| INDE | 10 | 30 | 30 | FOBS= | 178.8 | SIGMA= | 1.0 | PHAS= | 10.7 | FOM= | 0.90 | TEST= | 0 |
| INDE | 10 | 30 | 32 | FOBS= | 256.6 | SIGMA= | 0.8 | PHAS= | -173.8 | FOM= | 0.99 | TEST= | 0 |
| INDE | 10 | 30 | 34 | FOBS= | 262.8 | SIGMA= | 0.8 | PHAS= | 105.1 | FOM= | 0.97 | TEST= | 0 |
| INDE | 10 | 30 | 36 | FOBS= | 46.3 | SIGMA= | 4.6 | PHAS= | -78.9 | FOM= | 0.67 | TEST= | 0 |
| INDE | 10 | 30 | 38 | FOBS= | 289.7 | SIGMA= | 1.0 | PHAS= | -116.7 | FOM= | 0.97 | TEST= | 0 |
| INDE | 10 | 30 | 40 | FOBS= | 211.5 | SIGMA= | 1.2 | PHAS= | -123.1 | FOM= | 0.89 | TEST= | 0 |
| INDE | 10 | 30 | 42 | FOBS= | 69.8 | SIGMA= | 3.1 | PHAS= | -146.0 | FOM= | 0.64 | TEST= | 0 |
| INDE | 10 | 30 | 44 | FOBS= | 116.0 | SIGMA= | 1.8 | PHAS= | 167.2 | FOM= | 0.82 | TEST= | 0 |
| INDE | 10 | 30 | 46 | FOBS= | 198.3 | SIGMA= | 1.1 | PHAS= | 104.1 | FOM= | 0.96 | TEST= | 0 |
| INDE | 10 | 30 | 48 | FOBS= | 152.7 | SIGMA= | 1.4 | PHAS= | 87.0 | FOM= | 0.90 | TEST= | 0 |
| INDE | 10 | 30 | 50 | FOBS= | 86.9 | SIGMA= | 2.1 | PHAS= | 66.8 | FOM= | 0.89 | TEST= | 0 |
| INDE | 10 | 30 | 52 | FOBS= | 147.6 | SIGMA= | 1.2 | PHAS= | 47.2 | FOM= | 0.78 | TEST= | 1 |
| INDE | 10 | 30 | 54 | FOBS= | 27.2 | SIGMA= | 7.5 | PHAS= | -94.9 | FOM= | 0.70 | TEST= | 0 |
| INDE | 10 | 30 | 56 | FOBS= | 0.0 | SIGMA= | 18.1 | PHAS= | 0.0 | FOM= | 0.00 | TEST= | 0 |
| INDE | 10 | 30 | 58 | FOBS= | 61.7 | SIGMA= | 3.0 | PHAS= | 51.5 | FOM= | 0.65 | TEST= | 0 |
| INDE | 10 | 30 | 60 | FOBS= | 127.2 | SIGMA= | 1.3 | PHAS= | -102.3 | FOM= | 0.94 | TEST= | 0 |
| INDE | 10 | 30 | 62 | FOBS= | 0.0 | SIGMA= | 20.7 | PHAS= | 0.0 | FOM= | 0.00 | TEST= | 0 |
| INDE | 10 | 30 | 64 | FOBS= | 0.0 | SIGMA= | 20.4 | PHAS= | 0.0 | FOM= | 0.00 | TEST= | 0 |
| INDE | 10 | 30 | 66 | FOBS= | 0.0 | SIGMA= | 21.4 | PHAS= | 0.0 | FOM= | 0.00 | TEST= | 0 |
| INDE | 10 | 30 | 68 | FOBS= | 35.0 | SIGMA= | 14.0 | PHAS= | 154.8 | FOM= | 0.10 | TEST= | 1 |
| INDE | 10 | 30 | 70 | FOBS= | 40.5 | SIGMA= | 12.8 | PHAS= | -133.9 | FOM= | 0.88 | TEST= | 0 |
| INDE | 10 | 31 | 11 | FOBS= | 233.8 | SIGMA= | 0.6 | PHAS= | 75.8 | FOM= | 0.95 | TEST= | 0 |
| INDE | 10 | 31 | 13 | FOBS= | 203.6 | SIGMA= | 0.7 | PHAS= | -163.6 | FOM= | 0.99 | TEST= | 0 |
| INDE | 10 | 31 | 15 | FOBS= | 96.4 | SIGMA= | 1.3 | PHAS= | -91.8 | FOM= | 0.89 | TEST= | 0 |
| INDE | 10 | 31 | 17 | FOBS= | 90.1 | SIGMA= | 1.5 | PHAS= | -11.3 | FOM= | 0.98 | TEST= | 0 |
| INDE | 10 | 31 | 19 | FOBS= | 53.5 | SIGMA= | 2.2 | PHAS= | 74.7 | FOM= | 0.73 | TEST= | 0 |
| INDE | 10 | 31 | 21 | FOBS= | 242.0 | SIGMA= | 0.7 | PHAS= | -3.5 | FOM= | 0.98 | TEST= | 0 |

*FIG. 12A - 266*

```
INDE 10 31 23 FOBS=   309.9 SIGMA=  0.8 PHAS=  -12.4 FOM= 0.96 TEST= 0
INDE 10 31 25 FOBS=   250.5 SIGMA=  0.8 PHAS=  -32.6 FOM= 0.98 TEST= 0
INDE 10 31 27 FOBS=   192.2 SIGMA=  1.0 PHAS= -146.3 FOM= 0.94 TEST= 0
INDE 10 31 29 FOBS=   220.4 SIGMA=  0.8 PHAS= -114.7 FOM= 0.98 TEST= 0
INDE 10 31 31 FOBS=   141.9 SIGMA=  1.3 PHAS= -148.0 FOM= 0.75 TEST= 0
INDE 10 31 33 FOBS=   224.0 SIGMA=  0.9 PHAS=   47.3 FOM= 0.93 TEST= 0
INDE 10 31 35 FOBS=   223.3 SIGMA=  1.0 PHAS=  -39.0 FOM= 0.97 TEST= 0
INDE 10 31 37 FOBS=   166.8 SIGMA=  1.2 PHAS=  152.4 FOM= 0.61 TEST= 1
INDE 10 31 39 FOBS=    12.7 SIGMA= 18.5 PHAS=    9.5 FOM= 0.08 TEST= 1
INDE 10 31 41 FOBS=   130.9 SIGMA=  1.8 PHAS=   99.2 FOM= 0.43 TEST= 1
INDE 10 31 43 FOBS=   170.4 SIGMA=  1.4 PHAS=   77.2 FOM= 0.93 TEST= 0
INDE 10 31 45 FOBS=   160.7 SIGMA=  1.3 PHAS=  -12.5 FOM= 0.93 TEST= 0
INDE 10 31 47 FOBS=   112.7 SIGMA=  1.8 PHAS=  -50.8 FOM= 0.92 TEST= 0
INDE 10 31 49 FOBS=   155.1 SIGMA=  1.3 PHAS=  -11.4 FOM= 0.96 TEST= 0
INDE 10 31 51 FOBS=   136.6 SIGMA=  1.5 PHAS=  -35.7 FOM= 0.92 TEST= 0
INDE 10 31 53 FOBS=    46.4 SIGMA=  3.9 PHAS=  -81.4 FOM= 0.92 TEST= 1
INDE 10 31 55 FOBS=   120.6 SIGMA=  1.5 PHAS=  -89.1 FOM= 0.95 TEST= 0
INDE 10 31 57 FOBS=     0.0 SIGMA= 19.0 PHAS=    0.0 FOM= 0.00 TEST= 0
INDE 10 31 59 FOBS=     0.0 SIGMA= 19.5 PHAS=    0.0 FOM= 0.00 TEST= 0
INDE 10 31 61 FOBS=     0.0 SIGMA= 18.2 PHAS=    0.0 FOM= 0.00 TEST= 0
INDE 10 31 63 FOBS=    19.2 SIGMA= 10.5 PHAS=  -14.9 FOM= 0.23 TEST= 0
INDE 10 31 65 FOBS=    47.3 SIGMA=  5.1 PHAS=  131.5 FOM= 0.86 TEST= 0
INDE 10 31 67 FOBS=     0.0 SIGMA= 21.9 PHAS=    0.0 FOM= 0.00 TEST= 0
INDE 10 31 69 FOBS=    81.5 SIGMA=  6.4 PHAS=  161.8 FOM= 0.92 TEST= 0
INDE 10 32 10 FOBS=    87.3 SIGMA=  1.1 PHAS=   91.9 FOM= 0.99 TEST= 0
INDE 10 32 12 FOBS=    82.2 SIGMA=  1.4 PHAS=   18.9 FOM= 0.92 TEST= 0
INDE 10 32 14 FOBS=   388.4 SIGMA=  0.5 PHAS=   85.6 FOM= 0.97 TEST= 0
INDE 10 32 16 FOBS=   264.5 SIGMA=  0.6 PHAS=  -31.5 FOM= 0.97 TEST= 0
INDE 10 32 18 FOBS=   202.8 SIGMA=  0.8 PHAS=  -17.7 FOM= 0.92 TEST= 0
INDE 10 32 20 FOBS=   100.3 SIGMA=  1.4 PHAS=   25.1 FOM= 0.82 TEST= 0
INDE 10 32 22 FOBS=   256.1 SIGMA=  0.8 PHAS=  -85.5 FOM= 0.97 TEST= 0
INDE 10 32 24 FOBS=    95.6 SIGMA=  2.0 PHAS=  -27.0 FOM= 0.74 TEST= 0
INDE 10 32 26 FOBS=    92.1 SIGMA=  1.9 PHAS=  -63.5 FOM= 0.80 TEST= 0
INDE 10 32 28 FOBS=   442.5 SIGMA=  0.9 PHAS=   93.6 FOM= 0.97 TEST= 0
INDE 10 32 30 FOBS=    71.4 SIGMA=  2.4 PHAS= -156.7 FOM= 0.90 TEST= 0
INDE 10 32 32 FOBS=   300.0 SIGMA=  0.8 PHAS=  176.5 FOM= 0.94 TEST= 0
INDE 10 32 34 FOBS=   246.1 SIGMA=  1.1 PHAS= -123.1 FOM= 0.86 TEST= 0
INDE 10 32 36 FOBS=     0.0 SIGMA= 20.5 PHAS=    0.0 FOM= 0.00 TEST= 0
INDE 10 32 38 FOBS=    62.8 SIGMA=  3.2 PHAS=   57.5 FOM= 0.68 TEST= 0
INDE 10 32 40 FOBS=    77.7 SIGMA=  3.0 PHAS= -150.5 FOM= 0.92 TEST= 0
INDE 10 32 42 FOBS=   158.1 SIGMA=  1.6 PHAS=   41.3 FOM= 0.92 TEST= 0
INDE 10 32 44 FOBS=   135.7 SIGMA=  1.7 PHAS=    4.5 FOM= 0.76 TEST= 0
INDE 10 32 46 FOBS=     0.0 SIGMA= 21.0 PHAS=    0.0 FOM= 0.00 TEST= 0
INDE 10 32 48 FOBS=   167.1 SIGMA=  1.3 PHAS= -139.5 FOM= 0.93 TEST= 0
INDE 10 32 50 FOBS=   109.5 SIGMA=  1.8 PHAS= -134.0 FOM= 0.87 TEST= 0
INDE 10 32 52 FOBS=    43.1 SIGMA=  4.4 PHAS=   20.8 FOM= 0.69 TEST= 0
INDE 10 32 54 FOBS=    52.1 SIGMA=  3.6 PHAS=  167.9 FOM= 0.81 TEST= 0
INDE 10 32 56 FOBS=    45.5 SIGMA=  4.0 PHAS=  124.8 FOM= 0.58 TEST= 0
INDE 10 32 58 FOBS=    58.4 SIGMA=  3.1 PHAS=   60.0 FOM= 0.71 TEST= 0
INDE 10 32 60 FOBS=    56.7 SIGMA=  3.0 PHAS=  -94.3 FOM= 0.78 TEST= 0
INDE 10 32 62 FOBS=     0.0 SIGMA= 21.2 PHAS=    0.0 FOM= 0.00 TEST= 0
INDE 10 32 64 FOBS=    49.9 SIGMA=  3.9 PHAS=   38.5 FOM= 0.77 TEST= 0
INDE 10 32 66 FOBS=     0.0 SIGMA= 22.6 PHAS=    0.0 FOM= 0.00 TEST= 0
INDE 10 32 68 FOBS=    46.8 SIGMA=  5.7 PHAS=  104.8 FOM= 0.15 TEST= 1
INDE 10 33 11 FOBS=   143.7 SIGMA=  0.8 PHAS=  143.6 FOM= 0.85 TEST= 0
INDE 10 33 13 FOBS=   289.8 SIGMA=  0.6 PHAS=  -74.2 FOM= 0.96 TEST= 0
INDE 10 33 15 FOBS=   376.5 SIGMA=  0.6 PHAS=  -23.0 FOM= 0.97 TEST= 0
INDE 10 33 17 FOBS=   111.3 SIGMA=  1.2 PHAS=  -41.8 FOM= 0.92 TEST= 0
INDE 10 33 19 FOBS=   366.8 SIGMA=  0.6 PHAS=  -54.5 FOM= 0.97 TEST= 0
INDE 10 33 21 FOBS=   102.1 SIGMA=  1.5 PHAS=   22.8 FOM= 0.84 TEST= 0
INDE 10 33 23 FOBS=   164.5 SIGMA=  1.0 PHAS=  106.9 FOM= 0.96 TEST= 0
INDE 10 33 25 FOBS=    53.1 SIGMA=  3.7 PHAS=  -13.2 FOM= 0.90 TEST= 0
INDE 10 33 27 FOBS=    42.6 SIGMA=  4.3 PHAS=    9.9 FOM= 0.28 TEST= 0
INDE 10 33 29 FOBS=    89.4 SIGMA=  2.2 PHAS=  158.4 FOM= 0.86 TEST= 0
INDE 10 33 31 FOBS=   126.8 SIGMA=  1.5 PHAS=  134.7 FOM= 0.89 TEST= 0
INDE 10 33 33 FOBS=   133.0 SIGMA=  1.7 PHAS=   98.2 FOM= 0.84 TEST= 0
INDE 10 33 35 FOBS=    92.9 SIGMA=  2.2 PHAS= -120.4 FOM= 0.85 TEST= 0
INDE 10 33 37 FOBS=   182.7 SIGMA=  1.2 PHAS=   88.4 FOM= 0.92 TEST= 0
INDE 10 33 39 FOBS=    67.4 SIGMA=  2.8 PHAS=   54.4 FOM= 0.66 TEST= 0
INDE 10 33 41 FOBS=   161.7 SIGMA=  1.5 PHAS=   27.9 FOM= 0.94 TEST= 0
```

*FIG. 12A - 267*

```
INDE 10 33 43 FOBS=   124.8 SIGMA=   1.9 PHAS= -165.2 FOM= 0.88 TEST= 0
INDE 10 33 45 FOBS=     0.0 SIGMA=  23.2 PHAS=    0.0 FOM= 0.00 TEST= 0
INDE 10 33 47 FOBS=     0.0 SIGMA=  21.9 PHAS=    0.0 FOM= 0.00 TEST= 0
INDE 10 33 49 FOBS=    30.0 SIGMA=   6.3 PHAS=  -91.0 FOM= 0.28 TEST= 1
INDE 10 33 51 FOBS=     0.0 SIGMA=  20.2 PHAS=    0.0 FOM= 0.00 TEST= 0
INDE 10 33 53 FOBS=    75.0 SIGMA=   2.5 PHAS=  169.6 FOM= 0.92 TEST= 0
INDE 10 33 55 FOBS=    58.5 SIGMA=   3.6 PHAS=  -36.2 FOM= 0.33 TEST= 1
INDE 10 33 57 FOBS=    43.6 SIGMA=   4.8 PHAS=   -3.0 FOM= 0.26 TEST= 0
INDE 10 33 59 FOBS=    29.3 SIGMA=   7.0 PHAS=  -50.9 FOM= 0.64 TEST= 0
INDE 10 33 61 FOBS=     0.0 SIGMA=  22.2 PHAS=    0.0 FOM= 0.00 TEST= 0
INDE 10 33 63 FOBS=    56.6 SIGMA=   3.0 PHAS=   16.0 FOM= 0.16 TEST= 1
INDE 10 33 65 FOBS=    15.2 SIGMA=  14.1 PHAS= -172.5 FOM= 0.41 TEST= 0
INDE 10 33 67 FOBS=     0.0 SIGMA=  22.7 PHAS=    0.0 FOM= 0.00 TEST= 0
INDE 10 33 69 FOBS=    15.3 SIGMA=  34.7 PHAS= -176.3 FOM= 0.31 TEST= 0
INDE 10 34 10 FOBS=    86.5 SIGMA=   1.2 PHAS=   36.9 FOM= 0.88 TEST= 0
INDE 10 34 12 FOBS=   251.4 SIGMA=   0.7 PHAS= -107.5 FOM= 0.94 TEST= 0
INDE 10 34 14 FOBS=   457.4 SIGMA=   0.6 PHAS= -134.9 FOM= 0.98 TEST= 0
INDE 10 34 16 FOBS=   139.4 SIGMA=   1.0 PHAS=   61.5 FOM= 0.97 TEST= 0
INDE 10 34 18 FOBS=   123.9 SIGMA=   1.3 PHAS= -124.6 FOM= 0.42 TEST= 0
INDE 10 34 20 FOBS=   154.2 SIGMA=   1.1 PHAS= -148.5 FOM= 0.92 TEST= 0
INDE 10 34 22 FOBS=   161.8 SIGMA=   1.0 PHAS=  -71.8 FOM= 0.90 TEST= 0
INDE 10 34 24 FOBS=    25.6 SIGMA=   6.2 PHAS= -179.3 FOM= 0.07 TEST= 0
INDE 10 34 26 FOBS=    96.0 SIGMA=   2.1 PHAS=   -8.7 FOM= 0.81 TEST= 0
INDE 10 34 28 FOBS=   101.5 SIGMA=   1.9 PHAS= -176.7 FOM= 0.89 TEST= 0
INDE 10 34 30 FOBS=   197.1 SIGMA=   1.1 PHAS=  136.6 FOM= 0.95 TEST= 0
INDE 10 34 32 FOBS=    96.8 SIGMA=   2.1 PHAS=  106.4 FOM= 0.87 TEST= 1
INDE 10 34 34 FOBS=    91.6 SIGMA=   2.3 PHAS= -132.0 FOM= 0.83 TEST= 0
INDE 10 34 36 FOBS=   241.3 SIGMA=   1.0 PHAS=  103.7 FOM= 0.93 TEST= 0
INDE 10 34 38 FOBS=    96.4 SIGMA=   2.1 PHAS=  -29.5 FOM= 0.92 TEST= 0
INDE 10 34 40 FOBS=   228.2 SIGMA=   0.9 PHAS=  -60.1 FOM= 0.96 TEST= 0
INDE 10 34 42 FOBS=    35.2 SIGMA=   6.5 PHAS= -171.9 FOM= 0.68 TEST= 0
INDE 10 34 44 FOBS=    81.4 SIGMA=   2.8 PHAS=   94.4 FOM= 0.83 TEST= 0
INDE 10 34 46 FOBS=     0.0 SIGMA=  22.0 PHAS=    0.0 FOM= 0.00 TEST= 0
INDE 10 34 48 FOBS=   137.1 SIGMA=   1.7 PHAS=  179.3 FOM= 0.56 TEST= 1
INDE 10 34 50 FOBS=     0.0 SIGMA=  20.6 PHAS=    0.0 FOM= 0.00 TEST= 0
INDE 10 34 52 FOBS=   131.5 SIGMA=   1.5 PHAS=   75.7 FOM= 0.95 TEST= 0
INDE 10 34 54 FOBS=   136.0 SIGMA=   1.8 PHAS=   59.9 FOM= 0.93 TEST= 0
INDE 10 34 56 FOBS=    35.2 SIGMA=   6.7 PHAS=  162.7 FOM= 0.49 TEST= 0
INDE 10 34 58 FOBS=    40.8 SIGMA=   5.1 PHAS=   53.5 FOM= 0.50 TEST= 0
INDE 10 34 60 FOBS=    17.9 SIGMA=  11.0 PHAS=  132.9 FOM= 0.09 TEST= 0
INDE 10 34 62 FOBS=    18.8 SIGMA=   9.2 PHAS=  -58.6 FOM= 0.42 TEST= 0
INDE 10 34 64 FOBS=    33.9 SIGMA=   5.1 PHAS=  -24.9 FOM= 0.05 TEST= 0
INDE 10 34 66 FOBS=    35.0 SIGMA=   5.8 PHAS=  168.3 FOM= 0.59 TEST= 0
INDE 10 34 68 FOBS=     0.0 SIGMA=  21.9 PHAS=    0.0 FOM= 0.00 TEST= 0
INDE 10 35 11 FOBS=   383.6 SIGMA=   0.6 PHAS=  130.9 FOM= 0.96 TEST= 0
INDE 10 35 13 FOBS=   289.6 SIGMA=   0.6 PHAS=  150.1 FOM= 0.97 TEST= 0
INDE 10 35 15 FOBS=   396.0 SIGMA=   0.7 PHAS=   21.6 FOM= 0.97 TEST= 0
INDE 10 35 17 FOBS=   394.3 SIGMA=   0.6 PHAS=   -5.4 FOM= 0.97 TEST= 0
INDE 10 35 19 FOBS=   219.7 SIGMA=   0.9 PHAS=  -29.0 FOM= 0.98 TEST= 0
INDE 10 35 21 FOBS=   259.4 SIGMA=   0.8 PHAS=   97.1 FOM= 0.95 TEST= 0
INDE 10 35 23 FOBS=   229.7 SIGMA=   0.9 PHAS=  132.7 FOM= 0.85 TEST= 0
INDE 10 35 25 FOBS=    85.7 SIGMA=   2.6 PHAS=  -30.3 FOM= 0.94 TEST= 0
INDE 10 35 27 FOBS=    98.4 SIGMA=   2.0 PHAS=  145.6 FOM= 0.81 TEST= 1
INDE 10 35 29 FOBS=   225.9 SIGMA=   1.0 PHAS=  157.9 FOM= 0.96 TEST= 0
INDE 10 35 31 FOBS=   100.3 SIGMA=   2.0 PHAS=   56.9 FOM= 0.69 TEST= 0
INDE 10 35 33 FOBS=    99.2 SIGMA=   2.2 PHAS=   33.3 FOM= 0.89 TEST= 1
INDE 10 35 35 FOBS=   150.2 SIGMA=   1.4 PHAS=  157.5 FOM= 0.40 TEST= 0
INDE 10 35 37 FOBS=    87.3 SIGMA=   2.3 PHAS=   47.3 FOM= 0.43 TEST= 0
INDE 10 35 39 FOBS=   181.1 SIGMA=   1.2 PHAS= -158.5 FOM= 0.94 TEST= 0
INDE 10 35 41 FOBS=   154.3 SIGMA=   1.3 PHAS= -101.9 FOM= 0.93 TEST= 0
INDE 10 35 43 FOBS=    93.4 SIGMA=   2.5 PHAS=  -58.3 FOM= 0.68 TEST= 0
INDE 10 35 45 FOBS=   107.8 SIGMA=   2.2 PHAS=  -65.9 FOM= 0.56 TEST= 0
INDE 10 35 47 FOBS=     0.0 SIGMA=  22.1 PHAS=    0.0 FOM= 0.00 TEST= 0
INDE 10 35 49 FOBS=    63.2 SIGMA=   3.5 PHAS=  133.4 FOM= 0.63 TEST= 0
INDE 10 35 51 FOBS=    55.1 SIGMA=   3.9 PHAS=  -52.8 FOM= 0.24 TEST= 0
INDE 10 35 53 FOBS=    56.2 SIGMA=   3.8 PHAS=  -34.6 FOM= 0.66 TEST= 0
INDE 10 35 55 FOBS=   128.3 SIGMA=   1.7 PHAS=   10.5 FOM= 0.90 TEST= 0
INDE 10 35 57 FOBS=    90.8 SIGMA=   2.4 PHAS=   -9.5 FOM= 0.91 TEST= 0
INDE 10 35 59 FOBS=    34.4 SIGMA=   6.0 PHAS=   -3.8 FOM= 0.47 TEST= 1
INDE 10 35 61 FOBS=    54.7 SIGMA=   3.2 PHAS=  115.2 FOM= 0.15 TEST= 1
```

*FIG. 12A - 268*

```
INDE 10 35 63 FOBS=    75.0 SIGMA=  2.4 PHAS=  149.4 FOM= 0.11 TEST= 1
INDE 10 35 65 FOBS=    40.9 SIGMA=  5.1 PHAS= -151.1 FOM= 0.39 TEST= 0
INDE 10 35 67 FOBS=    62.7 SIGMA=  3.6 PHAS= -167.2 FOM= 0.84 TEST= 0
INDE 10 36 10 FOBS=   172.6 SIGMA=  0.8 PHAS=   76.4 FOM= 0.92 TEST= 0
INDE 10 36 12 FOBS=   244.7 SIGMA=  0.8 PHAS=    4.4 FOM= 0.96 TEST= 1
INDE 10 36 14 FOBS=    47.6 SIGMA=  2.9 PHAS=  -45.2 FOM= 0.41 TEST= 0
INDE 10 36 16 FOBS=   234.9 SIGMA=  0.9 PHAS=  -56.9 FOM= 0.89 TEST= 0
INDE 10 36 18 FOBS=   417.5 SIGMA=  0.7 PHAS=  -54.4 FOM= 0.98 TEST= 0
INDE 10 36 20 FOBS=   313.8 SIGMA=  0.7 PHAS=  -36.3 FOM= 0.95 TEST= 0
INDE 10 36 22 FOBS=   395.2 SIGMA=  0.6 PHAS=   62.8 FOM= 0.97 TEST= 0
INDE 10 36 24 FOBS=    55.6 SIGMA=  3.2 PHAS=   97.5 FOM= 0.18 TEST= 0
INDE 10 36 26 FOBS=   192.1 SIGMA=  1.3 PHAS=   51.1 FOM= 0.92 TEST= 0
INDE 10 36 28 FOBS=   161.9 SIGMA=  1.4 PHAS=   -1.0 FOM= 0.97 TEST= 0
INDE 10 36 30 FOBS=   211.4 SIGMA=  1.2 PHAS=  161.6 FOM= 0.95 TEST= 0
INDE 10 36 32 FOBS=    56.2 SIGMA=  3.6 PHAS= -161.5 FOM= 0.23 TEST= 0
INDE 10 36 34 FOBS=   160.5 SIGMA=  1.3 PHAS=  -52.3 FOM= 0.95 TEST= 0
INDE 10 36 36 FOBS=   152.7 SIGMA=  1.5 PHAS=   58.8 FOM= 0.90 TEST= 0
INDE 10 36 38 FOBS=     0.0 SIGMA= 19.7 PHAS=    0.0 FOM= 0.00 TEST= 0
INDE 10 36 40 FOBS=   162.5 SIGMA=  1.2 PHAS=  115.3 FOM= 0.90 TEST= 0
INDE 10 36 42 FOBS=   187.3 SIGMA=  1.1 PHAS=  142.6 FOM= 0.96 TEST= 0
INDE 10 36 44 FOBS=    44.1 SIGMA=  5.1 PHAS= -164.5 FOM= 0.69 TEST= 0
INDE 10 36 46 FOBS=     0.0 SIGMA= 22.0 PHAS=    0.0 FOM= 0.00 TEST= 0
INDE 10 36 48 FOBS=    69.6 SIGMA=  3.2 PHAS=   97.8 FOM= 0.86 TEST= 0
INDE 10 36 50 FOBS=    43.6 SIGMA=  5.0 PHAS=  -74.9 FOM= 0.47 TEST= 0
INDE 10 36 52 FOBS=     9.8 SIGMA= 23.9 PHAS=   64.7 FOM= 0.51 TEST= 0
INDE 10 36 54 FOBS=     0.0 SIGMA= 20.5 PHAS=    0.0 FOM= 0.00 TEST= 0
INDE 10 36 56 FOBS=    97.4 SIGMA=  2.2 PHAS= -100.0 FOM= 0.95 TEST= 0
INDE 10 36 58 FOBS=    44.8 SIGMA=  4.6 PHAS=  -11.2 FOM= 0.67 TEST= 0
INDE 10 36 60 FOBS=    40.6 SIGMA=  4.5 PHAS=  -31.8 FOM= 0.62 TEST= 0
INDE 10 36 62 FOBS=    58.0 SIGMA=  3.2 PHAS=  138.4 FOM= 0.83 TEST= 0
INDE 10 36 64 FOBS=    63.7 SIGMA=  2.8 PHAS=  -99.1 FOM= 0.45 TEST= 0
INDE 10 36 66 FOBS=    58.9 SIGMA=  3.9 PHAS=  132.1 FOM= 0.86 TEST= 0
INDE 10 36 68 FOBS=    15.0 SIGMA= 15.3 PHAS= -119.3 FOM= 0.07 TEST= 1
INDE 10 37 11 FOBS=   103.5 SIGMA=  1.2 PHAS= -136.8 FOM= 0.97 TEST= 0
INDE 10 37 13 FOBS=   178.8 SIGMA=  0.9 PHAS= -142.9 FOM= 0.83 TEST= 0
INDE 10 37 15 FOBS=   109.4 SIGMA=  1.4 PHAS=   73.3 FOM= 0.90 TEST= 0
INDE 10 37 17 FOBS=   176.9 SIGMA=  1.0 PHAS= -114.2 FOM= 0.96 TEST= 0
INDE 10 37 19 FOBS=   377.8 SIGMA=  0.7 PHAS=    0.1 FOM= 0.80 TEST= 1
INDE 10 37 21 FOBS=   141.6 SIGMA=  1.4 PHAS=  -60.8 FOM= 0.93 TEST= 1
INDE 10 37 23 FOBS=   253.1 SIGMA=  0.9 PHAS=  -84.4 FOM= 0.95 TEST= 0
INDE 10 37 25 FOBS=   206.3 SIGMA=  1.0 PHAS=   67.4 FOM= 0.94 TEST= 0
INDE 10 37 27 FOBS=    23.8 SIGMA= 12.9 PHAS=  -36.3 FOM= 0.09 TEST= 0
INDE 10 37 29 FOBS=    61.5 SIGMA=  3.5 PHAS= -143.1 FOM= 0.24 TEST= 1
INDE 10 37 31 FOBS=   238.8 SIGMA=  1.1 PHAS=  100.6 FOM= 0.96 TEST= 0
INDE 10 37 33 FOBS=   133.4 SIGMA=  1.5 PHAS=  147.5 FOM= 0.83 TEST= 0
INDE 10 37 35 FOBS=   167.3 SIGMA=  1.3 PHAS= -133.8 FOM= 0.97 TEST= 0
INDE 10 37 37 FOBS=    51.8 SIGMA=  3.3 PHAS=   82.5 FOM= 0.26 TEST= 1
INDE 10 37 39 FOBS=    83.8 SIGMA=  2.3 PHAS=  127.7 FOM= 0.80 TEST= 0
INDE 10 37 41 FOBS=   252.2 SIGMA=  1.0 PHAS=   22.6 FOM= 0.96 TEST= 0
INDE 10 37 43 FOBS=    39.2 SIGMA=  4.7 PHAS=   20.8 FOM= 0.66 TEST= 0
INDE 10 37 45 FOBS=    60.5 SIGMA=  3.7 PHAS=  -44.1 FOM= 0.82 TEST= 0
INDE 10 37 47 FOBS=   147.1 SIGMA=  1.6 PHAS=  -12.9 FOM= 0.95 TEST= 0
INDE 10 37 49 FOBS=     0.0 SIGMA= 20.7 PHAS=    0.0 FOM= 0.00 TEST= 0
INDE 10 37 51 FOBS=    60.4 SIGMA=  3.6 PHAS=   97.9 FOM= 0.86 TEST= 0
INDE 10 37 53 FOBS=     0.0 SIGMA= 24.2 PHAS=    0.0 FOM= 0.00 TEST= 0
INDE 10 37 55 FOBS=    35.9 SIGMA=  3.1 PHAS=  104.4 FOM= 0.34 TEST= 0
INDE 10 37 57 FOBS=    22.3 SIGMA= 11.2 PHAS=  120.1 FOM= 0.20 TEST= 0
INDE 10 37 59 FOBS=    40.6 SIGMA=  5.2 PHAS=  171.4 FOM= 0.46 TEST= 0
INDE 10 37 61 FOBS=    57.3 SIGMA=  3.1 PHAS=   27.8 FOM= 0.66 TEST= 0
INDE 10 37 63 FOBS=    55.4 SIGMA=  3.3 PHAS=   27.9 FOM= 0.60 TEST= 0
INDE 10 37 65 FOBS=    44.4 SIGMA=  5.1 PHAS=   86.6 FOM= 0.13 TEST= 0
INDE 10 37 67 FOBS=     0.0 SIGMA= 21.5 PHAS=    0.0 FOM= 0.00 TEST= 0
INDE 10 38 10 FOBS=    86.9 SIGMA=  1.7 PHAS=  128.4 FOM= 0.94 TEST= 0
INDE 10 38 12 FOBS=   234.9 SIGMA=  0.8 PHAS=  165.5 FOM= 0.94 TEST= 1
INDE 10 38 14 FOBS=   259.2 SIGMA=  0.7 PHAS=   83.3 FOM= 0.93 TEST= 0
INDE 10 38 16 FOBS=    90.6 SIGMA=  1.8 PHAS=  114.1 FOM= 0.70 TEST= 0
INDE 10 38 18 FOBS=   135.9 SIGMA=  1.3 PHAS=   25.6 FOM= 0.98 TEST= 0
INDE 10 38 20 FOBS=   160.3 SIGMA=  1.2 PHAS=  174.2 FOM= 0.98 TEST= 1
INDE 10 38 22 FOBS=   248.6 SIGMA=  0.9 PHAS=  153.6 FOM= 0.96 TEST= 0
INDE 10 38 24 FOBS=    62.1 SIGMA=  3.1 PHAS=  100.4 FOM= 0.23 TEST= 0
```

*FIG. 12A - 269*

```
INDE 10 38 26 FOBS=   43.9 SIGMA=  4.5 PHAS=  128.0 FOM= 0.84 TEST= 0
INDE 10 38 28 FOBS=   78.5 SIGMA=  3.3 PHAS= -140.9 FOM= 0.85 TEST= 0
INDE 10 38 30 FOBS=   27.1 SIGMA=  9.1 PHAS=   38.5 FOM= 0.29 TEST= 0
INDE 10 38 32 FOBS=  142.3 SIGMA=  1.6 PHAS=   11.5 FOM= 0.92 TEST= 0
INDE 10 38 34 FOBS=  209.0 SIGMA=  1.1 PHAS=   74.8 FOM= 0.95 TEST= 0
INDE 10 38 36 FOBS=  173.3 SIGMA=  1.2 PHAS=   71.4 FOM= 0.92 TEST= 0
INDE 10 38 38 FOBS=  118.5 SIGMA=  1.7 PHAS=   91.1 FOM= 0.92 TEST= 0
INDE 10 38 40 FOBS=  167.1 SIGMA=  1.3 PHAS=  -17.1 FOM= 0.88 TEST= 0
INDE 10 38 42 FOBS=  105.9 SIGMA=  1.3 PHAS=  -52.4 FOM= 0.90 TEST= 0
INDE 10 38 44 FOBS=   64.5 SIGMA=  2.9 PHAS= -102.9 FOM= 0.64 TEST= 0
INDE 10 38 46 FOBS=  243.5 SIGMA=  1.2 PHAS= -107.4 FOM= 0.96 TEST= 0
INDE 10 38 48 FOBS=  113.7 SIGMA=  2.0 PHAS=  -63.1 FOM= 0.92 TEST= 0
INDE 10 38 50 FOBS=   76.0 SIGMA=  2.9 PHAS=  -85.2 FOM= 0.79 TEST= 0
INDE 10 38 52 FOBS=  158.2 SIGMA=  1.5 PHAS=  -18.2 FOM= 0.97 TEST= 0
INDE 10 38 54 FOBS=   50.0 SIGMA=  4.3 PHAS=    3.9 FOM= 0.58 TEST= 0
INDE 10 38 56 FOBS=   18.6 SIGMA= 12.3 PHAS= -170.3 FOM= 0.39 TEST= 0
INDE 10 38 58 FOBS=  139.6 SIGMA=  1.6 PHAS=   60.5 FOM= 0.97 TEST= 0
INDE 10 38 60 FOBS=   26.2 SIGMA=  8.9 PHAS= -174.5 FOM= 0.35 TEST= 0
INDE 10 38 62 FOBS=   77.4 SIGMA=  2.4 PHAS=  174.1 FOM= 0.01 TEST= 1
INDE 10 38 64 FOBS=    0.0 SIGMA= 19.6 PHAS=    0.0 FOM= 0.00 TEST= 0
INDE 10 38 66 FOBS=    0.0 SIGMA= 23.0 PHAS=    0.0 FOM= 0.00 TEST= 0
INDE 10 39 11 FOBS=  384.2 SIGMA=  0.7 PHAS=   78.7 FOM= 0.97 TEST= 0
INDE 10 39 13 FOBS=  202.9 SIGMA=  0.9 PHAS=   64.2 FOM= 0.88 TEST= 0
INDE 10 39 15 FOBS=  119.3 SIGMA=  1.4 PHAS=   10.0 FOM= 0.80 TEST= 0
INDE 10 39 17 FOBS=  193.9 SIGMA=  1.0 PHAS=  -82.3 FOM= 0.98 TEST= 0
INDE 10 39 19 FOBS=   50.8 SIGMA=  4.0 PHAS=  -73.5 FOM= 0.61 TEST= 0
INDE 10 39 21 FOBS=  226.1 SIGMA=  0.9 PHAS=   77.9 FOM= 0.95 TEST= 0
INDE 10 39 23 FOBS=  123.5 SIGMA=  1.7 PHAS= -106.1 FOM= 0.93 TEST= 0
INDE 10 39 25 FOBS=  195.6 SIGMA=  1.1 PHAS=   45.1 FOM= 0.95 TEST= 0
INDE 10 39 27 FOBS=  134.1 SIGMA=  1.7 PHAS=  146.0 FOM= 0.93 TEST= 0
INDE 10 39 29 FOBS=    0.0 SIGMA= 22.6 PHAS=    0.0 FOM= 0.00 TEST= 0
INDE 10 39 31 FOBS=    0.0 SIGMA= 21.8 PHAS=    0.0 FOM= 0.00 TEST= 0
INDE 10 39 33 FOBS=  204.6 SIGMA=  1.1 PHAS= -135.3 FOM= 0.96 TEST= 0
INDE 10 39 35 FOBS=  196.4 SIGMA=  1.1 PHAS=  -81.8 FOM= 0.96 TEST= 0
INDE 10 39 37 FOBS=  149.3 SIGMA=  1.4 PHAS=   48.8 FOM= 0.92 TEST= 0
INDE 10 39 39 FOBS=  211.3 SIGMA=  1.0 PHAS=   -1.3 FOM= 0.91 TEST= 0
INDE 10 39 41 FOBS=   61.3 SIGMA=  3.1 PHAS=  -32.6 FOM= 0.64 TEST= 0
INDE 10 39 43 FOBS=    0.0 SIGMA= 21.0 PHAS=    0.0 FOM= 0.00 TEST= 1
INDE 10 39 45 FOBS=  135.4 SIGMA=  1.4 PHAS=  169.7 FOM= 0.95 TEST= 0
INDE 10 39 47 FOBS=   87.8 SIGMA=  2.6 PHAS= -104.3 FOM= 0.83 TEST= 0
INDE 10 39 49 FOBS=   72.4 SIGMA=  3.1 PHAS=  170.0 FOM= 0.53 TEST= 0
INDE 10 39 51 FOBS=  117.5 SIGMA=  1.9 PHAS=  176.0 FOM= 0.92 TEST= 0
INDE 10 39 53 FOBS=   26.0 SIGMA=  9.3 PHAS= -177.1 FOM= 0.61 TEST= 0
INDE 10 39 55 FOBS=   49.2 SIGMA=  4.3 PHAS=   61.8 FOM= 0.45 TEST= 0
INDE 10 39 57 FOBS=  128.1 SIGMA=  1.8 PHAS=    8.3 FOM= 0.94 TEST= 0
INDE 10 39 59 FOBS=   43.0 SIGMA=  4.9 PHAS=  -23.8 FOM= 0.45 TEST= 0
INDE 10 39 61 FOBS=   46.4 SIGMA=  4.0 PHAS= -165.9 FOM= 0.58 TEST= 0
INDE 10 39 63 FOBS=    0.0 SIGMA= 21.5 PHAS=    0.0 FOM= 0.00 TEST= 0
INDE 10 39 65 FOBS=    0.0 SIGMA= 21.4 PHAS=    0.0 FOM= 0.00 TEST= 0
INDE 10 40 10 FOBS=  343.2 SIGMA=  0.9 PHAS=  -14.0 FOM= 0.97 TEST= 0
INDE 10 40 12 FOBS=  144.4 SIGMA=  1.2 PHAS=  -42.8 FOM= 0.93 TEST= 0
INDE 10 40 14 FOBS=   22.4 SIGMA=  7.4 PHAS=  148.1 FOM= 0.13 TEST= 0
INDE 10 40 16 FOBS=  107.9 SIGMA=  1.6 PHAS= -131.0 FOM= 0.91 TEST= 0
INDE 10 40 18 FOBS=  235.4 SIGMA=  0.9 PHAS=   95.4 FOM= 0.89 TEST= 1
INDE 10 40 20 FOBS=  154.4 SIGMA=  1.3 PHAS=  -98.1 FOM= 0.96 TEST= 0
INDE 10 40 22 FOBS=  178.9 SIGMA=  1.2 PHAS= -100.8 FOM= 0.91 TEST= 0
INDE 10 40 24 FOBS=  225.2 SIGMA=  1.0 PHAS=   64.7 FOM= 0.94 TEST= 0
INDE 10 40 26 FOBS=   45.0 SIGMA=  4.7 PHAS=  -49.5 FOM= 0.54 TEST= 0
INDE 10 40 28 FOBS=  269.8 SIGMA=  0.9 PHAS=  123.1 FOM= 0.94 TEST= 0
INDE 10 40 30 FOBS=  125.0 SIGMA=  1.8 PHAS=    1.8 FOM= 0.33 TEST= 1
INDE 10 40 32 FOBS=  223.7 SIGMA=  1.1 PHAS=  172.1 FOM= 0.95 TEST= 1
INDE 10 40 34 FOBS=  258.0 SIGMA=  1.0 PHAS=   97.8 FOM= 0.98 TEST= 0
INDE 10 40 36 FOBS=  219.3 SIGMA=  1.0 PHAS=    6.5 FOM= 0.97 TEST= 0
INDE 10 40 38 FOBS=  153.5 SIGMA=  1.4 PHAS=  154.9 FOM= 0.47 TEST= 1
INDE 10 40 40 FOBS=   61.8 SIGMA=  3.1 PHAS=  -92.8 FOM= 0.31 TEST= 0
INDE 10 40 42 FOBS=   99.3 SIGMA=  2.0 PHAS=  -99.3 FOM= 0.90 TEST= 0
INDE 10 40 44 FOBS=   54.4 SIGMA=  3.4 PHAS=   21.9 FOM= 0.91 TEST= 0
INDE 10 40 46 FOBS=   49.7 SIGMA=  3.7 PHAS=  -67.3 FOM= 0.31 TEST= 0
INDE 10 40 48 FOBS=  103.4 SIGMA=  2.2 PHAS=  -42.2 FOM= 0.89 TEST= 0
INDE 10 40 50 FOBS=    0.0 SIGMA= 20.9 PHAS=    0.0 FOM= 0.00 TEST= 0
```

*FIG. 12A - 270*

```
INDE 10 40 52 FOBS=    64.1 SIGMA=   3.4 PHAS=   53.9 FOM= 0.81 TEST= 0
INDE 10 40 54 FOBS=    40.8 SIGMA=   5.9 PHAS=    7.5 FOM= 0.66 TEST= 0
INDE 10 40 56 FOBS=   104.6 SIGMA=   2.1 PHAS= -119.9 FOM= 0.91 TEST= 0
INDE 10 40 58 FOBS=    73.4 SIGMA=   3.0 PHAS=   -8.5 FOM= 0.89 TEST= 0
INDE 10 40 60 FOBS=   130.2 SIGMA=   1.5 PHAS=  144.5 FOM= 0.96 TEST= 0
INDE 10 40 62 FOBS=    11.8 SIGMA=  15.5 PHAS=   -7.0 FOM= 0.01 TEST= 1
INDE 10 40 64 FOBS=     0.0 SIGMA=  22.6 PHAS=    0.0 FOM= 0.00 TEST= 0
INDE 10 41 11 FOBS=   186.2 SIGMA=   1.3 PHAS= -157.8 FOM= 0.93 TEST= 0
INDE 10 41 13 FOBS=   320.5 SIGMA=   0.8 PHAS=   96.5 FOM= 0.96 TEST= 0
INDE 10 41 15 FOBS=   158.5 SIGMA=   1.2 PHAS=   31.6 FOM= 0.87 TEST= 0
INDE 10 41 17 FOBS=   272.0 SIGMA=   0.8 PHAS=  -54.1 FOM= 0.97 TEST= 0
INDE 10 41 19 FOBS=   134.1 SIGMA=   1.6 PHAS=   41.6 FOM= 0.53 TEST= 1
INDE 10 41 21 FOBS=   221.2 SIGMA=   1.0 PHAS=  124.6 FOM= 0.69 TEST= 1
INDE 10 41 23 FOBS=   163.9 SIGMA=   1.5 PHAS=   12.2 FOM= 0.95 TEST= 0
INDE 10 41 25 FOBS=    88.8 SIGMA=   2.5 PHAS=  -10.0 FOM= 0.90 TEST= 0
INDE 10 41 27 FOBS=    69.0 SIGMA=   3.1 PHAS= -162.1 FOM= 0.85 TEST= 0
INDE 10 41 29 FOBS=   140.9 SIGMA=   1.9 PHAS=   80.3 FOM= 0.79 TEST= 0
INDE 10 41 31 FOBS=    65.1 SIGMA=   3.3 PHAS=   72.4 FOM= 0.59 TEST= 0
INDE 10 41 33 FOBS=    44.6 SIGMA=   4.9 PHAS= -137.9 FOM= 0.55 TEST= 0
INDE 10 41 35 FOBS=   209.2 SIGMA=   1.0 PHAS=  -48.6 FOM= 0.91 TEST= 0
INDE 10 41 37 FOBS=   114.5 SIGMA=   1.8 PHAS=  -27.2 FOM= 0.96 TEST= 0
INDE 10 41 39 FOBS=    45.6 SIGMA=   4.2 PHAS=    4.5 FOM= 0.89 TEST= 0
INDE 10 41 41 FOBS=    77.8 SIGMA=   2.5 PHAS=  -63.9 FOM= 0.84 TEST= 0
INDE 10 41 43 FOBS=    61.7 SIGMA=   3.1 PHAS=   39.8 FOM= 0.94 TEST= 0
INDE 10 41 45 FOBS=    25.2 SIGMA=   8.2 PHAS=   16.0 FOM= 0.22 TEST= 0
INDE 10 41 47 FOBS=    49.4 SIGMA=   3.6 PHAS=  -75.6 FOM= 0.71 TEST= 0
INDE 10 41 49 FOBS=    71.9 SIGMA=   3.1 PHAS=   50.8 FOM= 0.60 TEST= 0
INDE 10 41 51 FOBS=     0.0 SIGMA=  20.8 PHAS=    0.0 FOM= 0.00 TEST= 0
INDE 10 41 53 FOBS=    52.8 SIGMA=   4.1 PHAS=   92.4 FOM= 0.76 TEST= 0
INDE 10 41 55 FOBS=     0.0 SIGMA=  20.6 PHAS=    0.0 FOM= 0.00 TEST= 0
INDE 10 41 57 FOBS=    77.2 SIGMA=   2.8 PHAS= -137.8 FOM= 0.91 TEST= 0
INDE 10 41 59 FOBS=    54.5 SIGMA=   4.0 PHAS=   57.3 FOM= 0.74 TEST= 0
INDE 10 41 61 FOBS=    36.2 SIGMA=   5.4 PHAS=   50.7 FOM= 0.81 TEST= 0
INDE 10 41 63 FOBS=     0.0 SIGMA=  23.0 PHAS=    0.0 FOM= 0.00 TEST= 0
INDE 10 41 65 FOBS=    45.9 SIGMA=   4.9 PHAS=   10.2 FOM= 0.40 TEST= 0
INDE 10 42 10 FOBS=   349.6 SIGMA=   0.9 PHAS=   58.0 FOM= 0.98 TEST= 0
INDE 10 42 12 FOBS=   376.7 SIGMA=   0.9 PHAS=   61.0 FOM= 0.96 TEST= 0
INDE 10 42 14 FOBS=   188.5 SIGMA=   1.2 PHAS=  -20.5 FOM= 0.88 TEST= 0
INDE 10 42 16 FOBS=   248.6 SIGMA=   0.9 PHAS= -119.0 FOM= 0.95 TEST= 0
INDE 10 42 18 FOBS=   231.0 SIGMA=   1.0 PHAS=   14.9 FOM= 0.99 TEST= 0
INDE 10 42 20 FOBS=   110.9 SIGMA=   2.0 PHAS=   13.1 FOM= 0.80 TEST= 0
INDE 10 42 22 FOBS=   176.1 SIGMA=   1.3 PHAS=  -55.9 FOM= 0.96 TEST= 0
INDE 10 42 24 FOBS=   154.1 SIGMA=   1.5 PHAS=  -10.9 FOM= 0.90 TEST= 0
INDE 10 42 26 FOBS=   162.4 SIGMA=   1.4 PHAS=  156.8 FOM= 0.94 TEST= 0
INDE 10 42 28 FOBS=   121.8 SIGMA=   1.8 PHAS=   22.6 FOM= 0.12 TEST= 0
INDE 10 42 30 FOBS=   153.2 SIGMA=   1.7 PHAS=   24.7 FOM= 0.89 TEST= 0
INDE 10 42 32 FOBS=   203.9 SIGMA=   1.2 PHAS=  149.4 FOM= 0.96 TEST= 0
INDE 10 42 34 FOBS=    91.8 SIGMA=   2.4 PHAS= -146.4 FOM= 0.20 TEST= 0
INDE 10 42 36 FOBS=    40.7 SIGMA=   4.7 PHAS=  -69.8 FOM= 0.66 TEST= 1
INDE 10 42 38 FOBS=   102.9 SIGMA=   1.9 PHAS= -101.5 FOM= 0.96 TEST= 0
INDE 10 42 40 FOBS=     0.0 SIGMA=  19.4 PHAS=    0.0 FOM= 0.00 TEST= 1
INDE 10 42 42 FOBS=    62.3 SIGMA=   3.1 PHAS=  -67.4 FOM= 0.63 TEST= 0
INDE 10 42 44 FOBS=   141.3 SIGMA=   1.4 PHAS=  -85.7 FOM= 0.91 TEST= 0
INDE 10 42 46 FOBS=    96.5 SIGMA=   1.9 PHAS=  -93.5 FOM= 0.94 TEST= 0
INDE 10 42 48 FOBS=   105.3 SIGMA=   1.8 PHAS=  -67.3 FOM= 0.93 TEST= 0
INDE 10 42 50 FOBS=    59.2 SIGMA=   3.7 PHAS=    0.9 FOM= 0.81 TEST= 0
INDE 10 42 52 FOBS=    83.3 SIGMA=   2.7 PHAS=  -24.2 FOM= 0.88 TEST= 0
INDE 10 42 54 FOBS=    31.8 SIGMA=   7.4 PHAS=   92.9 FOM= 0.24 TEST= 0
INDE 10 42 56 FOBS=   113.8 SIGMA=   2.0 PHAS=  145.7 FOM= 0.89 TEST= 0
INDE 10 42 58 FOBS=     0.0 SIGMA=  20.7 PHAS=    0.0 FOM= 0.00 TEST= 1
INDE 10 42 60 FOBS=    34.7 SIGMA=   5.5 PHAS=  -18.7 FOM= 0.45 TEST= 0
INDE 10 42 62 FOBS=     0.0 SIGMA=  21.6 PHAS=    0.0 FOM= 0.00 TEST= 0
INDE 10 42 64 FOBS=    50.7 SIGMA=   4.4 PHAS= -154.3 FOM= 0.78 TEST= 0
INDE 10 43 11 FOBS=   374.2 SIGMA=   1.3 PHAS=  -56.1 FOM= 0.98 TEST= 0
INDE 10 43 13 FOBS=   239.2 SIGMA=   0.9 PHAS=  -30.6 FOM= 0.80 TEST= 1
INDE 10 43 15 FOBS=   193.7 SIGMA=   1.1 PHAS=  165.5 FOM= 0.97 TEST= 0
INDE 10 43 17 FOBS=   236.3 SIGMA=   1.0 PHAS=  -88.5 FOM= 0.96 TEST= 0
INDE 10 43 19 FOBS=   311.7 SIGMA=   0.8 PHAS=  -61.4 FOM= 0.98 TEST= 0
INDE 10 43 21 FOBS=    85.0 SIGMA=   2.5 PHAS=  -79.4 FOM= 0.92 TEST= 0
INDE 10 43 23 FOBS=   219.7 SIGMA=   1.1 PHAS=  -69.2 FOM= 0.94 TEST= 0
```

*FIG. 12A - 271*

| | | | | | | | | | | | | |
|---|---|---|---|---|---|---|---|---|---|---|---|---|
| INDE | 10 | 43 | 25 | FOBS= | 45.7 | SIGMA= | 4.7 | PHAS= | -18.0 | FOM= | 0.73 | TEST= 0 |
| INDE | 10 | 43 | 27 | FOBS= | 35.4 | SIGMA= | 6.0 | PHAS= | 179.6 | FOM= | 0.26 | TEST= 0 |
| INDE | 10 | 43 | 29 | FOBS= | 31.1 | SIGMA= | 8.0 | PHAS= | -130.9 | FOM= | 0.16 | TEST= 0 |
| INDE | 10 | 43 | 31 | FOBS= | 173.7 | SIGMA= | 1.5 | PHAS= | -23.6 | FOM= | 0.12 | TEST= 1 |
| INDE | 10 | 43 | 33 | FOBS= | 32.8 | SIGMA= | 6.8 | PHAS= | -109.1 | FOM= | 0.35 | TEST= 0 |
| INDE | 10 | 43 | 35 | FOBS= | 58.6 | SIGMA= | 3.7 | PHAS= | 109.3 | FOM= | 0.17 | TEST= 0 |
| INDE | 10 | 43 | 37 | FOBS= | 0.0 | SIGMA= | 20.5 | PHAS= | 0.0 | FOM= | 0.00 | TEST= 0 |
| INDE | 10 | 43 | 39 | FOBS= | 11.9 | SIGMA= | 19.9 | PHAS= | -135.5 | FOM= | 0.18 | TEST= 0 |
| INDE | 10 | 43 | 41 | FOBS= | 0.0 | SIGMA= | 20.3 | PHAS= | 0.0 | FOM= | 0.00 | TEST= 0 |
| INDE | 10 | 43 | 43 | FOBS= | 39.8 | SIGMA= | 5.0 | PHAS= | -96.1 | FOM= | 0.21 | TEST= 0 |
| INDE | 10 | 43 | 45 | FOBS= | 94.1 | SIGMA= | 2.0 | PHAS= | 95.0 | FOM= | 0.90 | TEST= 0 |
| INDE | 10 | 43 | 47 | FOBS= | 57.3 | SIGMA= | 3.2 | PHAS= | 157.0 | FOM= | 0.87 | TEST= 0 |
| INDE | 10 | 43 | 49 | FOBS= | 78.3 | SIGMA= | 2.4 | PHAS= | 177.2 | FOM= | 0.89 | TEST= 0 |
| INDE | 10 | 43 | 51 | FOBS= | 66.0 | SIGMA= | 3.3 | PHAS= | 136.0 | FOM= | 0.76 | TEST= 0 |
| INDE | 10 | 43 | 53 | FOBS= | 68.1 | SIGMA= | 3.3 | PHAS= | 112.5 | FOM= | 0.86 | TEST= 0 |
| INDE | 10 | 43 | 55 | FOBS= | 0.0 | SIGMA= | 20.8 | PHAS= | 0.0 | FOM= | 0.00 | TEST= 0 |
| INDE | 10 | 43 | 57 | FOBS= | 34.0 | SIGMA= | 6.4 | PHAS= | -69.6 | FOM= | 0.16 | TEST= 1 |
| INDE | 10 | 43 | 59 | FOBS= | 36.6 | SIGMA= | 6.5 | PHAS= | -47.7 | FOM= | 0.68 | TEST= 0 |
| INDE | 10 | 43 | 61 | FOBS= | 25.3 | SIGMA= | 8.8 | PHAS= | -115.5 | FOM= | 0.17 | TEST= 0 |
| INDE | 10 | 43 | 63 | FOBS= | 55.5 | SIGMA= | 4.1 | PHAS= | 126.8 | FOM= | 0.90 | TEST= 0 |
| INDE | 10 | 44 | 10 | FOBS= | 45.2 | SIGMA= | 4.3 | PHAS= | 28.2 | FOM= | 0.86 | TEST= 0 |
| INDE | 10 | 44 | 12 | FOBS= | 199.3 | SIGMA= | 1.4 | PHAS= | -165.0 | FOM= | 0.94 | TEST= 0 |
| INDE | 10 | 44 | 14 | FOBS= | 251.4 | SIGMA= | 0.9 | PHAS= | -103.0 | FOM= | 0.96 | TEST= 0 |
| INDE | 10 | 44 | 16 | FOBS= | 238.5 | SIGMA= | 1.0 | PHAS= | 144.4 | FOM= | 0.96 | TEST= 0 |
| INDE | 10 | 44 | 18 | FOBS= | 120.2 | SIGMA= | 1.8 | PHAS= | -159.0 | FOM= | 0.97 | TEST= 0 |
| INDE | 10 | 44 | 20 | FOBS= | 139.2 | SIGMA= | 1.7 | PHAS= | -153.3 | FOM= | 0.92 | TEST= 0 |
| INDE | 10 | 44 | 22 | FOBS= | 155.6 | SIGMA= | 1.4 | PHAS= | -96.2 | FOM= | 0.92 | TEST= 0 |
| INDE | 10 | 44 | 24 | FOBS= | 44.2 | SIGMA= | 4.7 | PHAS= | 157.3 | FOM= | 0.29 | TEST= 0 |
| INDE | 10 | 44 | 26 | FOBS= | 83.4 | SIGMA= | 2.5 | PHAS= | 91.1 | FOM= | 0.60 | TEST= 0 |
| INDE | 10 | 44 | 28 | FOBS= | 0.0 | SIGMA= | 21.1 | PHAS= | 0.0 | FOM= | 0.00 | TEST= 0 |
| INDE | 10 | 44 | 30 | FOBS= | 93.3 | SIGMA= | 2.2 | PHAS= | 50.7 | FOM= | 0.84 | TEST= 0 |
| INDE | 10 | 44 | 32 | FOBS= | 55.4 | SIGMA= | 4.1 | PHAS= | 14.2 | FOM= | 0.10 | TEST= 0 |
| INDE | 10 | 44 | 34 | FOBS= | 90.5 | SIGMA= | 2.4 | PHAS= | 34.6 | FOM= | 0.91 | TEST= 0 |
| INDE | 10 | 44 | 36 | FOBS= | 40.5 | SIGMA= | 5.1 | PHAS= | 36.0 | FOM= | 0.62 | TEST= 0 |
| INDE | 10 | 44 | 38 | FOBS= | 123.4 | SIGMA= | 1.6 | PHAS= | 156.9 | FOM= | 0.84 | TEST= 0 |
| INDE | 10 | 44 | 40 | FOBS= | 25.1 | SIGMA= | 7.8 | PHAS= | 1.5 | FOM= | 0.45 | TEST= 0 |
| INDE | 10 | 44 | 42 | FOBS= | 0.0 | SIGMA= | 19.7 | PHAS= | 0.0 | FOM= | 0.00 | TEST= 0 |
| INDE | 10 | 44 | 44 | FOBS= | 81.6 | SIGMA= | 2.3 | PHAS= | -121.0 | FOM= | 0.89 | TEST= 0 |
| INDE | 10 | 44 | 46 | FOBS= | 92.9 | SIGMA= | 2.1 | PHAS= | -74.7 | FOM= | 0.86 | TEST= 0 |
| INDE | 10 | 44 | 48 | FOBS= | 57.7 | SIGMA= | 3.2 | PHAS= | 21.4 | FOM= | 0.52 | TEST= 0 |
| INDE | 10 | 44 | 50 | FOBS= | 90.1 | SIGMA= | 2.3 | PHAS= | 51.2 | FOM= | 0.89 | TEST= 0 |
| INDE | 10 | 44 | 52 | FOBS= | 105.4 | SIGMA= | 2.2 | PHAS= | 6.5 | FOM= | 0.89 | TEST= 0 |
| INDE | 10 | 44 | 54 | FOBS= | 74.3 | SIGMA= | 3.0 | PHAS= | 84.4 | FOM= | 0.87 | TEST= 0 |
| INDE | 10 | 44 | 56 | FOBS= | 62.0 | SIGMA= | 3.6 | PHAS= | 166.2 | FOM= | 0.81 | TEST= 0 |
| INDE | 10 | 44 | 58 | FOBS= | 63.8 | SIGMA= | 3.5 | PHAS= | -96.7 | FOM= | 0.88 | TEST= 0 |
| INDE | 10 | 44 | 60 | FOBS= | 30.0 | SIGMA= | 6.4 | PHAS= | 163.0 | FOM= | 0.43 | TEST= 0 |
| INDE | 10 | 44 | 62 | FOBS= | 68.5 | SIGMA= | 3.4 | PHAS= | 26.6 | FOM= | 0.75 | TEST= 0 |
| INDE | 10 | 45 | 11 | FOBS= | 104.7 | SIGMA= | 2.6 | PHAS= | 172.9 | FOM= | 0.79 | TEST= 0 |
| INDE | 10 | 45 | 13 | FOBS= | 86.5 | SIGMA= | 3.1 | PHAS= | 73.8 | FOM= | 0.88 | TEST= 0 |
| INDE | 10 | 45 | 15 | FOBS= | 200.6 | SIGMA= | 1.1 | PHAS= | 140.5 | FOM= | 0.94 | TEST= 0 |
| INDE | 10 | 45 | 17 | FOBS= | 54.4 | SIGMA= | 3.8 | PHAS= | 139.5 | FOM= | 0.32 | TEST= 0 |
| INDE | 10 | 45 | 19 | FOBS= | 131.9 | SIGMA= | 1.6 | PHAS= | -143.3 | FOM= | 0.64 | TEST= 0 |
| INDE | 10 | 45 | 21 | FOBS= | 66.1 | SIGMA= | 3.1 | PHAS= | -123.4 | FOM= | 0.32 | TEST= 0 |
| INDE | 10 | 45 | 23 | FOBS= | 119.7 | SIGMA= | 1.8 | PHAS= | -34.7 | FOM= | 0.88 | TEST= 1 |
| INDE | 10 | 45 | 25 | FOBS= | 83.5 | SIGMA= | 2.5 | PHAS= | 69.3 | FOM= | 0.65 | TEST= 0 |
| INDE | 10 | 45 | 27 | FOBS= | 51.7 | SIGMA= | 4.0 | PHAS= | -97.2 | FOM= | 0.78 | TEST= 0 |
| INDE | 10 | 45 | 29 | FOBS= | 58.7 | SIGMA= | 3.5 | PHAS= | -120.8 | FOM= | 0.45 | TEST= 0 |
| INDE | 10 | 45 | 31 | FOBS= | 103.1 | SIGMA= | 2.0 | PHAS= | -119.0 | FOM= | 0.50 | TEST= 0 |
| INDE | 10 | 45 | 33 | FOBS= | 168.7 | SIGMA= | 1.3 | PHAS= | -137.8 | FOM= | 0.94 | TEST= 0 |
| INDE | 10 | 45 | 35 | FOBS= | 0.0 | SIGMA= | 20.4 | PHAS= | 0.0 | FOM= | 0.00 | TEST= 0 |
| INDE | 10 | 45 | 37 | FOBS= | 61.3 | SIGMA= | 3.1 | PHAS= | 172.4 | FOM= | 0.87 | TEST= 0 |
| INDE | 10 | 45 | 39 | FOBS= | 32.5 | SIGMA= | 5.8 | PHAS= | -97.7 | FOM= | 0.64 | TEST= 0 |
| INDE | 10 | 45 | 41 | FOBS= | 51.8 | SIGMA= | 3.7 | PHAS= | 177.0 | FOM= | 0.60 | TEST= 0 |
| INDE | 10 | 45 | 43 | FOBS= | 71.3 | SIGMA= | 2.7 | PHAS= | 133.2 | FOM= | 0.84 | TEST= 0 |
| INDE | 10 | 45 | 45 | FOBS= | 201.6 | SIGMA= | 1.1 | PHAS= | 125.1 | FOM= | 0.97 | TEST= 0 |
| INDE | 10 | 45 | 47 | FOBS= | 88.3 | SIGMA= | 2.1 | PHAS= | 77.7 | FOM= | 0.60 | TEST= 0 |
| INDE | 10 | 45 | 49 | FOBS= | 48.4 | SIGMA= | 3.8 | PHAS= | 74.4 | FOM= | 0.39 | TEST= 0 |
| INDE | 10 | 45 | 51 | FOBS= | 0.0 | SIGMA= | 19.9 | PHAS= | 0.0 | FOM= | 0.00 | TEST= 0 |
| INDE | 10 | 45 | 53 | FOBS= | 41.3 | SIGMA= | 5.4 | PHAS= | -6.3 | FOM= | 0.64 | TEST= 0 |
| INDE | 10 | 45 | 55 | FOBS= | 37.4 | SIGMA= | 5.8 | PHAS= | 12.1 | FOM= | 0.57 | TEST= 0 |

*FIG. 12A - 272*

```
INDE  10  45  57  FOBS=    0.0  SIGMA=  23.4  PHAS=     0.0  FOM=  0.00  TEST=  0
INDE  10  45  59  FOBS=    0.0  SIGMA=  22.0  PHAS=     0.0  FOM=  0.00  TEST=  0
INDE  10  45  61  FOBS=   38.9  SIGMA=   6.5  PHAS=    58.7  FOM=  0.45  TEST=  0
INDE  10  46  10  FOBS=  142.8  SIGMA=   1.2  PHAS=   128.7  FOM=  0.90  TEST=  1
INDE  10  46  12  FOBS=  147.9  SIGMA=   2.0  PHAS=    43.1  FOM=  0.24  TEST=  1
INDE  10  46  14  FOBS=    0.0  SIGMA=  20.2  PHAS=     0.0  FOM=  0.00  TEST=  0
INDE  10  46  16  FOBS=  228.1  SIGMA=   1.0  PHAS=   102.7  FOM=  0.94  TEST=  0
INDE  10  46  18  FOBS=   33.7  SIGMA=   6.1  PHAS=   152.8  FOM=  0.46  TEST=  0
INDE  10  46  20  FOBS=  205.3  SIGMA=   1.2  PHAS=   109.3  FOM=  0.95  TEST=  0
INDE  10  46  22  FOBS=  139.1  SIGMA=   1.5  PHAS=  -174.6  FOM=  0.88  TEST=  0
INDE  10  46  24  FOBS=   28.3  SIGMA=   7.3  PHAS=    92.4  FOM=  0.76  TEST=  0
INDE  10  46  26  FOBS=  199.7  SIGMA=   1.2  PHAS=    35.2  FOM=  0.96  TEST=  0
INDE  10  46  28  FOBS=   16.1  SIGMA=  12.7  PHAS=  -168.4  FOM=  0.31  TEST=  0
INDE  10  46  30  FOBS=  103.2  SIGMA=   2.0  PHAS=   135.6  FOM=  0.88  TEST=  0
INDE  10  46  32  FOBS=   53.8  SIGMA=   3.7  PHAS=   -15.4  FOM=  0.67  TEST=  0
INDE  10  46  34  FOBS=   54.0  SIGMA=   3.9  PHAS=    88.0  FOM=  0.56  TEST=  0
INDE  10  46  36  FOBS=   92.9  SIGMA=   2.3  PHAS=    23.9  FOM=  0.67  TEST=  0
INDE  10  46  38  FOBS=   36.3  SIGMA=   5.2  PHAS=   176.5  FOM=  0.86  TEST=  0
INDE  10  46  40  FOBS=    0.0  SIGMA=  23.5  PHAS=     0.0  FOM=  0.00  TEST=  0
INDE  10  46  42  FOBS=   77.6  SIGMA=   2.5  PHAS=     4.8  FOM=  0.91  TEST=  0
INDE  10  46  44  FOBS=   90.3  SIGMA=   2.1  PHAS=    36.7  FOM=  0.94  TEST=  0
INDE  10  46  46  FOBS=   68.2  SIGMA=   2.8  PHAS=    10.0  FOM=  0.87  TEST=  0
INDE  10  46  48  FOBS=  104.5  SIGMA=   1.9  PHAS=   -44.9  FOM=  0.93  TEST=  0
INDE  10  46  50  FOBS=   39.8  SIGMA=   5.1  PHAS=   -60.0  FOM=  0.25  TEST=  0
INDE  10  46  52  FOBS=   58.2  SIGMA=   3.5  PHAS=   125.2  FOM=  0.84  TEST=  0
INDE  10  46  54  FOBS=   61.0  SIGMA=   3.6  PHAS=   -67.0  FOM=  0.92  TEST=  0
INDE  10  46  56  FOBS=   27.4  SIGMA=   8.1  PHAS=  -168.6  FOM=  0.65  TEST=  0
INDE  10  46  58  FOBS=   16.9  SIGMA=  16.5  PHAS=   -66.6  FOM=  0.04  TEST=  0
INDE  10  46  60  FOBS=   44.7  SIGMA=   5.2  PHAS=  -105.2  FOM=  0.59  TEST=  0
INDE  10  47  11  FOBS=   86.6  SIGMA=   3.3  PHAS=    77.4  FOM=  0.82  TEST=  0
INDE  10  47  13  FOBS=  145.8  SIGMA=   2.0  PHAS=   -56.4  FOM=  0.96  TEST=  0
INDE  10  47  15  FOBS=   91.2  SIGMA=   2.3  PHAS=    17.8  FOM=  0.89  TEST=  0
INDE  10  47  17  FOBS=   10.2  SIGMA=  19.7  PHAS=   -11.5  FOM=  0.07  TEST=  0
INDE  10  47  19  FOBS=  159.7  SIGMA=   1.5  PHAS=   -56.6  FOM=  0.36  TEST=  1
INDE  10  47  21  FOBS=   69.2  SIGMA=   3.2  PHAS=   -51.5  FOM=  0.90  TEST=  0
INDE  10  47  23  FOBS=  176.0  SIGMA=   1.3  PHAS=    63.4  FOM=  0.91  TEST=  0
INDE  10  47  25  FOBS=   92.0  SIGMA=   2.3  PHAS=   -47.8  FOM=  0.90  TEST=  0
INDE  10  47  27  FOBS=   52.8  SIGMA=   3.9  PHAS=  -130.3  FOM=  0.83  TEST=  0
INDE  10  47  29  FOBS=  101.9  SIGMA=   2.1  PHAS=  -120.5  FOM=  0.66  TEST=  0
INDE  10  47  31  FOBS=  105.2  SIGMA=   2.0  PHAS=  -153.4  FOM=  0.83  TEST=  0
INDE  10  47  33  FOBS=  108.8  SIGMA=   1.9  PHAS=   -90.4  FOM=  0.88  TEST=  0
INDE  10  47  35  FOBS=  171.5  SIGMA=   1.3  PHAS=   -94.1  FOM=  0.97  TEST=  0
INDE  10  47  37  FOBS=   69.4  SIGMA=   3.0  PHAS=   158.0  FOM=  0.88  TEST=  0
INDE  10  47  39  FOBS=    0.0  SIGMA=  19.7  PHAS=     0.0  FOM=  0.00  TEST=  0
INDE  10  47  41  FOBS=   39.6  SIGMA=   4.9  PHAS=     4.7  FOM=  0.33  TEST=  0
INDE  10  47  43  FOBS=   83.8  SIGMA=   2.3  PHAS=   -53.7  FOM=  0.87  TEST=  0
INDE  10  47  45  FOBS=    0.0  SIGMA=  20.1  PHAS=     0.0  FOM=  0.00  TEST=  0
INDE  10  47  47  FOBS=   75.7  SIGMA=   2.5  PHAS=  -133.5  FOM=  0.92  TEST=  0
INDE  10  47  49  FOBS=    0.0  SIGMA=  20.0  PHAS=     0.0  FOM=  0.00  TEST=  0
INDE  10  47  51  FOBS=   28.6  SIGMA=   7.0  PHAS=    22.2  FOM=  0.77  TEST=  0
INDE  10  47  53  FOBS=   71.9  SIGMA=   2.9  PHAS=   -87.6  FOM=  0.84  TEST=  0
INDE  10  47  55  FOBS=    0.0  SIGMA=  22.0  PHAS=     0.0  FOM=  0.00  TEST=  0
INDE  10  47  57  FOBS=    0.0  SIGMA=  21.0  PHAS=     0.0  FOM=  0.00  TEST=  0
INDE  10  47  59  FOBS=   42.3  SIGMA=   6.5  PHAS=  -129.1  FOM=  0.25  TEST=  0
INDE  10  47  61  FOBS=   60.5  SIGMA=   4.0  PHAS=   -55.9  FOM=  0.81  TEST=  0
INDE  10  48  10  FOBS=   29.3  SIGMA=   4.4  PHAS=   -36.0  FOM=  0.22  TEST=  0
INDE  10  48  12  FOBS=  111.1  SIGMA=   2.5  PHAS=     8.5  FOM=  0.77  TEST=  0
INDE  10  48  14  FOBS=  265.1  SIGMA=   1.4  PHAS=   174.5  FOM=  0.98  TEST=  0
INDE  10  48  16  FOBS=    0.0  SIGMA=  21.5  PHAS=     0.0  FOM=  0.00  TEST=  0
INDE  10  48  18  FOBS=   58.9  SIGMA=   3.4  PHAS=    30.3  FOM=  0.85  TEST=  0
INDE  10  48  20  FOBS=  171.3  SIGMA=   1.3  PHAS=   122.1  FOM=  0.92  TEST=  0
INDE  10  48  22  FOBS=  116.2  SIGMA=   1.8  PHAS=   -78.2  FOM=  0.93  TEST=  0
INDE  10  48  24  FOBS=  124.0  SIGMA=   1.7  PHAS=   100.4  FOM=  0.32  TEST=  0
INDE  10  48  26  FOBS=   52.0  SIGMA=   3.9  PHAS=  -107.0  FOM=  0.81  TEST=  0
INDE  10  48  28  FOBS=    0.0  SIGMA=  20.2  PHAS=     0.0  FOM=  0.00  TEST=  0
INDE  10  48  30  FOBS=  189.0  SIGMA=   1.2  PHAS=   148.8  FOM=  0.85  TEST=  1
INDE  10  48  32  FOBS=   52.5  SIGMA=   3.8  PHAS=   -15.9  FOM=  0.11  TEST=  1
INDE  10  48  34  FOBS=   65.0  SIGMA=   2.9  PHAS=   160.6  FOM=  0.31  TEST=  0
INDE  10  48  36  FOBS=   84.9  SIGMA=   2.5  PHAS=   162.4  FOM=  0.92  TEST=  0
INDE  10  48  38  FOBS=   20.5  SIGMA=  10.0  PHAS=    -9.2  FOM=  0.46  TEST=  0
```

*FIG. 12A - 273*

```
INDE 10 48 40 FOBS=   71.3 SIGMA=  2.7 PHAS=  -36.6 FOM= 0.88 TEST= 0
INDE 10 48 42 FOBS=    0.0 SIGMA= 19.2 PHAS=    0.0 FOM= 0.00 TEST= 0
INDE 10 48 44 FOBS=    0.0 SIGMA= 22.5 PHAS=    0.0 FOM= 0.00 TEST= 0
INDE 10 48 46 FOBS=   65.2 SIGMA=  2.9 PHAS=  137.7 FOM= 0.83 TEST= 0
INDE 10 48 48 FOBS=   16.7 SIGMA= 11.0 PHAS= -104.5 FOM= 0.11 TEST= 0
INDE 10 48 50 FOBS=   16.8 SIGMA= 12.9 PHAS= -141.6 FOM= 0.15 TEST= 0
INDE 10 48 52 FOBS=   40.2 SIGMA=  5.0 PHAS=  149.3 FOM= 0.64 TEST= 0
INDE 10 48 54 FOBS=    0.0 SIGMA= 20.1 PHAS=    0.0 FOM= 0.00 TEST= 0
INDE 10 48 56 FOBS=   11.8 SIGMA= 20.7 PHAS=   64.2 FOM= 0.21 TEST= 0
INDE 10 48 58 FOBS=    0.0 SIGMA= 23.3 PHAS=    0.0 FOM= 0.00 TEST= 0
INDE 10 48 60 FOBS=   81.0 SIGMA=  3.0 PHAS= -119.8 FOM= 0.84 TEST= 0
INDE 10 49 11 FOBS=    0.0 SIGMA= 17.7 PHAS=    0.0 FOM= 0.00 TEST= 0
INDE 10 49 13 FOBS=    0.0 SIGMA= 27.5 PHAS=    0.0 FOM= 0.00 TEST= 0
INDE 10 49 15 FOBS=   76.8 SIGMA=  2.6 PHAS=   72.6 FOM= 0.82 TEST= 0
INDE 10 49 17 FOBS=  112.2 SIGMA=  1.8 PHAS=   27.8 FOM= 0.92 TEST= 0
INDE 10 49 19 FOBS=  130.0 SIGMA=  1.6 PHAS=  -15.5 FOM= 0.90 TEST= 0
INDE 10 49 21 FOBS=   44.2 SIGMA=  5.3 PHAS=    1.1 FOM= 0.86 TEST= 0
INDE 10 49 23 FOBS=   98.1 SIGMA=  2.1 PHAS=  -62.0 FOM= 0.88 TEST= 0
INDE 10 49 25 FOBS=   93.1 SIGMA=  2.2 PHAS= -146.7 FOM= 0.91 TEST= 0
INDE 10 49 27 FOBS=   48.4 SIGMA=  4.2 PHAS=   31.0 FOM= 0.15 TEST= 0
INDE 10 49 29 FOBS=   69.6 SIGMA=  2.9 PHAS=  150.3 FOM= 0.33 TEST= 1
INDE 10 49 31 FOBS=    0.0 SIGMA= 20.0 PHAS=    0.0 FOM= 0.00 TEST= 0
INDE 10 49 33 FOBS=   61.9 SIGMA=  3.3 PHAS=  -96.3 FOM= 0.59 TEST= 0
INDE 10 49 35 FOBS=    0.0 SIGMA= 20.1 PHAS=    0.0 FOM= 0.00 TEST= 0
INDE 10 49 37 FOBS=   26.6 SIGMA=  7.6 PHAS=    0.5 FOM= 0.22 TEST= 0
INDE 10 49 39 FOBS=  180.4 SIGMA=  1.1 PHAS= -111.9 FOM= 0.96 TEST= 0
INDE 10 49 41 FOBS=    0.0 SIGMA= 21.2 PHAS=    0.0 FOM= 0.00 TEST= 1
INDE 10 49 43 FOBS=   33.2 SIGMA=  6.4 PHAS=  -81.5 FOM= 0.48 TEST= 0
INDE 10 49 45 FOBS=    0.0 SIGMA= 19.3 PHAS=    0.0 FOM= 0.00 TEST= 0
INDE 10 49 47 FOBS=   70.2 SIGMA=  2.7 PHAS=   82.9 FOM= 0.48 TEST= 0
INDE 10 49 49 FOBS=   17.5 SIGMA= 15.3 PHAS= -102.1 FOM= 0.13 TEST= 0
INDE 10 49 51 FOBS=   72.1 SIGMA=  2.9 PHAS=   43.3 FOM= 0.81 TEST= 0
INDE 10 49 53 FOBS=   50.9 SIGMA=  4.0 PHAS=  -23.7 FOM= 0.70 TEST= 0
INDE 10 49 55 FOBS=   25.7 SIGMA=  8.5 PHAS=   28.7 FOM= 0.08 TEST= 0
INDE 10 49 57 FOBS=   22.6 SIGMA= 12.1 PHAS= -153.5 FOM= 0.31 TEST= 0
INDE 10 49 59 FOBS=   85.1 SIGMA=  3.4 PHAS=  168.0 FOM= 0.83 TEST= 0
INDE 10 50 10 FOBS=  226.8 SIGMA=  1.4 PHAS=  159.2 FOM= 0.82 TEST= 1
INDE 10 50 12 FOBS=   96.5 SIGMA=  2.0 PHAS=   12.2 FOM= 0.98 TEST= 0
INDE 10 50 14 FOBS=  103.4 SIGMA=  2.6 PHAS=  149.7 FOM= 0.68 TEST= 0
INDE 10 50 16 FOBS=  219.1 SIGMA=  1.0 PHAS= -103.5 FOM= 0.71 TEST= 1
INDE 10 50 18 FOBS=   97.3 SIGMA=  2.1 PHAS=   95.6 FOM= 0.06 TEST= 1
INDE 10 50 20 FOBS=    0.0 SIGMA= 20.9 PHAS=    0.0 FOM= 0.00 TEST= 0
INDE 10 50 22 FOBS=  125.8 SIGMA=  1.7 PHAS= -131.8 FOM= 0.82 TEST= 0
INDE 10 50 24 FOBS=  183.3 SIGMA=  1.2 PHAS= -117.9 FOM= 0.91 TEST= 0
INDE 10 50 26 FOBS=  142.8 SIGMA=  1.6 PHAS= -167.4 FOM= 0.90 TEST= 0
INDE 10 50 28 FOBS=   93.9 SIGMA=  2.2 PHAS=  132.4 FOM= 0.59 TEST= 0
INDE 10 50 30 FOBS=   59.4 SIGMA=  3.4 PHAS=  166.9 FOM= 0.82 TEST= 0
INDE 10 50 32 FOBS=  112.9 SIGMA=  1.8 PHAS=   25.5 FOM= 0.90 TEST= 0
INDE 10 50 34 FOBS=   93.6 SIGMA=  2.2 PHAS=  -58.6 FOM= 0.87 TEST= 0
INDE 10 50 36 FOBS=    0.0 SIGMA= 20.9 PHAS=    0.0 FOM= 0.00 TEST= 0
INDE 10 50 38 FOBS=  163.8 SIGMA=  1.4 PHAS= -169.6 FOM= 0.94 TEST= 0
INDE 10 50 40 FOBS=   87.6 SIGMA=  2.2 PHAS=   -7.8 FOM= 0.89 TEST= 0
INDE 10 50 42 FOBS=    0.0 SIGMA= 19.2 PHAS=    0.0 FOM= 0.00 TEST= 0
INDE 10 50 44 FOBS=  118.7 SIGMA=  1.6 PHAS= -129.0 FOM= 0.95 TEST= 0
INDE 10 50 46 FOBS=   77.6 SIGMA=  2.6 PHAS=  -68.1 FOM= 0.82 TEST= 0
INDE 10 50 48 FOBS=   28.8 SIGMA=  7.9 PHAS=  117.7 FOM= 0.27 TEST= 0
INDE 10 50 50 FOBS=   32.0 SIGMA=  6.8 PHAS= -127.1 FOM= 0.44 TEST= 0
INDE 10 50 52 FOBS=   36.4 SIGMA=  6.0 PHAS=   87.5 FOM= 0.14 TEST= 1
INDE 10 50 54 FOBS=   38.9 SIGMA=  5.7 PHAS= -139.4 FOM= 0.45 TEST= 0
INDE 10 50 56 FOBS=   37.6 SIGMA=  6.5 PHAS= -129.7 FOM= 0.28 TEST= 0
INDE 10 50 58 FOBS=    0.0 SIGMA= 25.8 PHAS=    0.0 FOM= 0.00 TEST= 0
INDE 10 51 11 FOBS=  124.8 SIGMA=  1.1 PHAS=   94.3 FOM= 0.95 TEST= 0
INDE 10 51 13 FOBS=  102.2 SIGMA=  1.6 PHAS=  -89.6 FOM= 0.87 TEST= 0
INDE 10 51 15 FOBS=  191.9 SIGMA=  1.5 PHAS=   38.5 FOM= 0.34 TEST= 1
INDE 10 51 17 FOBS=  178.9 SIGMA=  1.2 PHAS=  169.4 FOM= 0.16 TEST= 1
INDE 10 51 19 FOBS=   78.7 SIGMA=  2.5 PHAS= -172.6 FOM= 0.69 TEST= 0
INDE 10 51 21 FOBS=   48.3 SIGMA=  4.3 PHAS=  131.8 FOM= 0.70 TEST= 0
INDE 10 51 23 FOBS=  198.4 SIGMA=  1.1 PHAS= -155.4 FOM= 0.95 TEST= 0
INDE 10 51 25 FOBS=  236.6 SIGMA=  1.0 PHAS=  168.1 FOM= 0.97 TEST= 0
INDE 10 51 27 FOBS=  102.3 SIGMA=  2.0 PHAS= -173.0 FOM= 0.87 TEST= 0
```

*FIG. 12A - 274*

```
INDE 10 51 29 FOBS=   130.1 SIGMA=  1.6 PHAS=   34.8 FOM= 0.92 TEST= 0
INDE 10 51 31 FOBS=    78.9 SIGMA=  2.6 PHAS=   -4.8 FOM= 0.85 TEST= 0
INDE 10 51 33 FOBS=   106.5 SIGMA=  1.9 PHAS= -111.0 FOM= 0.84 TEST= 0
INDE 10 51 35 FOBS=    59.5 SIGMA=  3.4 PHAS= -106.3 FOM= 0.65 TEST= 0
INDE 10 51 37 FOBS=    65.9 SIGMA=  3.1 PHAS=   28.3 FOM= 0.90 TEST= 0
INDE 10 51 39 FOBS=     0.0 SIGMA= 20.2 PHAS=    0.0 FOM= 0.00 TEST= 0
INDE 10 51 41 FOBS=    16.0 SIGMA= 11.4 PHAS=   20.9 FOM= 0.19 TEST= 0
INDE 10 51 43 FOBS=   146.9 SIGMA=  1.5 PHAS=  133.1 FOM= 0.93 TEST= 0
INDE 10 51 45 FOBS=    90.0 SIGMA=  2.1 PHAS=  136.3 FOM= 0.72 TEST= 1
INDE 10 51 47 FOBS=   113.3 SIGMA=  1.7 PHAS=  173.6 FOM= 0.82 TEST= 0
INDE 10 51 49 FOBS=    20.6 SIGMA= 12.2 PHAS=   89.1 FOM= 0.38 TEST= 0
INDE 10 51 51 FOBS=    37.1 SIGMA=  6.0 PHAS=  -88.3 FOM= 0.53 TEST= 0
INDE 10 51 53 FOBS=    82.9 SIGMA=  2.5 PHAS=  102.2 FOM= 0.79 TEST= 0
INDE 10 51 55 FOBS=    39.5 SIGMA=  6.3 PHAS=   60.6 FOM= 0.58 TEST= 0
INDE 10 51 57 FOBS=     0.0 SIGMA= 23.4 PHAS=    0.0 FOM= 0.00 TEST= 0
INDE 10 52 10 FOBS=   169.6 SIGMA=  1.7 PHAS=   87.4 FOM= 0.92 TEST= 0
INDE 10 52 12 FOBS=    57.1 SIGMA=  2.5 PHAS=  143.1 FOM= 0.90 TEST= 0
INDE 10 52 14 FOBS=    33.2 SIGMA=  5.7 PHAS=   -5.4 FOM= 0.15 TEST= 0
INDE 10 52 16 FOBS=     0.0 SIGMA= 22.7 PHAS=    0.0 FOM= 0.00 TEST= 0
INDE 10 52 18 FOBS=   122.1 SIGMA=  1.7 PHAS=   20.1 FOM= 0.58 TEST= 0
INDE 10 52 20 FOBS=    15.8 SIGMA= 15.5 PHAS=   36.5 FOM= 0.13 TEST= 0
INDE 10 52 22 FOBS=   246.7 SIGMA=  1.0 PHAS=  158.6 FOM= 0.96 TEST= 0
INDE 10 52 24 FOBS=   135.1 SIGMA=  1.5 PHAS=  155.7 FOM= 0.89 TEST= 0
INDE 10 52 26 FOBS=    56.4 SIGMA=  3.9 PHAS= -168.7 FOM= 0.47 TEST= 0
INDE 10 52 28 FOBS=    87.8 SIGMA=  2.3 PHAS=  110.4 FOM= 0.95 TEST= 0
INDE 10 52 30 FOBS=    76.3 SIGMA=  2.7 PHAS=  -35.9 FOM= 0.78 TEST= 0
INDE 10 52 32 FOBS=    49.9 SIGMA=  4.0 PHAS=  -41.7 FOM= 0.45 TEST= 0
INDE 10 52 34 FOBS=     0.0 SIGMA= 20.9 PHAS=    0.0 FOM= 0.00 TEST= 0
INDE 10 52 36 FOBS=    78.7 SIGMA=  2.4 PHAS= -179.2 FOM= 0.87 TEST= 0
INDE 10 52 38 FOBS=    80.1 SIGMA=  2.6 PHAS= -101.4 FOM= 0.85 TEST= 0
INDE 10 52 40 FOBS=   129.7 SIGMA=  1.6 PHAS=  -55.1 FOM= 0.88 TEST= 0
INDE 10 52 42 FOBS=   129.8 SIGMA=  1.5 PHAS=  -11.7 FOM= 0.94 TEST= 0
INDE 10 52 44 FOBS=    33.0 SIGMA=  7.7 PHAS=   52.4 FOM= 0.58 TEST= 0
INDE 10 52 46 FOBS=    18.6 SIGMA= 10.7 PHAS=  -86.6 FOM= 0.20 TEST= 0
INDE 10 52 48 FOBS=    60.8 SIGMA=  3.5 PHAS=   33.4 FOM= 0.81 TEST= 0
INDE 10 52 50 FOBS=    33.6 SIGMA=  6.3 PHAS= -123.0 FOM= 0.69 TEST= 0
INDE 10 52 52 FOBS=    52.3 SIGMA=  4.1 PHAS=   27.4 FOM= 0.08 TEST= 1
INDE 10 52 54 FOBS=    42.9 SIGMA=  6.4 PHAS=   20.6 FOM= 0.78 TEST= 0
INDE 10 52 56 FOBS=     0.0 SIGMA= 25.4 PHAS=    0.0 FOM= 0.00 TEST= 0
INDE 10 53 11 FOBS=    46.2 SIGMA=  5.3 PHAS=  141.0 FOM= 0.23 TEST= 0
INDE 10 53 13 FOBS=    89.8 SIGMA=  1.7 PHAS=  -21.2 FOM= 0.90 TEST= 0
INDE 10 53 15 FOBS=    66.6 SIGMA=  3.9 PHAS=   41.6 FOM= 0.76 TEST= 0
INDE 10 53 17 FOBS=    81.1 SIGMA=  2.4 PHAS= -125.1 FOM= 0.51 TEST= 0
INDE 10 53 19 FOBS=    38.5 SIGMA=  5.0 PHAS=  -78.3 FOM= 0.51 TEST= 0
INDE 10 53 21 FOBS=   153.4 SIGMA=  1.4 PHAS=  122.7 FOM= 0.95 TEST= 0
INDE 10 53 23 FOBS=   196.8 SIGMA=  1.1 PHAS=   99.9 FOM= 0.96 TEST= 0
INDE 10 53 25 FOBS=   204.4 SIGMA=  1.1 PHAS=  135.6 FOM= 0.96 TEST= 0
INDE 10 53 27 FOBS=     0.0 SIGMA= 21.7 PHAS=    0.0 FOM= 0.00 TEST= 1
INDE 10 53 29 FOBS=   107.9 SIGMA=  1.9 PHAS=  -13.8 FOM= 0.89 TEST= 0
INDE 10 53 31 FOBS=     0.0 SIGMA= 22.1 PHAS=    0.0 FOM= 0.00 TEST= 0
INDE 10 53 33 FOBS=    85.8 SIGMA=  2.4 PHAS=  -42.7 FOM= 0.91 TEST= 0
INDE 10 53 35 FOBS=    31.1 SIGMA=  6.8 PHAS=   30.3 FOM= 0.64 TEST= 0
INDE 10 53 37 FOBS=    97.5 SIGMA=  1.9 PHAS=   10.6 FOM= 0.87 TEST= 0
INDE 10 53 39 FOBS=   103.1 SIGMA=  2.0 PHAS=  152.7 FOM= 0.80 TEST= 0
INDE 10 53 41 FOBS=   114.7 SIGMA=  1.7 PHAS= -167.1 FOM= 0.96 TEST= 0
INDE 10 53 43 FOBS=    73.2 SIGMA=  2.6 PHAS=  -22.0 FOM= 0.69 TEST= 0
INDE 10 53 45 FOBS=   114.7 SIGMA=  1.7 PHAS=  123.0 FOM= 0.93 TEST= 0
INDE 10 53 47 FOBS=    39.1 SIGMA=  5.9 PHAS=  -39.4 FOM= 0.31 TEST= 0
INDE 10 53 49 FOBS=    48.7 SIGMA=  4.3 PHAS=  168.5 FOM= 0.77 TEST= 0
INDE 10 53 51 FOBS=    55.2 SIGMA=  3.8 PHAS=  -67.2 FOM= 0.81 TEST= 0
INDE 10 53 53 FOBS=    11.3 SIGMA= 28.8 PHAS=   36.8 FOM= 0.17 TEST= 0
INDE 10 53 55 FOBS=    16.5 SIGMA= 17.5 PHAS=  -92.0 FOM= 0.20 TEST= 0
INDE 10 54 10 FOBS=   222.6 SIGMA=  1.4 PHAS=   53.3 FOM= 0.95 TEST= 0
INDE 10 54 12 FOBS=    80.5 SIGMA=  1.7 PHAS=   20.2 FOM= 0.67 TEST= 0
INDE 10 54 14 FOBS=    40.9 SIGMA=  4.3 PHAS=   45.3 FOM= 0.29 TEST= 0
INDE 10 54 16 FOBS=    92.6 SIGMA=  2.8 PHAS=  -76.9 FOM= 0.88 TEST= 0
INDE 10 54 18 FOBS=     0.0 SIGMA= 20.6 PHAS=    0.0 FOM= 0.00 TEST= 0
INDE 10 54 20 FOBS=    26.3 SIGMA= 10.1 PHAS=    9.3 FOM= 0.50 TEST= 0
INDE 10 54 22 FOBS=    41.6 SIGMA=  5.0 PHAS=   47.4 FOM= 0.76 TEST= 0
INDE 10 54 24 FOBS=   234.6 SIGMA=  1.0 PHAS=   -9.1 FOM= 0.94 TEST= 0
```

*FIG. 12A - 275*

```
INDE 10 54 26 FOBS=  120.0 SIGMA=  1.7 PHAS=   12.6 FOM= 0.93 TEST= 0
INDE 10 54 28 FOBS=   41.0 SIGMA=  4.8 PHAS=  102.0 FOM= 0.46 TEST= 0
INDE 10 54 30 FOBS=   42.9 SIGMA=  4.6 PHAS=   36.5 FOM= 0.59 TEST= 0
INDE 10 54 32 FOBS=  104.6 SIGMA=  2.0 PHAS= -105.2 FOM= 0.94 TEST= 0
INDE 10 54 34 FOBS=   33.6 SIGMA=  6.8 PHAS= -112.6 FOM= 0.39 TEST= 0
INDE 10 54 36 FOBS=   39.3 SIGMA=  5.4 PHAS=  159.0 FOM= 0.16 TEST= 0
INDE 10 54 38 FOBS=   62.0 SIGMA=  2.9 PHAS=  129.4 FOM= 0.75 TEST= 0
INDE 10 54 40 FOBS=  109.3 SIGMA=  1.9 PHAS=   78.3 FOM= 0.91 TEST= 0
INDE 10 54 42 FOBS=   36.0 SIGMA=  5.1 PHAS=   97.5 FOM= 0.53 TEST= 0
INDE 10 54 44 FOBS=  100.0 SIGMA=  1.9 PHAS=  -60.7 FOM= 0.65 TEST= 0
INDE 10 54 46 FOBS=   27.1 SIGMA=  7.3 PHAS=  163.3 FOM= 0.20 TEST= 0
INDE 10 54 48 FOBS=   27.4 SIGMA=  8.6 PHAS=   17.6 FOM= 0.48 TEST= 0
INDE 10 54 50 FOBS=   31.2 SIGMA=  9.3 PHAS=  -53.9 FOM= 0.42 TEST= 0
INDE 10 54 52 FOBS=   59.5 SIGMA=  4.9 PHAS=   43.6 FOM= 0.67 TEST= 0
INDE 10 54 54 FOBS=   51.4 SIGMA=  6.7 PHAS=  155.0 FOM= 0.85 TEST= 0
INDE 10 55 11 FOBS=  236.4 SIGMA=  1.3 PHAS=  -77.4 FOM= 0.96 TEST= 0
INDE 10 55 13 FOBS=   16.5 SIGMA=  8.6 PHAS=  -64.9 FOM= 0.39 TEST= 0
INDE 10 55 15 FOBS=   75.0 SIGMA=  2.2 PHAS=  106.3 FOM= 0.71 TEST= 0
INDE 10 55 17 FOBS=  129.2 SIGMA=  2.1 PHAS= -121.1 FOM= 0.81 TEST= 0
INDE 10 55 19 FOBS=   88.0 SIGMA=  2.2 PHAS= -156.2 FOM= 0.53 TEST= 0
INDE 10 55 21 FOBS=    0.0 SIGMA= 21.2 PHAS=    0.0 FOM= 0.00 TEST= 0
INDE 10 55 23 FOBS=   64.7 SIGMA=  3.0 PHAS=  -25.5 FOM= 0.31 TEST= 1
INDE 10 55 25 FOBS=  101.2 SIGMA=  2.0 PHAS=  -43.9 FOM= 0.78 TEST= 0
INDE 10 55 27 FOBS=   76.4 SIGMA=  2.6 PHAS=  -85.9 FOM= 0.59 TEST= 0
INDE 10 55 29 FOBS=   28.5 SIGMA=  6.8 PHAS=  -34.4 FOM= 0.43 TEST= 0
INDE 10 55 31 FOBS=   56.1 SIGMA=  3.5 PHAS=  164.0 FOM= 0.17 TEST= 1
INDE 10 55 33 FOBS=   28.1 SIGMA=  7.0 PHAS=  176.4 FOM= 0.28 TEST= 0
INDE 10 55 35 FOBS=   40.3 SIGMA=  4.9 PHAS= -164.5 FOM= 0.39 TEST= 0
INDE 10 55 37 FOBS=  142.0 SIGMA=  1.5 PHAS=    4.9 FOM= 0.96 TEST= 0
INDE 10 55 39 FOBS=   80.5 SIGMA=  2.2 PHAS=   95.3 FOM= 0.81 TEST= 0
INDE 10 55 41 FOBS=    0.0 SIGMA= 20.1 PHAS=    0.0 FOM= 0.00 TEST= 0
INDE 10 55 43 FOBS=    0.0 SIGMA= 22.9 PHAS=    0.0 FOM= 0.00 TEST= 0
INDE 10 55 45 FOBS=   78.3 SIGMA=  2.7 PHAS=  117.9 FOM= 0.94 TEST= 0
INDE 10 55 47 FOBS=   31.7 SIGMA=  8.4 PHAS=  -38.0 FOM= 0.41 TEST= 0
INDE 10 55 49 FOBS=    0.0 SIGMA= 24.4 PHAS=    0.0 FOM= 0.00 TEST= 0
INDE 10 55 51 FOBS=   65.2 SIGMA=  6.9 PHAS=  -46.5 FOM= 0.89 TEST= 0
INDE 10 55 53 FOBS=   64.3 SIGMA=  5.6 PHAS=   35.3 FOM= 0.84 TEST= 0
INDE 10 56 10 FOBS=  102.7 SIGMA=  2.6 PHAS=  -60.2 FOM= 0.87 TEST= 0
INDE 10 56 12 FOBS=   49.4 SIGMA=  5.3 PHAS= -123.5 FOM= 0.69 TEST= 0
INDE 10 56 14 FOBS=   29.0 SIGMA=  4.9 PHAS=  -94.7 FOM= 0.32 TEST= 0
INDE 10 56 16 FOBS=   64.8 SIGMA=  2.6 PHAS=    7.9 FOM= 0.77 TEST= 0
INDE 10 56 18 FOBS=  130.9 SIGMA=  1.5 PHAS=  177.8 FOM= 0.85 TEST= 0
INDE 10 56 20 FOBS=   26.2 SIGMA=  8.2 PHAS=   91.1 FOM= 0.44 TEST= 0
INDE 10 56 22 FOBS=    0.0 SIGMA= 20.1 PHAS=    0.0 FOM= 0.00 TEST= 0
INDE 10 56 24 FOBS=   34.6 SIGMA=  5.6 PHAS=   -8.7 FOM= 0.52 TEST= 0
INDE 10 56 26 FOBS=   62.2 SIGMA=  3.1 PHAS=  -63.7 FOM= 0.60 TEST= 0
INDE 10 56 28 FOBS=   46.8 SIGMA=  4.2 PHAS=  -20.9 FOM= 0.26 TEST= 1
INDE 10 56 30 FOBS=   93.1 SIGMA=  2.2 PHAS=   55.3 FOM= 0.91 TEST= 0
INDE 10 56 32 FOBS=   14.9 SIGMA= 14.6 PHAS=  152.8 FOM= 0.14 TEST= 0
INDE 10 56 34 FOBS=   81.4 SIGMA=  2.5 PHAS=  118.2 FOM= 0.90 TEST= 0
INDE 10 56 36 FOBS=   66.7 SIGMA=  3.0 PHAS=   42.1 FOM= 0.82 TEST= 0
INDE 10 56 38 FOBS=   27.9 SIGMA=  7.0 PHAS=   52.8 FOM= 0.39 TEST= 0
INDE 10 56 40 FOBS=    0.0 SIGMA= 20.2 PHAS=    0.0 FOM= 0.00 TEST= 0
INDE 10 56 42 FOBS=   89.1 SIGMA=  2.3 PHAS= -140.1 FOM= 0.86 TEST= 0
INDE 10 56 44 FOBS=   75.9 SIGMA=  2.9 PHAS=  -50.4 FOM= 0.87 TEST= 0
INDE 10 56 46 FOBS=   16.8 SIGMA= 20.6 PHAS=  110.0 FOM= 0.33 TEST= 0
INDE 10 56 48 FOBS=   46.3 SIGMA=  5.7 PHAS=  -92.4 FOM= 0.44 TEST= 0
INDE 10 56 50 FOBS=  111.2 SIGMA=  3.2 PHAS=  -39.7 FOM= 0.96 TEST= 0
INDE 10 56 52 FOBS=   32.8 SIGMA= 10.6 PHAS= -103.9 FOM= 0.23 TEST= 0
INDE 10 57 11 FOBS=  140.6 SIGMA=  2.0 PHAS= -165.4 FOM= 0.89 TEST= 0
INDE 10 57 13 FOBS=    0.0 SIGMA= 17.9 PHAS=    0.0 FOM= 0.00 TEST= 0
INDE 10 57 15 FOBS=  118.9 SIGMA=  1.3 PHAS=    8.0 FOM= 0.95 TEST= 0
INDE 10 57 17 FOBS=   79.4 SIGMA=  2.1 PHAS= -152.0 FOM= 0.87 TEST= 0
INDE 10 57 19 FOBS=   53.5 SIGMA=  3.5 PHAS=   86.2 FOM= 0.87 TEST= 0
INDE 10 57 21 FOBS=   59.7 SIGMA=  3.2 PHAS=   41.6 FOM= 0.88 TEST= 0
INDE 10 57 23 FOBS=    0.0 SIGMA= 19.5 PHAS=    0.0 FOM= 0.00 TEST= 0
INDE 10 57 25 FOBS=   84.5 SIGMA=  2.3 PHAS=  -81.3 FOM= 0.54 TEST= 1
INDE 10 57 27 FOBS=   39.4 SIGMA=  4.9 PHAS=  135.5 FOM= 0.53 TEST= 0
INDE 10 57 29 FOBS=   82.3 SIGMA=  2.4 PHAS= -112.0 FOM= 0.89 TEST= 0
INDE 10 57 31 FOBS=   35.7 SIGMA=  5.5 PHAS=   -6.7 FOM= 0.56 TEST= 0
```

*FIG. 12A - 276*

```
INDE  10  57  33  FOBS=   56.8  SIGMA=   3.5  PHAS=    96.6  FOM=  0.50  TEST= 0
INDE  10  57  35  FOBS=   67.7  SIGMA=   3.3  PHAS=    25.1  FOM=  0.92  TEST= 0
INDE  10  57  37  FOBS=   83.2  SIGMA=   2.7  PHAS=     5.5  FOM=  0.84  TEST= 0
INDE  10  57  39  FOBS=    0.0  SIGMA=  23.4  PHAS=     0.0  FOM=  0.00  TEST= 0
INDE  10  57  41  FOBS=   17.2  SIGMA=  11.9  PHAS=    74.3  FOM=  0.11  TEST= 0
INDE  10  57  43  FOBS=   80.7  SIGMA=   2.7  PHAS=  -156.7  FOM=  0.40  TEST= 1
INDE  10  57  45  FOBS=   42.6  SIGMA=   5.3  PHAS=    12.3  FOM=  0.77  TEST= 0
INDE  10  57  47  FOBS=   72.9  SIGMA=   4.0  PHAS=    80.3  FOM=  0.90  TEST= 0
INDE  10  57  49  FOBS=   94.4  SIGMA=   3.7  PHAS=  -116.9  FOM=  0.94  TEST= 0
INDE  10  57  51  FOBS=   45.9  SIGMA=  10.0  PHAS=    45.5  FOM=  0.03  TEST= 1
INDE  10  58  10  FOBS=  124.9  SIGMA=   2.2  PHAS=    68.8  FOM=  0.89  TEST= 0
INDE  10  58  12  FOBS=   63.1  SIGMA=   4.1  PHAS=    -3.2  FOM=  0.34  TEST= 0
INDE  10  58  14  FOBS=   45.1  SIGMA=   3.9  PHAS=    15.7  FOM=  0.77  TEST= 0
INDE  10  58  16  FOBS=   68.2  SIGMA=   2.8  PHAS=    23.5  FOM=  0.84  TEST= 0
INDE  10  58  18  FOBS=   86.0  SIGMA=   2.4  PHAS=   112.1  FOM=  0.89  TEST= 0
INDE  10  58  20  FOBS=   20.8  SIGMA=   9.7  PHAS=   -59.8  FOM=  0.20  TEST= 0
INDE  10  58  22  FOBS=   40.4  SIGMA=   4.7  PHAS=    -1.3  FOM=  0.79  TEST= 0
INDE  10  58  24  FOBS=   11.6  SIGMA=  17.7  PHAS=  -141.8  FOM=  0.16  TEST= 0
INDE  10  58  26  FOBS=   38.3  SIGMA=   5.1  PHAS=  -174.8  FOM=  0.65  TEST= 0
INDE  10  58  28  FOBS=   46.2  SIGMA=   4.2  PHAS=   104.6  FOM=  0.22  TEST= 0
INDE  10  58  30  FOBS=   74.2  SIGMA=   2.7  PHAS=   129.8  FOM=  0.75  TEST= 0
INDE  10  58  32  FOBS=   76.9  SIGMA=   2.8  PHAS=    82.2  FOM=  0.52  TEST= 0
INDE  10  58  34  FOBS=   43.1  SIGMA=   5.6  PHAS=   -62.6  FOM=  0.61  TEST= 0
INDE  10  58  36  FOBS=    0.0  SIGMA=  23.1  PHAS=     0.0  FOM=  0.00  TEST= 0
INDE  10  58  38  FOBS=   53.3  SIGMA=   4.6  PHAS=  -122.0  FOM=  0.78  TEST= 0
INDE  10  58  40  FOBS=   36.1  SIGMA=   7.1  PHAS=   -94.0  FOM=  0.39  TEST= 0
INDE  10  58  42  FOBS=    0.0  SIGMA=  22.6  PHAS=     0.0  FOM=  0.00  TEST= 0
INDE  10  58  44  FOBS=   35.1  SIGMA=   7.1  PHAS=   -86.4  FOM=  0.40  TEST= 0
INDE  10  58  46  FOBS=   55.0  SIGMA=   4.7  PHAS=   -99.7  FOM=  0.85  TEST= 0
INDE  10  58  48  FOBS=    0.0  SIGMA=  28.0  PHAS=     0.0  FOM=  0.00  TEST= 0
INDE  10  58  50  FOBS=    0.0  SIGMA=  28.6  PHAS=     0.0  FOM=  0.00  TEST= 0
INDE  10  59  11  FOBS=  130.6  SIGMA=   2.1  PHAS=   -13.6  FOM=  0.90  TEST= 0
INDE  10  59  13  FOBS=  102.8  SIGMA=   2.6  PHAS=  -104.1  FOM=  0.88  TEST= 0
INDE  10  59  15  FOBS=   83.7  SIGMA=   2.2  PHAS=   -20.6  FOM=  0.87  TEST= 0
INDE  10  59  17  FOBS=   65.6  SIGMA=   2.9  PHAS=    43.3  FOM=  0.39  TEST= 0
INDE  10  59  19  FOBS=   92.3  SIGMA=   2.2  PHAS=    64.2  FOM=  0.88  TEST= 0
INDE  10  59  21  FOBS=   89.8  SIGMA=   2.2  PHAS=  -104.8  FOM=  0.94  TEST= 0
INDE  10  59  23  FOBS=   95.3  SIGMA=   2.2  PHAS=  -171.5  FOM=  0.90  TEST= 0
INDE  10  59  25  FOBS=    0.0  SIGMA=  19.5  PHAS=     0.0  FOM=  0.00  TEST= 0
INDE  10  59  27  FOBS=   52.5  SIGMA=   4.1  PHAS=   126.2  FOM=  0.79  TEST= 0
INDE  10  59  29  FOBS=    0.0  SIGMA=  21.4  PHAS=     0.0  FOM=  0.00  TEST= 0
INDE  10  59  31  FOBS=   57.7  SIGMA=   4.1  PHAS=   -17.4  FOM=  0.47  TEST= 0
INDE  10  59  33  FOBS=    0.0  SIGMA=  21.7  PHAS=     0.0  FOM=  0.00  TEST= 0
INDE  10  59  35  FOBS=   46.7  SIGMA=   5.2  PHAS=    19.0  FOM=  0.63  TEST= 0
INDE  10  59  37  FOBS=    0.0  SIGMA=  23.6  PHAS=     0.0  FOM=  0.00  TEST= 1
INDE  10  59  39  FOBS=    0.0  SIGMA=  22.0  PHAS=     0.0  FOM=  0.00  TEST= 1
INDE  10  59  41  FOBS=    0.0  SIGMA=  20.4  PHAS=     0.0  FOM=  0.00  TEST= 0
INDE  10  59  43  FOBS=   44.8  SIGMA=   4.5  PHAS=   127.4  FOM=  0.74  TEST= 0
INDE  10  59  45  FOBS=    0.0  SIGMA=  23.6  PHAS=     0.0  FOM=  0.00  TEST= 0
INDE  10  59  47  FOBS=   59.8  SIGMA=   5.7  PHAS=   135.6  FOM=  0.69  TEST= 0
INDE  10  59  49  FOBS=   45.0  SIGMA=   9.1  PHAS=  -179.5  FOM=  0.18  TEST= 0
INDE  10  60  10  FOBS=   65.1  SIGMA=   3.9  PHAS=   102.8  FOM=  0.58  TEST= 0
INDE  10  60  12  FOBS=  113.7  SIGMA=   2.3  PHAS=   176.9  FOM=  0.85  TEST= 0
INDE  10  60  14  FOBS=    0.0  SIGMA=  22.4  PHAS=     0.0  FOM=  0.00  TEST= 0
INDE  10  60  16  FOBS=   98.8  SIGMA=   1.9  PHAS=  -102.8  FOM=  0.81  TEST= 0
INDE  10  60  18  FOBS=   37.7  SIGMA=   5.2  PHAS=    12.9  FOM=  0.69  TEST= 0
INDE  10  60  20  FOBS=    0.0  SIGMA=  19.0  PHAS=     0.0  FOM=  0.00  TEST= 0
INDE  10  60  22  FOBS=   92.3  SIGMA=   2.2  PHAS=   123.2  FOM=  0.96  TEST= 0
INDE  10  60  24  FOBS=   55.7  SIGMA=   4.2  PHAS=  -168.3  FOM=  0.56  TEST= 0
INDE  10  60  26  FOBS=    0.0  SIGMA=  21.5  PHAS=     0.0  FOM=  0.00  TEST= 0
INDE  10  60  28  FOBS=   85.8  SIGMA=   2.8  PHAS=   -82.9  FOM=  0.59  TEST= 1
INDE  10  60  30  FOBS=   56.8  SIGMA=   4.2  PHAS=  -162.8  FOM=  0.83  TEST= 0
INDE  10  60  32  FOBS=   48.6  SIGMA=   4.8  PHAS=   174.9  FOM=  0.24  TEST= 0
INDE  10  60  34  FOBS=    9.5  SIGMA=  25.2  PHAS=     2.3  FOM=  0.08  TEST= 0
INDE  10  60  36  FOBS=   33.2  SIGMA=   7.4  PHAS=  -125.1  FOM=  0.46  TEST= 0
INDE  10  60  38  FOBS=    0.0  SIGMA=  23.7  PHAS=     0.0  FOM=  0.00  TEST= 0
INDE  10  60  40  FOBS=    0.0  SIGMA=  21.3  PHAS=     0.0  FOM=  0.00  TEST= 0
INDE  10  60  42  FOBS=   72.0  SIGMA=   3.0  PHAS=  -145.2  FOM=  0.73  TEST= 0
INDE  10  60  44  FOBS=    0.0  SIGMA=  20.9  PHAS=     0.0  FOM=  0.00  TEST= 1
INDE  10  60  46  FOBS=    0.0  SIGMA=  25.6  PHAS=     0.0  FOM=  0.00  TEST= 0
```

*FIG. 12A - 277*

| | | | | | | | | | | | |
|---|---|---|---|---|---|---|---|---|---|---|---|
| INDE | 10 | 60 | 48 | FOBS= | 42.3 | SIGMA= | 9.6 | PHAS= | 90.9 | FOM= | 0.31 | TEST= 0
| INDE | 10 | 61 | 11 | FOBS= | 68.2 | SIGMA= | 3.7 | PHAS= | -12.9 | FOM= | 0.67 | TEST= 1
| INDE | 10 | 61 | 13 | FOBS= | 95.4 | SIGMA= | 2.7 | PHAS= | 48.2 | FOM= | 0.81 | TEST= 0
| INDE | 10 | 61 | 15 | FOBS= | 61.1 | SIGMA= | 2.7 | PHAS= | 58.4 | FOM= | 0.89 | TEST= 0
| INDE | 10 | 61 | 17 | FOBS= | 88.0 | SIGMA= | 2.3 | PHAS= | 172.0 | FOM= | 0.91 | TEST= 0
| INDE | 10 | 61 | 19 | FOBS= | 26.3 | SIGMA= | 8.3 | PHAS= | 94.1 | FOM= | 0.32 | TEST= 0
| INDE | 10 | 61 | 21 | FOBS= | 113.8 | SIGMA= | 2.0 | PHAS= | -4.3 | FOM= | 0.92 | TEST= 0
| INDE | 10 | 61 | 23 | FOBS= | 110.1 | SIGMA= | 2.1 | PHAS= | 142.0 | FOM= | 0.94 | TEST= 0
| INDE | 10 | 61 | 25 | FOBS= | 0.0 | SIGMA= | 21.3 | PHAS= | 0.0 | FOM= | 0.00 | TEST= 0
| INDE | 10 | 61 | 27 | FOBS= | 119.9 | SIGMA= | 2.0 | PHAS= | -151.4 | FOM= | 0.46 | TEST= 1
| INDE | 10 | 61 | 29 | FOBS= | 97.7 | SIGMA= | 2.5 | PHAS= | 138.6 | FOM= | 0.89 | TEST= 0
| INDE | 10 | 61 | 31 | FOBS= | 27.5 | SIGMA= | 8.5 | PHAS= | -87.2 | FOM= | 0.24 | TEST= 0
| INDE | 10 | 61 | 33 | FOBS= | 38.8 | SIGMA= | 8.8 | PHAS= | 35.8 | FOM= | 0.01 | TEST= 1
| INDE | 10 | 61 | 35 | FOBS= | 0.0 | SIGMA= | 23.7 | PHAS= | 0.0 | FOM= | 0.00 | TEST= 0
| INDE | 10 | 61 | 37 | FOBS= | 49.8 | SIGMA= | 7.2 | PHAS= | -136.8 | FOM= | 0.38 | TEST= 0
| INDE | 10 | 61 | 39 | FOBS= | 53.9 | SIGMA= | 5.3 | PHAS= | 14.6 | FOM= | 0.85 | TEST= 0
| INDE | 10 | 61 | 41 | FOBS= | 21.9 | SIGMA= | 10.7 | PHAS= | -120.2 | FOM= | 0.04 | TEST= 1
| INDE | 10 | 61 | 43 | FOBS= | 78.2 | SIGMA= | 3.1 | PHAS= | 116.0 | FOM= | 0.90 | TEST= 0
| INDE | 10 | 61 | 45 | FOBS= | 0.0 | SIGMA= | 25.5 | PHAS= | 0.0 | FOM= | 0.00 | TEST= 0
| INDE | 10 | 61 | 47 | FOBS= | 0.0 | SIGMA= | 32.3 | PHAS= | 0.0 | FOM= | 0.00 | TEST= 0
| INDE | 10 | 62 | 10 | FOBS= | 0.0 | SIGMA= | 22.2 | PHAS= | 0.0 | FOM= | 0.00 | TEST= 0
| INDE | 10 | 62 | 12 | FOBS= | 33.0 | SIGMA= | 7.4 | PHAS= | -13.7 | FOM= | 0.29 | TEST= 0
| INDE | 10 | 62 | 14 | FOBS= | 51.9 | SIGMA= | 4.8 | PHAS= | -51.3 | FOM= | 0.77 | TEST= 0
| INDE | 10 | 62 | 16 | FOBS= | 10.9 | SIGMA= | 18.6 | PHAS= | 84.7 | FOM= | 0.11 | TEST= 0
| INDE | 10 | 62 | 18 | FOBS= | 60.6 | SIGMA= | 3.7 | PHAS= | 16.4 | FOM= | 0.72 | TEST= 0
| INDE | 10 | 62 | 20 | FOBS= | 58.2 | SIGMA= | 4.4 | PHAS= | -142.3 | FOM= | 0.80 | TEST= 0
| INDE | 10 | 62 | 22 | FOBS= | 57.4 | SIGMA= | 4.6 | PHAS= | -140.4 | FOM= | 0.27 | TEST= 0
| INDE | 10 | 62 | 24 | FOBS= | 93.4 | SIGMA= | 2.9 | PHAS= | 130.5 | FOM= | 0.86 | TEST= 0
| INDE | 10 | 62 | 26 | FOBS= | 68.1 | SIGMA= | 4.0 | PHAS= | 87.5 | FOM= | 0.86 | TEST= 0
| INDE | 10 | 62 | 28 | FOBS= | 0.0 | SIGMA= | 23.2 | PHAS= | 0.0 | FOM= | 0.00 | TEST= 0
| INDE | 10 | 62 | 30 | FOBS= | 88.8 | SIGMA= | 3.2 | PHAS= | 115.0 | FOM= | 0.90 | TEST= 0
| INDE | 10 | 62 | 32 | FOBS= | 0.0 | SIGMA= | 26.0 | PHAS= | 0.0 | FOM= | 0.00 | TEST= 0
| INDE | 10 | 62 | 34 | FOBS= | 53.8 | SIGMA= | 5.2 | PHAS= | -167.5 | FOM= | 0.37 | TEST= 0
| INDE | 10 | 62 | 36 | FOBS= | 66.0 | SIGMA= | 4.4 | PHAS= | -141.3 | FOM= | 0.84 | TEST= 0
| INDE | 10 | 62 | 38 | FOBS= | 19.4 | SIGMA= | 17.0 | PHAS= | -99.3 | FOM= | 0.49 | TEST= 0
| INDE | 10 | 62 | 40 | FOBS= | 0.0 | SIGMA= | 24.0 | PHAS= | 0.0 | FOM= | 0.00 | TEST= 1
| INDE | 10 | 62 | 42 | FOBS= | 36.7 | SIGMA= | 7.9 | PHAS= | 53.8 | FOM= | 0.63 | TEST= 0
| INDE | 10 | 62 | 44 | FOBS= | 92.7 | SIGMA= | 3.6 | PHAS= | -43.0 | FOM= | 0.91 | TEST= 0
| INDE | 10 | 63 | 11 | FOBS= | 85.9 | SIGMA= | 4.2 | PHAS= | -141.2 | FOM= | 0.87 | TEST= 0
| INDE | 10 | 63 | 13 | FOBS= | 77.2 | SIGMA= | 4.6 | PHAS= | -155.7 | FOM= | 0.75 | TEST= 0
| INDE | 10 | 63 | 15 | FOBS= | 81.1 | SIGMA= | 4.3 | PHAS= | 73.8 | FOM= | 0.87 | TEST= 0
| INDE | 10 | 63 | 17 | FOBS= | 60.7 | SIGMA= | 3.5 | PHAS= | -179.8 | FOM= | 0.86 | TEST= 0
| INDE | 10 | 63 | 19 | FOBS= | 24.4 | SIGMA= | 10.5 | PHAS= | 151.7 | FOM= | 0.27 | TEST= 0
| INDE | 10 | 63 | 21 | FOBS= | 144.4 | SIGMA= | 1.9 | PHAS= | 84.2 | FOM= | 0.48 | TEST= 1
| INDE | 10 | 63 | 23 | FOBS= | 126.7 | SIGMA= | 2.2 | PHAS= | 134.2 | FOM= | 0.94 | TEST= 0
| INDE | 10 | 63 | 25 | FOBS= | 52.8 | SIGMA= | 5.0 | PHAS= | -21.5 | FOM= | 0.64 | TEST= 0
| INDE | 10 | 63 | 27 | FOBS= | 0.0 | SIGMA= | 23.2 | PHAS= | 0.0 | FOM= | 0.00 | TEST= 0
| INDE | 10 | 63 | 29 | FOBS= | 41.2 | SIGMA= | 6.7 | PHAS= | -91.0 | FOM= | 0.46 | TEST= 0
| INDE | 10 | 63 | 31 | FOBS= | 74.1 | SIGMA= | 3.8 | PHAS= | 20.4 | FOM= | 0.12 | TEST= 1
| INDE | 10 | 63 | 33 | FOBS= | 0.0 | SIGMA= | 26.1 | PHAS= | 0.0 | FOM= | 0.00 | TEST= 0
| INDE | 10 | 63 | 35 | FOBS= | 7.1 | SIGMA= | 49.1 | PHAS= | -140.8 | FOM= | 0.02 | TEST= 0
| INDE | 10 | 63 | 37 | FOBS= | 0.0 | SIGMA= | 23.9 | PHAS= | 0.0 | FOM= | 0.00 | TEST= 0
| INDE | 10 | 63 | 39 | FOBS= | 47.5 | SIGMA= | 6.2 | PHAS= | 106.5 | FOM= | 0.82 | TEST= 0
| INDE | 10 | 63 | 41 | FOBS= | 42.4 | SIGMA= | 8.8 | PHAS= | 36.3 | FOM= | 0.43 | TEST= 0
| INDE | 10 | 63 | 43 | FOBS= | 46.1 | SIGMA= | 6.6 | PHAS= | -130.3 | FOM= | 0.82 | TEST= 0
| INDE | 10 | 64 | 10 | FOBS= | 107.1 | SIGMA= | 3.5 | PHAS= | 91.6 | FOM= | 0.95 | TEST= 0
| INDE | 10 | 64 | 12 | FOBS= | 62.8 | SIGMA= | 5.6 | PHAS= | 65.9 | FOM= | 0.78 | TEST= 0
| INDE | 10 | 64 | 14 | FOBS= | 38.7 | SIGMA= | 8.9 | PHAS= | 104.1 | FOM= | 0.69 | TEST= 0
| INDE | 10 | 64 | 16 | FOBS= | 39.6 | SIGMA= | 8.6 | PHAS= | 122.8 | FOM= | 0.39 | TEST= 0
| INDE | 10 | 64 | 18 | FOBS= | 81.1 | SIGMA= | 2.7 | PHAS= | 130.2 | FOM= | 0.59 | TEST= 0
| INDE | 10 | 64 | 20 | FOBS= | 66.4 | SIGMA= | 3.6 | PHAS= | 120.2 | FOM= | 0.74 | TEST= 0
| INDE | 10 | 64 | 22 | FOBS= | 88.2 | SIGMA= | 2.5 | PHAS= | -42.0 | FOM= | 0.91 | TEST= 0
| INDE | 10 | 64 | 24 | FOBS= | 79.8 | SIGMA= | 3.4 | PHAS= | 83.0 | FOM= | 0.71 | TEST= 0
| INDE | 10 | 64 | 26 | FOBS= | 0.0 | SIGMA= | 23.1 | PHAS= | 0.0 | FOM= | 0.00 | TEST= 0
| INDE | 10 | 64 | 28 | FOBS= | 95.1 | SIGMA= | 3.0 | PHAS= | -146.7 | FOM= | 0.82 | TEST= 0
| INDE | 10 | 64 | 30 | FOBS= | 39.7 | SIGMA= | 8.3 | PHAS= | 19.2 | FOM= | 0.78 | TEST= 0
| INDE | 10 | 64 | 32 | FOBS= | 0.0 | SIGMA= | 23.5 | PHAS= | 0.0 | FOM= | 0.00 | TEST= 0
| INDE | 10 | 64 | 34 | FOBS= | 0.0 | SIGMA= | 23.5 | PHAS= | 0.0 | FOM= | 0.00 | TEST= 0
| INDE | 10 | 64 | 36 | FOBS= | 14.5 | SIGMA= | 24.8 | PHAS= | -66.5 | FOM= | 0.21 | TEST= 0
| INDE | 10 | 64 | 38 | FOBS= | 40.3 | SIGMA= | 7.3 | PHAS= | -11.7 | FOM= | 0.36 | TEST= 0

*FIG. 12A - 278*

```
INDE  10  64  40  FOBS=    0.0  SIGMA=  26.0  PHAS=    0.0  FOM=  0.00  TEST=  0
INDE  10  64  42  FOBS=   56.8  SIGMA=   5.3  PHAS= -166.7  FOM=  0.22  TEST=  0
INDE  10  65  11  FOBS=   79.2  SIGMA=   4.5  PHAS=  -40.5  FOM=  0.86  TEST=  0
INDE  10  65  13  FOBS=    0.0  SIGMA=  26.3  PHAS=    0.0  FOM=  0.00  TEST=  0
INDE  10  65  15  FOBS=   98.3  SIGMA=   3.6  PHAS=   57.2  FOM=  0.92  TEST=  0
INDE  10  65  17  FOBS=   71.2  SIGMA=   2.7  PHAS=   83.0  FOM=  0.72  TEST=  0
INDE  10  65  19  FOBS=   57.9  SIGMA=   3.8  PHAS=   25.5  FOM=  0.33  TEST=  0
INDE  10  65  21  FOBS=    0.0  SIGMA=  21.8  PHAS=    0.0  FOM=  0.00  TEST=  0
INDE  10  65  23  FOBS=  100.9  SIGMA=   2.2  PHAS= -179.0  FOM=  0.11  TEST=  1
INDE  10  65  25  FOBS=   75.8  SIGMA=   3.5  PHAS=  171.8  FOM=  0.36  TEST=  1
INDE  10  65  27  FOBS=    8.2  SIGMA=  40.4  PHAS=   93.1  FOM=  0.08  TEST=  0
INDE  10  65  29  FOBS=    0.0  SIGMA=  23.6  PHAS=    0.0  FOM=  0.00  TEST=  0
INDE  10  65  31  FOBS=   47.1  SIGMA=   6.0  PHAS=    2.3  FOM=  0.46  TEST=  0
INDE  10  65  33  FOBS=    0.0  SIGMA=  23.7  PHAS=    0.0  FOM=  0.00  TEST=  0
INDE  10  65  35  FOBS=   23.0  SIGMA=  12.3  PHAS=  -56.5  FOM=  0.52  TEST=  0
INDE  10  65  37  FOBS=    0.0  SIGMA=  24.1  PHAS=    0.0  FOM=  0.00  TEST=  0
INDE  10  65  39  FOBS=   47.7  SIGMA=   6.3  PHAS=   39.1  FOM=  0.75  TEST=  0
INDE  10  65  41  FOBS=    0.0  SIGMA=  26.4  PHAS=    0.0  FOM=  0.00  TEST=  0
INDE  10  66  10  FOBS=   94.5  SIGMA=   3.8  PHAS=  -78.6  FOM=  0.87  TEST=  0
INDE  10  66  12  FOBS=   28.7  SIGMA=  12.1  PHAS=  -63.1  FOM=  0.35  TEST=  0
INDE  10  66  14  FOBS=   34.9  SIGMA=  10.0  PHAS=  -11.0  FOM=  0.06  TEST=  1
INDE  10  66  16  FOBS=   35.1  SIGMA=   9.8  PHAS=  177.3  FOM=  0.37  TEST=  0
INDE  10  66  18  FOBS=   23.5  SIGMA=   8.7  PHAS= -105.0  FOM=  0.37  TEST=  0
INDE  10  66  20  FOBS=    0.0  SIGMA=  21.1  PHAS=    0.0  FOM=  0.00  TEST=  0
INDE  10  66  22  FOBS=   89.7  SIGMA=   2.8  PHAS=  133.4  FOM=  0.86  TEST=  0
INDE  10  66  24  FOBS=    0.0  SIGMA=  20.7  PHAS=    0.0  FOM=  0.00  TEST=  0
INDE  10  66  26  FOBS=    0.0  SIGMA=  23.0  PHAS=    0.0  FOM=  0.00  TEST=  0
INDE  10  66  28  FOBS=   28.7  SIGMA=   9.6  PHAS= -154.2  FOM=  0.35  TEST=  0
INDE  10  66  30  FOBS=    0.0  SIGMA=  23.7  PHAS=    0.0  FOM=  0.00  TEST=  0
INDE  10  66  32  FOBS=    0.0  SIGMA=  25.7  PHAS=    0.0  FOM=  0.00  TEST=  0
INDE  10  66  34  FOBS=   34.0  SIGMA=   9.9  PHAS=  -58.5  FOM=  0.50  TEST=  0
INDE  10  66  36  FOBS=    0.0  SIGMA=  23.9  PHAS=    0.0  FOM=  0.00  TEST=  0
INDE  10  66  38  FOBS=   59.5  SIGMA=   5.0  PHAS= -102.9  FOM=  0.74  TEST=  0
INDE  10  67  11  FOBS=   40.3  SIGMA=  12.5  PHAS=  179.6  FOM=  0.26  TEST=  0
INDE  10  67  13  FOBS=    0.0  SIGMA=  26.1  PHAS=    0.0  FOM=  0.00  TEST=  0
INDE  10  67  15  FOBS=   81.5  SIGMA=   4.4  PHAS=   94.6  FOM=  0.91  TEST=  0
INDE  10  67  17  FOBS=   95.1  SIGMA=   3.7  PHAS=  166.0  FOM=  0.82  TEST=  0
INDE  10  67  19  FOBS=    6.1  SIGMA=  38.7  PHAS=  148.4  FOM=  0.08  TEST=  0
INDE  10  67  21  FOBS=    0.0  SIGMA=  21.5  PHAS=    0.0  FOM=  0.00  TEST=  0
INDE  10  67  23  FOBS=   42.5  SIGMA=   5.8  PHAS=  -43.9  FOM=  0.59  TEST=  0
INDE  10  67  25  FOBS=    0.0  SIGMA=  20.9  PHAS=    0.0  FOM=  0.00  TEST=  0
INDE  10  67  27  FOBS=    0.0  SIGMA=  23.2  PHAS=    0.0  FOM=  0.00  TEST=  0
INDE  10  67  29  FOBS=   43.4  SIGMA=   6.5  PHAS=  131.5  FOM=  0.85  TEST=  0
INDE  10  67  31  FOBS=   48.7  SIGMA=   5.9  PHAS=  -72.1  FOM=  0.67  TEST=  0
INDE  10  67  33  FOBS=   80.1  SIGMA=   3.6  PHAS= -165.6  FOM=  0.74  TEST=  0
INDE  10  67  35  FOBS=   47.4  SIGMA=   6.1  PHAS=  -35.8  FOM=  0.44  TEST=  0
INDE  10  67  37  FOBS=   57.7  SIGMA=   5.2  PHAS=   63.5  FOM=  0.75  TEST=  0
INDE  10  68  14  FOBS=  113.2  SIGMA=   4.7  PHAS=   37.8  FOM=  0.92  TEST=  0
INDE  10  68  16  FOBS=   42.5  SIGMA=  11.8  PHAS=   68.5  FOM=  0.66  TEST=  0
INDE  10  68  18  FOBS=   58.9  SIGMA=   5.9  PHAS=  117.8  FOM=  0.82  TEST=  0
INDE  10  68  20  FOBS=   73.9  SIGMA=   3.1  PHAS= -104.0  FOM=  0.84  TEST=  0
INDE  10  68  22  FOBS=   82.3  SIGMA=   2.9  PHAS=  156.6  FOM=  0.88  TEST=  0
INDE  10  68  24  FOBS=    0.0  SIGMA=  25.9  PHAS=    0.0  FOM=  0.00  TEST=  0
INDE  10  68  26  FOBS=    0.0  SIGMA=  22.5  PHAS=    0.0  FOM=  0.00  TEST=  0
INDE  10  68  28  FOBS=   74.9  SIGMA=   3.8  PHAS=   16.4  FOM=  0.93  TEST=  0
INDE  10  68  30  FOBS=   28.5  SIGMA=  10.0  PHAS=  -65.5  FOM=  0.50  TEST=  0
INDE  10  68  32  FOBS=    0.0  SIGMA=  27.0  PHAS=    0.0  FOM=  0.00  TEST=  0
INDE  10  68  34  FOBS=   32.9  SIGMA=  10.4  PHAS=  -64.8  FOM=  0.10  TEST=  1
INDE  10  68  36  FOBS=    0.0  SIGMA=  27.2  PHAS=    0.0  FOM=  0.00  TEST=  0
INDE  10  69  19  FOBS=   49.1  SIGMA=   4.5  PHAS=  127.4  FOM=  0.27  TEST=  1
INDE  10  69  21  FOBS=    0.0  SIGMA=  22.9  PHAS=    0.0  FOM=  0.00  TEST=  0
INDE  10  69  23  FOBS=   38.2  SIGMA=   7.2  PHAS= -126.8  FOM=  0.54  TEST=  0
INDE  10  69  25  FOBS=    0.0  SIGMA=  25.1  PHAS=    0.0  FOM=  0.00  TEST=  1
INDE  10  69  27  FOBS=   91.2  SIGMA=   2.6  PHAS=  -47.7  FOM=  0.89  TEST=  0
INDE  10  69  29  FOBS=    0.0  SIGMA=  26.2  PHAS=    0.0  FOM=  0.00  TEST=  0
INDE  10  69  31  FOBS=    0.0  SIGMA=  26.9  PHAS=    0.0  FOM=  0.00  TEST=  0
INDE  10  69  33  FOBS=   35.6  SIGMA=  10.6  PHAS=  -18.8  FOM=  0.34  TEST=  0
INDE  10  70  20  FOBS=   84.3  SIGMA=   3.3  PHAS=    5.2  FOM=  0.61  TEST=  0
INDE  10  70  22  FOBS=   33.6  SIGMA=   9.7  PHAS=  174.7  FOM=  0.25  TEST=  0
INDE  10  70  24  FOBS=   47.3  SIGMA=   6.0  PHAS=  129.9  FOM=  0.69  TEST=  0
```

*FIG. 12A - 279*

```
INDE 10 70 26 FOBS=  94.8 SIGMA=  3.5 PHAS= -120.1 FOM= 0.89 TEST= 0
INDE 10 70 28 FOBS=   0.0 SIGMA= 21.6 PHAS=    0.0 FOM= 0.00 TEST= 0
INDE 10 70 30 FOBS=  73.2 SIGMA=  4.0 PHAS=   -0.5 FOM= 0.85 TEST= 0
INDE 10 70 32 FOBS= 101.3 SIGMA=  3.1 PHAS= -114.6 FOM= 0.86 TEST= 0
INDE 10 71 21 FOBS=  24.9 SIGMA= 11.4 PHAS= -125.4 FOM= 0.44 TEST= 0
INDE 10 71 23 FOBS=  49.2 SIGMA=  6.8 PHAS=   52.7 FOM= 0.04 TEST= 1
INDE 10 71 25 FOBS=  39.0 SIGMA=  9.5 PHAS=  142.2 FOM= 0.79 TEST= 0
INDE 10 71 27 FOBS=  25.7 SIGMA= 17.2 PHAS=  -46.6 FOM= 0.03 TEST= 1
INDE 10 71 29 FOBS=  72.2 SIGMA=  3.9 PHAS=  -26.5 FOM= 0.53 TEST= 0
INDE 10 72 22 FOBS=  10.3 SIGMA= 29.8 PHAS=  -49.5 FOM= 0.12 TEST= 0
INDE 10 72 24 FOBS=  40.9 SIGMA=  8.5 PHAS=  125.2 FOM= 0.43 TEST= 0
INDE 10 72 26 FOBS=  67.2 SIGMA=  6.0 PHAS=   92.3 FOM= 0.76 TEST= 0
INDE 10 73 23 FOBS=  61.6 SIGMA=  5.4 PHAS=  170.5 FOM= 0.69 TEST= 0
INDE 10 75 15 FOBS=  30.9 SIGMA=  7.7 PHAS=  -98.0 FOM= 0.23 TEST= 0
INDE 11 12 11 FOBS= 275.4 SIGMA=  0.5 PHAS=  -60.2 FOM= 0.93 TEST= 0
INDE 11 12 13 FOBS=  24.2 SIGMA=  2.1 PHAS=  -99.6 FOM= 0.14 TEST= 0
INDE 11 12 15 FOBS=  47.5 SIGMA=  1.2 PHAS=  -91.3 FOM= 0.91 TEST= 0
INDE 11 12 17 FOBS= 151.2 SIGMA=  0.5 PHAS=  -57.9 FOM= 0.93 TEST= 0
INDE 11 12 19 FOBS= 133.2 SIGMA=  0.5 PHAS=   31.4 FOM= 0.83 TEST= 0
INDE 11 12 21 FOBS= 117.9 SIGMA=  0.6 PHAS=    3.5 FOM= 0.87 TEST= 0
INDE 11 12 23 FOBS= 241.0 SIGMA=  0.4 PHAS= -129.8 FOM= 0.99 TEST= 0
INDE 11 12 25 FOBS=  43.6 SIGMA=  1.6 PHAS=  -48.6 FOM= 0.97 TEST= 0
INDE 11 12 27 FOBS= 216.9 SIGMA=  0.5 PHAS=   31.0 FOM= 0.98 TEST= 0
INDE 11 12 29 FOBS=  67.8 SIGMA=  1.1 PHAS=  -48.1 FOM= 0.92 TEST= 0
INDE 11 12 31 FOBS= 131.4 SIGMA=  0.7 PHAS=  -52.4 FOM= 0.98 TEST= 0
INDE 11 12 33 FOBS=  33.0 SIGMA=  2.8 PHAS=  -20.3 FOM= 0.98 TEST= 1
INDE 11 12 35 FOBS=   0.0 SIGMA= 14.9 PHAS=    0.0 FOM= 0.00 TEST= 0
INDE 11 12 37 FOBS=  30.7 SIGMA=  4.4 PHAS= -141.1 FOM= 0.82 TEST= 0
INDE 11 12 39 FOBS= 198.0 SIGMA=  1.2 PHAS=  120.7 FOM= 0.96 TEST= 0
INDE 11 12 41 FOBS= 404.2 SIGMA=  0.8 PHAS= -129.8 FOM= 0.97 TEST= 0
INDE 11 12 43 FOBS= 109.5 SIGMA=  1.8 PHAS= -168.8 FOM= 0.90 TEST= 0
INDE 11 12 45 FOBS= 252.0 SIGMA=  1.0 PHAS=  171.8 FOM= 0.96 TEST= 0
INDE 11 12 47 FOBS= 259.9 SIGMA=  1.0 PHAS=   87.8 FOM= 0.96 TEST= 0
INDE 11 12 49 FOBS=  88.1 SIGMA=  2.4 PHAS=   25.7 FOM= 0.65 TEST= 0
INDE 11 12 51 FOBS=  33.2 SIGMA=  4.3 PHAS=   87.4 FOM= 0.05 TEST= 0
INDE 11 12 53 FOBS=  49.9 SIGMA=  3.9 PHAS=  156.6 FOM= 0.68 TEST= 0
INDE 11 12 55 FOBS=  76.7 SIGMA=  2.1 PHAS=   23.9 FOM= 0.92 TEST= 0
INDE 11 12 57 FOBS=  96.5 SIGMA=  1.6 PHAS=   21.1 FOM= 0.93 TEST= 0
INDE 11 12 59 FOBS= 182.1 SIGMA=  1.1 PHAS=   17.5 FOM= 0.95 TEST= 0
INDE 11 12 61 FOBS= 100.2 SIGMA=  1.8 PHAS=  102.4 FOM= 0.92 TEST= 0
INDE 11 12 63 FOBS=   0.0 SIGMA= 26.3 PHAS=    0.0 FOM= 0.00 TEST= 0
INDE 11 12 65 FOBS=  70.7 SIGMA=  5.0 PHAS=   68.3 FOM= 0.62 TEST= 0
INDE 11 12 67 FOBS=  75.7 SIGMA=  6.7 PHAS=   88.1 FOM= 0.61 TEST= 0
INDE 11 13 12 FOBS= 140.7 SIGMA=  0.5 PHAS= -126.3 FOM= 0.94 TEST= 0
INDE 11 13 14 FOBS= 112.8 SIGMA=  0.7 PHAS=  162.6 FOM= 0.42 TEST= 0
INDE 11 13 16 FOBS= 123.8 SIGMA=  0.6 PHAS=  -94.5 FOM= 0.76 TEST= 0
INDE 11 13 18 FOBS= 238.1 SIGMA=  0.5 PHAS=  -97.4 FOM= 0.94 TEST= 0
INDE 11 13 20 FOBS=  27.5 SIGMA=  2.2 PHAS=   95.6 FOM= 0.90 TEST= 0
INDE 11 13 22 FOBS= 226.1 SIGMA=  0.4 PHAS=   96.0 FOM= 0.98 TEST= 0
INDE 11 13 24 FOBS= 139.2 SIGMA=  0.6 PHAS= -105.3 FOM= 0.94 TEST= 0
INDE 11 13 26 FOBS=  54.3 SIGMA=  1.3 PHAS= -100.4 FOM= 0.98 TEST= 0
INDE 11 13 28 FOBS=  84.8 SIGMA=  0.9 PHAS=  146.8 FOM= 0.96 TEST= 0
INDE 11 13 30 FOBS= 196.7 SIGMA=  0.5 PHAS=  142.5 FOM= 0.98 TEST= 0
INDE 11 13 32 FOBS=  26.9 SIGMA=  3.3 PHAS=   81.4 FOM= 0.90 TEST= 0
INDE 11 13 34 FOBS= 103.6 SIGMA=  1.0 PHAS=   26.4 FOM= 0.86 TEST= 0
INDE 11 13 36 FOBS= 126.8 SIGMA=  1.0 PHAS=   -0.4 FOM= 0.35 TEST= 0
INDE 11 13 38 FOBS= 292.7 SIGMA=  0.9 PHAS=  -81.6 FOM= 0.98 TEST= 0
INDE 11 13 40 FOBS= 225.1 SIGMA=  1.2 PHAS=  110.2 FOM= 0.95 TEST= 0
INDE 11 13 42 FOBS= 348.3 SIGMA=  0.7 PHAS=  126.5 FOM= 0.99 TEST= 0
INDE 11 13 44 FOBS=  40.6 SIGMA=  5.1 PHAS=  139.7 FOM= 0.89 TEST= 0
INDE 11 13 46 FOBS= 321.5 SIGMA=  0.8 PHAS=   47.9 FOM= 0.96 TEST= 0
INDE 11 13 48 FOBS= 152.3 SIGMA=  1.2 PHAS=    8.0 FOM= 0.91 TEST= 0
INDE 11 13 50 FOBS=  23.0 SIGMA=  8.0 PHAS=  -77.9 FOM= 0.41 TEST= 0
INDE 11 13 52 FOBS= 101.4 SIGMA=  1.5 PHAS=  140.4 FOM= 0.74 TEST= 0
INDE 11 13 54 FOBS=  97.3 SIGMA=  1.5 PHAS=   -6.5 FOM= 0.83 TEST= 0
INDE 11 13 56 FOBS= 134.7 SIGMA=  1.5 PHAS=  -98.3 FOM= 0.96 TEST= 0
INDE 11 13 58 FOBS= 145.4 SIGMA=  1.3 PHAS=  -37.8 FOM= 0.91 TEST= 0
INDE 11 13 60 FOBS=  69.7 SIGMA=  2.6 PHAS=   58.7 FOM= 0.15 TEST= 0
INDE 11 13 62 FOBS=  38.9 SIGMA=  6.3 PHAS= -167.9 FOM= 0.47 TEST= 1
INDE 11 13 64 FOBS=   0.0 SIGMA= 26.2 PHAS=    0.0 FOM= 0.00 TEST= 0
```

*FIG. 12A - 280*

```
INDE 11 13 66 FOBS=   66.2 SIGMA=  5.2 PHAS= -147.5 FOM= 0.68 TEST= 0
INDE 11 14 11 FOBS=  161.7 SIGMA=  0.5 PHAS=  111.9 FOM= 0.97 TEST= 0
INDE 11 14 13 FOBS=  206.7 SIGMA=  0.5 PHAS= -135.9 FOM= 0.88 TEST= 0
INDE 11 14 15 FOBS=  252.5 SIGMA=  0.5 PHAS=  162.5 FOM= 0.93 TEST= 0
INDE 11 14 17 FOBS=  185.0 SIGMA=  0.4 PHAS=  159.5 FOM= 0.99 TEST= 0
INDE 11 14 19 FOBS=   71.1 SIGMA=  0.9 PHAS= -142.8 FOM= 0.96 TEST= 0
INDE 11 14 21 FOBS=  319.6 SIGMA=  0.4 PHAS=   16.2 FOM= 0.99 TEST= 0
INDE 11 14 23 FOBS=   50.2 SIGMA=  1.3 PHAS=   44.7 FOM= 0.82 TEST= 0
INDE 11 14 25 FOBS=  137.0 SIGMA=  0.6 PHAS=   99.4 FOM= 0.96 TEST= 0
INDE 11 14 27 FOBS=  167.6 SIGMA=  0.5 PHAS=   23.1 FOM= 0.94 TEST= 0
INDE 11 14 29 FOBS=   80.6 SIGMA=  1.0 PHAS=  117.0 FOM= 0.09 TEST= 0
INDE 11 14 31 FOBS=  118.4 SIGMA=  0.8 PHAS=  -10.0 FOM= 0.99 TEST= 0
INDE 11 14 33 FOBS=   66.6 SIGMA=  1.4 PHAS=   53.4 FOM= 0.93 TEST= 0
INDE 11 14 35 FOBS=  288.0 SIGMA=  0.6 PHAS= -104.2 FOM= 0.95 TEST= 0
INDE 11 14 37 FOBS=  339.7 SIGMA=  0.7 PHAS= -164.7 FOM= 0.97 TEST= 0
INDE 11 14 39 FOBS=  135.3 SIGMA=  1.1 PHAS=  126.1 FOM= 0.96 TEST= 0
INDE 11 14 41 FOBS=  258.5 SIGMA=  0.8 PHAS=   -2.8 FOM= 0.89 TEST= 1
INDE 11 14 43 FOBS=  157.1 SIGMA=  1.1 PHAS=  114.3 FOM= 0.98 TEST= 0
INDE 11 14 45 FOBS=  101.6 SIGMA=  1.6 PHAS=    4.4 FOM= 0.38 TEST= 1
INDE 11 14 47 FOBS=  172.6 SIGMA=  1.0 PHAS=    0.6 FOM= 0.97 TEST= 0
INDE 11 14 49 FOBS=  195.1 SIGMA=  0.9 PHAS=  169.3 FOM= 0.66 TEST= 1
INDE 11 14 51 FOBS=  222.1 SIGMA=  0.8 PHAS=  113.3 FOM= 0.97 TEST= 0
INDE 11 14 53 FOBS=    0.0 SIGMA= 18.1 PHAS=    0.0 FOM= 0.00 TEST= 1
INDE 11 14 55 FOBS=   57.8 SIGMA=  2.5 PHAS=   53.7 FOM= 0.90 TEST= 0
INDE 11 14 57 FOBS=   93.4 SIGMA=  1.5 PHAS=  107.9 FOM= 0.90 TEST= 0
INDE 11 14 59 FOBS=  100.2 SIGMA=  1.9 PHAS=   84.0 FOM= 0.86 TEST= 0
INDE 11 14 61 FOBS=  129.7 SIGMA=  2.1 PHAS=   74.2 FOM= 0.97 TEST= 0
INDE 11 14 63 FOBS=    0.0 SIGMA= 26.2 PHAS=    0.0 FOM= 0.00 TEST= 0
INDE 11 14 65 FOBS=   70.6 SIGMA=  4.9 PHAS=  166.5 FOM= 0.87 TEST= 0
INDE 11 15 12 FOBS=  260.8 SIGMA=  0.4 PHAS=   -3.4 FOM= 0.93 TEST= 0
INDE 11 15 14 FOBS=  264.4 SIGMA=  0.4 PHAS=  110.0 FOM= 0.94 TEST= 0
INDE 11 15 16 FOBS=  158.6 SIGMA=  0.6 PHAS=   70.4 FOM= 0.96 TEST= 0
INDE 11 15 18 FOBS=  126.5 SIGMA=  0.5 PHAS=   46.8 FOM= 0.96 TEST= 0
INDE 11 15 20 FOBS=   80.8 SIGMA=  0.8 PHAS=  -59.0 FOM= 0.96 TEST= 0
INDE 11 15 22 FOBS=  180.6 SIGMA=  0.5 PHAS= -139.2 FOM= 0.99 TEST= 0
INDE 11 15 24 FOBS=  206.5 SIGMA=  0.4 PHAS=   -8.0 FOM= 0.97 TEST= 0
INDE 11 15 26 FOBS=  220.5 SIGMA=  0.4 PHAS=  -16.7 FOM= 0.98 TEST= 0
INDE 11 15 28 FOBS=  166.9 SIGMA=  0.5 PHAS= -117.9 FOM= 0.99 TEST= 0
INDE 11 15 30 FOBS=   53.7 SIGMA=  1.4 PHAS=  162.5 FOM= 0.78 TEST= 0
INDE 11 15 32 FOBS=  227.6 SIGMA=  0.5 PHAS=  -83.9 FOM= 0.92 TEST= 0
INDE 11 15 34 FOBS=   71.0 SIGMA=  1.3 PHAS=  107.7 FOM= 0.91 TEST= 0
INDE 11 15 36 FOBS=  219.4 SIGMA=  0.6 PHAS=  157.7 FOM= 0.92 TEST= 1
INDE 11 15 38 FOBS=  204.9 SIGMA=  0.7 PHAS=  107.4 FOM= 0.91 TEST= 0
INDE 11 15 40 FOBS=  100.2 SIGMA=  1.4 PHAS=   95.9 FOM= 0.68 TEST= 1
INDE 11 15 42 FOBS=  123.8 SIGMA=  1.3 PHAS= -127.4 FOM= 0.91 TEST= 0
INDE 11 15 44 FOBS=   58.7 SIGMA=  2.8 PHAS=  -23.6 FOM= 0.88 TEST= 1
INDE 11 15 46 FOBS=  241.6 SIGMA=  0.9 PHAS=  -80.8 FOM= 0.92 TEST= 0
INDE 11 15 48 FOBS=  115.9 SIGMA=  1.4 PHAS=  -19.3 FOM= 0.81 TEST= 1
INDE 11 15 50 FOBS=  260.8 SIGMA=  0.8 PHAS=   36.3 FOM= 0.96 TEST= 0
INDE 11 15 52 FOBS=   26.0 SIGMA=  5.7 PHAS=   28.6 FOM= 0.57 TEST= 0
INDE 11 15 54 FOBS=  103.4 SIGMA=  1.4 PHAS=   23.0 FOM= 0.86 TEST= 0
INDE 11 15 56 FOBS=   75.4 SIGMA=  1.9 PHAS=  -18.8 FOM= 0.89 TEST= 0
INDE 11 15 58 FOBS=   69.1 SIGMA=  2.3 PHAS=  -33.1 FOM= 0.88 TEST= 0
INDE 11 15 60 FOBS=   93.4 SIGMA=  2.2 PHAS=   -4.6 FOM= 0.93 TEST= 0
INDE 11 15 62 FOBS=   54.2 SIGMA=  6.5 PHAS=  -45.3 FOM= 0.85 TEST= 0
INDE 11 15 64 FOBS=    0.0 SIGMA= 26.0 PHAS=    0.0 FOM= 0.00 TEST= 0
INDE 11 15 66 FOBS=   37.2 SIGMA= 13.3 PHAS=  161.9 FOM= 0.22 TEST= 0
INDE 11 16 11 FOBS=   98.3 SIGMA=  0.6 PHAS=  -30.8 FOM= 0.91 TEST= 0
INDE 11 16 13 FOBS=  291.4 SIGMA=  0.4 PHAS=  -75.4 FOM= 0.93 TEST= 0
INDE 11 16 15 FOBS=  166.6 SIGMA=  0.5 PHAS=   -7.9 FOM= 0.91 TEST= 0
INDE 11 16 17 FOBS=   68.9 SIGMA=  1.1 PHAS= -169.1 FOM= 0.98 TEST= 0
INDE 11 16 19 FOBS=  198.1 SIGMA=  0.4 PHAS=  -10.2 FOM= 0.98 TEST= 0
INDE 11 16 21 FOBS=  186.5 SIGMA=  0.5 PHAS=   76.7 FOM= 0.98 TEST= 0
INDE 11 16 23 FOBS=  136.0 SIGMA=  0.6 PHAS= -125.8 FOM= 0.75 TEST= 0
INDE 11 16 25 FOBS=  118.2 SIGMA=  0.6 PHAS=   93.6 FOM= 0.84 TEST= 0
INDE 11 16 27 FOBS=  278.7 SIGMA=  0.4 PHAS=  175.3 FOM= 0.98 TEST= 1
INDE 11 16 29 FOBS=   29.2 SIGMA=  2.5 PHAS=  -46.6 FOM= 0.45 TEST= 0
INDE 11 16 31 FOBS=  188.5 SIGMA=  0.5 PHAS= -156.6 FOM= 0.94 TEST= 0
INDE 11 16 33 FOBS=  216.0 SIGMA=  0.5 PHAS=  156.5 FOM= 0.98 TEST= 0
INDE 11 16 35 FOBS=    0.0 SIGMA= 14.3 PHAS=    0.0 FOM= 0.00 TEST= 0
```

*FIG. 12A - 281*

| | | | | | | | | | | | |
|---|---|---|---|---|---|---|---|---|---|---|---|
| INDE | 11 | 16 | 37 | FOBS= | 137.2 | SIGMA= | 0.9 | PHAS= | 60.8 | FOM= | 0.97 | TEST= 0
| INDE | 11 | 16 | 39 | FOBS= | 144.2 | SIGMA= | 0.9 | PHAS= | -102.5 | FOM= | 0.87 | TEST= 0
| INDE | 11 | 16 | 41 | FOBS= | 106.6 | SIGMA= | 1.3 | PHAS= | 154.7 | FOM= | 0.84 | TEST= 0
| INDE | 11 | 16 | 43 | FOBS= | 65.6 | SIGMA= | 2.4 | PHAS= | 164.1 | FOM= | 0.94 | TEST= 0
| INDE | 11 | 16 | 45 | FOBS= | 239.5 | SIGMA= | 0.8 | PHAS= | 170.0 | FOM= | 0.96 | TEST= 0
| INDE | 11 | 16 | 47 | FOBS= | 101.1 | SIGMA= | 1.7 | PHAS= | -152.5 | FOM= | 0.78 | TEST= 0
| INDE | 11 | 16 | 49 | FOBS= | 90.2 | SIGMA= | 1.8 | PHAS= | 40.6 | FOM= | 0.92 | TEST= 0
| INDE | 11 | 16 | 51 | FOBS= | 43.6 | SIGMA= | 3.5 | PHAS= | -151.8 | FOM= | 0.62 | TEST= 0
| INDE | 11 | 16 | 53 | FOBS= | 59.0 | SIGMA= | 2.5 | PHAS= | -18.3 | FOM= | 0.54 | TEST= 0
| INDE | 11 | 16 | 55 | FOBS= | 160.0 | SIGMA= | 0.9 | PHAS= | -62.5 | FOM= | 0.95 | TEST= 0
| INDE | 11 | 16 | 57 | FOBS= | 50.8 | SIGMA= | 3.2 | PHAS= | -88.6 | FOM= | 0.65 | TEST= 0
| INDE | 11 | 16 | 59 | FOBS= | 116.9 | SIGMA= | 1.8 | PHAS= | 141.3 | FOM= | 0.93 | TEST= 0
| INDE | 11 | 16 | 61 | FOBS= | 36.1 | SIGMA= | 5.4 | PHAS= | -171.4 | FOM= | 0.13 | TEST= 1
| INDE | 11 | 16 | 63 | FOBS= | 0.0 | SIGMA= | 23.4 | PHAS= | 0.0 | FOM= | 0.00 | TEST= 0
| INDE | 11 | 16 | 65 | FOBS= | 0.0 | SIGMA= | 26.2 | PHAS= | 0.0 | FOM= | 0.00 | TEST= 0
| INDE | 11 | 17 | 12 | FOBS= | 153.4 | SIGMA= | 0.6 | PHAS= | -125.3 | FOM= | 0.94 | TEST= 0
| INDE | 11 | 17 | 14 | FOBS= | 157.7 | SIGMA= | 0.5 | PHAS= | -120.7 | FOM= | 0.80 | TEST= 0
| INDE | 11 | 17 | 16 | FOBS= | 33.7 | SIGMA= | 1.9 | PHAS= | -133.2 | FOM= | 0.23 | TEST= 0
| INDE | 11 | 17 | 18 | FOBS= | 68.5 | SIGMA= | 1.1 | PHAS= | -109.6 | FOM= | 0.84 | TEST= 1
| INDE | 11 | 17 | 20 | FOBS= | 247.6 | SIGMA= | 0.4 | PHAS= | -13.7 | FOM= | 0.94 | TEST= 0
| INDE | 11 | 17 | 22 | FOBS= | 54.9 | SIGMA= | 1.3 | PHAS= | -31.0 | FOM= | 0.95 | TEST= 0
| INDE | 11 | 17 | 24 | FOBS= | 222.3 | SIGMA= | 0.5 | PHAS= | -46.3 | FOM= | 0.99 | TEST= 0
| INDE | 11 | 17 | 26 | FOBS= | 105.1 | SIGMA= | 0.7 | PHAS= | 64.9 | FOM= | 0.95 | TEST= 0
| INDE | 11 | 17 | 28 | FOBS= | 84.3 | SIGMA= | 0.9 | PHAS= | 96.8 | FOM= | 0.37 | TEST= 0
| INDE | 11 | 17 | 30 | FOBS= | 77.1 | SIGMA= | 1.0 | PHAS= | -174.4 | FOM= | 0.75 | TEST= 0
| INDE | 11 | 17 | 32 | FOBS= | 56.2 | SIGMA= | 1.6 | PHAS= | -146.1 | FOM= | 0.98 | TEST= 1
| INDE | 11 | 17 | 34 | FOBS= | 107.5 | SIGMA= | 1.0 | PHAS= | 17.8 | FOM= | 0.60 | TEST= 0
| INDE | 11 | 17 | 36 | FOBS= | 93.4 | SIGMA= | 1.2 | PHAS= | -175.6 | FOM= | 0.87 | TEST= 0
| INDE | 11 | 17 | 38 | FOBS= | 255.8 | SIGMA= | 0.6 | PHAS= | 95.4 | FOM= | 0.96 | TEST= 0
| INDE | 11 | 17 | 40 | FOBS= | 143.2 | SIGMA= | 0.9 | PHAS= | 100.8 | FOM= | 0.92 | TEST= 1
| INDE | 11 | 17 | 42 | FOBS= | 111.5 | SIGMA= | 1.3 | PHAS= | 53.4 | FOM= | 0.87 | TEST= 0
| INDE | 11 | 17 | 44 | FOBS= | 228.0 | SIGMA= | 0.8 | PHAS= | 66.0 | FOM= | 0.95 | TEST= 0
| INDE | 11 | 17 | 46 | FOBS= | 0.0 | SIGMA= | 18.1 | PHAS= | 0.0 | FOM= | 0.00 | TEST= 0
| INDE | 11 | 17 | 48 | FOBS= | 115.8 | SIGMA= | 1.4 | PHAS= | 107.9 | FOM= | 0.88 | TEST= 0
| INDE | 11 | 17 | 50 | FOBS= | 96.0 | SIGMA= | 1.7 | PHAS= | -31.1 | FOM= | 0.91 | TEST= 0
| INDE | 11 | 17 | 52 | FOBS= | 51.3 | SIGMA= | 2.9 | PHAS= | 128.0 | FOM= | 0.74 | TEST= 0
| INDE | 11 | 17 | 54 | FOBS= | 168.1 | SIGMA= | 1.1 | PHAS= | 170.5 | FOM= | 0.93 | TEST= 0
| INDE | 11 | 17 | 56 | FOBS= | 134.2 | SIGMA= | 1.1 | PHAS= | -123.0 | FOM= | 0.92 | TEST= 0
| INDE | 11 | 17 | 58 | FOBS= | 103.2 | SIGMA= | 2.0 | PHAS= | -95.1 | FOM= | 0.81 | TEST= 0
| INDE | 11 | 17 | 60 | FOBS= | 139.1 | SIGMA= | 1.5 | PHAS= | 1.3 | FOM= | 0.96 | TEST= 0
| INDE | 11 | 17 | 62 | FOBS= | 51.2 | SIGMA= | 4.6 | PHAS= | 127.6 | FOM= | 0.80 | TEST= 0
| INDE | 11 | 17 | 64 | FOBS= | 85.9 | SIGMA= | 3.3 | PHAS= | -146.8 | FOM= | 0.89 | TEST= 0
| INDE | 11 | 17 | 66 | FOBS= | 29.3 | SIGMA= | 15.9 | PHAS= | -162.1 | FOM= | 0.52 | TEST= 0
| INDE | 11 | 18 | 11 | FOBS= | 170.7 | SIGMA= | 0.4 | PHAS= | -137.9 | FOM= | 0.87 | TEST= 0
| INDE | 11 | 18 | 13 | FOBS= | 20.8 | SIGMA= | 2.9 | PHAS= | -126.5 | FOM= | 0.88 | TEST= 0
| INDE | 11 | 18 | 15 | FOBS= | 108.8 | SIGMA= | 0.8 | PHAS= | 53.8 | FOM= | 0.97 | TEST= 0
| INDE | 11 | 18 | 17 | FOBS= | 134.5 | SIGMA= | 0.6 | PHAS= | 128.4 | FOM= | 0.96 | TEST= 0
| INDE | 11 | 18 | 19 | FOBS= | 23.8 | SIGMA= | 3.0 | PHAS= | -151.7 | FOM= | 0.69 | TEST= 0
| INDE | 11 | 18 | 21 | FOBS= | 74.9 | SIGMA= | 1.0 | PHAS= | 102.2 | FOM= | 0.63 | TEST= 0
| INDE | 11 | 18 | 23 | FOBS= | 291.9 | SIGMA= | 0.4 | PHAS= | -97.9 | FOM= | 0.96 | TEST= 0
| INDE | 11 | 18 | 25 | FOBS= | 22.0 | SIGMA= | 4.2 | PHAS= | 47.9 | FOM= | 0.44 | TEST= 0
| INDE | 11 | 18 | 27 | FOBS= | 95.4 | SIGMA= | 0.9 | PHAS= | -25.1 | FOM= | 0.99 | TEST= 0
| INDE | 11 | 18 | 29 | FOBS= | 69.5 | SIGMA= | 1.1 | PHAS= | -94.1 | FOM= | 0.58 | TEST= 0
| INDE | 11 | 18 | 31 | FOBS= | 342.0 | SIGMA= | 0.5 | PHAS= | -175.8 | FOM= | 0.99 | TEST= 0
| INDE | 11 | 18 | 33 | FOBS= | 144.2 | SIGMA= | 0.7 | PHAS= | 157.9 | FOM= | 0.96 | TEST= 0
| INDE | 11 | 18 | 35 | FOBS= | 262.3 | SIGMA= | 0.5 | PHAS= | -168.6 | FOM= | 0.94 | TEST= 0
| INDE | 11 | 18 | 37 | FOBS= | 244.6 | SIGMA= | 0.6 | PHAS= | 22.0 | FOM= | 0.91 | TEST= 0
| INDE | 11 | 18 | 39 | FOBS= | 238.9 | SIGMA= | 0.7 | PHAS= | -27.3 | FOM= | 0.97 | TEST= 0
| INDE | 11 | 18 | 41 | FOBS= | 182.1 | SIGMA= | 0.8 | PHAS= | 93.6 | FOM= | 0.93 | TEST= 0
| INDE | 11 | 18 | 43 | FOBS= | 216.1 | SIGMA= | 0.8 | PHAS= | -8.0 | FOM= | 0.96 | TEST= 0
| INDE | 11 | 18 | 45 | FOBS= | 41.6 | SIGMA= | 2.7 | PHAS= | -86.0 | FOM= | 0.68 | TEST= 0
| INDE | 11 | 18 | 47 | FOBS= | 144.3 | SIGMA= | 1.2 | PHAS= | -138.1 | FOM= | 0.61 | TEST= 1
| INDE | 11 | 18 | 49 | FOBS= | 210.6 | SIGMA= | 0.8 | PHAS= | 73.7 | FOM= | 0.96 | TEST= 0
| INDE | 11 | 18 | 51 | FOBS= | 33.2 | SIGMA= | 5.0 | PHAS= | -83.1 | FOM= | 0.18 | TEST= 0
| INDE | 11 | 18 | 53 | FOBS= | 118.7 | SIGMA= | 1.5 | PHAS= | 134.3 | FOM= | 0.95 | TEST= 0
| INDE | 11 | 18 | 55 | FOBS= | 146.8 | SIGMA= | 1.0 | PHAS= | 112.3 | FOM= | 0.94 | TEST= 0
| INDE | 11 | 18 | 57 | FOBS= | 143.9 | SIGMA= | 1.5 | PHAS= | 120.6 | FOM= | 0.94 | TEST= 0
| INDE | 11 | 18 | 59 | FOBS= | 66.4 | SIGMA= | 3.1 | PHAS= | -119.9 | FOM= | 0.77 | TEST= 0
| INDE | 11 | 18 | 61 | FOBS= | 26.4 | SIGMA= | 10.6 | PHAS= | -52.5 | FOM= | 0.51 | TEST= 0
| INDE | 11 | 18 | 63 | FOBS= | 136.0 | SIGMA= | 1.9 | PHAS= | 84.7 | FOM= | 0.93 | TEST= 0

*FIG. 12A - 282*

```
INDE  11  18  65  FOBS=   71.1  SIGMA=   4.9  PHAS=   77.5  FOM=  0.88  TEST= 0
INDE  11  18  67  FOBS=  100.3  SIGMA=   4.8  PHAS=  134.4  FOM=  0.92  TEST= 0
INDE  11  18  69  FOBS=   31.3  SIGMA=  15.3  PHAS=   -1.3  FOM=  0.48  TEST= 0
INDE  11  19  12  FOBS=  148.7  SIGMA=   0.5  PHAS= -144.1  FOM=  0.93  TEST= 0
INDE  11  19  14  FOBS=  221.6  SIGMA=   0.4  PHAS=   10.7  FOM=  0.93  TEST= 0
INDE  11  19  16  FOBS=   70.2  SIGMA=   1.1  PHAS=   87.8  FOM=  0.90  TEST= 0
INDE  11  19  18  FOBS=  125.7  SIGMA=   0.7  PHAS=  -78.0  FOM=  0.96  TEST= 0
INDE  11  19  20  FOBS=  135.3  SIGMA=   0.6  PHAS=  -48.7  FOM=  0.99  TEST= 0
INDE  11  19  22  FOBS=   78.1  SIGMA=   1.0  PHAS=  114.0  FOM=  0.94  TEST= 0
INDE  11  19  24  FOBS=   35.0  SIGMA=   2.1  PHAS= -111.2  FOM=  0.97  TEST= 0
INDE  11  19  26  FOBS=  159.6  SIGMA=   0.6  PHAS=  122.9  FOM=  0.92  TEST= 0
INDE  11  19  28  FOBS=  167.9  SIGMA=   0.6  PHAS=  138.6  FOM=  0.94  TEST= 0
INDE  11  19  30  FOBS=   89.0  SIGMA=   1.0  PHAS=   20.7  FOM=  0.99  TEST= 0
INDE  11  19  32  FOBS=  154.5  SIGMA=   0.7  PHAS=   92.5  FOM=  0.85  TEST= 0
INDE  11  19  34  FOBS=  242.6  SIGMA=   0.5  PHAS=  165.1  FOM=  0.94  TEST= 0
INDE  11  19  36  FOBS=  129.5  SIGMA=   0.9  PHAS=   33.2  FOM=  0.90  TEST= 0
INDE  11  19  38  FOBS=   40.3  SIGMA=   3.0  PHAS=   98.7  FOM=  0.83  TEST= 0
INDE  11  19  40  FOBS=  258.6  SIGMA=   0.7  PHAS=  -76.9  FOM=  0.93  TEST= 0
INDE  11  19  42  FOBS=  263.1  SIGMA=   0.7  PHAS=  -24.1  FOM=  0.92  TEST= 0
INDE  11  19  44  FOBS=   45.9  SIGMA=   3.6  PHAS=  149.3  FOM=  0.74  TEST= 0
INDE  11  19  46  FOBS=  196.6  SIGMA=   0.9  PHAS=  -85.5  FOM=  0.86  TEST= 0
INDE  11  19  48  FOBS=   33.3  SIGMA=   5.0  PHAS=   60.8  FOM=  0.29  TEST= 1
INDE  11  19  50  FOBS=   76.4  SIGMA=   2.1  PHAS=  -58.4  FOM=  0.85  TEST= 0
INDE  11  19  52  FOBS=   37.4  SIGMA=   4.1  PHAS=   83.7  FOM=  0.50  TEST= 0
INDE  11  19  54  FOBS=   93.1  SIGMA=   1.8  PHAS=   16.8  FOM=  0.92  TEST= 0
INDE  11  19  56  FOBS=  105.9  SIGMA=   2.0  PHAS=    5.2  FOM=  0.91  TEST= 0
INDE  11  19  58  FOBS=   19.4  SIGMA=  10.4  PHAS=  132.5  FOM=  0.17  TEST= 0
INDE  11  19  60  FOBS=  138.1  SIGMA=   1.9  PHAS=  -27.4  FOM=  0.91  TEST= 0
INDE  11  19  62  FOBS=    0.0  SIGMA=  21.9  PHAS=    0.0  FOM=  0.00  TEST= 0
INDE  11  19  64  FOBS=    0.0  SIGMA=  26.5  PHAS=    0.0  FOM=  0.00  TEST= 0
INDE  11  19  66  FOBS=  179.5  SIGMA=   2.9  PHAS=   12.0  FOM=  0.97  TEST= 0
INDE  11  19  68  FOBS=   45.4  SIGMA=  10.5  PHAS= -114.4  FOM=  0.83  TEST= 0
INDE  11  19  70  FOBS=   44.6  SIGMA=  10.8  PHAS= -129.9  FOM=  0.79  TEST= 0
INDE  11  20  11  FOBS=  111.6  SIGMA=   0.6  PHAS=  156.8  FOM=  0.89  TEST= 0
INDE  11  20  13  FOBS=  136.6  SIGMA=   0.6  PHAS= -100.5  FOM=  0.99  TEST= 0
INDE  11  20  15  FOBS=  230.9  SIGMA=   0.5  PHAS= -132.5  FOM=  0.97  TEST= 0
INDE  11  20  17  FOBS=  147.8  SIGMA=   0.5  PHAS=  153.9  FOM=  0.99  TEST= 0
INDE  11  20  19  FOBS=  167.0  SIGMA=   0.6  PHAS=  156.2  FOM=  0.93  TEST= 0
INDE  11  20  21  FOBS=  153.9  SIGMA=   0.6  PHAS= -165.9  FOM=  0.96  TEST= 0
INDE  11  20  23  FOBS=  153.9  SIGMA=   0.6  PHAS=  -36.2  FOM=  0.90  TEST= 0
INDE  11  20  25  FOBS=   99.2  SIGMA=   0.8  PHAS=   30.6  FOM=  0.89  TEST= 0
INDE  11  20  27  FOBS=  426.6  SIGMA=   0.5  PHAS=    8.3  FOM=  0.97  TEST= 0
INDE  11  20  29  FOBS=   99.6  SIGMA=   1.0  PHAS=   60.7  FOM=  0.99  TEST= 0
INDE  11  20  31  FOBS=  251.3  SIGMA=   0.5  PHAS= -148.4  FOM=  0.86  TEST= 1
INDE  11  20  33  FOBS=  154.3  SIGMA=   0.7  PHAS=   79.4  FOM=  0.96  TEST= 0
INDE  11  20  35  FOBS=  110.0  SIGMA=   1.1  PHAS=  -18.8  FOM=  0.65  TEST= 0
INDE  11  20  37  FOBS=  321.2  SIGMA=   0.5  PHAS=  -14.8  FOM=  0.93  TEST= 0
INDE  11  20  39  FOBS=  212.0  SIGMA=   0.7  PHAS= -101.0  FOM=  0.97  TEST= 0
INDE  11  20  41  FOBS=   89.6  SIGMA=   1.6  PHAS= -163.2  FOM=  0.93  TEST= 0
INDE  11  20  43  FOBS=  269.5  SIGMA=   0.7  PHAS=  -26.3  FOM=  0.86  TEST= 0
INDE  11  20  45  FOBS=  144.6  SIGMA=   1.1  PHAS= -135.9  FOM=  0.86  TEST= 0
INDE  11  20  47  FOBS=  140.5  SIGMA=   1.1  PHAS= -149.3  FOM=  0.91  TEST= 0
INDE  11  20  49  FOBS=   94.7  SIGMA=   1.6  PHAS=   65.4  FOM=  0.89  TEST= 0
INDE  11  20  51  FOBS=   30.0  SIGMA=   5.1  PHAS=   33.3  FOM=  0.64  TEST= 0
INDE  11  20  53  FOBS=   59.9  SIGMA=   2.9  PHAS=   47.6  FOM=  0.25  TEST= 1
INDE  11  20  55  FOBS=    0.0  SIGMA=  21.4  PHAS=    0.0  FOM=  0.00  TEST= 0
INDE  11  20  57  FOBS=   51.1  SIGMA=   4.1  PHAS=  155.1  FOM=  0.48  TEST= 0
INDE  11  20  59  FOBS=   46.6  SIGMA=   4.8  PHAS=  -85.4  FOM=  0.69  TEST= 0
INDE  11  20  61  FOBS=   56.3  SIGMA=   6.2  PHAS=  136.0  FOM=  0.61  TEST= 0
INDE  11  20  63  FOBS=  128.6  SIGMA=   2.0  PHAS=   58.0  FOM=  0.92  TEST= 0
INDE  11  20  65  FOBS=  101.9  SIGMA=   4.9  PHAS= -106.2  FOM=  0.94  TEST= 0
INDE  11  20  67  FOBS=   60.3  SIGMA=   8.0  PHAS= -164.7  FOM=  0.81  TEST= 0
INDE  11  20  69  FOBS=   64.9  SIGMA=   7.6  PHAS=  142.8  FOM=  0.77  TEST= 0
INDE  11  20  71  FOBS=   83.5  SIGMA=   6.1  PHAS=   64.1  FOM=  0.83  TEST= 0
INDE  11  20  73  FOBS=    0.0  SIGMA=  32.0  PHAS=    0.0  FOM=  0.00  TEST= 0
INDE  11  21  12  FOBS=  154.1  SIGMA=   0.5  PHAS=  141.8  FOM=  0.98  TEST= 0
INDE  11  21  14  FOBS=  175.6  SIGMA=   0.5  PHAS=   98.6  FOM=  0.96  TEST= 0
INDE  11  21  16  FOBS=  199.9  SIGMA=   0.6  PHAS=  118.2  FOM=  0.96  TEST= 0
INDE  11  21  18  FOBS=  203.2  SIGMA=   0.5  PHAS=   -3.1  FOM=  0.99  TEST= 0
INDE  11  21  20  FOBS=  268.5  SIGMA=   0.5  PHAS=  126.6  FOM=  0.99  TEST= 0
```

*FIG. 12A - 283*

| | | | | | | | | | | | |
|---|---|---|---|---|---|---|---|---|---|---|---|
| INDE | 11 | 21 | 22 | FOBS= | 67.3 | SIGMA= | 1.2 | PHAS= | -93.6 | FOM= 0.96 | TEST= 0 |
| INDE | 11 | 21 | 24 | FOBS= | 209.7 | SIGMA= | 0.5 | PHAS= | -53.9 | FOM= 0.99 | TEST= 1 |
| INDE | 11 | 21 | 26 | FOBS= | 167.0 | SIGMA= | 0.7 | PHAS= | -127.1 | FOM= 0.94 | TEST= 1 |
| INDE | 11 | 21 | 28 | FOBS= | 182.7 | SIGMA= | 0.6 | PHAS= | -19.3 | FOM= 0.93 | TEST= 0 |
| INDE | 11 | 21 | 30 | FOBS= | 75.9 | SIGMA= | 1.4 | PHAS= | 28.5 | FOM= 0.94 | TEST= 0 |
| INDE | 11 | 21 | 32 | FOBS= | 116.4 | SIGMA= | 1.0 | PHAS= | 174.3 | FOM= 0.99 | TEST= 0 |
| INDE | 11 | 21 | 34 | FOBS= | 87.4 | SIGMA= | 1.3 | PHAS= | -149.8 | FOM= 0.87 | TEST= 0 |
| INDE | 11 | 21 | 36 | FOBS= | 132.7 | SIGMA= | 1.0 | PHAS= | -130.7 | FOM= 0.70 | TEST= 1 |
| INDE | 11 | 21 | 38 | FOBS= | 115.5 | SIGMA= | 1.1 | PHAS= | -128.8 | FOM= 0.99 | TEST= 0 |
| INDE | 11 | 21 | 40 | FOBS= | 173.4 | SIGMA= | 0.9 | PHAS= | -129.9 | FOM= 0.96 | TEST= 0 |
| INDE | 11 | 21 | 42 | FOBS= | 144.6 | SIGMA= | 1.1 | PHAS= | -154.0 | FOM= 0.82 | TEST= 0 |
| INDE | 11 | 21 | 44 | FOBS= | 327.7 | SIGMA= | 0.6 | PHAS= | -140.2 | FOM= 0.97 | TEST= 0 |
| INDE | 11 | 21 | 46 | FOBS= | 78.4 | SIGMA= | 1.9 | PHAS= | 101.6 | FOM= 0.96 | TEST= 1 |
| INDE | 11 | 21 | 48 | FOBS= | 114.3 | SIGMA= | 1.3 | PHAS= | 153.9 | FOM= 0.94 | TEST= 0 |
| INDE | 11 | 21 | 50 | FOBS= | 173.8 | SIGMA= | 0.9 | PHAS= | -15.7 | FOM= 0.88 | TEST= 0 |
| INDE | 11 | 21 | 52 | FOBS= | 58.2 | SIGMA= | 3.7 | PHAS= | -67.5 | FOM= 0.41 | TEST= 0 |
| INDE | 11 | 21 | 54 | FOBS= | 93.1 | SIGMA= | 2.3 | PHAS= | -36.6 | FOM= 0.74 | TEST= 0 |
| INDE | 11 | 21 | 56 | FOBS= | 82.8 | SIGMA= | 2.6 | PHAS= | 142.7 | FOM= 0.68 | TEST= 0 |
| INDE | 11 | 21 | 58 | FOBS= | 33.5 | SIGMA= | 6.1 | PHAS= | 1.8 | FOM= 0.39 | TEST= 0 |
| INDE | 11 | 21 | 60 | FOBS= | 135.9 | SIGMA= | 1.9 | PHAS= | -29.5 | FOM= 0.94 | TEST= 0 |
| INDE | 11 | 21 | 62 | FOBS= | 97.6 | SIGMA= | 2.6 | PHAS= | -36.1 | FOM= 0.95 | TEST= 0 |
| INDE | 11 | 21 | 64 | FOBS= | 67.3 | SIGMA= | 5.1 | PHAS= | 160.2 | FOM= 0.56 | TEST= 0 |
| INDE | 11 | 21 | 66 | FOBS= | 133.5 | SIGMA= | 3.7 | PHAS= | 62.6 | FOM= 0.93 | TEST= 0 |
| INDE | 11 | 21 | 68 | FOBS= | 55.1 | SIGMA= | 8.8 | PHAS= | -147.6 | FOM= 0.68 | TEST= 0 |
| INDE | 11 | 21 | 70 | FOBS= | 40.1 | SIGMA= | 12.3 | PHAS= | -14.5 | FOM= 0.61 | TEST= 0 |
| INDE | 11 | 21 | 72 | FOBS= | 43.7 | SIGMA= | 11.6 | PHAS= | -73.9 | FOM= 0.61 | TEST= 0 |
| INDE | 11 | 21 | 74 | FOBS= | 45.8 | SIGMA= | 11.5 | PHAS= | -134.4 | FOM= 0.07 | TEST= 0 |
| INDE | 11 | 22 | 11 | FOBS= | 77.3 | SIGMA= | 0.8 | PHAS= | -62.3 | FOM= 0.98 | TEST= 0 |
| INDE | 11 | 22 | 13 | FOBS= | 158.9 | SIGMA= | 0.5 | PHAS= | -21.3 | FOM= 0.98 | TEST= 0 |
| INDE | 11 | 22 | 15 | FOBS= | 167.0 | SIGMA= | 0.6 | PHAS= | -55.4 | FOM= 0.99 | TEST= 0 |
| INDE | 11 | 22 | 17 | FOBS= | 155.6 | SIGMA= | 0.6 | PHAS= | -46.2 | FOM= 0.94 | TEST= 0 |
| INDE | 11 | 22 | 19 | FOBS= | 202.9 | SIGMA= | 0.5 | PHAS= | 50.1 | FOM= 0.87 | TEST= 1 |
| INDE | 11 | 22 | 21 | FOBS= | 72.1 | SIGMA= | 1.1 | PHAS= | -18.2 | FOM= 0.97 | TEST= 0 |
| INDE | 11 | 22 | 23 | FOBS= | 108.9 | SIGMA= | 0.9 | PHAS= | -138.4 | FOM= 0.98 | TEST= 0 |
| INDE | 11 | 22 | 25 | FOBS= | 275.2 | SIGMA= | 0.6 | PHAS= | -119.6 | FOM= 0.97 | TEST= 0 |
| INDE | 11 | 22 | 27 | FOBS= | 0.0 | SIGMA= | 14.0 | PHAS= | 0.0 | FOM= 0.00 | TEST= 0 |
| INDE | 11 | 22 | 29 | FOBS= | 116.0 | SIGMA= | 0.9 | PHAS= | 165.6 | FOM= 0.96 | TEST= 0 |
| INDE | 11 | 22 | 31 | FOBS= | 101.3 | SIGMA= | 1.1 | PHAS= | -127.5 | FOM= 0.96 | TEST= 0 |
| INDE | 11 | 22 | 33 | FOBS= | 88.8 | SIGMA= | 1.4 | PHAS= | 165.5 | FOM= 0.91 | TEST= 1 |
| INDE | 11 | 22 | 35 | FOBS= | 113.7 | SIGMA= | 1.1 | PHAS= | -81.0 | FOM= 0.47 | TEST= 1 |
| INDE | 11 | 22 | 37 | FOBS= | 87.3 | SIGMA= | 1.5 | PHAS= | -4.9 | FOM= 0.92 | TEST= 0 |
| INDE | 11 | 22 | 39 | FOBS= | 255.2 | SIGMA= | 0.6 | PHAS= | -157.6 | FOM= 0.97 | TEST= 0 |
| INDE | 11 | 22 | 41 | FOBS= | 102.4 | SIGMA= | 1.5 | PHAS= | 108.7 | FOM= 0.82 | TEST= 0 |
| INDE | 11 | 22 | 43 | FOBS= | 177.5 | SIGMA= | 1.0 | PHAS= | 85.8 | FOM= 0.93 | TEST= 0 |
| INDE | 11 | 22 | 45 | FOBS= | 150.3 | SIGMA= | 1.1 | PHAS= | 103.9 | FOM= 0.90 | TEST= 0 |
| INDE | 11 | 22 | 47 | FOBS= | 170.9 | SIGMA= | 0.9 | PHAS= | 15.1 | FOM= 0.94 | TEST= 0 |
| INDE | 11 | 22 | 49 | FOBS= | 105.1 | SIGMA= | 1.5 | PHAS= | -45.6 | FOM= 0.85 | TEST= 0 |
| INDE | 11 | 22 | 51 | FOBS= | 117.3 | SIGMA= | 1.6 | PHAS= | -75.7 | FOM= 0.84 | TEST= 0 |
| INDE | 11 | 22 | 53 | FOBS= | 0.0 | SIGMA= | 20.6 | PHAS= | 0.0 | FOM= 0.00 | TEST= 0 |
| INDE | 11 | 22 | 55 | FOBS= | 47.1 | SIGMA= | 4.4 | PHAS= | -85.3 | FOM= 0.15 | TEST= 1 |
| INDE | 11 | 22 | 57 | FOBS= | 27.7 | SIGMA= | 8.3 | PHAS= | -125.3 | FOM= 0.42 | TEST= 0 |
| INDE | 11 | 22 | 59 | FOBS= | 113.0 | SIGMA= | 2.0 | PHAS= | -117.6 | FOM= 0.93 | TEST= 0 |
| INDE | 11 | 22 | 61 | FOBS= | 109.6 | SIGMA= | 2.3 | PHAS= | -77.7 | FOM= 0.79 | TEST= 0 |
| INDE | 11 | 22 | 63 | FOBS= | 108.9 | SIGMA= | 2.3 | PHAS= | -104.7 | FOM= 0.87 | TEST= 0 |
| INDE | 11 | 22 | 65 | FOBS= | 108.5 | SIGMA= | 4.4 | PHAS= | -88.5 | FOM= 0.94 | TEST= 0 |
| INDE | 11 | 22 | 67 | FOBS= | 13.8 | SIGMA= | 34.0 | PHAS= | 137.6 | FOM= 0.18 | TEST= 0 |
| INDE | 11 | 22 | 69 | FOBS= | 38.5 | SIGMA= | 12.5 | PHAS= | -129.9 | FOM= 0.76 | TEST= 0 |
| INDE | 11 | 22 | 71 | FOBS= | 41.9 | SIGMA= | 12.0 | PHAS= | 34.3 | FOM= 0.75 | TEST= 0 |
| INDE | 11 | 22 | 73 | FOBS= | 53.1 | SIGMA= | 9.8 | PHAS= | 144.8 | FOM= 0.66 | TEST= 0 |
| INDE | 11 | 23 | 12 | FOBS= | 128.7 | SIGMA= | 0.6 | PHAS= | 110.1 | FOM= 0.71 | TEST= 0 |
| INDE | 11 | 23 | 14 | FOBS= | 86.0 | SIGMA= | 0.9 | PHAS= | 179.1 | FOM= 0.99 | TEST= 0 |
| INDE | 11 | 23 | 16 | FOBS= | 199.4 | SIGMA= | 0.6 | PHAS= | -138.3 | FOM= 0.90 | TEST= 0 |
| INDE | 11 | 23 | 18 | FOBS= | 183.4 | SIGMA= | 0.5 | PHAS= | -53.4 | FOM= 0.98 | TEST= 0 |
| INDE | 11 | 23 | 20 | FOBS= | 30.6 | SIGMA= | 2.6 | PHAS= | -69.5 | FOM= 0.91 | TEST= 0 |
| INDE | 11 | 23 | 22 | FOBS= | 92.4 | SIGMA= | 1.0 | PHAS= | -6.3 | FOM= 0.99 | TEST= 0 |
| INDE | 11 | 23 | 24 | FOBS= | 127.5 | SIGMA= | 0.9 | PHAS= | 80.0 | FOM= 0.43 | TEST= 1 |
| INDE | 11 | 23 | 26 | FOBS= | 225.6 | SIGMA= | 0.6 | PHAS= | 157.9 | FOM= 0.90 | TEST= 0 |
| INDE | 11 | 23 | 28 | FOBS= | 16.9 | SIGMA= | 7.1 | PHAS= | 75.2 | FOM= 0.06 | TEST= 0 |
| INDE | 11 | 23 | 30 | FOBS= | 54.4 | SIGMA= | 2.0 | PHAS= | 28.9 | FOM= 0.98 | TEST= 0 |
| INDE | 11 | 23 | 32 | FOBS= | 134.8 | SIGMA= | 0.9 | PHAS= | 54.2 | FOM= 0.79 | TEST= 0 |

*FIG. 12A - 284*

```
INDE 11 23 34 FOBS=  87.2 SIGMA=  1.5 PHAS=   97.9 FOM= 0.72 TEST= 0
INDE 11 23 36 FOBS= 131.0 SIGMA=  1.1 PHAS= -175.2 FOM= 0.96 TEST= 0
INDE 11 23 38 FOBS=  67.9 SIGMA=  2.0 PHAS=   51.8 FOM= 0.66 TEST= 0
INDE 11 23 40 FOBS= 200.9 SIGMA=  0.8 PHAS=  100.4 FOM= 0.96 TEST= 0
INDE 11 23 42 FOBS=  72.8 SIGMA=  2.1 PHAS=  -74.3 FOM= 0.66 TEST= 0
INDE 11 23 44 FOBS= 136.6 SIGMA=  1.1 PHAS=  -74.0 FOM= 0.91 TEST= 0
INDE 11 23 46 FOBS= 190.3 SIGMA=  0.8 PHAS=  -34.9 FOM= 0.94 TEST= 0
INDE 11 23 48 FOBS= 132.0 SIGMA=  1.2 PHAS= -154.5 FOM= 0.92 TEST= 0
INDE 11 23 50 FOBS=   0.0 SIGMA= 19.3 PHAS=    0.0 FOM= 0.00 TEST= 1
INDE 11 23 52 FOBS=   0.0 SIGMA= 19.2 PHAS=    0.0 FOM= 0.00 TEST= 1
INDE 11 23 54 FOBS=  80.9 SIGMA=  2.7 PHAS=   -1.2 FOM= 0.90 TEST= 0
INDE 11 23 56 FOBS= 120.8 SIGMA=  2.0 PHAS=  147.4 FOM= 0.94 TEST= 0
INDE 11 23 58 FOBS=  46.1 SIGMA=  4.5 PHAS=  164.2 FOM= 0.72 TEST= 0
INDE 11 23 60 FOBS=   0.0 SIGMA= 17.8 PHAS=    0.0 FOM= 0.00 TEST= 0
INDE 11 23 62 FOBS=  27.0 SIGMA= 12.9 PHAS=  144.9 FOM= 0.13 TEST= 0
INDE 11 23 64 FOBS= 129.1 SIGMA=  3.7 PHAS=  159.6 FOM= 0.89 TEST= 0
INDE 11 23 66 FOBS=  91.8 SIGMA=  5.1 PHAS=   48.1 FOM= 0.88 TEST= 0
INDE 11 23 68 FOBS=  49.3 SIGMA=  9.5 PHAS=  177.4 FOM= 0.67 TEST= 0
INDE 11 23 70 FOBS=  58.4 SIGMA=  8.3 PHAS=   53.2 FOM= 0.11 TEST= 0
INDE 11 23 72 FOBS=  51.9 SIGMA=  9.9 PHAS=  -52.0 FOM= 0.54 TEST= 0
INDE 11 24 11 FOBS=  99.8 SIGMA=  0.7 PHAS=  -58.1 FOM= 0.99 TEST= 0
INDE 11 24 13 FOBS= 118.1 SIGMA=  0.7 PHAS=   25.9 FOM= 0.90 TEST= 0
INDE 11 24 15 FOBS= 166.4 SIGMA=  0.6 PHAS= -166.4 FOM= 0.99 TEST= 0
INDE 11 24 17 FOBS= 226.4 SIGMA=  0.6 PHAS= -166.1 FOM= 0.98 TEST= 0
INDE 11 24 19 FOBS=  39.9 SIGMA=  1.9 PHAS=   69.1 FOM= 0.96 TEST= 0
INDE 11 24 21 FOBS= 363.9 SIGMA=  0.7 PHAS=  -36.2 FOM= 0.98 TEST= 1
INDE 11 24 23 FOBS= 107.6 SIGMA=  1.0 PHAS=  -71.5 FOM= 0.90 TEST= 0
INDE 11 24 25 FOBS= 204.8 SIGMA=  0.6 PHAS=  -23.9 FOM= 0.87 TEST= 0
INDE 11 24 27 FOBS= 168.7 SIGMA=  0.9 PHAS=  -40.4 FOM= 0.91 TEST= 0
INDE 11 24 29 FOBS= 135.8 SIGMA=  1.1 PHAS= -150.3 FOM= 0.99 TEST= 0
INDE 11 24 31 FOBS= 153.0 SIGMA=  0.9 PHAS=   22.0 FOM= 0.97 TEST= 0
INDE 11 24 33 FOBS= 219.3 SIGMA=  0.7 PHAS= -105.6 FOM= 0.95 TEST= 0
INDE 11 24 35 FOBS= 211.4 SIGMA=  0.7 PHAS=   -8.0 FOM= 0.91 TEST= 0
INDE 11 24 37 FOBS= 185.4 SIGMA=  0.9 PHAS=   27.2 FOM= 0.91 TEST= 0
INDE 11 24 39 FOBS=  40.7 SIGMA=  3.7 PHAS=  -51.2 FOM= 0.89 TEST= 0
INDE 11 24 41 FOBS= 275.2 SIGMA=  0.7 PHAS=   35.3 FOM= 0.95 TEST= 0
INDE 11 24 43 FOBS=  65.2 SIGMA=  2.4 PHAS= -144.0 FOM= 0.80 TEST= 0
INDE 11 24 45 FOBS= 113.9 SIGMA=  1.3 PHAS=  -24.2 FOM= 0.85 TEST= 0
INDE 11 24 47 FOBS=  63.6 SIGMA=  2.7 PHAS=   92.0 FOM= 0.72 TEST= 0
INDE 11 24 49 FOBS=  39.5 SIGMA=  4.6 PHAS=  -34.9 FOM= 0.24 TEST= 0
INDE 11 24 51 FOBS=  39.4 SIGMA=  4.3 PHAS= -108.0 FOM= 0.31 TEST= 0
INDE 11 24 53 FOBS=  49.9 SIGMA=  3.8 PHAS=   50.9 FOM= 0.50 TEST= 0
INDE 11 24 55 FOBS= 103.9 SIGMA=  2.0 PHAS=   10.4 FOM= 0.94 TEST= 0
INDE 11 24 57 FOBS=   0.0 SIGMA= 22.1 PHAS=    0.0 FOM= 0.00 TEST= 0
INDE 11 24 59 FOBS=  68.8 SIGMA=  3.6 PHAS= -144.4 FOM= 0.71 TEST= 0
INDE 11 24 61 FOBS=   0.0 SIGMA= 18.2 PHAS=    0.0 FOM= 0.00 TEST= 0
INDE 11 24 63 FOBS=  22.8 SIGMA= 12.2 PHAS=   87.2 FOM= 0.37 TEST= 0
INDE 11 24 65 FOBS=  40.6 SIGMA= 11.7 PHAS=  -52.8 FOM= 0.60 TEST= 0
INDE 11 24 69 FOBS=   0.0 SIGMA= 30.7 PHAS=    0.0 FOM= 0.00 TEST= 0
INDE 11 24 71 FOBS=  27.7 SIGMA= 17.7 PHAS=   15.8 FOM= 0.24 TEST= 0
INDE 11 24 73 FOBS=  46.2 SIGMA= 11.4 PHAS=   28.5 FOM= 0.32 TEST= 0
INDE 11 25 12 FOBS=  30.9 SIGMA=  2.2 PHAS=  170.1 FOM= 0.98 TEST= 1
INDE 11 25 14 FOBS=  77.8 SIGMA=  1.0 PHAS=  120.4 FOM= 0.80 TEST= 0
INDE 11 25 16 FOBS=  64.5 SIGMA=  1.3 PHAS= -173.7 FOM= 0.98 TEST= 0
INDE 11 25 18 FOBS=  91.4 SIGMA=  0.9 PHAS=  127.8 FOM= 0.99 TEST= 0
INDE 11 25 20 FOBS= 125.9 SIGMA=  0.8 PHAS= -100.9 FOM= 0.92 TEST= 0
INDE 11 25 22 FOBS=  84.5 SIGMA=  1.2 PHAS=  179.5 FOM= 0.95 TEST= 1
INDE 11 25 24 FOBS= 110.7 SIGMA=  1.0 PHAS= -102.4 FOM= 0.79 TEST= 0
INDE 11 25 26 FOBS= 179.3 SIGMA=  0.7 PHAS=  -86.4 FOM= 0.82 TEST= 0
INDE 11 25 28 FOBS= 193.3 SIGMA=  0.8 PHAS= -150.1 FOM= 0.98 TEST= 0
INDE 11 25 30 FOBS=  59.9 SIGMA=  2.2 PHAS=   89.2 FOM= 0.78 TEST= 0
INDE 11 25 32 FOBS= 125.7 SIGMA=  1.1 PHAS=   32.8 FOM= 0.98 TEST= 0
INDE 11 25 34 FOBS= 109.3 SIGMA=  1.3 PHAS=  164.0 FOM= 0.83 TEST= 0
INDE 11 25 36 FOBS= 219.3 SIGMA=  0.3 PHAS= -163.2 FOM= 0.95 TEST= 0
INDE 11 25 38 FOBS=  95.0 SIGMA=  1.7 PHAS=  178.2 FOM= 0.94 TEST= 0
INDE 11 25 40 FOBS= 144.4 SIGMA=  1.2 PHAS=  -41.7 FOM= 0.86 TEST= 0
INDE 11 25 42 FOBS= 242.9 SIGMA=  0.3 PHAS= -139.6 FOM= 0.94 TEST= 0
INDE 11 25 44 FOBS= 136.9 SIGMA=  1.2 PHAS= -119.9 FOM= 0.76 TEST= 0
INDE 11 25 46 FOBS= 221.9 SIGMA=  0.9 PHAS=   -0.2 FOM= 0.91 TEST= 0
INDE 11 25 48 FOBS= 115.1 SIGMA=  1.5 PHAS=  -75.0 FOM= 0.77 TEST= 1
```

*FIG. 12A - 285*

| | | | | | | | | | | | | |
|---|---|---|---|---|---|---|---|---|---|---|---|---|
| INDE | 11 | 25 | 50 | FOBS= | 105.7 | SIGMA= | 1.7 | PHAS= | -62.1 | FOM= | 0.82 | TEST= 0 |
| INDE | 11 | 25 | 52 | FOBS= | 40.4 | SIGMA= | 4.2 | PHAS= | 7.8 | FOM= | 0.39 | TEST= 0 |
| INDE | 11 | 25 | 54 | FOBS= | 120.4 | SIGMA= | 1.6 | PHAS= | -45.8 | FOM= | 0.95 | TEST= 0 |
| INDE | 11 | 25 | 56 | FOBS= | 79.4 | SIGMA= | 2.4 | PHAS= | 1.5 | FOM= | 0.85 | TEST= 0 |
| INDE | 11 | 25 | 58 | FOBS= | 112.7 | SIGMA= | 2.3 | PHAS= | 85.9 | FOM= | 0.62 | TEST= 1 |
| INDE | 11 | 25 | 60 | FOBS= | 97.4 | SIGMA= | 2.6 | PHAS= | 41.6 | FOM= | 0.82 | TEST= 0 |
| INDE | 11 | 25 | 62 | FOBS= | 0.0 | SIGMA= | 18.6 | PHAS= | 0.0 | FOM= | 0.00 | TEST= 0 |
| INDE | 11 | 25 | 64 | FOBS= | 98.7 | SIGMA= | 5.0 | PHAS= | 48.1 | FOM= | 0.90 | TEST= 0 |
| INDE | 11 | 25 | 66 | FOBS= | 90.8 | SIGMA= | 5.4 | PHAS= | 15.3 | FOM= | 0.91 | TEST= 0 |
| INDE | 11 | 25 | 68 | FOBS= | 41.8 | SIGMA= | 11.6 | PHAS= | -116.9 | FOM= | 0.38 | TEST= 0 |
| INDE | 11 | 25 | 70 | FOBS= | 0.0 | SIGMA= | 30.9 | PHAS= | 0.0 | FOM= | 0.00 | TEST= 0 |
| INDE | 11 | 25 | 72 | FOBS= | 43.1 | SIGMA= | 11.6 | PHAS= | 119.1 | FOM= | 0.03 | TEST= 1 |
| INDE | 11 | 26 | 11 | FOBS= | 96.1 | SIGMA= | 0.8 | PHAS= | 64.1 | FOM= | 0.94 | TEST= 0 |
| INDE | 11 | 26 | 13 | FOBS= | 67.4 | SIGMA= | 1.2 | PHAS= | 42.1 | FOM= | 0.98 | TEST= 0 |
| INDE | 11 | 26 | 15 | FOBS= | 35.5 | SIGMA= | 2.2 | PHAS= | 111.4 | FOM= | 0.95 | TEST= 0 |
| INDE | 11 | 26 | 17 | FOBS= | 119.5 | SIGMA= | 0.9 | PHAS= | 178.6 | FOM= | 0.96 | TEST= 0 |
| INDE | 11 | 26 | 19 | FOBS= | 76.7 | SIGMA= | 1.3 | PHAS= | 155.0 | FOM= | 0.81 | TEST= 0 |
| INDE | 11 | 26 | 21 | FOBS= | 339.4 | SIGMA= | 0.5 | PHAS= | -95.9 | FOM= | 0.94 | TEST= 0 |
| INDE | 11 | 26 | 23 | FOBS= | 158.0 | SIGMA= | 0.8 | PHAS= | -94.9 | FOM= | 0.77 | TEST= 1 |
| INDE | 11 | 26 | 25 | FOBS= | 234.9 | SIGMA= | 0.6 | PHAS= | 159.4 | FOM= | 0.97 | TEST= 0 |
| INDE | 11 | 26 | 27 | FOBS= | 48.4 | SIGMA= | 2.2 | PHAS= | 145.8 | FOM= | 0.81 | TEST= 0 |
| INDE | 11 | 26 | 29 | FOBS= | 115.2 | SIGMA= | 1.2 | PHAS= | -151.7 | FOM= | 0.79 | TEST= 0 |
| INDE | 11 | 26 | 31 | FOBS= | 185.0 | SIGMA= | 0.9 | PHAS= | -13.0 | FOM= | 0.91 | TEST= 0 |
| INDE | 11 | 26 | 33 | FOBS= | 142.7 | SIGMA= | 1.1 | PHAS= | -40.1 | FOM= | 0.97 | TEST= 0 |
| INDE | 11 | 26 | 35 | FOBS= | 48.9 | SIGMA= | 3.0 | PHAS= | 3.9 | FOM= | 0.27 | TEST= 0 |
| INDE | 11 | 26 | 37 | FOBS= | 192.4 | SIGMA= | 1.0 | PHAS= | -8.1 | FOM= | 0.97 | TEST= 0 |
| INDE | 11 | 26 | 39 | FOBS= | 115.4 | SIGMA= | 1.5 | PHAS= | -116.9 | FOM= | 0.79 | TEST= 0 |
| INDE | 11 | 26 | 41 | FOBS= | 166.9 | SIGMA= | 1.1 | PHAS= | 114.7 | FOM= | 0.89 | TEST= 0 |
| INDE | 11 | 26 | 43 | FOBS= | 60.4 | SIGMA= | 3.0 | PHAS= | 146.7 | FOM= | 0.14 | TEST= 0 |
| INDE | 11 | 26 | 45 | FOBS= | 57.8 | SIGMA= | 3.1 | PHAS= | -96.1 | FOM= | 0.52 | TEST= 0 |
| INDE | 11 | 26 | 47 | FOBS= | 182.3 | SIGMA= | 1.0 | PHAS= | -138.2 | FOM= | 0.86 | TEST= 0 |
| INDE | 11 | 26 | 49 | FOBS= | 87.1 | SIGMA= | 2.0 | PHAS= | -126.1 | FOM= | 0.89 | TEST= 1 |
| INDE | 11 | 26 | 51 | FOBS= | 101.8 | SIGMA= | 1.7 | PHAS= | -161.9 | FOM= | 0.69 | TEST= 0 |
| INDE | 11 | 26 | 53 | FOBS= | 118.9 | SIGMA= | 1.5 | PHAS= | -125.6 | FOM= | 0.94 | TEST= 0 |
| INDE | 11 | 26 | 55 | FOBS= | 200.7 | SIGMA= | 1.0 | PHAS= | -105.2 | FOM= | 0.97 | TEST= 0 |
| INDE | 11 | 26 | 57 | FOBS= | 147.0 | SIGMA= | 1.3 | PHAS= | -92.2 | FOM= | 0.95 | TEST= 0 |
| INDE | 11 | 26 | 59 | FOBS= | 65.4 | SIGMA= | 3.9 | PHAS= | -111.7 | FOM= | 0.28 | TEST= 1 |
| INDE | 11 | 26 | 61 | FOBS= | 52.8 | SIGMA= | 3.3 | PHAS= | -129.7 | FOM= | 0.39 | TEST= 0 |
| INDE | 11 | 26 | 63 | FOBS= | 0.0 | SIGMA= | 19.4 | PHAS= | 0.0 | FOM= | 0.00 | TEST= 0 |
| INDE | 11 | 26 | 65 | FOBS= | 136.8 | SIGMA= | 3.7 | PHAS= | -69.3 | FOM= | 0.96 | TEST= 0 |
| INDE | 11 | 26 | 67 | FOBS= | 61.7 | SIGMA= | 8.0 | PHAS= | -34.3 | FOM= | 0.88 | TEST= 0 |
| INDE | 11 | 26 | 69 | FOBS= | 56.2 | SIGMA= | 8.8 | PHAS= | 126.3 | FOM= | 0.78 | TEST= 0 |
| INDE | 11 | 26 | 71 | FOBS= | 0.0 | SIGMA= | 31.5 | PHAS= | 0.0 | FOM= | 0.00 | TEST= 0 |
| INDE | 11 | 27 | 12 | FOBS= | 99.5 | SIGMA= | 0.8 | PHAS= | -53.8 | FOM= | 0.95 | TEST= 0 |
| INDE | 11 | 27 | 14 | FOBS= | 19.3 | SIGMA= | 4.3 | PHAS= | -31.1 | FOM= | 0.91 | TEST= 1 |
| INDE | 11 | 27 | 16 | FOBS= | 97.5 | SIGMA= | 1.0 | PHAS= | -94.3 | FOM= | 0.97 | TEST= 0 |
| INDE | 11 | 27 | 18 | FOBS= | 202.3 | SIGMA= | 0.6 | PHAS= | 155.2 | FOM= | 0.97 | TEST= 0 |
| INDE | 11 | 27 | 20 | FOBS= | 150.9 | SIGMA= | 0.8 | PHAS= | 92.2 | FOM= | 0.81 | TEST= 0 |
| INDE | 11 | 27 | 22 | FOBS= | 294.8 | SIGMA= | 0.6 | PHAS= | 126.7 | FOM= | 0.97 | TEST= 0 |
| INDE | 11 | 27 | 24 | FOBS= | 111.3 | SIGMA= | 1.1 | PHAS= | -173.5 | FOM= | 0.93 | TEST= 0 |
| INDE | 11 | 27 | 26 | FOBS= | 260.9 | SIGMA= | 0.6 | PHAS= | 44.2 | FOM= | 0.93 | TEST= 0 |
| INDE | 11 | 27 | 28 | FOBS= | 116.7 | SIGMA= | 1.0 | PHAS= | 52.3 | FOM= | 0.82 | TEST= 0 |
| INDE | 11 | 27 | 30 | FOBS= | 76.3 | SIGMA= | 1.8 | PHAS= | 173.8 | FOM= | 0.87 | TEST= 0 |
| INDE | 11 | 27 | 32 | FOBS= | 85.1 | SIGMA= | 1.8 | PHAS= | -117.7 | FOM= | 0.85 | TEST= 0 |
| INDE | 11 | 27 | 34 | FOBS= | 90.8 | SIGMA= | 1.8 | PHAS= | -153.4 | FOM= | 0.96 | TEST= 0 |
| INDE | 11 | 27 | 36 | FOBS= | 253.3 | SIGMA= | 0.8 | PHAS= | 164.7 | FOM= | 0.96 | TEST= 1 |
| INDE | 11 | 27 | 38 | FOBS= | 333.6 | SIGMA= | 0.8 | PHAS= | -177.3 | FOM= | 0.97 | TEST= 0 |
| INDE | 11 | 27 | 40 | FOBS= | 129.8 | SIGMA= | 1.5 | PHAS= | 17.8 | FOM= | 0.91 | TEST= 0 |
| INDE | 11 | 27 | 42 | FOBS= | 259.2 | SIGMA= | 1.0 | PHAS= | -105.4 | FOM= | 0.93 | TEST= 1 |
| INDE | 11 | 27 | 44 | FOBS= | 77.3 | SIGMA= | 2.4 | PHAS= | 85.9 | FOM= | 0.74 | TEST= 0 |
| INDE | 11 | 27 | 46 | FOBS= | 25.4 | SIGMA= | 7.2 | PHAS= | -152.5 | FOM= | 0.09 | TEST= 0 |
| INDE | 11 | 27 | 48 | FOBS= | 131.1 | SIGMA= | 1.4 | PHAS= | -176.3 | FOM= | 0.93 | TEST= 0 |
| INDE | 11 | 27 | 50 | FOBS= | 80.6 | SIGMA= | 2.2 | PHAS= | 80.8 | FOM= | 0.90 | TEST= 0 |
| INDE | 11 | 27 | 52 | FOBS= | 38.4 | SIGMA= | 4.4 | PHAS= | -175.8 | FOM= | 0.04 | TEST= 0 |
| INDE | 11 | 27 | 54 | FOBS= | 142.3 | SIGMA= | 1.3 | PHAS= | 152.2 | FOM= | 0.94 | TEST= 0 |
| INDE | 11 | 27 | 56 | FOBS= | 60.7 | SIGMA= | 2.8 | PHAS= | 111.3 | FOM= | 0.57 | TEST= 0 |
| INDE | 11 | 27 | 58 | FOBS= | 26.3 | SIGMA= | 9.0 | PHAS= | -74.1 | FOM= | 0.18 | TEST= 0 |
| INDE | 11 | 27 | 60 | FOBS= | 55.1 | SIGMA= | 4.6 | PHAS= | 69.2 | FOM= | 0.86 | TEST= 0 |
| INDE | 11 | 27 | 62 | FOBS= | 14.8 | SIGMA= | 14.3 | PHAS= | 14.5 | FOM= | 0.20 | TEST= 0 |
| INDE | 11 | 27 | 64 | FOBS= | 77.0 | SIGMA= | 2.5 | PHAS= | -80.4 | FOM= | 0.70 | TEST= 0 |

*FIG. 12A - 286*

```
INDE 11 27 66 FOBS=  111.4 SIGMA=  4.5 PHAS= -164.0 FOM= 0.90 TEST= 0
INDE 11 27 68 FOBS=   39.5 SIGMA= 12.7 PHAS= -150.9 FOM= 0.04 TEST= 1
INDE 11 27 70 FOBS=    0.0 SIGMA= 31.5 PHAS=    0.0 FOM= 0.00 TEST= 0
INDE 11 27 72 FOBS=   45.3 SIGMA= 11.2 PHAS=   83.8 FOM= 0.57 TEST= 0
INDE 11 28 11 FOBS=  195.5 SIGMA=  0.5 PHAS=  111.7 FOM= 0.99 TEST= 0
INDE 11 28 13 FOBS=   87.2 SIGMA=  1.1 PHAS=  -91.5 FOM= 0.95 TEST= 0
INDE 11 28 15 FOBS=   92.0 SIGMA=  1.1 PHAS=  139.2 FOM= 0.95 TEST= 0
INDE 11 28 17 FOBS=   86.4 SIGMA=  1.2 PHAS=   75.6 FOM= 0.99 TEST= 0
INDE 11 28 19 FOBS=  207.2 SIGMA=  0.6 PHAS=   28.3 FOM= 0.96 TEST= 0
INDE 11 28 21 FOBS=  250.7 SIGMA=  0.6 PHAS=   -7.4 FOM= 0.99 TEST= 0
INDE 11 28 23 FOBS=  251.8 SIGMA=  0.6 PHAS=   39.8 FOM= 0.99 TEST= 0
INDE 11 28 25 FOBS=  193.7 SIGMA=  0.7 PHAS=   90.1 FOM= 0.97 TEST= 0
INDE 11 28 27 FOBS=  443.5 SIGMA=  0.6 PHAS=  -77.5 FOM= 0.97 TEST= 0
INDE 11 28 29 FOBS=  115.7 SIGMA=  1.1 PHAS=    1.8 FOM= 0.93 TEST= 0
INDE 11 28 31 FOBS=  132.1 SIGMA=  1.1 PHAS=   82.3 FOM= 0.72 TEST= 0
INDE 11 28 33 FOBS=  261.1 SIGMA=  1.0 PHAS=  121.7 FOM= 0.98 TEST= 0
INDE 11 28 35 FOBS=  137.6 SIGMA=  1.3 PHAS=   97.0 FOM= 0.81 TEST= 0
INDE 11 28 37 FOBS=   90.0 SIGMA=  2.3 PHAS=   91.2 FOM= 0.83 TEST= 0
INDE 11 28 39 FOBS=  146.5 SIGMA=  1.5 PHAS=  -58.9 FOM= 0.91 TEST= 0
INDE 11 28 41 FOBS=  189.2 SIGMA=  1.2 PHAS=  166.3 FOM= 0.94 TEST= 0
INDE 11 28 43 FOBS=   58.7 SIGMA=  3.6 PHAS= -111.9 FOM= 0.29 TEST= 0
INDE 11 28 45 FOBS=   72.7 SIGMA=  2.7 PHAS= -145.2 FOM= 0.76 TEST= 0
INDE 11 28 47 FOBS=  182.5 SIGMA=  1.1 PHAS=  152.8 FOM= 0.95 TEST= 0
INDE 11 28 49 FOBS=  135.7 SIGMA=  1.3 PHAS=   50.6 FOM= 0.91 TEST= 0
INDE 11 28 51 FOBS=   62.7 SIGMA=  2.7 PHAS=   21.5 FOM= 0.55 TEST= 0
INDE 11 28 53 FOBS=   27.7 SIGMA=  6.4 PHAS=  122.8 FOM= 0.44 TEST= 0
INDE 11 28 55 FOBS=  120.9 SIGMA=  1.5 PHAS=  -91.8 FOM= 0.61 TEST= 1
INDE 11 28 57 FOBS=  138.8 SIGMA=  1.4 PHAS=  -42.8 FOM= 0.94 TEST= 0
INDE 11 28 59 FOBS=  119.9 SIGMA=  1.8 PHAS= -105.4 FOM= 0.91 TEST= 0
INDE 11 28 61 FOBS=   80.3 SIGMA=  2.4 PHAS=  -74.4 FOM= 0.79 TEST= 1
INDE 11 28 63 FOBS=   19.6 SIGMA= 10.4 PHAS=  -87.9 FOM= 0.29 TEST= 0
INDE 11 28 65 FOBS=   60.8 SIGMA=  3.6 PHAS=   62.7 FOM= 0.42 TEST= 0
INDE 11 28 67 FOBS=   57.3 SIGMA=  8.6 PHAS=   34.3 FOM= 0.61 TEST= 0
INDE 11 28 69 FOBS=   44.2 SIGMA= 11.5 PHAS=   89.9 FOM= 0.72 TEST= 0
INDE 11 28 71 FOBS=    0.0 SIGMA= 32.1 PHAS=    0.0 FOM= 0.00 TEST= 0
INDE 11 29 12 FOBS=   52.7 SIGMA=  2.5 PHAS=   60.5 FOM= 0.98 TEST= 0
INDE 11 29 14 FOBS=  103.9 SIGMA=  1.0 PHAS=   65.0 FOM= 0.64 TEST= 0
INDE 11 29 16 FOBS=  138.5 SIGMA=  0.8 PHAS=  -28.7 FOM= 0.99 TEST= 0
INDE 11 29 18 FOBS=  207.3 SIGMA=  0.7 PHAS=  -98.4 FOM= 0.97 TEST= 0
INDE 11 29 20 FOBS=  183.5 SIGMA=  0.7 PHAS=  -50.6 FOM= 0.98 TEST= 0
INDE 11 29 22 FOBS=  274.9 SIGMA=  0.6 PHAS=  -63.9 FOM= 0.56 TEST= 1
INDE 11 29 24 FOBS=  470.0 SIGMA=  0.6 PHAS=  -96.7 FOM= 0.98 TEST= 1
INDE 11 29 26 FOBS=  137.4 SIGMA=  1.1 PHAS= -113.2 FOM= 0.91 TEST= 0
INDE 11 29 28 FOBS=  237.4 SIGMA=  0.7 PHAS=  178.7 FOM= 0.97 TEST= 0
INDE 11 29 30 FOBS=  148.9 SIGMA=  1.0 PHAS=  -25.3 FOM= 0.89 TEST= 0
INDE 11 29 32 FOBS=  170.8 SIGMA=  0.9 PHAS=  108.4 FOM= 0.91 TEST= 0
INDE 11 29 34 FOBS=  249.1 SIGMA=  1.0 PHAS=   34.3 FOM= 0.95 TEST= 0
INDE 11 29 36 FOBS=   54.0 SIGMA=  4.3 PHAS=  138.2 FOM= 0.50 TEST= 0
INDE 11 29 38 FOBS=  248.6 SIGMA=  1.2 PHAS=  177.9 FOM= 0.85 TEST= 1
INDE 11 29 40 FOBS=  151.9 SIGMA=  1.4 PHAS=  155.5 FOM= 0.86 TEST= 0
INDE 11 29 42 FOBS=   70.3 SIGMA=  2.9 PHAS=  159.8 FOM= 0.84 TEST= 0
INDE 11 29 44 FOBS=   74.8 SIGMA=  2.7 PHAS=   57.4 FOM= 0.35 TEST= 0
INDE 11 29 46 FOBS=    0.0 SIGMA= 19.7 PHAS=    0.0 FOM= 0.00 TEST= 0
INDE 11 29 48 FOBS=   82.5 SIGMA=  2.4 PHAS=   74.1 FOM= 0.84 TEST= 0
INDE 11 29 50 FOBS=  119.9 SIGMA=  1.5 PHAS=  -48.7 FOM= 0.87 TEST= 0
INDE 11 29 52 FOBS=  128.7 SIGMA=  1.4 PHAS= -105.5 FOM= 0.90 TEST= 0
INDE 11 29 54 FOBS=   51.6 SIGMA=  3.3 PHAS=  164.0 FOM= 0.84 TEST= 0
INDE 11 29 56 FOBS=   83.3 SIGMA=  2.2 PHAS= -126.6 FOM= 0.85 TEST= 0
INDE 11 29 58 FOBS=   61.4 SIGMA=  3.0 PHAS=  173.5 FOM= 0.29 TEST= 0
INDE 11 29 60 FOBS=  126.3 SIGMA=  1.7 PHAS=  135.9 FOM= 0.96 TEST= 0
INDE 11 29 62 FOBS=    0.0 SIGMA= 23.6 PHAS=    0.0 FOM= 0.00 TEST= 0
INDE 11 29 64 FOBS=   93.9 SIGMA=  2.3 PHAS=  -70.2 FOM= 0.93 TEST= 0
INDE 11 29 66 FOBS=    0.0 SIGMA= 21.0 PHAS=    0.0 FOM= 0.00 TEST= 0
INDE 11 29 68 FOBS=   57.0 SIGMA=  8.9 PHAS= -107.8 FOM= 0.87 TEST= 0
INDE 11 29 70 FOBS=   49.0 SIGMA= 10.6 PHAS=   81.9 FOM= 0.47 TEST= 0
INDE 11 30 11 FOBS=  174.9 SIGMA=  0.6 PHAS=   67.4 FOM= 0.92 TEST= 0
INDE 11 30 13 FOBS=  132.2 SIGMA=  0.8 PHAS=   59.9 FOM= 0.90 TEST= 0
INDE 11 30 15 FOBS=  100.5 SIGMA=  1.0 PHAS=  -14.1 FOM= 0.53 TEST= 0
INDE 11 30 17 FOBS=   61.1 SIGMA=  1.8 PHAS= -156.1 FOM= 0.95 TEST= 0
INDE 11 30 19 FOBS=  147.6 SIGMA=  0.8 PHAS= -133.0 FOM= 0.96 TEST= 0
```

*FIG. 12A - 287*

```
INDE  11  30  21  FOBS=    238.4  SIGMA=   0.6  PHAS=  -151.3  FOM=  0.98  TEST=  0
INDE  11  30  23  FOBS=    270.5  SIGMA=   0.7  PHAS=  -156.5  FOM=  0.94  TEST=  0
INDE  11  30  25  FOBS=    160.5  SIGMA=   0.9  PHAS=   -50.2  FOM=  0.91  TEST=  0
INDE  11  30  27  FOBS=     69.7  SIGMA=   2.0  PHAS=    87.1  FOM=  0.59  TEST=  0
INDE  11  30  29  FOBS=    173.1  SIGMA=   0.9  PHAS=    52.6  FOM=  0.87  TEST=  0
INDE  11  30  31  FOBS=     82.3  SIGMA=   1.9  PHAS=  -163.5  FOM=  0.97  TEST=  0
INDE  11  30  33  FOBS=    219.2  SIGMA=   1.1  PHAS=   135.9  FOM=  0.97  TEST=  0
INDE  11  30  35  FOBS=     52.7  SIGMA=   4.4  PHAS=   -33.1  FOM=  0.86  TEST=  0
INDE  11  30  37  FOBS=    177.3  SIGMA=   1.5  PHAS=   -73.9  FOM=  0.94  TEST=  0
INDE  11  30  39  FOBS=    137.9  SIGMA=   1.8  PHAS=    15.2  FOM=  0.93  TEST=  0
INDE  11  30  41  FOBS=    168.9  SIGMA=   1.5  PHAS=    62.5  FOM=  0.94  TEST=  0
INDE  11  30  43  FOBS=     56.1  SIGMA=   3.6  PHAS=   -71.1  FOM=  0.35  TEST=  0
INDE  11  30  45  FOBS=     42.6  SIGMA=   4.9  PHAS=   176.0  FOM=  0.27  TEST=  1
INDE  11  30  47  FOBS=    126.6  SIGMA=   1.6  PHAS=    40.1  FOM=  0.84  TEST=  0
INDE  11  30  49  FOBS=     17.9  SIGMA=  12.3  PHAS=    38.1  FOM=  0.09  TEST=  0
INDE  11  30  51  FOBS=    144.2  SIGMA=   1.3  PHAS=   131.7  FOM=  0.94  TEST=  0
INDE  11  30  53  FOBS=      2.3  SIGMA=  83.2  PHAS=   123.3  FOM=  0.07  TEST=  0
INDE  11  30  55  FOBS=     80.0  SIGMA=   2.1  PHAS=   160.6  FOM=  0.28  TEST=  1
INDE  11  30  57  FOBS=     68.1  SIGMA=   2.7  PHAS=  -134.2  FOM=  0.35  TEST=  0
INDE  11  30  59  FOBS=     70.5  SIGMA=   2.6  PHAS=    -9.6  FOM=  0.90  TEST=  0
INDE  11  30  61  FOBS=     20.0  SIGMA=  12.2  PHAS=   -38.8  FOM=  0.26  TEST=  0
INDE  11  30  63  FOBS=     53.5  SIGMA=   3.6  PHAS=   -98.6  FOM=  0.68  TEST=  0
INDE  11  30  65  FOBS=     21.1  SIGMA=  11.3  PHAS=    78.9  FOM=  0.42  TEST=  0
INDE  11  30  67  FOBS=      0.0  SIGMA=  21.3  PHAS=     0.0  FOM=  0.00  TEST=  0
INDE  11  30  69  FOBS=     30.6  SIGMA=  16.6  PHAS=   -47.6  FOM=  0.58  TEST=  0
INDE  11  31  12  FOBS=    153.2  SIGMA=   0.7  PHAS=    15.2  FOM=  0.96  TEST=  0
INDE  11  31  14  FOBS=     73.8  SIGMA=   1.4  PHAS=   -10.1  FOM=  0.99  TEST=  0
INDE  11  31  16  FOBS=    164.4  SIGMA=   0.7  PHAS=  -123.8  FOM=  0.96  TEST=  0
INDE  11  31  18  FOBS=    175.7  SIGMA=   0.8  PHAS=   -73.4  FOM=  0.94  TEST=  0
INDE  11  31  20  FOBS=    178.5  SIGMA=   0.8  PHAS=    85.5  FOM=  0.85  TEST=  0
INDE  11  31  22  FOBS=    166.2  SIGMA=   0.8  PHAS=   107.8  FOM=  0.98  TEST=  0
INDE  11  31  24  FOBS=    317.0  SIGMA=   0.6  PHAS=  -144.5  FOM=  0.78  TEST=  1
INDE  11  31  26  FOBS=    377.3  SIGMA=   0.8  PHAS=  -107.3  FOM=  0.97  TEST=  0
INDE  11  31  28  FOBS=    135.1  SIGMA=   1.6  PHAS=   -99.1  FOM=  0.94  TEST=  0
INDE  11  31  30  FOBS=    171.1  SIGMA=   1.1  PHAS=   -37.6  FOM=  0.96  TEST=  0
INDE  11  31  32  FOBS=    485.3  SIGMA=   0.9  PHAS=    63.7  FOM=  0.99  TEST=  0
INDE  11  31  34  FOBS=    178.0  SIGMA=   1.2  PHAS=    43.9  FOM=  0.95  TEST=  0
INDE  11  31  36  FOBS=    272.6  SIGMA=   1.0  PHAS=  -157.2  FOM=  0.99  TEST=  0
INDE  11  31  38  FOBS=     68.9  SIGMA=   3.5  PHAS=   120.9  FOM=  0.64  TEST=  0
INDE  11  31  40  FOBS=     94.0  SIGMA=   2.5  PHAS=  -164.6  FOM=  0.91  TEST=  0
INDE  11  31  42  FOBS=     38.4  SIGMA=   6.6  PHAS=   178.7  FOM=  0.61  TEST=  0
INDE  11  31  44  FOBS=     91.2  SIGMA=   2.3  PHAS=    -3.2  FOM=  0.89  TEST=  0
INDE  11  31  46  FOBS=    130.2  SIGMA=   1.6  PHAS=   -18.0  FOM=  0.92  TEST=  0
INDE  11  31  48  FOBS=     45.5  SIGMA=   4.2  PHAS=    -5.7  FOM=  0.74  TEST=  0
INDE  11  31  50  FOBS=     61.4  SIGMA=   3.1  PHAS=     3.6  FOM=  0.75  TEST=  1
INDE  11  31  52  FOBS=    140.6  SIGMA=   1.4  PHAS=     6.4  FOM=  0.93  TEST=  0
INDE  11  31  54  FOBS=     82.4  SIGMA=   2.1  PHAS=    -4.6  FOM=  0.81  TEST=  0
INDE  11  31  56  FOBS=     53.8  SIGMA=   3.4  PHAS=     4.5  FOM=  0.12  TEST=  0
INDE  11  31  58  FOBS=     53.5  SIGMA=   3.4  PHAS=   -57.3  FOM=  0.72  TEST=  0
INDE  11  31  60  FOBS=     38.8  SIGMA=   5.3  PHAS=  -162.0  FOM=  0.65  TEST=  0
INDE  11  31  62  FOBS=     32.1  SIGMA=   6.8  PHAS=  -100.1  FOM=  0.11  TEST=  0
INDE  11  31  64  FOBS=     82.2  SIGMA=   2.3  PHAS=  -108.8  FOM=  0.82  TEST=  0
INDE  11  31  66  FOBS=      0.0  SIGMA=  22.0  PHAS=     0.0  FOM=  0.00  TEST=  0
INDE  11  31  68  FOBS=     90.4  SIGMA=   2.7  PHAS=  -139.9  FOM=  0.93  TEST=  0
INDE  11  31  70  FOBS=     94.3  SIGMA=   5.8  PHAS=   152.2  FOM=  0.89  TEST=  0
INDE  11  32  11  FOBS=    245.0  SIGMA=   0.5  PHAS=    10.6  FOM=  0.99  TEST=  0
INDE  11  32  13  FOBS=    163.1  SIGMA=   0.8  PHAS=   148.1  FOM=  0.98  TEST=  0
INDE  11  32  15  FOBS=    126.8  SIGMA=   1.0  PHAS=   -19.8  FOM=  0.89  TEST=  0
INDE  11  32  17  FOBS=    171.2  SIGMA=   0.9  PHAS=  -162.9  FOM=  0.92  TEST=  1
INDE  11  32  19  FOBS=    254.2  SIGMA=   0.6  PHAS=  -123.6  FOM=  0.95  TEST=  0
INDE  11  32  21  FOBS=    331.4  SIGMA=   0.6  PHAS=   -28.2  FOM=  0.96  TEST=  0
INDE  11  32  23  FOBS=    160.3  SIGMA=   1.0  PHAS=  -133.5  FOM=  0.99  TEST=  0
INDE  11  32  25  FOBS=    132.2  SIGMA=   1.4  PHAS=   152.9  FOM=  0.60  TEST=  0
INDE  11  32  27  FOBS=    525.4  SIGMA=   0.9  PHAS=   154.9  FOM=  0.99  TEST=  0
INDE  11  32  29  FOBS=     37.8  SIGMA=   4.9  PHAS=   -48.7  FOM=  0.41  TEST=  1
INDE  11  32  31  FOBS=    164.3  SIGMA=   1.2  PHAS=   -93.2  FOM=  0.87  TEST=  0
INDE  11  32  33  FOBS=    242.4  SIGMA=   0.9  PHAS=   -49.1  FOM=  0.95  TEST=  0
INDE  11  32  35  FOBS=     29.5  SIGMA=   7.2  PHAS=   -29.0  FOM=  0.46  TEST=  0
INDE  11  32  37  FOBS=     27.3  SIGMA=  10.5  PHAS=   119.1  FOM=  0.19  TEST=  0
INDE  11  32  39  FOBS=      0.0  SIGMA=  22.4  PHAS=     0.0  FOM=  0.00  TEST=  0
```

*FIG. 12A - 288*

```
INDE 11 32 41 FOBS=  124.4 SIGMA=  1.9 PHAS=  101.0 FOM= 0.91 TEST= 1
INDE 11 32 43 FOBS=   93.0 SIGMA=  2.5 PHAS=   -1.1 FOM= 0.74 TEST= 0
INDE 11 32 45 FOBS=  102.7 SIGMA=  2.2 PHAS=  -88.1 FOM= 0.83 TEST= 0
INDE 11 32 47 FOBS=  120.4 SIGMA=  1.7 PHAS= -124.7 FOM= 0.93 TEST= 0
INDE 11 32 49 FOBS=  107.3 SIGMA=  1.8 PHAS= -154.3 FOM= 0.87 TEST= 0
INDE 11 32 51 FOBS=   91.7 SIGMA=  2.1 PHAS=  -55.0 FOM= 0.54 TEST= 0
INDE 11 32 53 FOBS=   77.8 SIGMA=  2.5 PHAS= -126.3 FOM= 0.88 TEST= 0
INDE 11 32 55 FOBS=   72.1 SIGMA=  2.9 PHAS=  169.9 FOM= 0.73 TEST= 0
INDE 11 32 57 FOBS=   23.9 SIGMA=  8.7 PHAS=  -85.1 FOM= 0.05 TEST= 1
INDE 11 32 59 FOBS=    0.0 SIGMA= 21.7 PHAS=    0.0 FOM= 0.00 TEST= 0
INDE 11 32 61 FOBS=   33.0 SIGMA=  6.2 PHAS= -129.8 FOM= 0.36 TEST= 0
INDE 11 32 63 FOBS=   34.7 SIGMA=  5.5 PHAS=  119.2 FOM= 0.21 TEST= 0
INDE 11 32 65 FOBS=   20.6 SIGMA= 10.4 PHAS= -151.4 FOM= 0.23 TEST= 1
INDE 11 32 67 FOBS=   54.4 SIGMA=  4.6 PHAS=  172.4 FOM= 0.79 TEST= 0
INDE 11 32 69 FOBS=   94.9 SIGMA=  2.7 PHAS=   91.8 FOM= 0.93 TEST= 0
INDE 11 33 12 FOBS=  171.4 SIGMA=  0.7 PHAS=   -1.9 FOM= 0.93 TEST= 0
INDE 11 33 14 FOBS=  220.0 SIGMA=  0.7 PHAS=   33.6 FOM= 0.98 TEST= 0
INDE 11 33 16 FOBS=  213.9 SIGMA=  0.8 PHAS=  -81.2 FOM= 0.99 TEST= 0
INDE 11 33 18 FOBS=  121.9 SIGMA=  1.3 PHAS=   24.5 FOM= 0.94 TEST= 0
INDE 11 33 20 FOBS=  296.6 SIGMA=  0.7 PHAS=  158.3 FOM= 0.96 TEST= 0
INDE 11 33 22 FOBS=  210.8 SIGMA=  0.9 PHAS= -133.3 FOM= 0.90 TEST= 0
INDE 11 33 24 FOBS=  160.4 SIGMA=  1.1 PHAS=   -8.4 FOM= 0.99 TEST= 1
INDE 11 33 26 FOBS=  170.7 SIGMA=  1.2 PHAS=   20.1 FOM= 0.99 TEST= 0
INDE 11 33 28 FOBS=  102.9 SIGMA=  1.9 PHAS=   94.2 FOM= 0.90 TEST= 0
INDE 11 33 30 FOBS=  190.4 SIGMA=  1.1 PHAS=  130.5 FOM= 0.93 TEST= 0
INDE 11 33 32 FOBS=  259.8 SIGMA=  0.9 PHAS=   87.7 FOM= 0.95 TEST= 0
INDE 11 33 34 FOBS=  300.3 SIGMA=  1.0 PHAS= -126.2 FOM= 0.96 TEST= 0
INDE 11 33 36 FOBS=   96.0 SIGMA=  2.1 PHAS=  148.1 FOM= 0.89 TEST= 0
INDE 11 33 38 FOBS=  144.1 SIGMA=  1.5 PHAS=    5.7 FOM= 0.75 TEST= 0
INDE 11 33 40 FOBS=  106.4 SIGMA=  2.3 PHAS=  125.2 FOM= 0.89 TEST= 0
INDE 11 33 42 FOBS=  129.0 SIGMA=  1.8 PHAS=  -85.0 FOM= 0.89 TEST= 0
INDE 11 33 44 FOBS=   74.2 SIGMA=  3.1 PHAS=  -63.2 FOM= 0.63 TEST= 0
INDE 11 33 46 FOBS=   83.3 SIGMA=  2.7 PHAS=   89.5 FOM= 0.93 TEST= 0
INDE 11 33 48 FOBS=  143.4 SIGMA=  1.6 PHAS=   95.5 FOM= 0.93 TEST= 0
INDE 11 33 50 FOBS=  115.9 SIGMA=  1.7 PHAS=   97.4 FOM= 0.89 TEST= 0
INDE 11 33 52 FOBS=   68.2 SIGMA=  2.8 PHAS=  -26.7 FOM= 0.75 TEST= 1
INDE 11 33 54 FOBS=   81.2 SIGMA=  2.4 PHAS=   44.6 FOM= 0.86 TEST= 1
INDE 11 33 56 FOBS=   47.7 SIGMA=  4.4 PHAS=  173.4 FOM= 0.06 TEST= 0
INDE 11 33 58 FOBS=   71.3 SIGMA=  2.7 PHAS=  -10.4 FOM= 0.87 TEST= 0
INDE 11 33 60 FOBS=   12.7 SIGMA= 23.3 PHAS= -171.8 FOM= 0.33 TEST= 0
INDE 11 33 62 FOBS=   46.6 SIGMA=  3.7 PHAS=  -89.2 FOM= 0.58 TEST= 0
INDE 11 33 64 FOBS=   45.3 SIGMA=  3.8 PHAS=  -96.6 FOM= 0.76 TEST= 0
INDE 11 33 66 FOBS=    0.0 SIGMA= 20.9 PHAS=    0.0 FOM= 0.00 TEST= 1
INDE 11 33 68 FOBS=    0.0 SIGMA= 22.6 PHAS=    0.0 FOM= 0.00 TEST= 0
INDE 11 34 11 FOBS=  123.1 SIGMA=  0.9 PHAS=   -2.4 FOM= 0.95 TEST= 0
INDE 11 34 13 FOBS=  306.5 SIGMA=  0.7 PHAS= -116.5 FOM= 0.95 TEST= 0
INDE 11 34 15 FOBS=  145.0 SIGMA=  1.0 PHAS= -112.1 FOM= 0.95 TEST= 0
INDE 11 34 17 FOBS=  255.9 SIGMA=  0.7 PHAS=  -92.5 FOM= 0.98 TEST= 0
INDE 11 34 19 FOBS=  126.8 SIGMA=  1.2 PHAS=  -56.3 FOM= 0.96 TEST= 0
INDE 11 34 21 FOBS=  121.2 SIGMA=  1.4 PHAS=   25.3 FOM= 0.89 TEST= 0
INDE 11 34 23 FOBS=  133.5 SIGMA=  1.3 PHAS=  -38.2 FOM= 0.94 TEST= 0
INDE 11 34 25 FOBS=  117.1 SIGMA=  1.5 PHAS=  -48.3 FOM= 0.95 TEST= 0
INDE 11 34 27 FOBS=  126.0 SIGMA=  1.6 PHAS= -113.8 FOM= 0.97 TEST= 0
INDE 11 34 29 FOBS=   74.5 SIGMA=  2.8 PHAS=  172.4 FOM= 0.76 TEST= 0
INDE 11 34 31 FOBS=  157.4 SIGMA=  1.3 PHAS=   68.5 FOM= 0.50 TEST= 0
INDE 11 34 33 FOBS=   72.9 SIGMA=  2.9 PHAS=   93.7 FOM= 0.86 TEST= 0
INDE 11 34 35 FOBS=  128.7 SIGMA=  1.6 PHAS=  155.3 FOM= 0.79 TEST= 0
INDE 11 34 37 FOBS=  285.7 SIGMA=  0.8 PHAS=   21.3 FOM= 0.97 TEST= 0
INDE 11 34 39 FOBS=  174.6 SIGMA=  1.3 PHAS=   15.3 FOM= 0.92 TEST= 0
INDE 11 34 41 FOBS=  193.6 SIGMA=  1.3 PHAS= -146.9 FOM= 0.96 TEST= 0
INDE 11 34 43 FOBS=  199.7 SIGMA=  1.3 PHAS=  128.4 FOM= 0.95 TEST= 0
INDE 11 34 45 FOBS=   73.6 SIGMA=  3.1 PHAS=  -61.1 FOM= 0.81 TEST= 0
INDE 11 34 47 FOBS=  105.2 SIGMA=  2.2 PHAS=  -90.8 FOM= 0.85 TEST= 0
INDE 11 34 49 FOBS=   61.4 SIGMA=  3.6 PHAS=   43.3 FOM= 0.84 TEST= 0
INDE 11 34 51 FOBS=   44.5 SIGMA=  4.8 PHAS=   49.6 FOM= 0.20 TEST= 0
INDE 11 34 53 FOBS=    0.0 SIGMA= 19.1 PHAS=    0.0 FOM= 0.00 TEST= 0
INDE 11 34 55 FOBS=  116.7 SIGMA=  1.9 PHAS=  -73.2 FOM= 0.94 TEST= 0
INDE 11 34 57 FOBS=   80.9 SIGMA=  2.6 PHAS= -119.1 FOM= 0.79 TEST= 0
INDE 11 34 59 FOBS=    0.0 SIGMA= 21.5 PHAS=    0.0 FOM= 0.00 TEST= 0
INDE 11 34 61 FOBS=   50.1 SIGMA=  4.1 PHAS=  165.2 FOM= 0.30 TEST= 0
```

*FIG. 12A - 289*

```
INDE  11  34  63  FOBS=   58.9  SIGMA=   2.9  PHAS=  -141.3  FOM=  0.45  TEST= 0
INDE  11  34  65  FOBS=   43.0  SIGMA=   4.4  PHAS=   -31.5  FOM=  0.51  TEST= 0
INDE  11  34  67  FOBS=    0.0  SIGMA=  20.9  PHAS=     0.0  FOM=  0.00  TEST= 0
INDE  11  34  69  FOBS=   23.5  SIGMA=  10.6  PHAS=  -155.3  FOM=  0.21  TEST= 0
INDE  11  35  12  FOBS=  179.4  SIGMA=   0.9  PHAS=   127.6  FOM=  0.92  TEST= 0
INDE  11  35  14  FOBS=  464.1  SIGMA=   0.7  PHAS=    88.7  FOM=  0.98  TEST= 0
INDE  11  35  16  FOBS=  139.7  SIGMA=   1.1  PHAS=   162.8  FOM=  0.95  TEST= 0
INDE  11  35  18  FOBS=   90.1  SIGMA=   1.8  PHAS=   -92.1  FOM=  0.91  TEST= 0
INDE  11  35  20  FOBS=  320.1  SIGMA=   0.7  PHAS=  -161.0  FOM=  0.96  TEST= 0
INDE  11  35  22  FOBS=  409.7  SIGMA=   0.7  PHAS=   -46.0  FOM=  0.91  TEST= 1
INDE  11  35  24  FOBS=  167.7  SIGMA=   1.1  PHAS=   -27.2  FOM=  0.94  TEST= 0
INDE  11  35  26  FOBS=   14.1  SIGMA=  14.0  PHAS=   -50.3  FOM=  0.30  TEST= 0
INDE  11  35  28  FOBS=  127.7  SIGMA=   1.7  PHAS=  -175.3  FOM=  0.95  TEST= 0
INDE  11  35  30  FOBS=  293.6  SIGMA=   0.9  PHAS=    84.6  FOM=  0.98  TEST= 0
INDE  11  35  32  FOBS=  160.3  SIGMA=   1.4  PHAS=    69.1  FOM=  0.93  TEST= 0
INDE  11  35  34  FOBS=  130.8  SIGMA=   1.6  PHAS=   -62.0  FOM=  0.93  TEST= 0
INDE  11  35  36  FOBS=  205.8  SIGMA=   1.1  PHAS=    71.2  FOM=  0.59  TEST= 1
INDE  11  35  38  FOBS=  238.1  SIGMA=   0.9  PHAS=   -76.5  FOM=  0.96  TEST= 0
INDE  11  35  40  FOBS=  101.0  SIGMA=   1.9  PHAS=    43.1  FOM=  0.80  TEST= 0
INDE  11  35  42  FOBS=  170.8  SIGMA=   1.5  PHAS=    60.9  FOM=  0.88  TEST= 1
INDE  11  35  44  FOBS=   90.1  SIGMA=   2.6  PHAS=    61.2  FOM=  0.90  TEST= 0
INDE  11  35  46  FOBS=    0.0  SIGMA=  21.1  PHAS=     0.0  FOM=  0.00  TEST= 0
INDE  11  35  48  FOBS=    0.0  SIGMA=  21.8  PHAS=     0.0  FOM=  0.00  TEST= 0
INDE  11  35  50  FOBS=   77.8  SIGMA=   2.8  PHAS=    48.6  FOM=  0.71  TEST= 0
INDE  11  35  52  FOBS=   64.9  SIGMA=   3.3  PHAS=   -73.1  FOM=  0.37  TEST= 0
INDE  11  35  54  FOBS=   19.5  SIGMA=  13.6  PHAS=  -115.2  FOM=  0.36  TEST= 0
INDE  11  35  56  FOBS=  124.5  SIGMA=   1.8  PHAS=  -160.5  FOM=  0.89  TEST= 0
INDE  11  35  58  FOBS=   27.9  SIGMA=   7.4  PHAS=    -0.9  FOM=  0.39  TEST= 0
INDE  11  35  60  FOBS=   69.1  SIGMA=   3.0  PHAS=   -14.9  FOM=  0.70  TEST= 0
INDE  11  35  62  FOBS=    0.0  SIGMA=  20.6  PHAS=     0.0  FOM=  0.00  TEST= 0
INDE  11  35  64  FOBS=   26.9  SIGMA=   7.3  PHAS=   -92.6  FOM=  0.46  TEST= 0
INDE  11  35  66  FOBS=   44.4  SIGMA=   5.0  PHAS=   -45.9  FOM=  0.60  TEST= 0
INDE  11  35  68  FOBS=    0.0  SIGMA=  21.2  PHAS=     0.0  FOM=  0.00  TEST= 0
INDE  11  36  11  FOBS=  472.4  SIGMA=   0.6  PHAS=   111.7  FOM=  0.99  TEST= 0
INDE  11  36  13  FOBS=  336.8  SIGMA=   0.6  PHAS=    30.6  FOM=  0.99  TEST= 0
INDE  11  36  15  FOBS=  323.9  SIGMA=   0.6  PHAS=   -33.6  FOM=  0.98  TEST= 0
INDE  11  36  17  FOBS=  109.3  SIGMA=   1.5  PHAS=   -11.7  FOM=  0.97  TEST= 0
INDE  11  36  19  FOBS=  227.7  SIGMA=   0.9  PHAS=  -137.6  FOM=  0.93  TEST= 0
INDE  11  36  21  FOBS=  411.7  SIGMA=   0.6  PHAS=  -177.3  FOM=  0.96  TEST= 0
INDE  11  36  23  FOBS=  208.6  SIGMA=   1.0  PHAS=  -123.8  FOM=  0.98  TEST= 1
INDE  11  36  25  FOBS=  157.9  SIGMA=   1.2  PHAS=  -131.9  FOM=  0.87  TEST= 0
INDE  11  36  27  FOBS=  298.3  SIGMA=   0.9  PHAS=    15.9  FOM=  0.96  TEST= 0
INDE  11  36  29  FOBS=  118.4  SIGMA=   1.9  PHAS=   -88.8  FOM=  0.57  TEST= 0
INDE  11  36  31  FOBS=  233.4  SIGMA=   1.1  PHAS=    31.2  FOM=  0.90  TEST= 1
INDE  11  36  33  FOBS=   70.3  SIGMA=   3.0  PHAS=    34.2  FOM=  0.78  TEST= 0
INDE  11  36  35  FOBS=  270.6  SIGMA=   0.9  PHAS=   158.2  FOM=  0.93  TEST= 0
INDE  11  36  37  FOBS=   65.5  SIGMA=   3.0  PHAS=    20.4  FOM=  0.81  TEST= 0
INDE  11  36  39  FOBS=   48.7  SIGMA=   4.2  PHAS=   152.6  FOM=  0.64  TEST= 0
INDE  11  36  41  FOBS=  121.3  SIGMA=   1.6  PHAS=   -51.8  FOM=  0.76  TEST= 1
INDE  11  36  43  FOBS=    0.0  SIGMA=  23.9  PHAS=     0.0  FOM=  0.00  TEST= 1
INDE  11  36  45  FOBS=   73.1  SIGMA=   3.1  PHAS=   177.7  FOM=  0.65  TEST= 0
INDE  11  36  47  FOBS=   66.3  SIGMA=   3.4  PHAS=  -150.0  FOM=  0.85  TEST= 0
INDE  11  36  49  FOBS=   48.5  SIGMA=   4.5  PHAS=   -50.4  FOM=  0.79  TEST= 1
INDE  11  36  51  FOBS=    0.0  SIGMA=  22.0  PHAS=     0.0  FOM=  0.00  TEST= 0
INDE  11  36  53  FOBS=    0.0  SIGMA=  23.1  PHAS=     0.0  FOM=  0.00  TEST= 0
INDE  11  36  55  FOBS=   20.1  SIGMA=  10.5  PHAS=   -55.9  FOM=  0.26  TEST= 1
INDE  11  36  57  FOBS=   30.0  SIGMA=   7.6  PHAS=   125.2  FOM=  0.53  TEST= 0
INDE  11  36  59  FOBS=  119.3  SIGMA=   1.8  PHAS=  -106.3  FOM=  0.46  TEST= 1
INDE  11  36  61  FOBS=   68.7  SIGMA=   3.1  PHAS=  -130.1  FOM=  0.91  TEST= 0
INDE  11  36  63  FOBS=   62.8  SIGMA=   2.8  PHAS=   113.2  FOM=  0.67  TEST= 0
INDE  11  36  65  FOBS=   12.4  SIGMA=  15.5  PHAS=  -140.8  FOM=  0.34  TEST= 0
INDE  11  36  67  FOBS=   23.6  SIGMA=   9.9  PHAS=   106.0  FOM=  0.07  TEST= 0
INDE  11  37  12  FOBS=  308.5  SIGMA=   0.7  PHAS=   -16.2  FOM=  0.97  TEST= 0
INDE  11  37  14  FOBS=  224.5  SIGMA=   0.8  PHAS=  -100.2  FOM=  0.95  TEST= 1
INDE  11  37  16  FOBS=  264.9  SIGMA=   0.7  PHAS=   -21.6  FOM=  0.79  TEST= 1
INDE  11  37  18  FOBS=  188.0  SIGMA=   1.0  PHAS=  -139.6  FOM=  0.91  TEST= 0
INDE  11  37  20  FOBS=  465.9  SIGMA=   0.6  PHAS=   141.4  FOM=  0.97  TEST= 0
INDE  11  37  22  FOBS=   63.8  SIGMA=   2.8  PHAS=   100.3  FOM=  0.43  TEST= 1
INDE  11  37  24  FOBS=  237.2  SIGMA=   0.9  PHAS=   141.8  FOM=  0.97  TEST= 0
INDE  11  37  26  FOBS=  286.8  SIGMA=   0.8  PHAS=    19.3  FOM=  0.98  TEST= 0
```

*FIG. 12A - 290*

```
INDE 11 37 28 FOBS=  228.5 SIGMA=  1.1 PHAS=  -22.5 FOM= 0.89 TEST= 0
INDE 11 37 30 FOBS=   72.7 SIGMA=  3.1 PHAS=   54.9 FOM= 0.64 TEST= 0
INDE 11 37 32 FOBS=   86.7 SIGMA=  2.5 PHAS=   76.7 FOM= 0.91 TEST= 0
INDE 11 37 34 FOBS=  203.3 SIGMA=  1.1 PHAS=    7.4 FOM= 0.97 TEST= 0
INDE 11 37 36 FOBS=   64.5 SIGMA=  3.1 PHAS=   48.7 FOM= 0.67 TEST= 0
INDE 11 37 38 FOBS=  140.9 SIGMA=  1.5 PHAS=  -31.6 FOM= 0.86 TEST= 0
INDE 11 37 40 FOBS=  125.0 SIGMA=  1.6 PHAS=  123.1 FOM= 0.87 TEST= 1
INDE 11 37 42 FOBS=  102.3 SIGMA=  1.9 PHAS= -145.3 FOM= 0.90 TEST= 0
INDE 11 37 44 FOBS=    0.0 SIGMA= 23.4 PHAS=    0.0 FOM= 0.00 TEST= 0
INDE 11 37 46 FOBS=   95.6 SIGMA=  2.4 PHAS=  134.0 FOM= 0.90 TEST= 0
INDE 11 37 48 FOBS=  115.7 SIGMA=  2.0 PHAS= -146.7 FOM= 0.92 TEST= 0
INDE 11 37 50 FOBS=   90.6 SIGMA=  2.5 PHAS= -169.0 FOM= 0.89 TEST= 0
INDE 11 37 52 FOBS=   60.5 SIGMA=  3.6 PHAS=  -69.9 FOM= 0.86 TEST= 0
INDE 11 37 54 FOBS=   68.8 SIGMA=  3.1 PHAS=  -81.1 FOM= 0.78 TEST= 0
INDE 11 37 56 FOBS=   56.8 SIGMA=  3.7 PHAS= -100.9 FOM= 0.15 TEST= 1
INDE 11 37 58 FOBS=   99.4 SIGMA=  2.2 PHAS=  -31.6 FOM= 0.93 TEST= 0
INDE 11 37 60 FOBS=   11.1 SIGMA= 23.6 PHAS=  134.4 FOM= 0.25 TEST= 0
INDE 11 37 62 FOBS=   38.8 SIGMA=  6.0 PHAS=   78.3 FOM= 0.82 TEST= 0
INDE 11 37 64 FOBS=    9.9 SIGMA= 20.8 PHAS= -157.8 FOM= 0.02 TEST= 0
INDE 11 37 66 FOBS=    0.0 SIGMA= 21.5 PHAS=    0.0 FOM= 0.00 TEST= 1
INDE 11 38 11 FOBS=  179.9 SIGMA=  0.8 PHAS= -118.1 FOM= 0.90 TEST= 1
INDE 11 38 13 FOBS=   69.3 SIGMA=  2.2 PHAS=  118.4 FOM= 0.95 TEST= 0
INDE 11 38 15 FOBS=  235.9 SIGMA=  0.8 PHAS=  -98.1 FOM= 0.95 TEST= 0
INDE 11 38 17 FOBS=  233.0 SIGMA=  0.8 PHAS= -177.4 FOM= 0.95 TEST= 0
INDE 11 38 19 FOBS=   32.7 SIGMA=  5.6 PHAS= -128.9 FOM= 0.45 TEST= 1
INDE 11 38 21 FOBS=  110.1 SIGMA=  1.7 PHAS=  -21.4 FOM= 0.73 TEST= 0
INDE 11 38 23 FOBS=  269.5 SIGMA=  0.9 PHAS=  104.7 FOM= 0.99 TEST= 0
INDE 11 38 25 FOBS=  252.3 SIGMA=  0.9 PHAS=  -64.6 FOM= 0.93 TEST= 0
INDE 11 38 27 FOBS=  258.4 SIGMA=  0.9 PHAS=  -35.2 FOM= 0.97 TEST= 1
INDE 11 38 29 FOBS=  173.6 SIGMA=  1.4 PHAS= -133.3 FOM= 0.89 TEST= 0
INDE 11 38 31 FOBS=  162.7 SIGMA=  1.5 PHAS=   23.2 FOM= 0.95 TEST= 0
INDE 11 38 33 FOBS=  110.3 SIGMA=  1.9 PHAS=   26.5 FOM= 0.90 TEST= 0
INDE 11 38 35 FOBS=   70.6 SIGMA=  3.1 PHAS=  -51.6 FOM= 0.74 TEST= 0
INDE 11 38 37 FOBS=  161.5 SIGMA=  1.3 PHAS=  -55.4 FOM= 0.86 TEST= 0
INDE 11 38 39 FOBS=  154.7 SIGMA=  1.3 PHAS=  -27.7 FOM= 0.74 TEST= 0
INDE 11 38 41 FOBS=   59.1 SIGMA=  3.2 PHAS=  152.1 FOM= 0.86 TEST= 0
INDE 11 38 43 FOBS=   22.3 SIGMA=  8.2 PHAS=  -85.6 FOM= 0.33 TEST= 0
INDE 11 38 45 FOBS=   58.4 SIGMA=  3.9 PHAS=   15.1 FOM= 0.85 TEST= 0
INDE 11 38 47 FOBS=   58.3 SIGMA=  3.8 PHAS=  171.8 FOM= 0.79 TEST= 0
INDE 11 38 49 FOBS=   91.5 SIGMA=  2.5 PHAS= -137.5 FOM= 0.84 TEST= 0
INDE 11 38 51 FOBS=   85.4 SIGMA=  2.6 PHAS=   94.2 FOM= 0.92 TEST= 0
INDE 11 38 53 FOBS=   79.2 SIGMA=  2.8 PHAS= -133.6 FOM= 0.83 TEST= 0
INDE 11 38 55 FOBS=   53.4 SIGMA=  4.0 PHAS=   82.3 FOM= 0.09 TEST= 1
INDE 11 38 57 FOBS=   77.6 SIGMA=  2.8 PHAS=  151.7 FOM= 0.86 TEST= 0
INDE 11 38 59 FOBS=   95.6 SIGMA=  2.3 PHAS=  -71.7 FOM= 0.93 TEST= 0
INDE 11 38 61 FOBS=   43.7 SIGMA=  4.8 PHAS=   23.3 FOM= 0.75 TEST= 0
INDE 11 38 63 FOBS=   56.5 SIGMA=  3.2 PHAS= -110.5 FOM= 0.52 TEST= 0
INDE 11 38 65 FOBS=    7.9 SIGMA= 31.0 PHAS=   60.0 FOM= 0.01 TEST= 1
INDE 11 39 12 FOBS=  202.8 SIGMA=  0.9 PHAS=   88.8 FOM= 0.93 TEST= 0
INDE 11 39 14 FOBS=  148.7 SIGMA=  1.2 PHAS=   11.1 FOM= 0.96 TEST= 1
INDE 11 39 16 FOBS=   43.2 SIGMA=  3.8 PHAS=  164.9 FOM= 0.10 TEST= 1
INDE 11 39 18 FOBS=   94.1 SIGMA=  1.9 PHAS=  175.7 FOM= 0.92 TEST= 0
INDE 11 39 20 FOBS=  250.2 SIGMA=  0.9 PHAS=  161.1 FOM= 0.96 TEST= 0
INDE 11 39 22 FOBS=  173.0 SIGMA=  1.2 PHAS=  -18.3 FOM= 0.89 TEST= 0
INDE 11 39 24 FOBS=  144.9 SIGMA=  1.5 PHAS= -149.3 FOM= 0.87 TEST= 0
INDE 11 39 26 FOBS=  223.4 SIGMA=  1.1 PHAS=  -87.3 FOM= 0.97 TEST= 0
INDE 11 39 28 FOBS=   92.5 SIGMA=  2.4 PHAS=  136.9 FOM= 0.91 TEST= 0
INDE 11 39 30 FOBS=   68.6 SIGMA=  3.3 PHAS=  -87.6 FOM= 0.20 TEST= 0
INDE 11 39 32 FOBS=  146.0 SIGMA=  1.6 PHAS=  -48.9 FOM= 0.95 TEST= 1
INDE 11 39 34 FOBS=   16.2 SIGMA= 12.1 PHAS=  -24.7 FOM= 0.59 TEST= 0
INDE 11 39 36 FOBS=  173.9 SIGMA=  1.3 PHAS= -131.4 FOM= 0.91 TEST= 1
INDE 11 39 38 FOBS=   86.3 SIGMA=  2.3 PHAS=   32.2 FOM= 0.73 TEST= 0
INDE 11 39 40 FOBS=  137.9 SIGMA=  1.5 PHAS= -152.8 FOM= 0.83 TEST= 0
INDE 11 39 42 FOBS=   56.6 SIGMA=  3.3 PHAS=   99.5 FOM= 0.46 TEST= 0
INDE 11 39 44 FOBS=  108.9 SIGMA=  1.7 PHAS= -102.1 FOM= 0.86 TEST= 0
INDE 11 39 46 FOBS=   75.5 SIGMA=  3.0 PHAS=  136.3 FOM= 0.80 TEST= 0
INDE 11 39 48 FOBS=   98.2 SIGMA=  2.3 PHAS= -168.7 FOM= 0.89 TEST= 0
INDE 11 39 50 FOBS=   41.5 SIGMA=  5.3 PHAS=   20.0 FOM= 0.53 TEST= 1
INDE 11 39 52 FOBS=   31.1 SIGMA=  7.0 PHAS= -136.6 FOM= 0.20 TEST= 0
INDE 11 39 54 FOBS=   60.2 SIGMA=  3.6 PHAS= -162.9 FOM= 0.60 TEST= 0
```

*FIG. 12A - 291*

```
INDE 11 39 56 FOBS=    33.4 SIGMA=  6.3 PHAS=  101.8 FOM= 0.22 TEST= 1
INDE 11 39 58 FOBS=    89.9 SIGMA=  2.4 PHAS=  -37.1 FOM= 0.90 TEST= 0
INDE 11 39 60 FOBS=    39.5 SIGMA=  6.0 PHAS= -174.2 FOM= 0.72 TEST= 0
INDE 11 39 62 FOBS=    36.0 SIGMA=  5.0 PHAS=  -48.4 FOM= 0.35 TEST= 0
INDE 11 39 64 FOBS=    34.1 SIGMA=  6.2 PHAS= -101.1 FOM= 0.62 TEST= 0
INDE 11 39 66 FOBS=     0.0 SIGMA= 21.7 PHAS=    0.0 FOM= 0.00 TEST= 0
INDE 11 40 11 FOBS=   208.2 SIGMA=  0.9 PHAS=  -77.3 FOM= 0.96 TEST= 0
INDE 11 40 13 FOBS=   317.3 SIGMA=  0.7 PHAS=   -8.9 FOM= 0.95 TEST= 0
INDE 11 40 15 FOBS=   250.1 SIGMA=  0.8 PHAS=  -18.8 FOM= 0.92 TEST= 0
INDE 11 40 17 FOBS=   199.4 SIGMA=  1.0 PHAS=  176.6 FOM= 0.99 TEST= 0
INDE 11 40 19 FOBS=   245.6 SIGMA=  1.0 PHAS=   38.8 FOM= 0.96 TEST= 0
INDE 11 40 21 FOBS=    89.5 SIGMA=  2.2 PHAS=    2.1 FOM= 0.78 TEST= 0
INDE 11 40 23 FOBS=   275.4 SIGMA=  0.9 PHAS=  166.6 FOM= 0.88 TEST= 1
INDE 11 40 25 FOBS=   125.7 SIGMA=  1.8 PHAS= -120.0 FOM= 0.90 TEST= 0
INDE 11 40 27 FOBS=   145.6 SIGMA=  1.5 PHAS=  161.0 FOM= 0.86 TEST= 0
INDE 11 40 29 FOBS=   297.7 SIGMA=  0.9 PHAS=   44.8 FOM= 0.96 TEST= 0
INDE 11 40 31 FOBS=   113.0 SIGMA=  2.0 PHAS=  -98.2 FOM= 0.90 TEST= 0
INDE 11 40 33 FOBS=   288.6 SIGMA=  1.4 PHAS=  118.1 FOM= 0.97 TEST= 0
INDE 11 40 35 FOBS=   202.0 SIGMA=  1.1 PHAS=   93.8 FOM= 0.82 TEST= 1
INDE 11 40 37 FOBS=   208.7 SIGMA=  1.1 PHAS= -107.6 FOM= 0.97 TEST= 0
INDE 11 40 39 FOBS=    90.9 SIGMA=  2.2 PHAS=   21.1 FOM= 0.66 TEST= 0
INDE 11 40 41 FOBS=    10.6 SIGMA= 18.9 PHAS=  -18.3 FOM= 0.27 TEST= 0
INDE 11 40 43 FOBS=    55.1 SIGMA=  3.7 PHAS=  175.2 FOM= 0.54 TEST= 0
INDE 11 40 45 FOBS=    44.8 SIGMA=  4.3 PHAS=  118.4 FOM= 0.33 TEST= 1
INDE 11 40 47 FOBS=    14.8 SIGMA= 15.0 PHAS=  -81.9 FOM= 0.22 TEST= 0
INDE 11 40 49 FOBS=   101.2 SIGMA=  2.2 PHAS=  -71.6 FOM= 0.29 TEST= 0
INDE 11 40 51 FOBS=    64.6 SIGMA=  3.4 PHAS=  107.4 FOM= 0.64 TEST= 0
INDE 11 40 53 FOBS=    59.5 SIGMA=  3.7 PHAS=   92.5 FOM= 0.70 TEST= 0
INDE 11 40 55 FOBS=    61.1 SIGMA=  3.5 PHAS=   75.4 FOM= 0.31 TEST= 0
INDE 11 40 57 FOBS=    31.4 SIGMA=  6.8 PHAS=  154.5 FOM= 0.64 TEST= 0
INDE 11 40 59 FOBS=    80.6 SIGMA=  2.7 PHAS=  -72.9 FOM= 0.90 TEST= 0
INDE 11 40 61 FOBS=    87.5 SIGMA=  2.5 PHAS=   48.5 FOM= 0.95 TEST= 0
INDE 11 40 63 FOBS=    47.6 SIGMA=  5.0 PHAS= -140.4 FOM= 0.85 TEST= 0
INDE 11 40 65 FOBS=    36.9 SIGMA=  5.9 PHAS=   47.2 FOM= 0.56 TEST= 0
INDE 11 41 12 FOBS=   343.9 SIGMA=  0.8 PHAS=  162.0 FOM= 0.96 TEST= 0
INDE 11 41 14 FOBS=    35.7 SIGMA=  4.9 PHAS= -113.6 FOM= 0.07 TEST= 0
INDE 11 41 16 FOBS=    57.7 SIGMA=  3.2 PHAS=  -31.6 FOM= 0.60 TEST= 1
INDE 11 41 18 FOBS=   132.9 SIGMA=  1.5 PHAS=  -67.9 FOM= 0.91 TEST= 0
INDE 11 41 20 FOBS=   196.7 SIGMA=  1.2 PHAS=  -75.9 FOM= 0.93 TEST= 0
INDE 11 41 22 FOBS=   172.3 SIGMA=  1.3 PHAS=   89.9 FOM= 0.92 TEST= 0
INDE 11 41 24 FOBS=   106.8 SIGMA=  2.1 PHAS=  -54.1 FOM= 0.90 TEST= 0
INDE 11 41 26 FOBS=   132.8 SIGMA=  1.7 PHAS=   17.3 FOM= 0.92 TEST= 0
INDE 11 41 28 FOBS=    57.9 SIGMA=  3.7 PHAS=  -38.8 FOM= 0.38 TEST= 0
INDE 11 41 30 FOBS=   207.0 SIGMA=  1.1 PHAS=  -70.6 FOM= 0.92 TEST= 0
INDE 11 41 32 FOBS=   253.8 SIGMA=  1.0 PHAS=   34.5 FOM= 0.96 TEST= 0
INDE 11 41 34 FOBS=   237.2 SIGMA=  1.2 PHAS=  -54.0 FOM= 0.18 TEST= 1
INDE 11 41 36 FOBS=   126.3 SIGMA=  1.6 PHAS=  113.1 FOM= 0.79 TEST= 1
INDE 11 41 38 FOBS=     0.0 SIGMA= 19.6 PHAS=    0.0 FOM= 0.00 TEST= 0
INDE 11 41 40 FOBS=   109.2 SIGMA=  1.8 PHAS=   23.4 FOM= 0.75 TEST= 0
INDE 11 41 42 FOBS=    96.5 SIGMA=  2.0 PHAS=   73.1 FOM= 0.45 TEST= 1
INDE 11 41 44 FOBS=   122.2 SIGMA=  1.6 PHAS= -178.4 FOM= 0.86 TEST= 0
INDE 11 41 46 FOBS=   147.1 SIGMA=  1.3 PHAS= -171.8 FOM= 0.93 TEST= 0
INDE 11 41 48 FOBS=   125.6 SIGMA=  1.5 PHAS= -168.3 FOM= 0.93 TEST= 0
INDE 11 41 50 FOBS=    43.7 SIGMA=  5.0 PHAS= -137.9 FOM= 0.50 TEST= 0
INDE 11 41 52 FOBS=    80.1 SIGMA=  2.8 PHAS= -125.0 FOM= 0.46 TEST= 0
INDE 11 41 54 FOBS=    82.0 SIGMA=  2.7 PHAS=   30.0 FOM= 0.87 TEST= 0
INDE 11 41 56 FOBS=     0.0 SIGMA= 20.7 PHAS=    0.0 FOM= 0.00 TEST= 0
INDE 11 41 58 FOBS=    96.1 SIGMA=  2.3 PHAS=  128.3 FOM= 0.62 TEST= 0
INDE 11 41 60 FOBS=    58.5 SIGMA=  3.7 PHAS=   -8.2 FOM= 0.88 TEST= 0
INDE 11 41 62 FOBS=    94.2 SIGMA=  2.4 PHAS=  -30.4 FOM= 0.26 TEST= 1
INDE 11 41 64 FOBS=    25.3 SIGMA= 10.6 PHAS=  124.6 FOM= 0.54 TEST= 0
INDE 11 42 11 FOBS=   208.1 SIGMA=  1.0 PHAS=  153.6 FOM= 0.92 TEST= 0
INDE 11 42 13 FOBS=   331.5 SIGMA=  0.8 PHAS=    3.6 FOM= 0.98 TEST= 0
INDE 11 42 15 FOBS=    91.0 SIGMA=  2.1 PHAS=   19.8 FOM= 0.86 TEST= 0
INDE 11 42 17 FOBS=   273.5 SIGMA=  0.9 PHAS=  159.7 FOM= 0.97 TEST= 0
INDE 11 42 19 FOBS=   200.7 SIGMA=  1.2 PHAS= -120.9 FOM= 0.94 TEST= 0
INDE 11 42 21 FOBS=   103.8 SIGMA=  2.1 PHAS=  -57.0 FOM= 0.77 TEST= 0
INDE 11 42 23 FOBS=   130.3 SIGMA=  1.7 PHAS= -130.0 FOM= 0.96 TEST= 0
INDE 11 42 25 FOBS=   160.2 SIGMA=  1.4 PHAS= -102.4 FOM= 0.94 TEST= 0
INDE 11 42 27 FOBS=    46.9 SIGMA=  4.5 PHAS=   46.0 FOM= 0.48 TEST= 0
```

*FIG. 12A - 292*

```
INDE  11  42  29  FOBS=   230.9  SIGMA=   1.0  PHAS=    50.7  FOM=  0.93  TEST= 0
INDE  11  42  31  FOBS=   103.2  SIGMA=   2.2  PHAS=  -135.2  FOM=  0.90  TEST= 0
INDE  11  42  33  FOBS=   140.9  SIGMA=   1.6  PHAS=   119.8  FOM=  0.90  TEST= 0
INDE  11  42  35  FOBS=   125.6  SIGMA=   1.7  PHAS=    44.6  FOM=  0.81  TEST= 0
INDE  11  42  37  FOBS=   105.9  SIGMA=   1.9  PHAS=   -21.0  FOM=  0.93  TEST= 0
INDE  11  42  39  FOBS=    58.5  SIGMA=   3.3  PHAS=   -80.6  FOM=  0.84  TEST= 0
INDE  11  42  41  FOBS=    90.1  SIGMA=   2.2  PHAS=   -16.6  FOM=  0.66  TEST= 0
INDE  11  42  43  FOBS=    94.6  SIGMA=   2.0  PHAS=    41.0  FOM=  0.92  TEST= 0
INDE  11  42  45  FOBS=    93.5  SIGMA=   2.0  PHAS=    23.5  FOM=  0.90  TEST= 0
INDE  11  42  47  FOBS=    71.0  SIGMA=   2.6  PHAS=    61.4  FOM=  0.79  TEST= 0
INDE  11  42  49  FOBS=   167.9  SIGMA=   1.4  PHAS=   105.2  FOM=  0.95  TEST= 0
INDE  11  42  51  FOBS=    94.2  SIGMA=   2.4  PHAS=    59.3  FOM=  0.93  TEST= 0
INDE  11  42  53  FOBS=     0.0  SIGMA=  21.8  PHAS=     0.0  FOM=  0.00  TEST= 0
INDE  11  42  55  FOBS=     0.0  SIGMA=  21.7  PHAS=     0.0  FOM=  0.00  TEST= 0
INDE  11  42  57  FOBS=    43.8  SIGMA=   6.1  PHAS=    90.3  FOM=  0.78  TEST= 0
INDE  11  42  59  FOBS=     0.0  SIGMA=  21.7  PHAS=     0.0  FOM=  0.00  TEST= 0
INDE  11  42  61  FOBS=     0.0  SIGMA=  20.8  PHAS=     0.0  FOM=  0.00  TEST= 0
INDE  11  42  63  FOBS=    56.5  SIGMA=   4.0  PHAS=   -59.7  FOM=  0.80  TEST= 0
INDE  11  43  12  FOBS=    51.2  SIGMA=   4.9  PHAS=   162.5  FOM=  0.20  TEST= 0
INDE  11  43  14  FOBS=   261.1  SIGMA=   0.9  PHAS=  -112.1  FOM=  0.98  TEST= 0
INDE  11  43  16  FOBS=   167.0  SIGMA=   1.3  PHAS=    60.6  FOM=  0.91  TEST= 0
INDE  11  43  18  FOBS=   171.8  SIGMA=   1.3  PHAS=    64.2  FOM=  0.94  TEST= 0
INDE  11  43  20  FOBS=   308.1  SIGMA=   0.9  PHAS=  -155.2  FOM=  0.98  TEST= 0
INDE  11  43  22  FOBS=   137.3  SIGMA=   1.6  PHAS=  -155.8  FOM=  0.83  TEST= 0
INDE  11  43  24  FOBS=    57.5  SIGMA=   3.7  PHAS=   -99.4  FOM=  0.79  TEST= 0
INDE  11  43  26  FOBS=   153.2  SIGMA=   1.5  PHAS=    15.4  FOM=  0.94  TEST= 0
INDE  11  43  28  FOBS=   149.9  SIGMA=   1.5  PHAS=   -85.0  FOM=  0.73  TEST= 0
INDE  11  43  30  FOBS=   101.2  SIGMA=   2.1  PHAS=   -53.7  FOM=  0.86  TEST= 0
INDE  11  43  32  FOBS=   225.0  SIGMA=   1.1  PHAS=    27.3  FOM=  0.93  TEST= 0
INDE  11  43  34  FOBS=    72.0  SIGMA=   3.0  PHAS=   -13.0  FOM=  0.78  TEST= 0
INDE  11  43  36  FOBS=    43.3  SIGMA=   4.4  PHAS=   -48.8  FOM=  0.91  TEST= 0
INDE  11  43  38  FOBS=    83.7  SIGMA=   2.3  PHAS=  -111.4  FOM=  0.89  TEST= 0
INDE  11  43  40  FOBS=     0.0  SIGMA=  19.5  PHAS=     0.0  FOM=  0.00  TEST= 0
INDE  11  43  42  FOBS=    55.2  SIGMA=   3.6  PHAS=    -6.6  FOM=  0.15  TEST= 0
INDE  11  43  44  FOBS=    50.9  SIGMA=   3.7  PHAS=  -154.7  FOM=  0.89  TEST= 0
INDE  11  43  46  FOBS=     0.0  SIGMA=  21.8  PHAS=     0.0  FOM=  0.00  TEST= 1
INDE  11  43  48  FOBS=     0.0  SIGMA=  19.1  PHAS=     0.0  FOM=  0.00  TEST= 0
INDE  11  43  50  FOBS=   100.4  SIGMA=   2.3  PHAS=     1.0  FOM=  0.94  TEST= 0
INDE  11  43  52  FOBS=    91.5  SIGMA=   2.4  PHAS=   -56.0  FOM=  0.90  TEST= 0
INDE  11  43  54  FOBS=    65.3  SIGMA=   3.4  PHAS=   -13.2  FOM=  0.77  TEST= 0
INDE  11  43  56  FOBS=    44.7  SIGMA=   4.9  PHAS=    74.5  FOM=  0.73  TEST= 0
INDE  11  43  58  FOBS=     0.0  SIGMA=  23.5  PHAS=     0.0  FOM=  0.00  TEST= 1
INDE  11  43  60  FOBS=     0.0  SIGMA=  22.1  PHAS=     0.0  FOM=  0.00  TEST= 1
INDE  11  43  62  FOBS=    79.6  SIGMA=   3.5  PHAS=   -95.7  FOM=  0.83  TEST= 0
INDE  11  44  11  FOBS=   318.0  SIGMA=   0.8  PHAS=  -109.1  FOM=  0.96  TEST= 0
INDE  11  44  13  FOBS=    75.9  SIGMA=   3.5  PHAS=  -111.2  FOM=  0.64  TEST= 0
INDE  11  44  15  FOBS=   201.5  SIGMA=   1.1  PHAS=   159.3  FOM=  0.95  TEST= 0
INDE  11  44  17  FOBS=   198.4  SIGMA=   1.2  PHAS=    20.5  FOM=  0.96  TEST= 1
INDE  11  44  19  FOBS=    75.5  SIGMA=   2.8  PHAS=   171.1  FOM=  0.88  TEST= 0
INDE  11  44  21  FOBS=   185.1  SIGMA=   1.2  PHAS=   139.1  FOM=  0.94  TEST= 0
INDE  11  44  23  FOBS=   156.8  SIGMA=   1.4  PHAS=  -105.6  FOM=  0.81  TEST= 0
INDE  11  44  25  FOBS=   110.2  SIGMA=   2.0  PHAS=   -63.4  FOM=  0.89  TEST= 0
INDE  11  44  27  FOBS=    55.7  SIGMA=   4.1  PHAS=  -110.1  FOM=  0.22  TEST= 0
INDE  11  44  29  FOBS=    18.6  SIGMA=  12.2  PHAS=   -32.2  FOM=  0.12  TEST= 0
INDE  11  44  31  FOBS=    65.1  SIGMA=   3.1  PHAS=    37.2  FOM=  0.30  TEST= 0
INDE  11  44  33  FOBS=   130.2  SIGMA=   1.7  PHAS=   162.8  FOM=  0.94  TEST= 1
INDE  11  44  35  FOBS=     0.0  SIGMA=  21.3  PHAS=     0.0  FOM=  0.00  TEST= 0
INDE  11  44  37  FOBS=    35.1  SIGMA=   6.3  PHAS=   -85.2  FOM=  0.81  TEST= 0
INDE  11  44  39  FOBS=   127.5  SIGMA=   1.6  PHAS=    84.5  FOM=  0.80  TEST= 0
INDE  11  44  41  FOBS=    36.4  SIGMA=   5.7  PHAS=    50.8  FOM=  0.28  TEST= 0
INDE  11  44  43  FOBS=    43.8  SIGMA=   4.4  PHAS=   -47.3  FOM=  0.34  TEST= 0
INDE  11  44  45  FOBS=   115.4  SIGMA=   1.7  PHAS=    18.6  FOM=  0.88  TEST= 0
INDE  11  44  47  FOBS=     9.9  SIGMA=  18.7  PHAS=    56.6  FOM=  0.06  TEST= 0
INDE  11  44  49  FOBS=     0.0  SIGMA=  18.9  PHAS=     0.0  FOM=  0.00  TEST= 0
INDE  11  44  51  FOBS=     0.0  SIGMA=  20.9  PHAS=     0.0  FOM=  0.00  TEST= 0
INDE  11  44  53  FOBS=    61.0  SIGMA=   3.6  PHAS=  -159.8  FOM=  0.86  TEST= 0
INDE  11  44  55  FOBS=    41.4  SIGMA=   5.3  PHAS=  -109.9  FOM=  0.61  TEST= 0
INDE  11  44  57  FOBS=    45.5  SIGMA=   4.9  PHAS=  -127.7  FOM=  0.49  TEST= 0
INDE  11  44  59  FOBS=   109.4  SIGMA=   2.1  PHAS=  -153.7  FOM=  0.94  TEST= 0
INDE  11  44  61  FOBS=    27.5  SIGMA=  10.0  PHAS=   -90.9  FOM=  0.22  TEST= 0
```

*FIG. 12A - 293*

| | | | | | | | | | | | |
|---|---|---|---|---|---|---|---|---|---|---|---|
| INDE | 11 | 44 | 63 | FOBS= | 0.0 | SIGMA= | 22.4 | PHAS= | 0.0 | FOM= 0.00 | TEST= 1 |
| INDE | 11 | 45 | 12 | FOBS= | 187.7 | SIGMA= | 1.6 | PHAS= | 89.5 | FOM= 0.97 | TEST= 0 |
| INDE | 11 | 45 | 14 | FOBS= | 0.0 | SIGMA= | 22.5 | PHAS= | 0.0 | FOM= 0.00 | TEST= 0 |
| INDE | 11 | 45 | 16 | FOBS= | 142.0 | SIGMA= | 1.5 | PHAS= | 23.6 | FOM= 0.89 | TEST= 1 |
| INDE | 11 | 45 | 18 | FOBS= | 125.5 | SIGMA= | 1.7 | PHAS= | -40.5 | FOM= 0.73 | TEST= 0 |
| INDE | 11 | 45 | 20 | FOBS= | 72.9 | SIGMA= | 3.1 | PHAS= | 81.2 | FOM= 0.81 | TEST= 0 |
| INDE | 11 | 45 | 22 | FOBS= | 74.3 | SIGMA= | 2.8 | PHAS= | 142.0 | FOM= 0.90 | TEST= 0 |
| INDE | 11 | 45 | 24 | FOBS= | 81.8 | SIGMA= | 2.6 | PHAS= | -138.2 | FOM= 0.91 | TEST= 0 |
| INDE | 11 | 45 | 26 | FOBS= | 93.7 | SIGMA= | 2.3 | PHAS= | -25.4 | FOM= 0.44 | TEST= 0 |
| INDE | 11 | 45 | 28 | FOBS= | 86.1 | SIGMA= | 2.4 | PHAS= | 128.6 | FOM= 0.83 | TEST= 0 |
| INDE | 11 | 45 | 30 | FOBS= | 118.3 | SIGMA= | 1.8 | PHAS= | -70.7 | FOM= 0.79 | TEST= 0 |
| INDE | 11 | 45 | 32 | FOBS= | 126.7 | SIGMA= | 1.7 | PHAS= | -14.7 | FOM= 0.95 | TEST= 0 |
| INDE | 11 | 45 | 34 | FOBS= | 45.2 | SIGMA= | 4.7 | PHAS= | -9.4 | FOM= 0.23 | TEST= 1 |
| INDE | 11 | 45 | 36 | FOBS= | 95.4 | SIGMA= | 2.3 | PHAS= | -140.4 | FOM= 0.83 | TEST= 0 |
| INDE | 11 | 45 | 38 | FOBS= | 0.0 | SIGMA= | 19.8 | PHAS= | 0.0 | FOM= 0.00 | TEST= 0 |
| INDE | 11 | 45 | 40 | FOBS= | 111.8 | SIGMA= | 1.8 | PHAS= | 95.0 | FOM= 0.25 | TEST= 1 |
| INDE | 11 | 45 | 42 | FOBS= | 49.2 | SIGMA= | 3.9 | PHAS= | 174.3 | FOM= 0.35 | TEST= 0 |
| INDE | 11 | 45 | 44 | FOBS= | 35.2 | SIGMA= | 5.7 | PHAS= | -104.0 | FOM= 0.47 | TEST= 0 |
| INDE | 11 | 45 | 46 | FOBS= | 93.0 | SIGMA= | 2.1 | PHAS= | 39.4 | FOM= 0.45 | TEST= 0 |
| INDE | 11 | 45 | 48 | FOBS= | 66.9 | SIGMA= | 2.8 | PHAS= | -127.3 | FOM= 0.82 | TEST= 0 |
| INDE | 11 | 45 | 50 | FOBS= | 26.6 | SIGMA= | 9.1 | PHAS= | -95.0 | FOM= 0.29 | TEST= 0 |
| INDE | 11 | 45 | 52 | FOBS= | 0.0 | SIGMA= | 21.8 | PHAS= | 0.0 | FOM= 0.00 | TEST= 0 |
| INDE | 11 | 45 | 54 | FOBS= | 47.1 | SIGMA= | 4.7 | PHAS= | 135.8 | FOM= 0.74 | TEST= 0 |
| INDE | 11 | 45 | 56 | FOBS= | 95.7 | SIGMA= | 2.4 | PHAS= | 108.5 | FOM= 0.92 | TEST= 0 |
| INDE | 11 | 45 | 58 | FOBS= | 111.0 | SIGMA= | 2.1 | PHAS= | 113.0 | FOM= 0.95 | TEST= 0 |
| INDE | 11 | 45 | 60 | FOBS= | 70.2 | SIGMA= | 3.9 | PHAS= | 131.7 | FOM= 0.66 | TEST= 0 |
| INDE | 11 | 45 | 62 | FOBS= | 70.1 | SIGMA= | 3.4 | PHAS= | -89.6 | FOM= 0.83 | TEST= 0 |
| INDE | 11 | 46 | 11 | FOBS= | 117.1 | SIGMA= | 2.5 | PHAS= | -26.1 | FOM= 0.47 | TEST= 0 |
| INDE | 11 | 46 | 13 | FOBS= | 191.4 | SIGMA= | 1.6 | PHAS= | -74.8 | FOM= 0.87 | TEST= 0 |
| INDE | 11 | 46 | 15 | FOBS= | 0.0 | SIGMA= | 22.4 | PHAS= | 0.0 | FOM= 0.00 | TEST= 0 |
| INDE | 11 | 46 | 17 | FOBS= | 133.6 | SIGMA= | 1.6 | PHAS= | 25.5 | FOM= 0.69 | TEST= 1 |
| INDE | 11 | 46 | 19 | FOBS= | 125.4 | SIGMA= | 1.7 | PHAS= | -137.7 | FOM= 0.86 | TEST= 0 |
| INDE | 11 | 46 | 21 | FOBS= | 91.6 | SIGMA= | 2.3 | PHAS= | -12.7 | FOM= 0.79 | TEST= 0 |
| INDE | 11 | 46 | 23 | FOBS= | 44.0 | SIGMA= | 4.7 | PHAS= | -178.5 | FOM= 0.77 | TEST= 0 |
| INDE | 11 | 46 | 25 | FOBS= | 121.9 | SIGMA= | 1.8 | PHAS= | 112.6 | FOM= 0.89 | TEST= 0 |
| INDE | 11 | 46 | 27 | FOBS= | 107.0 | SIGMA= | 2.0 | PHAS= | 0.0 | FOM= 0.59 | TEST= 1 |
| INDE | 11 | 46 | 29 | FOBS= | 111.8 | SIGMA= | 1.9 | PHAS= | 177.3 | FOM= 0.88 | TEST= 0 |
| INDE | 11 | 46 | 31 | FOBS= | 40.5 | SIGMA= | 5.0 | PHAS= | -145.9 | FOM= 0.44 | TEST= 0 |
| INDE | 11 | 46 | 33 | FOBS= | 53.2 | SIGMA= | 3.4 | PHAS= | -157.5 | FOM= 0.59 | TEST= 0 |
| INDE | 11 | 46 | 35 | FOBS= | 0.0 | SIGMA= | 20.5 | PHAS= | 0.0 | FOM= 0.00 | TEST= 0 |
| INDE | 11 | 46 | 37 | FOBS= | 0.0 | SIGMA= | 19.8 | PHAS= | 0.0 | FOM= 0.00 | TEST= 0 |
| INDE | 11 | 46 | 39 | FOBS= | 0.0 | SIGMA= | 19.9 | PHAS= | 0.0 | FOM= 0.00 | TEST= 0 |
| INDE | 11 | 46 | 41 | FOBS= | 65.2 | SIGMA= | 2.9 | PHAS= | 52.9 | FOM= 0.87 | TEST= 0 |
| INDE | 11 | 46 | 43 | FOBS= | 69.4 | SIGMA= | 2.8 | PHAS= | -55.2 | FOM= 0.86 | TEST= 0 |
| INDE | 11 | 46 | 45 | FOBS= | 34.4 | SIGMA= | 5.5 | PHAS= | -89.3 | FOM= 0.08 | TEST= 0 |
| INDE | 11 | 46 | 47 | FOBS= | 107.5 | SIGMA= | 1.8 | PHAS= | 124.7 | FOM= 0.80 | TEST= 0 |
| INDE | 11 | 46 | 49 | FOBS= | 0.0 | SIGMA= | 19.0 | PHAS= | 0.0 | FOM= 0.00 | TEST= 0 |
| INDE | 11 | 46 | 51 | FOBS= | 0.0 | SIGMA= | 20.7 | PHAS= | 0.0 | FOM= 0.00 | TEST= 0 |
| INDE | 11 | 46 | 53 | FOBS= | 73.3 | SIGMA= | 3.0 | PHAS= | 22.9 | FOM= 0.89 | TEST= 0 |
| INDE | 11 | 46 | 55 | FOBS= | 66.7 | SIGMA= | 3.4 | PHAS= | -150.4 | FOM= 0.06 | TEST= 1 |
| INDE | 11 | 46 | 57 | FOBS= | 40.9 | SIGMA= | 6.0 | PHAS= | 38.2 | FOM= 0.81 | TEST= 0 |
| INDE | 11 | 46 | 59 | FOBS= | 37.0 | SIGMA= | 7.4 | PHAS= | -7.8 | FOM= 0.47 | TEST= 0 |
| INDE | 11 | 46 | 61 | FOBS= | 33.4 | SIGMA= | 8.3 | PHAS= | -153.9 | FOM= 0.60 | TEST= 0 |
| INDE | 11 | 47 | 12 | FOBS= | 167.4 | SIGMA= | 1.8 | PHAS= | -8.4 | FOM= 0.55 | TEST= 1 |
| INDE | 11 | 47 | 14 | FOBS= | 45.0 | SIGMA= | 6.0 | PHAS= | 145.3 | FOM= 0.76 | TEST= 0 |
| INDE | 11 | 47 | 16 | FOBS= | 107.7 | SIGMA= | 1.9 | PHAS= | -51.3 | FOM= 0.88 | TEST= 0 |
| INDE | 11 | 47 | 18 | FOBS= | 228.5 | SIGMA= | 1.1 | PHAS= | 9.2 | FOM= 0.94 | TEST= 0 |
| INDE | 11 | 47 | 20 | FOBS= | 163.9 | SIGMA= | 1.3 | PHAS= | 2.0 | FOM= 0.89 | TEST= 1 |
| INDE | 11 | 47 | 22 | FOBS= | 17.1 | SIGMA= | 11.8 | PHAS= | 166.4 | FOM= 0.19 | TEST= 0 |
| INDE | 11 | 47 | 24 | FOBS= | 170.7 | SIGMA= | 1.3 | PHAS= | 20.6 | FOM= 0.93 | TEST= 0 |
| INDE | 11 | 47 | 26 | FOBS= | 83.4 | SIGMA= | 2.5 | PHAS= | -51.7 | FOM= 0.57 | TEST= 1 |
| INDE | 11 | 47 | 28 | FOBS= | 135.4 | SIGMA= | 1.6 | PHAS= | -153.2 | FOM= 0.83 | TEST= 0 |
| INDE | 11 | 47 | 30 | FOBS= | 88.3 | SIGMA= | 2.4 | PHAS= | 173.5 | FOM= 0.84 | TEST= 0 |
| INDE | 11 | 47 | 32 | FOBS= | 86.6 | SIGMA= | 2.4 | PHAS= | -131.3 | FOM= 0.93 | TEST= 0 |
| INDE | 11 | 47 | 34 | FOBS= | 0.0 | SIGMA= | 19.5 | PHAS= | 0.0 | FOM= 0.00 | TEST= 1 |
| INDE | 11 | 47 | 36 | FOBS= | 54.9 | SIGMA= | 3.8 | PHAS= | 176.0 | FOM= 0.80 | TEST= 0 |
| INDE | 11 | 47 | 38 | FOBS= | 0.0 | SIGMA= | 19.8 | PHAS= | 0.0 | FOM= 0.00 | TEST= 0 |
| INDE | 11 | 47 | 40 | FOBS= | 86.4 | SIGMA= | 2.2 | PHAS= | -25.6 | FOM= 0.87 | TEST= 0 |
| INDE | 11 | 47 | 42 | FOBS= | 72.4 | SIGMA= | 2.6 | PHAS= | -101.2 | FOM= 0.75 | TEST= 0 |
| INDE | 11 | 47 | 44 | FOBS= | 56.5 | SIGMA= | 3.5 | PHAS= | -143.9 | FOM= 0.66 | TEST= 0 |

*FIG. 12A - 294*

```
INDE 11 47 46 FOBS=   88.7 SIGMA=  2.2 PHAS=   38.8 FOM= 0.86 TEST= 0
INDE 11 47 48 FOBS=   39.6 SIGMA=  4.7 PHAS=   -5.1 FOM= 0.24 TEST= 1
INDE 11 47 50 FOBS=    0.0 SIGMA= 19.9 PHAS=    0.0 FOM= 0.00 TEST= 0
INDE 11 47 52 FOBS=  101.1 SIGMA=  2.1 PHAS=   -9.8 FOM= 0.90 TEST= 0
INDE 11 47 54 FOBS=   78.4 SIGMA=  2.9 PHAS= -131.2 FOM= 0.85 TEST= 0
INDE 11 47 56 FOBS=    0.0 SIGMA= 21.0 PHAS=    0.0 FOM= 0.00 TEST= 0
INDE 11 47 58 FOBS=   29.3 SIGMA= 10.5 PHAS=  118.8 FOM= 0.26 TEST= 0
INDE 11 47 60 FOBS=   42.5 SIGMA=  6.6 PHAS=   68.8 FOM= 0.19 TEST= 1
INDE 11 48 11 FOBS=   87.1 SIGMA=  3.1 PHAS=  147.4 FOM= 0.87 TEST= 0
INDE 11 48 13 FOBS=  250.7 SIGMA=  1.3 PHAS= -124.8 FOM= 0.94 TEST= 0
INDE 11 48 15 FOBS=  149.6 SIGMA=  1.4 PHAS=   59.5 FOM= 0.90 TEST= 1
INDE 11 48 17 FOBS=  232.9 SIGMA=  1.0 PHAS= -113.0 FOM= 0.96 TEST= 0
INDE 11 48 19 FOBS=  289.0 SIGMA=  0.9 PHAS= -103.8 FOM= 0.97 TEST= 0
INDE 11 48 21 FOBS=  147.0 SIGMA=  1.6 PHAS=  -64.4 FOM= 0.95 TEST= 0
INDE 11 48 23 FOBS=  197.0 SIGMA=  1.1 PHAS= -156.5 FOM= 0.96 TEST= 0
INDE 11 48 25 FOBS=  118.1 SIGMA=  1.8 PHAS=  -53.6 FOM= 0.84 TEST= 0
INDE 11 48 27 FOBS=  137.5 SIGMA=  1.6 PHAS=   84.5 FOM= 0.86 TEST= 0
INDE 11 48 29 FOBS=  155.0 SIGMA=  1.4 PHAS=  114.9 FOM= 0.92 TEST= 0
INDE 11 48 31 FOBS=  177.4 SIGMA=  1.3 PHAS=  116.5 FOM= 0.96 TEST= 0
INDE 11 48 33 FOBS=   23.4 SIGMA=  8.5 PHAS=  143.3 FOM= 0.69 TEST= 0
INDE 11 48 35 FOBS=   73.9 SIGMA=  2.5 PHAS= -159.1 FOM= 0.89 TEST= 0
INDE 11 48 37 FOBS=   79.3 SIGMA=  2.7 PHAS=   98.0 FOM= 0.96 TEST= 0
INDE 11 48 39 FOBS=   55.8 SIGMA=  3.4 PHAS=  173.2 FOM= 0.63 TEST= 1
INDE 11 48 41 FOBS=   88.9 SIGMA=  2.2 PHAS= -153.4 FOM= 0.84 TEST= 0
INDE 11 48 43 FOBS=   33.2 SIGMA=  6.5 PHAS=  -52.0 FOM= 0.26 TEST= 0
INDE 11 48 45 FOBS=   44.7 SIGMA=  4.2 PHAS=   12.7 FOM= 0.32 TEST= 1
INDE 11 48 47 FOBS=   53.1 SIGMA=  3.5 PHAS=   52.7 FOM= 0.71 TEST= 0
INDE 11 48 49 FOBS=    0.0 SIGMA= 21.1 PHAS=    0.0 FOM= 0.00 TEST= 0
INDE 11 48 51 FOBS=   17.6 SIGMA= 13.6 PHAS=  -35.4 FOM= 0.13 TEST= 0
INDE 11 48 53 FOBS=   36.7 SIGMA=  5.5 PHAS= -147.2 FOM= 0.63 TEST= 0
INDE 11 48 55 FOBS=    0.0 SIGMA= 22.0 PHAS=    0.0 FOM= 0.00 TEST= 0
INDE 11 48 57 FOBS=    0.0 SIGMA= 22.0 PHAS=    0.0 FOM= 0.00 TEST= 0
INDE 11 48 59 FOBS=   40.8 SIGMA=  6.9 PHAS=  -27.7 FOM= 0.38 TEST= 0
INDE 11 49 12 FOBS=   59.2 SIGMA=  4.6 PHAS=   97.9 FOM= 0.70 TEST= 0
INDE 11 49 14 FOBS=  217.4 SIGMA=  1.4 PHAS=   95.7 FOM= 0.92 TEST= 0
INDE 11 49 16 FOBS=   88.5 SIGMA=  2.3 PHAS= -177.5 FOM= 0.72 TEST= 0
INDE 11 49 18 FOBS=   81.0 SIGMA=  2.5 PHAS=  142.8 FOM= 0.83 TEST= 0
INDE 11 49 20 FOBS=   88.0 SIGMA=  2.3 PHAS= -177.8 FOM= 0.89 TEST= 0
INDE 11 49 22 FOBS=   89.6 SIGMA=  2.3 PHAS=  118.3 FOM= 0.40 TEST= 0
INDE 11 49 24 FOBS=  129.2 SIGMA=  1.6 PHAS=  137.2 FOM= 0.93 TEST= 0
INDE 11 49 26 FOBS=  129.3 SIGMA=  1.6 PHAS=  105.7 FOM= 0.94 TEST= 0
INDE 11 49 28 FOBS=  150.4 SIGMA=  1.4 PHAS=   -5.0 FOM= 0.96 TEST= 0
INDE 11 49 30 FOBS=  143.2 SIGMA=  1.5 PHAS=   27.7 FOM= 0.90 TEST= 0
INDE 11 49 32 FOBS=  167.7 SIGMA=  1.3 PHAS=  -69.6 FOM= 0.93 TEST= 0
INDE 11 49 34 FOBS=   29.9 SIGMA=  7.1 PHAS= -127.7 FOM= 0.46 TEST= 0
INDE 11 49 36 FOBS=  105.1 SIGMA=  1.8 PHAS=   78.6 FOM= 0.95 TEST= 0
INDE 11 49 38 FOBS=  144.7 SIGMA=  1.6 PHAS=   19.8 FOM= 0.84 TEST= 1
INDE 11 49 40 FOBS=   92.4 SIGMA=  2.1 PHAS=  179.8 FOM= 0.91 TEST= 0
INDE 11 49 42 FOBS=   28.6 SIGMA=  6.8 PHAS=   70.8 FOM= 0.05 TEST= 0
INDE 11 49 44 FOBS=   99.4 SIGMA=  2.0 PHAS=  167.8 FOM= 0.94 TEST= 0
INDE 11 49 46 FOBS=   53.2 SIGMA=  3.6 PHAS= -108.1 FOM= 0.72 TEST= 0
INDE 11 49 48 FOBS=   26.4 SIGMA=  8.9 PHAS=  -11.7 FOM= 0.34 TEST= 0
INDE 11 49 50 FOBS=    0.0 SIGMA= 22.2 PHAS=    0.0 FOM= 0.00 TEST= 0
INDE 11 49 52 FOBS=   33.5 SIGMA=  6.2 PHAS=   -3.5 FOM= 0.54 TEST= 0
INDE 11 49 54 FOBS=   42.9 SIGMA=  4.8 PHAS= -123.4 FOM= 0.30 TEST= 0
INDE 11 49 56 FOBS=    0.0 SIGMA= 21.2 PHAS=    0.0 FOM= 0.00 TEST= 0
INDE 11 49 58 FOBS=   86.6 SIGMA=  3.3 PHAS=  -62.4 FOM= 0.04 TEST= 1
INDE 11 50 11 FOBS=  173.9 SIGMA=  1.2 PHAS=   35.8 FOM= 0.89 TEST= 0
INDE 11 50 13 FOBS=    0.0 SIGMA= 22.8 PHAS=    0.0 FOM= 0.00 TEST= 0
INDE 11 50 15 FOBS=  131.4 SIGMA=  2.1 PHAS=   69.5 FOM= 0.47 TEST= 0
INDE 11 50 17 FOBS=   34.1 SIGMA=  6.5 PHAS=  125.2 FOM= 0.03 TEST= 0
INDE 11 50 19 FOBS=    0.0 SIGMA= 19.7 PHAS=    0.0 FOM= 0.00 TEST= 0
INDE 11 50 21 FOBS=   72.6 SIGMA=  3.0 PHAS=  -56.6 FOM= 0.55 TEST= 1
INDE 11 50 23 FOBS=   63.5 SIGMA=  3.2 PHAS=  163.0 FOM= 0.67 TEST= 0
INDE 11 50 25 FOBS=   19.2 SIGMA= 10.5 PHAS=   45.5 FOM= 0.42 TEST= 0
INDE 11 50 27 FOBS=   26.5 SIGMA=  7.6 PHAS=   90.3 FOM= 0.13 TEST= 1
INDE 11 50 29 FOBS=  142.7 SIGMA=  1.5 PHAS= -100.7 FOM= 0.96 TEST= 0
INDE 11 50 31 FOBS=   61.9 SIGMA=  3.3 PHAS= -161.8 FOM= 0.77 TEST= 0
INDE 11 50 33 FOBS=   42.1 SIGMA=  4.8 PHAS= -112.1 FOM= 0.29 TEST= 0
INDE 11 50 35 FOBS=    0.0 SIGMA= 19.8 PHAS=    0.0 FOM= 0.00 TEST= 0
```

*FIG. 12A - 295*

| | | | | | | | | | | | | |
|---|---|---|---|---|---|---|---|---|---|---|---|---|
| INDE | 11 | 50 | 37 | FOBS= | 85.9 | SIGMA= | 2.1 | PHAS= | -64.8 | FOM= | 0.69 | TEST= 1 |
| INDE | 11 | 50 | 39 | FOBS= | 0.0 | SIGMA= | 20.3 | PHAS= | 0.0 | FOM= | 0.00 | TEST= 0 |
| INDE | 11 | 50 | 41 | FOBS= | 12.5 | SIGMA= | 15.6 | PHAS= | 95.9 | FOM= | 0.01 | TEST= 0 |
| INDE | 11 | 50 | 43 | FOBS= | 47.9 | SIGMA= | 3.9 | PHAS= | 41.7 | FOM= | 0.71 | TEST= 0 |
| INDE | 11 | 50 | 45 | FOBS= | 45.4 | SIGMA= | 4.2 | PHAS= | 11.5 | FOM= | 0.54 | TEST= 0 |
| INDE | 11 | 50 | 47 | FOBS= | 120.0 | SIGMA= | 1.7 | PHAS= | 121.8 | FOM= | 0.89 | TEST= 0 |
| INDE | 11 | 50 | 49 | FOBS= | 41.8 | SIGMA= | 5.4 | PHAS= | -35.4 | FOM= | 0.11 | TEST= 0 |
| INDE | 11 | 50 | 51 | FOBS= | 52.4 | SIGMA= | 4.0 | PHAS= | -30.7 | FOM= | 0.71 | TEST= 0 |
| INDE | 11 | 50 | 53 | FOBS= | 0.0 | SIGMA= | 21.8 | PHAS= | 0.0 | FOM= | 0.00 | TEST= 0 |
| INDE | 11 | 50 | 55 | FOBS= | 29.9 | SIGMA= | 6.9 | PHAS= | 34.9 | FOM= | 0.19 | TEST= 0 |
| INDE | 11 | 50 | 57 | FOBS= | 56.0 | SIGMA= | 5.0 | PHAS= | 112.8 | FOM= | 0.08 | TEST= 0 |
| INDE | 11 | 51 | 12 | FOBS= | 190.8 | SIGMA= | 1.1 | PHAS= | 6.7 | FOM= | 0.94 | TEST= 0 |
| INDE | 11 | 51 | 14 | FOBS= | 78.5 | SIGMA= | 3.4 | PHAS= | 126.7 | FOM= | 0.83 | TEST= 0 |
| INDE | 11 | 51 | 16 | FOBS= | 37.0 | SIGMA= | 5.3 | PHAS= | -48.2 | FOM= | 0.25 | TEST= 0 |
| INDE | 11 | 51 | 18 | FOBS= | 93.4 | SIGMA= | 2.1 | PHAS= | -28.1 | FOM= | 0.22 | TEST= 0 |
| INDE | 11 | 51 | 20 | FOBS= | 0.0 | SIGMA= | 20.6 | PHAS= | 0.0 | FOM= | 0.00 | TEST= 1 |
| INDE | 11 | 51 | 22 | FOBS= | 58.1 | SIGMA= | 3.4 | PHAS= | 45.8 | FOM= | 0.65 | TEST= 0 |
| INDE | 11 | 51 | 24 | FOBS= | 242.2 | SIGMA= | 1.0 | PHAS= | 149.9 | FOM= | 0.98 | TEST= 0 |
| INDE | 11 | 51 | 26 | FOBS= | 109.1 | SIGMA= | 1.9 | PHAS= | 88.0 | FOM= | 0.93 | TEST= 0 |
| INDE | 11 | 51 | 28 | FOBS= | 89.7 | SIGMA= | 2.3 | PHAS= | 77.2 | FOM= | 0.82 | TEST= 0 |
| INDE | 11 | 51 | 30 | FOBS= | 22.4 | SIGMA= | 9.0 | PHAS= | -82.9 | FOM= | 0.10 | TEST= 0 |
| INDE | 11 | 51 | 32 | FOBS= | 144.9 | SIGMA= | 1.5 | PHAS= | -66.2 | FOM= | 0.89 | TEST= 0 |
| INDE | 11 | 51 | 34 | FOBS= | 32.4 | SIGMA= | 6.1 | PHAS= | -89.5 | FOM= | 0.31 | TEST= 0 |
| INDE | 11 | 51 | 36 | FOBS= | 85.0 | SIGMA= | 2.1 | PHAS= | 91.2 | FOM= | 0.89 | TEST= 0 |
| INDE | 11 | 51 | 38 | FOBS= | 56.8 | SIGMA= | 3.1 | PHAS= | 178.3 | FOM= | 0.50 | TEST= 0 |
| INDE | 11 | 51 | 40 | FOBS= | 64.1 | SIGMA= | 2.9 | PHAS= | 174.6 | FOM= | 0.85 | TEST= 0 |
| INDE | 11 | 51 | 42 | FOBS= | 96.9 | SIGMA= | 2.0 | PHAS= | -100.0 | FOM= | 0.91 | TEST= 0 |
| INDE | 11 | 51 | 44 | FOBS= | 71.2 | SIGMA= | 2.7 | PHAS= | 122.1 | FOM= | 0.91 | TEST= 0 |
| INDE | 11 | 51 | 46 | FOBS= | 41.4 | SIGMA= | 4.6 | PHAS= | -151.1 | FOM= | 0.32 | TEST= 0 |
| INDE | 11 | 51 | 48 | FOBS= | 85.5 | SIGMA= | 2.5 | PHAS= | 60.6 | FOM= | 0.29 | TEST= 1 |
| INDE | 11 | 51 | 50 | FOBS= | 0.0 | SIGMA= | 23.2 | PHAS= | 0.0 | FOM= | 0.00 | TEST= 0 |
| INDE | 11 | 51 | 52 | FOBS= | 27.9 | SIGMA= | 7.5 | PHAS= | 179.4 | FOM= | 0.47 | TEST= 0 |
| INDE | 11 | 51 | 54 | FOBS= | 22.4 | SIGMA= | 10.3 | PHAS= | 26.5 | FOM= | 0.19 | TEST= 0 |
| INDE | 11 | 51 | 56 | FOBS= | 0.0 | SIGMA= | 25.4 | PHAS= | 0.0 | FOM= | 0.00 | TEST= 0 |
| INDE | 11 | 52 | 11 | FOBS= | 94.0 | SIGMA= | 2.8 | PHAS= | -10.8 | FOM= | 0.93 | TEST= 0 |
| INDE | 11 | 52 | 13 | FOBS= | 0.0 | SIGMA= | 18.9 | PHAS= | 0.0 | FOM= | 0.00 | TEST= 0 |
| INDE | 11 | 52 | 15 | FOBS= | 58.4 | SIGMA= | 4.5 | PHAS= | 32.0 | FOM= | 0.22 | TEST= 0 |
| INDE | 11 | 52 | 17 | FOBS= | 109.4 | SIGMA= | 1.8 | PHAS= | -86.3 | FOM= | 0.37 | TEST= 1 |
| INDE | 11 | 52 | 19 | FOBS= | 42.7 | SIGMA= | 5.1 | PHAS= | -40.7 | FOM= | 0.38 | TEST= 0 |
| INDE | 11 | 52 | 21 | FOBS= | 131.6 | SIGMA= | 1.6 | PHAS= | -0.9 | FOM= | 0.42 | TEST= 0 |
| INDE | 11 | 52 | 23 | FOBS= | 257.8 | SIGMA= | 0.9 | PHAS= | 66.2 | FOM= | 0.98 | TEST= 0 |
| INDE | 11 | 52 | 25 | FOBS= | 222.6 | SIGMA= | 1.0 | PHAS= | 72.9 | FOM= | 0.98 | TEST= 0 |
| INDE | 11 | 52 | 27 | FOBS= | 44.1 | SIGMA= | 4.5 | PHAS= | -56.1 | FOM= | 0.41 | TEST= 0 |
| INDE | 11 | 52 | 29 | FOBS= | 91.2 | SIGMA= | 2.3 | PHAS= | -71.8 | FOM= | 0.81 | TEST= 0 |
| INDE | 11 | 52 | 31 | FOBS= | 99.8 | SIGMA= | 2.1 | PHAS= | -136.9 | FOM= | 0.92 | TEST= 0 |
| INDE | 11 | 52 | 33 | FOBS= | 110.9 | SIGMA= | 1.9 | PHAS= | -156.3 | FOM= | 0.93 | TEST= 0 |
| INDE | 11 | 52 | 35 | FOBS= | 30.4 | SIGMA= | 7.0 | PHAS= | -102.2 | FOM= | 0.23 | TEST= 0 |
| INDE | 11 | 52 | 37 | FOBS= | 0.0 | SIGMA= | 19.4 | PHAS= | 0.0 | FOM= | 0.00 | TEST= 0 |
| INDE | 11 | 52 | 39 | FOBS= | 68.9 | SIGMA= | 2.8 | PHAS= | 76.5 | FOM= | 0.91 | TEST= 0 |
| INDE | 11 | 52 | 41 | FOBS= | 173.6 | SIGMA= | 1.2 | PHAS= | -9.7 | FOM= | 0.93 | TEST= 0 |
| INDE | 11 | 52 | 43 | FOBS= | 62.1 | SIGMA= | 3.1 | PHAS= | -168.8 | FOM= | 0.28 | TEST= 0 |
| INDE | 11 | 52 | 45 | FOBS= | 77.7 | SIGMA= | 2.5 | PHAS= | -7.6 | FOM= | 0.92 | TEST= 0 |
| INDE | 11 | 52 | 47 | FOBS= | 59.7 | SIGMA= | 3.2 | PHAS= | 88.7 | FOM= | 0.80 | TEST= 0 |
| INDE | 11 | 52 | 49 | FOBS= | 33.6 | SIGMA= | 7.4 | PHAS= | -35.0 | FOM= | 0.63 | TEST= 0 |
| INDE | 11 | 52 | 51 | FOBS= | 73.4 | SIGMA= | 2.9 | PHAS= | -164.5 | FOM= | 0.86 | TEST= 0 |
| INDE | 11 | 52 | 53 | FOBS= | 50.4 | SIGMA= | 4.2 | PHAS= | -128.2 | FOM= | 0.24 | TEST= 1 |
| INDE | 11 | 52 | 55 | FOBS= | 50.4 | SIGMA= | 5.0 | PHAS= | -38.9 | FOM= | 0.82 | TEST= 0 |
| INDE | 11 | 53 | 12 | FOBS= | 169.8 | SIGMA= | 1.1 | PHAS= | 30.1 | FOM= | 0.93 | TEST= 0 |
| INDE | 11 | 53 | 14 | FOBS= | 38.1 | SIGMA= | 6.9 | PHAS= | 53.3 | FOM= | 0.58 | TEST= 0 |
| INDE | 11 | 53 | 16 | FOBS= | 42.5 | SIGMA= | 6.0 | PHAS= | 23.9 | FOM= | 0.18 | TEST= 1 |
| INDE | 11 | 53 | 18 | FOBS= | 87.1 | SIGMA= | 2.2 | PHAS= | -61.0 | FOM= | 0.74 | TEST= 0 |
| INDE | 11 | 53 | 20 | FOBS= | 142.9 | SIGMA= | 1.5 | PHAS= | -96.2 | FOM= | 0.82 | TEST= 0 |
| INDE | 11 | 53 | 22 | FOBS= | 44.8 | SIGMA= | 4.4 | PHAS= | 26.7 | FOM= | 0.47 | TEST= 0 |
| INDE | 11 | 53 | 24 | FOBS= | 115.9 | SIGMA= | 2.1 | PHAS= | -20.1 | FOM= | 0.95 | TEST= 0 |
| INDE | 11 | 53 | 26 | FOBS= | 137.1 | SIGMA= | 1.5 | PHAS= | -19.7 | FOM= | 0.90 | TEST= 0 |
| INDE | 11 | 53 | 28 | FOBS= | 76.2 | SIGMA= | 2.6 | PHAS= | 53.9 | FOM= | 0.82 | TEST= 0 |
| INDE | 11 | 53 | 30 | FOBS= | 0.0 | SIGMA= | 22.3 | PHAS= | 0.0 | FOM= | 0.00 | TEST= 0 |
| INDE | 11 | 53 | 32 | FOBS= | 45.2 | SIGMA= | 4.5 | PHAS= | 112.7 | FOM= | 0.65 | TEST= 0 |
| INDE | 11 | 53 | 34 | FOBS= | 54.1 | SIGMA= | 3.7 | PHAS= | 118.3 | FOM= | 0.77 | TEST= 0 |
| INDE | 11 | 53 | 36 | FOBS= | 100.7 | SIGMA= | 2.0 | PHAS= | 55.6 | FOM= | 0.91 | TEST= 0 |

*FIG. 12A - 296*

```
INDE 11 53 38 FOBS=    0.0 SIGMA= 18.8 PHAS=    0.0 FOM= 0.00 TEST= 0
INDE 11 53 40 FOBS=  158.0 SIGMA=  1.4 PHAS=  -15.0 FOM= 0.94 TEST= 0
INDE 11 53 42 FOBS=   83.2 SIGMA=  2.3 PHAS= -136.2 FOM= 0.89 TEST= 0
INDE 11 53 44 FOBS=  100.2 SIGMA=  2.0 PHAS=  173.0 FOM= 0.95 TEST= 0
INDE 11 53 46 FOBS=   32.1 SIGMA=  5.9 PHAS=   91.4 FOM= 0.12 TEST= 0
INDE 11 53 48 FOBS=   76.5 SIGMA=  2.8 PHAS= -107.3 FOM= 0.88 TEST= 0
INDE 11 53 50 FOBS=   39.6 SIGMA=  5.8 PHAS=  114.2 FOM= 0.78 TEST= 0
INDE 11 53 52 FOBS=   28.3 SIGMA=  9.2 PHAS=  124.9 FOM= 0.24 TEST= 0
INDE 11 53 54 FOBS=   69.5 SIGMA=  4.2 PHAS=  -64.5 FOM= 0.87 TEST= 0
INDE 11 54 11 FOBS=  105.2 SIGMA=  2.6 PHAS= -179.4 FOM= 0.76 TEST= 0
INDE 11 54 13 FOBS=  136.8 SIGMA=  1.1 PHAS= -103.6 FOM= 0.95 TEST= 0
INDE 11 54 15 FOBS=  104.3 SIGMA=  2.5 PHAS=  -69.8 FOM= 0.43 TEST= 0
INDE 11 54 17 FOBS=   79.5 SIGMA=  3.2 PHAS=  175.4 FOM= 0.81 TEST= 0
INDE 11 54 19 FOBS=    0.0 SIGMA= 20.3 PHAS=    0.0 FOM= 0.00 TEST= 0
INDE 11 54 21 FOBS=   36.9 SIGMA=  5.9 PHAS=   69.8 FOM= 0.52 TEST= 0
INDE 11 54 23 FOBS=  130.6 SIGMA=  1.6 PHAS=   39.4 FOM= 0.95 TEST= 0
INDE 11 54 25 FOBS=   68.8 SIGMA=  2.9 PHAS=   18.0 FOM= 0.22 TEST= 0
INDE 11 54 27 FOBS=  104.1 SIGMA=  2.0 PHAS= -154.2 FOM= 0.92 TEST= 0
INDE 11 54 29 FOBS=   60.8 SIGMA=  3.3 PHAS=   46.0 FOM= 0.32 TEST= 0
INDE 11 54 31 FOBS=  121.4 SIGMA=  1.7 PHAS=  -20.8 FOM= 0.92 TEST= 0
INDE 11 54 33 FOBS=   83.9 SIGMA=  2.4 PHAS= -165.6 FOM= 0.72 TEST= 0
INDE 11 54 35 FOBS=   77.3 SIGMA=  2.6 PHAS=  -29.0 FOM= 0.36 TEST= 0
INDE 11 54 37 FOBS=   73.2 SIGMA=  2.4 PHAS=  -66.9 FOM= 0.86 TEST= 0
INDE 11 54 39 FOBS=  109.0 SIGMA=  1.7 PHAS=   27.8 FOM= 0.83 TEST= 0
INDE 11 54 41 FOBS=   46.5 SIGMA=  4.2 PHAS=  143.8 FOM= 0.56 TEST= 0
INDE 11 54 43 FOBS=  141.7 SIGMA=  1.4 PHAS=   67.2 FOM= 0.95 TEST= 0
INDE 11 54 45 FOBS=  113.3 SIGMA=  1.9 PHAS=   69.5 FOM= 0.94 TEST= 0
INDE 11 54 47 FOBS=  105.3 SIGMA=  2.3 PHAS=   53.6 FOM= 0.91 TEST= 0
INDE 11 54 49 FOBS=   60.7 SIGMA=  4.4 PHAS=   65.2 FOM= 0.87 TEST= 0
INDE 11 54 51 FOBS=   67.5 SIGMA=  3.6 PHAS= -144.4 FOM= 0.87 TEST= 0
INDE 11 54 53 FOBS=    5.9 SIGMA= 58.2 PHAS= -112.9 FOM= 0.14 TEST= 0
INDE 11 55 12 FOBS=   55.7 SIGMA=  4.7 PHAS=  147.2 FOM= 0.38 TEST= 0
INDE 11 55 14 FOBS=  144.9 SIGMA=  1.1 PHAS=  154.8 FOM= 0.95 TEST= 0
INDE 11 55 16 FOBS=   37.1 SIGMA=  6.9 PHAS= -142.2 FOM= 0.65 TEST= 0
INDE 11 55 18 FOBS=   31.0 SIGMA=  6.2 PHAS=  178.6 FOM= 0.11 TEST= 0
INDE 11 55 20 FOBS=   76.4 SIGMA=  2.6 PHAS= -114.8 FOM= 0.18 TEST= 0
INDE 11 55 22 FOBS=   82.7 SIGMA=  2.6 PHAS=   -8.0 FOM= 0.89 TEST= 0
INDE 11 55 24 FOBS=  116.0 SIGMA=  1.8 PHAS=  -50.3 FOM= 0.62 TEST= 0
INDE 11 55 26 FOBS=   23.8 SIGMA=  8.2 PHAS= -120.7 FOM= 0.17 TEST= 0
INDE 11 55 28 FOBS=   56.6 SIGMA=  3.5 PHAS=   37.1 FOM= 0.69 TEST= 0
INDE 11 55 30 FOBS=   96.4 SIGMA=  2.1 PHAS=  -70.4 FOM= 0.88 TEST= 0
INDE 11 55 32 FOBS=   53.9 SIGMA=  3.7 PHAS= -131.8 FOM= 0.76 TEST= 0
INDE 11 55 34 FOBS=   54.3 SIGMA=  3.7 PHAS=    7.1 FOM= 0.79 TEST= 0
INDE 11 55 36 FOBS=  130.9 SIGMA=  1.6 PHAS=   78.0 FOM= 0.92 TEST= 0
INDE 11 55 38 FOBS=   32.9 SIGMA=  5.7 PHAS= -165.2 FOM= 0.23 TEST= 0
INDE 11 55 40 FOBS=   47.7 SIGMA=  3.7 PHAS=  -27.1 FOM= 0.75 TEST= 0
INDE 11 55 42 FOBS=    0.0 SIGMA= 19.8 PHAS=    0.0 FOM= 0.00 TEST= 0
INDE 11 55 44 FOBS=   67.8 SIGMA=  3.1 PHAS= -140.2 FOM= 0.47 TEST= 1
INDE 11 55 46 FOBS=   75.3 SIGMA=  2.8 PHAS=  -11.2 FOM= 0.92 TEST= 0
INDE 11 55 48 FOBS=   51.6 SIGMA=  5.2 PHAS=  -74.2 FOM= 0.79 TEST= 0
INDE 11 55 50 FOBS=    0.0 SIGMA= 24.7 PHAS=    0.0 FOM= 0.00 TEST= 0
INDE 11 55 52 FOBS=   32.1 SIGMA= 11.0 PHAS= -140.3 FOM= 0.47 TEST= 0
INDE 11 56 11 FOBS=  200.1 SIGMA=  1.5 PHAS= -175.2 FOM= 0.96 TEST= 0
INDE 11 56 13 FOBS=   43.1 SIGMA=  3.1 PHAS= -157.2 FOM= 0.18 TEST= 1
INDE 11 56 15 FOBS=   82.8 SIGMA=  2.0 PHAS=   74.3 FOM= 0.80 TEST= 0
INDE 11 56 17 FOBS=  129.7 SIGMA=  2.1 PHAS=   59.1 FOM= 0.53 TEST= 1
INDE 11 56 19 FOBS=   97.6 SIGMA=  2.0 PHAS=   33.1 FOM= 0.14 TEST= 1
INDE 11 56 21 FOBS=   30.0 SIGMA=  6.4 PHAS=   54.0 FOM= 0.57 TEST= 1
INDE 11 56 23 FOBS=   58.4 SIGMA=  3.3 PHAS=  170.8 FOM= 0.52 TEST= 0
INDE 11 56 25 FOBS=   68.9 SIGMA=  2.9 PHAS= -155.9 FOM= 0.75 TEST= 0
INDE 11 56 27 FOBS=  110.0 SIGMA=  1.9 PHAS=  -98.3 FOM= 0.61 TEST= 0
INDE 11 56 29 FOBS=   74.4 SIGMA=  2.7 PHAS= -127.0 FOM= 0.13 TEST= 1
INDE 11 56 31 FOBS=   42.0 SIGMA=  4.7 PHAS=  -36.9 FOM= 0.71 TEST= 0
INDE 11 56 33 FOBS=   90.3 SIGMA=  2.2 PHAS= -158.4 FOM= 0.77 TEST= 0
INDE 11 56 35 FOBS=   41.2 SIGMA=  5.1 PHAS=  -25.6 FOM= 0.57 TEST= 0
INDE 11 56 37 FOBS=   92.1 SIGMA=  2.2 PHAS=  -73.9 FOM= 0.94 TEST= 0
INDE 11 56 39 FOBS=   58.6 SIGMA=  3.3 PHAS= -148.1 FOM= 0.86 TEST= 1
INDE 11 56 41 FOBS=    0.0 SIGMA= 19.7 PHAS=    0.0 FOM= 0.00 TEST= 0
INDE 11 56 43 FOBS=   46.1 SIGMA=  5.4 PHAS=   85.1 FOM= 0.77 TEST= 0
INDE 11 56 45 FOBS=    0.0 SIGMA= 21.2 PHAS=    0.0 FOM= 0.00 TEST= 0
```

*FIG. 12A - 297*

```
INDE 11 56 47 FOBS=   57.3 SIGMA=  4.7 PHAS=   27.2 FOM= 0.75 TEST= 0
INDE 11 56 49 FOBS=   50.7 SIGMA=  5.4 PHAS=  -96.3 FOM= 0.36 TEST= 0
INDE 11 56 51 FOBS=   85.4 SIGMA=  4.2 PHAS= -135.4 FOM= 0.94 TEST= 0
INDE 11 57 12 FOBS=   44.8 SIGMA=  5.8 PHAS= -148.2 FOM= 0.32 TEST= 0
INDE 11 57 14 FOBS=   48.5 SIGMA=  2.9 PHAS=  -73.6 FOM= 0.62 TEST= 1
INDE 11 57 16 FOBS=  208.5 SIGMA=  0.9 PHAS=  -63.7 FOM= 0.97 TEST= 0
INDE 11 57 18 FOBS=   59.1 SIGMA=  4.2 PHAS=   99.2 FOM= 0.03 TEST= 1
INDE 11 57 20 FOBS=   45.8 SIGMA=  4.1 PHAS=   13.4 FOM= 0.73 TEST= 0
INDE 11 57 22 FOBS=   31.0 SIGMA=  6.0 PHAS=  -63.2 FOM= 0.22 TEST= 0
INDE 11 57 24 FOBS=   37.3 SIGMA=  5.2 PHAS=   22.4 FOM= 0.47 TEST= 0
INDE 11 57 26 FOBS=   43.0 SIGMA=  4.5 PHAS=  159.0 FOM= 0.61 TEST= 0
INDE 11 57 28 FOBS=    0.0 SIGMA= 21.7 PHAS=    0.0 FOM= 0.00 TEST= 1
INDE 11 57 30 FOBS=    0.0 SIGMA= 21.7 PHAS=    0.0 FOM= 0.00 TEST= 0
INDE 11 57 32 FOBS=   27.4 SIGMA=  7.9 PHAS= -134.8 FOM= 0.18 TEST= 0
INDE 11 57 34 FOBS=   25.1 SIGMA=  9.9 PHAS=  145.1 FOM= 0.06 TEST= 0
INDE 11 57 36 FOBS=   45.8 SIGMA=  4.8 PHAS=   39.6 FOM= 0.75 TEST= 0
INDE 11 57 38 FOBS=   53.2 SIGMA=  4.6 PHAS=  171.3 FOM= 0.80 TEST= 0
INDE 11 57 40 FOBS=    0.0 SIGMA= 22.8 PHAS=    0.0 FOM= 0.00 TEST= 1
INDE 11 57 42 FOBS=    0.0 SIGMA= 21.2 PHAS=    0.0 FOM= 0.00 TEST= 0
INDE 11 57 44 FOBS=   38.6 SIGMA=  5.8 PHAS=   96.6 FOM= 0.64 TEST= 0
INDE 11 57 46 FOBS=   57.1 SIGMA=  4.6 PHAS=  152.1 FOM= 0.08 TEST= 1
INDE 11 57 48 FOBS=   72.6 SIGMA=  4.3 PHAS=  177.2 FOM= 0.11 TEST= 1
INDE 11 57 50 FOBS=   62.1 SIGMA=  5.8 PHAS= -166.0 FOM= 0.91 TEST= 0
INDE 11 58 11 FOBS=  111.8 SIGMA=  2.4 PHAS=   24.8 FOM= 0.87 TEST= 0
INDE 11 58 13 FOBS=  132.4 SIGMA=  2.0 PHAS=   99.4 FOM= 0.77 TEST= 1
INDE 11 58 15 FOBS=  111.8 SIGMA=  1.7 PHAS= -176.5 FOM= 0.94 TEST= 0
INDE 11 58 17 FOBS=   97.8 SIGMA=  2.1 PHAS= -134.4 FOM= 0.88 TEST= 0
INDE 11 58 19 FOBS=   96.3 SIGMA=  2.6 PHAS=    3.1 FOM= 0.88 TEST= 0
INDE 11 58 21 FOBS=   31.5 SIGMA=  6.0 PHAS=  137.6 FOM= 0.70 TEST= 0
INDE 11 58 23 FOBS=    0.0 SIGMA= 19.4 PHAS=    0.0 FOM= 0.00 TEST= 0
INDE 11 58 25 FOBS=   40.8 SIGMA=  4.7 PHAS= -116.1 FOM= 0.45 TEST= 0
INDE 11 58 27 FOBS=   50.0 SIGMA=  4.3 PHAS=   85.9 FOM= 0.68 TEST= 0
INDE 11 58 29 FOBS=   50.2 SIGMA=  3.9 PHAS=  141.5 FOM= 0.67 TEST= 1
INDE 11 58 31 FOBS=   42.3 SIGMA=  5.1 PHAS=  121.0 FOM= 0.51 TEST= 0
INDE 11 58 33 FOBS=   28.3 SIGMA=  8.5 PHAS= -140.7 FOM= 0.04 TEST= 0
INDE 11 58 35 FOBS=    0.0 SIGMA= 22.0 PHAS=    0.0 FOM= 0.00 TEST= 0
INDE 11 58 37 FOBS=   50.3 SIGMA=  4.8 PHAS=  -12.2 FOM= 0.78 TEST= 0
INDE 11 58 39 FOBS=    0.0 SIGMA= 20.4 PHAS=    0.0 FOM= 0.00 TEST= 0
INDE 11 58 41 FOBS=    0.0 SIGMA= 20.4 PHAS=    0.0 FOM= 0.00 TEST= 0
INDE 11 58 43 FOBS=   12.6 SIGMA= 15.0 PHAS=  170.8 FOM= 0.07 TEST= 1
INDE 11 58 45 FOBS=   42.4 SIGMA=  5.3 PHAS=  -17.6 FOM= 0.75 TEST= 0
INDE 11 58 47 FOBS=    0.0 SIGMA= 28.0 PHAS=    0.0 FOM= 0.00 TEST= 0
INDE 11 58 49 FOBS=   22.5 SIGMA= 20.7 PHAS=  -39.6 FOM= 0.25 TEST= 0
INDE 11 59 12 FOBS=  235.3 SIGMA=  1.3 PHAS=  -81.4 FOM= 0.96 TEST= 0
INDE 11 59 14 FOBS=   62.3 SIGMA=  2.7 PHAS=   39.3 FOM= 0.83 TEST= 0
INDE 11 59 16 FOBS=   38.8 SIGMA=  4.8 PHAS= -159.9 FOM= 0.59 TEST= 0
INDE 11 59 18 FOBS=   86.9 SIGMA=  2.3 PHAS= -134.3 FOM= 0.78 TEST= 0
INDE 11 59 20 FOBS=   60.5 SIGMA=  3.1 PHAS=  -37.5 FOM= 0.83 TEST= 0
INDE 11 59 22 FOBS=   47.8 SIGMA=  4.0 PHAS=  -40.7 FOM= 0.80 TEST= 0
INDE 11 59 24 FOBS=   62.0 SIGMA=  3.1 PHAS=  112.8 FOM= 0.72 TEST= 0
INDE 11 59 26 FOBS=    0.0 SIGMA= 23.2 PHAS=    0.0 FOM= 0.00 TEST= 0
INDE 11 59 28 FOBS=   30.9 SIGMA=  7.6 PHAS=   41.7 FOM= 0.30 TEST= 0
INDE 11 59 30 FOBS=   60.4 SIGMA=  3.9 PHAS=  -13.5 FOM= 0.71 TEST= 0
INDE 11 59 32 FOBS=   26.2 SIGMA= 10.5 PHAS=  118.3 FOM= 0.33 TEST= 0
INDE 11 59 34 FOBS=    0.0 SIGMA= 25.4 PHAS=    0.0 FOM= 0.00 TEST= 0
INDE 11 59 36 FOBS=   36.8 SIGMA=  6.7 PHAS=  -60.9 FOM= 0.31 TEST= 0
INDE 11 59 38 FOBS=   35.0 SIGMA=  7.1 PHAS= -169.1 FOM= 0.67 TEST= 0
INDE 11 59 40 FOBS=    0.0 SIGMA= 21.4 PHAS=    0.0 FOM= 0.00 TEST= 0
INDE 11 59 42 FOBS=   85.8 SIGMA=  2.5 PHAS=  165.8 FOM= 0.93 TEST= 0
INDE 11 59 44 FOBS=   23.9 SIGMA=  8.1 PHAS=  162.8 FOM= 0.17 TEST= 0
INDE 11 59 46 FOBS=    0.0 SIGMA= 23.7 PHAS=    0.0 FOM= 0.00 TEST= 0
INDE 11 59 48 FOBS=   34.5 SIGMA= 10.1 PHAS= -177.0 FOM= 0.20 TEST= 0
INDE 11 60 11 FOBS=   55.5 SIGMA=  3.2 PHAS= -139.5 FOM= 0.82 TEST= 0
INDE 11 60 13 FOBS=   36.0 SIGMA=  6.9 PHAS=  -77.4 FOM= 0.39 TEST= 0
INDE 11 60 15 FOBS=   49.2 SIGMA=  3.5 PHAS=  126.5 FOM= 0.18 TEST= 0
INDE 11 60 17 FOBS=   20.5 SIGMA= 11.1 PHAS=   90.6 FOM= 0.55 TEST= 0
INDE 11 60 19 FOBS=    0.0 SIGMA= 21.9 PHAS=    0.0 FOM= 0.00 TEST= 0
INDE 11 60 21 FOBS=  115.2 SIGMA=  1.8 PHAS=  166.4 FOM= 0.90 TEST= 0
INDE 11 60 23 FOBS=   63.2 SIGMA=  3.6 PHAS=   77.5 FOM= 0.70 TEST= 1
INDE 11 60 25 FOBS=   29.1 SIGMA=  9.2 PHAS=   97.2 FOM= 0.52 TEST= 0
```

*FIG. 12A - 298*

```
INDE 11 60 27 FOBS=   104.8 SIGMA=  2.3 PHAS=   91.9 FOM= 0.90 TEST= 0
INDE 11 60 29 FOBS=    69.7 SIGMA=  3.4 PHAS= -166.0 FOM= 0.52 TEST= 0
INDE 11 60 31 FOBS=    70.8 SIGMA=  3.4 PHAS=  156.7 FOM= 0.69 TEST= 0
INDE 11 60 33 FOBS=    24.7 SIGMA= 11.4 PHAS=  -85.9 FOM= 0.07 TEST= 1
INDE 11 60 35 FOBS=    20.5 SIGMA= 11.8 PHAS=   -1.4 FOM= 0.27 TEST= 0
INDE 11 60 37 FOBS=    80.1 SIGMA=  3.2 PHAS=  113.6 FOM= 0.87 TEST= 0
INDE 11 60 39 FOBS=     0.0 SIGMA= 22.3 PHAS=    0.0 FOM= 0.00 TEST= 0
INDE 11 60 41 FOBS=    80.0 SIGMA=  2.7 PHAS=   25.2 FOM= 0.89 TEST= 0
INDE 11 60 43 FOBS=    64.4 SIGMA=  3.4 PHAS=   68.7 FOM= 0.90 TEST= 0
INDE 11 60 45 FOBS=     0.0 SIGMA= 24.0 PHAS=    0.0 FOM= 0.00 TEST= 0
INDE 11 60 47 FOBS=    57.5 SIGMA=  4.6 PHAS=   46.0 FOM= 0.07 TEST= 0
INDE 11 61 12 FOBS=    67.2 SIGMA=  3.8 PHAS=  -23.5 FOM= 0.59 TEST= 0
INDE 11 61 14 FOBS=    73.1 SIGMA=  3.5 PHAS= -102.5 FOM= 0.41 TEST= 0
INDE 11 61 16 FOBS=    89.1 SIGMA=  2.1 PHAS=  -84.8 FOM= 0.84 TEST= 0
INDE 11 61 18 FOBS=     0.0 SIGMA= 20.4 PHAS=    0.0 FOM= 0.00 TEST= 1
INDE 11 61 20 FOBS=    47.5 SIGMA=  5.9 PHAS=   52.9 FOM= 0.65 TEST= 0
INDE 11 61 22 FOBS=     0.0 SIGMA= 20.1 PHAS=    0.0 FOM= 0.00 TEST= 0
INDE 11 61 24 FOBS=   156.7 SIGMA=  1.6 PHAS=   28.7 FOM= 0.95 TEST= 0
INDE 11 61 26 FOBS=    68.1 SIGMA=  3.5 PHAS=   -7.4 FOM= 0.90 TEST= 0
INDE 11 61 28 FOBS=    41.5 SIGMA=  5.7 PHAS=   99.3 FOM= 0.45 TEST= 0
INDE 11 61 30 FOBS=   112.1 SIGMA=  2.2 PHAS=   25.4 FOM= 0.92 TEST= 0
INDE 11 61 32 FOBS=     0.0 SIGMA= 21.8 PHAS=    0.0 FOM= 0.00 TEST= 0
INDE 11 61 34 FOBS=    41.2 SIGMA=  5.9 PHAS=  -99.0 FOM= 0.35 TEST= 0
INDE 11 61 36 FOBS=    64.3 SIGMA=  4.5 PHAS= -119.1 FOM= 0.07 TEST= 1
INDE 11 61 38 FOBS=    39.2 SIGMA=  7.3 PHAS=   64.7 FOM= 0.76 TEST= 0
INDE 11 61 40 FOBS=    55.8 SIGMA=  5.5 PHAS=  -97.1 FOM= 0.85 TEST= 0
INDE 11 61 42 FOBS=    35.9 SIGMA=  6.6 PHAS=  -90.6 FOM= 0.50 TEST= 0
INDE 11 61 44 FOBS=    72.7 SIGMA=  3.8 PHAS=   11.3 FOM= 0.77 TEST= 0
INDE 11 61 46 FOBS=     0.0 SIGMA= 24.3 PHAS=    0.0 FOM= 0.00 TEST= 0
INDE 11 62 11 FOBS=    48.9 SIGMA=  3.3 PHAS= -145.0 FOM= 0.84 TEST= 0
INDE 11 62 13 FOBS=     0.0 SIGMA= 22.1 PHAS=    0.0 FOM= 0.00 TEST= 0
INDE 11 62 15 FOBS=    19.6 SIGMA= 17.4 PHAS=  134.9 FOM= 0.15 TEST= 0
INDE 11 62 17 FOBS=    91.6 SIGMA=  2.4 PHAS=   57.0 FOM= 0.86 TEST= 0
INDE 11 62 19 FOBS=    68.0 SIGMA=  3.6 PHAS=  -74.9 FOM= 0.90 TEST= 0
INDE 11 62 21 FOBS=   116.9 SIGMA=  3.0 PHAS=  -79.1 FOM= 0.90 TEST= 0
INDE 11 62 23 FOBS=    52.8 SIGMA=  5.0 PHAS=  -64.9 FOM= 0.72 TEST= 0
INDE 11 62 25 FOBS=     8.3 SIGMA= 32.5 PHAS= -122.9 FOM= 0.36 TEST= 0
INDE 11 62 27 FOBS=     0.0 SIGMA= 25.7 PHAS=    0.0 FOM= 0.00 TEST= 0
INDE 11 62 29 FOBS=     4.6 SIGMA= 60.2 PHAS=   96.5 FOM= 0.21 TEST= 0
INDE 11 62 31 FOBS=    51.6 SIGMA=  5.4 PHAS=  -51.3 FOM= 0.56 TEST= 0
INDE 11 62 33 FOBS=     0.0 SIGMA= 23.5 PHAS=    0.0 FOM= 0.00 TEST= 0
INDE 11 62 35 FOBS=   102.6 SIGMA=  2.8 PHAS= -169.6 FOM= 0.91 TEST= 0
INDE 11 62 37 FOBS=    50.4 SIGMA=  5.7 PHAS=  115.2 FOM= 0.56 TEST= 0
INDE 11 62 39 FOBS=     6.3 SIGMA= 45.6 PHAS=  -50.5 FOM= 0.08 TEST= 0
INDE 11 62 41 FOBS=    46.6 SIGMA=  5.1 PHAS=  133.7 FOM= 0.70 TEST= 0
INDE 11 62 43 FOBS=    48.1 SIGMA=  6.2 PHAS= -142.3 FOM= 0.09 TEST= 1
INDE 11 62 45 FOBS=    46.9 SIGMA=  7.2 PHAS= -127.3 FOM= 0.78 TEST= 0
INDE 11 63 12 FOBS=    24.0 SIGMA=  8.2 PHAS=   31.6 FOM= 0.42 TEST= 0
INDE 11 63 14 FOBS=    56.4 SIGMA=  6.1 PHAS=  102.3 FOM= 0.71 TEST= 0
INDE 11 63 16 FOBS=    98.5 SIGMA=  2.0 PHAS=  -28.4 FOM= 0.89 TEST= 0
INDE 11 63 18 FOBS=    22.6 SIGMA= 15.0 PHAS=    2.7 FOM= 0.31 TEST= 0
INDE 11 63 20 FOBS=   102.8 SIGMA=  2.5 PHAS=  147.7 FOM= 0.94 TEST= 0
INDE 11 63 22 FOBS=   121.4 SIGMA=  2.3 PHAS= -145.7 FOM= 0.96 TEST= 0
INDE 11 63 24 FOBS=    36.2 SIGMA=  7.3 PHAS=   96.2 FOM= 0.51 TEST= 0
INDE 11 63 26 FOBS=    35.4 SIGMA=  7.6 PHAS= -147.0 FOM= 0.30 TEST= 0
INDE 11 63 28 FOBS=     0.0 SIGMA= 25.6 PHAS=    0.0 FOM= 0.00 TEST= 0
INDE 11 63 30 FOBS=    56.6 SIGMA=  5.0 PHAS= -174.9 FOM= 0.60 TEST= 0
INDE 11 63 32 FOBS=     0.0 SIGMA= 26.2 PHAS=    0.0 FOM= 0.00 TEST= 0
INDE 11 63 34 FOBS=     0.0 SIGMA= 23.7 PHAS=    0.0 FOM= 0.00 TEST= 0
INDE 11 63 36 FOBS=    37.9 SIGMA=  8.7 PHAS=   99.4 FOM= 0.55 TEST= 0
INDE 11 63 38 FOBS=     0.0 SIGMA= 24.1 PHAS=    0.0 FOM= 0.00 TEST= 0
INDE 11 63 40 FOBS=    57.4 SIGMA=  5.2 PHAS=   65.3 FOM= 0.72 TEST= 0
INDE 11 63 42 FOBS=    53.4 SIGMA=  5.5 PHAS=   33.1 FOM= 0.50 TEST= 0
INDE 11 63 44 FOBS=    46.4 SIGMA=  8.5 PHAS=  160.9 FOM= 0.54 TEST= 0
INDE 11 64 11 FOBS=    57.6 SIGMA=  6.1 PHAS=  -35.2 FOM= 0.81 TEST= 1
INDE 11 64 13 FOBS=    36.5 SIGMA=  9.4 PHAS=  -36.0 FOM= 0.47 TEST= 0
INDE 11 64 15 FOBS=   107.4 SIGMA=  3.3 PHAS=  -40.3 FOM= 0.87 TEST= 0
INDE 11 64 17 FOBS=     0.0 SIGMA= 20.2 PHAS=    0.0 FOM= 0.00 TEST= 1
INDE 11 64 19 FOBS=    28.4 SIGMA=  7.3 PHAS=  -24.9 FOM= 0.45 TEST= 0
INDE 11 64 21 FOBS=    89.2 SIGMA=  2.9 PHAS=   58.8 FOM= 0.94 TEST= 0
```

*FIG. 12A - 299*

```
INDE 11 64 23 FOBS=   89.5 SIGMA=  3.0 PHAS=  148.4 FOM= 0.84 TEST= 0
INDE 11 64 25 FOBS=   71.8 SIGMA=  3.8 PHAS=   17.5 FOM= 0.82 TEST= 0
INDE 11 64 27 FOBS=   69.7 SIGMA=  3.9 PHAS=  -60.5 FOM= 0.82 TEST= 0
INDE 11 64 29 FOBS=  105.4 SIGMA=  2.8 PHAS=  118.6 FOM= 0.91 TEST= 0
INDE 11 64 31 FOBS=   28.4 SIGMA=  9.8 PHAS=    7.9 FOM= 0.10 TEST= 0
INDE 11 64 33 FOBS=    0.0 SIGMA= 23.6 PHAS=    0.0 FOM= 0.00 TEST= 0
INDE 11 64 35 FOBS=   52.0 SIGMA=  5.5 PHAS= -106.6 FOM= 0.84 TEST= 0
INDE 11 64 37 FOBS=    0.0 SIGMA= 23.9 PHAS=    0.0 FOM= 0.00 TEST= 0
INDE 11 64 39 FOBS=   54.8 SIGMA=  5.4 PHAS=  -22.5 FOM= 0.85 TEST= 0
INDE 11 64 41 FOBS=   18.6 SIGMA= 20.7 PHAS=   -4.4 FOM= 0.50 TEST= 0
INDE 11 65 12 FOBS=   22.2 SIGMA=  8.5 PHAS=  -67.6 FOM= 0.46 TEST= 0
INDE 11 65 14 FOBS=   53.0 SIGMA=  6.5 PHAS=  163.9 FOM= 0.65 TEST= 0
INDE 11 65 16 FOBS=   19.0 SIGMA= 18.0 PHAS=  150.3 FOM= 0.22 TEST= 0
INDE 11 65 18 FOBS=  118.6 SIGMA=  1.9 PHAS= -144.1 FOM= 0.38 TEST= 1
INDE 11 65 20 FOBS=   74.7 SIGMA=  3.2 PHAS=  -32.8 FOM= 0.25 TEST= 0
INDE 11 65 22 FOBS=   65.2 SIGMA=  3.9 PHAS=   12.4 FOM= 0.72 TEST= 0
INDE 11 65 24 FOBS=   33.6 SIGMA=  7.7 PHAS=   49.3 FOM= 0.54 TEST= 0
INDE 11 65 26 FOBS=   69.9 SIGMA=  3.8 PHAS= -140.3 FOM= 0.75 TEST= 0
INDE 11 65 28 FOBS=   33.4 SIGMA=  8.3 PHAS=  112.8 FOM= 0.57 TEST= 0
INDE 11 65 30 FOBS=   61.5 SIGMA=  4.6 PHAS=   -1.0 FOM= 0.76 TEST= 0
INDE 11 65 32 FOBS=    0.0 SIGMA= 25.6 PHAS=    0.0 FOM= 0.00 TEST= 0
INDE 11 65 34 FOBS=    0.0 SIGMA= 23.8 PHAS=    0.0 FOM= 0.00 TEST= 0
INDE 11 65 36 FOBS=   42.8 SIGMA=  6.8 PHAS= -150.2 FOM= 0.66 TEST= 0
INDE 11 65 38 FOBS=   50.8 SIGMA=  5.9 PHAS=  172.3 FOM= 0.49 TEST= 0
INDE 11 65 40 FOBS=   46.2 SIGMA=  6.6 PHAS= -120.0 FOM= 0.67 TEST= 0
INDE 11 66 11 FOBS=   86.5 SIGMA=  4.1 PHAS= -168.7 FOM= 0.80 TEST= 0
INDE 11 66 13 FOBS=   37.9 SIGMA=  9.1 PHAS=   99.2 FOM= 0.70 TEST= 0
INDE 11 66 15 FOBS=  106.2 SIGMA=  3.4 PHAS=   -2.6 FOM= 0.90 TEST= 0
INDE 11 66 17 FOBS=   97.2 SIGMA=  3.7 PHAS=   51.0 FOM= 0.89 TEST= 0
INDE 11 66 19 FOBS=   39.7 SIGMA=  5.4 PHAS=  -88.9 FOM= 0.15 TEST= 1
INDE 11 66 21 FOBS=   42.5 SIGMA=  5.5 PHAS= -131.7 FOM= 0.88 TEST= 0
INDE 11 66 23 FOBS=   35.1 SIGMA=  7.2 PHAS=   -7.0 FOM= 0.04 TEST= 1
INDE 11 66 25 FOBS=   47.0 SIGMA=  5.6 PHAS=  -17.8 FOM= 0.17 TEST= 0
INDE 11 66 27 FOBS=   33.5 SIGMA=  9.9 PHAS=   27.0 FOM= 0.56 TEST= 0
INDE 11 66 29 FOBS=    0.0 SIGMA= 23.4 PHAS=    0.0 FOM= 0.00 TEST= 0
INDE 11 66 31 FOBS=    0.0 SIGMA= 26.7 PHAS=    0.0 FOM= 0.00 TEST= 0
INDE 11 66 33 FOBS=   50.6 SIGMA=  5.7 PHAS=   50.8 FOM= 0.47 TEST= 0
INDE 11 66 35 FOBS=   25.3 SIGMA= 13.4 PHAS= -124.0 FOM= 0.54 TEST= 0
INDE 11 66 37 FOBS=   31.6 SIGMA= 10.9 PHAS=   -3.3 FOM= 0.59 TEST= 0
INDE 11 66 39 FOBS=   51.4 SIGMA=  5.9 PHAS=   68.2 FOM= 0.58 TEST= 0
INDE 11 67 12 FOBS=   60.6 SIGMA=  8.4 PHAS=  -48.2 FOM= 0.78 TEST= 0
INDE 11 67 14 FOBS=   50.3 SIGMA=  6.8 PHAS=  -99.4 FOM= 0.69 TEST= 0
INDE 11 67 16 FOBS=   31.8 SIGMA= 10.8 PHAS=  -72.6 FOM= 0.32 TEST= 1
INDE 11 67 18 FOBS=   71.4 SIGMA=  2.8 PHAS=  162.1 FOM= 0.82 TEST= 0
INDE 11 67 20 FOBS=   60.2 SIGMA=  3.7 PHAS=  153.4 FOM= 0.79 TEST= 0
INDE 11 67 22 FOBS=    0.0 SIGMA= 23.7 PHAS=    0.0 FOM= 0.00 TEST= 1
INDE 11 67 24 FOBS=    0.0 SIGMA= 20.8 PHAS=    0.0 FOM= 0.00 TEST= 0
INDE 11 67 26 FOBS=   17.7 SIGMA= 15.1 PHAS=  101.2 FOM= 0.14 TEST= 0
INDE 11 67 28 FOBS=   42.2 SIGMA=  6.5 PHAS= -156.1 FOM= 0.74 TEST= 0
INDE 11 67 30 FOBS=   62.3 SIGMA=  4.6 PHAS=  101.3 FOM= 0.64 TEST= 0
INDE 11 67 32 FOBS=   52.4 SIGMA=  5.6 PHAS= -102.2 FOM= 0.47 TEST= 0
INDE 11 67 34 FOBS=   24.2 SIGMA= 15.1 PHAS=  100.3 FOM= 0.19 TEST= 0
INDE 11 67 36 FOBS=   43.3 SIGMA=  6.9 PHAS= -146.9 FOM= 0.71 TEST= 0
INDE 11 68 13 FOBS=  122.8 SIGMA=  2.0 PHAS=  143.3 FOM= 0.88 TEST= 0
INDE 11 68 15 FOBS=   49.0 SIGMA= 10.1 PHAS=    1.3 FOM= 0.34 TEST= 0
INDE 11 68 17 FOBS=   67.8 SIGMA=  7.2 PHAS=   70.0 FOM= 0.76 TEST= 0
INDE 11 68 19 FOBS=   96.6 SIGMA=  2.2 PHAS=   33.7 FOM= 0.93 TEST= 0
INDE 11 68 21 FOBS=   53.8 SIGMA=  4.3 PHAS= -153.3 FOM= 0.87 TEST= 0
INDE 11 68 23 FOBS=   63.6 SIGMA=  3.8 PHAS=   81.8 FOM= 0.88 TEST= 0
INDE 11 68 25 FOBS=    0.0 SIGMA= 21.0 PHAS=    0.0 FOM= 0.00 TEST= 0
INDE 11 68 27 FOBS=   63.9 SIGMA=  4.4 PHAS=   76.5 FOM= 0.82 TEST= 0
INDE 11 68 29 FOBS=  100.1 SIGMA=  2.9 PHAS=   32.6 FOM= 0.91 TEST= 0
INDE 11 68 31 FOBS=    0.0 SIGMA= 23.9 PHAS=    0.0 FOM= 0.00 TEST= 0
INDE 11 68 33 FOBS=    0.0 SIGMA= 27.3 PHAS=    0.0 FOM= 0.00 TEST= 0
INDE 11 68 35 FOBS=    0.0 SIGMA= 27.1 PHAS=    0.0 FOM= 0.00 TEST= 0
INDE 11 69 20 FOBS=   27.7 SIGMA=  9.0 PHAS=  170.9 FOM= 0.50 TEST= 0
INDE 11 69 22 FOBS=   50.8 SIGMA=  5.3 PHAS=   38.7 FOM= 0.79 TEST= 0
INDE 11 69 24 FOBS=   30.0 SIGMA= 11.4 PHAS=   52.6 FOM= 0.65 TEST= 0
INDE 11 69 26 FOBS=   17.1 SIGMA= 14.9 PHAS=   79.5 FOM= 0.38 TEST= 0
INDE 11 69 28 FOBS=   69.3 SIGMA=  4.1 PHAS=  -98.1 FOM= 0.88 TEST= 0
```

*FIG. 12A - 300*

| | | | | | | | | | | | | |
|---|---|---|---|---|---|---|---|---|---|---|---|---|
| INDE | 11 | 69 | 30 | FOBS= | 61.6 | SIGMA= | 4.7 | PHAS= | -161.4 | FOM= | 0.68 | TEST= 0 |
| INDE | 11 | 69 | 32 | FOBS= | 32.1 | SIGMA= | 9.2 | PHAS= | -178.7 | FOM= | 0.36 | TEST= 0 |
| INDE | 11 | 69 | 34 | FOBS= | 0.0 | SIGMA= | 31.8 | PHAS= | 0.0 | FOM= | 0.00 | TEST= 0 |
| INDE | 11 | 70 | 21 | FOBS= | 0.0 | SIGMA= | 24.6 | PHAS= | 0.0 | FOM= | 0.00 | TEST= 0 |
| INDE | 11 | 70 | 23 | FOBS= | 13.0 | SIGMA= | 25.7 | PHAS= | -136.0 | FOM= | 0.09 | TEST= 0 |
| INDE | 11 | 70 | 25 | FOBS= | 110.9 | SIGMA= | 2.8 | PHAS= | -2.0 | FOM= | 0.93 | TEST= 0 |
| INDE | 11 | 70 | 27 | FOBS= | 28.2 | SIGMA= | 11.8 | PHAS= | -162.8 | FOM= | 0.55 | TEST= 0 |
| INDE | 11 | 70 | 29 | FOBS= | 73.6 | SIGMA= | 3.9 | PHAS= | 123.2 | FOM= | 0.88 | TEST= 0 |
| INDE | 11 | 70 | 31 | FOBS= | 36.3 | SIGMA= | 10.1 | PHAS= | -10.9 | FOM= | 0.64 | TEST= 0 |
| INDE | 11 | 71 | 14 | FOBS= | 22.3 | SIGMA= | 10.6 | PHAS= | -108.4 | FOM= | 0.26 | TEST= 0 |
| INDE | 11 | 71 | 20 | FOBS= | 5.2 | SIGMA= | 47.6 | PHAS= | -41.0 | FOM= | 0.02 | TEST= 0 |
| INDE | 11 | 71 | 22 | FOBS= | 53.9 | SIGMA= | 6.0 | PHAS= | 176.7 | FOM= | 0.73 | TEST= 0 |
| INDE | 11 | 71 | 24 | FOBS= | 51.7 | SIGMA= | 6.8 | PHAS= | -27.5 | FOM= | 0.65 | TEST= 0 |
| INDE | 11 | 71 | 28 | FOBS= | 50.4 | SIGMA= | 6.4 | PHAS= | 108.8 | FOM= | 0.15 | TEST= 1 |
| INDE | 11 | 72 | 15 | FOBS= | 0.0 | SIGMA= | 22.6 | PHAS= | 0.0 | FOM= | 0.00 | TEST= 0 |
| INDE | 11 | 72 | 21 | FOBS= | 41.9 | SIGMA= | 6.4 | PHAS= | -17.9 | FOM= | 0.41 | TEST= 0 |
| INDE | 11 | 72 | 23 | FOBS= | 0.0 | SIGMA= | 25.7 | PHAS= | 0.0 | FOM= | 0.00 | TEST= 0 |
| INDE | 11 | 72 | 25 | FOBS= | 80.7 | SIGMA= | 4.6 | PHAS= | -29.3 | FOM= | 0.24 | TEST= 1 |
| INDE | 11 | 72 | 27 | FOBS= | 105.6 | SIGMA= | 3.0 | PHAS= | -108.6 | FOM= | 0.86 | TEST= 0 |
| INDE | 11 | 73 | 22 | FOBS= | 41.7 | SIGMA= | 7.0 | PHAS= | -128.9 | FOM= | 0.39 | TEST= 0 |
| INDE | 11 | 73 | 24 | FOBS= | 27.6 | SIGMA= | 12.5 | PHAS= | 42.2 | FOM= | 0.35 | TEST= 0 |
| INDE | 11 | 74 | 15 | FOBS= | 36.6 | SIGMA= | 6.1 | PHAS= | 152.8 | FOM= | 0.31 | TEST= 0 |
| INDE | 11 | 75 | 16 | FOBS= | 69.9 | SIGMA= | 3.9 | PHAS= | 56.7 | FOM= | 0.56 | TEST= 0 |
| INDE | 12 | 12 | 12 | FOBS= | 276.2 | SIGMA= | 0.8 | PHAS= | -125.1 | FOM= | 0.99 | TEST= 0 |
| INDE | 12 | 13 | 13 | FOBS= | 154.4 | SIGMA= | 0.6 | PHAS= | 167.8 | FOM= | 0.96 | TEST= 0 |
| INDE | 12 | 13 | 15 | FOBS= | 41.0 | SIGMA= | 1.4 | PHAS= | 88.3 | FOM= | 0.92 | TEST= 0 |
| INDE | 12 | 13 | 17 | FOBS= | 112.5 | SIGMA= | 0.6 | PHAS= | -156.8 | FOM= | 0.95 | TEST= 0 |
| INDE | 12 | 13 | 19 | FOBS= | 93.2 | SIGMA= | 0.8 | PHAS= | -89.8 | FOM= | 0.89 | TEST= 0 |
| INDE | 12 | 13 | 21 | FOBS= | 181.2 | SIGMA= | 0.5 | PHAS= | -41.3 | FOM= | 0.90 | TEST= 0 |
| INDE | 12 | 13 | 23 | FOBS= | 168.6 | SIGMA= | 0.5 | PHAS= | 10.7 | FOM= | 0.97 | TEST= 0 |
| INDE | 12 | 13 | 25 | FOBS= | 25.0 | SIGMA= | 2.9 | PHAS= | 153.8 | FOM= | 0.46 | TEST= 0 |
| INDE | 12 | 13 | 27 | FOBS= | 140.7 | SIGMA= | 0.6 | PHAS= | -71.5 | FOM= | 0.92 | TEST= 0 |
| INDE | 12 | 13 | 29 | FOBS= | 103.0 | SIGMA= | 0.8 | PHAS= | -72.1 | FOM= | 0.93 | TEST= 0 |
| INDE | 12 | 13 | 31 | FOBS= | 15.9 | SIGMA= | 5.8 | PHAS= | 120.2 | FOM= | 0.88 | TEST= 0 |
| INDE | 12 | 13 | 33 | FOBS= | 88.4 | SIGMA= | 1.1 | PHAS= | 160.7 | FOM= | 0.89 | TEST= 0 |
| INDE | 12 | 13 | 35 | FOBS= | 52.9 | SIGMA= | 2.0 | PHAS= | 96.6 | FOM= | 0.95 | TEST= 0 |
| INDE | 12 | 13 | 37 | FOBS= | 295.0 | SIGMA= | 0.6 | PHAS= | -8.1 | FOM= | 0.93 | TEST= 0 |
| INDE | 12 | 13 | 39 | FOBS= | 238.2 | SIGMA= | 0.7 | PHAS= | 9.4 | FOM= | 0.90 | TEST= 0 |
| INDE | 12 | 13 | 41 | FOBS= | 128.7 | SIGMA= | 1.5 | PHAS= | -37.5 | FOM= | 0.96 | TEST= 0 |
| INDE | 12 | 13 | 43 | FOBS= | 117.4 | SIGMA= | 1.8 | PHAS= | 17.9 | FOM= | 0.91 | TEST= 0 |
| INDE | 12 | 13 | 45 | FOBS= | 196.9 | SIGMA= | 1.2 | PHAS= | -169.2 | FOM= | 0.91 | TEST= 0 |
| INDE | 12 | 13 | 47 | FOBS= | 103.7 | SIGMA= | 2.1 | PHAS= | -99.5 | FOM= | 0.90 | TEST= 1 |
| INDE | 12 | 13 | 49 | FOBS= | 59.8 | SIGMA= | 4.4 | PHAS= | 64.3 | FOM= | 0.10 | TEST= 1 |
| INDE | 12 | 13 | 51 | FOBS= | 69.1 | SIGMA= | 3.9 | PHAS= | -20.3 | FOM= | 0.85 | TEST= 0 |
| INDE | 12 | 13 | 53 | FOBS= | 35.1 | SIGMA= | 4.2 | PHAS= | 83.7 | FOM= | 0.35 | TEST= 0 |
| INDE | 12 | 13 | 55 | FOBS= | 188.1 | SIGMA= | 1.0 | PHAS= | -52.8 | FOM= | 0.96 | TEST= 0 |
| INDE | 12 | 13 | 57 | FOBS= | 50.7 | SIGMA= | 3.2 | PHAS= | 158.0 | FOM= | 0.59 | TEST= 0 |
| INDE | 12 | 13 | 59 | FOBS= | 89.9 | SIGMA= | 2.2 | PHAS= | -97.2 | FOM= | 0.94 | TEST= 0 |
| INDE | 12 | 13 | 61 | FOBS= | 172.6 | SIGMA= | 1.6 | PHAS= | -16.6 | FOM= | 0.97 | TEST= 0 |
| INDE | 12 | 13 | 63 | FOBS= | 62.9 | SIGMA= | 3.2 | PHAS= | -44.9 | FOM= | 0.69 | TEST= 0 |
| INDE | 12 | 13 | 65 | FOBS= | 0.0 | SIGMA= | 26.0 | PHAS= | 0.0 | FOM= | 0.00 | TEST= 0 |
| INDE | 12 | 13 | 67 | FOBS= | 86.7 | SIGMA= | 5.9 | PHAS= | -85.3 | FOM= | 0.20 | TEST= 1 |
| INDE | 12 | 14 | 12 | FOBS= | 226.2 | SIGMA= | 0.4 | PHAS= | -44.1 | FOM= | 0.74 | TEST= 0 |
| INDE | 12 | 14 | 14 | FOBS= | 131.1 | SIGMA= | 0.8 | PHAS= | 114.5 | FOM= | 0.80 | TEST= 0 |
| INDE | 12 | 14 | 16 | FOBS= | 148.7 | SIGMA= | 0.5 | PHAS= | 123.0 | FOM= | 0.98 | TEST= 0 |
| INDE | 12 | 14 | 18 | FOBS= | 115.9 | SIGMA= | 0.7 | PHAS= | 175.5 | FOM= | 0.98 | TEST= 0 |
| INDE | 12 | 14 | 20 | FOBS= | 165.9 | SIGMA= | 0.5 | PHAS= | 108.5 | FOM= | 0.93 | TEST= 0 |
| INDE | 12 | 14 | 22 | FOBS= | 102.3 | SIGMA= | 0.7 | PHAS= | -103.1 | FOM= | 0.91 | TEST= 1 |
| INDE | 12 | 14 | 24 | FOBS= | 200.9 | SIGMA= | 0.5 | PHAS= | -142.1 | FOM= | 0.96 | TEST= 0 |
| INDE | 12 | 14 | 26 | FOBS= | 118.8 | SIGMA= | 0.7 | PHAS= | -175.7 | FOM= | 0.91 | TEST= 0 |
| INDE | 12 | 14 | 28 | FOBS= | 84.4 | SIGMA= | 1.0 | PHAS= | 136.7 | FOM= | 0.96 | TEST= 0 |
| INDE | 12 | 14 | 30 | FOBS= | 42.7 | SIGMA= | 1.9 | PHAS= | 147.3 | FOM= | 0.86 | TEST= 0 |
| INDE | 12 | 14 | 32 | FOBS= | 24.3 | SIGMA= | 3.6 | PHAS= | -12.8 | FOM= | 0.86 | TEST= 0 |
| INDE | 12 | 14 | 34 | FOBS= | 302.6 | SIGMA= | 0.5 | PHAS= | 23.0 | FOM= | 0.98 | TEST= 0 |
| INDE | 12 | 14 | 36 | FOBS= | 224.7 | SIGMA= | 0.6 | PHAS= | 173.3 | FOM= | 0.95 | TEST= 0 |
| INDE | 12 | 14 | 38 | FOBS= | 0.0 | SIGMA= | 16.6 | PHAS= | 0.0 | FOM= | 0.00 | TEST= 0 |
| INDE | 12 | 14 | 40 | FOBS= | 270.3 | SIGMA= | 1.1 | PHAS= | -30.8 | FOM= | 0.95 | TEST= 0 |
| INDE | 12 | 14 | 42 | FOBS= | 130.9 | SIGMA= | 1.6 | PHAS= | -178.9 | FOM= | 0.93 | TEST= 0 |
| INDE | 12 | 14 | 44 | FOBS= | 118.5 | SIGMA= | 1.8 | PHAS= | 70.8 | FOM= | 0.96 | TEST= 0 |
| INDE | 12 | 14 | 46 | FOBS= | 43.0 | SIGMA= | 4.6 | PHAS= | 122.4 | FOM= | 0.15 | TEST= 0 |

*FIG. 12A - 301*

```
INDE  12  14  48  FOBS=  141.1  SIGMA=   1.2  PHAS=  -101.0  FOM=  0.89  TEST=  0
INDE  12  14  50  FOBS=   65.8  SIGMA=   2.4  PHAS=   -69.6  FOM=  0.44  TEST=  0
INDE  12  14  52  FOBS=  141.9  SIGMA=   1.1  PHAS=    54.4  FOM=  0.70  TEST=  0
INDE  12  14  54  FOBS=   27.2  SIGMA=   6.2  PHAS=   -41.0  FOM=  0.50  TEST=  0
INDE  12  14  56  FOBS=  124.5  SIGMA=   1.4  PHAS=  -173.2  FOM=  0.91  TEST=  0
INDE  12  14  58  FOBS=   69.7  SIGMA=   3.8  PHAS=  -171.0  FOM=  0.89  TEST=  1
INDE  12  14  60  FOBS=  138.5  SIGMA=   1.5  PHAS=   155.6  FOM=  0.92  TEST=  0
INDE  12  14  62  FOBS=    0.0  SIGMA=  21.0  PHAS=     0.0  FOM=  0.00  TEST=  0
INDE  12  14  64  FOBS=   56.5  SIGMA=   6.2  PHAS=    21.2  FOM=  0.38  TEST=  1
INDE  12  14  66  FOBS=   29.1  SIGMA=  11.9  PHAS=   147.2  FOM=  0.55  TEST=  0
INDE  12  15  13  FOBS=  152.3  SIGMA=   0.6  PHAS=  -109.6  FOM=  0.92  TEST=  0
INDE  12  15  15  FOBS=  183.0  SIGMA=   0.5  PHAS=    64.1  FOM=  0.95  TEST=  0
INDE  12  15  17  FOBS=  169.8  SIGMA=   0.4  PHAS=   112.5  FOM=  0.97  TEST=  0
INDE  12  15  19  FOBS=   75.2  SIGMA=   0.9  PHAS=   -22.1  FOM=  0.92  TEST=  0
INDE  12  15  21  FOBS=  157.6  SIGMA=   0.5  PHAS=   -54.5  FOM=  0.99  TEST=  0
INDE  12  15  23  FOBS=  135.3  SIGMA=   0.6  PHAS=    89.1  FOM=  0.99  TEST=  0
INDE  12  15  25  FOBS=  127.8  SIGMA=   0.6  PHAS=    83.5  FOM=  0.96  TEST=  0
INDE  12  15  27  FOBS=   62.2  SIGMA=   1.2  PHAS=    -4.7  FOM=  0.87  TEST=  0
INDE  12  15  29  FOBS=   64.9  SIGMA=   1.2  PHAS=    48.8  FOM=  0.96  TEST=  0
INDE  12  15  31  FOBS=  112.7  SIGMA=   0.8  PHAS=    35.3  FOM=  0.96  TEST=  0
INDE  12  15  33  FOBS=   84.7  SIGMA=   1.1  PHAS=  -160.5  FOM=  0.99  TEST=  0
INDE  12  15  35  FOBS=   94.4  SIGMA=   1.1  PHAS=    16.2  FOM=  0.73  TEST=  0
INDE  12  15  37  FOBS=  267.7  SIGMA=   0.6  PHAS=    73.1  FOM=  0.97  TEST=  1
INDE  12  15  39  FOBS=   80.2  SIGMA=   1.6  PHAS=   150.0  FOM=  0.96  TEST=  0
INDE  12  15  41  FOBS=  156.4  SIGMA=   1.1  PHAS=   -88.0  FOM=  0.93  TEST=  0
INDE  12  15  43  FOBS=   84.8  SIGMA=   1.9  PHAS=    74.6  FOM=  0.83  TEST=  0
INDE  12  15  45  FOBS=   85.5  SIGMA=   2.0  PHAS=    13.7  FOM=  0.94  TEST=  0
INDE  12  15  47  FOBS=    0.0  SIGMA=  18.2  PHAS=     0.0  FOM=  0.00  TEST=  0
INDE  12  15  49  FOBS=  142.7  SIGMA=   1.2  PHAS=    87.7  FOM=  0.91  TEST=  0
INDE  12  15  51  FOBS=  211.6  SIGMA=   0.8  PHAS=    12.5  FOM=  0.96  TEST=  0
INDE  12  15  53  FOBS=   46.9  SIGMA=   3.3  PHAS=    48.8  FOM=  0.06  TEST=  0
INDE  12  15  55  FOBS=   49.6  SIGMA=   3.0  PHAS=   -54.2  FOM=  0.70  TEST=  1
INDE  12  15  57  FOBS=   79.8  SIGMA=   2.3  PHAS=  -143.6  FOM=  0.13  TEST=  1
INDE  12  15  59  FOBS=  124.3  SIGMA=   1.6  PHAS=    25.6  FOM=  0.94  TEST=  0
INDE  12  15  61  FOBS=  109.4  SIGMA=   1.9  PHAS=   -27.5  FOM=  0.95  TEST=  0
INDE  12  15  63  FOBS=    0.0  SIGMA=  26.1  PHAS=     0.0  FOM=  0.00  TEST=  0
INDE  12  15  65  FOBS=    0.0  SIGMA=  26.2  PHAS=     0.0  FOM=  0.00  TEST=  0
INDE  12  16  12  FOBS=   99.3  SIGMA=   0.7  PHAS=     6.8  FOM=  0.63  TEST=  0
INDE  12  16  14  FOBS=  101.9  SIGMA=   0.7  PHAS=  -152.7  FOM=  0.78  TEST=  0
INDE  12  16  16  FOBS=  169.8  SIGMA=   0.5  PHAS=   -14.0  FOM=  0.98  TEST=  0
INDE  12  16  18  FOBS=   89.8  SIGMA=   0.7  PHAS=    40.6  FOM=  0.99  TEST=  0
INDE  12  16  20  FOBS=  153.4  SIGMA=   0.5  PHAS=  -159.6  FOM=  0.96  TEST=  0
INDE  12  16  22  FOBS=  100.9  SIGMA=   0.7  PHAS=    29.0  FOM=  0.81  TEST=  0
INDE  12  16  24  FOBS=  115.2  SIGMA=   0.7  PHAS=  -133.9  FOM=  0.98  TEST=  0
INDE  12  16  26  FOBS=  127.9  SIGMA=   0.6  PHAS=   -80.5  FOM=  0.92  TEST=  0
INDE  12  16  28  FOBS=  280.9  SIGMA=   0.4  PHAS=    95.5  FOM=  0.92  TEST=  0
INDE  12  16  30  FOBS=  163.5  SIGMA=   0.6  PHAS=   -82.3  FOM=  0.64  TEST=  0
INDE  12  16  32  FOBS=  108.3  SIGMA=   0.8  PHAS=   171.9  FOM=  0.99  TEST=  0
INDE  12  16  34  FOBS=  199.2  SIGMA=   0.5  PHAS=    90.1  FOM=  0.62  TEST=  0
INDE  12  16  36  FOBS=  105.9  SIGMA=   1.0  PHAS=   -29.1  FOM=  0.88  TEST=  0
INDE  12  16  38  FOBS=  390.6  SIGMA=   0.7  PHAS=   -10.7  FOM=  0.99  TEST=  0
INDE  12  16  40  FOBS=    0.0  SIGMA=  16.3  PHAS=     0.0  FOM=  0.00  TEST=  0
INDE  12  16  42  FOBS=  200.1  SIGMA=   0.8  PHAS=   135.7  FOM=  0.97  TEST=  0
INDE  12  16  44  FOBS=  232.0  SIGMA=   0.8  PHAS=   -99.9  FOM=  0.97  TEST=  0
INDE  12  16  46  FOBS=  184.1  SIGMA=   1.1  PHAS=  -115.0  FOM=  0.95  TEST=  0
INDE  12  16  48  FOBS=   52.1  SIGMA=   3.1  PHAS=    87.0  FOM=  0.41  TEST=  0
INDE  12  16  50  FOBS=  231.5  SIGMA=   0.8  PHAS=   -50.9  FOM=  0.96  TEST=  0
INDE  12  16  52  FOBS=   70.9  SIGMA=   2.2  PHAS=   122.9  FOM=  0.70  TEST=  0
INDE  12  16  54  FOBS=  110.9  SIGMA=   1.4  PHAS=   -60.4  FOM=  0.44  TEST=  0
INDE  12  16  56  FOBS=   65.7  SIGMA=   2.3  PHAS=   -88.1  FOM=  0.07  TEST=  1
INDE  12  16  58  FOBS=  110.5  SIGMA=   1.5  PHAS=  -108.7  FOM=  0.83  TEST=  0
INDE  12  16  60  FOBS=  211.1  SIGMA=   1.0  PHAS=   -93.5  FOM=  0.98  TEST=  0
INDE  12  16  62  FOBS=   64.1  SIGMA=   5.4  PHAS=   175.5  FOM=  0.82  TEST=  0
INDE  12  16  64  FOBS=   15.4  SIGMA=  22.2  PHAS=  -141.8  FOM=  0.07  TEST=  0
INDE  12  16  66  FOBS=   53.4  SIGMA=   9.4  PHAS=  -129.6  FOM=  0.48  TEST=  0
INDE  12  17  13  FOBS=   81.3  SIGMA=   0.8  PHAS=   168.9  FOM=  0.54  TEST=  0
INDE  12  17  15  FOBS=   92.1  SIGMA=   0.9  PHAS=  -143.7  FOM=  0.96  TEST=  0
INDE  12  17  17  FOBS=   94.3  SIGMA=   0.8  PHAS=    40.2  FOM=  0.94  TEST=  0
INDE  12  17  19  FOBS=   67.1  SIGMA=   1.0  PHAS=   -46.1  FOM=  0.98  TEST=  0
INDE  12  17  21  FOBS=  145.2  SIGMA=   0.6  PHAS=   -86.4  FOM=  0.99  TEST=  0
```

*FIG. 12A - 302*

```
INDE  12  17  23  FOBS=   77.2  SIGMA=   1.0  PHAS=   -40.0  FOM=  0.95  TEST=  0
INDE  12  17  25  FOBS=   77.2  SIGMA=   1.0  PHAS=   -88.2  FOM=  0.95  TEST=  1
INDE  12  17  27  FOBS=  128.5  SIGMA=   0.6  PHAS=   -18.2  FOM=  0.89  TEST=  0
INDE  12  17  29  FOBS=  115.0  SIGMA=   0.7  PHAS=   -32.1  FOM=  0.84  TEST=  0
INDE  12  17  31  FOBS=  235.7  SIGMA=   0.5  PHAS=    80.2  FOM=  0.97  TEST=  0
INDE  12  17  33  FOBS=  237.0  SIGMA=   0.5  PHAS=    69.2  FOM=  0.94  TEST=  0
INDE  12  17  35  FOBS=    0.0  SIGMA=  14.9  PHAS=     0.0  FOM=  0.00  TEST=  0
INDE  12  17  37  FOBS=  252.6  SIGMA=   0.6  PHAS=  -152.5  FOM=  0.92  TEST=  0
INDE  12  17  39  FOBS=  173.8  SIGMA=   0.8  PHAS=  -119.0  FOM=  0.92  TEST=  0
INDE  12  17  41  FOBS=   88.9  SIGMA=   1.6  PHAS=    44.4  FOM=  0.80  TEST=  0
INDE  12  17  43  FOBS=  297.0  SIGMA=   0.7  PHAS=   123.6  FOM=  0.97  TEST=  0
INDE  12  17  45  FOBS=  187.2  SIGMA=   1.0  PHAS=   108.8  FOM=  0.96  TEST=  0
INDE  12  17  47  FOBS=   87.7  SIGMA=   1.9  PHAS=    24.3  FOM=  0.78  TEST=  0
INDE  12  17  49  FOBS=   13.5  SIGMA=  11.9  PHAS=    11.2  FOM=  0.47  TEST=  0
INDE  12  17  51  FOBS=   37.0  SIGMA=   4.2  PHAS=  -162.0  FOM=  0.50  TEST=  0
INDE  12  17  53  FOBS=   73.1  SIGMA=   2.1  PHAS=    61.5  FOM=  0.40  TEST=  0
INDE  12  17  55  FOBS=   71.7  SIGMA=   2.1  PHAS=    -1.3  FOM=  0.53  TEST=  0
INDE  12  17  57  FOBS=   63.3  SIGMA=   2.7  PHAS=    -5.0  FOM=  0.64  TEST=  0
INDE  12  17  59  FOBS=  107.1  SIGMA=   1.6  PHAS=   126.9  FOM=  0.92  TEST=  0
INDE  12  17  61  FOBS=  135.6  SIGMA=   1.9  PHAS=  -160.0  FOM=  0.94  TEST=  0
INDE  12  17  63  FOBS=    0.0  SIGMA=  23.6  PHAS=     0.0  FOM=  0.00  TEST=  0
INDE  12  17  65  FOBS=   64.2  SIGMA=   5.5  PHAS=   172.1  FOM=  0.68  TEST=  0
INDE  12  18  12  FOBS=  205.9  SIGMA=   0.5  PHAS=   122.2  FOM=  0.92  TEST=  0
INDE  12  18  14  FOBS=  125.3  SIGMA=   0.6  PHAS=  -134.1  FOM=  0.98  TEST=  0
INDE  12  18  16  FOBS=  198.6  SIGMA=   0.5  PHAS=   -64.7  FOM=  0.97  TEST=  0
INDE  12  18  18  FOBS=  100.6  SIGMA=   0.8  PHAS=  -148.2  FOM=  0.93  TEST=  0
INDE  12  18  20  FOBS=  227.3  SIGMA=   0.5  PHAS=  -128.7  FOM=  0.98  TEST=  0
INDE  12  18  22  FOBS=  143.2  SIGMA=   0.6  PHAS=   -82.0  FOM=  0.96  TEST=  0
INDE  12  18  24  FOBS=  210.9  SIGMA=   0.5  PHAS=  -140.5  FOM=  0.93  TEST=  0
INDE  12  18  26  FOBS=   25.6  SIGMA=   3.1  PHAS=    59.0  FOM=  0.53  TEST=  0
INDE  12  18  28  FOBS=  124.7  SIGMA=   0.7  PHAS=   102.1  FOM=  0.92  TEST=  0
INDE  12  18  30  FOBS=  197.7  SIGMA=   0.5  PHAS=   -94.9  FOM=  0.95  TEST=  0
INDE  12  18  32  FOBS=  137.3  SIGMA=   0.7  PHAS=    45.5  FOM=  0.99  TEST=  0
INDE  12  18  34  FOBS=  221.0  SIGMA=   0.6  PHAS=    48.3  FOM=  0.94  TEST=  0
INDE  12  18  36  FOBS=   93.2  SIGMA=   1.2  PHAS=   100.0  FOM=  0.85  TEST=  0
INDE  12  18  38  FOBS=  168.9  SIGMA=   0.8  PHAS=   -44.5  FOM=  0.91  TEST=  1
INDE  12  18  40  FOBS=  282.0  SIGMA=   0.6  PHAS=  -179.5  FOM=  0.96  TEST=  0
INDE  12  18  42  FOBS=   47.2  SIGMA=   3.2  PHAS=    -4.9  FOM=  0.65  TEST=  0
INDE  12  18  44  FOBS=  286.0  SIGMA=   0.7  PHAS=   -40.6  FOM=  0.95  TEST=  0
INDE  12  18  46  FOBS=    0.0  SIGMA=  18.1  PHAS=     0.0  FOM=  0.00  TEST=  0
INDE  12  18  48  FOBS=  156.2  SIGMA=   1.1  PHAS=   161.9  FOM=  0.89  TEST=  0
INDE  12  18  50  FOBS=  143.6  SIGMA=   1.2  PHAS=   -28.0  FOM=  0.82  TEST=  0
INDE  12  18  52  FOBS=   50.2  SIGMA=   3.0  PHAS=    81.1  FOM=  0.56  TEST=  0
INDE  12  18  54  FOBS=   81.1  SIGMA=   1.9  PHAS=    83.1  FOM=  0.79  TEST=  0
INDE  12  18  56  FOBS=   72.4  SIGMA=   2.0  PHAS=   -61.8  FOM=  0.73  TEST=  0
INDE  12  18  58  FOBS=   21.6  SIGMA=   7.6  PHAS=    98.8  FOM=  0.26  TEST=  0
INDE  12  18  60  FOBS=    0.0  SIGMA=  19.9  PHAS=     0.0  FOM=  0.00  TEST=  0
INDE  12  18  62  FOBS=   69.2  SIGMA=   3.5  PHAS=   157.6  FOM=  0.82  TEST=  0
INDE  12  18  64  FOBS=   37.7  SIGMA=   7.4  PHAS=    62.1  FOM=  0.80  TEST=  0
INDE  12  19  13  FOBS=  314.9  SIGMA=   0.5  PHAS=   171.6  FOM=  0.94  TEST=  0
INDE  12  19  15  FOBS=  234.0  SIGMA=   0.5  PHAS=  -138.8  FOM=  0.95  TEST=  0
INDE  12  19  17  FOBS=  142.4  SIGMA=   0.6  PHAS=   106.9  FOM=  0.98  TEST=  0
INDE  12  19  19  FOBS=  154.3  SIGMA=   0.7  PHAS=   138.8  FOM=  0.96  TEST=  0
INDE  12  19  21  FOBS=  326.8  SIGMA=   0.4  PHAS=   157.0  FOM=  0.99  TEST=  0
INDE  12  19  23  FOBS=  123.2  SIGMA=   0.7  PHAS=  -172.2  FOM=  0.96  TEST=  0
INDE  12  19  25  FOBS=  236.7  SIGMA=   0.5  PHAS=  -123.6  FOM=  0.98  TEST=  0
INDE  12  19  27  FOBS=  125.8  SIGMA=   0.7  PHAS=   -63.5  FOM=  0.78  TEST=  0
INDE  12  19  29  FOBS=   80.3  SIGMA=   1.1  PHAS=    35.0  FOM=  0.96  TEST=  0
INDE  12  19  31  FOBS=  236.8  SIGMA=   0.5  PHAS=    98.4  FOM=  0.91  TEST=  0
INDE  12  19  33  FOBS=  104.2  SIGMA=   1.0  PHAS=   -17.8  FOM=  0.92  TEST=  0
INDE  12  19  35  FOBS=  123.2  SIGMA=   0.9  PHAS=   137.2  FOM=  0.72  TEST=  0
INDE  12  19  37  FOBS=  297.3  SIGMA=   0.6  PHAS=  -149.6  FOM=  0.96  TEST=  0
INDE  12  19  39  FOBS=  133.4  SIGMA=   1.0  PHAS=  -128.4  FOM=  0.98  TEST=  0
INDE  12  19  41  FOBS=  284.8  SIGMA=   0.6  PHAS=    94.5  FOM=  0.94  TEST=  0
INDE  12  19  43  FOBS=  180.2  SIGMA=   1.0  PHAS=   174.1  FOM=  0.93  TEST=  0
INDE  12  19  45  FOBS=    0.0  SIGMA=  17.6  PHAS=     0.0  FOM=  0.00  TEST=  0
INDE  12  19  47  FOBS=  106.5  SIGMA=   1.5  PHAS=   115.1  FOM=  0.89  TEST=  0
INDE  12  19  49  FOBS=   78.0  SIGMA=   2.1  PHAS=     0.0  FOM=  0.75  TEST=  0
INDE  12  19  51  FOBS=  171.4  SIGMA=   1.0  PHAS=   -78.8  FOM=  0.94  TEST=  0
INDE  12  19  53  FOBS=  120.3  SIGMA=   1.3  PHAS=    -3.7  FOM=  0.88  TEST=  0
```

*FIG. 12A - 303*

```
INDE 12 19 55 FOBS=    39.2 SIGMA=  4.1 PHAS=  -10.8 FOM= 0.53 TEST= 0
INDE 12 19 57 FOBS=    64.5 SIGMA=  2.6 PHAS=    4.1 FOM= 0.86 TEST= 0
INDE 12 19 59 FOBS=    55.3 SIGMA=  3.7 PHAS=  -42.9 FOM= 0.68 TEST= 0
INDE 12 19 61 FOBS=    72.2 SIGMA=  3.4 PHAS= -125.6 FOM= 0.83 TEST= 0
INDE 12 19 63 FOBS=    90.2 SIGMA=  2.7 PHAS=  -73.0 FOM= 0.91 TEST= 0
INDE 12 19 65 FOBS=    60.2 SIGMA=  5.8 PHAS=   13.2 FOM= 0.83 TEST= 0
INDE 12 19 67 FOBS=   138.2 SIGMA=  3.7 PHAS=  -51.4 FOM= 0.90 TEST= 0
INDE 12 20 12 FOBS=   242.9 SIGMA=  0.4 PHAS=   64.0 FOM= 0.96 TEST= 0
INDE 12 20 14 FOBS=   142.3 SIGMA=  0.6 PHAS=    9.5 FOM= 0.96 TEST= 0
INDE 12 20 16 FOBS=    16.4 SIGMA=  4.8 PHAS=  171.0 FOM= 0.78 TEST= 0
INDE 12 20 18 FOBS=    87.1 SIGMA=  0.9 PHAS=  -11.2 FOM= 0.99 TEST= 0
INDE 12 20 20 FOBS=   140.1 SIGMA=  0.7 PHAS=   76.3 FOM= 0.96 TEST= 0
INDE 12 20 22 FOBS=   146.9 SIGMA=  0.6 PHAS=   65.8 FOM= 0.56 TEST= 0
INDE 12 20 24 FOBS=   105.6 SIGMA=  0.8 PHAS= -162.0 FOM= 0.99 TEST= 0
INDE 12 20 26 FOBS=   252.4 SIGMA=  0.5 PHAS=   96.8 FOM= 0.95 TEST= 0
INDE 12 20 28 FOBS=   153.1 SIGMA=  0.6 PHAS=  -73.8 FOM= 0.97 TEST= 0
INDE 12 20 30 FOBS=   295.6 SIGMA=  0.5 PHAS=  -28.9 FOM= 0.98 TEST= 0
INDE 12 20 32 FOBS=   124.9 SIGMA=  0.9 PHAS=   77.9 FOM= 0.98 TEST= 0
INDE 12 20 34 FOBS=   208.3 SIGMA=  0.6 PHAS=  102.5 FOM= 0.75 TEST= 0
INDE 12 20 36 FOBS=   131.5 SIGMA=  1.0 PHAS=  109.8 FOM= 0.81 TEST= 0
INDE 12 20 38 FOBS=    17.1 SIGMA=  8.0 PHAS=  140.6 FOM= 0.05 TEST= 0
INDE 12 20 40 FOBS=   184.8 SIGMA=  0.9 PHAS=  148.3 FOM= 0.96 TEST= 0
INDE 12 20 42 FOBS=   191.4 SIGMA=  0.9 PHAS=   47.7 FOM= 0.90 TEST= 0
INDE 12 20 44 FOBS=    79.4 SIGMA=  1.9 PHAS=  -85.0 FOM= 0.34 TEST= 0
INDE 12 20 46 FOBS=    46.6 SIGMA=  3.3 PHAS=   69.3 FOM= 0.61 TEST= 0
INDE 12 20 48 FOBS=   209.5 SIGMA=  0.8 PHAS=  153.5 FOM= 0.94 TEST= 0
INDE 12 20 50 FOBS=   148.4 SIGMA=  1.1 PHAS= -145.0 FOM= 0.90 TEST= 0
INDE 12 20 52 FOBS=    57.7 SIGMA=  2.7 PHAS=  -99.2 FOM= 0.40 TEST= 0
INDE 12 20 54 FOBS=    12.9 SIGMA= 13.4 PHAS=  129.8 FOM= 0.22 TEST= 0
INDE 12 20 56 FOBS=    50.1 SIGMA=  3.6 PHAS=  -15.2 FOM= 0.29 TEST= 0
INDE 12 20 58 FOBS=     0.0 SIGMA= 21.1 PHAS=    0.0 FOM= 0.00 TEST= 0
INDE 12 20 60 FOBS=   118.3 SIGMA=  2.1 PHAS= -168.8 FOM= 0.92 TEST= 0
INDE 12 20 62 FOBS=   110.0 SIGMA=  2.3 PHAS=  178.4 FOM= 0.94 TEST= 0
INDE 12 20 64 FOBS=    51.5 SIGMA=  5.5 PHAS=  -85.8 FOM= 0.72 TEST= 0
INDE 12 20 66 FOBS=   117.9 SIGMA=  4.3 PHAS= -148.9 FOM= 0.96 TEST= 0
INDE 12 20 68 FOBS=    74.5 SIGMA=  6.6 PHAS=  136.4 FOM= 0.82 TEST= 0
INDE 12 20 70 FOBS=    76.4 SIGMA=  6.6 PHAS=  135.5 FOM= 0.89 TEST= 0
INDE 12 21 13 FOBS=    40.6 SIGMA=  1.7 PHAS=  -81.8 FOM= 0.57 TEST= 0
INDE 12 21 15 FOBS=    60.0 SIGMA=  1.3 PHAS=  130.0 FOM= 0.84 TEST= 0
INDE 12 21 17 FOBS=    88.2 SIGMA=  0.9 PHAS=   53.5 FOM= 0.98 TEST= 0
INDE 12 21 19 FOBS=   195.9 SIGMA=  0.5 PHAS= -110.4 FOM= 0.97 TEST= 0
INDE 12 21 21 FOBS=   147.8 SIGMA=  0.7 PHAS=   87.2 FOM= 0.96 TEST= 0
INDE 12 21 23 FOBS=    77.7 SIGMA=  1.1 PHAS=  135.9 FOM= 0.99 TEST= 0
INDE 12 21 25 FOBS=   180.3 SIGMA=  0.6 PHAS= -100.5 FOM= 0.98 TEST= 0
INDE 12 21 27 FOBS=   112.1 SIGMA=  0.8 PHAS=  166.7 FOM= 0.96 TEST= 0
INDE 12 21 29 FOBS=   155.6 SIGMA=  0.7 PHAS= -116.3 FOM= 0.98 TEST= 0
INDE 12 21 31 FOBS=    60.0 SIGMA=  1.8 PHAS=  -95.6 FOM= 0.98 TEST= 1
INDE 12 21 33 FOBS=    30.3 SIGMA=  4.1 PHAS=  -54.2 FOM= 0.53 TEST= 0
INDE 12 21 35 FOBS=   136.8 SIGMA=  0.9 PHAS=  -40.1 FOM= 0.85 TEST= 1
INDE 12 21 37 FOBS=   108.1 SIGMA=  1.2 PHAS= -166.2 FOM= 0.98 TEST= 0
INDE 12 21 39 FOBS=     0.0 SIGMA= 16.5 PHAS=    0.0 FOM= 0.00 TEST= 0
INDE 12 21 41 FOBS=   106.7 SIGMA=  1.4 PHAS=   10.0 FOM= 0.91 TEST= 0
INDE 12 21 43 FOBS=   196.3 SIGMA=  0.9 PHAS=  -71.3 FOM= 0.92 TEST= 0
INDE 12 21 45 FOBS=    88.5 SIGMA=  1.8 PHAS= -169.4 FOM= 0.88 TEST= 0
INDE 12 21 47 FOBS=    65.2 SIGMA=  2.3 PHAS=  104.2 FOM= 0.76 TEST= 0
INDE 12 21 49 FOBS=   202.8 SIGMA=  0.8 PHAS= -139.2 FOM= 0.13 TEST= 1
INDE 12 21 51 FOBS=    38.9 SIGMA=  4.0 PHAS= -170.9 FOM= 0.60 TEST= 0
INDE 12 21 53 FOBS=    60.6 SIGMA=  2.6 PHAS=  -33.2 FOM= 0.37 TEST= 0
INDE 12 21 55 FOBS=    83.2 SIGMA=  2.1 PHAS= -128.1 FOM= 0.86 TEST= 0
INDE 12 21 57 FOBS=   103.1 SIGMA=  2.1 PHAS=  112.7 FOM= 0.90 TEST= 0
INDE 12 21 59 FOBS=    86.6 SIGMA=  2.4 PHAS=  131.5 FOM= 0.87 TEST= 0
INDE 12 21 61 FOBS=    46.6 SIGMA=  5.3 PHAS=  -39.2 FOM= 0.78 TEST= 0
INDE 12 21 63 FOBS=    59.2 SIGMA=  4.1 PHAS= -139.6 FOM= 0.64 TEST= 0
INDE 12 21 65 FOBS=   148.0 SIGMA=  3.4 PHAS=  117.0 FOM= 0.97 TEST= 0
INDE 12 21 67 FOBS=    76.7 SIGMA=  6.5 PHAS=   36.6 FOM= 0.82 TEST= 0
INDE 12 21 69 FOBS=   112.9 SIGMA=  4.5 PHAS=   72.0 FOM= 0.95 TEST= 0
INDE 12 21 71 FOBS=    37.8 SIGMA= 13.4 PHAS=  -31.5 FOM= 0.58 TEST= 0
INDE 12 22 12 FOBS=    77.6 SIGMA=  0.9 PHAS=   51.4 FOM= 0.95 TEST= 0
INDE 12 22 14 FOBS=   168.5 SIGMA=  0.5 PHAS=  -24.5 FOM= 0.93 TEST= 0
INDE 12 22 16 FOBS=    71.3 SIGMA=  1.2 PHAS=  -78.1 FOM= 0.96 TEST= 0
```

*FIG. 12A - 304*

```
INDE 12 22 18 FOBS=    113.8 SIGMA=  0.7 PHAS=  153.4 FOM= 0.99 TEST= 0
INDE 12 22 20 FOBS=    109.8 SIGMA=  0.8 PHAS=   40.5 FOM= 0.81 TEST= 0
INDE 12 22 22 FOBS=    108.1 SIGMA=  0.9 PHAS=  -53.3 FOM= 0.99 TEST= 0
INDE 12 22 24 FOBS=     98.0 SIGMA=  1.0 PHAS=  -17.0 FOM= 0.89 TEST= 0
INDE 12 22 26 FOBS=    228.1 SIGMA=  0.6 PHAS=  147.2 FOM= 0.96 TEST= 0
INDE 12 22 28 FOBS=    124.0 SIGMA=  0.8 PHAS= -105.3 FOM= 0.98 TEST= 0
INDE 12 22 30 FOBS=    105.8 SIGMA=  1.1 PHAS=  140.8 FOM= 0.52 TEST= 0
INDE 12 22 32 FOBS=     69.2 SIGMA=  1.7 PHAS= -100.8 FOM= 0.82 TEST= 0
INDE 12 22 34 FOBS=     95.2 SIGMA=  1.3 PHAS=  -29.5 FOM= 0.50 TEST= 0
INDE 12 22 36 FOBS=     88.5 SIGMA=  1.4 PHAS= -174.0 FOM= 0.83 TEST= 1
INDE 12 22 38 FOBS=    108.4 SIGMA=  1.3 PHAS=  -84.4 FOM= 0.89 TEST= 0
INDE 12 22 40 FOBS=    126.3 SIGMA=  1.2 PHAS=   89.1 FOM= 0.84 TEST= 0
INDE 12 22 42 FOBS=    149.6 SIGMA=  1.1 PHAS= -167.0 FOM= 0.84 TEST= 0
INDE 12 22 44 FOBS=    304.6 SIGMA=  0.7 PHAS=  170.7 FOM= 0.97 TEST= 0
INDE 12 22 46 FOBS=    143.4 SIGMA=  1.1 PHAS=  125.4 FOM= 0.94 TEST= 0
INDE 12 22 48 FOBS=     34.7 SIGMA=  4.2 PHAS=  -56.6 FOM= 0.88 TEST= 0
INDE 12 22 50 FOBS=     31.7 SIGMA=  4.9 PHAS= -168.1 FOM= 0.32 TEST= 0
INDE 12 22 52 FOBS=     69.2 SIGMA=  2.2 PHAS= -137.0 FOM= 0.62 TEST= 0
INDE 12 22 54 FOBS=     29.6 SIGMA=  7.1 PHAS= -153.2 FOM= 0.61 TEST= 0
INDE 12 22 56 FOBS=     80.7 SIGMA=  2.6 PHAS=    1.5 FOM= 0.95 TEST= 0
INDE 12 22 58 FOBS=    110.9 SIGMA=  1.9 PHAS=   36.1 FOM= 0.91 TEST= 0
INDE 12 22 60 FOBS=     98.9 SIGMA=  2.6 PHAS=  174.4 FOM= 0.91 TEST= 0
INDE 12 22 62 FOBS=    161.9 SIGMA=  0.9 PHAS= -130.3 FOM= 0.96 TEST= 0
INDE 12 22 64 FOBS=    130.2 SIGMA=  2.9 PHAS=    8.8 FOM= 0.79 TEST= 1
INDE 12 22 66 FOBS=     62.8 SIGMA=  7.9 PHAS=    5.2 FOM= 0.68 TEST= 0
INDE 12 22 68 FOBS=     49.3 SIGMA= 10.1 PHAS=  -21.4 FOM= 0.88 TEST= 0
INDE 12 22 70 FOBS=      0.0 SIGMA= 31.7 PHAS=    0.0 FOM= 0.00 TEST= 1
INDE 12 22 72 FOBS=      0.0 SIGMA= 32.1 PHAS=    0.0 FOM= 0.00 TEST= 0
INDE 12 23 13 FOBS=     57.6 SIGMA=  1.3 PHAS= -149.8 FOM= 0.98 TEST= 0
INDE 12 23 15 FOBS=     61.8 SIGMA=  1.2 PHAS= -155.6 FOM= 0.98 TEST= 0
INDE 12 23 17 FOBS=     72.5 SIGMA=  1.2 PHAS=  113.6 FOM= 0.95 TEST= 0
INDE 12 23 19 FOBS=    129.7 SIGMA=  0.6 PHAS= -114.2 FOM= 0.98 TEST= 0
INDE 12 23 21 FOBS=    117.8 SIGMA=  0.8 PHAS= -126.6 FOM= 0.96 TEST= 0
INDE 12 23 23 FOBS=    241.6 SIGMA=  0.5 PHAS= -166.7 FOM= 0.97 TEST= 0
INDE 12 23 25 FOBS=    213.7 SIGMA=  0.6 PHAS= -160.5 FOM= 0.97 TEST= 0
INDE 12 23 27 FOBS=    191.7 SIGMA=  0.7 PHAS=  163.7 FOM= 0.96 TEST= 0
INDE 12 23 29 FOBS=    173.3 SIGMA=  0.7 PHAS=  128.6 FOM= 0.98 TEST= 0
INDE 12 23 31 FOBS=     66.6 SIGMA=  1.7 PHAS=  109.4 FOM= 0.99 TEST= 0
INDE 12 23 33 FOBS=    200.9 SIGMA=  0.7 PHAS= -166.3 FOM= 0.94 TEST= 0
INDE 12 23 35 FOBS=    232.8 SIGMA=  0.7 PHAS= -109.6 FOM= 0.94 TEST= 0
INDE 12 23 37 FOBS=    173.6 SIGMA=  0.8 PHAS=  138.9 FOM= 0.89 TEST= 0
INDE 12 23 39 FOBS=     88.1 SIGMA=  1.7 PHAS= -164.6 FOM= 0.97 TEST= 0
INDE 12 23 41 FOBS=    192.8 SIGMA=  0.9 PHAS=    7.7 FOM= 0.91 TEST= 0
INDE 12 23 43 FOBS=    200.5 SIGMA=  0.8 PHAS=   27.6 FOM= 0.82 TEST= 0
INDE 12 23 45 FOBS=     91.4 SIGMA=  1.7 PHAS=   20.3 FOM= 0.94 TEST= 0
INDE 12 23 47 FOBS=    150.7 SIGMA=  1.0 PHAS=  -14.3 FOM= 0.79 TEST= 0
INDE 12 23 49 FOBS=      6.4 SIGMA= 22.7 PHAS= -154.2 FOM= 0.08 TEST= 0
INDE 12 23 51 FOBS=     95.3 SIGMA=  1.6 PHAS= -153.4 FOM= 0.93 TEST= 0
INDE 12 23 53 FOBS=     46.5 SIGMA=  4.0 PHAS=    7.5 FOM= 0.60 TEST= 0
INDE 12 23 55 FOBS=    185.3 SIGMA=  1.3 PHAS=  -95.9 FOM= 0.98 TEST= 0
INDE 12 23 57 FOBS=     51.8 SIGMA=  4.0 PHAS= -115.2 FOM= 0.28 TEST= 1
INDE 12 23 59 FOBS=     60.6 SIGMA=  3.4 PHAS=  126.1 FOM= 0.85 TEST= 0
INDE 12 23 61 FOBS=     76.7 SIGMA=  3.3 PHAS=  158.7 FOM= 0.76 TEST= 0
INDE 12 23 63 FOBS=     35.9 SIGMA=  7.9 PHAS= -155.3 FOM= 0.68 TEST= 0
INDE 12 23 65 FOBS=     41.9 SIGMA= 10.9 PHAS=  107.8 FOM= 0.49 TEST= 0
INDE 12 23 67 FOBS=    105.6 SIGMA=  4.6 PHAS=  -66.6 FOM= 0.93 TEST= 0
INDE 12 23 69 FOBS=      0.0 SIGMA= 31.3 PHAS=    0.0 FOM= 0.00 TEST= 0
INDE 12 23 71 FOBS=      0.0 SIGMA= 31.9 PHAS=    0.0 FOM= 0.00 TEST= 1
INDE 12 23 73 FOBS=     10.8 SIGMA= 49.3 PHAS=   -4.6 FOM= 0.04 TEST= 0
INDE 12 24 12 FOBS=    137.8 SIGMA=  0.6 PHAS=  115.7 FOM= 0.99 TEST= 0
INDE 12 24 14 FOBS=     87.6 SIGMA=  0.9 PHAS=   47.6 FOM= 0.96 TEST= 0
INDE 12 24 16 FOBS=    119.1 SIGMA=  0.8 PHAS=   92.8 FOM= 0.83 TEST= 0
INDE 12 24 18 FOBS=    168.7 SIGMA=  0.6 PHAS=  127.8 FOM= 0.95 TEST= 0
INDE 12 24 20 FOBS=     81.6 SIGMA=  1.0 PHAS=  -13.4 FOM= 0.30 TEST= 0
INDE 12 24 22 FOBS=    131.6 SIGMA=  0.7 PHAS=  175.4 FOM= 0.95 TEST= 0
INDE 12 24 24 FOBS=    237.0 SIGMA=  0.5 PHAS=   67.4 FOM= 0.94 TEST= 0
INDE 12 24 26 FOBS=    202.3 SIGMA=  0.7 PHAS=   61.5 FOM= 0.97 TEST= 0
INDE 12 24 28 FOBS=    111.8 SIGMA=  1.1 PHAS=  -66.5 FOM= 0.77 TEST= 0
INDE 12 24 30 FOBS=     74.0 SIGMA=  1.7 PHAS=   70.8 FOM= 0.98 TEST= 1
INDE 12 24 32 FOBS=    331.8 SIGMA=  0.6 PHAS=  -29.5 FOM= 0.94 TEST= 0
```

*FIG. 12A - 305*

```
INDE 12 24 34 FOBS=  163.6 SIGMA=  0.9 PHAS=   76.6 FOM= 0.80 TEST= 0
INDE 12 24 36 FOBS=  171.1 SIGMA=  0.9 PHAS=  123.2 FOM= 0.90 TEST= 0
INDE 12 24 38 FOBS=   71.4 SIGMA=  2.2 PHAS=    5.4 FOM= 0.95 TEST= 0
INDE 12 24 40 FOBS=   87.1 SIGMA=  1.9 PHAS=  158.0 FOM= 0.95 TEST= 0
INDE 12 24 42 FOBS=  141.3 SIGMA=  1.2 PHAS=  -77.5 FOM= 0.67 TEST= 0
INDE 12 24 44 FOBS=  151.0 SIGMA=  1.1 PHAS= -172.7 FOM= 0.63 TEST= 1
INDE 12 24 46 FOBS=  164.9 SIGMA=  1.0 PHAS=  -86.6 FOM= 0.91 TEST= 0
INDE 12 24 48 FOBS=   90.5 SIGMA=  1.6 PHAS=   89.1 FOM= 0.48 TEST= 0
INDE 12 24 50 FOBS=   53.5 SIGMA=  2.9 PHAS=  172.1 FOM= 0.90 TEST= 0
INDE 12 24 52 FOBS=   30.2 SIGMA=  6.2 PHAS=  140.7 FOM= 0.08 TEST= 0
INDE 12 24 54 FOBS=   44.5 SIGMA=  4.2 PHAS= -154.3 FOM= 0.48 TEST= 0
INDE 12 24 56 FOBS=   23.1 SIGMA=  9.1 PHAS=   63.2 FOM= 0.05 TEST= 0
INDE 12 24 58 FOBS=   46.0 SIGMA=  5.4 PHAS=   14.8 FOM= 0.79 TEST= 0
INDE 12 24 60 FOBS=    0.0 SIGMA= 24.0 PHAS=    0.0 FOM= 0.00 TEST= 0
INDE 12 24 62 FOBS=    0.0 SIGMA= 22.2 PHAS=    0.0 FOM= 0.00 TEST= 0
INDE 12 24 64 FOBS=  112.6 SIGMA=  4.3 PHAS=    8.4 FOM= 0.90 TEST= 0
INDE 12 24 66 FOBS=   90.6 SIGMA=  5.4 PHAS=  -84.5 FOM= 0.93 TEST= 0
INDE 12 24 68 FOBS=   74.1 SIGMA=  6.7 PHAS= -155.0 FOM= 0.85 TEST= 0
INDE 12 24 70 FOBS=    0.0 SIGMA= 31.8 PHAS=    0.0 FOM= 0.00 TEST= 0
INDE 12 24 72 FOBS=   16.2 SIGMA= 32.4 PHAS= -128.6 FOM= 0.08 TEST= 0
INDE 12 25 13 FOBS=   73.9 SIGMA=  1.1 PHAS=  -21.9 FOM= 0.96 TEST= 1
INDE 12 25 15 FOBS=  152.9 SIGMA=  0.6 PHAS=   74.0 FOM= 0.99 TEST= 0
INDE 12 25 17 FOBS=  137.7 SIGMA=  0.7 PHAS=  166.2 FOM= 0.79 TEST= 0
INDE 12 25 19 FOBS=   36.7 SIGMA=  2.3 PHAS= -148.6 FOM= 0.75 TEST= 0
INDE 12 25 21 FOBS=  227.6 SIGMA=  0.5 PHAS= -123.3 FOM= 0.92 TEST= 0
INDE 12 25 23 FOBS=   55.8 SIGMA=  1.8 PHAS=  -56.9 FOM= 0.35 TEST= 0
INDE 12 25 25 FOBS=  103.9 SIGMA=  1.2 PHAS= -115.0 FOM= 0.93 TEST= 0
INDE 12 25 27 FOBS=  285.5 SIGMA=  0.6 PHAS= -130.9 FOM= 0.94 TEST= 0
INDE 12 25 29 FOBS=  225.0 SIGMA=  0.7 PHAS=  107.7 FOM= 0.99 TEST= 1
INDE 12 25 31 FOBS=  107.6 SIGMA=  1.3 PHAS=  -70.8 FOM= 0.68 TEST= 0
INDE 12 25 33 FOBS=  372.6 SIGMA=  0.6 PHAS= -120.1 FOM= 0.93 TEST= 0
INDE 12 25 35 FOBS=  320.4 SIGMA=  0.7 PHAS= -107.8 FOM= 0.97 TEST= 0
INDE 12 25 37 FOBS=   66.1 SIGMA=  2.3 PHAS= -124.9 FOM= 0.90 TEST= 0
INDE 12 25 39 FOBS=   82.5 SIGMA=  2.0 PHAS=  101.7 FOM= 0.44 TEST= 0
INDE 12 25 41 FOBS=   79.8 SIGMA=  2.0 PHAS=  -23.6 FOM= 0.96 TEST= 1
INDE 12 25 43 FOBS=   77.7 SIGMA=  2.0 PHAS=  151.1 FOM= 0.81 TEST= 0
INDE 12 25 45 FOBS=  143.4 SIGMA=  1.1 PHAS= -167.2 FOM= 0.86 TEST= 0
INDE 12 25 47 FOBS=   79.2 SIGMA=  1.9 PHAS=  173.1 FOM= 0.76 TEST= 0
INDE 12 25 49 FOBS=   58.6 SIGMA=  2.6 PHAS=   96.0 FOM= 0.82 TEST= 0
INDE 12 25 51 FOBS=   37.1 SIGMA=  4.6 PHAS=   86.7 FOM= 0.67 TEST= 0
INDE 12 25 53 FOBS=   65.5 SIGMA=  2.7 PHAS=  140.4 FOM= 0.20 TEST= 0
INDE 12 25 55 FOBS=  106.0 SIGMA=  1.8 PHAS= -143.3 FOM= 0.96 TEST= 0
INDE 12 25 57 FOBS=  112.0 SIGMA=  2.0 PHAS= -157.0 FOM= 0.12 TEST= 1
INDE 12 25 59 FOBS=   29.7 SIGMA=  8.4 PHAS=  106.5 FOM= 0.22 TEST= 1
INDE 12 25 61 FOBS=   25.7 SIGMA=  9.7 PHAS=  -37.8 FOM= 0.56 TEST= 0
INDE 12 25 63 FOBS=   79.6 SIGMA=  2.2 PHAS= -124.7 FOM= 0.81 TEST= 0
INDE 12 25 65 FOBS=   81.5 SIGMA=  6.0 PHAS= -158.6 FOM= 0.76 TEST= 0
INDE 12 25 67 FOBS=   84.0 SIGMA=  5.8 PHAS= -167.1 FOM= 0.93 TEST= 0
INDE 12 25 69 FOBS=    0.0 SIGMA= 31.2 PHAS=    0.0 FOM= 0.00 TEST= 0
INDE 12 25 71 FOBS=    0.0 SIGMA= 31.8 PHAS=    0.0 FOM= 0.00 TEST= 0
INDE 12 26 12 FOBS=   32.0 SIGMA=  2.2 PHAS=   72.9 FOM= 0.94 TEST= 0
INDE 12 26 14 FOBS=   74.2 SIGMA=  1.1 PHAS=    2.4 FOM= 0.99 TEST= 0
INDE 12 26 16 FOBS=   53.9 SIGMA=  1.6 PHAS=  146.8 FOM= 0.99 TEST= 0
INDE 12 26 18 FOBS=  168.7 SIGMA=  0.6 PHAS=  129.9 FOM= 0.87 TEST= 0
INDE 12 26 20 FOBS=   96.6 SIGMA=  0.9 PHAS=   14.0 FOM= 0.57 TEST= 0
INDE 12 26 22 FOBS=   76.6 SIGMA=  1.3 PHAS=  151.9 FOM= 0.97 TEST= 0
INDE 12 26 24 FOBS=  142.6 SIGMA=  0.9 PHAS=  170.7 FOM= 0.62 TEST= 1
INDE 12 26 26 FOBS=  162.8 SIGMA=  0.8 PHAS=   71.0 FOM= 0.72 TEST= 0
INDE 12 26 28 FOBS=   43.3 SIGMA=  3.0 PHAS=  143.2 FOM= 0.94 TEST= 0
INDE 12 26 30 FOBS=  236.3 SIGMA=  0.7 PHAS=   35.2 FOM= 0.95 TEST= 0
INDE 12 26 32 FOBS=    0.0 SIGMA= 17.0 PHAS=    0.0 FOM= 0.00 TEST= 1
INDE 12 26 34 FOBS=  159.5 SIGMA=  1.0 PHAS=  168.8 FOM= 0.94 TEST= 0
INDE 12 26 36 FOBS=  305.2 SIGMA=  0.7 PHAS=   93.1 FOM= 0.95 TEST= 0
INDE 12 26 38 FOBS=  194.5 SIGMA=  1.0 PHAS=   89.9 FOM= 0.88 TEST= 0
INDE 12 26 40 FOBS=  131.0 SIGMA=  1.3 PHAS= -154.7 FOM= 0.93 TEST= 0
INDE 12 26 42 FOBS=  175.5 SIGMA=  1.1 PHAS=   72.4 FOM= 0.91 TEST= 0
INDE 12 26 44 FOBS=   47.2 SIGMA=  3.2 PHAS=  105.6 FOM= 0.06 TEST= 1
INDE 12 26 46 FOBS=   99.2 SIGMA=  2.6 PHAS=   35.1 FOM= 0.57 TEST= 0
INDE 12 26 48 FOBS=  131.1 SIGMA=  1.4 PHAS=   89.8 FOM= 0.95 TEST= 0
INDE 12 26 50 FOBS=  104.4 SIGMA=  1.7 PHAS=  154.7 FOM= 0.13 TEST= 0
```

*FIG. 12A - 306*

```
INDE  12  26  52  FOBS=   131.7  SIGMA=   1.4  PHAS=   -61.3  FOM=  0.93  TEST= 0
INDE  12  26  54  FOBS=    53.3  SIGMA=   3.2  PHAS=    87.8  FOM=  0.81  TEST= 0
INDE  12  26  56  FOBS=    37.1  SIGMA=   5.0  PHAS=    84.5  FOM=  0.46  TEST= 0
INDE  12  26  58  FOBS=    44.6  SIGMA=   5.1  PHAS=   -75.3  FOM=  0.37  TEST= 0
INDE  12  26  60  FOBS=    83.9  SIGMA=   3.1  PHAS=   -59.0  FOM=  0.81  TEST= 0
INDE  12  26  62  FOBS=    18.8  SIGMA=  15.2  PHAS=   163.6  FOM=  0.50  TEST= 0
INDE  12  26  64  FOBS=    23.6  SIGMA=   8.7  PHAS=     4.9  FOM=  0.02  TEST= 1
INDE  12  26  66  FOBS=    74.5  SIGMA=   6.5  PHAS=   165.9  FOM=  0.83  TEST= 0
INDE  12  26  68  FOBS=    22.1  SIGMA=  21.5  PHAS=  -128.9  FOM=  0.27  TEST= 0
INDE  12  26  70  FOBS=    47.1  SIGMA=  10.5  PHAS=   136.6  FOM=  0.58  TEST= 0
INDE  12  26  72  FOBS=     0.0  SIGMA=  31.9  PHAS=     0.0  FOM=  0.00  TEST= 0
INDE  12  27  13  FOBS=   130.1  SIGMA=   0.7  PHAS=   -43.1  FOM=  0.94  TEST= 0
INDE  12  27  15  FOBS=   239.5  SIGMA=   0.5  PHAS=    48.1  FOM=  0.95  TEST= 0
INDE  12  27  17  FOBS=    76.9  SIGMA=   1.3  PHAS=   151.4  FOM=  0.92  TEST= 0
INDE  12  27  19  FOBS=   123.6  SIGMA=   1.0  PHAS=   132.6  FOM=  0.93  TEST= 1
INDE  12  27  21  FOBS=   295.8  SIGMA=   0.5  PHAS=  -135.6  FOM=  0.99  TEST= 0
INDE  12  27  23  FOBS=   115.4  SIGMA=   1.0  PHAS=   -23.4  FOM=  0.97  TEST= 0
INDE  12  27  25  FOBS=   111.9  SIGMA=   1.1  PHAS=   128.2  FOM=  0.87  TEST= 0
INDE  12  27  27  FOBS=   208.4  SIGMA=   0.7  PHAS=  -131.1  FOM=  0.94  TEST= 0
INDE  12  27  29  FOBS=    96.3  SIGMA=   1.5  PHAS=    40.5  FOM=  0.21  TEST= 1
INDE  12  27  31  FOBS=     0.0  SIGMA=  19.0  PHAS=     0.0  FOM=  0.00  TEST= 0
INDE  12  27  33  FOBS=   130.1  SIGMA=   1.3  PHAS=   -74.0  FOM=  0.76  TEST= 0
INDE  12  27  35  FOBS=    58.1  SIGMA=   2.9  PHAS=   144.0  FOM=  0.73  TEST= 0
INDE  12  27  37  FOBS=    61.5  SIGMA=   2.7  PHAS=  -113.0  FOM=  0.62  TEST= 0
INDE  12  27  39  FOBS=   204.9  SIGMA=   1.0  PHAS=   126.5  FOM=  0.95  TEST= 0
INDE  12  27  41  FOBS=   200.9  SIGMA=   0.9  PHAS=   -22.8  FOM=  0.94  TEST= 0
INDE  12  27  43  FOBS=   138.8  SIGMA=   1.2  PHAS=  -137.9  FOM=  0.88  TEST= 0
INDE  12  27  45  FOBS=    61.5  SIGMA=   2.6  PHAS=   -73.8  FOM=  0.50  TEST= 0
INDE  12  27  47  FOBS=    33.3  SIGMA=   5.5  PHAS=    20.5  FOM=  0.76  TEST= 0
INDE  12  27  49  FOBS=    67.9  SIGMA=   2.6  PHAS=    80.0  FOM=  0.78  TEST= 0
INDE  12  27  51  FOBS=     0.0  SIGMA=  19.4  PHAS=     0.0  FOM=  0.00  TEST= 0
INDE  12  27  53  FOBS=    94.2  SIGMA=   1.8  PHAS=  -137.8  FOM=  0.90  TEST= 0
INDE  12  27  55  FOBS=    92.8  SIGMA=   1.8  PHAS=   139.0  FOM=  0.94  TEST= 0
INDE  12  27  57  FOBS=   141.9  SIGMA=   1.6  PHAS=   125.2  FOM=  0.06  TEST= 1
INDE  12  27  59  FOBS=   127.8  SIGMA=   1.9  PHAS=  -164.7  FOM=  0.92  TEST= 0
INDE  12  27  61  FOBS=     0.0  SIGMA=  22.3  PHAS=     0.0  FOM=  0.00  TEST= 0
INDE  12  27  63  FOBS=    15.8  SIGMA=  12.2  PHAS=    45.1  FOM=  0.18  TEST= 0
INDE  12  27  65  FOBS=    34.4  SIGMA=   6.1  PHAS=  -101.8  FOM=  0.81  TEST= 0
INDE  12  27  67  FOBS=    42.2  SIGMA=  11.6  PHAS=  -158.1  FOM=  0.14  TEST= 0
INDE  12  27  69  FOBS=     0.0  SIGMA=  31.1  PHAS=     0.0  FOM=  0.00  TEST= 0
INDE  12  27  71  FOBS=     0.0  SIGMA=  31.2  PHAS=     0.0  FOM=  0.00  TEST= 0
INDE  12  28  12  FOBS=   156.6  SIGMA=   0.6  PHAS=   -18.1  FOM=  0.96  TEST= 0
INDE  12  28  14  FOBS=   211.8  SIGMA=   0.5  PHAS=   -57.4  FOM=  0.94  TEST= 0
INDE  12  28  16  FOBS=   164.9  SIGMA=   0.6  PHAS=     4.0  FOM=  0.98  TEST= 0
INDE  12  28  18  FOBS=   287.6  SIGMA=   0.6  PHAS=   144.5  FOM=  0.96  TEST= 0
INDE  12  28  20  FOBS=   192.9  SIGMA=   0.7  PHAS=    89.8  FOM=  0.95  TEST= 0
INDE  12  28  22  FOBS=   144.6  SIGMA=   0.8  PHAS=   139.3  FOM=  0.71  TEST= 0
INDE  12  28  24  FOBS=   239.6  SIGMA=   0.7  PHAS=  -147.2  FOM=  0.99  TEST= 0
INDE  12  28  26  FOBS=   163.7  SIGMA=   0.9  PHAS=   -23.8  FOM=  0.95  TEST= 0
INDE  12  28  28  FOBS=   261.1  SIGMA=   0.6  PHAS=    50.0  FOM=  0.08  TEST= 1
INDE  12  28  30  FOBS=    98.2  SIGMA=   1.6  PHAS=   -72.4  FOM=  0.70  TEST= 0
INDE  12  28  32  FOBS=   155.4  SIGMA=   1.1  PHAS=  -122.0  FOM=  0.68  TEST= 0
INDE  12  28  34  FOBS=    90.5  SIGMA=   1.9  PHAS=   -27.0  FOM=  0.56  TEST= 0
INDE  12  28  36  FOBS=   227.3  SIGMA=   0.9  PHAS=    40.9  FOM=  0.94  TEST= 0
INDE  12  28  38  FOBS=   401.6  SIGMA=   0.9  PHAS=    81.3  FOM=  0.98  TEST= 0
INDE  12  28  40  FOBS=    46.8  SIGMA=   3.5  PHAS=  -152.3  FOM=  0.77  TEST= 0
INDE  12  28  42  FOBS=   105.5  SIGMA=   1.3  PHAS=   121.7  FOM=  0.87  TEST= 0
INDE  12  28  44  FOBS=    76.1  SIGMA=   2.5  PHAS=  -152.2  FOM=  0.91  TEST= 1
INDE  12  28  46  FOBS=    88.5  SIGMA=   2.2  PHAS=  -137.1  FOM=  0.80  TEST= 1
INDE  12  28  48  FOBS=   142.2  SIGMA=   1.3  PHAS=    -1.8  FOM=  0.90  TEST= 0
INDE  12  28  50  FOBS=    97.8  SIGMA=   1.3  PHAS=   -13.7  FOM=  0.77  TEST= 0
INDE  12  28  52  FOBS=    49.5  SIGMA=   3.4  PHAS=   157.5  FOM=  0.74  TEST= 0
INDE  12  28  54  FOBS=    44.8  SIGMA=   3.3  PHAS=    65.7  FOM=  0.78  TEST= 0
INDE  12  28  56  FOBS=    76.7  SIGMA=   2.2  PHAS=    94.0  FOM=  0.83  TEST= 0
INDE  12  28  58  FOBS=    28.9  SIGMA=   9.0  PHAS=   -70.4  FOM=  0.25  TEST= 0
INDE  12  28  60  FOBS=    55.0  SIGMA=   3.3  PHAS=    29.2  FOM=  0.82  TEST= 0
INDE  12  28  62  FOBS=    36.8  SIGMA=   9.2  PHAS=   -96.9  FOM=  0.42  TEST= 0
INDE  12  28  64  FOBS=    65.4  SIGMA=   3.1  PHAS=  -142.4  FOM=  0.89  TEST= 0
INDE  12  28  66  FOBS=    34.2  SIGMA=   6.3  PHAS=  -143.6  FOM=  0.58  TEST= 0
INDE  12  28  68  FOBS=    47.2  SIGMA=  10.5  PHAS=   134.4  FOM=  0.65  TEST= 0
```

*FIG. 12A - 307*

```
INDE 12 28 70 FOBS=   0.0 SIGMA= 31.8 PHAS=    0.0 FOM= 0.00 TEST= 1
INDE 12 29 13 FOBS= 191.1 SIGMA=  0.6 PHAS= -111.4 FOM= 0.92 TEST= 0
INDE 12 29 15 FOBS= 163.4 SIGMA=  0.7 PHAS=  -82.0 FOM= 0.98 TEST= 0
INDE 12 29 17 FOBS= 183.7 SIGMA=  0.7 PHAS=  -35.0 FOM= 0.92 TEST= 0
INDE 12 29 19 FOBS= 134.0 SIGMA=  0.9 PHAS=   66.5 FOM= 0.96 TEST= 0
INDE 12 29 21 FOBS=  89.4 SIGMA=  1.3 PHAS=  -98.9 FOM= 0.96 TEST= 0
INDE 12 29 23 FOBS= 191.3 SIGMA=  0.7 PHAS=   50.8 FOM= 0.94 TEST= 0
INDE 12 29 25 FOBS= 224.7 SIGMA=  0.7 PHAS= -129.5 FOM= 0.98 TEST= 0
INDE 12 29 27 FOBS= 256.5 SIGMA=  0.6 PHAS= -164.8 FOM= 0.94 TEST= 0
INDE 12 29 29 FOBS= 142.7 SIGMA=  1.0 PHAS=  120.2 FOM= 0.95 TEST= 0
INDE 12 29 31 FOBS= 276.8 SIGMA=  1.2 PHAS=  -73.9 FOM= 0.25 TEST= 1
INDE 12 29 33 FOBS= 221.1 SIGMA=  1.1 PHAS=   55.6 FOM= 0.92 TEST= 0
INDE 12 29 35 FOBS= 140.2 SIGMA=  1.3 PHAS=  -31.7 FOM= 0.88 TEST= 0
INDE 12 29 37 FOBS=  64.2 SIGMA=  3.1 PHAS=  133.7 FOM= 0.68 TEST= 0
INDE 12 29 39 FOBS=  97.7 SIGMA=  2.0 PHAS= -101.8 FOM= 0.94 TEST= 0
INDE 12 29 41 FOBS= 179.6 SIGMA=  1.2 PHAS=  -22.9 FOM= 0.93 TEST= 0
INDE 12 29 43 FOBS=  55.6 SIGMA=  3.6 PHAS=  -19.9 FOM= 0.70 TEST= 0
INDE 12 29 45 FOBS=   0.0 SIGMA= 20.4 PHAS=    0.0 FOM= 0.00 TEST= 0
INDE 12 29 47 FOBS=  18.3 SIGMA= 12.0 PHAS=  123.7 FOM= 0.10 TEST= 0
INDE 12 29 49 FOBS=  94.6 SIGMA=  2.0 PHAS=  -40.6 FOM= 0.94 TEST= 0
INDE 12 29 51 FOBS= 101.8 SIGMA=  1.7 PHAS=  -21.7 FOM= 0.76 TEST= 0
INDE 12 29 53 FOBS=  43.0 SIGMA=  4.2 PHAS=  119.5 FOM= 0.77 TEST= 0
INDE 12 29 55 FOBS=   0.0 SIGMA= 18.2 PHAS=    0.0 FOM= 0.00 TEST= 0
INDE 12 29 57 FOBS=  53.1 SIGMA=  3.4 PHAS=  169.9 FOM= 0.54 TEST= 0
INDE 12 29 59 FOBS= 136.9 SIGMA=  1.5 PHAS= -138.5 FOM= 0.94 TEST= 0
INDE 12 29 61 FOBS=  43.4 SIGMA=  5.3 PHAS=   37.3 FOM= 0.43 TEST= 0
INDE 12 29 63 FOBS=  63.4 SIGMA=  5.3 PHAS=  105.7 FOM= 0.63 TEST= 0
INDE 12 29 65 FOBS=  31.0 SIGMA=  7.4 PHAS= -168.0 FOM= 0.81 TEST= 0
INDE 12 29 67 FOBS=  96.2 SIGMA=  2.4 PHAS=   -3.6 FOM= 0.91 TEST= 0
INDE 12 29 69 FOBS=  37.8 SIGMA= 13.4 PHAS=   19.5 FOM= 0.33 TEST= 0
INDE 12 29 71 FOBS=  20.1 SIGMA= 25.6 PHAS=  -82.2 FOM= 0.03 TEST= 0
INDE 12 30 12 FOBS= 106.7 SIGMA=  0.8 PHAS=   40.7 FOM= 0.99 TEST= 0
INDE 12 30 14 FOBS= 123.5 SIGMA=  0.9 PHAS=  -76.7 FOM= 0.86 TEST= 0
INDE 12 30 16 FOBS= 218.9 SIGMA=  0.6 PHAS= -143.1 FOM= 0.99 TEST= 0
INDE 12 30 18 FOBS=  85.9 SIGMA=  1.4 PHAS= -128.6 FOM= 0.95 TEST= 1
INDE 12 30 20 FOBS=  84.3 SIGMA=  1.4 PHAS=  -26.8 FOM= 0.91 TEST= 0
INDE 12 30 22 FOBS= 104.3 SIGMA=  1.2 PHAS=  -78.1 FOM= 0.99 TEST= 0
INDE 12 30 24 FOBS= 238.6 SIGMA=  0.6 PHAS=  155.4 FOM= 0.98 TEST= 0
INDE 12 30 26 FOBS=  52.5 SIGMA=  2.6 PHAS=  -86.1 FOM= 0.40 TEST= 1
INDE 12 30 28 FOBS= 205.2 SIGMA=  0.8 PHAS=  112.1 FOM= 0.99 TEST= 0
INDE 12 30 30 FOBS=  65.2 SIGMA=  2.2 PHAS=  -71.9 FOM= 0.94 TEST= 0
INDE 12 30 32 FOBS= 211.1 SIGMA=  0.9 PHAS=   24.7 FOM= 0.92 TEST= 0
INDE 12 30 34 FOBS= 225.8 SIGMA=  1.1 PHAS=  -21.2 FOM= 0.97 TEST= 0
INDE 12 30 36 FOBS= 198.5 SIGMA=  1.2 PHAS=    4.8 FOM= 0.89 TEST= 0
INDE 12 30 38 FOBS= 280.3 SIGMA=  1.0 PHAS=  101.7 FOM= 0.96 TEST= 0
INDE 12 30 40 FOBS= 140.3 SIGMA=  1.7 PHAS=  164.3 FOM= 0.95 TEST= 0
INDE 12 30 42 FOBS= 142.4 SIGMA=  1.5 PHAS= -112.0 FOM= 0.83 TEST= 0
INDE 12 30 44 FOBS=  94.2 SIGMA=  2.1 PHAS= -125.8 FOM= 0.88 TEST= 0
INDE 12 30 46 FOBS=  55.4 SIGMA=  3.6 PHAS=  126.2 FOM= 0.39 TEST= 1
INDE 12 30 48 FOBS=  64.1 SIGMA=  3.0 PHAS=  -58.6 FOM= 0.94 TEST= 0
INDE 12 30 50 FOBS=  55.8 SIGMA=  3.4 PHAS=  139.7 FOM= 0.47 TEST= 0
INDE 12 30 52 FOBS=  50.6 SIGMA=  3.4 PHAS=   16.4 FOM= 0.86 TEST= 0
INDE 12 30 54 FOBS=  50.5 SIGMA=  3.3 PHAS=   34.8 FOM= 0.78 TEST= 0
INDE 12 30 56 FOBS=  44.0 SIGMA=  4.7 PHAS=  161.4 FOM= 0.39 TEST= 0
INDE 12 30 58 FOBS=   0.0 SIGMA= 19.6 PHAS=    0.0 FOM= 0.00 TEST= 0
INDE 12 30 60 FOBS=   0.0 SIGMA= 20.2 PHAS=    0.0 FOM= 0.00 TEST= 0
INDE 12 30 62 FOBS=  45.8 SIGMA=  5.5 PHAS=  -72.7 FOM= 0.51 TEST= 0
INDE 12 30 64 FOBS=  27.9 SIGMA=  7.5 PHAS=  179.5 FOM= 0.56 TEST= 0
INDE 12 30 66 FOBS=  51.6 SIGMA=  4.7 PHAS= -116.9 FOM= 0.74 TEST= 0
INDE 12 30 68 FOBS=  54.8 SIGMA=  4.1 PHAS= -150.0 FOM= 0.64 TEST= 0
INDE 12 30 70 FOBS=   0.0 SIGMA= 32.1 PHAS=    0.0 FOM= 0.00 TEST= 0
INDE 12 31 13 FOBS=  75.4 SIGMA=  1.4 PHAS=  -51.0 FOM= 0.95 TEST= 0
INDE 12 31 15 FOBS=  90.1 SIGMA=  1.2 PHAS= -151.7 FOM= 0.97 TEST= 0
INDE 12 31 17 FOBS= 111.6 SIGMA=  1.1 PHAS=  131.9 FOM= 0.98 TEST= 0
INDE 12 31 19 FOBS= 293.7 SIGMA=  0.6 PHAS=  173.7 FOM= 0.97 TEST= 0
INDE 12 31 21 FOBS= 255.9 SIGMA=  0.6 PHAS= -128.0 FOM= 0.94 TEST= 0
INDE 12 31 23 FOBS= 152.7 SIGMA=  0.9 PHAS=   69.0 FOM= 0.95 TEST= 0
INDE 12 31 25 FOBS= 225.1 SIGMA=  0.8 PHAS=  -95.1 FOM= 0.95 TEST= 0
INDE 12 31 27 FOBS=  46.1 SIGMA=  3.5 PHAS=   69.6 FOM= 0.66 TEST= 0
INDE 12 31 29 FOBS= 198.5 SIGMA=  0.8 PHAS=   66.3 FOM= 0.97 TEST= 0
```

*FIG. 12A - 308*

```
INDE 12 31 31 FOBS=  259.3 SIGMA=  0.8 PHAS= -169.0 FOM= 0.96 TEST= 0
INDE 12 31 33 FOBS=  258.3 SIGMA=  0.8 PHAS=  -40.0 FOM= 0.98 TEST= 0
INDE 12 31 35 FOBS=  349.1 SIGMA=  0.8 PHAS=  -93.8 FOM= 0.97 TEST= 0
INDE 12 31 37 FOBS=  240.1 SIGMA=  1.1 PHAS=  114.0 FOM= 0.98 TEST= 0
INDE 12 31 39 FOBS=   58.4 SIGMA=  4.0 PHAS=  -43.0 FOM= 0.28 TEST= 0
INDE 12 31 41 FOBS=   91.5 SIGMA=  2.6 PHAS=  101.6 FOM= 0.87 TEST= 0
INDE 12 31 43 FOBS=  187.1 SIGMA=  1.3 PHAS=  103.6 FOM= 0.92 TEST= 0
INDE 12 31 45 FOBS=   39.8 SIGMA=  4.9 PHAS=   86.6 FOM= 0.76 TEST= 0
INDE 12 31 47 FOBS=   52.0 SIGMA=  3.7 PHAS=  147.7 FOM= 0.61 TEST= 0
INDE 12 31 49 FOBS=   90.8 SIGMA=  2.1 PHAS=   58.4 FOM= 0.90 TEST= 0
INDE 12 31 51 FOBS=  202.1 SIGMA=  1.1 PHAS=  -43.8 FOM= 0.65 TEST= 1
INDE 12 31 53 FOBS=   93.4 SIGMA=  2.1 PHAS=  -44.9 FOM= 0.91 TEST= 0
INDE 12 31 55 FOBS=    0.0 SIGMA= 18.6 PHAS=    0.0 FOM= 0.00 TEST= 0
INDE 12 31 57 FOBS=    0.0 SIGMA= 19.5 PHAS=    0.0 FOM= 0.00 TEST= 0
INDE 12 31 59 FOBS=   23.6 SIGMA=  8.1 PHAS= -139.7 FOM= 0.41 TEST= 0
INDE 12 31 61 FOBS=   44.0 SIGMA=  4.7 PHAS=  145.2 FOM= 0.68 TEST= 0
INDE 12 31 63 FOBS=    0.0 SIGMA= 26.3 PHAS=    0.0 FOM= 0.00 TEST= 0
INDE 12 31 65 FOBS=   87.4 SIGMA=  2.9 PHAS=   91.3 FOM= 0.84 TEST= 0
INDE 12 31 67 FOBS=   60.3 SIGMA=  4.1 PHAS= -158.1 FOM= 0.85 TEST= 0
INDE 12 31 69 FOBS=   56.8 SIGMA=  4.1 PHAS= -161.2 FOM= 0.86 TEST= 0
INDE 12 32 12 FOBS=  146.6 SIGMA=  0.7 PHAS= -118.2 FOM= 0.99 TEST= 0
INDE 12 32 14 FOBS=  129.3 SIGMA=  0.9 PHAS=   74.9 FOM= 0.98 TEST= 0
INDE 12 32 16 FOBS=  124.6 SIGMA=  1.0 PHAS= -142.7 FOM= 0.96 TEST= 0
INDE 12 32 18 FOBS=  122.1 SIGMA=  1.1 PHAS=   32.6 FOM= 0.98 TEST= 1
INDE 12 32 20 FOBS=  225.7 SIGMA=  0.7 PHAS=   83.2 FOM= 0.86 TEST= 0
INDE 12 32 22 FOBS=  128.3 SIGMA=  1.1 PHAS= -129.3 FOM= 0.93 TEST= 0
INDE 12 32 24 FOBS=  261.0 SIGMA=  0.7 PHAS=  178.8 FOM= 0.98 TEST= 0
INDE 12 32 26 FOBS=  470.5 SIGMA=  0.8 PHAS= -125.3 FOM= 0.98 TEST= 0
INDE 12 32 28 FOBS=  153.1 SIGMA=  1.1 PHAS=   47.4 FOM= 0.90 TEST= 0
INDE 12 32 30 FOBS=   99.8 SIGMA=  1.7 PHAS=  -70.8 FOM= 0.91 TEST= 0
INDE 12 32 32 FOBS=  206.5 SIGMA=  1.0 PHAS=   -2.2 FOM= 0.94 TEST= 0
INDE 12 32 34 FOBS=  207.0 SIGMA=  1.1 PHAS=  152.6 FOM= 0.95 TEST= 0
INDE 12 32 36 FOBS=  167.9 SIGMA=  1.6 PHAS=  118.5 FOM= 0.85 TEST= 0
INDE 12 32 38 FOBS=   81.6 SIGMA=  2.9 PHAS=   80.4 FOM= 0.83 TEST= 0
INDE 12 32 40 FOBS=   27.3 SIGMA=  8.4 PHAS=   65.1 FOM= 0.06 TEST= 0
INDE 12 32 42 FOBS=  152.4 SIGMA=  1.6 PHAS=   63.8 FOM= 0.86 TEST= 0
INDE 12 32 44 FOBS=   75.2 SIGMA=  3.0 PHAS=   -8.1 FOM= 0.81 TEST= 0
INDE 12 32 46 FOBS=  107.1 SIGMA=  2.0 PHAS=  -18.3 FOM= 0.94 TEST= 0
INDE 12 32 48 FOBS=   32.2 SIGMA=  5.9 PHAS=  155.1 FOM= 0.22 TEST= 0
INDE 12 32 50 FOBS=   55.3 SIGMA=  3.5 PHAS=  -53.6 FOM= 0.49 TEST= 0
INDE 12 32 52 FOBS=  133.2 SIGMA=  1.5 PHAS=  -59.5 FOM= 0.94 TEST= 0
INDE 12 32 54 FOBS=   50.1 SIGMA=  3.7 PHAS= -155.7 FOM= 0.62 TEST= 0
INDE 12 32 56 FOBS=   86.8 SIGMA=  2.3 PHAS=  179.1 FOM= 0.87 TEST= 0
INDE 12 32 58 FOBS=    0.0 SIGMA= 22.9 PHAS=    0.0 FOM= 0.00 TEST= 0
INDE 12 32 60 FOBS=   49.8 SIGMA=  4.2 PHAS=   33.5 FOM= 0.52 TEST= 0
INDE 12 32 62 FOBS=    0.0 SIGMA= 22.1 PHAS=    0.0 FOM= 0.00 TEST= 0
INDE 12 32 64 FOBS=   72.1 SIGMA=  2.7 PHAS= -155.8 FOM= 0.75 TEST= 0
INDE 12 32 66 FOBS=   52.3 SIGMA=  4.4 PHAS=  -64.4 FOM= 0.14 TEST= 1
INDE 12 32 68 FOBS=   87.3 SIGMA=  2.9 PHAS=  135.2 FOM= 0.93 TEST= 0
INDE 12 33 13 FOBS=  153.4 SIGMA=  0.8 PHAS=   96.2 FOM= 0.93 TEST= 1
INDE 12 33 15 FOBS=   96.3 SIGMA=  1.2 PHAS=  -23.7 FOM= 0.96 TEST= 0
INDE 12 33 17 FOBS=  244.9 SIGMA=  0.6 PHAS=  161.4 FOM= 0.97 TEST= 0
INDE 12 33 19 FOBS=  263.1 SIGMA=  0.7 PHAS= -161.8 FOM= 0.92 TEST= 0
INDE 12 33 21 FOBS=   85.6 SIGMA=  1.6 PHAS=  156.0 FOM= 0.95 TEST= 0
INDE 12 33 23 FOBS=  231.5 SIGMA=  0.7 PHAS=  148.5 FOM= 0.75 TEST= 1
INDE 12 33 25 FOBS=  257.3 SIGMA=  0.7 PHAS=  177.2 FOM= 0.97 TEST= 0
INDE 12 33 27 FOBS=  142.9 SIGMA=  1.3 PHAS=  156.2 FOM= 0.82 TEST= 0
INDE 12 33 29 FOBS=  242.4 SIGMA=  1.0 PHAS=  177.7 FOM= 0.89 TEST= 0
INDE 12 33 31 FOBS=    0.0 SIGMA= 19.5 PHAS=    0.0 FOM= 0.00 TEST= 0
INDE 12 33 33 FOBS=  363.0 SIGMA=  0.8 PHAS=  -28.8 FOM= 0.97 TEST= 0
INDE 12 33 35 FOBS=  146.6 SIGMA=  1.4 PHAS= -163.5 FOM= 0.81 TEST= 0
INDE 12 33 37 FOBS=  142.4 SIGMA=  1.8 PHAS=  103.0 FOM= 0.80 TEST= 0
INDE 12 33 39 FOBS=  106.3 SIGMA=  2.2 PHAS= -112.0 FOM= 0.69 TEST= 0
INDE 12 33 41 FOBS=  207.2 SIGMA=  1.3 PHAS=   19.3 FOM= 0.94 TEST= 0
INDE 12 33 43 FOBS=  101.3 SIGMA=  2.3 PHAS=   -4.5 FOM= 0.92 TEST= 0
INDE 12 33 45 FOBS=  126.8 SIGMA=  1.8 PHAS= -148.6 FOM= 0.81 TEST= 0
INDE 12 33 47 FOBS=   50.4 SIGMA=  4.4 PHAS=   90.1 FOM= 0.61 TEST= 0
INDE 12 33 49 FOBS=   78.9 SIGMA=  2.5 PHAS=   95.9 FOM= 0.40 TEST= 1
INDE 12 33 51 FOBS=   55.6 SIGMA=  3.4 PHAS=  107.0 FOM= 0.27 TEST= 0
INDE 12 33 53 FOBS=  113.4 SIGMA=  1.7 PHAS=   43.7 FOM= 0.15 TEST= 1
```

*FIG. 12A - 309*

```
INDE 12 33 55 FOBS=   29.1 SIGMA=  8.2 PHAS=  133.0 FOM= 0.29 TEST= 0
INDE 12 33 57 FOBS=   37.4 SIGMA=  6.0 PHAS=  136.8 FOM= 0.47 TEST= 1
INDE 12 33 59 FOBS=   40.8 SIGMA=  5.5 PHAS=  -61.6 FOM= 0.76 TEST= 0
INDE 12 33 61 FOBS=   49.1 SIGMA=  4.2 PHAS=   30.7 FOM= 0.53 TEST= 0
INDE 12 33 63 FOBS=   30.8 SIGMA=  8.5 PHAS=  168.1 FOM= 0.21 TEST= 0
INDE 12 33 65 FOBS=   45.4 SIGMA=  4.7 PHAS=  102.3 FOM= 0.64 TEST= 0
INDE 12 33 67 FOBS=   38.3 SIGMA=  6.8 PHAS= -118.9 FOM= 0.04 TEST= 0
INDE 12 33 69 FOBS=    9.6 SIGMA= 27.0 PHAS=   33.5 FOM= 0.15 TEST= 0
INDE 12 34 12 FOBS=  161.3 SIGMA=  0.7 PHAS=  -62.5 FOM= 0.93 TEST= 0
INDE 12 34 14 FOBS=  173.7 SIGMA=  0.8 PHAS=  -14.9 FOM= 0.88 TEST= 0
INDE 12 34 16 FOBS=   70.0 SIGMA=  1.9 PHAS=   43.9 FOM= 0.99 TEST= 0
INDE 12 34 18 FOBS=  248.7 SIGMA=  0.7 PHAS=   91.4 FOM= 0.97 TEST= 0
INDE 12 34 20 FOBS=  248.5 SIGMA=  0.7 PHAS=   72.5 FOM= 0.99 TEST= 0
INDE 12 34 22 FOBS=  218.7 SIGMA=  0.9 PHAS= -178.4 FOM= 0.81 TEST= 0
INDE 12 34 24 FOBS=   84.1 SIGMA=  2.1 PHAS= -179.5 FOM= 0.74 TEST= 0
INDE 12 34 26 FOBS=  203.6 SIGMA=  0.9 PHAS=  -76.2 FOM= 0.98 TEST= 0
INDE 12 34 28 FOBS=  241.3 SIGMA=  1.0 PHAS=   67.8 FOM= 0.96 TEST= 0
INDE 12 34 30 FOBS=   84.2 SIGMA=  2.6 PHAS=   36.8 FOM= 0.80 TEST= 0
INDE 12 34 32 FOBS=  228.7 SIGMA=  1.0 PHAS=  -70.0 FOM= 0.95 TEST= 0
INDE 12 34 34 FOBS=  158.8 SIGMA=  1.3 PHAS= -147.0 FOM= 0.87 TEST= 0
INDE 12 34 36 FOBS=  235.1 SIGMA=  1.0 PHAS=   90.0 FOM= 0.96 TEST= 0
INDE 12 34 38 FOBS=   34.8 SIGMA=  6.8 PHAS=  168.6 FOM= 0.36 TEST= 1
INDE 12 34 40 FOBS=  289.9 SIGMA=  1.3 PHAS=  -48.6 FOM= 0.97 TEST= 0
INDE 12 34 42 FOBS=  101.1 SIGMA=  2.3 PHAS= -120.5 FOM= 0.91 TEST= 0
INDE 12 34 44 FOBS=  130.4 SIGMA=  1.8 PHAS=   15.4 FOM= 0.90 TEST= 0
INDE 12 34 46 FOBS=  100.6 SIGMA=  2.3 PHAS=   -8.3 FOM= 0.88 TEST= 0
INDE 12 34 48 FOBS=    0.0 SIGMA= 20.8 PHAS=    0.0 FOM= 0.00 TEST= 0
INDE 12 34 50 FOBS=   53.9 SIGMA=  4.0 PHAS=   18.8 FOM= 0.87 TEST= 0
INDE 12 34 52 FOBS=    0.0 SIGMA= 19.9 PHAS=    0.0 FOM= 0.00 TEST= 0
INDE 12 34 54 FOBS=    0.0 SIGMA= 22.5 PHAS=    0.0 FOM= 0.00 TEST= 0
INDE 12 34 56 FOBS=   76.4 SIGMA=  2.8 PHAS=  163.2 FOM= 0.78 TEST= 0
INDE 12 34 58 FOBS=   66.0 SIGMA=  3.1 PHAS= -116.3 FOM= 0.88 TEST= 0
INDE 12 34 60 FOBS=   56.8 SIGMA=  3.7 PHAS= -113.4 FOM= 0.83 TEST= 0
INDE 12 34 62 FOBS=    0.0 SIGMA= 21.2 PHAS=    0.0 FOM= 0.00 TEST= 0
INDE 12 34 64 FOBS=   40.4 SIGMA=  4.6 PHAS=  129.5 FOM= 0.64 TEST= 0
INDE 12 34 66 FOBS=    0.0 SIGMA= 21.9 PHAS=    0.0 FOM= 0.00 TEST= 0
INDE 12 34 68 FOBS=    0.0 SIGMA= 23.6 PHAS=    0.0 FOM= 0.00 TEST= 0
INDE 12 35 13 FOBS=  101.8 SIGMA=  1.4 PHAS= -130.5 FOM= 0.91 TEST= 0
INDE 12 35 15 FOBS=  308.5 SIGMA=  0.7 PHAS=  -82.2 FOM= 0.97 TEST= 0
INDE 12 35 17 FOBS=  135.5 SIGMA=  1.2 PHAS=   45.3 FOM= 0.99 TEST= 0
INDE 12 35 19 FOBS=   11.9 SIGMA= 17.9 PHAS= -134.7 FOM= 0.01 TEST= 1
INDE 12 35 21 FOBS=  345.5 SIGMA=  0.9 PHAS=   43.4 FOM= 0.98 TEST= 0
INDE 12 35 23 FOBS=  251.1 SIGMA=  0.9 PHAS=  148.0 FOM= 0.97 TEST= 0
INDE 12 35 25 FOBS=  159.4 SIGMA=  1.2 PHAS= -152.4 FOM= 0.94 TEST= 0
INDE 12 35 27 FOBS=  256.2 SIGMA=  0.8 PHAS=  -56.0 FOM= 0.98 TEST= 0
INDE 12 35 29 FOBS=  128.1 SIGMA=  1.8 PHAS=  177.5 FOM= 0.91 TEST= 0
INDE 12 35 31 FOBS=   83.5 SIGMA=  2.8 PHAS=  100.4 FOM= 0.52 TEST= 0
INDE 12 35 33 FOBS=   77.2 SIGMA=  2.7 PHAS=   34.5 FOM= 0.89 TEST= 0
INDE 12 35 35 FOBS=   62.9 SIGMA=  3.2 PHAS=  154.7 FOM= 0.33 TEST= 0
INDE 12 35 37 FOBS=  196.7 SIGMA=  1.1 PHAS=  -36.4 FOM= 0.97 TEST= 0
INDE 12 35 39 FOBS=  227.7 SIGMA=  1.2 PHAS= -143.0 FOM= 0.95 TEST= 0
INDE 12 35 41 FOBS=  121.2 SIGMA=  2.0 PHAS= -171.5 FOM= 0.76 TEST= 1
INDE 12 35 43 FOBS=   62.4 SIGMA=  3.7 PHAS=   25.8 FOM= 0.25 TEST= 0
INDE 12 35 45 FOBS=   72.5 SIGMA=  3.1 PHAS= -171.0 FOM= 0.68 TEST= 0
INDE 12 35 47 FOBS=   71.8 SIGMA=  3.1 PHAS= -149.1 FOM= 0.62 TEST= 0
INDE 12 35 49 FOBS=  103.2 SIGMA=  2.2 PHAS=  154.6 FOM= 0.76 TEST= 0
INDE 12 35 51 FOBS=   68.2 SIGMA=  3.2 PHAS=  -10.5 FOM= 0.52 TEST= 0
INDE 12 35 53 FOBS=    0.0 SIGMA= 20.5 PHAS=    0.0 FOM= 0.00 TEST= 1
INDE 12 35 55 FOBS=   31.0 SIGMA=  7.5 PHAS=  123.5 FOM= 0.11 TEST= 0
INDE 12 35 57 FOBS=  102.2 SIGMA=  2.1 PHAS=  113.7 FOM= 0.90 TEST= 0
INDE 12 35 59 FOBS=   69.0 SIGMA=  3.1 PHAS=  102.4 FOM= 0.48 TEST= 1
INDE 12 35 61 FOBS=    0.0 SIGMA= 21.3 PHAS=    0.0 FOM= 0.00 TEST= 0
INDE 12 35 63 FOBS=    0.0 SIGMA= 21.3 PHAS=    0.0 FOM= 0.00 TEST= 0
INDE 12 35 65 FOBS=    9.3 SIGMA= 20.4 PHAS=  -14.8 FOM= 0.10 TEST= 0
INDE 12 35 67 FOBS=   28.3 SIGMA= 13.9 PHAS= -152.9 FOM= 0.69 TEST= 0
INDE 12 36 12 FOBS=   56.3 SIGMA=  2.1 PHAS=   75.1 FOM= 0.78 TEST= 0
INDE 12 36 14 FOBS=  230.7 SIGMA=  0.8 PHAS= -110.1 FOM= 0.92 TEST= 0
INDE 12 36 16 FOBS=  317.8 SIGMA=  0.7 PHAS= -151.5 FOM= 0.99 TEST= 0
INDE 12 36 18 FOBS=  130.2 SIGMA=  1.4 PHAS=  -28.2 FOM= 0.85 TEST= 0
INDE 12 36 20 FOBS=  184.5 SIGMA=  1.3 PHAS=   -9.5 FOM= 0.94 TEST= 0
```

*FIG. 12A - 310*

```
INDE 12 36 22 FOBS=  62.5 SIGMA=  2.8 PHAS=   76.7 FOM= 0.95 TEST= 0
INDE 12 36 24 FOBS=  44.9 SIGMA=  4.5 PHAS=   79.0 FOM= 0.47 TEST= 0
INDE 12 36 26 FOBS= 153.2 SIGMA=  1.3 PHAS= -176.5 FOM= 0.97 TEST= 0
INDE 12 36 28 FOBS= 264.7 SIGMA=  1.2 PHAS=  -90.9 FOM= 0.90 TEST= 1
INDE 12 36 30 FOBS= 138.8 SIGMA=  1.7 PHAS=   79.8 FOM= 0.60 TEST= 0
INDE 12 36 32 FOBS= 348.6 SIGMA=  1.0 PHAS=  -13.3 FOM= 0.97 TEST= 0
INDE 12 36 34 FOBS= 259.0 SIGMA=  0.9 PHAS=  -96.4 FOM= 0.96 TEST= 0
INDE 12 36 36 FOBS=  69.1 SIGMA=  2.9 PHAS= -175.2 FOM= 0.46 TEST= 0
INDE 12 36 38 FOBS= 120.8 SIGMA=  1.7 PHAS=  140.9 FOM= 0.97 TEST= 0
INDE 12 36 40 FOBS= 130.5 SIGMA=  1.7 PHAS=  128.1 FOM= 0.83 TEST= 0
INDE 12 36 42 FOBS=  71.8 SIGMA=  3.2 PHAS= -138.8 FOM= 0.81 TEST= 0
INDE 12 36 44 FOBS=  68.5 SIGMA=  3.3 PHAS=   17.7 FOM= 0.30 TEST= 0
INDE 12 36 46 FOBS=   0.0 SIGMA= 21.9 PHAS=    0.0 FOM= 0.00 TEST= 0
INDE 12 36 48 FOBS= 138.3 SIGMA=  1.7 PHAS=  126.5 FOM= 0.85 TEST= 1
INDE 12 36 50 FOBS=  56.1 SIGMA=  3.9 PHAS=  123.0 FOM= 0.73 TEST= 0
INDE 12 36 52 FOBS=  41.5 SIGMA=  5.2 PHAS=  175.1 FOM= 0.69 TEST= 0
INDE 12 36 54 FOBS=   0.0 SIGMA= 23.1 PHAS=    0.0 FOM= 0.00 TEST= 0
INDE 12 36 56 FOBS=  51.0 SIGMA=  4.1 PHAS= -175.8 FOM= 0.51 TEST= 0
INDE 12 36 58 FOBS=  78.0 SIGMA=  2.7 PHAS=  -30.5 FOM= 0.86 TEST= 0
INDE 12 36 60 FOBS=  67.3 SIGMA=  3.1 PHAS=  -54.2 FOM= 0.78 TEST= 0
INDE 12 36 62 FOBS=  40.1 SIGMA=  5.3 PHAS= -130.5 FOM= 0.03 TEST= 1
INDE 12 36 64 FOBS=   0.0 SIGMA= 20.6 PHAS=    0.0 FOM= 0.00 TEST= 1
INDE 12 36 66 FOBS=  82.8 SIGMA=  2.8 PHAS= -143.8 FOM= 0.90 TEST= 0
INDE 12 37 13 FOBS= 146.6 SIGMA=  1.1 PHAS= -106.9 FOM= 0.95 TEST= 0
INDE 12 37 15 FOBS= 244.3 SIGMA=  0.8 PHAS=  128.0 FOM= 0.97 TEST= 0
INDE 12 37 17 FOBS= 208.8 SIGMA=  0.9 PHAS=  174.0 FOM= 0.95 TEST= 0
INDE 12 37 19 FOBS= 336.3 SIGMA=  0.7 PHAS= -171.9 FOM= 0.96 TEST= 0
INDE 12 37 21 FOBS= 218.4 SIGMA=  0.9 PHAS=   51.3 FOM= 0.95 TEST= 0
INDE 12 37 23 FOBS=   0.0 SIGMA= 19.3 PHAS=    0.0 FOM= 0.00 TEST= 0
INDE 12 37 25 FOBS= 152.7 SIGMA=  1.4 PHAS=  109.5 FOM= 0.97 TEST= 0
INDE 12 37 27 FOBS= 112.2 SIGMA=  1.9 PHAS= -112.0 FOM= 0.96 TEST= 0
INDE 12 37 29 FOBS= 236.7 SIGMA=  1.1 PHAS= -171.2 FOM= 0.92 TEST= 0
INDE 12 37 31 FOBS= 138.5 SIGMA=  1.7 PHAS=  -86.3 FOM= 0.92 TEST= 0
INDE 12 37 33 FOBS= 141.2 SIGMA=  1.6 PHAS=  164.3 FOM= 0.81 TEST= 0
INDE 12 37 35 FOBS=   0.0 SIGMA= 20.6 PHAS=    0.0 FOM= 0.00 TEST= 0
INDE 12 37 37 FOBS=  77.4 SIGMA=  2.6 PHAS=  113.8 FOM= 0.07 TEST= 0
INDE 12 37 39 FOBS= 196.6 SIGMA=  1.1 PHAS=   49.7 FOM= 0.95 TEST= 0
INDE 12 37 41 FOBS= 138.1 SIGMA=  1.6 PHAS=   71.2 FOM= 0.92 TEST= 0
INDE 12 37 43 FOBS= 138.9 SIGMA=  1.7 PHAS=  125.5 FOM= 0.92 TEST= 1
INDE 12 37 45 FOBS=  34.6 SIGMA=  7.8 PHAS=   38.8 FOM= 0.26 TEST= 0
INDE 12 37 47 FOBS=   0.0 SIGMA= 23.6 PHAS=    0.0 FOM= 0.00 TEST= 0
INDE 12 37 49 FOBS=  36.8 SIGMA=  5.9 PHAS=   77.3 FOM= 0.48 TEST= 0
INDE 12 37 51 FOBS=  59.0 SIGMA=  3.7 PHAS=   50.6 FOM= 0.82 TEST= 0
INDE 12 37 53 FOBS=   0.0 SIGMA= 20.4 PHAS=    0.0 FOM= 0.00 TEST= 0
INDE 12 37 55 FOBS=  36.5 SIGMA=  7.1 PHAS= -148.1 FOM= 0.37 TEST= 0
INDE 12 37 57 FOBS=  40.9 SIGMA=  5.2 PHAS=  138.3 FOM= 0.66 TEST= 0
INDE 12 37 59 FOBS=  76.9 SIGMA=  3.0 PHAS= -153.2 FOM= 0.88 TEST= 0
INDE 12 37 61 FOBS=  81.4 SIGMA=  2.6 PHAS=  171.3 FOM= 0.84 TEST= 0
INDE 12 37 63 FOBS=   3.3 SIGMA= 70.9 PHAS=  166.5 FOM= 0.06 TEST= 0
INDE 12 37 65 FOBS=  57.9 SIGMA=  4.0 PHAS=  144.0 FOM= 0.90 TEST= 0
INDE 12 37 67 FOBS=  79.4 SIGMA=  3.0 PHAS=  163.2 FOM= 0.88 TEST= 0
INDE 12 38 12 FOBS= 233.6 SIGMA=  0.7 PHAS=  130.3 FOM= 0.84 TEST= 0
INDE 12 38 14 FOBS= 125.7 SIGMA=  1.3 PHAS=   -1.7 FOM= 0.91 TEST= 0
INDE 12 38 16 FOBS=  57.5 SIGMA=  2.8 PHAS= -120.3 FOM= 0.55 TEST= 0
INDE 12 38 18 FOBS= 280.9 SIGMA=  1.0 PHAS=   48.8 FOM= 0.94 TEST= 0
INDE 12 38 20 FOBS= 245.8 SIGMA=  0.9 PHAS=   49.1 FOM= 0.95 TEST= 0
INDE 12 38 22 FOBS= 251.6 SIGMA=  0.9 PHAS= -144.7 FOM= 0.98 TEST= 0
INDE 12 38 24 FOBS= 108.2 SIGMA=  1.9 PHAS=  101.1 FOM= 0.79 TEST= 0
INDE 12 38 26 FOBS= 126.7 SIGMA=  1.7 PHAS= -121.9 FOM= 0.86 TEST= 0
INDE 12 38 28 FOBS= 211.9 SIGMA=  1.1 PHAS=  -95.3 FOM= 0.95 TEST= 0
INDE 12 38 30 FOBS= 210.5 SIGMA=  1.2 PHAS=  123.7 FOM= 0.94 TEST= 0
INDE 12 38 32 FOBS= 138.0 SIGMA=  1.7 PHAS=    7.1 FOM= 0.83 TEST= 0
INDE 12 38 34 FOBS=  42.4 SIGMA=  5.8 PHAS=   56.4 FOM= 0.78 TEST= 0
INDE 12 38 36 FOBS=  61.5 SIGMA=  3.5 PHAS=  107.0 FOM= 0.86 TEST= 0
INDE 12 38 38 FOBS=  78.0 SIGMA=  2.5 PHAS=  -74.1 FOM= 0.84 TEST= 0
INDE 12 38 40 FOBS= 134.1 SIGMA=  1.5 PHAS=  -17.1 FOM= 0.89 TEST= 0
INDE 12 38 42 FOBS= 146.6 SIGMA=  1.5 PHAS=    4.2 FOM= 0.96 TEST= 0
INDE 12 38 44 FOBS=   0.0 SIGMA= 22.0 PHAS=    0.0 FOM= 0.00 TEST= 0
INDE 12 38 46 FOBS=   0.0 SIGMA= 20.9 PHAS=    0.0 FOM= 0.00 TEST= 1
INDE 12 38 48 FOBS=  70.1 SIGMA=  3.2 PHAS=   82.3 FOM= 0.58 TEST= 0
```

*FIG. 12A - 311*

```
INDE  12  38  50  FOBS=   45.8  SIGMA=   4.7  PHAS=   114.8  FOM=  0.58  TEST= 0
INDE  12  38  52  FOBS=   33.8  SIGMA=   7.2  PHAS=    30.4  FOM=  0.60  TEST= 0
INDE  12  38  54  FOBS=   37.4  SIGMA=   5.7  PHAS=   144.9  FOM=  0.74  TEST= 0
INDE  12  38  56  FOBS=   77.5  SIGMA=   2.8  PHAS=   156.6  FOM=  0.60  TEST= 0
INDE  12  38  58  FOBS=   67.5  SIGMA=   3.2  PHAS=     5.9  FOM=  0.87  TEST= 0
INDE  12  38  60  FOBS=   82.4  SIGMA=   2.6  PHAS=   110.9  FOM=  0.89  TEST= 0
INDE  12  38  62  FOBS=   73.5  SIGMA=   2.9  PHAS=   -19.0  FOM=  0.23  TEST= 0
INDE  12  38  64  FOBS=   50.7  SIGMA=   4.7  PHAS=    95.2  FOM=  0.83  TEST= 0
INDE  12  38  66  FOBS=   48.8  SIGMA=   4.9  PHAS=     1.6  FOM=  0.79  TEST= 0
INDE  12  39  13  FOBS=   71.3  SIGMA=   2.3  PHAS=   -96.9  FOM=  0.61  TEST= 0
INDE  12  39  15  FOBS=  134.8  SIGMA=   1.3  PHAS=  -177.9  FOM=  0.92  TEST= 1
INDE  12  39  17  FOBS=   72.9  SIGMA=   2.4  PHAS=  -142.9  FOM=  0.93  TEST= 0
INDE  12  39  19  FOBS=  137.7  SIGMA=   1.5  PHAS=  -109.9  FOM=  0.93  TEST= 0
INDE  12  39  21  FOBS=  194.3  SIGMA=   1.1  PHAS=    69.8  FOM=  0.91  TEST= 0
INDE  12  39  23  FOBS=  147.8  SIGMA=   1.5  PHAS=    45.1  FOM=  0.97  TEST= 0
INDE  12  39  25  FOBS=  206.0  SIGMA=   1.1  PHAS=   124.8  FOM=  0.96  TEST= 0
INDE  12  39  27  FOBS=  342.2  SIGMA=   0.8  PHAS=  -170.3  FOM=  0.98  TEST= 0
INDE  12  39  29  FOBS=  103.8  SIGMA=   1.9  PHAS=   -94.7  FOM=  0.93  TEST= 0
INDE  12  39  31  FOBS=  149.0  SIGMA=   1.6  PHAS=   -46.1  FOM=  0.90  TEST= 0
INDE  12  39  33  FOBS=  257.6  SIGMA=   1.1  PHAS=   -31.8  FOM=  0.98  TEST= 0
INDE  12  39  35  FOBS=  163.1  SIGMA=   1.4  PHAS=    -5.4  FOM=  0.94  TEST= 0
INDE  12  39  37  FOBS=  147.8  SIGMA=   1.4  PHAS=   178.3  FOM=  0.92  TEST= 0
INDE  12  39  39  FOBS=    0.0  SIGMA=  20.4  PHAS=     0.0  FOM=  0.00  TEST= 1
INDE  12  39  41  FOBS=   86.6  SIGMA=   2.2  PHAS=   -55.6  FOM=  0.90  TEST= 0
INDE  12  39  43  FOBS=    0.0  SIGMA=  20.2  PHAS=     0.0  FOM=  0.00  TEST= 0
INDE  12  39  45  FOBS=  116.4  SIGMA=   2.0  PHAS=  -137.9  FOM=  0.94  TEST= 0
INDE  12  39  47  FOBS=   65.8  SIGMA=   3.4  PHAS=   164.9  FOM=  0.36  TEST= 0
INDE  12  39  49  FOBS=  154.4  SIGMA=   1.5  PHAS=   -38.4  FOM=  0.32  TEST= 1
INDE  12  39  51  FOBS=   43.6  SIGMA=   5.0  PHAS=   -37.8  FOM=  0.61  TEST= 0
INDE  12  39  53  FOBS=   33.9  SIGMA=   6.4  PHAS=    18.7  FOM=  0.70  TEST= 0
INDE  12  39  55  FOBS=   75.9  SIGMA=   2.9  PHAS=    34.0  FOM=  0.75  TEST= 0
INDE  12  39  57  FOBS=   16.1  SIGMA=  14.4  PHAS=    47.3  FOM=  0.16  TEST= 0
INDE  12  39  59  FOBS=   60.5  SIGMA=   3.5  PHAS=  -132.8  FOM=  0.84  TEST= 0
INDE  12  39  61  FOBS=   47.4  SIGMA=   4.5  PHAS=   -24.2  FOM=  0.71  TEST= 0
INDE  12  39  63  FOBS=   97.6  SIGMA=   2.5  PHAS=    52.3  FOM=  0.23  TEST= 1
INDE  12  39  65  FOBS=   78.4  SIGMA=   2.8  PHAS=  -114.2  FOM=  0.87  TEST= 0
INDE  12  40  12  FOBS=  303.9  SIGMA=   0.9  PHAS=    49.5  FOM=  0.96  TEST= 0
INDE  12  40  14  FOBS=   74.3  SIGMA=   2.3  PHAS=   -48.7  FOM=  0.49  TEST= 1
INDE  12  40  16  FOBS=  181.0  SIGMA=   1.1  PHAS=  -145.1  FOM=  0.94  TEST= 0
INDE  12  40  18  FOBS=  302.7  SIGMA=   0.8  PHAS=   118.0  FOM=  0.98  TEST= 0
INDE  12  40  20  FOBS=    0.0  SIGMA=  19.7  PHAS=     0.0  FOM=  0.00  TEST= 0
INDE  12  40  22  FOBS=  152.7  SIGMA=   1.4  PHAS=   -95.7  FOM=  0.86  TEST= 0
INDE  12  40  24  FOBS=  108.7  SIGMA=   2.0  PHAS=    62.2  FOM=  0.89  TEST= 0
INDE  12  40  26  FOBS=  142.6  SIGMA=   1.6  PHAS=    55.9  FOM=  0.82  TEST= 0
INDE  12  40  28  FOBS=  227.7  SIGMA=   1.1  PHAS=    94.9  FOM=  0.94  TEST= 0
INDE  12  40  30  FOBS=   89.9  SIGMA=   2.2  PHAS=   -54.4  FOM=  0.90  TEST= 0
INDE  12  40  32  FOBS=  357.4  SIGMA=   0.8  PHAS=  -155.3  FOM=  0.98  TEST= 0
INDE  12  40  34  FOBS=   33.5  SIGMA=   6.3  PHAS=     5.6  FOM=  0.13  TEST= 0
INDE  12  40  36  FOBS=  194.4  SIGMA=   1.1  PHAS=    -7.6  FOM=  0.98  TEST= 0
INDE  12  40  38  FOBS=  100.3  SIGMA=   2.0  PHAS=   131.5  FOM=  0.72  TEST= 0
INDE  12  40  40  FOBS=   89.2  SIGMA=   2.2  PHAS=    16.2  FOM=  0.75  TEST= 0
INDE  12  40  42  FOBS=   46.5  SIGMA=   4.0  PHAS=  -111.8  FOM=  0.55  TEST= 0
INDE  12  40  44  FOBS=  112.3  SIGMA=   1.9  PHAS=   142.1  FOM=  0.91  TEST= 0
INDE  12  40  46  FOBS=   99.5  SIGMA=   2.3  PHAS=   103.1  FOM=  0.91  TEST= 0
INDE  12  40  48  FOBS=    0.0  SIGMA=  22.3  PHAS=     0.0  FOM=  0.00  TEST= 1
INDE  12  40  50  FOBS=   39.7  SIGMA=   5.5  PHAS=    44.1  FOM=  0.55  TEST= 0
INDE  12  40  52  FOBS=   83.2  SIGMA=   2.6  PHAS=   -88.1  FOM=  0.67  TEST= 0
INDE  12  40  54  FOBS=   50.7  SIGMA=   4.3  PHAS=   -33.1  FOM=  0.72  TEST= 0
INDE  12  40  56  FOBS=    0.0  SIGMA=  22.6  PHAS=     0.0  FOM=  0.00  TEST= 0
INDE  12  40  58  FOBS=   37.4  SIGMA=   6.1  PHAS=    93.7  FOM=  0.44  TEST= 0
INDE  12  40  60  FOBS=  100.0  SIGMA=   2.2  PHAS=   122.1  FOM=  0.93  TEST= 0
INDE  12  40  62  FOBS=   39.8  SIGMA=   5.5  PHAS=   -86.1  FOM=  0.81  TEST= 0
INDE  12  40  64  FOBS=  101.1  SIGMA=   2.8  PHAS=   147.4  FOM=  0.95  TEST= 0
INDE  12  41  13  FOBS=  125.3  SIGMA=   1.5  PHAS=   -74.9  FOM=  0.80  TEST= 0
INDE  12  41  15  FOBS=  103.8  SIGMA=   1.8  PHAS=   -29.2  FOM=  0.74  TEST= 0
INDE  12  41  17  FOBS=  132.4  SIGMA=   1.5  PHAS=    55.4  FOM=  0.88  TEST= 0
INDE  12  41  19  FOBS=  102.9  SIGMA=   2.1  PHAS=    33.2  FOM=  0.96  TEST= 0
INDE  12  41  21  FOBS=  216.6  SIGMA=   1.1  PHAS=   175.7  FOM=  0.93  TEST= 0
INDE  12  41  23  FOBS=  170.7  SIGMA=   1.3  PHAS=    12.9  FOM=  0.91  TEST= 0
INDE  12  41  25  FOBS=    0.0  SIGMA=  20.7  PHAS=     0.0  FOM=  0.00  TEST= 0
```

*FIG. 12A - 312*

| | | | | | | | | | | | | |
|---|---|---|---|---|---|---|---|---|---|---|---|---|
| INDE | 12 | 41 | 27 | FOBS= | 212.8 | SIGMA= | 1.1 | PHAS= | -40.2 | FOM= | 0.98 | TEST= 0 |
| INDE | 12 | 41 | 29 | FOBS= | 365.0 | SIGMA= | 0.9 | PHAS= | -46.8 | FOM= | 0.98 | TEST= 0 |
| INDE | 12 | 41 | 31 | FOBS= | 164.5 | SIGMA= | 1.2 | PHAS= | 115.8 | FOM= | 0.94 | TEST= 0 |
| INDE | 12 | 41 | 33 | FOBS= | 220.7 | SIGMA= | 1.1 | PHAS= | 18.6 | FOM= | 0.96 | TEST= 0 |
| INDE | 12 | 41 | 35 | FOBS= | 197.3 | SIGMA= | 1.1 | PHAS= | -76.9 | FOM= | 0.94 | TEST= 0 |
| INDE | 12 | 41 | 37 | FOBS= | 61.1 | SIGMA= | 3.2 | PHAS= | -54.4 | FOM= | 0.91 | TEST= 0 |
| INDE | 12 | 41 | 39 | FOBS= | 0.0 | SIGMA= | 20.1 | PHAS= | 0.0 | FOM= | 0.00 | TEST= 0 |
| INDE | 12 | 41 | 41 | FOBS= | 104.5 | SIGMA= | 1.9 | PHAS= | -101.9 | FOM= | 0.64 | TEST= 0 |
| INDE | 12 | 41 | 43 | FOBS= | 127.2 | SIGMA= | 1.5 | PHAS= | 21.4 | FOM= | 0.95 | TEST= 0 |
| INDE | 12 | 41 | 45 | FOBS= | 0.0 | SIGMA= | 21.0 | PHAS= | 0.0 | FOM= | 0.00 | TEST= 0 |
| INDE | 12 | 41 | 47 | FOBS= | 31.1 | SIGMA= | 7.1 | PHAS= | -140.1 | FOM= | 0.02 | TEST= 1 |
| INDE | 12 | 41 | 49 | FOBS= | 88.5 | SIGMA= | 2.6 | PHAS= | 10.8 | FOM= | 0.86 | TEST= 0 |
| INDE | 12 | 41 | 51 | FOBS= | 101.2 | SIGMA= | 2.2 | PHAS= | -26.7 | FOM= | 0.93 | TEST= 0 |
| INDE | 12 | 41 | 53 | FOBS= | 77.0 | SIGMA= | 2.9 | PHAS= | 170.2 | FOM= | 0.57 | TEST= 1 |
| INDE | 12 | 41 | 55 | FOBS= | 57.6 | SIGMA= | 3.8 | PHAS= | -83.7 | FOM= | 0.71 | TEST= 0 |
| INDE | 12 | 41 | 57 | FOBS= | 0.0 | SIGMA= | 26.6 | PHAS= | 0.0 | FOM= | 0.00 | TEST= 0 |
| INDE | 12 | 41 | 59 | FOBS= | 119.2 | SIGMA= | 1.9 | PHAS= | 30.1 | FOM= | 0.94 | TEST= 0 |
| INDE | 12 | 41 | 61 | FOBS= | 77.8 | SIGMA= | 2.8 | PHAS= | -22.7 | FOM= | 0.88 | TEST= 0 |
| INDE | 12 | 41 | 63 | FOBS= | 84.9 | SIGMA= | 3.2 | PHAS= | -174.8 | FOM= | 0.90 | TEST= 0 |
| INDE | 12 | 42 | 12 | FOBS= | 392.6 | SIGMA= | 0.8 | PHAS= | 88.4 | FOM= | 0.98 | TEST= 0 |
| INDE | 12 | 42 | 14 | FOBS= | 142.1 | SIGMA= | 1.4 | PHAS= | -122.8 | FOM= | 0.91 | TEST= 0 |
| INDE | 12 | 42 | 16 | FOBS= | 256.4 | SIGMA= | 0.9 | PHAS= | -109.9 | FOM= | 0.95 | TEST= 0 |
| INDE | 12 | 42 | 18 | FOBS= | 235.4 | SIGMA= | 1.0 | PHAS= | 12.9 | FOM= | 0.69 | TEST= 1 |
| INDE | 12 | 42 | 20 | FOBS= | 167.8 | SIGMA= | 1.4 | PHAS= | 113.0 | FOM= | 0.91 | TEST= 0 |
| INDE | 12 | 42 | 22 | FOBS= | 106.6 | SIGMA= | 2.0 | PHAS= | 54.5 | FOM= | 0.43 | TEST= 1 |
| INDE | 12 | 42 | 24 | FOBS= | 98.6 | SIGMA= | 2.2 | PHAS= | -166.5 | FOM= | 0.85 | TEST= 0 |
| INDE | 12 | 42 | 26 | FOBS= | 166.2 | SIGMA= | 1.4 | PHAS= | -122.2 | FOM= | 0.97 | TEST= 0 |
| INDE | 12 | 42 | 28 | FOBS= | 223.4 | SIGMA= | 1.1 | PHAS= | -178.3 | FOM= | 0.93 | TEST= 0 |
| INDE | 12 | 42 | 30 | FOBS= | 166.3 | SIGMA= | 1.3 | PHAS= | -92.7 | FOM= | 0.91 | TEST= 0 |
| INDE | 12 | 42 | 32 | FOBS= | 232.8 | SIGMA= | 0.9 | PHAS= | -134.6 | FOM= | 0.92 | TEST= 0 |
| INDE | 12 | 42 | 34 | FOBS= | 28.1 | SIGMA= | 8.3 | PHAS= | 162.4 | FOM= | 0.09 | TEST= 0 |
| INDE | 12 | 42 | 36 | FOBS= | 0.0 | SIGMA= | 20.1 | PHAS= | 0.0 | FOM= | 0.00 | TEST= 0 |
| INDE | 12 | 42 | 38 | FOBS= | 176.1 | SIGMA= | 1.2 | PHAS= | -82.9 | FOM= | 0.93 | TEST= 0 |
| INDE | 12 | 42 | 40 | FOBS= | 32.0 | SIGMA= | 6.1 | PHAS= | 40.3 | FOM= | 0.39 | TEST= 0 |
| INDE | 12 | 42 | 42 | FOBS= | 27.0 | SIGMA= | 7.6 | PHAS= | -109.6 | FOM= | 0.32 | TEST= 0 |
| INDE | 12 | 42 | 44 | FOBS= | 62.6 | SIGMA= | 3.0 | PHAS= | 80.2 | FOM= | 0.93 | TEST= 0 |
| INDE | 12 | 42 | 46 | FOBS= | 93.0 | SIGMA= | 2.2 | PHAS= | 78.4 | FOM= | 0.81 | TEST= 0 |
| INDE | 12 | 42 | 48 | FOBS= | 49.0 | SIGMA= | 4.5 | PHAS= | 78.8 | FOM= | 0.43 | TEST= 0 |
| INDE | 12 | 42 | 50 | FOBS= | 66.3 | SIGMA= | 3.4 | PHAS= | -62.3 | FOM= | 0.65 | TEST= 0 |
| INDE | 12 | 42 | 52 | FOBS= | 35.5 | SIGMA= | 6.1 | PHAS= | -56.8 | FOM= | 0.74 | TEST= 0 |
| INDE | 12 | 42 | 54 | FOBS= | 7.2 | SIGMA= | 29.9 | PHAS= | 34.4 | FOM= | 0.25 | TEST= 0 |
| INDE | 12 | 42 | 56 | FOBS= | 0.0 | SIGMA= | 21.8 | PHAS= | 0.0 | FOM= | 0.00 | TEST= 0 |
| INDE | 12 | 42 | 58 | FOBS= | 44.1 | SIGMA= | 4.9 | PHAS= | -54.0 | FOM= | 0.72 | TEST= 0 |
| INDE | 12 | 42 | 60 | FOBS= | 48.9 | SIGMA= | 4.5 | PHAS= | -65.8 | FOM= | 0.74 | TEST= 0 |
| INDE | 12 | 42 | 62 | FOBS= | 49.4 | SIGMA= | 5.5 | PHAS= | -154.5 | FOM= | 0.77 | TEST= 0 |
| INDE | 12 | 42 | 64 | FOBS= | 112.8 | SIGMA= | 2.5 | PHAS= | 147.3 | FOM= | 0.93 | TEST= 0 |
| INDE | 12 | 43 | 13 | FOBS= | 149.7 | SIGMA= | 1.8 | PHAS= | 29.0 | FOM= | 0.97 | TEST= 0 |
| INDE | 12 | 43 | 15 | FOBS= | 192.1 | SIGMA= | 1.1 | PHAS= | 132.9 | FOM= | 0.81 | TEST= 0 |
| INDE | 12 | 43 | 17 | FOBS= | 111.9 | SIGMA= | 1.9 | PHAS= | -110.0 | FOM= | 0.92 | TEST= 0 |
| INDE | 12 | 43 | 19 | FOBS= | 221.4 | SIGMA= | 1.1 | PHAS= | -69.3 | FOM= | 0.96 | TEST= 0 |
| INDE | 12 | 43 | 21 | FOBS= | 120.7 | SIGMA= | 1.8 | PHAS= | 98.5 | FOM= | 0.92 | TEST= 0 |
| INDE | 12 | 43 | 23 | FOBS= | 97.3 | SIGMA= | 2.2 | PHAS= | 119.4 | FOM= | 0.55 | TEST= 1 |
| INDE | 12 | 43 | 25 | FOBS= | 192.5 | SIGMA= | 1.2 | PHAS= | -160.2 | FOM= | 0.92 | TEST= 0 |
| INDE | 12 | 43 | 27 | FOBS= | 114.9 | SIGMA= | 2.1 | PHAS= | -101.7 | FOM= | 0.41 | TEST= 1 |
| INDE | 12 | 43 | 29 | FOBS= | 63.4 | SIGMA= | 3.3 | PHAS= | -33.7 | FOM= | 0.71 | TEST= 0 |
| INDE | 12 | 43 | 31 | FOBS= | 100.6 | SIGMA= | 2.0 | PHAS= | 92.7 | FOM= | 0.88 | TEST= 0 |
| INDE | 12 | 43 | 33 | FOBS= | 126.6 | SIGMA= | 1.8 | PHAS= | -65.5 | FOM= | 0.64 | TEST= 1 |
| INDE | 12 | 43 | 35 | FOBS= | 42.9 | SIGMA= | 5.0 | PHAS= | 3.3 | FOM= | 0.58 | TEST= 0 |
| INDE | 12 | 43 | 37 | FOBS= | 0.0 | SIGMA= | 19.6 | PHAS= | 0.0 | FOM= | 0.00 | TEST= 0 |
| INDE | 12 | 43 | 39 | FOBS= | 130.2 | SIGMA= | 1.6 | PHAS= | -162.9 | FOM= | 0.91 | TEST= 0 |
| INDE | 12 | 43 | 41 | FOBS= | 39.8 | SIGMA= | 5.6 | PHAS= | -19.5 | FOM= | 0.17 | TEST= 0 |
| INDE | 12 | 43 | 43 | FOBS= | 115.3 | SIGMA= | 1.7 | PHAS= | -19.0 | FOM= | 0.89 | TEST= 0 |
| INDE | 12 | 43 | 45 | FOBS= | 125.1 | SIGMA= | 1.5 | PHAS= | -47.4 | FOM= | 0.94 | TEST= 0 |
| INDE | 12 | 43 | 47 | FOBS= | 109.6 | SIGMA= | 1.9 | PHAS= | -31.0 | FOM= | 0.90 | TEST= 0 |
| INDE | 12 | 43 | 49 | FOBS= | 52.6 | SIGMA= | 4.2 | PHAS= | 53.0 | FOM= | 0.65 | TEST= 0 |
| INDE | 12 | 43 | 51 | FOBS= | 57.0 | SIGMA= | 3.9 | PHAS= | -23.2 | FOM= | 0.85 | TEST= 0 |
| INDE | 12 | 43 | 53 | FOBS= | 55.8 | SIGMA= | 3.9 | PHAS= | 58.3 | FOM= | 0.67 | TEST= 0 |
| INDE | 12 | 43 | 55 | FOBS= | 49.3 | SIGMA= | 4.4 | PHAS= | 169.8 | FOM= | 0.66 | TEST= 0 |
| INDE | 12 | 43 | 57 | FOBS= | 27.3 | SIGMA= | 8.1 | PHAS= | -1.1 | FOM= | 0.35 | TEST= 0 |
| INDE | 12 | 43 | 59 | FOBS= | 44.9 | SIGMA= | 5.4 | PHAS= | 146.9 | FOM= | 0.70 | TEST= 0 |

*FIG. 12A - 313*

| | | | | | | | | | | | |
|---|---|---|---|---|---|---|---|---|---|---|---|
| INDE | 12 | 43 | 61 | FOBS= | 0.0 | SIGMA= | 25.5 | PHAS= | 0.0 | FOM= | 0.00 | TEST= 0
| INDE | 12 | 43 | 63 | FOBS= | 59.9 | SIGMA= | 4.7 | PHAS= | -110.5 | FOM= | 0.14 | TEST= 1
| INDE | 12 | 44 | 12 | FOBS= | 80.3 | SIGMA= | 3.3 | PHAS= | 14.3 | FOM= | 0.66 | TEST= 0
| INDE | 12 | 44 | 14 | FOBS= | 172.9 | SIGMA= | 1.3 | PHAS= | -110.0 | FOM= | 0.98 | TEST= 0
| INDE | 12 | 44 | 16 | FOBS= | 108.1 | SIGMA= | 2.0 | PHAS= | 100.0 | FOM= | 0.91 | TEST= 0
| INDE | 12 | 44 | 18 | FOBS= | 239.4 | SIGMA= | 1.0 | PHAS= | -84.6 | FOM= | 0.96 | TEST= 0
| INDE | 12 | 44 | 20 | FOBS= | 165.0 | SIGMA= | 1.5 | PHAS= | -173.3 | FOM= | 0.81 | TEST= 0
| INDE | 12 | 44 | 22 | FOBS= | 43.7 | SIGMA= | 5.3 | PHAS= | 10.4 | FOM= | 0.59 | TEST= 0
| INDE | 12 | 44 | 24 | FOBS= | 136.2 | SIGMA= | 1.6 | PHAS= | 179.8 | FOM= | 0.87 | TEST= 0
| INDE | 12 | 44 | 26 | FOBS= | 73.2 | SIGMA= | 2.9 | PHAS= | -142.2 | FOM= | 0.89 | TEST= 0
| INDE | 12 | 44 | 28 | FOBS= | 102.6 | SIGMA= | 2.1 | PHAS= | 87.9 | FOM= | 0.88 | TEST= 0
| INDE | 12 | 44 | 30 | FOBS= | 149.7 | SIGMA= | 1.5 | PHAS= | -116.4 | FOM= | 0.88 | TEST= 1
| INDE | 12 | 44 | 32 | FOBS= | 237.8 | SIGMA= | 0.9 | PHAS= | -108.0 | FOM= | 0.97 | TEST= 0
| INDE | 12 | 44 | 34 | FOBS= | 46.4 | SIGMA= | 4.6 | PHAS= | 48.5 | FOM= | 0.19 | TEST= 1
| INDE | 12 | 44 | 36 | FOBS= | 77.3 | SIGMA= | 2.6 | PHAS= | 165.8 | FOM= | 0.82 | TEST= 0
| INDE | 12 | 44 | 38 | FOBS= | 111.5 | SIGMA= | 1.8 | PHAS= | 163.8 | FOM= | 0.89 | TEST= 0
| INDE | 12 | 44 | 40 | FOBS= | 67.0 | SIGMA= | 2.9 | PHAS= | -9.1 | FOM= | 0.69 | TEST= 0
| INDE | 12 | 44 | 42 | FOBS= | 31.0 | SIGMA= | 6.5 | PHAS= | -39.2 | FOM= | 0.34 | TEST= 0
| INDE | 12 | 44 | 44 | FOBS= | 114.4 | SIGMA= | 1.7 | PHAS= | -136.9 | FOM= | 0.94 | TEST= 0
| INDE | 12 | 44 | 46 | FOBS= | 107.7 | SIGMA= | 1.8 | PHAS= | -141.9 | FOM= | 0.95 | TEST= 0
| INDE | 12 | 44 | 48 | FOBS= | 69.0 | SIGMA= | 3.0 | PHAS= | -158.3 | FOM= | 0.16 | TEST= 1
| INDE | 12 | 44 | 50 | FOBS= | 55.4 | SIGMA= | 4.0 | PHAS= | -39.4 | FOM= | 0.66 | TEST= 0
| INDE | 12 | 44 | 52 | FOBS= | 59.1 | SIGMA= | 3.8 | PHAS= | -83.2 | FOM= | 0.84 | TEST= 0
| INDE | 12 | 44 | 54 | FOBS= | 72.2 | SIGMA= | 3.1 | PHAS= | 37.6 | FOM= | 0.86 | TEST= 0
| INDE | 12 | 44 | 56 | FOBS= | 24.9 | SIGMA= | 11.0 | PHAS= | 4.6 | FOM= | 0.50 | TEST= 0
| INDE | 12 | 44 | 58 | FOBS= | 64.1 | SIGMA= | 3.5 | PHAS= | -15.8 | FOM= | 0.86 | TEST= 0
| INDE | 12 | 44 | 60 | FOBS= | 0.0 | SIGMA= | 28.3 | PHAS= | 0.0 | FOM= | 0.00 | TEST= 0
| INDE | 12 | 44 | 62 | FOBS= | 62.8 | SIGMA= | 4.5 | PHAS= | -172.9 | FOM= | 0.72 | TEST= 0
| INDE | 12 | 45 | 13 | FOBS= | 149.6 | SIGMA= | 2.0 | PHAS= | 104.8 | FOM= | 0.85 | TEST= 0
| INDE | 12 | 45 | 15 | FOBS= | 106.5 | SIGMA= | 2.0 | PHAS= | 92.7 | FOM= | 0.75 | TEST= 0
| INDE | 12 | 45 | 17 | FOBS= | 84.1 | SIGMA= | 2.5 | PHAS= | -82.6 | FOM= | 0.93 | TEST= 0
| INDE | 12 | 45 | 19 | FOBS= | 226.1 | SIGMA= | 1.1 | PHAS= | -168.6 | FOM= | 0.94 | TEST= 0
| INDE | 12 | 45 | 21 | FOBS= | 124.7 | SIGMA= | 1.7 | PHAS= | 125.0 | FOM= | 0.83 | TEST= 0
| INDE | 12 | 45 | 23 | FOBS= | 102.5 | SIGMA= | 2.1 | PHAS= | 120.1 | FOM= | 0.92 | TEST= 0
| INDE | 12 | 45 | 25 | FOBS= | 48.3 | SIGMA= | 4.3 | PHAS= | 166.3 | FOM= | 0.60 | TEST= 0
| INDE | 12 | 45 | 27 | FOBS= | 162.1 | SIGMA= | 1.4 | PHAS= | -68.6 | FOM= | 0.88 | TEST= 1
| INDE | 12 | 45 | 29 | FOBS= | 112.2 | SIGMA= | 1.9 | PHAS= | 50.1 | FOM= | 0.96 | TEST= 0
| INDE | 12 | 45 | 31 | FOBS= | 162.3 | SIGMA= | 1.4 | PHAS= | 159.2 | FOM= | 0.94 | TEST= 0
| INDE | 12 | 45 | 33 | FOBS= | 61.8 | SIGMA= | 3.0 | PHAS= | -169.0 | FOM= | 0.51 | TEST= 0
| INDE | 12 | 45 | 35 | FOBS= | 0.0 | SIGMA= | 23.3 | PHAS= | 0.0 | FOM= | 0.00 | TEST= 0
| INDE | 12 | 45 | 37 | FOBS= | 92.3 | SIGMA= | 2.1 | PHAS= | 139.6 | FOM= | 0.76 | TEST= 1
| INDE | 12 | 45 | 39 | FOBS= | 111.6 | SIGMA= | 1.8 | PHAS= | 86.5 | FOM= | 0.90 | TEST= 0
| INDE | 12 | 45 | 41 | FOBS= | 112.6 | SIGMA= | 1.8 | PHAS= | -67.2 | FOM= | 0.40 | TEST= 1
| INDE | 12 | 45 | 43 | FOBS= | 71.1 | SIGMA= | 2.7 | PHAS= | 135.2 | FOM= | 0.89 | TEST= 0
| INDE | 12 | 45 | 45 | FOBS= | 115.0 | SIGMA= | 1.7 | PHAS= | 97.0 | FOM= | 0.90 | TEST= 0
| INDE | 12 | 45 | 47 | FOBS= | 59.2 | SIGMA= | 3.1 | PHAS= | 40.7 | FOM= | 0.65 | TEST= 0
| INDE | 12 | 45 | 49 | FOBS= | 62.3 | SIGMA= | 3.3 | PHAS= | 155.0 | FOM= | 0.56 | TEST= 0
| INDE | 12 | 45 | 51 | FOBS= | 0.0 | SIGMA= | 20.8 | PHAS= | 0.0 | FOM= | 0.00 | TEST= 0
| INDE | 12 | 45 | 53 | FOBS= | 66.2 | SIGMA= | 3.4 | PHAS= | -45.4 | FOM= | 0.83 | TEST= 0
| INDE | 12 | 45 | 55 | FOBS= | 0.0 | SIGMA= | 21.0 | PHAS= | 0.0 | FOM= | 0.00 | TEST= 0
| INDE | 12 | 45 | 57 | FOBS= | 0.0 | SIGMA= | 20.9 | PHAS= | 0.0 | FOM= | 0.00 | TEST= 0
| INDE | 12 | 45 | 59 | FOBS= | 55.8 | SIGMA= | 4.0 | PHAS= | 107.0 | FOM= | 0.45 | TEST= 0
| INDE | 12 | 45 | 61 | FOBS= | 44.5 | SIGMA= | 7.4 | PHAS= | 124.7 | FOM= | 0.65 | TEST= 0
| INDE | 12 | 46 | 12 | FOBS= | 214.7 | SIGMA= | 1.4 | PHAS= | -30.0 | FOM= | 0.96 | TEST= 0
| INDE | 12 | 46 | 14 | FOBS= | 81.4 | SIGMA= | 3.4 | PHAS= | -153.8 | FOM= | 0.11 | TEST= 0
| INDE | 12 | 46 | 16 | FOBS= | 104.8 | SIGMA= | 2.0 | PHAS= | 170.8 | FOM= | 0.93 | TEST= 0
| INDE | 12 | 46 | 18 | FOBS= | 69.0 | SIGMA= | 3.0 | PHAS= | -91.8 | FOM= | 0.42 | TEST= 0
| INDE | 12 | 46 | 20 | FOBS= | 68.8 | SIGMA= | 3.3 | PHAS= | 97.0 | FOM= | 0.63 | TEST= 0
| INDE | 12 | 46 | 22 | FOBS= | 124.6 | SIGMA= | 1.7 | PHAS= | 13.2 | FOM= | 0.80 | TEST= 0
| INDE | 12 | 46 | 24 | FOBS= | 57.8 | SIGMA= | 3.6 | PHAS= | -1.2 | FOM= | 0.28 | TEST= 0
| INDE | 12 | 46 | 26 | FOBS= | 105.7 | SIGMA= | 2.0 | PHAS= | 73.5 | FOM= | 0.91 | TEST= 0
| INDE | 12 | 46 | 28 | FOBS= | 0.0 | SIGMA= | 24.6 | PHAS= | 0.0 | FOM= | 0.00 | TEST= 0
| INDE | 12 | 46 | 30 | FOBS= | 68.8 | SIGMA= | 3.0 | PHAS= | 114.9 | FOM= | 0.90 | TEST= 0
| INDE | 12 | 46 | 32 | FOBS= | 114.6 | SIGMA= | 1.9 | PHAS= | 176.5 | FOM= | 0.91 | TEST= 1
| INDE | 12 | 46 | 34 | FOBS= | 0.0 | SIGMA= | 19.8 | PHAS= | 0.0 | FOM= | 0.00 | TEST= 0
| INDE | 12 | 46 | 36 | FOBS= | 60.6 | SIGMA= | 3.5 | PHAS= | 100.8 | FOM= | 0.87 | TEST= 0
| INDE | 12 | 46 | 38 | FOBS= | 66.8 | SIGMA= | 2.8 | PHAS= | 52.0 | FOM= | 0.77 | TEST= 0
| INDE | 12 | 46 | 40 | FOBS= | 30.8 | SIGMA= | 7.3 | PHAS= | -70.4 | FOM= | 0.22 | TEST= 0
| INDE | 12 | 46 | 42 | FOBS= | 119.0 | SIGMA= | 1.7 | PHAS= | 31.2 | FOM= | 0.91 | TEST= 0
| INDE | 12 | 46 | 44 | FOBS= | 104.7 | SIGMA= | 1.9 | PHAS= | -56.1 | FOM= | 0.76 | TEST= 1

*FIG. 12A - 314*

```
INDE 12 46 46 FOBS=    28.8 SIGMA=  6.9 PHAS=  -90.3 FOM= 0.41 TEST= 0
INDE 12 46 48 FOBS=    39.0 SIGMA=  5.4 PHAS=   39.0 FOM= 0.57 TEST= 0
INDE 12 46 50 FOBS=     0.0 SIGMA= 21.8 PHAS=    0.0 FOM= 0.00 TEST= 0
INDE 12 46 52 FOBS=     0.0 SIGMA= 20.9 PHAS=    0.0 FOM= 0.00 TEST= 0
INDE 12 46 54 FOBS=    51.7 SIGMA=  4.3 PHAS= -106.2 FOM= 0.18 TEST= 1
INDE 12 46 56 FOBS=    32.4 SIGMA=  8.2 PHAS=  -70.9 FOM= 0.32 TEST= 0
INDE 12 46 58 FOBS=    61.0 SIGMA=  3.7 PHAS=    5.2 FOM= 0.87 TEST= 0
INDE 12 46 60 FOBS=    21.7 SIGMA= 15.1 PHAS=   16.3 FOM= 0.66 TEST= 0
INDE 12 47 13 FOBS=   127.7 SIGMA=  2.2 PHAS= -149.7 FOM= 0.86 TEST= 0
INDE 12 47 15 FOBS=   116.1 SIGMA=  1.8 PHAS=   51.1 FOM= 0.85 TEST= 0
INDE 12 47 17 FOBS=    97.0 SIGMA=  2.2 PHAS=  106.1 FOM= 0.87 TEST= 0
INDE 12 47 19 FOBS=    92.8 SIGMA=  2.3 PHAS= -149.6 FOM= 0.85 TEST= 0
INDE 12 47 21 FOBS=   123.7 SIGMA=  1.7 PHAS= -106.2 FOM= 0.37 TEST= 1
INDE 12 47 23 FOBS=    89.9 SIGMA=  2.3 PHAS=  129.4 FOM= 0.54 TEST= 0
INDE 12 47 25 FOBS=   161.3 SIGMA=  1.4 PHAS=  -24.8 FOM= 0.92 TEST= 0
INDE 12 47 27 FOBS=   186.1 SIGMA=  1.2 PHAS=  -58.5 FOM= 0.94 TEST= 0
INDE 12 47 29 FOBS=    15.4 SIGMA= 16.0 PHAS=   15.1 FOM= 0.19 TEST= 0
INDE 12 47 31 FOBS=    55.9 SIGMA=  3.7 PHAS=    8.2 FOM= 0.75 TEST= 0
INDE 12 47 33 FOBS=    30.4 SIGMA=  6.3 PHAS=   95.0 FOM= 0.30 TEST= 0
INDE 12 47 35 FOBS=     0.0 SIGMA= 19.7 PHAS=    0.0 FOM= 0.00 TEST= 0
INDE 12 47 37 FOBS=    74.9 SIGMA=  2.9 PHAS=   38.7 FOM= 0.91 TEST= 0
INDE 12 47 39 FOBS=   109.9 SIGMA=  1.8 PHAS=   32.3 FOM= 0.92 TEST= 0
INDE 12 47 41 FOBS=    82.1 SIGMA=  2.4 PHAS=  108.1 FOM= 0.03 TEST= 1
INDE 12 47 43 FOBS=    68.5 SIGMA=  2.8 PHAS= -134.1 FOM= 0.82 TEST= 0
INDE 12 47 45 FOBS=    62.8 SIGMA=  3.0 PHAS=  163.0 FOM= 0.74 TEST= 0
INDE 12 47 47 FOBS=   123.9 SIGMA=  1.6 PHAS=  -32.5 FOM= 0.90 TEST= 0
INDE 12 47 49 FOBS=    45.2 SIGMA=  4.5 PHAS=  -81.7 FOM= 0.61 TEST= 0
INDE 12 47 51 FOBS=     0.0 SIGMA= 19.9 PHAS=    0.0 FOM= 0.00 TEST= 0
INDE 12 47 53 FOBS=    52.4 SIGMA=  4.3 PHAS= -104.6 FOM= 0.76 TEST= 0
INDE 12 47 55 FOBS=    37.3 SIGMA=  6.5 PHAS=  169.8 FOM= 0.79 TEST= 0
INDE 12 47 57 FOBS=    44.3 SIGMA=  6.2 PHAS=  -83.9 FOM= 0.41 TEST= 0
INDE 12 47 59 FOBS=    23.7 SIGMA= 11.7 PHAS= -107.4 FOM= 0.45 TEST= 0
INDE 12 48 12 FOBS=   100.9 SIGMA=  2.8 PHAS=  -85.1 FOM= 0.76 TEST= 1
INDE 12 48 14 FOBS=   114.3 SIGMA=  2.4 PHAS=  103.2 FOM= 0.84 TEST= 1
INDE 12 48 16 FOBS=   223.4 SIGMA=  1.0 PHAS=  -21.7 FOM= 0.94 TEST= 0
INDE 12 48 18 FOBS=    72.2 SIGMA=  2.9 PHAS=  132.1 FOM= 0.85 TEST= 0
INDE 12 48 20 FOBS=   140.0 SIGMA=  1.5 PHAS= -174.8 FOM= 0.91 TEST= 0
INDE 12 48 22 FOBS=   169.8 SIGMA=  1.3 PHAS= -104.2 FOM= 0.97 TEST= 0
INDE 12 48 24 FOBS=    39.5 SIGMA=  5.2 PHAS= -165.7 FOM= 0.15 TEST= 0
INDE 12 48 26 FOBS=    83.7 SIGMA=  2.5 PHAS=  164.0 FOM= 0.90 TEST= 0
INDE 12 48 28 FOBS=    43.3 SIGMA=  4.7 PHAS= -116.4 FOM= 0.39 TEST= 0
INDE 12 48 30 FOBS=     0.0 SIGMA= 20.3 PHAS=    0.0 FOM= 0.00 TEST= 0
INDE 12 48 32 FOBS=    98.7 SIGMA=  2.1 PHAS=  171.3 FOM= 0.92 TEST= 0
INDE 12 48 34 FOBS=     0.0 SIGMA= 18.9 PHAS=    0.0 FOM= 0.00 TEST= 0
INDE 12 48 36 FOBS=     0.0 SIGMA= 19.7 PHAS=    0.0 FOM= 0.00 TEST= 0
INDE 12 48 38 FOBS=    87.9 SIGMA=  2.3 PHAS=   -7.7 FOM= 0.91 TEST= 0
INDE 12 48 40 FOBS=    54.3 SIGMA=  3.5 PHAS=  -62.4 FOM= 0.66 TEST= 0
INDE 12 48 42 FOBS=    47.7 SIGMA=  4.4 PHAS=   56.4 FOM= 0.33 TEST= 1
INDE 12 48 44 FOBS=    62.0 SIGMA=  3.1 PHAS=   48.0 FOM= 0.85 TEST= 0
INDE 12 48 46 FOBS=    51.2 SIGMA=  3.7 PHAS= -173.7 FOM= 0.67 TEST= 0
INDE 12 48 48 FOBS=     0.0 SIGMA= 20.3 PHAS=    0.0 FOM= 0.00 TEST= 0
INDE 12 48 50 FOBS=    11.7 SIGMA= 20.5 PHAS=  149.4 FOM= 0.25 TEST= 0
INDE 12 48 52 FOBS=     7.7 SIGMA= 28.5 PHAS=  -81.4 FOM= 0.17 TEST= 1
INDE 12 48 54 FOBS=     0.0 SIGMA= 21.0 PHAS=    0.0 FOM= 0.00 TEST= 0
INDE 12 48 56 FOBS=     0.0 SIGMA= 22.1 PHAS=    0.0 FOM= 0.00 TEST= 0
INDE 12 48 58 FOBS=    45.3 SIGMA=  6.1 PHAS=   57.1 FOM= 0.47 TEST= 0
INDE 12 48 60 FOBS=     0.0 SIGMA= 28.9 PHAS=    0.0 FOM= 0.00 TEST= 1
INDE 12 49 13 FOBS=    61.5 SIGMA=  4.3 PHAS=  127.1 FOM= 0.69 TEST= 0
INDE 12 49 15 FOBS=   138.4 SIGMA=  2.0 PHAS=   40.4 FOM= 0.86 TEST= 0
INDE 12 49 17 FOBS=    65.0 SIGMA=  3.1 PHAS=   78.5 FOM= 0.72 TEST= 0
INDE 12 49 19 FOBS=    86.1 SIGMA=  2.4 PHAS=   87.6 FOM= 0.30 TEST= 1
INDE 12 49 21 FOBS=    99.4 SIGMA=  2.2 PHAS=  156.0 FOM= 0.92 TEST= 0
INDE 12 49 23 FOBS=   150.7 SIGMA=  1.4 PHAS=  168.6 FOM= 0.90 TEST= 0
INDE 12 49 25 FOBS=     0.0 SIGMA= 20.1 PHAS=    0.0 FOM= 0.00 TEST= 0
INDE 12 49 27 FOBS=   178.9 SIGMA=  1.3 PHAS=   33.4 FOM= 0.96 TEST= 0
INDE 12 49 29 FOBS=     0.0 SIGMA= 21.0 PHAS=    0.0 FOM= 0.00 TEST= 0
INDE 12 49 31 FOBS=   114.3 SIGMA=  1.9 PHAS=   28.7 FOM= 0.90 TEST= 0
INDE 12 49 33 FOBS=     0.0 SIGMA= 21.0 PHAS=    0.0 FOM= 0.00 TEST= 0
INDE 12 49 35 FOBS=    85.5 SIGMA=  2.2 PHAS= -175.3 FOM= 0.85 TEST= 0
INDE 12 49 37 FOBS=   112.3 SIGMA=  1.7 PHAS=   29.1 FOM= 0.97 TEST= 0
```

*FIG. 12A - 315*

```
INDE  12  49  39  FOBS=   42.6  SIGMA=   4.4  PHAS=   -77.5  FOM=  0.76  TEST= 0
INDE  12  49  41  FOBS=   37.6  SIGMA=   5.6  PHAS=   153.6  FOM=  0.75  TEST= 0
INDE  12  49  43  FOBS=   65.9  SIGMA=   2.9  PHAS=   -83.4  FOM=  0.85  TEST= 0
INDE  12  49  45  FOBS=   19.3  SIGMA=  10.8  PHAS=   -33.2  FOM=  0.22  TEST= 0
INDE  12  49  47  FOBS=   43.5  SIGMA=   4.3  PHAS=    27.7  FOM=  0.40  TEST= 0
INDE  12  49  49  FOBS=   38.5  SIGMA=   5.4  PHAS=   -79.6  FOM=  0.69  TEST= 0
INDE  12  49  51  FOBS=    0.0  SIGMA=  21.0  PHAS=     0.0  FOM=  0.00  TEST= 0
INDE  12  49  53  FOBS=   44.6  SIGMA=   5.0  PHAS=   170.6  FOM=  0.37  TEST= 0
INDE  12  49  55  FOBS=   35.5  SIGMA=   6.9  PHAS=   179.2  FOM=  0.53  TEST= 0
INDE  12  49  57  FOBS=    0.0  SIGMA=  23.5  PHAS=     0.0  FOM=  0.00  TEST= 0
INDE  12  49  59  FOBS=   31.4  SIGMA=  10.8  PHAS=    75.7  FOM=  0.21  TEST= 0
INDE  12  50  12  FOBS=  111.8  SIGMA=   2.5  PHAS=    17.3  FOM=  0.11  TEST= 1
INDE  12  50  14  FOBS=  208.0  SIGMA=   1.4  PHAS=    23.6  FOM=  0.81  TEST= 1
INDE  12  50  16  FOBS=  220.4  SIGMA=   1.0  PHAS=   -27.0  FOM=  0.95  TEST= 0
INDE  12  50  18  FOBS=  101.8  SIGMA=   2.0  PHAS=   -12.7  FOM=  0.72  TEST= 0
INDE  12  50  20  FOBS=    0.0  SIGMA=  23.7  PHAS=     0.0  FOM=  0.00  TEST= 0
INDE  12  50  22  FOBS=  105.8  SIGMA=   2.0  PHAS=   -82.7  FOM=  0.63  TEST= 0
INDE  12  50  24  FOBS=  155.1  SIGMA=   1.4  PHAS=    31.8  FOM=  0.91  TEST= 0
INDE  12  50  26  FOBS=   83.3  SIGMA=   2.5  PHAS=    41.1  FOM=  0.36  TEST= 0
INDE  12  50  28  FOBS=  171.7  SIGMA=   1.3  PHAS=   -32.7  FOM=  0.95  TEST= 1
INDE  12  50  30  FOBS=  109.5  SIGMA=   1.9  PHAS=  -125.4  FOM=  0.88  TEST= 0
INDE  12  50  32  FOBS=  155.3  SIGMA=   1.4  PHAS=   168.9  FOM=  0.87  TEST= 0
INDE  12  50  34  FOBS=    0.0  SIGMA=  20.1  PHAS=     0.0  FOM=  0.00  TEST= 0
INDE  12  50  36  FOBS=  133.8  SIGMA=   1.4  PHAS=   -29.1  FOM=  0.93  TEST= 0
INDE  12  50  38  FOBS=   38.9  SIGMA=   5.1  PHAS=   -61.3  FOM=  0.59  TEST= 0
INDE  12  50  40  FOBS=   58.9  SIGMA=   3.2  PHAS=    15.0  FOM=  0.44  TEST= 1
INDE  12  50  42  FOBS=   50.6  SIGMA=   4.0  PHAS=  -149.5  FOM=  0.81  TEST= 0
INDE  12  50  44  FOBS=   62.8  SIGMA=   3.1  PHAS=   125.5  FOM=  0.85  TEST= 0
INDE  12  50  46  FOBS=  100.7  SIGMA=   2.0  PHAS=  -137.3  FOM=  0.88  TEST= 0
INDE  12  50  48  FOBS=    0.0  SIGMA=  22.3  PHAS=     0.0  FOM=  0.00  TEST= 0
INDE  12  50  50  FOBS=   32.6  SIGMA=   6.9  PHAS=     4.2  FOM=  0.21  TEST= 0
INDE  12  50  52  FOBS=   89.3  SIGMA=   2.4  PHAS=   -99.0  FOM=  0.81  TEST= 0
INDE  12  50  54  FOBS=    0.0  SIGMA=  23.5  PHAS=     0.0  FOM=  0.00  TEST= 0
INDE  12  50  56  FOBS=    8.6  SIGMA=  38.6  PHAS=  -118.4  FOM=  0.11  TEST= 0
INDE  12  50  58  FOBS=   81.6  SIGMA=   3.5  PHAS=  -105.0  FOM=  0.31  TEST= 0
INDE  12  51  13  FOBS=  170.5  SIGMA=   1.7  PHAS=   -82.9  FOM=  0.93  TEST= 0
INDE  12  51  15  FOBS=  117.2  SIGMA=   2.3  PHAS=   -40.7  FOM=  0.88  TEST= 0
INDE  12  51  17  FOBS=   82.7  SIGMA=   2.4  PHAS=   176.9  FOM=  0.88  TEST= 0
INDE  12  51  19  FOBS=  108.0  SIGMA=   1.9  PHAS=  -152.6  FOM=  0.74  TEST= 0
INDE  12  51  21  FOBS=  117.2  SIGMA=   1.9  PHAS=     5.3  FOM=  0.76  TEST= 0
INDE  12  51  23  FOBS=   80.6  SIGMA=   2.6  PHAS=   -91.5  FOM=  0.77  TEST= 0
INDE  12  51  25  FOBS=   80.9  SIGMA=   2.6  PHAS=    76.8  FOM=  0.89  TEST= 0
INDE  12  51  27  FOBS=   56.7  SIGMA=   3.6  PHAS=   -98.9  FOM=  0.51  TEST= 0
INDE  12  51  29  FOBS=   94.2  SIGMA=   2.2  PHAS=  -163.9  FOM=  0.94  TEST= 0
INDE  12  51  31  FOBS=  160.2  SIGMA=   1.4  PHAS=   113.1  FOM=  0.95  TEST= 0
INDE  12  51  33  FOBS=  127.8  SIGMA=   1.7  PHAS=   162.4  FOM=  0.91  TEST= 0
INDE  12  51  35  FOBS=   77.2  SIGMA=   2.5  PHAS=  -160.8  FOM=  0.75  TEST= 0
INDE  12  51  37  FOBS=    0.0  SIGMA=  19.6  PHAS=     0.0  FOM=  0.00  TEST= 0
INDE  12  51  39  FOBS=   81.3  SIGMA=   2.3  PHAS=   -98.8  FOM=  0.89  TEST= 0
INDE  12  51  41  FOBS=   69.6  SIGMA=   2.7  PHAS=    34.4  FOM=  0.48  TEST= 0
INDE  12  51  43  FOBS=   83.1  SIGMA=   2.3  PHAS=  -158.2  FOM=  0.88  TEST= 0
INDE  12  51  45  FOBS=   51.2  SIGMA=   3.7  PHAS=    82.9  FOM=  0.19  TEST= 1
INDE  12  51  47  FOBS=   83.1  SIGMA=   2.4  PHAS=   100.8  FOM=  0.83  TEST= 0
INDE  12  51  49  FOBS=    0.0  SIGMA=  20.5  PHAS=     0.0  FOM=  0.00  TEST= 1
INDE  12  51  51  FOBS=   66.4  SIGMA=   3.4  PHAS=   118.5  FOM=  0.59  TEST= 0
INDE  12  51  53  FOBS=    1.1  SIGMA= 207.4  PHAS=   159.6  FOM=  0.01  TEST= 0
INDE  12  51  55  FOBS=   57.1  SIGMA=   4.9  PHAS=   165.9  FOM=  0.76  TEST= 0
INDE  12  51  57  FOBS=   26.7  SIGMA=  12.5  PHAS=  -164.6  FOM=  0.07  TEST= 0
INDE  12  52  12  FOBS=  119.3  SIGMA=   1.3  PHAS=  -106.9  FOM=  0.57  TEST= 0
INDE  12  52  14  FOBS=    0.0  SIGMA=  22.7  PHAS=     0.0  FOM=  0.00  TEST= 0
INDE  12  52  16  FOBS=  119.5  SIGMA=   2.2  PHAS=  -177.1  FOM=  0.89  TEST= 0
INDE  12  52  18  FOBS=   83.3  SIGMA=   2.4  PHAS=    -6.0  FOM=  0.85  TEST= 0
INDE  12  52  20  FOBS=  126.8  SIGMA=   1.6  PHAS=   171.2  FOM=  0.73  TEST= 0
INDE  12  52  22  FOBS=  114.8  SIGMA=   1.8  PHAS=   154.4  FOM=  0.90  TEST= 0
INDE  12  52  24  FOBS=  155.6  SIGMA=   1.4  PHAS=    71.6  FOM=  0.90  TEST= 0
INDE  12  52  26  FOBS=   65.4  SIGMA=   3.1  PHAS=   -51.0  FOM=  0.68  TEST= 0
INDE  12  52  28  FOBS=    0.0  SIGMA=  22.2  PHAS=     0.0  FOM=  0.00  TEST= 0
INDE  12  52  30  FOBS=   54.7  SIGMA=   3.7  PHAS=    83.9  FOM=  0.78  TEST= 0
INDE  12  52  32  FOBS=   54.0  SIGMA=   3.7  PHAS=   103.9  FOM=  0.59  TEST= 0
INDE  12  52  34  FOBS=   40.2  SIGMA=   5.0  PHAS=   140.8  FOM=  0.35  TEST= 0
```

*FIG. 12A - 316*

```
INDE 12 52 36 FOBS=   89.7 SIGMA=  2.0 PHAS=  -14.2 FOM= 0.81 TEST= 0
INDE 12 52 38 FOBS=   44.6 SIGMA=  4.0 PHAS=   90.3 FOM= 0.58 TEST= 0
INDE 12 52 40 FOBS=   95.8 SIGMA=  1.9 PHAS= -169.9 FOM= 0.33 TEST= 0
INDE 12 52 42 FOBS=  133.9 SIGMA=  1.5 PHAS=  107.2 FOM= 0.94 TEST= 0
INDE 12 52 44 FOBS=   91.0 SIGMA=  2.1 PHAS=   70.3 FOM= 0.95 TEST= 0
INDE 12 52 46 FOBS=   39.5 SIGMA=  5.6 PHAS= -135.2 FOM= 0.20 TEST= 0
INDE 12 52 48 FOBS=   45.8 SIGMA=  5.1 PHAS=   10.8 FOM= 0.80 TEST= 0
INDE 12 52 50 FOBS=   96.5 SIGMA=  2.3 PHAS=  -31.8 FOM= 0.93 TEST= 0
INDE 12 52 52 FOBS=   30.4 SIGMA=  7.6 PHAS=   63.4 FOM= 0.32 TEST= 0
INDE 12 52 54 FOBS=    0.0 SIGMA= 27.8 PHAS=    0.0 FOM= 0.00 TEST= 0
INDE 12 52 56 FOBS=   58.5 SIGMA=  5.8 PHAS=  -66.9 FOM= 0.24 TEST= 0
INDE 12 53 13 FOBS=   99.1 SIGMA=  2.7 PHAS=  137.7 FOM= 0.52 TEST= 0
INDE 12 53 15 FOBS=   93.3 SIGMA=  2.8 PHAS=   63.8 FOM= 0.78 TEST= 0
INDE 12 53 17 FOBS=  107.0 SIGMA=  2.5 PHAS=   92.7 FOM= 0.74 TEST= 0
INDE 12 53 19 FOBS=  121.9 SIGMA=  1.7 PHAS=  -65.5 FOM= 0.78 TEST= 1
INDE 12 53 21 FOBS=   22.7 SIGMA=  8.7 PHAS=   56.5 FOM= 0.17 TEST= 0
INDE 12 53 23 FOBS=  157.5 SIGMA=  1.4 PHAS=    1.7 FOM= 0.96 TEST= 0
INDE 12 53 25 FOBS=  140.6 SIGMA=  1.5 PHAS=   34.1 FOM= 0.93 TEST= 0
INDE 12 53 27 FOBS=  131.4 SIGMA=  1.6 PHAS=  112.3 FOM= 0.93 TEST= 0
INDE 12 53 29 FOBS=    0.0 SIGMA= 20.8 PHAS=    0.0 FOM= 0.00 TEST= 0
INDE 12 53 31 FOBS=   45.4 SIGMA=  4.4 PHAS=  -49.3 FOM= 0.53 TEST= 0
INDE 12 53 33 FOBS=   86.4 SIGMA=  2.4 PHAS=  144.1 FOM= 0.62 TEST= 0
INDE 12 53 35 FOBS=    7.9 SIGMA= 27.6 PHAS=   78.3 FOM= 0.05 TEST= 1
INDE 12 53 37 FOBS=   47.3 SIGMA=  3.8 PHAS= -140.8 FOM= 0.47 TEST= 0
INDE 12 53 39 FOBS=   47.5 SIGMA=  4.0 PHAS=    3.7 FOM= 0.65 TEST= 0
INDE 12 53 41 FOBS=   82.8 SIGMA=  2.1 PHAS=   -2.2 FOM= 0.94 TEST= 0
INDE 12 53 43 FOBS=   46.9 SIGMA=  4.0 PHAS=  -23.2 FOM= 0.79 TEST= 0
INDE 12 53 45 FOBS=   70.6 SIGMA=  2.7 PHAS=  -11.1 FOM= 0.88 TEST= 0
INDE 12 53 47 FOBS=  101.9 SIGMA=  2.2 PHAS=  -50.5 FOM= 0.94 TEST= 0
INDE 12 53 49 FOBS=   65.9 SIGMA=  3.3 PHAS= -143.0 FOM= 0.86 TEST= 0
INDE 12 53 51 FOBS=   33.9 SIGMA=  7.5 PHAS= -169.7 FOM= 0.32 TEST= 0
INDE 12 53 53 FOBS=   89.1 SIGMA=  3.3 PHAS=  -18.6 FOM= 0.94 TEST= 0
INDE 12 53 55 FOBS=   36.4 SIGMA=  9.6 PHAS=  -79.8 FOM= 0.61 TEST= 0
INDE 12 54 12 FOBS=   30.5 SIGMA=  5.4 PHAS=  -16.3 FOM= 0.32 TEST= 0
INDE 12 54 14 FOBS=  113.0 SIGMA=  2.4 PHAS=  -25.8 FOM= 0.86 TEST= 1
INDE 12 54 16 FOBS=   87.1 SIGMA=  3.0 PHAS=  114.4 FOM= 0.76 TEST= 0
INDE 12 54 18 FOBS=   59.9 SIGMA=  3.2 PHAS=   12.6 FOM= 0.89 TEST= 0
INDE 12 54 20 FOBS=  110.9 SIGMA=  1.8 PHAS= -162.3 FOM= 0.86 TEST= 0
INDE 12 54 22 FOBS=   29.0 SIGMA=  8.1 PHAS= -157.5 FOM= 0.16 TEST= 0
INDE 12 54 24 FOBS=  177.2 SIGMA=  1.4 PHAS=  -54.6 FOM= 0.97 TEST= 0
INDE 12 54 26 FOBS=  124.7 SIGMA=  1.7 PHAS=  -49.8 FOM= 0.92 TEST= 0
INDE 12 54 28 FOBS=   47.7 SIGMA=  4.2 PHAS= -147.5 FOM= 0.23 TEST= 0
INDE 12 54 30 FOBS=   43.8 SIGMA=  4.6 PHAS= -135.9 FOM= 0.35 TEST= 0
INDE 12 54 32 FOBS=   35.0 SIGMA=  6.3 PHAS= -108.7 FOM= 0.57 TEST= 0
INDE 12 54 34 FOBS=   49.4 SIGMA=  4.1 PHAS=  -51.8 FOM= 0.53 TEST= 0
INDE 12 54 36 FOBS=   40.4 SIGMA=  5.4 PHAS=  -31.3 FOM= 0.85 TEST= 0
INDE 12 54 38 FOBS=    0.0 SIGMA= 18.9 PHAS=    0.0 FOM= 0.00 TEST= 0
INDE 12 54 40 FOBS=   72.5 SIGMA=  2.5 PHAS=  -67.2 FOM= 0.90 TEST= 0
INDE 12 54 42 FOBS=   64.7 SIGMA=  2.6 PHAS=  161.3 FOM= 0.82 TEST= 0
INDE 12 54 44 FOBS=    0.0 SIGMA= 19.4 PHAS=    0.0 FOM= 0.00 TEST= 0
INDE 12 54 46 FOBS=   52.9 SIGMA=  3.7 PHAS=  -84.1 FOM= 0.74 TEST= 0
INDE 12 54 48 FOBS=   58.8 SIGMA=  4.1 PHAS=  169.6 FOM= 0.73 TEST= 0
INDE 12 54 50 FOBS=   41.9 SIGMA= 10.1 PHAS=  -28.2 FOM= 0.72 TEST= 0
INDE 12 54 52 FOBS=  107.1 SIGMA=  3.3 PHAS= -127.6 FOM= 0.90 TEST= 0
INDE 12 54 54 FOBS=   94.5 SIGMA=  3.8 PHAS= -137.5 FOM= 0.93 TEST= 0
INDE 12 55 13 FOBS=   88.3 SIGMA=  1.6 PHAS= -160.8 FOM= 0.86 TEST= 0
INDE 12 55 15 FOBS=  114.5 SIGMA=  2.3 PHAS=    1.9 FOM= 0.93 TEST= 0
INDE 12 55 17 FOBS=  171.9 SIGMA=  1.6 PHAS=   33.6 FOM= 0.94 TEST= 0
INDE 12 55 19 FOBS=   69.5 SIGMA=  2.8 PHAS=  -94.7 FOM= 0.87 TEST= 0
INDE 12 55 21 FOBS=   74.2 SIGMA=  2.6 PHAS= -106.8 FOM= 0.62 TEST= 0
INDE 12 55 23 FOBS=   46.4 SIGMA=  4.2 PHAS=  -97.2 FOM= 0.47 TEST= 0
INDE 12 55 25 FOBS=   99.5 SIGMA=  2.0 PHAS= -154.3 FOM= 0.76 TEST= 0
INDE 12 55 27 FOBS=   94.8 SIGMA=  2.1 PHAS=  141.2 FOM= 0.92 TEST= 0
INDE 12 55 29 FOBS=    0.0 SIGMA= 20.9 PHAS=    0.0 FOM= 0.00 TEST= 0
INDE 12 55 31 FOBS=   57.9 SIGMA=  3.4 PHAS= -141.6 FOM= 0.77 TEST= 0
INDE 12 55 33 FOBS=  125.8 SIGMA=  1.7 PHAS=  120.2 FOM= 0.93 TEST= 0
INDE 12 55 35 FOBS=  105.5 SIGMA=  2.0 PHAS= -141.0 FOM= 0.85 TEST= 0
INDE 12 55 37 FOBS=   22.2 SIGMA= 10.1 PHAS= -126.0 FOM= 0.15 TEST= 0
INDE 12 55 39 FOBS=   60.3 SIGMA=  3.0 PHAS= -103.4 FOM= 0.51 TEST= 0
INDE 12 55 41 FOBS=    6.4 SIGMA= 30.8 PHAS=   84.1 FOM= 0.06 TEST= 0
```

*FIG. 12A - 317*

```
INDE 12 55 43 FOBS=   55.1 SIGMA=  3.3 PHAS=  -37.5 FOM= 0.42 TEST= 0
INDE 12 55 45 FOBS=   51.3 SIGMA=  4.1 PHAS=   15.6 FOM= 0.44 TEST= 0
INDE 12 55 47 FOBS=   76.4 SIGMA=  3.5 PHAS=  -63.1 FOM= 0.82 TEST= 0
INDE 12 55 49 FOBS=   24.5 SIGMA= 15.2 PHAS= -112.6 FOM= 0.22 TEST= 0
INDE 12 55 51 FOBS=   60.2 SIGMA=  6.0 PHAS=  130.1 FOM= 0.84 TEST= 0
INDE 12 55 53 FOBS=   62.0 SIGMA=  5.8 PHAS=  101.6 FOM= 0.88 TEST= 0
INDE 12 56 12 FOBS=   78.2 SIGMA=  3.3 PHAS=  106.1 FOM= 0.84 TEST= 0
INDE 12 56 14 FOBS=  100.4 SIGMA=  1.6 PHAS= -138.1 FOM= 0.91 TEST= 0
INDE 12 56 16 FOBS=  117.4 SIGMA=  2.2 PHAS= -125.9 FOM= 0.95 TEST= 0
INDE 12 56 18 FOBS=   62.0 SIGMA=  4.1 PHAS= -145.0 FOM= 0.66 TEST= 0
INDE 12 56 20 FOBS=  118.7 SIGMA=  1.7 PHAS=  174.2 FOM= 0.80 TEST= 0
INDE 12 56 22 FOBS=   32.5 SIGMA=  7.3 PHAS=  110.3 FOM= 0.57 TEST= 0
INDE 12 56 24 FOBS=   29.2 SIGMA=  6.7 PHAS=   53.0 FOM= 0.34 TEST= 0
INDE 12 56 26 FOBS=   68.6 SIGMA=  2.9 PHAS=   34.2 FOM= 0.88 TEST= 0
INDE 12 56 28 FOBS=   24.6 SIGMA=  9.6 PHAS= -132.9 FOM= 0.39 TEST= 0
INDE 12 56 30 FOBS=   43.1 SIGMA=  4.6 PHAS=  170.7 FOM= 0.51 TEST= 0
INDE 12 56 32 FOBS=   48.8 SIGMA=  4.1 PHAS=   34.5 FOM= 0.35 TEST= 0
INDE 12 56 34 FOBS=   46.7 SIGMA=  4.3 PHAS=   59.0 FOM= 0.57 TEST= 0
INDE 12 56 36 FOBS=  115.2 SIGMA=  1.8 PHAS=  -12.2 FOM= 0.91 TEST= 0
INDE 12 56 38 FOBS=   37.2 SIGMA=  5.5 PHAS=  -14.3 FOM= 0.41 TEST= 0
INDE 12 56 40 FOBS=    0.0 SIGMA= 19.6 PHAS=    0.0 FOM= 0.00 TEST= 0
INDE 12 56 42 FOBS=   29.4 SIGMA=  7.9 PHAS=   46.1 FOM= 0.49 TEST= 0
INDE 12 56 44 FOBS=    0.0 SIGMA= 19.6 PHAS=    0.0 FOM= 0.00 TEST= 0
INDE 12 56 46 FOBS=   36.6 SIGMA=  7.2 PHAS=  -56.4 FOM= 0.15 TEST= 0
INDE 12 56 48 FOBS=   45.3 SIGMA=  5.9 PHAS=  -55.2 FOM= 0.54 TEST= 0
INDE 12 56 50 FOBS=   59.2 SIGMA=  6.2 PHAS= -136.3 FOM= 0.84 TEST= 0
INDE 12 56 52 FOBS=   38.1 SIGMA=  9.5 PHAS=  144.2 FOM= 0.68 TEST= 0
INDE 12 57 13 FOBS=   68.9 SIGMA=  2.3 PHAS=  -12.3 FOM= 0.72 TEST= 0
INDE 12 57 15 FOBS=   84.5 SIGMA=  2.4 PHAS=   71.6 FOM= 0.94 TEST= 0
INDE 12 57 17 FOBS=   57.6 SIGMA=  4.4 PHAS=  129.4 FOM= 0.31 TEST= 0
INDE 12 57 19 FOBS=   38.6 SIGMA=  6.1 PHAS=  -29.3 FOM= 0.04 TEST= 1
INDE 12 57 21 FOBS=   50.3 SIGMA=  3.8 PHAS=  -47.0 FOM= 0.42 TEST= 1
INDE 12 57 23 FOBS=    0.0 SIGMA= 20.5 PHAS=    0.0 FOM= 0.00 TEST= 1
INDE 12 57 25 FOBS=   77.7 SIGMA=  2.6 PHAS=  -86.6 FOM= 0.62 TEST= 0
INDE 12 57 27 FOBS=    0.0 SIGMA= 19.7 PHAS=    0.0 FOM= 0.00 TEST= 0
INDE 12 57 29 FOBS=    2.9 SIGMA= 67.8 PHAS= -129.2 FOM= 0.07 TEST= 0
INDE 12 57 31 FOBS=    0.0 SIGMA= 19.8 PHAS=    0.0 FOM= 0.00 TEST= 0
INDE 12 57 33 FOBS=   45.2 SIGMA=  4.4 PHAS=   99.4 FOM= 0.61 TEST= 0
INDE 12 57 35 FOBS=    0.0 SIGMA= 22.4 PHAS=    0.0 FOM= 0.00 TEST= 0
INDE 12 57 37 FOBS=   61.1 SIGMA=  4.1 PHAS= -113.3 FOM= 0.87 TEST= 0
INDE 12 57 39 FOBS=   56.0 SIGMA=  3.8 PHAS=   84.3 FOM= 0.51 TEST= 0
INDE 12 57 41 FOBS=    0.0 SIGMA= 22.6 PHAS=    0.0 FOM= 0.00 TEST= 0
INDE 12 57 43 FOBS=   33.3 SIGMA=  6.1 PHAS= -102.0 FOM= 0.45 TEST= 0
INDE 12 57 45 FOBS=   60.0 SIGMA=  3.3 PHAS=  -36.6 FOM= 0.37 TEST= 0
INDE 12 57 47 FOBS=   34.6 SIGMA=  8.6 PHAS=  -65.7 FOM= 0.42 TEST= 0
INDE 12 57 49 FOBS=   53.5 SIGMA=  8.7 PHAS= -141.0 FOM= 0.79 TEST= 0
INDE 12 57 51 FOBS=   88.6 SIGMA=  4.3 PHAS=  102.2 FOM= 0.92 TEST= 0
INDE 12 58 12 FOBS=  127.2 SIGMA=  2.1 PHAS= -132.4 FOM= 0.90 TEST= 0
INDE 12 58 14 FOBS=  180.3 SIGMA=  1.1 PHAS= -172.9 FOM= 0.67 TEST= 1
INDE 12 58 16 FOBS=   52.9 SIGMA=  3.7 PHAS=  -52.7 FOM= 0.55 TEST= 0
INDE 12 58 18 FOBS=  107.8 SIGMA=  2.4 PHAS=  167.3 FOM= 0.48 TEST= 1
INDE 12 58 20 FOBS=  102.4 SIGMA=  1.9 PHAS= -131.6 FOM= 0.90 TEST= 0
INDE 12 58 22 FOBS=    0.0 SIGMA= 20.2 PHAS=    0.0 FOM= 0.00 TEST= 0
INDE 12 58 24 FOBS=   59.1 SIGMA=  3.3 PHAS=  -88.3 FOM= 0.85 TEST= 0
INDE 12 58 26 FOBS=    0.0 SIGMA= 21.7 PHAS=    0.0 FOM= 0.00 TEST= 0
INDE 12 58 28 FOBS=    0.0 SIGMA= 19.7 PHAS=    0.0 FOM= 0.00 TEST= 1
INDE 12 58 30 FOBS=    0.0 SIGMA= 20.7 PHAS=    0.0 FOM= 0.00 TEST= 0
INDE 12 58 32 FOBS=   42.2 SIGMA=  6.5 PHAS=   14.6 FOM= 0.72 TEST= 0
INDE 12 58 34 FOBS=    0.0 SIGMA= 23.7 PHAS=    0.0 FOM= 0.00 TEST= 0
INDE 12 58 36 FOBS=   85.1 SIGMA=  3.0 PHAS=   -4.7 FOM= 0.87 TEST= 0
INDE 12 58 38 FOBS=   52.9 SIGMA=  4.8 PHAS=  -21.2 FOM= 0.77 TEST= 0
INDE 12 58 40 FOBS=    0.0 SIGMA= 20.6 PHAS=    0.0 FOM= 0.00 TEST= 0
INDE 12 58 42 FOBS=    0.0 SIGMA= 20.8 PHAS=    0.0 FOM= 0.00 TEST= 0
INDE 12 58 44 FOBS=   35.9 SIGMA=  5.8 PHAS=  153.5 FOM= 0.67 TEST= 0
INDE 12 58 46 FOBS=    0.0 SIGMA= 21.0 PHAS=    0.0 FOM= 0.00 TEST= 0
INDE 12 58 48 FOBS=    0.0 SIGMA= 26.3 PHAS=    0.0 FOM= 0.00 TEST= 0
INDE 12 58 50 FOBS=   45.1 SIGMA= 10.6 PHAS= -165.0 FOM= 0.44 TEST= 0
INDE 12 59 13 FOBS=  125.6 SIGMA=  2.4 PHAS=  177.4 FOM= 0.93 TEST= 0
INDE 12 59 15 FOBS=   22.0 SIGMA=  8.4 PHAS= -118.0 FOM= 0.20 TEST= 0
INDE 12 59 17 FOBS=   26.6 SIGMA=  7.3 PHAS=    4.8 FOM= 0.35 TEST= 0
```

*FIG. 12A - 318*

```
INDE 12 59 19 FOBS=   57.9 SIGMA=  4.2 PHAS=   93.4 FOM= 0.70 TEST= 0
INDE 12 59 21 FOBS=   59.5 SIGMA=  3.2 PHAS=   73.0 FOM= 0.74 TEST= 0
INDE 12 59 23 FOBS=   39.7 SIGMA=  5.2 PHAS=   73.9 FOM= 0.69 TEST= 0
INDE 12 59 25 FOBS=   73.1 SIGMA=  3.0 PHAS=  147.3 FOM= 0.76 TEST= 0
INDE 12 59 27 FOBS=   67.6 SIGMA=  3.5 PHAS=   61.1 FOM= 0.64 TEST= 0
INDE 12 59 29 FOBS=  119.4 SIGMA=  2.1 PHAS=   38.4 FOM= 0.93 TEST= 0
INDE 12 59 31 FOBS=   27.7 SIGMA=  8.6 PHAS=   -4.5 FOM= 0.12 TEST= 0
INDE 12 59 33 FOBS=    0.0 SIGMA= 26.7 PHAS=    0.0 FOM= 0.00 TEST= 0
INDE 12 59 35 FOBS=   80.6 SIGMA=  3.1 PHAS= -102.8 FOM= 0.84 TEST= 0
INDE 12 59 37 FOBS=   84.0 SIGMA=  3.1 PHAS=  -68.5 FOM= 0.94 TEST= 0
INDE 12 59 39 FOBS=    0.0 SIGMA= 22.8 PHAS=    0.0 FOM= 0.00 TEST= 0
INDE 12 59 41 FOBS=   70.8 SIGMA=  3.1 PHAS=  -76.8 FOM= 0.87 TEST= 0
INDE 12 59 43 FOBS=   47.0 SIGMA=  4.4 PHAS=   29.0 FOM= 0.73 TEST= 0
INDE 12 59 45 FOBS=   22.3 SIGMA= 10.7 PHAS=  178.4 FOM= 0.06 TEST= 0
INDE 12 59 47 FOBS=    0.0 SIGMA= 22.9 PHAS=    0.0 FOM= 0.00 TEST= 0
INDE 12 59 49 FOBS=   81.9 SIGMA=  5.2 PHAS=  -40.0 FOM= 0.10 TEST= 1
INDE 12 60 12 FOBS=   14.6 SIGMA= 12.6 PHAS= -154.6 FOM= 0.56 TEST= 0
INDE 12 60 14 FOBS=   44.5 SIGMA=  3.5 PHAS= -171.0 FOM= 0.74 TEST= 0
INDE 12 60 16 FOBS=   41.5 SIGMA=  4.4 PHAS=  166.8 FOM= 0.38 TEST= 0
INDE 12 60 18 FOBS=   54.7 SIGMA=  3.5 PHAS=  161.5 FOM= 0.36 TEST= 0
INDE 12 60 20 FOBS=   72.3 SIGMA=  3.8 PHAS= -142.7 FOM= 0.80 TEST= 0
INDE 12 60 22 FOBS=   84.6 SIGMA=  2.5 PHAS=  -34.0 FOM= 0.83 TEST= 1
INDE 12 60 24 FOBS=  112.8 SIGMA=  2.1 PHAS=  -68.6 FOM= 0.89 TEST= 0
INDE 12 60 26 FOBS=   39.3 SIGMA=  6.0 PHAS= -150.6 FOM= 0.12 TEST= 1
INDE 12 60 28 FOBS=  134.8 SIGMA=  1.9 PHAS=  -24.4 FOM= 0.93 TEST= 0
INDE 12 60 30 FOBS=   65.9 SIGMA=  3.7 PHAS=  -59.5 FOM= 0.85 TEST= 0
INDE 12 60 32 FOBS=    8.7 SIGMA= 27.5 PHAS=   56.1 FOM= 0.03 TEST= 0
INDE 12 60 34 FOBS=   74.3 SIGMA=  3.3 PHAS=  165.5 FOM= 0.86 TEST= 0
INDE 12 60 36 FOBS=  135.5 SIGMA=  2.0 PHAS= -172.2 FOM= 0.95 TEST= 0
INDE 12 60 38 FOBS=   10.9 SIGMA= 25.8 PHAS=  -93.0 FOM= 0.20 TEST= 0
INDE 12 60 40 FOBS=   33.6 SIGMA=  7.2 PHAS=  144.4 FOM= 0.59 TEST= 0
INDE 12 60 42 FOBS=   17.2 SIGMA= 13.8 PHAS= -153.1 FOM= 0.38 TEST= 0
INDE 12 60 44 FOBS=   53.4 SIGMA=  3.7 PHAS=  -57.7 FOM= 0.80 TEST= 0
INDE 12 60 46 FOBS=    0.0 SIGMA= 28.4 PHAS=    0.0 FOM= 0.00 TEST= 0
INDE 12 60 48 FOBS=   95.5 SIGMA=  4.6 PHAS=   89.5 FOM= 0.84 TEST= 0
INDE 12 61 13 FOBS=   74.3 SIGMA=  3.4 PHAS= -142.0 FOM= 0.77 TEST= 0
INDE 12 61 15 FOBS=   66.7 SIGMA=  2.5 PHAS=   -5.4 FOM= 0.84 TEST= 0
INDE 12 61 17 FOBS=   23.5 SIGMA= 11.9 PHAS=   29.1 FOM= 0.14 TEST= 1
INDE 12 61 19 FOBS=   54.2 SIGMA=  5.1 PHAS=  164.6 FOM= 0.84 TEST= 0
INDE 12 61 21 FOBS=  104.9 SIGMA=  2.6 PHAS=  147.3 FOM= 0.89 TEST= 0
INDE 12 61 23 FOBS=  141.1 SIGMA=  1.7 PHAS=  138.9 FOM= 0.96 TEST= 0
INDE 12 61 25 FOBS=   47.5 SIGMA=  4.8 PHAS=  134.2 FOM= 0.75 TEST= 0
INDE 12 61 27 FOBS=    0.0 SIGMA= 21.7 PHAS=    0.0 FOM= 0.00 TEST= 1
INDE 12 61 29 FOBS=    0.0 SIGMA= 21.9 PHAS=    0.0 FOM= 0.00 TEST= 0
INDE 12 61 31 FOBS=   36.9 SIGMA=  6.6 PHAS= -115.9 FOM= 0.58 TEST= 0
INDE 12 61 33 FOBS=   54.2 SIGMA=  4.5 PHAS=   92.5 FOM= 0.67 TEST= 0
INDE 12 61 35 FOBS=  145.7 SIGMA=  1.8 PHAS=   75.6 FOM= 0.96 TEST= 0
INDE 12 61 37 FOBS=   52.6 SIGMA=  4.8 PHAS=   57.0 FOM= 0.84 TEST= 0
INDE 12 61 39 FOBS=   53.5 SIGMA=  6.9 PHAS=  -20.3 FOM= 0.56 TEST= 0
INDE 12 61 41 FOBS=   45.5 SIGMA=  5.3 PHAS=  129.9 FOM= 0.37 TEST= 0
INDE 12 61 43 FOBS=   46.8 SIGMA=  6.5 PHAS=  140.9 FOM= 0.72 TEST= 0
INDE 12 61 45 FOBS=    0.0 SIGMA= 24.2 PHAS=    0.0 FOM= 0.00 TEST= 0
INDE 12 62 12 FOBS=   34.2 SIGMA=  5.5 PHAS=   44.1 FOM= 0.75 TEST= 0
INDE 12 62 14 FOBS=   23.3 SIGMA= 14.7 PHAS= -156.7 FOM= 0.34 TEST= 0
INDE 12 62 16 FOBS=  124.0 SIGMA=  1.7 PHAS= -165.4 FOM= 0.83 TEST= 0
INDE 12 62 18 FOBS=   73.2 SIGMA=  3.1 PHAS=    8.8 FOM= 0.91 TEST= 0
INDE 12 62 20 FOBS=  110.7 SIGMA=  3.2 PHAS=   77.0 FOM= 0.90 TEST= 0
INDE 12 62 22 FOBS=  126.4 SIGMA=  2.2 PHAS=   80.8 FOM= 0.95 TEST= 0
INDE 12 62 24 FOBS=   97.2 SIGMA=  2.8 PHAS=   48.0 FOM= 0.91 TEST= 0
INDE 12 62 26 FOBS=   39.6 SIGMA=  6.8 PHAS=  150.4 FOM= 0.19 TEST= 0
INDE 12 62 28 FOBS=    0.0 SIGMA= 25.5 PHAS=    0.0 FOM= 0.00 TEST= 0
INDE 12 62 30 FOBS=  100.3 SIGMA=  2.9 PHAS=  112.0 FOM= 0.78 TEST= 0
INDE 12 62 32 FOBS=    0.0 SIGMA= 23.3 PHAS=    0.0 FOM= 0.00 TEST= 0
INDE 12 62 34 FOBS=   80.7 SIGMA=  3.5 PHAS=  -33.7 FOM= 0.90 TEST= 0
INDE 12 62 36 FOBS=   37.4 SIGMA=  7.7 PHAS=   -3.2 FOM= 0.12 TEST= 1
INDE 12 62 38 FOBS=    0.0 SIGMA= 24.2 PHAS=    0.0 FOM= 0.00 TEST= 0
INDE 12 62 40 FOBS=   32.3 SIGMA=  8.1 PHAS=   75.9 FOM= 0.06 TEST= 1
INDE 12 62 42 FOBS=   71.6 SIGMA=  4.3 PHAS=   26.6 FOM= 0.30 TEST= 1
INDE 12 62 44 FOBS=   65.0 SIGMA=  6.2 PHAS=  -38.1 FOM= 0.15 TEST= 1
INDE 12 63 13 FOBS=   66.8 SIGMA=  3.2 PHAS= -119.6 FOM= 0.69 TEST= 0
```

*FIG. 12A - 319*

```
INDE 12 63 15 FOBS=   87.4 SIGMA=  4.0 PHAS=  106.4 FOM= 0.71 TEST= 0
INDE 12 63 17 FOBS=    0.0 SIGMA= 21.3 PHAS=    0.0 FOM= 0.00 TEST= 0
INDE 12 63 19 FOBS=   21.7 SIGMA= 15.4 PHAS=  -86.0 FOM= 0.45 TEST= 0
INDE 12 63 21 FOBS=   77.9 SIGMA=  4.4 PHAS=  -28.4 FOM= 0.88 TEST= 0
INDE 12 63 23 FOBS=   85.8 SIGMA=  3.1 PHAS=   53.9 FOM= 0.90 TEST= 0
INDE 12 63 25 FOBS=   53.2 SIGMA=  5.0 PHAS=  -34.8 FOM= 0.65 TEST= 0
INDE 12 63 27 FOBS=   11.6 SIGMA= 28.6 PHAS=  168.3 FOM= 0.07 TEST= 0
INDE 12 63 29 FOBS=   93.4 SIGMA=  3.1 PHAS=   35.5 FOM= 0.86 TEST= 0
INDE 12 63 31 FOBS=   68.9 SIGMA=  4.2 PHAS=   63.2 FOM= 0.89 TEST= 0
INDE 12 63 33 FOBS=   18.2 SIGMA= 15.3 PHAS=   14.9 FOM= 0.09 TEST= 0
INDE 12 63 35 FOBS=   77.2 SIGMA=  3.7 PHAS=  154.3 FOM= 0.88 TEST= 0
INDE 12 63 37 FOBS=   11.0 SIGMA= 26.0 PHAS=   39.8 FOM= 0.15 TEST= 0
INDE 12 63 39 FOBS=   57.8 SIGMA=  5.2 PHAS=    7.7 FOM= 0.56 TEST= 0
INDE 12 63 41 FOBS=   17.0 SIGMA= 20.1 PHAS=    2.2 FOM= 0.38 TEST= 0
INDE 12 63 43 FOBS=   27.6 SIGMA= 11.3 PHAS=   15.7 FOM= 0.07 TEST= 0
INDE 12 64 12 FOBS=   34.5 SIGMA=  5.7 PHAS=   76.3 FOM= 0.24 TEST= 0
INDE 12 64 14 FOBS=   94.3 SIGMA=  3.7 PHAS=   51.5 FOM= 0.93 TEST= 0
INDE 12 64 16 FOBS=    0.0 SIGMA= 19.5 PHAS=    0.0 FOM= 0.00 TEST= 0
INDE 12 64 18 FOBS=   48.9 SIGMA=  4.4 PHAS=   -8.2 FOM= 0.52 TEST= 0
INDE 12 64 20 FOBS=    7.0 SIGMA= 47.7 PHAS=   71.6 FOM= 0.02 TEST= 0
INDE 12 64 22 FOBS=    0.0 SIGMA= 25.7 PHAS=    0.0 FOM= 0.00 TEST= 0
INDE 12 64 24 FOBS=   96.3 SIGMA=  2.8 PHAS=   85.9 FOM= 0.81 TEST= 0
INDE 12 64 26 FOBS=   53.4 SIGMA=  5.0 PHAS= -101.1 FOM= 0.72 TEST= 0
INDE 12 64 28 FOBS=   79.9 SIGMA=  3.5 PHAS= -130.1 FOM= 0.92 TEST= 0
INDE 12 64 30 FOBS=   46.9 SIGMA=  6.1 PHAS=  -20.3 FOM= 0.68 TEST= 0
INDE 12 64 32 FOBS=   89.5 SIGMA=  3.3 PHAS=  -63.4 FOM= 0.87 TEST= 0
INDE 12 64 34 FOBS=   47.4 SIGMA=  6.0 PHAS=   21.4 FOM= 0.76 TEST= 0
INDE 12 64 36 FOBS=   14.7 SIGMA= 19.5 PHAS=  138.6 FOM= 0.30 TEST= 0
INDE 12 64 38 FOBS=   38.8 SIGMA=  8.8 PHAS=  -60.3 FOM= 0.39 TEST= 0
INDE 12 64 40 FOBS=   87.6 SIGMA=  3.6 PHAS= -167.1 FOM= 0.18 TEST= 1
INDE 12 64 42 FOBS=   52.6 SIGMA=  7.5 PHAS=  -50.6 FOM= 0.84 TEST= 0
INDE 12 65 13 FOBS=   73.7 SIGMA=  2.9 PHAS=  -30.3 FOM= 0.76 TEST= 0
INDE 12 65 15 FOBS=   32.5 SIGMA= 10.6 PHAS=  -62.5 FOM= 0.38 TEST= 0
INDE 12 65 17 FOBS=   39.4 SIGMA=  5.1 PHAS=  116.4 FOM= 0.27 TEST= 1
INDE 12 65 19 FOBS=   43.3 SIGMA=  7.7 PHAS= -107.3 FOM= 0.66 TEST= 0
INDE 12 65 21 FOBS=   70.5 SIGMA=  3.5 PHAS=  -94.5 FOM= 0.80 TEST= 0
INDE 12 65 23 FOBS=    0.0 SIGMA= 25.8 PHAS=    0.0 FOM= 0.00 TEST= 0
INDE 12 65 25 FOBS=   18.7 SIGMA= 14.1 PHAS=  -76.8 FOM= 0.38 TEST= 0
INDE 12 65 27 FOBS=  111.6 SIGMA=  2.5 PHAS=  162.1 FOM= 0.90 TEST= 0
INDE 12 65 29 FOBS=   55.0 SIGMA=  5.1 PHAS=  125.3 FOM= 0.75 TEST= 0
INDE 12 65 31 FOBS=   48.0 SIGMA=  6.0 PHAS= -174.9 FOM= 0.58 TEST= 0
INDE 12 65 33 FOBS=   39.7 SIGMA=  7.2 PHAS= -102.2 FOM= 0.50 TEST= 0
INDE 12 65 35 FOBS=   43.5 SIGMA=  6.6 PHAS= -151.0 FOM= 0.70 TEST= 0
INDE 12 65 37 FOBS=   60.5 SIGMA=  4.9 PHAS= -113.4 FOM= 0.79 TEST= 0
INDE 12 65 39 FOBS=   72.7 SIGMA=  4.2 PHAS=  -32.0 FOM= 0.80 TEST= 0
INDE 12 66 12 FOBS=   85.6 SIGMA=  4.1 PHAS=  176.8 FOM= 0.83 TEST= 0
INDE 12 66 14 FOBS=   66.4 SIGMA=  3.2 PHAS=    4.7 FOM= 0.89 TEST= 0
INDE 12 66 16 FOBS=   44.3 SIGMA=  7.7 PHAS= -152.7 FOM= 0.40 TEST= 0
INDE 12 66 18 FOBS=  114.9 SIGMA=  1.9 PHAS=  178.4 FOM= 0.17 TEST= 1
INDE 12 66 20 FOBS=   17.0 SIGMA= 13.3 PHAS=   88.7 FOM= 0.03 TEST= 1
INDE 12 66 22 FOBS=    0.0 SIGMA= 25.9 PHAS=    0.0 FOM= 0.00 TEST= 0
INDE 12 66 24 FOBS=   42.8 SIGMA=  7.4 PHAS=  -22.7 FOM= 0.65 TEST= 0
INDE 12 66 26 FOBS=   64.7 SIGMA=  4.2 PHAS=  116.5 FOM= 0.63 TEST= 0
INDE 12 66 28 FOBS=   47.0 SIGMA=  5.9 PHAS=   32.9 FOM= 0.77 TEST= 0
INDE 12 66 30 FOBS=    0.0 SIGMA= 23.6 PHAS=    0.0 FOM= 0.00 TEST= 1
INDE 12 66 32 FOBS=    0.0 SIGMA= 27.0 PHAS=    0.0 FOM= 0.00 TEST= 0
INDE 12 66 34 FOBS=   37.3 SIGMA=  7.8 PHAS=   97.7 FOM= 0.51 TEST= 0
INDE 12 66 36 FOBS=  108.8 SIGMA=  2.8 PHAS=  143.1 FOM= 0.95 TEST= 0
INDE 12 66 38 FOBS=   44.3 SIGMA=  6.8 PHAS=  151.1 FOM= 0.67 TEST= 0
INDE 12 67 13 FOBS=    0.0 SIGMA= 19.9 PHAS=    0.0 FOM= 0.00 TEST= 0
INDE 12 67 15 FOBS=   61.2 SIGMA=  5.6 PHAS= -108.0 FOM= 0.79 TEST= 0
INDE 12 67 17 FOBS=  115.1 SIGMA=  3.1 PHAS=  -53.5 FOM= 0.90 TEST= 0
INDE 12 67 19 FOBS=   27.2 SIGMA=  7.8 PHAS=   29.5 FOM= 0.29 TEST= 0
INDE 12 67 21 FOBS=   45.8 SIGMA=  5.1 PHAS=  113.7 FOM= 0.88 TEST= 0
INDE 12 67 23 FOBS=   50.2 SIGMA=  5.1 PHAS=  -47.6 FOM= 0.62 TEST= 0
INDE 12 67 25 FOBS=   28.0 SIGMA= 11.5 PHAS=  -56.7 FOM= 0.20 TEST= 0
INDE 12 67 27 FOBS=   56.3 SIGMA=  4.9 PHAS=  -34.9 FOM= 0.78 TEST= 0
INDE 12 67 29 FOBS=   51.7 SIGMA=  5.5 PHAS=  -39.9 FOM= 0.66 TEST= 0
INDE 12 67 31 FOBS=   14.7 SIGMA= 19.4 PHAS=   -5.3 FOM= 0.26 TEST= 0
INDE 12 67 33 FOBS=   18.4 SIGMA= 16.0 PHAS= -159.1 FOM= 0.28 TEST= 0
```

*FIG. 12A - 320*

```
INDE 12 67 35 FOBS=    59.7 SIGMA=  5.0 PHAS=   19.4 FOM= 0.72 TEST= 0
INDE 12 67 37 FOBS=     7.8 SIGMA= 38.2 PHAS=   47.3 FOM= 0.14 TEST= 0
INDE 12 68 14 FOBS=    69.8 SIGMA=  3.8 PHAS=   80.8 FOM= 0.83 TEST= 0
INDE 12 68 16 FOBS=    34.7 SIGMA= 13.9 PHAS=  136.1 FOM= 0.60 TEST= 0
INDE 12 68 18 FOBS=    60.5 SIGMA=  8.1 PHAS=   66.3 FOM= 0.81 TEST= 0
INDE 12 68 20 FOBS=     0.0 SIGMA= 20.8 PHAS=    0.0 FOM= 0.00 TEST= 0
INDE 12 68 22 FOBS=    49.4 SIGMA=  4.9 PHAS=   94.4 FOM= 0.54 TEST= 1
INDE 12 68 24 FOBS=    78.4 SIGMA=  3.4 PHAS=  -31.5 FOM= 0.92 TEST= 0
INDE 12 68 26 FOBS=    37.3 SIGMA=  7.3 PHAS= -152.3 FOM= 0.53 TEST= 0
INDE 12 68 28 FOBS=    23.1 SIGMA= 14.8 PHAS=  153.5 FOM= 0.45 TEST= 0
INDE 12 68 30 FOBS=     0.0 SIGMA= 23.9 PHAS=    0.0 FOM= 0.00 TEST= 0
INDE 12 68 32 FOBS=     0.0 SIGMA= 27.0 PHAS=    0.0 FOM= 0.00 TEST= 1
INDE 12 68 34 FOBS=     0.0 SIGMA= 24.4 PHAS=    0.0 FOM= 0.00 TEST= 1
INDE 12 69 15 FOBS=    92.6 SIGMA=  3.0 PHAS=  -23.1 FOM= 0.92 TEST= 0
INDE 12 69 19 FOBS=    28.1 SIGMA=  8.7 PHAS= -105.2 FOM= 0.63 TEST= 0
INDE 12 69 21 FOBS=   105.5 SIGMA=  2.5 PHAS=   93.6 FOM= 0.90 TEST= 0
INDE 12 69 23 FOBS=    24.4 SIGMA= 20.0 PHAS=  -58.0 FOM= 0.22 TEST= 0
INDE 12 69 25 FOBS=    96.2 SIGMA=  2.8 PHAS= -122.4 FOM= 0.10 TEST= 1
INDE 12 69 27 FOBS=    16.9 SIGMA= 19.8 PHAS=  -60.3 FOM= 0.16 TEST= 0
INDE 12 69 29 FOBS=    34.8 SIGMA=  8.2 PHAS=  -50.5 FOM= 0.54 TEST= 0
INDE 12 69 31 FOBS=     0.0 SIGMA= 24.1 PHAS=    0.0 FOM= 0.00 TEST= 0
INDE 12 69 33 FOBS=     9.4 SIGMA= 39.9 PHAS= -119.0 FOM= 0.08 TEST= 0
INDE 12 70 14 FOBS=    73.4 SIGMA=  3.0 PHAS= -176.8 FOM= 0.86 TEST= 0
INDE 12 70 20 FOBS=     0.0 SIGMA= 23.2 PHAS=    0.0 FOM= 0.00 TEST= 0
INDE 12 70 22 FOBS=    14.7 SIGMA= 21.2 PHAS=  -80.2 FOM= 0.05 TEST= 1
INDE 12 70 26 FOBS=    56.7 SIGMA=  4.6 PHAS=  -85.4 FOM= 0.60 TEST= 0
INDE 12 70 28 FOBS=   105.7 SIGMA=  3.3 PHAS= -146.4 FOM= 0.19 TEST= 1
INDE 12 70 30 FOBS=    15.1 SIGMA= 19.2 PHAS=   98.8 FOM= 0.37 TEST= 0
INDE 12 71 15 FOBS=    53.8 SIGMA=  5.0 PHAS=   47.1 FOM= 0.66 TEST= 0
INDE 12 71 21 FOBS=    60.0 SIGMA=  4.9 PHAS=  -93.3 FOM= 0.81 TEST= 0
INDE 12 71 23 FOBS=    41.9 SIGMA=  7.8 PHAS=  129.3 FOM= 0.15 TEST= 0
INDE 12 71 27 FOBS=    35.0 SIGMA=  8.9 PHAS= -120.0 FOM= 0.17 TEST= 0
INDE 12 71 29 FOBS=    50.4 SIGMA=  9.8 PHAS=    6.3 FOM= 0.57 TEST= 0
INDE 12 72 16 FOBS=     0.0 SIGMA= 23.7 PHAS=    0.0 FOM= 0.00 TEST= 0
INDE 12 72 22 FOBS=    14.2 SIGMA= 22.0 PHAS=  -11.3 FOM= 0.04 TEST= 1
INDE 12 72 24 FOBS=    28.8 SIGMA= 11.9 PHAS=   -4.6 FOM= 0.17 TEST= 0
INDE 12 72 26 FOBS=   123.6 SIGMA=  3.3 PHAS=   23.1 FOM= 0.83 TEST= 0
INDE 12 73 15 FOBS=     0.0 SIGMA= 20.8 PHAS=    0.0 FOM= 0.00 TEST= 0
INDE 12 73 21 FOBS=    53.2 SIGMA=  4.9 PHAS=  -54.5 FOM= 0.19 TEST= 1
INDE 12 73 23 FOBS=    41.9 SIGMA=  8.0 PHAS=  -77.0 FOM= 0.05 TEST= 1
INDE 12 74 16 FOBS=    47.0 SIGMA=  5.9 PHAS=  -50.7 FOM= 0.59 TEST= 0
INDE 13 14 13 FOBS=   122.3 SIGMA=  0.6 PHAS=  154.7 FOM= 0.95 TEST= 0
INDE 13 14 15 FOBS=    51.1 SIGMA=  1.5 PHAS=   58.4 FOM= 0.72 TEST= 0
INDE 13 14 17 FOBS=    62.2 SIGMA=  1.1 PHAS=   18.8 FOM= 0.99 TEST= 0
INDE 13 14 19 FOBS=    63.6 SIGMA=  1.1 PHAS=   39.4 FOM= 0.90 TEST= 0
INDE 13 14 21 FOBS=   107.0 SIGMA=  0.7 PHAS=  -45.4 FOM= 0.92 TEST= 0
INDE 13 14 23 FOBS=    74.4 SIGMA=  1.0 PHAS=  -86.9 FOM= 0.91 TEST= 0
INDE 13 14 25 FOBS=    90.1 SIGMA=  0.9 PHAS=  172.4 FOM= 0.98 TEST= 0
INDE 13 14 27 FOBS=    94.0 SIGMA=  0.9 PHAS=  -97.9 FOM= 0.94 TEST= 1
INDE 13 14 29 FOBS=   190.8 SIGMA=  0.5 PHAS=  -62.0 FOM= 0.97 TEST= 0
INDE 13 14 31 FOBS=   103.8 SIGMA=  0.9 PHAS=    7.4 FOM= 0.95 TEST= 0
INDE 13 14 33 FOBS=   253.0 SIGMA=  0.5 PHAS=  107.4 FOM= 0.99 TEST= 0
INDE 13 14 35 FOBS=   297.5 SIGMA=  0.6 PHAS=  -88.1 FOM= 0.96 TEST= 0
INDE 13 14 37 FOBS=   111.5 SIGMA=  1.1 PHAS=  -41.8 FOM= 0.92 TEST= 0
INDE 13 14 39 FOBS=   134.9 SIGMA=  1.1 PHAS=  -88.9 FOM= 0.88 TEST= 0
INDE 13 14 41 FOBS=   279.3 SIGMA=  1.1 PHAS= -126.5 FOM= 0.98 TEST= 0
INDE 13 14 43 FOBS=   144.8 SIGMA=  1.5 PHAS=  169.2 FOM= 0.74 TEST= 0
INDE 13 14 45 FOBS=    86.8 SIGMA=  2.5 PHAS= -141.2 FOM= 0.93 TEST= 1
INDE 13 14 47 FOBS=   116.9 SIGMA=  2.1 PHAS=    8.2 FOM= 0.90 TEST= 1
INDE 13 14 49 FOBS=   148.0 SIGMA=  1.9 PHAS=    9.9 FOM= 0.88 TEST= 0
INDE 13 14 51 FOBS=   118.3 SIGMA=  2.3 PHAS=  -95.5 FOM= 0.86 TEST= 0
INDE 13 14 53 FOBS=    64.1 SIGMA=  3.2 PHAS= -162.3 FOM= 0.84 TEST= 0
INDE 13 14 55 FOBS=   229.0 SIGMA=  0.9 PHAS= -124.7 FOM= 0.98 TEST= 0
INDE 13 14 57 FOBS=    28.4 SIGMA=  5.2 PHAS=  143.1 FOM= 0.47 TEST= 0
INDE 13 14 59 FOBS=   109.7 SIGMA=  1.9 PHAS= -119.9 FOM= 0.90 TEST= 0
INDE 13 14 61 FOBS=   120.7 SIGMA=  1.9 PHAS= -133.6 FOM= 0.89 TEST= 0
INDE 13 14 63 FOBS=    39.2 SIGMA=  5.5 PHAS=  135.3 FOM= 0.58 TEST= 0
INDE 13 14 65 FOBS=    47.1 SIGMA=  4.8 PHAS=   58.4 FOM= 0.37 TEST= 0
INDE 13 14 67 FOBS=    97.9 SIGMA=  5.1 PHAS=  -17.6 FOM= 0.66 TEST= 0
INDE 13 15 14 FOBS=   101.5 SIGMA=  0.8 PHAS=   77.6 FOM= 0.94 TEST= 0
```

*FIG. 12A - 321*

```
INDE 13 15 16 FOBS=    101.1 SIGMA=  0.7 PHAS=   60.5 FOM= 0.99 TEST= 0
INDE 13 15 18 FOBS=     84.8 SIGMA=  0.8 PHAS=   28.6 FOM= 0.99 TEST= 0
INDE 13 15 20 FOBS=    138.8 SIGMA=  0.6 PHAS=  -90.0 FOM= 0.96 TEST= 0
INDE 13 15 22 FOBS=     81.4 SIGMA=  1.0 PHAS=  152.4 FOM= 0.83 TEST= 0
INDE 13 15 24 FOBS=    162.8 SIGMA=  0.5 PHAS=  158.0 FOM= 0.94 TEST= 0
INDE 13 15 26 FOBS=     67.2 SIGMA=  1.2 PHAS=  -39.8 FOM= 0.51 TEST= 0
INDE 13 15 28 FOBS=     41.6 SIGMA=  2.0 PHAS=  -99.3 FOM= 0.98 TEST= 0
INDE 13 15 30 FOBS=    108.8 SIGMA=  0.9 PHAS= -122.4 FOM= 0.98 TEST= 1
INDE 13 15 32 FOBS=    216.4 SIGMA=  0.5 PHAS=  -15.6 FOM= 0.98 TEST= 0
INDE 13 15 34 FOBS=    309.8 SIGMA=  0.6 PHAS=   12.0 FOM= 0.94 TEST= 0
INDE 13 15 36 FOBS=    156.3 SIGMA=  0.8 PHAS= -152.7 FOM= 0.83 TEST= 0
INDE 13 15 38 FOBS=    291.4 SIGMA=  0.6 PHAS= -118.3 FOM= 0.94 TEST= 0
INDE 13 15 40 FOBS=     91.2 SIGMA=  2.0 PHAS=  -59.3 FOM= 0.31 TEST= 0
INDE 13 15 42 FOBS=    278.9 SIGMA=  0.9 PHAS=  145.2 FOM= 0.97 TEST= 0
INDE 13 15 44 FOBS=    171.2 SIGMA=  1.2 PHAS=  107.0 FOM= 0.90 TEST= 0
INDE 13 15 46 FOBS=     97.9 SIGMA=  1.9 PHAS=  168.3 FOM= 0.93 TEST= 0
INDE 13 15 48 FOBS=    187.4 SIGMA=  0.9 PHAS=  -85.6 FOM= 0.93 TEST= 0
INDE 13 15 50 FOBS=     82.2 SIGMA=  2.0 PHAS=  101.9 FOM= 0.84 TEST= 0
INDE 13 15 52 FOBS=     54.8 SIGMA=  3.1 PHAS=   42.5 FOM= 0.81 TEST= 0
INDE 13 15 54 FOBS=     89.7 SIGMA=  2.0 PHAS=   48.8 FOM= 0.89 TEST= 0
INDE 13 15 56 FOBS=    109.6 SIGMA=  1.6 PHAS=   98.6 FOM= 0.43 TEST= 0
INDE 13 15 58 FOBS=    105.0 SIGMA=  1.9 PHAS=   96.8 FOM= 0.92 TEST= 0
INDE 13 15 60 FOBS=    110.3 SIGMA=  1.8 PHAS=  100.8 FOM= 0.86 TEST= 0
INDE 13 15 62 FOBS=     30.4 SIGMA=  7.2 PHAS= -157.2 FOM= 0.60 TEST= 0
INDE 13 15 64 FOBS=     25.1 SIGMA=  8.3 PHAS=  -75.1 FOM= 0.06 TEST= 0
INDE 13 15 66 FOBS=     90.8 SIGMA=  5.7 PHAS=   89.9 FOM= 0.87 TEST= 0
INDE 13 16 13 FOBS=    143.5 SIGMA=  0.5 PHAS=  -50.8 FOM= 0.90 TEST= 0
INDE 13 16 15 FOBS=    189.7 SIGMA=  0.5 PHAS=   -0.8 FOM= 0.98 TEST= 0
INDE 13 16 17 FOBS=    166.1 SIGMA=  0.6 PHAS=  -30.3 FOM= 0.98 TEST= 0
INDE 13 16 19 FOBS=     41.1 SIGMA=  1.6 PHAS=  -79.3 FOM= 0.72 TEST= 0
INDE 13 16 21 FOBS=    222.9 SIGMA=  0.4 PHAS=  149.8 FOM= 0.98 TEST= 0
INDE 13 16 23 FOBS=    117.5 SIGMA=  0.7 PHAS=  -22.7 FOM= 0.99 TEST= 0
INDE 13 16 25 FOBS=     48.2 SIGMA=  1.5 PHAS=  152.6 FOM= 0.96 TEST= 0
INDE 13 16 27 FOBS=    317.7 SIGMA=  0.4 PHAS= -167.5 FOM= 0.97 TEST= 0
INDE 13 16 29 FOBS=    204.8 SIGMA=  0.5 PHAS=  -45.4 FOM= 0.88 TEST= 0
INDE 13 16 31 FOBS=    149.5 SIGMA=  0.7 PHAS= -132.6 FOM= 0.96 TEST= 0
INDE 13 16 33 FOBS=    162.3 SIGMA=  0.7 PHAS=  -73.6 FOM= 0.84 TEST= 0
INDE 13 16 35 FOBS=    257.6 SIGMA=  0.5 PHAS=  -26.6 FOM= 0.89 TEST= 0
INDE 13 16 37 FOBS=    238.6 SIGMA=  0.6 PHAS=   93.0 FOM= 0.96 TEST= 0
INDE 13 16 39 FOBS=    281.0 SIGMA=  0.7 PHAS= -172.6 FOM= 0.96 TEST= 0
INDE 13 16 41 FOBS=    189.2 SIGMA=  0.9 PHAS=  175.9 FOM= 0.98 TEST= 1
INDE 13 16 43 FOBS=    324.5 SIGMA=  0.7 PHAS=   43.5 FOM= 0.97 TEST= 0
INDE 13 16 45 FOBS=     25.1 SIGMA=  6.8 PHAS=   67.8 FOM= 0.87 TEST= 0
INDE 13 16 47 FOBS=    135.5 SIGMA=  1.3 PHAS= -176.1 FOM= 0.92 TEST= 0
INDE 13 16 49 FOBS=    130.6 SIGMA=  1.3 PHAS=   -4.6 FOM= 0.95 TEST= 0
INDE 13 16 51 FOBS=    196.6 SIGMA=  1.0 PHAS=  -38.4 FOM= 0.95 TEST= 0
INDE 13 16 53 FOBS=     64.4 SIGMA=  2.4 PHAS=  -58.0 FOM= 0.41 TEST= 0
INDE 13 16 55 FOBS=     81.1 SIGMA=  1.9 PHAS=  -65.0 FOM= 0.76 TEST= 0
INDE 13 16 57 FOBS=     62.9 SIGMA=  3.2 PHAS=  -50.0 FOM= 0.61 TEST= 0
INDE 13 16 59 FOBS=     86.8 SIGMA=  2.3 PHAS=  -30.7 FOM= 0.87 TEST= 0
INDE 13 16 61 FOBS=    159.7 SIGMA=  1.5 PHAS=  170.6 FOM= 0.97 TEST= 0
INDE 13 16 63 FOBS=     36.3 SIGMA=  5.6 PHAS=   88.3 FOM= 0.68 TEST= 0
INDE 13 16 65 FOBS=      0.0 SIGMA= 26.1 PHAS=    0.0 FOM= 0.00 TEST= 0
INDE 13 17 14 FOBS=    190.5 SIGMA=  0.5 PHAS=  -72.9 FOM= 0.91 TEST= 0
INDE 13 17 16 FOBS=    234.7 SIGMA=  0.4 PHAS= -132.5 FOM= 0.94 TEST= 0
INDE 13 17 18 FOBS=     66.8 SIGMA=  1.1 PHAS= -113.8 FOM= 0.95 TEST= 0
INDE 13 17 20 FOBS=     43.2 SIGMA=  1.6 PHAS=  177.1 FOM= 0.79 TEST= 0
INDE 13 17 22 FOBS=    124.8 SIGMA=  0.6 PHAS=  128.6 FOM= 0.96 TEST= 0
INDE 13 17 24 FOBS=     43.5 SIGMA=  1.7 PHAS= -156.3 FOM= 0.87 TEST= 0
INDE 13 17 26 FOBS=    110.7 SIGMA=  0.8 PHAS=    1.2 FOM= 0.43 TEST= 0
INDE 13 17 28 FOBS=    217.2 SIGMA=  0.5 PHAS=   35.5 FOM= 0.91 TEST= 0
INDE 13 17 30 FOBS=    222.8 SIGMA=  0.5 PHAS=  162.9 FOM= 0.95 TEST= 0
INDE 13 17 32 FOBS=     97.9 SIGMA=  0.9 PHAS=   95.4 FOM= 0.99 TEST= 0
INDE 13 17 34 FOBS=    172.9 SIGMA=  0.6 PHAS=  -39.4 FOM= 0.88 TEST= 0
INDE 13 17 36 FOBS=    182.6 SIGMA=  0.6 PHAS= -104.7 FOM= 0.96 TEST= 0
INDE 13 17 38 FOBS=     46.4 SIGMA=  2.6 PHAS=  160.3 FOM= 0.93 TEST= 0
INDE 13 17 40 FOBS=    288.7 SIGMA=  0.6 PHAS=   96.0 FOM= 0.97 TEST= 0
INDE 13 17 42 FOBS=    193.5 SIGMA=  0.9 PHAS=  158.5 FOM= 0.98 TEST= 0
INDE 13 17 44 FOBS=     92.5 SIGMA=  2.5 PHAS=  145.8 FOM= 0.88 TEST= 0
INDE 13 17 46 FOBS=    124.2 SIGMA=  1.4 PHAS=  128.1 FOM= 0.85 TEST= 0
```

*FIG. 12A - 322*

```
INDE  13  17  48  FOBS=   128.3  SIGMA=   1.3  PHAS=   -95.7  FOM=  0.76  TEST= 0
INDE  13  17  50  FOBS=   206.7  SIGMA=   0.9  PHAS=  -108.8  FOM=  0.96  TEST= 0
INDE  13  17  52  FOBS=    88.6  SIGMA=   1.8  PHAS=  -115.8  FOM=  0.27  TEST= 0
INDE  13  17  54  FOBS=    73.3  SIGMA=   2.1  PHAS=   155.1  FOM=  0.25  TEST= 0
INDE  13  17  56  FOBS=    62.4  SIGMA=   2.4  PHAS=   -11.2  FOM=  0.89  TEST= 1
INDE  13  17  58  FOBS=    67.1  SIGMA=   2.6  PHAS=    93.1  FOM=  0.65  TEST= 0
INDE  13  17  60  FOBS=    70.3  SIGMA=   3.7  PHAS=    91.0  FOM=  0.73  TEST= 0
INDE  13  17  62  FOBS=   147.4  SIGMA=   1.5  PHAS=    89.1  FOM=  0.96  TEST= 0
INDE  13  17  64  FOBS=    70.7  SIGMA=   5.0  PHAS=   146.7  FOM=  0.32  TEST= 1
INDE  13  17  66  FOBS=    43.1  SIGMA=  11.5  PHAS=   160.0  FOM=  0.39  TEST= 0
INDE  13  18  13  FOBS=   149.2  SIGMA=   0.5  PHAS=    79.2  FOM=  0.99  TEST= 0
INDE  13  18  15  FOBS=   231.4  SIGMA=   0.5  PHAS=   112.4  FOM=  0.95  TEST= 0
INDE  13  18  17  FOBS=    33.7  SIGMA=   2.2  PHAS=  -102.3  FOM=  0.61  TEST= 0
INDE  13  18  19  FOBS=    97.5  SIGMA=   0.8  PHAS=    47.3  FOM=  0.78  TEST= 0
INDE  13  18  21  FOBS=   224.7  SIGMA=   0.5  PHAS=   108.4  FOM=  0.96  TEST= 0
INDE  13  18  23  FOBS=    57.6  SIGMA=   1.3  PHAS=   -13.9  FOM=  0.44  TEST= 1
INDE  13  18  25  FOBS=   157.2  SIGMA=   0.6  PHAS=  -164.7  FOM=  0.83  TEST= 1
INDE  13  18  27  FOBS=   263.4  SIGMA=   0.5  PHAS=  -136.5  FOM=  0.94  TEST= 0
INDE  13  18  29  FOBS=   241.9  SIGMA=   0.4  PHAS=     7.1  FOM=  0.95  TEST= 0
INDE  13  18  31  FOBS=   123.3  SIGMA=   0.8  PHAS=   -11.5  FOM=  0.98  TEST= 0
INDE  13  18  33  FOBS=   106.2  SIGMA=   0.9  PHAS=   -75.9  FOM=  0.95  TEST= 0
INDE  13  18  35  FOBS=   191.4  SIGMA=   0.6  PHAS=    33.1  FOM=  0.87  TEST= 0
INDE  13  18  37  FOBS=   365.7  SIGMA=   0.6  PHAS=   100.5  FOM=  0.97  TEST= 0
INDE  13  18  39  FOBS=    52.1  SIGMA=   2.5  PHAS=   -82.5  FOM=  0.87  TEST= 1
INDE  13  18  41  FOBS=   247.8  SIGMA=   0.7  PHAS=    40.9  FOM=  0.96  TEST= 0
INDE  13  18  43  FOBS=   442.1  SIGMA=   0.7  PHAS=    41.1  FOM=  0.99  TEST= 0
INDE  13  18  45  FOBS=   100.6  SIGMA=   1.6  PHAS=    21.5  FOM=  0.89  TEST= 1
INDE  13  18  47  FOBS=    80.4  SIGMA=   2.1  PHAS=   -59.5  FOM=  0.51  TEST= 0
INDE  13  18  49  FOBS=   226.6  SIGMA=   0.8  PHAS=  -100.5  FOM=  0.18  TEST= 1
INDE  13  18  51  FOBS=   196.1  SIGMA=   0.9  PHAS=  -139.0  FOM=  0.94  TEST= 0
INDE  13  18  53  FOBS=    94.0  SIGMA=   1.7  PHAS=   110.7  FOM=  0.10  TEST= 1
INDE  13  18  55  FOBS=    71.9  SIGMA=   2.2  PHAS=    59.3  FOM=  0.75  TEST= 0
INDE  13  18  57  FOBS=   101.1  SIGMA=   1.7  PHAS=   -93.7  FOM=  0.87  TEST= 0
INDE  13  18  59  FOBS=    72.4  SIGMA=   2.5  PHAS=   -15.2  FOM=  0.92  TEST= 0
INDE  13  18  61  FOBS=    57.4  SIGMA=   3.2  PHAS=    90.6  FOM=  0.29  TEST= 0
INDE  13  18  63  FOBS=    56.6  SIGMA=   6.2  PHAS=   102.2  FOM=  0.74  TEST= 0
INDE  13  18  65  FOBS=    58.0  SIGMA=   6.0  PHAS=    80.2  FOM=  0.41  TEST= 0
INDE  13  19  14  FOBS=   141.7  SIGMA=   0.6  PHAS=   -16.7  FOM=  0.97  TEST= 0
INDE  13  19  16  FOBS=   173.3  SIGMA=   0.6  PHAS=   157.8  FOM=  0.98  TEST= 0
INDE  13  19  18  FOBS=    84.2  SIGMA=   0.9  PHAS=   -20.9  FOM=  0.86  TEST= 0
INDE  13  19  20  FOBS=    51.4  SIGMA=   1.5  PHAS=   -95.8  FOM=  0.96  TEST= 1
INDE  13  19  22  FOBS=   103.4  SIGMA=   0.8  PHAS=    75.5  FOM=  0.96  TEST= 0
INDE  13  19  24  FOBS=    81.0  SIGMA=   1.0  PHAS=   -38.5  FOM=  0.84  TEST= 0
INDE  13  19  26  FOBS=   157.0  SIGMA=   0.6  PHAS=   145.2  FOM=  0.90  TEST= 0
INDE  13  19  28  FOBS=   114.3  SIGMA=   0.8  PHAS=   118.2  FOM=  0.85  TEST= 0
INDE  13  19  30  FOBS=   281.7  SIGMA=   0.5  PHAS=  -178.6  FOM=  0.99  TEST= 0
INDE  13  19  32  FOBS=   199.8  SIGMA=   0.5  PHAS=    10.5  FOM=  0.98  TEST= 0
INDE  13  19  34  FOBS=   104.0  SIGMA=   1.0  PHAS=   -64.4  FOM=  0.95  TEST= 0
INDE  13  19  36  FOBS=   289.6  SIGMA=   0.6  PHAS=   -71.4  FOM=  0.94  TEST= 0
INDE  13  19  38  FOBS=    85.3  SIGMA=   1.5  PHAS=    23.4  FOM=  0.98  TEST= 0
INDE  13  19  40  FOBS=   129.3  SIGMA=   1.1  PHAS=  -150.6  FOM=  0.91  TEST= 0
INDE  13  19  42  FOBS=   305.5  SIGMA=   0.6  PHAS=   -67.6  FOM=  0.97  TEST= 0
INDE  13  19  44  FOBS=   169.9  SIGMA=   1.0  PHAS=   -87.2  FOM=  0.91  TEST= 0
INDE  13  19  46  FOBS=    15.2  SIGMA=  11.0  PHAS=   139.5  FOM=  0.18  TEST= 0
INDE  13  19  48  FOBS=   216.1  SIGMA=   0.9  PHAS=    66.9  FOM=  0.94  TEST= 0
INDE  13  19  50  FOBS=   195.4  SIGMA=   0.9  PHAS=   101.0  FOM=  0.86  TEST= 0
INDE  13  19  52  FOBS=    97.2  SIGMA=   1.7  PHAS=    90.3  FOM=  0.35  TEST= 0
INDE  13  19  54  FOBS=   160.7  SIGMA=   1.0  PHAS=     2.5  FOM=  0.95  TEST= 0
INDE  13  19  56  FOBS=    88.8  SIGMA=   1.7  PHAS=    57.1  FOM=  0.93  TEST= 0
INDE  13  19  58  FOBS=    44.6  SIGMA=   3.9  PHAS=    67.6  FOM=  0.85  TEST= 0
INDE  13  19  60  FOBS=     0.0  SIGMA=  18.6  PHAS=     0.0  FOM=  0.00  TEST= 0
INDE  13  19  62  FOBS=    41.4  SIGMA=   6.8  PHAS=    35.9  FOM=  0.80  TEST= 0
INDE  13  19  64  FOBS=    17.5  SIGMA=  19.3  PHAS=    56.4  FOM=  0.18  TEST= 0
INDE  13  20  13  FOBS=   170.6  SIGMA=   0.5  PHAS=   102.8  FOM=  0.80  TEST= 0
INDE  13  20  15  FOBS=    69.1  SIGMA=   1.2  PHAS=     3.5  FOM=  0.72  TEST= 0
INDE  13  20  17  FOBS=    99.9  SIGMA=   0.8  PHAS=    67.0  FOM=  0.92  TEST= 0
INDE  13  20  19  FOBS=    82.0  SIGMA=   1.0  PHAS=   125.9  FOM=  0.99  TEST= 0
INDE  13  20  21  FOBS=   207.5  SIGMA=   0.5  PHAS=    59.7  FOM=  0.99  TEST= 0
INDE  13  20  23  FOBS=    95.2  SIGMA=   0.9  PHAS=    76.5  FOM=  0.98  TEST= 0
INDE  13  20  25  FOBS=   283.8  SIGMA=   0.5  PHAS=  -157.4  FOM=  0.98  TEST= 0
```

*FIG. 12A - 323*

```
INDE 13 20 27 FOBS=  191.0 SIGMA=  0.6 PHAS=   74.9 FOM= 0.98 TEST= 0
INDE 13 20 29 FOBS=  225.4 SIGMA=  0.5 PHAS=  102.2 FOM= 0.96 TEST= 0
INDE 13 20 31 FOBS=  124.9 SIGMA=  0.8 PHAS=  -81.4 FOM= 0.98 TEST= 0
INDE 13 20 33 FOBS=   46.7 SIGMA=  2.1 PHAS=  -87.0 FOM= 0.74 TEST= 0
INDE 13 20 35 FOBS=   91.8 SIGMA=  1.3 PHAS=   62.3 FOM= 0.71 TEST= 0
INDE 13 20 37 FOBS=  191.2 SIGMA=  0.7 PHAS=  148.1 FOM= 0.88 TEST= 0
INDE 13 20 39 FOBS=  141.1 SIGMA=  1.0 PHAS=  144.3 FOM= 0.82 TEST= 0
INDE 13 20 41 FOBS=   52.0 SIGMA=  2.9 PHAS=   57.4 FOM= 0.81 TEST= 0
INDE 13 20 43 FOBS=  162.3 SIGMA=  1.0 PHAS=  176.2 FOM= 0.93 TEST= 0
INDE 13 20 45 FOBS=  164.3 SIGMA=  1.0 PHAS=  160.4 FOM= 0.92 TEST= 0
INDE 13 20 47 FOBS=   49.7 SIGMA=  3.3 PHAS=  -52.8 FOM= 0.80 TEST= 1
INDE 13 20 49 FOBS=   82.0 SIGMA=  2.0 PHAS=   22.3 FOM= 0.93 TEST= 0
INDE 13 20 51 FOBS=   46.4 SIGMA=  3.5 PHAS=  149.9 FOM= 0.77 TEST= 0
INDE 13 20 53 FOBS=  123.8 SIGMA=  1.3 PHAS= -109.1 FOM= 0.93 TEST= 0
INDE 13 20 55 FOBS=   92.8 SIGMA=  1.7 PHAS=  -47.8 FOM= 0.92 TEST= 1
INDE 13 20 57 FOBS=  166.4 SIGMA=  1.1 PHAS=  -46.8 FOM= 0.94 TEST= 0
INDE 13 20 59 FOBS=   55.9 SIGMA=  3.0 PHAS=  -46.9 FOM= 0.85 TEST= 0
INDE 13 20 61 FOBS=   46.7 SIGMA=  5.2 PHAS= -169.1 FOM= 0.63 TEST= 0
INDE 13 20 63 FOBS=    0.0 SIGMA= 21.9 PHAS=    0.0 FOM= 0.00 TEST= 0
INDE 13 20 65 FOBS=   67.6 SIGMA=  5.3 PHAS=  -74.8 FOM= 0.91 TEST= 0
INDE 13 20 67 FOBS=   67.4 SIGMA=  7.5 PHAS=  107.9 FOM= 0.57 TEST= 0
INDE 13 21 14 FOBS=   69.8 SIGMA=  1.1 PHAS= -138.2 FOM= 0.82 TEST= 0
INDE 13 21 16 FOBS=   17.4 SIGMA=  5.8 PHAS=   74.1 FOM= 0.22 TEST= 0
INDE 13 21 18 FOBS=  206.1 SIGMA=  0.5 PHAS=  -17.0 FOM= 0.96 TEST= 0
INDE 13 21 20 FOBS=   17.7 SIGMA=  4.8 PHAS=  -79.6 FOM= 0.25 TEST= 0
INDE 13 21 22 FOBS=  128.7 SIGMA=  0.7 PHAS=  -58.6 FOM= 0.98 TEST= 0
INDE 13 21 24 FOBS=   99.3 SIGMA=  1.0 PHAS=  -34.9 FOM= 0.27 TEST= 0
INDE 13 21 26 FOBS=  171.2 SIGMA=  0.6 PHAS=  142.2 FOM= 0.98 TEST= 0
INDE 13 21 28 FOBS=  148.2 SIGMA=  0.7 PHAS=   67.2 FOM= 0.92 TEST= 0
INDE 13 21 30 FOBS=  107.7 SIGMA=  1.0 PHAS=  160.8 FOM= 0.99 TEST= 0
INDE 13 21 32 FOBS=  158.2 SIGMA=  0.7 PHAS=  -33.5 FOM= 0.89 TEST= 0
INDE 13 21 34 FOBS=  185.0 SIGMA=  0.7 PHAS=  -48.6 FOM= 0.89 TEST= 0
INDE 13 21 36 FOBS=   78.1 SIGMA=  1.6 PHAS=   13.0 FOM= 0.02 TEST= 0
INDE 13 21 38 FOBS=  142.6 SIGMA=  1.0 PHAS=   71.3 FOM= 0.96 TEST= 0
INDE 13 21 40 FOBS=  113.1 SIGMA=  1.3 PHAS=    3.5 FOM= 0.89 TEST= 0
INDE 13 21 42 FOBS=   55.5 SIGMA=  3.0 PHAS=   15.8 FOM= 0.93 TEST= 0
INDE 13 21 44 FOBS=  141.2 SIGMA=  1.2 PHAS=   62.3 FOM= 0.95 TEST= 0
INDE 13 21 46 FOBS=  126.4 SIGMA=  1.2 PHAS=  101.4 FOM= 0.60 TEST= 1
INDE 13 21 48 FOBS=  102.2 SIGMA=  1.5 PHAS=  136.1 FOM= 0.88 TEST= 0
INDE 13 21 50 FOBS=  217.8 SIGMA=  0.8 PHAS=   50.9 FOM= 0.83 TEST= 0
INDE 13 21 52 FOBS=   43.4 SIGMA=  3.6 PHAS=   32.1 FOM= 0.62 TEST= 0
INDE 13 21 54 FOBS=   79.9 SIGMA=  2.0 PHAS=  -78.1 FOM= 0.92 TEST= 0
INDE 13 21 56 FOBS=  196.9 SIGMA=  1.0 PHAS= -133.9 FOM= 0.97 TEST= 0
INDE 13 21 58 FOBS=  123.7 SIGMA=  1.5 PHAS=  -89.8 FOM= 0.90 TEST= 0
INDE 13 21 60 FOBS=  112.1 SIGMA=  2.3 PHAS=   75.1 FOM= 0.93 TEST= 0
INDE 13 21 62 FOBS=   67.9 SIGMA=  3.6 PHAS=  137.5 FOM= 0.88 TEST= 0
INDE 13 21 64 FOBS=  122.3 SIGMA=  2.5 PHAS= -165.3 FOM= 0.97 TEST= 0
INDE 13 21 66 FOBS=  124.3 SIGMA=  4.1 PHAS=   32.8 FOM= 0.93 TEST= 0
INDE 13 21 68 FOBS=   59.8 SIGMA=  8.5 PHAS= -136.5 FOM= 0.77 TEST= 0
INDE 13 22 13 FOBS=  137.4 SIGMA=  0.6 PHAS=   60.3 FOM= 0.96 TEST= 0
INDE 13 22 15 FOBS=   85.0 SIGMA=  1.0 PHAS=    9.8 FOM= 0.80 TEST= 0
INDE 13 22 17 FOBS=  129.9 SIGMA=  0.7 PHAS= -122.8 FOM= 0.98 TEST= 0
INDE 13 22 19 FOBS=  105.8 SIGMA=  0.8 PHAS=  155.8 FOM= 0.93 TEST= 0
INDE 13 22 21 FOBS=   52.2 SIGMA=  1.6 PHAS=   31.4 FOM= 0.97 TEST= 0
INDE 13 22 23 FOBS=  204.4 SIGMA=  0.6 PHAS=  102.6 FOM= 0.98 TEST= 0
INDE 13 22 25 FOBS=  198.7 SIGMA=  0.6 PHAS=  140.5 FOM= 0.89 TEST= 0
INDE 13 22 27 FOBS=  427.9 SIGMA=  0.5 PHAS=   74.6 FOM= 0.97 TEST= 0
INDE 13 22 29 FOBS=  141.0 SIGMA=  0.8 PHAS=  131.0 FOM= 0.33 TEST= 1
INDE 13 22 31 FOBS=   80.3 SIGMA=  1.3 PHAS=   79.2 FOM= 0.93 TEST= 0
INDE 13 22 33 FOBS=   94.6 SIGMA=  1.3 PHAS=  164.3 FOM= 0.87 TEST= 0
INDE 13 22 35 FOBS=   84.2 SIGMA=  1.6 PHAS= -170.1 FOM= 0.80 TEST= 0
INDE 13 22 37 FOBS=  149.4 SIGMA=  1.0 PHAS=   72.0 FOM= 0.97 TEST= 0
INDE 13 22 39 FOBS=   68.3 SIGMA=  2.1 PHAS=  167.3 FOM= 0.92 TEST= 1
INDE 13 22 41 FOBS=  157.4 SIGMA=  1.0 PHAS=  -41.5 FOM= 0.91 TEST= 0
INDE 13 22 43 FOBS=  170.2 SIGMA=  1.0 PHAS= -137.6 FOM= 0.84 TEST= 0
INDE 13 22 45 FOBS=   64.4 SIGMA=  2.3 PHAS=  -64.1 FOM= 0.75 TEST= 0
INDE 13 22 47 FOBS=   97.1 SIGMA=  1.5 PHAS=   -4.2 FOM= 0.97 TEST= 0
INDE 13 22 49 FOBS=  120.9 SIGMA=  1.3 PHAS=  -30.2 FOM= 0.40 TEST= 1
INDE 13 22 51 FOBS=   45.3 SIGMA=  3.3 PHAS= -125.2 FOM= 0.70 TEST= 0
INDE 13 22 53 FOBS=   87.0 SIGMA=  1.9 PHAS= -137.0 FOM= 0.82 TEST= 0
```

*FIG. 12A - 324*

```
INDE 13 22 55 FOBS=  141.5 SIGMA=  1.2 PHAS=  167.0 FOM= 0.92 TEST= 0
INDE 13 22 57 FOBS=  121.4 SIGMA=  1.5 PHAS=  172.3 FOM= 0.93 TEST= 0
INDE 13 22 59 FOBS=   85.1 SIGMA=  2.7 PHAS= -115.8 FOM= 0.84 TEST= 0
INDE 13 22 61 FOBS=  110.7 SIGMA=  2.3 PHAS=   38.4 FOM= 0.86 TEST= 0
INDE 13 22 63 FOBS=   83.6 SIGMA=  3.0 PHAS=  103.5 FOM= 0.95 TEST= 0
INDE 13 22 65 FOBS=   63.4 SIGMA=  7.8 PHAS=  -55.9 FOM= 0.82 TEST= 0
INDE 13 22 67 FOBS=    6.7 SIGMA= 74.6 PHAS= -126.6 FOM= 0.21 TEST= 0
INDE 13 22 69 FOBS=   13.3 SIGMA= 38.1 PHAS=  -22.1 FOM= 0.35 TEST= 0
INDE 13 22 71 FOBS=   22.1 SIGMA= 23.5 PHAS=   32.1 FOM= 0.15 TEST= 0
INDE 13 23 14 FOBS=  173.5 SIGMA=  0.5 PHAS=  -69.0 FOM= 0.98 TEST= 1
INDE 13 23 16 FOBS=   83.8 SIGMA=  1.1 PHAS=  156.4 FOM= 0.98 TEST= 0
INDE 13 23 18 FOBS=   71.4 SIGMA=  1.1 PHAS=   69.6 FOM= 0.72 TEST= 0
INDE 13 23 20 FOBS=   65.1 SIGMA=  1.3 PHAS=  -61.2 FOM= 0.92 TEST= 0
INDE 13 23 22 FOBS=  143.5 SIGMA=  0.8 PHAS=    3.3 FOM= 0.77 TEST= 1
INDE 13 23 24 FOBS=  196.3 SIGMA=  0.6 PHAS=    7.2 FOM= 0.97 TEST= 0
INDE 13 23 26 FOBS=  180.9 SIGMA=  0.7 PHAS=   28.7 FOM= 0.89 TEST= 0
INDE 13 23 28 FOBS=  177.1 SIGMA=  0.7 PHAS=   21.8 FOM= 0.66 TEST= 1
INDE 13 23 30 FOBS=   77.3 SIGMA=  1.5 PHAS=   42.7 FOM= 0.98 TEST= 0
INDE 13 23 32 FOBS=  337.6 SIGMA=  0.7 PHAS=  -91.5 FOM= 0.96 TEST= 0
INDE 13 23 34 FOBS=  120.8 SIGMA=  1.1 PHAS=  -22.4 FOM= 0.55 TEST= 0
INDE 13 23 36 FOBS=  175.1 SIGMA=  0.9 PHAS=  165.2 FOM= 0.85 TEST= 0
INDE 13 23 38 FOBS=   85.3 SIGMA=  1.7 PHAS=  -40.4 FOM= 0.93 TEST= 0
INDE 13 23 40 FOBS=  142.0 SIGMA=  1.1 PHAS=   90.2 FOM= 0.82 TEST= 0
INDE 13 23 42 FOBS=  136.0 SIGMA=  1.2 PHAS=  171.0 FOM= 0.46 TEST= 0
INDE 13 23 44 FOBS=  166.3 SIGMA=  1.0 PHAS=  100.6 FOM= 0.90 TEST= 0
INDE 13 23 46 FOBS=  133.5 SIGMA=  1.2 PHAS=  -63.4 FOM= 0.85 TEST= 0
INDE 13 23 48 FOBS=  112.2 SIGMA=  1.3 PHAS=  -77.7 FOM= 0.60 TEST= 0
INDE 13 23 50 FOBS=   74.0 SIGMA=  2.0 PHAS= -159.1 FOM= 0.70 TEST= 0
INDE 13 23 52 FOBS=  131.5 SIGMA=  1.2 PHAS=  140.4 FOM= 0.92 TEST= 0
INDE 13 23 54 FOBS=    0.0 SIGMA= 17.6 PHAS=    0.0 FOM= 0.00 TEST= 1
INDE 13 23 56 FOBS=   93.4 SIGMA=  2.0 PHAS= -177.1 FOM= 0.92 TEST= 0
INDE 13 23 58 FOBS=   55.8 SIGMA=  3.7 PHAS=  179.4 FOM= 0.83 TEST= 0
INDE 13 23 60 FOBS=  105.6 SIGMA=  2.4 PHAS=   29.6 FOM= 0.83 TEST= 0
INDE 13 23 62 FOBS=   35.0 SIGMA=  7.2 PHAS=   91.0 FOM= 0.42 TEST= 0
INDE 13 23 64 FOBS=   61.0 SIGMA=  2.6 PHAS= -111.7 FOM= 0.79 TEST= 0
INDE 13 23 66 FOBS=    0.0 SIGMA= 31.2 PHAS=    0.0 FOM= 0.00 TEST= 0
INDE 13 23 68 FOBS=   87.7 SIGMA=  5.8 PHAS= -144.5 FOM= 0.88 TEST= 0
INDE 13 23 70 FOBS=    0.0 SIGMA= 32.0 PHAS=    0.0 FOM= 0.00 TEST= 0
INDE 13 23 72 FOBS=    0.0 SIGMA= 32.5 PHAS=    0.0 FOM= 0.00 TEST= 0
INDE 13 24 13 FOBS=  102.5 SIGMA=  0.7 PHAS= -140.3 FOM= 0.92 TEST= 0
INDE 13 24 15 FOBS=  103.3 SIGMA=  0.8 PHAS=  -73.8 FOM= 0.99 TEST= 0
INDE 13 24 17 FOBS=   63.4 SIGMA=  1.6 PHAS=  115.5 FOM= 0.72 TEST= 0
INDE 13 24 19 FOBS=  126.9 SIGMA=  0.7 PHAS=   75.9 FOM= 0.52 TEST= 0
INDE 13 24 21 FOBS=  166.2 SIGMA=  0.6 PHAS= -133.9 FOM= 0.97 TEST= 0
INDE 13 24 23 FOBS=  116.0 SIGMA=  1.0 PHAS=  151.3 FOM= 0.60 TEST= 0
INDE 13 24 25 FOBS=  115.7 SIGMA=  0.9 PHAS=   54.0 FOM= 0.98 TEST= 0
INDE 13 24 27 FOBS=  219.8 SIGMA=  0.7 PHAS=   51.1 FOM= 0.91 TEST= 0
INDE 13 24 29 FOBS=   59.1 SIGMA=  2.3 PHAS=  -77.2 FOM= 0.92 TEST= 0
INDE 13 24 31 FOBS=  343.0 SIGMA=  0.6 PHAS=   87.2 FOM= 0.90 TEST= 0
INDE 13 24 33 FOBS=  400.1 SIGMA=  0.7 PHAS=  176.8 FOM= 0.96 TEST= 0
INDE 13 24 35 FOBS=  224.9 SIGMA=  0.7 PHAS=  156.6 FOM= 0.95 TEST= 0
INDE 13 24 37 FOBS=   58.8 SIGMA=  2.6 PHAS=  112.7 FOM= 0.86 TEST= 0
INDE 13 24 39 FOBS=  100.8 SIGMA=  1.6 PHAS=  -82.5 FOM= 0.95 TEST= 0
INDE 13 24 41 FOBS=  167.2 SIGMA=  1.0 PHAS=    8.8 FOM= 0.93 TEST= 0
INDE 13 24 43 FOBS=   62.5 SIGMA=  2.5 PHAS=  -70.8 FOM= 0.80 TEST= 0
INDE 13 24 45 FOBS=  103.0 SIGMA=  1.5 PHAS= -109.7 FOM= 0.67 TEST= 1
INDE 13 24 47 FOBS=    0.0 SIGMA= 18.1 PHAS=    0.0 FOM= 0.00 TEST= 0
INDE 13 24 49 FOBS=    0.0 SIGMA= 17.5 PHAS=    0.0 FOM= 0.00 TEST= 0
INDE 13 24 51 FOBS=  140.1 SIGMA=  1.1 PHAS=   85.9 FOM= 0.94 TEST= 0
INDE 13 24 53 FOBS=   23.0 SIGMA=  7.2 PHAS=   69.9 FOM= 0.56 TEST= 0
INDE 13 24 55 FOBS=  159.7 SIGMA=  1.4 PHAS=  104.9 FOM= 0.96 TEST= 0
INDE 13 24 57 FOBS=  172.9 SIGMA=  1.4 PHAS=   95.5 FOM= 0.97 TEST= 0
INDE 13 24 59 FOBS=   66.6 SIGMA=  3.8 PHAS=  -35.4 FOM= 0.81 TEST= 0
INDE 13 24 61 FOBS=    0.0 SIGMA= 27.1 PHAS=    0.0 FOM= 0.00 TEST= 0
INDE 13 24 63 FOBS=   92.6 SIGMA=  3.2 PHAS=  142.1 FOM= 0.88 TEST= 0
INDE 13 24 65 FOBS=    0.0 SIGMA= 18.1 PHAS=    0.0 FOM= 0.00 TEST= 0
INDE 13 24 67 FOBS=   57.9 SIGMA=  8.8 PHAS= -150.2 FOM= 0.88 TEST= 0
INDE 13 24 69 FOBS=    0.0 SIGMA= 31.9 PHAS=    0.0 FOM= 0.00 TEST= 0
INDE 13 24 71 FOBS=    0.0 SIGMA= 32.4 PHAS=    0.0 FOM= 0.00 TEST= 0
INDE 13 25 14 FOBS=   76.4 SIGMA=  1.1 PHAS=  161.2 FOM= 0.98 TEST= 0
```

*FIG. 12A - 325*

```
INDE 13 25 16 FOBS=    82.8 SIGMA=  1.1 PHAS=   71.5 FOM= 0.97 TEST= 0
INDE 13 25 18 FOBS=   193.0 SIGMA=  0.6 PHAS= -144.8 FOM= 0.34 TEST= 1
INDE 13 25 20 FOBS=    33.5 SIGMA=  2.4 PHAS= -158.1 FOM= 0.78 TEST= 0
INDE 13 25 22 FOBS=    55.4 SIGMA=  1.6 PHAS= -161.2 FOM= 0.95 TEST= 0
INDE 13 25 24 FOBS=   258.0 SIGMA=  0.6 PHAS=  -71.6 FOM= 0.98 TEST= 0
INDE 13 25 26 FOBS=   325.3 SIGMA=  0.6 PHAS=  -38.4 FOM= 0.96 TEST= 0
INDE 13 25 28 FOBS=   327.6 SIGMA=  0.7 PHAS=  175.0 FOM= 0.98 TEST= 0
INDE 13 25 30 FOBS=   111.7 SIGMA=  1.3 PHAS=   -1.3 FOM= 0.99 TEST= 0
INDE 13 25 32 FOBS=   228.7 SIGMA=  0.7 PHAS=  -55.2 FOM= 0.85 TEST= 0
INDE 13 25 34 FOBS=   130.7 SIGMA=  1.1 PHAS=   28.4 FOM= 0.83 TEST= 0
INDE 13 25 36 FOBS=    31.1 SIGMA=  4.8 PHAS=   68.4 FOM= 0.59 TEST= 0
INDE 13 25 38 FOBS=     0.0 SIGMA= 19.1 PHAS=    0.0 FOM= 0.00 TEST= 0
INDE 13 25 40 FOBS=     0.0 SIGMA= 18.4 PHAS=    0.0 FOM= 0.00 TEST= 0
INDE 13 25 42 FOBS=   136.1 SIGMA=  1.2 PHAS=  -37.6 FOM= 0.87 TEST= 0
INDE 13 25 44 FOBS=   116.7 SIGMA=  1.3 PHAS= -172.4 FOM= 0.39 TEST= 1
INDE 13 25 46 FOBS=   113.0 SIGMA=  1.4 PHAS= -134.3 FOM= 0.91 TEST= 0
INDE 13 25 48 FOBS=     0.0 SIGMA= 18.9 PHAS=    0.0 FOM= 0.00 TEST= 0
INDE 13 25 50 FOBS=    68.1 SIGMA=  2.1 PHAS=   45.2 FOM= 0.89 TEST= 0
INDE 13 25 52 FOBS=    33.6 SIGMA=  4.8 PHAS=  -72.7 FOM= 0.38 TEST= 0
INDE 13 25 54 FOBS=   135.9 SIGMA=  1.5 PHAS=   -6.8 FOM= 0.97 TEST= 0
INDE 13 25 56 FOBS=   132.2 SIGMA=  1.5 PHAS=   -5.2 FOM= 0.95 TEST= 0
INDE 13 25 58 FOBS=    59.0 SIGMA=  3.9 PHAS=   96.1 FOM= 0.23 TEST= 0
INDE 13 25 60 FOBS=     0.0 SIGMA= 23.7 PHAS=    0.0 FOM= 0.00 TEST= 0
INDE 13 25 62 FOBS=    17.6 SIGMA= 21.4 PHAS=   10.8 FOM= 0.00 TEST= 1
INDE 13 25 64 FOBS=     0.0 SIGMA= 31.0 PHAS=    0.0 FOM= 0.00 TEST= 0
INDE 13 25 66 FOBS=    58.3 SIGMA=  2.8 PHAS= -147.6 FOM= 0.83 TEST= 0
INDE 13 25 68 FOBS=   126.0 SIGMA=  4.0 PHAS=  147.5 FOM= 0.96 TEST= 0
INDE 13 25 70 FOBS=    30.9 SIGMA= 16.8 PHAS=  -18.3 FOM= 0.51 TEST= 0
INDE 13 25 72 FOBS=     0.0 SIGMA= 32.9 PHAS=    0.0 FOM= 0.00 TEST= 0
INDE 13 26 13 FOBS=     9.4 SIGMA=  9.0 PHAS=  -77.3 FOM= 0.05 TEST= 0
INDE 13 26 15 FOBS=   179.3 SIGMA=  0.6 PHAS=  -18.1 FOM= 0.95 TEST= 0
INDE 13 26 17 FOBS=   144.7 SIGMA=  0.8 PHAS=   50.6 FOM= 0.88 TEST= 0
INDE 13 26 19 FOBS=   285.8 SIGMA=  0.5 PHAS=   93.8 FOM= 0.94 TEST= 0
INDE 13 26 21 FOBS=   253.8 SIGMA=  0.5 PHAS=  155.0 FOM= 0.94 TEST= 0
INDE 13 26 23 FOBS=   297.1 SIGMA=  0.5 PHAS= -166.5 FOM= 0.98 TEST= 0
INDE 13 26 25 FOBS=   265.0 SIGMA=  0.6 PHAS=  149.6 FOM= 0.90 TEST= 0
INDE 13 26 27 FOBS=   236.0 SIGMA=  0.7 PHAS=  145.1 FOM= 0.98 TEST= 0
INDE 13 26 29 FOBS=   291.7 SIGMA=  0.7 PHAS=   95.9 FOM= 0.97 TEST= 0
INDE 13 26 31 FOBS=   101.7 SIGMA=  1.5 PHAS=    1.6 FOM= 0.90 TEST= 0
INDE 13 26 33 FOBS=    15.7 SIGMA= 10.9 PHAS= -169.1 FOM= 0.39 TEST= 0
INDE 13 26 35 FOBS=   212.5 SIGMA=  0.8 PHAS=  104.4 FOM= 0.92 TEST= 0
INDE 13 26 37 FOBS=    55.0 SIGMA=  2.9 PHAS=  101.1 FOM= 0.94 TEST= 0
INDE 13 26 39 FOBS=   138.1 SIGMA=  1.3 PHAS=    0.9 FOM= 0.87 TEST= 0
INDE 13 26 41 FOBS=   128.0 SIGMA=  1.4 PHAS= -120.0 FOM= 0.72 TEST= 1
INDE 13 26 43 FOBS=   140.5 SIGMA=  1.2 PHAS=  -88.0 FOM= 0.59 TEST= 1
INDE 13 26 45 FOBS=   174.9 SIGMA=  0.9 PHAS=  146.3 FOM= 0.93 TEST= 0
INDE 13 26 47 FOBS=   108.2 SIGMA=  1.4 PHAS=  144.8 FOM= 0.92 TEST= 0
INDE 13 26 49 FOBS=   174.4 SIGMA=  0.9 PHAS=   -6.2 FOM= 0.91 TEST= 0
INDE 13 26 51 FOBS=   119.3 SIGMA=  1.3 PHAS=  -73.3 FOM= 0.59 TEST= 1
INDE 13 26 53 FOBS=   100.9 SIGMA=  1.7 PHAS= -136.0 FOM= 0.94 TEST= 0
INDE 13 26 55 FOBS=    44.1 SIGMA=  4.5 PHAS=   -2.7 FOM= 0.27 TEST= 1
INDE 13 26 57 FOBS=    81.9 SIGMA=  2.4 PHAS=   57.9 FOM= 0.37 TEST= 0
INDE 13 26 59 FOBS=   100.4 SIGMA=  2.6 PHAS=   41.1 FOM= 0.90 TEST= 0
INDE 13 26 61 FOBS=    49.8 SIGMA=  5.1 PHAS= -172.8 FOM= 0.67 TEST= 0
INDE 13 26 63 FOBS=    59.4 SIGMA=  5.7 PHAS=  154.2 FOM= 0.54 TEST= 0
INDE 13 26 65 FOBS=     0.0 SIGMA= 19.7 PHAS=    0.0 FOM= 0.00 TEST= 0
INDE 13 26 67 FOBS=   103.6 SIGMA=  1.8 PHAS=   75.0 FOM= 0.94 TEST= 0
INDE 13 26 69 FOBS=    55.8 SIGMA=  9.1 PHAS=   34.8 FOM= 0.08 TEST= 1
INDE 13 26 71 FOBS=     0.0 SIGMA= 32.6 PHAS=    0.0 FOM= 0.00 TEST= 0
INDE 13 27 14 FOBS=   246.2 SIGMA=  0.5 PHAS= -152.5 FOM= 0.99 TEST= 0
INDE 13 27 16 FOBS=   249.9 SIGMA=  0.6 PHAS=  -29.7 FOM= 0.95 TEST= 0
INDE 13 27 18 FOBS=   188.5 SIGMA=  0.6 PHAS=   -8.4 FOM= 0.94 TEST= 0
INDE 13 27 20 FOBS=   183.6 SIGMA=  0.6 PHAS=   41.4 FOM= 0.99 TEST= 0
INDE 13 27 22 FOBS=   308.0 SIGMA=  0.5 PHAS=  101.3 FOM= 0.93 TEST= 0
INDE 13 27 24 FOBS=   151.3 SIGMA=  0.9 PHAS=  123.6 FOM= 0.98 TEST= 0
INDE 13 27 26 FOBS=   235.3 SIGMA=  0.7 PHAS=   14.1 FOM= 0.96 TEST= 0
INDE 13 27 28 FOBS=   166.1 SIGMA=  0.9 PHAS=  115.7 FOM= 0.93 TEST= 0
INDE 13 27 30 FOBS=    77.6 SIGMA=  1.9 PHAS= -122.8 FOM= 0.86 TEST= 0
INDE 13 27 32 FOBS=    55.9 SIGMA=  2.8 PHAS= -136.1 FOM= 0.13 TEST= 0
INDE 13 27 34 FOBS=   201.7 SIGMA=  0.9 PHAS=  -84.9 FOM= 0.94 TEST= 0
```

*FIG. 12A - 326*

| | | | | | | | | | | | |
|---|---|---|---|---|---|---|---|---|---|---|---|
| INDE | 13 | 27 | 36 | FOBS= | 180.9 | SIGMA= | 1.0 | PHAS= | -7.0 | FOM= | 0.92 | TEST= 0
| INDE | 13 | 27 | 38 | FOBS= | 188.2 | SIGMA= | 1.6 | PHAS= | -16.7 | FOM= | 0.93 | TEST= 0
| INDE | 13 | 27 | 40 | FOBS= | 229.1 | SIGMA= | 0.9 | PHAS= | 85.0 | FOM= | 0.94 | TEST= 0
| INDE | 13 | 27 | 42 | FOBS= | 117.2 | SIGMA= | 1.5 | PHAS= | -123.7 | FOM= | 0.90 | TEST= 0
| INDE | 13 | 27 | 44 | FOBS= | 136.8 | SIGMA= | 1.2 | PHAS= | 110.6 | FOM= | 0.93 | TEST= 0
| INDE | 13 | 27 | 46 | FOBS= | 81.5 | SIGMA= | 1.9 | PHAS= | 58.4 | FOM= | 0.91 | TEST= 0
| INDE | 13 | 27 | 48 | FOBS= | 103.6 | SIGMA= | 1.4 | PHAS= | -122.9 | FOM= | 0.76 | TEST= 0
| INDE | 13 | 27 | 50 | FOBS= | 145.5 | SIGMA= | 1.3 | PHAS= | -172.1 | FOM= | 0.92 | TEST= 0
| INDE | 13 | 27 | 52 | FOBS= | 27.2 | SIGMA= | 6.5 | PHAS= | -150.0 | FOM= | 0.62 | TEST= 0
| INDE | 13 | 27 | 54 | FOBS= | 92.4 | SIGMA= | 1.9 | PHAS= | -178.5 | FOM= | 0.88 | TEST= 0
| INDE | 13 | 27 | 56 | FOBS= | 153.6 | SIGMA= | 1.2 | PHAS= | -33.8 | FOM= | 0.93 | TEST= 0
| INDE | 13 | 27 | 58 | FOBS= | 120.9 | SIGMA= | 1.8 | PHAS= | -74.2 | FOM= | 0.91 | TEST= 0
| INDE | 13 | 27 | 60 | FOBS= | 73.5 | SIGMA= | 3.5 | PHAS= | -129.3 | FOM= | 0.88 | TEST= 0
| INDE | 13 | 27 | 62 | FOBS= | 31.0 | SIGMA= | 10.8 | PHAS= | 157.9 | FOM= | 0.45 | TEST= 0
| INDE | 13 | 27 | 64 | FOBS= | 0.0 | SIGMA= | 31.1 | PHAS= | 0.0 | FOM= | 0.00 | TEST= 0
| INDE | 13 | 27 | 66 | FOBS= | 0.0 | SIGMA= | 20.5 | PHAS= | 0.0 | FOM= | 0.00 | TEST= 0
| INDE | 13 | 27 | 68 | FOBS= | 0.0 | SIGMA= | 31.4 | PHAS= | 0.0 | FOM= | 0.00 | TEST= 0
| INDE | 13 | 27 | 70 | FOBS= | 0.0 | SIGMA= | 31.8 | PHAS= | 0.0 | FOM= | 0.00 | TEST= 0
| INDE | 13 | 28 | 13 | FOBS= | 56.7 | SIGMA= | 1.4 | PHAS= | 114.0 | FOM= | 0.42 | TEST= 0
| INDE | 13 | 28 | 15 | FOBS= | 98.8 | SIGMA= | 0.9 | PHAS= | -160.1 | FOM= | 0.91 | TEST= 0
| INDE | 13 | 28 | 17 | FOBS= | 259.6 | SIGMA= | 0.6 | PHAS= | -53.8 | FOM= | 0.93 | TEST= 0
| INDE | 13 | 28 | 19 | FOBS= | 312.7 | SIGMA= | 0.5 | PHAS= | 98.5 | FOM= | 0.95 | TEST= 0
| INDE | 13 | 28 | 21 | FOBS= | 257.3 | SIGMA= | 0.5 | PHAS= | 85.5 | FOM= | 0.94 | TEST= 0
| INDE | 13 | 28 | 23 | FOBS= | 0.0 | SIGMA= | 15.3 | PHAS= | 0.0 | FOM= | 0.00 | TEST= 0
| INDE | 13 | 28 | 25 | FOBS= | 289.0 | SIGMA= | 0.7 | PHAS= | 90.7 | FOM= | 0.99 | TEST= 0
| INDE | 13 | 28 | 27 | FOBS= | 0.0 | SIGMA= | 16.0 | PHAS= | 0.0 | FOM= | 0.00 | TEST= 0
| INDE | 13 | 28 | 29 | FOBS= | 253.5 | SIGMA= | 0.7 | PHAS= | 80.3 | FOM= | 0.96 | TEST= 0
| INDE | 13 | 28 | 31 | FOBS= | 95.6 | SIGMA= | 1.7 | PHAS= | 47.2 | FOM= | 0.90 | TEST= 0
| INDE | 13 | 28 | 33 | FOBS= | 67.3 | SIGMA= | 2.5 | PHAS= | 94.4 | FOM= | 0.57 | TEST= 0
| INDE | 13 | 28 | 35 | FOBS= | 82.6 | SIGMA= | 2.2 | PHAS= | 136.0 | FOM= | 0.44 | TEST= 0
| INDE | 13 | 28 | 37 | FOBS= | 0.0 | SIGMA= | 19.9 | PHAS= | 0.0 | FOM= | 0.00 | TEST= 0
| INDE | 13 | 28 | 39 | FOBS= | 248.9 | SIGMA= | 0.8 | PHAS= | 18.1 | FOM= | 0.96 | TEST= 0
| INDE | 13 | 28 | 41 | FOBS= | 156.5 | SIGMA= | 1.2 | PHAS= | -168.7 | FOM= | 0.88 | TEST= 0
| INDE | 13 | 28 | 43 | FOBS= | 108.2 | SIGMA= | 1.6 | PHAS= | 158.5 | FOM= | 0.92 | TEST= 0
| INDE | 13 | 28 | 45 | FOBS= | 27.0 | SIGMA= | 6.4 | PHAS= | -79.3 | FOM= | 0.45 | TEST= 0
| INDE | 13 | 28 | 47 | FOBS= | 160.8 | SIGMA= | 1.1 | PHAS= | 53.5 | FOM= | 0.96 | TEST= 1
| INDE | 13 | 28 | 49 | FOBS= | 0.0 | SIGMA= | 18.5 | PHAS= | 0.0 | FOM= | 0.00 | TEST= 0
| INDE | 13 | 28 | 51 | FOBS= | 48.2 | SIGMA= | 3.6 | PHAS= | 10.0 | FOM= | 0.71 | TEST= 0
| INDE | 13 | 28 | 53 | FOBS= | 99.3 | SIGMA= | 1.8 | PHAS= | 64.2 | FOM= | 0.86 | TEST= 0
| INDE | 13 | 28 | 55 | FOBS= | 64.9 | SIGMA= | 2.6 | PHAS= | -109.7 | FOM= | 0.45 | TEST= 0
| INDE | 13 | 28 | 57 | FOBS= | 106.7 | SIGMA= | 1.9 | PHAS= | -121.0 | FOM= | 0.60 | TEST= 1
| INDE | 13 | 28 | 59 | FOBS= | 82.4 | SIGMA= | 2.6 | PHAS= | 128.8 | FOM= | 0.86 | TEST= 0
| INDE | 13 | 28 | 61 | FOBS= | 0.0 | SIGMA= | 23.6 | PHAS= | 0.0 | FOM= | 0.00 | TEST= 1
| INDE | 13 | 28 | 63 | FOBS= | 75.7 | SIGMA= | 4.6 | PHAS= | 8.2 | FOM= | 0.86 | TEST= 0
| INDE | 13 | 28 | 65 | FOBS= | 55.7 | SIGMA= | 3.9 | PHAS= | 94.5 | FOM= | 0.43 | TEST= 0
| INDE | 13 | 28 | 67 | FOBS= | 55.5 | SIGMA= | 3.9 | PHAS= | -135.5 | FOM= | 0.70 | TEST= 0
| INDE | 13 | 28 | 69 | FOBS= | 0.0 | SIGMA= | 31.7 | PHAS= | 0.0 | FOM= | 0.00 | TEST= 0
| INDE | 13 | 28 | 71 | FOBS= | 0.0 | SIGMA= | 32.4 | PHAS= | 0.0 | FOM= | 0.00 | TEST= 0
| INDE | 13 | 29 | 14 | FOBS= | 162.8 | SIGMA= | 0.6 | PHAS= | -176.4 | FOM= | 0.94 | TEST= 0
| INDE | 13 | 29 | 16 | FOBS= | 109.8 | SIGMA= | 0.9 | PHAS= | -114.4 | FOM= | 0.71 | TEST= 1
| INDE | 13 | 29 | 18 | FOBS= | 183.0 | SIGMA= | 0.7 | PHAS= | -51.4 | FOM= | 0.92 | TEST= 0
| INDE | 13 | 29 | 20 | FOBS= | 380.3 | SIGMA= | 0.5 | PHAS= | -21.4 | FOM= | 0.97 | TEST= 0
| INDE | 13 | 29 | 22 | FOBS= | 61.6 | SIGMA= | 1.7 | PHAS= | 59.3 | FOM= | 0.94 | TEST= 0
| INDE | 13 | 29 | 24 | FOBS= | 262.5 | SIGMA= | 0.6 | PHAS= | 37.9 | FOM= | 0.89 | TEST= 0
| INDE | 13 | 29 | 26 | FOBS= | 130.6 | SIGMA= | 1.1 | PHAS= | -87.0 | FOM= | 0.96 | TEST= 0
| INDE | 13 | 29 | 28 | FOBS= | 41.3 | SIGMA= | 3.4 | PHAS= | 109.3 | FOM= | 0.90 | TEST= 0
| INDE | 13 | 29 | 30 | FOBS= | 317.9 | SIGMA= | 0.9 | PHAS= | -84.9 | FOM= | 0.92 | TEST= 0
| INDE | 13 | 29 | 32 | FOBS= | 187.8 | SIGMA= | 1.1 | PHAS= | -72.6 | FOM= | 0.79 | TEST= 0
| INDE | 13 | 29 | 34 | FOBS= | 218.6 | SIGMA= | 0.9 | PHAS= | -141.3 | FOM= | 0.93 | TEST= 0
| INDE | 13 | 29 | 36 | FOBS= | 197.1 | SIGMA= | 1.0 | PHAS= | -105.0 | FOM= | 0.93 | TEST= 0
| INDE | 13 | 29 | 38 | FOBS= | 361.9 | SIGMA= | 1.1 | PHAS= | 1.5 | FOM= | 0.98 | TEST= 0
| INDE | 13 | 29 | 40 | FOBS= | 216.1 | SIGMA= | 0.9 | PHAS= | 40.6 | FOM= | 0.96 | TEST= 0
| INDE | 13 | 29 | 42 | FOBS= | 91.9 | SIGMA= | 2.0 | PHAS= | 113.2 | FOM= | 0.90 | TEST= 0
| INDE | 13 | 29 | 44 | FOBS= | 83.8 | SIGMA= | 2.0 | PHAS= | 132.6 | FOM= | 0.91 | TEST= 0
| INDE | 13 | 29 | 46 | FOBS= | 67.0 | SIGMA= | 2.9 | PHAS= | 11.5 | FOM= | 0.94 | TEST= 0
| INDE | 13 | 29 | 48 | FOBS= | 25.4 | SIGMA= | 7.5 | PHAS= | -65.8 | FOM= | 0.84 | TEST= 0
| INDE | 13 | 29 | 50 | FOBS= | 39.2 | SIGMA= | 4.5 | PHAS= | -70.1 | FOM= | 0.41 | TEST= 0
| INDE | 13 | 29 | 52 | FOBS= | 113.6 | SIGMA= | 1.5 | PHAS= | -69.7 | FOM= | 0.92 | TEST= 0
| INDE | 13 | 29 | 54 | FOBS= | 0.0 | SIGMA= | 18.3 | PHAS= | 0.0 | FOM= | 0.00 | TEST= 0
| INDE | 13 | 29 | 56 | FOBS= | 86.1 | SIGMA= | 2.2 | PHAS= | 153.4 | FOM= | 0.86 | TEST= 0

*FIG. 12A - 327*

```
INDE 13 29 58 FOBS=    0.0 SIGMA= 22.7 PHAS=    0.0 FOM= 0.00 TEST= 0
INDE 13 29 60 FOBS=   58.8 SIGMA=  3.6 PHAS=  179.9 FOM= 0.83 TEST= 0
INDE 13 29 62 FOBS=   39.8 SIGMA=  7.2 PHAS=  -99.8 FOM= 0.48 TEST= 1
INDE 13 29 64 FOBS=   54.8 SIGMA=  6.3 PHAS=  -88.8 FOM= 0.74 TEST= 0
INDE 13 29 66 FOBS=   96.6 SIGMA=  2.4 PHAS=  142.3 FOM= 0.88 TEST= 0
INDE 13 29 68 FOBS=   13.3 SIGMA= 16.4 PHAS=   85.1 FOM= 0.09 TEST= 0
INDE 13 29 70 FOBS=    0.0 SIGMA= 31.9 PHAS=    0.0 FOM= 0.00 TEST= 0
INDE 13 30 13 FOBS=   52.9 SIGMA=  1.5 PHAS= -122.5 FOM= 0.94 TEST= 0
INDE 13 30 15 FOBS=  218.3 SIGMA=  0.5 PHAS=  168.2 FOM= 0.96 TEST= 0
INDE 13 30 17 FOBS=  221.3 SIGMA=  0.5 PHAS=  157.0 FOM= 0.98 TEST= 0
INDE 13 30 19 FOBS=   91.6 SIGMA=  1.3 PHAS=  170.8 FOM= 0.90 TEST= 0
INDE 13 30 21 FOBS=   41.5 SIGMA=  2.9 PHAS= -157.7 FOM= 0.86 TEST= 0
INDE 13 30 23 FOBS=  295.3 SIGMA=  0.5 PHAS=  -80.2 FOM= 0.66 TEST= 1
INDE 13 30 25 FOBS=  137.9 SIGMA=  0.9 PHAS=  115.5 FOM= 0.92 TEST= 1
INDE 13 30 27 FOBS=  150.3 SIGMA=  1.0 PHAS= -158.2 FOM= 0.81 TEST= 0
INDE 13 30 29 FOBS=    0.0 SIGMA= 17.8 PHAS=    0.0 FOM= 0.00 TEST= 0
INDE 13 30 31 FOBS=  396.4 SIGMA=  1.0 PHAS=  147.1 FOM= 0.97 TEST= 0
INDE 13 30 33 FOBS=  145.2 SIGMA=  1.3 PHAS=  164.4 FOM= 0.94 TEST= 0
INDE 13 30 35 FOBS=  117.7 SIGMA=  1.7 PHAS=  101.0 FOM= 0.17 TEST= 1
INDE 13 30 37 FOBS=   47.3 SIGMA=  4.1 PHAS= -122.7 FOM= 0.80 TEST= 0
INDE 13 30 39 FOBS=  122.9 SIGMA=  1.6 PHAS=  -26.8 FOM= 0.84 TEST= 0
INDE 13 30 41 FOBS=  139.0 SIGMA=  1.4 PHAS=  -62.5 FOM= 0.86 TEST= 0
INDE 13 30 43 FOBS=   68.0 SIGMA=  2.7 PHAS=  -98.4 FOM= 0.92 TEST= 0
INDE 13 30 45 FOBS=   65.0 SIGMA=  3.0 PHAS=   -6.1 FOM= 0.58 TEST= 0
INDE 13 30 47 FOBS=   80.2 SIGMA=  2.4 PHAS=   44.3 FOM= 0.93 TEST= 0
INDE 13 30 49 FOBS=  128.3 SIGMA=  1.6 PHAS= -121.1 FOM= 0.92 TEST= 0
INDE 13 30 51 FOBS=   47.8 SIGMA=  4.0 PHAS=   10.9 FOM= 0.31 TEST= 1
INDE 13 30 53 FOBS=   90.0 SIGMA=  1.9 PHAS= -159.1 FOM= 0.84 TEST= 0
INDE 13 30 55 FOBS=   28.2 SIGMA=  5.9 PHAS=   95.9 FOM= 0.25 TEST= 0
INDE 13 30 57 FOBS=  103.8 SIGMA=  1.8 PHAS=  143.1 FOM= 0.82 TEST= 0
INDE 13 30 59 FOBS=   53.5 SIGMA=  3.4 PHAS=  115.1 FOM= 0.64 TEST= 0
INDE 13 30 61 FOBS=    0.0 SIGMA= 24.0 PHAS=    0.0 FOM= 0.00 TEST= 0
INDE 13 30 63 FOBS=   36.6 SIGMA=  7.9 PHAS=  -31.1 FOM= 0.58 TEST= 0
INDE 13 30 65 FOBS=   21.4 SIGMA= 23.2 PHAS=   32.6 FOM= 0.47 TEST= 0
INDE 13 30 67 FOBS=   57.3 SIGMA=  4.1 PHAS= -101.7 FOM= 0.08 TEST= 1
INDE 13 30 69 FOBS=    0.0 SIGMA= 21.3 PHAS=    0.0 FOM= 0.00 TEST= 0
INDE 13 31 14 FOBS=   55.6 SIGMA=  1.7 PHAS=  -50.6 FOM= 0.84 TEST= 0
INDE 13 31 16 FOBS=  231.2 SIGMA=  0.7 PHAS=   94.2 FOM= 0.99 TEST= 0
INDE 13 31 18 FOBS=   68.9 SIGMA=  1.8 PHAS=  -36.4 FOM= 0.90 TEST= 0
INDE 13 31 20 FOBS=  114.4 SIGMA=  1.1 PHAS=  -31.4 FOM= 0.96 TEST= 0
INDE 13 31 22 FOBS=  267.1 SIGMA=  0.7 PHAS=  156.8 FOM= 0.98 TEST= 0
INDE 13 31 24 FOBS=  169.1 SIGMA=  0.8 PHAS=   52.3 FOM= 0.93 TEST= 1
INDE 13 31 26 FOBS=  203.3 SIGMA=  0.8 PHAS= -154.8 FOM= 0.85 TEST= 0
INDE 13 31 28 FOBS=  145.4 SIGMA=  1.1 PHAS=  111.0 FOM= 0.86 TEST= 0
INDE 13 31 30 FOBS=   83.8 SIGMA=  1.8 PHAS=   31.1 FOM= 0.55 TEST= 0
INDE 13 31 32 FOBS=  184.9 SIGMA=  1.2 PHAS=   80.2 FOM= 0.95 TEST= 0
INDE 13 31 34 FOBS=  113.1 SIGMA=  1.8 PHAS=  -50.2 FOM= 0.96 TEST= 0
INDE 13 31 36 FOBS=  217.7 SIGMA=  1.0 PHAS= -142.2 FOM= 0.92 TEST= 1
INDE 13 31 38 FOBS=  280.0 SIGMA=  1.0 PHAS=    0.1 FOM= 0.95 TEST= 0
INDE 13 31 40 FOBS=    0.0 SIGMA= 20.9 PHAS=    0.0 FOM= 0.00 TEST= 0
INDE 13 31 42 FOBS=  145.3 SIGMA=  1.6 PHAS= -168.9 FOM= 0.86 TEST= 0
INDE 13 31 44 FOBS=    6.8 SIGMA= 33.7 PHAS=  122.7 FOM= 0.03 TEST= 0
INDE 13 31 46 FOBS=  126.6 SIGMA=  1.6 PHAS= -116.7 FOM= 0.80 TEST= 0
INDE 13 31 48 FOBS=   49.9 SIGMA=  3.8 PHAS=  126.2 FOM= 0.83 TEST= 0
INDE 13 31 50 FOBS=  151.7 SIGMA=  1.3 PHAS=   27.8 FOM= 0.93 TEST= 0
INDE 13 31 52 FOBS=  117.9 SIGMA=  1.7 PHAS=  -70.0 FOM= 0.91 TEST= 0
INDE 13 31 54 FOBS=   42.8 SIGMA=  4.6 PHAS=  -24.1 FOM= 0.74 TEST= 0
INDE 13 31 56 FOBS=   62.9 SIGMA=  3.0 PHAS=   88.3 FOM= 0.32 TEST= 1
INDE 13 31 58 FOBS=   41.1 SIGMA=  4.5 PHAS=  144.8 FOM= 0.59 TEST= 0
INDE 13 31 60 FOBS=   43.6 SIGMA=  4.5 PHAS= -166.8 FOM= 0.62 TEST= 0
INDE 13 31 62 FOBS=    0.0 SIGMA= 22.4 PHAS=    0.0 FOM= 0.00 TEST= 0
INDE 13 31 64 FOBS=   31.8 SIGMA=  8.0 PHAS= -123.8 FOM= 0.53 TEST= 0
INDE 13 31 66 FOBS=  116.3 SIGMA=  2.2 PHAS=  -91.1 FOM= 0.93 TEST= 0
INDE 13 31 68 FOBS=   62.3 SIGMA=  4.0 PHAS=  131.7 FOM= 0.81 TEST= 0
INDE 13 31 70 FOBS=   33.4 SIGMA=  7.0 PHAS=  163.2 FOM= 0.57 TEST= 0
INDE 13 32 13 FOBS=   83.4 SIGMA=  1.2 PHAS=  153.4 FOM= 0.99 TEST= 0
INDE 13 32 15 FOBS=   51.9 SIGMA=  2.2 PHAS=    8.9 FOM= 0.95 TEST= 0
INDE 13 32 17 FOBS=  225.0 SIGMA=  0.7 PHAS=   93.5 FOM= 0.95 TEST= 0
INDE 13 32 19 FOBS=  103.3 SIGMA=  1.2 PHAS= -176.2 FOM= 0.94 TEST= 0
INDE 13 32 21 FOBS=   38.1 SIGMA=  3.4 PHAS=   38.5 FOM= 0.95 TEST= 0
```

*FIG. 12A - 328*

```
INDE 13 32 23 FOBS=    11.8 SIGMA= 12.9 PHAS=  113.7 FOM= 0.05 TEST= 0
INDE 13 32 25 FOBS=   203.0 SIGMA=  0.8 PHAS=   79.7 FOM= 0.95 TEST= 0
INDE 13 32 27 FOBS=   196.6 SIGMA=  0.9 PHAS=  103.7 FOM= 0.96 TEST= 0
INDE 13 32 29 FOBS=   313.5 SIGMA=  0.7 PHAS=  -20.2 FOM= 0.96 TEST= 0
INDE 13 32 31 FOBS=   234.5 SIGMA=  0.8 PHAS=   94.5 FOM= 0.87 TEST= 0
INDE 13 32 33 FOBS=   370.5 SIGMA=  1.1 PHAS= -117.8 FOM= 0.99 TEST= 0
INDE 13 32 35 FOBS=   191.1 SIGMA=  1.1 PHAS=  141.2 FOM= 0.90 TEST= 0
INDE 13 32 37 FOBS=   102.0 SIGMA=  2.1 PHAS=   65.2 FOM= 0.92 TEST= 0
INDE 13 32 39 FOBS=    24.0 SIGMA=  9.6 PHAS= -150.0 FOM= 0.13 TEST= 0
INDE 13 32 41 FOBS=    79.4 SIGMA=  2.9 PHAS= -107.2 FOM= 0.71 TEST= 0
INDE 13 32 43 FOBS=   111.4 SIGMA=  2.1 PHAS=   16.6 FOM= 0.87 TEST= 0
INDE 13 32 45 FOBS=   123.7 SIGMA=  1.9 PHAS=  102.5 FOM= 0.93 TEST= 0
INDE 13 32 47 FOBS=    65.5 SIGMA=  3.0 PHAS=  -99.3 FOM= 0.72 TEST= 0
INDE 13 32 49 FOBS=    92.0 SIGMA=  2.1 PHAS=  -24.3 FOM= 0.92 TEST= 0
INDE 13 32 51 FOBS=    22.2 SIGMA=  8.5 PHAS=  -74.1 FOM= 0.56 TEST= 0
INDE 13 32 53 FOBS=   169.5 SIGMA=  1.2 PHAS= -103.5 FOM= 0.96 TEST= 0
INDE 13 32 55 FOBS=     0.0 SIGMA= 20.3 PHAS=    0.0 FOM= 0.00 TEST= 0
INDE 13 32 57 FOBS=   112.9 SIGMA=  1.8 PHAS=   76.8 FOM= 0.96 TEST= 0
INDE 13 32 59 FOBS=    64.7 SIGMA=  3.0 PHAS=   81.8 FOM= 0.89 TEST= 0
INDE 13 32 61 FOBS=     0.0 SIGMA= 23.7 PHAS=    0.0 FOM= 0.00 TEST= 0
INDE 13 32 63 FOBS=    17.9 SIGMA= 16.3 PHAS=  109.2 FOM= 0.22 TEST= 0
INDE 13 32 65 FOBS=    67.3 SIGMA=  4.6 PHAS=  141.4 FOM= 0.84 TEST= 0
INDE 13 32 67 FOBS=    19.3 SIGMA= 12.9 PHAS=  116.9 FOM= 0.61 TEST= 0
INDE 13 32 69 FOBS=    89.5 SIGMA=  2.9 PHAS=   98.0 FOM= 0.91 TEST= 0
INDE 13 33 14 FOBS=   279.7 SIGMA=  0.6 PHAS=  -21.7 FOM= 0.94 TEST= 0
INDE 13 33 16 FOBS=   206.9 SIGMA=  0.7 PHAS=  -66.0 FOM= 0.98 TEST= 0
INDE 13 33 18 FOBS=   239.6 SIGMA=  0.7 PHAS=    2.3 FOM= 0.88 TEST= 0
INDE 13 33 20 FOBS=   131.8 SIGMA=  1.1 PHAS=  115.0 FOM= 0.96 TEST= 0
INDE 13 33 22 FOBS=   162.7 SIGMA=  0.9 PHAS=   88.0 FOM= 0.94 TEST= 0
INDE 13 33 24 FOBS=   113.6 SIGMA=  1.3 PHAS=   42.3 FOM= 0.77 TEST= 0
INDE 13 33 26 FOBS=   140.6 SIGMA=  1.1 PHAS=  173.7 FOM= 0.90 TEST= 0
INDE 13 33 28 FOBS=   241.2 SIGMA=  0.8 PHAS=  -74.8 FOM= 0.96 TEST= 0
INDE 13 33 30 FOBS=   191.8 SIGMA=  0.9 PHAS= -155.6 FOM= 0.91 TEST= 0
INDE 13 33 32 FOBS=   145.4 SIGMA=  1.3 PHAS=  177.2 FOM= 0.91 TEST= 0
INDE 13 33 34 FOBS=   132.7 SIGMA=  1.6 PHAS= -145.5 FOM= 0.83 TEST= 0
INDE 13 33 36 FOBS=   145.5 SIGMA=  1.8 PHAS=   47.8 FOM= 0.96 TEST= 0
INDE 13 33 38 FOBS=   155.0 SIGMA=  1.6 PHAS=   17.3 FOM= 0.74 TEST= 0
INDE 13 33 40 FOBS=   102.4 SIGMA=  2.3 PHAS=  137.9 FOM= 0.78 TEST= 0
INDE 13 33 42 FOBS=    35.7 SIGMA=  7.5 PHAS=  -47.8 FOM= 0.79 TEST= 0
INDE 13 33 44 FOBS=   178.4 SIGMA=  1.4 PHAS=  -58.4 FOM= 0.94 TEST= 0
INDE 13 33 46 FOBS=    31.3 SIGMA=  8.8 PHAS= -155.5 FOM= 0.43 TEST= 0
INDE 13 33 48 FOBS=    88.8 SIGMA=  2.3 PHAS=   75.6 FOM= 0.86 TEST= 0
INDE 13 33 50 FOBS=    52.9 SIGMA=  3.6 PHAS=   37.5 FOM= 0.82 TEST= 0
INDE 13 33 52 FOBS=    53.7 SIGMA=  3.6 PHAS= -123.4 FOM= 0.86 TEST= 0
INDE 13 33 54 FOBS=    62.9 SIGMA=  3.1 PHAS=  141.6 FOM= 0.80 TEST= 0
INDE 13 33 56 FOBS=    82.1 SIGMA=  2.6 PHAS=   55.9 FOM= 0.67 TEST= 0
INDE 13 33 58 FOBS=    53.2 SIGMA=  3.9 PHAS=   -2.5 FOM= 0.89 TEST= 0
INDE 13 33 60 FOBS=    54.3 SIGMA=  3.8 PHAS= -166.4 FOM= 0.63 TEST= 0
INDE 13 33 62 FOBS=    35.7 SIGMA=  5.9 PHAS=   98.9 FOM= 0.26 TEST= 0
INDE 13 33 64 FOBS=    30.9 SIGMA=  7.4 PHAS=   67.2 FOM= 0.23 TEST= 0
INDE 13 33 66 FOBS=   103.5 SIGMA=  2.2 PHAS=    5.2 FOM= 0.95 TEST= 0
INDE 13 33 68 FOBS=    70.9 SIGMA=  3.7 PHAS=   36.2 FOM= 0.74 TEST= 0
INDE 13 34 13 FOBS=    79.6 SIGMA=  1.3 PHAS=  -81.2 FOM= 0.92 TEST= 0
INDE 13 34 15 FOBS=   246.2 SIGMA=  0.7 PHAS= -122.6 FOM= 0.95 TEST= 0
INDE 13 34 17 FOBS=   206.8 SIGMA=  0.7 PHAS= -167.7 FOM= 0.95 TEST= 1
INDE 13 34 19 FOBS=   118.9 SIGMA=  1.2 PHAS=   35.2 FOM= 0.94 TEST= 0
INDE 13 34 21 FOBS=   223.1 SIGMA=  0.8 PHAS=   -3.1 FOM= 0.93 TEST= 0
INDE 13 34 23 FOBS=   244.1 SIGMA=  0.7 PHAS=   80.4 FOM= 0.92 TEST= 0
INDE 13 34 25 FOBS=   268.5 SIGMA=  0.7 PHAS=   78.3 FOM= 0.96 TEST= 0
INDE 13 34 27 FOBS=   228.5 SIGMA=  0.8 PHAS=  174.9 FOM= 0.77 TEST= 1
INDE 13 34 29 FOBS=   118.5 SIGMA=  1.5 PHAS=   59.0 FOM= 0.82 TEST= 0
INDE 13 34 31 FOBS=   314.4 SIGMA=  0.8 PHAS=   76.4 FOM= 0.96 TEST= 0
INDE 13 34 33 FOBS=   222.1 SIGMA=  1.0 PHAS= -141.3 FOM= 0.81 TEST= 0
INDE 13 34 35 FOBS=   115.3 SIGMA=  2.0 PHAS=  133.3 FOM= 0.79 TEST= 0
INDE 13 34 37 FOBS=   116.8 SIGMA=  2.1 PHAS=  -28.6 FOM= 0.84 TEST= 0
INDE 13 34 39 FOBS=   123.5 SIGMA=  2.0 PHAS=   20.2 FOM= 0.71 TEST= 1
INDE 13 34 41 FOBS=   160.5 SIGMA=  1.5 PHAS= -109.6 FOM= 0.89 TEST= 0
INDE 13 34 43 FOBS=    91.7 SIGMA=  2.5 PHAS=  150.4 FOM= 0.81 TEST= 0
INDE 13 34 45 FOBS=    82.2 SIGMA=  2.8 PHAS=  -40.2 FOM= 0.24 TEST= 0
INDE 13 34 47 FOBS=    67.9 SIGMA=  3.3 PHAS=  -65.5 FOM= 0.86 TEST= 0
```

*FIG. 12A - 329*

```
INDE 13 34 49 FOBS=  57.9 SIGMA=  3.3 PHAS=   95.4 FOM= 0.63 TEST= 0
INDE 13 34 51 FOBS=   0.0 SIGMA= 19.4 PHAS=    0.0 FOM= 0.00 TEST= 0
INDE 13 34 53 FOBS=  25.0 SIGMA=  8.5 PHAS=  -69.5 FOM= 0.11 TEST= 1
INDE 13 34 55 FOBS=  77.9 SIGMA=  2.8 PHAS=  -44.7 FOM= 0.23 TEST= 1
INDE 13 34 57 FOBS=  94.4 SIGMA=  2.3 PHAS=  -15.4 FOM= 0.92 TEST= 0
INDE 13 34 59 FOBS=  45.9 SIGMA=  4.6 PHAS=  -71.9 FOM= 0.25 TEST= 0
INDE 13 34 61 FOBS=   0.0 SIGMA= 22.1 PHAS=    0.0 FOM= 0.00 TEST= 0
INDE 13 34 63 FOBS=   0.0 SIGMA= 21.3 PHAS=    0.0 FOM= 0.00 TEST= 0
INDE 13 34 65 FOBS=  58.1 SIGMA=  4.6 PHAS=  -74.5 FOM= 0.82 TEST= 0
INDE 13 34 67 FOBS=  59.2 SIGMA=  3.8 PHAS= -149.2 FOM= 0.02 TEST= 1
INDE 13 35 14 FOBS= 108.9 SIGMA=  1.2 PHAS=  108.4 FOM= 0.66 TEST= 0
INDE 13 35 16 FOBS= 259.3 SIGMA=  0.7 PHAS=  165.6 FOM= 0.98 TEST= 0
INDE 13 35 18 FOBS= 268.3 SIGMA=  0.7 PHAS=  -50.5 FOM= 0.97 TEST= 0
INDE 13 35 20 FOBS= 115.5 SIGMA=  1.3 PHAS= -122.6 FOM= 0.85 TEST= 0
INDE 13 35 22 FOBS= 110.1 SIGMA=  1.4 PHAS=   -4.2 FOM= 0.93 TEST= 0
INDE 13 35 24 FOBS= 199.5 SIGMA=  0.9 PHAS=  -20.2 FOM= 0.88 TEST= 0
INDE 13 35 26 FOBS= 112.4 SIGMA=  1.5 PHAS=   82.2 FOM= 0.86 TEST= 0
INDE 13 35 28 FOBS= 237.6 SIGMA=  0.9 PHAS=  -89.1 FOM= 0.96 TEST= 0
INDE 13 35 30 FOBS= 119.4 SIGMA=  2.0 PHAS=  -29.9 FOM= 0.56 TEST= 0
INDE 13 35 32 FOBS= 301.0 SIGMA=  0.8 PHAS=  171.5 FOM= 0.35 TEST= 1
INDE 13 35 34 FOBS= 184.1 SIGMA=  1.2 PHAS= -153.4 FOM= 0.91 TEST= 0
INDE 13 35 36 FOBS= 151.5 SIGMA=  1.4 PHAS=   32.0 FOM= 0.94 TEST= 0
INDE 13 35 38 FOBS= 207.0 SIGMA=  1.3 PHAS=  -88.5 FOM= 0.91 TEST= 0
INDE 13 35 40 FOBS=  88.3 SIGMA=  2.7 PHAS=  153.2 FOM= 0.77 TEST= 0
INDE 13 35 42 FOBS= 143.3 SIGMA=  1.7 PHAS=  111.1 FOM= 0.96 TEST= 0
INDE 13 35 44 FOBS=  37.6 SIGMA=  6.4 PHAS=  -71.1 FOM= 0.50 TEST= 0
INDE 13 35 46 FOBS=  59.9 SIGMA=  3.7 PHAS=  -52.8 FOM= 0.23 TEST= 1
INDE 13 35 48 FOBS=   0.0 SIGMA= 20.7 PHAS=    0.0 FOM= 0.00 TEST= 0
INDE 13 35 50 FOBS= 119.5 SIGMA=  1.9 PHAS=   70.0 FOM= 0.86 TEST= 1
INDE 13 35 52 FOBS=   0.0 SIGMA= 21.6 PHAS=    0.0 FOM= 0.00 TEST= 0
INDE 13 35 54 FOBS=   0.0 SIGMA= 21.8 PHAS=    0.0 FOM= 0.00 TEST= 0
INDE 13 35 56 FOBS=  84.2 SIGMA=  2.6 PHAS= -137.1 FOM= 0.90 TEST= 0
INDE 13 35 58 FOBS=  84.5 SIGMA=  2.5 PHAS= -174.3 FOM= 0.87 TEST= 0
INDE 13 35 60 FOBS=  21.5 SIGMA= 10.6 PHAS=  101.4 FOM= 0.14 TEST= 0
INDE 13 35 62 FOBS=   0.0 SIGMA= 21.4 PHAS=    0.0 FOM= 0.00 TEST= 0
INDE 13 35 64 FOBS=   0.0 SIGMA= 20.6 PHAS=    0.0 FOM= 0.00 TEST= 1
INDE 13 35 66 FOBS=  48.2 SIGMA=  4.7 PHAS=  165.3 FOM= 0.79 TEST= 0
INDE 13 35 68 FOBS=  68.5 SIGMA=  3.4 PHAS=  179.3 FOM= 0.33 TEST= 1
INDE 13 36 13 FOBS= 223.3 SIGMA=  0.7 PHAS=   -0.9 FOM= 0.95 TEST= 0
INDE 13 36 15 FOBS= 179.4 SIGMA=  0.9 PHAS=   75.5 FOM= 0.93 TEST= 0
INDE 13 36 17 FOBS= 206.1 SIGMA=  0.8 PHAS=  162.8 FOM= 0.85 TEST= 0
INDE 13 36 19 FOBS= 129.8 SIGMA=  1.3 PHAS=  178.6 FOM= 0.85 TEST= 0
INDE 13 36 21 FOBS= 255.9 SIGMA=  0.8 PHAS= -108.6 FOM= 0.98 TEST= 0
INDE 13 36 23 FOBS= 157.2 SIGMA=  1.3 PHAS=    0.1 FOM= 0.87 TEST= 0
INDE 13 36 25 FOBS=   0.0 SIGMA= 19.6 PHAS=    0.0 FOM= 0.00 TEST= 0
INDE 13 36 27 FOBS=  88.4 SIGMA=  2.2 PHAS=   95.6 FOM= 0.72 TEST= 0
INDE 13 36 29 FOBS= 190.1 SIGMA=  1.2 PHAS=  159.6 FOM= 0.93 TEST= 0
INDE 13 36 31 FOBS= 282.0 SIGMA=  1.0 PHAS=   83.1 FOM= 0.95 TEST= 0
INDE 13 36 33 FOBS= 126.8 SIGMA=  1.7 PHAS=  -71.5 FOM= 0.32 TEST= 0
INDE 13 36 35 FOBS= 184.7 SIGMA=  1.2 PHAS=  162.2 FOM= 0.96 TEST= 0
INDE 13 36 37 FOBS= 187.7 SIGMA=  1.1 PHAS= -109.5 FOM= 0.70 TEST= 1
INDE 13 36 39 FOBS=   0.0 SIGMA= 22.5 PHAS=    0.0 FOM= 0.00 TEST= 0
INDE 13 36 41 FOBS=  96.0 SIGMA=  2.5 PHAS=   29.8 FOM= 0.88 TEST= 0
INDE 13 36 43 FOBS= 104.6 SIGMA=  2.2 PHAS=   30.9 FOM= 0.46 TEST= 0
INDE 13 36 45 FOBS=  44.0 SIGMA=  5.1 PHAS=   75.0 FOM= 0.61 TEST= 0
INDE 13 36 47 FOBS=  21.1 SIGMA= 11.5 PHAS=  113.5 FOM= 0.39 TEST= 0
INDE 13 36 49 FOBS=   0.0 SIGMA= 22.1 PHAS=    0.0 FOM= 0.00 TEST= 0
INDE 13 36 51 FOBS=  35.4 SIGMA=  6.5 PHAS=  -39.1 FOM= 0.61 TEST= 0
INDE 13 36 53 FOBS=  54.5 SIGMA=  3.9 PHAS= -119.4 FOM= 0.40 TEST= 0
INDE 13 36 55 FOBS=   0.0 SIGMA= 20.5 PHAS=    0.0 FOM= 0.00 TEST= 0
INDE 13 36 57 FOBS= 141.0 SIGMA=  1.6 PHAS=   77.7 FOM= 0.96 TEST= 0
INDE 13 36 59 FOBS=   0.0 SIGMA= 21.4 PHAS=    0.0 FOM= 0.00 TEST= 0
INDE 13 36 61 FOBS=  33.9 SIGMA=  6.1 PHAS=   92.2 FOM= 0.50 TEST= 0
INDE 13 36 63 FOBS=   0.0 SIGMA= 20.5 PHAS=    0.0 FOM= 0.00 TEST= 1
INDE 13 36 65 FOBS=  62.2 SIGMA=  5.2 PHAS=   81.6 FOM= 0.83 TEST= 0
INDE 13 36 67 FOBS=  93.1 SIGMA=  2.5 PHAS=   86.3 FOM= 0.94 TEST= 0
INDE 13 37 14 FOBS= 154.7 SIGMA=  1.1 PHAS= -131.5 FOM= 0.95 TEST= 0
INDE 13 37 16 FOBS=  58.6 SIGMA=  2.7 PHAS= -103.6 FOM= 0.93 TEST= 0
INDE 13 37 18 FOBS= 119.9 SIGMA=  1.6 PHAS=  -89.1 FOM= 0.84 TEST= 0
INDE 13 37 20 FOBS= 122.6 SIGMA=  1.5 PHAS=  172.6 FOM= 0.96 TEST= 0
```

*FIG. 12A - 330*

```
INDE 13 37 22 FOBS=   67.2 SIGMA=  2.8 PHAS=  150.6 FOM= 0.57 TEST= 0
INDE 13 37 24 FOBS=  209.2 SIGMA=  1.1 PHAS= -152.0 FOM= 0.96 TEST= 0
INDE 13 37 26 FOBS=  103.4 SIGMA=  2.1 PHAS=  118.2 FOM= 0.82 TEST= 0
INDE 13 37 28 FOBS=  163.2 SIGMA=  1.3 PHAS= -170.7 FOM= 0.93 TEST= 0
INDE 13 37 30 FOBS=  210.3 SIGMA=  1.3 PHAS=  -12.8 FOM= 0.95 TEST= 0
INDE 13 37 32 FOBS=  165.9 SIGMA=  1.5 PHAS=  -96.6 FOM= 0.90 TEST= 0
INDE 13 37 34 FOBS=   59.8 SIGMA=  3.5 PHAS=  -86.4 FOM= 0.19 TEST= 1
INDE 13 37 36 FOBS=   88.6 SIGMA=  2.3 PHAS=   53.3 FOM= 0.42 TEST= 0
INDE 13 37 38 FOBS=   64.1 SIGMA=  3.0 PHAS=   93.5 FOM= 0.84 TEST= 0
INDE 13 37 40 FOBS=   37.2 SIGMA=  6.3 PHAS=    7.3 FOM= 0.75 TEST= 0
INDE 13 37 42 FOBS=   77.2 SIGMA=  3.0 PHAS=  -88.3 FOM= 0.80 TEST= 0
INDE 13 37 44 FOBS=  102.6 SIGMA=  2.3 PHAS=   63.7 FOM= 0.48 TEST= 1
INDE 13 37 46 FOBS=   46.3 SIGMA=  4.8 PHAS=   44.8 FOM= 0.37 TEST= 0
INDE 13 37 48 FOBS=   53.0 SIGMA=  4.2 PHAS=   59.3 FOM= 0.30 TEST= 0
INDE 13 37 50 FOBS=    0.0 SIGMA= 22.6 PHAS=    0.0 FOM= 0.00 TEST= 0
INDE 13 37 52 FOBS=   18.5 SIGMA= 13.0 PHAS=  -10.6 FOM= 0.08 TEST= 0
INDE 13 37 54 FOBS=    0.0 SIGMA= 21.6 PHAS=    0.0 FOM= 0.00 TEST= 0
INDE 13 37 56 FOBS=   59.6 SIGMA=  3.6 PHAS=  -58.1 FOM= 0.39 TEST= 0
INDE 13 37 58 FOBS=   48.5 SIGMA=  4.9 PHAS=  -16.5 FOM= 0.21 TEST= 1
INDE 13 37 60 FOBS=   55.7 SIGMA=  3.8 PHAS=  -29.0 FOM= 0.84 TEST= 0
INDE 13 37 62 FOBS=   51.7 SIGMA=  4.1 PHAS=   18.8 FOM= 0.39 TEST= 0
INDE 13 37 64 FOBS=    7.6 SIGMA= 34.3 PHAS=   61.3 FOM= 0.12 TEST= 0
INDE 13 37 66 FOBS=   49.5 SIGMA=  4.8 PHAS=  -20.4 FOM= 0.65 TEST= 0
INDE 13 38 13 FOBS=   51.1 SIGMA=  2.6 PHAS=  102.0 FOM= 0.83 TEST= 0
INDE 13 38 15 FOBS=   94.6 SIGMA=  1.8 PHAS=   93.4 FOM= 0.95 TEST= 0
INDE 13 38 17 FOBS=  177.4 SIGMA=  1.1 PHAS=  143.7 FOM= 0.94 TEST= 0
INDE 13 38 19 FOBS=  193.6 SIGMA=  1.1 PHAS=   90.1 FOM= 0.94 TEST= 1
INDE 13 38 21 FOBS=  262.3 SIGMA=  0.9 PHAS=  -77.6 FOM= 0.96 TEST= 0
INDE 13 38 23 FOBS=  157.7 SIGMA=  1.3 PHAS=   81.1 FOM= 0.95 TEST= 0
INDE 13 38 25 FOBS=  244.6 SIGMA=  1.0 PHAS=   59.5 FOM= 0.96 TEST= 0
INDE 13 38 27 FOBS=  116.1 SIGMA=  1.9 PHAS=   58.9 FOM= 0.89 TEST= 0
INDE 13 38 29 FOBS=  270.9 SIGMA=  0.9 PHAS= -174.8 FOM= 0.97 TEST= 0
INDE 13 38 31 FOBS=  175.5 SIGMA=  1.4 PHAS= -169.5 FOM= 0.90 TEST= 0
INDE 13 38 33 FOBS=  147.9 SIGMA=  1.4 PHAS= -136.8 FOM= 0.92 TEST= 0
INDE 13 38 35 FOBS=    0.0 SIGMA= 19.8 PHAS=    0.0 FOM= 0.00 TEST= 0
INDE 13 38 37 FOBS=   38.4 SIGMA=  6.3 PHAS=   81.0 FOM= 0.18 TEST= 0
INDE 13 38 39 FOBS=   98.4 SIGMA=  2.0 PHAS=  -41.7 FOM= 0.96 TEST= 0
INDE 13 38 41 FOBS=   42.7 SIGMA=  6.0 PHAS=  -10.7 FOM= 0.58 TEST= 0
INDE 13 38 43 FOBS=  102.7 SIGMA=  2.3 PHAS=  -44.2 FOM= 0.93 TEST= 0
INDE 13 38 45 FOBS=   19.4 SIGMA= 14.4 PHAS=   75.7 FOM= 0.08 TEST= 0
INDE 13 38 47 FOBS=    0.0 SIGMA= 21.9 PHAS=    0.0 FOM= 0.00 TEST= 0
INDE 13 38 49 FOBS=   18.2 SIGMA= 11.9 PHAS=   74.7 FOM= 0.18 TEST= 0
INDE 13 38 51 FOBS=    0.0 SIGMA= 22.6 PHAS=    0.0 FOM= 0.00 TEST= 0
INDE 13 38 53 FOBS=   30.3 SIGMA=  7.1 PHAS=  -68.1 FOM= 0.52 TEST= 0
INDE 13 38 55 FOBS=   33.6 SIGMA=  6.8 PHAS=  -30.3 FOM= 0.43 TEST= 0
INDE 13 38 57 FOBS=    0.0 SIGMA= 20.4 PHAS=    0.0 FOM= 0.00 TEST= 0
INDE 13 38 59 FOBS=   76.9 SIGMA=  2.8 PHAS= -109.6 FOM= 0.89 TEST= 0
INDE 13 38 61 FOBS=   55.9 SIGMA=  3.8 PHAS=  -28.3 FOM= 0.05 TEST= 1
INDE 13 38 63 FOBS=   94.6 SIGMA=  2.4 PHAS=  155.6 FOM= 0.80 TEST= 0
INDE 13 38 65 FOBS=   40.2 SIGMA=  7.9 PHAS=   63.9 FOM= 0.01 TEST= 1
INDE 13 39 14 FOBS=   97.6 SIGMA=  1.7 PHAS=  -95.5 FOM= 0.71 TEST= 0
INDE 13 39 16 FOBS=    0.0 SIGMA= 18.5 PHAS=    0.0 FOM= 0.00 TEST= 0
INDE 13 39 18 FOBS=  172.5 SIGMA=  1.2 PHAS=   51.5 FOM= 0.96 TEST= 0
INDE 13 39 20 FOBS=  175.3 SIGMA=  1.2 PHAS= -143.4 FOM= 0.96 TEST= 0
INDE 13 39 22 FOBS=  137.0 SIGMA=  1.5 PHAS=   87.0 FOM= 0.85 TEST= 0
INDE 13 39 24 FOBS=  154.0 SIGMA=  1.5 PHAS=  -41.7 FOM= 0.93 TEST= 0
INDE 13 39 26 FOBS=  137.1 SIGMA=  1.7 PHAS=  -77.3 FOM= 0.88 TEST= 0
INDE 13 39 28 FOBS=  119.1 SIGMA=  1.9 PHAS=  134.3 FOM= 0.95 TEST= 0
INDE 13 39 30 FOBS=  104.6 SIGMA=  1.9 PHAS=   86.8 FOM= 0.86 TEST= 0
INDE 13 39 32 FOBS=  173.9 SIGMA=  1.5 PHAS=  107.0 FOM= 0.95 TEST= 0
INDE 13 39 34 FOBS=    0.0 SIGMA= 20.8 PHAS=    0.0 FOM= 0.00 TEST= 0
INDE 13 39 36 FOBS=  199.7 SIGMA=  1.1 PHAS=  -46.1 FOM= 0.94 TEST= 0
INDE 13 39 38 FOBS=    0.0 SIGMA= 19.6 PHAS=    0.0 FOM= 0.00 TEST= 0
INDE 13 39 40 FOBS=   60.4 SIGMA=  3.2 PHAS=  -70.4 FOM= 0.82 TEST= 0
INDE 13 39 42 FOBS=  136.6 SIGMA=  1.8 PHAS=  -96.6 FOM= 0.95 TEST= 0
INDE 13 39 44 FOBS=   78.7 SIGMA=  2.9 PHAS=  -38.7 FOM= 0.89 TEST= 0
INDE 13 39 46 FOBS=   17.8 SIGMA= 13.6 PHAS=   95.0 FOM= 0.19 TEST= 0
INDE 13 39 48 FOBS=  119.6 SIGMA=  1.9 PHAS=   55.2 FOM= 0.72 TEST= 0
INDE 13 39 50 FOBS=  112.4 SIGMA=  2.0 PHAS=  -42.6 FOM= 0.94 TEST= 0
INDE 13 39 52 FOBS=   55.5 SIGMA=  3.9 PHAS=  136.2 FOM= 0.81 TEST= 0
```

*FIG. 12A - 331*

```
INDE 13 39 54 FOBS=  102.3 SIGMA=  2.2 PHAS=  152.7 FOM= 0.78 TEST= 0
INDE 13 39 56 FOBS=   29.9 SIGMA=  7.7 PHAS= -113.5 FOM= 0.08 TEST= 1
INDE 13 39 58 FOBS=   34.6 SIGMA=  7.7 PHAS= -138.2 FOM= 0.07 TEST= 0
INDE 13 39 60 FOBS=   60.8 SIGMA=  3.5 PHAS=   51.6 FOM= 0.77 TEST= 0
INDE 13 39 62 FOBS=   33.2 SIGMA=  6.4 PHAS=   82.8 FOM= 0.37 TEST= 0
INDE 13 39 64 FOBS=   80.8 SIGMA=  3.4 PHAS=   38.5 FOM= 0.92 TEST= 0
INDE 13 39 66 FOBS=   24.0 SIGMA= 17.1 PHAS= -165.5 FOM= 0.60 TEST= 0
INDE 13 40 13 FOBS=  205.6 SIGMA=  0.8 PHAS=  -53.7 FOM= 0.90 TEST= 0
INDE 13 40 15 FOBS=  115.5 SIGMA=  1.6 PHAS= -172.4 FOM= 0.74 TEST= 1
INDE 13 40 17 FOBS=  115.5 SIGMA=  1.7 PHAS=  108.6 FOM= 0.81 TEST= 0
INDE 13 40 19 FOBS=  174.0 SIGMA=  1.3 PHAS=   55.8 FOM= 0.85 TEST= 0
INDE 13 40 21 FOBS=  166.9 SIGMA=  1.3 PHAS=  -12.3 FOM= 0.45 TEST= 0
INDE 13 40 23 FOBS=  130.9 SIGMA=  1.7 PHAS=  -79.7 FOM= 0.84 TEST= 0
INDE 13 40 25 FOBS=   79.4 SIGMA=  2.8 PHAS=   67.2 FOM= 0.80 TEST= 0
INDE 13 40 27 FOBS=  110.9 SIGMA=  2.0 PHAS= -168.8 FOM= 0.80 TEST= 0
INDE 13 40 29 FOBS=   72.9 SIGMA=  3.0 PHAS=   59.4 FOM= 0.77 TEST= 0
INDE 13 40 31 FOBS=  131.6 SIGMA=  1.5 PHAS=  -40.0 FOM= 0.81 TEST= 0
INDE 13 40 33 FOBS=  138.3 SIGMA=  1.9 PHAS=  -99.6 FOM= 0.97 TEST= 0
INDE 13 40 35 FOBS=   79.7 SIGMA=  2.5 PHAS=  -86.8 FOM= 0.86 TEST= 0
INDE 13 40 37 FOBS=   91.4 SIGMA=  2.2 PHAS= -126.9 FOM= 0.96 TEST= 0
INDE 13 40 39 FOBS=   50.6 SIGMA=  4.0 PHAS=  117.9 FOM= 0.64 TEST= 0
INDE 13 40 41 FOBS=   89.0 SIGMA=  2.2 PHAS= -123.6 FOM= 0.82 TEST= 0
INDE 13 40 43 FOBS=  141.4 SIGMA=  1.7 PHAS= -115.1 FOM= 0.97 TEST= 0
INDE 13 40 45 FOBS=   60.6 SIGMA=  3.7 PHAS=  143.4 FOM= 0.84 TEST= 0
INDE 13 40 47 FOBS=   47.4 SIGMA=  4.7 PHAS=   66.5 FOM= 0.63 TEST= 0
INDE 13 40 49 FOBS=   83.8 SIGMA=  2.7 PHAS= -133.5 FOM= 0.87 TEST= 0
INDE 13 40 51 FOBS=  128.1 SIGMA=  1.8 PHAS=  -58.8 FOM= 0.94 TEST= 0
INDE 13 40 53 FOBS=   96.9 SIGMA=  2.3 PHAS=   57.4 FOM= 0.93 TEST= 0
INDE 13 40 55 FOBS=   53.3 SIGMA=  4.0 PHAS=   50.8 FOM= 0.70 TEST= 0
INDE 13 40 57 FOBS=   40.9 SIGMA=  5.2 PHAS= -144.1 FOM= 0.45 TEST= 0
INDE 13 40 59 FOBS=   71.4 SIGMA=  3.1 PHAS=  153.6 FOM= 0.11 TEST= 1
INDE 13 40 61 FOBS=  104.2 SIGMA=  2.1 PHAS=  -31.7 FOM= 0.39 TEST= 1
INDE 13 40 63 FOBS=   65.9 SIGMA=  4.1 PHAS=  137.0 FOM= 0.77 TEST= 0
INDE 13 40 65 FOBS=   79.4 SIGMA=  3.6 PHAS=   80.7 FOM= 0.92 TEST= 0
INDE 13 41 14 FOBS=   50.0 SIGMA=  3.6 PHAS=   56.7 FOM= 0.43 TEST= 0
INDE 13 41 16 FOBS=   47.5 SIGMA=  4.0 PHAS=   46.7 FOM= 0.30 TEST= 0
INDE 13 41 18 FOBS=    0.0 SIGMA= 19.8 PHAS=    0.0 FOM= 0.00 TEST= 1
INDE 13 41 20 FOBS=  172.3 SIGMA=  1.3 PHAS=  -63.5 FOM= 0.94 TEST= 0
INDE 13 41 22 FOBS=  195.6 SIGMA=  1.2 PHAS=   51.0 FOM= 0.93 TEST= 0
INDE 13 41 24 FOBS=   13.8 SIGMA= 15.6 PHAS=   75.8 FOM= 0.09 TEST= 0
INDE 13 41 26 FOBS=   67.8 SIGMA=  3.3 PHAS=   43.3 FOM= 0.93 TEST= 0
INDE 13 41 28 FOBS=  129.7 SIGMA=  1.7 PHAS=   14.6 FOM= 0.95 TEST= 0
INDE 13 41 30 FOBS=  253.1 SIGMA=  0.9 PHAS= -147.5 FOM= 0.94 TEST= 0
INDE 13 41 32 FOBS=  209.9 SIGMA=  1.0 PHAS=   99.6 FOM= 0.95 TEST= 0
INDE 13 41 34 FOBS=   85.1 SIGMA=  2.7 PHAS=  -60.4 FOM= 0.93 TEST= 0
INDE 13 41 36 FOBS=   25.6 SIGMA=  7.6 PHAS= -177.9 FOM= 0.70 TEST= 0
INDE 13 41 38 FOBS=   57.7 SIGMA=  3.4 PHAS= -131.4 FOM= 0.64 TEST= 0
INDE 13 41 40 FOBS=   19.3 SIGMA=  9.9 PHAS= -122.3 FOM= 0.14 TEST= 0
INDE 13 41 42 FOBS=  147.7 SIGMA=  1.4 PHAS=  143.4 FOM= 0.97 TEST= 0
INDE 13 41 44 FOBS=    0.0 SIGMA= 21.2 PHAS=    0.0 FOM= 0.00 TEST= 0
INDE 13 41 46 FOBS=   38.3 SIGMA=  6.3 PHAS=   45.5 FOM= 0.80 TEST= 0
INDE 13 41 48 FOBS=   46.0 SIGMA=  4.8 PHAS=  111.3 FOM= 0.82 TEST= 0
INDE 13 41 50 FOBS=   49.5 SIGMA=  4.5 PHAS= -118.6 FOM= 0.56 TEST= 0
INDE 13 41 52 FOBS=  114.8 SIGMA=  2.0 PHAS= -114.6 FOM= 0.97 TEST= 0
INDE 13 41 54 FOBS=   66.3 SIGMA=  3.3 PHAS=  -19.6 FOM= 0.86 TEST= 0
INDE 13 41 56 FOBS=   47.0 SIGMA=  4.6 PHAS=  -85.6 FOM= 0.61 TEST= 0
INDE 13 41 58 FOBS=   20.4 SIGMA= 11.4 PHAS=   86.6 FOM= 0.50 TEST= 0
INDE 13 41 60 FOBS=   14.9 SIGMA= 17.8 PHAS=  -54.9 FOM= 0.47 TEST= 0
INDE 13 41 62 FOBS=   23.9 SIGMA= 11.3 PHAS= -134.0 FOM= 0.24 TEST= 0
INDE 13 41 64 FOBS=  111.4 SIGMA=  2.6 PHAS=   33.4 FOM= 0.95 TEST= 0
INDE 13 42 13 FOBS=  177.5 SIGMA=  1.5 PHAS=  -20.4 FOM= 0.94 TEST= 0
INDE 13 42 15 FOBS=  129.1 SIGMA=  1.6 PHAS=  -79.5 FOM= 0.78 TEST= 0
INDE 13 42 17 FOBS=  185.2 SIGMA=  1.2 PHAS=   56.3 FOM= 0.93 TEST= 0
INDE 13 42 19 FOBS=  154.2 SIGMA=  1.5 PHAS= -106.4 FOM= 0.90 TEST= 0
INDE 13 42 21 FOBS=   94.3 SIGMA=  2.3 PHAS=  -97.0 FOM= 0.66 TEST= 0
INDE 13 42 23 FOBS=  159.7 SIGMA=  1.4 PHAS=  -58.7 FOM= 0.87 TEST= 0
INDE 13 42 25 FOBS=  104.4 SIGMA=  2.2 PHAS=  127.1 FOM= 0.97 TEST= 0
INDE 13 42 27 FOBS=  282.1 SIGMA=  0.9 PHAS= -137.5 FOM= 0.97 TEST= 0
INDE 13 42 29 FOBS=  126.4 SIGMA=  1.7 PHAS=  151.5 FOM= 0.89 TEST= 0
INDE 13 42 31 FOBS=   64.2 SIGMA=  3.0 PHAS= -115.5 FOM= 0.55 TEST= 0
```

*FIG. 12A - 332*

```
INDE 13 42 33 FOBS=   173.9 SIGMA=  1.2 PHAS=  -93.0 FOM= 0.89 TEST= 0
INDE 13 42 35 FOBS=   134.7 SIGMA=  1.6 PHAS= -169.8 FOM= 0.90 TEST= 0
INDE 13 42 37 FOBS=    40.9 SIGMA=  5.5 PHAS=   -7.9 FOM= 0.31 TEST= 0
INDE 13 42 39 FOBS=   117.0 SIGMA=  1.7 PHAS=  140.9 FOM= 0.91 TEST= 0
INDE 13 42 41 FOBS=     0.0 SIGMA= 20.4 PHAS=    0.0 FOM= 0.00 TEST= 0
INDE 13 42 43 FOBS=     0.0 SIGMA= 20.4 PHAS=    0.0 FOM= 0.00 TEST= 0
INDE 13 42 45 FOBS=    17.2 SIGMA= 14.2 PHAS= -125.9 FOM= 0.18 TEST= 1
INDE 13 42 47 FOBS=     0.0 SIGMA= 21.0 PHAS=    0.0 FOM= 0.00 TEST= 0
INDE 13 42 49 FOBS=    35.2 SIGMA=  6.9 PHAS=  -32.9 FOM= 0.54 TEST= 0
INDE 13 42 51 FOBS=    20.6 SIGMA= 11.7 PHAS= -124.5 FOM= 0.30 TEST= 0
INDE 13 42 53 FOBS=    22.6 SIGMA= 10.4 PHAS= -179.0 FOM= 0.46 TEST= 0
INDE 13 42 55 FOBS=    53.7 SIGMA=  4.1 PHAS=   89.2 FOM= 0.38 TEST= 0
INDE 13 42 57 FOBS=     0.0 SIGMA= 21.8 PHAS=    0.0 FOM= 0.00 TEST= 0
INDE 13 42 59 FOBS=    54.3 SIGMA=  4.1 PHAS= -123.0 FOM= 0.61 TEST= 0
INDE 13 42 61 FOBS=    20.2 SIGMA= 10.2 PHAS=  -71.4 FOM= 0.56 TEST= 0
INDE 13 42 63 FOBS=    52.2 SIGMA=  5.4 PHAS= -135.6 FOM= 0.72 TEST= 0
INDE 13 43 14 FOBS=     0.0 SIGMA= 21.1 PHAS=    0.0 FOM= 0.00 TEST= 1
INDE 13 43 16 FOBS=    72.0 SIGMA=  2.9 PHAS=  -96.1 FOM= 0.84 TEST= 0
INDE 13 43 18 FOBS=   224.7 SIGMA=  1.1 PHAS= -134.9 FOM= 0.93 TEST= 0
INDE 13 43 20 FOBS=   227.3 SIGMA=  1.2 PHAS=  163.3 FOM= 0.92 TEST= 0
INDE 13 43 22 FOBS=   148.0 SIGMA=  1.5 PHAS=   42.0 FOM= 0.83 TEST= 0
INDE 13 43 24 FOBS=   163.2 SIGMA=  1.4 PHAS=   64.7 FOM= 0.92 TEST= 0
INDE 13 43 26 FOBS=   227.2 SIGMA=  1.1 PHAS=  133.0 FOM= 0.97 TEST= 0
INDE 13 43 28 FOBS=    93.0 SIGMA=  2.3 PHAS=   65.5 FOM= 0.81 TEST= 0
INDE 13 43 30 FOBS=   156.5 SIGMA=  1.4 PHAS=  138.3 FOM= 0.97 TEST= 0
INDE 13 43 32 FOBS=   152.1 SIGMA=  1.3 PHAS=  138.2 FOM= 0.82 TEST= 0
INDE 13 43 34 FOBS=    55.4 SIGMA=  3.4 PHAS=  108.5 FOM= 0.72 TEST= 0
INDE 13 43 36 FOBS=   114.5 SIGMA=  1.8 PHAS=  132.6 FOM= 0.49 TEST= 0
INDE 13 43 38 FOBS=   144.6 SIGMA=  1.4 PHAS= -149.6 FOM= 0.86 TEST= 0
INDE 13 43 40 FOBS=    39.0 SIGMA=  4.9 PHAS=   15.7 FOM= 0.52 TEST= 0
INDE 13 43 42 FOBS=    31.6 SIGMA=  6.3 PHAS=  -11.8 FOM= 0.38 TEST= 0
INDE 13 43 44 FOBS=     0.0 SIGMA= 21.2 PHAS=    0.0 FOM= 0.00 TEST= 0
INDE 13 43 46 FOBS=    37.6 SIGMA=  6.6 PHAS=   89.5 FOM= 0.47 TEST= 0
INDE 13 43 48 FOBS=    73.1 SIGMA=  3.1 PHAS= -116.2 FOM= 0.74 TEST= 0
INDE 13 43 50 FOBS=     0.0 SIGMA= 20.8 PHAS=    0.0 FOM= 0.00 TEST= 0
INDE 13 43 52 FOBS=    85.1 SIGMA=  2.7 PHAS= -146.6 FOM= 0.78 TEST= 0
INDE 13 43 54 FOBS=   112.2 SIGMA=  2.0 PHAS=  -38.1 FOM= 0.95 TEST= 0
INDE 13 43 56 FOBS=    54.3 SIGMA=  4.0 PHAS=   32.1 FOM= 0.80 TEST= 0
INDE 13 43 58 FOBS=    47.4 SIGMA=  4.6 PHAS=  165.2 FOM= 0.41 TEST= 0
INDE 13 43 60 FOBS=     0.0 SIGMA= 20.9 PHAS=    0.0 FOM= 0.00 TEST= 0
INDE 13 43 62 FOBS=     0.0 SIGMA= 23.2 PHAS=    0.0 FOM= 0.00 TEST= 0
INDE 13 44 13 FOBS=   214.6 SIGMA=  1.6 PHAS=  -24.2 FOM= 0.97 TEST= 0
INDE 13 44 15 FOBS=    99.0 SIGMA=  2.1 PHAS= -176.4 FOM= 0.87 TEST= 0
INDE 13 44 17 FOBS=   192.8 SIGMA=  1.2 PHAS=   99.5 FOM= 0.95 TEST= 0
INDE 13 44 19 FOBS=   257.4 SIGMA=  1.1 PHAS=  161.5 FOM= 0.94 TEST= 0
INDE 13 44 21 FOBS=   161.4 SIGMA=  1.4 PHAS=   50.1 FOM= 0.95 TEST= 0
INDE 13 44 23 FOBS=   243.8 SIGMA=  1.0 PHAS=  -29.6 FOM= 0.95 TEST= 0
INDE 13 44 25 FOBS=    80.2 SIGMA=  2.7 PHAS=   43.6 FOM= 0.91 TEST= 0
INDE 13 44 27 FOBS=   117.2 SIGMA=  1.9 PHAS= -163.3 FOM= 0.95 TEST= 0
INDE 13 44 29 FOBS=   163.0 SIGMA=  1.4 PHAS=  -49.5 FOM= 0.94 TEST= 0
INDE 13 44 31 FOBS=    56.5 SIGMA=  3.7 PHAS=   23.7 FOM= 0.88 TEST= 0
INDE 13 44 33 FOBS=   108.8 SIGMA=  1.8 PHAS=  132.0 FOM= 0.83 TEST= 0
INDE 13 44 35 FOBS=    70.7 SIGMA=  2.7 PHAS=  -25.1 FOM= 0.79 TEST= 0
INDE 13 44 37 FOBS=   122.0 SIGMA=  1.7 PHAS=   92.7 FOM= 0.95 TEST= 0
INDE 13 44 39 FOBS=   164.9 SIGMA=  1.3 PHAS=   66.1 FOM= 0.93 TEST= 0
INDE 13 44 41 FOBS=    72.2 SIGMA=  2.7 PHAS= -114.6 FOM= 0.81 TEST= 0
INDE 13 44 43 FOBS=   129.8 SIGMA=  1.5 PHAS=  -47.1 FOM= 0.95 TEST= 0
INDE 13 44 45 FOBS=    74.8 SIGMA=  2.6 PHAS=  -94.1 FOM= 0.80 TEST= 0
INDE 13 44 47 FOBS=     0.0 SIGMA= 21.9 PHAS=    0.0 FOM= 0.00 TEST= 0
INDE 13 44 49 FOBS=    32.9 SIGMA=  7.3 PHAS=   55.3 FOM= 0.30 TEST= 0
INDE 13 44 51 FOBS=    18.6 SIGMA= 14.2 PHAS=  -57.7 FOM= 0.12 TEST= 0
INDE 13 44 53 FOBS=    83.6 SIGMA=  2.7 PHAS= -123.1 FOM= 0.90 TEST= 0
INDE 13 44 55 FOBS=    85.3 SIGMA=  2.6 PHAS= -105.7 FOM= 0.88 TEST= 0
INDE 13 44 57 FOBS=     0.0 SIGMA= 21.9 PHAS=    0.0 FOM= 0.00 TEST= 1
INDE 13 44 59 FOBS=     0.0 SIGMA= 20.9 PHAS=    0.0 FOM= 0.00 TEST= 0
INDE 13 44 61 FOBS=    16.9 SIGMA= 16.2 PHAS=   19.6 FOM= 0.23 TEST= 0
INDE 13 45 14 FOBS=    42.4 SIGMA=  6.5 PHAS=   11.1 FOM= 0.25 TEST= 0
INDE 13 45 16 FOBS=   181.5 SIGMA=  1.2 PHAS=   37.0 FOM= 0.93 TEST= 0
INDE 13 45 18 FOBS=     0.0 SIGMA= 22.4 PHAS=    0.0 FOM= 0.00 TEST= 0
INDE 13 45 20 FOBS=   154.9 SIGMA=  1.5 PHAS=  165.3 FOM= 0.50 TEST= 1
```

*FIG. 12A - 333*

```
INDE 13 45 22 FOBS=    82.0 SIGMA=  2.6 PHAS= -100.2 FOM= 0.78 TEST= 0
INDE 13 45 24 FOBS=   148.2 SIGMA=  1.5 PHAS=  -66.0 FOM= 0.97 TEST= 0
INDE 13 45 26 FOBS=   124.7 SIGMA=  1.8 PHAS=   22.4 FOM= 0.89 TEST= 0
INDE 13 45 28 FOBS=    84.2 SIGMA=  2.5 PHAS=  173.5 FOM= 0.93 TEST= 0
INDE 13 45 30 FOBS=    71.3 SIGMA=  3.0 PHAS= -175.3 FOM= 0.85 TEST= 0
INDE 13 45 32 FOBS=   186.1 SIGMA=  1.1 PHAS=   52.3 FOM= 0.89 TEST= 0
INDE 13 45 34 FOBS=    65.6 SIGMA=  2.8 PHAS=  102.8 FOM= 0.56 TEST= 0
INDE 13 45 36 FOBS=     0.0 SIGMA= 20.6 PHAS=    0.0 FOM= 0.00 TEST= 0
INDE 13 45 38 FOBS=     0.0 SIGMA= 20.2 PHAS=    0.0 FOM= 0.00 TEST= 0
INDE 13 45 40 FOBS=   102.9 SIGMA=  1.9 PHAS=  -26.6 FOM= 0.93 TEST= 0
INDE 13 45 42 FOBS=    93.9 SIGMA=  2.1 PHAS= -101.5 FOM= 0.93 TEST= 0
INDE 13 45 44 FOBS=   148.2 SIGMA=  1.4 PHAS=  174.7 FOM= 0.96 TEST= 0
INDE 13 45 46 FOBS=     0.0 SIGMA= 20.3 PHAS=    0.0 FOM= 0.00 TEST= 0
INDE 13 45 48 FOBS=    75.6 SIGMA=  3.0 PHAS=  -99.9 FOM= 0.66 TEST= 0
INDE 13 45 50 FOBS=     6.3 SIGMA= 34.9 PHAS=  134.2 FOM= 0.15 TEST= 0
INDE 13 45 52 FOBS=     0.0 SIGMA= 20.8 PHAS=    0.0 FOM= 0.00 TEST= 0
INDE 13 45 54 FOBS=    62.0 SIGMA=  3.6 PHAS= -124.0 FOM= 0.70 TEST= 0
INDE 13 45 56 FOBS=    65.5 SIGMA=  3.4 PHAS=  164.2 FOM= 0.85 TEST= 0
INDE 13 45 58 FOBS=    31.4 SIGMA=  7.8 PHAS= -118.3 FOM= 0.76 TEST= 0
INDE 13 45 60 FOBS=    55.6 SIGMA=  5.0 PHAS=  -98.7 FOM= 0.81 TEST= 0
INDE 13 45 62 FOBS=     0.0 SIGMA= 28.9 PHAS=    0.0 FOM= 0.00 TEST= 1
INDE 13 46 13 FOBS=    66.2 SIGMA=  4.2 PHAS= -176.0 FOM= 0.15 TEST= 0
INDE 13 46 15 FOBS=    98.4 SIGMA=  2.2 PHAS=   18.2 FOM= 0.84 TEST= 0
INDE 13 46 17 FOBS=   124.7 SIGMA=  1.7 PHAS=   49.7 FOM= 0.92 TEST= 0
INDE 13 46 19 FOBS=   143.2 SIGMA=  1.5 PHAS=  135.4 FOM= 0.73 TEST= 0
INDE 13 46 21 FOBS=   188.0 SIGMA=  1.2 PHAS=   61.5 FOM= 0.92 TEST= 0
INDE 13 46 23 FOBS=   134.8 SIGMA=  1.6 PHAS=  174.7 FOM= 0.91 TEST= 0
INDE 13 46 25 FOBS=   193.2 SIGMA=  1.2 PHAS= -145.9 FOM= 0.97 TEST= 0
INDE 13 46 27 FOBS=    13.6 SIGMA= 19.1 PHAS=  -65.1 FOM= 0.21 TEST= 0
INDE 13 46 29 FOBS=     0.0 SIGMA= 21.2 PHAS=    0.0 FOM= 0.00 TEST= 0
INDE 13 46 31 FOBS=    62.4 SIGMA=  3.4 PHAS=   29.4 FOM= 0.24 TEST= 0
INDE 13 46 33 FOBS=    79.7 SIGMA=  2.4 PHAS=   44.5 FOM= 0.73 TEST= 0
INDE 13 46 35 FOBS=    89.0 SIGMA=  2.1 PHAS= -103.7 FOM= 0.79 TEST= 0
INDE 13 46 37 FOBS=    99.7 SIGMA=  2.2 PHAS=   51.9 FOM= 0.87 TEST= 0
INDE 13 46 39 FOBS=   109.3 SIGMA=  1.8 PHAS=  -20.8 FOM= 0.94 TEST= 0
INDE 13 46 41 FOBS=   140.5 SIGMA=  1.4 PHAS= -152.8 FOM= 0.94 TEST= 0
INDE 13 46 43 FOBS=   181.8 SIGMA=  1.2 PHAS= -108.5 FOM= 0.19 TEST= 1
INDE 13 46 45 FOBS=    49.2 SIGMA=  3.8 PHAS=  107.4 FOM= 0.68 TEST= 0
INDE 13 46 47 FOBS=    60.3 SIGMA=  3.1 PHAS= -162.8 FOM= 0.47 TEST= 0
INDE 13 46 49 FOBS=    45.4 SIGMA=  4.9 PHAS=  -39.8 FOM= 0.36 TEST= 0
INDE 13 46 51 FOBS=     0.0 SIGMA= 20.9 PHAS=    0.0 FOM= 0.00 TEST= 0
INDE 13 46 53 FOBS=    30.8 SIGMA=  7.8 PHAS=  -50.1 FOM= 0.40 TEST= 0
INDE 13 46 55 FOBS=    53.7 SIGMA=  4.5 PHAS=    1.6 FOM= 0.67 TEST= 0
INDE 13 46 57 FOBS=     0.0 SIGMA= 21.1 PHAS=    0.0 FOM= 0.00 TEST= 0
INDE 13 46 59 FOBS=    73.5 SIGMA=  3.8 PHAS=  138.4 FOM= 0.90 TEST= 0
INDE 13 46 61 FOBS=     0.0 SIGMA= 23.6 PHAS=    0.0 FOM= 0.00 TEST= 0
INDE 13 47 14 FOBS=     0.0 SIGMA= 23.0 PHAS=    0.0 FOM= 0.00 TEST= 0
INDE 13 47 16 FOBS=    90.1 SIGMA=  2.3 PHAS=  -75.8 FOM= 0.69 TEST= 0
INDE 13 47 18 FOBS=   197.0 SIGMA=  1.2 PHAS=   -0.5 FOM= 0.93 TEST= 0
INDE 13 47 20 FOBS=    41.2 SIGMA=  5.4 PHAS=   90.5 FOM= 0.46 TEST= 0
INDE 13 47 22 FOBS=   100.3 SIGMA=  2.1 PHAS= -159.4 FOM= 0.78 TEST= 0
INDE 13 47 24 FOBS=    70.6 SIGMA=  2.9 PHAS=  114.9 FOM= 0.02 TEST= 1
INDE 13 47 26 FOBS=    76.5 SIGMA=  2.8 PHAS=   25.3 FOM= 0.60 TEST= 0
INDE 13 47 28 FOBS=    48.3 SIGMA=  4.3 PHAS=    5.5 FOM= 0.53 TEST= 0
INDE 13 47 30 FOBS=     0.0 SIGMA= 21.5 PHAS=    0.0 FOM= 0.00 TEST= 0
INDE 13 47 32 FOBS=   111.9 SIGMA=  1.9 PHAS=  114.1 FOM= 0.94 TEST= 0
INDE 13 47 34 FOBS=     0.0 SIGMA= 19.1 PHAS=    0.0 FOM= 0.00 TEST= 0
INDE 13 47 36 FOBS=    27.0 SIGMA=  8.2 PHAS=  -27.4 FOM= 0.11 TEST= 0
INDE 13 47 38 FOBS=    86.0 SIGMA=  2.2 PHAS=  -52.3 FOM= 0.91 TEST= 0
INDE 13 47 40 FOBS=   104.3 SIGMA=  2.0 PHAS=  -89.2 FOM= 0.92 TEST= 0
INDE 13 47 42 FOBS=   130.4 SIGMA=  1.6 PHAS=  -88.2 FOM= 0.94 TEST= 0
INDE 13 47 44 FOBS=    87.9 SIGMA=  2.2 PHAS= -135.9 FOM= 0.92 TEST= 0
INDE 13 47 46 FOBS=    61.7 SIGMA=  3.1 PHAS=   61.4 FOM= 0.81 TEST= 0
INDE 13 47 48 FOBS=    47.1 SIGMA=  4.0 PHAS=  -84.8 FOM= 0.65 TEST= 0
INDE 13 47 50 FOBS=    25.3 SIGMA=  8.7 PHAS= -121.1 FOM= 0.09 TEST= 1
INDE 13 47 52 FOBS=    53.8 SIGMA=  4.1 PHAS= -153.7 FOM= 0.38 TEST= 0
INDE 13 47 54 FOBS=    77.9 SIGMA=  2.9 PHAS= -129.3 FOM= 0.87 TEST= 0
INDE 13 47 56 FOBS=     0.0 SIGMA= 21.1 PHAS=    0.0 FOM= 0.00 TEST= 0
INDE 13 47 58 FOBS=    38.5 SIGMA=  9.6 PHAS=  -39.5 FOM= 0.48 TEST= 0
INDE 13 47 60 FOBS=     0.0 SIGMA= 23.6 PHAS=    0.0 FOM= 0.00 TEST= 0
```

*FIG. 12A - 334*

```
INDE  13  48  13  FOBS=   120.3  SIGMA=   2.3  PHAS=  -170.7  FOM=  0.88  TEST= 0
INDE  13  48  15  FOBS=   154.0  SIGMA=   1.9  PHAS=    15.8  FOM=  0.90  TEST= 0
INDE  13  48  17  FOBS=   296.1  SIGMA=   0.9  PHAS=   -90.3  FOM=  0.97  TEST= 0
INDE  13  48  19  FOBS=    57.2  SIGMA=   3.6  PHAS=     2.8  FOM=  0.70  TEST= 0
INDE  13  48  21  FOBS=   165.6  SIGMA=   1.4  PHAS=    76.1  FOM=  0.92  TEST= 0
INDE  13  48  23  FOBS=    73.2  SIGMA=   2.8  PHAS=   155.0  FOM=  0.85  TEST= 0
INDE  13  48  25  FOBS=   164.8  SIGMA=   1.3  PHAS=   -90.4  FOM=  0.80  TEST= 0
INDE  13  48  27  FOBS=   103.6  SIGMA=   2.0  PHAS=   -31.6  FOM=  0.90  TEST= 0
INDE  13  48  29  FOBS=    59.3  SIGMA=   3.5  PHAS=    87.8  FOM=  0.70  TEST= 0
INDE  13  48  31  FOBS=    55.4  SIGMA=   3.8  PHAS=    10.0  FOM=  0.86  TEST= 0
INDE  13  48  33  FOBS=   100.7  SIGMA=   2.1  PHAS=    37.1  FOM=  0.86  TEST= 0
INDE  13  48  35  FOBS=    56.5  SIGMA=   3.2  PHAS=  -102.3  FOM=  0.80  TEST= 0
INDE  13  48  37  FOBS=    66.3  SIGMA=   2.8  PHAS=  -124.5  FOM=  0.89  TEST= 0
INDE  13  48  39  FOBS=   102.4  SIGMA=   1.9  PHAS=   -78.2  FOM=  0.90  TEST= 0
INDE  13  48  41  FOBS=   135.3  SIGMA=   1.5  PHAS=   123.0  FOM=  0.92  TEST= 0
INDE  13  48  43  FOBS=    82.7  SIGMA=   2.3  PHAS=   157.7  FOM=  0.76  TEST= 1
INDE  13  48  45  FOBS=    54.9  SIGMA=   3.5  PHAS=  -120.2  FOM=  0.42  TEST= 0
INDE  13  48  47  FOBS=    48.5  SIGMA=   3.9  PHAS=  -140.1  FOM=  0.59  TEST= 0
INDE  13  48  49  FOBS=    83.3  SIGMA=   2.5  PHAS=  -156.0  FOM=  0.82  TEST= 0
INDE  13  48  51  FOBS=    27.1  SIGMA=   8.9  PHAS=  -170.7  FOM=  0.44  TEST= 0
INDE  13  48  53  FOBS=    61.6  SIGMA=   3.7  PHAS=   112.8  FOM=  0.83  TEST= 0
INDE  13  48  55  FOBS=     0.0  SIGMA=  21.1  PHAS=     0.0  FOM=  0.00  TEST= 0
INDE  13  48  57  FOBS=    48.3  SIGMA=   7.6  PHAS=   144.2  FOM=  0.08  TEST= 1
INDE  13  48  59  FOBS=    53.3  SIGMA=   5.4  PHAS=    88.3  FOM=  0.51  TEST= 0
INDE  13  49  14  FOBS=   126.2  SIGMA=   2.2  PHAS=  -142.2  FOM=  0.48  TEST= 1
INDE  13  49  16  FOBS=   272.3  SIGMA=   1.0  PHAS=  -156.1  FOM=  0.96  TEST= 0
INDE  13  49  18  FOBS=   113.0  SIGMA=   1.8  PHAS=   -79.4  FOM=  0.78  TEST= 0
INDE  13  49  20  FOBS=    55.0  SIGMA=   3.7  PHAS=    -9.1  FOM=  0.48  TEST= 0
INDE  13  49  22  FOBS=   134.2  SIGMA=   1.6  PHAS=  -162.1  FOM=  0.84  TEST= 0
INDE  13  49  24  FOBS=     0.0  SIGMA=  20.2  PHAS=     0.0  FOM=  0.00  TEST= 0
INDE  13  49  26  FOBS=    74.3  SIGMA=   2.8  PHAS=   -20.5  FOM=  0.26  TEST= 0
INDE  13  49  28  FOBS=   181.9  SIGMA=   1.2  PHAS=   -52.2  FOM=  0.97  TEST= 0
INDE  13  49  30  FOBS=    24.3  SIGMA=   8.4  PHAS=   114.0  FOM=  0.17  TEST= 1
INDE  13  49  32  FOBS=     0.0  SIGMA=  20.3  PHAS=     0.0  FOM=  0.00  TEST= 0
INDE  13  49  34  FOBS=    99.2  SIGMA=   1.9  PHAS=  -107.5  FOM=  0.90  TEST= 0
INDE  13  49  36  FOBS=   171.6  SIGMA=   1.2  PHAS=   157.9  FOM=  0.96  TEST= 0
INDE  13  49  38  FOBS=     0.0  SIGMA=  20.0  PHAS=     0.0  FOM=  0.00  TEST= 1
INDE  13  49  40  FOBS=    60.9  SIGMA=   3.1  PHAS=  -158.2  FOM=  0.82  TEST= 0
INDE  13  49  42  FOBS=    58.2  SIGMA=   3.3  PHAS=    57.0  FOM=  0.32  TEST= 0
INDE  13  49  44  FOBS=    55.9  SIGMA=   3.4  PHAS=    32.0  FOM=  0.80  TEST= 0
INDE  13  49  46  FOBS=    70.2  SIGMA=   2.7  PHAS=   122.5  FOM=  0.84  TEST= 0
INDE  13  49  48  FOBS=     0.0  SIGMA=  19.3  PHAS=     0.0  FOM=  0.00  TEST= 0
INDE  13  49  50  FOBS=    29.3  SIGMA=   7.1  PHAS=    10.0  FOM=  0.38  TEST= 0
INDE  13  49  52  FOBS=     0.0  SIGMA=  23.8  PHAS=     0.0  FOM=  0.00  TEST= 0
INDE  13  49  54  FOBS=    55.7  SIGMA=   4.1  PHAS=    59.7  FOM=  0.79  TEST= 0
INDE  13  49  56  FOBS=    16.3  SIGMA=  16.8  PHAS=    84.3  FOM=  0.47  TEST= 0
INDE  13  49  58  FOBS=    33.0  SIGMA=  10.1  PHAS=   -30.6  FOM=  0.22  TEST= 0
INDE  13  50  13  FOBS=    91.7  SIGMA=   2.9  PHAS=   105.9  FOM=  0.87  TEST= 0
INDE  13  50  15  FOBS=    59.2  SIGMA=   4.5  PHAS=    69.2  FOM=  0.75  TEST= 0
INDE  13  50  17  FOBS=    19.6  SIGMA=  10.2  PHAS=   164.7  FOM=  0.40  TEST= 0
INDE  13  50  19  FOBS=    59.2  SIGMA=   3.4  PHAS=   149.2  FOM=  0.54  TEST= 0
INDE  13  50  21  FOBS=   118.8  SIGMA=   1.9  PHAS=    55.1  FOM=  0.78  TEST= 0
INDE  13  50  23  FOBS=    85.6  SIGMA=   2.4  PHAS=   134.5  FOM=  0.50  TEST= 0
INDE  13  50  25  FOBS=    43.3  SIGMA=   5.1  PHAS=   -52.3  FOM=  0.45  TEST= 0
INDE  13  50  27  FOBS=    70.6  SIGMA=   2.9  PHAS=    18.0  FOM=  0.20  TEST= 0
INDE  13  50  29  FOBS=   103.4  SIGMA=   2.0  PHAS=  -134.7  FOM=  0.82  TEST= 0
INDE  13  50  31  FOBS=    64.5  SIGMA=   3.2  PHAS=  -162.5  FOM=  0.04  TEST= 1
INDE  13  50  33  FOBS=   162.8  SIGMA=   1.4  PHAS=   119.0  FOM=  0.95  TEST= 0
INDE  13  50  35  FOBS=   130.3  SIGMA=   1.5  PHAS=   112.8  FOM=  0.96  TEST= 0
INDE  13  50  37  FOBS=    22.8  SIGMA=   8.5  PHAS=   152.4  FOM=  0.38  TEST= 0
INDE  13  50  39  FOBS=     0.0  SIGMA=  20.0  PHAS=     0.0  FOM=  0.00  TEST= 0
INDE  13  50  41  FOBS=    54.8  SIGMA=   3.5  PHAS=   -24.3  FOM=  0.47  TEST= 0
INDE  13  50  43  FOBS=    98.3  SIGMA=   2.0  PHAS=   -75.4  FOM=  0.11  TEST= 1
INDE  13  50  45  FOBS=    41.8  SIGMA=   4.9  PHAS=   -53.7  FOM=  0.66  TEST= 0
INDE  13  50  47  FOBS=     0.0  SIGMA=  19.4  PHAS=     0.0  FOM=  0.00  TEST= 0
INDE  13  50  49  FOBS=    50.7  SIGMA=   4.1  PHAS=  -119.4  FOM=  0.81  TEST= 0
INDE  13  50  51  FOBS=    83.2  SIGMA=   2.6  PHAS=   -41.9  FOM=  0.88  TEST= 0
INDE  13  50  53  FOBS=    25.4  SIGMA=   8.9  PHAS=   -27.2  FOM=  0.28  TEST= 0
INDE  13  50  55  FOBS=     0.0  SIGMA=  27.0  PHAS=     0.0  FOM=  0.00  TEST= 0
INDE  13  50  57  FOBS=    43.2  SIGMA=   6.5  PHAS=    48.6  FOM=  0.16  TEST= 0
```

*FIG. 12A - 335*

```
INDE 13 51 14 FOBS=    86.9 SIGMA=  3.1 PHAS= -104.2 FOM= 0.73 TEST= 0
INDE 13 51 16 FOBS=    73.1 SIGMA=  3.6 PHAS=  175.8 FOM= 0.72 TEST= 1
INDE 13 51 18 FOBS=   103.3 SIGMA=  2.0 PHAS=  -94.2 FOM= 0.89 TEST= 0
INDE 13 51 20 FOBS=    56.3 SIGMA=  3.5 PHAS=  143.1 FOM= 0.27 TEST= 1
INDE 13 51 22 FOBS=    73.3 SIGMA=  2.8 PHAS=  -89.5 FOM= 0.54 TEST= 0
INDE 13 51 24 FOBS=    84.7 SIGMA=  2.5 PHAS= -142.7 FOM= 0.59 TEST= 0
INDE 13 51 26 FOBS=   156.0 SIGMA=  1.4 PHAS=    5.4 FOM= 0.92 TEST= 0
INDE 13 51 28 FOBS=    61.1 SIGMA=  3.4 PHAS= -100.8 FOM= 0.61 TEST= 0
INDE 13 51 30 FOBS=    42.4 SIGMA=  4.7 PHAS=  157.9 FOM= 0.63 TEST= 0
INDE 13 51 32 FOBS=   129.5 SIGMA=  1.7 PHAS=   33.6 FOM= 0.94 TEST= 0
INDE 13 51 34 FOBS=   108.2 SIGMA=  2.0 PHAS=   55.9 FOM= 0.80 TEST= 1
INDE 13 51 36 FOBS=    92.8 SIGMA=  2.0 PHAS=   60.5 FOM= 0.08 TEST= 1
INDE 13 51 38 FOBS=   108.9 SIGMA=  1.7 PHAS=  -34.2 FOM= 0.93 TEST= 0
INDE 13 51 40 FOBS=    89.4 SIGMA=  1.9 PHAS= -146.1 FOM= 0.86 TEST= 0
INDE 13 51 42 FOBS=    69.8 SIGMA=  2.8 PHAS=   19.3 FOM= 0.79 TEST= 0
INDE 13 51 44 FOBS=   134.6 SIGMA=  1.5 PHAS=   -7.5 FOM= 0.95 TEST= 0
INDE 13 51 46 FOBS=    90.1 SIGMA=  2.2 PHAS=  164.7 FOM= 0.10 TEST= 1
INDE 13 51 48 FOBS=    26.0 SIGMA=  8.8 PHAS=  -58.8 FOM= 0.17 TEST= 0
INDE 13 51 50 FOBS=    94.3 SIGMA=  2.3 PHAS= -128.0 FOM= 0.95 TEST= 0
INDE 13 51 52 FOBS=    62.5 SIGMA=  3.4 PHAS= -128.0 FOM= 0.62 TEST= 0
INDE 13 51 54 FOBS=    70.8 SIGMA=  4.0 PHAS= -160.0 FOM= 0.66 TEST= 0
INDE 13 51 56 FOBS=    41.4 SIGMA=  8.2 PHAS=   82.8 FOM= 0.52 TEST= 0
INDE 13 52 13 FOBS=    68.0 SIGMA=  3.9 PHAS= -109.2 FOM= 0.70 TEST= 0
INDE 13 52 15 FOBS=    34.3 SIGMA=  7.4 PHAS= -122.4 FOM= 0.20 TEST= 0
INDE 13 52 17 FOBS=   275.9 SIGMA=  1.1 PHAS=   87.6 FOM= 0.96 TEST= 0
INDE 13 52 19 FOBS=    99.8 SIGMA=  2.0 PHAS=  155.7 FOM= 0.60 TEST= 0
INDE 13 52 21 FOBS=    87.7 SIGMA=  2.3 PHAS= -171.8 FOM= 0.81 TEST= 0
INDE 13 52 23 FOBS=    99.1 SIGMA=  2.1 PHAS=  175.5 FOM= 0.86 TEST= 0
INDE 13 52 25 FOBS=   191.1 SIGMA=  1.2 PHAS= -174.3 FOM= 0.12 TEST= 1
INDE 13 52 27 FOBS=    28.3 SIGMA=  7.9 PHAS=  -22.7 FOM= 0.20 TEST= 0
INDE 13 52 29 FOBS=    31.0 SIGMA=  7.0 PHAS=  167.6 FOM= 0.44 TEST= 0
INDE 13 52 31 FOBS=    62.4 SIGMA=  3.2 PHAS=   11.4 FOM= 0.76 TEST= 0
INDE 13 52 33 FOBS=    80.8 SIGMA=  2.6 PHAS=   -6.8 FOM= 0.79 TEST= 0
INDE 13 52 35 FOBS=    44.7 SIGMA=  4.6 PHAS=   64.7 FOM= 0.19 TEST= 0
INDE 13 52 37 FOBS=    84.5 SIGMA=  2.2 PHAS= -131.3 FOM= 0.89 TEST= 0
INDE 13 52 39 FOBS=    47.9 SIGMA=  3.8 PHAS=  158.8 FOM= 0.74 TEST= 0
INDE 13 52 41 FOBS=    73.1 SIGMA=  2.3 PHAS= -104.1 FOM= 0.89 TEST= 0
INDE 13 52 43 FOBS=     0.0 SIGMA= 19.4 PHAS=    0.0 FOM= 0.00 TEST= 0
INDE 13 52 45 FOBS=   154.9 SIGMA=  1.3 PHAS=  -81.1 FOM= 0.63 TEST= 1
INDE 13 52 47 FOBS=    68.1 SIGMA=  2.9 PHAS= -153.1 FOM= 0.58 TEST= 0
INDE 13 52 49 FOBS=     0.0 SIGMA= 23.0 PHAS=    0.0 FOM= 0.00 TEST= 0
INDE 13 52 51 FOBS=    38.1 SIGMA=  5.5 PHAS= -174.0 FOM= 0.65 TEST= 0
INDE 13 52 53 FOBS=    44.7 SIGMA=  5.6 PHAS=  -43.8 FOM= 0.01 TEST= 1
INDE 13 52 55 FOBS=     9.4 SIGMA= 36.2 PHAS=   30.7 FOM= 0.17 TEST= 0
INDE 13 53 14 FOBS=   101.7 SIGMA=  2.6 PHAS=  126.1 FOM= 0.73 TEST= 0
INDE 13 53 16 FOBS=   157.2 SIGMA=  1.8 PHAS=  -30.6 FOM= 0.89 TEST= 0
INDE 13 53 18 FOBS=   211.8 SIGMA=  1.1 PHAS=  -25.7 FOM= 0.98 TEST= 0
INDE 13 53 20 FOBS=    86.8 SIGMA=  2.3 PHAS=  134.8 FOM= 0.81 TEST= 0
INDE 13 53 22 FOBS=    86.8 SIGMA=  2.3 PHAS=   95.5 FOM= 0.89 TEST= 1
INDE 13 53 24 FOBS=    43.5 SIGMA=  4.7 PHAS= -163.8 FOM= 0.20 TEST= 0
INDE 13 53 26 FOBS=   213.6 SIGMA=  1.1 PHAS= -133.1 FOM= 0.94 TEST= 0
INDE 13 53 28 FOBS=    33.8 SIGMA=  5.9 PHAS=  133.2 FOM= 0.51 TEST= 0
INDE 13 53 30 FOBS=    80.6 SIGMA=  2.5 PHAS=   90.0 FOM= 0.79 TEST= 0
INDE 13 53 32 FOBS=    55.5 SIGMA=  3.6 PHAS=  -24.3 FOM= 0.32 TEST= 0
INDE 13 53 34 FOBS=    24.0 SIGMA=  9.3 PHAS=  120.2 FOM= 0.17 TEST= 0
INDE 13 53 36 FOBS=    23.2 SIGMA=  8.5 PHAS= -113.2 FOM= 0.54 TEST= 0
INDE 13 53 38 FOBS=     0.0 SIGMA= 19.0 PHAS=    0.0 FOM= 0.00 TEST= 0
INDE 13 53 40 FOBS=    35.5 SIGMA=  5.1 PHAS=  105.0 FOM= 0.34 TEST= 0
INDE 13 53 42 FOBS=    29.6 SIGMA=  6.4 PHAS=    9.6 FOM= 0.57 TEST= 0
INDE 13 53 44 FOBS=    78.9 SIGMA=  2.5 PHAS= -135.4 FOM= 0.71 TEST= 0
INDE 13 53 46 FOBS=    57.0 SIGMA=  3.4 PHAS= -172.0 FOM= 0.80 TEST= 0
INDE 13 53 48 FOBS=    82.9 SIGMA=  2.7 PHAS= -145.8 FOM= 0.92 TEST= 0
INDE 13 53 50 FOBS=    46.7 SIGMA=  5.1 PHAS= -167.2 FOM= 0.79 TEST= 0
INDE 13 53 52 FOBS=    92.0 SIGMA=  2.9 PHAS=  107.5 FOM= 0.92 TEST= 0
INDE 13 53 54 FOBS=    52.2 SIGMA=  5.7 PHAS= -165.4 FOM= 0.76 TEST= 0
INDE 13 54 13 FOBS=   157.1 SIGMA=  1.8 PHAS=   23.9 FOM= 0.94 TEST= 0
INDE 13 54 15 FOBS=   168.2 SIGMA=  1.7 PHAS= -115.9 FOM= 0.95 TEST= 0
INDE 13 54 17 FOBS=   100.3 SIGMA=  2.6 PHAS=  -64.2 FOM= 0.96 TEST= 0
INDE 13 54 19 FOBS=   196.4 SIGMA=  1.1 PHAS= -124.0 FOM= 0.95 TEST= 0
INDE 13 54 21 FOBS=   143.3 SIGMA=  1.5 PHAS=  157.7 FOM= 0.94 TEST= 0
```

*FIG. 12A - 336*

```
INDE 13 54 23 FOBS=   36.4 SIGMA=  6.1 PHAS=   16.1 FOM= 0.83 TEST= 0
INDE 13 54 25 FOBS=   37.8 SIGMA=  5.3 PHAS=    5.6 FOM= 0.80 TEST= 0
INDE 13 54 27 FOBS=   89.9 SIGMA=  2.3 PHAS=   48.4 FOM= 0.90 TEST= 0
INDE 13 54 29 FOBS=   47.3 SIGMA=  4.2 PHAS=   38.8 FOM= 0.66 TEST= 0
INDE 13 54 31 FOBS=    0.0 SIGMA= 21.0 PHAS=    0.0 FOM= 0.00 TEST= 0
INDE 13 54 33 FOBS=   46.4 SIGMA=  4.3 PHAS=   23.3 FOM= 0.53 TEST= 0
INDE 13 54 35 FOBS=   42.7 SIGMA=  4.8 PHAS=  153.5 FOM= 0.37 TEST= 0
INDE 13 54 37 FOBS=    0.0 SIGMA= 19.0 PHAS=    0.0 FOM= 0.00 TEST= 0
INDE 13 54 39 FOBS=   52.7 SIGMA=  3.4 PHAS=   28.8 FOM= 0.42 TEST= 0
INDE 13 54 41 FOBS=   48.9 SIGMA=  3.6 PHAS=  -78.8 FOM= 0.84 TEST= 0
INDE 13 54 43 FOBS=   42.2 SIGMA=  4.3 PHAS=   69.9 FOM= 0.41 TEST= 0
INDE 13 54 45 FOBS=   21.8 SIGMA=  9.8 PHAS=  134.5 FOM= 0.29 TEST= 0
INDE 13 54 47 FOBS=   96.0 SIGMA=  2.6 PHAS=  139.1 FOM= 0.91 TEST= 0
INDE 13 54 49 FOBS=   76.5 SIGMA=  3.2 PHAS=   98.9 FOM= 0.92 TEST= 0
INDE 13 54 51 FOBS=    0.0 SIGMA= 23.0 PHAS=    0.0 FOM= 0.00 TEST= 0
INDE 13 54 53 FOBS=   53.6 SIGMA=  6.6 PHAS= -142.8 FOM= 0.26 TEST= 1
INDE 13 55 14 FOBS=  111.7 SIGMA=  2.4 PHAS=  137.1 FOM= 0.93 TEST= 0
INDE 13 55 16 FOBS=  136.1 SIGMA=  2.0 PHAS=  168.7 FOM= 0.96 TEST= 1
INDE 13 55 18 FOBS=   27.3 SIGMA=  9.2 PHAS= -118.7 FOM= 0.41 TEST= 1
INDE 13 55 20 FOBS=  121.2 SIGMA=  1.7 PHAS=  133.9 FOM= 0.93 TEST= 0
INDE 13 55 22 FOBS=    0.0 SIGMA= 20.6 PHAS=    0.0 FOM= 0.00 TEST= 0
INDE 13 55 24 FOBS=  137.8 SIGMA=  1.5 PHAS=  -60.9 FOM= 0.92 TEST= 0
INDE 13 55 26 FOBS=  137.8 SIGMA=  1.5 PHAS=  -86.4 FOM= 0.94 TEST= 0
INDE 13 55 28 FOBS=   69.1 SIGMA=  2.9 PHAS=  -20.9 FOM= 0.56 TEST= 1
INDE 13 55 30 FOBS=    0.0 SIGMA= 20.7 PHAS=    0.0 FOM= 0.00 TEST= 0
INDE 13 55 32 FOBS=  105.1 SIGMA=  2.0 PHAS= -179.7 FOM= 0.87 TEST= 0
INDE 13 55 34 FOBS=   48.1 SIGMA=  4.2 PHAS=  -68.2 FOM= 0.73 TEST= 0
INDE 13 55 36 FOBS=   89.7 SIGMA=  2.3 PHAS=  -96.4 FOM= 0.84 TEST= 0
INDE 13 55 38 FOBS=   16.7 SIGMA= 10.9 PHAS=  -70.7 FOM= 0.40 TEST= 0
INDE 13 55 40 FOBS=   21.1 SIGMA= 10.6 PHAS=   -0.8 FOM= 0.05 TEST= 0
INDE 13 55 42 FOBS=   14.6 SIGMA= 12.3 PHAS=  -34.5 FOM= 0.30 TEST= 0
INDE 13 55 44 FOBS=   34.1 SIGMA=  5.7 PHAS=   89.0 FOM= 0.74 TEST= 0
INDE 13 55 46 FOBS=   55.7 SIGMA=  4.2 PHAS=  -24.3 FOM= 0.68 TEST= 0
INDE 13 55 48 FOBS=   57.6 SIGMA=  4.7 PHAS=   -3.2 FOM= 0.45 TEST= 1
INDE 13 55 50 FOBS=    0.0 SIGMA= 26.5 PHAS=    0.0 FOM= 0.00 TEST= 0
INDE 13 55 52 FOBS=    0.0 SIGMA= 28.8 PHAS=    0.0 FOM= 0.00 TEST= 0
INDE 13 56 13 FOBS=  116.1 SIGMA=  1.2 PHAS=  -20.5 FOM= 0.93 TEST= 0
INDE 13 56 15 FOBS=   41.1 SIGMA=  6.1 PHAS=   19.1 FOM= 0.56 TEST= 0
INDE 13 56 17 FOBS=    0.0 SIGMA= 24.0 PHAS=    0.0 FOM= 0.00 TEST= 0
INDE 13 56 19 FOBS=  105.3 SIGMA=  1.9 PHAS= -173.4 FOM= 0.69 TEST= 0
INDE 13 56 21 FOBS=  106.7 SIGMA=  1.9 PHAS=  122.9 FOM= 0.76 TEST= 1
INDE 13 56 23 FOBS=   41.0 SIGMA=  4.8 PHAS= -164.9 FOM= 0.53 TEST= 0
INDE 13 56 25 FOBS=   41.4 SIGMA=  4.8 PHAS=  163.2 FOM= 0.84 TEST= 0
INDE 13 56 27 FOBS=   58.6 SIGMA=  3.4 PHAS= -107.8 FOM= 0.48 TEST= 0
INDE 13 56 29 FOBS=    0.0 SIGMA= 19.8 PHAS=    0.0 FOM= 0.00 TEST= 0
INDE 13 56 31 FOBS=   75.6 SIGMA=  2.7 PHAS=  111.5 FOM= 0.65 TEST= 0
INDE 13 56 33 FOBS=    0.0 SIGMA= 20.9 PHAS=    0.0 FOM= 0.00 TEST= 0
INDE 13 56 35 FOBS=   97.8 SIGMA=  2.1 PHAS=  150.4 FOM= 0.77 TEST= 0
INDE 13 56 37 FOBS=   32.3 SIGMA= 11.8 PHAS= -125.8 FOM= 0.44 TEST= 0
INDE 13 56 39 FOBS=   57.6 SIGMA=  3.4 PHAS=  -94.2 FOM= 0.81 TEST= 0
INDE 13 56 41 FOBS=    0.0 SIGMA= 20.5 PHAS=    0.0 FOM= 0.00 TEST= 0
INDE 13 56 43 FOBS=   31.0 SIGMA=  6.6 PHAS=  -38.7 FOM= 0.11 TEST= 0
INDE 13 56 45 FOBS=   62.5 SIGMA=  3.2 PHAS=   11.9 FOM= 0.82 TEST= 0
INDE 13 56 47 FOBS=   53.2 SIGMA=  5.2 PHAS= -108.3 FOM= 0.41 TEST= 0
INDE 13 56 49 FOBS=   23.5 SIGMA= 15.2 PHAS= -126.7 FOM= 0.35 TEST= 0
INDE 13 56 51 FOBS=   17.9 SIGMA= 20.3 PHAS=  113.0 FOM= 0.02 TEST= 1
INDE 13 57 14 FOBS=  142.8 SIGMA=  1.4 PHAS=  165.7 FOM= 0.96 TEST= 0
INDE 13 57 16 FOBS=   59.7 SIGMA=  4.3 PHAS=  123.1 FOM= 0.48 TEST= 0
INDE 13 57 18 FOBS=  113.3 SIGMA=  2.3 PHAS=   83.9 FOM= 0.76 TEST= 0
INDE 13 57 20 FOBS=   88.8 SIGMA=  2.2 PHAS=   15.1 FOM= 0.89 TEST= 0
INDE 13 57 22 FOBS=    3.3 SIGMA= 61.0 PHAS=  -39.7 FOM= 0.05 TEST= 0
INDE 13 57 24 FOBS=   34.6 SIGMA=  5.6 PHAS=  -39.3 FOM= 0.13 TEST= 0
INDE 13 57 26 FOBS=   67.0 SIGMA=  3.0 PHAS= -134.8 FOM= 0.26 TEST= 0
INDE 13 57 28 FOBS=    0.0 SIGMA= 19.8 PHAS=    0.0 FOM= 0.00 TEST= 1
INDE 13 57 30 FOBS=   60.7 SIGMA=  3.3 PHAS=  100.4 FOM= 0.82 TEST= 0
INDE 13 57 32 FOBS=    0.0 SIGMA= 20.6 PHAS=    0.0 FOM= 0.00 TEST= 0
INDE 13 57 34 FOBS=   51.4 SIGMA=  4.3 PHAS=  -76.4 FOM= 0.34 TEST= 0
INDE 13 57 36 FOBS=   82.5 SIGMA=  3.1 PHAS=  -84.5 FOM= 0.89 TEST= 0
INDE 13 57 38 FOBS=   91.2 SIGMA=  2.4 PHAS= -156.5 FOM= 0.89 TEST= 0
INDE 13 57 40 FOBS=    0.0 SIGMA= 20.7 PHAS=    0.0 FOM= 0.00 TEST= 0
```

*FIG. 12A - 337*

```
INDE 13 57 42 FOBS=   0.0 SIGMA= 20.7 PHAS=    0.0 FOM= 0.00 TEST= 0
INDE 13 57 44 FOBS=  29.5 SIGMA=  7.0 PHAS=   -5.7 FOM= 0.26 TEST= 0
INDE 13 57 46 FOBS=  94.6 SIGMA=  2.4 PHAS=  -75.8 FOM= 0.91 TEST= 0
INDE 13 57 48 FOBS=  37.5 SIGMA= 12.1 PHAS=  -57.0 FOM= 0.61 TEST= 0
INDE 13 57 50 FOBS= 108.4 SIGMA=  3.5 PHAS=  135.1 FOM= 0.92 TEST= 0
INDE 13 58 13 FOBS=  92.0 SIGMA=  2.8 PHAS=   22.6 FOM= 0.86 TEST= 0
INDE 13 58 15 FOBS=  45.4 SIGMA=  4.3 PHAS=   23.4 FOM= 0.17 TEST= 1
INDE 13 58 17 FOBS=  49.2 SIGMA=  5.1 PHAS=  -93.6 FOM= 0.66 TEST= 0
INDE 13 58 19 FOBS=  52.6 SIGMA=  4.8 PHAS=  -77.3 FOM= 0.84 TEST= 0
INDE 13 58 21 FOBS=  72.7 SIGMA=  2.7 PHAS=  -96.1 FOM= 0.69 TEST= 0
INDE 13 58 23 FOBS=  74.5 SIGMA=  2.6 PHAS=  -32.5 FOM= 0.94 TEST= 0
INDE 13 58 25 FOBS= 117.4 SIGMA=  1.8 PHAS=   91.9 FOM= 0.88 TEST= 0
INDE 13 58 27 FOBS=  31.5 SIGMA=  6.2 PHAS=   -3.5 FOM= 0.43 TEST= 0
INDE 13 58 29 FOBS= 101.3 SIGMA=  2.2 PHAS=  -22.0 FOM= 0.87 TEST= 0
INDE 13 58 31 FOBS=  64.3 SIGMA=  3.8 PHAS=   36.8 FOM= 0.78 TEST= 0
INDE 13 58 33 FOBS=   0.0 SIGMA= 21.8 PHAS=    0.0 FOM= 0.00 TEST= 0
INDE 13 58 35 FOBS=  30.4 SIGMA=  9.0 PHAS=  153.1 FOM= 0.55 TEST= 0
INDE 13 58 37 FOBS=  67.0 SIGMA=  3.8 PHAS= -163.7 FOM= 0.66 TEST= 0
INDE 13 58 39 FOBS=  24.1 SIGMA=  9.8 PHAS=  -67.3 FOM= 0.32 TEST= 0
INDE 13 58 41 FOBS=  43.3 SIGMA=  5.0 PHAS= -163.2 FOM= 0.62 TEST= 0
INDE 13 58 43 FOBS=  48.3 SIGMA=  4.3 PHAS= -146.4 FOM= 0.79 TEST= 0
INDE 13 58 45 FOBS=  27.0 SIGMA=  7.8 PHAS=  123.7 FOM= 0.26 TEST= 0
INDE 13 58 47 FOBS=   0.0 SIGMA= 26.0 PHAS=    0.0 FOM= 0.00 TEST= 0
INDE 13 58 49 FOBS=  89.3 SIGMA=  4.1 PHAS=  -56.0 FOM= 0.31 TEST= 1
INDE 13 59 14 FOBS=  93.7 SIGMA=  1.8 PHAS=  109.2 FOM= 0.82 TEST= 0
INDE 13 59 16 FOBS=  58.8 SIGMA=  3.3 PHAS=  155.2 FOM= 0.76 TEST= 0
INDE 13 59 18 FOBS=  65.2 SIGMA=  3.9 PHAS=   31.3 FOM= 0.12 TEST= 0
INDE 13 59 20 FOBS=  83.9 SIGMA=  3.0 PHAS=  103.9 FOM= 0.74 TEST= 0
INDE 13 59 22 FOBS=  37.2 SIGMA=  5.7 PHAS= -133.1 FOM= 0.76 TEST= 0
INDE 13 59 24 FOBS=  78.2 SIGMA=  2.8 PHAS=  -79.5 FOM= 0.69 TEST= 0
INDE 13 59 26 FOBS=   0.0 SIGMA= 23.4 PHAS=    0.0 FOM= 0.00 TEST= 0
INDE 13 59 28 FOBS=  37.2 SIGMA=  6.4 PHAS=  138.1 FOM= 0.27 TEST= 1
INDE 13 59 30 FOBS= 106.2 SIGMA=  2.3 PHAS=  -54.1 FOM= 0.88 TEST= 0
INDE 13 59 32 FOBS=   0.0 SIGMA= 23.7 PHAS=    0.0 FOM= 0.00 TEST= 0
INDE 13 59 34 FOBS=   0.0 SIGMA= 22.0 PHAS=    0.0 FOM= 0.00 TEST= 0
INDE 13 59 36 FOBS=  83.1 SIGMA=  3.1 PHAS=   94.5 FOM= 0.74 TEST= 0
INDE 13 59 38 FOBS= 158.1 SIGMA=  2.1 PHAS= -149.6 FOM= 0.97 TEST= 0
INDE 13 59 40 FOBS=  62.6 SIGMA=  3.5 PHAS=   46.8 FOM= 0.73 TEST= 0
INDE 13 59 42 FOBS=   0.0 SIGMA= 21.0 PHAS=    0.0 FOM= 0.00 TEST= 0
INDE 13 59 44 FOBS=  29.4 SIGMA=  7.2 PHAS=  116.2 FOM= 0.27 TEST= 0
INDE 13 59 46 FOBS=   0.0 SIGMA= 26.3 PHAS=    0.0 FOM= 0.00 TEST= 0
INDE 13 59 48 FOBS=  52.1 SIGMA=  5.8 PHAS=  -79.8 FOM= 0.53 TEST= 0
INDE 13 60 13 FOBS=  87.3 SIGMA=  2.3 PHAS=  109.9 FOM= 0.94 TEST= 0
INDE 13 60 15 FOBS=  33.9 SIGMA=  5.1 PHAS=   97.1 FOM= 0.45 TEST= 0
INDE 13 60 17 FOBS=  65.2 SIGMA=  2.9 PHAS= -117.9 FOM= 0.85 TEST= 0
INDE 13 60 19 FOBS=  57.7 SIGMA=  4.8 PHAS=  -84.5 FOM= 0.38 TEST= 0
INDE 13 60 21 FOBS= 106.3 SIGMA=  2.2 PHAS=    7.1 FOM= 0.86 TEST= 0
INDE 13 60 23 FOBS=  56.8 SIGMA=  4.1 PHAS=   -2.9 FOM= 0.90 TEST= 0
INDE 13 60 25 FOBS= 138.6 SIGMA=  1.3 PHAS=  -17.9 FOM= 0.87 TEST= 0
INDE 13 60 27 FOBS=  30.0 SIGMA=  9.2 PHAS=   49.7 FOM= 0.65 TEST= 0
INDE 13 60 29 FOBS=  91.2 SIGMA=  2.7 PHAS=  -74.3 FOM= 0.90 TEST= 0
INDE 13 60 31 FOBS=  45.6 SIGMA=  5.3 PHAS=  -73.5 FOM= 0.66 TEST= 0
INDE 13 60 33 FOBS=  34.6 SIGMA=  7.0 PHAS=  141.3 FOM= 0.10 TEST= 0
INDE 13 60 35 FOBS=  49.9 SIGMA=  5.6 PHAS=  -59.6 FOM= 0.53 TEST= 0
INDE 13 60 37 FOBS= 106.6 SIGMA=  2.5 PHAS=  -69.2 FOM= 0.11 TEST= 1
INDE 13 60 39 FOBS=  49.5 SIGMA=  4.7 PHAS=  159.6 FOM= 0.74 TEST= 0
INDE 13 60 41 FOBS=   0.0 SIGMA= 21.0 PHAS=    0.0 FOM= 0.00 TEST= 0
INDE 13 60 43 FOBS=  24.5 SIGMA=  9.1 PHAS=  137.4 FOM= 0.32 TEST= 0
INDE 13 60 45 FOBS=   0.0 SIGMA= 25.9 PHAS=    0.0 FOM= 0.00 TEST= 0
INDE 13 60 47 FOBS=   0.0 SIGMA= 23.3 PHAS=    0.0 FOM= 0.00 TEST= 0
INDE 13 61 14 FOBS=  73.5 SIGMA=  3.4 PHAS=   63.4 FOM= 0.90 TEST= 0
INDE 13 61 16 FOBS=  27.3 SIGMA=  7.6 PHAS=   64.4 FOM= 0.28 TEST= 0
INDE 13 61 18 FOBS=  21.1 SIGMA= 13.2 PHAS= -160.3 FOM= 0.29 TEST= 0
INDE 13 61 20 FOBS=  32.4 SIGMA= 10.4 PHAS=   26.2 FOM= 0.38 TEST= 0
INDE 13 61 22 FOBS=  42.8 SIGMA=  5.3 PHAS= -105.6 FOM= 0.80 TEST= 0
INDE 13 61 24 FOBS=  55.7 SIGMA=  4.1 PHAS= -103.3 FOM= 0.57 TEST= 0
INDE 13 61 26 FOBS=  87.6 SIGMA=  2.7 PHAS= -100.3 FOM= 0.88 TEST= 0
INDE 13 61 28 FOBS=  61.6 SIGMA=  3.9 PHAS=  141.0 FOM= 0.62 TEST= 0
INDE 13 61 30 FOBS=  16.3 SIGMA= 14.8 PHAS=  -85.1 FOM= 0.30 TEST= 1
INDE 13 61 32 FOBS=  31.0 SIGMA=  9.2 PHAS= -166.3 FOM= 0.29 TEST= 0
```

*FIG. 12A - 338*

```
INDE 13 61 34 FOBS=   60.7 SIGMA=  4.1 PHAS=  133.4 FOM= 0.78 TEST= 0
INDE 13 61 36 FOBS=   50.0 SIGMA=  5.1 PHAS=   77.1 FOM= 0.51 TEST= 0
INDE 13 61 38 FOBS=    0.0 SIGMA= 22.7 PHAS=    0.0 FOM= 0.00 TEST= 0
INDE 13 61 40 FOBS=   36.9 SIGMA=  8.5 PHAS=  116.9 FOM= 0.36 TEST= 0
INDE 13 61 42 FOBS=   76.4 SIGMA=  3.3 PHAS= -128.4 FOM= 0.79 TEST= 0
INDE 13 61 44 FOBS=   16.6 SIGMA= 16.6 PHAS=  167.6 FOM= 0.07 TEST= 1
INDE 13 61 46 FOBS=   18.0 SIGMA= 17.1 PHAS=  173.3 FOM= 0.26 TEST= 0
INDE 13 62 13 FOBS=   66.5 SIGMA=  3.3 PHAS=  -86.7 FOM= 0.84 TEST= 0
INDE 13 62 15 FOBS=    0.0 SIGMA= 19.4 PHAS=    0.0 FOM= 0.00 TEST= 0
INDE 13 62 17 FOBS=   92.2 SIGMA=  2.4 PHAS=  100.0 FOM= 0.88 TEST= 0
INDE 13 62 19 FOBS=   44.5 SIGMA=  7.6 PHAS=    0.7 FOM= 0.32 TEST= 0
INDE 13 62 21 FOBS=   53.1 SIGMA=  6.4 PHAS=   35.1 FOM= 0.80 TEST= 0
INDE 13 62 23 FOBS=  129.9 SIGMA=  1.9 PHAS=   34.6 FOM= 0.90 TEST= 0
INDE 13 62 25 FOBS=   58.8 SIGMA=  4.6 PHAS=   -5.4 FOM= 0.70 TEST= 0
INDE 13 62 27 FOBS=   39.0 SIGMA=  6.9 PHAS= -172.5 FOM= 0.12 TEST= 0
INDE 13 62 29 FOBS=   12.6 SIGMA= 27.3 PHAS=  -63.7 FOM= 0.25 TEST= 0
INDE 13 62 31 FOBS=   71.4 SIGMA=  4.0 PHAS=  -44.4 FOM= 0.08 TEST= 1
INDE 13 62 33 FOBS=   61.6 SIGMA=  4.6 PHAS=   40.8 FOM= 0.86 TEST= 0
INDE 13 62 35 FOBS=   44.3 SIGMA=  6.5 PHAS=   22.8 FOM= 0.74 TEST= 0
INDE 13 62 37 FOBS=   39.2 SIGMA=  7.4 PHAS=  -67.7 FOM= 0.75 TEST= 0
INDE 13 62 39 FOBS=   55.0 SIGMA=  5.5 PHAS=  168.0 FOM= 0.31 TEST= 1
INDE 13 62 41 FOBS=   49.5 SIGMA=  5.0 PHAS=  101.9 FOM= 0.52 TEST= 0
INDE 13 62 43 FOBS=    0.0 SIGMA= 26.9 PHAS=    0.0 FOM= 0.00 TEST= 1
INDE 13 62 45 FOBS=    0.0 SIGMA= 28.9 PHAS=    0.0 FOM= 0.00 TEST= 0
INDE 13 63 14 FOBS=   65.7 SIGMA=  3.4 PHAS=   29.5 FOM= 0.70 TEST= 0
INDE 13 63 16 FOBS=   98.2 SIGMA=  2.0 PHAS=   43.1 FOM= 0.92 TEST= 0
INDE 13 63 18 FOBS=   71.1 SIGMA=  3.2 PHAS=  -44.5 FOM= 0.89 TEST= 0
INDE 13 63 20 FOBS=   83.1 SIGMA=  4.1 PHAS=  -44.4 FOM= 0.86 TEST= 0
INDE 13 63 22 FOBS=   74.8 SIGMA=  4.6 PHAS=  -45.2 FOM= 0.90 TEST= 0
INDE 13 63 24 FOBS=   95.4 SIGMA=  2.9 PHAS=  -19.9 FOM= 0.90 TEST= 0
INDE 13 63 26 FOBS=   81.2 SIGMA=  3.4 PHAS= -131.8 FOM= 0.57 TEST= 0
INDE 13 63 28 FOBS=   79.5 SIGMA=  3.6 PHAS=  150.0 FOM= 0.90 TEST= 0
INDE 13 63 30 FOBS=    0.0 SIGMA= 26.6 PHAS=    0.0 FOM= 0.00 TEST= 0
INDE 13 63 32 FOBS=   61.6 SIGMA=  4.7 PHAS=  -52.2 FOM= 0.90 TEST= 0
INDE 13 63 34 FOBS=   82.5 SIGMA=  3.5 PHAS= -109.3 FOM= 0.91 TEST= 0
INDE 13 63 36 FOBS=   64.0 SIGMA=  4.6 PHAS=   65.7 FOM= 0.74 TEST= 0
INDE 13 63 38 FOBS=   84.4 SIGMA=  3.6 PHAS=  121.4 FOM= 0.61 TEST= 1
INDE 13 63 40 FOBS=    7.9 SIGMA= 38.9 PHAS=  162.6 FOM= 0.03 TEST= 0
INDE 13 63 42 FOBS=   56.6 SIGMA=  5.6 PHAS= -121.1 FOM= 0.85 TEST= 0
INDE 13 64 13 FOBS=   76.2 SIGMA=  2.7 PHAS= -166.7 FOM= 0.69 TEST= 0
INDE 13 64 15 FOBS=   73.1 SIGMA=  4.7 PHAS=  -27.3 FOM= 0.84 TEST= 0
INDE 13 64 17 FOBS=   29.5 SIGMA=  6.7 PHAS= -162.0 FOM= 0.26 TEST= 0
INDE 13 64 19 FOBS=   71.8 SIGMA=  4.8 PHAS= -138.7 FOM= 0.88 TEST= 0
INDE 13 64 21 FOBS=   46.0 SIGMA=  7.3 PHAS= -150.8 FOM= 0.39 TEST= 0
INDE 13 64 23 FOBS=    0.0 SIGMA= 22.8 PHAS=    0.0 FOM= 0.00 TEST= 0
INDE 13 64 25 FOBS=    0.0 SIGMA= 25.2 PHAS=    0.0 FOM= 0.00 TEST= 0
INDE 13 64 27 FOBS=   75.8 SIGMA=  3.7 PHAS=   25.4 FOM= 0.03 TEST= 1
INDE 13 64 29 FOBS=   90.3 SIGMA=  3.2 PHAS=   95.3 FOM= 0.75 TEST= 0
INDE 13 64 31 FOBS=   69.3 SIGMA=  4.2 PHAS=    7.1 FOM= 0.58 TEST= 0
INDE 13 64 33 FOBS=   46.8 SIGMA=  6.2 PHAS=  161.5 FOM= 0.75 TEST= 0
INDE 13 64 35 FOBS=    0.0 SIGMA= 26.7 PHAS=    0.0 FOM= 0.00 TEST= 0
INDE 13 64 37 FOBS=   10.1 SIGMA= 29.0 PHAS=  -10.1 FOM= 0.11 TEST= 0
INDE 13 64 39 FOBS=    0.0 SIGMA= 27.5 PHAS=    0.0 FOM= 0.00 TEST= 1
INDE 13 64 41 FOBS=   60.4 SIGMA=  5.3 PHAS=   56.0 FOM= 0.37 TEST= 0
INDE 13 65 14 FOBS=   64.5 SIGMA=  3.4 PHAS=  -46.4 FOM= 0.76 TEST= 0
INDE 13 65 16 FOBS=    0.0 SIGMA= 25.8 PHAS=    0.0 FOM= 0.00 TEST= 0
INDE 13 65 18 FOBS=   77.4 SIGMA=  2.7 PHAS= -116.7 FOM= 0.71 TEST= 0
INDE 13 65 20 FOBS=   68.5 SIGMA=  5.0 PHAS=  -89.8 FOM= 0.77 TEST= 0
INDE 13 65 22 FOBS=   24.0 SIGMA= 14.0 PHAS=   18.9 FOM= 0.46 TEST= 0
INDE 13 65 24 FOBS=   39.2 SIGMA=  6.8 PHAS=  144.2 FOM= 0.29 TEST= 0
INDE 13 65 26 FOBS=   74.6 SIGMA=  3.7 PHAS=  167.5 FOM= 0.89 TEST= 0
INDE 13 65 28 FOBS=    0.0 SIGMA= 23.4 PHAS=    0.0 FOM= 0.00 TEST= 0
INDE 13 65 30 FOBS=   45.2 SIGMA=  6.3 PHAS=  -73.5 FOM= 0.33 TEST= 0
INDE 13 65 32 FOBS=    0.0 SIGMA= 24.0 PHAS=    0.0 FOM= 0.00 TEST= 0
INDE 13 65 34 FOBS=    0.0 SIGMA= 24.1 PHAS=    0.0 FOM= 0.00 TEST= 0
INDE 13 65 36 FOBS=   56.4 SIGMA=  5.2 PHAS=   75.7 FOM= 0.71 TEST= 0
INDE 13 65 38 FOBS=    0.0 SIGMA= 24.4 PHAS=    0.0 FOM= 0.00 TEST= 1
INDE 13 65 40 FOBS=   86.2 SIGMA=  3.7 PHAS= -151.9 FOM= 0.84 TEST= 0
INDE 13 66 13 FOBS=  109.7 SIGMA=  1.9 PHAS=   79.1 FOM= 0.88 TEST= 0
INDE 13 66 15 FOBS=  103.7 SIGMA=  2.2 PHAS= -133.2 FOM= 0.86 TEST= 0
```

*FIG. 12A - 339*

```
INDE 13 66 17 FOBS=    15.8 SIGMA=  11.7 PHAS= -138.7 FOM= 0.30 TEST= 0
INDE 13 66 19 FOBS=    77.8 SIGMA=   2.8 PHAS=  131.8 FOM= 0.85 TEST= 0
INDE 13 66 21 FOBS=     7.4 SIGMA=  44.9 PHAS=  -19.5 FOM= 0.09 TEST= 1
INDE 13 66 23 FOBS=     0.0 SIGMA=  25.8 PHAS=    0.0 FOM= 0.00 TEST= 0
INDE 13 66 25 FOBS=    50.6 SIGMA=   5.3 PHAS= -110.0 FOM= 0.57 TEST= 0
INDE 13 66 27 FOBS=    45.8 SIGMA=   6.1 PHAS=   11.7 FOM= 0.69 TEST= 0
INDE 13 66 29 FOBS=     0.0 SIGMA=  23.6 PHAS=    0.0 FOM= 0.00 TEST= 0
INDE 13 66 31 FOBS=    55.5 SIGMA=   5.2 PHAS=   73.6 FOM= 0.39 TEST= 0
INDE 13 66 33 FOBS=     0.0 SIGMA=  27.2 PHAS=    0.0 FOM= 0.00 TEST= 0
INDE 13 66 35 FOBS=    17.4 SIGMA=  21.4 PHAS=  -78.1 FOM= 0.15 TEST= 0
INDE 13 66 37 FOBS=    46.8 SIGMA=   6.5 PHAS=   66.5 FOM= 0.50 TEST= 0
INDE 13 66 39 FOBS=    23.3 SIGMA=  21.6 PHAS=  115.6 FOM= 0.45 TEST= 0
INDE 13 67 14 FOBS=    53.1 SIGMA=   4.3 PHAS=  -32.8 FOM= 0.84 TEST= 0
INDE 13 67 16 FOBS=    63.7 SIGMA=   5.4 PHAS=  171.6 FOM= 0.71 TEST= 0
INDE 13 67 18 FOBS=    34.9 SIGMA=   5.7 PHAS=  -31.4 FOM= 0.80 TEST= 0
INDE 13 67 20 FOBS=     0.0 SIGMA=  21.1 PHAS=    0.0 FOM= 0.00 TEST= 0
INDE 13 67 22 FOBS=    90.1 SIGMA=   2.9 PHAS=   76.3 FOM= 0.90 TEST= 0
INDE 13 67 24 FOBS=    68.6 SIGMA=   5.0 PHAS= -146.2 FOM= 0.89 TEST= 0
INDE 13 67 26 FOBS=    85.3 SIGMA=   3.2 PHAS=  169.9 FOM= 0.92 TEST= 0
INDE 13 67 28 FOBS=     0.0 SIGMA=  23.5 PHAS=    0.0 FOM= 0.00 TEST= 0
INDE 13 67 30 FOBS=     0.0 SIGMA=  23.8 PHAS=    0.0 FOM= 0.00 TEST= 0
INDE 13 67 32 FOBS=    38.4 SIGMA=   7.6 PHAS=  -79.6 FOM= 0.56 TEST= 0
INDE 13 67 34 FOBS=    17.8 SIGMA=  16.7 PHAS=  -46.7 FOM= 0.09 TEST= 0
INDE 13 67 36 FOBS=    71.5 SIGMA=   4.3 PHAS=  118.5 FOM= 0.11 TEST= 1
INDE 13 68 15 FOBS=    86.0 SIGMA=   3.4 PHAS= -137.5 FOM= 0.90 TEST= 0
INDE 13 68 17 FOBS=   101.3 SIGMA=   4.9 PHAS=  120.5 FOM= 0.44 TEST= 1
INDE 13 68 19 FOBS=     0.0 SIGMA=  21.5 PHAS=    0.0 FOM= 0.00 TEST= 0
INDE 13 68 21 FOBS=    48.7 SIGMA=   4.8 PHAS= -123.7 FOM= 0.27 TEST= 0
INDE 13 68 23 FOBS=    77.0 SIGMA=   3.3 PHAS=   94.2 FOM= 0.79 TEST= 0
INDE 13 68 25 FOBS=    52.3 SIGMA=   6.5 PHAS=  153.8 FOM= 0.67 TEST= 0
INDE 13 68 27 FOBS=    45.6 SIGMA=   6.0 PHAS=  105.4 FOM= 0.82 TEST= 0
INDE 13 68 29 FOBS=     0.0 SIGMA=  23.8 PHAS=    0.0 FOM= 0.00 TEST= 0
INDE 13 68 31 FOBS=    45.3 SIGMA=   8.0 PHAS=  170.6 FOM= 0.33 TEST= 0
INDE 13 68 33 FOBS=     0.0 SIGMA=  24.4 PHAS=    0.0 FOM= 0.00 TEST= 0
INDE 13 68 35 FOBS=     0.0 SIGMA=  24.7 PHAS=    0.0 FOM= 0.00 TEST= 0
INDE 13 69 14 FOBS=   119.1 SIGMA=   2.1 PHAS=   73.5 FOM= 0.94 TEST= 0
INDE 13 69 16 FOBS=     0.0 SIGMA=  24.3 PHAS=    0.0 FOM= 0.00 TEST= 0
INDE 13 69 20 FOBS=     0.0 SIGMA=  23.2 PHAS=    0.0 FOM= 0.00 TEST= 0
INDE 13 69 22 FOBS=    68.0 SIGMA=   4.1 PHAS=   41.3 FOM= 0.46 TEST= 0
INDE 13 69 24 FOBS=   105.0 SIGMA=   3.0 PHAS= -167.7 FOM= 0.12 TEST= 1
INDE 13 69 26 FOBS=    70.1 SIGMA=   4.0 PHAS=   46.7 FOM= 0.86 TEST= 0
INDE 13 69 28 FOBS=    90.3 SIGMA=   3.2 PHAS=   67.0 FOM= 0.87 TEST= 0
INDE 13 69 30 FOBS=     0.0 SIGMA=  24.0 PHAS=    0.0 FOM= 0.00 TEST= 0
INDE 13 69 32 FOBS=    21.9 SIGMA=  13.8 PHAS=   -9.3 FOM= 0.11 TEST= 0
INDE 13 70 15 FOBS=     0.0 SIGMA=  22.7 PHAS=    0.0 FOM= 0.00 TEST= 0
INDE 13 70 19 FOBS=     0.0 SIGMA=  21.1 PHAS=    0.0 FOM= 0.00 TEST= 0
INDE 13 70 21 FOBS=    74.0 SIGMA=   4.0 PHAS=   20.6 FOM= 0.82 TEST= 0
INDE 13 70 25 FOBS=    52.0 SIGMA=   7.7 PHAS=  -60.3 FOM= 0.86 TEST= 0
INDE 13 70 27 FOBS=    27.0 SIGMA=  12.5 PHAS=  -49.7 FOM= 0.50 TEST= 0
INDE 13 70 29 FOBS=     0.0 SIGMA=  26.4 PHAS=    0.0 FOM= 0.00 TEST= 0
INDE 13 70 31 FOBS=     0.0 SIGMA=  24.4 PHAS=    0.0 FOM= 0.00 TEST= 0
INDE 13 71 16 FOBS=    56.4 SIGMA=   5.2 PHAS=  -64.7 FOM= 0.80 TEST= 0
INDE 13 71 20 FOBS=    18.8 SIGMA=  13.4 PHAS=  -14.0 FOM= 0.39 TEST= 0
INDE 13 71 22 FOBS=    66.9 SIGMA=   4.7 PHAS= -104.5 FOM= 0.90 TEST= 0
INDE 13 71 24 FOBS=    51.6 SIGMA=   6.9 PHAS= -162.4 FOM= 0.49 TEST= 0
INDE 13 71 26 FOBS=    54.3 SIGMA=   7.6 PHAS= -133.7 FOM= 0.76 TEST= 0
INDE 13 71 28 FOBS=    25.1 SIGMA=  19.5 PHAS=  109.3 FOM= 0.08 TEST= 1
INDE 13 72 15 FOBS=    59.7 SIGMA=   4.0 PHAS=   64.1 FOM= 0.34 TEST= 0
INDE 13 72 17 FOBS=    37.9 SIGMA=   8.1 PHAS= -166.4 FOM= 0.23 TEST= 0
INDE 13 72 21 FOBS=    96.0 SIGMA=   3.0 PHAS=  164.7 FOM= 0.93 TEST= 0
INDE 13 72 23 FOBS=    47.0 SIGMA=   6.9 PHAS=  167.2 FOM= 0.76 TEST= 0
INDE 13 73 16 FOBS=    32.6 SIGMA=   7.8 PHAS=  -85.4 FOM= 0.29 TEST= 0
INDE 13 73 22 FOBS=    86.9 SIGMA=   3.5 PHAS=   76.1 FOM= 0.90 TEST= 0
INDE 13 74 17 FOBS=    29.6 SIGMA=  10.3 PHAS= -154.8 FOM= 0.29 TEST= 0
INDE 14 14 14 FOBS=    63.8 SIGMA=   1.5 PHAS= -112.8 FOM= 0.99 TEST= 0
INDE 14 15 15 FOBS=   100.5 SIGMA=   1.1 PHAS=  -17.3 FOM= 0.94 TEST= 0
INDE 14 15 17 FOBS=    94.7 SIGMA=   0.8 PHAS=  -73.8 FOM= 0.98 TEST= 0
INDE 14 15 19 FOBS=   208.5 SIGMA=   0.5 PHAS=    6.4 FOM= 0.98 TEST= 0
INDE 14 15 21 FOBS=    96.6 SIGMA=   0.8 PHAS=  136.9 FOM= 0.98 TEST= 0
INDE 14 15 23 FOBS=    35.7 SIGMA=   2.2 PHAS= -104.3 FOM= 0.95 TEST= 0
```

*FIG. 12A - 340*

```
INDE 14 15 25 FOBS=   157.8 SIGMA=  0.6 PHAS=   22.3 FOM= 0.87 TEST= 0
INDE 14 15 27 FOBS=   208.1 SIGMA=  0.5 PHAS=  142.7 FOM= 0.98 TEST= 0
INDE 14 15 29 FOBS=   234.3 SIGMA=  0.5 PHAS= -168.9 FOM= 0.93 TEST= 0
INDE 14 15 31 FOBS=   171.6 SIGMA=  0.6 PHAS=  169.7 FOM= 0.93 TEST= 0
INDE 14 15 33 FOBS=   188.9 SIGMA=  0.6 PHAS=  178.9 FOM= 0.96 TEST= 0
INDE 14 15 35 FOBS=   320.2 SIGMA=  0.5 PHAS= -116.7 FOM= 0.92 TEST= 0
INDE 14 15 37 FOBS=    69.7 SIGMA=  1.8 PHAS=   18.2 FOM= 0.75 TEST= 0
INDE 14 15 39 FOBS=   421.7 SIGMA=  0.6 PHAS=  136.4 FOM= 0.97 TEST= 0
INDE 14 15 41 FOBS=   216.4 SIGMA=  0.9 PHAS=  157.3 FOM= 0.95 TEST= 0
INDE 14 15 43 FOBS=   152.7 SIGMA=  1.5 PHAS=   32.2 FOM= 0.97 TEST= 0
INDE 14 15 45 FOBS=   139.6 SIGMA=  1.6 PHAS=   21.3 FOM= 0.96 TEST= 0
INDE 14 15 47 FOBS=   195.9 SIGMA=  1.5 PHAS=   19.7 FOM= 0.92 TEST= 0
INDE 14 15 49 FOBS=   146.6 SIGMA=  1.9 PHAS= -163.9 FOM= 0.93 TEST= 0
INDE 14 15 51 FOBS=    68.9 SIGMA=  3.1 PHAS=  -57.8 FOM= 0.51 TEST= 0
INDE 14 15 53 FOBS=    70.0 SIGMA=  2.5 PHAS=  178.4 FOM= 0.80 TEST= 0
INDE 14 15 55 FOBS=   147.7 SIGMA=  1.3 PHAS=  129.4 FOM= 0.89 TEST= 0
INDE 14 15 57 FOBS=    28.2 SIGMA=  6.4 PHAS=   76.4 FOM= 0.16 TEST= 0
INDE 14 15 59 FOBS=    72.6 SIGMA=  2.3 PHAS=   -8.2 FOM= 0.36 TEST= 0
INDE 14 15 61 FOBS=   130.2 SIGMA=  1.8 PHAS=   19.8 FOM= 0.90 TEST= 0
INDE 14 15 63 FOBS=     0.0 SIGMA= 26.0 PHAS=    0.0 FOM= 0.00 TEST= 1
INDE 14 15 65 FOBS=     6.1 SIGMA= 35.2 PHAS= -142.8 FOM= 0.12 TEST= 0
INDE 14 15 67 FOBS=    76.2 SIGMA=  3.4 PHAS=  -42.5 FOM= 0.88 TEST= 0
INDE 14 16 14 FOBS=    19.6 SIGMA=  3.9 PHAS=  132.6 FOM= 0.13 TEST= 0
INDE 14 16 16 FOBS=   128.8 SIGMA=  0.7 PHAS= -175.8 FOM= 0.75 TEST= 0
INDE 14 16 18 FOBS=   152.2 SIGMA=  0.6 PHAS= -127.7 FOM= 0.86 TEST= 0
INDE 14 16 20 FOBS=   103.3 SIGMA=  0.8 PHAS=  178.2 FOM= 0.99 TEST= 0
INDE 14 16 22 FOBS=   176.1 SIGMA=  0.6 PHAS=   38.6 FOM= 0.98 TEST= 0
INDE 14 16 24 FOBS=   114.6 SIGMA=  0.8 PHAS=  -67.2 FOM= 0.98 TEST= 1
INDE 14 16 26 FOBS=    27.3 SIGMA=  2.9 PHAS= -127.4 FOM= 0.96 TEST= 0
INDE 14 16 28 FOBS=   419.6 SIGMA=  0.4 PHAS=  100.9 FOM= 0.98 TEST= 0
INDE 14 16 30 FOBS=    50.7 SIGMA=  1.8 PHAS=   90.5 FOM= 0.75 TEST= 0
INDE 14 16 32 FOBS=   111.9 SIGMA=  0.9 PHAS=   45.3 FOM= 0.96 TEST= 0
INDE 14 16 34 FOBS=    30.4 SIGMA=  3.6 PHAS= -168.7 FOM= 0.77 TEST= 0
INDE 14 16 36 FOBS=   322.1 SIGMA=  0.5 PHAS=  159.1 FOM= 0.94 TEST= 0
INDE 14 16 38 FOBS=   110.7 SIGMA=  1.3 PHAS=   62.4 FOM= 0.90 TEST= 0
INDE 14 16 40 FOBS=   210.4 SIGMA=  0.8 PHAS=  115.8 FOM= 0.96 TEST= 0
INDE 14 16 42 FOBS=   330.8 SIGMA=  0.8 PHAS=   97.6 FOM= 0.97 TEST= 0
INDE 14 16 44 FOBS=   307.8 SIGMA=  0.8 PHAS=  -72.4 FOM= 0.98 TEST= 0
INDE 14 16 46 FOBS=    48.4 SIGMA=  3.5 PHAS=  -89.9 FOM= 0.83 TEST= 0
INDE 14 16 48 FOBS=   254.7 SIGMA=  0.8 PHAS=  127.3 FOM= 0.95 TEST= 0
INDE 14 16 50 FOBS=    73.2 SIGMA=  2.3 PHAS=  174.7 FOM= 0.70 TEST= 0
INDE 14 16 52 FOBS=   131.2 SIGMA=  1.5 PHAS= -109.5 FOM= 0.89 TEST= 0
INDE 14 16 54 FOBS=    34.4 SIGMA=  5.6 PHAS=  101.6 FOM= 0.38 TEST= 1
INDE 14 16 56 FOBS=     0.0 SIGMA= 18.6 PHAS=    0.0 FOM= 0.00 TEST= 0
INDE 14 16 58 FOBS=   117.0 SIGMA=  1.8 PHAS=  -49.7 FOM= 0.91 TEST= 0
INDE 14 16 60 FOBS=   137.5 SIGMA=  1.2 PHAS= -116.3 FOM= 0.96 TEST= 0
INDE 14 16 62 FOBS=    49.6 SIGMA=  4.7 PHAS=   74.8 FOM= 0.81 TEST= 0
INDE 14 16 64 FOBS=    47.5 SIGMA=  4.7 PHAS=  -41.8 FOM= 0.56 TEST= 0
INDE 14 16 66 FOBS=    28.7 SIGMA=  7.6 PHAS=   -2.7 FOM= 0.27 TEST= 0
INDE 14 17 15 FOBS=   217.1 SIGMA=  0.5 PHAS= -105.3 FOM= 0.98 TEST= 0
INDE 14 17 17 FOBS=    79.9 SIGMA=  1.0 PHAS= -136.6 FOM= 0.96 TEST= 0
INDE 14 17 19 FOBS=    58.6 SIGMA=  1.1 PHAS=    2.2 FOM= 0.78 TEST= 0
INDE 14 17 21 FOBS=    90.5 SIGMA=  0.8 PHAS=   58.0 FOM= 0.82 TEST= 1
INDE 14 17 23 FOBS=   175.4 SIGMA=  0.5 PHAS=  -41.9 FOM= 0.96 TEST= 0
INDE 14 17 25 FOBS=    77.4 SIGMA=  1.0 PHAS=   70.5 FOM= 0.40 TEST= 1
INDE 14 17 27 FOBS=   331.7 SIGMA=  0.4 PHAS=   96.0 FOM= 0.98 TEST= 0
INDE 14 17 29 FOBS=   338.0 SIGMA=  0.4 PHAS=  -27.4 FOM= 0.96 TEST= 0
INDE 14 17 31 FOBS=    73.6 SIGMA=  1.2 PHAS= -124.1 FOM= 0.97 TEST= 0
INDE 14 17 33 FOBS=   161.1 SIGMA=  0.6 PHAS=  146.4 FOM= 0.90 TEST= 0
INDE 14 17 35 FOBS=   176.1 SIGMA=  0.6 PHAS=  -80.6 FOM= 0.88 TEST= 0
INDE 14 17 37 FOBS=   166.8 SIGMA=  0.7 PHAS=   44.4 FOM= 0.88 TEST= 0
INDE 14 17 39 FOBS=   171.6 SIGMA=  0.7 PHAS=   79.9 FOM= 0.94 TEST= 0
INDE 14 17 41 FOBS=   154.9 SIGMA=  1.0 PHAS=   10.2 FOM= 0.91 TEST= 0
INDE 14 17 43 FOBS=   164.3 SIGMA=  1.1 PHAS=  -25.9 FOM= 0.96 TEST= 0
INDE 14 17 45 FOBS=   157.4 SIGMA=  1.2 PHAS= -130.5 FOM= 0.92 TEST= 0
INDE 14 17 47 FOBS=   134.2 SIGMA=  1.3 PHAS=   30.1 FOM= 0.79 TEST= 0
INDE 14 17 49 FOBS=   162.7 SIGMA=  1.1 PHAS=  120.8 FOM= 0.96 TEST= 0
INDE 14 17 51 FOBS=   130.8 SIGMA=  1.3 PHAS=   98.1 FOM= 0.48 TEST= 1
INDE 14 17 53 FOBS=    70.3 SIGMA=  2.3 PHAS=   42.0 FOM= 0.68 TEST= 0
INDE 14 17 55 FOBS=   119.3 SIGMA=  1.5 PHAS=   72.4 FOM= 0.94 TEST= 0
```

*FIG. 12A - 341*

```
INDE  14  17  57  FOBS=    90.7  SIGMA=   2.3  PHAS=   169.7  FOM=  0.90  TEST= 0
INDE  14  17  59  FOBS=    99.5  SIGMA=   2.1  PHAS=   161.7  FOM=  0.87  TEST= 0
INDE  14  17  61  FOBS=    74.5  SIGMA=   3.2  PHAS=    99.4  FOM=  0.88  TEST= 0
INDE  14  17  63  FOBS=     0.0  SIGMA=  21.9  PHAS=     0.0  FOM=  0.00  TEST= 1
INDE  14  17  65  FOBS=    21.2  SIGMA=  10.8  PHAS=    93.5  FOM=  0.04  TEST= 0
INDE  14  18  14  FOBS=   110.5  SIGMA=   0.7  PHAS=  -177.8  FOM=  0.84  TEST= 0
INDE  14  18  16  FOBS=   155.0  SIGMA=   0.6  PHAS=   107.2  FOM=  0.99  TEST= 0
INDE  14  18  18  FOBS=   191.0  SIGMA=   0.5  PHAS=   177.1  FOM=  0.87  TEST= 0
INDE  14  18  20  FOBS=    80.8  SIGMA=   0.9  PHAS=   152.4  FOM=  0.97  TEST= 0
INDE  14  18  22  FOBS=    85.3  SIGMA=   0.9  PHAS=    24.2  FOM=  0.81  TEST= 0
INDE  14  18  24  FOBS=   240.4  SIGMA=   0.5  PHAS=   -49.3  FOM=  0.98  TEST= 1
INDE  14  18  26  FOBS=   282.0  SIGMA=   0.5  PHAS=   -83.3  FOM=  0.97  TEST= 0
INDE  14  18  28  FOBS=   126.6  SIGMA=   0.8  PHAS=  -170.8  FOM=  0.86  TEST= 0
INDE  14  18  30  FOBS=    30.1  SIGMA=   3.0  PHAS=  -147.8  FOM=  0.85  TEST= 0
INDE  14  18  32  FOBS=    97.3  SIGMA=   1.0  PHAS=   -36.5  FOM=  0.81  TEST= 0
INDE  14  18  34  FOBS=   193.1  SIGMA=   0.6  PHAS=   114.2  FOM=  0.97  TEST= 0
INDE  14  18  36  FOBS=   310.0  SIGMA=   0.5  PHAS=  -163.6  FOM=  0.97  TEST= 0
INDE  14  18  38  FOBS=   174.5  SIGMA=   0.8  PHAS=   -26.1  FOM=  0.97  TEST= 0
INDE  14  18  40  FOBS=   150.9  SIGMA=   1.0  PHAS=    98.9  FOM=  0.85  TEST= 0
INDE  14  18  42  FOBS=   132.3  SIGMA=   1.3  PHAS=    97.5  FOM=  0.96  TEST= 0
INDE  14  18  44  FOBS=   107.1  SIGMA=   1.7  PHAS=  -137.6  FOM=  0.73  TEST= 0
INDE  14  18  46  FOBS=     0.0  SIGMA=  19.1  PHAS=     0.0  FOM=  0.00  TEST= 0
INDE  14  18  48  FOBS=    26.4  SIGMA=   7.6  PHAS=    17.7  FOM=  0.39  TEST= 0
INDE  14  18  50  FOBS=    76.8  SIGMA=   2.2  PHAS=    62.3  FOM=  0.87  TEST= 1
INDE  14  18  52  FOBS=    88.3  SIGMA=   1.8  PHAS=  -136.8  FOM=  0.81  TEST= 0
INDE  14  18  54  FOBS=   138.5  SIGMA=   1.2  PHAS=   -41.7  FOM=  0.95  TEST= 0
INDE  14  18  56  FOBS=   223.8  SIGMA=   0.8  PHAS=   -17.8  FOM=  0.97  TEST= 0
INDE  14  18  58  FOBS=   143.8  SIGMA=   1.5  PHAS=   -15.8  FOM=  0.95  TEST= 0
INDE  14  18  60  FOBS=    63.8  SIGMA=   3.1  PHAS=   -24.2  FOM=  0.78  TEST= 0
INDE  14  18  62  FOBS=    76.2  SIGMA=   2.9  PHAS=    69.8  FOM=  0.80  TEST= 0
INDE  14  18  64  FOBS=    77.3  SIGMA=   2.9  PHAS=    55.9  FOM=  0.94  TEST= 0
INDE  14  18  66  FOBS=    69.4  SIGMA=   7.3  PHAS=    73.6  FOM=  0.70  TEST= 0
INDE  14  19  15  FOBS=   114.4  SIGMA=   0.8  PHAS=   -73.6  FOM=  0.84  TEST= 0
INDE  14  19  17  FOBS=   198.1  SIGMA=   0.5  PHAS=    75.2  FOM=  0.98  TEST= 0
INDE  14  19  19  FOBS=    53.9  SIGMA=   1.5  PHAS=     7.6  FOM=  0.94  TEST= 0
INDE  14  19  21  FOBS=    45.2  SIGMA=   1.6  PHAS=    -9.3  FOM=  0.96  TEST= 0
INDE  14  19  23  FOBS=    78.8  SIGMA=   1.0  PHAS=    23.3  FOM=  0.91  TEST= 0
INDE  14  19  25  FOBS=   343.6  SIGMA=   0.4  PHAS=   177.0  FOM=  0.97  TEST= 0
INDE  14  19  27  FOBS=   144.3  SIGMA=   0.7  PHAS=   110.1  FOM=  0.87  TEST= 0
INDE  14  19  29  FOBS=   171.1  SIGMA=   0.6  PHAS=   -66.7  FOM=  0.86  TEST= 0
INDE  14  19  31  FOBS=   119.7  SIGMA=   0.8  PHAS=   119.6  FOM=  0.94  TEST= 0
INDE  14  19  33  FOBS=   134.3  SIGMA=   0.8  PHAS=   -67.3  FOM=  0.98  TEST= 1
INDE  14  19  35  FOBS=   271.5  SIGMA=   0.6  PHAS=    11.1  FOM=  0.93  TEST= 0
INDE  14  19  37  FOBS=   188.8  SIGMA=   0.7  PHAS=   101.7  FOM=  0.97  TEST= 0
INDE  14  19  39  FOBS=   162.5  SIGMA=   0.9  PHAS=   -45.5  FOM=  0.94  TEST= 0
INDE  14  19  41  FOBS=   155.7  SIGMA=   1.0  PHAS=    14.2  FOM=  0.93  TEST= 0
INDE  14  19  43  FOBS=   208.0  SIGMA=   0.8  PHAS=   -36.4  FOM=  0.94  TEST= 0
INDE  14  19  45  FOBS=     0.0  SIGMA=  21.3  PHAS=     0.0  FOM=  0.00  TEST= 0
INDE  14  19  47  FOBS=    69.6  SIGMA=   2.4  PHAS=  -122.8  FOM=  0.48  TEST= 0
INDE  14  19  49  FOBS=   112.4  SIGMA=   1.5  PHAS=   120.9  FOM=  0.93  TEST= 0
INDE  14  19  51  FOBS=    54.1  SIGMA=   3.0  PHAS=   -44.0  FOM=  0.16  TEST= 0
INDE  14  19  53  FOBS=     0.0  SIGMA=  18.3  PHAS=     0.0  FOM=  0.00  TEST= 0
INDE  14  19  55  FOBS=   142.0  SIGMA=   1.2  PHAS=  -129.0  FOM=  0.93  TEST= 0
INDE  14  19  57  FOBS=   156.5  SIGMA=   1.2  PHAS=  -128.6  FOM=  0.97  TEST= 0
INDE  14  19  59  FOBS=    76.8  SIGMA=   2.3  PHAS=  -117.3  FOM=  0.91  TEST= 0
INDE  14  19  61  FOBS=    10.4  SIGMA=  21.7  PHAS=   -38.0  FOM=  0.15  TEST= 0
INDE  14  19  63  FOBS=    26.3  SIGMA=   9.4  PHAS=   -57.7  FOM=  0.24  TEST= 0
INDE  14  19  65  FOBS=    56.3  SIGMA=   8.9  PHAS=    10.7  FOM=  0.71  TEST= 1
INDE  14  20  14  FOBS=    62.4  SIGMA=   1.2  PHAS=   160.7  FOM=  0.96  TEST= 0
INDE  14  20  16  FOBS=   173.1  SIGMA=   0.6  PHAS=    81.5  FOM=  0.97  TEST= 0
INDE  14  20  18  FOBS=    20.0  SIGMA=   3.9  PHAS=   -44.6  FOM=  0.43  TEST= 0
INDE  14  20  20  FOBS=   134.3  SIGMA=   0.7  PHAS=   128.2  FOM=  0.97  TEST= 0
INDE  14  20  22  FOBS=    33.7  SIGMA=   2.5  PHAS=  -124.2  FOM=  0.85  TEST= 0
INDE  14  20  24  FOBS=    42.0  SIGMA=   2.0  PHAS=   -52.1  FOM=  0.98  TEST= 0
INDE  14  20  26  FOBS=   217.3  SIGMA=   0.6  PHAS=    81.7  FOM=  0.90  TEST= 0
INDE  14  20  28  FOBS=   124.7  SIGMA=   0.8  PHAS=    -9.6  FOM=  0.94  TEST= 0
INDE  14  20  30  FOBS=   238.2  SIGMA=   0.5  PHAS=    25.6  FOM=  0.90  TEST= 0
INDE  14  20  32  FOBS=   220.0  SIGMA=   0.6  PHAS=  -110.3  FOM=  0.99  TEST= 0
INDE  14  20  34  FOBS=    82.2  SIGMA=   1.3  PHAS=   179.0  FOM=  0.30  TEST= 0
INDE  14  20  36  FOBS=   116.5  SIGMA=   1.0  PHAS=   -37.6  FOM=  0.78  TEST= 0
```

*FIG. 12A - 342*

```
INDE  14  20  38  FOBS=   113.3  SIGMA=   1.2  PHAS=   111.9  FOM=  0.85  TEST= 1
INDE  14  20  40  FOBS=   121.3  SIGMA=   1.2  PHAS=   170.4  FOM=  0.81  TEST= 1
INDE  14  20  42  FOBS=   116.4  SIGMA=   1.5  PHAS=   -98.1  FOM=  0.87  TEST= 0
INDE  14  20  44  FOBS=   205.6  SIGMA=   0.8  PHAS=  -114.1  FOM=  0.92  TEST= 0
INDE  14  20  46  FOBS=    76.2  SIGMA=   2.1  PHAS=    76.5  FOM=  0.91  TEST= 0
INDE  14  20  48  FOBS=     0.0  SIGMA=  17.9  PHAS=     0.0  FOM=  0.00  TEST= 0
INDE  14  20  50  FOBS=    88.4  SIGMA=   2.0  PHAS=   -63.2  FOM=  0.51  TEST= 0
INDE  14  20  52  FOBS=   118.8  SIGMA=   1.4  PHAS=   -77.2  FOM=  0.84  TEST= 1
INDE  14  20  54  FOBS=    65.9  SIGMA=   2.5  PHAS=   -90.5  FOM=  0.66  TEST= 0
INDE  14  20  56  FOBS=    54.4  SIGMA=   2.9  PHAS=    47.3  FOM=  0.89  TEST= 0
INDE  14  20  58  FOBS=    74.8  SIGMA=   2.4  PHAS=   172.2  FOM=  0.64  TEST= 0
INDE  14  20  60  FOBS=     0.0  SIGMA=  19.7  PHAS=     0.0  FOM=  0.00  TEST= 0
INDE  14  20  62  FOBS=    59.2  SIGMA=   3.2  PHAS=   -24.9  FOM=  0.45  TEST= 1
INDE  14  20  64  FOBS=    13.4  SIGMA=  26.2  PHAS=   -94.2  FOM=  0.20  TEST= 0
INDE  14  21  15  FOBS=   195.3  SIGMA=   0.6  PHAS=    12.5  FOM=  0.92  TEST= 0
INDE  14  21  17  FOBS=   228.4  SIGMA=   0.5  PHAS=    34.2  FOM=  0.95  TEST= 0
INDE  14  21  19  FOBS=    51.0  SIGMA=   1.6  PHAS=   -40.9  FOM=  0.96  TEST= 1
INDE  14  21  21  FOBS=   143.2  SIGMA=   0.7  PHAS=    17.3  FOM=  0.99  TEST= 0
INDE  14  21  23  FOBS=   178.9  SIGMA=   0.6  PHAS=    11.7  FOM=  0.99  TEST= 0
INDE  14  21  25  FOBS=     0.0  SIGMA=  13.0  PHAS=     0.0  FOM=  0.00  TEST= 0
INDE  14  21  27  FOBS=   188.3  SIGMA=   0.6  PHAS=   -58.2  FOM=  0.91  TEST= 0
INDE  14  21  29  FOBS=   201.8  SIGMA=   0.6  PHAS=   -47.1  FOM=  0.90  TEST= 0
INDE  14  21  31  FOBS=    59.4  SIGMA=   1.7  PHAS=   126.2  FOM=  0.54  TEST= 0
INDE  14  21  33  FOBS=   157.4  SIGMA=   0.8  PHAS=  -135.1  FOM=  0.86  TEST= 0
INDE  14  21  35  FOBS=   356.1  SIGMA=   0.5  PHAS=   -84.6  FOM=  0.95  TEST= 0
INDE  14  21  37  FOBS=    92.4  SIGMA=   1.4  PHAS=   -13.2  FOM=  0.76  TEST= 0
INDE  14  21  39  FOBS=   230.2  SIGMA=   0.7  PHAS=    42.9  FOM=  0.97  TEST= 0
INDE  14  21  41  FOBS=     0.0  SIGMA=  17.7  PHAS=     0.0  FOM=  0.00  TEST= 0
INDE  14  21  43  FOBS=   215.4  SIGMA=   0.8  PHAS=    55.7  FOM=  0.49  TEST= 1
INDE  14  21  45  FOBS=    60.8  SIGMA=   2.5  PHAS=   140.4  FOM=  0.37  TEST= 0
INDE  14  21  47  FOBS=   139.4  SIGMA=   1.2  PHAS=   -90.8  FOM=  0.94  TEST= 0
INDE  14  21  49  FOBS=   241.9  SIGMA=   0.8  PHAS=   139.2  FOM=  0.95  TEST= 0
INDE  14  21  51  FOBS=    98.9  SIGMA=   1.7  PHAS=    64.8  FOM=  0.92  TEST= 0
INDE  14  21  53  FOBS=    73.1  SIGMA=   2.2  PHAS=   175.9  FOM=  0.81  TEST= 0
INDE  14  21  55  FOBS=    79.8  SIGMA=   2.0  PHAS=  -128.2  FOM=  0.87  TEST= 0
INDE  14  21  57  FOBS=     0.0  SIGMA=  18.9  PHAS=     0.0  FOM=  0.00  TEST= 0
INDE  14  21  59  FOBS=   156.7  SIGMA=   1.4  PHAS=   140.8  FOM=  0.93  TEST= 0
INDE  14  21  61  FOBS=    80.4  SIGMA=   2.4  PHAS=   -72.4  FOM=  0.82  TEST= 0
INDE  14  21  63  FOBS=    54.2  SIGMA=   4.6  PHAS=   -49.2  FOM=  0.79  TEST= 0
INDE  14  21  65  FOBS=   118.7  SIGMA=   3.1  PHAS=   122.2  FOM=  0.95  TEST= 0
INDE  14  22  14  FOBS=   143.1  SIGMA=   0.6  PHAS=   -89.1  FOM=  0.94  TEST= 0
INDE  14  22  16  FOBS=   256.5  SIGMA=   0.6  PHAS=   -63.3  FOM=  0.99  TEST= 0
INDE  14  22  18  FOBS=   190.1  SIGMA=   0.6  PHAS=   -95.7  FOM=  0.92  TEST= 0
INDE  14  22  20  FOBS=   112.1  SIGMA=   0.8  PHAS=  -160.2  FOM=  0.99  TEST= 0
INDE  14  22  22  FOBS=   284.2  SIGMA=   0.5  PHAS=  -111.1  FOM=  0.97  TEST= 0
INDE  14  22  24  FOBS=   103.6  SIGMA=   1.0  PHAS=   -92.3  FOM=  0.88  TEST= 0
INDE  14  22  26  FOBS=   136.3  SIGMA=   0.8  PHAS=   155.9  FOM=  0.94  TEST= 0
INDE  14  22  28  FOBS=   259.1  SIGMA=   0.5  PHAS=   -14.9  FOM=  0.95  TEST= 0
INDE  14  22  30  FOBS=   183.2  SIGMA=   0.6  PHAS=   114.5  FOM=  0.98  TEST= 0
INDE  14  22  32  FOBS=   225.6  SIGMA=   0.6  PHAS=  -138.8  FOM=  0.94  TEST= 0
INDE  14  22  34  FOBS=    85.0  SIGMA=   1.4  PHAS=  -160.9  FOM=  0.85  TEST= 0
INDE  14  22  36  FOBS=   268.4  SIGMA=   0.6  PHAS=  -162.0  FOM=  0.97  TEST= 0
INDE  14  22  38  FOBS=   143.3  SIGMA=   1.0  PHAS=  -138.7  FOM=  0.84  TEST= 0
INDE  14  22  40  FOBS=    72.4  SIGMA=   2.1  PHAS=   -58.3  FOM=  0.41  TEST= 0
INDE  14  22  42  FOBS=    27.6  SIGMA=   6.0  PHAS=  -113.7  FOM=  0.85  TEST= 0
INDE  14  22  44  FOBS=     0.0  SIGMA=  17.7  PHAS=     0.0  FOM=  0.00  TEST= 0
INDE  14  22  46  FOBS=    50.9  SIGMA=   2.9  PHAS=   103.9  FOM=  0.80  TEST= 0
INDE  14  22  48  FOBS=   146.5  SIGMA=   1.1  PHAS=   -40.1  FOM=  0.83  TEST= 0
INDE  14  22  50  FOBS=   152.6  SIGMA=   1.1  PHAS=   -37.9  FOM=  0.91  TEST= 0
INDE  14  22  52  FOBS=   115.9  SIGMA=   1.4  PHAS=   -28.4  FOM=  0.95  TEST= 0
INDE  14  22  54  FOBS=    73.6  SIGMA=   2.2  PHAS=   109.5  FOM=  0.92  TEST= 0
INDE  14  22  56  FOBS=    81.9  SIGMA=   2.3  PHAS=   120.8  FOM=  0.94  TEST= 0
INDE  14  22  58  FOBS=    67.1  SIGMA=   2.7  PHAS=    74.5  FOM=  0.90  TEST= 0
INDE  14  22  60  FOBS=    57.4  SIGMA=   3.5  PHAS=    89.4  FOM=  0.83  TEST= 0
INDE  14  22  62  FOBS=    58.3  SIGMA=   4.3  PHAS=   142.2  FOM=  0.49  TEST= 0
INDE  14  22  64  FOBS=    43.0  SIGMA=   8.4  PHAS=    26.7  FOM=  0.72  TEST= 0
INDE  14  22  66  FOBS=     0.0  SIGMA=  31.5  PHAS=     0.0  FOM=  0.00  TEST= 0
INDE  14  22  68  FOBS=    85.5  SIGMA=   6.1  PHAS=   163.8  FOM=  0.89  TEST= 0
INDE  14  23  15  FOBS=   271.4  SIGMA=   0.5  PHAS=  -145.5  FOM=  0.97  TEST= 0
INDE  14  23  17  FOBS=   172.6  SIGMA=   0.7  PHAS=  -166.1  FOM=  0.99  TEST= 0
```

*FIG. 12A - 343*

```
INDE  14  23  19  FOBS=   124.4  SIGMA=   0.8  PHAS=   146.7  FOM=  0.96  TEST=  0
INDE  14  23  21  FOBS=   223.5  SIGMA=   0.5  PHAS=   122.8  FOM=  0.97  TEST=  0
INDE  14  23  23  FOBS=   208.2  SIGMA=   0.5  PHAS=    69.5  FOM=  0.97  TEST=  0
INDE  14  23  25  FOBS=   225.7  SIGMA=   0.6  PHAS=    24.1  FOM=  0.99  TEST=  0
INDE  14  23  27  FOBS=   229.5  SIGMA=   0.6  PHAS=   -25.1  FOM=  0.95  TEST=  0
INDE  14  23  29  FOBS=   222.1  SIGMA=   0.6  PHAS=   -13.6  FOM=  0.94  TEST=  0
INDE  14  23  31  FOBS=   376.3  SIGMA=   0.7  PHAS=    34.5  FOM=  0.92  TEST=  0
INDE  14  23  33  FOBS=   286.9  SIGMA=   0.7  PHAS=   106.5  FOM=  0.97  TEST=  0
INDE  14  23  35  FOBS=    77.2  SIGMA=   1.8  PHAS=   -89.4  FOM=  0.96  TEST=  0
INDE  14  23  37  FOBS=   219.0  SIGMA=   0.8  PHAS=   144.0  FOM=  0.97  TEST=  0
INDE  14  23  39  FOBS=   161.6  SIGMA=   1.0  PHAS=   128.2  FOM=  0.97  TEST=  0
INDE  14  23  41  FOBS=    46.7  SIGMA=   3.3  PHAS=  -168.1  FOM=  0.27  TEST=  0
INDE  14  23  43  FOBS=     0.0  SIGMA=  18.5  PHAS=     0.0  FOM=  0.00  TEST=  0
INDE  14  23  45  FOBS=   155.0  SIGMA=   1.0  PHAS=   127.6  FOM=  0.07  TEST=  1
INDE  14  23  47  FOBS=   184.4  SIGMA=   0.9  PHAS=  -118.1  FOM=  0.93  TEST=  0
INDE  14  23  49  FOBS=   148.2  SIGMA=   1.0  PHAS=  -173.8  FOM=  0.95  TEST=  0
INDE  14  23  51  FOBS=    23.2  SIGMA=   7.6  PHAS=   120.6  FOM=  0.04  TEST=  0
INDE  14  23  53  FOBS=     0.0  SIGMA=  17.8  PHAS=     0.0  FOM=  0.00  TEST=  0
INDE  14  23  55  FOBS=    40.3  SIGMA=   4.0  PHAS=    12.6  FOM=  0.72  TEST=  0
INDE  14  23  57  FOBS=   140.6  SIGMA=   1.4  PHAS=     7.3  FOM=  0.95  TEST=  0
INDE  14  23  59  FOBS=    53.5  SIGMA=   3.7  PHAS=   118.5  FOM=  0.61  TEST=  0
INDE  14  23  61  FOBS=    19.5  SIGMA=  12.8  PHAS=     8.8  FOM=  0.23  TEST=  0
INDE  14  23  63  FOBS=    42.7  SIGMA=   5.9  PHAS=   -33.6  FOM=  0.62  TEST=  0
INDE  14  23  65  FOBS=    15.3  SIGMA=  32.0  PHAS=   152.9  FOM=  0.05  TEST=  0
INDE  14  23  67  FOBS=    53.5  SIGMA=   9.6  PHAS=  -173.9  FOM=  0.69  TEST=  0
INDE  14  23  69  FOBS=    57.8  SIGMA=   8.9  PHAS=   -97.2  FOM=  0.48  TEST=  0
INDE  14  24  14  FOBS=    89.8  SIGMA=   0.8  PHAS=   116.3  FOM=  0.99  TEST=  0
INDE  14  24  16  FOBS=    77.8  SIGMA=   1.2  PHAS=   149.0  FOM=  0.98  TEST=  0
INDE  14  24  18  FOBS=    39.6  SIGMA=   2.2  PHAS=    60.5  FOM=  0.95  TEST=  0
INDE  14  24  20  FOBS=   181.1  SIGMA=   0.6  PHAS=    48.0  FOM=  0.97  TEST=  0
INDE  14  24  22  FOBS=    33.9  SIGMA=   2.7  PHAS=   136.1  FOM=  0.93  TEST=  0
INDE  14  24  24  FOBS=   154.5  SIGMA=   0.7  PHAS=  -101.8  FOM=  0.91  TEST=  0
INDE  14  24  26  FOBS=   209.4  SIGMA=   0.6  PHAS=   -80.5  FOM=  0.77  TEST=  1
INDE  14  24  28  FOBS=   266.0  SIGMA=   0.6  PHAS=   -69.4  FOM=  0.94  TEST=  0
INDE  14  24  30  FOBS=   263.2  SIGMA=   0.6  PHAS=  -174.1  FOM=  0.96  TEST=  0
INDE  14  24  32  FOBS=    42.5  SIGMA=   2.9  PHAS=   -60.1  FOM=  0.95  TEST=  0
INDE  14  24  34  FOBS=   126.9  SIGMA=   1.1  PHAS=    28.5  FOM=  0.91  TEST=  0
INDE  14  24  36  FOBS=   177.1  SIGMA=   0.9  PHAS=    84.9  FOM=  0.95  TEST=  0
INDE  14  24  38  FOBS=   176.7  SIGMA=   1.0  PHAS=    16.9  FOM=  0.93  TEST=  0
INDE  14  24  40  FOBS=     0.0  SIGMA=  18.5  PHAS=     0.0  FOM=  0.00  TEST=  0
INDE  14  24  42  FOBS=   155.4  SIGMA=   1.0  PHAS=   -71.7  FOM=  0.87  TEST=  0
INDE  14  24  44  FOBS=   159.9  SIGMA=   1.0  PHAS=   -65.7  FOM=  0.71  TEST=  0
INDE  14  24  46  FOBS=   174.5  SIGMA=   0.9  PHAS=   159.0  FOM=  0.94  TEST=  0
INDE  14  24  48  FOBS=    72.3  SIGMA=   2.0  PHAS=   141.4  FOM=  0.84  TEST=  0
INDE  14  24  50  FOBS=    82.6  SIGMA=   1.8  PHAS=   142.3  FOM=  0.90  TEST=  0
INDE  14  24  52  FOBS=   101.3  SIGMA=   1.5  PHAS=   -18.8  FOM=  0.29  TEST=  1
INDE  14  24  54  FOBS=     0.0  SIGMA=  19.3  PHAS=     0.0  FOM=  0.00  TEST=  0
INDE  14  24  56  FOBS=    71.7  SIGMA=   2.6  PHAS=  -107.7  FOM=  0.84  TEST=  0
INDE  14  24  58  FOBS=   102.6  SIGMA=   2.0  PHAS=    -2.8  FOM=  0.86  TEST=  0
INDE  14  24  60  FOBS=    61.1  SIGMA=   4.2  PHAS=   -60.1  FOM=  0.70  TEST=  0
INDE  14  24  62  FOBS=    34.9  SIGMA=   7.2  PHAS=   -57.1  FOM=  0.28  TEST=  0
INDE  14  24  64  FOBS=     0.0  SIGMA=  31.7  PHAS=     0.0  FOM=  0.00  TEST=  0
INDE  14  24  66  FOBS=     7.8  SIGMA=  64.3  PHAS=     0.0  FOM=  0.00  TEST=  1
INDE  14  24  68  FOBS=    83.2  SIGMA=   6.3  PHAS=   133.8  FOM=  0.93  TEST=  0
INDE  14  24  70  FOBS=    63.4  SIGMA=   8.4  PHAS=  -151.7  FOM=  0.82  TEST=  0
INDE  14  24  72  FOBS=    14.6  SIGMA=  37.1  PHAS=   142.9  FOM=  0.19  TEST=  0
INDE  14  25  15  FOBS=    53.7  SIGMA=   1.5  PHAS=  -176.5  FOM=  0.80  TEST=  0
INDE  14  25  17  FOBS=    41.4  SIGMA=   2.2  PHAS=   -59.7  FOM=  0.43  TEST=  0
INDE  14  25  19  FOBS=   168.8  SIGMA=   0.6  PHAS=    -7.0  FOM=  0.92  TEST=  0
INDE  14  25  21  FOBS=   126.8  SIGMA=   0.8  PHAS=    30.6  FOM=  0.91  TEST=  0
INDE  14  25  23  FOBS=   138.9  SIGMA=   0.8  PHAS=    77.3  FOM=  0.89  TEST=  0
INDE  14  25  25  FOBS=    30.6  SIGMA=   3.6  PHAS=  -106.2  FOM=  0.20  TEST=  0
INDE  14  25  27  FOBS=   343.7  SIGMA=   0.5  PHAS=  -127.8  FOM=  0.93  TEST=  1
INDE  14  25  29  FOBS=   227.0  SIGMA=   0.7  PHAS=    71.0  FOM=  0.98  TEST=  0
INDE  14  25  31  FOBS=   234.8  SIGMA=   0.7  PHAS=    28.6  FOM=  0.95  TEST=  0
INDE  14  25  33  FOBS=   253.9  SIGMA=   0.7  PHAS=   -11.2  FOM=  0.94  TEST=  0
INDE  14  25  35  FOBS=   145.1  SIGMA=   1.1  PHAS=   -34.8  FOM=  0.92  TEST=  0
INDE  14  25  37  FOBS=    81.6  SIGMA=   2.0  PHAS=   -64.1  FOM=  0.68  TEST=  0
INDE  14  25  39  FOBS=    84.8  SIGMA=   2.0  PHAS=  -124.6  FOM=  0.69  TEST=  0
INDE  14  25  41  FOBS=    75.9  SIGMA=   2.3  PHAS=  -125.0  FOM=  0.69  TEST=  0
```

*FIG. 12A - 344*

```
INDE  14  25  43  FOBS=    180.6  SIGMA=   0.9  PHAS=  -179.2  FOM=  0.85  TEST= 0
INDE  14  25  45  FOBS=     67.6  SIGMA=   2.2  PHAS=    52.8  FOM=  0.52  TEST= 0
INDE  14  25  47  FOBS=     81.7  SIGMA=   1.8  PHAS=   127.4  FOM=  0.54  TEST= 0
INDE  14  25  49  FOBS=     34.0  SIGMA=   4.6  PHAS=   -92.0  FOM=  0.46  TEST= 0
INDE  14  25  51  FOBS=     61.7  SIGMA=   2.3  PHAS=   -13.1  FOM=  0.88  TEST= 0
INDE  14  25  53  FOBS=     79.5  SIGMA=   1.9  PHAS=    70.9  FOM=  0.84  TEST= 0
INDE  14  25  55  FOBS=     13.9  SIGMA=  12.6  PHAS=   -82.4  FOM=  0.05  TEST= 0
INDE  14  25  57  FOBS=     73.4  SIGMA=   2.9  PHAS=   -96.3  FOM=  0.89  TEST= 0
INDE  14  25  59  FOBS=     96.5  SIGMA=   2.7  PHAS=  -145.3  FOM=  0.79  TEST= 0
INDE  14  25  61  FOBS=     49.9  SIGMA=   5.1  PHAS=  -130.9  FOM=  0.37  TEST= 1
INDE  14  25  63  FOBS=     65.5  SIGMA=   4.5  PHAS=   115.1  FOM=  0.12  TEST= 1
INDE  14  25  65  FOBS=     27.2  SIGMA=  18.3  PHAS=   -70.8  FOM=  0.09  TEST= 0
INDE  14  25  67  FOBS=     29.3  SIGMA=   6.0  PHAS=  -148.4  FOM=  0.13  TEST= 0
INDE  14  25  69  FOBS=     94.6  SIGMA=   5.6  PHAS=    73.7  FOM=  0.93  TEST= 0
INDE  14  25  71  FOBS=     37.1  SIGMA=  14.6  PHAS=   114.1  FOM=  0.69  TEST= 0
INDE  14  26  14  FOBS=    146.6  SIGMA=   0.6  PHAS=    93.0  FOM=  0.97  TEST= 0
INDE  14  26  16  FOBS=     24.8  SIGMA=   3.8  PHAS=   139.9  FOM=  0.92  TEST= 0
INDE  14  26  18  FOBS=     60.8  SIGMA=   1.5  PHAS=   -57.4  FOM=  0.87  TEST= 0
INDE  14  26  20  FOBS=    200.4  SIGMA=   0.5  PHAS=   -66.8  FOM=  0.99  TEST= 0
INDE  14  26  22  FOBS=     21.5  SIGMA=   4.9  PHAS=   -73.3  FOM=  0.51  TEST= 0
INDE  14  26  24  FOBS=    227.0  SIGMA=   0.6  PHAS=  -151.5  FOM=  0.99  TEST= 0
INDE  14  26  26  FOBS=     86.5  SIGMA=   1.4  PHAS=  -178.5  FOM=  0.88  TEST= 0
INDE  14  26  28  FOBS=    183.1  SIGMA=   0.8  PHAS=   114.4  FOM=  0.99  TEST= 0
INDE  14  26  30  FOBS=    163.4  SIGMA=   1.0  PHAS=    26.0  FOM=  0.91  TEST= 0
INDE  14  26  32  FOBS=     84.0  SIGMA=   1.8  PHAS=  -137.6  FOM=  0.88  TEST= 0
INDE  14  26  34  FOBS=    255.7  SIGMA=   0.7  PHAS=   151.4  FOM=  0.90  TEST= 1
INDE  14  26  36  FOBS=     84.7  SIGMA=   1.9  PHAS=   -82.7  FOM=  0.92  TEST= 0
INDE  14  26  38  FOBS=    148.1  SIGMA=   1.2  PHAS=   -67.9  FOM=  0.50  TEST= 0
INDE  14  26  40  FOBS=    144.6  SIGMA=   1.2  PHAS=   -52.6  FOM=  0.92  TEST= 0
INDE  14  26  42  FOBS=     77.4  SIGMA=   2.2  PHAS=    61.0  FOM=  0.78  TEST= 0
INDE  14  26  44  FOBS=     60.6  SIGMA=   2.5  PHAS=    12.6  FOM=  0.30  TEST= 0
INDE  14  26  46  FOBS=     86.6  SIGMA=   1.8  PHAS=   135.2  FOM=  0.83  TEST= 0
INDE  14  26  48  FOBS=     98.5  SIGMA=   1.5  PHAS=   159.9  FOM=  0.55  TEST= 0
INDE  14  26  50  FOBS=     70.9  SIGMA=   2.1  PHAS=   139.4  FOM=  0.90  TEST= 0
INDE  14  26  52  FOBS=    151.6  SIGMA=   1.0  PHAS=   -22.7  FOM=  0.90  TEST= 0
INDE  14  26  54  FOBS=     39.7  SIGMA=   4.0  PHAS=    94.9  FOM=  0.68  TEST= 0
INDE  14  26  56  FOBS=     81.0  SIGMA=   2.4  PHAS=  -159.1  FOM=  0.83  TEST= 0
INDE  14  26  58  FOBS=     71.4  SIGMA=   3.3  PHAS=   155.2  FOM=  0.83  TEST= 0
INDE  14  26  60  FOBS=     33.7  SIGMA=   7.6  PHAS=  -176.4  FOM=  0.08  TEST= 0
INDE  14  26  62  FOBS=     27.4  SIGMA=  13.3  PHAS=    84.1  FOM=  0.17  TEST= 0
INDE  14  26  64  FOBS=     18.5  SIGMA=  26.1  PHAS=   104.6  FOM=  0.29  TEST= 0
INDE  14  26  66  FOBS=     83.9  SIGMA=   6.1  PHAS=   157.3  FOM=  0.79  TEST= 0
INDE  14  26  68  FOBS=      0.0  SIGMA=  18.6  PHAS=     0.0  FOM=  0.00  TEST= 0
INDE  14  26  70  FOBS=      0.0  SIGMA=  32.4  PHAS=     0.0  FOM=  0.00  TEST= 0
INDE  14  27  15  FOBS=    230.9  SIGMA=   0.5  PHAS=     7.6  FOM=  0.98  TEST= 1
INDE  14  27  17  FOBS=    143.9  SIGMA=   0.8  PHAS=   -38.4  FOM=  0.90  TEST= 0
INDE  14  27  19  FOBS=    155.2  SIGMA=   0.7  PHAS=   -60.7  FOM=  0.99  TEST= 0
INDE  14  27  21  FOBS=    116.8  SIGMA=   0.8  PHAS=   -30.6  FOM=  0.92  TEST= 0
INDE  14  27  23  FOBS=    218.4  SIGMA=   0.6  PHAS=    82.1  FOM=  0.93  TEST= 0
INDE  14  27  25  FOBS=    211.7  SIGMA=   0.7  PHAS=    58.3  FOM=  0.99  TEST= 0
INDE  14  27  27  FOBS=    145.6  SIGMA=   1.0  PHAS=     9.8  FOM=  0.91  TEST= 0
INDE  14  27  29  FOBS=    304.4  SIGMA=   0.8  PHAS=    -3.9  FOM=  0.94  TEST= 0
INDE  14  27  31  FOBS=    176.4  SIGMA=   1.0  PHAS=   -28.6  FOM=  0.95  TEST= 0
INDE  14  27  33  FOBS=    200.1  SIGMA=   0.9  PHAS=     2.1  FOM=  0.95  TEST= 0
INDE  14  27  35  FOBS=     61.5  SIGMA=   3.0  PHAS=   151.0  FOM=  0.93  TEST= 0
INDE  14  27  37  FOBS=    150.7  SIGMA=   1.2  PHAS=  -117.1  FOM=  0.93  TEST= 0
INDE  14  27  39  FOBS=    167.9  SIGMA=   1.1  PHAS=  -121.7  FOM=  0.96  TEST= 0
INDE  14  27  41  FOBS=     87.4  SIGMA=   2.0  PHAS=  -119.1  FOM=  0.77  TEST= 0
INDE  14  27  43  FOBS=    104.3  SIGMA=   1.6  PHAS=   174.5  FOM=  0.86  TEST= 0
INDE  14  27  45  FOBS=     94.1  SIGMA=   1.8  PHAS=    93.5  FOM=  0.88  TEST= 0
INDE  14  27  47  FOBS=    138.4  SIGMA=   1.1  PHAS=    -9.2  FOM=  0.91  TEST= 0
INDE  14  27  49  FOBS=     12.2  SIGMA=  13.3  PHAS=  -100.8  FOM=  0.08  TEST= 0
INDE  14  27  51  FOBS=    105.6  SIGMA=   1.4  PHAS=   -88.2  FOM=  0.91  TEST= 0
INDE  14  27  53  FOBS=     60.0  SIGMA=   2.6  PHAS=  -152.0  FOM=  0.53  TEST= 0
INDE  14  27  55  FOBS=    119.1  SIGMA=   1.5  PHAS=    76.4  FOM=  0.93  TEST= 0
INDE  14  27  57  FOBS=      1.2  SIGMA= 167.4  PHAS=  -170.3  FOM=  0.04  TEST= 0
INDE  14  27  59  FOBS=     65.4  SIGMA=   3.6  PHAS=   -79.6  FOM=  0.88  TEST= 0
INDE  14  27  61  FOBS=     32.2  SIGMA=  11.6  PHAS=   117.5  FOM=  0.37  TEST= 0
INDE  14  27  63  FOBS=     93.7  SIGMA=   3.8  PHAS=   -21.7  FOM=  0.88  TEST= 0
INDE  14  27  65  FOBS=      0.0  SIGMA=  31.2  PHAS=     0.0  FOM=  0.00  TEST= 0
```

*FIG. 12A - 345*

```
INDE  14  27  67  FOBS=   51.5  SIGMA=   4.0  PHAS=   -0.1  FOM= 0.62  TEST= 0
INDE  14  27  69  FOBS=   48.2  SIGMA=   3.6  PHAS=   26.9  FOM= 0.26  TEST= 0
INDE  14  27  71  FOBS=   56.0  SIGMA=   9.8  PHAS=  136.8  FOM= 0.80  TEST= 0
INDE  14  28  14  FOBS=   62.4  SIGMA=   1.3  PHAS=   63.3  FOM= 0.95  TEST= 0
INDE  14  28  16  FOBS=  148.0  SIGMA=   0.7  PHAS=    2.1  FOM= 0.84  TEST= 0
INDE  14  28  18  FOBS=  372.5  SIGMA=   0.6  PHAS= -112.0  FOM= 0.99  TEST= 0
INDE  14  28  20  FOBS=  150.8  SIGMA=   0.8  PHAS= -134.4  FOM= 0.96  TEST= 0
INDE  14  28  22  FOBS=  255.7  SIGMA=   0.5  PHAS= -124.8  FOM= 0.80  TEST= 1
INDE  14  28  24  FOBS=   99.2  SIGMA=   1.1  PHAS=  114.8  FOM= 0.96  TEST= 0
INDE  14  28  26  FOBS=  183.8  SIGMA=   1.0  PHAS=  -31.2  FOM= 0.96  TEST= 0
INDE  14  28  28  FOBS=  138.4  SIGMA=   1.1  PHAS= -139.7  FOM= 0.91  TEST= 0
INDE  14  28  30  FOBS=  151.3  SIGMA=   1.1  PHAS= -103.3  FOM= 0.88  TEST= 1
INDE  14  28  32  FOBS=  139.8  SIGMA=   1.2  PHAS= -133.1  FOM= 0.89  TEST= 0
INDE  14  28  34  FOBS=  260.0  SIGMA=   1.0  PHAS=   79.5  FOM= 0.94  TEST= 0
INDE  14  28  36  FOBS=  129.3  SIGMA=   1.5  PHAS=  149.2  FOM= 0.86  TEST= 1
INDE  14  28  38  FOBS=   23.7  SIGMA=   8.4  PHAS=  -75.4  FOM= 0.33  TEST= 0
INDE  14  28  40  FOBS=  160.9  SIGMA=   1.1  PHAS=  -67.0  FOM= 0.91  TEST= 0
INDE  14  28  42  FOBS=   66.0  SIGMA=   2.5  PHAS=   93.7  FOM= 0.77  TEST= 1
INDE  14  28  44  FOBS=   91.5  SIGMA=   1.8  PHAS=   68.7  FOM= 0.92  TEST= 0
INDE  14  28  46  FOBS=   24.4  SIGMA=   7.5  PHAS=  174.1  FOM= 0.44  TEST= 0
INDE  14  28  48  FOBS=    0.0  SIGMA=  17.7  PHAS=    0.0  FOM= 0.00  TEST= 0
INDE  14  28  50  FOBS=  127.7  SIGMA=   1.2  PHAS=  124.9  FOM= 0.97  TEST= 0
INDE  14  28  52  FOBS=  115.3  SIGMA=   1.5  PHAS= -165.6  FOM= 0.84  TEST= 0
INDE  14  28  54  FOBS=   25.4  SIGMA=   6.6  PHAS=  -40.4  FOM= 0.55  TEST= 0
INDE  14  28  56  FOBS=    6.3  SIGMA=  27.9  PHAS= -104.1  FOM= 0.22  TEST= 0
INDE  14  28  58  FOBS=  112.0  SIGMA=   2.0  PHAS=  159.8  FOM= 0.95  TEST= 0
INDE  14  28  60  FOBS=   42.4  SIGMA=   5.0  PHAS=   42.4  FOM= 0.24  TEST= 1
INDE  14  28  62  FOBS=  111.3  SIGMA=   2.7  PHAS=  163.4  FOM= 0.90  TEST= 0
INDE  14  28  64  FOBS=   49.1  SIGMA=   7.1  PHAS= -146.4  FOM= 0.72  TEST= 0
INDE  14  28  66  FOBS=    0.0  SIGMA=  30.9  PHAS=    0.0  FOM= 0.00  TEST= 0
INDE  14  28  68  FOBS=    0.0  SIGMA=  20.7  PHAS=    0.0  FOM= 0.00  TEST= 1
INDE  14  28  70  FOBS=   69.5  SIGMA=   7.7  PHAS=   91.9  FOM= 0.75  TEST= 0
INDE  14  29  15  FOBS=   90.8  SIGMA=   1.1  PHAS=   45.8  FOM= 0.96  TEST= 0
INDE  14  29  17  FOBS=  157.7  SIGMA=   0.8  PHAS=   55.3  FOM= 0.64  TEST= 1
INDE  14  29  19  FOBS=  244.8  SIGMA=   0.6  PHAS=   77.0  FOM= 0.94  TEST= 1
INDE  14  29  21  FOBS=  101.3  SIGMA=   1.1  PHAS=  121.3  FOM= 0.64  TEST= 0
INDE  14  29  23  FOBS=  161.7  SIGMA=   0.8  PHAS=   93.9  FOM= 0.98  TEST= 0
INDE  14  29  25  FOBS=  234.5  SIGMA=   0.7  PHAS=  -38.8  FOM= 0.93  TEST= 0
INDE  14  29  27  FOBS=  160.7  SIGMA=   1.1  PHAS=  103.4  FOM= 0.96  TEST= 0
INDE  14  29  29  FOBS=  230.6  SIGMA=   0.8  PHAS=   38.6  FOM= 0.97  TEST= 0
INDE  14  29  31  FOBS=  112.4  SIGMA=   1.5  PHAS=  117.6  FOM= 0.43  TEST= 0
INDE  14  29  33  FOBS=  110.0  SIGMA=   1.7  PHAS=  -89.0  FOM= 0.68  TEST= 0
INDE  14  29  35  FOBS=  135.6  SIGMA=   1.4  PHAS=   48.4  FOM= 0.62  TEST= 0
INDE  14  29  37  FOBS=  140.8  SIGMA=   1.4  PHAS=   96.2  FOM= 0.76  TEST= 0
INDE  14  29  39  FOBS=  123.1  SIGMA=   1.5  PHAS= -102.2  FOM= 0.87  TEST= 0
INDE  14  29  41  FOBS=  104.5  SIGMA=   1.6  PHAS=    3.6  FOM= 0.96  TEST= 0
INDE  14  29  43  FOBS=   80.6  SIGMA=   2.1  PHAS=   58.9  FOM= 0.92  TEST= 0
INDE  14  29  45  FOBS=   46.9  SIGMA=   3.4  PHAS=   -4.4  FOM= 0.91  TEST= 0
INDE  14  29  47  FOBS=  141.9  SIGMA=   1.2  PHAS=  -49.8  FOM= 0.88  TEST= 0
INDE  14  29  49  FOBS=  136.8  SIGMA=   1.3  PHAS=   54.1  FOM= 0.91  TEST= 0
INDE  14  29  51  FOBS=   56.4  SIGMA=   3.1  PHAS=   74.8  FOM= 0.68  TEST= 0
INDE  14  29  53  FOBS=   68.9  SIGMA=   2.5  PHAS=  179.4  FOM= 0.38  TEST= 1
INDE  14  29  55  FOBS=   32.2  SIGMA=   5.9  PHAS=  172.7  FOM= 0.62  TEST= 0
INDE  14  29  57  FOBS=  139.5  SIGMA=   1.4  PHAS=   75.1  FOM= 0.96  TEST= 0
INDE  14  29  59  FOBS=    0.0  SIGMA=  22.4  PHAS=    0.0  FOM= 0.00  TEST= 0
INDE  14  29  61  FOBS=   49.6  SIGMA=   5.1  PHAS=   79.1  FOM= 0.75  TEST= 0
INDE  14  29  63  FOBS=   56.0  SIGMA=   6.2  PHAS=  -68.1  FOM= 0.81  TEST= 0
INDE  14  29  65  FOBS=   20.2  SIGMA=  24.1  PHAS=  -99.3  FOM= 0.40  TEST= 0
INDE  14  29  67  FOBS=   76.3  SIGMA=   6.6  PHAS=  107.8  FOM= 0.76  TEST= 0
INDE  14  29  69  FOBS=   12.4  SIGMA=  17.8  PHAS=   29.4  FOM= 0.12  TEST= 1
INDE  14  30  14  FOBS=  271.2  SIGMA=   0.5  PHAS= -133.5  FOM= 0.98  TEST= 0
INDE  14  30  16  FOBS=  163.6  SIGMA=   0.7  PHAS=  -67.7  FOM= 0.91  TEST= 0
INDE  14  30  18  FOBS=  139.3  SIGMA=   0.9  PHAS=  -55.4  FOM= 0.75  TEST= 0
INDE  14  30  20  FOBS=  173.1  SIGMA=   0.7  PHAS=  -71.4  FOM= 0.94  TEST= 0
INDE  14  30  22  FOBS=  286.9  SIGMA=   0.6  PHAS=  -16.3  FOM= 0.99  TEST= 0
INDE  14  30  24  FOBS=  148.5  SIGMA=   0.9  PHAS= -128.0  FOM= 0.92  TEST= 0
INDE  14  30  26  FOBS=  123.2  SIGMA=   1.1  PHAS=  -81.9  FOM= 0.80  TEST= 0
INDE  14  30  28  FOBS=  158.2  SIGMA=   1.2  PHAS=  -11.6  FOM= 0.91  TEST= 0
INDE  14  30  30  FOBS=  179.0  SIGMA=   1.0  PHAS= -100.7  FOM= 0.92  TEST= 0
INDE  14  30  32  FOBS=  128.7  SIGMA=   1.5  PHAS=   61.0  FOM= 0.91  TEST= 0
```

*FIG. 12A - 346*

| | | | | | | | | | | | |
|---|---|---|---|---|---|---|---|---|---|---|---|
| INDE | 14 | 30 | 34 | FOBS= | 92.8 | SIGMA= | 2.1 | PHAS= | -147.9 | FOM= 0.91 | TEST= 0 |
| INDE | 14 | 30 | 36 | FOBS= | 13.8 | SIGMA= | 16.6 | PHAS= | 138.5 | FOM= 0.20 | TEST= 0 |
| INDE | 14 | 30 | 38 | FOBS= | 182.4 | SIGMA= | 1.1 | PHAS= | -75.7 | FOM= 0.94 | TEST= 0 |
| INDE | 14 | 30 | 40 | FOBS= | 236.2 | SIGMA= | 0.9 | PHAS= | -52.6 | FOM= 0.90 | TEST= 0 |
| INDE | 14 | 30 | 42 | FOBS= | 116.8 | SIGMA= | 1.5 | PHAS= | -72.9 | FOM= 0.87 | TEST= 0 |
| INDE | 14 | 30 | 44 | FOBS= | 128.6 | SIGMA= | 1.3 | PHAS= | 174.3 | FOM= 0.88 | TEST= 0 |
| INDE | 14 | 30 | 46 | FOBS= | 64.4 | SIGMA= | 2.5 | PHAS= | -162.2 | FOM= 0.84 | TEST= 0 |
| INDE | 14 | 30 | 48 | FOBS= | 125.7 | SIGMA= | 1.4 | PHAS= | -44.6 | FOM= 0.91 | TEST= 1 |
| INDE | 14 | 30 | 50 | FOBS= | 71.8 | SIGMA= | 2.7 | PHAS= | -23.1 | FOM= 0.41 | TEST= 0 |
| INDE | 14 | 30 | 52 | FOBS= | 78.6 | SIGMA= | 2.5 | PHAS= | -107.9 | FOM= 0.89 | TEST= 0 |
| INDE | 14 | 30 | 54 | FOBS= | 83.6 | SIGMA= | 2.1 | PHAS= | 134.3 | FOM= 0.68 | TEST= 0 |
| INDE | 14 | 30 | 56 | FOBS= | 63.1 | SIGMA= | 3.0 | PHAS= | -22.2 | FOM= 0.68 | TEST= 0 |
| INDE | 14 | 30 | 58 | FOBS= | 93.2 | SIGMA= | 2.0 | PHAS= | 26.4 | FOM= 0.88 | TEST= 0 |
| INDE | 14 | 30 | 60 | FOBS= | 37.5 | SIGMA= | 5.6 | PHAS= | 83.1 | FOM= 0.65 | TEST= 0 |
| INDE | 14 | 30 | 62 | FOBS= | 0.0 | SIGMA= | 24.2 | PHAS= | 0.0 | FOM= 0.00 | TEST= 0 |
| INDE | 14 | 30 | 64 | FOBS= | 54.3 | SIGMA= | 6.3 | PHAS= | -155.7 | FOM= 0.90 | TEST= 0 |
| INDE | 14 | 30 | 66 | FOBS= | 106.4 | SIGMA= | 4.9 | PHAS= | 177.7 | FOM= 0.37 | TEST= 0 |
| INDE | 14 | 30 | 68 | FOBS= | 0.0 | SIGMA= | 21.4 | PHAS= | 0.0 | FOM= 0.00 | TEST= 0 |
| INDE | 14 | 30 | 70 | FOBS= | 0.0 | SIGMA= | 21.4 | PHAS= | 0.0 | FOM= 0.00 | TEST= 0 |
| INDE | 14 | 31 | 15 | FOBS= | 172.0 | SIGMA= | 0.7 | PHAS= | 150.4 | FOM= 0.96 | TEST= 0 |
| INDE | 14 | 31 | 17 | FOBS= | 164.7 | SIGMA= | 0.8 | PHAS= | -18.3 | FOM= 0.96 | TEST= 0 |
| INDE | 14 | 31 | 19 | FOBS= | 0.0 | SIGMA= | 15.5 | PHAS= | 0.0 | FOM= 0.00 | TEST= 1 |
| INDE | 14 | 31 | 21 | FOBS= | 219.6 | SIGMA= | 0.7 | PHAS= | -141.1 | FOM= 0.95 | TEST= 0 |
| INDE | 14 | 31 | 23 | FOBS= | 137.1 | SIGMA= | 1.0 | PHAS= | 155.0 | FOM= 0.88 | TEST= 0 |
| INDE | 14 | 31 | 25 | FOBS= | 315.4 | SIGMA= | 0.6 | PHAS= | -11.1 | FOM= 0.95 | TEST= 0 |
| INDE | 14 | 31 | 27 | FOBS= | 121.2 | SIGMA= | 1.2 | PHAS= | 172.5 | FOM= 0.90 | TEST= 0 |
| INDE | 14 | 31 | 29 | FOBS= | 40.9 | SIGMA= | 3.8 | PHAS= | 122.2 | FOM= 0.91 | TEST= 0 |
| INDE | 14 | 31 | 31 | FOBS= | 213.3 | SIGMA= | 1.0 | PHAS= | 147.1 | FOM= 0.95 | TEST= 0 |
| INDE | 14 | 31 | 33 | FOBS= | 157.9 | SIGMA= | 1.5 | PHAS= | 125.3 | FOM= 0.94 | TEST= 0 |
| INDE | 14 | 31 | 35 | FOBS= | 90.1 | SIGMA= | 2.2 | PHAS= | -134.1 | FOM= 0.79 | TEST= 0 |
| INDE | 14 | 31 | 37 | FOBS= | 126.7 | SIGMA= | 1.6 | PHAS= | 112.5 | FOM= 0.88 | TEST= 0 |
| INDE | 14 | 31 | 39 | FOBS= | 115.8 | SIGMA= | 1.7 | PHAS= | -142.4 | FOM= 0.87 | TEST= 0 |
| INDE | 14 | 31 | 41 | FOBS= | 217.2 | SIGMA= | 1.0 | PHAS= | -127.1 | FOM= 0.03 | TEST= 1 |
| INDE | 14 | 31 | 43 | FOBS= | 138.9 | SIGMA= | 1.3 | PHAS= | 171.1 | FOM= 0.91 | TEST= 0 |
| INDE | 14 | 31 | 45 | FOBS= | 146.6 | SIGMA= | 1.3 | PHAS= | 31.6 | FOM= 0.92 | TEST= 0 |
| INDE | 14 | 31 | 47 | FOBS= | 41.4 | SIGMA= | 4.6 | PHAS= | -155.4 | FOM= 0.84 | TEST= 1 |
| INDE | 14 | 31 | 49 | FOBS= | 46.0 | SIGMA= | 4.1 | PHAS= | 90.1 | FOM= 0.32 | TEST= 0 |
| INDE | 14 | 31 | 51 | FOBS= | 104.1 | SIGMA= | 1.9 | PHAS= | -62.6 | FOM= 0.46 | TEST= 1 |
| INDE | 14 | 31 | 53 | FOBS= | 108.2 | SIGMA= | 1.8 | PHAS= | 163.4 | FOM= 0.92 | TEST= 0 |
| INDE | 14 | 31 | 55 | FOBS= | 9.6 | SIGMA= | 22.8 | PHAS= | -62.3 | FOM= 0.06 | TEST= 0 |
| INDE | 14 | 31 | 57 | FOBS= | 60.7 | SIGMA= | 3.0 | PHAS= | -31.9 | FOM= 0.80 | TEST= 1 |
| INDE | 14 | 31 | 59 | FOBS= | 86.2 | SIGMA= | 2.2 | PHAS= | -46.7 | FOM= 0.80 | TEST= 1 |
| INDE | 14 | 31 | 61 | FOBS= | 0.0 | SIGMA= | 22.4 | PHAS= | 0.0 | FOM= 0.00 | TEST= 0 |
| INDE | 14 | 31 | 63 | FOBS= | 0.0 | SIGMA= | 24.1 | PHAS= | 0.0 | FOM= 0.00 | TEST= 0 |
| INDE | 14 | 31 | 65 | FOBS= | 49.0 | SIGMA= | 10.2 | PHAS= | 20.2 | FOM= 0.79 | TEST= 0 |
| INDE | 14 | 31 | 67 | FOBS= | 42.6 | SIGMA= | 12.0 | PHAS= | -146.5 | FOM= 0.76 | TEST= 0 |
| INDE | 14 | 31 | 69 | FOBS= | 5.8 | SIGMA= | 41.4 | PHAS= | -54.6 | FOM= 0.08 | TEST= 0 |
| INDE | 14 | 32 | 14 | FOBS= | 169.9 | SIGMA= | 0.6 | PHAS= | -89.2 | FOM= 0.66 | TEST= 0 |
| INDE | 14 | 32 | 16 | FOBS= | 178.5 | SIGMA= | 0.7 | PHAS= | -130.1 | FOM= 0.79 | TEST= 1 |
| INDE | 14 | 32 | 18 | FOBS= | 207.8 | SIGMA= | 0.7 | PHAS= | -108.3 | FOM= 0.87 | TEST= 0 |
| INDE | 14 | 32 | 20 | FOBS= | 94.2 | SIGMA= | 1.4 | PHAS= | -176.4 | FOM= 0.84 | TEST= 0 |
| INDE | 14 | 32 | 22 | FOBS= | 124.3 | SIGMA= | 1.2 | PHAS= | 42.1 | FOM= 0.85 | TEST= 0 |
| INDE | 14 | 32 | 24 | FOBS= | 119.9 | SIGMA= | 1.1 | PHAS= | -82.1 | FOM= 0.63 | TEST= 0 |
| INDE | 14 | 32 | 26 | FOBS= | 58.1 | SIGMA= | 2.4 | PHAS= | 149.5 | FOM= 0.92 | TEST= 0 |
| INDE | 14 | 32 | 28 | FOBS= | 250.9 | SIGMA= | 0.7 | PHAS= | 19.6 | FOM= 0.97 | TEST= 0 |
| INDE | 14 | 32 | 30 | FOBS= | 0.0 | SIGMA= | 18.4 | PHAS= | 0.0 | FOM= 0.00 | TEST= 0 |
| INDE | 14 | 32 | 32 | FOBS= | 463.6 | SIGMA= | 1.0 | PHAS= | 25.4 | FOM= 0.99 | TEST= 0 |
| INDE | 14 | 32 | 34 | FOBS= | 281.1 | SIGMA= | 1.1 | PHAS= | 115.5 | FOM= 0.96 | TEST= 0 |
| INDE | 14 | 32 | 36 | FOBS= | 135.4 | SIGMA= | 1.5 | PHAS= | 101.6 | FOM= 0.66 | TEST= 0 |
| INDE | 14 | 32 | 38 | FOBS= | 85.6 | SIGMA= | 2.3 | PHAS= | -77.8 | FOM= 0.94 | TEST= 0 |
| INDE | 14 | 32 | 40 | FOBS= | 150.7 | SIGMA= | 1.3 | PHAS= | 8.1 | FOM= 0.87 | TEST= 0 |
| INDE | 14 | 32 | 42 | FOBS= | 162.3 | SIGMA= | 1.2 | PHAS= | 84.2 | FOM= 0.88 | TEST= 0 |
| INDE | 14 | 32 | 44 | FOBS= | 32.6 | SIGMA= | 7.6 | PHAS= | -1.2 | FOM= 0.19 | TEST= 0 |
| INDE | 14 | 32 | 46 | FOBS= | 143.7 | SIGMA= | 1.4 | PHAS= | -22.6 | FOM= 0.91 | TEST= 0 |
| INDE | 14 | 32 | 48 | FOBS= | 57.0 | SIGMA= | 3.4 | PHAS= | -56.6 | FOM= 0.79 | TEST= 1 |
| INDE | 14 | 32 | 50 | FOBS= | 114.6 | SIGMA= | 1.7 | PHAS= | -90.6 | FOM= 0.90 | TEST= 0 |
| INDE | 14 | 32 | 52 | FOBS= | 91.8 | SIGMA= | 2.1 | PHAS= | -116.0 | FOM= 0.87 | TEST= 0 |
| INDE | 14 | 32 | 54 | FOBS= | 40.5 | SIGMA= | 4.9 | PHAS= | -178.8 | FOM= 0.63 | TEST= 0 |
| INDE | 14 | 32 | 56 | FOBS= | 0.0 | SIGMA= | 21.3 | PHAS= | 0.0 | FOM= 0.00 | TEST= 0 |
| INDE | 14 | 32 | 58 | FOBS= | 0.0 | SIGMA= | 20.7 | PHAS= | 0.0 | FOM= 0.00 | TEST= 0 |

*FIG. 12A - 347*

```
INDE 14 32 60 FOBS=     0.0 SIGMA=  20.4 PHAS=    0.0 FOM= 0.00 TEST= 0
INDE 14 32 62 FOBS=    28.1 SIGMA=   8.1 PHAS= -159.7 FOM= 0.12 TEST= 0
INDE 14 32 64 FOBS=     0.9 SIGMA= 269.5 PHAS=  -95.0 FOM= 0.02 TEST= 0
INDE 14 32 66 FOBS=    76.4 SIGMA=   5.0 PHAS= -144.4 FOM= 0.88 TEST= 0
INDE 14 32 68 FOBS=    25.8 SIGMA=   9.6 PHAS=  150.7 FOM= 0.35 TEST= 0
INDE 14 33 15 FOBS=    51.8 SIGMA=   2.2 PHAS=   80.8 FOM= 0.87 TEST= 0
INDE 14 33 17 FOBS=    83.1 SIGMA=   1.5 PHAS=   93.5 FOM= 0.90 TEST= 0
INDE 14 33 19 FOBS=   205.9 SIGMA=   0.8 PHAS= -148.4 FOM= 0.83 TEST= 0
INDE 14 33 21 FOBS=    15.2 SIGMA=   9.6 PHAS=  151.1 FOM= 0.02 TEST= 0
INDE 14 33 23 FOBS=    65.0 SIGMA=   2.3 PHAS=  -42.9 FOM= 0.74 TEST= 0
INDE 14 33 25 FOBS=   298.6 SIGMA=   0.6 PHAS=  -45.2 FOM= 0.94 TEST= 0
INDE 14 33 27 FOBS=   180.1 SIGMA=   0.9 PHAS=  -27.5 FOM= 0.99 TEST= 0
INDE 14 33 29 FOBS=   198.6 SIGMA=   1.0 PHAS= -154.3 FOM= 0.95 TEST= 1
INDE 14 33 31 FOBS=   393.0 SIGMA=   0.6 PHAS=    2.9 FOM= 0.98 TEST= 0
INDE 14 33 33 FOBS=   164.6 SIGMA=   1.3 PHAS=    3.8 FOM= 0.96 TEST= 0
INDE 14 33 35 FOBS=   209.3 SIGMA=   1.1 PHAS=   65.5 FOM= 0.94 TEST= 0
INDE 14 33 37 FOBS=   107.2 SIGMA=   1.9 PHAS=  -15.2 FOM= 0.87 TEST= 0
INDE 14 33 39 FOBS=    86.8 SIGMA=   2.2 PHAS=  152.2 FOM= 0.44 TEST= 0
INDE 14 33 41 FOBS=    90.3 SIGMA=   2.3 PHAS= -117.0 FOM= 0.82 TEST= 0
INDE 14 33 43 FOBS=    99.6 SIGMA=   2.3 PHAS=  -42.9 FOM= 0.85 TEST= 1
INDE 14 33 45 FOBS=   110.2 SIGMA=   2.1 PHAS=  -98.2 FOM= 0.92 TEST= 0
INDE 14 33 47 FOBS=   184.7 SIGMA=   1.3 PHAS=  179.2 FOM= 0.96 TEST= 0
INDE 14 33 49 FOBS=    84.1 SIGMA=   2.3 PHAS=  159.8 FOM= 0.91 TEST= 0
INDE 14 33 51 FOBS=    87.7 SIGMA=   2.2 PHAS=  -36.9 FOM= 0.70 TEST= 0
INDE 14 33 53 FOBS=   137.4 SIGMA=   1.7 PHAS= -148.0 FOM= 0.90 TEST= 0
INDE 14 33 55 FOBS=    47.9 SIGMA=   4.4 PHAS=  100.2 FOM= 0.58 TEST= 0
INDE 14 33 57 FOBS=   118.2 SIGMA=   1.9 PHAS=   16.8 FOM= 0.89 TEST= 0
INDE 14 33 59 FOBS=    91.2 SIGMA=   2.4 PHAS=  -62.9 FOM= 0.90 TEST= 0
INDE 14 33 61 FOBS=     0.0 SIGMA=  20.3 PHAS=    0.0 FOM= 0.00 TEST= 0
INDE 14 33 63 FOBS=     0.0 SIGMA=  20.3 PHAS=    0.0 FOM= 0.00 TEST= 0
INDE 14 33 65 FOBS=    61.5 SIGMA=   5.0 PHAS=  119.1 FOM= 0.89 TEST= 0
INDE 14 33 67 FOBS=     0.0 SIGMA=  27.7 PHAS=    0.0 FOM= 0.00 TEST= 0
INDE 14 33 69 FOBS=    65.1 SIGMA=   8.2 PHAS=   20.5 FOM= 0.79 TEST= 0
INDE 14 34 14 FOBS=   254.4 SIGMA=   0.6 PHAS=  -38.6 FOM= 0.96 TEST= 0
INDE 14 34 16 FOBS=   191.7 SIGMA=   0.8 PHAS= -129.4 FOM= 0.98 TEST= 0
INDE 14 34 18 FOBS=   277.3 SIGMA=   0.7 PHAS=  168.6 FOM= 0.95 TEST= 0
INDE 14 34 20 FOBS=    35.5 SIGMA=   4.1 PHAS=   24.7 FOM= 0.49 TEST= 0
INDE 14 34 22 FOBS=    74.4 SIGMA=   2.0 PHAS=   51.2 FOM= 0.98 TEST= 0
INDE 14 34 24 FOBS=   153.8 SIGMA=   1.1 PHAS=  147.7 FOM= 0.90 TEST= 0
INDE 14 34 26 FOBS=    97.9 SIGMA=   1.5 PHAS= -154.9 FOM= 0.85 TEST= 1
INDE 14 34 28 FOBS=   183.1 SIGMA=   0.9 PHAS=  100.6 FOM= 0.96 TEST= 0
INDE 14 34 30 FOBS=   111.5 SIGMA=   1.8 PHAS= -148.1 FOM= 0.96 TEST= 0
INDE 14 34 32 FOBS=   353.9 SIGMA=   0.9 PHAS=  -19.5 FOM= 0.95 TEST= 0
INDE 14 34 34 FOBS=    91.8 SIGMA=   2.2 PHAS= -151.9 FOM= 0.56 TEST= 1
INDE 14 34 36 FOBS=    95.6 SIGMA=   2.1 PHAS=  -30.5 FOM= 0.87 TEST= 0
INDE 14 34 38 FOBS=     0.0 SIGMA=  21.8 PHAS=    0.0 FOM= 0.00 TEST= 0
INDE 14 34 40 FOBS=   127.6 SIGMA=   1.9 PHAS=  -10.5 FOM= 0.89 TEST= 0
INDE 14 34 42 FOBS=    60.9 SIGMA=   3.7 PHAS= -157.2 FOM= 0.86 TEST= 0
INDE 14 34 44 FOBS=    91.2 SIGMA=   2.5 PHAS= -170.0 FOM= 0.68 TEST= 0
INDE 14 34 46 FOBS=   153.9 SIGMA=   1.6 PHAS=   54.9 FOM= 0.95 TEST= 0
INDE 14 34 48 FOBS=     0.0 SIGMA=  23.7 PHAS=    0.0 FOM= 0.00 TEST= 0
INDE 14 34 50 FOBS=   115.4 SIGMA=   1.8 PHAS=  -18.9 FOM= 0.90 TEST= 0
INDE 14 34 52 FOBS=    39.4 SIGMA=   5.5 PHAS= -177.3 FOM= 0.39 TEST= 0
INDE 14 34 54 FOBS=    81.1 SIGMA=   2.7 PHAS=  -47.7 FOM= 0.50 TEST= 0
INDE 14 34 56 FOBS=    36.4 SIGMA=   6.3 PHAS= -152.5 FOM= 0.56 TEST= 0
INDE 14 34 58 FOBS=   104.5 SIGMA=   2.1 PHAS= -131.6 FOM= 0.92 TEST= 0
INDE 14 34 60 FOBS=    60.5 SIGMA=   3.5 PHAS= -127.1 FOM= 0.60 TEST= 0
INDE 14 34 62 FOBS=     0.0 SIGMA=  22.5 PHAS=    0.0 FOM= 0.00 TEST= 0
INDE 14 34 64 FOBS=     0.0 SIGMA=  21.5 PHAS=    0.0 FOM= 0.00 TEST= 0
INDE 14 34 66 FOBS=    55.7 SIGMA=   5.7 PHAS=  -12.1 FOM= 0.66 TEST= 0
INDE 14 34 68 FOBS=    18.6 SIGMA=  14.8 PHAS=   25.9 FOM= 0.25 TEST= 0
INDE 14 35 15 FOBS=   158.0 SIGMA=   0.9 PHAS= -118.0 FOM= 0.90 TEST= 1
INDE 14 35 17 FOBS=   354.5 SIGMA=   0.6 PHAS=   74.2 FOM= 0.97 TEST= 0
INDE 14 35 19 FOBS=    14.0 SIGMA=  12.8 PHAS=  -31.7 FOM= 0.12 TEST= 0
INDE 14 35 21 FOBS=     0.0 SIGMA=  17.7 PHAS=    0.0 FOM= 0.00 TEST= 0
INDE 14 35 23 FOBS=   287.7 SIGMA=   0.7 PHAS=  -19.7 FOM= 0.95 TEST= 0
INDE 14 35 25 FOBS=   155.0 SIGMA=   1.1 PHAS=  -80.2 FOM= 0.96 TEST= 0
INDE 14 35 27 FOBS=   210.6 SIGMA=   0.9 PHAS=  -32.1 FOM= 0.47 TEST= 1
INDE 14 35 29 FOBS=   163.4 SIGMA=   1.1 PHAS=   67.4 FOM= 0.91 TEST= 0
INDE 14 35 31 FOBS=   337.2 SIGMA=   0.8 PHAS=  -70.2 FOM= 0.93 TEST= 0
```

*FIG. 12A - 348*

```
INDE 14 35 33 FOBS=    86.1 SIGMA=  2.1 PHAS= -129.0 FOM= 0.66 TEST= 0
INDE 14 35 35 FOBS=   264.0 SIGMA=  1.1 PHAS=   86.3 FOM= 0.96 TEST= 0
INDE 14 35 37 FOBS=   117.0 SIGMA=  2.1 PHAS=  -38.3 FOM= 0.86 TEST= 0
INDE 14 35 39 FOBS=   178.4 SIGMA=  1.4 PHAS= -154.4 FOM= 0.92 TEST= 0
INDE 14 35 41 FOBS=    69.8 SIGMA=  3.3 PHAS= -112.2 FOM= 0.74 TEST= 0
INDE 14 35 43 FOBS=    65.6 SIGMA=  3.5 PHAS=  -64.0 FOM= 0.30 TEST= 0
INDE 14 35 45 FOBS=   112.3 SIGMA=  2.1 PHAS=  -41.2 FOM= 0.83 TEST= 0
INDE 14 35 47 FOBS=     0.0 SIGMA= 20.7 PHAS=    0.0 FOM= 0.00 TEST= 0
INDE 14 35 49 FOBS=    57.0 SIGMA=  3.8 PHAS=  170.4 FOM= 0.48 TEST= 0
INDE 14 35 51 FOBS=     0.0 SIGMA= 21.6 PHAS=    0.0 FOM= 0.00 TEST= 0
INDE 14 35 53 FOBS=    62.6 SIGMA=  3.4 PHAS= -146.3 FOM= 0.70 TEST= 0
INDE 14 35 55 FOBS=    60.0 SIGMA=  3.5 PHAS= -135.0 FOM= 0.71 TEST= 0
INDE 14 35 57 FOBS=    44.2 SIGMA=  6.1 PHAS= -133.5 FOM= 0.46 TEST= 0
INDE 14 35 59 FOBS=   101.8 SIGMA=  2.1 PHAS=  123.8 FOM= 0.92 TEST= 0
INDE 14 35 61 FOBS=     0.0 SIGMA= 21.3 PHAS=    0.0 FOM= 0.00 TEST= 0
INDE 14 35 63 FOBS=     2.5 SIGMA= 91.1 PHAS=    9.8 FOM= 0.02 TEST= 0
INDE 14 35 65 FOBS=    47.4 SIGMA=  5.1 PHAS= -106.4 FOM= 0.27 TEST= 1
INDE 14 35 67 FOBS=     0.0 SIGMA= 25.3 PHAS=    0.0 FOM= 0.00 TEST= 0
INDE 14 36 14 FOBS=   177.8 SIGMA=  0.7 PHAS= -138.1 FOM= 0.92 TEST= 0
INDE 14 36 16 FOBS=   142.6 SIGMA=  1.0 PHAS=  -70.6 FOM= 0.92 TEST= 0
INDE 14 36 18 FOBS=   138.3 SIGMA=  1.2 PHAS= -138.5 FOM= 0.90 TEST= 0
INDE 14 36 20 FOBS=   101.9 SIGMA=  1.5 PHAS=   -1.3 FOM= 0.73 TEST= 0
INDE 14 36 22 FOBS=    78.2 SIGMA=  2.0 PHAS= -154.5 FOM= 0.17 TEST= 0
INDE 14 36 24 FOBS=   191.9 SIGMA=  1.0 PHAS= -165.5 FOM= 0.93 TEST= 0
INDE 14 36 26 FOBS=    38.7 SIGMA=  4.9 PHAS= -160.8 FOM= 0.69 TEST= 0
INDE 14 36 28 FOBS=   101.5 SIGMA=  1.7 PHAS= -113.5 FOM= 0.96 TEST= 0
INDE 14 36 30 FOBS=   222.8 SIGMA=  0.9 PHAS= -136.3 FOM= 0.96 TEST= 0
INDE 14 36 32 FOBS=   165.2 SIGMA=  1.2 PHAS= -115.1 FOM= 0.90 TEST= 0
INDE 14 36 34 FOBS=    21.8 SIGMA= 10.7 PHAS=  101.9 FOM= 0.67 TEST= 0
INDE 14 36 36 FOBS=   118.8 SIGMA=  2.1 PHAS=  -13.7 FOM= 0.91 TEST= 0
INDE 14 36 38 FOBS=    43.7 SIGMA=  5.4 PHAS=  166.0 FOM= 0.39 TEST= 0
INDE 14 36 40 FOBS=    55.0 SIGMA=  4.2 PHAS=  -92.6 FOM= 0.18 TEST= 0
INDE 14 36 42 FOBS=    31.7 SIGMA=  7.2 PHAS= -142.3 FOM= 0.36 TEST= 0
INDE 14 36 44 FOBS=     0.0 SIGMA= 21.1 PHAS=    0.0 FOM= 0.00 TEST= 0
INDE 14 36 46 FOBS=     0.0 SIGMA= 21.8 PHAS=    0.0 FOM= 0.00 TEST= 1
INDE 14 36 48 FOBS=     0.0 SIGMA= 21.7 PHAS=    0.0 FOM= 0.00 TEST= 0
INDE 14 36 50 FOBS=     0.0 SIGMA= 21.6 PHAS=    0.0 FOM= 0.00 TEST= 0
INDE 14 36 52 FOBS=    28.4 SIGMA=  8.2 PHAS= -148.6 FOM= 0.03 TEST= 0
INDE 14 36 54 FOBS=     0.0 SIGMA= 23.0 PHAS=    0.0 FOM= 0.00 TEST= 0
INDE 14 36 56 FOBS=   113.6 SIGMA=  1.9 PHAS=  161.6 FOM= 0.96 TEST= 0
INDE 14 36 58 FOBS=    75.2 SIGMA=  2.8 PHAS=    5.0 FOM= 0.89 TEST= 0
INDE 14 36 60 FOBS=    36.9 SIGMA=  6.1 PHAS=  -63.9 FOM= 0.25 TEST= 0
INDE 14 36 62 FOBS=     0.0 SIGMA= 24.0 PHAS=    0.0 FOM= 0.00 TEST= 0
INDE 14 36 64 FOBS=    45.9 SIGMA=  4.7 PHAS= -150.5 FOM= 0.67 TEST= 0
INDE 14 36 66 FOBS=    32.3 SIGMA=  9.8 PHAS=  130.0 FOM= 0.36 TEST= 0
INDE 14 37 15 FOBS=    71.3 SIGMA=  2.0 PHAS=  -49.7 FOM= 0.72 TEST= 0
INDE 14 37 17 FOBS=    40.2 SIGMA=  3.6 PHAS= -161.2 FOM= 0.65 TEST= 0
INDE 14 37 19 FOBS=   117.3 SIGMA=  1.4 PHAS=  -26.0 FOM= 0.33 TEST= 0
INDE 14 37 21 FOBS=   210.5 SIGMA=  0.9 PHAS= -172.4 FOM= 0.97 TEST= 0
INDE 14 37 23 FOBS=   122.7 SIGMA=  1.4 PHAS=  -54.0 FOM= 0.88 TEST= 0
INDE 14 37 25 FOBS=    36.6 SIGMA=  5.3 PHAS=  130.1 FOM= 0.79 TEST= 0
INDE 14 37 27 FOBS=    51.1 SIGMA=  3.6 PHAS=  142.0 FOM= 0.93 TEST= 0
INDE 14 37 29 FOBS=   314.1 SIGMA=  0.8 PHAS=  127.9 FOM= 0.97 TEST= 0
INDE 14 37 31 FOBS=    21.0 SIGMA=  9.4 PHAS=  121.6 FOM= 0.13 TEST= 0
INDE 14 37 33 FOBS=   194.1 SIGMA=  1.1 PHAS=  113.0 FOM= 0.94 TEST= 0
INDE 14 37 35 FOBS=   137.1 SIGMA=  1.5 PHAS=   39.6 FOM= 0.93 TEST= 0
INDE 14 37 37 FOBS=     0.0 SIGMA= 22.9 PHAS=    0.0 FOM= 0.00 TEST= 1
INDE 14 37 39 FOBS=   161.3 SIGMA=  1.6 PHAS= -154.7 FOM= 0.89 TEST= 0
INDE 14 37 41 FOBS=    38.7 SIGMA=  6.6 PHAS=  -15.8 FOM= 0.11 TEST= 0
INDE 14 37 43 FOBS=     0.0 SIGMA= 22.1 PHAS=    0.0 FOM= 0.00 TEST= 0
INDE 14 37 45 FOBS=    29.7 SIGMA=  7.4 PHAS=  -48.9 FOM= 0.43 TEST= 0
INDE 14 37 47 FOBS=    48.2 SIGMA=  4.6 PHAS=  120.9 FOM= 0.67 TEST= 0
INDE 14 37 49 FOBS=     0.0 SIGMA= 20.7 PHAS=    0.0 FOM= 0.00 TEST= 0
INDE 14 37 51 FOBS=    38.1 SIGMA=  6.2 PHAS=  150.9 FOM= 0.53 TEST= 0
INDE 14 37 53 FOBS=    68.6 SIGMA=  3.1 PHAS=  149.8 FOM= 0.65 TEST= 0
INDE 14 37 55 FOBS=    62.5 SIGMA=  3.4 PHAS=  111.0 FOM= 0.67 TEST= 0
INDE 14 37 57 FOBS=     0.0 SIGMA= 22.4 PHAS=    0.0 FOM= 0.00 TEST= 1
INDE 14 37 59 FOBS=    26.2 SIGMA=  9.0 PHAS= -107.3 FOM= 0.16 TEST= 0
INDE 14 37 61 FOBS=    35.2 SIGMA=  7.5 PHAS= -118.2 FOM= 0.39 TEST= 0
INDE 14 37 63 FOBS=    21.3 SIGMA= 11.3 PHAS=   54.4 FOM= 0.03 TEST= 1
```

*FIG. 12A - 349*

```
INDE  14  37  65  FOBS=   70.7  SIGMA=   4.6  PHAS=    46.6  FOM=  0.92  TEST=  0
INDE  14  38  14  FOBS=  123.7  SIGMA=   1.1  PHAS=  -177.0  FOM=  0.92  TEST=  0
INDE  14  38  16  FOBS=   79.4  SIGMA=   2.0  PHAS=  -154.6  FOM=  0.63  TEST=  0
INDE  14  38  18  FOBS=  135.7  SIGMA=   1.4  PHAS=   148.6  FOM=  0.90  TEST=  0
INDE  14  38  20  FOBS=  236.8  SIGMA=   0.9  PHAS=    48.1  FOM=  0.98  TEST=  0
INDE  14  38  22  FOBS=   43.6  SIGMA=   4.8  PHAS=   113.7  FOM=  0.81  TEST=  0
INDE  14  38  24  FOBS=   92.9  SIGMA=   2.3  PHAS=   -94.4  FOM=  0.29  TEST=  1
INDE  14  38  26  FOBS=  219.1  SIGMA=   1.1  PHAS=    39.7  FOM=  0.92  TEST=  0
INDE  14  38  28  FOBS=   45.2  SIGMA=   4.8  PHAS=    27.4  FOM=  0.86  TEST=  0
INDE  14  38  30  FOBS=  175.2  SIGMA=   1.2  PHAS=    86.7  FOM=  0.95  TEST=  0
INDE  14  38  32  FOBS=  148.4  SIGMA=   1.5  PHAS=    16.6  FOM=  0.96  TEST=  0
INDE  14  38  34  FOBS=   33.6  SIGMA=   6.0  PHAS=   136.1  FOM=  0.49  TEST=  0
INDE  14  38  36  FOBS=   39.4  SIGMA=   5.0  PHAS=   -41.2  FOM=  0.24  TEST=  0
INDE  14  38  38  FOBS=   58.3  SIGMA=   3.7  PHAS=    40.1  FOM=  0.82  TEST=  0
INDE  14  38  40  FOBS=    0.0  SIGMA=  22.3  PHAS=     0.0  FOM=  0.00  TEST=  0
INDE  14  38  42  FOBS=   70.6  SIGMA=   3.3  PHAS=   -12.1  FOM=  0.91  TEST=  0
INDE  14  38  44  FOBS=   26.7  SIGMA=   8.4  PHAS=   -76.7  FOM=  0.55  TEST=  0
INDE  14  38  46  FOBS=   45.0  SIGMA=   5.0  PHAS=   170.4  FOM=  0.24  TEST=  0
INDE  14  38  48  FOBS=   71.0  SIGMA=   3.1  PHAS=    39.2  FOM=  0.88  TEST=  0
INDE  14  38  50  FOBS=   54.2  SIGMA=   4.1  PHAS=     2.0  FOM=  0.11  TEST=  1
INDE  14  38  52  FOBS=   72.6  SIGMA=   3.0  PHAS=    36.8  FOM=  0.91  TEST=  0
INDE  14  38  54  FOBS=   94.4  SIGMA=   2.3  PHAS=    65.8  FOM=  0.92  TEST=  0
INDE  14  38  56  FOBS=    0.0  SIGMA=  21.5  PHAS=     0.0  FOM=  0.00  TEST=  0
INDE  14  38  58  FOBS=   54.2  SIGMA=   3.9  PHAS=   -24.5  FOM=  0.78  TEST=  0
INDE  14  38  60  FOBS=   60.6  SIGMA=   3.5  PHAS=  -152.0  FOM=  0.85  TEST=  0
INDE  14  38  62  FOBS=    0.0  SIGMA=  22.7  PHAS=     0.0  FOM=  0.00  TEST=  0
INDE  14  38  64  FOBS=   97.0  SIGMA=   2.8  PHAS=    -9.3  FOM=  0.93  TEST=  0
INDE  14  38  66  FOBS=   42.9  SIGMA=   9.7  PHAS=   -10.6  FOM=  0.88  TEST=  0
INDE  14  39  15  FOBS=  106.3  SIGMA=   1.9  PHAS=   -45.5  FOM=  0.91  TEST=  0
INDE  14  39  17  FOBS=  116.0  SIGMA=   1.6  PHAS=     0.2  FOM=  0.74  TEST=  0
INDE  14  39  19  FOBS=  200.3  SIGMA=   1.2  PHAS=   -23.2  FOM=  0.97  TEST=  0
INDE  14  39  21  FOBS=  178.5  SIGMA=   1.2  PHAS=   150.6  FOM=  0.95  TEST=  0
INDE  14  39  23  FOBS=   71.2  SIGMA=   3.0  PHAS=    20.0  FOM=  0.64  TEST=  0
INDE  14  39  25  FOBS=  188.6  SIGMA=   1.3  PHAS=   -78.0  FOM=  0.94  TEST=  0
INDE  14  39  27  FOBS=  102.4  SIGMA=   2.3  PHAS=   121.6  FOM=  0.52  TEST=  0
INDE  14  39  29  FOBS=  230.3  SIGMA=   1.0  PHAS=    65.2  FOM=  0.92  TEST=  0
INDE  14  39  31  FOBS=  155.9  SIGMA=   1.3  PHAS=    16.0  FOM=  0.92  TEST=  0
INDE  14  39  33  FOBS=   85.1  SIGMA=   2.7  PHAS=   107.9  FOM=  0.85  TEST=  0
INDE  14  39  35  FOBS=   90.4  SIGMA=   2.2  PHAS=    11.3  FOM=  0.81  TEST=  0
INDE  14  39  37  FOBS=  122.0  SIGMA=   1.7  PHAS=   -86.4  FOM=  0.60  TEST=  0
INDE  14  39  39  FOBS=   36.7  SIGMA=   5.8  PHAS=   105.6  FOM=  0.38  TEST=  0
INDE  14  39  41  FOBS=   92.8  SIGMA=   2.5  PHAS=  -118.6  FOM=  0.90  TEST=  0
INDE  14  39  43  FOBS=   66.3  SIGMA=   3.5  PHAS=  -169.9  FOM=  0.73  TEST=  0
INDE  14  39  45  FOBS=    0.0  SIGMA=  22.0  PHAS=     0.0  FOM=  0.00  TEST=  0
INDE  14  39  47  FOBS=   36.0  SIGMA=   6.1  PHAS=   102.9  FOM=  0.52  TEST=  0
INDE  14  39  49  FOBS=  121.9  SIGMA=   1.9  PHAS=    21.2  FOM=  0.94  TEST=  0
INDE  14  39  51  FOBS=   98.3  SIGMA=   2.3  PHAS=  -111.8  FOM=  0.96  TEST=  0
INDE  14  39  53  FOBS=  120.6  SIGMA=   1.9  PHAS=   -15.5  FOM=  0.95  TEST=  0
INDE  14  39  55  FOBS=  132.7  SIGMA=   1.7  PHAS=    -0.4  FOM=  0.94  TEST=  0
INDE  14  39  57  FOBS=   60.4  SIGMA=   3.6  PHAS=  -121.2  FOM=  0.69  TEST=  0
INDE  14  39  59  FOBS=   62.7  SIGMA=   3.4  PHAS=   131.0  FOM=  0.87  TEST=  0
INDE  14  39  61  FOBS=   54.9  SIGMA=   3.9  PHAS=  -134.3  FOM=  0.68  TEST=  0
INDE  14  39  63  FOBS=    0.0  SIGMA=  24.4  PHAS=     0.0  FOM=  0.00  TEST=  0
INDE  14  39  65  FOBS=  106.1  SIGMA=   2.7  PHAS=   -72.7  FOM=  0.96  TEST=  0
INDE  14  40  14  FOBS=  272.5  SIGMA=   0.8  PHAS=  -123.7  FOM=  0.95  TEST=  0
INDE  14  40  16  FOBS=  239.9  SIGMA=   0.9  PHAS=   -67.2  FOM=  0.90  TEST=  0
INDE  14  40  18  FOBS=   27.2  SIGMA=   7.2  PHAS=    33.3  FOM=  0.05  TEST=  1
INDE  14  40  20  FOBS=   96.0  SIGMA=   2.2  PHAS=    93.4  FOM=  0.95  TEST=  0
INDE  14  40  22  FOBS=  244.0  SIGMA=   1.0  PHAS=    13.3  FOM=  0.96  TEST=  0
INDE  14  40  24  FOBS=   74.5  SIGMA=   3.0  PHAS=   151.9  FOM=  0.32  TEST=  0
INDE  14  40  26  FOBS=  141.4  SIGMA=   1.6  PHAS=    90.2  FOM=  0.92  TEST=  1
INDE  14  40  28  FOBS=    0.0  SIGMA=  21.0  PHAS=     0.0  FOM=  0.00  TEST=  0
INDE  14  40  30  FOBS=  139.9  SIGMA=   1.5  PHAS=    -0.5  FOM=  0.88  TEST=  0
INDE  14  40  32  FOBS=  200.1  SIGMA=   1.2  PHAS=     3.9  FOM=  0.96  TEST=  0
INDE  14  40  34  FOBS=   99.6  SIGMA=   2.2  PHAS=  -101.2  FOM=  0.89  TEST=  0
INDE  14  40  36  FOBS=  101.2  SIGMA=   2.0  PHAS=  -147.2  FOM=  0.90  TEST=  0
INDE  14  40  38  FOBS=   67.8  SIGMA=   2.9  PHAS=  -169.7  FOM=  0.12  TEST=  0
INDE  14  40  40  FOBS=   62.8  SIGMA=   3.4  PHAS=    34.6  FOM=  0.84  TEST=  0
INDE  14  40  42  FOBS=   75.4  SIGMA=   3.1  PHAS=    37.8  FOM=  0.86  TEST=  0
INDE  14  40  44  FOBS=   81.1  SIGMA=   2.8  PHAS=  -169.6  FOM=  0.92  TEST=  0
```

*FIG. 12A - 350*

```
INDE  14  40  46  FOBS=   69.8  SIGMA=   3.2  PHAS=   39.0  FOM=  0.64  TEST=  0
INDE  14  40  48  FOBS=  132.5  SIGMA=   1.8  PHAS=  -37.4  FOM=  0.92  TEST=  0
INDE  14  40  50  FOBS=   73.4  SIGMA=   3.0  PHAS= -171.7  FOM=  0.49  TEST=  1
INDE  14  40  52  FOBS=   83.8  SIGMA=   2.7  PHAS= -159.4  FOM=  0.93  TEST=  0
INDE  14  40  54  FOBS=   76.5  SIGMA=   2.9  PHAS=  -42.8  FOM=  0.76  TEST=  0
INDE  14  40  56  FOBS=   64.6  SIGMA=   3.7  PHAS=  -68.2  FOM=  0.86  TEST=  0
INDE  14  40  58  FOBS=    0.0  SIGMA=  22.7  PHAS=    0.0  FOM=  0.00  TEST=  0
INDE  14  40  60  FOBS=   75.6  SIGMA=   2.9  PHAS=   11.5  FOM=  0.79  TEST=  0
INDE  14  40  62  FOBS=    0.0  SIGMA=  20.8  PHAS=    0.0  FOM=  0.00  TEST=  0
INDE  14  40  64  FOBS=   18.3  SIGMA=  15.0  PHAS= -108.7  FOM=  0.38  TEST=  0
INDE  14  41  15  FOBS=  212.1  SIGMA=   1.0  PHAS=  159.7  FOM=  0.83  TEST=  0
INDE  14  41  17  FOBS=  120.3  SIGMA=   1.7  PHAS= -104.9  FOM=  0.94  TEST=  0
INDE  14  41  19  FOBS=   59.5  SIGMA=   3.8  PHAS=  -36.6  FOM=  0.89  TEST=  0
INDE  14  41  21  FOBS=   46.4  SIGMA=   4.6  PHAS=  110.2  FOM=  0.80  TEST=  0
INDE  14  41  23  FOBS=   98.3  SIGMA=   2.3  PHAS= -117.7  FOM=  0.55  TEST=  1
INDE  14  41  25  FOBS=  122.1  SIGMA=   1.8  PHAS=   -3.1  FOM=  0.91  TEST=  0
INDE  14  41  27  FOBS=  137.8  SIGMA=   1.7  PHAS=   81.0  FOM=  0.74  TEST=  0
INDE  14  41  29  FOBS=    0.0  SIGMA=  20.9  PHAS=    0.0  FOM=  0.00  TEST=  0
INDE  14  41  31  FOBS=   58.2  SIGMA=   3.4  PHAS= -165.3  FOM=  0.66  TEST=  0
INDE  14  41  33  FOBS=  148.9  SIGMA=   1.4  PHAS= -158.3  FOM=  0.80  TEST=  1
INDE  14  41  35  FOBS=  151.2  SIGMA=   1.4  PHAS= -179.4  FOM=  0.96  TEST=  0
INDE  14  41  37  FOBS=   37.7  SIGMA=   5.2  PHAS=  116.6  FOM=  0.65  TEST=  0
INDE  14  41  39  FOBS=   81.1  SIGMA=   2.4  PHAS=  142.6  FOM=  0.09  TEST=  1
INDE  14  41  41  FOBS=   83.8  SIGMA=   2.6  PHAS=  -75.6  FOM=  0.91  TEST=  0
INDE  14  41  43  FOBS=   59.5  SIGMA=   3.9  PHAS=   11.5  FOM=  0.47  TEST=  0
INDE  14  41  45  FOBS=    0.0  SIGMA=  22.2  PHAS=    0.0  FOM=  0.00  TEST=  0
INDE  14  41  47  FOBS=   84.0  SIGMA=   2.7  PHAS=  -66.8  FOM=  0.72  TEST=  0
INDE  14  41  49  FOBS=   40.8  SIGMA=   5.4  PHAS=  136.9  FOM=  0.16  TEST=  0
INDE  14  41  51  FOBS=   94.1  SIGMA=   2.4  PHAS=  -65.2  FOM=  0.79  TEST=  0
INDE  14  41  53  FOBS=    0.0  SIGMA=  22.1  PHAS=    0.0  FOM=  0.00  TEST=  0
INDE  14  41  55  FOBS=   59.0  SIGMA=   3.7  PHAS=  -64.2  FOM=  0.78  TEST=  0
INDE  14  41  57  FOBS=   66.2  SIGMA=   3.2  PHAS=  140.4  FOM=  0.88  TEST=  0
INDE  14  41  59  FOBS=    0.0  SIGMA=  20.7  PHAS=    0.0  FOM=  0.00  TEST=  0
INDE  14  41  61  FOBS=   70.0  SIGMA=   3.1  PHAS= -119.6  FOM=  0.89  TEST=  0
INDE  14  41  63  FOBS=   51.4  SIGMA=   5.4  PHAS=   70.9  FOM=  0.14  TEST=  1
INDE  14  42  14  FOBS=   45.5  SIGMA=   4.3  PHAS=   78.6  FOM=  0.83  TEST=  0
INDE  14  42  16  FOBS=  244.9  SIGMA=   1.0  PHAS=  105.4  FOM=  0.97  TEST=  0
INDE  14  42  18  FOBS=  105.9  SIGMA=   2.0  PHAS=   12.8  FOM=  0.97  TEST=  0
INDE  14  42  20  FOBS=   78.5  SIGMA=   3.0  PHAS=  171.7  FOM=  0.61  TEST=  0
INDE  14  42  22  FOBS=  201.1  SIGMA=   1.2  PHAS=  -27.2  FOM=  0.92  TEST=  0
INDE  14  42  24  FOBS=  164.7  SIGMA=   1.4  PHAS=  -42.5  FOM=  0.95  TEST=  0
INDE  14  42  26  FOBS=  204.4  SIGMA=   1.2  PHAS=   -2.8  FOM=  0.93  TEST=  0
INDE  14  42  28  FOBS=  116.8  SIGMA=   1.9  PHAS=  165.1  FOM=  0.93  TEST=  0
INDE  14  42  30  FOBS=  127.0  SIGMA=   1.6  PHAS=   56.7  FOM=  0.87  TEST=  0
INDE  14  42  32  FOBS=  185.4  SIGMA=   1.1  PHAS=    5.3  FOM=  0.49  TEST=  1
INDE  14  42  34  FOBS=  103.8  SIGMA=   1.9  PHAS=  100.9  FOM=  0.80  TEST=  0
INDE  14  42  36  FOBS=    0.0  SIGMA=  20.4  PHAS=    0.0  FOM=  0.00  TEST=  0
INDE  14  42  38  FOBS=   36.7  SIGMA=   5.3  PHAS= -134.5  FOM=  0.33  TEST=  0
INDE  14  42  40  FOBS=  106.2  SIGMA=   1.9  PHAS=  158.8  FOM=  0.93  TEST=  0
INDE  14  42  42  FOBS=   57.0  SIGMA=   3.7  PHAS=  121.3  FOM=  0.69  TEST=  0
INDE  14  42  44  FOBS=    0.0  SIGMA=  21.1  PHAS=    0.0  FOM=  0.00  TEST=  0
INDE  14  42  46  FOBS=    0.0  SIGMA=  22.1  PHAS=    0.0  FOM=  0.00  TEST=  0
INDE  14  42  48  FOBS=  114.1  SIGMA=   2.0  PHAS=   72.3  FOM=  0.67  TEST=  0
INDE  14  42  50  FOBS=   71.9  SIGMA=   3.1  PHAS=  155.4  FOM=  0.60  TEST=  0
INDE  14  42  52  FOBS=  125.5  SIGMA=   1.8  PHAS= -176.4  FOM=  0.96  TEST=  0
INDE  14  42  54  FOBS=  133.2  SIGMA=   1.7  PHAS= -155.9  FOM=  0.96  TEST=  0
INDE  14  42  56  FOBS=   74.3  SIGMA=   3.0  PHAS=  -89.9  FOM=  0.88  TEST=  0
INDE  14  42  58  FOBS=   40.6  SIGMA=   5.3  PHAS=   71.7  FOM=  0.08  TEST=  1
INDE  14  42  60  FOBS=   38.9  SIGMA=   6.2  PHAS=  106.2  FOM=  0.58  TEST=  0
INDE  14  42  62  FOBS=    0.0  SIGMA=  23.2  PHAS=    0.0  FOM=  0.00  TEST=  0
INDE  14  43  15  FOBS=  188.7  SIGMA=   1.2  PHAS=  -25.8  FOM=  0.98  TEST=  0
INDE  14  43  17  FOBS=  328.9  SIGMA=   0.8  PHAS=  -30.4  FOM=  0.96  TEST=  0
INDE  14  43  19  FOBS=   37.5  SIGMA=   5.8  PHAS=  131.2  FOM=  0.79  TEST=  1
INDE  14  43  21  FOBS=    0.0  SIGMA=  20.7  PHAS=    0.0  FOM=  0.00  TEST=  0
INDE  14  43  23  FOBS=  197.2  SIGMA=   1.2  PHAS= -131.7  FOM=  0.97  TEST=  0
INDE  14  43  25  FOBS=  147.0  SIGMA=   1.5  PHAS=  -84.0  FOM=  0.98  TEST=  0
INDE  14  43  27  FOBS=  133.0  SIGMA=   1.7  PHAS=   78.4  FOM=  0.95  TEST=  0
INDE  14  43  29  FOBS=    0.0  SIGMA=  23.0  PHAS=    0.0  FOM=  0.00  TEST=  0
INDE  14  43  31  FOBS=   64.3  SIGMA=   3.0  PHAS=  -23.5  FOM=  0.83  TEST=  1
INDE  14  43  33  FOBS=    0.0  SIGMA=  20.2  PHAS=    0.0  FOM=  0.00  TEST=  0
```

*FIG. 12A - 351*

```
INDE  14  43  35  FOBS=   105.6  SIGMA=   1.8  PHAS=    55.3  FOM=  0.37  TEST= 1
INDE  14  43  37  FOBS=    81.9  SIGMA=   2.4  PHAS=    -8.1  FOM=  0.85  TEST= 1
INDE  14  43  39  FOBS=   151.2  SIGMA=   1.4  PHAS=    49.0  FOM=  0.95  TEST= 0
INDE  14  43  41  FOBS=    66.8  SIGMA=   2.9  PHAS=    88.9  FOM=  0.79  TEST= 0
INDE  14  43  43  FOBS=    11.7  SIGMA=  17.9  PHAS=   -59.1  FOM=  0.21  TEST= 0
INDE  14  43  45  FOBS=     0.0  SIGMA=  21.1  PHAS=     0.0  FOM=  0.00  TEST= 0
INDE  14  43  47  FOBS=    45.4  SIGMA=   4.9  PHAS=   144.8  FOM=  0.01  TEST= 1
INDE  14  43  49  FOBS=     0.0  SIGMA=  23.2  PHAS=     0.0  FOM=  0.00  TEST= 0
INDE  14  43  51  FOBS=    48.6  SIGMA=   4.5  PHAS=    29.3  FOM=  0.51  TEST= 0
INDE  14  43  53  FOBS=   106.5  SIGMA=   2.1  PHAS=   100.2  FOM=  0.95  TEST= 0
INDE  14  43  55  FOBS=   111.7  SIGMA=   2.0  PHAS=   162.2  FOM=  0.95  TEST= 0
INDE  14  43  57  FOBS=     0.0  SIGMA=  22.0  PHAS=     0.0  FOM=  0.00  TEST= 0
INDE  14  43  59  FOBS=     0.0  SIGMA=  23.0  PHAS=     0.0  FOM=  0.00  TEST= 0
INDE  14  43  61  FOBS=    13.7  SIGMA=  19.8  PHAS=   -18.4  FOM=  0.33  TEST= 0
INDE  14  43  63  FOBS=     0.0  SIGMA=  25.4  PHAS=     0.0  FOM=  0.00  TEST= 0
INDE  14  44  14  FOBS=    96.6  SIGMA=   2.9  PHAS=   -31.4  FOM=  0.67  TEST= 0
INDE  14  44  16  FOBS=    68.4  SIGMA=   3.2  PHAS=  -135.8  FOM=  0.90  TEST= 0
INDE  14  44  18  FOBS=   109.4  SIGMA=   2.0  PHAS=  -116.0  FOM=  0.74  TEST= 0
INDE  14  44  20  FOBS=   152.9  SIGMA=   1.6  PHAS=    79.6  FOM=  0.93  TEST= 0
INDE  14  44  22  FOBS=    83.7  SIGMA=   2.6  PHAS=    45.0  FOM=  0.66  TEST= 0
INDE  14  44  24  FOBS=   164.4  SIGMA=   1.4  PHAS=  -112.2  FOM=  0.97  TEST= 0
INDE  14  44  26  FOBS=   107.0  SIGMA=   2.0  PHAS=   -60.4  FOM=  0.83  TEST= 0
INDE  14  44  28  FOBS=    92.7  SIGMA=   2.3  PHAS=    53.4  FOM=  0.91  TEST= 0
INDE  14  44  30  FOBS=   109.7  SIGMA=   2.0  PHAS=   -89.5  FOM=  0.76  TEST= 0
INDE  14  44  32  FOBS=    95.0  SIGMA=   2.1  PHAS=   -92.1  FOM=  0.89  TEST= 0
INDE  14  44  34  FOBS=   191.0  SIGMA=   1.1  PHAS=     8.6  FOM=  0.96  TEST= 0
INDE  14  44  36  FOBS=     0.0  SIGMA=  19.3  PHAS=     0.0  FOM=  0.00  TEST= 0
INDE  14  44  38  FOBS=    36.2  SIGMA=   5.4  PHAS=    26.0  FOM=  0.62  TEST= 0
INDE  14  44  40  FOBS=    52.4  SIGMA=   3.6  PHAS=   -62.4  FOM=  0.65  TEST= 1
INDE  14  44  42  FOBS=    60.9  SIGMA=   3.1  PHAS=   149.7  FOM=  0.56  TEST= 0
INDE  14  44  44  FOBS=    20.0  SIGMA=  11.2  PHAS=   -74.3  FOM=  0.17  TEST= 0
INDE  14  44  46  FOBS=     0.0  SIGMA=  21.1  PHAS=     0.0  FOM=  0.00  TEST= 0
INDE  14  44  48  FOBS=    54.1  SIGMA=   4.1  PHAS=   145.1  FOM=  0.29  TEST= 0
INDE  14  44  50  FOBS=    27.2  SIGMA=   8.2  PHAS=   -41.2  FOM=  0.30  TEST= 0
INDE  14  44  52  FOBS=     0.0  SIGMA=  20.9  PHAS=     0.0  FOM=  0.00  TEST= 0
INDE  14  44  54  FOBS=     0.0  SIGMA=  24.4  PHAS=     0.0  FOM=  0.00  TEST= 0
INDE  14  44  56  FOBS=    18.0  SIGMA=  12.0  PHAS=    47.2  FOM=  0.41  TEST= 0
INDE  14  44  58  FOBS=    59.0  SIGMA=   3.8  PHAS=    55.8  FOM=  0.77  TEST= 0
INDE  14  44  60  FOBS=    40.6  SIGMA=   6.8  PHAS=  -141.9  FOM=  0.62  TEST= 0
INDE  14  44  62  FOBS=     0.0  SIGMA=  25.9  PHAS=     0.0  FOM=  0.00  TEST= 0
INDE  14  45  15  FOBS=   135.4  SIGMA=   1.6  PHAS=  -137.3  FOM=  0.89  TEST= 0
INDE  14  45  17  FOBS=   164.2  SIGMA=   1.4  PHAS=   -41.4  FOM=  0.69  TEST= 1
INDE  14  45  19  FOBS=    66.0  SIGMA=   3.2  PHAS=    49.5  FOM=  0.61  TEST= 0
INDE  14  45  21  FOBS=   125.3  SIGMA=   1.8  PHAS=   -42.1  FOM=  0.96  TEST= 0
INDE  14  45  23  FOBS=    11.4  SIGMA=  20.2  PHAS=   -99.8  FOM=  0.01  TEST= 1
INDE  14  45  25  FOBS=   254.1  SIGMA=   1.0  PHAS=   148.3  FOM=  0.95  TEST= 0
INDE  14  45  27  FOBS=     0.0  SIGMA=  20.5  PHAS=     0.0  FOM=  0.00  TEST= 0
INDE  14  45  29  FOBS=    52.0  SIGMA=   4.4  PHAS=   -67.0  FOM=  0.64  TEST= 0
INDE  14  45  31  FOBS=   232.8  SIGMA=   1.1  PHAS=   138.0  FOM=  0.96  TEST= 0
INDE  14  45  33  FOBS=   128.0  SIGMA=   1.5  PHAS=   -36.0  FOM=  0.93  TEST= 1
INDE  14  45  35  FOBS=    97.7  SIGMA=   1.9  PHAS=  -139.6  FOM=  0.85  TEST= 0
INDE  14  45  37  FOBS=    90.7  SIGMA=   1.9  PHAS=   -21.4  FOM=  0.81  TEST= 0
INDE  14  45  39  FOBS=    58.8  SIGMA=   3.3  PHAS=   -41.3  FOM=  0.21  TEST= 1
INDE  14  45  41  FOBS=    38.5  SIGMA=   4.9  PHAS=  -145.8  FOM=  0.58  TEST= 0
INDE  14  45  43  FOBS=   135.1  SIGMA=   1.5  PHAS=  -140.5  FOM=  0.95  TEST= 0
INDE  14  45  45  FOBS=     0.0  SIGMA=  20.9  PHAS=     0.0  FOM=  0.00  TEST= 0
INDE  14  45  47  FOBS=    55.5  SIGMA=   4.1  PHAS=  -108.2  FOM=  0.52  TEST= 0
INDE  14  45  49  FOBS=    35.1  SIGMA=   6.3  PHAS=  -169.8  FOM=  0.56  TEST= 0
INDE  14  45  51  FOBS=     0.0  SIGMA=  20.7  PHAS=     0.0  FOM=  0.00  TEST= 0
INDE  14  45  53  FOBS=    73.9  SIGMA=   3.1  PHAS=  -126.8  FOM=  0.87  TEST= 0
INDE  14  45  55  FOBS=    85.9  SIGMA=   2.6  PHAS=  -130.4  FOM=  0.93  TEST= 0
INDE  14  45  57  FOBS=    28.8  SIGMA=   7.6  PHAS=    -1.2  FOM=  0.77  TEST= 0
INDE  14  45  59  FOBS=    36.8  SIGMA=   8.9  PHAS=     8.0  FOM=  0.49  TEST= 0
INDE  14  45  61  FOBS=    68.2  SIGMA=   4.2  PHAS=   136.9  FOM=  0.88  TEST= 0
INDE  14  46  14  FOBS=   163.5  SIGMA=   1.8  PHAS=   144.2  FOM=  0.89  TEST= 0
INDE  14  46  16  FOBS=    67.0  SIGMA=   3.1  PHAS=  -139.9  FOM=  0.93  TEST= 0
INDE  14  46  18  FOBS=   245.0  SIGMA=   1.0  PHAS=   -82.9  FOM=  0.96  TEST= 0
INDE  14  46  20  FOBS=    77.1  SIGMA=   2.9  PHAS=    91.6  FOM=  0.87  TEST= 0
INDE  14  46  22  FOBS=    21.7  SIGMA=   9.5  PHAS=  -113.4  FOM=  0.73  TEST= 0
INDE  14  46  24  FOBS=    64.6  SIGMA=   3.2  PHAS=    28.1  FOM=  0.93  TEST= 0
```

*FIG. 12A - 352*

```
INDE 14 46 26 FOBS=   0.0 SIGMA= 21.4 PHAS=   0.0 FOM= 0.00 TEST= 0
INDE 14 46 28 FOBS=  92.9 SIGMA=  2.3 PHAS= -78.1 FOM= 0.76 TEST= 0
INDE 14 46 30 FOBS= 149.1 SIGMA=  1.5 PHAS= 127.9 FOM= 0.81 TEST= 0
INDE 14 46 32 FOBS=  77.2 SIGMA=  2.6 PHAS=   4.8 FOM= 0.87 TEST= 0
INDE 14 46 34 FOBS=  68.4 SIGMA=  2.9 PHAS= -28.6 FOM= 0.83 TEST= 0
INDE 14 46 36 FOBS= 125.4 SIGMA=  1.6 PHAS= 150.6 FOM= 0.92 TEST= 0
INDE 14 46 38 FOBS=   0.0 SIGMA= 19.5 PHAS=   0.0 FOM= 0.00 TEST= 1
INDE 14 46 40 FOBS= 191.2 SIGMA=  1.1 PHAS=-133.1 FOM= 0.96 TEST= 0
INDE 14 46 42 FOBS= 226.6 SIGMA=  1.2 PHAS= 114.8 FOM= 0.97 TEST= 0
INDE 14 46 44 FOBS=   7.5 SIGMA= 28.4 PHAS= 155.8 FOM= 0.04 TEST= 0
INDE 14 46 46 FOBS=   0.0 SIGMA= 20.1 PHAS=   0.0 FOM= 0.00 TEST= 0
INDE 14 46 48 FOBS=   0.0 SIGMA= 21.1 PHAS=   0.0 FOM= 0.00 TEST= 0
INDE 14 46 50 FOBS=  17.0 SIGMA= 14.2 PHAS=  90.3 FOM= 0.10 TEST= 0
INDE 14 46 52 FOBS=  36.0 SIGMA=  6.1 PHAS= -38.6 FOM= 0.26 TEST= 0
INDE 14 46 54 FOBS=  86.3 SIGMA=  2.7 PHAS= 156.3 FOM= 0.93 TEST= 0
INDE 14 46 56 FOBS=   0.0 SIGMA= 22.0 PHAS=   0.0 FOM= 0.00 TEST= 0
INDE 14 46 58 FOBS=  61.6 SIGMA=  3.7 PHAS=-134.0 FOM= 0.80 TEST= 0
INDE 14 46 60 FOBS=  54.1 SIGMA=  5.2 PHAS=  12.1 FOM= 0.77 TEST= 0
INDE 14 47 15 FOBS= 117.3 SIGMA=  2.4 PHAS= 174.4 FOM= 0.90 TEST= 0
INDE 14 47 17 FOBS= 181.5 SIGMA=  1.2 PHAS= 161.6 FOM= 0.95 TEST= 0
INDE 14 47 19 FOBS= 146.4 SIGMA=  1.5 PHAS= -79.6 FOM= 0.83 TEST= 0
INDE 14 47 21 FOBS= 126.8 SIGMA=  1.7 PHAS= -20.3 FOM= 0.87 TEST= 0
INDE 14 47 23 FOBS=  64.1 SIGMA=  3.3 PHAS=-151.3 FOM= 0.32 TEST= 0
INDE 14 47 25 FOBS= 154.6 SIGMA=  1.4 PHAS= 123.1 FOM= 0.97 TEST= 0
INDE 14 47 27 FOBS=  26.8 SIGMA=  8.4 PHAS=-172.5 FOM= 0.22 TEST= 0
INDE 14 47 29 FOBS= 162.2 SIGMA=  1.4 PHAS=   0.2 FOM= 0.93 TEST= 0
INDE 14 47 31 FOBS=   0.0 SIGMA= 20.4 PHAS=   0.0 FOM= 0.00 TEST= 0
INDE 14 47 33 FOBS= 102.9 SIGMA=  1.9 PHAS= -62.3 FOM= 0.49 TEST= 0
INDE 14 47 35 FOBS=  25.8 SIGMA=  7.6 PHAS=-130.7 FOM= 0.02 TEST= 0
INDE 14 47 37 FOBS=  52.0 SIGMA=  3.6 PHAS=  76.3 FOM= 0.67 TEST= 0
INDE 14 47 39 FOBS=  69.2 SIGMA=  2.7 PHAS=-124.2 FOM= 0.86 TEST= 0
INDE 14 47 41 FOBS=  90.5 SIGMA=  2.2 PHAS=  34.1 FOM= 0.91 TEST= 0
INDE 14 47 43 FOBS=  32.5 SIGMA=  6.5 PHAS= -33.2 FOM= 0.30 TEST= 0
INDE 14 47 45 FOBS=  45.7 SIGMA=  4.2 PHAS= 108.6 FOM= 0.66 TEST= 0
INDE 14 47 47 FOBS=  53.2 SIGMA=  3.9 PHAS=   2.0 FOM= 0.39 TEST= 1
INDE 14 47 49 FOBS=   0.0 SIGMA= 21.1 PHAS=   0.0 FOM= 0.00 TEST= 1
INDE 14 47 51 FOBS=   0.0 SIGMA= 22.3 PHAS=   0.0 FOM= 0.00 TEST= 0
INDE 14 47 53 FOBS=   0.0 SIGMA= 20.9 PHAS=   0.0 FOM= 0.00 TEST= 0
INDE 14 47 55 FOBS=   0.0 SIGMA= 21.1 PHAS=   0.0 FOM= 0.00 TEST= 0
INDE 14 47 57 FOBS=   0.0 SIGMA= 23.4 PHAS=   0.0 FOM= 0.00 TEST= 0
INDE 14 47 59 FOBS=  49.5 SIGMA=  5.7 PHAS=  21.3 FOM= 0.63 TEST= 0
INDE 14 48 14 FOBS= 224.6 SIGMA=  1.4 PHAS= 139.1 FOM= 0.95 TEST= 0
INDE 14 48 16 FOBS=   0.0 SIGMA= 22.1 PHAS=   0.0 FOM= 0.00 TEST= 0
INDE 14 48 18 FOBS= 185.4 SIGMA=  1.2 PHAS= 157.8 FOM= 0.95 TEST= 0
INDE 14 48 20 FOBS=  77.3 SIGMA=  2.7 PHAS= 165.5 FOM= 0.84 TEST= 0
INDE 14 48 22 FOBS=   9.1 SIGMA= 24.4 PHAS= 102.1 FOM= 0.07 TEST= 0
INDE 14 48 24 FOBS= 101.2 SIGMA=  2.1 PHAS=  87.6 FOM= 0.91 TEST= 0
INDE 14 48 26 FOBS=  32.2 SIGMA=  6.5 PHAS= 122.8 FOM= 0.33 TEST= 1
INDE 14 48 28 FOBS= 216.7 SIGMA=  1.1 PHAS=-123.6 FOM= 0.97 TEST= 0
INDE 14 48 30 FOBS=   0.0 SIGMA= 20.3 PHAS=   0.0 FOM= 0.00 TEST= 0
INDE 14 48 32 FOBS=   0.0 SIGMA= 20.3 PHAS=   0.0 FOM= 0.00 TEST= 0
INDE 14 48 34 FOBS=  76.9 SIGMA=  2.4 PHAS= -94.5 FOM= 0.32 TEST= 0
INDE 14 48 36 FOBS=  36.2 SIGMA=  5.1 PHAS=-155.8 FOM= 0.29 TEST= 0
INDE 14 48 38 FOBS=  44.9 SIGMA=  4.2 PHAS= 142.9 FOM= 0.73 TEST= 0
INDE 14 48 40 FOBS= 141.3 SIGMA=  1.5 PHAS=-152.9 FOM= 0.95 TEST= 0
INDE 14 48 42 FOBS=  33.2 SIGMA=  6.2 PHAS=-129.2 FOM= 0.57 TEST= 0
INDE 14 48 44 FOBS=  48.9 SIGMA=  3.9 PHAS= -36.3 FOM= 0.69 TEST= 0
INDE 14 48 46 FOBS=  40.4 SIGMA=  4.7 PHAS= -77.3 FOM= 0.57 TEST= 0
INDE 14 48 48 FOBS=  71.6 SIGMA=  2.9 PHAS=-133.6 FOM= 0.81 TEST= 0
INDE 14 48 50 FOBS=  74.4 SIGMA=  3.1 PHAS= 162.9 FOM= 0.81 TEST= 0
INDE 14 48 52 FOBS=  33.7 SIGMA=  6.6 PHAS= 153.4 FOM= 0.56 TEST= 0
INDE 14 48 54 FOBS=  66.6 SIGMA=  3.4 PHAS=  16.1 FOM= 0.69 TEST= 0
INDE 14 48 56 FOBS=  24.4 SIGMA= 11.1 PHAS=  27.5 FOM= 0.50 TEST= 0
INDE 14 48 58 FOBS=  50.6 SIGMA=  5.6 PHAS=-110.0 FOM= 0.11 TEST= 1
INDE 14 49 15 FOBS=  27.0 SIGMA=  9.9 PHAS=  57.2 FOM= 0.49 TEST= 0
INDE 14 49 17 FOBS= 177.5 SIGMA=  1.3 PHAS=  77.9 FOM= 0.95 TEST= 0
INDE 14 49 19 FOBS= 130.9 SIGMA=  1.6 PHAS=  54.1 FOM= 0.79 TEST= 0
INDE 14 49 21 FOBS= 160.5 SIGMA=  1.5 PHAS=  -6.8 FOM= 0.91 TEST= 0
INDE 14 49 23 FOBS=   0.0 SIGMA= 20.2 PHAS=   0.0 FOM= 0.00 TEST= 0
INDE 14 49 25 FOBS=  97.7 SIGMA=  2.2 PHAS=-126.0 FOM= 0.54 TEST= 0
```

*FIG. 12A - 353*

```
INDE 14 49 27 FOBS=    71.0 SIGMA=  3.0 PHAS=   29.1 FOM= 0.88 TEST= 0
INDE 14 49 29 FOBS=    49.3 SIGMA=  4.3 PHAS= -119.9 FOM= 0.75 TEST= 0
INDE 14 49 31 FOBS=     0.0 SIGMA= 21.3 PHAS=    0.0 FOM= 0.00 TEST= 0
INDE 14 49 33 FOBS=    98.3 SIGMA=  2.2 PHAS=   38.1 FOM= 0.79 TEST= 0
INDE 14 49 35 FOBS=   117.3 SIGMA=  1.6 PHAS= -156.2 FOM= 0.92 TEST= 0
INDE 14 49 37 FOBS=   127.3 SIGMA=  1.5 PHAS=  101.8 FOM= 0.93 TEST= 0
INDE 14 49 39 FOBS=     0.0 SIGMA= 18.8 PHAS=    0.0 FOM= 0.00 TEST= 0
INDE 14 49 41 FOBS=   110.9 SIGMA=  1.8 PHAS=   75.5 FOM= 0.88 TEST= 0
INDE 14 49 43 FOBS=   130.4 SIGMA=  1.5 PHAS=  125.2 FOM= 0.90 TEST= 0
INDE 14 49 45 FOBS=    47.5 SIGMA=  4.3 PHAS= -114.5 FOM= 0.52 TEST= 0
INDE 14 49 47 FOBS=     0.0 SIGMA= 20.4 PHAS=    0.0 FOM= 0.00 TEST= 0
INDE 14 49 49 FOBS=    77.9 SIGMA=  2.7 PHAS=   86.3 FOM= 0.83 TEST= 0
INDE 14 49 51 FOBS=    64.7 SIGMA=  3.5 PHAS=   85.2 FOM= 0.50 TEST= 0
INDE 14 49 53 FOBS=     0.0 SIGMA= 23.1 PHAS=    0.0 FOM= 0.00 TEST= 0
INDE 14 49 55 FOBS=    56.3 SIGMA=  4.1 PHAS=  -28.9 FOM= 0.14 TEST= 1
INDE 14 49 57 FOBS=    77.3 SIGMA=  3.7 PHAS=  -55.5 FOM= 0.77 TEST= 0
INDE 14 50 14 FOBS=    12.5 SIGMA= 30.6 PHAS= -111.7 FOM= 0.05 TEST= 0
INDE 14 50 16 FOBS=   174.9 SIGMA=  1.6 PHAS=   -5.0 FOM= 0.75 TEST= 1
INDE 14 50 18 FOBS=   104.2 SIGMA=  2.0 PHAS= -150.9 FOM= 0.61 TEST= 0
INDE 14 50 20 FOBS=    47.4 SIGMA=  4.7 PHAS=  -21.1 FOM= 0.35 TEST= 0
INDE 14 50 22 FOBS=   109.7 SIGMA=  1.9 PHAS=  171.7 FOM= 0.78 TEST= 0
INDE 14 50 24 FOBS=   115.0 SIGMA=  1.9 PHAS=  156.2 FOM= 0.89 TEST= 0
INDE 14 50 26 FOBS=   107.7 SIGMA=  2.0 PHAS= -121.4 FOM= 0.90 TEST= 0
INDE 14 50 28 FOBS=   126.2 SIGMA=  1.7 PHAS=  -88.0 FOM= 0.86 TEST= 0
INDE 14 50 30 FOBS=    50.6 SIGMA=  4.1 PHAS=  179.6 FOM= 0.24 TEST= 1
INDE 14 50 32 FOBS=    90.9 SIGMA=  2.4 PHAS=  -75.3 FOM= 0.89 TEST= 0
INDE 14 50 34 FOBS=    47.2 SIGMA=  4.2 PHAS=   99.0 FOM= 0.87 TEST= 0
INDE 14 50 36 FOBS=   102.6 SIGMA=  1.8 PHAS=   52.4 FOM= 0.91 TEST= 0
INDE 14 50 38 FOBS=    38.7 SIGMA=  4.8 PHAS=  178.2 FOM= 0.31 TEST= 0
INDE 14 50 40 FOBS=    54.7 SIGMA=  3.1 PHAS=   22.1 FOM= 0.61 TEST= 0
INDE 14 50 42 FOBS=    95.6 SIGMA=  2.1 PHAS=  -86.8 FOM= 0.83 TEST= 0
INDE 14 50 44 FOBS=   111.8 SIGMA=  1.8 PHAS=  -87.1 FOM= 0.08 TEST= 1
INDE 14 50 46 FOBS=    70.4 SIGMA=  2.8 PHAS= -124.1 FOM= 0.78 TEST= 0
INDE 14 50 48 FOBS=    23.1 SIGMA=  9.8 PHAS= -137.5 FOM= 0.17 TEST= 0
INDE 14 50 50 FOBS=    19.6 SIGMA= 11.3 PHAS=  145.6 FOM= 0.38 TEST= 0
INDE 14 50 52 FOBS=    34.4 SIGMA=  6.6 PHAS= -161.2 FOM= 0.54 TEST= 0
INDE 14 50 54 FOBS=    50.5 SIGMA=  4.5 PHAS=  -17.5 FOM= 0.18 TEST= 1
INDE 14 50 56 FOBS=    51.7 SIGMA=  5.4 PHAS=  -54.7 FOM= 0.42 TEST= 0
INDE 14 51 15 FOBS=    84.8 SIGMA=  3.2 PHAS= -134.6 FOM= 0.80 TEST= 0
INDE 14 51 17 FOBS=   241.2 SIGMA=  1.1 PHAS=  -33.2 FOM= 0.95 TEST= 0
INDE 14 51 19 FOBS=   100.0 SIGMA=  2.1 PHAS=  -34.2 FOM= 0.19 TEST= 1
INDE 14 51 21 FOBS=    41.4 SIGMA=  5.7 PHAS= -105.1 FOM= 0.29 TEST= 1
INDE 14 51 23 FOBS=   181.4 SIGMA=  1.2 PHAS=   98.8 FOM= 0.76 TEST= 1
INDE 14 51 25 FOBS=    85.3 SIGMA=  2.4 PHAS=  106.8 FOM= 0.93 TEST= 0
INDE 14 51 27 FOBS=    84.6 SIGMA=  2.5 PHAS=  -57.8 FOM= 0.91 TEST= 0
INDE 14 51 29 FOBS=    51.5 SIGMA=  4.0 PHAS= -166.3 FOM= 0.19 TEST= 0
INDE 14 51 31 FOBS=    61.2 SIGMA=  3.4 PHAS=  158.0 FOM= 0.69 TEST= 0
INDE 14 51 33 FOBS=    76.2 SIGMA=  2.7 PHAS=  -21.7 FOM= 0.54 TEST= 1
INDE 14 51 35 FOBS=    96.4 SIGMA=  2.0 PHAS=   37.7 FOM= 0.78 TEST= 0
INDE 14 51 37 FOBS=   110.2 SIGMA=  1.7 PHAS=  108.5 FOM= 0.93 TEST= 0
INDE 14 51 39 FOBS=    83.3 SIGMA=  2.3 PHAS=  -84.4 FOM= 0.88 TEST= 0
INDE 14 51 41 FOBS=    93.2 SIGMA=  1.9 PHAS=  175.3 FOM= 0.88 TEST= 0
INDE 14 51 43 FOBS=    51.6 SIGMA=  3.8 PHAS=  171.6 FOM= 0.33 TEST= 0
INDE 14 51 45 FOBS=   100.3 SIGMA=  2.0 PHAS= -130.9 FOM= 0.92 TEST= 0
INDE 14 51 47 FOBS=    21.3 SIGMA=  9.0 PHAS=  131.1 FOM= 0.54 TEST= 0
INDE 14 51 49 FOBS=    64.7 SIGMA=  3.3 PHAS=   77.6 FOM= 0.83 TEST= 0
INDE 14 51 51 FOBS=   120.4 SIGMA=  2.0 PHAS=  120.2 FOM= 0.94 TEST= 0
INDE 14 51 53 FOBS=    34.4 SIGMA=  8.3 PHAS=  178.5 FOM= 0.67 TEST= 0
INDE 14 51 55 FOBS=    78.0 SIGMA=  3.7 PHAS=  157.5 FOM= 0.89 TEST= 0
INDE 14 51 57 FOBS=    45.2 SIGMA=  9.3 PHAS=  178.3 FOM= 0.80 TEST= 0
INDE 14 52 14 FOBS=    71.8 SIGMA=  3.7 PHAS=  147.8 FOM= 0.81 TEST= 0
INDE 14 52 16 FOBS=   161.8 SIGMA=  1.7 PHAS= -177.9 FOM= 0.93 TEST= 0
INDE 14 52 18 FOBS=   118.3 SIGMA=  1.7 PHAS= -139.6 FOM= 0.91 TEST= 0
INDE 14 52 20 FOBS=   155.5 SIGMA=  1.4 PHAS=  142.9 FOM= 0.78 TEST= 0
INDE 14 52 22 FOBS=    76.1 SIGMA=  2.7 PHAS=   41.2 FOM= 0.72 TEST= 0
INDE 14 52 24 FOBS=   125.8 SIGMA=  1.7 PHAS=    0.0 FOM= 0.83 TEST= 0
INDE 14 52 26 FOBS=   134.9 SIGMA=  1.6 PHAS= -120.4 FOM= 0.91 TEST= 0
INDE 14 52 28 FOBS=    87.0 SIGMA=  2.4 PHAS= -121.4 FOM= 0.62 TEST= 1
INDE 14 52 30 FOBS=    30.1 SIGMA=  7.3 PHAS=  140.7 FOM= 0.33 TEST= 0
INDE 14 52 32 FOBS=    38.6 SIGMA=  5.8 PHAS=  -10.9 FOM= 0.59 TEST= 0
```

*FIG. 12A - 354*

| | | | | | | | | | | | | |
|---|---|---|---|---|---|---|---|---|---|---|---|---|
| INDE | 14 | 52 | 34 | FOBS= | 58.4 | SIGMA= | 3.5 | PHAS= | 68.0 | FOM= | 0.22 | TEST= 1 |
| INDE | 14 | 52 | 36 | FOBS= | 0.0 | SIGMA= | 19.1 | PHAS= | 0.0 | FOM= | 0.00 | TEST= 0 |
| INDE | 14 | 52 | 38 | FOBS= | 78.6 | SIGMA= | 2.4 | PHAS= | 173.9 | FOM= | 0.88 | TEST= 0 |
| INDE | 14 | 52 | 40 | FOBS= | 62.9 | SIGMA= | 3.0 | PHAS= | 81.7 | FOM= | 0.83 | TEST= 0 |
| INDE | 14 | 52 | 42 | FOBS= | 0.0 | SIGMA= | 18.8 | PHAS= | 0.0 | FOM= | 0.00 | TEST= 0 |
| INDE | 14 | 52 | 44 | FOBS= | 96.8 | SIGMA= | 2.1 | PHAS= | -176.4 | FOM= | 0.68 | TEST= 0 |
| INDE | 14 | 52 | 46 | FOBS= | 0.0 | SIGMA= | 20.0 | PHAS= | 0.0 | FOM= | 0.00 | TEST= 0 |
| INDE | 14 | 52 | 48 | FOBS= | 65.1 | SIGMA= | 3.3 | PHAS= | 65.5 | FOM= | 0.85 | TEST= 0 |
| INDE | 14 | 52 | 50 | FOBS= | 70.1 | SIGMA= | 3.3 | PHAS= | 71.4 | FOM= | 0.85 | TEST= 0 |
| INDE | 14 | 52 | 52 | FOBS= | 86.3 | SIGMA= | 2.7 | PHAS= | 32.5 | FOM= | 0.93 | TEST= 0 |
| INDE | 14 | 52 | 54 | FOBS= | 98.7 | SIGMA= | 3.6 | PHAS= | 63.9 | FOM= | 0.95 | TEST= 0 |
| INDE | 14 | 52 | 56 | FOBS= | 78.3 | SIGMA= | 4.5 | PHAS= | 52.4 | FOM= | 0.92 | TEST= 0 |
| INDE | 14 | 53 | 15 | FOBS= | 103.4 | SIGMA= | 2.6 | PHAS= | 83.5 | FOM= | 0.93 | TEST= 0 |
| INDE | 14 | 53 | 17 | FOBS= | 100.7 | SIGMA= | 2.6 | PHAS= | 10.2 | FOM= | 0.87 | TEST= 0 |
| INDE | 14 | 53 | 19 | FOBS= | 116.1 | SIGMA= | 1.8 | PHAS= | 166.3 | FOM= | 0.82 | TEST= 0 |
| INDE | 14 | 53 | 21 | FOBS= | 155.7 | SIGMA= | 1.4 | PHAS= | 66.8 | FOM= | 0.91 | TEST= 0 |
| INDE | 14 | 53 | 23 | FOBS= | 0.0 | SIGMA= | 20.0 | PHAS= | 0.0 | FOM= | 0.00 | TEST= 0 |
| INDE | 14 | 53 | 25 | FOBS= | 61.8 | SIGMA= | 3.3 | PHAS= | -97.6 | FOM= | 0.90 | TEST= 0 |
| INDE | 14 | 53 | 27 | FOBS= | 79.4 | SIGMA= | 2.6 | PHAS= | -168.2 | FOM= | 0.92 | TEST= 0 |
| INDE | 14 | 53 | 29 | FOBS= | 18.2 | SIGMA= | 11.0 | PHAS= | 76.6 | FOM= | 0.05 | TEST= 0 |
| INDE | 14 | 53 | 31 | FOBS= | 60.1 | SIGMA= | 3.4 | PHAS= | -31.1 | FOM= | 0.90 | TEST= 0 |
| INDE | 14 | 53 | 33 | FOBS= | 70.1 | SIGMA= | 2.9 | PHAS= | -112.1 | FOM= | 0.80 | TEST= 0 |
| INDE | 14 | 53 | 35 | FOBS= | 55.3 | SIGMA= | 3.7 | PHAS= | -158.4 | FOM= | 0.03 | TEST= 1 |
| INDE | 14 | 53 | 37 | FOBS= | 41.5 | SIGMA= | 4.4 | PHAS= | 127.0 | FOM= | 0.16 | TEST= 0 |
| INDE | 14 | 53 | 39 | FOBS= | 41.3 | SIGMA= | 4.5 | PHAS= | 43.7 | FOM= | 0.64 | TEST= 0 |
| INDE | 14 | 53 | 41 | FOBS= | 66.5 | SIGMA= | 2.6 | PHAS= | 111.1 | FOM= | 0.66 | TEST= 0 |
| INDE | 14 | 53 | 43 | FOBS= | 24.7 | SIGMA= | 8.1 | PHAS= | -124.7 | FOM= | 0.13 | TEST= 0 |
| INDE | 14 | 53 | 45 | FOBS= | 19.4 | SIGMA= | 10.0 | PHAS= | 113.8 | FOM= | 0.36 | TEST= 0 |
| INDE | 14 | 53 | 47 | FOBS= | 35.9 | SIGMA= | 6.7 | PHAS= | 16.3 | FOM= | 0.73 | TEST= 0 |
| INDE | 14 | 53 | 49 | FOBS= | 30.1 | SIGMA= | 8.6 | PHAS= | 10.2 | FOM= | 0.29 | TEST= 0 |
| INDE | 14 | 53 | 51 | FOBS= | 0.0 | SIGMA= | 21.6 | PHAS= | 0.0 | FOM= | 0.00 | TEST= 0 |
| INDE | 14 | 53 | 53 | FOBS= | 129.4 | SIGMA= | 2.8 | PHAS= | -42.4 | FOM= | 0.96 | TEST= 0 |
| INDE | 14 | 53 | 55 | FOBS= | 89.8 | SIGMA= | 5.1 | PHAS= | -34.1 | FOM= | 0.90 | TEST= 0 |
| INDE | 14 | 54 | 14 | FOBS= | 139.4 | SIGMA= | 2.0 | PHAS= | -41.3 | FOM= | 0.93 | TEST= 0 |
| INDE | 14 | 54 | 16 | FOBS= | 124.0 | SIGMA= | 2.2 | PHAS= | 110.9 | FOM= | 0.92 | TEST= 0 |
| INDE | 14 | 54 | 18 | FOBS= | 84.9 | SIGMA= | 3.1 | PHAS= | -86.0 | FOM= | 0.59 | TEST= 0 |
| INDE | 14 | 54 | 20 | FOBS= | 151.8 | SIGMA= | 1.4 | PHAS= | -150.7 | FOM= | 0.83 | TEST= 0 |
| INDE | 14 | 54 | 22 | FOBS= | 158.6 | SIGMA= | 1.5 | PHAS= | 75.2 | FOM= | 0.83 | TEST= 0 |
| INDE | 14 | 54 | 24 | FOBS= | 0.0 | SIGMA= | 21.1 | PHAS= | 0.0 | FOM= | 0.00 | TEST= 1 |
| INDE | 14 | 54 | 26 | FOBS= | 95.9 | SIGMA= | 2.2 | PHAS= | 131.6 | FOM= | 0.85 | TEST= 0 |
| INDE | 14 | 54 | 28 | FOBS= | 41.9 | SIGMA= | 4.8 | PHAS= | -65.4 | FOM= | 0.20 | TEST= 0 |
| INDE | 14 | 54 | 30 | FOBS= | 52.4 | SIGMA= | 3.9 | PHAS= | -101.7 | FOM= | 0.73 | TEST= 0 |
| INDE | 14 | 54 | 32 | FOBS= | 54.3 | SIGMA= | 3.7 | PHAS= | -120.4 | FOM= | 0.27 | TEST= 0 |
| INDE | 14 | 54 | 34 | FOBS= | 47.7 | SIGMA= | 4.3 | PHAS= | 167.5 | FOM= | 0.70 | TEST= 0 |
| INDE | 14 | 54 | 36 | FOBS= | 105.7 | SIGMA= | 1.9 | PHAS= | 151.7 | FOM= | 0.93 | TEST= 0 |
| INDE | 14 | 54 | 38 | FOBS= | 0.0 | SIGMA= | 20.5 | PHAS= | 0.0 | FOM= | 0.00 | TEST= 0 |
| INDE | 14 | 54 | 40 | FOBS= | 89.8 | SIGMA= | 2.1 | PHAS= | -35.4 | FOM= | 0.78 | TEST= 0 |
| INDE | 14 | 54 | 42 | FOBS= | 26.6 | SIGMA= | 6.4 | PHAS= | 169.6 | FOM= | 0.18 | TEST= 0 |
| INDE | 14 | 54 | 44 | FOBS= | 84.9 | SIGMA= | 2.1 | PHAS= | 17.9 | FOM= | 0.86 | TEST= 0 |
| INDE | 14 | 54 | 46 | FOBS= | 0.0 | SIGMA= | 20.6 | PHAS= | 0.0 | FOM= | 0.00 | TEST= 0 |
| INDE | 14 | 54 | 48 | FOBS= | 0.0 | SIGMA= | 22.9 | PHAS= | 0.0 | FOM= | 0.00 | TEST= 0 |
| INDE | 14 | 54 | 50 | FOBS= | 0.0 | SIGMA= | 23.1 | PHAS= | 0.0 | FOM= | 0.00 | TEST= 0 |
| INDE | 14 | 54 | 52 | FOBS= | 0.0 | SIGMA= | 26.6 | PHAS= | 0.0 | FOM= | 0.00 | TEST= 0 |
| INDE | 14 | 54 | 54 | FOBS= | 65.0 | SIGMA= | 7.1 | PHAS= | -123.8 | FOM= | 0.85 | TEST= 0 |
| INDE | 14 | 55 | 15 | FOBS= | 53.0 | SIGMA= | 4.8 | PHAS= | -47.0 | FOM= | 0.43 | TEST= 0 |
| INDE | 14 | 55 | 17 | FOBS= | 96.9 | SIGMA= | 2.7 | PHAS= | -101.2 | FOM= | 0.27 | TEST= 1 |
| INDE | 14 | 55 | 19 | FOBS= | 114.1 | SIGMA= | 1.8 | PHAS= | 142.9 | FOM= | 0.69 | TEST= 1 |
| INDE | 14 | 55 | 21 | FOBS= | 173.7 | SIGMA= | 1.2 | PHAS= | 74.1 | FOM= | 0.95 | TEST= 0 |
| INDE | 14 | 55 | 23 | FOBS= | 124.9 | SIGMA= | 1.7 | PHAS= | 40.6 | FOM= | 0.92 | TEST= 0 |
| INDE | 14 | 55 | 25 | FOBS= | 114.8 | SIGMA= | 1.8 | PHAS= | -67.1 | FOM= | 0.83 | TEST= 0 |
| INDE | 14 | 55 | 27 | FOBS= | 36.8 | SIGMA= | 5.4 | PHAS= | -140.9 | FOM= | 0.39 | TEST= 0 |
| INDE | 14 | 55 | 29 | FOBS= | 34.9 | SIGMA= | 6.9 | PHAS= | -147.8 | FOM= | 0.17 | TEST= 0 |
| INDE | 14 | 55 | 31 | FOBS= | 0.0 | SIGMA= | 23.2 | PHAS= | 0.0 | FOM= | 0.00 | TEST= 1 |
| INDE | 14 | 55 | 33 | FOBS= | 24.8 | SIGMA= | 8.8 | PHAS= | 131.7 | FOM= | 0.26 | TEST= 0 |
| INDE | 14 | 55 | 35 | FOBS= | 74.9 | SIGMA= | 2.8 | PHAS= | 54.4 | FOM= | 0.91 | TEST= 0 |
| INDE | 14 | 55 | 37 | FOBS= | 0.0 | SIGMA= | 20.6 | PHAS= | 0.0 | FOM= | 0.00 | TEST= 0 |
| INDE | 14 | 55 | 39 | FOBS= | 23.0 | SIGMA= | 9.4 | PHAS= | 139.3 | FOM= | 0.37 | TEST= 0 |
| INDE | 14 | 55 | 41 | FOBS= | 45.4 | SIGMA= | 4.4 | PHAS= | 24.8 | FOM= | 0.22 | TEST= 0 |
| INDE | 14 | 55 | 43 | FOBS= | 26.5 | SIGMA= | 6.9 | PHAS= | -112.4 | FOM= | 0.39 | TEST= 0 |
| INDE | 14 | 55 | 45 | FOBS= | 90.8 | SIGMA= | 2.3 | PHAS= | -31.1 | FOM= | 0.91 | TEST= 0 |

*FIG. 12A - 355*

```
INDE 14 55 47 FOBS=    0.0 SIGMA= 25.9 PHAS=    0.0 FOM= 0.00 TEST= 0
INDE 14 55 49 FOBS=   42.0 SIGMA=  7.5 PHAS=  -72.6 FOM= 0.19 TEST= 0
INDE 14 55 51 FOBS=    0.0 SIGMA= 26.5 PHAS=    0.0 FOM= 0.00 TEST= 1
INDE 14 55 53 FOBS=    0.0 SIGMA= 29.4 PHAS=    0.0 FOM= 0.00 TEST= 0
INDE 14 56 14 FOBS=   30.2 SIGMA=  6.6 PHAS= -161.6 FOM= 0.75 TEST= 0
INDE 14 56 16 FOBS=   81.2 SIGMA=  3.2 PHAS=   49.5 FOM= 0.88 TEST= 0
INDE 14 56 18 FOBS=  120.6 SIGMA=  2.2 PHAS=   42.9 FOM= 0.92 TEST= 0
INDE 14 56 20 FOBS=   75.6 SIGMA=  2.6 PHAS= -103.1 FOM= 0.17 TEST= 0
INDE 14 56 22 FOBS=   98.7 SIGMA=  2.2 PHAS=  -17.7 FOM= 0.93 TEST= 0
INDE 14 56 24 FOBS=  104.1 SIGMA=  2.0 PHAS= -151.9 FOM= 0.71 TEST= 1
INDE 14 56 26 FOBS=   72.0 SIGMA=  2.8 PHAS= -150.7 FOM= 0.84 TEST= 0
INDE 14 56 28 FOBS=   34.1 SIGMA=  5.8 PHAS=  151.0 FOM= 0.16 TEST= 1
INDE 14 56 30 FOBS=    0.0 SIGMA= 21.0 PHAS=    0.0 FOM= 0.00 TEST= 0
INDE 14 56 32 FOBS=   69.0 SIGMA=  2.9 PHAS=   17.9 FOM= 0.51 TEST= 0
INDE 14 56 34 FOBS=   64.6 SIGMA=  3.2 PHAS= -108.7 FOM= 0.11 TEST= 1
INDE 14 56 36 FOBS=    7.6 SIGMA= 33.7 PHAS=  136.6 FOM= 0.10 TEST= 0
INDE 14 56 38 FOBS=   79.6 SIGMA=  2.5 PHAS=   53.0 FOM= 0.82 TEST= 0
INDE 14 56 40 FOBS=   50.3 SIGMA=  4.3 PHAS=  -72.0 FOM= 0.73 TEST= 0
INDE 14 56 42 FOBS=   11.1 SIGMA= 19.9 PHAS=  -76.1 FOM= 0.10 TEST= 0
INDE 14 56 44 FOBS=   23.9 SIGMA= 10.0 PHAS=   39.0 FOM= 0.02 TEST= 1
INDE 14 56 46 FOBS=   59.4 SIGMA=  3.8 PHAS= -113.0 FOM= 0.81 TEST= 0
INDE 14 56 48 FOBS=   57.6 SIGMA=  4.7 PHAS=  -91.5 FOM= 0.74 TEST= 0
INDE 14 56 50 FOBS=    0.0 SIGMA= 27.0 PHAS=    0.0 FOM= 0.00 TEST= 0
INDE 14 56 52 FOBS=   43.2 SIGMA= 14.6 PHAS=   51.2 FOM= 0.72 TEST= 0
INDE 14 57 15 FOBS=    0.0 SIGMA= 26.7 PHAS=    0.0 FOM= 0.00 TEST= 0
INDE 14 57 17 FOBS=  108.0 SIGMA=  2.5 PHAS=   55.9 FOM= 0.94 TEST= 0
INDE 14 57 19 FOBS=  128.6 SIGMA=  2.1 PHAS=   56.8 FOM= 0.96 TEST= 0
INDE 14 57 21 FOBS=   77.5 SIGMA=  2.6 PHAS= -110.4 FOM= 0.85 TEST= 0
INDE 14 57 23 FOBS=   31.4 SIGMA=  6.1 PHAS= -176.5 FOM= 0.39 TEST= 0
INDE 14 57 25 FOBS=   40.4 SIGMA=  4.9 PHAS=   57.5 FOM= 0.53 TEST= 0
INDE 14 57 27 FOBS=   53.7 SIGMA=  4.1 PHAS=  -84.2 FOM= 0.32 TEST= 1
INDE 14 57 29 FOBS=   28.4 SIGMA=  7.8 PHAS= -152.7 FOM= 0.20 TEST= 0
INDE 14 57 31 FOBS=  100.3 SIGMA=  2.1 PHAS=   36.1 FOM= 0.59 TEST= 0
INDE 14 57 33 FOBS=   22.9 SIGMA=  9.6 PHAS=  -40.1 FOM= 0.21 TEST= 0
INDE 14 57 35 FOBS=   51.2 SIGMA=  4.9 PHAS=   37.5 FOM= 0.71 TEST= 0
INDE 14 57 37 FOBS=   52.9 SIGMA=  4.9 PHAS=  -72.9 FOM= 0.76 TEST= 0
INDE 14 57 39 FOBS=   21.5 SIGMA= 10.8 PHAS=  137.5 FOM= 0.24 TEST= 0
INDE 14 57 41 FOBS=   23.5 SIGMA=  9.3 PHAS= -120.7 FOM= 0.38 TEST= 0
INDE 14 57 43 FOBS=   84.9 SIGMA=  2.3 PHAS=   91.3 FOM= 0.84 TEST= 0
INDE 14 57 45 FOBS=   79.7 SIGMA=  2.6 PHAS=  -34.6 FOM= 0.93 TEST= 0
INDE 14 57 47 FOBS=   69.0 SIGMA=  3.3 PHAS= -175.5 FOM= 0.90 TEST= 0
INDE 14 57 49 FOBS=   46.0 SIGMA=  7.9 PHAS= -164.5 FOM= 0.88 TEST= 0
INDE 14 57 51 FOBS=   98.0 SIGMA=  6.7 PHAS=  -48.1 FOM= 0.75 TEST= 0
INDE 14 58 14 FOBS=  112.3 SIGMA=  1.5 PHAS=   15.1 FOM= 0.89 TEST= 0
INDE 14 58 16 FOBS=  139.3 SIGMA=  1.9 PHAS=  -27.5 FOM= 0.96 TEST= 0
INDE 14 58 18 FOBS=  193.7 SIGMA=  1.5 PHAS=  -22.6 FOM= 0.96 TEST= 0
INDE 14 58 20 FOBS=  116.3 SIGMA=  2.2 PHAS=  -65.6 FOM= 0.92 TEST= 0
INDE 14 58 22 FOBS=   40.8 SIGMA=  5.1 PHAS= -165.9 FOM= 0.49 TEST= 0
INDE 14 58 24 FOBS=   98.0 SIGMA=  2.1 PHAS= -123.8 FOM= 0.91 TEST= 0
INDE 14 58 26 FOBS=  135.0 SIGMA=  1.6 PHAS=  -41.7 FOM= 0.88 TEST= 0
INDE 14 58 28 FOBS=   59.8 SIGMA=  3.7 PHAS= -106.2 FOM= 0.26 TEST= 0
INDE 14 58 30 FOBS=   84.9 SIGMA=  2.9 PHAS=  160.0 FOM= 0.25 TEST= 1
INDE 14 58 32 FOBS=   56.0 SIGMA=  4.4 PHAS=  -54.6 FOM= 0.81 TEST= 0
INDE 14 58 34 FOBS=   58.9 SIGMA=  4.2 PHAS=  -82.1 FOM= 0.66 TEST= 0
INDE 14 58 36 FOBS=   23.4 SIGMA= 10.7 PHAS= -104.3 FOM= 0.26 TEST= 0
INDE 14 58 38 FOBS=   80.4 SIGMA=  2.7 PHAS=  106.4 FOM= 0.26 TEST= 1
INDE 14 58 40 FOBS=    0.0 SIGMA= 24.4 PHAS=    0.0 FOM= 0.00 TEST= 0
INDE 14 58 42 FOBS=   56.5 SIGMA=  3.9 PHAS=  -56.0 FOM= 0.07 TEST= 1
INDE 14 58 44 FOBS=   38.0 SIGMA=  6.1 PHAS= -162.8 FOM= 0.14 TEST= 0
INDE 14 58 46 FOBS=   61.0 SIGMA=  3.8 PHAS=  151.7 FOM= 0.85 TEST= 0
INDE 14 58 48 FOBS=   37.7 SIGMA=  7.2 PHAS=   95.9 FOM= 0.52 TEST= 0
INDE 14 59 15 FOBS=  150.2 SIGMA=  1.3 PHAS= -101.1 FOM= 0.95 TEST= 0
INDE 14 59 17 FOBS=   48.6 SIGMA=  5.2 PHAS=  176.1 FOM= 0.74 TEST= 0
INDE 14 59 19 FOBS=   91.7 SIGMA=  2.8 PHAS= -162.1 FOM= 0.90 TEST= 0
INDE 14 59 21 FOBS=  112.3 SIGMA=  1.8 PHAS= -120.9 FOM= 0.95 TEST= 0
INDE 14 59 23 FOBS=   79.4 SIGMA=  2.5 PHAS= -124.2 FOM= 0.90 TEST= 0
INDE 14 59 25 FOBS=  186.2 SIGMA=  1.4 PHAS= -148.3 FOM= 0.95 TEST= 0
INDE 14 59 27 FOBS=   54.2 SIGMA=  4.5 PHAS=  -99.3 FOM= 0.66 TEST= 0
INDE 14 59 29 FOBS=    0.0 SIGMA= 22.0 PHAS=    0.0 FOM= 0.00 TEST= 0
INDE 14 59 31 FOBS=   80.1 SIGMA=  3.1 PHAS= -113.7 FOM= 0.89 TEST= 0
```

*FIG. 12A - 356*

```
INDE  14  59  33  FOBS=    0.0  SIGMA=  24.0  PHAS=    0.0  FOM= 0.00  TEST= 0
INDE  14  59  35  FOBS=   64.7  SIGMA=   3.9  PHAS= -147.8  FOM= 0.68  TEST= 0
INDE  14  59  37  FOBS=  106.8  SIGMA=   2.5  PHAS=  -69.6  FOM= 0.94  TEST= 0
INDE  14  59  39  FOBS=   90.5  SIGMA=   2.5  PHAS=  100.6  FOM= 0.30  TEST= 1
INDE  14  59  41  FOBS=    0.0  SIGMA=  21.9  PHAS=    0.0  FOM= 0.00  TEST= 0
INDE  14  59  43  FOBS=   57.8  SIGMA=   3.9  PHAS=  103.6  FOM= 0.88  TEST= 0
INDE  14  59  45  FOBS=    0.0  SIGMA=  23.0  PHAS=    0.0  FOM= 0.00  TEST= 0
INDE  14  59  47  FOBS=    0.0  SIGMA=  24.8  PHAS=    0.0  FOM= 0.00  TEST= 1
INDE  14  60  14  FOBS=   18.9  SIGMA=  10.5  PHAS=   20.1  FOM= 0.38  TEST= 0
INDE  14  60  16  FOBS=   47.9  SIGMA=   3.9  PHAS=  -83.9  FOM= 0.70  TEST= 0
INDE  14  60  18  FOBS=   48.8  SIGMA=   4.9  PHAS= -133.1  FOM= 0.62  TEST= 0
INDE  14  60  20  FOBS=   50.7  SIGMA=   5.6  PHAS=  121.6  FOM= 0.61  TEST= 0
INDE  14  60  22  FOBS=  116.2  SIGMA=   2.1  PHAS=  174.0  FOM= 0.95  TEST= 0
INDE  14  60  24  FOBS=   53.5  SIGMA=   4.3  PHAS= -173.7  FOM= 0.88  TEST= 0
INDE  14  60  26  FOBS=   96.4  SIGMA=   2.5  PHAS= -169.7  FOM= 0.92  TEST= 0
INDE  14  60  28  FOBS=    0.0  SIGMA=  21.8  PHAS=    0.0  FOM= 0.00  TEST= 1
INDE  14  60  30  FOBS=   91.7  SIGMA=   2.7  PHAS=  134.4  FOM= 0.87  TEST= 0
INDE  14  60  32  FOBS=   65.3  SIGMA=   3.8  PHAS= -147.5  FOM= 0.89  TEST= 0
INDE  14  60  34  FOBS=   51.6  SIGMA=   4.8  PHAS=   23.1  FOM= 0.57  TEST= 0
INDE  14  60  36  FOBS=  126.3  SIGMA=   2.1  PHAS=  127.7  FOM= 0.17  TEST= 1
INDE  14  60  38  FOBS=   41.3  SIGMA=   6.3  PHAS=  146.0  FOM= 0.76  TEST= 0
INDE  14  60  40  FOBS=   68.5  SIGMA=   3.3  PHAS=   20.8  FOM= 0.89  TEST= 0
INDE  14  60  42  FOBS=   38.7  SIGMA=   6.4  PHAS=  -74.7  FOM= 0.60  TEST= 0
INDE  14  60  44  FOBS=   28.1  SIGMA=  11.1  PHAS=   78.9  FOM= 0.23  TEST= 0
INDE  14  60  46  FOBS=   44.5  SIGMA=   9.5  PHAS=  135.3  FOM= 0.73  TEST= 0
INDE  14  61  15  FOBS=   17.7  SIGMA=  15.7  PHAS=  -39.4  FOM= 0.39  TEST= 0
INDE  14  61  17  FOBS=   75.7  SIGMA=   3.8  PHAS=  163.6  FOM= 0.85  TEST= 0
INDE  14  61  19  FOBS=   63.0  SIGMA=   5.4  PHAS=  139.9  FOM= 0.84  TEST= 0
INDE  14  61  21  FOBS=    0.0  SIGMA=  26.0  PHAS=    0.0  FOM= 0.00  TEST= 0
INDE  14  61  23  FOBS=   13.4  SIGMA=  19.7  PHAS= -167.6  FOM= 0.65  TEST= 0
INDE  14  61  25  FOBS=   70.6  SIGMA=   3.3  PHAS=  -94.3  FOM= 0.14  TEST= 1
INDE  14  61  27  FOBS=   61.2  SIGMA=   3.9  PHAS= -170.6  FOM= 0.61  TEST= 0
INDE  14  61  29  FOBS=   41.3  SIGMA=   5.9  PHAS=   -7.4  FOM= 0.65  TEST= 0
INDE  14  61  31  FOBS=   26.0  SIGMA=   9.5  PHAS= -105.5  FOM= 0.46  TEST= 0
INDE  14  61  33  FOBS=   52.2  SIGMA=   4.8  PHAS=   96.7  FOM= 0.14  TEST= 0
INDE  14  61  35  FOBS=   78.1  SIGMA=   3.3  PHAS=   36.4  FOM= 0.83  TEST= 0
INDE  14  61  37  FOBS=   46.4  SIGMA=   5.6  PHAS= -177.9  FOM= 0.41  TEST= 0
INDE  14  61  39  FOBS=   43.2  SIGMA=   5.6  PHAS=   41.0  FOM= 0.72  TEST= 0
INDE  14  61  41  FOBS=   59.1  SIGMA=   3.8  PHAS=    0.0  FOM= 0.78  TEST= 0
INDE  14  61  43  FOBS=   53.7  SIGMA=   5.9  PHAS=  141.9  FOM= 0.80  TEST= 0
INDE  14  61  45  FOBS=   16.7  SIGMA=  18.3  PHAS=   18.9  FOM= 0.33  TEST= 0
INDE  14  62  14  FOBS=   64.1  SIGMA=   3.6  PHAS= -150.5  FOM= 0.24  TEST= 0
INDE  14  62  16  FOBS=   39.6  SIGMA=   5.0  PHAS=  -49.9  FOM= 0.76  TEST= 0
INDE  14  62  18  FOBS=   28.9  SIGMA=  11.6  PHAS=   97.8  FOM= 0.21  TEST= 0
INDE  14  62  20  FOBS=    0.0  SIGMA=  25.8  PHAS=    0.0  FOM= 0.00  TEST= 0
INDE  14  62  22  FOBS=   35.9  SIGMA=   9.5  PHAS=  -27.5  FOM= 0.44  TEST= 0
INDE  14  62  24  FOBS=   45.2  SIGMA=   5.9  PHAS=  -87.5  FOM= 0.54  TEST= 0
INDE  14  62  26  FOBS=   50.7  SIGMA=   4.6  PHAS=  142.9  FOM= 0.41  TEST= 0
INDE  14  62  28  FOBS=   57.0  SIGMA=   4.9  PHAS=   55.7  FOM= 0.66  TEST= 0
INDE  14  62  30  FOBS=   56.2  SIGMA=   5.1  PHAS= -152.5  FOM= 0.84  TEST= 0
INDE  14  62  32  FOBS=   54.4  SIGMA=   5.3  PHAS=  179.8  FOM= 0.75  TEST= 0
INDE  14  62  34  FOBS=   32.6  SIGMA=   8.8  PHAS=   67.3  FOM= 0.58  TEST= 0
INDE  14  62  36  FOBS=   54.9  SIGMA=   5.3  PHAS=    7.1  FOM= 0.84  TEST= 0
INDE  14  62  38  FOBS=   50.4  SIGMA=   6.0  PHAS=   34.9  FOM= 0.75  TEST= 0
INDE  14  62  40  FOBS=   26.9  SIGMA=   9.1  PHAS=  -71.1  FOM= 0.45  TEST= 0
INDE  14  62  42  FOBS=    0.0  SIGMA=  28.8  PHAS=    0.0  FOM= 0.00  TEST= 0
INDE  14  62  44  FOBS=    0.0  SIGMA=  33.4  PHAS=    0.0  FOM= 0.00  TEST= 0
INDE  14  63  15  FOBS=   56.2  SIGMA=   4.1  PHAS=  -49.8  FOM= 0.69  TEST= 1
INDE  14  63  17  FOBS=    0.0  SIGMA=  20.3  PHAS=    0.0  FOM= 0.00  TEST= 0
INDE  14  63  19  FOBS=    0.0  SIGMA=  25.7  PHAS=    0.0  FOM= 0.00  TEST= 0
INDE  14  63  21  FOBS=   74.6  SIGMA=   4.6  PHAS=  -90.8  FOM= 0.90  TEST= 0
INDE  14  63  23  FOBS=   82.4  SIGMA=   3.3  PHAS= -102.5  FOM= 0.87  TEST= 0
INDE  14  63  25  FOBS=   41.2  SIGMA=   6.6  PHAS= -116.2  FOM= 0.74  TEST= 0
INDE  14  63  27  FOBS=   69.3  SIGMA=   4.0  PHAS= -141.4  FOM= 0.79  TEST= 0
INDE  14  63  29  FOBS=   45.3  SIGMA=   6.3  PHAS=   52.9  FOM= 0.73  TEST= 0
INDE  14  63  31  FOBS=   83.2  SIGMA=   3.5  PHAS=   30.7  FOM= 0.83  TEST= 0
INDE  14  63  33  FOBS=   35.6  SIGMA=   8.1  PHAS=  -13.4  FOM= 0.56  TEST= 0
INDE  14  63  35  FOBS=   27.1  SIGMA=  10.7  PHAS=  -81.5  FOM= 0.07  TEST= 1
INDE  14  63  37  FOBS=   59.3  SIGMA=   5.0  PHAS= -113.1  FOM= 0.78  TEST= 0
INDE  14  63  39  FOBS=   56.0  SIGMA=   5.5  PHAS=   -8.1  FOM= 0.74  TEST= 0
```

*FIG. 12A - 357*

```
INDE 14 63 41 FOBS=   0.0 SIGMA= 26.9 PHAS=    0.0 FOM= 0.00 TEST= 0
INDE 14 63 43 FOBS=   0.0 SIGMA= 25.5 PHAS=    0.0 FOM= 0.00 TEST= 0
INDE 14 64 14 FOBS=  92.1 SIGMA=  2.4 PHAS=  109.4 FOM= 0.65 TEST= 0
INDE 14 64 16 FOBS=  56.4 SIGMA=  3.1 PHAS=  -50.1 FOM= 0.74 TEST= 0
INDE 14 64 18 FOBS=  24.7 SIGMA= 13.6 PHAS=  148.4 FOM= 0.32 TEST= 0
INDE 14 64 20 FOBS= 128.7 SIGMA=  2.8 PHAS=  169.6 FOM= 0.91 TEST= 0
INDE 14 64 22 FOBS=  97.7 SIGMA=  3.6 PHAS= -123.0 FOM= 0.85 TEST= 0
INDE 14 64 24 FOBS=  61.5 SIGMA=  4.4 PHAS= -157.8 FOM= 0.37 TEST= 1
INDE 14 64 26 FOBS=  55.2 SIGMA=  4.9 PHAS=   96.7 FOM= 0.86 TEST= 0
INDE 14 64 28 FOBS=   0.0 SIGMA= 26.1 PHAS=    0.0 FOM= 0.00 TEST= 0
INDE 14 64 30 FOBS=  60.1 SIGMA=  4.8 PHAS=  -21.5 FOM= 0.52 TEST= 0
INDE 14 64 32 FOBS=  42.4 SIGMA=  6.9 PHAS=  -73.2 FOM= 0.69 TEST= 0
INDE 14 64 34 FOBS=   0.0 SIGMA= 27.0 PHAS=    0.0 FOM= 0.00 TEST= 0
INDE 14 64 36 FOBS=   0.0 SIGMA= 24.3 PHAS=    0.0 FOM= 0.00 TEST= 0
INDE 14 64 38 FOBS=  31.8 SIGMA=  9.5 PHAS=  -23.0 FOM= 0.41 TEST= 0
INDE 14 64 40 FOBS=   0.0 SIGMA= 25.1 PHAS=    0.0 FOM= 0.00 TEST= 0
INDE 14 65 15 FOBS=  53.9 SIGMA=  4.2 PHAS= -168.6 FOM= 0.57 TEST= 0
INDE 14 65 17 FOBS=   0.0 SIGMA= 19.4 PHAS=    0.0 FOM= 0.00 TEST= 0
INDE 14 65 19 FOBS=  88.5 SIGMA=  2.7 PHAS=   58.7 FOM= 0.94 TEST= 0
INDE 14 65 21 FOBS=  72.2 SIGMA=  4.8 PHAS=  150.0 FOM= 0.87 TEST= 0
INDE 14 65 23 FOBS=   0.0 SIGMA= 25.9 PHAS=    0.0 FOM= 0.00 TEST= 0
INDE 14 65 25 FOBS=  46.7 SIGMA=  5.8 PHAS=  -10.4 FOM= 0.29 TEST= 0
INDE 14 65 27 FOBS=   0.0 SIGMA= 23.4 PHAS=    0.0 FOM= 0.00 TEST= 0
INDE 14 65 29 FOBS=   3.3 SIGMA= 84.7 PHAS=   -5.9 FOM= 0.05 TEST= 0
INDE 14 65 31 FOBS=  37.1 SIGMA=  7.8 PHAS=  176.9 FOM= 0.05 TEST= 1
INDE 14 65 33 FOBS=  51.1 SIGMA=  5.8 PHAS=  177.7 FOM= 0.22 TEST= 1
INDE 14 65 35 FOBS=  43.2 SIGMA=  6.9 PHAS= -115.8 FOM= 0.74 TEST= 0
INDE 14 65 37 FOBS=   0.0 SIGMA= 24.5 PHAS=    0.0 FOM= 0.00 TEST= 0
INDE 14 65 39 FOBS=   0.0 SIGMA= 26.9 PHAS=    0.0 FOM= 0.00 TEST= 0
INDE 14 66 14 FOBS= 110.3 SIGMA=  2.0 PHAS=  -26.2 FOM= 0.92 TEST= 0
INDE 14 66 16 FOBS=  31.0 SIGMA=  7.4 PHAS=   64.7 FOM= 0.44 TEST= 0
INDE 14 66 18 FOBS=  60.7 SIGMA=  3.4 PHAS= -146.4 FOM= 0.85 TEST= 0
INDE 14 66 20 FOBS= 122.2 SIGMA=  2.9 PHAS=  -10.7 FOM= 0.88 TEST= 0
INDE 14 66 22 FOBS=  62.0 SIGMA=  5.5 PHAS=  -37.8 FOM= 0.72 TEST= 0
INDE 14 66 24 FOBS=  77.3 SIGMA=  4.5 PHAS=   45.8 FOM= 0.86 TEST= 0
INDE 14 66 26 FOBS=  86.2 SIGMA=  3.3 PHAS=   75.6 FOM= 0.93 TEST= 0
INDE 14 66 28 FOBS=   0.0 SIGMA= 26.0 PHAS=    0.0 FOM= 0.00 TEST= 0
INDE 14 66 30 FOBS=  50.8 SIGMA=  5.6 PHAS=  119.8 FOM= 0.86 TEST= 0
INDE 14 66 32 FOBS=  87.5 SIGMA=  3.4 PHAS=  138.2 FOM= 0.78 TEST= 0
INDE 14 66 34 FOBS=  68.9 SIGMA=  4.4 PHAS=  153.3 FOM= 0.84 TEST= 0
INDE 14 66 36 FOBS=   0.0 SIGMA= 24.6 PHAS=    0.0 FOM= 0.00 TEST= 0
INDE 14 66 38 FOBS=  40.6 SIGMA=  7.6 PHAS=   99.1 FOM= 0.22 TEST= 0
INDE 14 67 15 FOBS= 115.4 SIGMA=  2.2 PHAS= -132.2 FOM= 0.91 TEST= 0
INDE 14 67 17 FOBS=  80.5 SIGMA=  4.3 PHAS=   73.5 FOM= 0.84 TEST= 0
INDE 14 67 19 FOBS=  85.6 SIGMA=  2.5 PHAS=  160.4 FOM= 0.85 TEST= 0
INDE 14 67 21 FOBS=  45.3 SIGMA=  7.5 PHAS= -133.1 FOM= 0.72 TEST= 0
INDE 14 67 23 FOBS=  90.1 SIGMA=  3.9 PHAS=  -13.2 FOM= 0.87 TEST= 0
INDE 14 67 25 FOBS=  25.7 SIGMA= 10.5 PHAS=  -52.7 FOM= 0.13 TEST= 0
INDE 14 67 27 FOBS=  51.2 SIGMA=  5.4 PHAS=   42.2 FOM= 0.78 TEST= 0
INDE 14 67 29 FOBS=   0.0 SIGMA= 23.7 PHAS=    0.0 FOM= 0.00 TEST= 1
INDE 14 67 31 FOBS=  56.4 SIGMA=  5.2 PHAS=   22.2 FOM= 0.51 TEST= 0
INDE 14 67 33 FOBS=  38.6 SIGMA=  7.7 PHAS=   67.3 FOM= 0.76 TEST= 0
INDE 14 67 35 FOBS=  40.7 SIGMA=  7.5 PHAS=    5.3 FOM= 0.55 TEST= 0
INDE 14 68 14 FOBS=  47.2 SIGMA=  5.3 PHAS=  -49.0 FOM= 0.65 TEST= 0
INDE 14 68 16 FOBS=  47.0 SIGMA=  6.8 PHAS=  145.7 FOM= 0.66 TEST= 0
INDE 14 68 18 FOBS=  53.5 SIGMA=  3.9 PHAS=  -43.2 FOM= 0.34 TEST= 0
INDE 14 68 20 FOBS=   0.0 SIGMA= 22.0 PHAS=    0.0 FOM= 0.00 TEST= 0
INDE 14 68 22 FOBS= 104.4 SIGMA=  2.9 PHAS=    5.7 FOM= 0.19 TEST= 1
INDE 14 68 24 FOBS=  47.5 SIGMA=  7.3 PHAS=   49.7 FOM= 0.08 TEST= 1
INDE 14 68 26 FOBS=   0.0 SIGMA= 23.4 PHAS=    0.0 FOM= 0.00 TEST= 0
INDE 14 68 28 FOBS=  80.5 SIGMA=  3.6 PHAS=   -2.6 FOM= 0.88 TEST= 0
INDE 14 68 30 FOBS=   0.0 SIGMA= 23.9 PHAS=    0.0 FOM= 0.00 TEST= 0
INDE 14 68 32 FOBS=  62.9 SIGMA=  4.8 PHAS=   -3.2 FOM= 0.33 TEST= 0
INDE 14 68 34 FOBS=  17.8 SIGMA= 17.3 PHAS=  150.6 FOM= 0.23 TEST= 0
INDE 14 69 15 FOBS=  84.5 SIGMA=  3.4 PHAS=  -15.5 FOM= 0.89 TEST= 0
INDE 14 69 17 FOBS=  56.0 SIGMA=  5.8 PHAS=  123.4 FOM= 0.49 TEST= 0
INDE 14 69 19 FOBS=  19.9 SIGMA= 12.4 PHAS=  -85.8 FOM= 0.39 TEST= 0
INDE 14 69 21 FOBS=   0.0 SIGMA= 24.6 PHAS=    0.0 FOM= 0.00 TEST= 0
INDE 14 69 23 FOBS=  50.4 SIGMA=  9.8 PHAS=    3.4 FOM= 0.33 TEST= 0
INDE 14 69 25 FOBS=  63.7 SIGMA=  8.0 PHAS=  136.2 FOM= 0.77 TEST= 0
```

*FIG. 12A - 358*

```
INDE 14 69 27 FOBS=   18.3 SIGMA= 15.3 PHAS=  -93.9 FOM= 0.31 TEST= 0
INDE 14 69 29 FOBS=   34.2 SIGMA= 10.3 PHAS=  -30.9 FOM= 0.59 TEST= 0
INDE 14 69 31 FOBS=   14.4 SIGMA= 20.6 PHAS=   44.5 FOM= 0.02 TEST= 1
INDE 14 69 33 FOBS=    0.0 SIGMA= 31.8 PHAS=    0.0 FOM= 0.00 TEST= 0
INDE 14 70 16 FOBS=   59.0 SIGMA=  4.8 PHAS= -154.7 FOM= 0.85 TEST= 0
INDE 14 70 20 FOBS=   16.6 SIGMA= 15.9 PHAS=  -47.9 FOM= 0.18 TEST= 0
INDE 14 70 22 FOBS=   68.5 SIGMA=  4.8 PHAS=  -97.9 FOM= 0.66 TEST= 0
INDE 14 70 24 FOBS=   75.3 SIGMA=  5.1 PHAS=   16.6 FOM= 0.71 TEST= 0
INDE 14 70 28 FOBS=   35.1 SIGMA= 10.0 PHAS=  -36.7 FOM= 0.42 TEST= 0
INDE 14 70 30 FOBS=    0.0 SIGMA= 27.0 PHAS=    0.0 FOM= 0.00 TEST= 0
INDE 14 71 15 FOBS=   66.4 SIGMA=  3.7 PHAS=   41.8 FOM= 0.71 TEST= 0
INDE 14 71 17 FOBS=   36.7 SIGMA=  8.7 PHAS=  162.1 FOM= 0.50 TEST= 0
INDE 14 71 21 FOBS=    0.0 SIGMA= 23.6 PHAS=    0.0 FOM= 0.00 TEST= 0
INDE 14 71 23 FOBS=   71.8 SIGMA=  4.7 PHAS= -172.4 FOM= 0.90 TEST= 0
INDE 14 71 25 FOBS=   62.6 SIGMA=  6.3 PHAS= -161.9 FOM= 0.81 TEST= 0
INDE 14 72 16 FOBS=   47.6 SIGMA=  5.9 PHAS=  -41.2 FOM= 0.28 TEST= 0
INDE 14 72 18 FOBS=    0.0 SIGMA= 25.7 PHAS=    0.0 FOM= 0.00 TEST= 0
INDE 14 72 20 FOBS=   60.6 SIGMA=  3.9 PHAS=  -78.1 FOM= 0.88 TEST= 0
INDE 14 72 22 FOBS=   42.4 SIGMA=  7.2 PHAS=   69.6 FOM= 0.54 TEST= 0
INDE 14 72 24 FOBS=   62.6 SIGMA=  5.7 PHAS=   84.6 FOM= 0.85 TEST= 0
INDE 14 73 17 FOBS=   33.2 SIGMA=  8.8 PHAS=  -29.7 FOM= 0.25 TEST= 0
INDE 14 73 21 FOBS=    0.0 SIGMA= 22.7 PHAS=    0.0 FOM= 0.00 TEST= 0
INDE 14 74 16 FOBS=   25.1 SIGMA=  9.5 PHAS=   -9.5 FOM= 0.48 TEST= 0
INDE 14 74 18 FOBS=   50.0 SIGMA=  6.7 PHAS= -155.1 FOM= 0.53 TEST= 0
INDE 15 16 15 FOBS=   37.4 SIGMA=  2.6 PHAS= -137.6 FOM= 0.87 TEST= 1
INDE 15 16 17 FOBS=  152.2 SIGMA=  0.7 PHAS= -125.6 FOM= 0.98 TEST= 0
INDE 15 16 19 FOBS=  138.6 SIGMA=  0.6 PHAS= -103.4 FOM= 0.91 TEST= 1
INDE 15 16 21 FOBS=  121.2 SIGMA=  0.7 PHAS=   52.3 FOM= 0.98 TEST= 0
INDE 15 16 23 FOBS=   54.9 SIGMA=  1.5 PHAS=  -96.3 FOM= 0.97 TEST= 0
INDE 15 16 25 FOBS=  135.3 SIGMA=  0.7 PHAS= -142.0 FOM= 0.99 TEST= 0
INDE 15 16 27 FOBS=   48.3 SIGMA=  1.8 PHAS=  139.8 FOM= 0.98 TEST= 1
INDE 15 16 29 FOBS=  135.9 SIGMA=  0.7 PHAS=   36.5 FOM= 0.66 TEST= 0
INDE 15 16 31 FOBS=  196.9 SIGMA=  0.6 PHAS=  162.3 FOM= 0.94 TEST= 1
INDE 15 16 33 FOBS=   35.9 SIGMA=  2.9 PHAS=  -81.9 FOM= 0.55 TEST= 0
INDE 15 16 35 FOBS=  195.6 SIGMA=  0.7 PHAS=  113.8 FOM= 0.40 TEST= 0
INDE 15 16 37 FOBS=  239.8 SIGMA=  0.6 PHAS=  121.9 FOM= 0.94 TEST= 0
INDE 15 16 39 FOBS=   98.6 SIGMA=  1.5 PHAS=  -84.6 FOM= 0.74 TEST= 0
INDE 15 16 41 FOBS=  177.5 SIGMA=  1.0 PHAS=   65.7 FOM= 0.94 TEST= 0
INDE 15 16 43 FOBS=  245.6 SIGMA=  0.9 PHAS=   17.8 FOM= 0.96 TEST= 0
INDE 15 16 45 FOBS=  161.9 SIGMA=  1.8 PHAS= -146.0 FOM= 0.90 TEST= 0
INDE 15 16 47 FOBS=  267.0 SIGMA=  1.2 PHAS=  103.9 FOM= 0.02 TEST= 1
INDE 15 16 49 FOBS=  207.9 SIGMA=  1.4 PHAS=   12.7 FOM= 0.97 TEST= 0
INDE 15 16 51 FOBS=  111.1 SIGMA=  2.0 PHAS=  -42.1 FOM= 0.60 TEST= 0
INDE 15 16 53 FOBS=  123.1 SIGMA=  1.5 PHAS=  159.7 FOM= 0.88 TEST= 0
INDE 15 16 55 FOBS=  135.9 SIGMA=  1.4 PHAS=    9.3 FOM= 0.94 TEST= 0
INDE 15 16 57 FOBS=  103.8 SIGMA=  2.1 PHAS=    9.8 FOM= 0.89 TEST= 0
INDE 15 16 59 FOBS=  152.9 SIGMA=  1.4 PHAS=  -82.3 FOM= 0.94 TEST= 0
INDE 15 16 61 FOBS=   35.0 SIGMA=  4.8 PHAS=  -13.7 FOM= 0.17 TEST= 0
INDE 15 16 63 FOBS=   57.3 SIGMA=  4.0 PHAS=   92.7 FOM= 0.70 TEST= 0
INDE 15 16 65 FOBS=   58.5 SIGMA=  3.9 PHAS=  107.6 FOM= 0.76 TEST= 0
INDE 15 16 67 FOBS=   58.2 SIGMA=  5.0 PHAS= -145.6 FOM= 0.75 TEST= 0
INDE 15 16 69 FOBS=   54.8 SIGMA=  4.4 PHAS=  167.5 FOM= 0.79 TEST= 0
INDE 15 17 16 FOBS=  164.8 SIGMA=  0.6 PHAS=  153.5 FOM= 0.99 TEST= 0
INDE 15 17 18 FOBS=  292.7 SIGMA=  0.6 PHAS=  110.8 FOM= 0.98 TEST= 0
INDE 15 17 20 FOBS=   76.4 SIGMA=  1.0 PHAS=  120.3 FOM= 0.98 TEST= 0
INDE 15 17 22 FOBS=   51.6 SIGMA=  1.7 PHAS=   23.0 FOM= 0.98 TEST= 0
INDE 15 17 24 FOBS=  272.5 SIGMA=  0.5 PHAS= -159.5 FOM= 0.99 TEST= 0
INDE 15 17 26 FOBS=  268.0 SIGMA=  0.5 PHAS=  159.8 FOM= 0.99 TEST= 0
INDE 15 17 28 FOBS=  400.0 SIGMA=  0.5 PHAS=   32.4 FOM= 0.99 TEST= 0
INDE 15 17 30 FOBS=  135.2 SIGMA=  0.8 PHAS=   12.2 FOM= 0.96 TEST= 0
INDE 15 17 32 FOBS=  112.6 SIGMA=  1.0 PHAS=  -79.4 FOM= 0.79 TEST= 0
INDE 15 17 34 FOBS=  184.7 SIGMA=  0.7 PHAS=   61.5 FOM= 0.91 TEST= 0
INDE 15 17 36 FOBS=  297.0 SIGMA=  0.6 PHAS=   87.5 FOM= 0.96 TEST= 0
INDE 15 17 38 FOBS=  122.7 SIGMA=  1.1 PHAS=   55.0 FOM= 0.96 TEST= 0
INDE 15 17 40 FOBS=  282.7 SIGMA=  0.7 PHAS=   57.2 FOM= 0.96 TEST= 0
INDE 15 17 42 FOBS=  207.8 SIGMA=  0.8 PHAS=  -31.7 FOM= 0.85 TEST= 0
INDE 15 17 44 FOBS=  121.5 SIGMA=  1.5 PHAS=  -90.2 FOM= 0.88 TEST= 0
INDE 15 17 46 FOBS=  184.4 SIGMA=  1.0 PHAS=  115.4 FOM= 0.94 TEST= 0
INDE 15 17 48 FOBS=  121.8 SIGMA=  1.4 PHAS=  -58.4 FOM= 0.42 TEST= 0
INDE 15 17 50 FOBS=   48.8 SIGMA=  3.9 PHAS=   69.9 FOM= 0.74 TEST= 0
```

*FIG. 12A - 359*

```
INDE 15 17 52 FOBS=  128.9 SIGMA=  1.5 PHAS=  165.7 FOM= 0.85 TEST= 0
INDE 15 17 54 FOBS=   68.9 SIGMA=  2.7 PHAS= -107.6 FOM= 0.80 TEST= 0
INDE 15 17 56 FOBS=  174.6 SIGMA=  1.1 PHAS=  -85.2 FOM= 0.97 TEST= 0
INDE 15 17 58 FOBS=  199.0 SIGMA=  1.2 PHAS= -128.4 FOM= 0.97 TEST= 0
INDE 15 17 60 FOBS=   84.2 SIGMA=  2.6 PHAS=  150.5 FOM= 0.89 TEST= 0
INDE 15 17 62 FOBS=   54.9 SIGMA=  4.4 PHAS=  -32.1 FOM= 0.59 TEST= 0
INDE 15 17 64 FOBS=   30.2 SIGMA=  7.6 PHAS=   29.3 FOM= 0.34 TEST= 0
INDE 15 17 66 FOBS=  105.9 SIGMA=  2.3 PHAS=    5.4 FOM= 0.87 TEST= 0
INDE 15 17 68 FOBS=   77.6 SIGMA=  3.4 PHAS=   60.4 FOM= 0.85 TEST= 0
INDE 15 18 15 FOBS=  182.9 SIGMA=  0.6 PHAS=  137.7 FOM= 0.97 TEST= 0
INDE 15 18 17 FOBS=  170.0 SIGMA=  0.6 PHAS=   10.4 FOM= 0.99 TEST= 0
INDE 15 18 19 FOBS=  164.9 SIGMA=  0.6 PHAS=   55.7 FOM= 0.97 TEST= 0
INDE 15 18 21 FOBS=   78.5 SIGMA=  0.9 PHAS=   30.9 FOM= 0.99 TEST= 0
INDE 15 18 23 FOBS=  105.7 SIGMA=  0.8 PHAS=   23.0 FOM= 0.99 TEST= 0
INDE 15 18 25 FOBS=  210.9 SIGMA=  0.5 PHAS=   55.7 FOM= 0.97 TEST= 0
INDE 15 18 27 FOBS=  241.2 SIGMA=  0.5 PHAS=  -47.6 FOM= 0.96 TEST= 0
INDE 15 18 29 FOBS=  161.8 SIGMA=  0.6 PHAS=  -38.2 FOM= 0.96 TEST= 0
INDE 15 18 31 FOBS=   46.6 SIGMA=  1.9 PHAS=  100.4 FOM= 0.93 TEST= 0
INDE 15 18 33 FOBS=   57.6 SIGMA=  1.7 PHAS= -153.9 FOM= 0.92 TEST= 0
INDE 15 18 35 FOBS=  298.1 SIGMA=  0.5 PHAS=  -48.3 FOM= 0.98 TEST= 0
INDE 15 18 37 FOBS=  279.6 SIGMA=  0.5 PHAS=   10.5 FOM= 0.97 TEST= 0
INDE 15 18 39 FOBS=  100.2 SIGMA=  1.3 PHAS= -101.6 FOM= 0.97 TEST= 0
INDE 15 18 41 FOBS=  122.9 SIGMA=  1.2 PHAS=  -76.2 FOM= 0.86 TEST= 0
INDE 15 18 43 FOBS=  100.4 SIGMA=  1.7 PHAS=  -62.6 FOM= 0.92 TEST= 0
INDE 15 18 45 FOBS=  149.2 SIGMA=  1.1 PHAS=  125.2 FOM= 0.17 TEST= 1
INDE 15 18 47 FOBS=   95.1 SIGMA=  1.9 PHAS=  -82.0 FOM= 0.17 TEST= 0
INDE 15 18 49 FOBS=   72.3 SIGMA=  2.4 PHAS=   35.6 FOM= 0.49 TEST= 0
INDE 15 18 51 FOBS=   64.1 SIGMA=  2.6 PHAS=  157.5 FOM= 0.77 TEST= 0
INDE 15 18 53 FOBS=   54.1 SIGMA=  3.4 PHAS=  145.2 FOM= 0.81 TEST= 0
INDE 15 18 55 FOBS=   40.4 SIGMA=  4.5 PHAS=   16.8 FOM= 0.47 TEST= 0
INDE 15 18 57 FOBS=   59.9 SIGMA=  3.6 PHAS=   80.9 FOM= 0.90 TEST= 0
INDE 15 18 59 FOBS=   43.6 SIGMA=  4.8 PHAS=  141.5 FOM= 0.59 TEST= 0
INDE 15 18 61 FOBS=    0.0 SIGMA= 21.9 PHAS=    0.0 FOM= 0.00 TEST= 1
INDE 15 18 63 FOBS=   49.0 SIGMA=  4.8 PHAS=   84.3 FOM= 0.93 TEST= 0
INDE 15 18 65 FOBS=   65.3 SIGMA=  3.4 PHAS=  -53.9 FOM= 0.78 TEST= 0
INDE 15 18 67 FOBS=  103.9 SIGMA=  2.7 PHAS=  -94.9 FOM= 0.12 TEST= 1
INDE 15 19 16 FOBS=  159.2 SIGMA=  0.7 PHAS=   26.5 FOM= 0.90 TEST= 0
INDE 15 19 18 FOBS=  230.4 SIGMA=  0.5 PHAS=   -1.8 FOM= 0.92 TEST= 1
INDE 15 19 20 FOBS=  147.7 SIGMA=  0.6 PHAS=   -0.3 FOM= 0.97 TEST= 0
INDE 15 19 22 FOBS=   44.0 SIGMA=  1.7 PHAS=   25.7 FOM= 0.95 TEST= 0
INDE 15 19 24 FOBS=  335.1 SIGMA=  0.4 PHAS=  -96.7 FOM= 0.97 TEST= 0
INDE 15 19 26 FOBS=  169.3 SIGMA=  0.6 PHAS=  179.7 FOM= 0.90 TEST= 0
INDE 15 19 28 FOBS=   72.7 SIGMA=  1.3 PHAS= -121.1 FOM= 0.94 TEST= 0
INDE 15 19 30 FOBS=  188.3 SIGMA=  0.6 PHAS= -152.5 FOM= 0.54 TEST= 0
INDE 15 19 32 FOBS=   14.9 SIGMA=  7.0 PHAS=  129.8 FOM= 0.00 TEST= 1
INDE 15 19 34 FOBS=   71.0 SIGMA=  1.5 PHAS= -161.7 FOM= 0.88 TEST= 0
INDE 15 19 36 FOBS=  177.4 SIGMA=  0.7 PHAS= -122.3 FOM= 0.85 TEST= 0
INDE 15 19 38 FOBS=  201.1 SIGMA=  0.7 PHAS=    8.4 FOM= 0.85 TEST= 0
INDE 15 19 40 FOBS=   49.7 SIGMA=  2.7 PHAS= -126.5 FOM= 0.64 TEST= 0
INDE 15 19 42 FOBS=  109.2 SIGMA=  1.5 PHAS=  -55.0 FOM= 0.64 TEST= 0
INDE 15 19 44 FOBS=  140.0 SIGMA=  1.2 PHAS=  163.5 FOM= 0.85 TEST= 0
INDE 15 19 46 FOBS=   28.6 SIGMA=  5.6 PHAS=  -21.4 FOM= 0.51 TEST= 0
INDE 15 19 48 FOBS=   60.3 SIGMA=  2.9 PHAS= -125.5 FOM= 0.50 TEST= 0
INDE 15 19 50 FOBS=  101.4 SIGMA=  1.7 PHAS=   48.3 FOM= 0.95 TEST= 0
INDE 15 19 52 FOBS=  124.3 SIGMA=  1.4 PHAS=  137.3 FOM= 0.86 TEST= 0
INDE 15 19 54 FOBS=   87.4 SIGMA=  1.9 PHAS=  -93.9 FOM= 0.69 TEST= 1
INDE 15 19 56 FOBS=  131.5 SIGMA=  1.3 PHAS=  -80.1 FOM= 0.95 TEST= 0
INDE 15 19 58 FOBS=   98.1 SIGMA=  2.2 PHAS=  -90.9 FOM= 0.91 TEST= 0
INDE 15 19 60 FOBS=    0.0 SIGMA= 23.7 PHAS=    0.0 FOM= 0.00 TEST= 1
INDE 15 19 62 FOBS=   66.8 SIGMA=  3.5 PHAS=  -20.2 FOM= 0.74 TEST= 0
INDE 15 19 64 FOBS=   17.9 SIGMA= 12.6 PHAS= -142.2 FOM= 0.10 TEST= 0
INDE 15 19 66 FOBS=   23.3 SIGMA= 11.0 PHAS= -119.8 FOM= 0.10 TEST= 0
INDE 15 20 15 FOBS=  142.6 SIGMA=  0.7 PHAS= -142.8 FOM= 0.77 TEST= 0
INDE 15 20 17 FOBS=  347.7 SIGMA=  0.5 PHAS=  -39.8 FOM= 0.98 TEST= 0
INDE 15 20 19 FOBS=  206.6 SIGMA=  0.6 PHAS=  -49.9 FOM= 0.97 TEST= 0
INDE 15 20 21 FOBS=   69.1 SIGMA=  1.1 PHAS=  -37.3 FOM= 0.83 TEST= 0
INDE 15 20 23 FOBS=  141.3 SIGMA=  0.7 PHAS= -148.5 FOM= 0.70 TEST= 0
INDE 15 20 25 FOBS=  210.5 SIGMA=  0.5 PHAS=  154.3 FOM= 0.98 TEST= 0
INDE 15 20 27 FOBS=   18.4 SIGMA=  5.3 PHAS=  160.7 FOM= 0.17 TEST= 0
INDE 15 20 29 FOBS=   24.5 SIGMA=  3.9 PHAS=   28.7 FOM= 0.42 TEST= 0
```

*FIG. 12A - 360*

```
INDE 15 20 31 FOBS=   173.5 SIGMA=  0.7 PHAS=   -8.5 FOM= 0.91 TEST= 0
INDE 15 20 33 FOBS=   158.1 SIGMA=  0.7 PHAS=  152.6 FOM= 0.99 TEST= 0
INDE 15 20 35 FOBS=   155.9 SIGMA=  0.8 PHAS= -110.9 FOM= 0.85 TEST= 0
INDE 15 20 37 FOBS=   152.5 SIGMA=  0.9 PHAS= -100.8 FOM= 0.98 TEST= 0
INDE 15 20 39 FOBS=    48.8 SIGMA=  2.7 PHAS=  -90.9 FOM= 0.79 TEST= 0
INDE 15 20 41 FOBS=   133.2 SIGMA=  1.2 PHAS=  155.3 FOM= 0.56 TEST= 0
INDE 15 20 43 FOBS=   187.3 SIGMA=  0.9 PHAS=  110.7 FOM= 0.38 TEST= 1
INDE 15 20 45 FOBS=   242.4 SIGMA=  0.8 PHAS=  130.1 FOM= 0.94 TEST= 0
INDE 15 20 47 FOBS=   135.8 SIGMA=  1.2 PHAS=  144.2 FOM= 0.52 TEST= 1
INDE 15 20 49 FOBS=   103.8 SIGMA=  1.6 PHAS=    5.1 FOM= 0.93 TEST= 0
INDE 15 20 51 FOBS=   112.8 SIGMA=  1.5 PHAS=    7.6 FOM= 0.91 TEST= 0
INDE 15 20 53 FOBS=     0.0 SIGMA= 19.0 PHAS=    0.0 FOM= 0.00 TEST= 0
INDE 15 20 55 FOBS=   140.6 SIGMA=  1.2 PHAS=  110.4 FOM= 0.93 TEST= 0
INDE 15 20 57 FOBS=     0.0 SIGMA= 19.7 PHAS=    0.0 FOM= 0.00 TEST= 0
INDE 15 20 59 FOBS=    98.9 SIGMA=  1.9 PHAS=  163.1 FOM= 0.90 TEST= 0
INDE 15 20 61 FOBS=    84.0 SIGMA=  2.9 PHAS=  167.9 FOM= 0.85 TEST= 0
INDE 15 20 63 FOBS=     0.0 SIGMA= 21.4 PHAS=    0.0 FOM= 0.00 TEST= 0
INDE 15 20 65 FOBS=    86.7 SIGMA=  3.0 PHAS=   99.9 FOM= 0.35 TEST= 0
INDE 15 21 16 FOBS=   207.1 SIGMA=  0.6 PHAS= -113.2 FOM= 0.98 TEST= 0
INDE 15 21 18 FOBS=   311.6 SIGMA=  0.5 PHAS= -112.9 FOM= 0.98 TEST= 0
INDE 15 21 20 FOBS=    96.8 SIGMA=  1.0 PHAS=  136.7 FOM= 0.93 TEST= 0
INDE 15 21 22 FOBS=   291.2 SIGMA=  0.4 PHAS=  111.2 FOM= 0.99 TEST= 0
INDE 15 21 24 FOBS=   140.2 SIGMA=  0.7 PHAS=   87.5 FOM= 0.99 TEST= 0
INDE 15 21 26 FOBS=   109.6 SIGMA=  0.9 PHAS=   29.4 FOM= 0.37 TEST= 0
INDE 15 21 28 FOBS=   210.1 SIGMA=  0.6 PHAS= -102.9 FOM= 0.95 TEST= 0
INDE 15 21 30 FOBS=   156.9 SIGMA=  0.7 PHAS=  -43.1 FOM= 0.60 TEST= 0
INDE 15 21 32 FOBS=    94.5 SIGMA=  1.2 PHAS= -169.8 FOM= 0.88 TEST= 0
INDE 15 21 34 FOBS=   139.7 SIGMA=  0.9 PHAS=   44.4 FOM= 0.98 TEST= 0
INDE 15 21 36 FOBS=   266.9 SIGMA=  0.6 PHAS= -156.8 FOM= 0.97 TEST= 0
INDE 15 21 38 FOBS=   342.7 SIGMA=  0.6 PHAS=  127.3 FOM= 0.97 TEST= 0
INDE 15 21 40 FOBS=   229.1 SIGMA=  0.8 PHAS=   82.7 FOM= 0.96 TEST= 0
INDE 15 21 42 FOBS=   126.8 SIGMA=  1.3 PHAS=   84.3 FOM= 0.81 TEST= 0
INDE 15 21 44 FOBS=   215.1 SIGMA=  0.8 PHAS=   60.7 FOM= 0.95 TEST= 0
INDE 15 21 46 FOBS=   233.6 SIGMA=  0.8 PHAS=   22.0 FOM= 0.97 TEST= 0
INDE 15 21 48 FOBS=    45.1 SIGMA=  3.7 PHAS= -108.6 FOM= 0.89 TEST= 0
INDE 15 21 50 FOBS=   111.5 SIGMA=  1.4 PHAS=   52.3 FOM= 0.81 TEST= 0
INDE 15 21 52 FOBS=   108.5 SIGMA=  1.6 PHAS= -100.8 FOM= 0.75 TEST= 0
INDE 15 21 54 FOBS=    68.8 SIGMA=  2.4 PHAS=  -52.1 FOM= 0.85 TEST= 0
INDE 15 21 56 FOBS=     0.0 SIGMA= 20.5 PHAS=    0.0 FOM= 0.00 TEST= 0
INDE 15 21 58 FOBS=     0.0 SIGMA= 18.9 PHAS=    0.0 FOM= 0.00 TEST= 1
INDE 15 21 60 FOBS=   169.9 SIGMA=  1.3 PHAS=   25.3 FOM= 0.96 TEST= 0
INDE 15 21 62 FOBS=     0.0 SIGMA= 19.7 PHAS=    0.0 FOM= 0.00 TEST= 0
INDE 15 21 64 FOBS=    91.9 SIGMA=  2.5 PHAS= -171.1 FOM= 0.86 TEST= 0
INDE 15 22 15 FOBS=    51.7 SIGMA=  1.6 PHAS=  166.6 FOM= 0.99 TEST= 0
INDE 15 22 17 FOBS=   194.1 SIGMA=  0.6 PHAS= -176.4 FOM= 0.97 TEST= 0
INDE 15 22 19 FOBS=   192.6 SIGMA=  0.6 PHAS=  135.4 FOM= 0.92 TEST= 0
INDE 15 22 21 FOBS=   203.2 SIGMA=  0.6 PHAS=    7.6 FOM= 0.95 TEST= 0
INDE 15 22 23 FOBS=   230.4 SIGMA=  0.5 PHAS=  -59.3 FOM= 0.53 TEST= 1
INDE 15 22 25 FOBS=   105.0 SIGMA=  1.0 PHAS=  -40.4 FOM= 0.80 TEST= 0
INDE 15 22 27 FOBS=    95.2 SIGMA=  1.1 PHAS= -173.4 FOM= 0.84 TEST= 0
INDE 15 22 29 FOBS=   367.2 SIGMA=  0.6 PHAS=  -61.5 FOM= 0.64 TEST= 1
INDE 15 22 31 FOBS=   128.9 SIGMA=  0.9 PHAS=   19.1 FOM= 0.87 TEST= 0
INDE 15 22 33 FOBS=    98.7 SIGMA=  1.2 PHAS=  103.2 FOM= 0.92 TEST= 0
INDE 15 22 35 FOBS=   106.6 SIGMA=  1.2 PHAS= -152.5 FOM= 0.97 TEST= 0
INDE 15 22 37 FOBS=   234.8 SIGMA=  0.6 PHAS=  110.8 FOM= 0.95 TEST= 0
INDE 15 22 39 FOBS=   397.5 SIGMA=  0.6 PHAS=   18.5 FOM= 0.98 TEST= 0
INDE 15 22 41 FOBS=   172.4 SIGMA=  1.0 PHAS=  -23.6 FOM= 0.86 TEST= 0
INDE 15 22 43 FOBS=    66.0 SIGMA=  2.3 PHAS=  -58.8 FOM= 0.79 TEST= 0
INDE 15 22 45 FOBS=   161.3 SIGMA=  1.0 PHAS=  -76.9 FOM= 0.93 TEST= 0
INDE 15 22 47 FOBS=    63.2 SIGMA=  2.4 PHAS= -179.9 FOM= 0.49 TEST= 0
INDE 15 22 49 FOBS=   207.2 SIGMA=  0.9 PHAS=   -4.8 FOM= 0.93 TEST= 0
INDE 15 22 51 FOBS=    89.0 SIGMA=  1.8 PHAS=   29.2 FOM= 0.92 TEST= 0
INDE 15 22 53 FOBS=   112.5 SIGMA=  1.5 PHAS= -171.0 FOM= 0.85 TEST= 0
INDE 15 22 55 FOBS=    78.8 SIGMA=  2.1 PHAS=  170.9 FOM= 0.91 TEST= 0
INDE 15 22 57 FOBS=     0.0 SIGMA= 19.1 PHAS=    0.0 FOM= 0.00 TEST= 1
INDE 15 22 59 FOBS=    51.8 SIGMA=  4.0 PHAS=  -90.7 FOM= 0.74 TEST= 0
INDE 15 22 61 FOBS=    57.7 SIGMA=  3.4 PHAS=  -89.3 FOM= 0.55 TEST= 0
INDE 15 22 63 FOBS=    11.0 SIGMA= 18.6 PHAS=  132.4 FOM= 0.37 TEST= 0
INDE 15 22 65 FOBS=    43.2 SIGMA= 11.7 PHAS=  155.2 FOM= 0.46 TEST= 0
INDE 15 23 16 FOBS=   107.4 SIGMA=  1.0 PHAS=  172.1 FOM= 0.98 TEST= 0
```

*FIG. 12A - 361*

```
INDE  15  23  18  FOBS=   199.6  SIGMA=   0.6  PHAS=   117.1  FOM=  0.99  TEST= 0
INDE  15  23  20  FOBS=   132.8  SIGMA=   0.8  PHAS=   100.4  FOM=  0.99  TEST= 0
INDE  15  23  22  FOBS=   105.5  SIGMA=   0.9  PHAS=    72.9  FOM=  0.97  TEST= 0
INDE  15  23  24  FOBS=     0.0  SIGMA=  15.0  PHAS=     0.0  FOM=  0.00  TEST= 0
INDE  15  23  26  FOBS=   168.1  SIGMA=   0.7  PHAS=    82.8  FOM=  0.25  TEST= 1
INDE  15  23  28  FOBS=    92.9  SIGMA=   1.1  PHAS=  -174.5  FOM=  0.95  TEST= 0
INDE  15  23  30  FOBS=   151.5  SIGMA=   0.8  PHAS=   140.6  FOM=  0.88  TEST= 0
INDE  15  23  32  FOBS=   116.4  SIGMA=   1.1  PHAS=  -144.4  FOM=  0.48  TEST= 0
INDE  15  23  34  FOBS=   219.4  SIGMA=   0.7  PHAS=    24.4  FOM=  0.95  TEST= 0
INDE  15  23  36  FOBS=    70.2  SIGMA=   2.0  PHAS=    33.8  FOM=  0.53  TEST= 0
INDE  15  23  38  FOBS=    65.5  SIGMA=   2.5  PHAS=    43.2  FOM=  0.82  TEST= 1
INDE  15  23  40  FOBS=   152.4  SIGMA=   1.1  PHAS=  -102.3  FOM=  0.88  TEST= 0
INDE  15  23  42  FOBS=   145.7  SIGMA=   1.1  PHAS=  -155.0  FOM=  0.85  TEST= 0
INDE  15  23  44  FOBS=   121.4  SIGMA=   1.3  PHAS=  -177.6  FOM=  0.90  TEST= 0
INDE  15  23  46  FOBS=     0.0  SIGMA=  18.6  PHAS=     0.0  FOM=  0.00  TEST= 0
INDE  15  23  48  FOBS=    90.8  SIGMA=   1.7  PHAS=  -132.2  FOM=  0.92  TEST= 0
INDE  15  23  50  FOBS=    76.7  SIGMA=   2.1  PHAS=   137.8  FOM=  0.73  TEST= 0
INDE  15  23  52  FOBS=    54.5  SIGMA=   2.8  PHAS=   -55.1  FOM=  0.92  TEST= 0
INDE  15  23  54  FOBS=    19.7  SIGMA=   9.4  PHAS=  -139.8  FOM=  0.17  TEST= 0
INDE  15  23  56  FOBS=   108.6  SIGMA=   1.8  PHAS=   125.2  FOM=  0.98  TEST= 0
INDE  15  23  58  FOBS=    38.2  SIGMA=   5.9  PHAS=  -138.9  FOM=  0.56  TEST= 0
INDE  15  23  60  FOBS=    40.6  SIGMA=   4.9  PHAS=   166.8  FOM=  0.40  TEST= 0
INDE  15  23  62  FOBS=     9.9  SIGMA=  21.5  PHAS=   -85.0  FOM=  0.11  TEST= 0
INDE  15  23  64  FOBS=    23.3  SIGMA=  15.9  PHAS=   112.3  FOM=  0.54  TEST= 0
INDE  15  23  66  FOBS=    52.6  SIGMA=   9.7  PHAS=    58.4  FOM=  0.43  TEST= 0
INDE  15  24  15  FOBS=   102.2  SIGMA=   0.9  PHAS=   160.4  FOM=  0.95  TEST= 1
INDE  15  24  17  FOBS=   133.8  SIGMA=   0.8  PHAS=    56.4  FOM=  0.98  TEST= 0
INDE  15  24  19  FOBS=   192.5  SIGMA=   0.6  PHAS=    60.5  FOM=  0.99  TEST= 0
INDE  15  24  21  FOBS=   257.6  SIGMA=   0.6  PHAS=     0.6  FOM=  0.98  TEST= 0
INDE  15  24  23  FOBS=   305.0  SIGMA=   0.5  PHAS=   -62.8  FOM=  0.97  TEST= 0
INDE  15  24  25  FOBS=    30.9  SIGMA=   3.9  PHAS=  -130.0  FOM=  0.58  TEST= 0
INDE  15  24  27  FOBS=   120.7  SIGMA=   1.0  PHAS=  -150.0  FOM=  0.98  TEST= 0
INDE  15  24  29  FOBS=   309.4  SIGMA=   0.7  PHAS=  -123.2  FOM=  0.96  TEST= 0
INDE  15  24  31  FOBS=    78.3  SIGMA=   1.5  PHAS=   162.9  FOM=  0.95  TEST= 0
INDE  15  24  33  FOBS=   116.6  SIGMA=   1.1  PHAS=   -83.5  FOM=  0.91  TEST= 0
INDE  15  24  35  FOBS=   268.7  SIGMA=   0.6  PHAS=  -137.4  FOM=  0.95  TEST= 0
INDE  15  24  37  FOBS=   158.1  SIGMA=   1.1  PHAS=   179.8  FOM=  0.95  TEST= 0
INDE  15  24  39  FOBS=   129.8  SIGMA=   1.4  PHAS=    22.1  FOM=  0.58  TEST= 0
INDE  15  24  41  FOBS=   144.8  SIGMA=   1.2  PHAS=   149.8  FOM=  0.96  TEST= 0
INDE  15  24  43  FOBS=    50.7  SIGMA=   3.0  PHAS=    89.0  FOM=  0.91  TEST= 0
INDE  15  24  45  FOBS=    29.9  SIGMA=   5.0  PHAS=  -138.4  FOM=  0.83  TEST= 0
INDE  15  24  47  FOBS=   141.2  SIGMA=   1.1  PHAS=   102.1  FOM=  0.86  TEST= 0
INDE  15  24  49  FOBS=    79.1  SIGMA=   1.9  PHAS=    76.0  FOM=  0.67  TEST= 0
INDE  15  24  51  FOBS=   115.2  SIGMA=   1.3  PHAS=    88.5  FOM=  0.95  TEST= 0
INDE  15  24  53  FOBS=     0.0  SIGMA=  18.3  PHAS=     0.0  FOM=  0.00  TEST= 0
INDE  15  24  55  FOBS=    83.1  SIGMA=   1.9  PHAS=    19.7  FOM=  0.96  TEST= 0
INDE  15  24  57  FOBS=    65.0  SIGMA=   2.9  PHAS=    93.0  FOM=  0.92  TEST= 0
INDE  15  24  59  FOBS=    97.0  SIGMA=   2.2  PHAS=    49.9  FOM=  0.81  TEST= 0
INDE  15  24  61  FOBS=    35.7  SIGMA=   5.6  PHAS=    89.3  FOM=  0.69  TEST= 0
INDE  15  24  63  FOBS=    44.4  SIGMA=   5.8  PHAS=    83.2  FOM=  0.15  TEST= 0
INDE  15  24  65  FOBS=    50.0  SIGMA=  10.1  PHAS=   -63.5  FOM=  0.72  TEST= 0
INDE  15  24  67  FOBS=    56.2  SIGMA=   9.2  PHAS=  -176.3  FOM=  0.85  TEST= 0
INDE  15  24  69  FOBS=    47.2  SIGMA=  11.3  PHAS=    37.3  FOM=  0.41  TEST= 0
INDE  15  25  16  FOBS=    61.9  SIGMA=   1.5  PHAS=   -55.0  FOM=  0.96  TEST= 0
INDE  15  25  18  FOBS=    46.7  SIGMA=   2.1  PHAS=    78.4  FOM=  0.97  TEST= 0
INDE  15  25  20  FOBS=   137.0  SIGMA=   0.8  PHAS=   -37.8  FOM=  0.99  TEST= 0
INDE  15  25  22  FOBS=   186.6  SIGMA=   0.7  PHAS=  -104.8  FOM=  0.98  TEST= 0
INDE  15  25  24  FOBS=   139.7  SIGMA=   0.8  PHAS=  -172.2  FOM=  0.92  TEST= 0
INDE  15  25  26  FOBS=    81.2  SIGMA=   1.4  PHAS=  -102.9  FOM=  0.85  TEST= 0
INDE  15  25  28  FOBS=   359.5  SIGMA=   0.5  PHAS=   136.5  FOM=  0.96  TEST= 0
INDE  15  25  30  FOBS=   254.1  SIGMA=   0.6  PHAS=    90.2  FOM=  0.96  TEST= 0
INDE  15  25  32  FOBS=   278.3  SIGMA=   0.7  PHAS=    44.4  FOM=  0.95  TEST= 0
INDE  15  25  34  FOBS=    34.3  SIGMA=   5.0  PHAS=    63.9  FOM=  0.72  TEST= 1
INDE  15  25  36  FOBS=    18.6  SIGMA=   9.3  PHAS=   121.2  FOM=  0.58  TEST= 0
INDE  15  25  38  FOBS=    95.5  SIGMA=   1.8  PHAS=  -101.6  FOM=  0.71  TEST= 0
INDE  15  25  40  FOBS=    89.3  SIGMA=   1.9  PHAS=   -97.4  FOM=  0.82  TEST= 0
INDE  15  25  42  FOBS=     0.0  SIGMA=  19.8  PHAS=     0.0  FOM=  0.00  TEST= 0
INDE  15  25  44  FOBS=     0.0  SIGMA=  17.6  PHAS=     0.0  FOM=  0.00  TEST= 0
INDE  15  25  46  FOBS=    89.2  SIGMA=   1.7  PHAS=    32.5  FOM=  0.80  TEST= 0
INDE  15  25  48  FOBS=     5.6  SIGMA=  29.4  PHAS=   136.1  FOM=  0.06  TEST= 0
```

*FIG. 12A - 362*

```
INDE 15 25 50 FOBS=  107.3 SIGMA=  1.4 PHAS=   50.9 FOM= 0.89 TEST= 0
INDE 15 25 52 FOBS=  103.4 SIGMA=  1.4 PHAS=   -9.9 FOM= 0.93 TEST= 0
INDE 15 25 54 FOBS=   97.7 SIGMA=  1.6 PHAS=  -32.8 FOM= 0.92 TEST= 0
INDE 15 25 56 FOBS=   87.0 SIGMA=  2.0 PHAS=  -29.9 FOM= 0.87 TEST= 0
INDE 15 25 58 FOBS=   61.8 SIGMA=  3.4 PHAS=    0.3 FOM= 0.55 TEST= 0
INDE 15 25 60 FOBS=   43.1 SIGMA=  6.9 PHAS=  174.1 FOM= 0.39 TEST= 0
INDE 15 25 62 FOBS=  122.0 SIGMA=  2.2 PHAS=  -37.4 FOM= 0.88 TEST= 0
INDE 15 25 64 FOBS=    0.0 SIGMA= 31.7 PHAS=    0.0 FOM= 0.00 TEST= 0
INDE 15 25 66 FOBS=   95.6 SIGMA=  5.6 PHAS=  100.6 FOM= 0.86 TEST= 0
INDE 15 25 68 FOBS=   91.3 SIGMA=  5.9 PHAS=   89.6 FOM= 0.91 TEST= 0
INDE 15 25 70 FOBS=   25.6 SIGMA= 20.8 PHAS=   50.6 FOM= 0.40 TEST= 0
INDE 15 26 15 FOBS=  115.5 SIGMA=  0.7 PHAS=  -81.3 FOM= 0.99 TEST= 0
INDE 15 26 17 FOBS=  156.0 SIGMA=  0.7 PHAS=  -69.5 FOM= 0.92 TEST= 1
INDE 15 26 19 FOBS=   39.3 SIGMA=  2.7 PHAS=  -47.0 FOM= 0.95 TEST= 0
INDE 15 26 21 FOBS=  156.2 SIGMA=  0.8 PHAS=  -91.3 FOM= 0.96 TEST= 0
INDE 15 26 23 FOBS=   78.3 SIGMA=  1.4 PHAS= -129.6 FOM= 0.82 TEST= 0
INDE 15 26 25 FOBS=  205.7 SIGMA=  0.7 PHAS=   99.1 FOM= 0.99 TEST= 0
INDE 15 26 27 FOBS=   60.5 SIGMA=  2.0 PHAS=  109.2 FOM= 0.48 TEST= 1
INDE 15 26 29 FOBS=  183.2 SIGMA=  0.8 PHAS=  -13.1 FOM= 0.98 TEST= 0
INDE 15 26 31 FOBS=  285.4 SIGMA=  0.6 PHAS=  -74.2 FOM= 0.96 TEST= 0
INDE 15 26 33 FOBS=  316.7 SIGMA=  0.7 PHAS=  -79.0 FOM= 0.96 TEST= 0
INDE 15 26 35 FOBS=  176.2 SIGMA=  1.0 PHAS=  132.3 FOM= 0.88 TEST= 1
INDE 15 26 37 FOBS=  190.2 SIGMA=  1.0 PHAS=  177.4 FOM= 0.91 TEST= 0
INDE 15 26 39 FOBS=  209.3 SIGMA=  0.9 PHAS= -136.5 FOM= 0.96 TEST= 0
INDE 15 26 41 FOBS=  195.9 SIGMA=  1.0 PHAS=  151.3 FOM= 0.94 TEST= 0
INDE 15 26 43 FOBS=    0.0 SIGMA= 18.6 PHAS=    0.0 FOM= 0.00 TEST= 1
INDE 15 26 45 FOBS=  116.7 SIGMA=  1.3 PHAS=  -56.3 FOM= 0.85 TEST= 1
INDE 15 26 47 FOBS=   52.6 SIGMA=  2.8 PHAS=   -9.0 FOM= 0.59 TEST= 0
INDE 15 26 49 FOBS=   61.9 SIGMA=  2.4 PHAS=   66.7 FOM= 0.43 TEST= 0
INDE 15 26 51 FOBS=   84.8 SIGMA=  1.8 PHAS=   42.2 FOM= 0.64 TEST= 0
INDE 15 26 53 FOBS=  185.9 SIGMA=  0.8 PHAS=  -86.2 FOM= 0.97 TEST= 0
INDE 15 26 55 FOBS=  135.2 SIGMA=  1.3 PHAS=  -80.8 FOM= 0.93 TEST= 0
INDE 15 26 57 FOBS=    0.0 SIGMA= 19.0 PHAS=    0.0 FOM= 0.00 TEST= 1
INDE 15 26 59 FOBS=   59.8 SIGMA=  4.4 PHAS=   53.1 FOM= 0.75 TEST= 0
INDE 15 26 61 FOBS=   36.7 SIGMA=  8.1 PHAS=  131.7 FOM= 0.27 TEST= 0
INDE 15 26 63 FOBS=   70.6 SIGMA=  4.3 PHAS= -111.4 FOM= 0.89 TEST= 0
INDE 15 26 65 FOBS=   47.6 SIGMA= 10.7 PHAS=  -20.9 FOM= 0.60 TEST= 0
INDE 15 26 67 FOBS=   35.9 SIGMA= 14.5 PHAS= -112.2 FOM= 0.48 TEST= 0
INDE 15 26 69 FOBS=    0.0 SIGMA= 19.0 PHAS=    0.0 FOM= 0.00 TEST= 0
INDE 15 26 71 FOBS=   67.8 SIGMA=  8.3 PHAS=   21.3 FOM= 0.87 TEST= 0
INDE 15 27 16 FOBS=   46.5 SIGMA=  2.0 PHAS=  -61.7 FOM= 0.96 TEST= 0
INDE 15 27 18 FOBS=  135.5 SIGMA=  0.8 PHAS= -175.6 FOM= 0.93 TEST= 0
INDE 15 27 20 FOBS=  122.2 SIGMA=  0.9 PHAS=   45.1 FOM= 0.76 TEST= 1
INDE 15 27 22 FOBS=  147.9 SIGMA=  0.8 PHAS=  152.4 FOM= 0.91 TEST= 0
INDE 15 27 24 FOBS=  191.2 SIGMA=  0.7 PHAS=   63.4 FOM= 0.94 TEST= 0
INDE 15 27 26 FOBS=   95.6 SIGMA=  1.2 PHAS=   65.0 FOM= 0.97 TEST= 0
INDE 15 27 28 FOBS=    0.0 SIGMA= 15.9 PHAS=    0.0 FOM= 0.00 TEST= 0
INDE 15 27 30 FOBS=   75.9 SIGMA=  1.8 PHAS= -136.8 FOM= 0.92 TEST= 0
INDE 15 27 32 FOBS=  165.3 SIGMA=  1.1 PHAS=  137.6 FOM= 0.86 TEST= 0
INDE 15 27 34 FOBS=   69.4 SIGMA=  2.5 PHAS=  -15.1 FOM= 0.74 TEST= 0
INDE 15 27 36 FOBS=  133.8 SIGMA=  1.3 PHAS=   62.6 FOM= 0.92 TEST= 0
INDE 15 27 38 FOBS=   98.1 SIGMA=  1.8 PHAS=  141.4 FOM= 0.88 TEST= 0
INDE 15 27 40 FOBS=  224.3 SIGMA=  0.9 PHAS=  100.3 FOM= 0.94 TEST= 0
INDE 15 27 42 FOBS=   68.0 SIGMA=  2.5 PHAS=   21.8 FOM= 0.79 TEST= 1
INDE 15 27 44 FOBS=   50.6 SIGMA=  3.2 PHAS=  -19.8 FOM= 0.77 TEST= 0
INDE 15 27 46 FOBS=   44.2 SIGMA=  3.8 PHAS=  120.3 FOM= 0.34 TEST= 0
INDE 15 27 48 FOBS=   30.2 SIGMA=  4.9 PHAS=  136.9 FOM= 0.24 TEST= 0
INDE 15 27 50 FOBS=  121.5 SIGMA=  1.3 PHAS=    4.5 FOM= 0.96 TEST= 0
INDE 15 27 52 FOBS=   87.8 SIGMA=  1.7 PHAS= -151.8 FOM= 0.89 TEST= 0
INDE 15 27 54 FOBS=  122.9 SIGMA=  1.2 PHAS= -179.4 FOM= 0.93 TEST= 0
INDE 15 27 56 FOBS=   24.3 SIGMA=  6.7 PHAS=  -51.0 FOM= 0.27 TEST= 1
INDE 15 27 58 FOBS=   87.9 SIGMA=  2.5 PHAS=   46.7 FOM= 0.87 TEST= 0
INDE 15 27 60 FOBS=   56.8 SIGMA=  4.5 PHAS=  169.8 FOM= 0.73 TEST= 0
INDE 15 27 62 FOBS=   99.3 SIGMA=  3.1 PHAS=   54.8 FOM= 0.91 TEST= 0
INDE 15 27 64 FOBS=   27.7 SIGMA= 17.8 PHAS= -147.9 FOM= 0.60 TEST= 0
INDE 15 27 66 FOBS=   46.5 SIGMA= 11.0 PHAS=  106.8 FOM= 0.51 TEST= 0
INDE 15 27 68 FOBS=   29.7 SIGMA= 17.8 PHAS=   28.5 FOM= 0.34 TEST= 0
INDE 15 27 70 FOBS=   58.6 SIGMA=  3.3 PHAS=  -66.6 FOM= 0.86 TEST= 0
INDE 15 28 15 FOBS=  229.1 SIGMA=  0.5 PHAS=   14.2 FOM= 0.94 TEST= 0
INDE 15 28 17 FOBS=  363.8 SIGMA=  0.5 PHAS=  -44.9 FOM= 0.95 TEST= 1
```

*FIG. 12A - 363*

```
INDE 15 28 19 FOBS=    66.2 SIGMA=  1.5 PHAS=   53.9 FOM= 0.87 TEST= 0
INDE 15 28 21 FOBS=    81.5 SIGMA=  1.3 PHAS=    4.3 FOM= 0.32 TEST= 0
INDE 15 28 23 FOBS=   178.8 SIGMA=  0.7 PHAS=  -67.4 FOM= 0.55 TEST= 0
INDE 15 28 25 FOBS=   291.0 SIGMA=  0.6 PHAS=   -8.2 FOM= 0.95 TEST= 0
INDE 15 28 27 FOBS=   213.0 SIGMA=  0.7 PHAS=  -48.6 FOM= 0.96 TEST= 0
INDE 15 28 29 FOBS=   124.3 SIGMA=  1.2 PHAS=  -42.3 FOM= 0.78 TEST= 0
INDE 15 28 31 FOBS=    29.4 SIGMA=  5.5 PHAS=  -98.8 FOM= 0.05 TEST= 0
INDE 15 28 33 FOBS=   201.8 SIGMA=  1.0 PHAS= -101.3 FOM= 0.95 TEST= 0
INDE 15 28 35 FOBS=   128.5 SIGMA=  1.5 PHAS=  -62.1 FOM= 0.85 TEST= 0
INDE 15 28 37 FOBS=    50.7 SIGMA=  3.6 PHAS=   65.2 FOM= 0.88 TEST= 0
INDE 15 28 39 FOBS=    76.2 SIGMA=  2.4 PHAS=   -4.4 FOM= 0.68 TEST= 0
INDE 15 28 41 FOBS=    51.5 SIGMA=  3.3 PHAS=   24.3 FOM= 0.40 TEST= 0
INDE 15 28 43 FOBS=    43.1 SIGMA=  3.8 PHAS= -145.3 FOM= 0.63 TEST= 1
INDE 15 28 45 FOBS=    73.0 SIGMA=  2.3 PHAS=  -40.3 FOM= 0.67 TEST= 0
INDE 15 28 47 FOBS=    75.1 SIGMA=  2.2 PHAS=  -67.4 FOM= 0.64 TEST= 0
INDE 15 28 49 FOBS=    66.9 SIGMA=  2.3 PHAS=  -60.4 FOM= 0.71 TEST= 0
INDE 15 28 51 FOBS=    49.7 SIGMA=  2.9 PHAS=   67.7 FOM= 0.94 TEST= 0
INDE 15 28 53 FOBS=    16.0 SIGMA=  9.3 PHAS=   64.8 FOM= 0.32 TEST= 0
INDE 15 28 55 FOBS=    48.1 SIGMA=  3.2 PHAS=  -52.3 FOM= 0.89 TEST= 0
INDE 15 28 57 FOBS=    31.2 SIGMA=  7.5 PHAS= -104.6 FOM= 0.43 TEST= 0
INDE 15 28 59 FOBS=    25.6 SIGMA=  8.3 PHAS=   90.6 FOM= 0.52 TEST= 0
INDE 15 28 61 FOBS=    45.9 SIGMA=  7.7 PHAS=  -71.9 FOM= 0.40 TEST= 0
INDE 15 28 63 FOBS=     0.0 SIGMA= 30.9 PHAS=    0.0 FOM= 0.00 TEST= 1
INDE 15 28 65 FOBS=    47.4 SIGMA= 10.5 PHAS=  139.9 FOM= 0.67 TEST= 0
INDE 15 28 67 FOBS=     0.0 SIGMA= 32.2 PHAS=    0.0 FOM= 0.00 TEST= 0
INDE 15 28 69 FOBS=    25.3 SIGMA=  8.4 PHAS= -130.6 FOM= 0.54 TEST= 0
INDE 15 29 16 FOBS=   206.7 SIGMA=  0.6 PHAS= -121.8 FOM= 0.93 TEST= 0
INDE 15 29 18 FOBS=   266.0 SIGMA=  0.6 PHAS= -157.9 FOM= 0.99 TEST= 0
INDE 15 29 20 FOBS=     0.0 SIGMA= 15.8 PHAS=    0.0 FOM= 0.00 TEST= 0
INDE 15 29 22 FOBS=   193.7 SIGMA=  0.7 PHAS=  166.2 FOM= 0.99 TEST= 0
INDE 15 29 24 FOBS=     0.0 SIGMA= 15.4 PHAS=    0.0 FOM= 0.00 TEST= 0
INDE 15 29 26 FOBS=   328.7 SIGMA=  0.6 PHAS=  171.7 FOM= 0.91 TEST= 0
INDE 15 29 28 FOBS=   102.2 SIGMA=  1.6 PHAS=  178.5 FOM= 0.82 TEST= 1
INDE 15 29 30 FOBS=   228.6 SIGMA=  0.8 PHAS=  -61.1 FOM= 0.87 TEST= 0
INDE 15 29 32 FOBS=    36.3 SIGMA=  5.3 PHAS=   39.0 FOM= 0.44 TEST= 0
INDE 15 29 34 FOBS=   146.2 SIGMA=  1.3 PHAS=  166.9 FOM= 0.89 TEST= 0
INDE 15 29 36 FOBS=    84.8 SIGMA=  2.3 PHAS= -129.3 FOM= 0.71 TEST= 0
INDE 15 29 38 FOBS=   131.2 SIGMA=  1.5 PHAS= -106.2 FOM= 0.86 TEST= 0
INDE 15 29 40 FOBS=    79.2 SIGMA=  2.2 PHAS=  109.4 FOM= 0.88 TEST= 0
INDE 15 29 42 FOBS=    55.0 SIGMA=  3.0 PHAS= -130.3 FOM= 0.81 TEST= 0
INDE 15 29 44 FOBS=   127.2 SIGMA=  1.4 PHAS=   13.4 FOM= 0.89 TEST= 0
INDE 15 29 46 FOBS=    43.6 SIGMA=  3.7 PHAS=   49.3 FOM= 0.73 TEST= 0
INDE 15 29 48 FOBS=   118.9 SIGMA=  1.4 PHAS= -112.4 FOM= 0.90 TEST= 0
INDE 15 29 50 FOBS=    76.1 SIGMA=  2.1 PHAS=  -41.5 FOM= 0.84 TEST= 1
INDE 15 29 52 FOBS=    97.6 SIGMA=  1.5 PHAS= -107.0 FOM= 0.85 TEST= 0
INDE 15 29 54 FOBS=    77.9 SIGMA=  2.2 PHAS= -172.1 FOM= 0.86 TEST= 0
INDE 15 29 56 FOBS=   133.1 SIGMA=  1.5 PHAS=  168.9 FOM= 0.95 TEST= 0
INDE 15 29 58 FOBS=    74.4 SIGMA=  2.7 PHAS=   -9.8 FOM= 0.81 TEST= 0
INDE 15 29 60 FOBS=    64.4 SIGMA=  3.3 PHAS=  162.9 FOM= 0.42 TEST= 0
INDE 15 29 62 FOBS=    89.8 SIGMA=  3.3 PHAS=   47.3 FOM= 0.91 TEST= 0
INDE 15 29 64 FOBS=    73.5 SIGMA=  4.9 PHAS=  123.6 FOM= 0.63 TEST= 1
INDE 15 29 66 FOBS=     0.0 SIGMA= 31.6 PHAS=    0.0 FOM= 0.00 TEST= 0
INDE 15 29 68 FOBS=    28.0 SIGMA= 18.4 PHAS=   32.3 FOM= 0.45 TEST= 0
INDE 15 29 70 FOBS=     0.0 SIGMA= 21.3 PHAS=    0.0 FOM= 0.00 TEST= 0
INDE 15 30 15 FOBS=   150.8 SIGMA=  0.7 PHAS=   99.3 FOM= 0.90 TEST= 0
INDE 15 30 17 FOBS=   164.0 SIGMA=  0.8 PHAS= -156.3 FOM= 0.86 TEST= 0
INDE 15 30 19 FOBS=    35.0 SIGMA=  3.0 PHAS=  -88.9 FOM= 0.90 TEST= 0
INDE 15 30 21 FOBS=   113.8 SIGMA=  1.0 PHAS=   72.8 FOM= 0.99 TEST= 0
INDE 15 30 23 FOBS=   138.2 SIGMA=  0.9 PHAS=  -69.3 FOM= 0.72 TEST= 0
INDE 15 30 25 FOBS=   189.2 SIGMA=  0.7 PHAS= -110.2 FOM= 0.90 TEST= 1
INDE 15 30 27 FOBS=    54.6 SIGMA=  2.8 PHAS=   10.4 FOM= 0.84 TEST= 0
INDE 15 30 29 FOBS=   108.6 SIGMA=  1.6 PHAS= -121.0 FOM= 0.98 TEST= 0
INDE 15 30 31 FOBS=   144.9 SIGMA=  1.3 PHAS=  130.7 FOM= 0.95 TEST= 0
INDE 15 30 33 FOBS=    38.5 SIGMA=  5.3 PHAS=  -36.3 FOM= 0.59 TEST= 0
INDE 15 30 35 FOBS=    44.0 SIGMA=  4.5 PHAS=  147.1 FOM= 0.30 TEST= 0
INDE 15 30 37 FOBS=    40.9 SIGMA=  5.0 PHAS=   42.4 FOM= 0.82 TEST= 0
INDE 15 30 39 FOBS=   107.6 SIGMA=  1.8 PHAS=   42.3 FOM= 0.86 TEST= 0
INDE 15 30 41 FOBS=   120.9 SIGMA=  1.6 PHAS=  -16.8 FOM= 0.98 TEST= 0
INDE 15 30 43 FOBS=    87.2 SIGMA=  2.0 PHAS=  -54.6 FOM= 0.84 TEST= 0
INDE 15 30 45 FOBS=   118.9 SIGMA=  1.4 PHAS=  -44.9 FOM= 0.96 TEST= 0
```

*FIG. 12A - 364*

```
INDE  15  30  47  FOBS=   58.1  SIGMA=   2.8  PHAS=  -160.0  FOM=  0.76  TEST= 0
INDE  15  30  49  FOBS=   74.3  SIGMA=   2.2  PHAS=  -116.1  FOM=  0.92  TEST= 0
INDE  15  30  51  FOBS=   67.2  SIGMA=   2.6  PHAS=  -111.2  FOM=  0.80  TEST= 0
INDE  15  30  53  FOBS=   69.4  SIGMA=   2.6  PHAS=   133.4  FOM=  0.81  TEST= 0
INDE  15  30  55  FOBS=  162.6  SIGMA=   1.2  PHAS=    71.4  FOM=  0.93  TEST= 0
INDE  15  30  57  FOBS=   66.1  SIGMA=   2.8  PHAS=  -128.6  FOM=  0.30  TEST= 1
INDE  15  30  59  FOBS=   69.9  SIGMA=   2.7  PHAS=  -127.3  FOM=  0.88  TEST= 0
INDE  15  30  61  FOBS=   49.5  SIGMA=   5.1  PHAS=   -18.4  FOM=  0.60  TEST= 0
INDE  15  30  63  FOBS=  102.7  SIGMA=   3.0  PHAS=   -42.6  FOM=  0.84  TEST= 0
INDE  15  30  65  FOBS=   47.2  SIGMA=  10.5  PHAS=  -107.8  FOM=  0.82  TEST= 0
INDE  15  30  67  FOBS=   34.1  SIGMA=  14.7  PHAS=  -173.2  FOM=  0.06  TEST= 1
INDE  15  30  69  FOBS=    0.0  SIGMA=  32.3  PHAS=     0.0  FOM=  0.00  TEST= 0
INDE  15  31  16  FOBS=  253.2  SIGMA=   0.6  PHAS=    81.0  FOM=  0.92  TEST= 0
INDE  15  31  18  FOBS=  190.6  SIGMA=   0.7  PHAS=  -168.6  FOM=  0.87  TEST= 1
INDE  15  31  20  FOBS=   37.1  SIGMA=   3.0  PHAS=  -100.4  FOM=  0.75  TEST= 0
INDE  15  31  22  FOBS=  113.8  SIGMA=   1.1  PHAS=  -116.7  FOM=  0.93  TEST= 0
INDE  15  31  24  FOBS=  220.9  SIGMA=   0.7  PHAS=   141.8  FOM=  0.91  TEST= 0
INDE  15  31  26  FOBS=  294.8  SIGMA=   0.7  PHAS=  -112.6  FOM=  0.89  TEST= 0
INDE  15  31  28  FOBS=  104.2  SIGMA=   1.6  PHAS=   173.7  FOM=  0.94  TEST= 1
INDE  15  31  30  FOBS=    0.0  SIGMA=  18.7  PHAS=     0.0  FOM=  0.00  TEST= 0
INDE  15  31  32  FOBS=  274.9  SIGMA=   1.3  PHAS=  -146.9  FOM=  0.36  TEST= 1
INDE  15  31  34  FOBS=  228.7  SIGMA=   1.1  PHAS=   -45.7  FOM=  0.97  TEST= 0
INDE  15  31  36  FOBS=    0.0  SIGMA=  19.8  PHAS=     0.0  FOM=  0.00  TEST= 0
INDE  15  31  38  FOBS=   83.5  SIGMA=   2.3  PHAS=   -74.5  FOM=  0.91  TEST= 0
INDE  15  31  40  FOBS=  198.6  SIGMA=   1.0  PHAS=   -63.4  FOM=  0.94  TEST= 0
INDE  15  31  42  FOBS=  191.3  SIGMA=   1.1  PHAS=   -84.3  FOM=  0.95  TEST= 0
INDE  15  31  44  FOBS=   49.9  SIGMA=   3.3  PHAS=   104.0  FOM=  0.82  TEST= 0
INDE  15  31  46  FOBS=  105.5  SIGMA=   1.6  PHAS=  -153.1  FOM=  0.91  TEST= 0
INDE  15  31  48  FOBS=  163.1  SIGMA=   1.1  PHAS=  -176.8  FOM=  0.94  TEST= 0
INDE  15  31  50  FOBS=  138.5  SIGMA=   1.3  PHAS=   144.7  FOM=  0.93  TEST= 0
INDE  15  31  52  FOBS=  109.3  SIGMA=   1.8  PHAS=   162.0  FOM=  0.93  TEST= 0
INDE  15  31  54  FOBS=  138.2  SIGMA=   1.5  PHAS=    73.9  FOM=  0.91  TEST= 0
INDE  15  31  56  FOBS=   55.5  SIGMA=   3.6  PHAS=    88.4  FOM=  0.63  TEST= 0
INDE  15  31  58  FOBS=   27.5  SIGMA=   7.2  PHAS=    -5.6  FOM=  0.48  TEST= 0
INDE  15  31  60  FOBS=   77.3  SIGMA=   2.6  PHAS=   114.6  FOM=  0.80  TEST= 0
INDE  15  31  62  FOBS=   45.3  SIGMA=   5.7  PHAS=  -154.9  FOM=  0.64  TEST= 0
INDE  15  31  64  FOBS=   62.9  SIGMA=   4.1  PHAS=   145.1  FOM=  0.64  TEST= 0
INDE  15  31  66  FOBS=   10.7  SIGMA=  46.6  PHAS=  -146.0  FOM=  0.15  TEST= 0
INDE  15  31  68  FOBS=   41.7  SIGMA=  12.5  PHAS=   120.9  FOM=  0.57  TEST= 0
INDE  15  32  15  FOBS=   92.3  SIGMA=   1.1  PHAS=   -68.6  FOM=  0.90  TEST= 0
INDE  15  32  17  FOBS=   94.9  SIGMA=   1.3  PHAS=   -38.5  FOM=  0.91  TEST= 0
INDE  15  32  19  FOBS=   31.0  SIGMA=   3.7  PHAS=  -118.2  FOM=  0.40  TEST= 0
INDE  15  32  21  FOBS=  125.2  SIGMA=   1.0  PHAS=   121.2  FOM=  0.79  TEST= 0
INDE  15  32  23  FOBS=   32.3  SIGMA=   4.4  PHAS=    62.3  FOM=  0.57  TEST= 1
INDE  15  32  25  FOBS=  188.8  SIGMA=   0.8  PHAS=  -154.1  FOM=  0.92  TEST= 0
INDE  15  32  27  FOBS=  171.2  SIGMA=   0.9  PHAS=    66.3  FOM=  0.95  TEST= 0
INDE  15  32  29  FOBS=    0.0  SIGMA=  20.1  PHAS=     0.0  FOM=  0.00  TEST= 0
INDE  15  32  31  FOBS=   83.3  SIGMA=   2.3  PHAS=   111.1  FOM=  0.94  TEST= 0
INDE  15  32  33  FOBS=  233.2  SIGMA=   1.3  PHAS=   -82.5  FOM=  0.76  TEST= 0
INDE  15  32  35  FOBS=   88.8  SIGMA=   2.3  PHAS=   143.4  FOM=  0.03  TEST= 0
INDE  15  32  37  FOBS=   33.5  SIGMA=   5.7  PHAS=    38.4  FOM=  0.05  TEST= 1
INDE  15  32  39  FOBS=  100.5  SIGMA=   1.9  PHAS=    74.3  FOM=  0.93  TEST= 0
INDE  15  32  41  FOBS=  143.2  SIGMA=   1.4  PHAS=   172.3  FOM=  0.87  TEST= 0
INDE  15  32  43  FOBS=   45.3  SIGMA=   4.0  PHAS=  -131.7  FOM=  0.83  TEST= 0
INDE  15  32  45  FOBS=  170.0  SIGMA=   1.1  PHAS=    77.8  FOM=  0.97  TEST= 0
INDE  15  32  47  FOBS=  144.9  SIGMA=   1.3  PHAS=    86.3  FOM=  0.96  TEST= 0
INDE  15  32  49  FOBS=  146.1  SIGMA=   1.4  PHAS=    48.0  FOM=  0.93  TEST= 0
INDE  15  32  51  FOBS=   70.3  SIGMA=   2.7  PHAS=    61.2  FOM=  0.90  TEST= 0
INDE  15  32  53  FOBS=  139.1  SIGMA=   1.5  PHAS=    12.2  FOM=  0.94  TEST= 0
INDE  15  32  55  FOBS=   76.6  SIGMA=   2.8  PHAS=    23.4  FOM=  0.77  TEST= 0
INDE  15  32  57  FOBS=    0.0  SIGMA=  21.5  PHAS=     0.0  FOM=  0.00  TEST= 0
INDE  15  32  59  FOBS=    0.0  SIGMA=  19.7  PHAS=     0.0  FOM=  0.00  TEST= 0
INDE  15  32  61  FOBS=   39.5  SIGMA=   5.3  PHAS=   135.4  FOM=  0.26  TEST= 0
INDE  15  32  63  FOBS=   35.3  SIGMA=   8.2  PHAS=  -143.2  FOM=  0.17  TEST= 1
INDE  15  32  65  FOBS=   20.2  SIGMA=  18.4  PHAS=  -102.5  FOM=  0.13  TEST= 0
INDE  15  32  67  FOBS=   60.3  SIGMA=   8.5  PHAS=    97.8  FOM=  0.70  TEST= 0
INDE  15  32  69  FOBS=   37.6  SIGMA=  13.9  PHAS=   -61.6  FOM=  0.27  TEST= 0
INDE  15  33  16  FOBS=  332.4  SIGMA=   0.5  PHAS=   138.4  FOM=  0.97  TEST= 0
INDE  15  33  18  FOBS=  154.9  SIGMA=   0.9  PHAS=   124.7  FOM=  0.82  TEST= 0
INDE  15  33  20  FOBS=  241.0  SIGMA=   0.7  PHAS=   113.9  FOM=  0.95  TEST= 0
```

*FIG. 12A - 365*

```
INDE 15 33 22 FOBS=  171.9 SIGMA=  0.9 PHAS=  -10.4 FOM= 0.92 TEST= 0
INDE 15 33 24 FOBS=  205.1 SIGMA=  0.8 PHAS=   61.1 FOM= 0.91 TEST= 0
INDE 15 33 26 FOBS=   60.8 SIGMA=  2.4 PHAS= -118.7 FOM= 0.81 TEST= 1
INDE 15 33 28 FOBS=  274.1 SIGMA=  0.8 PHAS=  -52.2 FOM= 0.98 TEST= 0
INDE 15 33 30 FOBS=  144.9 SIGMA=  1.4 PHAS=   47.8 FOM= 0.90 TEST= 0
INDE 15 33 32 FOBS=  390.6 SIGMA=  0.9 PHAS=  -51.0 FOM= 0.99 TEST= 0
INDE 15 33 34 FOBS=  100.5 SIGMA=  2.0 PHAS=  -30.8 FOM= 0.82 TEST= 0
INDE 15 33 36 FOBS=   57.9 SIGMA=  3.4 PHAS=  -18.1 FOM= 0.80 TEST= 0
INDE 15 33 38 FOBS=  123.9 SIGMA=  1.6 PHAS= -148.3 FOM= 0.95 TEST= 1
INDE 15 33 40 FOBS=    0.0 SIGMA= 19.4 PHAS=    0.0 FOM= 0.00 TEST= 0
INDE 15 33 42 FOBS=   28.3 SIGMA=  6.5 PHAS=   77.7 FOM= 0.66 TEST= 0
INDE 15 33 44 FOBS=  172.1 SIGMA=  1.1 PHAS=  -22.6 FOM= 0.91 TEST= 0
INDE 15 33 46 FOBS=  239.2 SIGMA=  1.1 PHAS=  -37.7 FOM= 0.96 TEST= 0
INDE 15 33 48 FOBS=   39.9 SIGMA=  5.1 PHAS= -105.6 FOM= 0.28 TEST= 0
INDE 15 33 50 FOBS=   33.9 SIGMA=  5.9 PHAS=  -39.4 FOM= 0.03 TEST= 0
INDE 15 33 52 FOBS=  118.8 SIGMA=  1.7 PHAS=  -69.9 FOM= 0.94 TEST= 0
INDE 15 33 54 FOBS=   36.7 SIGMA=  5.8 PHAS=  -76.7 FOM= 0.55 TEST= 0
INDE 15 33 56 FOBS=  106.6 SIGMA=  2.0 PHAS=   47.2 FOM= 0.92 TEST= 0
INDE 15 33 58 FOBS=   66.9 SIGMA=  3.2 PHAS=   56.0 FOM= 0.86 TEST= 0
INDE 15 33 60 FOBS=    0.0 SIGMA= 21.4 PHAS=    0.0 FOM= 0.00 TEST= 0
INDE 15 33 62 FOBS=    0.0 SIGMA= 24.3 PHAS=    0.0 FOM= 0.00 TEST= 0
INDE 15 33 64 FOBS=   64.3 SIGMA=  4.1 PHAS= -156.1 FOM= 0.33 TEST= 0
INDE 15 33 66 FOBS=    0.0 SIGMA= 27.2 PHAS=    0.0 FOM= 0.00 TEST= 0
INDE 15 33 68 FOBS=   36.5 SIGMA= 14.4 PHAS=  143.7 FOM= 0.43 TEST= 0
INDE 15 34 15 FOBS=  206.7 SIGMA=  0.6 PHAS=  -12.1 FOM= 0.91 TEST= 0
INDE 15 34 17 FOBS=  108.5 SIGMA=  1.2 PHAS=   -6.4 FOM= 0.87 TEST= 0
INDE 15 34 19 FOBS=  226.1 SIGMA=  0.8 PHAS=   42.4 FOM= 0.86 TEST= 0
INDE 15 34 21 FOBS=   78.9 SIGMA=  1.9 PHAS= -126.9 FOM= 0.94 TEST= 0
INDE 15 34 23 FOBS=  287.3 SIGMA=  0.7 PHAS= -115.3 FOM= 0.97 TEST= 0
INDE 15 34 25 FOBS=  272.6 SIGMA=  0.7 PHAS= -165.2 FOM= 0.30 TEST= 1
INDE 15 34 27 FOBS=  300.9 SIGMA=  0.7 PHAS=  -11.7 FOM= 0.47 TEST= 1
INDE 15 34 29 FOBS=  225.9 SIGMA=  0.8 PHAS=  -83.0 FOM= 0.99 TEST= 1
INDE 15 34 31 FOBS=   69.9 SIGMA=  2.9 PHAS= -153.1 FOM= 0.96 TEST= 0
INDE 15 34 33 FOBS=  350.1 SIGMA=  1.2 PHAS= -114.6 FOM= 0.98 TEST= 0
INDE 15 34 35 FOBS=  145.9 SIGMA=  1.4 PHAS=  -64.8 FOM= 0.89 TEST= 0
INDE 15 34 37 FOBS=    0.0 SIGMA= 19.7 PHAS=    0.0 FOM= 0.00 TEST= 0
INDE 15 34 39 FOBS=  234.3 SIGMA=  0.9 PHAS=   66.4 FOM= 0.96 TEST= 0
INDE 15 34 41 FOBS=    0.0 SIGMA= 19.7 PHAS=    0.0 FOM= 0.00 TEST= 0
INDE 15 34 43 FOBS=  150.2 SIGMA=  1.4 PHAS= -142.8 FOM= 0.95 TEST= 0
INDE 15 34 45 FOBS=  135.7 SIGMA=  1.7 PHAS= -159.6 FOM= 0.90 TEST= 0
INDE 15 34 47 FOBS=    0.0 SIGMA= 21.0 PHAS=    0.0 FOM= 0.00 TEST= 0
INDE 15 34 49 FOBS=   85.7 SIGMA=  2.6 PHAS=   62.9 FOM= 0.84 TEST= 0
INDE 15 34 51 FOBS=   51.9 SIGMA=  3.6 PHAS= -114.9 FOM= 0.79 TEST= 0
INDE 15 34 53 FOBS=   59.2 SIGMA=  3.4 PHAS=  150.9 FOM= 0.75 TEST= 0
INDE 15 34 55 FOBS=  103.0 SIGMA=  2.1 PHAS=  -98.6 FOM= 0.85 TEST= 0
INDE 15 34 57 FOBS=  150.8 SIGMA=  1.5 PHAS=  -46.4 FOM= 0.95 TEST= 0
INDE 15 34 59 FOBS=   55.3 SIGMA=  3.9 PHAS=  -20.0 FOM= 0.76 TEST= 0
INDE 15 34 61 FOBS=   17.8 SIGMA= 14.4 PHAS= -166.4 FOM= 0.21 TEST= 0
INDE 15 34 63 FOBS=    0.0 SIGMA= 20.5 PHAS=    0.0 FOM= 0.00 TEST= 0
INDE 15 34 65 FOBS=   40.2 SIGMA=  7.7 PHAS=   85.3 FOM= 0.63 TEST= 0
INDE 15 34 67 FOBS=    0.0 SIGMA= 25.2 PHAS=    0.0 FOM= 0.00 TEST= 0
INDE 15 35 16 FOBS=  303.4 SIGMA=  0.6 PHAS= -154.8 FOM= 0.95 TEST= 0
INDE 15 35 18 FOBS=   55.4 SIGMA=  2.7 PHAS= -150.8 FOM= 0.66 TEST= 0
INDE 15 35 20 FOBS=  184.2 SIGMA=  0.9 PHAS= -169.5 FOM= 0.91 TEST= 0
INDE 15 35 22 FOBS=  253.0 SIGMA=  0.8 PHAS=   63.4 FOM= 0.94 TEST= 0
INDE 15 35 24 FOBS=  199.4 SIGMA=  0.9 PHAS=   36.8 FOM= 0.96 TEST= 0
INDE 15 35 26 FOBS=  355.5 SIGMA=  0.6 PHAS=  116.6 FOM= 0.95 TEST= 0
INDE 15 35 28 FOBS=  222.9 SIGMA=  0.8 PHAS=  149.2 FOM= 0.99 TEST= 0
INDE 15 35 30 FOBS=   92.6 SIGMA=  1.9 PHAS=  176.9 FOM= 0.72 TEST= 0
INDE 15 35 32 FOBS=  338.9 SIGMA=  0.8 PHAS= -174.0 FOM= 0.99 TEST= 0
INDE 15 35 34 FOBS=  192.0 SIGMA=  1.1 PHAS=  166.3 FOM= 0.96 TEST= 0
INDE 15 35 36 FOBS=  187.4 SIGMA=  1.2 PHAS=  -40.4 FOM= 0.94 TEST= 0
INDE 15 35 38 FOBS=  169.1 SIGMA=  1.2 PHAS=  -74.9 FOM= 0.95 TEST= 0
INDE 15 35 40 FOBS=   27.1 SIGMA=  9.3 PHAS=  -10.3 FOM= 0.16 TEST= 0
INDE 15 35 42 FOBS=   27.4 SIGMA=  8.3 PHAS= -179.3 FOM= 0.52 TEST= 1
INDE 15 35 44 FOBS=   60.9 SIGMA=  3.7 PHAS=   64.1 FOM= 0.79 TEST= 0
INDE 15 35 46 FOBS=   58.8 SIGMA=  3.8 PHAS=  -14.7 FOM= 0.55 TEST= 0
INDE 15 35 48 FOBS=   56.0 SIGMA=  4.0 PHAS= -132.2 FOM= 0.73 TEST= 0
INDE 15 35 50 FOBS=   71.4 SIGMA=  3.1 PHAS= -141.0 FOM= 0.35 TEST= 1
INDE 15 35 52 FOBS=  140.8 SIGMA=  1.6 PHAS=  -78.0 FOM= 0.92 TEST= 0
```

*FIG. 12A - 366*

```
INDE 15 35 54 FOBS=    87.7 SIGMA=  2.5 PHAS= -100.8 FOM= 0.23 TEST= 1
INDE 15 35 56 FOBS=   117.1 SIGMA=  1.9 PHAS=  101.6 FOM= 0.60 TEST= 0
INDE 15 35 58 FOBS=   150.6 SIGMA=  1.5 PHAS= -134.6 FOM= 0.96 TEST= 0
INDE 15 35 60 FOBS=    39.6 SIGMA=  5.3 PHAS=  157.1 FOM= 0.07 TEST= 1
INDE 15 35 62 FOBS=    38.0 SIGMA=  5.6 PHAS=   25.6 FOM= 0.41 TEST= 0
INDE 15 35 64 FOBS=    45.7 SIGMA=  4.8 PHAS=   59.6 FOM= 0.58 TEST= 0
INDE 15 35 66 FOBS=    13.4 SIGMA= 23.4 PHAS=  -70.2 FOM= 0.20 TEST= 0
INDE 15 36 15 FOBS=   165.1 SIGMA=  1.0 PHAS=  170.8 FOM= 0.86 TEST= 1
INDE 15 36 17 FOBS=    76.9 SIGMA=  1.9 PHAS=  159.5 FOM= 0.86 TEST= 0
INDE 15 36 19 FOBS=   267.9 SIGMA=  0.8 PHAS=   77.0 FOM= 0.97 TEST= 0
INDE 15 36 21 FOBS=   134.3 SIGMA=  1.2 PHAS=   22.1 FOM= 0.94 TEST= 0
INDE 15 36 23 FOBS=   296.5 SIGMA=  0.8 PHAS=  -84.7 FOM= 0.97 TEST= 0
INDE 15 36 25 FOBS=   110.7 SIGMA=  1.7 PHAS=  -72.0 FOM= 0.76 TEST= 0
INDE 15 36 27 FOBS=   243.6 SIGMA=  0.8 PHAS=   36.1 FOM= 0.97 TEST= 0
INDE 15 36 29 FOBS=   121.4 SIGMA=  1.5 PHAS=   30.0 FOM= 0.95 TEST= 0
INDE 15 36 31 FOBS=   173.4 SIGMA=  1.1 PHAS=   77.9 FOM= 0.96 TEST= 0
INDE 15 36 33 FOBS=   133.4 SIGMA=  1.5 PHAS=   99.0 FOM= 0.96 TEST= 0
INDE 15 36 35 FOBS=   121.1 SIGMA=  1.7 PHAS=  -21.3 FOM= 0.80 TEST= 0
INDE 15 36 37 FOBS=   132.4 SIGMA=  1.7 PHAS= -120.0 FOM= 0.96 TEST= 0
INDE 15 36 39 FOBS=    97.5 SIGMA=  2.4 PHAS=  104.1 FOM= 0.85 TEST= 0
INDE 15 36 41 FOBS=   131.3 SIGMA=  1.8 PHAS=  170.4 FOM= 0.92 TEST= 0
INDE 15 36 43 FOBS=     0.0 SIGMA= 21.1 PHAS=    0.0 FOM= 0.00 TEST= 0
INDE 15 36 45 FOBS=    60.4 SIGMA=  3.7 PHAS= -151.4 FOM= 0.25 TEST= 1
INDE 15 36 47 FOBS=    28.0 SIGMA=  7.9 PHAS= -143.0 FOM= 0.03 TEST= 1
INDE 15 36 49 FOBS=    89.4 SIGMA=  2.5 PHAS=   64.1 FOM= 0.91 TEST= 0
INDE 15 36 51 FOBS=     9.6 SIGMA= 22.5 PHAS=   56.6 FOM= 0.04 TEST= 0
INDE 15 36 53 FOBS=   102.3 SIGMA=  2.1 PHAS= -157.8 FOM= 0.66 TEST= 0
INDE 15 36 55 FOBS=     0.0 SIGMA= 21.4 PHAS=    0.0 FOM= 0.00 TEST= 1
INDE 15 36 57 FOBS=   136.1 SIGMA=  1.7 PHAS=   87.5 FOM= 0.96 TEST= 0
INDE 15 36 59 FOBS=    78.6 SIGMA=  2.7 PHAS=  140.8 FOM= 0.69 TEST= 0
INDE 15 36 61 FOBS=    25.1 SIGMA= 12.4 PHAS=  -90.7 FOM= 0.38 TEST= 0
INDE 15 36 63 FOBS=    71.1 SIGMA=  3.1 PHAS=  -31.2 FOM= 0.84 TEST= 0
INDE 15 36 65 FOBS=    47.3 SIGMA=  6.7 PHAS=   91.9 FOM= 0.17 TEST= 1
INDE 15 36 67 FOBS=     0.0 SIGMA= 27.8 PHAS=    0.0 FOM= 0.00 TEST= 0
INDE 15 37 16 FOBS=    97.9 SIGMA=  1.6 PHAS=  -49.7 FOM= 0.57 TEST= 0
INDE 15 37 18 FOBS=   102.2 SIGMA=  1.6 PHAS=   58.3 FOM= 0.57 TEST= 0
INDE 15 37 20 FOBS=   220.5 SIGMA=  0.8 PHAS=  -87.8 FOM= 0.97 TEST= 0
INDE 15 37 22 FOBS=    92.4 SIGMA=  1.9 PHAS=   27.9 FOM= 0.94 TEST= 0
INDE 15 37 24 FOBS=   149.3 SIGMA=  1.3 PHAS= -158.1 FOM= 0.79 TEST= 0
INDE 15 37 26 FOBS=   203.3 SIGMA=  1.0 PHAS=  -72.5 FOM= 0.94 TEST= 0
INDE 15 37 28 FOBS=    44.8 SIGMA=  3.9 PHAS=   23.0 FOM= 0.79 TEST= 0
INDE 15 37 30 FOBS=   195.8 SIGMA=  1.0 PHAS=   33.2 FOM= 0.74 TEST= 1
INDE 15 37 32 FOBS=     0.0 SIGMA= 19.0 PHAS=    0.0 FOM= 0.00 TEST= 0
INDE 15 37 34 FOBS=   164.5 SIGMA=  1.2 PHAS=   36.2 FOM= 0.91 TEST= 0
INDE 15 37 36 FOBS=   124.0 SIGMA=  2.0 PHAS= -115.9 FOM= 0.87 TEST= 0
INDE 15 37 38 FOBS=   123.6 SIGMA=  2.0 PHAS=  -20.7 FOM= 0.86 TEST= 0
INDE 15 37 40 FOBS=   139.9 SIGMA=  1.8 PHAS=  139.3 FOM= 0.92 TEST= 0
INDE 15 37 42 FOBS=     0.0 SIGMA= 21.2 PHAS=    0.0 FOM= 0.00 TEST= 0
INDE 15 37 44 FOBS=    57.4 SIGMA=  3.9 PHAS=   27.8 FOM= 0.53 TEST= 0
INDE 15 37 46 FOBS=    57.0 SIGMA=  3.9 PHAS=  136.4 FOM= 0.65 TEST= 0
INDE 15 37 48 FOBS=    35.0 SIGMA=  6.3 PHAS=  136.8 FOM= 0.30 TEST= 0
INDE 15 37 50 FOBS=     0.0 SIGMA= 20.7 PHAS=    0.0 FOM= 0.00 TEST= 0
INDE 15 37 52 FOBS=    98.4 SIGMA=  2.2 PHAS=  -72.7 FOM= 0.91 TEST= 0
INDE 15 37 54 FOBS=    46.1 SIGMA=  4.6 PHAS=  -50.1 FOM= 0.74 TEST= 0
INDE 15 37 56 FOBS=    38.8 SIGMA=  5.5 PHAS=  -40.4 FOM= 0.82 TEST= 0
INDE 15 37 58 FOBS=    36.1 SIGMA=  5.9 PHAS=  -59.5 FOM= 0.49 TEST= 0
INDE 15 37 60 FOBS=    39.6 SIGMA=  5.9 PHAS=   68.5 FOM= 0.42 TEST= 0
INDE 15 37 62 FOBS=    37.8 SIGMA=  5.7 PHAS= -100.1 FOM= 0.66 TEST= 0
INDE 15 37 64 FOBS=    50.4 SIGMA=  5.4 PHAS= -165.5 FOM= 0.86 TEST= 0
INDE 15 37 66 FOBS=    79.2 SIGMA=  4.2 PHAS=  -98.5 FOM= 0.81 TEST= 0
INDE 15 38 15 FOBS=   329.1 SIGMA=  0.7 PHAS=  -61.8 FOM= 0.70 TEST= 1
INDE 15 38 17 FOBS=   396.8 SIGMA=  0.7 PHAS= -140.7 FOM= 0.96 TEST= 0
INDE 15 38 19 FOBS=   228.8 SIGMA=  0.9 PHAS= -178.6 FOM= 0.96 TEST= 0
INDE 15 38 21 FOBS=     0.0 SIGMA= 19.0 PHAS=    0.0 FOM= 0.00 TEST= 0
INDE 15 38 23 FOBS=   150.0 SIGMA=  1.3 PHAS=  177.9 FOM= 0.80 TEST= 0
INDE 15 38 25 FOBS=   184.8 SIGMA=  1.1 PHAS=  112.1 FOM= 0.82 TEST= 0
INDE 15 38 27 FOBS=    32.8 SIGMA=  6.0 PHAS=  -81.4 FOM= 0.42 TEST= 0
INDE 15 38 29 FOBS=    99.9 SIGMA=  1.8 PHAS=   30.6 FOM= 0.92 TEST= 1
INDE 15 38 31 FOBS=   132.1 SIGMA=  1.4 PHAS=  -28.8 FOM= 0.81 TEST= 0
INDE 15 38 33 FOBS=   162.7 SIGMA=  1.2 PHAS=  -57.4 FOM= 0.85 TEST= 0
```

*FIG. 12A - 367*

| | | | | | | | | | | | |
|---|---|---|---|---|---|---|---|---|---|---|---|
| INDE | 15 | 38 | 35 | FOBS= | 86.0 | SIGMA= | 2.3 | PHAS= | -65.4 | FOM= | 0.91 | TEST= 0 |
| INDE | 15 | 38 | 37 | FOBS= | 109.9 | SIGMA= | 2.2 | PHAS= | -151.5 | FOM= | 0.45 | TEST= 0 |
| INDE | 15 | 38 | 39 | FOBS= | 90.8 | SIGMA= | 2.6 | PHAS= | 48.6 | FOM= | 0.55 | TEST= 1 |
| INDE | 15 | 38 | 41 | FOBS= | 47.4 | SIGMA= | 4.8 | PHAS= | 92.9 | FOM= | 0.78 | TEST= 0 |
| INDE | 15 | 38 | 43 | FOBS= | 114.9 | SIGMA= | 2.0 | PHAS= | -7.6 | FOM= | 0.89 | TEST= 0 |
| INDE | 15 | 38 | 45 | FOBS= | 133.5 | SIGMA= | 1.8 | PHAS= | -42.9 | FOM= | 0.95 | TEST= 0 |
| INDE | 15 | 38 | 47 | FOBS= | 131.0 | SIGMA= | 1.8 | PHAS= | 46.3 | FOM= | 0.94 | TEST= 0 |
| INDE | 15 | 38 | 49 | FOBS= | 0.0 | SIGMA= | 22.8 | PHAS= | 0.0 | FOM= | 0.00 | TEST= 0 |
| INDE | 15 | 38 | 51 | FOBS= | 78.5 | SIGMA= | 2.8 | PHAS= | 116.5 | FOM= | 0.92 | TEST= 0 |
| INDE | 15 | 38 | 53 | FOBS= | 146.1 | SIGMA= | 1.6 | PHAS= | -148.5 | FOM= | 0.89 | TEST= 0 |
| INDE | 15 | 38 | 55 | FOBS= | 70.5 | SIGMA= | 3.1 | PHAS= | -36.2 | FOM= | 0.46 | TEST= 1 |
| INDE | 15 | 38 | 57 | FOBS= | 6.3 | SIGMA= | 36.2 | PHAS= | -59.7 | FOM= | 0.05 | TEST= 0 |
| INDE | 15 | 38 | 59 | FOBS= | 37.9 | SIGMA= | 6.1 | PHAS= | 149.8 | FOM= | 0.67 | TEST= 0 |
| INDE | 15 | 38 | 61 | FOBS= | 46.9 | SIGMA= | 4.6 | PHAS= | 154.8 | FOM= | 0.81 | TEST= 0 |
| INDE | 15 | 38 | 63 | FOBS= | 70.0 | SIGMA= | 3.2 | PHAS= | 56.8 | FOM= | 0.71 | TEST= 0 |
| INDE | 15 | 38 | 65 | FOBS= | 66.1 | SIGMA= | 5.0 | PHAS= | 128.5 | FOM= | 0.87 | TEST= 0 |
| INDE | 15 | 39 | 16 | FOBS= | 378.2 | SIGMA= | 0.7 | PHAS= | 154.7 | FOM= | 0.96 | TEST= 0 |
| INDE | 15 | 39 | 18 | FOBS= | 299.6 | SIGMA= | 0.8 | PHAS= | 107.0 | FOM= | 0.98 | TEST= 0 |
| INDE | 15 | 39 | 20 | FOBS= | 104.9 | SIGMA= | 1.7 | PHAS= | -150.6 | FOM= | 0.89 | TEST= 0 |
| INDE | 15 | 39 | 22 | FOBS= | 225.6 | SIGMA= | 0.9 | PHAS= | 20.2 | FOM= | 0.97 | TEST= 0 |
| INDE | 15 | 39 | 24 | FOBS= | 246.4 | SIGMA= | 0.9 | PHAS= | -1.6 | FOM= | 0.94 | TEST= 0 |
| INDE | 15 | 39 | 26 | FOBS= | 223.7 | SIGMA= | 1.0 | PHAS= | -73.6 | FOM= | 0.93 | TEST= 0 |
| INDE | 15 | 39 | 28 | FOBS= | 115.9 | SIGMA= | 1.8 | PHAS= | 31.9 | FOM= | 0.94 | TEST= 0 |
| INDE | 15 | 39 | 30 | FOBS= | 165.0 | SIGMA= | 1.3 | PHAS= | -21.4 | FOM= | 0.71 | TEST= 1 |
| INDE | 15 | 39 | 32 | FOBS= | 159.7 | SIGMA= | 1.4 | PHAS= | -116.0 | FOM= | 0.96 | TEST= 0 |
| INDE | 15 | 39 | 34 | FOBS= | 36.0 | SIGMA= | 4.9 | PHAS= | 25.3 | FOM= | 0.85 | TEST= 0 |
| INDE | 15 | 39 | 36 | FOBS= | 40.9 | SIGMA= | 4.8 | PHAS= | 173.2 | FOM= | 0.83 | TEST= 0 |
| INDE | 15 | 39 | 38 | FOBS= | 0.0 | SIGMA= | 26.4 | PHAS= | 0.0 | FOM= | 0.00 | TEST= 0 |
| INDE | 15 | 39 | 40 | FOBS= | 118.8 | SIGMA= | 2.0 | PHAS= | -36.7 | FOM= | 0.89 | TEST= 0 |
| INDE | 15 | 39 | 42 | FOBS= | 138.8 | SIGMA= | 1.8 | PHAS= | -75.8 | FOM= | 0.94 | TEST= 0 |
| INDE | 15 | 39 | 44 | FOBS= | 91.5 | SIGMA= | 2.5 | PHAS= | -101.6 | FOM= | 0.93 | TEST= 0 |
| INDE | 15 | 39 | 46 | FOBS= | 146.0 | SIGMA= | 1.6 | PHAS= | -87.6 | FOM= | 0.95 | TEST= 0 |
| INDE | 15 | 39 | 48 | FOBS= | 45.8 | SIGMA= | 4.8 | PHAS= | 18.4 | FOM= | 0.68 | TEST= 0 |
| INDE | 15 | 39 | 50 | FOBS= | 95.7 | SIGMA= | 2.3 | PHAS= | -9.9 | FOM= | 0.91 | TEST= 0 |
| INDE | 15 | 39 | 52 | FOBS= | 128.6 | SIGMA= | 1.8 | PHAS= | 164.0 | FOM= | 0.38 | TEST= 1 |
| INDE | 15 | 39 | 54 | FOBS= | 102.6 | SIGMA= | 2.2 | PHAS= | -72.8 | FOM= | 0.87 | TEST= 0 |
| INDE | 15 | 39 | 56 | FOBS= | 103.4 | SIGMA= | 2.1 | PHAS= | -84.1 | FOM= | 0.94 | TEST= 0 |
| INDE | 15 | 39 | 58 | FOBS= | 31.1 | SIGMA= | 8.6 | PHAS= | 130.5 | FOM= | 0.04 | TEST= 1 |
| INDE | 15 | 39 | 60 | FOBS= | 89.8 | SIGMA= | 2.5 | PHAS= | 43.6 | FOM= | 0.92 | TEST= 0 |
| INDE | 15 | 39 | 62 | FOBS= | 0.0 | SIGMA= | 21.9 | PHAS= | 0.0 | FOM= | 0.00 | TEST= 0 |
| INDE | 15 | 39 | 64 | FOBS= | 57.4 | SIGMA= | 4.9 | PHAS= | -35.1 | FOM= | 0.80 | TEST= 0 |
| INDE | 15 | 40 | 15 | FOBS= | 191.2 | SIGMA= | 1.1 | PHAS= | 54.8 | FOM= | 0.87 | TEST= 1 |
| INDE | 15 | 40 | 17 | FOBS= | 202.1 | SIGMA= | 1.0 | PHAS= | 60.0 | FOM= | 0.92 | TEST= 0 |
| INDE | 15 | 40 | 19 | FOBS= | 25.1 | SIGMA= | 8.1 | PHAS= | -161.8 | FOM= | 0.48 | TEST= 0 |
| INDE | 15 | 40 | 21 | FOBS= | 136.0 | SIGMA= | 1.6 | PHAS= | 47.6 | FOM= | 0.98 | TEST= 1 |
| INDE | 15 | 40 | 23 | FOBS= | 186.1 | SIGMA= | 1.3 | PHAS= | -101.8 | FOM= | 0.91 | TEST= 0 |
| INDE | 15 | 40 | 25 | FOBS= | 131.9 | SIGMA= | 1.7 | PHAS= | -146.3 | FOM= | 0.96 | TEST= 0 |
| INDE | 15 | 40 | 27 | FOBS= | 184.2 | SIGMA= | 1.3 | PHAS= | -95.6 | FOM= | 0.91 | TEST= 0 |
| INDE | 15 | 40 | 29 | FOBS= | 122.3 | SIGMA= | 1.8 | PHAS= | -59.9 | FOM= | 0.88 | TEST= 0 |
| INDE | 15 | 40 | 31 | FOBS= | 158.1 | SIGMA= | 1.3 | PHAS= | -88.0 | FOM= | 0.96 | TEST= 0 |
| INDE | 15 | 40 | 33 | FOBS= | 128.4 | SIGMA= | 1.6 | PHAS= | -93.6 | FOM= | 0.89 | TEST= 0 |
| INDE | 15 | 40 | 35 | FOBS= | 68.2 | SIGMA= | 3.0 | PHAS= | -123.6 | FOM= | 0.14 | TEST= 0 |
| INDE | 15 | 40 | 37 | FOBS= | 85.6 | SIGMA= | 2.3 | PHAS= | 60.4 | FOM= | 0.82 | TEST= 0 |
| INDE | 15 | 40 | 39 | FOBS= | 42.7 | SIGMA= | 5.5 | PHAS= | 50.9 | FOM= | 0.12 | TEST= 1 |
| INDE | 15 | 40 | 41 | FOBS= | 97.6 | SIGMA= | 2.4 | PHAS= | -107.7 | FOM= | 0.92 | TEST= 0 |
| INDE | 15 | 40 | 43 | FOBS= | 105.5 | SIGMA= | 2.2 | PHAS= | -124.9 | FOM= | 0.92 | TEST= 0 |
| INDE | 15 | 40 | 45 | FOBS= | 85.0 | SIGMA= | 2.7 | PHAS= | 166.8 | FOM= | 0.93 | TEST= 0 |
| INDE | 15 | 40 | 47 | FOBS= | 35.2 | SIGMA= | 7.6 | PHAS= | 115.3 | FOM= | 0.25 | TEST= 0 |
| INDE | 15 | 40 | 49 | FOBS= | 139.1 | SIGMA= | 1.7 | PHAS= | -86.3 | FOM= | 0.96 | TEST= 0 |
| INDE | 15 | 40 | 51 | FOBS= | 0.0 | SIGMA= | 25.2 | PHAS= | 0.0 | FOM= | 0.00 | TEST= 0 |
| INDE | 15 | 40 | 53 | FOBS= | 53.0 | SIGMA= | 4.1 | PHAS= | -91.4 | FOM= | 0.65 | TEST= 0 |
| INDE | 15 | 40 | 55 | FOBS= | 40.1 | SIGMA= | 5.4 | PHAS= | -88.0 | FOM= | 0.86 | TEST= 0 |
| INDE | 15 | 40 | 57 | FOBS= | 42.4 | SIGMA= | 6.1 | PHAS= | 31.5 | FOM= | 0.08 | TEST= 1 |
| INDE | 15 | 40 | 59 | FOBS= | 0.0 | SIGMA= | 22.5 | PHAS= | 0.0 | FOM= | 0.00 | TEST= 1 |
| INDE | 15 | 40 | 61 | FOBS= | 8.3 | SIGMA= | 31.8 | PHAS= | -148.5 | FOM= | 0.11 | TEST= 0 |
| INDE | 15 | 40 | 63 | FOBS= | 25.6 | SIGMA= | 11.7 | PHAS= | 9.3 | FOM= | 0.63 | TEST= 0 |
| INDE | 15 | 41 | 16 | FOBS= | 288.0 | SIGMA= | 0.9 | PHAS= | -22.5 | FOM= | 0.97 | TEST= 0 |
| INDE | 15 | 41 | 18 | FOBS= | 78.3 | SIGMA= | 2.7 | PHAS= | -86.7 | FOM= | 0.95 | TEST= 0 |
| INDE | 15 | 41 | 20 | FOBS= | 35.6 | SIGMA= | 6.7 | PHAS= | -148.8 | FOM= | 0.49 | TEST= 0 |
| INDE | 15 | 41 | 22 | FOBS= | 239.7 | SIGMA= | 1.1 | PHAS= | -74.9 | FOM= | 0.96 | TEST= 0 |

*FIG. 12A - 368*

```
INDE  15  41  24  FOBS=    99.8  SIGMA=   2.2  PHAS=   -93.4  FOM=  0.34  TEST= 1
INDE  15  41  26  FOBS=   109.5  SIGMA=   2.1  PHAS=   -71.6  FOM=  0.86  TEST= 0
INDE  15  41  28  FOBS=     0.0  SIGMA=  21.0  PHAS=     0.0  FOM=  0.00  TEST= 0
INDE  15  41  30  FOBS=   163.9  SIGMA=   1.3  PHAS=  -170.9  FOM=  0.88  TEST= 0
INDE  15  41  32  FOBS=   232.6  SIGMA=   1.0  PHAS=  -135.2  FOM=  0.93  TEST= 0
INDE  15  41  34  FOBS=    82.4  SIGMA=   2.4  PHAS=   165.6  FOM=  0.55  TEST= 0
INDE  15  41  36  FOBS=    47.1  SIGMA=   4.1  PHAS=    94.3  FOM=  0.11  TEST= 0
INDE  15  41  38  FOBS=   118.1  SIGMA=   1.7  PHAS=   -28.4  FOM=  0.91  TEST= 0
INDE  15  41  40  FOBS=   153.8  SIGMA=   1.6  PHAS=   -61.5  FOM=  0.91  TEST= 0
INDE  15  41  42  FOBS=    88.5  SIGMA=   2.7  PHAS=   171.0  FOM=  0.90  TEST= 0
INDE  15  41  44  FOBS=   120.7  SIGMA=   2.0  PHAS=    98.9  FOM=  0.90  TEST= 0
INDE  15  41  46  FOBS=    50.2  SIGMA=   4.4  PHAS=    38.8  FOM=  0.73  TEST= 0
INDE  15  41  48  FOBS=    35.8  SIGMA=   6.1  PHAS=   156.5  FOM=  0.28  TEST= 1
INDE  15  41  50  FOBS=    38.1  SIGMA=   5.8  PHAS=     4.4  FOM=  0.53  TEST= 0
INDE  15  41  52  FOBS=    86.9  SIGMA=   2.6  PHAS=   162.2  FOM=  0.83  TEST= 0
INDE  15  41  54  FOBS=    87.5  SIGMA=   2.6  PHAS=   179.2  FOM=  0.89  TEST= 0
INDE  15  41  56  FOBS=   156.0  SIGMA=   1.5  PHAS=  -160.1  FOM=  0.97  TEST= 0
INDE  15  41  58  FOBS=     0.0  SIGMA=  20.5  PHAS=     0.0  FOM=  0.00  TEST= 0
INDE  15  41  60  FOBS=    51.4  SIGMA=   4.2  PHAS=   -32.7  FOM=  0.70  TEST= 0
INDE  15  41  62  FOBS=     0.0  SIGMA=  25.4  PHAS=     0.0  FOM=  0.00  TEST= 0
INDE  15  41  64  FOBS=    76.9  SIGMA=   3.7  PHAS=   -40.2  FOM=  0.93  TEST= 0
INDE  15  42  15  FOBS=    49.1  SIGMA=   4.1  PHAS=  -115.4  FOM=  0.87  TEST= 0
INDE  15  42  17  FOBS=    13.7  SIGMA=  15.5  PHAS=   -94.5  FOM=  0.09  TEST= 0
INDE  15  42  19  FOBS=     6.7  SIGMA=  39.1  PHAS=  -125.3  FOM=  0.00  TEST= 1
INDE  15  42  21  FOBS=   132.3  SIGMA=   1.7  PHAS=    93.9  FOM=  0.90  TEST= 0
INDE  15  42  23  FOBS=   177.0  SIGMA=   1.3  PHAS=  -163.2  FOM=  0.94  TEST= 0
INDE  15  42  25  FOBS=   213.0  SIGMA=   1.1  PHAS=  -136.5  FOM=  0.95  TEST= 0
INDE  15  42  27  FOBS=   142.1  SIGMA=   1.6  PHAS=   -80.0  FOM=  0.91  TEST= 0
INDE  15  42  29  FOBS=   137.9  SIGMA=   1.7  PHAS=   -30.7  FOM=  0.34  TEST= 1
INDE  15  42  31  FOBS=    54.9  SIGMA=   3.8  PHAS=    92.3  FOM=  0.53  TEST= 0
INDE  15  42  33  FOBS=    89.2  SIGMA=   2.2  PHAS=   107.4  FOM=  0.66  TEST= 0
INDE  15  42  35  FOBS=     0.0  SIGMA=  20.3  PHAS=     0.0  FOM=  0.00  TEST= 0
INDE  15  42  37  FOBS=    48.5  SIGMA=   4.0  PHAS=   -66.5  FOM=  0.27  TEST= 0
INDE  15  42  39  FOBS=   148.4  SIGMA=   1.4  PHAS=  -124.2  FOM=  0.93  TEST= 0
INDE  15  42  41  FOBS=    20.5  SIGMA=  11.4  PHAS=   142.2  FOM=  0.67  TEST= 0
INDE  15  42  43  FOBS=    57.8  SIGMA=   4.0  PHAS=    -0.4  FOM=  0.64  TEST= 0
INDE  15  42  45  FOBS=     0.0  SIGMA=  22.0  PHAS=     0.0  FOM=  0.00  TEST= 0
INDE  15  42  47  FOBS=     0.0  SIGMA=  21.0  PHAS=     0.0  FOM=  0.00  TEST= 0
INDE  15  42  49  FOBS=     0.0  SIGMA=  20.9  PHAS=     0.0  FOM=  0.00  TEST= 0
INDE  15  42  51  FOBS=    22.1  SIGMA=   9.9  PHAS=  -167.6  FOM=  0.81  TEST= 0
INDE  15  42  53  FOBS=    43.8  SIGMA=   5.0  PHAS=   161.0  FOM=  0.67  TEST= 0
INDE  15  42  55  FOBS=   122.2  SIGMA=   1.9  PHAS=    90.6  FOM=  0.95  TEST= 0
INDE  15  42  57  FOBS=    80.6  SIGMA=   2.7  PHAS=    75.4  FOM=  0.89  TEST= 0
INDE  15  42  59  FOBS=    47.8  SIGMA=   4.5  PHAS=  -167.1  FOM=  0.39  TEST= 0
INDE  15  42  61  FOBS=     0.0  SIGMA=  23.2  PHAS=     0.0  FOM=  0.00  TEST= 0
INDE  15  42  63  FOBS=    51.0  SIGMA=   5.5  PHAS=  -147.4  FOM=  0.76  TEST= 0
INDE  15  43  16  FOBS=   240.1  SIGMA=   1.0  PHAS=   -34.0  FOM=  0.95  TEST= 0
INDE  15  43  18  FOBS=   223.6  SIGMA=   1.1  PHAS=   -61.3  FOM=  0.94  TEST= 0
INDE  15  43  20  FOBS=   125.2  SIGMA=   1.9  PHAS=    22.3  FOM=  0.38  TEST= 1
INDE  15  43  22  FOBS=    84.4  SIGMA=   2.6  PHAS=  -117.5  FOM=  0.83  TEST= 0
INDE  15  43  24  FOBS=   183.4  SIGMA=   1.3  PHAS=   167.8  FOM=  0.93  TEST= 0
INDE  15  43  26  FOBS=   160.3  SIGMA=   1.4  PHAS=   168.4  FOM=  0.91  TEST= 0
INDE  15  43  28  FOBS=   115.4  SIGMA=   1.9  PHAS=    33.4  FOM=  0.87  TEST= 1
INDE  15  43  30  FOBS=     0.0  SIGMA=  20.2  PHAS=     0.0  FOM=  0.00  TEST= 1
INDE  15  43  32  FOBS=   141.3  SIGMA=   1.4  PHAS=   -82.7  FOM=  0.93  TEST= 0
INDE  15  43  34  FOBS=   123.8  SIGMA=   1.6  PHAS=   -85.3  FOM=  0.90  TEST= 0
INDE  15  43  36  FOBS=    29.4  SIGMA=   6.6  PHAS=   121.1  FOM=  0.30  TEST= 0
INDE  15  43  38  FOBS=    56.0  SIGMA=   3.9  PHAS=   177.7  FOM=  0.84  TEST= 0
INDE  15  43  40  FOBS=    36.8  SIGMA=   5.2  PHAS=  -113.3  FOM=  0.36  TEST= 0
INDE  15  43  42  FOBS=    87.4  SIGMA=   2.7  PHAS=    55.6  FOM=  0.92  TEST= 0
INDE  15  43  44  FOBS=     0.0  SIGMA=  24.5  PHAS=     0.0  FOM=  0.00  TEST= 0
INDE  15  43  46  FOBS=     0.0  SIGMA=  21.1  PHAS=     0.0  FOM=  0.00  TEST= 1
INDE  15  43  48  FOBS=    63.4  SIGMA=   3.5  PHAS=   -46.6  FOM=  0.88  TEST= 0
INDE  15  43  50  FOBS=    62.1  SIGMA=   3.6  PHAS=    52.8  FOM=  0.56  TEST= 1
INDE  15  43  52  FOBS=    50.4  SIGMA=   4.4  PHAS=   130.4  FOM=  0.58  TEST= 0
INDE  15  43  54  FOBS=    36.8  SIGMA=   6.0  PHAS=    62.1  FOM=  0.52  TEST= 0
INDE  15  43  56  FOBS=    39.7  SIGMA=   5.4  PHAS=    68.5  FOM=  0.40  TEST= 0
INDE  15  43  58  FOBS=    86.6  SIGMA=   2.6  PHAS=   -48.7  FOM=  0.93  TEST= 0
INDE  15  43  60  FOBS=    45.1  SIGMA=   5.4  PHAS=     0.1  FOM=  0.43  TEST= 0
INDE  15  43  62  FOBS=     0.0  SIGMA=  25.8  PHAS=     0.0  FOM=  0.00  TEST= 0
```

*FIG. 12A - 369*

```
INDE  15  44  15  FOBS=   228.1  SIGMA=   1.1  PHAS=  -148.5  FOM=  0.98  TEST= 0
INDE  15  44  17  FOBS=   261.1  SIGMA=   1.0  PHAS=  -127.1  FOM=  0.95  TEST= 0
INDE  15  44  19  FOBS=   265.2  SIGMA=   1.0  PHAS=  -143.0  FOM=  0.97  TEST= 0
INDE  15  44  21  FOBS=    23.0  SIGMA=   9.2  PHAS=    76.8  FOM=  0.07  TEST= 1
INDE  15  44  23  FOBS=    95.4  SIGMA=   2.3  PHAS=    31.0  FOM=  0.45  TEST= 0
INDE  15  44  25  FOBS=    67.6  SIGMA=   3.2  PHAS=     2.9  FOM=  0.73  TEST= 0
INDE  15  44  27  FOBS=    88.6  SIGMA=   2.5  PHAS=    -7.5  FOM=  0.61  TEST= 0
INDE  15  44  29  FOBS=   151.1  SIGMA=   1.5  PHAS=   -34.5  FOM=  0.94  TEST= 0
INDE  15  44  31  FOBS=    71.5  SIGMA=   2.7  PHAS=   152.9  FOM=  0.73  TEST= 0
INDE  15  44  33  FOBS=   187.7  SIGMA=   1.1  PHAS=   161.0  FOM=  0.95  TEST= 0
INDE  15  44  35  FOBS=     0.0  SIGMA=  20.8  PHAS=     0.0  FOM=  0.00  TEST= 0
INDE  15  44  37  FOBS=    61.0  SIGMA=   2.9  PHAS=   165.4  FOM=  0.75  TEST= 0
INDE  15  44  39  FOBS=     0.0  SIGMA=  22.4  PHAS=     0.0  FOM=  0.00  TEST= 0
INDE  15  44  41  FOBS=    40.7  SIGMA=   4.7  PHAS=  -114.9  FOM=  0.62  TEST= 0
INDE  15  44  43  FOBS=     0.0  SIGMA=  21.3  PHAS=     0.0  FOM=  0.00  TEST= 0
INDE  15  44  45  FOBS=    35.0  SIGMA=   7.2  PHAS=  -110.8  FOM=  0.65  TEST= 0
INDE  15  44  47  FOBS=    72.8  SIGMA=   3.1  PHAS=  -150.9  FOM=  0.83  TEST= 0
INDE  15  44  49  FOBS=     0.0  SIGMA=  21.8  PHAS=     0.0  FOM=  0.00  TEST= 0
INDE  15  44  51  FOBS=    50.6  SIGMA=   4.4  PHAS=   -99.3  FOM=  0.79  TEST= 0
INDE  15  44  53  FOBS=    46.7  SIGMA=   4.8  PHAS=  -112.5  FOM=  0.26  TEST= 0
INDE  15  44  55  FOBS=    42.9  SIGMA=   5.2  PHAS=   103.0  FOM=  0.86  TEST= 0
INDE  15  44  57  FOBS=   102.0  SIGMA=   2.2  PHAS=   174.0  FOM=  0.27  TEST= 1
INDE  15  44  59  FOBS=    29.4  SIGMA=   9.1  PHAS=   -89.5  FOM=  0.33  TEST= 0
INDE  15  44  61  FOBS=    92.6  SIGMA=   3.1  PHAS=    12.9  FOM=  0.07  TEST= 1
INDE  15  45  16  FOBS=   339.8  SIGMA=   0.8  PHAS=    98.8  FOM=  0.98  TEST= 0
INDE  15  45  18  FOBS=   213.9  SIGMA=   1.2  PHAS=   146.3  FOM=  0.96  TEST= 0
INDE  15  45  20  FOBS=    12.6  SIGMA=  20.4  PHAS=    85.0  FOM=  0.01  TEST= 1
INDE  15  45  22  FOBS=    12.8  SIGMA=  20.1  PHAS=    51.5  FOM=  0.12  TEST= 0
INDE  15  45  24  FOBS=   206.0  SIGMA=   1.1  PHAS=  -132.8  FOM=  0.97  TEST= 0
INDE  15  45  26  FOBS=   116.7  SIGMA=   1.9  PHAS=   150.1  FOM=  0.80  TEST= 0
INDE  15  45  28  FOBS=   108.3  SIGMA=   2.0  PHAS=  -142.3  FOM=  0.61  TEST= 0
INDE  15  45  30  FOBS=   243.3  SIGMA=   1.0  PHAS=  -154.7  FOM=  0.93  TEST= 0
INDE  15  45  32  FOBS=   144.8  SIGMA=   1.4  PHAS=    51.2  FOM=  0.93  TEST= 0
INDE  15  45  34  FOBS=   101.8  SIGMA=   1.9  PHAS=  -101.3  FOM=  0.96  TEST= 0
INDE  15  45  36  FOBS=    95.1  SIGMA=   2.0  PHAS=    77.6  FOM=  0.86  TEST= 0
INDE  15  45  38  FOBS=    55.5  SIGMA=   3.1  PHAS=   109.1  FOM=  0.62  TEST= 0
INDE  15  45  40  FOBS=    58.7  SIGMA=   3.3  PHAS=   141.5  FOM=  0.87  TEST= 0
INDE  15  45  42  FOBS=    54.6  SIGMA=   3.5  PHAS=    -1.8  FOM=  0.81  TEST= 0
INDE  15  45  44  FOBS=   104.0  SIGMA=   2.3  PHAS=   154.9  FOM=  0.90  TEST= 0
INDE  15  45  46  FOBS=    29.8  SIGMA=   8.3  PHAS=   173.8  FOM=  0.27  TEST= 0
INDE  15  45  48  FOBS=     0.0  SIGMA=  21.1  PHAS=     0.0  FOM=  0.00  TEST= 0
INDE  15  45  50  FOBS=    75.1  SIGMA=   3.0  PHAS=   124.1  FOM=  0.79  TEST= 0
INDE  15  45  52  FOBS=     0.0  SIGMA=  20.8  PHAS=     0.0  FOM=  0.00  TEST= 0
INDE  15  45  54  FOBS=     0.0  SIGMA=  23.6  PHAS=     0.0  FOM=  0.00  TEST= 0
INDE  15  45  56  FOBS=    53.2  SIGMA=   4.2  PHAS=    99.9  FOM=  0.86  TEST= 0
INDE  15  45  58  FOBS=    35.2  SIGMA=   6.3  PHAS=   -22.8  FOM=  0.59  TEST= 0
INDE  15  45  60  FOBS=    36.3  SIGMA=   7.7  PHAS=  -109.9  FOM=  0.66  TEST= 0
INDE  15  46  15  FOBS=   244.6  SIGMA=   1.3  PHAS=    45.5  FOM=  0.97  TEST= 0
INDE  15  46  17  FOBS=   288.3  SIGMA=   0.9  PHAS=    19.2  FOM=  0.96  TEST= 0
INDE  15  46  19  FOBS=   106.0  SIGMA=   2.0  PHAS=  -125.4  FOM=  0.94  TEST= 0
INDE  15  46  21  FOBS=     0.0  SIGMA=  20.5  PHAS=     0.0  FOM=  0.00  TEST= 0
INDE  15  46  23  FOBS=   116.5  SIGMA=   1.9  PHAS=   121.1  FOM=  0.96  TEST= 0
INDE  15  46  25  FOBS=   153.1  SIGMA=   1.5  PHAS=    72.6  FOM=  0.94  TEST= 0
INDE  15  46  27  FOBS=   128.2  SIGMA=   1.7  PHAS=    50.2  FOM=  0.76  TEST= 1
INDE  15  46  29  FOBS=   231.5  SIGMA=   1.1  PHAS=  -137.2  FOM=  0.94  TEST= 0
INDE  15  46  31  FOBS=    50.9  SIGMA=   4.2  PHAS=    11.3  FOM=  0.81  TEST= 0
INDE  15  46  33  FOBS=    37.1  SIGMA=   5.1  PHAS=  -112.7  FOM=  0.51  TEST= 0
INDE  15  46  35  FOBS=   105.3  SIGMA=   1.9  PHAS=  -171.3  FOM=  0.86  TEST= 0
INDE  15  46  37  FOBS=   111.6  SIGMA=   1.8  PHAS=    30.4  FOM=  0.82  TEST= 0
INDE  15  46  39  FOBS=   110.4  SIGMA=   1.6  PHAS=   -28.7  FOM=  0.90  TEST= 0
INDE  15  46  41  FOBS=    96.3  SIGMA=   2.1  PHAS=  -169.0  FOM=  0.67  TEST= 0
INDE  15  46  43  FOBS=   120.4  SIGMA=   1.7  PHAS=    92.9  FOM=  0.41  TEST= 1
INDE  15  46  45  FOBS=     0.0  SIGMA=  22.2  PHAS=     0.0  FOM=  0.00  TEST= 0
INDE  15  46  47  FOBS=    60.5  SIGMA=   3.7  PHAS=   -96.6  FOM=  0.65  TEST= 0
INDE  15  46  49  FOBS=     0.0  SIGMA=  21.0  PHAS=     0.0  FOM=  0.00  TEST= 0
INDE  15  46  51  FOBS=     0.0  SIGMA=  23.2  PHAS=     0.0  FOM=  0.00  TEST= 0
INDE  15  46  53  FOBS=    42.6  SIGMA=   5.2  PHAS=   174.8  FOM=  0.40  TEST= 0
INDE  15  46  55  FOBS=    71.5  SIGMA=   3.2  PHAS=    95.8  FOM=  0.89  TEST= 0
INDE  15  46  57  FOBS=    42.6  SIGMA=   5.2  PHAS=  -105.7  FOM=  0.78  TEST= 0
INDE  15  46  59  FOBS=     0.0  SIGMA=  23.4  PHAS=     0.0  FOM=  0.00  TEST= 0
```

*FIG. 12A - 370*

```
INDE  15  47  16  FOBS=   49.9  SIGMA=   4.7  PHAS=  118.6  FOM=  0.17  TEST= 1
INDE  15  47  18  FOBS=    0.0  SIGMA=  20.4  PHAS=    0.0  FOM=  0.00  TEST= 0
INDE  15  47  20  FOBS=    0.0  SIGMA=  22.2  PHAS=    0.0  FOM=  0.00  TEST= 1
INDE  15  47  22  FOBS=   87.0  SIGMA=   2.4  PHAS=   65.0  FOM=  0.96  TEST= 0
INDE  15  47  24  FOBS=    0.0  SIGMA=  22.3  PHAS=    0.0  FOM=  0.00  TEST= 0
INDE  15  47  26  FOBS=   48.7  SIGMA=   4.3  PHAS=  -47.7  FOM=  0.65  TEST= 0
INDE  15  47  28  FOBS=   55.2  SIGMA=   3.8  PHAS=  108.5  FOM=  0.74  TEST= 1
INDE  15  47  30  FOBS=   43.5  SIGMA=   4.9  PHAS=  151.6  FOM=  0.55  TEST= 0
INDE  15  47  32  FOBS=   26.4  SIGMA=   8.0  PHAS=  -20.5  FOM=  0.03  TEST= 1
INDE  15  47  34  FOBS=  106.8  SIGMA=   1.8  PHAS=  130.6  FOM=  0.35  TEST= 1
INDE  15  47  36  FOBS=   27.9  SIGMA=   6.8  PHAS=  -46.9  FOM=  0.14  TEST= 0
INDE  15  47  38  FOBS=  121.0  SIGMA=   1.5  PHAS=  -69.9  FOM=  0.84  TEST= 1
INDE  15  47  40  FOBS=  133.8  SIGMA=   1.4  PHAS=  148.0  FOM=  0.96  TEST= 0
INDE  15  47  42  FOBS=  107.9  SIGMA=   1.8  PHAS=    7.3  FOM=  0.91  TEST= 0
INDE  15  47  44  FOBS=   74.5  SIGMA=   2.6  PHAS=   95.4  FOM=  0.63  TEST= 0
INDE  15  47  46  FOBS=    0.0  SIGMA=  21.9  PHAS=    0.0  FOM=  0.00  TEST= 0
INDE  15  47  48  FOBS=   70.8  SIGMA=   3.2  PHAS=  167.1  FOM=  0.91  TEST= 0
INDE  15  47  50  FOBS=   38.9  SIGMA=   5.8  PHAS=   22.6  FOM=  0.34  TEST= 0
INDE  15  47  52  FOBS=   14.1  SIGMA=  21.7  PHAS=   25.9  FOM=  0.12  TEST= 0
INDE  15  47  54  FOBS=   30.3  SIGMA=   7.4  PHAS=  -37.6  FOM=  0.47  TEST= 0
INDE  15  47  56  FOBS=    0.0  SIGMA=  23.4  PHAS=    0.0  FOM=  0.00  TEST= 0
INDE  15  47  58  FOBS=   41.1  SIGMA=   7.6  PHAS=  140.8  FOM=  0.61  TEST= 0
INDE  15  47  60  FOBS=   98.1  SIGMA=   3.0  PHAS= -135.6  FOM=  0.86  TEST= 0
INDE  15  48  15  FOBS=  161.4  SIGMA=   1.8  PHAS=   30.0  FOM=  0.92  TEST= 0
INDE  15  48  17  FOBS=   73.8  SIGMA=   2.8  PHAS=  -36.8  FOM=  0.75  TEST= 1
INDE  15  48  19  FOBS=   14.8  SIGMA=  15.1  PHAS=   46.0  FOM=  0.12  TEST= 0
INDE  15  48  21  FOBS=   94.8  SIGMA=   2.2  PHAS= -118.4  FOM=  0.77  TEST= 0
INDE  15  48  23  FOBS=   28.6  SIGMA=   7.2  PHAS=  122.5  FOM=  0.37  TEST= 0
INDE  15  48  25  FOBS=  137.6  SIGMA=   1.6  PHAS=  109.6  FOM=  0.89  TEST= 0
INDE  15  48  27  FOBS=  109.7  SIGMA=   2.0  PHAS=  -71.0  FOM=  0.84  TEST= 0
INDE  15  48  29  FOBS=  184.5  SIGMA=   1.3  PHAS=  173.4  FOM=  0.90  TEST= 0
INDE  15  48  31  FOBS=   54.4  SIGMA=   3.9  PHAS=   19.4  FOM=  0.83  TEST= 0
INDE  15  48  33  FOBS=    0.0  SIGMA=  19.4  PHAS=    0.0  FOM=  0.00  TEST= 0
INDE  15  48  35  FOBS=  159.0  SIGMA=   1.3  PHAS=  170.0  FOM=  0.93  TEST= 0
INDE  15  48  37  FOBS=   46.6  SIGMA=   4.0  PHAS= -154.6  FOM=  0.64  TEST= 1
INDE  15  48  39  FOBS=   33.6  SIGMA=   5.1  PHAS=  -42.8  FOM=  0.64  TEST= 0
INDE  15  48  41  FOBS=   35.2  SIGMA=   5.6  PHAS=  -37.7  FOM=  0.54  TEST= 0
INDE  15  48  43  FOBS=  142.7  SIGMA=   1.4  PHAS=   -4.3  FOM=  0.94  TEST= 0
INDE  15  48  45  FOBS=   62.5  SIGMA=   3.1  PHAS=  -51.3  FOM=  0.88  TEST= 0
INDE  15  48  47  FOBS=    0.0  SIGMA=  22.2  PHAS=    0.0  FOM=  0.00  TEST= 0
INDE  15  48  49  FOBS=   32.9  SIGMA=   6.9  PHAS= -135.8  FOM=  0.34  TEST= 0
INDE  15  48  51  FOBS=    0.0  SIGMA=  21.9  PHAS=    0.0  FOM=  0.00  TEST= 0
INDE  15  48  53  FOBS=    6.1  SIGMA=  36.7  PHAS=   -9.6  FOM=  0.09  TEST= 0
INDE  15  48  55  FOBS=    0.0  SIGMA=  22.0  PHAS=    0.0  FOM=  0.00  TEST= 0
INDE  15  48  57  FOBS=    0.0  SIGMA=  25.9  PHAS=    0.0  FOM=  0.00  TEST= 0
INDE  15  48  59  FOBS=   14.1  SIGMA=  19.9  PHAS=  104.6  FOM=  0.24  TEST= 0
INDE  15  49  16  FOBS=  169.9  SIGMA=   1.7  PHAS= -154.6  FOM=  0.96  TEST= 0
INDE  15  49  18  FOBS=  126.7  SIGMA=   1.7  PHAS=   -7.7  FOM=  0.89  TEST= 0
INDE  15  49  20  FOBS=   56.6  SIGMA=   3.6  PHAS=   57.2  FOM=  0.07  TEST= 0
INDE  15  49  22  FOBS=   60.2  SIGMA=   3.4  PHAS=   86.2  FOM=  0.49  TEST= 0
INDE  15  49  24  FOBS=  180.5  SIGMA=   1.3  PHAS=   64.3  FOM=  0.97  TEST= 0
INDE  15  49  26  FOBS=  119.0  SIGMA=   1.8  PHAS=  118.1  FOM=  0.97  TEST= 0
INDE  15  49  28  FOBS=   79.4  SIGMA=   2.7  PHAS=  117.6  FOM=  0.75  TEST= 1
INDE  15  49  30  FOBS=   27.5  SIGMA=   7.5  PHAS=  -84.3  FOM=  0.09  TEST= 1
INDE  15  49  32  FOBS=    0.0  SIGMA=  20.4  PHAS=    0.0  FOM=  0.00  TEST= 0
INDE  15  49  34  FOBS=   77.8  SIGMA=   2.4  PHAS=   -4.4  FOM=  0.92  TEST= 0
INDE  15  49  36  FOBS=  116.0  SIGMA=   1.7  PHAS=  149.4  FOM=  0.96  TEST= 0
INDE  15  49  38  FOBS=   60.4  SIGMA=   3.1  PHAS=   59.0  FOM=  0.76  TEST= 0
INDE  15  49  40  FOBS=   67.2  SIGMA=   2.6  PHAS=  157.0  FOM=  0.80  TEST= 0
INDE  15  49  42  FOBS=  104.9  SIGMA=   1.7  PHAS= -154.0  FOM=  0.01  TEST= 1
INDE  15  49  44  FOBS=   48.2  SIGMA=   4.2  PHAS= -158.4  FOM=  0.73  TEST= 0
INDE  15  49  46  FOBS=   53.5  SIGMA=   3.6  PHAS= -153.2  FOM=  0.82  TEST= 0
INDE  15  49  48  FOBS=   88.7  SIGMA=   2.6  PHAS=  145.2  FOM=  0.91  TEST= 0
INDE  15  49  50  FOBS=    0.0  SIGMA=  21.3  PHAS=    0.0  FOM=  0.00  TEST= 0
INDE  15  49  52  FOBS=    0.0  SIGMA=  22.1  PHAS=    0.0  FOM=  0.00  TEST= 1
INDE  15  49  54  FOBS=   61.1  SIGMA=   3.7  PHAS= -102.3  FOM=  0.58  TEST= 0
INDE  15  49  56  FOBS=   87.9  SIGMA=   3.3  PHAS= -119.3  FOM=  0.15  TEST= 1
INDE  15  49  58  FOBS=   54.1  SIGMA=   5.3  PHAS= -178.2  FOM=  0.74  TEST= 0
INDE  15  50  15  FOBS=  303.0  SIGMA=   1.1  PHAS=   93.2  FOM=  0.88  TEST= 1
INDE  15  50  17  FOBS=  177.8  SIGMA=   1.2  PHAS= -139.8  FOM=  0.93  TEST= 0
```

*FIG. 12A - 371*

```
INDE 15 50 19 FOBS=    152.0 SIGMA=  1.4 PHAS= -105.9 FOM= 0.23 TEST= 1
INDE 15 50 21 FOBS=     46.1 SIGMA=  4.7 PHAS=  -66.7 FOM= 0.53 TEST= 0
INDE 15 50 23 FOBS=    128.7 SIGMA=  1.7 PHAS=   23.7 FOM= 0.84 TEST= 0
INDE 15 50 25 FOBS=     46.2 SIGMA=  4.5 PHAS=    6.2 FOM= 0.83 TEST= 0
INDE 15 50 27 FOBS=     11.4 SIGMA= 18.1 PHAS=   -6.4 FOM= 0.25 TEST= 0
INDE 15 50 29 FOBS=     72.4 SIGMA=  2.9 PHAS=   62.3 FOM= 0.47 TEST= 0
INDE 15 50 31 FOBS=    101.1 SIGMA=  2.1 PHAS=   60.8 FOM= 0.96 TEST= 0
INDE 15 50 33 FOBS=     63.0 SIGMA=  3.4 PHAS= -172.9 FOM= 0.86 TEST= 0
INDE 15 50 35 FOBS=     42.3 SIGMA=  4.4 PHAS=   74.8 FOM= 0.84 TEST= 0
INDE 15 50 37 FOBS=    123.2 SIGMA=  1.6 PHAS=   73.6 FOM= 0.40 TEST= 1
INDE 15 50 39 FOBS=     94.0 SIGMA=  2.1 PHAS=   68.6 FOM= 0.92 TEST= 0
INDE 15 50 41 FOBS=     36.0 SIGMA=  4.9 PHAS=  -22.3 FOM= 0.62 TEST= 0
INDE 15 50 43 FOBS=      0.0 SIGMA= 18.8 PHAS=    0.0 FOM= 0.00 TEST= 1
INDE 15 50 45 FOBS=      0.0 SIGMA= 19.9 PHAS=    0.0 FOM= 0.00 TEST= 1
INDE 15 50 47 FOBS=     51.6 SIGMA=  3.7 PHAS=  123.4 FOM= 0.77 TEST= 0
INDE 15 50 49 FOBS=     50.3 SIGMA=  4.6 PHAS=    8.6 FOM= 0.71 TEST= 0
INDE 15 50 51 FOBS=     53.0 SIGMA=  4.3 PHAS=   23.7 FOM= 0.72 TEST= 0
INDE 15 50 53 FOBS=      0.0 SIGMA= 21.9 PHAS=    0.0 FOM= 0.00 TEST= 0
INDE 15 50 55 FOBS=     88.8 SIGMA=  3.2 PHAS=   91.7 FOM= 0.73 TEST= 0
INDE 15 50 57 FOBS=     32.1 SIGMA= 10.1 PHAS=  119.0 FOM= 0.67 TEST= 0
INDE 15 51 16 FOBS=    135.9 SIGMA=  2.1 PHAS=   23.8 FOM= 0.77 TEST= 1
INDE 15 51 18 FOBS=     38.8 SIGMA=  5.2 PHAS=  148.2 FOM= 0.37 TEST= 1
INDE 15 51 20 FOBS=     36.1 SIGMA=  6.5 PHAS= -124.2 FOM= 0.16 TEST= 0
INDE 15 51 22 FOBS=      0.0 SIGMA= 20.1 PHAS=    0.0 FOM= 0.00 TEST= 0
INDE 15 51 24 FOBS=      0.0 SIGMA= 20.2 PHAS=    0.0 FOM= 0.00 TEST= 0
INDE 15 51 26 FOBS=     28.2 SIGMA=  7.4 PHAS=  -24.8 FOM= 0.15 TEST= 0
INDE 15 51 28 FOBS=    136.9 SIGMA=  1.6 PHAS= -117.7 FOM= 0.91 TEST= 0
INDE 15 51 30 FOBS=     22.7 SIGMA= 11.0 PHAS=  167.4 FOM= 0.16 TEST= 0
INDE 15 51 32 FOBS=    117.6 SIGMA=  1.8 PHAS=   86.4 FOM= 0.92 TEST= 0
INDE 15 51 34 FOBS=     61.7 SIGMA=  3.4 PHAS=   19.0 FOM= 0.85 TEST= 0
INDE 15 51 36 FOBS=      0.0 SIGMA= 19.7 PHAS=    0.0 FOM= 0.00 TEST= 0
INDE 15 51 38 FOBS=    121.0 SIGMA=  1.6 PHAS=   28.5 FOM= 0.94 TEST= 0
INDE 15 51 40 FOBS=     66.9 SIGMA=  2.7 PHAS=  -79.9 FOM= 0.89 TEST= 0
INDE 15 51 42 FOBS=     24.6 SIGMA=  7.0 PHAS=  155.3 FOM= 0.55 TEST= 0
INDE 15 51 44 FOBS=     37.0 SIGMA=  4.6 PHAS=  137.2 FOM= 0.61 TEST= 0
INDE 15 51 46 FOBS=     46.2 SIGMA=  4.2 PHAS=  134.5 FOM= 0.79 TEST= 0
INDE 15 51 48 FOBS=     53.0 SIGMA=  4.0 PHAS=  103.4 FOM= 0.46 TEST= 0
INDE 15 51 50 FOBS=      0.0 SIGMA= 22.0 PHAS=    0.0 FOM= 0.00 TEST= 0
INDE 15 51 52 FOBS=     31.3 SIGMA= 10.4 PHAS=   34.6 FOM= 0.66 TEST= 0
INDE 15 51 54 FOBS=     18.0 SIGMA= 18.8 PHAS=  -46.9 FOM= 0.38 TEST= 0
INDE 15 51 56 FOBS=     95.1 SIGMA=  3.1 PHAS=  -48.4 FOM= 0.90 TEST= 0
INDE 15 52 15 FOBS=     26.2 SIGMA= 10.0 PHAS= -156.4 FOM= 0.22 TEST= 0
INDE 15 52 17 FOBS=     32.0 SIGMA= 11.3 PHAS=  -93.2 FOM= 0.45 TEST= 0
INDE 15 52 19 FOBS=    143.5 SIGMA=  1.5 PHAS= -166.8 FOM= 0.93 TEST= 0
INDE 15 52 21 FOBS=    118.3 SIGMA=  1.8 PHAS=  110.5 FOM= 0.61 TEST= 0
INDE 15 52 23 FOBS=    117.1 SIGMA=  1.8 PHAS=   55.2 FOM= 0.83 TEST= 0
INDE 15 52 25 FOBS=     98.3 SIGMA=  2.2 PHAS= -100.7 FOM= 0.93 TEST= 0
INDE 15 52 27 FOBS=      0.0 SIGMA= 22.1 PHAS=    0.0 FOM= 0.00 TEST= 0
INDE 15 52 29 FOBS=     50.6 SIGMA=  4.1 PHAS= -152.1 FOM= 0.70 TEST= 0
INDE 15 52 31 FOBS=     75.5 SIGMA=  2.8 PHAS=   61.8 FOM= 0.82 TEST= 1
INDE 15 52 33 FOBS=     40.5 SIGMA=  5.1 PHAS=  -29.1 FOM= 0.26 TEST= 0
INDE 15 52 35 FOBS=     56.3 SIGMA=  3.3 PHAS=  -81.9 FOM= 0.60 TEST= 0
INDE 15 52 37 FOBS=     65.9 SIGMA=  2.8 PHAS=   -4.7 FOM= 0.74 TEST= 0
INDE 15 52 39 FOBS=     47.0 SIGMA=  4.0 PHAS= -168.6 FOM= 0.52 TEST= 0
INDE 15 52 41 FOBS=     54.8 SIGMA=  3.1 PHAS=   33.3 FOM= 0.73 TEST= 0
INDE 15 52 43 FOBS=     66.5 SIGMA=  2.6 PHAS=   69.7 FOM= 0.66 TEST= 0
INDE 15 52 45 FOBS=      0.0 SIGMA= 18.9 PHAS=    0.0 FOM= 0.00 TEST= 0
INDE 15 52 47 FOBS=     50.9 SIGMA=  3.8 PHAS= -150.3 FOM= 0.11 TEST= 0
INDE 15 52 49 FOBS=     71.4 SIGMA=  3.0 PHAS=  -51.6 FOM= 0.90 TEST= 0
INDE 15 52 51 FOBS=     53.2 SIGMA=  4.4 PHAS=   -8.7 FOM= 0.82 TEST= 0
INDE 15 52 53 FOBS=     41.1 SIGMA=  8.5 PHAS=   -1.4 FOM= 0.25 TEST= 1
INDE 15 52 55 FOBS=      0.0 SIGMA= 26.2 PHAS=    0.0 FOM= 0.00 TEST= 0
INDE 15 53 16 FOBS=    157.5 SIGMA=  1.8 PHAS=   46.7 FOM= 0.92 TEST= 0
INDE 15 53 18 FOBS=     51.6 SIGMA=  5.1 PHAS= -134.9 FOM= 0.40 TEST= 0
INDE 15 53 20 FOBS=    162.5 SIGMA=  1.3 PHAS=  110.0 FOM= 0.97 TEST= 0
INDE 15 53 22 FOBS=    162.8 SIGMA=  1.3 PHAS=   82.2 FOM= 0.34 TEST= 1
INDE 15 53 24 FOBS=      0.0 SIGMA= 20.2 PHAS=    0.0 FOM= 0.00 TEST= 0
INDE 15 53 26 FOBS=    119.9 SIGMA=  1.8 PHAS= -166.7 FOM= 0.95 TEST= 0
INDE 15 53 28 FOBS=    136.7 SIGMA=  1.6 PHAS=  162.0 FOM= 0.94 TEST= 0
INDE 15 53 30 FOBS=      0.0 SIGMA= 20.1 PHAS=    0.0 FOM= 0.00 TEST= 0
```

*FIG. 12A - 372*

```
INDE  15  53  32  FOBS=   36.4  SIGMA=   5.6  PHAS=  -124.6  FOM=  0.56  TEST=  0
INDE  15  53  34  FOBS=   19.4  SIGMA=  11.7  PHAS=    62.9  FOM=  0.07  TEST=  1
INDE  15  53  36  FOBS=   38.4  SIGMA=   4.7  PHAS=   127.3  FOM=  0.41  TEST=  0
INDE  15  53  38  FOBS=   88.7  SIGMA=   2.1  PHAS=   148.6  FOM=  0.91  TEST=  0
INDE  15  53  40  FOBS=   63.6  SIGMA=   3.0  PHAS=   -96.2  FOM=  0.51  TEST=  1
INDE  15  53  42  FOBS=   44.1  SIGMA=   4.4  PHAS=   -73.6  FOM=  0.27  TEST=  0
INDE  15  53  44  FOBS=   47.3  SIGMA=   3.7  PHAS=    80.7  FOM=  0.49  TEST=  0
INDE  15  53  46  FOBS=    0.0  SIGMA=  19.6  PHAS=     0.0  FOM=  0.00  TEST=  0
INDE  15  53  48  FOBS=    0.0  SIGMA=  21.8  PHAS=     0.0  FOM=  0.00  TEST=  0
INDE  15  53  50  FOBS=   52.9  SIGMA=   4.8  PHAS=    12.0  FOM=  0.08  TEST=  1
INDE  15  53  52  FOBS=   63.3  SIGMA=   5.6  PHAS=   -85.3  FOM=  0.86  TEST=  0
INDE  15  53  54  FOBS=   21.9  SIGMA=  20.6  PHAS=   -99.5  FOM=  0.46  TEST=  0
INDE  15  54  15  FOBS=  154.7  SIGMA=   1.8  PHAS=  -139.1  FOM=  0.85  TEST=  0
INDE  15  54  17  FOBS=  104.3  SIGMA=   2.6  PHAS=     4.4  FOM=  0.75  TEST=  1
INDE  15  54  19  FOBS=  117.7  SIGMA=   1.8  PHAS=   -37.9  FOM=  0.80  TEST=  0
INDE  15  54  21  FOBS=  117.8  SIGMA=   1.8  PHAS=    48.5  FOM=  0.50  TEST=  1
INDE  15  54  23  FOBS=   69.9  SIGMA=   2.9  PHAS=    13.9  FOM=  0.52  TEST=  0
INDE  15  54  25  FOBS=   74.5  SIGMA=   2.8  PHAS=   142.9  FOM=  0.76  TEST=  0
INDE  15  54  27  FOBS=  114.1  SIGMA=   1.8  PHAS=    73.1  FOM=  0.91  TEST=  0
INDE  15  54  29  FOBS=    0.0  SIGMA=  20.1  PHAS=     0.0  FOM=  0.00  TEST=  0
INDE  15  54  31  FOBS=    0.0  SIGMA=  22.0  PHAS=     0.0  FOM=  0.00  TEST=  0
INDE  15  54  33  FOBS=   70.5  SIGMA=   3.0  PHAS=   141.4  FOM=  0.56  TEST=  0
INDE  15  54  35  FOBS=   49.9  SIGMA=   4.2  PHAS=   -23.4  FOM=  0.34  TEST=  0
INDE  15  54  37  FOBS=  111.3  SIGMA=   1.7  PHAS=    43.9  FOM=  0.94  TEST=  0
INDE  15  54  39  FOBS=   31.2  SIGMA=   6.7  PHAS=    55.9  FOM=  0.34  TEST=  0
INDE  15  54  41  FOBS=   80.1  SIGMA=   2.4  PHAS=  -131.7  FOM=  0.80  TEST=  0
INDE  15  54  43  FOBS=   79.2  SIGMA=   2.2  PHAS=   103.6  FOM=  0.87  TEST=  0
INDE  15  54  45  FOBS=   55.0  SIGMA=   3.4  PHAS=    31.7  FOM=  0.02  TEST=  1
INDE  15  54  47  FOBS=    0.0  SIGMA=  21.9  PHAS=     0.0  FOM=  0.00  TEST=  0
INDE  15  54  49  FOBS=    0.0  SIGMA=  23.3  PHAS=     0.0  FOM=  0.00  TEST=  0
INDE  15  54  51  FOBS=    0.0  SIGMA=  26.6  PHAS=     0.0  FOM=  0.00  TEST=  1
INDE  15  54  53  FOBS=   43.4  SIGMA=  10.7  PHAS=   154.4  FOM=  0.62  TEST=  0
INDE  15  55  16  FOBS=   19.9  SIGMA=  15.0  PHAS=   100.2  FOM=  0.17  TEST=  0
INDE  15  55  18  FOBS=   76.9  SIGMA=   3.3  PHAS=   -70.1  FOM=  0.75  TEST=  0
INDE  15  55  20  FOBS=  195.2  SIGMA=   1.2  PHAS=   151.8  FOM=  0.96  TEST=  0
INDE  15  55  22  FOBS=   70.0  SIGMA=   3.1  PHAS=  -121.8  FOM=  0.07  TEST=  1
INDE  15  55  24  FOBS=  113.3  SIGMA=   1.9  PHAS=   -10.4  FOM=  0.90  TEST=  0
INDE  15  55  26  FOBS=   76.7  SIGMA=   2.7  PHAS=  -145.8  FOM=  0.88  TEST=  0
INDE  15  55  28  FOBS=   56.6  SIGMA=   3.5  PHAS=   176.7  FOM=  0.14  TEST=  1
INDE  15  55  30  FOBS=   64.4  SIGMA=   3.2  PHAS=   171.1  FOM=  0.45  TEST=  0
INDE  15  55  32  FOBS=   46.3  SIGMA=   4.4  PHAS=   -65.5  FOM=  0.69  TEST=  0
INDE  15  55  34  FOBS=   85.4  SIGMA=   2.5  PHAS=   127.1  FOM=  0.87  TEST=  0
INDE  15  55  36  FOBS=   12.0  SIGMA=  17.3  PHAS=   -34.1  FOM=  0.43  TEST=  0
INDE  15  55  38  FOBS=   46.2  SIGMA=   4.0  PHAS=  -107.4  FOM=  0.74  TEST=  0
INDE  15  55  40  FOBS=   90.1  SIGMA=   2.3  PHAS=   144.7  FOM=  0.87  TEST=  0
INDE  15  55  42  FOBS=   57.7  SIGMA=   3.2  PHAS=   -36.6  FOM=  0.73  TEST=  0
INDE  15  55  44  FOBS=  126.9  SIGMA=   1.7  PHAS=    11.9  FOM=  0.96  TEST=  0
INDE  15  55  46  FOBS=    0.0  SIGMA=  20.0  PHAS=     0.0  FOM=  0.00  TEST=  0
INDE  15  55  48  FOBS=    0.0  SIGMA=  22.9  PHAS=     0.0  FOM=  0.00  TEST=  0
INDE  15  55  50  FOBS=    0.0  SIGMA=  26.6  PHAS=     0.0  FOM=  0.00  TEST=  0
INDE  15  55  52  FOBS=   66.4  SIGMA=   5.6  PHAS=   -47.8  FOM=  0.88  TEST=  0
INDE  15  56  15  FOBS=   32.6  SIGMA=   6.3  PHAS=    84.5  FOM=  0.08  TEST=  1
INDE  15  56  17  FOBS=  152.3  SIGMA=   1.8  PHAS=   -10.2  FOM=  0.94  TEST=  0
INDE  15  56  19  FOBS=  155.3  SIGMA=   1.8  PHAS=     3.7  FOM=  0.94  TEST=  0
INDE  15  56  21  FOBS=  179.6  SIGMA=   1.2  PHAS=   118.1  FOM=  0.58  TEST=  1
INDE  15  56  23  FOBS=   93.2  SIGMA=   2.2  PHAS=  -112.1  FOM=  0.71  TEST=  0
INDE  15  56  25  FOBS=  115.9  SIGMA=   1.8  PHAS=  -178.3  FOM=  0.89  TEST=  0
INDE  15  56  27  FOBS=   92.2  SIGMA=   2.3  PHAS=   144.8  FOM=  0.94  TEST=  0
INDE  15  56  29  FOBS=   60.5  SIGMA=   3.4  PHAS=   105.6  FOM=  0.35  TEST=  0
INDE  15  56  31  FOBS=   69.2  SIGMA=   3.0  PHAS=     0.9  FOM=  0.12  TEST=  1
INDE  15  56  33  FOBS=   19.8  SIGMA=  10.2  PHAS=  -176.0  FOM=  0.24  TEST=  1
INDE  15  56  35  FOBS=   76.1  SIGMA=   3.1  PHAS=   -71.9  FOM=  0.87  TEST=  0
INDE  15  56  37  FOBS=   46.3  SIGMA=   4.6  PHAS=   177.8  FOM=  0.82  TEST=  0
INDE  15  56  39  FOBS=   73.3  SIGMA=   3.0  PHAS=     7.1  FOM=  0.93  TEST=  0
INDE  15  56  41  FOBS=   10.1  SIGMA=  24.1  PHAS=  -179.4  FOM=  0.01  TEST=  1
INDE  15  56  43  FOBS=   51.2  SIGMA=   3.9  PHAS=  -114.5  FOM=  0.83  TEST=  0
INDE  15  56  45  FOBS=   86.1  SIGMA=   2.4  PHAS=  -114.9  FOM=  0.90  TEST=  0
INDE  15  56  47  FOBS=   59.5  SIGMA=   3.8  PHAS=    31.2  FOM=  0.59  TEST=  0
INDE  15  56  49  FOBS=   54.9  SIGMA=   5.0  PHAS=   155.3  FOM=  0.36  TEST=  0
INDE  15  56  51  FOBS=   73.0  SIGMA=   5.0  PHAS=   174.3  FOM=  0.90  TEST=  0
```

*FIG. 12A - 373*

```
INDE  15  57  16  FOBS=   179.7  SIGMA=   1.6  PHAS=  -103.4  FOM=  0.95  TEST= 0
INDE  15  57  18  FOBS=   179.3  SIGMA=   1.6  PHAS=   -79.0  FOM=  0.96  TEST= 0
INDE  15  57  20  FOBS=   109.9  SIGMA=   2.4  PHAS=   -45.6  FOM=  0.94  TEST= 0
INDE  15  57  22  FOBS=    21.3  SIGMA=   9.8  PHAS=   125.9  FOM=  0.49  TEST= 0
INDE  15  57  24  FOBS=    81.7  SIGMA=   2.5  PHAS=   111.2  FOM=  0.94  TEST= 0
INDE  15  57  26  FOBS=   141.3  SIGMA=   1.5  PHAS=   117.5  FOM=  0.94  TEST= 0
INDE  15  57  28  FOBS=    94.2  SIGMA=   2.2  PHAS=    51.4  FOM=  0.85  TEST= 0
INDE  15  57  30  FOBS=    68.9  SIGMA=   3.0  PHAS=   102.3  FOM=  0.80  TEST= 0
INDE  15  57  32  FOBS=     0.0  SIGMA=  21.1  PHAS=     0.0  FOM=  0.00  TEST= 0
INDE  15  57  34  FOBS=   107.5  SIGMA=   2.4  PHAS=   157.3  FOM=  0.90  TEST= 0
INDE  15  57  36  FOBS=    40.2  SIGMA=   6.3  PHAS=  -173.2  FOM=  0.08  TEST= 0
INDE  15  57  38  FOBS=    75.8  SIGMA=   2.9  PHAS=   -79.8  FOM=  0.83  TEST= 0
INDE  15  57  40  FOBS=    17.8  SIGMA=  12.2  PHAS=  -121.9  FOM=  0.43  TEST= 0
INDE  15  57  42  FOBS=    48.9  SIGMA=   5.0  PHAS=  -163.9  FOM=  0.82  TEST= 0
INDE  15  57  44  FOBS=   100.9  SIGMA=   2.1  PHAS=    29.6  FOM=  0.95  TEST= 0
INDE  15  57  46  FOBS=    94.4  SIGMA=   2.5  PHAS=   -93.9  FOM=  0.94  TEST= 0
INDE  15  57  48  FOBS=    57.6  SIGMA=   4.7  PHAS=    96.2  FOM=  0.15  TEST= 1
INDE  15  57  50  FOBS=    86.6  SIGMA=   3.3  PHAS=    71.2  FOM=  0.87  TEST= 0
INDE  15  58  15  FOBS=   109.3  SIGMA=   1.9  PHAS=  -156.0  FOM=  0.66  TEST= 0
INDE  15  58  17  FOBS=    79.5  SIGMA=   3.2  PHAS=  -132.0  FOM=  0.42  TEST= 0
INDE  15  58  19  FOBS=    85.2  SIGMA=   3.0  PHAS=   -14.9  FOM=  0.74  TEST= 0
INDE  15  58  21  FOBS=    89.9  SIGMA=   2.2  PHAS=   154.4  FOM=  0.95  TEST= 0
INDE  15  58  23  FOBS=    94.8  SIGMA=   2.1  PHAS=    49.0  FOM=  0.67  TEST= 0
INDE  15  58  25  FOBS=    84.1  SIGMA=   2.4  PHAS=    49.1  FOM=  0.90  TEST= 0
INDE  15  58  27  FOBS=    84.3  SIGMA=   2.7  PHAS=  -124.9  FOM=  0.11  TEST= 0
INDE  15  58  29  FOBS=    62.0  SIGMA=   4.0  PHAS=   111.5  FOM=  0.37  TEST= 0
INDE  15  58  31  FOBS=     0.0  SIGMA=  22.1  PHAS=     0.0  FOM=  0.00  TEST= 0
INDE  15  58  33  FOBS=    48.8  SIGMA=   5.1  PHAS=    15.6  FOM=  0.43  TEST= 0
INDE  15  58  35  FOBS=    24.5  SIGMA=  10.3  PHAS=  -136.5  FOM=  0.33  TEST= 0
INDE  15  58  37  FOBS=   100.0  SIGMA=   2.7  PHAS=   176.1  FOM=  0.95  TEST= 0
INDE  15  58  39  FOBS=     0.0  SIGMA=  20.8  PHAS=     0.0  FOM=  0.00  TEST= 0
INDE  15  58  41  FOBS=    40.3  SIGMA=   7.6  PHAS=  -147.1  FOM=  0.49  TEST= 0
INDE  15  58  43  FOBS=   110.3  SIGMA=   2.0  PHAS=   -32.8  FOM=  0.96  TEST= 0
INDE  15  58  45  FOBS=   115.7  SIGMA=   1.8  PHAS=  -133.0  FOM=  0.96  TEST= 0
INDE  15  58  47  FOBS=    50.9  SIGMA=   5.4  PHAS=   129.9  FOM=  0.86  TEST= 0
INDE  15  58  49  FOBS=    42.8  SIGMA=   8.6  PHAS=    35.3  FOM=  0.22  TEST= 0
INDE  15  59  16  FOBS=   146.6  SIGMA=   1.8  PHAS=  -167.6  FOM=  0.97  TEST= 0
INDE  15  59  18  FOBS=    90.2  SIGMA=   2.8  PHAS=  -120.8  FOM=  0.91  TEST= 0
INDE  15  59  20  FOBS=    86.8  SIGMA=   2.9  PHAS=     7.0  FOM=  0.86  TEST= 0
INDE  15  59  22  FOBS=    87.2  SIGMA=   2.5  PHAS=    86.5  FOM=  0.87  TEST= 0
INDE  15  59  24  FOBS=    27.7  SIGMA=   8.3  PHAS=   -43.7  FOM=  0.22  TEST= 0
INDE  15  59  26  FOBS=   125.6  SIGMA=   2.0  PHAS=  -179.0  FOM=  0.05  TEST= 1
INDE  15  59  28  FOBS=    94.3  SIGMA=   2.7  PHAS=   -43.2  FOM=  0.64  TEST= 0
INDE  15  59  30  FOBS=     0.0  SIGMA=  22.2  PHAS=     0.0  FOM=  0.00  TEST= 0
INDE  15  59  32  FOBS=   112.4  SIGMA=   2.3  PHAS=   165.2  FOM=  0.94  TEST= 0
INDE  15  59  34  FOBS=    34.0  SIGMA=   8.6  PHAS=  -169.7  FOM=  0.08  TEST= 0
INDE  15  59  36  FOBS=   125.2  SIGMA=   2.2  PHAS=    53.9  FOM=  0.95  TEST= 0
INDE  15  59  38  FOBS=    59.5  SIGMA=   4.1  PHAS=   162.2  FOM=  0.81  TEST= 0
INDE  15  59  40  FOBS=     9.7  SIGMA=  27.4  PHAS=   -86.3  FOM=  0.06  TEST= 1
INDE  15  59  42  FOBS=   112.7  SIGMA=   2.1  PHAS=  -136.6  FOM=  0.95  TEST= 0
INDE  15  59  44  FOBS=    57.3  SIGMA=   3.9  PHAS=    41.0  FOM=  0.41  TEST= 0
INDE  15  59  46  FOBS=    53.6  SIGMA=   6.4  PHAS=    73.2  FOM=  0.91  TEST= 0
INDE  15  59  48  FOBS=     0.0  SIGMA=  25.2  PHAS=     0.0  FOM=  0.00  TEST= 0
INDE  15  60  15  FOBS=    57.6  SIGMA=   2.8  PHAS=   107.1  FOM=  0.86  TEST= 0
INDE  15  60  17  FOBS=    57.5  SIGMA=   4.9  PHAS=    46.5  FOM=  0.03  TEST= 1
INDE  15  60  19  FOBS=    73.7  SIGMA=   3.9  PHAS=    49.1  FOM=  0.83  TEST= 0
INDE  15  60  21  FOBS=    47.0  SIGMA=   6.1  PHAS=   -58.4  FOM=  0.40  TEST= 0
INDE  15  60  23  FOBS=     0.0  SIGMA=  23.1  PHAS=     0.0  FOM=  0.00  TEST= 0
INDE  15  60  25  FOBS=    44.9  SIGMA=   7.2  PHAS=   169.9  FOM=  0.55  TEST= 0
INDE  15  60  27  FOBS=    20.7  SIGMA=  11.4  PHAS=  -151.8  FOM=  0.43  TEST= 0
INDE  15  60  29  FOBS=    81.4  SIGMA=   3.1  PHAS=  -129.6  FOM=  0.88  TEST= 0
INDE  15  60  31  FOBS=    48.2  SIGMA=   5.1  PHAS=    32.2  FOM=  0.70  TEST= 0
INDE  15  60  33  FOBS=    30.1  SIGMA=   8.3  PHAS=    82.8  FOM=  0.67  TEST= 0
INDE  15  60  35  FOBS=    92.0  SIGMA=   2.9  PHAS=   -23.4  FOM=  0.82  TEST= 0
INDE  15  60  37  FOBS=    70.6  SIGMA=   3.8  PHAS=    71.5  FOM=  0.85  TEST= 0
INDE  15  60  39  FOBS=    46.6  SIGMA=   5.2  PHAS=    26.9  FOM=  0.52  TEST= 0
INDE  15  60  41  FOBS=    71.4  SIGMA=   3.5  PHAS=   -45.8  FOM=  0.92  TEST= 0
INDE  15  60  43  FOBS=    57.7  SIGMA=   4.5  PHAS=    45.9  FOM=  0.78  TEST= 0
INDE  15  60  45  FOBS=    19.9  SIGMA=  15.3  PHAS=  -142.5  FOM=  0.01  TEST= 1
INDE  15  60  47  FOBS=    83.9  SIGMA=   3.4  PHAS=     3.8  FOM=  0.84  TEST= 0
```

*FIG. 12A - 374*

```
INDE 15 61 16 FOBS=   62.0 SIGMA=  3.8 PHAS= -136.3 FOM= 0.76 TEST= 0
INDE 15 61 18 FOBS=   35.2 SIGMA=  9.7 PHAS= -163.7 FOM= 0.40 TEST= 0
INDE 15 61 20 FOBS=   17.4 SIGMA= 19.6 PHAS=   23.3 FOM= 0.02 TEST= 1
INDE 15 61 22 FOBS=    0.0 SIGMA= 26.0 PHAS=    0.0 FOM= 0.00 TEST= 0
INDE 15 61 24 FOBS=   43.7 SIGMA=  5.3 PHAS=  144.0 FOM= 0.78 TEST= 0
INDE 15 61 26 FOBS=   56.1 SIGMA=  4.2 PHAS=  150.0 FOM= 0.84 TEST= 0
INDE 15 61 28 FOBS=   13.4 SIGMA= 20.8 PHAS=  112.9 FOM= 0.31 TEST= 0
INDE 15 61 30 FOBS=   22.2 SIGMA= 11.0 PHAS=   97.7 FOM= 0.32 TEST= 0
INDE 15 61 32 FOBS=   42.6 SIGMA=  5.9 PHAS=  148.7 FOM= 0.60 TEST= 0
INDE 15 61 34 FOBS=   28.8 SIGMA=  8.8 PHAS=  -82.6 FOM= 0.06 TEST= 1
INDE 15 61 36 FOBS=  107.0 SIGMA=  2.5 PHAS=  -26.2 FOM= 0.95 TEST= 0
INDE 15 61 38 FOBS=   30.6 SIGMA=  8.6 PHAS=   71.0 FOM= 0.03 TEST= 1
INDE 15 61 40 FOBS=   64.6 SIGMA=  3.5 PHAS=  -91.2 FOM= 0.75 TEST= 0
INDE 15 61 42 FOBS=  104.7 SIGMA=  2.5 PHAS= -113.3 FOM= 0.95 TEST= 0
INDE 15 61 44 FOBS=   49.8 SIGMA=  5.7 PHAS=  -59.1 FOM= 0.07 TEST= 0
INDE 15 62 15 FOBS=   53.9 SIGMA=  2.9 PHAS= -147.2 FOM= 0.22 TEST= 0
INDE 15 62 17 FOBS=    0.0 SIGMA= 26.0 PHAS=    0.0 FOM= 0.00 TEST= 0
INDE 15 62 19 FOBS=   67.3 SIGMA=  5.1 PHAS=   54.6 FOM= 0.63 TEST= 0
INDE 15 62 21 FOBS=    0.0 SIGMA= 26.0 PHAS=    0.0 FOM= 0.00 TEST= 0
INDE 15 62 23 FOBS=    0.0 SIGMA= 21.5 PHAS=    0.0 FOM= 0.00 TEST= 0
INDE 15 62 25 FOBS=   74.6 SIGMA=  3.2 PHAS=  131.5 FOM= 0.84 TEST= 0
INDE 15 62 27 FOBS=   70.8 SIGMA=  3.4 PHAS=   85.1 FOM= 0.81 TEST= 0
INDE 15 62 29 FOBS=   28.9 SIGMA= 12.3 PHAS=  -34.5 FOM= 0.61 TEST= 0
INDE 15 62 31 FOBS=    0.0 SIGMA= 23.8 PHAS=    0.0 FOM= 0.00 TEST= 0
INDE 15 62 33 FOBS=   42.3 SIGMA=  6.8 PHAS=  169.4 FOM= 0.36 TEST= 0
INDE 15 62 35 FOBS=   39.4 SIGMA=  8.8 PHAS=   14.7 FOM= 0.42 TEST= 0
INDE 15 62 37 FOBS=   47.6 SIGMA=  6.3 PHAS= -177.5 FOM= 0.84 TEST= 0
INDE 15 62 39 FOBS=   39.3 SIGMA=  8.0 PHAS=  -78.2 FOM= 0.36 TEST= 0
INDE 15 62 41 FOBS=   15.8 SIGMA= 20.1 PHAS= -141.8 FOM= 0.40 TEST= 0
INDE 15 62 43 FOBS=    0.0 SIGMA= 25.4 PHAS=    0.0 FOM= 0.00 TEST= 0
INDE 15 63 16 FOBS=   66.1 SIGMA=  2.5 PHAS= -123.8 FOM= 0.51 TEST= 0
INDE 15 63 18 FOBS=   13.8 SIGMA= 24.2 PHAS=  143.4 FOM= 0.28 TEST= 0
INDE 15 63 20 FOBS=   24.5 SIGMA= 13.8 PHAS=  -74.7 FOM= 0.12 TEST= 0
INDE 15 63 22 FOBS=    0.0 SIGMA= 25.8 PHAS=    0.0 FOM= 0.00 TEST= 0
INDE 15 63 24 FOBS=   39.6 SIGMA=  6.7 PHAS=   74.1 FOM= 0.66 TEST= 0
INDE 15 63 26 FOBS=   51.3 SIGMA=  5.3 PHAS=  -13.3 FOM= 0.64 TEST= 1
INDE 15 63 28 FOBS=   83.2 SIGMA=  3.4 PHAS= -115.0 FOM= 0.23 TEST= 1
INDE 15 63 30 FOBS=   61.2 SIGMA=  4.7 PHAS=  -46.4 FOM= 0.32 TEST= 1
INDE 15 63 32 FOBS=    0.0 SIGMA= 24.1 PHAS=    0.0 FOM= 0.00 TEST= 0
INDE 15 63 34 FOBS=   31.5 SIGMA=  9.3 PHAS=   76.2 FOM= 0.68 TEST= 0
INDE 15 63 36 FOBS=   76.1 SIGMA=  4.0 PHAS=  -36.5 FOM= 0.13 TEST= 1
INDE 15 63 38 FOBS=   53.6 SIGMA=  6.7 PHAS=   74.2 FOM= 0.44 TEST= 0
INDE 15 63 40 FOBS=    0.0 SIGMA= 25.1 PHAS=    0.0 FOM= 0.00 TEST= 0
INDE 15 63 42 FOBS=    0.0 SIGMA= 25.5 PHAS=    0.0 FOM= 0.00 TEST= 0
INDE 15 64 15 FOBS=   27.6 SIGMA=  8.2 PHAS= -162.6 FOM= 0.17 TEST= 1
INDE 15 64 17 FOBS=   38.7 SIGMA=  5.3 PHAS= -145.7 FOM= 0.19 TEST= 0
INDE 15 64 19 FOBS=    0.0 SIGMA= 26.1 PHAS=    0.0 FOM= 0.00 TEST= 0
INDE 15 64 21 FOBS=   14.1 SIGMA= 24.0 PHAS=  133.8 FOM= 0.19 TEST= 0
INDE 15 64 23 FOBS=   68.2 SIGMA=  5.0 PHAS= -161.5 FOM= 0.77 TEST= 0
INDE 15 64 25 FOBS=   57.6 SIGMA=  4.7 PHAS=  157.7 FOM= 0.75 TEST= 0
INDE 15 64 27 FOBS=   24.3 SIGMA= 11.4 PHAS=   30.9 FOM= 0.39 TEST= 0
INDE 15 64 29 FOBS=   61.6 SIGMA=  4.6 PHAS= -138.0 FOM= 0.70 TEST= 0
INDE 15 64 31 FOBS=    0.0 SIGMA= 24.0 PHAS=    0.0 FOM= 0.00 TEST= 0
INDE 15 64 33 FOBS=    0.0 SIGMA= 27.1 PHAS=    0.0 FOM= 0.00 TEST= 0
INDE 15 64 35 FOBS=    0.0 SIGMA= 27.5 PHAS=    0.0 FOM= 0.00 TEST= 0
INDE 15 64 37 FOBS=   17.8 SIGMA= 17.1 PHAS=    3.8 FOM= 0.07 TEST= 0
INDE 15 64 39 FOBS=    0.0 SIGMA= 27.0 PHAS=    0.0 FOM= 0.00 TEST= 1
INDE 15 64 41 FOBS=    0.0 SIGMA= 25.5 PHAS=    0.0 FOM= 0.00 TEST= 0
INDE 15 65 16 FOBS=   42.3 SIGMA=  5.6 PHAS=   13.6 FOM= 0.56 TEST= 0
INDE 15 65 18 FOBS=   68.5 SIGMA=  3.2 PHAS=  140.0 FOM= 0.82 TEST= 0
INDE 15 65 20 FOBS=  109.7 SIGMA=  3.3 PHAS=  160.8 FOM= 0.33 TEST= 0
INDE 15 65 22 FOBS=   83.5 SIGMA=  4.1 PHAS=  119.9 FOM= 0.89 TEST= 0
INDE 15 65 24 FOBS=   91.6 SIGMA=  3.8 PHAS=    4.5 FOM= 0.46 TEST= 1
INDE 15 65 26 FOBS=   68.5 SIGMA=  4.1 PHAS=  -14.0 FOM= 0.91 TEST= 0
INDE 15 65 28 FOBS=   43.9 SIGMA=  6.3 PHAS=  -15.7 FOM= 0.52 TEST= 0
INDE 15 65 30 FOBS=    0.0 SIGMA= 26.5 PHAS=    0.0 FOM= 0.00 TEST= 0
INDE 15 65 32 FOBS=  102.1 SIGMA=  3.0 PHAS=  160.5 FOM= 0.10 TEST= 1
INDE 15 65 34 FOBS=   73.3 SIGMA=  4.1 PHAS=   66.1 FOM= 0.59 TEST= 0
INDE 15 65 36 FOBS=   27.3 SIGMA= 11.2 PHAS=  137.9 FOM= 0.39 TEST= 0
INDE 15 65 38 FOBS=    0.0 SIGMA= 25.0 PHAS=    0.0 FOM= 0.00 TEST= 0
```

*FIG. 12A - 375*

```
INDE 15 66 15 FOBS=   42.8 SIGMA=  5.2 PHAS= -178.1 FOM= 0.05 TEST= 1
INDE 15 66 17 FOBS=   71.7 SIGMA=  2.3 PHAS=  -30.5 FOM= 0.87 TEST= 0
INDE 15 66 19 FOBS=   74.7 SIGMA=  3.2 PHAS=   66.5 FOM= 0.75 TEST= 0
INDE 15 66 21 FOBS=  114.1 SIGMA=  3.2 PHAS= -139.2 FOM= 0.06 TEST= 1
INDE 15 66 23 FOBS=   73.8 SIGMA=  4.7 PHAS=  -89.9 FOM= 0.81 TEST= 0
INDE 15 66 25 FOBS=   95.8 SIGMA=  2.9 PHAS= -118.1 FOM= 0.91 TEST= 0
INDE 15 66 27 FOBS=   57.5 SIGMA=  4.8 PHAS=  -62.5 FOM= 0.86 TEST= 0
INDE 15 66 29 FOBS=   73.0 SIGMA=  4.0 PHAS= -175.7 FOM= 0.86 TEST= 0
INDE 15 66 31 FOBS=  101.6 SIGMA=  3.0 PHAS=  -18.1 FOM= 0.09 TEST= 1
INDE 15 66 33 FOBS=   22.5 SIGMA= 13.2 PHAS= -119.4 FOM= 0.33 TEST= 0
INDE 15 66 35 FOBS=   16.4 SIGMA= 18.6 PHAS= -129.9 FOM= 0.24 TEST= 0
INDE 15 66 37 FOBS=   24.4 SIGMA= 12.8 PHAS= -143.7 FOM= 0.13 TEST= 0
INDE 15 67 16 FOBS=   31.0 SIGMA=  8.4 PHAS=  -96.9 FOM= 0.21 TEST= 0
INDE 15 67 18 FOBS=    0.0 SIGMA= 20.8 PHAS=    0.0 FOM= 0.00 TEST= 0
INDE 15 67 20 FOBS=   41.1 SIGMA=  8.4 PHAS=  -32.3 FOM= 0.08 TEST= 0
INDE 15 67 22 FOBS=   43.6 SIGMA=  7.9 PHAS=  161.5 FOM= 0.81 TEST= 0
INDE 15 67 24 FOBS=   35.9 SIGMA=  9.6 PHAS= -137.3 FOM= 0.71 TEST= 0
INDE 15 67 26 FOBS=   48.0 SIGMA=  5.8 PHAS=  172.6 FOM= 0.61 TEST= 0
INDE 15 67 28 FOBS=   44.8 SIGMA=  6.3 PHAS=  147.6 FOM= 0.30 TEST= 0
INDE 15 67 30 FOBS=   46.8 SIGMA=  6.2 PHAS=   51.1 FOM= 0.78 TEST= 0
INDE 15 67 32 FOBS=    0.0 SIGMA= 27.2 PHAS=    0.0 FOM= 0.00 TEST= 0
INDE 15 67 34 FOBS=   40.4 SIGMA=  7.5 PHAS=   58.3 FOM= 0.75 TEST= 0
INDE 15 67 36 FOBS=   60.2 SIGMA=  5.3 PHAS=   34.1 FOM= 0.34 TEST= 1
INDE 15 68 15 FOBS=   92.3 SIGMA=  3.1 PHAS= -115.2 FOM= 0.91 TEST= 0
INDE 15 68 17 FOBS=   24.1 SIGMA= 13.8 PHAS=  -22.2 FOM= 0.09 TEST= 0
INDE 15 68 19 FOBS=    0.0 SIGMA= 21.1 PHAS=    0.0 FOM= 0.00 TEST= 0
INDE 15 68 21 FOBS=   26.1 SIGMA= 19.4 PHAS=  134.3 FOM= 0.43 TEST= 0
INDE 15 68 23 FOBS=    0.0 SIGMA= 31.5 PHAS=    0.0 FOM= 0.00 TEST= 0
INDE 15 68 25 FOBS=   52.1 SIGMA=  6.7 PHAS=   76.7 FOM= 0.77 TEST= 0
INDE 15 68 27 FOBS=   28.8 SIGMA=  9.8 PHAS=   38.3 FOM= 0.62 TEST= 0
INDE 15 68 29 FOBS=   49.5 SIGMA=  5.8 PHAS=  -95.9 FOM= 0.71 TEST= 0
INDE 15 68 31 FOBS=   40.8 SIGMA=  7.3 PHAS=  -26.0 FOM= 0.39 TEST= 0
INDE 15 68 33 FOBS=   25.6 SIGMA= 11.8 PHAS=  -44.8 FOM= 0.43 TEST= 0
INDE 15 69 16 FOBS=   60.0 SIGMA=  5.0 PHAS=  149.8 FOM= 0.62 TEST= 1
INDE 15 69 18 FOBS=   37.2 SIGMA=  9.1 PHAS=  159.3 FOM= 0.48 TEST= 0
INDE 15 69 20 FOBS=    0.0 SIGMA= 23.0 PHAS=    0.0 FOM= 0.00 TEST= 0
INDE 15 69 22 FOBS=   94.7 SIGMA=  3.9 PHAS=  175.5 FOM= 0.41 TEST= 0
INDE 15 69 24 FOBS=   51.9 SIGMA=  9.5 PHAS=   -3.1 FOM= 0.44 TEST= 0
INDE 15 69 26 FOBS=   60.8 SIGMA=  8.3 PHAS=  -35.9 FOM= 0.82 TEST= 0
INDE 15 69 28 FOBS=   43.7 SIGMA=  8.0 PHAS=   37.0 FOM= 0.04 TEST= 1
INDE 15 69 30 FOBS=    0.0 SIGMA= 26.9 PHAS=    0.0 FOM= 0.00 TEST= 0
INDE 15 69 32 FOBS=    0.0 SIGMA= 24.6 PHAS=    0.0 FOM= 0.00 TEST= 0
INDE 15 70 15 FOBS=   66.8 SIGMA=  3.9 PHAS= -108.6 FOM= 0.88 TEST= 0
INDE 15 70 17 FOBS=   23.4 SIGMA= 13.1 PHAS=  104.5 FOM= 0.56 TEST= 0
INDE 15 70 19 FOBS=    0.0 SIGMA= 19.5 PHAS=    0.0 FOM= 0.00 TEST= 0
INDE 15 70 21 FOBS=    0.0 SIGMA= 24.3 PHAS=    0.0 FOM= 0.00 TEST= 0
INDE 15 70 29 FOBS=    0.0 SIGMA= 26.7 PHAS=    0.0 FOM= 0.00 TEST= 0
INDE 15 71 18 FOBS=   65.2 SIGMA=  5.3 PHAS=  148.9 FOM= 0.58 TEST= 0
INDE 15 71 20 FOBS=    0.0 SIGMA= 22.5 PHAS=    0.0 FOM= 0.00 TEST= 0
INDE 15 71 22 FOBS=    0.0 SIGMA= 25.0 PHAS=    0.0 FOM= 0.00 TEST= 0
INDE 15 71 24 FOBS=   27.1 SIGMA= 14.0 PHAS=   -5.2 FOM= 0.28 TEST= 0
INDE 15 72 17 FOBS=   38.2 SIGMA=  8.1 PHAS=    2.7 FOM= 0.51 TEST= 0
INDE 15 72 19 FOBS=   52.0 SIGMA=  7.0 PHAS=   80.5 FOM= 0.27 TEST= 0
INDE 15 72 21 FOBS=    0.0 SIGMA= 23.6 PHAS=    0.0 FOM= 0.00 TEST= 0
INDE 15 72 23 FOBS=   32.3 SIGMA= 10.6 PHAS=  142.2 FOM= 0.04 TEST= 1
INDE 15 72 25 FOBS=   38.9 SIGMA= 10.1 PHAS=   71.3 FOM= 0.60 TEST= 0
INDE 15 73 16 FOBS=   14.2 SIGMA= 17.6 PHAS=  -21.6 FOM= 0.17 TEST= 0
INDE 15 73 18 FOBS=   44.4 SIGMA=  7.2 PHAS=  150.7 FOM= 0.39 TEST= 0
INDE 15 73 20 FOBS=    0.0 SIGMA= 26.6 PHAS=    0.0 FOM= 0.00 TEST= 0
INDE 15 73 22 FOBS=    0.0 SIGMA= 18.9 PHAS=    0.0 FOM= 0.00 TEST= 0
INDE 15 74 17 FOBS=   50.9 SIGMA=  5.6 PHAS=  -67.2 FOM= 0.54 TEST= 0
INDE 16 16 16 FOBS=  239.3 SIGMA=  1.0 PHAS=    9.5 FOM= 0.96 TEST= 0
INDE 16 17 17 FOBS=  138.1 SIGMA=  0.7 PHAS= -109.1 FOM= 0.97 TEST= 0
INDE 16 17 19 FOBS=  162.9 SIGMA=  0.6 PHAS=   -4.4 FOM= 0.98 TEST= 0
INDE 16 17 21 FOBS=   60.8 SIGMA=  1.4 PHAS=   91.2 FOM= 0.92 TEST= 0
INDE 16 17 23 FOBS=   89.3 SIGMA=  1.1 PHAS=  -12.8 FOM= 0.99 TEST= 1
INDE 16 17 25 FOBS=   60.8 SIGMA=  1.6 PHAS=  -57.9 FOM= 0.99 TEST= 1
INDE 16 17 27 FOBS=  129.9 SIGMA=  0.9 PHAS=   70.8 FOM= 0.96 TEST= 0
INDE 16 17 29 FOBS=  220.2 SIGMA=  0.5 PHAS=  -57.2 FOM= 0.26 TEST= 1
INDE 16 17 31 FOBS=  356.7 SIGMA=  0.4 PHAS=  -19.9 FOM= 0.97 TEST= 0
```

*FIG. 12A - 376*

```
INDE 16 17 33 FOBS=    51.6 SIGMA=  2.1 PHAS=  -14.4 FOM= 0.83 TEST= 0
INDE 16 17 35 FOBS=    16.7 SIGMA=  7.0 PHAS=  125.7 FOM= 0.02 TEST= 0
INDE 16 17 37 FOBS=   136.6 SIGMA=  1.0 PHAS=  -22.8 FOM= 0.97 TEST= 0
INDE 16 17 39 FOBS=   135.8 SIGMA=  1.2 PHAS=   77.7 FOM= 0.98 TEST= 0
INDE 16 17 41 FOBS=   105.6 SIGMA=  1.8 PHAS=   39.4 FOM= 0.76 TEST= 0
INDE 16 17 43 FOBS=   103.1 SIGMA=  2.1 PHAS=  -79.2 FOM= 0.86 TEST= 0
INDE 16 17 45 FOBS=    58.5 SIGMA=  3.7 PHAS=  -89.3 FOM= 0.91 TEST= 0
INDE 16 17 47 FOBS=    88.4 SIGMA=  3.2 PHAS=  -68.2 FOM= 0.79 TEST= 1
INDE 16 17 49 FOBS=   106.7 SIGMA=  2.6 PHAS= -148.7 FOM= 0.90 TEST= 0
INDE 16 17 51 FOBS=    98.5 SIGMA=  2.0 PHAS=  -84.7 FOM= 0.88 TEST= 0
INDE 16 17 53 FOBS=   142.9 SIGMA=  1.4 PHAS=   88.6 FOM= 0.95 TEST= 0
INDE 16 17 55 FOBS=   118.6 SIGMA=  1.6 PHAS=   26.7 FOM= 0.86 TEST= 0
INDE 16 17 57 FOBS=    66.7 SIGMA=  3.2 PHAS=   30.2 FOM= 0.61 TEST= 0
INDE 16 17 59 FOBS=   100.9 SIGMA=  2.2 PHAS=  146.9 FOM= 0.94 TEST= 0
INDE 16 17 61 FOBS=    67.6 SIGMA=  3.6 PHAS=   15.5 FOM= 0.71 TEST= 0
INDE 16 17 63 FOBS=    80.9 SIGMA=  3.0 PHAS=   33.8 FOM= 0.89 TEST= 0
INDE 16 17 65 FOBS=    84.0 SIGMA=  2.9 PHAS=   24.1 FOM= 0.92 TEST= 0
INDE 16 17 67 FOBS=    24.3 SIGMA= 13.3 PHAS= -166.4 FOM= 0.45 TEST= 0
INDE 16 17 69 FOBS=    52.4 SIGMA=  5.2 PHAS=  -53.0 FOM= 0.59 TEST= 0
INDE 16 17 71 FOBS=    37.8 SIGMA=  6.7 PHAS=   74.2 FOM= 0.40 TEST= 0
INDE 16 18 16 FOBS=   146.6 SIGMA=  0.6 PHAS=   11.0 FOM= 0.95 TEST= 0
INDE 16 18 18 FOBS=   140.6 SIGMA=  0.7 PHAS=  -31.0 FOM= 0.98 TEST= 0
INDE 16 18 20 FOBS=   232.7 SIGMA=  0.5 PHAS=  -12.0 FOM= 0.83 TEST= 0
INDE 16 18 22 FOBS=    42.1 SIGMA=  2.0 PHAS=   15.6 FOM= 0.88 TEST= 0
INDE 16 18 24 FOBS=   154.7 SIGMA=  0.8 PHAS=  139.6 FOM= 0.99 TEST= 0
INDE 16 18 26 FOBS=   171.1 SIGMA=  0.7 PHAS=   57.5 FOM= 0.98 TEST= 0
INDE 16 18 28 FOBS=   184.1 SIGMA=  0.7 PHAS= -129.0 FOM= 0.92 TEST= 0
INDE 16 18 30 FOBS=   295.5 SIGMA=  0.5 PHAS=  -90.3 FOM= 0.94 TEST= 0
INDE 16 18 32 FOBS=    98.5 SIGMA=  1.1 PHAS= -108.0 FOM= 0.80 TEST= 0
INDE 16 18 34 FOBS=   144.9 SIGMA=  0.9 PHAS=  -17.1 FOM= 0.91 TEST= 0
INDE 16 18 36 FOBS=   169.1 SIGMA=  0.8 PHAS=  -43.7 FOM= 0.88 TEST= 0
INDE 16 18 38 FOBS=   424.4 SIGMA=  0.6 PHAS=  -51.5 FOM= 0.98 TEST= 0
INDE 16 18 40 FOBS=   216.7 SIGMA=  0.7 PHAS=  -11.7 FOM= 0.96 TEST= 0
INDE 16 18 42 FOBS=    26.5 SIGMA=  6.2 PHAS=   49.8 FOM= 0.20 TEST= 0
INDE 16 18 44 FOBS=   141.7 SIGMA=  1.1 PHAS=  148.3 FOM= 0.86 TEST= 0
INDE 16 18 46 FOBS=    97.0 SIGMA=  1.8 PHAS=   41.1 FOM= 0.86 TEST= 0
INDE 16 18 48 FOBS=   110.4 SIGMA=  1.8 PHAS=   59.8 FOM= 0.44 TEST= 0
INDE 16 18 50 FOBS=    44.8 SIGMA=  4.3 PHAS=    5.0 FOM= 0.45 TEST= 0
INDE 16 18 52 FOBS=   113.7 SIGMA=  1.7 PHAS=   33.4 FOM= 0.96 TEST= 0
INDE 16 18 54 FOBS=    49.9 SIGMA=  3.8 PHAS=   63.4 FOM= 0.61 TEST= 0
INDE 16 18 56 FOBS=   108.2 SIGMA=  1.8 PHAS= -149.3 FOM= 0.88 TEST= 0
INDE 16 18 58 FOBS=    19.6 SIGMA= 10.7 PHAS= -142.8 FOM= 0.44 TEST= 0
INDE 16 18 60 FOBS=    37.2 SIGMA=  6.0 PHAS=  170.6 FOM= 0.45 TEST= 0
INDE 16 18 62 FOBS=   122.6 SIGMA=  2.1 PHAS= -171.3 FOM= 0.84 TEST= 0
INDE 16 18 64 FOBS=    87.6 SIGMA=  2.8 PHAS=  -47.6 FOM= 0.88 TEST= 0
INDE 16 18 66 FOBS=     0.0 SIGMA= 23.2 PHAS=    0.0 FOM= 0.00 TEST= 0
INDE 16 18 68 FOBS=     0.0 SIGMA= 23.6 PHAS=    0.0 FOM= 0.00 TEST= 1
INDE 16 18 70 FOBS=    29.4 SIGMA=  9.3 PHAS= -152.6 FOM= 0.06 TEST= 0
INDE 16 19 17 FOBS=   293.4 SIGMA=  0.4 PHAS= -104.5 FOM= 0.98 TEST= 0
INDE 16 19 19 FOBS=   271.4 SIGMA=  0.5 PHAS=  -85.2 FOM= 0.98 TEST= 0
INDE 16 19 21 FOBS=    91.3 SIGMA=  0.9 PHAS=  -61.5 FOM= 0.96 TEST= 0
INDE 16 19 23 FOBS=   305.6 SIGMA=  0.4 PHAS=   16.8 FOM= 0.98 TEST= 0
INDE 16 19 25 FOBS=    39.4 SIGMA=  2.3 PHAS=   -0.1 FOM= 0.20 TEST= 0
INDE 16 19 27 FOBS=   108.9 SIGMA=  0.9 PHAS=  156.5 FOM= 0.99 TEST= 0
INDE 16 19 29 FOBS=   114.4 SIGMA=  0.9 PHAS=   38.2 FOM= 0.08 TEST= 1
INDE 16 19 31 FOBS=   121.3 SIGMA=  0.9 PHAS=  -58.1 FOM= 0.94 TEST= 0
INDE 16 19 33 FOBS=    19.4 SIGMA=  5.6 PHAS= -126.5 FOM= 0.58 TEST= 0
INDE 16 19 35 FOBS=   104.7 SIGMA=  1.1 PHAS= -171.3 FOM= 0.86 TEST= 1
INDE 16 19 37 FOBS=   319.3 SIGMA=  0.6 PHAS= -141.0 FOM= 0.97 TEST= 0
INDE 16 19 39 FOBS=   277.5 SIGMA=  0.6 PHAS= -105.8 FOM= 0.96 TEST= 0
INDE 16 19 41 FOBS=    86.0 SIGMA=  1.7 PHAS=  -75.7 FOM= 0.76 TEST= 0
INDE 16 19 43 FOBS=   106.4 SIGMA=  1.5 PHAS=   17.4 FOM= 0.64 TEST= 0
INDE 16 19 45 FOBS=   173.1 SIGMA=  1.0 PHAS=   28.1 FOM= 0.92 TEST= 0
INDE 16 19 47 FOBS=   182.8 SIGMA=  1.0 PHAS=  -67.2 FOM= 0.81 TEST= 0
INDE 16 19 49 FOBS=     0.0 SIGMA= 18.5 PHAS=    0.0 FOM= 0.00 TEST= 0
INDE 16 19 51 FOBS=   121.0 SIGMA=  1.5 PHAS=  -56.4 FOM= 0.86 TEST= 0
INDE 16 19 53 FOBS=    39.4 SIGMA=  4.8 PHAS= -167.6 FOM= 0.07 TEST= 0
INDE 16 19 55 FOBS=    52.7 SIGMA=  3.5 PHAS=  141.8 FOM= 0.88 TEST= 0
INDE 16 19 57 FOBS=    17.7 SIGMA= 13.0 PHAS=  -70.8 FOM= 0.04 TEST= 0
INDE 16 19 59 FOBS=    89.7 SIGMA=  2.6 PHAS=  162.8 FOM= 0.93 TEST= 0
```

*FIG. 12A - 377*

```
INDE  16  19  61  FOBS=   66.2  SIGMA=   3.8  PHAS=   89.7  FOM= 0.86  TEST= 0
INDE  16  19  63  FOBS=   50.0  SIGMA=   4.9  PHAS=  -12.6  FOM= 0.70  TEST= 0
INDE  16  19  65  FOBS=    0.0  SIGMA=  21.4  PHAS=    0.0  FOM= 0.00  TEST= 0
INDE  16  19  67  FOBS=  157.8  SIGMA=   2.0  PHAS= -138.2  FOM= 0.94  TEST= 0
INDE  16  19  69  FOBS=   27.5  SIGMA=  10.6  PHAS=  -54.2  FOM= 0.14  TEST= 0
INDE  16  20  16  FOBS=  168.4  SIGMA=   0.7  PHAS=  125.5  FOM= 0.99  TEST= 0
INDE  16  20  18  FOBS=  307.1  SIGMA=   0.5  PHAS= -176.1  FOM= 0.97  TEST= 0
INDE  16  20  20  FOBS=   98.8  SIGMA=   1.0  PHAS=  -79.8  FOM= 0.89  TEST= 0
INDE  16  20  22  FOBS=  259.8  SIGMA=   0.5  PHAS=  -49.7  FOM= 0.95  TEST= 0
INDE  16  20  24  FOBS=   91.8  SIGMA=   1.0  PHAS=  -14.1  FOM= 0.96  TEST= 0
INDE  16  20  26  FOBS=  145.5  SIGMA=   0.8  PHAS=   56.5  FOM= 0.99  TEST= 0
INDE  16  20  28  FOBS=  226.0  SIGMA=   0.6  PHAS=  138.7  FOM= 0.93  TEST= 0
INDE  16  20  30  FOBS=   50.3  SIGMA=   2.0  PHAS=  -86.4  FOM= 0.35  TEST= 0
INDE  16  20  32  FOBS=  191.5  SIGMA=   0.7  PHAS= -110.6  FOM= 0.94  TEST= 0
INDE  16  20  34  FOBS=   35.3  SIGMA=   3.2  PHAS=   48.8  FOM= 0.78  TEST= 0
INDE  16  20  36  FOBS=  134.2  SIGMA=   0.9  PHAS=  120.6  FOM= 0.99  TEST= 0
INDE  16  20  38  FOBS=  104.3  SIGMA=   1.3  PHAS=   78.7  FOM= 0.94  TEST= 0
INDE  16  20  40  FOBS=    0.0  SIGMA=  17.2  PHAS=    0.0  FOM= 0.00  TEST= 0
INDE  16  20  42  FOBS=   37.4  SIGMA=   3.9  PHAS=   76.1  FOM= 0.53  TEST= 0
INDE  16  20  44  FOBS=    0.0  SIGMA=  18.2  PHAS=    0.0  FOM= 0.00  TEST= 0
INDE  16  20  46  FOBS=   67.9  SIGMA=   2.4  PHAS= -105.6  FOM= 0.90  TEST= 0
INDE  16  20  48  FOBS=   62.1  SIGMA=   2.6  PHAS=   37.5  FOM= 0.39  TEST= 0
INDE  16  20  50  FOBS=    0.0  SIGMA=  19.5  PHAS=    0.0  FOM= 0.00  TEST= 0
INDE  16  20  52  FOBS=   54.3  SIGMA=   3.1  PHAS=    1.8  FOM= 0.55  TEST= 0
INDE  16  20  54  FOBS=  118.2  SIGMA=   1.5  PHAS=  115.8  FOM= 0.94  TEST= 0
INDE  16  20  56  FOBS=   75.0  SIGMA=   2.5  PHAS=   -5.6  FOM= 0.15  TEST= 1
INDE  16  20  58  FOBS=   56.4  SIGMA=   3.8  PHAS=  124.8  FOM= 0.75  TEST= 0
INDE  16  20  60  FOBS=  103.6  SIGMA=   2.6  PHAS=  -83.2  FOM= 0.65  TEST= 0
INDE  16  20  62  FOBS=   19.6  SIGMA=  12.2  PHAS= -115.2  FOM= 0.23  TEST= 0
INDE  16  20  64  FOBS=    0.0  SIGMA=  21.7  PHAS=    0.0  FOM= 0.00  TEST= 0
INDE  16  20  66  FOBS=  118.7  SIGMA=   2.7  PHAS=  101.3  FOM= 0.92  TEST= 0
INDE  16  20  68  FOBS=   41.5  SIGMA=   7.0  PHAS= -170.9  FOM= 0.69  TEST= 0
INDE  16  21  17  FOBS=  108.0  SIGMA=   0.8  PHAS=   48.9  FOM= 0.95  TEST= 0
INDE  16  21  19  FOBS=  120.0  SIGMA=   0.8  PHAS=  135.9  FOM= 0.95  TEST= 0
INDE  16  21  21  FOBS=  170.8  SIGMA=   0.7  PHAS= -107.8  FOM= 0.96  TEST= 0
INDE  16  21  23  FOBS=  235.1  SIGMA=   0.5  PHAS= -129.1  FOM= 0.73  TEST= 1
INDE  16  21  25  FOBS=  147.1  SIGMA=   0.8  PHAS=  -57.9  FOM= 0.99  TEST= 0
INDE  16  21  27  FOBS=  194.0  SIGMA=   0.6  PHAS=  -40.3  FOM= 0.89  TEST= 0
INDE  16  21  29  FOBS=  196.3  SIGMA=   0.6  PHAS=  161.6  FOM= 0.97  TEST= 0
INDE  16  21  31  FOBS=  210.5  SIGMA=   0.6  PHAS= -137.2  FOM= 0.87  TEST= 0
INDE  16  21  33  FOBS=  133.7  SIGMA=   0.9  PHAS=  165.8  FOM= 0.92  TEST= 0
INDE  16  21  35  FOBS=   85.3  SIGMA=   1.5  PHAS=    1.7  FOM= 0.87  TEST= 0
INDE  16  21  37  FOBS=   18.7  SIGMA=   6.8  PHAS=   85.9  FOM= 0.60  TEST= 0
INDE  16  21  39  FOBS=  170.1  SIGMA=   0.9  PHAS=  -54.5  FOM= 0.94  TEST= 0
INDE  16  21  41  FOBS=    0.0  SIGMA=  17.2  PHAS=    0.0  FOM= 0.00  TEST= 0
INDE  16  21  43  FOBS=   94.4  SIGMA=   1.7  PHAS=   40.9  FOM= 0.34  TEST= 0
INDE  16  21  45  FOBS=  168.0  SIGMA=   1.0  PHAS=   80.7  FOM= 0.96  TEST= 0
INDE  16  21  47  FOBS=    0.0  SIGMA=  18.3  PHAS=    0.0  FOM= 0.00  TEST= 0
INDE  16  21  49  FOBS=   82.4  SIGMA=   2.0  PHAS=  169.1  FOM= 0.53  TEST= 0
INDE  16  21  51  FOBS=  130.1  SIGMA=   1.4  PHAS=  -41.2  FOM= 0.94  TEST= 0
INDE  16  21  53  FOBS=  130.7  SIGMA=   1.3  PHAS=   50.7  FOM= 0.89  TEST= 0
INDE  16  21  55  FOBS=  102.4  SIGMA=   1.7  PHAS=   29.3  FOM= 0.88  TEST= 0
INDE  16  21  57  FOBS=   63.7  SIGMA=   2.9  PHAS=  -10.0  FOM= 0.80  TEST= 0
INDE  16  21  59  FOBS=   93.9  SIGMA=   2.8  PHAS=  129.6  FOM= 0.94  TEST= 0
INDE  16  21  61  FOBS=    0.0  SIGMA=  22.2  PHAS=    0.0  FOM= 0.00  TEST= 0
INDE  16  21  63  FOBS=    0.0  SIGMA=  23.3  PHAS=    0.0  FOM= 0.00  TEST= 0
INDE  16  21  65  FOBS=   92.5  SIGMA=   3.0  PHAS=   55.0  FOM= 0.94  TEST= 0
INDE  16  21  67  FOBS=   33.9  SIGMA=   8.6  PHAS=  -98.5  FOM= 0.29  TEST= 0
INDE  16  22  16  FOBS=   51.2  SIGMA=   1.8  PHAS= -101.2  FOM= 0.91  TEST= 0
INDE  16  22  18  FOBS=   12.5  SIGMA=   7.2  PHAS=  136.2  FOM= 0.71  TEST= 0
INDE  16  22  20  FOBS=  222.3  SIGMA=   0.6  PHAS=   70.3  FOM= 0.98  TEST= 0
INDE  16  22  22  FOBS=   43.1  SIGMA=   2.3  PHAS=  -69.0  FOM= 0.91  TEST= 0
INDE  16  22  24  FOBS=  150.4  SIGMA=   0.7  PHAS= -169.2  FOM= 0.99  TEST= 0
INDE  16  22  26  FOBS=  319.4  SIGMA=   0.5  PHAS= -125.1  FOM= 0.94  TEST= 0
INDE  16  22  28  FOBS=  124.4  SIGMA=   0.9  PHAS=  163.1  FOM= 0.98  TEST= 0
INDE  16  22  30  FOBS=  394.8  SIGMA=   0.5  PHAS=  127.1  FOM= 0.96  TEST= 0
INDE  16  22  32  FOBS=   92.8  SIGMA=   1.3  PHAS=   93.8  FOM= 0.71  TEST= 0
INDE  16  22  34  FOBS=  102.4  SIGMA=   1.3  PHAS=    5.3  FOM= 0.76  TEST= 0
INDE  16  22  36  FOBS=  254.6  SIGMA=   0.7  PHAS= -153.9  FOM= 0.96  TEST= 0
INDE  16  22  38  FOBS=  234.4  SIGMA=   0.7  PHAS=   51.8  FOM= 0.82  TEST= 1
```

*FIG. 12A - 378*

```
INDE 16 22 40 FOBS=   129.1 SIGMA=   1.2 PHAS=  -55.2 FOM= 0.96 TEST= 0
INDE 16 22 42 FOBS=    20.8 SIGMA=   7.4 PHAS=   28.8 FOM= 0.10 TEST= 0
INDE 16 22 44 FOBS=   129.0 SIGMA=   1.2 PHAS=   52.9 FOM= 0.86 TEST= 0
INDE 16 22 46 FOBS=    34.2 SIGMA=   4.6 PHAS=  -67.0 FOM= 0.91 TEST= 0
INDE 16 22 48 FOBS=   260.5 SIGMA=   0.8 PHAS=   42.2 FOM= 0.96 TEST= 0
INDE 16 22 50 FOBS=   107.5 SIGMA=   1.5 PHAS=    9.2 FOM= 0.90 TEST= 0
INDE 16 22 52 FOBS=    51.7 SIGMA=   3.1 PHAS=  -89.6 FOM= 0.73 TEST= 1
INDE 16 22 54 FOBS=    22.1 SIGMA=   8.0 PHAS=   89.0 FOM= 0.37 TEST= 0
INDE 16 22 56 FOBS=     0.0 SIGMA=  21.7 PHAS=    0.0 FOM= 0.00 TEST= 0
INDE 16 22 58 FOBS=    89.7 SIGMA=   2.2 PHAS=   94.1 FOM= 0.89 TEST= 0
INDE 16 22 60 FOBS=    29.1 SIGMA=   6.9 PHAS=    5.8 FOM= 0.50 TEST= 0
INDE 16 22 62 FOBS=    40.7 SIGMA=   6.1 PHAS= -159.3 FOM= 0.24 TEST= 0
INDE 16 22 64 FOBS=     0.0 SIGMA=  22.0 PHAS=    0.0 FOM= 0.00 TEST= 0
INDE 16 22 66 FOBS=     2.9 SIGMA= 102.9 PHAS=   40.4 FOM= 0.05 TEST= 0
INDE 16 23 17 FOBS=    47.4 SIGMA=   1.8 PHAS= -161.8 FOM= 0.81 TEST= 0
INDE 16 23 19 FOBS=   232.5 SIGMA=   0.5 PHAS=   33.0 FOM= 0.96 TEST= 0
INDE 16 23 21 FOBS=   123.6 SIGMA=   0.9 PHAS=  -16.2 FOM= 0.97 TEST= 0
INDE 16 23 23 FOBS=   203.3 SIGMA=   0.6 PHAS= -130.1 FOM= 0.97 TEST= 0
INDE 16 23 25 FOBS=   195.8 SIGMA=   0.6 PHAS=  108.1 FOM= 0.05 TEST= 1
INDE 16 23 27 FOBS=   267.6 SIGMA=   0.6 PHAS=  150.1 FOM= 0.97 TEST= 1
INDE 16 23 29 FOBS=   198.5 SIGMA=   0.7 PHAS=  108.3 FOM= 0.87 TEST= 0
INDE 16 23 31 FOBS=   291.8 SIGMA=   0.6 PHAS=   -3.4 FOM= 0.94 TEST= 0
INDE 16 23 33 FOBS=   159.3 SIGMA=   0.9 PHAS=   87.2 FOM= 0.85 TEST= 0
INDE 16 23 35 FOBS=   158.2 SIGMA=   0.9 PHAS=   92.1 FOM= 0.98 TEST= 0
INDE 16 23 37 FOBS=   176.6 SIGMA=   0.9 PHAS=   88.5 FOM= 0.93 TEST= 0
INDE 16 23 39 FOBS=   145.8 SIGMA=   1.1 PHAS=  -83.9 FOM= 0.93 TEST= 0
INDE 16 23 41 FOBS=    21.9 SIGMA=   7.8 PHAS= -107.1 FOM= 0.16 TEST= 1
INDE 16 23 43 FOBS=    89.6 SIGMA=   1.7 PHAS=    6.9 FOM= 0.96 TEST= 0
INDE 16 23 45 FOBS=    31.6 SIGMA=   4.9 PHAS= -138.4 FOM= 0.40 TEST= 0
INDE 16 23 47 FOBS=   140.8 SIGMA=   1.1 PHAS=  -75.6 FOM= 0.90 TEST= 0
INDE 16 23 49 FOBS=   228.8 SIGMA=   0.8 PHAS=  -97.4 FOM= 0.97 TEST= 0
INDE 16 23 51 FOBS=   113.8 SIGMA=   1.4 PHAS=  -37.9 FOM= 0.95 TEST= 0
INDE 16 23 53 FOBS=    48.6 SIGMA=   3.2 PHAS=  -83.0 FOM= 0.11 TEST= 1
INDE 16 23 55 FOBS=    45.7 SIGMA=   3.6 PHAS=  125.8 FOM= 0.63 TEST= 0
INDE 16 23 57 FOBS=    88.5 SIGMA=   2.1 PHAS=  -12.9 FOM= 0.93 TEST= 0
INDE 16 23 59 FOBS=    54.0 SIGMA=   3.8 PHAS=  -51.8 FOM= 0.71 TEST= 0
INDE 16 23 61 FOBS=    52.0 SIGMA=   3.9 PHAS=  -44.1 FOM= 0.53 TEST= 0
INDE 16 23 63 FOBS=    52.7 SIGMA=   3.8 PHAS=  -72.5 FOM= 0.61 TEST= 0
INDE 16 23 65 FOBS=    49.8 SIGMA=   6.3 PHAS=  146.8 FOM= 0.40 TEST= 0
INDE 16 24 16 FOBS=    88.5 SIGMA=   1.3 PHAS=  110.5 FOM= 0.92 TEST= 0
INDE 16 24 18 FOBS=   195.0 SIGMA=   0.6 PHAS=  -44.2 FOM= 0.90 TEST= 0
INDE 16 24 20 FOBS=   253.7 SIGMA=   0.5 PHAS=    0.1 FOM= 0.98 TEST= 0
INDE 16 24 22 FOBS=   138.6 SIGMA=   0.8 PHAS=   19.4 FOM= 0.94 TEST= 0
INDE 16 24 24 FOBS=   147.7 SIGMA=   0.8 PHAS=  166.5 FOM= 0.98 TEST= 0
INDE 16 24 26 FOBS=   206.9 SIGMA=   0.6 PHAS=   62.0 FOM= 0.94 TEST= 0
INDE 16 24 28 FOBS=   243.9 SIGMA=   0.6 PHAS=    8.5 FOM= 0.97 TEST= 0
INDE 16 24 30 FOBS=    71.7 SIGMA=   1.6 PHAS= -165.4 FOM= 0.66 TEST= 0
INDE 16 24 32 FOBS=   307.7 SIGMA=   0.6 PHAS=  -27.6 FOM= 0.91 TEST= 0
INDE 16 24 34 FOBS=   269.3 SIGMA=   0.6 PHAS=  -52.8 FOM= 0.97 TEST= 0
INDE 16 24 36 FOBS=    91.8 SIGMA=   1.6 PHAS= -143.8 FOM= 0.88 TEST= 0
INDE 16 24 38 FOBS=   240.0 SIGMA=   0.7 PHAS=   79.7 FOM= 0.94 TEST= 0
INDE 16 24 40 FOBS=    49.4 SIGMA=   3.5 PHAS=   67.2 FOM= 0.32 TEST= 0
INDE 16 24 42 FOBS=    52.6 SIGMA=   3.0 PHAS=  -31.3 FOM= 0.93 TEST= 0
INDE 16 24 44 FOBS=   137.3 SIGMA=   1.2 PHAS=  -68.5 FOM= 0.89 TEST= 0
INDE 16 24 46 FOBS=    38.9 SIGMA=   4.0 PHAS=  135.0 FOM= 0.11 TEST= 0
INDE 16 24 48 FOBS=   157.2 SIGMA=   1.0 PHAS=   55.9 FOM= 0.91 TEST= 0
INDE 16 24 50 FOBS=    49.8 SIGMA=   2.9 PHAS=  165.7 FOM= 0.73 TEST= 0
INDE 16 24 52 FOBS=    84.2 SIGMA=   1.9 PHAS= -112.2 FOM= 0.89 TEST= 0
INDE 16 24 54 FOBS=    47.5 SIGMA=   3.3 PHAS=  174.6 FOM= 0.71 TEST= 0
INDE 16 24 56 FOBS=   115.7 SIGMA=   1.7 PHAS= -102.6 FOM= 0.92 TEST= 0
INDE 16 24 58 FOBS=    57.3 SIGMA=   3.5 PHAS=   34.9 FOM= 0.36 TEST= 0
INDE 16 24 60 FOBS=    46.1 SIGMA=   4.5 PHAS=  158.5 FOM= 0.44 TEST= 0
INDE 16 24 62 FOBS=    93.1 SIGMA=   2.3 PHAS= -153.8 FOM= 0.85 TEST= 0
INDE 16 24 64 FOBS=    40.0 SIGMA=   6.0 PHAS=  -21.1 FOM= 0.58 TEST= 0
INDE 16 24 66 FOBS=    37.8 SIGMA=  14.1 PHAS= -117.2 FOM= 0.59 TEST= 0
INDE 16 25 17 FOBS=   254.7 SIGMA=   0.7 PHAS= -120.0 FOM= 0.96 TEST= 0
INDE 16 25 19 FOBS=    61.3 SIGMA=   1.6 PHAS=  -71.1 FOM= 0.97 TEST= 0
INDE 16 25 21 FOBS=   340.1 SIGMA=   0.5 PHAS=  -72.7 FOM= 0.99 TEST= 0
INDE 16 25 23 FOBS=   123.8 SIGMA=   0.9 PHAS= -120.7 FOM= 0.79 TEST= 1
INDE 16 25 25 FOBS=   183.7 SIGMA=   0.7 PHAS=    3.3 FOM= 0.99 TEST= 0
```

*FIG. 12A - 379*

```
INDE  16  25  27 FOBS=   301.5 SIGMA=   0.6 PHAS=  -111.8 FOM=  0.94 TEST= 0
INDE  16  25  29 FOBS=   139.2 SIGMA=   1.0 PHAS=  -179.2 FOM=  0.97 TEST= 0
INDE  16  25  31 FOBS=   126.7 SIGMA=   1.1 PHAS=   143.7 FOM=  0.77 TEST= 0
INDE  16  25  33 FOBS=   194.9 SIGMA=   0.8 PHAS=  -122.2 FOM=  0.94 TEST= 0
INDE  16  25  35 FOBS=    76.4 SIGMA=   2.0 PHAS=    70.3 FOM=  0.86 TEST= 1
INDE  16  25  37 FOBS=   180.6 SIGMA=   1.0 PHAS=    61.6 FOM=  0.89 TEST= 0
INDE  16  25  39 FOBS=     0.0 SIGMA=  18.7 PHAS=     0.0 FOM=  0.00 TEST= 0
INDE  16  25  41 FOBS=    56.0 SIGMA=   3.2 PHAS=    85.5 FOM=  0.81 TEST= 0
INDE  16  25  43 FOBS=     0.0 SIGMA=  17.9 PHAS=     0.0 FOM=  0.00 TEST= 0
INDE  16  25  45 FOBS=   122.5 SIGMA=   1.3 PHAS=  -151.2 FOM=  0.94 TEST= 0
INDE  16  25  47 FOBS=   210.1 SIGMA=   0.8 PHAS=   -82.6 FOM=  0.95 TEST= 0
INDE  16  25  49 FOBS=    49.4 SIGMA=   3.0 PHAS=   -65.1 FOM=  0.68 TEST= 0
INDE  16  25  51 FOBS=   144.1 SIGMA=   1.1 PHAS=    55.9 FOM=  0.83 TEST= 1
INDE  16  25  53 FOBS=    47.9 SIGMA=   3.3 PHAS=    81.6 FOM=  0.67 TEST= 0
INDE  16  25  55 FOBS=    63.0 SIGMA=   2.7 PHAS=   177.3 FOM=  0.63 TEST= 0
INDE  16  25  57 FOBS=   115.6 SIGMA=   1.8 PHAS=    22.4 FOM=  0.05 TEST= 1
INDE  16  25  59 FOBS=   143.3 SIGMA=   1.6 PHAS=   -78.7 FOM=  0.94 TEST= 0
INDE  16  25  61 FOBS=    99.7 SIGMA=   2.1 PHAS=    64.0 FOM=  0.87 TEST= 0
INDE  16  25  63 FOBS=     0.0 SIGMA=  21.6 PHAS=     0.0 FOM=  0.00 TEST= 0
INDE  16  25  65 FOBS=   133.4 SIGMA=   4.1 PHAS=   176.3 FOM=  0.95 TEST= 0
INDE  16  25  67 FOBS=    19.0 SIGMA=  27.1 PHAS=   145.3 FOM=  0.39 TEST= 0
INDE  16  26  16 FOBS=   193.5 SIGMA=   0.7 PHAS=   124.7 FOM=  0.97 TEST= 0
INDE  16  26  18 FOBS=   165.5 SIGMA=   0.7 PHAS=   160.7 FOM=  0.97 TEST= 0
INDE  16  26  20 FOBS=   168.1 SIGMA=   0.7 PHAS=   -77.4 FOM=  0.87 TEST= 0
INDE  16  26  22 FOBS=    96.8 SIGMA=   1.2 PHAS=  -160.9 FOM=  0.96 TEST= 0
INDE  16  26  24 FOBS=   204.4 SIGMA=   0.7 PHAS=   146.4 FOM=  0.90 TEST= 0
INDE  16  26  26 FOBS=   156.9 SIGMA=   0.8 PHAS=   101.5 FOM=  0.99 TEST= 0
INDE  16  26  28 FOBS=   121.1 SIGMA=   1.1 PHAS=   140.5 FOM=  0.89 TEST= 0
INDE  16  26  30 FOBS=   120.1 SIGMA=   1.2 PHAS=   -46.3 FOM=  0.98 TEST= 1
INDE  16  26  32 FOBS=   163.1 SIGMA=   1.0 PHAS=   -10.4 FOM=  0.90 TEST= 0
INDE  16  26  34 FOBS=   223.8 SIGMA=   0.8 PHAS=  -122.1 FOM=  0.95 TEST= 0
INDE  16  26  36 FOBS=   101.0 SIGMA=   1.7 PHAS=   -62.7 FOM=  0.91 TEST= 0
INDE  16  26  38 FOBS=    61.1 SIGMA=   2.9 PHAS=   118.6 FOM=  0.05 TEST= 0
INDE  16  26  40 FOBS=   126.4 SIGMA=   1.4 PHAS=   -65.5 FOM=  0.75 TEST= 0
INDE  16  26  42 FOBS=   101.1 SIGMA=   1.7 PHAS=    22.0 FOM=  0.79 TEST= 0
INDE  16  26  44 FOBS=    47.1 SIGMA=   3.5 PHAS=   -54.7 FOM=  0.84 TEST= 0
INDE  16  26  46 FOBS=    58.6 SIGMA=   3.3 PHAS=   -28.0 FOM=  0.80 TEST= 0
INDE  16  26  48 FOBS=    93.7 SIGMA=   1.6 PHAS=   162.5 FOM=  0.78 TEST= 0
INDE  16  26  50 FOBS=    30.5 SIGMA=   5.0 PHAS=  -138.2 FOM=  0.09 TEST= 0
INDE  16  26  52 FOBS=   123.6 SIGMA=   1.2 PHAS=    -3.8 FOM=  0.92 TEST= 0
INDE  16  26  54 FOBS=    71.0 SIGMA=   2.2 PHAS=  -157.4 FOM=  0.86 TEST= 0
INDE  16  26  56 FOBS=    88.4 SIGMA=   2.0 PHAS=  -153.1 FOM=  0.85 TEST= 0
INDE  16  26  58 FOBS=    54.0 SIGMA=   3.6 PHAS=   138.8 FOM=  0.18 TEST= 0
INDE  16  26  60 FOBS=    50.8 SIGMA=   4.1 PHAS=   134.0 FOM=  0.69 TEST= 0
INDE  16  26  62 FOBS=    68.3 SIGMA=   3.9 PHAS=   -79.2 FOM=  0.81 TEST= 0
INDE  16  26  64 FOBS=    47.8 SIGMA=  10.8 PHAS=   124.4 FOM=  0.81 TEST= 0
INDE  16  26  66 FOBS=    43.1 SIGMA=  12.4 PHAS=    -6.7 FOM=  0.77 TEST= 0
INDE  16  26  68 FOBS=    79.6 SIGMA=   6.8 PHAS=    -9.0 FOM=  0.85 TEST= 0
INDE  16  26  70 FOBS=    25.3 SIGMA=  21.9 PHAS=  -110.7 FOM=  0.06 TEST= 1
INDE  16  27  17 FOBS=   109.6 SIGMA=   1.1 PHAS=  -144.3 FOM=  0.94 TEST= 0
INDE  16  27  19 FOBS=   223.2 SIGMA=   0.6 PHAS=   172.0 FOM=  0.92 TEST= 0
INDE  16  27  21 FOBS=    76.4 SIGMA=   1.5 PHAS=  -151.3 FOM=  0.91 TEST= 0
INDE  16  27  23 FOBS=   208.2 SIGMA=   0.7 PHAS=   113.2 FOM=  0.93 TEST= 0
INDE  16  27  25 FOBS=   175.9 SIGMA=   0.8 PHAS=   -48.9 FOM=  0.92 TEST= 0
INDE  16  27  27 FOBS=   234.9 SIGMA=   0.6 PHAS=   -51.2 FOM=  0.97 TEST= 0
INDE  16  27  29 FOBS=    83.5 SIGMA=   1.6 PHAS=  -133.6 FOM=  0.52 TEST= 0
INDE  16  27  31 FOBS=   176.4 SIGMA=   0.9 PHAS=   178.7 FOM=  0.95 TEST= 0
INDE  16  27  33 FOBS=   140.5 SIGMA=   1.1 PHAS=   175.7 FOM=  0.79 TEST= 0
INDE  16  27  35 FOBS=   122.7 SIGMA=   1.4 PHAS=   164.4 FOM=  0.96 TEST= 0
INDE  16  27  37 FOBS=    56.6 SIGMA=   3.6 PHAS=   128.1 FOM=  0.65 TEST= 0
INDE  16  27  39 FOBS=   193.5 SIGMA=   1.0 PHAS=  -159.4 FOM=  0.93 TEST= 0
INDE  16  27  41 FOBS=    77.9 SIGMA=   2.2 PHAS=    35.7 FOM=  0.69 TEST= 0
INDE  16  27  43 FOBS=    49.2 SIGMA=   3.4 PHAS=  -126.9 FOM=  0.50 TEST= 0
INDE  16  27  45 FOBS=   142.7 SIGMA=   1.2 PHAS=  -130.4 FOM=  0.59 TEST= 1
INDE  16  27  47 FOBS=   117.8 SIGMA=   1.4 PHAS=  -165.3 FOM=  0.87 TEST= 0
INDE  16  27  49 FOBS=    81.3 SIGMA=   1.8 PHAS=    47.6 FOM=  0.93 TEST= 0
INDE  16  27  51 FOBS=   163.8 SIGMA=   1.0 PHAS=   -59.7 FOM=  0.95 TEST= 0
INDE  16  27  53 FOBS=    74.8 SIGMA=   2.0 PHAS=  -125.5 FOM=  0.83 TEST= 0
INDE  16  27  55 FOBS=    55.3 SIGMA=   3.0 PHAS=   151.5 FOM=  0.82 TEST= 0
INDE  16  27  57 FOBS=    57.7 SIGMA=   3.2 PHAS=  -141.2 FOM=  0.01 TEST= 1
```

*FIG. 12A - 380*

```
INDE 16 27 59 FOBS=   99.9 SIGMA=  2.0 PHAS=  -32.5 FOM= 0.90 TEST= 0
INDE 16 27 61 FOBS=  103.3 SIGMA=  2.6 PHAS=  137.3 FOM= 0.92 TEST= 0
INDE 16 27 63 FOBS=   30.7 SIGMA= 10.0 PHAS= -136.7 FOM= 0.22 TEST= 0
INDE 16 27 65 FOBS=    0.0 SIGMA= 32.4 PHAS=    0.0 FOM= 0.00 TEST= 0
INDE 16 27 67 FOBS=   56.4 SIGMA=  9.5 PHAS= -149.5 FOM= 0.77 TEST= 0
INDE 16 27 69 FOBS=    0.0 SIGMA= 33.2 PHAS=    0.0 FOM= 0.00 TEST= 0
INDE 16 27 71 FOBS=    0.0 SIGMA= 19.6 PHAS=    0.0 FOM= 0.00 TEST= 0
INDE 16 28 16 FOBS=   20.6 SIGMA=  4.8 PHAS=   60.4 FOM= 0.19 TEST= 0
INDE 16 28 18 FOBS=  384.2 SIGMA=  0.5 PHAS=  141.9 FOM= 0.98 TEST= 0
INDE 16 28 20 FOBS=   95.8 SIGMA=  1.3 PHAS=  100.4 FOM= 0.93 TEST= 0
INDE 16 28 22 FOBS=  132.9 SIGMA=  1.0 PHAS=   43.2 FOM= 0.98 TEST= 0
INDE 16 28 24 FOBS=   85.2 SIGMA=  1.5 PHAS=  156.3 FOM= 0.46 TEST= 0
INDE 16 28 26 FOBS=  115.5 SIGMA=  1.2 PHAS= -128.9 FOM= 0.90 TEST= 0
INDE 16 28 28 FOBS=  209.3 SIGMA=  0.7 PHAS=  141.5 FOM= 0.95 TEST= 0
INDE 16 28 30 FOBS=  180.9 SIGMA=  0.9 PHAS= -148.3 FOM= 0.91 TEST= 1
INDE 16 28 32 FOBS=   93.5 SIGMA=  1.7 PHAS=   -4.5 FOM= 0.78 TEST= 0
INDE 16 28 34 FOBS=   46.9 SIGMA=  3.9 PHAS= -176.4 FOM= 0.27 TEST= 0
INDE 16 28 36 FOBS=  133.1 SIGMA=  1.5 PHAS=  167.0 FOM= 0.92 TEST= 1
INDE 16 28 38 FOBS=  170.3 SIGMA=  1.1 PHAS=   94.3 FOM= 0.88 TEST= 0
INDE 16 28 40 FOBS=   95.2 SIGMA=  1.8 PHAS=  -19.0 FOM= 0.47 TEST= 0
INDE 16 28 42 FOBS=   79.7 SIGMA=  2.1 PHAS=    3.7 FOM= 0.94 TEST= 0
INDE 16 28 44 FOBS=   25.5 SIGMA=  6.7 PHAS=   38.1 FOM= 0.01 TEST= 0
INDE 16 28 46 FOBS=   30.6 SIGMA=  5.6 PHAS=   75.9 FOM= 0.43 TEST= 0
INDE 16 28 48 FOBS=  100.2 SIGMA=  1.6 PHAS=  150.0 FOM= 0.94 TEST= 0
INDE 16 28 50 FOBS=  116.4 SIGMA=  1.3 PHAS= -143.1 FOM= 0.93 TEST= 0
INDE 16 28 52 FOBS=   62.9 SIGMA=  2.3 PHAS=  137.1 FOM= 0.88 TEST= 0
INDE 16 28 54 FOBS=   91.7 SIGMA=  1.6 PHAS= -170.4 FOM= 0.15 TEST= 1
INDE 16 28 56 FOBS=   80.0 SIGMA=  2.0 PHAS=  172.8 FOM= 0.89 TEST= 0
INDE 16 28 58 FOBS=   89.4 SIGMA=  2.1 PHAS=  123.8 FOM= 0.36 TEST= 1
INDE 16 28 60 FOBS=   34.8 SIGMA=  6.1 PHAS=   61.7 FOM= 0.60 TEST= 0
INDE 16 28 62 FOBS=   38.0 SIGMA=  8.0 PHAS=   14.4 FOM= 0.75 TEST= 0
INDE 16 28 64 FOBS=    0.0 SIGMA= 31.8 PHAS=    0.0 FOM= 0.00 TEST= 0
INDE 16 28 66 FOBS=    0.0 SIGMA= 32.2 PHAS=    0.0 FOM= 0.00 TEST= 1
INDE 16 28 68 FOBS=    0.0 SIGMA= 32.7 PHAS=    0.0 FOM= 0.00 TEST= 0
INDE 16 28 70 FOBS=    0.0 SIGMA= 33.6 PHAS=    0.0 FOM= 0.00 TEST= 0
INDE 16 29 17 FOBS=  182.1 SIGMA=  0.7 PHAS=  107.7 FOM= 0.94 TEST= 0
INDE 16 29 19 FOBS=  257.4 SIGMA=  0.5 PHAS=   95.3 FOM= 0.99 TEST= 0
INDE 16 29 21 FOBS=   76.4 SIGMA=  1.6 PHAS=  -89.7 FOM= 0.99 TEST= 0
INDE 16 29 23 FOBS=   98.6 SIGMA=  1.3 PHAS=   61.4 FOM= 0.93 TEST= 0
INDE 16 29 25 FOBS=  251.3 SIGMA=  0.7 PHAS= -151.3 FOM= 0.93 TEST= 0
INDE 16 29 27 FOBS=  203.0 SIGMA=  0.8 PHAS=   73.3 FOM= 0.84 TEST= 0
INDE 16 29 29 FOBS=  225.5 SIGMA=  0.7 PHAS=   44.8 FOM= 0.98 TEST= 0
INDE 16 29 31 FOBS=  101.8 SIGMA=  1.6 PHAS=  125.9 FOM= 0.66 TEST= 0
INDE 16 29 33 FOBS=   72.8 SIGMA=  2.6 PHAS=  175.0 FOM= 0.93 TEST= 0
INDE 16 29 35 FOBS=  166.3 SIGMA=  1.2 PHAS=   93.5 FOM= 0.85 TEST= 0
INDE 16 29 37 FOBS=  113.7 SIGMA=  1.8 PHAS=   14.6 FOM= 0.90 TEST= 0
INDE 16 29 39 FOBS=    0.0 SIGMA= 18.5 PHAS=    0.0 FOM= 0.00 TEST= 0
INDE 16 29 41 FOBS=  157.0 SIGMA=  1.1 PHAS=  -46.7 FOM= 0.89 TEST= 0
INDE 16 29 43 FOBS=   60.4 SIGMA=  2.8 PHAS= -164.2 FOM= 0.57 TEST= 1
INDE 16 29 45 FOBS=    0.0 SIGMA= 18.5 PHAS=    0.0 FOM= 0.00 TEST= 1
INDE 16 29 47 FOBS=   31.1 SIGMA=  5.4 PHAS=  104.8 FOM= 0.67 TEST= 0
INDE 16 29 49 FOBS=  129.9 SIGMA=  1.3 PHAS=  102.4 FOM= 0.92 TEST= 0
INDE 16 29 51 FOBS=   44.2 SIGMA=  3.6 PHAS=    7.5 FOM= 0.94 TEST= 0
INDE 16 29 53 FOBS=    0.0 SIGMA= 17.9 PHAS=    0.0 FOM= 0.00 TEST= 0
INDE 16 29 55 FOBS=    0.0 SIGMA= 17.8 PHAS=    0.0 FOM= 0.00 TEST= 0
INDE 16 29 57 FOBS=  109.1 SIGMA=  1.6 PHAS=   36.7 FOM= 0.91 TEST= 0
INDE 16 29 59 FOBS=   51.4 SIGMA=  4.1 PHAS=   44.5 FOM= 0.06 TEST= 0
INDE 16 29 61 FOBS=   55.9 SIGMA=  4.2 PHAS=   17.0 FOM= 0.59 TEST= 0
INDE 16 29 63 FOBS=   36.9 SIGMA=  9.6 PHAS= -127.7 FOM= 0.57 TEST= 0
INDE 16 29 65 FOBS=   73.0 SIGMA=  6.9 PHAS=   61.8 FOM= 0.83 TEST= 0
INDE 16 29 67 FOBS=   30.0 SIGMA= 18.0 PHAS=  109.5 FOM= 0.49 TEST= 0
INDE 16 29 69 FOBS=    0.0 SIGMA= 32.9 PHAS=    0.0 FOM= 0.00 TEST= 0
INDE 16 30 16 FOBS=  200.1 SIGMA=  0.6 PHAS=   -3.6 FOM= 0.73 TEST= 1
INDE 16 30 18 FOBS=  258.0 SIGMA=  0.6 PHAS=   46.6 FOM= 0.95 TEST= 0
INDE 16 30 20 FOBS=  115.8 SIGMA=  1.0 PHAS=   64.8 FOM= 0.96 TEST= 0
INDE 16 30 22 FOBS=   32.0 SIGMA=  3.7 PHAS=   43.6 FOM= 0.22 TEST= 0
INDE 16 30 24 FOBS=  242.0 SIGMA=  0.7 PHAS=   87.8 FOM= 0.97 TEST= 0
INDE 16 30 26 FOBS=  403.1 SIGMA=  0.7 PHAS=  -43.5 FOM= 0.51 TEST= 1
INDE 16 30 28 FOBS=   36.9 SIGMA=  3.9 PHAS=    7.7 FOM= 0.83 TEST= 0
INDE 16 30 30 FOBS=  197.5 SIGMA=  1.0 PHAS= -113.1 FOM= 0.96 TEST= 0
```

*FIG. 12A - 381*

```
INDE 16 30 32 FOBS=  134.3 SIGMA=  1.4 PHAS=  -77.8 FOM= 0.87 TEST= 0
INDE 16 30 34 FOBS=  245.1 SIGMA=  1.0 PHAS=  -96.7 FOM= 0.92 TEST= 0
INDE 16 30 36 FOBS=   52.6 SIGMA=  3.9 PHAS=  174.1 FOM= 0.82 TEST= 0
INDE 16 30 38 FOBS=   98.5 SIGMA=  2.0 PHAS= -145.9 FOM= 0.45 TEST= 0
INDE 16 30 40 FOBS=   69.6 SIGMA=  2.7 PHAS=    3.6 FOM= 0.83 TEST= 0
INDE 16 30 42 FOBS=   59.9 SIGMA=  2.8 PHAS= -129.7 FOM= 0.64 TEST= 0
INDE 16 30 44 FOBS=   41.9 SIGMA=  4.2 PHAS=  113.4 FOM= 0.74 TEST= 0
INDE 16 30 46 FOBS=   70.3 SIGMA=  2.4 PHAS=   16.6 FOM= 0.92 TEST= 0
INDE 16 30 48 FOBS=  180.7 SIGMA=  1.0 PHAS=   96.5 FOM= 0.95 TEST= 0
INDE 16 30 50 FOBS=   75.0 SIGMA=  2.1 PHAS=  -92.9 FOM= 0.78 TEST= 1
INDE 16 30 52 FOBS=   35.8 SIGMA=  4.3 PHAS=  116.9 FOM= 0.62 TEST= 0
INDE 16 30 54 FOBS=   40.6 SIGMA=  4.0 PHAS=  170.7 FOM= 0.17 TEST= 1
INDE 16 30 56 FOBS=   40.6 SIGMA=  4.8 PHAS=   28.5 FOM= 0.40 TEST= 0
INDE 16 30 58 FOBS=   84.5 SIGMA=  2.2 PHAS=  -38.7 FOM= 0.79 TEST= 0
INDE 16 30 60 FOBS=   83.5 SIGMA=  2.6 PHAS=   41.9 FOM= 0.79 TEST= 0
INDE 16 30 62 FOBS=   37.6 SIGMA=  7.9 PHAS=    1.9 FOM= 0.41 TEST= 0
INDE 16 30 64 FOBS=   37.8 SIGMA= 13.1 PHAS=  -30.5 FOM= 0.67 TEST= 0
INDE 16 30 66 FOBS=    0.0 SIGMA= 32.2 PHAS=    0.0 FOM= 0.00 TEST= 1
INDE 16 30 68 FOBS=    0.0 SIGMA= 32.7 PHAS=    0.0 FOM= 0.00 TEST= 0
INDE 16 31 17 FOBS=  119.7 SIGMA=  1.0 PHAS= -157.7 FOM= 0.93 TEST= 0
INDE 16 31 19 FOBS=   79.8 SIGMA=  1.4 PHAS=  -67.3 FOM= 0.92 TEST= 0
INDE 16 31 21 FOBS=   56.6 SIGMA=  2.1 PHAS=  -13.2 FOM= 0.82 TEST= 0
INDE 16 31 23 FOBS=   33.7 SIGMA=  3.6 PHAS= -124.5 FOM= 0.23 TEST= 0
INDE 16 31 25 FOBS=   58.6 SIGMA=  2.5 PHAS=   67.3 FOM= 0.86 TEST= 0
INDE 16 31 27 FOBS=  120.3 SIGMA=  1.3 PHAS=  154.4 FOM= 0.32 TEST= 1
INDE 16 31 29 FOBS=  132.9 SIGMA=  1.2 PHAS=   52.9 FOM= 0.86 TEST= 0
INDE 16 31 31 FOBS=   84.3 SIGMA=  2.2 PHAS=  178.8 FOM= 0.92 TEST= 0
INDE 16 31 33 FOBS=  216.9 SIGMA=  1.0 PHAS=  169.6 FOM= 0.83 TEST= 1
INDE 16 31 35 FOBS=  136.0 SIGMA=  1.5 PHAS= -129.0 FOM= 0.94 TEST= 0
INDE 16 31 37 FOBS=   54.6 SIGMA=  3.6 PHAS=  -48.7 FOM= 0.76 TEST= 0
INDE 16 31 39 FOBS=   66.8 SIGMA=  2.9 PHAS= -104.1 FOM= 0.71 TEST= 0
INDE 16 31 41 FOBS=  116.8 SIGMA=  1.7 PHAS= -118.6 FOM= 0.86 TEST= 0
INDE 16 31 43 FOBS=  101.0 SIGMA=  1.8 PHAS=  142.3 FOM= 0.86 TEST= 0
INDE 16 31 45 FOBS=  172.6 SIGMA=  1.1 PHAS=  -18.0 FOM= 0.96 TEST= 0
INDE 16 31 47 FOBS=  154.8 SIGMA=  1.1 PHAS=   -8.7 FOM= 0.94 TEST= 0
INDE 16 31 49 FOBS=  163.9 SIGMA=  1.2 PHAS=  -36.6 FOM= 0.90 TEST= 0
INDE 16 31 51 FOBS=   78.6 SIGMA=  2.0 PHAS=  -58.6 FOM= 0.89 TEST= 0
INDE 16 31 53 FOBS=   12.0 SIGMA= 15.9 PHAS=  152.2 FOM= 0.17 TEST= 0
INDE 16 31 55 FOBS=  103.4 SIGMA=  2.1 PHAS=  -56.3 FOM= 0.91 TEST= 0
INDE 16 31 57 FOBS=    0.0 SIGMA= 19.8 PHAS=    0.0 FOM= 0.00 TEST= 0
INDE 16 31 59 FOBS=   15.3 SIGMA= 12.0 PHAS= -156.3 FOM= 0.15 TEST= 0
INDE 16 31 61 FOBS=   93.1 SIGMA=  2.8 PHAS=  -41.9 FOM= 0.93 TEST= 0
INDE 16 31 63 FOBS=   39.1 SIGMA=  7.6 PHAS=  167.3 FOM= 0.77 TEST= 0
INDE 16 31 65 FOBS=    0.0 SIGMA= 31.7 PHAS=    0.0 FOM= 0.00 TEST= 0
INDE 16 31 67 FOBS=    0.0 SIGMA= 32.3 PHAS=    0.0 FOM= 0.00 TEST= 0
INDE 16 31 69 FOBS=    0.0 SIGMA= 33.2 PHAS=    0.0 FOM= 0.00 TEST= 0
INDE 16 32 16 FOBS=  319.5 SIGMA=  0.5 PHAS=   69.7 FOM= 0.95 TEST= 0
INDE 16 32 18 FOBS=  187.5 SIGMA=  0.8 PHAS=   99.2 FOM= 0.88 TEST= 0
INDE 16 32 20 FOBS=   44.1 SIGMA=  2.7 PHAS= -155.1 FOM= 0.96 TEST= 0
INDE 16 32 22 FOBS=  196.9 SIGMA=  0.8 PHAS= -119.5 FOM= 0.89 TEST= 0
INDE 16 32 24 FOBS=  172.6 SIGMA=  0.8 PHAS=   13.6 FOM= 0.94 TEST= 0
INDE 16 32 26 FOBS=  328.2 SIGMA=  0.7 PHAS=   86.3 FOM= 0.94 TEST= 0
INDE 16 32 28 FOBS=   59.4 SIGMA=  3.0 PHAS=  -22.3 FOM= 0.90 TEST= 0
INDE 16 32 30 FOBS=  182.3 SIGMA=  1.0 PHAS=  173.0 FOM= 0.98 TEST= 0
INDE 16 32 32 FOBS=  188.0 SIGMA=  1.8 PHAS= -177.3 FOM= 0.76 TEST= 1
INDE 16 32 34 FOBS=   75.2 SIGMA=  2.7 PHAS=  176.8 FOM= 0.93 TEST= 0
INDE 16 32 36 FOBS=  166.1 SIGMA=  1.3 PHAS= -158.4 FOM= 0.58 TEST= 1
INDE 16 32 38 FOBS=  211.4 SIGMA=  1.0 PHAS=  118.8 FOM= 0.92 TEST= 0
INDE 16 32 40 FOBS=   71.1 SIGMA=  2.7 PHAS= -114.1 FOM= 0.63 TEST= 0
INDE 16 32 42 FOBS=   46.9 SIGMA=  4.2 PHAS=  -69.3 FOM= 0.53 TEST= 0
INDE 16 32 44 FOBS=  168.8 SIGMA=  1.2 PHAS= -138.7 FOM= 0.94 TEST= 0
INDE 16 32 46 FOBS=  222.1 SIGMA=  0.9 PHAS= -112.6 FOM= 0.96 TEST= 0
INDE 16 32 48 FOBS=  117.7 SIGMA=  1.4 PHAS= -155.0 FOM= 0.71 TEST= 0
INDE 16 32 50 FOBS=   41.9 SIGMA=  3.8 PHAS= -147.2 FOM= 0.82 TEST= 0
INDE 16 32 52 FOBS=   75.4 SIGMA=  2.3 PHAS=   70.6 FOM= 0.94 TEST= 0
INDE 16 32 54 FOBS=   50.8 SIGMA=  3.9 PHAS= -133.1 FOM= 0.51 TEST= 0
INDE 16 32 56 FOBS=   44.4 SIGMA=  4.8 PHAS=  -65.5 FOM= 0.47 TEST= 0
INDE 16 32 58 FOBS=    0.0 SIGMA= 22.6 PHAS=    0.0 FOM= 0.00 TEST= 0
INDE 16 32 60 FOBS=    7.4 SIGMA= 28.8 PHAS=   55.7 FOM= 0.04 TEST= 0
INDE 16 32 62 FOBS=   37.8 SIGMA=  6.8 PHAS=  -13.3 FOM= 0.31 TEST= 0
```

*FIG. 12A - 382*

```
INDE  16  32  64  FOBS=   35.7  SIGMA=   8.5  PHAS=   74.8  FOM=  0.63  TEST= 0
INDE  16  32  66  FOBS=   28.1  SIGMA=  13.6  PHAS= -170.0  FOM=  0.35  TEST= 0
INDE  16  32  68  FOBS=    0.0  SIGMA=  32.4  PHAS=    0.0  FOM=  0.00  TEST= 0
INDE  16  33  17  FOBS=   89.9  SIGMA=   1.4  PHAS=  -43.9  FOM=  0.51  TEST= 0
INDE  16  33  19  FOBS=  174.6  SIGMA=   0.8  PHAS= -145.9  FOM=  0.91  TEST= 0
INDE  16  33  21  FOBS=  326.5  SIGMA=   0.6  PHAS=  101.7  FOM=  0.98  TEST= 0
INDE  16  33  23  FOBS=  135.1  SIGMA=   1.1  PHAS=  177.8  FOM=  0.94  TEST= 0
INDE  16  33  25  FOBS=    0.0  SIGMA=  17.4  PHAS=    0.0  FOM=  0.00  TEST= 0
INDE  16  33  27  FOBS=   24.6  SIGMA=   7.0  PHAS=   -5.6  FOM=  0.36  TEST= 0
INDE  16  33  29  FOBS=  177.7  SIGMA=   1.1  PHAS= -171.9  FOM=  0.93  TEST= 0
INDE  16  33  31  FOBS=  317.1  SIGMA=   0.8  PHAS=   57.6  FOM=  0.95  TEST= 0
INDE  16  33  33  FOBS=  108.7  SIGMA=   2.1  PHAS=   98.6  FOM=  0.92  TEST= 0
INDE  16  33  35  FOBS=   84.1  SIGMA=   2.4  PHAS=   48.0  FOM=  0.84  TEST= 0
INDE  16  33  37  FOBS=   68.6  SIGMA=   2.8  PHAS=  -71.7  FOM=  0.69  TEST= 0
INDE  16  33  39  FOBS=   78.4  SIGMA=   2.5  PHAS=   71.0  FOM=  0.84  TEST= 1
INDE  16  33  41  FOBS=    0.0  SIGMA=  19.3  PHAS=    0.0  FOM=  0.00  TEST= 0
INDE  16  33  43  FOBS=  112.4  SIGMA=   1.7  PHAS=  108.7  FOM=  0.90  TEST= 0
INDE  16  33  45  FOBS=   77.8  SIGMA=   2.4  PHAS=  122.0  FOM=  0.87  TEST= 0
INDE  16  33  47  FOBS=  103.7  SIGMA=   1.8  PHAS= -170.3  FOM=  0.94  TEST= 0
INDE  16  33  49  FOBS=    0.0  SIGMA=  18.7  PHAS=    0.0  FOM=  0.00  TEST= 0
INDE  16  33  51  FOBS=   61.4  SIGMA=   3.1  PHAS=  -29.4  FOM=  0.79  TEST= 0
INDE  16  33  53  FOBS=  136.7  SIGMA=   1.7  PHAS=  -57.5  FOM=  0.95  TEST= 0
INDE  16  33  55  FOBS=   67.5  SIGMA=   3.2  PHAS=   97.8  FOM=  0.51  TEST= 0
INDE  16  33  57  FOBS=   20.9  SIGMA=  10.1  PHAS= -164.0  FOM=  0.17  TEST= 0
INDE  16  33  59  FOBS=   58.9  SIGMA=   3.6  PHAS=  -64.9  FOM=  0.78  TEST= 0
INDE  16  33  61  FOBS=   61.7  SIGMA=   3.4  PHAS=  -31.9  FOM=  0.61  TEST= 0
INDE  16  33  63  FOBS=   53.9  SIGMA=   4.3  PHAS=   97.9  FOM=  0.70  TEST= 0
INDE  16  33  65  FOBS=   22.1  SIGMA=  13.9  PHAS=   28.6  FOM=  0.25  TEST= 0
INDE  16  33  67  FOBS=    0.0  SIGMA=  27.6  PHAS=    0.0  FOM=  0.00  TEST= 0
INDE  16  34  16  FOBS=  119.8  SIGMA=   1.1  PHAS=   96.0  FOM=  0.53  TEST= 0
INDE  16  34  18  FOBS=  360.7  SIGMA=   0.6  PHAS=  101.5  FOM=  0.96  TEST= 0
INDE  16  34  20  FOBS=  277.7  SIGMA=   0.7  PHAS=   57.8  FOM=  0.95  TEST= 0
INDE  16  34  22  FOBS=   64.6  SIGMA=   2.3  PHAS=    6.0  FOM=  0.52  TEST= 0
INDE  16  34  24  FOBS=  187.8  SIGMA=   1.0  PHAS=  -29.0  FOM=  0.79  TEST= 0
INDE  16  34  26  FOBS=   71.5  SIGMA=   2.3  PHAS=   63.3  FOM=  0.90  TEST= 0
INDE  16  34  28  FOBS=  175.9  SIGMA=   1.1  PHAS=   98.6  FOM=  0.93  TEST= 0
INDE  16  34  30  FOBS=  186.2  SIGMA=   1.1  PHAS= -174.5  FOM=  0.96  TEST= 0
INDE  16  34  32  FOBS=  141.0  SIGMA=   1.5  PHAS=   19.8  FOM=  0.92  TEST= 0
INDE  16  34  34  FOBS=   63.0  SIGMA=   3.2  PHAS=  -71.1  FOM=  0.95  TEST= 0
INDE  16  34  36  FOBS=  235.5  SIGMA=   1.0  PHAS= -112.5  FOM=  0.96  TEST= 0
INDE  16  34  38  FOBS=  123.7  SIGMA=   1.6  PHAS=  149.1  FOM=  0.98  TEST= 0
INDE  16  34  40  FOBS=  119.9  SIGMA=   1.6  PHAS=  -15.4  FOM=  0.89  TEST= 0
INDE  16  34  42  FOBS=   91.1  SIGMA=   2.1  PHAS=  -62.4  FOM=  0.92  TEST= 1
INDE  16  34  44  FOBS=  119.3  SIGMA=   1.6  PHAS=  -31.2  FOM=  0.60  TEST= 0
INDE  16  34  46  FOBS=   99.8  SIGMA=   1.9  PHAS=  130.5  FOM=  0.78  TEST= 0
INDE  16  34  48  FOBS=  148.5  SIGMA=   1.4  PHAS=  118.8  FOM=  0.95  TEST= 0
INDE  16  34  50  FOBS=  104.1  SIGMA=   1.9  PHAS=   80.1  FOM=  0.86  TEST= 0
INDE  16  34  52  FOBS=  163.1  SIGMA=   1.3  PHAS= -172.5  FOM=  0.97  TEST= 0
INDE  16  34  54  FOBS=   54.4  SIGMA=   3.9  PHAS= -107.1  FOM=  0.84  TEST= 0
INDE  16  34  56  FOBS=   88.9  SIGMA=   2.4  PHAS=  -57.9  FOM=  0.85  TEST= 0
INDE  16  34  58  FOBS=   40.7  SIGMA=   5.7  PHAS=   53.0  FOM=  0.32  TEST= 1
INDE  16  34  60  FOBS=   49.4  SIGMA=   4.3  PHAS=  -95.9  FOM=  0.87  TEST= 0
INDE  16  34  62  FOBS=    0.0  SIGMA=  20.6  PHAS=    0.0  FOM=  0.00  TEST= 0
INDE  16  34  64  FOBS=    0.0  SIGMA=  20.7  PHAS=    0.0  FOM=  0.00  TEST= 1
INDE  16  34  66  FOBS=    0.0  SIGMA=  25.0  PHAS=    0.0  FOM=  0.00  TEST= 0
INDE  16  34  68  FOBS=    0.0  SIGMA=  28.1  PHAS=    0.0  FOM=  0.00  TEST= 0
INDE  16  35  17  FOBS=  138.2  SIGMA=   1.0  PHAS=  100.2  FOM=  0.74  TEST= 0
INDE  16  35  19  FOBS=  287.5  SIGMA=   0.7  PHAS=  -19.7  FOM=  0.96  TEST= 0
INDE  16  35  21  FOBS=  146.1  SIGMA=   1.1  PHAS=  112.6  FOM=  0.88  TEST= 0
INDE  16  35  23  FOBS=  156.6  SIGMA=   1.1  PHAS=  169.2  FOM=  0.94  TEST= 0
INDE  16  35  25  FOBS=  217.1  SIGMA=   0.9  PHAS= -125.9  FOM=  0.94  TEST= 0
INDE  16  35  27  FOBS=  148.1  SIGMA=   1.3  PHAS=   15.7  FOM=  0.98  TEST= 0
INDE  16  35  29  FOBS=   77.2  SIGMA=   2.3  PHAS=   66.1  FOM=  0.96  TEST= 1
INDE  16  35  31  FOBS=  120.8  SIGMA=   1.9  PHAS= -108.1  FOM=  0.76  TEST= 0
INDE  16  35  33  FOBS=  143.2  SIGMA=   1.5  PHAS=  164.1  FOM=  0.98  TEST= 0
INDE  16  35  35  FOBS=  156.5  SIGMA=   1.3  PHAS=  109.4  FOM=  0.91  TEST= 0
INDE  16  35  37  FOBS=    0.0  SIGMA=  20.3  PHAS=    0.0  FOM=  0.00  TEST= 1
INDE  16  35  39  FOBS=   78.6  SIGMA=   2.5  PHAS=  -42.7  FOM=  0.86  TEST= 0
INDE  16  35  41  FOBS=    0.0  SIGMA=  21.4  PHAS=    0.0  FOM=  0.00  TEST= 0
INDE  16  35  43  FOBS=  115.5  SIGMA=   1.7  PHAS=  154.9  FOM=  0.93  TEST= 0
```

*FIG. 12A - 383*

```
INDE  16  35  45  FOBS=   83.0  SIGMA=   2.5  PHAS=   19.7  FOM=  0.85  TEST= 0
INDE  16  35  47  FOBS=   83.5  SIGMA=   2.7  PHAS=  -70.1  FOM=  0.28  TEST= 1
INDE  16  35  49  FOBS=  151.5  SIGMA=   1.7  PHAS=  -27.3  FOM=  0.96  TEST= 0
INDE  16  35  51  FOBS=  139.7  SIGMA=   1.7  PHAS=   15.5  FOM=  0.96  TEST= 0
INDE  16  35  53  FOBS=   44.3  SIGMA=   4.9  PHAS=   93.8  FOM=  0.36  TEST= 0
INDE  16  35  55  FOBS=  100.7  SIGMA=   2.2  PHAS= -178.5  FOM=  0.92  TEST= 0
INDE  16  35  57  FOBS=   56.7  SIGMA=   3.8  PHAS=  -85.3  FOM=  0.87  TEST= 0
INDE  16  35  59  FOBS=   63.1  SIGMA=   3.4  PHAS= -177.9  FOM=  0.86  TEST= 0
INDE  16  35  61  FOBS=    0.0  SIGMA=  24.2  PHAS=    0.0  FOM=  0.00  TEST= 0
INDE  16  35  63  FOBS=    0.0  SIGMA=  24.6  PHAS=    0.0  FOM=  0.00  TEST= 0
INDE  16  35  65  FOBS=   33.3  SIGMA=   9.5  PHAS=    6.0  FOM=  0.27  TEST= 0
INDE  16  35  67  FOBS=   36.6  SIGMA=   8.8  PHAS=   -0.2  FOM=  0.18  TEST= 0
INDE  16  36  16  FOBS=   89.8  SIGMA=   1.5  PHAS= -143.1  FOM=  0.85  TEST= 0
INDE  16  36  18  FOBS=  137.9  SIGMA=   1.2  PHAS= -141.6  FOM=  0.85  TEST= 0
INDE  16  36  20  FOBS=  153.3  SIGMA=   1.1  PHAS=  106.4  FOM=  0.97  TEST= 0
INDE  16  36  22  FOBS=  199.5  SIGMA=   0.9  PHAS=  -83.9  FOM=  0.90  TEST= 0
INDE  16  36  24  FOBS=  154.6  SIGMA=   1.2  PHAS= -169.7  FOM=  0.87  TEST= 0
INDE  16  36  26  FOBS=  135.6  SIGMA=   1.4  PHAS=  165.1  FOM=  0.94  TEST= 0
INDE  16  36  28  FOBS=  151.1  SIGMA=   1.3  PHAS=  -25.4  FOM=  0.81  TEST= 0
INDE  16  36  30  FOBS=  172.8  SIGMA=   1.1  PHAS= -168.6  FOM=  0.97  TEST= 0
INDE  16  36  32  FOBS=   39.7  SIGMA=   4.9  PHAS=  -14.7  FOM=  0.59  TEST= 0
INDE  16  36  34  FOBS=  138.4  SIGMA=   1.5  PHAS=    7.3  FOM=  0.88  TEST= 0
INDE  16  36  36  FOBS=  113.5  SIGMA=   1.8  PHAS= -146.0  FOM=  0.81  TEST= 0
INDE  16  36  38  FOBS=  241.1  SIGMA=   1.0  PHAS= -174.9  FOM=  0.97  TEST= 0
INDE  16  36  40  FOBS=  102.8  SIGMA=   1.9  PHAS=  -98.2  FOM=  0.91  TEST= 0
INDE  16  36  42  FOBS=   85.2  SIGMA=   2.2  PHAS=  131.0  FOM=  0.80  TEST= 0
INDE  16  36  44  FOBS=   67.9  SIGMA=   3.0  PHAS=   22.0  FOM=  0.80  TEST= 0
INDE  16  36  46  FOBS=   43.7  SIGMA=   5.2  PHAS=  -96.3  FOM=  0.42  TEST= 0
INDE  16  36  48  FOBS=   58.5  SIGMA=   3.8  PHAS=  162.8  FOM=  0.80  TEST= 0
INDE  16  36  50  FOBS=   23.9  SIGMA=   9.1  PHAS=  -89.5  FOM=  0.29  TEST= 0
INDE  16  36  52  FOBS=  161.6  SIGMA=   1.5  PHAS= -134.9  FOM=  0.94  TEST= 0
INDE  16  36  54  FOBS=   93.5  SIGMA=   2.4  PHAS=  128.5  FOM=  0.90  TEST= 0
INDE  16  36  56  FOBS=   93.8  SIGMA=   2.3  PHAS=  168.0  FOM=  0.88  TEST= 0
INDE  16  36  58  FOBS=  117.2  SIGMA=   1.9  PHAS=  164.5  FOM=  0.93  TEST= 0
INDE  16  36  60  FOBS=   29.6  SIGMA=   7.9  PHAS=   79.4  FOM=  0.18  TEST= 0
INDE  16  36  62  FOBS=   50.2  SIGMA=   4.3  PHAS= -172.3  FOM=  0.42  TEST= 0
INDE  16  36  64  FOBS=  101.0  SIGMA=   2.2  PHAS=   64.8  FOM=  0.68  TEST= 0
INDE  16  36  66  FOBS=   62.1  SIGMA=   5.2  PHAS=  150.2  FOM=  0.78  TEST= 0
INDE  16  37  17  FOBS=  219.3  SIGMA=   0.8  PHAS=  141.3  FOM=  0.93  TEST= 0
INDE  16  37  19  FOBS=  109.0  SIGMA=   1.6  PHAS=   64.2  FOM=  0.77  TEST= 0
INDE  16  37  21  FOBS=   74.5  SIGMA=   2.3  PHAS=  160.1  FOM=  0.85  TEST= 1
INDE  16  37  23  FOBS=   85.8  SIGMA=   2.1  PHAS=  100.0  FOM=  0.92  TEST= 1
INDE  16  37  25  FOBS=  102.6  SIGMA=   1.9  PHAS=  109.3  FOM=  0.64  TEST= 0
INDE  16  37  27  FOBS=  183.0  SIGMA=   1.2  PHAS=  165.1  FOM=  0.91  TEST= 0
INDE  16  37  29  FOBS=   24.0  SIGMA=   8.2  PHAS=  -75.0  FOM=  0.17  TEST= 0
INDE  16  37  31  FOBS=   88.6  SIGMA=   2.0  PHAS= -122.2  FOM=  0.87  TEST= 0
INDE  16  37  33  FOBS=  144.0  SIGMA=   1.3  PHAS=  156.1  FOM=  0.95  TEST= 0
INDE  16  37  35  FOBS=    0.0  SIGMA=  20.3  PHAS=    0.0  FOM=  0.00  TEST= 0
INDE  16  37  37  FOBS=  164.9  SIGMA=   1.3  PHAS=  116.5  FOM=  0.93  TEST= 0
INDE  16  37  39  FOBS=  108.0  SIGMA=   1.8  PHAS= -167.9  FOM=  0.83  TEST= 0
INDE  16  37  41  FOBS=  139.1  SIGMA=   1.6  PHAS=  110.8  FOM=  0.90  TEST= 0
INDE  16  37  43  FOBS=    0.0  SIGMA=  21.2  PHAS=    0.0  FOM=  0.00  TEST= 0
INDE  16  37  45  FOBS=  202.9  SIGMA=   1.2  PHAS= -117.6  FOM=  0.96  TEST= 0
INDE  16  37  47  FOBS=  138.3  SIGMA=   1.7  PHAS=  -67.2  FOM=  0.93  TEST= 0
INDE  16  37  49  FOBS=   49.6  SIGMA=   4.4  PHAS=   -9.7  FOM=  0.18  TEST= 0
INDE  16  37  51  FOBS=   92.4  SIGMA=   2.4  PHAS=   46.3  FOM=  0.93  TEST= 0
INDE  16  37  53  FOBS=   89.0  SIGMA=   2.5  PHAS=  132.5  FOM=  0.10  TEST= 1
INDE  16  37  55  FOBS=  129.6  SIGMA=   1.7  PHAS=    3.7  FOM=  0.93  TEST= 0
INDE  16  37  57  FOBS=   46.0  SIGMA=   4.7  PHAS=   17.9  FOM=  0.07  TEST= 1
INDE  16  37  59  FOBS=   43.6  SIGMA=   5.4  PHAS=   83.6  FOM=  0.84  TEST= 0
INDE  16  37  61  FOBS=    4.1  SIGMA=  62.8  PHAS=   51.6  FOM=  0.11  TEST= 0
INDE  16  37  63  FOBS=   99.0  SIGMA=   2.3  PHAS= -113.0  FOM=  0.80  TEST= 0
INDE  16  37  65  FOBS=   27.3  SIGMA=  14.8  PHAS=   71.8  FOM=  0.02  TEST= 1
INDE  16  38  16  FOBS=  175.7  SIGMA=   1.0  PHAS=  -15.3  FOM=  0.96  TEST= 0
INDE  16  38  18  FOBS=  171.6  SIGMA=   1.1  PHAS=   92.4  FOM=  0.71  TEST= 0
INDE  16  38  20  FOBS=  166.8  SIGMA=   1.1  PHAS=  131.0  FOM=  0.93  TEST= 0
INDE  16  38  22  FOBS=  249.1  SIGMA=   0.9  PHAS=  -60.8  FOM=  0.96  TEST= 0
INDE  16  38  24  FOBS=  114.7  SIGMA=   1.7  PHAS= -167.6  FOM=  0.46  TEST= 0
INDE  16  38  26  FOBS=   44.3  SIGMA=   4.4  PHAS=   -9.9  FOM=  0.79  TEST= 1
INDE  16  38  28  FOBS=   67.3  SIGMA=   2.9  PHAS=  159.4  FOM=  0.30  TEST= 0
```

*FIG. 12A - 384*

```
INDE  16  38  30  FOBS=   117.1  SIGMA=   1.5  PHAS=  -100.9  FOM=  0.84  TEST= 0
INDE  16  38  32  FOBS=     0.0  SIGMA=  18.9  PHAS=     0.0  FOM=  0.00  TEST= 0
INDE  16  38  34  FOBS=    36.0  SIGMA=   4.9  PHAS=  -142.2  FOM=  0.63  TEST= 0
INDE  16  38  36  FOBS=     0.0  SIGMA=  19.8  PHAS=     0.0  FOM=  0.00  TEST= 0
INDE  16  38  38  FOBS=    46.4  SIGMA=   4.6  PHAS=   127.1  FOM=  0.36  TEST= 0
INDE  16  38  40  FOBS=    79.2  SIGMA=   2.9  PHAS=    72.4  FOM=  0.86  TEST= 0
INDE  16  38  42  FOBS=    28.1  SIGMA=   8.8  PHAS=   122.2  FOM=  0.11  TEST= 0
INDE  16  38  44  FOBS=    81.2  SIGMA=   2.8  PHAS=  -168.0  FOM=  0.09  TEST= 0
INDE  16  38  46  FOBS=   173.4  SIGMA=   1.4  PHAS=  -169.4  FOM=  0.97  TEST= 0
INDE  16  38  48  FOBS=     0.0  SIGMA=  23.0  PHAS=     0.0  FOM=  0.00  TEST= 0
INDE  16  38  50  FOBS=     0.0  SIGMA=  20.9  PHAS=     0.0  FOM=  0.00  TEST= 0
INDE  16  38  52  FOBS=   136.4  SIGMA=   1.7  PHAS=   -24.9  FOM=  0.90  TEST= 0
INDE  16  38  54  FOBS=   165.0  SIGMA=   1.4  PHAS=  -153.0  FOM=  0.95  TEST= 0
INDE  16  38  56  FOBS=    40.7  SIGMA=   5.3  PHAS=  -160.6  FOM=  0.86  TEST= 0
INDE  16  38  58  FOBS=    67.7  SIGMA=   3.2  PHAS=  -117.2  FOM=  0.88  TEST= 0
INDE  16  38  60  FOBS=    67.6  SIGMA=   3.2  PHAS=   -51.2  FOM=  0.74  TEST= 0
INDE  16  38  62  FOBS=    45.6  SIGMA=   4.8  PHAS=  -151.5  FOM=  0.62  TEST= 0
INDE  16  38  64  FOBS=     0.0  SIGMA=  27.1  PHAS=     0.0  FOM=  0.00  TEST= 0
INDE  16  39  17  FOBS=    54.0  SIGMA=   3.2  PHAS=   142.8  FOM=  0.61  TEST= 0
INDE  16  39  19  FOBS=   177.2  SIGMA=   1.1  PHAS=   108.2  FOM=  0.93  TEST= 0
INDE  16  39  21  FOBS=   191.9  SIGMA=   1.1  PHAS=   160.9  FOM=  0.98  TEST= 0
INDE  16  39  23  FOBS=   101.6  SIGMA=   2.0  PHAS=   143.0  FOM=  0.59  TEST= 0
INDE  16  39  25  FOBS=    22.7  SIGMA=   9.1  PHAS=   -87.4  FOM=  0.85  TEST= 0
INDE  16  39  27  FOBS=   252.2  SIGMA=   0.9  PHAS=   145.9  FOM=  0.95  TEST= 0
INDE  16  39  29  FOBS=    95.7  SIGMA=   1.9  PHAS=  -140.4  FOM=  0.86  TEST= 0
INDE  16  39  31  FOBS=   110.2  SIGMA=   1.6  PHAS=  -143.6  FOM=  0.79  TEST= 0
INDE  16  39  33  FOBS=   204.1  SIGMA=   0.9  PHAS=   167.7  FOM=  0.53  TEST= 1
INDE  16  39  35  FOBS=   135.8  SIGMA=   1.4  PHAS=  -107.8  FOM=  0.88  TEST= 0
INDE  16  39  37  FOBS=    61.3  SIGMA=   3.9  PHAS=    42.1  FOM=  0.10  TEST= 0
INDE  16  39  39  FOBS=   168.3  SIGMA=   1.5  PHAS=   -24.4  FOM=  0.93  TEST= 0
INDE  16  39  41  FOBS=   109.5  SIGMA=   2.2  PHAS=   -26.1  FOM=  0.90  TEST= 0
INDE  16  39  43  FOBS=     0.0  SIGMA=  21.3  PHAS=     0.0  FOM=  0.00  TEST= 0
INDE  16  39  45  FOBS=    47.2  SIGMA=   4.8  PHAS=    -6.0  FOM=  0.84  TEST= 0
INDE  16  39  47  FOBS=    57.2  SIGMA=   3.9  PHAS=    27.5  FOM=  0.09  TEST= 1
INDE  16  39  49  FOBS=     0.0  SIGMA=  20.9  PHAS=     0.0  FOM=  0.00  TEST= 0
INDE  16  39  51  FOBS=     0.0  SIGMA=  20.7  PHAS=     0.0  FOM=  0.00  TEST= 1
INDE  16  39  53  FOBS=     0.0  SIGMA=  20.9  PHAS=     0.0  FOM=  0.00  TEST= 0
INDE  16  39  55  FOBS=     0.0  SIGMA=  23.2  PHAS=     0.0  FOM=  0.00  TEST= 0
INDE  16  39  57  FOBS=    52.6  SIGMA=   4.1  PHAS=   175.5  FOM=  0.80  TEST= 0
INDE  16  39  59  FOBS=    84.9  SIGMA=   2.6  PHAS=   129.6  FOM=  0.91  TEST= 0
INDE  16  39  61  FOBS=     0.0  SIGMA=  20.8  PHAS=     0.0  FOM=  0.00  TEST= 0
INDE  16  39  63  FOBS=    36.7  SIGMA=   7.5  PHAS=    -2.3  FOM=  0.63  TEST= 0
INDE  16  39  65  FOBS=   102.5  SIGMA=   3.3  PHAS=    -0.5  FOM=  0.93  TEST= 0
INDE  16  40  16  FOBS=    72.7  SIGMA=   2.4  PHAS=   -24.0  FOM=  0.54  TEST= 0
INDE  16  40  18  FOBS=   141.7  SIGMA=   1.3  PHAS=    39.8  FOM=  0.91  TEST= 0
INDE  16  40  20  FOBS=   309.8  SIGMA=   0.7  PHAS=    83.8  FOM=  0.99  TEST= 0
INDE  16  40  22  FOBS=     8.5  SIGMA=  24.1  PHAS=    93.9  FOM=  0.18  TEST= 0
INDE  16  40  24  FOBS=   134.0  SIGMA=   1.5  PHAS=   174.0  FOM=  0.96  TEST= 0
INDE  16  40  26  FOBS=     0.0  SIGMA=  20.2  PHAS=     0.0  FOM=  0.00  TEST= 0
INDE  16  40  28  FOBS=     0.0  SIGMA=  19.4  PHAS=     0.0  FOM=  0.00  TEST= 0
INDE  16  40  30  FOBS=    23.9  SIGMA=   7.7  PHAS=   -34.0  FOM=  0.32  TEST= 0
INDE  16  40  32  FOBS=    95.0  SIGMA=   2.1  PHAS=   117.9  FOM=  0.80  TEST= 0
INDE  16  40  34  FOBS=    45.7  SIGMA=   4.2  PHAS=  -178.3  FOM=  0.36  TEST= 0
INDE  16  40  36  FOBS=   113.2  SIGMA=   1.7  PHAS=  -179.6  FOM=  0.91  TEST= 1
INDE  16  40  38  FOBS=   221.3  SIGMA=   1.2  PHAS=  -115.4  FOM=  0.97  TEST= 0
INDE  16  40  40  FOBS=   168.8  SIGMA=   1.5  PHAS=   -34.8  FOM=  0.40  TEST= 1
INDE  16  40  42  FOBS=    54.5  SIGMA=   4.2  PHAS=  -165.8  FOM=  0.68  TEST= 1
INDE  16  40  44  FOBS=    62.9  SIGMA=   4.0  PHAS=   117.5  FOM=  0.66  TEST= 0
INDE  16  40  46  FOBS=    79.2  SIGMA=   2.8  PHAS=  -113.1  FOM=  0.88  TEST= 0
INDE  16  40  48  FOBS=    83.3  SIGMA=   2.7  PHAS=   -25.3  FOM=  0.93  TEST= 0
INDE  16  40  50  FOBS=    77.7  SIGMA=   2.8  PHAS=  -123.8  FOM=  0.95  TEST= 0
INDE  16  40  52  FOBS=    90.9  SIGMA=   2.5  PHAS=  -114.8  FOM=  0.49  TEST= 1
INDE  16  40  54  FOBS=    49.1  SIGMA=   4.4  PHAS=   132.4  FOM=  0.53  TEST= 0
INDE  16  40  56  FOBS=   133.7  SIGMA=   1.7  PHAS=   155.1  FOM=  0.94  TEST= 0
INDE  16  40  58  FOBS=    36.1  SIGMA=   6.0  PHAS=  -128.0  FOM=  0.15  TEST= 0
INDE  16  40  60  FOBS=    34.8  SIGMA=   6.3  PHAS=   -67.4  FOM=  0.48  TEST= 0
INDE  16  40  62  FOBS=    29.5  SIGMA=  10.9  PHAS=   171.5  FOM=  0.50  TEST= 0
INDE  16  40  64  FOBS=   103.2  SIGMA=   2.8  PHAS=  -137.2  FOM=  0.96  TEST= 0
INDE  16  41  17  FOBS=   219.8  SIGMA=   0.9  PHAS=   -47.4  FOM=  0.94  TEST= 0
INDE  16  41  19  FOBS=    66.0  SIGMA=   3.0  PHAS=     8.4  FOM=  0.90  TEST= 0
```

*FIG. 12A - 385*

| | | | | | | | | | | | |
|---|---|---|---|---|---|---|---|---|---|---|---|
| INDE | 16 | 41 | 21 | FOBS= | 322.8 | SIGMA= | 0.8 | PHAS= | 12.1 | FOM= | 0.97 | TEST= 0 |
| INDE | 16 | 41 | 23 | FOBS= | 135.2 | SIGMA= | 1.6 | PHAS= | 93.9 | FOM= | 0.94 | TEST= 0 |
| INDE | 16 | 41 | 25 | FOBS= | 86.2 | SIGMA= | 2.4 | PHAS= | -122.4 | FOM= | 0.80 | TEST= 0 |
| INDE | 16 | 41 | 27 | FOBS= | 138.4 | SIGMA= | 1.8 | PHAS= | 144.8 | FOM= | 0.84 | TEST= 0 |
| INDE | 16 | 41 | 29 | FOBS= | 134.2 | SIGMA= | 1.6 | PHAS= | -127.1 | FOM= | 0.90 | TEST= 0 |
| INDE | 16 | 41 | 31 | FOBS= | 96.4 | SIGMA= | 2.1 | PHAS= | 140.7 | FOM= | 0.74 | TEST= 0 |
| INDE | 16 | 41 | 33 | FOBS= | 132.7 | SIGMA= | 1.5 | PHAS= | 127.0 | FOM= | 0.82 | TEST= 0 |
| INDE | 16 | 41 | 35 | FOBS= | 97.3 | SIGMA= | 1.8 | PHAS= | -178.9 | FOM= | 0.65 | TEST= 0 |
| INDE | 16 | 41 | 37 | FOBS= | 94.7 | SIGMA= | 2.0 | PHAS= | 89.1 | FOM= | 0.89 | TEST= 0 |
| INDE | 16 | 41 | 39 | FOBS= | 77.5 | SIGMA= | 3.0 | PHAS= | -122.6 | FOM= | 0.71 | TEST= 0 |
| INDE | 16 | 41 | 41 | FOBS= | 111.6 | SIGMA= | 2.1 | PHAS= | -137.5 | FOM= | 0.93 | TEST= 0 |
| INDE | 16 | 41 | 43 | FOBS= | 113.9 | SIGMA= | 2.1 | PHAS= | 107.4 | FOM= | 0.89 | TEST= 0 |
| INDE | 16 | 41 | 45 | FOBS= | 0.0 | SIGMA= | 22.5 | PHAS= | 0.0 | FOM= | 0.00 | TEST= 0 |
| INDE | 16 | 41 | 47 | FOBS= | 123.1 | SIGMA= | 1.9 | PHAS= | -99.7 | FOM= | 0.94 | TEST= 0 |
| INDE | 16 | 41 | 49 | FOBS= | 88.3 | SIGMA= | 2.5 | PHAS= | 167.8 | FOM= | 0.90 | TEST= 0 |
| INDE | 16 | 41 | 51 | FOBS= | 0.0 | SIGMA= | 21.8 | PHAS= | 0.0 | FOM= | 0.00 | TEST= 0 |
| INDE | 16 | 41 | 53 | FOBS= | 0.0 | SIGMA= | 20.7 | PHAS= | 0.0 | FOM= | 0.00 | TEST= 0 |
| INDE | 16 | 41 | 55 | FOBS= | 86.8 | SIGMA= | 2.6 | PHAS= | 0.0 | FOM= | 0.00 | TEST= 1 |
| INDE | 16 | 41 | 57 | FOBS= | 47.2 | SIGMA= | 4.6 | PHAS= | 62.4 | FOM= | 0.31 | TEST= 0 |
| INDE | 16 | 41 | 59 | FOBS= | 0.0 | SIGMA= | 21.7 | PHAS= | 0.0 | FOM= | 0.00 | TEST= 0 |
| INDE | 16 | 41 | 61 | FOBS= | 0.0 | SIGMA= | 23.3 | PHAS= | 0.0 | FOM= | 0.00 | TEST= 0 |
| INDE | 16 | 41 | 63 | FOBS= | 94.3 | SIGMA= | 3.0 | PHAS= | 73.9 | FOM= | 0.81 | TEST= 0 |
| INDE | 16 | 42 | 16 | FOBS= | 51.1 | SIGMA= | 3.9 | PHAS= | -152.5 | FOM= | 0.74 | TEST= 0 |
| INDE | 16 | 42 | 18 | FOBS= | 236.0 | SIGMA= | 1.0 | PHAS= | -97.7 | FOM= | 0.95 | TEST= 0 |
| INDE | 16 | 42 | 20 | FOBS= | 144.2 | SIGMA= | 1.7 | PHAS= | -150.7 | FOM= | 0.87 | TEST= 0 |
| INDE | 16 | 42 | 22 | FOBS= | 90.7 | SIGMA= | 2.5 | PHAS= | -60.1 | FOM= | 0.65 | TEST= 0 |
| INDE | 16 | 42 | 24 | FOBS= | 110.4 | SIGMA= | 2.0 | PHAS= | 73.1 | FOM= | 0.80 | TEST= 0 |
| INDE | 16 | 42 | 26 | FOBS= | 79.2 | SIGMA= | 2.8 | PHAS= | -156.9 | FOM= | 0.59 | TEST= 0 |
| INDE | 16 | 42 | 28 | FOBS= | 82.1 | SIGMA= | 2.7 | PHAS= | 129.1 | FOM= | 0.76 | TEST= 0 |
| INDE | 16 | 42 | 30 | FOBS= | 168.5 | SIGMA= | 1.3 | PHAS= | 85.1 | FOM= | 0.87 | TEST= 0 |
| INDE | 16 | 42 | 32 | FOBS= | 150.1 | SIGMA= | 1.4 | PHAS= | 103.8 | FOM= | 0.87 | TEST= 1 |
| INDE | 16 | 42 | 34 | FOBS= | 87.1 | SIGMA= | 2.2 | PHAS= | 52.4 | FOM= | 0.69 | TEST= 0 |
| INDE | 16 | 42 | 36 | FOBS= | 90.5 | SIGMA= | 2.0 | PHAS= | -149.2 | FOM= | 0.51 | TEST= 0 |
| INDE | 16 | 42 | 38 | FOBS= | 52.4 | SIGMA= | 4.1 | PHAS= | -146.8 | FOM= | 0.77 | TEST= 0 |
| INDE | 16 | 42 | 40 | FOBS= | 178.2 | SIGMA= | 1.4 | PHAS= | 176.3 | FOM= | 0.96 | TEST= 0 |
| INDE | 16 | 42 | 42 | FOBS= | 67.3 | SIGMA= | 3.5 | PHAS= | 47.0 | FOM= | 0.81 | TEST= 0 |
| INDE | 16 | 42 | 44 | FOBS= | 71.9 | SIGMA= | 3.2 | PHAS= | -30.9 | FOM= | 0.80 | TEST= 0 |
| INDE | 16 | 42 | 46 | FOBS= | 71.3 | SIGMA= | 3.2 | PHAS= | 160.6 | FOM= | 0.61 | TEST= 0 |
| INDE | 16 | 42 | 48 | FOBS= | 31.9 | SIGMA= | 7.5 | PHAS= | 138.1 | FOM= | 0.25 | TEST= 1 |
| INDE | 16 | 42 | 50 | FOBS= | 30.0 | SIGMA= | 7.3 | PHAS= | -46.1 | FOM= | 0.64 | TEST= 1 |
| INDE | 16 | 42 | 52 | FOBS= | 63.1 | SIGMA= | 3.5 | PHAS= | 33.6 | FOM= | 0.63 | TEST= 0 |
| INDE | 16 | 42 | 54 | FOBS= | 0.0 | SIGMA= | 20.9 | PHAS= | 0.0 | FOM= | 0.00 | TEST= 0 |
| INDE | 16 | 42 | 56 | FOBS= | 0.0 | SIGMA= | 21.6 | PHAS= | 0.0 | FOM= | 0.00 | TEST= 0 |
| INDE | 16 | 42 | 58 | FOBS= | 42.6 | SIGMA= | 5.1 | PHAS= | -148.6 | FOM= | 0.77 | TEST= 0 |
| INDE | 16 | 42 | 60 | FOBS= | 26.7 | SIGMA= | 10.1 | PHAS= | 178.3 | FOM= | 0.56 | TEST= 0 |
| INDE | 16 | 42 | 62 | FOBS= | 25.9 | SIGMA= | 10.7 | PHAS= | -78.1 | FOM= | 0.58 | TEST= 0 |
| INDE | 16 | 43 | 17 | FOBS= | 0.0 | SIGMA= | 21.0 | PHAS= | 0.0 | FOM= | 0.00 | TEST= 0 |
| INDE | 16 | 43 | 19 | FOBS= | 246.5 | SIGMA= | 1.0 | PHAS= | 142.9 | FOM= | 0.93 | TEST= 0 |
| INDE | 16 | 43 | 21 | FOBS= | 83.6 | SIGMA= | 2.7 | PHAS= | 2.0 | FOM= | 0.80 | TEST= 0 |
| INDE | 16 | 43 | 23 | FOBS= | 0.0 | SIGMA= | 20.8 | PHAS= | 0.0 | FOM= | 0.00 | TEST= 0 |
| INDE | 16 | 43 | 25 | FOBS= | 151.6 | SIGMA= | 1.5 | PHAS= | 163.0 | FOM= | 0.90 | TEST= 0 |
| INDE | 16 | 43 | 27 | FOBS= | 39.7 | SIGMA= | 5.5 | PHAS= | 124.4 | FOM= | 0.41 | TEST= 0 |
| INDE | 16 | 43 | 29 | FOBS= | 151.6 | SIGMA= | 1.5 | PHAS= | -67.2 | FOM= | 0.89 | TEST= 0 |
| INDE | 16 | 43 | 31 | FOBS= | 169.7 | SIGMA= | 1.2 | PHAS= | -13.9 | FOM= | 0.70 | TEST= 1 |
| INDE | 16 | 43 | 33 | FOBS= | 30.5 | SIGMA= | 6.7 | PHAS= | 12.5 | FOM= | 0.81 | TEST= 0 |
| INDE | 16 | 43 | 35 | FOBS= | 53.2 | SIGMA= | 3.6 | PHAS= | -154.0 | FOM= | 0.62 | TEST= 0 |
| INDE | 16 | 43 | 37 | FOBS= | 88.4 | SIGMA= | 2.0 | PHAS= | 69.7 | FOM= | 0.75 | TEST= 0 |
| INDE | 16 | 43 | 39 | FOBS= | 145.6 | SIGMA= | 1.6 | PHAS= | 105.4 | FOM= | 0.95 | TEST= 0 |
| INDE | 16 | 43 | 41 | FOBS= | 68.8 | SIGMA= | 3.4 | PHAS= | 152.4 | FOM= | 0.63 | TEST= 0 |
| INDE | 16 | 43 | 43 | FOBS= | 79.4 | SIGMA= | 2.9 | PHAS= | -94.5 | FOM= | 0.81 | TEST= 0 |
| INDE | 16 | 43 | 45 | FOBS= | 7.8 | SIGMA= | 29.2 | PHAS= | -97.0 | FOM= | 0.02 | TEST= 0 |
| INDE | 16 | 43 | 47 | FOBS= | 50.5 | SIGMA= | 4.4 | PHAS= | 93.3 | FOM= | 0.70 | TEST= 0 |
| INDE | 16 | 43 | 49 | FOBS= | 96.0 | SIGMA= | 2.4 | PHAS= | 160.3 | FOM= | 0.89 | TEST= 0 |
| INDE | 16 | 43 | 51 | FOBS= | 0.0 | SIGMA= | 20.9 | PHAS= | 0.0 | FOM= | 0.00 | TEST= 0 |
| INDE | 16 | 43 | 53 | FOBS= | 0.0 | SIGMA= | 21.8 | PHAS= | 0.0 | FOM= | 0.00 | TEST= 0 |
| INDE | 16 | 43 | 55 | FOBS= | 41.7 | SIGMA= | 5.3 | PHAS= | 53.4 | FOM= | 0.52 | TEST= 0 |
| INDE | 16 | 43 | 57 | FOBS= | 63.8 | SIGMA= | 3.4 | PHAS= | 37.3 | FOM= | 0.89 | TEST= 0 |
| INDE | 16 | 43 | 59 | FOBS= | 57.8 | SIGMA= | 3.8 | PHAS= | 64.0 | FOM= | 0.85 | TEST= 0 |
| INDE | 16 | 43 | 61 | FOBS= | 39.8 | SIGMA= | 7.0 | PHAS= | 58.1 | FOM= | 0.72 | TEST= 0 |
| INDE | 16 | 44 | 16 | FOBS= | 216.7 | SIGMA= | 1.1 | PHAS= | -43.8 | FOM= | 0.95 | TEST= 0 |

*FIG. 12A - 386*

```
INDE  16  44  18  FOBS=   155.9  SIGMA=   1.5  PHAS=   -55.9  FOM=  0.90  TEST=  0
INDE  16  44  20  FOBS=    90.2  SIGMA=   2.7  PHAS=  -159.0  FOM=  0.78  TEST=  0
INDE  16  44  22  FOBS=    57.9  SIGMA=   3.8  PHAS=    80.3  FOM=  0.49  TEST=  1
INDE  16  44  24  FOBS=   228.3  SIGMA=   1.1  PHAS=    72.8  FOM=  0.97  TEST=  0
INDE  16  44  26  FOBS=    98.1  SIGMA=   2.2  PHAS=    88.9  FOM=  0.89  TEST=  0
INDE  16  44  28  FOBS=   136.1  SIGMA=   1.7  PHAS=     1.3  FOM=  0.89  TEST=  0
INDE  16  44  30  FOBS=    18.5  SIGMA=  11.8  PHAS=    14.2  FOM=  0.07  TEST=  0
INDE  16  44  32  FOBS=    26.0  SIGMA=   7.5  PHAS=   -86.2  FOM=  0.82  TEST=  0
INDE  16  44  34  FOBS=   102.4  SIGMA=   1.9  PHAS=    88.7  FOM=  0.74  TEST=  0
INDE  16  44  36  FOBS=    68.2  SIGMA=   2.8  PHAS=   -72.8  FOM=  0.75  TEST=  0
INDE  16  44  38  FOBS=    79.8  SIGMA=   2.2  PHAS=    27.3  FOM=  0.84  TEST=  0
INDE  16  44  40  FOBS=    66.7  SIGMA=   3.2  PHAS=    11.9  FOM=  0.84  TEST=  0
INDE  16  44  42  FOBS=     0.0  SIGMA=  24.4  PHAS=     0.0  FOM=  0.00  TEST=  0
INDE  16  44  44  FOBS=     0.0  SIGMA=  21.2  PHAS=     0.0  FOM=  0.00  TEST=  0
INDE  16  44  46  FOBS=    17.0  SIGMA=  14.2  PHAS=    71.5  FOM=  0.26  TEST=  0
INDE  16  44  48  FOBS=    39.3  SIGMA=   6.8  PHAS=   -30.9  FOM=  0.22  TEST=  0
INDE  16  44  50  FOBS=    74.3  SIGMA=   3.0  PHAS=    -0.7  FOM=  0.90  TEST=  0
INDE  16  44  52  FOBS=     0.0  SIGMA=  24.3  PHAS=     0.0  FOM=  0.00  TEST=  0
INDE  16  44  54  FOBS=    31.1  SIGMA=   7.1  PHAS=    47.0  FOM=  0.12  TEST=  0
INDE  16  44  56  FOBS=    89.2  SIGMA=   2.5  PHAS=   -18.2  FOM=  0.90  TEST=  0
INDE  16  44  58  FOBS=    43.5  SIGMA=   5.1  PHAS=  -126.5  FOM=  0.77  TEST=  0
INDE  16  44  60  FOBS=    87.8  SIGMA=   3.2  PHAS=   -69.4  FOM=  0.84  TEST=  0
INDE  16  44  62  FOBS=    21.2  SIGMA=  13.3  PHAS=     5.7  FOM=  0.06  TEST=  0
INDE  16  45  17  FOBS=   213.2  SIGMA=   1.3  PHAS=  -102.9  FOM=  0.95  TEST=  0
INDE  16  45  19  FOBS=   163.4  SIGMA=   1.4  PHAS=  -169.6  FOM=  0.88  TEST=  0
INDE  16  45  21  FOBS=    83.6  SIGMA=   2.6  PHAS=   129.8  FOM=  0.75  TEST=  0
INDE  16  45  23  FOBS=   222.8  SIGMA=   1.1  PHAS=   -11.9  FOM=  0.97  TEST=  0
INDE  16  45  25  FOBS=    86.2  SIGMA=   2.5  PHAS=  -127.2  FOM=  0.40  TEST=  1
INDE  16  45  27  FOBS=   141.4  SIGMA=   1.6  PHAS=   -78.9  FOM=  0.71  TEST=  0
INDE  16  45  29  FOBS=   149.3  SIGMA=   1.6  PHAS=   -57.6  FOM=  0.90  TEST=  1
INDE  16  45  31  FOBS=   132.4  SIGMA=   1.6  PHAS=   144.5  FOM=  0.91  TEST=  0
INDE  16  45  33  FOBS=   132.4  SIGMA=   1.5  PHAS=    54.9  FOM=  0.31  TEST=  0
INDE  16  45  35  FOBS=   102.4  SIGMA=   1.9  PHAS=   171.7  FOM=  0.76  TEST=  1
INDE  16  45  37  FOBS=    27.7  SIGMA=   7.3  PHAS=    40.1  FOM=  0.02  TEST=  1
INDE  16  45  39  FOBS=   106.4  SIGMA=   1.7  PHAS=   -85.4  FOM=  0.91  TEST=  0
INDE  16  45  41  FOBS=    47.1  SIGMA=   4.0  PHAS=  -163.6  FOM=  0.05  TEST=  0
INDE  16  45  43  FOBS=     0.0  SIGMA=  23.5  PHAS=     0.0  FOM=  0.00  TEST=  0
INDE  16  45  45  FOBS=    76.7  SIGMA=   3.0  PHAS=    42.1  FOM=  0.67  TEST=  0
INDE  16  45  47  FOBS=    69.9  SIGMA=   3.3  PHAS=   156.7  FOM=  0.87  TEST=  0
INDE  16  45  49  FOBS=    38.9  SIGMA=   5.7  PHAS=  -136.9  FOM=  0.46  TEST=  0
INDE  16  45  51  FOBS=     5.4  SIGMA=  40.4  PHAS=   -58.3  FOM=  0.06  TEST=  0
INDE  16  45  53  FOBS=    24.9  SIGMA=   8.9  PHAS=    57.9  FOM=  0.20  TEST=  0
INDE  16  45  55  FOBS=    64.4  SIGMA=   3.5  PHAS=   -19.7  FOM=  0.14  TEST=  1
INDE  16  45  57  FOBS=    68.1  SIGMA=   3.3  PHAS=    80.7  FOM=  0.84  TEST=  0
INDE  16  45  59  FOBS=    23.4  SIGMA=  11.8  PHAS=   -72.4  FOM=  0.04  TEST=  1
INDE  16  45  61  FOBS=    33.1  SIGMA=   8.5  PHAS=   176.1  FOM=  0.60  TEST=  0
INDE  16  46  16  FOBS=   237.3  SIGMA=   1.1  PHAS=   -22.7  FOM=  0.84  TEST=  1
INDE  16  46  18  FOBS=    67.6  SIGMA=   3.2  PHAS=  -143.6  FOM=  0.12  TEST=  0
INDE  16  46  20  FOBS=    72.6  SIGMA=   3.2  PHAS=   165.7  FOM=  0.69  TEST=  0
INDE  16  46  22  FOBS=    90.5  SIGMA=   2.4  PHAS=    -6.9  FOM=  0.90  TEST=  0
INDE  16  46  24  FOBS=   140.4  SIGMA=   1.6  PHAS=   121.2  FOM=  0.83  TEST=  0
INDE  16  46  26  FOBS=   124.8  SIGMA=   1.8  PHAS=   119.1  FOM=  0.76  TEST=  0
INDE  16  46  28  FOBS=   144.3  SIGMA=   1.6  PHAS=   -39.5  FOM=  0.89  TEST=  0
INDE  16  46  30  FOBS=   185.3  SIGMA=   1.3  PHAS=    92.0  FOM=  0.94  TEST=  0
INDE  16  46  32  FOBS=    72.8  SIGMA=   2.7  PHAS=   -75.3  FOM=  0.38  TEST=  0
INDE  16  46  34  FOBS=    71.4  SIGMA=   2.7  PHAS=   157.3  FOM=  0.33  TEST=  1
INDE  16  46  36  FOBS=    97.0  SIGMA=   2.0  PHAS=   169.6  FOM=  0.80  TEST=  0
INDE  16  46  38  FOBS=    64.7  SIGMA=   2.7  PHAS=  -111.5  FOM=  0.40  TEST=  0
INDE  16  46  40  FOBS=     0.0  SIGMA=  18.4  PHAS=     0.0  FOM=  0.00  TEST=  0
INDE  16  46  42  FOBS=    53.4  SIGMA=   5.0  PHAS=    30.0  FOM=  0.66  TEST=  0
INDE  16  46  44  FOBS=   133.0  SIGMA=   1.8  PHAS=   -30.4  FOM=  0.90  TEST=  0
INDE  16  46  46  FOBS=    95.0  SIGMA=   2.4  PHAS=    38.0  FOM=  0.93  TEST=  0
INDE  16  46  48  FOBS=     0.0  SIGMA=  21.1  PHAS=     0.0  FOM=  0.00  TEST=  0
INDE  16  46  50  FOBS=     0.0  SIGMA=  21.9  PHAS=     0.0  FOM=  0.00  TEST=  0
INDE  16  46  52  FOBS=     0.0  SIGMA=  20.9  PHAS=     0.0  FOM=  0.00  TEST=  0
INDE  16  46  54  FOBS=     0.0  SIGMA=  22.0  PHAS=     0.0  FOM=  0.00  TEST=  0
INDE  16  46  56  FOBS=    43.8  SIGMA=   5.1  PHAS=   -34.3  FOM=  0.87  TEST=  0
INDE  16  46  58  FOBS=    20.7  SIGMA=  14.9  PHAS=  -102.6  FOM=  0.22  TEST=  0
INDE  16  46  60  FOBS=    18.6  SIGMA=  18.3  PHAS=    68.9  FOM=  0.58  TEST=  0
INDE  16  47  17  FOBS=   186.4  SIGMA=   1.2  PHAS=   -77.1  FOM=  0.40  TEST=  1
```

*FIG. 12A - 387*

```
INDE 16 47 19 FOBS=   122.8 SIGMA=  1.8 PHAS=  172.8 FOM= 0.80 TEST= 0
INDE 16 47 21 FOBS=   102.9 SIGMA=  2.1 PHAS=  167.2 FOM= 0.94 TEST= 0
INDE 16 47 23 FOBS=   112.3 SIGMA=  2.0 PHAS=    6.0 FOM= 0.94 TEST= 0
INDE 16 47 25 FOBS=   187.1 SIGMA=  1.3 PHAS=   17.9 FOM= 0.98 TEST= 0
INDE 16 47 27 FOBS=    63.2 SIGMA=  3.4 PHAS=  111.9 FOM= 0.84 TEST= 0
INDE 16 47 29 FOBS=   111.8 SIGMA=  2.0 PHAS= -167.0 FOM= 0.80 TEST= 0
INDE 16 47 31 FOBS=     0.0 SIGMA= 23.0 PHAS=    0.0 FOM= 0.00 TEST= 1
INDE 16 47 33 FOBS=    65.1 SIGMA=  3.0 PHAS=  -38.3 FOM= 0.61 TEST= 0
INDE 16 47 35 FOBS=   216.8 SIGMA=  1.0 PHAS=   71.3 FOM= 0.97 TEST= 0
INDE 16 47 37 FOBS=    87.5 SIGMA=  2.2 PHAS=  120.9 FOM= 0.90 TEST= 0
INDE 16 47 39 FOBS=   153.6 SIGMA=  1.2 PHAS= -124.8 FOM= 0.96 TEST= 0
INDE 16 47 41 FOBS=    72.2 SIGMA=  2.4 PHAS=   68.4 FOM= 0.35 TEST= 0
INDE 16 47 43 FOBS=   116.2 SIGMA=  1.9 PHAS=  -85.8 FOM= 0.93 TEST= 0
INDE 16 47 45 FOBS=   112.9 SIGMA=  2.1 PHAS=  -85.2 FOM= 0.92 TEST= 0
INDE 16 47 47 FOBS=    82.1 SIGMA=  2.8 PHAS= -130.2 FOM= 0.93 TEST= 0
INDE 16 47 49 FOBS=     0.0 SIGMA= 21.9 PHAS=    0.0 FOM= 0.00 TEST= 0
INDE 16 47 51 FOBS=    44.3 SIGMA=  5.0 PHAS=  -57.9 FOM= 0.58 TEST= 0
INDE 16 47 53 FOBS=    24.5 SIGMA=  9.1 PHAS=   90.4 FOM= 0.17 TEST= 0
INDE 16 47 55 FOBS=    26.1 SIGMA= 15.4 PHAS=  -87.8 FOM= 0.19 TEST= 0
INDE 16 47 57 FOBS=    43.6 SIGMA=  6.3 PHAS=  162.8 FOM= 0.62 TEST= 0
INDE 16 47 59 FOBS=    64.2 SIGMA=  4.5 PHAS=   -1.3 FOM= 0.86 TEST= 0
INDE 16 48 16 FOBS=    88.3 SIGMA=  3.1 PHAS=   60.1 FOM= 0.50 TEST= 0
INDE 16 48 18 FOBS=   138.0 SIGMA=  1.6 PHAS=  137.3 FOM= 0.91 TEST= 0
INDE 16 48 20 FOBS=     0.0 SIGMA= 24.1 PHAS=    0.0 FOM= 0.00 TEST= 0
INDE 16 48 22 FOBS=    98.0 SIGMA=  2.2 PHAS=    1.8 FOM= 0.90 TEST= 0
INDE 16 48 24 FOBS=    73.7 SIGMA=  2.9 PHAS=  -68.5 FOM= 0.96 TEST= 0
INDE 16 48 26 FOBS=   124.3 SIGMA=  1.8 PHAS=  -10.8 FOM= 0.96 TEST= 0
INDE 16 48 28 FOBS=   113.8 SIGMA=  1.9 PHAS=   28.3 FOM= 0.88 TEST= 0
INDE 16 48 30 FOBS=   152.8 SIGMA=  1.5 PHAS=   91.6 FOM= 0.97 TEST= 0
INDE 16 48 32 FOBS=   106.9 SIGMA=  2.1 PHAS=  -91.9 FOM= 0.47 TEST= 1
INDE 16 48 34 FOBS=   102.6 SIGMA=  1.9 PHAS=  -61.0 FOM= 0.94 TEST= 0
INDE 16 48 36 FOBS=   134.8 SIGMA=  1.5 PHAS=   19.7 FOM= 0.91 TEST= 0
INDE 16 48 38 FOBS=    33.5 SIGMA=  5.6 PHAS=  134.9 FOM= 0.72 TEST= 0
INDE 16 48 40 FOBS=    36.1 SIGMA=  4.8 PHAS=  162.6 FOM= 0.50 TEST= 0
INDE 16 48 42 FOBS=    29.2 SIGMA=  5.8 PHAS=  130.1 FOM= 0.06 TEST= 1
INDE 16 48 44 FOBS=    80.2 SIGMA=  2.7 PHAS=  -17.1 FOM= 0.67 TEST= 0
INDE 16 48 46 FOBS=    95.2 SIGMA=  2.5 PHAS=  153.3 FOM= 0.95 TEST= 0
INDE 16 48 48 FOBS=    86.2 SIGMA=  2.7 PHAS=   50.1 FOM= 0.89 TEST= 0
INDE 16 48 50 FOBS=    21.5 SIGMA= 16.8 PHAS=  179.0 FOM= 0.11 TEST= 0
INDE 16 48 52 FOBS=    31.9 SIGMA=  7.6 PHAS=  124.9 FOM= 0.11 TEST= 0
INDE 16 48 54 FOBS=     0.0 SIGMA= 22.0 PHAS=    0.0 FOM= 0.00 TEST= 0
INDE 16 48 56 FOBS=    29.6 SIGMA=  8.4 PHAS= -160.5 FOM= 0.18 TEST= 0
INDE 16 48 58 FOBS=     0.0 SIGMA= 23.7 PHAS=    0.0 FOM= 0.00 TEST= 0
INDE 16 49 17 FOBS=   307.2 SIGMA=  0.8 PHAS=   73.9 FOM= 0.97 TEST= 0
INDE 16 49 19 FOBS=    35.7 SIGMA=  7.4 PHAS=   88.2 FOM= 0.30 TEST= 0
INDE 16 49 21 FOBS=   108.4 SIGMA=  2.1 PHAS= -123.8 FOM= 0.86 TEST= 0
INDE 16 49 23 FOBS=    19.1 SIGMA= 11.9 PHAS=   63.5 FOM= 0.07 TEST= 0
INDE 16 49 25 FOBS=   143.5 SIGMA=  1.6 PHAS=  -40.3 FOM= 0.92 TEST= 0
INDE 16 49 27 FOBS=    74.4 SIGMA=  2.9 PHAS=  -33.0 FOM= 0.40 TEST= 0
INDE 16 49 29 FOBS=   120.7 SIGMA=  1.8 PHAS=    0.3 FOM= 0.84 TEST= 0
INDE 16 49 31 FOBS=    94.8 SIGMA=  2.3 PHAS=  -18.3 FOM= 0.94 TEST= 0
INDE 16 49 33 FOBS=    58.2 SIGMA=  3.4 PHAS=  133.9 FOM= 0.91 TEST= 0
INDE 16 49 35 FOBS=    24.3 SIGMA=  9.1 PHAS=  -56.1 FOM= 0.50 TEST= 0
INDE 16 49 37 FOBS=    82.7 SIGMA=  2.3 PHAS=   69.6 FOM= 0.92 TEST= 0
INDE 16 49 39 FOBS=    43.4 SIGMA=  4.1 PHAS=  -35.1 FOM= 0.28 TEST= 0
INDE 16 49 41 FOBS=     0.0 SIGMA= 20.2 PHAS=    0.0 FOM= 0.00 TEST= 0
INDE 16 49 43 FOBS=    98.3 SIGMA=  1.8 PHAS= -105.8 FOM= 0.92 TEST= 0
INDE 16 49 45 FOBS=    25.6 SIGMA=  8.2 PHAS= -133.3 FOM= 0.17 TEST= 0
INDE 16 49 47 FOBS=     0.0 SIGMA= 21.3 PHAS=    0.0 FOM= 0.00 TEST= 1
INDE 16 49 49 FOBS=    35.0 SIGMA=  6.5 PHAS=   54.5 FOM= 0.50 TEST= 0
INDE 16 49 51 FOBS=    21.8 SIGMA= 12.5 PHAS=    7.7 FOM= 0.06 TEST= 0
INDE 16 49 53 FOBS=     0.0 SIGMA= 24.0 PHAS=    0.0 FOM= 0.00 TEST= 0
INDE 16 49 55 FOBS=    42.9 SIGMA=  5.3 PHAS=  -22.0 FOM= 0.64 TEST= 0
INDE 16 49 57 FOBS=    67.9 SIGMA=  4.2 PHAS=  -91.8 FOM= 0.80 TEST= 0
INDE 16 50 16 FOBS=   308.2 SIGMA=  1.1 PHAS=  -30.3 FOM= 0.98 TEST= 0
INDE 16 50 18 FOBS=   175.6 SIGMA=  1.3 PHAS=   45.7 FOM= 0.92 TEST= 0
INDE 16 50 20 FOBS=   108.4 SIGMA=  1.9 PHAS= -110.1 FOM= 0.83 TEST= 0
INDE 16 50 22 FOBS=    13.8 SIGMA= 18.7 PHAS= -137.6 FOM= 0.12 TEST= 0
INDE 16 50 24 FOBS=    60.4 SIGMA=  3.5 PHAS=  -80.4 FOM= 0.86 TEST= 0
INDE 16 50 26 FOBS=    59.7 SIGMA=  3.6 PHAS=   74.4 FOM= 0.77 TEST= 1
```

*FIG. 12A - 388*

```
INDE 16 50 28 FOBS=   91.1 SIGMA=  2.4 PHAS=  123.1 FOM= 0.70 TEST= 0
INDE 16 50 30 FOBS=   89.6 SIGMA=  2.4 PHAS=   90.9 FOM= 0.66 TEST= 0
INDE 16 50 32 FOBS=  130.5 SIGMA=  1.7 PHAS=  -41.3 FOM= 0.91 TEST= 1
INDE 16 50 34 FOBS=   55.5 SIGMA=  3.6 PHAS=    0.7 FOM= 0.48 TEST= 0
INDE 16 50 36 FOBS=   64.7 SIGMA=  2.9 PHAS=   10.6 FOM= 0.72 TEST= 0
INDE 16 50 38 FOBS=   95.9 SIGMA=  2.0 PHAS=   14.0 FOM= 0.90 TEST= 0
INDE 16 50 40 FOBS=   48.7 SIGMA=  3.5 PHAS=   36.8 FOM= 0.26 TEST= 1
INDE 16 50 42 FOBS=    0.0 SIGMA= 18.4 PHAS=    0.0 FOM= 0.00 TEST= 0
INDE 16 50 44 FOBS=   56.4 SIGMA=  3.0 PHAS=   63.9 FOM= 0.62 TEST= 0
INDE 16 50 46 FOBS=    0.0 SIGMA= 21.4 PHAS=    0.0 FOM= 0.00 TEST= 1
INDE 16 50 48 FOBS=   76.3 SIGMA=  3.0 PHAS=   62.5 FOM= 0.90 TEST= 0
INDE 16 50 50 FOBS=   16.2 SIGMA= 20.0 PHAS=  -64.7 FOM= 0.19 TEST= 0
INDE 16 50 52 FOBS=    0.0 SIGMA= 22.0 PHAS=    0.0 FOM= 0.00 TEST= 0
INDE 16 50 54 FOBS=    8.5 SIGMA= 26.9 PHAS=   72.1 FOM= 0.04 TEST= 1
INDE 16 50 56 FOBS=  120.9 SIGMA=  2.4 PHAS= -176.8 FOM= 0.95 TEST= 0
INDE 16 51 17 FOBS=    0.0 SIGMA= 23.0 PHAS=    0.0 FOM= 0.00 TEST= 0
INDE 16 51 19 FOBS=   58.6 SIGMA=  3.5 PHAS=   49.4 FOM= 0.60 TEST= 0
INDE 16 51 21 FOBS=   46.1 SIGMA=  4.8 PHAS=  173.2 FOM= 0.34 TEST= 0
INDE 16 51 23 FOBS=   27.7 SIGMA=  7.5 PHAS=  -31.9 FOM= 0.72 TEST= 0
INDE 16 51 25 FOBS=    0.0 SIGMA= 20.4 PHAS=    0.0 FOM= 0.00 TEST= 0
INDE 16 51 27 FOBS=   41.9 SIGMA=  5.0 PHAS=  -48.1 FOM= 0.65 TEST= 0
INDE 16 51 29 FOBS=   63.2 SIGMA=  3.3 PHAS= -141.2 FOM= 0.59 TEST= 0
INDE 16 51 31 FOBS=   39.9 SIGMA=  5.2 PHAS=  -13.9 FOM= 0.41 TEST= 0
INDE 16 51 33 FOBS=   42.8 SIGMA=  4.8 PHAS=    3.6 FOM= 0.54 TEST= 0
INDE 16 51 35 FOBS=  108.7 SIGMA=  1.8 PHAS= -117.0 FOM= 0.93 TEST= 0
INDE 16 51 37 FOBS=   30.5 SIGMA=  6.6 PHAS=  -52.1 FOM= 0.42 TEST= 0
INDE 16 51 39 FOBS=  109.1 SIGMA=  1.8 PHAS=  -47.5 FOM= 0.94 TEST= 0
INDE 16 51 41 FOBS=   96.7 SIGMA=  1.8 PHAS= -129.4 FOM= 0.87 TEST= 0
INDE 16 51 43 FOBS=    0.0 SIGMA= 18.8 PHAS=    0.0 FOM= 0.00 TEST= 0
INDE 16 51 45 FOBS=    0.0 SIGMA= 18.4 PHAS=    0.0 FOM= 0.00 TEST= 1
INDE 16 51 47 FOBS=   19.2 SIGMA= 14.9 PHAS=   88.9 FOM= 0.04 TEST= 0
INDE 16 51 49 FOBS=   22.0 SIGMA= 10.4 PHAS= -144.7 FOM= 0.26 TEST= 0
INDE 16 51 51 FOBS=    0.0 SIGMA= 22.3 PHAS=    0.0 FOM= 0.00 TEST= 0
INDE 16 51 53 FOBS=    0.0 SIGMA= 21.4 PHAS=    0.0 FOM= 0.00 TEST= 0
INDE 16 51 55 FOBS=   46.2 SIGMA=  6.2 PHAS=   44.1 FOM= 0.80 TEST= 0
INDE 16 52 16 FOBS=   34.8 SIGMA=  8.6 PHAS= -154.5 FOM= 0.07 TEST= 0
INDE 16 52 18 FOBS=  129.8 SIGMA=  2.1 PHAS= -105.6 FOM= 0.91 TEST= 0
INDE 16 52 20 FOBS=   52.4 SIGMA=  4.3 PHAS=  -72.2 FOM= 0.52 TEST= 0
INDE 16 52 22 FOBS=   26.9 SIGMA=  7.5 PHAS=  -63.8 FOM= 0.25 TEST= 0
INDE 16 52 24 FOBS=    0.0 SIGMA= 20.3 PHAS=    0.0 FOM= 0.00 TEST= 0
INDE 16 52 26 FOBS=  103.2 SIGMA=  2.1 PHAS=  151.8 FOM= 0.92 TEST= 0
INDE 16 52 28 FOBS=   58.5 SIGMA=  3.6 PHAS=  147.4 FOM= 0.79 TEST= 0
INDE 16 52 30 FOBS=   52.5 SIGMA=  4.0 PHAS=  154.7 FOM= 0.79 TEST= 0
INDE 16 52 32 FOBS=   61.4 SIGMA=  3.4 PHAS=  -33.5 FOM= 0.66 TEST= 0
INDE 16 52 34 FOBS=   15.4 SIGMA= 13.4 PHAS=   71.4 FOM= 0.21 TEST= 0
INDE 16 52 36 FOBS=  108.4 SIGMA=  1.8 PHAS=  134.1 FOM= 0.94 TEST= 0
INDE 16 52 38 FOBS=   43.1 SIGMA=  4.3 PHAS=  -60.5 FOM= 0.47 TEST= 0
INDE 16 52 40 FOBS=   89.8 SIGMA=  2.2 PHAS=  153.4 FOM= 0.89 TEST= 0
INDE 16 52 42 FOBS=    0.0 SIGMA= 18.8 PHAS=    0.0 FOM= 0.00 TEST= 0
INDE 16 52 44 FOBS=   44.5 SIGMA=  3.9 PHAS=   35.5 FOM= 0.59 TEST= 0
INDE 16 52 46 FOBS=   50.2 SIGMA=  3.5 PHAS=   50.6 FOM= 0.62 TEST= 0
INDE 16 52 48 FOBS=   34.2 SIGMA=  6.2 PHAS=   23.6 FOM= 0.71 TEST= 0
INDE 16 52 50 FOBS=   49.9 SIGMA=  4.7 PHAS=   28.9 FOM= 0.80 TEST= 0
INDE 16 52 52 FOBS=   29.8 SIGMA= 10.1 PHAS=  -28.1 FOM= 0.39 TEST= 0
INDE 16 52 54 FOBS=   30.3 SIGMA= 11.5 PHAS= -136.1 FOM= 0.44 TEST= 0
INDE 16 53 17 FOBS=   65.9 SIGMA=  4.0 PHAS= -142.6 FOM= 0.81 TEST= 0
INDE 16 53 19 FOBS=  214.3 SIGMA=  1.1 PHAS= -170.7 FOM= 0.96 TEST= 0
INDE 16 53 21 FOBS=   33.8 SIGMA=  6.5 PHAS=   58.8 FOM= 0.36 TEST= 0
INDE 16 53 23 FOBS=   94.4 SIGMA=  2.2 PHAS=   23.8 FOM= 0.73 TEST= 0
INDE 16 53 25 FOBS=    9.5 SIGMA= 24.1 PHAS=   71.4 FOM= 0.10 TEST= 0
INDE 16 53 27 FOBS=   59.4 SIGMA=  3.5 PHAS=  142.2 FOM= 0.75 TEST= 0
INDE 16 53 29 FOBS=  115.7 SIGMA=  1.9 PHAS=  134.4 FOM= 0.53 TEST= 1
INDE 16 53 31 FOBS=    0.0 SIGMA= 24.4 PHAS=    0.0 FOM= 0.00 TEST= 0
INDE 16 53 33 FOBS=   10.6 SIGMA= 23.7 PHAS=   -3.5 FOM= 0.20 TEST= 0
INDE 16 53 35 FOBS=    0.0 SIGMA= 20.5 PHAS=    0.0 FOM= 0.00 TEST= 0
INDE 16 53 37 FOBS=   60.3 SIGMA=  3.1 PHAS=  -70.0 FOM= 0.75 TEST= 0
INDE 16 53 39 FOBS=   56.7 SIGMA=  3.3 PHAS=   96.3 FOM= 0.82 TEST= 0
INDE 16 53 41 FOBS=   38.0 SIGMA=  4.9 PHAS= -130.5 FOM= 0.36 TEST= 0
INDE 16 53 43 FOBS=   56.8 SIGMA=  3.1 PHAS= -124.0 FOM= 0.32 TEST= 0
INDE 16 53 45 FOBS=   38.3 SIGMA=  4.9 PHAS=  -16.9 FOM= 0.44 TEST= 0
```

*FIG. 12A - 389*

| | | | | | | | | | | | | |
|---|---|---|---|---|---|---|---|---|---|---|---|---|
| INDE | 16 | 53 | 47 | FOBS= | 0.0 | SIGMA= | 20.8 | PHAS= | 0.0 | FOM= | 0.00 | TEST= 0 |
| INDE | 16 | 53 | 49 | FOBS= | 91.0 | SIGMA= | 2.7 | PHAS= | -115.0 | FOM= | 0.92 | TEST= 0 |
| INDE | 16 | 53 | 51 | FOBS= | 34.2 | SIGMA= | 8.7 | PHAS= | -94.4 | FOM= | 0.62 | TEST= 0 |
| INDE | 16 | 53 | 53 | FOBS= | 57.5 | SIGMA= | 8.1 | PHAS= | -133.5 | FOM= | 0.80 | TEST= 0 |
| INDE | 16 | 54 | 16 | FOBS= | 157.4 | SIGMA= | 1.8 | PHAS= | 123.8 | FOM= | 0.95 | TEST= 0 |
| INDE | 16 | 54 | 18 | FOBS= | 53.8 | SIGMA= | 4.9 | PHAS= | 172.5 | FOM= | 0.54 | TEST= 0 |
| INDE | 16 | 54 | 20 | FOBS= | 168.0 | SIGMA= | 1.3 | PHAS= | 132.1 | FOM= | 0.43 | TEST= 1 |
| INDE | 16 | 54 | 22 | FOBS= | 21.6 | SIGMA= | 9.4 | PHAS= | -117.3 | FOM= | 0.14 | TEST= 0 |
| INDE | 16 | 54 | 24 | FOBS= | 32.5 | SIGMA= | 6.3 | PHAS= | -168.4 | FOM= | 0.56 | TEST= 1 |
| INDE | 16 | 54 | 26 | FOBS= | 153.4 | SIGMA= | 1.4 | PHAS= | 113.3 | FOM= | 0.95 | TEST= 0 |
| INDE | 16 | 54 | 28 | FOBS= | 132.3 | SIGMA= | 1.6 | PHAS= | 46.0 | FOM= | 0.94 | TEST= 0 |
| INDE | 16 | 54 | 30 | FOBS= | 68.2 | SIGMA= | 3.1 | PHAS= | 123.2 | FOM= | 0.75 | TEST= 0 |
| INDE | 16 | 54 | 32 | FOBS= | 52.2 | SIGMA= | 4.0 | PHAS= | -130.1 | FOM= | 0.78 | TEST= 0 |
| INDE | 16 | 54 | 34 | FOBS= | 0.0 | SIGMA= | 21.5 | PHAS= | 0.0 | FOM= | 0.00 | TEST= 0 |
| INDE | 16 | 54 | 36 | FOBS= | 131.7 | SIGMA= | 1.5 | PHAS= | 131.6 | FOM= | 0.96 | TEST= 0 |
| INDE | 16 | 54 | 38 | FOBS= | 0.0 | SIGMA= | 20.6 | PHAS= | 0.0 | FOM= | 0.00 | TEST= 0 |
| INDE | 16 | 54 | 40 | FOBS= | 78.4 | SIGMA= | 2.4 | PHAS= | 48.8 | FOM= | 0.90 | TEST= 0 |
| INDE | 16 | 54 | 42 | FOBS= | 77.2 | SIGMA= | 2.3 | PHAS= | 160.7 | FOM= | 0.90 | TEST= 0 |
| INDE | 16 | 54 | 44 | FOBS= | 47.6 | SIGMA= | 3.9 | PHAS= | -81.5 | FOM= | 0.58 | TEST= 0 |
| INDE | 16 | 54 | 46 | FOBS= | 45.7 | SIGMA= | 4.1 | PHAS= | 72.2 | FOM= | 0.66 | TEST= 0 |
| INDE | 16 | 54 | 48 | FOBS= | 0.0 | SIGMA= | 23.0 | PHAS= | 0.0 | FOM= | 0.00 | TEST= 0 |
| INDE | 16 | 54 | 50 | FOBS= | 52.3 | SIGMA= | 5.9 | PHAS= | 118.3 | FOM= | 0.61 | TEST= 0 |
| INDE | 16 | 54 | 52 | FOBS= | 57.3 | SIGMA= | 8.2 | PHAS= | -179.4 | FOM= | 0.91 | TEST= 0 |
| INDE | 16 | 55 | 17 | FOBS= | 64.3 | SIGMA= | 4.0 | PHAS= | -84.9 | FOM= | 0.79 | TEST= 0 |
| INDE | 16 | 55 | 19 | FOBS= | 104.9 | SIGMA= | 2.5 | PHAS= | -171.1 | FOM= | 0.90 | TEST= 0 |
| INDE | 16 | 55 | 21 | FOBS= | 224.4 | SIGMA= | 1.0 | PHAS= | 73.0 | FOM= | 0.97 | TEST= 0 |
| INDE | 16 | 55 | 23 | FOBS= | 132.0 | SIGMA= | 1.6 | PHAS= | 53.0 | FOM= | 0.90 | TEST= 0 |
| INDE | 16 | 55 | 25 | FOBS= | 37.7 | SIGMA= | 5.4 | PHAS= | -8.4 | FOM= | 0.70 | TEST= 0 |
| INDE | 16 | 55 | 27 | FOBS= | 57.0 | SIGMA= | 3.6 | PHAS= | 37.9 | FOM= | 0.84 | TEST= 0 |
| INDE | 16 | 55 | 29 | FOBS= | 25.9 | SIGMA= | 7.9 | PHAS= | 30.6 | FOM= | 0.64 | TEST= 0 |
| INDE | 16 | 55 | 31 | FOBS= | 44.4 | SIGMA= | 4.7 | PHAS= | 81.3 | FOM= | 0.76 | TEST= 0 |
| INDE | 16 | 55 | 33 | FOBS= | 54.7 | SIGMA= | 3.8 | PHAS= | 150.2 | FOM= | 0.81 | TEST= 0 |
| INDE | 16 | 55 | 35 | FOBS= | 152.8 | SIGMA= | 1.6 | PHAS= | 56.5 | FOM= | 0.97 | TEST= 0 |
| INDE | 16 | 55 | 37 | FOBS= | 9.4 | SIGMA= | 19.9 | PHAS= | -10.3 | FOM= | 0.19 | TEST= 0 |
| INDE | 16 | 55 | 39 | FOBS= | 112.0 | SIGMA= | 1.9 | PHAS= | -106.2 | FOM= | 0.93 | TEST= 0 |
| INDE | 16 | 55 | 41 | FOBS= | 54.1 | SIGMA= | 4.0 | PHAS= | 40.5 | FOM= | 0.86 | TEST= 0 |
| INDE | 16 | 55 | 43 | FOBS= | 64.0 | SIGMA= | 3.2 | PHAS= | 89.5 | FOM= | 0.85 | TEST= 0 |
| INDE | 16 | 55 | 45 | FOBS= | 43.2 | SIGMA= | 4.9 | PHAS= | -29.6 | FOM= | 0.59 | TEST= 0 |
| INDE | 16 | 55 | 47 | FOBS= | 0.0 | SIGMA= | 22.8 | PHAS= | 0.0 | FOM= | 0.00 | TEST= 1 |
| INDE | 16 | 55 | 49 | FOBS= | 39.5 | SIGMA= | 7.1 | PHAS= | -107.2 | FOM= | 0.56 | TEST= 0 |
| INDE | 16 | 55 | 51 | FOBS= | 23.8 | SIGMA= | 19.9 | PHAS= | 59.0 | FOM= | 0.79 | TEST= 0 |
| INDE | 16 | 56 | 16 | FOBS= | 129.7 | SIGMA= | 1.7 | PHAS= | 179.2 | FOM= | 0.94 | TEST= 0 |
| INDE | 16 | 56 | 18 | FOBS= | 17.2 | SIGMA= | 15.1 | PHAS= | 172.3 | FOM= | 0.11 | TEST= 1 |
| INDE | 16 | 56 | 20 | FOBS= | 71.1 | SIGMA= | 3.7 | PHAS= | 60.2 | FOM= | 0.80 | TEST= 0 |
| INDE | 16 | 56 | 22 | FOBS= | 189.6 | SIGMA= | 1.3 | PHAS= | 16.0 | FOM= | 0.96 | TEST= 0 |
| INDE | 16 | 56 | 24 | FOBS= | 87.9 | SIGMA= | 2.3 | PHAS= | -74.0 | FOM= | 0.18 | TEST= 1 |
| INDE | 16 | 56 | 26 | FOBS= | 86.2 | SIGMA= | 2.4 | PHAS= | -75.9 | FOM= | 0.26 | TEST= 0 |
| INDE | 16 | 56 | 28 | FOBS= | 108.7 | SIGMA= | 2.0 | PHAS= | 0.2 | FOM= | 0.89 | TEST= 0 |
| INDE | 16 | 56 | 30 | FOBS= | 69.8 | SIGMA= | 3.0 | PHAS= | -9.2 | FOM= | 0.71 | TEST= 0 |
| INDE | 16 | 56 | 32 | FOBS= | 52.3 | SIGMA= | 4.0 | PHAS= | 4.5 | FOM= | 0.66 | TEST= 0 |
| INDE | 16 | 56 | 34 | FOBS= | 152.5 | SIGMA= | 1.6 | PHAS= | 9.3 | FOM= | 0.97 | TEST= 0 |
| INDE | 16 | 56 | 36 | FOBS= | 18.9 | SIGMA= | 13.7 | PHAS= | 28.5 | FOM= | 0.25 | TEST= 0 |
| INDE | 16 | 56 | 38 | FOBS= | 112.7 | SIGMA= | 2.0 | PHAS= | 144.5 | FOM= | 0.73 | TEST= 1 |
| INDE | 16 | 56 | 40 | FOBS= | 24.0 | SIGMA= | 10.2 | PHAS= | 13.6 | FOM= | 0.00 | TEST= 1 |
| INDE | 16 | 56 | 42 | FOBS= | 49.3 | SIGMA= | 5.1 | PHAS= | -127.9 | FOM= | 0.82 | TEST= 0 |
| INDE | 16 | 56 | 44 | FOBS= | 112.4 | SIGMA= | 1.9 | PHAS= | -82.2 | FOM= | 0.96 | TEST= 0 |
| INDE | 16 | 56 | 46 | FOBS= | 83.7 | SIGMA= | 2.8 | PHAS= | 115.3 | FOM= | 0.13 | TEST= 1 |
| INDE | 16 | 56 | 48 | FOBS= | 0.0 | SIGMA= | 21.4 | PHAS= | 0.0 | FOM= | 0.00 | TEST= 0 |
| INDE | 16 | 56 | 50 | FOBS= | 0.0 | SIGMA= | 24.5 | PHAS= | 0.0 | FOM= | 0.00 | TEST= 0 |
| INDE | 16 | 57 | 17 | FOBS= | 0.0 | SIGMA= | 24.5 | PHAS= | 0.0 | FOM= | 0.00 | TEST= 0 |
| INDE | 16 | 57 | 19 | FOBS= | 56.7 | SIGMA= | 4.5 | PHAS= | -51.5 | FOM= | 0.74 | TEST= 0 |
| INDE | 16 | 57 | 21 | FOBS= | 66.8 | SIGMA= | 3.0 | PHAS= | -27.7 | FOM= | 0.90 | TEST= 0 |
| INDE | 16 | 57 | 23 | FOBS= | 35.2 | SIGMA= | 5.7 | PHAS= | 14.3 | FOM= | 0.68 | TEST= 0 |
| INDE | 16 | 57 | 25 | FOBS= | 23.8 | SIGMA= | 14.0 | PHAS= | 77.2 | FOM= | 0.13 | TEST= 0 |
| INDE | 16 | 57 | 27 | FOBS= | 85.6 | SIGMA= | 2.4 | PHAS= | 63.1 | FOM= | 0.84 | TEST= 0 |
| INDE | 16 | 57 | 29 | FOBS= | 55.6 | SIGMA= | 3.7 | PHAS= | -158.5 | FOM= | 0.60 | TEST= 0 |
| INDE | 16 | 57 | 31 | FOBS= | 0.0 | SIGMA= | 21.2 | PHAS= | 0.0 | FOM= | 0.00 | TEST= 0 |
| INDE | 16 | 57 | 33 | FOBS= | 97.2 | SIGMA= | 2.7 | PHAS= | -93.1 | FOM= | 0.95 | TEST= 0 |
| INDE | 16 | 57 | 35 | FOBS= | 45.9 | SIGMA= | 5.6 | PHAS= | -23.1 | FOM= | 0.69 | TEST= 0 |
| INDE | 16 | 57 | 37 | FOBS= | 90.8 | SIGMA= | 2.5 | PHAS= | 59.5 | FOM= | 0.95 | TEST= 0 |

*FIG. 12A - 390*

```
INDE  16  57  39  FOBS=    39.1  SIGMA=   6.2  PHAS=   -17.8  FOM=  0.20  TEST=  0
INDE  16  57  41  FOBS=    86.8  SIGMA=   2.7  PHAS=   105.2  FOM=  0.86  TEST=  0
INDE  16  57  43  FOBS=   163.3  SIGMA=   1.4  PHAS=   156.4  FOM=  0.98  TEST=  0
INDE  16  57  45  FOBS=    33.2  SIGMA=   7.0  PHAS=  -146.1  FOM=  0.81  TEST=  0
INDE  16  57  47  FOBS=    40.2  SIGMA=   5.7  PHAS=  -124.4  FOM=  0.30  TEST=  1
INDE  16  57  49  FOBS=    31.6  SIGMA=   9.7  PHAS=   161.9  FOM=  0.50  TEST=  0
INDE  16  58  16  FOBS=   110.4  SIGMA=   1.9  PHAS=   165.0  FOM=  0.90  TEST=  0
INDE  16  58  18  FOBS=    88.4  SIGMA=   2.9  PHAS=   150.6  FOM=  0.85  TEST=  0
INDE  16  58  20  FOBS=   173.5  SIGMA=   1.6  PHAS=  -113.7  FOM=  0.97  TEST=  0
INDE  16  58  22  FOBS=    35.2  SIGMA=   5.4  PHAS=   -84.5  FOM=  0.64  TEST=  0
INDE  16  58  24  FOBS=    21.6  SIGMA=  10.9  PHAS=    73.8  FOM=  0.16  TEST=  0
INDE  16  58  26  FOBS=    46.0  SIGMA=   4.8  PHAS=   -18.6  FOM=  0.63  TEST=  0
INDE  16  58  28  FOBS=    32.9  SIGMA=   8.6  PHAS=   -37.5  FOM=  0.20  TEST=  0
INDE  16  58  30  FOBS=    55.3  SIGMA=   5.2  PHAS=    51.0  FOM=  0.81  TEST=  0
INDE  16  58  32  FOBS=    54.7  SIGMA=   4.6  PHAS=    84.9  FOM=  0.75  TEST=  0
INDE  16  58  34  FOBS=    63.5  SIGMA=   4.0  PHAS=   -35.7  FOM=  0.53  TEST=  1
INDE  16  58  36  FOBS=    73.9  SIGMA=   3.6  PHAS=   -65.8  FOM=  0.88  TEST=  0
INDE  16  58  38  FOBS=    42.0  SIGMA=   5.2  PHAS=    61.4  FOM=  0.35  TEST=  0
INDE  16  58  40  FOBS=    76.7  SIGMA=   3.0  PHAS=   102.8  FOM=  0.39  TEST=  1
INDE  16  58  42  FOBS=   118.5  SIGMA=   2.0  PHAS=    66.5  FOM=  0.97  TEST=  0
INDE  16  58  44  FOBS=    48.8  SIGMA=   4.2  PHAS=   -67.4  FOM=  0.79  TEST=  0
INDE  16  58  46  FOBS=   114.0  SIGMA=   2.3  PHAS=   165.0  FOM=  0.96  TEST=  0
INDE  16  58  48  FOBS=     0.0  SIGMA=  24.8  PHAS=     0.0  FOM=  0.00  TEST=  1
INDE  16  59  17  FOBS=    67.2  SIGMA=   3.8  PHAS=    -1.9  FOM=  0.40  TEST=  1
INDE  16  59  19  FOBS=    24.4  SIGMA=  10.1  PHAS=   -78.4  FOM=  0.32  TEST=  0
INDE  16  59  21  FOBS=    55.5  SIGMA=   4.4  PHAS=  -127.9  FOM=  0.70  TEST=  0
INDE  16  59  23  FOBS=    25.9  SIGMA=   8.9  PHAS=   -19.8  FOM=  0.12  TEST=  0
INDE  16  59  25  FOBS=    57.7  SIGMA=   4.2  PHAS=    20.2  FOM=  0.20  TEST=  0
INDE  16  59  27  FOBS=    89.5  SIGMA=   2.8  PHAS=  -156.6  FOM=  0.32  TEST=  1
INDE  16  59  29  FOBS=   105.6  SIGMA=   2.8  PHAS=  -148.7  FOM=  0.46  TEST=  1
INDE  16  59  31  FOBS=   108.1  SIGMA=   2.4  PHAS=   -82.0  FOM=  0.95  TEST=  0
INDE  16  59  33  FOBS=    20.8  SIGMA=  12.2  PHAS=   -29.5  FOM=  0.21  TEST=  0
INDE  16  59  35  FOBS=    69.4  SIGMA=   3.8  PHAS=   174.6  FOM=  0.91  TEST=  0
INDE  16  59  37  FOBS=    40.4  SIGMA=   6.5  PHAS=   -39.8  FOM=  0.27  TEST=  0
INDE  16  59  39  FOBS=    43.8  SIGMA=   5.1  PHAS=    43.3  FOM=  0.27  TEST=  1
INDE  16  59  41  FOBS=   115.2  SIGMA=   2.1  PHAS=   -86.2  FOM=  0.96  TEST=  0
INDE  16  59  43  FOBS=   113.2  SIGMA=   2.2  PHAS=  -122.3  FOM=  0.92  TEST=  0
INDE  16  59  45  FOBS=    68.0  SIGMA=   4.0  PHAS=   171.6  FOM=  0.92  TEST=  0
INDE  16  59  47  FOBS=    17.0  SIGMA=  18.5  PHAS=    -5.4  FOM=  0.21  TEST=  0
INDE  16  60  16  FOBS=   102.5  SIGMA=   2.2  PHAS=  -153.9  FOM=  0.11  TEST=  1
INDE  16  60  18  FOBS=    58.9  SIGMA=   6.0  PHAS=   125.8  FOM=  0.87  TEST=  0
INDE  16  60  20  FOBS=    64.5  SIGMA=   4.4  PHAS=   -69.3  FOM=  0.82  TEST=  0
INDE  16  60  22  FOBS=     0.0  SIGMA=  21.7  PHAS=     0.0  FOM=  0.00  TEST=  0
INDE  16  60  24  FOBS=     0.0  SIGMA=  21.5  PHAS=     0.0  FOM=  0.00  TEST=  0
INDE  16  60  26  FOBS=    97.3  SIGMA=   2.5  PHAS=    19.3  FOM=  0.79  TEST=  0
INDE  16  60  28  FOBS=     6.4  SIGMA=  38.2  PHAS=    74.7  FOM=  0.11  TEST=  0
INDE  16  60  30  FOBS=   104.2  SIGMA=   2.5  PHAS=   132.5  FOM=  0.90  TEST=  0
INDE  16  60  32  FOBS=    69.4  SIGMA=   3.7  PHAS=    74.7  FOM=  0.51  TEST=  0
INDE  16  60  34  FOBS=    76.7  SIGMA=   3.4  PHAS=    92.2  FOM=  0.38  TEST=  0
INDE  16  60  36  FOBS=    60.2  SIGMA=   4.4  PHAS=  -168.1  FOM=  0.25  TEST=  1
INDE  16  60  38  FOBS=    26.3  SIGMA=   9.1  PHAS=    -0.5  FOM=  0.39  TEST=  0
INDE  16  60  40  FOBS=    42.9  SIGMA=   5.8  PHAS=   128.7  FOM=  0.81  TEST=  0
INDE  16  60  42  FOBS=   134.9  SIGMA=   1.8  PHAS=   142.8  FOM=  0.98  TEST=  0
INDE  16  60  44  FOBS=    72.9  SIGMA=   3.6  PHAS=   127.0  FOM=  0.92  TEST=  0
INDE  16  60  46  FOBS=    74.4  SIGMA=   3.8  PHAS=   133.3  FOM=  0.81  TEST=  0
INDE  16  61  17  FOBS=     0.0  SIGMA=  26.2  PHAS=     0.0  FOM=  0.00  TEST=  0
INDE  16  61  19  FOBS=     0.0  SIGMA=  26.1  PHAS=     0.0  FOM=  0.00  TEST=  0
INDE  16  61  21  FOBS=     0.0  SIGMA=  26.1  PHAS=     0.0  FOM=  0.00  TEST=  0
INDE  16  61  23  FOBS=     0.0  SIGMA=  21.4  PHAS=     0.0  FOM=  0.00  TEST=  0
INDE  16  61  25  FOBS=     0.0  SIGMA=  21.5  PHAS=     0.0  FOM=  0.00  TEST=  0
INDE  16  61  27  FOBS=    13.8  SIGMA=  17.2  PHAS=     9.9  FOM=  0.10  TEST=  0
INDE  16  61  29  FOBS=     0.0  SIGMA=  23.5  PHAS=     0.0  FOM=  0.00  TEST=  0
INDE  16  61  31  FOBS=     0.0  SIGMA=  24.4  PHAS=     0.0  FOM=  0.00  TEST=  0
INDE  16  61  33  FOBS=    77.1  SIGMA=   3.4  PHAS=   -65.0  FOM=  0.75  TEST=  0
INDE  16  61  35  FOBS=    51.1  SIGMA=   5.2  PHAS=    -3.2  FOM=  0.51  TEST=  0
INDE  16  61  37  FOBS=     0.0  SIGMA=  25.2  PHAS=     0.0  FOM=  0.00  TEST=  0
INDE  16  61  39  FOBS=    51.9  SIGMA=   4.4  PHAS=    82.5  FOM=  0.58  TEST=  0
INDE  16  61  41  FOBS=    42.1  SIGMA=   6.0  PHAS=     6.3  FOM=  0.73  TEST=  0
INDE  16  61  43  FOBS=    55.8  SIGMA=   5.2  PHAS=    37.0  FOM=  0.80  TEST=  0
INDE  16  61  45  FOBS=    83.9  SIGMA=   3.4  PHAS=    58.8  FOM=  0.82  TEST=  0
```

*FIG. 12A - 391*

```
INDE  16  62  16  FOBS=   51.3  SIGMA=   4.7  PHAS=  149.1  FOM=  0.75  TEST=  0
INDE  16  62  18  FOBS=   74.5  SIGMA=   4.7  PHAS=   78.9  FOM=  0.87  TEST=  0
INDE  16  62  20  FOBS=   57.2  SIGMA=   6.0  PHAS=  112.4  FOM=  0.15  TEST=  0
INDE  16  62  22  FOBS=    0.0  SIGMA=  25.8  PHAS=    0.0  FOM=  0.00  TEST=  0
INDE  16  62  24  FOBS=    0.0  SIGMA=  21.6  PHAS=    0.0  FOM=  0.00  TEST=  1
INDE  16  62  26  FOBS=   58.6  SIGMA=   4.1  PHAS=  106.9  FOM=  0.73  TEST=  0
INDE  16  62  28  FOBS=   19.6  SIGMA=  17.3  PHAS=   60.3  FOM=  0.57  TEST=  0
INDE  16  62  30  FOBS=    0.0  SIGMA=  22.3  PHAS=    0.0  FOM=  0.00  TEST=  0
INDE  16  62  32  FOBS=    0.0  SIGMA=  22.6  PHAS=    0.0  FOM=  0.00  TEST=  0
INDE  16  62  34  FOBS=   46.2  SIGMA=   6.5  PHAS= -159.7  FOM=  0.30  TEST=  0
INDE  16  62  36  FOBS=   56.9  SIGMA=   5.4  PHAS=  -95.0  FOM=  0.89  TEST=  0
INDE  16  62  38  FOBS=    0.0  SIGMA=  26.7  PHAS=    0.0  FOM=  0.00  TEST=  0
INDE  16  62  40  FOBS=    0.0  SIGMA=  24.0  PHAS=    0.0  FOM=  0.00  TEST=  0
INDE  16  62  42  FOBS=    0.0  SIGMA=  28.1  PHAS=    0.0  FOM=  0.00  TEST=  1
INDE  16  63  17  FOBS=   43.2  SIGMA=   5.7  PHAS=  -87.9  FOM=  0.47  TEST=  0
INDE  16  63  19  FOBS=   44.3  SIGMA=   7.7  PHAS=   12.3  FOM=  0.23  TEST=  1
INDE  16  63  21  FOBS=    0.0  SIGMA=  26.1  PHAS=    0.0  FOM=  0.00  TEST=  1
INDE  16  63  23  FOBS=    0.0  SIGMA=  25.9  PHAS=    0.0  FOM=  0.00  TEST=  0
INDE  16  63  25  FOBS=  117.8  SIGMA=   2.4  PHAS=   10.8  FOM=  0.94  TEST=  0
INDE  16  63  27  FOBS=   52.8  SIGMA=   5.3  PHAS=   46.6  FOM=  0.88  TEST=  0
INDE  16  63  29  FOBS=   47.4  SIGMA=   6.0  PHAS=   64.6  FOM=  0.55  TEST=  0
INDE  16  63  31  FOBS=   48.6  SIGMA=   6.0  PHAS=  -12.3  FOM=  0.65  TEST=  0
INDE  16  63  33  FOBS=   32.8  SIGMA=   9.2  PHAS=  159.8  FOM=  0.34  TEST=  0
INDE  16  63  35  FOBS=   43.2  SIGMA=   9.1  PHAS=   34.6  FOM=  0.41  TEST=  0
INDE  16  63  37  FOBS=   34.7  SIGMA=   9.0  PHAS=   11.5  FOM=  0.26  TEST=  0
INDE  16  63  39  FOBS=   59.5  SIGMA=   5.3  PHAS=   92.5  FOM=  0.30  TEST=  0
INDE  16  63  41  FOBS=   49.0  SIGMA=   6.7  PHAS= -156.1  FOM=  0.78  TEST=  0
INDE  16  64  16  FOBS=   57.7  SIGMA=   2.7  PHAS=  174.5  FOM=  0.66  TEST=  0
INDE  16  64  18  FOBS=   52.6  SIGMA=   4.6  PHAS=   49.9  FOM=  0.71  TEST=  0
INDE  16  64  20  FOBS=   47.5  SIGMA=   7.3  PHAS=  -82.6  FOM=  0.40  TEST=  0
INDE  16  64  22  FOBS=   48.0  SIGMA=   7.1  PHAS=   53.3  FOM=  0.72  TEST=  0
INDE  16  64  24  FOBS=   98.6  SIGMA=   3.6  PHAS= -119.2  FOM=  0.92  TEST=  0
INDE  16  64  26  FOBS=   95.6  SIGMA=   3.0  PHAS=  -64.2  FOM=  0.87  TEST=  0
INDE  16  64  28  FOBS=  103.2  SIGMA=   2.8  PHAS=  -48.6  FOM=  0.96  TEST=  0
INDE  16  64  30  FOBS=    0.0  SIGMA=  24.0  PHAS=    0.0  FOM=  0.00  TEST=  0
INDE  16  64  32  FOBS=   43.9  SIGMA=   6.8  PHAS=  -80.4  FOM=  0.78  TEST=  0
INDE  16  64  34  FOBS=  108.8  SIGMA=   2.9  PHAS=  -24.5  FOM=  0.96  TEST=  0
INDE  16  64  36  FOBS=   82.7  SIGMA=   3.8  PHAS= -111.5  FOM=  0.87  TEST=  0
INDE  16  64  38  FOBS=    0.0  SIGMA=  25.0  PHAS=    0.0  FOM=  0.00  TEST=  0
INDE  16  64  40  FOBS=   15.3  SIGMA=  20.8  PHAS=  117.9  FOM=  0.25  TEST=  0
INDE  16  65  17  FOBS=   71.5  SIGMA=   2.4  PHAS= -107.5  FOM=  0.84  TEST=  0
INDE  16  65  19  FOBS=   83.9  SIGMA=   4.2  PHAS=  -29.0  FOM=  0.20  TEST=  1
INDE  16  65  21  FOBS=   64.0  SIGMA=   5.4  PHAS= -166.6  FOM=  0.83  TEST=  0
INDE  16  65  23  FOBS=  140.5  SIGMA=   2.6  PHAS=  109.5  FOM=  0.96  TEST=  0
INDE  16  65  25  FOBS=   75.2  SIGMA=   3.7  PHAS=  159.0  FOM=  0.90  TEST=  0
INDE  16  65  27  FOBS=   87.0  SIGMA=   3.3  PHAS= -137.5  FOM=  0.91  TEST=  0
INDE  16  65  29  FOBS=   75.5  SIGMA=   3.9  PHAS= -148.7  FOM=  0.81  TEST=  0
INDE  16  65  31  FOBS=   42.0  SIGMA=   7.0  PHAS=  -55.1  FOM=  0.16  TEST=  1
INDE  16  65  33  FOBS=  116.3  SIGMA=   2.7  PHAS= -144.4  FOM=  0.93  TEST=  0
INDE  16  65  35  FOBS=   62.9  SIGMA=   5.0  PHAS= -177.2  FOM=  0.92  TEST=  0
INDE  16  65  37  FOBS=    0.0  SIGMA=  25.0  PHAS=    0.0  FOM=  0.00  TEST=  0
INDE  16  65  39  FOBS=    0.0  SIGMA=  28.8  PHAS=    0.0  FOM=  0.00  TEST=  0
INDE  16  66  16  FOBS=    0.0  SIGMA=  26.2  PHAS=    0.0  FOM=  0.00  TEST=  0
INDE  16  66  18  FOBS=   43.6  SIGMA=   4.6  PHAS= -161.6  FOM=  0.03  TEST=  1
INDE  16  66  20  FOBS=    0.0  SIGMA=  26.2  PHAS=    0.0  FOM=  0.00  TEST=  0
INDE  16  66  22  FOBS=   93.7  SIGMA=   3.8  PHAS=   47.9  FOM=  0.93  TEST=  0
INDE  16  66  24  FOBS=   73.3  SIGMA=   4.8  PHAS=   74.7  FOM=  0.77  TEST=  0
INDE  16  66  26  FOBS=   26.8  SIGMA=  12.4  PHAS=  112.0  FOM=  0.59  TEST=  0
INDE  16  66  28  FOBS=    9.3  SIGMA=  37.1  PHAS= -126.6  FOM=  0.23  TEST=  0
INDE  16  66  30  FOBS=   86.1  SIGMA=   3.4  PHAS=  105.6  FOM=  0.76  TEST=  0
INDE  16  66  32  FOBS=   57.5  SIGMA=   5.2  PHAS=   69.4  FOM=  0.76  TEST=  0
INDE  16  66  34  FOBS=   51.5  SIGMA=   6.0  PHAS=   57.0  FOM=  0.85  TEST=  0
INDE  16  66  36  FOBS=   69.3  SIGMA=   4.6  PHAS=   -4.7  FOM=  0.72  TEST=  0
INDE  16  67  17  FOBS=   47.2  SIGMA=   5.8  PHAS=  105.5  FOM=  0.09  TEST=  0
INDE  16  67  19  FOBS=   22.1  SIGMA=  12.8  PHAS=   18.3  FOM=  0.23  TEST=  0
INDE  16  67  21  FOBS=   36.5  SIGMA=   9.4  PHAS= -126.2  FOM=  0.25  TEST=  0
INDE  16  67  23  FOBS=   33.3  SIGMA=  10.3  PHAS=   -2.3  FOM=  0.27  TEST=  0
INDE  16  67  25  FOBS=   55.6  SIGMA=   6.2  PHAS=   70.1  FOM=  0.80  TEST=  0
INDE  16  67  27  FOBS=   31.4  SIGMA=   9.0  PHAS=   17.9  FOM=  0.13  TEST=  0
INDE  16  67  29  FOBS=   51.4  SIGMA=   5.6  PHAS=  105.3  FOM=  0.70  TEST=  0
```

*FIG. 12A - 392*

```
INDE 16 67 31 FOBS=    70.0 SIGMA=  4.3 PHAS=  -65.5 FOM= 0.74 TEST= 0
INDE 16 67 33 FOBS=    16.7 SIGMA= 22.5 PHAS=   35.1 FOM= 0.27 TEST= 0
INDE 16 67 35 FOBS=    47.3 SIGMA=  6.7 PHAS= -118.8 FOM= 0.33 TEST= 0
INDE 16 68 16 FOBS=     0.0 SIGMA= 24.8 PHAS=    0.0 FOM= 0.00 TEST= 1
INDE 16 68 18 FOBS=     0.0 SIGMA= 19.3 PHAS=    0.0 FOM= 0.00 TEST= 0
INDE 16 68 20 FOBS=     0.0 SIGMA= 31.4 PHAS=    0.0 FOM= 0.00 TEST= 0
INDE 16 68 22 FOBS=     0.0 SIGMA= 31.2 PHAS=    0.0 FOM= 0.00 TEST= 0
INDE 16 68 24 FOBS=    78.1 SIGMA=  6.4 PHAS=   12.2 FOM= 0.84 TEST= 0
INDE 16 68 26 FOBS=    25.7 SIGMA= 13.6 PHAS=   37.7 FOM= 0.51 TEST= 0
INDE 16 68 28 FOBS=     0.0 SIGMA= 23.8 PHAS=    0.0 FOM= 0.00 TEST= 0
INDE 16 68 30 FOBS=     0.0 SIGMA= 24.1 PHAS=    0.0 FOM= 0.00 TEST= 1
INDE 16 68 32 FOBS=     0.0 SIGMA= 26.7 PHAS=    0.0 FOM= 0.00 TEST= 0
INDE 16 68 34 FOBS=    91.6 SIGMA=  3.5 PHAS=  -21.0 FOM= 0.41 TEST= 0
INDE 16 69 17 FOBS=     0.0 SIGMA= 25.4 PHAS=    0.0 FOM= 0.00 TEST= 0
INDE 16 69 19 FOBS=    15.4 SIGMA= 13.2 PHAS=   24.5 FOM= 0.33 TEST= 0
INDE 16 69 25 FOBS=    84.9 SIGMA=  6.1 PHAS=  -19.7 FOM= 0.90 TEST= 0
INDE 16 69 27 FOBS=    59.4 SIGMA=  5.9 PHAS=  -62.9 FOM= 0.61 TEST= 0
INDE 16 69 29 FOBS=     0.0 SIGMA= 26.8 PHAS=    0.0 FOM= 0.00 TEST= 0
INDE 16 69 31 FOBS=     0.0 SIGMA= 24.3 PHAS=    0.0 FOM= 0.00 TEST= 0
INDE 16 70 16 FOBS=    65.1 SIGMA=  4.5 PHAS=  101.3 FOM= 0.74 TEST= 0
INDE 16 70 18 FOBS=    27.7 SIGMA= 12.0 PHAS=   16.4 FOM= 0.25 TEST= 0
INDE 16 70 20 FOBS=     0.0 SIGMA= 20.5 PHAS=    0.0 FOM= 0.00 TEST= 0
INDE 16 70 28 FOBS=    53.6 SIGMA=  9.4 PHAS=  147.8 FOM= 0.31 TEST= 0
INDE 16 71 17 FOBS=    55.3 SIGMA=  5.6 PHAS=  -51.4 FOM= 0.67 TEST= 0
INDE 16 71 19 FOBS=    49.2 SIGMA=  3.6 PHAS=   85.1 FOM= 0.82 TEST= 0
INDE 16 71 21 FOBS=     0.0 SIGMA= 23.8 PHAS=    0.0 FOM= 0.00 TEST= 0
INDE 16 71 23 FOBS=    89.0 SIGMA=  4.2 PHAS=   37.1 FOM= 0.33 TEST= 1
INDE 16 72 16 FOBS=    40.4 SIGMA=  5.8 PHAS=  -19.1 FOM= 0.32 TEST= 0
INDE 16 72 18 FOBS=     0.0 SIGMA= 25.8 PHAS=    0.0 FOM= 0.00 TEST= 0
INDE 16 72 20 FOBS=    50.1 SIGMA=  4.0 PHAS=   -5.6 FOM= 0.85 TEST= 0
INDE 16 72 22 FOBS=     0.0 SIGMA= 24.9 PHAS=    0.0 FOM= 0.00 TEST= 0
INDE 16 72 24 FOBS=     0.0 SIGMA= 27.6 PHAS=    0.0 FOM= 0.00 TEST= 0
INDE 16 73 17 FOBS=    63.6 SIGMA=  4.7 PHAS= -127.8 FOM= 0.76 TEST= 0
INDE 16 73 19 FOBS=     0.0 SIGMA= 26.2 PHAS=    0.0 FOM= 0.00 TEST= 0
INDE 16 73 21 FOBS=    24.0 SIGMA=  8.9 PHAS=  140.6 FOM= 0.05 TEST= 1
INDE 17 18 17 FOBS=   241.8 SIGMA=  0.6 PHAS=  178.8 FOM= 0.97 TEST= 0
INDE 17 18 19 FOBS=   164.7 SIGMA=  0.7 PHAS=  101.5 FOM= 0.98 TEST= 0
INDE 17 18 21 FOBS=    25.5 SIGMA=  3.1 PHAS= -176.5 FOM= 0.91 TEST= 1
INDE 17 18 23 FOBS=   166.3 SIGMA=  0.6 PHAS=  -75.6 FOM= 0.99 TEST= 0
INDE 17 18 25 FOBS=    24.0 SIGMA=  4.1 PHAS= -153.5 FOM= 0.96 TEST= 0
INDE 17 18 27 FOBS=   110.9 SIGMA=  1.1 PHAS= -117.9 FOM= 0.94 TEST= 0
INDE 17 18 29 FOBS=   137.3 SIGMA=  0.9 PHAS=   87.3 FOM= 0.92 TEST= 0
INDE 17 18 31 FOBS=   332.6 SIGMA=  0.6 PHAS= -123.8 FOM= 0.95 TEST= 0
INDE 17 18 33 FOBS=    34.0 SIGMA=  3.6 PHAS= -103.6 FOM= 0.22 TEST= 0
INDE 17 18 35 FOBS=   130.9 SIGMA=  1.0 PHAS=  -21.6 FOM= 0.93 TEST= 0
INDE 17 18 37 FOBS=   165.4 SIGMA=  1.0 PHAS=  113.4 FOM= 0.89 TEST= 0
INDE 17 18 39 FOBS=   117.1 SIGMA=  1.4 PHAS=  150.3 FOM= 0.85 TEST= 0
INDE 17 18 41 FOBS=   171.1 SIGMA=  1.2 PHAS=  -48.7 FOM= 0.92 TEST= 0
INDE 17 18 43 FOBS=   257.8 SIGMA=  0.9 PHAS=  -96.8 FOM= 0.94 TEST= 0
INDE 17 18 45 FOBS=    56.4 SIGMA=  3.4 PHAS= -148.5 FOM= 0.84 TEST= 0
INDE 17 18 47 FOBS=   100.9 SIGMA=  1.9 PHAS=   95.8 FOM= 0.57 TEST= 0
INDE 17 18 49 FOBS=     0.0 SIGMA= 21.2 PHAS=    0.0 FOM= 0.00 TEST= 0
INDE 17 18 51 FOBS=    26.9 SIGMA=  7.1 PHAS=   83.2 FOM= 0.16 TEST= 0
INDE 17 18 53 FOBS=   132.6 SIGMA=  1.5 PHAS=  -39.2 FOM= 0.91 TEST= 0
INDE 17 18 55 FOBS=   128.9 SIGMA=  1.5 PHAS=  -14.2 FOM= 0.86 TEST= 0
INDE 17 18 57 FOBS=    50.0 SIGMA=  4.6 PHAS=   54.0 FOM= 0.52 TEST= 0
INDE 17 18 59 FOBS=   114.7 SIGMA=  2.3 PHAS=   67.9 FOM= 0.94 TEST= 0
INDE 17 18 61 FOBS=    68.7 SIGMA=  3.6 PHAS= -110.6 FOM= 0.18 TEST= 0
INDE 17 18 63 FOBS=    60.2 SIGMA=  4.1 PHAS=  -16.7 FOM= 0.85 TEST= 0
INDE 17 18 65 FOBS=     0.0 SIGMA= 22.1 PHAS=    0.0 FOM= 0.00 TEST= 1
INDE 17 18 67 FOBS=    31.1 SIGMA=  5.7 PHAS=  180.0 FOM= 0.33 TEST= 0
INDE 17 18 69 FOBS=    18.2 SIGMA= 17.8 PHAS= -131.9 FOM= 0.42 TEST= 0
INDE 17 18 71 FOBS=    36.0 SIGMA=  7.8 PHAS=  140.1 FOM= 0.48 TEST= 0
INDE 17 18 73 FOBS=    66.5 SIGMA=  4.2 PHAS=  -25.9 FOM= 0.11 TEST= 1
INDE 17 19 18 FOBS=   181.9 SIGMA=  0.6 PHAS=   81.0 FOM= 0.99 TEST= 0
INDE 17 19 20 FOBS=   100.9 SIGMA=  1.0 PHAS= -138.9 FOM= 0.96 TEST= 1
INDE 17 19 22 FOBS=    93.2 SIGMA=  0.9 PHAS= -139.2 FOM= 0.99 TEST= 0
INDE 17 19 24 FOBS=   279.9 SIGMA=  0.5 PHAS=  -60.9 FOM= 0.99 TEST= 0
INDE 17 19 26 FOBS=    94.1 SIGMA=  1.2 PHAS=  -43.5 FOM= 0.90 TEST= 0
INDE 17 19 28 FOBS=   186.4 SIGMA=  0.8 PHAS=   59.8 FOM= 0.98 TEST= 0
```

*FIG. 12A - 393*

```
INDE 17 19 30 FOBS=    204.2 SIGMA=  0.7 PHAS=   79.6 FOM= 0.86 TEST= 0
INDE 17 19 32 FOBS=    220.9 SIGMA=  0.7 PHAS= -178.1 FOM= 0.96 TEST= 0
INDE 17 19 34 FOBS=    214.6 SIGMA=  0.7 PHAS= -130.0 FOM= 0.97 TEST= 0
INDE 17 19 36 FOBS=    147.4 SIGMA=  0.9 PHAS=  -75.1 FOM= 0.96 TEST= 0
INDE 17 19 38 FOBS=     91.2 SIGMA=  1.5 PHAS=  -37.1 FOM= 0.94 TEST= 0
INDE 17 19 40 FOBS=    135.1 SIGMA=  1.1 PHAS=  -92.1 FOM= 0.92 TEST= 0
INDE 17 19 42 FOBS=    243.6 SIGMA=  0.7 PHAS=  166.3 FOM= 0.93 TEST= 0
INDE 17 19 44 FOBS=     42.8 SIGMA=  3.6 PHAS=   86.7 FOM= 0.73 TEST= 0
INDE 17 19 46 FOBS=    116.1 SIGMA=  1.4 PHAS=  -81.8 FOM= 0.84 TEST= 0
INDE 17 19 48 FOBS=    128.1 SIGMA=  1.6 PHAS= -138.3 FOM= 0.89 TEST= 0
INDE 17 19 50 FOBS=     23.1 SIGMA=  9.1 PHAS=   17.5 FOM= 0.46 TEST= 0
INDE 17 19 52 FOBS=    160.4 SIGMA=  1.3 PHAS= -100.3 FOM= 0.96 TEST= 0
INDE 17 19 54 FOBS=      0.0 SIGMA= 19.6 PHAS=    0.0 FOM= 0.00 TEST= 0
INDE 17 19 56 FOBS=     47.8 SIGMA=  3.9 PHAS=   73.1 FOM= 0.79 TEST= 0
INDE 17 19 58 FOBS=     90.2 SIGMA=  2.4 PHAS= -125.3 FOM= 0.90 TEST= 0
INDE 17 19 60 FOBS=     88.5 SIGMA=  2.9 PHAS=   82.0 FOM= 0.74 TEST= 0
INDE 17 19 62 FOBS=     50.1 SIGMA=  5.0 PHAS=   94.5 FOM= 0.85 TEST= 0
INDE 17 19 64 FOBS=     54.1 SIGMA=  4.6 PHAS= -166.2 FOM= 0.83 TEST= 0
INDE 17 19 66 FOBS=     32.1 SIGMA=  8.9 PHAS=  -61.8 FOM= 0.49 TEST= 0
INDE 17 19 68 FOBS=     92.5 SIGMA=  3.4 PHAS=  148.1 FOM= 0.95 TEST= 0
INDE 17 19 70 FOBS=     52.7 SIGMA=  5.6 PHAS=   84.6 FOM= 0.84 TEST= 0
INDE 17 19 72 FOBS=     37.4 SIGMA=  7.7 PHAS=  112.5 FOM= 0.61 TEST= 0
INDE 17 20 17 FOBS=    188.0 SIGMA=  0.6 PHAS= -110.3 FOM= 0.96 TEST= 0
INDE 17 20 19 FOBS=    123.2 SIGMA=  0.8 PHAS=   60.8 FOM= 0.99 TEST= 0
INDE 17 20 21 FOBS=     78.9 SIGMA=  1.1 PHAS= -150.3 FOM= 0.67 TEST= 0
INDE 17 20 23 FOBS=    342.7 SIGMA=  0.4 PHAS= -175.4 FOM= 0.98 TEST= 0
INDE 17 20 25 FOBS=    274.2 SIGMA=  0.5 PHAS= -139.8 FOM= 0.99 TEST= 0
INDE 17 20 27 FOBS=    222.0 SIGMA=  0.6 PHAS= -107.1 FOM= 0.97 TEST= 0
INDE 17 20 29 FOBS=    227.9 SIGMA=  0.6 PHAS=   -4.7 FOM= 0.97 TEST= 0
INDE 17 20 31 FOBS=     45.3 SIGMA=  2.4 PHAS=  158.7 FOM= 0.58 TEST= 0
INDE 17 20 33 FOBS=     70.9 SIGMA=  1.7 PHAS=   23.0 FOM= 0.54 TEST= 0
INDE 17 20 35 FOBS=     89.1 SIGMA=  1.3 PHAS= -128.6 FOM= 0.94 TEST= 0
INDE 17 20 37 FOBS=    200.5 SIGMA=  0.7 PHAS= -166.1 FOM= 0.96 TEST= 0
INDE 17 20 39 FOBS=    199.2 SIGMA=  0.8 PHAS= -131.5 FOM= 0.91 TEST= 0
INDE 17 20 41 FOBS=     61.8 SIGMA=  2.4 PHAS=   63.6 FOM= 0.79 TEST= 0
INDE 17 20 43 FOBS=     23.2 SIGMA=  6.7 PHAS=  -42.4 FOM= 0.62 TEST= 0
INDE 17 20 45 FOBS=      0.0 SIGMA= 17.2 PHAS=    0.0 FOM= 0.00 TEST= 0
INDE 17 20 47 FOBS=    113.7 SIGMA=  1.5 PHAS=  129.9 FOM= 0.86 TEST= 0
INDE 17 20 49 FOBS=     99.6 SIGMA=  1.9 PHAS= -144.5 FOM= 0.85 TEST= 0
INDE 17 20 51 FOBS=      0.0 SIGMA= 25.5 PHAS=    0.0 FOM= 0.00 TEST= 0
INDE 17 20 53 FOBS=     45.7 SIGMA=  4.2 PHAS=   15.9 FOM= 0.11 TEST= 0
INDE 17 20 55 FOBS=    103.1 SIGMA=  1.9 PHAS=   77.2 FOM= 0.92 TEST= 0
INDE 17 20 57 FOBS=     87.0 SIGMA=  2.5 PHAS=  141.9 FOM= 0.91 TEST= 0
INDE 17 20 59 FOBS=    180.5 SIGMA=  1.6 PHAS=   66.5 FOM= 0.96 TEST= 0
INDE 17 20 61 FOBS=     37.0 SIGMA=  6.9 PHAS=   11.6 FOM= 0.73 TEST= 0
INDE 17 20 63 FOBS=     46.5 SIGMA=  5.4 PHAS= -147.4 FOM= 0.14 TEST= 0
INDE 17 20 65 FOBS=     34.2 SIGMA=  7.3 PHAS=  -98.4 FOM= 0.15 TEST= 0
INDE 17 20 67 FOBS=    115.7 SIGMA=  2.8 PHAS=   67.6 FOM= 0.93 TEST= 0
INDE 17 20 69 FOBS=     64.6 SIGMA=  4.8 PHAS=   52.9 FOM= 0.93 TEST= 0
INDE 17 20 71 FOBS=     36.9 SIGMA=  7.9 PHAS=  -23.3 FOM= 0.77 TEST= 0
INDE 17 21 18 FOBS=     88.4 SIGMA=  1.0 PHAS=  157.0 FOM= 0.92 TEST= 0
INDE 17 21 20 FOBS=    180.8 SIGMA=  0.7 PHAS=  -67.8 FOM= 0.99 TEST= 0
INDE 17 21 22 FOBS=    118.9 SIGMA=  0.8 PHAS= -111.2 FOM= 0.90 TEST= 0
INDE 17 21 24 FOBS=    265.4 SIGMA=  0.5 PHAS=  118.3 FOM= 0.97 TEST= 0
INDE 17 21 26 FOBS=    288.2 SIGMA=  0.6 PHAS=  122.5 FOM= 0.95 TEST= 0
INDE 17 21 28 FOBS=     83.3 SIGMA=  1.3 PHAS=  -12.4 FOM= 0.96 TEST= 0
INDE 17 21 30 FOBS=    268.0 SIGMA=  0.7 PHAS=   70.5 FOM= 0.94 TEST= 0
INDE 17 21 32 FOBS=    116.1 SIGMA=  1.1 PHAS=  161.9 FOM= 0.95 TEST= 0
INDE 17 21 34 FOBS=    111.7 SIGMA=  1.2 PHAS=  132.7 FOM= 0.85 TEST= 0
INDE 17 21 36 FOBS=    131.7 SIGMA=  1.0 PHAS=  143.1 FOM= 0.98 TEST= 0
INDE 17 21 38 FOBS=     36.9 SIGMA=  3.8 PHAS= -100.5 FOM= 0.24 TEST= 0
INDE 17 21 40 FOBS=    171.0 SIGMA=  1.0 PHAS=  177.6 FOM= 0.92 TEST= 0
INDE 17 21 42 FOBS=     99.1 SIGMA=  1.5 PHAS=   32.8 FOM= 0.76 TEST= 0
INDE 17 21 44 FOBS=     97.1 SIGMA=  1.5 PHAS=   -8.2 FOM= 0.86 TEST= 0
INDE 17 21 46 FOBS=      0.0 SIGMA= 18.0 PHAS=    0.0 FOM= 0.00 TEST= 0
INDE 17 21 48 FOBS=     88.8 SIGMA=  1.9 PHAS=  -90.3 FOM= 0.74 TEST= 0
INDE 17 21 50 FOBS=     67.0 SIGMA=  2.5 PHAS=   64.9 FOM= 0.39 TEST= 0
INDE 17 21 52 FOBS=     99.9 SIGMA=  1.7 PHAS= -130.1 FOM= 0.79 TEST= 0
INDE 17 21 54 FOBS=     59.7 SIGMA=  3.2 PHAS=   -4.1 FOM= 0.85 TEST= 0
INDE 17 21 56 FOBS=    149.4 SIGMA=  1.6 PHAS=   28.0 FOM= 0.96 TEST= 0
```

*FIG. 12A - 394*

```
INDE  17  21  58  FOBS=   128.2  SIGMA=   1.9  PHAS=   -24.4  FOM=  0.92  TEST= 0
INDE  17  21  60  FOBS=    19.4  SIGMA=  15.6  PHAS=   -56.5  FOM=  0.06  TEST= 0
INDE  17  21  62  FOBS=     0.0  SIGMA=  24.5  PHAS=     0.0  FOM=  0.00  TEST= 1
INDE  17  21  64  FOBS=    32.6  SIGMA=  11.0  PHAS=   142.8  FOM=  0.05  TEST= 1
INDE  17  21  66  FOBS=    89.4  SIGMA=   3.7  PHAS=   -24.2  FOM=  0.92  TEST= 0
INDE  17  21  68  FOBS=    54.9  SIGMA=   6.0  PHAS=    11.7  FOM=  0.86  TEST= 0
INDE  17  21  70  FOBS=    21.0  SIGMA=  14.0  PHAS=   -46.8  FOM=  0.69  TEST= 0
INDE  17  22  17  FOBS=    50.9  SIGMA=   1.7  PHAS=   150.2  FOM=  0.97  TEST= 0
INDE  17  22  19  FOBS=   158.3  SIGMA=   0.7  PHAS=  -149.9  FOM=  0.93  TEST= 0
INDE  17  22  21  FOBS=   136.9  SIGMA=   0.8  PHAS=  -124.7  FOM=  0.95  TEST= 0
INDE  17  22  23  FOBS=   155.1  SIGMA=   0.7  PHAS=   177.1  FOM=  0.99  TEST= 0
INDE  17  22  25  FOBS=   247.3  SIGMA=   0.5  PHAS=     1.6  FOM=  0.99  TEST= 0
INDE  17  22  27  FOBS=    87.0  SIGMA=   1.3  PHAS=   -22.3  FOM=  0.95  TEST= 0
INDE  17  22  29  FOBS=    53.7  SIGMA=   2.2  PHAS=  -150.5  FOM=  0.93  TEST= 0
INDE  17  22  31  FOBS=   148.7  SIGMA=   0.9  PHAS=   -12.8  FOM=  0.93  TEST= 0
INDE  17  22  33  FOBS=   249.2  SIGMA=   0.7  PHAS=     2.0  FOM=  0.92  TEST= 0
INDE  17  22  35  FOBS=   214.1  SIGMA=   0.7  PHAS=   -12.4  FOM=  0.97  TEST= 1
INDE  17  22  37  FOBS=   229.1  SIGMA=   0.7  PHAS=    96.7  FOM=  0.95  TEST= 0
INDE  17  22  39  FOBS=   253.9  SIGMA=   0.7  PHAS=    74.1  FOM=  0.95  TEST= 0
INDE  17  22  41  FOBS=    84.7  SIGMA=   1.7  PHAS=    16.3  FOM=  0.96  TEST= 0
INDE  17  22  43  FOBS=.  242.0  SIGMA=   0.7  PHAS=   -78.3  FOM=  0.94  TEST= 0
INDE  17  22  45  FOBS=   152.0  SIGMA=   1.1  PHAS=   -61.1  FOM=  0.97  TEST= 0
INDE  17  22  47  FOBS=   139.6  SIGMA=   1.2  PHAS=   129.4  FOM=  0.85  TEST= 0
INDE  17  22  49  FOBS=    49.6  SIGMA=   3.3  PHAS=  -133.6  FOM=  0.23  TEST= 0
INDE  17  22  51  FOBS=    37.4  SIGMA=   4.2  PHAS=   -80.7  FOM=  0.35  TEST= 1
INDE  17  22  53  FOBS=    30.3  SIGMA=   5.9  PHAS=   -47.9  FOM=  0.40  TEST= 0
INDE  17  22  55  FOBS=    85.4  SIGMA=   2.0  PHAS=   -83.6  FOM=  0.85  TEST= 0
INDE  17  22  57  FOBS=   124.1  SIGMA=   1.9  PHAS=  -118.9  FOM=  0.95  TEST= 0
INDE  17  22  59  FOBS=     0.0  SIGMA=  23.0  PHAS=     0.0  FOM=  0.00  TEST= 1
INDE  17  22  61  FOBS=    58.6  SIGMA=   4.4  PHAS=  -101.4  FOM=  0.66  TEST= 1
INDE  17  22  63  FOBS=    63.8  SIGMA=   4.0  PHAS=   -89.2  FOM=  0.75  TEST= 0
INDE  17  22  65  FOBS=    55.2  SIGMA=   5.2  PHAS=   -54.2  FOM=  0.39  TEST= 0
INDE  17  22  67  FOBS=    82.3  SIGMA=   4.0  PHAS=    11.9  FOM=  0.54  TEST= 0
INDE  17  22  69  FOBS=    18.4  SIGMA=  16.6  PHAS=    44.3  FOM=  0.32  TEST= 0
INDE  17  23  18  FOBS=   247.9  SIGMA=   0.5  PHAS=    96.4  FOM=  0.51  TEST= 1
INDE  17  23  20  FOBS=    66.4  SIGMA=   1.5  PHAS=     7.8  FOM=  0.85  TEST= 0
INDE  17  23  22  FOBS=   127.3  SIGMA=   0.9  PHAS=   -43.6  FOM=  0.98  TEST= 0
INDE  17  23  24  FOBS=   199.8  SIGMA=   0.6  PHAS=   145.7  FOM=  0.98  TEST= 1
INDE  17  23  26  FOBS=    12.8  SIGMA=   8.5  PHAS=   -96.9  FOM=  0.14  TEST= 0
INDE  17  23  28  FOBS=    92.9  SIGMA=   1.3  PHAS=    23.1  FOM=  0.98  TEST= 0
INDE  17  23  30  FOBS=   106.0  SIGMA=   1.2  PHAS=   -67.9  FOM=  0.87  TEST= 0
INDE  17  23  32  FOBS=   358.9  SIGMA=   0.6  PHAS=   -66.5  FOM=  0.96  TEST= 0
INDE  17  23  34  FOBS=   177.9  SIGMA=   0.9  PHAS=   -75.8  FOM=  0.91  TEST= 0
INDE  17  23  36  FOBS=     0.0  SIGMA=  17.2  PHAS=     0.0  FOM=  0.00  TEST= 1
INDE  17  23  38  FOBS=   342.7  SIGMA=   0.6  PHAS=   -18.3  FOM=  0.97  TEST= 0
INDE  17  23  40  FOBS=   131.7  SIGMA=   1.2  PHAS=   -13.1  FOM=  0.11  TEST= 1
INDE  17  23  42  FOBS=     0.0  SIGMA=  17.8  PHAS=     0.0  FOM=  0.00  TEST= 0
INDE  17  23  44  FOBS=   285.6  SIGMA=   0.7  PHAS=  -179.8  FOM=  0.82  TEST= 1
INDE  17  23  46  FOBS=   129.7  SIGMA=   1.2  PHAS=  -117.0  FOM=  0.95  TEST= 0
INDE  17  23  48  FOBS=   260.0  SIGMA=   0.7  PHAS=   -43.5  FOM=  0.96  TEST= 0
INDE  17  23  50  FOBS=    93.0  SIGMA=   1.7  PHAS=    58.2  FOM=  0.90  TEST= 0
INDE  17  23  52  FOBS=    43.0  SIGMA=   3.6  PHAS=  -154.5  FOM=  0.32  TEST= 0
INDE  17  23  54  FOBS=    91.5  SIGMA=   1.9  PHAS=   130.3  FOM=  0.94  TEST= 0
INDE  17  23  56  FOBS=    67.3  SIGMA=   2.8  PHAS=   125.7  FOM=  0.86  TEST= 0
INDE  17  23  58  FOBS=    83.3  SIGMA=   2.6  PHAS=     2.4  FOM=  0.12  TEST= 1
INDE  17  23  60  FOBS=    98.1  SIGMA=   2.7  PHAS=   159.0  FOM=  0.78  TEST= 0
INDE  17  23  62  FOBS=    54.5  SIGMA=   4.7  PHAS=   124.9  FOM=  0.79  TEST= 0
INDE  17  23  64  FOBS=    95.9  SIGMA=   2.7  PHAS=  -152.5  FOM=  0.93  TEST= 0
INDE  17  23  66  FOBS=     9.0  SIGMA=  36.0  PHAS=    18.7  FOM=  0.07  TEST= 0
INDE  17  23  68  FOBS=    98.5  SIGMA=   3.3  PHAS=   -54.2  FOM=  0.89  TEST= 0
INDE  17  24  17  FOBS=   148.7  SIGMA=   0.7  PHAS=     9.9  FOM=  0.96  TEST= 0
INDE  17  24  19  FOBS=    76.7  SIGMA=   1.3  PHAS=   125.0  FOM=  0.92  TEST= 0
INDE  17  24  21  FOBS=   219.4  SIGMA=   0.7  PHAS=  -115.0  FOM=  0.98  TEST= 0
INDE  17  24  23  FOBS=   187.5  SIGMA=   0.7  PHAS=  -148.0  FOM=  0.90  TEST= 1
INDE  17  24  25  FOBS=   144.6  SIGMA=   0.8  PHAS=   136.0  FOM=  0.94  TEST= 0
INDE  17  24  27  FOBS=    18.8  SIGMA=   6.6  PHAS=    49.4  FOM=  0.04  TEST= 0
INDE  17  24  29  FOBS=   164.0  SIGMA=   0.9  PHAS=  -121.3  FOM=  0.90  TEST= 0
INDE  17  24  31  FOBS=   114.5  SIGMA=   1.2  PHAS=  -157.5  FOM=  0.93  TEST= 0
INDE  17  24  33  FOBS=   216.6  SIGMA=   0.8  PHAS=  -108.2  FOM=  0.96  TEST= 0
INDE  17  24  35  FOBS=   285.8  SIGMA=   0.7  PHAS=   -83.3  FOM=  0.96  TEST= 0
```

*FIG. 12A - 395*

```
INDE  17  24  37  FOBS=   61.1  SIGMA=   2.7  PHAS= -158.1  FOM= 0.83  TEST= 1
INDE  17  24  39  FOBS=    0.0  SIGMA=  18.2  PHAS=    0.0  FOM= 0.00  TEST= 0
INDE  17  24  41  FOBS=   37.2  SIGMA=   4.4  PHAS=   66.4  FOM= 0.62  TEST= 0
INDE  17  24  43  FOBS=   66.5  SIGMA=   2.4  PHAS=  -54.7  FOM= 0.49  TEST= 0
INDE  17  24  45  FOBS=  257.2  SIGMA=   0.7  PHAS=  151.9  FOM= 0.97  TEST= 0
INDE  17  24  47  FOBS=  294.3  SIGMA=   0.7  PHAS=  140.8  FOM= 0.97  TEST= 0
INDE  17  24  49  FOBS=   82.8  SIGMA=   1.8  PHAS= -111.2  FOM= 0.93  TEST= 0
INDE  17  24  51  FOBS=  182.0  SIGMA=   1.0  PHAS=  -54.7  FOM= 0.95  TEST= 0
INDE  17  24  53  FOBS=   85.7  SIGMA=   1.9  PHAS=   -3.2  FOM= 0.88  TEST= 0
INDE  17  24  55  FOBS=   88.9  SIGMA=   1.9  PHAS=   20.9  FOM= 0.89  TEST= 0
INDE  17  24  57  FOBS=   98.8  SIGMA=   2.1  PHAS= -139.1  FOM= 0.88  TEST= 0
INDE  17  24  59  FOBS=   86.0  SIGMA=   2.5  PHAS=  156.6  FOM= 0.81  TEST= 0
INDE  17  24  61  FOBS=   79.3  SIGMA=   2.7  PHAS=  114.0  FOM= 0.80  TEST= 0
INDE  17  24  63  FOBS=   74.9  SIGMA=   3.5  PHAS=  102.0  FOM= 0.88  TEST= 0
INDE  17  24  65  FOBS=   49.7  SIGMA=   6.9  PHAS=  109.4  FOM= 0.58  TEST= 0
INDE  17  24  67  FOBS=    0.0  SIGMA=  25.3  PHAS=    0.0  FOM= 0.00  TEST= 0
INDE  17  25  18  FOBS=  128.9  SIGMA=   0.8  PHAS=  144.6  FOM= 0.96  TEST= 0
INDE  17  25  20  FOBS=  111.9  SIGMA=   1.0  PHAS=   16.8  FOM= 0.95  TEST= 0
INDE  17  25  22  FOBS=  108.7  SIGMA=   1.0  PHAS= -178.0  FOM= 0.93  TEST= 0
INDE  17  25  24  FOBS=  319.6  SIGMA=   0.5  PHAS=   70.0  FOM= 0.98  TEST= 0
INDE  17  25  26  FOBS=  313.3  SIGMA=   0.5  PHAS=   27.7  FOM= 0.93  TEST= 0
INDE  17  25  28  FOBS=  103.1  SIGMA=   1.2  PHAS=  117.3  FOM= 0.95  TEST= 0
INDE  17  25  30  FOBS=  162.7  SIGMA=   0.9  PHAS=  132.6  FOM= 0.97  TEST= 0
INDE  17  25  32  FOBS=  127.5  SIGMA=   1.1  PHAS=  -10.9  FOM= 0.84  TEST= 0
INDE  17  25  34  FOBS=  359.2  SIGMA=   0.6  PHAS=  165.2  FOM= 0.98  TEST= 0
INDE  17  25  36  FOBS=  226.9  SIGMA=   0.8  PHAS=  162.2  FOM= 0.87  TEST= 0
INDE  17  25  38  FOBS=  137.5  SIGMA=   1.4  PHAS=   37.7  FOM= 0.90  TEST= 0
INDE  17  25  40  FOBS=   90.2  SIGMA=   2.0  PHAS=   78.7  FOM= 0.68  TEST= 0
INDE  17  25  42  FOBS=   19.6  SIGMA=   9.0  PHAS= -114.8  FOM= 0.56  TEST= 0
INDE  17  25  44  FOBS=   44.5  SIGMA=   3.5  PHAS=  147.4  FOM= 0.66  TEST= 0
INDE  17  25  46  FOBS=  224.2  SIGMA=   0.8  PHAS=   34.9  FOM= 0.91  TEST= 0
INDE  17  25  48  FOBS=  100.3  SIGMA=   1.5  PHAS=  -39.0  FOM= 0.91  TEST= 0
INDE  17  25  50  FOBS=    0.0  SIGMA=  18.6  PHAS=    0.0  FOM= 0.00  TEST= 0
INDE  17  25  52  FOBS=   53.1  SIGMA=   3.0  PHAS= -128.0  FOM= 0.80  TEST= 1
INDE  17  25  54  FOBS=   80.4  SIGMA=   2.0  PHAS= -168.8  FOM= 0.90  TEST= 0
INDE  17  25  56  FOBS=   26.3  SIGMA=   6.8  PHAS= -177.8  FOM= 0.63  TEST= 0
INDE  17  25  58  FOBS=    0.0  SIGMA=  21.7  PHAS=    0.0  FOM= 0.00  TEST= 0
INDE  17  25  60  FOBS=   65.4  SIGMA=   3.3  PHAS=   51.9  FOM= 0.69  TEST= 0
INDE  17  25  62  FOBS=   57.7  SIGMA=   3.6  PHAS=   36.1  FOM= 0.75  TEST= 0
INDE  17  25  64  FOBS=   16.8  SIGMA=  17.5  PHAS= -108.7  FOM= 0.32  TEST= 0
INDE  17  26  17  FOBS=   19.4  SIGMA=   6.0  PHAS=  134.8  FOM= 0.08  TEST= 0
INDE  17  26  19  FOBS=   92.5  SIGMA=   1.1  PHAS=   -8.1  FOM= 0.99  TEST= 0
INDE  17  26  21  FOBS=  135.4  SIGMA=   0.8  PHAS= -118.4  FOM= 0.83  TEST= 0
INDE  17  26  23  FOBS=  223.4  SIGMA=   0.6  PHAS=  -71.6  FOM= 0.95  TEST= 0
INDE  17  26  25  FOBS=   90.2  SIGMA=   1.4  PHAS= -139.2  FOM= 0.97  TEST= 0
INDE  17  26  27  FOBS=  137.4  SIGMA=   0.9  PHAS= -128.9  FOM= 0.93  TEST= 0
INDE  17  26  29  FOBS=   86.2  SIGMA=   1.7  PHAS=  -13.3  FOM= 0.94  TEST= 0
INDE  17  26  31  FOBS=  119.7  SIGMA=   1.3  PHAS=   94.5  FOM= 0.61  TEST= 0
INDE  17  26  33  FOBS=   77.2  SIGMA=   1.9  PHAS=    8.5  FOM= 0.41  TEST= 0
INDE  17  26  35  FOBS=  148.5  SIGMA=   1.1  PHAS=  114.0  FOM= 0.92  TEST= 1
INDE  17  26  37  FOBS=   65.4  SIGMA=   2.5  PHAS=   51.4  FOM= 0.55  TEST= 0
INDE  17  26  39  FOBS=   65.2  SIGMA=   2.8  PHAS=   70.9  FOM= 0.54  TEST= 0
INDE  17  26  41  FOBS=  138.8  SIGMA=   1.3  PHAS=  109.9  FOM= 0.93  TEST= 0
INDE  17  26  43  FOBS=   38.6  SIGMA=   4.6  PHAS=   39.1  FOM= 0.81  TEST= 0
INDE  17  26  45  FOBS=    0.0  SIGMA=  18.3  PHAS=    0.0  FOM= 0.00  TEST= 0
INDE  17  26  47  FOBS=  254.4  SIGMA=   0.7  PHAS=  177.8  FOM= 0.94  TEST= 0
INDE  17  26  49  FOBS=   11.7  SIGMA=  13.4  PHAS= -139.8  FOM= 0.42  TEST= 0
INDE  17  26  51  FOBS=   74.3  SIGMA=   2.0  PHAS=   49.0  FOM= 0.92  TEST= 0
INDE  17  26  53  FOBS=   40.4  SIGMA=   3.9  PHAS=  -30.6  FOM= 0.82  TEST= 0
INDE  17  26  55  FOBS=   95.0  SIGMA=   1.8  PHAS=  106.9  FOM= 0.80  TEST= 0
INDE  17  26  57  FOBS=  125.9  SIGMA=   1.6  PHAS= -177.6  FOM= 0.94  TEST= 0
INDE  17  26  59  FOBS=   95.6  SIGMA=   2.3  PHAS= -150.4  FOM= 0.94  TEST= 0
INDE  17  26  61  FOBS=   88.8  SIGMA=   2.4  PHAS=  -21.8  FOM= 0.83  TEST= 0
INDE  17  26  63  FOBS=    0.0  SIGMA=  21.4  PHAS=    0.0  FOM= 0.00  TEST= 0
INDE  17  26  65  FOBS=   70.1  SIGMA=   7.5  PHAS=   65.5  FOM= 0.81  TEST= 0
INDE  17  26  67  FOBS=   42.6  SIGMA=  12.7  PHAS=   81.6  FOM= 0.36  TEST= 0
INDE  17  27  18  FOBS=  132.5  SIGMA=   0.9  PHAS=  153.7  FOM= 0.91  TEST= 0
INDE  17  27  20  FOBS=   69.6  SIGMA=   1.5  PHAS=  149.6  FOM= 0.79  TEST= 0
INDE  17  27  22  FOBS=  181.3  SIGMA=   0.7  PHAS= -154.9  FOM= 0.89  TEST= 1
INDE  17  27  24  FOBS=  295.4  SIGMA=   0.6  PHAS=   47.5  FOM= 0.96  TEST= 0
```

*FIG. 12A - 396*

```
INDE  17  27  26  FOBS=  171.2  SIGMA=   0.8  PHAS=    40.0  FOM=  0.98  TEST= 0
INDE  17  27  28  FOBS=  153.8  SIGMA=   0.9  PHAS=  -178.1  FOM=  0.97  TEST= 0
INDE  17  27  30  FOBS=  164.8  SIGMA=   1.0  PHAS=   150.4  FOM=  0.98  TEST= 0
INDE  17  27  32  FOBS=   39.9  SIGMA=   3.9  PHAS=   125.7  FOM=  0.78  TEST= 0
INDE  17  27  34  FOBS=  172.8  SIGMA=   1.0  PHAS=   143.7  FOM=  0.95  TEST= 0
INDE  17  27  36  FOBS=  184.5  SIGMA=   0.9  PHAS=    58.3  FOM=  0.33  TEST= 1
INDE  17  27  38  FOBS=  133.1  SIGMA=   1.4  PHAS=   -15.9  FOM=  0.84  TEST= 0
INDE  17  27  40  FOBS=  103.9  SIGMA=   1.7  PHAS=   173.6  FOM=  0.80  TEST= 0
INDE  17  27  42  FOBS=  165.7  SIGMA=   1.1  PHAS=   -51.0  FOM=  0.93  TEST= 0
INDE  17  27  44  FOBS=   85.3  SIGMA=   2.0  PHAS=  -113.8  FOM=  0.77  TEST= 0
INDE  17  27  46  FOBS=   55.8  SIGMA=   3.2  PHAS=   166.5  FOM=  0.10  TEST= 1
INDE  17  27  48  FOBS=  199.3  SIGMA=   0.9  PHAS=    89.4  FOM=  0.97  TEST= 0
INDE  17  27  50  FOBS=  106.0  SIGMA=   1.4  PHAS=    18.8  FOM=  0.86  TEST= 0
INDE  17  27  52  FOBS=  114.2  SIGMA=   1.3  PHAS=   -56.7  FOM=  0.96  TEST= 0
INDE  17  27  54  FOBS=    0.0  SIGMA=  18.0  PHAS=     0.0  FOM=  0.00  TEST= 0
INDE  17  27  56  FOBS=  153.6  SIGMA=   1.3  PHAS=    72.2  FOM=  0.96  TEST= 0
INDE  17  27  58  FOBS=   93.9  SIGMA=   2.1  PHAS=    75.2  FOM=  0.86  TEST= 0
INDE  17  27  60  FOBS=    0.0  SIGMA=  23.9  PHAS=     0.0  FOM=  0.00  TEST= 0
INDE  17  27  62  FOBS=    0.0  SIGMA=  20.5  PHAS=     0.0  FOM=  0.00  TEST= 0
INDE  17  27  64  FOBS=   65.2  SIGMA=   8.0  PHAS=   -42.5  FOM=  0.76  TEST= 0
INDE  17  27  66  FOBS=   11.6  SIGMA=  46.5  PHAS=  -176.6  FOM=  0.05  TEST= 0
INDE  17  27  68  FOBS=   46.8  SIGMA=  11.5  PHAS=    99.1  FOM=  0.01  TEST= 1
INDE  17  28  17  FOBS=   70.7  SIGMA=   1.9  PHAS=   150.8  FOM=  0.76  TEST= 0
INDE  17  28  19  FOBS=  292.7  SIGMA=   0.6  PHAS=    66.5  FOM=  0.94  TEST= 0
INDE  17  28  21  FOBS=  154.1  SIGMA=   0.8  PHAS=   110.5  FOM=  0.99  TEST= 0
INDE  17  28  23  FOBS=  185.3  SIGMA=   0.7  PHAS=   -43.2  FOM=  0.96  TEST= 0
INDE  17  28  25  FOBS=  108.3  SIGMA=   1.3  PHAS=   -97.4  FOM=  0.95  TEST= 0
INDE  17  28  27  FOBS=  177.2  SIGMA=   0.8  PHAS=  -165.9  FOM=  0.92  TEST= 0
INDE  17  28  29  FOBS=  212.2  SIGMA=   0.7  PHAS=     5.4  FOM=  0.98  TEST= 0
INDE  17  28  31  FOBS=  217.5  SIGMA=   0.8  PHAS=    79.1  FOM=  0.97  TEST= 0
INDE  17  28  33  FOBS=  189.0  SIGMA=   0.9  PHAS=    14.6  FOM=  0.82  TEST= 0
INDE  17  28  35  FOBS=  122.1  SIGMA=   1.5  PHAS=    33.8  FOM=  0.91  TEST= 0
INDE  17  28  37  FOBS=  100.3  SIGMA=   1.8  PHAS=    62.1  FOM=  0.61  TEST= 0
INDE  17  28  39  FOBS=  202.6  SIGMA=   0.9  PHAS=   130.7  FOM=  0.92  TEST= 0
INDE  17  28  41  FOBS=  126.8  SIGMA=   1.4  PHAS=   154.4  FOM=  0.70  TEST= 0
INDE  17  28  43  FOBS=   86.5  SIGMA=   2.0  PHAS=  -130.1  FOM=  0.83  TEST= 0
INDE  17  28  45  FOBS=    0.0  SIGMA=  18.1  PHAS=     0.0  FOM=  0.00  TEST= 0
INDE  17  28  47  FOBS=   22.0  SIGMA=   9.6  PHAS=    -9.6  FOM=  0.58  TEST= 0
INDE  17  28  49  FOBS=  136.7  SIGMA=   1.2  PHAS=   -40.9  FOM=  0.93  TEST= 0
INDE  17  28  51  FOBS=  113.5  SIGMA=   1.4  PHAS=  -114.4  FOM=  0.82  TEST= 0
INDE  17  28  53  FOBS=   19.8  SIGMA=   7.3  PHAS=   -90.7  FOM=  0.10  TEST= 0
INDE  17  28  55  FOBS=  100.2  SIGMA=   1.7  PHAS=  -106.9  FOM=  0.90  TEST= 0
INDE  17  28  57  FOBS=   89.6  SIGMA=   2.1  PHAS=  -130.4  FOM=  0.78  TEST= 0
INDE  17  28  59  FOBS=   58.6  SIGMA=   3.2  PHAS=  -124.4  FOM=  0.60  TEST= 0
INDE  17  28  61  FOBS=   36.3  SIGMA=   5.8  PHAS=    75.7  FOM=  0.59  TEST= 0
INDE  17  28  63  FOBS=   37.9  SIGMA=  13.1  PHAS=  -163.6  FOM=  0.59  TEST= 0
INDE  17  28  65  FOBS=   57.3  SIGMA=   9.3  PHAS=   151.3  FOM=  0.61  TEST= 0
INDE  17  28  67  FOBS=   34.0  SIGMA=  15.8  PHAS=    24.5  FOM=  0.43  TEST= 0
INDE  17  28  69  FOBS=   22.7  SIGMA=  24.5  PHAS=   -73.0  FOM=  0.27  TEST= 0
INDE  17  29  18  FOBS=  186.5  SIGMA=   0.8  PHAS=    17.2  FOM=  0.96  TEST= 0
INDE  17  29  20  FOBS=  211.8  SIGMA=   0.7  PHAS=   -16.7  FOM=  0.96  TEST= 0
INDE  17  29  22  FOBS=   93.8  SIGMA=   1.3  PHAS=   108.4  FOM=  0.75  TEST= 1
INDE  17  29  24  FOBS=  173.6  SIGMA=   0.8  PHAS=   -10.3  FOM=  0.92  TEST= 0
INDE  17  29  26  FOBS=  113.2  SIGMA=   1.3  PHAS=    85.4  FOM=  0.94  TEST= 1
INDE  17  29  28  FOBS=  237.8  SIGMA=   0.7  PHAS=   123.9  FOM=  0.96  TEST= 0
INDE  17  29  30  FOBS=   59.5  SIGMA=   2.4  PHAS=    15.7  FOM=  0.61  TEST= 0
INDE  17  29  32  FOBS=   41.4  SIGMA=   4.1  PHAS=  -132.2  FOM=  0.83  TEST= 0
INDE  17  29  34  FOBS=  190.9  SIGMA=   1.0  PHAS=  -135.4  FOM=  0.92  TEST= 0
INDE  17  29  36  FOBS=  238.3  SIGMA=   1.1  PHAS=    49.1  FOM=  0.97  TEST= 0
INDE  17  29  38  FOBS=   69.5  SIGMA=   2.8  PHAS=  -157.3  FOM=  0.56  TEST= 0
INDE  17  29  40  FOBS=  126.3  SIGMA=   1.5  PHAS=    51.6  FOM=  0.86  TEST= 0
INDE  17  29  42  FOBS=    0.0  SIGMA=  18.3  PHAS=     0.0  FOM=  0.00  TEST= 1
INDE  17  29  44  FOBS=  103.4  SIGMA=   1.6  PHAS=    45.4  FOM=  0.90  TEST= 0
INDE  17  29  46  FOBS=   72.7  SIGMA=   2.3  PHAS=   -76.6  FOM=  0.85  TEST= 0
INDE  17  29  48  FOBS=   40.8  SIGMA=   4.7  PHAS=    64.2  FOM=  0.34  TEST= 0
INDE  17  29  50  FOBS=   18.5  SIGMA=   9.0  PHAS=   154.1  FOM=  0.15  TEST= 0
INDE  17  29  52  FOBS=   64.1  SIGMA=   2.4  PHAS=   -71.2  FOM=  0.90  TEST= 0
INDE  17  29  54  FOBS=   20.6  SIGMA=   7.4  PHAS=   149.5  FOM=  0.27  TEST= 0
INDE  17  29  56  FOBS=   73.5  SIGMA=   2.3  PHAS=   114.8  FOM=  0.91  TEST= 0
INDE  17  29  58  FOBS=    0.0  SIGMA=  19.2  PHAS=     0.0  FOM=  0.00  TEST= 0
```

*FIG. 12A - 397*

```
INDE  17  29  60 FOBS=    43.0 SIGMA=   4.6 PHAS=    35.0 FOM= 0.37 TEST= 0
INDE  17  29  62 FOBS=    71.5 SIGMA=   3.7 PHAS=   -33.3 FOM= 0.90 TEST= 0
INDE  17  29  64 FOBS=    56.9 SIGMA=   9.2 PHAS=    61.9 FOM= 0.74 TEST= 0
INDE  17  29  66 FOBS=    61.4 SIGMA=   8.8 PHAS=    21.7 FOM= 0.82 TEST= 0
INDE  17  29  68 FOBS=    19.2 SIGMA=  28.7 PHAS=   -31.2 FOM= 0.13 TEST= 0
INDE  17  29  70 FOBS=     0.0 SIGMA=  33.8 PHAS=     0.0 FOM= 0.00 TEST= 0
INDE  17  30  17 FOBS=    30.0 SIGMA=   3.7 PHAS=     9.0 FOM= 0.30 TEST= 0
INDE  17  30  19 FOBS=    52.7 SIGMA=   2.2 PHAS=   -78.9 FOM= 0.91 TEST= 0
INDE  17  30  21 FOBS=     0.0 SIGMA=  17.1 PHAS=     0.0 FOM= 0.00 TEST= 0
INDE  17  30  23 FOBS=   240.1 SIGMA=   0.9 PHAS=  -170.5 FOM= 0.93 TEST= 0
INDE  17  30  25 FOBS=   153.7 SIGMA=   1.0 PHAS=   107.9 FOM= 0.89 TEST= 0
INDE  17  30  27 FOBS=   261.1 SIGMA=   0.7 PHAS=    25.1 FOM= 0.86 TEST= 0
INDE  17  30  29 FOBS=   206.8 SIGMA=   0.8 PHAS=   -37.1 FOM= 0.91 TEST= 0
INDE  17  30  31 FOBS=   119.1 SIGMA=   1.4 PHAS=    61.9 FOM= 0.93 TEST= 0
INDE  17  30  33 FOBS=   209.7 SIGMA=   1.1 PHAS=    77.4 FOM= 0.90 TEST= 0
INDE  17  30  35 FOBS=    51.9 SIGMA=   3.8 PHAS=   -47.1 FOM= 0.89 TEST= 0
INDE  17  30  37 FOBS=     0.0 SIGMA=  19.6 PHAS=     0.0 FOM= 0.00 TEST= 0
INDE  17  30  39 FOBS=    79.4 SIGMA=   2.4 PHAS=   114.9 FOM= 0.83 TEST= 0
INDE  17  30  41 FOBS=   232.9 SIGMA=   0.9 PHAS=   -14.3 FOM= 0.78 TEST= 1
INDE  17  30  43 FOBS=    57.0 SIGMA=   3.0 PHAS=     5.4 FOM= 0.54 TEST= 0
INDE  17  30  45 FOBS=    82.8 SIGMA=   2.0 PHAS=   -99.5 FOM= 0.39 TEST= 0
INDE  17  30  47 FOBS=   166.7 SIGMA=   1.1 PHAS=  -152.6 FOM= 0.96 TEST= 0
INDE  17  30  49 FOBS=    99.1 SIGMA=   1.7 PHAS=   132.6 FOM= 0.05 TEST= 1
INDE  17  30  51 FOBS=   168.5 SIGMA=   1.0 PHAS=  -133.4 FOM= 0.98 TEST= 0
INDE  17  30  53 FOBS=    41.0 SIGMA=   3.8 PHAS=   127.1 FOM= 0.29 TEST= 0
INDE  17  30  55 FOBS=     0.0 SIGMA=  18.4 PHAS=     0.0 FOM= 0.00 TEST= 0
INDE  17  30  57 FOBS=    34.1 SIGMA=   5.1 PHAS=    -9.2 FOM= 0.49 TEST= 0
INDE  17  30  59 FOBS=    13.0 SIGMA=  14.3 PHAS=    17.0 FOM= 0.12 TEST= 0
INDE  17  30  61 FOBS=    73.4 SIGMA=   3.3 PHAS=   -87.3 FOM= 0.89 TEST= 0
INDE  17  30  63 FOBS=    48.1 SIGMA=   6.3 PHAS=   150.5 FOM= 0.30 TEST= 0
INDE  17  30  65 FOBS=    47.3 SIGMA=  11.1 PHAS=   -69.7 FOM= 0.77 TEST= 0
INDE  17  30  67 FOBS=    53.3 SIGMA=  10.3 PHAS=   -94.6 FOM= 0.89 TEST= 0
INDE  17  30  69 FOBS=     0.0 SIGMA=  33.8 PHAS=     0.0 FOM= 0.00 TEST= 0
INDE  17  31  18 FOBS=   164.2 SIGMA=   0.9 PHAS=   -26.5 FOM= 0.34 TEST= 1
INDE  17  31  20 FOBS=    61.2 SIGMA=   1.9 PHAS=   103.1 FOM= 0.99 TEST= 0
INDE  17  31  22 FOBS=   272.5 SIGMA=   0.6 PHAS=    77.3 FOM= 0.95 TEST= 0
INDE  17  31  24 FOBS=   183.2 SIGMA=   0.8 PHAS=    18.7 FOM= 0.95 TEST= 0
INDE  17  31  26 FOBS=   251.2 SIGMA=   0.7 PHAS=   -69.9 FOM= 0.88 TEST= 0
INDE  17  31  28 FOBS=   170.4 SIGMA=   1.0 PHAS=   119.4 FOM= 0.96 TEST= 0
INDE  17  31  30 FOBS=   132.0 SIGMA=   1.2 PHAS=    64.1 FOM= 0.97 TEST= 0
INDE  17  31  32 FOBS=    92.9 SIGMA=   2.3 PHAS=    15.5 FOM= 0.85 TEST= 0
INDE  17  31  34 FOBS=   110.7 SIGMA=   1.9 PHAS=   151.8 FOM= 0.54 TEST= 1
INDE  17  31  36 FOBS=   152.7 SIGMA=   1.4 PHAS=    58.5 FOM= 0.84 TEST= 0
INDE  17  31  38 FOBS=    56.1 SIGMA=   3.5 PHAS=    35.9 FOM= 0.52 TEST= 0
INDE  17  31  40 FOBS=   194.7 SIGMA=   1.1 PHAS=  -107.3 FOM= 0.74 TEST= 0
INDE  17  31  42 FOBS=   211.9 SIGMA=   1.0 PHAS=  -145.2 FOM= 0.95 TEST= 0
INDE  17  31  44 FOBS=   133.1 SIGMA=   1.3 PHAS=   107.3 FOM= 0.93 TEST= 0
INDE  17  31  46 FOBS=   169.5 SIGMA=   1.1 PHAS=   141.2 FOM= 0.95 TEST= 0
INDE  17  31  48 FOBS=   117.9 SIGMA=   1.4 PHAS=    94.4 FOM= 0.92 TEST= 0
INDE  17  31  50 FOBS=   149.4 SIGMA=   1.2 PHAS=   147.8 FOM= 0.96 TEST= 0
INDE  17  31  52 FOBS=    52.6 SIGMA=   3.0 PHAS=    -9.6 FOM= 0.18 TEST= 0
INDE  17  31  54 FOBS=    58.7 SIGMA=   3.1 PHAS=   155.9 FOM= 0.71 TEST= 0
INDE  17  31  56 FOBS=     0.0 SIGMA=  19.9 PHAS=     0.0 FOM= 0.00 TEST= 0
INDE  17  31  58 FOBS=     0.0 SIGMA=  21.6 PHAS=     0.0 FOM= 0.00 TEST= 0
INDE  17  31  60 FOBS=    52.6 SIGMA=   4.1 PHAS=     4.6 FOM= 0.63 TEST= 0
INDE  17  31  62 FOBS=    92.9 SIGMA=   2.9 PHAS=  -132.9 FOM= 0.92 TEST= 0
INDE  17  31  64 FOBS=     0.0 SIGMA=  22.9 PHAS=     0.0 FOM= 0.00 TEST= 0
INDE  17  31  66 FOBS=     6.0 SIGMA=  87.6 PHAS=   150.2 FOM= 0.05 TEST= 0
INDE  17  31  68 FOBS=    19.9 SIGMA=  27.8 PHAS=   113.1 FOM= 0.30 TEST= 0
INDE  17  32  17 FOBS=   156.5 SIGMA=   0.9 PHAS=   -96.5 FOM= 0.94 TEST= 0
INDE  17  32  19 FOBS=    49.0 SIGMA=   2.5 PHAS=     9.0 FOM= 0.64 TEST= 0
INDE  17  32  21 FOBS=   228.8 SIGMA=   0.7 PHAS=   -19.4 FOM= 0.96 TEST= 0
INDE  17  32  23 FOBS=   156.4 SIGMA=   0.9 PHAS=    87.2 FOM= 0.94 TEST= 0
INDE  17  32  25 FOBS=    49.5 SIGMA=   3.0 PHAS=   166.6 FOM= 0.51 TEST= 0
INDE  17  32  27 FOBS=   374.2 SIGMA=   0.7 PHAS=    54.0 FOM= 0.95 TEST= 0
INDE  17  32  29 FOBS=     0.0 SIGMA=  19.0 PHAS=     0.0 FOM= 0.00 TEST= 0
INDE  17  32  31 FOBS=    69.1 SIGMA=   2.7 PHAS=    -7.9 FOM= 0.75 TEST= 0
INDE  17  32  33 FOBS=   186.6 SIGMA=   1.5 PHAS=     8.8 FOM= 0.87 TEST= 0
INDE  17  32  35 FOBS=   275.8 SIGMA=   0.9 PHAS=   -54.4 FOM= 0.95 TEST= 0
INDE  17  32  37 FOBS=   111.9 SIGMA=   1.8 PHAS=  -166.3 FOM= 0.89 TEST= 0
```

*FIG. 12A - 398*

```
INDE 17 32 39 FOBS=    163.4 SIGMA=  1.3 PHAS=   18.5 FOM= 0.88 TEST= 0
INDE 17 32 41 FOBS=     59.7 SIGMA=  3.2 PHAS=  157.3 FOM= 0.75 TEST= 0
INDE 17 32 43 FOBS=      3.3 SIGMA= 56.1 PHAS=  -97.2 FOM= 0.04 TEST= 0
INDE 17 32 45 FOBS=    146.6 SIGMA=  1.3 PHAS=   63.1 FOM= 0.91 TEST= 0
INDE 17 32 47 FOBS=     70.2 SIGMA=  2.4 PHAS=  101.5 FOM= 0.70 TEST= 1
INDE 17 32 49 FOBS=     65.4 SIGMA=  2.5 PHAS=   36.7 FOM= 0.72 TEST= 0
INDE 17 32 51 FOBS=    103.1 SIGMA=  1.6 PHAS=  129.6 FOM= 0.93 TEST= 0
INDE 17 32 53 FOBS=     34.6 SIGMA=  5.0 PHAS=    3.3 FOM= 0.60 TEST= 0
INDE 17 32 55 FOBS=     16.0 SIGMA= 14.4 PHAS=  -37.0 FOM= 0.01 TEST= 1
INDE 17 32 57 FOBS=     10.5 SIGMA= 19.8 PHAS=  -66.5 FOM= 0.07 TEST= 0
INDE 17 32 59 FOBS=      0.0 SIGMA= 22.8 PHAS=    0.0 FOM= 0.00 TEST= 0
INDE 17 32 61 FOBS=      0.0 SIGMA= 21.6 PHAS=    0.0 FOM= 0.00 TEST= 0
INDE 17 32 63 FOBS=     61.5 SIGMA=  4.3 PHAS=  119.2 FOM= 0.79 TEST= 0
INDE 17 32 65 FOBS=     63.3 SIGMA=  5.0 PHAS=   -3.0 FOM= 0.30 TEST= 0
INDE 17 32 67 FOBS=     52.5 SIGMA= 10.1 PHAS= -125.5 FOM= 0.68 TEST= 0
INDE 17 33 18 FOBS=    155.1 SIGMA=  1.0 PHAS=    9.2 FOM= 0.95 TEST= 0
INDE 17 33 20 FOBS=    131.3 SIGMA=  1.1 PHAS=  126.1 FOM= 0.55 TEST= 0
INDE 17 33 22 FOBS=    205.4 SIGMA=  0.8 PHAS=   51.5 FOM= 0.97 TEST= 0
INDE 17 33 24 FOBS=      0.0 SIGMA= 17.4 PHAS=    0.0 FOM= 0.00 TEST= 0
INDE 17 33 26 FOBS=    224.8 SIGMA=  0.8 PHAS=  -17.3 FOM= 0.88 TEST= 1
INDE 17 33 28 FOBS=    219.7 SIGMA=  0.9 PHAS=    7.9 FOM= 0.97 TEST= 0
INDE 17 33 30 FOBS=    233.5 SIGMA=  1.0 PHAS=   95.6 FOM= 0.91 TEST= 1
INDE 17 33 32 FOBS=    137.2 SIGMA=  1.5 PHAS=   92.0 FOM= 0.68 TEST= 0
INDE 17 33 34 FOBS=    167.5 SIGMA=  1.3 PHAS= -147.5 FOM= 0.92 TEST= 0
INDE 17 33 36 FOBS=    113.7 SIGMA=  1.8 PHAS= -179.6 FOM= 0.51 TEST= 0
INDE 17 33 38 FOBS=     70.5 SIGMA=  2.8 PHAS= -107.9 FOM= 0.56 TEST= 0
INDE 17 33 40 FOBS=      0.0 SIGMA= 20.4 PHAS=    0.0 FOM= 0.00 TEST= 0
INDE 17 33 42 FOBS=     98.4 SIGMA=  1.9 PHAS=  166.8 FOM= 0.96 TEST= 0
INDE 17 33 44 FOBS=     93.8 SIGMA=  2.0 PHAS=  132.2 FOM= 0.88 TEST= 0
INDE 17 33 46 FOBS=     61.9 SIGMA=  3.0 PHAS=  -13.6 FOM= 0.42 TEST= 0
INDE 17 33 48 FOBS=    112.0 SIGMA=  1.5 PHAS=    2.1 FOM= 0.86 TEST= 0
INDE 17 33 50 FOBS=    127.2 SIGMA=  1.3 PHAS=   13.9 FOM= 0.94 TEST= 0
INDE 17 33 52 FOBS=    150.7 SIGMA=  1.2 PHAS=   18.4 FOM= 0.95 TEST= 0
INDE 17 33 54 FOBS=     62.7 SIGMA=  3.0 PHAS= -114.9 FOM= 0.74 TEST= 0
INDE 17 33 56 FOBS=     43.7 SIGMA=  4.8 PHAS= -108.7 FOM= 0.38 TEST= 0
INDE 17 33 58 FOBS=     75.5 SIGMA=  2.9 PHAS=  -30.8 FOM= 0.75 TEST= 0
INDE 17 33 60 FOBS=      0.0 SIGMA= 21.5 PHAS=    0.0 FOM= 0.00 TEST= 0
INDE 17 33 62 FOBS=     61.5 SIGMA=  3.5 PHAS= -134.5 FOM= 0.79 TEST= 0
INDE 17 33 64 FOBS=     76.5 SIGMA=  3.6 PHAS=    9.4 FOM= 0.81 TEST= 0
INDE 17 33 66 FOBS=     48.5 SIGMA=  6.5 PHAS=   44.3 FOM= 0.35 TEST= 0
INDE 17 33 68 FOBS=     62.5 SIGMA=  8.7 PHAS=  127.6 FOM= 0.80 TEST= 0
INDE 17 34 17 FOBS=     90.5 SIGMA=  1.4 PHAS=  -93.6 FOM= 0.86 TEST= 0
INDE 17 34 19 FOBS=     75.6 SIGMA=  1.9 PHAS=   86.4 FOM= 0.43 TEST= 0
INDE 17 34 21 FOBS=    270.4 SIGMA=  0.7 PHAS=    3.1 FOM= 0.95 TEST= 0
INDE 17 34 23 FOBS=    199.4 SIGMA=  0.8 PHAS=   76.0 FOM= 0.95 TEST= 0
INDE 17 34 25 FOBS=    161.3 SIGMA=  1.0 PHAS= -144.7 FOM= 0.93 TEST= 0
INDE 17 34 27 FOBS=    158.1 SIGMA=  1.4 PHAS=  -66.4 FOM= 0.92 TEST= 0
INDE 17 34 29 FOBS=    240.3 SIGMA=  1.0 PHAS=  -65.5 FOM= 0.93 TEST= 0
INDE 17 34 31 FOBS=     78.4 SIGMA=  2.5 PHAS=  125.0 FOM= 0.88 TEST= 0
INDE 17 34 33 FOBS=     56.4 SIGMA=  3.3 PHAS=  -86.8 FOM= 0.55 TEST= 0
INDE 17 34 35 FOBS=     50.9 SIGMA=  3.9 PHAS= -120.8 FOM= 0.83 TEST= 0
INDE 17 34 37 FOBS=    191.6 SIGMA=  1.1 PHAS= -179.2 FOM= 0.93 TEST= 0
INDE 17 34 39 FOBS=    196.4 SIGMA=  1.1 PHAS=   64.0 FOM= 0.97 TEST= 0
INDE 17 34 41 FOBS=     55.8 SIGMA=  3.4 PHAS=   53.1 FOM= 0.77 TEST= 0
INDE 17 34 43 FOBS=      0.0 SIGMA= 19.2 PHAS=    0.0 FOM= 0.00 TEST= 0
INDE 17 34 45 FOBS=     63.3 SIGMA=  2.9 PHAS= -109.6 FOM= 0.36 TEST= 0
INDE 17 34 47 FOBS=     71.8 SIGMA=  2.5 PHAS= -174.1 FOM= 0.77 TEST= 1
INDE 17 34 49 FOBS=     87.9 SIGMA=  2.1 PHAS=  -94.9 FOM= 0.78 TEST= 0
INDE 17 34 51 FOBS=    191.1 SIGMA=  1.0 PHAS=  -80.6 FOM= 0.98 TEST= 0
INDE 17 34 53 FOBS=    114.6 SIGMA=  1.9 PHAS= -109.7 FOM= 0.88 TEST= 0
INDE 17 34 55 FOBS=      0.0 SIGMA= 20.6 PHAS=    0.0 FOM= 0.00 TEST= 0
INDE 17 34 57 FOBS=     80.7 SIGMA=  2.7 PHAS=  176.9 FOM= 0.84 TEST= 0
INDE 17 34 59 FOBS=     66.6 SIGMA=  3.2 PHAS= -150.0 FOM= 0.73 TEST= 0
INDE 17 34 61 FOBS=     60.2 SIGMA=  3.6 PHAS=  175.4 FOM= 0.92 TEST= 0
INDE 17 34 63 FOBS=     30.3 SIGMA=  9.8 PHAS=   89.9 FOM= 0.38 TEST= 0
INDE 17 34 65 FOBS=      0.0 SIGMA= 24.9 PHAS=    0.0 FOM= 0.00 TEST= 0
INDE 17 34 67 FOBS=      0.0 SIGMA= 25.4 PHAS=    0.0 FOM= 0.00 TEST= 0
INDE 17 35 18 FOBS=    184.5 SIGMA=  0.8 PHAS=   63.3 FOM= 0.90 TEST= 0
INDE 17 35 20 FOBS=    155.4 SIGMA=  1.0 PHAS=  -54.5 FOM= 0.96 TEST= 0
INDE 17 35 22 FOBS=     60.6 SIGMA=  2.4 PHAS=   28.5 FOM= 0.83 TEST= 0
```

*FIG. 12A - 399*

```
INDE 17 35 24 FOBS=   44.4 SIGMA=  3.6 PHAS=  106.1 FOM= 0.19 TEST= 0
INDE 17 35 26 FOBS=  397.0 SIGMA=  0.7 PHAS=  143.9 FOM= 0.97 TEST= 0
INDE 17 35 28 FOBS=  163.6 SIGMA=  1.4 PHAS=  137.2 FOM= 0.96 TEST= 0
INDE 17 35 30 FOBS=  214.4 SIGMA=  1.1 PHAS=   79.0 FOM= 0.93 TEST= 1
INDE 17 35 32 FOBS=  244.0 SIGMA=  0.9 PHAS=  135.1 FOM= 0.96 TEST= 0
INDE 17 35 34 FOBS=  201.9 SIGMA=  1.0 PHAS=  136.6 FOM= 0.95 TEST= 0
INDE 17 35 36 FOBS=  160.9 SIGMA=  1.3 PHAS=  113.7 FOM= 0.97 TEST= 0
INDE 17 35 38 FOBS=  180.0 SIGMA=  1.2 PHAS=   56.5 FOM= 0.94 TEST= 0
INDE 17 35 40 FOBS=   77.8 SIGMA=  2.5 PHAS=  -87.7 FOM= 0.85 TEST= 0
INDE 17 35 42 FOBS=   25.4 SIGMA=  7.8 PHAS= -175.5 FOM= 0.71 TEST= 1
INDE 17 35 44 FOBS=   64.0 SIGMA=  2.9 PHAS=   84.2 FOM= 0.79 TEST= 0
INDE 17 35 46 FOBS=  135.9 SIGMA=  1.4 PHAS= -103.4 FOM= 0.81 TEST= 0
INDE 17 35 48 FOBS=  113.0 SIGMA=  1.6 PHAS=    7.4 FOM= 0.93 TEST= 0
INDE 17 35 50 FOBS=   35.1 SIGMA=  5.9 PHAS=  145.7 FOM= 0.45 TEST= 0
INDE 17 35 52 FOBS=   84.4 SIGMA=  2.6 PHAS=  144.6 FOM= 0.88 TEST= 0
INDE 17 35 54 FOBS=   16.8 SIGMA= 12.8 PHAS=  -94.8 FOM= 0.27 TEST= 0
INDE 17 35 56 FOBS=   26.2 SIGMA=  8.8 PHAS=   91.6 FOM= 0.25 TEST= 0
INDE 17 35 58 FOBS=   83.1 SIGMA=  2.6 PHAS=   90.6 FOM= 0.89 TEST= 0
INDE 17 35 60 FOBS=   93.9 SIGMA=  3.0 PHAS=  121.7 FOM= 0.94 TEST= 0
INDE 17 35 62 FOBS=    0.0 SIGMA= 22.9 PHAS=    0.0 FOM= 0.00 TEST= 0
INDE 17 35 64 FOBS=   29.6 SIGMA=  8.1 PHAS=   36.1 FOM= 0.39 TEST= 0
INDE 17 35 66 FOBS=   42.5 SIGMA=  7.5 PHAS=   56.9 FOM= 0.71 TEST= 0
INDE 17 36 17 FOBS=   22.0 SIGMA=  6.6 PHAS=   57.6 FOM= 0.13 TEST= 0
INDE 17 36 19 FOBS=  212.3 SIGMA=  0.8 PHAS=  178.2 FOM= 0.93 TEST= 0
INDE 17 36 21 FOBS=  141.7 SIGMA=  1.1 PHAS=    7.5 FOM= 0.85 TEST= 0
INDE 17 36 23 FOBS=  159.2 SIGMA=  1.2 PHAS=   27.9 FOM= 0.78 TEST= 0
INDE 17 36 25 FOBS=  214.2 SIGMA=  1.0 PHAS=   56.5 FOM= 0.93 TEST= 0
INDE 17 36 27 FOBS=  315.4 SIGMA=  0.8 PHAS=   43.9 FOM= 0.98 TEST= 0
INDE 17 36 29 FOBS=   70.5 SIGMA=  2.8 PHAS= -128.7 FOM= 0.74 TEST= 0
INDE 17 36 31 FOBS=  289.2 SIGMA=  0.9 PHAS=   57.0 FOM= 0.96 TEST= 0
INDE 17 36 33 FOBS=  290.2 SIGMA=  0.8 PHAS=  -27.8 FOM= 0.48 TEST= 1
INDE 17 36 35 FOBS=  137.1 SIGMA=  1.5 PHAS=   -4.1 FOM= 0.85 TEST= 0
INDE 17 36 37 FOBS=  150.0 SIGMA=  1.4 PHAS=    2.5 FOM= 0.86 TEST= 1
INDE 17 36 39 FOBS=   75.0 SIGMA=  2.6 PHAS=   18.8 FOM= 0.77 TEST= 0
INDE 17 36 41 FOBS=   53.0 SIGMA=  3.6 PHAS= -129.8 FOM= 0.33 TEST= 0
INDE 17 36 43 FOBS=  100.4 SIGMA=  1.9 PHAS=   90.2 FOM= 0.92 TEST= 0
INDE 17 36 45 FOBS=   67.8 SIGMA=  2.7 PHAS= -140.4 FOM= 0.83 TEST= 0
INDE 17 36 47 FOBS=  246.1 SIGMA=  1.1 PHAS= -142.3 FOM= 0.98 TEST= 0
INDE 17 36 49 FOBS=  128.9 SIGMA=  1.8 PHAS= -128.4 FOM= 0.94 TEST= 0
INDE 17 36 51 FOBS=  209.4 SIGMA=  1.2 PHAS=  -57.8 FOM= 0.98 TEST= 0
INDE 17 36 53 FOBS=   48.3 SIGMA=  4.5 PHAS= -152.4 FOM= 0.77 TEST= 0
INDE 17 36 55 FOBS=   89.9 SIGMA=  2.4 PHAS=  -39.2 FOM= 0.17 TEST= 1
INDE 17 36 57 FOBS=    0.0 SIGMA= 21.4 PHAS=    0.0 FOM= 0.00 TEST= 0
INDE 17 36 59 FOBS=  125.9 SIGMA=  1.8 PHAS=   43.8 FOM= 0.88 TEST= 0
INDE 17 36 61 FOBS=   48.4 SIGMA=  4.5 PHAS= -170.5 FOM= 0.28 TEST= 0
INDE 17 36 63 FOBS=   56.2 SIGMA=  3.9 PHAS=   33.7 FOM= 0.27 TEST= 0
INDE 17 36 65 FOBS=   33.3 SIGMA=  9.6 PHAS=  -82.5 FOM= 0.84 TEST= 0
INDE 17 37 18 FOBS=  129.9 SIGMA=  1.3 PHAS=   39.0 FOM= 0.90 TEST= 0
INDE 17 37 20 FOBS=  165.9 SIGMA=  1.0 PHAS=   38.9 FOM= 0.95 TEST= 1
INDE 17 37 22 FOBS=  140.9 SIGMA=  1.3 PHAS=  172.6 FOM= 0.96 TEST= 0
INDE 17 37 24 FOBS=   50.0 SIGMA=  3.7 PHAS=  -97.7 FOM= 0.81 TEST= 1
INDE 17 37 26 FOBS=   99.9 SIGMA=  1.8 PHAS= -105.3 FOM= 0.84 TEST= 0
INDE 17 37 28 FOBS=  112.5 SIGMA=  1.7 PHAS=   86.3 FOM= 0.72 TEST= 0
INDE 17 37 30 FOBS=  134.4 SIGMA=  1.5 PHAS=   99.3 FOM= 0.92 TEST= 0
INDE 17 37 32 FOBS=  135.2 SIGMA=  1.6 PHAS=  -97.1 FOM= 0.93 TEST= 0
INDE 17 37 34 FOBS=    9.5 SIGMA= 19.4 PHAS= -176.7 FOM= 0.04 TEST= 0
INDE 17 37 36 FOBS=  129.7 SIGMA=  1.6 PHAS= -142.2 FOM= 0.89 TEST= 0
INDE 17 37 38 FOBS=   63.9 SIGMA=  3.1 PHAS=  -12.2 FOM= 0.90 TEST= 0
INDE 17 37 40 FOBS=   54.5 SIGMA=  3.5 PHAS= -148.1 FOM= 0.64 TEST= 0
INDE 17 37 42 FOBS=   86.1 SIGMA=  2.2 PHAS=   54.5 FOM= 0.93 TEST= 0
INDE 17 37 44 FOBS=  101.4 SIGMA=  1.9 PHAS=  -19.3 FOM= 0.94 TEST= 0
INDE 17 37 46 FOBS=  171.1 SIGMA=  1.3 PHAS=  129.9 FOM= 0.95 TEST= 0
INDE 17 37 48 FOBS=   87.2 SIGMA=  2.5 PHAS=  140.8 FOM= 0.91 TEST= 0
INDE 17 37 50 FOBS=  115.0 SIGMA=  2.0 PHAS=  145.7 FOM= 0.94 TEST= 0
INDE 17 37 52 FOBS=  164.5 SIGMA=  1.4 PHAS= -132.7 FOM= 0.96 TEST= 0
INDE 17 37 54 FOBS=  111.6 SIGMA=  2.0 PHAS=   87.6 FOM= 0.93 TEST= 0
INDE 17 37 56 FOBS=   96.3 SIGMA=  2.3 PHAS= -106.4 FOM= 0.74 TEST= 0
INDE 17 37 58 FOBS=  103.9 SIGMA=  2.1 PHAS=  121.5 FOM= 0.91 TEST= 0
INDE 17 37 60 FOBS=   48.2 SIGMA=  6.1 PHAS=  121.1 FOM= 0.48 TEST= 0
INDE 17 37 62 FOBS=  116.9 SIGMA=  1.9 PHAS=  151.4 FOM= 0.94 TEST= 0
```

*FIG. 12A - 400*

```
INDE  17  37  64  FOBS=   51.3  SIGMA=   5.3  PHAS=    54.0  FOM=  0.72  TEST= 0
INDE  17  37  66  FOBS=   43.7  SIGMA=   7.4  PHAS=    77.5  FOM=  0.46  TEST= 0
INDE  17  38  17  FOBS=  252.1  SIGMA=   0.7  PHAS=  -158.3  FOM=  0.97  TEST= 0
INDE  17  38  19  FOBS=   47.7  SIGMA=   3.8  PHAS=    89.4  FOM=  0.69  TEST= 0
INDE  17  38  21  FOBS=  301.8  SIGMA=   0.9  PHAS=    26.5  FOM=  0.94  TEST= 0
INDE  17  38  23  FOBS=    0.0  SIGMA=  19.1  PHAS=     0.0  FOM=  0.00  TEST= 0
INDE  17  38  25  FOBS=  260.1  SIGMA=   0.9  PHAS=    85.7  FOM=  0.95  TEST= 0
INDE  17  38  27  FOBS=  216.9  SIGMA=   0.9  PHAS=    61.2  FOM=  0.91  TEST= 0
INDE  17  38  29  FOBS=  142.1  SIGMA=   1.3  PHAS=    30.3  FOM=  0.98  TEST= 0
INDE  17  38  31  FOBS=   92.7  SIGMA=   2.1  PHAS=    93.1  FOM=  0.83  TEST= 0
INDE  17  38  33  FOBS=   37.1  SIGMA=   6.0  PHAS=    30.0  FOM=  0.85  TEST= 0
INDE  17  38  35  FOBS=  126.3  SIGMA=   1.5  PHAS=   100.1  FOM=  0.88  TEST= 0
INDE  17  38  37  FOBS=  134.6  SIGMA=   1.5  PHAS=    51.9  FOM=  0.14  TEST= 0
INDE  17  38  39  FOBS=   11.8  SIGMA=  19.0  PHAS=  -150.0  FOM=  0.50  TEST= 0
INDE  17  38  41  FOBS=   69.7  SIGMA=   2.7  PHAS=   -89.8  FOM=  0.73  TEST= 0
INDE  17  38  43  FOBS=   60.6  SIGMA=   3.4  PHAS=   -66.7  FOM=  0.58  TEST= 0
INDE  17  38  45  FOBS=   84.0  SIGMA=   2.7  PHAS=   -85.8  FOM=  0.85  TEST= 0
INDE  17  38  47  FOBS=   95.4  SIGMA=   2.4  PHAS=   128.6  FOM=  0.89  TEST= 0
INDE  17  38  49  FOBS=    0.0  SIGMA=  20.8  PHAS=     0.0  FOM=  0.00  TEST= 0
INDE  17  38  51  FOBS=   42.6  SIGMA=   5.7  PHAS=    44.6  FOM=  0.30  TEST= 0
INDE  17  38  53  FOBS=  151.4  SIGMA=   1.6  PHAS=  -140.2  FOM=  0.92  TEST= 0
INDE  17  38  55  FOBS=   52.6  SIGMA=   4.1  PHAS=   -73.1  FOM=  0.23  TEST= 1
INDE  17  38  57  FOBS=   55.6  SIGMA=   3.9  PHAS=   -12.4  FOM=  0.49  TEST= 0
INDE  17  38  59  FOBS=   99.3  SIGMA=   2.3  PHAS=    92.6  FOM=  0.94  TEST= 0
INDE  17  38  61  FOBS=   59.5  SIGMA=   3.7  PHAS=    52.5  FOM=  0.83  TEST= 0
INDE  17  38  63  FOBS=   53.5  SIGMA=   5.1  PHAS=    44.7  FOM=  0.30  TEST= 0
INDE  17  38  65  FOBS=   93.7  SIGMA=   3.6  PHAS=  -138.8  FOM=  0.93  TEST= 0
INDE  17  39  18  FOBS=  181.4  SIGMA=   1.1  PHAS=    99.4  FOM=  0.88  TEST= 0
INDE  17  39  20  FOBS=  267.5  SIGMA=   0.9  PHAS=    19.9  FOM=  0.99  TEST= 0
INDE  17  39  22  FOBS=   44.0  SIGMA=   4.7  PHAS=    77.2  FOM=  0.68  TEST= 0
INDE  17  39  24  FOBS=  204.0  SIGMA=   1.1  PHAS=     7.0  FOM=  0.95  TEST= 0
INDE  17  39  26  FOBS=  195.6  SIGMA=   1.1  PHAS=   -87.9  FOM=  0.93  TEST= 0
INDE  17  39  28  FOBS=  117.0  SIGMA=   1.6  PHAS=   -35.9  FOM=  0.89  TEST= 0
INDE  17  39  30  FOBS=   68.4  SIGMA=   2.7  PHAS=   -78.0  FOM=  0.76  TEST= 0
INDE  17  39  32  FOBS=   21.7  SIGMA=   8.7  PHAS=   -43.3  FOM=  0.16  TEST= 0
INDE  17  39  34  FOBS=   85.4  SIGMA=   2.2  PHAS=    -6.7  FOM=  0.62  TEST= 0
INDE  17  39  36  FOBS=  147.9  SIGMA=   1.3  PHAS=   136.0  FOM=  0.87  TEST= 0
INDE  17  39  38  FOBS=  121.6  SIGMA=   1.7  PHAS=    99.8  FOM=  0.71  TEST= 1
INDE  17  39  40  FOBS=   38.8  SIGMA=   5.7  PHAS=    90.2  FOM=  0.18  TEST= 0
INDE  17  39  42  FOBS=   67.9  SIGMA=   3.4  PHAS=   141.3  FOM=  0.75  TEST= 0
INDE  17  39  44  FOBS=    0.0  SIGMA=  22.2  PHAS=     0.0  FOM=  0.00  TEST= 0
INDE  17  39  46  FOBS=   50.7  SIGMA=   4.4  PHAS=   161.9  FOM=  0.68  TEST= 0
INDE  17  39  48  FOBS=   41.8  SIGMA=   5.7  PHAS=  -131.8  FOM=  0.55  TEST= 0
INDE  17  39  50  FOBS=   17.5  SIGMA=  13.6  PHAS=    92.6  FOM=  0.36  TEST= 0
INDE  17  39  52  FOBS=    0.0  SIGMA=  22.8  PHAS=     0.0  FOM=  0.00  TEST= 0
INDE  17  39  54  FOBS=   41.5  SIGMA=   5.3  PHAS=   -38.3  FOM=  0.32  TEST= 1
INDE  17  39  56  FOBS=   45.7  SIGMA=   4.8  PHAS=    97.4  FOM=  0.70  TEST= 0
INDE  17  39  58  FOBS=    0.0  SIGMA=  20.7  PHAS=     0.0  FOM=  0.00  TEST= 0
INDE  17  39  60  FOBS=   35.1  SIGMA=   6.2  PHAS=     8.0  FOM=  0.74  TEST= 0
INDE  17  39  62  FOBS=    0.0  SIGMA=  22.0  PHAS=     0.0  FOM=  0.00  TEST= 0
INDE  17  39  64  FOBS=  142.9  SIGMA=   2.1  PHAS=   101.0  FOM=  0.97  TEST= 0
INDE  17  40  17  FOBS=   76.1  SIGMA=   2.4  PHAS=   -37.6  FOM=  0.75  TEST= 0
INDE  17  40  19  FOBS=   59.6  SIGMA=   3.3  PHAS=     3.8  FOM=  0.76  TEST= 0
INDE  17  40  21  FOBS=  158.8  SIGMA=   1.3  PHAS=   -37.0  FOM=  0.94  TEST= 0
INDE  17  40  23  FOBS=  131.4  SIGMA=   1.5  PHAS=  -108.4  FOM=  0.33  TEST= 0
INDE  17  40  25  FOBS=  121.2  SIGMA=   1.6  PHAS=   103.6  FOM=  0.83  TEST= 0
INDE  17  40  27  FOBS=   89.8  SIGMA=   2.2  PHAS=   -98.1  FOM=  0.75  TEST= 0
INDE  17  40  29  FOBS=  179.8  SIGMA=   1.2  PHAS=   153.4  FOM=  0.93  TEST= 0
INDE  17  40  31  FOBS=   36.6  SIGMA=   4.9  PHAS=    72.2  FOM=  0.51  TEST= 0
INDE  17  40  33  FOBS=  107.2  SIGMA=   1.7  PHAS=    56.2  FOM=  0.82  TEST= 0
INDE  17  40  35  FOBS=   78.1  SIGMA=   2.3  PHAS=  -173.8  FOM=  0.91  TEST= 0
INDE  17  40  37  FOBS=  145.8  SIGMA=   1.4  PHAS=    52.1  FOM=  0.89  TEST= 0
INDE  17  40  39  FOBS=  121.6  SIGMA=   2.0  PHAS=  -175.7  FOM=  0.89  TEST= 0
INDE  17  40  41  FOBS=   73.1  SIGMA=   3.2  PHAS=  -123.5  FOM=  0.79  TEST= 0
INDE  17  40  43  FOBS=    0.0  SIGMA=  21.3  PHAS=     0.0  FOM=  0.00  TEST= 0
INDE  17  40  45  FOBS=   69.2  SIGMA=   3.3  PHAS=   -92.2  FOM=  0.76  TEST= 0
INDE  17  40  47  FOBS=  121.8  SIGMA=   1.9  PHAS=   146.2  FOM=  0.91  TEST= 0
INDE  17  40  49  FOBS=   56.5  SIGMA=   3.9  PHAS=   -64.8  FOM=  0.90  TEST= 0
INDE  17  40  51  FOBS=   27.0  SIGMA=   8.8  PHAS=   -13.9  FOM=  0.44  TEST= 0
INDE  17  40  53  FOBS=    0.0  SIGMA=  20.8  PHAS=     0.0  FOM=  0.00  TEST= 0
```

*FIG. 12A - 401*

```
INDE  17  40  55  FOBS=   81.9  SIGMA=   2.7  PHAS=  -81.0  FOM=  0.79  TEST=  0
INDE  17  40  57  FOBS=   44.1  SIGMA=   4.9  PHAS=  125.9  FOM=  0.40  TEST=  0
INDE  17  40  59  FOBS=   50.8  SIGMA=   4.3  PHAS=  117.4  FOM=  0.47  TEST=  0
INDE  17  40  61  FOBS=    0.0  SIGMA=  21.8  PHAS=    0.0  FOM=  0.00  TEST=  0
INDE  17  40  63  FOBS=   61.1  SIGMA=   4.6  PHAS=  -10.3  FOM=  0.92  TEST=  0
INDE  17  41  18  FOBS=  148.4  SIGMA=   1.4  PHAS= -131.5  FOM=  0.96  TEST=  0
INDE  17  41  20  FOBS=  144.4  SIGMA=   1.4  PHAS=  -22.4  FOM=  0.97  TEST=  0
INDE  17  41  22  FOBS=  180.9  SIGMA=   1.2  PHAS=   -9.9  FOM=  0.88  TEST=  0
INDE  17  41  24  FOBS=  270.7  SIGMA=   0.9  PHAS=  -17.6  FOM=  0.98  TEST=  0
INDE  17  41  26  FOBS=  156.6  SIGMA=   1.3  PHAS= -155.7  FOM=  0.95  TEST=  0
INDE  17  41  28  FOBS=   37.1  SIGMA=   5.1  PHAS=  -71.7  FOM=  0.79  TEST=  0
INDE  17  41  30  FOBS=    0.0  SIGMA=  20.3  PHAS=    0.0  FOM=  0.00  TEST=  0
INDE  17  41  32  FOBS=   67.2  SIGMA=   2.7  PHAS=   13.7  FOM=  0.74  TEST=  0
INDE  17  41  34  FOBS=   97.2  SIGMA=   2.0  PHAS=  -22.7  FOM=  0.94  TEST=  0
INDE  17  41  36  FOBS=   78.9  SIGMA=   2.6  PHAS=  110.7  FOM=  0.71  TEST=  0
INDE  17  41  38  FOBS=  140.2  SIGMA=   1.5  PHAS=   79.8  FOM=  0.94  TEST=  0
INDE  17  41  40  FOBS=  134.5  SIGMA=   1.8  PHAS=  135.1  FOM=  0.87  TEST=  0
INDE  17  41  42  FOBS=  116.0  SIGMA=   2.1  PHAS=  162.4  FOM=  0.94  TEST=  0
INDE  17  41  44  FOBS=   36.6  SIGMA=   6.7  PHAS=   29.6  FOM=  0.06  TEST=  0
INDE  17  41  46  FOBS=    0.0  SIGMA=  21.1  PHAS=    0.0  FOM=  0.00  TEST=  0
INDE  17  41  48  FOBS=  137.0  SIGMA=   1.7  PHAS= -160.1  FOM=  0.95  TEST=  0
INDE  17  41  50  FOBS=   21.2  SIGMA=  11.3  PHAS=  175.1  FOM=  0.46  TEST=  1
INDE  17  41  52  FOBS=   97.9  SIGMA=   2.3  PHAS= -104.1  FOM=  0.86  TEST=  0
INDE  17  41  54  FOBS=   27.5  SIGMA=   7.9  PHAS= -125.5  FOM=  0.36  TEST=  0
INDE  17  41  56  FOBS=    0.0  SIGMA=  20.8  PHAS=    0.0  FOM=  0.00  TEST=  0
INDE  17  41  58  FOBS=   14.8  SIGMA=  17.9  PHAS=  135.3  FOM=  0.32  TEST=  0
INDE  17  41  60  FOBS=    0.0  SIGMA=  20.9  PHAS=    0.0  FOM=  0.00  TEST=  1
INDE  17  41  62  FOBS=   17.7  SIGMA=  15.5  PHAS=   96.4  FOM=  0.07  TEST=  0
INDE  17  42  17  FOBS=   81.6  SIGMA=   2.4  PHAS=  -24.1  FOM=  0.83  TEST=  0
INDE  17  42  19  FOBS=  153.0  SIGMA=   1.4  PHAS= -146.3  FOM=  0.92  TEST=  0
INDE  17  42  21  FOBS=  180.5  SIGMA=   1.2  PHAS= -133.5  FOM=  0.89  TEST=  0
INDE  17  42  23  FOBS=  208.2  SIGMA=   1.0  PHAS= -117.5  FOM=  0.96  TEST=  0
INDE  17  42  25  FOBS=   86.5  SIGMA=   2.2  PHAS= -147.6  FOM=  0.75  TEST=  0
INDE  17  42  27  FOBS=  100.4  SIGMA=   1.9  PHAS=  102.9  FOM=  0.84  TEST=  0
INDE  17  42  29  FOBS=  122.1  SIGMA=   1.6  PHAS=  127.8  FOM=  0.95  TEST=  0
INDE  17  42  31  FOBS=  185.0  SIGMA=   1.2  PHAS=   63.1  FOM=  0.88  TEST=  0
INDE  17  42  33  FOBS=  197.5  SIGMA=   1.1  PHAS=   16.8  FOM=  0.97  TEST=  0
INDE  17  42  35  FOBS=   92.8  SIGMA=   2.2  PHAS=  -72.1  FOM=  0.89  TEST=  0
INDE  17  42  37  FOBS=   86.1  SIGMA=   2.4  PHAS=  -13.5  FOM=  0.87  TEST=  0
INDE  17  42  39  FOBS=   64.5  SIGMA=   3.1  PHAS=  -57.5  FOM=  0.56  TEST=  0
INDE  17  42  41  FOBS=  170.6  SIGMA=   1.5  PHAS=   98.7  FOM=  0.96  TEST=  0
INDE  17  42  43  FOBS=   54.8  SIGMA=   4.2  PHAS=   67.1  FOM=  0.69  TEST=  0
INDE  17  42  45  FOBS=   46.5  SIGMA=   4.9  PHAS= -172.1  FOM=  0.72  TEST=  0
INDE  17  42  47  FOBS=   73.6  SIGMA=   3.0  PHAS=  116.0  FOM=  0.41  TEST=  0
INDE  17  42  49  FOBS=   72.6  SIGMA=   3.1  PHAS=  104.6  FOM=  0.85  TEST=  0
INDE  17  42  51  FOBS=   99.4  SIGMA=   2.3  PHAS=  150.1  FOM=  0.86  TEST=  0
INDE  17  42  53  FOBS=    6.3  SIGMA=  34.5  PHAS=  112.8  FOM=  0.10  TEST=  0
INDE  17  42  55  FOBS=    0.0  SIGMA=  22.8  PHAS=    0.0  FOM=  0.00  TEST=  0
INDE  17  42  57  FOBS=   26.2  SIGMA=   8.3  PHAS=  -65.7  FOM=  0.47  TEST=  0
INDE  17  42  59  FOBS=   15.8  SIGMA=  15.0  PHAS=   23.8  FOM=  0.19  TEST=  0
INDE  17  42  61  FOBS=   94.7  SIGMA=   3.0  PHAS=  -28.7  FOM=  0.89  TEST=  0
INDE  17  42  63  FOBS=   54.0  SIGMA=   5.4  PHAS=  -60.5  FOM=  0.76  TEST=  0
INDE  17  43  18  FOBS=  248.6  SIGMA=   0.9  PHAS= -159.0  FOM=  0.95  TEST=  0
INDE  17  43  20  FOBS=  212.4  SIGMA=   1.1  PHAS=   96.1  FOM=  0.88  TEST=  0
INDE  17  43  22  FOBS=   52.1  SIGMA=   4.2  PHAS=   -5.5  FOM=  0.19  TEST=  0
INDE  17  43  24  FOBS=  161.5  SIGMA=   1.3  PHAS=  -47.3  FOM=  0.93  TEST=  0
INDE  17  43  26  FOBS=   92.2  SIGMA=   2.4  PHAS=  139.9  FOM=  0.86  TEST=  0
INDE  17  43  28  FOBS=  110.3  SIGMA=   2.1  PHAS=    7.7  FOM=  0.86  TEST=  0
INDE  17  43  30  FOBS=  200.6  SIGMA=   1.1  PHAS=  -57.1  FOM=  0.94  TEST=  0
INDE  17  43  32  FOBS=  269.8  SIGMA=   1.0  PHAS=  -36.4  FOM=  0.96  TEST=  0
INDE  17  43  34  FOBS=  103.5  SIGMA=   2.0  PHAS=  -89.2  FOM=  0.91  TEST=  0
INDE  17  43  36  FOBS=  147.4  SIGMA=   1.3  PHAS=  166.3  FOM=  0.92  TEST=  0
INDE  17  43  38  FOBS=   56.3  SIGMA=   3.8  PHAS=  175.4  FOM=  0.14  TEST=  1
INDE  17  43  40  FOBS=   62.8  SIGMA=   3.2  PHAS=   -9.2  FOM=  0.81  TEST=  0
INDE  17  43  42  FOBS=   77.3  SIGMA=   3.0  PHAS=   11.9  FOM=  0.83  TEST=  0
INDE  17  43  44  FOBS=   15.6  SIGMA=  16.5  PHAS=  121.6  FOM=  0.20  TEST=  0
INDE  17  43  46  FOBS=   47.0  SIGMA=   4.8  PHAS=   90.5  FOM=  0.05  TEST=  1
INDE  17  43  48  FOBS=    0.0  SIGMA=  22.4  PHAS=    0.0  FOM=  0.00  TEST=  0
INDE  17  43  50  FOBS=    0.0  SIGMA=  21.0  PHAS=    0.0  FOM=  0.00  TEST=  0
INDE  17  43  52  FOBS=   57.9  SIGMA=   3.8  PHAS=  -59.5  FOM=  0.63  TEST=  0
```

*FIG. 12A - 402*

```
INDE  17  43  54  FOBS=    25.6  SIGMA=  10.9  PHAS=  -106.2  FOM=  0.46  TEST=  0
INDE  17  43  56  FOBS=     0.0  SIGMA=  23.6  PHAS=     0.0  FOM=  0.00  TEST=  0
INDE  17  43  58  FOBS=    13.1  SIGMA=  20.7  PHAS=   168.0  FOM=  0.30  TEST=  0
INDE  17  43  60  FOBS=    63.7  SIGMA=   4.4  PHAS=  -129.7  FOM=  0.83  TEST=  0
INDE  17  43  62  FOBS=    95.1  SIGMA=   3.1  PHAS=  -145.2  FOM=  0.43  TEST=  0
INDE  17  44  17  FOBS=    29.4  SIGMA=   8.0  PHAS=    22.9  FOM=  0.12  TEST=  0
INDE  17  44  19  FOBS=    16.6  SIGMA=  13.0  PHAS=   -24.3  FOM=  0.03  TEST=  1
INDE  17  44  21  FOBS=    85.2  SIGMA=   2.6  PHAS=    53.6  FOM=  0.45  TEST=  0
INDE  17  44  23  FOBS=   141.9  SIGMA=   1.6  PHAS=  -162.9  FOM=  0.80  TEST=  0
INDE  17  44  25  FOBS=     0.0  SIGMA=  21.8  PHAS=     0.0  FOM=  0.00  TEST=  0
INDE  17  44  27  FOBS=   115.7  SIGMA=   2.0  PHAS=    81.0  FOM=  0.89  TEST=  0
INDE  17  44  29  FOBS=   200.5  SIGMA=   1.2  PHAS=  -124.0  FOM=  0.96  TEST=  0
INDE  17  44  31  FOBS=   167.7  SIGMA=   1.3  PHAS=   -86.1  FOM=  0.93  TEST=  0
INDE  17  44  33  FOBS=    55.8  SIGMA=   3.9  PHAS=  -147.0  FOM=  0.86  TEST=  0
INDE  17  44  35  FOBS=   111.9  SIGMA=   1.9  PHAS=   -28.7  FOM=  0.55  TEST=  0
INDE  17  44  37  FOBS=   102.3  SIGMA=   1.7  PHAS=    89.0  FOM=  0.81  TEST=  0
INDE  17  44  39  FOBS=    38.3  SIGMA=   5.2  PHAS=    84.9  FOM=  0.74  TEST=  0
INDE  17  44  41  FOBS=    49.4  SIGMA=   4.2  PHAS=   -91.7  FOM=  0.51  TEST=  0
INDE  17  44  43  FOBS=     0.0  SIGMA=  21.3  PHAS=     0.0  FOM=  0.00  TEST=  0
INDE  17  44  45  FOBS=     0.0  SIGMA=  21.3  PHAS=     0.0  FOM=  0.00  TEST=  0
INDE  17  44  47  FOBS=    78.2  SIGMA=   2.9  PHAS=    26.0  FOM=  0.70  TEST=  0
INDE  17  44  49  FOBS=     0.0  SIGMA=  20.9  PHAS=     0.0  FOM=  0.00  TEST=  0
INDE  17  44  51  FOBS=    16.3  SIGMA=  14.8  PHAS=  -132.8  FOM=  0.18  TEST=  0
INDE  17  44  53  FOBS=    23.2  SIGMA=  10.6  PHAS=   -51.4  FOM=  0.06  TEST=  0
INDE  17  44  55  FOBS=    50.0  SIGMA=   4.4  PHAS=    15.6  FOM=  0.56  TEST=  0
INDE  17  44  57  FOBS=    59.6  SIGMA=   3.7  PHAS=   -56.0  FOM=  0.81  TEST=  0
INDE  17  44  59  FOBS=     0.0  SIGMA=  23.4  PHAS=     0.0  FOM=  0.00  TEST=  0
INDE  17  44  61  FOBS=    39.6  SIGMA=   7.1  PHAS=    10.7  FOM=  0.02  TEST=  1
INDE  17  45  18  FOBS=   208.5  SIGMA=   1.2  PHAS=  -142.4  FOM=  0.94  TEST=  0
INDE  17  45  20  FOBS=    83.0  SIGMA=   2.8  PHAS=   124.8  FOM=  0.76  TEST=  0
INDE  17  45  22  FOBS=   148.7  SIGMA=   1.5  PHAS=    35.9  FOM=  0.88  TEST=  0
INDE  17  45  24  FOBS=   172.0  SIGMA=   1.4  PHAS=   -35.6  FOM=  0.90  TEST=  0
INDE  17  45  26  FOBS=    87.5  SIGMA=   2.5  PHAS=    59.6  FOM=  0.62  TEST=  0
INDE  17  45  28  FOBS=    75.7  SIGMA=   2.9  PHAS=  -124.7  FOM=  0.49  TEST=  0
INDE  17  45  30  FOBS=   161.8  SIGMA=   1.8  PHAS=  -103.0  FOM=  0.95  TEST=  1
INDE  17  45  32  FOBS=   102.8  SIGMA=   2.0  PHAS=    70.3  FOM=  0.69  TEST=  1
INDE  17  45  34  FOBS=    86.9  SIGMA=   2.4  PHAS=  -133.7  FOM=  0.88  TEST=  0
INDE  17  45  36  FOBS=    64.7  SIGMA=   3.1  PHAS=   157.3  FOM=  0.83  TEST=  0
INDE  17  45  38  FOBS=    57.6  SIGMA=   3.0  PHAS=   -58.3  FOM=  0.80  TEST=  0
INDE  17  45  40  FOBS=     0.0  SIGMA=  22.9  PHAS=     0.0  FOM=  0.00  TEST=  0
INDE  17  45  42  FOBS=    58.4  SIGMA=   3.6  PHAS=  -133.5  FOM=  0.35  TEST=  0
INDE  17  45  44  FOBS=    29.6  SIGMA=   8.4  PHAS=  -119.9  FOM=  0.57  TEST=  0
INDE  17  45  46  FOBS=   144.5  SIGMA=   1.7  PHAS=   -69.9  FOM=  0.94  TEST=  0
INDE  17  45  48  FOBS=     0.0  SIGMA=  21.0  PHAS=     0.0  FOM=  0.00  TEST=  0
INDE  17  45  50  FOBS=    61.6  SIGMA=   3.6  PHAS=   -52.0  FOM=  0.51  TEST=  0
INDE  17  45  52  FOBS=    41.9  SIGMA=   5.3  PHAS=  -130.5  FOM=  0.38  TEST=  0
INDE  17  45  54  FOBS=     0.0  SIGMA=  21.0  PHAS=     0.0  FOM=  0.00  TEST=  0
INDE  17  45  56  FOBS=    85.0  SIGMA=   2.6  PHAS=  -144.3  FOM=  0.93  TEST=  0
INDE  17  45  58  FOBS=    49.5  SIGMA=   4.6  PHAS=    26.3  FOM=  0.73  TEST=  0
INDE  17  45  60  FOBS=    78.8  SIGMA=   3.6  PHAS=   -60.0  FOM=  0.90  TEST=  0
INDE  17  46  17  FOBS=   160.5  SIGMA=   1.4  PHAS=  -121.9  FOM=  0.93  TEST=  0
INDE  17  46  19  FOBS=   174.7  SIGMA=   1.3  PHAS=   113.7  FOM=  0.85  TEST=  0
INDE  17  46  21  FOBS=   205.3  SIGMA=   1.2  PHAS=    80.9  FOM=  0.95  TEST=  0
INDE  17  46  23  FOBS=   194.2  SIGMA=   1.2  PHAS=   -90.5  FOM=  0.96  TEST=  0
INDE  17  46  25  FOBS=    58.7  SIGMA=   3.7  PHAS=   -52.0  FOM=  0.53  TEST=  0
INDE  17  46  27  FOBS=    51.0  SIGMA=   4.2  PHAS=    16.3  FOM=  0.32  TEST=  0
INDE  17  46  29  FOBS=   205.1  SIGMA=   1.2  PHAS=  -163.2  FOM=  0.78  TEST=  0
INDE  17  46  31  FOBS=   111.0  SIGMA=   2.0  PHAS=    12.7  FOM=  0.41  TEST=  1
INDE  17  46  33  FOBS=    76.0  SIGMA=   2.7  PHAS=    82.0  FOM=  0.50  TEST=  0
INDE  17  46  35  FOBS=   145.2  SIGMA=   1.5  PHAS=    55.8  FOM=  0.88  TEST=  0
INDE  17  46  37  FOBS=   107.8  SIGMA=   1.8  PHAS=    77.7  FOM=  0.89  TEST=  0
INDE  17  46  39  FOBS=    83.2  SIGMA=   2.1  PHAS=   164.8  FOM=  0.69  TEST=  1
INDE  17  46  41  FOBS=    54.7  SIGMA=   3.6  PHAS=    92.0  FOM=  0.42  TEST=  1
INDE  17  46  43  FOBS=    13.7  SIGMA=  16.8  PHAS=    48.9  FOM=  0.08  TEST=  0
INDE  17  46  45  FOBS=    93.5  SIGMA=   2.5  PHAS=  -175.3  FOM=  0.94  TEST=  0
INDE  17  46  47  FOBS=    40.9  SIGMA=   5.5  PHAS=    74.5  FOM=  0.68  TEST=  0
INDE  17  46  49  FOBS=    33.7  SIGMA=   7.0  PHAS=   161.4  FOM=  0.60  TEST=  0
INDE  17  46  51  FOBS=    57.3  SIGMA=   3.9  PHAS=  -140.8  FOM=  0.64  TEST=  0
INDE  17  46  53  FOBS=    46.6  SIGMA=   4.8  PHAS=   165.7  FOM=  0.52  TEST=  0
INDE  17  46  55  FOBS=     0.0  SIGMA=  23.1  PHAS=     0.0  FOM=  0.00  TEST=  0
```

*FIG. 12A - 403*

```
INDE  17  46  57 FOBS=   37.8 SIGMA=  5.9 PHAS=  -59.0 FOM= 0.62 TEST= 0
INDE  17  46  59 FOBS=   73.8 SIGMA=  3.9 PHAS= -112.1 FOM= 0.88 TEST= 0
INDE  17  47  18 FOBS=   51.3 SIGMA=  4.1 PHAS=   -7.3 FOM= 0.14 TEST= 1
INDE  17  47  20 FOBS=  128.3 SIGMA=  1.9 PHAS=   31.5 FOM= 0.92 TEST= 0
INDE  17  47  22 FOBS=   57.9 SIGMA=  3.7 PHAS=  -93.8 FOM= 0.85 TEST= 0
INDE  17  47  24 FOBS=    0.0 SIGMA= 21.6 PHAS=    0.0 FOM= 0.00 TEST= 0
INDE  17  47  26 FOBS=    0.0 SIGMA= 20.6 PHAS=    0.0 FOM= 0.00 TEST= 0
INDE  17  47  28 FOBS=  211.3 SIGMA=  1.2 PHAS=  -86.4 FOM= 0.95 TEST= 0
INDE  17  47  30 FOBS=  145.5 SIGMA=  1.6 PHAS=   38.7 FOM= 0.87 TEST= 0
INDE  17  47  32 FOBS=   93.6 SIGMA=  2.2 PHAS= -126.3 FOM= 0.29 TEST= 1
INDE  17  47  34 FOBS=  158.0 SIGMA=  1.4 PHAS= -151.1 FOM= 0.94 TEST= 0
INDE  17  47  36 FOBS=  105.1 SIGMA=  2.0 PHAS=  -37.7 FOM= 0.51 TEST= 1
INDE  17  47  38 FOBS=   85.1 SIGMA=  2.2 PHAS=   23.1 FOM= 0.88 TEST= 0
INDE  17  47  40 FOBS=   42.3 SIGMA=  4.0 PHAS=  145.4 FOM= 0.74 TEST= 0
INDE  17  47  42 FOBS=   32.2 SIGMA=  6.1 PHAS=    0.6 FOM= 0.58 TEST= 0
INDE  17  47  44 FOBS=   17.3 SIGMA= 20.3 PHAS=   33.1 FOM= 0.14 TEST= 0
INDE  17  47  46 FOBS=   74.0 SIGMA=  3.1 PHAS=   -2.3 FOM= 0.87 TEST= 0
INDE  17  47  48 FOBS=   33.6 SIGMA=  7.2 PHAS=  153.5 FOM= 0.20 TEST= 1
INDE  17  47  50 FOBS=   69.1 SIGMA=  3.3 PHAS=   44.9 FOM= 0.60 TEST= 0
INDE  17  47  52 FOBS=   44.6 SIGMA=  5.0 PHAS=   81.9 FOM= 0.07 TEST= 1
INDE  17  47  54 FOBS=    0.0 SIGMA= 21.2 PHAS=    0.0 FOM= 0.00 TEST= 0
INDE  17  47  56 FOBS=   92.9 SIGMA=  2.5 PHAS= -174.8 FOM= 0.86 TEST= 0
INDE  17  47  58 FOBS=   51.2 SIGMA=  5.5 PHAS=  128.0 FOM= 0.67 TEST= 0
INDE  17  48  17 FOBS=  182.3 SIGMA=  1.3 PHAS= -114.0 FOM= 0.93 TEST= 0
INDE  17  48  19 FOBS=  148.2 SIGMA=  1.5 PHAS=   43.4 FOM= 0.95 TEST= 0
INDE  17  48  21 FOBS=  166.6 SIGMA=  1.4 PHAS=   96.0 FOM= 0.94 TEST= 0
INDE  17  48  23 FOBS=   73.0 SIGMA=  2.9 PHAS= -109.2 FOM= 0.95 TEST= 0
INDE  17  48  25 FOBS=   18.1 SIGMA= 13.0 PHAS=   15.8 FOM= 0.06 TEST= 0
INDE  17  48  27 FOBS=  104.9 SIGMA=  2.1 PHAS= -167.2 FOM= 0.26 TEST= 0
INDE  17  48  29 FOBS=  144.0 SIGMA=  1.6 PHAS= -170.7 FOM= 0.95 TEST= 0
INDE  17  48  31 FOBS=  101.5 SIGMA=  2.2 PHAS=  -39.4 FOM= 0.92 TEST= 0
INDE  17  48  33 FOBS=   46.3 SIGMA=  4.7 PHAS= -128.1 FOM= 0.67 TEST= 1
INDE  17  48  35 FOBS=   60.3 SIGMA=  3.4 PHAS=  114.4 FOM= 0.88 TEST= 0
INDE  17  48  37 FOBS=   77.9 SIGMA=  2.6 PHAS=  -64.8 FOM= 0.82 TEST= 0
INDE  17  48  39 FOBS=   19.0 SIGMA= 10.8 PHAS=   50.4 FOM= 0.13 TEST= 0
INDE  17  48  41 FOBS=   51.9 SIGMA=  3.3 PHAS=   65.7 FOM= 0.32 TEST= 0
INDE  17  48  43 FOBS=   29.1 SIGMA=  6.8 PHAS=   97.6 FOM= 0.46 TEST= 0
INDE  17  48  45 FOBS=  112.3 SIGMA=  2.1 PHAS= -121.4 FOM= 0.94 TEST= 0
INDE  17  48  47 FOBS=   98.9 SIGMA=  2.3 PHAS=   81.9 FOM= 0.93 TEST= 0
INDE  17  48  49 FOBS=  112.8 SIGMA=  2.1 PHAS=  -19.6 FOM= 0.90 TEST= 0
INDE  17  48  51 FOBS=   59.3 SIGMA=  3.8 PHAS=  -87.6 FOM= 0.23 TEST= 1
INDE  17  48  53 FOBS=   25.5 SIGMA=  9.6 PHAS=   18.9 FOM= 0.67 TEST= 0
INDE  17  48  55 FOBS=   35.1 SIGMA=  7.9 PHAS=  118.3 FOM= 0.20 TEST= 1
INDE  17  48  57 FOBS=   70.3 SIGMA=  4.0 PHAS=  115.7 FOM= 0.87 TEST= 0
INDE  17  49  18 FOBS=  134.0 SIGMA=  1.6 PHAS=  -19.9 FOM= 0.83 TEST= 0
INDE  17  49  20 FOBS=   55.7 SIGMA=  3.7 PHAS=  -16.4 FOM= 0.78 TEST= 0
INDE  17  49  22 FOBS=    0.0 SIGMA= 22.2 PHAS=    0.0 FOM= 0.00 TEST= 0
INDE  17  49  24 FOBS=   66.7 SIGMA=  3.5 PHAS=   76.7 FOM= 0.89 TEST= 0
INDE  17  49  26 FOBS=  152.1 SIGMA=  1.5 PHAS=  -37.7 FOM= 0.83 TEST= 0
INDE  17  49  28 FOBS=  148.1 SIGMA=  1.5 PHAS=   47.6 FOM= 0.93 TEST= 0
INDE  17  49  30 FOBS=  157.5 SIGMA=  1.5 PHAS=   29.4 FOM= 0.91 TEST= 0
INDE  17  49  32 FOBS=  182.5 SIGMA=  1.3 PHAS= -141.9 FOM= 0.98 TEST= 0
INDE  17  49  34 FOBS=    0.0 SIGMA= 20.7 PHAS=    0.0 FOM= 0.00 TEST= 0
INDE  17  49  36 FOBS=   54.2 SIGMA=  3.7 PHAS= -166.1 FOM= 0.35 TEST= 0
INDE  17  49  38 FOBS=   32.8 SIGMA=  5.8 PHAS=  -64.4 FOM= 0.73 TEST= 0
INDE  17  49  40 FOBS=   34.8 SIGMA=  5.2 PHAS=  -53.7 FOM= 0.48 TEST= 0
INDE  17  49  42 FOBS=   37.7 SIGMA=  4.5 PHAS=  -21.4 FOM= 0.56 TEST= 0
INDE  17  49  44 FOBS=   69.5 SIGMA=  2.9 PHAS= -112.9 FOM= 0.59 TEST= 0
INDE  17  49  46 FOBS=   62.7 SIGMA=  3.7 PHAS=   -3.2 FOM= 0.51 TEST= 0
INDE  17  49  48 FOBS=   51.7 SIGMA=  4.4 PHAS=  -43.4 FOM= 0.66 TEST= 0
INDE  17  49  50 FOBS=   11.7 SIGMA= 19.3 PHAS= -105.4 FOM= 0.16 TEST= 0
INDE  17  49  52 FOBS=   59.4 SIGMA=  3.9 PHAS=  -85.7 FOM= 0.85 TEST= 0
INDE  17  49  54 FOBS=   64.8 SIGMA=  3.6 PHAS=  -82.3 FOM= 0.25 TEST= 1
INDE  17  49  56 FOBS=   39.6 SIGMA=  7.1 PHAS=   29.8 FOM= 0.87 TEST= 0
INDE  17  50  17 FOBS=   79.4 SIGMA=  3.5 PHAS=   -6.9 FOM= 0.50 TEST= 1
INDE  17  50  19 FOBS=  112.4 SIGMA=  1.9 PHAS=  -16.7 FOM= 0.90 TEST= 0
INDE  17  50  21 FOBS=  133.3 SIGMA=  1.8 PHAS=  138.4 FOM= 0.41 TEST= 1
INDE  17  50  23 FOBS=   67.3 SIGMA=  3.2 PHAS= -106.8 FOM= 0.58 TEST= 0
INDE  17  50  25 FOBS=  121.0 SIGMA=  1.8 PHAS= -109.1 FOM= 0.93 TEST= 0
INDE  17  50  27 FOBS=    0.0 SIGMA= 20.5 PHAS=    0.0 FOM= 0.00 TEST= 0
```

*FIG. 12A - 404*

| | | | | | | | | | | | | |
|---|---|---|---|---|---|---|---|---|---|---|---|---|
| INDE | 17 | 50 | 29 | FOBS= | 35.7 | SIGMA= | 6.5 | PHAS= | -79.0 | FOM= | 0.59 | TEST= 0 |
| INDE | 17 | 50 | 31 | FOBS= | 0.0 | SIGMA= | 22.4 | PHAS= | 0.0 | FOM= | 0.00 | TEST= 0 |
| INDE | 17 | 50 | 33 | FOBS= | 0.0 | SIGMA= | 20.6 | PHAS= | 0.0 | FOM= | 0.00 | TEST= 0 |
| INDE | 17 | 50 | 35 | FOBS= | 57.8 | SIGMA= | 3.5 | PHAS= | 117.3 | FOM= | 0.77 | TEST= 0 |
| INDE | 17 | 50 | 37 | FOBS= | 0.0 | SIGMA= | 20.9 | PHAS= | 0.0 | FOM= | 0.00 | TEST= 0 |
| INDE | 17 | 50 | 39 | FOBS= | 0.0 | SIGMA= | 20.5 | PHAS= | 0.0 | FOM= | 0.00 | TEST= 0 |
| INDE | 17 | 50 | 41 | FOBS= | 30.6 | SIGMA= | 5.6 | PHAS= | 165.4 | FOM= | 0.35 | TEST= 0 |
| INDE | 17 | 50 | 43 | FOBS= | 82.7 | SIGMA= | 2.1 | PHAS= | 168.8 | FOM= | 0.79 | TEST= 0 |
| INDE | 17 | 50 | 45 | FOBS= | 35.5 | SIGMA= | 5.6 | PHAS= | 11.2 | FOM= | 0.35 | TEST= 0 |
| INDE | 17 | 50 | 47 | FOBS= | 36.5 | SIGMA= | 6.9 | PHAS= | 153.2 | FOM= | 0.64 | TEST= 0 |
| INDE | 17 | 50 | 49 | FOBS= | 32.9 | SIGMA= | 6.9 | PHAS= | -69.3 | FOM= | 0.44 | TEST= 0 |
| INDE | 17 | 50 | 51 | FOBS= | 16.9 | SIGMA= | 24.6 | PHAS= | 168.8 | FOM= | 0.37 | TEST= 0 |
| INDE | 17 | 50 | 53 | FOBS= | 48.0 | SIGMA= | 5.2 | PHAS= | -45.2 | FOM= | 0.34 | TEST= 0 |
| INDE | 17 | 50 | 55 | FOBS= | 109.2 | SIGMA= | 2.7 | PHAS= | -81.9 | FOM= | 0.95 | TEST= 0 |
| INDE | 17 | 50 | 57 | FOBS= | 44.2 | SIGMA= | 7.5 | PHAS= | 138.4 | FOM= | 0.22 | TEST= 0 |
| INDE | 17 | 51 | 18 | FOBS= | 104.2 | SIGMA= | 2.6 | PHAS= | -61.9 | FOM= | 0.93 | TEST= 0 |
| INDE | 17 | 51 | 20 | FOBS= | 174.0 | SIGMA= | 1.3 | PHAS= | -121.0 | FOM= | 0.93 | TEST= 0 |
| INDE | 17 | 51 | 22 | FOBS= | 123.2 | SIGMA= | 1.8 | PHAS= | 113.4 | FOM= | 0.94 | TEST= 0 |
| INDE | 17 | 51 | 24 | FOBS= | 145.3 | SIGMA= | 1.6 | PHAS= | 134.7 | FOM= | 0.93 | TEST= 0 |
| INDE | 17 | 51 | 26 | FOBS= | 87.8 | SIGMA= | 2.5 | PHAS= | 76.5 | FOM= | 0.82 | TEST= 0 |
| INDE | 17 | 51 | 28 | FOBS= | 98.2 | SIGMA= | 2.2 | PHAS= | 61.5 | FOM= | 0.90 | TEST= 0 |
| INDE | 17 | 51 | 30 | FOBS= | 142.4 | SIGMA= | 1.6 | PHAS= | 86.0 | FOM= | 0.91 | TEST= 0 |
| INDE | 17 | 51 | 32 | FOBS= | 0.0 | SIGMA= | 22.4 | PHAS= | 0.0 | FOM= | 0.00 | TEST= 0 |
| INDE | 17 | 51 | 34 | FOBS= | 91.4 | SIGMA= | 2.2 | PHAS= | -19.1 | FOM= | 0.90 | TEST= 0 |
| INDE | 17 | 51 | 36 | FOBS= | 77.0 | SIGMA= | 2.6 | PHAS= | 66.2 | FOM= | 0.85 | TEST= 0 |
| INDE | 17 | 51 | 38 | FOBS= | 49.4 | SIGMA= | 4.1 | PHAS= | -10.2 | FOM= | 0.75 | TEST= 0 |
| INDE | 17 | 51 | 40 | FOBS= | 119.1 | SIGMA= | 1.6 | PHAS= | -27.7 | FOM= | 0.91 | TEST= 0 |
| INDE | 17 | 51 | 42 | FOBS= | 38.1 | SIGMA= | 5.0 | PHAS= | 125.4 | FOM= | 0.55 | TEST= 0 |
| INDE | 17 | 51 | 44 | FOBS= | 68.6 | SIGMA= | 2.6 | PHAS= | -109.1 | FOM= | 0.56 | TEST= 0 |
| INDE | 17 | 51 | 46 | FOBS= | 0.0 | SIGMA= | 21.0 | PHAS= | 0.0 | FOM= | 0.00 | TEST= 0 |
| INDE | 17 | 51 | 48 | FOBS= | 44.0 | SIGMA= | 5.3 | PHAS= | 62.9 | FOM= | 0.25 | TEST= 0 |
| INDE | 17 | 51 | 50 | FOBS= | 43.5 | SIGMA= | 5.4 | PHAS= | 147.2 | FOM= | 0.19 | TEST= 0 |
| INDE | 17 | 51 | 52 | FOBS= | 34.9 | SIGMA= | 6.6 | PHAS= | -35.7 | FOM= | 0.47 | TEST= 0 |
| INDE | 17 | 51 | 54 | FOBS= | 31.3 | SIGMA= | 10.3 | PHAS= | 153.4 | FOM= | 0.00 | TEST= 1 |
| INDE | 17 | 51 | 56 | FOBS= | 70.3 | SIGMA= | 5.0 | PHAS= | 157.4 | FOM= | 0.67 | TEST= 0 |
| INDE | 17 | 52 | 17 | FOBS= | 0.0 | SIGMA= | 22.9 | PHAS= | 0.0 | FOM= | 0.00 | TEST= 0 |
| INDE | 17 | 52 | 19 | FOBS= | 41.1 | SIGMA= | 5.0 | PHAS= | -73.7 | FOM= | 0.23 | TEST= 0 |
| INDE | 17 | 52 | 21 | FOBS= | 33.5 | SIGMA= | 6.5 | PHAS= | -136.3 | FOM= | 0.34 | TEST= 0 |
| INDE | 17 | 52 | 23 | FOBS= | 105.2 | SIGMA= | 2.0 | PHAS= | -38.6 | FOM= | 0.94 | TEST= 0 |
| INDE | 17 | 52 | 25 | FOBS= | 112.9 | SIGMA= | 1.9 | PHAS= | -25.2 | FOM= | 0.92 | TEST= 0 |
| INDE | 17 | 52 | 27 | FOBS= | 56.1 | SIGMA= | 3.8 | PHAS= | 25.6 | FOM= | 0.68 | TEST= 0 |
| INDE | 17 | 52 | 29 | FOBS= | 95.7 | SIGMA= | 2.2 | PHAS= | 22.8 | FOM= | 0.66 | TEST= 0 |
| INDE | 17 | 52 | 31 | FOBS= | 43.5 | SIGMA= | 4.8 | PHAS= | -0.9 | FOM= | 0.83 | TEST= 0 |
| INDE | 17 | 52 | 33 | FOBS= | 45.3 | SIGMA= | 4.6 | PHAS= | -85.7 | FOM= | 0.54 | TEST= 0 |
| INDE | 17 | 52 | 35 | FOBS= | 52.6 | SIGMA= | 3.8 | PHAS= | -138.8 | FOM= | 0.87 | TEST= 0 |
| INDE | 17 | 52 | 37 | FOBS= | 46.1 | SIGMA= | 4.3 | PHAS= | 9.6 | FOM= | 0.26 | TEST= 0 |
| INDE | 17 | 52 | 39 | FOBS= | 95.5 | SIGMA= | 2.0 | PHAS= | -131.3 | FOM= | 0.92 | TEST= 0 |
| INDE | 17 | 52 | 41 | FOBS= | 36.3 | SIGMA= | 5.2 | PHAS= | 51.9 | FOM= | 0.13 | TEST= 0 |
| INDE | 17 | 52 | 43 | FOBS= | 0.0 | SIGMA= | 18.8 | PHAS= | 0.0 | FOM= | 0.00 | TEST= 0 |
| INDE | 17 | 52 | 45 | FOBS= | 44.7 | SIGMA= | 3.9 | PHAS= | -8.1 | FOM= | 0.50 | TEST= 0 |
| INDE | 17 | 52 | 47 | FOBS= | 78.7 | SIGMA= | 2.6 | PHAS= | 45.6 | FOM= | 0.42 | TEST= 1 |
| INDE | 17 | 52 | 49 | FOBS= | 61.8 | SIGMA= | 3.8 | PHAS= | -142.8 | FOM= | 0.04 | TEST= 1 |
| INDE | 17 | 52 | 51 | FOBS= | 0.0 | SIGMA= | 24.5 | PHAS= | 0.0 | FOM= | 0.00 | TEST= 0 |
| INDE | 17 | 52 | 53 | FOBS= | 0.0 | SIGMA= | 26.4 | PHAS= | 0.0 | FOM= | 0.00 | TEST= 0 |
| INDE | 17 | 52 | 55 | FOBS= | 0.0 | SIGMA= | 30.2 | PHAS= | 0.0 | FOM= | 0.00 | TEST= 1 |
| INDE | 17 | 53 | 18 | FOBS= | 120.8 | SIGMA= | 2.3 | PHAS= | 177.0 | FOM= | 0.93 | TEST= 0 |
| INDE | 17 | 53 | 20 | FOBS= | 76.2 | SIGMA= | 2.7 | PHAS= | 125.4 | FOM= | 0.87 | TEST= 0 |
| INDE | 17 | 53 | 22 | FOBS= | 98.0 | SIGMA= | 2.2 | PHAS= | 162.8 | FOM= | 0.89 | TEST= 0 |
| INDE | 17 | 53 | 24 | FOBS= | 68.2 | SIGMA= | 3.1 | PHAS= | 73.9 | FOM= | 0.04 | TEST= 1 |
| INDE | 17 | 53 | 26 | FOBS= | 53.5 | SIGMA= | 3.9 | PHAS= | 74.6 | FOM= | 0.57 | TEST= 0 |
| INDE | 17 | 53 | 28 | FOBS= | 0.0 | SIGMA= | 21.5 | PHAS= | 0.0 | FOM= | 0.00 | TEST= 0 |
| INDE | 17 | 53 | 30 | FOBS= | 29.4 | SIGMA= | 7.1 | PHAS= | -8.3 | FOM= | 0.30 | TEST= 0 |
| INDE | 17 | 53 | 32 | FOBS= | 29.6 | SIGMA= | 7.0 | PHAS= | -13.8 | FOM= | 0.16 | TEST= 0 |
| INDE | 17 | 53 | 34 | FOBS= | 14.6 | SIGMA= | 14.2 | PHAS= | -22.3 | FOM= | 0.18 | TEST= 0 |
| INDE | 17 | 53 | 36 | FOBS= | 117.1 | SIGMA= | 1.8 | PHAS= | 43.0 | FOM= | 0.94 | TEST= 0 |
| INDE | 17 | 53 | 38 | FOBS= | 44.7 | SIGMA= | 4.5 | PHAS= | 138.3 | FOM= | 0.55 | TEST= 0 |
| INDE | 17 | 53 | 40 | FOBS= | 64.8 | SIGMA= | 2.9 | PHAS= | -10.9 | FOM= | 0.83 | TEST= 0 |
| INDE | 17 | 53 | 42 | FOBS= | 0.0 | SIGMA= | 18.5 | PHAS= | 0.0 | FOM= | 0.00 | TEST= 0 |
| INDE | 17 | 53 | 44 | FOBS= | 0.0 | SIGMA= | 18.6 | PHAS= | 0.0 | FOM= | 0.00 | TEST= 0 |
| INDE | 17 | 53 | 46 | FOBS= | 59.8 | SIGMA= | 3.2 | PHAS= | -69.0 | FOM= | 0.87 | TEST= 0 |

*FIG. 12A - 405*

```
INDE  17  53  48  FOBS=   49.9  SIGMA=   4.5  PHAS=   -76.2  FOM=  0.69  TEST=  0
INDE  17  53  50  FOBS=   89.1  SIGMA=   3.1  PHAS=  -119.5  FOM=  0.90  TEST=  0
INDE  17  53  52  FOBS=    0.0  SIGMA=  30.7  PHAS=     0.0  FOM=  0.00  TEST=  0
INDE  17  53  54  FOBS=    0.0  SIGMA=  30.3  PHAS=     0.0  FOM=  0.00  TEST=  0
INDE  17  54  17  FOBS=  105.7  SIGMA=   2.1  PHAS=    50.1  FOM=  0.95  TEST=  0
INDE  17  54  19  FOBS=   90.4  SIGMA=   2.9  PHAS=   113.4  FOM=  0.89  TEST=  0
INDE  17  54  21  FOBS=  162.6  SIGMA=   1.5  PHAS=    13.7  FOM=  0.96  TEST=  0
INDE  17  54  23  FOBS=   99.3  SIGMA=   2.1  PHAS=   -53.7  FOM=  0.72  TEST=  0
INDE  17  54  25  FOBS=   49.5  SIGMA=   4.2  PHAS=   -75.7  FOM=  0.66  TEST=  0
INDE  17  54  27  FOBS=  113.1  SIGMA=   1.9  PHAS=    79.3  FOM=  0.93  TEST=  0
INDE  17  54  29  FOBS=   22.7  SIGMA=   9.2  PHAS=   -92.1  FOM=  0.19  TEST=  0
INDE  17  54  31  FOBS=    0.0  SIGMA=  21.2  PHAS=     0.0  FOM=  0.00  TEST=  0
INDE  17  54  33  FOBS=   39.3  SIGMA=   5.3  PHAS=   -11.1  FOM=  0.44  TEST=  0
INDE  17  54  35  FOBS=   89.3  SIGMA=   2.4  PHAS=   -63.0  FOM=  0.93  TEST=  0
INDE  17  54  37  FOBS=   67.6  SIGMA=   3.0  PHAS=    31.7  FOM=  0.90  TEST=  0
INDE  17  54  39  FOBS=   61.1  SIGMA=   3.3  PHAS=   125.4  FOM=  0.83  TEST=  0
INDE  17  54  41  FOBS=   38.4  SIGMA=   5.7  PHAS=   -75.3  FOM=  0.39  TEST=  0
INDE  17  54  43  FOBS=    0.0  SIGMA=  19.7  PHAS=     0.0  FOM=  0.00  TEST=  0
INDE  17  54  45  FOBS=   78.6  SIGMA=   2.5  PHAS=   155.7  FOM=  0.84  TEST=  0
INDE  17  54  47  FOBS=   35.7  SIGMA=   6.7  PHAS=   152.6  FOM=  0.75  TEST=  0
INDE  17  54  49  FOBS=  148.4  SIGMA=   1.8  PHAS=   137.8  FOM=  0.97  TEST=  0
INDE  17  54  51  FOBS=    0.0  SIGMA=  30.2  PHAS=     0.0  FOM=  0.00  TEST=  0
INDE  17  54  53  FOBS=   64.7  SIGMA=   7.5  PHAS=    93.6  FOM=  0.72  TEST=  0
INDE  17  55  18  FOBS=   51.3  SIGMA=   5.1  PHAS=   133.1  FOM=  0.35  TEST=  0
INDE  17  55  20  FOBS=   79.1  SIGMA=   2.6  PHAS=   149.4  FOM=  0.12  TEST=  1
INDE  17  55  22  FOBS=  110.5  SIGMA=   2.1  PHAS=   -29.9  FOM=  0.89  TEST=  0
INDE  17  55  24  FOBS=   14.9  SIGMA=  14.8  PHAS=   118.3  FOM=  0.05  TEST=  0
INDE  17  55  26  FOBS=   30.9  SIGMA=   7.3  PHAS=    75.7  FOM=  0.17  TEST=  0
INDE  17  55  28  FOBS=   76.5  SIGMA=   2.8  PHAS=    -1.6  FOM=  0.79  TEST=  0
INDE  17  55  30  FOBS=   73.7  SIGMA=   2.8  PHAS=   -12.2  FOM=  0.70  TEST=  0
INDE  17  55  32  FOBS=   51.4  SIGMA=   4.4  PHAS=  -105.3  FOM=  0.53  TEST=  0
INDE  17  55  34  FOBS=   83.2  SIGMA=   2.6  PHAS=  -149.7  FOM=  0.79  TEST=  0
INDE  17  55  36  FOBS=  168.0  SIGMA=   1.3  PHAS=   -17.1  FOM=  0.98  TEST=  0
INDE  17  55  38  FOBS=  140.0  SIGMA=   1.7  PHAS=    -9.4  FOM=  0.96  TEST=  0
INDE  17  55  40  FOBS=   44.0  SIGMA=   4.7  PHAS=    29.2  FOM=  0.41  TEST=  0
INDE  17  55  42  FOBS=   43.3  SIGMA=   5.4  PHAS=  -122.0  FOM=  0.12  TEST=  1
INDE  17  55  44  FOBS=   58.2  SIGMA=   3.5  PHAS=    89.9  FOM=  0.85  TEST=  0
INDE  17  55  46  FOBS=   69.5  SIGMA=   3.0  PHAS=    24.8  FOM=  0.86  TEST=  0
INDE  17  55  48  FOBS=   53.0  SIGMA=   4.4  PHAS=    44.3  FOM=  0.87  TEST=  0
INDE  17  55  50  FOBS=    0.0  SIGMA=  25.2  PHAS=     0.0  FOM=  0.00  TEST=  1
INDE  17  55  52  FOBS=   96.0  SIGMA=   5.0  PHAS=   -12.9  FOM=  0.91  TEST=  0
INDE  17  56  17  FOBS=   94.7  SIGMA=   2.0  PHAS=   106.0  FOM=  0.87  TEST=  0
INDE  17  56  19  FOBS=    0.0  SIGMA=  22.7  PHAS=     0.0  FOM=  0.00  TEST=  1
INDE  17  56  21  FOBS=   76.0  SIGMA=   2.7  PHAS=   -47.4  FOM=  0.82  TEST=  0
INDE  17  56  23  FOBS=  128.8  SIGMA=   1.7  PHAS=   -95.1  FOM=  0.95  TEST=  0
INDE  17  56  25  FOBS=   84.5  SIGMA=   2.5  PHAS=  -137.4  FOM=  0.27  TEST=  1
INDE  17  56  27  FOBS=   24.3  SIGMA=   9.3  PHAS=   178.9  FOM=  0.10  TEST=  0
INDE  17  56  29  FOBS=   36.2  SIGMA=   7.0  PHAS=  -117.0  FOM=  0.45  TEST=  0
INDE  17  56  31  FOBS=    0.0  SIGMA=  21.5  PHAS=     0.0  FOM=  0.00  TEST=  0
INDE  17  56  33  FOBS=   79.5  SIGMA=   3.0  PHAS=   110.6  FOM=  0.93  TEST=  0
INDE  17  56  35  FOBS=  132.8  SIGMA=   1.9  PHAS=   -80.4  FOM=  0.97  TEST=  0
INDE  17  56  37  FOBS=  119.0  SIGMA=   2.1  PHAS=   -93.2  FOM=  0.95  TEST=  0
INDE  17  56  39  FOBS=   46.0  SIGMA=   5.3  PHAS=   151.7  FOM=  0.75  TEST=  0
INDE  17  56  41  FOBS=  105.7  SIGMA=   2.2  PHAS=   -17.0  FOM=  0.93  TEST=  0
INDE  17  56  43  FOBS=  112.3  SIGMA=   1.9  PHAS=    44.0  FOM=  0.95  TEST=  0
INDE  17  56  45  FOBS=   51.0  SIGMA=   4.0  PHAS=  -178.0  FOM=  0.55  TEST=  0
INDE  17  56  47  FOBS=    0.0  SIGMA=  24.6  PHAS=     0.0  FOM=  0.00  TEST=  0
INDE  17  56  49  FOBS=    0.0  SIGMA=  23.4  PHAS=     0.0  FOM=  0.00  TEST=  0
INDE  17  56  51  FOBS=   48.0  SIGMA=   6.8  PHAS=  -128.7  FOM=  0.79  TEST=  0
INDE  17  57  18  FOBS=   83.8  SIGMA=   3.1  PHAS=    12.5  FOM=  0.88  TEST=  0
INDE  17  57  20  FOBS=   71.6  SIGMA=   3.6  PHAS=   110.6  FOM=  0.65  TEST=  0
INDE  17  57  22  FOBS=  130.2  SIGMA=   1.7  PHAS=   160.7  FOM=  0.91  TEST=  0
INDE  17  57  24  FOBS=  129.1  SIGMA=   1.6  PHAS=   111.8  FOM=  0.94  TEST=  0
INDE  17  57  26  FOBS=   99.9  SIGMA=   2.1  PHAS=    95.1  FOM=  0.85  TEST=  0
INDE  17  57  28  FOBS=   38.7  SIGMA=   5.3  PHAS=    89.0  FOM=  0.12  TEST=  0
INDE  17  57  30  FOBS=   43.2  SIGMA=   5.3  PHAS=   -35.8  FOM=  0.45  TEST=  0
INDE  17  57  32  FOBS=   71.1  SIGMA=   3.6  PHAS=   -18.8  FOM=  0.90  TEST=  0
INDE  17  57  34  FOBS=  124.4  SIGMA=   2.2  PHAS=  -140.1  FOM=  0.94  TEST=  0
INDE  17  57  36  FOBS=   38.6  SIGMA=   6.8  PHAS=  -171.9  FOM=  0.57  TEST=  1
INDE  17  57  38  FOBS=   92.1  SIGMA=   2.7  PHAS=    32.4  FOM=  0.94  TEST=  0
```

*FIG. 12A - 406*

```
INDE 17 57 40 FOBS=    49.2 SIGMA=  5.0 PHAS=  -16.4 FOM= 0.55 TEST= 0
INDE 17 57 42 FOBS=    97.1 SIGMA=  2.5 PHAS=  -36.6 FOM= 0.95 TEST= 0
INDE 17 57 44 FOBS=    44.0 SIGMA=  4.9 PHAS=   -2.6 FOM= 0.76 TEST= 0
INDE 17 57 46 FOBS=    51.4 SIGMA=  4.9 PHAS=  100.6 FOM= 0.70 TEST= 0
INDE 17 57 48 FOBS=    88.0 SIGMA=  3.2 PHAS=  125.1 FOM= 0.03 TEST= 1
INDE 17 57 50 FOBS=    21.3 SIGMA= 20.7 PHAS=   79.8 FOM= 0.27 TEST= 0
INDE 17 58 17 FOBS=    86.2 SIGMA=  2.5 PHAS=  180.0 FOM= 0.95 TEST= 0
INDE 17 58 19 FOBS=   100.7 SIGMA=  2.6 PHAS=  -28.7 FOM= 0.92 TEST= 0
INDE 17 58 21 FOBS=    47.5 SIGMA=  5.4 PHAS= -140.1 FOM= 0.78 TEST= 0
INDE 17 58 23 FOBS=    37.2 SIGMA=  5.7 PHAS=   27.4 FOM= 0.76 TEST= 0
INDE 17 58 25 FOBS=   151.4 SIGMA=  1.6 PHAS=  -81.6 FOM= 0.17 TEST= 1
INDE 17 58 27 FOBS=    97.2 SIGMA=  2.6 PHAS=    3.1 FOM= 0.89 TEST= 0
INDE 17 58 29 FOBS=    89.1 SIGMA=  2.9 PHAS=   84.0 FOM= 0.82 TEST= 0
INDE 17 58 31 FOBS=    87.6 SIGMA=  3.0 PHAS= -153.6 FOM= 0.86 TEST= 0
INDE 17 58 33 FOBS=    80.7 SIGMA=  3.2 PHAS=  125.8 FOM= 0.77 TEST= 0
INDE 17 58 35 FOBS=    37.0 SIGMA=  7.0 PHAS=  148.6 FOM= 0.77 TEST= 0
INDE 17 58 37 FOBS=    27.9 SIGMA=  9.6 PHAS=  -35.4 FOM= 0.29 TEST= 0
INDE 17 58 39 FOBS=    24.9 SIGMA=  9.8 PHAS=   -0.1 FOM= 0.19 TEST= 0
INDE 17 58 41 FOBS=    55.1 SIGMA=  4.6 PHAS=  -56.9 FOM= 0.75 TEST= 0
INDE 17 58 43 FOBS=     8.6 SIGMA= 25.2 PHAS=  152.5 FOM= 0.05 TEST= 0
INDE 17 58 45 FOBS=    55.2 SIGMA=  3.8 PHAS= -159.4 FOM= 0.89 TEST= 0
INDE 17 58 47 FOBS=    73.7 SIGMA=  3.8 PHAS=   86.4 FOM= 0.91 TEST= 0
INDE 17 59 18 FOBS=    50.6 SIGMA=  5.6 PHAS=   50.3 FOM= 0.68 TEST= 0
INDE 17 59 20 FOBS=    75.0 SIGMA=  3.9 PHAS=  164.5 FOM= 0.86 TEST= 0
INDE 17 59 22 FOBS=    54.8 SIGMA=  4.3 PHAS=  172.8 FOM= 0.63 TEST= 0
INDE 17 59 24 FOBS=    42.7 SIGMA=  5.6 PHAS=  -30.9 FOM= 0.70 TEST= 0
INDE 17 59 26 FOBS=    54.6 SIGMA=  4.4 PHAS=  -96.8 FOM= 0.85 TEST= 0
INDE 17 59 28 FOBS=   157.4 SIGMA=  1.7 PHAS=  -36.6 FOM= 0.95 TEST= 0
INDE 17 59 30 FOBS=    79.7 SIGMA=  3.3 PHAS=   35.5 FOM= 0.92 TEST= 0
INDE 17 59 32 FOBS=    49.4 SIGMA=  5.2 PHAS=  -65.8 FOM= 0.38 TEST= 0
INDE 17 59 34 FOBS=     0.0 SIGMA= 26.4 PHAS=    0.0 FOM= 0.00 TEST= 0
INDE 17 59 36 FOBS=    41.5 SIGMA=  7.4 PHAS=   98.2 FOM= 0.62 TEST= 0
INDE 17 59 38 FOBS=    16.8 SIGMA= 18.3 PHAS=  123.4 FOM= 0.44 TEST= 0
INDE 17 59 40 FOBS=   117.4 SIGMA=  2.2 PHAS=  -17.6 FOM= 0.94 TEST= 0
INDE 17 59 42 FOBS=    53.1 SIGMA=  4.5 PHAS=   18.8 FOM= 0.71 TEST= 0
INDE 17 59 44 FOBS=    55.6 SIGMA=  3.8 PHAS=   99.5 FOM= 0.88 TEST= 0
INDE 17 59 46 FOBS=   104.4 SIGMA=  2.7 PHAS=   60.5 FOM= 0.96 TEST= 0
INDE 17 60 17 FOBS=     7.3 SIGMA= 30.9 PHAS=   51.7 FOM= 0.10 TEST= 0
INDE 17 60 19 FOBS=    31.2 SIGMA=  9.2 PHAS=   28.8 FOM= 0.81 TEST= 0
INDE 17 60 21 FOBS=    51.5 SIGMA=  6.7 PHAS=  174.2 FOM= 0.69 TEST= 0
INDE 17 60 23 FOBS=    42.7 SIGMA=  5.5 PHAS= -132.7 FOM= 0.53 TEST= 0
INDE 17 60 25 FOBS=    15.0 SIGMA= 18.0 PHAS=  -16.9 FOM= 0.13 TEST= 0
INDE 17 60 27 FOBS=     0.0 SIGMA= 26.1 PHAS=    0.0 FOM= 0.00 TEST= 0
INDE 17 60 29 FOBS=    70.2 SIGMA=  3.6 PHAS= -122.7 FOM= 0.32 TEST= 1
INDE 17 60 31 FOBS=    40.6 SIGMA=  6.3 PHAS= -155.9 FOM= 0.64 TEST= 0
INDE 17 60 33 FOBS=     0.0 SIGMA= 24.5 PHAS=    0.0 FOM= 0.00 TEST= 0
INDE 17 60 35 FOBS=    82.8 SIGMA=  3.3 PHAS= -100.6 FOM= 0.84 TEST= 0
INDE 17 60 37 FOBS=    65.4 SIGMA=  4.2 PHAS=   33.4 FOM= 0.69 TEST= 0
INDE 17 60 39 FOBS=    53.6 SIGMA=  5.2 PHAS=  -44.4 FOM= 0.73 TEST= 0
INDE 17 60 41 FOBS=    36.6 SIGMA=  7.7 PHAS= -155.2 FOM= 0.73 TEST= 0
INDE 17 60 43 FOBS=    32.0 SIGMA=  7.4 PHAS=   74.9 FOM= 0.58 TEST= 0
INDE 17 60 45 FOBS=    40.4 SIGMA=  6.9 PHAS=  -55.5 FOM= 0.80 TEST= 0
INDE 17 61 18 FOBS=     0.0 SIGMA= 23.9 PHAS=    0.0 FOM= 0.00 TEST= 0
INDE 17 61 20 FOBS=    37.9 SIGMA=  9.0 PHAS=  -76.1 FOM= 0.24 TEST= 0
INDE 17 61 22 FOBS=    52.2 SIGMA=  6.6 PHAS=   28.8 FOM= 0.48 TEST= 0
INDE 17 61 24 FOBS=    13.8 SIGMA= 19.8 PHAS= -178.6 FOM= 0.11 TEST= 0
INDE 17 61 26 FOBS=     0.0 SIGMA= 21.7 PHAS=    0.0 FOM= 0.00 TEST= 0
INDE 17 61 28 FOBS=     0.0 SIGMA= 23.5 PHAS=    0.0 FOM= 0.00 TEST= 1
INDE 17 61 30 FOBS=     0.0 SIGMA= 22.3 PHAS=    0.0 FOM= 0.00 TEST= 0
INDE 17 61 32 FOBS=    54.1 SIGMA=  4.8 PHAS=  -83.9 FOM= 0.36 TEST= 0
INDE 17 61 34 FOBS=   123.3 SIGMA=  2.3 PHAS= -124.3 FOM= 0.87 TEST= 0
INDE 17 61 36 FOBS=     0.0 SIGMA= 23.1 PHAS=    0.0 FOM= 0.00 TEST= 0
INDE 17 61 38 FOBS=    80.3 SIGMA=  3.4 PHAS= -123.5 FOM= 0.92 TEST= 0
INDE 17 61 40 FOBS=    55.8 SIGMA=  4.5 PHAS=    9.3 FOM= 0.78 TEST= 0
INDE 17 61 42 FOBS=    45.0 SIGMA=  6.4 PHAS=   34.7 FOM= 0.71 TEST= 0
INDE 17 61 44 FOBS=    53.1 SIGMA=  5.6 PHAS=  147.4 FOM= 0.62 TEST= 0
INDE 17 62 17 FOBS=    86.1 SIGMA=  2.9 PHAS=  144.2 FOM= 0.84 TEST= 0
INDE 17 62 19 FOBS=    33.3 SIGMA= 10.3 PHAS= -154.7 FOM= 0.01 TEST= 1
INDE 17 62 21 FOBS=     6.6 SIGMA= 51.2 PHAS= -124.7 FOM= 0.10 TEST= 0
INDE 17 62 23 FOBS=    51.8 SIGMA=  6.5 PHAS= -144.0 FOM= 0.83 TEST= 0
```

*FIG. 12A - 407*

```
INDE  17  62  25 FOBS=   54.5 SIGMA=   4.4 PHAS=  -98.4 FOM= 0.55 TEST= 0
INDE  17  62  27 FOBS=   39.1 SIGMA=   6.2 PHAS=   18.9 FOM= 0.21 TEST= 0
INDE  17  62  29 FOBS=    0.0 SIGMA=  22.1 PHAS=    0.0 FOM= 0.00 TEST= 1
INDE  17  62  31 FOBS=   23.0 SIGMA=  11.3 PHAS=   33.2 FOM= 0.08 TEST= 0
INDE  17  62  33 FOBS=   22.1 SIGMA=  12.0 PHAS=  156.5 FOM= 0.41 TEST= 0
INDE  17  62  35 FOBS=   34.8 SIGMA=   7.7 PHAS=   81.0 FOM= 0.36 TEST= 0
INDE  17  62  37 FOBS=   23.0 SIGMA=  13.3 PHAS= -158.1 FOM= 0.39 TEST= 0
INDE  17  62  39 FOBS=   17.4 SIGMA=  15.9 PHAS=  107.5 FOM= 0.27 TEST= 0
INDE  17  62  41 FOBS=   46.0 SIGMA=   7.1 PHAS= -174.1 FOM= 0.70 TEST= 0
INDE  17  62  43 FOBS=   45.4 SIGMA=   7.6 PHAS= -147.5 FOM= 0.26 TEST= 0
INDE  17  63  18 FOBS=   58.8 SIGMA=   4.3 PHAS=  -14.3 FOM= 0.18 TEST= 0
INDE  17  63  20 FOBS=   82.1 SIGMA=   4.3 PHAS= -169.0 FOM= 0.88 TEST= 0
INDE  17  63  22 FOBS=   15.5 SIGMA=  21.6 PHAS=   52.9 FOM= 0.12 TEST= 0
INDE  17  63  24 FOBS=   97.7 SIGMA=   2.9 PHAS=  113.0 FOM= 0.94 TEST= 0
INDE  17  63  26 FOBS=    0.0 SIGMA=  23.6 PHAS=    0.0 FOM= 0.00 TEST= 0
INDE  17  63  28 FOBS=   39.0 SIGMA=   7.3 PHAS=  -37.8 FOM= 0.62 TEST= 0
INDE  17  63  30 FOBS=   74.5 SIGMA=   4.0 PHAS=  -43.1 FOM= 0.90 TEST= 0
INDE  17  63  32 FOBS=   66.5 SIGMA=   4.6 PHAS= -119.4 FOM= 0.81 TEST= 0
INDE  17  63  34 FOBS=   39.3 SIGMA=   7.9 PHAS=  146.5 FOM= 0.50 TEST= 0
INDE  17  63  36 FOBS=    0.0 SIGMA=  24.8 PHAS=    0.0 FOM= 0.00 TEST= 1
INDE  17  63  38 FOBS=   34.4 SIGMA=   9.2 PHAS=  -56.4 FOM= 0.45 TEST= 0
INDE  17  63  40 FOBS=   50.7 SIGMA=   7.5 PHAS=   16.1 FOM= 0.78 TEST= 0
INDE  17  63  42 FOBS=   46.8 SIGMA=   8.5 PHAS=  102.0 FOM= 0.71 TEST= 0
INDE  17  64  17 FOBS=  102.0 SIGMA=   2.5 PHAS=  114.4 FOM= 0.81 TEST= 0
INDE  17  64  19 FOBS=   77.5 SIGMA=   3.3 PHAS=   73.2 FOM= 0.70 TEST= 0
INDE  17  64  21 FOBS=   50.9 SIGMA=   6.7 PHAS=  164.9 FOM= 0.64 TEST= 0
INDE  17  64  23 FOBS=  125.3 SIGMA=   2.9 PHAS=   -3.4 FOM= 0.96 TEST= 0
INDE  17  64  25 FOBS=   24.4 SIGMA=  11.3 PHAS=   49.3 FOM= 0.69 TEST= 0
INDE  17  64  27 FOBS=   59.2 SIGMA=   6.0 PHAS=   18.0 FOM= 0.85 TEST= 0
INDE  17  64  29 FOBS=   93.1 SIGMA=   3.2 PHAS= -139.9 FOM= 0.93 TEST= 0
INDE  17  64  31 FOBS=   45.7 SIGMA=   6.5 PHAS= -169.5 FOM= 0.18 TEST= 0
INDE  17  64  33 FOBS=  108.6 SIGMA=   3.0 PHAS=  105.5 FOM= 0.95 TEST= 0
INDE  17  64  35 FOBS=   43.7 SIGMA=   7.3 PHAS=   -9.6 FOM= 0.76 TEST= 0
INDE  17  64  37 FOBS=   31.8 SIGMA=   9.9 PHAS= -154.0 FOM= 0.41 TEST= 0
INDE  17  64  39 FOBS=   43.3 SIGMA=   7.5 PHAS=  -97.5 FOM= 0.03 TEST= 0
INDE  17  65  18 FOBS=   47.9 SIGMA=   6.0 PHAS=  -19.3 FOM= 0.62 TEST= 0
INDE  17  65  20 FOBS=    0.0 SIGMA=  26.2 PHAS=    0.0 FOM= 0.00 TEST= 0
INDE  17  65  22 FOBS=   26.2 SIGMA=  13.0 PHAS= -128.3 FOM= 0.48 TEST= 0
INDE  17  65  24 FOBS=   53.9 SIGMA=   6.4 PHAS=  -39.3 FOM= 0.82 TEST= 0
INDE  17  65  26 FOBS=   59.1 SIGMA=   4.8 PHAS=  -66.5 FOM= 0.74 TEST= 0
INDE  17  65  28 FOBS=   53.1 SIGMA=   5.4 PHAS=  -75.3 FOM= 0.80 TEST= 0
INDE  17  65  30 FOBS=   51.5 SIGMA=   5.8 PHAS=   34.5 FOM= 0.70 TEST= 0
INDE  17  65  32 FOBS=  103.8 SIGMA=   3.1 PHAS=  110.8 FOM= 0.06 TEST= 1
INDE  17  65  34 FOBS=   93.5 SIGMA=   3.5 PHAS=  -88.0 FOM= 0.92 TEST= 0
INDE  17  65  36 FOBS=   45.5 SIGMA=   7.0 PHAS=  148.9 FOM= 0.62 TEST= 0
INDE  17  65  38 FOBS=   11.4 SIGMA=  28.6 PHAS=   11.5 FOM= 0.16 TEST= 0
INDE  17  66  17 FOBS=   31.4 SIGMA=   5.3 PHAS=  -34.8 FOM= 0.30 TEST= 0
INDE  17  66  19 FOBS=   23.8 SIGMA=  12.3 PHAS=  -42.7 FOM= 0.37 TEST= 0
INDE  17  66  21 FOBS=    0.0 SIGMA=  26.1 PHAS=    0.0 FOM= 0.00 TEST= 0
INDE  17  66  23 FOBS=    0.0 SIGMA=  26.1 PHAS=    0.0 FOM= 0.00 TEST= 0
INDE  17  66  25 FOBS=    0.0 SIGMA=  26.2 PHAS=    0.0 FOM= 0.00 TEST= 0
INDE  17  66  27 FOBS=    0.0 SIGMA=  23.7 PHAS=    0.0 FOM= 0.00 TEST= 0
INDE  17  66  29 FOBS=    0.0 SIGMA=  26.7 PHAS=    0.0 FOM= 0.00 TEST= 0
INDE  17  66  31 FOBS=   42.6 SIGMA=   7.0 PHAS= -150.0 FOM= 0.29 TEST= 0
INDE  17  66  33 FOBS=   59.5 SIGMA=   5.2 PHAS=  164.1 FOM= 0.84 TEST= 0
INDE  17  66  35 FOBS=   50.7 SIGMA=   6.4 PHAS=   40.5 FOM= 0.84 TEST= 0
INDE  17  66  37 FOBS=   26.7 SIGMA=  12.3 PHAS= -110.5 FOM= 0.46 TEST= 0
INDE  17  67  18 FOBS=   24.4 SIGMA=  11.6 PHAS=   52.2 FOM= 0.08 TEST= 1
INDE  17  67  20 FOBS=    0.0 SIGMA=  24.2 PHAS=    0.0 FOM= 0.00 TEST= 0
INDE  17  67  22 FOBS=   28.5 SIGMA=  12.1 PHAS=  -33.6 FOM= 0.39 TEST= 0
INDE  17  67  24 FOBS=   12.0 SIGMA=  28.8 PHAS=   90.2 FOM= 0.12 TEST= 0
INDE  17  67  26 FOBS=   44.9 SIGMA=   7.8 PHAS=  -13.5 FOM= 0.82 TEST= 0
INDE  17  67  28 FOBS=   13.4 SIGMA=  21.1 PHAS=  172.1 FOM= 0.04 TEST= 0
INDE  17  67  30 FOBS=   58.5 SIGMA=   5.1 PHAS=  -42.0 FOM= 0.73 TEST= 0
INDE  17  67  32 FOBS=    0.0 SIGMA=  24.6 PHAS=    0.0 FOM= 0.00 TEST= 0
INDE  17  67  34 FOBS=   70.4 SIGMA=   4.6 PHAS=  -77.4 FOM= 0.87 TEST= 0
INDE  17  68  17 FOBS=    0.0 SIGMA=  25.7 PHAS=    0.0 FOM= 0.00 TEST= 0
INDE  17  68  19 FOBS=   81.7 SIGMA=   2.9 PHAS=  -78.7 FOM= 0.89 TEST= 0
INDE  17  68  23 FOBS=   43.5 SIGMA=  11.7 PHAS=  120.0 FOM= 0.73 TEST= 0
INDE  17  68  25 FOBS=   97.8 SIGMA=   5.4 PHAS=  -78.8 FOM= 0.91 TEST= 0
```

*FIG. 12A - 408*

```
INDE  17  68  27  FOBS=   48.0  SIGMA=   6.0  PHAS=   -90.9  FOM=  0.75  TEST= 0
INDE  17  68  29  FOBS=    0.0  SIGMA=  26.6  PHAS=     0.0  FOM=  0.00  TEST= 0
INDE  17  68  31  FOBS=    0.0  SIGMA=  27.1  PHAS=     0.0  FOM=  0.00  TEST= 0
INDE  17  68  33  FOBS=    8.1  SIGMA=  39.1  PHAS=   163.0  FOM=  0.13  TEST= 0
INDE  17  69  18  FOBS=   20.9  SIGMA=  16.9  PHAS=  -169.0  FOM=  0.42  TEST= 0
INDE  17  69  20  FOBS=   39.0  SIGMA=   9.5  PHAS=  -134.7  FOM=  0.70  TEST= 0
INDE  17  69  26  FOBS=   33.5  SIGMA=  15.2  PHAS=  -137.7  FOM=  0.70  TEST= 0
INDE  17  69  28  FOBS=   35.3  SIGMA=  10.2  PHAS=    78.2  FOM=  0.29  TEST= 0
INDE  17  69  30  FOBS=   39.1  SIGMA=   9.5  PHAS=   -21.8  FOM=  0.41  TEST= 0
INDE  17  70  17  FOBS=   18.1  SIGMA=  17.6  PHAS=  -161.3  FOM=  0.22  TEST= 0
INDE  17  70  19  FOBS=   28.7  SIGMA=   6.8  PHAS=     1.7  FOM=  0.29  TEST= 0
INDE  17  70  21  FOBS=    0.0  SIGMA=  27.6  PHAS=     0.0  FOM=  0.00  TEST= 1
INDE  17  70  29  FOBS=    0.0  SIGMA=  32.1  PHAS=     0.0  FOM=  0.00  TEST= 0
INDE  17  71  18  FOBS=   14.6  SIGMA=  22.9  PHAS=   150.9  FOM=  0.41  TEST= 0
INDE  17  71  20  FOBS=    0.0  SIGMA=  20.5  PHAS=     0.0  FOM=  0.00  TEST= 0
INDE  17  72  17  FOBS=   18.4  SIGMA=  15.0  PHAS=   130.4  FOM=  0.24  TEST= 0
INDE  17  72  19  FOBS=   61.3  SIGMA=   6.0  PHAS=    33.5  FOM=  0.86  TEST= 0
INDE  17  72  21  FOBS=   58.8  SIGMA=   3.8  PHAS=   -73.4  FOM=  0.78  TEST= 0
INDE  17  73  18  FOBS=    0.0  SIGMA=  25.7  PHAS=     0.0  FOM=  0.00  TEST= 0
INDE  17  73  20  FOBS=   91.9  SIGMA=   4.1  PHAS=   -98.8  FOM=  0.89  TEST= 0
INDE  18  18  18  FOBS=  235.0  SIGMA=   1.1  PHAS=    72.1  FOM=  0.92  TEST= 0
INDE  18  19  19  FOBS=  188.3  SIGMA=   0.7  PHAS=    15.5  FOM=  0.94  TEST= 0
INDE  18  19  21  FOBS=   33.2  SIGMA=   3.0  PHAS=   -27.3  FOM=  0.21  TEST= 0
INDE  18  19  23  FOBS=  163.6  SIGMA=   0.7  PHAS=   106.0  FOM=  0.96  TEST= 0
INDE  18  19  25  FOBS=   88.0  SIGMA=   1.2  PHAS=   156.5  FOM=  0.96  TEST= 0
INDE  18  19  27  FOBS=  154.6  SIGMA=   0.9  PHAS=   123.7  FOM=  0.75  TEST= 0
INDE  18  19  29  FOBS=  151.4  SIGMA=   1.0  PHAS=    31.1  FOM=  0.99  TEST= 0
INDE  18  19  31  FOBS=   65.3  SIGMA=   2.4  PHAS=   -53.5  FOM=  0.95  TEST= 0
INDE  18  19  33  FOBS=  147.4  SIGMA=   1.1  PHAS=  -121.3  FOM=  0.91  TEST= 0
INDE  18  19  35  FOBS=  246.2  SIGMA=   0.8  PHAS=  -133.9  FOM=  0.94  TEST= 0
INDE  18  19  37  FOBS=  203.6  SIGMA=   0.9  PHAS=   176.7  FOM=  0.93  TEST= 0
INDE  18  19  39  FOBS=   61.9  SIGMA=   2.7  PHAS=   136.3  FOM=  0.86  TEST= 0
INDE  18  19  41  FOBS=  281.1  SIGMA=   0.8  PHAS=  -142.3  FOM=  0.95  TEST= 0
INDE  18  19  43  FOBS=  144.5  SIGMA=   1.4  PHAS=   134.7  FOM=  0.96  TEST= 0
INDE  18  19  45  FOBS=   12.6  SIGMA=  13.8  PHAS=    48.3  FOM=  0.07  TEST= 0
INDE  18  19  47  FOBS=   27.4  SIGMA=   6.8  PHAS=   120.0  FOM=  0.09  TEST= 1
INDE  18  19  49  FOBS=   69.3  SIGMA=   2.9  PHAS=   121.2  FOM=  0.65  TEST= 0
INDE  18  19  51  FOBS=  124.3  SIGMA=   1.6  PHAS=     1.6  FOM=  0.75  TEST= 1
INDE  18  19  53  FOBS=   49.2  SIGMA=   4.6  PHAS=  -152.9  FOM=  0.41  TEST= 0
INDE  18  19  55  FOBS=   59.9  SIGMA=   3.2  PHAS=   -55.2  FOM=  0.61  TEST= 0
INDE  18  19  57  FOBS=  119.4  SIGMA=   1.9  PHAS=     3.1  FOM=  0.94  TEST= 0
INDE  18  19  59  FOBS=   63.0  SIGMA=   3.8  PHAS=    13.9  FOM=  0.82  TEST= 0
INDE  18  19  61  FOBS=   43.0  SIGMA=   5.9  PHAS=  -169.7  FOM=  0.42  TEST= 0
INDE  18  19  63  FOBS=   32.2  SIGMA=   7.9  PHAS=   123.4  FOM=  0.22  TEST= 0
INDE  18  19  65  FOBS=    9.5  SIGMA=  31.1  PHAS=    23.3  FOM=  0.12  TEST= 0
INDE  18  19  67  FOBS=   57.1  SIGMA=   6.3  PHAS=   -64.7  FOM=  0.77  TEST= 0
INDE  18  19  69  FOBS=    0.0  SIGMA=  26.5  PHAS=     0.0  FOM=  0.00  TEST= 0
INDE  18  19  71  FOBS=   65.8  SIGMA=   4.8  PHAS=    -1.8  FOM=  0.84  TEST= 0
INDE  18  19  73  FOBS=   75.6  SIGMA=   4.0  PHAS=   -18.1  FOM=  0.88  TEST= 0
INDE  18  20  18  FOBS=  135.0  SIGMA=   0.7  PHAS=   103.8  FOM=  0.99  TEST= 0
INDE  18  20  20  FOBS=   64.6  SIGMA=   1.4  PHAS=   -85.7  FOM=  0.94  TEST= 0
INDE  18  20  22  FOBS=  166.4  SIGMA=   0.6  PHAS=  -109.9  FOM=  0.98  TEST= 0
INDE  18  20  24  FOBS=  130.0  SIGMA=   0.7  PHAS=     6.2  FOM=  0.94  TEST= 0
INDE  18  20  26  FOBS=  234.0  SIGMA=   0.5  PHAS=    -9.7  FOM=  0.99  TEST= 0
INDE  18  20  28  FOBS=  144.2  SIGMA=   0.8  PHAS=   -74.9  FOM=  0.95  TEST= 0
INDE  18  20  30  FOBS=  367.5  SIGMA=   0.6  PHAS=   -84.8  FOM=  0.96  TEST= 0
INDE  18  20  32  FOBS=  249.6  SIGMA=   0.7  PHAS=    74.2  FOM=  0.97  TEST= 0
INDE  18  20  34  FOBS=  182.0  SIGMA=   0.9  PHAS=   173.8  FOM=  0.99  TEST= 0
INDE  18  20  36  FOBS=  252.0  SIGMA=   0.6  PHAS=  -168.8  FOM=  0.98  TEST= 0
INDE  18  20  38  FOBS=  167.5  SIGMA=   0.9  PHAS=   121.7  FOM=  0.98  TEST= 0
INDE  18  20  40  FOBS=  200.3  SIGMA=   0.8  PHAS=   120.7  FOM=  0.96  TEST= 0
INDE  18  20  42  FOBS=  193.7  SIGMA=   0.9  PHAS=    47.4  FOM=  0.94  TEST= 0
INDE  18  20  44  FOBS=   31.8  SIGMA=   5.1  PHAS=   113.5  FOM=  0.56  TEST= 0
INDE  18  20  46  FOBS=  162.9  SIGMA=   1.1  PHAS=   167.1  FOM=  0.90  TEST= 0
INDE  18  20  48  FOBS=    0.0  SIGMA=  19.3  PHAS=     0.0  FOM=  0.00  TEST= 0
INDE  18  20  50  FOBS=   58.9  SIGMA=   3.4  PHAS=  -176.5  FOM=  0.88  TEST= 0
INDE  18  20  52  FOBS=   57.4  SIGMA=   3.4  PHAS=  -177.5  FOM=  0.86  TEST= 0
INDE  18  20  54  FOBS=   76.0  SIGMA=   2.6  PHAS=  -172.2  FOM=  0.91  TEST= 0
INDE  18  20  56  FOBS=   87.8  SIGMA=   2.2  PHAS=   -42.7  FOM=  0.81  TEST= 0
INDE  18  20  58  FOBS=   51.8  SIGMA=   4.2  PHAS=   156.1  FOM=  0.51  TEST= 0
```

*FIG. 12A - 409*

```
INDE 18 20 60 FOBS=   120.7 SIGMA=  2.2 PHAS=    5.1 FOM= 0.88 TEST= 0
INDE 18 20 62 FOBS=    70.4 SIGMA=  3.7 PHAS=  -11.2 FOM= 0.82 TEST= 0
INDE 18 20 64 FOBS=    64.0 SIGMA=  4.0 PHAS=   65.8 FOM= 0.58 TEST= 0
INDE 18 20 66 FOBS=    91.5 SIGMA=  3.3 PHAS= -156.4 FOM= 0.90 TEST= 0
INDE 18 20 68 FOBS=     0.0 SIGMA= 26.7 PHAS=    0.0 FOM= 0.00 TEST= 0
INDE 18 20 70 FOBS=    87.3 SIGMA=  3.7 PHAS=  -33.9 FOM= 0.92 TEST= 0
INDE 18 20 72 FOBS=    73.4 SIGMA=  4.3 PHAS= -110.0 FOM= 0.85 TEST= 0
INDE 18 21 19 FOBS=    88.6 SIGMA=  1.1 PHAS=   77.7 FOM= 0.84 TEST= 0
INDE 18 21 21 FOBS=   302.8 SIGMA=  0.5 PHAS= -169.4 FOM= 0.99 TEST= 0
INDE 18 21 23 FOBS=   253.3 SIGMA=  0.5 PHAS=  171.6 FOM= 0.96 TEST= 0
INDE 18 21 25 FOBS=   157.2 SIGMA=  0.6 PHAS=  -94.7 FOM= 0.97 TEST= 0
INDE 18 21 27 FOBS=    53.0 SIGMA=  1.8 PHAS=  121.6 FOM= 0.57 TEST= 1
INDE 18 21 29 FOBS=   185.0 SIGMA=  0.7 PHAS= -174.1 FOM= 0.99 TEST= 0
INDE 18 21 31 FOBS=   181.5 SIGMA=  0.7 PHAS= -129.0 FOM= 0.94 TEST= 1
INDE 18 21 33 FOBS=   125.0 SIGMA=  1.1 PHAS= -124.7 FOM= 0.96 TEST= 0
INDE 18 21 35 FOBS=   190.0 SIGMA=  0.8 PHAS=  134.9 FOM= 0.99 TEST= 0
INDE 18 21 37 FOBS=   211.7 SIGMA=  0.7 PHAS=  116.8 FOM= 0.92 TEST= 0
INDE 18 21 39 FOBS=    54.5 SIGMA=  2.7 PHAS=    0.5 FOM= 0.84 TEST= 0
INDE 18 21 41 FOBS=    72.3 SIGMA=  2.0 PHAS=    0.8 FOM= 0.89 TEST= 0
INDE 18 21 43 FOBS=     0.0 SIGMA= 17.1 PHAS=    0.0 FOM= 0.00 TEST= 0
INDE 18 21 45 FOBS=     0.0 SIGMA= 17.3 PHAS=    0.0 FOM= 0.00 TEST= 0
INDE 18 21 47 FOBS=   146.2 SIGMA=  1.3 PHAS=   63.2 FOM= 0.86 TEST= 0
INDE 18 21 49 FOBS=   166.0 SIGMA=  1.2 PHAS=  129.0 FOM= 0.94 TEST= 0
INDE 18 21 51 FOBS=    56.2 SIGMA=  3.6 PHAS=  -53.5 FOM= 0.84 TEST= 1
INDE 18 21 53 FOBS=    18.8 SIGMA= 10.3 PHAS=  167.3 FOM= 0.36 TEST= 0
INDE 18 21 55 FOBS=     0.0 SIGMA= 19.5 PHAS=    0.0 FOM= 0.00 TEST= 0
INDE 18 21 57 FOBS=    99.4 SIGMA=  2.3 PHAS=   37.2 FOM= 0.90 TEST= 0
INDE 18 21 59 FOBS=   133.2 SIGMA=  2.1 PHAS=  -64.7 FOM= 0.95 TEST= 0
INDE 18 21 61 FOBS=    20.8 SIGMA= 12.5 PHAS= -101.3 FOM= 0.03 TEST= 0
INDE 18 21 63 FOBS=    35.2 SIGMA=  7.4 PHAS= -132.1 FOM= 0.58 TEST= 0
INDE 18 21 65 FOBS=    33.9 SIGMA=  7.6 PHAS=   84.8 FOM= 0.44 TEST= 0
INDE 18 21 67 FOBS=    27.3 SIGMA= 12.3 PHAS=   -2.5 FOM= 0.37 TEST= 0
INDE 18 21 69 FOBS=    65.7 SIGMA=  5.1 PHAS=  -85.4 FOM= 0.84 TEST= 0
INDE 18 21 71 FOBS=    58.4 SIGMA=  5.7 PHAS= -132.9 FOM= 0.86 TEST= 0
INDE 18 22 18 FOBS=   137.5 SIGMA=  0.7 PHAS=  175.5 FOM= 0.44 TEST= 0
INDE 18 22 20 FOBS=   238.3 SIGMA=  0.5 PHAS=  137.4 FOM= 0.95 TEST= 0
INDE 18 22 22 FOBS=   224.9 SIGMA=  0.6 PHAS=  157.3 FOM= 0.94 TEST= 0
INDE 18 22 24 FOBS=   178.4 SIGMA=  0.6 PHAS=   73.9 FOM= 0.98 TEST= 0
INDE 18 22 26 FOBS=   292.4 SIGMA=  0.5 PHAS=  -86.0 FOM= 0.92 TEST= 0
INDE 18 22 28 FOBS=   230.8 SIGMA=  0.6 PHAS=  -81.7 FOM= 0.98 TEST= 0
INDE 18 22 30 FOBS=   141.7 SIGMA=  0.9 PHAS=  108.9 FOM= 0.82 TEST= 0
INDE 18 22 32 FOBS=   294.0 SIGMA=  0.6 PHAS=  123.2 FOM= 0.95 TEST= 0
INDE 18 22 34 FOBS=   114.0 SIGMA=  1.3 PHAS=   55.5 FOM= 0.98 TEST= 0
INDE 18 22 36 FOBS=    31.0 SIGMA=  4.8 PHAS= -143.5 FOM= 0.63 TEST= 0
INDE 18 22 38 FOBS=   209.9 SIGMA=  0.9 PHAS= -178.8 FOM= 0.93 TEST= 0
INDE 18 22 40 FOBS=    77.0 SIGMA=  1.9 PHAS=  -28.8 FOM= 0.65 TEST= 0
INDE 18 22 42 FOBS=   157.3 SIGMA=  1.0 PHAS=   -3.4 FOM= 0.93 TEST= 0
INDE 18 22 44 FOBS=   109.8 SIGMA=  1.4 PHAS=  133.9 FOM= 0.81 TEST= 0
INDE 18 22 46 FOBS=    99.0 SIGMA=  1.6 PHAS=  171.7 FOM= 0.80 TEST= 0
INDE 18 22 48 FOBS=    69.7 SIGMA=  2.4 PHAS=  -25.7 FOM= 0.89 TEST= 0
INDE 18 22 50 FOBS=   120.6 SIGMA=  1.4 PHAS=   11.3 FOM= 0.78 TEST= 0
INDE 18 22 52 FOBS=    24.9 SIGMA=  8.4 PHAS=   92.6 FOM= 0.07 TEST= 0
INDE 18 22 54 FOBS=    36.9 SIGMA=  5.3 PHAS=  -67.1 FOM= 0.11 TEST= 1
INDE 18 22 56 FOBS=    93.1 SIGMA=  2.5 PHAS=  -80.7 FOM= 0.89 TEST= 0
INDE 18 22 58 FOBS=   165.7 SIGMA=  1.8 PHAS= -131.7 FOM= 0.97 TEST= 0
INDE 18 22 60 FOBS=    14.4 SIGMA= 18.6 PHAS=  105.9 FOM= 0.18 TEST= 0
INDE 18 22 62 FOBS=    79.9 SIGMA=  3.4 PHAS=   24.9 FOM= 0.91 TEST= 0
INDE 18 22 64 FOBS=    45.2 SIGMA=  5.7 PHAS=  115.7 FOM= 0.77 TEST= 0
INDE 18 22 66 FOBS=    19.2 SIGMA= 17.9 PHAS=   18.6 FOM= 0.05 TEST= 1
INDE 18 22 68 FOBS=    22.7 SIGMA= 15.1 PHAS= -133.2 FOM= 0.45 TEST= 1
INDE 18 22 70 FOBS=    44.5 SIGMA=  7.6 PHAS= -141.3 FOM= 0.48 TEST= 0
INDE 18 23 19 FOBS=   359.8 SIGMA=  0.5 PHAS=   89.3 FOM= 0.97 TEST= 0
INDE 18 23 21 FOBS=   238.0 SIGMA=  0.6 PHAS=   85.9 FOM= 0.98 TEST= 0
INDE 18 23 23 FOBS=   231.4 SIGMA=  0.6 PHAS=  152.2 FOM= 0.99 TEST= 0
INDE 18 23 25 FOBS=   258.2 SIGMA=  0.5 PHAS=   99.1 FOM= 0.96 TEST= 0
INDE 18 23 27 FOBS=   324.1 SIGMA=  0.5 PHAS=  134.4 FOM= 0.97 TEST= 0
INDE 18 23 29 FOBS=   167.1 SIGMA=  0.8 PHAS=  -47.0 FOM= 0.34 TEST= 1
INDE 18 23 31 FOBS=   180.3 SIGMA=  0.8 PHAS=   29.3 FOM= 0.90 TEST= 0
INDE 18 23 33 FOBS=   156.2 SIGMA=  1.0 PHAS=  167.2 FOM= 0.65 TEST= 0
INDE 18 23 35 FOBS=   150.3 SIGMA=  1.2 PHAS= -142.5 FOM= 0.88 TEST= 0
```

*FIG. 12A - 410*

```
INDE  18  23  37  FOBS=   192.8  SIGMA=   0.9  PHAS=   60.6  FOM=  0.91  TEST=  0
INDE  18  23  39  FOBS=   256.7  SIGMA=   0.8  PHAS=   32.8  FOM=  0.93  TEST=  0
INDE  18  23  41  FOBS=    87.7  SIGMA=   1.7  PHAS=  139.1  FOM=  0.88  TEST=  1
INDE  18  23  43  FOBS=   130.4  SIGMA=   1.1  PHAS= -125.5  FOM=  0.91  TEST=  0
INDE  18  23  45  FOBS=   113.4  SIGMA=   1.4  PHAS=   95.4  FOM=  0.88  TEST=  0
INDE  18  23  47  FOBS=   225.5  SIGMA=   0.8  PHAS=   41.6  FOM=  0.95  TEST=  0
INDE  18  23  49  FOBS=    96.3  SIGMA=   1.7  PHAS= -105.5  FOM=  0.74  TEST=  0
INDE  18  23  51  FOBS=   168.0  SIGMA=   1.0  PHAS= -102.3  FOM=  0.94  TEST=  0
INDE  18  23  53  FOBS=   144.7  SIGMA=   1.2  PHAS= -119.1  FOM=  0.93  TEST=  0
INDE  18  23  55  FOBS=    65.4  SIGMA=   3.0  PHAS=  144.0  FOM=  0.87  TEST=  1
INDE  18  23  57  FOBS=   189.5  SIGMA=   1.6  PHAS=  130.2  FOM=  0.97  TEST=  0
INDE  18  23  59  FOBS=    13.6  SIGMA=  20.2  PHAS=  142.8  FOM=  0.15  TEST=  0
INDE  18  23  61  FOBS=    50.7  SIGMA=   5.3  PHAS=   13.4  FOM=  0.28  TEST=  0
INDE  18  23  63  FOBS=   127.8  SIGMA=   2.1  PHAS=  -44.5  FOM=  0.94  TEST=  0
INDE  18  23  65  FOBS=    43.6  SIGMA=   7.0  PHAS=   78.5  FOM=  0.18  TEST=  0
INDE  18  23  67  FOBS=   115.2  SIGMA=   3.2  PHAS=   17.1  FOM=  0.92  TEST=  0
INDE  18  23  69  FOBS=     0.0  SIGMA=  25.6  PHAS=    0.0  FOM=  0.00  TEST=  0
INDE  18  24  18  FOBS=    94.2  SIGMA=   1.1  PHAS=  -62.4  FOM=  0.98  TEST=  0
INDE  18  24  20  FOBS=   321.9  SIGMA=   0.5  PHAS=  -25.7  FOM=  0.97  TEST=  0
INDE  18  24  22  FOBS=   268.1  SIGMA=   0.6  PHAS=   -4.2  FOM=  0.93  TEST=  0
INDE  18  24  24  FOBS=   295.0  SIGMA=   0.6  PHAS=   -7.9  FOM=  0.94  TEST=  0
INDE  18  24  26  FOBS=   347.2  SIGMA=   0.5  PHAS=    5.3  FOM=  0.97  TEST=  0
INDE  18  24  28  FOBS=   164.0  SIGMA=   0.8  PHAS=  -25.8  FOM=  0.87  TEST=  0
INDE  18  24  30  FOBS=    80.1  SIGMA=   1.6  PHAS=  157.0  FOM=  0.48  TEST=  0
INDE  18  24  32  FOBS=   114.4  SIGMA=   1.2  PHAS= -133.3  FOM=  0.96  TEST=  0
INDE  18  24  34  FOBS=   107.7  SIGMA=   1.5  PHAS=   42.2  FOM=  0.92  TEST=  0
INDE  18  24  36  FOBS=   115.9  SIGMA=   1.5  PHAS= -148.7  FOM=  0.82  TEST=  0
INDE  18  24  38  FOBS=   182.4  SIGMA=   1.0  PHAS= -113.3  FOM=  0.98  TEST=  0
INDE  18  24  40  FOBS=   143.5  SIGMA=   1.2  PHAS=  -16.7  FOM=  0.94  TEST=  0
INDE  18  24  42  FOBS=   198.8  SIGMA=   0.8  PHAS=    7.9  FOM=  0.95  TEST=  0
INDE  18  24  44  FOBS=    95.3  SIGMA=   1.6  PHAS= -156.7  FOM=  0.70  TEST=  1
INDE  18  24  46  FOBS=   105.1  SIGMA=   1.5  PHAS=  143.8  FOM=  0.53  TEST=  0
INDE  18  24  48  FOBS=    65.8  SIGMA=   2.3  PHAS= -129.6  FOM=  0.86  TEST=  0
INDE  18  24  50  FOBS=    41.1  SIGMA=   3.7  PHAS= -129.2  FOM=  0.59  TEST=  0
INDE  18  24  52  FOBS=    29.1  SIGMA=   5.8  PHAS=  169.9  FOM=  0.68  TEST=  0
INDE  18  24  54  FOBS=   146.2  SIGMA=   1.1  PHAS=   86.3  FOM=  0.95  TEST=  0
INDE  18  24  56  FOBS=   117.5  SIGMA=   1.7  PHAS=   11.3  FOM=  0.95  TEST=  0
INDE  18  24  58  FOBS=     0.0  SIGMA=  22.2  PHAS=    0.0  FOM=  0.00  TEST=  0
INDE  18  24  60  FOBS=    73.3  SIGMA=   3.7  PHAS=   39.9  FOM=  0.79  TEST=  0
INDE  18  24  62  FOBS=    42.0  SIGMA=   6.3  PHAS= -159.2  FOM=  0.61  TEST=  0
INDE  18  24  64  FOBS=    86.5  SIGMA=   3.6  PHAS= -153.2  FOM=  0.85  TEST=  0
INDE  18  24  66  FOBS=    79.2  SIGMA=   4.7  PHAS=   -8.6  FOM=  0.15  TEST=  1
INDE  18  24  68  FOBS=    89.9  SIGMA=   3.8  PHAS= -114.1  FOM=  0.54  TEST=  1
INDE  18  25  19  FOBS=   108.8  SIGMA=   1.0  PHAS=  153.8  FOM=  0.95  TEST=  0
INDE  18  25  21  FOBS=   237.0  SIGMA=   0.6  PHAS= -134.3  FOM=  0.99  TEST=  0
INDE  18  25  23  FOBS=   328.0  SIGMA=   0.5  PHAS= -157.0  FOM=  0.97  TEST=  0
INDE  18  25  25  FOBS=   116.6  SIGMA=   1.0  PHAS=    6.7  FOM=  0.89  TEST=  0
INDE  18  25  27  FOBS=   128.3  SIGMA=   1.0  PHAS= -137.7  FOM=  0.79  TEST=  0
INDE  18  25  29  FOBS=    58.2  SIGMA=   2.1  PHAS=   34.1  FOM=  0.71  TEST=  0
INDE  18  25  31  FOBS=   182.4  SIGMA=   0.9  PHAS=   91.7  FOM=  0.97  TEST=  0
INDE  18  25  33  FOBS=   240.0  SIGMA=   0.7  PHAS= -174.1  FOM=  0.95  TEST=  0
INDE  18  25  35  FOBS=   138.1  SIGMA=   1.2  PHAS= -156.7  FOM=  0.96  TEST=  0
INDE  18  25  37  FOBS=   144.8  SIGMA=   1.2  PHAS=   96.6  FOM=  0.89  TEST=  0
INDE  18  25  39  FOBS=    47.5  SIGMA=   3.5  PHAS=  -46.2  FOM=  0.96  TEST=  1
INDE  18  25  41  FOBS=   194.4  SIGMA=   0.9  PHAS=  -49.5  FOM=  0.89  TEST=  0
INDE  18  25  43  FOBS=   151.3  SIGMA=   1.2  PHAS= -151.7  FOM=  0.88  TEST=  0
INDE  18  25  45  FOBS=   140.7  SIGMA=   1.2  PHAS=   85.8  FOM=  0.91  TEST=  0
INDE  18  25  47  FOBS=   136.6  SIGMA=   1.2  PHAS=   68.3  FOM=  0.90  TEST=  1
INDE  18  25  49  FOBS=    76.3  SIGMA=   2.0  PHAS=  -89.5  FOM=  0.48  TEST=  0
INDE  18  25  51  FOBS=   113.3  SIGMA=   1.4  PHAS=  -98.7  FOM=  0.97  TEST=  0
INDE  18  25  53  FOBS=   152.2  SIGMA=   1.1  PHAS=  -72.6  FOM=  0.94  TEST=  0
INDE  18  25  55  FOBS=    74.2  SIGMA=   2.1  PHAS=  -64.6  FOM=  0.91  TEST=  0
INDE  18  25  57  FOBS=    65.6  SIGMA=   3.4  PHAS=   95.0  FOM=  0.86  TEST=  0
INDE  18  25  59  FOBS=     0.0  SIGMA=  21.7  PHAS=    0.0  FOM=  0.00  TEST=  0
INDE  18  25  61  FOBS=    36.5  SIGMA=   6.5  PHAS=   59.0  FOM=  0.53  TEST=  0
INDE  18  25  63  FOBS=    39.5  SIGMA=   6.8  PHAS=   23.1  FOM=  0.41  TEST=  0
INDE  18  25  65  FOBS=    55.1  SIGMA=   6.6  PHAS=  141.5  FOM=  0.88  TEST=  0
INDE  18  25  67  FOBS=     0.0  SIGMA=  26.1  PHAS=    0.0  FOM=  0.00  TEST=  0
INDE  18  26  18  FOBS=   158.0  SIGMA=   0.8  PHAS=  115.3  FOM=  0.40  TEST=  1
INDE  18  26  20  FOBS=    71.4  SIGMA=   1.5  PHAS= -121.8  FOM=  0.88  TEST=  0
```

*FIG. 12A - 411*

```
INDE  18  26  22  FOBS=   222.1  SIGMA=   0.6  PHAS=   56.4  FOM=  0.95  TEST= 0
INDE  18  26  24  FOBS=   215.4  SIGMA=   0.7  PHAS=  -60.1  FOM=  0.90  TEST= 1
INDE  18  26  26  FOBS=   214.1  SIGMA=   0.6  PHAS=  -48.0  FOM=  0.92  TEST= 0
INDE  18  26  28  FOBS=   148.9  SIGMA=   0.9  PHAS=   56.1  FOM=  0.92  TEST= 0
INDE  18  26  30  FOBS=    56.8  SIGMA=   2.5  PHAS=   14.5  FOM=  0.82  TEST= 0
INDE  18  26  32  FOBS=    84.8  SIGMA=   1.9  PHAS=  -20.0  FOM=  0.93  TEST= 0
INDE  18  26  34  FOBS=   231.5  SIGMA=   0.8  PHAS=   92.3  FOM=  0.95  TEST= 0
INDE  18  26  36  FOBS=    64.8  SIGMA=   2.6  PHAS=  118.9  FOM=  0.62  TEST= 0
INDE  18  26  38  FOBS=   145.9  SIGMA=   1.2  PHAS=  -45.1  FOM=  0.92  TEST= 1
INDE  18  26  40  FOBS=    42.8  SIGMA=   3.8  PHAS= -123.4  FOM=  0.55  TEST= 1
INDE  18  26  42  FOBS=    75.9  SIGMA=   2.3  PHAS=   18.4  FOM=  0.74  TEST= 0
INDE  18  26  44  FOBS=    67.1  SIGMA=   2.6  PHAS=  119.0  FOM=  0.55  TEST= 0
INDE  18  26  46  FOBS=   235.8  SIGMA=   0.8  PHAS=  -66.1  FOM=  0.96  TEST= 0
INDE  18  26  48  FOBS=     0.0  SIGMA=  18.5  PHAS=    0.0  FOM=  0.00  TEST= 0
INDE  18  26  50  FOBS=    51.8  SIGMA=   3.1  PHAS=  160.2  FOM=  0.85  TEST= 0
INDE  18  26  52  FOBS=    75.3  SIGMA=   2.0  PHAS= -104.0  FOM=  0.71  TEST= 0
INDE  18  26  54  FOBS=   114.7  SIGMA=   1.4  PHAS=  155.2  FOM=  0.92  TEST= 0
INDE  18  26  56  FOBS=    86.4  SIGMA=   2.1  PHAS=  -19.8  FOM=  0.86  TEST= 0
INDE  18  26  58  FOBS=     0.0  SIGMA=  20.8  PHAS=    0.0  FOM=  0.00  TEST= 0
INDE  18  26  60  FOBS=    57.3  SIGMA=   3.8  PHAS=   51.7  FOM=  0.65  TEST= 0
INDE  18  26  62  FOBS=    20.3  SIGMA=  10.6  PHAS=   67.2  FOM=  0.16  TEST= 0
INDE  18  26  64  FOBS=    16.5  SIGMA=  21.9  PHAS=   23.0  FOM=  0.21  TEST= 0
INDE  18  26  66  FOBS=    80.2  SIGMA=   4.5  PHAS=   33.3  FOM=  0.91  TEST= 0
INDE  18  27  19  FOBS=     0.0  SIGMA=  15.3  PHAS=    0.0  FOM=  0.00  TEST= 0
INDE  18  27  21  FOBS=   110.2  SIGMA=   1.1  PHAS= -119.1  FOM=  0.60  TEST= 0
INDE  18  27  23  FOBS=   297.6  SIGMA=   0.6  PHAS= -151.5  FOM=  0.93  TEST= 0
INDE  18  27  25  FOBS=    82.7  SIGMA=   1.6  PHAS=    3.3  FOM=  0.92  TEST= 0
INDE  18  27  27  FOBS=   166.6  SIGMA=   0.8  PHAS=  -96.4  FOM=  0.95  TEST= 0
INDE  18  27  29  FOBS=   107.7  SIGMA=   1.3  PHAS= -110.4  FOM=  0.88  TEST= 0
INDE  18  27  31  FOBS=    33.9  SIGMA=   4.7  PHAS=  174.0  FOM=  0.42  TEST= 0
INDE  18  27  33  FOBS=    31.9  SIGMA=   5.3  PHAS=   38.5  FOM=  0.20  TEST= 0
INDE  18  27  35  FOBS=   193.8  SIGMA=   1.0  PHAS=   49.3  FOM=  0.93  TEST= 0
INDE  18  27  37  FOBS=    69.7  SIGMA=   2.6  PHAS=  -53.0  FOM=  0.68  TEST= 0
INDE  18  27  39  FOBS=     0.0  SIGMA=  18.5  PHAS=    0.0  FOM=  0.00  TEST= 0
INDE  18  27  41  FOBS=   226.5  SIGMA=   0.9  PHAS=   65.9  FOM=  0.96  TEST= 0
INDE  18  27  43  FOBS=    99.6  SIGMA=   1.7  PHAS= -139.6  FOM=  0.80  TEST= 0
INDE  18  27  45  FOBS=   187.9  SIGMA=   1.0  PHAS= -156.9  FOM=  0.85  TEST= 1
INDE  18  27  47  FOBS=   261.5  SIGMA=   0.8  PHAS=  164.6  FOM=  0.96  TEST= 0
INDE  18  27  49  FOBS=    65.4  SIGMA=   2.3  PHAS=  -64.4  FOM=  0.07  TEST= 1
INDE  18  27  51  FOBS=    44.1  SIGMA=   3.3  PHAS= -135.1  FOM=  0.60  TEST= 0
INDE  18  27  53  FOBS=    58.4  SIGMA=   2.5  PHAS=  -74.3  FOM=  0.71  TEST= 0
INDE  18  27  55  FOBS=    53.7  SIGMA=   3.2  PHAS=  164.0  FOM=  0.81  TEST= 0
INDE  18  27  57  FOBS=    46.5  SIGMA=   4.1  PHAS=   80.1  FOM=  0.79  TEST= 0
INDE  18  27  59  FOBS=    40.5  SIGMA=   5.0  PHAS=  130.1  FOM=  0.84  TEST= 0
INDE  18  27  61  FOBS=    19.5  SIGMA=  10.9  PHAS=   72.5  FOM=  0.57  TEST= 0
INDE  18  27  63  FOBS=    95.7  SIGMA=   2.5  PHAS=   -5.9  FOM=  0.88  TEST= 0
INDE  18  27  65  FOBS=    38.1  SIGMA=   7.8  PHAS= -105.4  FOM=  0.44  TEST= 0
INDE  18  28  18  FOBS=   216.8  SIGMA=   0.7  PHAS=  158.9  FOM=  0.98  TEST= 0
INDE  18  28  20  FOBS=    88.9  SIGMA=   1.3  PHAS=  165.3  FOM=  0.67  TEST= 0
INDE  18  28  22  FOBS=   211.1  SIGMA=   0.7  PHAS=   52.9  FOM=  0.95  TEST= 0
INDE  18  28  24  FOBS=   374.0  SIGMA=   0.6  PHAS= -109.3  FOM=  0.98  TEST= 0
INDE  18  28  26  FOBS=   277.6  SIGMA=   0.6  PHAS=  -99.7  FOM=  0.96  TEST= 0
INDE  18  28  28  FOBS=   277.2  SIGMA=   0.6  PHAS=   82.7  FOM=  0.99  TEST= 0
INDE  18  28  30  FOBS=    78.3  SIGMA=   1.8  PHAS=  -86.8  FOM=  0.19  TEST= 0
INDE  18  28  32  FOBS=   152.9  SIGMA=   1.2  PHAS=   10.7  FOM=  0.97  TEST= 0
INDE  18  28  34  FOBS=    84.2  SIGMA=   2.2  PHAS=  -15.6  FOM=  0.92  TEST= 1
INDE  18  28  36  FOBS=   154.0  SIGMA=   1.3  PHAS=  -62.1  FOM=  0.90  TEST= 0
INDE  18  28  38  FOBS=   161.7  SIGMA=   1.1  PHAS=   22.6  FOM=  0.46  TEST= 0
INDE  18  28  40  FOBS=   209.9  SIGMA=   0.9  PHAS=   25.7  FOM=  0.95  TEST= 0
INDE  18  28  42  FOBS=    58.7  SIGMA=   2.9  PHAS=  -48.1  FOM=  0.88  TEST= 0
INDE  18  28  44  FOBS=    89.2  SIGMA=   1.9  PHAS=  167.3  FOM=  0.64  TEST= 0
INDE  18  28  46  FOBS=   160.7  SIGMA=   1.1  PHAS=  128.5  FOM=  0.94  TEST= 0
INDE  18  28  48  FOBS=    95.0  SIGMA=   1.8  PHAS=   23.7  FOM=  0.93  TEST= 0
INDE  18  28  50  FOBS=    97.9  SIGMA=   1.7  PHAS=  -99.4  FOM=  0.16  TEST= 1
INDE  18  28  52  FOBS=   124.7  SIGMA=   1.2  PHAS= -175.4  FOM=  0.96  TEST= 0
INDE  18  28  54  FOBS=    27.6  SIGMA=   5.8  PHAS=    2.7  FOM=  0.32  TEST= 0
INDE  18  28  56  FOBS=    83.6  SIGMA=   2.2  PHAS=  -46.6  FOM=  0.89  TEST= 0
INDE  18  28  58  FOBS=    55.3  SIGMA=   3.4  PHAS= -110.5  FOM=  0.67  TEST= 0
INDE  18  28  60  FOBS=    15.9  SIGMA=  12.7  PHAS=  -22.6  FOM=  0.43  TEST= 0
INDE  18  28  62  FOBS=    46.8  SIGMA=   5.1  PHAS=  -62.0  FOM=  0.89  TEST= 0
```

*FIG. 12A - 412*

```
INDE  18  28  64  FOBS=   36.9  SIGMA=   8.0  PHAS=  -144.0  FOM=  0.63  TEST=  0
INDE  18  28  66  FOBS=   54.1  SIGMA=  10.0  PHAS=    39.7  FOM=  0.72  TEST=  0
INDE  18  28  68  FOBS=   40.4  SIGMA=  13.9  PHAS=   -31.1  FOM=  0.52  TEST=  0
INDE  18  29  19  FOBS=  203.0  SIGMA=   0.7  PHAS=    53.4  FOM=  0.98  TEST=  0
INDE  18  29  21  FOBS=   88.4  SIGMA=   1.4  PHAS=   120.9  FOM=  0.85  TEST=  0
INDE  18  29  23  FOBS=  271.3  SIGMA=   0.6  PHAS=    79.7  FOM=  0.99  TEST=  0
INDE  18  29  25  FOBS=  307.5  SIGMA=   0.6  PHAS=   133.7  FOM=  0.95  TEST=  1
INDE  18  29  27  FOBS=  138.1  SIGMA=   1.1  PHAS=   179.5  FOM=  0.95  TEST=  0
INDE  18  29  29  FOBS=    0.0  SIGMA=  17.0  PHAS=     0.0  FOM=  0.00  TEST=  0
INDE  18  29  31  FOBS=  199.2  SIGMA=   0.9  PHAS=   -53.2  FOM=  0.91  TEST=  1
INDE  18  29  33  FOBS=  173.1  SIGMA=   1.1  PHAS=   -52.6  FOM=  0.97  TEST=  0
INDE  18  29  35  FOBS=  172.0  SIGMA=   1.2  PHAS=   161.9  FOM=  0.92  TEST=  0
INDE  18  29  37  FOBS=  187.4  SIGMA=   1.1  PHAS=   -65.5  FOM=  0.93  TEST=  0
INDE  18  29  39  FOBS=   49.7  SIGMA=   3.8  PHAS=    30.7  FOM=  0.56  TEST=  0
INDE  18  29  41  FOBS=   97.8  SIGMA=   1.8  PHAS=  -144.0  FOM=  0.76  TEST=  0
INDE  18  29  43  FOBS=  155.4  SIGMA=   1.2  PHAS=  -174.4  FOM=  0.89  TEST=  0
INDE  18  29  45  FOBS=   90.5  SIGMA=   1.9  PHAS=    64.5  FOM=  0.90  TEST=  0
INDE  18  29  47  FOBS=  171.7  SIGMA=   1.0  PHAS=   141.1  FOM=  0.96  TEST=  0
INDE  18  29  49  FOBS=   65.8  SIGMA=   2.5  PHAS=  -171.9  FOM=  0.71  TEST=  0
INDE  18  29  51  FOBS=  103.3  SIGMA=   1.6  PHAS=   124.4  FOM=  0.95  TEST=  0
INDE  18  29  53  FOBS=   74.4  SIGMA=   2.1  PHAS=  -116.7  FOM=  0.88  TEST=  0
INDE  18  29  55  FOBS=  127.9  SIGMA=   1.4  PHAS=   175.1  FOM=  0.96  TEST=  0
INDE  18  29  57  FOBS=   18.3  SIGMA=  10.1  PHAS=    78.5  FOM=  0.44  TEST=  0
INDE  18  29  59  FOBS=   16.4  SIGMA=  11.4  PHAS=   122.8  FOM=  0.45  TEST=  0
INDE  18  29  61  FOBS=   34.1  SIGMA=   5.5  PHAS=  -173.9  FOM=  0.50  TEST=  0
INDE  18  29  63  FOBS=   36.5  SIGMA=   7.0  PHAS=   139.3  FOM=  0.49  TEST=  0
INDE  18  29  65  FOBS=   19.5  SIGMA=  27.8  PHAS=    50.6  FOM=  0.05  TEST=  0
INDE  18  29  67  FOBS=  119.3  SIGMA=   4.8  PHAS=  -138.1  FOM=  0.93  TEST=  0
INDE  18  29  69  FOBS=   38.5  SIGMA=  14.9  PHAS=  -157.6  FOM=  0.65  TEST=  0
INDE  18  30  18  FOBS=  281.3  SIGMA=   0.7  PHAS=   -52.5  FOM=  0.95  TEST=  0
INDE  18  30  20  FOBS=  127.7  SIGMA=   1.1  PHAS=    13.8  FOM=  0.97  TEST=  0
INDE  18  30  22  FOBS=  246.3  SIGMA=   0.7  PHAS=   -20.5  FOM=  0.98  TEST=  0
INDE  18  30  24  FOBS=  184.4  SIGMA=   0.8  PHAS=    -1.9  FOM=  0.96  TEST=  0
INDE  18  30  26  FOBS=  177.5  SIGMA=   0.9  PHAS=    75.8  FOM=  0.92  TEST=  0
INDE  18  30  28  FOBS=  231.7  SIGMA=   0.8  PHAS=    32.5  FOM=  0.94  TEST=  0
INDE  18  30  30  FOBS=  118.6  SIGMA=   1.3  PHAS=  -132.3  FOM=  0.91  TEST=  0
INDE  18  30  32  FOBS=   60.6  SIGMA=   2.7  PHAS=   -84.4  FOM=  0.88  TEST=  0
INDE  18  30  34  FOBS=  127.0  SIGMA=   1.5  PHAS=   -59.4  FOM=  0.85  TEST=  0
INDE  18  30  36  FOBS=   81.6  SIGMA=   2.4  PHAS=   -97.1  FOM=  0.64  TEST=  0
INDE  18  30  38  FOBS=   51.5  SIGMA=   3.9  PHAS=    81.6  FOM=  0.40  TEST=  0
INDE  18  30  40  FOBS=  276.1  SIGMA=   0.9  PHAS=    77.4  FOM=  0.96  TEST=  0
INDE  18  30  42  FOBS=  205.8  SIGMA=   0.9  PHAS=   128.6  FOM=  0.94  TEST=  0
INDE  18  30  44  FOBS=  126.1  SIGMA=   1.4  PHAS=    28.5  FOM=  0.94  TEST=  0
INDE  18  30  46  FOBS=  114.4  SIGMA=   1.5  PHAS=    27.1  FOM=  0.89  TEST=  0
INDE  18  30  48  FOBS=  146.2  SIGMA=   1.2  PHAS=    49.3  FOM=  0.97  TEST=  0
INDE  18  30  50  FOBS=   46.2  SIGMA=   3.5  PHAS=    47.8  FOM=  0.48  TEST=  1
INDE  18  30  52  FOBS=  128.0  SIGMA=   1.3  PHAS=   153.6  FOM=  0.94  TEST=  0
INDE  18  30  54  FOBS=   33.7  SIGMA=   5.1  PHAS=   -28.1  FOM=  0.16  TEST=  0
INDE  18  30  56  FOBS=   60.7  SIGMA=   3.0  PHAS=    45.7  FOM=  0.91  TEST=  0
INDE  18  30  58  FOBS=    0.0  SIGMA=  18.2  PHAS=     0.0  FOM=  0.00  TEST=  0
INDE  18  30  60  FOBS=   71.3  SIGMA=   2.7  PHAS=   -44.8  FOM=  0.75  TEST=  0
INDE  18  30  62  FOBS=   77.3  SIGMA=   2.8  PHAS=  -168.3  FOM=  0.87  TEST=  0
INDE  18  30  64  FOBS=   37.2  SIGMA=  14.4  PHAS=   148.1  FOM=  0.02  TEST=  1
INDE  18  30  66  FOBS=   39.8  SIGMA=  13.7  PHAS=   -23.5  FOM=  0.60  TEST=  0
INDE  18  30  68  FOBS=   83.2  SIGMA=   6.9  PHAS=   151.3  FOM=  0.89  TEST=  0
INDE  18  31  19  FOBS=  147.2  SIGMA=   1.0  PHAS=  -137.7  FOM=  0.96  TEST=  0
INDE  18  31  21  FOBS=  150.1  SIGMA=   1.0  PHAS=   156.8  FOM=  0.97  TEST=  0
INDE  18  31  23  FOBS=  266.5  SIGMA=   0.7  PHAS=    37.1  FOM=  0.97  TEST=  0
INDE  18  31  25  FOBS=  161.5  SIGMA=   1.0  PHAS=    24.4  FOM=  0.83  TEST=  1
INDE  18  31  27  FOBS=  252.6  SIGMA=   0.8  PHAS=  -108.9  FOM=  0.93  TEST=  0
INDE  18  31  29  FOBS=   40.5  SIGMA=   4.2  PHAS=   149.8  FOM=  0.76  TEST=  0
INDE  18  31  31  FOBS=  119.9  SIGMA=   1.4  PHAS=   -50.6  FOM=  0.79  TEST=  0
INDE  18  31  33  FOBS=  204.5  SIGMA=   1.0  PHAS=  -119.5  FOM=  0.88  TEST=  1
INDE  18  31  35  FOBS=  247.7  SIGMA=   1.1  PHAS=  -162.0  FOM=  0.95  TEST=  0
INDE  18  31  37  FOBS=   83.8  SIGMA=   2.5  PHAS=   -60.4  FOM=  0.86  TEST=  0
INDE  18  31  39  FOBS=  134.8  SIGMA=   1.5  PHAS=    26.2  FOM=  0.90  TEST=  0
INDE  18  31  41  FOBS=  159.9  SIGMA=   1.3  PHAS=    26.1  FOM=  0.94  TEST=  0
INDE  18  31  43  FOBS=   72.8  SIGMA=   2.3  PHAS=  -163.1  FOM=  0.68  TEST=  0
INDE  18  31  45  FOBS=  126.4  SIGMA=   1.4  PHAS=   -61.0  FOM=  0.96  TEST=  0
INDE  18  31  47  FOBS=   30.3  SIGMA=   5.7  PHAS=    23.5  FOM=  0.29  TEST=  0
```

*FIG. 12A - 413*

```
INDE 18 31 49 FOBS=  70.8 SIGMA=  2.3 PHAS=  -33.9 FOM= 0.92 TEST= 1
INDE 18 31 51 FOBS= 121.1 SIGMA=  1.4 PHAS=   80.8 FOM= 0.93 TEST= 0
INDE 18 31 53 FOBS=  55.9 SIGMA=  2.8 PHAS= -149.2 FOM= 0.75 TEST= 0
INDE 18 31 55 FOBS=  38.1 SIGMA=  5.7 PHAS=  169.1 FOM= 0.34 TEST= 0
INDE 18 31 57 FOBS=  68.5 SIGMA=  2.8 PHAS=  -81.0 FOM= 0.88 TEST= 0
INDE 18 31 59 FOBS=  48.4 SIGMA=  3.9 PHAS= -153.1 FOM= 0.78 TEST= 0
INDE 18 31 61 FOBS=  34.1 SIGMA=  7.9 PHAS= -174.1 FOM= 0.47 TEST= 0
INDE 18 31 63 FOBS=  66.6 SIGMA=  4.0 PHAS=  117.4 FOM= 0.84 TEST= 0
INDE 18 31 65 FOBS=  91.9 SIGMA=  6.0 PHAS= -144.1 FOM= 0.85 TEST= 0
INDE 18 31 67 FOBS=  93.4 SIGMA=  6.2 PHAS=  174.9 FOM= 0.90 TEST= 0
INDE 18 31 69 FOBS=  58.8 SIGMA= 10.0 PHAS=   17.7 FOM= 0.64 TEST= 0
INDE 18 32 18 FOBS= 109.3 SIGMA=  1.3 PHAS=  112.2 FOM= 0.76 TEST= 0
INDE 18 32 20 FOBS= 245.1 SIGMA=  0.7 PHAS=   15.4 FOM= 0.94 TEST= 0
INDE 18 32 22 FOBS= 346.7 SIGMA=  0.6 PHAS=  -23.0 FOM= 0.97 TEST= 0
INDE 18 32 24 FOBS= 244.7 SIGMA=  0.8 PHAS=   11.9 FOM= 0.96 TEST= 0
INDE 18 32 26 FOBS=  69.7 SIGMA=  2.3 PHAS=   17.5 FOM= 0.93 TEST= 0
INDE 18 32 28 FOBS= 258.1 SIGMA=  0.8 PHAS=  -13.6 FOM= 0.90 TEST= 1
INDE 18 32 30 FOBS=  40.7 SIGMA=  3.9 PHAS=  -10.9 FOM= 0.71 TEST= 0
INDE 18 32 32 FOBS=  96.7 SIGMA=  1.8 PHAS=   84.4 FOM= 0.86 TEST= 1
INDE 18 32 34 FOBS= 164.2 SIGMA=  1.4 PHAS=  128.7 FOM= 0.90 TEST= 0
INDE 18 32 36 FOBS=  88.7 SIGMA=  2.4 PHAS= -153.7 FOM= 0.88 TEST= 0
INDE 18 32 38 FOBS= 138.6 SIGMA=  1.6 PHAS=   87.9 FOM= 0.95 TEST= 0
INDE 18 32 40 FOBS= 123.9 SIGMA=  1.6 PHAS=  -24.1 FOM= 0.93 TEST= 0
INDE 18 32 42 FOBS=  36.1 SIGMA=  5.5 PHAS=   50.5 FOM= 0.54 TEST= 0
INDE 18 32 44 FOBS=  87.2 SIGMA=  2.2 PHAS=  149.2 FOM= 0.95 TEST= 0
INDE 18 32 46 FOBS=  67.1 SIGMA=  2.5 PHAS=   -3.4 FOM= 0.91 TEST= 0
INDE 18 32 48 FOBS=  96.2 SIGMA=  1.8 PHAS=  -23.9 FOM= 0.95 TEST= 0
INDE 18 32 50 FOBS=  85.0 SIGMA=  1.9 PHAS= -104.5 FOM= 0.87 TEST= 0
INDE 18 32 52 FOBS=  52.6 SIGMA=  3.0 PHAS=   67.6 FOM= 0.04 TEST= 1
INDE 18 32 54 FOBS=  59.0 SIGMA=  3.1 PHAS=  158.5 FOM= 0.63 TEST= 0
INDE 18 32 56 FOBS=  53.4 SIGMA=  3.6 PHAS= -157.8 FOM= 0.79 TEST= 0
INDE 18 32 58 FOBS=  48.1 SIGMA=  3.9 PHAS= -154.0 FOM= 0.82 TEST= 0
INDE 18 32 60 FOBS=  20.4 SIGMA= 10.4 PHAS= -126.0 FOM= 0.05 TEST= 0
INDE 18 32 62 FOBS=  51.4 SIGMA=  5.1 PHAS=  160.7 FOM= 0.85 TEST= 0
INDE 18 32 64 FOBS=  28.2 SIGMA= 10.8 PHAS=  127.1 FOM= 0.31 TEST= 0
INDE 18 32 66 FOBS=  34.2 SIGMA= 11.5 PHAS= -133.7 FOM= 0.05 TEST= 1
INDE 18 33 19 FOBS= 198.4 SIGMA=  0.8 PHAS=  -59.8 FOM= 0.87 TEST= 0
INDE 18 33 21 FOBS= 207.1 SIGMA=  0.8 PHAS= -149.5 FOM= 0.92 TEST= 0
INDE 18 33 23 FOBS= 312.4 SIGMA=  0.6 PHAS=  -29.7 FOM= 0.97 TEST= 0
INDE 18 33 25 FOBS= 139.6 SIGMA=  1.2 PHAS=  -30.4 FOM= 0.91 TEST= 1
INDE 18 33 27 FOBS= 196.1 SIGMA=  0.9 PHAS= -112.3 FOM= 0.91 TEST= 0
INDE 18 33 29 FOBS= 127.0 SIGMA=  1.4 PHAS= -122.3 FOM= 0.91 TEST= 0
INDE 18 33 31 FOBS=  66.7 SIGMA=  2.6 PHAS=  122.2 FOM= 0.32 TEST= 0
INDE 18 33 33 FOBS= 130.4 SIGMA=  1.5 PHAS=  114.8 FOM= 0.96 TEST= 0
INDE 18 33 35 FOBS= 151.2 SIGMA=  1.5 PHAS=  134.0 FOM= 0.94 TEST= 0
INDE 18 33 37 FOBS=  45.8 SIGMA=  4.6 PHAS=   25.7 FOM= 0.41 TEST= 0
INDE 18 33 39 FOBS= 180.2 SIGMA=  1.2 PHAS=  -59.7 FOM= 0.89 TEST= 0
INDE 18 33 41 FOBS=  96.1 SIGMA=  2.0 PHAS=   -3.8 FOM= 0.76 TEST= 0
INDE 18 33 43 FOBS=  53.6 SIGMA=  3.5 PHAS= -162.3 FOM= 0.28 TEST= 0
INDE 18 33 45 FOBS=   0.0 SIGMA= 21.9 PHAS=    0.0 FOM= 0.00 TEST= 0
INDE 18 33 47 FOBS=  31.3 SIGMA=  5.5 PHAS= -125.7 FOM= 0.22 TEST= 0
INDE 18 33 49 FOBS= 108.8 SIGMA=  1.6 PHAS= -155.2 FOM= 0.93 TEST= 0
INDE 18 33 51 FOBS=  47.8 SIGMA=  3.4 PHAS=  136.8 FOM= 0.44 TEST= 0
INDE 18 33 53 FOBS=  56.7 SIGMA=  2.9 PHAS=   65.9 FOM= 0.78 TEST= 0
INDE 18 33 55 FOBS=  39.7 SIGMA=  5.1 PHAS=  137.0 FOM= 0.40 TEST= 0
INDE 18 33 57 FOBS=  64.5 SIGMA=  3.0 PHAS=  124.0 FOM= 0.90 TEST= 0
INDE 18 33 59 FOBS=   0.0 SIGMA= 21.5 PHAS=    0.0 FOM= 0.00 TEST= 1
INDE 18 33 61 FOBS=  43.9 SIGMA=  5.0 PHAS=   73.8 FOM= 0.71 TEST= 0
INDE 18 33 63 FOBS=  42.8 SIGMA=  6.2 PHAS=  111.8 FOM= 0.62 TEST= 0
INDE 18 33 65 FOBS=  67.7 SIGMA=  4.7 PHAS=  130.1 FOM= 0.69 TEST= 0
INDE 18 33 67 FOBS=  40.6 SIGMA=  9.9 PHAS=  167.8 FOM= 0.87 TEST= 0
INDE 18 34 18 FOBS=  88.2 SIGMA=  1.7 PHAS=  -82.8 FOM= 0.88 TEST= 0
INDE 18 34 20 FOBS=  65.9 SIGMA=  2.1 PHAS=   88.1 FOM= 0.86 TEST= 0
INDE 18 34 22 FOBS= 133.3 SIGMA=  1.1 PHAS= -105.2 FOM= 0.92 TEST= 0
INDE 18 34 24 FOBS= 171.7 SIGMA=  1.0 PHAS=  -70.9 FOM= 0.86 TEST= 0
INDE 18 34 26 FOBS= 113.8 SIGMA=  1.5 PHAS=   25.0 FOM= 0.91 TEST= 0
INDE 18 34 28 FOBS=  97.3 SIGMA=  1.9 PHAS=  -33.5 FOM= 0.84 TEST= 0
INDE 18 34 30 FOBS=  49.9 SIGMA=  3.9 PHAS=  132.8 FOM= 0.57 TEST= 1
INDE 18 34 32 FOBS= 299.2 SIGMA=  1.0 PHAS=   37.8 FOM= 0.97 TEST= 0
INDE 18 34 34 FOBS= 243.6 SIGMA=  0.9 PHAS=   33.6 FOM= 0.94 TEST= 0
```

*FIG. 12A - 414*

```
INDE  18  34  36  FOBS=    0.0  SIGMA=  21.0  PHAS=    0.0  FOM=  0.00  TEST= 0
INDE  18  34  38  FOBS=   56.3  SIGMA=   3.7  PHAS=  165.7  FOM=  0.79  TEST= 0
INDE  18  34  40  FOBS=  100.8  SIGMA=   1.9  PHAS= -103.5  FOM=  0.86  TEST= 0
INDE  18  34  42  FOBS=   90.1  SIGMA=   2.1  PHAS=    4.2  FOM=  0.91  TEST= 0
INDE  18  34  44  FOBS=   94.3  SIGMA=   2.0  PHAS=   66.0  FOM=  0.90  TEST= 0
INDE  18  34  46  FOBS=  117.5  SIGMA=   1.6  PHAS=  -77.3  FOM=  0.05  TEST= 1
INDE  18  34  48  FOBS=   15.5  SIGMA=  13.9  PHAS=  176.6  FOM=  0.04  TEST= 0
INDE  18  34  50  FOBS=   50.2  SIGMA=   3.2  PHAS=   25.6  FOM=  0.54  TEST= 0
INDE  18  34  52  FOBS=  128.1  SIGMA=   1.5  PHAS=  -44.8  FOM=  0.89  TEST= 0
INDE  18  34  54  FOBS=   38.3  SIGMA=   5.0  PHAS=  125.3  FOM=  0.56  TEST= 0
INDE  18  34  56  FOBS=   31.2  SIGMA=   6.0  PHAS= -145.9  FOM=  0.36  TEST= 0
INDE  18  34  58  FOBS=   67.6  SIGMA=   3.5  PHAS=   12.2  FOM=  0.90  TEST= 0
INDE  18  34  60  FOBS=   65.1  SIGMA=   3.3  PHAS=    1.1  FOM=  0.42  TEST= 0
INDE  18  34  62  FOBS=   21.4  SIGMA=  11.0  PHAS=  110.9  FOM=  0.24  TEST= 0
INDE  18  34  64  FOBS=   76.8  SIGMA=   3.2  PHAS=  -26.0  FOM=  0.87  TEST= 0
INDE  18  34  66  FOBS=   32.6  SIGMA=  10.0  PHAS= -118.5  FOM=  0.07  TEST= 1
INDE  18  35  19  FOBS=   37.4  SIGMA=   4.2  PHAS=    5.6  FOM=  0.40  TEST= 0
INDE  18  35  21  FOBS=   51.0  SIGMA=   2.9  PHAS= -170.5  FOM=  0.85  TEST= 0
INDE  18  35  23  FOBS=  143.5  SIGMA=   1.1  PHAS=  -30.4  FOM=  0.90  TEST= 0
INDE  18  35  25  FOBS=  252.7  SIGMA=   0.7  PHAS= -117.9  FOM=  0.97  TEST= 0
INDE  18  35  27  FOBS=  197.6  SIGMA=   1.0  PHAS=   99.6  FOM=  0.37  TEST= 1
INDE  18  35  29  FOBS=  154.0  SIGMA=   1.4  PHAS=   97.1  FOM=  0.95  TEST= 0
INDE  18  35  31  FOBS=  136.3  SIGMA=   1.6  PHAS=  -11.5  FOM=  0.90  TEST= 0
INDE  18  35  33  FOBS=  149.6  SIGMA=   1.3  PHAS=  -30.7  FOM=  0.84  TEST= 0
INDE  18  35  35  FOBS=   37.2  SIGMA=   5.2  PHAS= -126.7  FOM=  0.43  TEST= 0
INDE  18  35  37  FOBS=    0.0  SIGMA=  20.4  PHAS=    0.0  FOM=  0.00  TEST= 0
INDE  18  35  39  FOBS=  117.7  SIGMA=   1.7  PHAS=  -73.9  FOM=  0.35  TEST= 1
INDE  18  35  41  FOBS=   92.5  SIGMA=   2.1  PHAS= -146.0  FOM=  0.77  TEST= 0
INDE  18  35  43  FOBS=    7.8  SIGMA=  27.0  PHAS=    5.2  FOM=  0.01  TEST= 0
INDE  18  35  45  FOBS=   38.1  SIGMA=   5.1  PHAS=   12.8  FOM=  0.73  TEST= 0
INDE  18  35  47  FOBS=   69.6  SIGMA=   2.9  PHAS=   77.7  FOM=  0.67  TEST= 1
INDE  18  35  49  FOBS=   75.0  SIGMA=   2.4  PHAS= -134.7  FOM=  0.81  TEST= 0
INDE  18  35  51  FOBS=  167.1  SIGMA=   1.2  PHAS= -139.5  FOM=  0.56  TEST= 1
INDE  18  35  53  FOBS=   30.7  SIGMA=   6.3  PHAS=  125.2  FOM=  0.55  TEST= 0
INDE  18  35  55  FOBS=   63.6  SIGMA=   3.4  PHAS=  177.9  FOM=  0.71  TEST= 0
INDE  18  35  57  FOBS=   75.0  SIGMA=   2.9  PHAS=  172.2  FOM=  0.83  TEST= 0
INDE  18  35  59  FOBS=   77.6  SIGMA=   2.8  PHAS=  -96.2  FOM=  0.86  TEST= 0
INDE  18  35  61  FOBS=   58.2  SIGMA=   4.7  PHAS=  112.6  FOM=  0.87  TEST= 0
INDE  18  35  63  FOBS=   54.7  SIGMA=   4.1  PHAS= -175.9  FOM=  0.77  TEST= 0
INDE  18  35  65  FOBS=   70.3  SIGMA=   4.6  PHAS= -162.2  FOM=  0.91  TEST= 0
INDE  18  35  67  FOBS=   26.8  SIGMA=  15.2  PHAS= -135.9  FOM=  0.36  TEST= 0
INDE  18  36  18  FOBS=  269.1  SIGMA=   0.7  PHAS=  -93.2  FOM=  0.92  TEST= 0
INDE  18  36  20  FOBS=   11.4  SIGMA=  14.6  PHAS=  110.5  FOM=  0.04  TEST= 0
INDE  18  36  22  FOBS=  134.3  SIGMA=   1.2  PHAS=  163.6  FOM=  0.63  TEST= 0
INDE  18  36  24  FOBS=   55.8  SIGMA=   3.0  PHAS= -168.7  FOM=  0.94  TEST= 0
INDE  18  36  26  FOBS=  121.4  SIGMA=   1.5  PHAS=   -1.8  FOM=  0.87  TEST= 0
INDE  18  36  28  FOBS=  367.0  SIGMA=   0.8  PHAS=  -39.0  FOM=  0.98  TEST= 0
INDE  18  36  30  FOBS=    0.0  SIGMA=  21.0  PHAS=    0.0  FOM=  0.00  TEST= 1
INDE  18  36  32  FOBS=  198.0  SIGMA=   1.1  PHAS=  -10.6  FOM=  0.94  TEST= 0
INDE  18  36  34  FOBS=  178.6  SIGMA=   1.1  PHAS=   16.3  FOM=  0.92  TEST= 0
INDE  18  36  36  FOBS=   98.7  SIGMA=   1.9  PHAS=  113.6  FOM=  0.93  TEST= 0
INDE  18  36  38  FOBS=   61.3  SIGMA=   3.4  PHAS=  171.6  FOM=  0.28  TEST= 0
INDE  18  36  40  FOBS=   21.3  SIGMA=  10.4  PHAS=   84.1  FOM=  0.15  TEST= 0
INDE  18  36  42  FOBS=   31.5  SIGMA=   6.0  PHAS=  -41.0  FOM=  0.14  TEST= 0
INDE  18  36  44  FOBS=   82.9  SIGMA=   2.3  PHAS=  -26.1  FOM=  0.78  TEST= 0
INDE  18  36  46  FOBS=  173.3  SIGMA=   1.3  PHAS=  -45.9  FOM=  0.96  TEST= 0
INDE  18  36  48  FOBS=   52.6  SIGMA=   3.5  PHAS= -116.4  FOM=  0.84  TEST= 0
INDE  18  36  50  FOBS=   75.1  SIGMA=   2.6  PHAS=   46.8  FOM=  0.76  TEST= 1
INDE  18  36  52  FOBS=   92.1  SIGMA=   2.1  PHAS= -163.1  FOM=  0.77  TEST= 0
INDE  18  36  54  FOBS=  114.4  SIGMA=   2.0  PHAS=   72.7  FOM=  0.93  TEST= 0
INDE  18  36  56  FOBS=   61.7  SIGMA=   3.5  PHAS=  -49.4  FOM=  0.63  TEST= 0
INDE  18  36  58  FOBS=   72.7  SIGMA=   3.0  PHAS= -162.4  FOM=  0.54  TEST= 0
INDE  18  36  60  FOBS=  105.3  SIGMA=   2.3  PHAS=   58.2  FOM=  0.95  TEST= 0
INDE  18  36  62  FOBS=   87.3  SIGMA=   2.6  PHAS=   61.8  FOM=  0.95  TEST= 0
INDE  18  36  64  FOBS=  106.1  SIGMA=   2.7  PHAS=    8.6  FOM=  0.94  TEST= 0
INDE  18  36  66  FOBS=   26.1  SIGMA=  12.4  PHAS=   37.0  FOM=  0.43  TEST= 0
INDE  18  37  19  FOBS=  264.7  SIGMA=   0.8  PHAS=  130.4  FOM=  0.96  TEST= 0
INDE  18  37  21  FOBS=  121.8  SIGMA=   1.4  PHAS=  -36.6  FOM=  0.80  TEST= 0
INDE  18  37  23  FOBS=   49.9  SIGMA=   3.5  PHAS=    6.7  FOM=  0.53  TEST= 0
INDE  18  37  25  FOBS=  285.1  SIGMA=   0.8  PHAS=  -55.9  FOM=  0.97  TEST= 0
```

*FIG. 12A - 415*

```
INDE  18  37  27  FOBS=  191.2  SIGMA=   1.0  PHAS=  -140.4  FOM=  0.89  TEST=  0
INDE  18  37  29  FOBS=   76.1  SIGMA=   2.8  PHAS=  -120.9  FOM=  0.87  TEST=  0
INDE  18  37  31  FOBS=  233.5  SIGMA=   1.0  PHAS=   -35.3  FOM=  0.94  TEST=  0
INDE  18  37  33  FOBS=  281.7  SIGMA=   0.8  PHAS=   -98.3  FOM=  0.98  TEST=  0
INDE  18  37  35  FOBS=  139.8  SIGMA=   1.4  PHAS=   -57.9  FOM=  0.95  TEST=  0
INDE  18  37  37  FOBS=   77.6  SIGMA=   2.4  PHAS=  -176.1  FOM=  0.70  TEST=  0
INDE  18  37  39  FOBS=  100.5  SIGMA=   2.1  PHAS=   -75.2  FOM=  0.81  TEST=  0
INDE  18  37  41  FOBS=   44.4  SIGMA=   4.3  PHAS=   168.4  FOM=  0.81  TEST=  0
INDE  18  37  43  FOBS=   40.2  SIGMA=   4.6  PHAS=    13.9  FOM=  0.56  TEST=  0
INDE  18  37  45  FOBS=  222.0  SIGMA=   1.0  PHAS=  -110.5  FOM=  0.98  TEST=  0
INDE  18  37  47  FOBS=  227.4  SIGMA=   0.9  PHAS=   148.8  FOM=  0.98  TEST=  0
INDE  18  37  49  FOBS=  106.4  SIGMA=   1.9  PHAS=  -178.9  FOM=  0.96  TEST=  0
INDE  18  37  51  FOBS=  100.1  SIGMA=   2.3  PHAS=   -63.8  FOM=  0.91  TEST=  0
INDE  18  37  53  FOBS=  122.7  SIGMA=   1.8  PHAS=   141.4  FOM=  0.92  TEST=  0
INDE  18  37  55  FOBS=   82.8  SIGMA=   2.7  PHAS=   -76.9  FOM=  0.84  TEST=  0
INDE  18  37  57  FOBS=   80.2  SIGMA=   2.7  PHAS=   169.9  FOM=  0.92  TEST=  0
INDE  18  37  59  FOBS=  147.0  SIGMA=   1.6  PHAS=    93.4  FOM=  0.39  TEST=  1
INDE  18  37  61  FOBS=   77.8  SIGMA=   2.8  PHAS=   -36.4  FOM=  0.93  TEST=  0
INDE  18  37  63  FOBS=   90.4  SIGMA=   2.5  PHAS=    -2.5  FOM=  0.92  TEST=  0
INDE  18  37  65  FOBS=   86.9  SIGMA=   3.8  PHAS=  -122.1  FOM=  0.92  TEST=  0
INDE  18  38  18  FOBS=   77.1  SIGMA=   2.2  PHAS=    81.7  FOM=  0.91  TEST=  0
INDE  18  38  20  FOBS=   98.9  SIGMA=   1.7  PHAS=    61.0  FOM=  0.66  TEST=  0
INDE  18  38  22  FOBS=  145.6  SIGMA=   1.3  PHAS=     2.6  FOM=  0.97  TEST=  0
INDE  18  38  24  FOBS=  152.1  SIGMA=   1.3  PHAS=   177.3  FOM=  0.87  TEST=  0
INDE  18  38  26  FOBS=   27.5  SIGMA=   7.7  PHAS=    30.2  FOM=  0.02  TEST=  1
INDE  18  38  28  FOBS=   35.6  SIGMA=   5.2  PHAS=    59.9  FOM=  0.52  TEST=  0
INDE  18  38  30  FOBS=   38.9  SIGMA=   5.2  PHAS=  -166.1  FOM=  0.79  TEST=  0
INDE  18  38  32  FOBS=  102.2  SIGMA=   2.0  PHAS=  -172.6  FOM=  0.75  TEST=  0
INDE  18  38  34  FOBS=  195.9  SIGMA=   1.0  PHAS=  -167.7  FOM=  0.71  TEST=  1
INDE  18  38  36  FOBS=  210.3  SIGMA=   1.0  PHAS=   135.6  FOM=  0.91  TEST=  0
INDE  18  38  38  FOBS=   34.0  SIGMA=   6.6  PHAS=  -117.5  FOM=  0.19  TEST=  0
INDE  18  38  40  FOBS=   46.6  SIGMA=   4.1  PHAS=    78.9  FOM=  0.64  TEST=  1
INDE  18  38  42  FOBS=   57.5  SIGMA=   3.3  PHAS=    86.1  FOM=  0.62  TEST=  0
INDE  18  38  44  FOBS=    0.0  SIGMA=  20.2  PHAS=     0.0  FOM=  0.00  TEST=  1
INDE  18  38  46  FOBS=  124.8  SIGMA=   1.6  PHAS=   134.8  FOM=  0.90  TEST=  0
INDE  18  38  48  FOBS=  130.7  SIGMA=   1.6  PHAS=    91.8  FOM=  0.94  TEST=  0
INDE  18  38  50  FOBS=   35.7  SIGMA=   8.4  PHAS=   149.2  FOM=  0.55  TEST=  0
INDE  18  38  52  FOBS=   89.1  SIGMA=   2.5  PHAS=  -151.1  FOM=  0.87  TEST=  0
INDE  18  38  54  FOBS=   88.9  SIGMA=   2.5  PHAS=   162.7  FOM=  0.88  TEST=  0
INDE  18  38  56  FOBS=   73.9  SIGMA=   3.0  PHAS=   169.7  FOM=  0.43  TEST=  0
INDE  18  38  58  FOBS=   76.2  SIGMA=   2.9  PHAS=   -67.1  FOM=  0.78  TEST=  0
INDE  18  38  60  FOBS=   69.5  SIGMA=   3.2  PHAS=     0.0  FOM=  0.91  TEST=  0
INDE  18  38  62  FOBS=   49.7  SIGMA=   4.5  PHAS=     9.5  FOM=  0.77  TEST=  0
INDE  18  38  64  FOBS=  127.1  SIGMA=   2.3  PHAS=   -56.6  FOM=  0.97  TEST=  0
INDE  18  39  19  FOBS=  193.3  SIGMA=   1.1  PHAS=    60.9  FOM=  0.97  TEST=  0
INDE  18  39  21  FOBS=  211.4  SIGMA=   1.0  PHAS=   -92.3  FOM=  0.94  TEST=  0
INDE  18  39  23  FOBS=   62.3  SIGMA=   3.1  PHAS=    49.8  FOM=  0.75  TEST=  0
INDE  18  39  25  FOBS=  336.3  SIGMA=   0.8  PHAS=   -31.9  FOM=  0.97  TEST=  0
INDE  18  39  27  FOBS=  104.2  SIGMA=   1.7  PHAS=  -111.8  FOM=  0.80  TEST=  0
INDE  18  39  29  FOBS=   25.4  SIGMA=   6.9  PHAS=   -71.0  FOM=  0.43  TEST=  1
INDE  18  39  31  FOBS=    0.0  SIGMA=  21.5  PHAS=     0.0  FOM=  0.00  TEST=  0
INDE  18  39  33  FOBS=   84.7  SIGMA=   2.5  PHAS=    67.7  FOM=  0.88  TEST=  1
INDE  18  39  35  FOBS=   74.6  SIGMA=   2.5  PHAS=   112.7  FOM=  0.60  TEST=  0
INDE  18  39  37  FOBS=   50.8  SIGMA=   3.6  PHAS=    40.7  FOM=  0.80  TEST=  0
INDE  18  39  39  FOBS=   74.1  SIGMA=   2.8  PHAS=    29.1  FOM=  0.85  TEST=  0
INDE  18  39  41  FOBS=    0.0  SIGMA=  20.0  PHAS=     0.0  FOM=  0.00  TEST=  0
INDE  18  39  43  FOBS=   29.2  SIGMA=   6.3  PHAS=  -154.0  FOM=  0.01  TEST=  0
INDE  18  39  45  FOBS=    0.0  SIGMA=  20.1  PHAS=     0.0  FOM=  0.00  TEST=  0
INDE  18  39  47  FOBS=  118.0  SIGMA=   2.0  PHAS=    65.9  FOM=  0.95  TEST=  0
INDE  18  39  49  FOBS=   54.6  SIGMA=   4.1  PHAS=  -151.9  FOM=  0.45  TEST=  0
INDE  18  39  51  FOBS=   46.3  SIGMA=   4.8  PHAS=   136.1  FOM=  0.34  TEST=  0
INDE  18  39  53  FOBS=   74.0  SIGMA=   3.0  PHAS=   118.2  FOM=  0.90  TEST=  0
INDE  18  39  55  FOBS=   91.8  SIGMA=   2.7  PHAS=   179.1  FOM=  0.88  TEST=  0
INDE  18  39  57  FOBS=    0.0  SIGMA=  22.0  PHAS=     0.0  FOM=  0.00  TEST=  0
INDE  18  39  59  FOBS=   32.5  SIGMA=   7.3  PHAS=    74.3  FOM=  0.12  TEST=  1
INDE  18  39  61  FOBS=   96.2  SIGMA=   2.4  PHAS=   -78.2  FOM=  0.95  TEST=  0
INDE  18  39  63  FOBS=   47.4  SIGMA=   6.9  PHAS=  -149.2  FOM=  0.86  TEST=  0
INDE  18  40  18  FOBS=   69.5  SIGMA=   2.9  PHAS=    35.8  FOM=  0.72  TEST=  0
INDE  18  40  20  FOBS=   82.5  SIGMA=   2.4  PHAS=   -61.1  FOM=  0.93  TEST=  0
INDE  18  40  22  FOBS=  135.2  SIGMA=   1.5  PHAS=  -128.7  FOM=  0.94  TEST=  0
```

*FIG. 12A - 416*

```
INDE  18  40  24 FOBS=   203.6 SIGMA=   1.1 PHAS=  -141.0 FOM=  0.98 TEST= 0
INDE  18  40  26 FOBS=   181.2 SIGMA=   1.1 PHAS=  -163.6 FOM=  0.95 TEST= 0
INDE  18  40  28 FOBS=   335.1 SIGMA=   0.7 PHAS=  -168.7 FOM=  0.97 TEST= 0
INDE  18  40  30 FOBS=   138.8 SIGMA=   1.3 PHAS=   109.1 FOM=  0.93 TEST= 0
INDE  18  40  32 FOBS=     0.0 SIGMA=  20.7 PHAS=     0.0 FOM=  0.00 TEST= 0
INDE  18  40  34 FOBS=    97.1 SIGMA=   2.2 PHAS=   -83.5 FOM=  0.90 TEST= 1
INDE  18  40  36 FOBS=    85.4 SIGMA=   2.2 PHAS=    95.5 FOM=  0.66 TEST= 0
INDE  18  40  38 FOBS=   195.5 SIGMA=   1.1 PHAS=   -11.3 FOM=  0.96 TEST= 0
INDE  18  40  40 FOBS=     0.0 SIGMA=  20.2 PHAS=     0.0 FOM=  0.00 TEST= 0
INDE  18  40  42 FOBS=     0.0 SIGMA=  21.4 PHAS=     0.0 FOM=  0.00 TEST= 0
INDE  18  40  44 FOBS=     0.0 SIGMA=  21.2 PHAS=     0.0 FOM=  0.00 TEST= 0
INDE  18  40  46 FOBS=    18.4 SIGMA=  12.0 PHAS=  -114.4 FOM=  0.50 TEST= 0
INDE  18  40  48 FOBS=    85.7 SIGMA=   2.6 PHAS=    60.1 FOM=  0.94 TEST= 0
INDE  18  40  50 FOBS=     0.0 SIGMA=  21.0 PHAS=     0.0 FOM=  0.00 TEST= 0
INDE  18  40  52 FOBS=    60.9 SIGMA=   3.6 PHAS=  -145.8 FOM=  0.78 TEST= 0
INDE  18  40  54 FOBS=    71.2 SIGMA=   3.1 PHAS=   105.9 FOM=  0.85 TEST= 0
INDE  18  40  56 FOBS=     0.0 SIGMA=  20.8 PHAS=     0.0 FOM=  0.00 TEST= 0
INDE  18  40  58 FOBS=     0.0 SIGMA=  20.8 PHAS=     0.0 FOM=  0.00 TEST= 0
INDE  18  40  60 FOBS=     8.2 SIGMA=  32.7 PHAS=   116.1 FOM=  0.01 TEST= 1
INDE  18  40  62 FOBS=    23.5 SIGMA=  13.3 PHAS=   134.1 FOM=  0.58 TEST= 0
INDE  18  40  64 FOBS=    55.9 SIGMA=   5.2 PHAS=   -37.6 FOM=  0.86 TEST= 0
INDE  18  41  19 FOBS=   215.5 SIGMA=   1.1 PHAS=    65.8 FOM=  0.96 TEST= 0
INDE  18  41  21 FOBS=    41.0 SIGMA=   5.1 PHAS=    91.0 FOM=  0.44 TEST= 0
INDE  18  41  23 FOBS=   321.7 SIGMA=   0.8 PHAS=    90.2 FOM=  0.97 TEST= 0
INDE  18  41  25 FOBS=    76.4 SIGMA=   2.5 PHAS=  -110.9 FOM=  0.88 TEST= 0
INDE  18  41  27 FOBS=   265.4 SIGMA=   1.0 PHAS=   110.1 FOM=  0.97 TEST= 0
INDE  18  41  29 FOBS=   144.3 SIGMA=   1.3 PHAS=    61.0 FOM=  0.87 TEST= 0
INDE  18  41  31 FOBS=   118.9 SIGMA=   1.5 PHAS=    19.2 FOM=  0.91 TEST= 0
INDE  18  41  33 FOBS=   211.0 SIGMA=   1.0 PHAS=   -50.4 FOM=  0.96 TEST= 0
INDE  18  41  35 FOBS=    85.4 SIGMA=   2.3 PHAS=  -166.6 FOM=  0.93 TEST= 0
INDE  18  41  37 FOBS=    39.7 SIGMA=   4.8 PHAS=  -171.6 FOM=  0.38 TEST= 0
INDE  18  41  39 FOBS=    34.5 SIGMA=   5.6 PHAS=   -80.2 FOM=  0.25 TEST= 0
INDE  18  41  41 FOBS=     0.0 SIGMA=  22.4 PHAS=     0.0 FOM=  0.00 TEST= 0
INDE  18  41  43 FOBS=    33.7 SIGMA=   6.8 PHAS=   110.9 FOM=  0.36 TEST= 0
INDE  18  41  45 FOBS=    52.1 SIGMA=   4.3 PHAS=   116.2 FOM=  0.74 TEST= 0
INDE  18  41  47 FOBS=     0.0 SIGMA=  21.0 PHAS=     0.0 FOM=  0.00 TEST= 0
INDE  18  41  49 FOBS=    37.2 SIGMA=   5.9 PHAS=   116.3 FOM=  0.39 TEST= 0
INDE  18  41  51 FOBS=    64.2 SIGMA=   3.5 PHAS=    36.7 FOM=  0.83 TEST= 0
INDE  18  41  53 FOBS=     0.0 SIGMA=  21.0 PHAS=     0.0 FOM=  0.00 TEST= 0
INDE  18  41  55 FOBS=     0.0 SIGMA=  23.0 PHAS=     0.0 FOM=  0.00 TEST= 0
INDE  18  41  57 FOBS=     0.0 SIGMA=  23.3 PHAS=     0.0 FOM=  0.00 TEST= 0
INDE  18  41  59 FOBS=    45.3 SIGMA=   4.9 PHAS=   -22.5 FOM=  0.08 TEST= 1
INDE  18  41  61 FOBS=    48.2 SIGMA=   5.7 PHAS=    -2.7 FOM=  0.10 TEST= 1
INDE  18  41  63 FOBS=     0.0 SIGMA=  23.8 PHAS=     0.0 FOM=  0.00 TEST= 0
INDE  18  42  18 FOBS=   107.8 SIGMA=   1.9 PHAS=   -47.7 FOM=  0.92 TEST= 0
INDE  18  42  20 FOBS=   145.8 SIGMA=   1.4 PHAS=  -100.5 FOM=  0.94 TEST= 0
INDE  18  42  22 FOBS=   258.9 SIGMA=   0.9 PHAS=   -65.2 FOM=  0.93 TEST= 0
INDE  18  42  24 FOBS=   119.4 SIGMA=   1.7 PHAS=   176.6 FOM=  0.76 TEST= 1
INDE  18  42  26 FOBS=   130.2 SIGMA=   1.5 PHAS=    99.6 FOM=  0.91 TEST= 0
INDE  18  42  28 FOBS=    48.9 SIGMA=   3.8 PHAS=   -64.2 FOM=  0.84 TEST= 0
INDE  18  42  30 FOBS=    91.2 SIGMA=   1.9 PHAS=   166.8 FOM=  0.69 TEST= 0
INDE  18  42  32 FOBS=   244.7 SIGMA=   0.9 PHAS=  -120.3 FOM=  0.97 TEST= 0
INDE  18  42  34 FOBS=    78.6 SIGMA=   2.5 PHAS=  -126.9 FOM=  0.82 TEST= 0
INDE  18  42  36 FOBS=   123.4 SIGMA=   1.7 PHAS=    90.5 FOM=  0.95 TEST= 0
INDE  18  42  38 FOBS=   143.5 SIGMA=   1.6 PHAS=    25.4 FOM=  0.93 TEST= 0
INDE  18  42  40 FOBS=    41.9 SIGMA=   5.0 PHAS=    -9.3 FOM=  0.59 TEST= 0
INDE  18  42  42 FOBS=   119.8 SIGMA=   2.0 PHAS=    30.4 FOM=  0.92 TEST= 0
INDE  18  42  44 FOBS=    64.1 SIGMA=   3.6 PHAS=   -11.3 FOM=  0.61 TEST= 0
INDE  18  42  46 FOBS=    13.5 SIGMA=  22.7 PHAS=   158.3 FOM=  0.14 TEST= 0
INDE  18  42  48 FOBS=    64.6 SIGMA=   3.5 PHAS=    69.6 FOM=  0.87 TEST= 0
INDE  18  42  50 FOBS=     0.0 SIGMA=  20.9 PHAS=     0.0 FOM=  0.00 TEST= 0
INDE  18  42  52 FOBS=     0.0 SIGMA=  21.9 PHAS=     0.0 FOM=  0.00 TEST= 0
INDE  18  42  54 FOBS=     0.0 SIGMA=  20.8 PHAS=     0.0 FOM=  0.00 TEST= 0
INDE  18  42  56 FOBS=    24.1 SIGMA=   9.1 PHAS=   -21.0 FOM=  0.10 TEST= 1
INDE  18  42  58 FOBS=     0.0 SIGMA=  22.1 PHAS=     0.0 FOM=  0.00 TEST= 0
INDE  18  42  60 FOBS=     0.0 SIGMA=  22.0 PHAS=     0.0 FOM=  0.00 TEST= 0
INDE  18  42  62 FOBS=     0.0 SIGMA=  23.7 PHAS=     0.0 FOM=  0.00 TEST= 0
INDE  18  43  19 FOBS=   148.9 SIGMA=   1.5 PHAS=   133.2 FOM=  0.85 TEST= 0
INDE  18  43  21 FOBS=   124.0 SIGMA=   1.6 PHAS=    11.5 FOM=  0.48 TEST= 1
INDE  18  43  23 FOBS=   220.5 SIGMA=   1.0 PHAS=    74.9 FOM=  0.91 TEST= 0
```

*FIG. 12A - 417*

```
INDE  18  43  25  FOBS=    28.3  SIGMA=   7.2  PHAS=  -103.2  FOM=  0.18  TEST=  1
INDE  18  43  27  FOBS=   165.3  SIGMA=   1.2  PHAS=    54.6  FOM=  0.93  TEST=  0
INDE  18  43  29  FOBS=    76.5  SIGMA=   2.5  PHAS=    20.0  FOM=  0.69  TEST=  0
INDE  18  43  31  FOBS=   208.8  SIGMA=   1.0  PHAS=   154.7  FOM=  0.96  TEST=  1
INDE  18  43  33  FOBS=    99.0  SIGMA=   1.9  PHAS=   -66.8  FOM=  0.47  TEST=  0
INDE  18  43  35  FOBS=   134.3  SIGMA=   1.7  PHAS=  -133.5  FOM=  0.92  TEST=  0
INDE  18  43  37  FOBS=    73.6  SIGMA=   2.9  PHAS=   -65.7  FOM=  0.88  TEST=  0
INDE  18  43  39  FOBS=    54.4  SIGMA=   3.9  PHAS=   -39.3  FOM=  0.89  TEST=  0
INDE  18  43  41  FOBS=    75.2  SIGMA=   2.8  PHAS=   -78.0  FOM=  0.85  TEST=  0
INDE  18  43  43  FOBS=    68.0  SIGMA=   3.4  PHAS=   -38.9  FOM=  0.73  TEST=  0
INDE  18  43  45  FOBS=    81.3  SIGMA=   2.9  PHAS=     6.6  FOM=  0.86  TEST=  0
INDE  18  43  47  FOBS=    56.7  SIGMA=   4.0  PHAS=  -107.8  FOM=  0.80  TEST=  1
INDE  18  43  49  FOBS=     0.0  SIGMA=  21.0  PHAS=     0.0  FOM=  0.00  TEST=  0
INDE  18  43  51  FOBS=    60.0  SIGMA=   3.7  PHAS=    13.4  FOM=  0.67  TEST=  0
INDE  18  43  53  FOBS=     0.0  SIGMA=  20.9  PHAS=     0.0  FOM=  0.00  TEST=  0
INDE  18  43  55  FOBS=    52.3  SIGMA=   4.3  PHAS=   148.9  FOM=  0.76  TEST=  0
INDE  18  43  57  FOBS=    66.8  SIGMA=   3.3  PHAS=  -172.1  FOM=  0.56  TEST=  0
INDE  18  43  59  FOBS=     5.7  SIGMA=  43.4  PHAS=    73.3  FOM=  0.04  TEST=  0
INDE  18  43  61  FOBS=    31.6  SIGMA=   9.0  PHAS=  -109.7  FOM=  0.67  TEST=  0
INDE  18  44  18  FOBS=   147.1  SIGMA=   1.4  PHAS=   155.1  FOM=  0.91  TEST=  0
INDE  18  44  20  FOBS=    78.6  SIGMA=   2.6  PHAS=  -117.5  FOM=  0.83  TEST=  0
INDE  18  44  22  FOBS=   143.5  SIGMA=   1.4  PHAS=   -79.5  FOM=  0.92  TEST=  0
INDE  18  44  24  FOBS=     0.0  SIGMA=  19.4  PHAS=     0.0  FOM=  0.00  TEST=  0
INDE  18  44  26  FOBS=    55.0  SIGMA=   3.6  PHAS=    92.3  FOM=  0.61  TEST=  0
INDE  18  44  28  FOBS=   148.1  SIGMA=   1.5  PHAS=   -39.2  FOM=  0.82  TEST=  0
INDE  18  44  30  FOBS=    84.9  SIGMA=   2.3  PHAS=   151.0  FOM=  0.90  TEST=  1
INDE  18  44  32  FOBS=    94.0  SIGMA=   2.1  PHAS=  -172.7  FOM=  0.91  TEST=  0
INDE  18  44  34  FOBS=   108.9  SIGMA=   1.8  PHAS=   110.0  FOM=  0.93  TEST=  0
INDE  18  44  36  FOBS=   139.2  SIGMA=   1.7  PHAS=   149.3  FOM=  0.96  TEST=  0
INDE  18  44  38  FOBS=     0.0  SIGMA=  21.2  PHAS=     0.0  FOM=  0.00  TEST=  0
INDE  18  44  40  FOBS=    31.5  SIGMA=   6.5  PHAS=   -65.7  FOM=  0.81  TEST=  0
INDE  18  44  42  FOBS=    85.2  SIGMA=   2.4  PHAS=  -110.2  FOM=  0.16  TEST=  1
INDE  18  44  44  FOBS=    92.0  SIGMA=   2.5  PHAS=  -106.1  FOM=  0.85  TEST=  0
INDE  18  44  46  FOBS=    82.0  SIGMA=   2.8  PHAS=   156.9  FOM=  0.64  TEST=  0
INDE  18  44  48  FOBS=    28.8  SIGMA=   7.7  PHAS=    93.0  FOM=  0.53  TEST=  0
INDE  18  44  50  FOBS=    68.2  SIGMA=   3.3  PHAS=   130.8  FOM=  0.62  TEST=  0
INDE  18  44  52  FOBS=    42.5  SIGMA=   5.2  PHAS=   176.5  FOM=  0.65  TEST=  0
INDE  18  44  54  FOBS=    51.8  SIGMA=   4.3  PHAS=   119.2  FOM=  0.83  TEST=  0
INDE  18  44  56  FOBS=    29.9  SIGMA=   7.4  PHAS=    53.1  FOM=  0.50  TEST=  0
INDE  18  44  58  FOBS=    63.6  SIGMA=   3.6  PHAS=  -162.7  FOM=  0.13  TEST=  0
INDE  18  44  60  FOBS=     0.0  SIGMA=  25.5  PHAS=     0.0  FOM=  0.00  TEST=  0
INDE  18  45  19  FOBS=    97.7  SIGMA=   2.1  PHAS=    70.1  FOM=  0.27  TEST=  1
INDE  18  45  21  FOBS=   142.5  SIGMA=   1.5  PHAS=   115.9  FOM=  0.61  TEST=  0
INDE  18  45  23  FOBS=    42.9  SIGMA=   4.7  PHAS=  -136.9  FOM=  0.18  TEST=  0
INDE  18  45  25  FOBS=     0.0  SIGMA=  21.8  PHAS=     0.0  FOM=  0.00  TEST=  0
INDE  18  45  27  FOBS=   142.7  SIGMA=   1.6  PHAS=    -9.6  FOM=  0.89  TEST=  0
INDE  18  45  29  FOBS=    58.0  SIGMA=   3.8  PHAS=    13.6  FOM=  0.74  TEST=  0
INDE  18  45  31  FOBS=   120.5  SIGMA=   1.7  PHAS=  -177.2  FOM=  0.96  TEST=  0
INDE  18  45  33  FOBS=   144.9  SIGMA=   1.4  PHAS=   -25.0  FOM=  0.94  TEST=  0
INDE  18  45  35  FOBS=    58.9  SIGMA=   3.4  PHAS=    83.2  FOM=  0.46  TEST=  1
INDE  18  45  37  FOBS=    27.4  SIGMA=   8.0  PHAS=    66.4  FOM=  0.59  TEST=  0
INDE  18  45  39  FOBS=     9.9  SIGMA=  20.9  PHAS=  -157.9  FOM=  0.42  TEST=  0
INDE  18  45  41  FOBS=    68.4  SIGMA=   3.1  PHAS=  -168.4  FOM=  0.62  TEST=  0
INDE  18  45  43  FOBS=     0.0  SIGMA=  20.2  PHAS=     0.0  FOM=  0.00  TEST=  0
INDE  18  45  45  FOBS=    68.7  SIGMA=   3.4  PHAS=    19.0  FOM=  0.86  TEST=  0
INDE  18  45  47  FOBS=    56.5  SIGMA=   4.0  PHAS=   -69.0  FOM=  0.27  TEST=  1
INDE  18  45  49  FOBS=   108.8  SIGMA=   2.1  PHAS=    32.3  FOM=  0.89  TEST=  0
INDE  18  45  51  FOBS=    42.8  SIGMA=   5.2  PHAS=    54.7  FOM=  0.72  TEST=  0
INDE  18  45  53  FOBS=    33.8  SIGMA=   6.6  PHAS=    87.0  FOM=  0.76  TEST=  0
INDE  18  45  55  FOBS=    53.4  SIGMA=   4.2  PHAS=   -49.9  FOM=  0.76  TEST=  0
INDE  18  45  57  FOBS=    38.8  SIGMA=   5.8  PHAS=   168.4  FOM=  0.65  TEST=  0
INDE  18  45  59  FOBS=    76.8  SIGMA=   3.7  PHAS=  -120.3  FOM=  0.76  TEST=  0
INDE  18  46  18  FOBS=   237.8  SIGMA=   1.0  PHAS=  -179.1  FOM=  0.95  TEST=  0
INDE  18  46  20  FOBS=    17.6  SIGMA=  13.1  PHAS=    12.9  FOM=  0.03  TEST=  0
INDE  18  46  22  FOBS=    63.6  SIGMA=   3.4  PHAS=    29.3  FOM=  0.67  TEST=  0
INDE  18  46  24  FOBS=   153.8  SIGMA=   1.5  PHAS=  -151.4  FOM=  0.90  TEST=  0
INDE  18  46  26  FOBS=    23.8  SIGMA=   9.2  PHAS=   -68.3  FOM=  0.08  TEST=  1
INDE  18  46  28  FOBS=    50.6  SIGMA=   4.7  PHAS=   165.9  FOM=  0.18  TEST=  0
INDE  18  46  30  FOBS=    31.6  SIGMA=   7.6  PHAS=   108.4  FOM=  0.23  TEST=  0
INDE  18  46  32  FOBS=   117.0  SIGMA=   1.7  PHAS=  -143.6  FOM=  0.89  TEST=  0
```

*FIG. 12A - 418*

```
INDE 18 46 34 FOBS=  173.1 SIGMA=  1.2 PHAS=  156.7 FOM= 0.94 TEST= 0
INDE 18 46 36 FOBS=   63.4 SIGMA=  3.2 PHAS=  135.5 FOM= 0.54 TEST= 0
INDE 18 46 38 FOBS=   96.9 SIGMA=  2.0 PHAS=   43.0 FOM= 0.52 TEST= 0
INDE 18 46 40 FOBS=  118.3 SIGMA=  1.8 PHAS=   71.7 FOM= 0.91 TEST= 0
INDE 18 46 42 FOBS=   46.5 SIGMA=  4.5 PHAS= -129.0 FOM= 0.36 TEST= 1
INDE 18 46 44 FOBS=   92.3 SIGMA=  2.2 PHAS= -112.2 FOM= 0.95 TEST= 0
INDE 18 46 46 FOBS=   91.0 SIGMA=  2.5 PHAS=  174.1 FOM= 0.86 TEST= 0
INDE 18 46 48 FOBS=   82.3 SIGMA=  2.8 PHAS=  -74.2 FOM= 0.91 TEST= 0
INDE 18 46 50 FOBS=   71.4 SIGMA=  3.2 PHAS=  -33.6 FOM= 0.81 TEST= 0
INDE 18 46 52 FOBS=   55.4 SIGMA=  4.1 PHAS= -107.8 FOM= 0.59 TEST= 0
INDE 18 46 54 FOBS=    0.0 SIGMA= 25.3 PHAS=    0.0 FOM= 0.00 TEST= 0
INDE 18 46 56 FOBS=   54.6 SIGMA=  4.1 PHAS=  122.6 FOM= 0.81 TEST= 0
INDE 18 46 58 FOBS=    0.0 SIGMA= 23.6 PHAS=    0.0 FOM= 0.00 TEST= 0
INDE 18 46 60 FOBS=   44.5 SIGMA=  9.4 PHAS= -171.7 FOM= 0.50 TEST= 0
INDE 18 47 19 FOBS=  103.8 SIGMA=  2.1 PHAS=   69.0 FOM= 0.94 TEST= 0
INDE 18 47 21 FOBS=  235.6 SIGMA=  1.1 PHAS=   -9.6 FOM= 0.96 TEST= 0
INDE 18 47 23 FOBS=  149.0 SIGMA=  1.5 PHAS=  158.0 FOM= 0.94 TEST= 0
INDE 18 47 25 FOBS=   62.3 SIGMA=  3.8 PHAS= -115.4 FOM= 0.54 TEST= 0
INDE 18 47 27 FOBS=   38.9 SIGMA=  6.0 PHAS= -146.0 FOM= 0.56 TEST= 0
INDE 18 47 29 FOBS=  235.1 SIGMA=  1.1 PHAS=  164.1 FOM= 0.97 TEST= 0
INDE 18 47 31 FOBS=   64.9 SIGMA=  3.4 PHAS= -121.0 FOM= 0.84 TEST= 0
INDE 18 47 33 FOBS=   60.6 SIGMA=  3.2 PHAS=  131.9 FOM= 0.38 TEST= 0
INDE 18 47 35 FOBS=   71.1 SIGMA=  2.9 PHAS=   31.3 FOM= 0.89 TEST= 0
INDE 18 47 37 FOBS=   61.8 SIGMA=  3.3 PHAS=  -63.7 FOM= 0.56 TEST= 0
INDE 18 47 39 FOBS=   45.9 SIGMA=  4.2 PHAS=  -30.7 FOM= 0.74 TEST= 0
INDE 18 47 41 FOBS=   58.2 SIGMA=  3.6 PHAS=   33.5 FOM= 0.69 TEST= 0
INDE 18 47 43 FOBS=   35.9 SIGMA=  5.5 PHAS=   63.9 FOM= 0.67 TEST= 0
INDE 18 47 45 FOBS=   65.6 SIGMA=  3.0 PHAS=   92.0 FOM= 0.73 TEST= 0
INDE 18 47 47 FOBS=   16.0 SIGMA= 15.2 PHAS=  -97.5 FOM= 0.01 TEST= 1
INDE 18 47 49 FOBS=   49.6 SIGMA=  4.5 PHAS=  175.5 FOM= 0.69 TEST= 0
INDE 18 47 51 FOBS=   45.3 SIGMA=  5.0 PHAS= -179.4 FOM= 0.75 TEST= 0
INDE 18 47 53 FOBS=   35.3 SIGMA=  6.4 PHAS=  106.7 FOM= 0.59 TEST= 0
INDE 18 47 55 FOBS=    0.0 SIGMA= 21.2 PHAS=    0.0 FOM= 0.00 TEST= 0
INDE 18 47 57 FOBS=   60.7 SIGMA=  4.6 PHAS=  172.6 FOM= 0.14 TEST= 1
INDE 18 47 59 FOBS=    0.0 SIGMA= 29.7 PHAS=    0.0 FOM= 0.00 TEST= 0
INDE 18 48 18 FOBS=  106.2 SIGMA=  2.1 PHAS=  162.9 FOM= 0.93 TEST= 0
INDE 18 48 20 FOBS=  218.6 SIGMA=  1.1 PHAS=  -43.3 FOM= 0.10 TEST= 1
INDE 18 48 22 FOBS=   48.8 SIGMA=  4.3 PHAS=  -23.8 FOM= 0.57 TEST= 0
INDE 18 48 24 FOBS=    0.0 SIGMA= 21.8 PHAS=    0.0 FOM= 0.00 TEST= 0
INDE 18 48 26 FOBS=  116.6 SIGMA=  1.9 PHAS=  137.6 FOM= 0.45 TEST= 0
INDE 18 48 28 FOBS=  120.6 SIGMA=  1.9 PHAS=   32.5 FOM= 0.76 TEST= 0
INDE 18 48 30 FOBS=  204.6 SIGMA=  1.2 PHAS=   71.4 FOM= 0.95 TEST= 0
INDE 18 48 32 FOBS=  136.4 SIGMA=  1.5 PHAS= -179.4 FOM= 0.50 TEST= 1
INDE 18 48 34 FOBS=  122.5 SIGMA=  1.6 PHAS=  150.4 FOM= 0.94 TEST= 0
INDE 18 48 36 FOBS=   21.8 SIGMA= 11.0 PHAS=    3.3 FOM= 0.17 TEST= 0
INDE 18 48 38 FOBS=   91.8 SIGMA=  2.2 PHAS=  153.6 FOM= 0.76 TEST= 0
INDE 18 48 40 FOBS=    0.0 SIGMA= 19.6 PHAS=    0.0 FOM= 0.00 TEST= 0
INDE 18 48 42 FOBS=   79.9 SIGMA=  2.7 PHAS=  -94.1 FOM= 0.54 TEST= 0
INDE 18 48 44 FOBS=  114.7 SIGMA=  1.8 PHAS=  -57.6 FOM= 0.86 TEST= 0
INDE 18 48 46 FOBS=   66.9 SIGMA=  3.0 PHAS= -158.4 FOM= 0.88 TEST= 0
INDE 18 48 48 FOBS=   93.6 SIGMA=  2.5 PHAS=  -11.1 FOM= 0.42 TEST= 1
INDE 18 48 50 FOBS=   25.7 SIGMA=  8.7 PHAS=  -90.0 FOM= 0.24 TEST= 0
INDE 18 48 52 FOBS=  103.7 SIGMA=  2.2 PHAS=  133.5 FOM= 0.91 TEST= 0
INDE 18 48 54 FOBS=   62.9 SIGMA=  3.6 PHAS=  -58.4 FOM= 0.90 TEST= 0
INDE 18 48 56 FOBS=   58.2 SIGMA=  4.8 PHAS=  -74.7 FOM= 0.65 TEST= 0
INDE 18 48 58 FOBS=    0.0 SIGMA= 25.6 PHAS=    0.0 FOM= 0.00 TEST= 0
INDE 18 49 19 FOBS=   86.9 SIGMA=  2.4 PHAS=  -92.1 FOM= 0.86 TEST= 0
INDE 18 49 21 FOBS=  114.7 SIGMA=  2.0 PHAS=  135.2 FOM= 0.87 TEST= 1
INDE 18 49 23 FOBS=  162.4 SIGMA=  1.4 PHAS=  101.9 FOM= 0.93 TEST= 0
INDE 18 49 25 FOBS=  106.4 SIGMA=  2.1 PHAS=   20.8 FOM= 0.92 TEST= 0
INDE 18 49 27 FOBS=   68.8 SIGMA=  3.2 PHAS= -167.4 FOM= 0.61 TEST= 0
INDE 18 49 29 FOBS=   89.4 SIGMA=  2.5 PHAS=   13.5 FOM= 0.82 TEST= 0
INDE 18 49 31 FOBS=   70.6 SIGMA=  3.1 PHAS=  -70.4 FOM= 0.77 TEST= 0
INDE 18 49 33 FOBS=  158.7 SIGMA=  1.3 PHAS=  102.1 FOM= 0.96 TEST= 0
INDE 18 49 35 FOBS=   83.9 SIGMA=  2.3 PHAS=  -13.9 FOM= 0.92 TEST= 0
INDE 18 49 37 FOBS=   54.8 SIGMA=  3.7 PHAS=   67.4 FOM= 0.10 TEST= 0
INDE 18 49 39 FOBS=    0.0 SIGMA= 19.9 PHAS=    0.0 FOM= 0.00 TEST= 1
INDE 18 49 41 FOBS=   71.6 SIGMA=  2.7 PHAS=  -52.9 FOM= 0.67 TEST= 0
INDE 18 49 43 FOBS=   40.4 SIGMA=  5.3 PHAS=  146.4 FOM= 0.06 TEST= 0
INDE 18 49 45 FOBS=   48.9 SIGMA=  4.0 PHAS= -124.6 FOM= 0.23 TEST= 0
```

*FIG. 12A - 419*

```
INDE 18 49 47 FOBS=   48.3 SIGMA=  4.1 PHAS= -119.1 FOM= 0.55 TEST= 0
INDE 18 49 49 FOBS=   43.5 SIGMA=  5.2 PHAS= -169.6 FOM= 0.76 TEST= 0
INDE 18 49 51 FOBS=   32.4 SIGMA=  7.0 PHAS=   24.2 FOM= 0.51 TEST= 0
INDE 18 49 53 FOBS=   49.8 SIGMA=  4.6 PHAS= -117.9 FOM= 0.69 TEST= 0
INDE 18 49 55 FOBS=   68.8 SIGMA=  4.1 PHAS=  176.4 FOM= 0.89 TEST= 0
INDE 18 49 57 FOBS=    0.0 SIGMA= 26.2 PHAS=    0.0 FOM= 0.00 TEST= 0
INDE 18 50 18 FOBS=   50.2 SIGMA=  5.4 PHAS=  136.0 FOM= 0.48 TEST= 0
INDE 18 50 20 FOBS=   65.7 SIGMA=  3.2 PHAS= -171.4 FOM= 0.91 TEST= 1
INDE 18 50 22 FOBS=  223.1 SIGMA=  1.1 PHAS=   48.6 FOM= 0.97 TEST= 0
INDE 18 50 24 FOBS=  231.5 SIGMA=  1.1 PHAS=   28.4 FOM= 0.91 TEST= 1
INDE 18 50 26 FOBS=   35.0 SIGMA=  6.2 PHAS= -151.2 FOM= 0.70 TEST= 0
INDE 18 50 28 FOBS=  122.3 SIGMA=  1.8 PHAS=  -44.4 FOM= 0.93 TEST= 0
INDE 18 50 30 FOBS=  103.2 SIGMA=  2.2 PHAS=  -10.2 FOM= 0.93 TEST= 0
INDE 18 50 32 FOBS=  122.8 SIGMA=  1.8 PHAS=   65.3 FOM= 0.93 TEST= 0
INDE 18 50 34 FOBS=   91.3 SIGMA=  2.1 PHAS=  -92.1 FOM= 0.85 TEST= 0
INDE 18 50 36 FOBS=   77.1 SIGMA=  2.6 PHAS=  -63.0 FOM= 0.91 TEST= 0
INDE 18 50 38 FOBS=    0.0 SIGMA= 20.7 PHAS=    0.0 FOM= 0.00 TEST= 0
INDE 18 50 40 FOBS=   46.5 SIGMA=  4.0 PHAS=  -75.6 FOM= 0.40 TEST= 0
INDE 18 50 42 FOBS=   60.2 SIGMA=  3.2 PHAS= -138.7 FOM= 0.83 TEST= 0
INDE 18 50 44 FOBS=  133.1 SIGMA=  1.6 PHAS=   60.7 FOM= 0.17 TEST= 1
INDE 18 50 46 FOBS=    2.2 SIGMA= 88.4 PHAS= -175.2 FOM= 0.02 TEST= 0
INDE 18 50 48 FOBS=   63.8 SIGMA=  3.1 PHAS=   27.8 FOM= 0.88 TEST= 0
INDE 18 50 50 FOBS=    0.0 SIGMA= 22.1 PHAS=    0.0 FOM= 0.00 TEST= 0
INDE 18 50 52 FOBS=   65.1 SIGMA=  3.6 PHAS= -178.3 FOM= 0.91 TEST= 0
INDE 18 50 54 FOBS=   31.4 SIGMA=  9.0 PHAS=  -42.1 FOM= 0.65 TEST= 0
INDE 18 50 56 FOBS=   19.7 SIGMA= 16.5 PHAS= -141.9 FOM= 0.33 TEST= 0
INDE 18 51 19 FOBS=  104.8 SIGMA=  2.1 PHAS=  -62.7 FOM= 0.95 TEST= 0
INDE 18 51 21 FOBS=  125.9 SIGMA=  1.9 PHAS=  134.8 FOM= 0.94 TEST= 0
INDE 18 51 23 FOBS=  133.9 SIGMA=  1.7 PHAS=  -44.4 FOM= 0.83 TEST= 1
INDE 18 51 25 FOBS=   66.3 SIGMA=  3.3 PHAS=  -51.1 FOM= 0.80 TEST= 0
INDE 18 51 27 FOBS=   10.0 SIGMA= 23.6 PHAS=  175.4 FOM= 0.15 TEST= 0
INDE 18 51 29 FOBS=   91.1 SIGMA=  2.4 PHAS= -139.4 FOM= 0.86 TEST= 0
INDE 18 51 31 FOBS=   69.1 SIGMA=  3.1 PHAS=  -75.7 FOM= 0.87 TEST= 0
INDE 18 51 33 FOBS=   36.1 SIGMA=  6.5 PHAS=   54.8 FOM= 0.40 TEST= 0
INDE 18 51 35 FOBS=  118.6 SIGMA=  1.7 PHAS= -166.2 FOM= 0.91 TEST= 0
INDE 18 51 37 FOBS=    0.0 SIGMA= 19.9 PHAS=    0.0 FOM= 0.00 TEST= 0
INDE 18 51 39 FOBS=   22.2 SIGMA=  8.9 PHAS=   83.3 FOM= 0.35 TEST= 0
INDE 18 51 41 FOBS=    0.0 SIGMA= 20.2 PHAS=    0.0 FOM= 0.00 TEST= 1
INDE 18 51 43 FOBS=    0.0 SIGMA= 20.5 PHAS=    0.0 FOM= 0.00 TEST= 0
INDE 18 51 45 FOBS=   79.9 SIGMA=  2.5 PHAS=  -45.9 FOM= 0.88 TEST= 0
INDE 18 51 47 FOBS=   94.8 SIGMA=  2.2 PHAS= -108.0 FOM= 0.88 TEST= 0
INDE 18 51 49 FOBS=   44.2 SIGMA=  4.5 PHAS=  -66.9 FOM= 0.37 TEST= 0
INDE 18 51 51 FOBS=   15.1 SIGMA= 16.2 PHAS=   99.4 FOM= 0.56 TEST= 0
INDE 18 51 53 FOBS=   49.0 SIGMA=  5.8 PHAS=  169.5 FOM= 0.78 TEST= 0
INDE 18 51 55 FOBS=   28.5 SIGMA= 12.2 PHAS= -159.8 FOM= 0.39 TEST= 0
INDE 18 52 18 FOBS=   20.9 SIGMA= 10.5 PHAS= -131.3 FOM= 0.11 TEST= 0
INDE 18 52 20 FOBS=   65.4 SIGMA=  3.2 PHAS=  151.5 FOM= 0.55 TEST= 0
INDE 18 52 22 FOBS=  194.7 SIGMA=  1.2 PHAS=   61.2 FOM= 0.95 TEST= 0
INDE 18 52 24 FOBS=  102.2 SIGMA=  2.1 PHAS=   25.9 FOM= 0.67 TEST= 0
INDE 18 52 26 FOBS=   90.8 SIGMA=  2.4 PHAS=  -84.1 FOM= 0.87 TEST= 0
INDE 18 52 28 FOBS=   58.8 SIGMA=  3.6 PHAS=   12.1 FOM= 0.82 TEST= 0
INDE 18 52 30 FOBS=    0.0 SIGMA= 24.1 PHAS=    0.0 FOM= 0.00 TEST= 0
INDE 18 52 32 FOBS=   31.1 SIGMA=  6.8 PHAS= -104.0 FOM= 0.30 TEST= 0
INDE 18 52 34 FOBS=   86.2 SIGMA=  2.4 PHAS=  -89.7 FOM= 0.85 TEST= 0
INDE 18 52 36 FOBS=   34.9 SIGMA=  5.8 PHAS=   18.3 FOM= 0.30 TEST= 1
INDE 18 52 38 FOBS=   68.5 SIGMA=  3.2 PHAS=  -80.3 FOM= 0.78 TEST= 0
INDE 18 52 40 FOBS=   69.7 SIGMA=  2.9 PHAS=  -78.5 FOM= 0.88 TEST= 0
INDE 18 52 42 FOBS=   19.3 SIGMA= 10.7 PHAS=  151.8 FOM= 0.23 TEST= 0
INDE 18 52 44 FOBS=    0.0 SIGMA= 19.3 PHAS=    0.0 FOM= 0.00 TEST= 0
INDE 18 52 46 FOBS=   82.1 SIGMA=  2.5 PHAS= -161.5 FOM= 0.90 TEST= 0
INDE 18 52 48 FOBS=   37.5 SIGMA=  5.4 PHAS=  176.8 FOM= 0.58 TEST= 0
INDE 18 52 50 FOBS=   73.8 SIGMA=  3.1 PHAS=  112.1 FOM= 0.90 TEST= 0
INDE 18 52 52 FOBS=   31.9 SIGMA=  9.4 PHAS=  -14.2 FOM= 0.13 TEST= 0
INDE 18 52 54 FOBS=    0.0 SIGMA= 29.9 PHAS=    0.0 FOM= 0.00 TEST= 0
INDE 18 53 19 FOBS=    9.6 SIGMA= 31.3 PHAS=  162.2 FOM= 0.32 TEST= 1
INDE 18 53 21 FOBS=  168.9 SIGMA=  1.3 PHAS= -100.9 FOM= 0.96 TEST= 0
INDE 18 53 23 FOBS=  102.9 SIGMA=  2.1 PHAS= -175.0 FOM= 0.77 TEST= 0
INDE 18 53 25 FOBS=  120.3 SIGMA=  1.8 PHAS= -136.5 FOM= 0.85 TEST= 0
INDE 18 53 27 FOBS=   70.8 SIGMA=  3.0 PHAS=  -22.3 FOM= 0.72 TEST= 0
INDE 18 53 29 FOBS=    5.9 SIGMA= 39.8 PHAS=   48.6 FOM= 0.05 TEST= 0
```

*FIG. 12A - 420*

```
INDE 18 53 31 FOBS=   35.4 SIGMA=  6.0 PHAS=  112.5 FOM= 0.34 TEST= 0
INDE 18 53 33 FOBS=   39.2 SIGMA=  5.4 PHAS= -113.9 FOM= 0.62 TEST= 0
INDE 18 53 35 FOBS=   43.4 SIGMA=  4.7 PHAS= -147.4 FOM= 0.55 TEST= 0
INDE 18 53 37 FOBS=   54.3 SIGMA=  3.7 PHAS=  -55.1 FOM= 0.66 TEST= 0
INDE 18 53 39 FOBS=   46.9 SIGMA=  4.3 PHAS=  115.5 FOM= 0.67 TEST= 0
INDE 18 53 41 FOBS=    0.0 SIGMA= 20.0 PHAS=    0.0 FOM= 0.00 TEST= 0
INDE 18 53 43 FOBS=    0.0 SIGMA= 18.9 PHAS=    0.0 FOM= 0.00 TEST= 0
INDE 18 53 45 FOBS=    0.0 SIGMA= 21.0 PHAS=    0.0 FOM= 0.00 TEST= 0
INDE 18 53 47 FOBS=   59.0 SIGMA=  3.8 PHAS=   78.9 FOM= 0.68 TEST= 0
INDE 18 53 49 FOBS=  121.8 SIGMA=  2.0 PHAS=   21.2 FOM= 0.96 TEST= 0
INDE 18 53 51 FOBS=   40.0 SIGMA=  8.6 PHAS=  -30.2 FOM= 0.42 TEST= 0
INDE 18 53 53 FOBS=    0.0 SIGMA= 30.4 PHAS=    0.0 FOM= 0.00 TEST= 0
INDE 18 54 18 FOBS=   53.5 SIGMA=  4.1 PHAS=  157.1 FOM= 0.33 TEST= 0
INDE 18 54 20 FOBS=  159.9 SIGMA=  1.4 PHAS=  117.5 FOM= 0.94 TEST= 0
INDE 18 54 22 FOBS=   91.2 SIGMA=  2.3 PHAS=  111.1 FOM= 0.83 TEST= 0
INDE 18 54 24 FOBS=   58.4 SIGMA=  3.6 PHAS=   69.1 FOM= 0.84 TEST= 0
INDE 18 54 26 FOBS=    0.0 SIGMA= 20.4 PHAS=    0.0 FOM= 0.00 TEST= 1
INDE 18 54 28 FOBS=   68.3 SIGMA=  3.1 PHAS=  -37.7 FOM= 0.40 TEST= 1
INDE 18 54 30 FOBS=   30.1 SIGMA=  7.0 PHAS=  -27.3 FOM= 0.22 TEST= 0
INDE 18 54 32 FOBS=   95.1 SIGMA=  2.3 PHAS= -145.3 FOM= 0.34 TEST= 0
INDE 18 54 34 FOBS=   48.1 SIGMA=  4.4 PHAS= -158.8 FOM= 0.58 TEST= 0
INDE 18 54 36 FOBS=  121.4 SIGMA=  1.6 PHAS= -122.0 FOM= 0.95 TEST= 0
INDE 18 54 38 FOBS=  143.0 SIGMA=  1.5 PHAS=  -99.9 FOM= 0.91 TEST= 0
INDE 18 54 40 FOBS=   30.2 SIGMA=  8.0 PHAS= -106.1 FOM= 0.21 TEST= 1
INDE 18 54 42 FOBS=   34.0 SIGMA=  6.1 PHAS=  168.7 FOM= 0.55 TEST= 0
INDE 18 54 44 FOBS=    0.0 SIGMA= 19.8 PHAS=    0.0 FOM= 0.00 TEST= 0
INDE 18 54 46 FOBS=   31.4 SIGMA=  7.1 PHAS=  -81.2 FOM= 0.45 TEST= 0
INDE 18 54 48 FOBS=   99.4 SIGMA=  2.6 PHAS=  -87.1 FOM= 0.94 TEST= 0
INDE 18 54 50 FOBS=   30.5 SIGMA=  9.1 PHAS=  178.2 FOM= 0.43 TEST= 0
INDE 18 54 52 FOBS=   55.0 SIGMA=  5.9 PHAS= -142.0 FOM= 0.79 TEST= 0
INDE 18 55 19 FOBS=   82.3 SIGMA=  3.3 PHAS=   46.6 FOM= 0.86 TEST= 0
INDE 18 55 21 FOBS=   95.2 SIGMA=  2.2 PHAS=  -51.7 FOM= 0.66 TEST= 0
INDE 18 55 23 FOBS=    0.0 SIGMA= 22.3 PHAS=    0.0 FOM= 0.00 TEST= 0
INDE 18 55 25 FOBS=   49.1 SIGMA=  4.2 PHAS= -148.8 FOM= 0.78 TEST= 0
INDE 18 55 27 FOBS=    0.0 SIGMA= 22.5 PHAS=    0.0 FOM= 0.00 TEST= 0
INDE 18 55 29 FOBS=   60.2 SIGMA=  3.5 PHAS=   58.2 FOM= 0.87 TEST= 0
INDE 18 55 31 FOBS=   95.7 SIGMA=  2.3 PHAS=  -17.0 FOM= 0.75 TEST= 0
INDE 18 55 33 FOBS=   47.6 SIGMA=  4.8 PHAS= -166.0 FOM= 0.10 TEST= 1
INDE 18 55 35 FOBS=  152.6 SIGMA=  1.5 PHAS=  133.7 FOM= 0.95 TEST= 0
INDE 18 55 37 FOBS=  118.1 SIGMA=  1.8 PHAS= -144.8 FOM= 0.58 TEST= 1
INDE 18 55 39 FOBS=   49.7 SIGMA=  4.5 PHAS=    6.3 FOM= 0.78 TEST= 0
INDE 18 55 41 FOBS=   51.3 SIGMA=  4.8 PHAS= -123.7 FOM= 0.74 TEST= 0
INDE 18 55 43 FOBS=   64.2 SIGMA=  3.3 PHAS=   -9.0 FOM= 0.88 TEST= 0
INDE 18 55 45 FOBS=   59.3 SIGMA=  3.7 PHAS=   47.7 FOM= 0.85 TEST= 0
INDE 18 55 47 FOBS=   42.2 SIGMA=  7.3 PHAS=  -68.9 FOM= 0.09 TEST= 1
INDE 18 55 49 FOBS=   94.0 SIGMA=  3.1 PHAS=   47.5 FOM= 0.92 TEST= 0
INDE 18 55 51 FOBS=   78.6 SIGMA=  4.2 PHAS=   84.5 FOM= 0.90 TEST= 0
INDE 18 56 18 FOBS=   50.8 SIGMA=  3.7 PHAS=  -22.3 FOM= 0.85 TEST= 0
INDE 18 56 20 FOBS=  107.4 SIGMA=  2.5 PHAS=    6.2 FOM= 0.89 TEST= 0
INDE 18 56 22 FOBS=   82.2 SIGMA=  2.7 PHAS=  -38.8 FOM= 0.79 TEST= 0
INDE 18 56 24 FOBS=   90.9 SIGMA=  2.3 PHAS=   72.3 FOM= 0.90 TEST= 0
INDE 18 56 26 FOBS=   62.5 SIGMA=  3.3 PHAS=   11.2 FOM= 0.82 TEST= 0
INDE 18 56 28 FOBS=   72.8 SIGMA=  2.9 PHAS=  -27.5 FOM= 0.77 TEST= 0
INDE 18 56 30 FOBS=   45.8 SIGMA=  4.6 PHAS=  -87.4 FOM= 0.66 TEST= 0
INDE 18 56 32 FOBS=   64.7 SIGMA=  3.7 PHAS=  152.1 FOM= 0.71 TEST= 0
INDE 18 56 34 FOBS=  111.6 SIGMA=  2.2 PHAS=   53.6 FOM= 0.94 TEST= 0
INDE 18 56 36 FOBS=   38.4 SIGMA=  7.9 PHAS=  158.8 FOM= 0.59 TEST= 0
INDE 18 56 38 FOBS=   88.4 SIGMA=  2.8 PHAS= -106.0 FOM= 0.92 TEST= 0
INDE 18 56 40 FOBS=   16.8 SIGMA= 16.2 PHAS=    3.5 FOM= 0.20 TEST= 0
INDE 18 56 42 FOBS=  122.9 SIGMA=  2.1 PHAS= -119.3 FOM= 0.97 TEST= 0
INDE 18 56 44 FOBS=  107.6 SIGMA=  2.1 PHAS=  -83.3 FOM= 0.92 TEST= 0
INDE 18 56 46 FOBS=   77.8 SIGMA=  3.0 PHAS=  -15.7 FOM= 0.90 TEST= 0
INDE 18 56 48 FOBS=   47.1 SIGMA=  7.7 PHAS=  -80.3 FOM= 0.82 TEST= 0
INDE 18 56 50 FOBS=   55.9 SIGMA=  5.9 PHAS=  -59.5 FOM= 0.77 TEST= 0
INDE 18 57 19 FOBS=  129.7 SIGMA=  2.1 PHAS=  -96.7 FOM= 0.96 TEST= 0
INDE 18 57 21 FOBS=   85.0 SIGMA=  3.1 PHAS= -102.1 FOM= 0.93 TEST= 0
INDE 18 57 23 FOBS=   76.4 SIGMA=  2.7 PHAS= -145.5 FOM= 0.80 TEST= 0
INDE 18 57 25 FOBS=   56.0 SIGMA=  3.7 PHAS=  -42.7 FOM= 0.65 TEST= 0
INDE 18 57 27 FOBS=   90.4 SIGMA=  2.6 PHAS=  -98.2 FOM= 0.80 TEST= 0
INDE 18 57 29 FOBS=   94.1 SIGMA=  2.5 PHAS=  -46.7 FOM= 0.37 TEST= 0
```

*FIG. 12A - 421*

```
INDE 18 57 31 FOBS=   44.1 SIGMA=  5.9 PHAS=  -39.9 FOM= 0.42 TEST= 0
INDE 18 57 33 FOBS=  107.7 SIGMA=  2.5 PHAS=  -15.8 FOM= 0.89 TEST= 0
INDE 18 57 35 FOBS=   46.8 SIGMA=  5.7 PHAS=   97.4 FOM= 0.26 TEST= 0
INDE 18 57 37 FOBS=   75.9 SIGMA=  3.0 PHAS=  127.0 FOM= 0.71 TEST= 0
INDE 18 57 39 FOBS=    0.0 SIGMA= 22.0 PHAS=    0.0 FOM= 0.00 TEST= 0
INDE 18 57 41 FOBS=   55.7 SIGMA=  4.5 PHAS=  152.2 FOM= 0.84 TEST= 0
INDE 18 57 43 FOBS=   35.4 SIGMA=  7.5 PHAS=  119.5 FOM= 0.72 TEST= 0
INDE 18 57 45 FOBS=   42.4 SIGMA=  5.7 PHAS= -176.8 FOM= 0.49 TEST= 0
INDE 18 57 47 FOBS=   47.9 SIGMA=  5.8 PHAS=    4.5 FOM= 0.04 TEST= 1
INDE 18 57 49 FOBS=   44.5 SIGMA=  8.5 PHAS=   97.4 FOM= 0.70 TEST= 0
INDE 18 58 18 FOBS=   64.9 SIGMA=  3.3 PHAS=  105.9 FOM= 0.83 TEST= 0
INDE 18 58 20 FOBS=   75.2 SIGMA=  3.5 PHAS= -151.7 FOM= 0.81 TEST= 0
INDE 18 58 22 FOBS=   49.5 SIGMA=  4.3 PHAS=   99.1 FOM= 0.86 TEST= 0
INDE 18 58 24 FOBS=   95.9 SIGMA=  2.6 PHAS=   62.7 FOM= 0.94 TEST= 0
INDE 18 58 26 FOBS=    0.0 SIGMA= 23.8 PHAS=    0.0 FOM= 0.00 TEST= 0
INDE 18 58 28 FOBS=  105.5 SIGMA=  2.5 PHAS= -156.8 FOM= 0.85 TEST= 0
INDE 18 58 30 FOBS=   76.8 SIGMA=  3.4 PHAS=  -16.8 FOM= 0.10 TEST= 1
INDE 18 58 32 FOBS=   41.7 SIGMA=  6.3 PHAS= -146.1 FOM= 0.58 TEST= 0
INDE 18 58 34 FOBS=    0.0 SIGMA= 25.0 PHAS=    0.0 FOM= 0.00 TEST= 0
INDE 18 58 36 FOBS=   53.1 SIGMA=  5.1 PHAS=   60.4 FOM= 0.82 TEST= 0
INDE 18 58 38 FOBS=   46.5 SIGMA=  4.9 PHAS=  -41.6 FOM= 0.39 TEST= 0
INDE 18 58 40 FOBS=   38.1 SIGMA=  7.3 PHAS=   34.5 FOM= 0.64 TEST= 0
INDE 18 58 42 FOBS=   97.2 SIGMA=  2.7 PHAS=  -67.9 FOM= 0.95 TEST= 0
INDE 18 58 44 FOBS=   67.6 SIGMA=  3.3 PHAS=  -34.1 FOM= 0.85 TEST= 0
INDE 18 58 46 FOBS=    0.0 SIGMA= 24.5 PHAS=    0.0 FOM= 0.00 TEST= 0
INDE 18 58 48 FOBS=   23.2 SIGMA= 13.8 PHAS=  -73.2 FOM= 0.31 TEST= 0
INDE 18 59 19 FOBS=   62.4 SIGMA=  3.7 PHAS=  -62.6 FOM= 0.52 TEST= 0
INDE 18 59 21 FOBS=  125.5 SIGMA=  2.9 PHAS=  113.2 FOM= 0.87 TEST= 0
INDE 18 59 23 FOBS=   33.9 SIGMA=  7.1 PHAS=   64.3 FOM= 0.45 TEST= 0
INDE 18 59 25 FOBS=   79.7 SIGMA=  3.1 PHAS=  -49.8 FOM= 0.90 TEST= 0
INDE 18 59 27 FOBS=   61.6 SIGMA=  4.1 PHAS=   82.3 FOM= 0.85 TEST= 0
INDE 18 59 29 FOBS=    0.0 SIGMA= 22.6 PHAS=    0.0 FOM= 0.00 TEST= 0
INDE 18 59 31 FOBS=    0.0 SIGMA= 22.7 PHAS=    0.0 FOM= 0.00 TEST= 0
INDE 18 59 33 FOBS=   11.6 SIGMA= 25.8 PHAS= -113.4 FOM= 0.09 TEST= 0
INDE 18 59 35 FOBS=    0.0 SIGMA= 23.0 PHAS=    0.0 FOM= 0.00 TEST= 0
INDE 18 59 37 FOBS=   65.2 SIGMA=  3.8 PHAS=  -37.1 FOM= 0.67 TEST= 0
INDE 18 59 39 FOBS=   62.5 SIGMA=  4.0 PHAS=   13.3 FOM= 0.87 TEST= 0
INDE 18 59 41 FOBS=   92.5 SIGMA=  2.8 PHAS= -117.5 FOM= 0.95 TEST= 0
INDE 18 59 43 FOBS=   55.8 SIGMA=  4.7 PHAS=  166.9 FOM= 0.87 TEST= 0
INDE 18 59 45 FOBS=   83.1 SIGMA=  3.4 PHAS=  136.9 FOM= 0.92 TEST= 0
INDE 18 59 47 FOBS=   19.9 SIGMA= 15.8 PHAS=   -3.3 FOM= 0.12 TEST= 0
INDE 18 60 18 FOBS=   32.6 SIGMA=  8.0 PHAS=  -14.2 FOM= 0.31 TEST= 0
INDE 18 60 20 FOBS=    0.0 SIGMA= 26.2 PHAS=    0.0 FOM= 0.00 TEST= 0
INDE 18 60 22 FOBS=   94.1 SIGMA=  3.8 PHAS=   15.3 FOM= 0.89 TEST= 0
INDE 18 60 24 FOBS=   20.1 SIGMA= 11.8 PHAS=   48.5 FOM= 0.41 TEST= 0
INDE 18 60 26 FOBS=   38.2 SIGMA=  6.4 PHAS=  -42.9 FOM= 0.31 TEST= 0
INDE 18 60 28 FOBS=   14.2 SIGMA= 20.3 PHAS=  -95.0 FOM= 0.25 TEST= 0
INDE 18 60 30 FOBS=    0.0 SIGMA= 22.6 PHAS=    0.0 FOM= 0.00 TEST= 0
INDE 18 60 32 FOBS=   85.1 SIGMA=  3.2 PHAS=  157.5 FOM= 0.79 TEST= 0
INDE 18 60 34 FOBS=   46.2 SIGMA=  5.8 PHAS=  161.4 FOM= 0.66 TEST= 0
INDE 18 60 36 FOBS=   57.3 SIGMA=  4.8 PHAS= -179.1 FOM= 0.85 TEST= 0
INDE 18 60 38 FOBS=  113.0 SIGMA=  2.1 PHAS=  -27.5 FOM= 0.92 TEST= 0
INDE 18 60 40 FOBS=   81.4 SIGMA=  3.2 PHAS= -134.2 FOM= 0.92 TEST= 0
INDE 18 60 42 FOBS=    0.0 SIGMA= 22.7 PHAS=    0.0 FOM= 0.00 TEST= 1
INDE 18 60 44 FOBS=   67.5 SIGMA=  4.0 PHAS=   19.1 FOM= 0.95 TEST= 0
INDE 18 60 46 FOBS=   39.0 SIGMA= 11.5 PHAS=   45.1 FOM= 0.37 TEST= 0
INDE 18 61 19 FOBS=   44.0 SIGMA=  5.8 PHAS=   36.7 FOM= 0.58 TEST= 0
INDE 18 61 21 FOBS=   29.7 SIGMA= 11.5 PHAS=  132.8 FOM= 0.49 TEST= 0
INDE 18 61 23 FOBS=    0.0 SIGMA= 26.1 PHAS=    0.0 FOM= 0.00 TEST= 0
INDE 18 61 25 FOBS=   22.2 SIGMA= 10.8 PHAS=  -97.0 FOM= 0.13 TEST= 0
INDE 18 61 27 FOBS=    0.0 SIGMA= 22.1 PHAS=    0.0 FOM= 0.00 TEST= 0
INDE 18 61 29 FOBS=    0.0 SIGMA= 22.4 PHAS=    0.0 FOM= 0.00 TEST= 0
INDE 18 61 31 FOBS=    0.0 SIGMA= 24.4 PHAS=    0.0 FOM= 0.00 TEST= 0
INDE 18 61 33 FOBS=   92.7 SIGMA=  2.9 PHAS=   39.6 FOM= 0.54 TEST= 0
INDE 18 61 35 FOBS=   65.4 SIGMA=  4.2 PHAS=   61.8 FOM= 0.80 TEST= 0
INDE 18 61 37 FOBS=   51.3 SIGMA=  5.4 PHAS= -123.6 FOM= 0.52 TEST= 0
INDE 18 61 39 FOBS=    8.3 SIGMA= 30.0 PHAS= -154.4 FOM= 0.32 TEST= 0
INDE 18 61 41 FOBS=   13.5 SIGMA= 21.8 PHAS=   30.6 FOM= 0.25 TEST= 0
INDE 18 61 43 FOBS=   54.7 SIGMA=  7.2 PHAS=  -62.0 FOM= 0.82 TEST= 0
INDE 18 62 18 FOBS=    8.3 SIGMA= 35.4 PHAS=  -17.3 FOM= 0.12 TEST= 0
```

*FIG. 12A - 422*

```
INDE 18 62 20 FOBS=    0.0 SIGMA= 22.4 PHAS=    0.0 FOM= 0.00 TEST= 0
INDE 18 62 22 FOBS=   59.1 SIGMA=  5.9 PHAS=   19.7 FOM= 0.77 TEST= 0
INDE 18 62 24 FOBS=   86.1 SIGMA=  2.8 PHAS=   64.8 FOM= 0.88 TEST= 0
INDE 18 62 26 FOBS=   56.2 SIGMA=  4.4 PHAS=  149.6 FOM= 0.69 TEST= 0
INDE 18 62 28 FOBS=   83.3 SIGMA=  3.1 PHAS= -123.2 FOM= 0.67 TEST= 0
INDE 18 62 30 FOBS=   60.5 SIGMA=  4.3 PHAS=  140.0 FOM= 0.69 TEST= 0
INDE 18 62 32 FOBS=   86.3 SIGMA=  3.1 PHAS=  -42.0 FOM= 0.28 TEST= 0
INDE 18 62 34 FOBS=   16.7 SIGMA= 18.6 PHAS=   57.7 FOM= 0.08 TEST= 1
INDE 18 62 36 FOBS=    0.0 SIGMA= 23.4 PHAS=    0.0 FOM= 0.00 TEST= 0
INDE 18 62 38 FOBS=   58.2 SIGMA=  4.8 PHAS= -156.7 FOM= 0.83 TEST= 0
INDE 18 62 40 FOBS=   59.1 SIGMA=  5.6 PHAS= -100.2 FOM= 0.88 TEST= 0
INDE 18 62 42 FOBS=    0.0 SIGMA= 25.8 PHAS=    0.0 FOM= 0.00 TEST= 0
INDE 18 63 19 FOBS=   72.3 SIGMA=  3.6 PHAS=  -33.2 FOM= 0.82 TEST= 0
INDE 18 63 21 FOBS=   19.9 SIGMA= 17.5 PHAS=   93.5 FOM= 0.29 TEST= 0
INDE 18 63 23 FOBS=   71.0 SIGMA=  5.0 PHAS= -142.9 FOM= 0.89 TEST= 0
INDE 18 63 25 FOBS=   30.8 SIGMA= 10.9 PHAS=   25.0 FOM= 0.60 TEST= 0
INDE 18 63 27 FOBS=   67.8 SIGMA=  4.3 PHAS=   19.9 FOM= 0.08 TEST= 0
INDE 18 63 29 FOBS=   82.2 SIGMA=  3.7 PHAS=   31.6 FOM= 0.91 TEST= 0
INDE 18 63 31 FOBS=    3.9 SIGMA= 96.1 PHAS=   23.9 FOM= 0.07 TEST= 1
INDE 18 63 33 FOBS=   88.3 SIGMA=  3.6 PHAS= -168.1 FOM= 0.16 TEST= 1
INDE 18 63 35 FOBS=   44.7 SIGMA=  7.1 PHAS=  -38.5 FOM= 0.54 TEST= 0
INDE 18 63 37 FOBS=   24.8 SIGMA= 12.8 PHAS=  163.7 FOM= 0.01 TEST= 0
INDE 18 63 39 FOBS=   35.3 SIGMA= 11.2 PHAS=  143.7 FOM= 0.68 TEST= 0
INDE 18 63 41 FOBS=   49.8 SIGMA=  8.0 PHAS=   84.6 FOM= 0.46 TEST= 0
INDE 18 64 18 FOBS=   84.0 SIGMA=  3.0 PHAS= -163.7 FOM= 0.67 TEST= 0
INDE 18 64 20 FOBS=    8.0 SIGMA= 37.6 PHAS= -138.5 FOM= 0.06 TEST= 0
INDE 18 64 22 FOBS=   78.8 SIGMA=  4.5 PHAS=  123.2 FOM= 0.87 TEST= 0
INDE 18 64 24 FOBS=   64.9 SIGMA=  5.5 PHAS=  -79.1 FOM= 0.83 TEST= 0
INDE 18 64 26 FOBS=    0.0 SIGMA= 26.3 PHAS=    0.0 FOM= 0.00 TEST= 0
INDE 18 64 28 FOBS=  172.2 SIGMA=  1.9 PHAS=  -80.2 FOM= 0.98 TEST= 0
INDE 18 64 30 FOBS=   54.3 SIGMA=  5.6 PHAS= -119.5 FOM= 0.89 TEST= 0
INDE 18 64 32 FOBS=  105.3 SIGMA=  3.0 PHAS=  176.7 FOM= 0.91 TEST= 0
INDE 18 64 34 FOBS=    0.0 SIGMA= 28.3 PHAS=    0.0 FOM= 0.00 TEST= 0
INDE 18 64 36 FOBS=   55.3 SIGMA=  5.8 PHAS= -136.2 FOM= 0.84 TEST= 0
INDE 18 64 38 FOBS=   77.6 SIGMA=  4.3 PHAS=  140.1 FOM= 0.31 TEST= 1
INDE 18 64 40 FOBS=   55.4 SIGMA=  6.1 PHAS= -143.6 FOM= 0.23 TEST= 1
INDE 18 65 19 FOBS=   47.4 SIGMA=  5.4 PHAS= -108.8 FOM= 0.24 TEST= 1
INDE 18 65 21 FOBS=    0.0 SIGMA= 22.6 PHAS=    0.0 FOM= 0.00 TEST= 0
INDE 18 65 23 FOBS=    0.0 SIGMA= 26.3 PHAS=    0.0 FOM= 0.00 TEST= 0
INDE 18 65 25 FOBS=   70.6 SIGMA=  5.1 PHAS= -133.3 FOM= 0.76 TEST= 0
INDE 18 65 27 FOBS=  111.4 SIGMA=  2.7 PHAS=  179.4 FOM= 0.91 TEST= 0
INDE 18 65 29 FOBS=   67.2 SIGMA=  4.5 PHAS=  177.0 FOM= 0.94 TEST= 0
INDE 18 65 31 FOBS=   58.0 SIGMA=  5.3 PHAS=  136.2 FOM= 0.09 TEST= 1
INDE 18 65 33 FOBS=   56.3 SIGMA=  5.6 PHAS=   64.3 FOM= 0.87 TEST= 0
INDE 18 65 35 FOBS=  109.2 SIGMA=  3.1 PHAS=  129.6 FOM= 0.15 TEST= 1
INDE 18 65 37 FOBS=   48.6 SIGMA=  6.8 PHAS=   94.7 FOM= 0.64 TEST= 0
INDE 18 66 18 FOBS=   15.5 SIGMA= 22.5 PHAS=    0.0 FOM= 0.00 TEST= 1
INDE 18 66 20 FOBS=   39.5 SIGMA=  6.5 PHAS=   93.2 FOM= 0.60 TEST= 0
INDE 18 66 22 FOBS=    0.0 SIGMA= 26.4 PHAS=    0.0 FOM= 0.00 TEST= 0
INDE 18 66 24 FOBS=   19.7 SIGMA= 17.7 PHAS=  136.6 FOM= 0.49 TEST= 0
INDE 18 66 26 FOBS=   57.5 SIGMA=  6.2 PHAS=  142.3 FOM= 0.15 TEST= 1
INDE 18 66 28 FOBS=   24.0 SIGMA= 14.7 PHAS=  179.6 FOM= 0.09 TEST= 1
INDE 18 66 30 FOBS=   61.7 SIGMA=  4.9 PHAS= -118.1 FOM= 0.53 TEST= 0
INDE 18 66 32 FOBS=    0.0 SIGMA= 24.8 PHAS=    0.0 FOM= 0.00 TEST= 0
INDE 18 66 34 FOBS=   93.2 SIGMA=  3.5 PHAS=   85.2 FOM= 0.88 TEST= 0
INDE 18 66 36 FOBS=   76.9 SIGMA=  4.4 PHAS=   -6.3 FOM= 0.89 TEST= 0
INDE 18 67 19 FOBS=   88.4 SIGMA=  3.4 PHAS=  -82.7 FOM= 0.90 TEST= 0
INDE 18 67 21 FOBS=   50.2 SIGMA=  6.2 PHAS=  -91.1 FOM= 0.58 TEST= 0
INDE 18 67 23 FOBS=    0.0 SIGMA= 26.5 PHAS=    0.0 FOM= 0.00 TEST= 0
INDE 18 67 25 FOBS=   79.6 SIGMA=  4.6 PHAS=   98.1 FOM= 0.70 TEST= 0
INDE 18 67 27 FOBS=   39.1 SIGMA=  9.1 PHAS= -162.6 FOM= 0.59 TEST= 0
INDE 18 67 29 FOBS=    0.0 SIGMA= 26.9 PHAS=    0.0 FOM= 0.00 TEST= 0
INDE 18 67 31 FOBS=    0.0 SIGMA= 24.6 PHAS=    0.0 FOM= 0.00 TEST= 0
INDE 18 67 33 FOBS=    0.0 SIGMA= 28.3 PHAS=    0.0 FOM= 0.00 TEST= 0
INDE 18 67 35 FOBS=   88.4 SIGMA=  4.5 PHAS=  -83.8 FOM= 0.91 TEST= 0
INDE 18 68 18 FOBS=   46.3 SIGMA=  7.7 PHAS=   54.1 FOM= 0.47 TEST= 0
INDE 18 68 20 FOBS=   82.8 SIGMA=  4.7 PHAS=  152.2 FOM= 0.88 TEST= 0
INDE 18 68 22 FOBS=   63.4 SIGMA=  6.1 PHAS= -140.7 FOM= 0.76 TEST= 0
INDE 18 68 24 FOBS=  124.4 SIGMA=  4.3 PHAS=   29.7 FOM= 0.92 TEST= 0
INDE 18 68 26 FOBS=    0.0 SIGMA= 31.9 PHAS=    0.0 FOM= 0.00 TEST= 0
```

*FIG. 12A - 423*

```
INDE  18  68  28  FOBS=   35.3  SIGMA=   8.4  PHAS=  152.7  FOM=  0.55  TEST= 0
INDE  18  68  30  FOBS=   50.4  SIGMA=   6.1  PHAS= -100.6  FOM=  0.66  TEST= 0
INDE  18  68  32  FOBS=    0.0  SIGMA=  25.0  PHAS=    0.0  FOM=  0.00  TEST= 0
INDE  18  69  19  FOBS=   30.9  SIGMA=  12.1  PHAS=   11.8  FOM=  0.29  TEST= 0
INDE  18  69  21  FOBS=   55.1  SIGMA=   7.2  PHAS=  104.9  FOM=  0.67  TEST= 0
INDE  18  69  29  FOBS=   45.9  SIGMA=   8.1  PHAS=  -20.4  FOM=  0.63  TEST= 0
INDE  18  70  18  FOBS=    0.0  SIGMA=  26.3  PHAS=    0.0  FOM=  0.00  TEST= 1
INDE  18  70  20  FOBS=    0.0  SIGMA=  27.3  PHAS=    0.0  FOM=  0.00  TEST= 0
INDE  18  70  22  FOBS=    0.0  SIGMA=  28.1  PHAS=    0.0  FOM=  0.00  TEST= 0
INDE  18  71  19  FOBS=   67.9  SIGMA=   5.4  PHAS=  -73.6  FOM=  0.56  TEST= 0
INDE  18  71  21  FOBS=   83.4  SIGMA=   3.1  PHAS=  -88.3  FOM=  0.86  TEST= 0
INDE  18  71  23  FOBS=   45.8  SIGMA=   8.8  PHAS= -178.1  FOM=  0.33  TEST= 0
INDE  18  72  18  FOBS=   66.6  SIGMA=   5.0  PHAS=   66.3  FOM=  0.87  TEST= 0
INDE  18  72  20  FOBS=   30.7  SIGMA=   6.7  PHAS=  176.6  FOM=  0.33  TEST= 0
INDE  18  72  22  FOBS=   70.8  SIGMA=   5.9  PHAS=  174.6  FOM=  0.86  TEST= 0
INDE  18  73  19  FOBS=   30.0  SIGMA=  11.9  PHAS=  -33.3  FOM=  0.64  TEST= 0
INDE  19  20  19  FOBS=  127.9  SIGMA=   1.0  PHAS=  -25.7  FOM=  0.96  TEST= 0
INDE  19  20  21  FOBS=  120.2  SIGMA=   1.1  PHAS=   44.5  FOM=  0.96  TEST= 0
INDE  19  20  23  FOBS=  207.9  SIGMA=   0.6  PHAS=  111.9  FOM=  0.99  TEST= 0
INDE  19  20  25  FOBS=   85.7  SIGMA=   1.3  PHAS=  175.6  FOM=  0.53  TEST= 0
INDE  19  20  27  FOBS=  303.5  SIGMA=   0.5  PHAS=  -65.9  FOM=  0.97  TEST= 0
INDE  19  20  29  FOBS=  119.7  SIGMA=   1.2  PHAS=   30.8  FOM=  0.98  TEST= 0
INDE  19  20  31  FOBS=  364.9  SIGMA=   0.6  PHAS=  132.2  FOM=  0.98  TEST= 0
INDE  19  20  33  FOBS=  146.4  SIGMA=   1.2  PHAS=   15.7  FOM=  0.98  TEST= 1
INDE  19  20  35  FOBS=  126.1  SIGMA=   1.5  PHAS=   97.7  FOM=  0.92  TEST= 0
INDE  19  20  37  FOBS=  116.2  SIGMA=   1.6  PHAS=  117.3  FOM=  0.99  TEST= 0
INDE  19  20  39  FOBS=  150.9  SIGMA=   1.4  PHAS=  -59.7  FOM=  0.92  TEST= 0
INDE  19  20  41  FOBS=   95.7  SIGMA=   2.0  PHAS=   52.2  FOM=  0.96  TEST= 0
INDE  19  20  43  FOBS=  175.4  SIGMA=   1.1  PHAS=  -94.3  FOM=  0.92  TEST= 0
INDE  19  20  45  FOBS=  133.3  SIGMA=   1.4  PHAS= -113.5  FOM=  0.94  TEST= 0
INDE  19  20  47  FOBS=   81.8  SIGMA=   2.0  PHAS=  -72.4  FOM=  0.53  TEST= 0
INDE  19  20  49  FOBS=   40.5  SIGMA=   5.5  PHAS=  117.3  FOM=  0.13  TEST= 0
INDE  19  20  51  FOBS=    0.0  SIGMA=  21.0  PHAS=    0.0  FOM=  0.00  TEST= 0
INDE  19  20  53  FOBS=   64.9  SIGMA=   3.0  PHAS=  170.3  FOM=  0.90  TEST= 0
INDE  19  20  55  FOBS=   97.1  SIGMA=   2.1  PHAS=  106.8  FOM=  0.93  TEST= 0
INDE  19  20  57  FOBS=   80.0  SIGMA=   2.8  PHAS= -177.5  FOM=  0.04  TEST= 1
INDE  19  20  59  FOBS=  104.5  SIGMA=   2.7  PHAS= -150.3  FOM=  0.87  TEST= 0
INDE  19  20  61  FOBS=   46.4  SIGMA=   6.5  PHAS=  -61.5  FOM=  0.35  TEST= 0
INDE  19  20  63  FOBS=   54.9  SIGMA=   4.8  PHAS=  104.6  FOM=  0.58  TEST= 0
INDE  19  20  65  FOBS=    3.0  SIGMA=  86.2  PHAS=  -41.9  FOM=  0.00  TEST= 1
INDE  19  20  67  FOBS=   61.4  SIGMA=   6.1  PHAS=  100.2  FOM=  0.85  TEST= 0
INDE  19  20  69  FOBS=   87.8  SIGMA=   4.3  PHAS=   56.4  FOM=  0.91  TEST= 0
INDE  19  20  71  FOBS=   35.1  SIGMA=   6.0  PHAS=   68.5  FOM=  0.19  TEST= 1
INDE  19  21  20  FOBS=  221.3  SIGMA=   0.6  PHAS=  -37.0  FOM=  0.97  TEST= 0
INDE  19  21  22  FOBS=   39.6  SIGMA=   2.3  PHAS=  131.0  FOM=  0.98  TEST= 1
INDE  19  21  24  FOBS=  113.3  SIGMA=   0.8  PHAS=   -0.1  FOM=  0.88  TEST= 1
INDE  19  21  26  FOBS=  220.6  SIGMA=   0.5  PHAS= -144.4  FOM=  0.96  TEST= 0
INDE  19  21  28  FOBS=  305.2  SIGMA=   0.5  PHAS= -169.6  FOM=  0.94  TEST= 0
INDE  19  21  30  FOBS=  142.1  SIGMA=   0.9  PHAS=   18.3  FOM=  0.78  TEST= 0
INDE  19  21  32  FOBS=  320.5  SIGMA=   0.8  PHAS=   -1.2  FOM=  0.97  TEST= 0
INDE  19  21  34  FOBS=  190.0  SIGMA=   0.8  PHAS=  155.3  FOM=  0.94  TEST= 1
INDE  19  21  36  FOBS=   75.0  SIGMA=   2.0  PHAS=  102.5  FOM=  0.97  TEST= 0
INDE  19  21  38  FOBS=  126.7  SIGMA=   1.3  PHAS=  116.8  FOM=  0.72  TEST= 0
INDE  19  21  40  FOBS=  102.0  SIGMA=   1.7  PHAS=  -24.1  FOM=  0.73  TEST= 0
INDE  19  21  42  FOBS=  171.4  SIGMA=   1.0  PHAS= -100.4  FOM=  0.94  TEST= 0
INDE  19  21  44  FOBS=   65.3  SIGMA=   2.3  PHAS=   42.4  FOM=  0.49  TEST= 0
INDE  19  21  46  FOBS=   35.0  SIGMA=   4.6  PHAS= -131.0  FOM=  0.21  TEST= 1
INDE  19  21  48  FOBS=   69.3  SIGMA=   2.5  PHAS= -103.5  FOM=  0.89  TEST= 0
INDE  19  21  50  FOBS=   95.6  SIGMA=   2.0  PHAS=   22.4  FOM=  0.59  TEST= 0
INDE  19  21  52  FOBS=   56.2  SIGMA=   3.6  PHAS=  -69.9  FOM=  0.61  TEST= 0
INDE  19  21  54  FOBS=   33.0  SIGMA=   6.0  PHAS=   25.4  FOM=  0.27  TEST= 0
INDE  19  21  56  FOBS=   81.5  SIGMA=   2.8  PHAS=   52.8  FOM=  0.93  TEST= 0
INDE  19  21  58  FOBS=  116.8  SIGMA=   2.4  PHAS=   36.7  FOM=  0.44  TEST= 1
INDE  19  21  60  FOBS=   46.3  SIGMA=   5.8  PHAS= -177.4  FOM=  0.53  TEST= 0
INDE  19  21  62  FOBS=   81.5  SIGMA=   3.4  PHAS=  -56.2  FOM=  0.89  TEST= 0
INDE  19  21  64  FOBS=    0.0  SIGMA=  22.9  PHAS=    0.0  FOM=  0.00  TEST= 0
INDE  19  21  66  FOBS=    0.0  SIGMA=  24.7  PHAS=    0.0  FOM=  0.00  TEST= 0
INDE  19  21  68  FOBS=   34.1  SIGMA=  11.0  PHAS=   -6.3  FOM=  0.72  TEST= 0
INDE  19  21  70  FOBS=    0.0  SIGMA=  26.0  PHAS=    0.0  FOM=  0.00  TEST= 0
INDE  19  21  72  FOBS=    0.0  SIGMA=  25.9  PHAS=    0.0  FOM=  0.00  TEST= 0
```

*FIG. 12A - 424*

```
INDE 19 22 19 FOBS=    36.5 SIGMA=  2.7 PHAS=  107.5 FOM= 0.84 TEST= 0
INDE 19 22 21 FOBS=   106.1 SIGMA=  1.0 PHAS=   51.2 FOM= 0.76 TEST= 0
INDE 19 22 23 FOBS=   135.5 SIGMA=  0.8 PHAS=  134.3 FOM= 0.69 TEST= 0
INDE 19 22 25 FOBS=   134.4 SIGMA=  0.8 PHAS=   48.9 FOM= 0.87 TEST= 0
INDE 19 22 27 FOBS=    28.2 SIGMA=  3.5 PHAS=  -47.2 FOM= 0.36 TEST= 0
INDE 19 22 29 FOBS=    17.9 SIGMA=  6.0 PHAS=   -2.9 FOM= 0.66 TEST= 0
INDE 19 22 31 FOBS=    94.2 SIGMA=  1.3 PHAS= -118.1 FOM= 0.87 TEST= 0
INDE 19 22 33 FOBS=   265.0 SIGMA=  0.6 PHAS=   73.4 FOM= 0.94 TEST= 0
INDE 19 22 35 FOBS=   172.6 SIGMA=  0.9 PHAS=   62.9 FOM= 0.95 TEST= 0
INDE 19 22 37 FOBS=     0.0 SIGMA= 17.7 PHAS=    0.0 FOM= 0.00 TEST= 0
INDE 19 22 39 FOBS=    72.6 SIGMA=  2.2 PHAS=  115.0 FOM= 0.85 TEST= 0
INDE 19 22 41 FOBS=     0.0 SIGMA= 17.5 PHAS=    0.0 FOM= 0.00 TEST= 0
INDE 19 22 43 FOBS=    90.5 SIGMA=  1.7 PHAS=  -89.8 FOM= 0.77 TEST= 0
INDE 19 22 45 FOBS=    46.1 SIGMA=  3.5 PHAS=   52.7 FOM= 0.20 TEST= 0
INDE 19 22 47 FOBS=   134.8 SIGMA=  1.3 PHAS=  -22.2 FOM= 0.88 TEST= 0
INDE 19 22 49 FOBS=    26.6 SIGMA=  7.2 PHAS=   69.5 FOM= 0.79 TEST= 0
INDE 19 22 51 FOBS=    62.6 SIGMA=  2.9 PHAS=  127.3 FOM= 0.50 TEST= 0
INDE 19 22 53 FOBS=    67.7 SIGMA=  3.0 PHAS= -176.2 FOM= 0.69 TEST= 0
INDE 19 22 55 FOBS=   108.0 SIGMA=  1.9 PHAS=  -29.7 FOM= 0.92 TEST= 0
INDE 19 22 57 FOBS=   213.6 SIGMA=  1.2 PHAS=  -30.5 FOM= 0.98 TEST= 0
INDE 19 22 59 FOBS=    51.1 SIGMA=  5.3 PHAS=  175.1 FOM= 0.76 TEST= 0
INDE 19 22 61 FOBS=    53.6 SIGMA=  5.1 PHAS=  -13.6 FOM= 0.38 TEST= 1
INDE 19 22 63 FOBS=   121.4 SIGMA=  2.3 PHAS= -115.5 FOM= 0.95 TEST= 0
INDE 19 22 65 FOBS=   111.1 SIGMA=  2.9 PHAS=  -19.3 FOM= 0.72 TEST= 0
INDE 19 22 67 FOBS=    66.0 SIGMA=  5.5 PHAS=  -28.0 FOM= 0.88 TEST= 0
INDE 19 22 69 FOBS=     0.0 SIGMA= 26.4 PHAS=    0.0 FOM= 0.00 TEST= 0
INDE 19 22 71 FOBS=    50.3 SIGMA=  6.9 PHAS=  166.9 FOM= 0.76 TEST= 0
INDE 19 23 20 FOBS=   221.8 SIGMA=  0.6 PHAS=   -2.8 FOM= 0.95 TEST= 0
INDE 19 23 22 FOBS=   210.7 SIGMA=  0.6 PHAS=  -78.5 FOM= 0.97 TEST= 0
INDE 19 23 24 FOBS=   279.3 SIGMA=  0.6 PHAS= -111.0 FOM= 0.94 TEST= 0
INDE 19 23 26 FOBS=   323.4 SIGMA=  0.5 PHAS=   31.6 FOM= 0.64 TEST= 1
INDE 19 23 28 FOBS=   236.9 SIGMA=  0.6 PHAS=  178.3 FOM= 0.94 TEST= 0
INDE 19 23 30 FOBS=    89.2 SIGMA=  1.4 PHAS= -176.4 FOM= 0.81 TEST= 0
INDE 19 23 32 FOBS=   206.7 SIGMA=  0.7 PHAS=   24.7 FOM= 0.92 TEST= 0
INDE 19 23 34 FOBS=   171.0 SIGMA=  0.9 PHAS=  -39.8 FOM= 0.95 TEST= 0
INDE 19 23 36 FOBS=   161.3 SIGMA=  1.0 PHAS=   -0.1 FOM= 0.77 TEST= 0
INDE 19 23 38 FOBS=   165.9 SIGMA=  1.1 PHAS=   88.1 FOM= 0.91 TEST= 0
INDE 19 23 40 FOBS=   179.9 SIGMA=  1.0 PHAS= -114.9 FOM= 0.54 TEST= 1
INDE 19 23 42 FOBS=   218.4 SIGMA=  0.8 PHAS=  -76.7 FOM= 0.95 TEST= 0
INDE 19 23 44 FOBS=    28.8 SIGMA=  5.0 PHAS=   77.9 FOM= 0.16 TEST= 0
INDE 19 23 46 FOBS=    38.7 SIGMA=  3.6 PHAS=  -41.2 FOM= 0.74 TEST= 0
INDE 19 23 48 FOBS=   167.2 SIGMA=  1.0 PHAS=  -65.9 FOM= 0.89 TEST= 0
INDE 19 23 50 FOBS=    97.1 SIGMA=  1.9 PHAS=   -8.6 FOM= 0.85 TEST= 0
INDE 19 23 52 FOBS=    42.2 SIGMA=  4.6 PHAS=  -46.4 FOM= 0.78 TEST= 0
INDE 19 23 54 FOBS=     0.0 SIGMA= 20.6 PHAS=    0.0 FOM= 0.00 TEST= 0
INDE 19 23 56 FOBS=   114.4 SIGMA=  2.1 PHAS= -115.4 FOM= 0.94 TEST= 0
INDE 19 23 58 FOBS=    47.4 SIGMA=  5.3 PHAS= -136.8 FOM= 0.68 TEST= 0
INDE 19 23 60 FOBS=    24.4 SIGMA= 11.2 PHAS=  146.0 FOM= 0.13 TEST= 0
INDE 19 23 62 FOBS=    29.0 SIGMA=  9.3 PHAS=   45.0 FOM= 0.24 TEST= 0
INDE 19 23 64 FOBS=   161.0 SIGMA=  1.8 PHAS= -114.4 FOM= 0.10 TEST= 1
INDE 19 23 66 FOBS=   110.3 SIGMA=  3.4 PHAS=  134.4 FOM= 0.18 TEST= 1
INDE 19 23 68 FOBS=    75.5 SIGMA=  4.8 PHAS=  -36.6 FOM= 0.91 TEST= 0
INDE 19 23 70 FOBS=    35.9 SIGMA= 10.1 PHAS= -100.1 FOM= 0.09 TEST= 0
INDE 19 24 19 FOBS=   173.8 SIGMA=  0.7 PHAS=   -3.4 FOM= 0.96 TEST= 0
INDE 19 24 21 FOBS=   136.9 SIGMA=  0.9 PHAS=  141.4 FOM= 0.91 TEST= 0
INDE 19 24 23 FOBS=   383.0 SIGMA=  0.5 PHAS=  104.9 FOM= 0.96 TEST= 1
INDE 19 24 25 FOBS=   417.2 SIGMA=  0.5 PHAS=   82.3 FOM= 0.96 TEST= 0
INDE 19 24 27 FOBS=   199.7 SIGMA=  0.7 PHAS=   61.7 FOM= 0.81 TEST= 0
INDE 19 24 29 FOBS=   105.6 SIGMA=  1.1 PHAS=   38.3 FOM= 0.89 TEST= 0
INDE 19 24 31 FOBS=   135.3 SIGMA=  1.0 PHAS=  -55.7 FOM= 0.96 TEST= 0
INDE 19 24 33 FOBS=   192.3 SIGMA=  0.8 PHAS=  114.2 FOM= 0.95 TEST= 0
INDE 19 24 35 FOBS=   147.3 SIGMA=  1.1 PHAS= -131.6 FOM= 0.90 TEST= 0
INDE 19 24 37 FOBS=   197.1 SIGMA=  0.9 PHAS=  -71.4 FOM= 0.92 TEST= 0
INDE 19 24 39 FOBS=    40.2 SIGMA=  4.5 PHAS=   69.2 FOM= 0.36 TEST= 0
INDE 19 24 41 FOBS=    50.3 SIGMA=  3.4 PHAS=  157.0 FOM= 0.57 TEST= 0
INDE 19 24 43 FOBS=     7.5 SIGMA= 19.5 PHAS=   -0.4 FOM= 0.04 TEST= 0
INDE 19 24 45 FOBS=    72.1 SIGMA=  2.0 PHAS=   38.1 FOM= 0.54 TEST= 0
INDE 19 24 47 FOBS=    35.6 SIGMA=  4.3 PHAS=  -51.2 FOM= 0.65 TEST= 0
INDE 19 24 49 FOBS=    92.5 SIGMA=  1.7 PHAS= -132.8 FOM= 0.84 TEST= 0
INDE 19 24 51 FOBS=   107.7 SIGMA=  1.5 PHAS= -157.4 FOM= 0.89 TEST= 0
```

*FIG. 12A - 425*

```
INDE 19 24 53 FOBS=   181.8 SIGMA=  1.1 PHAS= -176.6 FOM= 0.97 TEST= 0
INDE 19 24 55 FOBS=     0.0 SIGMA= 19.5 PHAS=    0.0 FOM= 0.00 TEST= 0
INDE 19 24 57 FOBS=    58.2 SIGMA=  5.6 PHAS=   40.6 FOM= 0.72 TEST= 0
INDE 19 24 59 FOBS=    74.8 SIGMA=  3.8 PHAS=  167.8 FOM= 0.79 TEST= 0
INDE 19 24 61 FOBS=    48.3 SIGMA=  5.7 PHAS=  -49.6 FOM= 0.82 TEST= 0
INDE 19 24 63 FOBS=     0.0 SIGMA= 27.4 PHAS=    0.0 FOM= 0.00 TEST= 0
INDE 19 24 65 FOBS=    86.0 SIGMA=  3.7 PHAS=  141.2 FOM= 0.89 TEST= 0
INDE 19 24 67 FOBS=    31.9 SIGMA= 11.4 PHAS=  -53.7 FOM= 0.64 TEST= 0
INDE 19 24 69 FOBS=    88.1 SIGMA=  4.3 PHAS= -112.4 FOM= 0.91 TEST= 0
INDE 19 24 71 FOBS=    81.0 SIGMA=  4.3 PHAS= -159.5 FOM= 0.79 TEST= 0
INDE 19 25 20 FOBS=    35.3 SIGMA=  3.5 PHAS=  136.7 FOM= 0.19 TEST= 0
INDE 19 25 22 FOBS=   312.3 SIGMA=  0.6 PHAS=  -29.7 FOM= 0.96 TEST= 0
INDE 19 25 24 FOBS=    86.5 SIGMA=  1.4 PHAS=  -80.4 FOM= 0.65 TEST= 1
INDE 19 25 26 FOBS=   101.8 SIGMA=  1.2 PHAS= -105.3 FOM= 0.45 TEST= 0
INDE 19 25 28 FOBS=    74.3 SIGMA=  1.6 PHAS=  -59.4 FOM= 0.76 TEST= 0
INDE 19 25 30 FOBS=   111.9 SIGMA=  1.2 PHAS=  171.3 FOM= 0.90 TEST= 1
INDE 19 25 32 FOBS=   157.0 SIGMA=  0.9 PHAS=  170.1 FOM= 0.98 TEST= 0
INDE 19 25 34 FOBS=    79.1 SIGMA=  1.9 PHAS=  109.6 FOM= 0.86 TEST= 0
INDE 19 25 36 FOBS=   159.3 SIGMA=  1.1 PHAS=  174.1 FOM= 0.95 TEST= 0
INDE 19 25 38 FOBS=    50.7 SIGMA=  3.3 PHAS=  173.4 FOM= 0.76 TEST= 0
INDE 19 25 40 FOBS=    66.8 SIGMA=  2.6 PHAS=  175.0 FOM= 0.75 TEST= 0
INDE 19 25 42 FOBS=   257.3 SIGMA=  0.7 PHAS=  -61.0 FOM= 0.97 TEST= 0
INDE 19 25 44 FOBS=    20.6 SIGMA=  7.7 PHAS=   10.4 FOM= 0.22 TEST= 0
INDE 19 25 46 FOBS=    75.0 SIGMA=  2.1 PHAS=  -30.7 FOM= 0.25 TEST= 0
INDE 19 25 48 FOBS=    75.1 SIGMA=  2.1 PHAS= -138.1 FOM= 0.59 TEST= 0
INDE 19 25 50 FOBS=    89.4 SIGMA=  1.7 PHAS=  128.1 FOM= 0.88 TEST= 0
INDE 19 25 52 FOBS=   108.9 SIGMA=  1.5 PHAS=   94.2 FOM= 0.94 TEST= 0
INDE 19 25 54 FOBS=    93.8 SIGMA=  1.7 PHAS=   63.4 FOM= 0.93 TEST= 0
INDE 19 25 56 FOBS=     0.0 SIGMA= 19.5 PHAS=    0.0 FOM= 0.00 TEST= 1
INDE 19 25 58 FOBS=     0.0 SIGMA= 27.5 PHAS=    0.0 FOM= 0.00 TEST= 0
INDE 19 25 60 FOBS=    60.1 SIGMA=  4.6 PHAS= -138.2 FOM= 0.65 TEST= 0
INDE 19 25 62 FOBS=    21.7 SIGMA= 12.4 PHAS=   58.0 FOM= 0.15 TEST= 0
INDE 19 25 64 FOBS=     0.0 SIGMA= 25.3 PHAS=    0.0 FOM= 0.00 TEST= 0
INDE 19 25 66 FOBS=    14.7 SIGMA= 25.9 PHAS= -113.1 FOM= 0.26 TEST= 0
INDE 19 25 68 FOBS=    39.7 SIGMA=  9.3 PHAS= -148.9 FOM= 0.08 TEST= 1
INDE 19 25 70 FOBS=    42.5 SIGMA=  8.4 PHAS=  148.4 FOM= 0.62 TEST= 0
INDE 19 26 19 FOBS=    85.2 SIGMA=  1.3 PHAS=   10.7 FOM= 0.97 TEST= 0
INDE 19 26 21 FOBS=   264.7 SIGMA=  0.6 PHAS=  116.4 FOM= 0.91 TEST= 0
INDE 19 26 23 FOBS=    30.1 SIGMA=  4.0 PHAS=  141.0 FOM= 0.76 TEST= 0
INDE 19 26 25 FOBS=     0.0 SIGMA= 16.3 PHAS=    0.0 FOM= 0.00 TEST= 0
INDE 19 26 27 FOBS=   140.8 SIGMA=  0.9 PHAS=  141.6 FOM= 0.77 TEST= 0
INDE 19 26 29 FOBS=   179.4 SIGMA=  0.8 PHAS=  -17.2 FOM= 0.94 TEST= 0
INDE 19 26 31 FOBS=   191.8 SIGMA=  0.8 PHAS=   69.8 FOM= 0.90 TEST= 1
INDE 19 26 33 FOBS=   159.6 SIGMA=  1.0 PHAS=  118.2 FOM= 0.91 TEST= 0
INDE 19 26 35 FOBS=   153.1 SIGMA=  1.1 PHAS=   15.6 FOM= 0.83 TEST= 0
INDE 19 26 37 FOBS=    72.7 SIGMA=  2.3 PHAS=   96.5 FOM= 0.63 TEST= 0
INDE 19 26 39 FOBS=   136.5 SIGMA=  1.3 PHAS=  -92.7 FOM= 0.90 TEST= 0
INDE 19 26 41 FOBS=   175.6 SIGMA=  1.1 PHAS=   -6.4 FOM= 0.93 TEST= 0
INDE 19 26 43 FOBS=   119.4 SIGMA=  1.4 PHAS= -139.9 FOM= 0.88 TEST= 0
INDE 19 26 45 FOBS=   103.8 SIGMA=  1.7 PHAS=   18.2 FOM= 0.91 TEST= 0
INDE 19 26 47 FOBS=   134.2 SIGMA=  1.3 PHAS=   83.8 FOM= 0.67 TEST= 0
INDE 19 26 49 FOBS=    37.2 SIGMA=  4.0 PHAS=  -57.4 FOM= 0.77 TEST= 0
INDE 19 26 51 FOBS=   115.3 SIGMA=  1.3 PHAS=   70.3 FOM= 0.94 TEST= 0
INDE 19 26 53 FOBS=    98.2 SIGMA=  1.7 PHAS= -132.2 FOM= 0.82 TEST= 0
INDE 19 26 55 FOBS=    78.5 SIGMA=  2.2 PHAS=   50.0 FOM= 0.91 TEST= 0
INDE 19 26 57 FOBS=     0.0 SIGMA= 19.4 PHAS=    0.0 FOM= 0.00 TEST= 0
INDE 19 26 59 FOBS=    58.5 SIGMA=  3.7 PHAS=   77.4 FOM= 0.27 TEST= 0
INDE 19 26 61 FOBS=    37.5 SIGMA=  7.4 PHAS=  -33.5 FOM= 0.66 TEST= 0
INDE 19 26 63 FOBS=    41.3 SIGMA=  6.6 PHAS=   -4.4 FOM= 0.85 TEST= 0
INDE 19 26 65 FOBS=    64.0 SIGMA=  6.1 PHAS=   87.0 FOM= 0.79 TEST= 0
INDE 19 26 67 FOBS=    10.7 SIGMA= 33.6 PHAS= -159.4 FOM= 0.09 TEST= 1
INDE 19 26 69 FOBS=     0.0 SIGMA= 26.7 PHAS=    0.0 FOM= 0.00 TEST= 0
INDE 19 27 20 FOBS=    67.9 SIGMA=  1.7 PHAS=  118.8 FOM= 0.88 TEST= 0
INDE 19 27 22 FOBS=   260.7 SIGMA=  0.6 PHAS=  -43.3 FOM= 0.94 TEST= 0
INDE 19 27 24 FOBS=   328.5 SIGMA=  0.6 PHAS=  154.4 FOM= 0.98 TEST= 0
INDE 19 27 26 FOBS=   180.2 SIGMA=  0.8 PHAS= -102.9 FOM= 0.98 TEST= 0
INDE 19 27 28 FOBS=   149.2 SIGMA=  0.9 PHAS=    1.2 FOM= 0.93 TEST= 0
INDE 19 27 30 FOBS=    53.0 SIGMA=  2.6 PHAS= -126.0 FOM= 0.89 TEST= 0
INDE 19 27 32 FOBS=   105.9 SIGMA=  1.5 PHAS=  -74.9 FOM= 0.96 TEST= 1
INDE 19 27 34 FOBS=    78.0 SIGMA=  2.2 PHAS= -149.2 FOM= 0.64 TEST= 1
```

*FIG. 12A - 426*

```
INDE  19  27  36  FOBS=  119.4  SIGMA=   1.5  PHAS=   -39.9  FOM=  0.45  TEST= 0
INDE  19  27  38  FOBS=  164.8  SIGMA=   1.1  PHAS=  -135.1  FOM=  0.98  TEST= 0
INDE  19  27  40  FOBS=  203.5  SIGMA=   0.9  PHAS=  -131.7  FOM=  0.94  TEST= 0
INDE  19  27  42  FOBS=  199.6  SIGMA=   0.9  PHAS=   -55.6  FOM=  0.93  TEST= 0
INDE  19  27  44  FOBS=   33.3  SIGMA=   5.3  PHAS=   129.8  FOM=  0.38  TEST= 0
INDE  19  27  46  FOBS=   81.9  SIGMA=   2.1  PHAS=   179.9  FOM=  0.95  TEST= 0
INDE  19  27  48  FOBS=   81.9  SIGMA=   2.1  PHAS=   168.1  FOM=  0.82  TEST= 0
INDE  19  27  50  FOBS=   66.2  SIGMA=   2.3  PHAS=   -62.7  FOM=  0.82  TEST= 0
INDE  19  27  52  FOBS=   87.5  SIGMA=   1.7  PHAS=   -13.8  FOM=  0.89  TEST= 0
INDE  19  27  54  FOBS=   43.5  SIGMA=   3.5  PHAS=   -47.8  FOM=  0.83  TEST= 0
INDE  19  27  56  FOBS=    0.0  SIGMA=  19.4  PHAS=     0.0  FOM=  0.00  TEST= 0
INDE  19  27  58  FOBS=    0.0  SIGMA=  19.4  PHAS=     0.0  FOM=  0.00  TEST= 0
INDE  19  27  60  FOBS=   35.1  SIGMA=   6.2  PHAS=  -130.6  FOM=  0.74  TEST= 0
INDE  19  27  62  FOBS=   35.3  SIGMA=   8.8  PHAS=   -25.7  FOM=  0.41  TEST= 0
INDE  19  27  64  FOBS=   57.9  SIGMA=   6.7  PHAS=   -62.3  FOM=  0.93  TEST= 0
INDE  19  27  66  FOBS=   52.4  SIGMA=   7.2  PHAS=   -66.0  FOM=  0.73  TEST= 0
INDE  19  27  68  FOBS=   46.9  SIGMA=   7.7  PHAS=   178.6  FOM=  0.00  TEST= 1
INDE  19  28  19  FOBS=  159.4  SIGMA=   0.9  PHAS=    73.8  FOM=  0.97  TEST= 0
INDE  19  28  21  FOBS=  214.4  SIGMA=   0.7  PHAS=   100.5  FOM=  0.92  TEST= 0
INDE  19  28  23  FOBS=  345.6  SIGMA=   0.7  PHAS=    26.0  FOM=  0.97  TEST= 0
INDE  19  28  25  FOBS=   12.5  SIGMA=  10.7  PHAS=  -145.1  FOM=  0.08  TEST= 0
INDE  19  28  27  FOBS=  249.7  SIGMA=   0.7  PHAS=   171.7  FOM=  0.97  TEST= 0
INDE  19  28  29  FOBS=  169.1  SIGMA=   0.9  PHAS=    -6.6  FOM=  0.92  TEST= 0
INDE  19  28  31  FOBS=  162.1  SIGMA=   1.0  PHAS=   150.8  FOM=  0.91  TEST= 0
INDE  19  28  33  FOBS=   50.6  SIGMA=   3.4  PHAS=   -91.8  FOM=  0.45  TEST= 0
INDE  19  28  35  FOBS=  117.5  SIGMA=   1.7  PHAS=    15.1  FOM=  0.89  TEST= 0
INDE  19  28  37  FOBS=  194.4  SIGMA=   0.9  PHAS=   173.3  FOM=  0.95  TEST= 0
INDE  19  28  39  FOBS=   85.2  SIGMA=   2.0  PHAS=    99.8  FOM=  0.91  TEST= 0
INDE  19  28  41  FOBS=  102.2  SIGMA=   1.7  PHAS=   -40.0  FOM=  0.82  TEST= 0
INDE  19  28  43  FOBS=   96.7  SIGMA=   1.9  PHAS=   161.7  FOM=  0.75  TEST= 0
INDE  19  28  45  FOBS=   97.1  SIGMA=   1.8  PHAS=   135.1  FOM=  0.92  TEST= 0
INDE  19  28  47  FOBS=  279.5  SIGMA=   0.8  PHAS=    66.2  FOM=  0.98  TEST= 0
INDE  19  28  49  FOBS=   39.5  SIGMA=   4.1  PHAS=   127.7  FOM=  0.58  TEST= 0
INDE  19  28  51  FOBS=   47.8  SIGMA=   3.3  PHAS=  -153.8  FOM=  0.86  TEST= 0
INDE  19  28  53  FOBS=  130.7  SIGMA=   1.2  PHAS=   177.0  FOM=  0.95  TEST= 0
INDE  19  28  55  FOBS=   60.2  SIGMA=   2.7  PHAS=   102.9  FOM=  0.81  TEST= 0
INDE  19  28  57  FOBS=   51.3  SIGMA=   3.7  PHAS=  -114.9  FOM=  0.56  TEST= 0
INDE  19  28  59  FOBS=   57.4  SIGMA=   3.3  PHAS=    32.3  FOM=  0.75  TEST= 1
INDE  19  28  61  FOBS=   69.7  SIGMA=   3.2  PHAS=    10.0  FOM=  0.72  TEST= 0
INDE  19  28  63  FOBS=  113.3  SIGMA=   2.2  PHAS=  -118.1  FOM=  0.94  TEST= 0
INDE  19  28  65  FOBS=   55.9  SIGMA=   6.8  PHAS=    70.1  FOM=  0.11  TEST= 1
INDE  19  28  67  FOBS=   68.8  SIGMA=   5.3  PHAS=   140.6  FOM=  0.71  TEST= 0
INDE  19  29  20  FOBS=  134.7  SIGMA=   1.0  PHAS=   -63.9  FOM=  0.87  TEST= 1
INDE  19  29  22  FOBS=  243.2  SIGMA=   0.7  PHAS=   -78.1  FOM=  0.98  TEST= 0
INDE  19  29  24  FOBS=  273.4  SIGMA=   0.6  PHAS=  -172.8  FOM=  0.98  TEST= 0
INDE  19  29  26  FOBS=   42.5  SIGMA=   3.8  PHAS=  -158.1  FOM=  0.84  TEST= 0
INDE  19  29  28  FOBS=    0.0  SIGMA=  16.6  PHAS=     0.0  FOM=  0.00  TEST= 1
INDE  19  29  30  FOBS=   67.9  SIGMA=   2.3  PHAS=  -136.6  FOM=  0.48  TEST= 0
INDE  19  29  32  FOBS=  152.4  SIGMA=   1.1  PHAS=  -128.4  FOM=  0.71  TEST= 0
INDE  19  29  34  FOBS=  209.7  SIGMA=   1.0  PHAS=  -138.7  FOM=  0.94  TEST= 0
INDE  19  29  36  FOBS=  170.7  SIGMA=   1.2  PHAS=    69.4  FOM=  0.94  TEST= 0
INDE  19  29  38  FOBS=   10.7  SIGMA=  20.2  PHAS=   -44.0  FOM=  0.60  TEST= 0
INDE  19  29  40  FOBS=  237.6  SIGMA=   0.8  PHAS=   -45.1  FOM=  0.97  TEST= 0
INDE  19  29  42  FOBS=   35.1  SIGMA=   5.7  PHAS=   -47.3  FOM=  0.48  TEST= 0
INDE  19  29  44  FOBS=  136.1  SIGMA=   1.4  PHAS=    74.0  FOM=  0.90  TEST= 0
INDE  19  29  46  FOBS=  161.5  SIGMA=   1.1  PHAS=   -64.0  FOM=  0.93  TEST= 0
INDE  19  29  48  FOBS=  142.5  SIGMA=   1.2  PHAS=   -24.6  FOM=  0.96  TEST= 0
INDE  19  29  50  FOBS=    0.0  SIGMA=  18.8  PHAS=     0.0  FOM=  0.00  TEST= 0
INDE  19  29  52  FOBS=  181.5  SIGMA=   1.1  PHAS=    54.3  FOM=  0.96  TEST= 0
INDE  19  29  54  FOBS=    0.0  SIGMA=  17.4  PHAS=     0.0  FOM=  0.00  TEST= 0
INDE  19  29  56  FOBS=   21.1  SIGMA=   8.0  PHAS=    97.3  FOM=  0.51  TEST= 0
INDE  19  29  58  FOBS=   61.8  SIGMA=   3.1  PHAS=   176.7  FOM=  0.21  TEST= 0
INDE  19  29  60  FOBS=   52.0  SIGMA=   3.7  PHAS=   -52.1  FOM=  0.42  TEST= 1
INDE  19  29  62  FOBS=   83.3  SIGMA=   2.7  PHAS=   175.0  FOM=  0.88  TEST= 0
INDE  19  29  64  FOBS=    0.0  SIGMA=  25.0  PHAS=     0.0  FOM=  0.00  TEST= 0
INDE  19  29  66  FOBS=   75.0  SIGMA=   4.1  PHAS=   -52.7  FOM=  0.92  TEST= 0
INDE  19  30  19  FOBS=  127.3  SIGMA=   1.2  PHAS=  -108.4  FOM=  0.98  TEST= 0
INDE  19  30  21  FOBS=  180.3  SIGMA=   0.8  PHAS=    86.8  FOM=  0.99  TEST= 0
INDE  19  30  23  FOBS=  180.2  SIGMA=   0.8  PHAS=    25.5  FOM=  0.97  TEST= 1
INDE  19  30  25  FOBS=  133.1  SIGMA=   1.2  PHAS=    62.0  FOM=  0.98  TEST= 0
```

*FIG. 12A - 427*

```
INDE  19  30  27  FOBS=  164.5  SIGMA=   1.0  PHAS=   74.5  FOM=  0.89  TEST=  0
INDE  19  30  29  FOBS=   46.5  SIGMA=   3.2  PHAS= -135.0  FOM=  0.64  TEST=  0
INDE  19  30  31  FOBS=  268.4  SIGMA=   0.7  PHAS=  168.4  FOM=  0.96  TEST=  0
INDE  19  30  33  FOBS=   91.5  SIGMA=   1.8  PHAS=  137.2  FOM=  0.95  TEST=  0
INDE  19  30  35  FOBS=  100.9  SIGMA=   1.8  PHAS=  126.0  FOM=  0.85  TEST=  0
INDE  19  30  37  FOBS=    0.0  SIGMA=  19.1  PHAS=    0.0  FOM=  0.00  TEST=  0
INDE  19  30  39  FOBS=    0.0  SIGMA=  19.5  PHAS=    0.0  FOM=  0.00  TEST=  0
INDE  19  30  41  FOBS=  181.1  SIGMA=   1.2  PHAS=  -67.9  FOM=  0.93  TEST=  0
INDE  19  30  43  FOBS=  185.9  SIGMA=   1.1  PHAS=   74.4  FOM=  0.95  TEST=  0
INDE  19  30  45  FOBS=  102.4  SIGMA=   1.7  PHAS= -124.7  FOM=  0.90  TEST=  0
INDE  19  30  47  FOBS=   26.7  SIGMA=   6.5  PHAS= -147.3  FOM=  0.38  TEST=  0
INDE  19  30  49  FOBS=   61.1  SIGMA=   2.7  PHAS= -127.2  FOM=  0.84  TEST=  0
INDE  19  30  51  FOBS=  107.2  SIGMA=   1.6  PHAS=  -92.8  FOM=  0.89  TEST=  0
INDE  19  30  53  FOBS=    0.0  SIGMA=  18.6  PHAS=    0.0  FOM=  0.00  TEST=  0
INDE  19  30  55  FOBS=   83.2  SIGMA=   2.4  PHAS=   84.3  FOM=  0.92  TEST=  0
INDE  19  30  57  FOBS=   68.1  SIGMA=   2.5  PHAS=   62.4  FOM=  0.42  TEST=  0
INDE  19  30  59  FOBS=   42.8  SIGMA=   4.7  PHAS=   89.5  FOM=  0.78  TEST=  0
INDE  19  30  61  FOBS=   61.5  SIGMA=   3.1  PHAS=   69.5  FOM=  0.45  TEST=  0
INDE  19  30  63  FOBS=    9.8  SIGMA=  24.5  PHAS=   83.7  FOM=  0.20  TEST=  0
INDE  19  30  65  FOBS=    0.0  SIGMA=  24.9  PHAS=    0.0  FOM=  0.00  TEST=  0
INDE  19  30  67  FOBS=   58.3  SIGMA=   9.7  PHAS=  149.7  FOM=  0.76  TEST=  0
INDE  19  30  69  FOBS=   93.5  SIGMA=   6.5  PHAS=  119.4  FOM=  0.93  TEST=  0
INDE  19  31  20  FOBS=  125.2  SIGMA=   1.2  PHAS=  -48.3  FOM=  0.89  TEST=  0
INDE  19  31  22  FOBS=  109.6  SIGMA=   1.3  PHAS=  -42.1  FOM=  0.86  TEST=  0
INDE  19  31  24  FOBS=  281.7  SIGMA=   0.7  PHAS=  -61.4  FOM=  0.99  TEST=  0
INDE  19  31  26  FOBS=  358.2  SIGMA=   0.6  PHAS=  -33.5  FOM=  0.97  TEST=  0
INDE  19  31  28  FOBS=  145.9  SIGMA=   1.2  PHAS= -163.9  FOM=  0.71  TEST=  0
INDE  19  31  30  FOBS=  200.9  SIGMA=   0.9  PHAS=   85.9  FOM=  0.91  TEST=  0
INDE  19  31  32  FOBS=  159.0  SIGMA=   1.1  PHAS=  -84.1  FOM=  0.88  TEST=  0
INDE  19  31  34  FOBS=   48.7  SIGMA=   3.6  PHAS=   38.8  FOM=  0.94  TEST=  0
INDE  19  31  36  FOBS=  103.0  SIGMA=   1.8  PHAS=   99.4  FOM=  0.58  TEST=  0
INDE  19  31  38  FOBS=  119.5  SIGMA=   1.8  PHAS= -157.9  FOM=  0.43  TEST=  1
INDE  19  31  40  FOBS=  128.6  SIGMA=   1.6  PHAS= -138.2  FOM=  0.78  TEST=  0
INDE  19  31  42  FOBS=  144.2  SIGMA=   1.5  PHAS=  -42.5  FOM=  0.93  TEST=  0
INDE  19  31  44  FOBS=    0.0  SIGMA=  19.5  PHAS=    0.0  FOM=  0.00  TEST=  0
INDE  19  31  46  FOBS=   50.7  SIGMA=   3.5  PHAS=  179.5  FOM=  0.85  TEST=  0
INDE  19  31  48  FOBS=   33.1  SIGMA=   4.9  PHAS=  -56.3  FOM=  0.15  TEST=  0
INDE  19  31  50  FOBS=  150.4  SIGMA=   1.2  PHAS=   90.7  FOM=  0.68  TEST=  1
INDE  19  31  52  FOBS=   39.6  SIGMA=   4.3  PHAS=  133.3  FOM=  0.61  TEST=  0
INDE  19  31  54  FOBS=   14.0  SIGMA=  14.2  PHAS=  -69.2  FOM=  0.25  TEST=  0
INDE  19  31  56  FOBS=  108.8  SIGMA=   1.8  PHAS=   25.9  FOM=  0.95  TEST=  0
INDE  19  31  58  FOBS=   42.8  SIGMA=   4.8  PHAS=   55.4  FOM=  0.53  TEST=  0
INDE  19  31  60  FOBS=   47.1  SIGMA=   4.7  PHAS=   64.4  FOM=  0.72  TEST=  0
INDE  19  31  62  FOBS=   54.1  SIGMA=   4.1  PHAS=   56.1  FOM=  0.75  TEST=  0
INDE  19  31  64  FOBS=    4.9  SIGMA=  79.0  PHAS=   81.0  FOM=  0.01  TEST=  0
INDE  19  31  66  FOBS=   75.9  SIGMA=   7.4  PHAS=  138.8  FOM=  0.70  TEST=  0
INDE  19  31  68  FOBS=   94.0  SIGMA=   6.4  PHAS=   80.5  FOM=  0.93  TEST=  0
INDE  19  32  19  FOBS=   66.0  SIGMA=   2.2  PHAS=  -81.7  FOM=  0.27  TEST=  0
INDE  19  32  21  FOBS=  253.0  SIGMA=   0.7  PHAS=  -13.8  FOM=  0.93  TEST=  0
INDE  19  32  23  FOBS=  294.0  SIGMA=   0.7  PHAS= -151.2  FOM=  0.97  TEST=  0
INDE  19  32  25  FOBS=  223.6  SIGMA=   0.8  PHAS= -119.1  FOM=  0.92  TEST=  0
INDE  19  32  27  FOBS=    0.0  SIGMA=  18.2  PHAS=    0.0  FOM=  0.00  TEST=  0
INDE  19  32  29  FOBS=   26.3  SIGMA=   6.6  PHAS=  -80.7  FOM=  0.65  TEST=  0
INDE  19  32  31  FOBS=  143.0  SIGMA=   1.2  PHAS=  151.5  FOM=  0.90  TEST=  0
INDE  19  32  33  FOBS=    0.0  SIGMA=  18.5  PHAS=    0.0  FOM=  0.00  TEST=  1
INDE  19  32  35  FOBS=  150.6  SIGMA=   1.1  PHAS=   78.8  FOM=  0.92  TEST=  0
INDE  19  32  37  FOBS=  114.2  SIGMA=   1.9  PHAS=  178.1  FOM=  0.93  TEST=  0
INDE  19  32  39  FOBS=   55.2  SIGMA=   3.7  PHAS=   59.4  FOM=  0.76  TEST=  0
INDE  19  32  41  FOBS=  115.8  SIGMA=   1.8  PHAS=  -39.2  FOM=  0.46  TEST=  1
INDE  19  32  43  FOBS=   72.0  SIGMA=   2.8  PHAS=  147.8  FOM=  0.91  TEST=  0
INDE  19  32  45  FOBS=  100.7  SIGMA=   1.7  PHAS=   84.5  FOM=  0.84  TEST=  0
INDE  19  32  47  FOBS=   82.4  SIGMA=   2.1  PHAS=   21.8  FOM=  0.92  TEST=  1
INDE  19  32  49  FOBS=  117.8  SIGMA=   1.5  PHAS=  -24.9  FOM=  0.92  TEST=  0
INDE  19  32  51  FOBS=   79.3  SIGMA=   2.1  PHAS=   42.3  FOM=  0.91  TEST=  0
INDE  19  32  53  FOBS=   60.9  SIGMA=   2.7  PHAS=   89.4  FOM=  0.42  TEST=  0
INDE  19  32  55  FOBS=   53.5  SIGMA=   3.6  PHAS=   22.3  FOM=  0.76  TEST=  0
INDE  19  32  57  FOBS=   15.4  SIGMA=  17.5  PHAS= -157.0  FOM=  0.13  TEST=  0
INDE  19  32  59  FOBS=    0.0  SIGMA=  20.1  PHAS=    0.0  FOM=  0.00  TEST=  0
INDE  19  32  61  FOBS=   85.0  SIGMA=   2.4  PHAS=  -51.4  FOM=  0.91  TEST=  0
INDE  19  32  63  FOBS=    0.0  SIGMA=  23.1  PHAS=    0.0  FOM=  0.00  TEST=  0
```

*FIG. 12A - 428*

```
INDE 19 32 65 FOBS=    38.9 SIGMA=  8.3 PHAS=   75.4 FOM= 0.84 TEST= 0
INDE 19 32 67 FOBS=    84.9 SIGMA=  6.8 PHAS=   27.3 FOM= 0.93 TEST= 0
INDE 19 33 20 FOBS=   346.2 SIGMA=  0.7 PHAS= -104.1 FOM= 0.98 TEST= 0
INDE 19 33 22 FOBS=   223.8 SIGMA=  1.0 PHAS=  121.2 FOM= 0.96 TEST= 0
INDE 19 33 24 FOBS=   127.1 SIGMA=  1.3 PHAS=   67.0 FOM= 0.56 TEST= 1
INDE 19 33 26 FOBS=   177.6 SIGMA=  1.0 PHAS=  -58.6 FOM= 0.97 TEST= 0
INDE 19 33 28 FOBS=   247.4 SIGMA=  0.8 PHAS= -165.0 FOM= 0.96 TEST= 0
INDE 19 33 30 FOBS=    31.0 SIGMA=  6.1 PHAS= -124.7 FOM= 0.39 TEST= 0
INDE 19 33 32 FOBS=   182.0 SIGMA=  1.0 PHAS=  178.0 FOM= 0.22 TEST= 1
INDE 19 33 34 FOBS=   206.1 SIGMA=  0.9 PHAS=  -32.7 FOM= 0.96 TEST= 0
INDE 19 33 36 FOBS=   153.5 SIGMA=  1.5 PHAS=   23.1 FOM= 0.92 TEST= 0
INDE 19 33 38 FOBS=   121.8 SIGMA=  1.8 PHAS=  -13.5 FOM= 0.90 TEST= 1
INDE 19 33 40 FOBS=    93.8 SIGMA=  2.2 PHAS= -142.3 FOM= 0.75 TEST= 0
INDE 19 33 42 FOBS=   105.2 SIGMA=  2.0 PHAS=  -70.7 FOM= 0.83 TEST= 0
INDE 19 33 44 FOBS=    76.9 SIGMA=  2.4 PHAS=  -56.0 FOM= 0.64 TEST= 0
INDE 19 33 46 FOBS=   107.4 SIGMA=  1.8 PHAS=  -63.2 FOM= 0.89 TEST= 0
INDE 19 33 48 FOBS=   226.1 SIGMA=  0.8 PHAS=  -72.2 FOM= 0.98 TEST= 0
INDE 19 33 50 FOBS=    81.2 SIGMA=  2.0 PHAS= -122.6 FOM= 0.64 TEST= 0
INDE 19 33 52 FOBS=     0.0 SIGMA= 18.7 PHAS=    0.0 FOM= 0.00 TEST= 0
INDE 19 33 54 FOBS=   121.7 SIGMA=  1.7 PHAS=  -11.4 FOM= 0.94 TEST= 0
INDE 19 33 56 FOBS=     4.3 SIGMA= 51.0 PHAS=  107.2 FOM= 0.00 TEST= 1
INDE 19 33 58 FOBS=    44.6 SIGMA=  4.3 PHAS=   99.1 FOM= 0.18 TEST= 0
INDE 19 33 60 FOBS=     0.0 SIGMA= 21.7 PHAS=    0.0 FOM= 0.00 TEST= 0
INDE 19 33 62 FOBS=    52.6 SIGMA=  5.1 PHAS= -132.8 FOM= 0.66 TEST= 0
INDE 19 33 64 FOBS=     0.0 SIGMA= 27.3 PHAS=    0.0 FOM= 0.00 TEST= 0
INDE 19 33 66 FOBS=    53.8 SIGMA=  6.2 PHAS=  -81.7 FOM= 0.86 TEST= 0
INDE 19 34 19 FOBS=   140.2 SIGMA=  1.1 PHAS=  160.4 FOM= 0.96 TEST= 0
INDE 19 34 21 FOBS=   152.0 SIGMA=  1.2 PHAS=   57.3 FOM= 0.86 TEST= 0
INDE 19 34 23 FOBS=    86.8 SIGMA=  2.0 PHAS=  -48.7 FOM= 0.91 TEST= 0
INDE 19 34 25 FOBS=   149.8 SIGMA=  1.2 PHAS= -154.9 FOM= 0.99 TEST= 0
INDE 19 34 27 FOBS=   167.1 SIGMA=  1.1 PHAS=  -63.3 FOM= 0.91 TEST= 0
INDE 19 34 29 FOBS=    28.3 SIGMA=  6.5 PHAS=  -20.2 FOM= 0.78 TEST= 0
INDE 19 34 31 FOBS=   163.9 SIGMA=  1.1 PHAS= -165.5 FOM= 0.67 TEST= 1
INDE 19 34 33 FOBS=    90.9 SIGMA=  1.9 PHAS=  -32.6 FOM= 0.76 TEST= 0
INDE 19 34 35 FOBS=   131.4 SIGMA=  1.4 PHAS= -148.7 FOM= 0.76 TEST= 0
INDE 19 34 37 FOBS=    93.0 SIGMA=  2.3 PHAS= -137.6 FOM= 0.75 TEST= 0
INDE 19 34 39 FOBS=     0.0 SIGMA= 23.6 PHAS=    0.0 FOM= 0.00 TEST= 0
INDE 19 34 41 FOBS=    36.5 SIGMA=  5.4 PHAS= -164.5 FOM= 0.68 TEST= 0
INDE 19 34 43 FOBS=   107.8 SIGMA=  1.9 PHAS= -147.0 FOM= 0.89 TEST= 0
INDE 19 34 45 FOBS=    45.4 SIGMA=  4.1 PHAS=   94.8 FOM= 0.28 TEST= 0
INDE 19 34 47 FOBS=   162.3 SIGMA=  1.2 PHAS= -165.2 FOM= 0.96 TEST= 0
INDE 19 34 49 FOBS=   135.2 SIGMA=  1.3 PHAS= -172.3 FOM= 0.92 TEST= 0
INDE 19 34 51 FOBS=    55.1 SIGMA=  3.0 PHAS=  155.1 FOM= 0.72 TEST= 1
INDE 19 34 53 FOBS=   132.6 SIGMA=  1.6 PHAS=  -82.8 FOM= 0.91 TEST= 0
INDE 19 34 55 FOBS=     0.0 SIGMA= 20.3 PHAS=    0.0 FOM= 0.00 TEST= 0
INDE 19 34 57 FOBS=    58.3 SIGMA=  3.3 PHAS=   90.3 FOM= 0.85 TEST= 0
INDE 19 34 59 FOBS=    68.2 SIGMA=  2.8 PHAS=  163.4 FOM= 0.84 TEST= 0
INDE 19 34 61 FOBS=    82.1 SIGMA=  3.0 PHAS=   95.9 FOM= 0.75 TEST= 0
INDE 19 34 63 FOBS=    44.3 SIGMA=  5.3 PHAS=   98.5 FOM= 0.70 TEST= 0
INDE 19 34 65 FOBS=     0.0 SIGMA= 25.4 PHAS=    0.0 FOM= 0.00 TEST= 0
INDE 19 34 67 FOBS=     9.6 SIGMA= 34.7 PHAS=  104.4 FOM= 0.13 TEST= 0
INDE 19 35 20 FOBS=   164.6 SIGMA=  1.0 PHAS=  -57.0 FOM= 0.92 TEST= 1
INDE 19 35 22 FOBS=    27.7 SIGMA=  6.2 PHAS=   43.4 FOM= 0.13 TEST= 0
INDE 19 35 24 FOBS=   282.6 SIGMA=  0.8 PHAS=  -67.6 FOM= 0.98 TEST= 0
INDE 19 35 26 FOBS=   189.3 SIGMA=  1.0 PHAS= -161.7 FOM= 0.92 TEST= 0
INDE 19 35 28 FOBS=   327.7 SIGMA=  0.9 PHAS= -128.0 FOM= 0.95 TEST= 0
INDE 19 35 30 FOBS=    33.4 SIGMA=  5.9 PHAS= -103.3 FOM= 0.12 TEST= 0
INDE 19 35 32 FOBS=    69.4 SIGMA=  2.7 PHAS= -113.1 FOM= 0.53 TEST= 0
INDE 19 35 34 FOBS=   137.9 SIGMA=  1.4 PHAS=  -30.2 FOM= 0.90 TEST= 0
INDE 19 35 36 FOBS=   119.5 SIGMA=  1.5 PHAS=    2.2 FOM= 0.86 TEST= 0
INDE 19 35 38 FOBS=   137.4 SIGMA=  1.6 PHAS=   58.0 FOM= 0.79 TEST= 0
INDE 19 35 40 FOBS=    69.2 SIGMA=  3.0 PHAS=   -8.5 FOM= 0.44 TEST= 0
INDE 19 35 42 FOBS=    43.7 SIGMA=  4.8 PHAS=  179.7 FOM= 0.50 TEST= 0
INDE 19 35 44 FOBS=    62.3 SIGMA=  3.2 PHAS= -103.6 FOM= 0.67 TEST= 0
INDE 19 35 46 FOBS=    69.9 SIGMA=  2.7 PHAS= -156.1 FOM= 0.90 TEST= 0
INDE 19 35 48 FOBS=    12.4 SIGMA= 16.7 PHAS=  100.3 FOM= 0.22 TEST= 0
INDE 19 35 50 FOBS=    41.7 SIGMA=  4.3 PHAS= -122.8 FOM= 0.18 TEST= 0
INDE 19 35 52 FOBS=   104.7 SIGMA=  1.8 PHAS=  158.8 FOM= 0.90 TEST= 0
INDE 19 35 54 FOBS=    78.0 SIGMA=  2.5 PHAS=   22.0 FOM= 0.73 TEST= 0
INDE 19 35 56 FOBS=    48.5 SIGMA=  4.0 PHAS= -177.7 FOM= 0.62 TEST= 0
```

*FIG. 12A - 429*

```
INDE  19  35  58  FOBS=   105.7  SIGMA=   2.1  PHAS=   32.3  FOM=  0.90  TEST= 0
INDE  19  35  60  FOBS=    52.1  SIGMA=   4.7  PHAS=   15.7  FOM=  0.49  TEST= 0
INDE  19  35  62  FOBS=    66.7  SIGMA=   3.3  PHAS=   -4.2  FOM=  0.88  TEST= 0
INDE  19  35  64  FOBS=    38.7  SIGMA=   5.8  PHAS=  -88.0  FOM=  0.66  TEST= 0
INDE  19  35  66  FOBS=     0.0  SIGMA=  28.5  PHAS=    0.0  FOM=  0.00  TEST= 0
INDE  19  36  19  FOBS=   206.0  SIGMA=   0.9  PHAS=  174.2  FOM=  0.91  TEST= 0
INDE  19  36  21  FOBS=   116.0  SIGMA=   1.4  PHAS=  -53.7  FOM=  0.49  TEST= 0
INDE  19  36  23  FOBS=   132.5  SIGMA=   1.3  PHAS= -175.2  FOM=  0.90  TEST= 0
INDE  19  36  25  FOBS=   257.5  SIGMA=   0.8  PHAS=  177.5  FOM=  0.95  TEST= 0
INDE  19  36  27  FOBS=    53.1  SIGMA=   3.5  PHAS=  104.2  FOM=  0.46  TEST= 0
INDE  19  36  29  FOBS=   106.8  SIGMA=   1.8  PHAS=  -80.6  FOM=  0.61  TEST= 0
INDE  19  36  31  FOBS=    53.9  SIGMA=   3.8  PHAS=   93.1  FOM=  0.92  TEST= 0
INDE  19  36  33  FOBS=    71.3  SIGMA=   2.6  PHAS= -107.6  FOM=  0.83  TEST= 0
INDE  19  36  35  FOBS=   273.6  SIGMA=   0.8  PHAS= -122.7  FOM=  0.97  TEST= 0
INDE  19  36  37  FOBS=   110.9  SIGMA=   1.7  PHAS=   31.6  FOM=  0.24  TEST= 0
INDE  19  36  39  FOBS=    80.1  SIGMA=   2.6  PHAS= -167.1  FOM=  0.45  TEST= 0
INDE  19  36  41  FOBS=     0.0  SIGMA=  20.8  PHAS=    0.0  FOM=  0.00  TEST= 0
INDE  19  36  43  FOBS=    51.1  SIGMA=   3.9  PHAS=  144.9  FOM=  0.80  TEST= 0
INDE  19  36  45  FOBS=   108.9  SIGMA=   1.8  PHAS=  125.4  FOM=  0.87  TEST= 0
INDE  19  36  47  FOBS=     0.0  SIGMA=  19.7  PHAS=    0.0  FOM=  0.00  TEST= 0
INDE  19  36  49  FOBS=   113.0  SIGMA=   1.7  PHAS=  122.3  FOM=  0.94  TEST= 0
INDE  19  36  51  FOBS=    49.7  SIGMA=   3.9  PHAS=  -77.0  FOM=  0.65  TEST= 0
INDE  19  36  53  FOBS=    75.5  SIGMA=   2.6  PHAS= -120.9  FOM=  0.08  TEST= 1
INDE  19  36  55  FOBS=    92.6  SIGMA=   2.2  PHAS=   51.2  FOM=  0.93  TEST= 0
INDE  19  36  57  FOBS=    69.3  SIGMA=   3.1  PHAS=   48.1  FOM=  0.37  TEST= 1
INDE  19  36  59  FOBS=    47.2  SIGMA=   4.6  PHAS= -127.5  FOM=  0.76  TEST= 0
INDE  19  36  61  FOBS=    32.5  SIGMA=   6.7  PHAS= -132.9  FOM=  0.29  TEST= 0
INDE  19  36  63  FOBS=     0.0  SIGMA=  21.1  PHAS=    0.0  FOM=  0.00  TEST= 0
INDE  19  36  65  FOBS=    58.4  SIGMA=   5.7  PHAS=  170.7  FOM=  0.86  TEST= 0
INDE  19  37  20  FOBS=   189.6  SIGMA=   0.9  PHAS=   66.8  FOM=  0.88  TEST= 1
INDE  19  37  22  FOBS=    76.7  SIGMA=   2.2  PHAS=   62.6  FOM=  0.67  TEST= 0
INDE  19  37  24  FOBS=   124.3  SIGMA=   1.5  PHAS=   15.3  FOM=  0.96  TEST= 0
INDE  19  37  26  FOBS=   215.9  SIGMA=   0.9  PHAS= -157.6  FOM=  0.95  TEST= 0
INDE  19  37  28  FOBS=   198.5  SIGMA=   1.1  PHAS= -162.0  FOM=  0.95  TEST= 0
INDE  19  37  30  FOBS=   107.2  SIGMA=   1.9  PHAS=   75.3  FOM=  0.94  TEST= 0
INDE  19  37  32  FOBS=   154.4  SIGMA=   1.4  PHAS=  -71.6  FOM=  0.93  TEST= 0
INDE  19  37  34  FOBS=   205.9  SIGMA=   1.0  PHAS=  158.0  FOM=  0.95  TEST= 1
INDE  19  37  36  FOBS=    54.5  SIGMA=   3.3  PHAS= -156.7  FOM=  0.83  TEST= 0
INDE  19  37  38  FOBS=   112.9  SIGMA=   1.7  PHAS=   27.2  FOM=  0.81  TEST= 0
INDE  19  37  40  FOBS=   110.2  SIGMA=   1.9  PHAS=  -99.8  FOM=  0.82  TEST= 0
INDE  19  37  42  FOBS=    39.2  SIGMA=   5.1  PHAS=   85.5  FOM=  0.55  TEST= 0
INDE  19  37  44  FOBS=   119.3  SIGMA=   1.7  PHAS=   16.1  FOM=  0.92  TEST= 0
INDE  19  37  46  FOBS=    94.9  SIGMA=   2.0  PHAS= -163.8  FOM=  0.96  TEST= 0
INDE  19  37  48  FOBS=    59.4  SIGMA=   3.1  PHAS=   62.5  FOM=  0.89  TEST= 0
INDE  19  37  50  FOBS=     0.0  SIGMA=  18.9  PHAS=    0.0  FOM=  0.00  TEST= 0
INDE  19  37  52  FOBS=   155.4  SIGMA=   1.2  PHAS=  176.1  FOM=  0.95  TEST= 0
INDE  19  37  54  FOBS=    79.7  SIGMA=   2.5  PHAS=   -7.1  FOM=  0.81  TEST= 0
INDE  19  37  56  FOBS=    88.0  SIGMA=   2.5  PHAS= -120.0  FOM=  0.91  TEST= 0
INDE  19  37  58  FOBS=   131.7  SIGMA=   1.8  PHAS=  130.5  FOM=  0.92  TEST= 0
INDE  19  37  60  FOBS=    77.5  SIGMA=   2.8  PHAS=  -30.0  FOM=  0.83  TEST= 0
INDE  19  37  62  FOBS=     0.0  SIGMA=  25.2  PHAS=    0.0  FOM=  0.00  TEST= 0
INDE  19  37  64  FOBS=    89.4  SIGMA=   3.2  PHAS=  -97.2  FOM=  0.93  TEST= 0
INDE  19  38  19  FOBS=   281.3  SIGMA=   0.8  PHAS=   34.8  FOM=  0.97  TEST= 0
INDE  19  38  21  FOBS=   188.9  SIGMA=   1.0  PHAS=   59.1  FOM=  0.93  TEST= 0
INDE  19  38  23  FOBS=   172.7  SIGMA=   1.1  PHAS=  -99.4  FOM=  0.88  TEST= 0
INDE  19  38  25  FOBS=   224.4  SIGMA=   0.9  PHAS=  148.4  FOM=  0.97  TEST= 0
INDE  19  38  27  FOBS=   218.3  SIGMA=   1.0  PHAS=  140.8  FOM=  0.95  TEST= 0
INDE  19  38  29  FOBS=   124.1  SIGMA=   1.7  PHAS=   37.4  FOM=  0.93  TEST= 0
INDE  19  38  31  FOBS=    78.7  SIGMA=   2.6  PHAS=   51.2  FOM=  0.48  TEST= 1
INDE  19  38  33  FOBS=    41.0  SIGMA=   5.1  PHAS=  153.6  FOM=  0.66  TEST= 0
INDE  19  38  35  FOBS=   203.4  SIGMA=   1.0  PHAS=  124.9  FOM=  0.90  TEST= 0
INDE  19  38  37  FOBS=   199.0  SIGMA=   1.0  PHAS=   -1.3  FOM=  0.95  TEST= 0
INDE  19  38  39  FOBS=    57.0  SIGMA=   3.2  PHAS=  150.9  FOM=  0.55  TEST= 0
INDE  19  38  41  FOBS=    68.9  SIGMA=   3.0  PHAS= -160.0  FOM=  0.72  TEST= 0
INDE  19  38  43  FOBS=    82.4  SIGMA=   2.5  PHAS= -143.4  FOM=  0.79  TEST= 0
INDE  19  38  45  FOBS=   101.8  SIGMA=   2.0  PHAS= -173.2  FOM=  0.73  TEST= 0
INDE  19  38  47  FOBS=   196.9  SIGMA=   1.1  PHAS=   44.4  FOM=  0.97  TEST= 0
INDE  19  38  49  FOBS=   139.7  SIGMA=   1.4  PHAS=   70.8  FOM=  0.94  TEST= 0
INDE  19  38  51  FOBS=    84.9  SIGMA=   2.4  PHAS=  138.4  FOM=  0.90  TEST= 0
INDE  19  38  53  FOBS=    87.4  SIGMA=   2.5  PHAS=    5.2  FOM=  0.12  TEST= 1
```

*FIG. 12A - 430*

```
INDE  19  38  55  FOBS=   89.9  SIGMA=   2.5  PHAS=  109.7  FOM=  0.93  TEST=  0
INDE  19  38  57  FOBS=   44.8  SIGMA=   4.9  PHAS=   63.8  FOM=  0.73  TEST=  0
INDE  19  38  59  FOBS=   31.9  SIGMA=   6.8  PHAS= -135.4  FOM=  0.02  TEST=  1
INDE  19  38  61  FOBS=   56.9  SIGMA=   3.9  PHAS= -101.9  FOM=  0.83  TEST=  0
INDE  19  38  63  FOBS=   25.0  SIGMA=  12.9  PHAS=   16.3  FOM=  0.35  TEST=  0
INDE  19  38  65  FOBS=  106.5  SIGMA=   3.9  PHAS=  177.3  FOM=  0.96  TEST=  0
INDE  19  39  20  FOBS=  222.4  SIGMA=   1.0  PHAS=  -32.9  FOM=  0.95  TEST=  0
INDE  19  39  22  FOBS=  174.8  SIGMA=   1.1  PHAS=   98.0  FOM=  0.86  TEST=  0
INDE  19  39  24  FOBS=  297.3  SIGMA=   0.8  PHAS=   57.0  FOM=  0.97  TEST=  0
INDE  19  39  26  FOBS=   89.3  SIGMA=   2.2  PHAS=  124.5  FOM=  0.23  TEST=  0
INDE  19  39  28  FOBS=  162.4  SIGMA=   1.2  PHAS=   83.9  FOM=  0.49  TEST=  1
INDE  19  39  30  FOBS=  100.7  SIGMA=   2.0  PHAS=    4.9  FOM=  0.89  TEST=  0
INDE  19  39  32  FOBS=   66.2  SIGMA=   3.0  PHAS=    2.4  FOM=  0.61  TEST=  0
INDE  19  39  34  FOBS=   55.4  SIGMA=   3.4  PHAS=  179.4  FOM=  0.09  TEST=  1
INDE  19  39  36  FOBS=   55.9  SIGMA=   3.2  PHAS=   41.0  FOM=  0.12  TEST=  0
INDE  19  39  38  FOBS=  138.4  SIGMA=   1.4  PHAS=  -64.4  FOM=  0.82  TEST=  0
INDE  19  39  40  FOBS=    0.0  SIGMA=  19.4  PHAS=    0.0  FOM=  0.00  TEST=  0
INDE  19  39  42  FOBS=   33.9  SIGMA=   6.3  PHAS=   77.5  FOM=  0.65  TEST=  0
INDE  19  39  44  FOBS=   25.9  SIGMA=   7.7  PHAS=  160.7  FOM=  0.14  TEST=  0
INDE  19  39  46  FOBS=   22.7  SIGMA=   8.3  PHAS=  153.2  FOM=  0.22  TEST=  1
INDE  19  39  48  FOBS=  157.1  SIGMA=   1.3  PHAS=  -33.2  FOM=  0.97  TEST=  0
INDE  19  39  50  FOBS=   96.4  SIGMA=   2.1  PHAS=   27.9  FOM=  0.92  TEST=  0
INDE  19  39  52  FOBS=  148.3  SIGMA=   1.6  PHAS=   89.7  FOM=  0.96  TEST=  0
INDE  19  39  54  FOBS=  132.1  SIGMA=   1.7  PHAS=   72.8  FOM=  0.11  TEST=  1
INDE  19  39  56  FOBS=    0.0  SIGMA=  21.7  PHAS=    0.0  FOM=  0.00  TEST=  0
INDE  19  39  58  FOBS=    0.0  SIGMA=  20.8  PHAS=    0.0  FOM=  0.00  TEST=  1
INDE  19  39  60  FOBS=   85.7  SIGMA=   2.6  PHAS=  -24.9  FOM=  0.92  TEST=  0
INDE  19  39  62  FOBS=    0.0  SIGMA=  28.2  PHAS=    0.0  FOM=  0.00  TEST=  1
INDE  19  39  64  FOBS=    0.0  SIGMA=  24.1  PHAS=    0.0  FOM=  0.00  TEST=  0
INDE  19  40  19  FOBS=  308.2  SIGMA=   0.8  PHAS=  -25.0  FOM=  0.98  TEST=  0
INDE  19  40  21  FOBS=  135.1  SIGMA=   1.4  PHAS=   16.4  FOM=  0.95  TEST=  0
INDE  19  40  23  FOBS=  171.7  SIGMA=   1.3  PHAS=  -36.7  FOM=  0.44  TEST=  1
INDE  19  40  25  FOBS=   88.4  SIGMA=   2.2  PHAS=  -38.0  FOM=  0.96  TEST=  0
INDE  19  40  27  FOBS=  116.6  SIGMA=   1.6  PHAS=  -31.7  FOM=  0.77  TEST=  0
INDE  19  40  29  FOBS=   64.4  SIGMA=   2.9  PHAS=   93.6  FOM=  0.56  TEST=  0
INDE  19  40  31  FOBS=  107.8  SIGMA=   1.9  PHAS=  -40.7  FOM=  0.93  TEST=  0
INDE  19  40  33  FOBS=  174.5  SIGMA=   1.2  PHAS= -117.2  FOM=  0.93  TEST=  0
INDE  19  40  35  FOBS=  132.9  SIGMA=   1.4  PHAS=  166.0  FOM=  0.94  TEST=  0
INDE  19  40  37  FOBS=  102.7  SIGMA=   1.8  PHAS=   82.6  FOM=  0.90  TEST=  0
INDE  19  40  39  FOBS=    0.0  SIGMA=  19.7  PHAS=    0.0  FOM=  0.00  TEST=  0
INDE  19  40  41  FOBS=    0.0  SIGMA=  22.2  PHAS=    0.0  FOM=  0.00  TEST=  0
INDE  19  40  43  FOBS=   25.7  SIGMA=   7.8  PHAS= -160.4  FOM=  0.18  TEST=  0
INDE  19  40  45  FOBS=    0.0  SIGMA=  20.7  PHAS=    0.0  FOM=  0.00  TEST=  0
INDE  19  40  47  FOBS=    0.0  SIGMA=  21.0  PHAS=    0.0  FOM=  0.00  TEST=  0
INDE  19  40  49  FOBS=   90.4  SIGMA=   2.5  PHAS=  -44.3  FOM=  0.89  TEST=  0
INDE  19  40  51  FOBS=  134.8  SIGMA=   1.8  PHAS=  -29.6  FOM=  0.96  TEST=  0
INDE  19  40  53  FOBS=   47.8  SIGMA=   4.5  PHAS=  -16.4  FOM=  0.70  TEST=  0
INDE  19  40  55  FOBS=   59.4  SIGMA=   3.7  PHAS=   38.2  FOM=  0.85  TEST=  0
INDE  19  40  57  FOBS=    0.0  SIGMA=  20.8  PHAS=    0.0  FOM=  0.00  TEST=  0
INDE  19  40  59  FOBS=   36.4  SIGMA=   6.1  PHAS= -123.5  FOM=  0.67  TEST=  0
INDE  19  40  61  FOBS=   62.4  SIGMA=   3.6  PHAS= -105.8  FOM=  0.71  TEST=  0
INDE  19  40  63  FOBS=    0.0  SIGMA=  23.7  PHAS=    0.0  FOM=  0.00  TEST=  0
INDE  19  41  20  FOBS=  201.6  SIGMA=   1.1  PHAS= -118.2  FOM=  0.92  TEST=  0
INDE  19  41  22  FOBS=  227.7  SIGMA=   1.0  PHAS= -118.4  FOM=  0.44  TEST=  1
INDE  19  41  24  FOBS=  245.4  SIGMA=   0.9  PHAS=   15.1  FOM=  0.96  TEST=  0
INDE  19  41  26  FOBS=  117.7  SIGMA=   1.7  PHAS=  169.6  FOM=  0.85  TEST=  0
INDE  19  41  28  FOBS=  155.1  SIGMA=   1.2  PHAS=   79.9  FOM=  0.84  TEST=  0
INDE  19  41  30  FOBS=   51.8  SIGMA=   3.6  PHAS=   57.2  FOM=  0.49  TEST=  0
INDE  19  41  32  FOBS=  142.1  SIGMA=   1.5  PHAS=  111.5  FOM=  0.77  TEST=  0
INDE  19  41  34  FOBS=   89.7  SIGMA=   2.3  PHAS=  149.4  FOM=  0.96  TEST=  0
INDE  19  41  36  FOBS=  154.4  SIGMA=   1.2  PHAS=   47.2  FOM=  0.94  TEST=  0
INDE  19  41  38  FOBS=  137.4  SIGMA=   1.3  PHAS=  -48.7  FOM=  0.95  TEST=  0
INDE  19  41  40  FOBS=   70.1  SIGMA=   2.6  PHAS=  -48.0  FOM=  0.85  TEST=  0
INDE  19  41  42  FOBS=    0.0  SIGMA=  20.1  PHAS=    0.0  FOM=  0.00  TEST=  0
INDE  19  41  44  FOBS=   29.7  SIGMA=   7.9  PHAS= -150.8  FOM=  0.44  TEST=  0
INDE  19  41  46  FOBS=    0.0  SIGMA=  21.3  PHAS=    0.0  FOM=  0.00  TEST=  0
INDE  19  41  48  FOBS=   66.1  SIGMA=   3.4  PHAS= -118.4  FOM=  0.85  TEST=  0
INDE  19  41  50  FOBS=    0.0  SIGMA=  22.3  PHAS=    0.0  FOM=  0.00  TEST=  1
INDE  19  41  52  FOBS=   51.4  SIGMA=   4.8  PHAS=   90.7  FOM=  0.33  TEST=  0
INDE  19  41  54  FOBS=   39.4  SIGMA=   5.6  PHAS= -105.3  FOM=  0.60  TEST=  0
```

*FIG. 12A - 431*

```
INDE   19  41  56  FOBS=    0.0  SIGMA=  20.8  PHAS=    0.0  FOM=  0.00  TEST= 0
INDE   19  41  58  FOBS=   41.1  SIGMA=   6.0  PHAS=    9.5  FOM=  0.32  TEST= 1
INDE   19  41  60  FOBS=    0.0  SIGMA=  20.9  PHAS=    0.0  FOM=  0.00  TEST= 0
INDE   19  41  62  FOBS=    0.0  SIGMA=  25.7  PHAS=    0.0  FOM=  0.00  TEST= 0
INDE   19  42  19  FOBS=  108.5  SIGMA=   2.1  PHAS=  174.0  FOM=  0.84  TEST= 0
INDE   19  42  21  FOBS=   70.6  SIGMA=   2.8  PHAS=  -24.5  FOM=  0.43  TEST= 1
INDE   19  42  23  FOBS=  146.4  SIGMA=   1.4  PHAS=  -99.8  FOM=  0.90  TEST= 0
INDE   19  42  25  FOBS=   34.9  SIGMA=   5.4  PHAS=  -37.0  FOM=  0.59  TEST= 0
INDE   19  42  27  FOBS=  231.7  SIGMA=   0.9  PHAS=    8.0  FOM=  0.97  TEST= 0
INDE   19  42  29  FOBS=    0.0  SIGMA=  19.4  PHAS=    0.0  FOM=  0.00  TEST= 0
INDE   19  42  31  FOBS=  152.4  SIGMA=   1.2  PHAS=   -1.4  FOM=  0.93  TEST= 0
INDE   19  42  33  FOBS=    9.2  SIGMA=  23.2  PHAS= -178.2  FOM=  0.05  TEST= 0
INDE   19  42  35  FOBS=   44.6  SIGMA=   4.4  PHAS=  -46.8  FOM=  0.64  TEST= 1
INDE   19  42  37  FOBS=   46.5  SIGMA=   3.8  PHAS=  120.5  FOM=  0.81  TEST= 0
INDE   19  42  39  FOBS=   34.0  SIGMA=   5.9  PHAS= -109.7  FOM=  0.62  TEST= 0
INDE   19  42  41  FOBS=    0.0  SIGMA=  19.7  PHAS=    0.0  FOM=  0.00  TEST= 0
INDE   19  42  43  FOBS=   57.5  SIGMA=   3.9  PHAS= -118.0  FOM=  0.20  TEST= 0
INDE   19  42  45  FOBS=    0.0  SIGMA=  22.1  PHAS=    0.0  FOM=  0.00  TEST= 0
INDE   19  42  47  FOBS=  102.5  SIGMA=   2.3  PHAS=  131.8  FOM=  0.81  TEST= 0
INDE   19  42  49  FOBS=    0.0  SIGMA=  22.4  PHAS=    0.0  FOM=  0.00  TEST= 0
INDE   19  42  51  FOBS=   61.0  SIGMA=   3.7  PHAS=  -70.2  FOM=  0.57  TEST= 0
INDE   19  42  53  FOBS=   17.2  SIGMA=  15.1  PHAS=  131.4  FOM=  0.01  TEST= 1
INDE   19  42  55  FOBS=   61.4  SIGMA=   3.7  PHAS=   67.0  FOM=  0.78  TEST= 0
INDE   19  42  57  FOBS=   41.1  SIGMA=   5.4  PHAS=  139.9  FOM=  0.09  TEST= 1
INDE   19  42  59  FOBS=    0.0  SIGMA=  21.0  PHAS=    0.0  FOM=  0.00  TEST= 1
INDE   19  42  61  FOBS=    0.0  SIGMA=  23.7  PHAS=    0.0  FOM=  0.00  TEST= 0
INDE   19  43  20  FOBS=  243.6  SIGMA=   1.0  PHAS=  137.0  FOM=  0.96  TEST= 0
INDE   19  43  22  FOBS=  236.2  SIGMA=   0.9  PHAS=  143.0  FOM=  0.96  TEST= 0
INDE   19  43  24  FOBS=   74.6  SIGMA=   2.6  PHAS=    0.2  FOM=  0.79  TEST= 0
INDE   19  43  26  FOBS=   66.1  SIGMA=   2.9  PHAS=   -7.5  FOM=  0.91  TEST= 1
INDE   19  43  28  FOBS=  109.7  SIGMA=   1.8  PHAS=  -68.6  FOM=  0.94  TEST= 0
INDE   19  43  30  FOBS=  110.1  SIGMA=   1.6  PHAS=  -79.2  FOM=  0.93  TEST= 0
INDE   19  43  32  FOBS=  229.0  SIGMA=   1.0  PHAS=   57.2  FOM=  0.86  TEST= 1
INDE   19  43  34  FOBS=    0.0  SIGMA=  20.6  PHAS=    0.0  FOM=  0.00  TEST= 0
INDE   19  43  36  FOBS=  169.1  SIGMA=   1.2  PHAS=   86.7  FOM=  0.88  TEST= 0
INDE   19  43  38  FOBS=   35.9  SIGMA=   4.9  PHAS=  154.3  FOM=  0.79  TEST= 0
INDE   19  43  40  FOBS=   55.0  SIGMA=   3.5  PHAS=  -98.9  FOM=  0.73  TEST= 0
INDE   19  43  42  FOBS=   43.4  SIGMA=   4.8  PHAS=  -40.2  FOM=  0.67  TEST= 0
INDE   19  43  44  FOBS=    0.0  SIGMA=  25.2  PHAS=    0.0  FOM=  0.00  TEST= 0
INDE   19  43  46  FOBS=   41.3  SIGMA=   6.0  PHAS=  -51.7  FOM=  0.58  TEST= 0
INDE   19  43  48  FOBS=    0.0  SIGMA=  22.0  PHAS=    0.0  FOM=  0.00  TEST= 0
INDE   19  43  50  FOBS=   69.0  SIGMA=   3.3  PHAS=   69.9  FOM=  0.89  TEST= 0
INDE   19  43  52  FOBS=   50.0  SIGMA=   4.4  PHAS=   15.2  FOM=  0.40  TEST= 0
INDE   19  43  54  FOBS=   46.8  SIGMA=   4.7  PHAS=   45.2  FOM=  0.48  TEST= 0
INDE   19  43  56  FOBS=   61.3  SIGMA=   3.7  PHAS=    5.5  FOM=  0.41  TEST= 0
INDE   19  43  58  FOBS=    0.0  SIGMA=  22.1  PHAS=    0.0  FOM=  0.00  TEST= 0
INDE   19  43  60  FOBS=    3.3  SIGMA=  86.0  PHAS=  125.5  FOM=  0.07  TEST= 0
INDE   19  44  19  FOBS=  242.1  SIGMA=   0.9  PHAS=   14.4  FOM=  0.95  TEST= 0
INDE   19  44  21  FOBS=  156.1  SIGMA=   1.3  PHAS=   -5.6  FOM=  0.86  TEST= 0
INDE   19  44  23  FOBS=  121.2  SIGMA=   1.6  PHAS=  -47.8  FOM=  0.87  TEST= 0
INDE   19  44  25  FOBS=   87.6  SIGMA=   2.2  PHAS=  -97.3  FOM=  0.73  TEST= 0
INDE   19  44  27  FOBS=  105.2  SIGMA=   1.8  PHAS=   27.4  FOM=  0.50  TEST= 1
INDE   19  44  29  FOBS=  110.7  SIGMA=   1.8  PHAS= -161.7  FOM=  0.97  TEST= 0
INDE   19  44  31  FOBS=   37.0  SIGMA=   5.1  PHAS= -156.1  FOM=  0.47  TEST= 0
INDE   19  44  33  FOBS=   52.6  SIGMA=   3.3  PHAS= -153.0  FOM=  0.86  TEST= 0
INDE   19  44  35  FOBS=   91.9  SIGMA=   2.4  PHAS= -179.0  FOM=  0.34  TEST= 1
INDE   19  44  37  FOBS=  128.1  SIGMA=   1.6  PHAS=   67.1  FOM=  0.66  TEST= 1
INDE   19  44  39  FOBS=   67.2  SIGMA=   3.0  PHAS=  104.2  FOM=  0.77  TEST= 0
INDE   19  44  41  FOBS=    0.0  SIGMA=  22.9  PHAS=    0.0  FOM=  0.00  TEST= 0
INDE   19  44  43  FOBS=   86.1  SIGMA=   2.5  PHAS=  -88.3  FOM=  0.92  TEST= 0
INDE   19  44  45  FOBS=  140.8  SIGMA=   1.9  PHAS=  -97.1  FOM=  0.94  TEST= 0
INDE   19  44  47  FOBS=   34.8  SIGMA=   6.5  PHAS=   54.1  FOM=  0.47  TEST= 0
INDE   19  44  49  FOBS=  108.8  SIGMA=   2.1  PHAS=  -75.9  FOM=  0.90  TEST= 0
INDE   19  44  51  FOBS=  111.7  SIGMA=   2.1  PHAS=  -17.9  FOM=  0.94  TEST= 0
INDE   19  44  53  FOBS=   34.9  SIGMA=   6.4  PHAS=  -54.9  FOM=  0.35  TEST= 0
INDE   19  44  55  FOBS=   39.9  SIGMA=   5.6  PHAS=  -85.2  FOM=  0.72  TEST= 0
INDE   19  44  57  FOBS=   62.0  SIGMA=   3.7  PHAS=   88.0  FOM=  0.75  TEST= 0
INDE   19  44  59  FOBS=   50.0  SIGMA=   5.6  PHAS=   83.1  FOM=  0.36  TEST= 0
INDE   19  44  61  FOBS=  111.7  SIGMA=   2.7  PHAS=  176.4  FOM=  0.92  TEST= 0
INDE   19  45  20  FOBS=   56.5  SIGMA=   3.6  PHAS=  173.3  FOM=  0.86  TEST= 0
```

*FIG. 12A - 432*

```
INDE  19  45  22  FOBS=    43.1  SIGMA=   4.4  PHAS=  -164.2  FOM=  0.59  TEST= 0
INDE  19  45  24  FOBS=   126.1  SIGMA=   1.6  PHAS=   176.8  FOM=  0.85  TEST= 0
INDE  19  45  26  FOBS=    57.9  SIGMA=   3.3  PHAS=    63.0  FOM=  0.15  TEST= 0
INDE  19  45  28  FOBS=    23.2  SIGMA=   8.6  PHAS=  -125.4  FOM=  0.64  TEST= 0
INDE  19  45  30  FOBS=     0.0  SIGMA=  18.8  PHAS=     0.0  FOM=  0.00  TEST= 0
INDE  19  45  32  FOBS=   213.9  SIGMA=   1.0  PHAS=    85.7  FOM=  0.96  TEST= 0
INDE  19  45  34  FOBS=     0.0  SIGMA=  22.1  PHAS=     0.0  FOM=  0.00  TEST= 1
INDE  19  45  36  FOBS=    91.8  SIGMA=   2.6  PHAS=    43.4  FOM=  0.91  TEST= 0
INDE  19  45  38  FOBS=   151.7  SIGMA=   1.4  PHAS=   -16.1  FOM=  0.95  TEST= 0
INDE  19  45  40  FOBS=    60.6  SIGMA=   3.4  PHAS=    -8.5  FOM=  0.78  TEST= 0
INDE  19  45  42  FOBS=   100.6  SIGMA=   2.1  PHAS=  -158.9  FOM=  0.88  TEST= 0
INDE  19  45  44  FOBS=   145.2  SIGMA=   1.5  PHAS=   162.5  FOM=  0.95  TEST= 0
INDE  19  45  46  FOBS=    43.3  SIGMA=   5.7  PHAS=   143.8  FOM=  0.29  TEST= 1
INDE  19  45  48  FOBS=    48.8  SIGMA=   4.7  PHAS=  -167.3  FOM=  0.44  TEST= 0
INDE  19  45  50  FOBS=    54.1  SIGMA=   4.1  PHAS=  -103.8  FOM=  0.54  TEST= 0
INDE  19  45  52  FOBS=   104.6  SIGMA=   2.2  PHAS=  -135.5  FOM=  0.91  TEST= 0
INDE  19  45  54  FOBS=    55.1  SIGMA=   4.1  PHAS=   130.1  FOM=  0.48  TEST= 0
INDE  19  45  56  FOBS=     0.0  SIGMA=  22.3  PHAS=     0.0  FOM=  0.00  TEST= 0
INDE  19  45  58  FOBS=    16.7  SIGMA=  20.0  PHAS=   -72.3  FOM=  0.11  TEST= 0
INDE  19  45  60  FOBS=   147.0  SIGMA=   2.1  PHAS=   -40.6  FOM=  0.93  TEST= 0
INDE  19  46  19  FOBS=   127.4  SIGMA=   1.5  PHAS=     1.1  FOM=  0.91  TEST= 0
INDE  19  46  21  FOBS=    70.3  SIGMA=   2.7  PHAS=   -62.0  FOM=  0.64  TEST= 1
INDE  19  46  23  FOBS=    12.1  SIGMA=  15.5  PHAS=    33.2  FOM=  0.05  TEST= 0
INDE  19  46  25  FOBS=    77.3  SIGMA=   2.7  PHAS=   115.4  FOM=  0.38  TEST= 0
INDE  19  46  27  FOBS=    71.2  SIGMA=   2.9  PHAS=   -83.7  FOM=  0.66  TEST= 0
INDE  19  46  29  FOBS=   144.0  SIGMA=   1.6  PHAS=    33.5  FOM=  0.92  TEST= 0
INDE  19  46  31  FOBS=    43.6  SIGMA=   4.4  PHAS=    24.3  FOM=  0.83  TEST= 0
INDE  19  46  33  FOBS=    75.2  SIGMA=   2.6  PHAS=   -94.8  FOM=  0.52  TEST= 0
INDE  19  46  35  FOBS=    59.7  SIGMA=   3.3  PHAS=   -24.8  FOM=  0.75  TEST= 0
INDE  19  46  37  FOBS=    69.0  SIGMA=   3.4  PHAS=  -101.0  FOM=  0.78  TEST= 0
INDE  19  46  39  FOBS=     9.4  SIGMA=  22.4  PHAS=   152.4  FOM=  0.14  TEST= 1
INDE  19  46  41  FOBS=    32.8  SIGMA=   6.4  PHAS=    70.7  FOM=  0.36  TEST= 0
INDE  19  46  43  FOBS=     0.0  SIGMA=  21.3  PHAS=     0.0  FOM=  0.00  TEST= 0
INDE  19  46  45  FOBS=    60.9  SIGMA=   3.5  PHAS=  -169.2  FOM=  0.80  TEST= 0
INDE  19  46  47  FOBS=    38.8  SIGMA=   6.4  PHAS=    -4.5  FOM=  0.65  TEST= 0
INDE  19  46  49  FOBS=    53.9  SIGMA=   4.2  PHAS=   169.7  FOM=  0.50  TEST= 0
INDE  19  46  51  FOBS=    46.0  SIGMA=   4.9  PHAS=    73.2  FOM=  0.37  TEST= 0
INDE  19  46  53  FOBS=    60.1  SIGMA=   3.8  PHAS=    92.6  FOM=  0.74  TEST= 0
INDE  19  46  55  FOBS=     0.0  SIGMA=  22.3  PHAS=     0.0  FOM=  0.00  TEST= 0
INDE  19  46  57  FOBS=    74.4  SIGMA=   3.4  PHAS=    59.1  FOM=  0.61  TEST= 0
INDE  19  46  59  FOBS=    42.0  SIGMA=   6.9  PHAS=   -63.9  FOM=  0.63  TEST= 0
INDE  19  47  20  FOBS=   144.2  SIGMA=   1.6  PHAS=    94.7  FOM=  0.83  TEST= 0
INDE  19  47  22  FOBS=   104.6  SIGMA=   2.1  PHAS=  -119.0  FOM=  0.66  TEST= 0
INDE  19  47  24  FOBS=   128.8  SIGMA=   1.8  PHAS=    88.4  FOM=  0.90  TEST= 0
INDE  19  47  26  FOBS=    79.3  SIGMA=   2.8  PHAS=   -97.9  FOM=  0.08  TEST= 0
INDE  19  47  28  FOBS=   188.7  SIGMA=   1.3  PHAS=  -103.8  FOM=  0.94  TEST= 0
INDE  19  47  30  FOBS=   151.2  SIGMA=   1.5  PHAS=   -42.0  FOM=  0.92  TEST= 0
INDE  19  47  32  FOBS=    95.6  SIGMA=   2.0  PHAS=    73.7  FOM=  0.78  TEST= 0
INDE  19  47  34  FOBS=   121.8  SIGMA=   1.6  PHAS=    32.0  FOM=  0.87  TEST= 0
INDE  19  47  36  FOBS=    63.1  SIGMA=   3.1  PHAS=   -85.9  FOM=  0.71  TEST= 0
INDE  19  47  38  FOBS=    94.6  SIGMA=   2.5  PHAS=    55.1  FOM=  0.83  TEST= 0
INDE  19  47  40  FOBS=    94.2  SIGMA=   2.2  PHAS=   -42.3  FOM=  0.86  TEST= 0
INDE  19  47  42  FOBS=    87.6  SIGMA=   2.4  PHAS=    34.3  FOM=  0.09  TEST= 1
INDE  19  47  44  FOBS=    80.0  SIGMA=   2.7  PHAS=   146.2  FOM=  0.67  TEST= 0
INDE  19  47  46  FOBS=     0.0  SIGMA=  20.4  PHAS=     0.0  FOM=  0.00  TEST= 1
INDE  19  47  48  FOBS=    30.6  SIGMA=   8.8  PHAS=  -140.7  FOM=  0.41  TEST= 0
INDE  19  47  50  FOBS=    17.9  SIGMA=  15.8  PHAS=    27.7  FOM=  0.07  TEST= 0
INDE  19  47  52  FOBS=   130.4  SIGMA=   1.8  PHAS=   110.4  FOM=  0.94  TEST= 0
INDE  19  47  54  FOBS=    46.1  SIGMA=   4.9  PHAS=   167.9  FOM=  0.47  TEST= 0
INDE  19  47  56  FOBS=     0.0  SIGMA=  21.4  PHAS=     0.0  FOM=  0.00  TEST= 0
INDE  19  47  58  FOBS=    40.2  SIGMA=   7.1  PHAS=   -24.3  FOM=  0.05  TEST= 1
INDE  19  48  19  FOBS=    82.1  SIGMA=   2.6  PHAS=   -12.6  FOM=  0.75  TEST= 0
INDE  19  48  21  FOBS=   121.0  SIGMA=   1.8  PHAS=   -52.4  FOM=  0.78  TEST= 0
INDE  19  48  23  FOBS=   177.9  SIGMA=   1.3  PHAS=   -14.4  FOM=  0.46  TEST= 1
INDE  19  48  25  FOBS=   104.8  SIGMA=   2.1  PHAS=   -87.9  FOM=  0.62  TEST= 0
INDE  19  48  27  FOBS=   205.5  SIGMA=   1.2  PHAS=   100.6  FOM=  0.96  TEST= 0
INDE  19  48  29  FOBS=   108.0  SIGMA=   2.1  PHAS=   109.8  FOM=  0.93  TEST= 0
INDE  19  48  31  FOBS=    51.3  SIGMA=   4.2  PHAS=   -77.8  FOM=  0.70  TEST= 0
INDE  19  48  33  FOBS=    43.5  SIGMA=   4.7  PHAS=     8.3  FOM=  0.43  TEST= 0
INDE  19  48  35  FOBS=     0.0  SIGMA=  22.2  PHAS=     0.0  FOM=  0.00  TEST= 0
```

*FIG. 12A - 433*

```
INDE 19 48 37 FOBS=   181.2 SIGMA=  1.2 PHAS=  -151.0 FOM= 0.95 TEST= 0
INDE 19 48 39 FOBS=    53.6 SIGMA=  3.7 PHAS=   146.6 FOM= 0.35 TEST= 0
INDE 19 48 41 FOBS=    39.7 SIGMA=  6.7 PHAS=  -116.8 FOM= 0.56 TEST= 0
INDE 19 48 43 FOBS=     0.0 SIGMA= 22.2 PHAS=     0.0 FOM= 0.00 TEST= 0
INDE 19 48 45 FOBS=    49.3 SIGMA=  4.3 PHAS=   157.2 FOM= 0.13 TEST= 0
INDE 19 48 47 FOBS=   102.0 SIGMA=  2.1 PHAS=    75.5 FOM= 0.79 TEST= 0
INDE 19 48 49 FOBS=    65.5 SIGMA=  3.5 PHAS=    33.9 FOM= 0.78 TEST= 0
INDE 19 48 51 FOBS=    36.7 SIGMA=  6.2 PHAS=   136.7 FOM= 0.43 TEST= 0
INDE 19 48 53 FOBS=    95.9 SIGMA=  2.5 PHAS=    49.3 FOM= 0.95 TEST= 0
INDE 19 48 55 FOBS=     0.0 SIGMA= 21.4 PHAS=     0.0 FOM= 0.00 TEST= 1
INDE 19 48 57 FOBS=     0.0 SIGMA= 25.6 PHAS=     0.0 FOM= 0.00 TEST= 0
INDE 19 49 20 FOBS=    88.9 SIGMA=  2.4 PHAS=  -176.2 FOM= 0.49 TEST= 0
INDE 19 49 22 FOBS=   260.2 SIGMA=  1.0 PHAS=   -53.0 FOM= 0.97 TEST= 0
INDE 19 49 24 FOBS=   136.7 SIGMA=  1.7 PHAS=    -7.6 FOM= 0.91 TEST= 0
INDE 19 49 26 FOBS=   172.8 SIGMA=  1.4 PHAS=   -34.3 FOM= 0.96 TEST= 0
INDE 19 49 28 FOBS=    88.4 SIGMA=  2.8 PHAS=    -9.2 FOM= 0.93 TEST= 0
INDE 19 49 30 FOBS=   145.7 SIGMA=  1.6 PHAS=   -65.5 FOM= 0.95 TEST= 0
INDE 19 49 32 FOBS=    52.0 SIGMA=  3.9 PHAS=    78.1 FOM= 0.48 TEST= 0
INDE 19 49 34 FOBS=   102.9 SIGMA=  1.9 PHAS=    59.7 FOM= 0.93 TEST= 0
INDE 19 49 36 FOBS=    65.4 SIGMA=  2.9 PHAS=   175.2 FOM= 0.82 TEST= 0
INDE 19 49 38 FOBS=    92.3 SIGMA=  2.1 PHAS=    40.0 FOM= 0.73 TEST= 0
INDE 19 49 40 FOBS=     0.0 SIGMA= 20.8 PHAS=     0.0 FOM= 0.00 TEST= 0
INDE 19 49 42 FOBS=   103.0 SIGMA=  2.1 PHAS=   127.8 FOM= 0.92 TEST= 0
INDE 19 49 44 FOBS=    29.3 SIGMA=  7.1 PHAS=  -110.9 FOM= 0.34 TEST= 0
INDE 19 49 46 FOBS=   112.6 SIGMA=  2.0 PHAS=   -73.6 FOM= 0.95 TEST= 0
INDE 19 49 48 FOBS=   116.5 SIGMA=  1.9 PHAS=  -102.3 FOM= 0.93 TEST= 0
INDE 19 49 50 FOBS=     0.0 SIGMA= 21.3 PHAS=     0.0 FOM= 0.00 TEST= 0
INDE 19 49 52 FOBS=    64.8 SIGMA=  3.6 PHAS=    46.5 FOM= 0.83 TEST= 0
INDE 19 49 54 FOBS=    55.4 SIGMA=  4.2 PHAS=  -172.4 FOM= 0.78 TEST= 0
INDE 19 49 56 FOBS=     0.0 SIGMA= 26.3 PHAS=     0.0 FOM= 0.00 TEST= 1
INDE 19 50 19 FOBS=    69.7 SIGMA=  3.0 PHAS=    62.5 FOM= 0.87 TEST= 0
INDE 19 50 21 FOBS=   210.3 SIGMA=  1.2 PHAS=    94.4 FOM= 0.95 TEST= 0
INDE 19 50 23 FOBS=    52.8 SIGMA=  4.1 PHAS=   -74.9 FOM= 0.38 TEST= 0
INDE 19 50 25 FOBS=   257.0 SIGMA=  1.3 PHAS=  -110.7 FOM= 0.97 TEST= 0
INDE 19 50 27 FOBS=    10.4 SIGMA= 20.7 PHAS=   130.5 FOM= 0.10 TEST= 0
INDE 19 50 29 FOBS=    77.5 SIGMA=  2.9 PHAS=  -151.5 FOM= 0.56 TEST= 0
INDE 19 50 31 FOBS=    78.9 SIGMA=  2.8 PHAS=  -158.7 FOM= 0.93 TEST= 0
INDE 19 50 33 FOBS=   145.0 SIGMA=  1.4 PHAS=   -24.8 FOM= 0.97 TEST= 0
INDE 19 50 35 FOBS=    40.3 SIGMA=  5.5 PHAS=   124.0 FOM= 0.53 TEST= 0
INDE 19 50 37 FOBS=    93.1 SIGMA=  2.1 PHAS=   174.4 FOM= 0.86 TEST= 0
INDE 19 50 39 FOBS=    40.7 SIGMA=  5.0 PHAS=   -18.0 FOM= 0.11 TEST= 0
INDE 19 50 41 FOBS=    23.4 SIGMA= 10.7 PHAS=   -48.6 FOM= 0.51 TEST= 0
INDE 19 50 43 FOBS=    19.8 SIGMA= 12.5 PHAS=   -22.6 FOM= 0.12 TEST= 0
INDE 19 50 45 FOBS=   140.1 SIGMA=  1.6 PHAS=  -164.4 FOM= 0.95 TEST= 0
INDE 19 50 47 FOBS=   136.4 SIGMA=  1.7 PHAS=   151.2 FOM= 0.97 TEST= 0
INDE 19 50 49 FOBS=    62.8 SIGMA=  3.2 PHAS=   149.0 FOM= 0.73 TEST= 0
INDE 19 50 51 FOBS=    36.0 SIGMA=  7.5 PHAS=  -106.8 FOM= 0.60 TEST= 0
INDE 19 50 53 FOBS=    84.8 SIGMA=  2.8 PHAS=    70.5 FOM= 0.87 TEST= 0
INDE 19 50 55 FOBS=     0.0 SIGMA= 25.5 PHAS=     0.0 FOM= 0.00 TEST= 0
INDE 19 51 20 FOBS=     0.0 SIGMA= 21.5 PHAS=     0.0 FOM= 0.00 TEST= 0
INDE 19 51 22 FOBS=   182.1 SIGMA=  1.3 PHAS=    -7.2 FOM= 0.97 TEST= 0
INDE 19 51 24 FOBS=    81.2 SIGMA=  2.6 PHAS=     8.9 FOM= 0.32 TEST= 0
INDE 19 51 26 FOBS=   113.5 SIGMA=  2.0 PHAS=  -143.9 FOM= 0.93 TEST= 0
INDE 19 51 28 FOBS=    42.3 SIGMA=  5.5 PHAS=  -133.4 FOM= 0.41 TEST= 0
INDE 19 51 30 FOBS=     6.1 SIGMA= 35.5 PHAS=    67.5 FOM= 0.04 TEST= 0
INDE 19 51 32 FOBS=    69.7 SIGMA=  3.1 PHAS=   125.4 FOM= 0.60 TEST= 0
INDE 19 51 34 FOBS=   127.5 SIGMA=  1.6 PHAS=   163.5 FOM= 0.91 TEST= 0
INDE 19 51 36 FOBS=    67.3 SIGMA=  2.8 PHAS=   104.7 FOM= 0.70 TEST= 0
INDE 19 51 38 FOBS=     0.0 SIGMA= 21.1 PHAS=     0.0 FOM= 0.00 TEST= 0
INDE 19 51 40 FOBS=     0.0 SIGMA= 20.1 PHAS=     0.0 FOM= 0.00 TEST= 0
INDE 19 51 42 FOBS=    27.7 SIGMA=  7.5 PHAS=    77.7 FOM= 0.51 TEST= 0
INDE 19 51 44 FOBS=    57.1 SIGMA=  3.8 PHAS=    29.2 FOM= 0.35 TEST= 0
INDE 19 51 46 FOBS=    59.8 SIGMA=  3.6 PHAS=    19.7 FOM= 0.88 TEST= 0
INDE 19 51 48 FOBS=    77.6 SIGMA=  2.8 PHAS=    87.0 FOM= 0.92 TEST= 0
INDE 19 51 50 FOBS=    52.3 SIGMA=  3.9 PHAS=    73.2 FOM= 0.81 TEST= 0
INDE 19 51 52 FOBS=     0.0 SIGMA= 24.1 PHAS=     0.0 FOM= 0.00 TEST= 0
INDE 19 51 54 FOBS=     0.0 SIGMA= 26.5 PHAS=     0.0 FOM= 0.00 TEST= 0
INDE 19 52 19 FOBS=    52.2 SIGMA=  4.2 PHAS=  -168.3 FOM= 0.86 TEST= 0
INDE 19 52 21 FOBS=   176.4 SIGMA=  1.4 PHAS=   148.1 FOM= 0.97 TEST= 0
INDE 19 52 23 FOBS=    33.5 SIGMA=  6.7 PHAS=  -122.2 FOM= 0.33 TEST= 0
```

*FIG. 12A - 434*

```
INDE 19 52 25 FOBS=   79.5 SIGMA=  2.7 PHAS=  103.8 FOM= 0.65 TEST= 0
INDE 19 52 27 FOBS=    0.0 SIGMA= 22.7 PHAS=    0.0 FOM= 0.00 TEST= 0
INDE 19 52 29 FOBS=   58.6 SIGMA=  3.7 PHAS=  -59.9 FOM= 0.91 TEST= 0
INDE 19 52 31 FOBS=   51.9 SIGMA=  4.2 PHAS=   10.3 FOM= 0.73 TEST= 0
INDE 19 52 33 FOBS=  104.1 SIGMA=  2.1 PHAS=   30.7 FOM= 0.92 TEST= 0
INDE 19 52 35 FOBS=   96.2 SIGMA=  2.0 PHAS=  110.4 FOM= 0.19 TEST= 1
INDE 19 52 37 FOBS=   21.9 SIGMA=  9.7 PHAS=  -36.3 FOM= 0.41 TEST= 0
INDE 19 52 39 FOBS=   36.7 SIGMA=  6.1 PHAS=  -32.8 FOM= 0.46 TEST= 0
INDE 19 52 41 FOBS=   42.1 SIGMA=  4.4 PHAS= -108.8 FOM= 0.74 TEST= 0
INDE 19 52 43 FOBS=   35.8 SIGMA=  7.2 PHAS=  -70.8 FOM= 0.33 TEST= 0
INDE 19 52 45 FOBS=  121.7 SIGMA=  1.8 PHAS= -113.6 FOM= 0.93 TEST= 0
INDE 19 52 47 FOBS=   21.6 SIGMA= 10.7 PHAS=  -15.9 FOM= 0.44 TEST= 0
INDE 19 52 49 FOBS=   41.3 SIGMA=  6.4 PHAS=  -61.2 FOM= 0.75 TEST= 0
INDE 19 52 51 FOBS=   55.8 SIGMA=  4.0 PHAS=   58.2 FOM= 0.69 TEST= 0
INDE 19 52 53 FOBS=   53.8 SIGMA=  8.4 PHAS=  111.4 FOM= 0.38 TEST= 0
INDE 19 53 20 FOBS=  110.4 SIGMA=  2.0 PHAS=   28.9 FOM= 0.94 TEST= 1
INDE 19 53 22 FOBS=   50.7 SIGMA=  4.1 PHAS=   75.6 FOM= 0.73 TEST= 0
INDE 19 53 24 FOBS=   71.2 SIGMA=  3.0 PHAS=  -17.8 FOM= 0.76 TEST= 0
INDE 19 53 26 FOBS=   21.4 SIGMA= 10.7 PHAS=  148.9 FOM= 0.40 TEST= 0
INDE 19 53 28 FOBS=  142.7 SIGMA=  1.6 PHAS= -117.8 FOM= 0.66 TEST= 1
INDE 19 53 30 FOBS=  130.6 SIGMA=  1.7 PHAS=  -98.0 FOM= 0.95 TEST= 0
INDE 19 53 32 FOBS=  102.8 SIGMA=  2.1 PHAS=  -36.5 FOM= 0.77 TEST= 0
INDE 19 53 34 FOBS=   54.0 SIGMA=  3.7 PHAS= -171.7 FOM= 0.22 TEST= 0
INDE 19 53 36 FOBS=    0.0 SIGMA= 19.3 PHAS=    0.0 FOM= 0.00 TEST= 0
INDE 19 53 38 FOBS=  104.7 SIGMA=  1.9 PHAS= -170.8 FOM= 0.89 TEST= 0
INDE 19 53 40 FOBS=   65.2 SIGMA=  3.0 PHAS= -162.5 FOM= 0.76 TEST= 0
INDE 19 53 42 FOBS=   80.0 SIGMA=  2.3 PHAS=  163.6 FOM= 0.84 TEST= 0
INDE 19 53 44 FOBS=    8.3 SIGMA= 28.2 PHAS= -134.6 FOM= 0.08 TEST= 0
INDE 19 53 46 FOBS=   67.3 SIGMA=  3.6 PHAS=  178.5 FOM= 0.92 TEST= 0
INDE 19 53 48 FOBS=   85.5 SIGMA=  3.3 PHAS= -163.3 FOM= 0.91 TEST= 0
INDE 19 53 50 FOBS=   50.1 SIGMA=  5.5 PHAS=  -45.2 FOM= 0.82 TEST= 0
INDE 19 53 52 FOBS=   33.5 SIGMA=  9.3 PHAS=   94.4 FOM= 0.34 TEST= 0
INDE 19 54 19 FOBS=    7.6 SIGMA= 25.2 PHAS= -101.2 FOM= 0.09 TEST= 0
INDE 19 54 21 FOBS=    0.0 SIGMA= 21.4 PHAS=    0.0 FOM= 0.00 TEST= 1
INDE 19 54 23 FOBS=   49.2 SIGMA=  4.2 PHAS=   89.1 FOM= 0.69 TEST= 0
INDE 19 54 25 FOBS=   88.4 SIGMA=  2.4 PHAS=   52.7 FOM= 0.89 TEST= 0
INDE 19 54 27 FOBS=   10.7 SIGMA= 23.6 PHAS=   47.2 FOM= 0.16 TEST= 0
INDE 19 54 29 FOBS=   77.4 SIGMA=  2.8 PHAS= -131.3 FOM= 0.71 TEST= 0
INDE 19 54 31 FOBS=  106.7 SIGMA=  2.1 PHAS= -122.4 FOM= 0.62 TEST= 0
INDE 19 54 33 FOBS=   65.7 SIGMA=  3.3 PHAS=   24.7 FOM= 0.46 TEST= 0
INDE 19 54 35 FOBS=   38.1 SIGMA=  5.0 PHAS=  137.5 FOM= 0.59 TEST= 0
INDE 19 54 37 FOBS=   90.0 SIGMA=  2.2 PHAS=   73.9 FOM= 0.48 TEST= 0
INDE 19 54 39 FOBS=   33.3 SIGMA=  6.9 PHAS=   70.6 FOM= 0.28 TEST= 0
INDE 19 54 41 FOBS=   12.3 SIGMA= 17.1 PHAS=  149.4 FOM= 0.45 TEST= 0
INDE 19 54 43 FOBS=    7.7 SIGMA= 27.3 PHAS= -154.2 FOM= 0.20 TEST= 0
INDE 19 54 45 FOBS=    0.0 SIGMA= 22.9 PHAS=    0.0 FOM= 0.00 TEST= 0
INDE 19 54 47 FOBS=   61.9 SIGMA=  4.4 PHAS=   81.9 FOM= 0.84 TEST= 0
INDE 19 54 49 FOBS=   56.1 SIGMA=  5.0 PHAS= -149.1 FOM= 0.84 TEST= 0
INDE 19 54 51 FOBS=   33.7 SIGMA=  9.4 PHAS=  -76.5 FOM= 0.10 TEST= 1
INDE 19 55 20 FOBS=  163.8 SIGMA=  1.8 PHAS=  -23.2 FOM= 0.95 TEST= 0
INDE 19 55 22 FOBS=   91.6 SIGMA=  2.5 PHAS=  -58.3 FOM= 0.80 TEST= 0
INDE 19 55 24 FOBS=  171.3 SIGMA=  1.3 PHAS=  -51.3 FOM= 0.96 TEST= 0
INDE 19 55 26 FOBS=   21.1 SIGMA=  9.8 PHAS=  -41.1 FOM= 0.25 TEST= 1
INDE 19 55 28 FOBS=   27.4 SIGMA=  7.7 PHAS= -131.9 FOM= 0.37 TEST= 0
INDE 19 55 30 FOBS=   98.1 SIGMA=  2.2 PHAS=  -63.7 FOM= 0.90 TEST= 0
INDE 19 55 32 FOBS=   51.4 SIGMA=  4.2 PHAS=  -20.7 FOM= 0.13 TEST= 1
INDE 19 55 34 FOBS=   85.9 SIGMA=  2.6 PHAS= -148.4 FOM= 0.77 TEST= 0
INDE 19 55 36 FOBS=   60.5 SIGMA=  3.4 PHAS=   34.5 FOM= 0.44 TEST= 0
INDE 19 55 38 FOBS=    0.0 SIGMA= 22.0 PHAS=    0.0 FOM= 0.00 TEST= 0
INDE 19 55 40 FOBS=   49.4 SIGMA=  4.6 PHAS= -101.6 FOM= 0.78 TEST= 0
INDE 19 55 42 FOBS=  119.6 SIGMA=  1.9 PHAS=  134.3 FOM= 0.95 TEST= 0
INDE 19 55 44 FOBS=    0.0 SIGMA= 22.3 PHAS=    0.0 FOM= 0.00 TEST= 0
INDE 19 55 46 FOBS=    0.0 SIGMA= 23.1 PHAS=    0.0 FOM= 0.00 TEST= 1
INDE 19 55 48 FOBS=   69.2 SIGMA=  4.1 PHAS=   97.4 FOM= 0.84 TEST= 0
INDE 19 55 50 FOBS=    0.0 SIGMA= 25.2 PHAS=    0.0 FOM= 0.00 TEST= 1
INDE 19 56 19 FOBS=   74.8 SIGMA=  2.6 PHAS= -147.0 FOM= 0.91 TEST= 0
INDE 19 56 21 FOBS=  134.5 SIGMA=  2.1 PHAS= -174.9 FOM= 0.95 TEST= 0
INDE 19 56 23 FOBS=  141.6 SIGMA=  1.6 PHAS=  171.2 FOM= 0.96 TEST= 0
INDE 19 56 25 FOBS=   83.6 SIGMA=  2.5 PHAS=  105.9 FOM= 0.72 TEST= 0
INDE 19 56 27 FOBS=    0.0 SIGMA= 20.4 PHAS=    0.0 FOM= 0.00 TEST= 0
```

*FIG. 12A - 435*

```
INDE 19 56 29 FOBS=   124.7 SIGMA=  1.8 PHAS=  -91.6 FOM= 0.89 TEST= 0
INDE 19 56 31 FOBS=   119.0 SIGMA=  2.1 PHAS= -128.6 FOM= 0.94 TEST= 0
INDE 19 56 33 FOBS=    51.9 SIGMA=  5.2 PHAS=  107.9 FOM= 0.38 TEST= 1
INDE 19 56 35 FOBS=    35.7 SIGMA=  7.5 PHAS=  167.7 FOM= 0.29 TEST= 0
INDE 19 56 37 FOBS=    37.9 SIGMA=  5.8 PHAS=   60.1 FOM= 0.70 TEST= 0
INDE 19 56 39 FOBS=    28.5 SIGMA=  7.9 PHAS=  170.5 FOM= 0.55 TEST= 0
INDE 19 56 41 FOBS=    96.9 SIGMA=  2.4 PHAS=   10.1 FOM= 0.93 TEST= 0
INDE 19 56 43 FOBS=    45.4 SIGMA=  4.6 PHAS=   89.8 FOM= 0.44 TEST= 0
INDE 19 56 45 FOBS=    12.6 SIGMA= 21.3 PHAS= -133.0 FOM= 0.01 TEST= 1
INDE 19 56 47 FOBS=    86.3 SIGMA=  3.2 PHAS=  -35.5 FOM= 0.91 TEST= 0
INDE 19 56 49 FOBS=    64.5 SIGMA=  5.0 PHAS=  -46.2 FOM= 0.71 TEST= 0
INDE 19 57 20 FOBS=     0.0 SIGMA= 24.4 PHAS=    0.0 FOM= 0.00 TEST= 0
INDE 19 57 22 FOBS=    29.1 SIGMA=  8.4 PHAS=   77.6 FOM= 0.77 TEST= 0
INDE 19 57 24 FOBS=    77.4 SIGMA=  2.7 PHAS=   19.4 FOM= 0.90 TEST= 0
INDE 19 57 26 FOBS=    45.5 SIGMA=  5.0 PHAS=  -14.3 FOM= 0.49 TEST= 0
INDE 19 57 28 FOBS=    62.9 SIGMA=  4.1 PHAS=   68.2 FOM= 0.28 TEST= 0
INDE 19 57 30 FOBS=    78.0 SIGMA=  3.4 PHAS=  124.7 FOM= 0.63 TEST= 0
INDE 19 57 32 FOBS=    57.0 SIGMA=  4.7 PHAS=  117.9 FOM= 0.87 TEST= 0
INDE 19 57 34 FOBS=    40.5 SIGMA=  9.1 PHAS=   81.3 FOM= 0.10 TEST= 1
INDE 19 57 36 FOBS=    60.5 SIGMA=  4.0 PHAS=   38.8 FOM= 0.85 TEST= 0
INDE 19 57 38 FOBS=    41.6 SIGMA=  5.4 PHAS=   56.2 FOM= 0.29 TEST= 0
INDE 19 57 40 FOBS=    79.6 SIGMA=  2.9 PHAS= -100.2 FOM= 0.88 TEST= 0
INDE 19 57 42 FOBS=    76.8 SIGMA=  3.1 PHAS= -176.9 FOM= 0.92 TEST= 0
INDE 19 57 44 FOBS=    29.1 SIGMA=  8.2 PHAS=  -31.3 FOM= 0.54 TEST= 0
INDE 19 57 46 FOBS=    54.8 SIGMA=  4.6 PHAS= -108.4 FOM= 0.84 TEST= 0
INDE 19 57 48 FOBS=    57.4 SIGMA=  5.6 PHAS= -170.9 FOM= 0.76 TEST= 0
INDE 19 58 19 FOBS=     6.6 SIGMA= 36.2 PHAS=   21.1 FOM= 0.03 TEST= 0
INDE 19 58 21 FOBS=    46.0 SIGMA=  5.5 PHAS=  125.5 FOM= 0.62 TEST= 0
INDE 19 58 23 FOBS=    28.5 SIGMA=  8.6 PHAS=   66.6 FOM= 0.63 TEST= 0
INDE 19 58 25 FOBS=    59.8 SIGMA=  4.1 PHAS=  -66.1 FOM= 0.82 TEST= 0
INDE 19 58 27 FOBS=     0.0 SIGMA= 24.1 PHAS=    0.0 FOM= 0.00 TEST= 0
INDE 19 58 29 FOBS=    48.1 SIGMA=  5.4 PHAS=   69.4 FOM= 0.07 TEST= 0
INDE 19 58 31 FOBS=    43.7 SIGMA=  6.0 PHAS=  146.0 FOM= 0.48 TEST= 0
INDE 19 58 33 FOBS=     0.0 SIGMA= 23.0 PHAS=    0.0 FOM= 0.00 TEST= 0
INDE 19 58 35 FOBS=    45.2 SIGMA=  6.9 PHAS=  -35.4 FOM= 0.59 TEST= 0
INDE 19 58 37 FOBS=     0.0 SIGMA= 22.1 PHAS=    0.0 FOM= 0.00 TEST= 0
INDE 19 58 39 FOBS=    78.4 SIGMA=  3.0 PHAS= -127.4 FOM= 0.18 TEST= 1
INDE 19 58 41 FOBS=    70.0 SIGMA=  3.3 PHAS=   86.0 FOM= 0.40 TEST= 1
INDE 19 58 43 FOBS=    46.6 SIGMA=  5.6 PHAS=    1.4 FOM= 0.16 TEST= 0
INDE 19 58 45 FOBS=    41.4 SIGMA=  5.8 PHAS=  126.3 FOM= 0.11 TEST= 0
INDE 19 58 47 FOBS=     0.0 SIGMA= 23.7 PHAS=    0.0 FOM= 0.00 TEST= 0
INDE 19 59 20 FOBS=    44.1 SIGMA=  5.3 PHAS=   -5.4 FOM= 0.57 TEST= 0
INDE 19 59 22 FOBS=    93.6 SIGMA=  3.9 PHAS=  -31.5 FOM= 0.91 TEST= 0
INDE 19 59 24 FOBS=   126.5 SIGMA=  2.0 PHAS=  -19.5 FOM= 0.96 TEST= 0
INDE 19 59 26 FOBS=    33.0 SIGMA=  7.5 PHAS= -174.2 FOM= 0.48 TEST= 0
INDE 19 59 28 FOBS=    62.6 SIGMA=  4.1 PHAS=   72.1 FOM= 0.88 TEST= 0
INDE 19 59 30 FOBS=    19.6 SIGMA= 18.0 PHAS=   94.3 FOM= 0.30 TEST= 0
INDE 19 59 32 FOBS=    40.1 SIGMA=  6.6 PHAS=   37.0 FOM= 0.61 TEST= 0
INDE 19 59 34 FOBS=    29.7 SIGMA=  9.1 PHAS=  101.0 FOM= 0.46 TEST= 0
INDE 19 59 36 FOBS=    57.5 SIGMA=  4.8 PHAS=  104.7 FOM= 0.51 TEST= 0
INDE 19 59 38 FOBS=    65.2 SIGMA=  3.6 PHAS=  125.2 FOM= 0.82 TEST= 0
INDE 19 59 40 FOBS=    38.9 SIGMA=  7.6 PHAS=  -68.4 FOM= 0.65 TEST= 0
INDE 19 59 42 FOBS=   104.6 SIGMA=  2.4 PHAS= -145.3 FOM= 0.95 TEST= 0
INDE 19 59 44 FOBS=    67.0 SIGMA=  3.7 PHAS= -125.0 FOM= 0.72 TEST= 0
INDE 19 59 46 FOBS=    14.3 SIGMA= 19.7 PHAS=  -24.7 FOM= 0.06 TEST= 0
INDE 19 60 19 FOBS=    70.5 SIGMA=  3.8 PHAS=  -61.3 FOM= 0.78 TEST= 0
INDE 19 60 21 FOBS=    51.0 SIGMA=  6.9 PHAS=  -13.6 FOM= 0.41 TEST= 0
INDE 19 60 23 FOBS=    57.9 SIGMA=  6.1 PHAS=  -69.7 FOM= 0.62 TEST= 0
INDE 19 60 25 FOBS=    98.0 SIGMA=  2.6 PHAS=  -78.3 FOM= 0.89 TEST= 0
INDE 19 60 27 FOBS=   119.8 SIGMA=  2.2 PHAS=   -2.6 FOM= 0.91 TEST= 0
INDE 19 60 29 FOBS=    80.9 SIGMA=  3.2 PHAS=  -15.3 FOM= 0.76 TEST= 0
INDE 19 60 31 FOBS=    32.2 SIGMA=  8.1 PHAS=  155.6 FOM= 0.41 TEST= 0
INDE 19 60 33 FOBS=   116.6 SIGMA=  2.4 PHAS=  -55.4 FOM= 0.92 TEST= 0
INDE 19 60 35 FOBS=   103.9 SIGMA=  2.7 PHAS=  -41.6 FOM= 0.91 TEST= 0
INDE 19 60 37 FOBS=    85.8 SIGMA=  3.3 PHAS=   46.6 FOM= 0.92 TEST= 0
INDE 19 60 39 FOBS=    75.3 SIGMA=  3.1 PHAS= -117.0 FOM= 0.26 TEST= 1
INDE 19 60 41 FOBS=    82.1 SIGMA=  2.9 PHAS=  136.2 FOM= 0.94 TEST= 0
INDE 19 60 43 FOBS=    67.2 SIGMA=  4.4 PHAS=   88.7 FOM= 0.90 TEST= 0
INDE 19 60 45 FOBS=     0.0 SIGMA= 23.7 PHAS=    0.0 FOM= 0.00 TEST= 0
INDE 19 61 20 FOBS=    84.4 SIGMA=  3.2 PHAS=  -96.1 FOM= 0.90 TEST= 0
```

*FIG. 12A - 436*

```
INDE 19 61 22 FOBS=    59.5 SIGMA=   5.9 PHAS= -115.4 FOM= 0.76 TEST= 0
INDE 19 61 24 FOBS=     0.0 SIGMA=  21.9 PHAS=    0.0 FOM= 0.00 TEST= 0
INDE 19 61 26 FOBS=    75.8 SIGMA=   3.3 PHAS= -119.8 FOM= 0.76 TEST= 0
INDE 19 61 28 FOBS=    93.6 SIGMA=   2.8 PHAS= -114.7 FOM= 0.86 TEST= 0
INDE 19 61 30 FOBS=     0.0 SIGMA=  22.6 PHAS=    0.0 FOM= 0.00 TEST= 0
INDE 19 61 32 FOBS=    47.1 SIGMA=   5.7 PHAS= -156.4 FOM= 0.09 TEST= 1
INDE 19 61 34 FOBS=   105.5 SIGMA=   2.7 PHAS= -149.2 FOM= 0.95 TEST= 0
INDE 19 61 36 FOBS=    50.5 SIGMA=   6.2 PHAS= -105.0 FOM= 0.72 TEST= 0
INDE 19 61 38 FOBS=    71.9 SIGMA=   3.3 PHAS=  -98.0 FOM= 0.83 TEST= 0
INDE 19 61 40 FOBS=    45.3 SIGMA=   5.7 PHAS=  138.2 FOM= 0.85 TEST= 0
INDE 19 61 42 FOBS=    58.2 SIGMA=   5.7 PHAS=  -37.4 FOM= 0.67 TEST= 0
INDE 19 61 44 FOBS=    61.0 SIGMA=   5.0 PHAS= -108.2 FOM= 0.80 TEST= 0
INDE 19 62 19 FOBS=    26.2 SIGMA=  11.6 PHAS= -159.8 FOM= 0.57 TEST= 0
INDE 19 62 21 FOBS=    41.2 SIGMA=   6.2 PHAS=  144.9 FOM= 0.65 TEST= 0
INDE 19 62 23 FOBS=    49.0 SIGMA=   7.2 PHAS=  146.2 FOM= 0.47 TEST= 0
INDE 19 62 25 FOBS=    30.3 SIGMA=   9.3 PHAS=  -56.3 FOM= 0.27 TEST= 0
INDE 19 62 27 FOBS=    99.2 SIGMA=   2.6 PHAS=  144.2 FOM= 0.87 TEST= 0
INDE 19 62 29 FOBS=    58.8 SIGMA=   4.4 PHAS= -142.9 FOM= 0.83 TEST= 0
INDE 19 62 31 FOBS=    39.9 SIGMA=   6.6 PHAS=   57.9 FOM= 0.43 TEST= 0
INDE 19 62 33 FOBS=   101.7 SIGMA=   2.7 PHAS= -126.6 FOM= 0.04 TEST= 1
INDE 19 62 35 FOBS=    47.4 SIGMA=   5.8 PHAS=  123.4 FOM= 0.49 TEST= 0
INDE 19 62 37 FOBS=    40.5 SIGMA=   8.0 PHAS=  165.8 FOM= 0.12 TEST= 1
INDE 19 62 39 FOBS=    51.4 SIGMA=   4.6 PHAS=  172.3 FOM= 0.79 TEST= 0
INDE 19 62 41 FOBS=    68.7 SIGMA=   6.0 PHAS= -108.4 FOM= 0.08 TEST= 1
INDE 19 63 20 FOBS=    51.9 SIGMA=   5.1 PHAS=   62.6 FOM= 0.58 TEST= 0
INDE 19 63 22 FOBS=    48.0 SIGMA=   7.3 PHAS=   27.0 FOM= 0.73 TEST= 0
INDE 19 63 24 FOBS=    10.2 SIGMA=  34.5 PHAS=  -59.6 FOM= 0.12 TEST= 0
INDE 19 63 26 FOBS=    74.8 SIGMA=   3.9 PHAS=   60.5 FOM= 0.74 TEST= 0
INDE 19 63 28 FOBS=   138.1 SIGMA=   2.3 PHAS=  115.7 FOM= 0.93 TEST= 0
INDE 19 63 30 FOBS=     0.0 SIGMA=  26.9 PHAS=    0.0 FOM= 0.00 TEST= 0
INDE 19 63 32 FOBS=    44.9 SIGMA=   6.9 PHAS=  123.4 FOM= 0.42 TEST= 0
INDE 19 63 34 FOBS=    59.6 SIGMA=   5.3 PHAS=   -0.2 FOM= 0.78 TEST= 0
INDE 19 63 36 FOBS=    72.2 SIGMA=   4.6 PHAS= -147.3 FOM= 0.11 TEST= 1
INDE 19 63 38 FOBS=    50.7 SIGMA=   6.5 PHAS= -149.2 FOM= 0.46 TEST= 0
INDE 19 63 40 FOBS=   102.3 SIGMA=   3.4 PHAS=  131.7 FOM= 0.92 TEST= 0
INDE 19 64 19 FOBS=     0.0 SIGMA=  22.5 PHAS=    0.0 FOM= 0.00 TEST= 0
INDE 19 64 21 FOBS=    50.3 SIGMA=   5.2 PHAS=  -57.2 FOM= 0.60 TEST= 0
INDE 19 64 23 FOBS=    44.2 SIGMA=   8.0 PHAS=   61.3 FOM= 0.70 TEST= 0
INDE 19 64 25 FOBS=    15.4 SIGMA=  22.8 PHAS=  144.7 FOM= 0.15 TEST= 0
INDE 19 64 27 FOBS=   166.7 SIGMA=   1.9 PHAS=    8.2 FOM= 0.96 TEST= 0
INDE 19 64 29 FOBS=    22.5 SIGMA=  15.9 PHAS=   -5.4 FOM= 0.33 TEST= 0
INDE 19 64 31 FOBS=    58.2 SIGMA=   5.3 PHAS= -154.4 FOM= 0.86 TEST= 0
INDE 19 64 33 FOBS=    47.5 SIGMA=   8.1 PHAS=  -16.1 FOM= 0.50 TEST= 0
INDE 19 64 35 FOBS=    27.1 SIGMA=  11.9 PHAS=  -39.6 FOM= 0.39 TEST= 0
INDE 19 64 37 FOBS=    52.8 SIGMA=   6.3 PHAS=  165.0 FOM= 0.89 TEST= 0
INDE 19 64 39 FOBS=    13.9 SIGMA=  29.2 PHAS=   66.2 FOM= 0.15 TEST= 0
INDE 19 65 20 FOBS=     6.1 SIGMA=  42.8 PHAS=  -92.3 FOM= 0.09 TEST= 0
INDE 19 65 22 FOBS=    33.6 SIGMA=   7.8 PHAS=   18.4 FOM= 0.49 TEST= 0
INDE 19 65 24 FOBS=    74.6 SIGMA=   4.9 PHAS=   13.3 FOM= 0.56 TEST= 0
INDE 19 65 26 FOBS=    67.0 SIGMA=   4.4 PHAS= -127.7 FOM= 0.90 TEST= 0
INDE 19 65 28 FOBS=    47.2 SIGMA=   6.3 PHAS= -121.9 FOM= 0.82 TEST= 0
INDE 19 65 30 FOBS=   104.9 SIGMA=   3.0 PHAS=  117.0 FOM= 0.93 TEST= 0
INDE 19 65 32 FOBS=    54.3 SIGMA=   7.0 PHAS=  121.3 FOM= 0.77 TEST= 0
INDE 19 65 34 FOBS=    33.2 SIGMA=   9.6 PHAS=  -10.2 FOM= 0.77 TEST= 0
INDE 19 65 36 FOBS=    69.4 SIGMA=   4.8 PHAS=  117.1 FOM= 0.87 TEST= 0
INDE 19 65 38 FOBS=    67.2 SIGMA=   6.3 PHAS=   46.1 FOM= 0.54 TEST= 0
INDE 19 66 19 FOBS=    93.1 SIGMA=   3.3 PHAS= -178.1 FOM= 0.89 TEST= 0
INDE 19 66 21 FOBS=     0.0 SIGMA=  24.7 PHAS=    0.0 FOM= 0.00 TEST= 0
INDE 19 66 23 FOBS=    61.5 SIGMA=   5.8 PHAS= -169.3 FOM= 0.71 TEST= 0
INDE 19 66 25 FOBS=    95.5 SIGMA=   3.9 PHAS=  116.9 FOM= 0.89 TEST= 0
INDE 19 66 27 FOBS=    86.9 SIGMA=   3.5 PHAS=   79.9 FOM= 0.65 TEST= 0
INDE 19 66 29 FOBS=    58.8 SIGMA=   5.2 PHAS=   89.1 FOM= 0.20 TEST= 1
INDE 19 66 31 FOBS=     0.0 SIGMA=  27.9 PHAS=    0.0 FOM= 0.00 TEST= 0
INDE 19 66 33 FOBS=    54.0 SIGMA=   5.9 PHAS=   94.8 FOM= 0.11 TEST= 1
INDE 19 66 35 FOBS=    59.9 SIGMA=   5.6 PHAS=   54.5 FOM= 0.78 TEST= 0
INDE 19 67 20 FOBS=    67.7 SIGMA=   4.5 PHAS=    4.6 FOM= 0.69 TEST= 0
INDE 19 67 22 FOBS=     0.0 SIGMA=  24.8 PHAS=    0.0 FOM= 0.00 TEST= 1
INDE 19 67 24 FOBS=    49.7 SIGMA=  10.4 PHAS=   50.4 FOM= 0.82 TEST= 0
INDE 19 67 26 FOBS=     0.0 SIGMA=  26.9 PHAS=    0.0 FOM= 0.00 TEST= 0
INDE 19 67 28 FOBS=     0.0 SIGMA=  24.4 PHAS=    0.0 FOM= 0.00 TEST= 0
```

*FIG. 12A - 437*

```
INDE 19 67 30 FOBS=    67.6 SIGMA=  4.6 PHAS= -162.9 FOM= 0.81 TEST= 0
INDE 19 67 32 FOBS=    10.5 SIGMA= 36.2 PHAS=  167.6 FOM= 0.11 TEST= 0
INDE 19 67 34 FOBS=    72.9 SIGMA=  4.6 PHAS=   18.7 FOM= 0.78 TEST= 0
INDE 19 68 19 FOBS=    28.2 SIGMA= 13.3 PHAS= -145.8 FOM= 0.81 TEST= 0
INDE 19 68 21 FOBS=     7.6 SIGMA= 52.2 PHAS=  -29.0 FOM= 0.16 TEST= 0
INDE 19 68 23 FOBS=    54.7 SIGMA=  7.4 PHAS=  109.0 FOM= 0.70 TEST= 0
INDE 19 68 25 FOBS=    35.8 SIGMA= 15.1 PHAS=  -12.8 FOM= 0.60 TEST= 0
INDE 19 68 27 FOBS=     0.0 SIGMA= 32.7 PHAS=    0.0 FOM= 0.00 TEST= 0
INDE 19 68 29 FOBS=    61.5 SIGMA=  6.2 PHAS=  123.8 FOM= 0.13 TEST= 1
INDE 19 68 31 FOBS=    63.5 SIGMA=  5.0 PHAS=  123.8 FOM= 0.54 TEST= 0
INDE 19 69 20 FOBS=    45.0 SIGMA=  8.7 PHAS= -131.8 FOM= 0.50 TEST= 0
INDE 19 69 22 FOBS=    39.5 SIGMA= 10.5 PHAS=   33.9 FOM= 0.30 TEST= 0
INDE 19 69 30 FOBS=    47.1 SIGMA=  8.3 PHAS=  -85.2 FOM= 0.47 TEST= 0
INDE 19 70 19 FOBS=    97.2 SIGMA=  2.3 PHAS=  154.2 FOM= 0.87 TEST= 0
INDE 19 70 21 FOBS=     0.0 SIGMA= 28.0 PHAS=    0.0 FOM= 0.00 TEST= 1
INDE 19 70 23 FOBS=     0.0 SIGMA= 28.6 PHAS=    0.0 FOM= 0.00 TEST= 0
INDE 19 71 20 FOBS=    58.9 SIGMA=  6.6 PHAS= -153.5 FOM= 0.05 TEST= 1
INDE 19 71 22 FOBS=    37.4 SIGMA= 11.2 PHAS= -166.4 FOM= 0.54 TEST= 0
INDE 19 71 24 FOBS=    20.7 SIGMA= 20.7 PHAS=   10.4 FOM= 0.44 TEST= 0
INDE 19 72 19 FOBS=    38.0 SIGMA=  9.5 PHAS=  135.8 FOM= 0.59 TEST= 0
INDE 19 72 21 FOBS=    44.0 SIGMA=  9.3 PHAS= -166.3 FOM= 0.58 TEST= 0
INDE 20 20 20 FOBS=   181.3 SIGMA=  1.4 PHAS=  -72.3 FOM= 0.99 TEST= 1
INDE 20 21 21 FOBS=   130.7 SIGMA=  1.1 PHAS=  -91.5 FOM= 0.98 TEST= 0
INDE 20 21 23 FOBS=   105.8 SIGMA=  1.2 PHAS=   96.7 FOM= 0.98 TEST= 0
INDE 20 21 25 FOBS=   178.8 SIGMA=  0.7 PHAS= -168.0 FOM= 0.77 TEST= 0
INDE 20 21 27 FOBS=   197.6 SIGMA=  0.8 PHAS= -154.4 FOM= 0.96 TEST= 0
INDE 20 21 29 FOBS=   296.0 SIGMA=  0.6 PHAS=  120.2 FOM= 0.98 TEST= 0
INDE 20 21 31 FOBS=   264.2 SIGMA=  0.7 PHAS=   47.6 FOM= 0.97 TEST= 0
INDE 20 21 33 FOBS=   422.3 SIGMA=  0.7 PHAS=  -45.7 FOM= 0.92 TEST= 1
INDE 20 21 35 FOBS=   243.7 SIGMA=  0.9 PHAS=   81.2 FOM= 0.97 TEST= 0
INDE 20 21 37 FOBS=   169.1 SIGMA=  1.2 PHAS= -151.9 FOM= 0.87 TEST= 0
INDE 20 21 39 FOBS=   116.0 SIGMA=  1.7 PHAS=   59.4 FOM= 0.88 TEST= 0
INDE 20 21 41 FOBS=   142.0 SIGMA=  1.3 PHAS=  -50.1 FOM= 0.73 TEST= 1
INDE 20 21 43 FOBS=   143.4 SIGMA=  1.3 PHAS= -135.8 FOM= 0.71 TEST= 0
INDE 20 21 45 FOBS=    89.5 SIGMA=  1.9 PHAS=   -2.9 FOM= 0.24 TEST= 1
INDE 20 21 47 FOBS=    43.7 SIGMA=  3.8 PHAS=  152.1 FOM= 0.88 TEST= 0
INDE 20 21 49 FOBS=    21.8 SIGMA=  7.3 PHAS=   35.7 FOM= 0.24 TEST= 0
INDE 20 21 51 FOBS=     0.0 SIGMA= 20.6 PHAS=    0.0 FOM= 0.00 TEST= 0
INDE 20 21 53 FOBS=   127.2 SIGMA=  1.6 PHAS=  161.9 FOM= 0.94 TEST= 0
INDE 20 21 55 FOBS=    75.9 SIGMA=  2.6 PHAS= -175.3 FOM= 0.91 TEST= 0
INDE 20 21 57 FOBS=   134.2 SIGMA=  1.8 PHAS=  -97.0 FOM= 0.95 TEST= 0
INDE 20 21 59 FOBS=    45.0 SIGMA=  6.0 PHAS=  -62.4 FOM= 0.15 TEST= 1
INDE 20 21 61 FOBS=    34.8 SIGMA=  7.7 PHAS=  -73.2 FOM= 0.32 TEST= 0
INDE 20 21 63 FOBS=    82.7 SIGMA=  3.3 PHAS=  171.6 FOM= 0.87 TEST= 0
INDE 20 21 65 FOBS=    86.2 SIGMA=  3.2 PHAS= -134.0 FOM= 0.83 TEST= 0
INDE 20 21 67 FOBS=    13.4 SIGMA= 29.2 PHAS=   93.3 FOM= 0.24 TEST= 1
INDE 20 21 69 FOBS=    62.3 SIGMA=  6.3 PHAS=  -70.4 FOM= 0.85 TEST= 0
INDE 20 21 71 FOBS=    28.2 SIGMA= 13.8 PHAS=    8.9 FOM= 0.34 TEST= 0
INDE 20 22 20 FOBS=   132.2 SIGMA=  0.9 PHAS=  -99.3 FOM= 0.91 TEST= 0
INDE 20 22 22 FOBS=   140.3 SIGMA=  0.9 PHAS=  111.6 FOM= 0.98 TEST= 0
INDE 20 22 24 FOBS=   261.2 SIGMA=  0.6 PHAS=  153.1 FOM= 0.98 TEST= 0
INDE 20 22 26 FOBS=   360.0 SIGMA=  0.5 PHAS=   55.1 FOM= 0.97 TEST= 0
INDE 20 22 28 FOBS=   307.6 SIGMA=  0.5 PHAS=   73.3 FOM= 0.95 TEST= 0
INDE 20 22 30 FOBS=   178.8 SIGMA=  0.8 PHAS=  -81.4 FOM= 0.87 TEST= 0
INDE 20 22 32 FOBS=   193.1 SIGMA=  0.8 PHAS= -127.8 FOM= 0.97 TEST= 0
INDE 20 22 34 FOBS=    66.6 SIGMA=  2.3 PHAS=  -60.0 FOM= 0.92 TEST= 0
INDE 20 22 36 FOBS=    75.2 SIGMA=  2.2 PHAS=  158.4 FOM= 0.53 TEST= 0
INDE 20 22 38 FOBS=   136.7 SIGMA=  1.3 PHAS=  110.7 FOM= 0.87 TEST= 0
INDE 20 22 40 FOBS=    39.6 SIGMA=  4.1 PHAS=   86.4 FOM= 0.48 TEST= 0
INDE 20 22 42 FOBS=   122.0 SIGMA=  1.4 PHAS= -143.0 FOM= 0.91 TEST= 0
INDE 20 22 44 FOBS=   201.7 SIGMA=  0.9 PHAS=  -79.5 FOM= 0.93 TEST= 0
INDE 20 22 46 FOBS=    38.0 SIGMA=  4.4 PHAS=   81.3 FOM= 0.92 TEST= 0
INDE 20 22 48 FOBS=   108.6 SIGMA=  1.6 PHAS=  168.6 FOM= 0.93 TEST= 0
INDE 20 22 50 FOBS=    45.0 SIGMA=  3.7 PHAS= -129.6 FOM= 0.52 TEST= 0
INDE 20 22 52 FOBS=    39.2 SIGMA=  5.2 PHAS=   69.6 FOM= 0.26 TEST= 0
INDE 20 22 54 FOBS=    49.6 SIGMA=  4.1 PHAS=   29.1 FOM= 0.67 TEST= 0
INDE 20 22 56 FOBS=    50.5 SIGMA=  4.5 PHAS=   87.5 FOM= 0.13 TEST= 0
INDE 20 22 58 FOBS=   131.1 SIGMA=  2.2 PHAS= -136.8 FOM= 0.95 TEST= 0
INDE 20 22 60 FOBS=    37.2 SIGMA=  9.8 PHAS=   50.0 FOM= 0.06 TEST= 1
INDE 20 22 62 FOBS=    33.7 SIGMA=  8.2 PHAS=  -51.7 FOM= 0.64 TEST= 0
```

*FIG. 12A - 438*

```
INDE 20 22 64 FOBS=   0.0 SIGMA= 25.5 PHAS=   0.0 FOM= 0.00 TEST= 0
INDE 20 22 66 FOBS= 103.8 SIGMA=  3.2 PHAS=  21.4 FOM= 0.87 TEST= 0
INDE 20 22 68 FOBS=  45.5 SIGMA=  8.6 PHAS= -25.8 FOM= 0.61 TEST= 0
INDE 20 22 70 FOBS=  63.4 SIGMA=  5.8 PHAS= -43.1 FOM= 0.48 TEST= 0
INDE 20 23 21 FOBS= 300.1 SIGMA=  0.6 PHAS=  18.1 FOM= 0.99 TEST= 0
INDE 20 23 23 FOBS= 300.2 SIGMA=  0.6 PHAS=  70.3 FOM= 0.93 TEST= 0
INDE 20 23 25 FOBS=  68.9 SIGMA=  1.6 PHAS= 100.2 FOM= 0.61 TEST= 0
INDE 20 23 27 FOBS= 240.1 SIGMA=  0.6 PHAS= -11.0 FOM= 0.91 TEST= 1
INDE 20 23 29 FOBS= 107.8 SIGMA=  1.1 PHAS= 151.7 FOM= 0.75 TEST= 0
INDE 20 23 31 FOBS= 306.4 SIGMA=  0.6 PHAS= 161.4 FOM= 0.98 TEST= 0
INDE 20 23 33 FOBS= 138.9 SIGMA=  1.1 PHAS=   2.2 FOM= 0.93 TEST= 0
INDE 20 23 35 FOBS= 154.5 SIGMA=  1.0 PHAS=  55.1 FOM= 0.92 TEST= 0
INDE 20 23 37 FOBS= 165.7 SIGMA=  1.1 PHAS= -66.2 FOM= 0.83 TEST= 1
INDE 20 23 39 FOBS= 145.6 SIGMA=  1.1 PHAS=  33.6 FOM= 0.86 TEST= 0
INDE 20 23 41 FOBS= 114.3 SIGMA=  1.6 PHAS=  -2.4 FOM= 0.41 TEST= 1
INDE 20 23 43 FOBS= 102.5 SIGMA=  1.6 PHAS=-138.1 FOM= 0.92 TEST= 0
INDE 20 23 45 FOBS= 114.2 SIGMA=  1.5 PHAS= -39.2 FOM= 0.74 TEST= 0
INDE 20 23 47 FOBS= 119.7 SIGMA=  1.4 PHAS= -25.4 FOM= 0.89 TEST= 0
INDE 20 23 49 FOBS=  81.0 SIGMA=  2.0 PHAS= 112.2 FOM= 0.83 TEST= 0
INDE 20 23 51 FOBS=  41.0 SIGMA=  4.4 PHAS=  24.2 FOM= 0.43 TEST= 0
INDE 20 23 53 FOBS=  87.9 SIGMA=  2.2 PHAS= 115.5 FOM= 0.84 TEST= 0
INDE 20 23 55 FOBS=  43.6 SIGMA=  4.6 PHAS= -66.9 FOM= 0.29 TEST= 1
INDE 20 23 57 FOBS=  57.0 SIGMA=  3.9 PHAS=-144.3 FOM= 0.69 TEST= 0
INDE 20 23 59 FOBS= 116.4 SIGMA=  2.5 PHAS= 153.5 FOM= 0.92 TEST= 0
INDE 20 23 61 FOBS=  80.7 SIGMA=  3.5 PHAS=-158.3 FOM= 0.89 TEST= 0
INDE 20 23 63 FOBS=  73.7 SIGMA=  3.8 PHAS=-100.3 FOM= 0.38 TEST= 0
INDE 20 23 65 FOBS=  40.5 SIGMA=  8.0 PHAS= -79.5 FOM= 0.43 TEST= 0
INDE 20 23 67 FOBS=  49.7 SIGMA=  8.0 PHAS= -94.8 FOM= 0.76 TEST= 0
INDE 20 23 69 FOBS= 102.8 SIGMA=  3.7 PHAS=-123.4 FOM= 0.96 TEST= 0
INDE 20 23 71 FOBS=  49.6 SIGMA=  7.4 PHAS= 100.9 FOM= 0.61 TEST= 0
INDE 20 24 20 FOBS= 251.0 SIGMA=  0.6 PHAS= -88.2 FOM= 0.97 TEST= 0
INDE 20 24 22 FOBS= 233.3 SIGMA=  0.6 PHAS=-126.1 FOM= 0.96 TEST= 0
INDE 20 24 24 FOBS= 219.6 SIGMA=  0.7 PHAS=  99.8 FOM= 0.94 TEST= 0
INDE 20 24 26 FOBS= 242.5 SIGMA=  0.6 PHAS=  37.4 FOM= 0.95 TEST= 0
INDE 20 24 28 FOBS= 186.1 SIGMA=  0.7 PHAS=  97.8 FOM= 0.90 TEST= 0
INDE 20 24 30 FOBS= 208.1 SIGMA=  0.7 PHAS=  62.2 FOM= 0.98 TEST= 0
INDE 20 24 32 FOBS= 160.2 SIGMA=  0.9 PHAS=  70.5 FOM= 0.93 TEST= 0
INDE 20 24 34 FOBS= 176.2 SIGMA=  0.9 PHAS=  22.7 FOM= 0.92 TEST= 0
INDE 20 24 36 FOBS= 111.3 SIGMA=  1.5 PHAS=  -7.7 FOM= 0.71 TEST= 1
INDE 20 24 38 FOBS= 115.7 SIGMA=  1.4 PHAS= 147.9 FOM= 0.80 TEST= 0
INDE 20 24 40 FOBS=  47.4 SIGMA=  3.5 PHAS= -29.7 FOM= 0.70 TEST= 0
INDE 20 24 42 FOBS= 102.5 SIGMA=  1.6 PHAS= 144.1 FOM= 0.75 TEST= 0
INDE 20 24 44 FOBS= 133.9 SIGMA=  1.2 PHAS=-116.3 FOM= 0.93 TEST= 0
INDE 20 24 46 FOBS= 185.9 SIGMA=  0.9 PHAS=-130.8 FOM= 0.95 TEST= 0
INDE 20 24 48 FOBS=  66.8 SIGMA=  2.4 PHAS=-156.5 FOM= 0.71 TEST= 0
INDE 20 24 50 FOBS=  16.6 SIGMA= 12.9 PHAS= 118.3 FOM= 0.13 TEST= 0
INDE 20 24 52 FOBS=  62.2 SIGMA=  2.9 PHAS=  29.9 FOM= 0.80 TEST= 0
INDE 20 24 54 FOBS=  92.8 SIGMA=  2.0 PHAS=   2.0 FOM= 0.90 TEST= 0
INDE 20 24 56 FOBS=  19.0 SIGMA= 12.1 PHAS= 171.0 FOM= 0.47 TEST= 0
INDE 20 24 58 FOBS=   0.0 SIGMA= 23.8 PHAS=   0.0 FOM= 0.00 TEST= 0
INDE 20 24 60 FOBS= 110.2 SIGMA=  2.6 PHAS=  83.5 FOM= 0.93 TEST= 0
INDE 20 24 62 FOBS=   0.0 SIGMA= 23.6 PHAS=   0.0 FOM= 0.00 TEST= 0
INDE 20 24 64 FOBS=  44.4 SIGMA=  7.4 PHAS=-118.3 FOM= 0.66 TEST= 0
INDE 20 24 66 FOBS= 109.4 SIGMA=  3.6 PHAS= 123.1 FOM= 0.93 TEST= 0
INDE 20 24 68 FOBS=  47.4 SIGMA=  7.9 PHAS=-133.1 FOM= 0.67 TEST= 0
INDE 20 24 70 FOBS=  45.9 SIGMA=  8.2 PHAS= 138.7 FOM= 0.10 TEST= 1
INDE 20 25 21 FOBS= 296.2 SIGMA=  0.6 PHAS=  74.4 FOM= 0.97 TEST= 0
INDE 20 25 23 FOBS= 106.3 SIGMA=  1.2 PHAS=  48.1 FOM= 0.92 TEST= 0
INDE 20 25 25 FOBS= 313.6 SIGMA=  0.6 PHAS= -86.4 FOM= 0.99 TEST= 0
INDE 20 25 27 FOBS= 272.1 SIGMA=  0.6 PHAS=  45.6 FOM= 0.93 TEST= 0
INDE 20 25 29 FOBS= 312.5 SIGMA=  0.6 PHAS= -54.2 FOM= 0.97 TEST= 0
INDE 20 25 31 FOBS= 317.6 SIGMA=  0.6 PHAS= -63.3 FOM= 0.97 TEST= 0
INDE 20 25 33 FOBS= 191.6 SIGMA=  0.9 PHAS=   4.6 FOM= 0.96 TEST= 0
INDE 20 25 35 FOBS=  89.5 SIGMA=  1.8 PHAS= -11.6 FOM= 0.59 TEST= 0
INDE 20 25 37 FOBS=  46.1 SIGMA=  3.7 PHAS= 127.0 FOM= 0.85 TEST= 0
INDE 20 25 39 FOBS= 103.5 SIGMA=  1.6 PHAS=-141.6 FOM= 0.90 TEST= 0
INDE 20 25 41 FOBS= 120.7 SIGMA=  1.4 PHAS=  25.8 FOM= 0.90 TEST= 0
INDE 20 25 43 FOBS= 109.0 SIGMA=  1.5 PHAS=-168.0 FOM= 0.90 TEST= 0
INDE 20 25 45 FOBS=  72.1 SIGMA=  2.3 PHAS= 128.7 FOM= 0.58 TEST= 0
INDE 20 25 47 FOBS=  80.5 SIGMA=  1.9 PHAS=  14.1 FOM= 0.65 TEST= 1
```

*FIG. 12A - 439*

| | | | | | | | | | | | |
|---|---|---|---|---|---|---|---|---|---|---|---|
| INDE | 20 | 25 | 49 | FOBS= | 47.0 | SIGMA= | 3.3 | PHAS= | -90.9 | FOM= 0.39 | TEST= 0 |
| INDE | 20 | 25 | 51 | FOBS= | 109.3 | SIGMA= | 1.7 | PHAS= | -3.2 | FOM= 0.77 | TEST= 0 |
| INDE | 20 | 25 | 53 | FOBS= | 30.6 | SIGMA= | 6.2 | PHAS= | -18.3 | FOM= 0.29 | TEST= 0 |
| INDE | 20 | 25 | 55 | FOBS= | 90.4 | SIGMA= | 2.0 | PHAS= | -112.8 | FOM= 0.66 | TEST= 0 |
| INDE | 20 | 25 | 57 | FOBS= | 19.0 | SIGMA= | 13.2 | PHAS= | -80.7 | FOM= 0.37 | TEST= 0 |
| INDE | 20 | 25 | 59 | FOBS= | 45.7 | SIGMA= | 6.3 | PHAS= | -115.3 | FOM= 0.18 | TEST= 1 |
| INDE | 20 | 25 | 61 | FOBS= | 49.6 | SIGMA= | 5.7 | PHAS= | -123.6 | FOM= 0.51 | TEST= 0 |
| INDE | 20 | 25 | 63 | FOBS= | 9.6 | SIGMA= | 28.7 | PHAS= | -133.8 | FOM= 0.25 | TEST= 0 |
| INDE | 20 | 25 | 65 | FOBS= | 64.8 | SIGMA= | 6.0 | PHAS= | 33.4 | FOM= 0.84 | TEST= 0 |
| INDE | 20 | 25 | 67 | FOBS= | 0.0 | SIGMA= | 27.6 | PHAS= | 0.0 | FOM= 0.00 | TEST= 0 |
| INDE | 20 | 25 | 69 | FOBS= | 42.5 | SIGMA= | 9.1 | PHAS= | 155.9 | FOM= 0.78 | TEST= 0 |
| INDE | 20 | 26 | 20 | FOBS= | 93.8 | SIGMA= | 1.2 | PHAS= | 74.5 | FOM= 0.93 | TEST= 0 |
| INDE | 20 | 26 | 22 | FOBS= | 101.8 | SIGMA= | 1.2 | PHAS= | -86.7 | FOM= 0.79 | TEST= 0 |
| INDE | 20 | 26 | 24 | FOBS= | 172.5 | SIGMA= | 0.9 | PHAS= | 133.1 | FOM= 0.99 | TEST= 1 |
| INDE | 20 | 26 | 26 | FOBS= | 90.8 | SIGMA= | 1.4 | PHAS= | -157.4 | FOM= 0.97 | TEST= 0 |
| INDE | 20 | 26 | 28 | FOBS= | 194.1 | SIGMA= | 0.8 | PHAS= | -19.4 | FOM= 0.98 | TEST= 0 |
| INDE | 20 | 26 | 30 | FOBS= | 220.0 | SIGMA= | 0.7 | PHAS= | -153.3 | FOM= 0.95 | TEST= 0 |
| INDE | 20 | 26 | 32 | FOBS= | 116.0 | SIGMA= | 1.3 | PHAS= | -177.7 | FOM= 0.99 | TEST= 0 |
| INDE | 20 | 26 | 34 | FOBS= | 154.1 | SIGMA= | 1.1 | PHAS= | 80.9 | FOM= 0.82 | TEST= 0 |
| INDE | 20 | 26 | 36 | FOBS= | 100.9 | SIGMA= | 1.6 | PHAS= | -92.9 | FOM= 0.87 | TEST= 0 |
| INDE | 20 | 26 | 38 | FOBS= | 112.8 | SIGMA= | 1.5 | PHAS= | 81.2 | FOM= 0.93 | TEST= 0 |
| INDE | 20 | 26 | 40 | FOBS= | 171.1 | SIGMA= | 1.0 | PHAS= | 137.1 | FOM= 0.94 | TEST= 0 |
| INDE | 20 | 26 | 42 | FOBS= | 313.5 | SIGMA= | 0.7 | PHAS= | -86.9 | FOM= 0.86 | TEST= 1 |
| INDE | 20 | 26 | 44 | FOBS= | 50.3 | SIGMA= | 3.2 | PHAS= | 10.3 | FOM= 0.17 | TEST= 0 |
| INDE | 20 | 26 | 46 | FOBS= | 63.1 | SIGMA= | 2.6 | PHAS= | -98.2 | FOM= 0.89 | TEST= 0 |
| INDE | 20 | 26 | 48 | FOBS= | 32.5 | SIGMA= | 5.4 | PHAS= | 7.8 | FOM= 0.12 | TEST= 0 |
| INDE | 20 | 26 | 50 | FOBS= | 112.7 | SIGMA= | 1.4 | PHAS= | 168.8 | FOM= 0.92 | TEST= 0 |
| INDE | 20 | 26 | 52 | FOBS= | 100.1 | SIGMA= | 1.6 | PHAS= | -104.8 | FOM= 0.81 | TEST= 0 |
| INDE | 20 | 26 | 54 | FOBS= | 31.0 | SIGMA= | 6.3 | PHAS= | -119.4 | FOM= 0.37 | TEST= 0 |
| INDE | 20 | 26 | 56 | FOBS= | 76.2 | SIGMA= | 3.1 | PHAS= | -65.1 | FOM= 0.45 | TEST= 0 |
| INDE | 20 | 26 | 58 | FOBS= | 27.0 | SIGMA= | 12.0 | PHAS= | 110.1 | FOM= 0.16 | TEST= 0 |
| INDE | 20 | 26 | 60 | FOBS= | 14.1 | SIGMA= | 19.9 | PHAS= | -89.9 | FOM= 0.01 | TEST= 1 |
| INDE | 20 | 26 | 62 | FOBS= | 56.4 | SIGMA= | 5.0 | PHAS= | 99.8 | FOM= 0.76 | TEST= 0 |
| INDE | 20 | 26 | 64 | FOBS= | 62.7 | SIGMA= | 5.4 | PHAS= | -128.5 | FOM= 0.84 | TEST= 0 |
| INDE | 20 | 26 | 66 | FOBS= | 46.3 | SIGMA= | 8.5 | PHAS= | -134.0 | FOM= 0.11 | TEST= 1 |
| INDE | 20 | 26 | 68 | FOBS= | 42.8 | SIGMA= | 9.3 | PHAS= | 62.8 | FOM= 0.54 | TEST= 0 |
| INDE | 20 | 26 | 70 | FOBS= | 40.0 | SIGMA= | 9.4 | PHAS= | 52.5 | FOM= 0.22 | TEST= 0 |
| INDE | 20 | 27 | 21 | FOBS= | 297.4 | SIGMA= | 0.6 | PHAS= | 29.4 | FOM= 0.95 | TEST= 0 |
| INDE | 20 | 27 | 23 | FOBS= | 202.7 | SIGMA= | 0.8 | PHAS= | -95.8 | FOM= 0.96 | TEST= 0 |
| INDE | 20 | 27 | 25 | FOBS= | 220.1 | SIGMA= | 0.7 | PHAS= | 27.0 | FOM= 0.93 | TEST= 0 |
| INDE | 20 | 27 | 27 | FOBS= | 128.7 | SIGMA= | 1.1 | PHAS= | 123.6 | FOM= 0.98 | TEST= 0 |
| INDE | 20 | 27 | 29 | FOBS= | 258.9 | SIGMA= | 0.6 | PHAS= | -86.9 | FOM= 0.95 | TEST= 0 |
| INDE | 20 | 27 | 31 | FOBS= | 39.3 | SIGMA= | 3.7 | PHAS= | 47.4 | FOM= 0.98 | TEST= 1 |
| INDE | 20 | 27 | 33 | FOBS= | 37.7 | SIGMA= | 4.3 | PHAS= | 83.0 | FOM= 0.50 | TEST= 0 |
| INDE | 20 | 27 | 35 | FOBS= | 45.9 | SIGMA= | 3.5 | PHAS= | 132.7 | FOM= 0.19 | TEST= 0 |
| INDE | 20 | 27 | 37 | FOBS= | 32.2 | SIGMA= | 5.0 | PHAS= | -35.9 | FOM= 0.71 | TEST= 0 |
| INDE | 20 | 27 | 39 | FOBS= | 50.8 | SIGMA= | 3.3 | PHAS= | 63.8 | FOM= 0.86 | TEST= 0 |
| INDE | 20 | 27 | 41 | FOBS= | 141.7 | SIGMA= | 1.2 | PHAS= | 116.2 | FOM= 0.75 | TEST= 0 |
| INDE | 20 | 27 | 43 | FOBS= | 145.8 | SIGMA= | 1.2 | PHAS= | -160.0 | FOM= 0.95 | TEST= 0 |
| INDE | 20 | 27 | 45 | FOBS= | 13.2 | SIGMA= | 13.7 | PHAS= | -106.4 | FOM= 0.06 | TEST= 1 |
| INDE | 20 | 27 | 47 | FOBS= | 43.4 | SIGMA= | 4.3 | PHAS= | -76.3 | FOM= 0.77 | TEST= 0 |
| INDE | 20 | 27 | 49 | FOBS= | 47.0 | SIGMA= | 3.6 | PHAS= | 57.2 | FOM= 0.78 | TEST= 0 |
| INDE | 20 | 27 | 51 | FOBS= | 90.2 | SIGMA= | 1.7 | PHAS= | 91.6 | FOM= 0.86 | TEST= 0 |
| INDE | 20 | 27 | 53 | FOBS= | 84.5 | SIGMA= | 1.8 | PHAS= | 73.9 | FOM= 0.77 | TEST= 0 |
| INDE | 20 | 27 | 55 | FOBS= | 0.0 | SIGMA= | 18.5 | PHAS= | 0.0 | FOM= 0.00 | TEST= 0 |
| INDE | 20 | 27 | 57 | FOBS= | 62.0 | SIGMA= | 3.1 | PHAS= | -104.3 | FOM= 0.69 | TEST= 0 |
| INDE | 20 | 27 | 59 | FOBS= | 104.9 | SIGMA= | 2.5 | PHAS= | -60.8 | FOM= 0.84 | TEST= 0 |
| INDE | 20 | 27 | 61 | FOBS= | 65.3 | SIGMA= | 4.3 | PHAS= | -18.6 | FOM= 0.63 | TEST= 0 |
| INDE | 20 | 27 | 63 | FOBS= | 0.0 | SIGMA= | 25.8 | PHAS= | 0.0 | FOM= 0.00 | TEST= 0 |
| INDE | 20 | 27 | 65 | FOBS= | 6.8 | SIGMA= | 59.3 | PHAS= | -40.7 | FOM= 0.06 | TEST= 0 |
| INDE | 20 | 27 | 67 | FOBS= | 0.0 | SIGMA= | 27.7 | PHAS= | 0.0 | FOM= 0.00 | TEST= 0 |
| INDE | 20 | 27 | 69 | FOBS= | 0.0 | SIGMA= | 27.6 | PHAS= | 0.0 | FOM= 0.00 | TEST= 0 |
| INDE | 20 | 28 | 20 | FOBS= | 128.9 | SIGMA= | 1.0 | PHAS= | -151.3 | FOM= 0.99 | TEST= 0 |
| INDE | 20 | 28 | 22 | FOBS= | 269.7 | SIGMA= | 0.6 | PHAS= | 177.3 | FOM= 0.93 | TEST= 0 |
| INDE | 20 | 28 | 24 | FOBS= | 41.5 | SIGMA= | 3.5 | PHAS= | 23.3 | FOM= 0.95 | TEST= 0 |
| INDE | 20 | 28 | 26 | FOBS= | 67.8 | SIGMA= | 2.1 | PHAS= | -151.0 | FOM= 0.96 | TEST= 0 |
| INDE | 20 | 28 | 28 | FOBS= | 76.9 | SIGMA= | 1.8 | PHAS= | 64.2 | FOM= 0.87 | TEST= 0 |
| INDE | 20 | 28 | 30 | FOBS= | 151.5 | SIGMA= | 1.0 | PHAS= | -111.8 | FOM= 0.90 | TEST= 0 |
| INDE | 20 | 28 | 32 | FOBS= | 175.0 | SIGMA= | 1.0 | PHAS= | 95.9 | FOM= 0.80 | TEST= 0 |
| INDE | 20 | 28 | 34 | FOBS= | 85.8 | SIGMA= | 1.9 | PHAS= | 78.4 | FOM= 0.42 | TEST= 1 |

*FIG. 12A - 440*

```
INDE  20  28  36  FOBS=   146.1  SIGMA=   1.3  PHAS=   -74.9  FOM=  0.91  TEST= 0
INDE  20  28  38  FOBS=   129.0  SIGMA=   1.3  PHAS=    78.5  FOM=  0.93  TEST= 0
INDE  20  28  40  FOBS=     0.0  SIGMA=  18.1  PHAS=     0.0  FOM=  0.00  TEST= 0
INDE  20  28  42  FOBS=   235.7  SIGMA=   0.8  PHAS=  -120.2  FOM=  0.95  TEST= 0
INDE  20  28  44  FOBS=    40.1  SIGMA=   4.2  PHAS=   122.4  FOM=  0.29  TEST= 0
INDE  20  28  46  FOBS=   158.5  SIGMA=   1.3  PHAS=   139.6  FOM=  0.97  TEST= 0
INDE  20  28  48  FOBS=   103.0  SIGMA=   1.7  PHAS=   -47.1  FOM=  0.89  TEST= 0
INDE  20  28  50  FOBS=    35.5  SIGMA=   4.8  PHAS=    16.8  FOM=  0.66  TEST= 0
INDE  20  28  52  FOBS=   136.6  SIGMA=   1.2  PHAS=   -93.2  FOM=  0.92  TEST= 0
INDE  20  28  54  FOBS=    18.3  SIGMA=   7.9  PHAS=  -119.5  FOM=  0.50  TEST= 0
INDE  20  28  56  FOBS=    36.4  SIGMA=   5.7  PHAS=    -0.3  FOM=  0.39  TEST= 0
INDE  20  28  58  FOBS=   117.7  SIGMA=   1.7  PHAS=   149.6  FOM=  0.91  TEST= 0
INDE  20  28  60  FOBS=    34.4  SIGMA=   5.5  PHAS=   176.3  FOM=  0.17  TEST= 0
INDE  20  28  62  FOBS=    37.2  SIGMA=   7.5  PHAS=   -76.8  FOM=  0.57  TEST= 0
INDE  20  28  64  FOBS=    94.8  SIGMA=   4.5  PHAS=   168.3  FOM=  0.95  TEST= 0
INDE  20  28  66  FOBS=    68.3  SIGMA=   5.9  PHAS=  -109.1  FOM=  0.90  TEST= 0
INDE  20  28  68  FOBS=    54.2  SIGMA=   7.4  PHAS=    81.2  FOM=  0.75  TEST= 0
INDE  20  29  21  FOBS=   214.8  SIGMA=   0.7  PHAS=    26.4  FOM=  0.93  TEST= 0
INDE  20  29  23  FOBS=   270.9  SIGMA=   0.7  PHAS=   -77.3  FOM=  0.93  TEST= 0
INDE  20  29  25  FOBS=   108.9  SIGMA=   1.4  PHAS=    66.8  FOM=  0.99  TEST= 0
INDE  20  29  27  FOBS=     7.0  SIGMA=  28.1  PHAS=   102.4  FOM=  0.08  TEST= 0
INDE  20  29  29  FOBS=    23.7  SIGMA=   6.2  PHAS=    89.1  FOM=  0.57  TEST= 0
INDE  20  29  31  FOBS=   253.5  SIGMA=   0.7  PHAS=   102.5  FOM=  0.85  TEST= 1
INDE  20  29  33  FOBS=     0.0  SIGMA=  18.9  PHAS=     0.0  FOM=  0.00  TEST= 0
INDE  20  29  35  FOBS=    82.3  SIGMA=   2.2  PHAS=   145.8  FOM=  0.87  TEST= 1
INDE  20  29  37  FOBS=   150.5  SIGMA=   1.2  PHAS=   -39.7  FOM=  0.93  TEST= 0
INDE  20  29  39  FOBS=   149.4  SIGMA=   1.1  PHAS=    41.0  FOM=  0.86  TEST= 0
INDE  20  29  41  FOBS=   304.9  SIGMA=   0.7  PHAS=   179.8  FOM=  0.97  TEST= 0
INDE  20  29  43  FOBS=   137.4  SIGMA=   1.3  PHAS=    56.7  FOM=  0.19  TEST= 1
INDE  20  29  45  FOBS=   197.7  SIGMA=   1.0  PHAS=    33.6  FOM=  0.96  TEST= 0
INDE  20  29  47  FOBS=    56.9  SIGMA=   3.2  PHAS=   -57.5  FOM=  0.51  TEST= 0
INDE  20  29  49  FOBS=    25.3  SIGMA=   7.1  PHAS=  -128.9  FOM=  0.19  TEST= 0
INDE  20  29  51  FOBS=   172.4  SIGMA=   1.0  PHAS=   130.9  FOM=  0.97  TEST= 0
INDE  20  29  53  FOBS=     0.0  SIGMA=  18.2  PHAS=     0.0  FOM=  0.00  TEST= 0
INDE  20  29  55  FOBS=    15.1  SIGMA=  11.3  PHAS=   135.9  FOM=  0.27  TEST= 0
INDE  20  29  57  FOBS=    52.3  SIGMA=   3.7  PHAS=    64.4  FOM=  0.82  TEST= 0
INDE  20  29  59  FOBS=    46.2  SIGMA=   4.1  PHAS=    14.3  FOM=  0.75  TEST= 0
INDE  20  29  61  FOBS=    80.8  SIGMA=   2.4  PHAS=   -69.0  FOM=  0.66  TEST= 0
INDE  20  29  63  FOBS=    70.3  SIGMA=   5.9  PHAS=   121.0  FOM=  0.78  TEST= 0
INDE  20  29  65  FOBS=    60.1  SIGMA=   6.8  PHAS=    96.2  FOM=  0.45  TEST= 1
INDE  20  29  67  FOBS=    43.3  SIGMA=   9.2  PHAS=   -27.3  FOM=  0.36  TEST= 0
INDE  20  29  69  FOBS=    96.1  SIGMA=   4.0  PHAS=    24.2  FOM=  0.94  TEST= 0
INDE  20  30  20  FOBS=   290.7  SIGMA=   0.7  PHAS=  -144.1  FOM=  0.97  TEST= 0
INDE  20  30  22  FOBS=   179.5  SIGMA=   0.9  PHAS=  -143.2  FOM=  0.95  TEST= 0
INDE  20  30  24  FOBS=    55.2  SIGMA=   2.6  PHAS=    20.6  FOM=  0.79  TEST= 0
INDE  20  30  26  FOBS=   147.5  SIGMA=   1.1  PHAS=  -166.2  FOM=  0.97  TEST= 0
INDE  20  30  28  FOBS=   149.7  SIGMA=   1.2  PHAS=   -13.6  FOM=  0.93  TEST= 0
INDE  20  30  30  FOBS=   171.1  SIGMA=   1.0  PHAS=    -6.1  FOM=  0.92  TEST= 0
INDE  20  30  32  FOBS=   193.1  SIGMA=   1.0  PHAS=   107.1  FOM=  0.96  TEST= 0
INDE  20  30  34  FOBS=    91.2  SIGMA=   1.9  PHAS=   -74.2  FOM=  0.50  TEST= 0
INDE  20  30  36  FOBS=    40.1  SIGMA=   4.4  PHAS=  -124.5  FOM=  0.51  TEST= 0
INDE  20  30  38  FOBS=   116.4  SIGMA=   1.5  PHAS=  -126.4  FOM=  0.75  TEST= 0
INDE  20  30  40  FOBS=   152.6  SIGMA=   1.1  PHAS=   103.6  FOM=  0.92  TEST= 1
INDE  20  30  42  FOBS=   245.3  SIGMA=   0.9  PHAS=   162.7  FOM=  0.51  TEST= 1
INDE  20  30  44  FOBS=   137.5  SIGMA=   1.4  PHAS=     0.4  FOM=  0.92  TEST= 0
INDE  20  30  46  FOBS=    46.4  SIGMA=   4.3  PHAS=    18.9  FOM=  0.18  TEST= 0
INDE  20  30  48  FOBS=   103.6  SIGMA=   1.8  PHAS=  -110.7  FOM=  0.30  TEST= 1
INDE  20  30  50  FOBS=   139.1  SIGMA=   1.2  PHAS=    22.5  FOM=  0.93  TEST= 0
INDE  20  30  52  FOBS=    60.0  SIGMA=   2.7  PHAS=    48.1  FOM=  0.87  TEST= 0
INDE  20  30  54  FOBS=    43.3  SIGMA=   4.1  PHAS=   -81.8  FOM=  0.28  TEST= 0
INDE  20  30  56  FOBS=   140.4  SIGMA=   1.5  PHAS=   -35.1  FOM=  0.95  TEST= 0
INDE  20  30  58  FOBS=    59.7  SIGMA=   3.1  PHAS=   -84.1  FOM=  0.60  TEST= 0
INDE  20  30  60  FOBS=    34.6  SIGMA=   5.9  PHAS=   -82.5  FOM=  0.75  TEST= 0
INDE  20  30  62  FOBS=    50.0  SIGMA=   4.5  PHAS=    28.5  FOM=  0.44  TEST= 0
INDE  20  30  64  FOBS=    37.6  SIGMA=   8.6  PHAS=   119.9  FOM=  0.31  TEST= 0
INDE  20  30  66  FOBS=    69.3  SIGMA=   5.8  PHAS=   -68.4  FOM=  0.87  TEST= 0
INDE  20  31  21  FOBS=   146.5  SIGMA=   1.1  PHAS=   145.0  FOM=  0.80  TEST= 0
INDE  20  31  23  FOBS=    68.8  SIGMA=   2.1  PHAS=    -6.3  FOM=  0.96  TEST= 0
INDE  20  31  25  FOBS=    94.5  SIGMA=   1.7  PHAS=    13.6  FOM=  0.84  TEST= 0
INDE  20  31  27  FOBS=   245.9  SIGMA=   0.8  PHAS=  -131.4  FOM=  0.95  TEST= 0
```

*FIG. 12A - 441*

```
INDE 20 31 29 FOBS=   92.8 SIGMA=  1.8 PHAS=  152.3 FOM= 0.78 TEST= 0
INDE 20 31 31 FOBS=  373.2 SIGMA=  0.7 PHAS=   44.0 FOM= 0.98 TEST= 0
INDE 20 31 33 FOBS=   27.1 SIGMA=  6.4 PHAS=  154.6 FOM= 0.77 TEST= 0
INDE 20 31 35 FOBS=    0.0 SIGMA= 18.1 PHAS=    0.0 FOM= 0.00 TEST= 0
INDE 20 31 37 FOBS=   66.2 SIGMA=  2.7 PHAS=   52.5 FOM= 0.11 TEST= 0
INDE 20 31 39 FOBS=  112.1 SIGMA=  1.6 PHAS=  -28.5 FOM= 0.89 TEST= 0
INDE 20 31 41 FOBS=  117.8 SIGMA=  1.8 PHAS=   32.3 FOM= 0.92 TEST= 0
INDE 20 31 43 FOBS=  102.3 SIGMA=  1.8 PHAS=  -25.5 FOM= 0.86 TEST= 0
INDE 20 31 45 FOBS=    0.0 SIGMA= 18.7 PHAS=    0.0 FOM= 0.00 TEST= 0
INDE 20 31 47 FOBS=    0.0 SIGMA= 19.1 PHAS=    0.0 FOM= 0.00 TEST= 1
INDE 20 31 49 FOBS=  137.6 SIGMA=  1.3 PHAS= -171.6 FOM= 0.88 TEST= 0
INDE 20 31 51 FOBS=   51.4 SIGMA=  3.3 PHAS=  -53.3 FOM= 0.61 TEST= 0
INDE 20 31 53 FOBS=   58.3 SIGMA=  2.7 PHAS=   33.9 FOM= 0.61 TEST= 1
INDE 20 31 55 FOBS=   78.6 SIGMA=  2.5 PHAS= -165.3 FOM= 0.80 TEST= 0
INDE 20 31 57 FOBS=   66.9 SIGMA=  2.9 PHAS= -115.1 FOM= 0.24 TEST= 0
INDE 20 31 59 FOBS=   39.2 SIGMA=  5.2 PHAS=  130.2 FOM= 0.49 TEST= 0
INDE 20 31 61 FOBS=   49.2 SIGMA=  4.3 PHAS=  -66.2 FOM= 0.47 TEST= 0
INDE 20 31 63 FOBS=   28.0 SIGMA=  9.8 PHAS= -174.0 FOM= 0.06 TEST= 0
INDE 20 31 65 FOBS=   75.0 SIGMA=  4.4 PHAS=  104.8 FOM= 0.19 TEST= 1
INDE 20 31 67 FOBS=    0.0 SIGMA= 34.3 PHAS=    0.0 FOM= 0.00 TEST= 0
INDE 20 32 20 FOBS=  209.2 SIGMA=  0.9 PHAS=   62.4 FOM= 0.92 TEST= 0
INDE 20 32 22 FOBS=  365.3 SIGMA=  0.7 PHAS=  -40.7 FOM= 0.98 TEST= 0
INDE 20 32 24 FOBS=   93.8 SIGMA=  1.7 PHAS= -138.7 FOM= 0.95 TEST= 0
INDE 20 32 26 FOBS=  117.0 SIGMA=  1.5 PHAS=  179.1 FOM= 0.96 TEST= 0
INDE 20 32 28 FOBS=  284.5 SIGMA=  0.8 PHAS=   80.6 FOM= 0.96 TEST= 0
INDE 20 32 30 FOBS=  126.8 SIGMA=  1.4 PHAS=  -22.9 FOM= 0.94 TEST= 0
INDE 20 32 32 FOBS=    0.0 SIGMA= 19.0 PHAS=    0.0 FOM= 0.00 TEST= 0
INDE 20 32 34 FOBS=  138.4 SIGMA=  1.3 PHAS= -116.2 FOM= 0.96 TEST= 0
INDE 20 32 36 FOBS=  168.1 SIGMA=  1.0 PHAS=  -75.4 FOM= 0.86 TEST= 0
INDE 20 32 38 FOBS=  175.8 SIGMA=  1.1 PHAS= -144.1 FOM= 0.92 TEST= 0
INDE 20 32 40 FOBS=    0.0 SIGMA= 19.6 PHAS=    0.0 FOM= 0.00 TEST= 0
INDE 20 32 42 FOBS=  193.3 SIGMA=  1.1 PHAS= -119.8 FOM= 0.97 TEST= 0
INDE 20 32 44 FOBS=   53.1 SIGMA=  3.7 PHAS= -176.8 FOM= 0.73 TEST= 0
INDE 20 32 46 FOBS=   27.1 SIGMA=  6.8 PHAS= -135.7 FOM= 0.05 TEST= 0
INDE 20 32 48 FOBS=   18.8 SIGMA=  9.8 PHAS=  -56.8 FOM= 0.04 TEST= 1
INDE 20 32 50 FOBS=   32.5 SIGMA=  5.1 PHAS=  -46.8 FOM= 0.12 TEST= 0
INDE 20 32 52 FOBS=   50.5 SIGMA=  3.2 PHAS= -179.9 FOM= 0.81 TEST= 0
INDE 20 32 54 FOBS=    0.0 SIGMA= 19.7 PHAS=    0.0 FOM= 0.00 TEST= 0
INDE 20 32 56 FOBS=   99.0 SIGMA=  2.0 PHAS=  -87.2 FOM= 0.93 TEST= 0
INDE 20 32 58 FOBS=   18.2 SIGMA= 12.8 PHAS=    5.5 FOM= 0.16 TEST= 0
INDE 20 32 60 FOBS=   82.2 SIGMA=  2.4 PHAS=   -7.7 FOM= 0.88 TEST= 0
INDE 20 32 62 FOBS=    0.0 SIGMA= 21.1 PHAS=    0.0 FOM= 0.00 TEST= 0
INDE 20 32 64 FOBS=   38.3 SIGMA=  7.1 PHAS=  129.4 FOM= 0.21 TEST= 0
INDE 20 32 66 FOBS=   74.2 SIGMA=  7.8 PHAS=  101.1 FOM= 0.84 TEST= 0
INDE 20 32 68 FOBS=   96.3 SIGMA=  6.5 PHAS=  -92.4 FOM= 0.90 TEST= 0
INDE 20 33 21 FOBS=  411.1 SIGMA=  0.6 PHAS= -116.0 FOM= 0.97 TEST= 0
INDE 20 33 23 FOBS=  127.6 SIGMA=  1.3 PHAS= -102.5 FOM= 0.87 TEST= 1
INDE 20 33 25 FOBS=   57.6 SIGMA=  2.9 PHAS=   91.2 FOM= 0.99 TEST= 0
INDE 20 33 27 FOBS=  197.8 SIGMA=  1.0 PHAS= -132.2 FOM= 0.90 TEST= 0
INDE 20 33 29 FOBS=   63.7 SIGMA=  2.9 PHAS=   57.0 FOM= 0.85 TEST= 0
INDE 20 33 31 FOBS=  166.1 SIGMA=  1.1 PHAS=   -4.1 FOM= 0.41 TEST= 0
INDE 20 33 33 FOBS=   89.7 SIGMA=  1.9 PHAS=   30.1 FOM= 0.79 TEST= 0
INDE 20 33 35 FOBS=  138.7 SIGMA=  1.2 PHAS=   78.4 FOM= 0.55 TEST= 0
INDE 20 33 37 FOBS=  138.2 SIGMA=  1.2 PHAS=   90.6 FOM= 0.13 TEST= 1
INDE 20 33 39 FOBS=    6.7 SIGMA= 33.7 PHAS=  -58.6 FOM= 0.00 TEST= 1
INDE 20 33 41 FOBS=  132.3 SIGMA=  1.5 PHAS=  144.6 FOM= 0.65 TEST= 0
INDE 20 33 43 FOBS=    0.0 SIGMA= 21.7 PHAS=    0.0 FOM= 0.00 TEST= 1
INDE 20 33 45 FOBS=   33.2 SIGMA=  5.9 PHAS=  120.0 FOM= 0.14 TEST= 1
INDE 20 33 47 FOBS=   25.6 SIGMA=  7.1 PHAS= -160.7 FOM= 0.35 TEST= 0
INDE 20 33 49 FOBS=  180.2 SIGMA=  1.1 PHAS= -165.2 FOM= 0.98 TEST= 0
INDE 20 33 51 FOBS=   71.7 SIGMA=  2.3 PHAS=   79.8 FOM= 0.67 TEST= 0
INDE 20 33 53 FOBS=  114.6 SIGMA=  1.6 PHAS=   97.9 FOM= 0.90 TEST= 0
INDE 20 33 55 FOBS=   84.8 SIGMA=  2.3 PHAS= -173.6 FOM= 0.85 TEST= 0
INDE 20 33 57 FOBS=   34.8 SIGMA=  5.6 PHAS=  102.8 FOM= 0.48 TEST= 0
INDE 20 33 59 FOBS=   23.6 SIGMA=  8.2 PHAS=  -50.2 FOM= 0.21 TEST= 0
INDE 20 33 61 FOBS=   97.0 SIGMA=  2.1 PHAS=  -97.2 FOM= 0.54 TEST= 1
INDE 20 33 63 FOBS=   76.3 SIGMA=  3.0 PHAS=  141.5 FOM= 0.91 TEST= 0
INDE 20 33 65 FOBS=   84.7 SIGMA=  4.0 PHAS=   18.4 FOM= 0.82 TEST= 0
INDE 20 33 67 FOBS=   28.7 SIGMA= 14.6 PHAS=  -69.3 FOM= 0.35 TEST= 0
INDE 20 34 20 FOBS=  225.9 SIGMA=  0.9 PHAS=  148.0 FOM= 0.82 TEST= 1
```

*FIG. 12A - 442*

| | | | | | | | | | | | |
|---|---|---|---|---|---|---|---|---|---|---|---|
| INDE | 20 | 34 | 22 | FOBS= | 131.7 | SIGMA= | 1.4 | PHAS= | 109.2 | FOM= | 0.89 | TEST= 0
| INDE | 20 | 34 | 24 | FOBS= | 145.2 | SIGMA= | 1.2 | PHAS= | -138.1 | FOM= | 0.91 | TEST= 0
| INDE | 20 | 34 | 26 | FOBS= | 71.7 | SIGMA= | 2.5 | PHAS= | 98.2 | FOM= | 0.71 | TEST= 0
| INDE | 20 | 34 | 28 | FOBS= | 185.6 | SIGMA= | 1.1 | PHAS= | 134.2 | FOM= | 0.93 | TEST= 0
| INDE | 20 | 34 | 30 | FOBS= | 50.2 | SIGMA= | 3.8 | PHAS= | -66.7 | FOM= | 0.80 | TEST= 1
| INDE | 20 | 34 | 32 | FOBS= | 129.1 | SIGMA= | 1.3 | PHAS= | -125.8 | FOM= | 0.83 | TEST= 1
| INDE | 20 | 34 | 34 | FOBS= | 209.1 | SIGMA= | 0.9 | PHAS= | -117.8 | FOM= | 0.95 | TEST= 0
| INDE | 20 | 34 | 36 | FOBS= | 42.0 | SIGMA= | 4.0 | PHAS= | -114.1 | FOM= | 0.46 | TEST= 0
| INDE | 20 | 34 | 38 | FOBS= | 129.5 | SIGMA= | 1.5 | PHAS= | -80.2 | FOM= | 0.93 | TEST= 0
| INDE | 20 | 34 | 40 | FOBS= | 58.6 | SIGMA= | 3.5 | PHAS= | 94.3 | FOM= | 0.79 | TEST= 0
| INDE | 20 | 34 | 42 | FOBS= | 0.0 | SIGMA= | 20.9 | PHAS= | 0.0 | FOM= | 0.00 | TEST= 0
| INDE | 20 | 34 | 44 | FOBS= | 165.0 | SIGMA= | 1.3 | PHAS= | 142.8 | FOM= | 0.94 | TEST= 0
| INDE | 20 | 34 | 46 | FOBS= | 56.2 | SIGMA= | 3.5 | PHAS= | 127.3 | FOM= | 0.32 | TEST= 1
| INDE | 20 | 34 | 48 | FOBS= | 165.5 | SIGMA= | 1.3 | PHAS= | 120.1 | FOM= | 0.97 | TEST= 0
| INDE | 20 | 34 | 50 | FOBS= | 121.1 | SIGMA= | 1.5 | PHAS= | 98.0 | FOM= | 0.95 | TEST= 0
| INDE | 20 | 34 | 52 | FOBS= | 79.9 | SIGMA= | 2.3 | PHAS= | 24.4 | FOM= | 0.81 | TEST= 0
| INDE | 20 | 34 | 54 | FOBS= | 20.9 | SIGMA= | 10.8 | PHAS= | -148.8 | FOM= | 0.11 | TEST= 0
| INDE | 20 | 34 | 56 | FOBS= | 48.1 | SIGMA= | 4.0 | PHAS= | 48.2 | FOM= | 0.58 | TEST= 0
| INDE | 20 | 34 | 58 | FOBS= | 81.4 | SIGMA= | 2.4 | PHAS= | -43.4 | FOM= | 0.82 | TEST= 0
| INDE | 20 | 34 | 60 | FOBS= | 88.9 | SIGMA= | 2.2 | PHAS= | 139.2 | FOM= | 0.64 | TEST= 0
| INDE | 20 | 34 | 62 | FOBS= | 28.4 | SIGMA= | 7.3 | PHAS= | -74.1 | FOM= | 0.39 | TEST= 0
| INDE | 20 | 34 | 64 | FOBS= | 67.9 | SIGMA= | 4.1 | PHAS= | 8.7 | FOM= | 0.86 | TEST= 0
| INDE | 20 | 34 | 66 | FOBS= | 0.0 | SIGMA= | 25.8 | PHAS= | 0.0 | FOM= | 0.00 | TEST= 0
| INDE | 20 | 35 | 21 | FOBS= | 135.3 | SIGMA= | 1.4 | PHAS= | -60.3 | FOM= | 0.85 | TEST= 0
| INDE | 20 | 35 | 23 | FOBS= | 310.9 | SIGMA= | 0.7 | PHAS= | 9.7 | FOM= | 0.97 | TEST= 0
| INDE | 20 | 35 | 25 | FOBS= | 70.7 | SIGMA= | 2.5 | PHAS= | 179.0 | FOM= | 0.96 | TEST= 0
| INDE | 20 | 35 | 27 | FOBS= | 40.5 | SIGMA= | 4.7 | PHAS= | -46.0 | FOM= | 0.78 | TEST= 0
| INDE | 20 | 35 | 29 | FOBS= | 134.7 | SIGMA= | 1.4 | PHAS= | -139.5 | FOM= | 0.78 | TEST= 0
| INDE | 20 | 35 | 31 | FOBS= | 0.0 | SIGMA= | 20.0 | PHAS= | 0.0 | FOM= | 0.00 | TEST= 0
| INDE | 20 | 35 | 33 | FOBS= | 159.8 | SIGMA= | 1.1 | PHAS= | 98.2 | FOM= | 0.93 | TEST= 0
| INDE | 20 | 35 | 35 | FOBS= | 177.7 | SIGMA= | 1.1 | PHAS= | 111.6 | FOM= | 0.90 | TEST= 0
| INDE | 20 | 35 | 37 | FOBS= | 184.6 | SIGMA= | 1.1 | PHAS= | 162.3 | FOM= | 0.55 | TEST= 1
| INDE | 20 | 35 | 39 | FOBS= | 4.2 | SIGMA= | 48.2 | PHAS= | 2.3 | FOM= | 0.06 | TEST= 0
| INDE | 20 | 35 | 41 | FOBS= | 77.6 | SIGMA= | 2.5 | PHAS= | -166.1 | FOM= | 0.85 | TEST= 0
| INDE | 20 | 35 | 43 | FOBS= | 151.9 | SIGMA= | 1.4 | PHAS= | 29.9 | FOM= | 0.94 | TEST= 0
| INDE | 20 | 35 | 45 | FOBS= | 137.8 | SIGMA= | 1.5 | PHAS= | 56.3 | FOM= | 0.96 | TEST= 0
| INDE | 20 | 35 | 47 | FOBS= | 156.0 | SIGMA= | 1.4 | PHAS= | 62.5 | FOM= | 0.96 | TEST= 0
| INDE | 20 | 35 | 49 | FOBS= | 128.5 | SIGMA= | 1.6 | PHAS= | 21.0 | FOM= | 0.82 | TEST= 1
| INDE | 20 | 35 | 51 | FOBS= | 35.7 | SIGMA= | 5.0 | PHAS= | 97.1 | FOM= | 0.69 | TEST= 0
| INDE | 20 | 35 | 53 | FOBS= | 0.0 | SIGMA= | 20.4 | PHAS= | 0.0 | FOM= | 0.00 | TEST= 0
| INDE | 20 | 35 | 55 | FOBS= | 108.8 | SIGMA= | 1.9 | PHAS= | -42.9 | FOM= | 0.91 | TEST= 0
| INDE | 20 | 35 | 57 | FOBS= | 51.6 | SIGMA= | 3.8 | PHAS= | 15.5 | FOM= | 0.34 | TEST= 0
| INDE | 20 | 35 | 59 | FOBS= | 69.5 | SIGMA= | 3.0 | PHAS= | 90.3 | FOM= | 0.11 | TEST= 0
| INDE | 20 | 35 | 61 | FOBS= | 20.6 | SIGMA= | 10.7 | PHAS= | 62.0 | FOM= | 0.15 | TEST= 0
| INDE | 20 | 35 | 63 | FOBS= | 67.5 | SIGMA= | 3.4 | PHAS= | 166.5 | FOM= | 0.81 | TEST= 0
| INDE | 20 | 35 | 65 | FOBS= | 37.3 | SIGMA= | 8.8 | PHAS= | -171.3 | FOM= | 0.50 | TEST= 0
| INDE | 20 | 36 | 20 | FOBS= | 56.8 | SIGMA= | 2.8 | PHAS= | -153.5 | FOM= | 0.83 | TEST= 0
| INDE | 20 | 36 | 22 | FOBS= | 224.1 | SIGMA= | 0.9 | PHAS= | -111.8 | FOM= | 0.94 | TEST= 0
| INDE | 20 | 36 | 24 | FOBS= | 219.4 | SIGMA= | 1.0 | PHAS= | -117.4 | FOM= | 0.97 | TEST= 0
| INDE | 20 | 36 | 26 | FOBS= | 137.8 | SIGMA= | 1.4 | PHAS= | 75.6 | FOM= | 0.96 | TEST= 0
| INDE | 20 | 36 | 28 | FOBS= | 133.1 | SIGMA= | 1.4 | PHAS= | 166.9 | FOM= | 0.75 | TEST= 0
| INDE | 20 | 36 | 30 | FOBS= | 125.3 | SIGMA= | 1.5 | PHAS= | 146.6 | FOM= | 0.90 | TEST= 0
| INDE | 20 | 36 | 32 | FOBS= | 61.5 | SIGMA= | 2.9 | PHAS= | 34.5 | FOM= | 0.83 | TEST= 0
| INDE | 20 | 36 | 34 | FOBS= | 185.3 | SIGMA= | 1.1 | PHAS= | -17.3 | FOM= | 0.94 | TEST= 0
| INDE | 20 | 36 | 36 | FOBS= | 121.8 | SIGMA= | 1.5 | PHAS= | 129.8 | FOM= | 0.84 | TEST= 0
| INDE | 20 | 36 | 38 | FOBS= | 63.6 | SIGMA= | 2.9 | PHAS= | -113.5 | FOM= | 0.71 | TEST= 0
| INDE | 20 | 36 | 40 | FOBS= | 176.6 | SIGMA= | 1.2 | PHAS= | 74.3 | FOM= | 0.94 | TEST= 0
| INDE | 20 | 36 | 42 | FOBS= | 44.6 | SIGMA= | 4.3 | PHAS= | -165.4 | FOM= | 0.36 | TEST= 0
| INDE | 20 | 36 | 44 | FOBS= | 155.8 | SIGMA= | 1.4 | PHAS= | -55.6 | FOM= | 0.93 | TEST= 0
| INDE | 20 | 36 | 46 | FOBS= | 124.0 | SIGMA= | 1.7 | PHAS= | -2.7 | FOM= | 0.95 | TEST= 0
| INDE | 20 | 36 | 48 | FOBS= | 67.4 | SIGMA= | 2.9 | PHAS= | -95.3 | FOM= | 0.85 | TEST= 0
| INDE | 20 | 36 | 50 | FOBS= | 56.5 | SIGMA= | 3.4 | PHAS= | -1.1 | FOM= | 0.86 | TEST= 0
| INDE | 20 | 36 | 52 | FOBS= | 41.5 | SIGMA= | 4.8 | PHAS= | 64.7 | FOM= | 0.83 | TEST= 0
| INDE | 20 | 36 | 54 | FOBS= | 79.5 | SIGMA= | 2.5 | PHAS= | -135.5 | FOM= | 0.88 | TEST= 0
| INDE | 20 | 36 | 56 | FOBS= | 51.5 | SIGMA= | 4.1 | PHAS= | 23.0 | FOM= | 0.07 | TEST= 0
| INDE | 20 | 36 | 58 | FOBS= | 47.2 | SIGMA= | 4.2 | PHAS= | 8.1 | FOM= | 0.64 | TEST= 0
| INDE | 20 | 36 | 60 | FOBS= | 0.0 | SIGMA= | 25.1 | PHAS= | 0.0 | FOM= | 0.00 | TEST= 0
| INDE | 20 | 36 | 62 | FOBS= | 42.7 | SIGMA= | 6.5 | PHAS= | 108.0 | FOM= | 0.62 | TEST= 0
| INDE | 20 | 36 | 64 | FOBS= | 74.1 | SIGMA= | 3.9 | PHAS= | 124.0 | FOM= | 0.91 | TEST= 0
| INDE | 20 | 37 | 21 | FOBS= | 35.2 | SIGMA= | 5.3 | PHAS= | -40.2 | FOM= | 0.68 | TEST= 0

*FIG. 12A - 443*

```
INDE  20  37  23  FOBS=   125.7  SIGMA=    1.6  PHAS=   91.2  FOM= 0.91  TEST= 0
INDE  20  37  25  FOBS=    99.9  SIGMA=    1.9  PHAS=  -65.4  FOM= 0.95  TEST= 0
INDE  20  37  27  FOBS=   155.4  SIGMA=    1.3  PHAS=  137.2  FOM= 0.89  TEST= 0
INDE  20  37  29  FOBS=   167.7  SIGMA=    1.2  PHAS=  117.9  FOM= 0.39  TEST= 1
INDE  20  37  31  FOBS=   175.5  SIGMA=    1.1  PHAS=  -25.2  FOM= 0.97  TEST= 0
INDE  20  37  33  FOBS=   221.2  SIGMA=    0.9  PHAS=  -94.4  FOM= 0.97  TEST= 0
INDE  20  37  35  FOBS=   105.6  SIGMA=    1.7  PHAS=   70.0  FOM= 0.90  TEST= 0
INDE  20  37  37  FOBS=    54.7  SIGMA=    3.4  PHAS= -175.0  FOM= 0.37  TEST= 0
INDE  20  37  39  FOBS=   203.4  SIGMA=    1.0  PHAS=  -19.2  FOM= 0.96  TEST= 0
INDE  20  37  41  FOBS=     0.0  SIGMA=   21.0  PHAS=    0.0  FOM= 0.00  TEST= 0
INDE  20  37  43  FOBS=    93.2  SIGMA=    2.2  PHAS=  108.7  FOM= 0.88  TEST= 0
INDE  20  37  45  FOBS=    18.5  SIGMA=   10.8  PHAS=   39.9  FOM= 0.16  TEST= 1
INDE  20  37  47  FOBS=    49.8  SIGMA=    5.0  PHAS= -150.1  FOM= 0.71  TEST= 0
INDE  20  37  49  FOBS=    69.2  SIGMA=    2.8  PHAS=  -75.9  FOM= 0.72  TEST= 0
INDE  20  37  51  FOBS=    40.3  SIGMA=    4.8  PHAS= -153.9  FOM= 0.77  TEST= 0
INDE  20  37  53  FOBS=   125.7  SIGMA=    1.7  PHAS=  149.6  FOM= 0.45  TEST= 1
INDE  20  37  55  FOBS=    73.3  SIGMA=    2.7  PHAS=   -2.1  FOM= 0.91  TEST= 0
INDE  20  37  57  FOBS=   100.3  SIGMA=    2.0  PHAS=   56.6  FOM= 0.04  TEST= 1
INDE  20  37  59  FOBS=    71.0  SIGMA=    3.2  PHAS=   -4.5  FOM= 0.07  TEST= 1
INDE  20  37  61  FOBS=     0.0  SIGMA=   22.0  PHAS=    0.0  FOM= 0.00  TEST= 0
INDE  20  37  63  FOBS=   125.3  SIGMA=    2.4  PHAS=   22.0  FOM= 0.96  TEST= 0
INDE  20  37  65  FOBS=   108.6  SIGMA=    3.2  PHAS=   34.2  FOM= 0.95  TEST= 0
INDE  20  38  20  FOBS=   118.7  SIGMA=    1.5  PHAS=  -62.7  FOM= 0.76  TEST= 0
INDE  20  38  22  FOBS=   298.5  SIGMA=    0.7  PHAS=  -15.5  FOM= 0.96  TEST= 0
INDE  20  38  24  FOBS=    20.5  SIGMA=    9.3  PHAS= -152.1  FOM= 0.24  TEST= 0
INDE  20  38  26  FOBS=   181.4  SIGMA=    1.1  PHAS=   73.8  FOM= 0.94  TEST= 0
INDE  20  38  28  FOBS=   243.3  SIGMA=    0.9  PHAS=   84.8  FOM= 0.97  TEST= 0
INDE  20  38  30  FOBS=   107.4  SIGMA=    1.9  PHAS=   -8.7  FOM= 0.90  TEST= 0
INDE  20  38  32  FOBS=   190.8  SIGMA=    1.3  PHAS= -150.3  FOM= 0.98  TEST= 0
INDE  20  38  34  FOBS=    73.3  SIGMA=    2.5  PHAS=  148.5  FOM= 0.93  TEST= 1
INDE  20  38  36  FOBS=   213.5  SIGMA=    0.9  PHAS=   92.3  FOM= 0.93  TEST= 0
INDE  20  38  38  FOBS=   147.7  SIGMA=    1.3  PHAS= -112.5  FOM= 0.94  TEST= 0
INDE  20  38  40  FOBS=    96.1  SIGMA=    1.8  PHAS=  -81.3  FOM= 0.70  TEST= 0
INDE  20  38  42  FOBS=     0.0  SIGMA=   19.5  PHAS=    0.0  FOM= 0.00  TEST= 0
INDE  20  38  44  FOBS=    32.9  SIGMA=    6.1  PHAS=  -28.5  FOM= 0.50  TEST= 0
INDE  20  38  46  FOBS=   160.2  SIGMA=    1.4  PHAS=  114.3  FOM= 0.95  TEST= 0
INDE  20  38  48  FOBS=    51.7  SIGMA=    3.8  PHAS=   63.9  FOM= 0.11  TEST= 1
INDE  20  38  50  FOBS=    30.2  SIGMA=    7.4  PHAS= -155.1  FOM= 0.39  TEST= 0
INDE  20  38  52  FOBS=    85.1  SIGMA=    2.2  PHAS=   39.4  FOM= 0.95  TEST= 0
INDE  20  38  54  FOBS=    55.4  SIGMA=    3.6  PHAS=  -77.2  FOM= 0.68  TEST= 0
INDE  20  38  56  FOBS=    44.1  SIGMA=    5.0  PHAS=   25.8  FOM= 0.50  TEST= 0
INDE  20  38  58  FOBS=    32.2  SIGMA=    6.8  PHAS=   68.3  FOM= 0.52  TEST= 0
INDE  20  38  60  FOBS=    51.8  SIGMA=    4.3  PHAS=  -78.7  FOM= 0.71  TEST= 0
INDE  20  38  62  FOBS=    84.9  SIGMA=    2.7  PHAS=  -58.3  FOM= 0.88  TEST= 0
INDE  20  38  64  FOBS=   110.5  SIGMA=    2.7  PHAS=  -97.5  FOM= 0.97  TEST= 0
INDE  20  39  21  FOBS=   344.8  SIGMA=    0.7  PHAS=  -69.5  FOM= 0.96  TEST= 0
INDE  20  39  23  FOBS=   110.1  SIGMA=    1.7  PHAS=  156.9  FOM= 0.52  TEST= 0
INDE  20  39  25  FOBS=   172.4  SIGMA=    1.2  PHAS=  -53.7  FOM= 0.95  TEST= 0
INDE  20  39  27  FOBS=     0.9  SIGMA=  231.6  PHAS=  -75.2  FOM= 0.01  TEST= 0
INDE  20  39  29  FOBS=   165.4  SIGMA=    1.3  PHAS=  -42.5  FOM= 0.93  TEST= 0
INDE  20  39  31  FOBS=   100.7  SIGMA=    2.0  PHAS=  -82.5  FOM= 0.80  TEST= 0
INDE  20  39  33  FOBS=    27.9  SIGMA=    7.1  PHAS= -179.4  FOM= 0.79  TEST= 0
INDE  20  39  35  FOBS=   179.1  SIGMA=    1.1  PHAS=   56.1  FOM= 0.97  TEST= 0
INDE  20  39  37  FOBS=    96.1  SIGMA=    1.9  PHAS=  -32.2  FOM= 0.81  TEST= 0
INDE  20  39  39  FOBS=   107.6  SIGMA=    1.7  PHAS=  -63.0  FOM= 0.90  TEST= 0
INDE  20  39  41  FOBS=    84.1  SIGMA=    2.1  PHAS= -174.7  FOM= 0.88  TEST= 0
INDE  20  39  43  FOBS=    39.4  SIGMA=    4.8  PHAS=   92.7  FOM= 0.82  TEST= 0
INDE  20  39  45  FOBS=    88.8  SIGMA=    2.3  PHAS=  -11.7  FOM= 0.89  TEST= 0
INDE  20  39  47  FOBS=    81.8  SIGMA=    2.5  PHAS=  -14.0  FOM= 0.80  TEST= 0
INDE  20  39  49  FOBS=    44.2  SIGMA=    4.4  PHAS=  164.7  FOM= 0.59  TEST= 0
INDE  20  39  51  FOBS=    59.7  SIGMA=    3.1  PHAS= -134.6  FOM= 0.73  TEST= 0
INDE  20  39  53  FOBS=    39.9  SIGMA=    5.5  PHAS=   97.0  FOM= 0.08  TEST= 1
INDE  20  39  55  FOBS=    44.5  SIGMA=    4.9  PHAS=   10.9  FOM= 0.58  TEST= 0
INDE  20  39  57  FOBS=    55.3  SIGMA=    4.0  PHAS=  -29.2  FOM= 0.47  TEST= 0
INDE  20  39  59  FOBS=    61.3  SIGMA=    3.6  PHAS=  110.8  FOM= 0.58  TEST= 0
INDE  20  39  61  FOBS=    75.1  SIGMA=    3.0  PHAS= -137.6  FOM= 0.89  TEST= 0
INDE  20  39  63  FOBS=    66.5  SIGMA=    4.4  PHAS=  166.2  FOM= 0.92  TEST= 0
INDE  20  40  20  FOBS=   259.2  SIGMA=    0.9  PHAS=  151.1  FOM= 0.89  TEST= 0
INDE  20  40  22  FOBS=   123.0  SIGMA=    1.5  PHAS=  100.7  FOM= 0.27  TEST= 0
INDE  20  40  24  FOBS=   169.7  SIGMA=    1.1  PHAS=  -53.5  FOM= 0.89  TEST= 0
```

*FIG. 12A - 444*

```
INDE  20  40  26  FOBS=   25.6  SIGMA=   7.6  PHAS=    57.1  FOM=  0.19  TEST= 0
INDE  20  40  28  FOBS=   78.7  SIGMA=   2.6  PHAS=  -139.0  FOM=  0.90  TEST= 0
INDE  20  40  30  FOBS=   26.8  SIGMA=   7.3  PHAS=    96.9  FOM=  0.11  TEST= 0
INDE  20  40  32  FOBS=   15.5  SIGMA=  12.8  PHAS=   -39.6  FOM=  0.19  TEST= 0
INDE  20  40  34  FOBS=   53.0  SIGMA=   3.7  PHAS=    12.7  FOM=  0.31  TEST= 0
INDE  20  40  36  FOBS=   73.4  SIGMA=   2.5  PHAS=   -50.6  FOM=  0.89  TEST= 0
INDE  20  40  38  FOBS=  133.7  SIGMA=   1.4  PHAS=  -167.8  FOM=  0.94  TEST= 0
INDE  20  40  40  FOBS=   47.7  SIGMA=   3.9  PHAS=   175.4  FOM=  0.65  TEST= 0
INDE  20  40  42  FOBS=   40.7  SIGMA=   4.2  PHAS=   -69.0  FOM=  0.22  TEST= 0
INDE  20  40  44  FOBS=   73.2  SIGMA=   2.8  PHAS=   169.1  FOM=  0.68  TEST= 0
INDE  20  40  46  FOBS=   44.1  SIGMA=   5.4  PHAS=   -92.9  FOM=  0.19  TEST= 1
INDE  20  40  48  FOBS=   47.3  SIGMA=   4.1  PHAS=  -168.0  FOM=  0.20  TEST= 0
INDE  20  40  50  FOBS=   54.9  SIGMA=   3.6  PHAS=  -169.2  FOM=  0.30  TEST= 1
INDE  20  40  52  FOBS=   36.4  SIGMA=   6.1  PHAS=   -40.9  FOM=  0.74  TEST= 0
INDE  20  40  54  FOBS=    0.0  SIGMA=  22.0  PHAS=     0.0  FOM=  0.00  TEST= 0
INDE  20  40  56  FOBS=   32.8  SIGMA=   7.2  PHAS=    58.5  FOM=  0.45  TEST= 0
INDE  20  40  58  FOBS=   51.3  SIGMA=   4.3  PHAS=    27.2  FOM=  0.43  TEST= 0
INDE  20  40  60  FOBS=   23.9  SIGMA=  13.4  PHAS=    92.7  FOM=  0.50  TEST= 0
INDE  20  40  62  FOBS=    0.0  SIGMA=  25.6  PHAS=     0.0  FOM=  0.00  TEST= 0
INDE  20  41  21  FOBS=   47.3  SIGMA=   4.0  PHAS=   -38.0  FOM=  0.44  TEST= 0
INDE  20  41  23  FOBS=  155.5  SIGMA=   1.2  PHAS=    77.1  FOM=  0.91  TEST= 0
INDE  20  41  25  FOBS=  252.5  SIGMA=   0.9  PHAS=   -86.1  FOM=  0.96  TEST= 0
INDE  20  41  27  FOBS=  148.0  SIGMA=   1.4  PHAS=  -109.8  FOM=  0.07  TEST= 1
INDE  20  41  29  FOBS=   55.4  SIGMA=   3.8  PHAS=   -39.9  FOM=  0.55  TEST= 0
INDE  20  41  31  FOBS=  106.8  SIGMA=   1.9  PHAS=   -80.5  FOM=  0.88  TEST= 0
INDE  20  41  33  FOBS=  109.7  SIGMA=   1.9  PHAS=  -138.5  FOM=  0.91  TEST= 0
INDE  20  41  35  FOBS=  148.6  SIGMA=   1.3  PHAS=   161.7  FOM=  0.92  TEST= 0
INDE  20  41  37  FOBS=  130.0  SIGMA=   1.4  PHAS=    14.6  FOM=  0.84  TEST= 0
INDE  20  41  39  FOBS=    0.0  SIGMA=  20.6  PHAS=     0.0  FOM=  0.00  TEST= 0
INDE  20  41  41  FOBS=   94.9  SIGMA=   1.9  PHAS=    99.9  FOM=  0.63  TEST= 0
INDE  20  41  43  FOBS=   58.1  SIGMA=   3.0  PHAS=    97.6  FOM=  0.63  TEST= 0
INDE  20  41  45  FOBS=    0.0  SIGMA=  19.9  PHAS=     0.0  FOM=  0.00  TEST= 0
INDE  20  41  47  FOBS=    0.0  SIGMA=  20.5  PHAS=     0.0  FOM=  0.00  TEST= 0
INDE  20  41  49  FOBS=    0.0  SIGMA=  21.9  PHAS=     0.0  FOM=  0.00  TEST= 1
INDE  20  41  51  FOBS=   94.7  SIGMA=   2.6  PHAS=  -145.7  FOM=  0.91  TEST= 0
INDE  20  41  53  FOBS=   18.7  SIGMA=  11.8  PHAS=   -46.0  FOM=  0.34  TEST= 0
INDE  20  41  55  FOBS=   48.2  SIGMA=   4.6  PHAS=   -23.1  FOM=  0.67  TEST= 0
INDE  20  41  57  FOBS=    0.0  SIGMA=  20.9  PHAS=     0.0  FOM=  0.00  TEST= 0
INDE  20  41  59  FOBS=   33.8  SIGMA=   6.6  PHAS=   118.5  FOM=  0.29  TEST= 0
INDE  20  41  61  FOBS=    0.0  SIGMA=  23.7  PHAS=     0.0  FOM=  0.00  TEST= 0
INDE  20  42  20  FOBS=  147.2  SIGMA=   1.3  PHAS=    52.8  FOM=  0.89  TEST= 0
INDE  20  42  22  FOBS=  245.2  SIGMA=   0.9  PHAS=   -33.5  FOM=  0.93  TEST= 0
INDE  20  42  24  FOBS=  220.7  SIGMA=   1.0  PHAS=   -95.6  FOM=  0.93  TEST= 0
INDE  20  42  26  FOBS=   71.2  SIGMA=   2.7  PHAS=   161.3  FOM=  0.60  TEST= 1
INDE  20  42  28  FOBS=  159.2  SIGMA=   1.2  PHAS=  -142.0  FOM=  0.95  TEST= 0
INDE  20  42  30  FOBS=  111.7  SIGMA=   1.8  PHAS=   136.5  FOM=  0.89  TEST= 0
INDE  20  42  32  FOBS=  107.5  SIGMA=   1.9  PHAS=   -59.0  FOM=  0.95  TEST= 0
INDE  20  42  34  FOBS=   87.0  SIGMA=   2.5  PHAS=    70.6  FOM=  0.94  TEST= 0
INDE  20  42  36  FOBS=  102.3  SIGMA=   1.8  PHAS=  -147.8  FOM=  0.18  TEST= 0
INDE  20  42  38  FOBS=   53.0  SIGMA=   3.3  PHAS=   172.9  FOM=  0.26  TEST= 0
INDE  20  42  40  FOBS=   67.4  SIGMA=   2.6  PHAS=     1.9  FOM=  0.62  TEST= 0
INDE  20  42  42  FOBS=   80.6  SIGMA=   2.2  PHAS=   -69.2  FOM=  0.84  TEST= 0
INDE  20  42  44  FOBS=    0.0  SIGMA=  22.3  PHAS=     0.0  FOM=  0.00  TEST= 0
INDE  20  42  46  FOBS=    0.0  SIGMA=  21.9  PHAS=     0.0  FOM=  0.00  TEST= 0
INDE  20  42  48  FOBS=    5.2  SIGMA=  46.6  PHAS=    -0.5  FOM=  0.06  TEST= 0
INDE  20  42  50  FOBS=  102.8  SIGMA=   2.4  PHAS=   -66.0  FOM=  0.32  TEST= 0
INDE  20  42  52  FOBS=   74.5  SIGMA=   3.0  PHAS=   -41.3  FOM=  0.76  TEST= 0
INDE  20  42  54  FOBS=  100.5  SIGMA=   2.3  PHAS=  -140.6  FOM=  0.20  TEST= 1
INDE  20  42  56  FOBS=    0.0  SIGMA=  21.9  PHAS=     0.0  FOM=  0.00  TEST= 0
INDE  20  42  58  FOBS=   55.0  SIGMA=   4.1  PHAS=    59.5  FOM=  0.54  TEST= 0
INDE  20  42  60  FOBS=   44.0  SIGMA=   6.4  PHAS=    82.9  FOM=  0.72  TEST= 0
INDE  20  42  62  FOBS=   23.3  SIGMA=  12.4  PHAS=   155.7  FOM=  0.08  TEST= 0
INDE  20  43  21  FOBS=  187.1  SIGMA=   1.1  PHAS=  -112.6  FOM=  0.93  TEST= 0
INDE  20  43  23  FOBS=  193.1  SIGMA=   1.1  PHAS=   164.3  FOM=  0.93  TEST= 0
INDE  20  43  25  FOBS=  188.7  SIGMA=   1.1  PHAS=  -154.6  FOM=  0.96  TEST= 0
INDE  20  43  27  FOBS=   47.8  SIGMA=   3.9  PHAS=  -118.0  FOM=  0.92  TEST= 0
INDE  20  43  29  FOBS=  157.5  SIGMA=   1.2  PHAS=    75.0  FOM=  0.97  TEST= 0
INDE  20  43  31  FOBS=  171.4  SIGMA=   1.2  PHAS=   159.2  FOM=  0.97  TEST= 0
INDE  20  43  33  FOBS=  110.9  SIGMA=   1.8  PHAS=   -92.1  FOM=  0.86  TEST= 0
INDE  20  43  35  FOBS=  119.0  SIGMA=   1.7  PHAS=   131.0  FOM=  0.71  TEST= 0
```

*FIG. 12A - 445*

```
INDE  20  43  37  FOBS=    82.3  SIGMA=   2.2  PHAS=   20.4  FOM=  0.90  TEST=  0
INDE  20  43  39  FOBS=    97.0  SIGMA=   1.9  PHAS=  -46.2  FOM=  0.86  TEST=  0
INDE  20  43  41  FOBS=    67.7  SIGMA=   2.6  PHAS=  -82.6  FOM=  0.77  TEST=  1
INDE  20  43  43  FOBS=    83.0  SIGMA=   2.1  PHAS=  162.5  FOM=  0.91  TEST=  0
INDE  20  43  45  FOBS=    91.2  SIGMA=   2.1  PHAS= -163.5  FOM=  0.89  TEST=  0
INDE  20  43  47  FOBS=    42.1  SIGMA=   5.8  PHAS=  170.4  FOM=  0.71  TEST=  0
INDE  20  43  49  FOBS=   117.4  SIGMA=   2.2  PHAS=  177.0  FOM=  0.93  TEST=  0
INDE  20  43  51  FOBS=    58.6  SIGMA=   4.2  PHAS=  -90.7  FOM=  0.90  TEST=  0
INDE  20  43  53  FOBS=     0.0  SIGMA=  27.1  PHAS=    0.0  FOM=  0.00  TEST=  0
INDE  20  43  55  FOBS=    52.3  SIGMA=   4.3  PHAS=  122.2  FOM=  0.55  TEST=  0
INDE  20  43  57  FOBS=     0.0  SIGMA=  22.1  PHAS=    0.0  FOM=  0.00  TEST=  0
INDE  20  43  59  FOBS=    28.6  SIGMA=   9.6  PHAS=  119.7  FOM=  0.03  TEST=  1
INDE  20  43  61  FOBS=     0.0  SIGMA=  25.7  PHAS=    0.0  FOM=  0.00  TEST=  1
INDE  20  44  20  FOBS=    48.2  SIGMA=   4.2  PHAS=   60.0  FOM=  0.81  TEST=  0
INDE  20  44  22  FOBS=   183.0  SIGMA=   1.2  PHAS=   49.3  FOM=  0.93  TEST=  0
INDE  20  44  24  FOBS=   127.7  SIGMA=   1.6  PHAS=   67.8  FOM=  0.93  TEST=  0
INDE  20  44  26  FOBS=    50.7  SIGMA=   3.7  PHAS=  136.7  FOM=  0.53  TEST=  0
INDE  20  44  28  FOBS=   102.9  SIGMA=   1.9  PHAS= -109.2  FOM=  0.97  TEST=  0
INDE  20  44  30  FOBS=    79.7  SIGMA=   2.2  PHAS=   50.2  FOM=  0.59  TEST=  0
INDE  20  44  32  FOBS=   162.6  SIGMA=   1.2  PHAS=   12.8  FOM=  0.94  TEST=  0
INDE  20  44  34  FOBS=   130.3  SIGMA=   1.6  PHAS=   30.1  FOM=  0.89  TEST=  0
INDE  20  44  36  FOBS=    34.7  SIGMA=   6.0  PHAS=  159.5  FOM=  0.72  TEST=  0
INDE  20  44  38  FOBS=    86.8  SIGMA=   2.1  PHAS=  -81.3  FOM=  0.82  TEST=  0
INDE  20  44  40  FOBS=    68.8  SIGMA=   2.6  PHAS= -140.1  FOM=  0.75  TEST=  0
INDE  20  44  42  FOBS=    48.8  SIGMA=   4.1  PHAS=   57.6  FOM=  0.72  TEST=  0
INDE  20  44  44  FOBS=    75.6  SIGMA=   2.6  PHAS=   21.4  FOM=  0.82  TEST=  0
INDE  20  44  46  FOBS=    95.2  SIGMA=   2.5  PHAS=  117.2  FOM=  0.88  TEST=  0
INDE  20  44  48  FOBS=    78.4  SIGMA=   3.2  PHAS=   32.2  FOM=  0.90  TEST=  0
INDE  20  44  50  FOBS=    82.6  SIGMA=   3.0  PHAS=  137.8  FOM=  0.92  TEST=  0
INDE  20  44  52  FOBS=     0.0  SIGMA=  23.5  PHAS=    0.0  FOM=  0.00  TEST=  0
INDE  20  44  54  FOBS=    76.0  SIGMA=   3.0  PHAS=   12.6  FOM=  0.85  TEST=  0
INDE  20  44  56  FOBS=     0.0  SIGMA=  22.2  PHAS=    0.0  FOM=  0.00  TEST=  0
INDE  20  44  58  FOBS=    65.3  SIGMA=   3.5  PHAS=   58.0  FOM=  0.87  TEST=  0
INDE  20  44  60  FOBS=    70.7  SIGMA=   4.1  PHAS=  127.9  FOM=  0.87  TEST=  0
INDE  20  45  21  FOBS=   142.9  SIGMA=   1.4  PHAS= -153.7  FOM=  0.79  TEST=  0
INDE  20  45  23  FOBS=    86.9  SIGMA=   2.2  PHAS=  -56.6  FOM=  0.74  TEST=  0
INDE  20  45  25  FOBS=    32.5  SIGMA=   6.2  PHAS= -106.6  FOM=  0.14  TEST=  1
INDE  20  45  27  FOBS=    40.4  SIGMA=   4.7  PHAS=  -50.7  FOM=  0.40  TEST=  0
INDE  20  45  29  FOBS=     0.0  SIGMA=  19.9  PHAS=    0.0  FOM=  0.00  TEST=  0
INDE  20  45  31  FOBS=    86.9  SIGMA=   2.0  PHAS=  161.9  FOM=  0.71  TEST=  1
INDE  20  45  33  FOBS=   103.8  SIGMA=   1.8  PHAS=  -10.4  FOM=  0.87  TEST=  0
INDE  20  45  35  FOBS=     0.0  SIGMA=  19.6  PHAS=    0.0  FOM=  0.00  TEST=  0
INDE  20  45  37  FOBS=    83.6  SIGMA=   2.4  PHAS=   48.4  FOM=  0.89  TEST=  0
INDE  20  45  39  FOBS=     0.0  SIGMA=  20.6  PHAS=    0.0  FOM=  0.00  TEST=  0
INDE  20  45  41  FOBS=    65.9  SIGMA=   3.1  PHAS=  -93.2  FOM=  0.58  TEST=  0
INDE  20  45  43  FOBS=    84.5  SIGMA=   2.4  PHAS= -133.4  FOM=  0.90  TEST=  0
INDE  20  45  45  FOBS=    63.0  SIGMA=   3.4  PHAS= -175.7  FOM=  0.70  TEST=  0
INDE  20  45  47  FOBS=    42.5  SIGMA=   5.8  PHAS= -105.8  FOM=  0.61  TEST=  0
INDE  20  45  49  FOBS=     1.3  SIGMA= 188.5  PHAS=   94.6  FOM=  0.01  TEST=  0
INDE  20  45  51  FOBS=    71.7  SIGMA=   3.5  PHAS=  -50.4  FOM=  0.87  TEST=  0
INDE  20  45  53  FOBS=     0.0  SIGMA=  22.0  PHAS=    0.0  FOM=  0.00  TEST=  1
INDE  20  45  55  FOBS=    12.1  SIGMA=  25.4  PHAS=  176.7  FOM=  0.32  TEST=  0
INDE  20  45  57  FOBS=    94.4  SIGMA=   2.5  PHAS=  -29.6  FOM=  0.79  TEST=  0
INDE  20  45  59  FOBS=   100.6  SIGMA=   3.0  PHAS= -120.5  FOM=  0.91  TEST=  0
INDE  20  46  20  FOBS=    73.3  SIGMA=   2.8  PHAS=  177.8  FOM=  0.69  TEST=  0
INDE  20  46  22  FOBS=   107.3  SIGMA=   1.8  PHAS=   94.6  FOM=  0.62  TEST=  0
INDE  20  46  24  FOBS=   105.6  SIGMA=   1.9  PHAS=    8.9  FOM=  0.67  TEST=  0
INDE  20  46  26  FOBS=   109.7  SIGMA=   1.8  PHAS=  -96.2  FOM=  0.75  TEST=  0
INDE  20  46  28  FOBS=     0.0  SIGMA=  20.2  PHAS=    0.0  FOM=  0.00  TEST=  0
INDE  20  46  30  FOBS=    55.6  SIGMA=   3.4  PHAS= -105.7  FOM=  0.72  TEST=  0
INDE  20  46  32  FOBS=    72.0  SIGMA=   2.4  PHAS=  -56.6  FOM=  0.69  TEST=  1
INDE  20  46  34  FOBS=   107.4  SIGMA=   1.9  PHAS=  -64.6  FOM=  0.90  TEST=  0
INDE  20  46  36  FOBS=   165.3  SIGMA=   1.5  PHAS=  -50.3  FOM=  0.94  TEST=  0
INDE  20  46  38  FOBS=    84.4  SIGMA=   2.4  PHAS=  -79.9  FOM=  0.90  TEST=  0
INDE  20  46  40  FOBS=     0.0  SIGMA=  22.2  PHAS=    0.0  FOM=  0.00  TEST=  0
INDE  20  46  42  FOBS=    79.3  SIGMA=   2.6  PHAS=  138.5  FOM=  0.90  TEST=  0
INDE  20  46  44  FOBS=   103.0  SIGMA=   2.0  PHAS=  106.6  FOM=  0.74  TEST=  0
INDE  20  46  46  FOBS=   103.2  SIGMA=   2.1  PHAS=   97.4  FOM=  0.90  TEST=  0
INDE  20  46  48  FOBS=    80.6  SIGMA=   3.1  PHAS=  -88.6  FOM=  0.69  TEST=  0
INDE  20  46  50  FOBS=    59.9  SIGMA=   4.2  PHAS=  126.1  FOM=  0.14  TEST=  0
```

*FIG. 12A - 446*

```
INDE 20 46 52 FOBS=    91.0 SIGMA=  2.8 PHAS=  141.9 FOM= 0.23 TEST= 1
INDE 20 46 54 FOBS=   107.0 SIGMA=  2.2 PHAS=   85.9 FOM= 0.95 TEST= 0
INDE 20 46 56 FOBS=    67.4 SIGMA=  3.5 PHAS=  -80.2 FOM= 0.16 TEST= 0
INDE 20 46 58 FOBS=    18.8 SIGMA= 15.1 PHAS=  -74.0 FOM= 0.23 TEST= 0
INDE 20 47 21 FOBS=    99.8 SIGMA=  1.9 PHAS=   67.2 FOM= 0.91 TEST= 0
INDE 20 47 23 FOBS=    15.4 SIGMA= 13.0 PHAS=  174.3 FOM= 0.07 TEST= 0
INDE 20 47 25 FOBS=   106.4 SIGMA=  1.8 PHAS= -130.1 FOM= 0.81 TEST= 0
INDE 20 47 27 FOBS=   172.5 SIGMA=  1.2 PHAS=  -65.7 FOM= 0.97 TEST= 0
INDE 20 47 29 FOBS=     0.0 SIGMA= 20.8 PHAS=    0.0 FOM= 0.00 TEST= 0
INDE 20 47 31 FOBS=   100.7 SIGMA=  1.8 PHAS= -105.1 FOM= 0.86 TEST= 0
INDE 20 47 33 FOBS=    57.0 SIGMA=  3.4 PHAS= -141.9 FOM= 0.66 TEST= 0
INDE 20 47 35 FOBS=    74.1 SIGMA=  2.9 PHAS= -133.9 FOM= 0.90 TEST= 0
INDE 20 47 37 FOBS=    90.6 SIGMA=  2.6 PHAS=  162.8 FOM= 0.93 TEST= 0
INDE 20 47 39 FOBS=     0.0 SIGMA= 20.7 PHAS=    0.0 FOM= 0.00 TEST= 0
INDE 20 47 41 FOBS=     0.0 SIGMA= 20.5 PHAS=    0.0 FOM= 0.00 TEST= 0
INDE 20 47 43 FOBS=    84.7 SIGMA=  2.4 PHAS=   46.3 FOM= 0.88 TEST= 0
INDE 20 47 45 FOBS=    61.8 SIGMA=  3.2 PHAS=   21.5 FOM= 0.79 TEST= 0
INDE 20 47 47 FOBS=    41.4 SIGMA=  5.5 PHAS=  -81.4 FOM= 0.61 TEST= 0
INDE 20 47 49 FOBS=    38.5 SIGMA=  7.2 PHAS= -111.0 FOM= 0.45 TEST= 0
INDE 20 47 51 FOBS=    45.0 SIGMA=  5.5 PHAS=  -15.6 FOM= 0.49 TEST= 0
INDE 20 47 53 FOBS=   121.7 SIGMA=  2.2 PHAS=    6.6 FOM= 0.97 TEST= 0
INDE 20 47 55 FOBS=    30.2 SIGMA=  7.6 PHAS=   14.4 FOM= 0.65 TEST= 0
INDE 20 47 57 FOBS=    27.8 SIGMA= 10.3 PHAS= -140.6 FOM= 0.59 TEST= 0
INDE 20 48 20 FOBS=    98.7 SIGMA=  1.9 PHAS=   -5.9 FOM= 0.67 TEST= 0
INDE 20 48 22 FOBS=    66.8 SIGMA=  3.1 PHAS= -100.6 FOM= 0.87 TEST= 0
INDE 20 48 24 FOBS=    92.4 SIGMA=  2.3 PHAS=  -39.0 FOM= 0.81 TEST= 0
INDE 20 48 26 FOBS=   228.6 SIGMA=  1.1 PHAS= -161.2 FOM= 0.97 TEST= 0
INDE 20 48 28 FOBS=     4.2 SIGMA= 51.7 PHAS=  175.9 FOM= 0.12 TEST= 0
INDE 20 48 30 FOBS=     0.0 SIGMA= 20.7 PHAS=    0.0 FOM= 0.00 TEST= 0
INDE 20 48 32 FOBS=     0.0 SIGMA= 20.1 PHAS=    0.0 FOM= 0.00 TEST= 0
INDE 20 48 34 FOBS=    32.9 SIGMA=  6.5 PHAS= -142.4 FOM= 0.37 TEST= 0
INDE 20 48 36 FOBS=    21.8 SIGMA= 10.6 PHAS= -158.9 FOM= 0.19 TEST= 0
INDE 20 48 38 FOBS=    60.2 SIGMA=  3.9 PHAS=   67.8 FOM= 0.25 TEST= 0
INDE 20 48 40 FOBS=     0.0 SIGMA= 21.8 PHAS=    0.0 FOM= 0.00 TEST= 0
INDE 20 48 42 FOBS=    46.8 SIGMA=  4.5 PHAS=  -26.1 FOM= 0.67 TEST= 0
INDE 20 48 44 FOBS=    49.4 SIGMA=  4.0 PHAS=  -63.3 FOM= 0.73 TEST= 0
INDE 20 48 46 FOBS=    78.8 SIGMA=  2.7 PHAS= -163.6 FOM= 0.86 TEST= 0
INDE 20 48 48 FOBS=    34.2 SIGMA=  6.2 PHAS= -170.6 FOM= 0.59 TEST= 0
INDE 20 48 50 FOBS=    78.7 SIGMA=  3.2 PHAS=  -84.2 FOM= 0.82 TEST= 0
INDE 20 48 52 FOBS=    41.7 SIGMA=  6.1 PHAS=   22.5 FOM= 0.82 TEST= 0
INDE 20 48 54 FOBS=    83.5 SIGMA=  2.8 PHAS=  -66.0 FOM= 0.77 TEST= 0
INDE 20 48 56 FOBS=    56.6 SIGMA=  5.1 PHAS=  125.5 FOM= 0.18 TEST= 1
INDE 20 49 21 FOBS=   211.8 SIGMA=  1.2 PHAS= -105.2 FOM= 0.38 TEST= 1
INDE 20 49 23 FOBS=    86.4 SIGMA=  2.6 PHAS=  166.8 FOM= 0.87 TEST= 0
INDE 20 49 25 FOBS=   131.9 SIGMA=  1.8 PHAS=  129.0 FOM= 0.92 TEST= 0
INDE 20 49 27 FOBS=    55.3 SIGMA=  4.0 PHAS=  -32.7 FOM= 0.83 TEST= 0
INDE 20 49 29 FOBS=   147.1 SIGMA=  1.6 PHAS=  -16.1 FOM= 0.89 TEST= 0
INDE 20 49 31 FOBS=    49.9 SIGMA=  4.4 PHAS= -178.0 FOM= 0.81 TEST= 0
INDE 20 49 33 FOBS=    30.2 SIGMA=  6.2 PHAS=  -52.0 FOM= 0.16 TEST= 0
INDE 20 49 35 FOBS=     0.0 SIGMA= 19.4 PHAS=    0.0 FOM= 0.00 TEST= 0
INDE 20 49 37 FOBS=    48.5 SIGMA=  4.3 PHAS=   80.9 FOM= 0.72 TEST= 0
INDE 20 49 39 FOBS=    70.4 SIGMA=  3.3 PHAS=  124.9 FOM= 0.53 TEST= 0
INDE 20 49 41 FOBS=   124.8 SIGMA=  1.7 PHAS= -145.5 FOM= 0.95 TEST= 0
INDE 20 49 43 FOBS=     0.0 SIGMA= 20.5 PHAS=    0.0 FOM= 0.00 TEST= 0
INDE 20 49 45 FOBS=    94.8 SIGMA=  2.2 PHAS=   68.6 FOM= 0.89 TEST= 0
INDE 20 49 47 FOBS=    40.8 SIGMA=  5.7 PHAS= -173.9 FOM= 0.13 TEST= 1
INDE 20 49 49 FOBS=    85.6 SIGMA=  2.6 PHAS=   95.7 FOM= 0.91 TEST= 0
INDE 20 49 51 FOBS=    14.9 SIGMA= 18.7 PHAS=   -0.5 FOM= 0.11 TEST= 0
INDE 20 49 53 FOBS=   114.2 SIGMA=  2.3 PHAS=  -18.0 FOM= 0.95 TEST= 0
INDE 20 49 55 FOBS=    70.3 SIGMA=  4.1 PHAS=   48.3 FOM= 0.86 TEST= 0
INDE 20 50 20 FOBS=    40.9 SIGMA=  4.7 PHAS= -147.5 FOM= 0.52 TEST= 0
INDE 20 50 22 FOBS=    61.1 SIGMA=  3.5 PHAS= -116.3 FOM= 0.58 TEST= 0
INDE 20 50 24 FOBS=    24.8 SIGMA=  8.7 PHAS=  -50.1 FOM= 0.44 TEST= 0
INDE 20 50 26 FOBS=   167.6 SIGMA=  1.4 PHAS=  165.2 FOM= 0.94 TEST= 0
INDE 20 50 28 FOBS=   161.3 SIGMA=  1.5 PHAS=  -81.3 FOM= 0.93 TEST= 0
INDE 20 50 30 FOBS=    51.9 SIGMA=  4.6 PHAS= -145.5 FOM= 0.77 TEST= 0
INDE 20 50 32 FOBS=   106.4 SIGMA=  2.1 PHAS=   24.4 FOM= 0.95 TEST= 0
INDE 20 50 34 FOBS=    39.5 SIGMA=  4.9 PHAS= -171.1 FOM= 0.22 TEST= 0
INDE 20 50 36 FOBS=    35.2 SIGMA=  6.4 PHAS= -166.0 FOM= 0.24 TEST= 0
INDE 20 50 38 FOBS=    25.3 SIGMA= 11.0 PHAS=   48.7 FOM= 0.38 TEST= 0
```

*FIG. 12A - 447*

```
INDE  20  50  40  FOBS=   66.5  SIGMA=   3.1  PHAS=   109.7  FOM=  0.82  TEST= 0
INDE  20  50  42  FOBS=   56.6  SIGMA=   3.6  PHAS=  -179.9  FOM=  0.22  TEST= 0
INDE  20  50  44  FOBS=   98.8  SIGMA=   2.1  PHAS=  -121.5  FOM=  0.86  TEST= 0
INDE  20  50  46  FOBS=  119.4  SIGMA=   1.8  PHAS=  -154.7  FOM=  0.96  TEST= 0
INDE  20  50  48  FOBS=   42.8  SIGMA=   5.4  PHAS=    43.1  FOM=  0.78  TEST= 0
INDE  20  50  50  FOBS=   77.1  SIGMA=   2.8  PHAS=    12.9  FOM=  0.46  TEST= 1
INDE  20  50  52  FOBS=    0.0  SIGMA=  21.6  PHAS=     0.0  FOM=  0.00  TEST= 0
INDE  20  50  54  FOBS=   70.1  SIGMA=   4.1  PHAS=   -30.5  FOM=  0.47  TEST= 0
INDE  20  50  56  FOBS=    0.0  SIGMA=  26.4  PHAS=     0.0  FOM=  0.00  TEST= 0
INDE  20  51  21  FOBS=  141.9  SIGMA=   1.7  PHAS=    38.9  FOM=  0.93  TEST= 0
INDE  20  51  23  FOBS=    0.0  SIGMA=  20.5  PHAS=     0.0  FOM=  0.00  TEST= 0
INDE  20  51  25  FOBS=   79.9  SIGMA=   2.7  PHAS=   109.5  FOM=  0.66  TEST= 0
INDE  20  51  27  FOBS=   81.3  SIGMA=   2.7  PHAS=   178.7  FOM=  0.11  TEST= 1
INDE  20  51  29  FOBS=  108.8  SIGMA=   2.1  PHAS=  -109.9  FOM=  0.95  TEST= 0
INDE  20  51  31  FOBS=   44.0  SIGMA=   5.3  PHAS=     1.7  FOM=  0.07  TEST= 1
INDE  20  51  33  FOBS=  176.8  SIGMA=   1.2  PHAS=   -74.9  FOM=  0.96  TEST= 0
INDE  20  51  35  FOBS=  114.2  SIGMA=   1.7  PHAS=    48.4  FOM=  0.89  TEST= 0
INDE  20  51  37  FOBS=   59.4  SIGMA=   3.2  PHAS=    31.1  FOM=  0.47  TEST= 0
INDE  20  51  39  FOBS=    0.0  SIGMA=  21.1  PHAS=     0.0  FOM=  0.00  TEST= 0
INDE  20  51  41  FOBS=   64.7  SIGMA=   3.1  PHAS=   160.6  FOM=  0.88  TEST= 0
INDE  20  51  43  FOBS=   33.9  SIGMA=   6.7  PHAS=  -114.5  FOM=  0.44  TEST= 0
INDE  20  51  45  FOBS=  178.1  SIGMA=   1.4  PHAS=   106.2  FOM=  0.98  TEST= 0
INDE  20  51  47  FOBS=   73.2  SIGMA=   3.0  PHAS=   159.8  FOM=  0.72  TEST= 0
INDE  20  51  49  FOBS=   10.7  SIGMA=  22.4  PHAS=   -67.6  FOM=  0.16  TEST= 0
INDE  20  51  51  FOBS=   48.1  SIGMA=   5.1  PHAS=   -56.8  FOM=  0.75  TEST= 0
INDE  20  51  53  FOBS=   41.6  SIGMA=   7.4  PHAS=    69.1  FOM=  0.64  TEST= 0
INDE  20  51  55  FOBS=   14.9  SIGMA=  23.6  PHAS=   147.3  FOM=  0.14  TEST= 0
INDE  20  52  20  FOBS=  108.1  SIGMA=   1.6  PHAS=   -81.1  FOM=  0.91  TEST= 0
INDE  20  52  22  FOBS=   90.8  SIGMA=   2.4  PHAS=   -26.4  FOM=  0.93  TEST= 0
INDE  20  52  24  FOBS=   75.0  SIGMA=   2.8  PHAS=   -89.4  FOM=  0.87  TEST= 0
INDE  20  52  26  FOBS=  106.0  SIGMA=   2.1  PHAS=    69.8  FOM=  0.85  TEST= 0
INDE  20  52  28  FOBS=  111.3  SIGMA=   2.0  PHAS=   155.9  FOM=  0.90  TEST= 0
INDE  20  52  30  FOBS=  114.2  SIGMA=   2.0  PHAS=   171.1  FOM=  0.94  TEST= 0
INDE  20  52  32  FOBS=   57.0  SIGMA=   3.8  PHAS=   117.0  FOM=  0.62  TEST= 0
INDE  20  52  34  FOBS=   37.8  SIGMA=   6.2  PHAS=  -130.3  FOM=  0.75  TEST= 0
INDE  20  52  36  FOBS=   71.6  SIGMA=   2.7  PHAS=    64.4  FOM=  0.66  TEST= 0
INDE  20  52  38  FOBS=    0.0  SIGMA=  19.4  PHAS=     0.0  FOM=  0.00  TEST= 0
INDE  20  52  40  FOBS=   31.5  SIGMA=   7.2  PHAS=    24.5  FOM=  0.87  TEST= 0
INDE  20  52  42  FOBS=   42.9  SIGMA=   4.7  PHAS=    86.4  FOM=  0.58  TEST= 0
INDE  20  52  44  FOBS=   19.2  SIGMA=  11.2  PHAS=    36.2  FOM=  0.30  TEST= 0
INDE  20  52  46  FOBS=   49.1  SIGMA=   4.6  PHAS=    94.7  FOM=  0.57  TEST= 0
INDE  20  52  48  FOBS=   49.1  SIGMA=   4.9  PHAS=    61.2  FOM=  0.71  TEST= 0
INDE  20  52  50  FOBS=   26.7  SIGMA=   9.9  PHAS=  -174.4  FOM=  0.61  TEST= 0
INDE  20  52  52  FOBS=   44.9  SIGMA=   7.1  PHAS=    12.8  FOM=  0.49  TEST= 0
INDE  20  52  54  FOBS=   42.1  SIGMA=   8.9  PHAS=    34.0  FOM=  0.71  TEST= 0
INDE  20  53  21  FOBS=    0.0  SIGMA=  21.1  PHAS=     0.0  FOM=  0.00  TEST= 0
INDE  20  53  23  FOBS=   46.8  SIGMA=   4.5  PHAS=    -4.7  FOM=  0.53  TEST= 0
INDE  20  53  25  FOBS=   50.9  SIGMA=   4.2  PHAS=   -32.9  FOM=  0.60  TEST= 0
INDE  20  53  27  FOBS=  109.2  SIGMA=   2.0  PHAS=    -1.1  FOM=  0.96  TEST= 0
INDE  20  53  29  FOBS=   83.3  SIGMA=   2.6  PHAS=    44.3  FOM=  0.88  TEST= 0
INDE  20  53  31  FOBS=   85.9  SIGMA=   2.6  PHAS=   108.7  FOM=  0.90  TEST= 0
INDE  20  53  33  FOBS=   86.6  SIGMA=   2.5  PHAS=   -62.3  FOM=  0.80  TEST= 0
INDE  20  53  35  FOBS=   48.3  SIGMA=   3.9  PHAS=    15.8  FOM=  0.80  TEST= 0
INDE  20  53  37  FOBS=   39.9  SIGMA=   4.7  PHAS=   -76.9  FOM=  0.43  TEST= 0
INDE  20  53  39  FOBS=   20.9  SIGMA=  10.0  PHAS=   -50.3  FOM=  0.14  TEST= 0
INDE  20  53  41  FOBS=   22.0  SIGMA=   9.0  PHAS=   137.5  FOM=  0.26  TEST= 0
INDE  20  53  43  FOBS=   32.9  SIGMA=   6.8  PHAS=    90.0  FOM=  0.35  TEST= 1
INDE  20  53  45  FOBS=   35.7  SIGMA=   6.8  PHAS=  -179.5  FOM=  0.54  TEST= 0
INDE  20  53  47  FOBS=    0.0  SIGMA=  22.1  PHAS=     0.0  FOM=  0.00  TEST= 1
INDE  20  53  49  FOBS=   63.0  SIGMA=   4.4  PHAS=    60.1  FOM=  0.87  TEST= 0
INDE  20  53  51  FOBS=    0.0  SIGMA=  26.9  PHAS=     0.0  FOM=  0.00  TEST= 0
INDE  20  53  53  FOBS=   39.0  SIGMA=   8.3  PHAS=    -9.9  FOM=  0.64  TEST= 0
INDE  20  54  20  FOBS=  121.5  SIGMA=   1.7  PHAS=  -109.1  FOM=  0.94  TEST= 0
INDE  20  54  22  FOBS=   21.4  SIGMA=  10.7  PHAS=   174.9  FOM=  0.64  TEST= 0
INDE  20  54  24  FOBS=  115.9  SIGMA=   1.9  PHAS=  -146.6  FOM=  0.94  TEST= 0
INDE  20  54  26  FOBS=   31.9  SIGMA=   6.6  PHAS=   -30.6  FOM=  0.48  TEST= 0
INDE  20  54  28  FOBS=   62.9  SIGMA=   3.4  PHAS=   -70.4  FOM=  0.84  TEST= 0
INDE  20  54  30  FOBS=   73.4  SIGMA=   3.0  PHAS=   130.1  FOM=  0.02  TEST= 1
INDE  20  54  32  FOBS=   45.9  SIGMA=   4.7  PHAS=    46.2  FOM=  0.42  TEST= 0
INDE  20  54  34  FOBS=   43.9  SIGMA=   4.9  PHAS=   -97.0  FOM=  0.78  TEST= 0
```

*FIG. 12A - 448*

```
INDE 20 54 36 FOBS=   0.0 SIGMA= 19.9 PHAS=   0.0 FOM= 0.00 TEST= 0
INDE 20 54 38 FOBS=   0.0 SIGMA= 20.2 PHAS=   0.0 FOM= 0.00 TEST= 1
INDE 20 54 40 FOBS=  43.0 SIGMA=  4.9 PHAS=-155.4 FOM= 0.19 TEST= 0
INDE 20 54 42 FOBS=  68.7 SIGMA=  3.3 PHAS=  39.4 FOM= 0.68 TEST= 0
INDE 20 54 44 FOBS=  29.8 SIGMA=  8.3 PHAS= 111.3 FOM= 0.52 TEST= 0
INDE 20 54 46 FOBS=  58.4 SIGMA=  4.3 PHAS= 130.8 FOM= 0.78 TEST= 0
INDE 20 54 48 FOBS=  27.4 SIGMA= 13.1 PHAS=  52.8 FOM= 0.39 TEST= 0
INDE 20 54 50 FOBS=  46.4 SIGMA=  7.9 PHAS=-123.4 FOM= 0.32 TEST= 1
INDE 20 54 52 FOBS=  66.3 SIGMA=  5.0 PHAS= -68.7 FOM= 0.52 TEST= 0
INDE 20 55 21 FOBS= 105.9 SIGMA=  2.2 PHAS= 112.8 FOM= 0.89 TEST= 0
INDE 20 55 23 FOBS= 129.1 SIGMA=  1.7 PHAS=  33.9 FOM= 0.94 TEST= 0
INDE 20 55 25 FOBS=  60.4 SIGMA=  3.5 PHAS=  50.6 FOM= 0.83 TEST= 0
INDE 20 55 27 FOBS=  35.9 SIGMA=  5.9 PHAS= -21.4 FOM= 0.36 TEST= 0
INDE 20 55 29 FOBS=  52.3 SIGMA=  4.1 PHAS=  65.5 FOM= 0.46 TEST= 0
INDE 20 55 31 FOBS=  54.4 SIGMA=  4.0 PHAS=-176.8 FOM= 0.76 TEST= 0
INDE 20 55 33 FOBS=   0.0 SIGMA= 21.8 PHAS=   0.0 FOM= 0.00 TEST= 0
INDE 20 55 35 FOBS=  80.2 SIGMA=  2.6 PHAS=  80.1 FOM= 0.88 TEST= 0
INDE 20 55 37 FOBS=   0.0 SIGMA= 23.7 PHAS=   0.0 FOM= 0.00 TEST= 0
INDE 20 55 39 FOBS=  20.5 SIGMA= 11.9 PHAS= -78.2 FOM= 0.33 TEST= 0
INDE 20 55 41 FOBS=  46.5 SIGMA=  5.0 PHAS=-108.2 FOM= 0.60 TEST= 0
INDE 20 55 43 FOBS=  56.4 SIGMA=  4.0 PHAS=  36.5 FOM= 0.85 TEST= 0
INDE 20 55 45 FOBS=  48.7 SIGMA=  5.6 PHAS=  26.6 FOM= 0.79 TEST= 0
INDE 20 55 47 FOBS=  56.9 SIGMA=  4.5 PHAS= -14.4 FOM= 0.80 TEST= 0
INDE 20 55 49 FOBS=  47.1 SIGMA=  6.9 PHAS=  84.7 FOM= 0.70 TEST= 0
INDE 20 55 51 FOBS=  60.0 SIGMA=  5.5 PHAS=-133.7 FOM= 0.78 TEST= 0
INDE 20 56 20 FOBS=  94.0 SIGMA=  2.1 PHAS= -39.4 FOM= 0.77 TEST= 0
INDE 20 56 22 FOBS=  54.0 SIGMA=  4.1 PHAS= -80.9 FOM= 0.75 TEST= 0
INDE 20 56 24 FOBS=  42.7 SIGMA=  4.9 PHAS=  87.8 FOM= 0.15 TEST= 0
INDE 20 56 26 FOBS=  52.1 SIGMA=  4.1 PHAS= -37.3 FOM= 0.58 TEST= 0
INDE 20 56 28 FOBS=  36.6 SIGMA=  5.7 PHAS= -74.2 FOM= 0.50 TEST= 0
INDE 20 56 30 FOBS=  84.4 SIGMA=  2.9 PHAS= -79.6 FOM= 0.78 TEST= 0
INDE 20 56 32 FOBS=  61.9 SIGMA=  4.9 PHAS= 175.3 FOM= 0.79 TEST= 0
INDE 20 56 34 FOBS=  33.3 SIGMA=  8.0 PHAS= -19.5 FOM= 0.75 TEST= 0
INDE 20 56 36 FOBS=   0.0 SIGMA= 23.5 PHAS=   0.0 FOM= 0.00 TEST= 0
INDE 20 56 38 FOBS=   0.0 SIGMA= 22.1 PHAS=   0.0 FOM= 0.00 TEST= 1
INDE 20 56 40 FOBS=  98.4 SIGMA=  2.4 PHAS= 138.5 FOM= 0.92 TEST= 0
INDE 20 56 42 FOBS=  33.4 SIGMA=  7.0 PHAS= 112.1 FOM= 0.48 TEST= 0
INDE 20 56 44 FOBS=  27.4 SIGMA=  9.1 PHAS=  10.5 FOM= 0.30 TEST= 0
INDE 20 56 46 FOBS=  66.1 SIGMA=  3.9 PHAS= -47.1 FOM= 0.55 TEST= 0
INDE 20 56 48 FOBS=  38.7 SIGMA=  9.8 PHAS= -59.1 FOM= 0.70 TEST= 0
INDE 20 56 50 FOBS=  46.6 SIGMA=  9.8 PHAS= 147.1 FOM= 0.56 TEST= 0
INDE 20 57 21 FOBS=  66.5 SIGMA=  3.3 PHAS= 108.1 FOM= 0.85 TEST= 0
INDE 20 57 23 FOBS=  39.7 SIGMA=  5.2 PHAS=   6.5 FOM= 0.41 TEST= 0
INDE 20 57 25 FOBS=  52.7 SIGMA=  4.3 PHAS=  27.4 FOM= 0.48 TEST= 0
INDE 20 57 27 FOBS=  80.4 SIGMA=  3.2 PHAS=  84.3 FOM= 0.64 TEST= 0
INDE 20 57 29 FOBS=  18.8 SIGMA= 16.0 PHAS=-140.0 FOM= 0.13 TEST= 0
INDE 20 57 31 FOBS= 117.6 SIGMA=  2.4 PHAS= 179.8 FOM= 0.93 TEST= 0
INDE 20 57 33 FOBS=  20.7 SIGMA= 12.9 PHAS= 142.1 FOM= 0.38 TEST= 0
INDE 20 57 35 FOBS=  12.5 SIGMA= 21.5 PHAS= 143.4 FOM= 0.06 TEST= 0
INDE 20 57 37 FOBS=  75.6 SIGMA=  3.0 PHAS= -69.1 FOM= 0.86 TEST= 0
INDE 20 57 39 FOBS=  52.3 SIGMA=  4.4 PHAS=  63.4 FOM= 0.68 TEST= 0
INDE 20 57 41 FOBS=   1.8 SIGMA=135.3 PHAS= -28.6 FOM= 0.03 TEST= 0
INDE 20 57 43 FOBS=   0.0 SIGMA= 21.0 PHAS=   0.0 FOM= 0.00 TEST= 0
INDE 20 57 45 FOBS=  94.5 SIGMA=  2.8 PHAS= -28.2 FOM= 0.88 TEST= 0
INDE 20 57 47 FOBS=  66.6 SIGMA=  4.9 PHAS=-148.0 FOM= 0.85 TEST= 0
INDE 20 58 20 FOBS=  82.5 SIGMA=  3.0 PHAS= -65.0 FOM= 0.85 TEST= 0
INDE 20 58 22 FOBS=  85.1 SIGMA=  4.3 PHAS=-105.6 FOM= 0.72 TEST= 0
INDE 20 58 24 FOBS=  59.5 SIGMA=  4.2 PHAS=-114.6 FOM= 0.31 TEST= 1
INDE 20 58 26 FOBS= 125.9 SIGMA=  2.1 PHAS= -85.0 FOM= 0.91 TEST= 0
INDE 20 58 28 FOBS=  70.6 SIGMA=  3.7 PHAS= -72.9 FOM= 0.81 TEST= 0
INDE 20 58 30 FOBS=  22.0 SIGMA= 13.6 PHAS=  39.1 FOM= 0.09 TEST= 1
INDE 20 58 32 FOBS=  85.0 SIGMA=  3.2 PHAS=  46.5 FOM= 0.86 TEST= 0
INDE 20 58 34 FOBS=  57.7 SIGMA=  4.8 PHAS=   9.3 FOM= 0.80 TEST= 0
INDE 20 58 36 FOBS=   0.0 SIGMA= 23.8 PHAS=   0.0 FOM= 0.00 TEST= 0
INDE 20 58 38 FOBS=   0.0 SIGMA= 23.4 PHAS=   0.0 FOM= 0.00 TEST= 0
INDE 20 58 40 FOBS=  93.7 SIGMA=  2.5 PHAS= 154.4 FOM= 0.85 TEST= 0
INDE 20 58 42 FOBS=  83.1 SIGMA=  2.9 PHAS= -63.3 FOM= 0.22 TEST= 1
INDE 20 58 44 FOBS=  47.9 SIGMA=  4.5 PHAS= -87.7 FOM= 0.68 TEST= 0
INDE 20 58 46 FOBS=  24.5 SIGMA= 13.1 PHAS=  96.1 FOM= 0.37 TEST= 0
INDE 20 59 21 FOBS=  90.0 SIGMA=  3.0 PHAS= 154.0 FOM= 0.83 TEST= 0
```

*FIG. 12A - 449*

```
INDE 20 59 23 FOBS=    0.0 SIGMA= 26.7 PHAS=    0.0 FOM= 0.00 TEST= 0
INDE 20 59 25 FOBS=   56.9 SIGMA=  4.4 PHAS= -170.5 FOM= 0.75 TEST= 0
INDE 20 59 27 FOBS=  106.1 SIGMA=  2.5 PHAS=  165.9 FOM= 0.94 TEST= 0
INDE 20 59 29 FOBS=   45.9 SIGMA=  6.5 PHAS=  -53.9 FOM= 0.10 TEST= 0
INDE 20 59 31 FOBS=   67.2 SIGMA=  4.0 PHAS=   80.9 FOM= 0.77 TEST= 0
INDE 20 59 33 FOBS=   95.5 SIGMA=  2.9 PHAS= -108.3 FOM= 0.93 TEST= 0
INDE 20 59 35 FOBS=   55.9 SIGMA=  4.9 PHAS= -118.2 FOM= 0.75 TEST= 0
INDE 20 59 37 FOBS=   22.3 SIGMA= 14.8 PHAS=   -8.8 FOM= 0.43 TEST= 0
INDE 20 59 39 FOBS=   78.3 SIGMA=  3.0 PHAS=   63.6 FOM= 0.91 TEST= 0
INDE 20 59 41 FOBS=   95.0 SIGMA=  2.6 PHAS=  -42.2 FOM= 0.59 TEST= 0
INDE 20 59 43 FOBS=   43.9 SIGMA=  5.5 PHAS=  175.1 FOM= 0.84 TEST= 0
INDE 20 59 45 FOBS=    0.0 SIGMA= 25.0 PHAS=    0.0 FOM= 0.00 TEST= 0
INDE 20 60 20 FOBS=   63.5 SIGMA=  4.2 PHAS=   91.5 FOM= 0.59 TEST= 0
INDE 20 60 22 FOBS=    0.0 SIGMA= 23.0 PHAS=    0.0 FOM= 0.00 TEST= 0
INDE 20 60 24 FOBS=   65.1 SIGMA=  3.8 PHAS=  -31.7 FOM= 0.56 TEST= 0
INDE 20 60 26 FOBS=   83.4 SIGMA=  3.0 PHAS=   86.1 FOM= 0.88 TEST= 0
INDE 20 60 28 FOBS=   73.3 SIGMA=  3.5 PHAS=   28.6 FOM= 0.30 TEST= 1
INDE 20 60 30 FOBS=   33.1 SIGMA=  7.8 PHAS=  -72.0 FOM= 0.24 TEST= 0
INDE 20 60 32 FOBS=   80.1 SIGMA=  3.4 PHAS=   52.0 FOM= 0.89 TEST= 0
INDE 20 60 34 FOBS=   89.0 SIGMA=  3.2 PHAS=  126.3 FOM= 0.93 TEST= 0
INDE 20 60 36 FOBS=   35.0 SIGMA=  9.2 PHAS=  128.2 FOM= 0.18 TEST= 0
INDE 20 60 38 FOBS=   67.7 SIGMA=  3.5 PHAS=  -31.9 FOM= 0.88 TEST= 0
INDE 20 60 40 FOBS=   76.7 SIGMA=  3.1 PHAS=  113.9 FOM= 0.86 TEST= 0
INDE 20 60 42 FOBS=   97.0 SIGMA=  2.5 PHAS=  105.1 FOM= 0.94 TEST= 0
INDE 20 60 44 FOBS=   61.4 SIGMA=  4.4 PHAS=   88.3 FOM= 0.84 TEST= 0
INDE 20 61 21 FOBS=   32.2 SIGMA= 11.0 PHAS= -154.0 FOM= 0.47 TEST= 0
INDE 20 61 23 FOBS=   61.6 SIGMA=  5.8 PHAS= -108.1 FOM= 0.49 TEST= 0
INDE 20 61 25 FOBS=   86.4 SIGMA=  2.9 PHAS=  -79.1 FOM= 0.91 TEST= 0
INDE 20 61 27 FOBS=   81.7 SIGMA=  3.2 PHAS=   -2.4 FOM= 0.83 TEST= 0
INDE 20 61 29 FOBS=   43.7 SIGMA=  5.9 PHAS=   92.6 FOM= 0.50 TEST= 0
INDE 20 61 31 FOBS=    0.0 SIGMA= 22.8 PHAS=    0.0 FOM= 0.00 TEST= 0
INDE 20 61 33 FOBS=   96.5 SIGMA=  2.9 PHAS=  -65.4 FOM= 0.93 TEST= 0
INDE 20 61 35 FOBS=   30.7 SIGMA=  9.2 PHAS= -121.9 FOM= 0.13 TEST= 0
INDE 20 61 37 FOBS=   41.3 SIGMA=  7.7 PHAS=  -72.4 FOM= 0.11 TEST= 0
INDE 20 61 39 FOBS=   20.8 SIGMA= 13.7 PHAS=   -2.7 FOM= 0.38 TEST= 0
INDE 20 61 41 FOBS=  105.7 SIGMA=  2.6 PHAS=   21.7 FOM= 0.95 TEST= 0
INDE 20 61 43 FOBS=   41.4 SIGMA=  7.2 PHAS=    7.3 FOM= 0.73 TEST= 0
INDE 20 62 20 FOBS=   65.3 SIGMA=  4.1 PHAS= -142.8 FOM= 0.79 TEST= 0
INDE 20 62 22 FOBS=   87.0 SIGMA=  3.7 PHAS=  122.9 FOM= 0.69 TEST= 0
INDE 20 62 24 FOBS=   43.7 SIGMA=  8.2 PHAS=   95.4 FOM= 0.20 TEST= 0
INDE 20 62 26 FOBS=  104.7 SIGMA=  2.5 PHAS= -131.3 FOM= 0.91 TEST= 0
INDE 20 62 28 FOBS=   59.0 SIGMA=  4.4 PHAS=   31.3 FOM= 0.77 TEST= 0
INDE 20 62 30 FOBS=    0.0 SIGMA= 24.3 PHAS=    0.0 FOM= 0.00 TEST= 1
INDE 20 62 32 FOBS=   55.8 SIGMA=  4.9 PHAS=  -82.6 FOM= 0.72 TEST= 0
INDE 20 62 34 FOBS=  130.6 SIGMA=  2.3 PHAS=  -98.5 FOM= 0.88 TEST= 0
INDE 20 62 36 FOBS=   20.7 SIGMA= 20.5 PHAS=  138.5 FOM= 0.42 TEST= 0
INDE 20 62 38 FOBS=    0.0 SIGMA= 21.6 PHAS=    0.0 FOM= 0.00 TEST= 1
INDE 20 62 40 FOBS=   37.4 SIGMA=  9.5 PHAS=    6.7 FOM= 0.48 TEST= 0
INDE 20 62 42 FOBS=   39.1 SIGMA=  7.7 PHAS= -139.9 FOM= 0.56 TEST= 0
INDE 20 63 21 FOBS=   54.9 SIGMA=  4.9 PHAS=   -3.2 FOM= 0.54 TEST= 0
INDE 20 63 23 FOBS=   94.7 SIGMA=  2.9 PHAS=  -24.5 FOM= 0.85 TEST= 0
INDE 20 63 25 FOBS=   44.4 SIGMA=  8.1 PHAS= -145.1 FOM= 0.38 TEST= 0
INDE 20 63 27 FOBS=   85.6 SIGMA=  3.1 PHAS=  -99.4 FOM= 0.32 TEST= 1
INDE 20 63 29 FOBS=   49.1 SIGMA=  6.2 PHAS=   27.3 FOM= 0.34 TEST= 0
INDE 20 63 31 FOBS=   37.5 SIGMA=  8.3 PHAS= -172.8 FOM= 0.45 TEST= 0
INDE 20 63 33 FOBS=   71.4 SIGMA=  4.5 PHAS=   64.2 FOM= 0.73 TEST= 0
INDE 20 63 35 FOBS=   59.2 SIGMA=  5.5 PHAS=   29.3 FOM= 0.32 TEST= 0
INDE 20 63 37 FOBS=   54.7 SIGMA=  6.1 PHAS=   97.1 FOM= 0.86 TEST= 0
INDE 20 63 39 FOBS=   57.3 SIGMA=  6.0 PHAS=  155.3 FOM= 0.86 TEST= 0
INDE 20 64 20 FOBS=   76.6 SIGMA=  3.5 PHAS=  -63.4 FOM= 0.86 TEST= 0
INDE 20 64 22 FOBS=   91.8 SIGMA=  3.0 PHAS=  -92.7 FOM= 0.76 TEST= 0
INDE 20 64 24 FOBS=   18.5 SIGMA= 19.4 PHAS=  -43.8 FOM= 0.40 TEST= 0
INDE 20 64 26 FOBS=   79.6 SIGMA=  3.8 PHAS=  129.9 FOM= 0.92 TEST= 0
INDE 20 64 28 FOBS=   47.5 SIGMA=  6.3 PHAS=   69.8 FOM= 0.62 TEST= 0
INDE 20 64 30 FOBS=   46.0 SIGMA=  6.6 PHAS=  -12.5 FOM= 0.60 TEST= 0
INDE 20 64 32 FOBS=   49.2 SIGMA=  6.4 PHAS=   88.9 FOM= 0.69 TEST= 0
INDE 20 64 34 FOBS=   53.2 SIGMA=  6.1 PHAS=  -19.8 FOM= 0.58 TEST= 0
INDE 20 64 36 FOBS=   50.6 SIGMA=  7.8 PHAS=    8.6 FOM= 0.52 TEST= 0
INDE 20 64 38 FOBS=   75.1 SIGMA=  4.6 PHAS=   77.8 FOM= 0.81 TEST= 0
INDE 20 65 21 FOBS=   84.4 SIGMA=  3.2 PHAS=  178.0 FOM= 0.87 TEST= 0
```

*FIG. 12A - 450*

| | | | | | | | | | | | |
|---|---|---|---|---|---|---|---|---|---|---|---|
| INDE | 20 | 65 | 23 | FOBS= | 31.9 | SIGMA= | 9.8 | PHAS= | -112.2 | FOM= | 0.12 | TEST= | 0 |
| INDE | 20 | 65 | 25 | FOBS= | 70.2 | SIGMA= | 5.3 | PHAS= | -21.2 | FOM= | 0.92 | TEST= | 0 |
| INDE | 20 | 65 | 27 | FOBS= | 96.9 | SIGMA= | 3.2 | PHAS= | -29.0 | FOM= | 0.32 | TEST= | 1 |
| INDE | 20 | 65 | 29 | FOBS= | 77.8 | SIGMA= | 4.0 | PHAS= | -164.7 | FOM= | 0.85 | TEST= | 0 |
| INDE | 20 | 65 | 31 | FOBS= | 17.3 | SIGMA= | 21.8 | PHAS= | 143.6 | FOM= | 0.31 | TEST= | 0 |
| INDE | 20 | 65 | 33 | FOBS= | 42.0 | SIGMA= | 7.6 | PHAS= | 43.9 | FOM= | 0.21 | TEST= | 1 |
| INDE | 20 | 65 | 35 | FOBS= | 22.9 | SIGMA= | 14.4 | PHAS= | -106.1 | FOM= | 0.67 | TEST= | 0 |
| INDE | 20 | 65 | 37 | FOBS= | 35.3 | SIGMA= | 9.8 | PHAS= | 51.9 | FOM= | 0.44 | TEST= | 0 |
| INDE | 20 | 66 | 20 | FOBS= | 36.8 | SIGMA= | 8.5 | PHAS= | 114.2 | FOM= | 0.46 | TEST= | 0 |
| INDE | 20 | 66 | 22 | FOBS= | 27.6 | SIGMA= | 11.8 | PHAS= | -79.9 | FOM= | 0.23 | TEST= | 0 |
| INDE | 20 | 66 | 24 | FOBS= | 75.7 | SIGMA= | 3.6 | PHAS= | -124.9 | FOM= | 0.73 | TEST= | 0 |
| INDE | 20 | 66 | 26 | FOBS= | 27.1 | SIGMA= | 13.5 | PHAS= | -141.9 | FOM= | 0.18 | TEST= | 0 |
| INDE | 20 | 66 | 28 | FOBS= | 48.3 | SIGMA= | 6.3 | PHAS= | 90.2 | FOM= | 0.81 | TEST= | 0 |
| INDE | 20 | 66 | 30 | FOBS= | 61.3 | SIGMA= | 5.1 | PHAS= | 61.2 | FOM= | 0.88 | TEST= | 0 |
| INDE | 20 | 66 | 32 | FOBS= | 39.0 | SIGMA= | 8.1 | PHAS= | -113.5 | FOM= | 0.07 | TEST= | 0 |
| INDE | 20 | 66 | 34 | FOBS= | 23.6 | SIGMA= | 13.9 | PHAS= | -33.7 | FOM= | 0.23 | TEST= | 0 |
| INDE | 20 | 67 | 21 | FOBS= | 23.3 | SIGMA= | 17.0 | PHAS= | 92.3 | FOM= | 0.07 | TEST= | 0 |
| INDE | 20 | 67 | 23 | FOBS= | 0.0 | SIGMA= | 32.7 | PHAS= | 0.0 | FOM= | 0.00 | TEST= | 1 |
| INDE | 20 | 67 | 25 | FOBS= | 0.0 | SIGMA= | 32.9 | PHAS= | 0.0 | FOM= | 0.00 | TEST= | 0 |
| INDE | 20 | 67 | 27 | FOBS= | 57.8 | SIGMA= | 6.5 | PHAS= | -12.1 | FOM= | 0.52 | TEST= | 0 |
| INDE | 20 | 67 | 29 | FOBS= | 99.1 | SIGMA= | 3.2 | PHAS= | -11.6 | FOM= | 0.88 | TEST= | 0 |
| INDE | 20 | 67 | 31 | FOBS= | 0.0 | SIGMA= | 25.2 | PHAS= | 0.0 | FOM= | 0.00 | TEST= | 0 |
| INDE | 20 | 67 | 33 | FOBS= | 54.8 | SIGMA= | 6.1 | PHAS= | -146.3 | FOM= | 0.70 | TEST= | 0 |
| INDE | 20 | 68 | 20 | FOBS= | 26.2 | SIGMA= | 15.1 | PHAS= | 86.4 | FOM= | 0.36 | TEST= | 0 |
| INDE | 20 | 68 | 22 | FOBS= | 50.7 | SIGMA= | 8.2 | PHAS= | -119.3 | FOM= | 0.67 | TEST= | 0 |
| INDE | 20 | 68 | 24 | FOBS= | 61.7 | SIGMA= | 6.8 | PHAS= | 4.5 | FOM= | 0.62 | TEST= | 0 |
| INDE | 20 | 68 | 26 | FOBS= | 0.0 | SIGMA= | 32.8 | PHAS= | 0.0 | FOM= | 0.00 | TEST= | 0 |
| INDE | 20 | 68 | 28 | FOBS= | 0.0 | SIGMA= | 33.2 | PHAS= | 0.0 | FOM= | 0.00 | TEST= | 0 |
| INDE | 20 | 68 | 30 | FOBS= | 34.3 | SIGMA= | 11.5 | PHAS= | -81.7 | FOM= | 0.50 | TEST= | 0 |
| INDE | 20 | 69 | 21 | FOBS= | 31.7 | SIGMA= | 12.9 | PHAS= | 152.8 | FOM= | 0.73 | TEST= | 0 |
| INDE | 20 | 69 | 23 | FOBS= | 64.5 | SIGMA= | 6.7 | PHAS= | 10.7 | FOM= | 0.08 | TEST= | 0 |
| INDE | 20 | 69 | 25 | FOBS= | 78.8 | SIGMA= | 5.4 | PHAS= | -67.1 | FOM= | 0.73 | TEST= | 0 |
| INDE | 20 | 69 | 29 | FOBS= | 65.3 | SIGMA= | 8.2 | PHAS= | 66.9 | FOM= | 0.34 | TEST= | 0 |
| INDE | 20 | 70 | 20 | FOBS= | 116.5 | SIGMA= | 3.4 | PHAS= | 59.3 | FOM= | 0.92 | TEST= | 0 |
| INDE | 20 | 70 | 22 | FOBS= | 0.0 | SIGMA= | 28.5 | PHAS= | 0.0 | FOM= | 0.00 | TEST= | 0 |
| INDE | 20 | 70 | 24 | FOBS= | 77.2 | SIGMA= | 5.7 | PHAS= | -83.4 | FOM= | 0.87 | TEST= | 0 |
| INDE | 20 | 71 | 21 | FOBS= | 23.2 | SIGMA= | 17.5 | PHAS= | 2.3 | FOM= | 0.53 | TEST= | 0 |
| INDE | 20 | 71 | 23 | FOBS= | 47.5 | SIGMA= | 9.1 | PHAS= | 141.5 | FOM= | 0.72 | TEST= | 0 |
| INDE | 20 | 72 | 20 | FOBS= | 32.4 | SIGMA= | 11.6 | PHAS= | -36.2 | FOM= | 0.34 | TEST= | 0 |
| INDE | 21 | 22 | 21 | FOBS= | 88.4 | SIGMA= | 1.5 | PHAS= | -114.7 | FOM= | 0.95 | TEST= | 1 |
| INDE | 21 | 22 | 23 | FOBS= | 337.5 | SIGMA= | 0.6 | PHAS= | -11.8 | FOM= | 0.99 | TEST= | 0 |
| INDE | 21 | 22 | 25 | FOBS= | 237.0 | SIGMA= | 0.8 | PHAS= | 123.3 | FOM= | 0.92 | TEST= | 0 |
| INDE | 21 | 22 | 27 | FOBS= | 240.0 | SIGMA= | 0.7 | PHAS= | -100.9 | FOM= | 0.95 | TEST= | 0 |
| INDE | 21 | 22 | 29 | FOBS= | 207.7 | SIGMA= | 0.8 | PHAS= | 5.4 | FOM= | 0.90 | TEST= | 0 |
| INDE | 21 | 22 | 31 | FOBS= | 133.5 | SIGMA= | 1.2 | PHAS= | 71.4 | FOM= | 0.91 | TEST= | 0 |
| INDE | 21 | 22 | 33 | FOBS= | 24.3 | SIGMA= | 7.1 | PHAS= | 136.0 | FOM= | 0.04 | TEST= | 1 |
| INDE | 21 | 22 | 35 | FOBS= | 96.7 | SIGMA= | 2.0 | PHAS= | 49.3 | FOM= | 0.35 | TEST= | 0 |
| INDE | 21 | 22 | 37 | FOBS= | 180.5 | SIGMA= | 1.1 | PHAS= | 177.6 | FOM= | 0.91 | TEST= | 0 |
| INDE | 21 | 22 | 39 | FOBS= | 111.2 | SIGMA= | 1.7 | PHAS= | 14.4 | FOM= | 0.91 | TEST= | 0 |
| INDE | 21 | 22 | 41 | FOBS= | 221.1 | SIGMA= | 0.8 | PHAS= | -48.6 | FOM= | 0.88 | TEST= | 0 |
| INDE | 21 | 22 | 43 | FOBS= | 77.0 | SIGMA= | 2.0 | PHAS= | -44.0 | FOM= | 0.29 | TEST= | 0 |
| INDE | 21 | 22 | 45 | FOBS= | 84.6 | SIGMA= | 1.9 | PHAS= | -155.1 | FOM= | 0.96 | TEST= | 0 |
| INDE | 21 | 22 | 47 | FOBS= | 95.4 | SIGMA= | 1.7 | PHAS= | -59.8 | FOM= | 0.93 | TEST= | 0 |
| INDE | 21 | 22 | 49 | FOBS= | 110.0 | SIGMA= | 1.5 | PHAS= | 36.1 | FOM= | 0.82 | TEST= | 0 |
| INDE | 21 | 22 | 51 | FOBS= | 60.5 | SIGMA= | 2.8 | PHAS= | 58.4 | FOM= | 0.75 | TEST= | 0 |
| INDE | 21 | 22 | 53 | FOBS= | 124.7 | SIGMA= | 1.7 | PHAS= | 72.7 | FOM= | 0.90 | TEST= | 0 |
| INDE | 21 | 22 | 55 | FOBS= | 13.6 | SIGMA= | 14.7 | PHAS= | 3.1 | FOM= | 0.13 | TEST= | 0 |
| INDE | 21 | 22 | 57 | FOBS= | 48.7 | SIGMA= | 5.1 | PHAS= | 172.3 | FOM= | 0.72 | TEST= | 0 |
| INDE | 21 | 22 | 59 | FOBS= | 106.8 | SIGMA= | 2.7 | PHAS= | 117.2 | FOM= | 0.93 | TEST= | 0 |
| INDE | 21 | 22 | 61 | FOBS= | 95.3 | SIGMA= | 2.9 | PHAS= | 88.6 | FOM= | 0.90 | TEST= | 0 |
| INDE | 21 | 22 | 63 | FOBS= | 50.1 | SIGMA= | 5.5 | PHAS= | 76.3 | FOM= | 0.72 | TEST= | 0 |
| INDE | 21 | 22 | 65 | FOBS= | 44.0 | SIGMA= | 6.3 | PHAS= | 93.7 | FOM= | 0.81 | TEST= | 0 |
| INDE | 21 | 22 | 67 | FOBS= | 88.6 | SIGMA= | 4.7 | PHAS= | 124.3 | FOM= | 0.83 | TEST= | 0 |
| INDE | 21 | 22 | 69 | FOBS= | 90.0 | SIGMA= | 4.7 | PHAS= | 160.7 | FOM= | 0.90 | TEST= | 0 |
| INDE | 21 | 22 | 71 | FOBS= | 70.1 | SIGMA= | 5.9 | PHAS= | -21.1 | FOM= | 0.78 | TEST= | 0 |
| INDE | 21 | 23 | 22 | FOBS= | 233.5 | SIGMA= | 0.7 | PHAS= | -119.8 | FOM= | 0.98 | TEST= | 0 |
| INDE | 21 | 23 | 24 | FOBS= | 141.6 | SIGMA= | 0.9 | PHAS= | -16.8 | FOM= | 0.94 | TEST= | 0 |
| INDE | 21 | 23 | 26 | FOBS= | 316.2 | SIGMA= | 0.6 | PHAS= | 20.0 | FOM= | 0.94 | TEST= | 0 |
| INDE | 21 | 23 | 28 | FOBS= | 261.2 | SIGMA= | 0.6 | PHAS= | -45.1 | FOM= | 0.94 | TEST= | 0 |
| INDE | 21 | 23 | 30 | FOBS= | 323.0 | SIGMA= | 0.6 | PHAS= | -36.5 | FOM= | 0.97 | TEST= | 0 |

*FIG. 12A - 451*

```
INDE 21 23 32 FOBS=   133.1 SIGMA=  1.1 PHAS=   67.9 FOM= 0.93 TEST= 0
INDE 21 23 34 FOBS=   138.0 SIGMA=  1.2 PHAS= -107.9 FOM= 0.87 TEST= 0
INDE 21 23 36 FOBS=   288.0 SIGMA=  0.7 PHAS=    8.5 FOM= 0.95 TEST= 0
INDE 21 23 38 FOBS=   110.1 SIGMA=  1.7 PHAS=   99.1 FOM= 0.91 TEST= 0
INDE 21 23 40 FOBS=    64.7 SIGMA=  2.7 PHAS= -119.8 FOM= 0.87 TEST= 1
INDE 21 23 42 FOBS=   192.2 SIGMA=  0.9 PHAS=  -87.1 FOM= 0.92 TEST= 0
INDE 21 23 44 FOBS=   180.9 SIGMA=  0.9 PHAS=  166.7 FOM= 0.96 TEST= 0
INDE 21 23 46 FOBS=   127.8 SIGMA=  1.3 PHAS=   78.1 FOM= 0.36 TEST= 1
INDE 21 23 48 FOBS=     0.0 SIGMA= 18.8 PHAS=    0.0 FOM= 0.00 TEST= 1
INDE 21 23 50 FOBS=    90.8 SIGMA=  1.8 PHAS=   36.7 FOM= 0.88 TEST= 0
INDE 21 23 52 FOBS=    80.9 SIGMA=  2.4 PHAS=  -44.0 FOM= 0.93 TEST= 0
INDE 21 23 54 FOBS=    83.5 SIGMA=  2.5 PHAS=  -43.0 FOM= 0.91 TEST= 0
INDE 21 23 56 FOBS=    35.4 SIGMA=  6.5 PHAS= -174.6 FOM= 0.67 TEST= 0
INDE 21 23 58 FOBS=    48.4 SIGMA=  7.8 PHAS= -144.8 FOM= 0.03 TEST= 1
INDE 21 23 60 FOBS=   101.8 SIGMA=  2.8 PHAS=   16.8 FOM= 0.94 TEST= 0
INDE 21 23 62 FOBS=    27.1 SIGMA= 10.3 PHAS=  -78.7 FOM= 0.17 TEST= 0
INDE 21 23 64 FOBS=    32.8 SIGMA=  9.8 PHAS= -116.5 FOM= 0.51 TEST= 0
INDE 21 23 66 FOBS=    67.0 SIGMA=  6.2 PHAS=  -19.1 FOM= 0.91 TEST= 0
INDE 21 23 68 FOBS=    95.1 SIGMA=  4.4 PHAS=  -38.5 FOM= 0.93 TEST= 0
INDE 21 23 70 FOBS=    33.2 SIGMA= 12.4 PHAS=  171.4 FOM= 0.73 TEST= 0
INDE 21 24 21 FOBS=   169.5 SIGMA=  0.8 PHAS=  -35.4 FOM= 0.95 TEST= 0
INDE 21 24 23 FOBS=   122.9 SIGMA=  1.0 PHAS=  146.4 FOM= 0.98 TEST= 0
INDE 21 24 25 FOBS=    97.9 SIGMA=  1.2 PHAS=  125.4 FOM= 0.77 TEST= 0
INDE 21 24 27 FOBS=   391.6 SIGMA=  0.6 PHAS=  -97.4 FOM= 0.97 TEST= 0
INDE 21 24 29 FOBS=   254.7 SIGMA=  0.6 PHAS= -154.0 FOM= 0.95 TEST= 0
INDE 21 24 31 FOBS=   370.4 SIGMA=  0.7 PHAS= -138.7 FOM= 0.97 TEST= 0
INDE 21 24 33 FOBS=    92.6 SIGMA=  1.5 PHAS=  -55.3 FOM= 0.98 TEST= 0
INDE 21 24 35 FOBS=   236.8 SIGMA=  0.7 PHAS=  -47.3 FOM= 0.95 TEST= 0
INDE 21 24 37 FOBS=   205.9 SIGMA=  1.0 PHAS= -115.0 FOM= 0.81 TEST= 1
INDE 21 24 39 FOBS=   126.9 SIGMA=  1.5 PHAS=  101.8 FOM= 0.93 TEST= 0
INDE 21 24 41 FOBS=    55.5 SIGMA=  3.2 PHAS=  173.0 FOM= 0.63 TEST= 0
INDE 21 24 43 FOBS=    32.2 SIGMA=  5.3 PHAS=   52.7 FOM= 0.62 TEST= 0
INDE 21 24 45 FOBS=   119.6 SIGMA=  1.4 PHAS=  -79.1 FOM= 0.85 TEST= 0
INDE 21 24 47 FOBS=    81.6 SIGMA=  2.0 PHAS= -100.8 FOM= 0.89 TEST= 0
INDE 21 24 49 FOBS=   114.0 SIGMA=  1.5 PHAS= -102.6 FOM= 0.95 TEST= 0
INDE 21 24 51 FOBS=   104.3 SIGMA=  1.9 PHAS= -115.5 FOM= 0.90 TEST= 0
INDE 21 24 53 FOBS=    12.5 SIGMA= 19.2 PHAS= -171.0 FOM= 0.06 TEST= 0
INDE 21 24 55 FOBS=   111.2 SIGMA=  2.0 PHAS=  144.2 FOM= 0.88 TEST= 0
INDE 21 24 57 FOBS=     8.3 SIGMA= 34.3 PHAS=   71.1 FOM= 0.06 TEST= 0
INDE 21 24 59 FOBS=    69.7 SIGMA=  4.2 PHAS=  174.4 FOM= 0.77 TEST= 0
INDE 21 24 61 FOBS=    40.3 SIGMA=  7.0 PHAS=   78.8 FOM= 0.31 TEST= 0
INDE 21 24 63 FOBS=    52.4 SIGMA=  5.4 PHAS=   78.2 FOM= 0.71 TEST= 0
INDE 21 24 65 FOBS=   132.8 SIGMA=  2.7 PHAS= -162.9 FOM= 0.97 TEST= 0
INDE 21 24 67 FOBS=    33.4 SIGMA= 12.5 PHAS=   -9.7 FOM= 0.16 TEST= 0
INDE 21 24 69 FOBS=    76.4 SIGMA=  5.1 PHAS=  164.8 FOM= 0.90 TEST= 0
INDE 21 25 22 FOBS=   222.2 SIGMA=  0.7 PHAS=   72.7 FOM= 0.98 TEST= 0
INDE 21 25 24 FOBS=   344.0 SIGMA=  0.6 PHAS=   22.8 FOM= 0.96 TEST= 0
INDE 21 25 26 FOBS=   272.8 SIGMA=  0.6 PHAS=  156.5 FOM= 0.98 TEST= 0
INDE 21 25 28 FOBS=    50.6 SIGMA=  2.6 PHAS=  -41.5 FOM= 0.92 TEST= 0
INDE 21 25 30 FOBS=   101.2 SIGMA=  1.4 PHAS=  106.6 FOM= 0.98 TEST= 0
INDE 21 25 32 FOBS=   251.9 SIGMA=  0.7 PHAS=  148.1 FOM= 0.96 TEST= 0
INDE 21 25 34 FOBS=    54.4 SIGMA=  2.9 PHAS=  -61.8 FOM= 0.84 TEST= 0
INDE 21 25 36 FOBS=   234.3 SIGMA=  0.8 PHAS= -164.7 FOM= 0.93 TEST= 0
INDE 21 25 38 FOBS=    95.9 SIGMA=  1.7 PHAS=  -28.6 FOM= 0.58 TEST= 1
INDE 21 25 40 FOBS=   246.7 SIGMA=  0.7 PHAS=   74.5 FOM= 0.97 TEST= 0
INDE 21 25 42 FOBS=    80.4 SIGMA=  2.0 PHAS=  -75.4 FOM= 0.76 TEST= 0
INDE 21 25 44 FOBS=   181.2 SIGMA=  1.0 PHAS= -145.2 FOM= 0.95 TEST= 0
INDE 21 25 46 FOBS=   274.1 SIGMA=  0.8 PHAS=  152.5 FOM= 0.97 TEST= 0
INDE 21 25 48 FOBS=   128.6 SIGMA=  1.3 PHAS= -178.5 FOM= 0.93 TEST= 0
INDE 21 25 50 FOBS=   136.7 SIGMA=  1.3 PHAS=  109.5 FOM= 0.95 TEST= 0
INDE 21 25 52 FOBS=   105.1 SIGMA=  1.9 PHAS=  156.8 FOM= 0.84 TEST= 0
INDE 21 25 54 FOBS=    87.6 SIGMA=  2.2 PHAS=  163.8 FOM= 0.80 TEST= 0
INDE 21 25 56 FOBS=    26.2 SIGMA=  8.7 PHAS=   64.4 FOM= 0.08 TEST= 0
INDE 21 25 58 FOBS=     0.0 SIGMA= 23.9 PHAS=    0.0 FOM= 0.00 TEST= 0
INDE 21 25 60 FOBS=    33.7 SIGMA= 11.3 PHAS=  -43.4 FOM= 0.31 TEST= 0
INDE 21 25 62 FOBS=    36.2 SIGMA=  7.9 PHAS=  -32.3 FOM= 0.50 TEST= 0
INDE 21 25 64 FOBS=   104.0 SIGMA=  3.4 PHAS=  102.4 FOM= 0.93 TEST= 0
INDE 21 25 66 FOBS=    68.8 SIGMA=  5.9 PHAS=   52.9 FOM= 0.55 TEST= 0
INDE 21 25 68 FOBS=    54.5 SIGMA=  7.3 PHAS=   43.8 FOM= 0.03 TEST= 1
INDE 21 25 70 FOBS=    64.4 SIGMA=  6.2 PHAS=   61.3 FOM= 0.75 TEST= 0
```

*FIG. 12A - 452*

```
INDE  21  26  21  FOBS=    390.3  SIGMA=   0.6  PHAS=   -25.8  FOM=  0.98  TEST= 0
INDE  21  26  23  FOBS=    187.8  SIGMA=   0.8  PHAS=   -87.6  FOM=  0.97  TEST= 0
INDE  21  26  25  FOBS=     62.3  SIGMA=   2.2  PHAS=   -44.9  FOM=  0.24  TEST= 0
INDE  21  26  27  FOBS=    240.9  SIGMA=   0.6  PHAS=    42.1  FOM=  0.99  TEST= 0
INDE  21  26  29  FOBS=    280.1  SIGMA=   0.6  PHAS=  -112.1  FOM=  0.95  TEST= 0
INDE  21  26  31  FOBS=    104.8  SIGMA=   1.4  PHAS=   166.8  FOM=  0.98  TEST= 0
INDE  21  26  33  FOBS=     75.6  SIGMA=   1.9  PHAS=  -169.3  FOM=  0.92  TEST= 0
INDE  21  26  35  FOBS=    143.6  SIGMA=   1.2  PHAS=    39.2  FOM=  0.85  TEST= 0
INDE  21  26  37  FOBS=    107.8  SIGMA=   1.6  PHAS=   160.7  FOM=  0.93  TEST= 0
INDE  21  26  39  FOBS=    134.3  SIGMA=   1.3  PHAS=   -51.2  FOM=  0.84  TEST= 0
INDE  21  26  41  FOBS=    140.7  SIGMA=   1.2  PHAS=   -20.6  FOM=  0.91  TEST= 0
INDE  21  26  43  FOBS=    246.4  SIGMA=   0.8  PHAS=   141.8  FOM=  0.97  TEST= 0
INDE  21  26  45  FOBS=     70.7  SIGMA=   2.2  PHAS=    62.2  FOM=  0.73  TEST= 0
INDE  21  26  47  FOBS=    107.6  SIGMA=   1.5  PHAS=    58.6  FOM=  0.92  TEST= 0
INDE  21  26  49  FOBS=      0.0  SIGMA=  18.6  PHAS=     0.0  FOM=  0.00  TEST= 1
INDE  21  26  51  FOBS=     81.0  SIGMA=   2.3  PHAS=    -2.8  FOM=  0.90  TEST= 0
INDE  21  26  53  FOBS=    117.3  SIGMA=   1.7  PHAS=    44.6  FOM=  0.86  TEST= 0
INDE  21  26  55  FOBS=     46.8  SIGMA=   4.2  PHAS=    16.4  FOM=  0.74  TEST= 0
INDE  21  26  57  FOBS=     52.9  SIGMA=   4.4  PHAS=   163.6  FOM=  0.74  TEST= 0
INDE  21  26  59  FOBS=     12.0  SIGMA=  24.0  PHAS=   110.6  FOM=  0.25  TEST= 0
INDE  21  26  61  FOBS=     93.5  SIGMA=   3.1  PHAS=   168.5  FOM=  0.79  TEST= 0
INDE  21  26  63  FOBS=      9.5  SIGMA=  30.1  PHAS=   -10.3  FOM=  0.13  TEST= 0
INDE  21  26  65  FOBS=     15.5  SIGMA=  25.9  PHAS=   141.7  FOM=  0.14  TEST= 1
INDE  21  26  67  FOBS=      0.0  SIGMA=  28.2  PHAS=     0.0  FOM=  0.00  TEST= 0
INDE  21  26  69  FOBS=      0.0  SIGMA=  28.5  PHAS=     0.0  FOM=  0.00  TEST= 0
INDE  21  27  22  FOBS=     95.4  SIGMA=   1.4  PHAS=    94.8  FOM=  0.74  TEST= 0
INDE  21  27  24  FOBS=     59.5  SIGMA=   2.3  PHAS=   145.6  FOM=  0.88  TEST= 0
INDE  21  27  26  FOBS=    192.1  SIGMA=   0.8  PHAS=   -41.7  FOM=  0.92  TEST= 0
INDE  21  27  28  FOBS=     99.8  SIGMA=   1.4  PHAS=   -20.7  FOM=  0.87  TEST= 0
INDE  21  27  30  FOBS=    198.5  SIGMA=   0.8  PHAS=  -160.0  FOM=  0.93  TEST= 0
INDE  21  27  32  FOBS=    207.6  SIGMA=   0.8  PHAS=    84.1  FOM=  0.95  TEST= 0
INDE  21  27  34  FOBS=    154.4  SIGMA=   1.1  PHAS=    41.8  FOM=  0.65  TEST= 1
INDE  21  27  36  FOBS=      0.0  SIGMA=  18.4  PHAS=     0.0  FOM=  0.00  TEST= 0
INDE  21  27  38  FOBS=     46.8  SIGMA=   3.4  PHAS=   -77.8  FOM=  0.49  TEST= 0
INDE  21  27  40  FOBS=    116.2  SIGMA=   1.4  PHAS=   136.6  FOM=  0.82  TEST= 0
INDE  21  27  42  FOBS=     65.6  SIGMA=   2.4  PHAS=    75.3  FOM=  0.52  TEST= 0
INDE  21  27  44  FOBS=     41.5  SIGMA=   4.0  PHAS=   123.3  FOM=  0.33  TEST= 0
INDE  21  27  46  FOBS=     33.1  SIGMA=   5.1  PHAS=    37.5  FOM=  0.74  TEST= 0
INDE  21  27  48  FOBS=      6.1  SIGMA=  28.3  PHAS=  -122.7  FOM=  0.14  TEST= 0
INDE  21  27  50  FOBS=      0.0  SIGMA=  19.5  PHAS=     0.0  FOM=  0.00  TEST= 0
INDE  21  27  52  FOBS=      0.0  SIGMA=  16.8  PHAS=     0.0  FOM=  0.00  TEST= 0
INDE  21  27  54  FOBS=     68.4  SIGMA=   2.5  PHAS=  -116.2  FOM=  0.86  TEST= 0
INDE  21  27  56  FOBS=     52.9  SIGMA=   4.4  PHAS=   -83.9  FOM=  0.48  TEST= 0
INDE  21  27  58  FOBS=     59.9  SIGMA=   3.9  PHAS=    36.0  FOM=  0.90  TEST= 0
INDE  21  27  60  FOBS=     55.4  SIGMA=   5.2  PHAS=  -122.5  FOM=  0.15  TEST= 0
INDE  21  27  62  FOBS=     44.7  SIGMA=   6.4  PHAS=    89.3  FOM=  0.00  TEST= 1
INDE  21  27  64  FOBS=     27.2  SIGMA=  12.5  PHAS=    76.5  FOM=  0.53  TEST= 0
INDE  21  27  66  FOBS=      0.0  SIGMA=  28.6  PHAS=     0.0  FOM=  0.00  TEST= 0
INDE  21  27  68  FOBS=      0.0  SIGMA=  29.0  PHAS=     0.0  FOM=  0.00  TEST= 0
INDE  21  28  21  FOBS=    207.1  SIGMA=   0.7  PHAS=   -43.8  FOM=  0.94  TEST= 0
INDE  21  28  23  FOBS=    140.2  SIGMA=   1.0  PHAS=    76.9  FOM=  0.95  TEST= 0
INDE  21  28  25  FOBS=    259.1  SIGMA=   0.7  PHAS=   -73.4  FOM=  0.95  TEST= 0
INDE  21  28  27  FOBS=     78.4  SIGMA=   1.9  PHAS=   -42.4  FOM=  0.89  TEST= 0
INDE  21  28  29  FOBS=    131.3  SIGMA=   1.2  PHAS=   -95.8  FOM=  0.12  TEST= 1
INDE  21  28  31  FOBS=    105.9  SIGMA=   1.5  PHAS=     9.3  FOM=  0.86  TEST= 1
INDE  21  28  33  FOBS=    130.8  SIGMA=   1.3  PHAS=    68.7  FOM=  0.29  TEST= 1
INDE  21  28  35  FOBS=     58.9  SIGMA=   2.9  PHAS=    61.3  FOM=  0.91  TEST= 0
INDE  21  28  37  FOBS=    186.2  SIGMA=   0.9  PHAS=   175.9  FOM=  0.93  TEST= 0
INDE  21  28  39  FOBS=    131.0  SIGMA=   1.3  PHAS=    -7.3  FOM=  0.95  TEST= 0
INDE  21  28  41  FOBS=    200.7  SIGMA=   0.9  PHAS=    13.4  FOM=  0.92  TEST= 0
INDE  21  28  43  FOBS=    225.9  SIGMA=   0.8  PHAS=   127.4  FOM=  0.95  TEST= 0
INDE  21  28  45  FOBS=     78.1  SIGMA=   2.0  PHAS=  -164.6  FOM=  0.95  TEST= 0
INDE  21  28  47  FOBS=     85.9  SIGMA=   2.1  PHAS=    50.7  FOM=  0.50  TEST= 1
INDE  21  28  49  FOBS=     25.7  SIGMA=   7.1  PHAS=    20.7  FOM=  0.24  TEST= 0
INDE  21  28  51  FOBS=    100.2  SIGMA=   1.8  PHAS=    -6.4  FOM=  0.87  TEST= 0
INDE  21  28  53  FOBS=      0.0  SIGMA=  18.3  PHAS=     0.0  FOM=  0.00  TEST= 0
INDE  21  28  55  FOBS=     66.8  SIGMA=   3.0  PHAS=   165.4  FOM=  0.64  TEST= 0
INDE  21  28  57  FOBS=     98.7  SIGMA=   2.4  PHAS=  -112.2  FOM=  0.80  TEST= 0
INDE  21  28  59  FOBS=     33.9  SIGMA=   6.7  PHAS=    -3.3  FOM=  0.18  TEST= 0
INDE  21  28  61  FOBS=     45.2  SIGMA=   6.3  PHAS=  -141.0  FOM=  0.49  TEST= 0
```

*FIG. 12A - 453*

```
INDE 21 28 63 FOBS=    52.0 SIGMA=  6.6 PHAS=  149.4 FOM= 0.48 TEST= 0
INDE 21 28 65 FOBS=    96.7 SIGMA=  4.4 PHAS=   17.6 FOM= 0.91 TEST= 0
INDE 21 28 67 FOBS=     0.0 SIGMA= 29.1 PHAS=    0.0 FOM= 0.00 TEST= 0
INDE 21 28 69 FOBS=     0.0 SIGMA= 28.7 PHAS=    0.0 FOM= 0.00 TEST= 0
INDE 21 29 22 FOBS=   125.3 SIGMA=  1.1 PHAS=   36.1 FOM= 0.88 TEST= 1
INDE 21 29 24 FOBS=   178.6 SIGMA=  0.9 PHAS= -139.9 FOM= 0.97 TEST= 0
INDE 21 29 26 FOBS=   139.6 SIGMA=  1.1 PHAS= -110.7 FOM= 0.93 TEST= 0
INDE 21 29 28 FOBS=   150.1 SIGMA=  1.0 PHAS= -171.6 FOM= 0.77 TEST= 0
INDE 21 29 30 FOBS=   202.7 SIGMA=  0.9 PHAS= -112.3 FOM= 0.94 TEST= 0
INDE 21 29 32 FOBS=   213.1 SIGMA=  0.9 PHAS=    2.0 FOM= 0.96 TEST= 0
INDE 21 29 34 FOBS=   143.1 SIGMA=  1.2 PHAS=  142.5 FOM= 0.95 TEST= 0
INDE 21 29 36 FOBS=   145.3 SIGMA=  1.2 PHAS=   88.3 FOM= 0.84 TEST= 0
INDE 21 29 38 FOBS=    40.3 SIGMA=  4.1 PHAS= -130.0 FOM= 0.54 TEST= 0
INDE 21 29 40 FOBS=   292.9 SIGMA=  0.7 PHAS=  -86.3 FOM= 0.97 TEST= 0
INDE 21 29 42 FOBS=   108.8 SIGMA=  1.5 PHAS=   92.1 FOM= 0.75 TEST= 0
INDE 21 29 44 FOBS=   115.5 SIGMA=  1.4 PHAS=  101.6 FOM= 0.89 TEST= 0
INDE 21 29 46 FOBS=   177.8 SIGMA=  1.1 PHAS=    3.6 FOM= 0.97 TEST= 0
INDE 21 29 48 FOBS=    82.8 SIGMA=  2.2 PHAS=  -71.7 FOM= 0.51 TEST= 0
INDE 21 29 50 FOBS=    94.5 SIGMA=  2.0 PHAS=  -99.0 FOM= 0.89 TEST= 0
INDE 21 29 52 FOBS=    51.5 SIGMA=  3.5 PHAS=   57.3 FOM= 0.79 TEST= 0
INDE 21 29 54 FOBS=    27.4 SIGMA=  7.1 PHAS= -150.6 FOM= 0.48 TEST= 0
INDE 21 29 56 FOBS=    33.0 SIGMA=  5.8 PHAS=  144.5 FOM= 0.60 TEST= 0
INDE 21 29 58 FOBS=    94.5 SIGMA=  2.1 PHAS=   91.0 FOM= 0.91 TEST= 0
INDE 21 29 60 FOBS=    67.8 SIGMA=  3.4 PHAS= -144.4 FOM= 0.69 TEST= 0
INDE 21 29 62 FOBS=     0.0 SIGMA= 26.0 PHAS=    0.0 FOM= 0.00 TEST= 0
INDE 21 29 64 FOBS=    47.7 SIGMA=  8.9 PHAS=   26.9 FOM= 0.69 TEST= 0
INDE 21 29 66 FOBS=     0.0 SIGMA= 28.8 PHAS=    0.0 FOM= 0.00 TEST= 0
INDE 21 29 68 FOBS=     0.0 SIGMA= 28.9 PHAS=    0.0 FOM= 0.00 TEST= 0
INDE 21 30 21 FOBS=   138.1 SIGMA=  1.1 PHAS=   70.8 FOM= 0.95 TEST= 0
INDE 21 30 23 FOBS=   190.9 SIGMA=  0.8 PHAS=  157.9 FOM= 0.94 TEST= 0
INDE 21 30 25 FOBS=   178.1 SIGMA=  0.9 PHAS= -103.7 FOM= 0.97 TEST= 0
INDE 21 30 27 FOBS=   251.8 SIGMA=  0.8 PHAS=  112.0 FOM= 0.88 TEST= 1
INDE 21 30 29 FOBS=    79.3 SIGMA=  2.0 PHAS=   93.5 FOM= 0.89 TEST= 0
INDE 21 30 31 FOBS=   138.1 SIGMA=  1.3 PHAS=  -68.8 FOM= 0.47 TEST= 0
INDE 21 30 33 FOBS=   229.1 SIGMA=  0.8 PHAS=   43.3 FOM= 0.96 TEST= 0
INDE 21 30 35 FOBS=    56.3 SIGMA=  2.9 PHAS=  104.3 FOM= 0.58 TEST= 0
INDE 21 30 37 FOBS=    56.1 SIGMA=  3.2 PHAS=  -25.7 FOM= 0.35 TEST= 0
INDE 21 30 39 FOBS=   216.9 SIGMA=  0.9 PHAS= -159.4 FOM= 0.95 TEST= 0
INDE 21 30 41 FOBS=    24.9 SIGMA=  6.3 PHAS=  113.1 FOM= 0.25 TEST= 0
INDE 21 30 43 FOBS=   118.9 SIGMA=  1.3 PHAS=  141.0 FOM= 0.69 TEST= 0
INDE 21 30 45 FOBS=   118.2 SIGMA=  1.5 PHAS= -114.2 FOM= 0.93 TEST= 0
INDE 21 30 47 FOBS=   104.3 SIGMA=  1.7 PHAS=  -68.9 FOM= 0.70 TEST= 0
INDE 21 30 49 FOBS=   102.6 SIGMA=  1.7 PHAS=   82.7 FOM= 0.85 TEST= 0
INDE 21 30 51 FOBS=    11.3 SIGMA= 16.5 PHAS=   59.8 FOM= 0.18 TEST= 0
INDE 21 30 53 FOBS=    80.2 SIGMA=  2.3 PHAS=  -28.0 FOM= 0.82 TEST= 0
INDE 21 30 55 FOBS=   117.9 SIGMA=  1.7 PHAS=   74.8 FOM= 0.92 TEST= 0
INDE 21 30 57 FOBS=    80.2 SIGMA=  2.4 PHAS=  -61.9 FOM= 0.93 TEST= 0
INDE 21 30 59 FOBS=    50.5 SIGMA=  3.8 PHAS=   26.7 FOM= 0.56 TEST= 0
INDE 21 30 61 FOBS=    71.5 SIGMA=  2.8 PHAS=  176.2 FOM= 0.83 TEST= 0
INDE 21 30 63 FOBS=    21.0 SIGMA= 16.2 PHAS=  -67.6 FOM= 0.50 TEST= 0
INDE 21 30 65 FOBS=    39.7 SIGMA= 10.5 PHAS=   53.1 FOM= 0.70 TEST= 0
INDE 21 30 67 FOBS=    72.6 SIGMA=  5.8 PHAS= -109.1 FOM= 0.87 TEST= 0
INDE 21 31 22 FOBS=    53.6 SIGMA=  2.7 PHAS=   29.4 FOM= 0.52 TEST= 0
INDE 21 31 24 FOBS=   146.0 SIGMA=  1.1 PHAS=  150.7 FOM= 0.93 TEST= 0
INDE 21 31 26 FOBS=   137.1 SIGMA=  1.3 PHAS=  -54.5 FOM= 0.96 TEST= 1
INDE 21 31 28 FOBS=   153.1 SIGMA=  1.2 PHAS=   16.3 FOM= 0.91 TEST= 0
INDE 21 31 30 FOBS=    73.8 SIGMA=  2.4 PHAS=   72.3 FOM= 0.78 TEST= 0
INDE 21 31 32 FOBS=   216.6 SIGMA=  0.9 PHAS=  -29.6 FOM= 0.96 TEST= 0
INDE 21 31 34 FOBS=   106.8 SIGMA=  1.6 PHAS= -129.1 FOM= 0.43 TEST= 1
INDE 21 31 36 FOBS=   134.2 SIGMA=  1.3 PHAS=  173.7 FOM= 0.87 TEST= 0
INDE 21 31 38 FOBS=   243.6 SIGMA=  0.8 PHAS=  119.4 FOM= 0.96 TEST= 0
INDE 21 31 40 FOBS=    52.4 SIGMA=  3.3 PHAS= -114.1 FOM= 0.81 TEST= 0
INDE 21 31 42 FOBS=   112.4 SIGMA=  1.6 PHAS=   78.1 FOM= 0.87 TEST= 0
INDE 21 31 44 FOBS=    52.8 SIGMA=  3.2 PHAS=  153.8 FOM= 0.64 TEST= 0
INDE 21 31 46 FOBS=    51.4 SIGMA=  3.3 PHAS=  156.6 FOM= 0.84 TEST= 0
INDE 21 31 48 FOBS=    46.6 SIGMA=  4.0 PHAS= -121.1 FOM= 0.76 TEST= 0
INDE 21 31 50 FOBS=    34.6 SIGMA=  5.3 PHAS=   -6.7 FOM= 0.54 TEST= 0
INDE 21 31 52 FOBS=    24.3 SIGMA=  7.7 PHAS=  110.4 FOM= 0.32 TEST= 0
INDE 21 31 54 FOBS=    64.3 SIGMA=  3.3 PHAS=  -69.5 FOM= 0.72 TEST= 0
INDE 21 31 56 FOBS=   111.2 SIGMA=  1.8 PHAS=  170.2 FOM= 0.89 TEST= 0
```

*FIG. 12A - 454*

```
INDE 21 31 58 FOBS=    0.0 SIGMA= 20.3 PHAS=    0.0 FOM= 0.00 TEST= 0
INDE 21 31 60 FOBS=   22.3 SIGMA= 11.6 PHAS=  -51.8 FOM= 0.13 TEST= 0
INDE 21 31 62 FOBS=   13.3 SIGMA= 19.2 PHAS= -135.0 FOM= 0.31 TEST= 0
INDE 21 31 64 FOBS=   45.2 SIGMA=  7.5 PHAS=  -97.7 FOM= 0.08 TEST= 0
INDE 21 31 66 FOBS=   46.4 SIGMA=  9.3 PHAS=  -65.7 FOM= 0.23 TEST= 0
INDE 21 31 68 FOBS=  122.7 SIGMA=  3.5 PHAS=  175.7 FOM= 0.96 TEST= 0
INDE 21 32 21 FOBS=  294.5 SIGMA=  0.8 PHAS=   82.1 FOM= 0.94 TEST= 0
INDE 21 32 23 FOBS=  128.0 SIGMA=  1.3 PHAS= -115.9 FOM= 0.88 TEST= 0
INDE 21 32 25 FOBS=  148.6 SIGMA=  1.2 PHAS= -120.5 FOM= 0.90 TEST= 0
INDE 21 32 27 FOBS=  173.7 SIGMA=  1.1 PHAS=  144.3 FOM= 0.85 TEST= 0
INDE 21 32 29 FOBS=  266.2 SIGMA=  0.8 PHAS=    8.7 FOM= 0.95 TEST= 0
INDE 21 32 31 FOBS=  215.1 SIGMA=  0.9 PHAS=  -66.0 FOM= 0.95 TEST= 0
INDE 21 32 33 FOBS=  136.0 SIGMA=  1.3 PHAS=  -15.4 FOM= 0.95 TEST= 0
INDE 21 32 35 FOBS=  123.4 SIGMA=  1.4 PHAS=  101.3 FOM= 0.91 TEST= 0
INDE 21 32 37 FOBS=  220.7 SIGMA=  0.8 PHAS=   58.8 FOM= 0.94 TEST= 0
INDE 21 32 39 FOBS=  170.2 SIGMA=  1.1 PHAS=  166.5 FOM= 0.93 TEST= 0
INDE 21 32 41 FOBS=   62.5 SIGMA=  2.8 PHAS=   40.5 FOM= 0.36 TEST= 0
INDE 21 32 43 FOBS=   20.7 SIGMA=  9.1 PHAS=  -31.1 FOM= 0.16 TEST= 0
INDE 21 32 45 FOBS=  164.8 SIGMA=  1.1 PHAS=   50.1 FOM= 0.96 TEST= 0
INDE 21 32 47 FOBS=  104.7 SIGMA=  1.7 PHAS=   65.6 FOM= 0.90 TEST= 0
INDE 21 32 49 FOBS=  101.2 SIGMA=  1.8 PHAS=  100.2 FOM= 0.93 TEST= 0
INDE 21 32 51 FOBS=    0.0 SIGMA= 21.5 PHAS=    0.0 FOM= 0.00 TEST= 0
INDE 21 32 53 FOBS=    0.0 SIGMA= 19.3 PHAS=    0.0 FOM= 0.00 TEST= 0
INDE 21 32 55 FOBS=  103.3 SIGMA=  2.0 PHAS=   35.8 FOM= 0.89 TEST= 0
INDE 21 32 57 FOBS=    0.0 SIGMA= 20.4 PHAS=    0.0 FOM= 0.00 TEST= 0
INDE 21 32 59 FOBS=   72.9 SIGMA=  2.7 PHAS=   32.5 FOM= 0.36 TEST= 0
INDE 21 32 61 FOBS=    0.0 SIGMA= 21.3 PHAS=    0.0 FOM= 0.00 TEST= 0
INDE 21 32 63 FOBS=   61.8 SIGMA=  3.8 PHAS=   14.5 FOM= 0.79 TEST= 0
INDE 21 32 65 FOBS=   74.4 SIGMA=  3.5 PHAS=   22.8 FOM= 0.57 TEST= 0
INDE 21 32 67 FOBS=   34.7 SIGMA= 11.8 PHAS=   41.4 FOM= 0.71 TEST= 0
INDE 21 33 22 FOBS=   63.7 SIGMA=  2.6 PHAS=  -56.0 FOM= 0.40 TEST= 1
INDE 21 33 24 FOBS=  137.1 SIGMA=  1.3 PHAS=  111.3 FOM= 0.97 TEST= 0
INDE 21 33 26 FOBS=  163.0 SIGMA=  1.2 PHAS=    9.3 FOM= 0.95 TEST= 0
INDE 21 33 28 FOBS=   88.3 SIGMA=  2.3 PHAS=    2.5 FOM= 0.50 TEST= 0
INDE 21 33 30 FOBS=  150.2 SIGMA=  1.4 PHAS= -117.7 FOM= 0.87 TEST= 0
INDE 21 33 32 FOBS=  187.0 SIGMA=  1.0 PHAS= -129.8 FOM= 0.83 TEST= 1
INDE 21 33 34 FOBS=  127.8 SIGMA=  1.4 PHAS=  177.4 FOM= 0.77 TEST= 0
INDE 21 33 36 FOBS=  131.4 SIGMA=  1.3 PHAS=   10.3 FOM= 0.82 TEST= 0
INDE 21 33 38 FOBS=  222.4 SIGMA=  0.8 PHAS=  108.8 FOM= 0.93 TEST= 0
INDE 21 33 40 FOBS=   93.0 SIGMA=  1.9 PHAS=   42.0 FOM= 0.87 TEST= 0
INDE 21 33 42 FOBS=  120.7 SIGMA=  1.6 PHAS=   -9.2 FOM= 0.44 TEST= 1
INDE 21 33 44 FOBS=  128.5 SIGMA=  1.5 PHAS=  -16.7 FOM= 0.94 TEST= 0
INDE 21 33 46 FOBS=   62.0 SIGMA=  3.0 PHAS= -138.7 FOM= 0.37 TEST= 1
INDE 21 33 48 FOBS=  160.9 SIGMA=  1.2 PHAS=  -49.8 FOM= 0.70 TEST= 1
INDE 21 33 50 FOBS=   57.0 SIGMA=  3.1 PHAS=   68.5 FOM= 0.79 TEST= 0
INDE 21 33 52 FOBS=    0.0 SIGMA= 19.5 PHAS=    0.0 FOM= 0.00 TEST= 0
INDE 21 33 54 FOBS=  105.4 SIGMA=  2.1 PHAS=  -19.4 FOM= 0.89 TEST= 0
INDE 21 33 56 FOBS=   55.5 SIGMA=  3.5 PHAS= -166.9 FOM= 0.82 TEST= 0
INDE 21 33 58 FOBS=    0.0 SIGMA= 21.0 PHAS=    0.0 FOM= 0.00 TEST= 0
INDE 21 33 60 FOBS=   49.7 SIGMA=  4.0 PHAS= -139.5 FOM= 0.12 TEST= 0
INDE 21 33 62 FOBS=  121.5 SIGMA=  2.0 PHAS= -133.1 FOM= 0.97 TEST= 0
INDE 21 33 64 FOBS=   46.5 SIGMA=  5.0 PHAS= -101.3 FOM= 0.69 TEST= 0
INDE 21 33 66 FOBS=   21.0 SIGMA= 12.4 PHAS=  -37.9 FOM= 0.33 TEST= 0
INDE 21 34 21 FOBS=  363.2 SIGMA=  0.8 PHAS= -162.0 FOM= 0.98 TEST= 0
INDE 21 34 23 FOBS=  166.0 SIGMA=  1.1 PHAS=  -20.4 FOM= 0.92 TEST= 0
INDE 21 34 25 FOBS=   96.3 SIGMA=  1.8 PHAS=  -14.1 FOM= 0.99 TEST= 0
INDE 21 34 27 FOBS=   22.9 SIGMA=  8.4 PHAS= -144.9 FOM= 0.07 TEST= 0
INDE 21 34 29 FOBS=  146.3 SIGMA=  1.3 PHAS=   63.4 FOM= 0.94 TEST= 0
INDE 21 34 31 FOBS=  170.3 SIGMA=  1.2 PHAS=  162.2 FOM= 0.90 TEST= 0
INDE 21 34 33 FOBS=   51.3 SIGMA=  3.5 PHAS=  102.7 FOM= 0.34 TEST= 0
INDE 21 34 35 FOBS=   63.0 SIGMA=  2.6 PHAS=   50.7 FOM= 0.16 TEST= 0
INDE 21 34 37 FOBS=  260.4 SIGMA=  0.8 PHAS=   89.3 FOM= 0.50 TEST= 1
INDE 21 34 39 FOBS=  123.2 SIGMA=  1.4 PHAS=   43.3 FOM= 0.87 TEST= 0
INDE 21 34 41 FOBS=  130.5 SIGMA=  1.5 PHAS=   42.0 FOM= 0.87 TEST= 0
INDE 21 34 43 FOBS=  166.6 SIGMA=  1.2 PHAS= -125.8 FOM= 0.95 TEST= 0
INDE 21 34 45 FOBS=  149.8 SIGMA=  1.3 PHAS=   35.6 FOM= 0.91 TEST= 0
INDE 21 34 47 FOBS=   77.1 SIGMA=  2.5 PHAS= -144.5 FOM= 0.76 TEST= 0
INDE 21 34 49 FOBS=  108.0 SIGMA=  1.8 PHAS=   97.0 FOM= 0.93 TEST= 0
INDE 21 34 51 FOBS=   91.8 SIGMA=  1.9 PHAS=    6.4 FOM= 0.80 TEST= 0
INDE 21 34 53 FOBS=    0.0 SIGMA= 21.7 PHAS=    0.0 FOM= 0.00 TEST= 0
```

*FIG. 12A - 455*

```
INDE 21 34 55 FOBS=    3.4 SIGMA= 62.6 PHAS= -126.8 FOM= 0.07 TEST= 0
INDE 21 34 57 FOBS=   17.3 SIGMA= 12.2 PHAS=   34.3 FOM= 0.07 TEST= 1
INDE 21 34 59 FOBS=   66.0 SIGMA=  3.0 PHAS= -104.0 FOM= 0.15 TEST= 0
INDE 21 34 61 FOBS=   41.5 SIGMA=  4.8 PHAS=  107.5 FOM= 0.78 TEST= 0
INDE 21 34 63 FOBS=  114.7 SIGMA=  1.9 PHAS=   99.2 FOM= 0.96 TEST= 0
INDE 21 34 65 FOBS=   26.8 SIGMA=  9.7 PHAS=  -47.9 FOM= 0.36 TEST= 0
INDE 21 35 22 FOBS=  154.8 SIGMA=  1.3 PHAS=  116.4 FOM= 0.93 TEST= 0
INDE 21 35 24 FOBS=  287.3 SIGMA=  0.8 PHAS=  -56.2 FOM= 0.98 TEST= 0
INDE 21 35 26 FOBS=  151.4 SIGMA=  1.3 PHAS=  -72.6 FOM= 0.98 TEST= 0
INDE 21 35 28 FOBS=    0.0 SIGMA= 19.2 PHAS=    0.0 FOM= 0.00 TEST= 0
INDE 21 35 30 FOBS=   93.1 SIGMA=  2.0 PHAS= -125.5 FOM= 0.42 TEST= 0
INDE 21 35 32 FOBS=  174.3 SIGMA=  1.1 PHAS=  135.1 FOM= 0.94 TEST= 0
INDE 21 35 34 FOBS=   90.2 SIGMA=  1.9 PHAS=  119.5 FOM= 0.79 TEST= 0
INDE 21 35 36 FOBS=  174.1 SIGMA=  1.0 PHAS=  -42.7 FOM= 0.93 TEST= 0
INDE 21 35 38 FOBS=   52.4 SIGMA=  3.5 PHAS=   88.3 FOM= 0.59 TEST= 0
INDE 21 35 40 FOBS=  155.1 SIGMA=  1.2 PHAS=  -39.0 FOM= 0.97 TEST= 0
INDE 21 35 42 FOBS=   90.4 SIGMA=  2.2 PHAS=   56.0 FOM= 0.93 TEST= 0
INDE 21 35 44 FOBS=  149.1 SIGMA=  1.4 PHAS= -144.7 FOM= 0.95 TEST= 0
INDE 21 35 46 FOBS=    0.0 SIGMA= 20.0 PHAS=    0.0 FOM= 0.00 TEST= 0
INDE 21 35 48 FOBS=  141.1 SIGMA=  1.5 PHAS=   31.6 FOM= 0.94 TEST= 0
INDE 21 35 50 FOBS=   49.9 SIGMA=  3.9 PHAS=  -59.8 FOM= 0.70 TEST= 0
INDE 21 35 52 FOBS=    0.0 SIGMA= 19.4 PHAS=    0.0 FOM= 0.00 TEST= 1
INDE 21 35 54 FOBS=   57.0 SIGMA=  3.8 PHAS=  100.5 FOM= 0.88 TEST= 0
INDE 21 35 56 FOBS=   42.5 SIGMA=  4.6 PHAS=  -83.4 FOM= 0.29 TEST= 0
INDE 21 35 58 FOBS=    0.0 SIGMA= 20.5 PHAS=    0.0 FOM= 0.00 TEST= 0
INDE 21 35 60 FOBS=   67.7 SIGMA=  3.0 PHAS=   16.0 FOM= 0.20 TEST= 1
INDE 21 35 62 FOBS=   75.0 SIGMA=  2.7 PHAS=  -59.7 FOM= 0.85 TEST= 0
INDE 21 35 64 FOBS=   66.4 SIGMA=  4.3 PHAS=   -8.3 FOM= 0.90 TEST= 0
INDE 21 35 66 FOBS=   43.3 SIGMA=  8.0 PHAS= -129.9 FOM= 0.42 TEST= 0
INDE 21 36 21 FOBS=  171.8 SIGMA=  1.2 PHAS=  -51.5 FOM= 0.93 TEST= 0
INDE 21 36 23 FOBS=  196.4 SIGMA=  1.1 PHAS= -107.1 FOM= 0.97 TEST= 0
INDE 21 36 25 FOBS=  213.6 SIGMA=  1.0 PHAS=  162.2 FOM= 0.96 TEST= 0
INDE 21 36 27 FOBS=    0.0 SIGMA= 19.1 PHAS=    0.0 FOM= 0.00 TEST= 0
INDE 21 36 29 FOBS=  187.1 SIGMA=  1.1 PHAS=  153.5 FOM= 0.94 TEST= 0
INDE 21 36 31 FOBS=  149.1 SIGMA=  1.3 PHAS=   97.9 FOM= 0.90 TEST= 0
INDE 21 36 33 FOBS=  163.4 SIGMA=  1.1 PHAS=   71.1 FOM= 0.91 TEST= 1
INDE 21 36 35 FOBS=  114.9 SIGMA=  1.5 PHAS= -108.9 FOM= 0.82 TEST= 0
INDE 21 36 37 FOBS=   64.3 SIGMA=  2.8 PHAS=   82.0 FOM= 0.51 TEST= 0
INDE 21 36 39 FOBS=  172.6 SIGMA=  1.1 PHAS=  173.1 FOM= 0.92 TEST= 0
INDE 21 36 41 FOBS=  129.5 SIGMA=  1.5 PHAS=  -36.8 FOM= 0.92 TEST= 0
INDE 21 36 43 FOBS=   91.0 SIGMA=  2.2 PHAS=   -1.2 FOM= 0.76 TEST= 0
INDE 21 36 45 FOBS=    0.0 SIGMA= 19.3 PHAS=    0.0 FOM= 0.00 TEST= 0
INDE 21 36 47 FOBS=   87.3 SIGMA=  2.2 PHAS=  -52.7 FOM= 0.91 TEST= 0
INDE 21 36 49 FOBS=   42.1 SIGMA=  4.7 PHAS=  154.7 FOM= 0.60 TEST= 0
INDE 21 36 51 FOBS=    0.0 SIGMA= 19.6 PHAS=    0.0 FOM= 0.00 TEST= 0
INDE 21 36 53 FOBS=  110.5 SIGMA=  2.0 PHAS=  -16.7 FOM= 0.95 TEST= 0
INDE 21 36 55 FOBS=   92.1 SIGMA=  2.4 PHAS=   16.2 FOM= 0.27 TEST= 1
INDE 21 36 57 FOBS=   74.3 SIGMA=  2.7 PHAS= -162.2 FOM= 0.77 TEST= 0
INDE 21 36 59 FOBS=   66.7 SIGMA=  3.0 PHAS= -127.4 FOM= 0.42 TEST= 1
INDE 21 36 61 FOBS=   75.1 SIGMA=  2.7 PHAS=  163.5 FOM= 0.64 TEST= 0
INDE 21 36 63 FOBS=    0.0 SIGMA= 21.1 PHAS=    0.0 FOM= 0.00 TEST= 0
INDE 21 36 65 FOBS=   46.5 SIGMA=  7.4 PHAS=  -28.6 FOM= 0.72 TEST= 0
INDE 21 37 22 FOBS=  229.6 SIGMA=  1.0 PHAS= -155.9 FOM= 0.94 TEST= 0
INDE 21 37 24 FOBS=   89.2 SIGMA=  2.3 PHAS=   59.5 FOM= 0.90 TEST= 0
INDE 21 37 26 FOBS=   57.3 SIGMA=  3.2 PHAS=    6.1 FOM= 0.75 TEST= 0
INDE 21 37 28 FOBS=   21.6 SIGMA=  8.4 PHAS=   44.0 FOM= 0.31 TEST= 0
INDE 21 37 30 FOBS=  306.9 SIGMA=  0.7 PHAS=   59.7 FOM= 0.96 TEST= 0
INDE 21 37 32 FOBS=  207.7 SIGMA=  1.0 PHAS=    7.2 FOM= 0.96 TEST= 0
INDE 21 37 34 FOBS=  158.2 SIGMA=  1.1 PHAS= -170.1 FOM= 0.94 TEST= 0
INDE 21 37 36 FOBS=    0.0 SIGMA= 19.3 PHAS=    0.0 FOM= 0.00 TEST= 0
INDE 21 37 38 FOBS=  167.9 SIGMA=  1.1 PHAS=   88.7 FOM= 0.92 TEST= 0
INDE 21 37 40 FOBS=  113.1 SIGMA=  1.6 PHAS= -104.1 FOM= 0.90 TEST= 0
INDE 21 37 42 FOBS=   53.7 SIGMA=  3.6 PHAS= -123.9 FOM= 0.72 TEST= 0
INDE 21 37 44 FOBS=   40.0 SIGMA=  4.8 PHAS= -158.3 FOM= 0.67 TEST= 0
INDE 21 37 46 FOBS=   52.8 SIGMA=  3.6 PHAS= -101.7 FOM= 0.72 TEST= 0
INDE 21 37 48 FOBS=   72.8 SIGMA=  2.7 PHAS=  111.9 FOM= 0.45 TEST= 0
INDE 21 37 50 FOBS=   18.4 SIGMA= 10.4 PHAS=  142.0 FOM= 0.19 TEST= 0
INDE 21 37 52 FOBS=   75.9 SIGMA=  2.6 PHAS=  -89.1 FOM= 0.60 TEST= 0
INDE 21 37 54 FOBS=   54.3 SIGMA=  4.0 PHAS= -136.8 FOM= 0.86 TEST= 0
INDE 21 37 56 FOBS=   43.8 SIGMA=  4.8 PHAS=    0.9 FOM= 0.72 TEST= 0
```

*FIG. 12A - 456*

```
INDE 21 37 58 FOBS=  68.1 SIGMA=  2.9 PHAS=   54.6 FOM= 0.85 TEST= 0
INDE 21 37 60 FOBS=   0.0 SIGMA= 20.6 PHAS=    0.0 FOM= 0.00 TEST= 0
INDE 21 37 62 FOBS=  84.3 SIGMA=  2.7 PHAS=  141.8 FOM= 0.91 TEST= 0
INDE 21 37 64 FOBS=   0.0 SIGMA= 23.9 PHAS=    0.0 FOM= 0.00 TEST= 0
INDE 21 38 21 FOBS= 200.3 SIGMA=  1.0 PHAS=  128.2 FOM= 0.89 TEST= 0
INDE 21 38 23 FOBS=  46.3 SIGMA=  5.1 PHAS= -167.5 FOM= 0.25 TEST= 0
INDE 21 38 25 FOBS=  72.4 SIGMA=  2.8 PHAS= -173.0 FOM= 0.78 TEST= 0
INDE 21 38 27 FOBS=  87.9 SIGMA=  2.1 PHAS=   31.6 FOM= 0.39 TEST= 0
INDE 21 38 29 FOBS=   0.0 SIGMA= 19.5 PHAS=    0.0 FOM= 0.00 TEST= 0
INDE 21 38 31 FOBS= 257.0 SIGMA=  0.8 PHAS=  -87.9 FOM= 0.94 TEST= 0
INDE 21 38 33 FOBS= 135.5 SIGMA=  1.6 PHAS=  117.4 FOM= 0.94 TEST= 0
INDE 21 38 35 FOBS=  91.1 SIGMA=  2.0 PHAS=   77.3 FOM= 0.94 TEST= 0
INDE 21 38 37 FOBS= 133.4 SIGMA=  1.4 PHAS=   -2.0 FOM= 0.90 TEST= 0
INDE 21 38 39 FOBS=  79.2 SIGMA=  2.3 PHAS= -168.3 FOM= 0.69 TEST= 0
INDE 21 38 41 FOBS=  75.1 SIGMA=  2.3 PHAS=  152.9 FOM= 0.68 TEST= 0
INDE 21 38 43 FOBS= 104.2 SIGMA=  1.9 PHAS=   75.0 FOM= 0.93 TEST= 0
INDE 21 38 45 FOBS=   0.0 SIGMA= 20.9 PHAS=    0.0 FOM= 0.00 TEST= 0
INDE 21 38 47 FOBS=  35.6 SIGMA=  5.6 PHAS=  161.3 FOM= 0.58 TEST= 0
INDE 21 38 49 FOBS=  46.5 SIGMA=  4.2 PHAS=   84.3 FOM= 0.44 TEST= 0
INDE 21 38 51 FOBS= 131.4 SIGMA=  1.6 PHAS=  129.8 FOM= 0.95 TEST= 0
INDE 21 38 53 FOBS=  56.5 SIGMA=  3.8 PHAS=   13.9 FOM= 0.25 TEST= 0
INDE 21 38 55 FOBS=  97.4 SIGMA=  2.3 PHAS= -107.6 FOM= 0.37 TEST= 1
INDE 21 38 57 FOBS=  73.7 SIGMA=  2.7 PHAS=  -52.4 FOM= 0.84 TEST= 0
INDE 21 38 59 FOBS=  32.3 SIGMA=  6.6 PHAS=  -14.5 FOM= 0.59 TEST= 0
INDE 21 38 61 FOBS=  77.7 SIGMA=  2.9 PHAS=   38.3 FOM= 0.90 TEST= 0
INDE 21 38 63 FOBS=  93.8 SIGMA=  3.2 PHAS=  -17.1 FOM= 0.95 TEST= 0
INDE 21 39 22 FOBS=  99.6 SIGMA=  1.8 PHAS= -155.8 FOM= 0.87 TEST= 0
INDE 21 39 24 FOBS= 176.2 SIGMA=  1.2 PHAS=   23.8 FOM= 0.92 TEST= 0
INDE 21 39 26 FOBS=  55.9 SIGMA=  3.2 PHAS= -123.2 FOM= 0.89 TEST= 0
INDE 21 39 28 FOBS=  36.2 SIGMA=  5.2 PHAS=   12.6 FOM= 0.48 TEST= 0
INDE 21 39 30 FOBS=   0.0 SIGMA= 18.9 PHAS=    0.0 FOM= 0.00 TEST= 1
INDE 21 39 32 FOBS=  91.9 SIGMA=  2.2 PHAS=  -42.6 FOM= 0.86 TEST= 0
INDE 21 39 34 FOBS=   0.0 SIGMA= 19.4 PHAS=    0.0 FOM= 0.00 TEST= 0
INDE 21 39 36 FOBS= 200.9 SIGMA=  1.0 PHAS=  -81.3 FOM= 0.88 TEST= 0
INDE 21 39 38 FOBS=  43.2 SIGMA=  4.1 PHAS=  -28.0 FOM= 0.40 TEST= 0
INDE 21 39 40 FOBS=  71.5 SIGMA=  2.5 PHAS= -151.1 FOM= 0.77 TEST= 0
INDE 21 39 42 FOBS=  63.8 SIGMA=  2.7 PHAS=  120.4 FOM= 0.89 TEST= 0
INDE 21 39 44 FOBS=  43.9 SIGMA=  4.5 PHAS=   50.1 FOM= 0.69 TEST= 0
INDE 21 39 46 FOBS= 113.3 SIGMA=  1.7 PHAS=    6.9 FOM= 0.91 TEST= 0
INDE 21 39 48 FOBS=  80.5 SIGMA=  2.4 PHAS=   28.7 FOM= 0.82 TEST= 0
INDE 21 39 50 FOBS= 115.8 SIGMA=  1.8 PHAS=   20.5 FOM= 0.93 TEST= 0
INDE 21 39 52 FOBS=  23.3 SIGMA= 11.0 PHAS=   51.0 FOM= 0.35 TEST= 0
INDE 21 39 54 FOBS=   0.0 SIGMA= 20.8 PHAS=    0.0 FOM= 0.00 TEST= 1
INDE 21 39 56 FOBS= 108.9 SIGMA=  2.1 PHAS=  -71.6 FOM= 0.79 TEST= 0
INDE 21 39 58 FOBS=  34.7 SIGMA=  7.8 PHAS=  -82.1 FOM= 0.27 TEST= 0
INDE 21 39 60 FOBS=  62.4 SIGMA=  3.6 PHAS=  -23.9 FOM= 0.89 TEST= 0
INDE 21 39 62 FOBS= 128.1 SIGMA=  2.3 PHAS= -147.2 FOM= 0.94 TEST= 0
INDE 21 40 21 FOBS= 105.2 SIGMA=  1.7 PHAS=    2.3 FOM= 0.86 TEST= 0
INDE 21 40 23 FOBS= 139.3 SIGMA=  1.3 PHAS=    8.5 FOM= 0.88 TEST= 0
INDE 21 40 25 FOBS= 223.3 SIGMA=  1.1 PHAS= -155.2 FOM= 0.96 TEST= 0
INDE 21 40 27 FOBS= 104.0 SIGMA=  1.8 PHAS=  105.3 FOM= 0.86 TEST= 0
INDE 21 40 29 FOBS= 155.1 SIGMA=  1.3 PHAS= -171.7 FOM= 0.91 TEST= 0
INDE 21 40 31 FOBS= 117.0 SIGMA=  1.8 PHAS= -134.2 FOM= 0.87 TEST= 0
INDE 21 40 33 FOBS=   0.0 SIGMA= 20.5 PHAS=    0.0 FOM= 0.00 TEST= 0
INDE 21 40 35 FOBS=  19.9 SIGMA=  9.5 PHAS=   34.1 FOM= 0.74 TEST= 1
INDE 21 40 37 FOBS= 180.3 SIGMA=  1.1 PHAS= -150.6 FOM= 0.95 TEST= 0
INDE 21 40 39 FOBS= 119.2 SIGMA=  1.5 PHAS=  124.1 FOM= 0.91 TEST= 0
INDE 21 40 41 FOBS= 133.4 SIGMA=  1.4 PHAS=   84.1 FOM= 0.90 TEST= 0
INDE 21 40 43 FOBS=  70.3 SIGMA=  2.5 PHAS=  -19.8 FOM= 0.87 TEST= 0
INDE 21 40 45 FOBS=   0.0 SIGMA= 19.5 PHAS=    0.0 FOM= 0.00 TEST= 0
INDE 21 40 47 FOBS=  71.6 SIGMA=  2.6 PHAS=  -98.6 FOM= 0.70 TEST= 0
INDE 21 40 49 FOBS= 117.8 SIGMA=  1.8 PHAS=  -65.4 FOM= 0.92 TEST= 0
INDE 21 40 51 FOBS=   0.0 SIGMA= 20.4 PHAS=    0.0 FOM= 0.00 TEST= 0
INDE 21 40 53 FOBS=  19.5 SIGMA= 10.9 PHAS= -148.8 FOM= 0.20 TEST= 0
INDE 21 40 55 FOBS=   0.0 SIGMA= 25.5 PHAS=    0.0 FOM= 0.00 TEST= 0
INDE 21 40 57 FOBS=  28.4 SIGMA=  9.4 PHAS=  124.3 FOM= 0.04 TEST= 0
INDE 21 40 59 FOBS=  45.7 SIGMA=  5.0 PHAS=  162.6 FOM= 0.55 TEST= 0
INDE 21 40 61 FOBS=  47.6 SIGMA=  7.0 PHAS=   51.2 FOM= 0.77 TEST= 0
INDE 21 40 63 FOBS=  60.0 SIGMA=  5.4 PHAS=  -73.3 FOM= 0.17 TEST= 1
INDE 21 41 22 FOBS= 170.6 SIGMA=  1.1 PHAS= -116.5 FOM= 0.89 TEST= 0
```

*FIG. 12A - 457*

```
INDE  21  41  24  FOBS=  105.1  SIGMA=   1.7  PHAS=   -33.2  FOM=  0.81  TEST=  0
INDE  21  41  26  FOBS=  117.2  SIGMA=   1.7  PHAS=  -177.0  FOM=  0.84  TEST=  0
INDE  21  41  28  FOBS=  231.2  SIGMA=   1.0  PHAS=    82.4  FOM=  0.96  TEST=  0
INDE  21  41  30  FOBS=  110.8  SIGMA=   1.8  PHAS=    79.6  FOM=  0.81  TEST=  0
INDE  21  41  32  FOBS=   80.6  SIGMA=   2.5  PHAS=   -78.1  FOM=  0.61  TEST=  0
INDE  21  41  34  FOBS=  182.0  SIGMA=   1.2  PHAS=  -119.2  FOM=  0.95  TEST=  0
INDE  21  41  36  FOBS=   25.4  SIGMA=   7.4  PHAS=    59.3  FOM=  0.64  TEST=  0
INDE  21  41  38  FOBS=  111.8  SIGMA=   1.6  PHAS=    50.3  FOM=  0.94  TEST=  0
INDE  21  41  40  FOBS=   92.0  SIGMA=   2.0  PHAS=    13.7  FOM=  0.87  TEST=  0
INDE  21  41  42  FOBS=   56.3  SIGMA=   3.1  PHAS=  -163.2  FOM=  0.86  TEST=  0
INDE  21  41  44  FOBS=    0.0  SIGMA=  19.8  PHAS=     0.0  FOM=  0.00  TEST=  1
INDE  21  41  46  FOBS=   45.2  SIGMA=   4.2  PHAS=    72.5  FOM=  0.43  TEST=  0
INDE  21  41  48  FOBS=   64.5  SIGMA=   3.0  PHAS=  -173.5  FOM=  0.66  TEST=  0
INDE  21  41  50  FOBS=   65.9  SIGMA=   3.0  PHAS=  -171.7  FOM=  0.81  TEST=  0
INDE  21  41  52  FOBS=   57.7  SIGMA=   3.8  PHAS=  -172.3  FOM=  0.74  TEST=  1
INDE  21  41  54  FOBS=   58.7  SIGMA=   4.2  PHAS=    15.1  FOM=  0.77  TEST=  0
INDE  21  41  56  FOBS=   30.6  SIGMA=  10.5  PHAS=    86.4  FOM=  0.18  TEST=  0
INDE  21  41  58  FOBS=    0.0  SIGMA=  25.0  PHAS=     0.0  FOM=  0.00  TEST=  0
INDE  21  41  60  FOBS=   66.9  SIGMA=   4.8  PHAS=    15.7  FOM=  0.93  TEST=  0
INDE  21  41  62  FOBS=    0.0  SIGMA=  25.9  PHAS=     0.0  FOM=  0.00  TEST=  0
INDE  21  42  21  FOBS=   24.1  SIGMA=   7.3  PHAS=   105.4  FOM=  0.01  TEST=  0
INDE  21  42  23  FOBS=   47.8  SIGMA=   3.9  PHAS=   -86.2  FOM=  0.08  TEST=  0
INDE  21  42  25  FOBS=  146.0  SIGMA=   1.3  PHAS=   147.1  FOM=  0.92  TEST=  0
INDE  21  42  27  FOBS=   26.3  SIGMA=   8.5  PHAS=   -38.0  FOM=  0.38  TEST=  0
INDE  21  42  29  FOBS=   56.9  SIGMA=   3.4  PHAS=   -16.1  FOM=  0.61  TEST=  0
INDE  21  42  31  FOBS=   42.1  SIGMA=   4.7  PHAS=    37.2  FOM=  0.64  TEST=  0
INDE  21  42  33  FOBS=  237.9  SIGMA=   1.0  PHAS=   164.6  FOM=  0.97  TEST=  0
INDE  21  42  35  FOBS=  106.2  SIGMA=   1.9  PHAS=    24.3  FOM=  0.91  TEST=  0
INDE  21  42  37  FOBS=  140.8  SIGMA=   1.4  PHAS=   -56.6  FOM=  0.91  TEST=  0
INDE  21  42  39  FOBS=   25.4  SIGMA=   6.9  PHAS=  -154.0  FOM=  0.33  TEST=  0
INDE  21  42  41  FOBS=   52.5  SIGMA=   3.3  PHAS=    12.0  FOM=  0.36  TEST=  0
INDE  21  42  43  FOBS=   25.0  SIGMA=   7.2  PHAS=    32.6  FOM=  0.45  TEST=  0
INDE  21  42  45  FOBS=  114.0  SIGMA=   1.6  PHAS=    89.1  FOM=  0.90  TEST=  0
INDE  21  42  47  FOBS=  111.1  SIGMA=   1.8  PHAS=    52.8  FOM=  0.90  TEST=  0
INDE  21  42  49  FOBS=   69.1  SIGMA=   2.8  PHAS=   124.4  FOM=  0.87  TEST=  0
INDE  21  42  51  FOBS=   96.2  SIGMA=   2.3  PHAS=   122.5  FOM=  0.96  TEST=  0
INDE  21  42  53  FOBS=   85.0  SIGMA=   2.9  PHAS=  -130.2  FOM=  0.79  TEST=  0
INDE  21  42  55  FOBS=   44.5  SIGMA=   5.5  PHAS=     2.5  FOM=  0.74  TEST=  0
INDE  21  42  57  FOBS=   63.1  SIGMA=   4.0  PHAS=   -33.0  FOM=  0.85  TEST=  0
INDE  21  42  59  FOBS=   83.3  SIGMA=   2.8  PHAS=   -89.2  FOM=  0.88  TEST=  0
INDE  21  42  61  FOBS=   27.7  SIGMA=  12.2  PHAS=    -6.5  FOM=  0.44  TEST=  0
INDE  21  43  22  FOBS=  261.4  SIGMA=   0.8  PHAS=  -119.4  FOM=  0.94  TEST=  0
INDE  21  43  24  FOBS=   98.5  SIGMA=   2.0  PHAS=   -64.1  FOM=  0.90  TEST=  0
INDE  21  43  26  FOBS=   65.8  SIGMA=   2.9  PHAS=    88.7  FOM=  0.92  TEST=  0
INDE  21  43  28  FOBS=  158.3  SIGMA=   1.4  PHAS=   149.9  FOM=  0.89  TEST=  0
INDE  21  43  30  FOBS=   94.8  SIGMA=   2.1  PHAS=   -78.4  FOM=  0.87  TEST=  1
INDE  21  43  32  FOBS=  108.3  SIGMA=   1.9  PHAS=    28.1  FOM=  0.92  TEST=  0
INDE  21  43  34  FOBS=   91.5  SIGMA=   2.2  PHAS=   -60.4  FOM=  0.91  TEST=  0
INDE  21  43  36  FOBS=    0.0  SIGMA=  21.6  PHAS=     0.0  FOM=  0.00  TEST=  0
INDE  21  43  38  FOBS=   59.9  SIGMA=   3.0  PHAS=    68.7  FOM=  0.05  TEST=  1
INDE  21  43  40  FOBS=    0.0  SIGMA=  19.6  PHAS=     0.0  FOM=  0.00  TEST=  0
INDE  21  43  42  FOBS=  130.6  SIGMA=   1.4  PHAS=  -145.3  FOM=  0.91  TEST=  0
INDE  21  43  44  FOBS=   78.0  SIGMA=   2.2  PHAS=   -33.0  FOM=  0.88  TEST=  0
INDE  21  43  46  FOBS=   95.1  SIGMA=   1.9  PHAS=   -39.6  FOM=  0.83  TEST=  0
INDE  21  43  48  FOBS=   35.9  SIGMA=   5.7  PHAS=   -38.6  FOM=  0.52  TEST=  0
INDE  21  43  50  FOBS=  164.0  SIGMA=   1.6  PHAS=    71.9  FOM=  0.98  TEST=  0
INDE  21  43  52  FOBS=   52.7  SIGMA=   5.2  PHAS=   -13.1  FOM=  0.35  TEST=  0
INDE  21  43  54  FOBS=  125.9  SIGMA=   2.1  PHAS=    20.3  FOM=  0.88  TEST=  0
INDE  21  43  56  FOBS=    6.6  SIGMA=  37.1  PHAS=  -125.9  FOM=  0.16  TEST=  0
INDE  21  43  58  FOBS=   16.4  SIGMA=  14.0  PHAS=   -90.5  FOM=  0.30  TEST=  0
INDE  21  43  60  FOBS=   60.3  SIGMA=   4.8  PHAS=    -4.2  FOM=  0.72  TEST=  0
INDE  21  44  21  FOBS=  290.7  SIGMA=   0.9  PHAS=   157.6  FOM=  0.23  TEST=  1
INDE  21  44  23  FOBS=  120.2  SIGMA=   1.7  PHAS=   145.8  FOM=  0.91  TEST=  1
INDE  21  44  25  FOBS=    0.0  SIGMA=  19.5  PHAS=     0.0  FOM=  0.00  TEST=  0
INDE  21  44  27  FOBS=   78.4  SIGMA=   2.5  PHAS=   -33.0  FOM=  0.95  TEST=  0
INDE  21  44  29  FOBS=   47.8  SIGMA=   3.8  PHAS=  -177.5  FOM=  0.24  TEST=  0
INDE  21  44  31  FOBS=   85.1  SIGMA=   2.3  PHAS=    93.4  FOM=  0.91  TEST=  0
INDE  21  44  33  FOBS=  138.6  SIGMA=   1.5  PHAS=  -154.5  FOM=  0.89  TEST=  0
INDE  21  44  35  FOBS=   67.8  SIGMA=   2.9  PHAS=   -80.1  FOM=  0.71  TEST=  1
INDE  21  44  37  FOBS=   74.5  SIGMA=   2.4  PHAS=   -38.3  FOM=  0.89  TEST=  0
```

*FIG. 12A - 458*

```
INDE 21 44 39 FOBS=    0.0 SIGMA= 19.2 PHAS=    0.0 FOM= 0.00 TEST= 0
INDE 21 44 41 FOBS=  107.0 SIGMA=  1.7 PHAS=  131.8 FOM= 0.92 TEST= 0
INDE 21 44 43 FOBS=   50.6 SIGMA=  3.4 PHAS=  119.4 FOM= 0.83 TEST= 0
INDE 21 44 45 FOBS=    0.0 SIGMA= 19.6 PHAS=    0.0 FOM= 0.00 TEST= 0
INDE 21 44 47 FOBS=   94.3 SIGMA=  2.1 PHAS=   86.2 FOM= 0.91 TEST= 0
INDE 21 44 49 FOBS=   70.5 SIGMA=  3.3 PHAS=  -18.0 FOM= 0.90 TEST= 0
INDE 21 44 51 FOBS=   74.7 SIGMA=  3.3 PHAS=   55.9 FOM= 0.79 TEST= 0
INDE 21 44 53 FOBS=   59.7 SIGMA=  4.2 PHAS= -105.3 FOM= 0.81 TEST= 0
INDE 21 44 55 FOBS=   59.3 SIGMA=  4.2 PHAS=  -38.7 FOM= 0.77 TEST= 0
INDE 21 44 57 FOBS=   37.2 SIGMA=  6.8 PHAS=  120.0 FOM= 0.74 TEST= 0
INDE 21 44 59 FOBS=   41.5 SIGMA=  6.9 PHAS= -115.8 FOM= 0.71 TEST= 0
INDE 21 45 22 FOBS=  112.8 SIGMA=  1.7 PHAS=   54.7 FOM= 0.63 TEST= 0
INDE 21 45 24 FOBS=   99.5 SIGMA=  2.0 PHAS=  -44.0 FOM= 0.70 TEST= 0
INDE 21 45 26 FOBS=   91.5 SIGMA=  2.1 PHAS= -170.0 FOM= 0.55 TEST= 1
INDE 21 45 28 FOBS=   78.9 SIGMA=  2.4 PHAS=  150.0 FOM= 0.95 TEST= 0
INDE 21 45 30 FOBS=   29.9 SIGMA=  6.4 PHAS=  -53.1 FOM= 0.37 TEST= 0
INDE 21 45 32 FOBS=   31.5 SIGMA=  6.1 PHAS=   65.8 FOM= 0.67 TEST= 0
INDE 21 45 34 FOBS=  105.2 SIGMA=  1.9 PHAS= -152.7 FOM= 0.92 TEST= 0
INDE 21 45 36 FOBS=  128.6 SIGMA=  1.6 PHAS= -172.6 FOM= 0.66 TEST= 0
INDE 21 45 38 FOBS=   85.4 SIGMA=  2.1 PHAS=  -76.5 FOM= 0.75 TEST= 1
INDE 21 45 40 FOBS=   37.0 SIGMA=  5.0 PHAS=  179.3 FOM= 0.44 TEST= 0
INDE 21 45 42 FOBS=    0.0 SIGMA= 19.2 PHAS=    0.0 FOM= 0.00 TEST= 0
INDE 21 45 44 FOBS=   25.9 SIGMA=  7.5 PHAS=  -35.1 FOM= 0.12 TEST= 0
INDE 21 45 46 FOBS=   26.0 SIGMA=  7.6 PHAS=  -12.6 FOM= 0.53 TEST= 0
INDE 21 45 48 FOBS=   89.3 SIGMA=  2.3 PHAS=  -71.8 FOM= 0.91 TEST= 0
INDE 21 45 50 FOBS=   95.8 SIGMA=  2.5 PHAS=    8.6 FOM= 0.92 TEST= 0
INDE 21 45 52 FOBS=    0.0 SIGMA= 22.2 PHAS=    0.0 FOM= 0.00 TEST= 0
INDE 21 45 54 FOBS=   62.5 SIGMA=  4.0 PHAS=  -94.8 FOM= 0.85 TEST= 0
INDE 21 45 56 FOBS=   61.4 SIGMA=  4.6 PHAS=   35.8 FOM= 0.78 TEST= 0
INDE 21 45 58 FOBS=   25.2 SIGMA= 11.4 PHAS=  -43.8 FOM= 0.36 TEST= 0
INDE 21 46 21 FOBS=   13.0 SIGMA= 14.5 PHAS=   26.3 FOM= 0.15 TEST= 0
INDE 21 46 23 FOBS=   44.6 SIGMA=  4.5 PHAS=    1.2 FOM= 0.13 TEST= 0
INDE 21 46 25 FOBS=  133.1 SIGMA=  1.5 PHAS= -153.9 FOM= 0.85 TEST= 0
INDE 21 46 27 FOBS=  123.5 SIGMA=  1.6 PHAS= -166.9 FOM= 0.92 TEST= 0
INDE 21 46 29 FOBS=    0.0 SIGMA= 19.5 PHAS=    0.0 FOM= 0.00 TEST= 0
INDE 21 46 31 FOBS=   86.8 SIGMA=  2.0 PHAS=  -29.6 FOM= 0.09 TEST= 1
INDE 21 46 33 FOBS=   73.9 SIGMA=  2.7 PHAS=  -51.2 FOM= 0.36 TEST= 1
INDE 21 46 35 FOBS=    7.9 SIGMA= 24.3 PHAS=  114.8 FOM= 0.16 TEST= 0
INDE 21 46 37 FOBS=   99.4 SIGMA=  2.0 PHAS=  -33.3 FOM= 0.59 TEST= 0
INDE 21 46 39 FOBS=    0.0 SIGMA= 19.2 PHAS=    0.0 FOM= 0.00 TEST= 0
INDE 21 46 41 FOBS=   59.1 SIGMA=  3.2 PHAS=  153.5 FOM= 0.77 TEST= 0
INDE 21 46 43 FOBS=   39.6 SIGMA=  6.0 PHAS=   67.5 FOM= 0.46 TEST= 0
INDE 21 46 45 FOBS=    0.0 SIGMA= 21.1 PHAS=    0.0 FOM= 0.00 TEST= 0
INDE 21 46 47 FOBS=   24.4 SIGMA=  8.7 PHAS=  -95.7 FOM= 0.39 TEST= 0
INDE 21 46 49 FOBS=   92.2 SIGMA=  2.2 PHAS= -129.4 FOM= 0.93 TEST= 0
INDE 21 46 51 FOBS=   86.2 SIGMA=  3.0 PHAS= -117.2 FOM= 0.89 TEST= 0
INDE 21 46 53 FOBS=   35.6 SIGMA=  7.0 PHAS=  -31.3 FOM= 0.28 TEST= 1
INDE 21 46 55 FOBS=   76.9 SIGMA=  3.3 PHAS=   56.0 FOM= 0.86 TEST= 0
INDE 21 46 57 FOBS=   56.3 SIGMA=  6.0 PHAS=  176.3 FOM= 0.76 TEST= 0
INDE 21 46 59 FOBS=   67.5 SIGMA=  5.1 PHAS= -141.4 FOM= 0.70 TEST= 0
INDE 21 47 22 FOBS=  142.0 SIGMA=  1.4 PHAS=  148.4 FOM= 0.94 TEST= 0
INDE 21 47 24 FOBS=  102.4 SIGMA=  1.9 PHAS=  157.3 FOM= 0.79 TEST= 0
INDE 21 47 26 FOBS=  177.0 SIGMA=  1.2 PHAS=  133.3 FOM= 0.96 TEST= 0
INDE 21 47 28 FOBS=   97.6 SIGMA=  2.0 PHAS= -140.9 FOM= 0.88 TEST= 0
INDE 21 47 30 FOBS=  116.9 SIGMA=  1.7 PHAS=  -68.3 FOM= 0.16 TEST= 1
INDE 21 47 32 FOBS=  142.0 SIGMA=  1.3 PHAS= -140.1 FOM= 0.88 TEST= 0
INDE 21 47 34 FOBS=   43.7 SIGMA=  4.4 PHAS=  -71.1 FOM= 0.59 TEST= 0
INDE 21 47 36 FOBS=   36.4 SIGMA=  6.9 PHAS= -140.7 FOM= 0.69 TEST= 0
INDE 21 47 38 FOBS=    0.0 SIGMA= 21.2 PHAS=    0.0 FOM= 0.00 TEST= 1
INDE 21 47 40 FOBS=    0.0 SIGMA= 20.6 PHAS=    0.0 FOM= 0.00 TEST= 1
INDE 21 47 42 FOBS=    0.0 SIGMA= 20.4 PHAS=    0.0 FOM= 0.00 TEST= 0
INDE 21 47 44 FOBS=   39.2 SIGMA=  5.5 PHAS=   -6.4 FOM= 0.34 TEST= 0
INDE 21 47 46 FOBS=    0.0 SIGMA= 20.6 PHAS=    0.0 FOM= 0.00 TEST= 0
INDE 21 47 48 FOBS=   64.0 SIGMA=  3.2 PHAS=  171.0 FOM= 0.91 TEST= 0
INDE 21 47 50 FOBS=   77.2 SIGMA=  2.6 PHAS=  171.3 FOM= 0.88 TEST= 0
INDE 21 47 52 FOBS=   37.0 SIGMA=  6.8 PHAS=  120.2 FOM= 0.68 TEST= 0
INDE 21 47 54 FOBS=  105.1 SIGMA=  2.5 PHAS=  -33.3 FOM= 0.94 TEST= 0
INDE 21 47 56 FOBS=   86.9 SIGMA=  3.4 PHAS=    9.6 FOM= 0.94 TEST= 0
INDE 21 47 58 FOBS=  103.8 SIGMA=  2.9 PHAS=  113.2 FOM= 0.41 TEST= 1
INDE 21 48 21 FOBS=  173.4 SIGMA=  1.1 PHAS=   68.8 FOM= 0.94 TEST= 0
```

*FIG. 12A - 459*

```
INDE 21 48 23 FOBS=   230.9 SIGMA=  1.0 PHAS=   59.7 FOM= 0.98 TEST= 0
INDE 21 48 25 FOBS=   113.0 SIGMA=  1.8 PHAS=   57.3 FOM= 0.90 TEST= 0
INDE 21 48 27 FOBS=   215.1 SIGMA=  1.0 PHAS=  138.6 FOM= 0.96 TEST= 0
INDE 21 48 29 FOBS=   126.8 SIGMA=  1.6 PHAS=  174.9 FOM= 0.89 TEST= 0
INDE 21 48 31 FOBS=    89.9 SIGMA=  2.0 PHAS=  163.7 FOM= 0.91 TEST= 0
INDE 21 48 33 FOBS=    62.2 SIGMA=  2.9 PHAS= -127.3 FOM= 0.86 TEST= 0
INDE 21 48 35 FOBS=    41.0 SIGMA=  6.0 PHAS=  159.8 FOM= 0.37 TEST= 0
INDE 21 48 37 FOBS=    44.7 SIGMA=  5.8 PHAS=  153.9 FOM= 0.68 TEST= 0
INDE 21 48 39 FOBS=    42.8 SIGMA=  5.0 PHAS= -132.4 FOM= 0.50 TEST= 0
INDE 21 48 41 FOBS=    37.7 SIGMA=  5.4 PHAS=  141.2 FOM= 0.60 TEST= 0
INDE 21 48 43 FOBS=    36.7 SIGMA=  5.4 PHAS=  -85.9 FOM= 0.60 TEST= 0
INDE 21 48 45 FOBS=    88.5 SIGMA=  2.3 PHAS=  -92.3 FOM= 0.90 TEST= 0
INDE 21 48 47 FOBS=    43.6 SIGMA=  4.6 PHAS=  132.8 FOM= 0.49 TEST= 0
INDE 21 48 49 FOBS=    51.1 SIGMA=  3.9 PHAS=   68.7 FOM= 0.85 TEST= 0
INDE 21 48 51 FOBS=    51.0 SIGMA=  3.9 PHAS=  113.4 FOM= 0.82 TEST= 0
INDE 21 48 53 FOBS=    97.6 SIGMA=  2.7 PHAS=  -94.5 FOM= 0.94 TEST= 0
INDE 21 48 55 FOBS=    99.3 SIGMA=  3.0 PHAS= -107.6 FOM= 0.95 TEST= 0
INDE 21 48 57 FOBS=    32.6 SIGMA=  9.0 PHAS=  -59.8 FOM= 0.50 TEST= 0
INDE 21 49 22 FOBS=   170.5 SIGMA=  1.2 PHAS=  -63.3 FOM= 0.94 TEST= 0
INDE 21 49 24 FOBS=    72.9 SIGMA=  2.6 PHAS=  -96.2 FOM= 0.80 TEST= 0
INDE 21 49 26 FOBS=   148.4 SIGMA=  1.4 PHAS=   55.4 FOM= 0.96 TEST= 0
INDE 21 49 28 FOBS=    56.2 SIGMA=  3.6 PHAS=   57.8 FOM= 0.51 TEST= 0
INDE 21 49 30 FOBS=    49.3 SIGMA=  4.1 PHAS=  106.2 FOM= 0.27 TEST= 0
INDE 21 49 32 FOBS=    70.2 SIGMA=  2.8 PHAS=    5.5 FOM= 0.51 TEST= 1
INDE 21 49 34 FOBS=    79.1 SIGMA=  2.5 PHAS=  104.3 FOM= 0.64 TEST= 0
INDE 21 49 36 FOBS=    98.0 SIGMA=  2.4 PHAS=  120.9 FOM= 0.81 TEST= 1
INDE 21 49 38 FOBS=    60.7 SIGMA=  3.8 PHAS=  138.6 FOM= 0.84 TEST= 0
INDE 21 49 40 FOBS=    36.1 SIGMA=  5.8 PHAS=  -12.2 FOM= 0.63 TEST= 0
INDE 21 49 42 FOBS=    68.1 SIGMA=  3.0 PHAS=  161.3 FOM= 0.85 TEST= 0
INDE 21 49 44 FOBS=   149.9 SIGMA=  1.4 PHAS=  167.9 FOM= 0.96 TEST= 0
INDE 21 49 46 FOBS=    31.8 SIGMA=  6.4 PHAS=   -6.4 FOM= 0.02 TEST= 1
INDE 21 49 48 FOBS=    14.5 SIGMA= 13.9 PHAS=  127.9 FOM= 0.13 TEST= 0
INDE 21 49 50 FOBS=    91.2 SIGMA=  2.3 PHAS=   -7.1 FOM= 0.91 TEST= 0
INDE 21 49 52 FOBS=    39.2 SIGMA=  5.6 PHAS=   60.9 FOM= 0.06 TEST= 0
INDE 21 49 54 FOBS=    12.2 SIGMA= 23.5 PHAS=  156.4 FOM= 0.13 TEST= 0
INDE 21 49 56 FOBS=     0.0 SIGMA= 26.0 PHAS=    0.0 FOM= 0.00 TEST= 0
INDE 21 50 21 FOBS=    45.5 SIGMA=  4.2 PHAS=    2.5 FOM= 0.16 TEST= 0
INDE 21 50 23 FOBS=    32.4 SIGMA=  6.2 PHAS=  -53.0 FOM= 0.17 TEST= 0
INDE 21 50 25 FOBS=    37.4 SIGMA=  6.3 PHAS=   51.9 FOM= 0.13 TEST= 0
INDE 21 50 27 FOBS=     5.5 SIGMA= 43.2 PHAS= -149.0 FOM= 0.07 TEST= 0
INDE 21 50 29 FOBS=   168.1 SIGMA=  1.4 PHAS= -139.0 FOM= 0.97 TEST= 0
INDE 21 50 31 FOBS=   138.9 SIGMA=  1.7 PHAS=  123.3 FOM= 0.95 TEST= 0
INDE 21 50 33 FOBS=    69.1 SIGMA=  2.8 PHAS= -101.5 FOM= 0.89 TEST= 0
INDE 21 50 35 FOBS=    85.9 SIGMA=  2.3 PHAS=  -30.6 FOM= 0.91 TEST= 0
INDE 21 50 37 FOBS=    56.6 SIGMA=  4.0 PHAS=   49.3 FOM= 0.56 TEST= 0
INDE 21 50 39 FOBS=    25.6 SIGMA=  8.9 PHAS=  -17.2 FOM= 0.12 TEST= 0
INDE 21 50 41 FOBS=    65.3 SIGMA=  3.1 PHAS=   65.3 FOM= 0.86 TEST= 0
INDE 21 50 43 FOBS=   106.1 SIGMA=  2.0 PHAS=  139.5 FOM= 0.88 TEST= 0
INDE 21 50 45 FOBS=    57.1 SIGMA=  3.6 PHAS=  -10.6 FOM= 0.82 TEST= 0
INDE 21 50 47 FOBS=    44.4 SIGMA=  4.6 PHAS=   85.8 FOM= 0.65 TEST= 0
INDE 21 50 49 FOBS=    55.2 SIGMA=  3.7 PHAS=  -36.6 FOM= 0.86 TEST= 0
INDE 21 50 51 FOBS=    88.3 SIGMA=  2.4 PHAS=  -87.5 FOM= 0.92 TEST= 0
INDE 21 50 53 FOBS=    76.8 SIGMA=  3.2 PHAS=  -29.3 FOM= 0.88 TEST= 0
INDE 21 50 55 FOBS=    63.5 SIGMA=  5.6 PHAS=  -19.7 FOM= 0.88 TEST= 0
INDE 21 51 22 FOBS=    70.5 SIGMA=  3.1 PHAS=  -75.8 FOM= 0.89 TEST= 0
INDE 21 51 24 FOBS=    45.3 SIGMA=  5.1 PHAS= -160.4 FOM= 0.77 TEST= 0
INDE 21 51 26 FOBS=    74.0 SIGMA=  2.9 PHAS=   41.2 FOM= 0.85 TEST= 0
INDE 21 51 28 FOBS=   122.8 SIGMA=  1.8 PHAS=   79.4 FOM= 0.92 TEST= 0
INDE 21 51 30 FOBS=   116.3 SIGMA=  1.9 PHAS=  132.6 FOM= 0.94 TEST= 0
INDE 21 51 32 FOBS=    94.3 SIGMA=  2.3 PHAS=   24.2 FOM= 0.88 TEST= 0
INDE 21 51 34 FOBS=   153.1 SIGMA=  1.3 PHAS=  158.2 FOM= 0.64 TEST= 1
INDE 21 51 36 FOBS=    39.4 SIGMA=  5.1 PHAS=   38.8 FOM= 0.16 TEST= 0
INDE 21 51 38 FOBS=    21.6 SIGMA= 10.3 PHAS=  164.2 FOM= 0.17 TEST= 0
INDE 21 51 40 FOBS=    55.4 SIGMA=  4.2 PHAS=  -57.5 FOM= 0.64 TEST= 0
INDE 21 51 42 FOBS=    44.9 SIGMA=  5.1 PHAS=    9.7 FOM= 0.71 TEST= 0
INDE 21 51 44 FOBS=    96.6 SIGMA=  2.2 PHAS=  155.5 FOM= 0.90 TEST= 0
INDE 21 51 46 FOBS=     0.0 SIGMA= 23.1 PHAS=    0.0 FOM= 0.00 TEST= 0
INDE 21 51 48 FOBS=    39.5 SIGMA=  5.1 PHAS=  -15.8 FOM= 0.59 TEST= 0
INDE 21 51 50 FOBS=    15.4 SIGMA= 15.5 PHAS=  -50.9 FOM= 0.19 TEST= 0
INDE 21 51 52 FOBS=    55.4 SIGMA=  4.5 PHAS= -148.5 FOM= 0.91 TEST= 0
```

*FIG. 12A - 460*

```
INDE 21 51 54 FOBS=  102.1 SIGMA=  3.2 PHAS=  -85.4 FOM= 0.92 TEST= 0
INDE 21 52 21 FOBS=   76.7 SIGMA=  2.4 PHAS= -143.3 FOM= 0.88 TEST= 0
INDE 21 52 23 FOBS=   70.8 SIGMA=  3.0 PHAS= -125.1 FOM= 0.82 TEST= 0
INDE 21 52 25 FOBS=   55.8 SIGMA=  3.9 PHAS= -127.2 FOM= 0.89 TEST= 0
INDE 21 52 27 FOBS=  175.4 SIGMA=  1.4 PHAS=  -66.9 FOM= 0.97 TEST= 0
INDE 21 52 29 FOBS=   57.7 SIGMA=  3.8 PHAS=  -99.2 FOM= 0.53 TEST= 0
INDE 21 52 31 FOBS=   97.3 SIGMA=  2.3 PHAS=   37.3 FOM= 0.81 TEST= 0
INDE 21 52 33 FOBS=   58.8 SIGMA=  3.5 PHAS=   15.0 FOM= 0.61 TEST= 0
INDE 21 52 35 FOBS=   66.5 SIGMA=  2.9 PHAS=   25.5 FOM= 0.46 TEST= 0
INDE 21 52 37 FOBS=   46.7 SIGMA=  4.1 PHAS=   -4.1 FOM= 0.47 TEST= 0
INDE 21 52 39 FOBS=   32.5 SIGMA=  9.9 PHAS=  -27.2 FOM= 0.23 TEST= 0
INDE 21 52 41 FOBS=    0.0 SIGMA= 19.9 PHAS=    0.0 FOM= 0.00 TEST= 0
INDE 21 52 43 FOBS=   11.7 SIGMA= 17.5 PHAS=  177.4 FOM= 0.21 TEST= 0
INDE 21 52 45 FOBS=   58.2 SIGMA=  3.9 PHAS=   25.1 FOM= 0.89 TEST= 0
INDE 21 52 47 FOBS=   29.6 SIGMA=  7.6 PHAS=  -17.1 FOM= 0.15 TEST= 0
INDE 21 52 49 FOBS=   71.8 SIGMA=  3.2 PHAS=  -73.1 FOM= 0.84 TEST= 0
INDE 21 52 51 FOBS=    0.0 SIGMA= 24.4 PHAS=    0.0 FOM= 0.00 TEST= 0
INDE 21 52 53 FOBS=    0.0 SIGMA= 25.2 PHAS=    0.0 FOM= 0.00 TEST= 0
INDE 21 53 22 FOBS=   56.5 SIGMA=  3.6 PHAS=  102.5 FOM= 0.77 TEST= 0
INDE 21 53 24 FOBS=  133.3 SIGMA=  1.7 PHAS=  151.5 FOM= 0.95 TEST= 0
INDE 21 53 26 FOBS=   42.9 SIGMA=  5.0 PHAS=   85.3 FOM= 0.37 TEST= 0
INDE 21 53 28 FOBS=   52.5 SIGMA=  4.1 PHAS= -178.2 FOM= 0.81 TEST= 0
INDE 21 53 30 FOBS=   57.5 SIGMA=  3.8 PHAS=  -48.2 FOM= 0.75 TEST= 0
INDE 21 53 32 FOBS=   86.8 SIGMA=  2.5 PHAS=  -18.5 FOM= 0.93 TEST= 0
INDE 21 53 34 FOBS=   72.2 SIGMA=  2.7 PHAS=  117.3 FOM= 0.80 TEST= 0
INDE 21 53 36 FOBS=   10.5 SIGMA= 19.6 PHAS=  -15.0 FOM= 0.16 TEST= 0
INDE 21 53 38 FOBS=   61.2 SIGMA=  3.1 PHAS=  -91.7 FOM= 0.60 TEST= 0
INDE 21 53 40 FOBS=   59.7 SIGMA=  3.9 PHAS= -148.1 FOM= 0.59 TEST= 0
INDE 21 53 42 FOBS=    0.0 SIGMA= 22.1 PHAS=    0.0 FOM= 0.00 TEST= 0
INDE 21 53 44 FOBS=   29.0 SIGMA=  7.8 PHAS= -145.4 FOM= 0.35 TEST= 0
INDE 21 53 46 FOBS=    0.0 SIGMA= 24.7 PHAS=    0.0 FOM= 0.00 TEST= 0
INDE 21 53 48 FOBS=   39.8 SIGMA=  6.4 PHAS=  145.8 FOM= 0.42 TEST= 0
INDE 21 53 50 FOBS=    0.0 SIGMA= 22.3 PHAS=    0.0 FOM= 0.00 TEST= 0
INDE 21 53 52 FOBS=   46.4 SIGMA=  7.0 PHAS= -178.7 FOM= 0.57 TEST= 0
INDE 21 54 21 FOBS=   59.0 SIGMA=  3.4 PHAS=   37.8 FOM= 0.55 TEST= 0
INDE 21 54 23 FOBS=  141.3 SIGMA=  1.6 PHAS=  -34.1 FOM= 0.95 TEST= 0
INDE 21 54 25 FOBS=   69.6 SIGMA=  3.1 PHAS=    7.4 FOM= 0.81 TEST= 0
INDE 21 54 27 FOBS=  108.3 SIGMA=  2.0 PHAS=  -41.3 FOM= 0.93 TEST= 0
INDE 21 54 29 FOBS=   91.6 SIGMA=  2.4 PHAS=  -51.8 FOM= 0.85 TEST= 0
INDE 21 54 31 FOBS=    0.0 SIGMA= 20.7 PHAS=    0.0 FOM= 0.00 TEST= 0
INDE 21 54 33 FOBS=   78.4 SIGMA=  2.8 PHAS=  -63.7 FOM= 0.85 TEST= 0
INDE 21 54 35 FOBS=    0.0 SIGMA= 20.7 PHAS=    0.0 FOM= 0.00 TEST= 0
INDE 21 54 37 FOBS=    0.0 SIGMA= 21.8 PHAS=    0.0 FOM= 0.00 TEST= 0
INDE 21 54 39 FOBS=   78.8 SIGMA=  2.7 PHAS=  162.5 FOM= 0.87 TEST= 0
INDE 21 54 41 FOBS=   35.6 SIGMA=  8.4 PHAS=  172.2 FOM= 0.44 TEST= 0
INDE 21 54 43 FOBS=   10.5 SIGMA= 28.5 PHAS=   97.1 FOM= 0.20 TEST= 0
INDE 21 54 45 FOBS=   56.8 SIGMA=  4.5 PHAS=   60.4 FOM= 0.63 TEST= 0
INDE 21 54 47 FOBS=   52.5 SIGMA=  4.8 PHAS= -169.3 FOM= 0.48 TEST= 0
INDE 21 54 49 FOBS=   73.6 SIGMA=  3.5 PHAS=   26.3 FOM= 0.86 TEST= 0
INDE 21 54 51 FOBS=   50.5 SIGMA=  6.4 PHAS=   49.8 FOM= 0.02 TEST= 1
INDE 21 55 22 FOBS=    0.0 SIGMA= 18.3 PHAS=    0.0 FOM= 0.00 TEST= 0
INDE 21 55 24 FOBS=   83.6 SIGMA=  2.6 PHAS= -123.3 FOM= 0.91 TEST= 0
INDE 21 55 26 FOBS=  125.2 SIGMA=  1.8 PHAS=  -48.6 FOM= 0.81 TEST= 0
INDE 21 55 28 FOBS=   85.7 SIGMA=  2.8 PHAS= -157.8 FOM= 0.86 TEST= 0
INDE 21 55 30 FOBS=   56.0 SIGMA=  3.9 PHAS= -115.7 FOM= 0.84 TEST= 0
INDE 21 55 32 FOBS=   18.6 SIGMA= 12.9 PHAS=   35.8 FOM= 0.41 TEST= 0
INDE 21 55 34 FOBS=   59.7 SIGMA=  4.1 PHAS=  175.8 FOM= 0.87 TEST= 0
INDE 21 55 36 FOBS=    0.0 SIGMA= 23.3 PHAS=    0.0 FOM= 0.00 TEST= 0
INDE 21 55 38 FOBS=    0.0 SIGMA= 23.9 PHAS=    0.0 FOM= 0.00 TEST= 0
INDE 21 55 40 FOBS=   71.9 SIGMA=  3.2 PHAS=   80.7 FOM= 0.91 TEST= 0
INDE 21 55 42 FOBS=   29.8 SIGMA= 10.2 PHAS=   85.5 FOM= 0.55 TEST= 0
INDE 21 55 44 FOBS=   58.7 SIGMA=  4.3 PHAS=  -28.9 FOM= 0.79 TEST= 0
INDE 21 55 46 FOBS=   97.3 SIGMA=  2.7 PHAS=   38.6 FOM= 0.93 TEST= 0
INDE 21 55 48 FOBS=    0.0 SIGMA= 25.1 PHAS=    0.0 FOM= 0.00 TEST= 0
INDE 21 55 50 FOBS=   63.1 SIGMA=  5.3 PHAS=  -15.2 FOM= 0.81 TEST= 0
INDE 21 56 21 FOBS=   29.4 SIGMA=  8.2 PHAS= -104.6 FOM= 0.10 TEST= 1
INDE 21 56 23 FOBS=   56.4 SIGMA=  3.7 PHAS= -154.8 FOM= 0.65 TEST= 0
INDE 21 56 25 FOBS=   13.6 SIGMA= 16.5 PHAS=  -83.1 FOM= 0.13 TEST= 0
INDE 21 56 27 FOBS=   84.1 SIGMA=  2.6 PHAS=  -56.2 FOM= 0.84 TEST= 0
INDE 21 56 29 FOBS=   67.1 SIGMA=  3.6 PHAS=    5.1 FOM= 0.50 TEST= 0
```

*FIG. 12A - 461*

```
INDE  21  56  31  FOBS=    0.0  SIGMA=  25.2  PHAS=    0.0  FOM=  0.00  TEST= 1
INDE  21  56  33  FOBS=   69.5  SIGMA=   4.0  PHAS=  103.2  FOM=  0.40  TEST= 0
INDE  21  56  35  FOBS=    0.0  SIGMA=  22.3  PHAS=    0.0  FOM=  0.00  TEST= 0
INDE  21  56  37  FOBS=   37.4  SIGMA=   6.0  PHAS= -107.0  FOM=  0.61  TEST= 0
INDE  21  56  39  FOBS=   58.3  SIGMA=   4.0  PHAS=  -45.2  FOM=  0.51  TEST= 0
INDE  21  56  41  FOBS=   52.7  SIGMA=   5.1  PHAS=   -0.6  FOM=  0.42  TEST= 1
INDE  21  56  43  FOBS=   43.7  SIGMA=   5.7  PHAS=  -75.0  FOM=  0.15  TEST= 1
INDE  21  56  45  FOBS=   69.1  SIGMA=   3.8  PHAS=  -79.6  FOM=  0.90  TEST= 0
INDE  21  56  47  FOBS=   42.6  SIGMA=   7.6  PHAS= -101.7  FOM=  0.57  TEST= 0
INDE  21  56  49  FOBS=   35.0  SIGMA=  11.4  PHAS=  -41.4  FOM=  0.52  TEST= 0
INDE  21  57  22  FOBS=   37.5  SIGMA=   7.1  PHAS=   83.2  FOM=  0.43  TEST= 0
INDE  21  57  24  FOBS=   54.2  SIGMA=   4.3  PHAS= -158.1  FOM=  0.40  TEST= 0
INDE  21  57  26  FOBS=  101.0  SIGMA=   2.6  PHAS=  178.0  FOM=  0.84  TEST= 0
INDE  21  57  28  FOBS=  115.1  SIGMA=   2.4  PHAS= -115.2  FOM=  0.18  TEST= 1
INDE  21  57  30  FOBS=  104.2  SIGMA=   2.7  PHAS= -135.6  FOM=  0.86  TEST= 0
INDE  21  57  32  FOBS=   43.2  SIGMA=   7.3  PHAS=  129.7  FOM=  0.63  TEST= 0
INDE  21  57  34  FOBS=    0.0  SIGMA=  25.3  PHAS=    0.0  FOM=  0.00  TEST= 1
INDE  21  57  36  FOBS=    0.0  SIGMA=  21.1  PHAS=    0.0  FOM=  0.00  TEST= 0
INDE  21  57  38  FOBS=   94.5  SIGMA=   2.5  PHAS= -151.8  FOM=  0.90  TEST= 0
INDE  21  57  40  FOBS=    0.0  SIGMA=  22.4  PHAS=    0.0  FOM=  0.00  TEST= 0
INDE  21  57  42  FOBS=   78.0  SIGMA=   3.5  PHAS=   86.7  FOM=  0.12  TEST= 0
INDE  21  57  44  FOBS=   66.7  SIGMA=   4.2  PHAS=    9.4  FOM=  0.68  TEST= 0
INDE  21  57  46  FOBS=   19.5  SIGMA=  16.9  PHAS=  -71.2  FOM=  0.39  TEST= 0
INDE  21  57  48  FOBS=   21.6  SIGMA=  15.4  PHAS=  120.7  FOM=  0.16  TEST= 0
INDE  21  58  21  FOBS=   29.0  SIGMA=   8.4  PHAS=  176.3  FOM=  0.48  TEST= 0
INDE  21  58  23  FOBS=   51.4  SIGMA=   7.1  PHAS=  167.3  FOM=  0.91  TEST= 0
INDE  21  58  25  FOBS=   89.8  SIGMA=   2.9  PHAS=   30.4  FOM=  0.85  TEST= 0
INDE  21  58  27  FOBS=   35.6  SIGMA=   7.1  PHAS=   17.5  FOM=  0.53  TEST= 0
INDE  21  58  29  FOBS=   54.9  SIGMA=   4.8  PHAS=  114.7  FOM=  0.59  TEST= 0
INDE  21  58  31  FOBS=  124.8  SIGMA=   2.2  PHAS=   98.5  FOM=  0.94  TEST= 0
INDE  21  58  33  FOBS=   82.1  SIGMA=   3.4  PHAS=   76.2  FOM=  0.91  TEST= 0
INDE  21  58  35  FOBS=   41.4  SIGMA=   6.6  PHAS=  -12.6  FOM=  0.26  TEST= 0
INDE  21  58  37  FOBS=   31.1  SIGMA=   7.9  PHAS= -156.6  FOM=  0.46  TEST= 0
INDE  21  58  39  FOBS=    0.0  SIGMA=  22.3  PHAS=    0.0  FOM=  0.00  TEST= 0
INDE  21  58  41  FOBS=    0.0  SIGMA=  22.6  PHAS=    0.0  FOM=  0.00  TEST= 0
INDE  21  58  43  FOBS=   65.5  SIGMA=   4.2  PHAS= -118.2  FOM=  0.42  TEST= 0
INDE  21  58  45  FOBS=   61.5  SIGMA=   4.7  PHAS= -103.1  FOM=  0.91  TEST= 0
INDE  21  58  47  FOBS=    0.0  SIGMA=  25.7  PHAS=    0.0  FOM=  0.00  TEST= 0
INDE  21  59  22  FOBS=   59.3  SIGMA=   4.6  PHAS=   73.7  FOM=  0.87  TEST= 0
INDE  21  59  24  FOBS=   25.0  SIGMA=   9.9  PHAS=  -89.7  FOM=  0.30  TEST= 0
INDE  21  59  26  FOBS=   60.6  SIGMA=   4.2  PHAS= -141.6  FOM=  0.71  TEST= 0
INDE  21  59  28  FOBS=    0.0  SIGMA=  22.6  PHAS=    0.0  FOM=  0.00  TEST= 0
INDE  21  59  30  FOBS=    0.0  SIGMA=  24.3  PHAS=    0.0  FOM=  0.00  TEST= 0
INDE  21  59  32  FOBS=  177.4  SIGMA=   1.7  PHAS=   -0.3  FOM=  0.98  TEST= 0
INDE  21  59  34  FOBS=   47.8  SIGMA=   6.6  PHAS=  -15.9  FOM=  0.50  TEST= 0
INDE  21  59  36  FOBS=   44.5  SIGMA=   6.3  PHAS=   55.5  FOM=  0.35  TEST= 0
INDE  21  59  38  FOBS=    9.7  SIGMA=  26.0  PHAS=   44.4  FOM=  0.19  TEST= 0
INDE  21  59  40  FOBS=   74.5  SIGMA=   3.2  PHAS=   13.3  FOM=  0.91  TEST= 0
INDE  21  59  42  FOBS=   41.4  SIGMA=   6.5  PHAS=  -93.4  FOM=  0.45  TEST= 0
INDE  21  59  44  FOBS=   34.4  SIGMA=  10.6  PHAS=  127.3  FOM=  0.67  TEST= 0
INDE  21  59  46  FOBS=    0.0  SIGMA=  27.5  PHAS=    0.0  FOM=  0.00  TEST= 1
INDE  21  60  21  FOBS=   24.9  SIGMA=  11.0  PHAS=   33.2  FOM=  0.54  TEST= 0
INDE  21  60  23  FOBS=    0.0  SIGMA=  26.9  PHAS=    0.0  FOM=  0.00  TEST= 0
INDE  21  60  25  FOBS=    0.0  SIGMA=  22.4  PHAS=    0.0  FOM=  0.00  TEST= 0
INDE  21  60  27  FOBS=   10.9  SIGMA=  23.4  PHAS=   -3.3  FOM=  0.17  TEST= 0
INDE  21  60  29  FOBS=   71.5  SIGMA=   3.7  PHAS=  -12.1  FOM=  0.25  TEST= 1
INDE  21  60  31  FOBS=   39.4  SIGMA=   7.7  PHAS=  -59.8  FOM=  0.70  TEST= 0
INDE  21  60  33  FOBS=   93.2  SIGMA=   3.0  PHAS= -101.5  FOM=  0.91  TEST= 0
INDE  21  60  35  FOBS=    0.0  SIGMA=  26.0  PHAS=    0.0  FOM=  0.00  TEST= 0
INDE  21  60  37  FOBS=   39.6  SIGMA=   6.4  PHAS=  -45.3  FOM=  0.82  TEST= 0
INDE  21  60  39  FOBS=   87.4  SIGMA=   2.8  PHAS=  -99.2  FOM=  0.91  TEST= 0
INDE  21  60  41  FOBS=   46.9  SIGMA=   5.1  PHAS=  -61.7  FOM=  0.80  TEST= 0
INDE  21  60  43  FOBS=   46.2  SIGMA=   6.5  PHAS=   71.4  FOM=  0.72  TEST= 0
INDE  21  61  22  FOBS=   56.4  SIGMA=   4.9  PHAS=    8.9  FOM=  0.80  TEST= 0
INDE  21  61  24  FOBS=   37.4  SIGMA=   9.7  PHAS=  -83.2  FOM=  0.37  TEST= 0
INDE  21  61  26  FOBS=   47.7  SIGMA=   5.4  PHAS=  149.1  FOM=  0.60  TEST= 0
INDE  21  61  28  FOBS=   71.7  SIGMA=   3.7  PHAS=  -72.0  FOM=  0.73  TEST= 0
INDE  21  61  30  FOBS=   32.6  SIGMA=   8.0  PHAS=  174.4  FOM=  0.06  TEST= 1
INDE  21  61  32  FOBS=   49.7  SIGMA=   5.5  PHAS=   24.6  FOM=  0.56  TEST= 0
INDE  21  61  34  FOBS=  117.2  SIGMA=   2.5  PHAS=   50.4  FOM=  0.90  TEST= 0
```

*FIG. 12A - 462*

```
INDE 21 61 36 FOBS=    0.0 SIGMA= 23.6 PHAS=    0.0 FOM= 0.00 TEST= 0
INDE 21 61 38 FOBS=   48.2 SIGMA=  5.3 PHAS=  113.3 FOM= 0.55 TEST= 0
INDE 21 61 40 FOBS=    0.0 SIGMA= 24.0 PHAS=    0.0 FOM= 0.00 TEST= 0
INDE 21 61 42 FOBS=   84.0 SIGMA=  3.6 PHAS=  -53.3 FOM= 0.87 TEST= 0
INDE 21 62 21 FOBS=   45.0 SIGMA=  7.3 PHAS= -155.5 FOM= 0.75 TEST= 0
INDE 21 62 23 FOBS=   15.9 SIGMA= 17.1 PHAS=   71.2 FOM= 0.04 TEST= 0
INDE 21 62 25 FOBS=    0.0 SIGMA= 27.0 PHAS=    0.0 FOM= 0.00 TEST= 0
INDE 21 62 27 FOBS=    0.0 SIGMA= 22.7 PHAS=    0.0 FOM= 0.00 TEST= 0
INDE 21 62 29 FOBS=    0.0 SIGMA= 22.7 PHAS=    0.0 FOM= 0.00 TEST= 0
INDE 21 62 31 FOBS=   73.3 SIGMA=  3.7 PHAS=    8.6 FOM= 0.61 TEST= 0
INDE 21 62 33 FOBS=   42.6 SIGMA=  7.4 PHAS=  -51.5 FOM= 0.72 TEST= 0
INDE 21 62 35 FOBS=   29.0 SIGMA=  9.7 PHAS=   55.7 FOM= 0.22 TEST= 0
INDE 21 62 37 FOBS=   83.6 SIGMA=  3.5 PHAS=    9.2 FOM= 0.92 TEST= 0
INDE 21 62 39 FOBS=    0.0 SIGMA= 21.8 PHAS=    0.0 FOM= 0.00 TEST= 1
INDE 21 62 41 FOBS=   65.8 SIGMA=  4.6 PHAS= -105.9 FOM= 0.81 TEST= 0
INDE 21 63 22 FOBS=   76.8 SIGMA=  3.6 PHAS= -177.1 FOM= 0.07 TEST= 1
INDE 21 63 24 FOBS=   64.8 SIGMA=  4.2 PHAS=  -54.4 FOM= 0.83 TEST= 0
INDE 21 63 26 FOBS=   16.6 SIGMA= 18.0 PHAS=   35.6 FOM= 0.14 TEST= 0
INDE 21 63 28 FOBS=   22.0 SIGMA= 11.9 PHAS=   -7.9 FOM= 0.45 TEST= 0
INDE 21 63 30 FOBS=   48.1 SIGMA=  5.5 PHAS=  -68.3 FOM= 0.67 TEST= 0
INDE 21 63 32 FOBS=    0.0 SIGMA= 25.2 PHAS=    0.0 FOM= 0.00 TEST= 0
INDE 21 63 34 FOBS=   74.3 SIGMA=  4.4 PHAS=  -51.2 FOM= 0.83 TEST= 0
INDE 21 63 36 FOBS=   31.4 SIGMA= 10.6 PHAS= -116.3 FOM= 0.47 TEST= 0
INDE 21 63 38 FOBS=   25.6 SIGMA= 11.3 PHAS=   22.9 FOM= 0.02 TEST= 1
INDE 21 63 40 FOBS=   54.2 SIGMA=  6.4 PHAS=  129.0 FOM= 0.71 TEST= 0
INDE 21 64 21 FOBS=   52.2 SIGMA=  5.2 PHAS=  163.2 FOM= 0.41 TEST= 0
INDE 21 64 23 FOBS=    0.0 SIGMA= 25.6 PHAS=    0.0 FOM= 0.00 TEST= 0
INDE 21 64 25 FOBS=   90.8 SIGMA=  4.2 PHAS= -133.1 FOM= 0.92 TEST= 0
INDE 21 64 27 FOBS=    0.0 SIGMA= 27.3 PHAS=    0.0 FOM= 0.00 TEST= 1
INDE 21 64 29 FOBS=   23.0 SIGMA= 13.1 PHAS=   75.4 FOM= 0.34 TEST= 0
INDE 21 64 31 FOBS=   63.4 SIGMA=  5.0 PHAS=  159.2 FOM= 0.82 TEST= 0
INDE 21 64 33 FOBS=   39.4 SIGMA=  8.3 PHAS=  126.4 FOM= 0.50 TEST= 0
INDE 21 64 35 FOBS=   56.2 SIGMA=  6.0 PHAS= -160.5 FOM= 0.89 TEST= 0
INDE 21 64 37 FOBS=   41.5 SIGMA=  8.4 PHAS=   46.2 FOM= 0.38 TEST= 0
INDE 21 65 22 FOBS=   30.1 SIGMA=  9.2 PHAS=   35.8 FOM= 0.13 TEST= 0
INDE 21 65 24 FOBS=    0.0 SIGMA= 23.6 PHAS=    0.0 FOM= 0.00 TEST= 0
INDE 21 65 26 FOBS=    0.0 SIGMA= 27.3 PHAS=    0.0 FOM= 0.00 TEST= 1
INDE 21 65 28 FOBS=  106.1 SIGMA=  3.0 PHAS=  -31.5 FOM= 0.96 TEST= 0
INDE 21 65 30 FOBS=   39.6 SIGMA=  7.8 PHAS=   34.8 FOM= 0.70 TEST= 0
INDE 21 65 32 FOBS=   66.8 SIGMA=  4.8 PHAS=  134.6 FOM= 0.80 TEST= 0
INDE 21 65 34 FOBS=   22.3 SIGMA= 17.6 PHAS=  111.1 FOM= 0.01 TEST= 1
INDE 21 65 36 FOBS=   31.9 SIGMA= 10.7 PHAS=  103.6 FOM= 0.29 TEST= 0
INDE 21 66 21 FOBS=    0.0 SIGMA= 25.4 PHAS=    0.0 FOM= 0.00 TEST= 0
INDE 21 66 23 FOBS=    6.1 SIGMA= 54.8 PHAS= -171.5 FOM= 0.07 TEST= 0
INDE 21 66 25 FOBS=   15.3 SIGMA= 18.1 PHAS= -172.0 FOM= 0.27 TEST= 0
INDE 21 66 27 FOBS=  107.6 SIGMA=  3.7 PHAS= -118.1 FOM= 0.96 TEST= 0
INDE 21 66 29 FOBS=   73.0 SIGMA=  4.3 PHAS= -105.7 FOM= 0.70 TEST= 0
INDE 21 66 31 FOBS=   33.8 SIGMA=  9.3 PHAS=   18.7 FOM= 0.68 TEST= 0
INDE 21 66 33 FOBS=   66.5 SIGMA=  5.0 PHAS=  105.8 FOM= 0.91 TEST= 0
INDE 21 66 35 FOBS=    6.8 SIGMA= 65.1 PHAS= -142.2 FOM= 0.13 TEST= 0
INDE 21 67 22 FOBS=    0.0 SIGMA= 28.6 PHAS=    0.0 FOM= 0.00 TEST= 0
INDE 21 67 24 FOBS=   29.6 SIGMA= 11.4 PHAS=   78.6 FOM= 0.12 TEST= 0
INDE 21 67 26 FOBS=    0.0 SIGMA= 32.9 PHAS=    0.0 FOM= 0.00 TEST= 0
INDE 21 67 28 FOBS=   54.0 SIGMA=  7.3 PHAS=  171.4 FOM= 0.53 TEST= 0
INDE 21 67 30 FOBS=    0.0 SIGMA= 24.9 PHAS=    0.0 FOM= 0.00 TEST= 0
INDE 21 67 32 FOBS=   63.2 SIGMA=  6.3 PHAS=  -22.9 FOM= 0.71 TEST= 0
INDE 21 68 21 FOBS=   54.9 SIGMA=  7.5 PHAS=  -68.9 FOM= 0.81 TEST= 0
INDE 21 68 23 FOBS=   22.4 SIGMA= 18.8 PHAS=    9.6 FOM= 0.17 TEST= 0
INDE 21 68 25 FOBS=   23.4 SIGMA= 18.6 PHAS=   32.3 FOM= 0.16 TEST= 0
INDE 21 68 29 FOBS=   38.1 SIGMA= 10.3 PHAS=  -12.9 FOM= 0.27 TEST= 0
INDE 21 68 31 FOBS=   48.0 SIGMA=  8.5 PHAS= -107.1 FOM= 0.51 TEST= 0
INDE 21 69 22 FOBS=   13.9 SIGMA= 30.4 PHAS=  107.5 FOM= 0.26 TEST= 0
INDE 21 69 24 FOBS=  105.9 SIGMA=  4.3 PHAS=  -20.5 FOM= 0.25 TEST= 1
INDE 21 69 26 FOBS=    0.0 SIGMA= 29.6 PHAS=    0.0 FOM= 0.00 TEST= 0
INDE 21 70 21 FOBS=   20.0 SIGMA= 19.8 PHAS= -112.2 FOM= 0.35 TEST= 0
INDE 21 70 23 FOBS=   86.1 SIGMA=  5.0 PHAS=   17.6 FOM= 0.91 TEST= 0
INDE 21 70 25 FOBS=   16.2 SIGMA= 28.1 PHAS= -103.2 FOM= 0.27 TEST= 0
INDE 21 71 22 FOBS=    0.0 SIGMA= 29.2 PHAS=    0.0 FOM= 0.00 TEST= 0
INDE 22 22 22 FOBS=  284.0 SIGMA=  1.2 PHAS=   86.7 FOM= 0.97 TEST= 0
INDE 22 23 23 FOBS=   33.9 SIGMA=  4.1 PHAS=  -46.1 FOM= 0.86 TEST= 1
```

*FIG. 12A - 463*

```
INDE 22 23 25 FOBS=  136.6 SIGMA=  1.1 PHAS=  100.8 FOM= 0.98 TEST= 0
INDE 22 23 27 FOBS=   69.5 SIGMA=  2.1 PHAS=  105.3 FOM= 0.12 TEST= 0
INDE 22 23 29 FOBS=  156.0 SIGMA=  1.0 PHAS=  122.3 FOM= 0.93 TEST= 0
INDE 22 23 31 FOBS=  339.7 SIGMA=  0.6 PHAS=  141.0 FOM= 0.97 TEST= 0
INDE 22 23 33 FOBS=  110.9 SIGMA=  1.4 PHAS=  -30.0 FOM= 0.88 TEST= 1
INDE 22 23 35 FOBS=  116.7 SIGMA=  1.6 PHAS=  121.5 FOM= 0.91 TEST= 0
INDE 22 23 37 FOBS=  201.0 SIGMA=  1.1 PHAS= -165.0 FOM= 0.92 TEST= 0
INDE 22 23 39 FOBS=  135.3 SIGMA=  1.3 PHAS= -115.0 FOM= 0.86 TEST= 0
INDE 22 23 41 FOBS=   81.8 SIGMA=  2.3 PHAS=  -28.5 FOM= 0.93 TEST= 0
INDE 22 23 43 FOBS=  198.7 SIGMA=  0.9 PHAS= -165.3 FOM= 0.97 TEST= 0
INDE 22 23 45 FOBS=   50.1 SIGMA=  3.2 PHAS=  144.9 FOM= 0.75 TEST= 0
INDE 22 23 47 FOBS=   22.0 SIGMA=  8.1 PHAS=   50.4 FOM= 0.75 TEST= 1
INDE 22 23 49 FOBS=   87.4 SIGMA=  1.9 PHAS=  149.4 FOM= 0.93 TEST= 0
INDE 22 23 51 FOBS=    0.0 SIGMA= 18.3 PHAS=    0.0 FOM= 0.00 TEST= 0
INDE 22 23 53 FOBS=   87.2 SIGMA=  2.0 PHAS=  -12.6 FOM= 0.90 TEST= 0
INDE 22 23 55 FOBS=   90.4 SIGMA=  2.3 PHAS=   -7.7 FOM= 0.92 TEST= 0
INDE 22 23 57 FOBS=  106.2 SIGMA=  2.8 PHAS=   76.1 FOM= 0.58 TEST= 1
INDE 22 23 59 FOBS=   94.9 SIGMA=  3.1 PHAS=  129.7 FOM= 0.49 TEST= 1
INDE 22 23 61 FOBS=    0.0 SIGMA= 25.3 PHAS=    0.0 FOM= 0.00 TEST= 0
INDE 22 23 63 FOBS=   61.0 SIGMA=  4.6 PHAS=   11.7 FOM= 0.79 TEST= 0
INDE 22 23 65 FOBS=   89.4 SIGMA=  3.9 PHAS=   73.5 FOM= 0.95 TEST= 0
INDE 22 23 67 FOBS=   80.2 SIGMA=  5.3 PHAS=   58.9 FOM= 0.92 TEST= 0
INDE 22 23 69 FOBS=   62.7 SIGMA=  6.9 PHAS=  -14.9 FOM= 0.77 TEST= 0
INDE 22 24 22 FOBS=  293.9 SIGMA=  0.7 PHAS= -127.7 FOM= 0.99 TEST= 0
INDE 22 24 24 FOBS=  235.2 SIGMA=  0.7 PHAS=  -75.9 FOM= 0.96 TEST= 0
INDE 22 24 26 FOBS=  289.6 SIGMA=  0.6 PHAS=    9.6 FOM= 0.96 TEST= 0
INDE 22 24 28 FOBS=   79.2 SIGMA=  1.8 PHAS= -100.1 FOM= 0.74 TEST= 0
INDE 22 24 30 FOBS=  127.1 SIGMA=  1.1 PHAS=   -1.9 FOM= 0.91 TEST= 0
INDE 22 24 32 FOBS=  379.1 SIGMA=  0.7 PHAS=   78.2 FOM= 0.99 TEST= 0
INDE 22 24 34 FOBS=   86.7 SIGMA=  1.8 PHAS=   39.1 FOM= 0.73 TEST= 0
INDE 22 24 36 FOBS=   60.0 SIGMA=  3.0 PHAS= -127.3 FOM= 0.47 TEST= 0
INDE 22 24 38 FOBS=  213.9 SIGMA=  1.0 PHAS=  133.9 FOM= 0.96 TEST= 0
INDE 22 24 40 FOBS=  111.8 SIGMA=  1.6 PHAS= -102.2 FOM= 0.94 TEST= 0
INDE 22 24 42 FOBS=  136.0 SIGMA=  1.3 PHAS=  147.2 FOM= 0.93 TEST= 0
INDE 22 24 44 FOBS=  106.8 SIGMA=  1.6 PHAS=  142.8 FOM= 0.94 TEST= 0
INDE 22 24 46 FOBS=   65.8 SIGMA=  2.4 PHAS=  107.8 FOM= 0.86 TEST= 0
INDE 22 24 48 FOBS=  111.5 SIGMA=  1.4 PHAS=   33.2 FOM= 0.69 TEST= 0
INDE 22 24 50 FOBS=   78.5 SIGMA=  2.1 PHAS=  -10.2 FOM= 0.88 TEST= 0
INDE 22 24 52 FOBS=   15.1 SIGMA= 12.4 PHAS=  -56.5 FOM= 0.07 TEST= 0
INDE 22 24 54 FOBS=  100.8 SIGMA=  1.9 PHAS=  -66.4 FOM= 0.91 TEST= 0
INDE 22 24 56 FOBS=   75.6 SIGMA=  3.4 PHAS=   38.6 FOM= 0.93 TEST= 0
INDE 22 24 58 FOBS=   71.9 SIGMA=  4.0 PHAS=  -46.5 FOM= 0.84 TEST= 0
INDE 22 24 60 FOBS=   30.4 SIGMA=  9.4 PHAS= -147.3 FOM= 0.02 TEST= 1
INDE 22 24 62 FOBS=   40.6 SIGMA=  7.1 PHAS= -172.2 FOM= 0.56 TEST= 0
INDE 22 24 64 FOBS=   96.6 SIGMA=  3.1 PHAS=  -49.1 FOM= 0.92 TEST= 0
INDE 22 24 66 FOBS=    0.0 SIGMA= 29.1 PHAS=    0.0 FOM= 0.00 TEST= 0
INDE 22 24 68 FOBS=   99.7 SIGMA=  4.4 PHAS=  -88.7 FOM= 0.96 TEST= 0
INDE 22 24 70 FOBS=   14.4 SIGMA= 29.7 PHAS=   -3.4 FOM= 0.17 TEST= 0
INDE 22 25 23 FOBS=  183.2 SIGMA=  0.9 PHAS=  121.7 FOM= 0.89 TEST= 0
INDE 22 25 25 FOBS=  329.6 SIGMA=  0.7 PHAS= -118.9 FOM= 0.97 TEST= 0
INDE 22 25 27 FOBS=   50.0 SIGMA=  2.8 PHAS=  169.4 FOM= 0.61 TEST= 0
INDE 22 25 29 FOBS=  156.2 SIGMA=  1.1 PHAS= -167.2 FOM= 0.98 TEST= 0
INDE 22 25 31 FOBS=    0.0 SIGMA= 17.1 PHAS=    0.0 FOM= 0.00 TEST= 0
INDE 22 25 33 FOBS=  163.8 SIGMA=  1.1 PHAS=   15.3 FOM= 0.97 TEST= 0
INDE 22 25 35 FOBS=    0.0 SIGMA= 18.8 PHAS=    0.0 FOM= 0.00 TEST= 0
INDE 22 25 37 FOBS=  289.1 SIGMA=  0.7 PHAS=   92.5 FOM= 0.98 TEST= 0
INDE 22 25 39 FOBS=  196.5 SIGMA=  1.0 PHAS= -175.0 FOM= 0.99 TEST= 0
INDE 22 25 41 FOBS=   67.1 SIGMA=  2.6 PHAS=   21.0 FOM= 0.93 TEST= 0
INDE 22 25 43 FOBS=  146.4 SIGMA=  1.2 PHAS=   63.4 FOM= 0.91 TEST= 0
INDE 22 25 45 FOBS=  136.5 SIGMA=  1.3 PHAS=  136.2 FOM= 0.93 TEST= 0
INDE 22 25 47 FOBS=   76.9 SIGMA=  2.1 PHAS=   29.1 FOM= 0.86 TEST= 0
INDE 22 25 49 FOBS=  108.6 SIGMA=  1.4 PHAS=  177.4 FOM= 0.85 TEST= 0
INDE 22 25 51 FOBS=  137.6 SIGMA=  1.2 PHAS=  -68.9 FOM= 0.36 TEST= 0
INDE 22 25 53 FOBS=  107.7 SIGMA=  1.7 PHAS=  -43.2 FOM= 0.96 TEST= 0
INDE 22 25 55 FOBS=   82.8 SIGMA=  2.3 PHAS=   13.1 FOM= 0.86 TEST= 0
INDE 22 25 57 FOBS=    0.0 SIGMA= 23.9 PHAS=    0.0 FOM= 0.00 TEST= 0
INDE 22 25 59 FOBS=   36.9 SIGMA=  7.9 PHAS= -111.4 FOM= 0.38 TEST= 0
INDE 22 25 61 FOBS=   72.8 SIGMA=  4.0 PHAS=   97.9 FOM= 0.12 TEST= 0
INDE 22 25 63 FOBS=   31.9 SIGMA=  9.1 PHAS= -159.6 FOM= 0.41 TEST= 0
INDE 22 25 65 FOBS=   46.7 SIGMA=  7.6 PHAS=   55.9 FOM= 0.78 TEST= 0
```

*FIG. 12A - 464*

```
INDE 22 25 67 FOBS=    45.7 SIGMA=  9.4 PHAS=  153.7 FOM= 0.38 TEST= 0
INDE 22 25 69 FOBS=    32.7 SIGMA= 12.4 PHAS=  174.8 FOM= 0.78 TEST= 0
INDE 22 26 22 FOBS=   266.9 SIGMA=  0.6 PHAS=   -3.9 FOM= 0.93 TEST= 0
INDE 22 26 24 FOBS=    52.2 SIGMA=  2.7 PHAS=  142.2 FOM= 0.45 TEST= 0
INDE 22 26 26 FOBS=   284.4 SIGMA=  0.6 PHAS=  129.2 FOM= 0.94 TEST= 0
INDE 22 26 28 FOBS=    19.8 SIGMA=  6.9 PHAS=   61.9 FOM= 0.33 TEST= 0
INDE 22 26 30 FOBS=   268.8 SIGMA=  0.7 PHAS=  152.0 FOM= 0.95 TEST= 0
INDE 22 26 32 FOBS=   129.5 SIGMA=  1.3 PHAS=  -13.6 FOM= 0.95 TEST= 0
INDE 22 26 34 FOBS=    57.5 SIGMA=  2.7 PHAS=   27.0 FOM= 0.93 TEST= 0
INDE 22 26 36 FOBS=   155.4 SIGMA=  1.1 PHAS=    6.1 FOM= 0.90 TEST= 0
INDE 22 26 38 FOBS=   149.9 SIGMA=  1.1 PHAS=   70.7 FOM= 0.98 TEST= 0
INDE 22 26 40 FOBS=    74.0 SIGMA=  2.4 PHAS=   79.4 FOM= 0.52 TEST= 0
INDE 22 26 42 FOBS=    50.6 SIGMA=  3.7 PHAS=  -98.7 FOM= 0.78 TEST= 0
INDE 22 26 44 FOBS=   239.9 SIGMA=  0.8 PHAS=   68.5 FOM= 0.96 TEST= 0
INDE 22 26 46 FOBS=   141.7 SIGMA=  1.3 PHAS=   88.4 FOM= 0.86 TEST= 0
INDE 22 26 48 FOBS=    23.3 SIGMA=  7.5 PHAS=   38.2 FOM= 0.47 TEST= 0
INDE 22 26 50 FOBS=    38.9 SIGMA=  3.9 PHAS=   85.6 FOM= 0.29 TEST= 0
INDE 22 26 52 FOBS=   108.7 SIGMA=  1.7 PHAS= -155.3 FOM= 0.93 TEST= 0
INDE 22 26 54 FOBS=    75.4 SIGMA=  2.4 PHAS=  -46.0 FOM= 0.71 TEST= 0
INDE 22 26 56 FOBS=    72.4 SIGMA=  3.2 PHAS=  -59.6 FOM= 0.67 TEST= 0
INDE 22 26 58 FOBS=     0.0 SIGMA= 24.0 PHAS=    0.0 FOM= 0.00 TEST= 0
INDE 22 26 60 FOBS=    61.1 SIGMA=  4.8 PHAS=  172.2 FOM= 0.75 TEST= 0
INDE 22 26 62 FOBS=    33.7 SIGMA=  8.6 PHAS=  124.1 FOM= 0.73 TEST= 0
INDE 22 26 64 FOBS=    22.4 SIGMA= 16.0 PHAS=  -94.4 FOM= 0.21 TEST= 0
INDE 22 26 66 FOBS=    39.9 SIGMA= 10.9 PHAS=   -6.7 FOM= 0.58 TEST= 0
INDE 22 26 68 FOBS=    16.3 SIGMA= 25.4 PHAS=   79.4 FOM= 0.28 TEST= 0
INDE 22 27 23 FOBS=   149.6 SIGMA=  1.0 PHAS=  -40.4 FOM= 0.95 TEST= 1
INDE 22 27 25 FOBS=    61.2 SIGMA=  2.3 PHAS=   56.4 FOM= 0.84 TEST= 0
INDE 22 27 27 FOBS=   172.6 SIGMA=  0.9 PHAS=  -58.5 FOM= 0.96 TEST= 0
INDE 22 27 29 FOBS=    47.9 SIGMA=  3.5 PHAS=   58.0 FOM= 0.75 TEST= 0
INDE 22 27 31 FOBS=   160.7 SIGMA=  1.0 PHAS= -174.5 FOM= 0.90 TEST= 0
INDE 22 27 33 FOBS=    15.7 SIGMA= 10.9 PHAS=  -76.0 FOM= 0.51 TEST= 0
INDE 22 27 35 FOBS=   148.1 SIGMA=  1.1 PHAS=  -18.5 FOM= 0.89 TEST= 0
INDE 22 27 37 FOBS=   118.4 SIGMA=  1.4 PHAS=   -4.0 FOM= 0.88 TEST= 0
INDE 22 27 39 FOBS=   136.0 SIGMA=  1.2 PHAS= -123.9 FOM= 0.91 TEST= 0
INDE 22 27 41 FOBS=     0.0 SIGMA= 17.8 PHAS=    0.0 FOM= 0.00 TEST= 0
INDE 22 27 43 FOBS=   182.2 SIGMA=  0.9 PHAS=  -19.3 FOM= 0.97 TEST= 0
INDE 22 27 45 FOBS=   131.3 SIGMA=  1.2 PHAS=   42.3 FOM= 0.95 TEST= 0
INDE 22 27 47 FOBS=   114.1 SIGMA=  1.5 PHAS=  -19.6 FOM= 0.58 TEST= 1
INDE 22 27 49 FOBS=     0.0 SIGMA= 18.9 PHAS=    0.0 FOM= 0.00 TEST= 1
INDE 22 27 51 FOBS=    78.5 SIGMA=  2.4 PHAS=   62.0 FOM= 0.63 TEST= 0
INDE 22 27 53 FOBS=    46.2 SIGMA=  3.7 PHAS=  -27.3 FOM= 0.78 TEST= 0
INDE 22 27 55 FOBS=    40.8 SIGMA=  5.7 PHAS= -173.8 FOM= 0.55 TEST= 0
INDE 22 27 57 FOBS=   104.2 SIGMA=  2.3 PHAS=  143.2 FOM= 0.84 TEST= 0
INDE 22 27 59 FOBS=     0.0 SIGMA= 22.6 PHAS=    0.0 FOM= 0.00 TEST= 0
INDE 22 27 61 FOBS=    10.9 SIGMA= 26.5 PHAS=   45.9 FOM= 0.21 TEST= 0
INDE 22 27 63 FOBS=    72.4 SIGMA=  4.1 PHAS=   70.7 FOM= 0.77 TEST= 0
INDE 22 27 65 FOBS=    36.8 SIGMA= 11.4 PHAS=  -66.5 FOM= 0.37 TEST= 0
INDE 22 27 67 FOBS=     0.0 SIGMA= 29.0 PHAS=    0.0 FOM= 0.00 TEST= 0
INDE 22 27 69 FOBS=    21.5 SIGMA= 19.7 PHAS=  -45.8 FOM= 0.22 TEST= 0
INDE 22 28 22 FOBS=   127.8 SIGMA=  1.1 PHAS= -168.1 FOM= 0.88 TEST= 0
INDE 22 28 24 FOBS=    94.2 SIGMA=  1.5 PHAS=   17.2 FOM= 0.84 TEST= 0
INDE 22 28 26 FOBS=   190.2 SIGMA=  0.9 PHAS=  166.6 FOM= 0.81 TEST= 0
INDE 22 28 28 FOBS=    89.2 SIGMA=  1.7 PHAS= -174.0 FOM= 0.90 TEST= 0
INDE 22 28 30 FOBS=   288.3 SIGMA=  0.7 PHAS=  131.5 FOM= 0.97 TEST= 0
INDE 22 28 32 FOBS=   175.6 SIGMA=  1.0 PHAS=   79.8 FOM= 0.33 TEST= 1
INDE 22 28 34 FOBS=   156.1 SIGMA=  1.1 PHAS=   26.1 FOM= 0.96 TEST= 0
INDE 22 28 36 FOBS=   150.0 SIGMA=  1.1 PHAS=  -56.7 FOM= 0.92 TEST= 0
INDE 22 28 38 FOBS=   127.5 SIGMA=  1.3 PHAS=   62.6 FOM= 0.91 TEST= 0
INDE 22 28 40 FOBS=    89.6 SIGMA=  1.8 PHAS=  113.8 FOM= 0.79 TEST= 0
INDE 22 28 42 FOBS=   215.7 SIGMA=  0.8 PHAS= -127.8 FOM= 0.91 TEST= 0
INDE 22 28 44 FOBS=    83.4 SIGMA=  1.9 PHAS=  -93.2 FOM= 0.80 TEST= 0
INDE 22 28 46 FOBS=     0.0 SIGMA= 17.5 PHAS=    0.0 FOM= 0.00 TEST= 0
INDE 22 28 48 FOBS=   115.6 SIGMA=  1.4 PHAS= -139.9 FOM= 0.90 TEST= 0
INDE 22 28 50 FOBS=    42.7 SIGMA=  4.6 PHAS=   65.6 FOM= 0.87 TEST= 0
INDE 22 28 52 FOBS=    51.2 SIGMA=  3.8 PHAS=  -67.6 FOM= 0.72 TEST= 0
INDE 22 28 54 FOBS=    45.1 SIGMA=  4.0 PHAS=  157.9 FOM= 0.76 TEST= 0
INDE 22 28 56 FOBS=    27.6 SIGMA=  8.5 PHAS=   56.6 FOM= 0.32 TEST= 0
INDE 22 28 58 FOBS=    30.1 SIGMA=  8.5 PHAS=   55.8 FOM= 0.41 TEST= 0
INDE 22 28 60 FOBS=    63.4 SIGMA=  4.1 PHAS=  -42.4 FOM= 0.24 TEST= 0
```

*FIG. 12A - 465*

```
INDE 22 28 62 FOBS=   23.8 SIGMA= 16.2 PHAS= -117.3 FOM= 0.20 TEST= 0
INDE 22 28 64 FOBS=   97.6 SIGMA=  4.5 PHAS=  -44.3 FOM= 0.25 TEST= 1
INDE 22 28 66 FOBS=    0.0 SIGMA= 29.2 PHAS=    0.0 FOM= 0.00 TEST= 0
INDE 22 28 68 FOBS=    0.0 SIGMA= 29.4 PHAS=    0.0 FOM= 0.00 TEST= 0
INDE 22 29 23 FOBS=  258.0 SIGMA=  0.7 PHAS=  -20.5 FOM= 0.93 TEST= 0
INDE 22 29 25 FOBS=  175.3 SIGMA=  0.9 PHAS= -160.7 FOM= 0.96 TEST= 0
INDE 22 29 27 FOBS=   98.9 SIGMA=  1.7 PHAS= -109.2 FOM= 0.80 TEST= 0
INDE 22 29 29 FOBS=  270.3 SIGMA=  0.7 PHAS=   48.4 FOM= 0.97 TEST= 0
INDE 22 29 31 FOBS=   40.1 SIGMA=  4.3 PHAS=   45.6 FOM= 0.95 TEST= 0
INDE 22 29 33 FOBS=  327.2 SIGMA=  0.7 PHAS=  -27.5 FOM= 0.97 TEST= 0
INDE 22 29 35 FOBS=    0.0 SIGMA= 18.5 PHAS=    0.0 FOM= 0.00 TEST= 1
INDE 22 29 37 FOBS=   49.2 SIGMA=  3.3 PHAS=  -64.2 FOM= 0.59 TEST= 0
INDE 22 29 39 FOBS=  149.2 SIGMA=  1.1 PHAS=  -26.5 FOM= 0.95 TEST= 0
INDE 22 29 41 FOBS=  209.4 SIGMA=  0.9 PHAS=  166.3 FOM= 0.47 TEST= 1
INDE 22 29 43 FOBS=  120.0 SIGMA=  1.4 PHAS=  115.8 FOM= 0.43 TEST= 1
INDE 22 29 45 FOBS=  179.9 SIGMA=  0.9 PHAS=   82.5 FOM= 0.97 TEST= 0
INDE 22 29 47 FOBS=   22.1 SIGMA=  6.8 PHAS=  104.1 FOM= 0.10 TEST= 1
INDE 22 29 49 FOBS=   49.6 SIGMA=  3.5 PHAS=   42.5 FOM= 0.70 TEST= 0
INDE 22 29 51 FOBS=   15.2 SIGMA= 12.1 PHAS=   82.1 FOM= 0.06 TEST= 0
INDE 22 29 53 FOBS=   63.4 SIGMA=  2.7 PHAS=  -16.2 FOM= 0.75 TEST= 0
INDE 22 29 55 FOBS=   37.2 SIGMA=  7.0 PHAS=  141.6 FOM= 0.17 TEST= 0
INDE 22 29 57 FOBS=   67.0 SIGMA=  3.5 PHAS= -176.5 FOM= 0.87 TEST= 0
INDE 22 29 59 FOBS=   95.8 SIGMA=  2.5 PHAS=  -21.1 FOM= 0.88 TEST= 0
INDE 22 29 61 FOBS=   42.0 SIGMA=  5.4 PHAS=  129.1 FOM= 0.68 TEST= 0
INDE 22 29 63 FOBS=    0.0 SIGMA= 26.2 PHAS=    0.0 FOM= 0.00 TEST= 0
INDE 22 29 65 FOBS=   32.9 SIGMA= 12.9 PHAS=  -85.3 FOM= 0.67 TEST= 0
INDE 22 29 67 FOBS=   62.6 SIGMA=  7.0 PHAS=  122.3 FOM= 0.58 TEST= 0
INDE 22 30 22 FOBS=  287.2 SIGMA=  0.7 PHAS= -105.5 FOM= 0.95 TEST= 0
INDE 22 30 24 FOBS=  237.2 SIGMA=  0.8 PHAS=  156.2 FOM= 0.82 TEST= 0
INDE 22 30 26 FOBS=  331.0 SIGMA=  0.7 PHAS=  172.5 FOM= 0.98 TEST= 0
INDE 22 30 28 FOBS=   95.2 SIGMA=  1.8 PHAS=  -14.6 FOM= 0.89 TEST= 0
INDE 22 30 30 FOBS=   75.7 SIGMA=  2.3 PHAS=  -66.7 FOM= 0.92 TEST= 0
INDE 22 30 32 FOBS=   90.8 SIGMA=  1.9 PHAS= -125.1 FOM= 0.89 TEST= 0
INDE 22 30 34 FOBS=   87.1 SIGMA=  2.0 PHAS=  -37.5 FOM= 0.51 TEST= 0
INDE 22 30 36 FOBS=  141.2 SIGMA=  1.2 PHAS=   95.4 FOM= 0.81 TEST= 0
INDE 22 30 38 FOBS=   68.5 SIGMA=  2.4 PHAS=   69.9 FOM= 0.54 TEST= 0
INDE 22 30 40 FOBS=  263.6 SIGMA=  0.8 PHAS=  137.9 FOM= 0.96 TEST= 0
INDE 22 30 42 FOBS=   98.7 SIGMA=  1.6 PHAS=   -0.4 FOM= 0.90 TEST= 0
INDE 22 30 44 FOBS=  148.6 SIGMA=  1.1 PHAS=  -14.2 FOM= 0.96 TEST= 0
INDE 22 30 46 FOBS=   64.5 SIGMA=  2.4 PHAS=   26.7 FOM= 0.82 TEST= 0
INDE 22 30 48 FOBS=  115.4 SIGMA=  1.5 PHAS=  159.8 FOM= 0.85 TEST= 0
INDE 22 30 50 FOBS=    0.0 SIGMA= 19.0 PHAS=    0.0 FOM= 0.00 TEST= 0
INDE 22 30 52 FOBS=   90.4 SIGMA=  2.0 PHAS=   -7.3 FOM= 0.66 TEST= 0
INDE 22 30 54 FOBS=   53.4 SIGMA=  4.0 PHAS=  176.7 FOM= 0.79 TEST= 0
INDE 22 30 56 FOBS=   40.3 SIGMA=  5.2 PHAS=   52.1 FOM= 0.74 TEST= 0
INDE 22 30 58 FOBS=   72.5 SIGMA=  4.1 PHAS= -128.6 FOM= 0.85 TEST= 0
INDE 22 30 60 FOBS=   25.7 SIGMA=  9.7 PHAS=   34.7 FOM= 0.07 TEST= 0
INDE 22 30 62 FOBS=    0.0 SIGMA= 24.1 PHAS=    0.0 FOM= 0.00 TEST= 1
INDE 22 30 64 FOBS=   80.0 SIGMA=  5.5 PHAS=  164.9 FOM= 0.91 TEST= 0
INDE 22 30 66 FOBS=    0.0 SIGMA= 29.7 PHAS=    0.0 FOM= 0.00 TEST= 0
INDE 22 30 68 FOBS=   24.3 SIGMA= 18.2 PHAS=  -57.9 FOM= 0.05 TEST= 1
INDE 22 31 23 FOBS=  260.4 SIGMA=  0.7 PHAS=  104.4 FOM= 0.93 TEST= 0
INDE 22 31 25 FOBS=  354.1 SIGMA=  0.6 PHAS=  125.4 FOM= 0.42 TEST= 1
INDE 22 31 27 FOBS=   59.7 SIGMA=  3.0 PHAS=  123.1 FOM= 0.89 TEST= 0
INDE 22 31 29 FOBS=  266.3 SIGMA=  0.8 PHAS= -108.2 FOM= 0.97 TEST= 0
INDE 22 31 31 FOBS=   56.0 SIGMA=  3.2 PHAS= -129.7 FOM= 0.81 TEST= 0
INDE 22 31 33 FOBS=  173.6 SIGMA=  1.0 PHAS=  -32.1 FOM= 0.90 TEST= 0
INDE 22 31 35 FOBS=  124.9 SIGMA=  1.4 PHAS=    7.2 FOM= 0.92 TEST= 0
INDE 22 31 37 FOBS=  172.2 SIGMA=  1.0 PHAS=  -18.8 FOM= 0.93 TEST= 0
INDE 22 31 39 FOBS=  286.5 SIGMA=  0.8 PHAS=   41.5 FOM= 0.97 TEST= 0
INDE 22 31 41 FOBS=   56.8 SIGMA=  3.1 PHAS=   42.2 FOM= 0.53 TEST= 0
INDE 22 31 43 FOBS=  102.6 SIGMA=  1.6 PHAS=  -51.1 FOM= 0.94 TEST= 0
INDE 22 31 45 FOBS=    0.0 SIGMA= 18.2 PHAS=    0.0 FOM= 0.00 TEST= 0
INDE 22 31 47 FOBS=   53.8 SIGMA=  3.1 PHAS=  -13.5 FOM= 0.74 TEST= 0
INDE 22 31 49 FOBS=    0.0 SIGMA= 18.6 PHAS=    0.0 FOM= 0.00 TEST= 0
INDE 22 31 51 FOBS=   29.6 SIGMA=  5.5 PHAS=   85.3 FOM= 0.14 TEST= 0
INDE 22 31 53 FOBS=   42.8 SIGMA=  4.8 PHAS=   16.8 FOM= 0.57 TEST= 0
INDE 22 31 55 FOBS=    0.0 SIGMA= 20.5 PHAS=    0.0 FOM= 0.00 TEST= 0
INDE 22 31 57 FOBS=   74.5 SIGMA=  2.9 PHAS=  151.0 FOM= 0.95 TEST= 0
INDE 22 31 59 FOBS=   17.5 SIGMA= 14.5 PHAS= -109.1 FOM= 0.16 TEST= 0
```

*FIG. 12A - 466*

```
INDE  22  31  61 FOBS=    0.0 SIGMA= 24.1 PHAS=    0.0 FOM= 0.00 TEST= 0
INDE  22  31  63 FOBS=    0.0 SIGMA= 24.3 PHAS=    0.0 FOM= 0.00 TEST= 0
INDE  22  31  65 FOBS=    0.0 SIGMA= 29.8 PHAS=    0.0 FOM= 0.00 TEST= 0
INDE  22  31  67 FOBS=   56.5 SIGMA=  7.7 PHAS= -115.4 FOM= 0.80 TEST= 0
INDE  22  32  22 FOBS=  179.4 SIGMA=  0.9 PHAS=   14.9 FOM= 0.96 TEST= 0
INDE  22  32  24 FOBS=  136.2 SIGMA=  1.3 PHAS=   47.3 FOM= 0.91 TEST= 0
INDE  22  32  26 FOBS=   84.8 SIGMA=  2.1 PHAS=   37.4 FOM= 0.15 TEST= 1
INDE  22  32  28 FOBS=  190.5 SIGMA=  1.0 PHAS=  106.2 FOM= 0.93 TEST= 0
INDE  22  32  30 FOBS=  254.6 SIGMA=  0.8 PHAS=  140.8 FOM= 0.95 TEST= 0
INDE  22  32  32 FOBS=  138.3 SIGMA=  1.3 PHAS=  179.8 FOM= 0.72 TEST= 0
INDE  22  32  34 FOBS=   58.4 SIGMA=  3.0 PHAS=  -25.3 FOM= 0.43 TEST= 0
INDE  22  32  36 FOBS=   63.7 SIGMA=  2.6 PHAS=  156.4 FOM= 0.75 TEST= 0
INDE  22  32  38 FOBS=  256.7 SIGMA=  0.8 PHAS=  -57.2 FOM= 0.97 TEST= 0
INDE  22  32  40 FOBS=  164.4 SIGMA=  1.1 PHAS=  -63.8 FOM= 0.91 TEST= 0
INDE  22  32  42 FOBS=  169.3 SIGMA=  1.1 PHAS=  -81.7 FOM= 0.92 TEST= 0
INDE  22  32  44 FOBS=   21.4 SIGMA=  8.2 PHAS=  -83.3 FOM= 0.57 TEST= 0
INDE  22  32  46 FOBS=   57.2 SIGMA=  3.0 PHAS=    4.6 FOM= 0.71 TEST= 0
INDE  22  32  48 FOBS=   84.3 SIGMA=  2.0 PHAS= -169.3 FOM= 0.50 TEST= 1
INDE  22  32  50 FOBS=   68.6 SIGMA=  2.4 PHAS=  -24.1 FOM= 0.93 TEST= 0
INDE  22  32  52 FOBS=   51.3 SIGMA=  3.2 PHAS= -134.1 FOM= 0.35 TEST= 0
INDE  22  32  54 FOBS=   45.7 SIGMA=  5.0 PHAS=  125.3 FOM= 0.56 TEST= 0
INDE  22  32  56 FOBS=  108.4 SIGMA=  2.0 PHAS=   51.2 FOM= 0.93 TEST= 0
INDE  22  32  58 FOBS=   43.7 SIGMA=  5.8 PHAS=   77.6 FOM= 0.34 TEST= 0
INDE  22  32  60 FOBS=    0.0 SIGMA= 20.5 PHAS=    0.0 FOM= 0.00 TEST= 0
INDE  22  32  62 FOBS=   62.7 SIGMA=  4.8 PHAS=  107.7 FOM= 0.86 TEST= 0
INDE  22  32  64 FOBS=   42.5 SIGMA=  7.0 PHAS= -174.3 FOM= 0.80 TEST= 0
INDE  22  32  66 FOBS=   42.2 SIGMA= 10.4 PHAS=  146.7 FOM= 0.67 TEST= 0
INDE  22  33  23 FOBS=   27.5 SIGMA=  6.3 PHAS=  -93.9 FOM= 0.43 TEST= 0
INDE  22  33  25 FOBS=   41.7 SIGMA=  4.1 PHAS=  -52.0 FOM= 0.39 TEST= 0
INDE  22  33  27 FOBS=  153.4 SIGMA=  1.3 PHAS=  -73.0 FOM= 0.94 TEST= 0
INDE  22  33  29 FOBS=  196.2 SIGMA=  1.0 PHAS=    2.3 FOM= 0.95 TEST= 0
INDE  22  33  31 FOBS=  145.1 SIGMA=  1.2 PHAS=   50.1 FOM= 0.97 TEST= 0
INDE  22  33  33 FOBS=   72.5 SIGMA=  2.4 PHAS=  -20.8 FOM= 0.44 TEST= 0
INDE  22  33  35 FOBS=  104.2 SIGMA=  1.6 PHAS=   85.4 FOM= 0.62 TEST= 0
INDE  22  33  37 FOBS=  197.5 SIGMA=  0.9 PHAS=  -73.4 FOM= 0.96 TEST= 0
INDE  22  33  39 FOBS=  117.3 SIGMA=  1.4 PHAS=  105.1 FOM= 0.79 TEST= 0
INDE  22  33  41 FOBS=   90.6 SIGMA=  1.9 PHAS=  -89.8 FOM= 0.25 TEST= 0
INDE  22  33  43 FOBS=   94.3 SIGMA=  1.9 PHAS= -111.7 FOM= 0.85 TEST= 0
INDE  22  33  45 FOBS=  239.9 SIGMA=  0.9 PHAS=  -71.1 FOM= 0.98 TEST= 0
INDE  22  33  47 FOBS=   81.6 SIGMA=  2.1 PHAS=    8.7 FOM= 0.81 TEST= 0
INDE  22  33  49 FOBS=   55.1 SIGMA=  3.0 PHAS=  -82.0 FOM= 0.42 TEST= 0
INDE  22  33  51 FOBS=    0.0 SIGMA= 18.5 PHAS=    0.0 FOM= 0.00 TEST= 0
INDE  22  33  53 FOBS=   39.6 SIGMA=  5.2 PHAS=   97.4 FOM= 0.66 TEST= 0
INDE  22  33  55 FOBS=   50.2 SIGMA=  4.3 PHAS=  -52.3 FOM= 0.81 TEST= 0
INDE  22  33  57 FOBS=    0.0 SIGMA= 21.4 PHAS=    0.0 FOM= 0.00 TEST= 1
INDE  22  33  59 FOBS=    0.0 SIGMA= 20.5 PHAS=    0.0 FOM= 0.00 TEST= 0
INDE  22  33  61 FOBS=   76.0 SIGMA=  2.6 PHAS=  -22.0 FOM= 0.89 TEST= 0
INDE  22  33  63 FOBS=    0.0 SIGMA= 22.7 PHAS=    0.0 FOM= 0.00 TEST= 0
INDE  22  33  65 FOBS=    0.0 SIGMA= 24.4 PHAS=    0.0 FOM= 0.00 TEST= 0
INDE  22  34  22 FOBS=  158.9 SIGMA=  1.3 PHAS=   82.8 FOM= 0.94 TEST= 0
INDE  22  34  24 FOBS=   66.0 SIGMA=  2.8 PHAS= -176.5 FOM= 0.87 TEST= 1
INDE  22  34  26 FOBS=  211.3 SIGMA=  1.0 PHAS= -148.3 FOM= 0.99 TEST= 0
INDE  22  34  28 FOBS=  150.4 SIGMA=  1.3 PHAS= -171.0 FOM= 0.91 TEST= 0
INDE  22  34  30 FOBS=  124.9 SIGMA=  1.5 PHAS=  -66.5 FOM= 0.96 TEST= 0
INDE  22  34  32 FOBS=    0.0 SIGMA= 19.5 PHAS=    0.0 FOM= 0.00 TEST= 0
INDE  22  34  34 FOBS=   85.7 SIGMA=  2.0 PHAS=   63.8 FOM= 0.65 TEST= 0
INDE  22  34  36 FOBS=  130.1 SIGMA=  1.3 PHAS= -158.4 FOM= 0.89 TEST= 0
INDE  22  34  38 FOBS=   84.7 SIGMA=  1.9 PHAS=  -87.6 FOM= 0.56 TEST= 0
INDE  22  34  40 FOBS=  105.5 SIGMA=  1.6 PHAS=   60.4 FOM= 0.83 TEST= 0
INDE  22  34  42 FOBS=   85.6 SIGMA=  2.3 PHAS=  -86.3 FOM= 0.88 TEST= 0
INDE  22  34  44 FOBS=  278.0 SIGMA=  1.0 PHAS=  152.0 FOM= 0.99 TEST= 0
INDE  22  34  46 FOBS=  115.2 SIGMA=  1.8 PHAS= -131.1 FOM= 0.86 TEST= 0
INDE  22  34  48 FOBS=   83.7 SIGMA=  2.3 PHAS= -168.3 FOM= 0.85 TEST= 0
INDE  22  34  50 FOBS=  107.8 SIGMA=  1.6 PHAS=   58.2 FOM= 0.86 TEST= 0
INDE  22  34  52 FOBS=    9.4 SIGMA= 20.2 PHAS=  -34.4 FOM= 0.05 TEST= 0
INDE  22  34  54 FOBS=    0.0 SIGMA= 20.6 PHAS=    0.0 FOM= 0.00 TEST= 0
INDE  22  34  56 FOBS=    0.0 SIGMA= 21.3 PHAS=    0.0 FOM= 0.00 TEST= 1
INDE  22  34  58 FOBS=   58.4 SIGMA=  4.0 PHAS= -166.0 FOM= 0.37 TEST= 0
INDE  22  34  60 FOBS=   48.9 SIGMA=  4.4 PHAS= -155.3 FOM= 0.58 TEST= 1
INDE  22  34  62 FOBS=   97.8 SIGMA=  2.1 PHAS=  168.3 FOM= 0.94 TEST= 0
```

*FIG. 12A - 467*

```
INDE 22 34 64 FOBS=   0.0 SIGMA= 25.5 PHAS=   0.0 FOM= 0.00 TEST= 0
INDE 22 34 66 FOBS=  60.7 SIGMA=  4.5 PHAS= 106.7 FOM= 0.82 TEST= 0
INDE 22 35 23 FOBS= 176.4 SIGMA=  1.1 PHAS=   5.9 FOM= 0.98 TEST= 0
INDE 22 35 25 FOBS=   0.0 SIGMA= 19.6 PHAS=   0.0 FOM= 0.00 TEST= 0
INDE 22 35 27 FOBS=  75.9 SIGMA=  2.5 PHAS=-146.1 FOM= 0.96 TEST= 1
INDE 22 35 29 FOBS= 216.8 SIGMA=  1.0 PHAS=  39.1 FOM= 0.98 TEST= 0
INDE 22 35 31 FOBS= 105.3 SIGMA=  1.8 PHAS= -21.3 FOM= 0.60 TEST= 0
INDE 22 35 33 FOBS= 117.4 SIGMA=  1.5 PHAS=  23.6 FOM= 0.83 TEST= 0
INDE 22 35 35 FOBS=   0.0 SIGMA= 19.0 PHAS=   0.0 FOM= 0.00 TEST= 0
INDE 22 35 37 FOBS= 163.6 SIGMA=  1.1 PHAS= 167.5 FOM= 0.86 TEST= 0
INDE 22 35 39 FOBS= 104.4 SIGMA=  1.6 PHAS=  24.1 FOM= 0.82 TEST= 0
INDE 22 35 41 FOBS=  87.9 SIGMA=  2.0 PHAS=-131.8 FOM= 0.91 TEST= 0
INDE 22 35 43 FOBS= 151.6 SIGMA=  1.4 PHAS=   5.7 FOM= 0.87 TEST= 1
INDE 22 35 45 FOBS=  43.4 SIGMA=  4.3 PHAS= 119.5 FOM= 0.67 TEST= 1
INDE 22 35 47 FOBS= 106.4 SIGMA=  1.8 PHAS= 121.1 FOM= 0.92 TEST= 0
INDE 22 35 49 FOBS= 173.8 SIGMA=  1.2 PHAS=  16.8 FOM= 0.30 TEST= 1
INDE 22 35 51 FOBS=  48.8 SIGMA=  3.8 PHAS=  31.2 FOM= 0.79 TEST= 0
INDE 22 35 53 FOBS=   0.0 SIGMA= 21.8 PHAS=   0.0 FOM= 0.00 TEST= 0
INDE 22 35 55 FOBS=   0.0 SIGMA= 20.7 PHAS=   0.0 FOM= 0.00 TEST= 0
INDE 22 35 57 FOBS=  57.3 SIGMA=  3.7 PHAS= 179.9 FOM= 0.54 TEST= 0
INDE 22 35 59 FOBS=   0.0 SIGMA= 20.7 PHAS=   0.0 FOM= 0.00 TEST= 0
INDE 22 35 61 FOBS=  14.7 SIGMA= 16.1 PHAS=  52.9 FOM= 0.36 TEST= 0
INDE 22 35 63 FOBS=  41.3 SIGMA=  4.9 PHAS=  71.7 FOM= 0.78 TEST= 0
INDE 22 35 65 FOBS=   0.0 SIGMA= 24.9 PHAS=   0.0 FOM= 0.00 TEST= 0
INDE 22 36 22 FOBS= 235.0 SIGMA=  1.0 PHAS= -83.5 FOM= 0.91 TEST= 0
INDE 22 36 24 FOBS= 239.9 SIGMA=  0.9 PHAS=-117.8 FOM= 0.95 TEST= 0
INDE 22 36 26 FOBS=  48.4 SIGMA=  3.8 PHAS= -95.2 FOM= 0.76 TEST= 0
INDE 22 36 28 FOBS=  51.2 SIGMA=  3.6 PHAS= -91.4 FOM= 0.85 TEST= 0
INDE 22 36 30 FOBS= 147.1 SIGMA=  1.4 PHAS= -76.3 FOM= 0.92 TEST= 0
INDE 22 36 32 FOBS= 148.9 SIGMA=  1.4 PHAS= -52.1 FOM= 0.88 TEST= 0
INDE 22 36 34 FOBS= 171.9 SIGMA=  1.0 PHAS= -17.0 FOM= 0.94 TEST= 0
INDE 22 36 36 FOBS= 225.2 SIGMA=  0.9 PHAS=  71.4 FOM= 0.91 TEST= 0
INDE 22 36 38 FOBS=   0.0 SIGMA= 18.3 PHAS=   0.0 FOM= 0.00 TEST= 0
INDE 22 36 40 FOBS=  81.7 SIGMA=  2.2 PHAS=  94.4 FOM= 0.90 TEST= 0
INDE 22 36 42 FOBS= 162.0 SIGMA=  1.2 PHAS= -96.1 FOM= 0.94 TEST= 0
INDE 22 36 44 FOBS=  21.3 SIGMA= 10.2 PHAS= -46.5 FOM= 0.46 TEST= 0
INDE 22 36 46 FOBS=  80.6 SIGMA=  2.4 PHAS=  68.1 FOM= 0.75 TEST= 0
INDE 22 36 48 FOBS= 137.9 SIGMA=  1.5 PHAS= -83.0 FOM= 0.94 TEST= 0
INDE 22 36 50 FOBS=  89.9 SIGMA=  2.1 PHAS= -52.9 FOM= 0.86 TEST= 0
INDE 22 36 52 FOBS=  44.9 SIGMA=  4.1 PHAS=  34.4 FOM= 0.72 TEST= 0
INDE 22 36 54 FOBS=  48.8 SIGMA=  4.5 PHAS= 165.4 FOM= 0.75 TEST= 0
INDE 22 36 56 FOBS=  20.4 SIGMA= 11.4 PHAS=-128.4 FOM= 0.37 TEST= 0
INDE 22 36 58 FOBS=   0.0 SIGMA= 20.7 PHAS=   0.0 FOM= 0.00 TEST= 0
INDE 22 36 60 FOBS=  41.5 SIGMA=  6.3 PHAS=-178.5 FOM= 0.25 TEST= 0
INDE 22 36 62 FOBS=   0.0 SIGMA= 20.8 PHAS=   0.0 FOM= 0.00 TEST= 0
INDE 22 36 64 FOBS=  53.2 SIGMA=  5.2 PHAS= -95.3 FOM= 0.76 TEST= 0
INDE 22 37 23 FOBS= 294.9 SIGMA=  0.9 PHAS= 142.5 FOM= 0.97 TEST= 0
INDE 22 37 25 FOBS=  86.5 SIGMA=  2.2 PHAS= -61.5 FOM= 0.72 TEST= 0
INDE 22 37 27 FOBS= 185.6 SIGMA=  1.1 PHAS= -89.3 FOM= 0.95 TEST= 0
INDE 22 37 29 FOBS= 190.2 SIGMA=  1.1 PHAS= 135.0 FOM= 0.92 TEST= 0
INDE 22 37 31 FOBS=  51.1 SIGMA=  4.0 PHAS=  39.4 FOM= 0.77 TEST= 0
INDE 22 37 33 FOBS= 236.7 SIGMA=  0.9 PHAS= -68.3 FOM= 0.96 TEST= 0
INDE 22 37 35 FOBS=  91.9 SIGMA=  1.8 PHAS= -36.0 FOM= 0.83 TEST= 0
INDE 22 37 37 FOBS=  52.0 SIGMA=  3.5 PHAS= -17.9 FOM= 0.84 TEST= 0
INDE 22 37 39 FOBS= 210.4 SIGMA=  1.0 PHAS=   1.6 FOM= 0.94 TEST= 0
INDE 22 37 41 FOBS=  98.2 SIGMA=  1.8 PHAS=-137.9 FOM= 0.86 TEST= 0
INDE 22 37 43 FOBS=  83.3 SIGMA=  2.1 PHAS=-108.7 FOM= 0.93 TEST= 0
INDE 22 37 45 FOBS=  25.6 SIGMA=  7.8 PHAS= 122.8 FOM= 0.15 TEST= 0
INDE 22 37 47 FOBS= 115.0 SIGMA=  1.7 PHAS= 116.1 FOM= 0.85 TEST= 0
INDE 22 37 49 FOBS=  59.4 SIGMA=  3.2 PHAS= 139.9 FOM= 0.24 TEST= 0
INDE 22 37 51 FOBS= 104.9 SIGMA=  1.8 PHAS=  24.9 FOM= 0.92 TEST= 0
INDE 22 37 53 FOBS=  67.8 SIGMA=  3.0 PHAS=   4.3 FOM= 0.87 TEST= 0
INDE 22 37 55 FOBS= 135.9 SIGMA=  1.7 PHAS= 102.0 FOM= 0.95 TEST= 0
INDE 22 37 57 FOBS=  67.7 SIGMA=  3.2 PHAS= 179.9 FOM= 0.60 TEST= 0
INDE 22 37 59 FOBS=   0.0 SIGMA= 20.8 PHAS=   0.0 FOM= 0.00 TEST= 0
INDE 22 37 61 FOBS=  88.3 SIGMA=  2.6 PHAS=   2.4 FOM= 0.32 TEST= 0
INDE 22 37 63 FOBS=   0.0 SIGMA= 22.0 PHAS=   0.0 FOM= 0.00 TEST= 0
INDE 22 38 22 FOBS= 165.9 SIGMA=  1.3 PHAS=  88.5 FOM= 0.92 TEST= 0
INDE 22 38 24 FOBS= 147.6 SIGMA=  1.5 PHAS=-106.9 FOM= 0.94 TEST= 0
INDE 22 38 26 FOBS= 221.0 SIGMA=  0.9 PHAS=-164.3 FOM= 0.96 TEST= 0
```

*FIG. 12A - 468*

```
INDE 22 38 28 FOBS=   34.3 SIGMA=  5.2 PHAS=  138.4 FOM= 0.58 TEST= 0
INDE 22 38 30 FOBS=  180.2 SIGMA=  1.1 PHAS=   27.1 FOM= 0.94 TEST= 0
INDE 22 38 32 FOBS=  168.6 SIGMA=  1.1 PHAS= -139.4 FOM= 0.96 TEST= 0
INDE 22 38 34 FOBS=   74.4 SIGMA=  2.3 PHAS=  -83.4 FOM= 0.72 TEST= 0
INDE 22 38 36 FOBS=   38.2 SIGMA=  4.9 PHAS=  -58.8 FOM= 0.61 TEST= 0
INDE 22 38 38 FOBS=  182.1 SIGMA=  1.1 PHAS=  -87.0 FOM= 0.95 TEST= 0
INDE 22 38 40 FOBS=    0.0 SIGMA= 19.2 PHAS=    0.0 FOM= 0.00 TEST= 0
INDE 22 38 42 FOBS=  167.6 SIGMA=  1.1 PHAS=  138.1 FOM= 0.94 TEST= 0
INDE 22 38 44 FOBS=   39.6 SIGMA=  4.6 PHAS=   54.7 FOM= 0.82 TEST= 0
INDE 22 38 46 FOBS=   73.3 SIGMA=  2.6 PHAS= -136.3 FOM= 0.46 TEST= 0
INDE 22 38 48 FOBS=   87.6 SIGMA=  2.2 PHAS=   -9.1 FOM= 0.79 TEST= 0
INDE 22 38 50 FOBS=   88.7 SIGMA=  2.2 PHAS=  -81.2 FOM= 0.91 TEST= 0
INDE 22 38 52 FOBS=    0.0 SIGMA= 21.7 PHAS=    0.0 FOM= 0.00 TEST= 0
INDE 22 38 54 FOBS=   57.2 SIGMA=  3.8 PHAS=    1.6 FOM= 0.76 TEST= 0
INDE 22 38 56 FOBS=   90.6 SIGMA=  2.5 PHAS=  -60.0 FOM= 0.88 TEST= 0
INDE 22 38 58 FOBS=   55.3 SIGMA=  4.0 PHAS=  -99.1 FOM= 0.71 TEST= 0
INDE 22 38 60 FOBS=   65.5 SIGMA=  3.4 PHAS=   82.8 FOM= 0.03 TEST= 1
INDE 22 38 62 FOBS=   78.3 SIGMA=  3.2 PHAS=   47.8 FOM= 0.84 TEST= 0
INDE 22 38 64 FOBS=   46.5 SIGMA=  6.4 PHAS= -129.9 FOM= 0.61 TEST= 0
INDE 22 39 23 FOBS=  171.1 SIGMA=  1.3 PHAS=  101.4 FOM= 0.91 TEST= 0
INDE 22 39 25 FOBS=  107.9 SIGMA=  1.9 PHAS=  137.4 FOM= 0.66 TEST= 0
INDE 22 39 27 FOBS=  135.6 SIGMA=  1.4 PHAS=  113.6 FOM= 0.88 TEST= 0
INDE 22 39 29 FOBS=   34.7 SIGMA=  5.4 PHAS=    6.3 FOM= 0.25 TEST= 0
INDE 22 39 31 FOBS=  118.2 SIGMA=  1.6 PHAS=  109.2 FOM= 0.79 TEST= 0
INDE 22 39 33 FOBS=   85.9 SIGMA=  2.1 PHAS=  -46.1 FOM= 0.88 TEST= 0
INDE 22 39 35 FOBS=    0.0 SIGMA= 18.9 PHAS=    0.0 FOM= 0.00 TEST= 0
INDE 22 39 37 FOBS=  136.5 SIGMA=  1.4 PHAS= -178.1 FOM= 0.78 TEST= 1
INDE 22 39 39 FOBS=    0.0 SIGMA= 19.2 PHAS=    0.0 FOM= 0.00 TEST= 0
INDE 22 39 41 FOBS=   44.9 SIGMA=  4.1 PHAS=   43.6 FOM= 0.28 TEST= 1
INDE 22 39 43 FOBS=   89.2 SIGMA=  2.0 PHAS=  -36.2 FOM= 0.93 TEST= 0
INDE 22 39 45 FOBS=   80.3 SIGMA=  2.2 PHAS=  -13.3 FOM= 0.84 TEST= 0
INDE 22 39 47 FOBS=   54.0 SIGMA=  3.5 PHAS=  142.5 FOM= 0.48 TEST= 0
INDE 22 39 49 FOBS=   85.9 SIGMA=  2.2 PHAS= -128.4 FOM= 0.09 TEST= 1
INDE 22 39 51 FOBS=   62.5 SIGMA=  3.0 PHAS=  -79.6 FOM= 0.53 TEST= 0
INDE 22 39 53 FOBS=   73.8 SIGMA=  2.8 PHAS=  -35.5 FOM= 0.80 TEST= 0
INDE 22 39 55 FOBS=    0.0 SIGMA= 21.8 PHAS=    0.0 FOM= 0.00 TEST= 0
INDE 22 39 57 FOBS=   53.1 SIGMA=  4.2 PHAS= -131.8 FOM= 0.78 TEST= 0
INDE 22 39 59 FOBS=    0.0 SIGMA= 21.9 PHAS=    0.0 FOM= 0.00 TEST= 0
INDE 22 39 61 FOBS=  130.1 SIGMA=  2.1 PHAS=  -75.6 FOM= 0.97 TEST= 0
INDE 22 39 63 FOBS=   44.0 SIGMA=  7.9 PHAS=  -90.3 FOM= 0.04 TEST= 1
INDE 22 40 22 FOBS=   65.8 SIGMA=  3.1 PHAS=   53.3 FOM= 0.34 TEST= 0
INDE 22 40 24 FOBS=  178.8 SIGMA=  1.2 PHAS=  -25.5 FOM= 0.90 TEST= 0
INDE 22 40 26 FOBS=  157.6 SIGMA=  1.3 PHAS=  105.6 FOM= 0.87 TEST= 1
INDE 22 40 28 FOBS=  116.2 SIGMA=  1.6 PHAS=  -27.8 FOM= 0.86 TEST= 1
INDE 22 40 30 FOBS=   85.5 SIGMA=  2.1 PHAS=  -12.2 FOM= 0.81 TEST= 0
INDE 22 40 32 FOBS=  145.9 SIGMA=  1.3 PHAS= -170.1 FOM= 0.89 TEST= 0
INDE 22 40 34 FOBS=   44.4 SIGMA=  4.7 PHAS=  172.5 FOM= 0.66 TEST= 0
INDE 22 40 36 FOBS=   77.5 SIGMA=  2.4 PHAS= -107.4 FOM= 0.72 TEST= 0
INDE 22 40 38 FOBS=   18.5 SIGMA= 10.2 PHAS=  143.8 FOM= 0.29 TEST= 0
INDE 22 40 40 FOBS=   60.4 SIGMA=  3.0 PHAS=   74.3 FOM= 0.43 TEST= 1
INDE 22 40 42 FOBS=   58.2 SIGMA=  3.0 PHAS=   68.1 FOM= 0.87 TEST= 0
INDE 22 40 44 FOBS=   48.6 SIGMA=  3.7 PHAS= -149.9 FOM= 0.84 TEST= 0
INDE 22 40 46 FOBS=   80.1 SIGMA=  2.3 PHAS=  -72.8 FOM= 0.81 TEST= 0
INDE 22 40 48 FOBS=   30.1 SIGMA=  6.7 PHAS=  -13.0 FOM= 0.42 TEST= 0
INDE 22 40 50 FOBS=   52.3 SIGMA=  3.6 PHAS= -149.4 FOM= 0.82 TEST= 0
INDE 22 40 52 FOBS=    0.0 SIGMA= 20.2 PHAS=    0.0 FOM= 0.00 TEST= 0
INDE 22 40 54 FOBS=    0.0 SIGMA= 21.8 PHAS=    0.0 FOM= 0.00 TEST= 0
INDE 22 40 56 FOBS=   64.7 SIGMA=  3.5 PHAS= -101.6 FOM= 0.55 TEST= 0
INDE 22 40 58 FOBS=   69.1 SIGMA=  3.2 PHAS=  -94.9 FOM= 0.67 TEST= 0
INDE 22 40 60 FOBS=    0.0 SIGMA= 25.6 PHAS=    0.0 FOM= 0.00 TEST= 1
INDE 22 40 62 FOBS=   53.7 SIGMA=  7.9 PHAS=  165.9 FOM= 0.83 TEST= 0
INDE 22 41 23 FOBS=  128.6 SIGMA=  1.5 PHAS=  -32.0 FOM= 0.80 TEST= 0
INDE 22 41 25 FOBS=   54.4 SIGMA=  3.6 PHAS=  -56.9 FOM= 0.68 TEST= 0
INDE 22 41 27 FOBS=  121.5 SIGMA=  1.5 PHAS=   76.8 FOM= 0.92 TEST= 0
INDE 22 41 29 FOBS=    0.0 SIGMA= 19.2 PHAS=    0.0 FOM= 0.00 TEST= 0
INDE 22 41 31 FOBS=  149.4 SIGMA=  1.4 PHAS=   52.9 FOM= 0.93 TEST= 0
INDE 22 41 33 FOBS=   99.5 SIGMA=  2.1 PHAS=   18.2 FOM= 0.92 TEST= 1
INDE 22 41 35 FOBS=   38.3 SIGMA=  4.9 PHAS=  153.2 FOM= 0.66 TEST= 0
INDE 22 41 37 FOBS=   66.6 SIGMA=  2.7 PHAS=   80.8 FOM= 0.76 TEST= 0
INDE 22 41 39 FOBS=  157.2 SIGMA=  1.2 PHAS=    6.2 FOM= 0.94 TEST= 0
```

*FIG. 12A - 469*

```
INDE 22 41 41 FOBS=   120.5 SIGMA=  1.5 PHAS=  -58.7 FOM= 0.93 TEST= 0
INDE 22 41 43 FOBS=    46.2 SIGMA=  4.1 PHAS=   19.9 FOM= 0.60 TEST= 0
INDE 22 41 45 FOBS=    84.0 SIGMA=  2.1 PHAS=   16.3 FOM= 0.75 TEST= 0
INDE 22 41 47 FOBS=    62.6 SIGMA=  3.1 PHAS=  -84.3 FOM= 0.41 TEST= 0
INDE 22 41 49 FOBS=   139.2 SIGMA=  1.4 PHAS=  108.4 FOM= 0.45 TEST= 1
INDE 22 41 51 FOBS=    99.3 SIGMA=  1.9 PHAS=   70.7 FOM= 0.86 TEST= 0
INDE 22 41 53 FOBS=    98.9 SIGMA=  2.1 PHAS=   77.2 FOM= 0.94 TEST= 0
INDE 22 41 55 FOBS=    85.2 SIGMA=  2.6 PHAS=  -92.6 FOM= 0.92 TEST= 0
INDE 22 41 57 FOBS=    48.4 SIGMA=  5.7 PHAS=  175.6 FOM= 0.70 TEST= 0
INDE 22 41 59 FOBS=    65.8 SIGMA=  4.9 PHAS=  152.5 FOM= 0.92 TEST= 0
INDE 22 41 61 FOBS=   104.7 SIGMA=  2.9 PHAS=  -44.3 FOM= 0.94 TEST= 0
INDE 22 42 22 FOBS=   172.7 SIGMA=  1.1 PHAS= -130.6 FOM= 0.92 TEST= 0
INDE 22 42 24 FOBS=    83.6 SIGMA=  2.3 PHAS= -151.6 FOM= 0.88 TEST= 0
INDE 22 42 26 FOBS=     0.0 SIGMA= 20.5 PHAS=    0.0 FOM= 0.00 TEST= 0
INDE 22 42 28 FOBS=   152.9 SIGMA=  1.2 PHAS=  -30.6 FOM= 0.91 TEST= 0
INDE 22 42 30 FOBS=    88.8 SIGMA=  2.3 PHAS=  -51.0 FOM= 0.78 TEST= 0
INDE 22 42 32 FOBS=   228.8 SIGMA=  1.0 PHAS= -102.7 FOM= 0.97 TEST= 0
INDE 22 42 34 FOBS=   144.0 SIGMA=  1.5 PHAS=   94.6 FOM= 0.87 TEST= 0
INDE 22 42 36 FOBS=   108.5 SIGMA=  1.7 PHAS=  -75.7 FOM= 0.91 TEST= 0
INDE 22 42 38 FOBS=    88.7 SIGMA=  2.0 PHAS= -105.4 FOM= 0.91 TEST= 0
INDE 22 42 40 FOBS=    39.7 SIGMA=  4.6 PHAS=  152.5 FOM= 0.33 TEST= 0
INDE 22 42 42 FOBS=    63.6 SIGMA=  2.8 PHAS=  149.6 FOM= 0.69 TEST= 1
INDE 22 42 44 FOBS=    98.1 SIGMA=  1.8 PHAS= -121.9 FOM= 0.82 TEST= 0
INDE 22 42 46 FOBS=    20.5 SIGMA=  8.7 PHAS=  -94.6 FOM= 0.18 TEST= 0
INDE 22 42 48 FOBS=    83.0 SIGMA=  2.3 PHAS=    5.9 FOM= 0.42 TEST= 1
INDE 22 42 50 FOBS=    82.1 SIGMA=  2.4 PHAS=   38.5 FOM= 0.96 TEST= 0
INDE 22 42 52 FOBS=    79.2 SIGMA=  2.6 PHAS=   -9.8 FOM= 0.92 TEST= 0
INDE 22 42 54 FOBS=    89.7 SIGMA=  2.3 PHAS= -110.4 FOM= 0.93 TEST= 0
INDE 22 42 56 FOBS=    39.8 SIGMA=  7.8 PHAS=   44.9 FOM= 0.70 TEST= 0
INDE 22 42 58 FOBS=    61.5 SIGMA=  4.7 PHAS=   -5.3 FOM= 0.16 TEST= 1
INDE 22 42 60 FOBS=    43.9 SIGMA=  7.8 PHAS=  179.4 FOM= 0.34 TEST= 0
INDE 22 43 23 FOBS=    54.6 SIGMA=  3.2 PHAS=  129.0 FOM= 0.82 TEST= 0
INDE 22 43 25 FOBS=   120.0 SIGMA=  1.6 PHAS=  145.0 FOM= 0.58 TEST= 0
INDE 22 43 27 FOBS=   123.3 SIGMA=  1.8 PHAS= -135.3 FOM= 0.79 TEST= 0
INDE 22 43 29 FOBS=    29.2 SIGMA=  7.2 PHAS=  123.0 FOM= 0.21 TEST= 0
INDE 22 43 31 FOBS=   183.8 SIGMA=  1.2 PHAS=  115.7 FOM= 0.92 TEST= 0
INDE 22 43 33 FOBS=   140.3 SIGMA=  1.5 PHAS=  105.2 FOM= 0.23 TEST= 1
INDE 22 43 35 FOBS=    55.3 SIGMA=  3.6 PHAS=  164.0 FOM= 0.84 TEST= 0
INDE 22 43 37 FOBS=    62.0 SIGMA=  2.9 PHAS= -168.0 FOM= 0.83 TEST= 0
INDE 22 43 39 FOBS=    66.3 SIGMA=  2.7 PHAS=   21.0 FOM= 0.85 TEST= 0
INDE 22 43 41 FOBS=   123.6 SIGMA=  1.5 PHAS=   11.4 FOM= 0.93 TEST= 0
INDE 22 43 43 FOBS=   107.8 SIGMA=  1.7 PHAS=   72.4 FOM= 0.90 TEST= 0
INDE 22 43 45 FOBS=     0.0 SIGMA= 19.0 PHAS=    0.0 FOM= 0.00 TEST= 0
INDE 22 43 47 FOBS=    52.2 SIGMA=  3.3 PHAS=  -54.0 FOM= 0.66 TEST= 0
INDE 22 43 49 FOBS=    31.4 SIGMA=  6.1 PHAS=  -66.7 FOM= 0.58 TEST= 0
INDE 22 43 51 FOBS=   107.0 SIGMA=  2.0 PHAS=    2.2 FOM= 0.94 TEST= 0
INDE 22 43 53 FOBS=   110.3 SIGMA=  1.9 PHAS=  156.5 FOM= 0.96 TEST= 0
INDE 22 43 55 FOBS=    87.9 SIGMA=  2.6 PHAS= -103.2 FOM= 0.93 TEST= 0
INDE 22 43 57 FOBS=    40.3 SIGMA=  7.0 PHAS=  -76.2 FOM= 0.22 TEST= 0
INDE 22 43 59 FOBS=    53.6 SIGMA=  6.2 PHAS=  129.5 FOM= 0.87 TEST= 0
INDE 22 44 22 FOBS=    71.4 SIGMA=  2.5 PHAS=  121.5 FOM= 0.44 TEST= 1
INDE 22 44 24 FOBS=    66.8 SIGMA=  2.6 PHAS=  135.8 FOM= 0.18 TEST= 0
INDE 22 44 26 FOBS=    75.7 SIGMA=  2.6 PHAS=  143.4 FOM= 0.85 TEST= 0
INDE 22 44 28 FOBS=    35.8 SIGMA=  6.2 PHAS= -139.5 FOM= 0.07 TEST= 1
INDE 22 44 30 FOBS=    88.4 SIGMA=  2.3 PHAS=   95.7 FOM= 0.62 TEST= 0
INDE 22 44 32 FOBS=   149.6 SIGMA=  1.4 PHAS=  -23.7 FOM= 0.93 TEST= 0
INDE 22 44 34 FOBS=   140.1 SIGMA=  1.5 PHAS=   75.9 FOM= 0.92 TEST= 0
INDE 22 44 36 FOBS=    65.9 SIGMA=  3.1 PHAS=  168.3 FOM= 0.42 TEST= 0
INDE 22 44 38 FOBS=    43.2 SIGMA=  4.6 PHAS= -115.0 FOM= 0.89 TEST= 0
INDE 22 44 40 FOBS=     0.0 SIGMA= 19.7 PHAS=    0.0 FOM= 0.00 TEST= 0
INDE 22 44 42 FOBS=    17.5 SIGMA= 10.0 PHAS=   18.1 FOM= 0.21 TEST= 0
INDE 22 44 44 FOBS=     0.0 SIGMA= 19.0 PHAS=    0.0 FOM= 0.00 TEST= 0
INDE 22 44 46 FOBS=    41.5 SIGMA=  4.2 PHAS= -166.0 FOM= 0.84 TEST= 0
INDE 22 44 48 FOBS=    41.2 SIGMA=  5.0 PHAS=  -88.5 FOM= 0.34 TEST= 1
INDE 22 44 50 FOBS=    95.0 SIGMA=  2.3 PHAS=  -47.4 FOM= 0.31 TEST= 1
INDE 22 44 52 FOBS=   107.2 SIGMA=  2.2 PHAS=    1.7 FOM= 0.94 TEST= 0
INDE 22 44 54 FOBS=    50.0 SIGMA=  5.0 PHAS=  135.0 FOM= 0.77 TEST= 0
INDE 22 44 56 FOBS=    46.1 SIGMA=  6.9 PHAS= -114.3 FOM= 0.18 TEST= 0
INDE 22 44 58 FOBS=     0.0 SIGMA= 25.9 PHAS=    0.0 FOM= 0.00 TEST= 0
INDE 22 44 60 FOBS=    36.3 SIGMA=  8.3 PHAS=   87.0 FOM= 0.62 TEST= 0
```

*FIG. 12A - 470*

```
INDE 22 45 23 FOBS=   148.4 SIGMA=  1.4 PHAS=   98.2 FOM= 0.88 TEST= 0
INDE 22 45 25 FOBS=    43.9 SIGMA=  4.4 PHAS=   33.5 FOM= 0.59 TEST= 0
INDE 22 45 27 FOBS=    43.0 SIGMA=  4.4 PHAS=  159.6 FOM= 0.76 TEST= 0
INDE 22 45 29 FOBS=    95.0 SIGMA=  2.2 PHAS=   14.2 FOM= 0.94 TEST= 0
INDE 22 45 31 FOBS=    46.9 SIGMA=  4.1 PHAS= -146.4 FOM= 0.58 TEST= 0
INDE 22 45 33 FOBS=    40.5 SIGMA=  5.1 PHAS=  -34.2 FOM= 0.53 TEST= 0
INDE 22 45 35 FOBS=    69.3 SIGMA=  2.9 PHAS=   81.7 FOM= 0.62 TEST= 0
INDE 22 45 37 FOBS=    51.4 SIGMA=  3.8 PHAS=  158.7 FOM= 0.41 TEST= 0
INDE 22 45 39 FOBS=    62.2 SIGMA=  2.9 PHAS= -154.7 FOM= 0.82 TEST= 0
INDE 22 45 41 FOBS=   119.1 SIGMA=  1.6 PHAS=   19.8 FOM= 0.91 TEST= 0
INDE 22 45 43 FOBS=    21.1 SIGMA=  8.7 PHAS=  -20.3 FOM= 0.09 TEST= 0
INDE 22 45 45 FOBS=     0.0 SIGMA= 18.5 PHAS=    0.0 FOM= 0.00 TEST= 0
INDE 22 45 47 FOBS=    62.6 SIGMA=  3.0 PHAS=   70.3 FOM= 0.67 TEST= 0
INDE 22 45 49 FOBS=     0.0 SIGMA= 20.5 PHAS=    0.0 FOM= 0.00 TEST= 0
INDE 22 45 51 FOBS=    42.5 SIGMA=  6.5 PHAS=  -46.4 FOM= 0.28 TEST= 1
INDE 22 45 53 FOBS=    24.2 SIGMA=  9.4 PHAS=  -49.9 FOM= 0.63 TEST= 0
INDE 22 45 55 FOBS=    39.2 SIGMA=  7.1 PHAS=  104.6 FOM= 0.60 TEST= 0
INDE 22 45 57 FOBS=    78.2 SIGMA=  3.8 PHAS=   38.2 FOM= 0.83 TEST= 0
INDE 22 45 59 FOBS=     0.0 SIGMA= 26.2 PHAS=    0.0 FOM= 0.00 TEST= 0
INDE 22 46 22 FOBS=   122.0 SIGMA=  1.5 PHAS=   68.4 FOM= 0.93 TEST= 0
INDE 22 46 24 FOBS=    56.6 SIGMA=  3.4 PHAS= -159.7 FOM= 0.06 TEST= 1
INDE 22 46 26 FOBS=   134.8 SIGMA=  1.5 PHAS=  138.7 FOM= 0.95 TEST= 0
INDE 22 46 28 FOBS=    94.4 SIGMA=  2.1 PHAS=  130.7 FOM= 0.45 TEST= 1
INDE 22 46 30 FOBS=    80.7 SIGMA=  2.4 PHAS= -124.6 FOM= 0.82 TEST= 0
INDE 22 46 32 FOBS=     0.0 SIGMA= 19.7 PHAS=    0.0 FOM= 0.00 TEST= 0
INDE 22 46 34 FOBS=    45.4 SIGMA=  4.3 PHAS=   69.5 FOM= 0.32 TEST= 0
INDE 22 46 36 FOBS=    52.4 SIGMA=  4.0 PHAS=  -88.8 FOM= 0.54 TEST= 0
INDE 22 46 38 FOBS=     4.9 SIGMA= 39.6 PHAS=  156.1 FOM= 0.11 TEST= 0
INDE 22 46 40 FOBS=    70.0 SIGMA=  2.6 PHAS= -167.1 FOM= 0.55 TEST= 0
INDE 22 46 42 FOBS=    30.0 SIGMA=  6.6 PHAS=   84.1 FOM= 0.47 TEST= 0
INDE 22 46 44 FOBS=     0.0 SIGMA= 19.2 PHAS=    0.0 FOM= 0.00 TEST= 0
INDE 22 46 46 FOBS=     0.0 SIGMA= 19.8 PHAS=    0.0 FOM= 0.00 TEST= 0
INDE 22 46 48 FOBS=    12.4 SIGMA= 18.3 PHAS=   71.5 FOM= 0.22 TEST= 0
INDE 22 46 50 FOBS=    58.6 SIGMA=  3.4 PHAS= -128.4 FOM= 0.64 TEST= 0
INDE 22 46 52 FOBS=     0.0 SIGMA= 21.4 PHAS=    0.0 FOM= 0.00 TEST= 0
INDE 22 46 54 FOBS=    42.4 SIGMA=  5.9 PHAS= -124.9 FOM= 0.82 TEST= 0
INDE 22 46 56 FOBS=   150.4 SIGMA=  1.8 PHAS=  -45.9 FOM= 0.97 TEST= 0
INDE 22 46 58 FOBS=    73.9 SIGMA=  4.1 PHAS=  -59.4 FOM= 0.87 TEST= 0
INDE 22 47 23 FOBS=    78.3 SIGMA=  2.5 PHAS=  -34.9 FOM= 0.61 TEST= 0
INDE 22 47 25 FOBS=    85.7 SIGMA=  2.3 PHAS=   37.5 FOM= 0.92 TEST= 0
INDE 22 47 27 FOBS=   246.6 SIGMA=  1.0 PHAS=   36.8 FOM= 0.97 TEST= 0
INDE 22 47 29 FOBS=    95.7 SIGMA=  2.0 PHAS=   87.6 FOM= 0.85 TEST= 1
INDE 22 47 31 FOBS=    91.3 SIGMA=  2.2 PHAS=   65.5 FOM= 0.67 TEST= 0
INDE 22 47 33 FOBS=    55.0 SIGMA=  3.5 PHAS=  141.3 FOM= 0.70 TEST= 0
INDE 22 47 35 FOBS=     0.0 SIGMA= 21.7 PHAS=    0.0 FOM= 0.00 TEST= 0
INDE 22 47 37 FOBS=   113.2 SIGMA=  1.8 PHAS=   78.2 FOM= 0.05 TEST= 1
INDE 22 47 39 FOBS=    40.3 SIGMA=  4.4 PHAS=   78.7 FOM= 0.29 TEST= 0
INDE 22 47 41 FOBS=    71.4 SIGMA=  2.5 PHAS=  -15.5 FOM= 0.90 TEST= 0
INDE 22 47 43 FOBS=     0.0 SIGMA= 19.7 PHAS=    0.0 FOM= 0.00 TEST= 0
INDE 22 47 45 FOBS=     0.0 SIGMA= 20.6 PHAS=    0.0 FOM= 0.00 TEST= 0
INDE 22 47 47 FOBS=    41.9 SIGMA=  4.8 PHAS=  -65.5 FOM= 0.28 TEST= 0
INDE 22 47 49 FOBS=     0.0 SIGMA= 20.0 PHAS=    0.0 FOM= 0.00 TEST= 0
INDE 22 47 51 FOBS=     0.0 SIGMA= 20.0 PHAS=    0.0 FOM= 0.00 TEST= 0
INDE 22 47 53 FOBS=    32.7 SIGMA=  7.1 PHAS=  156.9 FOM= 0.70 TEST= 0
INDE 22 47 55 FOBS=   136.3 SIGMA=  1.8 PHAS=  147.9 FOM= 0.97 TEST= 0
INDE 22 47 57 FOBS=    79.0 SIGMA=  3.8 PHAS= -149.4 FOM= 0.87 TEST= 0
INDE 22 48 22 FOBS=    23.1 SIGMA=  7.5 PHAS=  174.0 FOM= 0.11 TEST= 0
INDE 22 48 24 FOBS=    50.9 SIGMA=  3.7 PHAS=   99.8 FOM= 0.79 TEST= 0
INDE 22 48 26 FOBS=   105.4 SIGMA=  1.9 PHAS=  -70.8 FOM= 0.50 TEST= 1
INDE 22 48 28 FOBS=    39.9 SIGMA=  5.1 PHAS=  -96.2 FOM= 0.40 TEST= 0
INDE 22 48 30 FOBS=    75.3 SIGMA=  2.6 PHAS=  -61.5 FOM= 0.23 TEST= 0
INDE 22 48 32 FOBS=    32.9 SIGMA=  6.3 PHAS=   32.6 FOM= 0.72 TEST= 0
INDE 22 48 34 FOBS=    45.9 SIGMA=  4.5 PHAS=  -83.5 FOM= 0.26 TEST= 1
INDE 22 48 36 FOBS=    38.7 SIGMA=  5.3 PHAS=  -56.6 FOM= 0.65 TEST= 0
INDE 22 48 38 FOBS=    68.8 SIGMA=  2.9 PHAS=   52.1 FOM= 0.85 TEST= 0
INDE 22 48 40 FOBS=    57.3 SIGMA=  3.3 PHAS= -144.8 FOM= 0.74 TEST= 0
INDE 22 48 42 FOBS=    21.0 SIGMA=  9.6 PHAS=  -83.7 FOM= 0.03 TEST= 1
INDE 22 48 44 FOBS=    32.6 SIGMA=  6.2 PHAS=  115.2 FOM= 0.56 TEST= 0
INDE 22 48 46 FOBS=    82.5 SIGMA=  2.5 PHAS=  176.7 FOM= 0.90 TEST= 0
INDE 22 48 48 FOBS=     0.0 SIGMA= 20.1 PHAS=    0.0 FOM= 0.00 TEST= 0
```

*FIG. 12A - 471*

```
INDE 22 48 50 FOBS=   48.9 SIGMA=  4.2 PHAS= -111.2 FOM= 0.36 TEST= 0
INDE 22 48 52 FOBS=   67.1 SIGMA=  3.1 PHAS=   14.6 FOM= 0.84 TEST= 0
INDE 22 48 54 FOBS=   10.2 SIGMA= 23.2 PHAS=  -57.3 FOM= 0.28 TEST= 0
INDE 22 48 56 FOBS=    0.0 SIGMA= 26.1 PHAS=    0.0 FOM= 0.00 TEST= 1
INDE 22 49 23 FOBS=  106.4 SIGMA=  1.8 PHAS=   -3.8 FOM= 0.90 TEST= 0
INDE 22 49 25 FOBS=    0.0 SIGMA= 19.4 PHAS=    0.0 FOM= 0.00 TEST= 0
INDE 22 49 27 FOBS=  144.4 SIGMA=  1.4 PHAS=   56.2 FOM= 0.96 TEST= 0
INDE 22 49 29 FOBS=   99.2 SIGMA=  2.0 PHAS=  130.3 FOM= 0.84 TEST= 0
INDE 22 49 31 FOBS=  179.7 SIGMA=  1.1 PHAS=    5.0 FOM= 0.92 TEST= 0
INDE 22 49 33 FOBS=  103.3 SIGMA=  1.8 PHAS=  152.7 FOM= 0.92 TEST= 0
INDE 22 49 35 FOBS=   95.1 SIGMA=  2.2 PHAS= -171.8 FOM= 0.93 TEST= 0
INDE 22 49 37 FOBS=   37.6 SIGMA=  6.1 PHAS=   -6.6 FOM= 0.15 TEST= 1
INDE 22 49 39 FOBS=   30.8 SIGMA=  8.1 PHAS=  102.5 FOM= 0.46 TEST= 0
INDE 22 49 41 FOBS=   47.6 SIGMA=  4.3 PHAS= -149.6 FOM= 0.77 TEST= 0
INDE 22 49 43 FOBS=   94.8 SIGMA=  2.2 PHAS=  -43.7 FOM= 0.76 TEST= 0
INDE 22 49 45 FOBS=    0.0 SIGMA= 20.8 PHAS=    0.0 FOM= 0.00 TEST= 0
INDE 22 49 47 FOBS=   33.2 SIGMA=  6.1 PHAS=  163.5 FOM= 0.63 TEST= 0
INDE 22 49 49 FOBS=   44.6 SIGMA=  4.6 PHAS=  159.3 FOM= 0.31 TEST= 0
INDE 22 49 51 FOBS=   62.4 SIGMA=  3.3 PHAS= -124.3 FOM= 0.83 TEST= 0
INDE 22 49 53 FOBS=   54.6 SIGMA=  3.8 PHAS= -171.8 FOM= 0.81 TEST= 0
INDE 22 49 55 FOBS=   42.4 SIGMA=  6.9 PHAS= -157.6 FOM= 0.78 TEST= 0
INDE 22 50 22 FOBS=  105.2 SIGMA=  1.6 PHAS= -110.6 FOM= 0.80 TEST= 1
INDE 22 50 24 FOBS=   67.9 SIGMA=  2.8 PHAS= -164.3 FOM= 0.79 TEST= 0
INDE 22 50 26 FOBS=  149.3 SIGMA=  1.3 PHAS=  -40.7 FOM= 0.95 TEST= 0
INDE 22 50 28 FOBS=  169.2 SIGMA=  1.2 PHAS=  -56.7 FOM= 0.97 TEST= 0
INDE 22 50 30 FOBS=   49.8 SIGMA=  4.1 PHAS= -126.6 FOM= 0.76 TEST= 0
INDE 22 50 32 FOBS=  101.4 SIGMA=  1.8 PHAS=    0.3 FOM= 0.90 TEST= 0
INDE 22 50 34 FOBS=  123.6 SIGMA=  1.8 PHAS=   69.1 FOM= 0.90 TEST= 0
INDE 22 50 36 FOBS=    0.0 SIGMA= 22.2 PHAS=    0.0 FOM= 0.00 TEST= 0
INDE 22 50 38 FOBS=   93.3 SIGMA=  2.5 PHAS=   68.9 FOM= 0.91 TEST= 0
INDE 22 50 40 FOBS=  109.4 SIGMA=  2.0 PHAS=  137.6 FOM= 0.90 TEST= 0
INDE 22 50 42 FOBS=   46.3 SIGMA=  4.4 PHAS=  174.8 FOM= 0.78 TEST= 0
INDE 22 50 44 FOBS=   89.3 SIGMA=  2.3 PHAS=  102.5 FOM= 0.93 TEST= 0
INDE 22 50 46 FOBS=   49.2 SIGMA=  4.2 PHAS=  142.7 FOM= 0.68 TEST= 0
INDE 22 50 48 FOBS=   85.6 SIGMA=  2.5 PHAS=   43.6 FOM= 0.86 TEST= 0
INDE 22 50 50 FOBS=   70.1 SIGMA=  3.0 PHAS=  -63.7 FOM= 0.67 TEST= 0
INDE 22 50 52 FOBS=   42.3 SIGMA=  5.0 PHAS=   53.5 FOM= 0.72 TEST= 0
INDE 22 50 54 FOBS=   41.4 SIGMA=  6.6 PHAS=  155.6 FOM= 0.55 TEST= 0
INDE 22 51 23 FOBS=   12.5 SIGMA= 14.4 PHAS=   85.6 FOM= 0.28 TEST= 0
INDE 22 51 25 FOBS=  111.5 SIGMA=  1.8 PHAS=  158.1 FOM= 0.92 TEST= 0
INDE 22 51 27 FOBS=  212.8 SIGMA=  1.1 PHAS= -169.4 FOM= 0.98 TEST= 0
INDE 22 51 29 FOBS=  132.9 SIGMA=  1.7 PHAS= -170.9 FOM= 0.97 TEST= 0
INDE 22 51 31 FOBS=   46.3 SIGMA=  4.7 PHAS=   30.1 FOM= 0.68 TEST= 0
INDE 22 51 33 FOBS=  110.7 SIGMA=  1.8 PHAS=  -96.2 FOM= 0.93 TEST= 0
INDE 22 51 35 FOBS=    0.0 SIGMA= 21.0 PHAS=    0.0 FOM= 0.00 TEST= 0
INDE 22 51 37 FOBS=  124.6 SIGMA=  1.9 PHAS=  -15.2 FOM= 0.91 TEST= 0
INDE 22 51 39 FOBS=   29.6 SIGMA=  7.7 PHAS=    0.9 FOM= 0.53 TEST= 0
INDE 22 51 41 FOBS=   48.5 SIGMA=  4.2 PHAS=  100.4 FOM= 0.85 TEST= 0
INDE 22 51 43 FOBS=  105.4 SIGMA=  2.0 PHAS=   75.5 FOM= 0.91 TEST= 0
INDE 22 51 45 FOBS=   24.0 SIGMA=  9.1 PHAS=  -17.1 FOM= 0.36 TEST= 0
INDE 22 51 47 FOBS=   34.2 SIGMA=  6.4 PHAS= -176.7 FOM= 0.20 TEST= 0
INDE 22 51 49 FOBS=   81.9 SIGMA=  2.8 PHAS= -127.5 FOM= 0.91 TEST= 0
INDE 22 51 51 FOBS=   94.8 SIGMA=  2.5 PHAS= -126.8 FOM= 0.94 TEST= 0
INDE 22 51 53 FOBS=   23.3 SIGMA= 13.5 PHAS=   96.5 FOM= 0.18 TEST= 0
INDE 22 52 22 FOBS=   16.6 SIGMA= 11.4 PHAS=   19.2 FOM= 0.22 TEST= 0
INDE 22 52 24 FOBS=   83.7 SIGMA=  2.6 PHAS=   58.4 FOM= 0.86 TEST= 0
INDE 22 52 26 FOBS=  178.4 SIGMA=  1.3 PHAS=   57.1 FOM= 0.96 TEST= 0
INDE 22 52 28 FOBS=   52.0 SIGMA=  4.2 PHAS=  162.3 FOM= 0.50 TEST= 0
INDE 22 52 30 FOBS=   83.5 SIGMA=  2.6 PHAS=  160.7 FOM= 0.85 TEST= 0
INDE 22 52 32 FOBS=   40.0 SIGMA=  5.4 PHAS= -159.7 FOM= 0.53 TEST= 0
INDE 22 52 34 FOBS=   28.8 SIGMA=  6.6 PHAS=  -68.1 FOM= 0.23 TEST= 0
INDE 22 52 36 FOBS=   33.7 SIGMA=  6.1 PHAS=  -45.7 FOM= 0.58 TEST= 0
INDE 22 52 38 FOBS=   49.9 SIGMA=  4.9 PHAS= -108.0 FOM= 0.56 TEST= 0
INDE 22 52 40 FOBS=   84.8 SIGMA=  2.8 PHAS=  173.2 FOM= 0.91 TEST= 0
INDE 22 52 42 FOBS=   49.0 SIGMA=  4.2 PHAS=    3.3 FOM= 0.42 TEST= 0
INDE 22 52 44 FOBS=   86.6 SIGMA=  2.7 PHAS=   97.9 FOM= 0.93 TEST= 0
INDE 22 52 46 FOBS=   52.8 SIGMA=  4.4 PHAS=  109.4 FOM= 0.52 TEST= 0
INDE 22 52 48 FOBS=    0.0 SIGMA= 25.2 PHAS=    0.0 FOM= 0.00 TEST= 1
INDE 22 52 50 FOBS=   16.7 SIGMA= 16.5 PHAS=  111.9 FOM= 0.48 TEST= 0
INDE 22 52 52 FOBS=    0.0 SIGMA= 27.1 PHAS=    0.0 FOM= 0.00 TEST= 0
```

*FIG. 12A - 472*

```
INDE 22 53 23 FOBS=   122.5 SIGMA=  1.6 PHAS=  -95.7 FOM= 0.90 TEST= 1
INDE 22 53 25 FOBS=    13.9 SIGMA= 16.8 PHAS= -137.3 FOM= 0.19 TEST= 0
INDE 22 53 27 FOBS=    59.7 SIGMA=  3.6 PHAS= -131.4 FOM= 0.85 TEST= 0
INDE 22 53 29 FOBS=    83.3 SIGMA=  2.7 PHAS=   92.6 FOM= 0.82 TEST= 0
INDE 22 53 31 FOBS=     0.0 SIGMA= 20.7 PHAS=    0.0 FOM= 0.00 TEST= 0
INDE 22 53 33 FOBS=   135.0 SIGMA=  1.6 PHAS= -162.1 FOM= 0.89 TEST= 0
INDE 22 53 35 FOBS=     0.0 SIGMA= 20.3 PHAS=    0.0 FOM= 0.00 TEST= 0
INDE 22 53 37 FOBS=     0.0 SIGMA= 20.4 PHAS=    0.0 FOM= 0.00 TEST= 0
INDE 22 53 39 FOBS=    34.6 SIGMA=  7.5 PHAS=  145.1 FOM= 0.61 TEST= 0
INDE 22 53 41 FOBS=    82.3 SIGMA=  3.3 PHAS=   69.5 FOM= 0.90 TEST= 0
INDE 22 53 43 FOBS=    81.2 SIGMA=  3.1 PHAS=   12.6 FOM= 0.90 TEST= 0
INDE 22 53 45 FOBS=    60.4 SIGMA=  4.2 PHAS=    5.5 FOM= 0.84 TEST= 0
INDE 22 53 47 FOBS=    38.6 SIGMA=  7.2 PHAS=   44.5 FOM= 0.38 TEST= 0
INDE 22 53 49 FOBS=    85.1 SIGMA=  3.1 PHAS=  -41.0 FOM= 0.84 TEST= 0
INDE 22 53 51 FOBS=    62.2 SIGMA=  5.2 PHAS=  -91.7 FOM= 0.87 TEST= 0
INDE 22 54 22 FOBS=    43.3 SIGMA=  4.0 PHAS=   26.6 FOM= 0.55 TEST= 0
INDE 22 54 24 FOBS=    74.0 SIGMA=  2.9 PHAS=  153.6 FOM= 0.87 TEST= 0
INDE 22 54 26 FOBS=     2.3 SIGMA= 94.6 PHAS= -158.8 FOM= 0.02 TEST= 0
INDE 22 54 28 FOBS=    68.8 SIGMA=  3.2 PHAS=  -24.8 FOM= 0.87 TEST= 0
INDE 22 54 30 FOBS=     0.0 SIGMA= 21.9 PHAS=    0.0 FOM= 0.00 TEST= 0
INDE 22 54 32 FOBS=    36.9 SIGMA=  7.1 PHAS=   99.8 FOM= 0.23 TEST= 1
INDE 22 54 34 FOBS=    46.0 SIGMA=  4.7 PHAS=   24.7 FOM= 0.77 TEST= 0
INDE 22 54 36 FOBS=     0.0 SIGMA= 21.1 PHAS=    0.0 FOM= 0.00 TEST= 0
INDE 22 54 38 FOBS=     0.0 SIGMA= 21.4 PHAS=    0.0 FOM= 0.00 TEST= 0
INDE 22 54 40 FOBS=    64.1 SIGMA=  4.7 PHAS=   30.8 FOM= 0.76 TEST= 0
INDE 22 54 42 FOBS=    76.7 SIGMA=  3.3 PHAS=  -74.3 FOM= 0.84 TEST= 0
INDE 22 54 44 FOBS=     0.0 SIGMA= 22.3 PHAS=    0.0 FOM= 0.00 TEST= 0
INDE 22 54 46 FOBS=    61.2 SIGMA=  4.2 PHAS=  -68.7 FOM= 0.88 TEST= 0
INDE 22 54 48 FOBS=     0.0 SIGMA= 22.7 PHAS=    0.0 FOM= 0.00 TEST= 0
INDE 22 54 50 FOBS=    82.6 SIGMA=  4.1 PHAS=  -93.9 FOM= 0.90 TEST= 0
INDE 22 55 23 FOBS=   115.3 SIGMA=  1.6 PHAS=   15.1 FOM= 0.45 TEST= 1
INDE 22 55 25 FOBS=     0.0 SIGMA= 21.8 PHAS=    0.0 FOM= 0.00 TEST= 0
INDE 22 55 27 FOBS=   176.4 SIGMA=  1.3 PHAS= -124.3 FOM= 0.96 TEST= 0
INDE 22 55 29 FOBS=    62.3 SIGMA=  3.5 PHAS= -104.9 FOM= 0.77 TEST= 0
INDE 22 55 31 FOBS=    39.8 SIGMA=  6.0 PHAS= -163.5 FOM= 0.58 TEST= 0
INDE 22 55 33 FOBS=    96.3 SIGMA=  2.6 PHAS=  -74.3 FOM= 0.31 TEST= 1
INDE 22 55 35 FOBS=    41.7 SIGMA=  5.4 PHAS=  162.3 FOM= 0.24 TEST= 0
INDE 22 55 37 FOBS=    40.4 SIGMA=  5.6 PHAS=  163.9 FOM= 0.26 TEST= 0
INDE 22 55 39 FOBS=    71.1 SIGMA=  4.2 PHAS= -152.2 FOM= 0.81 TEST= 0
INDE 22 55 41 FOBS=    31.6 SIGMA= 12.8 PHAS=  107.5 FOM= 0.18 TEST= 0
INDE 22 55 43 FOBS=     0.0 SIGMA= 23.5 PHAS=    0.0 FOM= 0.00 TEST= 1
INDE 22 55 45 FOBS=    85.5 SIGMA=  3.0 PHAS=  171.2 FOM= 0.86 TEST= 0
INDE 22 55 47 FOBS=     0.0 SIGMA= 25.3 PHAS=    0.0 FOM= 0.00 TEST= 0
INDE 22 55 49 FOBS=     0.0 SIGMA= 25.6 PHAS=    0.0 FOM= 0.00 TEST= 0
INDE 22 56 22 FOBS=    88.7 SIGMA=  2.8 PHAS=   89.8 FOM= 0.59 TEST= 0
INDE 22 56 24 FOBS=   136.9 SIGMA=  1.8 PHAS=  158.1 FOM= 0.91 TEST= 0
INDE 22 56 26 FOBS=    38.5 SIGMA=  6.1 PHAS= -170.9 FOM= 0.42 TEST= 0
INDE 22 56 28 FOBS=    68.0 SIGMA=  3.9 PHAS=  146.6 FOM= 0.63 TEST= 0
INDE 22 56 30 FOBS=    55.5 SIGMA=  4.9 PHAS=  126.0 FOM= 0.93 TEST= 0
INDE 22 56 32 FOBS=     0.0 SIGMA= 23.1 PHAS=    0.0 FOM= 0.00 TEST= 0
INDE 22 56 34 FOBS=    33.2 SIGMA=  8.1 PHAS=  -30.4 FOM= 0.43 TEST= 1
INDE 22 56 36 FOBS=     0.0 SIGMA= 21.2 PHAS=    0.0 FOM= 0.00 TEST= 0
INDE 22 56 38 FOBS=    88.5 SIGMA=  2.6 PHAS=  125.3 FOM= 0.88 TEST= 0
INDE 22 56 40 FOBS=    19.1 SIGMA= 18.2 PHAS=   89.1 FOM= 0.39 TEST= 0
INDE 22 56 42 FOBS=     0.0 SIGMA= 26.8 PHAS=    0.0 FOM= 0.00 TEST= 0
INDE 22 56 44 FOBS=    83.1 SIGMA=  3.1 PHAS=  -27.3 FOM= 0.74 TEST= 0
INDE 22 56 46 FOBS=    68.6 SIGMA=  3.9 PHAS= -107.3 FOM= 0.81 TEST= 0
INDE 22 56 48 FOBS=     0.0 SIGMA= 27.4 PHAS=    0.0 FOM= 0.00 TEST= 0
INDE 22 57 23 FOBS=    61.1 SIGMA=  3.6 PHAS=   37.3 FOM= 0.07 TEST= 1
INDE 22 57 25 FOBS=    55.8 SIGMA=  4.6 PHAS=  111.9 FOM= 0.59 TEST= 0
INDE 22 57 27 FOBS=    56.4 SIGMA=  4.7 PHAS=  -96.2 FOM= 0.80 TEST= 0
INDE 22 57 29 FOBS=    81.2 SIGMA=  3.3 PHAS=  -58.2 FOM= 0.92 TEST= 0
INDE 22 57 31 FOBS=     0.0 SIGMA= 23.0 PHAS=    0.0 FOM= 0.00 TEST= 0
INDE 22 57 33 FOBS=    84.9 SIGMA=  3.3 PHAS=  122.1 FOM= 0.38 TEST= 0
INDE 22 57 35 FOBS=    30.0 SIGMA=  9.1 PHAS=  152.8 FOM= 0.68 TEST= 0
INDE 22 57 37 FOBS=    25.9 SIGMA= 10.7 PHAS=  -32.5 FOM= 0.13 TEST= 0
INDE 22 57 39 FOBS=     0.0 SIGMA= 22.4 PHAS=    0.0 FOM= 0.00 TEST= 0
INDE 22 57 41 FOBS=    18.5 SIGMA= 16.2 PHAS=   27.3 FOM= 0.10 TEST= 0
INDE 22 57 43 FOBS=    30.5 SIGMA=  9.1 PHAS=  175.8 FOM= 0.48 TEST= 0
INDE 22 57 45 FOBS=    86.7 SIGMA=  3.1 PHAS= -171.8 FOM= 0.92 TEST= 0
```

*FIG. 12A - 473*

```
INDE 22 57 47 FOBS=    0.0 SIGMA= 30.2 PHAS=    0.0 FOM= 0.00 TEST= 0
INDE 22 58 22 FOBS=   81.9 SIGMA=  3.5 PHAS=  -54.0 FOM= 0.72 TEST= 0
INDE 22 58 24 FOBS=  102.2 SIGMA=  2.2 PHAS=  129.9 FOM= 0.92 TEST= 0
INDE 22 58 26 FOBS=   12.6 SIGMA= 20.3 PHAS=   -9.3 FOM= 0.29 TEST= 0
INDE 22 58 28 FOBS=   94.8 SIGMA=  2.8 PHAS= -175.7 FOM= 0.90 TEST= 0
INDE 22 58 30 FOBS=   57.3 SIGMA=  4.7 PHAS= -171.0 FOM= 0.80 TEST= 0
INDE 22 58 32 FOBS=   60.8 SIGMA=  4.5 PHAS=  -12.7 FOM= 0.74 TEST= 0
INDE 22 58 34 FOBS=   97.7 SIGMA=  2.9 PHAS=    3.2 FOM= 0.91 TEST= 0
INDE 22 58 36 FOBS=    0.0 SIGMA= 21.3 PHAS=    0.0 FOM= 0.00 TEST= 0
INDE 22 58 38 FOBS=   50.6 SIGMA=  4.6 PHAS=  134.8 FOM= 0.82 TEST= 0
INDE 22 58 40 FOBS=    0.0 SIGMA= 21.6 PHAS=    0.0 FOM= 0.00 TEST= 0
INDE 22 58 42 FOBS=   28.2 SIGMA= 11.0 PHAS=  115.9 FOM= 0.11 TEST= 0
INDE 22 58 44 FOBS=    0.0 SIGMA= 23.7 PHAS=    0.0 FOM= 0.00 TEST= 0
INDE 22 58 46 FOBS=   61.1 SIGMA=  5.4 PHAS= -163.0 FOM= 0.64 TEST= 0
INDE 22 59 23 FOBS=   81.8 SIGMA=  3.5 PHAS=   51.2 FOM= 0.81 TEST= 0
INDE 22 59 25 FOBS=   43.5 SIGMA=  5.9 PHAS=   14.8 FOM= 0.60 TEST= 0
INDE 22 59 27 FOBS=   47.3 SIGMA=  5.5 PHAS= -161.6 FOM= 0.31 TEST= 0
INDE 22 59 29 FOBS=   50.4 SIGMA=  5.2 PHAS= -144.9 FOM= 0.46 TEST= 0
INDE 22 59 31 FOBS=   57.7 SIGMA=  4.7 PHAS=  150.9 FOM= 0.79 TEST= 0
INDE 22 59 33 FOBS=   92.3 SIGMA=  3.1 PHAS=  -51.1 FOM= 0.89 TEST= 0
INDE 22 59 35 FOBS=   36.9 SIGMA=  7.6 PHAS=   71.4 FOM= 0.13 TEST= 0
INDE 22 59 37 FOBS=   47.3 SIGMA=  4.9 PHAS=  133.3 FOM= 0.14 TEST= 1
INDE 22 59 39 FOBS=   35.1 SIGMA=  8.5 PHAS=  -35.9 FOM= 0.09 TEST= 1
INDE 22 59 41 FOBS=    0.0 SIGMA= 23.3 PHAS=    0.0 FOM= 0.00 TEST= 0
INDE 22 59 43 FOBS=    0.0 SIGMA= 25.1 PHAS=    0.0 FOM= 0.00 TEST= 0
INDE 22 59 45 FOBS=   23.2 SIGMA= 16.1 PHAS=  123.5 FOM= 0.47 TEST= 0
INDE 22 60 22 FOBS=   86.0 SIGMA=  3.3 PHAS=  -69.2 FOM= 0.89 TEST= 0
INDE 22 60 24 FOBS=   48.6 SIGMA=  5.8 PHAS=   14.6 FOM= 0.55 TEST= 0
INDE 22 60 26 FOBS=   41.0 SIGMA=  7.3 PHAS=   12.6 FOM= 0.77 TEST= 0
INDE 22 60 28 FOBS=   65.9 SIGMA=  4.0 PHAS=   88.9 FOM= 0.69 TEST= 0
INDE 22 60 30 FOBS=   14.1 SIGMA= 18.7 PHAS=   -4.9 FOM= 0.04 TEST= 0
INDE 22 60 32 FOBS=   63.7 SIGMA=  4.3 PHAS=  -67.5 FOM= 0.88 TEST= 0
INDE 22 60 34 FOBS=   67.1 SIGMA=  4.2 PHAS= -170.4 FOM= 0.51 TEST= 0
INDE 22 60 36 FOBS=   60.6 SIGMA=  4.7 PHAS=    3.4 FOM= 0.60 TEST= 0
INDE 22 60 38 FOBS=   97.1 SIGMA=  2.5 PHAS=  -68.5 FOM= 0.85 TEST= 0
INDE 22 60 40 FOBS=    0.0 SIGMA= 22.8 PHAS=    0.0 FOM= 0.00 TEST= 0
INDE 22 60 42 FOBS=   53.5 SIGMA=  5.1 PHAS= -179.5 FOM= 0.80 TEST= 0
INDE 22 60 44 FOBS=   28.7 SIGMA= 16.4 PHAS=  -15.0 FOM= 0.37 TEST= 0
INDE 22 61 23 FOBS=   51.2 SIGMA=  5.4 PHAS=  -50.8 FOM= 0.12 TEST= 1
INDE 22 61 25 FOBS=    0.0 SIGMA= 23.7 PHAS=    0.0 FOM= 0.00 TEST= 0
INDE 22 61 27 FOBS=   43.6 SIGMA=  6.0 PHAS=  152.1 FOM= 0.04 TEST= 1
INDE 22 61 29 FOBS=   53.7 SIGMA=  4.9 PHAS=  -70.9 FOM= 0.35 TEST= 1
INDE 22 61 31 FOBS=    0.0 SIGMA= 25.1 PHAS=    0.0 FOM= 0.00 TEST= 0
INDE 22 61 33 FOBS=  107.9 SIGMA=  2.7 PHAS= -153.3 FOM= 0.34 TEST= 1
INDE 22 61 35 FOBS=    0.0 SIGMA= 23.6 PHAS=    0.0 FOM= 0.00 TEST= 0
INDE 22 61 37 FOBS=   45.9 SIGMA=  5.1 PHAS=  150.9 FOM= 0.59 TEST= 0
INDE 22 61 39 FOBS=   36.9 SIGMA=  6.5 PHAS=   -3.7 FOM= 0.04 TEST= 0
INDE 22 61 41 FOBS=   27.9 SIGMA= 10.7 PHAS=  144.3 FOM= 0.61 TEST= 0
INDE 22 62 22 FOBS=    0.0 SIGMA= 23.6 PHAS=    0.0 FOM= 0.00 TEST= 1
INDE 22 62 24 FOBS=    0.0 SIGMA= 23.6 PHAS=    0.0 FOM= 0.00 TEST= 0
INDE 22 62 26 FOBS=   58.9 SIGMA=  4.4 PHAS=  113.2 FOM= 0.38 TEST= 0
INDE 22 62 28 FOBS=   86.9 SIGMA=  3.1 PHAS= -145.3 FOM= 0.83 TEST= 0
INDE 22 62 30 FOBS=   58.9 SIGMA=  4.6 PHAS= -120.3 FOM= 0.65 TEST= 0
INDE 22 62 32 FOBS=   71.4 SIGMA=  3.9 PHAS=  115.0 FOM= 0.66 TEST= 0
INDE 22 62 34 FOBS=   46.9 SIGMA=  6.0 PHAS= -167.7 FOM= 0.53 TEST= 0
INDE 22 62 36 FOBS=   55.6 SIGMA=  5.2 PHAS=   50.1 FOM= 0.79 TEST= 0
INDE 22 62 38 FOBS=   87.5 SIGMA=  2.8 PHAS=  -41.0 FOM= 0.94 TEST= 0
INDE 22 62 40 FOBS=    0.0 SIGMA= 24.3 PHAS=    0.0 FOM= 0.00 TEST= 0
INDE 22 63 23 FOBS=   84.9 SIGMA=  3.4 PHAS=    6.3 FOM= 0.89 TEST= 0
INDE 22 63 25 FOBS=   46.7 SIGMA=  6.1 PHAS=   72.5 FOM= 0.22 TEST= 0
INDE 22 63 27 FOBS=   66.5 SIGMA=  4.0 PHAS=  112.3 FOM= 0.87 TEST= 0
INDE 22 63 29 FOBS=   22.7 SIGMA= 11.6 PHAS=   76.5 FOM= 0.44 TEST= 0
INDE 22 63 31 FOBS=   60.0 SIGMA=  4.5 PHAS=   -2.9 FOM= 0.85 TEST= 0
INDE 22 63 33 FOBS=   13.8 SIGMA= 20.1 PHAS=   10.6 FOM= 0.22 TEST= 0
INDE 22 63 35 FOBS=   29.9 SIGMA= 11.0 PHAS= -128.2 FOM= 0.51 TEST= 0
INDE 22 63 37 FOBS=   38.1 SIGMA=  8.9 PHAS= -118.8 FOM= 0.60 TEST= 0
INDE 22 63 39 FOBS=   40.2 SIGMA=  8.6 PHAS= -144.5 FOM= 0.83 TEST= 0
INDE 22 64 22 FOBS=   31.6 SIGMA=  8.7 PHAS= -145.6 FOM= 0.34 TEST= 0
INDE 22 64 24 FOBS=   75.8 SIGMA=  3.8 PHAS=  -90.0 FOM= 0.88 TEST= 0
INDE 22 64 26 FOBS=    0.0 SIGMA= 23.8 PHAS=    0.0 FOM= 0.00 TEST= 0
```

*FIG. 12A - 474*

```
INDE 22 64 28 FOBS=    27.7 SIGMA=  11.0 PHAS= -102.5 FOM= 0.61 TEST= 0
INDE 22 64 30 FOBS=    77.1 SIGMA=   4.1 PHAS=  -88.3 FOM= 0.89 TEST= 0
INDE 22 64 32 FOBS=     0.0 SIGMA=  25.2 PHAS=    0.0 FOM= 0.00 TEST= 0
INDE 22 64 34 FOBS=    54.4 SIGMA=   6.1 PHAS= -131.4 FOM= 0.80 TEST= 0
INDE 22 64 36 FOBS=    59.2 SIGMA=   5.8 PHAS=  135.4 FOM= 0.91 TEST= 0
INDE 22 64 38 FOBS=    10.4 SIGMA=  41.5 PHAS=  -38.5 FOM= 0.35 TEST= 0
INDE 22 65 23 FOBS=     0.0 SIGMA=  23.6 PHAS=    0.0 FOM= 0.00 TEST= 0
INDE 22 65 25 FOBS=    46.4 SIGMA=   6.2 PHAS=   85.6 FOM= 0.17 TEST= 1
INDE 22 65 27 FOBS=    67.6 SIGMA=   5.7 PHAS=  118.7 FOM= 0.81 TEST= 0
INDE 22 65 29 FOBS=    42.5 SIGMA=   7.4 PHAS= -144.6 FOM= 0.07 TEST= 1
INDE 22 65 31 FOBS=    57.7 SIGMA=   5.6 PHAS=  -99.9 FOM= 0.68 TEST= 0
INDE 22 65 33 FOBS=    83.3 SIGMA=   4.0 PHAS=   53.9 FOM= 0.90 TEST= 0
INDE 22 65 35 FOBS=   104.1 SIGMA=   3.4 PHAS=   81.1 FOM= 0.94 TEST= 0
INDE 22 66 22 FOBS=    34.9 SIGMA=   9.6 PHAS= -165.3 FOM= 0.79 TEST= 0
INDE 22 66 24 FOBS=    29.8 SIGMA=  11.5 PHAS=  179.8 FOM= 0.33 TEST= 0
INDE 22 66 26 FOBS=    74.2 SIGMA=   3.9 PHAS=  -10.0 FOM= 0.88 TEST= 0
INDE 22 66 28 FOBS=    50.8 SIGMA=   6.2 PHAS=  159.2 FOM= 0.81 TEST= 0
INDE 22 66 30 FOBS=    47.5 SIGMA=   6.7 PHAS=   75.9 FOM= 0.72 TEST= 0
INDE 22 66 32 FOBS=    36.3 SIGMA=  10.7 PHAS=  -67.6 FOM= 0.47 TEST= 0
INDE 22 66 34 FOBS=    81.9 SIGMA=   4.2 PHAS=  -16.7 FOM= 0.93 TEST= 0
INDE 22 67 23 FOBS=    51.0 SIGMA=   8.3 PHAS=   75.5 FOM= 0.30 TEST= 0
INDE 22 67 25 FOBS=    22.3 SIGMA=  16.0 PHAS= -134.0 FOM= 0.18 TEST= 0
INDE 22 67 27 FOBS=    40.2 SIGMA=   8.7 PHAS=  118.1 FOM= 0.06 TEST= 1
INDE 22 67 29 FOBS=    35.5 SIGMA=  11.2 PHAS=    5.5 FOM= 0.58 TEST= 0
INDE 22 67 31 FOBS=    62.6 SIGMA=   5.3 PHAS=  -63.1 FOM= 0.58 TEST= 0
INDE 22 68 22 FOBS=     0.0 SIGMA=  29.1 PHAS=    0.0 FOM= 0.00 TEST= 0
INDE 22 68 24 FOBS=    30.2 SIGMA=  14.7 PHAS= -163.2 FOM= 0.18 TEST= 0
INDE 22 68 26 FOBS=    56.1 SIGMA=   8.2 PHAS=  -72.5 FOM= 0.78 TEST= 0
INDE 22 68 30 FOBS=   118.5 SIGMA=   3.6 PHAS= -141.0 FOM= 0.59 TEST= 0
INDE 22 69 23 FOBS=    57.0 SIGMA=   7.8 PHAS= -115.2 FOM= 0.73 TEST= 0
INDE 22 69 25 FOBS=    60.6 SIGMA=   7.5 PHAS= -179.5 FOM= 0.50 TEST= 0
INDE 22 69 27 FOBS=     0.0 SIGMA=  30.3 PHAS=    0.0 FOM= 0.00 TEST= 0
INDE 22 70 22 FOBS=    96.1 SIGMA=   4.5 PHAS=  109.2 FOM= 0.88 TEST= 0
INDE 23 24 23 FOBS=    49.4 SIGMA=   3.0 PHAS= -138.6 FOM= 0.94 TEST= 0
INDE 23 24 25 FOBS=   354.0 SIGMA=   0.6 PHAS=  175.9 FOM= 0.97 TEST= 0
INDE 23 24 27 FOBS=    54.9 SIGMA=   2.5 PHAS= -145.8 FOM= 0.32 TEST= 0
INDE 23 24 29 FOBS=   135.4 SIGMA=   1.1 PHAS=  116.5 FOM= 0.91 TEST= 0
INDE 23 24 31 FOBS=   181.2 SIGMA=   0.9 PHAS=  168.3 FOM= 0.98 TEST= 0
INDE 23 24 33 FOBS=   127.8 SIGMA=   1.3 PHAS=  -38.3 FOM= 0.86 TEST= 0
INDE 23 24 35 FOBS=    71.3 SIGMA=   2.3 PHAS=  -32.4 FOM= 0.70 TEST= 0
INDE 23 24 37 FOBS=    40.7 SIGMA=   4.4 PHAS=   54.4 FOM= 0.63 TEST= 0
INDE 23 24 39 FOBS=   204.1 SIGMA=   1.0 PHAS=   99.3 FOM= 0.95 TEST= 0
INDE 23 24 41 FOBS=    78.2 SIGMA=   2.2 PHAS=  168.3 FOM= 0.97 TEST= 0
INDE 23 24 43 FOBS=   167.6 SIGMA=   1.2 PHAS=   17.5 FOM= 0.89 TEST= 0
INDE 23 24 45 FOBS=     0.0 SIGMA=  18.2 PHAS=    0.0 FOM= 0.00 TEST= 0
INDE 23 24 47 FOBS=    54.4 SIGMA=   2.8 PHAS= -157.9 FOM= 0.85 TEST= 0
INDE 23 24 49 FOBS=    66.2 SIGMA=   2.5 PHAS=   18.5 FOM= 0.94 TEST= 0
INDE 23 24 51 FOBS=    90.7 SIGMA=   1.8 PHAS=  140.2 FOM= 0.63 TEST= 0
INDE 23 24 53 FOBS=    61.0 SIGMA=   2.7 PHAS= -117.3 FOM= 0.82 TEST= 0
INDE 23 24 55 FOBS=    91.8 SIGMA=   2.0 PHAS= -133.8 FOM= 0.93 TEST= 0
INDE 23 24 57 FOBS=   120.0 SIGMA=   2.6 PHAS=  -22.1 FOM= 0.96 TEST= 0
INDE 23 24 59 FOBS=    45.5 SIGMA=   6.4 PHAS=  122.1 FOM= 0.65 TEST= 0
INDE 23 24 61 FOBS=    60.1 SIGMA=   4.9 PHAS=  142.1 FOM= 0.81 TEST= 0
INDE 23 24 63 FOBS=    25.7 SIGMA=  11.3 PHAS=  138.2 FOM= 0.33 TEST= 0
INDE 23 24 65 FOBS=    62.4 SIGMA=   7.1 PHAS=  -86.8 FOM= 0.83 TEST= 0
INDE 23 24 67 FOBS=    61.2 SIGMA=   7.4 PHAS=    2.0 FOM= 0.87 TEST= 0
INDE 23 24 69 FOBS=    58.9 SIGMA=   7.4 PHAS=  157.3 FOM= 0.83 TEST= 0
INDE 23 25 24 FOBS=   125.4 SIGMA=   1.3 PHAS=   64.5 FOM= 0.88 TEST= 0
INDE 23 25 26 FOBS=   119.0 SIGMA=   1.2 PHAS=   79.6 FOM= 0.91 TEST= 0
INDE 23 25 28 FOBS=    51.2 SIGMA=   2.9 PHAS=  -23.2 FOM= 0.88 TEST= 0
INDE 23 25 30 FOBS=   183.2 SIGMA=   1.0 PHAS=   -1.4 FOM= 0.97 TEST= 0
INDE 23 25 32 FOBS=   100.5 SIGMA=   1.6 PHAS=  -27.8 FOM= 0.98 TEST= 0
INDE 23 25 34 FOBS=   151.3 SIGMA=   1.1 PHAS= -118.6 FOM= 0.89 TEST= 0
INDE 23 25 36 FOBS=    74.6 SIGMA=   2.2 PHAS= -106.5 FOM= 0.78 TEST= 0
INDE 23 25 38 FOBS=   295.0 SIGMA=   0.8 PHAS=   -8.4 FOM= 0.97 TEST= 0
INDE 23 25 40 FOBS=   239.7 SIGMA=   0.8 PHAS=  101.1 FOM= 0.97 TEST= 0
INDE 23 25 42 FOBS=    56.1 SIGMA=   3.1 PHAS= -121.3 FOM= 0.66 TEST= 0
INDE 23 25 44 FOBS=    47.2 SIGMA=   4.1 PHAS= -113.9 FOM= 0.30 TEST= 0
INDE 23 25 46 FOBS=   133.1 SIGMA=   1.3 PHAS=   93.8 FOM= 0.91 TEST= 0
INDE 23 25 48 FOBS=    82.3 SIGMA=   1.9 PHAS= -111.4 FOM= 0.94 TEST= 0
```

*FIG. 12A - 475*

```
INDE 23 25 50 FOBS=    96.4 SIGMA=  1.8 PHAS=   21.2 FOM= 0.88 TEST= 0
INDE 23 25 52 FOBS=    48.5 SIGMA=  3.4 PHAS=  116.9 FOM= 0.86 TEST= 0
INDE 23 25 54 FOBS=   191.1 SIGMA=  1.0 PHAS= -171.9 FOM= 0.98 TEST= 0
INDE 23 25 56 FOBS=    78.3 SIGMA=  3.3 PHAS=  -94.6 FOM= 0.84 TEST= 0
INDE 23 25 58 FOBS=    40.9 SIGMA=  7.0 PHAS=  -83.8 FOM= 0.49 TEST= 0
INDE 23 25 60 FOBS=   114.2 SIGMA=  2.6 PHAS=   83.1 FOM= 0.93 TEST= 0
INDE 23 25 62 FOBS=    78.0 SIGMA=  3.8 PHAS=   88.1 FOM= 0.92 TEST= 0
INDE 23 25 64 FOBS=    82.5 SIGMA=  3.6 PHAS=  124.0 FOM= 0.91 TEST= 0
INDE 23 25 66 FOBS=    39.9 SIGMA= 11.2 PHAS= -101.2 FOM= 0.63 TEST= 0
INDE 23 25 68 FOBS=    19.4 SIGMA= 23.2 PHAS= -125.2 FOM= 0.45 TEST= 0
INDE 23 26 23 FOBS=   235.1 SIGMA=  0.8 PHAS=  -45.1 FOM= 0.97 TEST= 0
INDE 23 26 25 FOBS=   127.5 SIGMA=  1.3 PHAS=  114.9 FOM= 0.86 TEST= 0
INDE 23 26 27 FOBS=   137.2 SIGMA=  1.2 PHAS=  150.3 FOM= 0.95 TEST= 0
INDE 23 26 29 FOBS=   127.7 SIGMA=  1.3 PHAS=  -93.7 FOM= 0.93 TEST= 0
INDE 23 26 31 FOBS=   145.6 SIGMA=  1.2 PHAS=   44.9 FOM= 0.96 TEST= 0
INDE 23 26 33 FOBS=   154.4 SIGMA=  1.1 PHAS= -165.0 FOM= 0.48 TEST= 0
INDE 23 26 35 FOBS=   138.6 SIGMA=  1.3 PHAS= -105.5 FOM= 0.80 TEST= 0
INDE 23 26 37 FOBS=   146.0 SIGMA=  1.2 PHAS=  -50.9 FOM= 0.95 TEST= 0
INDE 23 26 39 FOBS=    53.7 SIGMA=  3.5 PHAS=   10.9 FOM= 0.70 TEST= 0
INDE 23 26 41 FOBS=     0.0 SIGMA= 19.8 PHAS=    0.0 FOM= 0.00 TEST= 0
INDE 23 26 43 FOBS=   125.2 SIGMA=  1.5 PHAS=  165.5 FOM= 0.74 TEST= 0
INDE 23 26 45 FOBS=    87.6 SIGMA=  2.0 PHAS=  -73.9 FOM= 0.13 TEST= 1
INDE 23 26 47 FOBS=    54.9 SIGMA=  3.1 PHAS=   -4.9 FOM= 0.23 TEST= 0
INDE 23 26 49 FOBS=   111.5 SIGMA=  1.5 PHAS= -171.8 FOM= 0.92 TEST= 0
INDE 23 26 51 FOBS=    97.6 SIGMA=  1.7 PHAS=  -51.8 FOM= 0.77 TEST= 0
INDE 23 26 53 FOBS=   107.5 SIGMA=  1.6 PHAS=   85.2 FOM= 0.95 TEST= 0
INDE 23 26 55 FOBS=    54.5 SIGMA=  3.9 PHAS=  112.0 FOM= 0.59 TEST= 0
INDE 23 26 57 FOBS=    22.4 SIGMA= 11.4 PHAS=  121.7 FOM= 0.10 TEST= 0
INDE 23 26 59 FOBS=    54.1 SIGMA=  5.4 PHAS=  -66.4 FOM= 0.21 TEST= 0
INDE 23 26 61 FOBS=    52.9 SIGMA=  5.5 PHAS=   38.4 FOM= 0.79 TEST= 0
INDE 23 26 63 FOBS=    93.0 SIGMA=  3.3 PHAS=    2.0 FOM= 0.94 TEST= 0
INDE 23 26 65 FOBS=    50.4 SIGMA=  8.9 PHAS=   19.6 FOM= 0.63 TEST= 0
INDE 23 26 67 FOBS=    36.9 SIGMA= 12.2 PHAS=  132.2 FOM= 0.17 TEST= 0
INDE 23 26 69 FOBS=    36.4 SIGMA= 12.4 PHAS=  111.6 FOM= 0.61 TEST= 0
INDE 23 27 24 FOBS=   122.6 SIGMA=  1.3 PHAS=  -43.2 FOM= 0.97 TEST= 0
INDE 23 27 26 FOBS=   317.8 SIGMA=  0.7 PHAS=   32.7 FOM= 0.98 TEST= 0
INDE 23 27 28 FOBS=   169.6 SIGMA=  0.9 PHAS=  146.5 FOM= 0.94 TEST= 0
INDE 23 27 30 FOBS=   181.9 SIGMA=  1.0 PHAS=   30.1 FOM= 0.88 TEST= 0
INDE 23 27 32 FOBS=   126.4 SIGMA=  1.4 PHAS=  -24.6 FOM= 0.89 TEST= 0
INDE 23 27 34 FOBS=     0.0 SIGMA= 19.8 PHAS=    0.0 FOM= 0.00 TEST= 0
INDE 23 27 36 FOBS=    76.4 SIGMA=  2.2 PHAS= -115.7 FOM= 0.88 TEST= 0
INDE 23 27 38 FOBS=   206.6 SIGMA=  0.9 PHAS=  -54.0 FOM= 0.97 TEST= 0
INDE 23 27 40 FOBS=   126.7 SIGMA=  1.5 PHAS=   24.9 FOM= 0.84 TEST= 0
INDE 23 27 42 FOBS=   238.3 SIGMA=  0.9 PHAS=   44.6 FOM= 0.96 TEST= 0
INDE 23 27 44 FOBS=   125.5 SIGMA=  1.4 PHAS= -176.1 FOM= 0.91 TEST= 0
INDE 23 27 46 FOBS=     0.0 SIGMA= 18.8 PHAS=    0.0 FOM= 0.00 TEST= 1
INDE 23 27 48 FOBS=    42.3 SIGMA=  4.0 PHAS=  159.7 FOM= 0.69 TEST= 0
INDE 23 27 50 FOBS=   130.2 SIGMA=  1.3 PHAS=  115.9 FOM= 0.89 TEST= 0
INDE 23 27 52 FOBS=   108.5 SIGMA=  1.5 PHAS=   50.1 FOM= 0.86 TEST= 0
INDE 23 27 54 FOBS=   105.1 SIGMA=  1.8 PHAS=  -66.4 FOM= 0.83 TEST= 0
INDE 23 27 56 FOBS=    79.3 SIGMA=  3.0 PHAS=  103.7 FOM= 0.01 TEST= 1
INDE 23 27 58 FOBS=     0.0 SIGMA= 24.5 PHAS=    0.0 FOM= 0.00 TEST= 0
INDE 23 27 60 FOBS=    69.8 SIGMA=  4.3 PHAS=   83.0 FOM= 0.72 TEST= 0
INDE 23 27 62 FOBS=    21.9 SIGMA= 13.4 PHAS=  -27.0 FOM= 0.02 TEST= 1
INDE 23 27 64 FOBS=    55.1 SIGMA=  6.5 PHAS= -166.8 FOM= 0.41 TEST= 0
INDE 23 27 66 FOBS=    18.7 SIGMA= 24.0 PHAS=  -78.7 FOM= 0.08 TEST= 0
INDE 23 27 68 FOBS=     0.0 SIGMA= 29.5 PHAS=    0.0 FOM= 0.00 TEST= 0
INDE 23 28 23 FOBS=    92.0 SIGMA=  1.6 PHAS=  -93.0 FOM= 0.90 TEST= 0
INDE 23 28 25 FOBS=    29.3 SIGMA=  5.7 PHAS=   -6.9 FOM= 0.41 TEST= 0
INDE 23 28 27 FOBS=   171.2 SIGMA=  1.0 PHAS= -126.4 FOM= 0.94 TEST= 0
INDE 23 28 29 FOBS=   182.0 SIGMA=  0.9 PHAS=   -3.3 FOM= 0.96 TEST= 0
INDE 23 28 31 FOBS=   305.8 SIGMA=  0.7 PHAS=   20.5 FOM= 0.95 TEST= 1
INDE 23 28 33 FOBS=   195.1 SIGMA=  1.0 PHAS= -101.5 FOM= 0.94 TEST= 0
INDE 23 28 35 FOBS=   100.3 SIGMA=  1.7 PHAS=  -15.4 FOM= 0.96 TEST= 0
INDE 23 28 37 FOBS=   127.0 SIGMA=  1.2 PHAS= -169.2 FOM= 0.96 TEST= 0
INDE 23 28 39 FOBS=   145.7 SIGMA=  1.2 PHAS= -110.1 FOM= 0.94 TEST= 0
INDE 23 28 41 FOBS=   251.3 SIGMA=  0.7 PHAS=  -44.5 FOM= 0.97 TEST= 0
INDE 23 28 43 FOBS=   136.4 SIGMA=  1.3 PHAS=   13.0 FOM= 0.93 TEST= 0
INDE 23 28 45 FOBS=    31.7 SIGMA=  5.6 PHAS=   72.7 FOM= 0.28 TEST= 1
INDE 23 28 47 FOBS=   102.4 SIGMA=  1.7 PHAS=  -96.5 FOM= 0.92 TEST= 0
```

*FIG. 12A - 476*

```
INDE 23 28 49 FOBS=    0.0 SIGMA= 18.2 PHAS=    0.0 FOM= 0.00 TEST= 0
INDE 23 28 51 FOBS=  135.4 SIGMA=  1.3 PHAS=  -61.3 FOM= 0.96 TEST= 0
INDE 23 28 53 FOBS=  131.3 SIGMA=  1.5 PHAS=  -74.1 FOM= 0.94 TEST= 0
INDE 23 28 55 FOBS=   40.4 SIGMA=  6.5 PHAS=  127.4 FOM= 0.49 TEST= 0
INDE 23 28 57 FOBS=   67.5 SIGMA=  3.5 PHAS=  133.0 FOM= 0.87 TEST= 0
INDE 23 28 59 FOBS=   31.8 SIGMA=  7.3 PHAS= -159.2 FOM= 0.07 TEST= 0
INDE 23 28 61 FOBS=    0.0 SIGMA= 24.2 PHAS=    0.0 FOM= 0.00 TEST= 1
INDE 23 28 63 FOBS=    0.0 SIGMA= 26.8 PHAS=    0.0 FOM= 0.00 TEST= 0
INDE 23 28 65 FOBS=   83.1 SIGMA=  5.4 PHAS=  120.1 FOM= 0.90 TEST= 0
INDE 23 28 67 FOBS=   16.6 SIGMA= 26.4 PHAS=    4.9 FOM= 0.02 TEST= 1
INDE 23 29 24 FOBS=  274.3 SIGMA=  0.7 PHAS=  -13.6 FOM= 0.95 TEST= 0
INDE 23 29 26 FOBS=  234.8 SIGMA=  0.8 PHAS=   63.3 FOM= 0.96 TEST= 0
INDE 23 29 28 FOBS=  223.3 SIGMA=  0.8 PHAS=  138.5 FOM= 0.97 TEST= 0
INDE 23 29 30 FOBS=  174.9 SIGMA=  1.0 PHAS=  -23.5 FOM= 0.96 TEST= 0
INDE 23 29 32 FOBS=  188.1 SIGMA=  1.0 PHAS=  -47.5 FOM= 0.95 TEST= 0
INDE 23 29 34 FOBS=  276.0 SIGMA=  0.7 PHAS=  -85.3 FOM= 0.96 TEST= 0
INDE 23 29 36 FOBS=   64.1 SIGMA=  2.6 PHAS=    7.5 FOM= 0.91 TEST= 0
INDE 23 29 38 FOBS=   95.0 SIGMA=  1.7 PHAS=  -30.9 FOM= 0.94 TEST= 0
INDE 23 29 40 FOBS=  168.7 SIGMA=  1.0 PHAS= -151.3 FOM= 0.93 TEST= 0
INDE 23 29 42 FOBS=   23.7 SIGMA=  6.9 PHAS=  169.8 FOM= 0.20 TEST= 0
INDE 23 29 44 FOBS=   41.2 SIGMA=  4.2 PHAS= -144.8 FOM= 0.70 TEST= 1
INDE 23 29 46 FOBS=   25.8 SIGMA=  6.5 PHAS= -165.2 FOM= 0.06 TEST= 0
INDE 23 29 48 FOBS=   75.9 SIGMA=  2.2 PHAS=  146.4 FOM= 0.90 TEST= 0
INDE 23 29 50 FOBS=   16.8 SIGMA= 10.4 PHAS= -149.8 FOM= 0.09 TEST= 0
INDE 23 29 52 FOBS=   42.5 SIGMA=  4.3 PHAS=  177.8 FOM= 0.89 TEST= 0
INDE 23 29 54 FOBS=   34.8 SIGMA=  5.9 PHAS= -161.8 FOM= 0.54 TEST= 0
INDE 23 29 56 FOBS=   49.4 SIGMA=  6.1 PHAS=   44.6 FOM= 0.53 TEST= 0
INDE 23 29 58 FOBS=  126.5 SIGMA=  2.0 PHAS=   63.4 FOM= 0.94 TEST= 0
INDE 23 29 60 FOBS=    0.0 SIGMA= 21.6 PHAS=    0.0 FOM= 0.00 TEST= 0
INDE 23 29 62 FOBS=   31.3 SIGMA=  9.4 PHAS=   69.8 FOM= 0.54 TEST= 0
INDE 23 29 64 FOBS=   97.6 SIGMA=  4.7 PHAS=   50.9 FOM= 0.88 TEST= 0
INDE 23 29 66 FOBS=   53.1 SIGMA=  8.3 PHAS=   67.4 FOM= 0.79 TEST= 0
INDE 23 29 68 FOBS=    0.0 SIGMA= 29.9 PHAS=    0.0 FOM= 0.00 TEST= 0
INDE 23 30 23 FOBS=  277.2 SIGMA=  0.7 PHAS=  -92.9 FOM= 0.93 TEST= 0
INDE 23 30 25 FOBS=  173.4 SIGMA=  1.0 PHAS=  -40.4 FOM= 0.81 TEST= 0
INDE 23 30 27 FOBS=   92.2 SIGMA=  1.9 PHAS=   54.2 FOM= 0.93 TEST= 0
INDE 23 30 29 FOBS=  199.9 SIGMA=  0.9 PHAS=  -80.3 FOM= 0.96 TEST= 0
INDE 23 30 31 FOBS=  184.9 SIGMA=  1.0 PHAS= -134.6 FOM= 0.94 TEST= 0
INDE 23 30 33 FOBS=  326.5 SIGMA=  0.7 PHAS= -125.0 FOM= 0.96 TEST= 0
INDE 23 30 35 FOBS=  111.2 SIGMA=  1.5 PHAS= -138.7 FOM= 0.78 TEST= 0
INDE 23 30 37 FOBS=  139.5 SIGMA=  1.2 PHAS= -145.6 FOM= 0.88 TEST= 0
INDE 23 30 39 FOBS=  179.9 SIGMA=  1.0 PHAS= -110.3 FOM= 0.91 TEST= 0
INDE 23 30 41 FOBS=  126.9 SIGMA=  1.3 PHAS=   55.0 FOM= 0.77 TEST= 0
INDE 23 30 43 FOBS=   80.6 SIGMA=  2.0 PHAS=  -70.3 FOM= 0.91 TEST= 0
INDE 23 30 45 FOBS=   56.5 SIGMA=  2.7 PHAS=   45.3 FOM= 0.62 TEST= 1
INDE 23 30 47 FOBS=   69.7 SIGMA=  2.2 PHAS= -128.9 FOM= 0.11 TEST= 1
INDE 23 30 49 FOBS=    0.0 SIGMA= 17.7 PHAS=    0.0 FOM= 0.00 TEST= 0
INDE 23 30 51 FOBS=   56.4 SIGMA=  3.3 PHAS=  -32.3 FOM= 0.85 TEST= 0
INDE 23 30 53 FOBS=   82.0 SIGMA=  2.3 PHAS=  -65.0 FOM= 0.84 TEST= 0
INDE 23 30 55 FOBS=   55.0 SIGMA=  4.3 PHAS=   23.4 FOM= 0.79 TEST= 0
INDE 23 30 57 FOBS=  110.5 SIGMA=  2.5 PHAS=   20.6 FOM= 0.94 TEST= 0
INDE 23 30 59 FOBS=   13.2 SIGMA= 22.3 PHAS= -140.3 FOM= 0.21 TEST= 0
INDE 23 30 61 FOBS=    0.0 SIGMA= 25.2 PHAS=    0.0 FOM= 0.00 TEST= 0
INDE 23 30 63 FOBS=   69.7 SIGMA=  5.1 PHAS= -111.8 FOM= 0.87 TEST= 0
INDE 23 30 65 FOBS=    0.0 SIGMA= 30.1 PHAS=    0.0 FOM= 0.00 TEST= 0
INDE 23 30 67 FOBS=    9.3 SIGMA= 48.9 PHAS=   55.7 FOM= 0.05 TEST= 0
INDE 23 31 24 FOBS=   31.8 SIGMA=  5.1 PHAS=   57.8 FOM= 0.60 TEST= 0
INDE 23 31 26 FOBS=  188.6 SIGMA=  1.0 PHAS=  -35.3 FOM= 0.90 TEST= 0
INDE 23 31 28 FOBS=   93.2 SIGMA=  2.0 PHAS=   -9.6 FOM= 0.81 TEST= 0
INDE 23 31 30 FOBS=  267.8 SIGMA=  0.8 PHAS=  117.5 FOM= 0.97 TEST= 0
INDE 23 31 32 FOBS=  287.4 SIGMA=  0.7 PHAS=  110.7 FOM= 0.96 TEST= 0
INDE 23 31 34 FOBS=   88.3 SIGMA=  1.9 PHAS=  -40.9 FOM= 0.89 TEST= 0
INDE 23 31 36 FOBS=  205.8 SIGMA=  0.9 PHAS=   59.2 FOM= 0.94 TEST= 0
INDE 23 31 38 FOBS=  106.9 SIGMA=  1.6 PHAS= -177.8 FOM= 0.88 TEST= 0
INDE 23 31 40 FOBS=  110.0 SIGMA=  1.5 PHAS= -113.1 FOM= 0.80 TEST= 0
INDE 23 31 42 FOBS=   86.2 SIGMA=  1.9 PHAS= -145.8 FOM= 0.85 TEST= 0
INDE 23 31 44 FOBS=   83.9 SIGMA=  1.9 PHAS= -103.6 FOM= 0.75 TEST= 0
INDE 23 31 46 FOBS=   52.3 SIGMA=  3.0 PHAS=  -42.8 FOM= 0.83 TEST= 1
INDE 23 31 48 FOBS=   21.2 SIGMA=  8.3 PHAS=  157.6 FOM= 0.17 TEST= 0
INDE 23 31 50 FOBS=  108.6 SIGMA=  1.6 PHAS= -138.3 FOM= 0.95 TEST= 0
```

*FIG. 12A - 477*

```
INDE 23 31 52 FOBS=   111.1 SIGMA=  1.5 PHAS=   50.0 FOM= 0.13 TEST= 1
INDE 23 31 54 FOBS=    60.0 SIGMA=  3.3 PHAS=  -32.6 FOM= 0.78 TEST= 0
INDE 23 31 56 FOBS=    95.4 SIGMA=  2.5 PHAS=  -60.7 FOM= 0.92 TEST= 0
INDE 23 31 58 FOBS=    53.7 SIGMA=  4.8 PHAS=   37.2 FOM= 0.77 TEST= 0
INDE 23 31 60 FOBS=     0.0 SIGMA= 26.8 PHAS=    0.0 FOM= 0.00 TEST= 1
INDE 23 31 62 FOBS=     0.0 SIGMA= 26.3 PHAS=    0.0 FOM= 0.00 TEST= 0
INDE 23 31 64 FOBS=   100.6 SIGMA=  3.7 PHAS=  101.7 FOM= 0.88 TEST= 0
INDE 23 31 66 FOBS=    35.9 SIGMA= 12.8 PHAS=   52.2 FOM= 0.41 TEST= 0
INDE 23 32 23 FOBS=   306.1 SIGMA=  0.7 PHAS=   -5.5 FOM= 0.97 TEST= 0
INDE 23 32 25 FOBS=     5.2 SIGMA= 34.2 PHAS= -126.0 FOM= 0.03 TEST= 0
INDE 23 32 27 FOBS=   320.1 SIGMA=  0.7 PHAS= -125.6 FOM= 0.95 TEST= 0
INDE 23 32 29 FOBS=   215.9 SIGMA=  1.0 PHAS=  -84.6 FOM= 0.96 TEST= 0
INDE 23 32 31 FOBS=   202.7 SIGMA=  0.9 PHAS=    0.5 FOM= 0.97 TEST= 0
INDE 23 32 33 FOBS=   237.3 SIGMA=  0.8 PHAS=  -39.0 FOM= 0.90 TEST= 0
INDE 23 32 35 FOBS=   184.7 SIGMA=  1.0 PHAS=  -84.1 FOM= 0.94 TEST= 0
INDE 23 32 37 FOBS=    79.4 SIGMA=  2.1 PHAS=   75.5 FOM= 0.90 TEST= 0
INDE 23 32 39 FOBS=   101.2 SIGMA=  1.6 PHAS= -169.8 FOM= 0.69 TEST= 0
INDE 23 32 41 FOBS=     0.0 SIGMA= 18.4 PHAS=    0.0 FOM= 0.00 TEST= 0
INDE 23 32 43 FOBS=   126.8 SIGMA=  1.5 PHAS= -170.3 FOM= 0.89 TEST= 0
INDE 23 32 45 FOBS=    77.6 SIGMA=  2.1 PHAS= -158.1 FOM= 0.93 TEST= 0
INDE 23 32 47 FOBS=   125.8 SIGMA=  1.4 PHAS= -104.1 FOM= 0.94 TEST= 0
INDE 23 32 49 FOBS=    92.0 SIGMA=  1.9 PHAS=  126.3 FOM= 0.93 TEST= 0
INDE 23 32 51 FOBS=    17.0 SIGMA= 10.7 PHAS=   -1.9 FOM= 0.17 TEST= 0
INDE 23 32 53 FOBS=    26.6 SIGMA=  6.7 PHAS=   59.6 FOM= 0.08 TEST= 0
INDE 23 32 55 FOBS=    28.9 SIGMA=  6.8 PHAS=   37.2 FOM= 0.21 TEST= 0
INDE 23 32 57 FOBS=    90.2 SIGMA=  2.2 PHAS=  -21.2 FOM= 0.89 TEST= 0
INDE 23 32 59 FOBS=    48.8 SIGMA=  5.3 PHAS= -172.4 FOM= 0.80 TEST= 0
INDE 23 32 61 FOBS=     0.0 SIGMA= 26.4 PHAS=    0.0 FOM= 0.00 TEST= 0
INDE 23 32 63 FOBS=    53.8 SIGMA=  5.7 PHAS=  -53.8 FOM= 0.75 TEST= 0
INDE 23 32 65 FOBS=     0.0 SIGMA= 24.7 PHAS=    0.0 FOM= 0.00 TEST= 0
INDE 23 32 67 FOBS=    12.9 SIGMA= 35.7 PHAS=  115.6 FOM= 0.41 TEST= 0
INDE 23 33 24 FOBS=   153.0 SIGMA=  1.2 PHAS= -104.3 FOM= 0.94 TEST= 0
INDE 23 33 26 FOBS=    49.0 SIGMA=  3.7 PHAS=  166.5 FOM= 0.96 TEST= 0
INDE 23 33 28 FOBS=   281.1 SIGMA=  0.8 PHAS=  131.0 FOM= 0.91 TEST= 0
INDE 23 33 30 FOBS=    24.8 SIGMA=  7.4 PHAS=  154.6 FOM= 0.43 TEST= 0
INDE 23 33 32 FOBS=   114.1 SIGMA=  1.5 PHAS=  -68.3 FOM= 0.91 TEST= 0
INDE 23 33 34 FOBS=     0.0 SIGMA= 18.2 PHAS=    0.0 FOM= 0.00 TEST= 0
INDE 23 33 36 FOBS=   191.3 SIGMA=  0.9 PHAS=   44.7 FOM= 0.98 TEST= 0
INDE 23 33 38 FOBS=    72.5 SIGMA=  2.3 PHAS=   13.1 FOM= 0.82 TEST= 0
INDE 23 33 40 FOBS=    48.6 SIGMA=  3.3 PHAS=   66.1 FOM= 0.12 TEST= 0
INDE 23 33 42 FOBS=   118.2 SIGMA=  1.4 PHAS=  172.1 FOM= 0.86 TEST= 0
INDE 23 33 44 FOBS=   118.7 SIGMA=  1.5 PHAS=   80.6 FOM= 0.96 TEST= 0
INDE 23 33 46 FOBS=    93.5 SIGMA=  2.1 PHAS= -155.1 FOM= 0.89 TEST= 0
INDE 23 33 48 FOBS=    24.5 SIGMA=  7.3 PHAS=   70.1 FOM= 0.25 TEST= 0
INDE 23 33 50 FOBS=     0.0 SIGMA= 18.6 PHAS=    0.0 FOM= 0.00 TEST= 0
INDE 23 33 52 FOBS=     0.0 SIGMA= 20.5 PHAS=    0.0 FOM= 0.00 TEST= 0
INDE 23 33 54 FOBS=     0.0 SIGMA= 21.3 PHAS=    0.0 FOM= 0.00 TEST= 0
INDE 23 33 56 FOBS=    27.6 SIGMA=  7.2 PHAS=  -62.3 FOM= 0.63 TEST= 0
INDE 23 33 58 FOBS=    54.9 SIGMA=  3.6 PHAS=   59.7 FOM= 0.58 TEST= 0
INDE 23 33 60 FOBS=    59.2 SIGMA=  4.5 PHAS=  100.1 FOM= 0.84 TEST= 0
INDE 23 33 62 FOBS=     0.0 SIGMA= 24.6 PHAS=    0.0 FOM= 0.00 TEST= 0
INDE 23 33 64 FOBS=    31.5 SIGMA=  9.6 PHAS=   11.5 FOM= 0.13 TEST= 1
INDE 23 33 66 FOBS=    88.8 SIGMA=  3.5 PHAS=   27.5 FOM= 0.85 TEST= 0
INDE 23 34 23 FOBS=    86.1 SIGMA=  2.1 PHAS= -117.8 FOM= 0.71 TEST= 0
INDE 23 34 25 FOBS=   100.9 SIGMA=  1.8 PHAS= -175.2 FOM= 0.96 TEST= 0
INDE 23 34 27 FOBS=   239.3 SIGMA=  0.9 PHAS=  165.4 FOM= 0.96 TEST= 0
INDE 23 34 29 FOBS=   199.2 SIGMA=  1.0 PHAS=  -32.6 FOM= 0.96 TEST= 0
INDE 23 34 31 FOBS=   208.1 SIGMA=  0.9 PHAS=  -82.2 FOM= 0.93 TEST= 0
INDE 23 34 33 FOBS=    87.2 SIGMA=  1.9 PHAS=  -90.6 FOM= 0.56 TEST= 0
INDE 23 34 35 FOBS=   146.5 SIGMA=  1.2 PHAS=  -76.1 FOM= 0.95 TEST= 0
INDE 23 34 37 FOBS=    74.8 SIGMA=  2.2 PHAS=  -54.0 FOM= 0.84 TEST= 0
INDE 23 34 39 FOBS=    40.7 SIGMA=  4.0 PHAS=  -91.6 FOM= 0.31 TEST= 0
INDE 23 34 41 FOBS=   109.6 SIGMA=  1.5 PHAS=  -28.1 FOM= 0.93 TEST= 0
INDE 23 34 43 FOBS=   150.2 SIGMA=  1.2 PHAS= -135.8 FOM= 0.92 TEST= 0
INDE 23 34 45 FOBS=    92.1 SIGMA=  2.1 PHAS=   61.5 FOM= 0.91 TEST= 0
INDE 23 34 47 FOBS=    60.9 SIGMA=  3.1 PHAS= -146.0 FOM= 0.53 TEST= 0
INDE 23 34 49 FOBS=     0.0 SIGMA= 18.6 PHAS=    0.0 FOM= 0.00 TEST= 0
INDE 23 34 51 FOBS=    88.1 SIGMA=  2.1 PHAS=  -33.8 FOM= 0.91 TEST= 0
INDE 23 34 53 FOBS=    16.8 SIGMA= 12.9 PHAS=  150.1 FOM= 0.05 TEST= 0
INDE 23 34 55 FOBS=     0.0 SIGMA= 19.8 PHAS=    0.0 FOM= 0.00 TEST= 0
```

*FIG. 12A - 478*

```
INDE 23 34 57 FOBS=    60.9 SIGMA=  3.3 PHAS=  143.8 FOM= 0.05 TEST= 1
INDE 23 34 59 FOBS=     0.0 SIGMA= 20.7 PHAS=    0.0 FOM= 0.00 TEST= 0
INDE 23 34 61 FOBS=    35.4 SIGMA=  6.6 PHAS=  -77.9 FOM= 0.58 TEST= 0
INDE 23 34 63 FOBS=   112.9 SIGMA=  2.8 PHAS=  -35.2 FOM= 0.45 TEST= 1
INDE 23 34 65 FOBS=     0.0 SIGMA= 28.6 PHAS=    0.0 FOM= 0.00 TEST= 0
INDE 23 35 24 FOBS=    90.8 SIGMA=  2.1 PHAS=  171.9 FOM= 0.92 TEST= 1
INDE 23 35 26 FOBS=   101.0 SIGMA=  1.9 PHAS=   56.9 FOM= 0.84 TEST= 0
INDE 23 35 28 FOBS=   193.3 SIGMA=  1.1 PHAS=  125.4 FOM= 0.95 TEST= 0
INDE 23 35 30 FOBS=    89.6 SIGMA=  2.1 PHAS= -111.3 FOM= 0.74 TEST= 0
INDE 23 35 32 FOBS=   135.9 SIGMA=  1.3 PHAS= -173.0 FOM= 0.92 TEST= 0
INDE 23 35 34 FOBS=    99.2 SIGMA=  1.7 PHAS= -156.8 FOM= 0.70 TEST= 0
INDE 23 35 36 FOBS=   154.6 SIGMA=  1.1 PHAS=  -76.1 FOM= 0.77 TEST= 0
INDE 23 35 38 FOBS=    61.9 SIGMA=  2.6 PHAS=  123.2 FOM= 0.66 TEST= 0
INDE 23 35 40 FOBS=   118.2 SIGMA=  1.4 PHAS=  -85.4 FOM= 0.88 TEST= 0
INDE 23 35 42 FOBS=   234.8 SIGMA=  0.8 PHAS=  143.6 FOM= 0.97 TEST= 0
INDE 23 35 44 FOBS=    43.5 SIGMA=  4.7 PHAS=  136.0 FOM= 0.68 TEST= 0
INDE 23 35 46 FOBS=    59.3 SIGMA=  3.2 PHAS=    6.9 FOM= 0.26 TEST= 0
INDE 23 35 48 FOBS=    61.7 SIGMA=  3.0 PHAS=   57.7 FOM= 0.72 TEST= 0
INDE 23 35 50 FOBS=    85.4 SIGMA=  2.2 PHAS=  -57.4 FOM= 0.85 TEST= 0
INDE 23 35 52 FOBS=    47.2 SIGMA=  3.9 PHAS=   35.5 FOM= 0.68 TEST= 0
INDE 23 35 54 FOBS=     0.0 SIGMA= 21.7 PHAS=    0.0 FOM= 0.00 TEST= 0
INDE 23 35 56 FOBS=    29.9 SIGMA=  8.1 PHAS= -120.6 FOM= 0.26 TEST= 0
INDE 23 35 58 FOBS=    23.0 SIGMA=  8.6 PHAS=   74.7 FOM= 0.44 TEST= 0
INDE 23 35 60 FOBS=     0.0 SIGMA= 24.2 PHAS=    0.0 FOM= 0.00 TEST= 0
INDE 23 35 62 FOBS=     0.0 SIGMA= 21.0 PHAS=    0.0 FOM= 0.00 TEST= 0
INDE 23 35 64 FOBS=     0.0 SIGMA= 25.8 PHAS=    0.0 FOM= 0.00 TEST= 0
INDE 23 36 23 FOBS=    60.4 SIGMA=  3.7 PHAS=   48.4 FOM= 0.51 TEST= 0
INDE 23 36 25 FOBS=    94.7 SIGMA=  2.0 PHAS=  151.4 FOM= 0.88 TEST= 0
INDE 23 36 27 FOBS=   246.9 SIGMA=  0.9 PHAS= -168.7 FOM= 0.92 TEST= 1
INDE 23 36 29 FOBS=    62.2 SIGMA=  3.0 PHAS=  -48.9 FOM= 0.79 TEST= 0
INDE 23 36 31 FOBS=    74.2 SIGMA=  2.5 PHAS=  166.1 FOM= 0.65 TEST= 0
INDE 23 36 33 FOBS=    17.0 SIGMA=  9.8 PHAS=  145.5 FOM= 0.12 TEST= 0
INDE 23 36 35 FOBS=   230.5 SIGMA=  0.8 PHAS= -114.5 FOM= 0.88 TEST= 1
INDE 23 36 37 FOBS=    98.8 SIGMA=  1.7 PHAS=  -68.4 FOM= 0.94 TEST= 0
INDE 23 36 39 FOBS=   146.8 SIGMA=  1.2 PHAS= -171.0 FOM= 0.86 TEST= 0
INDE 23 36 41 FOBS=   131.6 SIGMA=  1.3 PHAS=   12.2 FOM= 0.89 TEST= 0
INDE 23 36 43 FOBS=    26.5 SIGMA=  7.2 PHAS=  154.1 FOM= 0.81 TEST= 0
INDE 23 36 45 FOBS=    50.6 SIGMA=  3.8 PHAS=  162.6 FOM= 0.79 TEST= 0
INDE 23 36 47 FOBS=    77.7 SIGMA=  2.5 PHAS=  -19.9 FOM= 0.93 TEST= 0
INDE 23 36 49 FOBS=    85.6 SIGMA=  2.2 PHAS=  -79.9 FOM= 0.89 TEST= 0
INDE 23 36 51 FOBS=   133.9 SIGMA=  1.5 PHAS=  -30.1 FOM= 0.94 TEST= 0
INDE 23 36 53 FOBS=   153.9 SIGMA=  1.4 PHAS=  -46.5 FOM= 0.98 TEST= 0
INDE 23 36 55 FOBS=    77.5 SIGMA=  2.7 PHAS=   11.6 FOM= 0.87 TEST= 0
INDE 23 36 57 FOBS=     0.0 SIGMA= 21.6 PHAS=    0.0 FOM= 0.00 TEST= 0
INDE 23 36 59 FOBS=     0.0 SIGMA= 20.8 PHAS=    0.0 FOM= 0.00 TEST= 0
INDE 23 36 61 FOBS=     0.0 SIGMA= 20.9 PHAS=    0.0 FOM= 0.00 TEST= 0
INDE 23 36 63 FOBS=    19.8 SIGMA= 12.3 PHAS=   22.3 FOM= 0.49 TEST= 0
INDE 23 37 24 FOBS=   193.4 SIGMA=  1.1 PHAS=  100.9 FOM= 0.91 TEST= 0
INDE 23 37 26 FOBS=    88.4 SIGMA=  2.1 PHAS=   47.7 FOM= 0.88 TEST= 0
INDE 23 37 28 FOBS=   206.7 SIGMA=  1.0 PHAS=   71.8 FOM= 0.35 TEST= 1
INDE 23 37 30 FOBS=    66.9 SIGMA=  2.8 PHAS=   37.7 FOM= 0.94 TEST= 0
INDE 23 37 32 FOBS=   138.7 SIGMA=  1.4 PHAS=  110.7 FOM= 0.66 TEST= 0
INDE 23 37 34 FOBS=   168.0 SIGMA=  1.1 PHAS= -163.8 FOM= 0.86 TEST= 0
INDE 23 37 36 FOBS=    54.6 SIGMA=  3.0 PHAS=  154.7 FOM= 0.95 TEST= 0
INDE 23 37 38 FOBS=   182.4 SIGMA=  1.0 PHAS= -149.0 FOM= 0.90 TEST= 0
INDE 23 37 40 FOBS=    63.8 SIGMA=  2.7 PHAS=   57.3 FOM= 0.26 TEST= 0
INDE 23 37 42 FOBS=   107.6 SIGMA=  1.7 PHAS=  128.0 FOM= 0.79 TEST= 0
INDE 23 37 44 FOBS=     0.0 SIGMA= 18.9 PHAS=    0.0 FOM= 0.00 TEST= 0
INDE 23 37 46 FOBS=    44.8 SIGMA=  4.3 PHAS= -124.5 FOM= 0.71 TEST= 0
INDE 23 37 48 FOBS=   110.0 SIGMA=  1.8 PHAS= -109.0 FOM= 0.91 TEST= 0
INDE 23 37 50 FOBS=   108.3 SIGMA=  1.8 PHAS= -149.7 FOM= 0.89 TEST= 0
INDE 23 37 52 FOBS=    71.8 SIGMA=  2.6 PHAS=  -95.4 FOM= 0.92 TEST= 0
INDE 23 37 54 FOBS=   153.1 SIGMA=  1.4 PHAS= -116.1 FOM= 0.95 TEST= 1
INDE 23 37 56 FOBS=    48.6 SIGMA=  4.2 PHAS=   11.3 FOM= 0.51 TEST= 1
INDE 23 37 58 FOBS=    54.4 SIGMA=  4.1 PHAS=  116.0 FOM= 0.72 TEST= 0
INDE 23 37 60 FOBS=    48.1 SIGMA=  4.6 PHAS= -162.4 FOM= 0.29 TEST= 1
INDE 23 37 62 FOBS=    10.7 SIGMA= 23.0 PHAS=  110.5 FOM= 0.11 TEST= 0
INDE 23 37 64 FOBS=     9.6 SIGMA= 25.8 PHAS=    0.8 FOM= 0.26 TEST= 0
INDE 23 38 23 FOBS=   260.3 SIGMA=  1.0 PHAS=   31.0 FOM= 0.98 TEST= 0
INDE 23 38 25 FOBS=    47.9 SIGMA=  3.8 PHAS=  -96.5 FOM= 0.65 TEST= 0
```

*FIG. 12A - 479*

```
INDE 23 38 27 FOBS=  73.1 SIGMA=  2.6 PHAS= -128.9 FOM= 0.63 TEST= 0
INDE 23 38 29 FOBS=  53.6 SIGMA=  3.4 PHAS=   16.0 FOM= 0.85 TEST= 1
INDE 23 38 31 FOBS= 246.5 SIGMA=  0.9 PHAS=  -38.1 FOM= 0.97 TEST= 0
INDE 23 38 33 FOBS= 150.0 SIGMA=  1.3 PHAS=  167.7 FOM= 0.89 TEST= 0
INDE 23 38 35 FOBS=  79.3 SIGMA=  2.1 PHAS=  177.2 FOM= 0.85 TEST= 0
INDE 23 38 37 FOBS= 100.8 SIGMA=  1.7 PHAS=   68.2 FOM= 0.87 TEST= 0
INDE 23 38 39 FOBS=   0.0 SIGMA= 18.8 PHAS=    0.0 FOM= 0.00 TEST= 0
INDE 23 38 41 FOBS=  11.5 SIGMA= 16.1 PHAS= -154.0 FOM= 0.16 TEST= 0
INDE 23 38 43 FOBS=  39.2 SIGMA=  5.1 PHAS=  149.7 FOM= 0.49 TEST= 0
INDE 23 38 45 FOBS= 110.4 SIGMA=  1.6 PHAS= -159.0 FOM= 0.03 TEST= 1
INDE 23 38 47 FOBS=  41.0 SIGMA=  4.6 PHAS=  149.8 FOM= 0.57 TEST= 0
INDE 23 38 49 FOBS=  52.9 SIGMA=  3.6 PHAS= -132.7 FOM= 0.49 TEST= 0
INDE 23 38 51 FOBS=  77.8 SIGMA=  2.4 PHAS= -151.2 FOM= 0.93 TEST= 0
INDE 23 38 53 FOBS=  88.2 SIGMA=  2.4 PHAS= -101.4 FOM= 0.89 TEST= 0
INDE 23 38 55 FOBS=  42.5 SIGMA=  4.8 PHAS=   85.2 FOM= 0.31 TEST= 0
INDE 23 38 57 FOBS=  52.3 SIGMA=  3.9 PHAS=  141.7 FOM= 0.39 TEST= 0
INDE 23 38 59 FOBS=   0.0 SIGMA= 20.0 PHAS=    0.0 FOM= 0.00 TEST= 0
INDE 23 38 61 FOBS=  29.8 SIGMA=  7.6 PHAS= -150.8 FOM= 0.30 TEST= 0
INDE 23 38 63 FOBS=  90.8 SIGMA=  2.8 PHAS=  -96.5 FOM= 0.90 TEST= 0
INDE 23 39 24 FOBS= 150.4 SIGMA=  1.4 PHAS=  -49.2 FOM= 0.91 TEST= 0
INDE 23 39 26 FOBS=  54.1 SIGMA=  3.4 PHAS=   68.7 FOM= 0.52 TEST= 0
INDE 23 39 28 FOBS=  40.9 SIGMA=  4.4 PHAS=  -34.0 FOM= 0.35 TEST= 0
INDE 23 39 30 FOBS= 136.1 SIGMA=  1.4 PHAS= -119.2 FOM= 0.85 TEST= 0
INDE 23 39 32 FOBS=  29.9 SIGMA=  6.4 PHAS=  138.6 FOM= 0.71 TEST= 0
INDE 23 39 34 FOBS=  60.7 SIGMA=  2.8 PHAS=  135.5 FOM= 0.80 TEST= 0
INDE 23 39 36 FOBS=  23.2 SIGMA=  7.3 PHAS=  161.6 FOM= 0.26 TEST= 0
INDE 23 39 38 FOBS=   0.0 SIGMA= 18.8 PHAS=    0.0 FOM= 0.00 TEST= 0
INDE 23 39 40 FOBS=  87.0 SIGMA=  2.1 PHAS=  -13.6 FOM= 0.71 TEST= 0
INDE 23 39 42 FOBS= 104.7 SIGMA=  1.7 PHAS=   33.6 FOM= 0.83 TEST= 0
INDE 23 39 44 FOBS=   0.0 SIGMA= 18.6 PHAS=    0.0 FOM= 0.00 TEST= 0
INDE 23 39 46 FOBS=  59.4 SIGMA=  2.9 PHAS= -157.8 FOM= 0.72 TEST= 0
INDE 23 39 48 FOBS=  93.0 SIGMA=  2.1 PHAS= -173.6 FOM= 0.56 TEST= 0
INDE 23 39 50 FOBS= 111.1 SIGMA=  1.7 PHAS=  125.9 FOM= 0.94 TEST= 0
INDE 23 39 52 FOBS=  57.3 SIGMA=  3.9 PHAS=  147.1 FOM= 0.84 TEST= 0
INDE 23 39 54 FOBS=   0.0 SIGMA= 21.1 PHAS=    0.0 FOM= 0.00 TEST= 0
INDE 23 39 56 FOBS=  41.2 SIGMA=  4.9 PHAS= -157.0 FOM= 0.09 TEST= 1
INDE 23 39 58 FOBS=  26.8 SIGMA=  8.8 PHAS=  133.7 FOM= 0.34 TEST= 0
INDE 23 39 60 FOBS=  76.8 SIGMA=  3.2 PHAS=   -1.0 FOM= 0.92 TEST= 0
INDE 23 39 62 FOBS= 117.9 SIGMA=  2.2 PHAS=  146.2 FOM= 0.91 TEST= 0
INDE 23 40 23 FOBS= 165.1 SIGMA=  1.3 PHAS=   70.8 FOM= 0.88 TEST= 0
INDE 23 40 25 FOBS= 139.4 SIGMA=  1.5 PHAS= -178.7 FOM= 0.41 TEST= 1
INDE 23 40 27 FOBS=  84.6 SIGMA=  2.1 PHAS=   26.5 FOM= 0.96 TEST= 0
INDE 23 40 29 FOBS= 102.2 SIGMA=  1.8 PHAS=  147.1 FOM= 0.86 TEST= 0
INDE 23 40 31 FOBS= 133.3 SIGMA=  1.4 PHAS=  -84.0 FOM= 0.88 TEST= 0
INDE 23 40 33 FOBS=   0.0 SIGMA= 19.2 PHAS=    0.0 FOM= 0.00 TEST= 0
INDE 23 40 35 FOBS=  49.2 SIGMA=  3.8 PHAS=  -14.9 FOM= 0.80 TEST= 0
INDE 23 40 37 FOBS=   0.0 SIGMA= 20.0 PHAS=    0.0 FOM= 0.00 TEST= 0
INDE 23 40 39 FOBS=  97.9 SIGMA=  1.9 PHAS=  144.4 FOM= 0.80 TEST= 0
INDE 23 40 41 FOBS= 147.9 SIGMA=  1.3 PHAS= -152.4 FOM= 0.96 TEST= 0
INDE 23 40 43 FOBS= 102.2 SIGMA=  1.8 PHAS= -101.9 FOM= 0.93 TEST= 1
INDE 23 40 45 FOBS=  46.6 SIGMA=  3.7 PHAS=  -40.8 FOM= 0.70 TEST= 0
INDE 23 40 47 FOBS= 108.1 SIGMA=  1.6 PHAS=   32.7 FOM= 0.53 TEST= 1
INDE 23 40 49 FOBS=  88.8 SIGMA=  2.2 PHAS=  -10.2 FOM= 0.87 TEST= 0
INDE 23 40 51 FOBS=  55.0 SIGMA=  3.5 PHAS=   31.3 FOM= 0.77 TEST= 0
INDE 23 40 53 FOBS=  80.1 SIGMA=  2.6 PHAS=  -42.5 FOM= 0.88 TEST= 0
INDE 23 40 55 FOBS=   0.0 SIGMA= 20.2 PHAS=    0.0 FOM= 0.00 TEST= 1
INDE 23 40 57 FOBS=  84.8 SIGMA=  2.5 PHAS=   -4.6 FOM= 0.15 TEST= 1
INDE 23 40 59 FOBS=  38.1 SIGMA=  5.4 PHAS=   12.1 FOM= 0.30 TEST= 0
INDE 23 40 61 FOBS=  88.8 SIGMA=  2.9 PHAS=  -81.2 FOM= 0.86 TEST= 0
INDE 23 41 24 FOBS=  95.9 SIGMA=  2.1 PHAS=  -35.2 FOM= 0.85 TEST= 0
INDE 23 41 26 FOBS=  91.0 SIGMA=  2.2 PHAS=   88.4 FOM= 0.86 TEST= 0
INDE 23 41 28 FOBS=  74.1 SIGMA=  2.4 PHAS=  -80.1 FOM= 0.90 TEST= 0
INDE 23 41 30 FOBS= 171.6 SIGMA=  1.1 PHAS=  119.9 FOM= 0.92 TEST= 0
INDE 23 41 32 FOBS=  95.2 SIGMA=  1.9 PHAS=  116.7 FOM= 0.95 TEST= 0
INDE 23 41 34 FOBS=  29.5 SIGMA=  6.7 PHAS= -118.0 FOM= 0.51 TEST= 0
INDE 23 41 36 FOBS=   0.0 SIGMA= 19.4 PHAS=    0.0 FOM= 0.00 TEST= 0
INDE 23 41 38 FOBS= 131.9 SIGMA=  1.4 PHAS=   67.9 FOM= 0.97 TEST= 0
INDE 23 41 40 FOBS=  57.7 SIGMA=  3.3 PHAS=   15.7 FOM= 0.79 TEST= 0
INDE 23 41 42 FOBS= 101.0 SIGMA=  1.8 PHAS=  132.4 FOM= 0.95 TEST= 0
INDE 23 41 44 FOBS=  69.8 SIGMA=  2.5 PHAS=  135.8 FOM= 0.88 TEST= 0
```

*FIG. 12A - 480*

```
INDE 23 41 46 FOBS=   94.2 SIGMA=  1.9 PHAS= -123.1 FOM= 0.87 TEST= 0
INDE 23 41 48 FOBS=   90.4 SIGMA=  2.0 PHAS= -163.1 FOM= 0.90 TEST= 0
INDE 23 41 50 FOBS=    7.8 SIGMA= 26.1 PHAS=  -34.3 FOM= 0.07 TEST= 0
INDE 23 41 52 FOBS=   39.8 SIGMA=  5.6 PHAS= -171.4 FOM= 0.82 TEST= 0
INDE 23 41 54 FOBS=   29.1 SIGMA=  7.5 PHAS=  178.3 FOM= 0.63 TEST= 0
INDE 23 41 56 FOBS=  113.9 SIGMA=  1.9 PHAS= -136.3 FOM= 0.95 TEST= 0
INDE 23 41 58 FOBS=   88.0 SIGMA=  2.4 PHAS= -104.5 FOM= 0.91 TEST= 0
INDE 23 41 60 FOBS=   86.3 SIGMA=  3.0 PHAS=   49.0 FOM= 0.87 TEST= 0
INDE 23 42 23 FOBS=  145.5 SIGMA=  1.4 PHAS= -150.7 FOM= 0.97 TEST= 0
INDE 23 42 25 FOBS=   57.9 SIGMA=  3.4 PHAS=  -64.2 FOM= 0.39 TEST= 0
INDE 23 42 27 FOBS=   41.2 SIGMA=  4.3 PHAS=   78.8 FOM= 0.92 TEST= 0
INDE 23 42 29 FOBS=    0.0 SIGMA= 20.4 PHAS=    0.0 FOM= 0.00 TEST= 0
INDE 23 42 31 FOBS=  240.3 SIGMA=  0.9 PHAS=  -19.4 FOM= 0.95 TEST= 0
INDE 23 42 33 FOBS=    0.0 SIGMA= 19.9 PHAS=    0.0 FOM= 0.00 TEST= 0
INDE 23 42 35 FOBS=  161.4 SIGMA=  1.3 PHAS=    9.0 FOM= 0.90 TEST= 0
INDE 23 42 37 FOBS=   52.5 SIGMA=  3.4 PHAS=  -33.3 FOM= 0.91 TEST= 0
INDE 23 42 39 FOBS=  126.4 SIGMA=  1.5 PHAS=  -81.0 FOM= 0.91 TEST= 0
INDE 23 42 41 FOBS=  143.7 SIGMA=  1.3 PHAS=  -95.9 FOM= 0.95 TEST= 0
INDE 23 42 43 FOBS=   86.1 SIGMA=  2.1 PHAS=   27.4 FOM= 0.87 TEST= 0
INDE 23 42 45 FOBS=   26.0 SIGMA=  7.4 PHAS=   84.2 FOM= 0.02 TEST= 1
INDE 23 42 47 FOBS=   50.3 SIGMA=  3.7 PHAS= -105.1 FOM= 0.24 TEST= 0
INDE 23 42 49 FOBS=   36.7 SIGMA=  4.9 PHAS= -177.3 FOM= 0.53 TEST= 0
INDE 23 42 51 FOBS=  103.0 SIGMA=  1.9 PHAS=  -15.7 FOM= 0.93 TEST= 0
INDE 23 42 53 FOBS=  127.4 SIGMA=  1.7 PHAS=   22.0 FOM= 0.93 TEST= 0
INDE 23 42 55 FOBS=  113.3 SIGMA=  1.9 PHAS=  155.0 FOM= 0.96 TEST= 0
INDE 23 42 57 FOBS=   44.1 SIGMA=  6.2 PHAS=  163.1 FOM= 0.73 TEST= 0
INDE 23 42 59 FOBS=   63.9 SIGMA=  4.0 PHAS=   74.5 FOM= 0.83 TEST= 0
INDE 23 42 61 FOBS=    0.0 SIGMA= 25.8 PHAS=    0.0 FOM= 0.00 TEST= 0
INDE 23 43 24 FOBS=  108.0 SIGMA=  1.9 PHAS=  159.3 FOM= 0.94 TEST= 0
INDE 23 43 26 FOBS=   40.3 SIGMA=  5.7 PHAS=   37.8 FOM= 0.82 TEST= 0
INDE 23 43 28 FOBS=   83.0 SIGMA=  2.1 PHAS= -129.5 FOM= 0.86 TEST= 0
INDE 23 43 30 FOBS=  176.0 SIGMA=  1.1 PHAS= -162.3 FOM= 0.46 TEST= 1
INDE 23 43 32 FOBS=   49.0 SIGMA=  4.1 PHAS= -107.5 FOM= 0.49 TEST= 0
INDE 23 43 34 FOBS=  119.9 SIGMA=  1.7 PHAS=  -50.3 FOM= 0.91 TEST= 0
INDE 23 43 36 FOBS=    6.1 SIGMA= 37.6 PHAS= -102.9 FOM= 0.07 TEST= 0
INDE 23 43 38 FOBS=   75.6 SIGMA=  2.4 PHAS=  153.5 FOM= 0.85 TEST= 1
INDE 23 43 40 FOBS=   63.7 SIGMA=  2.8 PHAS=  162.1 FOM= 0.83 TEST= 0
INDE 23 43 42 FOBS=   77.4 SIGMA=  2.3 PHAS= -111.6 FOM= 0.77 TEST= 0
INDE 23 43 44 FOBS=   65.9 SIGMA=  2.7 PHAS=   15.6 FOM= 0.17 TEST= 1
INDE 23 43 46 FOBS=   91.9 SIGMA=  1.9 PHAS=  147.4 FOM= 0.81 TEST= 0
INDE 23 43 48 FOBS=   68.2 SIGMA=  2.6 PHAS=  142.3 FOM= 0.89 TEST= 0
INDE 23 43 50 FOBS=   25.8 SIGMA=  7.6 PHAS=   94.0 FOM= 0.28 TEST= 0
INDE 23 43 52 FOBS=  172.6 SIGMA=  1.3 PHAS=  -97.9 FOM= 0.98 TEST= 0
INDE 23 43 54 FOBS=   42.3 SIGMA=  5.3 PHAS=   55.3 FOM= 0.68 TEST= 0
INDE 23 43 56 FOBS=   22.2 SIGMA= 13.9 PHAS=  165.0 FOM= 0.25 TEST= 0
INDE 23 43 58 FOBS=    0.0 SIGMA= 21.4 PHAS=    0.0 FOM= 0.00 TEST= 0
INDE 23 43 60 FOBS=   35.1 SIGMA=  8.5 PHAS=  -13.5 FOM= 0.78 TEST= 0
INDE 23 44 23 FOBS=  139.2 SIGMA=  1.2 PHAS=   77.7 FOM= 0.90 TEST= 1
INDE 23 44 25 FOBS=   77.0 SIGMA=  2.6 PHAS=  -53.7 FOM= 0.41 TEST= 0
INDE 23 44 27 FOBS=   54.3 SIGMA=  3.6 PHAS=  117.7 FOM= 0.80 TEST= 0
INDE 23 44 29 FOBS=    0.0 SIGMA= 20.5 PHAS=    0.0 FOM= 0.00 TEST= 0
INDE 23 44 31 FOBS=  118.1 SIGMA=  1.7 PHAS=   58.1 FOM= 0.94 TEST= 0
INDE 23 44 33 FOBS=   72.7 SIGMA=  2.7 PHAS= -140.7 FOM= 0.82 TEST= 0
INDE 23 44 35 FOBS=   35.3 SIGMA=  5.6 PHAS=   33.8 FOM= 0.59 TEST= 0
INDE 23 44 37 FOBS=   44.8 SIGMA=  4.2 PHAS=  130.1 FOM= 0.27 TEST= 0
INDE 23 44 39 FOBS=   46.5 SIGMA=  3.8 PHAS=   50.7 FOM= 0.41 TEST= 0
INDE 23 44 41 FOBS=   45.2 SIGMA=  3.9 PHAS=  -83.4 FOM= 0.47 TEST= 0
INDE 23 44 43 FOBS=    0.0 SIGMA= 19.8 PHAS=    0.0 FOM= 0.00 TEST= 0
INDE 23 44 45 FOBS=    6.7 SIGMA= 29.2 PHAS=   46.5 FOM= 0.03 TEST= 0
INDE 23 44 47 FOBS=   98.8 SIGMA=  1.8 PHAS=   44.9 FOM= 0.80 TEST= 0
INDE 23 44 49 FOBS=   74.2 SIGMA=  2.4 PHAS=  -12.6 FOM= 0.74 TEST= 0
INDE 23 44 51 FOBS=   46.3 SIGMA=  4.5 PHAS=  -56.9 FOM= 0.52 TEST= 0
INDE 23 44 53 FOBS=   53.0 SIGMA=  4.2 PHAS=  -27.1 FOM= 0.14 TEST= 1
INDE 23 44 55 FOBS=   77.0 SIGMA=  3.1 PHAS=   69.9 FOM= 0.90 TEST= 0
INDE 23 44 57 FOBS=    0.0 SIGMA= 22.5 PHAS=    0.0 FOM= 0.00 TEST= 0
INDE 23 44 59 FOBS=    0.0 SIGMA= 26.4 PHAS=    0.0 FOM= 0.00 TEST= 0
INDE 23 45 24 FOBS=   97.5 SIGMA=  1.8 PHAS=   71.5 FOM= 0.81 TEST= 0
INDE 23 45 26 FOBS=  122.4 SIGMA=  1.8 PHAS=  118.2 FOM= 0.78 TEST= 0
INDE 23 45 28 FOBS=   63.7 SIGMA=  3.5 PHAS=   76.2 FOM= 0.76 TEST= 0
INDE 23 45 30 FOBS=  101.7 SIGMA=  2.0 PHAS=  -83.5 FOM= 0.92 TEST= 0
```

*FIG. 12A - 481*

```
INDE 23 45 32 FOBS=    52.1 SIGMA=  3.8 PHAS=  -79.1 FOM= 0.19 TEST= 0
INDE 23 45 34 FOBS=     0.0 SIGMA= 19.6 PHAS=    0.0 FOM= 0.00 TEST= 0
INDE 23 45 36 FOBS=     0.0 SIGMA= 19.9 PHAS=    0.0 FOM= 0.00 TEST= 1
INDE 23 45 38 FOBS=    58.9 SIGMA=  3.1 PHAS= -107.2 FOM= 0.72 TEST= 0
INDE 23 45 40 FOBS=    70.3 SIGMA=  2.7 PHAS= -145.4 FOM= 0.17 TEST= 1
INDE 23 45 42 FOBS=    95.6 SIGMA=  1.9 PHAS=  -73.0 FOM= 0.93 TEST= 0
INDE 23 45 44 FOBS=     0.0 SIGMA= 19.4 PHAS=    0.0 FOM= 0.00 TEST= 0
INDE 23 45 46 FOBS=     0.0 SIGMA= 19.6 PHAS=    0.0 FOM= 0.00 TEST= 0
INDE 23 45 48 FOBS=    20.3 SIGMA=  9.4 PHAS=    1.4 FOM= 0.35 TEST= 0
INDE 23 45 50 FOBS=     0.0 SIGMA= 18.7 PHAS=    0.0 FOM= 0.00 TEST= 0
INDE 23 45 52 FOBS=     6.0 SIGMA= 30.7 PHAS= -104.2 FOM= 0.18 TEST= 0
INDE 23 45 54 FOBS=    35.2 SIGMA=  7.3 PHAS= -119.0 FOM= 0.69 TEST= 0
INDE 23 45 56 FOBS=   117.2 SIGMA=  2.1 PHAS=  151.9 FOM= 0.87 TEST= 0
INDE 23 45 58 FOBS=    56.1 SIGMA=  5.3 PHAS=  137.0 FOM= 0.70 TEST= 0
INDE 23 46 23 FOBS=    29.4 SIGMA=  6.0 PHAS=   80.5 FOM= 0.09 TEST= 1
INDE 23 46 25 FOBS=   137.6 SIGMA=  1.5 PHAS=  -86.5 FOM= 0.91 TEST= 0
INDE 23 46 27 FOBS=    95.4 SIGMA=  2.2 PHAS=  -24.6 FOM= 0.91 TEST= 0
INDE 23 46 29 FOBS=    95.7 SIGMA=  2.4 PHAS=  -39.2 FOM= 0.93 TEST= 0
INDE 23 46 31 FOBS=    14.6 SIGMA= 14.5 PHAS=   34.6 FOM= 0.07 TEST= 0
INDE 23 46 33 FOBS=    77.6 SIGMA=  2.6 PHAS=   50.3 FOM= 0.86 TEST= 0
INDE 23 46 35 FOBS=   123.1 SIGMA=  1.7 PHAS=    0.2 FOM= 0.94 TEST= 0
INDE 23 46 37 FOBS=    26.2 SIGMA=  8.0 PHAS=  178.5 FOM= 0.23 TEST= 0
INDE 23 46 39 FOBS=    39.8 SIGMA=  4.8 PHAS= -159.7 FOM= 0.67 TEST= 0
INDE 23 46 41 FOBS=    88.5 SIGMA=  2.1 PHAS= -136.8 FOM= 0.95 TEST= 0
INDE 23 46 43 FOBS=    79.1 SIGMA=  2.3 PHAS= -139.2 FOM= 0.69 TEST= 0
INDE 23 46 45 FOBS=    36.9 SIGMA=  4.8 PHAS= -178.8 FOM= 0.62 TEST= 0
INDE 23 46 47 FOBS=    34.0 SIGMA=  5.4 PHAS=  -11.2 FOM= 0.06 TEST= 1
INDE 23 46 49 FOBS=    91.7 SIGMA=  2.1 PHAS=  -69.3 FOM= 0.86 TEST= 0
INDE 23 46 51 FOBS=     0.0 SIGMA= 22.8 PHAS=    0.0 FOM= 0.00 TEST= 0
INDE 23 46 53 FOBS=    43.8 SIGMA=  5.4 PHAS=  121.7 FOM= 0.43 TEST= 0
INDE 23 46 55 FOBS=    80.3 SIGMA=  3.0 PHAS=   28.3 FOM= 0.38 TEST= 0
INDE 23 46 57 FOBS=    69.7 SIGMA=  4.3 PHAS=  -25.6 FOM= 0.88 TEST= 0
INDE 23 47 24 FOBS=    89.6 SIGMA=  2.2 PHAS=   90.7 FOM= 0.95 TEST= 0
INDE 23 47 26 FOBS=   123.0 SIGMA=  1.8 PHAS=   94.9 FOM= 0.92 TEST= 0
INDE 23 47 28 FOBS=     0.0 SIGMA= 20.3 PHAS=    0.0 FOM= 0.00 TEST= 0
INDE 23 47 30 FOBS=     0.0 SIGMA= 19.6 PHAS=    0.0 FOM= 0.00 TEST= 0
INDE 23 47 32 FOBS=   144.4 SIGMA=  1.4 PHAS=  -77.4 FOM= 0.91 TEST= 0
INDE 23 47 34 FOBS=   141.7 SIGMA=  1.5 PHAS=  -56.1 FOM= 0.95 TEST= 0
INDE 23 47 36 FOBS=     0.0 SIGMA= 20.6 PHAS=    0.0 FOM= 0.00 TEST= 0
INDE 23 47 38 FOBS=   131.3 SIGMA=  1.6 PHAS=  -18.3 FOM= 0.91 TEST= 0
INDE 23 47 40 FOBS=   147.1 SIGMA=  1.3 PHAS=   92.7 FOM= 0.93 TEST= 0
INDE 23 47 42 FOBS=    57.5 SIGMA=  3.1 PHAS=   -7.5 FOM= 0.41 TEST= 1
INDE 23 47 44 FOBS=    60.9 SIGMA=  2.9 PHAS=   67.7 FOM= 0.59 TEST= 0
INDE 23 47 46 FOBS=     0.0 SIGMA= 19.4 PHAS=    0.0 FOM= 0.00 TEST= 0
INDE 23 47 48 FOBS=    46.4 SIGMA=  4.4 PHAS= -121.8 FOM= 0.62 TEST= 0
INDE 23 47 50 FOBS=    65.3 SIGMA=  3.1 PHAS=  163.5 FOM= 0.82 TEST= 0
INDE 23 47 52 FOBS=    49.4 SIGMA=  4.2 PHAS= -136.0 FOM= 0.54 TEST= 0
INDE 23 47 54 FOBS=    71.7 SIGMA=  2.9 PHAS= -149.2 FOM= 0.89 TEST= 0
INDE 23 47 56 FOBS=    24.2 SIGMA= 13.7 PHAS= -134.5 FOM= 0.51 TEST= 0
INDE 23 48 23 FOBS=    74.9 SIGMA=  2.2 PHAS=  -53.9 FOM= 0.90 TEST= 0
INDE 23 48 25 FOBS=   204.6 SIGMA=  1.0 PHAS=    0.0 FOM= 0.97 TEST= 0
INDE 23 48 27 FOBS=   265.0 SIGMA=  0.9 PHAS=  -32.7 FOM= 0.98 TEST= 0
INDE 23 48 29 FOBS=    54.1 SIGMA=  3.9 PHAS=   58.0 FOM= 0.55 TEST= 0
INDE 23 48 31 FOBS=    51.5 SIGMA=  3.8 PHAS= -147.2 FOM= 0.75 TEST= 0
INDE 23 48 33 FOBS=    62.1 SIGMA=  3.2 PHAS= -130.2 FOM= 0.73 TEST= 0
INDE 23 48 35 FOBS=    45.7 SIGMA=  4.3 PHAS=  175.8 FOM= 0.50 TEST= 0
INDE 23 48 37 FOBS=    82.6 SIGMA=  2.4 PHAS= -143.3 FOM= 0.71 TEST= 0
INDE 23 48 39 FOBS=   138.9 SIGMA=  1.4 PHAS=  -57.6 FOM= 0.94 TEST= 0
INDE 23 48 41 FOBS=    40.6 SIGMA=  4.4 PHAS= -129.0 FOM= 0.24 TEST= 0
INDE 23 48 43 FOBS=    70.8 SIGMA=  2.5 PHAS= -130.1 FOM= 0.53 TEST= 0
INDE 23 48 45 FOBS=    30.5 SIGMA=  6.3 PHAS= -108.1 FOM= 0.32 TEST= 0
INDE 23 48 47 FOBS=    44.3 SIGMA=  4.6 PHAS=  129.3 FOM= 0.77 TEST= 0
INDE 23 48 49 FOBS=     0.0 SIGMA= 21.7 PHAS=    0.0 FOM= 0.00 TEST= 0
INDE 23 48 51 FOBS=    69.0 SIGMA=  3.0 PHAS=  114.1 FOM= 0.80 TEST= 0
INDE 23 48 53 FOBS=    88.2 SIGMA=  2.4 PHAS=  113.5 FOM= 0.85 TEST= 0
INDE 23 48 55 FOBS=    58.6 SIGMA=  4.2 PHAS=   72.9 FOM= 0.83 TEST= 0
INDE 23 49 24 FOBS=    89.2 SIGMA=  2.0 PHAS=  -18.6 FOM= 0.93 TEST= 0
INDE 23 49 26 FOBS=   179.6 SIGMA=  1.3 PHAS= -136.5 FOM= 0.96 TEST= 0
INDE 23 49 28 FOBS=   140.9 SIGMA=  1.4 PHAS= -123.5 FOM= 0.94 TEST= 0
INDE 23 49 30 FOBS=   108.0 SIGMA=  2.0 PHAS=  131.3 FOM= 0.88 TEST= 0
```

*FIG. 12A - 482*

```
INDE  23  49  32  FOBS=   156.0  SIGMA=   1.3  PHAS=   -98.1  FOM=  0.96  TEST= 0
INDE  23  49  34  FOBS=    48.7  SIGMA=   4.0  PHAS=  -142.3  FOM=  0.60  TEST= 0
INDE  23  49  36  FOBS=    89.4  SIGMA=   2.2  PHAS=   110.0  FOM=  0.86  TEST= 0
INDE  23  49  38  FOBS=    90.5  SIGMA=   2.2  PHAS=   -56.8  FOM=  0.63  TEST= 0
INDE  23  49  40  FOBS=    80.4  SIGMA=   2.2  PHAS=    52.0  FOM=  0.55  TEST= 0
INDE  23  49  42  FOBS=    76.5  SIGMA=   2.5  PHAS=    84.5  FOM=  0.90  TEST= 0
INDE  23  49  44  FOBS=     0.0  SIGMA=  20.1  PHAS=     0.0  FOM=  0.00  TEST= 0
INDE  23  49  46  FOBS=    12.1  SIGMA=  19.7  PHAS=    57.9  FOM=  0.21  TEST= 0
INDE  23  49  48  FOBS=    67.3  SIGMA=   3.1  PHAS=     5.4  FOM=  0.83  TEST= 0
INDE  23  49  50  FOBS=     0.0  SIGMA=  20.8  PHAS=     0.0  FOM=  0.00  TEST= 0
INDE  23  49  52  FOBS=    32.2  SIGMA=   9.1  PHAS=  -178.5  FOM=  0.34  TEST= 0
INDE  23  49  54  FOBS=    31.1  SIGMA=   8.8  PHAS=   -18.7  FOM=  0.53  TEST= 0
INDE  23  50  23  FOBS=    68.8  SIGMA=   2.4  PHAS=   -76.1  FOM=  0.90  TEST= 0
INDE  23  50  25  FOBS=   162.7  SIGMA=   1.3  PHAS=    73.0  FOM=  0.94  TEST= 0
INDE  23  50  27  FOBS=   104.4  SIGMA=   1.9  PHAS=    32.5  FOM=  0.65  TEST= 1
INDE  23  50  29  FOBS=    80.0  SIGMA=   2.4  PHAS=   154.7  FOM=  0.89  TEST= 0
INDE  23  50  31  FOBS=    66.1  SIGMA=   3.1  PHAS=  -178.9  FOM=  0.55  TEST= 1
INDE  23  50  33  FOBS=   122.0  SIGMA=   1.7  PHAS=   162.0  FOM=  0.92  TEST= 0
INDE  23  50  35  FOBS=    42.1  SIGMA=   4.6  PHAS=    79.0  FOM=  0.66  TEST= 0
INDE  23  50  37  FOBS=    34.9  SIGMA=   6.4  PHAS=  -127.0  FOM=  0.74  TEST= 0
INDE  23  50  39  FOBS=    93.9  SIGMA=   2.3  PHAS=   -70.0  FOM=  0.88  TEST= 0
INDE  23  50  41  FOBS=   103.8  SIGMA=   2.0  PHAS=    22.9  FOM=  0.79  TEST= 0
INDE  23  50  43  FOBS=     0.0  SIGMA=  21.1  PHAS=     0.0  FOM=  0.00  TEST= 1
INDE  23  50  45  FOBS=     0.0  SIGMA=  20.2  PHAS=     0.0  FOM=  0.00  TEST= 0
INDE  23  50  47  FOBS=    41.9  SIGMA=   5.0  PHAS=   115.5  FOM=  0.71  TEST= 0
INDE  23  50  49  FOBS=    41.6  SIGMA=   5.0  PHAS=    75.7  FOM=  0.19  TEST= 0
INDE  23  50  51  FOBS=    62.9  SIGMA=   3.7  PHAS=    96.9  FOM=  0.85  TEST= 0
INDE  23  50  53  FOBS=     0.0  SIGMA=  24.7  PHAS=     0.0  FOM=  0.00  TEST= 0
INDE  23  51  24  FOBS=    77.2  SIGMA=   2.3  PHAS=   -56.9  FOM=  0.92  TEST= 0
INDE  23  51  26  FOBS=   140.3  SIGMA=   1.4  PHAS=   -73.3  FOM=  0.92  TEST= 0
INDE  23  51  28  FOBS=    48.1  SIGMA=   3.9  PHAS=   122.3  FOM=  0.83  TEST= 0
INDE  23  51  30  FOBS=   162.1  SIGMA=   1.3  PHAS=   128.6  FOM=  0.97  TEST= 0
INDE  23  51  32  FOBS=     0.0  SIGMA=  19.6  PHAS=     0.0  FOM=  0.00  TEST= 1
INDE  23  51  34  FOBS=     8.4  SIGMA=  32.5  PHAS=    -4.1  FOM=  0.04  TEST= 0
INDE  23  51  36  FOBS=    54.9  SIGMA=   4.1  PHAS=    83.9  FOM=  0.68  TEST= 0
INDE  23  51  38  FOBS=    64.2  SIGMA=   3.6  PHAS=  -134.4  FOM=  0.68  TEST= 0
INDE  23  51  40  FOBS=    32.5  SIGMA=   7.1  PHAS=   101.8  FOM=  0.79  TEST= 0
INDE  23  51  42  FOBS=   105.0  SIGMA=   2.0  PHAS=    75.6  FOM=  0.95  TEST= 0
INDE  23  51  44  FOBS=   136.6  SIGMA=   1.6  PHAS=    14.4  FOM=  0.97  TEST= 0
INDE  23  51  46  FOBS=    77.9  SIGMA=   3.0  PHAS=    17.3  FOM=  0.89  TEST= 0
INDE  23  51  48  FOBS=    45.6  SIGMA=   5.0  PHAS=   -59.3  FOM=  0.79  TEST= 0
INDE  23  51  50  FOBS=   120.3  SIGMA=   2.0  PHAS=   -73.6  FOM=  0.96  TEST= 0
INDE  23  51  52  FOBS=     0.0  SIGMA=  25.0  PHAS=     0.0  FOM=  0.00  TEST= 0
INDE  23  51  54  FOBS=     0.0  SIGMA=  30.0  PHAS=     0.0  FOM=  0.00  TEST= 0
INDE  23  52  23  FOBS=    55.7  SIGMA=   2.9  PHAS=  -170.6  FOM=  0.76  TEST= 0
INDE  23  52  25  FOBS=    36.5  SIGMA=   5.4  PHAS=   114.1  FOM=  0.32  TEST= 0
INDE  23  52  27  FOBS=    75.3  SIGMA=   2.5  PHAS=    50.5  FOM=  0.94  TEST= 0
INDE  23  52  29  FOBS=    92.5  SIGMA=   2.2  PHAS=    69.5  FOM=  0.73  TEST= 1
INDE  23  52  31  FOBS=    68.3  SIGMA=   3.0  PHAS=  -169.6  FOM=  0.68  TEST= 0
INDE  23  52  33  FOBS=     0.0  SIGMA=  21.3  PHAS=     0.0  FOM=  0.00  TEST= 0
INDE  23  52  35  FOBS=    24.0  SIGMA=  10.2  PHAS=    91.7  FOM=  0.12  TEST= 0
INDE  23  52  37  FOBS=    69.0  SIGMA=   3.3  PHAS=  -117.8  FOM=  0.61  TEST= 0
INDE  23  52  39  FOBS=    39.4  SIGMA=   7.0  PHAS=   119.5  FOM=  0.44  TEST= 0
INDE  23  52  41  FOBS=   143.6  SIGMA=   1.8  PHAS=     0.4  FOM=  0.96  TEST= 0
INDE  23  52  43  FOBS=   140.1  SIGMA=   1.7  PHAS=   -59.8  FOM=  0.96  TEST= 0
INDE  23  52  45  FOBS=    95.3  SIGMA=   2.5  PHAS=   -81.5  FOM=  0.93  TEST= 0
INDE  23  52  47  FOBS=    25.8  SIGMA=   9.8  PHAS=   -23.5  FOM=  0.06  TEST= 0
INDE  23  52  49  FOBS=   139.6  SIGMA=   2.0  PHAS=  -179.2  FOM=  0.98  TEST= 0
INDE  23  52  51  FOBS=    49.7  SIGMA=   5.7  PHAS=   159.1  FOM=  0.93  TEST= 0
INDE  23  52  53  FOBS=    31.6  SIGMA=  14.8  PHAS=  -129.6  FOM=  0.37  TEST= 0
INDE  23  53  24  FOBS=    52.7  SIGMA=   3.4  PHAS=   174.9  FOM=  0.50  TEST= 0
INDE  23  53  26  FOBS=     8.8  SIGMA=  26.0  PHAS=    39.2  FOM=  0.17  TEST= 0
INDE  23  53  28  FOBS=    52.2  SIGMA=   4.2  PHAS=  -138.4  FOM=  0.73  TEST= 0
INDE  23  53  30  FOBS=    48.4  SIGMA=   4.5  PHAS=    -1.1  FOM=  0.51  TEST= 0
INDE  23  53  32  FOBS=    62.4  SIGMA=   3.5  PHAS=   179.2  FOM=  0.42  TEST= 0
INDE  23  53  34  FOBS=     0.0  SIGMA=  21.3  PHAS=     0.0  FOM=  0.00  TEST= 0
INDE  23  53  36  FOBS=    42.8  SIGMA=   5.2  PHAS=   -73.8  FOM=  0.19  TEST= 0
INDE  23  53  38  FOBS=     0.0  SIGMA=  22.6  PHAS=     0.0  FOM=  0.00  TEST= 0
INDE  23  53  40  FOBS=    71.6  SIGMA=   3.7  PHAS=    99.5  FOM=  0.58  TEST= 0
INDE  23  53  42  FOBS=    47.2  SIGMA=   5.7  PHAS=   173.7  FOM=  0.33  TEST= 1
```

*FIG. 12A - 483*

```
INDE 23 53 44 FOBS=    0.0 SIGMA= 22.4 PHAS=    0.0 FOM= 0.00 TEST= 0
INDE 23 53 46 FOBS=   44.2 SIGMA=  7.1 PHAS=  157.8 FOM= 0.34 TEST= 0
INDE 23 53 48 FOBS=   65.4 SIGMA=  4.0 PHAS=  106.4 FOM= 0.91 TEST= 0
INDE 23 53 50 FOBS=   43.2 SIGMA=  7.6 PHAS=  -84.2 FOM= 0.07 TEST= 0
INDE 23 53 52 FOBS=   51.8 SIGMA=  8.8 PHAS= -174.9 FOM= 0.66 TEST= 0
INDE 23 54 23 FOBS=  120.2 SIGMA=  1.5 PHAS= -128.4 FOM= 0.91 TEST= 0
INDE 23 54 25 FOBS=    0.0 SIGMA= 22.0 PHAS=    0.0 FOM= 0.00 TEST= 0
INDE 23 54 27 FOBS=  130.2 SIGMA=  1.7 PHAS=   98.8 FOM= 0.79 TEST= 1
INDE 23 54 29 FOBS=    0.0 SIGMA= 21.8 PHAS=    0.0 FOM= 0.00 TEST= 1
INDE 23 54 31 FOBS=   23.4 SIGMA= 10.1 PHAS= -156.8 FOM= 0.15 TEST= 0
INDE 23 54 33 FOBS=   30.7 SIGMA=  8.8 PHAS=   82.2 FOM= 0.58 TEST= 0
INDE 23 54 35 FOBS=   28.2 SIGMA=  8.1 PHAS=  -29.4 FOM= 0.22 TEST= 0
INDE 23 54 37 FOBS=    0.0 SIGMA= 23.8 PHAS=    0.0 FOM= 0.00 TEST= 0
INDE 23 54 39 FOBS=   71.2 SIGMA=  4.2 PHAS=  163.1 FOM= 0.82 TEST= 0
INDE 23 54 41 FOBS=   66.3 SIGMA=  4.6 PHAS=    1.8 FOM= 0.89 TEST= 0
INDE 23 54 43 FOBS=   32.1 SIGMA=  7.8 PHAS=  158.4 FOM= 0.48 TEST= 0
INDE 23 54 45 FOBS=   45.4 SIGMA=  5.6 PHAS=   -3.9 FOM= 0.69 TEST= 0
INDE 23 54 47 FOBS=    0.0 SIGMA= 22.8 PHAS=    0.0 FOM= 0.00 TEST= 0
INDE 23 54 49 FOBS=   29.8 SIGMA=  9.8 PHAS=   51.0 FOM= 0.58 TEST= 0
INDE 23 54 51 FOBS=   63.0 SIGMA=  9.9 PHAS=  155.3 FOM= 0.90 TEST= 0
INDE 23 55 24 FOBS=  177.5 SIGMA=  1.1 PHAS=  146.2 FOM= 0.96 TEST= 0
INDE 23 55 26 FOBS=   61.4 SIGMA=  3.5 PHAS=  -17.1 FOM= 0.58 TEST= 0
INDE 23 55 28 FOBS=   27.2 SIGMA=  8.9 PHAS= -115.4 FOM= 0.27 TEST= 1
INDE 23 55 30 FOBS=  112.4 SIGMA=  2.2 PHAS=  -67.4 FOM= 0.93 TEST= 0
INDE 23 55 32 FOBS=   32.8 SIGMA=  8.1 PHAS=  125.7 FOM= 0.20 TEST= 0
INDE 23 55 34 FOBS=  121.3 SIGMA=  2.0 PHAS=  -83.1 FOM= 0.92 TEST= 0
INDE 23 55 36 FOBS=    0.0 SIGMA= 25.5 PHAS=    0.0 FOM= 0.00 TEST= 0
INDE 23 55 38 FOBS=    4.1 SIGMA= 70.0 PHAS=   43.4 FOM= 0.02 TEST= 0
INDE 23 55 40 FOBS=   31.9 SIGMA=  9.3 PHAS=   82.4 FOM= 0.22 TEST= 0
INDE 23 55 42 FOBS=    0.0 SIGMA= 24.7 PHAS=    0.0 FOM= 0.00 TEST= 0
INDE 23 55 44 FOBS=   58.0 SIGMA=  4.4 PHAS=  -86.0 FOM= 0.76 TEST= 0
INDE 23 55 46 FOBS=   35.5 SIGMA=  8.0 PHAS= -119.0 FOM= 0.16 TEST= 0
INDE 23 55 48 FOBS=   48.5 SIGMA=  6.1 PHAS= -102.2 FOM= 0.67 TEST= 0
INDE 23 56 23 FOBS=   45.6 SIGMA=  5.8 PHAS=  -88.6 FOM= 0.53 TEST= 0
INDE 23 56 25 FOBS=   98.6 SIGMA=  2.2 PHAS=   25.9 FOM= 0.89 TEST= 0
INDE 23 56 27 FOBS=   74.4 SIGMA=  3.6 PHAS=  142.1 FOM= 0.84 TEST= 0
INDE 23 56 29 FOBS=  170.2 SIGMA=  1.7 PHAS= -168.1 FOM= 0.98 TEST= 0
INDE 23 56 31 FOBS=    0.0 SIGMA= 24.7 PHAS=    0.0 FOM= 0.00 TEST= 0
INDE 23 56 33 FOBS=    0.0 SIGMA= 23.3 PHAS=    0.0 FOM= 0.00 TEST= 0
INDE 23 56 35 FOBS=   41.6 SIGMA=  6.0 PHAS= -155.7 FOM= 0.44 TEST= 0
INDE 23 56 37 FOBS=   30.8 SIGMA=  9.2 PHAS=  169.9 FOM= 0.28 TEST= 0
INDE 23 56 39 FOBS=   36.9 SIGMA=  8.0 PHAS=   21.8 FOM= 0.32 TEST= 0
INDE 23 56 41 FOBS=    0.0 SIGMA= 24.5 PHAS=    0.0 FOM= 0.00 TEST= 0
INDE 23 56 43 FOBS=   34.7 SIGMA=  7.3 PHAS=   75.3 FOM= 0.74 TEST= 0
INDE 23 56 45 FOBS=    0.0 SIGMA= 24.0 PHAS=    0.0 FOM= 0.00 TEST= 1
INDE 23 56 47 FOBS=   95.3 SIGMA=  3.2 PHAS= -175.4 FOM= 0.88 TEST= 0
INDE 23 57 24 FOBS=   75.5 SIGMA=  3.0 PHAS=  177.6 FOM= 0.81 TEST= 0
INDE 23 57 26 FOBS=   89.2 SIGMA=  3.0 PHAS=  -44.7 FOM= 0.89 TEST= 0
INDE 23 57 28 FOBS=   62.8 SIGMA=  4.8 PHAS=   46.1 FOM= 0.84 TEST= 0
INDE 23 57 30 FOBS=    0.0 SIGMA= 25.1 PHAS=    0.0 FOM= 0.00 TEST= 0
INDE 23 57 32 FOBS=    0.0 SIGMA= 25.3 PHAS=    0.0 FOM= 0.00 TEST= 0
INDE 23 57 34 FOBS=  123.2 SIGMA=  2.4 PHAS=  -80.2 FOM= 0.91 TEST= 0
INDE 23 57 36 FOBS=   25.6 SIGMA=  9.8 PHAS=  131.7 FOM= 0.42 TEST= 0
INDE 23 57 38 FOBS=    0.0 SIGMA= 24.1 PHAS=    0.0 FOM= 0.00 TEST= 0
INDE 23 57 40 FOBS=    0.0 SIGMA= 24.4 PHAS=    0.0 FOM= 0.00 TEST= 0
INDE 23 57 42 FOBS=   64.9 SIGMA=  4.8 PHAS=  -11.2 FOM= 0.88 TEST= 0
INDE 23 57 44 FOBS=    0.0 SIGMA= 23.6 PHAS=    0.0 FOM= 0.00 TEST= 0
INDE 23 57 46 FOBS=  134.2 SIGMA=  2.6 PHAS=  130.2 FOM= 0.96 TEST= 0
INDE 23 58 23 FOBS=   42.0 SIGMA=  6.8 PHAS= -165.1 FOM= 0.43 TEST= 0
INDE 23 58 25 FOBS=   96.2 SIGMA=  2.7 PHAS=   77.6 FOM= 0.89 TEST= 0
INDE 23 58 27 FOBS=  131.8 SIGMA=  2.1 PHAS= -154.0 FOM= 0.95 TEST= 0
INDE 23 58 29 FOBS=   78.0 SIGMA=  3.4 PHAS=  153.6 FOM= 0.50 TEST= 1
INDE 23 58 31 FOBS=    0.0 SIGMA= 23.1 PHAS=    0.0 FOM= 0.00 TEST= 0
INDE 23 58 33 FOBS=    0.0 SIGMA= 23.3 PHAS=    0.0 FOM= 0.00 TEST= 0
INDE 23 58 35 FOBS=    0.0 SIGMA= 22.2 PHAS=    0.0 FOM= 0.00 TEST= 0
INDE 23 58 37 FOBS=   10.2 SIGMA= 22.7 PHAS= -162.5 FOM= 0.12 TEST= 0
INDE 23 58 39 FOBS=   12.7 SIGMA= 26.9 PHAS=   81.1 FOM= 0.16 TEST= 0
INDE 23 58 41 FOBS=   47.3 SIGMA=  6.6 PHAS= -139.7 FOM= 0.34 TEST= 0
INDE 23 58 43 FOBS=    0.0 SIGMA= 25.1 PHAS=    0.0 FOM= 0.00 TEST= 0
INDE 23 58 45 FOBS=   62.1 SIGMA=  5.3 PHAS=   44.3 FOM= 0.90 TEST= 0
```

*FIG. 12A - 484*

```
INDE 23 59 24 FOBS=   52.7 SIGMA=  5.4 PHAS=   62.2 FOM= 0.81 TEST= 0
INDE 23 59 26 FOBS=  118.6 SIGMA=  2.3 PHAS=  -34.4 FOM= 0.93 TEST= 0
INDE 23 59 28 FOBS=  102.6 SIGMA=  2.7 PHAS=   32.7 FOM= 0.89 TEST= 0
INDE 23 59 30 FOBS=    0.0 SIGMA= 24.4 PHAS=    0.0 FOM= 0.00 TEST= 0
INDE 23 59 32 FOBS=   25.2 SIGMA= 12.1 PHAS= -145.8 FOM= 0.32 TEST= 0
INDE 23 59 34 FOBS=  100.9 SIGMA=  2.8 PHAS= -133.9 FOM= 0.93 TEST= 0
INDE 23 59 36 FOBS=   27.5 SIGMA= 10.3 PHAS=  -65.8 FOM= 0.21 TEST= 0
INDE 23 59 38 FOBS=   56.5 SIGMA=  4.2 PHAS=    7.9 FOM= 0.27 TEST= 1
INDE 23 59 40 FOBS=   32.7 SIGMA= 10.6 PHAS=   24.2 FOM= 0.10 TEST= 0
INDE 23 59 42 FOBS=    0.0 SIGMA= 27.1 PHAS=    0.0 FOM= 0.00 TEST= 0
INDE 23 59 44 FOBS=    0.0 SIGMA= 29.8 PHAS=    0.0 FOM= 0.00 TEST= 1
INDE 23 60 23 FOBS=   51.1 SIGMA=  6.5 PHAS=  134.2 FOM= 0.69 TEST= 0
INDE 23 60 25 FOBS=   91.4 SIGMA=  2.5 PHAS=  140.5 FOM= 0.06 TEST= 1
INDE 23 60 27 FOBS=  123.3 SIGMA=  2.2 PHAS= -102.6 FOM= 0.93 TEST= 0
INDE 23 60 29 FOBS=   22.4 SIGMA= 13.7 PHAS=  102.5 FOM= 0.14 TEST= 0
INDE 23 60 31 FOBS=    0.0 SIGMA= 24.9 PHAS=    0.0 FOM= 0.00 TEST= 0
INDE 23 60 33 FOBS=   43.1 SIGMA=  6.4 PHAS=  125.4 FOM= 0.18 TEST= 1
INDE 23 60 35 FOBS=    0.0 SIGMA= 23.6 PHAS=    0.0 FOM= 0.00 TEST= 0
INDE 23 60 37 FOBS=   37.8 SIGMA=  8.7 PHAS=  -42.7 FOM= 0.23 TEST= 0
INDE 23 60 39 FOBS=   68.6 SIGMA=  3.5 PHAS= -108.1 FOM= 0.21 TEST= 1
INDE 23 60 41 FOBS=    0.0 SIGMA= 26.7 PHAS=    0.0 FOM= 0.00 TEST= 0
INDE 23 60 43 FOBS=   51.4 SIGMA=  9.1 PHAS=   69.4 FOM= 0.74 TEST= 0
INDE 23 61 24 FOBS=   58.4 SIGMA=  4.9 PHAS=   36.8 FOM= 0.67 TEST= 0
INDE 23 61 26 FOBS=   85.8 SIGMA=  2.7 PHAS=  -64.8 FOM= 0.85 TEST= 0
INDE 23 61 28 FOBS=   39.1 SIGMA=  8.0 PHAS=  -13.8 FOM= 0.51 TEST= 0
INDE 23 61 30 FOBS=    0.0 SIGMA= 23.0 PHAS=    0.0 FOM= 0.00 TEST= 1
INDE 23 61 32 FOBS=   76.1 SIGMA=  3.7 PHAS=  -35.7 FOM= 0.87 TEST= 0
INDE 23 61 34 FOBS=    0.0 SIGMA= 23.8 PHAS=    0.0 FOM= 0.00 TEST= 0
INDE 23 61 36 FOBS=   40.4 SIGMA=  7.1 PHAS=  174.1 FOM= 0.28 TEST= 0
INDE 23 61 38 FOBS=    0.0 SIGMA= 24.3 PHAS=    0.0 FOM= 0.00 TEST= 0
INDE 23 61 40 FOBS=   37.9 SIGMA=  6.4 PHAS= -135.7 FOM= 0.54 TEST= 0
INDE 23 61 42 FOBS=    0.0 SIGMA= 30.4 PHAS=    0.0 FOM= 0.00 TEST= 0
INDE 23 62 23 FOBS=    6.4 SIGMA= 44.3 PHAS= -144.3 FOM= 0.07 TEST= 0
INDE 23 62 25 FOBS=   93.8 SIGMA=  3.2 PHAS=  -64.8 FOM= 0.90 TEST= 0
INDE 23 62 27 FOBS=   65.9 SIGMA=  4.0 PHAS=  -86.2 FOM= 0.82 TEST= 0
INDE 23 62 29 FOBS=    0.0 SIGMA= 27.0 PHAS=    0.0 FOM= 0.00 TEST= 0
INDE 23 62 31 FOBS=  101.0 SIGMA=  2.8 PHAS= -163.7 FOM= 0.67 TEST= 1
INDE 23 62 33 FOBS=   38.1 SIGMA=  7.3 PHAS= -155.8 FOM= 0.24 TEST= 0
INDE 23 62 35 FOBS=    0.0 SIGMA= 25.6 PHAS=    0.0 FOM= 0.00 TEST= 0
INDE 23 62 37 FOBS=   69.6 SIGMA=  3.5 PHAS=   -5.1 FOM= 0.91 TEST= 0
INDE 23 62 39 FOBS=   41.5 SIGMA=  6.5 PHAS= -159.3 FOM= 0.47 TEST= 0
INDE 23 63 24 FOBS=   32.3 SIGMA= 10.8 PHAS= -108.0 FOM= 0.45 TEST= 0
INDE 23 63 26 FOBS=   71.5 SIGMA=  4.1 PHAS= -154.2 FOM= 0.90 TEST= 0
INDE 23 63 28 FOBS=   61.2 SIGMA=  4.4 PHAS=  101.4 FOM= 0.84 TEST= 0
INDE 23 63 30 FOBS=   52.0 SIGMA=  5.2 PHAS=  112.2 FOM= 0.79 TEST= 0
INDE 23 63 32 FOBS=    0.0 SIGMA= 23.4 PHAS=    0.0 FOM= 0.00 TEST= 0
INDE 23 63 34 FOBS=   22.3 SIGMA= 12.8 PHAS= -110.9 FOM= 0.24 TEST= 0
INDE 23 63 36 FOBS=    0.0 SIGMA= 24.2 PHAS=    0.0 FOM= 0.00 TEST= 0
INDE 23 63 38 FOBS=   95.3 SIGMA=  3.8 PHAS= -105.7 FOM= 0.90 TEST= 0
INDE 23 64 23 FOBS=   67.0 SIGMA=  4.3 PHAS= -132.1 FOM= 0.81 TEST= 0
INDE 23 64 25 FOBS=   23.0 SIGMA= 15.2 PHAS=   66.3 FOM= 0.04 TEST= 0
INDE 23 64 27 FOBS=   54.2 SIGMA=  5.4 PHAS=   16.8 FOM= 0.84 TEST= 0
INDE 23 64 29 FOBS=   84.8 SIGMA=  3.8 PHAS=    9.5 FOM= 0.88 TEST= 0
INDE 23 64 31 FOBS=    0.0 SIGMA= 27.4 PHAS=    0.0 FOM= 0.00 TEST= 0
INDE 23 64 33 FOBS=   87.5 SIGMA=  3.8 PHAS=  -47.7 FOM= 0.93 TEST= 0
INDE 23 64 35 FOBS=  103.9 SIGMA=  3.4 PHAS= -137.5 FOM= 0.92 TEST= 0
INDE 23 64 37 FOBS=   39.0 SIGMA=  9.0 PHAS=  115.3 FOM= 0.20 TEST= 1
INDE 23 65 24 FOBS=   47.6 SIGMA=  6.1 PHAS=  168.1 FOM= 0.61 TEST= 0
INDE 23 65 26 FOBS=   61.1 SIGMA=  4.9 PHAS=  -63.3 FOM= 0.87 TEST= 0
INDE 23 65 28 FOBS=   46.3 SIGMA=  6.8 PHAS= -140.2 FOM= 0.65 TEST= 0
INDE 23 65 30 FOBS=   69.3 SIGMA=  4.6 PHAS=  -45.4 FOM= 0.87 TEST= 0
INDE 23 65 32 FOBS=   28.4 SIGMA= 13.7 PHAS= -137.9 FOM= 0.65 TEST= 0
INDE 23 65 34 FOBS=   95.3 SIGMA=  3.7 PHAS= -168.9 FOM= 0.95 TEST= 0
INDE 23 66 23 FOBS=   26.9 SIGMA= 12.9 PHAS=    0.0 FOM= 0.00 TEST= 1
INDE 23 66 25 FOBS=   27.1 SIGMA= 21.2 PHAS=  111.7 FOM= 0.54 TEST= 0
INDE 23 66 27 FOBS=   77.5 SIGMA=  4.7 PHAS= -119.2 FOM= 0.89 TEST= 0
INDE 23 66 29 FOBS=   49.2 SIGMA=  6.5 PHAS=  132.4 FOM= 0.67 TEST= 0
INDE 23 66 31 FOBS=   30.5 SIGMA= 10.7 PHAS= -149.5 FOM= 0.67 TEST= 0
INDE 23 66 33 FOBS=   64.6 SIGMA=  5.3 PHAS=   74.8 FOM= 0.88 TEST= 0
INDE 23 67 24 FOBS=   40.8 SIGMA= 10.6 PHAS=   16.4 FOM= 0.51 TEST= 0
```

*FIG. 12A - 485*

```
INDE 23 67 26 FOBS=  81.4 SIGMA=  5.8 PHAS= -177.9 FOM= 0.75 TEST= 0
INDE 23 67 28 FOBS=  48.9 SIGMA=  7.5 PHAS=  113.7 FOM= 0.81 TEST= 0
INDE 23 67 30 FOBS=  73.4 SIGMA=  5.7 PHAS=   21.7 FOM= 0.88 TEST= 0
INDE 23 68 23 FOBS=  34.9 SIGMA= 12.8 PHAS= -151.3 FOM= 0.60 TEST= 0
INDE 23 68 25 FOBS=  36.8 SIGMA= 12.5 PHAS=   55.4 FOM= 0.56 TEST= 0
INDE 23 68 27 FOBS=  30.2 SIGMA= 15.9 PHAS=  -47.6 FOM= 0.32 TEST= 0
INDE 23 69 24 FOBS=  45.3 SIGMA= 10.1 PHAS=   65.5 FOM= 0.64 TEST= 0
INDE 23 69 26 FOBS=  36.6 SIGMA= 13.2 PHAS=  148.4 FOM= 0.50 TEST= 0
INDE 23 70 23 FOBS=  58.0 SIGMA=  7.6 PHAS= -176.4 FOM= 0.26 TEST= 0
INDE 24 24 24 FOBS= 492.5 SIGMA=  1.1 PHAS=  -94.0 FOM= 0.99 TEST= 0
INDE 24 25 25 FOBS= 347.1 SIGMA=  0.6 PHAS=  161.8 FOM= 0.94 TEST= 0
INDE 24 25 27 FOBS= 112.9 SIGMA=  1.3 PHAS= -132.9 FOM= 0.60 TEST= 0
INDE 24 25 29 FOBS= 140.4 SIGMA=  1.2 PHAS=  177.5 FOM= 0.88 TEST= 0
INDE 24 25 31 FOBS=  54.7 SIGMA=  2.9 PHAS= -102.7 FOM= 0.89 TEST= 0
INDE 24 25 33 FOBS=  49.9 SIGMA=  3.3 PHAS=   41.0 FOM= 0.53 TEST= 0
INDE 24 25 35 FOBS= 210.5 SIGMA=  0.9 PHAS=  133.2 FOM= 0.92 TEST= 0
INDE 24 25 37 FOBS= 196.1 SIGMA=  1.0 PHAS=  128.7 FOM= 0.95 TEST= 0
INDE 24 25 39 FOBS= 219.6 SIGMA=  0.9 PHAS= -129.1 FOM= 0.96 TEST= 0
INDE 24 25 41 FOBS= 231.9 SIGMA=  0.9 PHAS=   13.0 FOM= 0.96 TEST= 0
INDE 24 25 43 FOBS=  35.1 SIGMA=  4.9 PHAS= -126.1 FOM= 0.83 TEST= 0
INDE 24 25 45 FOBS= 146.3 SIGMA=  1.3 PHAS= -168.9 FOM= 0.93 TEST= 0
INDE 24 25 47 FOBS=  20.6 SIGMA=  9.1 PHAS=   98.7 FOM= 0.05 TEST= 0
INDE 24 25 49 FOBS= 175.4 SIGMA=  1.0 PHAS=  106.1 FOM= 0.89 TEST= 0
INDE 24 25 51 FOBS=  41.6 SIGMA=  3.9 PHAS=  173.1 FOM= 0.25 TEST= 0
INDE 24 25 53 FOBS= 111.1 SIGMA=  1.5 PHAS=  -32.2 FOM= 0.94 TEST= 0
INDE 24 25 55 FOBS= 120.2 SIGMA=  1.5 PHAS=   25.1 FOM= 0.92 TEST= 0
INDE 24 25 57 FOBS=  85.1 SIGMA=  3.5 PHAS=  -87.7 FOM= 0.90 TEST= 0
INDE 24 25 59 FOBS=  34.6 SIGMA=  9.8 PHAS= -103.3 FOM= 0.28 TEST= 0
INDE 24 25 61 FOBS=  78.6 SIGMA=  3.8 PHAS=  -25.7 FOM= 0.91 TEST= 0
INDE 24 25 63 FOBS=  20.0 SIGMA= 19.2 PHAS=  -55.3 FOM= 0.48 TEST= 0
INDE 24 25 65 FOBS=   0.0 SIGMA= 27.0 PHAS=    0.0 FOM= 0.00 TEST= 0
INDE 24 25 67 FOBS=  16.6 SIGMA= 27.5 PHAS= -101.2 FOM= 0.21 TEST= 0
INDE 24 25 69 FOBS=   7.5 SIGMA= 62.1 PHAS=  -21.6 FOM= 0.16 TEST= 0
INDE 24 26 24 FOBS= 109.6 SIGMA=  1.5 PHAS= -134.6 FOM= 0.95 TEST= 0
INDE 24 26 26 FOBS=   0.0 SIGMA= 18.1 PHAS=    0.0 FOM= 0.00 TEST= 0
INDE 24 26 28 FOBS= 236.6 SIGMA=  0.8 PHAS=  123.0 FOM= 0.95 TEST= 0
INDE 24 26 30 FOBS= 159.0 SIGMA=  1.1 PHAS= -149.9 FOM= 0.97 TEST= 0
INDE 24 26 32 FOBS= 298.4 SIGMA=  0.8 PHAS=  -86.7 FOM= 0.98 TEST= 1
INDE 24 26 34 FOBS= 119.3 SIGMA=  1.5 PHAS=   88.9 FOM= 0.83 TEST= 0
INDE 24 26 36 FOBS= 308.0 SIGMA=  0.7 PHAS=  104.0 FOM= 0.97 TEST= 0
INDE 24 26 38 FOBS=  33.7 SIGMA=  4.9 PHAS=  152.5 FOM= 0.87 TEST= 0
INDE 24 26 40 FOBS= 111.9 SIGMA=  1.6 PHAS=  -22.2 FOM= 0.79 TEST= 0
INDE 24 26 42 FOBS=  59.5 SIGMA=  3.0 PHAS=  -11.2 FOM= 0.16 TEST= 0
INDE 24 26 44 FOBS= 269.0 SIGMA=  0.8 PHAS=   70.0 FOM= 0.97 TEST= 0
INDE 24 26 46 FOBS=  76.8 SIGMA=  2.2 PHAS=   54.5 FOM= 0.78 TEST= 0
INDE 24 26 48 FOBS= 115.6 SIGMA=  1.5 PHAS= -104.2 FOM= 0.89 TEST= 0
INDE 24 26 50 FOBS= 123.7 SIGMA=  1.4 PHAS=  -54.9 FOM= 0.87 TEST= 0
INDE 24 26 52 FOBS=  76.5 SIGMA=  2.2 PHAS=    0.5 FOM= 0.01 TEST= 1
INDE 24 26 54 FOBS=  47.2 SIGMA=  3.5 PHAS= -178.6 FOM= 0.72 TEST= 0
INDE 24 26 56 FOBS=  41.4 SIGMA=  5.6 PHAS=    1.6 FOM= 0.12 TEST= 1
INDE 24 26 58 FOBS=  52.8 SIGMA=  5.5 PHAS= -161.5 FOM= 0.63 TEST= 0
INDE 24 26 60 FOBS=  54.8 SIGMA=  6.2 PHAS=  -42.2 FOM= 0.61 TEST= 0
INDE 24 26 62 FOBS=  53.5 SIGMA=  5.6 PHAS=   -2.7 FOM= 0.77 TEST= 0
INDE 24 26 64 FOBS=  54.8 SIGMA=  5.5 PHAS=   27.3 FOM= 0.48 TEST= 0
INDE 24 26 66 FOBS=  47.5 SIGMA=  9.7 PHAS=   64.8 FOM= 0.72 TEST= 0
INDE 24 26 68 FOBS=  34.2 SIGMA= 13.4 PHAS=  157.7 FOM= 0.42 TEST= 0
INDE 24 27 25 FOBS= 189.1 SIGMA=  1.0 PHAS=   83.5 FOM= 0.97 TEST= 0
INDE 24 27 27 FOBS=  54.9 SIGMA=  2.9 PHAS=    0.2 FOM= 0.87 TEST= 0
INDE 24 27 29 FOBS= 188.6 SIGMA=  1.0 PHAS=   99.6 FOM= 0.90 TEST= 0
INDE 24 27 31 FOBS=  80.4 SIGMA=  2.4 PHAS= -113.9 FOM= 0.70 TEST= 0
INDE 24 27 33 FOBS= 168.1 SIGMA=  1.2 PHAS= -162.4 FOM= 0.92 TEST= 0
INDE 24 27 35 FOBS= 133.8 SIGMA=  1.4 PHAS=   66.7 FOM= 0.90 TEST= 0
INDE 24 27 37 FOBS= 271.6 SIGMA=  0.8 PHAS=   35.5 FOM= 0.97 TEST= 0
INDE 24 27 39 FOBS=  49.1 SIGMA=  3.4 PHAS=  162.6 FOM= 0.60 TEST= 0
INDE 24 27 41 FOBS= 100.1 SIGMA=  1.8 PHAS= -167.5 FOM= 0.47 TEST= 0
INDE 24 27 43 FOBS= 413.7 SIGMA=  0.7 PHAS=  -55.9 FOM= 0.99 TEST= 0
INDE 24 27 45 FOBS=  53.0 SIGMA=  3.2 PHAS=  -51.1 FOM= 0.36 TEST= 0
INDE 24 27 47 FOBS= 151.8 SIGMA=  1.3 PHAS=  176.2 FOM= 0.92 TEST= 0
INDE 24 27 49 FOBS= 143.9 SIGMA=  1.3 PHAS=  159.8 FOM= 0.97 TEST= 0
INDE 24 27 51 FOBS=  98.2 SIGMA=  1.7 PHAS=  124.6 FOM= 0.87 TEST= 0
```

*FIG. 12A - 486*

```
INDE 24 27 53 FOBS=    0.0 SIGMA= 19.1 PHAS=    0.0 FOM= 0.00 TEST= 0
INDE 24 27 55 FOBS=    0.0 SIGMA= 22.9 PHAS=    0.0 FOM= 0.00 TEST= 0
INDE 24 27 57 FOBS=   33.2 SIGMA=  8.8 PHAS=  113.1 FOM= 0.42 TEST= 0
INDE 24 27 59 FOBS=    0.0 SIGMA= 27.1 PHAS=    0.0 FOM= 0.00 TEST= 0
INDE 24 27 61 FOBS=   79.3 SIGMA=  3.8 PHAS=   -7.2 FOM= 0.54 TEST= 1
INDE 24 27 63 FOBS=   30.6 SIGMA=  9.8 PHAS=  -95.9 FOM= 0.32 TEST= 0
INDE 24 27 65 FOBS=   58.0 SIGMA=  8.3 PHAS=  -15.6 FOM= 0.44 TEST= 1
INDE 24 27 67 FOBS=   65.9 SIGMA=  7.3 PHAS=  -36.3 FOM= 0.89 TEST= 0
INDE 24 28 24 FOBS=  201.6 SIGMA=  1.0 PHAS=  -98.5 FOM= 0.95 TEST= 0
INDE 24 28 26 FOBS=  431.9 SIGMA=  0.7 PHAS=  -34.0 FOM= 0.98 TEST= 0
INDE 24 28 28 FOBS=  283.7 SIGMA=  0.7 PHAS=   50.1 FOM= 0.96 TEST= 0
INDE 24 28 30 FOBS=   52.1 SIGMA=  3.5 PHAS=   42.8 FOM= 0.79 TEST= 0
INDE 24 28 32 FOBS=  166.2 SIGMA=  1.2 PHAS=  100.2 FOM= 0.38 TEST= 1
INDE 24 28 34 FOBS=  158.4 SIGMA=  1.3 PHAS=  167.5 FOM= 0.95 TEST= 0
INDE 24 28 36 FOBS=  198.3 SIGMA=  1.0 PHAS=  -64.4 FOM= 0.93 TEST= 0
INDE 24 28 38 FOBS=  189.3 SIGMA=  0.9 PHAS=  -47.7 FOM= 0.92 TEST= 0
INDE 24 28 40 FOBS=   43.8 SIGMA=  3.7 PHAS=   69.4 FOM= 0.81 TEST= 0
INDE 24 28 42 FOBS=  216.8 SIGMA=  1.0 PHAS= -127.6 FOM= 0.95 TEST= 0
INDE 24 28 44 FOBS=  107.2 SIGMA=  1.7 PHAS=  165.5 FOM= 0.94 TEST= 0
INDE 24 28 46 FOBS=  141.4 SIGMA=  1.3 PHAS=   75.3 FOM= 0.89 TEST= 0
INDE 24 28 48 FOBS=  144.4 SIGMA=  1.2 PHAS=  115.1 FOM= 0.94 TEST= 0
INDE 24 28 50 FOBS=  171.6 SIGMA=  1.1 PHAS=    6.7 FOM= 0.87 TEST= 1
INDE 24 28 52 FOBS=   63.8 SIGMA=  2.6 PHAS=   29.7 FOM= 0.78 TEST= 0
INDE 24 28 54 FOBS=   62.1 SIGMA=  3.7 PHAS=  171.6 FOM= 0.59 TEST= 0
INDE 24 28 56 FOBS=   55.8 SIGMA=  4.2 PHAS= -107.4 FOM= 0.70 TEST= 0
INDE 24 28 58 FOBS=   46.6 SIGMA=  5.1 PHAS=    6.4 FOM= 0.30 TEST= 0
INDE 24 28 60 FOBS=    0.0 SIGMA= 22.9 PHAS=    0.0 FOM= 0.00 TEST= 0
INDE 24 28 62 FOBS=   63.7 SIGMA=  4.8 PHAS= -140.6 FOM= 0.14 TEST= 1
INDE 24 28 64 FOBS=    0.0 SIGMA= 27.2 PHAS=    0.0 FOM= 0.00 TEST= 0
INDE 24 28 66 FOBS=   30.4 SIGMA= 15.4 PHAS=   49.0 FOM= 0.63 TEST= 0
INDE 24 28 68 FOBS=   76.9 SIGMA=  6.1 PHAS=  177.1 FOM= 0.74 TEST= 0
INDE 24 29 25 FOBS=  209.1 SIGMA=  0.9 PHAS=  -83.8 FOM= 0.89 TEST= 0
INDE 24 29 27 FOBS=  195.9 SIGMA=  1.0 PHAS= -129.7 FOM= 0.96 TEST= 0
INDE 24 29 29 FOBS=   58.7 SIGMA=  2.8 PHAS=  144.8 FOM= 0.90 TEST= 0
INDE 24 29 31 FOBS=   73.1 SIGMA=  2.5 PHAS=  -45.4 FOM= 0.69 TEST= 0
INDE 24 29 33 FOBS=  134.6 SIGMA=  1.5 PHAS=  174.2 FOM= 0.93 TEST= 0
INDE 24 29 35 FOBS=  246.1 SIGMA=  0.8 PHAS=  152.8 FOM= 0.97 TEST= 0
INDE 24 29 37 FOBS=  101.4 SIGMA=  1.8 PHAS=   63.3 FOM= 0.96 TEST= 0
INDE 24 29 39 FOBS=   69.2 SIGMA=  2.4 PHAS= -116.5 FOM= 0.80 TEST= 0
INDE 24 29 41 FOBS=  152.1 SIGMA=  1.2 PHAS=  141.2 FOM= 0.95 TEST= 0
INDE 24 29 43 FOBS=   25.9 SIGMA=  7.4 PHAS=   68.1 FOM= 0.23 TEST= 0
INDE 24 29 45 FOBS=   57.2 SIGMA=  3.0 PHAS=  -12.9 FOM= 0.63 TEST= 1
INDE 24 29 47 FOBS=   71.0 SIGMA=  2.4 PHAS=  104.1 FOM= 0.74 TEST= 0
INDE 24 29 49 FOBS=    0.0 SIGMA= 18.3 PHAS=    0.0 FOM= 0.00 TEST= 0
INDE 24 29 51 FOBS=  161.2 SIGMA=  1.1 PHAS= -124.0 FOM= 0.97 TEST= 0
INDE 24 29 53 FOBS=   40.9 SIGMA=  5.0 PHAS= -124.7 FOM= 0.78 TEST= 0
INDE 24 29 55 FOBS=   11.3 SIGMA= 23.0 PHAS=  -83.9 FOM= 0.15 TEST= 0
INDE 24 29 57 FOBS=    0.0 SIGMA= 24.5 PHAS=    0.0 FOM= 0.00 TEST= 0
INDE 24 29 59 FOBS=   46.4 SIGMA=  5.1 PHAS=    8.8 FOM= 0.67 TEST= 0
INDE 24 29 61 FOBS=    0.0 SIGMA= 21.7 PHAS=    0.0 FOM= 0.00 TEST= 0
INDE 24 29 63 FOBS=    0.0 SIGMA= 27.2 PHAS=    0.0 FOM= 0.00 TEST= 0
INDE 24 29 65 FOBS=  101.9 SIGMA=  4.6 PHAS=   28.7 FOM= 0.88 TEST= 0
INDE 24 29 67 FOBS=   74.5 SIGMA=  6.3 PHAS=  -16.5 FOM= 0.91 TEST= 0
INDE 24 30 24 FOBS=  273.5 SIGMA=  0.7 PHAS= -109.2 FOM= 0.97 TEST= 0
INDE 24 30 26 FOBS=  203.7 SIGMA=  1.0 PHAS= -113.3 FOM= 0.83 TEST= 1
INDE 24 30 28 FOBS=   81.1 SIGMA=  2.2 PHAS=   56.4 FOM= 0.92 TEST= 0
INDE 24 30 30 FOBS=  128.5 SIGMA=  1.4 PHAS=  -93.9 FOM= 0.96 TEST= 0
INDE 24 30 32 FOBS=  135.9 SIGMA=  1.3 PHAS=    7.4 FOM= 0.94 TEST= 0
INDE 24 30 34 FOBS=  119.9 SIGMA=  1.5 PHAS= -179.2 FOM= 0.87 TEST= 0
INDE 24 30 36 FOBS=  221.9 SIGMA=  0.9 PHAS=  -49.7 FOM= 0.98 TEST= 0
INDE 24 30 38 FOBS=   38.3 SIGMA=  4.3 PHAS=  -68.4 FOM= 0.33 TEST= 0
INDE 24 30 40 FOBS=  198.2 SIGMA=  0.9 PHAS=  137.2 FOM= 0.95 TEST= 0
INDE 24 30 42 FOBS=  112.6 SIGMA=  1.4 PHAS=   25.4 FOM= 0.91 TEST= 0
INDE 24 30 44 FOBS=    3.0 SIGMA= 63.6 PHAS=  -51.8 FOM= 0.03 TEST= 0
INDE 24 30 46 FOBS=   48.5 SIGMA=  3.5 PHAS=   87.9 FOM= 0.13 TEST= 0
INDE 24 30 48 FOBS=   37.8 SIGMA=  4.4 PHAS=  120.7 FOM= 0.75 TEST= 1
INDE 24 30 50 FOBS=  112.7 SIGMA=  1.5 PHAS=   84.7 FOM= 0.90 TEST= 0
INDE 24 30 52 FOBS=  118.8 SIGMA=  1.6 PHAS=  170.4 FOM= 0.92 TEST= 0
INDE 24 30 54 FOBS=   24.4 SIGMA= 12.6 PHAS=  126.7 FOM= 0.25 TEST= 0
INDE 24 30 56 FOBS=   68.5 SIGMA=  3.5 PHAS= -138.1 FOM= 0.84 TEST= 0
```

*FIG. 12A - 487*

```
INDE 24 30 58 FOBS=    89.1 SIGMA=  3.5 PHAS=  -38.7 FOM= 0.92 TEST= 0
INDE 24 30 60 FOBS=    21.5 SIGMA= 14.0 PHAS=   61.2 FOM= 0.20 TEST= 0
INDE 24 30 62 FOBS=    72.6 SIGMA=  3.8 PHAS=  -29.8 FOM= 0.88 TEST= 0
INDE 24 30 64 FOBS=    42.7 SIGMA= 11.0 PHAS=  -60.4 FOM= 0.53 TEST= 0
INDE 24 30 66 FOBS=    63.0 SIGMA=  7.3 PHAS=  -75.7 FOM= 0.89 TEST= 0
INDE 24 31 25 FOBS=   106.2 SIGMA=  1.7 PHAS= -146.7 FOM= 0.92 TEST= 0
INDE 24 31 27 FOBS=   290.3 SIGMA=  0.8 PHAS= -159.5 FOM= 0.97 TEST= 0
INDE 24 31 29 FOBS=   418.6 SIGMA=  0.8 PHAS= -146.7 FOM= 0.98 TEST= 0
INDE 24 31 31 FOBS=   176.0 SIGMA=  1.0 PHAS=  171.2 FOM= 0.72 TEST= 1
INDE 24 31 33 FOBS=    73.0 SIGMA=  2.4 PHAS=  137.0 FOM= 0.67 TEST= 0
INDE 24 31 35 FOBS=   320.7 SIGMA=  0.7 PHAS= -167.3 FOM= 0.97 TEST= 0
INDE 24 31 37 FOBS=     0.0 SIGMA= 18.8 PHAS=    0.0 FOM= 0.00 TEST= 0
INDE 24 31 39 FOBS=   193.9 SIGMA=  0.9 PHAS=   47.6 FOM= 0.86 TEST= 0
INDE 24 31 41 FOBS=    68.2 SIGMA=  2.5 PHAS=  153.1 FOM= 0.95 TEST= 0
INDE 24 31 43 FOBS=   113.8 SIGMA=  1.4 PHAS=  166.3 FOM= 0.83 TEST= 1
INDE 24 31 45 FOBS=     0.0 SIGMA= 18.0 PHAS=    0.0 FOM= 0.00 TEST= 0
INDE 24 31 47 FOBS=    30.1 SIGMA=  5.3 PHAS= -179.0 FOM= 0.46 TEST= 0
INDE 24 31 49 FOBS=     0.0 SIGMA= 19.2 PHAS=    0.0 FOM= 0.00 TEST= 0
INDE 24 31 51 FOBS=    42.0 SIGMA=  4.4 PHAS=   94.4 FOM= 0.56 TEST= 0
INDE 24 31 53 FOBS=    14.7 SIGMA= 19.2 PHAS=  119.5 FOM= 0.04 TEST= 1
INDE 24 31 55 FOBS=    63.6 SIGMA=  3.7 PHAS= -151.9 FOM= 0.70 TEST= 0
INDE 24 31 57 FOBS=   130.2 SIGMA=  1.9 PHAS= -134.8 FOM= 0.53 TEST= 1
INDE 24 31 59 FOBS=    56.3 SIGMA=  5.4 PHAS=   38.5 FOM= 0.12 TEST= 1
INDE 24 31 61 FOBS=    33.4 SIGMA=  9.0 PHAS=  -85.2 FOM= 0.47 TEST= 0
INDE 24 31 63 FOBS=    77.7 SIGMA=  4.0 PHAS=  169.8 FOM= 0.87 TEST= 0
INDE 24 31 65 FOBS=    44.8 SIGMA= 10.5 PHAS= -176.2 FOM= 0.71 TEST= 0
INDE 24 31 67 FOBS=     0.0 SIGMA= 30.9 PHAS=    0.0 FOM= 0.00 TEST= 0
INDE 24 32 24 FOBS=   108.2 SIGMA=  1.6 PHAS= -122.9 FOM= 0.62 TEST= 0
INDE 24 32 26 FOBS=    76.8 SIGMA=  2.5 PHAS=   90.3 FOM= 0.75 TEST= 0
INDE 24 32 28 FOBS=   300.0 SIGMA=  0.8 PHAS=   98.2 FOM= 0.97 TEST= 0
INDE 24 32 30 FOBS=   247.0 SIGMA=  0.8 PHAS=   94.2 FOM= 0.96 TEST= 0
INDE 24 32 32 FOBS=   110.5 SIGMA=  1.6 PHAS=   -8.1 FOM= 0.83 TEST= 0
INDE 24 32 34 FOBS=   105.8 SIGMA=  1.6 PHAS=  -76.6 FOM= 0.77 TEST= 0
INDE 24 32 36 FOBS=    14.3 SIGMA= 13.7 PHAS=   54.4 FOM= 0.41 TEST= 0
INDE 24 32 38 FOBS=   155.1 SIGMA=  1.1 PHAS=  -77.6 FOM= 0.78 TEST= 0
INDE 24 32 40 FOBS=   111.3 SIGMA=  1.5 PHAS=   26.2 FOM= 0.90 TEST= 0
INDE 24 32 42 FOBS=   159.4 SIGMA=  1.1 PHAS=   76.7 FOM= 0.96 TEST= 0
INDE 24 32 44 FOBS=    78.9 SIGMA=  2.1 PHAS=   51.8 FOM= 0.88 TEST= 0
INDE 24 32 46 FOBS=     0.0 SIGMA= 17.5 PHAS=    0.0 FOM= 0.00 TEST= 1
INDE 24 32 48 FOBS=   121.1 SIGMA=  1.3 PHAS= -155.7 FOM= 0.90 TEST= 0
INDE 24 32 50 FOBS=     0.0 SIGMA= 18.8 PHAS=    0.0 FOM= 0.00 TEST= 0
INDE 24 32 52 FOBS=    30.9 SIGMA=  6.8 PHAS= -140.2 FOM= 0.58 TEST= 0
INDE 24 32 54 FOBS=     3.6 SIGMA= 71.6 PHAS=    0.0 FOM= 0.00 TEST= 1
INDE 24 32 56 FOBS=     0.0 SIGMA= 22.6 PHAS=    0.0 FOM= 0.00 TEST= 0
INDE 24 32 58 FOBS=    53.2 SIGMA=  4.4 PHAS= -121.5 FOM= 0.75 TEST= 0
INDE 24 32 60 FOBS=    86.2 SIGMA=  3.6 PHAS=  120.3 FOM= 0.93 TEST= 0
INDE 24 32 62 FOBS=    80.9 SIGMA=  3.8 PHAS=   15.5 FOM= 0.84 TEST= 0
INDE 24 32 64 FOBS=    82.8 SIGMA=  3.8 PHAS=   51.0 FOM= 0.78 TEST= 0
INDE 24 32 66 FOBS=    27.7 SIGMA= 17.1 PHAS=  -40.9 FOM= 0.11 TEST= 0
INDE 24 33 25 FOBS=   124.5 SIGMA=  1.5 PHAS=  115.9 FOM= 0.93 TEST= 0
INDE 24 33 27 FOBS=    75.1 SIGMA=  2.6 PHAS=  143.8 FOM= 0.83 TEST= 0
INDE 24 33 29 FOBS=     0.0 SIGMA= 19.8 PHAS=    0.0 FOM= 0.00 TEST= 0
INDE 24 33 31 FOBS=   162.0 SIGMA=  1.1 PHAS=  -84.9 FOM= 0.76 TEST= 1
INDE 24 33 33 FOBS=   174.4 SIGMA=  1.0 PHAS= -154.3 FOM= 0.90 TEST= 0
INDE 24 33 35 FOBS=   155.2 SIGMA=  1.1 PHAS=  158.5 FOM= 0.94 TEST= 0
INDE 24 33 37 FOBS=    52.1 SIGMA=  3.1 PHAS=  -76.1 FOM= 0.78 TEST= 0
INDE 24 33 39 FOBS=   109.0 SIGMA=  1.5 PHAS=  -41.0 FOM= 0.86 TEST= 0
INDE 24 33 41 FOBS=   130.9 SIGMA=  1.3 PHAS= -110.1 FOM= 0.95 TEST= 0
INDE 24 33 43 FOBS=    68.2 SIGMA=  2.3 PHAS=  129.0 FOM= 0.81 TEST= 0
INDE 24 33 45 FOBS=    20.3 SIGMA=  8.3 PHAS=  -56.6 FOM= 0.25 TEST= 0
INDE 24 33 47 FOBS=    83.1 SIGMA=  1.9 PHAS=  154.8 FOM= 0.73 TEST= 0
INDE 24 33 49 FOBS=     0.0 SIGMA= 18.2 PHAS=    0.0 FOM= 0.00 TEST= 0
INDE 24 33 51 FOBS=     0.0 SIGMA= 18.6 PHAS=    0.0 FOM= 0.00 TEST= 0
INDE 24 33 53 FOBS=    34.2 SIGMA=  5.6 PHAS=  -70.9 FOM= 0.19 TEST= 0
INDE 24 33 55 FOBS=     0.0 SIGMA= 20.5 PHAS=    0.0 FOM= 0.00 TEST= 0
INDE 24 33 57 FOBS=    82.7 SIGMA=  3.1 PHAS= -131.0 FOM= 0.75 TEST= 0
INDE 24 33 59 FOBS=    62.6 SIGMA=  3.8 PHAS=   26.5 FOM= 0.82 TEST= 0
INDE 24 33 61 FOBS=    55.5 SIGMA=  5.5 PHAS=  -22.1 FOM= 0.74 TEST= 0
INDE 24 33 63 FOBS=   107.9 SIGMA=  3.0 PHAS= -114.4 FOM= 0.89 TEST= 0
INDE 24 33 65 FOBS=     0.0 SIGMA= 26.9 PHAS=    0.0 FOM= 0.00 TEST= 0
```

*FIG. 12A - 488*

| | | | | | | | | | | | |
|---|---|---|---|---|---|---|---|---|---|---|---|
| INDE | 24 | 34 | 24 | FOBS= | 106.3 | SIGMA= | 1.8 | PHAS= | 147.6 | FOM= 0.89 | TEST= 0 |
| INDE | 24 | 34 | 26 | FOBS= | 30.2 | SIGMA= | 6.2 | PHAS= | -66.2 | FOM= 0.71 | TEST= 0 |
| INDE | 24 | 34 | 28 | FOBS= | 185.5 | SIGMA= | 1.1 | PHAS= | 77.1 | FOM= 0.95 | TEST= 0 |
| INDE | 24 | 34 | 30 | FOBS= | 108.7 | SIGMA= | 1.7 | PHAS= | -81.4 | FOM= 0.93 | TEST= 0 |
| INDE | 24 | 34 | 32 | FOBS= | 182.8 | SIGMA= | 1.0 | PHAS= | 83.9 | FOM= 0.66 | TEST= 1 |
| INDE | 24 | 34 | 34 | FOBS= | 115.5 | SIGMA= | 1.5 | PHAS= | 30.8 | FOM= 0.91 | TEST= 0 |
| INDE | 24 | 34 | 36 | FOBS= | 0.0 | SIGMA= | 18.1 | PHAS= | 0.0 | FOM= 0.00 | TEST= 1 |
| INDE | 24 | 34 | 38 | FOBS= | 197.6 | SIGMA= | 0.9 | PHAS= | -93.4 | FOM= 0.97 | TEST= 0 |
| INDE | 24 | 34 | 40 | FOBS= | 60.7 | SIGMA= | 2.7 | PHAS= | 112.3 | FOM= 0.86 | TEST= 0 |
| INDE | 24 | 34 | 42 | FOBS= | 106.5 | SIGMA= | 1.6 | PHAS= | 84.8 | FOM= 0.90 | TEST= 0 |
| INDE | 24 | 34 | 44 | FOBS= | 47.1 | SIGMA= | 3.5 | PHAS= | 100.5 | FOM= 0.79 | TEST= 0 |
| INDE | 24 | 34 | 46 | FOBS= | 44.0 | SIGMA= | 3.8 | PHAS= | -148.5 | FOM= 0.47 | TEST= 0 |
| INDE | 24 | 34 | 48 | FOBS= | 47.3 | SIGMA= | 4.0 | PHAS= | -162.5 | FOM= 0.77 | TEST= 0 |
| INDE | 24 | 34 | 50 | FOBS= | 0.0 | SIGMA= | 20.4 | PHAS= | 0.0 | FOM= 0.00 | TEST= 0 |
| INDE | 24 | 34 | 52 | FOBS= | 0.0 | SIGMA= | 19.6 | PHAS= | 0.0 | FOM= 0.00 | TEST= 0 |
| INDE | 24 | 34 | 54 | FOBS= | 0.0 | SIGMA= | 21.5 | PHAS= | 0.0 | FOM= 0.00 | TEST= 0 |
| INDE | 24 | 34 | 56 | FOBS= | 0.0 | SIGMA= | 20.6 | PHAS= | 0.0 | FOM= 0.00 | TEST= 0 |
| INDE | 24 | 34 | 58 | FOBS= | 62.5 | SIGMA= | 3.9 | PHAS= | -63.4 | FOM= 0.82 | TEST= 0 |
| INDE | 24 | 34 | 60 | FOBS= | 40.9 | SIGMA= | 5.8 | PHAS= | -0.4 | FOM= 0.52 | TEST= 0 |
| INDE | 24 | 34 | 62 | FOBS= | 77.5 | SIGMA= | 3.6 | PHAS= | 136.6 | FOM= 0.89 | TEST= 0 |
| INDE | 24 | 34 | 64 | FOBS= | 0.0 | SIGMA= | 24.9 | PHAS= | 0.0 | FOM= 0.00 | TEST= 0 |
| INDE | 24 | 35 | 25 | FOBS= | 249.1 | SIGMA= | 0.9 | PHAS= | 87.4 | FOM= 0.95 | TEST= 0 |
| INDE | 24 | 35 | 27 | FOBS= | 172.9 | SIGMA= | 1.2 | PHAS= | 90.7 | FOM= 0.94 | TEST= 0 |
| INDE | 24 | 35 | 29 | FOBS= | 155.3 | SIGMA= | 1.3 | PHAS= | 135.5 | FOM= 0.83 | TEST= 0 |
| INDE | 24 | 35 | 31 | FOBS= | 182.2 | SIGMA= | 1.1 | PHAS= | -119.1 | FOM= 0.93 | TEST= 0 |
| INDE | 24 | 35 | 33 | FOBS= | 50.5 | SIGMA= | 3.3 | PHAS= | -60.7 | FOM= 0.75 | TEST= 1 |
| INDE | 24 | 35 | 35 | FOBS= | 49.0 | SIGMA= | 3.4 | PHAS= | 177.7 | FOM= 0.88 | TEST= 0 |
| INDE | 24 | 35 | 37 | FOBS= | 191.0 | SIGMA= | 0.9 | PHAS= | -172.8 | FOM= 0.97 | TEST= 0 |
| INDE | 24 | 35 | 39 | FOBS= | 0.0 | SIGMA= | 18.0 | PHAS= | 0.0 | FOM= 0.00 | TEST= 0 |
| INDE | 24 | 35 | 41 | FOBS= | 172.0 | SIGMA= | 1.0 | PHAS= | -119.8 | FOM= 0.94 | TEST= 0 |
| INDE | 24 | 35 | 43 | FOBS= | 152.3 | SIGMA= | 1.1 | PHAS= | 47.0 | FOM= 0.97 | TEST= 0 |
| INDE | 24 | 35 | 45 | FOBS= | 128.2 | SIGMA= | 1.3 | PHAS= | 50.2 | FOM= 0.89 | TEST= 0 |
| INDE | 24 | 35 | 47 | FOBS= | 44.7 | SIGMA= | 4.5 | PHAS= | 154.5 | FOM= 0.69 | TEST= 0 |
| INDE | 24 | 35 | 49 | FOBS= | 56.7 | SIGMA= | 3.3 | PHAS= | -71.2 | FOM= 0.53 | TEST= 0 |
| INDE | 24 | 35 | 51 | FOBS= | 93.2 | SIGMA= | 2.0 | PHAS= | -121.5 | FOM= 0.86 | TEST= 0 |
| INDE | 24 | 35 | 53 | FOBS= | 65.8 | SIGMA= | 3.1 | PHAS= | -96.9 | FOM= 0.88 | TEST= 0 |
| INDE | 24 | 35 | 55 | FOBS= | 91.1 | SIGMA= | 2.3 | PHAS= | -82.6 | FOM= 0.86 | TEST= 0 |
| INDE | 24 | 35 | 57 | FOBS= | 68.6 | SIGMA= | 3.0 | PHAS= | -166.6 | FOM= 0.84 | TEST= 0 |
| INDE | 24 | 35 | 59 | FOBS= | 67.2 | SIGMA= | 3.1 | PHAS= | -107.8 | FOM= 0.77 | TEST= 0 |
| INDE | 24 | 35 | 61 | FOBS= | 0.0 | SIGMA= | 21.8 | PHAS= | 0.0 | FOM= 0.00 | TEST= 0 |
| INDE | 24 | 35 | 63 | FOBS= | 52.5 | SIGMA= | 6.0 | PHAS= | 159.7 | FOM= 0.11 | TEST= 1 |
| INDE | 24 | 35 | 65 | FOBS= | 62.2 | SIGMA= | 5.2 | PHAS= | 57.9 | FOM= 0.86 | TEST= 0 |
| INDE | 24 | 36 | 24 | FOBS= | 63.2 | SIGMA= | 3.0 | PHAS= | 138.4 | FOM= 0.73 | TEST= 0 |
| INDE | 24 | 36 | 26 | FOBS= | 207.6 | SIGMA= | 1.0 | PHAS= | -27.7 | FOM= 0.90 | TEST= 0 |
| INDE | 24 | 36 | 28 | FOBS= | 269.1 | SIGMA= | 0.8 | PHAS= | 54.2 | FOM= 0.97 | TEST= 0 |
| INDE | 24 | 36 | 30 | FOBS= | 76.3 | SIGMA= | 2.4 | PHAS= | 90.0 | FOM= 0.89 | TEST= 0 |
| INDE | 24 | 36 | 32 | FOBS= | 172.8 | SIGMA= | 1.1 | PHAS= | 132.0 | FOM= 0.94 | TEST= 0 |
| INDE | 24 | 36 | 34 | FOBS= | 62.8 | SIGMA= | 2.6 | PHAS= | -83.6 | FOM= 0.82 | TEST= 0 |
| INDE | 24 | 36 | 36 | FOBS= | 81.3 | SIGMA= | 2.1 | PHAS= | 74.8 | FOM= 0.92 | TEST= 0 |
| INDE | 24 | 36 | 38 | FOBS= | 69.4 | SIGMA= | 2.4 | PHAS= | -104.9 | FOM= 0.87 | TEST= 0 |
| INDE | 24 | 36 | 40 | FOBS= | 40.0 | SIGMA= | 4.1 | PHAS= | 80.2 | FOM= 0.82 | TEST= 0 |
| INDE | 24 | 36 | 42 | FOBS= | 108.7 | SIGMA= | 1.5 | PHAS= | -25.6 | FOM= 0.31 | TEST= 1 |
| INDE | 24 | 36 | 44 | FOBS= | 100.8 | SIGMA= | 1.7 | PHAS= | -79.9 | FOM= 0.86 | TEST= 0 |
| INDE | 24 | 36 | 46 | FOBS= | 42.9 | SIGMA= | 4.0 | PHAS= | 87.0 | FOM= 0.40 | TEST= 0 |
| INDE | 24 | 36 | 48 | FOBS= | 62.9 | SIGMA= | 3.0 | PHAS= | -139.9 | FOM= 0.78 | TEST= 0 |
| INDE | 24 | 36 | 50 | FOBS= | 31.4 | SIGMA= | 6.8 | PHAS= | -152.1 | FOM= 0.46 | TEST= 0 |
| INDE | 24 | 36 | 52 | FOBS= | 43.0 | SIGMA= | 4.3 | PHAS= | -13.6 | FOM= 0.22 | TEST= 0 |
| INDE | 24 | 36 | 54 | FOBS= | 160.0 | SIGMA= | 1.4 | PHAS= | -155.9 | FOM= 0.97 | TEST= 0 |
| INDE | 24 | 36 | 56 | FOBS= | 0.0 | SIGMA= | 20.9 | PHAS= | 0.0 | FOM= 0.00 | TEST= 0 |
| INDE | 24 | 36 | 58 | FOBS= | 0.0 | SIGMA= | 21.0 | PHAS= | 0.0 | FOM= 0.00 | TEST= 0 |
| INDE | 24 | 36 | 60 | FOBS= | 16.2 | SIGMA= | 14.7 | PHAS= | 58.8 | FOM= 0.44 | TEST= 0 |
| INDE | 24 | 36 | 62 | FOBS= | 32.6 | SIGMA= | 6.8 | PHAS= | -157.8 | FOM= 0.37 | TEST= 0 |
| INDE | 24 | 36 | 64 | FOBS= | 76.3 | SIGMA= | 4.3 | PHAS= | -82.1 | FOM= 0.89 | TEST= 0 |
| INDE | 24 | 37 | 25 | FOBS= | 252.9 | SIGMA= | 0.9 | PHAS= | 32.8 | FOM= 0.95 | TEST= 0 |
| INDE | 24 | 37 | 27 | FOBS= | 54.4 | SIGMA= | 3.4 | PHAS= | -159.2 | FOM= 0.67 | TEST= 0 |
| INDE | 24 | 37 | 29 | FOBS= | 77.5 | SIGMA= | 2.4 | PHAS= | 59.5 | FOM= 0.51 | TEST= 0 |
| INDE | 24 | 37 | 31 | FOBS= | 7.1 | SIGMA= | 26.8 | PHAS= | 168.7 | FOM= 0.03 | TEST= 0 |
| INDE | 24 | 37 | 33 | FOBS= | 42.8 | SIGMA= | 4.2 | PHAS= | 33.3 | FOM= 0.28 | TEST= 0 |
| INDE | 24 | 37 | 35 | FOBS= | 121.1 | SIGMA= | 1.4 | PHAS= | 119.4 | FOM= 0.74 | TEST= 0 |
| INDE | 24 | 37 | 37 | FOBS= | 58.8 | SIGMA= | 2.8 | PHAS= | -174.5 | FOM= 0.86 | TEST= 0 |

*FIG. 12A - 489*

```
INDE  24  37  39  FOBS=    55.2  SIGMA=   2.9  PHAS=  -123.6  FOM=  0.32  TEST= 0
INDE  24  37  41  FOBS=   218.7  SIGMA=   0.8  PHAS=   -81.6  FOM=  0.94  TEST= 0
INDE  24  37  43  FOBS=    26.8  SIGMA=   6.8  PHAS=   109.6  FOM=  0.35  TEST= 0
INDE  24  37  45  FOBS=    95.6  SIGMA=   1.8  PHAS=    54.2  FOM=  0.75  TEST= 0
INDE  24  37  47  FOBS=    57.9  SIGMA=   3.1  PHAS=  -161.0  FOM=  0.71  TEST= 0
INDE  24  37  49  FOBS=    87.5  SIGMA=   2.2  PHAS=   172.6  FOM=  0.92  TEST= 0
INDE  24  37  51  FOBS=    62.2  SIGMA=   3.0  PHAS=   174.4  FOM=  0.88  TEST= 0
INDE  24  37  53  FOBS=    79.1  SIGMA=   2.6  PHAS=  -157.4  FOM=  0.91  TEST= 0
INDE  24  37  55  FOBS=    90.6  SIGMA=   2.3  PHAS=   131.7  FOM=  0.93  TEST= 0
INDE  24  37  57  FOBS=    38.4  SIGMA=   5.3  PHAS=   167.7  FOM=  0.43  TEST= 0
INDE  24  37  59  FOBS=    16.6  SIGMA=  12.2  PHAS=   -29.0  FOM=  0.20  TEST= 1
INDE  24  37  61  FOBS=     0.0  SIGMA=  20.3  PHAS=     0.0  FOM=  0.00  TEST= 0
INDE  24  37  63  FOBS=     0.0  SIGMA=  23.3  PHAS=     0.0  FOM=  0.00  TEST= 1
INDE  24  38  24  FOBS=   247.5  SIGMA=   1.0  PHAS=   -95.5  FOM=  0.96  TEST= 0
INDE  24  38  26  FOBS=   205.3  SIGMA=   1.0  PHAS=   -86.8  FOM=  0.96  TEST= 0
INDE  24  38  28  FOBS=    76.1  SIGMA=   2.4  PHAS=   -44.8  FOM=  0.78  TEST= 0
INDE  24  38  30  FOBS=   133.8  SIGMA=   1.4  PHAS=    21.2  FOM=  0.90  TEST= 0
INDE  24  38  32  FOBS=   125.2  SIGMA=   1.5  PHAS=  -117.0  FOM=  0.85  TEST= 0
INDE  24  38  34  FOBS=    19.9  SIGMA=   8.2  PHAS=   151.7  FOM=  0.03  TEST= 0
INDE  24  38  36  FOBS=    82.9  SIGMA=   2.0  PHAS=   107.0  FOM=  0.92  TEST= 0
INDE  24  38  38  FOBS=    51.0  SIGMA=   3.2  PHAS=    20.4  FOM=  0.85  TEST= 0
INDE  24  38  40  FOBS=    46.2  SIGMA=   3.6  PHAS=  -139.7  FOM=  0.57  TEST= 0
INDE  24  38  42  FOBS=    32.2  SIGMA=   6.3  PHAS=    21.2  FOM=  0.00  TEST= 0
INDE  24  38  44  FOBS=     0.0  SIGMA=  19.1  PHAS=     0.0  FOM=  0.00  TEST= 0
INDE  24  38  46  FOBS=    26.0  SIGMA=   7.7  PHAS=    60.1  FOM=  0.12  TEST= 0
INDE  24  38  48  FOBS=    72.4  SIGMA=   2.7  PHAS=    72.6  FOM=  0.87  TEST= 0
INDE  24  38  50  FOBS=   116.0  SIGMA=   1.7  PHAS=    41.9  FOM=  0.79  TEST= 1
INDE  24  38  52  FOBS=    77.3  SIGMA=   2.5  PHAS=    73.5  FOM=  0.94  TEST= 0
INDE  24  38  54  FOBS=    84.2  SIGMA=   2.5  PHAS=   157.9  FOM=  0.89  TEST= 0
INDE  24  38  56  FOBS=    97.5  SIGMA=   2.2  PHAS=     3.5  FOM=  0.95  TEST= 0
INDE  24  38  58  FOBS=    17.3  SIGMA=  12.7  PHAS=   -68.2  FOM=  0.29  TEST= 0
INDE  24  38  60  FOBS=    73.1  SIGMA=   2.9  PHAS=   110.0  FOM=  0.69  TEST= 0
INDE  24  38  62  FOBS=    98.9  SIGMA=   2.6  PHAS=    31.2  FOM=  0.92  TEST= 0
INDE  24  39  25  FOBS=   203.4  SIGMA=   1.0  PHAS=   153.6  FOM=  0.94  TEST= 0
INDE  24  39  27  FOBS=   118.3  SIGMA=   1.6  PHAS=  -169.9  FOM=  0.91  TEST= 0
INDE  24  39  29  FOBS=    76.6  SIGMA=   2.4  PHAS=  -129.6  FOM=  0.84  TEST= 0
INDE  24  39  31  FOBS=    73.3  SIGMA=   2.5  PHAS=  -139.4  FOM=  0.78  TEST= 0
INDE  24  39  33  FOBS=    54.8  SIGMA=   3.3  PHAS=   169.1  FOM=  0.38  TEST= 0
INDE  24  39  35  FOBS=   108.0  SIGMA=   1.6  PHAS=   159.7  FOM=  0.78  TEST= 0
INDE  24  39  37  FOBS=    22.1  SIGMA=   7.3  PHAS=     2.1  FOM=  0.42  TEST= 0
INDE  24  39  39  FOBS=   119.1  SIGMA=   1.4  PHAS=    79.1  FOM=  0.87  TEST= 0
INDE  24  39  41  FOBS=    63.5  SIGMA=   2.8  PHAS=   144.0  FOM=  0.90  TEST= 0
INDE  24  39  43  FOBS=     0.0  SIGMA=  19.0  PHAS=     0.0  FOM=  0.00  TEST= 1
INDE  24  39  45  FOBS=    49.7  SIGMA=   3.5  PHAS=  -142.6  FOM=  0.70  TEST= 0
INDE  24  39  47  FOBS=     0.0  SIGMA=  21.4  PHAS=     0.0  FOM=  0.00  TEST= 0
INDE  24  39  49  FOBS=     0.0  SIGMA=  19.9  PHAS=     0.0  FOM=  0.00  TEST= 0
INDE  24  39  51  FOBS=    34.3  SIGMA=   5.8  PHAS=   -87.0  FOM=  0.38  TEST= 0
INDE  24  39  53  FOBS=    70.0  SIGMA=   3.0  PHAS=  -132.1  FOM=  0.73  TEST= 0
INDE  24  39  55  FOBS=    39.1  SIGMA=   5.2  PHAS=  -144.6  FOM=  0.60  TEST= 0
INDE  24  39  57  FOBS=    72.4  SIGMA=   2.9  PHAS=   -99.7  FOM=  0.81  TEST= 0
INDE  24  39  59  FOBS=    35.0  SIGMA=   6.9  PHAS=    35.9  FOM=  0.59  TEST= 0
INDE  24  39  61  FOBS=    70.9  SIGMA=   3.6  PHAS=  -105.3  FOM=  0.93  TEST= 0
INDE  24  40  24  FOBS=   176.4  SIGMA=   1.2  PHAS=   -15.3  FOM=  0.93  TEST= 0
INDE  24  40  26  FOBS=    78.7  SIGMA=   2.3  PHAS=    86.2  FOM=  0.85  TEST= 0
INDE  24  40  28  FOBS=    29.0  SIGMA=   6.4  PHAS=   146.5  FOM=  0.32  TEST= 0
INDE  24  40  30  FOBS=   237.1  SIGMA=   0.9  PHAS=    54.6  FOM=  0.95  TEST= 0
INDE  24  40  32  FOBS=    52.9  SIGMA=   3.4  PHAS=   130.3  FOM=  0.91  TEST= 0
INDE  24  40  34  FOBS=   133.8  SIGMA=   1.4  PHAS=    79.7  FOM=  0.80  TEST= 0
INDE  24  40  36  FOBS=    26.7  SIGMA=   6.3  PHAS=   -58.3  FOM=  0.71  TEST= 0
INDE  24  40  38  FOBS=   137.6  SIGMA=   1.3  PHAS=   -31.1  FOM=  0.95  TEST= 0
INDE  24  40  40  FOBS=   116.5  SIGMA=   1.6  PHAS=   -38.1  FOM=  0.92  TEST= 0
INDE  24  40  42  FOBS=    53.8  SIGMA=   3.5  PHAS=    84.8  FOM=  0.02  TEST= 1
INDE  24  40  44  FOBS=    52.2  SIGMA=   3.3  PHAS=   107.9  FOM=  0.87  TEST= 0
INDE  24  40  46  FOBS=     0.0  SIGMA=  19.0  PHAS=     0.0  FOM=  0.00  TEST= 0
INDE  24  40  48  FOBS=   108.5  SIGMA=   1.6  PHAS=    27.5  FOM=  0.90  TEST= 0
INDE  24  40  50  FOBS=    47.4  SIGMA=   4.0  PHAS=    21.9  FOM=  0.60  TEST= 0
INDE  24  40  52  FOBS=    83.6  SIGMA=   2.5  PHAS=    47.6  FOM=  0.91  TEST= 0
INDE  24  40  54  FOBS=     0.0  SIGMA=  20.3  PHAS=     0.0  FOM=  0.00  TEST= 0
INDE  24  40  56  FOBS=    42.4  SIGMA=   5.3  PHAS=   -47.5  FOM=  0.11  TEST= 1
INDE  24  40  58  FOBS=    83.9  SIGMA=   2.5  PHAS=  -156.5  FOM=  0.92  TEST= 0
```

*FIG. 12A - 490*

```
INDE  24  40  60 FOBS=   50.3 SIGMA=  4.2 PHAS= -158.9 FOM= 0.30 TEST= 1
INDE  24  40  62 FOBS=   47.7 SIGMA=  5.4 PHAS= -136.5 FOM= 0.42 TEST= 0
INDE  24  41  25 FOBS=  165.8 SIGMA=  1.3 PHAS= -147.9 FOM= 0.95 TEST= 0
INDE  24  41  27 FOBS=  146.2 SIGMA=  1.3 PHAS=   20.4 FOM= 0.98 TEST= 0
INDE  24  41  29 FOBS=   20.8 SIGMA=  9.0 PHAS=  117.5 FOM= 0.07 TEST= 1
INDE  24  41  31 FOBS=    0.0 SIGMA= 19.7 PHAS=    0.0 FOM= 0.00 TEST= 0
INDE  24  41  33 FOBS=  144.9 SIGMA=  1.3 PHAS=  -32.5 FOM= 0.92 TEST= 0
INDE  24  41  35 FOBS=   77.4 SIGMA=  2.3 PHAS=  -77.4 FOM= 0.66 TEST= 0
INDE  24  41  37 FOBS=   41.7 SIGMA=  4.3 PHAS= -138.2 FOM= 0.77 TEST= 0
INDE  24  41  39 FOBS=    0.0 SIGMA= 20.0 PHAS=    0.0 FOM= 0.00 TEST= 0
INDE  24  41  41 FOBS=  180.9 SIGMA=  1.1 PHAS= -132.8 FOM= 0.95 TEST= 0
INDE  24  41  43 FOBS=    0.0 SIGMA= 19.1 PHAS=    0.0 FOM= 0.00 TEST= 0
INDE  24  41  45 FOBS=   92.3 SIGMA=  1.9 PHAS=   64.4 FOM= 0.72 TEST= 0
INDE  24  41  47 FOBS=  156.8 SIGMA=  1.2 PHAS= -134.8 FOM= 0.97 TEST= 0
INDE  24  41  49 FOBS=    5.3 SIGMA= 33.8 PHAS=  -81.4 FOM= 0.06 TEST= 0
INDE  24  41  51 FOBS=   87.4 SIGMA=  2.2 PHAS= -105.6 FOM= 0.93 TEST= 0
INDE  24  41  53 FOBS=  100.6 SIGMA=  2.1 PHAS= -131.0 FOM= 0.88 TEST= 0
INDE  24  41  55 FOBS=   37.0 SIGMA=  5.7 PHAS= -102.2 FOM= 0.66 TEST= 0
INDE  24  41  57 FOBS=   57.0 SIGMA=  3.7 PHAS=  146.8 FOM= 0.62 TEST= 0
INDE  24  41  59 FOBS=   60.4 SIGMA=  3.5 PHAS=  179.5 FOM= 0.74 TEST= 0
INDE  24  41  61 FOBS=   46.6 SIGMA=  5.5 PHAS= -115.7 FOM= 0.81 TEST= 0
INDE  24  42  24 FOBS=  195.3 SIGMA=  1.0 PHAS=  107.8 FOM= 0.97 TEST= 0
INDE  24  42  26 FOBS=   33.2 SIGMA=  6.4 PHAS=  -45.6 FOM= 0.20 TEST= 1
INDE  24  42  28 FOBS=    0.0 SIGMA= 18.8 PHAS=    0.0 FOM= 0.00 TEST= 0
INDE  24  42  30 FOBS=  158.2 SIGMA=  1.3 PHAS=   53.0 FOM= 0.92 TEST= 0
INDE  24  42  32 FOBS=  101.2 SIGMA=  1.8 PHAS= -111.7 FOM= 0.85 TEST= 0
INDE  24  42  34 FOBS=   61.8 SIGMA=  3.0 PHAS= -161.1 FOM= 0.86 TEST= 0
INDE  24  42  36 FOBS=    0.0 SIGMA= 21.3 PHAS=    0.0 FOM= 0.00 TEST= 0
INDE  24  42  38 FOBS=   40.1 SIGMA=  5.3 PHAS=    1.1 FOM= 0.28 TEST= 0
INDE  24  42  40 FOBS=   83.9 SIGMA=  2.2 PHAS=   40.9 FOM= 0.15 TEST= 0
INDE  24  42  42 FOBS=   86.4 SIGMA=  2.1 PHAS=  144.3 FOM= 0.89 TEST= 0
INDE  24  42  44 FOBS=   76.4 SIGMA=  2.3 PHAS=  -14.3 FOM= 0.82 TEST= 0
INDE  24  42  46 FOBS=   58.9 SIGMA=  3.1 PHAS=   78.7 FOM= 0.77 TEST= 0
INDE  24  42  48 FOBS=   74.6 SIGMA=  2.4 PHAS=   62.1 FOM= 0.94 TEST= 0
INDE  24  42  50 FOBS=   84.7 SIGMA=  2.1 PHAS=   62.6 FOM= 0.92 TEST= 0
INDE  24  42  52 FOBS=   89.2 SIGMA=  2.4 PHAS=  124.2 FOM= 0.93 TEST= 0
INDE  24  42  54 FOBS=  120.4 SIGMA=  1.8 PHAS=  168.6 FOM= 0.85 TEST= 0
INDE  24  42  56 FOBS=   74.4 SIGMA=  2.9 PHAS=  112.1 FOM= 0.95 TEST= 0
INDE  24  42  58 FOBS=   78.1 SIGMA=  2.7 PHAS=  134.8 FOM= 0.88 TEST= 0
INDE  24  42  60 FOBS=    0.0 SIGMA= 22.7 PHAS=    0.0 FOM= 0.00 TEST= 0
INDE  24  43  25 FOBS=   91.5 SIGMA=  2.2 PHAS=   72.2 FOM= 0.92 TEST= 0
INDE  24  43  27 FOBS=  113.3 SIGMA=  1.8 PHAS=  -68.5 FOM= 0.83 TEST= 0
INDE  24  43  29 FOBS=   57.4 SIGMA=  3.1 PHAS=  -78.0 FOM= 0.75 TEST= 0
INDE  24  43  31 FOBS=  105.7 SIGMA=  1.7 PHAS=  -91.1 FOM= 0.90 TEST= 0
INDE  24  43  33 FOBS=    0.0 SIGMA= 19.3 PHAS=    0.0 FOM= 0.00 TEST= 0
INDE  24  43  35 FOBS=   73.1 SIGMA=  2.8 PHAS= -110.1 FOM= 0.72 TEST= 0
INDE  24  43  37 FOBS=   46.1 SIGMA=  3.9 PHAS=  -82.1 FOM= 0.56 TEST= 0
INDE  24  43  39 FOBS=   29.7 SIGMA=  6.7 PHAS=  122.9 FOM= 0.32 TEST= 0
INDE  24  43  41 FOBS=   40.6 SIGMA=  4.6 PHAS=   42.0 FOM= 0.29 TEST= 0
INDE  24  43  43 FOBS=   43.9 SIGMA=  4.5 PHAS=  159.8 FOM= 0.60 TEST= 1
INDE  24  43  45 FOBS=    9.6 SIGMA= 19.2 PHAS=  -63.9 FOM= 0.17 TEST= 0
INDE  24  43  47 FOBS=  100.5 SIGMA=  1.8 PHAS=  -87.1 FOM= 0.91 TEST= 0
INDE  24  43  49 FOBS=   82.0 SIGMA=  2.2 PHAS=   -1.3 FOM= 0.63 TEST= 1
INDE  24  43  51 FOBS=   73.1 SIGMA=  2.6 PHAS=  -71.6 FOM= 0.79 TEST= 0
INDE  24  43  53 FOBS=  107.7 SIGMA=  2.0 PHAS=  125.1 FOM= 0.32 TEST= 1
INDE  24  43  55 FOBS=  114.1 SIGMA=  1.9 PHAS=   26.9 FOM= 0.94 TEST= 0
INDE  24  43  57 FOBS=   33.9 SIGMA=  6.6 PHAS=    6.4 FOM= 0.68 TEST= 0
INDE  24  43  59 FOBS=   41.0 SIGMA=  6.3 PHAS=    4.0 FOM= 0.75 TEST= 0
INDE  24  44  24 FOBS=  102.5 SIGMA=  1.7 PHAS=  -17.8 FOM= 0.87 TEST= 0
INDE  24  44  26 FOBS=   67.5 SIGMA=  2.9 PHAS=  -86.2 FOM= 0.71 TEST= 0
INDE  24  44  28 FOBS=   50.2 SIGMA=  3.5 PHAS=  144.6 FOM= 0.89 TEST= 1
INDE  24  44  30 FOBS=  167.2 SIGMA=  1.1 PHAS=  178.5 FOM= 0.96 TEST= 0
INDE  24  44  32 FOBS=   28.4 SIGMA=  8.7 PHAS=  -38.0 FOM= 0.18 TEST= 0
INDE  24  44  34 FOBS=   67.6 SIGMA=  3.0 PHAS=  180.0 FOM= 0.88 TEST= 0
INDE  24  44  36 FOBS=   16.4 SIGMA= 12.9 PHAS=  -98.0 FOM= 0.49 TEST= 0
INDE  24  44  38 FOBS=   33.8 SIGMA=  5.6 PHAS= -102.3 FOM= 0.22 TEST= 0
INDE  24  44  40 FOBS=   84.6 SIGMA=  2.1 PHAS= -158.8 FOM= 0.43 TEST= 0
INDE  24  44  42 FOBS=   72.9 SIGMA=  2.5 PHAS= -171.4 FOM= 0.84 TEST= 0
INDE  24  44  44 FOBS=   38.2 SIGMA=  4.6 PHAS=  -75.9 FOM= 0.18 TEST= 0
INDE  24  44  46 FOBS=   56.6 SIGMA=  3.1 PHAS=  125.8 FOM= 0.34 TEST= 0
```

*FIG. 12A - 491*

```
INDE 24 44 48 FOBS=   26.9 SIGMA=  7.0 PHAS=    0.1 FOM= 0.40 TEST= 0
INDE 24 44 50 FOBS=   30.1 SIGMA=  6.5 PHAS=   62.0 FOM= 0.47 TEST= 0
INDE 24 44 52 FOBS=   73.0 SIGMA=  2.6 PHAS=  173.7 FOM= 0.83 TEST= 0
INDE 24 44 54 FOBS=   85.8 SIGMA=  2.5 PHAS=  137.6 FOM= 0.81 TEST= 0
INDE 24 44 56 FOBS=   73.1 SIGMA=  3.0 PHAS=  -14.8 FOM= 0.91 TEST= 0
INDE 24 44 58 FOBS=   52.2 SIGMA=  5.7 PHAS= -113.2 FOM= 0.85 TEST= 0
INDE 24 45 25 FOBS=   35.7 SIGMA=  5.4 PHAS=  113.6 FOM= 0.44 TEST= 0
INDE 24 45 27 FOBS=   87.1 SIGMA=  2.3 PHAS=  -68.3 FOM= 0.93 TEST= 0
INDE 24 45 29 FOBS=   61.6 SIGMA=  2.9 PHAS=  -40.6 FOM= 0.55 TEST= 0
INDE 24 45 31 FOBS=   65.5 SIGMA=  3.0 PHAS=  -42.1 FOM= 0.61 TEST= 0
INDE 24 45 33 FOBS=   34.5 SIGMA=  6.1 PHAS=  -68.1 FOM= 0.35 TEST= 0
INDE 24 45 35 FOBS=   49.8 SIGMA=  4.0 PHAS= -109.0 FOM= 0.72 TEST= 0
INDE 24 45 37 FOBS=  101.0 SIGMA=  2.0 PHAS=  -97.3 FOM= 0.83 TEST= 0
INDE 24 45 39 FOBS=   82.1 SIGMA=  2.2 PHAS= -175.0 FOM= 0.91 TEST= 0
INDE 24 45 41 FOBS=   53.7 SIGMA=  3.4 PHAS=   87.9 FOM= 0.77 TEST= 0
INDE 24 45 43 FOBS=   72.4 SIGMA=  2.5 PHAS= -165.9 FOM= 0.83 TEST= 0
INDE 24 45 45 FOBS=    0.0 SIGMA= 18.7 PHAS=    0.0 FOM= 0.00 TEST= 0
INDE 24 45 47 FOBS=   38.0 SIGMA=  4.6 PHAS=  -88.6 FOM= 0.56 TEST= 0
INDE 24 45 49 FOBS=   82.5 SIGMA=  2.2 PHAS= -117.3 FOM= 0.88 TEST= 0
INDE 24 45 51 FOBS=    0.0 SIGMA= 20.9 PHAS=    0.0 FOM= 0.00 TEST= 1
INDE 24 45 53 FOBS=   60.0 SIGMA=  3.2 PHAS=   15.1 FOM= 0.85 TEST= 0
INDE 24 45 55 FOBS=    0.0 SIGMA= 20.6 PHAS=    0.0 FOM= 0.00 TEST= 0
INDE 24 45 57 FOBS=   79.7 SIGMA=  3.8 PHAS= -123.5 FOM= 0.95 TEST= 0
INDE 24 46 24 FOBS=  160.7 SIGMA=  1.1 PHAS=    3.4 FOM= 0.95 TEST= 0
INDE 24 46 26 FOBS=   54.6 SIGMA=  3.6 PHAS=   22.7 FOM= 0.88 TEST= 0
INDE 24 46 28 FOBS=    0.0 SIGMA= 21.1 PHAS=    0.0 FOM= 0.00 TEST= 0
INDE 24 46 30 FOBS=  124.3 SIGMA=  1.6 PHAS= -150.1 FOM= 0.94 TEST= 0
INDE 24 46 32 FOBS=  129.9 SIGMA=  1.6 PHAS=  163.2 FOM= 0.95 TEST= 0
INDE 24 46 34 FOBS=   38.8 SIGMA=  5.1 PHAS=  157.5 FOM= 0.40 TEST= 0
INDE 24 46 36 FOBS=  120.4 SIGMA=  1.7 PHAS= -129.0 FOM= 0.93 TEST= 0
INDE 24 46 38 FOBS=  159.1 SIGMA=  1.4 PHAS= -171.6 FOM= 0.95 TEST= 0
INDE 24 46 40 FOBS=   74.6 SIGMA=  2.4 PHAS=  -47.2 FOM= 0.81 TEST= 0
INDE 24 46 42 FOBS=   71.5 SIGMA=  2.5 PHAS= -154.4 FOM= 0.28 TEST= 0
INDE 24 46 44 FOBS=   10.0 SIGMA= 18.5 PHAS=   71.5 FOM= 0.09 TEST= 0
INDE 24 46 46 FOBS=   70.8 SIGMA=  2.5 PHAS=   35.2 FOM= 0.85 TEST= 0
INDE 24 46 48 FOBS=    0.0 SIGMA= 19.9 PHAS=    0.0 FOM= 0.00 TEST= 1
INDE 24 46 50 FOBS=    0.0 SIGMA= 20.8 PHAS=    0.0 FOM= 0.00 TEST= 0
INDE 24 46 52 FOBS=   35.4 SIGMA=  5.9 PHAS=  -83.5 FOM= 0.50 TEST= 0
INDE 24 46 54 FOBS=    0.0 SIGMA= 20.9 PHAS=    0.0 FOM= 0.00 TEST= 0
INDE 24 46 56 FOBS=   43.7 SIGMA=  6.7 PHAS=  111.1 FOM= 0.71 TEST= 0
INDE 24 47 25 FOBS=  109.6 SIGMA=  1.7 PHAS=  -92.6 FOM= 0.82 TEST= 0
INDE 24 47 27 FOBS=  174.7 SIGMA=  1.4 PHAS= -114.5 FOM= 0.95 TEST= 0
INDE 24 47 29 FOBS=   62.6 SIGMA=  3.6 PHAS=  -95.3 FOM= 0.52 TEST= 0
INDE 24 47 31 FOBS=   74.4 SIGMA=  2.7 PHAS=  113.2 FOM= 0.60 TEST= 0
INDE 24 47 33 FOBS=   45.9 SIGMA=  4.3 PHAS=   24.2 FOM= 0.53 TEST= 0
INDE 24 47 35 FOBS=   80.8 SIGMA=  2.5 PHAS= -138.6 FOM= 0.91 TEST= 0
INDE 24 47 37 FOBS=   67.2 SIGMA=  3.0 PHAS=   44.9 FOM= 0.30 TEST= 1
INDE 24 47 39 FOBS=  161.9 SIGMA=  1.2 PHAS=  175.0 FOM= 0.96 TEST= 0
INDE 24 47 41 FOBS=   79.2 SIGMA=  2.3 PHAS=  120.8 FOM= 0.83 TEST= 0
INDE 24 47 43 FOBS=   60.7 SIGMA=  3.0 PHAS= -143.4 FOM= 0.76 TEST= 0
INDE 24 47 45 FOBS=    0.0 SIGMA= 19.5 PHAS=    0.0 FOM= 0.00 TEST= 0
INDE 24 47 47 FOBS=   44.1 SIGMA=  4.8 PHAS=  -14.3 FOM= 0.69 TEST= 0
INDE 24 47 49 FOBS=   91.5 SIGMA=  2.0 PHAS= -124.8 FOM= 0.89 TEST= 0
INDE 24 47 51 FOBS=   40.6 SIGMA=  5.1 PHAS=  -57.1 FOM= 0.46 TEST= 0
INDE 24 47 53 FOBS=   45.2 SIGMA=  4.6 PHAS=  -90.4 FOM= 0.73 TEST= 0
INDE 24 47 55 FOBS=    0.0 SIGMA= 24.4 PHAS=    0.0 FOM= 0.00 TEST= 0
INDE 24 47 57 FOBS=   35.5 SIGMA=  9.9 PHAS=  -96.8 FOM= 0.65 TEST= 0
INDE 24 48 24 FOBS=   67.3 SIGMA=  2.5 PHAS=   71.0 FOM= 0.67 TEST= 0
INDE 24 48 26 FOBS=  146.0 SIGMA=  1.5 PHAS=   38.8 FOM= 0.93 TEST= 0
INDE 24 48 28 FOBS=   64.8 SIGMA=  3.5 PHAS= -156.7 FOM= 0.86 TEST= 0
INDE 24 48 30 FOBS=   25.0 SIGMA=  8.9 PHAS=  101.6 FOM= 0.32 TEST= 0
INDE 24 48 32 FOBS=  148.7 SIGMA=  1.4 PHAS= -173.9 FOM= 0.95 TEST= 0
INDE 24 48 34 FOBS=   74.7 SIGMA=  2.7 PHAS=  171.6 FOM= 0.86 TEST= 0
INDE 24 48 36 FOBS=    0.0 SIGMA= 20.6 PHAS=    0.0 FOM= 0.00 TEST= 0
INDE 24 48 38 FOBS=   22.5 SIGMA=  9.4 PHAS=   32.8 FOM= 0.29 TEST= 0
INDE 24 48 40 FOBS=   47.7 SIGMA=  3.9 PHAS=   13.3 FOM= 0.69 TEST= 0
INDE 24 48 42 FOBS=   74.6 SIGMA=  2.4 PHAS=    5.1 FOM= 0.68 TEST= 0
INDE 24 48 44 FOBS=    0.0 SIGMA= 19.8 PHAS=    0.0 FOM= 0.00 TEST= 0
INDE 24 48 46 FOBS=   48.6 SIGMA=  4.0 PHAS= -170.2 FOM= 0.09 TEST= 0
INDE 24 48 48 FOBS=   29.0 SIGMA=  7.6 PHAS= -145.9 FOM= 0.39 TEST= 0
```

*FIG. 12A - 492*

```
INDE  24  48  50  FOBS=   60.1  SIGMA=   3.4  PHAS=  -154.7  FOM=  0.09  TEST= 1
INDE  24  48  52  FOBS=   63.9  SIGMA=   3.3  PHAS=  -180.0  FOM=  0.90  TEST= 0
INDE  24  48  54  FOBS=   86.3  SIGMA=   2.5  PHAS=   132.5  FOM=  0.93  TEST= 0
INDE  24  48  56  FOBS=    0.0  SIGMA=  26.3  PHAS=     0.0  FOM=  0.00  TEST= 0
INDE  24  49  25  FOBS=  290.5  SIGMA=   0.8  PHAS=   -53.0  FOM=  0.98  TEST= 0
INDE  24  49  27  FOBS=  195.3  SIGMA=   1.1  PHAS=   -92.7  FOM=  0.80  TEST= 1
INDE  24  49  29  FOBS=    0.0  SIGMA=  22.2  PHAS=     0.0  FOM=  0.00  TEST= 0
INDE  24  49  31  FOBS=  146.0  SIGMA=   1.4  PHAS=    46.0  FOM=  0.95  TEST= 0
INDE  24  49  33  FOBS=   67.2  SIGMA=   2.9  PHAS=   129.5  FOM=  0.93  TEST= 0
INDE  24  49  35  FOBS=   75.7  SIGMA=   2.6  PHAS=   127.9  FOM=  0.79  TEST= 0
INDE  24  49  37  FOBS=   45.5  SIGMA=   4.4  PHAS=   -27.7  FOM=  0.50  TEST= 0
INDE  24  49  39  FOBS=  119.3  SIGMA=   1.7  PHAS=   -70.9  FOM=  0.09  TEST= 1
INDE  24  49  41  FOBS=   51.7  SIGMA=   3.5  PHAS=   -88.6  FOM=  0.43  TEST= 0
INDE  24  49  43  FOBS=   19.0  SIGMA=   9.9  PHAS=   -89.7  FOM=  0.24  TEST= 0
INDE  24  49  45  FOBS=   48.0  SIGMA=   4.0  PHAS=   117.8  FOM=  0.70  TEST= 0
INDE  24  49  47  FOBS=   88.5  SIGMA=   2.4  PHAS=    77.8  FOM=  0.91  TEST= 0
INDE  24  49  49  FOBS=   28.5  SIGMA=   7.3  PHAS=  -123.5  FOM=  0.42  TEST= 0
INDE  24  49  51  FOBS=   24.9  SIGMA=  10.3  PHAS=   -36.6  FOM=  0.53  TEST= 0
INDE  24  49  53  FOBS=  139.6  SIGMA=   1.6  PHAS=    46.1  FOM=  0.96  TEST= 0
INDE  24  49  55  FOBS=   75.1  SIGMA=   3.7  PHAS=    60.7  FOM=  0.07  TEST= 1
INDE  24  50  24  FOBS=  156.4  SIGMA=   1.1  PHAS=  -126.4  FOM=  0.96  TEST= 0
INDE  24  50  26  FOBS=  120.3  SIGMA=   1.7  PHAS=   163.1  FOM=  0.92  TEST= 0
INDE  24  50  28  FOBS=   90.7  SIGMA=   2.2  PHAS=  -141.1  FOM=  0.95  TEST= 0
INDE  24  50  30  FOBS=  112.1  SIGMA=   2.1  PHAS=    16.3  FOM=  0.84  TEST= 0
INDE  24  50  32  FOBS=    0.0  SIGMA=  22.3  PHAS=     0.0  FOM=  0.00  TEST= 0
INDE  24  50  34  FOBS=   17.5  SIGMA=  12.7  PHAS=    87.1  FOM=  0.18  TEST= 0
INDE  24  50  36  FOBS=   77.7  SIGMA=   2.5  PHAS=   -23.1  FOM=  0.86  TEST= 0
INDE  24  50  38  FOBS=   31.0  SIGMA=   6.4  PHAS=   103.1  FOM=  0.28  TEST= 0
INDE  24  50  40  FOBS=    0.0  SIGMA=  20.5  PHAS=     0.0  FOM=  0.00  TEST= 0
INDE  24  50  42  FOBS=  126.1  SIGMA=   1.6  PHAS=   -38.2  FOM=  0.94  TEST= 0
INDE  24  50  44  FOBS=   49.1  SIGMA=   4.3  PHAS=  -135.2  FOM=  0.55  TEST= 0
INDE  24  50  46  FOBS=   84.7  SIGMA=   2.5  PHAS=     1.9  FOM=  0.86  TEST= 0
INDE  24  50  48  FOBS=   44.7  SIGMA=   4.9  PHAS=   118.2  FOM=  0.50  TEST= 0
INDE  24  50  50  FOBS=   63.6  SIGMA=   3.6  PHAS=   157.0  FOM=  0.93  TEST= 0
INDE  24  50  52  FOBS=   34.9  SIGMA=   7.7  PHAS=    -0.1  FOM=  0.62  TEST= 0
INDE  24  50  54  FOBS=   45.5  SIGMA=   7.0  PHAS=     3.9  FOM=  0.65  TEST= 0
INDE  24  51  25  FOBS=    0.0  SIGMA=  18.3  PHAS=     0.0  FOM=  0.00  TEST= 0
INDE  24  51  27  FOBS=    0.0  SIGMA=  19.3  PHAS=     0.0  FOM=  0.00  TEST= 1
INDE  24  51  29  FOBS=   26.4  SIGMA=   7.6  PHAS=   170.6  FOM=  0.37  TEST= 0
INDE  24  51  31  FOBS=   67.1  SIGMA=   3.3  PHAS=    48.8  FOM=  0.85  TEST= 0
INDE  24  51  33  FOBS=   71.7  SIGMA=   2.7  PHAS=   132.8  FOM=  0.81  TEST= 0
INDE  24  51  35  FOBS=    0.0  SIGMA=  20.2  PHAS=     0.0  FOM=  0.00  TEST= 0
INDE  24  51  37  FOBS=   50.1  SIGMA=   3.9  PHAS=   -26.4  FOM=  0.47  TEST= 0
INDE  24  51  39  FOBS=  101.2  SIGMA=   2.2  PHAS=   162.2  FOM=  0.87  TEST= 0
INDE  24  51  41  FOBS=   96.7  SIGMA=   2.0  PHAS=  -149.1  FOM=  0.86  TEST= 0
INDE  24  51  43  FOBS=   34.3  SIGMA=   6.5  PHAS=   153.8  FOM=  0.21  TEST= 0
INDE  24  51  45  FOBS=   78.1  SIGMA=   3.0  PHAS=    67.5  FOM=  0.25  TEST= 1
INDE  24  51  47  FOBS=   68.6  SIGMA=   3.4  PHAS=     3.2  FOM=  0.92  TEST= 0
INDE  24  51  49  FOBS=   98.6  SIGMA=   2.4  PHAS=    38.9  FOM=  0.91  TEST= 0
INDE  24  51  51  FOBS=    0.0  SIGMA=  22.6  PHAS=     0.0  FOM=  0.00  TEST= 0
INDE  24  51  53  FOBS=    0.0  SIGMA=  25.4  PHAS=     0.0  FOM=  0.00  TEST= 0
INDE  24  52  24  FOBS=    7.4  SIGMA=  27.5  PHAS=    51.8  FOM=  0.07  TEST= 0
INDE  24  52  26  FOBS=   24.3  SIGMA=   7.9  PHAS=    79.4  FOM=  0.24  TEST= 0
INDE  24  52  28  FOBS=   55.2  SIGMA=   3.4  PHAS=    57.9  FOM=  0.83  TEST= 0
INDE  24  52  30  FOBS=   25.9  SIGMA=   7.8  PHAS=   -42.8  FOM=  0.43  TEST= 0
INDE  24  52  32  FOBS=   94.3  SIGMA=   2.3  PHAS=    77.7  FOM=  0.91  TEST= 0
INDE  24  52  34  FOBS=   18.9  SIGMA=  10.9  PHAS=    73.0  FOM=  0.01  TEST= 1
INDE  24  52  36  FOBS=   83.5  SIGMA=   2.6  PHAS=   -37.4  FOM=  0.83  TEST= 0
INDE  24  52  38  FOBS=   46.0  SIGMA=   5.0  PHAS=   120.2  FOM=  0.33  TEST= 0
INDE  24  52  40  FOBS=  116.4  SIGMA=   2.3  PHAS=    63.8  FOM=  0.94  TEST= 0
INDE  24  52  42  FOBS=  126.5  SIGMA=   1.9  PHAS=   -21.3  FOM=  0.81  TEST= 0
INDE  24  52  44  FOBS=   37.8  SIGMA=   6.1  PHAS=   -90.2  FOM=  0.76  TEST= 0
INDE  24  52  46  FOBS=   71.4  SIGMA=   3.6  PHAS=  -107.0  FOM=  0.86  TEST= 0
INDE  24  52  48  FOBS=  109.7  SIGMA=   2.4  PHAS=  -100.3  FOM=  0.94  TEST= 0
INDE  24  52  50  FOBS=   79.3  SIGMA=   3.3  PHAS=   161.8  FOM=  0.93  TEST= 0
INDE  24  52  52  FOBS=   27.0  SIGMA=  18.2  PHAS=    80.0  FOM=  0.39  TEST= 0
INDE  24  53  25  FOBS=    0.0  SIGMA=  17.9  PHAS=     0.0  FOM=  0.00  TEST= 1
INDE  24  53  27  FOBS=  112.0  SIGMA=   1.7  PHAS=    -8.1  FOM=  0.92  TEST= 0
INDE  24  53  29  FOBS=   33.7  SIGMA=   5.6  PHAS=    59.5  FOM=  0.42  TEST= 0
INDE  24  53  31  FOBS=   11.7  SIGMA=  17.2  PHAS=  -111.4  FOM=  0.14  TEST= 0
```

*FIG. 12A - 493*

```
INDE 24 53 33 FOBS=    0.0 SIGMA= 21.9 PHAS=    0.0 FOM= 0.00 TEST= 0
INDE 24 53 35 FOBS=   19.8 SIGMA= 12.2 PHAS=  159.4 FOM= 0.05 TEST= 0
INDE 24 53 37 FOBS=    0.0 SIGMA= 23.7 PHAS=    0.0 FOM= 0.00 TEST= 1
INDE 24 53 39 FOBS=   45.1 SIGMA=  5.8 PHAS=  178.0 FOM= 0.21 TEST= 0
INDE 24 53 41 FOBS=   63.6 SIGMA=  4.8 PHAS=  -90.4 FOM= 0.84 TEST= 0
INDE 24 53 43 FOBS=   81.0 SIGMA=  3.2 PHAS=  101.3 FOM= 0.83 TEST= 0
INDE 24 53 45 FOBS=   71.6 SIGMA=  3.6 PHAS=  144.2 FOM= 0.88 TEST= 0
INDE 24 53 47 FOBS=    0.0 SIGMA= 23.6 PHAS=    0.0 FOM= 0.00 TEST= 0
INDE 24 53 49 FOBS=   87.0 SIGMA=  3.1 PHAS=   43.5 FOM= 0.93 TEST= 0
INDE 24 53 51 FOBS=   22.0 SIGMA= 20.6 PHAS=   36.4 FOM= 0.57 TEST= 0
INDE 24 54 24 FOBS=  152.5 SIGMA=  1.2 PHAS=   98.6 FOM= 0.97 TEST= 0
INDE 24 54 26 FOBS=    0.0 SIGMA= 19.0 PHAS=    0.0 FOM= 0.00 TEST= 1
INDE 24 54 28 FOBS=   51.9 SIGMA=  3.9 PHAS=    9.1 FOM= 0.74 TEST= 0
INDE 24 54 30 FOBS=   68.9 SIGMA=  3.2 PHAS= -163.2 FOM= 0.77 TEST= 0
INDE 24 54 32 FOBS=   11.2 SIGMA= 24.0 PHAS=  128.4 FOM= 0.14 TEST= 0
INDE 24 54 34 FOBS=    0.0 SIGMA= 23.7 PHAS=    0.0 FOM= 0.00 TEST= 0
INDE 24 54 36 FOBS=    0.0 SIGMA= 23.8 PHAS=    0.0 FOM= 0.00 TEST= 0
INDE 24 54 38 FOBS=    0.0 SIGMA= 24.1 PHAS=    0.0 FOM= 0.00 TEST= 0
INDE 24 54 40 FOBS=   55.4 SIGMA=  5.4 PHAS=   94.5 FOM= 0.76 TEST= 0
INDE 24 54 42 FOBS=   63.9 SIGMA=  4.3 PHAS=  -43.3 FOM= 0.85 TEST= 0
INDE 24 54 44 FOBS=   88.3 SIGMA=  2.9 PHAS=   27.9 FOM= 0.90 TEST= 0
INDE 24 54 46 FOBS=    0.0 SIGMA= 22.6 PHAS=    0.0 FOM= 0.00 TEST= 1
INDE 24 54 48 FOBS=   49.1 SIGMA=  5.4 PHAS=  143.0 FOM= 0.32 TEST= 0
INDE 24 54 50 FOBS=   89.2 SIGMA=  3.9 PHAS= -107.4 FOM= 0.31 TEST= 1
INDE 24 55 25 FOBS=   47.2 SIGMA=  4.1 PHAS=   29.2 FOM= 0.57 TEST= 0
INDE 24 55 27 FOBS=   83.9 SIGMA=  2.9 PHAS=   -5.1 FOM= 0.91 TEST= 0
INDE 24 55 29 FOBS=   93.4 SIGMA=  2.6 PHAS=   48.3 FOM= 0.93 TEST= 0
INDE 24 55 31 FOBS=   54.7 SIGMA=  5.6 PHAS= -154.2 FOM= 0.85 TEST= 0
INDE 24 55 33 FOBS=   99.3 SIGMA=  2.9 PHAS=   -0.5 FOM= 0.75 TEST= 0
INDE 24 55 35 FOBS=   19.2 SIGMA= 14.8 PHAS= -130.4 FOM= 0.40 TEST= 0
INDE 24 55 37 FOBS=    0.0 SIGMA= 24.0 PHAS=    0.0 FOM= 0.00 TEST= 1
INDE 24 55 39 FOBS=   17.2 SIGMA= 17.4 PHAS= -113.5 FOM= 0.00 TEST= 1
INDE 24 55 41 FOBS=   14.6 SIGMA= 20.7 PHAS=   51.5 FOM= 0.22 TEST= 0
INDE 24 55 43 FOBS=   31.1 SIGMA=  9.1 PHAS=  -59.2 FOM= 0.06 TEST= 1
INDE 24 55 45 FOBS=    0.0 SIGMA= 27.1 PHAS=    0.0 FOM= 0.00 TEST= 0
INDE 24 55 47 FOBS=    0.0 SIGMA= 23.7 PHAS=    0.0 FOM= 0.00 TEST= 0
INDE 24 55 49 FOBS=   49.4 SIGMA=  7.0 PHAS=   72.3 FOM= 0.80 TEST= 0
INDE 24 56 24 FOBS=  196.5 SIGMA=  1.3 PHAS=   90.0 FOM= 0.97 TEST= 0
INDE 24 56 26 FOBS=  101.6 SIGMA=  2.3 PHAS= -157.2 FOM= 0.94 TEST= 0
INDE 24 56 28 FOBS=  153.2 SIGMA=  1.8 PHAS=  -79.9 FOM= 0.96 TEST= 0
INDE 24 56 30 FOBS=   42.6 SIGMA=  7.4 PHAS=  152.8 FOM= 0.18 TEST= 0
INDE 24 56 32 FOBS=    0.0 SIGMA= 23.2 PHAS=    0.0 FOM= 0.00 TEST= 1
INDE 24 56 34 FOBS=   92.2 SIGMA=  2.5 PHAS=  178.3 FOM= 0.84 TEST= 0
INDE 24 56 36 FOBS=   12.7 SIGMA= 22.5 PHAS=  147.1 FOM= 0.26 TEST= 0
INDE 24 56 38 FOBS=    0.0 SIGMA= 25.8 PHAS=    0.0 FOM= 0.00 TEST= 0
INDE 24 56 40 FOBS=    0.0 SIGMA= 26.3 PHAS=    0.0 FOM= 0.00 TEST= 0
INDE 24 56 42 FOBS=   42.1 SIGMA=  7.4 PHAS= -104.1 FOM= 0.62 TEST= 0
INDE 24 56 44 FOBS=   46.4 SIGMA=  5.6 PHAS=   25.5 FOM= 0.88 TEST= 0
INDE 24 56 46 FOBS=   79.4 SIGMA=  3.4 PHAS=   15.6 FOM= 0.69 TEST= 0
INDE 24 56 48 FOBS=   41.8 SIGMA=  8.1 PHAS=  134.8 FOM= 0.74 TEST= 0
INDE 24 57 25 FOBS=  118.6 SIGMA=  2.0 PHAS=   43.6 FOM= 0.95 TEST= 0
INDE 24 57 27 FOBS=  151.1 SIGMA=  1.9 PHAS=  103.8 FOM= 0.96 TEST= 0
INDE 24 57 29 FOBS=  130.1 SIGMA=  2.2 PHAS=   97.0 FOM= 0.94 TEST= 0
INDE 24 57 31 FOBS=    0.0 SIGMA= 24.7 PHAS=    0.0 FOM= 0.00 TEST= 0
INDE 24 57 33 FOBS=   31.7 SIGMA=  8.7 PHAS=  -82.9 FOM= 0.73 TEST= 0
INDE 24 57 35 FOBS=   73.5 SIGMA=  3.2 PHAS=  146.6 FOM= 0.85 TEST= 0
INDE 24 57 37 FOBS=   47.5 SIGMA=  6.2 PHAS=   20.3 FOM= 0.78 TEST= 0
INDE 24 57 39 FOBS=   44.5 SIGMA=  6.8 PHAS=  -39.3 FOM= 0.28 TEST= 1
INDE 24 57 41 FOBS=   42.3 SIGMA=  7.2 PHAS=   90.0 FOM= 0.77 TEST= 0
INDE 24 57 43 FOBS=   61.0 SIGMA=  4.7 PHAS=  -57.0 FOM= 0.90 TEST= 0
INDE 24 57 45 FOBS=   77.8 SIGMA=  3.5 PHAS=  -91.8 FOM= 0.85 TEST= 0
INDE 24 57 47 FOBS=   40.7 SIGMA= 11.5 PHAS=   24.6 FOM= 0.77 TEST= 0
INDE 24 58 24 FOBS=   20.6 SIGMA= 17.5 PHAS=   38.9 FOM= 0.16 TEST= 0
INDE 24 58 26 FOBS=   77.1 SIGMA=  3.0 PHAS=  -62.5 FOM= 0.90 TEST= 0
INDE 24 58 28 FOBS=   78.8 SIGMA=  3.4 PHAS= -100.0 FOM= 0.66 TEST= 0
INDE 24 58 30 FOBS=    0.0 SIGMA= 22.9 PHAS=    0.0 FOM= 0.00 TEST= 0
INDE 24 58 32 FOBS=    0.0 SIGMA= 23.1 PHAS=    0.0 FOM= 0.00 TEST= 1
INDE 24 58 34 FOBS=  109.0 SIGMA=  2.7 PHAS=  141.1 FOM= 0.95 TEST= 0
INDE 24 58 36 FOBS=   31.9 SIGMA=  7.3 PHAS=  159.6 FOM= 0.31 TEST= 0
INDE 24 58 38 FOBS=   73.6 SIGMA=  4.1 PHAS= -177.6 FOM= 0.27 TEST= 1
```

*FIG. 12A - 494*

```
INDE 24 58 40 FOBS=   0.0 SIGMA= 24.5 PHAS=   0.0 FOM= 0.00 TEST= 0
INDE 24 58 42 FOBS=  88.2 SIGMA=  3.7 PHAS=-132.9 FOM= 0.91 TEST= 0
INDE 24 58 44 FOBS=  41.7 SIGMA=  7.0 PHAS= 158.1 FOM= 0.33 TEST= 0
INDE 24 59 25 FOBS=  52.4 SIGMA=  4.3 PHAS=  24.3 FOM= 0.71 TEST= 0
INDE 24 59 27 FOBS= 106.6 SIGMA=  2.2 PHAS= 126.9 FOM= 0.93 TEST= 0
INDE 24 59 29 FOBS=  40.6 SIGMA=  6.5 PHAS= 118.3 FOM= 0.49 TEST= 0
INDE 24 59 31 FOBS=  29.2 SIGMA= 10.7 PHAS= 129.3 FOM= 0.34 TEST= 0
INDE 24 59 33 FOBS=  63.2 SIGMA=  4.4 PHAS=-101.7 FOM= 0.34 TEST= 0
INDE 24 59 35 FOBS=  64.9 SIGMA=  4.4 PHAS=  76.9 FOM= 0.88 TEST= 0
INDE 24 59 37 FOBS=  63.1 SIGMA=  3.8 PHAS= 112.1 FOM= 0.04 TEST= 1
INDE 24 59 39 FOBS=  41.2 SIGMA=  8.7 PHAS= -12.7 FOM= 0.08 TEST= 0
INDE 24 59 41 FOBS= 131.9 SIGMA=  2.5 PHAS=-110.6 FOM= 0.01 TEST= 1
INDE 24 59 43 FOBS=  49.6 SIGMA=  9.3 PHAS= 143.9 FOM= 0.36 TEST= 0
INDE 24 60 24 FOBS= 124.6 SIGMA=  2.5 PHAS=  11.0 FOM= 0.93 TEST= 0
INDE 24 60 26 FOBS= 130.0 SIGMA=  2.1 PHAS=-110.0 FOM= 0.86 TEST= 0
INDE 24 60 28 FOBS=  48.7 SIGMA=  5.4 PHAS=-144.3 FOM= 0.74 TEST= 0
INDE 24 60 30 FOBS=   0.0 SIGMA= 23.0 PHAS=   0.0 FOM= 0.00 TEST= 0
INDE 24 60 32 FOBS=   0.0 SIGMA= 27.3 PHAS=   0.0 FOM= 0.00 TEST= 0
INDE 24 60 34 FOBS=   0.0 SIGMA= 23.6 PHAS=   0.0 FOM= 0.00 TEST= 0
INDE 24 60 36 FOBS=  26.6 SIGMA=  9.7 PHAS=  16.1 FOM= 0.37 TEST= 0
INDE 24 60 38 FOBS=  73.7 SIGMA=  3.7 PHAS=-121.1 FOM= 0.70 TEST= 0
INDE 24 60 40 FOBS=  61.1 SIGMA=  5.1 PHAS= 101.7 FOM= 0.73 TEST= 0
INDE 24 60 42 FOBS=  38.3 SIGMA= 12.1 PHAS= -59.8 FOM= 0.54 TEST= 0
INDE 24 61 25 FOBS= 118.5 SIGMA=  2.6 PHAS= -76.2 FOM= 0.71 TEST= 0
INDE 24 61 27 FOBS=  40.0 SIGMA=  5.7 PHAS= 159.9 FOM= 0.70 TEST= 0
INDE 24 61 29 FOBS=   0.0 SIGMA= 23.0 PHAS=   0.0 FOM= 0.00 TEST= 1
INDE 24 61 31 FOBS=  71.4 SIGMA=  3.8 PHAS=  70.8 FOM= 0.92 TEST= 0
INDE 24 61 33 FOBS=   0.0 SIGMA= 25.5 PHAS=   0.0 FOM= 0.00 TEST= 0
INDE 24 61 35 FOBS=  45.2 SIGMA=  9.0 PHAS=-104.6 FOM= 0.47 TEST= 0
INDE 24 61 37 FOBS=   0.0 SIGMA= 26.0 PHAS=   0.0 FOM= 0.00 TEST= 0
INDE 24 61 39 FOBS=   0.0 SIGMA= 24.6 PHAS=   0.0 FOM= 0.00 TEST= 0
INDE 24 61 41 FOBS=   0.0 SIGMA= 30.4 PHAS=   0.0 FOM= 0.00 TEST= 0
INDE 24 62 24 FOBS=  93.0 SIGMA=  3.3 PHAS=  33.2 FOM= 0.89 TEST= 0
INDE 24 62 26 FOBS=  26.0 SIGMA= 11.5 PHAS=-145.5 FOM= 0.73 TEST= 0
INDE 24 62 28 FOBS=  48.9 SIGMA=  4.8 PHAS=-117.4 FOM= 0.81 TEST= 0
INDE 24 62 30 FOBS=  62.3 SIGMA=  4.4 PHAS= -39.4 FOM= 0.88 TEST= 0
INDE 24 62 32 FOBS=   0.0 SIGMA= 25.3 PHAS=   0.0 FOM= 0.00 TEST= 0
INDE 24 62 34 FOBS=   0.0 SIGMA= 23.6 PHAS=   0.0 FOM= 0.00 TEST= 0
INDE 24 62 36 FOBS=   0.0 SIGMA= 24.1 PHAS=   0.0 FOM= 0.00 TEST= 0
INDE 24 62 38 FOBS=  55.7 SIGMA=  4.9 PHAS=-112.4 FOM= 0.86 TEST= 0
INDE 24 62 40 FOBS=  31.0 SIGMA= 12.0 PHAS= 119.1 FOM= 0.15 TEST= 0
INDE 24 63 25 FOBS=  23.9 SIGMA= 12.4 PHAS=-121.7 FOM= 0.58 TEST= 0
INDE 24 63 27 FOBS=  80.5 SIGMA=  3.8 PHAS= 162.2 FOM= 0.94 TEST= 0
INDE 24 63 29 FOBS=  43.7 SIGMA=  7.2 PHAS=-159.5 FOM= 0.61 TEST= 0
INDE 24 63 31 FOBS=  25.1 SIGMA= 12.7 PHAS= 128.8 FOM= 0.37 TEST= 0
INDE 24 63 33 FOBS=  65.5 SIGMA=  4.3 PHAS=-137.6 FOM= 0.85 TEST= 0
INDE 24 63 35 FOBS=  60.9 SIGMA=  4.8 PHAS=-155.4 FOM= 0.47 TEST= 0
INDE 24 63 37 FOBS=  81.4 SIGMA=  3.4 PHAS=-156.6 FOM= 0.21 TEST= 1
INDE 24 64 24 FOBS=  23.3 SIGMA= 14.4 PHAS=  49.6 FOM= 0.39 TEST= 0
INDE 24 64 26 FOBS=  44.6 SIGMA=  6.7 PHAS= 134.8 FOM= 0.59 TEST= 0
INDE 24 64 28 FOBS=  76.2 SIGMA=  3.5 PHAS=  47.6 FOM= 0.90 TEST= 0
INDE 24 64 30 FOBS=  49.0 SIGMA=  6.5 PHAS=-120.3 FOM= 0.71 TEST= 0
INDE 24 64 32 FOBS=  34.9 SIGMA=  9.3 PHAS=  71.0 FOM= 0.80 TEST= 0
INDE 24 64 34 FOBS=  67.2 SIGMA=  5.1 PHAS=-164.2 FOM= 0.65 TEST= 0
INDE 24 64 36 FOBS= 132.1 SIGMA=  2.8 PHAS= 177.5 FOM= 0.95 TEST= 0
INDE 24 65 25 FOBS=  42.6 SIGMA=  7.0 PHAS=-135.5 FOM= 0.26 TEST= 0
INDE 24 65 27 FOBS=  71.2 SIGMA=  4.3 PHAS=-118.4 FOM= 0.91 TEST= 0
INDE 24 65 29 FOBS=  45.4 SIGMA=  5.9 PHAS=  73.3 FOM= 0.78 TEST= 0
INDE 24 65 31 FOBS=   0.0 SIGMA= 25.4 PHAS=   0.0 FOM= 0.00 TEST= 0
INDE 24 65 33 FOBS=  79.6 SIGMA=  4.3 PHAS=-118.8 FOM= 0.52 TEST= 1
INDE 24 65 35 FOBS=  77.2 SIGMA=  4.6 PHAS= 100.9 FOM= 0.95 TEST= 0
INDE 24 66 24 FOBS=  26.5 SIGMA= 13.4 PHAS=-173.9 FOM= 0.29 TEST= 0
INDE 24 66 26 FOBS=  20.2 SIGMA= 18.5 PHAS=  91.4 FOM= 0.26 TEST= 0
INDE 24 66 28 FOBS=  24.2 SIGMA= 15.9 PHAS=  95.9 FOM= 0.49 TEST= 0
INDE 24 66 30 FOBS=  73.8 SIGMA=  4.5 PHAS= -74.2 FOM= 0.92 TEST= 0
INDE 24 66 32 FOBS=  79.9 SIGMA=  4.3 PHAS= 156.6 FOM= 0.87 TEST= 0
INDE 24 67 25 FOBS=  43.0 SIGMA= 10.5 PHAS= -25.4 FOM= 0.63 TEST= 0
INDE 24 67 27 FOBS=  74.7 SIGMA=  6.6 PHAS=-168.5 FOM= 0.21 TEST= 1
INDE 24 67 29 FOBS=  33.4 SIGMA= 11.5 PHAS=  98.2 FOM= 0.72 TEST= 0
INDE 24 67 31 FOBS=  47.6 SIGMA=  9.0 PHAS=-118.6 FOM= 0.76 TEST= 0
```

*FIG. 12A - 495*

```
INDE  24 68 24 FOBS=   0.0 SIGMA= 30.4 PHAS=    0.0 FOM= 0.00 TEST= 0
INDE  24 68 26 FOBS=   0.0 SIGMA= 30.8 PHAS=    0.0 FOM= 0.00 TEST= 0
INDE  24 68 28 FOBS=   0.0 SIGMA= 31.5 PHAS=    0.0 FOM= 0.00 TEST= 0
INDE  24 69 25 FOBS=  36.1 SIGMA= 13.2 PHAS= -101.6 FOM= 0.77 TEST= 0
INDE  25 26 25 FOBS= 217.2 SIGMA=  0.9 PHAS=   77.7 FOM= 0.84 TEST= 0
INDE  25 26 27 FOBS=  93.5 SIGMA=  1.7 PHAS=  177.9 FOM= 0.98 TEST= 0
INDE  25 26 29 FOBS= 226.0 SIGMA=  0.8 PHAS=   -9.4 FOM= 0.95 TEST= 0
INDE  25 26 31 FOBS= 191.2 SIGMA=  1.0 PHAS=   78.2 FOM= 0.94 TEST= 0
INDE  25 26 33 FOBS= 253.0 SIGMA=  0.8 PHAS=  109.1 FOM= 0.97 TEST= 0
INDE  25 26 35 FOBS= 234.9 SIGMA=  0.8 PHAS=  -75.4 FOM= 0.82 TEST= 0
INDE  25 26 37 FOBS= 218.4 SIGMA=  0.8 PHAS=  -21.3 FOM= 0.98 TEST= 0
INDE  25 26 39 FOBS=  61.3 SIGMA=  2.7 PHAS=   47.4 FOM= 0.62 TEST= 0
INDE  25 26 41 FOBS= 177.2 SIGMA=  1.1 PHAS= -120.4 FOM= 0.93 TEST= 0
INDE  25 26 43 FOBS= 319.8 SIGMA=  0.7 PHAS= -162.3 FOM= 0.98 TEST= 0
INDE  25 26 45 FOBS=   0.0 SIGMA= 19.4 PHAS=    0.0 FOM= 0.00 TEST= 0
INDE  25 26 47 FOBS= 138.9 SIGMA=  1.4 PHAS=   78.6 FOM= 0.92 TEST= 0
INDE  25 26 49 FOBS= 117.3 SIGMA=  1.5 PHAS=   91.6 FOM= 0.98 TEST= 0
INDE  25 26 51 FOBS=  14.3 SIGMA= 13.8 PHAS=  157.0 FOM= 0.11 TEST= 0
INDE  25 26 53 FOBS=   0.0 SIGMA= 18.6 PHAS=    0.0 FOM= 0.00 TEST= 0
INDE  25 26 55 FOBS=  71.6 SIGMA=  2.8 PHAS=  160.9 FOM= 0.86 TEST= 0
INDE  25 26 57 FOBS=  97.6 SIGMA=  2.3 PHAS= -135.3 FOM= 0.80 TEST= 1
INDE  25 26 59 FOBS=  15.0 SIGMA= 19.6 PHAS=   27.7 FOM= 0.10 TEST= 0
INDE  25 26 61 FOBS= 108.5 SIGMA=  2.8 PHAS=  -98.4 FOM= 0.92 TEST= 0
INDE  25 26 63 FOBS=  30.2 SIGMA=  9.8 PHAS=   70.9 FOM= 0.09 TEST= 0
INDE  25 26 65 FOBS=   0.0 SIGMA= 27.4 PHAS=    0.0 FOM= 0.00 TEST= 0
INDE  25 26 67 FOBS=  41.3 SIGMA= 11.8 PHAS=  -80.1 FOM= 0.69 TEST= 0
INDE  25 27 26 FOBS=  37.7 SIGMA=  5.0 PHAS= -144.1 FOM= 0.93 TEST= 0
INDE  25 27 28 FOBS=  84.5 SIGMA=  2.0 PHAS=  -83.0 FOM= 0.87 TEST= 1
INDE  25 27 30 FOBS=  66.5 SIGMA=  2.8 PHAS=  -19.0 FOM= 0.86 TEST= 0
INDE  25 27 32 FOBS=  81.1 SIGMA=  2.5 PHAS=   73.7 FOM= 0.25 TEST= 0
INDE  25 27 34 FOBS= 221.3 SIGMA=  0.9 PHAS=  110.6 FOM= 0.91 TEST= 0
INDE  25 27 36 FOBS= 131.0 SIGMA=  1.3 PHAS=   49.9 FOM= 0.93 TEST= 0
INDE  25 27 38 FOBS= 219.2 SIGMA=  0.8 PHAS=  -88.0 FOM= 0.95 TEST= 0
INDE  25 27 40 FOBS=   0.0 SIGMA= 18.3 PHAS=    0.0 FOM= 0.00 TEST= 0
INDE  25 27 42 FOBS= 274.8 SIGMA=  0.8 PHAS=   76.3 FOM= 0.98 TEST= 0
INDE  25 27 44 FOBS=  34.3 SIGMA=  5.0 PHAS=  103.5 FOM= 0.55 TEST= 1
INDE  25 27 46 FOBS= 188.6 SIGMA=  1.0 PHAS=  -78.1 FOM= 0.60 TEST= 1
INDE  25 27 48 FOBS=  83.9 SIGMA=  2.1 PHAS=    2.7 FOM= 0.70 TEST= 0
INDE  25 27 50 FOBS=  75.6 SIGMA=  2.3 PHAS=  111.3 FOM= 0.70 TEST= 0
INDE  25 27 52 FOBS=   0.0 SIGMA= 19.9 PHAS=    0.0 FOM= 0.00 TEST= 0
INDE  25 27 54 FOBS=  90.9 SIGMA=  2.1 PHAS=   29.5 FOM= 0.86 TEST= 0
INDE  25 27 56 FOBS=  42.5 SIGMA=  4.7 PHAS=  112.5 FOM= 0.63 TEST= 0
INDE  25 27 58 FOBS=  36.3 SIGMA=  6.5 PHAS= -157.4 FOM= 0.56 TEST= 0
INDE  25 27 60 FOBS=   4.7 SIGMA= 63.4 PHAS=  140.6 FOM= 0.10 TEST= 0
INDE  25 27 62 FOBS=  31.8 SIGMA= 11.8 PHAS= -119.5 FOM= 0.48 TEST= 0
INDE  25 27 64 FOBS=  35.1 SIGMA= 10.6 PHAS=   34.0 FOM= 0.48 TEST= 0
INDE  25 27 66 FOBS=   7.2 SIGMA= 66.0 PHAS=  -36.2 FOM= 0.17 TEST= 0
INDE  25 27 68 FOBS=   0.0 SIGMA= 31.0 PHAS=    0.0 FOM= 0.00 TEST= 0
INDE  25 28 25 FOBS=  80.1 SIGMA=  2.3 PHAS=   50.5 FOM= 0.91 TEST= 0
INDE  25 28 27 FOBS= 347.1 SIGMA=  0.7 PHAS=  171.2 FOM= 0.97 TEST= 0
INDE  25 28 29 FOBS= 157.8 SIGMA=  1.2 PHAS=   41.7 FOM= 0.82 TEST= 0
INDE  25 28 31 FOBS= 170.1 SIGMA=  1.2 PHAS=   39.6 FOM= 0.88 TEST= 0
INDE  25 28 33 FOBS=  99.7 SIGMA=  2.0 PHAS=    5.0 FOM= 0.86 TEST= 1
INDE  25 28 35 FOBS= 275.9 SIGMA=  0.8 PHAS=   23.4 FOM= 0.98 TEST= 0
INDE  25 28 37 FOBS= 203.6 SIGMA=  0.9 PHAS=  -46.1 FOM= 0.95 TEST= 0
INDE  25 28 39 FOBS= 103.1 SIGMA=  1.6 PHAS= -163.2 FOM= 0.83 TEST= 0
INDE  25 28 41 FOBS= 119.3 SIGMA=  1.4 PHAS=  -36.4 FOM= 0.94 TEST= 0
INDE  25 28 43 FOBS=  95.9 SIGMA=  1.9 PHAS=  -26.1 FOM= 0.65 TEST= 0
INDE  25 28 45 FOBS=   0.0 SIGMA= 19.0 PHAS=    0.0 FOM= 0.00 TEST= 0
INDE  25 28 47 FOBS=  62.7 SIGMA=  2.7 PHAS= -116.0 FOM= 0.77 TEST= 0
INDE  25 28 49 FOBS= 239.2 SIGMA=  0.8 PHAS=   46.2 FOM= 0.98 TEST= 0
INDE  25 28 51 FOBS=   0.0 SIGMA= 18.2 PHAS=    0.0 FOM= 0.00 TEST= 0
INDE  25 28 53 FOBS=  78.5 SIGMA=  2.1 PHAS=  -81.7 FOM= 0.06 TEST= 1
INDE  25 28 55 FOBS= 100.3 SIGMA=  2.4 PHAS=  -81.4 FOM= 0.62 TEST= 0
INDE  25 28 57 FOBS=  44.9 SIGMA=  5.2 PHAS= -170.6 FOM= 0.46 TEST= 0
INDE  25 28 59 FOBS=  53.6 SIGMA=  4.4 PHAS=   64.6 FOM= 0.84 TEST= 0
INDE  25 28 61 FOBS=  18.1 SIGMA= 20.4 PHAS=  -48.8 FOM= 0.29 TEST= 0
INDE  25 28 63 FOBS=   0.0 SIGMA= 24.5 PHAS=    0.0 FOM= 0.00 TEST= 0
INDE  25 28 65 FOBS=  18.5 SIGMA= 26.2 PHAS= -114.3 FOM= 0.48 TEST= 0
INDE  25 28 67 FOBS= 101.9 SIGMA=  5.0 PHAS= -111.4 FOM= 0.94 TEST= 0
```

*FIG. 12A - 496*

```
INDE 25 29 26 FOBS=   215.9 SIGMA=  1.0 PHAS=  178.4 FOM= 0.96 TEST= 0
INDE 25 29 28 FOBS=   150.5 SIGMA=  1.3 PHAS=   48.1 FOM= 0.97 TEST= 0
INDE 25 29 30 FOBS=     0.0 SIGMA= 20.4 PHAS=    0.0 FOM= 0.00 TEST= 1
INDE 25 29 32 FOBS=   310.6 SIGMA=  0.8 PHAS=  -93.4 FOM= 0.97 TEST= 0
INDE 25 29 34 FOBS=   142.1 SIGMA=  1.4 PHAS=  -67.9 FOM= 0.88 TEST= 0
INDE 25 29 36 FOBS=   177.8 SIGMA=  1.1 PHAS= -129.5 FOM= 0.91 TEST= 0
INDE 25 29 38 FOBS=   160.8 SIGMA=  1.1 PHAS= -127.6 FOM= 0.92 TEST= 0
INDE 25 29 40 FOBS=    79.9 SIGMA=  2.1 PHAS=  179.9 FOM= 0.94 TEST= 0
INDE 25 29 42 FOBS=    63.6 SIGMA=  2.6 PHAS=  131.8 FOM= 0.79 TEST= 0
INDE 25 29 44 FOBS=    94.3 SIGMA=  1.9 PHAS=   15.9 FOM= 0.83 TEST= 0
INDE 25 29 46 FOBS=    52.2 SIGMA=  3.5 PHAS=  -30.5 FOM= 0.60 TEST= 0
INDE 25 29 48 FOBS=    44.7 SIGMA=  4.0 PHAS=   -9.6 FOM= 0.70 TEST= 0
INDE 25 29 50 FOBS=   104.5 SIGMA=  1.7 PHAS=  -48.6 FOM= 0.95 TEST= 0
INDE 25 29 52 FOBS=    86.7 SIGMA=  2.0 PHAS=   73.3 FOM= 0.36 TEST= 0
INDE 25 29 54 FOBS=    48.0 SIGMA=  4.0 PHAS=  150.2 FOM= 0.70 TEST= 0
INDE 25 29 56 FOBS=    69.2 SIGMA=  4.4 PHAS=  167.3 FOM= 0.92 TEST= 0
INDE 25 29 58 FOBS=    25.5 SIGMA= 11.9 PHAS=  -40.3 FOM= 0.14 TEST= 0
INDE 25 29 60 FOBS=    70.9 SIGMA=  3.4 PHAS=  -46.0 FOM= 0.82 TEST= 0
INDE 25 29 62 FOBS=    41.3 SIGMA=  7.4 PHAS= -130.3 FOM= 0.61 TEST= 0
INDE 25 29 64 FOBS=    46.2 SIGMA= 10.6 PHAS=  102.2 FOM= 0.71 TEST= 0
INDE 25 29 66 FOBS=    17.8 SIGMA= 27.4 PHAS=   87.3 FOM= 0.04 TEST= 1
INDE 25 30 25 FOBS=   188.1 SIGMA=  1.1 PHAS=   90.0 FOM= 0.96 TEST= 0
INDE 25 30 27 FOBS=   227.7 SIGMA=  1.1 PHAS=  122.0 FOM= 0.97 TEST= 0
INDE 25 30 29 FOBS=   199.0 SIGMA=  1.2 PHAS=   58.2 FOM= 0.94 TEST= 0
INDE 25 30 31 FOBS=   357.4 SIGMA=  0.7 PHAS=  140.1 FOM= 0.96 TEST= 0
INDE 25 30 33 FOBS=   207.0 SIGMA=  1.0 PHAS= -167.0 FOM= 0.94 TEST= 0
INDE 25 30 35 FOBS=   281.4 SIGMA=  0.8 PHAS=   67.0 FOM= 0.96 TEST= 0
INDE 25 30 37 FOBS=     0.0 SIGMA= 19.1 PHAS=    0.0 FOM= 0.00 TEST= 0
INDE 25 30 39 FOBS=    78.4 SIGMA=  2.3 PHAS=  120.6 FOM= 0.43 TEST= 0
INDE 25 30 41 FOBS=   293.1 SIGMA=  0.7 PHAS=   79.5 FOM= 0.65 TEST= 1
INDE 25 30 43 FOBS=   102.3 SIGMA=  1.6 PHAS=    0.4 FOM= 0.84 TEST= 1
INDE 25 30 45 FOBS=    32.0 SIGMA=  5.7 PHAS=    5.5 FOM= 0.16 TEST= 1
INDE 25 30 47 FOBS=    64.2 SIGMA=  2.7 PHAS=  -54.0 FOM= 0.40 TEST= 0
INDE 25 30 49 FOBS=    13.1 SIGMA= 14.3 PHAS=  152.4 FOM= 0.16 TEST= 0
INDE 25 30 51 FOBS=    57.4 SIGMA=  2.9 PHAS= -112.6 FOM= 0.30 TEST= 1
INDE 25 30 53 FOBS=    59.1 SIGMA=  3.1 PHAS=  125.1 FOM= 0.80 TEST= 0
INDE 25 30 55 FOBS=     8.9 SIGMA= 26.2 PHAS=  -12.4 FOM= 0.11 TEST= 0
INDE 25 30 57 FOBS=    91.0 SIGMA=  3.5 PHAS=  133.6 FOM= 0.93 TEST= 0
INDE 25 30 59 FOBS=    46.1 SIGMA=  6.7 PHAS= -147.4 FOM= 0.58 TEST= 0
INDE 25 30 61 FOBS=     0.0 SIGMA= 27.8 PHAS=    0.0 FOM= 0.00 TEST= 0
INDE 25 30 63 FOBS=     0.0 SIGMA= 27.6 PHAS=    0.0 FOM= 0.00 TEST= 1
INDE 25 30 65 FOBS=    57.8 SIGMA=  8.7 PHAS=   17.7 FOM= 0.47 TEST= 0
INDE 25 30 67 FOBS=    41.4 SIGMA= 11.9 PHAS=  -86.7 FOM= 0.64 TEST= 0
INDE 25 31 26 FOBS=   202.9 SIGMA=  1.0 PHAS=  -61.3 FOM= 0.95 TEST= 0
INDE 25 31 28 FOBS=   210.8 SIGMA=  1.0 PHAS=  -27.9 FOM= 0.97 TEST= 0
INDE 25 31 30 FOBS=   329.1 SIGMA=  0.7 PHAS=   87.1 FOM= 0.98 TEST= 0
INDE 25 31 32 FOBS=   152.6 SIGMA=  1.2 PHAS=   83.2 FOM= 0.82 TEST= 0
INDE 25 31 34 FOBS=   157.7 SIGMA=  1.2 PHAS=  -44.6 FOM= 0.87 TEST= 0
INDE 25 31 36 FOBS=     0.0 SIGMA= 18.2 PHAS=    0.0 FOM= 0.00 TEST= 0
INDE 25 31 38 FOBS=     0.0 SIGMA= 18.4 PHAS=    0.0 FOM= 0.00 TEST= 0
INDE 25 31 40 FOBS=   298.9 SIGMA=  0.7 PHAS=  -72.4 FOM= 0.97 TEST= 0
INDE 25 31 42 FOBS=   164.4 SIGMA=  1.1 PHAS=  -53.4 FOM= 0.96 TEST= 0
INDE 25 31 44 FOBS=    50.7 SIGMA=  3.3 PHAS=  -32.0 FOM= 0.93 TEST= 0
INDE 25 31 46 FOBS=    46.7 SIGMA=  3.7 PHAS=  -58.1 FOM= 0.80 TEST= 0
INDE 25 31 48 FOBS=     0.0 SIGMA= 18.7 PHAS=    0.0 FOM= 0.00 TEST= 0
INDE 25 31 50 FOBS=    35.9 SIGMA=  4.9 PHAS=  144.6 FOM= 0.34 TEST= 0
INDE 25 31 52 FOBS=    44.0 SIGMA=  3.9 PHAS=   51.5 FOM= 0.56 TEST= 0
INDE 25 31 54 FOBS=    78.0 SIGMA=  3.1 PHAS=   15.7 FOM= 0.14 TEST= 1
INDE 25 31 56 FOBS=    29.1 SIGMA= 12.8 PHAS=   -1.3 FOM= 0.13 TEST= 0
INDE 25 31 58 FOBS=    39.4 SIGMA=  7.9 PHAS=   55.8 FOM= 0.51 TEST= 0
INDE 25 31 60 FOBS=    87.7 SIGMA=  3.6 PHAS=   19.0 FOM= 0.93 TEST= 0
INDE 25 31 62 FOBS=    62.2 SIGMA=  5.0 PHAS= -115.2 FOM= 0.86 TEST= 0
INDE 25 31 64 FOBS=    22.8 SIGMA= 16.4 PHAS=  -32.4 FOM= 0.11 TEST= 1
INDE 25 31 66 FOBS=     0.0 SIGMA= 30.9 PHAS=    0.0 FOM= 0.00 TEST= 0
INDE 25 32 25 FOBS=   215.6 SIGMA=  0.9 PHAS=  156.9 FOM= 0.95 TEST= 0
INDE 25 32 27 FOBS=   166.1 SIGMA=  1.2 PHAS=  160.7 FOM= 0.94 TEST= 0
INDE 25 32 29 FOBS=    96.6 SIGMA=  2.0 PHAS=   72.7 FOM= 0.60 TEST= 0
INDE 25 32 31 FOBS=   169.3 SIGMA=  1.1 PHAS=   57.9 FOM= 0.88 TEST= 0
INDE 25 32 33 FOBS=   171.4 SIGMA=  1.1 PHAS=   72.2 FOM= 0.88 TEST= 0
INDE 25 32 35 FOBS=    67.3 SIGMA=  2.5 PHAS=  128.4 FOM= 0.90 TEST= 0
```

*FIG. 12A - 497*

```
INDE 25 32 37 FOBS=     0.0 SIGMA= 18.0 PHAS=    0.0 FOM= 0.00 TEST= 0
INDE 25 32 39 FOBS=   195.2 SIGMA=  0.9 PHAS= -142.1 FOM= 0.88 TEST= 1
INDE 25 32 41 FOBS=   116.6 SIGMA=  1.4 PHAS=  171.8 FOM= 0.94 TEST= 0
INDE 25 32 43 FOBS=   113.3 SIGMA=  1.4 PHAS=   77.5 FOM= 0.95 TEST= 0
INDE 25 32 45 FOBS=    49.4 SIGMA=  3.3 PHAS= -117.7 FOM= 0.73 TEST= 0
INDE 25 32 47 FOBS=   102.0 SIGMA=  1.7 PHAS= -167.2 FOM= 0.96 TEST= 0
INDE 25 32 49 FOBS=    87.8 SIGMA=  1.9 PHAS=  128.9 FOM= 0.92 TEST= 0
INDE 25 32 51 FOBS=     0.0 SIGMA= 18.6 PHAS=    0.0 FOM= 0.00 TEST= 0
INDE 25 32 53 FOBS=    89.2 SIGMA=  2.4 PHAS=  144.6 FOM= 0.89 TEST= 0
INDE 25 32 55 FOBS=    94.3 SIGMA=  2.6 PHAS=  127.0 FOM= 0.93 TEST= 0
INDE 25 32 57 FOBS=    70.6 SIGMA=  3.4 PHAS= -163.1 FOM= 0.77 TEST= 0
INDE 25 32 59 FOBS=    99.0 SIGMA=  2.8 PHAS= -115.5 FOM= 0.93 TEST= 0
INDE 25 32 61 FOBS=    18.3 SIGMA= 16.7 PHAS=    6.2 FOM= 0.47 TEST= 0
INDE 25 32 63 FOBS=     0.0 SIGMA= 24.8 PHAS=    0.0 FOM= 0.00 TEST= 0
INDE 25 32 65 FOBS=    87.4 SIGMA=  4.4 PHAS=  -94.7 FOM= 0.04 TEST= 1
INDE 25 33 26 FOBS=   189.6 SIGMA=  1.1 PHAS=   20.7 FOM= 0.89 TEST= 0
INDE 25 33 28 FOBS=    97.1 SIGMA=  2.0 PHAS=   47.6 FOM= 0.92 TEST= 0
INDE 25 33 30 FOBS=    62.8 SIGMA=  3.0 PHAS=   60.0 FOM= 0.11 TEST= 0
INDE 25 33 32 FOBS=   156.1 SIGMA=  1.1 PHAS=  -46.0 FOM= 0.92 TEST= 0
INDE 25 33 34 FOBS=   203.4 SIGMA=  0.9 PHAS=  -81.3 FOM= 0.93 TEST= 0
INDE 25 33 36 FOBS=    31.3 SIGMA=  5.5 PHAS=  150.3 FOM= 0.46 TEST= 0
INDE 25 33 38 FOBS=    85.4 SIGMA=  2.0 PHAS=  162.3 FOM= 0.90 TEST= 0
INDE 25 33 40 FOBS=    80.7 SIGMA=  2.0 PHAS=  -63.0 FOM= 0.94 TEST= 0
INDE 25 33 42 FOBS=    63.7 SIGMA=  2.5 PHAS= -167.3 FOM= 0.16 TEST= 1
INDE 25 33 44 FOBS=    63.7 SIGMA=  2.6 PHAS=  -12.3 FOM= 0.86 TEST= 0
INDE 25 33 46 FOBS=    63.0 SIGMA=  2.7 PHAS=  168.0 FOM= 0.57 TEST= 0
INDE 25 33 48 FOBS=   137.4 SIGMA=  1.2 PHAS=  100.7 FOM= 0.94 TEST= 0
INDE 25 33 50 FOBS=    46.3 SIGMA=  4.0 PHAS=  100.0 FOM= 0.75 TEST= 0
INDE 25 33 52 FOBS=   108.3 SIGMA=  2.0 PHAS=   53.6 FOM= 0.88 TEST= 0
INDE 25 33 54 FOBS=     0.0 SIGMA= 23.0 PHAS=    0.0 FOM= 0.00 TEST= 0
INDE 25 33 56 FOBS=     0.0 SIGMA= 21.7 PHAS=    0.0 FOM= 0.00 TEST= 0
INDE 25 33 58 FOBS=    74.9 SIGMA=  3.2 PHAS=  144.7 FOM= 0.92 TEST= 0
INDE 25 33 60 FOBS=    29.1 SIGMA=  9.1 PHAS=   61.4 FOM= 0.65 TEST= 0
INDE 25 33 62 FOBS=    27.1 SIGMA= 11.5 PHAS=  -56.3 FOM= 0.55 TEST= 0
INDE 25 33 64 FOBS=    33.8 SIGMA= 11.3 PHAS=   66.9 FOM= 0.41 TEST= 0
INDE 25 34 25 FOBS=   107.6 SIGMA=  1.7 PHAS=   13.4 FOM= 0.95 TEST= 0
INDE 25 34 27 FOBS=   106.9 SIGMA=  1.9 PHAS=  -99.6 FOM= 0.87 TEST= 1
INDE 25 34 29 FOBS=   188.6 SIGMA=  1.1 PHAS=    5.2 FOM= 0.96 TEST= 0
INDE 25 34 31 FOBS=   197.6 SIGMA=  1.0 PHAS=  169.9 FOM= 0.95 TEST= 0
INDE 25 34 33 FOBS=   188.0 SIGMA=  1.0 PHAS=  134.7 FOM= 0.90 TEST= 0
INDE 25 34 35 FOBS=     0.0 SIGMA= 19.0 PHAS=    0.0 FOM= 0.00 TEST= 0
INDE 25 34 37 FOBS=   111.8 SIGMA=  1.5 PHAS=  -31.0 FOM= 0.82 TEST= 0
INDE 25 34 39 FOBS=   159.9 SIGMA=  1.1 PHAS= -153.3 FOM= 0.95 TEST= 0
INDE 25 34 41 FOBS=   139.6 SIGMA=  1.2 PHAS= -159.4 FOM= 0.94 TEST= 0
INDE 25 34 43 FOBS=    10.5 SIGMA= 15.0 PHAS=  -35.8 FOM= 0.49 TEST= 1
INDE 25 34 45 FOBS=    25.0 SIGMA=  7.2 PHAS=    0.0 FOM= 0.29 TEST= 0
INDE 25 34 47 FOBS=    25.9 SIGMA=  8.3 PHAS=   -0.8 FOM= 0.07 TEST= 0
INDE 25 34 49 FOBS=    23.7 SIGMA=  7.6 PHAS=  122.8 FOM= 0.09 TEST= 1
INDE 25 34 51 FOBS=     0.0 SIGMA= 19.7 PHAS=    0.0 FOM= 0.00 TEST= 0
INDE 25 34 53 FOBS=    30.4 SIGMA=  7.8 PHAS= -120.5 FOM= 0.13 TEST= 1
INDE 25 34 55 FOBS=    52.2 SIGMA=  4.6 PHAS=  106.5 FOM= 0.73 TEST= 0
INDE 25 34 57 FOBS=    27.1 SIGMA=  8.8 PHAS=   20.4 FOM= 0.61 TEST= 0
INDE 25 34 59 FOBS=    81.0 SIGMA=  3.0 PHAS=  163.8 FOM= 0.03 TEST= 1
INDE 25 34 61 FOBS=    56.6 SIGMA=  4.3 PHAS=  -93.2 FOM= 0.76 TEST= 0
INDE 25 34 63 FOBS=     0.0 SIGMA= 24.9 PHAS=    0.0 FOM= 0.00 TEST= 1
INDE 25 34 65 FOBS=    52.1 SIGMA=  6.2 PHAS=  -74.7 FOM= 0.70 TEST= 0
INDE 25 35 26 FOBS=   117.7 SIGMA=  1.6 PHAS=  170.8 FOM= 0.85 TEST= 0
INDE 25 35 28 FOBS=    61.2 SIGMA=  3.1 PHAS= -102.6 FOM= 0.76 TEST= 0
INDE 25 35 30 FOBS=    97.6 SIGMA=  1.9 PHAS=  -25.8 FOM= 0.85 TEST= 0
INDE 25 35 32 FOBS=   152.6 SIGMA=  1.2 PHAS=   33.4 FOM= 0.95 TEST= 0
INDE 25 35 34 FOBS=    39.0 SIGMA=  4.6 PHAS=  -81.5 FOM= 0.18 TEST= 0
INDE 25 35 36 FOBS=    55.5 SIGMA=  3.0 PHAS=  -69.8 FOM= 0.47 TEST= 0
INDE 25 35 38 FOBS=    83.2 SIGMA=  2.0 PHAS=  147.7 FOM= 0.94 TEST= 0
INDE 25 35 40 FOBS=    41.1 SIGMA=  4.0 PHAS=  -75.9 FOM= 0.89 TEST= 0
INDE 25 35 42 FOBS=    88.0 SIGMA=  1.9 PHAS=  139.4 FOM= 0.85 TEST= 0
INDE 25 35 44 FOBS=    35.8 SIGMA=  4.6 PHAS=   20.1 FOM= 0.52 TEST= 0
INDE 25 35 46 FOBS=    51.3 SIGMA=  3.2 PHAS=   61.5 FOM= 0.69 TEST= 0
INDE 25 35 48 FOBS=    23.7 SIGMA=  8.5 PHAS=   99.5 FOM= 0.45 TEST= 0
INDE 25 35 50 FOBS=    93.4 SIGMA=  2.1 PHAS=  175.5 FOM= 0.89 TEST= 0
INDE 25 35 52 FOBS=    43.0 SIGMA=  4.3 PHAS=   31.9 FOM= 0.69 TEST= 0
```

*FIG. 12A - 498*

```
INDE 25 35 54 FOBS=   25.8 SIGMA=  7.8 PHAS=  114.0 FOM= 0.09 TEST= 1
INDE 25 35 56 FOBS=   95.4 SIGMA=  2.6 PHAS= -106.5 FOM= 0.92 TEST= 0
INDE 25 35 58 FOBS=   37.3 SIGMA=  6.4 PHAS=  -80.2 FOM= 0.55 TEST= 0
INDE 25 35 60 FOBS=    0.0 SIGMA= 24.8 PHAS=    0.0 FOM= 0.00 TEST= 0
INDE 25 35 62 FOBS=   48.6 SIGMA=  5.0 PHAS=   77.3 FOM= 0.74 TEST= 0
INDE 25 35 64 FOBS=   45.1 SIGMA=  7.3 PHAS= -178.0 FOM= 0.78 TEST= 0
INDE 25 36 25 FOBS=  422.0 SIGMA=  0.6 PHAS=    7.5 FOM= 0.98 TEST= 0
INDE 25 36 27 FOBS=  142.6 SIGMA=  1.4 PHAS=   72.8 FOM= 0.96 TEST= 0
INDE 25 36 29 FOBS=   87.0 SIGMA=  2.2 PHAS=   30.4 FOM= 0.72 TEST= 0
INDE 25 36 31 FOBS=   64.8 SIGMA=  2.8 PHAS=  -65.4 FOM= 0.87 TEST= 0
INDE 25 36 33 FOBS=   72.5 SIGMA=  2.3 PHAS=   13.7 FOM= 0.79 TEST= 0
INDE 25 36 35 FOBS=   77.3 SIGMA=  2.1 PHAS=  152.1 FOM= 0.36 TEST= 0
INDE 25 36 37 FOBS=  148.9 SIGMA=  1.2 PHAS=   19.6 FOM= 0.93 TEST= 0
INDE 25 36 39 FOBS=   92.3 SIGMA=  1.8 PHAS=  165.7 FOM= 0.92 TEST= 0
INDE 25 36 41 FOBS=  142.3 SIGMA=  1.2 PHAS=  164.8 FOM= 0.91 TEST= 0
INDE 25 36 43 FOBS=   40.5 SIGMA=  4.1 PHAS=  -22.0 FOM= 0.86 TEST= 0
INDE 25 36 45 FOBS=   35.7 SIGMA=  4.6 PHAS=  -35.1 FOM= 0.38 TEST= 0
INDE 25 36 47 FOBS=   80.3 SIGMA=  2.2 PHAS=    4.5 FOM= 0.85 TEST= 0
INDE 25 36 49 FOBS=  112.1 SIGMA=  1.7 PHAS=   70.6 FOM= 0.90 TEST= 0
INDE 25 36 51 FOBS=   64.4 SIGMA=  2.9 PHAS=   82.2 FOM= 0.26 TEST= 1
INDE 25 36 53 FOBS=    0.0 SIGMA= 20.8 PHAS=    0.0 FOM= 0.00 TEST= 1
INDE 25 36 55 FOBS=  180.2 SIGMA=  1.4 PHAS=  113.7 FOM= 0.84 TEST= 1
INDE 25 36 57 FOBS=   37.8 SIGMA=  5.4 PHAS=  114.5 FOM= 0.77 TEST= 0
INDE 25 36 59 FOBS=   37.1 SIGMA=  6.5 PHAS= -176.5 FOM= 0.78 TEST= 0
INDE 25 36 61 FOBS=    0.0 SIGMA= 22.0 PHAS=    0.0 FOM= 0.00 TEST= 0
INDE 25 36 63 FOBS=    0.0 SIGMA= 25.5 PHAS=    0.0 FOM= 0.00 TEST= 0
INDE 25 37 26 FOBS=  242.1 SIGMA=  0.9 PHAS= -110.5 FOM= 0.96 TEST= 0
INDE 25 37 28 FOBS=   64.8 SIGMA=  2.8 PHAS=  144.3 FOM= 0.10 TEST= 0
INDE 25 37 30 FOBS=   96.5 SIGMA=  1.9 PHAS=    7.0 FOM= 0.86 TEST= 0
INDE 25 37 32 FOBS=   58.6 SIGMA=  3.1 PHAS=  -74.8 FOM= 0.39 TEST= 0
INDE 25 37 34 FOBS=    0.0 SIGMA= 19.3 PHAS=    0.0 FOM= 0.00 TEST= 0
INDE 25 37 36 FOBS=   34.9 SIGMA=  4.9 PHAS=  -65.1 FOM= 0.83 TEST= 0
INDE 25 37 38 FOBS=  122.2 SIGMA=  1.4 PHAS= -151.4 FOM= 0.85 TEST= 0
INDE 25 37 40 FOBS=  136.1 SIGMA=  1.3 PHAS=   -8.0 FOM= 0.77 TEST= 0
INDE 25 37 42 FOBS=   97.5 SIGMA=  1.7 PHAS=  148.8 FOM= 0.90 TEST= 0
INDE 25 37 44 FOBS=   90.7 SIGMA=  1.8 PHAS=  161.8 FOM= 0.93 TEST= 0
INDE 25 37 46 FOBS=    0.0 SIGMA= 19.0 PHAS=    0.0 FOM= 0.00 TEST= 0
INDE 25 37 48 FOBS=   60.4 SIGMA=  2.8 PHAS=  -53.1 FOM= 0.41 TEST= 1
INDE 25 37 50 FOBS=   43.8 SIGMA=  4.3 PHAS=  -64.8 FOM= 0.66 TEST= 0
INDE 25 37 52 FOBS=   66.3 SIGMA=  2.9 PHAS=  -50.9 FOM= 0.85 TEST= 0
INDE 25 37 54 FOBS=   79.2 SIGMA=  2.6 PHAS=  109.6 FOM= 0.92 TEST= 0
INDE 25 37 56 FOBS=   46.1 SIGMA=  4.8 PHAS=  -46.2 FOM= 0.73 TEST= 0
INDE 25 37 58 FOBS=    0.0 SIGMA= 22.0 PHAS=    0.0 FOM= 0.00 TEST= 0
INDE 25 37 60 FOBS=   26.8 SIGMA=  7.8 PHAS=   26.6 FOM= 0.32 TEST= 0
INDE 25 37 62 FOBS=   44.9 SIGMA=  7.3 PHAS=   37.5 FOM= 0.44 TEST= 0
INDE 25 38 25 FOBS=  123.4 SIGMA=  1.5 PHAS=  -11.4 FOM= 0.92 TEST= 0
INDE 25 38 27 FOBS=  188.9 SIGMA=  1.1 PHAS=   74.2 FOM= 0.91 TEST= 0
INDE 25 38 29 FOBS=   57.3 SIGMA=  3.2 PHAS= -127.3 FOM= 0.18 TEST= 0
INDE 25 38 31 FOBS=   84.3 SIGMA=  2.2 PHAS=  -85.6 FOM= 0.75 TEST= 0
INDE 25 38 33 FOBS=   95.5 SIGMA=  1.9 PHAS=  142.9 FOM= 0.63 TEST= 0
INDE 25 38 35 FOBS=   85.8 SIGMA=  1.9 PHAS=  132.6 FOM= 0.93 TEST= 0
INDE 25 38 37 FOBS=   72.5 SIGMA=  2.3 PHAS=   95.8 FOM= 0.86 TEST= 0
INDE 25 38 39 FOBS=    0.0 SIGMA= 19.6 PHAS=    0.0 FOM= 0.00 TEST= 0
INDE 25 38 41 FOBS=   35.0 SIGMA=  5.0 PHAS=   67.4 FOM= 0.51 TEST= 0
INDE 25 38 43 FOBS=   82.9 SIGMA=  2.0 PHAS=   31.0 FOM= 0.91 TEST= 0
INDE 25 38 45 FOBS=   61.5 SIGMA=  2.8 PHAS=   64.3 FOM= 0.83 TEST= 0
INDE 25 38 47 FOBS=   40.0 SIGMA=  4.5 PHAS= -116.2 FOM= 0.18 TEST= 1
INDE 25 38 49 FOBS=   51.4 SIGMA=  3.3 PHAS=  122.5 FOM= 0.83 TEST= 0
INDE 25 38 51 FOBS=   17.0 SIGMA= 13.1 PHAS=  158.2 FOM= 0.52 TEST= 0
INDE 25 38 53 FOBS=    0.0 SIGMA= 20.4 PHAS=    0.0 FOM= 0.00 TEST= 0
INDE 25 38 55 FOBS=  125.9 SIGMA=  1.7 PHAS=   93.5 FOM= 0.95 TEST= 0
INDE 25 38 57 FOBS=    0.0 SIGMA= 21.0 PHAS=    0.0 FOM= 0.00 TEST= 1
INDE 25 38 59 FOBS=   71.9 SIGMA=  3.1 PHAS= -170.7 FOM= 0.87 TEST= 0
INDE 25 38 61 FOBS=    0.0 SIGMA= 21.4 PHAS=    0.0 FOM= 0.00 TEST= 0
INDE 25 38 63 FOBS=   28.4 SIGMA= 12.1 PHAS= -127.5 FOM= 0.20 TEST= 0
INDE 25 39 26 FOBS=  119.1 SIGMA=  1.6 PHAS= -122.9 FOM= 0.90 TEST= 0
INDE 25 39 28 FOBS=   74.7 SIGMA=  2.5 PHAS= -112.1 FOM= 0.74 TEST= 0
INDE 25 39 30 FOBS=  157.2 SIGMA=  1.2 PHAS= -128.2 FOM= 0.48 TEST= 1
INDE 25 39 32 FOBS=    0.0 SIGMA= 18.9 PHAS=    0.0 FOM= 0.00 TEST= 0
INDE 25 39 34 FOBS=   37.6 SIGMA=  4.8 PHAS=  178.8 FOM= 0.42 TEST= 0
```

*FIG. 12A - 499*

```
INDE 25 39 36 FOBS=   106.1 SIGMA=  1.6 PHAS=   54.3 FOM= 0.87 TEST= 0
INDE 25 39 38 FOBS=   179.3 SIGMA=  1.0 PHAS= -111.0 FOM= 0.95 TEST= 0
INDE 25 39 40 FOBS=   154.4 SIGMA=  1.1 PHAS=  -66.6 FOM= 0.95 TEST= 0
INDE 25 39 42 FOBS=    63.6 SIGMA=  2.5 PHAS=  -80.1 FOM= 0.84 TEST= 0
INDE 25 39 44 FOBS=    58.0 SIGMA=  3.1 PHAS=  -55.6 FOM= 0.79 TEST= 0
INDE 25 39 46 FOBS=     0.0 SIGMA= 18.5 PHAS=    0.0 FOM= 0.00 TEST= 0
INDE 25 39 48 FOBS=     0.0 SIGMA= 18.5 PHAS=    0.0 FOM= 0.00 TEST= 1
INDE 25 39 50 FOBS=    87.7 SIGMA=  2.0 PHAS=  -20.2 FOM= 0.93 TEST= 0
INDE 25 39 52 FOBS=    90.2 SIGMA=  2.4 PHAS=  -49.8 FOM= 0.91 TEST= 0
INDE 25 39 54 FOBS=    46.7 SIGMA=  5.9 PHAS=   43.2 FOM= 0.73 TEST= 0
INDE 25 39 56 FOBS=    19.9 SIGMA= 10.4 PHAS=  -10.5 FOM= 0.36 TEST= 0
INDE 25 39 58 FOBS=    75.5 SIGMA=  2.8 PHAS=  127.3 FOM= 0.92 TEST= 0
INDE 25 39 60 FOBS=    70.5 SIGMA=  3.1 PHAS=   33.5 FOM= 0.83 TEST= 0
INDE 25 39 62 FOBS=     0.0 SIGMA= 23.7 PHAS=    0.0 FOM= 0.00 TEST= 0
INDE 25 40 25 FOBS=   115.5 SIGMA=  1.6 PHAS=  132.5 FOM= 0.93 TEST= 0
INDE 25 40 27 FOBS=    94.0 SIGMA=  2.0 PHAS=   96.0 FOM= 0.95 TEST= 0
INDE 25 40 29 FOBS=    95.7 SIGMA=  1.9 PHAS=  119.6 FOM= 0.80 TEST= 0
INDE 25 40 31 FOBS=   101.9 SIGMA=  1.8 PHAS=  -79.3 FOM= 0.97 TEST= 0
INDE 25 40 33 FOBS=    91.1 SIGMA=  2.0 PHAS=   93.5 FOM= 0.87 TEST= 0
INDE 25 40 35 FOBS=     0.0 SIGMA= 18.4 PHAS=    0.0 FOM= 0.00 TEST= 0
INDE 25 40 37 FOBS=     0.0 SIGMA= 18.0 PHAS=    0.0 FOM= 0.00 TEST= 0
INDE 25 40 39 FOBS=    90.6 SIGMA=  1.8 PHAS= -163.5 FOM= 0.87 TEST= 0
INDE 25 40 41 FOBS=   147.5 SIGMA=  1.2 PHAS= -157.1 FOM= 0.97 TEST= 0
INDE 25 40 43 FOBS=   115.6 SIGMA=  1.6 PHAS= -142.8 FOM= 0.95 TEST= 0
INDE 25 40 45 FOBS=     0.0 SIGMA= 18.6 PHAS=    0.0 FOM= 0.00 TEST= 0
INDE 25 40 47 FOBS=    65.4 SIGMA=  2.7 PHAS=  112.0 FOM= 0.87 TEST= 0
INDE 25 40 49 FOBS=    35.4 SIGMA=  4.9 PHAS=  -56.3 FOM= 0.39 TEST= 0
INDE 25 40 51 FOBS=    71.4 SIGMA=  2.5 PHAS=  132.5 FOM= 0.76 TEST= 0
INDE 25 40 53 FOBS=    49.4 SIGMA=  4.2 PHAS=  125.1 FOM= 0.86 TEST= 0
INDE 25 40 55 FOBS=     0.0 SIGMA= 20.4 PHAS=    0.0 FOM= 0.00 TEST= 0
INDE 25 40 57 FOBS=     0.0 SIGMA= 21.1 PHAS=    0.0 FOM= 0.00 TEST= 0
INDE 25 40 59 FOBS=    50.2 SIGMA=  4.2 PHAS=  108.7 FOM= 0.76 TEST= 0
INDE 25 40 61 FOBS=    28.6 SIGMA= 10.3 PHAS= -179.8 FOM= 0.54 TEST= 0
INDE 25 41 26 FOBS=   191.1 SIGMA=  1.0 PHAS=  107.5 FOM= 0.94 TEST= 0
INDE 25 41 28 FOBS=    72.7 SIGMA=  2.5 PHAS=  -61.4 FOM= 0.88 TEST= 0
INDE 25 41 30 FOBS=    94.1 SIGMA=  2.0 PHAS=   -0.1 FOM= 0.81 TEST= 0
INDE 25 41 32 FOBS=    97.4 SIGMA=  1.9 PHAS=  101.5 FOM= 0.82 TEST= 0
INDE 25 41 34 FOBS=    59.1 SIGMA=  3.0 PHAS=   60.6 FOM= 0.33 TEST= 0
INDE 25 41 36 FOBS=     0.0 SIGMA= 18.0 PHAS=    0.0 FOM= 0.00 TEST= 0
INDE 25 41 38 FOBS=    58.5 SIGMA=  2.8 PHAS= -145.2 FOM= 0.67 TEST= 0
INDE 25 41 40 FOBS=    47.8 SIGMA=  3.8 PHAS=   69.3 FOM= 0.48 TEST= 0
INDE 25 41 42 FOBS=   176.8 SIGMA=  1.1 PHAS=  115.1 FOM= 0.97 TEST= 0
INDE 25 41 44 FOBS=    31.5 SIGMA=  6.6 PHAS= -179.5 FOM= 0.35 TEST= 0
INDE 25 41 46 FOBS=   116.4 SIGMA=  1.6 PHAS=  -53.9 FOM= 0.95 TEST= 0
INDE 25 41 48 FOBS=    86.1 SIGMA=  2.1 PHAS=  -63.7 FOM= 0.57 TEST= 0
INDE 25 41 50 FOBS=   144.4 SIGMA=  1.3 PHAS=  -54.8 FOM= 0.96 TEST= 0
INDE 25 41 52 FOBS=   124.0 SIGMA=  1.6 PHAS=    3.6 FOM= 0.94 TEST= 0
INDE 25 41 54 FOBS=     0.0 SIGMA= 20.5 PHAS=    0.0 FOM= 0.00 TEST= 0
INDE 25 41 56 FOBS=    42.5 SIGMA=  5.0 PHAS= -171.9 FOM= 0.46 TEST= 0
INDE 25 41 58 FOBS=    62.2 SIGMA=  3.5 PHAS=   97.9 FOM= 0.68 TEST= 0
INDE 25 41 60 FOBS=    80.1 SIGMA=  3.3 PHAS=   11.6 FOM= 0.63 TEST= 0
INDE 25 42 25 FOBS=   202.0 SIGMA=  1.0 PHAS=  -18.3 FOM= 0.93 TEST= 0
INDE 25 42 27 FOBS=   123.1 SIGMA=  1.5 PHAS=  -73.7 FOM= 0.91 TEST= 0
INDE 25 42 29 FOBS=    84.6 SIGMA=  2.2 PHAS= -132.2 FOM= 0.50 TEST= 0
INDE 25 42 31 FOBS=    79.0 SIGMA=  2.3 PHAS= -130.3 FOM= 0.23 TEST= 0
INDE 25 42 33 FOBS=    36.4 SIGMA=  4.9 PHAS= -122.8 FOM= 0.29 TEST= 1
INDE 25 42 35 FOBS=    57.5 SIGMA=  3.2 PHAS= -140.6 FOM= 0.81 TEST= 0
INDE 25 42 37 FOBS=    86.1 SIGMA=  1.9 PHAS= -122.2 FOM= 0.91 TEST= 0
INDE 25 42 39 FOBS=    44.6 SIGMA=  4.8 PHAS=  -69.0 FOM= 0.28 TEST= 0
INDE 25 42 41 FOBS=    56.7 SIGMA=  3.2 PHAS=  -45.9 FOM= 0.78 TEST= 0
INDE 25 42 43 FOBS=    50.1 SIGMA=  3.5 PHAS=    5.8 FOM= 0.76 TEST= 0
INDE 25 42 45 FOBS=    89.1 SIGMA=  2.0 PHAS= -104.4 FOM= 0.57 TEST= 0
INDE 25 42 47 FOBS=   163.5 SIGMA=  1.2 PHAS=  167.1 FOM= 0.97 TEST= 0
INDE 25 42 49 FOBS=    75.5 SIGMA=  2.4 PHAS= -145.9 FOM= 0.34 TEST= 1
INDE 25 42 51 FOBS=    59.9 SIGMA=  3.2 PHAS= -119.5 FOM= 0.22 TEST= 1
INDE 25 42 53 FOBS=    27.9 SIGMA=  6.8 PHAS=  -19.5 FOM= 0.48 TEST= 0
INDE 25 42 55 FOBS=    51.4 SIGMA=  4.1 PHAS=  157.2 FOM= 0.72 TEST= 0
INDE 25 42 57 FOBS=     0.0 SIGMA= 20.6 PHAS=    0.0 FOM= 0.00 TEST= 0
INDE 25 42 59 FOBS=    29.1 SIGMA=  9.9 PHAS=  158.2 FOM= 0.59 TEST= 0
INDE 25 43 26 FOBS=    84.3 SIGMA=  2.8 PHAS=  126.7 FOM= 0.06 TEST= 1
```

*FIG. 12A - 500*

```
INDE 25 43 28 FOBS=    52.9 SIGMA=  3.4 PHAS=   76.5 FOM= 0.14 TEST= 0
INDE 25 43 30 FOBS=    59.1 SIGMA=  3.2 PHAS=   65.1 FOM= 0.83 TEST= 0
INDE 25 43 32 FOBS=     0.0 SIGMA= 19.4 PHAS=    0.0 FOM= 0.00 TEST= 0
INDE 25 43 34 FOBS=     0.0 SIGMA= 19.5 PHAS=    0.0 FOM= 0.00 TEST= 0
INDE 25 43 36 FOBS=    84.4 SIGMA=  2.3 PHAS=  163.5 FOM= 0.91 TEST= 0
INDE 25 43 38 FOBS=    96.7 SIGMA=  1.9 PHAS= -177.1 FOM= 0.89 TEST= 0
INDE 25 43 40 FOBS=    57.7 SIGMA=  3.1 PHAS=  163.1 FOM= 0.88 TEST= 0
INDE 25 43 42 FOBS=    60.2 SIGMA=  3.0 PHAS=  129.2 FOM= 0.58 TEST= 0
INDE 25 43 44 FOBS=    62.1 SIGMA=  2.9 PHAS= -107.9 FOM= 0.71 TEST= 0
INDE 25 43 46 FOBS=    43.3 SIGMA=  4.6 PHAS=  -36.0 FOM= 0.26 TEST= 0
INDE 25 43 48 FOBS=    59.6 SIGMA=  3.0 PHAS=   25.9 FOM= 0.83 TEST= 0
INDE 25 43 50 FOBS=   127.1 SIGMA=  1.5 PHAS=  -73.4 FOM= 0.97 TEST= 0
INDE 25 43 52 FOBS=    47.1 SIGMA=  4.0 PHAS=  -93.8 FOM= 0.75 TEST= 0
INDE 25 43 54 FOBS=    36.2 SIGMA=  6.0 PHAS= -109.1 FOM= 0.15 TEST= 1
INDE 25 43 56 FOBS=    79.4 SIGMA=  2.8 PHAS=    6.8 FOM= 0.93 TEST= 0
INDE 25 43 58 FOBS=    74.9 SIGMA=  3.2 PHAS=  154.8 FOM= 0.69 TEST= 0
INDE 25 44 25 FOBS=   201.4 SIGMA=  1.1 PHAS=  -42.8 FOM= 0.91 TEST= 0
INDE 25 44 27 FOBS=   149.6 SIGMA=  1.4 PHAS= -133.6 FOM= 0.88 TEST= 0
INDE 25 44 29 FOBS=    84.3 SIGMA=  2.1 PHAS= -124.2 FOM= 0.88 TEST= 0
INDE 25 44 31 FOBS=   105.6 SIGMA=  1.7 PHAS=  153.9 FOM= 0.90 TEST= 0
INDE 25 44 33 FOBS=   108.2 SIGMA=  1.7 PHAS= -143.8 FOM= 0.87 TEST= 0
INDE 25 44 35 FOBS=    34.8 SIGMA=  6.7 PHAS= -152.7 FOM= 0.45 TEST= 0
INDE 25 44 37 FOBS=    48.8 SIGMA=  3.9 PHAS= -176.4 FOM= 0.74 TEST= 0
INDE 25 44 39 FOBS=    97.2 SIGMA=  1.9 PHAS=   99.4 FOM= 0.91 TEST= 0
INDE 25 44 41 FOBS=    70.2 SIGMA=  2.6 PHAS=   36.6 FOM= 0.72 TEST= 0
INDE 25 44 43 FOBS=    28.9 SIGMA=  6.4 PHAS=   -3.3 FOM= 0.20 TEST= 0
INDE 25 44 45 FOBS=     0.0 SIGMA= 19.3 PHAS=    0.0 FOM= 0.00 TEST= 0
INDE 25 44 47 FOBS=    86.5 SIGMA=  2.1 PHAS= -160.2 FOM= 0.87 TEST= 0
INDE 25 44 49 FOBS=   123.4 SIGMA=  1.5 PHAS= -153.7 FOM= 0.94 TEST= 0
INDE 25 44 51 FOBS=    71.3 SIGMA=  2.7 PHAS= -178.0 FOM= 0.88 TEST= 0
INDE 25 44 53 FOBS=    45.7 SIGMA=  4.4 PHAS= -163.7 FOM= 0.86 TEST= 0
INDE 25 44 55 FOBS=    42.4 SIGMA=  4.5 PHAS=   36.5 FOM= 0.58 TEST= 0
INDE 25 44 57 FOBS=   102.1 SIGMA=  2.4 PHAS=  -77.3 FOM= 0.87 TEST= 0
INDE 25 44 59 FOBS=     0.0 SIGMA= 26.5 PHAS=    0.0 FOM= 0.00 TEST= 0
INDE 25 45 26 FOBS=    94.4 SIGMA=  2.0 PHAS=  -64.3 FOM= 0.84 TEST= 0
INDE 25 45 28 FOBS=     0.0 SIGMA= 19.1 PHAS=    0.0 FOM= 0.00 TEST= 0
INDE 25 45 30 FOBS=   106.5 SIGMA=  1.7 PHAS=  127.4 FOM= 0.15 TEST= 1
INDE 25 45 32 FOBS=   109.0 SIGMA=  1.7 PHAS=   18.9 FOM= 0.83 TEST= 0
INDE 25 45 34 FOBS=   147.3 SIGMA=  1.4 PHAS=  104.5 FOM= 0.66 TEST= 0
INDE 25 45 36 FOBS=    95.7 SIGMA=  2.1 PHAS=  134.3 FOM= 0.80 TEST= 0
INDE 25 45 38 FOBS=    48.5 SIGMA=  3.7 PHAS=  149.9 FOM= 0.80 TEST= 0
INDE 25 45 40 FOBS=    98.4 SIGMA=  1.9 PHAS=  127.4 FOM= 0.89 TEST= 0
INDE 25 45 42 FOBS=    25.7 SIGMA=  7.0 PHAS=  -89.9 FOM= 0.58 TEST= 0
INDE 25 45 44 FOBS=    68.2 SIGMA=  2.7 PHAS=  122.1 FOM= 0.37 TEST= 1
INDE 25 45 46 FOBS=    51.4 SIGMA=  3.5 PHAS=  176.3 FOM= 0.62 TEST= 0
INDE 25 45 48 FOBS=    37.6 SIGMA=  4.8 PHAS=   21.4 FOM= 0.43 TEST= 0
INDE 25 45 50 FOBS=    39.8 SIGMA=  4.7 PHAS=  139.9 FOM= 0.29 TEST= 0
INDE 25 45 52 FOBS=    55.9 SIGMA=  3.4 PHAS=   92.2 FOM= 0.87 TEST= 0
INDE 25 45 54 FOBS=    13.7 SIGMA= 17.1 PHAS= -108.1 FOM= 0.00 TEST= 0
INDE 25 45 56 FOBS=    65.9 SIGMA=  3.0 PHAS=  -53.9 FOM= 0.88 TEST= 0
INDE 25 45 58 FOBS=    67.9 SIGMA=  4.0 PHAS=  167.7 FOM= 0.90 TEST= 0
INDE 25 46 25 FOBS=    81.7 SIGMA=  2.1 PHAS= -173.0 FOM= 0.28 TEST= 0
INDE 25 46 27 FOBS=   140.1 SIGMA=  1.5 PHAS= -175.9 FOM= 0.95 TEST= 0
INDE 25 46 29 FOBS=   111.5 SIGMA=  1.6 PHAS= -153.5 FOM= 0.92 TEST= 0
INDE 25 46 31 FOBS=    81.9 SIGMA=  2.3 PHAS= -166.6 FOM= 0.81 TEST= 1
INDE 25 46 33 FOBS=    52.2 SIGMA=  3.8 PHAS=  167.7 FOM= 0.48 TEST= 0
INDE 25 46 35 FOBS=    60.4 SIGMA=  3.3 PHAS=  -79.1 FOM= 0.81 TEST= 0
INDE 25 46 37 FOBS=    37.9 SIGMA=  5.6 PHAS= -175.2 FOM= 0.51 TEST= 0
INDE 25 46 39 FOBS=   204.6 SIGMA=  1.0 PHAS=   87.1 FOM= 0.98 TEST= 0
INDE 25 46 41 FOBS=    62.0 SIGMA=  2.9 PHAS=   75.9 FOM= 0.66 TEST= 1
INDE 25 46 43 FOBS=    75.2 SIGMA=  2.4 PHAS= -179.4 FOM= 0.76 TEST= 0
INDE 25 46 45 FOBS=    68.8 SIGMA=  2.7 PHAS=   79.3 FOM= 0.68 TEST= 0
INDE 25 46 47 FOBS=    84.8 SIGMA=  2.2 PHAS=  -36.1 FOM= 0.22 TEST= 1
INDE 25 46 49 FOBS=     0.0 SIGMA= 19.4 PHAS=    0.0 FOM= 0.00 TEST= 0
INDE 25 46 51 FOBS=    22.4 SIGMA=  9.1 PHAS=  -19.8 FOM= 0.28 TEST= 0
INDE 25 46 53 FOBS=    30.6 SIGMA=  7.6 PHAS= -152.0 FOM= 0.53 TEST= 0
INDE 25 46 55 FOBS=    55.6 SIGMA=  3.5 PHAS=  163.1 FOM= 0.86 TEST= 0
INDE 25 46 57 FOBS=    69.3 SIGMA=  3.3 PHAS=  140.4 FOM= 0.89 TEST= 0
INDE 25 47 26 FOBS=   129.3 SIGMA=  1.5 PHAS=  -47.9 FOM= 0.93 TEST= 0
INDE 25 47 28 FOBS=    73.3 SIGMA=  2.7 PHAS=  131.3 FOM= 0.77 TEST= 0
```

*FIG. 12A - 501*

```
INDE  25  47  30 FOBS=    142.9 SIGMA=    1.5 PHAS=    117.5 FOM=  0.96 TEST= 0
INDE  25  47  32 FOBS=    157.6 SIGMA=    1.4 PHAS=    100.7 FOM=  0.97 TEST= 0
INDE  25  47  34 FOBS=     63.2 SIGMA=    3.2 PHAS=     56.3 FOM=  0.31 TEST= 0
INDE  25  47  36 FOBS=     71.4 SIGMA=    3.1 PHAS=    128.4 FOM=  0.78 TEST= 0
INDE  25  47  38 FOBS=     95.7 SIGMA=    2.1 PHAS=      1.2 FOM=  0.88 TEST= 0
INDE  25  47  40 FOBS=     75.0 SIGMA=    2.4 PHAS=     83.8 FOM=  0.68 TEST= 0
INDE  25  47  42 FOBS=     39.4 SIGMA=    4.5 PHAS=      5.4 FOM=  0.65 TEST= 0
INDE  25  47  44 FOBS=     79.6 SIGMA=    2.3 PHAS=    131.4 FOM=  0.90 TEST= 0
INDE  25  47  46 FOBS=     61.2 SIGMA=    3.2 PHAS=      8.6 FOM=  0.46 TEST= 0
INDE  25  47  48 FOBS=     90.7 SIGMA=    2.0 PHAS=    -65.1 FOM=  0.93 TEST= 0
INDE  25  47  50 FOBS=     17.4 SIGMA=   12.6 PHAS=   -121.0 FOM=  0.30 TEST= 0
INDE  25  47  52 FOBS=     68.5 SIGMA=    2.9 PHAS=     58.8 FOM=  0.84 TEST= 0
INDE  25  47  54 FOBS=      1.2 SIGMA=  190.7 PHAS=     53.7 FOM=  0.01 TEST= 0
INDE  25  47  56 FOBS=     77.9 SIGMA=    3.3 PHAS=     15.6 FOM=  0.87 TEST= 0
INDE  25  48  25 FOBS=    184.1 SIGMA=    1.0 PHAS=   -163.6 FOM=  0.97 TEST= 0
INDE  25  48  27 FOBS=     70.6 SIGMA=    3.2 PHAS=   -134.8 FOM=  0.83 TEST= 0
INDE  25  48  29 FOBS=      5.1 SIGMA=   43.9 PHAS=    107.5 FOM=  0.05 TEST= 0
INDE  25  48  31 FOBS=    122.8 SIGMA=    1.7 PHAS=      3.7 FOM=  0.93 TEST= 0
INDE  25  48  33 FOBS=    106.2 SIGMA=    1.9 PHAS=     41.0 FOM=  0.85 TEST= 0
INDE  25  48  35 FOBS=     38.2 SIGMA=    5.2 PHAS=     80.3 FOM=  0.36 TEST= 0
INDE  25  48  37 FOBS=    115.5 SIGMA=    1.8 PHAS=   -105.8 FOM=  0.92 TEST= 0
INDE  25  48  39 FOBS=     22.4 SIGMA=    8.9 PHAS=    130.4 FOM=  0.17 TEST= 0
INDE  25  48  41 FOBS=     42.4 SIGMA=    4.2 PHAS=     -4.8 FOM=  0.65 TEST= 0
INDE  25  48  43 FOBS=     47.5 SIGMA=    3.8 PHAS=    120.9 FOM=  0.25 TEST= 0
INDE  25  48  45 FOBS=     79.3 SIGMA=    2.3 PHAS=     71.0 FOM=  0.91 TEST= 0
INDE  25  48  47 FOBS=     46.2 SIGMA=    4.2 PHAS=    -71.9 FOM=  0.73 TEST= 0
INDE  25  48  49 FOBS=    107.0 SIGMA=    1.8 PHAS=    174.5 FOM=  0.94 TEST= 0
INDE  25  48  51 FOBS=     52.4 SIGMA=    3.8 PHAS=   -109.5 FOM=  0.87 TEST= 0
INDE  25  48  53 FOBS=     31.6 SIGMA=    6.7 PHAS=    150.0 FOM=  0.42 TEST= 0
INDE  25  48  55 FOBS=     97.4 SIGMA=    2.6 PHAS=    102.5 FOM=  0.06 TEST= 1
INDE  25  49  26 FOBS=     87.3 SIGMA=    2.2 PHAS=    -36.2 FOM=  0.90 TEST= 0
INDE  25  49  28 FOBS=     58.5 SIGMA=    3.9 PHAS=    135.4 FOM=  0.89 TEST= 0
INDE  25  49  30 FOBS=      6.8 SIGMA=   33.5 PHAS=      1.9 FOM=  0.08 TEST= 0
INDE  25  49  32 FOBS=     32.2 SIGMA=    6.6 PHAS=   -125.9 FOM=  0.41 TEST= 0
INDE  25  49  34 FOBS=     14.6 SIGMA=   15.9 PHAS=   -173.0 FOM=  0.14 TEST= 1
INDE  25  49  36 FOBS=     68.5 SIGMA=    2.9 PHAS=     69.1 FOM=  0.83 TEST= 0
INDE  25  49  38 FOBS=     54.6 SIGMA=    3.7 PHAS=    -72.5 FOM=  0.38 TEST= 1
INDE  25  49  40 FOBS=     22.8 SIGMA=    8.6 PHAS=    -99.9 FOM=  0.21 TEST= 0
INDE  25  49  42 FOBS=     68.1 SIGMA=    2.7 PHAS=    -80.5 FOM=  0.83 TEST= 0
INDE  25  49  44 FOBS=      0.0 SIGMA=   19.7 PHAS=      0.0 FOM=  0.00 TEST= 0
INDE  25  49  46 FOBS=     16.7 SIGMA=   11.7 PHAS=    -23.4 FOM=  0.14 TEST= 0
INDE  25  49  48 FOBS=     93.7 SIGMA=    2.0 PHAS=      7.9 FOM=  0.93 TEST= 0
INDE  25  49  50 FOBS=     90.0 SIGMA=    2.2 PHAS=     70.6 FOM=  0.91 TEST= 0
INDE  25  49  52 FOBS=     89.7 SIGMA=    2.6 PHAS=    151.7 FOM=  0.94 TEST= 0
INDE  25  49  54 FOBS=     88.9 SIGMA=    3.2 PHAS=    -47.9 FOM=  0.91 TEST= 0
INDE  25  50  25 FOBS=    124.6 SIGMA=    1.4 PHAS=   -163.1 FOM=  0.97 TEST= 0
INDE  25  50  27 FOBS=     91.9 SIGMA=    2.2 PHAS=    -60.6 FOM=  0.69 TEST= 0
INDE  25  50  29 FOBS=     92.7 SIGMA=    2.5 PHAS=    153.1 FOM=  0.69 TEST= 1
INDE  25  50  31 FOBS=     51.5 SIGMA=    3.8 PHAS=   -125.5 FOM=  0.81 TEST= 0
INDE  25  50  33 FOBS=     85.2 SIGMA=    2.3 PHAS=     91.9 FOM=  0.88 TEST= 0
INDE  25  50  35 FOBS=     74.6 SIGMA=    2.7 PHAS=     52.1 FOM=  0.87 TEST= 0
INDE  25  50  37 FOBS=      0.0 SIGMA=   20.4 PHAS=      0.0 FOM=  0.00 TEST= 0
INDE  25  50  39 FOBS=     81.5 SIGMA=    2.5 PHAS=    -10.3 FOM=  0.48 TEST= 0
INDE  25  50  41 FOBS=     31.9 SIGMA=    6.0 PHAS=    -25.7 FOM=  0.11 TEST= 1
INDE  25  50  43 FOBS=     31.6 SIGMA=    6.0 PHAS=   -156.4 FOM=  0.06 TEST= 1
INDE  25  50  45 FOBS=     84.4 SIGMA=    2.2 PHAS=     64.0 FOM=  0.91 TEST= 0
INDE  25  50  47 FOBS=    104.5 SIGMA=    2.1 PHAS=    -69.0 FOM=  0.94 TEST= 0
INDE  25  50  49 FOBS=     64.5 SIGMA=    3.6 PHAS=    -87.4 FOM=  0.91 TEST= 0
INDE  25  50  51 FOBS=     49.0 SIGMA=    4.8 PHAS=     58.8 FOM=  0.85 TEST= 0
INDE  25  50  53 FOBS=     38.2 SIGMA=    9.6 PHAS=   -148.1 FOM=  0.56 TEST= 0
INDE  25  51  26 FOBS=     34.0 SIGMA=    4.8 PHAS=     89.8 FOM=  0.37 TEST= 1
INDE  25  51  28 FOBS=     64.2 SIGMA=    3.5 PHAS=     62.6 FOM=  0.75 TEST= 0
INDE  25  51  30 FOBS=     87.5 SIGMA=    2.6 PHAS=     68.5 FOM=  0.94 TEST= 0
INDE  25  51  32 FOBS=     47.0 SIGMA=    4.1 PHAS=    -22.2 FOM=  0.71 TEST= 0
INDE  25  51  34 FOBS=      0.0 SIGMA=   20.3 PHAS=      0.0 FOM=  0.00 TEST= 0
INDE  25  51  36 FOBS=     14.7 SIGMA=   15.1 PHAS=    -95.7 FOM=  0.09 TEST= 1
INDE  25  51  38 FOBS=     84.3 SIGMA=    2.4 PHAS=   -100.3 FOM=  0.90 TEST= 0
INDE  25  51  40 FOBS=     91.2 SIGMA=    2.3 PHAS=    -86.0 FOM=  0.73 TEST= 0
INDE  25  51  42 FOBS=     56.9 SIGMA=    3.5 PHAS=   -123.9 FOM=  0.70 TEST= 0
INDE  25  51  44 FOBS=     95.3 SIGMA=    2.3 PHAS=   -151.8 FOM=  0.85 TEST= 0
```

*FIG. 12A - 502*

```
INDE 25 51 46 FOBS=    57.8 SIGMA=  4.0 PHAS=   63.8 FOM= 0.04 TEST= 1
INDE 25 51 48 FOBS=    42.7 SIGMA=  6.5 PHAS= -154.9 FOM= 0.60 TEST= 0
INDE 25 51 50 FOBS=    48.8 SIGMA=  5.3 PHAS=    5.3 FOM= 0.74 TEST= 0
INDE 25 51 52 FOBS=     0.0 SIGMA= 25.5 PHAS=    0.0 FOM= 0.00 TEST= 0
INDE 25 52 25 FOBS=    25.7 SIGMA=  6.7 PHAS=   70.3 FOM= 0.40 TEST= 0
INDE 25 52 27 FOBS=    69.4 SIGMA=  2.5 PHAS=  -28.9 FOM= 0.80 TEST= 0
INDE 25 52 29 FOBS=   111.3 SIGMA=  2.1 PHAS=  -18.5 FOM= 0.90 TEST= 0
INDE 25 52 31 FOBS=    54.1 SIGMA=  4.5 PHAS= -150.1 FOM= 0.78 TEST= 0
INDE 25 52 33 FOBS=    59.4 SIGMA=  3.3 PHAS=   48.8 FOM= 0.24 TEST= 1
INDE 25 52 35 FOBS=     0.0 SIGMA= 20.3 PHAS=    0.0 FOM= 0.00 TEST= 1
INDE 25 52 37 FOBS=    83.0 SIGMA=  2.4 PHAS= -146.6 FOM= 0.85 TEST= 0
INDE 25 52 39 FOBS=    25.8 SIGMA= 10.1 PHAS=  134.1 FOM= 0.53 TEST= 0
INDE 25 52 41 FOBS=    14.7 SIGMA= 18.2 PHAS=   51.2 FOM= 0.17 TEST= 0
INDE 25 52 43 FOBS=    68.7 SIGMA=  3.7 PHAS=  -70.1 FOM= 0.01 TEST= 1
INDE 25 52 45 FOBS=    20.5 SIGMA= 13.4 PHAS=  -39.6 FOM= 0.29 TEST= 0
INDE 25 52 47 FOBS=    55.0 SIGMA=  4.7 PHAS=  -61.8 FOM= 0.74 TEST= 0
INDE 25 52 49 FOBS=   105.6 SIGMA=  2.5 PHAS= -131.4 FOM= 0.95 TEST= 0
INDE 25 52 51 FOBS=    40.1 SIGMA=  8.3 PHAS= -105.9 FOM= 0.17 TEST= 0
INDE 25 53 26 FOBS=    17.0 SIGMA= 12.3 PHAS=   12.9 FOM= 0.18 TEST= 0
INDE 25 53 28 FOBS=    70.9 SIGMA=  2.7 PHAS=  -80.7 FOM= 0.90 TEST= 0
INDE 25 53 30 FOBS=    79.2 SIGMA=  2.9 PHAS=  143.3 FOM= 0.47 TEST= 1
INDE 25 53 32 FOBS=    11.8 SIGMA= 21.2 PHAS=   23.0 FOM= 0.06 TEST= 0
INDE 25 53 34 FOBS=    12.5 SIGMA= 20.0 PHAS=   41.6 FOM= 0.07 TEST= 0
INDE 25 53 36 FOBS=     9.8 SIGMA= 21.5 PHAS= -154.0 FOM= 0.13 TEST= 0
INDE 25 53 38 FOBS=     0.0 SIGMA= 22.7 PHAS=    0.0 FOM= 0.00 TEST= 0
INDE 25 53 40 FOBS=    23.0 SIGMA= 13.3 PHAS=    0.9 FOM= 0.29 TEST= 0
INDE 25 53 42 FOBS=    55.3 SIGMA=  4.5 PHAS= -163.2 FOM= 0.83 TEST= 0
INDE 25 53 44 FOBS=    27.2 SIGMA= 10.0 PHAS= -145.4 FOM= 0.82 TEST= 0
INDE 25 53 46 FOBS=    67.0 SIGMA=  3.9 PHAS=  155.7 FOM= 0.81 TEST= 0
INDE 25 53 48 FOBS=    74.1 SIGMA=  3.6 PHAS=  119.7 FOM= 0.91 TEST= 0
INDE 25 53 50 FOBS=   106.4 SIGMA=  3.3 PHAS=  115.4 FOM= 0.94 TEST= 0
INDE 25 54 25 FOBS=    32.2 SIGMA=  6.0 PHAS=    2.1 FOM= 0.25 TEST= 0
INDE 25 54 27 FOBS=    36.4 SIGMA=  4.5 PHAS=  113.1 FOM= 0.54 TEST= 0
INDE 25 54 29 FOBS=   144.7 SIGMA=  1.4 PHAS=  -74.9 FOM= 0.93 TEST= 0
INDE 25 54 31 FOBS=    77.8 SIGMA=  2.9 PHAS=   19.0 FOM= 0.74 TEST= 0
INDE 25 54 33 FOBS=     0.0 SIGMA= 22.3 PHAS=    0.0 FOM= 0.00 TEST= 0
INDE 25 54 35 FOBS=     0.0 SIGMA= 23.9 PHAS=    0.0 FOM= 0.00 TEST= 0
INDE 25 54 37 FOBS=     0.0 SIGMA= 26.0 PHAS=    0.0 FOM= 0.00 TEST= 0
INDE 25 54 39 FOBS=    18.1 SIGMA= 18.7 PHAS=   69.2 FOM= 0.07 TEST= 1
INDE 25 54 41 FOBS=    59.4 SIGMA=  5.2 PHAS=   60.3 FOM= 0.89 TEST= 0
INDE 25 54 43 FOBS=    77.2 SIGMA=  3.3 PHAS=   83.6 FOM= 0.89 TEST= 0
INDE 25 54 45 FOBS=    51.3 SIGMA=  5.1 PHAS=   14.0 FOM= 0.77 TEST= 0
INDE 25 54 47 FOBS=     0.0 SIGMA= 24.1 PHAS=    0.0 FOM= 0.00 TEST= 0
INDE 25 54 49 FOBS=   112.6 SIGMA=  3.2 PHAS=  -11.1 FOM= 0.94 TEST= 0
INDE 25 55 26 FOBS=   119.4 SIGMA=  1.5 PHAS=   40.9 FOM= 0.95 TEST= 0
INDE 25 55 28 FOBS=    36.1 SIGMA=  6.3 PHAS=  141.0 FOM= 0.33 TEST= 0
INDE 25 55 30 FOBS=   100.3 SIGMA=  2.5 PHAS=  -90.4 FOM= 0.93 TEST= 0
INDE 25 55 32 FOBS=    67.7 SIGMA=  4.8 PHAS= -156.9 FOM= 0.72 TEST= 1
INDE 25 55 34 FOBS=    37.2 SIGMA=  7.7 PHAS=  -47.1 FOM= 0.05 TEST= 1
INDE 25 55 36 FOBS=     0.0 SIGMA= 23.7 PHAS=    0.0 FOM= 0.00 TEST= 1
INDE 25 55 38 FOBS=     0.0 SIGMA= 24.3 PHAS=    0.0 FOM= 0.00 TEST= 0
INDE 25 55 40 FOBS=     0.0 SIGMA= 24.5 PHAS=    0.0 FOM= 0.00 TEST= 0
INDE 25 55 42 FOBS=    45.1 SIGMA=  6.9 PHAS=   -5.8 FOM= 0.40 TEST= 0
INDE 25 55 44 FOBS=     0.0 SIGMA= 23.4 PHAS=    0.0 FOM= 0.00 TEST= 0
INDE 25 55 46 FOBS=     0.0 SIGMA= 22.9 PHAS=    0.0 FOM= 0.00 TEST= 0
INDE 25 55 48 FOBS=     0.0 SIGMA= 27.7 PHAS=    0.0 FOM= 0.00 TEST= 0
INDE 25 56 25 FOBS=   165.2 SIGMA=  1.5 PHAS=  -52.8 FOM= 0.97 TEST= 0
INDE 25 56 27 FOBS=    80.6 SIGMA=  2.9 PHAS=  -23.0 FOM= 0.92 TEST= 0
INDE 25 56 29 FOBS=    81.7 SIGMA=  3.3 PHAS=   26.8 FOM= 0.17 TEST= 1
INDE 25 56 31 FOBS=    78.0 SIGMA=  3.5 PHAS=  137.7 FOM= 0.92 TEST= 0
INDE 25 56 33 FOBS=   111.0 SIGMA=  3.0 PHAS= -159.4 FOM= 0.85 TEST= 0
INDE 25 56 35 FOBS=    61.7 SIGMA=  4.7 PHAS=  115.2 FOM= 0.82 TEST= 0
INDE 25 56 37 FOBS=    61.5 SIGMA=  4.8 PHAS= -148.1 FOM= 0.74 TEST= 0
INDE 25 56 39 FOBS=     0.0 SIGMA= 24.3 PHAS=    0.0 FOM= 0.00 TEST= 0
INDE 25 56 41 FOBS=    34.6 SIGMA=  8.9 PHAS=   60.9 FOM= 0.60 TEST= 0
INDE 25 56 43 FOBS=    18.4 SIGMA= 13.9 PHAS=  134.5 FOM= 0.40 TEST= 0
INDE 25 56 45 FOBS=    86.4 SIGMA=  3.5 PHAS=  -45.4 FOM= 0.84 TEST= 0
INDE 25 56 47 FOBS=    42.2 SIGMA=  8.0 PHAS= -127.3 FOM= 0.64 TEST= 0
INDE 25 57 26 FOBS=   118.0 SIGMA=  2.3 PHAS=  173.5 FOM= 0.95 TEST= 0
INDE 25 57 28 FOBS=   238.5 SIGMA=  1.1 PHAS= -114.7 FOM= 0.45 TEST= 1
```

*FIG. 12A - 503*

```
INDE  25  57  30 FOBS=   28.1 SIGMA=   9.6 PHAS= -129.7 FOM= 0.25 TEST= 0
INDE  25  57  32 FOBS=   61.6 SIGMA=   4.4 PHAS=   67.9 FOM= 0.84 TEST= 0
INDE  25  57  34 FOBS=   54.6 SIGMA=   6.1 PHAS=   59.6 FOM= 0.77 TEST= 0
INDE  25  57  36 FOBS=  134.5 SIGMA=   2.3 PHAS=   58.6 FOM= 0.96 TEST= 0
INDE  25  57  38 FOBS=   79.2 SIGMA=   3.8 PHAS=  -17.7 FOM= 0.78 TEST= 0
INDE  25  57  40 FOBS=    0.0 SIGMA=  24.6 PHAS=    0.0 FOM= 0.00 TEST= 0
INDE  25  57  42 FOBS=   88.1 SIGMA=   3.7 PHAS=   79.3 FOM= 0.80 TEST= 0
INDE  25  57  44 FOBS=   78.5 SIGMA=   3.4 PHAS= -117.1 FOM= 0.88 TEST= 0
INDE  25  57  46 FOBS=   56.1 SIGMA=   5.9 PHAS= -124.9 FOM= 0.82 TEST= 0
INDE  25  58  25 FOBS=    1.4 SIGMA= 163.7 PHAS=  -11.3 FOM= 0.01 TEST= 0
INDE  25  58  27 FOBS=  136.2 SIGMA=   1.8 PHAS=   23.0 FOM= 0.95 TEST= 0
INDE  25  58  29 FOBS=  121.9 SIGMA=   2.3 PHAS=   51.2 FOM= 0.95 TEST= 0
INDE  25  58  31 FOBS=    0.0 SIGMA=  23.2 PHAS=    0.0 FOM= 0.00 TEST= 0
INDE  25  58  33 FOBS=   53.8 SIGMA=   5.2 PHAS= -100.9 FOM= 0.76 TEST= 0
INDE  25  58  35 FOBS=   96.7 SIGMA=   3.1 PHAS=   -0.2 FOM= 0.95 TEST= 0
INDE  25  58  37 FOBS=   66.3 SIGMA=   4.5 PHAS=  -44.8 FOM= 0.79 TEST= 0
INDE  25  58  39 FOBS=    0.0 SIGMA=  24.4 PHAS=    0.0 FOM= 0.00 TEST= 0
INDE  25  58  41 FOBS=  145.7 SIGMA=   2.3 PHAS=   32.6 FOM= 0.96 TEST= 0
INDE  25  58  43 FOBS=    0.0 SIGMA=  25.3 PHAS=    0.0 FOM= 0.00 TEST= 0
INDE  25  58  45 FOBS=   38.0 SIGMA=   8.7 PHAS=  169.4 FOM= 0.80 TEST= 0
INDE  25  59  26 FOBS=   48.7 SIGMA=   7.1 PHAS= -123.4 FOM= 0.26 TEST= 0
INDE  25  59  28 FOBS=   36.7 SIGMA=   6.3 PHAS=    5.6 FOM= 0.54 TEST= 0
INDE  25  59  30 FOBS=   33.7 SIGMA=   8.0 PHAS=  -51.6 FOM= 0.50 TEST= 0
INDE  25  59  32 FOBS=   14.0 SIGMA=  19.6 PHAS=  -29.0 FOM= 0.21 TEST= 0
INDE  25  59  34 FOBS=    0.0 SIGMA=  23.6 PHAS=    0.0 FOM= 0.00 TEST= 0
INDE  25  59  36 FOBS=   48.6 SIGMA=   6.1 PHAS=   11.2 FOM= 0.64 TEST= 0
INDE  25  59  38 FOBS=   22.4 SIGMA=  13.4 PHAS=  159.6 FOM= 0.36 TEST= 0
INDE  25  59  40 FOBS=  102.6 SIGMA=   3.6 PHAS=  -82.7 FOM= 0.83 TEST= 0
INDE  25  59  42 FOBS=    0.0 SIGMA=  25.2 PHAS=    0.0 FOM= 0.00 TEST= 0
INDE  25  59  44 FOBS=  114.2 SIGMA=   6.0 PHAS=   38.8 FOM= 0.91 TEST= 0
INDE  25  60  25 FOBS=   15.3 SIGMA=  24.5 PHAS=  -62.2 FOM= 0.30 TEST= 0
INDE  25  60  27 FOBS=   75.9 SIGMA=   3.1 PHAS=  -66.2 FOM= 0.92 TEST= 0
INDE  25  60  29 FOBS=    0.0 SIGMA=  22.6 PHAS=    0.0 FOM= 0.00 TEST= 0
INDE  25  60  31 FOBS=    0.0 SIGMA=  25.1 PHAS=    0.0 FOM= 0.00 TEST= 0
INDE  25  60  33 FOBS=   14.8 SIGMA=  19.0 PHAS=   30.0 FOM= 0.30 TEST= 0
INDE  25  60  35 FOBS=   32.0 SIGMA=   9.0 PHAS=  104.7 FOM= 0.14 TEST= 0
INDE  25  60  37 FOBS=   45.4 SIGMA=   6.6 PHAS=  -11.8 FOM= 0.69 TEST= 0
INDE  25  60  39 FOBS=    0.0 SIGMA=  26.3 PHAS=    0.0 FOM= 0.00 TEST= 0
INDE  25  60  41 FOBS=   42.5 SIGMA=   7.5 PHAS=   35.9 FOM= 0.37 TEST= 0
INDE  25  61  26 FOBS=  104.4 SIGMA=   2.9 PHAS=  136.2 FOM= 0.28 TEST= 1
INDE  25  61  28 FOBS=   98.2 SIGMA=   2.5 PHAS=  163.3 FOM= 0.94 TEST= 0
INDE  25  61  30 FOBS=   76.2 SIGMA=   3.6 PHAS= -175.7 FOM= 0.79 TEST= 0
INDE  25  61  32 FOBS=   41.6 SIGMA=   6.7 PHAS=  -20.1 FOM= 0.74 TEST= 0
INDE  25  61  34 FOBS=   35.8 SIGMA=   7.9 PHAS=   39.2 FOM= 0.32 TEST= 0
INDE  25  61  36 FOBS=    0.0 SIGMA=  21.7 PHAS=    0.0 FOM= 0.00 TEST= 1
INDE  25  61  38 FOBS=    0.0 SIGMA=  24.8 PHAS=    0.0 FOM= 0.00 TEST= 0
INDE  25  61  40 FOBS=    0.0 SIGMA=  30.2 PHAS=    0.0 FOM= 0.00 TEST= 0
INDE  25  62  25 FOBS=   31.3 SIGMA=   9.4 PHAS=  -72.6 FOM= 0.60 TEST= 0
INDE  25  62  27 FOBS=   73.4 SIGMA=   3.2 PHAS=   66.6 FOM= 0.77 TEST= 0
INDE  25  62  29 FOBS=   74.8 SIGMA=   3.2 PHAS=   62.3 FOM= 0.86 TEST= 0
INDE  25  62  31 FOBS=    0.0 SIGMA=  24.9 PHAS=    0.0 FOM= 0.00 TEST= 0
INDE  25  62  33 FOBS=   36.3 SIGMA=   7.8 PHAS=  132.6 FOM= 0.55 TEST= 0
INDE  25  62  35 FOBS=   47.5 SIGMA=   6.1 PHAS=  136.9 FOM= 0.76 TEST= 0
INDE  25  62  37 FOBS=    0.0 SIGMA=  21.9 PHAS=    0.0 FOM= 0.00 TEST= 0
INDE  25  62  39 FOBS=    0.0 SIGMA=  30.5 PHAS=    0.0 FOM= 0.00 TEST= 0
INDE  25  63  26 FOBS=   77.1 SIGMA=   4.0 PHAS= -170.0 FOM= 0.63 TEST= 1
INDE  25  63  28 FOBS=    0.0 SIGMA=  22.7 PHAS=    0.0 FOM= 0.00 TEST= 0
INDE  25  63  30 FOBS=   25.4 SIGMA=   9.4 PHAS=  163.2 FOM= 0.15 TEST= 0
INDE  25  63  32 FOBS=   41.8 SIGMA=   6.7 PHAS=   -9.3 FOM= 0.86 TEST= 0
INDE  25  63  34 FOBS=   95.0 SIGMA=   3.1 PHAS=  101.3 FOM= 0.91 TEST= 0
INDE  25  63  36 FOBS=   60.6 SIGMA=   5.0 PHAS=   73.6 FOM= 0.43 TEST= 1
INDE  25  63  38 FOBS=   33.3 SIGMA=  12.6 PHAS=  116.0 FOM= 0.36 TEST= 0
INDE  25  64  25 FOBS=   42.2 SIGMA=   7.0 PHAS=  152.9 FOM= 0.28 TEST= 0
INDE  25  64  27 FOBS=   80.1 SIGMA=   3.9 PHAS=  130.4 FOM= 0.83 TEST= 0
INDE  25  64  29 FOBS=   59.4 SIGMA=   4.5 PHAS=  -55.9 FOM= 0.87 TEST= 0
INDE  25  64  31 FOBS=   26.9 SIGMA=  14.2 PHAS= -162.2 FOM= 0.56 TEST= 0
INDE  25  64  33 FOBS=   30.4 SIGMA=  13.1 PHAS=  -31.3 FOM= 0.39 TEST= 0
INDE  25  64  35 FOBS=   74.9 SIGMA=   4.7 PHAS=  -35.9 FOM= 0.91 TEST= 0
INDE  25  65  26 FOBS=   37.3 SIGMA=  10.1 PHAS=   34.7 FOM= 0.53 TEST= 0
INDE  25  65  28 FOBS=   30.2 SIGMA=  10.3 PHAS=  176.3 FOM= 0.59 TEST= 0
```

*FIG. 12A - 504*

```
INDE 25 65 30 FOBS=    29.6 SIGMA=  9.1 PHAS=  120.7 FOM= 0.15 TEST= 0
INDE 25 65 32 FOBS=    66.1 SIGMA=  5.1 PHAS=   -3.3 FOM= 0.82 TEST= 0
INDE 25 65 34 FOBS=    88.2 SIGMA=  4.0 PHAS= -175.4 FOM= 0.95 TEST= 0
INDE 25 66 25 FOBS=     0.0 SIGMA= 30.5 PHAS=    0.0 FOM= 0.00 TEST= 0
INDE 25 66 27 FOBS=    27.3 SIGMA= 14.0 PHAS=  135.6 FOM= 0.41 TEST= 0
INDE 25 66 29 FOBS=    79.0 SIGMA=  5.0 PHAS=   40.0 FOM= 0.90 TEST= 0
INDE 25 66 31 FOBS=    76.6 SIGMA=  4.3 PHAS= -162.3 FOM= 0.91 TEST= 0
INDE 25 67 26 FOBS=    16.5 SIGMA= 28.5 PHAS=    1.3 FOM= 0.17 TEST= 0
INDE 25 67 28 FOBS=    19.1 SIGMA= 26.7 PHAS=  179.6 FOM= 0.24 TEST= 0
INDE 25 67 30 FOBS=    59.7 SIGMA=  6.5 PHAS=    2.2 FOM= 0.71 TEST= 0
INDE 25 68 25 FOBS=     0.0 SIGMA= 30.9 PHAS=    0.0 FOM= 0.00 TEST= 0
INDE 25 68 27 FOBS=    41.5 SIGMA= 12.1 PHAS=    7.7 FOM= 0.47 TEST= 0
INDE 26 26 26 FOBS=   180.4 SIGMA=  1.7 PHAS= -118.9 FOM= 0.97 TEST= 0
INDE 26 27 27 FOBS=   133.7 SIGMA=  1.3 PHAS=   88.9 FOM= 0.88 TEST= 0
INDE 26 27 29 FOBS=    50.4 SIGMA=  3.5 PHAS=  106.3 FOM= 0.72 TEST= 0
INDE 26 27 31 FOBS=    15.1 SIGMA= 12.5 PHAS=  -68.6 FOM= 0.28 TEST= 0
INDE 26 27 33 FOBS=   232.8 SIGMA=  0.9 PHAS=  -25.9 FOM= 0.96 TEST= 0
INDE 26 27 35 FOBS=   161.7 SIGMA=  1.1 PHAS=  -60.7 FOM= 0.92 TEST= 0
INDE 26 27 37 FOBS=   196.1 SIGMA=  0.9 PHAS=   -9.5 FOM= 0.93 TEST= 0
INDE 26 27 39 FOBS=     0.0 SIGMA= 18.8 PHAS=    0.0 FOM= 0.00 TEST= 0
INDE 26 27 41 FOBS=    80.4 SIGMA=  2.0 PHAS=  145.1 FOM= 0.84 TEST= 0
INDE 26 27 43 FOBS=    33.7 SIGMA=  4.9 PHAS=  -60.7 FOM= 0.21 TEST= 1
INDE 26 27 45 FOBS=     0.0 SIGMA= 18.4 PHAS=    0.0 FOM= 0.00 TEST= 0
INDE 26 27 47 FOBS=    82.8 SIGMA=  2.1 PHAS=  168.0 FOM= 0.90 TEST= 0
INDE 26 27 49 FOBS=   114.7 SIGMA=  1.5 PHAS=  -83.4 FOM= 0.95 TEST= 0
INDE 26 27 51 FOBS=    77.0 SIGMA=  2.2 PHAS=  -33.8 FOM= 0.80 TEST= 0
INDE 26 27 53 FOBS=    72.9 SIGMA=  2.6 PHAS=  150.6 FOM= 0.80 TEST= 0
INDE 26 27 55 FOBS=    77.2 SIGMA=  2.9 PHAS= -103.1 FOM= 0.60 TEST= 0
INDE 26 27 57 FOBS=    22.4 SIGMA=  9.0 PHAS=  -39.6 FOM= 0.31 TEST= 0
INDE 26 27 59 FOBS=    64.9 SIGMA=  4.7 PHAS=  -55.2 FOM= 0.84 TEST= 0
INDE 26 27 61 FOBS=     0.0 SIGMA= 24.4 PHAS=    0.0 FOM= 0.00 TEST= 0
INDE 26 27 63 FOBS=     0.0 SIGMA= 24.4 PHAS=    0.0 FOM= 0.00 TEST= 0
INDE 26 27 65 FOBS=     0.0 SIGMA= 27.8 PHAS=    0.0 FOM= 0.00 TEST= 0
INDE 26 27 67 FOBS=    39.7 SIGMA= 12.8 PHAS=  108.6 FOM= 0.55 TEST= 0
INDE 26 28 26 FOBS=    39.0 SIGMA=  4.8 PHAS=  135.8 FOM= 0.57 TEST= 0
INDE 26 28 28 FOBS=   150.4 SIGMA=  1.2 PHAS=   43.9 FOM= 0.93 TEST= 0
INDE 26 28 30 FOBS=   107.7 SIGMA=  1.8 PHAS=   56.4 FOM= 0.92 TEST= 1
INDE 26 28 32 FOBS=   224.9 SIGMA=  1.0 PHAS=  -96.6 FOM= 0.95 TEST= 0
INDE 26 28 34 FOBS=   303.3 SIGMA=  0.8 PHAS= -117.8 FOM= 0.99 TEST= 0
INDE 26 28 36 FOBS=   100.2 SIGMA=  1.7 PHAS=   -9.5 FOM= 0.89 TEST= 0
INDE 26 28 38 FOBS=   137.1 SIGMA=  1.3 PHAS= -169.3 FOM= 0.85 TEST= 0
INDE 26 28 40 FOBS=    67.8 SIGMA=  2.4 PHAS=  137.3 FOM= 0.66 TEST= 0
INDE 26 28 42 FOBS=   123.9 SIGMA=  1.4 PHAS=  -50.3 FOM= 0.72 TEST= 0
INDE 26 28 44 FOBS=    31.2 SIGMA=  5.5 PHAS=  178.0 FOM= 0.17 TEST= 0
INDE 26 28 46 FOBS=     5.0 SIGMA= 38.1 PHAS=   60.8 FOM= 0.02 TEST= 0
INDE 26 28 48 FOBS=   171.2 SIGMA=  1.1 PHAS=  123.8 FOM= 0.96 TEST= 0
INDE 26 28 50 FOBS=    50.4 SIGMA=  3.8 PHAS=  -46.7 FOM= 0.25 TEST= 0
INDE 26 28 52 FOBS=    29.2 SIGMA=  6.4 PHAS= -162.2 FOM= 0.32 TEST= 0
INDE 26 28 54 FOBS=    34.7 SIGMA=  6.8 PHAS=   71.5 FOM= 0.24 TEST= 0
INDE 26 28 56 FOBS=    32.7 SIGMA=  7.1 PHAS=  131.2 FOM= 0.33 TEST= 0
INDE 26 28 58 FOBS=   115.7 SIGMA=  2.1 PHAS=  156.5 FOM= 0.94 TEST= 0
INDE 26 28 60 FOBS=     0.0 SIGMA= 24.6 PHAS=    0.0 FOM= 0.00 TEST= 0
INDE 26 28 62 FOBS=     0.0 SIGMA= 27.5 PHAS=    0.0 FOM= 0.00 TEST= 0
INDE 26 28 64 FOBS=    67.3 SIGMA=  5.7 PHAS=   26.4 FOM= 0.62 TEST= 0
INDE 26 28 66 FOBS=    52.2 SIGMA=  9.7 PHAS=  -66.7 FOM= 0.24 TEST= 1
INDE 26 29 27 FOBS=   209.2 SIGMA=  1.1 PHAS=   36.0 FOM= 0.97 TEST= 0
INDE 26 29 29 FOBS=   281.5 SIGMA=  0.8 PHAS=  -65.7 FOM= 0.95 TEST= 0
INDE 26 29 31 FOBS=   179.4 SIGMA=  1.1 PHAS=   -2.7 FOM= 0.94 TEST= 0
INDE 26 29 33 FOBS=   237.0 SIGMA=  1.0 PHAS=  148.9 FOM= 0.93 TEST= 1
INDE 26 29 35 FOBS=   277.4 SIGMA=  0.8 PHAS= -119.2 FOM= 0.95 TEST= 0
INDE 26 29 37 FOBS=    78.4 SIGMA=  2.4 PHAS=  -95.7 FOM= 0.79 TEST= 0
INDE 26 29 39 FOBS=     3.9 SIGMA= 42.2 PHAS=   51.9 FOM= 0.01 TEST= 0
INDE 26 29 41 FOBS=     0.0 SIGMA= 18.3 PHAS=    0.0 FOM= 0.00 TEST= 1
INDE 26 29 43 FOBS=    40.5 SIGMA=  3.9 PHAS=   64.2 FOM= 0.43 TEST= 0
INDE 26 29 45 FOBS=    48.6 SIGMA=  3.6 PHAS=  -39.9 FOM= 0.60 TEST= 0
INDE 26 29 47 FOBS=    64.1 SIGMA=  2.7 PHAS=   -5.9 FOM= 0.86 TEST= 0
INDE 26 29 49 FOBS=   110.3 SIGMA=  1.6 PHAS=  -36.0 FOM= 0.71 TEST= 1
INDE 26 29 51 FOBS=    50.3 SIGMA=  3.3 PHAS= -152.4 FOM= 0.57 TEST= 0
INDE 26 29 53 FOBS=     0.0 SIGMA= 19.9 PHAS=    0.0 FOM= 0.00 TEST= 0
INDE 26 29 55 FOBS=   102.1 SIGMA=  2.4 PHAS= -151.5 FOM= 0.78 TEST= 0
```

*FIG. 12A - 505*

```
INDE  26  29  57  FOBS=   74.2  SIGMA=   4.2  PHAS=   90.1  FOM=  0.92  TEST=  0
INDE  26  29  59  FOBS=   93.4  SIGMA=   3.4  PHAS=   35.5  FOM=  0.92  TEST=  0
INDE  26  29  61  FOBS=    2.9  SIGMA=  92.2  PHAS=  -65.9  FOM=  0.04  TEST=  0
INDE  26  29  63  FOBS=    0.0  SIGMA=  27.5  PHAS=    0.0  FOM=  0.00  TEST=  1
INDE  26  29  65  FOBS=   43.0  SIGMA=  11.7  PHAS=   20.6  FOM=  0.62  TEST=  0
INDE  26  29  67  FOBS=   44.7  SIGMA=  11.5  PHAS=  -52.7  FOM=  0.05  TEST=  1
INDE  26  30  26  FOBS=  130.0  SIGMA=   1.5  PHAS= -125.6  FOM=  0.90  TEST=  0
INDE  26  30  28  FOBS=  140.2  SIGMA=   1.7  PHAS= -115.1  FOM=  0.95  TEST=  0
INDE  26  30  30  FOBS=  139.5  SIGMA=   1.4  PHAS= -158.0  FOM=  0.92  TEST=  0
INDE  26  30  32  FOBS=   47.8  SIGMA=   4.0  PHAS=  -22.5  FOM=  0.22  TEST=  0
INDE  26  30  34  FOBS=  138.2  SIGMA=   1.5  PHAS=  139.6  FOM=  0.87  TEST=  0
INDE  26  30  36  FOBS=    9.3  SIGMA=  19.8  PHAS=  179.8  FOM=  0.06  TEST=  0
INDE  26  30  38  FOBS=  165.4  SIGMA=   1.2  PHAS= -142.6  FOM=  0.56  TEST=  1
INDE  26  30  40  FOBS=   82.1  SIGMA=   2.0  PHAS=  151.6  FOM=  0.93  TEST=  0
INDE  26  30  42  FOBS=  134.5  SIGMA=   1.3  PHAS=  -18.8  FOM=  0.76  TEST=  0
INDE  26  30  44  FOBS=  102.3  SIGMA=   1.6  PHAS= -111.6  FOM=  0.91  TEST=  0
INDE  26  30  46  FOBS=   97.4  SIGMA=   1.8  PHAS= -131.0  FOM=  0.89  TEST=  0
INDE  26  30  48  FOBS=   35.9  SIGMA=   4.7  PHAS= -173.3  FOM=  0.39  TEST=  0
INDE  26  30  50  FOBS=   74.3  SIGMA=   2.3  PHAS=   41.3  FOM=  0.84  TEST=  0
INDE  26  30  52  FOBS=   69.8  SIGMA=   2.4  PHAS= -164.6  FOM=  0.87  TEST=  0
INDE  26  30  54  FOBS=   75.9  SIGMA=   2.7  PHAS=  104.7  FOM=  0.83  TEST=  0
INDE  26  30  56  FOBS=   46.6  SIGMA=   6.6  PHAS=  153.5  FOM=  0.67  TEST=  0
INDE  26  30  58  FOBS=   26.2  SIGMA=  14.8  PHAS=    6.9  FOM=  0.47  TEST=  0
INDE  26  30  60  FOBS=   59.9  SIGMA=   5.2  PHAS=  -88.6  FOM=  0.79  TEST=  0
INDE  26  30  62  FOBS=    0.0  SIGMA=  24.7  PHAS=    0.0  FOM=  0.00  TEST=  0
INDE  26  30  64  FOBS=   55.1  SIGMA=   9.3  PHAS=  -72.0  FOM=  0.83  TEST=  0
INDE  26  30  66  FOBS=   20.8  SIGMA=  24.8  PHAS=  -64.9  FOM=  0.57  TEST=  0
INDE  26  31  27  FOBS=  120.5  SIGMA=   1.8  PHAS=   87.5  FOM=  0.95  TEST=  0
INDE  26  31  29  FOBS=  170.0  SIGMA=   1.3  PHAS=  104.0  FOM=  0.95  TEST=  0
INDE  26  31  31  FOBS=  312.7  SIGMA=   0.7  PHAS=   43.4  FOM=  0.97  TEST=  0
INDE  26  31  33  FOBS=  186.0  SIGMA=   1.1  PHAS=   20.3  FOM=  0.91  TEST=  0
INDE  26  31  35  FOBS=  157.2  SIGMA=   1.3  PHAS= -142.2  FOM=  0.91  TEST=  0
INDE  26  31  37  FOBS=  154.0  SIGMA=   1.3  PHAS=  166.1  FOM=  0.94  TEST=  0
INDE  26  31  39  FOBS=  142.0  SIGMA=   1.3  PHAS=   42.9  FOM=  0.92  TEST=  0
INDE  26  31  41  FOBS=  124.8  SIGMA=   1.5  PHAS=  -54.1  FOM=  0.55  TEST=  1
INDE  26  31  43  FOBS=   48.0  SIGMA=   3.3  PHAS=  -38.8  FOM=  0.65  TEST=  0
INDE  26  31  45  FOBS=    0.0  SIGMA=  18.1  PHAS=    0.0  FOM=  0.00  TEST=  0
INDE  26  31  47  FOBS=   81.3  SIGMA=   2.1  PHAS=  121.2  FOM=  0.88  TEST=  0
INDE  26  31  49  FOBS=   36.3  SIGMA=   4.6  PHAS=   56.8  FOM=  0.40  TEST=  0
INDE  26  31  51  FOBS=  107.0  SIGMA=   1.6  PHAS=  116.6  FOM=  0.90  TEST=  0
INDE  26  31  53  FOBS=   84.2  SIGMA=   2.2  PHAS=   85.5  FOM=  0.33  TEST=  1
INDE  26  31  55  FOBS=   57.3  SIGMA=   4.1  PHAS=   98.7  FOM=  0.53  TEST=  0
INDE  26  31  57  FOBS=   97.0  SIGMA=   2.9  PHAS=  100.7  FOM=  0.91  TEST=  0
INDE  26  31  59  FOBS=   73.5  SIGMA=   4.3  PHAS=  118.0  FOM=  0.28  TEST=  1
INDE  26  31  61  FOBS=   65.3  SIGMA=   4.8  PHAS=  -84.7  FOM=  0.89  TEST=  0
INDE  26  31  63  FOBS=   33.0  SIGMA=   9.6  PHAS=  172.6  FOM=  0.74  TEST=  0
INDE  26  31  65  FOBS=  100.0  SIGMA=   5.3  PHAS= -167.1  FOM=  0.90  TEST=  0
INDE  26  32  26  FOBS=  149.0  SIGMA=   1.4  PHAS=  -66.1  FOM=  0.92  TEST=  0
INDE  26  32  28  FOBS=  222.4  SIGMA=   1.0  PHAS=    4.4  FOM=  0.89  TEST=  0
INDE  26  32  30  FOBS=  270.7  SIGMA=   0.9  PHAS=   -1.3  FOM=  0.97  TEST=  0
INDE  26  32  32  FOBS=   79.1  SIGMA=   2.4  PHAS= -139.0  FOM=  0.77  TEST=  0
INDE  26  32  34  FOBS=  106.3  SIGMA=   1.8  PHAS=  165.6  FOM=  0.89  TEST=  0
INDE  26  32  36  FOBS=  164.0  SIGMA=   1.2  PHAS=  107.0  FOM=  0.71  TEST=  1
INDE  26  32  38  FOBS=   27.6  SIGMA=   7.0  PHAS=   29.9  FOM=  0.30  TEST=  0
INDE  26  32  40  FOBS=   89.8  SIGMA=   2.0  PHAS= -175.0  FOM=  0.86  TEST=  0
INDE  26  32  42  FOBS=  125.7  SIGMA=   1.5  PHAS= -160.7  FOM=  0.92  TEST=  0
INDE  26  32  44  FOBS=  113.9  SIGMA=   1.5  PHAS=  -84.0  FOM=  0.92  TEST=  0
INDE  26  32  46  FOBS=   60.0  SIGMA=   2.7  PHAS=  -90.8  FOM=  0.91  TEST=  0
INDE  26  32  48  FOBS=   96.2  SIGMA=   1.8  PHAS=   44.1  FOM=  0.92  TEST=  0
INDE  26  32  50  FOBS=  162.0  SIGMA=   1.1  PHAS=   31.8  FOM=  0.83  TEST=  1
INDE  26  32  52  FOBS=   21.1  SIGMA=  14.7  PHAS=   20.2  FOM=  0.20  TEST=  0
INDE  26  32  54  FOBS=   36.0  SIGMA=   7.5  PHAS=  128.5  FOM=  0.43  TEST=  0
INDE  26  32  56  FOBS=   25.4  SIGMA=  10.5  PHAS=    2.4  FOM=  0.42  TEST=  0
INDE  26  32  58  FOBS=   58.3  SIGMA=   4.1  PHAS=  -14.6  FOM=  0.65  TEST=  0
INDE  26  32  60  FOBS=   78.7  SIGMA=   4.1  PHAS=  152.7  FOM=  0.86  TEST=  0
INDE  26  32  62  FOBS=   40.0  SIGMA=   8.0  PHAS=   92.1  FOM=  0.46  TEST=  0
INDE  26  32  64  FOBS=    0.0  SIGMA=  27.8  PHAS=    0.0  FOM=  0.00  TEST=  0
INDE  26  33  27  FOBS=  136.4  SIGMA=   1.5  PHAS= -138.4  FOM=  0.95  TEST=  0
INDE  26  33  29  FOBS=  286.5  SIGMA=   0.8  PHAS=  -81.7  FOM=  0.97  TEST=  0
INDE  26  33  31  FOBS=  265.3  SIGMA=   0.8  PHAS=    6.2  FOM=  0.95  TEST=  0
```

*FIG. 12A - 506*

```
INDE 26 33 33 FOBS=    244.7 SIGMA=   0.8 PHAS=   20.2 FOM= 0.97 TEST= 0
INDE 26 33 35 FOBS=      0.0 SIGMA=  19.0 PHAS=    0.0 FOM= 0.00 TEST= 0
INDE 26 33 37 FOBS=      0.0 SIGMA=  18.5 PHAS=    0.0 FOM= 0.00 TEST= 0
INDE 26 33 39 FOBS=    105.2 SIGMA=   1.6 PHAS=   62.4 FOM= 0.87 TEST= 0
INDE 26 33 41 FOBS=     53.4 SIGMA=   3.3 PHAS=  109.7 FOM= 0.70 TEST= 0
INDE 26 33 43 FOBS=    117.7 SIGMA=   1.5 PHAS=  136.9 FOM= 0.63 TEST= 0
INDE 26 33 45 FOBS=    102.4 SIGMA=   1.7 PHAS=  174.0 FOM= 0.93 TEST= 0
INDE 26 33 47 FOBS=     72.0 SIGMA=   2.2 PHAS=  175.5 FOM= 0.72 TEST= 1
INDE 26 33 49 FOBS=     58.3 SIGMA=   2.9 PHAS=  -85.2 FOM= 0.82 TEST= 0
INDE 26 33 51 FOBS=     70.1 SIGMA=   2.5 PHAS=   39.7 FOM= 0.85 TEST= 0
INDE 26 33 53 FOBS=    105.4 SIGMA=   2.1 PHAS=  -27.7 FOM= 0.95 TEST= 0
INDE 26 33 55 FOBS=     97.2 SIGMA=   2.5 PHAS=   25.7 FOM= 0.93 TEST= 0
INDE 26 33 57 FOBS=      0.0 SIGMA=  21.9 PHAS=    0.0 FOM= 0.00 TEST= 0
INDE 26 33 59 FOBS=     64.0 SIGMA=   3.8 PHAS=  111.6 FOM= 0.76 TEST= 0
INDE 26 33 61 FOBS=      0.0 SIGMA=  25.1 PHAS=    0.0 FOM= 0.00 TEST= 0
INDE 26 33 63 FOBS=      0.0 SIGMA=  25.0 PHAS=    0.0 FOM= 0.00 TEST= 0
INDE 26 33 65 FOBS=     28.3 SIGMA=  11.5 PHAS=  122.5 FOM= 0.33 TEST= 0
INDE 26 34 26 FOBS=    242.5 SIGMA=   0.9 PHAS=  -11.9 FOM= 0.98 TEST= 0
INDE 26 34 28 FOBS=    181.9 SIGMA=   1.1 PHAS=  135.2 FOM= 0.91 TEST= 0
INDE 26 34 30 FOBS=    197.7 SIGMA=   1.0 PHAS= -115.3 FOM= 0.94 TEST= 0
INDE 26 34 32 FOBS=    151.3 SIGMA=   1.2 PHAS=  -88.6 FOM= 0.94 TEST= 0
INDE 26 34 34 FOBS=     87.0 SIGMA=   1.9 PHAS= -109.6 FOM= 0.79 TEST= 0
INDE 26 34 36 FOBS=     51.5 SIGMA=   3.3 PHAS=   26.5 FOM= 0.13 TEST= 0
INDE 26 34 38 FOBS=      0.0 SIGMA=  18.5 PHAS=    0.0 FOM= 0.00 TEST= 0
INDE 26 34 40 FOBS=     56.5 SIGMA=   2.9 PHAS= -176.8 FOM= 0.36 TEST= 1
INDE 26 34 42 FOBS=     83.3 SIGMA=   2.0 PHAS=  106.7 FOM= 0.80 TEST= 0
INDE 26 34 44 FOBS=     63.5 SIGMA=   2.5 PHAS=   13.2 FOM= 0.76 TEST= 0
INDE 26 34 46 FOBS=     69.0 SIGMA=   2.5 PHAS=   71.5 FOM= 0.88 TEST= 0
INDE 26 34 48 FOBS=     85.4 SIGMA=   2.0 PHAS=   68.4 FOM= 0.94 TEST= 0
INDE 26 34 50 FOBS=     45.6 SIGMA=   4.1 PHAS=   41.9 FOM= 0.69 TEST= 0
INDE 26 34 52 FOBS=    126.6 SIGMA=   1.8 PHAS=  -98.1 FOM= 0.91 TEST= 0
INDE 26 34 54 FOBS=     82.6 SIGMA=   3.0 PHAS=  -96.8 FOM= 0.93 TEST= 0
INDE 26 34 56 FOBS=      0.0 SIGMA=  23.4 PHAS=    0.0 FOM= 0.00 TEST= 0
INDE 26 34 58 FOBS=     72.7 SIGMA=   3.4 PHAS=  -57.0 FOM= 0.11 TEST= 1
INDE 26 34 60 FOBS=     32.4 SIGMA=   7.4 PHAS=   75.0 FOM= 0.45 TEST= 0
INDE 26 34 62 FOBS=      0.0 SIGMA=  24.9 PHAS=    0.0 FOM= 0.00 TEST= 0
INDE 26 34 64 FOBS=      0.0 SIGMA=  27.4 PHAS=    0.0 FOM= 0.00 TEST= 0
INDE 26 35 27 FOBS=    192.9 SIGMA=   1.1 PHAS= -108.7 FOM= 0.87 TEST= 0
INDE 26 35 29 FOBS=      0.0 SIGMA=  19.2 PHAS=    0.0 FOM= 0.00 TEST= 0
INDE 26 35 31 FOBS=     95.0 SIGMA=   1.9 PHAS=  179.4 FOM= 0.91 TEST= 0
INDE 26 35 33 FOBS=    102.5 SIGMA=   1.6 PHAS=  158.4 FOM= 0.31 TEST= 1
INDE 26 35 35 FOBS=     85.6 SIGMA=   2.0 PHAS=   93.4 FOM= 0.77 TEST= 0
INDE 26 35 37 FOBS=     61.4 SIGMA=   2.8 PHAS=  -42.8 FOM= 0.62 TEST= 0
INDE 26 35 39 FOBS=     88.2 SIGMA=   1.9 PHAS=   56.6 FOM= 0.91 TEST= 0
INDE 26 35 41 FOBS=    165.5 SIGMA=   1.1 PHAS=  100.8 FOM= 0.71 TEST= 1
INDE 26 35 43 FOBS=      0.0 SIGMA=  18.1 PHAS=    0.0 FOM= 0.00 TEST= 1
INDE 26 35 45 FOBS=     21.0 SIGMA=   8.6 PHAS=  -17.7 FOM= 0.24 TEST= 0
INDE 26 35 47 FOBS=     60.7 SIGMA=   2.6 PHAS=   -2.9 FOM= 0.80 TEST= 0
INDE 26 35 49 FOBS=     91.9 SIGMA=   1.8 PHAS=  -35.0 FOM= 0.87 TEST= 0
INDE 26 35 51 FOBS=    109.1 SIGMA=   2.1 PHAS=   85.1 FOM= 0.94 TEST= 0
INDE 26 35 53 FOBS=     41.3 SIGMA=   5.9 PHAS=  -84.7 FOM= 0.60 TEST= 0
INDE 26 35 55 FOBS=    126.0 SIGMA=   2.0 PHAS=   -0.5 FOM= 0.93 TEST= 0
INDE 26 35 57 FOBS=     60.2 SIGMA=   4.1 PHAS=   44.4 FOM= 0.08 TEST= 1
INDE 26 35 59 FOBS=      0.0 SIGMA=  23.0 PHAS=    0.0 FOM= 0.00 TEST= 0
INDE 26 35 61 FOBS=     35.9 SIGMA=   7.6 PHAS=  137.1 FOM= 0.05 TEST= 1
INDE 26 35 63 FOBS=     42.1 SIGMA=   7.8 PHAS=  -23.6 FOM= 0.59 TEST= 0
INDE 26 36 26 FOBS=    184.6 SIGMA=   1.0 PHAS=  129.1 FOM= 0.97 TEST= 0
INDE 26 36 28 FOBS=    211.9 SIGMA=   1.0 PHAS=   80.8 FOM= 0.94 TEST= 0
INDE 26 36 30 FOBS=     88.7 SIGMA=   2.1 PHAS=   59.4 FOM= 0.91 TEST= 0
INDE 26 36 32 FOBS=     68.4 SIGMA=   2.6 PHAS= -179.5 FOM= 0.68 TEST= 0
INDE 26 36 34 FOBS=    119.4 SIGMA=   1.4 PHAS=  -45.3 FOM= 0.90 TEST= 0
INDE 26 36 36 FOBS=    110.2 SIGMA=   1.5 PHAS=  -25.5 FOM= 0.87 TEST= 0
INDE 26 36 38 FOBS=    102.7 SIGMA=   1.6 PHAS=  -94.0 FOM= 0.82 TEST= 0
INDE 26 36 40 FOBS=     32.5 SIGMA=   5.2 PHAS= -171.6 FOM= 0.77 TEST= 0
INDE 26 36 42 FOBS=    158.0 SIGMA=   1.1 PHAS=   41.9 FOM= 0.95 TEST= 0
INDE 26 36 44 FOBS=     79.2 SIGMA=   2.0 PHAS=   33.4 FOM= 0.89 TEST= 0
INDE 26 36 46 FOBS=      0.0 SIGMA=  18.5 PHAS=    0.0 FOM= 0.00 TEST= 0
INDE 26 36 48 FOBS=    104.8 SIGMA=   1.5 PHAS= -113.3 FOM= 0.79 TEST= 0
INDE 26 36 50 FOBS=      0.0 SIGMA=  19.4 PHAS=    0.0 FOM= 0.00 TEST= 0
INDE 26 36 52 FOBS=     19.5 SIGMA=   9.6 PHAS=  -90.0 FOM= 0.30 TEST= 0
```

*FIG. 12A - 507*

```
INDE 26 36 54 FOBS=   161.9 SIGMA=  1.6 PHAS= -124.0 FOM= 0.55 TEST= 1
INDE 26 36 56 FOBS=   107.5 SIGMA=  2.3 PHAS=  148.3 FOM= 0.88 TEST= 0
INDE 26 36 58 FOBS=    52.9 SIGMA=  4.7 PHAS= -151.7 FOM= 0.84 TEST= 0
INDE 26 36 60 FOBS=    26.2 SIGMA= 10.6 PHAS=   -1.9 FOM= 0.41 TEST= 0
INDE 26 36 62 FOBS=    25.1 SIGMA= 13.1 PHAS=  -21.4 FOM= 0.49 TEST= 0
INDE 26 37 27 FOBS=   142.3 SIGMA=  1.4 PHAS=  -42.4 FOM= 0.92 TEST= 0
INDE 26 37 29 FOBS=   206.3 SIGMA=  1.0 PHAS=    9.9 FOM= 0.96 TEST= 0
INDE 26 37 31 FOBS=    82.2 SIGMA=  2.2 PHAS=  -35.1 FOM= 0.86 TEST= 0
INDE 26 37 33 FOBS=    31.6 SIGMA=  6.0 PHAS=  163.9 FOM= 0.46 TEST= 1
INDE 26 37 35 FOBS=    51.7 SIGMA=  3.2 PHAS=  -95.9 FOM= 0.80 TEST= 0
INDE 26 37 37 FOBS=   133.5 SIGMA=  1.3 PHAS=  -43.6 FOM= 0.87 TEST= 0
INDE 26 37 39 FOBS=   163.1 SIGMA=  1.1 PHAS=  105.8 FOM= 0.93 TEST= 0
INDE 26 37 41 FOBS=    47.0 SIGMA=  3.5 PHAS= -115.6 FOM= 0.37 TEST= 0
INDE 26 37 43 FOBS=    78.0 SIGMA=  2.1 PHAS=  -75.8 FOM= 0.82 TEST= 0
INDE 26 37 45 FOBS=    58.8 SIGMA=  2.7 PHAS=   42.1 FOM= 0.18 TEST= 1
INDE 26 37 47 FOBS=     0.0 SIGMA= 17.6 PHAS=    0.0 FOM= 0.00 TEST= 0
INDE 26 37 49 FOBS=     0.0 SIGMA= 18.8 PHAS=    0.0 FOM= 0.00 TEST= 0
INDE 26 37 51 FOBS=    17.9 SIGMA= 13.2 PHAS=  160.6 FOM= 0.06 TEST= 0
INDE 26 37 53 FOBS=   109.5 SIGMA=  2.0 PHAS= -178.7 FOM= 0.89 TEST= 0
INDE 26 37 55 FOBS=   144.8 SIGMA=  1.5 PHAS=   25.0 FOM= 0.97 TEST= 0
INDE 26 37 57 FOBS=    51.9 SIGMA=  4.8 PHAS=   61.5 FOM= 0.82 TEST= 0
INDE 26 37 59 FOBS=    52.4 SIGMA=  5.4 PHAS=  129.0 FOM= 0.66 TEST= 0
INDE 26 37 61 FOBS=     0.0 SIGMA= 23.6 PHAS=    0.0 FOM= 0.00 TEST= 0
INDE 26 37 63 FOBS=     0.0 SIGMA= 29.0 PHAS=    0.0 FOM= 0.00 TEST= 0
INDE 26 38 26 FOBS=   175.4 SIGMA=  1.0 PHAS=  171.9 FOM= 0.97 TEST= 0
INDE 26 38 28 FOBS=   156.4 SIGMA=  1.2 PHAS=  -41.1 FOM= 0.90 TEST= 0
INDE 26 38 30 FOBS=   203.1 SIGMA=  1.0 PHAS=  -62.7 FOM= 0.93 TEST= 0
INDE 26 38 32 FOBS=    60.8 SIGMA=  3.0 PHAS=  159.3 FOM= 0.51 TEST= 0
INDE 26 38 34 FOBS=    78.7 SIGMA=  2.1 PHAS= -170.3 FOM= 0.96 TEST= 0
INDE 26 38 36 FOBS=    61.7 SIGMA=  2.7 PHAS=  122.3 FOM= 0.69 TEST= 0
INDE 26 38 38 FOBS=    51.8 SIGMA=  3.2 PHAS=  143.8 FOM= 0.82 TEST= 0
INDE 26 38 40 FOBS=    80.7 SIGMA=  2.1 PHAS= -177.1 FOM= 0.86 TEST= 0
INDE 26 38 42 FOBS=    95.3 SIGMA=  1.7 PHAS=  114.7 FOM= 0.90 TEST= 0
INDE 26 38 44 FOBS=     0.0 SIGMA= 19.5 PHAS=    0.0 FOM= 0.00 TEST= 0
INDE 26 38 46 FOBS=    62.5 SIGMA=  2.7 PHAS=  -32.1 FOM= 0.92 TEST= 0
INDE 26 38 48 FOBS=    49.4 SIGMA=  3.5 PHAS=  170.3 FOM= 0.85 TEST= 0
INDE 26 38 50 FOBS=    46.2 SIGMA=  3.7 PHAS=  155.2 FOM= 0.69 TEST= 0
INDE 26 38 52 FOBS=    56.9 SIGMA=  3.4 PHAS=  162.2 FOM= 0.60 TEST= 0
INDE 26 38 54 FOBS=    60.1 SIGMA=  3.5 PHAS=  -81.7 FOM= 0.91 TEST= 0
INDE 26 38 56 FOBS=    17.5 SIGMA= 11.8 PHAS=  -27.6 FOM= 0.53 TEST= 0
INDE 26 38 58 FOBS=     0.0 SIGMA= 21.2 PHAS=    0.0 FOM= 0.00 TEST= 0
INDE 26 38 60 FOBS=    14.5 SIGMA= 17.4 PHAS=   42.1 FOM= 0.23 TEST= 0
INDE 26 38 62 FOBS=    39.8 SIGMA=  8.4 PHAS=  -57.0 FOM= 0.20 TEST= 0
INDE 26 39 27 FOBS=   119.0 SIGMA=  1.6 PHAS=  -39.8 FOM= 0.91 TEST= 0
INDE 26 39 29 FOBS=   170.8 SIGMA=  1.2 PHAS= -175.6 FOM= 0.92 TEST= 0
INDE 26 39 31 FOBS=   176.5 SIGMA=  1.1 PHAS= -156.9 FOM= 0.96 TEST= 0
INDE 26 39 33 FOBS=    40.6 SIGMA=  4.6 PHAS=    6.5 FOM= 0.45 TEST= 0
INDE 26 39 35 FOBS=   169.8 SIGMA=  1.0 PHAS=  104.4 FOM= 0.96 TEST= 0
INDE 26 39 37 FOBS=   141.4 SIGMA=  1.2 PHAS=   -6.6 FOM= 0.92 TEST= 0
INDE 26 39 39 FOBS=   143.7 SIGMA=  1.2 PHAS=   99.5 FOM= 0.96 TEST= 0
INDE 26 39 41 FOBS=    44.7 SIGMA=  3.7 PHAS=  156.4 FOM= 0.23 TEST= 0
INDE 26 39 43 FOBS=    41.1 SIGMA=  4.3 PHAS=  105.6 FOM= 0.45 TEST= 0
INDE 26 39 45 FOBS=     0.0 SIGMA= 19.2 PHAS=    0.0 FOM= 0.00 TEST= 1
INDE 26 39 47 FOBS=     0.0 SIGMA= 18.5 PHAS=    0.0 FOM= 0.00 TEST= 1
INDE 26 39 49 FOBS=   101.2 SIGMA=  1.7 PHAS=   75.1 FOM= 0.91 TEST= 0
INDE 26 39 51 FOBS=    92.0 SIGMA=  1.9 PHAS=   17.0 FOM= 0.45 TEST= 1
INDE 26 39 53 FOBS=     0.0 SIGMA= 20.4 PHAS=    0.0 FOM= 0.00 TEST= 0
INDE 26 39 55 FOBS=    68.2 SIGMA=  3.1 PHAS=   10.7 FOM= 0.81 TEST= 0
INDE 26 39 57 FOBS=    14.0 SIGMA= 17.4 PHAS= -118.2 FOM= 0.15 TEST= 0
INDE 26 39 59 FOBS=   109.0 SIGMA=  2.0 PHAS=   68.8 FOM= 0.93 TEST= 0
INDE 26 39 61 FOBS=     0.0 SIGMA= 23.8 PHAS=    0.0 FOM= 0.00 TEST= 0
INDE 26 40 26 FOBS=     0.0 SIGMA= 18.3 PHAS=    0.0 FOM= 0.00 TEST= 1
INDE 26 40 28 FOBS=    57.5 SIGMA=  3.2 PHAS=  -41.9 FOM= 0.65 TEST= 0
INDE 26 40 30 FOBS=    99.7 SIGMA=  1.9 PHAS=   31.9 FOM= 0.76 TEST= 0
INDE 26 40 32 FOBS=    83.2 SIGMA=  2.2 PHAS=  123.8 FOM= 0.90 TEST= 0
INDE 26 40 34 FOBS=    38.3 SIGMA=  4.9 PHAS=   53.5 FOM= 0.65 TEST= 0
INDE 26 40 36 FOBS=    57.7 SIGMA=  2.9 PHAS=   18.9 FOM= 0.54 TEST= 0
INDE 26 40 38 FOBS=    56.4 SIGMA=  2.9 PHAS= -135.9 FOM= 0.67 TEST= 0
INDE 26 40 40 FOBS=    42.4 SIGMA=  4.0 PHAS=  -68.8 FOM= 0.69 TEST= 0
INDE 26 40 42 FOBS=    53.7 SIGMA=  3.0 PHAS=   97.4 FOM= 0.45 TEST= 0
```

*FIG. 12A - 508*

| | | | | | | | | | | | |
|---|---|---|---|---|---|---|---|---|---|---|---|
|INDE|26|40|44|FOBS=|79.9|SIGMA=|2.3|PHAS=|103.3|FOM=|0.81|TEST= 0
|INDE|26|40|46|FOBS=|42.4|SIGMA=|4.1|PHAS=|-130.0|FOM=|0.30|TEST= 0
|INDE|26|40|48|FOBS=|52.7|SIGMA=|3.3|PHAS=|36.3|FOM=|0.85|TEST= 0
|INDE|26|40|50|FOBS=|150.8|SIGMA=|1.2|PHAS=|-106.4|FOM=|0.94|TEST= 0
|INDE|26|40|52|FOBS=|107.7|SIGMA=|1.8|PHAS=|-126.2|FOM=|0.95|TEST= 0
|INDE|26|40|54|FOBS=|0.0|SIGMA=|21.3|PHAS=|0.0|FOM=|0.00|TEST= 0
|INDE|26|40|56|FOBS=|0.0|SIGMA=|21.2|PHAS=|0.0|FOM=|0.00|TEST= 0
|INDE|26|40|58|FOBS=|64.7|SIGMA=|3.3|PHAS=|-12.4|FOM=|0.82|TEST= 0
|INDE|26|40|60|FOBS=|109.1|SIGMA=|2.5|PHAS=|3.7|FOM=|0.96|TEST= 0
|INDE|26|41|27|FOBS=|79.6|SIGMA=|2.2|PHAS=|79.6|FOM=|0.84|TEST= 0
|INDE|26|41|29|FOBS=|109.6|SIGMA=|1.7|PHAS=|-155.5|FOM=|0.87|TEST= 0
|INDE|26|41|31|FOBS=|53.2|SIGMA=|3.4|PHAS=|-111.3|FOM=|0.87|TEST= 0
|INDE|26|41|33|FOBS=|149.8|SIGMA=|1.3|PHAS=|18.6|FOM=|0.95|TEST= 0
|INDE|26|41|35|FOBS=|129.5|SIGMA=|1.4|PHAS=|10.5|FOM=|0.77|TEST= 0
|INDE|26|41|37|FOBS=|73.3|SIGMA=|2.3|PHAS=|-159.6|FOM=|0.72|TEST= 0
|INDE|26|41|39|FOBS=|99.7|SIGMA=|1.7|PHAS=|144.0|FOM=|0.94|TEST= 0
|INDE|26|41|41|FOBS=|110.3|SIGMA=|1.5|PHAS=|162.2|FOM=|0.92|TEST= 0
|INDE|26|41|43|FOBS=|147.3|SIGMA=|1.3|PHAS=|131.5|FOM=|0.18|TEST= 1
|INDE|26|41|45|FOBS=|77.0|SIGMA=|2.3|PHAS=|-49.9|FOM=|0.51|TEST= 0
|INDE|26|41|47|FOBS=|62.6|SIGMA=|2.9|PHAS=|170.8|FOM=|0.32|TEST= 0
|INDE|26|41|49|FOBS=|40.3|SIGMA=|4.6|PHAS=|-9.3|FOM=|0.37|TEST= 0
|INDE|26|41|51|FOBS=|46.9|SIGMA=|3.7|PHAS=|166.4|FOM=|0.81|TEST= 0
|INDE|26|41|53|FOBS=|19.1|SIGMA=|11.2|PHAS=|-66.5|FOM=|0.07|TEST= 1
|INDE|26|41|55|FOBS=|36.3|SIGMA=|6.3|PHAS=|-57.5|FOM=|0.55|TEST= 0
|INDE|26|41|57|FOBS=|38.3|SIGMA=|5.6|PHAS=|-42.2|FOM=|0.49|TEST= 0
|INDE|26|41|59|FOBS=|8.3|SIGMA=|30.8|PHAS=|-36.1|FOM=|0.24|TEST= 0
|INDE|26|42|26|FOBS=|142.7|SIGMA=|1.2|PHAS=|-54.5|FOM=|0.84|TEST= 0
|INDE|26|42|28|FOBS=|99.1|SIGMA=|1.8|PHAS=|82.9|FOM=|0.28|TEST= 0
|INDE|26|42|30|FOBS=|93.5|SIGMA=|1.9|PHAS=|-177.7|FOM=|0.61|TEST= 0
|INDE|26|42|32|FOBS=|0.0|SIGMA=|19.4|PHAS=|0.0|FOM=|0.00|TEST= 0
|INDE|26|42|34|FOBS=|112.0|SIGMA=|1.7|PHAS=|-39.5|FOM=|0.92|TEST= 0
|INDE|26|42|36|FOBS=|58.3|SIGMA=|2.9|PHAS=|23.3|FOM=|0.58|TEST= 0
|INDE|26|42|38|FOBS=|138.1|SIGMA=|1.3|PHAS=|120.6|FOM=|0.92|TEST= 0
|INDE|26|42|40|FOBS=|105.0|SIGMA=|1.6|PHAS=|38.2|FOM=|0.91|TEST= 0
|INDE|26|42|42|FOBS=|90.2|SIGMA=|2.0|PHAS=|51.0|FOM=|0.87|TEST= 0
|INDE|26|42|44|FOBS=|66.9|SIGMA=|2.7|PHAS=|114.7|FOM=|0.82|TEST= 0
|INDE|26|42|46|FOBS=|130.7|SIGMA=|1.4|PHAS=|-144.8|FOM=|0.94|TEST= 0
|INDE|26|42|48|FOBS=|39.8|SIGMA=|4.7|PHAS=|84.5|FOM=|0.45|TEST= 0
|INDE|26|42|50|FOBS=|129.5|SIGMA=|1.4|PHAS=|-173.7|FOM=|0.95|TEST= 0
|INDE|26|42|52|FOBS=|95.6|SIGMA=|2.1|PHAS=|-158.7|FOM=|0.91|TEST= 0
|INDE|26|42|54|FOBS=|73.3|SIGMA=|2.6|PHAS=|-154.4|FOM=|0.91|TEST= 0
|INDE|26|42|56|FOBS=|0.0|SIGMA=|21.3|PHAS=|0.0|FOM=|0.00|TEST= 0
|INDE|26|42|58|FOBS=|0.0|SIGMA=|20.7|PHAS=|0.0|FOM=|0.00|TEST= 0
|INDE|26|42|60|FOBS=|45.7|SIGMA=|7.6|PHAS=|61.4|FOM=|0.67|TEST= 0
|INDE|26|43|27|FOBS=|141.7|SIGMA=|1.3|PHAS=|141.3|FOM=|0.74|TEST= 0
|INDE|26|43|29|FOBS=|24.9|SIGMA=|7.5|PHAS=|72.7|FOM=|0.17|TEST= 0
|INDE|26|43|31|FOBS=|146.0|SIGMA=|1.3|PHAS=|29.1|FOM=|0.95|TEST= 0
|INDE|26|43|33|FOBS=|70.1|SIGMA=|2.6|PHAS=|83.5|FOM=|0.19|TEST= 0
|INDE|26|43|35|FOBS=|68.0|SIGMA=|2.6|PHAS=|-148.7|FOM=|0.91|TEST= 1
|INDE|26|43|37|FOBS=|42.2|SIGMA=|3.9|PHAS=|105.0|FOM=|0.61|TEST= 0
|INDE|26|43|39|FOBS=|84.2|SIGMA=|2.1|PHAS=|8.7|FOM=|0.91|TEST= 1
|INDE|26|43|41|FOBS=|23.9|SIGMA=|8.4|PHAS=|-65.5|FOM=|0.29|TEST= 0
|INDE|26|43|43|FOBS=|0.0|SIGMA=|19.4|PHAS=|0.0|FOM=|0.00|TEST= 0
|INDE|26|43|45|FOBS=|60.4|SIGMA=|3.0|PHAS=|-173.7|FOM=|0.72|TEST= 0
|INDE|26|43|47|FOBS=|135.7|SIGMA=|1.4|PHAS=|114.5|FOM=|0.95|TEST= 0
|INDE|26|43|49|FOBS=|89.5|SIGMA=|2.0|PHAS=|51.8|FOM=|0.87|TEST= 0
|INDE|26|43|51|FOBS=|49.6|SIGMA=|3.9|PHAS=|-178.2|FOM=|0.69|TEST= 0
|INDE|26|43|53|FOBS=|42.8|SIGMA=|4.5|PHAS=|117.6|FOM=|0.82|TEST= 0
|INDE|26|43|55|FOBS=|84.0|SIGMA=|2.3|PHAS=|80.9|FOM=|0.93|TEST= 0
|INDE|26|43|57|FOBS=|0.0|SIGMA=|21.6|PHAS=|0.0|FOM=|0.00|TEST= 0
|INDE|26|43|59|FOBS=|65.8|SIGMA=|4.1|PHAS=|-27.3|FOM=|0.66|TEST= 0
|INDE|26|44|26|FOBS=|25.3|SIGMA=|6.7|PHAS=|-18.3|FOM=|0.24|TEST= 0
|INDE|26|44|28|FOBS=|0.0|SIGMA=|19.2|PHAS=|0.0|FOM=|0.00|TEST= 0
|INDE|26|44|30|FOBS=|101.4|SIGMA=|1.8|PHAS=|-100.1|FOM=|0.90|TEST= 0
|INDE|26|44|32|FOBS=|96.8|SIGMA=|1.9|PHAS=|-81.1|FOM=|0.72|TEST= 0
|INDE|26|44|34|FOBS=|87.4|SIGMA=|2.1|PHAS=|-18.8|FOM=|0.82|TEST= 0
|INDE|26|44|36|FOBS=|110.2|SIGMA=|1.7|PHAS=|-22.2|FOM=|0.93|TEST= 0
|INDE|26|44|38|FOBS=|0.0|SIGMA=|20.7|PHAS=|0.0|FOM=|0.00|TEST= 0
|INDE|26|44|40|FOBS=|42.1|SIGMA=|4.3|PHAS=|-17.8|FOM=|0.77|TEST= 0
|INDE|26|44|42|FOBS=|0.0|SIGMA=|19.4|PHAS=|0.0|FOM=|0.00|TEST= 0

*FIG. 12A - 509*

```
INDE  26  44  44  FOBS=   74.6  SIGMA=   2.4  PHAS=  118.4  FOM= 0.85  TEST= 0
INDE  26  44  46  FOBS=    0.0  SIGMA=  19.5  PHAS=    0.0  FOM= 0.00  TEST= 0
INDE  26  44  48  FOBS=   40.9  SIGMA=   4.4  PHAS=  -53.6  FOM= 0.67  TEST= 0
INDE  26  44  50  FOBS=   86.8  SIGMA=   2.1  PHAS= -173.4  FOM= 0.90  TEST= 0
INDE  26  44  52  FOBS=    0.0  SIGMA=  20.2  PHAS=    0.0  FOM= 0.00  TEST= 0
INDE  26  44  54  FOBS=   53.4  SIGMA=   3.6  PHAS=  117.4  FOM= 0.71  TEST= 0
INDE  26  44  56  FOBS=   22.1  SIGMA=   9.4  PHAS=  -45.3  FOM= 0.62  TEST= 0
INDE  26  44  58  FOBS=   65.8  SIGMA=   4.1  PHAS=  126.2  FOM= 0.89  TEST= 0
INDE  26  45  27  FOBS=   49.1  SIGMA=   3.5  PHAS=   58.2  FOM= 0.20  TEST= 0
INDE  26  45  29  FOBS=  140.7  SIGMA=   1.3  PHAS=  150.5  FOM= 0.94  TEST= 0
INDE  26  45  31  FOBS=  170.6  SIGMA=   1.1  PHAS=   92.2  FOM= 0.97  TEST= 0
INDE  26  45  33  FOBS=   86.0  SIGMA=   2.1  PHAS= -171.7  FOM= 0.59  TEST= 0
INDE  26  45  35  FOBS=  112.3  SIGMA=   1.6  PHAS= -165.1  FOM= 0.90  TEST= 0
INDE  26  45  37  FOBS=   76.3  SIGMA=   2.7  PHAS= -139.5  FOM= 0.87  TEST= 0
INDE  26  45  39  FOBS=  114.7  SIGMA=   1.6  PHAS=  -37.0  FOM= 0.89  TEST= 0
INDE  26  45  41  FOBS=   44.9  SIGMA=   4.6  PHAS=   62.4  FOM= 0.67  TEST= 0
INDE  26  45  43  FOBS=    0.0  SIGMA=  19.6  PHAS=    0.0  FOM= 0.00  TEST= 0
INDE  26  45  45  FOBS=   61.8  SIGMA=   2.9  PHAS=   73.3  FOM= 0.78  TEST= 0
INDE  26  45  47  FOBS=  102.0  SIGMA=   1.8  PHAS=   93.2  FOM= 0.88  TEST= 0
INDE  26  45  49  FOBS=   12.0  SIGMA=  15.0  PHAS=  -33.7  FOM= 0.10  TEST= 0
INDE  26  45  51  FOBS=   55.3  SIGMA=   3.5  PHAS=   91.7  FOM= 0.89  TEST= 0
INDE  26  45  53  FOBS=   86.3  SIGMA=   2.3  PHAS=   46.9  FOM= 0.92  TEST= 0
INDE  26  45  55  FOBS=   53.9  SIGMA=   3.9  PHAS=   37.7  FOM= 0.84  TEST= 0
INDE  26  45  57  FOBS=   11.7  SIGMA=  23.3  PHAS=   44.3  FOM= 0.24  TEST= 0
INDE  26  46  26  FOBS=  166.0  SIGMA=   1.2  PHAS= -141.3  FOM= 0.95  TEST= 0
INDE  26  46  28  FOBS=   91.4  SIGMA=   2.1  PHAS=  -22.6  FOM= 0.86  TEST= 0
INDE  26  46  30  FOBS=   77.3  SIGMA=   2.3  PHAS=    4.8  FOM= 0.62  TEST= 0
INDE  26  46  32  FOBS=  142.3  SIGMA=   1.3  PHAS=   49.4  FOM= 0.90  TEST= 0
INDE  26  46  34  FOBS=   68.0  SIGMA=   2.8  PHAS=   36.5  FOM= 0.78  TEST= 0
INDE  26  46  36  FOBS=   56.4  SIGMA=   3.6  PHAS= -124.7  FOM= 0.76  TEST= 0
INDE  26  46  38  FOBS=   95.8  SIGMA=   2.0  PHAS=  171.4  FOM= 0.92  TEST= 0
INDE  26  46  40  FOBS=   59.4  SIGMA=   3.2  PHAS=   17.7  FOM= 0.87  TEST= 0
INDE  26  46  42  FOBS=   55.1  SIGMA=   3.4  PHAS=  -36.9  FOM= 0.89  TEST= 0
INDE  26  46  44  FOBS=   69.4  SIGMA=   2.7  PHAS=   69.1  FOM= 0.89  TEST= 0
INDE  26  46  46  FOBS=  110.8  SIGMA=   1.7  PHAS=   48.3  FOM= 0.17  TEST= 1
INDE  26  46  48  FOBS=   53.9  SIGMA=   3.6  PHAS= -110.7  FOM= 0.66  TEST= 0
INDE  26  46  50  FOBS=   50.8  SIGMA=   3.9  PHAS=  -93.9  FOM= 0.66  TEST= 0
INDE  26  46  52  FOBS=  102.9  SIGMA=   2.0  PHAS=  -41.2  FOM= 0.95  TEST= 0
INDE  26  46  54  FOBS=   36.7  SIGMA=   6.1  PHAS=  -72.1  FOM= 0.26  TEST= 1
INDE  26  46  56  FOBS=    0.0  SIGMA=  21.3  PHAS=    0.0  FOM= 0.00  TEST= 0
INDE  26  47  27  FOBS=   86.5  SIGMA=   2.0  PHAS=  144.1  FOM= 0.91  TEST= 0
INDE  26  47  29  FOBS=   87.2  SIGMA=   2.1  PHAS= -176.5  FOM= 0.81  TEST= 0
INDE  26  47  31  FOBS=   73.0  SIGMA=   2.4  PHAS=  112.1  FOM= 0.88  TEST= 0
INDE  26  47  33  FOBS=   72.1  SIGMA=   2.8  PHAS=  -20.3  FOM= 0.67  TEST= 0
INDE  26  47  35  FOBS=   94.4  SIGMA=   2.2  PHAS=  172.7  FOM= 0.86  TEST= 0
INDE  26  47  37  FOBS=   85.9  SIGMA=   2.4  PHAS=  119.1  FOM= 0.91  TEST= 0
INDE  26  47  39  FOBS=   64.1  SIGMA=   2.8  PHAS=  -88.2  FOM= 0.81  TEST= 0
INDE  26  47  41  FOBS=   35.6  SIGMA=   5.0  PHAS=  177.9  FOM= 0.33  TEST= 1
INDE  26  47  43  FOBS=   50.3  SIGMA=   3.6  PHAS= -126.4  FOM= 0.71  TEST= 0
INDE  26  47  45  FOBS=  132.3  SIGMA=   1.5  PHAS=  -17.1  FOM= 0.57  TEST= 1
INDE  26  47  47  FOBS=   56.3  SIGMA=   3.3  PHAS=   67.8  FOM= 0.44  TEST= 0
INDE  26  47  49  FOBS=   44.1  SIGMA=   4.2  PHAS= -167.9  FOM= 0.79  TEST= 0
INDE  26  47  51  FOBS=   84.2  SIGMA=   2.4  PHAS=  168.0  FOM= 0.94  TEST= 0
INDE  26  47  53  FOBS=    0.0  SIGMA=  21.2  PHAS=    0.0  FOM= 0.00  TEST= 0
INDE  26  47  55  FOBS=    0.0  SIGMA=  21.3  PHAS=    0.0  FOM= 0.00  TEST= 0
INDE  26  48  26  FOBS=    0.0  SIGMA=  18.9  PHAS=    0.0  FOM= 0.00  TEST= 0
INDE  26  48  28  FOBS=    0.0  SIGMA=  18.9  PHAS=    0.0  FOM= 0.00  TEST= 0
INDE  26  48  30  FOBS=  128.3  SIGMA=   1.5  PHAS=   44.2  FOM= 0.94  TEST= 0
INDE  26  48  32  FOBS=  153.5  SIGMA=   1.4  PHAS=   67.5  FOM= 0.95  TEST= 0
INDE  26  48  34  FOBS=   46.6  SIGMA=   4.7  PHAS=   46.1  FOM= 0.47  TEST= 1
INDE  26  48  36  FOBS=  160.3  SIGMA=   1.4  PHAS=  -29.0  FOM= 0.95  TEST= 0
INDE  26  48  38  FOBS=   22.0  SIGMA=   9.0  PHAS=  125.0  FOM= 0.33  TEST= 0
INDE  26  48  40  FOBS=   13.7  SIGMA=  13.2  PHAS=  102.5  FOM= 0.27  TEST= 0
INDE  26  48  42  FOBS=    0.0  SIGMA=  20.2  PHAS=    0.0  FOM= 0.00  TEST= 1
INDE  26  48  44  FOBS=    0.0  SIGMA=  22.3  PHAS=    0.0  FOM= 0.00  TEST= 0
INDE  26  48  46  FOBS=  123.3  SIGMA=   1.6  PHAS=  -21.8  FOM= 0.95  TEST= 0
INDE  26  48  48  FOBS=  104.5  SIGMA=   1.8  PHAS= -101.7  FOM= 0.92  TEST= 0
INDE  26  48  50  FOBS=   42.6  SIGMA=   4.7  PHAS=   87.8  FOM= 0.76  TEST= 0
INDE  26  48  52  FOBS=   81.8  SIGMA=   2.5  PHAS=  145.2  FOM= 0.78  TEST= 0
INDE  26  48  54  FOBS=   48.0  SIGMA=   5.2  PHAS= -163.6  FOM= 0.81  TEST= 0
```

*FIG. 12A - 510*

```
INDE 26 49 27 FOBS=    89.6 SIGMA=  1.9 PHAS=  168.2 FOM= 0.92 TEST= 0
INDE 26 49 29 FOBS=    94.9 SIGMA=  2.4 PHAS=   50.0 FOM= 0.87 TEST= 0
INDE 26 49 31 FOBS=   127.8 SIGMA=  1.6 PHAS=  -14.4 FOM= 0.95 TEST= 0
INDE 26 49 33 FOBS=   131.6 SIGMA=  1.6 PHAS=    7.0 FOM= 0.82 TEST= 0
INDE 26 49 35 FOBS=    20.7 SIGMA= 10.1 PHAS=   43.2 FOM= 0.20 TEST= 0
INDE 26 49 37 FOBS=    53.9 SIGMA=  3.9 PHAS=   97.9 FOM= 0.12 TEST= 1
INDE 26 49 39 FOBS=    20.6 SIGMA= 11.1 PHAS=  146.0 FOM= 0.23 TEST= 0
INDE 26 49 41 FOBS=     0.0 SIGMA= 20.2 PHAS=    0.0 FOM= 0.00 TEST= 0
INDE 26 49 43 FOBS=    81.7 SIGMA=  2.3 PHAS= -132.6 FOM= 0.80 TEST= 0
INDE 26 49 45 FOBS=   104.9 SIGMA=  1.8 PHAS=  -69.8 FOM= 0.70 TEST= 1
INDE 26 49 47 FOBS=    98.4 SIGMA=  1.9 PHAS= -152.4 FOM= 0.94 TEST= 0
INDE 26 49 49 FOBS=    66.7 SIGMA=  3.0 PHAS=  148.8 FOM= 0.56 TEST= 1
INDE 26 49 51 FOBS=    51.1 SIGMA=  4.2 PHAS=  115.2 FOM= 0.30 TEST= 0
INDE 26 49 53 FOBS=   121.5 SIGMA=  2.0 PHAS=   80.6 FOM= 0.97 TEST= 0
INDE 26 50 26 FOBS=   104.8 SIGMA=  1.7 PHAS=   54.8 FOM= 0.92 TEST= 0
INDE 26 50 28 FOBS=    46.9 SIGMA=  4.3 PHAS= -101.8 FOM= 0.81 TEST= 0
INDE 26 50 30 FOBS=   106.4 SIGMA=  2.2 PHAS=  -36.8 FOM= 0.95 TEST= 0
INDE 26 50 32 FOBS=    34.7 SIGMA=  5.6 PHAS= -112.7 FOM= 0.43 TEST= 0
INDE 26 50 34 FOBS=    68.8 SIGMA=  2.9 PHAS=   -7.3 FOM= 0.77 TEST= 0
INDE 26 50 36 FOBS=   101.2 SIGMA=  2.0 PHAS=  -76.6 FOM= 0.87 TEST= 0
INDE 26 50 38 FOBS=    39.1 SIGMA=  6.4 PHAS= -172.3 FOM= 0.41 TEST= 0
INDE 26 50 40 FOBS=    58.1 SIGMA=  3.3 PHAS= -176.1 FOM= 0.80 TEST= 0
INDE 26 50 42 FOBS=    32.3 SIGMA=  6.5 PHAS=  174.4 FOM= 0.59 TEST= 0
INDE 26 50 44 FOBS=   106.8 SIGMA=  1.8 PHAS= -179.3 FOM= 0.95 TEST= 0
INDE 26 50 46 FOBS=    38.2 SIGMA=  5.2 PHAS=   -6.0 FOM= 0.36 TEST= 0
INDE 26 50 48 FOBS=    27.3 SIGMA=  7.8 PHAS=  119.8 FOM= 0.40 TEST= 0
INDE 26 50 50 FOBS=     0.0 SIGMA= 21.6 PHAS=    0.0 FOM= 0.00 TEST= 0
INDE 26 50 52 FOBS=    87.3 SIGMA=  3.0 PHAS=    1.6 FOM= 0.92 TEST= 0
INDE 26 51 27 FOBS=    62.2 SIGMA=  3.0 PHAS= -148.7 FOM= 0.88 TEST= 0
INDE 26 51 29 FOBS=     0.0 SIGMA= 24.9 PHAS=    0.0 FOM= 0.00 TEST= 0
INDE 26 51 31 FOBS=    57.7 SIGMA=  3.4 PHAS=   58.1 FOM= 0.76 TEST= 0
INDE 26 51 33 FOBS=    88.0 SIGMA=  2.3 PHAS= -146.3 FOM= 0.82 TEST= 0
INDE 26 51 35 FOBS=    47.1 SIGMA=  4.5 PHAS= -111.7 FOM= 0.08 TEST= 1
INDE 26 51 37 FOBS=     9.9 SIGMA= 21.5 PHAS=  134.2 FOM= 0.22 TEST= 0
INDE 26 51 39 FOBS=    86.4 SIGMA=  2.4 PHAS=  150.3 FOM= 0.77 TEST= 0
INDE 26 51 41 FOBS=     0.0 SIGMA= 19.6 PHAS=    0.0 FOM= 0.00 TEST= 0
INDE 26 51 43 FOBS=    35.5 SIGMA=  6.1 PHAS= -142.8 FOM= 0.26 TEST= 0
INDE 26 51 45 FOBS=    71.6 SIGMA=  2.8 PHAS=  149.2 FOM= 0.77 TEST= 0
INDE 26 51 47 FOBS=    65.7 SIGMA=  3.3 PHAS=   14.1 FOM= 0.01 TEST= 0
INDE 26 51 49 FOBS=    26.1 SIGMA=  9.1 PHAS=  131.1 FOM= 0.60 TEST= 0
INDE 26 51 51 FOBS=     0.0 SIGMA= 25.8 PHAS=    0.0 FOM= 0.00 TEST= 0
INDE 26 52 26 FOBS=    34.4 SIGMA=  5.0 PHAS=   64.9 FOM= 0.20 TEST= 0
INDE 26 52 28 FOBS=    15.2 SIGMA= 15.4 PHAS= -131.6 FOM= 0.02 TEST= 1
INDE 26 52 30 FOBS=   162.0 SIGMA=  1.5 PHAS=  -42.8 FOM= 0.95 TEST= 0
INDE 26 52 32 FOBS=    51.1 SIGMA=  3.8 PHAS=  165.2 FOM= 0.43 TEST= 0
INDE 26 52 34 FOBS=    12.1 SIGMA= 16.1 PHAS=  172.0 FOM= 0.45 TEST= 0
INDE 26 52 36 FOBS=    38.3 SIGMA=  5.9 PHAS=  149.5 FOM= 0.04 TEST= 0
INDE 26 52 38 FOBS=    40.9 SIGMA=  6.3 PHAS=  152.2 FOM= 0.32 TEST= 0
INDE 26 52 40 FOBS=    16.9 SIGMA= 15.0 PHAS= -176.5 FOM= 0.14 TEST= 0
INDE 26 52 42 FOBS=     0.0 SIGMA= 22.3 PHAS=    0.0 FOM= 0.00 TEST= 0
INDE 26 52 44 FOBS=    64.7 SIGMA=  3.3 PHAS=  112.0 FOM= 0.87 TEST= 0
INDE 26 52 46 FOBS=    66.2 SIGMA=  3.6 PHAS=   77.0 FOM= 0.79 TEST= 0
INDE 26 52 48 FOBS=    52.7 SIGMA=  5.0 PHAS=  -56.7 FOM= 0.79 TEST= 0
INDE 26 52 50 FOBS=    74.8 SIGMA=  3.6 PHAS=   -7.2 FOM= 0.49 TEST= 0
INDE 26 53 27 FOBS=    67.8 SIGMA=  2.6 PHAS=  -51.3 FOM= 0.86 TEST= 0
INDE 26 53 29 FOBS=   173.0 SIGMA=  1.3 PHAS= -134.7 FOM= 0.97 TEST= 0
INDE 26 53 31 FOBS=     0.0 SIGMA= 21.0 PHAS=    0.0 FOM= 0.00 TEST= 1
INDE 26 53 33 FOBS=    35.1 SIGMA=  7.7 PHAS=  177.1 FOM= 0.38 TEST= 0
INDE 26 53 35 FOBS=    31.7 SIGMA=  8.7 PHAS=  155.7 FOM= 0.45 TEST= 0
INDE 26 53 37 FOBS=    37.3 SIGMA=  6.9 PHAS=  126.9 FOM= 0.67 TEST= 0
INDE 26 53 39 FOBS=     0.0 SIGMA= 22.5 PHAS=    0.0 FOM= 0.00 TEST= 0
INDE 26 53 41 FOBS=     0.0 SIGMA= 24.7 PHAS=    0.0 FOM= 0.00 TEST= 0
INDE 26 53 43 FOBS=    68.1 SIGMA=  3.4 PHAS=  -53.7 FOM= 0.75 TEST= 0
INDE 26 53 45 FOBS=     0.0 SIGMA= 22.5 PHAS=    0.0 FOM= 0.00 TEST= 0
INDE 26 53 47 FOBS=    44.6 SIGMA=  5.9 PHAS=  152.3 FOM= 0.74 TEST= 0
INDE 26 53 49 FOBS=    88.4 SIGMA=  3.4 PHAS= -158.0 FOM= 0.92 TEST= 0
INDE 26 54 26 FOBS=   157.7 SIGMA=  1.1 PHAS= -121.9 FOM= 0.91 TEST= 0
INDE 26 54 28 FOBS=    60.0 SIGMA=  3.1 PHAS= -115.3 FOM= 0.50 TEST= 0
INDE 26 54 30 FOBS=    69.8 SIGMA=  4.0 PHAS=  142.6 FOM= 0.82 TEST= 0
INDE 26 54 32 FOBS=     0.0 SIGMA= 23.4 PHAS=    0.0 FOM= 0.00 TEST= 0
```

*FIG. 12A - 511*

```
INDE 26 54 34 FOBS=   0.0 SIGMA= 21.3 PHAS=    0.0 FOM= 0.00 TEST= 0
INDE 26 54 36 FOBS=   0.0 SIGMA= 22.5 PHAS=    0.0 FOM= 0.00 TEST= 0
INDE 26 54 38 FOBS=   0.0 SIGMA= 22.7 PHAS=    0.0 FOM= 0.00 TEST= 0
INDE 26 54 40 FOBS=  23.4 SIGMA= 12.6 PHAS=  150.9 FOM= 0.32 TEST= 0
INDE 26 54 42 FOBS=   0.0 SIGMA= 23.4 PHAS=    0.0 FOM= 0.00 TEST= 0
INDE 26 54 44 FOBS=  64.6 SIGMA=  4.0 PHAS=   86.8 FOM= 0.67 TEST= 0
INDE 26 54 46 FOBS=   0.0 SIGMA= 23.7 PHAS=    0.0 FOM= 0.00 TEST= 0
INDE 26 54 48 FOBS=  39.1 SIGMA=  7.7 PHAS=   92.3 FOM= 0.68 TEST= 0
INDE 26 55 27 FOBS=  26.5 SIGMA=  8.0 PHAS= -175.6 FOM= 0.35 TEST= 0
INDE 26 55 29 FOBS=  92.0 SIGMA=  2.4 PHAS= -138.3 FOM= 0.94 TEST= 0
INDE 26 55 31 FOBS=  39.4 SIGMA=  7.0 PHAS= -119.3 FOM= 0.25 TEST= 0
INDE 26 55 33 FOBS=   0.0 SIGMA= 22.1 PHAS=    0.0 FOM= 0.00 TEST= 0
INDE 26 55 35 FOBS=   0.0 SIGMA= 22.4 PHAS=    0.0 FOM= 0.00 TEST= 0
INDE 26 55 37 FOBS=  12.3 SIGMA= 21.3 PHAS=   21.0 FOM= 0.25 TEST= 0
INDE 26 55 39 FOBS=   0.0 SIGMA= 26.6 PHAS=    0.0 FOM= 0.00 TEST= 0
INDE 26 55 41 FOBS=  39.6 SIGMA=  7.7 PHAS=   40.4 FOM= 0.80 TEST= 0
INDE 26 55 43 FOBS=  57.5 SIGMA=  4.5 PHAS=   -9.7 FOM= 0.68 TEST= 0
INDE 26 55 45 FOBS=  61.1 SIGMA=  4.3 PHAS=  -74.7 FOM= 0.80 TEST= 0
INDE 26 55 47 FOBS=  44.4 SIGMA=  6.7 PHAS=  116.7 FOM= 0.14 TEST= 0
INDE 26 56 26 FOBS=  82.7 SIGMA=  2.4 PHAS=   20.3 FOM= 0.84 TEST= 0
INDE 26 56 28 FOBS=  22.3 SIGMA=  8.9 PHAS=   41.1 FOM= 0.41 TEST= 0
INDE 26 56 30 FOBS= 137.5 SIGMA=  2.1 PHAS=  151.4 FOM= 0.94 TEST= 0
INDE 26 56 32 FOBS=   0.0 SIGMA= 28.2 PHAS=    0.0 FOM= 0.00 TEST= 0
INDE 26 56 34 FOBS=  41.1 SIGMA=  6.9 PHAS= -149.2 FOM= 0.46 TEST= 0
INDE 26 56 36 FOBS= 112.0 SIGMA=  2.7 PHAS=  -63.8 FOM= 0.94 TEST= 0
INDE 26 56 38 FOBS=   0.0 SIGMA= 24.4 PHAS=    0.0 FOM= 0.00 TEST= 0
INDE 26 56 40 FOBS=  10.1 SIGMA= 30.3 PHAS= -140.1 FOM= 0.12 TEST= 0
INDE 26 56 42 FOBS= 111.7 SIGMA=  2.9 PHAS=    9.4 FOM= 0.95 TEST= 0
INDE 26 56 44 FOBS=  17.0 SIGMA= 15.4 PHAS=   73.1 FOM= 0.38 TEST= 0
INDE 26 56 46 FOBS= 100.8 SIGMA=  3.1 PHAS= -124.0 FOM= 0.25 TEST= 1
INDE 26 57 27 FOBS=  99.3 SIGMA=  2.2 PHAS=  -76.5 FOM= 0.92 TEST= 0
INDE 26 57 29 FOBS= 150.0 SIGMA=  1.7 PHAS=  -34.7 FOM= 0.92 TEST= 0
INDE 26 57 31 FOBS=  75.1 SIGMA=  4.4 PHAS=   78.8 FOM= 0.79 TEST= 0
INDE 26 57 33 FOBS=  62.4 SIGMA=  6.5 PHAS=  138.7 FOM= 0.68 TEST= 0
INDE 26 57 35 FOBS=  60.1 SIGMA=  4.8 PHAS= -173.5 FOM= 0.83 TEST= 0
INDE 26 57 37 FOBS=   4.2 SIGMA= 81.6 PHAS=   -8.3 FOM= 0.05 TEST= 1
INDE 26 57 39 FOBS=  63.0 SIGMA=  4.9 PHAS=  -11.5 FOM= 0.76 TEST= 0
INDE 26 57 41 FOBS=  77.7 SIGMA=  4.1 PHAS=  -52.4 FOM= 0.92 TEST= 0
INDE 26 57 43 FOBS= 109.3 SIGMA=  2.7 PHAS=  -45.9 FOM= 0.97 TEST= 0
INDE 26 57 45 FOBS=   0.0 SIGMA= 24.4 PHAS=    0.0 FOM= 0.00 TEST= 1
INDE 26 58 26 FOBS=  82.2 SIGMA=  2.9 PHAS=  104.7 FOM= 0.90 TEST= 0
INDE 26 58 28 FOBS=  88.8 SIGMA=  2.7 PHAS= -128.7 FOM= 0.94 TEST= 0
INDE 26 58 30 FOBS=  45.6 SIGMA=  6.9 PHAS=  -36.2 FOM= 0.64 TEST= 0
INDE 26 58 32 FOBS=  71.9 SIGMA=  4.6 PHAS=   12.0 FOM= 0.34 TEST= 0
INDE 26 58 34 FOBS=  22.2 SIGMA= 17.8 PHAS=   91.8 FOM= 0.47 TEST= 0
INDE 26 58 36 FOBS= 121.0 SIGMA=  2.6 PHAS=  -51.9 FOM= 0.96 TEST= 0
INDE 26 58 38 FOBS=  67.0 SIGMA=  4.6 PHAS=  -26.3 FOM= 0.37 TEST= 1
INDE 26 58 40 FOBS=  74.8 SIGMA=  4.3 PHAS= -177.9 FOM= 0.91 TEST= 0
INDE 26 58 42 FOBS=  86.3 SIGMA=  3.8 PHAS=  -96.8 FOM= 0.95 TEST= 0
INDE 26 58 44 FOBS=  54.9 SIGMA=  5.5 PHAS=  -58.7 FOM= 0.67 TEST= 0
INDE 26 59 27 FOBS=   0.0 SIGMA= 21.1 PHAS=    0.0 FOM= 0.00 TEST= 0
INDE 26 59 29 FOBS=  83.7 SIGMA=  2.9 PHAS=   77.5 FOM= 0.31 TEST= 1
INDE 26 59 31 FOBS=   0.0 SIGMA= 23.3 PHAS=    0.0 FOM= 0.00 TEST= 1
INDE 26 59 33 FOBS=   0.0 SIGMA= 25.7 PHAS=    0.0 FOM= 0.00 TEST= 0
INDE 26 59 35 FOBS=  34.9 SIGMA= 11.7 PHAS= -157.1 FOM= 0.60 TEST= 0
INDE 26 59 37 FOBS=  57.6 SIGMA=  5.2 PHAS= -118.3 FOM= 0.89 TEST= 0
INDE 26 59 39 FOBS=  88.9 SIGMA=  3.6 PHAS=  -46.3 FOM= 0.10 TEST= 1
INDE 26 59 41 FOBS=  43.1 SIGMA=  8.7 PHAS=  -99.3 FOM= 0.42 TEST= 0
INDE 26 59 43 FOBS=  34.5 SIGMA= 13.7 PHAS=  157.5 FOM= 0.60 TEST= 0
INDE 26 60 26 FOBS=  82.6 SIGMA=  3.7 PHAS=    5.9 FOM= 0.86 TEST= 0
INDE 26 60 28 FOBS=  47.2 SIGMA=  5.0 PHAS=   12.4 FOM= 0.48 TEST= 0
INDE 26 60 30 FOBS=   0.0 SIGMA= 21.7 PHAS=    0.0 FOM= 0.00 TEST= 0
INDE 26 60 32 FOBS=  76.5 SIGMA=  3.7 PHAS=  111.1 FOM= 0.91 TEST= 0
INDE 26 60 34 FOBS=   0.0 SIGMA= 25.9 PHAS=    0.0 FOM= 0.00 TEST= 0
INDE 26 60 36 FOBS=   0.0 SIGMA= 25.7 PHAS=    0.0 FOM= 0.00 TEST= 0
INDE 26 60 38 FOBS=  54.0 SIGMA=  8.3 PHAS=  125.9 FOM= 0.51 TEST= 0
INDE 26 60 40 FOBS=  49.9 SIGMA=  6.4 PHAS= -142.2 FOM= 0.50 TEST= 0
INDE 26 60 42 FOBS=  27.4 SIGMA= 23.0 PHAS=  -39.5 FOM= 0.18 TEST= 0
INDE 26 61 27 FOBS=  63.3 SIGMA=  3.7 PHAS= -104.6 FOM= 0.89 TEST= 0
INDE 26 61 29 FOBS=  28.4 SIGMA=  8.4 PHAS=  -61.7 FOM= 0.47 TEST= 0
```

*FIG. 12A - 512*

```
INDE 26 61 31 FOBS=  134.7 SIGMA=  2.2 PHAS=    9.4 FOM= 0.92 TEST= 0
INDE 26 61 33 FOBS=   56.0 SIGMA=  5.1 PHAS=    2.7 FOM= 0.79 TEST= 0
INDE 26 61 35 FOBS=    0.0 SIGMA= 26.0 PHAS=    0.0 FOM= 0.00 TEST= 0
INDE 26 61 37 FOBS=    0.0 SIGMA= 26.4 PHAS=    0.0 FOM= 0.00 TEST= 1
INDE 26 61 39 FOBS=    0.0 SIGMA= 24.9 PHAS=    0.0 FOM= 0.00 TEST= 0
INDE 26 62 26 FOBS=   93.2 SIGMA=  3.3 PHAS=  175.0 FOM= 0.87 TEST= 0
INDE 26 62 28 FOBS=    0.0 SIGMA= 23.1 PHAS=    0.0 FOM= 0.00 TEST= 0
INDE 26 62 30 FOBS=  110.2 SIGMA=  2.3 PHAS=    9.9 FOM= 0.05 TEST= 1
INDE 26 62 32 FOBS=  111.1 SIGMA=  2.6 PHAS=  -75.4 FOM= 0.92 TEST= 0
INDE 26 62 34 FOBS=   85.2 SIGMA=  3.5 PHAS=   -7.1 FOM= 0.06 TEST= 1
INDE 26 62 36 FOBS=    6.5 SIGMA= 41.3 PHAS=    6.1 FOM= 0.08 TEST= 0
INDE 26 62 38 FOBS=    0.0 SIGMA= 26.6 PHAS=    0.0 FOM= 0.00 TEST= 1
INDE 26 63 27 FOBS=   54.5 SIGMA=  5.7 PHAS=  111.3 FOM= 0.73 TEST= 0
INDE 26 63 29 FOBS=   56.2 SIGMA=  4.3 PHAS= -122.8 FOM= 0.59 TEST= 0
INDE 26 63 31 FOBS=   10.2 SIGMA= 26.5 PHAS=  164.0 FOM= 0.18 TEST= 0
INDE 26 63 33 FOBS=   92.6 SIGMA=  3.2 PHAS= -142.8 FOM= 0.90 TEST= 0
INDE 26 63 35 FOBS=    0.0 SIGMA= 24.4 PHAS=    0.0 FOM= 0.00 TEST= 0
INDE 26 63 37 FOBS=   61.0 SIGMA=  6.0 PHAS=  124.0 FOM= 0.45 TEST= 0
INDE 26 64 26 FOBS=    0.0 SIGMA= 24.5 PHAS=    0.0 FOM= 0.00 TEST= 1
INDE 26 64 28 FOBS=   19.9 SIGMA= 19.2 PHAS=   32.9 FOM= 0.16 TEST= 0
INDE 26 64 30 FOBS=    0.0 SIGMA= 27.7 PHAS=    0.0 FOM= 0.00 TEST= 0
INDE 26 64 32 FOBS=   25.3 SIGMA= 12.9 PHAS=  164.2 FOM= 0.04 TEST= 1
INDE 26 64 34 FOBS=   97.5 SIGMA=  3.6 PHAS=   52.4 FOM= 0.92 TEST= 0
INDE 26 65 27 FOBS=   27.6 SIGMA= 13.6 PHAS= -141.7 FOM= 0.20 TEST= 0
INDE 26 65 29 FOBS=   53.5 SIGMA=  6.0 PHAS= -156.5 FOM= 0.53 TEST= 0
INDE 26 65 31 FOBS=   49.5 SIGMA=  7.6 PHAS=  129.4 FOM= 0.84 TEST= 0
INDE 26 65 33 FOBS=   91.0 SIGMA=  3.8 PHAS=  -74.2 FOM= 0.93 TEST= 0
INDE 26 66 26 FOBS=    0.0 SIGMA= 31.3 PHAS=    0.0 FOM= 0.00 TEST= 0
INDE 26 66 28 FOBS=   78.1 SIGMA=  6.7 PHAS=  126.5 FOM= 0.84 TEST= 0
INDE 26 66 30 FOBS=    0.0 SIGMA= 25.6 PHAS=    0.0 FOM= 0.00 TEST= 0
INDE 26 67 27 FOBS=   65.4 SIGMA=  7.6 PHAS=  -58.9 FOM= 0.86 TEST= 0
INDE 26 67 29 FOBS=   52.7 SIGMA=  9.9 PHAS=   40.0 FOM= 0.74 TEST= 0
INDE 26 68 26 FOBS=   68.4 SIGMA=  7.5 PHAS= -159.4 FOM= 0.81 TEST= 0
INDE 27 28 27 FOBS=  114.2 SIGMA=  1.6 PHAS=  -48.7 FOM= 0.84 TEST= 1
INDE 27 28 29 FOBS=  276.6 SIGMA=  0.8 PHAS= -110.0 FOM= 0.97 TEST= 0
INDE 27 28 31 FOBS=  263.9 SIGMA=  0.8 PHAS=  -44.9 FOM= 0.91 TEST= 0
INDE 27 28 33 FOBS=  129.9 SIGMA=  1.5 PHAS=  -23.6 FOM= 0.85 TEST= 0
INDE 27 28 35 FOBS=  335.4 SIGMA=  0.7 PHAS=  135.3 FOM= 0.98 TEST= 0
INDE 27 28 37 FOBS=   88.1 SIGMA=  1.9 PHAS= -139.1 FOM= 0.65 TEST= 0
INDE 27 28 39 FOBS=   67.4 SIGMA=  2.4 PHAS=  -42.2 FOM= 0.33 TEST= 0
INDE 27 28 41 FOBS=   88.5 SIGMA=  1.9 PHAS=   -4.4 FOM= 0.18 TEST= 0
INDE 27 28 43 FOBS=   35.9 SIGMA=  4.6 PHAS=  -76.5 FOM= 0.04 TEST= 1
INDE 27 28 45 FOBS=   73.8 SIGMA=  2.2 PHAS=  -73.1 FOM= 0.39 TEST= 0
INDE 27 28 47 FOBS=   90.2 SIGMA=  1.9 PHAS= -105.1 FOM= 0.94 TEST= 0
INDE 27 28 49 FOBS=   50.8 SIGMA=  3.4 PHAS=  130.9 FOM= 0.47 TEST= 0
INDE 27 28 51 FOBS=   51.3 SIGMA=  3.3 PHAS= -129.9 FOM= 0.25 TEST= 0
INDE 27 28 53 FOBS=  132.9 SIGMA=  1.5 PHAS=   70.2 FOM= 0.97 TEST= 0
INDE 27 28 55 FOBS=   78.0 SIGMA=  3.1 PHAS=  125.3 FOM= 0.82 TEST= 1
INDE 27 28 57 FOBS=   69.0 SIGMA=  3.5 PHAS= -140.2 FOM= 0.83 TEST= 0
INDE 27 28 59 FOBS=   32.0 SIGMA=  6.7 PHAS=  -93.6 FOM= 0.61 TEST= 0
INDE 27 28 61 FOBS=   44.5 SIGMA=  6.9 PHAS=   11.5 FOM= 0.26 TEST= 0
INDE 27 28 63 FOBS=    0.0 SIGMA= 24.8 PHAS=    0.0 FOM= 0.00 TEST= 0
INDE 27 28 65 FOBS=   69.9 SIGMA=  7.6 PHAS= -131.5 FOM= 0.75 TEST= 0
INDE 27 28 67 FOBS=   26.4 SIGMA= 20.0 PHAS= -168.6 FOM= 0.35 TEST= 0
INDE 27 29 28 FOBS=   42.8 SIGMA=  4.9 PHAS= -119.9 FOM= 0.43 TEST= 0
INDE 27 29 30 FOBS=  269.7 SIGMA=  0.8 PHAS=  142.1 FOM= 0.96 TEST= 0
INDE 27 29 32 FOBS=  240.7 SIGMA=  0.9 PHAS= -145.5 FOM= 0.97 TEST= 0
INDE 27 29 34 FOBS=    0.0 SIGMA= 19.3 PHAS=    0.0 FOM= 0.00 TEST= 0
INDE 27 29 36 FOBS=  174.1 SIGMA=  1.1 PHAS=   72.2 FOM= 0.94 TEST= 0
INDE 27 29 38 FOBS=  124.8 SIGMA=  1.4 PHAS=  127.5 FOM= 0.90 TEST= 0
INDE 27 29 40 FOBS=    0.0 SIGMA= 18.0 PHAS=    0.0 FOM= 0.00 TEST= 0
INDE 27 29 42 FOBS=  107.4 SIGMA=  1.5 PHAS=  157.1 FOM= 0.73 TEST= 0
INDE 27 29 44 FOBS=   39.9 SIGMA=  4.6 PHAS=   25.4 FOM= 0.40 TEST= 0
INDE 27 29 46 FOBS=   70.7 SIGMA=  2.3 PHAS=  145.6 FOM= 0.80 TEST= 0
INDE 27 29 48 FOBS=   37.0 SIGMA=  4.6 PHAS=  -27.1 FOM= 0.63 TEST= 0
INDE 27 29 50 FOBS=   79.7 SIGMA=  2.2 PHAS=  -33.3 FOM= 0.66 TEST= 0
INDE 27 29 52 FOBS=   81.9 SIGMA=  2.1 PHAS=   53.9 FOM= 0.91 TEST= 0
INDE 27 29 54 FOBS=   60.7 SIGMA=  3.5 PHAS=  -17.1 FOM= 0.89 TEST= 0
INDE 27 29 56 FOBS=   77.3 SIGMA=  3.1 PHAS=   71.1 FOM= 0.63 TEST= 1
INDE 27 29 58 FOBS=  116.7 SIGMA=  2.1 PHAS=   87.3 FOM= 0.96 TEST= 0
```

*FIG. 12A - 513*

```
INDE  27  29  60 FOBS=    0.0 SIGMA= 27.7 PHAS=    0.0 FOM= 0.00 TEST= 1
INDE  27  29  62 FOBS=    0.0 SIGMA= 24.9 PHAS=    0.0 FOM= 0.00 TEST= 0
INDE  27  29  64 FOBS=   16.1 SIGMA= 24.2 PHAS=   91.2 FOM= 0.17 TEST= 0
INDE  27  29  66 FOBS=    0.0 SIGMA= 32.2 PHAS=    0.0 FOM= 0.00 TEST= 0
INDE  27  30  27 FOBS=  137.6 SIGMA=  1.4 PHAS=  -36.6 FOM= 0.93 TEST= 0
INDE  27  30  29 FOBS=   66.6 SIGMA=  2.9 PHAS=  -58.6 FOM= 0.92 TEST= 0
INDE  27  30  31 FOBS=  144.7 SIGMA=  1.4 PHAS=   37.4 FOM= 0.96 TEST= 0
INDE  27  30  33 FOBS=  125.3 SIGMA=  1.6 PHAS=  118.9 FOM= 0.68 TEST= 1
INDE  27  30  35 FOBS=  132.1 SIGMA=  1.5 PHAS=  118.1 FOM= 0.82 TEST= 0
INDE  27  30  37 FOBS=  165.4 SIGMA=  1.2 PHAS=    3.7 FOM= 0.89 TEST= 0
INDE  27  30  39 FOBS=    0.0 SIGMA= 19.0 PHAS=    0.0 FOM= 0.00 TEST= 0
INDE  27  30  41 FOBS=   62.8 SIGMA=  2.6 PHAS=   80.8 FOM= 0.90 TEST= 0
INDE  27  30  43 FOBS=   71.1 SIGMA=  2.3 PHAS=  -30.5 FOM= 0.82 TEST= 0
INDE  27  30  45 FOBS=    0.0 SIGMA= 18.6 PHAS=    0.0 FOM= 0.00 TEST= 0
INDE  27  30  47 FOBS=   31.8 SIGMA=  5.2 PHAS=   91.4 FOM= 0.24 TEST= 0
INDE  27  30  49 FOBS=   88.7 SIGMA=  2.0 PHAS=  105.0 FOM= 0.88 TEST= 0
INDE  27  30  51 FOBS=  124.7 SIGMA=  1.4 PHAS=  -36.8 FOM= 0.95 TEST= 0
INDE  27  30  53 FOBS=   34.7 SIGMA=  5.7 PHAS=   38.8 FOM= 0.20 TEST= 1
INDE  27  30  55 FOBS=   33.3 SIGMA=  8.0 PHAS=  -84.3 FOM= 0.35 TEST= 1
INDE  27  30  57 FOBS=  121.2 SIGMA=  2.1 PHAS=   37.9 FOM= 0.94 TEST= 0
INDE  27  30  59 FOBS=  104.6 SIGMA=  3.2 PHAS=  -27.5 FOM= 0.93 TEST= 0
INDE  27  30  61 FOBS=    0.0 SIGMA= 24.9 PHAS=    0.0 FOM= 0.00 TEST= 0
INDE  27  30  63 FOBS=   49.6 SIGMA= 10.6 PHAS=   40.7 FOM= 0.49 TEST= 0
INDE  27  30  65 FOBS=    0.0 SIGMA= 32.3 PHAS=    0.0 FOM= 0.00 TEST= 0
INDE  27  31  28 FOBS=  117.2 SIGMA=  1.9 PHAS= -161.4 FOM= 0.82 TEST= 0
INDE  27  31  30 FOBS=  105.3 SIGMA=  1.8 PHAS=  135.3 FOM= 0.85 TEST= 0
INDE  27  31  32 FOBS=  183.3 SIGMA=  1.1 PHAS=  -20.6 FOM= 0.89 TEST= 0
INDE  27  31  34 FOBS=  129.3 SIGMA=  1.5 PHAS=  -12.2 FOM= 0.74 TEST= 0
INDE  27  31  36 FOBS=    0.0 SIGMA= 19.9 PHAS=    0.0 FOM= 0.00 TEST= 1
INDE  27  31  38 FOBS=   30.0 SIGMA=  6.4 PHAS=  -43.6 FOM= 0.28 TEST= 0
INDE  27  31  40 FOBS=  195.1 SIGMA=  1.0 PHAS=  -52.7 FOM= 0.90 TEST= 0
INDE  27  31  42 FOBS=   32.1 SIGMA=  5.3 PHAS=  -80.6 FOM= 0.40 TEST= 0
INDE  27  31  44 FOBS=   36.0 SIGMA=  4.6 PHAS= -106.6 FOM= 0.21 TEST= 1
INDE  27  31  46 FOBS=   71.1 SIGMA=  2.3 PHAS=  174.3 FOM= 0.83 TEST= 0
INDE  27  31  48 FOBS=  109.5 SIGMA=  1.6 PHAS=    0.0 FOM= 0.88 TEST= 0
INDE  27  31  50 FOBS=  134.0 SIGMA=  1.3 PHAS=  -69.9 FOM= 0.96 TEST= 0
INDE  27  31  52 FOBS=   53.9 SIGMA=  3.3 PHAS=  -90.5 FOM= 0.26 TEST= 0
INDE  27  31  54 FOBS=   71.5 SIGMA=  2.9 PHAS=  -88.4 FOM= 0.88 TEST= 0
INDE  27  31  56 FOBS=   11.3 SIGMA= 19.1 PHAS=  -94.2 FOM= 0.38 TEST= 0
INDE  27  31  58 FOBS=   43.9 SIGMA=  7.1 PHAS=  -21.7 FOM= 0.66 TEST= 0
INDE  27  31  60 FOBS=   40.0 SIGMA=  7.9 PHAS=  -87.8 FOM= 0.09 TEST= 1
INDE  27  31  62 FOBS=    0.0 SIGMA= 25.1 PHAS=    0.0 FOM= 0.00 TEST= 0
INDE  27  31  64 FOBS=   46.9 SIGMA= 11.3 PHAS=  -58.8 FOM= 0.67 TEST= 0
INDE  27  31  66 FOBS=    0.0 SIGMA= 32.7 PHAS=    0.0 FOM= 0.00 TEST= 0
INDE  27  32  27 FOBS=  256.3 SIGMA=  0.9 PHAS=  114.1 FOM= 0.94 TEST= 0
INDE  27  32  29 FOBS=  127.9 SIGMA=  1.7 PHAS=   81.5 FOM= 0.74 TEST= 0
INDE  27  32  31 FOBS=  386.8 SIGMA=  0.7 PHAS=  -62.0 FOM= 0.98 TEST= 0
INDE  27  32  33 FOBS=   74.7 SIGMA=  2.6 PHAS=  -48.3 FOM= 0.76 TEST= 0
INDE  27  32  35 FOBS=    0.0 SIGMA= 19.2 PHAS=    0.0 FOM= 0.00 TEST= 1
INDE  27  32  37 FOBS=  113.4 SIGMA=  1.7 PHAS=   67.9 FOM= 0.85 TEST= 0
INDE  27  32  39 FOBS=  160.3 SIGMA=  1.2 PHAS= -123.3 FOM= 0.94 TEST= 0
INDE  27  32  41 FOBS=  185.3 SIGMA=  1.1 PHAS= -136.0 FOM= 0.96 TEST= 0
INDE  27  32  43 FOBS=  147.8 SIGMA=  1.3 PHAS=  -60.9 FOM= 0.94 TEST= 0
INDE  27  32  45 FOBS=    9.3 SIGMA= 17.1 PHAS=  174.9 FOM= 0.08 TEST= 0
INDE  27  32  47 FOBS=   76.9 SIGMA=  2.1 PHAS=  145.9 FOM= 0.89 TEST= 0
INDE  27  32  49 FOBS=   60.6 SIGMA=  2.8 PHAS=  146.5 FOM= 0.81 TEST= 0
INDE  27  32  51 FOBS=   60.6 SIGMA=  2.9 PHAS=  -29.1 FOM= 0.52 TEST= 1
INDE  27  32  53 FOBS=   90.2 SIGMA=  2.1 PHAS= -122.0 FOM= 0.89 TEST= 0
INDE  27  32  55 FOBS=   25.7 SIGMA=  7.9 PHAS= -145.2 FOM= 0.61 TEST= 0
INDE  27  32  57 FOBS=   45.8 SIGMA=  5.4 PHAS=   10.4 FOM= 0.41 TEST= 0
INDE  27  32  59 FOBS=    0.0 SIGMA= 27.6 PHAS=    0.0 FOM= 0.00 TEST= 0
INDE  27  32  61 FOBS=   46.5 SIGMA=  6.9 PHAS=   85.1 FOM= 0.52 TEST= 0
INDE  27  32  63 FOBS=    0.0 SIGMA= 25.4 PHAS=    0.0 FOM= 0.00 TEST= 0
INDE  27  32  65 FOBS=   61.0 SIGMA=  6.7 PHAS=  136.3 FOM= 0.22 TEST= 1
INDE  27  33  28 FOBS=  281.2 SIGMA=  0.9 PHAS=   -3.1 FOM= 0.97 TEST= 0
INDE  27  33  30 FOBS=  165.4 SIGMA=  1.4 PHAS= -132.0 FOM= 0.90 TEST= 0
INDE  27  33  32 FOBS=    0.0 SIGMA= 19.2 PHAS=    0.0 FOM= 0.00 TEST= 0
INDE  27  33  34 FOBS=   61.1 SIGMA=  3.0 PHAS=  -60.1 FOM= 0.85 TEST= 0
INDE  27  33  36 FOBS=    0.0 SIGMA= 19.1 PHAS=    0.0 FOM= 0.00 TEST= 0
INDE  27  33  38 FOBS=   76.3 SIGMA=  2.4 PHAS=  154.6 FOM= 0.86 TEST= 0
```

*FIG. 12A - 514*

```
INDE  27  33  40  FOBS=   125.1  SIGMA=   1.5  PHAS=   148.6  FOM=  0.92  TEST= 0
INDE  27  33  42  FOBS=   202.0  SIGMA=   1.0  PHAS=   149.4  FOM=  0.94  TEST= 0
INDE  27  33  44  FOBS=   196.7  SIGMA=   1.0  PHAS=  -140.3  FOM=  0.50  TEST= 1
INDE  27  33  46  FOBS=    32.4  SIGMA=   6.0  PHAS=    97.2  FOM=  0.39  TEST= 0
INDE  27  33  48  FOBS=   104.1  SIGMA=   1.6  PHAS=    20.0  FOM=  0.94  TEST= 0
INDE  27  33  50  FOBS=    60.1  SIGMA=   2.8  PHAS=    43.9  FOM=  0.67  TEST= 0
INDE  27  33  52  FOBS=    88.5  SIGMA=   2.2  PHAS=    13.0  FOM=  0.89  TEST= 0
INDE  27  33  54  FOBS=    87.4  SIGMA=   2.4  PHAS=   151.8  FOM=  0.93  TEST= 0
INDE  27  33  56  FOBS=    11.0  SIGMA=  21.9  PHAS=   -30.2  FOM=  0.05  TEST= 0
INDE  27  33  58  FOBS=    40.6  SIGMA=   6.0  PHAS=  -177.5  FOM=  0.59  TEST= 0
INDE  27  33  60  FOBS=    93.3  SIGMA=   3.5  PHAS=    32.8  FOM=  0.92  TEST= 0
INDE  27  33  62  FOBS=    24.8  SIGMA=  13.0  PHAS=   -30.7  FOM=  0.35  TEST= 0
INDE  27  33  64  FOBS=     0.0  SIGMA=  25.6  PHAS=     0.0  FOM=  0.00  TEST= 0
INDE  27  34  27  FOBS=   263.4  SIGMA=   0.8  PHAS=  -145.6  FOM=  0.97  TEST= 0
INDE  27  34  29  FOBS=    60.8  SIGMA=   3.2  PHAS=  -157.1  FOM=  0.67  TEST= 0
INDE  27  34  31  FOBS=   140.3  SIGMA=   1.4  PHAS=  -132.0  FOM=  0.96  TEST= 0
INDE  27  34  33  FOBS=   120.7  SIGMA=   1.5  PHAS=   -62.8  FOM=  0.85  TEST= 1
INDE  27  34  35  FOBS=     0.0  SIGMA=  19.0  PHAS=     0.0  FOM=  0.00  TEST= 0
INDE  27  34  37  FOBS=     0.0  SIGMA=  20.4  PHAS=     0.0  FOM=  0.00  TEST= 0
INDE  27  34  39  FOBS=    75.5  SIGMA=   2.5  PHAS=    55.5  FOM=  0.77  TEST= 0
INDE  27  34  41  FOBS=   101.9  SIGMA=   1.8  PHAS=    61.1  FOM=  0.90  TEST= 0
INDE  27  34  43  FOBS=   100.1  SIGMA=   1.8  PHAS=    59.6  FOM=  0.93  TEST= 0
INDE  27  34  45  FOBS=    39.2  SIGMA=   4.7  PHAS=    23.4  FOM=  0.50  TEST= 0
INDE  27  34  47  FOBS=     0.0  SIGMA=  18.9  PHAS=     0.0  FOM=  0.00  TEST= 0
INDE  27  34  49  FOBS=    51.0  SIGMA=   3.1  PHAS=  -107.6  FOM=  0.68  TEST= 0
INDE  27  34  51  FOBS=   179.4  SIGMA=   1.2  PHAS=   -63.1  FOM=  0.80  TEST= 1
INDE  27  34  53  FOBS=    64.4  SIGMA=   3.2  PHAS=   -89.4  FOM=  0.74  TEST= 0
INDE  27  34  55  FOBS=     0.0  SIGMA=  23.3  PHAS=     0.0  FOM=  0.00  TEST= 0
INDE  27  34  57  FOBS=     0.0  SIGMA=  22.0  PHAS=     0.0  FOM=  0.00  TEST= 0
INDE  27  34  59  FOBS=    67.7  SIGMA=   3.6  PHAS=  -177.4  FOM=  0.81  TEST= 0
INDE  27  34  61  FOBS=    66.9  SIGMA=   4.9  PHAS=  -117.3  FOM=  0.70  TEST= 0
INDE  27  34  63  FOBS=    27.9  SIGMA=  11.8  PHAS=   -74.0  FOM=  0.64  TEST= 0
INDE  27  35  28  FOBS=   198.1  SIGMA=   1.1  PHAS=    45.8  FOM=  0.91  TEST= 0
INDE  27  35  30  FOBS=   130.9  SIGMA=   1.5  PHAS=    73.4  FOM=  0.93  TEST= 0
INDE  27  35  32  FOBS=   161.9  SIGMA=   1.1  PHAS=   138.3  FOM=  0.76  TEST= 1
INDE  27  35  34  FOBS=    84.0  SIGMA=   2.0  PHAS=  -131.6  FOM=  0.84  TEST= 0
INDE  27  35  36  FOBS=   116.0  SIGMA=   1.5  PHAS=   -25.0  FOM=  0.68  TEST= 0
INDE  27  35  38  FOBS=    95.8  SIGMA=   1.8  PHAS=    78.5  FOM=  0.63  TEST= 0
INDE  27  35  40  FOBS=    37.8  SIGMA=   4.3  PHAS=    38.2  FOM=  0.78  TEST= 0
INDE  27  35  42  FOBS=   116.9  SIGMA=   1.6  PHAS=   -25.4  FOM=  0.91  TEST= 0
INDE  27  35  44  FOBS=    69.3  SIGMA=   2.5  PHAS=   -94.7  FOM=  0.85  TEST= 0
INDE  27  35  46  FOBS=    24.8  SIGMA=   7.3  PHAS=    -5.6  FOM=  0.11  TEST= 0
INDE  27  35  48  FOBS=     0.0  SIGMA=  19.0  PHAS=     0.0  FOM=  0.00  TEST= 0
INDE  27  35  50  FOBS=    54.5  SIGMA=   3.2  PHAS=  -164.0  FOM=  0.82  TEST= 0
INDE  27  35  52  FOBS=    74.6  SIGMA=   2.5  PHAS=   -95.2  FOM=  0.24  TEST= 1
INDE  27  35  54  FOBS=   144.2  SIGMA=   1.8  PHAS=   159.2  FOM=  0.95  TEST= 0
INDE  27  35  56  FOBS=    84.2  SIGMA=   3.0  PHAS=   -31.3  FOM=  0.90  TEST= 0
INDE  27  35  58  FOBS=    59.2  SIGMA=   4.2  PHAS=    87.0  FOM=  0.87  TEST= 0
INDE  27  35  60  FOBS=    37.1  SIGMA=   7.6  PHAS=   138.2  FOM=  0.12  TEST= 1
INDE  27  35  62  FOBS=     0.0  SIGMA=  25.4  PHAS=     0.0  FOM=  0.00  TEST= 0
INDE  27  36  27  FOBS=    98.6  SIGMA=   1.7  PHAS=   155.3  FOM=  0.92  TEST= 0
INDE  27  36  29  FOBS=   156.4  SIGMA=   1.3  PHAS=   -67.9  FOM=  0.94  TEST= 0
INDE  27  36  31  FOBS=   114.3  SIGMA=   1.6  PHAS=   -21.9  FOM=  0.93  TEST= 0
INDE  27  36  33  FOBS=   120.6  SIGMA=   1.4  PHAS=    73.2  FOM=  0.93  TEST= 0
INDE  27  36  35  FOBS=     0.0  SIGMA=  18.0  PHAS=     0.0  FOM=  0.00  TEST= 0
INDE  27  36  37  FOBS=   208.9  SIGMA=   0.9  PHAS=   -86.4  FOM=  0.96  TEST= 0
INDE  27  36  39  FOBS=   123.7  SIGMA=   1.4  PHAS=   -20.6  FOM=  0.91  TEST= 0
INDE  27  36  41  FOBS=    69.8  SIGMA=   2.4  PHAS=    70.5  FOM=  0.83  TEST= 0
INDE  27  36  43  FOBS=    50.4  SIGMA=   3.2  PHAS=    84.7  FOM=  0.81  TEST= 0
INDE  27  36  45  FOBS=     0.0  SIGMA=  18.2  PHAS=     0.0  FOM=  0.00  TEST= 0
INDE  27  36  47  FOBS=    52.0  SIGMA=   3.3  PHAS=   -13.8  FOM=  0.83  TEST= 0
INDE  27  36  49  FOBS=   104.5  SIGMA=   1.7  PHAS=   154.4  FOM=  0.91  TEST= 0
INDE  27  36  51  FOBS=    36.4  SIGMA=   5.3  PHAS=    16.5  FOM=  0.46  TEST= 0
INDE  27  36  53  FOBS=    94.9  SIGMA=   2.7  PHAS=    20.7  FOM=  0.83  TEST= 0
INDE  27  36  55  FOBS=   105.6  SIGMA=   2.4  PHAS=  -120.3  FOM=  0.95  TEST= 0
INDE  27  36  57  FOBS=    43.8  SIGMA=   5.6  PHAS=   -63.3  FOM=  0.87  TEST= 0
INDE  27  36  59  FOBS=    28.8  SIGMA=   8.4  PHAS=     9.5  FOM=  0.05  TEST= 1
INDE  27  36  61  FOBS=     0.0  SIGMA=  23.0  PHAS=     0.0  FOM=  0.00  TEST= 0
INDE  27  36  63  FOBS=    44.3  SIGMA=   7.5  PHAS=    29.9  FOM=  0.11  TEST= 0
INDE  27  37  28  FOBS=    40.2  SIGMA=   4.5  PHAS=  -159.3  FOM=  0.48  TEST= 0
```

*FIG. 12A - 515*

```
INDE 27 37 30 FOBS=    89.3 SIGMA=  2.1 PHAS=  -62.9 FOM= 0.92 TEST= 0
INDE 27 37 32 FOBS=    37.8 SIGMA=  5.3 PHAS=  -96.7 FOM= 0.66 TEST= 0
INDE 27 37 34 FOBS=     0.0 SIGMA= 18.7 PHAS=    0.0 FOM= 0.00 TEST= 0
INDE 27 37 36 FOBS=    75.8 SIGMA=  2.2 PHAS=  125.0 FOM= 0.58 TEST= 0
INDE 27 37 38 FOBS=    83.1 SIGMA=  2.0 PHAS= -154.2 FOM= 0.89 TEST= 0
INDE 27 37 40 FOBS=   137.9 SIGMA=  1.3 PHAS=    6.7 FOM= 0.97 TEST= 0
INDE 27 37 42 FOBS=   130.3 SIGMA=  1.3 PHAS=   11.7 FOM= 0.90 TEST= 0
INDE 27 37 44 FOBS=    24.2 SIGMA=  6.8 PHAS=  -10.9 FOM= 0.44 TEST= 0
INDE 27 37 46 FOBS=    57.4 SIGMA=  2.8 PHAS= -112.1 FOM= 0.83 TEST= 0
INDE 27 37 48 FOBS=    86.7 SIGMA=  1.8 PHAS=   54.6 FOM= 0.90 TEST= 0
INDE 27 37 50 FOBS=    90.6 SIGMA=  2.0 PHAS=   19.0 FOM= 0.83 TEST= 0
INDE 27 37 52 FOBS=    75.0 SIGMA=  2.6 PHAS= -106.3 FOM= 0.72 TEST= 0
INDE 27 37 54 FOBS=   168.4 SIGMA=  1.6 PHAS=  161.7 FOM= 0.97 TEST= 0
INDE 27 37 56 FOBS=     0.0 SIGMA= 22.0 PHAS=    0.0 FOM= 0.00 TEST= 0
INDE 27 37 58 FOBS=    47.2 SIGMA=  5.2 PHAS=   92.1 FOM= 0.72 TEST= 0
INDE 27 37 60 FOBS=     0.0 SIGMA= 24.8 PHAS=    0.0 FOM= 0.00 TEST= 0
INDE 27 37 62 FOBS=     0.0 SIGMA= 29.0 PHAS=    0.0 FOM= 0.00 TEST= 0
INDE 27 38 27 FOBS=    13.0 SIGMA= 13.6 PHAS=  -53.4 FOM= 0.14 TEST= 0
INDE 27 38 29 FOBS=     0.0 SIGMA= 20.2 PHAS=    0.0 FOM= 0.00 TEST= 0
INDE 27 38 31 FOBS=    73.0 SIGMA=  2.5 PHAS=  180.0 FOM= 0.85 TEST= 0
INDE 27 38 33 FOBS=     0.0 SIGMA= 19.8 PHAS=    0.0 FOM= 0.00 TEST= 0
INDE 27 38 35 FOBS=     0.0 SIGMA= 18.6 PHAS=    0.0 FOM= 0.00 TEST= 0
INDE 27 38 37 FOBS=   108.2 SIGMA=  1.6 PHAS=  -85.0 FOM= 0.84 TEST= 0
INDE 27 38 39 FOBS=   111.7 SIGMA=  1.5 PHAS=  -32.2 FOM= 0.94 TEST= 0
INDE 27 38 41 FOBS=    38.8 SIGMA=  4.8 PHAS=  -70.2 FOM= 0.67 TEST= 0
INDE 27 38 43 FOBS=    54.8 SIGMA=  3.0 PHAS=  -20.1 FOM= 0.73 TEST= 0
INDE 27 38 45 FOBS=    41.3 SIGMA=  3.8 PHAS=    2.8 FOM= 0.77 TEST= 0
INDE 27 38 47 FOBS=    57.4 SIGMA=  2.8 PHAS=  -91.4 FOM= 0.85 TEST= 0
INDE 27 38 49 FOBS=    35.8 SIGMA=  5.9 PHAS=  -43.7 FOM= 0.32 TEST= 0
INDE 27 38 51 FOBS=    54.5 SIGMA=  3.2 PHAS= -117.4 FOM= 0.84 TEST= 0
INDE 27 38 53 FOBS=    81.6 SIGMA=  2.3 PHAS=   75.1 FOM= 0.92 TEST= 0
INDE 27 38 55 FOBS=     0.0 SIGMA= 22.2 PHAS=    0.0 FOM= 0.00 TEST= 0
INDE 27 38 57 FOBS=    71.1 SIGMA=  3.5 PHAS=  -24.3 FOM= 0.88 TEST= 0
INDE 27 38 59 FOBS=    45.9 SIGMA=  5.5 PHAS=  -14.4 FOM= 0.78 TEST= 0
INDE 27 38 61 FOBS=    45.2 SIGMA=  7.3 PHAS=  -36.6 FOM= 0.70 TEST= 0
INDE 27 39 28 FOBS=   288.9 SIGMA=  0.8 PHAS= -122.1 FOM= 0.95 TEST= 0
INDE 27 39 30 FOBS=   114.8 SIGMA=  1.6 PHAS=  -95.2 FOM= 0.47 TEST= 0
INDE 27 39 32 FOBS=    72.6 SIGMA=  2.5 PHAS=   89.7 FOM= 0.91 TEST= 0
INDE 27 39 34 FOBS=   122.2 SIGMA=  1.4 PHAS= -159.1 FOM= 0.83 TEST= 0
INDE 27 39 36 FOBS=    51.6 SIGMA=  3.1 PHAS=   76.7 FOM= 0.77 TEST= 0
INDE 27 39 38 FOBS=   171.9 SIGMA=  1.0 PHAS= -174.4 FOM= 0.96 TEST= 0
INDE 27 39 40 FOBS=    26.4 SIGMA=  6.4 PHAS=  -64.2 FOM= 0.33 TEST= 0
INDE 27 39 42 FOBS=    45.7 SIGMA=  3.7 PHAS=   28.3 FOM= 0.52 TEST= 0
INDE 27 39 44 FOBS=    59.2 SIGMA=  2.8 PHAS=  -80.6 FOM= 0.06 TEST= 1
INDE 27 39 46 FOBS=    77.6 SIGMA=  2.1 PHAS= -143.4 FOM= 0.87 TEST= 0
INDE 27 39 48 FOBS=     0.0 SIGMA= 19.5 PHAS=    0.0 FOM= 0.00 TEST= 0
INDE 27 39 50 FOBS=    63.8 SIGMA=  2.8 PHAS=   56.7 FOM= 0.88 TEST= 0
INDE 27 39 52 FOBS=     0.0 SIGMA= 19.9 PHAS=    0.0 FOM= 0.00 TEST= 0
INDE 27 39 54 FOBS=    39.4 SIGMA=  5.0 PHAS= -128.1 FOM= 0.10 TEST= 1
INDE 27 39 56 FOBS=    65.2 SIGMA=  3.5 PHAS=  -99.1 FOM= 0.78 TEST= 0
INDE 27 39 58 FOBS=    70.4 SIGMA=  3.6 PHAS= -118.3 FOM= 0.86 TEST= 0
INDE 27 39 60 FOBS=    65.3 SIGMA=  4.4 PHAS=  -94.2 FOM= 0.88 TEST= 0
INDE 27 40 27 FOBS=   100.9 SIGMA=  1.6 PHAS=  119.6 FOM= 0.77 TEST= 0
INDE 27 40 29 FOBS=   202.9 SIGMA=  1.0 PHAS=  108.1 FOM= 0.54 TEST= 1
INDE 27 40 31 FOBS=    71.5 SIGMA=  2.6 PHAS= -151.5 FOM= 0.89 TEST= 0
INDE 27 40 33 FOBS=   118.6 SIGMA=  1.6 PHAS=   18.1 FOM= 0.84 TEST= 0
INDE 27 40 35 FOBS=   111.8 SIGMA=  1.5 PHAS=   62.0 FOM= 0.88 TEST= 0
INDE 27 40 37 FOBS=    80.8 SIGMA=  2.1 PHAS=   84.5 FOM= 0.62 TEST= 0
INDE 27 40 39 FOBS=   145.0 SIGMA=  1.2 PHAS=   83.7 FOM= 0.94 TEST= 0
INDE 27 40 41 FOBS=    57.5 SIGMA=  2.9 PHAS= -154.7 FOM= 0.65 TEST= 0
INDE 27 40 43 FOBS=   107.2 SIGMA=  1.6 PHAS=  -14.3 FOM= 0.83 TEST= 0
INDE 27 40 45 FOBS=    37.6 SIGMA=  4.5 PHAS=   56.6 FOM= 0.74 TEST= 0
INDE 27 40 47 FOBS=    91.9 SIGMA=  2.0 PHAS=  124.3 FOM= 0.90 TEST= 0
INDE 27 40 49 FOBS=    97.8 SIGMA=  1.8 PHAS=  -57.6 FOM= 0.90 TEST= 0
INDE 27 40 51 FOBS=    92.3 SIGMA=  2.0 PHAS=  -96.5 FOM= 0.91 TEST= 0
INDE 27 40 53 FOBS=    15.4 SIGMA= 12.3 PHAS=  160.4 FOM= 0.26 TEST= 0
INDE 27 40 55 FOBS=     0.0 SIGMA= 20.0 PHAS=    0.0 FOM= 0.00 TEST= 0
INDE 27 40 57 FOBS=    80.6 SIGMA=  2.7 PHAS=  -48.6 FOM= 0.26 TEST= 1
INDE 27 40 59 FOBS=    45.7 SIGMA=  5.6 PHAS=  143.6 FOM= 0.84 TEST= 0
INDE 27 41 28 FOBS=    65.5 SIGMA=  2.6 PHAS=  -65.7 FOM= 0.82 TEST= 0
```

*FIG. 12A - 516*

```
INDE  27  41  30 FOBS=   110.5 SIGMA=   1.7 PHAS=    38.0 FOM=  0.86 TEST= 0
INDE  27  41  32 FOBS=    94.7 SIGMA=   1.9 PHAS=    63.1 FOM=  0.92 TEST= 1
INDE  27  41  34 FOBS=   171.2 SIGMA=   1.1 PHAS=   -90.2 FOM=  0.39 TEST= 1
INDE  27  41  36 FOBS=    96.3 SIGMA=   1.7 PHAS=   -10.8 FOM=  0.90 TEST= 0
INDE  27  41  38 FOBS=    80.2 SIGMA=   2.1 PHAS=    60.1 FOM=  0.67 TEST= 0
INDE  27  41  40 FOBS=    80.4 SIGMA=   2.1 PHAS=    -6.3 FOM=  0.84 TEST= 0
INDE  27  41  42 FOBS=    63.1 SIGMA=   2.6 PHAS=   173.2 FOM=  0.80 TEST= 0
INDE  27  41  44 FOBS=    18.0 SIGMA=   9.4 PHAS=    -0.4 FOM=  0.58 TEST= 0
INDE  27  41  46 FOBS=    56.9 SIGMA=   3.1 PHAS=    51.5 FOM=  0.56 TEST= 0
INDE  27  41  48 FOBS=    25.3 SIGMA=   7.9 PHAS=    98.8 FOM=  0.45 TEST= 0
INDE  27  41  50 FOBS=   129.5 SIGMA=   1.4 PHAS=   162.3 FOM=  0.95 TEST= 0
INDE  27  41  52 FOBS=   144.3 SIGMA=   1.4 PHAS=   124.6 FOM=  0.96 TEST= 0
INDE  27  41  54 FOBS=    30.0 SIGMA=   6.3 PHAS=   105.0 FOM=  0.25 TEST= 0
INDE  27  41  56 FOBS=    38.9 SIGMA=   5.3 PHAS=   104.5 FOM=  0.08 TEST= 0
INDE  27  41  58 FOBS=    30.4 SIGMA=   7.6 PHAS=    22.1 FOM=  0.76 TEST= 0
INDE  27  41  60 FOBS=     0.0 SIGMA=  24.5 PHAS=     0.0 FOM=  0.00 TEST= 0
INDE  27  42  27 FOBS=     0.0 SIGMA=  17.8 PHAS=     0.0 FOM=  0.00 TEST= 0
INDE  27  42  29 FOBS=    70.8 SIGMA=   2.5 PHAS=  -133.6 FOM=  0.57 TEST= 0
INDE  27  42  31 FOBS=    67.5 SIGMA=   2.7 PHAS=   -92.3 FOM=  0.76 TEST= 0
INDE  27  42  33 FOBS=    55.9 SIGMA=   3.2 PHAS=   -11.0 FOM=  0.73 TEST= 0
INDE  27  42  35 FOBS=     0.0 SIGMA=  21.2 PHAS=     0.0 FOM=  0.00 TEST= 0
INDE  27  42  37 FOBS=    61.9 SIGMA=   2.6 PHAS=  -139.8 FOM=  0.48 TEST= 0
INDE  27  42  39 FOBS=    51.8 SIGMA=   3.3 PHAS=   107.9 FOM=  0.75 TEST= 0
INDE  27  42  41 FOBS=    38.7 SIGMA=   4.2 PHAS=   145.6 FOM=  0.65 TEST= 0
INDE  27  42  43 FOBS=    98.9 SIGMA=   1.8 PHAS=  -134.7 FOM=  0.67 TEST= 0
INDE  27  42  45 FOBS=    75.4 SIGMA=   2.4 PHAS=    32.3 FOM=  0.06 TEST= 1
INDE  27  42  47 FOBS=   107.8 SIGMA=   1.7 PHAS=    85.6 FOM=  0.38 TEST= 1
INDE  27  42  49 FOBS=    23.7 SIGMA=   7.9 PHAS=  -125.8 FOM=  0.02 TEST= 1
INDE  27  42  51 FOBS=    68.7 SIGMA=   2.8 PHAS=    77.0 FOM=  0.87 TEST= 0
INDE  27  42  53 FOBS=    44.2 SIGMA=   4.3 PHAS=   -60.2 FOM=  0.78 TEST= 0
INDE  27  42  55 FOBS=    45.5 SIGMA=   4.6 PHAS=    19.7 FOM=  0.52 TEST= 0
INDE  27  42  57 FOBS=     0.0 SIGMA=  20.2 PHAS=     0.0 FOM=  0.00 TEST= 0
INDE  27  42  59 FOBS=    58.4 SIGMA=   4.6 PHAS=   176.9 FOM=  0.85 TEST= 0
INDE  27  43  28 FOBS=    41.4 SIGMA=   3.8 PHAS=    74.6 FOM=  0.49 TEST= 0
INDE  27  43  30 FOBS=   118.8 SIGMA=   1.6 PHAS=   101.2 FOM=  0.97 TEST= 0
INDE  27  43  32 FOBS=     0.0 SIGMA=  19.3 PHAS=     0.0 FOM=  0.00 TEST= 0
INDE  27  43  34 FOBS=   180.0 SIGMA=   1.1 PHAS=  -146.5 FOM=  0.95 TEST= 0
INDE  27  43  36 FOBS=    33.7 SIGMA=   5.3 PHAS=  -135.7 FOM=  0.80 TEST= 0
INDE  27  43  38 FOBS=    80.2 SIGMA=   2.1 PHAS=    84.3 FOM=  0.87 TEST= 0
INDE  27  43  40 FOBS=     0.0 SIGMA=  20.5 PHAS=     0.0 FOM=  0.00 TEST= 0
INDE  27  43  42 FOBS=    33.2 SIGMA=   5.4 PHAS=  -122.5 FOM=  0.26 TEST= 0
INDE  27  43  44 FOBS=    41.0 SIGMA=   4.6 PHAS=    -1.7 FOM=  0.65 TEST= 0
INDE  27  43  46 FOBS=    60.3 SIGMA=   3.1 PHAS=    82.1 FOM=  0.84 TEST= 0
INDE  27  43  48 FOBS=    50.7 SIGMA=   3.6 PHAS=    52.7 FOM=  0.79 TEST= 0
INDE  27  43  50 FOBS=    64.2 SIGMA=   2.8 PHAS=    92.9 FOM=  0.66 TEST= 0
INDE  27  43  52 FOBS=    78.0 SIGMA=   2.5 PHAS=   137.0 FOM=  0.89 TEST= 0
INDE  27  43  54 FOBS=     0.0 SIGMA=  20.1 PHAS=     0.0 FOM=  0.00 TEST= 0
INDE  27  43  56 FOBS=     0.0 SIGMA=  20.2 PHAS=     0.0 FOM=  0.00 TEST= 0
INDE  27  43  58 FOBS=    57.7 SIGMA=   4.0 PHAS=    58.0 FOM=  0.88 TEST= 0
INDE  27  44  27 FOBS=    66.7 SIGMA=   2.4 PHAS=    63.1 FOM=  0.23 TEST= 0
INDE  27  44  29 FOBS=   140.5 SIGMA=   1.3 PHAS=     6.4 FOM=  0.95 TEST= 0
INDE  27  44  31 FOBS=   127.9 SIGMA=   1.5 PHAS=   -37.7 FOM=  0.94 TEST= 0
INDE  27  44  33 FOBS=    88.5 SIGMA=   2.1 PHAS=   139.0 FOM=  0.66 TEST= 0
INDE  27  44  35 FOBS=   125.2 SIGMA=   1.5 PHAS=   111.5 FOM=  0.94 TEST= 0
INDE  27  44  37 FOBS=    24.1 SIGMA=   7.4 PHAS=   101.9 FOM=  0.50 TEST= 0
INDE  27  44  39 FOBS=     0.0 SIGMA=  18.7 PHAS=     0.0 FOM=  0.00 TEST= 1
INDE  27  44  41 FOBS=     0.0 SIGMA=  19.3 PHAS=     0.0 FOM=  0.00 TEST= 0
INDE  27  44  43 FOBS=     0.0 SIGMA=  20.5 PHAS=     0.0 FOM=  0.00 TEST= 0
INDE  27  44  45 FOBS=    82.3 SIGMA=   2.2 PHAS=    -9.7 FOM=  0.90 TEST= 0
INDE  27  44  47 FOBS=    82.4 SIGMA=   2.2 PHAS=    20.8 FOM=  0.93 TEST= 0
INDE  27  44  49 FOBS=    60.8 SIGMA=   3.0 PHAS=  -114.4 FOM=  0.39 TEST= 0
INDE  27  44  51 FOBS=    50.8 SIGMA=   3.8 PHAS=    60.3 FOM=  0.66 TEST= 0
INDE  27  44  53 FOBS=    49.8 SIGMA=   4.1 PHAS=   -37.8 FOM=  0.64 TEST= 0
INDE  27  44  55 FOBS=    40.1 SIGMA=   4.8 PHAS=    -8.6 FOM=  0.80 TEST= 0
INDE  27  44  57 FOBS=    78.8 SIGMA=   2.7 PHAS=   -88.8 FOM=  0.91 TEST= 0
INDE  27  45  28 FOBS=   116.6 SIGMA=   1.4 PHAS=  -119.8 FOM=  0.83 TEST= 0
INDE  27  45  30 FOBS=   129.8 SIGMA=   1.4 PHAS=   158.8 FOM=  0.92 TEST= 0
INDE  27  45  32 FOBS=     0.0 SIGMA=  19.2 PHAS=     0.0 FOM=  0.00 TEST= 0
INDE  27  45  34 FOBS=    62.9 SIGMA=   2.9 PHAS=   -11.6 FOM=  0.72 TEST= 0
INDE  27  45  36 FOBS=     0.0 SIGMA=  18.8 PHAS=     0.0 FOM=  0.00 TEST= 1
```

*FIG. 12A - 517*

```
INDE  27  45  38  FOBS=   38.8  SIGMA=   4.2  PHAS=  -158.6  FOM=  0.58  TEST= 0
INDE  27  45  40  FOBS=  141.7  SIGMA=   1.4  PHAS=  -145.8  FOM=  0.96  TEST= 0
INDE  27  45  42  FOBS=   31.3  SIGMA=   5.7  PHAS=  -120.2  FOM=  0.43  TEST= 0
INDE  27  45  44  FOBS=   21.6  SIGMA=   9.9  PHAS=   -55.8  FOM=  0.13  TEST= 0
INDE  27  45  46  FOBS=   90.2  SIGMA=   2.1  PHAS=   -78.0  FOM=  0.86  TEST= 0
INDE  27  45  48  FOBS=    0.0  SIGMA=  19.4  PHAS=     0.0  FOM=  0.00  TEST= 0
INDE  27  45  50  FOBS=   72.1  SIGMA=   2.6  PHAS=   157.0  FOM=  0.87  TEST= 0
INDE  27  45  52  FOBS=   31.6  SIGMA=   6.5  PHAS=   167.6  FOM=  0.61  TEST= 0
INDE  27  45  54  FOBS=    0.0  SIGMA=  20.3  PHAS=     0.0  FOM=  0.00  TEST= 0
INDE  27  45  56  FOBS=   36.4  SIGMA=   5.8  PHAS=  -163.8  FOM=  0.62  TEST= 0
INDE  27  46  27  FOBS=   45.6  SIGMA=   4.2  PHAS=  -135.6  FOM=  0.24  TEST= 0
INDE  27  46  29  FOBS=   21.4  SIGMA=   8.1  PHAS=    30.2  FOM=  0.31  TEST= 1
INDE  27  46  31  FOBS=  129.0  SIGMA=   1.4  PHAS=    31.9  FOM=  0.96  TEST= 0
INDE  27  46  33  FOBS=   30.3  SIGMA=   6.2  PHAS=     6.1  FOM=  0.76  TEST= 0
INDE  27  46  35  FOBS=   46.5  SIGMA=   4.2  PHAS=   145.3  FOM=  0.14  TEST= 0
INDE  27  46  37  FOBS=  107.2  SIGMA=   1.9  PHAS=   138.9  FOM=  0.94  TEST= 0
INDE  27  46  39  FOBS=  189.2  SIGMA=   1.1  PHAS=   144.0  FOM=  0.98  TEST= 0
INDE  27  46  41  FOBS=  136.2  SIGMA=   1.4  PHAS=    59.6  FOM=  0.96  TEST= 0
INDE  27  46  43  FOBS=   30.4  SIGMA=   6.3  PHAS=   175.8  FOM=  0.22  TEST= 0
INDE  27  46  45  FOBS=   48.1  SIGMA=   4.0  PHAS=   -25.1  FOM=  0.61  TEST= 0
INDE  27  46  47  FOBS=   92.1  SIGMA=   2.0  PHAS=    33.3  FOM=  0.78  TEST= 0
INDE  27  46  49  FOBS=   32.5  SIGMA=   6.3  PHAS=    29.1  FOM=  0.40  TEST= 0
INDE  27  46  51  FOBS=   88.2  SIGMA=   2.3  PHAS=    41.6  FOM=  0.94  TEST= 0
INDE  27  46  53  FOBS=   69.3  SIGMA=   2.9  PHAS=   -36.2  FOM=  0.83  TEST= 0
INDE  27  46  55  FOBS=    0.0  SIGMA=  21.3  PHAS=     0.0  FOM=  0.00  TEST= 0
INDE  27  47  28  FOBS=   93.6  SIGMA=   1.9  PHAS=  -159.6  FOM=  0.94  TEST= 0
INDE  27  47  30  FOBS=   40.4  SIGMA=   4.4  PHAS=   -65.4  FOM=  0.27  TEST= 0
INDE  27  47  32  FOBS=  130.9  SIGMA=   1.4  PHAS=   -11.7  FOM=  0.96  TEST= 0
INDE  27  47  34  FOBS=   31.7  SIGMA=   5.9  PHAS=   -69.4  FOM=  0.42  TEST= 0
INDE  27  47  36  FOBS=    0.0  SIGMA=  20.6  PHAS=     0.0  FOM=  0.00  TEST= 1
INDE  27  47  38  FOBS=  117.6  SIGMA=   1.8  PHAS=    59.7  FOM=  0.92  TEST= 0
INDE  27  47  40  FOBS=   66.1  SIGMA=   3.1  PHAS=   -27.9  FOM=  0.09  TEST= 1
INDE  27  47  42  FOBS=   65.7  SIGMA=   2.8  PHAS=   -72.1  FOM=  0.51  TEST= 1
INDE  27  47  44  FOBS=    2.4  SIGMA=  84.7  PHAS=    25.4  FOM=  0.00  TEST= 0
INDE  27  47  46  FOBS=  180.6  SIGMA=   1.1  PHAS=   -83.8  FOM=  0.97  TEST= 0
INDE  27  47  48  FOBS=   55.4  SIGMA=   3.4  PHAS=   -90.3  FOM=  0.72  TEST= 0
INDE  27  47  50  FOBS=   44.6  SIGMA=   4.5  PHAS=  -139.7  FOM=  0.70  TEST= 0
INDE  27  47  52  FOBS=   16.8  SIGMA=  13.4  PHAS=   116.6  FOM=  0.24  TEST= 0
INDE  27  47  54  FOBS=   14.6  SIGMA=  15.5  PHAS=   110.4  FOM=  0.21  TEST= 0
INDE  27  48  27  FOBS=  127.1  SIGMA=   1.4  PHAS=    25.3  FOM=  0.95  TEST= 0
INDE  27  48  29  FOBS=    0.0  SIGMA=  18.4  PHAS=     0.0  FOM=  0.00  TEST= 0
INDE  27  48  31  FOBS=   45.4  SIGMA=   3.9  PHAS=  -135.4  FOM=  0.77  TEST= 0
INDE  27  48  33  FOBS=  118.2  SIGMA=   1.7  PHAS=   -21.9  FOM=  0.86  TEST= 0
INDE  27  48  35  FOBS=  108.2  SIGMA=   1.9  PHAS=    36.2  FOM=  0.92  TEST= 0
INDE  27  48  37  FOBS=   92.3  SIGMA=   2.2  PHAS=  -165.8  FOM=  0.86  TEST= 0
INDE  27  48  39  FOBS=   79.8  SIGMA=   2.4  PHAS=   173.9  FOM=  0.87  TEST= 0
INDE  27  48  41  FOBS=   73.2  SIGMA=   2.5  PHAS=    54.6  FOM=  0.09  TEST= 1
INDE  27  48  43  FOBS=   82.9  SIGMA=   2.3  PHAS=   117.8  FOM=  0.76  TEST= 0
INDE  27  48  45  FOBS=   86.9  SIGMA=   2.2  PHAS=  -175.8  FOM=  0.92  TEST= 0
INDE  27  48  47  FOBS=   51.5  SIGMA=   3.6  PHAS=  -153.9  FOM=  0.86  TEST= 0
INDE  27  48  49  FOBS=   88.9  SIGMA=   2.2  PHAS=   179.5  FOM=  0.87  TEST= 0
INDE  27  48  51  FOBS=   72.4  SIGMA=   2.8  PHAS=    24.6  FOM=  0.86  TEST= 0
INDE  27  48  53  FOBS=   59.2  SIGMA=   3.7  PHAS=   -29.2  FOM=  0.90  TEST= 0
INDE  27  49  28  FOBS=   27.4  SIGMA=   6.8  PHAS=  -144.0  FOM=  0.63  TEST= 1
INDE  27  49  30  FOBS=   65.8  SIGMA=   2.7  PHAS=    89.8  FOM=  0.46  TEST= 1
INDE  27  49  32  FOBS=   68.0  SIGMA=   3.2  PHAS=   -50.1  FOM=  0.86  TEST= 0
INDE  27  49  34  FOBS=  127.8  SIGMA=   1.6  PHAS=   -70.0  FOM=  0.94  TEST= 0
INDE  27  49  36  FOBS=  107.8  SIGMA=   1.9  PHAS=    14.9  FOM=  0.31  TEST= 1
INDE  27  49  38  FOBS=   94.7  SIGMA=   2.2  PHAS=   147.9  FOM=  0.89  TEST= 0
INDE  27  49  40  FOBS=   61.5  SIGMA=   3.0  PHAS=    61.2  FOM=  0.81  TEST= 0
INDE  27  49  42  FOBS=   48.2  SIGMA=   3.8  PHAS=     7.2  FOM=  0.64  TEST= 0
INDE  27  49  44  FOBS=   94.3  SIGMA=   2.0  PHAS=    83.0  FOM=  0.90  TEST= 0
INDE  27  49  46  FOBS=   82.0  SIGMA=   2.3  PHAS=  -114.5  FOM=  0.94  TEST= 0
INDE  27  49  48  FOBS=   86.3  SIGMA=   2.5  PHAS=   150.3  FOM=  0.94  TEST= 0
INDE  27  49  50  FOBS=   78.7  SIGMA=   2.8  PHAS=    95.1  FOM=  0.85  TEST= 0
INDE  27  49  52  FOBS=   34.3  SIGMA=   6.8  PHAS=  -171.3  FOM=  0.69  TEST= 0
INDE  27  49  54  FOBS=   14.0  SIGMA=  26.5  PHAS=   -44.4  FOM=  0.14  TEST= 0
INDE  27  50  27  FOBS=   58.2  SIGMA=   2.9  PHAS=    34.2  FOM=  0.77  TEST= 0
INDE  27  50  29  FOBS=   30.0  SIGMA=   6.8  PHAS=   -54.2  FOM=  0.15  TEST= 0
INDE  27  50  31  FOBS=  138.6  SIGMA=   1.5  PHAS=  -107.6  FOM=  0.93  TEST= 0
```

*FIG. 12A - 518*

```
INDE  27  50  33  FOBS=   37.3  SIGMA=   5.3  PHAS=  170.7  FOM=  0.63  TEST=  0
INDE  27  50  35  FOBS=   78.9  SIGMA=   2.6  PHAS=  -36.0  FOM=  0.60  TEST=  0
INDE  27  50  37  FOBS=   77.2  SIGMA=   2.7  PHAS=   83.1  FOM=  0.82  TEST=  0
INDE  27  50  39  FOBS=  134.7  SIGMA=   1.6  PHAS=   29.6  FOM=  0.16  TEST=  1
INDE  27  50  41  FOBS=   52.6  SIGMA=   3.9  PHAS=   98.8  FOM=  0.39  TEST=  0
INDE  27  50  43  FOBS=    0.0  SIGMA=  20.3  PHAS=    0.0  FOM=  0.00  TEST=  0
INDE  27  50  45  FOBS=   69.1  SIGMA=   2.9  PHAS=  103.6  FOM=  0.84  TEST=  0
INDE  27  50  47  FOBS=   37.1  SIGMA=   6.1  PHAS= -127.0  FOM=  0.26  TEST=  1
INDE  27  50  49  FOBS=   87.0  SIGMA=   2.8  PHAS=   24.0  FOM=  0.93  TEST=  0
INDE  27  50  51  FOBS=   37.2  SIGMA=   7.5  PHAS=   26.8  FOM=  0.74  TEST=  0
INDE  27  50  53  FOBS=   97.6  SIGMA=   3.4  PHAS=  -18.9  FOM=  0.89  TEST=  0
INDE  27  51  28  FOBS=   82.3  SIGMA=   2.3  PHAS= -153.3  FOM=  0.88  TEST=  0
INDE  27  51  30  FOBS=   95.9  SIGMA=   2.2  PHAS= -175.1  FOM=  0.90  TEST=  0
INDE  27  51  32  FOBS=   37.2  SIGMA=   5.6  PHAS= -108.4  FOM=  0.47  TEST=  0
INDE  27  51  34  FOBS=    0.0  SIGMA=  19.8  PHAS=    0.0  FOM=  0.00  TEST=  1
INDE  27  51  36  FOBS=   26.2  SIGMA=   8.1  PHAS=  -40.5  FOM=  0.28  TEST=  0
INDE  27  51  38  FOBS=   61.9  SIGMA=   3.5  PHAS=  -24.5  FOM=  0.62  TEST=  0
INDE  27  51  40  FOBS=   48.6  SIGMA=   4.5  PHAS=   81.2  FOM=  0.02  TEST=  0
INDE  27  51  42  FOBS=    0.0  SIGMA=  21.3  PHAS=    0.0  FOM=  0.00  TEST=  0
INDE  27  51  44  FOBS=   97.8  SIGMA=   2.2  PHAS=  114.9  FOM=  0.83  TEST=  0
INDE  27  51  46  FOBS=    0.0  SIGMA=  20.6  PHAS=    0.0  FOM=  0.00  TEST=  0
INDE  27  51  48  FOBS=   52.4  SIGMA=   4.2  PHAS=  -99.9  FOM=  0.81  TEST=  0
INDE  27  51  50  FOBS=   25.9  SIGMA=  10.6  PHAS=  -90.7  FOM=  0.54  TEST=  0
INDE  27  51  52  FOBS=   39.9  SIGMA=   7.4  PHAS= -127.1  FOM=  0.50  TEST=  0
INDE  27  52  27  FOBS=   38.0  SIGMA=   4.9  PHAS=  174.3  FOM=  0.80  TEST=  0
INDE  27  52  29  FOBS=   83.6  SIGMA=   2.3  PHAS=   86.8  FOM=  0.86  TEST=  0
INDE  27  52  31  FOBS=   64.3  SIGMA=   3.1  PHAS=  -27.9  FOM=  0.59  TEST=  0
INDE  27  52  33  FOBS=  109.3  SIGMA=   1.9  PHAS=  101.2  FOM=  0.91  TEST=  0
INDE  27  52  35  FOBS=    0.0  SIGMA=  21.3  PHAS=    0.0  FOM=  0.00  TEST=  0
INDE  27  52  37  FOBS=   45.2  SIGMA=   5.2  PHAS=   42.7  FOM=  0.29  TEST=  0
INDE  27  52  39  FOBS=   28.2  SIGMA=   8.5  PHAS=  -38.9  FOM=  0.44  TEST=  0
INDE  27  52  41  FOBS=   13.6  SIGMA=  17.7  PHAS=  -10.8  FOM=  0.20  TEST=  0
INDE  27  52  43  FOBS=    0.0  SIGMA=  20.5  PHAS=    0.0  FOM=  0.00  TEST=  0
INDE  27  52  45  FOBS=    6.5  SIGMA=  32.6  PHAS=  145.9  FOM=  0.10  TEST=  0
INDE  27  52  47  FOBS=   50.8  SIGMA=   4.7  PHAS=  -29.3  FOM=  0.65  TEST=  0
INDE  27  52  49  FOBS=   61.3  SIGMA=   4.0  PHAS=  122.5  FOM=  0.85  TEST=  0
INDE  27  52  51  FOBS=   76.9  SIGMA=   3.9  PHAS=   56.0  FOM=  0.13  TEST=  0
INDE  27  53  28  FOBS=  150.6  SIGMA=   1.3  PHAS=  -82.8  FOM=  0.95  TEST=  0
INDE  27  53  30  FOBS=   36.8  SIGMA=   5.9  PHAS= -159.9  FOM=  0.63  TEST=  0
INDE  27  53  32  FOBS=   36.4  SIGMA=   6.2  PHAS=  -48.1  FOM=  0.62  TEST=  0
INDE  27  53  34  FOBS=   56.8  SIGMA=   4.0  PHAS=   20.4  FOM=  0.80  TEST=  0
INDE  27  53  36  FOBS=    7.1  SIGMA=  32.7  PHAS= -175.7  FOM=  0.14  TEST=  0
INDE  27  53  38  FOBS=   19.7  SIGMA=  12.0  PHAS=  -20.3  FOM=  0.33  TEST=  0
INDE  27  53  40  FOBS=  107.6  SIGMA=   2.3  PHAS= -146.7  FOM=  0.92  TEST=  0
INDE  27  53  42  FOBS=   16.8  SIGMA=  14.8  PHAS=  102.9  FOM=  0.06  TEST=  0
INDE  27  53  44  FOBS=    0.0  SIGMA=  21.9  PHAS=    0.0  FOM=  0.00  TEST=  0
INDE  27  53  46  FOBS=   12.6  SIGMA=  17.3  PHAS=  164.8  FOM=  0.16  TEST=  0
INDE  27  53  48  FOBS=   17.5  SIGMA=  16.3  PHAS=  -73.2  FOM=  0.44  TEST=  0
INDE  27  53  50  FOBS=   62.3  SIGMA=   6.5  PHAS=  -89.1  FOM=  0.39  TEST=  0
INDE  27  54  27  FOBS=   94.7  SIGMA=   2.3  PHAS=  101.4  FOM=  0.78  TEST=  1
INDE  27  54  29  FOBS=  147.2  SIGMA=   1.6  PHAS=  152.7  FOM=  0.97  TEST=  0
INDE  27  54  31  FOBS=   14.1  SIGMA=  22.1  PHAS=   64.0  FOM=  0.22  TEST=  0
INDE  27  54  33  FOBS=   29.7  SIGMA=  10.4  PHAS= -128.4  FOM=  0.11  TEST=  0
INDE  27  54  35  FOBS=   49.6  SIGMA=   4.7  PHAS=   30.6  FOM=  0.62  TEST=  0
INDE  27  54  37  FOBS=    0.0  SIGMA=  21.6  PHAS=    0.0  FOM=  0.00  TEST=  0
INDE  27  54  39  FOBS=   62.3  SIGMA=   3.9  PHAS=   24.6  FOM=  0.82  TEST=  0
INDE  27  54  41  FOBS=   58.7  SIGMA=   4.2  PHAS=  117.5  FOM=  0.76  TEST=  0
INDE  27  54  43  FOBS=    0.0  SIGMA=  22.4  PHAS=    0.0  FOM=  0.00  TEST=  0
INDE  27  54  45  FOBS=    0.0  SIGMA=  22.6  PHAS=    0.0  FOM=  0.00  TEST=  0
INDE  27  54  47  FOBS=   45.0  SIGMA=   6.6  PHAS=   77.9  FOM=  0.52  TEST=  0
INDE  27  54  49  FOBS=   59.6  SIGMA=   8.0  PHAS=  113.4  FOM=  0.76  TEST=  0
INDE  27  55  28  FOBS=   57.9  SIGMA=   4.1  PHAS=   14.4  FOM=  0.93  TEST=  0
INDE  27  55  30  FOBS=  116.6  SIGMA=   2.1  PHAS=   77.1  FOM=  0.94  TEST=  0
INDE  27  55  32  FOBS=    0.0  SIGMA=  23.4  PHAS=    0.0  FOM=  0.00  TEST=  0
INDE  27  55  34  FOBS=   13.0  SIGMA=  21.0  PHAS=   50.3  FOM=  0.18  TEST=  0
INDE  27  55  36  FOBS=   27.3  SIGMA=   9.4  PHAS= -151.7  FOM=  0.50  TEST=  0
INDE  27  55  38  FOBS=    0.0  SIGMA=  22.9  PHAS=    0.0  FOM=  0.00  TEST=  0
INDE  27  55  40  FOBS=   32.5  SIGMA=   7.5  PHAS=  140.2  FOM=  0.43  TEST=  0
INDE  27  55  42  FOBS=   45.6  SIGMA=   6.1  PHAS=  -13.3  FOM=  0.77  TEST=  0
INDE  27  55  44  FOBS=   10.0  SIGMA=  32.3  PHAS=  -69.4  FOM=  0.01  TEST=  1
```

*FIG. 12A - 519*

```
INDE  27  55  46  FOBS=    0.0  SIGMA=  23.0  PHAS=    0.0  FOM= 0.00  TEST= 0
INDE  27  56  27  FOBS=   65.5  SIGMA=   3.3  PHAS=  -92.4  FOM= 0.49  TEST= 0
INDE  27  56  29  FOBS=   87.6  SIGMA=   2.8  PHAS= -135.7  FOM= 0.89  TEST= 0
INDE  27  56  31  FOBS=   64.8  SIGMA=   4.3  PHAS=   29.2  FOM= 0.86  TEST= 0
INDE  27  56  33  FOBS=    0.0  SIGMA=  23.5  PHAS=    0.0  FOM= 0.00  TEST= 0
INDE  27  56  35  FOBS=   62.2  SIGMA=   3.8  PHAS=   58.7  FOM= 0.69  TEST= 0
INDE  27  56  37  FOBS=   38.9  SIGMA=   7.6  PHAS=  168.9  FOM= 0.42  TEST= 0
INDE  27  56  39  FOBS=    0.0  SIGMA=  24.5  PHAS=    0.0  FOM= 0.00  TEST= 1
INDE  27  56  41  FOBS=   50.4  SIGMA=   6.3  PHAS=   51.9  FOM= 0.72  TEST= 0
INDE  27  56  43  FOBS=  120.6  SIGMA=   2.5  PHAS= -127.1  FOM= 0.93  TEST= 0
INDE  27  56  45  FOBS=    7.0  SIGMA=  37.8  PHAS=  -59.1  FOM= 0.05  TEST= 0
INDE  27  57  28  FOBS=  103.4  SIGMA=   2.2  PHAS=  111.8  FOM= 0.75  TEST= 1
INDE  27  57  30  FOBS=   61.6  SIGMA=   3.9  PHAS=   54.1  FOM= 0.42  TEST= 1
INDE  27  57  32  FOBS=    0.0  SIGMA=  23.4  PHAS=    0.0  FOM= 0.00  TEST= 0
INDE  27  57  34  FOBS=    0.0  SIGMA=  22.6  PHAS=    0.0  FOM= 0.00  TEST= 0
INDE  27  57  36  FOBS=   53.2  SIGMA=   5.5  PHAS= -170.7  FOM= 0.73  TEST= 0
INDE  27  57  38  FOBS=    0.0  SIGMA=  26.6  PHAS=    0.0  FOM= 0.00  TEST= 0
INDE  27  57  40  FOBS=   76.8  SIGMA=   4.2  PHAS=   12.3  FOM= 0.88  TEST= 0
INDE  27  57  42  FOBS=   36.3  SIGMA=  10.5  PHAS=  -25.5  FOM= 0.73  TEST= 0
INDE  27  57  44  FOBS=   38.9  SIGMA=   6.9  PHAS= -138.7  FOM= 0.82  TEST= 0
INDE  27  58  27  FOBS=  107.9  SIGMA=   2.1  PHAS=    1.1  FOM= 0.94  TEST= 0
INDE  27  58  29  FOBS=  120.4  SIGMA=   2.1  PHAS=   20.2  FOM= 0.13  TEST= 1
INDE  27  58  31  FOBS=   46.7  SIGMA=   6.5  PHAS=   28.7  FOM= 0.77  TEST= 0
INDE  27  58  33  FOBS=   79.8  SIGMA=   5.1  PHAS=   67.0  FOM= 0.83  TEST= 0
INDE  27  58  35  FOBS=   97.6  SIGMA=   3.0  PHAS=   56.2  FOM= 0.63  TEST= 1
INDE  27  58  37  FOBS=   44.7  SIGMA=   6.7  PHAS= -171.1  FOM= 0.63  TEST= 0
INDE  27  58  39  FOBS=  127.6  SIGMA=   2.5  PHAS=  -87.0  FOM= 0.96  TEST= 0
INDE  27  58  41  FOBS=   59.2  SIGMA=   6.5  PHAS=  -14.7  FOM= 0.17  TEST= 1
INDE  27  58  43  FOBS=   78.2  SIGMA=   4.3  PHAS= -173.6  FOM= 0.92  TEST= 0
INDE  27  59  28  FOBS=   54.5  SIGMA=   4.4  PHAS= -146.5  FOM= 0.70  TEST= 0
INDE  27  59  30  FOBS=   73.2  SIGMA=   3.8  PHAS=   12.7  FOM= 0.80  TEST= 0
INDE  27  59  32  FOBS=  104.9  SIGMA=   3.9  PHAS=   10.2  FOM= 0.92  TEST= 0
INDE  27  59  34  FOBS=   38.9  SIGMA=   8.6  PHAS=  -18.6  FOM= 0.66  TEST= 0
INDE  27  59  36  FOBS=    0.0  SIGMA=  24.3  PHAS=    0.0  FOM= 0.00  TEST= 0
INDE  27  59  38  FOBS=   61.2  SIGMA=   5.0  PHAS=  160.7  FOM= 0.76  TEST= 0
INDE  27  59  40  FOBS=   63.1  SIGMA=   5.1  PHAS= -176.4  FOM= 0.68  TEST= 0
INDE  27  59  42  FOBS=   26.9  SIGMA=  18.6  PHAS=  133.9  FOM= 0.02  TEST= 1
INDE  27  60  27  FOBS=    0.0  SIGMA=  22.9  PHAS=    0.0  FOM= 0.00  TEST= 0
INDE  27  60  29  FOBS=  115.7  SIGMA=   2.2  PHAS=  173.7  FOM= 0.19  TEST= 1
INDE  27  60  31  FOBS=  120.9  SIGMA=   2.4  PHAS= -132.5  FOM= 0.95  TEST= 0
INDE  27  60  33  FOBS=   91.9  SIGMA=   4.5  PHAS=  -34.4  FOM= 0.95  TEST= 0
INDE  27  60  35  FOBS=    0.0  SIGMA=  24.2  PHAS=    0.0  FOM= 0.00  TEST= 0
INDE  27  60  37  FOBS=   46.0  SIGMA=   6.6  PHAS=  -11.4  FOM= 0.15  TEST= 1
INDE  27  60  39  FOBS=   55.1  SIGMA=   5.7  PHAS= -128.7  FOM= 0.01  TEST= 1
INDE  27  60  41  FOBS=    0.0  SIGMA=  28.0  PHAS=    0.0  FOM= 0.00  TEST= 0
INDE  27  61  28  FOBS=   52.9  SIGMA=   4.4  PHAS=  160.5  FOM= 0.69  TEST= 0
INDE  27  61  30  FOBS=  113.3  SIGMA=   2.2  PHAS=  137.6  FOM= 0.91  TEST= 0
INDE  27  61  32  FOBS=   22.2  SIGMA=  12.4  PHAS=  174.5  FOM= 0.37  TEST= 0
INDE  27  61  34  FOBS=   70.8  SIGMA=   5.9  PHAS= -139.5  FOM= 0.89  TEST= 0
INDE  27  61  36  FOBS=   27.5  SIGMA=  12.4  PHAS=  -44.0  FOM= 0.41  TEST= 0
INDE  27  61  38  FOBS=   42.1  SIGMA=   8.3  PHAS=   33.3  FOM= 0.61  TEST= 0
INDE  27  62  27  FOBS=    0.0  SIGMA=  27.9  PHAS=    0.0  FOM= 0.00  TEST= 1
INDE  27  62  29  FOBS=   85.9  SIGMA=   2.9  PHAS=   49.8  FOM= 0.90  TEST= 0
INDE  27  62  31  FOBS=   49.1  SIGMA=   5.5  PHAS=  -13.6  FOM= 0.56  TEST= 0
INDE  27  62  33  FOBS=    0.0  SIGMA=  28.7  PHAS=    0.0  FOM= 0.00  TEST= 0
INDE  27  62  35  FOBS=   23.9  SIGMA=  17.8  PHAS=  -74.5  FOM= 0.49  TEST= 0
INDE  27  62  37  FOBS=   70.7  SIGMA=   4.4  PHAS=  -92.0  FOM= 0.86  TEST= 0
INDE  27  63  28  FOBS=   72.4  SIGMA=   4.3  PHAS=  -34.6  FOM= 0.38  TEST= 1
INDE  27  63  30  FOBS=   72.6  SIGMA=   3.4  PHAS= -103.6  FOM= 0.86  TEST= 0
INDE  27  63  32  FOBS=   66.5  SIGMA=   3.8  PHAS= -106.3  FOM= 0.83  TEST= 0
INDE  27  63  34  FOBS=   44.7  SIGMA=   7.9  PHAS=  -91.9  FOM= 0.81  TEST= 0
INDE  27  63  36  FOBS=   46.6  SIGMA=   6.6  PHAS= -160.8  FOM= 0.05  TEST= 1
INDE  27  64  27  FOBS=    7.2  SIGMA=  42.8  PHAS=   10.5  FOM= 0.12  TEST= 0
INDE  27  64  29  FOBS=   42.8  SIGMA=   6.5  PHAS=  156.8  FOM= 0.85  TEST= 0
INDE  27  64  31  FOBS=   37.5  SIGMA=   6.7  PHAS=  138.9  FOM= 0.79  TEST= 0
INDE  27  64  33  FOBS=  110.2  SIGMA=   2.7  PHAS= -175.2  FOM= 0.95  TEST= 0
INDE  27  65  28  FOBS=   57.6  SIGMA=   6.8  PHAS=  149.0  FOM= 0.04  TEST= 1
INDE  27  65  30  FOBS=    0.0  SIGMA=  25.4  PHAS=    0.0  FOM= 0.00  TEST= 0
INDE  27  65  32  FOBS=   54.3  SIGMA=   5.4  PHAS=   40.8  FOM= 0.81  TEST= 0
INDE  27  66  27  FOBS=   43.6  SIGMA=  11.7  PHAS= -121.3  FOM= 0.68  TEST= 0
```

*FIG. 12A - 520*

```
INDE 27 66 29 FOBS=    0.0 SIGMA= 32.7 PHAS=    0.0 FOM= 0.00 TEST= 0
INDE 27 66 31 FOBS=    0.0 SIGMA= 33.0 PHAS=    0.0 FOM= 0.00 TEST= 0
INDE 27 67 28 FOBS=   58.0 SIGMA=  8.9 PHAS=  116.5 FOM= 0.56 TEST= 0
INDE 28 28 28 FOBS=  294.0 SIGMA=  1.2 PHAS=  -69.2 FOM= 0.93 TEST= 0
INDE 28 29 29 FOBS=  384.4 SIGMA=  0.7 PHAS= -149.5 FOM= 0.99 TEST= 0
INDE 28 29 31 FOBS=  131.5 SIGMA=  1.5 PHAS= -113.7 FOM= 0.82 TEST= 0
INDE 28 29 33 FOBS=    0.0 SIGMA= 20.3 PHAS=    0.0 FOM= 0.00 TEST= 0
INDE 28 29 35 FOBS=   18.8 SIGMA= 10.9 PHAS=  166.6 FOM= 0.33 TEST= 0
INDE 28 29 37 FOBS=   85.4 SIGMA=  2.3 PHAS=  -47.6 FOM= 0.92 TEST= 0
INDE 28 29 39 FOBS=   78.2 SIGMA=  2.1 PHAS=   82.9 FOM= 0.79 TEST= 0
INDE 28 29 41 FOBS=  105.5 SIGMA=  1.6 PHAS=  174.1 FOM= 0.94 TEST= 0
INDE 28 29 43 FOBS=   36.8 SIGMA=  4.5 PHAS=  129.2 FOM= 0.29 TEST= 0
INDE 28 29 45 FOBS=  108.7 SIGMA=  1.5 PHAS=  -76.5 FOM= 0.83 TEST= 0
INDE 28 29 47 FOBS=   38.2 SIGMA=  4.1 PHAS=  -75.9 FOM= 0.19 TEST= 0
INDE 28 29 49 FOBS=   50.8 SIGMA=  3.4 PHAS=   13.1 FOM= 0.79 TEST= 0
INDE 28 29 51 FOBS=   50.5 SIGMA=  3.8 PHAS= -128.1 FOM= 0.53 TEST= 0
INDE 28 29 53 FOBS=   64.0 SIGMA=  3.0 PHAS=  -35.9 FOM= 0.89 TEST= 0
INDE 28 29 55 FOBS=    8.3 SIGMA= 28.6 PHAS=   70.4 FOM= 0.00 TEST= 1
INDE 28 29 57 FOBS=   20.1 SIGMA= 18.8 PHAS=  -89.1 FOM= 0.12 TEST= 1
INDE 28 29 59 FOBS=  108.2 SIGMA=  2.3 PHAS=  -88.2 FOM= 0.92 TEST= 0
INDE 28 29 61 FOBS=   15.3 SIGMA= 24.9 PHAS=  162.4 FOM= 0.25 TEST= 0
INDE 28 29 63 FOBS=   22.1 SIGMA= 17.9 PHAS= -114.3 FOM= 0.30 TEST= 0
INDE 28 29 65 FOBS=    0.0 SIGMA= 33.0 PHAS=    0.0 FOM= 0.00 TEST= 0
INDE 28 30 28 FOBS=  125.1 SIGMA=  1.6 PHAS=   78.4 FOM= 0.39 TEST= 0
INDE 28 30 30 FOBS=  271.0 SIGMA=  0.8 PHAS=  131.9 FOM= 0.96 TEST= 0
INDE 28 30 32 FOBS=    0.0 SIGMA= 19.3 PHAS=    0.0 FOM= 0.00 TEST= 0
INDE 28 30 34 FOBS=  132.7 SIGMA=  1.5 PHAS=   71.0 FOM= 0.80 TEST= 0
INDE 28 30 36 FOBS=  122.7 SIGMA=  1.6 PHAS=   97.3 FOM= 0.93 TEST= 0
INDE 28 30 38 FOBS=  173.4 SIGMA=  1.1 PHAS=  -70.9 FOM= 0.94 TEST= 0
INDE 28 30 40 FOBS=   44.4 SIGMA=  4.1 PHAS= -138.0 FOM= 0.70 TEST= 0
INDE 28 30 42 FOBS=   72.9 SIGMA=  2.3 PHAS=   27.0 FOM= 0.62 TEST= 0
INDE 28 30 44 FOBS=   86.3 SIGMA=  1.9 PHAS= -126.7 FOM= 0.86 TEST= 0
INDE 28 30 46 FOBS=   96.7 SIGMA=  1.7 PHAS= -159.1 FOM= 0.90 TEST= 0
INDE 28 30 48 FOBS=   98.6 SIGMA=  1.6 PHAS=  174.7 FOM= 0.92 TEST= 0
INDE 28 30 50 FOBS=   51.8 SIGMA=  3.3 PHAS= -145.3 FOM= 0.05 TEST= 1
INDE 28 30 52 FOBS=  122.8 SIGMA=  1.5 PHAS= -147.8 FOM= 0.94 TEST= 0
INDE 28 30 54 FOBS=   48.8 SIGMA=  4.2 PHAS= -118.5 FOM= 0.83 TEST= 0
INDE 28 30 56 FOBS=   19.2 SIGMA= 14.1 PHAS= -178.9 FOM= 0.37 TEST= 0
INDE 28 30 58 FOBS=   52.4 SIGMA=  5.3 PHAS=    5.0 FOM= 0.44 TEST= 0
INDE 28 30 60 FOBS=   37.0 SIGMA=  8.6 PHAS=   31.6 FOM= 0.16 TEST= 1
INDE 28 30 62 FOBS=    0.0 SIGMA= 28.1 PHAS=    0.0 FOM= 0.00 TEST= 0
INDE 28 30 64 FOBS=   42.0 SIGMA= 12.8 PHAS=    7.1 FOM= 0.04 TEST= 1
INDE 28 30 66 FOBS=    0.0 SIGMA= 33.1 PHAS=    0.0 FOM= 0.00 TEST= 0
INDE 28 31 29 FOBS=   57.3 SIGMA=  3.7 PHAS= -178.8 FOM= 0.77 TEST= 0
INDE 28 31 31 FOBS=    0.0 SIGMA= 20.3 PHAS=    0.0 FOM= 0.00 TEST= 0
INDE 28 31 33 FOBS=  196.1 SIGMA=  1.1 PHAS=  -31.0 FOM= 0.50 TEST= 1
INDE 28 31 35 FOBS=  201.7 SIGMA=  1.0 PHAS=   -8.4 FOM= 0.94 TEST= 0
INDE 28 31 37 FOBS=  108.5 SIGMA=  1.8 PHAS=  -49.0 FOM= 0.50 TEST= 1
INDE 28 31 39 FOBS=   76.5 SIGMA=  2.5 PHAS=  162.9 FOM= 0.51 TEST= 0
INDE 28 31 41 FOBS=  215.8 SIGMA=  1.0 PHAS=  153.2 FOM= 0.96 TEST= 0
INDE 28 31 43 FOBS=  162.9 SIGMA=  1.1 PHAS=  165.6 FOM= 0.95 TEST= 0
INDE 28 31 45 FOBS=  120.0 SIGMA=  1.5 PHAS=  178.3 FOM= 0.92 TEST= 0
INDE 28 31 47 FOBS=  143.2 SIGMA=  1.2 PHAS=   84.1 FOM= 0.96 TEST= 0
INDE 28 31 49 FOBS=    0.0 SIGMA= 18.0 PHAS=    0.0 FOM= 0.00 TEST= 0
INDE 28 31 51 FOBS=   85.4 SIGMA=  2.0 PHAS= -178.0 FOM= 0.90 TEST= 0
INDE 28 31 53 FOBS=   38.6 SIGMA=  4.9 PHAS=  -90.5 FOM= 0.08 TEST= 1
INDE 28 31 55 FOBS=   17.4 SIGMA= 13.7 PHAS= -110.1 FOM= 0.03 TEST= 1
INDE 28 31 57 FOBS=   52.1 SIGMA=  4.7 PHAS=  -53.6 FOM= 0.65 TEST= 0
INDE 28 31 59 FOBS=   26.4 SIGMA= 12.1 PHAS= -168.6 FOM= 0.39 TEST= 0
INDE 28 31 61 FOBS=    0.0 SIGMA= 27.6 PHAS=    0.0 FOM= 0.00 TEST= 0
INDE 28 31 63 FOBS=   39.6 SIGMA=  9.7 PHAS=  -11.4 FOM= 0.52 TEST= 0
INDE 28 31 65 FOBS=   30.4 SIGMA= 18.0 PHAS= -171.0 FOM= 0.38 TEST= 0
INDE 28 32 28 FOBS=   34.5 SIGMA=  5.7 PHAS=   22.9 FOM= 0.49 TEST= 0
INDE 28 32 30 FOBS=  137.1 SIGMA=  1.5 PHAS=   13.7 FOM= 0.84 TEST= 0
INDE 28 32 32 FOBS=  268.2 SIGMA=  0.8 PHAS= -141.4 FOM= 0.98 TEST= 0
INDE 28 32 34 FOBS=  103.2 SIGMA=  1.9 PHAS= -146.4 FOM= 0.79 TEST= 0
INDE 28 32 36 FOBS=  117.1 SIGMA=  1.6 PHAS= -116.0 FOM= 0.87 TEST= 0
INDE 28 32 38 FOBS=   76.3 SIGMA=  2.5 PHAS= -113.7 FOM= 0.88 TEST= 0
INDE 28 32 40 FOBS=   71.8 SIGMA=  2.6 PHAS=   52.0 FOM= 0.81 TEST= 0
INDE 28 32 42 FOBS=  315.0 SIGMA=  0.8 PHAS=   54.1 FOM= 0.84 TEST= 1
```

*FIG. 12A - 521*

```
INDE 28 32 44 FOBS=  134.6 SIGMA=  1.3 PHAS=   61.5 FOM= 0.88 TEST= 0
INDE 28 32 46 FOBS=   56.9 SIGMA=  2.9 PHAS=  111.5 FOM= 0.32 TEST= 1
INDE 28 32 48 FOBS=   36.4 SIGMA=  4.5 PHAS=  -35.6 FOM= 0.19 TEST= 1
INDE 28 32 50 FOBS=    0.0 SIGMA= 18.4 PHAS=    0.0 FOM= 0.00 TEST= 0
INDE 28 32 52 FOBS=   66.4 SIGMA=  2.9 PHAS=  132.2 FOM= 0.77 TEST= 0
INDE 28 32 54 FOBS=   35.6 SIGMA=  6.8 PHAS=   43.3 FOM= 0.21 TEST= 0
INDE 28 32 56 FOBS=   43.4 SIGMA=  4.7 PHAS=   83.9 FOM= 0.69 TEST= 0
INDE 28 32 58 FOBS=   90.0 SIGMA=  3.7 PHAS= -100.3 FOM= 0.76 TEST= 0
INDE 28 32 60 FOBS=   43.8 SIGMA=  9.2 PHAS=  -64.0 FOM= 0.42 TEST= 0
INDE 28 32 62 FOBS=   19.1 SIGMA= 16.9 PHAS=  -43.6 FOM= 0.23 TEST= 0
INDE 28 32 64 FOBS=   34.1 SIGMA=  9.8 PHAS= -151.6 FOM= 0.70 TEST= 0
INDE 28 33 29 FOBS=  183.1 SIGMA=  1.2 PHAS=  -48.9 FOM= 0.86 TEST= 0
INDE 28 33 31 FOBS=  137.6 SIGMA=  1.4 PHAS=  109.2 FOM= 0.90 TEST= 1
INDE 28 33 33 FOBS=   53.0 SIGMA=  3.5 PHAS=   77.5 FOM= 0.59 TEST= 0
INDE 28 33 35 FOBS=    0.0 SIGMA= 19.8 PHAS=    0.0 FOM= 0.00 TEST= 1
INDE 28 33 37 FOBS=   14.1 SIGMA= 13.0 PHAS= -146.0 FOM= 0.26 TEST= 0
INDE 28 33 39 FOBS=    0.0 SIGMA= 19.2 PHAS=    0.0 FOM= 0.00 TEST= 0
INDE 28 33 41 FOBS=   35.5 SIGMA=  5.2 PHAS=  -68.0 FOM= 0.63 TEST= 0
INDE 28 33 43 FOBS=  177.5 SIGMA=  1.1 PHAS=  -58.0 FOM= 0.96 TEST= 0
INDE 28 33 45 FOBS=    0.0 SIGMA= 18.6 PHAS=    0.0 FOM= 0.00 TEST= 0
INDE 28 33 47 FOBS=   83.4 SIGMA=  1.9 PHAS=   -1.0 FOM= 0.58 TEST= 1
INDE 28 33 49 FOBS=   22.2 SIGMA=  7.1 PHAS=  116.7 FOM= 0.33 TEST= 0
INDE 28 33 51 FOBS=    7.6 SIGMA= 23.8 PHAS=  -43.2 FOM= 0.00 TEST= 0
INDE 28 33 53 FOBS=   46.0 SIGMA=  4.1 PHAS=  114.7 FOM= 0.01 TEST= 1
INDE 28 33 55 FOBS=   55.2 SIGMA=  3.8 PHAS=   62.1 FOM= 0.86 TEST= 0
INDE 28 33 57 FOBS=   46.2 SIGMA=  5.3 PHAS=  -34.6 FOM= 0.77 TEST= 0
INDE 28 33 59 FOBS=   90.9 SIGMA=  3.1 PHAS=   98.4 FOM= 0.94 TEST= 0
INDE 28 33 61 FOBS=   13.5 SIGMA= 24.1 PHAS= -113.8 FOM= 0.17 TEST= 0
INDE 28 33 63 FOBS=   82.3 SIGMA=  4.1 PHAS=  172.4 FOM= 0.72 TEST= 0
INDE 28 34 28 FOBS=  218.9 SIGMA=  0.9 PHAS= -114.9 FOM= 0.95 TEST= 0
INDE 28 34 30 FOBS=  234.5 SIGMA=  1.0 PHAS=  -68.2 FOM= 0.97 TEST= 0
INDE 28 34 32 FOBS=  142.2 SIGMA=  1.4 PHAS=  -45.0 FOM= 0.92 TEST= 0
INDE 28 34 34 FOBS=  114.3 SIGMA=  1.6 PHAS=  175.0 FOM= 0.94 TEST= 0
INDE 28 34 36 FOBS=    0.0 SIGMA= 19.5 PHAS=    0.0 FOM= 0.00 TEST= 0
INDE 28 34 38 FOBS=   87.7 SIGMA=  2.1 PHAS=  107.5 FOM= 0.87 TEST= 1
INDE 28 34 40 FOBS=    0.0 SIGMA= 19.6 PHAS=    0.0 FOM= 0.00 TEST= 0
INDE 28 34 42 FOBS=   28.9 SIGMA=  6.5 PHAS=  -75.9 FOM= 0.34 TEST= 1
INDE 28 34 44 FOBS=   39.6 SIGMA=  4.4 PHAS=  124.1 FOM= 0.65 TEST= 0
INDE 28 34 46 FOBS=    0.0 SIGMA= 19.2 PHAS=    0.0 FOM= 0.00 TEST= 0
INDE 28 34 48 FOBS=   76.5 SIGMA=  2.3 PHAS=  -16.1 FOM= 0.79 TEST= 0
INDE 28 34 50 FOBS=   75.2 SIGMA=  2.2 PHAS=    5.3 FOM= 0.89 TEST= 0
INDE 28 34 52 FOBS=   68.0 SIGMA=  2.7 PHAS= -146.8 FOM= 0.85 TEST= 0
INDE 28 34 54 FOBS=   30.3 SIGMA=  6.9 PHAS=   47.8 FOM= 0.52 TEST= 0
INDE 28 34 56 FOBS=   27.8 SIGMA=  8.8 PHAS=  -25.3 FOM= 0.56 TEST= 0
INDE 28 34 58 FOBS=   55.4 SIGMA=  4.5 PHAS=  -41.2 FOM= 0.89 TEST= 0
INDE 28 34 60 FOBS=   35.8 SIGMA=  7.8 PHAS=  -52.0 FOM= 0.67 TEST= 0
INDE 28 34 62 FOBS=   18.6 SIGMA= 17.9 PHAS=   74.2 FOM= 0.35 TEST= 0
INDE 28 34 64 FOBS=   34.3 SIGMA=  9.9 PHAS=  -28.1 FOM= 0.09 TEST= 1
INDE 28 35 29 FOBS=  242.7 SIGMA=  0.9 PHAS=  174.7 FOM= 0.87 TEST= 1
INDE 28 35 31 FOBS=  168.2 SIGMA=  1.3 PHAS= -160.1 FOM= 0.94 TEST= 0
INDE 28 35 33 FOBS=    0.0 SIGMA= 19.5 PHAS=    0.0 FOM= 0.00 TEST= 0
INDE 28 35 35 FOBS=    0.0 SIGMA= 19.0 PHAS=    0.0 FOM= 0.00 TEST= 0
INDE 28 35 37 FOBS=   60.0 SIGMA=  3.1 PHAS=  -60.0 FOM= 0.75 TEST= 0
INDE 28 35 39 FOBS=   67.3 SIGMA=  2.7 PHAS=  -98.5 FOM= 0.78 TEST= 0
INDE 28 35 41 FOBS=    0.0 SIGMA= 19.5 PHAS=    0.0 FOM= 0.00 TEST= 0
INDE 28 35 43 FOBS=   43.2 SIGMA=  4.4 PHAS=  -77.0 FOM= 0.59 TEST= 0
INDE 28 35 45 FOBS=    0.0 SIGMA= 19.1 PHAS=    0.0 FOM= 0.00 TEST= 0
INDE 28 35 47 FOBS=   51.4 SIGMA=  3.4 PHAS=  -61.0 FOM= 0.43 TEST= 0
INDE 28 35 49 FOBS=   19.0 SIGMA=  9.8 PHAS=  112.4 FOM= 0.19 TEST= 0
INDE 28 35 51 FOBS=   42.5 SIGMA=  4.1 PHAS=  -97.0 FOM= 0.63 TEST= 0
INDE 28 35 53 FOBS=   71.5 SIGMA=  2.8 PHAS= -142.6 FOM= 0.35 TEST= 1
INDE 28 35 55 FOBS=   51.3 SIGMA=  4.8 PHAS=  138.6 FOM= 0.78 TEST= 0
INDE 28 35 57 FOBS=  116.7 SIGMA=  2.2 PHAS= -146.9 FOM= 0.96 TEST= 0
INDE 28 35 59 FOBS=    0.0 SIGMA= 22.2 PHAS=    0.0 FOM= 0.00 TEST= 0
INDE 28 35 61 FOBS=   53.1 SIGMA=  4.7 PHAS=  131.9 FOM= 0.57 TEST= 0
INDE 28 35 63 FOBS=   46.6 SIGMA=  7.2 PHAS= -147.0 FOM= 0.61 TEST= 0
INDE 28 36 28 FOBS=  177.3 SIGMA=  1.0 PHAS=   31.8 FOM= 0.93 TEST= 0
INDE 28 36 30 FOBS=    0.0 SIGMA= 20.2 PHAS=    0.0 FOM= 0.00 TEST= 0
INDE 28 36 32 FOBS=   32.5 SIGMA=  7.0 PHAS=   51.5 FOM= 0.16 TEST= 0
INDE 28 36 34 FOBS=   23.0 SIGMA=  8.2 PHAS=  139.2 FOM= 0.23 TEST= 0
```

*FIG. 12A - 522*

```
INDE 28 36 36 FOBS=   74.4 SIGMA=  2.5 PHAS=    4.6 FOM= 0.84 TEST= 1
INDE 28 36 38 FOBS=   68.7 SIGMA=  2.7 PHAS= -150.4 FOM= 0.78 TEST= 0
INDE 28 36 40 FOBS=   79.9 SIGMA=  2.3 PHAS=  -78.4 FOM= 0.92 TEST= 0
INDE 28 36 42 FOBS=   84.5 SIGMA=  2.2 PHAS= -119.4 FOM= 0.79 TEST= 0
INDE 28 36 44 FOBS=   72.0 SIGMA=  2.5 PHAS=   65.4 FOM= 0.75 TEST= 0
INDE 28 36 46 FOBS=   38.9 SIGMA=  4.5 PHAS=   32.2 FOM= 0.69 TEST= 0
INDE 28 36 48 FOBS=  115.3 SIGMA=  1.6 PHAS=  -42.7 FOM= 0.91 TEST= 0
INDE 28 36 50 FOBS=   31.7 SIGMA=  5.5 PHAS=  -22.0 FOM= 0.42 TEST= 0
INDE 28 36 52 FOBS=   43.6 SIGMA=  4.0 PHAS=  148.6 FOM= 0.67 TEST= 0
INDE 28 36 54 FOBS=   85.7 SIGMA=  2.9 PHAS=   84.8 FOM= 0.78 TEST= 0
INDE 28 36 56 FOBS=   36.7 SIGMA=  8.9 PHAS=   91.0 FOM= 0.85 TEST= 0
INDE 28 36 58 FOBS=    0.0 SIGMA= 22.1 PHAS=    0.0 FOM= 0.00 TEST= 0
INDE 28 36 60 FOBS=   62.6 SIGMA=  4.0 PHAS= -175.9 FOM= 0.10 TEST= 1
INDE 28 36 62 FOBS=   21.5 SIGMA= 15.4 PHAS=    0.0 FOM= 0.00 TEST= 1
INDE 28 37 29 FOBS=    0.0 SIGMA= 18.9 PHAS=    0.0 FOM= 0.00 TEST= 0
INDE 28 37 31 FOBS=   71.9 SIGMA=  2.5 PHAS= -132.2 FOM= 0.80 TEST= 0
INDE 28 37 33 FOBS=   42.5 SIGMA=  4.0 PHAS= -108.5 FOM= 0.30 TEST= 0
INDE 28 37 35 FOBS=   59.9 SIGMA=  2.7 PHAS= -134.2 FOM= 0.32 TEST= 0
INDE 28 37 37 FOBS=  130.5 SIGMA=  1.3 PHAS= -135.0 FOM= 0.88 TEST= 0
INDE 28 37 39 FOBS=   59.7 SIGMA=  2.8 PHAS= -166.7 FOM= 0.93 TEST= 0
INDE 28 37 41 FOBS=   31.7 SIGMA=  5.6 PHAS=   36.5 FOM= 0.66 TEST= 0
INDE 28 37 43 FOBS=   51.3 SIGMA=  3.5 PHAS=  -10.4 FOM= 0.84 TEST= 0
INDE 28 37 45 FOBS=  137.3 SIGMA=  1.4 PHAS=  -67.6 FOM= 0.95 TEST= 0
INDE 28 37 47 FOBS=   43.1 SIGMA=  4.1 PHAS= -163.6 FOM= 0.87 TEST= 0
INDE 28 37 49 FOBS=    0.0 SIGMA= 20.6 PHAS=    0.0 FOM= 0.00 TEST= 0
INDE 28 37 51 FOBS=   21.9 SIGMA=  8.0 PHAS=   -0.8 FOM= 0.14 TEST= 0
INDE 28 37 53 FOBS=  102.2 SIGMA=  2.2 PHAS=   68.9 FOM= 0.05 TEST= 1
INDE 28 37 55 FOBS=    6.9 SIGMA= 40.6 PHAS=   85.7 FOM= 0.18 TEST= 0
INDE 28 37 57 FOBS=   82.4 SIGMA=  3.1 PHAS= -165.8 FOM= 0.88 TEST= 0
INDE 28 37 59 FOBS=   22.0 SIGMA= 11.3 PHAS=  -16.2 FOM= 0.22 TEST= 0
INDE 28 37 61 FOBS=    0.0 SIGMA= 23.7 PHAS=    0.0 FOM= 0.00 TEST= 0
INDE 28 38 28 FOBS=   68.1 SIGMA=  2.4 PHAS=  169.9 FOM= 0.90 TEST= 1
INDE 28 38 30 FOBS=  136.2 SIGMA=  1.4 PHAS= -176.8 FOM= 0.88 TEST= 0
INDE 28 38 32 FOBS=   30.4 SIGMA=  6.2 PHAS=   23.9 FOM= 0.20 TEST= 0
INDE 28 38 34 FOBS=   47.5 SIGMA=  3.5 PHAS=  118.8 FOM= 0.73 TEST= 0
INDE 28 38 36 FOBS=   51.3 SIGMA=  3.2 PHAS=   42.1 FOM= 0.64 TEST= 0
INDE 28 38 38 FOBS=  113.2 SIGMA=  1.5 PHAS=  145.7 FOM= 0.86 TEST= 0
INDE 28 38 40 FOBS=   64.8 SIGMA=  2.5 PHAS=  -93.9 FOM= 0.12 TEST= 1
INDE 28 38 42 FOBS=   86.5 SIGMA=  1.9 PHAS=  -75.5 FOM= 0.93 TEST= 0
INDE 28 38 44 FOBS=   46.4 SIGMA=  3.6 PHAS= -111.2 FOM= 0.60 TEST= 0
INDE 28 38 46 FOBS=   58.9 SIGMA=  2.8 PHAS=   33.8 FOM= 0.83 TEST= 0
INDE 28 38 48 FOBS=    0.0 SIGMA= 19.1 PHAS=    0.0 FOM= 0.00 TEST= 0
INDE 28 38 50 FOBS=   77.8 SIGMA=  2.3 PHAS=  -78.0 FOM= 0.88 TEST= 0
INDE 28 38 52 FOBS=   76.6 SIGMA=  2.9 PHAS=  132.3 FOM= 0.78 TEST= 0
INDE 28 38 54 FOBS=   38.4 SIGMA=  5.6 PHAS=  101.0 FOM= 0.26 TEST= 0
INDE 28 38 56 FOBS=   97.1 SIGMA=  2.6 PHAS=  106.0 FOM= 0.91 TEST= 0
INDE 28 38 58 FOBS=   23.8 SIGMA= 10.5 PHAS=   93.3 FOM= 0.44 TEST= 0
INDE 28 38 60 FOBS=    0.0 SIGMA= 28.8 PHAS=    0.0 FOM= 0.00 TEST= 0
INDE 28 39 29 FOBS=  151.7 SIGMA=  1.2 PHAS=   89.4 FOM= 0.95 TEST= 0
INDE 28 39 31 FOBS=    0.0 SIGMA= 18.9 PHAS=    0.0 FOM= 0.00 TEST= 0
INDE 28 39 33 FOBS=   98.5 SIGMA=  1.9 PHAS=  -54.1 FOM= 0.89 TEST= 0
INDE 28 39 35 FOBS=  112.4 SIGMA=  1.5 PHAS=   52.0 FOM= 0.86 TEST= 0
INDE 28 39 37 FOBS=    0.0 SIGMA= 17.9 PHAS=    0.0 FOM= 0.00 TEST= 0
INDE 28 39 39 FOBS=   37.2 SIGMA=  5.5 PHAS=   47.1 FOM= 0.61 TEST= 0
INDE 28 39 41 FOBS=   84.8 SIGMA=  2.0 PHAS= -148.8 FOM= 0.85 TEST= 0
INDE 28 39 43 FOBS=   42.5 SIGMA=  3.8 PHAS= -152.8 FOM= 0.78 TEST= 0
INDE 28 39 45 FOBS=  152.7 SIGMA=  1.1 PHAS=  -60.1 FOM= 0.95 TEST= 0
INDE 28 39 47 FOBS=   45.1 SIGMA=  3.9 PHAS=   76.2 FOM= 0.73 TEST= 0
INDE 28 39 49 FOBS=   70.5 SIGMA=  2.3 PHAS=  144.7 FOM= 0.85 TEST= 0
INDE 28 39 51 FOBS=   63.5 SIGMA=  3.1 PHAS=  127.0 FOM= 0.90 TEST= 0
INDE 28 39 53 FOBS=    0.0 SIGMA= 22.8 PHAS=    0.0 FOM= 0.00 TEST= 0
INDE 28 39 55 FOBS=   63.5 SIGMA=  3.4 PHAS=   27.4 FOM= 0.75 TEST= 0
INDE 28 39 57 FOBS=   12.8 SIGMA= 22.0 PHAS=   16.8 FOM= 0.27 TEST= 0
INDE 28 39 59 FOBS=   34.2 SIGMA=  7.5 PHAS=   74.0 FOM= 0.12 TEST= 1
INDE 28 39 61 FOBS=   70.9 SIGMA=  4.9 PHAS=  172.8 FOM= 0.86 TEST= 0
INDE 28 40 28 FOBS=  109.3 SIGMA=  1.5 PHAS= -152.0 FOM= 0.84 TEST= 0
INDE 28 40 30 FOBS=   25.2 SIGMA=  7.2 PHAS=  151.5 FOM= 0.57 TEST= 1
INDE 28 40 32 FOBS=   47.5 SIGMA=  4.0 PHAS=   42.6 FOM= 0.76 TEST= 0
INDE 28 40 34 FOBS=   24.3 SIGMA=  8.2 PHAS=  178.4 FOM= 0.17 TEST= 0
INDE 28 40 36 FOBS=   54.6 SIGMA=  3.1 PHAS=  -27.4 FOM= 0.86 TEST= 0
```

*FIG. 12A - 523*

| | | | | | | | | | | | | |
|---|---|---|---|---|---|---|---|---|---|---|---|---|
| INDE | 28 | 40 | 38 | FOBS= | 81.3 | SIGMA= | 2.0 | PHAS= | 107.5 | FOM= | 0.87 | TEST= 0 |
| INDE | 28 | 40 | 40 | FOBS= | 34.1 | SIGMA= | 5.6 | PHAS= | 130.5 | FOM= | 0.55 | TEST= 0 |
| INDE | 28 | 40 | 42 | FOBS= | 61.1 | SIGMA= | 2.8 | PHAS= | 70.9 | FOM= | 0.84 | TEST= 0 |
| INDE | 28 | 40 | 44 | FOBS= | 92.7 | SIGMA= | 1.8 | PHAS= | -132.6 | FOM= | 0.79 | TEST= 0 |
| INDE | 28 | 40 | 46 | FOBS= | 0.0 | SIGMA= | 17.9 | PHAS= | 0.0 | FOM= | 0.00 | TEST= 0 |
| INDE | 28 | 40 | 48 | FOBS= | 81.7 | SIGMA= | 2.1 | PHAS= | 82.6 | FOM= | 0.09 | TEST= 1 |
| INDE | 28 | 40 | 50 | FOBS= | 73.0 | SIGMA= | 2.5 | PHAS= | 17.3 | FOM= | 0.78 | TEST= 0 |
| INDE | 28 | 40 | 52 | FOBS= | 92.4 | SIGMA= | 2.1 | PHAS= | 56.5 | FOM= | 0.91 | TEST= 0 |
| INDE | 28 | 40 | 54 | FOBS= | 0.0 | SIGMA= | 20.9 | PHAS= | 0.0 | FOM= | 0.00 | TEST= 0 |
| INDE | 28 | 40 | 56 | FOBS= | 31.1 | SIGMA= | 7.4 | PHAS= | -78.9 | FOM= | 0.13 | TEST= 0 |
| INDE | 28 | 40 | 58 | FOBS= | 39.4 | SIGMA= | 6.5 | PHAS= | -86.4 | FOM= | 0.75 | TEST= 0 |
| INDE | 28 | 40 | 60 | FOBS= | 77.8 | SIGMA= | 4.5 | PHAS= | 70.5 | FOM= | 0.92 | TEST= 0 |
| INDE | 28 | 41 | 29 | FOBS= | 112.5 | SIGMA= | 1.5 | PHAS= | 151.4 | FOM= | 0.84 | TEST= 0 |
| INDE | 28 | 41 | 31 | FOBS= | 42.3 | SIGMA= | 4.5 | PHAS= | -154.0 | FOM= | 0.44 | TEST= 1 |
| INDE | 28 | 41 | 33 | FOBS= | 133.2 | SIGMA= | 1.4 | PHAS= | -37.1 | FOM= | 0.95 | TEST= 0 |
| INDE | 28 | 41 | 35 | FOBS= | 69.9 | SIGMA= | 2.5 | PHAS= | 149.3 | FOM= | 0.39 | TEST= 1 |
| INDE | 28 | 41 | 37 | FOBS= | 44.7 | SIGMA= | 3.6 | PHAS= | -28.0 | FOM= | 0.31 | TEST= 0 |
| INDE | 28 | 41 | 39 | FOBS= | 148.1 | SIGMA= | 1.2 | PHAS= | 30.1 | FOM= | 0.96 | TEST= 0 |
| INDE | 28 | 41 | 41 | FOBS= | 44.5 | SIGMA= | 3.7 | PHAS= | -7.7 | FOM= | 0.55 | TEST= 0 |
| INDE | 28 | 41 | 43 | FOBS= | 33.9 | SIGMA= | 4.8 | PHAS= | 160.6 | FOM= | 0.59 | TEST= 0 |
| INDE | 28 | 41 | 45 | FOBS= | 17.7 | SIGMA= | 10.6 | PHAS= | -82.9 | FOM= | 0.37 | TEST= 0 |
| INDE | 28 | 41 | 47 | FOBS= | 64.6 | SIGMA= | 2.6 | PHAS= | 23.8 | FOM= | 0.75 | TEST= 0 |
| INDE | 28 | 41 | 49 | FOBS= | 33.7 | SIGMA= | 5.3 | PHAS= | -115.3 | FOM= | 0.33 | TEST= 0 |
| INDE | 28 | 41 | 51 | FOBS= | 54.8 | SIGMA= | 3.2 | PHAS= | 118.3 | FOM= | 0.75 | TEST= 0 |
| INDE | 28 | 41 | 53 | FOBS= | 28.5 | SIGMA= | 6.7 | PHAS= | 45.2 | FOM= | 0.55 | TEST= 0 |
| INDE | 28 | 41 | 55 | FOBS= | 53.6 | SIGMA= | 3.6 | PHAS= | -86.9 | FOM= | 0.78 | TEST= 0 |
| INDE | 28 | 41 | 57 | FOBS= | 74.1 | SIGMA= | 3.0 | PHAS= | 124.5 | FOM= | 0.78 | TEST= 0 |
| INDE | 28 | 41 | 59 | FOBS= | 53.2 | SIGMA= | 6.7 | PHAS= | 6.0 | FOM= | 0.79 | TEST= 0 |
| INDE | 28 | 42 | 28 | FOBS= | 43.6 | SIGMA= | 4.0 | PHAS= | -131.0 | FOM= | 0.38 | TEST= 0 |
| INDE | 28 | 42 | 30 | FOBS= | 69.9 | SIGMA= | 2.4 | PHAS= | 3.9 | FOM= | 0.90 | TEST= 0 |
| INDE | 28 | 42 | 32 | FOBS= | 57.4 | SIGMA= | 3.3 | PHAS= | 110.0 | FOM= | 0.30 | TEST= 0 |
| INDE | 28 | 42 | 34 | FOBS= | 39.2 | SIGMA= | 4.6 | PHAS= | 56.8 | FOM= | 0.68 | TEST= 0 |
| INDE | 28 | 42 | 36 | FOBS= | 35.5 | SIGMA= | 4.8 | PHAS= | -33.1 | FOM= | 0.38 | TEST= 0 |
| INDE | 28 | 42 | 38 | FOBS= | 34.5 | SIGMA= | 4.9 | PHAS= | -32.6 | FOM= | 0.56 | TEST= 0 |
| INDE | 28 | 42 | 40 | FOBS= | 16.8 | SIGMA= | 9.7 | PHAS= | 31.2 | FOM= | 0.47 | TEST= 0 |
| INDE | 28 | 42 | 42 | FOBS= | 141.8 | SIGMA= | 1.2 | PHAS= | 77.5 | FOM= | 0.93 | TEST= 0 |
| INDE | 28 | 42 | 44 | FOBS= | 11.0 | SIGMA= | 15.2 | PHAS= | 167.0 | FOM= | 0.11 | TEST= 0 |
| INDE | 28 | 42 | 46 | FOBS= | 32.3 | SIGMA= | 5.6 | PHAS= | -44.0 | FOM= | 0.58 | TEST= 0 |
| INDE | 28 | 42 | 48 | FOBS= | 17.4 | SIGMA= | 10.8 | PHAS= | 14.6 | FOM= | 0.30 | TEST= 0 |
| INDE | 28 | 42 | 50 | FOBS= | 73.4 | SIGMA= | 2.5 | PHAS= | 51.6 | FOM= | 0.88 | TEST= 0 |
| INDE | 28 | 42 | 52 | FOBS= | 157.8 | SIGMA= | 1.3 | PHAS= | 38.0 | FOM= | 0.98 | TEST= 0 |
| INDE | 28 | 42 | 54 | FOBS= | 0.0 | SIGMA= | 22.7 | PHAS= | 0.0 | FOM= | 0.00 | TEST= 0 |
| INDE | 28 | 42 | 56 | FOBS= | 86.9 | SIGMA= | 2.3 | PHAS= | -162.9 | FOM= | 0.33 | TEST= 0 |
| INDE | 28 | 42 | 58 | FOBS= | 119.7 | SIGMA= | 1.8 | PHAS= | -82.0 | FOM= | 0.94 | TEST= 0 |
| INDE | 28 | 43 | 29 | FOBS= | 87.3 | SIGMA= | 1.9 | PHAS= | -147.1 | FOM= | 0.84 | TEST= 0 |
| INDE | 28 | 43 | 31 | FOBS= | 79.0 | SIGMA= | 2.3 | PHAS= | -107.4 | FOM= | 0.62 | TEST= 0 |
| INDE | 28 | 43 | 33 | FOBS= | 123.3 | SIGMA= | 1.5 | PHAS= | -3.1 | FOM= | 0.82 | TEST= 0 |
| INDE | 28 | 43 | 35 | FOBS= | 35.1 | SIGMA= | 5.1 | PHAS= | 95.2 | FOM= | 0.11 | TEST= 1 |
| INDE | 28 | 43 | 37 | FOBS= | 66.7 | SIGMA= | 2.5 | PHAS= | -0.4 | FOM= | 0.78 | TEST= 0 |
| INDE | 28 | 43 | 39 | FOBS= | 67.9 | SIGMA= | 2.4 | PHAS= | -23.2 | FOM= | 0.85 | TEST= 0 |
| INDE | 28 | 43 | 41 | FOBS= | 65.7 | SIGMA= | 2.5 | PHAS= | -1.2 | FOM= | 0.84 | TEST= 0 |
| INDE | 28 | 43 | 43 | FOBS= | 40.7 | SIGMA= | 4.0 | PHAS= | 87.6 | FOM= | 0.57 | TEST= 0 |
| INDE | 28 | 43 | 45 | FOBS= | 0.0 | SIGMA= | 20.2 | PHAS= | 0.0 | FOM= | 0.00 | TEST= 0 |
| INDE | 28 | 43 | 47 | FOBS= | 75.7 | SIGMA= | 2.4 | PHAS= | -23.9 | FOM= | 0.92 | TEST= 0 |
| INDE | 28 | 43 | 49 | FOBS= | 48.7 | SIGMA= | 3.7 | PHAS= | -36.7 | FOM= | 0.82 | TEST= 0 |
| INDE | 28 | 43 | 51 | FOBS= | 79.3 | SIGMA= | 2.5 | PHAS= | -49.8 | FOM= | 0.91 | TEST= 0 |
| INDE | 28 | 43 | 53 | FOBS= | 0.0 | SIGMA= | 19.5 | PHAS= | 0.0 | FOM= | 0.00 | TEST= 0 |
| INDE | 28 | 43 | 55 | FOBS= | 0.0 | SIGMA= | 20.3 | PHAS= | 0.0 | FOM= | 0.00 | TEST= 0 |
| INDE | 28 | 43 | 57 | FOBS= | 77.3 | SIGMA= | 2.6 | PHAS= | 159.3 | FOM= | 0.91 | TEST= 0 |
| INDE | 28 | 44 | 28 | FOBS= | 18.5 | SIGMA= | 9.9 | PHAS= | 90.1 | FOM= | 0.24 | TEST= 0 |
| INDE | 28 | 44 | 30 | FOBS= | 89.6 | SIGMA= | 1.9 | PHAS= | 43.7 | FOM= | 0.93 | TEST= 0 |
| INDE | 28 | 44 | 32 | FOBS= | 0.0 | SIGMA= | 18.8 | PHAS= | 0.0 | FOM= | 0.00 | TEST= 0 |
| INDE | 28 | 44 | 34 | FOBS= | 0.0 | SIGMA= | 19.3 | PHAS= | 0.0 | FOM= | 0.00 | TEST= 0 |
| INDE | 28 | 44 | 36 | FOBS= | 0.0 | SIGMA= | 20.4 | PHAS= | 0.0 | FOM= | 0.00 | TEST= 0 |
| INDE | 28 | 44 | 38 | FOBS= | 31.1 | SIGMA= | 5.5 | PHAS= | 152.5 | FOM= | 0.33 | TEST= 0 |
| INDE | 28 | 44 | 40 | FOBS= | 0.0 | SIGMA= | 18.4 | PHAS= | 0.0 | FOM= | 0.00 | TEST= 1 |
| INDE | 28 | 44 | 42 | FOBS= | 23.3 | SIGMA= | 7.6 | PHAS= | -0.5 | FOM= | 0.08 | TEST= 0 |
| INDE | 28 | 44 | 44 | FOBS= | 0.0 | SIGMA= | 21.4 | PHAS= | 0.0 | FOM= | 0.00 | TEST= 0 |
| INDE | 28 | 44 | 46 | FOBS= | 74.7 | SIGMA= | 2.5 | PHAS= | -117.7 | FOM= | 0.73 | TEST= 0 |
| INDE | 28 | 44 | 48 | FOBS= | 0.0 | SIGMA= | 19.4 | PHAS= | 0.0 | FOM= | 0.00 | TEST= 0 |

*FIG. 12A - 524*

```
INDE 28 44 50 FOBS=   23.0 SIGMA=  8.8 PHAS= -161.4 FOM= 0.19 TEST= 0
INDE 28 44 52 FOBS=   54.7 SIGMA=  3.8 PHAS=   37.6 FOM= 0.54 TEST= 0
INDE 28 44 54 FOBS=    0.0 SIGMA= 21.8 PHAS=    0.0 FOM= 0.00 TEST= 0
INDE 28 44 56 FOBS=    0.0 SIGMA= 21.2 PHAS=    0.0 FOM= 0.00 TEST= 0
INDE 28 45 29 FOBS=  155.1 SIGMA=  1.1 PHAS= -109.2 FOM= 0.95 TEST= 0
INDE 28 45 31 FOBS=   32.2 SIGMA=  7.2 PHAS=  -57.6 FOM= 0.78 TEST= 0
INDE 28 45 33 FOBS=   65.6 SIGMA=  2.7 PHAS=   -4.3 FOM= 0.83 TEST= 0
INDE 28 45 35 FOBS=   28.8 SIGMA=  6.1 PHAS= -147.7 FOM= 0.29 TEST= 0
INDE 28 45 37 FOBS=   87.3 SIGMA=  2.1 PHAS=   37.1 FOM= 0.83 TEST= 0
INDE 28 45 39 FOBS=    0.0 SIGMA= 18.0 PHAS=    0.0 FOM= 0.00 TEST= 0
INDE 28 45 41 FOBS=   20.8 SIGMA=  9.6 PHAS=  152.6 FOM= 0.27 TEST= 0
INDE 28 45 43 FOBS=   46.5 SIGMA=  4.1 PHAS=   90.1 FOM= 0.45 TEST= 0
INDE 28 45 45 FOBS=   35.0 SIGMA=  5.2 PHAS=   74.5 FOM= 0.67 TEST= 0
INDE 28 45 47 FOBS=   40.6 SIGMA=  4.5 PHAS=  -21.8 FOM= 0.56 TEST= 0
INDE 28 45 49 FOBS=   15.9 SIGMA= 11.5 PHAS=  -12.0 FOM= 0.02 TEST= 0
INDE 28 45 51 FOBS=   14.5 SIGMA= 14.3 PHAS=  -16.8 FOM= 0.17 TEST= 0
INDE 28 45 53 FOBS=    0.0 SIGMA= 19.7 PHAS=    0.0 FOM= 0.00 TEST= 0
INDE 28 45 55 FOBS=    0.0 SIGMA= 19.9 PHAS=    0.0 FOM= 0.00 TEST= 0
INDE 28 46 28 FOBS=   19.0 SIGMA=  9.0 PHAS= -143.5 FOM= 0.09 TEST= 0
INDE 28 46 30 FOBS=   58.2 SIGMA=  2.7 PHAS=  102.8 FOM= 0.77 TEST= 0
INDE 28 46 32 FOBS=   80.5 SIGMA=  2.2 PHAS=  -46.1 FOM= 0.93 TEST= 0
INDE 28 46 34 FOBS=    0.0 SIGMA= 19.7 PHAS=    0.0 FOM= 0.00 TEST= 0
INDE 28 46 36 FOBS=   54.0 SIGMA=  3.3 PHAS=  140.7 FOM= 0.36 TEST= 0
INDE 28 46 38 FOBS=   51.0 SIGMA=  3.4 PHAS= -153.0 FOM= 0.58 TEST= 0
INDE 28 46 40 FOBS=  232.5 SIGMA=  1.0 PHAS=  100.3 FOM= 0.98 TEST= 0
INDE 28 46 42 FOBS=   32.1 SIGMA=  5.9 PHAS=  -51.3 FOM= 0.06 TEST= 1
INDE 28 46 44 FOBS=   48.6 SIGMA=  3.8 PHAS=  -33.2 FOM= 0.09 TEST= 1
INDE 28 46 46 FOBS=   81.0 SIGMA=  2.3 PHAS= -169.3 FOM= 0.89 TEST= 0
INDE 28 46 48 FOBS=    0.0 SIGMA= 21.8 PHAS=    0.0 FOM= 0.00 TEST= 0
INDE 28 46 50 FOBS=   42.1 SIGMA=  5.0 PHAS=  125.9 FOM= 0.80 TEST= 0
INDE 28 46 52 FOBS=   47.4 SIGMA=  4.2 PHAS=  -10.8 FOM= 0.53 TEST= 0
INDE 28 46 54 FOBS=   15.9 SIGMA= 13.2 PHAS=  -80.1 FOM= 0.58 TEST= 0
INDE 28 46 56 FOBS=    0.0 SIGMA= 29.3 PHAS=    0.0 FOM= 0.00 TEST= 1
INDE 28 47 29 FOBS=   80.3 SIGMA=  2.0 PHAS= -164.6 FOM= 0.88 TEST= 0
INDE 28 47 31 FOBS=    0.0 SIGMA= 19.1 PHAS=    0.0 FOM= 0.00 TEST= 0
INDE 28 47 33 FOBS=  126.2 SIGMA=  1.5 PHAS= -129.9 FOM= 0.96 TEST= 0
INDE 28 47 35 FOBS=   59.0 SIGMA=  3.0 PHAS= -105.1 FOM= 0.44 TEST= 0
INDE 28 47 37 FOBS=  110.8 SIGMA=  1.7 PHAS=   63.2 FOM= 0.95 TEST= 0
INDE 28 47 39 FOBS=  148.8 SIGMA=  1.3 PHAS=   21.8 FOM= 0.97 TEST= 0
INDE 28 47 41 FOBS=  170.3 SIGMA=  1.2 PHAS=  -17.4 FOM= 0.97 TEST= 0
INDE 28 47 43 FOBS=   22.1 SIGMA=  8.2 PHAS=  -93.3 FOM= 0.43 TEST= 0
INDE 28 47 45 FOBS=   52.1 SIGMA=  3.5 PHAS=   87.8 FOM= 0.72 TEST= 0
INDE 28 47 47 FOBS=   73.7 SIGMA=  2.5 PHAS=  122.4 FOM= 0.31 TEST= 1
INDE 28 47 49 FOBS=   54.9 SIGMA=  3.6 PHAS=  153.6 FOM= 0.43 TEST= 0
INDE 28 47 51 FOBS=   24.3 SIGMA=  8.2 PHAS=  -54.3 FOM= 0.40 TEST= 0
INDE 28 47 53 FOBS=   60.0 SIGMA=  3.4 PHAS= -119.0 FOM= 0.92 TEST= 0
INDE 28 47 55 FOBS=   59.9 SIGMA=  4.3 PHAS=  107.0 FOM= 0.19 TEST= 1
INDE 28 48 28 FOBS=   54.9 SIGMA=  3.1 PHAS=  158.1 FOM= 0.71 TEST= 0
INDE 28 48 30 FOBS=    0.0 SIGMA= 18.1 PHAS=    0.0 FOM= 0.00 TEST= 0
INDE 28 48 32 FOBS=  117.8 SIGMA=  1.6 PHAS=  100.3 FOM= 0.92 TEST= 0
INDE 28 48 34 FOBS=  125.6 SIGMA=  1.5 PHAS=  155.7 FOM= 0.93 TEST= 0
INDE 28 48 36 FOBS=    0.0 SIGMA= 19.3 PHAS=    0.0 FOM= 0.00 TEST= 1
INDE 28 48 38 FOBS=   34.3 SIGMA=  5.9 PHAS=    3.4 FOM= 0.38 TEST= 0
INDE 28 48 40 FOBS=   53.2 SIGMA=  3.4 PHAS=  169.2 FOM= 0.76 TEST= 0
INDE 28 48 42 FOBS=   79.5 SIGMA=  2.3 PHAS= -138.8 FOM= 0.75 TEST= 0
INDE 28 48 44 FOBS=   23.6 SIGMA=  8.8 PHAS=  -60.8 FOM= 0.25 TEST= 0
INDE 28 48 46 FOBS=   34.2 SIGMA=  6.7 PHAS= -157.7 FOM= 0.66 TEST= 0
INDE 28 48 48 FOBS=   42.4 SIGMA=  5.1 PHAS=   55.2 FOM= 0.72 TEST= 0
INDE 28 48 50 FOBS=   34.5 SIGMA=  6.8 PHAS=  141.5 FOM= 0.61 TEST= 0
INDE 28 48 52 FOBS=   18.0 SIGMA= 13.0 PHAS=   71.3 FOM= 0.37 TEST= 0
INDE 28 48 54 FOBS=    0.0 SIGMA= 22.7 PHAS=    0.0 FOM= 0.00 TEST= 0
INDE 28 49 29 FOBS=   41.2 SIGMA=  4.0 PHAS=  157.7 FOM= 0.16 TEST= 1
INDE 28 49 31 FOBS=   65.0 SIGMA=  2.6 PHAS=   30.8 FOM= 0.73 TEST= 0
INDE 28 49 33 FOBS=   39.9 SIGMA=  4.6 PHAS=   -8.9 FOM= 0.64 TEST= 0
INDE 28 49 35 FOBS=   53.9 SIGMA=  3.7 PHAS=  -92.9 FOM= 0.62 TEST= 0
INDE 28 49 37 FOBS=   28.7 SIGMA=  8.1 PHAS=   20.3 FOM= 0.26 TEST= 1
INDE 28 49 39 FOBS=   66.5 SIGMA=  3.1 PHAS=   58.7 FOM= 0.86 TEST= 0
INDE 28 49 41 FOBS=   62.8 SIGMA=  2.9 PHAS=   32.3 FOM= 0.83 TEST= 0
INDE 28 49 43 FOBS=    0.0 SIGMA= 19.5 PHAS=    0.0 FOM= 0.00 TEST= 0
INDE 28 49 45 FOBS=   60.3 SIGMA=  3.3 PHAS=   -4.2 FOM= 0.88 TEST= 0
```

*FIG. 12A - 525*

```
INDE 28 49 47 FOBS=    103.0 SIGMA=  2.0 PHAS=  -162.5 FOM= 0.91 TEST= 0
INDE 28 49 49 FOBS=     72.1 SIGMA=  2.8 PHAS=   150.5 FOM= 0.83 TEST= 0
INDE 28 49 51 FOBS=     29.0 SIGMA=  9.0 PHAS=   -78.8 FOM= 0.63 TEST= 0
INDE 28 49 53 FOBS=     45.9 SIGMA=  8.1 PHAS=   -86.9 FOM= 0.74 TEST= 0
INDE 28 50 28 FOBS=      0.0 SIGMA= 19.4 PHAS=     0.0 FOM= 0.00 TEST= 1
INDE 28 50 30 FOBS=     57.2 SIGMA=  2.8 PHAS=    15.2 FOM= 0.72 TEST= 0
INDE 28 50 32 FOBS=    102.7 SIGMA=  1.9 PHAS=  -153.1 FOM= 0.87 TEST= 0
INDE 28 50 34 FOBS=      0.0 SIGMA= 21.3 PHAS=     0.0 FOM= 0.00 TEST= 0
INDE 28 50 36 FOBS=     99.4 SIGMA=  2.1 PHAS=  -131.3 FOM= 0.90 TEST= 0
INDE 28 50 38 FOBS=     34.5 SIGMA=  6.3 PHAS=    28.5 FOM= 0.42 TEST= 0
INDE 28 50 40 FOBS=     53.0 SIGMA=  3.6 PHAS=   -58.1 FOM= 0.20 TEST= 0
INDE 28 50 42 FOBS=     11.5 SIGMA= 18.8 PHAS=   -74.4 FOM= 0.33 TEST= 0
INDE 28 50 44 FOBS=      0.0 SIGMA= 21.2 PHAS=     0.0 FOM= 0.00 TEST= 0
INDE 28 50 46 FOBS=      0.0 SIGMA= 20.7 PHAS=     0.0 FOM= 0.00 TEST= 0
INDE 28 50 48 FOBS=    156.8 SIGMA=  1.5 PHAS=    97.6 FOM= 0.77 TEST= 1
INDE 28 50 50 FOBS=     21.9 SIGMA= 11.1 PHAS=    84.8 FOM= 0.31 TEST= 0
INDE 28 50 52 FOBS=     57.2 SIGMA=  5.2 PHAS=   102.7 FOM= 0.63 TEST= 0
INDE 28 51 29 FOBS=     53.6 SIGMA=  3.2 PHAS=  -122.2 FOM= 0.58 TEST= 1
INDE 28 51 31 FOBS=     61.8 SIGMA=  2.8 PHAS=    28.9 FOM= 0.78 TEST= 0
INDE 28 51 33 FOBS=     63.1 SIGMA=  3.2 PHAS=   -25.7 FOM= 0.87 TEST= 0
INDE 28 51 35 FOBS=      0.0 SIGMA= 19.9 PHAS=     0.0 FOM= 0.00 TEST= 0
INDE 28 51 37 FOBS=     11.6 SIGMA= 20.7 PHAS=   -20.5 FOM= 0.09 TEST= 0
INDE 28 51 39 FOBS=     69.2 SIGMA=  3.2 PHAS=   -87.0 FOM= 0.67 TEST= 0
INDE 28 51 41 FOBS=     46.9 SIGMA=  4.5 PHAS=   135.9 FOM= 0.62 TEST= 0
INDE 28 51 43 FOBS=     57.0 SIGMA=  3.7 PHAS=    48.2 FOM= 0.51 TEST= 0
INDE 28 51 45 FOBS=     26.6 SIGMA=  8.1 PHAS=    -4.1 FOM= 0.40 TEST= 0
INDE 28 51 47 FOBS=     31.9 SIGMA=  6.8 PHAS=   -49.9 FOM= 0.03 TEST= 1
INDE 28 51 49 FOBS=     55.6 SIGMA=  4.7 PHAS=   -42.8 FOM= 0.85 TEST= 0
INDE 28 51 51 FOBS=      0.0 SIGMA= 25.8 PHAS=     0.0 FOM= 0.00 TEST= 0
INDE 28 52 28 FOBS=    110.9 SIGMA=  1.7 PHAS=   174.4 FOM= 0.94 TEST= 0
INDE 28 52 30 FOBS=      0.0 SIGMA= 19.3 PHAS=     0.0 FOM= 0.00 TEST= 0
INDE 28 52 32 FOBS=    133.2 SIGMA=  1.5 PHAS=  -138.9 FOM= 0.96 TEST= 0
INDE 28 52 34 FOBS=     16.3 SIGMA= 13.2 PHAS=   -40.1 FOM= 0.14 TEST= 0
INDE 28 52 36 FOBS=      0.0 SIGMA= 22.3 PHAS=     0.0 FOM= 0.00 TEST= 0
INDE 28 52 38 FOBS=    120.8 SIGMA=  2.1 PHAS=   -75.5 FOM= 0.10 TEST= 1
INDE 28 52 40 FOBS=    108.6 SIGMA=  2.3 PHAS=   130.3 FOM= 0.91 TEST= 0
INDE 28 52 42 FOBS=      0.0 SIGMA= 21.2 PHAS=     0.0 FOM= 0.00 TEST= 0
INDE 28 52 44 FOBS=     56.8 SIGMA=  3.8 PHAS=    34.6 FOM= 0.77 TEST= 0
INDE 28 52 46 FOBS=     36.1 SIGMA=  6.5 PHAS=  -179.9 FOM= 0.38 TEST= 0
INDE 28 52 48 FOBS=    127.3 SIGMA=  1.9 PHAS=   177.0 FOM= 0.96 TEST= 0
INDE 28 52 50 FOBS=     52.4 SIGMA=  5.2 PHAS=   173.6 FOM= 0.46 TEST= 0
INDE 28 53 29 FOBS=     51.2 SIGMA=  4.2 PHAS=    89.9 FOM= 0.56 TEST= 0
INDE 28 53 31 FOBS=    127.2 SIGMA=  1.7 PHAS=    66.3 FOM= 0.93 TEST= 0
INDE 28 53 33 FOBS=     71.3 SIGMA=  3.2 PHAS=    81.9 FOM= 0.80 TEST= 0
INDE 28 53 35 FOBS=     51.3 SIGMA=  4.5 PHAS=  -140.4 FOM= 0.22 TEST= 1
INDE 28 53 37 FOBS=     76.8 SIGMA=  3.1 PHAS=   -53.1 FOM= 0.66 TEST= 0
INDE 28 53 39 FOBS=    118.5 SIGMA=  2.1 PHAS=   -49.6 FOM= 0.93 TEST= 0
INDE 28 53 41 FOBS=     15.1 SIGMA= 16.3 PHAS=    40.4 FOM= 0.47 TEST= 0
INDE 28 53 43 FOBS=      0.0 SIGMA= 22.4 PHAS=     0.0 FOM= 0.00 TEST= 0
INDE 28 53 45 FOBS=     38.4 SIGMA=  6.0 PHAS=   -38.2 FOM= 0.15 TEST= 1
INDE 28 53 47 FOBS=    104.8 SIGMA=  2.2 PHAS=    59.4 FOM= 0.94 TEST= 0
INDE 28 53 49 FOBS=     33.2 SIGMA=  9.0 PHAS=    84.2 FOM= 0.64 TEST= 0
INDE 28 54 28 FOBS=     79.6 SIGMA=  2.7 PHAS=  -101.4 FOM= 0.89 TEST= 0
INDE 28 54 30 FOBS=    108.3 SIGMA=  2.1 PHAS=    47.1 FOM= 0.92 TEST= 0
INDE 28 54 32 FOBS=     21.7 SIGMA= 11.4 PHAS=   -26.5 FOM= 0.77 TEST= 0
INDE 28 54 34 FOBS=     30.8 SIGMA=  9.1 PHAS=  -164.2 FOM= 0.12 TEST= 1
INDE 28 54 36 FOBS=     42.0 SIGMA=  6.6 PHAS=   -52.6 FOM= 0.53 TEST= 0
INDE 28 54 38 FOBS=     53.5 SIGMA=  4.5 PHAS=   154.2 FOM= 0.79 TEST= 0
INDE 28 54 40 FOBS=     48.3 SIGMA=  5.1 PHAS=  -171.6 FOM= 0.73 TEST= 0
INDE 28 54 42 FOBS=      0.0 SIGMA= 21.3 PHAS=     0.0 FOM= 0.00 TEST= 0
INDE 28 54 44 FOBS=      0.0 SIGMA= 20.9 PHAS=     0.0 FOM= 0.00 TEST= 0
INDE 28 54 46 FOBS=     15.3 SIGMA= 15.5 PHAS=   -34.1 FOM= 0.14 TEST= 0
INDE 28 54 48 FOBS=     71.7 SIGMA=  3.9 PHAS=    99.0 FOM= 0.06 TEST= 1
INDE 28 55 29 FOBS=     78.8 SIGMA=  3.1 PHAS=   158.5 FOM= 0.21 TEST= 1
INDE 28 55 31 FOBS=     54.2 SIGMA=  4.5 PHAS=    -6.6 FOM= 0.77 TEST= 0
INDE 28 55 33 FOBS=     21.6 SIGMA= 11.4 PHAS=   -86.2 FOM= 0.33 TEST= 0
INDE 28 55 35 FOBS=     29.5 SIGMA=  7.9 PHAS=   -86.9 FOM= 0.83 TEST= 0
INDE 28 55 37 FOBS=      0.0 SIGMA= 22.7 PHAS=     0.0 FOM= 0.00 TEST= 0
INDE 28 55 39 FOBS=     41.5 SIGMA=  5.8 PHAS=   -15.2 FOM= 0.53 TEST= 0
INDE 28 55 41 FOBS=     70.5 SIGMA=  3.5 PHAS=    26.7 FOM= 0.87 TEST= 0
```

*FIG. 12A - 526*

```
INDE  28  55  43 FOBS=    0.0 SIGMA=  23.2 PHAS=    0.0 FOM= 0.00 TEST= 0
INDE  28  55  45 FOBS=    0.0 SIGMA=  21.9 PHAS=    0.0 FOM= 0.00 TEST= 1
INDE  28  55  47 FOBS=   38.6 SIGMA=   7.0 PHAS=    2.5 FOM= 0.27 TEST= 0
INDE  28  56  28 FOBS=    0.0 SIGMA=  21.8 PHAS=    0.0 FOM= 0.00 TEST= 0
INDE  28  56  30 FOBS=   36.6 SIGMA=   6.6 PHAS=   16.8 FOM= 0.62 TEST= 0
INDE  28  56  32 FOBS=   70.4 SIGMA=   3.5 PHAS=  -47.9 FOM= 0.76 TEST= 0
INDE  28  56  34 FOBS=   75.5 SIGMA=   3.1 PHAS=  161.2 FOM= 0.86 TEST= 0
INDE  28  56  36 FOBS=    0.0 SIGMA=  24.1 PHAS=    0.0 FOM= 0.00 TEST= 0
INDE  28  56  38 FOBS=    0.0 SIGMA=  21.9 PHAS=    0.0 FOM= 0.00 TEST= 0
INDE  28  56  40 FOBS=    7.0 SIGMA=  37.3 PHAS= -150.0 FOM= 0.09 TEST= 0
INDE  28  56  42 FOBS=  105.7 SIGMA=   2.8 PHAS=  -54.1 FOM= 0.96 TEST= 0
INDE  28  56  44 FOBS=   24.4 SIGMA=  10.0 PHAS=  106.0 FOM= 0.53 TEST= 0
INDE  28  56  46 FOBS=   40.0 SIGMA=   8.6 PHAS= -164.8 FOM= 0.59 TEST= 0
INDE  28  57  29 FOBS=   59.0 SIGMA=   4.1 PHAS=  143.8 FOM= 0.72 TEST= 0
INDE  28  57  31 FOBS=   65.8 SIGMA=   3.7 PHAS= -111.3 FOM= 0.78 TEST= 0
INDE  28  57  33 FOBS=    0.0 SIGMA=  21.4 PHAS=    0.0 FOM= 0.00 TEST= 0
INDE  28  57  35 FOBS=   35.1 SIGMA=   7.3 PHAS=   24.6 FOM= 0.54 TEST= 0
INDE  28  57  37 FOBS=   39.7 SIGMA=   6.0 PHAS=   42.5 FOM= 0.47 TEST= 0
INDE  28  57  39 FOBS=   46.9 SIGMA=   5.9 PHAS=  146.2 FOM= 0.56 TEST= 0
INDE  28  57  41 FOBS=   77.2 SIGMA=   4.2 PHAS=  -93.0 FOM= 0.89 TEST= 0
INDE  28  57  43 FOBS=   39.3 SIGMA=   8.2 PHAS=   17.5 FOM= 0.07 TEST= 0
INDE  28  58  28 FOBS=   55.3 SIGMA=   4.4 PHAS=  -30.6 FOM= 0.76 TEST= 0
INDE  28  58  30 FOBS=    0.0 SIGMA=  21.9 PHAS=    0.0 FOM= 0.00 TEST= 1
INDE  28  58  32 FOBS=    0.0 SIGMA=  23.5 PHAS=    0.0 FOM= 0.00 TEST= 0
INDE  28  58  34 FOBS=   31.6 SIGMA=   8.0 PHAS=  -13.3 FOM= 0.21 TEST= 0
INDE  28  58  36 FOBS=   76.4 SIGMA=   3.5 PHAS=  -92.7 FOM= 0.82 TEST= 0
INDE  28  58  38 FOBS=   54.7 SIGMA=   5.6 PHAS=   -4.3 FOM= 0.74 TEST= 0
INDE  28  58  40 FOBS=   68.7 SIGMA=   4.7 PHAS= -166.6 FOM= 0.81 TEST= 0
INDE  28  58  42 FOBS=   91.7 SIGMA=   3.6 PHAS=  -87.4 FOM= 0.94 TEST= 0
INDE  28  59  29 FOBS=   56.3 SIGMA=   4.9 PHAS=  171.5 FOM= 0.86 TEST= 0
INDE  28  59  31 FOBS=    0.0 SIGMA=  23.5 PHAS=    0.0 FOM= 0.00 TEST= 0
INDE  28  59  33 FOBS=   50.3 SIGMA=   6.4 PHAS=  -58.7 FOM= 0.82 TEST= 0
INDE  28  59  35 FOBS=    0.0 SIGMA=  26.0 PHAS=    0.0 FOM= 0.00 TEST= 0
INDE  28  59  37 FOBS=   28.9 SIGMA=  10.3 PHAS=  163.3 FOM= 0.57 TEST= 0
INDE  28  59  39 FOBS=   27.9 SIGMA=  13.3 PHAS= -171.6 FOM= 0.58 TEST= 0
INDE  28  59  41 FOBS=   46.6 SIGMA=   7.8 PHAS= -170.7 FOM= 0.65 TEST= 0
INDE  28  60  28 FOBS=   53.6 SIGMA=   5.0 PHAS=   95.4 FOM= 0.75 TEST= 0
INDE  28  60  30 FOBS=   30.3 SIGMA=  12.5 PHAS=  -16.1 FOM= 0.33 TEST= 0
INDE  28  60  32 FOBS=   59.2 SIGMA=   5.4 PHAS=   86.0 FOM= 0.69 TEST= 0
INDE  28  60  34 FOBS=    0.0 SIGMA=  28.4 PHAS=    0.0 FOM= 0.00 TEST= 0
INDE  28  60  36 FOBS=    0.0 SIGMA=  24.2 PHAS=    0.0 FOM= 0.00 TEST= 0
INDE  28  60  38 FOBS=    0.0 SIGMA=  29.4 PHAS=    0.0 FOM= 0.00 TEST= 0
INDE  28  60  40 FOBS=    0.0 SIGMA=  25.3 PHAS=    0.0 FOM= 0.00 TEST= 0
INDE  28  61  29 FOBS=    0.0 SIGMA=  22.1 PHAS=    0.0 FOM= 0.00 TEST= 0
INDE  28  61  31 FOBS=   36.4 SIGMA=   8.7 PHAS=  121.8 FOM= 0.50 TEST= 0
INDE  28  61  33 FOBS=   48.6 SIGMA=   6.7 PHAS= -127.8 FOM= 0.05 TEST= 1
INDE  28  61  35 FOBS=   54.9 SIGMA=   5.4 PHAS=  166.2 FOM= 0.69 TEST= 0
INDE  28  61  37 FOBS=   71.1 SIGMA=   4.4 PHAS=  166.0 FOM= 0.92 TEST= 0
INDE  28  61  39 FOBS=    0.0 SIGMA=  30.4 PHAS=    0.0 FOM= 0.00 TEST= 1
INDE  28  62  28 FOBS=    0.0 SIGMA=  27.9 PHAS=    0.0 FOM= 0.00 TEST= 0
INDE  28  62  30 FOBS=   52.2 SIGMA=   4.8 PHAS=  -95.8 FOM= 0.21 TEST= 1
INDE  28  62  32 FOBS=   34.3 SIGMA=   9.5 PHAS=   16.6 FOM= 0.44 TEST= 0
INDE  28  62  34 FOBS=   19.7 SIGMA=  16.8 PHAS= -149.0 FOM= 0.18 TEST= 0
INDE  28  62  36 FOBS=   24.3 SIGMA=  14.4 PHAS=  113.5 FOM= 0.21 TEST= 0
INDE  28  63  29 FOBS=   68.9 SIGMA=   3.6 PHAS=   -1.5 FOM= 0.84 TEST= 0
INDE  28  63  31 FOBS=    0.0 SIGMA=  26.0 PHAS=    0.0 FOM= 0.00 TEST= 0
INDE  28  63  33 FOBS=    0.0 SIGMA=  25.6 PHAS=    0.0 FOM= 0.00 TEST= 0
INDE  28  63  35 FOBS=   87.2 SIGMA=   5.0 PHAS=  168.9 FOM= 0.86 TEST= 0
INDE  28  64  28 FOBS=   58.3 SIGMA=   6.7 PHAS=  -64.9 FOM= 0.82 TEST= 0
INDE  28  64  30 FOBS=    0.0 SIGMA=  22.6 PHAS=    0.0 FOM= 0.00 TEST= 0
INDE  28  64  32 FOBS=    0.0 SIGMA=  28.5 PHAS=    0.0 FOM= 0.00 TEST= 0
INDE  28  64  34 FOBS=   68.7 SIGMA=   6.1 PHAS=   77.5 FOM= 0.84 TEST= 0
INDE  28  65  29 FOBS=    0.0 SIGMA=  28.0 PHAS=    0.0 FOM= 0.00 TEST= 0
INDE  28  65  31 FOBS=    0.0 SIGMA=  26.0 PHAS=    0.0 FOM= 0.00 TEST= 0
INDE  28  66  28 FOBS=   47.0 SIGMA=  11.3 PHAS=  -22.7 FOM= 0.64 TEST= 0
INDE  28  66  30 FOBS=   22.7 SIGMA=  24.4 PHAS= -176.6 FOM= 0.28 TEST= 0
INDE  29  30  29 FOBS=  335.0 SIGMA=   0.6 PHAS=  179.0 FOM= 0.95 TEST= 1
INDE  29  30  31 FOBS=  238.6 SIGMA=   0.9 PHAS=   75.3 FOM= 0.95 TEST= 0
INDE  29  30  33 FOBS=   49.4 SIGMA=   3.8 PHAS= -117.6 FOM= 0.79 TEST= 0
INDE  29  30  35 FOBS=  290.4 SIGMA=   0.8 PHAS=  -80.0 FOM= 0.98 TEST= 0
```

*FIG. 12A - 527*

```
INDE 29 30 37 FOBS=   192.9 SIGMA=  1.1 PHAS=  -51.6 FOM= 0.96 TEST= 0
INDE 29 30 39 FOBS=    20.0 SIGMA=  9.5 PHAS=   74.6 FOM= 0.26 TEST= 0
INDE 29 30 41 FOBS=   200.7 SIGMA=  0.9 PHAS=   72.2 FOM= 0.98 TEST= 0
INDE 29 30 43 FOBS=   208.5 SIGMA=  0.9 PHAS=   60.0 FOM= 0.97 TEST= 0
INDE 29 30 45 FOBS=   133.4 SIGMA=  1.3 PHAS=   91.4 FOM= 0.95 TEST= 0
INDE 29 30 47 FOBS=    99.0 SIGMA=  1.6 PHAS=  129.2 FOM= 0.83 TEST= 0
INDE 29 30 49 FOBS=    64.8 SIGMA=  2.4 PHAS=  113.8 FOM= 0.36 TEST= 0
INDE 29 30 51 FOBS=    39.3 SIGMA=  4.9 PHAS= -156.5 FOM= 0.15 TEST= 0
INDE 29 30 53 FOBS=    52.5 SIGMA=  3.9 PHAS=   -4.4 FOM= 0.15 TEST= 0
INDE 29 30 55 FOBS=     0.0 SIGMA= 21.8 PHAS=    0.0 FOM= 0.00 TEST= 0
INDE 29 30 57 FOBS=    42.6 SIGMA=  6.5 PHAS=  -67.7 FOM= 0.46 TEST= 0
INDE 29 30 59 FOBS=     0.0 SIGMA= 23.6 PHAS=    0.0 FOM= 0.00 TEST= 0
INDE 29 30 61 FOBS=    42.8 SIGMA=  5.8 PHAS=  101.6 FOM= 0.21 TEST= 1
INDE 29 30 63 FOBS=    69.5 SIGMA=  7.7 PHAS=  -59.7 FOM= 0.43 TEST= 0
INDE 29 30 65 FOBS=     0.0 SIGMA= 33.7 PHAS=    0.0 FOM= 0.00 TEST= 0
INDE 29 31 30 FOBS=    82.6 SIGMA=  2.1 PHAS=   83.2 FOM= 0.94 TEST= 0
INDE 29 31 32 FOBS=   148.2 SIGMA=  1.3 PHAS=  136.1 FOM= 0.89 TEST= 0
INDE 29 31 34 FOBS=    96.4 SIGMA=  2.0 PHAS= -164.7 FOM= 0.74 TEST= 0
INDE 29 31 36 FOBS=   107.2 SIGMA=  1.8 PHAS=  160.8 FOM= 0.86 TEST= 0
INDE 29 31 38 FOBS=   197.7 SIGMA=  1.0 PHAS= -167.8 FOM= 0.94 TEST= 0
INDE 29 31 40 FOBS=   146.7 SIGMA=  1.3 PHAS=  -72.4 FOM= 0.97 TEST= 0
INDE 29 31 42 FOBS=   262.4 SIGMA=  0.9 PHAS=  -42.9 FOM= 0.98 TEST= 0
INDE 29 31 44 FOBS=   143.7 SIGMA=  1.2 PHAS=    2.2 FOM= 0.94 TEST= 0
INDE 29 31 46 FOBS=    84.9 SIGMA=  1.9 PHAS=   48.4 FOM= 0.86 TEST= 1
INDE 29 31 48 FOBS=    89.5 SIGMA=  1.8 PHAS=   45.1 FOM= 0.92 TEST= 0
INDE 29 31 50 FOBS=    20.4 SIGMA=  8.3 PHAS=  113.3 FOM= 0.01 TEST= 1
INDE 29 31 52 FOBS=   105.0 SIGMA=  1.9 PHAS=   88.0 FOM= 0.92 TEST= 0
INDE 29 31 54 FOBS=     0.0 SIGMA= 20.1 PHAS=    0.0 FOM= 0.00 TEST= 1
INDE 29 31 56 FOBS=    35.5 SIGMA=  7.8 PHAS=  -19.9 FOM= 0.38 TEST= 0
INDE 29 31 58 FOBS=    43.2 SIGMA=  5.8 PHAS= -136.0 FOM= 0.67 TEST= 0
INDE 29 31 60 FOBS=    37.9 SIGMA=  6.6 PHAS= -175.9 FOM= 0.14 TEST= 1
INDE 29 31 62 FOBS=    63.7 SIGMA=  5.2 PHAS=  127.3 FOM= 0.56 TEST= 0
INDE 29 31 64 FOBS=    39.0 SIGMA= 14.5 PHAS=  -97.5 FOM= 0.21 TEST= 0
INDE 29 32 29 FOBS=   144.2 SIGMA=  1.4 PHAS= -107.2 FOM= 0.70 TEST= 0
INDE 29 32 31 FOBS=   192.4 SIGMA=  1.1 PHAS=   17.2 FOM= 0.93 TEST= 0
INDE 29 32 33 FOBS=   112.5 SIGMA=  1.7 PHAS=  160.6 FOM= 0.87 TEST= 0
INDE 29 32 35 FOBS=    98.1 SIGMA=  2.0 PHAS=  -39.9 FOM= 0.70 TEST= 0
INDE 29 32 37 FOBS=    96.8 SIGMA=  2.0 PHAS=  173.1 FOM= 0.92 TEST= 0
INDE 29 32 39 FOBS=    98.8 SIGMA=  1.9 PHAS=  137.2 FOM= 0.90 TEST= 0
INDE 29 32 41 FOBS=   166.4 SIGMA=  1.2 PHAS=  148.9 FOM= 0.96 TEST= 0
INDE 29 32 43 FOBS=   144.0 SIGMA=  1.3 PHAS= -118.2 FOM= 0.87 TEST= 0
INDE 29 32 45 FOBS=     0.0 SIGMA= 18.2 PHAS=    0.0 FOM= 0.00 TEST= 0
INDE 29 32 47 FOBS=   113.1 SIGMA=  1.5 PHAS=  -30.7 FOM= 0.94 TEST= 0
INDE 29 32 49 FOBS=    46.6 SIGMA=  3.4 PHAS=  -26.0 FOM= 0.67 TEST= 0
INDE 29 32 51 FOBS=    32.3 SIGMA=  5.4 PHAS= -102.8 FOM= 0.59 TEST= 0
INDE 29 32 53 FOBS=    82.8 SIGMA=  2.3 PHAS=   13.4 FOM= 0.88 TEST= 0
INDE 29 32 55 FOBS=     0.0 SIGMA= 20.1 PHAS=    0.0 FOM= 0.00 TEST= 1
INDE 29 32 57 FOBS=    74.1 SIGMA=  3.1 PHAS= -117.0 FOM= 0.81 TEST= 0
INDE 29 32 59 FOBS=    48.0 SIGMA=  5.2 PHAS=   32.2 FOM= 0.74 TEST= 0
INDE 29 32 61 FOBS=    18.3 SIGMA= 17.7 PHAS=  139.4 FOM= 0.47 TEST= 0
INDE 29 32 63 FOBS=    69.0 SIGMA=  4.9 PHAS=  -87.5 FOM= 0.52 TEST= 0
INDE 29 33 30 FOBS=   133.8 SIGMA=  1.4 PHAS= -169.0 FOM= 0.83 TEST= 0
INDE 29 33 32 FOBS=   154.6 SIGMA=  1.3 PHAS= -175.9 FOM= 0.87 TEST= 0
INDE 29 33 34 FOBS=    66.9 SIGMA=  2.8 PHAS= -166.4 FOM= 0.72 TEST= 0
INDE 29 33 36 FOBS=    75.6 SIGMA=  2.5 PHAS=  128.8 FOM= 0.85 TEST= 0
INDE 29 33 38 FOBS=    41.6 SIGMA=  4.4 PHAS=   92.4 FOM= 0.91 TEST= 0
INDE 29 33 40 FOBS=     0.0 SIGMA= 19.7 PHAS=    0.0 FOM= 0.00 TEST= 0
INDE 29 33 42 FOBS=     0.0 SIGMA= 20.3 PHAS=    0.0 FOM= 0.00 TEST= 0
INDE 29 33 44 FOBS=     0.0 SIGMA= 19.3 PHAS=    0.0 FOM= 0.00 TEST= 0
INDE 29 33 46 FOBS=    73.3 SIGMA=  2.4 PHAS=  -31.4 FOM= 0.66 TEST= 0
INDE 29 33 48 FOBS=   120.2 SIGMA=  1.4 PHAS= -132.5 FOM= 0.80 TEST= 0
INDE 29 33 50 FOBS=    19.5 SIGMA=  8.9 PHAS=  -16.6 FOM= 0.15 TEST= 0
INDE 29 33 52 FOBS=    45.0 SIGMA=  3.8 PHAS=  122.7 FOM= 0.27 TEST= 0
INDE 29 33 54 FOBS=    29.1 SIGMA=  7.6 PHAS=  141.5 FOM= 0.27 TEST= 0
INDE 29 33 56 FOBS=     0.0 SIGMA= 20.4 PHAS=    0.0 FOM= 0.00 TEST= 0
INDE 29 33 58 FOBS=    80.5 SIGMA=  2.6 PHAS= -146.2 FOM= 0.92 TEST= 0
INDE 29 33 60 FOBS=    35.1 SIGMA=  9.5 PHAS=  -28.6 FOM= 0.69 TEST= 0
INDE 29 33 62 FOBS=    55.3 SIGMA=  6.1 PHAS=  145.9 FOM= 0.82 TEST= 0
INDE 29 33 64 FOBS=    95.1 SIGMA=  3.7 PHAS=  130.0 FOM= 0.92 TEST= 0
INDE 29 34 29 FOBS=   133.3 SIGMA=  1.4 PHAS=   20.0 FOM= 0.95 TEST= 0
```

*FIG. 12A - 528*

```
INDE 29 34 31 FOBS=   64.7 SIGMA=  3.3 PHAS=   23.9 FOM= 0.80 TEST= 0
INDE 29 34 33 FOBS=  140.0 SIGMA=  1.4 PHAS=  130.9 FOM= 0.83 TEST= 1
INDE 29 34 35 FOBS=  135.0 SIGMA=  1.4 PHAS=  104.4 FOM= 0.88 TEST= 0
INDE 29 34 37 FOBS=  115.1 SIGMA=  1.7 PHAS=  134.7 FOM= 0.83 TEST= 0
INDE 29 34 39 FOBS=   90.1 SIGMA=  2.1 PHAS=   85.6 FOM= 0.86 TEST= 0
INDE 29 34 41 FOBS=    0.0 SIGMA= 20.2 PHAS=    0.0 FOM= 0.00 TEST= 1
INDE 29 34 43 FOBS=   36.1 SIGMA=  5.0 PHAS= -171.1 FOM= 0.57 TEST= 0
INDE 29 34 45 FOBS=    0.0 SIGMA= 19.2 PHAS=    0.0 FOM= 0.00 TEST= 0
INDE 29 34 47 FOBS=   42.0 SIGMA=  4.3 PHAS= -138.0 FOM= 0.30 TEST= 0
INDE 29 34 49 FOBS=   30.3 SIGMA=  6.1 PHAS=  -31.4 FOM= 0.39 TEST= 0
INDE 29 34 51 FOBS=  108.6 SIGMA=  1.7 PHAS= -100.0 FOM= 0.90 TEST= 0
INDE 29 34 53 FOBS=   51.6 SIGMA=  3.8 PHAS=   68.6 FOM= 0.75 TEST= 0
INDE 29 34 55 FOBS=    0.0 SIGMA= 22.0 PHAS=    0.0 FOM= 0.00 TEST= 0
INDE 29 34 57 FOBS=   39.8 SIGMA=  5.3 PHAS=  117.9 FOM= 0.79 TEST= 0
INDE 29 34 59 FOBS=   52.3 SIGMA=  4.8 PHAS=  -36.8 FOM= 0.48 TEST= 0
INDE 29 34 61 FOBS=   38.0 SIGMA=  8.8 PHAS=   84.0 FOM= 0.67 TEST= 0
INDE 29 34 63 FOBS=  109.5 SIGMA=  3.2 PHAS=   24.7 FOM= 0.93 TEST= 0
INDE 29 35 30 FOBS=  252.3 SIGMA=  1.0 PHAS= -171.4 FOM= 0.97 TEST= 0
INDE 29 35 32 FOBS=  139.8 SIGMA=  1.5 PHAS=  166.3 FOM= 0.96 TEST= 0
INDE 29 35 34 FOBS=  157.4 SIGMA=  1.2 PHAS=   18.5 FOM= 0.85 TEST= 0
INDE 29 35 36 FOBS=  141.2 SIGMA=  1.4 PHAS=   56.5 FOM= 0.89 TEST= 0
INDE 29 35 38 FOBS=  141.5 SIGMA=  1.4 PHAS=   27.3 FOM= 0.96 TEST= 0
INDE 29 35 40 FOBS=    0.0 SIGMA= 19.6 PHAS=    0.0 FOM= 0.00 TEST= 1
INDE 29 35 42 FOBS=   67.6 SIGMA=  2.7 PHAS=  174.4 FOM= 0.16 TEST= 1
INDE 29 35 44 FOBS=   35.9 SIGMA=  4.9 PHAS=   -8.4 FOM= 0.30 TEST= 0
INDE 29 35 46 FOBS=   62.8 SIGMA=  3.0 PHAS=  -58.0 FOM= 0.84 TEST= 0
INDE 29 35 48 FOBS=  105.5 SIGMA=  1.7 PHAS= -125.6 FOM= 0.92 TEST= 0
INDE 29 35 50 FOBS=   42.4 SIGMA=  4.1 PHAS=   72.7 FOM= 0.47 TEST= 0
INDE 29 35 52 FOBS=   64.0 SIGMA=  2.7 PHAS=  127.4 FOM= 0.56 TEST= 1
INDE 29 35 54 FOBS=    0.0 SIGMA= 20.5 PHAS=    0.0 FOM= 0.00 TEST= 0
INDE 29 35 56 FOBS=  102.5 SIGMA=  2.1 PHAS=  -14.4 FOM= 0.92 TEST= 0
INDE 29 35 58 FOBS=   66.2 SIGMA=  3.8 PHAS=   88.9 FOM= 0.44 TEST= 0
INDE 29 35 60 FOBS=   39.7 SIGMA=  6.9 PHAS= -105.6 FOM= 0.43 TEST= 0
INDE 29 35 62 FOBS=   91.4 SIGMA=  3.8 PHAS=  -29.9 FOM= 0.87 TEST= 0
INDE 29 36 29 FOBS=  275.6 SIGMA=  0.8 PHAS=   43.7 FOM= 0.97 TEST= 0
INDE 29 36 31 FOBS=  185.9 SIGMA=  1.1 PHAS=   90.7 FOM= 0.96 TEST= 0
INDE 29 36 33 FOBS=   81.9 SIGMA=  2.3 PHAS= -170.5 FOM= 0.84 TEST= 0
INDE 29 36 35 FOBS=   74.2 SIGMA=  2.5 PHAS=   -0.7 FOM= 0.67 TEST= 0
INDE 29 36 37 FOBS=  114.4 SIGMA=  1.7 PHAS=  -62.7 FOM= 0.86 TEST= 0
INDE 29 36 39 FOBS=    0.0 SIGMA= 19.0 PHAS=    0.0 FOM= 0.00 TEST= 0
INDE 29 36 41 FOBS=  102.8 SIGMA=  1.8 PHAS=  -50.0 FOM= 0.71 TEST= 1
INDE 29 36 43 FOBS=   37.5 SIGMA=  4.8 PHAS=  146.0 FOM= 0.43 TEST= 0
INDE 29 36 45 FOBS=   98.4 SIGMA=  1.9 PHAS=  161.8 FOM= 0.92 TEST= 0
INDE 29 36 47 FOBS=    0.0 SIGMA= 19.1 PHAS=    0.0 FOM= 0.00 TEST= 0
INDE 29 36 49 FOBS=    0.0 SIGMA= 19.0 PHAS=    0.0 FOM= 0.00 TEST= 0
INDE 29 36 51 FOBS=   36.3 SIGMA=  5.1 PHAS=  -44.6 FOM= 0.51 TEST= 0
INDE 29 36 53 FOBS=   50.8 SIGMA=  3.7 PHAS=  151.2 FOM= 0.73 TEST= 0
INDE 29 36 55 FOBS=   63.0 SIGMA=  3.2 PHAS= -174.4 FOM= 0.79 TEST= 0
INDE 29 36 57 FOBS=   17.4 SIGMA= 16.2 PHAS=  -44.2 FOM= 0.08 TEST= 0
INDE 29 36 59 FOBS=   56.4 SIGMA=  4.5 PHAS=  -55.9 FOM= 0.82 TEST= 0
INDE 29 36 61 FOBS=    0.0 SIGMA= 23.9 PHAS=    0.0 FOM= 0.00 TEST= 0
INDE 29 37 30 FOBS=    0.0 SIGMA= 20.0 PHAS=    0.0 FOM= 0.00 TEST= 0
INDE 29 37 32 FOBS=   30.5 SIGMA=  6.6 PHAS=   96.0 FOM= 0.47 TEST= 0
INDE 29 37 34 FOBS=   49.3 SIGMA=  3.7 PHAS=  120.0 FOM= 0.33 TEST= 0
INDE 29 37 36 FOBS=    0.0 SIGMA= 19.5 PHAS=    0.0 FOM= 0.00 TEST= 0
INDE 29 37 38 FOBS=    0.0 SIGMA= 19.5 PHAS=    0.0 FOM= 0.00 TEST= 0
INDE 29 37 40 FOBS=   77.8 SIGMA=  2.4 PHAS= -138.4 FOM= 0.90 TEST= 0
INDE 29 37 42 FOBS=   42.6 SIGMA=  4.3 PHAS=  178.2 FOM= 0.49 TEST= 1
INDE 29 37 44 FOBS=   89.7 SIGMA=  2.0 PHAS=    6.0 FOM= 0.81 TEST= 0
INDE 29 37 46 FOBS=   47.7 SIGMA=  3.7 PHAS=  -79.7 FOM= 0.76 TEST= 0
INDE 29 37 48 FOBS=   58.5 SIGMA=  3.0 PHAS=   91.6 FOM= 0.43 TEST= 0
INDE 29 37 50 FOBS=    0.0 SIGMA= 19.2 PHAS=    0.0 FOM= 0.00 TEST= 0
INDE 29 37 52 FOBS=    0.0 SIGMA= 19.7 PHAS=    0.0 FOM= 0.00 TEST= 0
INDE 29 37 54 FOBS=   69.2 SIGMA=  2.9 PHAS=  123.8 FOM= 0.88 TEST= 0
INDE 29 37 56 FOBS=   77.3 SIGMA=  2.8 PHAS=   -5.5 FOM= 0.83 TEST= 0
INDE 29 37 58 FOBS=    9.1 SIGMA= 34.8 PHAS=  -17.8 FOM= 0.11 TEST= 0
INDE 29 37 60 FOBS=   54.7 SIGMA=  4.7 PHAS= -165.6 FOM= 0.69 TEST= 0
INDE 29 38 29 FOBS=   86.6 SIGMA=  1.9 PHAS=  108.7 FOM= 0.56 TEST= 0
INDE 29 38 31 FOBS=   73.6 SIGMA=  2.4 PHAS=  137.1 FOM= 0.93 TEST= 0
INDE 29 38 33 FOBS=   73.2 SIGMA=  2.6 PHAS= -153.6 FOM= 0.69 TEST= 0
```

*FIG. 12A - 529*

```
INDE  29  38  35  FOBS=    53.8  SIGMA=   3.2  PHAS=   18.5  FOM=  0.82  TEST=  0
INDE  29  38  37  FOBS=     0.0  SIGMA=  20.7  PHAS=    0.0  FOM=  0.00  TEST=  0
INDE  29  38  39  FOBS=    45.7  SIGMA=   4.0  PHAS=  139.9  FOM=  0.84  TEST=  0
INDE  29  38  41  FOBS=    45.8  SIGMA=   4.2  PHAS=   87.6  FOM=  0.52  TEST=  0
INDE  29  38  43  FOBS=    58.0  SIGMA=   3.1  PHAS=  173.1  FOM=  0.41  TEST=  1
INDE  29  38  45  FOBS=   167.7  SIGMA=   1.2  PHAS=  168.8  FOM=  0.96  TEST=  0
INDE  29  38  47  FOBS=    98.7  SIGMA=   1.8  PHAS=  -14.4  FOM=  0.86  TEST=  0
INDE  29  38  49  FOBS=    81.0  SIGMA=   2.2  PHAS=   33.1  FOM=  0.87  TEST=  0
INDE  29  38  51  FOBS=     0.0  SIGMA=  18.7  PHAS=    0.0  FOM=  0.00  TEST=  0
INDE  29  38  53  FOBS=    66.7  SIGMA=   3.3  PHAS=   52.2  FOM=  0.86  TEST=  0
INDE  29  38  55  FOBS=    66.7  SIGMA=   3.3  PHAS=  141.9  FOM=  0.65  TEST=  0
INDE  29  38  57  FOBS=     0.0  SIGMA=  22.4  PHAS=    0.0  FOM=  0.00  TEST=  0
INDE  29  38  59  FOBS=    26.0  SIGMA=  15.3  PHAS= -126.3  FOM=  0.01  TEST=  0
INDE  29  38  61  FOBS=     0.0  SIGMA=  26.2  PHAS=    0.0  FOM=  0.00  TEST=  0
INDE  29  39  30  FOBS=   128.7  SIGMA=   1.3  PHAS=   62.5  FOM=  0.95  TEST=  0
INDE  29  39  32  FOBS=    68.4  SIGMA=   2.6  PHAS=   72.1  FOM=  0.73  TEST=  0
INDE  29  39  34  FOBS=     0.0  SIGMA=  20.0  PHAS=    0.0  FOM=  0.00  TEST=  0
INDE  29  39  36  FOBS=    95.1  SIGMA=   1.7  PHAS=  -66.7  FOM=  0.81  TEST=  0
INDE  29  39  38  FOBS=    74.6  SIGMA=   2.2  PHAS=   46.7  FOM=  0.92  TEST=  0
INDE  29  39  40  FOBS=    27.3  SIGMA=   6.3  PHAS=  -81.7  FOM=  0.43  TEST=  0
INDE  29  39  42  FOBS=    22.1  SIGMA=   9.0  PHAS=  161.8  FOM=  0.12  TEST=  0
INDE  29  39  44  FOBS=    77.9  SIGMA=   2.4  PHAS=   51.4  FOM=  0.84  TEST=  0
INDE  29  39  46  FOBS=    80.1  SIGMA=   2.3  PHAS=  -81.2  FOM=  0.90  TEST=  0
INDE  29  39  48  FOBS=    90.3  SIGMA=   2.0  PHAS=  -99.1  FOM=  0.68  TEST=  0
INDE  29  39  50  FOBS=     0.0  SIGMA=  18.8  PHAS=    0.0  FOM=  0.00  TEST=  0
INDE  29  39  52  FOBS=   118.9  SIGMA=   1.9  PHAS=   18.6  FOM=  0.96  TEST=  0
INDE  29  39  54  FOBS=    66.1  SIGMA=   3.3  PHAS=   24.6  FOM=  0.38  TEST=  0
INDE  29  39  56  FOBS=    30.1  SIGMA=   7.7  PHAS=   69.9  FOM=  0.37  TEST=  0
INDE  29  39  58  FOBS=     0.0  SIGMA=  21.7  PHAS=    0.0  FOM=  0.00  TEST=  0
INDE  29  39  60  FOBS=    80.1  SIGMA=   4.4  PHAS=  -60.0  FOM=  0.92  TEST=  0
INDE  29  40  29  FOBS=     0.0  SIGMA=  18.4  PHAS=    0.0  FOM=  0.00  TEST=  0
INDE  29  40  31  FOBS=     0.0  SIGMA=  18.9  PHAS=    0.0  FOM=  0.00  TEST=  1
INDE  29  40  33  FOBS=   150.4  SIGMA=   1.3  PHAS=  -86.1  FOM=  0.95  TEST=  0
INDE  29  40  35  FOBS=    78.4  SIGMA=   2.1  PHAS=  -58.6  FOM=  0.80  TEST=  0
INDE  29  40  37  FOBS=    54.4  SIGMA=   3.0  PHAS= -119.2  FOM=  0.84  TEST=  0
INDE  29  40  39  FOBS=    10.5  SIGMA=  16.9  PHAS=  -54.6  FOM=  0.30  TEST=  0
INDE  29  40  41  FOBS=   108.1  SIGMA=   1.6  PHAS=  123.5  FOM=  0.86  TEST=  0
INDE  29  40  43  FOBS=    56.0  SIGMA=   2.9  PHAS=  108.7  FOM=  0.13  TEST=  1
INDE  29  40  45  FOBS=    81.6  SIGMA=   2.0  PHAS= -166.2  FOM=  0.93  TEST=  0
INDE  29  40  47  FOBS=     7.2  SIGMA=  24.6  PHAS= -125.3  FOM=  0.10  TEST=  0
INDE  29  40  49  FOBS=     0.0  SIGMA=  19.4  PHAS=    0.0  FOM=  0.00  TEST=  0
INDE  29  40  51  FOBS=     0.0  SIGMA=  19.9  PHAS=    0.0  FOM=  0.00  TEST=  0
INDE  29  40  53  FOBS=   126.5  SIGMA=   1.8  PHAS=  -45.7  FOM=  0.97  TEST=  0
INDE  29  40  55  FOBS=    66.9  SIGMA=   3.3  PHAS= -172.6  FOM=  0.76  TEST=  0
INDE  29  40  57  FOBS=     0.0  SIGMA=  21.0  PHAS=    0.0  FOM=  0.00  TEST=  0
INDE  29  40  59  FOBS=    88.9  SIGMA=   2.8  PHAS= -169.6  FOM=  0.91  TEST=  0
INDE  29  41  30  FOBS=    19.2  SIGMA=   8.7  PHAS= -125.5  FOM=  0.46  TEST=  0
INDE  29  41  32  FOBS=     0.0  SIGMA=  20.1  PHAS=    0.0  FOM=  0.00  TEST=  0
INDE  29  41  34  FOBS=    24.6  SIGMA=   7.6  PHAS= -154.9  FOM=  0.30  TEST=  1
INDE  29  41  36  FOBS=    56.6  SIGMA=   2.9  PHAS=  -65.8  FOM=  0.03  TEST=  0
INDE  29  41  38  FOBS=    78.3  SIGMA=   2.1  PHAS=  134.6  FOM=  0.11  TEST=  1
INDE  29  41  40  FOBS=    54.9  SIGMA=   3.0  PHAS=  -41.0  FOM=  0.80  TEST=  0
INDE  29  41  42  FOBS=   158.3  SIGMA=   1.1  PHAS=  -40.5  FOM=  0.92  TEST=  0
INDE  29  41  44  FOBS=    90.7  SIGMA=   1.9  PHAS=   46.1  FOM=  0.91  TEST=  0
INDE  29  41  46  FOBS=    34.1  SIGMA=   5.4  PHAS=  123.6  FOM=  0.61  TEST=  0
INDE  29  41  48  FOBS=    54.5  SIGMA=   3.0  PHAS=   99.1  FOM=  0.35  TEST=  0
INDE  29  41  50  FOBS=    52.5  SIGMA=   3.6  PHAS=  -49.7  FOM=  0.72  TEST=  0
INDE  29  41  52  FOBS=    64.8  SIGMA=   3.4  PHAS=  -61.2  FOM=  0.82  TEST=  0
INDE  29  41  54  FOBS=    53.3  SIGMA=   4.9  PHAS=   99.4  FOM=  0.75  TEST=  0
INDE  29  41  56  FOBS=    77.9  SIGMA=   2.9  PHAS=  138.9  FOM=  0.88  TEST=  0
INDE  29  41  58  FOBS=    37.7  SIGMA=   6.4  PHAS=   99.4  FOM=  0.51  TEST=  0
INDE  29  42  29  FOBS=    96.2  SIGMA=   1.7  PHAS=  114.9  FOM=  0.94  TEST=  0
INDE  29  42  31  FOBS=   153.1  SIGMA=   1.1  PHAS=  150.6  FOM=  0.89  TEST=  0
INDE  29  42  33  FOBS=    76.5  SIGMA=   2.4  PHAS= -109.4  FOM=  0.85  TEST=  0
INDE  29  42  35  FOBS=    79.9  SIGMA=   2.2  PHAS=  -44.4  FOM=  0.88  TEST=  0
INDE  29  42  37  FOBS=    91.1  SIGMA=   1.8  PHAS= -106.0  FOM=  0.91  TEST=  0
INDE  29  42  39  FOBS=    79.6  SIGMA=   2.1  PHAS=  -49.2  FOM=  0.77  TEST=  0
INDE  29  42  41  FOBS=    33.8  SIGMA=   4.9  PHAS= -141.5  FOM=  0.55  TEST=  0
INDE  29  42  43  FOBS=   104.5  SIGMA=   1.6  PHAS=  -48.5  FOM=  0.94  TEST=  0
INDE  29  42  45  FOBS=    34.8  SIGMA=   5.4  PHAS=  -42.9  FOM=  0.73  TEST=  0
```

*FIG. 12A - 530*

```
INDE 29 42 47 FOBS=   77.7 SIGMA=  2.1 PHAS=  -53.0 FOM= 0.89 TEST= 0
INDE 29 42 49 FOBS=    0.0 SIGMA= 20.7 PHAS=    0.0 FOM= 0.00 TEST= 0
INDE 29 42 51 FOBS=   66.0 SIGMA=  2.9 PHAS= -142.5 FOM= 0.47 TEST= 0
INDE 29 42 53 FOBS=   90.3 SIGMA=  2.3 PHAS=  -46.6 FOM= 0.94 TEST= 0
INDE 29 42 55 FOBS=    0.0 SIGMA= 23.1 PHAS=    0.0 FOM= 0.00 TEST= 0
INDE 29 42 57 FOBS=   54.4 SIGMA=  4.6 PHAS=   47.3 FOM= 0.92 TEST= 0
INDE 29 43 30 FOBS=   71.8 SIGMA=  2.4 PHAS=  -75.2 FOM= 0.92 TEST= 0
INDE 29 43 32 FOBS=   55.5 SIGMA=  3.2 PHAS=   73.5 FOM= 0.71 TEST= 0
INDE 29 43 34 FOBS=   23.6 SIGMA=  8.8 PHAS=  -63.2 FOM= 0.48 TEST= 0
INDE 29 43 36 FOBS=   45.4 SIGMA=  3.9 PHAS=   58.7 FOM= 0.32 TEST= 0
INDE 29 43 38 FOBS=   59.5 SIGMA=  2.8 PHAS=  150.8 FOM= 0.43 TEST= 0
INDE 29 43 40 FOBS=    0.0 SIGMA= 18.0 PHAS=    0.0 FOM= 0.00 TEST= 0
INDE 29 43 42 FOBS=   70.6 SIGMA=  2.4 PHAS=  -80.1 FOM= 0.79 TEST= 0
INDE 29 43 44 FOBS=   28.5 SIGMA=  6.6 PHAS=  147.3 FOM= 0.45 TEST= 0
INDE 29 43 46 FOBS=   30.6 SIGMA=  5.4 PHAS=   73.3 FOM= 0.53 TEST= 0
INDE 29 43 48 FOBS=   55.3 SIGMA=  3.3 PHAS=  -28.3 FOM= 0.52 TEST= 0
INDE 29 43 50 FOBS=   25.8 SIGMA=  8.5 PHAS=  -95.6 FOM= 0.55 TEST= 0
INDE 29 43 52 FOBS=   66.3 SIGMA=  3.0 PHAS=  -96.8 FOM= 0.86 TEST= 0
INDE 29 43 54 FOBS=    0.0 SIGMA= 19.6 PHAS=    0.0 FOM= 0.00 TEST= 1
INDE 29 43 56 FOBS=    0.0 SIGMA= 20.4 PHAS=    0.0 FOM= 0.00 TEST= 0
INDE 29 44 29 FOBS=  152.2 SIGMA=  1.1 PHAS=  146.1 FOM= 0.93 TEST= 0
INDE 29 44 31 FOBS=   82.2 SIGMA=  2.0 PHAS=  164.5 FOM= 0.92 TEST= 0
INDE 29 44 33 FOBS=    0.0 SIGMA= 20.6 PHAS=    0.0 FOM= 0.00 TEST= 0
INDE 29 44 35 FOBS=   55.6 SIGMA=  3.2 PHAS=    5.6 FOM= 0.65 TEST= 0
INDE 29 44 37 FOBS=   94.0 SIGMA=  1.8 PHAS=  -70.7 FOM= 0.91 TEST= 0
INDE 29 44 39 FOBS=    0.0 SIGMA= 18.3 PHAS=    0.0 FOM= 0.00 TEST= 0
INDE 29 44 41 FOBS=   44.5 SIGMA=  3.7 PHAS= -126.0 FOM= 0.72 TEST= 0
INDE 29 44 43 FOBS=   85.2 SIGMA=  2.0 PHAS=  -19.8 FOM= 0.87 TEST= 0
INDE 29 44 45 FOBS=  123.9 SIGMA=  1.5 PHAS=    5.0 FOM= 0.92 TEST= 0
INDE 29 44 47 FOBS=   83.0 SIGMA=  2.2 PHAS=  -98.2 FOM= 0.90 TEST= 0
INDE 29 44 49 FOBS=   66.7 SIGMA=  2.8 PHAS=  -95.3 FOM= 0.56 TEST= 0
INDE 29 44 51 FOBS=   67.0 SIGMA=  3.0 PHAS= -177.8 FOM= 0.77 TEST= 0
INDE 29 44 53 FOBS=    0.0 SIGMA= 19.8 PHAS=    0.0 FOM= 0.00 TEST= 1
INDE 29 44 55 FOBS=    0.0 SIGMA= 20.5 PHAS=    0.0 FOM= 0.00 TEST= 1
INDE 29 44 57 FOBS=   34.3 SIGMA=  6.9 PHAS=   75.3 FOM= 0.23 TEST= 0
INDE 29 45 30 FOBS=   53.5 SIGMA=  3.1 PHAS=   45.2 FOM= 0.79 TEST= 0
INDE 29 45 32 FOBS=   72.2 SIGMA=  2.3 PHAS=   14.8 FOM= 0.88 TEST= 0
INDE 29 45 34 FOBS=  128.0 SIGMA=  1.5 PHAS=  -30.0 FOM= 0.95 TEST= 0
INDE 29 45 36 FOBS=   30.1 SIGMA=  5.9 PHAS=  -87.4 FOM= 0.28 TEST= 0
INDE 29 45 38 FOBS=   41.3 SIGMA=  4.0 PHAS=  -35.2 FOM= 0.20 TEST= 0
INDE 29 45 40 FOBS=   86.9 SIGMA=  1.9 PHAS=  -39.1 FOM= 0.82 TEST= 0
INDE 29 45 42 FOBS=   52.2 SIGMA=  3.2 PHAS=  178.4 FOM= 0.72 TEST= 0
INDE 29 45 44 FOBS=   98.1 SIGMA=  1.9 PHAS= -149.6 FOM= 0.92 TEST= 0
INDE 29 45 46 FOBS=   71.5 SIGMA=  2.6 PHAS=  158.5 FOM= 0.83 TEST= 0
INDE 29 45 48 FOBS=   64.0 SIGMA=  2.9 PHAS= -121.3 FOM= 0.79 TEST= 0
INDE 29 45 50 FOBS=   49.5 SIGMA=  3.7 PHAS=   65.7 FOM= 0.36 TEST= 0
INDE 29 45 52 FOBS=    0.0 SIGMA= 20.4 PHAS=    0.0 FOM= 0.00 TEST= 0
INDE 29 45 54 FOBS=    0.0 SIGMA= 22.1 PHAS=    0.0 FOM= 0.00 TEST= 1
INDE 29 45 56 FOBS=   12.7 SIGMA= 20.0 PHAS=   45.8 FOM= 0.16 TEST= 0
INDE 29 46 29 FOBS=  147.5 SIGMA=  1.1 PHAS=  157.0 FOM= 0.96 TEST= 0
INDE 29 46 31 FOBS=    0.0 SIGMA= 18.6 PHAS=    0.0 FOM= 0.00 TEST= 0
INDE 29 46 33 FOBS=  101.2 SIGMA=  1.8 PHAS= -122.3 FOM= 0.63 TEST= 1
INDE 29 46 35 FOBS=   46.7 SIGMA=  3.8 PHAS= -152.1 FOM= 0.71 TEST= 0
INDE 29 46 37 FOBS=   48.3 SIGMA=  3.7 PHAS=  -81.5 FOM= 0.74 TEST= 0
INDE 29 46 39 FOBS=   97.0 SIGMA=  1.8 PHAS= -135.3 FOM= 0.89 TEST= 0
INDE 29 46 41 FOBS=  119.4 SIGMA=  1.4 PHAS=   68.7 FOM= 0.68 TEST= 0
INDE 29 46 43 FOBS=   44.6 SIGMA=  4.4 PHAS=   91.0 FOM= 0.79 TEST= 0
INDE 29 46 45 FOBS=   71.4 SIGMA=  2.6 PHAS=   41.8 FOM= 0.85 TEST= 0
INDE 29 46 47 FOBS=   37.6 SIGMA=  5.7 PHAS=  157.6 FOM= 0.47 TEST= 0
INDE 29 46 49 FOBS=   73.6 SIGMA=  2.6 PHAS=  -82.5 FOM= 0.68 TEST= 0
INDE 29 46 51 FOBS=   37.7 SIGMA=  5.3 PHAS=   -1.2 FOM= 0.57 TEST= 0
INDE 29 46 53 FOBS=   20.2 SIGMA= 10.4 PHAS=   28.5 FOM= 0.44 TEST= 0
INDE 29 46 55 FOBS=   38.2 SIGMA=  6.5 PHAS= -112.6 FOM= 0.04 TEST= 0
INDE 29 47 30 FOBS=   61.9 SIGMA=  2.6 PHAS=   89.8 FOM= 0.83 TEST= 0
INDE 29 47 32 FOBS=   79.8 SIGMA=  2.1 PHAS=  -40.6 FOM= 0.91 TEST= 0
INDE 29 47 34 FOBS=   92.8 SIGMA=  2.0 PHAS=   81.6 FOM= 0.88 TEST= 0
INDE 29 47 36 FOBS=   50.9 SIGMA=  3.5 PHAS=   71.6 FOM= 0.59 TEST= 0
INDE 29 47 38 FOBS=   43.5 SIGMA=  4.3 PHAS=   46.2 FOM= 0.71 TEST= 0
INDE 29 47 40 FOBS=  107.1 SIGMA=  1.6 PHAS=   20.1 FOM= 0.95 TEST= 0
INDE 29 47 42 FOBS=  113.8 SIGMA=  1.7 PHAS=  -77.0 FOM= 0.42 TEST= 1
```

*FIG. 12A - 531*

| | | | | | | | | | | | | |
|---|---|---|---|---|---|---|---|---|---|---|---|---|
| INDE | 29 | 47 | 44 | FOBS= | 55.0 | SIGMA= | 3.4 | PHAS= | 152.7 | FOM= | 0.36 | TEST= 0 |
| INDE | 29 | 47 | 46 | FOBS= | 71.3 | SIGMA= | 2.6 | PHAS= | -0.9 | FOM= | 0.65 | TEST= 0 |
| INDE | 29 | 47 | 48 | FOBS= | 64.7 | SIGMA= | 2.9 | PHAS= | -89.1 | FOM= | 0.89 | TEST= 0 |
| INDE | 29 | 47 | 50 | FOBS= | 31.2 | SIGMA= | 6.9 | PHAS= | -174.3 | FOM= | 0.57 | TEST= 0 |
| INDE | 29 | 47 | 52 | FOBS= | 95.6 | SIGMA= | 2.2 | PHAS= | -58.7 | FOM= | 0.91 | TEST= 0 |
| INDE | 29 | 47 | 54 | FOBS= | 51.3 | SIGMA= | 4.7 | PHAS= | -161.4 | FOM= | 0.77 | TEST= 0 |
| INDE | 29 | 48 | 29 | FOBS= | 115.9 | SIGMA= | 1.4 | PHAS= | 111.9 | FOM= | 0.86 | TEST= 0 |
| INDE | 29 | 48 | 31 | FOBS= | 84.0 | SIGMA= | 1.9 | PHAS= | -178.3 | FOM= | 0.87 | TEST= 0 |
| INDE | 29 | 48 | 33 | FOBS= | 27.5 | SIGMA= | 6.8 | PHAS= | -88.7 | FOM= | 0.39 | TEST= 0 |
| INDE | 29 | 48 | 35 | FOBS= | 48.0 | SIGMA= | 3.8 | PHAS= | -5.7 | FOM= | 0.53 | TEST= 0 |
| INDE | 29 | 48 | 37 | FOBS= | 83.4 | SIGMA= | 2.2 | PHAS= | -72.9 | FOM= | 0.92 | TEST= 0 |
| INDE | 29 | 48 | 39 | FOBS= | 153.1 | SIGMA= | 1.3 | PHAS= | -72.0 | FOM= | 0.95 | TEST= 0 |
| INDE | 29 | 48 | 41 | FOBS= | 63.4 | SIGMA= | 2.9 | PHAS= | -96.7 | FOM= | 0.88 | TEST= 0 |
| INDE | 29 | 48 | 43 | FOBS= | 44.9 | SIGMA= | 4.3 | PHAS= | -82.7 | FOM= | 0.40 | TEST= 0 |
| INDE | 29 | 48 | 45 | FOBS= | 35.2 | SIGMA= | 5.9 | PHAS= | -90.2 | FOM= | 0.63 | TEST= 0 |
| INDE | 29 | 48 | 47 | FOBS= | 117.7 | SIGMA= | 1.7 | PHAS= | 162.8 | FOM= | 0.95 | TEST= 0 |
| INDE | 29 | 48 | 49 | FOBS= | 0.0 | SIGMA= | 21.8 | PHAS= | 0.0 | FOM= | 0.00 | TEST= 0 |
| INDE | 29 | 48 | 51 | FOBS= | 104.7 | SIGMA= | 2.2 | PHAS= | 155.8 | FOM= | 0.94 | TEST= 0 |
| INDE | 29 | 48 | 53 | FOBS= | 69.3 | SIGMA= | 3.8 | PHAS= | 170.1 | FOM= | 0.85 | TEST= 0 |
| INDE | 29 | 49 | 30 | FOBS= | 68.8 | SIGMA= | 2.3 | PHAS= | 39.5 | FOM= | 0.62 | TEST= 0 |
| INDE | 29 | 49 | 32 | FOBS= | 46.2 | SIGMA= | 3.4 | PHAS= | -1.3 | FOM= | 0.66 | TEST= 0 |
| INDE | 29 | 49 | 34 | FOBS= | 0.0 | SIGMA= | 19.2 | PHAS= | 0.0 | FOM= | 0.00 | TEST= 1 |
| INDE | 29 | 49 | 36 | FOBS= | 138.3 | SIGMA= | 1.4 | PHAS= | 137.6 | FOM= | 0.95 | TEST= 0 |
| INDE | 29 | 49 | 38 | FOBS= | 62.0 | SIGMA= | 3.3 | PHAS= | -165.5 | FOM= | 0.76 | TEST= 0 |
| INDE | 29 | 49 | 40 | FOBS= | 69.2 | SIGMA= | 2.7 | PHAS= | 154.7 | FOM= | 0.83 | TEST= 0 |
| INDE | 29 | 49 | 42 | FOBS= | 0.0 | SIGMA= | 20.1 | PHAS= | 0.0 | FOM= | 0.00 | TEST= 0 |
| INDE | 29 | 49 | 44 | FOBS= | 20.8 | SIGMA= | 9.5 | PHAS= | -72.5 | FOM= | 0.18 | TEST= 0 |
| INDE | 29 | 49 | 46 | FOBS= | 24.2 | SIGMA= | 9.5 | PHAS= | -168.4 | FOM= | 0.52 | TEST= 0 |
| INDE | 29 | 49 | 48 | FOBS= | 55.4 | SIGMA= | 4.6 | PHAS= | 37.9 | FOM= | 0.58 | TEST= 0 |
| INDE | 29 | 49 | 50 | FOBS= | 75.3 | SIGMA= | 3.2 | PHAS= | 76.0 | FOM= | 0.92 | TEST= 0 |
| INDE | 29 | 49 | 52 | FOBS= | 25.7 | SIGMA= | 12.5 | PHAS= | 62.0 | FOM= | 0.80 | TEST= 0 |
| INDE | 29 | 50 | 29 | FOBS= | 16.7 | SIGMA= | 9.8 | PHAS= | -168.5 | FOM= | 0.16 | TEST= 0 |
| INDE | 29 | 50 | 31 | FOBS= | 151.8 | SIGMA= | 1.1 | PHAS= | -92.0 | FOM= | 0.93 | TEST= 0 |
| INDE | 29 | 50 | 33 | FOBS= | 56.6 | SIGMA= | 2.9 | PHAS= | -145.0 | FOM= | 0.64 | TEST= 0 |
| INDE | 29 | 50 | 35 | FOBS= | 59.0 | SIGMA= | 3.2 | PHAS= | 15.1 | FOM= | 0.81 | TEST= 0 |
| INDE | 29 | 50 | 37 | FOBS= | 63.2 | SIGMA= | 3.2 | PHAS= | -75.8 | FOM= | 0.14 | TEST= 1 |
| INDE | 29 | 50 | 39 | FOBS= | 41.5 | SIGMA= | 5.3 | PHAS= | 111.2 | FOM= | 0.23 | TEST= 0 |
| INDE | 29 | 50 | 41 | FOBS= | 48.7 | SIGMA= | 4.0 | PHAS= | 4.7 | FOM= | 0.63 | TEST= 0 |
| INDE | 29 | 50 | 43 | FOBS= | 47.3 | SIGMA= | 4.5 | PHAS= | 35.4 | FOM= | 0.63 | TEST= 0 |
| INDE | 29 | 50 | 45 | FOBS= | 6.2 | SIGMA= | 34.3 | PHAS= | -135.6 | FOM= | 0.20 | TEST= 0 |
| INDE | 29 | 50 | 47 | FOBS= | 123.2 | SIGMA= | 1.9 | PHAS= | 170.5 | FOM= | 0.52 | TEST= 1 |
| INDE | 29 | 50 | 49 | FOBS= | 60.3 | SIGMA= | 4.1 | PHAS= | 27.4 | FOM= | 0.89 | TEST= 0 |
| INDE | 29 | 50 | 51 | FOBS= | 72.5 | SIGMA= | 3.4 | PHAS= | -46.2 | FOM= | 0.67 | TEST= 0 |
| INDE | 29 | 51 | 30 | FOBS= | 57.3 | SIGMA= | 2.8 | PHAS= | 129.7 | FOM= | 0.74 | TEST= 0 |
| INDE | 29 | 51 | 32 | FOBS= | 88.8 | SIGMA= | 1.8 | PHAS= | 100.6 | FOM= | 0.92 | TEST= 0 |
| INDE | 29 | 51 | 34 | FOBS= | 74.3 | SIGMA= | 2.9 | PHAS= | -114.1 | FOM= | 0.39 | TEST= 1 |
| INDE | 29 | 51 | 36 | FOBS= | 52.7 | SIGMA= | 4.4 | PHAS= | 64.5 | FOM= | 0.78 | TEST= 0 |
| INDE | 29 | 51 | 38 | FOBS= | 135.8 | SIGMA= | 1.7 | PHAS= | 34.2 | FOM= | 0.95 | TEST= 0 |
| INDE | 29 | 51 | 40 | FOBS= | 46.7 | SIGMA= | 5.2 | PHAS= | -33.9 | FOM= | 0.58 | TEST= 0 |
| INDE | 29 | 51 | 42 | FOBS= | 63.3 | SIGMA= | 3.4 | PHAS= | 32.0 | FOM= | 0.85 | TEST= 0 |
| INDE | 29 | 51 | 44 | FOBS= | 91.9 | SIGMA= | 2.4 | PHAS= | -36.8 | FOM= | 0.87 | TEST= 0 |
| INDE | 29 | 51 | 46 | FOBS= | 31.3 | SIGMA= | 7.5 | PHAS= | 133.0 | FOM= | 0.53 | TEST= 0 |
| INDE | 29 | 51 | 48 | FOBS= | 113.9 | SIGMA= | 2.0 | PHAS= | 44.9 | FOM= | 0.97 | TEST= 0 |
| INDE | 29 | 51 | 50 | FOBS= | 29.7 | SIGMA= | 8.3 | PHAS= | 164.6 | FOM= | 0.43 | TEST= 0 |
| INDE | 29 | 52 | 29 | FOBS= | 63.5 | SIGMA= | 2.7 | PHAS= | 92.5 | FOM= | 0.90 | TEST= 0 |
| INDE | 29 | 52 | 31 | FOBS= | 112.5 | SIGMA= | 1.6 | PHAS= | -52.1 | FOM= | 0.95 | TEST= 0 |
| INDE | 29 | 52 | 33 | FOBS= | 37.1 | SIGMA= | 6.0 | PHAS= | 32.2 | FOM= | 0.31 | TEST= 0 |
| INDE | 29 | 52 | 35 | FOBS= | 47.1 | SIGMA= | 4.9 | PHAS= | -117.5 | FOM= | 0.44 | TEST= 0 |
| INDE | 29 | 52 | 37 | FOBS= | 100.3 | SIGMA= | 2.4 | PHAS= | -95.3 | FOM= | 0.95 | TEST= 0 |
| INDE | 29 | 52 | 39 | FOBS= | 119.6 | SIGMA= | 2.1 | PHAS= | -115.1 | FOM= | 0.96 | TEST= 0 |
| INDE | 29 | 52 | 41 | FOBS= | 67.5 | SIGMA= | 3.4 | PHAS= | -30.7 | FOM= | 0.82 | TEST= 0 |
| INDE | 29 | 52 | 43 | FOBS= | 25.5 | SIGMA= | 9.6 | PHAS= | -76.1 | FOM= | 0.25 | TEST= 0 |
| INDE | 29 | 52 | 45 | FOBS= | 59.5 | SIGMA= | 3.7 | PHAS= | -142.1 | FOM= | 0.63 | TEST= 1 |
| INDE | 29 | 52 | 47 | FOBS= | 57.8 | SIGMA= | 3.9 | PHAS= | -69.7 | FOM= | 0.91 | TEST= 0 |
| INDE | 29 | 52 | 49 | FOBS= | 129.5 | SIGMA= | 2.0 | PHAS= | 51.6 | FOM= | 0.34 | TEST= 1 |
| INDE | 29 | 53 | 30 | FOBS= | 28.4 | SIGMA= | 7.7 | PHAS= | -1.0 | FOM= | 0.37 | TEST= 0 |
| INDE | 29 | 53 | 32 | FOBS= | 41.8 | SIGMA= | 4.9 | PHAS= | 82.9 | FOM= | 0.47 | TEST= 0 |
| INDE | 29 | 53 | 34 | FOBS= | 5.1 | SIGMA= | 45.4 | PHAS= | -38.5 | FOM= | 0.08 | TEST= 0 |
| INDE | 29 | 53 | 36 | FOBS= | 128.8 | SIGMA= | 2.2 | PHAS= | 136.7 | FOM= | 0.93 | TEST= 0 |
| INDE | 29 | 53 | 38 | FOBS= | 99.8 | SIGMA= | 2.5 | PHAS= | 120.9 | FOM= | 0.93 | TEST= 0 |

*FIG. 12A - 532*

```
INDE  29  53  40  FOBS=   24.8  SIGMA=  12.6  PHAS=   144.8  FOM=  0.32  TEST= 0
INDE  29  53  42  FOBS=   11.5  SIGMA=  18.6  PHAS=    -0.8  FOM=  0.25  TEST= 0
INDE  29  53  44  FOBS=    0.0  SIGMA=  22.5  PHAS=     0.0  FOM=  0.00  TEST= 0
INDE  29  53  46  FOBS=   72.1  SIGMA=   3.1  PHAS=   133.6  FOM=  0.90  TEST= 0
INDE  29  53  48  FOBS=   86.3  SIGMA=   2.7  PHAS=   -14.5  FOM=  0.01  TEST= 1
INDE  29  54  29  FOBS=   66.6  SIGMA=   3.3  PHAS=   168.1  FOM=  0.87  TEST= 0
INDE  29  54  31  FOBS=   75.5  SIGMA=   2.8  PHAS=   -54.7  FOM=  0.88  TEST= 0
INDE  29  54  33  FOBS=   77.4  SIGMA=   2.7  PHAS=   -89.3  FOM=  0.85  TEST= 0
INDE  29  54  35  FOBS=   67.8  SIGMA=   3.5  PHAS=    77.7  FOM=  0.83  TEST= 0
INDE  29  54  37  FOBS=    0.0  SIGMA=  22.8  PHAS=     0.0  FOM=  0.00  TEST= 0
INDE  29  54  39  FOBS=   31.4  SIGMA=   9.4  PHAS=  -107.5  FOM=  0.45  TEST= 0
INDE  29  54  41  FOBS=   38.9  SIGMA=   6.4  PHAS=  -161.0  FOM=  0.35  TEST= 0
INDE  29  54  43  FOBS=   22.7  SIGMA=  10.1  PHAS=  -143.0  FOM=  0.08  TEST= 0
INDE  29  54  45  FOBS=   23.4  SIGMA=   9.5  PHAS=   -23.8  FOM=  0.33  TEST= 0
INDE  29  54  47  FOBS=   29.1  SIGMA=   7.9  PHAS=   -41.7  FOM=  0.60  TEST= 0
INDE  29  55  30  FOBS=    0.0  SIGMA=  21.8  PHAS=     0.0  FOM=  0.00  TEST= 0
INDE  29  55  32  FOBS=   22.0  SIGMA=  10.3  PHAS=   -37.0  FOM=  0.22  TEST= 0
INDE  29  55  34  FOBS=   42.0  SIGMA=   5.5  PHAS=    54.0  FOM=  0.44  TEST= 0
INDE  29  55  36  FOBS=    0.0  SIGMA=  23.0  PHAS=     0.0  FOM=  0.00  TEST= 0
INDE  29  55  38  FOBS=   79.5  SIGMA=   3.1  PHAS=   119.3  FOM=  0.15  TEST= 1
INDE  29  55  40  FOBS=    0.0  SIGMA=  25.0  PHAS=     0.0  FOM=  0.00  TEST= 0
INDE  29  55  42  FOBS=    0.0  SIGMA=  23.5  PHAS=     0.0  FOM=  0.00  TEST= 0
INDE  29  55  44  FOBS=    0.0  SIGMA=  21.9  PHAS=     0.0  FOM=  0.00  TEST= 0
INDE  29  55  46  FOBS=    0.0  SIGMA=  24.4  PHAS=     0.0  FOM=  0.00  TEST= 0
INDE  29  56  29  FOBS=   69.7  SIGMA=   3.5  PHAS=    77.5  FOM=  0.63  TEST= 0
INDE  29  56  31  FOBS=    0.0  SIGMA=  22.1  PHAS=     0.0  FOM=  0.00  TEST= 0
INDE  29  56  33  FOBS=  118.4  SIGMA=   1.9  PHAS=  -134.5  FOM=  0.88  TEST= 0
INDE  29  56  35  FOBS=   28.6  SIGMA=   8.9  PHAS=  -171.4  FOM=  0.35  TEST= 0
INDE  29  56  37  FOBS=   12.7  SIGMA=  19.0  PHAS=   -66.0  FOM=  0.38  TEST= 0
INDE  29  56  39  FOBS=    0.0  SIGMA=  22.1  PHAS=     0.0  FOM=  0.00  TEST= 0
INDE  29  56  41  FOBS=   88.3  SIGMA=   2.9  PHAS=   100.7  FOM=  0.90  TEST= 0
INDE  29  56  43  FOBS=   55.8  SIGMA=   4.3  PHAS=   167.5  FOM=  0.88  TEST= 0
INDE  29  56  45  FOBS=    0.0  SIGMA=  25.6  PHAS=     0.0  FOM=  0.00  TEST= 0
INDE  29  57  30  FOBS=    0.0  SIGMA=  23.3  PHAS=     0.0  FOM=  0.00  TEST= 0
INDE  29  57  32  FOBS=   65.1  SIGMA=   3.8  PHAS=  -171.3  FOM=  0.45  TEST= 0
INDE  29  57  34  FOBS=   73.0  SIGMA=   3.0  PHAS=   108.5  FOM=  0.76  TEST= 0
INDE  29  57  36  FOBS=   28.3  SIGMA=   8.4  PHAS=   121.5  FOM=  0.26  TEST= 0
INDE  29  57  38  FOBS=   41.1  SIGMA=   6.0  PHAS=   167.1  FOM=  0.05  TEST= 1
INDE  29  57  40  FOBS=   77.3  SIGMA=   3.3  PHAS=    33.8  FOM=  0.87  TEST= 0
INDE  29  57  42  FOBS=   65.0  SIGMA=   4.0  PHAS=  -176.1  FOM=  0.88  TEST= 0
INDE  29  57  44  FOBS=   45.7  SIGMA=   6.6  PHAS=    49.7  FOM=  0.61  TEST= 0
INDE  29  58  29  FOBS=   83.6  SIGMA=   3.0  PHAS=   103.0  FOM=  0.87  TEST= 0
INDE  29  58  31  FOBS=   35.0  SIGMA=   7.0  PHAS=   110.7  FOM=  0.38  TEST= 0
INDE  29  58  33  FOBS=   51.4  SIGMA=   4.5  PHAS=   -99.3  FOM=  0.16  TEST= 0
INDE  29  58  35  FOBS=    0.0  SIGMA=  22.6  PHAS=     0.0  FOM=  0.00  TEST= 1
INDE  29  58  37  FOBS=   39.4  SIGMA=   6.2  PHAS=   -39.6  FOM=  0.14  TEST= 0
INDE  29  58  39  FOBS=   21.3  SIGMA=  11.7  PHAS=  -120.2  FOM=  0.02  TEST= 1
INDE  29  58  41  FOBS=   59.7  SIGMA=   4.9  PHAS=    61.6  FOM=  0.34  TEST= 1
INDE  29  59  30  FOBS=   63.0  SIGMA=   4.0  PHAS=    13.3  FOM=  0.85  TEST= 0
INDE  29  59  32  FOBS=   79.5  SIGMA=   3.2  PHAS=   -84.3  FOM=  0.85  TEST= 0
INDE  29  59  34  FOBS=    0.0  SIGMA=  20.7  PHAS=     0.0  FOM=  0.00  TEST= 0
INDE  29  59  36  FOBS=   46.4  SIGMA=   5.8  PHAS=   141.3  FOM=  0.83  TEST= 0
INDE  29  59  38  FOBS=    0.0  SIGMA=  23.4  PHAS=     0.0  FOM=  0.00  TEST= 0
INDE  29  59  40  FOBS=    0.0  SIGMA=  25.4  PHAS=     0.0  FOM=  0.00  TEST= 0
INDE  29  60  29  FOBS=   49.9  SIGMA=   5.6  PHAS=  -118.7  FOM=  0.09  TEST= 1
INDE  29  60  31  FOBS=   80.0  SIGMA=   3.5  PHAS=  -161.2  FOM=  0.81  TEST= 0
INDE  29  60  33  FOBS=    0.0  SIGMA=  23.8  PHAS=     0.0  FOM=  0.00  TEST= 0
INDE  29  60  35  FOBS=   36.5  SIGMA=   7.1  PHAS=    99.2  FOM=  0.81  TEST= 0
INDE  29  60  37  FOBS=   81.9  SIGMA=   3.8  PHAS=    69.5  FOM=  0.90  TEST= 0
INDE  29  60  39  FOBS=   26.7  SIGMA=  11.9  PHAS=    18.8  FOM=  0.19  TEST= 0
INDE  29  61  30  FOBS=   74.3  SIGMA=   4.4  PHAS=   123.8  FOM=  0.49  TEST= 0
INDE  29  61  32  FOBS=    0.0  SIGMA=  25.6  PHAS=     0.0  FOM=  0.00  TEST= 0
INDE  29  61  34  FOBS=    0.0  SIGMA=  25.7  PHAS=     0.0  FOM=  0.00  TEST= 0
INDE  29  61  36  FOBS=   12.6  SIGMA=  27.5  PHAS=    14.3  FOM=  0.38  TEST= 0
INDE  29  61  38  FOBS=   42.8  SIGMA=   7.4  PHAS=    70.0  FOM=  0.66  TEST= 0
INDE  29  62  29  FOBS=   37.5  SIGMA=   8.4  PHAS=    15.6  FOM=  0.66  TEST= 0
INDE  29  62  31  FOBS=    0.0  SIGMA=  25.7  PHAS=     0.0  FOM=  0.00  TEST= 0
INDE  29  62  33  FOBS=    0.0  SIGMA=  28.7  PHAS=     0.0  FOM=  0.00  TEST= 0
INDE  29  62  35  FOBS=   30.4  SIGMA=   8.6  PHAS=   -17.7  FOM=  0.53  TEST= 0
INDE  29  63  30  FOBS=   79.4  SIGMA=   4.2  PHAS=   -87.4  FOM=  0.88  TEST= 0
```

*FIG. 12A - 533*

```
INDE 29 63 32 FOBS=   77.5 SIGMA=  4.4 PHAS=  -82.1 FOM= 0.87 TEST= 0
INDE 29 63 34 FOBS=   66.7 SIGMA=  5.2 PHAS= -105.6 FOM= 0.85 TEST= 0
INDE 29 64 29 FOBS=   47.8 SIGMA=  8.5 PHAS= -133.8 FOM= 0.79 TEST= 0
INDE 29 64 31 FOBS=    0.0 SIGMA= 28.8 PHAS=    0.0 FOM= 0.00 TEST= 0
INDE 29 64 33 FOBS=   52.7 SIGMA=  6.6 PHAS= -174.5 FOM= 0.87 TEST= 0
INDE 29 65 30 FOBS=    0.0 SIGMA= 33.1 PHAS=    0.0 FOM= 0.00 TEST= 0
INDE 29 66 29 FOBS=   13.0 SIGMA= 41.4 PHAS= -109.9 FOM= 0.09 TEST= 0
INDE 30 30 30 FOBS=  554.4 SIGMA=  0.9 PHAS=  127.1 FOM= 0.98 TEST= 0
INDE 30 31 31 FOBS=  244.4 SIGMA=  0.8 PHAS=    5.3 FOM= 0.95 TEST= 0
INDE 30 31 33 FOBS=  183.8 SIGMA=  1.1 PHAS=   38.4 FOM= 0.95 TEST= 0
INDE 30 31 35 FOBS=  110.8 SIGMA=  1.7 PHAS=  172.1 FOM= 0.87 TEST= 0
INDE 30 31 37 FOBS=   70.1 SIGMA=  2.7 PHAS=  -92.4 FOM= 0.92 TEST= 0
INDE 30 31 39 FOBS=   92.1 SIGMA=  2.0 PHAS=   45.9 FOM= 0.92 TEST= 0
INDE 30 31 41 FOBS=  162.3 SIGMA=  1.2 PHAS=   41.9 FOM= 0.95 TEST= 0
INDE 30 31 43 FOBS=   79.6 SIGMA=  2.1 PHAS=   93.4 FOM= 0.77 TEST= 0
INDE 30 31 45 FOBS=   42.9 SIGMA=  4.1 PHAS= -143.7 FOM= 0.46 TEST= 0
INDE 30 31 47 FOBS=   67.1 SIGMA=  2.4 PHAS=  -82.5 FOM= 0.47 TEST= 0
INDE 30 31 49 FOBS=   55.8 SIGMA=  3.0 PHAS=  -78.9 FOM= 0.32 TEST= 1
INDE 30 31 51 FOBS=   74.0 SIGMA=  2.3 PHAS=  163.3 FOM= 0.83 TEST= 0
INDE 30 31 53 FOBS=   66.5 SIGMA=  2.6 PHAS= -102.9 FOM= 0.90 TEST= 0
INDE 30 31 55 FOBS=   54.2 SIGMA=  3.8 PHAS=  -69.1 FOM= 0.58 TEST= 0
INDE 30 31 57 FOBS=   91.2 SIGMA=  2.8 PHAS= -127.8 FOM= 0.88 TEST= 0
INDE 30 31 59 FOBS=    0.0 SIGMA= 22.4 PHAS=    0.0 FOM= 0.00 TEST= 0
INDE 30 31 61 FOBS=   87.6 SIGMA=  3.0 PHAS=  128.7 FOM= 0.90 TEST= 0
INDE 30 31 63 FOBS=    0.0 SIGMA= 28.6 PHAS=    0.0 FOM= 0.00 TEST= 0
INDE 30 32 30 FOBS=  158.1 SIGMA=  1.2 PHAS=   81.7 FOM= 0.91 TEST= 0
INDE 30 32 32 FOBS=   28.7 SIGMA=  6.4 PHAS=   -8.2 FOM= 0.19 TEST= 0
INDE 30 32 34 FOBS=   99.5 SIGMA=  1.9 PHAS=   80.9 FOM= 0.90 TEST= 0
INDE 30 32 36 FOBS=   23.3 SIGMA=  8.9 PHAS=  -32.4 FOM= 0.22 TEST= 0
INDE 30 32 38 FOBS=  107.7 SIGMA=  1.8 PHAS=  150.8 FOM= 0.94 TEST= 0
INDE 30 32 40 FOBS=   58.9 SIGMA=  3.2 PHAS= -147.6 FOM= 0.84 TEST= 0
INDE 30 32 42 FOBS=   51.7 SIGMA=  3.5 PHAS=   41.0 FOM= 0.58 TEST= 0
INDE 30 32 44 FOBS=   45.0 SIGMA=  4.1 PHAS=  147.6 FOM= 0.37 TEST= 0
INDE 30 32 46 FOBS=    0.0 SIGMA= 18.8 PHAS=    0.0 FOM= 0.00 TEST= 0
INDE 30 32 48 FOBS=   60.1 SIGMA=  2.7 PHAS= -118.3 FOM= 0.81 TEST= 0
INDE 30 32 50 FOBS=    0.0 SIGMA= 17.6 PHAS=    0.0 FOM= 0.00 TEST= 1
INDE 30 32 52 FOBS=   78.1 SIGMA=  2.3 PHAS=  116.7 FOM= 0.73 TEST= 1
INDE 30 32 54 FOBS=   39.2 SIGMA=  4.7 PHAS=  -80.1 FOM= 0.48 TEST= 1
INDE 30 32 56 FOBS=   34.3 SIGMA=  6.5 PHAS=  150.5 FOM= 0.55 TEST= 0
INDE 30 32 58 FOBS=  117.6 SIGMA=  2.2 PHAS=  128.3 FOM= 0.96 TEST= 0
INDE 30 32 60 FOBS=   43.2 SIGMA=  5.9 PHAS= -124.2 FOM= 0.73 TEST= 0
INDE 30 32 62 FOBS=   92.3 SIGMA=  3.7 PHAS=   42.4 FOM= 0.93 TEST= 0
INDE 30 32 64 FOBS=   24.9 SIGMA= 13.9 PHAS=   48.9 FOM= 0.56 TEST= 0
INDE 30 33 31 FOBS=  204.0 SIGMA=  0.9 PHAS=  -43.7 FOM= 0.95 TEST= 0
INDE 30 33 33 FOBS=  175.2 SIGMA=  1.2 PHAS=   72.5 FOM= 0.95 TEST= 0
INDE 30 33 35 FOBS=  109.6 SIGMA=  1.8 PHAS=   93.7 FOM= 0.81 TEST= 0
INDE 30 33 37 FOBS=   58.8 SIGMA=  3.2 PHAS=   16.9 FOM= 0.84 TEST= 0
INDE 30 33 39 FOBS=  191.8 SIGMA=  1.1 PHAS=   -5.5 FOM= 0.92 TEST= 0
INDE 30 33 41 FOBS=   93.8 SIGMA=  2.0 PHAS=    2.8 FOM= 0.78 TEST= 0
INDE 30 33 43 FOBS=   29.1 SIGMA=  6.2 PHAS=   91.2 FOM= 0.43 TEST= 0
INDE 30 33 45 FOBS=   65.6 SIGMA=  2.7 PHAS=   29.7 FOM= 0.83 TEST= 0
INDE 30 33 47 FOBS=   51.3 SIGMA=  3.1 PHAS=  -87.1 FOM= 0.66 TEST= 0
INDE 30 33 49 FOBS=  119.6 SIGMA=  1.5 PHAS=  124.0 FOM= 0.47 TEST= 1
INDE 30 33 51 FOBS=   44.3 SIGMA=  4.1 PHAS=  154.2 FOM= 0.58 TEST= 0
INDE 30 33 53 FOBS=    0.0 SIGMA= 19.1 PHAS=    0.0 FOM= 0.00 TEST= 0
INDE 30 33 55 FOBS=   52.7 SIGMA=  3.7 PHAS=   40.1 FOM= 0.28 TEST= 1
INDE 30 33 57 FOBS=   16.3 SIGMA= 14.8 PHAS=  -56.3 FOM= 0.05 TEST= 0
INDE 30 33 59 FOBS=   90.5 SIGMA=  2.9 PHAS=   50.1 FOM= 0.86 TEST= 0
INDE 30 33 61 FOBS=    0.0 SIGMA= 26.1 PHAS=    0.0 FOM= 0.00 TEST= 0
INDE 30 33 63 FOBS=   77.5 SIGMA=  4.5 PHAS=  -76.7 FOM= 0.91 TEST= 0
INDE 30 34 30 FOBS=  108.6 SIGMA=  1.8 PHAS=   70.8 FOM= 0.84 TEST= 0
INDE 30 34 32 FOBS=   24.4 SIGMA=  7.2 PHAS= -157.5 FOM= 0.42 TEST= 0
INDE 30 34 34 FOBS=   99.3 SIGMA=  1.9 PHAS=   82.0 FOM= 0.94 TEST= 0
INDE 30 34 36 FOBS=  160.6 SIGMA=  1.2 PHAS=  -29.1 FOM= 0.95 TEST= 0
INDE 30 34 38 FOBS=  149.5 SIGMA=  1.3 PHAS= -119.2 FOM= 0.95 TEST= 0
INDE 30 34 40 FOBS=  109.0 SIGMA=  1.7 PHAS= -119.1 FOM= 0.91 TEST= 0
INDE 30 34 42 FOBS=    0.0 SIGMA= 20.9 PHAS=    0.0 FOM= 0.00 TEST= 0
INDE 30 34 44 FOBS=   81.2 SIGMA=  2.2 PHAS=  -77.3 FOM= 0.85 TEST= 0
INDE 30 34 46 FOBS=  111.9 SIGMA=  1.6 PHAS= -142.4 FOM= 0.90 TEST= 0
INDE 30 34 48 FOBS=   48.2 SIGMA=  3.7 PHAS=  103.2 FOM= 0.59 TEST= 0
```

*FIG. 12A - 534*

```
INDE 30 34 50 FOBS=   119.1 SIGMA=  1.5 PHAS=   -9.7 FOM= 0.94 TEST= 0
INDE 30 34 52 FOBS=    44.0 SIGMA=  4.0 PHAS=   58.2 FOM= 0.83 TEST= 0
INDE 30 34 54 FOBS=    86.1 SIGMA=  2.2 PHAS=  -51.7 FOM= 0.90 TEST= 0
INDE 30 34 56 FOBS=    52.3 SIGMA=  3.8 PHAS=  -81.0 FOM= 0.75 TEST= 0
INDE 30 34 58 FOBS=    58.0 SIGMA=  3.7 PHAS=   15.1 FOM= 0.81 TEST= 0
INDE 30 34 60 FOBS=     0.0 SIGMA= 28.1 PHAS=    0.0 FOM= 0.00 TEST= 0
INDE 30 34 62 FOBS=    38.1 SIGMA=  9.0 PHAS=  107.3 FOM= 0.63 TEST= 0
INDE 30 35 31 FOBS=   183.6 SIGMA=  1.1 PHAS=   15.0 FOM= 0.97 TEST= 0
INDE 30 35 33 FOBS=   200.3 SIGMA=  1.0 PHAS=   54.6 FOM= 0.95 TEST= 0
INDE 30 35 35 FOBS=    46.1 SIGMA=  4.5 PHAS=  -84.5 FOM= 0.56 TEST= 0
INDE 30 35 37 FOBS=   121.6 SIGMA=  1.6 PHAS=   78.5 FOM= 0.89 TEST= 0
INDE 30 35 39 FOBS=     0.0 SIGMA= 19.1 PHAS=    0.0 FOM= 0.00 TEST= 0
INDE 30 35 41 FOBS=   105.0 SIGMA=  1.8 PHAS=  177.9 FOM= 0.93 TEST= 0
INDE 30 35 43 FOBS=     0.0 SIGMA= 19.4 PHAS=    0.0 FOM= 0.00 TEST= 0
INDE 30 35 45 FOBS=    54.5 SIGMA=  3.3 PHAS=   63.5 FOM= 0.77 TEST= 0
INDE 30 35 47 FOBS=     0.0 SIGMA= 19.3 PHAS=    0.0 FOM= 0.00 TEST= 0
INDE 30 35 49 FOBS=    33.8 SIGMA=  5.4 PHAS= -110.7 FOM= 0.42 TEST= 0
INDE 30 35 51 FOBS=   123.3 SIGMA=  1.5 PHAS=  -84.4 FOM= 0.94 TEST= 0
INDE 30 35 53 FOBS=     0.0 SIGMA= 21.3 PHAS=    0.0 FOM= 0.00 TEST= 0
INDE 30 35 55 FOBS=     7.9 SIGMA= 26.9 PHAS=  115.1 FOM= 0.22 TEST= 0
INDE 30 35 57 FOBS=    58.3 SIGMA=  3.4 PHAS= -119.9 FOM= 0.76 TEST= 0
INDE 30 35 59 FOBS=    90.3 SIGMA=  2.9 PHAS=  -89.3 FOM= 0.91 TEST= 0
INDE 30 35 61 FOBS=     0.0 SIGMA= 24.0 PHAS=    0.0 FOM= 0.00 TEST= 0
INDE 30 36 30 FOBS=   100.5 SIGMA=  1.9 PHAS=   50.6 FOM= 0.86 TEST= 0
INDE 30 36 32 FOBS=   145.7 SIGMA=  1.4 PHAS=  -24.4 FOM= 0.82 TEST= 0
INDE 30 36 34 FOBS=   128.7 SIGMA=  1.5 PHAS=   68.8 FOM= 0.87 TEST= 0
INDE 30 36 36 FOBS=   128.7 SIGMA=  1.5 PHAS=  -28.4 FOM= 0.92 TEST= 0
INDE 30 36 38 FOBS=   126.3 SIGMA=  1.6 PHAS=  -58.1 FOM= 0.94 TEST= 0
INDE 30 36 40 FOBS=    59.4 SIGMA=  3.1 PHAS=   93.5 FOM= 0.80 TEST= 0
INDE 30 36 42 FOBS=    83.6 SIGMA=  2.2 PHAS=  152.9 FOM= 0.83 TEST= 0
INDE 30 36 44 FOBS=   136.2 SIGMA=  1.4 PHAS=  -98.8 FOM= 0.91 TEST= 0
INDE 30 36 46 FOBS=    47.3 SIGMA=  3.8 PHAS= -165.9 FOM= 0.70 TEST= 0
INDE 30 36 48 FOBS=    30.8 SIGMA=  6.4 PHAS=   57.1 FOM= 0.22 TEST= 0
INDE 30 36 50 FOBS=    35.7 SIGMA=  5.2 PHAS=  -86.7 FOM= 0.13 TEST= 0
INDE 30 36 52 FOBS=     8.6 SIGMA= 22.7 PHAS=  129.5 FOM= 0.06 TEST= 1
INDE 30 36 54 FOBS=    70.7 SIGMA=  2.7 PHAS=  -31.7 FOM= 0.16 TEST= 1
INDE 30 36 56 FOBS=    40.8 SIGMA=  5.2 PHAS=  -64.3 FOM= 0.48 TEST= 0
INDE 30 36 58 FOBS=     0.0 SIGMA= 26.0 PHAS=    0.0 FOM= 0.00 TEST= 0
INDE 30 36 60 FOBS=    50.9 SIGMA=  5.1 PHAS=  163.2 FOM= 0.87 TEST= 0
INDE 30 36 62 FOBS=    31.6 SIGMA= 14.1 PHAS=  141.0 FOM= 0.38 TEST= 0
INDE 30 37 31 FOBS=    68.4 SIGMA=  2.7 PHAS=  -25.3 FOM= 0.42 TEST= 0
INDE 30 37 33 FOBS=     0.0 SIGMA= 19.5 PHAS=    0.0 FOM= 0.00 TEST= 0
INDE 30 37 35 FOBS=   122.3 SIGMA=  1.5 PHAS=  -82.1 FOM= 0.89 TEST= 0
INDE 30 37 37 FOBS=    79.0 SIGMA=  2.4 PHAS= -113.2 FOM= 0.87 TEST= 0
INDE 30 37 39 FOBS=    82.6 SIGMA=  2.3 PHAS=  -51.5 FOM= 0.86 TEST= 0
INDE 30 37 41 FOBS=    74.2 SIGMA=  2.5 PHAS=  170.7 FOM= 0.78 TEST= 0
INDE 30 37 43 FOBS=    58.9 SIGMA=  3.1 PHAS=   98.4 FOM= 0.77 TEST= 0
INDE 30 37 45 FOBS=    71.8 SIGMA=  2.5 PHAS=   76.7 FOM= 0.58 TEST= 0
INDE 30 37 47 FOBS=    56.2 SIGMA=  3.2 PHAS= -134.0 FOM= 0.85 TEST= 0
INDE 30 37 49 FOBS=    13.3 SIGMA= 13.2 PHAS=  -98.0 FOM= 0.20 TEST= 0
INDE 30 37 51 FOBS=    44.2 SIGMA=  4.0 PHAS=  179.2 FOM= 0.01 TEST= 1
INDE 30 37 53 FOBS=    30.6 SIGMA=  6.5 PHAS=  -96.7 FOM= 0.48 TEST= 1
INDE 30 37 55 FOBS=    71.6 SIGMA=  2.7 PHAS=   85.7 FOM= 0.82 TEST= 0
INDE 30 37 57 FOBS=    33.1 SIGMA=  6.9 PHAS=  117.3 FOM= 0.17 TEST= 0
INDE 30 37 59 FOBS=    53.9 SIGMA=  4.4 PHAS=  -68.2 FOM= 0.64 TEST= 0
INDE 30 37 61 FOBS=     0.0 SIGMA= 26.4 PHAS=    0.0 FOM= 0.00 TEST= 0
INDE 30 38 30 FOBS=    42.7 SIGMA=  4.4 PHAS=   68.4 FOM= 0.35 TEST= 0
INDE 30 38 32 FOBS=    55.4 SIGMA=  3.2 PHAS=  -15.5 FOM= 0.73 TEST= 0
INDE 30 38 34 FOBS=    75.0 SIGMA=  2.4 PHAS=  143.0 FOM= 0.29 TEST= 1
INDE 30 38 36 FOBS=    84.8 SIGMA=  2.2 PHAS= -112.0 FOM= 0.76 TEST= 0
INDE 30 38 38 FOBS=    20.0 SIGMA=  9.6 PHAS= -114.2 FOM= 0.74 TEST= 0
INDE 30 38 40 FOBS=   112.1 SIGMA=  1.7 PHAS=  126.0 FOM= 0.94 TEST= 0
INDE 30 38 42 FOBS=     0.0 SIGMA= 19.0 PHAS=    0.0 FOM= 0.00 TEST= 0
INDE 30 38 44 FOBS=    54.5 SIGMA=  3.3 PHAS=  -37.1 FOM= 0.78 TEST= 0
INDE 30 38 46 FOBS=   123.8 SIGMA=  1.5 PHAS=  129.9 FOM= 0.95 TEST= 0
INDE 30 38 48 FOBS=    19.4 SIGMA= 10.9 PHAS=  122.7 FOM= 0.42 TEST= 0
INDE 30 38 50 FOBS=     0.0 SIGMA= 18.7 PHAS=    0.0 FOM= 0.00 TEST= 0
INDE 30 38 52 FOBS=    36.6 SIGMA=  5.6 PHAS=   91.4 FOM= 0.67 TEST= 0
INDE 30 38 54 FOBS=    17.6 SIGMA= 10.8 PHAS=  -49.6 FOM= 0.54 TEST= 0
INDE 30 38 56 FOBS=     0.0 SIGMA= 20.8 PHAS=    0.0 FOM= 0.00 TEST= 0
```

*FIG. 12A - 535*

```
INDE 30 38 58 FOBS=  78.5 SIGMA=  2.8 PHAS= -121.2 FOM= 0.64 TEST= 0
INDE 30 38 60 FOBS=  42.5 SIGMA=  6.3 PHAS= -176.8 FOM= 0.77 TEST= 0
INDE 30 39 31 FOBS=   0.0 SIGMA= 19.4 PHAS=    0.0 FOM= 0.00 TEST= 0
INDE 30 39 33 FOBS=   0.0 SIGMA= 20.1 PHAS=    0.0 FOM= 0.00 TEST= 0
INDE 30 39 35 FOBS=  54.8 SIGMA=  3.3 PHAS= -137.0 FOM= 0.40 TEST= 0
INDE 30 39 37 FOBS=  43.4 SIGMA=  4.2 PHAS=  162.8 FOM= 0.76 TEST= 0
INDE 30 39 39 FOBS=  70.7 SIGMA=  2.6 PHAS=  -19.8 FOM= 0.93 TEST= 0
INDE 30 39 41 FOBS=   0.0 SIGMA= 21.9 PHAS=    0.0 FOM= 0.00 TEST= 0
INDE 30 39 43 FOBS=   0.0 SIGMA= 19.5 PHAS=    0.0 FOM= 0.00 TEST= 0
INDE 30 39 45 FOBS=  89.2 SIGMA=  2.1 PHAS=   46.8 FOM= 0.94 TEST= 0
INDE 30 39 47 FOBS=  82.4 SIGMA=  2.2 PHAS=   84.8 FOM= 0.30 TEST= 0
INDE 30 39 49 FOBS=   0.0 SIGMA= 19.5 PHAS=    0.0 FOM= 0.00 TEST= 0
INDE 30 39 51 FOBS=  61.6 SIGMA=  2.9 PHAS=   37.0 FOM= 0.72 TEST= 0
INDE 30 39 53 FOBS=  37.8 SIGMA=  5.4 PHAS=  -90.8 FOM= 0.81 TEST= 0
INDE 30 39 55 FOBS=  60.0 SIGMA=  3.7 PHAS=   76.9 FOM= 0.84 TEST= 0
INDE 30 39 57 FOBS=  44.3 SIGMA=  5.0 PHAS=   35.2 FOM= 0.59 TEST= 0
INDE 30 39 59 FOBS=  77.3 SIGMA=  3.0 PHAS=   48.5 FOM= 0.63 TEST= 0
INDE 30 40 30 FOBS= 113.1 SIGMA=  1.5 PHAS=  172.3 FOM= 0.97 TEST= 0
INDE 30 40 32 FOBS= 117.6 SIGMA=  1.5 PHAS=   16.1 FOM= 0.93 TEST= 0
INDE 30 40 34 FOBS=  62.2 SIGMA=  3.0 PHAS= -180.0 FOM= 0.81 TEST= 0
INDE 30 40 36 FOBS= 148.6 SIGMA=  1.3 PHAS= -112.5 FOM= 0.94 TEST= 0
INDE 30 40 38 FOBS= 108.7 SIGMA=  1.7 PHAS=   11.0 FOM= 0.78 TEST= 0
INDE 30 40 40 FOBS= 109.5 SIGMA=  1.7 PHAS=  127.5 FOM= 0.91 TEST= 0
INDE 30 40 42 FOBS=  85.0 SIGMA=  2.2 PHAS=  -32.3 FOM= 0.80 TEST= 0
INDE 30 40 44 FOBS= 165.5 SIGMA=  1.2 PHAS=  -55.4 FOM= 0.98 TEST= 0
INDE 30 40 46 FOBS=   0.0 SIGMA= 20.9 PHAS=    0.0 FOM= 0.00 TEST= 0
INDE 30 40 48 FOBS=  50.3 SIGMA=  3.6 PHAS=  -75.3 FOM= 0.45 TEST= 0
INDE 30 40 50 FOBS=  42.3 SIGMA=  4.3 PHAS=   -1.5 FOM= 0.46 TEST= 0
INDE 30 40 52 FOBS=  71.6 SIGMA=  2.7 PHAS=  -18.0 FOM= 0.90 TEST= 0
INDE 30 40 54 FOBS= 102.2 SIGMA=  2.2 PHAS=  -55.2 FOM= 0.93 TEST= 0
INDE 30 40 56 FOBS=  81.0 SIGMA=  2.8 PHAS=   58.0 FOM= 0.77 TEST= 0
INDE 30 40 58 FOBS=   8.7 SIGMA= 30.2 PHAS=  -93.9 FOM= 0.35 TEST= 0
INDE 30 41 31 FOBS=  71.2 SIGMA=  2.3 PHAS=    7.5 FOM= 0.85 TEST= 0
INDE 30 41 33 FOBS=  75.1 SIGMA=  2.3 PHAS=  150.0 FOM= 0.78 TEST= 0
INDE 30 41 35 FOBS=  93.0 SIGMA=  2.0 PHAS=  162.6 FOM= 0.91 TEST= 0
INDE 30 41 37 FOBS= 127.4 SIGMA=  1.3 PHAS=  164.2 FOM= 0.94 TEST= 0
INDE 30 41 39 FOBS=  90.1 SIGMA=  1.9 PHAS=  -35.5 FOM= 0.87 TEST= 0
INDE 30 41 41 FOBS=  49.5 SIGMA=  3.5 PHAS=   19.1 FOM= 0.74 TEST= 0
INDE 30 41 43 FOBS= 121.4 SIGMA=  1.6 PHAS= -156.6 FOM= 0.94 TEST= 0
INDE 30 41 45 FOBS=  80.1 SIGMA=  2.3 PHAS=  -87.9 FOM= 0.82 TEST= 0
INDE 30 41 47 FOBS=  75.5 SIGMA=  2.4 PHAS= -143.0 FOM= 0.43 TEST= 0
INDE 30 41 49 FOBS=  69.8 SIGMA=  2.6 PHAS=  -44.6 FOM= 0.71 TEST= 0
INDE 30 41 51 FOBS=  37.0 SIGMA=  4.9 PHAS= -105.1 FOM= 0.04 TEST= 1
INDE 30 41 53 FOBS= 155.2 SIGMA=  1.5 PHAS= -144.3 FOM= 0.98 TEST= 0
INDE 30 41 55 FOBS=  24.3 SIGMA=  9.1 PHAS=  142.1 FOM= 0.25 TEST= 0
INDE 30 41 57 FOBS=  67.7 SIGMA=  3.3 PHAS=   -5.5 FOM= 0.90 TEST= 0
INDE 30 42 30 FOBS= 117.9 SIGMA=  1.5 PHAS= -173.8 FOM= 0.93 TEST= 0
INDE 30 42 32 FOBS= 100.8 SIGMA=  1.7 PHAS=   14.2 FOM= 0.92 TEST= 0
INDE 30 42 34 FOBS=  41.6 SIGMA=  4.3 PHAS=  -33.4 FOM= 0.43 TEST= 0
INDE 30 42 36 FOBS=  54.4 SIGMA=  3.1 PHAS=  -31.0 FOM= 0.90 TEST= 0
INDE 30 42 38 FOBS=  41.6 SIGMA=  4.1 PHAS=  114.5 FOM= 0.40 TEST= 0
INDE 30 42 40 FOBS=  32.0 SIGMA=  5.3 PHAS= -112.3 FOM= 0.65 TEST= 0
INDE 30 42 42 FOBS=  48.8 SIGMA=  3.4 PHAS=   50.0 FOM= 0.73 TEST= 0
INDE 30 42 44 FOBS=  78.9 SIGMA=  2.1 PHAS=  -93.0 FOM= 0.87 TEST= 0
INDE 30 42 46 FOBS=  12.7 SIGMA= 14.4 PHAS=  175.6 FOM= 0.13 TEST= 0
INDE 30 42 48 FOBS=  79.7 SIGMA=  2.3 PHAS=  -57.7 FOM= 0.80 TEST= 0
INDE 30 42 50 FOBS=  51.6 SIGMA=  4.0 PHAS=  -79.9 FOM= 0.22 TEST= 1
INDE 30 42 52 FOBS= 120.1 SIGMA=  2.0 PHAS=   93.2 FOM= 0.95 TEST= 0
INDE 30 42 54 FOBS=  39.1 SIGMA=  7.5 PHAS=   35.7 FOM= 0.42 TEST= 0
INDE 30 42 56 FOBS=  40.6 SIGMA=  5.6 PHAS=   13.1 FOM= 0.22 TEST= 0
INDE 30 42 58 FOBS=  73.8 SIGMA=  3.8 PHAS=  -82.7 FOM= 0.87 TEST= 0
INDE 30 43 31 FOBS= 118.4 SIGMA=  1.4 PHAS=   65.9 FOM= 0.88 TEST= 0
INDE 30 43 33 FOBS=  97.3 SIGMA=  1.8 PHAS=  -34.6 FOM= 0.87 TEST= 0
INDE 30 43 35 FOBS= 135.8 SIGMA=  1.4 PHAS= -135.1 FOM= 0.94 TEST= 0
INDE 30 43 37 FOBS= 108.5 SIGMA=  1.6 PHAS= -135.3 FOM= 0.90 TEST= 0
INDE 30 43 39 FOBS=   0.0 SIGMA= 18.5 PHAS=    0.0 FOM= 0.00 TEST= 0
INDE 30 43 41 FOBS=   0.0 SIGMA= 18.4 PHAS=    0.0 FOM= 0.00 TEST= 0
INDE 30 43 43 FOBS= 132.2 SIGMA=  1.3 PHAS= -145.5 FOM= 0.95 TEST= 0
INDE 30 43 45 FOBS= 115.8 SIGMA=  1.5 PHAS= -125.1 FOM= 0.90 TEST= 0
INDE 30 43 47 FOBS=  38.2 SIGMA=  4.5 PHAS= -133.6 FOM= 0.53 TEST= 0
```

*FIG. 12A - 536*

```
INDE 30 43 49 FOBS=    42.8 SIGMA=  4.3 PHAS=  -97.0 FOM= 0.70 TEST= 0
INDE 30 43 51 FOBS=    49.2 SIGMA=  5.0 PHAS=  -55.9 FOM= 0.50 TEST= 0
INDE 30 43 53 FOBS=    44.9 SIGMA=  5.1 PHAS=  -85.5 FOM= 0.76 TEST= 0
INDE 30 43 55 FOBS=     0.0 SIGMA= 23.0 PHAS=    0.0 FOM= 0.00 TEST= 0
INDE 30 43 57 FOBS=    44.5 SIGMA=  6.1 PHAS=  -18.5 FOM= 0.44 TEST= 0
INDE 30 44 30 FOBS=    83.2 SIGMA=  2.0 PHAS=  -61.7 FOM= 0.80 TEST= 0
INDE 30 44 32 FOBS=    36.5 SIGMA=  4.6 PHAS=  -76.4 FOM= 0.56 TEST= 0
INDE 30 44 34 FOBS=    68.8 SIGMA=  2.6 PHAS= -148.9 FOM= 0.90 TEST= 0
INDE 30 44 36 FOBS=    78.9 SIGMA=  2.3 PHAS=  153.6 FOM= 0.76 TEST= 0
INDE 30 44 38 FOBS=    68.6 SIGMA=  2.4 PHAS=  145.7 FOM= 0.85 TEST= 0
INDE 30 44 40 FOBS=     0.0 SIGMA= 19.3 PHAS=    0.0 FOM= 0.00 TEST= 0
INDE 30 44 42 FOBS=    45.1 SIGMA=  3.7 PHAS=  117.4 FOM= 0.82 TEST= 0
INDE 30 44 44 FOBS=   148.0 SIGMA=  1.2 PHAS=  110.1 FOM= 0.96 TEST= 0
INDE 30 44 46 FOBS=     0.0 SIGMA= 21.0 PHAS=    0.0 FOM= 0.00 TEST= 1
INDE 30 44 48 FOBS=    61.9 SIGMA=  3.0 PHAS=  155.9 FOM= 0.85 TEST= 0
INDE 30 44 50 FOBS=    59.8 SIGMA=  3.1 PHAS=  128.4 FOM= 0.73 TEST= 0
INDE 30 44 52 FOBS=     0.0 SIGMA= 20.9 PHAS=    0.0 FOM= 0.00 TEST= 0
INDE 30 44 54 FOBS=    45.5 SIGMA=  6.0 PHAS=  174.1 FOM= 0.05 TEST= 1
INDE 30 44 56 FOBS=     0.0 SIGMA= 22.4 PHAS=    0.0 FOM= 0.00 TEST= 0
INDE 30 45 31 FOBS=   139.2 SIGMA=  1.2 PHAS=   60.0 FOM= 0.93 TEST= 0
INDE 30 45 33 FOBS=   143.0 SIGMA=  1.2 PHAS=   36.8 FOM= 0.95 TEST= 0
INDE 30 45 35 FOBS=     0.0 SIGMA= 20.0 PHAS=    0.0 FOM= 0.00 TEST= 0
INDE 30 45 37 FOBS=   123.3 SIGMA=  1.5 PHAS= -160.4 FOM= 0.38 TEST= 0
INDE 30 45 39 FOBS=    28.0 SIGMA=  5.9 PHAS=  112.4 FOM= 0.29 TEST= 0
INDE 30 45 41 FOBS=    59.2 SIGMA=  2.8 PHAS= -119.6 FOM= 0.22 TEST= 1
INDE 30 45 43 FOBS=    74.9 SIGMA=  2.2 PHAS=    0.3 FOM= 0.89 TEST= 0
INDE 30 45 45 FOBS=    43.2 SIGMA=  3.9 PHAS=  -87.4 FOM= 0.67 TEST= 0
INDE 30 45 47 FOBS=     0.0 SIGMA= 19.7 PHAS=    0.0 FOM= 0.00 TEST= 0
INDE 30 45 49 FOBS=    70.6 SIGMA=  2.7 PHAS=  174.5 FOM= 0.81 TEST= 0
INDE 30 45 51 FOBS=    24.2 SIGMA=  8.2 PHAS= -130.5 FOM= 0.52 TEST= 0
INDE 30 45 53 FOBS=     0.0 SIGMA= 21.4 PHAS=    0.0 FOM= 0.00 TEST= 0
INDE 30 45 55 FOBS=    29.1 SIGMA= 11.2 PHAS=   98.5 FOM= 0.29 TEST= 0
INDE 30 46 30 FOBS=    59.3 SIGMA=  2.7 PHAS=  -15.6 FOM= 0.90 TEST= 0
INDE 30 46 32 FOBS=   199.3 SIGMA=  0.9 PHAS=  -66.2 FOM= 0.98 TEST= 0
INDE 30 46 34 FOBS=   129.8 SIGMA=  1.5 PHAS= -103.4 FOM= 0.93 TEST= 0
INDE 30 46 36 FOBS=    70.4 SIGMA=  2.6 PHAS=  -55.6 FOM= 0.71 TEST= 0
INDE 30 46 38 FOBS=   131.0 SIGMA=  1.4 PHAS=  -92.8 FOM= 0.19 TEST= 1
INDE 30 46 40 FOBS=    35.8 SIGMA=  4.6 PHAS= -160.5 FOM= 0.56 TEST= 0
INDE 30 46 42 FOBS=    16.5 SIGMA= 10.0 PHAS= -119.3 FOM= 0.17 TEST= 0
INDE 30 46 44 FOBS=    54.5 SIGMA=  3.1 PHAS=   97.7 FOM= 0.33 TEST= 1
INDE 30 46 46 FOBS=    52.3 SIGMA=  3.6 PHAS=  -80.0 FOM= 0.75 TEST= 0
INDE 30 46 48 FOBS=    72.4 SIGMA=  2.6 PHAS=  147.2 FOM= 0.84 TEST= 0
INDE 30 46 50 FOBS=    59.2 SIGMA=  3.4 PHAS=  119.0 FOM= 0.92 TEST= 0
INDE 30 46 52 FOBS=    64.9 SIGMA=  3.2 PHAS=  148.3 FOM= 0.90 TEST= 0
INDE 30 46 54 FOBS=    41.4 SIGMA=  5.3 PHAS= -173.7 FOM= 0.37 TEST= 1
INDE 30 47 31 FOBS=    37.0 SIGMA=  4.3 PHAS=  134.1 FOM= 0.81 TEST= 0
INDE 30 47 33 FOBS=   160.6 SIGMA=  1.1 PHAS= -172.1 FOM= 0.96 TEST= 0
INDE 30 47 35 FOBS=    87.2 SIGMA=  2.1 PHAS= -161.0 FOM= 0.32 TEST= 1
INDE 30 47 37 FOBS=    98.9 SIGMA=  1.9 PHAS= -142.4 FOM= 0.89 TEST= 0
INDE 30 47 39 FOBS=    93.1 SIGMA=  1.8 PHAS=  168.6 FOM= 0.89 TEST= 0
INDE 30 47 41 FOBS=    38.3 SIGMA=  4.7 PHAS=   -1.3 FOM= 0.59 TEST= 0
INDE 30 47 43 FOBS=    55.5 SIGMA=  3.2 PHAS=  -25.0 FOM= 0.51 TEST= 0
INDE 30 47 45 FOBS=     0.0 SIGMA= 19.8 PHAS=    0.0 FOM= 0.00 TEST= 0
INDE 30 47 47 FOBS=    73.8 SIGMA=  2.6 PHAS=    9.5 FOM= 0.15 TEST= 1
INDE 30 47 49 FOBS=    44.7 SIGMA=  4.9 PHAS=  160.0 FOM= 0.79 TEST= 0
INDE 30 47 51 FOBS=    95.3 SIGMA=  2.4 PHAS=   61.3 FOM= 0.96 TEST= 0
INDE 30 47 53 FOBS=     0.0 SIGMA= 21.1 PHAS=    0.0 FOM= 0.00 TEST= 0
INDE 30 48 30 FOBS=    83.8 SIGMA=  1.9 PHAS=  -24.8 FOM= 0.78 TEST= 0
INDE 30 48 32 FOBS=    75.3 SIGMA=  2.2 PHAS=  102.0 FOM= 0.87 TEST= 0
INDE 30 48 34 FOBS=    63.8 SIGMA=  2.6 PHAS=   76.3 FOM= 0.74 TEST= 0
INDE 30 48 36 FOBS=   107.0 SIGMA=  1.7 PHAS=   67.1 FOM= 0.91 TEST= 0
INDE 30 48 38 FOBS=    22.6 SIGMA= 10.2 PHAS=  113.5 FOM= 0.24 TEST= 0
INDE 30 48 40 FOBS=     0.0 SIGMA= 18.5 PHAS=    0.0 FOM= 0.00 TEST= 0
INDE 30 48 42 FOBS=    69.2 SIGMA=  2.7 PHAS=   38.9 FOM= 0.47 TEST= 0
INDE 30 48 44 FOBS=    12.3 SIGMA= 15.9 PHAS=  152.9 FOM= 0.13 TEST= 0
INDE 30 48 46 FOBS=    49.5 SIGMA=  4.0 PHAS= -153.3 FOM= 0.66 TEST= 0
INDE 30 48 48 FOBS=    48.6 SIGMA=  4.2 PHAS=   86.0 FOM= 0.84 TEST= 0
INDE 30 48 50 FOBS=    25.9 SIGMA=  9.1 PHAS=  -21.9 FOM= 0.66 TEST= 0
INDE 30 48 52 FOBS=    46.6 SIGMA=  5.2 PHAS=    3.8 FOM= 0.80 TEST= 0
INDE 30 49 31 FOBS=    43.6 SIGMA=  3.6 PHAS=   78.8 FOM= 0.46 TEST= 0
```

*FIG. 12A - 537*

```
INDE 30 49 33 FOBS=    28.7 SIGMA=  5.8 PHAS=  -44.4 FOM= 0.43 TEST= 0
INDE 30 49 35 FOBS=    95.3 SIGMA=  1.9 PHAS=  -54.8 FOM= 0.89 TEST= 0
INDE 30 49 37 FOBS=    25.5 SIGMA=  7.4 PHAS=  -22.7 FOM= 0.51 TEST= 0
INDE 30 49 39 FOBS=     0.0 SIGMA= 19.0 PHAS=    0.0 FOM= 0.00 TEST= 0
INDE 30 49 41 FOBS=     0.0 SIGMA= 20.3 PHAS=    0.0 FOM= 0.00 TEST= 1
INDE 30 49 43 FOBS=    45.3 SIGMA=  4.4 PHAS=  -39.0 FOM= 0.82 TEST= 0
INDE 30 49 45 FOBS=     0.0 SIGMA= 20.4 PHAS=    0.0 FOM= 0.00 TEST= 0
INDE 30 49 47 FOBS=   101.5 SIGMA=  2.2 PHAS=   94.9 FOM= 0.94 TEST= 0
INDE 30 49 49 FOBS=    37.5 SIGMA=  5.9 PHAS= -130.2 FOM= 0.83 TEST= 0
INDE 30 49 51 FOBS=    59.8 SIGMA=  4.1 PHAS=  175.9 FOM= 0.28 TEST= 0
INDE 30 50 30 FOBS=   121.2 SIGMA=  1.4 PHAS=   96.1 FOM= 0.20 TEST= 1
INDE 30 50 32 FOBS=     0.0 SIGMA= 19.6 PHAS=    0.0 FOM= 0.00 TEST= 0
INDE 30 50 34 FOBS=    66.0 SIGMA=  2.4 PHAS=  -85.5 FOM= 0.51 TEST= 0
INDE 30 50 36 FOBS=    46.1 SIGMA=  4.1 PHAS=  -15.0 FOM= 0.57 TEST= 0
INDE 30 50 38 FOBS=    65.5 SIGMA=  3.1 PHAS=  -73.1 FOM= 0.83 TEST= 0
INDE 30 50 40 FOBS=    38.8 SIGMA=  5.3 PHAS=  176.8 FOM= 0.46 TEST= 0
INDE 30 50 42 FOBS=    86.7 SIGMA=  2.5 PHAS= -159.8 FOM= 0.04 TEST= 1
INDE 30 50 44 FOBS=   107.1 SIGMA=  2.1 PHAS= -132.9 FOM= 0.90 TEST= 0
INDE 30 50 46 FOBS=    46.5 SIGMA=  4.7 PHAS=  158.1 FOM= 0.63 TEST= 0
INDE 30 50 48 FOBS=    90.9 SIGMA=  2.5 PHAS=   85.4 FOM= 0.93 TEST= 0
INDE 30 50 50 FOBS=    42.3 SIGMA=  6.3 PHAS=   48.2 FOM= 0.77 TEST= 0
INDE 30 51 31 FOBS=    97.6 SIGMA=  1.7 PHAS=  157.9 FOM= 0.71 TEST= 0
INDE 30 51 33 FOBS=    23.2 SIGMA=  8.3 PHAS=   56.4 FOM= 0.22 TEST= 0
INDE 30 51 35 FOBS=    86.2 SIGMA=  2.2 PHAS= -149.2 FOM= 0.79 TEST= 0
INDE 30 51 37 FOBS=    50.7 SIGMA=  4.7 PHAS= -169.8 FOM= 0.45 TEST= 0
INDE 30 51 39 FOBS=    46.8 SIGMA=  5.2 PHAS=  -28.9 FOM= 0.37 TEST= 0
INDE 30 51 41 FOBS=    84.5 SIGMA=  2.6 PHAS= -178.1 FOM= 0.93 TEST= 0
INDE 30 51 43 FOBS=    50.9 SIGMA=  4.2 PHAS=   59.2 FOM= 0.72 TEST= 0
INDE 30 51 45 FOBS=    62.6 SIGMA=  3.5 PHAS=  141.2 FOM= 0.72 TEST= 0
INDE 30 51 47 FOBS=    96.2 SIGMA=  2.4 PHAS=  104.4 FOM= 0.94 TEST= 0
INDE 30 51 49 FOBS=   119.5 SIGMA=  2.2 PHAS=  -36.2 FOM= 0.95 TEST= 0
INDE 30 52 30 FOBS=    48.4 SIGMA=  3.4 PHAS=   14.1 FOM= 0.82 TEST= 0
INDE 30 52 32 FOBS=     0.0 SIGMA= 18.5 PHAS=    0.0 FOM= 0.00 TEST= 0
INDE 30 52 34 FOBS=    34.2 SIGMA=  5.4 PHAS= -118.0 FOM= 0.41 TEST= 0
INDE 30 52 36 FOBS=    94.8 SIGMA=  2.6 PHAS=   15.0 FOM= 0.95 TEST= 0
INDE 30 52 38 FOBS=    88.7 SIGMA=  2.8 PHAS=  -33.8 FOM= 0.90 TEST= 0
INDE 30 52 40 FOBS=    43.6 SIGMA=  5.6 PHAS=  101.5 FOM= 0.79 TEST= 0
INDE 30 52 42 FOBS=    78.9 SIGMA=  2.8 PHAS=  -65.7 FOM= 0.79 TEST= 0
INDE 30 52 44 FOBS=    56.3 SIGMA=  3.9 PHAS=  -78.0 FOM= 0.76 TEST= 0
INDE 30 52 46 FOBS=    38.7 SIGMA=  6.8 PHAS=   47.3 FOM= 0.65 TEST= 0
INDE 30 52 48 FOBS=    39.7 SIGMA=  6.1 PHAS= -134.9 FOM= 0.67 TEST= 0
INDE 30 53 31 FOBS=    79.9 SIGMA=  2.2 PHAS=  168.7 FOM= 0.91 TEST= 0
INDE 30 53 33 FOBS=     0.0 SIGMA= 20.5 PHAS=    0.0 FOM= 0.00 TEST= 0
INDE 30 53 35 FOBS=    87.1 SIGMA=  2.5 PHAS= -114.6 FOM= 0.92 TEST= 0
INDE 30 53 37 FOBS=    61.5 SIGMA=  3.9 PHAS= -142.8 FOM= 0.85 TEST= 0
INDE 30 53 39 FOBS=     0.0 SIGMA= 22.0 PHAS=    0.0 FOM= 0.00 TEST= 0
INDE 30 53 41 FOBS=    80.1 SIGMA=  3.1 PHAS=  122.3 FOM= 0.10 TEST= 1
INDE 30 53 43 FOBS=     0.0 SIGMA= 20.8 PHAS=    0.0 FOM= 0.00 TEST= 0
INDE 30 53 45 FOBS=    40.9 SIGMA=  5.8 PHAS=  167.4 FOM= 0.66 TEST= 0
INDE 30 53 47 FOBS=    68.1 SIGMA=  3.4 PHAS=  115.6 FOM= 0.82 TEST= 0
INDE 30 54 30 FOBS=    73.8 SIGMA=  3.3 PHAS=   41.5 FOM= 0.88 TEST= 0
INDE 30 54 32 FOBS=    94.4 SIGMA=  2.3 PHAS=  -39.2 FOM= 0.92 TEST= 0
INDE 30 54 34 FOBS=    51.8 SIGMA=  4.1 PHAS= -152.1 FOM= 0.84 TEST= 0
INDE 30 54 36 FOBS=    54.0 SIGMA=  4.4 PHAS=   64.2 FOM= 0.83 TEST= 0
INDE 30 54 38 FOBS=    41.1 SIGMA=  6.0 PHAS=    0.3 FOM= 0.10 TEST= 1
INDE 30 54 40 FOBS=    49.4 SIGMA=  5.1 PHAS= -145.6 FOM= 0.52 TEST= 0
INDE 30 54 42 FOBS=    46.0 SIGMA=  5.1 PHAS= -108.7 FOM= 0.28 TEST= 0
INDE 30 54 44 FOBS=    46.4 SIGMA=  4.8 PHAS=  126.8 FOM= 0.07 TEST= 1
INDE 30 54 46 FOBS=    58.6 SIGMA=  3.9 PHAS=   57.7 FOM= 0.62 TEST= 0
INDE 30 55 31 FOBS=    76.3 SIGMA=  3.2 PHAS= -134.7 FOM= 0.14 TEST= 1
INDE 30 55 33 FOBS=    86.5 SIGMA=  2.5 PHAS= -146.6 FOM= 0.88 TEST= 0
INDE 30 55 35 FOBS=    31.6 SIGMA=  8.1 PHAS=   58.6 FOM= 0.62 TEST= 0
INDE 30 55 37 FOBS=    79.2 SIGMA=  3.1 PHAS= -162.4 FOM= 0.90 TEST= 0
INDE 30 55 39 FOBS=    49.8 SIGMA=  5.0 PHAS=   69.8 FOM= 0.71 TEST= 0
INDE 30 55 41 FOBS=     0.0 SIGMA= 23.3 PHAS=    0.0 FOM= 0.00 TEST= 0
INDE 30 55 43 FOBS=     0.0 SIGMA= 21.1 PHAS=    0.0 FOM= 0.00 TEST= 0
INDE 30 55 45 FOBS=    24.7 SIGMA= 10.6 PHAS=  -38.9 FOM= 0.02 TEST= 1
INDE 30 56 30 FOBS=    39.7 SIGMA=  6.8 PHAS=  -11.5 FOM= 0.69 TEST= 0
INDE 30 56 32 FOBS=    67.5 SIGMA=  3.2 PHAS=  -73.4 FOM= 0.79 TEST= 0
INDE 30 56 34 FOBS=    30.9 SIGMA=  6.9 PHAS= -141.1 FOM= 0.06 TEST= 0
```

*FIG. 12A - 538*

```
INDE  30  56  36  FOBS=   53.4  SIGMA=   4.5  PHAS=   18.6  FOM=  0.86  TEST= 0
INDE  30  56  38  FOBS=   25.9  SIGMA=  10.1  PHAS=  -34.8  FOM=  0.19  TEST= 0
INDE  30  56  40  FOBS=   62.8  SIGMA=   4.1  PHAS=   43.2  FOM=  0.32  TEST= 0
INDE  30  56  42  FOBS=   41.4  SIGMA=   6.2  PHAS=  -72.9  FOM=  0.09  TEST= 0
INDE  30  56  44  FOBS=   63.6  SIGMA=   3.6  PHAS=   55.3  FOM=  0.84  TEST= 0
INDE  30  57  31  FOBS=   27.6  SIGMA=   8.9  PHAS= -144.0  FOM=  0.56  TEST= 0
INDE  30  57  33  FOBS=   66.8  SIGMA=   3.2  PHAS= -154.7  FOM=  0.88  TEST= 0
INDE  30  57  35  FOBS=    0.0  SIGMA=  21.7  PHAS=    0.0  FOM=  0.00  TEST= 0
INDE  30  57  37  FOBS=   73.5  SIGMA=   3.3  PHAS= -120.9  FOM=  0.78  TEST= 0
INDE  30  57  39  FOBS=   42.3  SIGMA=   5.9  PHAS=   73.2  FOM=  0.37  TEST= 0
INDE  30  57  41  FOBS=   61.6  SIGMA=   4.2  PHAS=    7.4  FOM=  0.91  TEST= 0
INDE  30  57  43  FOBS=  102.8  SIGMA=   2.4  PHAS=   60.5  FOM=  0.92  TEST= 0
INDE  30  58  30  FOBS=   28.4  SIGMA=   9.7  PHAS=   60.2  FOM=  0.09  TEST= 0
INDE  30  58  32  FOBS=   56.8  SIGMA=   4.4  PHAS=  148.0  FOM=  0.87  TEST= 0
INDE  30  58  34  FOBS=   36.2  SIGMA=   6.0  PHAS=  120.4  FOM=  0.76  TEST= 0
INDE  30  58  36  FOBS=   40.9  SIGMA=   5.4  PHAS=   32.7  FOM=  0.76  TEST= 0
INDE  30  58  38  FOBS=    0.0  SIGMA=  23.0  PHAS=    0.0  FOM=  0.00  TEST= 0
INDE  30  58  40  FOBS=   68.1  SIGMA=   3.8  PHAS=  -91.8  FOM=  0.85  TEST= 0
INDE  30  58  42  FOBS=   47.4  SIGMA=   5.7  PHAS=  -42.3  FOM=  0.78  TEST= 0
INDE  30  59  31  FOBS=   62.0  SIGMA=   4.0  PHAS=  -15.8  FOM=  0.84  TEST= 0
INDE  30  59  33  FOBS=   36.2  SIGMA=   6.4  PHAS=  126.4  FOM=  0.28  TEST= 0
INDE  30  59  35  FOBS=   46.5  SIGMA=   4.7  PHAS=   15.1  FOM=  0.64  TEST= 0
INDE  30  59  37  FOBS=   40.1  SIGMA=   6.1  PHAS=   27.0  FOM=  0.65  TEST= 0
INDE  30  59  39  FOBS=   29.4  SIGMA=   8.6  PHAS= -172.7  FOM=  0.26  TEST= 1
INDE  30  60  30  FOBS=   44.7  SIGMA=   5.6  PHAS=  -99.7  FOM=  0.79  TEST= 0
INDE  30  60  32  FOBS=   79.3  SIGMA=   3.3  PHAS=  140.6  FOM=  0.90  TEST= 0
INDE  30  60  34  FOBS=    0.0  SIGMA=  21.7  PHAS=    0.0  FOM=  0.00  TEST= 0
INDE  30  60  36  FOBS=   24.5  SIGMA=   9.2  PHAS=  -11.6  FOM=  0.68  TEST= 0
INDE  30  60  38  FOBS=   46.9  SIGMA=   6.7  PHAS=   -9.6  FOM=  0.79  TEST= 0
INDE  30  61  31  FOBS=   19.3  SIGMA=  13.3  PHAS=   92.5  FOM=  0.03  TEST= 1
INDE  30  61  33  FOBS=    0.0  SIGMA=  24.1  PHAS=    0.0  FOM=  0.00  TEST= 0
INDE  30  61  35  FOBS=    0.0  SIGMA=  21.9  PHAS=    0.0  FOM=  0.00  TEST= 0
INDE  30  61  37  FOBS=   62.3  SIGMA=   4.5  PHAS=  -81.2  FOM=  0.84  TEST= 0
INDE  30  62  30  FOBS=   46.5  SIGMA=   6.1  PHAS= -137.4  FOM=  0.43  TEST= 0
INDE  30  62  32  FOBS=   42.7  SIGMA=   8.0  PHAS=  161.3  FOM=  0.71  TEST= 0
INDE  30  62  34  FOBS=    0.0  SIGMA=  26.1  PHAS=    0.0  FOM=  0.00  TEST= 0
INDE  30  62  36  FOBS=   72.8  SIGMA=   4.8  PHAS= -178.4  FOM=  0.78  TEST= 0
INDE  30  63  31  FOBS=   31.9  SIGMA=  12.9  PHAS=  118.9  FOM=  0.38  TEST= 0
INDE  30  63  33  FOBS=   15.3  SIGMA=  22.7  PHAS=   97.0  FOM=  0.03  TEST= 0
INDE  30  64  30  FOBS=    0.0  SIGMA=  33.6  PHAS=    0.0  FOM=  0.00  TEST= 0
INDE  30  64  32  FOBS=    0.0  SIGMA=  26.4  PHAS=    0.0  FOM=  0.00  TEST= 0
INDE  31  32  31  FOBS=  143.4  SIGMA=   1.2  PHAS= -132.8  FOM=  0.87  TEST= 0
INDE  31  32  33  FOBS=  148.4  SIGMA=   1.2  PHAS=  -81.1  FOM=  0.96  TEST= 0
INDE  31  32  35  FOBS=  117.9  SIGMA=   1.6  PHAS=    2.4  FOM=  0.77  TEST= 0
INDE  31  32  37  FOBS=   94.0  SIGMA=   2.0  PHAS= -152.1  FOM=  0.96  TEST= 0
INDE  31  32  39  FOBS=   90.0  SIGMA=   2.1  PHAS=  -32.5  FOM=  0.49  TEST= 0
INDE  31  32  41  FOBS=  154.4  SIGMA=   1.3  PHAS=  -11.6  FOM=  0.92  TEST= 0
INDE  31  32  43  FOBS=   74.3  SIGMA=   2.5  PHAS=  -60.5  FOM=  0.91  TEST= 0
INDE  31  32  45  FOBS=   82.1  SIGMA=   2.0  PHAS= -102.9  FOM=  0.77  TEST= 0
INDE  31  32  47  FOBS=   24.7  SIGMA=   7.0  PHAS= -163.4  FOM=  0.51  TEST= 0
INDE  31  32  49  FOBS=    0.0  SIGMA=  19.0  PHAS=    0.0  FOM=  0.00  TEST= 0
INDE  31  32  51  FOBS=    0.0  SIGMA=  18.6  PHAS=    0.0  FOM=  0.00  TEST= 1
INDE  31  32  53  FOBS=   85.5  SIGMA=   2.1  PHAS=   30.6  FOM=  0.84  TEST= 0
INDE  31  32  55  FOBS=   76.8  SIGMA=   2.5  PHAS= -165.4  FOM=  0.82  TEST= 0
INDE  31  32  57  FOBS=   41.0  SIGMA=   6.1  PHAS= -177.9  FOM=  0.62  TEST= 0
INDE  31  32  59  FOBS=    0.0  SIGMA=  22.5  PHAS=    0.0  FOM=  0.00  TEST= 0
INDE  31  32  61  FOBS=   92.7  SIGMA=   2.9  PHAS=  114.8  FOM=  0.94  TEST= 0
INDE  31  32  63  FOBS=   31.9  SIGMA=   9.4  PHAS= -159.2  FOM=  0.69  TEST= 0
INDE  31  33  32  FOBS=  123.7  SIGMA=   1.4  PHAS=  169.6  FOM=  0.95  TEST= 0
INDE  31  33  34  FOBS=  110.7  SIGMA=   1.6  PHAS=   12.2  FOM=  0.83  TEST= 0
INDE  31  33  36  FOBS=    0.0  SIGMA=  20.3  PHAS=    0.0  FOM=  0.00  TEST= 0
INDE  31  33  38  FOBS=  111.4  SIGMA=   1.7  PHAS=  107.2  FOM=  0.95  TEST= 0
INDE  31  33  40  FOBS=   54.1  SIGMA=   3.4  PHAS=  -63.5  FOM=  0.60  TEST= 0
INDE  31  33  42  FOBS=   50.0  SIGMA=   3.7  PHAS=   23.7  FOM=  0.45  TEST= 0
INDE  31  33  44  FOBS=   36.1  SIGMA=   5.0  PHAS=   84.0  FOM=  0.63  TEST= 0
INDE  31  33  46  FOBS=   46.4  SIGMA=   3.9  PHAS=  104.8  FOM=  0.37  TEST= 1
INDE  31  33  48  FOBS=   57.5  SIGMA=   2.8  PHAS=  160.6  FOM=  0.84  TEST= 0
INDE  31  33  50  FOBS=   88.1  SIGMA=   1.9  PHAS=  -32.8  FOM=  0.90  TEST= 0
INDE  31  33  52  FOBS=   37.6  SIGMA=   5.2  PHAS=  -89.3  FOM=  0.53  TEST= 0
INDE  31  33  54  FOBS=   53.8  SIGMA=   3.5  PHAS= -172.7  FOM=  0.64  TEST= 0
```

*FIG. 12A - 539*

```
INDE  31  33  56  FOBS=    0.0  SIGMA=  19.2  PHAS=    0.0  FOM=  0.00  TEST= 0
INDE  31  33  58  FOBS=   41.6  SIGMA=   6.2  PHAS=  -82.8  FOM=  0.01  TEST= 1
INDE  31  33  60  FOBS=    0.0  SIGMA=  24.0  PHAS=    0.0  FOM=  0.00  TEST= 0
INDE  31  33  62  FOBS=  119.1  SIGMA=   2.6  PHAS=   33.5  FOM=  0.94  TEST= 0
INDE  31  34  31  FOBS=  161.0  SIGMA=   1.2  PHAS=  -55.4  FOM=  0.95  TEST= 0
INDE  31  34  33  FOBS=   81.3  SIGMA=   2.1  PHAS=  -24.7  FOM=  0.85  TEST= 0
INDE  31  34  35  FOBS=   89.1  SIGMA=   2.1  PHAS=   17.5  FOM=  0.96  TEST= 0
INDE  31  34  37  FOBS=  136.4  SIGMA=   1.4  PHAS=  -41.5  FOM=  0.94  TEST= 0
INDE  31  34  39  FOBS=   67.0  SIGMA=   2.8  PHAS= -109.7  FOM=  0.89  TEST= 0
INDE  31  34  41  FOBS=  113.7  SIGMA=   1.7  PHAS= -135.5  FOM=  0.86  TEST= 0
INDE  31  34  43  FOBS=   97.2  SIGMA=   1.9  PHAS=  -23.0  FOM=  0.85  TEST= 0
INDE  31  34  45  FOBS=   92.4  SIGMA=   2.0  PHAS=  -68.3  FOM=  0.92  TEST= 0
INDE  31  34  47  FOBS=    0.0  SIGMA=  19.9  PHAS=    0.0  FOM=  0.00  TEST= 0
INDE  31  34  49  FOBS=   46.2  SIGMA=   3.7  PHAS=    0.8  FOM=  0.84  TEST= 0
INDE  31  34  51  FOBS=   39.9  SIGMA=   4.6  PHAS=  164.8  FOM=  0.75  TEST= 0
INDE  31  34  53  FOBS=  101.2  SIGMA=   1.9  PHAS=   41.8  FOM=  0.92  TEST= 0
INDE  31  34  55  FOBS=   26.3  SIGMA=   8.0  PHAS=  153.8  FOM=  0.62  TEST= 0
INDE  31  34  57  FOBS=   36.9  SIGMA=   5.9  PHAS= -173.2  FOM=  0.03  TEST= 1
INDE  31  34  59  FOBS=   54.0  SIGMA=   4.4  PHAS=  -26.5  FOM=  0.37  TEST= 0
INDE  31  34  61  FOBS=   25.8  SIGMA=  11.5  PHAS=  -55.7  FOM=  0.25  TEST= 0
INDE  31  35  32  FOBS=  142.2  SIGMA=   1.3  PHAS=  -95.7  FOM=  0.79  TEST= 0
INDE  31  35  34  FOBS=  189.2  SIGMA=   1.0  PHAS=  -15.3  FOM=  0.97  TEST= 0
INDE  31  35  36  FOBS=  128.4  SIGMA=   1.5  PHAS= -171.3  FOM=  0.91  TEST= 0
INDE  31  35  38  FOBS=  138.1  SIGMA=   1.4  PHAS= -158.7  FOM=  0.92  TEST= 0
INDE  31  35  40  FOBS=   83.3  SIGMA=   2.3  PHAS= -150.6  FOM=  0.88  TEST= 0
INDE  31  35  42  FOBS=   87.6  SIGMA=   2.1  PHAS=  114.0  FOM=  0.86  TEST= 0
INDE  31  35  44  FOBS=  100.4  SIGMA=   1.9  PHAS=  177.2  FOM=  0.87  TEST= 0
INDE  31  35  46  FOBS=   34.1  SIGMA=   5.5  PHAS= -177.9  FOM=  0.56  TEST= 0
INDE  31  35  48  FOBS=   30.9  SIGMA=   6.0  PHAS= -132.6  FOM=  0.48  TEST= 0
INDE  31  35  50  FOBS=  142.8  SIGMA=   1.3  PHAS=  -94.1  FOM=  0.14  TEST= 1
INDE  31  35  52  FOBS=   71.1  SIGMA=   2.5  PHAS=  -77.6  FOM=  0.89  TEST= 0
INDE  31  35  54  FOBS=   51.0  SIGMA=   3.7  PHAS= -169.4  FOM=  0.79  TEST= 0
INDE  31  35  56  FOBS=   32.6  SIGMA=   5.8  PHAS= -158.9  FOM=  0.21  TEST= 0
INDE  31  35  58  FOBS=   67.8  SIGMA=   2.9  PHAS=  -54.4  FOM=  0.02  TEST= 1
INDE  31  35  60  FOBS=   10.0  SIGMA=  25.7  PHAS=  -66.7  FOM=  0.19  TEST= 0
INDE  31  35  62  FOBS=    0.0  SIGMA=  26.7  PHAS=    0.0  FOM=  0.00  TEST= 0
INDE  31  36  31  FOBS=   84.0  SIGMA=   2.2  PHAS=  -52.2  FOM=  0.72  TEST= 0
INDE  31  36  33  FOBS=   98.1  SIGMA=   1.7  PHAS= -115.6  FOM=  0.90  TEST= 0
INDE  31  36  35  FOBS=    0.0  SIGMA=  19.6  PHAS=    0.0  FOM=  0.00  TEST= 1
INDE  31  36  37  FOBS=   85.2  SIGMA=   2.2  PHAS=   -4.4  FOM=  0.56  TEST= 0
INDE  31  36  39  FOBS=  169.1  SIGMA=   1.2  PHAS=  169.1  FOM=  0.97  TEST= 0
INDE  31  36  41  FOBS=  139.0  SIGMA=   1.4  PHAS=  103.1  FOM=  0.95  TEST= 0
INDE  31  36  43  FOBS=  143.3  SIGMA=   1.3  PHAS=   26.6  FOM=  0.95  TEST= 0
INDE  31  36  45  FOBS=   69.3  SIGMA=   2.6  PHAS= -153.7  FOM=  0.72  TEST= 0
INDE  31  36  47  FOBS=    0.0  SIGMA=  19.9  PHAS=    0.0  FOM=  0.00  TEST= 0
INDE  31  36  49  FOBS=   98.1  SIGMA=   1.9  PHAS=    2.9  FOM=  0.89  TEST= 0
INDE  31  36  51  FOBS=   93.0  SIGMA=   2.0  PHAS= -146.5  FOM=  0.16  TEST= 1
INDE  31  36  53  FOBS=    0.0  SIGMA=  20.0  PHAS=    0.0  FOM=  0.00  TEST= 0
INDE  31  36  55  FOBS=   77.2  SIGMA=   2.5  PHAS=   93.3  FOM=  0.87  TEST= 0
INDE  31  36  57  FOBS=    0.0  SIGMA=  21.0  PHAS=    0.0  FOM=  0.00  TEST= 0
INDE  31  36  59  FOBS=   82.0  SIGMA=   2.6  PHAS= -114.3  FOM=  0.92  TEST= 0
INDE  31  36  61  FOBS=   29.1  SIGMA=  12.2  PHAS= -142.4  FOM=  0.16  TEST= 0
INDE  31  37  32  FOBS=   52.0  SIGMA=   3.5  PHAS=  163.3  FOM=  0.83  TEST= 0
INDE  31  37  34  FOBS=    0.0  SIGMA=  19.0  PHAS=    0.0  FOM=  0.00  TEST= 0
INDE  31  37  36  FOBS=  134.2  SIGMA=   1.4  PHAS= -138.8  FOM=  0.92  TEST= 0
INDE  31  37  38  FOBS=   58.7  SIGMA=   3.2  PHAS=  150.3  FOM=  0.69  TEST= 0
INDE  31  37  40  FOBS=  144.7  SIGMA=   1.4  PHAS=   27.1  FOM=  0.97  TEST= 0
INDE  31  37  42  FOBS=    0.0  SIGMA=  19.6  PHAS=    0.0  FOM=  0.00  TEST= 0
INDE  31  37  44  FOBS=   24.2  SIGMA=   7.8  PHAS= -120.2  FOM=  0.33  TEST= 0
INDE  31  37  46  FOBS=   75.6  SIGMA=   2.4  PHAS=   43.2  FOM=  0.88  TEST= 0
INDE  31  37  48  FOBS=   67.5  SIGMA=   2.7  PHAS=  -87.7  FOM=  0.78  TEST= 0
INDE  31  37  50  FOBS=  125.6  SIGMA=   1.5  PHAS=  -43.5  FOM=  0.96  TEST= 0
INDE  31  37  52  FOBS=    0.0  SIGMA=  19.4  PHAS=    0.0  FOM=  0.00  TEST= 0
INDE  31  37  54  FOBS=    0.0  SIGMA=  19.5  PHAS=    0.0  FOM=  0.00  TEST= 0
INDE  31  37  56  FOBS=   38.0  SIGMA=   5.3  PHAS=  -25.0  FOM=  0.49  TEST= 0
INDE  31  37  58  FOBS=   20.1  SIGMA=  11.0  PHAS= -158.8  FOM=  0.14  TEST= 0
INDE  31  37  60  FOBS=   68.0  SIGMA=   3.4  PHAS=  134.3  FOM=  0.66  TEST= 0
INDE  31  38  31  FOBS=   56.7  SIGMA=   3.2  PHAS=   83.7  FOM=  0.31  TEST= 0
INDE  31  38  33  FOBS=    0.0  SIGMA=  18.9  PHAS=    0.0  FOM=  0.00  TEST= 0
INDE  31  38  35  FOBS=  143.8  SIGMA=   1.3  PHAS=  122.0  FOM=  0.94  TEST= 0
```

*FIG. 12A - 540*

```
INDE 31 38 37 FOBS=   54.6 SIGMA=  3.6 PHAS=  148.4 FOM= 0.53 TEST= 0
INDE 31 38 39 FOBS=  106.6 SIGMA=  1.8 PHAS= -119.2 FOM= 0.94 TEST= 0
INDE 31 38 41 FOBS=   52.1 SIGMA=  3.8 PHAS=    6.2 FOM= 0.68 TEST= 0
INDE 31 38 43 FOBS=    0.0 SIGMA= 19.5 PHAS=    0.0 FOM= 0.00 TEST= 0
INDE 31 38 45 FOBS=  107.6 SIGMA=  1.7 PHAS=  -94.8 FOM= 0.95 TEST= 0
INDE 31 38 47 FOBS=    0.0 SIGMA= 20.5 PHAS=    0.0 FOM= 0.00 TEST= 0
INDE 31 38 49 FOBS=   60.9 SIGMA=  3.1 PHAS= -144.3 FOM= 0.83 TEST= 0
INDE 31 38 51 FOBS=  100.0 SIGMA=  1.9 PHAS= -173.6 FOM= 0.91 TEST= 0
INDE 31 38 53 FOBS=    0.0 SIGMA= 20.9 PHAS=    0.0 FOM= 0.00 TEST= 0
INDE 31 38 55 FOBS=   32.5 SIGMA=  7.2 PHAS=  -94.6 FOM= 0.46 TEST= 0
INDE 31 38 57 FOBS=   35.4 SIGMA=  6.7 PHAS= -102.3 FOM= 0.74 TEST= 0
INDE 31 38 59 FOBS=   17.8 SIGMA= 14.5 PHAS=  125.2 FOM= 0.05 TEST= 1
INDE 31 39 32 FOBS=    0.0 SIGMA= 19.0 PHAS=    0.0 FOM= 0.00 TEST= 0
INDE 31 39 34 FOBS=   33.0 SIGMA=  5.4 PHAS=   71.0 FOM= 0.49 TEST= 0
INDE 31 39 36 FOBS=   91.6 SIGMA=  2.0 PHAS= -172.4 FOM= 0.89 TEST= 0
INDE 31 39 38 FOBS=   28.7 SIGMA=  7.1 PHAS=   20.6 FOM= 0.67 TEST= 0
INDE 31 39 40 FOBS=   47.6 SIGMA=  4.1 PHAS=   44.4 FOM= 0.75 TEST= 0
INDE 31 39 42 FOBS=   51.6 SIGMA=  3.6 PHAS=  166.5 FOM= 0.76 TEST= 0
INDE 31 39 44 FOBS=  120.5 SIGMA=  1.6 PHAS= -160.6 FOM= 0.91 TEST= 0
INDE 31 39 46 FOBS=   36.9 SIGMA=  5.4 PHAS=   17.5 FOM= 0.70 TEST= 0
INDE 31 39 48 FOBS=   74.5 SIGMA=  2.5 PHAS= -122.9 FOM= 0.56 TEST= 0
INDE 31 39 50 FOBS=   49.3 SIGMA=  3.7 PHAS=  -41.4 FOM= 0.63 TEST= 0
INDE 31 39 52 FOBS=   42.2 SIGMA=  4.9 PHAS=  -11.7 FOM= 0.65 TEST= 0
INDE 31 39 54 FOBS=   70.7 SIGMA=  2.8 PHAS=  179.4 FOM= 0.87 TEST= 0
INDE 31 39 56 FOBS=    0.0 SIGMA= 21.0 PHAS=    0.0 FOM= 0.00 TEST= 0
INDE 31 39 58 FOBS=   37.5 SIGMA=  6.0 PHAS=  154.0 FOM= 0.81 TEST= 0
INDE 31 40 31 FOBS=  142.6 SIGMA=  1.3 PHAS=   86.4 FOM= 0.95 TEST= 0
INDE 31 40 33 FOBS=    0.0 SIGMA= 20.2 PHAS=    0.0 FOM= 0.00 TEST= 0
INDE 31 40 35 FOBS=  118.2 SIGMA=  1.6 PHAS=   34.9 FOM= 0.93 TEST= 0
INDE 31 40 37 FOBS=   55.6 SIGMA=  3.3 PHAS=   68.0 FOM= 0.53 TEST= 0
INDE 31 40 39 FOBS=  171.5 SIGMA=  1.2 PHAS= -146.0 FOM= 0.96 TEST= 0
INDE 31 40 41 FOBS=  132.9 SIGMA=  1.5 PHAS=   34.1 FOM= 0.94 TEST= 0
INDE 31 40 43 FOBS=  111.5 SIGMA=  1.7 PHAS=   41.0 FOM= 0.89 TEST= 0
INDE 31 40 45 FOBS=   90.6 SIGMA=  2.0 PHAS= -134.3 FOM= 0.82 TEST= 0
INDE 31 40 47 FOBS=   85.7 SIGMA=  2.2 PHAS=  -20.1 FOM= 0.77 TEST= 0
INDE 31 40 49 FOBS=   85.7 SIGMA=  2.2 PHAS= -154.8 FOM= 0.89 TEST= 0
INDE 31 40 51 FOBS=   36.5 SIGMA=  5.0 PHAS=  171.3 FOM= 0.52 TEST= 0
INDE 31 40 53 FOBS=   45.2 SIGMA=  4.4 PHAS=   78.1 FOM= 0.64 TEST= 0
INDE 31 40 55 FOBS=   41.1 SIGMA=  5.4 PHAS=  -63.4 FOM= 0.72 TEST= 0
INDE 31 40 57 FOBS=   75.1 SIGMA=  3.0 PHAS=  -70.3 FOM= 0.91 TEST= 0
INDE 31 40 59 FOBS=    0.0 SIGMA= 29.8 PHAS=    0.0 FOM= 0.00 TEST= 0
INDE 31 41 32 FOBS=  109.2 SIGMA=  1.7 PHAS=  -67.1 FOM= 0.93 TEST= 0
INDE 31 41 34 FOBS=   57.0 SIGMA=  3.1 PHAS= -123.8 FOM= 0.78 TEST= 0
INDE 31 41 36 FOBS=  140.4 SIGMA=  1.4 PHAS= -125.2 FOM= 0.95 TEST= 0
INDE 31 41 38 FOBS=   60.0 SIGMA=  3.0 PHAS=   41.4 FOM= 0.85 TEST= 0
INDE 31 41 40 FOBS=   28.0 SIGMA=  6.8 PHAS=  -84.0 FOM= 0.31 TEST= 0
INDE 31 41 42 FOBS=   93.2 SIGMA=  2.0 PHAS=  -69.9 FOM= 0.91 TEST= 0
INDE 31 41 44 FOBS=   29.7 SIGMA=  6.5 PHAS=  117.7 FOM= 0.18 TEST= 0
INDE 31 41 46 FOBS=    0.0 SIGMA= 19.4 PHAS=    0.0 FOM= 0.00 TEST= 0
INDE 31 41 48 FOBS=   43.6 SIGMA=  4.4 PHAS= -153.2 FOM= 0.22 TEST= 1
INDE 31 41 50 FOBS=    0.0 SIGMA= 19.6 PHAS=    0.0 FOM= 0.00 TEST= 0
INDE 31 41 52 FOBS=  110.1 SIGMA=  1.8 PHAS=  -27.1 FOM= 0.95 TEST= 0
INDE 31 41 54 FOBS=   57.9 SIGMA=  3.9 PHAS=  164.6 FOM= 0.88 TEST= 0
INDE 31 41 56 FOBS=   54.5 SIGMA=  4.2 PHAS= -177.5 FOM= 0.77 TEST= 0
INDE 31 41 58 FOBS=   52.6 SIGMA=  4.8 PHAS= -179.0 FOM= 0.84 TEST= 0
INDE 31 42 31 FOBS=   83.4 SIGMA=  2.1 PHAS=   60.5 FOM= 0.91 TEST= 0
INDE 31 42 33 FOBS=   89.3 SIGMA=  1.9 PHAS= -146.6 FOM= 0.82 TEST= 0
INDE 31 42 35 FOBS=   91.9 SIGMA=  2.2 PHAS=  139.8 FOM= 0.91 TEST= 0
INDE 31 42 37 FOBS=   90.8 SIGMA=  2.0 PHAS= -155.2 FOM= 0.60 TEST= 0
INDE 31 42 39 FOBS=   95.3 SIGMA=  1.9 PHAS= -133.5 FOM= 0.17 TEST= 1
INDE 31 42 41 FOBS=   40.9 SIGMA=  4.5 PHAS=   53.5 FOM= 0.33 TEST= 0
INDE 31 42 43 FOBS=    0.0 SIGMA= 19.1 PHAS=    0.0 FOM= 0.00 TEST= 0
INDE 31 42 45 FOBS=  140.0 SIGMA=  1.4 PHAS= -174.4 FOM= 0.96 TEST= 0
INDE 31 42 47 FOBS=   35.5 SIGMA=  5.7 PHAS=  102.4 FOM= 0.19 TEST= 0
INDE 31 42 49 FOBS=   29.5 SIGMA=  6.6 PHAS= -124.7 FOM= 0.43 TEST= 0
INDE 31 42 51 FOBS=   82.9 SIGMA=  2.4 PHAS= -178.1 FOM= 0.90 TEST= 0
INDE 31 42 53 FOBS=   17.3 SIGMA= 13.0 PHAS=  168.4 FOM= 0.23 TEST= 0
INDE 31 42 55 FOBS=   77.6 SIGMA=  3.0 PHAS=   10.2 FOM= 0.80 TEST= 0
INDE 31 42 57 FOBS=    0.0 SIGMA= 26.2 PHAS=    0.0 FOM= 0.00 TEST= 0
INDE 31 43 32 FOBS=   71.0 SIGMA=  2.3 PHAS=  -46.8 FOM= 0.73 TEST= 0
```

*FIG. 12A - 541*

```
INDE 31 43 34 FOBS=   0.0 SIGMA= 18.3 PHAS=   0.0 FOM= 0.00 TEST= 0
INDE 31 43 36 FOBS=  61.2 SIGMA=  2.9 PHAS= -24.5 FOM= 0.05 TEST= 1
INDE 31 43 38 FOBS=  62.8 SIGMA=  2.6 PHAS= -19.1 FOM= 0.17 TEST= 0
INDE 31 43 40 FOBS=   0.0 SIGMA= 19.3 PHAS=   0.0 FOM= 0.00 TEST= 0
INDE 31 43 42 FOBS=  70.7 SIGMA=  2.6 PHAS= -84.3 FOM= 0.83 TEST= 0
INDE 31 43 44 FOBS=  72.3 SIGMA=  2.6 PHAS=  33.6 FOM= 0.87 TEST= 0
INDE 31 43 46 FOBS=  27.7 SIGMA=  6.7 PHAS= 116.3 FOM= 0.58 TEST= 0
INDE 31 43 48 FOBS=   0.0 SIGMA= 19.7 PHAS=   0.0 FOM= 0.00 TEST= 0
INDE 31 43 50 FOBS=  46.7 SIGMA=  4.0 PHAS= -27.3 FOM= 0.20 TEST= 0
INDE 31 43 52 FOBS=  61.7 SIGMA=  3.7 PHAS=  27.7 FOM= 0.81 TEST= 0
INDE 31 43 54 FOBS=   0.0 SIGMA= 22.1 PHAS=   0.0 FOM= 0.00 TEST= 0
INDE 31 43 56 FOBS=  25.4 SIGMA=  9.2 PHAS=-105.4 FOM= 0.16 TEST= 0
INDE 31 44 31 FOBS= 103.4 SIGMA=  1.6 PHAS=  -6.1 FOM= 0.39 TEST= 1
INDE 31 44 33 FOBS=  30.0 SIGMA=  5.6 PHAS=-105.9 FOM= 0.67 TEST= 0
INDE 31 44 35 FOBS=  60.5 SIGMA=  2.8 PHAS= 174.5 FOM= 0.62 TEST= 0
INDE 31 44 37 FOBS=  92.5 SIGMA=  1.9 PHAS= 135.7 FOM= 0.88 TEST= 0
INDE 31 44 39 FOBS=  29.9 SIGMA=  6.1 PHAS=  66.0 FOM= 0.33 TEST= 0
INDE 31 44 41 FOBS=  60.4 SIGMA=  2.8 PHAS=-150.6 FOM= 0.80 TEST= 0
INDE 31 44 43 FOBS=  59.6 SIGMA=  2.8 PHAS=-127.9 FOM= 0.86 TEST= 0
INDE 31 44 45 FOBS=   0.0 SIGMA= 20.6 PHAS=   0.0 FOM= 0.00 TEST= 0
INDE 31 44 47 FOBS=   0.0 SIGMA= 20.9 PHAS=   0.0 FOM= 0.00 TEST= 0
INDE 31 44 49 FOBS=  37.3 SIGMA=  5.0 PHAS= 164.6 FOM= 0.67 TEST= 0
INDE 31 44 51 FOBS=  79.7 SIGMA=  2.9 PHAS= 160.5 FOM= 0.94 TEST= 0
INDE 31 44 53 FOBS=  19.7 SIGMA= 12.7 PHAS= -71.1 FOM= 0.30 TEST= 0
INDE 31 44 55 FOBS=   0.0 SIGMA= 21.5 PHAS=   0.0 FOM= 0.00 TEST= 0
INDE 31 45 32 FOBS= 114.9 SIGMA=  1.5 PHAS=-162.2 FOM= 0.92 TEST= 0
INDE 31 45 34 FOBS=  83.2 SIGMA=  2.0 PHAS= 158.3 FOM= 0.55 TEST= 0
INDE 31 45 36 FOBS=  99.6 SIGMA=  1.8 PHAS=  55.8 FOM= 0.91 TEST= 0
INDE 31 45 38 FOBS=  86.6 SIGMA=  1.9 PHAS=  17.7 FOM= 0.81 TEST= 0
INDE 31 45 40 FOBS=   0.0 SIGMA= 18.4 PHAS=   0.0 FOM= 0.00 TEST= 0
INDE 31 45 42 FOBS=  77.3 SIGMA=  2.2 PHAS= 139.7 FOM= 0.89 TEST= 0
INDE 31 45 44 FOBS=  74.6 SIGMA=  2.3 PHAS= -34.4 FOM= 0.80 TEST= 0
INDE 31 45 46 FOBS=  19.9 SIGMA=  8.9 PHAS=-141.0 FOM= 0.27 TEST= 0
INDE 31 45 48 FOBS=  24.6 SIGMA=  8.5 PHAS=  85.0 FOM= 0.06 TEST= 1
INDE 31 45 50 FOBS= 124.7 SIGMA=  1.8 PHAS=  35.7 FOM= 0.97 TEST= 0
INDE 31 45 52 FOBS=  61.8 SIGMA=  3.8 PHAS=  69.2 FOM= 0.88 TEST= 0
INDE 31 45 54 FOBS=  90.3 SIGMA=  2.7 PHAS= 137.2 FOM= 0.87 TEST= 0
INDE 31 46 31 FOBS= 112.2 SIGMA=  1.5 PHAS=   8.7 FOM= 0.48 TEST= 1
INDE 31 46 33 FOBS=  73.1 SIGMA=  2.2 PHAS=-163.3 FOM= 0.67 TEST= 0
INDE 31 46 35 FOBS=  90.1 SIGMA=  1.9 PHAS=   9.0 FOM= 0.66 TEST= 0
INDE 31 46 37 FOBS=  40.6 SIGMA=  4.6 PHAS= 175.6 FOM= 0.42 TEST= 0
INDE 31 46 39 FOBS=  48.0 SIGMA=  3.6 PHAS=-120.6 FOM= 0.53 TEST= 0
INDE 31 46 41 FOBS=  36.1 SIGMA=  4.8 PHAS= 115.7 FOM= 0.23 TEST= 1
INDE 31 46 43 FOBS=  44.9 SIGMA=  3.8 PHAS= 133.0 FOM= 0.19 TEST= 0
INDE 31 46 45 FOBS=  68.3 SIGMA=  2.5 PHAS= -98.6 FOM= 0.53 TEST= 0
INDE 31 46 47 FOBS=   0.0 SIGMA= 19.3 PHAS=   0.0 FOM= 0.00 TEST= 0
INDE 31 46 49 FOBS= 109.6 SIGMA=  1.8 PHAS=  41.5 FOM= 0.87 TEST= 0
INDE 31 46 51 FOBS=  37.2 SIGMA=  6.9 PHAS=  25.7 FOM= 0.44 TEST= 1
INDE 31 46 53 FOBS=  95.7 SIGMA=  2.6 PHAS=  37.7 FOM= 0.94 TEST= 0
INDE 31 47 32 FOBS=  57.0 SIGMA=  2.8 PHAS=-124.5 FOM= 0.90 TEST= 0
INDE 31 47 34 FOBS=  66.3 SIGMA=  2.5 PHAS=  56.9 FOM= 0.37 TEST= 0
INDE 31 47 36 FOBS=  93.8 SIGMA=  2.0 PHAS=  -1.9 FOM= 0.83 TEST= 0
INDE 31 47 38 FOBS=  16.8 SIGMA= 10.6 PHAS=  81.9 FOM= 0.46 TEST= 0
INDE 31 47 40 FOBS=  96.7 SIGMA=  1.8 PHAS=  96.0 FOM= 0.83 TEST= 0
INDE 31 47 42 FOBS=  18.8 SIGMA=  9.7 PHAS= -48.6 FOM= 0.47 TEST= 0
INDE 31 47 44 FOBS=  67.0 SIGMA=  2.5 PHAS= -10.6 FOM= 0.89 TEST= 0
INDE 31 47 46 FOBS=  71.6 SIGMA=  2.7 PHAS=-145.1 FOM= 0.82 TEST= 0
INDE 31 47 48 FOBS=  74.4 SIGMA=  2.8 PHAS= -30.2 FOM= 0.90 TEST= 0
INDE 31 47 50 FOBS=  40.6 SIGMA=  5.5 PHAS=  10.6 FOM= 0.69 TEST= 0
INDE 31 47 52 FOBS=  95.7 SIGMA=  2.4 PHAS= -22.6 FOM= 0.96 TEST= 0
INDE 31 48 31 FOBS=  37.5 SIGMA=  4.5 PHAS=-166.9 FOM= 0.63 TEST= 0
INDE 31 48 33 FOBS=  15.6 SIGMA= 12.5 PHAS= 153.3 FOM= 0.05 TEST= 0
INDE 31 48 35 FOBS=  51.8 SIGMA=  3.2 PHAS=-114.3 FOM= 0.77 TEST= 0
INDE 31 48 37 FOBS=  10.3 SIGMA= 17.3 PHAS= -54.3 FOM= 0.20 TEST= 0
INDE 31 48 39 FOBS=   0.0 SIGMA= 19.0 PHAS=   0.0 FOM= 0.00 TEST= 0
INDE 31 48 41 FOBS=   0.0 SIGMA= 18.5 PHAS=   0.0 FOM= 0.00 TEST= 0
INDE 31 48 43 FOBS=  86.3 SIGMA=  2.1 PHAS=-113.4 FOM= 0.89 TEST= 0
INDE 31 48 45 FOBS=  79.2 SIGMA=  2.6 PHAS=-135.1 FOM= 0.90 TEST= 0
INDE 31 48 47 FOBS=   0.0 SIGMA= 20.2 PHAS=   0.0 FOM= 0.00 TEST= 0
INDE 31 48 49 FOBS=  85.3 SIGMA=  2.6 PHAS=   6.3 FOM= 0.07 TEST= 1
```

*FIG. 12A - 542*

```
INDE 31 48 51 FOBS=    28.9 SIGMA=  9.2 PHAS=  -87.7 FOM= 0.56 TEST= 0
INDE 31 49 32 FOBS=    23.9 SIGMA=  6.6 PHAS=   96.9 FOM= 0.07 TEST= 1
INDE 31 49 34 FOBS=    27.1 SIGMA=  6.5 PHAS=   84.7 FOM= 0.27 TEST= 0
INDE 31 49 36 FOBS=     0.0 SIGMA= 18.4 PHAS=    0.0 FOM= 0.00 TEST= 0
INDE 31 49 38 FOBS=     0.0 SIGMA= 19.5 PHAS=    0.0 FOM= 0.00 TEST= 0
INDE 31 49 40 FOBS=    50.3 SIGMA=  3.5 PHAS=  101.1 FOM= 0.45 TEST= 1
INDE 31 49 42 FOBS=    64.9 SIGMA=  2.9 PHAS=   41.7 FOM= 0.83 TEST= 0
INDE 31 49 44 FOBS=    94.4 SIGMA=  2.3 PHAS=  126.7 FOM= 0.94 TEST= 0
INDE 31 49 46 FOBS=    95.4 SIGMA=  2.3 PHAS=  144.9 FOM= 0.90 TEST= 0
INDE 31 49 48 FOBS=   126.9 SIGMA=  1.8 PHAS=   -2.3 FOM= 0.97 TEST= 0
INDE 31 49 50 FOBS=     0.0 SIGMA= 23.1 PHAS=    0.0 FOM= 0.00 TEST= 0
INDE 31 50 31 FOBS=     0.0 SIGMA= 18.5 PHAS=    0.0 FOM= 0.00 TEST= 0
INDE 31 50 33 FOBS=    70.9 SIGMA=  2.3 PHAS=  -24.2 FOM= 0.79 TEST= 0
INDE 31 50 35 FOBS=    84.8 SIGMA=  2.0 PHAS= -166.3 FOM= 0.20 TEST= 1
INDE 31 50 37 FOBS=    88.5 SIGMA=  2.2 PHAS=  -83.5 FOM= 0.79 TEST= 0
INDE 31 50 39 FOBS=    38.4 SIGMA=  5.7 PHAS= -110.8 FOM= 0.71 TEST= 0
INDE 31 50 41 FOBS=    45.9 SIGMA=  4.6 PHAS=   47.5 FOM= 0.71 TEST= 1
INDE 31 50 43 FOBS=    38.5 SIGMA=  6.5 PHAS=   69.8 FOM= 0.25 TEST= 0
INDE 31 50 45 FOBS=    15.5 SIGMA= 14.7 PHAS=   50.1 FOM= 0.29 TEST= 0
INDE 31 50 47 FOBS=     9.9 SIGMA= 22.4 PHAS=  -65.7 FOM= 0.12 TEST= 0
INDE 31 50 49 FOBS=     0.0 SIGMA= 23.1 PHAS=    0.0 FOM= 0.00 TEST= 0
INDE 31 51 32 FOBS=     0.0 SIGMA= 18.6 PHAS=    0.0 FOM= 0.00 TEST= 0
INDE 31 51 34 FOBS=    33.9 SIGMA=  5.5 PHAS= -105.3 FOM= 0.37 TEST= 0
INDE 31 51 36 FOBS=     0.0 SIGMA= 21.6 PHAS=    0.0 FOM= 0.00 TEST= 0
INDE 31 51 38 FOBS=   105.9 SIGMA=  2.0 PHAS= -144.5 FOM= 0.90 TEST= 0
INDE 31 51 40 FOBS=    33.8 SIGMA=  7.9 PHAS= -105.8 FOM= 0.70 TEST= 0
INDE 31 51 42 FOBS=    69.3 SIGMA=  3.1 PHAS=  113.3 FOM= 0.88 TEST= 0
INDE 31 51 44 FOBS=    64.7 SIGMA=  3.4 PHAS=   47.1 FOM= 0.56 TEST= 0
INDE 31 51 46 FOBS=    31.1 SIGMA=  7.1 PHAS= -170.0 FOM= 0.24 TEST= 0
INDE 31 51 48 FOBS=    86.3 SIGMA=  2.7 PHAS=   37.0 FOM= 0.91 TEST= 0
INDE 31 52 31 FOBS=    82.8 SIGMA=  2.2 PHAS=    9.0 FOM= 0.86 TEST= 0
INDE 31 52 33 FOBS=    44.4 SIGMA=  4.0 PHAS=  -13.2 FOM= 0.35 TEST= 0
INDE 31 52 35 FOBS=    79.4 SIGMA=  2.3 PHAS=  133.7 FOM= 0.94 TEST= 0
INDE 31 52 37 FOBS=    47.4 SIGMA=  5.1 PHAS= -179.0 FOM= 0.47 TEST= 0
INDE 31 52 39 FOBS=    60.2 SIGMA=  4.1 PHAS= -155.5 FOM= 0.91 TEST= 0
INDE 31 52 41 FOBS=    98.8 SIGMA=  2.4 PHAS=   82.1 FOM= 0.79 TEST= 0
INDE 31 52 43 FOBS=    27.2 SIGMA=  8.6 PHAS=   39.7 FOM= 0.37 TEST= 0
INDE 31 52 45 FOBS=    41.5 SIGMA=  5.3 PHAS=  -52.2 FOM= 0.47 TEST= 0
INDE 31 52 47 FOBS=    47.0 SIGMA=  4.9 PHAS=    4.4 FOM= 0.77 TEST= 0
INDE 31 53 32 FOBS=    69.9 SIGMA=  2.7 PHAS=  -45.0 FOM= 0.78 TEST= 0
INDE 31 53 34 FOBS=     0.0 SIGMA= 19.1 PHAS=    0.0 FOM= 0.00 TEST= 0
INDE 31 53 36 FOBS=    87.0 SIGMA=  2.4 PHAS= -102.3 FOM= 0.37 TEST= 1
INDE 31 53 38 FOBS=    73.5 SIGMA=  3.3 PHAS=  144.1 FOM= 0.89 TEST= 0
INDE 31 53 40 FOBS=    66.8 SIGMA=  3.8 PHAS=   29.5 FOM= 0.78 TEST= 0
INDE 31 53 42 FOBS=    45.7 SIGMA=  4.8 PHAS=  112.7 FOM= 0.67 TEST= 0
INDE 31 53 44 FOBS=    43.1 SIGMA=  5.1 PHAS=  -48.7 FOM= 0.28 TEST= 0
INDE 31 53 46 FOBS=    16.1 SIGMA= 16.2 PHAS= -105.4 FOM= 0.07 TEST= 0
INDE 31 54 31 FOBS=    56.3 SIGMA=  3.3 PHAS=   51.4 FOM= 0.79 TEST= 0
INDE 31 54 33 FOBS=    81.6 SIGMA=  2.5 PHAS= -123.7 FOM= 0.91 TEST= 0
INDE 31 54 35 FOBS=   104.9 SIGMA=  2.1 PHAS=  158.1 FOM= 0.94 TEST= 0
INDE 31 54 37 FOBS=    69.0 SIGMA=  3.5 PHAS=   64.1 FOM= 0.68 TEST= 0
INDE 31 54 39 FOBS=    40.0 SIGMA=  6.8 PHAS= -113.2 FOM= 0.24 TEST= 0
INDE 31 54 41 FOBS=    75.4 SIGMA=  3.4 PHAS=   -0.1 FOM= 0.87 TEST= 0
INDE 31 54 43 FOBS=     0.0 SIGMA= 21.7 PHAS=    0.0 FOM= 0.00 TEST= 0
INDE 31 54 45 FOBS=    55.2 SIGMA=  4.1 PHAS=  -59.4 FOM= 0.54 TEST= 0
INDE 31 55 32 FOBS=    35.8 SIGMA=  5.8 PHAS= -150.4 FOM= 0.06 TEST= 0
INDE 31 55 34 FOBS=    90.7 SIGMA=  2.4 PHAS=  141.7 FOM= 0.94 TEST= 0
INDE 31 55 36 FOBS=    77.1 SIGMA=  2.9 PHAS=  -67.3 FOM= 0.92 TEST= 0
INDE 31 55 38 FOBS=    95.0 SIGMA=  2.7 PHAS=  122.0 FOM= 0.89 TEST= 0
INDE 31 55 40 FOBS=    41.0 SIGMA=  6.1 PHAS=  -43.2 FOM= 0.39 TEST= 0
INDE 31 55 42 FOBS=    17.6 SIGMA= 18.2 PHAS= -147.7 FOM= 0.41 TEST= 0
INDE 31 55 44 FOBS=     0.0 SIGMA= 22.5 PHAS=    0.0 FOM= 0.00 TEST= 0
INDE 31 56 31 FOBS=    40.9 SIGMA=  6.8 PHAS=  -37.7 FOM= 0.05 TEST= 1
INDE 31 56 33 FOBS=     0.0 SIGMA= 22.5 PHAS=    0.0 FOM= 0.00 TEST= 0
INDE 31 56 35 FOBS=    46.4 SIGMA=  5.1 PHAS=   90.4 FOM= 0.74 TEST= 0
INDE 31 56 37 FOBS=    19.6 SIGMA= 12.5 PHAS=   54.4 FOM= 0.10 TEST= 0
INDE 31 56 39 FOBS=    34.7 SIGMA=  7.2 PHAS=  -70.6 FOM= 0.20 TEST= 0
INDE 31 56 41 FOBS=    64.8 SIGMA=  4.0 PHAS=    8.8 FOM= 0.87 TEST= 0
INDE 31 56 43 FOBS=     0.0 SIGMA= 21.9 PHAS=    0.0 FOM= 0.00 TEST= 0
INDE 31 57 32 FOBS=     0.0 SIGMA= 22.7 PHAS=    0.0 FOM= 0.00 TEST= 0
```

*FIG. 12A - 543*

```
INDE 31 57 34 FOBS=    0.0 SIGMA= 21.7 PHAS=    0.0 FOM= 0.00 TEST= 0
INDE 31 57 36 FOBS=   66.9 SIGMA=  3.4 PHAS=  -67.0 FOM= 0.89 TEST= 0
INDE 31 57 38 FOBS=   87.8 SIGMA=  2.9 PHAS=   95.7 FOM= 0.90 TEST= 0
INDE 31 57 40 FOBS=   36.2 SIGMA=  7.8 PHAS=  176.3 FOM= 0.62 TEST= 0
INDE 31 57 42 FOBS=    0.0 SIGMA= 23.0 PHAS=    0.0 FOM= 0.00 TEST= 1
INDE 31 58 31 FOBS=    0.0 SIGMA= 23.9 PHAS=    0.0 FOM= 0.00 TEST= 0
INDE 31 58 33 FOBS=   23.6 SIGMA=  9.7 PHAS=  109.5 FOM= 0.25 TEST= 0
INDE 31 58 35 FOBS=   54.9 SIGMA=  4.0 PHAS=  144.4 FOM= 0.01 TEST= 1
INDE 31 58 37 FOBS=   61.2 SIGMA=  3.9 PHAS=  -57.5 FOM= 0.60 TEST= 0
INDE 31 58 39 FOBS=   73.1 SIGMA=  3.5 PHAS=   27.4 FOM= 0.91 TEST= 0
INDE 31 58 41 FOBS=   67.6 SIGMA=  4.0 PHAS=    7.1 FOM= 0.81 TEST= 0
INDE 31 59 32 FOBS=   47.5 SIGMA=  7.0 PHAS=   52.1 FOM= 0.13 TEST= 1
INDE 31 59 34 FOBS=   29.6 SIGMA=  8.6 PHAS=   40.7 FOM= 0.03 TEST= 1
INDE 31 59 36 FOBS=   69.1 SIGMA=  3.3 PHAS= -106.7 FOM= 0.88 TEST= 0
INDE 31 59 38 FOBS=   51.2 SIGMA=  4.5 PHAS=  -87.0 FOM= 0.73 TEST= 0
INDE 31 59 40 FOBS=   57.6 SIGMA=  6.4 PHAS= -113.6 FOM= 0.77 TEST= 0
INDE 31 60 31 FOBS=  119.2 SIGMA=  2.2 PHAS= -155.5 FOM= 0.96 TEST= 0
INDE 31 60 33 FOBS=   36.5 SIGMA=  8.1 PHAS=   94.6 FOM= 0.06 TEST= 1
INDE 31 60 35 FOBS=   46.7 SIGMA=  5.7 PHAS=   94.3 FOM= 0.23 TEST= 1
INDE 31 60 37 FOBS=   19.8 SIGMA= 12.4 PHAS= -179.2 FOM= 0.41 TEST= 0
INDE 31 61 32 FOBS=  102.7 SIGMA=  2.6 PHAS=   75.7 FOM= 0.95 TEST= 0
INDE 31 61 34 FOBS=    0.0 SIGMA= 21.0 PHAS=    0.0 FOM= 0.00 TEST= 0
INDE 31 61 36 FOBS=   46.7 SIGMA=  4.9 PHAS=   48.6 FOM= 0.80 TEST= 0
INDE 31 62 31 FOBS=   52.1 SIGMA=  5.0 PHAS=   10.7 FOM= 0.50 TEST= 0
INDE 31 62 33 FOBS=   34.4 SIGMA=  8.6 PHAS=  -19.1 FOM= 0.47 TEST= 0
INDE 31 62 35 FOBS=   78.3 SIGMA=  3.2 PHAS=  -71.8 FOM= 0.87 TEST= 0
INDE 31 63 32 FOBS=    0.0 SIGMA= 29.0 PHAS=    0.0 FOM= 0.00 TEST= 0
INDE 31 64 31 FOBS=    0.0 SIGMA= 34.2 PHAS=    0.0 FOM= 0.00 TEST= 0
INDE 32 32 32 FOBS=  140.9 SIGMA=  2.2 PHAS=   54.2 FOM= 0.98 TEST= 0
INDE 32 33 33 FOBS=    0.0 SIGMA= 18.2 PHAS=    0.0 FOM= 0.00 TEST= 0
INDE 32 33 35 FOBS=   71.0 SIGMA=  2.4 PHAS= -118.3 FOM= 0.89 TEST= 0
INDE 32 33 37 FOBS=   14.9 SIGMA= 12.3 PHAS=  177.8 FOM= 0.09 TEST= 0
INDE 32 33 39 FOBS=   28.2 SIGMA=  6.5 PHAS=   32.2 FOM= 0.17 TEST= 0
INDE 32 33 41 FOBS=  131.4 SIGMA=  1.5 PHAS= -156.5 FOM= 0.96 TEST= 0
INDE 32 33 43 FOBS=   69.8 SIGMA=  2.7 PHAS=  159.7 FOM= 0.26 TEST= 1
INDE 32 33 45 FOBS=   89.8 SIGMA=  2.1 PHAS=  106.0 FOM= 0.87 TEST= 0
INDE 32 33 47 FOBS=    0.0 SIGMA= 19.3 PHAS=    0.0 FOM= 0.00 TEST= 0
INDE 32 33 49 FOBS=   27.8 SIGMA=  6.3 PHAS=  118.2 FOM= 0.44 TEST= 0
INDE 32 33 51 FOBS=   45.0 SIGMA=  4.5 PHAS=  -49.2 FOM= 0.75 TEST= 0
INDE 32 33 53 FOBS=   47.1 SIGMA=  4.0 PHAS=  -53.3 FOM= 0.81 TEST= 0
INDE 32 33 55 FOBS=   54.5 SIGMA=  3.5 PHAS=   77.4 FOM= 0.82 TEST= 0
INDE 32 33 57 FOBS=    0.0 SIGMA= 19.9 PHAS=    0.0 FOM= 0.00 TEST= 0
INDE 32 33 59 FOBS=    0.0 SIGMA= 20.9 PHAS=    0.0 FOM= 0.00 TEST= 0
INDE 32 33 61 FOBS=   51.5 SIGMA=  5.1 PHAS=  134.4 FOM= 0.85 TEST= 0
INDE 32 34 32 FOBS=  127.7 SIGMA=  1.4 PHAS=   97.4 FOM= 0.25 TEST= 0
INDE 32 34 34 FOBS=  108.3 SIGMA=  1.6 PHAS= -101.8 FOM= 0.81 TEST= 1
INDE 32 34 36 FOBS=    0.0 SIGMA= 19.2 PHAS=    0.0 FOM= 0.00 TEST= 0
INDE 32 34 38 FOBS=    9.6 SIGMA= 19.3 PHAS=  -91.1 FOM= 0.37 TEST= 0
INDE 32 34 40 FOBS=   64.9 SIGMA=  2.9 PHAS=   88.7 FOM= 0.80 TEST= 0
INDE 32 34 42 FOBS=  125.0 SIGMA=  1.5 PHAS=   84.1 FOM= 0.89 TEST= 0
INDE 32 34 44 FOBS=   70.5 SIGMA=  2.6 PHAS=  -48.9 FOM= 0.91 TEST= 0
INDE 32 34 46 FOBS=   40.5 SIGMA=  4.5 PHAS=  -99.0 FOM= 0.03 TEST= 1
INDE 32 34 48 FOBS=  101.0 SIGMA=  1.8 PHAS=   57.9 FOM= 0.90 TEST= 0
INDE 32 34 50 FOBS=   90.3 SIGMA=  2.0 PHAS= -142.7 FOM= 0.92 TEST= 0
INDE 32 34 52 FOBS=   87.4 SIGMA=  2.1 PHAS=  155.6 FOM= 0.89 TEST= 0
INDE 32 34 54 FOBS=   75.6 SIGMA=  2.5 PHAS=  -84.4 FOM= 0.89 TEST= 0
INDE 32 34 56 FOBS=   44.3 SIGMA=  4.5 PHAS=  101.0 FOM= 0.77 TEST= 0
INDE 32 34 58 FOBS=   53.5 SIGMA=  3.6 PHAS=  120.3 FOM= 0.78 TEST= 0
INDE 32 34 60 FOBS=    0.0 SIGMA= 22.0 PHAS=    0.0 FOM= 0.00 TEST= 1
INDE 32 34 62 FOBS=   93.3 SIGMA=  3.0 PHAS=  -29.3 FOM= 0.21 TEST= 1
INDE 32 35 33 FOBS=   66.0 SIGMA=  2.6 PHAS=  -73.4 FOM= 0.09 TEST= 1
INDE 32 35 35 FOBS=  112.1 SIGMA=  1.5 PHAS= -138.7 FOM= 0.92 TEST= 0
INDE 32 35 37 FOBS=   75.9 SIGMA=  2.5 PHAS=  174.7 FOM= 0.62 TEST= 0
INDE 32 35 39 FOBS=   96.1 SIGMA=  2.0 PHAS=   64.5 FOM= 0.71 TEST= 0
INDE 32 35 41 FOBS=   55.2 SIGMA=  3.3 PHAS=  110.8 FOM= 0.53 TEST= 0
INDE 32 35 43 FOBS=   40.3 SIGMA=  4.8 PHAS=  -83.6 FOM= 0.82 TEST= 0
INDE 32 35 45 FOBS=   76.9 SIGMA=  2.5 PHAS= -177.4 FOM= 0.58 TEST= 0
INDE 32 35 47 FOBS=   87.4 SIGMA=  2.1 PHAS= -148.2 FOM= 0.80 TEST= 0
INDE 32 35 49 FOBS=   90.4 SIGMA=  2.0 PHAS=  -61.4 FOM= 0.90 TEST= 0
INDE 32 35 51 FOBS=  100.1 SIGMA=  1.8 PHAS=    6.6 FOM= 0.20 TEST= 1
```

*FIG. 12A - 544*

```
INDE 32 35 53 FOBS=   0.0 SIGMA= 20.0 PHAS=   0.0 FOM= 0.00 TEST= 0
INDE 32 35 55 FOBS=  57.2 SIGMA=  3.3 PHAS=  71.2 FOM= 0.73 TEST= 0
INDE 32 35 57 FOBS=  23.8 SIGMA=  8.5 PHAS=  90.0 FOM= 0.52 TEST= 0
INDE 32 35 59 FOBS=   0.0 SIGMA= 19.8 PHAS=   0.0 FOM= 0.00 TEST= 0
INDE 32 35 61 FOBS=  32.0 SIGMA=  7.2 PHAS=-117.2 FOM= 0.53 TEST= 0
INDE 32 36 32 FOBS= 113.8 SIGMA=  1.8 PHAS= -90.2 FOM= 0.75 TEST= 0
INDE 32 36 34 FOBS=  49.6 SIGMA=  3.4 PHAS= 124.3 FOM= 0.86 TEST= 0
INDE 32 36 36 FOBS= 143.9 SIGMA=  1.4 PHAS=  92.0 FOM= 0.96 TEST= 0
INDE 32 36 38 FOBS=  67.4 SIGMA=  2.8 PHAS=   2.5 FOM= 0.81 TEST= 0
INDE 32 36 40 FOBS=  74.5 SIGMA=  2.5 PHAS= 142.2 FOM= 0.84 TEST= 0
INDE 32 36 42 FOBS=  89.1 SIGMA=  2.1 PHAS=  68.8 FOM= 0.92 TEST= 0
INDE 32 36 44 FOBS= 148.2 SIGMA=  1.3 PHAS=-100.9 FOM= 0.59 TEST= 1
INDE 32 36 46 FOBS=  33.3 SIGMA=  5.4 PHAS= 147.4 FOM= 0.66 TEST= 0
INDE 32 36 48 FOBS=  64.6 SIGMA=  2.8 PHAS=-154.7 FOM= 0.83 TEST= 0
INDE 32 36 50 FOBS= 255.9 SIGMA=  1.0 PHAS=-113.3 FOM= 0.99 TEST= 0
INDE 32 36 52 FOBS=   0.0 SIGMA= 19.4 PHAS=   0.0 FOM= 0.00 TEST= 0
INDE 32 36 54 FOBS=  50.2 SIGMA=  4.0 PHAS=-118.9 FOM= 0.76 TEST= 0
INDE 32 36 56 FOBS=  18.7 SIGMA= 12.6 PHAS=  54.4 FOM= 0.20 TEST= 0
INDE 32 36 58 FOBS=  91.1 SIGMA=  2.2 PHAS=  50.1 FOM= 0.88 TEST= 0
INDE 32 36 60 FOBS=  57.4 SIGMA=  3.5 PHAS= 174.8 FOM= 0.85 TEST= 0
INDE 32 37 33 FOBS=   0.0 SIGMA= 19.6 PHAS=   0.0 FOM= 0.00 TEST= 0
INDE 32 37 35 FOBS= 111.2 SIGMA=  1.6 PHAS=  11.8 FOM= 0.85 TEST= 0
INDE 32 37 37 FOBS=   0.0 SIGMA= 19.1 PHAS=   0.0 FOM= 0.00 TEST= 1
INDE 32 37 39 FOBS= 108.7 SIGMA=  1.8 PHAS=  81.8 FOM= 0.96 TEST= 0
INDE 32 37 41 FOBS= 139.7 SIGMA=  1.4 PHAS= -14.4 FOM= 0.98 TEST= 0
INDE 32 37 43 FOBS=  59.4 SIGMA=  3.1 PHAS= -57.6 FOM= 0.70 TEST= 0
INDE 32 37 45 FOBS= 143.1 SIGMA=  1.3 PHAS= 160.4 FOM= 0.97 TEST= 0
INDE 32 37 47 FOBS=  34.6 SIGMA=  5.7 PHAS=-119.5 FOM= 0.35 TEST= 0
INDE 32 37 49 FOBS=  73.4 SIGMA=  2.5 PHAS= 159.3 FOM= 0.88 TEST= 0
INDE 32 37 51 FOBS=  89.4 SIGMA=  2.1 PHAS=-175.7 FOM= 0.93 TEST= 0
INDE 32 37 53 FOBS=  62.2 SIGMA=  3.1 PHAS=-175.9 FOM= 0.82 TEST= 0
INDE 32 37 55 FOBS=  29.8 SIGMA=  7.8 PHAS=-115.6 FOM= 0.05 TEST= 1
INDE 32 37 57 FOBS=  31.9 SIGMA=  6.6 PHAS= 150.0 FOM= 0.03 TEST= 0
INDE 32 37 59 FOBS=  23.5 SIGMA=  8.5 PHAS=  78.3 FOM= 0.36 TEST= 0
INDE 32 38 32 FOBS=  92.6 SIGMA=  2.0 PHAS=  66.6 FOM= 0.89 TEST= 0
INDE 32 38 34 FOBS=  68.7 SIGMA=  2.4 PHAS= 160.5 FOM= 0.89 TEST= 0
INDE 32 38 36 FOBS=  36.8 SIGMA=  4.7 PHAS= 154.5 FOM= 0.12 TEST= 1
INDE 32 38 38 FOBS=  86.9 SIGMA=  2.2 PHAS= -14.9 FOM= 0.93 TEST= 0
INDE 32 38 40 FOBS=  76.8 SIGMA=  2.4 PHAS=-112.0 FOM= 0.90 TEST= 0
INDE 32 38 42 FOBS=  42.2 SIGMA=  4.3 PHAS=-113.6 FOM= 0.81 TEST= 0
INDE 32 38 44 FOBS=  62.3 SIGMA=  3.0 PHAS=  27.0 FOM= 0.76 TEST= 0
INDE 32 38 46 FOBS=  39.9 SIGMA=  4.5 PHAS= 134.5 FOM= 0.68 TEST= 0
INDE 32 38 48 FOBS= 103.9 SIGMA=  1.8 PHAS= 142.9 FOM= 0.79 TEST= 0
INDE 32 38 50 FOBS= 137.5 SIGMA=  1.4 PHAS=-169.5 FOM= 0.96 TEST= 0
INDE 32 38 52 FOBS= 109.9 SIGMA=  1.8 PHAS=  97.2 FOM= 0.96 TEST= 0
INDE 32 38 54 FOBS=   0.0 SIGMA= 20.2 PHAS=   0.0 FOM= 0.00 TEST= 1
INDE 32 38 56 FOBS=  40.3 SIGMA=  4.9 PHAS= -13.7 FOM= 0.13 TEST= 0
INDE 32 38 58 FOBS=   0.0 SIGMA= 20.5 PHAS=   0.0 FOM= 0.00 TEST= 0
INDE 32 39 33 FOBS=  84.0 SIGMA=  2.2 PHAS=  55.2 FOM= 0.92 TEST= 0
INDE 32 39 35 FOBS= 121.0 SIGMA=  1.4 PHAS= -13.7 FOM= 0.82 TEST= 0
INDE 32 39 37 FOBS=  20.0 SIGMA= 11.8 PHAS= 110.0 FOM= 0.24 TEST= 0
INDE 32 39 39 FOBS=  88.1 SIGMA=  2.1 PHAS= 151.1 FOM= 0.94 TEST= 0
INDE 32 39 41 FOBS=  66.1 SIGMA=  2.8 PHAS=-122.5 FOM= 0.68 TEST= 0
INDE 32 39 43 FOBS=  52.4 SIGMA=  3.5 PHAS= -40.9 FOM= 0.62 TEST= 0
INDE 32 39 45 FOBS=  70.2 SIGMA=  2.6 PHAS= 135.1 FOM= 0.82 TEST= 0
INDE 32 39 47 FOBS=   0.0 SIGMA= 19.1 PHAS=   0.0 FOM= 0.00 TEST= 0
INDE 32 39 49 FOBS= 106.2 SIGMA=  1.8 PHAS= 103.4 FOM= 0.96 TEST= 0
INDE 32 39 51 FOBS=  92.4 SIGMA=  2.2 PHAS=  71.3 FOM= 0.86 TEST= 0
INDE 32 39 53 FOBS=  44.3 SIGMA=  4.4 PHAS= -74.6 FOM= 0.46 TEST= 0
INDE 32 39 55 FOBS=  54.8 SIGMA=  3.6 PHAS= 152.1 FOM= 0.78 TEST= 0
INDE 32 39 57 FOBS=  80.0 SIGMA=  2.5 PHAS= 174.4 FOM= 0.93 TEST= 0
INDE 32 39 59 FOBS=  60.9 SIGMA=  4.1 PHAS=  87.9 FOM= 0.68 TEST= 0
INDE 32 40 32 FOBS=  82.8 SIGMA=  2.2 PHAS= -44.8 FOM= 0.82 TEST= 0
INDE 32 40 34 FOBS=  41.0 SIGMA=  5.3 PHAS= 166.7 FOM= 0.44 TEST= 0
INDE 32 40 36 FOBS=   0.0 SIGMA= 19.5 PHAS=   0.0 FOM= 0.00 TEST= 0
INDE 32 40 38 FOBS= 169.5 SIGMA=  1.2 PHAS= -88.6 FOM= 0.95 TEST= 0
INDE 32 40 40 FOBS= 103.6 SIGMA=  1.8 PHAS=  79.7 FOM= 0.93 TEST= 0
INDE 32 40 42 FOBS=  27.6 SIGMA=  7.1 PHAS= 134.0 FOM= 0.25 TEST= 0
INDE 32 40 44 FOBS=  75.8 SIGMA=  2.4 PHAS= -38.8 FOM= 0.79 TEST= 0
INDE 32 40 46 FOBS=   0.0 SIGMA= 19.0 PHAS=   0.0 FOM= 0.00 TEST= 1
```

*FIG. 12A - 545*

```
INDE 32 40 48 FOBS=    28.8 SIGMA=  6.8 PHAS=  115.2 FOM= 0.11 TEST= 0
INDE 32 40 50 FOBS=    27.8 SIGMA=  6.6 PHAS=    7.5 FOM= 0.52 TEST= 0
INDE 32 40 52 FOBS=     0.0 SIGMA= 20.4 PHAS=    0.0 FOM= 0.00 TEST= 0
INDE 32 40 54 FOBS=    91.5 SIGMA=  2.2 PHAS=   29.5 FOM= 0.95 TEST= 0
INDE 32 40 56 FOBS=    70.2 SIGMA=  2.9 PHAS=   62.6 FOM= 0.84 TEST= 0
INDE 32 40 58 FOBS=    64.2 SIGMA=  3.6 PHAS=   91.0 FOM= 0.84 TEST= 0
INDE 32 41 33 FOBS=    61.4 SIGMA=  2.9 PHAS=   85.2 FOM= 0.77 TEST= 0
INDE 32 41 35 FOBS=    10.5 SIGMA= 22.5 PHAS=  -76.5 FOM= 0.17 TEST= 0
INDE 32 41 37 FOBS=   111.5 SIGMA=  1.7 PHAS=  149.9 FOM= 0.95 TEST= 0
INDE 32 41 39 FOBS=    83.8 SIGMA=  2.2 PHAS=  -96.1 FOM= 0.56 TEST= 0
INDE 32 41 41 FOBS=    77.1 SIGMA=  2.4 PHAS=  -53.8 FOM= 0.90 TEST= 0
INDE 32 41 43 FOBS=     0.0 SIGMA= 19.6 PHAS=    0.0 FOM= 0.00 TEST= 0
INDE 32 41 45 FOBS=    56.8 SIGMA=  3.3 PHAS=   91.1 FOM= 0.65 TEST= 0
INDE 32 41 47 FOBS=    81.4 SIGMA=  2.3 PHAS=  -14.5 FOM= 0.17 TEST= 1
INDE 32 41 49 FOBS=    18.4 SIGMA= 10.5 PHAS=  170.8 FOM= 0.20 TEST= 0
INDE 32 41 51 FOBS=    45.2 SIGMA=  4.3 PHAS=  102.7 FOM= 0.67 TEST= 0
INDE 32 41 53 FOBS=    92.5 SIGMA=  2.2 PHAS= -100.4 FOM= 0.93 TEST= 0
INDE 32 41 55 FOBS=    88.8 SIGMA=  2.3 PHAS=  -98.4 FOM= 0.91 TEST= 0
INDE 32 41 57 FOBS=    39.9 SIGMA=  5.8 PHAS= -110.2 FOM= 0.54 TEST= 0
INDE 32 42 32 FOBS=   142.4 SIGMA=  1.4 PHAS=  -56.6 FOM= 0.97 TEST= 0
INDE 32 42 34 FOBS=     0.0 SIGMA= 19.3 PHAS=    0.0 FOM= 0.00 TEST= 0
INDE 32 42 36 FOBS=     0.0 SIGMA= 19.5 PHAS=    0.0 FOM= 0.00 TEST= 0
INDE 32 42 38 FOBS=    88.9 SIGMA=  2.1 PHAS= -137.8 FOM= 0.88 TEST= 0
INDE 32 42 40 FOBS=   107.0 SIGMA=  1.8 PHAS=  104.4 FOM= 0.87 TEST= 0
INDE 32 42 42 FOBS=     0.0 SIGMA= 19.1 PHAS=    0.0 FOM= 0.00 TEST= 0
INDE 32 42 44 FOBS=   128.3 SIGMA=  1.5 PHAS=  -97.9 FOM= 0.95 TEST= 0
INDE 32 42 46 FOBS=     9.8 SIGMA= 19.7 PHAS=  111.3 FOM= 0.18 TEST= 0
INDE 32 42 48 FOBS=    64.7 SIGMA=  2.9 PHAS= -118.9 FOM= 0.15 TEST= 1
INDE 32 42 50 FOBS=    38.0 SIGMA=  5.2 PHAS=  -84.8 FOM= 0.19 TEST= 1
INDE 32 42 52 FOBS=    42.7 SIGMA=  5.7 PHAS= -105.3 FOM= 0.48 TEST= 0
INDE 32 42 54 FOBS=    55.8 SIGMA=  4.1 PHAS=  116.1 FOM= 0.78 TEST= 0
INDE 32 42 56 FOBS=    51.1 SIGMA=  4.5 PHAS=  178.7 FOM= 0.46 TEST= 0
INDE 32 43 33 FOBS=     0.0 SIGMA= 20.0 PHAS=    0.0 FOM= 0.00 TEST= 1
INDE 32 43 35 FOBS=    91.1 SIGMA=  2.0 PHAS=  150.2 FOM= 0.87 TEST= 0
INDE 32 43 37 FOBS=    44.6 SIGMA=  4.1 PHAS=   45.2 FOM= 0.37 TEST= 0
INDE 32 43 39 FOBS=    39.3 SIGMA=  5.1 PHAS=  177.9 FOM= 0.12 TEST= 0
INDE 32 43 41 FOBS=     0.0 SIGMA= 19.1 PHAS=    0.0 FOM= 0.00 TEST= 0
INDE 32 43 43 FOBS=   128.5 SIGMA=  1.5 PHAS=  143.5 FOM= 0.95 TEST= 0
INDE 32 43 45 FOBS=    68.9 SIGMA=  2.7 PHAS=  175.5 FOM= 0.79 TEST= 0
INDE 32 43 47 FOBS=     0.0 SIGMA= 19.7 PHAS=    0.0 FOM= 0.00 TEST= 0
INDE 32 43 49 FOBS=     0.0 SIGMA= 19.3 PHAS=    0.0 FOM= 0.00 TEST= 0
INDE 32 43 51 FOBS=    97.8 SIGMA=  2.1 PHAS=  134.2 FOM= 0.67 TEST= 1
INDE 32 43 53 FOBS=     0.0 SIGMA= 23.0 PHAS=    0.0 FOM= 0.00 TEST= 0
INDE 32 43 55 FOBS=     9.0 SIGMA= 27.9 PHAS=  -59.7 FOM= 0.04 TEST= 0
INDE 32 44 32 FOBS=     0.0 SIGMA= 18.4 PHAS=    0.0 FOM= 0.00 TEST= 1
INDE 32 44 34 FOBS=   112.1 SIGMA=  1.7 PHAS=   99.8 FOM= 0.19 TEST= 1
INDE 32 44 36 FOBS=    53.6 SIGMA=  3.4 PHAS=  -62.6 FOM= 0.40 TEST= 0
INDE 32 44 38 FOBS=     0.0 SIGMA= 21.4 PHAS=    0.0 FOM= 0.00 TEST= 0
INDE 32 44 40 FOBS=    51.3 SIGMA=  3.8 PHAS=   82.6 FOM= 0.41 TEST= 0
INDE 32 44 42 FOBS=    97.1 SIGMA=  2.0 PHAS=   69.1 FOM= 0.91 TEST= 0
INDE 32 44 44 FOBS=    31.5 SIGMA=  6.6 PHAS= -152.1 FOM= 0.60 TEST= 0
INDE 32 44 46 FOBS=     0.0 SIGMA= 19.3 PHAS=    0.0 FOM= 0.00 TEST= 0
INDE 32 44 48 FOBS=     0.0 SIGMA= 19.2 PHAS=    0.0 FOM= 0.00 TEST= 0
INDE 32 44 50 FOBS=    84.7 SIGMA=  2.3 PHAS=  -79.1 FOM= 0.93 TEST= 0
INDE 32 44 52 FOBS=    94.6 SIGMA=  2.5 PHAS=   42.9 FOM= 0.95 TEST= 0
INDE 32 44 54 FOBS=     0.0 SIGMA= 21.7 PHAS=    0.0 FOM= 0.00 TEST= 0
INDE 32 45 33 FOBS=    86.0 SIGMA=  1.9 PHAS=   72.2 FOM= 0.12 TEST= 1
INDE 32 45 35 FOBS=    18.1 SIGMA=  9.9 PHAS=   69.7 FOM= 0.06 TEST= 0
INDE 32 45 37 FOBS=    75.6 SIGMA=  2.3 PHAS=   39.4 FOM= 0.88 TEST= 0
INDE 32 45 39 FOBS=    51.3 SIGMA=  3.6 PHAS= -109.4 FOM= 0.46 TEST= 0
INDE 32 45 41 FOBS=    54.5 SIGMA=  3.4 PHAS=   98.6 FOM= 0.02 TEST= 1
INDE 32 45 43 FOBS=   122.7 SIGMA=  1.6 PHAS=  111.8 FOM= 0.90 TEST= 0
INDE 32 45 45 FOBS=   100.3 SIGMA=  1.9 PHAS=   43.2 FOM= 0.08 TEST= 1
INDE 32 45 47 FOBS=    20.2 SIGMA=  9.8 PHAS= -111.8 FOM= 0.39 TEST= 0
INDE 32 45 49 FOBS=    35.1 SIGMA=  6.1 PHAS=  144.5 FOM= 0.80 TEST= 0
INDE 32 45 51 FOBS=    58.2 SIGMA=  4.1 PHAS=  -24.4 FOM= 0.83 TEST= 0
INDE 32 45 53 FOBS=    65.9 SIGMA=  3.7 PHAS=  -56.6 FOM= 0.90 TEST= 0
INDE 32 46 32 FOBS=     0.0 SIGMA= 19.3 PHAS=    0.0 FOM= 0.00 TEST= 0
INDE 32 46 34 FOBS=     0.0 SIGMA= 19.2 PHAS=    0.0 FOM= 0.00 TEST= 0
INDE 32 46 36 FOBS=   112.8 SIGMA=  1.5 PHAS=  -68.5 FOM= 0.94 TEST= 0
```

*FIG. 12A - 546*

```
INDE  32  46  38 FOBS=   76.1 SIGMA=  2.3 PHAS=  -53.6 FOM= 0.83 TEST= 0
INDE  32  46  40 FOBS=   12.3 SIGMA= 14.5 PHAS=    2.2 FOM= 0.11 TEST= 0
INDE  32  46  42 FOBS=   70.1 SIGMA=  2.4 PHAS=   86.1 FOM= 0.65 TEST= 0
INDE  32  46  44 FOBS=   48.9 SIGMA=  3.4 PHAS= -113.9 FOM= 0.61 TEST= 0
INDE  32  46  46 FOBS=  103.2 SIGMA=  1.9 PHAS= -174.5 FOM= 0.91 TEST= 0
INDE  32  46  48 FOBS=   17.6 SIGMA= 11.6 PHAS=   84.3 FOM= 0.03 TEST= 1
INDE  32  46  50 FOBS=   75.3 SIGMA=  3.2 PHAS=  -50.2 FOM= 0.94 TEST= 0
INDE  32  46  52 FOBS=   34.3 SIGMA=  7.0 PHAS= -145.1 FOM= 0.50 TEST= 0
INDE  32  47  33 FOBS=   55.7 SIGMA=  2.9 PHAS=  119.7 FOM= 0.82 TEST= 0
INDE  32  47  35 FOBS=    0.0 SIGMA= 19.8 PHAS=    0.0 FOM= 0.00 TEST= 0
INDE  32  47  37 FOBS=   72.9 SIGMA=  2.4 PHAS= -160.7 FOM= 0.49 TEST= 1
INDE  32  47  39 FOBS=    0.0 SIGMA= 19.1 PHAS=    0.0 FOM= 0.00 TEST= 0
INDE  32  47  41 FOBS=   47.2 SIGMA=  3.7 PHAS=   39.8 FOM= 0.41 TEST= 0
INDE  32  47  43 FOBS=   88.3 SIGMA=  1.9 PHAS=   94.7 FOM= 0.90 TEST= 0
INDE  32  47  45 FOBS=    0.0 SIGMA= 20.5 PHAS=    0.0 FOM= 0.00 TEST= 0
INDE  32  47  47 FOBS=   20.3 SIGMA=  9.0 PHAS=   85.6 FOM= 0.26 TEST= 0
INDE  32  47  49 FOBS=   89.8 SIGMA=  2.5 PHAS=  -57.1 FOM= 0.03 TEST= 1
INDE  32  47  51 FOBS=   74.2 SIGMA=  3.3 PHAS=    7.3 FOM= 0.70 TEST= 0
INDE  32  47  53 FOBS=   42.5 SIGMA=  9.1 PHAS=  -72.9 FOM= 0.78 TEST= 0
INDE  32  48  32 FOBS=   52.8 SIGMA=  3.1 PHAS=   51.6 FOM= 0.73 TEST= 0
INDE  32  48  34 FOBS=   88.0 SIGMA=  1.9 PHAS=  -48.8 FOM= 0.91 TEST= 0
INDE  32  48  36 FOBS=    0.0 SIGMA= 18.8 PHAS=    0.0 FOM= 0.00 TEST= 0
INDE  32  48  38 FOBS=   45.3 SIGMA=  4.0 PHAS=  -24.5 FOM= 0.77 TEST= 0
INDE  32  48  40 FOBS=   43.7 SIGMA=  4.3 PHAS=   42.1 FOM= 0.56 TEST= 0
INDE  32  48  42 FOBS=   80.9 SIGMA=  2.2 PHAS=    1.3 FOM= 0.88 TEST= 0
INDE  32  48  44 FOBS=   24.5 SIGMA=  7.7 PHAS=   -6.3 FOM= 0.73 TEST= 0
INDE  32  48  46 FOBS=   66.9 SIGMA=  3.1 PHAS=  142.1 FOM= 0.86 TEST= 0
INDE  32  48  48 FOBS=   74.6 SIGMA=  3.0 PHAS= -147.9 FOM= 0.85 TEST= 0
INDE  32  48  50 FOBS=   83.8 SIGMA=  3.0 PHAS=  -40.0 FOM= 0.78 TEST= 0
INDE  32  48  52 FOBS=   37.9 SIGMA=  6.6 PHAS= -108.0 FOM= 0.77 TEST= 0
INDE  32  49  33 FOBS=   54.4 SIGMA=  3.0 PHAS=  -88.1 FOM= 0.24 TEST= 1
INDE  32  49  35 FOBS=    0.0 SIGMA= 18.4 PHAS=    0.0 FOM= 0.00 TEST= 0
INDE  32  49  37 FOBS=   88.4 SIGMA=  2.0 PHAS= -178.6 FOM= 0.88 TEST= 0
INDE  32  49  39 FOBS=   57.6 SIGMA=  3.4 PHAS=  148.9 FOM= 0.56 TEST= 0
INDE  32  49  41 FOBS=    9.7 SIGMA= 19.9 PHAS=   55.6 FOM= 0.12 TEST= 0
INDE  32  49  43 FOBS=   30.0 SIGMA=  7.0 PHAS=  -58.5 FOM= 0.65 TEST= 0
INDE  32  49  45 FOBS=   29.9 SIGMA=  7.7 PHAS= -176.6 FOM= 0.15 TEST= 0
INDE  32  49  47 FOBS=   91.4 SIGMA=  2.5 PHAS=   86.3 FOM= 0.92 TEST= 0
INDE  32  49  49 FOBS=   56.0 SIGMA=  4.0 PHAS=  -96.7 FOM= 0.84 TEST= 0
INDE  32  49  51 FOBS=   13.6 SIGMA= 19.9 PHAS=  132.8 FOM= 0.26 TEST= 0
INDE  32  50  32 FOBS=    0.0 SIGMA= 19.3 PHAS=    0.0 FOM= 0.00 TEST= 0
INDE  32  50  34 FOBS=  120.9 SIGMA=  1.5 PHAS= -144.6 FOM= 0.34 TEST= 1
INDE  32  50  36 FOBS=  101.6 SIGMA=  1.8 PHAS=   49.8 FOM= 0.91 TEST= 0
INDE  32  50  38 FOBS=   29.3 SIGMA=  8.1 PHAS=   88.0 FOM= 0.36 TEST= 0
INDE  32  50  40 FOBS=    0.0 SIGMA= 22.0 PHAS=    0.0 FOM= 0.00 TEST= 0
INDE  32  50  42 FOBS=    0.0 SIGMA= 20.6 PHAS=    0.0 FOM= 0.00 TEST= 0
INDE  32  50  44 FOBS=   36.6 SIGMA=  5.9 PHAS=   32.9 FOM= 0.48 TEST= 0
INDE  32  50  46 FOBS=    0.0 SIGMA= 21.0 PHAS=    0.0 FOM= 0.00 TEST= 0
INDE  32  50  48 FOBS=    0.0 SIGMA= 22.8 PHAS=    0.0 FOM= 0.00 TEST= 0
INDE  32  50  50 FOBS=   16.4 SIGMA= 16.7 PHAS=   13.6 FOM= 0.30 TEST= 0
INDE  32  51  33 FOBS=   74.6 SIGMA=  2.4 PHAS= -162.8 FOM= 0.85 TEST= 0
INDE  32  51  35 FOBS=    0.0 SIGMA= 19.5 PHAS=    0.0 FOM= 0.00 TEST= 0
INDE  32  51  37 FOBS=    0.0 SIGMA= 19.0 PHAS=    0.0 FOM= 0.00 TEST= 0
INDE  32  51  39 FOBS=   36.1 SIGMA=  6.2 PHAS=  142.4 FOM= 0.43 TEST= 0
INDE  32  51  41 FOBS=   37.8 SIGMA=  5.3 PHAS=  128.3 FOM= 0.49 TEST= 0
INDE  32  51  43 FOBS=   48.9 SIGMA=  4.4 PHAS=   30.9 FOM= 0.85 TEST= 0
INDE  32  51  45 FOBS=   15.5 SIGMA= 15.1 PHAS=  -83.1 FOM= 0.17 TEST= 0
INDE  32  51  47 FOBS=    0.0 SIGMA= 23.0 PHAS=    0.0 FOM= 0.00 TEST= 0
INDE  32  51  49 FOBS=   43.4 SIGMA=  6.4 PHAS=  -48.1 FOM= 0.68 TEST= 0
INDE  32  52  32 FOBS=   39.3 SIGMA=  4.7 PHAS= -166.2 FOM= 0.11 TEST= 1
INDE  32  52  34 FOBS=   47.0 SIGMA=  3.8 PHAS= -154.8 FOM= 0.55 TEST= 0
INDE  32  52  36 FOBS=    7.1 SIGMA= 25.4 PHAS=   88.9 FOM= 0.18 TEST= 0
INDE  32  52  38 FOBS=   34.8 SIGMA=  5.8 PHAS=  174.2 FOM= 0.08 TEST= 1
INDE  32  52  40 FOBS=   93.7 SIGMA=  2.7 PHAS=  129.9 FOM= 0.36 TEST= 1
INDE  32  52  42 FOBS=   53.9 SIGMA=  4.0 PHAS=   -5.2 FOM= 0.87 TEST= 0
INDE  32  52  44 FOBS=   60.1 SIGMA=  3.7 PHAS=  -34.6 FOM= 0.78 TEST= 0
INDE  32  52  46 FOBS=    0.0 SIGMA= 22.5 PHAS=    0.0 FOM= 0.00 TEST= 0
INDE  32  52  48 FOBS=   63.8 SIGMA=  3.7 PHAS=   -0.8 FOM= 0.49 TEST= 0
INDE  32  53  33 FOBS=   10.1 SIGMA= 19.3 PHAS= -112.5 FOM= 0.06 TEST= 0
INDE  32  53  35 FOBS=   65.8 SIGMA=  2.9 PHAS=   69.1 FOM= 0.86 TEST= 0
```

*FIG. 12A - 547*

```
INDE 32 53 37 FOBS=   32.5 SIGMA=  6.4 PHAS=   97.2 FOM= 0.31 TEST= 0
INDE 32 53 39 FOBS=  105.7 SIGMA=  2.4 PHAS=   70.0 FOM= 0.95 TEST= 0
INDE 32 53 41 FOBS=   75.6 SIGMA=  3.4 PHAS=  -87.4 FOM= 0.77 TEST= 0
INDE 32 53 43 FOBS=    0.0 SIGMA= 20.8 PHAS=    0.0 FOM= 0.00 TEST= 0
INDE 32 53 45 FOBS=    0.0 SIGMA= 23.5 PHAS=    0.0 FOM= 0.00 TEST= 0
INDE 32 53 47 FOBS=   33.1 SIGMA= 10.0 PHAS=   53.4 FOM= 0.00 TEST= 1
INDE 32 54 32 FOBS=   85.5 SIGMA=  2.2 PHAS=  -54.9 FOM= 0.90 TEST= 0
INDE 32 54 34 FOBS=   19.2 SIGMA= 11.2 PHAS= -166.0 FOM= 0.44 TEST= 0
INDE 32 54 36 FOBS=   50.0 SIGMA=  4.5 PHAS=  119.5 FOM= 0.73 TEST= 0
INDE 32 54 38 FOBS=   55.2 SIGMA=  4.1 PHAS=  -26.5 FOM= 0.84 TEST= 0
INDE 32 54 40 FOBS=   28.2 SIGMA= 11.7 PHAS=   46.1 FOM= 0.44 TEST= 0
INDE 32 54 42 FOBS=   36.6 SIGMA=  6.9 PHAS=   -5.1 FOM= 0.80 TEST= 0
INDE 32 54 44 FOBS=    0.0 SIGMA= 21.9 PHAS=    0.0 FOM= 0.00 TEST= 0
INDE 32 55 33 FOBS=   79.7 SIGMA=  2.4 PHAS= -141.0 FOM= 0.81 TEST= 0
INDE 32 55 35 FOBS=  107.1 SIGMA=  2.1 PHAS=   55.4 FOM= 0.94 TEST= 0
INDE 32 55 37 FOBS=   81.1 SIGMA=  2.8 PHAS= -170.2 FOM= 0.92 TEST= 0
INDE 32 55 39 FOBS=   42.9 SIGMA=  6.4 PHAS=   14.3 FOM= 0.52 TEST= 0
INDE 32 55 41 FOBS=  104.6 SIGMA=  2.5 PHAS=  -92.9 FOM= 0.97 TEST= 0
INDE 32 55 43 FOBS=    0.0 SIGMA= 21.9 PHAS=    0.0 FOM= 0.00 TEST= 0
INDE 32 56 32 FOBS=   27.0 SIGMA=  7.4 PHAS=  103.5 FOM= 0.34 TEST= 0
INDE 32 56 34 FOBS=   39.8 SIGMA=  5.5 PHAS=   53.1 FOM= 0.62 TEST= 0
INDE 32 56 36 FOBS=   64.0 SIGMA=  3.5 PHAS=  118.7 FOM= 0.88 TEST= 0
INDE 32 56 38 FOBS=   80.2 SIGMA=  2.9 PHAS=   27.7 FOM= 0.83 TEST= 0
INDE 32 56 40 FOBS=   82.2 SIGMA=  3.2 PHAS=  121.7 FOM= 0.94 TEST= 0
INDE 32 56 42 FOBS=    0.0 SIGMA= 22.8 PHAS=    0.0 FOM= 0.00 TEST= 0
INDE 32 57 33 FOBS=    0.0 SIGMA= 22.7 PHAS=    0.0 FOM= 0.00 TEST= 0
INDE 32 57 35 FOBS=   95.7 SIGMA=  2.4 PHAS=  -21.3 FOM= 0.86 TEST= 0
INDE 32 57 37 FOBS=   15.0 SIGMA= 17.8 PHAS= -149.3 FOM= 0.34 TEST= 0
INDE 32 57 39 FOBS=   98.6 SIGMA=  2.4 PHAS=  -24.1 FOM= 0.96 TEST= 0
INDE 32 57 41 FOBS=   52.0 SIGMA=  5.1 PHAS=  -71.5 FOM= 0.80 TEST= 0
INDE 32 58 32 FOBS=    0.0 SIGMA= 20.8 PHAS=    0.0 FOM= 0.00 TEST= 0
INDE 32 58 34 FOBS=   15.9 SIGMA= 14.0 PHAS=  129.9 FOM= 0.25 TEST= 0
INDE 32 58 36 FOBS=   46.4 SIGMA=  5.8 PHAS=  137.1 FOM= 0.63 TEST= 0
INDE 32 58 38 FOBS=   27.6 SIGMA=  9.0 PHAS= -146.4 FOM= 0.27 TEST= 0
INDE 32 58 40 FOBS=   39.8 SIGMA=  7.4 PHAS=  132.7 FOM= 0.39 TEST= 0
INDE 32 59 33 FOBS=    0.0 SIGMA= 21.8 PHAS=    0.0 FOM= 0.00 TEST= 0
INDE 32 59 35 FOBS=   70.6 SIGMA=  3.2 PHAS=   -2.8 FOM= 0.85 TEST= 0
INDE 32 59 37 FOBS=    0.0 SIGMA= 23.5 PHAS=    0.0 FOM= 0.00 TEST= 0
INDE 32 59 39 FOBS=   57.6 SIGMA=  4.2 PHAS=  -64.8 FOM= 0.84 TEST= 0
INDE 32 60 32 FOBS=   56.2 SIGMA=  4.7 PHAS=  141.4 FOM= 0.54 TEST= 0
INDE 32 60 34 FOBS=   60.4 SIGMA=  3.8 PHAS= -123.8 FOM= 0.54 TEST= 0
INDE 32 60 36 FOBS=   28.2 SIGMA=  9.0 PHAS=  -68.2 FOM= 0.52 TEST= 0
INDE 32 61 33 FOBS=   49.6 SIGMA=  5.0 PHAS=   37.6 FOM= 0.67 TEST= 0
INDE 32 61 35 FOBS=   44.4 SIGMA=  6.2 PHAS=  178.3 FOM= 0.80 TEST= 0
INDE 32 62 32 FOBS=  106.2 SIGMA=  2.6 PHAS=  -42.4 FOM= 0.94 TEST= 0
INDE 32 62 34 FOBS=   39.9 SIGMA=  5.8 PHAS=   27.0 FOM= 0.45 TEST= 0
INDE 33 34 33 FOBS=   17.3 SIGMA= 10.2 PHAS=  168.7 FOM= 0.26 TEST= 0
INDE 33 34 35 FOBS=   49.4 SIGMA=  3.4 PHAS=   73.8 FOM= 0.87 TEST= 0
INDE 33 34 37 FOBS=   95.0 SIGMA=  1.9 PHAS=    1.1 FOM= 0.88 TEST= 0
INDE 33 34 39 FOBS=   93.7 SIGMA=  2.0 PHAS=  128.7 FOM= 0.79 TEST= 0
INDE 33 34 41 FOBS=   48.3 SIGMA=  4.0 PHAS=  107.8 FOM= 0.71 TEST= 0
INDE 33 34 43 FOBS=   78.2 SIGMA=  2.4 PHAS=   17.5 FOM= 0.81 TEST= 0
INDE 33 34 45 FOBS=   88.2 SIGMA=  2.1 PHAS=  143.9 FOM= 0.94 TEST= 0
INDE 33 34 47 FOBS=   55.4 SIGMA=  3.3 PHAS=  131.3 FOM= 0.70 TEST= 0
INDE 33 34 49 FOBS=  131.2 SIGMA=  1.4 PHAS=  -71.3 FOM= 0.92 TEST= 0
INDE 33 34 51 FOBS=   71.6 SIGMA=  2.6 PHAS= -109.2 FOM= 0.87 TEST= 0
INDE 33 34 53 FOBS=   78.8 SIGMA=  2.5 PHAS=  -16.7 FOM= 0.82 TEST= 0
INDE 33 34 55 FOBS=   41.2 SIGMA=  4.6 PHAS=  110.1 FOM= 0.65 TEST= 0
INDE 33 34 57 FOBS=   57.8 SIGMA=  3.3 PHAS=  173.7 FOM= 0.67 TEST= 0
INDE 33 34 59 FOBS=    0.0 SIGMA= 21.2 PHAS=    0.0 FOM= 0.00 TEST= 1
INDE 33 34 61 FOBS=   62.5 SIGMA=  3.7 PHAS=   86.1 FOM= 0.83 TEST= 0
INDE 33 35 34 FOBS=   99.2 SIGMA=  1.7 PHAS= -114.5 FOM= 0.90 TEST= 0
INDE 33 35 36 FOBS=   71.4 SIGMA=  2.4 PHAS= -132.9 FOM= 0.92 TEST= 0
INDE 33 35 38 FOBS=   45.5 SIGMA=  4.1 PHAS=  -66.6 FOM= 0.77 TEST= 0
INDE 33 35 40 FOBS=   68.6 SIGMA=  2.7 PHAS=  -13.6 FOM= 0.89 TEST= 0
INDE 33 35 42 FOBS=   41.2 SIGMA=  4.7 PHAS=  -57.5 FOM= 0.64 TEST= 0
INDE 33 35 44 FOBS=  121.8 SIGMA=  1.6 PHAS= -173.0 FOM= 0.95 TEST= 0
INDE 33 35 46 FOBS=   37.7 SIGMA=  5.1 PHAS=  -10.6 FOM= 0.36 TEST= 0
INDE 33 35 48 FOBS=   43.6 SIGMA=  4.2 PHAS=   89.8 FOM= 0.81 TEST= 0
INDE 33 35 50 FOBS=  157.6 SIGMA=  1.3 PHAS=  156.4 FOM= 0.96 TEST= 0
```

*FIG. 12A - 548*

```
INDE 33 35 52 FOBS=   0.0 SIGMA= 19.0 PHAS=   0.0 FOM= 0.00 TEST= 0
INDE 33 35 54 FOBS=  47.1 SIGMA=  4.1 PHAS= 166.7 FOM= 0.80 TEST= 0
INDE 33 35 56 FOBS=  66.3 SIGMA=  2.9 PHAS=  21.5 FOM= 0.77 TEST= 0
INDE 33 35 58 FOBS=  75.3 SIGMA=  2.6 PHAS=  44.5 FOM= 0.84 TEST= 0
INDE 33 35 60 FOBS=  78.2 SIGMA=  3.0 PHAS=  25.9 FOM= 0.89 TEST= 0
INDE 33 36 33 FOBS=  50.7 SIGMA=  3.3 PHAS= 147.8 FOM= 0.76 TEST= 0
INDE 33 36 35 FOBS= 117.8 SIGMA=  1.5 PHAS=  68.2 FOM= 0.87 TEST= 0
INDE 33 36 37 FOBS=  57.2 SIGMA=  3.1 PHAS=  95.1 FOM= 0.62 TEST= 1
INDE 33 36 39 FOBS=  64.4 SIGMA=  2.9 PHAS= -98.3 FOM= 0.81 TEST= 0
INDE 33 36 41 FOBS=  97.0 SIGMA=  2.0 PHAS=-154.9 FOM= 0.94 TEST= 0
INDE 33 36 43 FOBS=  59.3 SIGMA=  3.1 PHAS=  65.4 FOM= 0.46 TEST= 0
INDE 33 36 45 FOBS= 155.4 SIGMA=  1.3 PHAS= 119.3 FOM= 0.96 TEST= 0
INDE 33 36 47 FOBS=  76.0 SIGMA=  2.4 PHAS=  82.8 FOM= 0.87 TEST= 0
INDE 33 36 49 FOBS= 106.1 SIGMA=  1.8 PHAS=  -6.4 FOM= 0.87 TEST= 0
INDE 33 36 51 FOBS=  99.5 SIGMA=  1.9 PHAS= 129.1 FOM= 0.95 TEST= 0
INDE 33 36 53 FOBS=  74.5 SIGMA=  2.6 PHAS=  39.0 FOM= 0.92 TEST= 0
INDE 33 36 55 FOBS=  37.6 SIGMA=  5.5 PHAS=  73.9 FOM= 0.60 TEST= 0
INDE 33 36 57 FOBS=  45.1 SIGMA=  4.3 PHAS=  26.2 FOM= 0.59 TEST= 0
INDE 33 36 59 FOBS= 122.5 SIGMA=  1.7 PHAS= -51.9 FOM= 0.96 TEST= 0
INDE 33 37 34 FOBS=  96.6 SIGMA=  1.8 PHAS= -11.8 FOM= 0.80 TEST= 0
INDE 33 37 36 FOBS= 136.1 SIGMA=  1.3 PHAS= -33.0 FOM= 0.93 TEST= 0
INDE 33 37 38 FOBS=  66.8 SIGMA=  2.8 PHAS= 158.9 FOM= 0.72 TEST= 0
INDE 33 37 40 FOBS= 172.6 SIGMA=  1.2 PHAS=  68.2 FOM= 0.96 TEST= 0
INDE 33 37 42 FOBS=   0.0 SIGMA= 19.1 PHAS=   0.0 FOM= 0.00 TEST= 0
INDE 33 37 44 FOBS=  69.5 SIGMA=  2.7 PHAS=-151.9 FOM= 0.75 TEST= 0
INDE 33 37 46 FOBS= 115.9 SIGMA=  1.6 PHAS=  20.8 FOM= 0.96 TEST= 0
INDE 33 37 48 FOBS=   0.0 SIGMA= 19.6 PHAS=   0.0 FOM= 0.00 TEST= 1
INDE 33 37 50 FOBS=  63.1 SIGMA=  2.9 PHAS= 121.0 FOM= 0.79 TEST= 0
INDE 33 37 52 FOBS=  50.6 SIGMA=  3.6 PHAS= -49.6 FOM= 0.85 TEST= 0
INDE 33 37 54 FOBS=  25.9 SIGMA=  8.4 PHAS= -61.5 FOM= 0.57 TEST= 0
INDE 33 37 56 FOBS=  51.5 SIGMA=  3.9 PHAS=   0.1 FOM= 0.64 TEST= 0
INDE 33 37 58 FOBS=  49.0 SIGMA=  4.7 PHAS=-162.5 FOM= 0.08 TEST= 1
INDE 33 38 33 FOBS=  31.7 SIGMA=  5.8 PHAS= -86.7 FOM= 0.36 TEST= 0
INDE 33 38 35 FOBS=  53.5 SIGMA=  3.1 PHAS=-108.8 FOM= 0.50 TEST= 0
INDE 33 38 37 FOBS=   0.0 SIGMA= 18.2 PHAS=   0.0 FOM= 0.00 TEST= 0
INDE 33 38 39 FOBS= 130.0 SIGMA=  1.5 PHAS= -32.8 FOM= 0.95 TEST= 0
INDE 33 38 41 FOBS=  71.6 SIGMA=  2.6 PHAS= -81.6 FOM= 0.50 TEST= 1
INDE 33 38 43 FOBS=  48.6 SIGMA=  3.8 PHAS= 145.1 FOM= 0.33 TEST= 0
INDE 33 38 45 FOBS=   0.0 SIGMA= 20.1 PHAS=   0.0 FOM= 0.00 TEST= 0
INDE 33 38 47 FOBS=   0.0 SIGMA= 20.2 PHAS=   0.0 FOM= 0.00 TEST= 1
INDE 33 38 49 FOBS=  11.7 SIGMA= 17.3 PHAS=  45.0 FOM= 0.24 TEST= 0
INDE 33 38 51 FOBS= 144.4 SIGMA=  1.4 PHAS= 124.4 FOM= 0.97 TEST= 0
INDE 33 38 53 FOBS=   0.0 SIGMA= 21.1 PHAS=   0.0 FOM= 0.00 TEST= 0
INDE 33 38 55 FOBS=   0.0 SIGMA= 21.4 PHAS=   0.0 FOM= 0.00 TEST= 0
INDE 33 38 57 FOBS=  11.1 SIGMA= 18.0 PHAS=  37.5 FOM= 0.32 TEST= 0
INDE 33 38 59 FOBS=  64.5 SIGMA=  3.5 PHAS=   7.9 FOM= 0.67 TEST= 0
INDE 33 39 34 FOBS= 143.6 SIGMA=  1.3 PHAS=  12.1 FOM= 0.93 TEST= 0
INDE 33 39 36 FOBS=  29.5 SIGMA=  5.8 PHAS= 151.6 FOM= 0.18 TEST= 1
INDE 33 39 38 FOBS= 154.8 SIGMA=  1.3 PHAS=-167.8 FOM= 0.96 TEST= 0
INDE 33 39 40 FOBS=  44.8 SIGMA=  4.2 PHAS= 159.3 FOM= 0.27 TEST= 0
INDE 33 39 42 FOBS=  41.8 SIGMA=  4.7 PHAS= 156.5 FOM= 0.73 TEST= 0
INDE 33 39 44 FOBS= 105.0 SIGMA=  1.8 PHAS=-155.8 FOM= 0.93 TEST= 0
INDE 33 39 46 FOBS=  46.4 SIGMA=  3.9 PHAS=-137.4 FOM= 0.48 TEST= 0
INDE 33 39 48 FOBS=  59.9 SIGMA=  3.1 PHAS= 139.5 FOM= 0.81 TEST= 0
INDE 33 39 50 FOBS= 125.2 SIGMA=  1.5 PHAS=  29.0 FOM= 0.94 TEST= 0
INDE 33 39 52 FOBS=  93.9 SIGMA=  2.2 PHAS= -19.6 FOM= 0.91 TEST= 0
INDE 33 39 54 FOBS=  82.0 SIGMA=  2.5 PHAS= -56.6 FOM= 0.89 TEST= 0
INDE 33 39 56 FOBS=   0.0 SIGMA= 21.3 PHAS=   0.0 FOM= 0.00 TEST= 0
INDE 33 39 58 FOBS=   0.0 SIGMA= 20.2 PHAS=   0.0 FOM= 0.00 TEST= 0
INDE 33 40 33 FOBS= 146.9 SIGMA=  1.3 PHAS= -67.5 FOM= 0.95 TEST= 0
INDE 33 40 35 FOBS=  64.5 SIGMA=  2.6 PHAS= -72.5 FOM= 0.77 TEST= 0
INDE 33 40 37 FOBS= 108.3 SIGMA=  1.6 PHAS=  25.6 FOM= 0.93 TEST= 0
INDE 33 40 39 FOBS= 156.4 SIGMA=  1.3 PHAS= 130.7 FOM= 0.96 TEST= 0
INDE 33 40 41 FOBS=   0.0 SIGMA= 20.2 PHAS=   0.0 FOM= 0.00 TEST= 0
INDE 33 40 43 FOBS=  28.1 SIGMA=  6.8 PHAS=  73.7 FOM= 0.66 TEST= 0
INDE 33 40 45 FOBS=  92.4 SIGMA=  2.0 PHAS= 110.2 FOM= 0.90 TEST= 0
INDE 33 40 47 FOBS=  78.4 SIGMA=  2.4 PHAS= 139.2 FOM= 0.84 TEST= 0
INDE 33 40 49 FOBS=  84.9 SIGMA=  2.3 PHAS=  60.6 FOM= 0.86 TEST= 0
INDE 33 40 51 FOBS=  42.6 SIGMA=  4.3 PHAS= -48.6 FOM= 0.50 TEST= 0
INDE 33 40 53 FOBS=  83.8 SIGMA=  2.4 PHAS= 139.6 FOM= 0.31 TEST= 1
```

*FIG. 12A - 549*

```
INDE 33 40 55 FOBS=    0.0 SIGMA= 20.0 PHAS=    0.0 FOM= 0.00 TEST= 0
INDE 33 40 57 FOBS=    0.0 SIGMA= 21.6 PHAS=    0.0 FOM= 0.00 TEST= 0
INDE 33 41 34 FOBS=    0.0 SIGMA= 20.1 PHAS=    0.0 FOM= 0.00 TEST= 0
INDE 33 41 36 FOBS=  106.7 SIGMA=  1.6 PHAS= -168.1 FOM= 0.63 TEST= 1
INDE 33 41 38 FOBS=   31.1 SIGMA=  5.9 PHAS= -170.1 FOM= 0.21 TEST= 0
INDE 33 41 40 FOBS=  110.4 SIGMA=  1.7 PHAS=  -19.9 FOM= 0.90 TEST= 0
INDE 33 41 42 FOBS=    0.0 SIGMA= 20.4 PHAS=    0.0 FOM= 0.00 TEST= 0
INDE 33 41 44 FOBS=    0.0 SIGMA= 20.3 PHAS=    0.0 FOM= 0.00 TEST= 0
INDE 33 41 46 FOBS=   18.9 SIGMA=  9.7 PHAS=   33.7 FOM= 0.64 TEST= 0
INDE 33 41 48 FOBS=  143.4 SIGMA=  1.4 PHAS=   19.2 FOM= 0.94 TEST= 0
INDE 33 41 50 FOBS=   30.2 SIGMA=  6.9 PHAS=  -36.3 FOM= 0.49 TEST= 0
INDE 33 41 52 FOBS=   66.4 SIGMA=  3.1 PHAS=    7.5 FOM= 0.65 TEST= 0
INDE 33 41 54 FOBS=   54.9 SIGMA=  3.7 PHAS=  -60.5 FOM= 0.76 TEST= 0
INDE 33 41 56 FOBS=   58.0 SIGMA=  3.6 PHAS=  -84.7 FOM= 0.24 TEST= 0
INDE 33 42 33 FOBS=    0.0 SIGMA= 20.0 PHAS=    0.0 FOM= 0.00 TEST= 0
INDE 33 42 35 FOBS=  140.2 SIGMA=  1.4 PHAS=   63.7 FOM= 0.94 TEST= 0
INDE 33 42 37 FOBS=   93.9 SIGMA=  1.8 PHAS=   24.5 FOM= 0.79 TEST= 0
INDE 33 42 39 FOBS=  169.3 SIGMA=  1.2 PHAS=  159.0 FOM= 0.97 TEST= 0
INDE 33 42 41 FOBS=   18.3 SIGMA= 10.8 PHAS=  146.0 FOM= 0.25 TEST= 0
INDE 33 42 43 FOBS=   72.7 SIGMA=  2.6 PHAS=    1.1 FOM= 0.87 TEST= 0
INDE 33 42 45 FOBS=   76.6 SIGMA=  2.5 PHAS=  136.3 FOM= 0.87 TEST= 0
INDE 33 42 47 FOBS=    4.3 SIGMA= 42.9 PHAS=  -15.7 FOM= 0.15 TEST= 0
INDE 33 42 49 FOBS=   40.0 SIGMA=  4.7 PHAS= -143.8 FOM= 0.33 TEST= 0
INDE 33 42 51 FOBS=    0.0 SIGMA= 21.4 PHAS=    0.0 FOM= 0.00 TEST= 0
INDE 33 42 53 FOBS=   44.7 SIGMA=  4.5 PHAS= -164.0 FOM= 0.69 TEST= 0
INDE 33 42 55 FOBS=   27.0 SIGMA=  7.6 PHAS= -112.1 FOM= 0.28 TEST= 0
INDE 33 43 34 FOBS=  112.8 SIGMA=  1.7 PHAS=  -71.6 FOM= 0.95 TEST= 0
INDE 33 43 36 FOBS=   28.9 SIGMA=  6.2 PHAS=    8.3 FOM= 0.54 TEST= 0
INDE 33 43 38 FOBS=    0.0 SIGMA= 19.4 PHAS=    0.0 FOM= 0.00 TEST= 0
INDE 33 43 40 FOBS=  124.9 SIGMA=  1.5 PHAS=   41.2 FOM= 0.95 TEST= 0
INDE 33 43 42 FOBS=    0.0 SIGMA= 19.6 PHAS=    0.0 FOM= 0.00 TEST= 0
INDE 33 43 44 FOBS=    0.0 SIGMA= 20.9 PHAS=    0.0 FOM= 0.00 TEST= 0
INDE 33 43 46 FOBS=   22.9 SIGMA=  9.1 PHAS=   49.3 FOM= 0.35 TEST= 0
INDE 33 43 48 FOBS=   47.8 SIGMA=  4.1 PHAS=   -1.2 FOM= 0.76 TEST= 0
INDE 33 43 50 FOBS=   57.2 SIGMA=  3.3 PHAS= -139.5 FOM= 0.91 TEST= 0
INDE 33 43 52 FOBS=   53.2 SIGMA=  3.8 PHAS=  -48.1 FOM= 0.60 TEST= 0
INDE 33 43 54 FOBS=    0.0 SIGMA= 20.9 PHAS=    0.0 FOM= 0.00 TEST= 0
INDE 33 44 33 FOBS=  106.5 SIGMA=  1.8 PHAS= -176.6 FOM= 0.89 TEST= 0
INDE 33 44 35 FOBS=   31.8 SIGMA=  5.7 PHAS=  154.2 FOM= 0.24 TEST= 0
INDE 33 44 37 FOBS=   47.5 SIGMA=  3.6 PHAS=  -98.7 FOM= 0.83 TEST= 0
INDE 33 44 39 FOBS=   84.4 SIGMA=  2.2 PHAS=  159.3 FOM= 0.70 TEST= 0
INDE 33 44 41 FOBS=    0.0 SIGMA= 21.0 PHAS=    0.0 FOM= 0.00 TEST= 0
INDE 33 44 43 FOBS=  124.8 SIGMA=  1.6 PHAS=   -9.9 FOM= 0.93 TEST= 0
INDE 33 44 45 FOBS=   47.2 SIGMA=  4.0 PHAS= -127.5 FOM= 0.67 TEST= 0
INDE 33 44 47 FOBS=    0.0 SIGMA= 20.4 PHAS=    0.0 FOM= 0.00 TEST= 0
INDE 33 44 49 FOBS=   35.2 SIGMA=  6.7 PHAS=   73.0 FOM= 0.17 TEST= 0
INDE 33 44 51 FOBS=   82.3 SIGMA=  2.5 PHAS= -173.2 FOM= 0.40 TEST= 1
INDE 33 44 53 FOBS=   19.2 SIGMA= 10.7 PHAS=  -53.3 FOM= 0.54 TEST= 0
INDE 33 45 34 FOBS=   67.8 SIGMA=  2.7 PHAS=   24.2 FOM= 0.65 TEST= 0
INDE 33 45 36 FOBS=   60.8 SIGMA=  3.0 PHAS=  176.5 FOM= 0.81 TEST= 0
INDE 33 45 38 FOBS=  127.3 SIGMA=  1.4 PHAS=  -86.3 FOM= 0.92 TEST= 0
INDE 33 45 40 FOBS=   15.6 SIGMA= 12.9 PHAS= -109.3 FOM= 0.01 TEST= 1
INDE 33 45 42 FOBS=   45.2 SIGMA=  4.1 PHAS= -168.1 FOM= 0.25 TEST= 1
INDE 33 45 44 FOBS=  154.9 SIGMA=  1.3 PHAS= -168.9 FOM= 0.86 TEST= 0
INDE 33 45 46 FOBS=   53.0 SIGMA=  3.6 PHAS=   68.1 FOM= 0.62 TEST= 0
INDE 33 45 48 FOBS=   32.2 SIGMA=  6.7 PHAS= -173.4 FOM= 0.65 TEST= 0
INDE 33 45 50 FOBS=   52.5 SIGMA=  3.7 PHAS=  149.6 FOM= 0.90 TEST= 0
INDE 33 45 52 FOBS=    8.0 SIGMA= 29.2 PHAS=  -54.2 FOM= 0.16 TEST= 0
INDE 33 45 54 FOBS=   44.6 SIGMA=  5.5 PHAS= -111.3 FOM= 0.61 TEST= 0
INDE 33 46 33 FOBS=   54.0 SIGMA=  3.5 PHAS=  -46.9 FOM= 0.82 TEST= 0
INDE 33 46 35 FOBS=   36.2 SIGMA=  5.3 PHAS= -170.5 FOM= 0.32 TEST= 0
INDE 33 46 37 FOBS=   85.3 SIGMA=  2.2 PHAS=  150.1 FOM= 0.87 TEST= 0
INDE 33 46 39 FOBS=    0.0 SIGMA= 20.9 PHAS=    0.0 FOM= 0.00 TEST= 0
INDE 33 46 41 FOBS=    0.0 SIGMA= 19.1 PHAS=    0.0 FOM= 0.00 TEST= 0
INDE 33 46 43 FOBS=   89.7 SIGMA=  2.1 PHAS=    1.9 FOM= 0.94 TEST= 0
INDE 33 46 45 FOBS=   62.6 SIGMA=  3.0 PHAS=  -49.3 FOM= 0.86 TEST= 0
INDE 33 46 47 FOBS=   62.1 SIGMA=  3.1 PHAS=  105.2 FOM= 0.79 TEST= 0
INDE 33 46 49 FOBS=   96.4 SIGMA=  2.1 PHAS=   79.3 FOM= 0.95 TEST= 0
INDE 33 46 51 FOBS=   47.6 SIGMA=  4.7 PHAS= -120.5 FOM= 0.75 TEST= 0
INDE 33 46 53 FOBS=   32.0 SIGMA=  8.4 PHAS=   75.8 FOM= 0.30 TEST= 0
```

*FIG. 12A - 550*

```
INDE 33 47 34 FOBS=   0.0 SIGMA= 18.9 PHAS=    0.0 FOM= 0.00 TEST= 0
INDE 33 47 36 FOBS=  63.6 SIGMA=  2.6 PHAS= -173.2 FOM= 0.89 TEST= 0
INDE 33 47 38 FOBS=  10.7 SIGMA= 17.5 PHAS=  114.6 FOM= 0.08 TEST= 0
INDE 33 47 40 FOBS=   0.0 SIGMA= 19.1 PHAS=    0.0 FOM= 0.00 TEST= 0
INDE 33 47 42 FOBS=   0.0 SIGMA= 20.7 PHAS=    0.0 FOM= 0.00 TEST= 0
INDE 33 47 44 FOBS=  84.0 SIGMA=  2.3 PHAS=  -78.5 FOM= 0.81 TEST= 0
INDE 33 47 46 FOBS=  32.7 SIGMA=  5.8 PHAS=   73.4 FOM= 0.42 TEST= 0
INDE 33 47 48 FOBS=  61.2 SIGMA=  3.2 PHAS=   14.6 FOM= 0.89 TEST= 0
INDE 33 47 50 FOBS=  66.7 SIGMA=  3.7 PHAS=  134.9 FOM= 0.09 TEST= 0
INDE 33 47 52 FOBS=  36.7 SIGMA=  6.7 PHAS=  -60.7 FOM= 0.14 TEST= 0
INDE 33 48 33 FOBS=  49.7 SIGMA=  3.3 PHAS=   -7.5 FOM= 0.76 TEST= 0
INDE 33 48 35 FOBS=  46.8 SIGMA=  3.7 PHAS=  -86.6 FOM= 0.28 TEST= 0
INDE 33 48 37 FOBS=  58.6 SIGMA=  3.0 PHAS=   58.5 FOM= 0.86 TEST= 0
INDE 33 48 39 FOBS=   0.0 SIGMA= 20.0 PHAS=    0.0 FOM= 0.00 TEST= 0
INDE 33 48 41 FOBS=   0.0 SIGMA= 18.7 PHAS=    0.0 FOM= 0.00 TEST= 0
INDE 33 48 43 FOBS=  67.6 SIGMA=  2.8 PHAS=  -67.3 FOM= 0.21 TEST= 0
INDE 33 48 45 FOBS=  60.6 SIGMA=  3.2 PHAS= -127.8 FOM= 0.75 TEST= 0
INDE 33 48 47 FOBS=  49.1 SIGMA=  4.0 PHAS=  158.2 FOM= 0.11 TEST= 0
INDE 33 48 49 FOBS=  83.3 SIGMA=  2.8 PHAS=  173.1 FOM= 0.88 TEST= 0
INDE 33 48 51 FOBS=  45.4 SIGMA=  5.9 PHAS=  -72.9 FOM= 0.71 TEST= 0
INDE 33 49 34 FOBS= 143.3 SIGMA=  1.3 PHAS= -163.7 FOM= 0.93 TEST= 0
INDE 33 49 36 FOBS=  88.1 SIGMA=  2.0 PHAS= -124.6 FOM= 0.56 TEST= 1
INDE 33 49 38 FOBS=   0.0 SIGMA= 19.6 PHAS=    0.0 FOM= 0.00 TEST= 1
INDE 33 49 40 FOBS=   0.0 SIGMA= 19.1 PHAS=    0.0 FOM= 0.00 TEST= 0
INDE 33 49 42 FOBS=   0.0 SIGMA= 20.3 PHAS=    0.0 FOM= 0.00 TEST= 0
INDE 33 49 44 FOBS=  40.7 SIGMA=  4.7 PHAS=  -95.1 FOM= 0.75 TEST= 0
INDE 33 49 46 FOBS=  45.0 SIGMA=  4.3 PHAS=   85.5 FOM= 0.82 TEST= 0
INDE 33 49 48 FOBS=  39.8 SIGMA=  5.7 PHAS=   53.0 FOM= 0.80 TEST= 0
INDE 33 49 50 FOBS=  43.9 SIGMA=  5.8 PHAS=  137.4 FOM= 0.12 TEST= 1
INDE 33 50 33 FOBS=  75.0 SIGMA=  2.4 PHAS=   80.9 FOM= 0.90 TEST= 0
INDE 33 50 35 FOBS= 158.7 SIGMA=  1.2 PHAS=  135.3 FOM= 0.96 TEST= 0
INDE 33 50 37 FOBS=   0.0 SIGMA= 19.6 PHAS=    0.0 FOM= 0.00 TEST= 1
INDE 33 50 39 FOBS=   0.0 SIGMA= 19.6 PHAS=    0.0 FOM= 0.00 TEST= 0
INDE 33 50 41 FOBS=   0.0 SIGMA= 21.9 PHAS=    0.0 FOM= 0.00 TEST= 0
INDE 33 50 43 FOBS=  51.4 SIGMA=  3.7 PHAS= -123.3 FOM= 0.71 TEST= 0
INDE 33 50 45 FOBS=  42.7 SIGMA=  5.2 PHAS=  -51.2 FOM= 0.55 TEST= 0
INDE 33 50 47 FOBS=   0.0 SIGMA= 22.0 PHAS=    0.0 FOM= 0.00 TEST= 0
INDE 33 50 49 FOBS=  51.9 SIGMA=  4.9 PHAS=  142.3 FOM= 0.29 TEST= 0
INDE 33 51 34 FOBS=  85.0 SIGMA=  2.2 PHAS=   61.9 FOM= 0.87 TEST= 0
INDE 33 51 36 FOBS=  67.9 SIGMA=  2.7 PHAS=  -72.5 FOM= 0.33 TEST= 0
INDE 33 51 38 FOBS=   0.0 SIGMA= 20.2 PHAS=    0.0 FOM= 0.00 TEST= 0
INDE 33 51 40 FOBS=  28.3 SIGMA=  7.9 PHAS=  -76.0 FOM= 0.17 TEST= 0
INDE 33 51 42 FOBS=   0.0 SIGMA= 19.9 PHAS=    0.0 FOM= 0.00 TEST= 0
INDE 33 51 44 FOBS=  68.1 SIGMA=  3.3 PHAS= -107.4 FOM= 0.85 TEST= 0
INDE 33 51 46 FOBS=   0.0 SIGMA= 21.1 PHAS=    0.0 FOM= 0.00 TEST= 0
INDE 33 51 48 FOBS=  29.5 SIGMA=  7.8 PHAS=    6.3 FOM= 0.45 TEST= 0
INDE 33 52 33 FOBS=  17.8 SIGMA= 10.0 PHAS=  105.5 FOM= 0.21 TEST= 0
INDE 33 52 35 FOBS=  34.2 SIGMA=  5.6 PHAS=   29.7 FOM= 0.44 TEST= 0
INDE 33 52 37 FOBS=   0.0 SIGMA= 20.3 PHAS=    0.0 FOM= 0.00 TEST= 0
INDE 33 52 39 FOBS=  20.4 SIGMA= 10.1 PHAS=  -94.8 FOM= 0.63 TEST= 0
INDE 33 52 41 FOBS=  31.6 SIGMA=  8.6 PHAS=   48.1 FOM= 0.09 TEST= 1
INDE 33 52 43 FOBS=  48.3 SIGMA=  4.5 PHAS=  -83.8 FOM= 0.66 TEST= 0
INDE 33 52 45 FOBS=   0.0 SIGMA= 23.6 PHAS=    0.0 FOM= 0.00 TEST= 0
INDE 33 52 47 FOBS=   0.0 SIGMA= 21.4 PHAS=    0.0 FOM= 0.00 TEST= 0
INDE 33 53 34 FOBS=  18.3 SIGMA= 12.9 PHAS= -120.6 FOM= 0.31 TEST= 0
INDE 33 53 36 FOBS=  45.5 SIGMA=  4.0 PHAS=   17.8 FOM= 0.54 TEST= 0
INDE 33 53 38 FOBS=  88.4 SIGMA=  2.2 PHAS=  129.3 FOM= 0.89 TEST= 0
INDE 33 53 40 FOBS=  36.9 SIGMA=  6.2 PHAS=  -50.5 FOM= 0.56 TEST= 0
INDE 33 53 42 FOBS=  43.4 SIGMA=  5.4 PHAS= -147.6 FOM= 0.62 TEST= 0
INDE 33 53 44 FOBS=   0.0 SIGMA= 22.5 PHAS=    0.0 FOM= 0.00 TEST= 0
INDE 33 53 46 FOBS=   0.0 SIGMA= 23.9 PHAS=    0.0 FOM= 0.00 TEST= 0
INDE 33 54 33 FOBS= 117.8 SIGMA=  1.7 PHAS= -165.8 FOM= 0.95 TEST= 0
INDE 33 54 35 FOBS=  22.4 SIGMA=  9.2 PHAS=  146.2 FOM= 0.03 TEST= 0
INDE 33 54 37 FOBS=  67.8 SIGMA=  2.9 PHAS=   26.1 FOM= 0.90 TEST= 0
INDE 33 54 39 FOBS=  51.2 SIGMA=  4.5 PHAS=  -87.5 FOM= 0.49 TEST= 0
INDE 33 54 41 FOBS=  39.4 SIGMA=  6.5 PHAS=  147.1 FOM= 0.87 TEST= 0
INDE 33 54 43 FOBS=   0.0 SIGMA= 21.8 PHAS=    0.0 FOM= 0.00 TEST= 0
INDE 33 54 45 FOBS=  33.8 SIGMA=  6.9 PHAS= -155.9 FOM= 0.42 TEST= 0
INDE 33 55 34 FOBS= 100.3 SIGMA=  2.0 PHAS=  101.7 FOM= 0.90 TEST= 0
INDE 33 55 36 FOBS=  82.9 SIGMA=  2.4 PHAS=  -64.3 FOM= 0.30 TEST= 1
```

*FIG. 12A - 551*

```
INDE 33 55 38 FOBS=    27.2 SIGMA=  8.5 PHAS= -144.1 FOM= 0.06 TEST= 0
INDE 33 55 40 FOBS=    84.9 SIGMA=  2.8 PHAS=   -2.0 FOM= 0.94 TEST= 0
INDE 33 55 42 FOBS=    59.0 SIGMA=  4.4 PHAS= -138.0 FOM= 0.77 TEST= 0
INDE 33 56 33 FOBS=    50.6 SIGMA=  3.7 PHAS=   30.0 FOM= 0.80 TEST= 0
INDE 33 56 35 FOBS=    54.7 SIGMA=  3.8 PHAS= -133.5 FOM= 0.76 TEST= 0
INDE 33 56 37 FOBS=    15.4 SIGMA= 20.1 PHAS=  111.7 FOM= 0.19 TEST= 0
INDE 33 56 39 FOBS=   144.9 SIGMA=  1.7 PHAS= -128.9 FOM= 0.97 TEST= 0
INDE 33 56 41 FOBS=    42.7 SIGMA=  6.1 PHAS=  154.2 FOM= 0.65 TEST= 0
INDE 33 57 34 FOBS=    63.3 SIGMA=  3.5 PHAS=   12.4 FOM= 0.85 TEST= 0
INDE 33 57 36 FOBS=    21.8 SIGMA= 10.4 PHAS= -152.1 FOM= 0.00 TEST= 1
INDE 33 57 38 FOBS=    57.6 SIGMA=  4.1 PHAS=   80.4 FOM= 0.89 TEST= 0
INDE 33 57 40 FOBS=    35.0 SIGMA=  7.4 PHAS=  -12.4 FOM= 0.53 TEST= 0
INDE 33 58 33 FOBS=     0.0 SIGMA= 23.8 PHAS=    0.0 FOM= 0.00 TEST= 0
INDE 33 58 35 FOBS=    37.9 SIGMA=  6.9 PHAS=  -90.4 FOM= 0.58 TEST= 0
INDE 33 58 37 FOBS=     0.0 SIGMA= 23.4 PHAS=    0.0 FOM= 0.00 TEST= 0
INDE 33 58 39 FOBS=    85.0 SIGMA=  2.9 PHAS= -123.1 FOM= 0.84 TEST= 0
INDE 33 59 34 FOBS=     0.0 SIGMA= 22.0 PHAS=    0.0 FOM= 0.00 TEST= 0
INDE 33 59 36 FOBS=    14.4 SIGMA= 15.8 PHAS= -126.6 FOM= 0.21 TEST= 0
INDE 33 59 38 FOBS=    18.1 SIGMA= 14.1 PHAS=  103.0 FOM= 0.40 TEST= 0
INDE 33 60 33 FOBS=     2.9 SIGMA= 77.4 PHAS= -135.9 FOM= 0.04 TEST= 0
INDE 33 60 35 FOBS=    65.7 SIGMA=  3.5 PHAS=  114.7 FOM= 0.30 TEST= 0
INDE 33 61 34 FOBS=    38.1 SIGMA=  6.1 PHAS= -115.8 FOM= 0.29 TEST= 0
INDE 33 62 33 FOBS=    23.7 SIGMA= 11.6 PHAS= -179.6 FOM= 0.42 TEST= 0
INDE 34 34 34 FOBS=   194.3 SIGMA=  1.6 PHAS=  120.5 FOM= 0.98 TEST= 0
INDE 34 35 35 FOBS=    49.4 SIGMA=  3.4 PHAS= -144.5 FOM= 0.33 TEST= 0
INDE 34 35 37 FOBS=    50.1 SIGMA=  3.6 PHAS=   24.7 FOM= 0.90 TEST= 0
INDE 34 35 39 FOBS=    43.0 SIGMA=  4.1 PHAS=  -13.5 FOM= 0.39 TEST= 0
INDE 34 35 41 FOBS=    51.9 SIGMA=  3.6 PHAS=  101.4 FOM= 0.68 TEST= 0
INDE 34 35 43 FOBS=    47.1 SIGMA=  3.9 PHAS= -143.1 FOM= 0.18 TEST= 0
INDE 34 35 45 FOBS=   159.2 SIGMA=  1.2 PHAS=   66.1 FOM= 0.83 TEST= 1
INDE 34 35 47 FOBS=    15.7 SIGMA= 13.0 PHAS=  -87.7 FOM= 0.16 TEST= 0
INDE 34 35 49 FOBS=    81.9 SIGMA=  2.3 PHAS=   13.2 FOM= 0.12 TEST= 1
INDE 34 35 51 FOBS=   111.9 SIGMA=  1.7 PHAS=   63.9 FOM= 0.94 TEST= 0
INDE 34 35 53 FOBS=    89.6 SIGMA=  2.2 PHAS=  -69.8 FOM= 0.78 TEST= 1
INDE 34 35 55 FOBS=    17.1 SIGMA= 11.8 PHAS=   -7.6 FOM= 0.32 TEST= 0
INDE 34 35 57 FOBS=    27.2 SIGMA=  8.1 PHAS= -169.6 FOM= 0.23 TEST= 0
INDE 34 35 59 FOBS=    19.7 SIGMA= 11.6 PHAS= -113.9 FOM= 0.22 TEST= 0
INDE 34 36 34 FOBS=   115.9 SIGMA=  1.5 PHAS=   92.1 FOM= 0.89 TEST= 0
INDE 34 36 36 FOBS=     0.0 SIGMA= 19.3 PHAS=    0.0 FOM= 0.00 TEST= 0
INDE 34 36 38 FOBS=    80.2 SIGMA=  2.1 PHAS=  -77.9 FOM= 0.73 TEST= 0
INDE 34 36 40 FOBS=    94.1 SIGMA=  2.0 PHAS=  -31.3 FOM= 0.51 TEST= 1
INDE 34 36 42 FOBS=    46.5 SIGMA=  4.4 PHAS=   36.5 FOM= 0.67 TEST= 0
INDE 34 36 44 FOBS=    52.4 SIGMA=  3.5 PHAS=   80.5 FOM= 0.26 TEST= 0
INDE 34 36 46 FOBS=    35.8 SIGMA=  5.4 PHAS=  -68.3 FOM= 0.46 TEST= 0
INDE 34 36 48 FOBS=    95.7 SIGMA=  2.0 PHAS=   28.7 FOM= 0.91 TEST= 0
INDE 34 36 50 FOBS=   104.5 SIGMA=  1.8 PHAS=  177.4 FOM= 0.17 TEST= 1
INDE 34 36 52 FOBS=    42.1 SIGMA=  4.6 PHAS=  128.8 FOM= 0.66 TEST= 0
INDE 34 36 54 FOBS=    59.5 SIGMA=  3.3 PHAS= -141.1 FOM= 0.74 TEST= 0
INDE 34 36 56 FOBS=    35.3 SIGMA=  6.8 PHAS= -176.8 FOM= 0.05 TEST= 1
INDE 34 36 58 FOBS=    78.4 SIGMA=  2.6 PHAS=    9.2 FOM= 0.94 TEST= 0
INDE 34 37 35 FOBS=   131.4 SIGMA=  1.3 PHAS=  -15.2 FOM= 0.94 TEST= 0
INDE 34 37 37 FOBS=    82.3 SIGMA=  2.1 PHAS= -138.7 FOM= 0.85 TEST= 0
INDE 34 37 39 FOBS=    79.7 SIGMA=  2.3 PHAS=  152.4 FOM= 0.88 TEST= 0
INDE 34 37 41 FOBS=    14.7 SIGMA= 14.1 PHAS= -101.0 FOM= 0.13 TEST= 0
INDE 34 37 43 FOBS=    46.5 SIGMA=  4.2 PHAS=  -52.3 FOM= 0.63 TEST= 0
INDE 34 37 45 FOBS=   142.7 SIGMA=  1.4 PHAS=   96.4 FOM= 0.96 TEST= 0
INDE 34 37 47 FOBS=    27.0 SIGMA=  6.8 PHAS=   56.3 FOM= 0.61 TEST= 0
INDE 34 37 49 FOBS=    18.4 SIGMA= 12.0 PHAS=   33.6 FOM= 0.29 TEST= 0
INDE 34 37 51 FOBS=   137.1 SIGMA=  1.4 PHAS=   28.4 FOM= 0.97 TEST= 0
INDE 34 37 53 FOBS=    46.9 SIGMA=  4.2 PHAS=   35.0 FOM= 0.16 TEST= 1
INDE 34 37 55 FOBS=    22.8 SIGMA=  8.6 PHAS=  -78.6 FOM= 0.22 TEST= 0
INDE 34 37 57 FOBS=    73.8 SIGMA=  2.7 PHAS=  -66.5 FOM= 0.85 TEST= 0
INDE 34 37 59 FOBS=    55.8 SIGMA=  3.7 PHAS=  -78.5 FOM= 0.86 TEST= 0
INDE 34 38 34 FOBS=   125.4 SIGMA=  1.4 PHAS= -103.8 FOM= 0.93 TEST= 0
INDE 34 38 36 FOBS=    26.6 SIGMA=  6.5 PHAS= -111.6 FOM= 0.49 TEST= 0
INDE 34 38 38 FOBS=   155.4 SIGMA=  1.2 PHAS=   81.7 FOM= 0.57 TEST= 1
INDE 34 38 40 FOBS=    57.4 SIGMA=  3.3 PHAS= -115.8 FOM= 0.33 TEST= 0
INDE 34 38 42 FOBS=    73.1 SIGMA=  2.6 PHAS=   98.4 FOM= 0.07 TEST= 1
INDE 34 38 44 FOBS=   122.3 SIGMA=  1.6 PHAS=   46.1 FOM= 0.94 TEST= 0
INDE 34 38 46 FOBS=    66.1 SIGMA=  2.8 PHAS=  -12.6 FOM= 0.81 TEST= 0
```

*FIG. 12A - 552*

| | | | | | | | | | | | |
|---|---|---|---|---|---|---|---|---|---|---|---|
| INDE | 34 | 38 | 48 | FOBS= | 0.0 | SIGMA= | 20.1 | PHAS= | 0.0 | FOM= | 0.00 | TEST= 0
| INDE | 34 | 38 | 50 | FOBS= | 118.7 | SIGMA= | 1.6 | PHAS= | -97.3 | FOM= | 0.96 | TEST= 0
| INDE | 34 | 38 | 52 | FOBS= | 63.1 | SIGMA= | 3.2 | PHAS= | -33.4 | FOM= | 0.61 | TEST= 0
| INDE | 34 | 38 | 54 | FOBS= | 45.0 | SIGMA= | 4.4 | PHAS= | -98.8 | FOM= | 0.77 | TEST= 0
| INDE | 34 | 38 | 56 | FOBS= | 54.4 | SIGMA= | 3.7 | PHAS= | -174.1 | FOM= | 0.78 | TEST= 0
| INDE | 34 | 38 | 58 | FOBS= | 8.7 | SIGMA= | 23.5 | PHAS= | -135.9 | FOM= | 0.09 | TEST= 0
| INDE | 34 | 39 | 35 | FOBS= | 40.7 | SIGMA= | 4.3 | PHAS= | 162.7 | FOM= | 0.29 | TEST= 1
| INDE | 34 | 39 | 37 | FOBS= | 54.7 | SIGMA= | 3.1 | PHAS= | -55.1 | FOM= | 0.78 | TEST= 0
| INDE | 34 | 39 | 39 | FOBS= | 63.6 | SIGMA= | 2.8 | PHAS= | 81.3 | FOM= | 0.75 | TEST= 0
| INDE | 34 | 39 | 41 | FOBS= | 0.0 | SIGMA= | 21.0 | PHAS= | 0.0 | FOM= | 0.00 | TEST= 0
| INDE | 34 | 39 | 43 | FOBS= | 70.8 | SIGMA= | 2.6 | PHAS= | -44.3 | FOM= | 0.78 | TEST= 0
| INDE | 34 | 39 | 45 | FOBS= | 91.5 | SIGMA= | 2.1 | PHAS= | -10.2 | FOM= | 0.47 | TEST= 1
| INDE | 34 | 39 | 47 | FOBS= | 46.3 | SIGMA= | 4.0 | PHAS= | 158.9 | FOM= | 0.74 | TEST= 0
| INDE | 34 | 39 | 49 | FOBS= | 48.0 | SIGMA= | 4.0 | PHAS= | 98.2 | FOM= | 0.80 | TEST= 0
| INDE | 34 | 39 | 51 | FOBS= | 72.9 | SIGMA= | 2.6 | PHAS= | 114.2 | FOM= | 0.43 | TEST= 0
| INDE | 34 | 39 | 53 | FOBS= | 27.5 | SIGMA= | 7.3 | PHAS= | -32.3 | FOM= | 0.11 | TEST= 0
| INDE | 34 | 39 | 55 | FOBS= | 54.0 | SIGMA= | 3.8 | PHAS= | -153.3 | FOM= | 0.81 | TEST= 0
| INDE | 34 | 39 | 57 | FOBS= | 18.6 | SIGMA= | 12.6 | PHAS= | -88.6 | FOM= | 0.26 | TEST= 0
| INDE | 34 | 40 | 34 | FOBS= | 54.5 | SIGMA= | 3.4 | PHAS= | 2.4 | FOM= | 0.66 | TEST= 0
| INDE | 34 | 40 | 36 | FOBS= | 65.0 | SIGMA= | 2.6 | PHAS= | 65.8 | FOM= | 0.80 | TEST= 0
| INDE | 34 | 40 | 38 | FOBS= | 32.5 | SIGMA= | 6.3 | PHAS= | -165.6 | FOM= | 0.71 | TEST= 0
| INDE | 34 | 40 | 40 | FOBS= | 77.0 | SIGMA= | 2.4 | PHAS= | 21.9 | FOM= | 0.81 | TEST= 0
| INDE | 34 | 40 | 42 | FOBS= | 0.0 | SIGMA= | 19.8 | PHAS= | 0.0 | FOM= | 0.00 | TEST= 0
| INDE | 34 | 40 | 44 | FOBS= | 0.0 | SIGMA= | 19.2 | PHAS= | 0.0 | FOM= | 0.00 | TEST= 0
| INDE | 34 | 40 | 46 | FOBS= | 31.8 | SIGMA= | 6.1 | PHAS= | -106.5 | FOM= | 0.47 | TEST= 0
| INDE | 34 | 40 | 48 | FOBS= | 108.5 | SIGMA= | 1.8 | PHAS= | 32.1 | FOM= | 0.21 | TEST= 1
| INDE | 34 | 40 | 50 | FOBS= | 115.0 | SIGMA= | 1.7 | PHAS= | 11.9 | FOM= | 0.17 | TEST= 1
| INDE | 34 | 40 | 52 | FOBS= | 62.4 | SIGMA= | 3.2 | PHAS= | -150.2 | FOM= | 0.40 | TEST= 0
| INDE | 34 | 40 | 54 | FOBS= | 18.2 | SIGMA= | 11.9 | PHAS= | -154.6 | FOM= | 0.29 | TEST= 0
| INDE | 34 | 40 | 56 | FOBS= | 78.4 | SIGMA= | 2.7 | PHAS= | -143.4 | FOM= | 0.93 | TEST= 0
| INDE | 34 | 41 | 35 | FOBS= | 133.2 | SIGMA= | 1.4 | PHAS= | -67.5 | FOM= | 0.91 | TEST= 0
| INDE | 34 | 41 | 37 | FOBS= | 49.4 | SIGMA= | 3.4 | PHAS= | 24.2 | FOM= | 0.61 | TEST= 0
| INDE | 34 | 41 | 39 | FOBS= | 140.6 | SIGMA= | 1.3 | PHAS= | 104.1 | FOM= | 0.94 | TEST= 0
| INDE | 34 | 41 | 41 | FOBS= | 49.0 | SIGMA= | 3.8 | PHAS= | -171.5 | FOM= | 0.78 | TEST= 0
| INDE | 34 | 41 | 43 | FOBS= | 0.0 | SIGMA= | 19.6 | PHAS= | 0.0 | FOM= | 0.00 | TEST= 0
| INDE | 34 | 41 | 45 | FOBS= | 61.1 | SIGMA= | 3.1 | PHAS= | 52.9 | FOM= | 0.81 | TEST= 0
| INDE | 34 | 41 | 47 | FOBS= | 61.2 | SIGMA= | 3.2 | PHAS= | 76.3 | FOM= | 0.70 | TEST= 0
| INDE | 34 | 41 | 49 | FOBS= | 147.9 | SIGMA= | 1.4 | PHAS= | -22.2 | FOM= | 0.97 | TEST= 0
| INDE | 34 | 41 | 51 | FOBS= | 30.2 | SIGMA= | 6.6 | PHAS= | 120.0 | FOM= | 0.02 | TEST= 1
| INDE | 34 | 41 | 53 | FOBS= | 0.0 | SIGMA= | 20.1 | PHAS= | 0.0 | FOM= | 0.00 | TEST= 0
| INDE | 34 | 41 | 55 | FOBS= | 59.8 | SIGMA= | 3.5 | PHAS= | 166.8 | FOM= | 0.84 | TEST= 0
| INDE | 34 | 42 | 34 | FOBS= | 121.7 | SIGMA= | 1.6 | PHAS= | 163.7 | FOM= | 0.95 | TEST= 0
| INDE | 34 | 42 | 36 | FOBS= | 48.8 | SIGMA= | 3.5 | PHAS= | 68.3 | FOM= | 0.59 | TEST= 0
| INDE | 34 | 42 | 38 | FOBS= | 98.0 | SIGMA= | 1.7 | PHAS= | -157.0 | FOM= | 0.85 | TEST= 0
| INDE | 34 | 42 | 40 | FOBS= | 130.3 | SIGMA= | 1.5 | PHAS= | 82.5 | FOM= | 0.95 | TEST= 0
| INDE | 34 | 42 | 42 | FOBS= | 89.9 | SIGMA= | 2.1 | PHAS= | 43.2 | FOM= | 0.93 | TEST= 0
| INDE | 34 | 42 | 44 | FOBS= | 75.0 | SIGMA= | 2.5 | PHAS= | -104.1 | FOM= | 0.92 | TEST= 0
| INDE | 34 | 42 | 46 | FOBS= | 32.7 | SIGMA= | 5.7 | PHAS= | -17.1 | FOM= | 0.65 | TEST= 0
| INDE | 34 | 42 | 48 | FOBS= | 107.2 | SIGMA= | 1.8 | PHAS= | -102.2 | FOM= | 0.96 | TEST= 0
| INDE | 34 | 42 | 50 | FOBS= | 36.2 | SIGMA= | 6.4 | PHAS= | -115.6 | FOM= | 0.72 | TEST= 0
| INDE | 34 | 42 | 52 | FOBS= | 32.1 | SIGMA= | 7.0 | PHAS= | -85.5 | FOM= | 0.55 | TEST= 0
| INDE | 34 | 42 | 54 | FOBS= | 57.4 | SIGMA= | 4.2 | PHAS= | 92.6 | FOM= | 0.07 | TEST= 0
| INDE | 34 | 43 | 35 | FOBS= | 45.7 | SIGMA= | 4.2 | PHAS= | 74.8 | FOM= | 0.20 | TEST= 0
| INDE | 34 | 43 | 37 | FOBS= | 66.3 | SIGMA= | 2.5 | PHAS= | 22.8 | FOM= | 0.47 | TEST= 0
| INDE | 34 | 43 | 39 | FOBS= | 117.6 | SIGMA= | 1.5 | PHAS= | 113.4 | FOM= | 0.93 | TEST= 0
| INDE | 34 | 43 | 41 | FOBS= | 89.5 | SIGMA= | 2.1 | PHAS= | -44.8 | FOM= | 0.92 | TEST= 0
| INDE | 34 | 43 | 43 | FOBS= | 67.9 | SIGMA= | 2.8 | PHAS= | -71.4 | FOM= | 0.87 | TEST= 0
| INDE | 34 | 43 | 45 | FOBS= | 0.0 | SIGMA= | 21.0 | PHAS= | 0.0 | FOM= | 0.00 | TEST= 0
| INDE | 34 | 43 | 47 | FOBS= | 0.0 | SIGMA= | 21.2 | PHAS= | 0.0 | FOM= | 0.00 | TEST= 0
| INDE | 34 | 43 | 49 | FOBS= | 7.9 | SIGMA= | 25.3 | PHAS= | -47.7 | FOM= | 0.10 | TEST= 0
| INDE | 34 | 43 | 51 | FOBS= | 67.8 | SIGMA= | 3.0 | PHAS= | 146.3 | FOM= | 0.87 | TEST= 0
| INDE | 34 | 43 | 53 | FOBS= | 30.6 | SIGMA= | 7.8 | PHAS= | -125.1 | FOM= | 0.55 | TEST= 0
| INDE | 34 | 43 | 55 | FOBS= | 50.7 | SIGMA= | 4.2 | PHAS= | -47.3 | FOM= | 0.59 | TEST= 0
| INDE | 34 | 44 | 34 | FOBS= | 83.3 | SIGMA= | 2.2 | PHAS= | -177.9 | FOM= | 0.87 | TEST= 0
| INDE | 34 | 44 | 36 | FOBS= | 50.5 | SIGMA= | 3.8 | PHAS= | 82.7 | FOM= | 0.55 | TEST= 0
| INDE | 34 | 44 | 38 | FOBS= | 66.8 | SIGMA= | 2.5 | PHAS= | 177.6 | FOM= | 0.61 | TEST= 0
| INDE | 34 | 44 | 40 | FOBS= | 44.2 | SIGMA= | 3.9 | PHAS= | 50.2 | FOM= | 0.74 | TEST= 0
| INDE | 34 | 44 | 42 | FOBS= | 49.1 | SIGMA= | 3.8 | PHAS= | 81.6 | FOM= | 0.75 | TEST= 0
| INDE | 34 | 44 | 44 | FOBS= | 150.7 | SIGMA= | 1.3 | PHAS= | -115.5 | FOM= | 0.96 | TEST= 0
| INDE | 34 | 44 | 46 | FOBS= | 34.8 | SIGMA= | 5.5 | PHAS= | -75.8 | FOM= | 0.36 | TEST= 0

*FIG. 12A - 553*

```
INDE 34 44 48 FOBS=  51.1 SIGMA=  3.9 PHAS=  -99.6 FOM= 0.79 TEST= 0
INDE 34 44 50 FOBS=  31.7 SIGMA=  6.3 PHAS=  -35.5 FOM= 0.20 TEST= 1
INDE 34 44 52 FOBS=  45.2 SIGMA=  4.6 PHAS=   94.7 FOM= 0.69 TEST= 0
INDE 34 44 54 FOBS=  37.5 SIGMA=  5.7 PHAS= -165.2 FOM= 0.70 TEST= 0
INDE 34 45 35 FOBS=  22.3 SIGMA=  8.6 PHAS=   -0.5 FOM= 0.28 TEST= 0
INDE 34 45 37 FOBS=  41.5 SIGMA=  4.4 PHAS=   20.5 FOM= 0.83 TEST= 0
INDE 34 45 39 FOBS=  65.3 SIGMA=  2.6 PHAS= -126.0 FOM= 0.67 TEST= 0
INDE 34 45 41 FOBS=  78.3 SIGMA=  2.4 PHAS=  -10.0 FOM= 0.80 TEST= 0
INDE 34 45 43 FOBS=  24.3 SIGMA=  8.1 PHAS= -166.0 FOM= 0.61 TEST= 0
INDE 34 45 45 FOBS= 104.8 SIGMA=  1.9 PHAS=  162.3 FOM= 0.89 TEST= 0
INDE 34 45 47 FOBS=  16.0 SIGMA= 12.5 PHAS=   62.1 FOM= 0.04 TEST= 0
INDE 34 45 49 FOBS=   0.0 SIGMA= 19.6 PHAS=    0.0 FOM= 0.00 TEST= 0
INDE 34 45 51 FOBS=  47.3 SIGMA=  4.4 PHAS=   47.6 FOM= 0.68 TEST= 0
INDE 34 45 53 FOBS=  50.1 SIGMA=  4.2 PHAS=  -54.6 FOM= 0.72 TEST= 0
INDE 34 46 34 FOBS=  33.7 SIGMA=  5.6 PHAS=   25.6 FOM= 0.60 TEST= 0
INDE 34 46 36 FOBS=   0.0 SIGMA= 20.1 PHAS=    0.0 FOM= 0.00 TEST= 0
INDE 34 46 38 FOBS=  29.4 SIGMA=  5.8 PHAS=  141.0 FOM= 0.75 TEST= 0
INDE 34 46 40 FOBS=   0.0 SIGMA= 18.6 PHAS=    0.0 FOM= 0.00 TEST= 1
INDE 34 46 42 FOBS=   0.0 SIGMA= 20.4 PHAS=    0.0 FOM= 0.00 TEST= 1
INDE 34 46 44 FOBS=  62.4 SIGMA=  3.1 PHAS=   27.1 FOM= 0.81 TEST= 0
INDE 34 46 46 FOBS=  23.4 SIGMA=  9.1 PHAS= -165.6 FOM= 0.40 TEST= 0
INDE 34 46 48 FOBS=   0.0 SIGMA= 19.6 PHAS=    0.0 FOM= 0.00 TEST= 0
INDE 34 46 50 FOBS=  89.6 SIGMA=  2.4 PHAS=    0.1 FOM= 0.90 TEST= 0
INDE 34 46 52 FOBS=  60.1 SIGMA=  3.6 PHAS= -178.0 FOM= 0.78 TEST= 0
INDE 34 47 35 FOBS=  18.2 SIGMA= 11.9 PHAS=    2.5 FOM= 0.11 TEST= 0
INDE 34 47 37 FOBS=  46.8 SIGMA=  3.9 PHAS=   53.0 FOM= 0.60 TEST= 0
INDE 34 47 39 FOBS=   0.0 SIGMA= 18.7 PHAS=    0.0 FOM= 0.00 TEST= 0
INDE 34 47 41 FOBS=   0.0 SIGMA= 19.2 PHAS=    0.0 FOM= 0.00 TEST= 0
INDE 34 47 43 FOBS=  42.4 SIGMA=  4.5 PHAS=   35.4 FOM= 0.23 TEST= 0
INDE 34 47 45 FOBS=  38.4 SIGMA=  5.0 PHAS= -141.5 FOM= 0.22 TEST= 0
INDE 34 47 47 FOBS=   0.0 SIGMA= 20.2 PHAS=    0.0 FOM= 0.00 TEST= 0
INDE 34 47 49 FOBS=  77.1 SIGMA=  2.6 PHAS=  -42.4 FOM= 0.13 TEST= 1
INDE 34 47 51 FOBS=   0.0 SIGMA= 20.6 PHAS=    0.0 FOM= 0.00 TEST= 0
INDE 34 48 34 FOBS=  69.8 SIGMA=  2.6 PHAS=   -1.0 FOM= 0.82 TEST= 0
INDE 34 48 36 FOBS= 116.2 SIGMA=  1.7 PHAS=   77.6 FOM= 0.77 TEST= 0
INDE 34 48 38 FOBS=   0.0 SIGMA= 19.6 PHAS=    0.0 FOM= 0.00 TEST= 0
INDE 34 48 40 FOBS=  24.9 SIGMA=  7.4 PHAS= -135.1 FOM= 0.48 TEST= 0
INDE 34 48 42 FOBS=  31.5 SIGMA=  6.0 PHAS=   91.1 FOM= 0.57 TEST= 0
INDE 34 48 44 FOBS=   0.0 SIGMA= 20.6 PHAS=    0.0 FOM= 0.00 TEST= 0
INDE 34 48 46 FOBS=  19.9 SIGMA= 11.5 PHAS=  -80.2 FOM= 0.15 TEST= 0
INDE 34 48 48 FOBS=  47.8 SIGMA=  4.1 PHAS=  -94.1 FOM= 0.85 TEST= 0
INDE 34 48 50 FOBS=   0.0 SIGMA= 22.3 PHAS=    0.0 FOM= 0.00 TEST= 0
INDE 34 49 35 FOBS=  72.8 SIGMA=  2.7 PHAS=  -33.7 FOM= 0.80 TEST= 0
INDE 34 49 37 FOBS=  73.1 SIGMA=  2.6 PHAS=  176.1 FOM= 0.79 TEST= 0
INDE 34 49 39 FOBS=   0.0 SIGMA= 19.5 PHAS=    0.0 FOM= 0.00 TEST= 0
INDE 34 49 41 FOBS=   0.0 SIGMA= 19.3 PHAS=    0.0 FOM= 0.00 TEST= 0
INDE 34 49 43 FOBS=  26.6 SIGMA=  7.5 PHAS=   96.0 FOM= 0.36 TEST= 0
INDE 34 49 45 FOBS=  81.9 SIGMA=  2.4 PHAS=  176.4 FOM= 0.90 TEST= 0
INDE 34 49 47 FOBS=   0.0 SIGMA= 21.9 PHAS=    0.0 FOM= 0.00 TEST= 1
INDE 34 49 49 FOBS=  30.2 SIGMA=  8.7 PHAS=   89.9 FOM= 0.47 TEST= 0
INDE 34 50 34 FOBS=   0.0 SIGMA= 19.8 PHAS=    0.0 FOM= 0.00 TEST= 0
INDE 34 50 36 FOBS=  97.9 SIGMA=  1.9 PHAS=   90.6 FOM= 0.93 TEST= 0
INDE 34 50 38 FOBS=   0.0 SIGMA= 19.6 PHAS=    0.0 FOM= 0.00 TEST= 0
INDE 34 50 40 FOBS=   0.0 SIGMA= 20.2 PHAS=    0.0 FOM= 0.00 TEST= 0
INDE 34 50 42 FOBS=  72.9 SIGMA=  2.6 PHAS=   27.6 FOM= 0.43 TEST= 0
INDE 34 50 44 FOBS=  65.9 SIGMA=  3.0 PHAS=   89.0 FOM= 0.02 TEST= 1
INDE 34 50 46 FOBS=  38.5 SIGMA=  5.4 PHAS=  -83.0 FOM= 0.69 TEST= 0
INDE 34 50 48 FOBS=  51.0 SIGMA=  4.5 PHAS=  -58.2 FOM= 0.53 TEST= 0
INDE 34 51 35 FOBS=  66.7 SIGMA=  2.8 PHAS=  -42.1 FOM= 0.69 TEST= 0
INDE 34 51 37 FOBS=  24.1 SIGMA=  8.6 PHAS= -165.2 FOM= 0.39 TEST= 0
INDE 34 51 39 FOBS=  32.8 SIGMA=  5.7 PHAS=  149.0 FOM= 0.49 TEST= 0
INDE 34 51 41 FOBS=  28.8 SIGMA=  7.0 PHAS= -119.6 FOM= 0.08 TEST= 0
INDE 34 51 43 FOBS=  10.5 SIGMA= 21.6 PHAS= -124.1 FOM= 0.17 TEST= 0
INDE 34 51 45 FOBS=  85.2 SIGMA=  2.4 PHAS= -170.8 FOM= 0.95 TEST= 0
INDE 34 51 47 FOBS=   0.0 SIGMA= 21.5 PHAS=    0.0 FOM= 0.00 TEST= 0
INDE 34 52 34 FOBS=  56.6 SIGMA=  3.2 PHAS=   80.9 FOM= 0.53 TEST= 1
INDE 34 52 36 FOBS=  50.4 SIGMA=  3.7 PHAS= -113.8 FOM= 0.40 TEST= 0
INDE 34 52 38 FOBS=  25.1 SIGMA=  8.8 PHAS=   -8.7 FOM= 0.68 TEST= 0
INDE 34 52 40 FOBS=  51.2 SIGMA=  3.7 PHAS=  163.8 FOM= 0.77 TEST= 0
INDE 34 52 42 FOBS=  41.8 SIGMA=  4.4 PHAS=  114.2 FOM= 0.30 TEST= 0
```

*FIG. 12A - 554*

```
INDE  34  52  44  FOBS=   86.4  SIGMA=   2.5  PHAS=  112.5  FOM=  0.90  TEST=  0
INDE  34  52  46  FOBS=   12.6  SIGMA=  19.6  PHAS=   33.9  FOM=  0.23  TEST=  0
INDE  34  53  35  FOBS=   44.1  SIGMA=   4.7  PHAS= -179.3  FOM=  0.68  TEST=  0
INDE  34  53  37  FOBS=   64.7  SIGMA=   3.1  PHAS= -143.8  FOM=  0.84  TEST=  0
INDE  34  53  39  FOBS=   45.7  SIGMA=   4.4  PHAS=   81.3  FOM=  0.77  TEST=  0
INDE  34  53  41  FOBS=   80.8  SIGMA=   2.5  PHAS=   64.6  FOM=  0.88  TEST=  0
INDE  34  53  43  FOBS=    0.0  SIGMA=  24.1  PHAS=    0.0  FOM=  0.00  TEST=  0
INDE  34  53  45  FOBS=   34.2  SIGMA=   6.7  PHAS=  100.5  FOM=  0.05  TEST=  1
INDE  34  54  34  FOBS=   53.1  SIGMA=   3.7  PHAS=  105.7  FOM=  0.81  TEST=  0
INDE  34  54  36  FOBS=   36.8  SIGMA=   6.1  PHAS=  127.2  FOM=  0.36  TEST=  0
INDE  34  54  38  FOBS=   60.3  SIGMA=   3.3  PHAS=  -35.2  FOM=  0.76  TEST=  0
INDE  34  54  40  FOBS=   75.2  SIGMA=   2.7  PHAS=  -90.1  FOM=  0.88  TEST=  0
INDE  34  54  42  FOBS=    0.0  SIGMA=  21.8  PHAS=    0.0  FOM=  0.00  TEST=  0
INDE  34  54  44  FOBS=    0.0  SIGMA=  21.4  PHAS=    0.0  FOM=  0.00  TEST=  0
INDE  34  55  35  FOBS=   64.8  SIGMA=   3.0  PHAS=   80.3  FOM=  0.87  TEST=  0
INDE  34  55  37  FOBS=   45.1  SIGMA=   4.4  PHAS= -129.2  FOM=  0.79  TEST=  0
INDE  34  55  39  FOBS=   96.7  SIGMA=   2.3  PHAS=  159.3  FOM=  0.95  TEST=  0
INDE  34  55  41  FOBS=   37.0  SIGMA=   7.2  PHAS=  -95.0  FOM=  0.47  TEST=  0
INDE  34  55  43  FOBS=   41.4  SIGMA=   5.6  PHAS=  164.5  FOM=  0.69  TEST=  0
INDE  34  56  34  FOBS=   78.9  SIGMA=   2.5  PHAS=  -27.5  FOM=  0.92  TEST=  0
INDE  34  56  36  FOBS=    0.0  SIGMA=  21.6  PHAS=    0.0  FOM=  0.00  TEST=  1
INDE  34  56  38  FOBS=   75.2  SIGMA=   3.4  PHAS=   50.6  FOM=  0.41  TEST=  1
INDE  34  56  40  FOBS=   84.7  SIGMA=   2.9  PHAS=  133.9  FOM=  0.94  TEST=  0
INDE  34  57  35  FOBS=    0.0  SIGMA=  21.0  PHAS=    0.0  FOM=  0.00  TEST=  0
INDE  34  57  37  FOBS=    0.0  SIGMA=  22.4  PHAS=    0.0  FOM=  0.00  TEST=  0
INDE  34  57  39  FOBS=  110.1  SIGMA=   2.2  PHAS=   64.0  FOM=  0.94  TEST=  0
INDE  34  58  34  FOBS=    0.0  SIGMA=  21.2  PHAS=    0.0  FOM=  0.00  TEST=  0
INDE  34  58  36  FOBS=    0.0  SIGMA=  21.4  PHAS=    0.0  FOM=  0.00  TEST=  1
INDE  34  58  38  FOBS=   76.3  SIGMA=   3.2  PHAS=  -40.2  FOM=  0.83  TEST=  0
INDE  34  59  35  FOBS=   36.2  SIGMA=   6.4  PHAS=   57.3  FOM=  0.04  TEST=  1
INDE  34  59  37  FOBS=   40.3  SIGMA=   5.9  PHAS= -160.4  FOM=  0.65  TEST=  0
INDE  34  60  34  FOBS=    0.0  SIGMA=  22.3  PHAS=    0.0  FOM=  0.00  TEST=  0
INDE  35  36  35  FOBS=    0.0  SIGMA=  19.2  PHAS=    0.0  FOM=  0.00  TEST=  0
INDE  35  36  37  FOBS=   61.1  SIGMA=   2.8  PHAS= -117.2  FOM=  0.84  TEST=  1
INDE  35  36  39  FOBS=   10.3  SIGMA=  16.6  PHAS= -123.1  FOM=  0.19  TEST=  0
INDE  35  36  41  FOBS=   45.4  SIGMA=   4.6  PHAS=  169.2  FOM=  0.50  TEST=  0
INDE  35  36  43  FOBS=   82.7  SIGMA=   2.3  PHAS=  -38.6  FOM=  0.50  TEST=  1
INDE  35  36  45  FOBS=  113.2  SIGMA=   1.7  PHAS=   -4.4  FOM=  0.94  TEST=  0
INDE  35  36  47  FOBS=   59.4  SIGMA=   3.1  PHAS=   80.7  FOM=  0.76  TEST=  0
INDE  35  36  49  FOBS=  155.4  SIGMA=   1.3  PHAS=  -17.2  FOM=  0.97  TEST=  0
INDE  35  36  51  FOBS=  101.6  SIGMA=   1.9  PHAS=  -29.5  FOM=  0.93  TEST=  0
INDE  35  36  53  FOBS=   58.6  SIGMA=   3.4  PHAS=   24.9  FOM=  0.88  TEST=  0
INDE  35  36  55  FOBS=   34.9  SIGMA=   5.6  PHAS= -137.7  FOM=  0.33  TEST=  0
INDE  35  36  57  FOBS=    0.0  SIGMA=  20.5  PHAS=    0.0  FOM=  0.00  TEST=  0
INDE  35  36  59  FOBS=   29.0  SIGMA=   8.7  PHAS= -105.7  FOM=  0.47  TEST=  0
INDE  35  37  36  FOBS=   10.6  SIGMA=  19.5  PHAS= -132.5  FOM=  0.13  TEST=  0
INDE  35  37  38  FOBS=   67.0  SIGMA=   2.6  PHAS=  136.3  FOM=  0.84  TEST=  0
INDE  35  37  40  FOBS=   62.1  SIGMA=   2.8  PHAS= -167.1  FOM=  0.26  TEST=  1
INDE  35  37  42  FOBS=   68.1  SIGMA=   2.8  PHAS=   54.9  FOM=  0.25  TEST=  0
INDE  35  37  44  FOBS=   45.9  SIGMA=   4.2  PHAS= -118.7  FOM=  0.36  TEST=  0
INDE  35  37  46  FOBS=   89.9  SIGMA=   2.1  PHAS=  -26.2  FOM=  0.67  TEST=  1
INDE  35  37  48  FOBS=   56.6  SIGMA=   3.3  PHAS= -103.3  FOM=  0.85  TEST=  0
INDE  35  37  50  FOBS=  149.6  SIGMA=   1.4  PHAS= -140.2  FOM=  0.96  TEST=  0
INDE  35  37  52  FOBS=   85.1  SIGMA=   2.2  PHAS= -101.9  FOM=  0.09  TEST=  1
INDE  35  37  54  FOBS=    0.0  SIGMA=  21.1  PHAS=    0.0  FOM=  0.00  TEST=  0
INDE  35  37  56  FOBS=   11.7  SIGMA=  18.1  PHAS=   36.7  FOM=  0.03  TEST=  0
INDE  35  37  58  FOBS=   39.5  SIGMA=   5.2  PHAS=  -35.9  FOM=  0.35  TEST=  0
INDE  35  38  35  FOBS=   61.8  SIGMA=   2.7  PHAS=  -48.6  FOM=  0.69  TEST=  1
INDE  35  38  37  FOBS=   31.2  SIGMA=   5.7  PHAS=  149.1  FOM=  0.30  TEST=  0
INDE  35  38  39  FOBS=  102.2  SIGMA=   1.7  PHAS=   18.7  FOM=  0.88  TEST=  0
INDE  35  38  41  FOBS=   36.8  SIGMA=   4.8  PHAS=  -72.0  FOM=  0.28  TEST=  0
INDE  35  38  43  FOBS=   51.1  SIGMA=   3.8  PHAS=  162.1  FOM=  0.72  TEST=  0
INDE  35  38  45  FOBS=  107.8  SIGMA=   1.8  PHAS=  -46.5  FOM=  0.91  TEST=  0
INDE  35  38  47  FOBS=   83.3  SIGMA=   2.3  PHAS=    0.1  FOM=  0.87  TEST=  0
INDE  35  38  49  FOBS=   53.6  SIGMA=   3.7  PHAS=  -42.2  FOM=  0.86  TEST=  0
INDE  35  38  51  FOBS=   67.4  SIGMA=   2.8  PHAS=  -89.3  FOM=  0.05  TEST=  1
INDE  35  38  53  FOBS=   72.7  SIGMA=   2.8  PHAS=   29.2  FOM=  0.07  TEST=  1
INDE  35  38  55  FOBS=   81.3  SIGMA=   2.5  PHAS=  176.5  FOM=  0.93  TEST=  0
INDE  35  38  57  FOBS=   74.4  SIGMA=   2.8  PHAS=  157.3  FOM=  0.87  TEST=  0
INDE  35  39  36  FOBS=  112.3  SIGMA=   1.6  PHAS=  -60.9  FOM=  0.53  TEST=  1
```

*FIG. 12A - 555*

```
INDE 35 39 38 FOBS=  47.6 SIGMA=  3.6 PHAS=   91.2 FOM= 0.16 TEST= 1
INDE 35 39 40 FOBS=   0.0 SIGMA= 18.8 PHAS=    0.0 FOM= 0.00 TEST= 0
INDE 35 39 42 FOBS=  87.0 SIGMA=  2.2 PHAS=  -14.7 FOM= 0.35 TEST= 0
INDE 35 39 44 FOBS=   0.0 SIGMA= 19.2 PHAS=    0.0 FOM= 0.00 TEST= 0
INDE 35 39 46 FOBS= 150.0 SIGMA=  1.3 PHAS= -118.5 FOM= 0.96 TEST= 0
INDE 35 39 48 FOBS=  73.3 SIGMA=  2.6 PHAS= -160.7 FOM= 0.90 TEST= 0
INDE 35 39 50 FOBS=  41.8 SIGMA=  4.6 PHAS= -145.3 FOM= 0.67 TEST= 0
INDE 35 39 52 FOBS=  52.1 SIGMA=  3.9 PHAS=    3.2 FOM= 0.69 TEST= 0
INDE 35 39 54 FOBS=  80.6 SIGMA=  2.6 PHAS=   37.8 FOM= 0.69 TEST= 0
INDE 35 39 56 FOBS= 113.1 SIGMA=  1.9 PHAS=   86.3 FOM= 0.96 TEST= 0
INDE 35 40 35 FOBS= 145.0 SIGMA=  1.2 PHAS=  -94.7 FOM= 0.94 TEST= 0
INDE 35 40 37 FOBS=  90.1 SIGMA=  1.9 PHAS= -103.2 FOM= 0.90 TEST= 0
INDE 35 40 39 FOBS= 119.5 SIGMA=  1.5 PHAS=   82.6 FOM= 0.95 TEST= 0
INDE 35 40 41 FOBS=  42.4 SIGMA=  4.2 PHAS=   65.2 FOM= 0.72 TEST= 0
INDE 35 40 43 FOBS=  26.3 SIGMA=  8.4 PHAS= -171.7 FOM= 0.26 TEST= 0
INDE 35 40 45 FOBS=  51.0 SIGMA=  3.8 PHAS=  165.1 FOM= 0.76 TEST= 0
INDE 35 40 47 FOBS=  68.2 SIGMA=  2.8 PHAS=  105.2 FOM= 0.82 TEST= 0
INDE 35 40 49 FOBS=  24.1 SIGMA=  9.1 PHAS=   93.2 FOM= 0.18 TEST= 0
INDE 35 40 51 FOBS=  26.4 SIGMA=  7.1 PHAS=  -14.9 FOM= 0.38 TEST= 0
INDE 35 40 53 FOBS=  22.2 SIGMA=  9.8 PHAS=  -42.8 FOM= 0.35 TEST= 0
INDE 35 40 55 FOBS=  32.8 SIGMA=  6.8 PHAS= -107.7 FOM= 0.17 TEST= 0
INDE 35 41 36 FOBS=  82.5 SIGMA=  2.1 PHAS= -174.8 FOM= 0.87 TEST= 0
INDE 35 41 38 FOBS=  92.3 SIGMA=  1.9 PHAS= -138.8 FOM= 0.52 TEST= 1
INDE 35 41 40 FOBS= 100.2 SIGMA=  1.7 PHAS=   -5.0 FOM= 0.95 TEST= 0
INDE 35 41 42 FOBS=  82.1 SIGMA=  2.3 PHAS=    1.6 FOM= 0.90 TEST= 0
INDE 35 41 44 FOBS=  41.6 SIGMA=  4.7 PHAS=  136.5 FOM= 0.57 TEST= 0
INDE 35 41 46 FOBS=  44.9 SIGMA=  4.2 PHAS=   47.5 FOM= 0.51 TEST= 0
INDE 35 41 48 FOBS=  49.1 SIGMA=  4.0 PHAS=   67.8 FOM= 0.81 TEST= 0
INDE 35 41 50 FOBS= 115.3 SIGMA=  1.7 PHAS=  -98.3 FOM= 0.56 TEST= 1
INDE 35 41 52 FOBS=   0.0 SIGMA= 21.3 PHAS=    0.0 FOM= 0.00 TEST= 0
INDE 35 41 54 FOBS=  45.0 SIGMA=  4.6 PHAS= -176.9 FOM= 0.34 TEST= 0
INDE 35 41 56 FOBS=  99.4 SIGMA=  3.0 PHAS=  115.8 FOM= 0.92 TEST= 0
INDE 35 42 35 FOBS=  36.6 SIGMA=  5.3 PHAS=    5.4 FOM= 0.52 TEST= 0
INDE 35 42 37 FOBS=   0.0 SIGMA= 19.1 PHAS=    0.0 FOM= 0.00 TEST= 0
INDE 35 42 39 FOBS=  84.9 SIGMA=  2.0 PHAS=   79.8 FOM= 0.92 TEST= 0
INDE 35 42 41 FOBS=  49.9 SIGMA=  3.5 PHAS=   90.9 FOM= 0.31 TEST= 0
INDE 35 42 43 FOBS= 103.6 SIGMA=  1.9 PHAS=  -61.1 FOM= 0.94 TEST= 0
INDE 35 42 45 FOBS=   0.0 SIGMA= 19.8 PHAS=    0.0 FOM= 0.00 TEST= 1
INDE 35 42 47 FOBS=  82.9 SIGMA=  2.3 PHAS=  -68.1 FOM= 0.94 TEST= 0
INDE 35 42 49 FOBS=  59.9 SIGMA=  3.2 PHAS= -147.0 FOM= 0.88 TEST= 0
INDE 35 42 51 FOBS=   0.0 SIGMA= 22.9 PHAS=    0.0 FOM= 0.00 TEST= 0
INDE 35 42 53 FOBS=  33.8 SIGMA=  6.1 PHAS=  168.5 FOM= 0.30 TEST= 0
INDE 35 42 55 FOBS=   0.0 SIGMA= 22.8 PHAS=    0.0 FOM= 0.00 TEST= 0
INDE 35 43 36 FOBS=  55.1 SIGMA=  3.4 PHAS=  -71.1 FOM= 0.68 TEST= 0
INDE 35 43 38 FOBS=   0.0 SIGMA= 18.2 PHAS=    0.0 FOM= 0.00 TEST= 1
INDE 35 43 40 FOBS=  84.0 SIGMA=  2.0 PHAS=   -3.9 FOM= 0.95 TEST= 0
INDE 35 43 42 FOBS=  90.4 SIGMA=  2.1 PHAS=  -61.8 FOM= 0.94 TEST= 0
INDE 35 43 44 FOBS= 107.3 SIGMA=  1.8 PHAS= -176.9 FOM= 0.96 TEST= 0
INDE 35 43 46 FOBS=  28.5 SIGMA=  6.6 PHAS= -176.3 FOM= 0.57 TEST= 0
INDE 35 43 48 FOBS= 103.5 SIGMA=  1.9 PHAS=  157.2 FOM= 0.94 TEST= 0
INDE 35 43 50 FOBS=   0.0 SIGMA= 20.4 PHAS=    0.0 FOM= 0.00 TEST= 0
INDE 35 43 52 FOBS=  43.2 SIGMA=  4.8 PHAS=   14.6 FOM= 0.25 TEST= 0
INDE 35 43 54 FOBS=  14.9 SIGMA= 17.0 PHAS=   94.3 FOM= 0.09 TEST= 0
INDE 35 44 35 FOBS=  76.6 SIGMA=  2.5 PHAS=  136.9 FOM= 0.79 TEST= 0
INDE 35 44 37 FOBS=  30.1 SIGMA=  5.8 PHAS=  -81.4 FOM= 0.57 TEST= 0
INDE 35 44 39 FOBS=  32.2 SIGMA=  5.7 PHAS=   81.6 FOM= 0.27 TEST= 0
INDE 35 44 41 FOBS=  65.1 SIGMA=  2.6 PHAS= -148.9 FOM= 0.83 TEST= 0
INDE 35 44 43 FOBS=  41.6 SIGMA=  4.5 PHAS=   17.0 FOM= 0.64 TEST= 1
INDE 35 44 45 FOBS=  88.4 SIGMA=  2.2 PHAS=   48.4 FOM= 0.07 TEST= 1
INDE 35 44 47 FOBS=   0.0 SIGMA= 19.4 PHAS=    0.0 FOM= 0.00 TEST= 1
INDE 35 44 49 FOBS=   0.0 SIGMA= 19.5 PHAS=    0.0 FOM= 0.00 TEST= 0
INDE 35 44 51 FOBS=  61.0 SIGMA=  3.4 PHAS=  109.9 FOM= 0.01 TEST= 1
INDE 35 44 53 FOBS=  65.9 SIGMA=  3.3 PHAS= -125.5 FOM= 0.80 TEST= 0
INDE 35 45 36 FOBS=  49.0 SIGMA=  3.7 PHAS=  -53.3 FOM= 0.48 TEST= 0
INDE 35 45 38 FOBS=  47.1 SIGMA=  3.6 PHAS=  -71.1 FOM= 0.76 TEST= 0
INDE 35 45 40 FOBS=  43.9 SIGMA=  3.8 PHAS=  150.0 FOM= 0.62 TEST= 0
INDE 35 45 42 FOBS=  27.9 SIGMA=  6.6 PHAS=  -46.6 FOM= 0.44 TEST= 0
INDE 35 45 44 FOBS=   7.8 SIGMA= 25.8 PHAS=  -82.1 FOM= 0.13 TEST= 0
INDE 35 45 46 FOBS=   0.0 SIGMA= 21.6 PHAS=    0.0 FOM= 0.00 TEST= 0
INDE 35 45 48 FOBS=  56.3 SIGMA=  3.4 PHAS=  166.0 FOM= 0.45 TEST= 1
```

*FIG. 12A - 556*

```
INDE 35 45 50 FOBS=   0.0 SIGMA= 19.7 PHAS=    0.0 FOM= 0.00 TEST= 0
INDE 35 45 52 FOBS=  40.1 SIGMA=  5.3 PHAS=   55.5 FOM= 0.43 TEST= 0
INDE 35 46 35 FOBS=  75.4 SIGMA=  2.5 PHAS=  -57.0 FOM= 0.86 TEST= 0
INDE 35 46 37 FOBS=  55.0 SIGMA=  3.4 PHAS=  121.4 FOM= 0.77 TEST= 0
INDE 35 46 39 FOBS=  42.7 SIGMA=  3.9 PHAS=  120.0 FOM= 0.69 TEST= 0
INDE 35 46 41 FOBS=  31.7 SIGMA=  5.6 PHAS=  157.5 FOM= 0.45 TEST= 0
INDE 35 46 43 FOBS=   0.0 SIGMA= 19.4 PHAS=    0.0 FOM= 0.00 TEST= 0
INDE 35 46 45 FOBS=  52.5 SIGMA=  3.7 PHAS=  -37.9 FOM= 0.50 TEST= 0
INDE 35 46 47 FOBS=   0.0 SIGMA= 20.1 PHAS=    0.0 FOM= 0.00 TEST= 0
INDE 35 46 49 FOBS=   0.0 SIGMA= 19.8 PHAS=    0.0 FOM= 0.00 TEST= 0
INDE 35 46 51 FOBS=  50.2 SIGMA=  4.3 PHAS=  -91.8 FOM= 0.71 TEST= 0
INDE 35 47 36 FOBS=  52.6 SIGMA=  3.6 PHAS=  -27.6 FOM= 0.67 TEST= 1
INDE 35 47 38 FOBS=  83.3 SIGMA=  2.2 PHAS=   24.1 FOM= 0.90 TEST= 0
INDE 35 47 40 FOBS=   0.0 SIGMA= 19.2 PHAS=    0.0 FOM= 0.00 TEST= 0
INDE 35 47 42 FOBS=   0.0 SIGMA= 23.3 PHAS=    0.0 FOM= 0.00 TEST= 0
INDE 35 47 44 FOBS=  41.5 SIGMA=  4.6 PHAS=  -11.4 FOM= 0.65 TEST= 0
INDE 35 47 46 FOBS=  13.0 SIGMA= 16.7 PHAS=   32.0 FOM= 0.24 TEST= 0
INDE 35 47 48 FOBS=   0.0 SIGMA= 19.9 PHAS=    0.0 FOM= 0.00 TEST= 0
INDE 35 47 50 FOBS=  28.4 SIGMA=  7.9 PHAS= -143.9 FOM= 0.37 TEST= 0
INDE 35 48 35 FOBS=   4.6 SIGMA= 41.8 PHAS=  163.4 FOM= 0.03 TEST= 0
INDE 35 48 37 FOBS=  89.7 SIGMA=  2.1 PHAS=  -31.4 FOM= 0.92 TEST= 0
INDE 35 48 39 FOBS=   0.0 SIGMA= 19.1 PHAS=    0.0 FOM= 0.00 TEST= 0
INDE 35 48 41 FOBS=  51.7 SIGMA=  3.5 PHAS=  141.6 FOM= 0.62 TEST= 0
INDE 35 48 43 FOBS=  52.3 SIGMA=  3.7 PHAS=    3.4 FOM= 0.77 TEST= 0
INDE 35 48 45 FOBS=  28.6 SIGMA=  8.6 PHAS=  -65.0 FOM= 0.60 TEST= 0
INDE 35 48 47 FOBS=  52.5 SIGMA=  4.0 PHAS=  -71.4 FOM= 0.76 TEST= 0
INDE 35 48 49 FOBS=   0.0 SIGMA= 20.7 PHAS=    0.0 FOM= 0.00 TEST= 1
INDE 35 49 36 FOBS= 128.8 SIGMA=  1.5 PHAS= -101.2 FOM= 0.95 TEST= 0
INDE 35 49 38 FOBS=   0.0 SIGMA= 19.8 PHAS=    0.0 FOM= 0.00 TEST= 0
INDE 35 49 40 FOBS=   0.0 SIGMA= 18.8 PHAS=    0.0 FOM= 0.00 TEST= 0
INDE 35 49 42 FOBS=  50.0 SIGMA=  3.5 PHAS= -107.9 FOM= 0.41 TEST= 0
INDE 35 49 44 FOBS=  46.5 SIGMA=  4.2 PHAS=  -72.5 FOM= 0.69 TEST= 0
INDE 35 49 46 FOBS=  74.7 SIGMA=  2.7 PHAS=  150.0 FOM= 0.91 TEST= 0
INDE 35 49 48 FOBS=  26.5 SIGMA=  8.1 PHAS= -155.5 FOM= 0.50 TEST= 0
INDE 35 50 35 FOBS= 142.8 SIGMA=  1.4 PHAS=  143.4 FOM= 0.95 TEST= 0
INDE 35 50 37 FOBS=   0.0 SIGMA= 20.5 PHAS=    0.0 FOM= 0.00 TEST= 0
INDE 35 50 39 FOBS=   0.0 SIGMA= 19.8 PHAS=    0.0 FOM= 0.00 TEST= 1
INDE 35 50 41 FOBS=  50.7 SIGMA=  3.4 PHAS=  151.8 FOM= 0.69 TEST= 0
INDE 35 50 43 FOBS=  32.9 SIGMA=  5.6 PHAS= -174.6 FOM= 0.15 TEST= 1
INDE 35 50 45 FOBS=  87.8 SIGMA=  2.3 PHAS=   64.8 FOM= 0.93 TEST= 0
INDE 35 50 47 FOBS=  54.0 SIGMA=  4.2 PHAS=  106.2 FOM= 0.44 TEST= 0
INDE 35 51 36 FOBS=   0.0 SIGMA= 20.4 PHAS=    0.0 FOM= 0.00 TEST= 1
INDE 35 51 38 FOBS=  66.0 SIGMA=  2.9 PHAS=  129.1 FOM= 0.86 TEST= 0
INDE 35 51 40 FOBS=  83.5 SIGMA=  2.3 PHAS=   40.0 FOM= 0.84 TEST= 0
INDE 35 51 42 FOBS=  63.5 SIGMA=  2.8 PHAS=   19.8 FOM= 0.05 TEST= 1
INDE 35 51 44 FOBS=  62.5 SIGMA=  3.3 PHAS=  -41.1 FOM= 0.88 TEST= 0
INDE 35 51 46 FOBS=   0.0 SIGMA= 22.8 PHAS=    0.0 FOM= 0.00 TEST= 0
INDE 35 52 35 FOBS=  74.3 SIGMA=  2.5 PHAS=   16.0 FOM= 0.88 TEST= 0
INDE 35 52 37 FOBS=  89.4 SIGMA=  2.1 PHAS=   77.5 FOM= 0.93 TEST= 0
INDE 35 52 39 FOBS=  13.7 SIGMA= 15.5 PHAS=   22.8 FOM= 0.28 TEST= 0
INDE 35 52 41 FOBS=  69.9 SIGMA=  2.7 PHAS=   -9.9 FOM= 0.77 TEST= 0
INDE 35 52 43 FOBS=  55.7 SIGMA=  3.2 PHAS= -140.0 FOM= 0.46 TEST= 0
INDE 35 52 45 FOBS=  97.3 SIGMA=  2.1 PHAS=  119.1 FOM= 0.91 TEST= 0
INDE 35 53 36 FOBS=  32.9 SIGMA=  6.3 PHAS=  -62.4 FOM= 0.22 TEST= 0
INDE 35 53 38 FOBS=  19.0 SIGMA= 11.2 PHAS=  117.2 FOM= 0.01 TEST= 1
INDE 35 53 40 FOBS=  10.4 SIGMA= 19.6 PHAS=  102.2 FOM= 0.16 TEST= 1
INDE 35 53 42 FOBS=  22.0 SIGMA= 10.8 PHAS=  -80.2 FOM= 0.51 TEST= 0
INDE 35 53 44 FOBS=  70.4 SIGMA=  2.9 PHAS=   30.2 FOM= 0.94 TEST= 0
INDE 35 54 35 FOBS=  45.0 SIGMA=  4.3 PHAS=  102.4 FOM= 0.86 TEST= 0
INDE 35 54 37 FOBS=  61.9 SIGMA=  3.3 PHAS=  115.2 FOM= 0.87 TEST= 0
INDE 35 54 39 FOBS=  49.8 SIGMA=  4.1 PHAS=   67.8 FOM= 0.86 TEST= 0
INDE 35 54 41 FOBS=  30.1 SIGMA=  6.8 PHAS=  152.2 FOM= 0.08 TEST= 1
INDE 35 54 43 FOBS=   0.0 SIGMA= 21.4 PHAS=    0.0 FOM= 0.00 TEST= 0
INDE 35 55 36 FOBS=  56.0 SIGMA=  3.6 PHAS=   22.4 FOM= 0.80 TEST= 0
INDE 35 55 38 FOBS=  55.6 SIGMA=  3.7 PHAS=  -59.3 FOM= 0.27 TEST= 1
INDE 35 55 40 FOBS=  68.3 SIGMA=  3.1 PHAS=   51.7 FOM= 0.89 TEST= 0
INDE 35 55 42 FOBS=   0.0 SIGMA= 21.3 PHAS=    0.0 FOM= 0.00 TEST= 0
INDE 35 56 35 FOBS=   0.0 SIGMA= 19.7 PHAS=    0.0 FOM= 0.00 TEST= 0
INDE 35 56 37 FOBS=   0.0 SIGMA= 22.9 PHAS=    0.0 FOM= 0.00 TEST= 0
INDE 35 56 39 FOBS=  50.4 SIGMA=  4.3 PHAS=  -66.9 FOM= 0.61 TEST= 0
```

*FIG. 12A - 557*

```
INDE 35 56 41 FOBS=    49.3 SIGMA=  6.7 PHAS=   15.5 FOM= 0.66 TEST= 0
INDE 35 57 36 FOBS=     0.0 SIGMA= 19.8 PHAS=    0.0 FOM= 0.00 TEST= 0
INDE 35 57 38 FOBS=    35.9 SIGMA=  6.7 PHAS=  114.1 FOM= 0.43 TEST= 0
INDE 35 58 35 FOBS=    14.3 SIGMA= 19.3 PHAS=   71.8 FOM= 0.10 TEST= 0
INDE 35 58 37 FOBS=     0.0 SIGMA= 21.8 PHAS=    0.0 FOM= 0.00 TEST= 0
INDE 35 59 36 FOBS=     0.0 SIGMA= 24.7 PHAS=    0.0 FOM= 0.00 TEST= 0
INDE 36 36 36 FOBS=   103.5 SIGMA=  2.9 PHAS=  -76.2 FOM= 0.90 TEST= 0
INDE 36 37 37 FOBS=   111.9 SIGMA=  1.6 PHAS= -170.4 FOM= 0.93 TEST= 0
INDE 36 37 39 FOBS=    47.7 SIGMA=  3.6 PHAS=   -1.5 FOM= 0.55 TEST= 0
INDE 36 37 41 FOBS=    54.0 SIGMA=  3.3 PHAS=  151.2 FOM= 0.76 TEST= 0
INDE 36 37 43 FOBS=    45.4 SIGMA=  4.1 PHAS=  107.5 FOM= 0.21 TEST= 0
INDE 36 37 45 FOBS=    58.8 SIGMA=  3.2 PHAS=  114.7 FOM= 0.79 TEST= 0
INDE 36 37 47 FOBS=    35.4 SIGMA=  5.3 PHAS=  101.1 FOM= 0.45 TEST= 0
INDE 36 37 49 FOBS=   144.8 SIGMA=  1.4 PHAS=  -66.2 FOM= 0.61 TEST= 1
INDE 36 37 51 FOBS=    57.2 SIGMA=  3.3 PHAS=   -0.7 FOM= 0.07 TEST= 1
INDE 36 37 53 FOBS=    60.2 SIGMA=  3.3 PHAS=   26.8 FOM= 0.72 TEST= 0
INDE 36 37 55 FOBS=    47.8 SIGMA=  4.3 PHAS=   65.6 FOM= 0.47 TEST= 0
INDE 36 37 57 FOBS=     0.0 SIGMA= 20.9 PHAS=    0.0 FOM= 0.00 TEST= 0
INDE 36 38 36 FOBS=    39.8 SIGMA=  4.7 PHAS= -131.3 FOM= 0.36 TEST= 0
INDE 36 38 38 FOBS=    31.5 SIGMA=  5.7 PHAS=  145.6 FOM= 0.06 TEST= 1
INDE 36 38 40 FOBS=     0.0 SIGMA= 19.7 PHAS=    0.0 FOM= 0.00 TEST= 0
INDE 36 38 42 FOBS=     0.0 SIGMA= 18.7 PHAS=    0.0 FOM= 0.00 TEST= 0
INDE 36 38 44 FOBS=    44.8 SIGMA=  4.7 PHAS=   29.9 FOM= 0.68 TEST= 0
INDE 36 38 46 FOBS=    37.9 SIGMA=  5.5 PHAS=  112.0 FOM= 0.58 TEST= 0
INDE 36 38 48 FOBS=    62.3 SIGMA=  3.0 PHAS=   11.1 FOM= 0.38 TEST= 0
INDE 36 38 50 FOBS=    83.9 SIGMA=  2.3 PHAS=  170.4 FOM= 0.90 TEST= 0
INDE 36 38 52 FOBS=    43.7 SIGMA=  4.9 PHAS= -177.2 FOM= 0.38 TEST= 0
INDE 36 38 54 FOBS=   105.1 SIGMA=  2.0 PHAS=  -70.0 FOM= 0.94 TEST= 0
INDE 36 38 56 FOBS=    41.0 SIGMA=  5.1 PHAS= -144.4 FOM= 0.42 TEST= 0
INDE 36 39 37 FOBS=    87.5 SIGMA=  2.0 PHAS= -131.2 FOM= 0.86 TEST= 0
INDE 36 39 39 FOBS=    34.0 SIGMA=  5.3 PHAS=  -87.2 FOM= 0.37 TEST= 0
INDE 36 39 41 FOBS=   102.9 SIGMA=  1.7 PHAS=   54.4 FOM= 0.83 TEST= 0
INDE 36 39 43 FOBS=    13.6 SIGMA= 14.3 PHAS=   77.4 FOM= 0.19 TEST= 0
INDE 36 39 45 FOBS=    58.8 SIGMA=  3.2 PHAS=  -34.6 FOM= 0.86 TEST= 0
INDE 36 39 47 FOBS=    15.6 SIGMA= 12.6 PHAS=  -82.5 FOM= 0.21 TEST= 0
INDE 36 39 49 FOBS=     0.0 SIGMA= 19.3 PHAS=    0.0 FOM= 0.00 TEST= 0
INDE 36 39 51 FOBS=    49.3 SIGMA=  3.9 PHAS=  123.8 FOM= 0.61 TEST= 0
INDE 36 39 53 FOBS=    29.7 SIGMA=  6.8 PHAS=  128.5 FOM= 0.06 TEST= 1
INDE 36 39 55 FOBS=    42.7 SIGMA=  5.2 PHAS=  142.3 FOM= 0.80 TEST= 0
INDE 36 40 36 FOBS=   122.2 SIGMA=  1.5 PHAS=  169.3 FOM= 0.48 TEST= 1
INDE 36 40 38 FOBS=   137.0 SIGMA=  1.4 PHAS=  139.8 FOM= 0.95 TEST= 0
INDE 36 40 40 FOBS=   116.4 SIGMA=  1.5 PHAS=  -34.5 FOM= 0.90 TEST= 0
INDE 36 40 42 FOBS=   133.7 SIGMA=  1.3 PHAS=  -55.2 FOM= 0.92 TEST= 0
INDE 36 40 44 FOBS=    24.3 SIGMA= 10.8 PHAS= -103.3 FOM= 0.29 TEST= 0
INDE 36 40 46 FOBS=     0.0 SIGMA= 19.7 PHAS=    0.0 FOM= 0.00 TEST= 0
INDE 36 40 48 FOBS=    82.4 SIGMA=  2.3 PHAS=   40.3 FOM= 0.62 TEST= 0
INDE 36 40 50 FOBS=    69.3 SIGMA=  2.8 PHAS=   86.5 FOM= 0.17 TEST= 1
INDE 36 40 52 FOBS=     0.0 SIGMA= 20.8 PHAS=    0.0 FOM= 0.00 TEST= 0
INDE 36 40 54 FOBS=    59.5 SIGMA=  3.5 PHAS= -107.2 FOM= 0.40 TEST= 0
INDE 36 40 56 FOBS=    79.8 SIGMA=  2.7 PHAS=    5.7 FOM= 0.90 TEST= 0
INDE 36 41 37 FOBS=    87.5 SIGMA=  2.0 PHAS=   64.0 FOM= 0.92 TEST= 1
INDE 36 41 39 FOBS=     0.0 SIGMA= 19.8 PHAS=    0.0 FOM= 0.00 TEST= 0
INDE 36 41 41 FOBS=    83.8 SIGMA=  2.1 PHAS= -106.0 FOM= 0.87 TEST= 0
INDE 36 41 43 FOBS=    58.8 SIGMA=  3.0 PHAS= -121.1 FOM= 0.86 TEST= 0
INDE 36 41 45 FOBS=    23.0 SIGMA=  8.5 PHAS=   83.0 FOM= 0.65 TEST= 0
INDE 36 41 47 FOBS=    75.8 SIGMA=  2.5 PHAS=  -92.3 FOM= 0.79 TEST= 0
INDE 36 41 49 FOBS=    29.0 SIGMA=  7.2 PHAS=  -19.9 FOM= 0.83 TEST= 0
INDE 36 41 51 FOBS=     0.0 SIGMA= 20.6 PHAS=    0.0 FOM= 0.00 TEST= 0
INDE 36 41 53 FOBS=    38.6 SIGMA=  6.2 PHAS= -145.6 FOM= 0.25 TEST= 0
INDE 36 41 55 FOBS=    57.2 SIGMA=  3.7 PHAS=  -83.9 FOM= 0.19 TEST= 1
INDE 36 42 36 FOBS=     0.0 SIGMA= 19.1 PHAS=    0.0 FOM= 0.00 TEST= 0
INDE 36 42 38 FOBS=    23.2 SIGMA=  8.8 PHAS= -121.6 FOM= 0.44 TEST= 0
INDE 36 42 40 FOBS=    51.9 SIGMA=  3.3 PHAS= -143.1 FOM= 0.65 TEST= 0
INDE 36 42 42 FOBS=     0.0 SIGMA= 18.9 PHAS=    0.0 FOM= 0.00 TEST= 0
INDE 36 42 44 FOBS=    28.0 SIGMA=  7.6 PHAS=   19.0 FOM= 0.20 TEST= 0
INDE 36 42 46 FOBS=    46.7 SIGMA=  4.2 PHAS=   -9.9 FOM= 0.69 TEST= 0
INDE 36 42 48 FOBS=    18.3 SIGMA= 11.6 PHAS= -173.5 FOM= 0.32 TEST= 0
INDE 36 42 50 FOBS=    28.3 SIGMA=  7.1 PHAS=  153.0 FOM= 0.61 TEST= 0
INDE 36 42 52 FOBS=    32.1 SIGMA=  6.4 PHAS=   62.2 FOM= 0.00 TEST= 1
INDE 36 42 54 FOBS=     0.0 SIGMA= 20.5 PHAS=    0.0 FOM= 0.00 TEST= 0
```

*FIG. 12A - 558*

```
INDE 36 43 37 FOBS=   0.0 SIGMA= 19.7 PHAS=    0.0 FOM= 0.00 TEST= 0
INDE 36 43 39 FOBS=  17.8 SIGMA= 10.4 PHAS=   62.5 FOM= 0.24 TEST= 0
INDE 36 43 41 FOBS=   0.0 SIGMA= 19.3 PHAS=    0.0 FOM= 0.00 TEST= 0
INDE 36 43 43 FOBS=  93.1 SIGMA=  2.0 PHAS= -113.4 FOM= 0.93 TEST= 0
INDE 36 43 45 FOBS=   0.0 SIGMA= 19.9 PHAS=    0.0 FOM= 0.00 TEST= 1
INDE 36 43 47 FOBS=  83.8 SIGMA=  2.3 PHAS= -153.3 FOM= 0.88 TEST= 0
INDE 36 43 49 FOBS=  45.3 SIGMA=  4.4 PHAS=   57.1 FOM= 0.69 TEST= 0
INDE 36 43 51 FOBS=  36.3 SIGMA=  6.1 PHAS=  129.9 FOM= 0.36 TEST= 0
INDE 36 43 53 FOBS=  52.6 SIGMA=  4.0 PHAS=  152.6 FOM= 0.59 TEST= 0
INDE 36 44 36 FOBS=  14.4 SIGMA= 13.4 PHAS=   79.7 FOM= 0.26 TEST= 0
INDE 36 44 38 FOBS=  40.5 SIGMA=  4.1 PHAS=  143.1 FOM= 0.49 TEST= 0
INDE 36 44 40 FOBS=   0.0 SIGMA= 19.3 PHAS=    0.0 FOM= 0.00 TEST= 0
INDE 36 44 42 FOBS=  80.7 SIGMA=  2.2 PHAS=  135.4 FOM= 0.90 TEST= 0
INDE 36 44 44 FOBS=  42.3 SIGMA=  4.5 PHAS= -167.0 FOM= 0.48 TEST= 0
INDE 36 44 46 FOBS=  50.2 SIGMA=  3.8 PHAS=  149.3 FOM= 0.04 TEST= 1
INDE 36 44 48 FOBS=  49.5 SIGMA=  3.9 PHAS=  148.8 FOM= 0.06 TEST= 0
INDE 36 44 50 FOBS=  26.7 SIGMA=  8.2 PHAS= -157.8 FOM= 0.24 TEST= 0
INDE 36 44 52 FOBS=  32.9 SIGMA=  7.2 PHAS=   41.8 FOM= 0.28 TEST= 0
INDE 36 45 37 FOBS=  69.8 SIGMA=  2.6 PHAS=  -40.9 FOM= 0.91 TEST= 0
INDE 36 45 39 FOBS=  12.0 SIGMA= 16.2 PHAS=  -31.9 FOM= 0.02 TEST= 1
INDE 36 45 41 FOBS=  61.4 SIGMA=  2.8 PHAS=   74.8 FOM= 0.74 TEST= 0
INDE 36 45 43 FOBS=   0.0 SIGMA= 19.4 PHAS=    0.0 FOM= 0.00 TEST= 0
INDE 36 45 45 FOBS=   0.0 SIGMA= 19.5 PHAS=    0.0 FOM= 0.00 TEST= 0
INDE 36 45 47 FOBS=  33.6 SIGMA=  6.1 PHAS=  155.5 FOM= 0.59 TEST= 0
INDE 36 45 49 FOBS=   0.0 SIGMA= 20.9 PHAS=    0.0 FOM= 0.00 TEST= 0
INDE 36 45 51 FOBS=  55.9 SIGMA=  3.8 PHAS=   67.9 FOM= 0.18 TEST= 1
INDE 36 46 36 FOBS= 156.4 SIGMA=  1.3 PHAS= -146.4 FOM= 0.97 TEST= 0
INDE 36 46 38 FOBS=  49.8 SIGMA=  3.5 PHAS= -138.6 FOM= 0.87 TEST= 0
INDE 36 46 40 FOBS=  40.7 SIGMA=  4.2 PHAS= -130.4 FOM= 0.09 TEST= 0
INDE 36 46 42 FOBS=   0.0 SIGMA= 18.8 PHAS=    0.0 FOM= 0.00 TEST= 0
INDE 36 46 44 FOBS=   0.0 SIGMA= 20.6 PHAS=    0.0 FOM= 0.00 TEST= 0
INDE 36 46 46 FOBS=   0.0 SIGMA= 20.1 PHAS=    0.0 FOM= 0.00 TEST= 0
INDE 36 46 48 FOBS=   0.0 SIGMA= 20.3 PHAS=    0.0 FOM= 0.00 TEST= 0
INDE 36 46 50 FOBS=   0.0 SIGMA= 20.6 PHAS=    0.0 FOM= 0.00 TEST= 0
INDE 36 47 37 FOBS=  18.6 SIGMA= 11.2 PHAS=  126.7 FOM= 0.48 TEST= 0
INDE 36 47 39 FOBS=  62.7 SIGMA=  2.7 PHAS=   35.2 FOM= 0.64 TEST= 0
INDE 36 47 41 FOBS=   0.0 SIGMA= 19.0 PHAS=    0.0 FOM= 0.00 TEST= 0
INDE 36 47 43 FOBS=   0.0 SIGMA= 19.5 PHAS=    0.0 FOM= 0.00 TEST= 0
INDE 36 47 45 FOBS=  71.0 SIGMA=  2.8 PHAS= -150.9 FOM= 0.72 TEST= 0
INDE 36 47 47 FOBS=   0.0 SIGMA= 20.9 PHAS=    0.0 FOM= 0.00 TEST= 0
INDE 36 47 49 FOBS=   0.0 SIGMA= 20.6 PHAS=    0.0 FOM= 0.00 TEST= 0
INDE 36 48 36 FOBS=  65.8 SIGMA=  2.9 PHAS=   81.2 FOM= 0.87 TEST= 0
INDE 36 48 38 FOBS= 108.5 SIGMA=  1.8 PHAS=  -98.4 FOM= 0.89 TEST= 0
INDE 36 48 40 FOBS=   0.0 SIGMA= 18.8 PHAS=    0.0 FOM= 0.00 TEST= 0
INDE 36 48 42 FOBS=   0.0 SIGMA= 21.3 PHAS=    0.0 FOM= 0.00 TEST= 0
INDE 36 48 44 FOBS=  52.0 SIGMA=  3.6 PHAS=  -12.5 FOM= 0.68 TEST= 0
INDE 36 48 46 FOBS=  32.6 SIGMA=  7.4 PHAS=   72.1 FOM= 0.49 TEST= 0
INDE 36 48 48 FOBS=   0.0 SIGMA= 20.5 PHAS=    0.0 FOM= 0.00 TEST= 0
INDE 36 49 37 FOBS=  63.5 SIGMA=  3.0 PHAS=  163.4 FOM= 0.82 TEST= 0
INDE 36 49 39 FOBS=  47.5 SIGMA=  4.1 PHAS=  147.8 FOM= 0.68 TEST= 0
INDE 36 49 41 FOBS=   0.0 SIGMA= 19.4 PHAS=    0.0 FOM= 0.00 TEST= 0
INDE 36 49 43 FOBS=  34.8 SIGMA=  5.3 PHAS=  -59.8 FOM= 0.10 TEST= 0
INDE 36 49 45 FOBS=  69.0 SIGMA=  2.8 PHAS= -103.7 FOM= 0.89 TEST= 0
INDE 36 49 47 FOBS=  42.4 SIGMA=  5.0 PHAS=   73.3 FOM= 0.49 TEST= 0
INDE 36 50 36 FOBS=  82.6 SIGMA=  2.3 PHAS=  122.9 FOM= 0.16 TEST= 1
INDE 36 50 38 FOBS=  53.0 SIGMA=  3.6 PHAS=   61.4 FOM= 0.85 TEST= 0
INDE 36 50 40 FOBS=   0.0 SIGMA= 19.4 PHAS=    0.0 FOM= 0.00 TEST= 0
INDE 36 50 42 FOBS=   0.0 SIGMA= 19.5 PHAS=    0.0 FOM= 0.00 TEST= 0
INDE 36 50 44 FOBS=  75.5 SIGMA=  2.4 PHAS=  151.8 FOM= 0.13 TEST= 1
INDE 36 50 46 FOBS=   0.0 SIGMA= 23.0 PHAS=    0.0 FOM= 0.00 TEST= 0
INDE 36 51 37 FOBS=  63.4 SIGMA=  3.0 PHAS=  -25.2 FOM= 0.86 TEST= 0
INDE 36 51 39 FOBS=  54.4 SIGMA=  3.5 PHAS=   17.9 FOM= 0.85 TEST= 0
INDE 36 51 41 FOBS=   0.0 SIGMA= 19.0 PHAS=    0.0 FOM= 0.00 TEST= 0
INDE 36 51 43 FOBS=  27.7 SIGMA=  7.9 PHAS=   35.0 FOM= 0.31 TEST= 0
INDE 36 51 45 FOBS=  26.5 SIGMA=  7.7 PHAS=  -63.1 FOM= 0.44 TEST= 0
INDE 36 52 36 FOBS=  66.5 SIGMA=  2.9 PHAS= -177.3 FOM= 0.89 TEST= 0
INDE 36 52 38 FOBS=  73.4 SIGMA=  2.6 PHAS=    1.2 FOM= 0.35 TEST= 1
INDE 36 52 40 FOBS=  63.5 SIGMA=  3.1 PHAS=  -43.6 FOM= 0.65 TEST= 0
INDE 36 52 42 FOBS=  25.5 SIGMA=  8.6 PHAS= -127.6 FOM= 0.21 TEST= 0
INDE 36 52 44 FOBS= 112.4 SIGMA=  1.7 PHAS= -125.3 FOM= 0.95 TEST= 0
```

*FIG. 12A - 559*

```
INDE 36 53 37 FOBS=    73.3 SIGMA=  2.8 PHAS=   27.9 FOM= 0.85 TEST= 0
INDE 36 53 39 FOBS=    87.0 SIGMA=  2.4 PHAS=  -54.9 FOM= 0.65 TEST= 1
INDE 36 53 41 FOBS=    36.6 SIGMA=  5.6 PHAS=  -48.4 FOM= 0.52 TEST= 0
INDE 36 53 43 FOBS=   101.4 SIGMA=  2.0 PHAS=  140.3 FOM= 0.93 TEST= 0
INDE 36 54 36 FOBS=    30.7 SIGMA=  6.4 PHAS=  -22.1 FOM= 0.64 TEST= 0
INDE 36 54 38 FOBS=    34.0 SIGMA=  6.7 PHAS=  -65.8 FOM= 0.43 TEST= 0
INDE 36 54 40 FOBS=    84.2 SIGMA=  2.5 PHAS=  -47.3 FOM= 0.90 TEST= 0
INDE 36 54 42 FOBS=     0.0 SIGMA= 20.1 PHAS=    0.0 FOM= 0.00 TEST= 0
INDE 36 55 37 FOBS=     0.0 SIGMA= 20.1 PHAS=    0.0 FOM= 0.00 TEST= 0
INDE 36 55 39 FOBS=    15.3 SIGMA= 14.4 PHAS= -170.0 FOM= 0.37 TEST= 0
INDE 36 55 41 FOBS=     0.0 SIGMA= 21.1 PHAS=    0.0 FOM= 0.00 TEST= 0
INDE 36 56 36 FOBS=     0.0 SIGMA= 19.9 PHAS=    0.0 FOM= 0.00 TEST= 0
INDE 36 56 38 FOBS=    22.7 SIGMA=  9.7 PHAS=  -34.3 FOM= 0.26 TEST= 0
INDE 36 56 40 FOBS=     0.0 SIGMA= 20.5 PHAS=    0.0 FOM= 0.00 TEST= 0
INDE 36 57 37 FOBS=     0.0 SIGMA= 20.1 PHAS=    0.0 FOM= 0.00 TEST= 0
INDE 36 58 36 FOBS=     0.0 SIGMA= 20.2 PHAS=    0.0 FOM= 0.00 TEST= 1
INDE 37 38 37 FOBS=    85.2 SIGMA=  2.0 PHAS=  115.5 FOM= 0.87 TEST= 0
INDE 37 38 39 FOBS=   121.9 SIGMA=  1.5 PHAS=  117.8 FOM= 0.93 TEST= 0
INDE 37 38 41 FOBS=    36.9 SIGMA=  4.9 PHAS=   48.0 FOM= 0.19 TEST= 0
INDE 37 38 43 FOBS=     0.0 SIGMA= 18.6 PHAS=    0.0 FOM= 0.00 TEST= 0
INDE 37 38 45 FOBS=    40.1 SIGMA=  4.9 PHAS=  -98.3 FOM= 0.69 TEST= 0
INDE 37 38 47 FOBS=    89.0 SIGMA=  2.2 PHAS=  -22.0 FOM= 0.87 TEST= 0
INDE 37 38 49 FOBS=    87.2 SIGMA=  2.2 PHAS= -109.8 FOM= 0.93 TEST= 0
INDE 37 38 51 FOBS=    32.8 SIGMA=  6.1 PHAS=   63.8 FOM= 0.16 TEST= 0
INDE 37 38 53 FOBS=    54.0 SIGMA=  3.8 PHAS=   60.7 FOM= 0.63 TEST= 0
INDE 37 38 55 FOBS=     0.0 SIGMA= 20.2 PHAS=    0.0 FOM= 0.00 TEST= 1
INDE 37 39 38 FOBS=   104.6 SIGMA=  1.7 PHAS=    8.5 FOM= 0.92 TEST= 0
INDE 37 39 40 FOBS=     0.0 SIGMA= 19.8 PHAS=    0.0 FOM= 0.00 TEST= 0
INDE 37 39 42 FOBS=     2.9 SIGMA= 72.6 PHAS= -156.1 FOM= 0.01 TEST= 0
INDE 37 39 44 FOBS=    16.8 SIGMA= 10.5 PHAS=   65.5 FOM= 0.14 TEST= 0
INDE 37 39 46 FOBS=    77.5 SIGMA=  2.5 PHAS=  -88.2 FOM= 0.93 TEST= 0
INDE 37 39 48 FOBS=    55.6 SIGMA=  3.4 PHAS=  -57.1 FOM= 0.83 TEST= 0
INDE 37 39 50 FOBS=   104.1 SIGMA=  2.0 PHAS=  177.4 FOM= 0.07 TEST= 1
INDE 37 39 52 FOBS=     0.0 SIGMA= 20.1 PHAS=    0.0 FOM= 0.00 TEST= 0
INDE 37 39 54 FOBS=    22.1 SIGMA=  9.7 PHAS=   75.7 FOM= 0.32 TEST= 0
INDE 37 39 56 FOBS=     0.0 SIGMA= 21.1 PHAS=    0.0 FOM= 0.00 TEST= 0
INDE 37 40 37 FOBS=    63.5 SIGMA=  2.7 PHAS= -126.0 FOM= 0.89 TEST= 0
INDE 37 40 39 FOBS=    50.2 SIGMA=  3.5 PHAS=   83.3 FOM= 0.57 TEST= 0
INDE 37 40 41 FOBS=    56.1 SIGMA=  3.1 PHAS=  -96.0 FOM= 0.49 TEST= 0
INDE 37 40 43 FOBS=     0.0 SIGMA= 18.5 PHAS=    0.0 FOM= 0.00 TEST= 0
INDE 37 40 45 FOBS=    74.6 SIGMA=  2.4 PHAS= -155.7 FOM= 0.77 TEST= 0
INDE 37 40 47 FOBS=    68.4 SIGMA=  2.8 PHAS= -143.5 FOM= 0.86 TEST= 0
INDE 37 40 49 FOBS=    81.0 SIGMA=  2.4 PHAS= -149.5 FOM= 0.76 TEST= 0
INDE 37 40 51 FOBS=     0.0 SIGMA= 19.4 PHAS=    0.0 FOM= 0.00 TEST= 0
INDE 37 40 53 FOBS=     0.0 SIGMA= 20.3 PHAS=    0.0 FOM= 0.00 TEST= 0
INDE 37 40 55 FOBS=     0.0 SIGMA= 21.2 PHAS=    0.0 FOM= 0.00 TEST= 0
INDE 37 41 38 FOBS=    23.2 SIGMA=  7.7 PHAS=   24.7 FOM= 0.31 TEST= 0
INDE 37 41 40 FOBS=    52.2 SIGMA=  3.3 PHAS=  -86.1 FOM= 0.15 TEST= 1
INDE 37 41 42 FOBS=    31.9 SIGMA=  5.6 PHAS=  102.3 FOM= 0.44 TEST= 0
INDE 37 41 44 FOBS=    95.0 SIGMA=  1.9 PHAS=  163.1 FOM= 0.87 TEST= 0
INDE 37 41 46 FOBS=    50.5 SIGMA=  3.8 PHAS=  -40.2 FOM= 0.15 TEST= 1
INDE 37 41 48 FOBS=     0.0 SIGMA= 19.4 PHAS=    0.0 FOM= 0.00 TEST= 0
INDE 37 41 50 FOBS=     0.0 SIGMA= 20.6 PHAS=    0.0 FOM= 0.00 TEST= 0
INDE 37 41 52 FOBS=    27.7 SIGMA=  7.5 PHAS= -164.9 FOM= 0.09 TEST= 0
INDE 37 41 54 FOBS=     0.0 SIGMA= 20.5 PHAS=    0.0 FOM= 0.00 TEST= 0
INDE 37 42 37 FOBS=     0.0 SIGMA= 19.0 PHAS=    0.0 FOM= 0.00 TEST= 1
INDE 37 42 39 FOBS=    78.0 SIGMA=  2.2 PHAS= -123.8 FOM= 0.48 TEST= 0
INDE 37 42 41 FOBS=     0.0 SIGMA= 19.2 PHAS=    0.0 FOM= 0.00 TEST= 0
INDE 37 42 43 FOBS=    73.3 SIGMA=  2.4 PHAS=  119.4 FOM= 0.89 TEST= 0
INDE 37 42 45 FOBS=    40.8 SIGMA=  4.4 PHAS=   47.9 FOM= 0.63 TEST= 0
INDE 37 42 47 FOBS=    55.8 SIGMA=  3.4 PHAS= -145.6 FOM= 0.75 TEST= 0
INDE 37 42 49 FOBS=     0.0 SIGMA= 21.4 PHAS=    0.0 FOM= 0.00 TEST= 0
INDE 37 42 51 FOBS=    42.2 SIGMA=  4.9 PHAS=   17.9 FOM= 0.65 TEST= 0
INDE 37 42 53 FOBS=     0.0 SIGMA= 20.4 PHAS=    0.0 FOM= 0.00 TEST= 0
INDE 37 43 38 FOBS=    32.2 SIGMA=  6.5 PHAS= -111.6 FOM= 0.10 TEST= 0
INDE 37 43 40 FOBS=    40.4 SIGMA=  4.2 PHAS=  123.7 FOM= 0.37 TEST= 0
INDE 37 43 42 FOBS=    73.5 SIGMA=  2.4 PHAS=    9.3 FOM= 0.85 TEST= 0
INDE 37 43 44 FOBS=     8.1 SIGMA= 26.1 PHAS=  137.3 FOM= 0.15 TEST= 0
INDE 37 43 46 FOBS=     0.0 SIGMA= 20.0 PHAS=    0.0 FOM= 0.00 TEST= 0
INDE 37 43 48 FOBS=    68.2 SIGMA=  2.8 PHAS=  107.1 FOM= 0.77 TEST= 0
```

*FIG. 12A - 560*

```
INDE 37 43 50 FOBS=   27.5 SIGMA=  7.8 PHAS= -120.2 FOM= 0.20 TEST= 0
INDE 37 43 52 FOBS=    0.0 SIGMA= 21.5 PHAS=    0.0 FOM= 0.00 TEST= 0
INDE 37 44 37 FOBS=    0.0 SIGMA= 19.2 PHAS=    0.0 FOM= 0.00 TEST= 0
INDE 37 44 39 FOBS=    0.0 SIGMA= 19.7 PHAS=    0.0 FOM= 0.00 TEST= 0
INDE 37 44 41 FOBS=    0.0 SIGMA= 19.9 PHAS=    0.0 FOM= 0.00 TEST= 0
INDE 37 44 43 FOBS=    0.0 SIGMA= 18.9 PHAS=    0.0 FOM= 0.00 TEST= 0
INDE 37 44 45 FOBS=   13.2 SIGMA= 14.4 PHAS= -149.0 FOM= 0.31 TEST= 0
INDE 37 44 47 FOBS=   55.9 SIGMA=  3.5 PHAS=  130.1 FOM= 0.76 TEST= 0
INDE 37 44 49 FOBS=   50.7 SIGMA=  3.9 PHAS=  -68.5 FOM= 0.39 TEST= 0
INDE 37 44 51 FOBS=   52.0 SIGMA=  4.1 PHAS=   86.1 FOM= 0.66 TEST= 0
INDE 37 45 38 FOBS=   69.2 SIGMA=  2.5 PHAS= -161.0 FOM= 0.44 TEST= 0
INDE 37 45 40 FOBS=    0.0 SIGMA= 21.4 PHAS=    0.0 FOM= 0.00 TEST= 0
INDE 37 45 42 FOBS=    0.0 SIGMA= 18.8 PHAS=    0.0 FOM= 0.00 TEST= 1
INDE 37 45 44 FOBS=    0.0 SIGMA= 19.1 PHAS=    0.0 FOM= 0.00 TEST= 0
INDE 37 45 46 FOBS=   19.5 SIGMA=  9.4 PHAS=  175.0 FOM= 0.39 TEST= 0
INDE 37 45 48 FOBS=   67.4 SIGMA=  2.9 PHAS=  138.8 FOM= 0.91 TEST= 0
INDE 37 45 50 FOBS=    0.0 SIGMA= 21.2 PHAS=    0.0 FOM= 0.00 TEST= 0
INDE 37 46 37 FOBS=    0.0 SIGMA= 19.7 PHAS=    0.0 FOM= 0.00 TEST= 0
INDE 37 46 39 FOBS=   31.9 SIGMA=  5.3 PHAS= -112.0 FOM= 0.61 TEST= 0
INDE 37 46 41 FOBS=   25.8 SIGMA=  6.9 PHAS=   74.9 FOM= 0.27 TEST= 0
INDE 37 46 43 FOBS=    0.0 SIGMA= 18.9 PHAS=    0.0 FOM= 0.00 TEST= 0
INDE 37 46 45 FOBS=   96.4 SIGMA=  1.9 PHAS=   52.4 FOM= 0.11 TEST= 1
INDE 37 46 47 FOBS=   71.3 SIGMA=  2.8 PHAS=   76.5 FOM= 0.91 TEST= 0
INDE 37 46 49 FOBS=   58.3 SIGMA=  3.5 PHAS=   44.8 FOM= 0.59 TEST= 0
INDE 37 47 38 FOBS=  103.8 SIGMA=  1.9 PHAS=  130.5 FOM= 0.85 TEST= 0
INDE 37 47 40 FOBS=   62.4 SIGMA=  2.8 PHAS=  -71.2 FOM= 0.53 TEST= 0
INDE 37 47 42 FOBS=    0.0 SIGMA= 19.9 PHAS=    0.0 FOM= 0.00 TEST= 0
INDE 37 47 44 FOBS=   30.9 SIGMA=  6.0 PHAS=  -73.2 FOM= 0.66 TEST= 0
INDE 37 47 46 FOBS=    0.0 SIGMA= 20.6 PHAS=    0.0 FOM= 0.00 TEST= 0
INDE 37 47 48 FOBS=    0.0 SIGMA= 20.6 PHAS=    0.0 FOM= 0.00 TEST= 0
INDE 37 48 37 FOBS=  162.1 SIGMA=  1.3 PHAS=   20.4 FOM= 0.96 TEST= 0
INDE 37 48 39 FOBS=    0.0 SIGMA= 19.8 PHAS=    0.0 FOM= 0.00 TEST= 0
INDE 37 48 41 FOBS=    0.0 SIGMA= 19.6 PHAS=    0.0 FOM= 0.00 TEST= 0
INDE 37 48 43 FOBS=    0.0 SIGMA= 19.1 PHAS=    0.0 FOM= 0.00 TEST= 0
INDE 37 48 45 FOBS=   92.9 SIGMA=  2.0 PHAS= -160.6 FOM= 0.93 TEST= 0
INDE 37 48 47 FOBS=   50.0 SIGMA=  4.3 PHAS=   13.6 FOM= 0.71 TEST= 0
INDE 37 49 38 FOBS=   18.8 SIGMA= 12.0 PHAS= -105.4 FOM= 0.06 TEST= 0
INDE 37 49 40 FOBS=    0.0 SIGMA= 19.8 PHAS=    0.0 FOM= 0.00 TEST= 0
INDE 37 49 42 FOBS=   49.2 SIGMA=  3.6 PHAS=  179.3 FOM= 0.64 TEST= 0
INDE 37 49 44 FOBS=   36.3 SIGMA=  5.6 PHAS= -176.6 FOM= 0.60 TEST= 0
INDE 37 49 46 FOBS=   54.7 SIGMA=  3.7 PHAS= -170.2 FOM= 0.88 TEST= 0
INDE 37 50 37 FOBS=   31.8 SIGMA=  6.5 PHAS=    6.1 FOM= 0.31 TEST= 0
INDE 37 50 39 FOBS=   32.2 SIGMA=  6.2 PHAS=   -8.9 FOM= 0.67 TEST= 0
INDE 37 50 41 FOBS=   35.3 SIGMA=  5.7 PHAS=  133.5 FOM= 0.71 TEST= 0
INDE 37 50 43 FOBS=    0.0 SIGMA= 19.7 PHAS=    0.0 FOM= 0.00 TEST= 0
INDE 37 50 45 FOBS=   68.2 SIGMA=  2.7 PHAS=  140.1 FOM= 0.88 TEST= 0
INDE 37 51 38 FOBS=   42.7 SIGMA=  5.4 PHAS= -107.3 FOM= 0.42 TEST= 0
INDE 37 51 40 FOBS=   18.2 SIGMA= 11.8 PHAS= -121.0 FOM= 0.06 TEST= 1
INDE 37 51 42 FOBS=    0.0 SIGMA= 19.3 PHAS=    0.0 FOM= 0.00 TEST= 0
INDE 37 51 44 FOBS=   87.8 SIGMA=  2.1 PHAS=   98.3 FOM= 0.92 TEST= 0
INDE 37 52 37 FOBS=   64.6 SIGMA=  3.0 PHAS=  126.2 FOM= 0.68 TEST= 0
INDE 37 52 39 FOBS=    0.0 SIGMA= 20.1 PHAS=    0.0 FOM= 0.00 TEST= 0
INDE 37 52 41 FOBS=   86.4 SIGMA=  2.3 PHAS=  178.4 FOM= 0.86 TEST= 0
INDE 37 52 43 FOBS=   71.1 SIGMA=  2.7 PHAS=   -3.5 FOM= 0.88 TEST= 0
INDE 37 53 38 FOBS=   73.3 SIGMA=  2.8 PHAS=   15.8 FOM= 0.24 TEST= 1
INDE 37 53 40 FOBS=   53.2 SIGMA=  3.9 PHAS= -102.8 FOM= 0.82 TEST= 0
INDE 37 53 42 FOBS=   67.8 SIGMA=  2.9 PHAS=  -51.0 FOM= 0.72 TEST= 0
INDE 37 54 37 FOBS=   65.2 SIGMA=  3.1 PHAS= -101.2 FOM= 0.16 TEST= 1
INDE 37 54 39 FOBS=    0.0 SIGMA= 23.8 PHAS=    0.0 FOM= 0.00 TEST= 0
INDE 37 54 41 FOBS=   60.2 SIGMA=  3.5 PHAS= -152.8 FOM= 0.84 TEST= 0
INDE 37 55 38 FOBS=    0.0 SIGMA= 21.0 PHAS=    0.0 FOM= 0.00 TEST= 0
INDE 37 55 40 FOBS=    0.0 SIGMA= 23.0 PHAS=    0.0 FOM= 0.00 TEST= 0
INDE 37 56 37 FOBS=    0.0 SIGMA= 20.2 PHAS=    0.0 FOM= 0.00 TEST= 0
INDE 37 56 39 FOBS=    0.0 SIGMA= 22.3 PHAS=    0.0 FOM= 0.00 TEST= 1
INDE 38 38 38 FOBS=  208.1 SIGMA=  1.6 PHAS= -152.8 FOM= 0.97 TEST= 0
INDE 38 39 39 FOBS=  139.5 SIGMA=  1.3 PHAS=  127.0 FOM= 0.95 TEST= 0
INDE 38 39 41 FOBS=   61.1 SIGMA=  2.8 PHAS=   40.4 FOM= 0.78 TEST= 0
INDE 38 39 43 FOBS=    0.0 SIGMA= 18.9 PHAS=    0.0 FOM= 0.00 TEST= 0
INDE 38 39 45 FOBS=   63.9 SIGMA=  2.7 PHAS=   97.6 FOM= 0.40 TEST= 1
INDE 38 39 47 FOBS=  105.6 SIGMA=  1.8 PHAS=  158.3 FOM= 0.94 TEST= 0
```

*FIG. 12A - 561*

```
INDE 38 39 49 FOBS=  75.6 SIGMA=  2.5 PHAS=  177.4 FOM= 0.91 TEST= 0
INDE 38 39 51 FOBS=  38.5 SIGMA=  5.0 PHAS=  -71.2 FOM= 0.14 TEST= 0
INDE 38 39 53 FOBS=  46.6 SIGMA=  4.7 PHAS=  147.9 FOM= 0.73 TEST= 0
INDE 38 39 55 FOBS=   0.0 SIGMA= 22.1 PHAS=    0.0 FOM= 0.00 TEST= 0
INDE 38 40 38 FOBS=  63.8 SIGMA=  2.7 PHAS=  166.6 FOM= 0.74 TEST= 0
INDE 38 40 40 FOBS=  91.4 SIGMA=  1.9 PHAS=  -50.8 FOM= 0.26 TEST= 1
INDE 38 40 42 FOBS=   0.0 SIGMA= 18.4 PHAS=    0.0 FOM= 0.00 TEST= 0
INDE 38 40 44 FOBS=   0.0 SIGMA= 19.9 PHAS=    0.0 FOM= 0.00 TEST= 1
INDE 38 40 46 FOBS=  61.7 SIGMA=  2.8 PHAS=    6.1 FOM= 0.72 TEST= 0
INDE 38 40 48 FOBS=  11.1 SIGMA= 20.7 PHAS=  152.6 FOM= 0.26 TEST= 0
INDE 38 40 50 FOBS=  32.8 SIGMA=  7.0 PHAS=   67.0 FOM= 0.61 TEST= 0
INDE 38 40 52 FOBS=  10.2 SIGMA= 20.2 PHAS=  121.3 FOM= 0.21 TEST= 0
INDE 38 40 54 FOBS=   0.0 SIGMA= 21.1 PHAS=    0.0 FOM= 0.00 TEST= 0
INDE 38 41 39 FOBS=  31.5 SIGMA=  6.0 PHAS=   34.8 FOM= 0.24 TEST= 1
INDE 38 41 41 FOBS=  14.1 SIGMA= 13.5 PHAS=  178.2 FOM= 0.13 TEST= 0
INDE 38 41 43 FOBS=  86.6 SIGMA=  2.0 PHAS=  -34.5 FOM= 0.88 TEST= 0
INDE 38 41 45 FOBS=   0.0 SIGMA= 19.0 PHAS=    0.0 FOM= 0.00 TEST= 0
INDE 38 41 47 FOBS=  66.1 SIGMA=  2.8 PHAS=  161.8 FOM= 0.84 TEST= 0
INDE 38 41 49 FOBS=  78.8 SIGMA=  2.5 PHAS= -163.2 FOM= 0.92 TEST= 0
INDE 38 41 51 FOBS=  13.2 SIGMA= 15.5 PHAS=    7.4 FOM= 0.30 TEST= 0
INDE 38 41 53 FOBS=   0.0 SIGMA= 21.3 PHAS=    0.0 FOM= 0.00 TEST= 0
INDE 38 42 38 FOBS=   0.0 SIGMA= 18.9 PHAS=    0.0 FOM= 0.00 TEST= 0
INDE 38 42 40 FOBS=  34.1 SIGMA=  5.0 PHAS=  128.3 FOM= 0.62 TEST= 0
INDE 38 42 42 FOBS=   0.0 SIGMA= 18.6 PHAS=    0.0 FOM= 0.00 TEST= 0
INDE 38 42 44 FOBS=   0.0 SIGMA= 19.5 PHAS=    0.0 FOM= 0.00 TEST= 0
INDE 38 42 46 FOBS=  64.9 SIGMA=  2.7 PHAS=  -96.0 FOM= 0.67 TEST= 0
INDE 38 42 48 FOBS= 109.0 SIGMA=  1.8 PHAS=  130.2 FOM= 0.94 TEST= 0
INDE 38 42 50 FOBS=  50.8 SIGMA=  4.0 PHAS=   89.9 FOM= 0.85 TEST= 0
INDE 38 42 52 FOBS=  27.1 SIGMA=  8.9 PHAS=  -70.4 FOM= 0.00 TEST= 1
INDE 38 43 39 FOBS=  35.4 SIGMA=  5.3 PHAS=  -90.5 FOM= 0.04 TEST= 0
INDE 38 43 41 FOBS=  26.7 SIGMA=  6.8 PHAS=   72.2 FOM= 0.43 TEST= 0
INDE 38 43 43 FOBS=  78.4 SIGMA=  2.3 PHAS=   -8.1 FOM= 0.71 TEST= 0
INDE 38 43 45 FOBS=  27.1 SIGMA=  7.1 PHAS= -165.1 FOM= 0.30 TEST= 0
INDE 38 43 47 FOBS=   0.0 SIGMA= 20.3 PHAS=    0.0 FOM= 0.00 TEST= 0
INDE 38 43 49 FOBS=  28.8 SIGMA=  6.7 PHAS=   30.8 FOM= 0.61 TEST= 0
INDE 38 43 51 FOBS=  63.5 SIGMA=  3.4 PHAS=  -16.0 FOM= 0.78 TEST= 0
INDE 38 44 38 FOBS=   0.0 SIGMA= 19.3 PHAS=    0.0 FOM= 0.00 TEST= 0
INDE 38 44 40 FOBS=  68.4 SIGMA=  2.5 PHAS=  112.3 FOM= 0.32 TEST= 1
INDE 38 44 42 FOBS=   0.0 SIGMA= 19.1 PHAS=    0.0 FOM= 0.00 TEST= 0
INDE 38 44 44 FOBS=  53.8 SIGMA=  3.3 PHAS= -124.5 FOM= 0.69 TEST= 0
INDE 38 44 46 FOBS=  39.4 SIGMA=  4.5 PHAS=  139.8 FOM= 0.64 TEST= 0
INDE 38 44 48 FOBS= 102.9 SIGMA=  2.0 PHAS=   64.3 FOM= 0.95 TEST= 0
INDE 38 44 50 FOBS=  49.1 SIGMA=  4.0 PHAS= -148.4 FOM= 0.41 TEST= 0
INDE 38 45 39 FOBS=  32.6 SIGMA=  6.1 PHAS=  -53.1 FOM= 0.50 TEST= 0
INDE 38 45 41 FOBS=   0.0 SIGMA= 19.0 PHAS=    0.0 FOM= 0.00 TEST= 0
INDE 38 45 43 FOBS=  23.1 SIGMA=  7.6 PHAS=   79.1 FOM= 0.36 TEST= 0
INDE 38 45 45 FOBS=  45.3 SIGMA=  3.9 PHAS=  127.7 FOM= 0.66 TEST= 0
INDE 38 45 47 FOBS=  64.6 SIGMA=  2.8 PHAS=    4.8 FOM= 0.09 TEST= 1
INDE 38 45 49 FOBS=  81.7 SIGMA=  2.5 PHAS=   38.3 FOM= 0.72 TEST= 0
INDE 38 46 38 FOBS= 104.6 SIGMA=  1.8 PHAS=  149.4 FOM= 0.85 TEST= 0
INDE 38 46 40 FOBS=  89.4 SIGMA=  2.0 PHAS=  165.9 FOM= 0.91 TEST= 0
INDE 38 46 42 FOBS=   0.0 SIGMA= 19.0 PHAS=    0.0 FOM= 0.00 TEST= 0
INDE 38 46 44 FOBS=  58.3 SIGMA=  3.1 PHAS= -163.9 FOM= 0.64 TEST= 0
INDE 38 46 46 FOBS=  63.9 SIGMA=  3.0 PHAS=  138.7 FOM= 0.91 TEST= 0
INDE 38 46 48 FOBS=  30.0 SIGMA=  6.7 PHAS=   66.4 FOM= 0.54 TEST= 0
INDE 38 47 39 FOBS= 110.0 SIGMA=  1.6 PHAS=   47.6 FOM= 0.95 TEST= 0
INDE 38 47 41 FOBS=   0.0 SIGMA= 18.6 PHAS=    0.0 FOM= 0.00 TEST= 0
INDE 38 47 43 FOBS=  58.5 SIGMA=  3.1 PHAS=   95.3 FOM= 0.77 TEST= 0
INDE 38 47 45 FOBS=  87.4 SIGMA=  2.1 PHAS=  117.0 FOM= 0.93 TEST= 0
INDE 38 47 47 FOBS=  54.3 SIGMA=  3.5 PHAS=   20.1 FOM= 0.11 TEST= 1
INDE 38 48 38 FOBS=  79.5 SIGMA=  2.6 PHAS=  -79.7 FOM= 0.92 TEST= 0
INDE 38 48 40 FOBS=   0.0 SIGMA= 18.6 PHAS=    0.0 FOM= 0.00 TEST= 0
INDE 38 48 42 FOBS=  29.0 SIGMA=  6.1 PHAS=  143.6 FOM= 0.19 TEST= 1
INDE 38 48 44 FOBS=  22.1 SIGMA=  8.5 PHAS=   78.3 FOM= 0.21 TEST= 0
INDE 38 48 46 FOBS= 115.3 SIGMA=  1.7 PHAS=  106.4 FOM= 0.97 TEST= 0
INDE 38 49 39 FOBS=  19.9 SIGMA= 10.2 PHAS=  166.6 FOM= 0.44 TEST= 0
INDE 38 49 41 FOBS=   0.0 SIGMA= 20.8 PHAS=    0.0 FOM= 0.00 TEST= 1
INDE 38 49 43 FOBS=  40.3 SIGMA=  4.5 PHAS=  128.6 FOM= 0.19 TEST= 0
INDE 38 49 45 FOBS=  84.8 SIGMA=  2.2 PHAS=   49.5 FOM= 0.92 TEST= 0
INDE 38 50 38 FOBS=   0.0 SIGMA= 19.4 PHAS=    0.0 FOM= 0.00 TEST= 0
```

*FIG. 12A - 562*

| | | | | | | | | | | | |
|---|---|---|---|---|---|---|---|---|---|---|---|
| INDE | 38 | 50 | 40 | FOBS= | 6.2 | SIGMA= | 45.2 | PHAS= | -6.1 | FOM= | 0.09 | TEST= 0
| INDE | 38 | 50 | 42 | FOBS= | 62.1 | SIGMA= | 2.9 | PHAS= | 14.3 | FOM= | 0.09 | TEST= 0
| INDE | 38 | 50 | 44 | FOBS= | 11.9 | SIGMA= | 16.3 | PHAS= | -46.3 | FOM= | 0.23 | TEST= 0
| INDE | 38 | 51 | 39 | FOBS= | 0.0 | SIGMA= | 21.2 | PHAS= | 0.0 | FOM= | 0.00 | TEST= 0
| INDE | 38 | 51 | 41 | FOBS= | 0.0 | SIGMA= | 19.0 | PHAS= | 0.0 | FOM= | 0.00 | TEST= 0
| INDE | 38 | 51 | 43 | FOBS= | 30.5 | SIGMA= | 6.6 | PHAS= | -178.8 | FOM= | 0.69 | TEST= 0
| INDE | 38 | 52 | 38 | FOBS= | 32.1 | SIGMA= | 6.8 | PHAS= | 53.9 | FOM= | 0.07 | TEST= 1
| INDE | 38 | 52 | 40 | FOBS= | 0.0 | SIGMA= | 20.8 | PHAS= | 0.0 | FOM= | 0.00 | TEST= 0
| INDE | 38 | 52 | 42 | FOBS= | 0.0 | SIGMA= | 22.0 | PHAS= | 0.0 | FOM= | 0.00 | TEST= 0
| INDE | 38 | 53 | 39 | FOBS= | 93.0 | SIGMA= | 2.3 | PHAS= | 33.3 | FOM= | 0.93 | TEST= 0
| INDE | 38 | 53 | 41 | FOBS= | 41.9 | SIGMA= | 4.8 | PHAS= | 68.6 | FOM= | 0.78 | TEST= 0
| INDE | 38 | 54 | 38 | FOBS= | 48.5 | SIGMA= | 4.3 | PHAS= | -48.9 | FOM= | 0.82 | TEST= 0
| INDE | 38 | 54 | 40 | FOBS= | 77.2 | SIGMA= | 2.8 | PHAS= | -43.6 | FOM= | 0.92 | TEST= 0
| INDE | 38 | 55 | 39 | FOBS= | 10.2 | SIGMA= | 20.7 | PHAS= | -135.4 | FOM= | 0.08 | TEST= 0
| INDE | 38 | 56 | 38 | FOBS= | 0.0 | SIGMA= | 20.5 | PHAS= | 0.0 | FOM= | 0.00 | TEST= 1
| INDE | 39 | 40 | 39 | FOBS= | 100.9 | SIGMA= | 1.8 | PHAS= | 56.7 | FOM= | 0.95 | TEST= 0
| INDE | 39 | 40 | 41 | FOBS= | 86.5 | SIGMA= | 2.0 | PHAS= | -17.9 | FOM= | 0.57 | TEST= 1
| INDE | 39 | 40 | 43 | FOBS= | 74.4 | SIGMA= | 2.5 | PHAS= | -149.5 | FOM= | 0.88 | TEST= 0
| INDE | 39 | 40 | 45 | FOBS= | 44.9 | SIGMA= | 4.1 | PHAS= | 152.0 | FOM= | 0.72 | TEST= 0
| INDE | 39 | 40 | 47 | FOBS= | 60.5 | SIGMA= | 2.9 | PHAS= | 92.5 | FOM= | 0.87 | TEST= 0
| INDE | 39 | 40 | 49 | FOBS= | 110.3 | SIGMA= | 1.7 | PHAS= | 86.6 | FOM= | 0.96 | TEST= 0
| INDE | 39 | 40 | 51 | FOBS= | 33.4 | SIGMA= | 6.7 | PHAS= | -54.6 | FOM= | 0.61 | TEST= 0
| INDE | 39 | 40 | 53 | FOBS= | 66.5 | SIGMA= | 3.2 | PHAS= | 20.6 | FOM= | 0.79 | TEST= 0
| INDE | 39 | 41 | 40 | FOBS= | 27.5 | SIGMA= | 6.9 | PHAS= | 61.2 | FOM= | 0.05 | TEST= 1
| INDE | 39 | 41 | 42 | FOBS= | 51.6 | SIGMA= | 3.4 | PHAS= | 92.8 | FOM= | 0.86 | TEST= 0
| INDE | 39 | 41 | 44 | FOBS= | 0.0 | SIGMA= | 19.1 | PHAS= | 0.0 | FOM= | 0.00 | TEST= 0
| INDE | 39 | 41 | 46 | FOBS= | 56.1 | SIGMA= | 3.1 | PHAS= | -152.4 | FOM= | 0.20 | TEST= 0
| INDE | 39 | 41 | 48 | FOBS= | 86.8 | SIGMA= | 2.1 | PHAS= | 15.9 | FOM= | 0.92 | TEST= 0
| INDE | 39 | 41 | 50 | FOBS= | 74.8 | SIGMA= | 2.7 | PHAS= | 73.8 | FOM= | 0.90 | TEST= 0
| INDE | 39 | 41 | 52 | FOBS= | 40.1 | SIGMA= | 5.3 | PHAS= | -2.3 | FOM= | 0.57 | TEST= 0
| INDE | 39 | 42 | 39 | FOBS= | 52.3 | SIGMA= | 3.3 | PHAS= | -60.9 | FOM= | 0.55 | TEST= 0
| INDE | 39 | 42 | 41 | FOBS= | 68.7 | SIGMA= | 2.6 | PHAS= | 10.3 | FOM= | 0.87 | TEST= 0
| INDE | 39 | 42 | 43 | FOBS= | 0.0 | SIGMA= | 19.6 | PHAS= | 0.0 | FOM= | 0.00 | TEST= 0
| INDE | 39 | 42 | 45 | FOBS= | 28.6 | SIGMA= | 6.5 | PHAS= | 23.8 | FOM= | 0.77 | TEST= 0
| INDE | 39 | 42 | 47 | FOBS= | 0.0 | SIGMA= | 20.7 | PHAS= | 0.0 | FOM= | 0.00 | TEST= 0
| INDE | 39 | 42 | 49 | FOBS= | 70.8 | SIGMA= | 2.7 | PHAS= | 74.8 | FOM= | 0.91 | TEST= 0
| INDE | 39 | 42 | 51 | FOBS= | 66.8 | SIGMA= | 3.2 | PHAS= | -49.4 | FOM= | 0.85 | TEST= 0
| INDE | 39 | 43 | 40 | FOBS= | 23.5 | SIGMA= | 8.0 | PHAS= | 45.0 | FOM= | 0.25 | TEST= 0
| INDE | 39 | 43 | 42 | FOBS= | 41.4 | SIGMA= | 4.3 | PHAS= | 44.8 | FOM= | 0.58 | TEST= 0
| INDE | 39 | 43 | 44 | FOBS= | 52.2 | SIGMA= | 3.7 | PHAS= | -94.6 | FOM= | 0.77 | TEST= 0
| INDE | 39 | 43 | 46 | FOBS= | 0.0 | SIGMA= | 19.1 | PHAS= | 0.0 | FOM= | 0.00 | TEST= 0
| INDE | 39 | 43 | 48 | FOBS= | 75.2 | SIGMA= | 2.4 | PHAS= | 23.5 | FOM= | 0.94 | TEST= 0
| INDE | 39 | 43 | 50 | FOBS= | 46.0 | SIGMA= | 4.5 | PHAS= | 32.7 | FOM= | 0.51 | TEST= 0
| INDE | 39 | 44 | 39 | FOBS= | 37.8 | SIGMA= | 4.8 | PHAS= | -115.9 | FOM= | 0.61 | TEST= 0
| INDE | 39 | 44 | 41 | FOBS= | 73.6 | SIGMA= | 2.4 | PHAS= | 131.6 | FOM= | 0.20 | TEST= 1
| INDE | 39 | 44 | 43 | FOBS= | 60.3 | SIGMA= | 3.0 | PHAS= | -64.1 | FOM= | 0.82 | TEST= 0
| INDE | 39 | 44 | 45 | FOBS= | 0.0 | SIGMA= | 19.3 | PHAS= | 0.0 | FOM= | 0.00 | TEST= 0
| INDE | 39 | 44 | 47 | FOBS= | 71.2 | SIGMA= | 2.6 | PHAS= | 147.8 | FOM= | 0.57 | TEST= 0
| INDE | 39 | 44 | 49 | FOBS= | 57.4 | SIGMA= | 3.3 | PHAS= | -33.5 | FOM= | 0.90 | TEST= 0
| INDE | 39 | 45 | 40 | FOBS= | 134.4 | SIGMA= | 1.4 | PHAS= | 8.3 | FOM= | 0.93 | TEST= 0
| INDE | 39 | 45 | 42 | FOBS= | 0.0 | SIGMA= | 18.7 | PHAS= | 0.0 | FOM= | 0.00 | TEST= 0
| INDE | 39 | 45 | 44 | FOBS= | 0.0 | SIGMA= | 20.2 | PHAS= | 0.0 | FOM= | 0.00 | TEST= 0
| INDE | 39 | 45 | 46 | FOBS= | 84.4 | SIGMA= | 2.2 | PHAS= | 45.4 | FOM= | 0.93 | TEST= 0
| INDE | 39 | 45 | 48 | FOBS= | 68.7 | SIGMA= | 2.7 | PHAS= | 38.2 | FOM= | 0.79 | TEST= 0
| INDE | 39 | 45 | 50 | FOBS= | 33.2 | SIGMA= | 10.2 | PHAS= | -134.2 | FOM= | 0.21 | TEST= 0
| INDE | 39 | 46 | 39 | FOBS= | 147.2 | SIGMA= | 1.3 | PHAS= | -62.5 | FOM= | 0.96 | TEST= 0
| INDE | 39 | 46 | 41 | FOBS= | 12.1 | SIGMA= | 15.1 | PHAS= | -69.2 | FOM= | 0.04 | TEST= 0
| INDE | 39 | 46 | 43 | FOBS= | 17.0 | SIGMA= | 11.3 | PHAS= | -50.6 | FOM= | 0.19 | TEST= 0
| INDE | 39 | 46 | 45 | FOBS= | 0.0 | SIGMA= | 21.2 | PHAS= | 0.0 | FOM= | 0.00 | TEST= 0
| INDE | 39 | 46 | 47 | FOBS= | 70.9 | SIGMA= | 2.6 | PHAS= | -8.5 | FOM= | 0.83 | TEST= 0
| INDE | 39 | 46 | 49 | FOBS= | 40.0 | SIGMA= | 5.8 | PHAS= | -67.2 | FOM= | 0.27 | TEST= 0
| INDE | 39 | 47 | 40 | FOBS= | 26.3 | SIGMA= | 7.4 | PHAS= | 74.9 | FOM= | 0.22 | TEST= 0
| INDE | 39 | 47 | 42 | FOBS= | 34.5 | SIGMA= | 5.2 | PHAS= | 79.8 | FOM= | 0.32 | TEST= 0
| INDE | 39 | 47 | 44 | FOBS= | 60.0 | SIGMA= | 3.1 | PHAS= | 77.6 | FOM= | 0.57 | TEST= 0
| INDE | 39 | 47 | 46 | FOBS= | 143.5 | SIGMA= | 1.4 | PHAS= | 26.5 | FOM= | 0.97 | TEST= 0
| INDE | 39 | 47 | 48 | FOBS= | 47.6 | SIGMA= | 4.4 | PHAS= | 41.3 | FOM= | 0.83 | TEST= 0
| INDE | 39 | 48 | 39 | FOBS= | 49.8 | SIGMA= | 3.7 | PHAS= | 136.0 | FOM= | 0.64 | TEST= 0
| INDE | 39 | 48 | 41 | FOBS= | 36.0 | SIGMA= | 5.4 | PHAS= | 138.6 | FOM= | 0.36 | TEST= 0
| INDE | 39 | 48 | 43 | FOBS= | 109.2 | SIGMA= | 1.7 | PHAS= | -34.1 | FOM= | 0.18 | TEST= 1
| INDE | 39 | 48 | 45 | FOBS= | 70.3 | SIGMA= | 2.7 | PHAS= | -67.3 | FOM= | 0.90 | TEST= 0

*FIG. 12A - 563*

```
INDE 39 48 47 FOBS= 115.8 SIGMA=   1.7 PHAS=  -30.9 FOM= 0.97 TEST= 0
INDE 39 49 40 FOBS=  79.7 SIGMA=   2.4 PHAS=   44.2 FOM= 0.87 TEST= 0
INDE 39 49 42 FOBS=  59.6 SIGMA=   3.1 PHAS=  -66.6 FOM= 0.57 TEST= 0
INDE 39 49 44 FOBS=  48.1 SIGMA=   3.9 PHAS= -178.6 FOM= 0.85 TEST= 0
INDE 39 49 46 FOBS=  38.3 SIGMA=   7.1 PHAS=  -59.7 FOM= 0.57 TEST= 0
INDE 39 50 39 FOBS=  78.2 SIGMA=   2.5 PHAS=   98.2 FOM= 0.88 TEST= 0
INDE 39 50 41 FOBS=  64.3 SIGMA=   2.9 PHAS=  -74.7 FOM= 0.84 TEST= 0
INDE 39 50 43 FOBS=  95.4 SIGMA=   2.0 PHAS=   93.6 FOM= 0.89 TEST= 0
INDE 39 50 45 FOBS=   0.0 SIGMA=  24.4 PHAS=    0.0 FOM= 0.00 TEST= 0
INDE 39 51 40 FOBS=   0.0 SIGMA=  19.7 PHAS=    0.0 FOM= 0.00 TEST= 0
INDE 39 51 42 FOBS=  30.9 SIGMA=   6.0 PHAS=  -63.4 FOM= 0.64 TEST= 0
INDE 39 52 39 FOBS=  55.2 SIGMA=   3.8 PHAS=   17.0 FOM= 0.34 TEST= 0
INDE 39 52 41 FOBS=  24.7 SIGMA=   8.2 PHAS=   99.4 FOM= 0.04 TEST= 0
INDE 39 53 40 FOBS=  97.1 SIGMA=   2.2 PHAS=  -98.3 FOM= 0.90 TEST= 0
INDE 39 54 39 FOBS=  60.5 SIGMA=   3.5 PHAS=   27.2 FOM= 0.27 TEST= 0
INDE 40 40 40 FOBS= 127.4 SIGMA=   2.5 PHAS=   22.8 FOM= 0.94 TEST= 0
INDE 40 41 41 FOBS=  44.1 SIGMA=   4.0 PHAS=  -87.0 FOM= 0.22 TEST= 1
INDE 40 41 43 FOBS=   0.0 SIGMA=  19.7 PHAS=    0.0 FOM= 0.00 TEST= 0
INDE 40 41 45 FOBS=  24.0 SIGMA=   7.7 PHAS=   -4.8 FOM= 0.26 TEST= 0
INDE 40 41 47 FOBS=  37.2 SIGMA=   5.6 PHAS=   91.3 FOM= 0.26 TEST= 0
INDE 40 41 49 FOBS= 105.8 SIGMA=   1.8 PHAS=  -81.3 FOM= 0.94 TEST= 0
INDE 40 41 51 FOBS=  47.9 SIGMA=   4.2 PHAS= -126.1 FOM= 0.78 TEST= 0
INDE 40 42 40 FOBS=  64.2 SIGMA=   2.8 PHAS=  -73.2 FOM= 0.74 TEST= 0
INDE 40 42 42 FOBS=  76.0 SIGMA=   2.4 PHAS=  -13.4 FOM= 0.91 TEST= 0
INDE 40 42 44 FOBS=  63.0 SIGMA=   2.9 PHAS= -157.1 FOM= 0.65 TEST= 0
INDE 40 42 46 FOBS=   0.0 SIGMA=  19.2 PHAS=    0.0 FOM= 0.00 TEST= 0
INDE 40 42 48 FOBS=  10.9 SIGMA=  18.0 PHAS=  156.7 FOM= 0.06 TEST= 0
INDE 40 42 50 FOBS=  58.5 SIGMA=   3.2 PHAS=    5.1 FOM= 0.86 TEST= 0
INDE 40 43 41 FOBS=  91.7 SIGMA=   2.0 PHAS=  -85.4 FOM= 0.89 TEST= 0
INDE 40 43 43 FOBS=   0.0 SIGMA=  19.3 PHAS=    0.0 FOM= 0.00 TEST= 0
INDE 40 43 45 FOBS=  48.2 SIGMA=   3.7 PHAS= -110.8 FOM= 0.77 TEST= 0
INDE 40 43 47 FOBS=   0.0 SIGMA=  19.0 PHAS=    0.0 FOM= 0.00 TEST= 0
INDE 40 43 49 FOBS=  87.6 SIGMA=   2.1 PHAS=  -60.8 FOM= 0.94 TEST= 0
INDE 40 44 40 FOBS=  86.1 SIGMA=   2.1 PHAS= -125.1 FOM= 0.91 TEST= 0
INDE 40 44 42 FOBS=  63.2 SIGMA=   2.9 PHAS=  -24.2 FOM= 0.85 TEST= 0
INDE 40 44 44 FOBS=  77.0 SIGMA=   2.4 PHAS= -168.4 FOM= 0.89 TEST= 0
INDE 40 44 46 FOBS=  24.4 SIGMA=   7.7 PHAS=  -92.5 FOM= 0.36 TEST= 0
INDE 40 44 48 FOBS=  23.8 SIGMA=   8.5 PHAS= -117.1 FOM= 0.08 TEST= 0
INDE 40 44 50 FOBS=  55.5 SIGMA=   3.5 PHAS= -100.1 FOM= 0.76 TEST= 0
INDE 40 45 41 FOBS=  75.2 SIGMA=   2.4 PHAS= -162.8 FOM= 0.84 TEST= 0
INDE 40 45 43 FOBS=   0.0 SIGMA=  20.4 PHAS=    0.0 FOM= 0.00 TEST= 0
INDE 40 45 45 FOBS=  33.1 SIGMA=   5.8 PHAS=   91.8 FOM= 0.20 TEST= 0
INDE 40 45 47 FOBS=  17.4 SIGMA=  11.1 PHAS=   26.9 FOM= 0.04 TEST= 0
INDE 40 45 49 FOBS=  52.9 SIGMA=   3.6 PHAS= -103.3 FOM= 0.57 TEST= 0
INDE 40 46 40 FOBS=  63.5 SIGMA=   2.9 PHAS= -139.3 FOM= 0.52 TEST= 1
INDE 40 46 42 FOBS=   0.0 SIGMA=  20.8 PHAS=    0.0 FOM= 0.00 TEST= 0
INDE 40 46 44 FOBS=   1.8 SIGMA= 102.1 PHAS=  174.3 FOM= 0.00 TEST= 0
INDE 40 46 46 FOBS=  56.2 SIGMA=   3.5 PHAS=  -35.7 FOM= 0.90 TEST= 0
INDE 40 46 48 FOBS=  61.4 SIGMA=   3.1 PHAS=  -65.2 FOM= 0.81 TEST= 0
INDE 40 47 41 FOBS=  21.3 SIGMA=   9.6 PHAS=   86.2 FOM= 0.46 TEST= 0
INDE 40 47 43 FOBS=  29.5 SIGMA=   6.8 PHAS=  -20.6 FOM= 0.21 TEST= 0
INDE 40 47 45 FOBS=  46.8 SIGMA=   4.7 PHAS=   64.8 FOM= 0.74 TEST= 0
INDE 40 47 47 FOBS=  99.2 SIGMA=   2.0 PHAS= -134.7 FOM= 0.94 TEST= 0
INDE 40 48 40 FOBS=  81.1 SIGMA=   2.2 PHAS=   -8.9 FOM= 0.77 TEST= 0
INDE 40 48 42 FOBS=   0.0 SIGMA=  19.4 PHAS=    0.0 FOM= 0.00 TEST= 0
INDE 40 48 44 FOBS=  82.4 SIGMA=   2.3 PHAS=  -16.5 FOM= 0.83 TEST= 0
INDE 40 48 46 FOBS=  38.4 SIGMA=   5.4 PHAS=   22.6 FOM= 0.68 TEST= 0
INDE 40 49 41 FOBS=  20.2 SIGMA=  10.4 PHAS=   22.2 FOM= 0.49 TEST= 0
INDE 40 49 43 FOBS= 112.9 SIGMA=   1.7 PHAS=  -75.8 FOM= 0.93 TEST= 0
INDE 40 49 45 FOBS=   0.0 SIGMA=  21.0 PHAS=    0.0 FOM= 0.00 TEST= 0
INDE 40 50 40 FOBS= 133.3 SIGMA=   1.4 PHAS=   -7.3 FOM= 0.97 TEST= 0
INDE 40 50 42 FOBS=  67.9 SIGMA=   2.9 PHAS= -164.3 FOM= 0.93 TEST= 0
INDE 40 50 44 FOBS=   0.0 SIGMA=  20.3 PHAS=    0.0 FOM= 0.00 TEST= 0
INDE 40 51 41 FOBS=   0.0 SIGMA=  20.1 PHAS=    0.0 FOM= 0.00 TEST= 0
INDE 40 52 40 FOBS=  28.2 SIGMA=   8.6 PHAS= -162.7 FOM= 0.56 TEST= 0
INDE 41 42 41 FOBS=  68.3 SIGMA=   2.7 PHAS= -147.8 FOM= 0.69 TEST= 0
INDE 41 42 43 FOBS=  85.7 SIGMA=   2.1 PHAS=  -28.7 FOM= 0.95 TEST= 0
INDE 41 42 45 FOBS=  46.4 SIGMA=   3.9 PHAS=   36.3 FOM= 0.52 TEST= 0
INDE 41 42 47 FOBS=  61.1 SIGMA=   3.0 PHAS= -172.7 FOM= 0.89 TEST= 0
INDE 41 42 49 FOBS=  97.0 SIGMA=   2.0 PHAS=  176.9 FOM= 0.94 TEST= 0
```

*FIG. 12A - 564*

| | | | | | | | | | | | | |
|---|---|---|---|---|---|---|---|---|---|---|---|---|
| INDE | 41 | 42 | 51 | FOBS= | 48.1 | SIGMA= | 5.7 | PHAS= | -176.2 | FOM= | 0.57 | TEST= 0 |
| INDE | 41 | 43 | 42 | FOBS= | 159.1 | SIGMA= | 1.2 | PHAS= | -138.7 | FOM= | 0.96 | TEST= 0 |
| INDE | 41 | 43 | 44 | FOBS= | 54.0 | SIGMA= | 3.3 | PHAS= | -98.2 | FOM= | 0.08 | TEST= 1 |
| INDE | 41 | 43 | 46 | FOBS= | 0.0 | SIGMA= | 19.4 | PHAS= | 0.0 | FOM= | 0.00 | TEST= 0 |
| INDE | 41 | 43 | 48 | FOBS= | 0.0 | SIGMA= | 19.6 | PHAS= | 0.0 | FOM= | 0.00 | TEST= 0 |
| INDE | 41 | 43 | 50 | FOBS= | 27.1 | SIGMA= | 8.6 | PHAS= | -154.5 | FOM= | 0.49 | TEST= 0 |
| INDE | 41 | 44 | 41 | FOBS= | 105.4 | SIGMA= | 1.8 | PHAS= | 114.3 | FOM= | 0.96 | TEST= 0 |
| INDE | 41 | 44 | 43 | FOBS= | 0.0 | SIGMA= | 20.2 | PHAS= | 0.0 | FOM= | 0.00 | TEST= 0 |
| INDE | 41 | 44 | 45 | FOBS= | 51.4 | SIGMA= | 3.6 | PHAS= | 138.4 | FOM= | 0.69 | TEST= 0 |
| INDE | 41 | 44 | 47 | FOBS= | 0.0 | SIGMA= | 20.1 | PHAS= | 0.0 | FOM= | 0.00 | TEST= 0 |
| INDE | 41 | 44 | 49 | FOBS= | 19.9 | SIGMA= | 9.9 | PHAS= | -154.4 | FOM= | 0.12 | TEST= 0 |
| INDE | 41 | 45 | 42 | FOBS= | 0.0 | SIGMA= | 20.0 | PHAS= | 0.0 | FOM= | 0.00 | TEST= 0 |
| INDE | 41 | 45 | 44 | FOBS= | 54.4 | SIGMA= | 3.4 | PHAS= | 65.1 | FOM= | 0.59 | TEST= 0 |
| INDE | 41 | 45 | 46 | FOBS= | 0.0 | SIGMA= | 19.2 | PHAS= | 0.0 | FOM= | 0.00 | TEST= 1 |
| INDE | 41 | 45 | 48 | FOBS= | 0.0 | SIGMA= | 20.9 | PHAS= | 0.0 | FOM= | 0.00 | TEST= 0 |
| INDE | 41 | 46 | 41 | FOBS= | 62.6 | SIGMA= | 2.9 | PHAS= | 105.7 | FOM= | 0.56 | TEST= 0 |
| INDE | 41 | 46 | 43 | FOBS= | 91.6 | SIGMA= | 2.1 | PHAS= | -132.7 | FOM= | 0.82 | TEST= 0 |
| INDE | 41 | 46 | 45 | FOBS= | 2.2 | SIGMA= | 91.2 | PHAS= | 31.6 | FOM= | 0.04 | TEST= 0 |
| INDE | 41 | 46 | 47 | FOBS= | 0.0 | SIGMA= | 19.5 | PHAS= | 0.0 | FOM= | 0.00 | TEST= 0 |
| INDE | 41 | 47 | 42 | FOBS= | 68.9 | SIGMA= | 2.7 | PHAS= | 97.5 | FOM= | 0.68 | TEST= 0 |
| INDE | 41 | 47 | 44 | FOBS= | 0.0 | SIGMA= | 22.0 | PHAS= | 0.0 | FOM= | 0.00 | TEST= 0 |
| INDE | 41 | 47 | 46 | FOBS= | 69.7 | SIGMA= | 2.8 | PHAS= | -53.4 | FOM= | 0.92 | TEST= 0 |
| INDE | 41 | 48 | 41 | FOBS= | 55.7 | SIGMA= | 3.3 | PHAS= | -46.4 | FOM= | 0.87 | TEST= 0 |
| INDE | 41 | 48 | 43 | FOBS= | 0.0 | SIGMA= | 20.6 | PHAS= | 0.0 | FOM= | 0.00 | TEST= 0 |
| INDE | 41 | 48 | 45 | FOBS= | 94.3 | SIGMA= | 2.1 | PHAS= | -109.2 | FOM= | 0.86 | TEST= 0 |
| INDE | 41 | 49 | 42 | FOBS= | 30.9 | SIGMA= | 6.6 | PHAS= | -20.2 | FOM= | 0.26 | TEST= 0 |
| INDE | 41 | 49 | 44 | FOBS= | 73.3 | SIGMA= | 2.6 | PHAS= | -156.7 | FOM= | 0.90 | TEST= 0 |
| INDE | 41 | 50 | 41 | FOBS= | 103.3 | SIGMA= | 1.8 | PHAS= | -100.0 | FOM= | 0.96 | TEST= 0 |
| INDE | 41 | 50 | 43 | FOBS= | 49.2 | SIGMA= | 3.9 | PHAS= | 152.4 | FOM= | 0.81 | TEST= 0 |
| INDE | 41 | 51 | 42 | FOBS= | 35.5 | SIGMA= | 8.5 | PHAS= | 115.0 | FOM= | 0.61 | TEST= 0 |
| INDE | 42 | 42 | 42 | FOBS= | 166.5 | SIGMA= | 2.1 | PHAS= | 87.5 | FOM= | 0.90 | TEST= 0 |
| INDE | 42 | 43 | 43 | FOBS= | 44.1 | SIGMA= | 4.8 | PHAS= | -101.7 | FOM= | 0.51 | TEST= 0 |
| INDE | 42 | 43 | 45 | FOBS= | 37.8 | SIGMA= | 4.9 | PHAS= | 84.7 | FOM= | 0.27 | TEST= 0 |
| INDE | 42 | 43 | 47 | FOBS= | 0.0 | SIGMA= | 19.7 | PHAS= | 0.0 | FOM= | 0.00 | TEST= 0 |
| INDE | 42 | 43 | 49 | FOBS= | 21.0 | SIGMA= | 9.0 | PHAS= | 23.9 | FOM= | 0.29 | TEST= 0 |
| INDE | 42 | 44 | 42 | FOBS= | 58.6 | SIGMA= | 3.2 | PHAS= | 99.4 | FOM= | 0.59 | TEST= 0 |
| INDE | 42 | 44 | 44 | FOBS= | 0.0 | SIGMA= | 20.0 | PHAS= | 0.0 | FOM= | 0.00 | TEST= 0 |
| INDE | 42 | 44 | 46 | FOBS= | 0.0 | SIGMA= | 19.2 | PHAS= | 0.0 | FOM= | 0.00 | TEST= 0 |
| INDE | 42 | 44 | 48 | FOBS= | 0.0 | SIGMA= | 19.4 | PHAS= | 0.0 | FOM= | 0.00 | TEST= 0 |
| INDE | 42 | 45 | 43 | FOBS= | 18.2 | SIGMA= | 10.6 | PHAS= | 135.2 | FOM= | 0.20 | TEST= 0 |
| INDE | 42 | 45 | 45 | FOBS= | 0.0 | SIGMA= | 19.7 | PHAS= | 0.0 | FOM= | 0.00 | TEST= 0 |
| INDE | 42 | 45 | 47 | FOBS= | 0.0 | SIGMA= | 21.3 | PHAS= | 0.0 | FOM= | 0.00 | TEST= 0 |
| INDE | 42 | 46 | 42 | FOBS= | 34.0 | SIGMA= | 5.4 | PHAS= | -23.1 | FOM= | 0.59 | TEST= 0 |
| INDE | 42 | 46 | 44 | FOBS= | 0.0 | SIGMA= | 20.8 | PHAS= | 0.0 | FOM= | 0.00 | TEST= 0 |
| INDE | 42 | 46 | 46 | FOBS= | 0.0 | SIGMA= | 20.0 | PHAS= | 0.0 | FOM= | 0.00 | TEST= 0 |
| INDE | 42 | 47 | 43 | FOBS= | 27.2 | SIGMA= | 7.2 | PHAS= | 155.7 | FOM= | 0.58 | TEST= 0 |
| INDE | 42 | 47 | 45 | FOBS= | 55.9 | SIGMA= | 3.5 | PHAS= | 166.8 | FOM= | 0.40 | TEST= 0 |
| INDE | 42 | 48 | 42 | FOBS= | 0.0 | SIGMA= | 19.2 | PHAS= | 0.0 | FOM= | 0.00 | TEST= 1 |
| INDE | 42 | 48 | 44 | FOBS= | 46.3 | SIGMA= | 4.2 | PHAS= | 55.8 | FOM= | 0.75 | TEST= 0 |
| INDE | 42 | 49 | 43 | FOBS= | 0.0 | SIGMA= | 20.3 | PHAS= | 0.0 | FOM= | 0.00 | TEST= 0 |
| INDE | 42 | 50 | 42 | FOBS= | 47.8 | SIGMA= | 4.0 | PHAS= | -161.7 | FOM= | 0.71 | TEST= 0 |
| INDE | 43 | 44 | 43 | FOBS= | 33.9 | SIGMA= | 5.5 | PHAS= | 116.0 | FOM= | 0.37 | TEST= 0 |
| INDE | 43 | 44 | 45 | FOBS= | 0.0 | SIGMA= | 21.4 | PHAS= | 0.0 | FOM= | 0.00 | TEST= 0 |
| INDE | 43 | 44 | 47 | FOBS= | 0.0 | SIGMA= | 20.5 | PHAS= | 0.0 | FOM= | 0.00 | TEST= 0 |
| INDE | 43 | 45 | 44 | FOBS= | 0.0 | SIGMA= | 20.7 | PHAS= | 0.0 | FOM= | 0.00 | TEST= 0 |
| INDE | 43 | 45 | 46 | FOBS= | 39.6 | SIGMA= | 5.1 | PHAS= | -151.0 | FOM= | 0.42 | TEST= 0 |
| INDE | 43 | 46 | 43 | FOBS= | 0.0 | SIGMA= | 19.3 | PHAS= | 0.0 | FOM= | 0.00 | TEST= 0 |
| INDE | 43 | 46 | 45 | FOBS= | 39.0 | SIGMA= | 5.5 | PHAS= | 118.3 | FOM= | 0.62 | TEST= 0 |
| INDE | 43 | 47 | 44 | FOBS= | 0.0 | SIGMA= | 19.9 | PHAS= | 0.0 | FOM= | 0.00 | TEST= 0 |
| INDE | 43 | 48 | 43 | FOBS= | 30.1 | SIGMA= | 6.6 | PHAS= | 78.0 | FOM= | 0.40 | TEST= 0 |
| INDE | 44 | 44 | 44 | FOBS= | 63.4 | SIGMA= | 5.2 | PHAS= | 75.6 | FOM= | 0.41 | TEST= 0 |
| INDE | 44 | 45 | 45 | FOBS= | 0.0 | SIGMA= | 20.0 | PHAS= | 0.0 | FOM= | 0.00 | TEST= 0 |
| INDE | 44 | 46 | 44 | FOBS= | 37.9 | SIGMA= | 5.3 | PHAS= | 174.9 | FOM= | 0.53 | TEST= 0 |

*FIG. 12A - 565*

SEQUENCE LISTING

```
<160> NUMBER OF SEQ ID NOS: 11

<210> SEQ ID NO 1
<211> LENGTH: 326
<212> TYPE: PRT
<213> ORGANISM: Artificial Sequence
<220> FEATURE:
<223> OTHER INFORMATION: Description of Artificial Sequence: Recombinant
      S. aureus MurB protein including polyhistidine region

<400> SEQUENCE: 1

Met Arg Gly Ser His His His His His His Thr Asp Pro Ile Asn Lys
 1               5                  10                  15

Asp Ile Tyr Gln Ala Leu Gln Gln Leu Ile Pro Asn Glu Lys Ile Lys
            20                  25                  30

Val Asp Glu Pro Leu Lys Arg Tyr Thr Tyr Thr Lys Thr Gly Gly Asn
        35                  40                  45

Ala Asp Phe Tyr Ile Thr Pro Thr Lys Asn Glu Glu Val Gln Ala Val
    50                  55                  60

Val Lys Tyr Ala Tyr Gln Asn Glu Ile Pro Val Thr Tyr Leu Gly Asn
65                  70                  75                  80

Gly Ser Asn Ile Ile Ile Arg Glu Gly Gly Ile Arg Gly Ile Val Ile
                85                  90                  95

Ser Leu Leu Ser Leu Asp His Ile Glu Val Ser Asp Asp Ala Ile Ile
                100                 105                 110

Ala Gly Ser Gly Ala Ala Ile Ile Asp Val Ser Arg Val Ala Arg Asp
            115                 120                 125

Tyr Ala Leu Thr Gly Leu Glu Phe Ala Cys Gly Ile Pro Gly Ser Ile
    130                 135                 140

Gly Gly Ala Val Tyr Met Asn Ala Gly Ala Tyr Gly Gly Glu Val Lys
145                 150                 155                 160

Asp Cys Ile Asp Tyr Ala Leu Cys Val Asn Glu Gln Gly Ser Leu Ile
                165                 170                 175

Lys Leu Thr Thr Lys Glu Leu Glu Leu Asp Tyr Arg Asn Ser Ile Ile
                180                 185                 190

Gln Lys Glu His Leu Val Val Leu Glu Ala Ala Phe Thr Leu Ala Pro
            195                 200                 205

Gly Lys Met Thr Glu Ile Gln Ala Lys Met Asp Asp Leu Thr Glu Arg
    210                 215                 220

Arg Glu Ser Lys Gln Pro Leu Glu Tyr Pro Ser Cys Gly Ser Val Phe
225                 230                 235                 240

Gln Arg Pro Pro Gly His Phe Ala Gly Lys Leu Ile Gln Asp Ser Asn
                245                 250                 255

Leu Gln Gly His Arg Ile Gly Gly Val Glu Val Ser Thr Lys His Ala
            260                 265                 270

Gly Phe Met Val Asn Val Asp Asn Gly Thr Ala Thr Asp Tyr Glu Asn
    275                 280                 285

Leu Ile His Tyr Val Gln Lys Thr Val Lys Glu Lys Phe Gly Ile Glu
    290                 295                 300
```

```
Leu Asn Arg Glu Val Arg Ile Ile Gly Glu His Pro Lys Glu Ser Leu
305                 310                 315                 320

Gln Pro Ser Leu Ile Ser
            325
```

<210> SEQ ID NO 2
<211> LENGTH: 342
<212> TYPE: PRT
<213> ORGANISM: Escherichia coli

<400> SEQUENCE: 2

```
Met Asp His Ser Leu Lys Pro Trp Asn Thr Phe Gly Ile Asp His Asn
 1               5                  10                  15

Ala Gln His Ile Val Cys Ala Glu Asp Glu Gln Gln Leu Leu Asn Ala
            20                  25                  30

Trp Gln Tyr Ala Thr Ala Glu Gly Gln Pro Val Leu Ile Leu Gly Glu
        35                  40                  45

Gly Ser Asn Val Leu Phe Leu Glu Asp Tyr Arg Gly Thr Val Ile Ile
    50                  55                  60

Asn Arg Ile Lys Gly Ile Glu Ile His Asp Pro Asp Ala Trp Tyr
65                  70                  75                  80

Leu His Val Gly Ala Gly Glu Asn Trp His Arg Leu Val Lys Tyr Thr
                85                  90                  95

Leu Gln Glu Gly Met Pro Gly Leu Glu Asn Leu Ala Leu Ile Pro Gly
            100                 105                 110

Cys Val Gly Ser Ser Pro Ile Gln Asn Ile Gly Ala Tyr Gly Val Glu
        115                 120                 125

Leu Gln Arg Val Cys Ala Tyr Val Asp Ser Val Glu Leu Ala Thr Gly
    130                 135                 140

Lys Gln Val Arg Leu Thr Ala Lys Glu Cys Arg Phe Gly Tyr Arg Asp
145                 150                 155                 160

Ser Ile Phe Lys His Glu Tyr Gln Asp Arg Phe Ala Ile Val Ala Val
                165                 170                 175

Gly Leu Arg Leu Pro Lys Glu Trp Gln Pro Val Leu Thr Tyr Gly Asp
            180                 185                 190

Leu Thr Arg Leu Asp Pro Thr Thr Val Thr Pro Gln Gln Val Phe Asn
        195                 200                 205

Ala Val Cys His Met Arg Thr Thr Lys Leu Pro Asp Pro Lys Val Asn
    210                 215                 220

Gly Asn Ala Gly Ser Phe Phe Lys Asn Pro Val Val Ser Ala Glu Thr
225                 230                 235                 240

Ala Lys Ala Leu Leu Ser Gln Phe Pro Thr Ala Pro Asn Tyr Pro Gln
                245                 250                 255

Ala Asp Gly Ser Val Lys Leu Ala Ala Gly Trp Leu Ile Asp Gln Cys
            260                 265                 270

Gln Leu Lys Gly Met Gln Ile Gly Gly Ala Ala Val His Arg Gln Gln
        275                 280                 285

Ala Leu Val Leu Ile Asn Glu Asp Asn Ala Lys Ser Glu Asp Val Val
    290                 295                 300

Gln Leu Ala His His Val Arg Gln Lys Val Gly Glu Lys Phe Asn Val
305                 310                 315                 320

Trp Leu Glu Pro Glu Val Arg Phe Ile Gly Ala Ser Gly Glu Val Ser
                325                 330                 335

Ala Val Glu Thr Ile Ser
            340
```

```
<210> SEQ ID NO 3
<211> LENGTH: 259
<212> TYPE: PRT
<213> ORGANISM: Helicobacter pylori

<400> SEQUENCE: 3

Met Leu Glu Thr Thr Ile Asp Phe Ser Arg Tyr Ser Ser Val Lys Ile
 1               5                  10                  15

Gly Thr Pro Leu Lys Val Ser Val Leu Glu Asn Asp Asp Glu Ile Ser
            20                  25                  30

Gln Glu His Gln Ile Ile Gly Leu Ala Asn Asn Leu Leu Ile Ala Pro
        35                  40                  45

Ser Ala Lys Asn Leu Ala Leu Leu Gly Lys Asn Tyr Asp Tyr Ile Cys
    50                  55                  60

Asp Lys Gly Glu Cys Val Glu Ile Gly Ala Ala Asn Ala Ser Lys
65                  70                  75                  80

Ile Phe Asn Tyr Phe Arg Ala Asn Asp Leu Glu Gly Leu Glu Phe Leu
                85                  90                  95

Gly Gln Leu Pro Gly Thr Leu Gly Ala Leu Val Lys Met Asn Ala Gly
            100                 105                 110

Met Lys Glu Phe Glu Ile Lys Asn Val Leu Glu Ser Ala Cys Ile Asn
        115                 120                 125

Asn Gln Trp Leu Glu Lys Glu Ala Leu Gly Leu Gly Tyr Arg Ser Ser
    130                 135                 140

Gly Phe Ser Gly Val Val Leu Arg Ala Arg Phe Lys Lys Thr His Gly
145                 150                 155                 160

Phe Arg Glu Gly Val Leu Lys Ala Cys Gln Ser Met Arg Lys Ser His
                165                 170                 175

Pro Lys Leu Pro Asn Phe Gly Ser Cys Phe Lys Asn Pro Pro Asn Asp
            180                 185                 190

His Ala Gly Arg Leu Leu Glu Gly Val Gly Leu Arg Gly Tyr Cys Leu
        195                 200                 205

Lys Arg Val Gly Phe Ala Lys Glu His Ala Asn Phe Leu Val Asn Leu
    210                 215                 220

Gly Gly Ala Glu Phe Glu Ala Leu Asp Leu Ile Glu Leu Ala Lys
225                 230                 235                 240

Ala Arg Val Leu Gln Glu Tyr Gly Ile His Leu Glu Glu Val Lys
                245                 250                 255

Ile Leu Arg

<210> SEQ ID NO 4
<211> LENGTH: 297
<212> TYPE: PRT
<213> ORGANISM: Aquifex aeolicus

<400> SEQUENCE: 4

Met Leu Phe Leu Lys Asn Val Pro Leu Gln Asn Leu Thr Thr Ile Lys
 1               5                  10                  15

Ile Gly Gly Arg Val Ser Phe Tyr Ala Glu Pro Ser Asp Leu Lys Glu
            20                  25                  30

Ile Ser Leu Cys Ile Asp Phe Ser Lys Ser Arg Asp Ile Pro Leu Phe
        35                  40                  45

Val Leu Gly Asn Gly Ser Asn Thr Ile Phe Gly Asp Val Arg Gly Leu
    50                  55                  60

Val Val Asn Leu Lys Asn Leu Lys Gly Phe Lys Val Lys Glu Ile Lys
65                  70                  75                  80
```

-continued

```
Gly Lys Phe Phe Val Glu Ala Phe Ser Gly Thr Pro Leu Lys Asp Leu
                85                  90                  95

Ile Arg Phe Ser Val Lys Glu Asn Val Lys Ser Phe Tyr Lys Leu Leu
            100                 105                 110

Gly Phe Pro Ala Ser Val Gly Gly Ala Val Ser Met Asn Ala Gly Ala
        115                 120                 125

Phe Gly Val Glu Ile Ser Asp Phe Leu Lys Glu Val Tyr Phe Val Asp
    130                 135                 140

Trp Glu Gly Lys Leu Gln Lys Ala Lys Arg Asp Glu Leu Asn Phe Ser
145                 150                 155                 160

Tyr Arg Lys Ser Pro Phe Pro Lys Leu Gly Ile Val Phe Lys Val Val
                165                 170                 175

Phe Glu Phe Glu Arg Ser Lys Glu Asn Ile Leu Pro Lys Tyr Glu Lys
            180                 185                 190

Ile Arg Arg Ile Arg Lys Glu Lys Gln Pro Ile Asn Leu Pro Thr Ser
        195                 200                 205

Gly Ser Thr Phe Lys Asn Pro Glu Gly Asn Phe Ala Gly Lys Leu Leu
    210                 215                 220

Glu Lys Ala Gly Leu Lys Gly Phe Arg Leu Lys Asn Val Gly Phe Ser
225                 230                 235                 240

Glu Lys His Ala Asn Phe Leu Val Asn Tyr Gly Gly Gly Thr Phe Ser
                245                 250                 255

Glu Val Val Asp Leu Ile Asn Ile Ala Lys Glu Arg Val Tyr Glu Asn
            260                 265                 270

Phe Gly Ile Val Leu Glu Glu Val Lys Leu Ile Glu Ser Ser Gly
        275                 280                 285

Ser Asp Gly Trp Lys Val Leu Gly Ala
    290                 295
```

<210> SEQ ID NO 5
<211> LENGTH: 303
<212> TYPE: PRT
<213> ORGANISM: Bacillus subtilis

<400> SEQUENCE: 5

```
Met Glu Lys Val Ile Gln Glu Leu Lys Glu Arg Glu Val Gly Lys Val
1               5                   10                  15

Leu Ala Asn Glu Pro Leu Ala Asn His Thr Thr Met Lys Ile Gly Gly
            20                  25                  30

Pro Ala Asp Val Leu Val Ile Pro Ser Ser Val Asp Ala Val Lys Asp
        35                  40                  45

Ile Met Asp Val Ile Lys Lys Tyr Asp Val Lys Trp Thr Val Ile Gly
    50                  55                  60

Arg Gly Ser Asn Leu Leu Val Leu Asp Glu Gly Ile Arg Gly Val Val
65                  70                  75                  80

Ile Lys Leu Gly Ala Gly Leu Asp His Leu Glu Leu Glu Gly Glu Gln
                85                  90                  95

Val Thr Val Gly Gly Gly Tyr Ser Val Val Arg Leu Ala Thr Ser Leu
            100                 105                 110

Ser Lys Lys Gly Leu Ser Gly Leu Glu Phe Ala Ala Gly Ile Pro Gly
        115                 120                 125

Ser Val Gly Gly Ala Val Tyr Met Asn Ala Gly Ala His Gly Ser Asp
    130                 135                 140

Met Ser Glu Ile Leu Val Lys Ala His Ile Leu Phe Glu Asp Gly Thr
145                 150                 155                 160
```

```
Ile Glu Trp Leu Thr Asn Glu Gln Met Asp Phe Ser Tyr Arg Thr Ser
            165                 170                 175

Val Leu Gln Lys Lys Arg Pro Gly Val Cys Leu Glu Ala Val Leu Gln
            180                 185                 190

Leu Glu Gln Lys Asp Lys Glu Ser Ile Val Gln Gln Met Gln Ser Asn
            195                 200                 205

Lys Asp Tyr Arg Lys Asn Thr Gln Pro Tyr Ser Pro Cys Ala Gly
            210                 215                 220

Ser Ile Phe Arg Asn Pro Leu Pro Asn His Ala Gly Asn Leu Val Glu
225                 230                 235                 240

Lys Ala Gly Leu Lys Gly Tyr Gln Ile Gly Gly Ala Lys Ile Ser Glu
            245                 250                 255

Met His Gly Asn Phe Ile Val Asn Ala Gly Gly Ala Ser Ala Lys Asp
            260                 265                 270

Val Leu Asp Leu Ile Asp His Val Lys Lys Thr Ile Arg Glu Lys Tyr
            275                 280                 285

Glu Ile Asp Met His Thr Glu Val Glu Ile Ile Gly Gly Asn Arg
            290                 295                 300

<210> SEQ ID NO 6
<211> LENGTH: 302
<212> TYPE: PRT
<213> ORGANISM: Borrelia burgdorferi

<400> SEQUENCE: 6

Met Pro Lys Ser Leu Asn Asn Phe Leu Lys Lys Ile Asn Ile Lys Pro
1               5                   10                  15

Gln Thr Lys Asn Leu Ala Asn Tyr Thr Thr Tyr Lys Ile Gly Asn Ile
            20                  25                  30

Ser Lys Leu Phe Leu Thr Pro Lys Asn Ile Lys Glu Ala Glu Asn Ile
            35                  40                  45

Phe Lys Ala Ala Ile Glu Glu Lys Ile Lys Leu Phe Ile Leu Gly Gly
        50                  55                  60

Gly Ser Asn Ile Leu Val Asn Asp Glu Arg Glu Ile Asp Phe Pro Ile
65                  70                  75                  80

Ile Tyr Thr Gly Tyr Leu Asn Lys Ile Glu Ile His Glu Asn Lys Ile
            85                  90                  95

Val Gly Glu Cys Gly Ala Asp Phe Glu Ser Leu Cys Lys Ile Ala Leu
            100                 105                 110

Asp Asn Ser Leu Ser Gly Leu Glu Phe Ile Tyr Gly Leu Pro Gly Thr
            115                 120                 125

Leu Gly Gly Ala Val Trp Met Asn Ala Arg Cys Phe Gly Asn Glu Ile
            130                 135                 140

Ser Glu Ile Leu Lys Lys Ile Thr Phe Ile Asp Asp Lys Gly Lys Thr
145                 150                 155                 160

Ile Cys Lys Glu Phe Lys Lys Glu Asp Phe Lys Tyr Lys Ile Ser Pro
            165                 170                 175

Phe Gln Asn Lys Asn Phe Ile Leu Lys Ile Glu Leu Asn Leu Lys
            180                 185                 190

Lys Asp Asn Lys Lys Ile Ile Glu Glu Lys Met Asn Lys Asn Lys Gln
            195                 200                 205

Ala Arg Ile Asn Arg Gly His Tyr Leu Phe Pro Ser Gly Gly Ser Thr
            210                 215                 220

Phe Lys Asn Asn Lys Ala Phe Leu Lys Pro Ser Gly Gln Ile Ile Glu
225                 230                 235                 240
```

-continued

Glu Cys Lys Leu Lys Gly Leu Ser Ile Gly Gly Ala Thr Val Ser Lys
              245                 250                 255

Tyr His Gly Asn Phe Ile Ile Asn Ile Asn Asn Ala Thr Ser Lys Asp
              260                 265                 270

Ile Lys Ser Leu Ile Glu Lys Val Lys Ala Glu Val Tyr Leu Lys Thr
              275                 280                 285

Gly Leu Leu Glu Glu Val Leu Tyr Ile Gly Phe Lys
              290                 295                 300

<210> SEQ ID NO 7
<211> LENGTH: 304
<212> TYPE: PRT
<213> ORGANISM: Chlamydia pneumoniae

<400> SEQUENCE: 7

Met Lys Glu Ala Ala Pro Met His Phe Pro Phe Pro Val Arg Arg Ser
  1               5                  10                  15

Val Trp Leu Asn Arg Tyr Ser Thr Phe Arg Ile Gly Gly Pro Ala Asn
                 20                  25                  30

Tyr Phe Lys Ala Ile His Thr Ile Glu Glu Ala Arg Glu Val Ile Arg
             35                  40                  45

Phe Leu His Ser Ile Asn Tyr Pro Phe Leu Ile Ile Gly Lys Gly Ser
         50                  55                  60

Asn Cys Leu Phe Asp Asp Arg Gly Phe Asp Gly Phe Val Leu Tyr Asn
 65                  70                  75                  80

Ala Ile Tyr Gly Lys Gln Phe Leu Glu Asp Ala Arg Ile Lys Ala Tyr
                 85                  90                  95

Ser Gly Leu Ser Phe Ala Ala Leu Gly Lys Ala Thr Ala Tyr Asn Gly
            100                 105                 110

Tyr Ser Gly Leu Glu Phe Ala Ala Gly Ile Pro Gly Ser Val Gly Gly
            115                 120                 125

Ala Ile Phe Met Asn Ala Gly Thr Asn Glu Ser Asp Ile Ser Ser Val
        130                 135                 140

Val Arg Asn Val Glu Thr Ile Asn Ser Glu Gly Glu Leu Cys Ser Tyr
145                 150                 155                 160

Ser Val Glu Glu Leu Glu Leu Ser Tyr Arg Ser Ser Arg Phe His Arg
                165                 170                 175

Gln Gln Glu Phe Ile Leu Ser Ala Thr Phe Gln Leu Ser Lys Lys Gln
            180                 185                 190

Val Ser Ala Asp His Ser Lys Ser Ile Leu Gln His Arg Leu Met Thr
        195                 200                 205

Gln Pro Tyr Thr Gln Pro Ser Ala Gly Cys Ile Phe Arg Asn Pro Glu
    210                 215                 220

Gly Thr Ser Ala Gly Lys Leu Ile Asp Ala Ala Gly Leu Lys Gly Leu
225                 230                 235                 240

Ala Ile Gly Gly Ala Gln Ile Ser Pro Leu His Ala Asn Phe Ile Ile
                245                 250                 255

Asn Thr Gly Lys Ala Thr Ser Asp Glu Val Lys Gln Leu Ile Ala Ile
            260                 265                 270

Ile Gln Ser Thr Leu Lys Thr Gln Gly Ile Asp Leu Glu His Glu Ile
        275                 280                 285

Arg Ile Ile Pro Tyr Gln Pro Lys Ile His Ser Pro Val Ser Glu Lys
    290                 295                 300

```
<210> SEQ ID NO 8
<211> LENGTH: 310
<212> TYPE: PRT
<213> ORGANISM: Rickettsia prowazekii

<400> SEQUENCE: 8
```

| | | | | | | | | | | | | | | | |
|---|---|---|---|---|---|---|---|---|---|---|---|---|---|---|---|
| Met | Ile | Gln | Asn | Pro | Met | Ile | Lys | Leu | Cys | Asn | Glu | Ser | Asn | Asn | Met |
| 1 | | | | 5 | | | | | 10 | | | | | 15 | |
| Ser | Ile | Leu | Pro | Ile | Ile | Lys | Gly | Glu | Tyr | Lys | Lys | Asp | Tyr | Asn | Leu |
| | | | 20 | | | | | 25 | | | | | 30 | | |
| Lys | His | Leu | Thr | Trp | Phe | Lys | Val | Gly | Gly | Asn | Ala | Glu | Ile | Phe | Phe |
| | | 35 | | | | | 40 | | | | | 45 | | | |
| Lys | Pro | Phe | Asp | Phe | Ala | Asp | Leu | Lys | Ser | Phe | Leu | Ile | Gln | Asn | Lys |
| | 50 | | | | | 55 | | | | | 60 | | | | |
| Gln | Lys | Leu | Pro | Ile | Thr | Thr | Phe | Gly | Ser | Gly | Ser | Asn | Ile | Ile | Ile |
| 65 | | | | | 70 | | | | | 75 | | | | | 80 |
| Arg | Asp | Gly | Gly | Ile | Glu | Gly | Val | Val | Ile | Lys | Leu | Gly | Gln | Asn | Phe |
| | | | | 85 | | | | | 90 | | | | | 95 | |
| Asn | Lys | Ile | Glu | Phe | Leu | Asp | Asn | His | Leu | Ile | Val | Gly | Ser | Ser | Cys |
| | | | 100 | | | | | 105 | | | | | 110 | | |
| Leu | Asn | Tyr | Asn | Leu | Ala | Arg | Phe | Cys | Gln | Ala | Asn | Ala | Ile | Ser | Gly |
| | | 115 | | | | | 120 | | | | | 125 | | | |
| Phe | Glu | Phe | Leu | Val | Gly | Ile | Pro | Gly | Thr | Ile | Gly | Gly | Val | Ile | |
| 130 | | | | | 135 | | | | | 140 | | | | | |
| Met | Asn | Ala | Gly | Ala | Tyr | Gly | Ser | Ala | Phe | Gln | Asp | Ile | Ile | Val | Gln |
| 145 | | | | | 150 | | | | | 155 | | | | | 160 |
| Val | Glu | Ala | Leu | Asp | Phe | Ser | Gly | Asn | Phe | Leu | Thr | Phe | Thr | Asn | Lys |
| | | | | 165 | | | | | 170 | | | | | 175 | |
| Glu | Ile | Gly | Phe | Lys | Tyr | Arg | Gly | Asn | Asn | Leu | Pro | Lys | Asp | Leu | Ile |
| | | | 180 | | | | | 185 | | | | | 190 | | |
| Leu | Leu | Lys | Ala | Val | Phe | Lys | Val | Asn | Lys | Gly | Asp | Ser | Gln | Asn | Ile |
| | | 195 | | | | | 200 | | | | | 205 | | | |
| Leu | Leu | Lys | Met | Asn | Lys | Ile | Asn | Asn | Thr | Arg | Ser | Ser | Thr | Gln | Pro |
| 210 | | | | | 215 | | | | | 220 | | | | | |
| Ile | Lys | Glu | Arg | Thr | Gly | Gly | Ser | Thr | Phe | Ile | Asn | Pro | Glu | Gly | Arg |
| 225 | | | | | 230 | | | | | 235 | | | | | 240 |
| Lys | Ser | Trp | Glu | Leu | Ile | Asp | Lys | Ala | Gly | Leu | Arg | Gly | Tyr | Arg | Ile |
| | | | | 245 | | | | | 250 | | | | | 255 | |
| Gly | Gly | Ala | Ser | Ile | Ser | Glu | Leu | His | Cys | Asn | Phe | Met | Ile | Asn | Asn |
| | | | 260 | | | | | 265 | | | | | 270 | | |
| Gly | Asn | Ala | Thr | Ala | Lys | Asp | Leu | Glu | Asp | Leu | Gly | Asn | Phe | Val | Arg |
| | | 275 | | | | | 280 | | | | | 285 | | | |
| Gln | Lys | Val | Phe | Glu | Asp | Ser | Gly | Val | Glu | Leu | Asn | Trp | Glu | Ile | Lys |
| | 290 | | | | | 295 | | | | | 300 | | | | |
| Arg | Ile | Gly | Lys | Tyr | Val | | | | | | | | | | |
| 305 | | | | | 310 | | | | | | | | | | |

```
<210> SEQ ID NO 9
<211> LENGTH: 341
<212> TYPE: PRT
<213> ORGANISM: Haemophilus influenzae

<400> SEQUENCE: 9
```

| | | | | | | | | | | | | | | | |
|---|---|---|---|---|---|---|---|---|---|---|---|---|---|---|---|
| Met | Gln | Asn | Leu | Gln | Pro | Phe | His | Thr | Phe | His | Ile | Gln | Ser | Asn | Ala |
| 1 | | | | 5 | | | | | 10 | | | | | 15 | |

Arg Glu Ile Ile Glu Ala His Ser Ile Glu Gln Leu Gln Gln Val Trp
            20                  25                  30

Ala Asn Ser Lys Ser Glu Asn Leu Pro Thr Leu Phe Leu Gly Gln Gly
        35                  40                  45

Ser Asn Val Leu Phe Leu Asp Asp Phe Asn Gly Ile Val Ile Leu Asn
    50                  55                  60

Arg Leu Met Gly Ile Thr His Glu Gln Asp Ala Asn Phe His Tyr Leu
65                  70                  75                  80

His Val Asn Gly Gly Glu Asn Trp His Lys Leu Val Glu Trp Ser Ile
                85                  90                  95

Asn Asn Gly Ile Tyr Gly Leu Glu Asn Leu Ala Leu Ile Pro Gly Cys
            100                 105                 110

Ala Gly Ser Ala Pro Ile Gln Asn Ile Gly Ala Tyr Gly Val Glu Phe
        115                 120                 125

Lys Asp Val Cys Asp Tyr Val Glu Val Leu Asn Leu Asn Thr Asn Glu
130                 135                 140

Thr Phe Arg Leu Asp Thr Glu Gln Cys Glu Phe Gly Tyr Arg Glu Ser
145                 150                 155                 160

Ile Phe Lys His Arg Tyr Gln Gln Gly Tyr Val Ile Thr Ala Val Gly
                165                 170                 175

Leu Lys Leu Lys Lys Asp Trp Gln Pro Ile Leu Lys Tyr Gly Ser Leu
            180                 185                 190

Val Glu Phe Asp Pro Lys Thr Val Thr Ala Lys Gln Ile Phe Asp Glu
        195                 200                 205

Val Cys His Ile Arg Gln Ser Lys Leu Pro Asp Pro Asn Glu Val Gly
    210                 215                 220

Asn Ala Gly Ser Phe Phe Lys Asn Pro Val Val Ser Ser Glu His Phe
225                 230                 235                 240

Glu Glu Ile Lys Lys His His Glu Asn Leu Pro His Phe Pro Gln Ala
                245                 250                 255

Asp Gly Ser Val Lys Leu Ala Ala Gly Trp Leu Ile Asp Gln Cys Asn
            260                 265                 270

Leu Lys Gly Phe Gln Ile Gly Gly Ala Ala Val His Lys Lys Gln Ala
        275                 280                 285

Leu Val Leu Ile Asn Lys Asn Gly Ala Thr Gly Gln Asp Val Val Lys
    290                 295                 300

Leu Ala His His Val Arg Gln Thr Val Ala Glu Lys Phe Gly Val Tyr
305                 310                 315                 320

Leu Gln Pro Glu Val Arg Phe Ile Ser Ala Thr Gly Glu Val Asn Ser
                325                 330                 335

Glu Gln Ile Ile Thr
            340

<210> SEQ ID NO 10
<211> LENGTH: 342
<212> TYPE: PRT
<213> ORGANISM: Salmonella typhimurium

<400> SEQUENCE: 10

Met Thr His Ser Leu Lys Pro Trp Asn Thr Phe Gly Ile Asp His Cys
1               5                   10                  15

Ala Lys His Ile Val Cys Ala Glu Asn Glu Gln Gln Leu Leu Ser Ala
            20                  25                  30

Trp Gln Gln Ala Thr Arg Glu Gly Leu Pro Val Met Ile Leu Gly Glu
        35                  40                  45

-continued

```
Gly Ser Asn Val Leu Phe Leu Glu Asn Tyr Ala Gly Thr Val Ile Leu
        50                  55                  60

Asn Arg Leu Lys Gly Ile Glu Val Asn Glu Thr Ala Asp Ala Trp His
 65                  70                  75                  80

Leu His Val Gly Ala Gly Glu Asn Trp His Gln Leu Val Arg Tyr Ala
                 85                  90                  95

Leu Asp Asn Asn Met Pro Gly Leu Glu Asn Leu Ala Leu Ile Pro Gly
                100                 105                 110

Cys Val Gly Ser Ser Pro Ile Gln Asn Ile Gly Ala Tyr Gly Val Glu
                115                 120                 125

Leu Gln Arg Val Cys Asp Tyr Val Asp Cys Val Glu Leu Glu Thr Gly
        130                 135                 140

Lys Arg Leu Arg Leu Ser Ala Ala Glu Cys Arg Phe Gly Tyr Arg Asp
145                 150                 155                 160

Ser Ile Phe Lys Asn Glu Tyr Gln Asp Arg Val Ala Ile Val Ala Val
                165                 170                 175

Gly Leu Arg Leu Ser Lys Gln Trp Gln Pro Val Leu Thr Tyr Gly Asp
                180                 185                 190

Leu Thr Cys Leu Asp Pro Lys Thr Val Thr Ala Gln Val Phe Asp
        195                 200                 205

Ala Val Cys His Met Arg Thr Thr Lys Leu Pro Asp Pro Lys Val Asn
        210                 215                 220

Gly Asn Ala Gly Ser Phe Phe Lys Asn Pro Val Val Ala Ala Asp Ile
225                 230                 235                 240

Ala Met Glu Leu Leu Glu Arg Phe Pro Asn Ala Pro His Tyr Pro Gln
                245                 250                 255

Ala Asp Gly Ser Val Lys Leu Ala Ala Gly Trp Leu Ile Asp Gln Cys
                260                 265                 270

Gln Leu Lys Gly Val Thr Ile Gly Gly Ala Ala Val His Arg Gln Gln
        275                 280                 285

Ala Leu Val Leu Ile Asn Ala Asn Asp Ala Thr Ser Lys Asp Val Val
        290                 295                 300

Ala Leu Ala His His Val Arg Gln Lys Val Gly Glu Lys Phe Asn Val
305                 310                 315                 320

Trp Leu Glu Pro Glu Val Arg Phe Ile Gly Arg Ser Gly Glu Val Asn
                325                 330                 335

Ala Val Glu Ser Ile Ala
                340

<210> SEQ ID NO 11
<211> LENGTH: 351
<212> TYPE: PRT
<213> ORGANISM: Bordetella pertussis

<400> SEQUENCE: 11

Met Ser Thr Val Pro Ala Arg Ile Glu Pro Val Ala Pro Leu Ala Pro
 1               5                  10                  15

Gln Ala Gln Asp Leu Arg Cys Phe Asn Thr Leu Gly Leu Ala Ser His
                20                  25                  30

Ala Pro Ala Phe Val Ala Leu Thr Glu Pro Ser Gln Leu Pro Ala Leu
        35                  40                  45

Ser Ala Leu Ala Pro Arg Phe Arg Gln Leu Val Leu Gly Gly Gly
        50                  55                  60

Ser Asn Val Val Leu Pro Ala Ser Ile Asp Gly Leu Val Ala Gln Val
 65                  70                  75                  80
```

```
Arg Leu Pro Gly Val Arg Leu Val Gly Gln Cys Ala Asp Ala Trp Val
             85                  90                  95

Val Glu Ala Ala Ala Gly Glu Asn Trp His Gly Phe Val Thr Ala Cys
            100                 105                 110

Val Asp Asn Gly Trp Asp Gly Leu Glu Asn Leu Ala Leu Ile Pro Gly
            115                 120                 125

Thr Val Gly Ala Ala Pro Val Gln Asn Ile Gly Ala Tyr Gly Val Glu
            130                 135                 140

Leu Ala Asp Arg Phe His Ser Leu Thr Ala Trp Asp Val Lys Gly Gly
145                 150                 155                 160

Arg Trp Val Glu Met Gly Ala Ala Glu Cys Arg Phe Ala Tyr Arg Asp
                165                 170                 175

Ser Phe Phe Lys His Gln Glu Pro Gly Ala Trp Val Ile Gly Ser Val
            180                 185                 190

Arg Phe Ala Leu Pro Arg Pro Trp Gln Pro Val Leu Asp Tyr Pro Asp
            195                 200                 205

Leu Gln Arg His Ala Ala Leu Asp Gly Ala Ala Pro Thr Ala Arg Ala
    210                 215                 220

Val Tyr Asp Ala Val Cys Ala Ile Arg Arg Ala Lys Leu Pro Asp Pro
225                 230                 235                 240

Ala Val Val Gly Asn Ala Gly Ser Phe Phe Lys Asn Pro Leu Val Asp
            245                 250                 255

Ala Gly Thr Arg Gln Ala Leu Leu Gly Arg Phe Pro Gly Leu Val Ser
            260                 265                 270

Tyr Pro Gln Pro Asp Gly Arg Tyr Lys Leu Ala Ala Gly Trp Leu Ile
        275                 280                 285

Asp Gln Cys Gly Trp Lys Gly Arg Gln Leu Gly Ala Ala Gly Val His
    290                 295                 300

Asp Arg Gln Ala Leu Val Leu Val Asn Arg Gly Gly Ala Gln Ala Arg
305                 310                 315                 320

Asp Ile Met Ala Leu Ala Ala Ile Gln Gly Asp Val Glu Arg Arg
            325                 330                 335

Tyr Gly Val Arg Leu Glu Pro Glu Pro Val Val Val Pro Ala Arg
            340                 345                 350
```

CRYSTALLIZATION AND STRUCTURE DETERMINATION OF STAPHYLOCOCCUS AUREUS UDP-N-ACETYLENOLPYRUVYLGLUCOSAMINE REDUCTASE (S. AUREUS MURB)

This application claims the benefit of U.S. Provisional Application Serial No. 60/147,164 filed Aug. 4, 1999, which is incorporated herein by reference in its entirety.

FIELD OF THE INVENTION

This invention relates to the crystallization and structure determination of Staphylococcus aureus UDP-N-acetylenolpyruvylglucosamine reductase (S. aureus MurB).

BACKGROUND OF THE INVENTION

Reports of an increase in antibiotic resistant bacteria have stimulated efforts to find new classes of therapeutic agents that will prevent society from entering a "post-antibiotic age." Historically, three important cellular functions have been the major targets of antibiotics—cell wall biosynthesis, DNA replication, and protein translation. The biosynthesis of the bacterial cell wall, in particular the peptidoglycan polymer, is a particularly attractive target since this flexible structure provides protection for the cell against osmotic lysis. To date, most of the therapeutic agents discovered that target cell wall biosynthesis inhibit the later stages of peptidoglycan biosynthesis at the point where interstrand cross linking occurs between the peptide chains. Recent efforts have been directed toward purifying and characterizing all the enzymes in the peptidoglycan biosynthetic pathway with an eye toward designing novel enzyme inhibitors of these essential targets.

Bacterial peptidoglycan is a polymer which includes a repeating disaccharide subunit of N-acetylglucosamine and N-acetylmuramic acid and an extended four to five residue amino acid chain. The first step toward creating this peptidoglycan polymer involves the formation of UDP-N-acetylmuramic acid from UDP-N-acetylglucosamine by the enzymes MurA and MurB. MurA catalyzes the first stage of this transformation by transferring the enolpyruvate moiety of phosphoenolpyruvate to the 3' hydroxyl of UDP-N-acetylglucosamine with the release of inorganic phosphate. The resulting product, enolpyruvyl-UDP-N-acetylglucosamine (EP-UDPGlcNAc), undergoes a reduction catalyzed by the MurB enzyme by utilizing one equivalent of NADPH and a solvent derived proton. This two electron reduction creates the lactyl ether of UDP-N-acetylmuramic acid upon which a five residue peptide chain is built. Construction of this pentapeptide is catalyzed in a nonribosomal fashion by the enzymes MurC, MurD, MurE, and MurF (FIG. 1) in both Gram negative bacteria such as Escherichia coli and Gram positive bacteria such as Staphylococcus aureus. The resulting UDP-N-acetylmuramyl pentapeptide is subsequently attached to an undecaprenyl lipid moiety by MraY and joined to another sugar, UDP-N-acetylglucosamine by MurG. In Staphylococci the next steps of peptidoglycan biosynthesis involve another family of enzymes, FemX, FemA, and FemB which create a pentaglycine strand in a stepwise fashion on the amino terminus of the lysine side chain. This extended Lys-Gly$_5$ chain serves as the interstrand bridge between nearby peptide strands. Crosslinking between strands can then occur between the lysine-pentapeptide bridge and the carbonyl of the fourth residue (D-Ala) with release of the terminal D-Ala in a transpeptidation step catalyzed by penicillin binding proteins.

While several laboratories have characterized some of the peptidoglycan biosynthetic enzymes for E. coli little biochemistry or structural biology has been carried out on these enzymes in a clinically relevant Gram positive organism. Interest in the molecular mechanisms of peptidoglycan biosynthesis in Gram positive organisms has increased in recent years as methicillin resistant S. aureus strains have surfaced that have acquired resistance to the antibiotic vancomycin.

SUMMARY OF THE INVENTION

In one aspect, the present invention provides a method for crystallizing an S. aureus MurB molecule or molecular complex that includes preparing purified S. aureus MurB at a concentration of about 1 mg/ml to about 50 mg/ml and crystallizing S. aureus MurB from a solution comprising about 1 wt. % to about 50 wt. % PEG, 0 wt. % to about 40 wt. % DMSO, about 100 mM to about 1 M ammonium or lithium sulfate, about 0 mM to about 20 mM 2-mercaptoethanol, about 0.005 mM to about 40 mM EP-UDPGlcNAc substrate, and buffered to a pH of about 5 to about 8.

In another aspect, the present invention provides crystalline forms of an S. aureus MurB molecule. In one embodiment, a crystal of an S. aureus MurB is provided having the trigonal space group symmetry I2$_1$3.

In another aspect, the present invention provides a scalable three dimensional configuration of points derived from structure coordinates of at least a portion of an S. aureus MurB molecule or molecular complex. In one embodiment, the scalable three dimensional set of points is derived from structure coordinates of at least the backbone atoms of the amino acids representing a FAD and/or substrate binding pocket of an S. aureus MurB molecule or molecular complex. In another embodiment, the scalable three dimensional set of points is derived from structure coordinates of at least a portion of a molecule or a molecular complex that is structurally homologous to an S. aureus MurB molecule or molecular complex. On a molecular scale, the configuration of points derived from a homologous molecule or molecular complex have a root mean square deviation of less than about 1.0 Å from the structure coordinates of the molecule or complex.

In another aspect, the present invention provides a molecule or molecular complex that includes at least a portion of an S. aureus MurB FAD and/or substrate binding pocket. In one embodiment, the S. aureus MurB FAD binding pocket includes the amino acids listed in Table 1, preferably the amino acids listed in Table 2, and more preferably the amino acids listed in Table 3, the FAD binding pocket being defined by a set of points having a root mean square deviation of less than about 1.7 Å, preferably less than about 1.0 Å, from points representing the backbone atoms of the amino acids. In another embodiment, the S. aureus MurB substrate binding pocket includes the amino acids listed in Table 4, preferably the amino acids listed in Table 5, and more preferably the amino acids listed in Table 6, the substrate binding pocket being defined by a set of points having a root mean square deviation of less than about 1.0 Å from points representing the backbone atoms of the amino acids.

TABLE 1

Residues near the FAD binding site in *S. aureus* MurB
Identified residues 4Å away from the FAD

| | | | | | | | |
|---|---|---|---|---|---|---|---|
| TYR | 42 | LEU | 98 | TYR | 149 | VAL | 199 |
| TYR | 77 | SER | 115 | MET | 150 | ARG | 225 |
| LEU | 78 | ILE | 140 | ALA | 152 | GLN | 229 |
| GLY | 79 | PRO | 141 | GLY | 153 | LEU | 231 |
| ASN | 80 | GLY | 142 | ALA | 154 | SER | 235 |
| GLY | 81 | SER | 143 | ARG | 188 | GLY | 237 |
| SER | 82 | GLY | 145 | ILE | 192 | PHE | 274 |
| ASN | 83 | GLY | 146 | LEU | 197 | ARG | 310 |
| ILE | 84 | ALA | 147 | VAL | 198 | | |

TABLE 2

Residues near the FAD binding site in *S. aureus* MurB
Identified residues 7Å away from FAD

| | | | | | | | |
|---|---|---|---|---|---|---|---|
| THR | 41 | LEU | 99 | VAL | 148 | LEU | 200 |
| TYR | 42 | SER | 115 | TYR | 149 | GLU | 201 |
| THR | 43 | GLY | 116 | MET | 150 | ARG | 225 |
| THR | 76 | ALA | 117 | ASN | 151 | GLN | 229 |
| TYR | 77 | ILE | 119 | ALA | 152 | PRO | 230 |
| LEU | 78 | PHE | 136 | GLY | 153 | LEU | 231 |
| GLY | 79 | GLY | 139 | ALA | 154 | TYR | 233 |
| ASN | 80 | ILE | 140 | TYR | 155 | PRO | 234 |
| GLY | 81 | PRO | 141 | ARG | 188 | SER | 235 |
| SER | 82 | GLY | 142 | ILE | 192 | CYS | 236 |
| ASN | 83 | SER | 143 | GLN | 193 | GLY | 237 |
| ILE | 84 | ILE | 144 | HIS | 196 | SER | 238 |
| ILE | 85 | GLY | 145 | LEU | 197 | PHE | 274 |
| ILE | 96 | GLY | 146 | VAL | 198 | ARG | 310 |
| LEU | 98 | ALA | 147 | VAL | 199 | ILE | 312 |

TABLE 3

Residues near the FAD binding site in *S. aureus* MurB
Identified residues 10Å away

| | | | | | | | |
|---|---|---|---|---|---|---|---|
| LEU | 37 | SER | 100 | TYR | 155 | ARG | 225 |
| TYR | 40 | LEU | 101 | GLY | 156 | GLU | 226 |
| THR | 41 | ALA | 113 | GLY | 157 | LYS | 228 |
| TYR | 42 | GLY | 114 | GLU | 158 | GLN | 229 |
| THR | 43 | SER | 115 | VAL | 159 | PRO | 230 |
| LYS | 44 | GLY | 116 | LYS | 160 | LEU | 231 |
| THR | 45 | ALA | 117 | ALA | 166 | GLU | 232 |
| TYR | 52 | ALA | 118 | LEU | 167 | TYR | 233 |
| PRO | 55 | ILE | 119 | CYS | 168 | PRO | 234 |
| VAL | 61 | ILE | 120 | VAL | 169 | SER | 235 |
| VAL | 65 | GLU | 135 | ASN | 170 | CYS | 236 |
| VAL | 75 | PHE | 136 | LEU | 183 | GLY | 237 |
| THR | 76 | ALA | 137 | ASP | 186 | SER | 238 |
| TYR | 77 | CYS | 138 | TYR | 187 | VAL | 239 |
| LEU | 78 | GLY | 139 | ARG | 188 | SER | 268 |
| GLY | 79 | ILE | 140 | ASN | 189 | LYS | 270 |
| ASN | 80 | PRO | 141 | SER | 190 | HIS | 271 |
| GLY | 81 | GLY | 142 | ILE | 191 | GLY | 273 |
| SER | 82 | SER | 143 | ILE | 192 | PHE | 274 |
| ASN | 83 | ILE | 144 | GLN | 193 | MET | 275 |
| ILE | 84 | GLY | 145 | LYS | 194 | VAL | 276 |
| ILE | 85 | GLY | 146 | GLU | 195 | ASN | 277 |
| ILE | 86 | ALA | 147 | HIS | 196 | TYR | 286 |
| ILE | 91 | VAL | 148 | LEU | 197 | GLU | 308 |
| ILE | 94 | TYR | 149 | VAL | 198 | VAL | 309 |
| VAL | 95 | MET | 150 | VAL | 199 | ARG | 310 |
| ILE | 96 | ASN | 151 | LEU | 200 | ILE | 311 |
| SER | 97 | ALA | 152 | GLU | 201 | ILE | 312 |
| LEU | 98 | GLY | 153 | ALA | 202 | | |
| LEU | 99 | ALA | 154 | LEU | 221 | | |

TABLE 4

Residues near the EP-UDPGlcNAc binding site in *S. aureus* MurB
Identified residues 4Å away from EP-UDPGlcNAc

| | | | | | | | |
|---|---|---|---|---|---|---|---|
| TYR | 155 | GLN | 229 | GLN | 253 | PHE | 274 |
| TYR | 187 | GLY | 237 | GLN | 258 | FAD | 401 |
| ARG | 188 | SER | 238 | HIS | 271 | | |
| ARG | 225 | LYS | 250 | ALA | 272 | | |

TABLE 5

Residues near the EP-UDPGlcNAc binding site in *S. aureus* MurB
Identified residues 7Å away from EP-UDPGlcNAc

| | | | | | | | |
|---|---|---|---|---|---|---|---|
| SER | 82 | ARG | 188 | ARG | 242 | SER | 268 |
| ASN | 83 | ARG | 224 | PHE | 247 | THR | 269 |
| GLY | 139 | ARG | 225 | ALA | 248 | LYS | 270 |
| ILE | 140 | LYS | 228 | GLY | 249 | HIS | 271 |
| PRO | 141 | GLN | 229 | LYS | 250 | ALA | 272 |
| MET | 150 | CYS | 236 | LEU | 251 | GLY | 273 |
| GLY | 153 | GLY | 237 | ILE | 252 | PHE | 274 |
| ALA | 154 | SER | 238 | GLN | 253 | GLU | 308 |
| TYR | 155 | VAL | 239 | ASP | 254 | FAD | 401 |
| GLY | 156 | PHE | 240 | GLN | 258 | | |
| TYR | 187 | GLN | 241 | VAL | 267 | | |

TABLE 6

Residues near the EP-UDPGlcNAc binding site in *S. aureus* MurB
Identified residues 10Å away from EP-UDPGlcNAc

| | | | | | | | |
|---|---|---|---|---|---|---|---|
| TYR | 42 | TYR | 155 | SER | 238 | GLN | 258 |
| THR | 43 | GLY | 156 | VAL | 239 | GLY | 259 |
| GLY | 81 | GLY | 157 | PHE | 240 | VAL | 267 |
| SER | 82 | GLU | 158 | GLN | 241 | SER | 268 |
| ASN | 83 | TYR | 187 | ARG | 242 | TMR | 269 |
| ILE | 84 | ARG | 188 | PRO | 243 | LYS | 270 |
| PHE | 136 | LEU | 221 | HIS | 246 | HIS | 271 |
| ALA | 137 | ARG | 224 | PHE | 247 | ALA | 272 |
| CYS | 138 | ARG | 225 | ALA | 248 | GLY | 273 |
| GLY | 139 | GLU | 226 | GLY | 249 | PHE | 274 |
| ILE | 140 | SER | 227 | LYS | 250 | MET | 275 |
| PRO | 141 | LYS | 228 | LEU | 251 | ASN | 306 |
| GLY | 142 | GLN | 229 | ILE | 252 | ARG | 307 |
| MET | 150 | PRO | 230 | GLN | 253 | GLU | 308 |
| ASN | 151 | LEU | 231 | ASP | 254 | VAL | 309 |
| ALA | 152 | SER | 235 | SER | 255 | FAD | 401 |
| GLY | 153 | CYS | 236 | ASN | 256 | | |
| ALA | 154 | GLY | 237 | LEU | 257 | | |

In another aspect, the present invention provides molecules or molecular complexes that are structurally homologous to an *S. aureus* MurB molecule or molecular complex.

In another aspect, the present invention provides a machine readable storage medium including the structure coordinates of all or a portion of an *S. aureus* MurB molecule, molecular complex, a structurally homologous molecule or complex, including structurally equivalent structures, as defined herein, particularly an FAD or substrate binding pocket thereof, or a similarly shaped homologous binding pocket. A storage medium encoded with these data is capable of displaying on a computer screen, or similar viewing device, a three-dimensional graphical representation of a molecule or molecular complex which comprises a binding pocket or a similarly shaped homologous binding pocket.

In another aspect, the present invention provides a method for identifying inhibitors, ligands, and the like of an *S. aureus* MurB molecule by providing the coordinates of a molecule of *S. aureus* MurB to a computerized modeling system; identifying chemical entities that are likely to bind to or interfere with the molecule (e.g., screening a small molecule library); and, optionally, procuring or synthesizing and assaying the compounds or analogues derived therefrom for bioactivity. In another aspect, the present invention provides methods for designing inhibitors, ligands, and the like by providing the coordinates of a molecule of S. aureus MurB to a computerized modeling system; designing a chemical entity that is likely to bind to or interfere with the molecule; and, optionally, synthesizing the chemical entity and assaying the chemical entity for bioactivity. In another aspect, the present invention provides inhibitors and ligands designed by the above method. In one embodiment, a composition is provided that includes an inhibitor or ligand designed or identified by the above method. In another embodiment, the composition is a pharmaceutical composition.

In another aspect, the present invention provides a method involving molecular replacement to obtain structural information about a molecule or molecular complex of unknown structure. The method includes crystallizing the molecule or molecular complex, generating an x-ray diffraction pattern from the crystallized molecule or molecular complex, and applying at least a portion of the structure coordinates set forth in FIG. 4 to the x-ray diffraction pattern to generate a three-dimensional electron density map of at least a portion of the molecule or molecular complex.

In another aspect, the present invention provides a method for homology modeling an S. aureus MurB homolog.

Definitions

Two crystallographic data sets (with structure factors F) are considered isomorphous if, after scaling, $$\frac{\Delta F}{F} = \frac{\sum |F_1 - F_2|}{\sum F_1}$$

is less than about 35% for the reflections between 8 Å and 4 Å.

Abbreviations

The following abbreviations are used throughout this disclosure:

UDP-N-acetylenolpyruvylglucosamine reductase (MurB).
Uridine diphospho-N-acetylglucosamine (UDPGlcNAc).
Uridine diphospho-N-acetylglucosamine enolpyruvate (EP-UDPGlcNAc).
Uridine diphospho-N-acetylmuramic acid (UDPMurNAc).
Reduced β-nicotinamide adenine dinucleotide phosphate (NADPH).
Isopropylthio-β-D-galactoside (IPTG).
Dithiothreitol (DTT).
Flavin adenine dinucleotide (FAD).
Dimethyl sulfoxide (DMSO).
Multiple anomalous dispersion (MAD).

The following amino acid abbreviations are used throughout this disclosure:

A = Ala = Alanine
V = Val = Valine
T = Thr = Threonine
C = Cys = Cysteine

-continued

L = Leu = Leucine
I = Ile = Isoleucine
P = Pro = Proline
F = Phe = Phenylalanine
W = Trp = Tryptophan
M = Met = Methionine
G = Gly = Glycine
S = Ser = Serine
Y = Tyr = Tyrosine
N = Asn = Asparagine
Q = Gln = Glutamine
D = Asp = Aspartic Acid
E = Glu = Glutamic Acid
K = Lys = Lysine
R = Arg = Arginine
H = His = Histidine

BRIEF DESCRIPTION OF THE FIGURES

FIG. 2 shows an amino acid sequence alignment for recombinant S. aureus (SEQ ID NO:1, which includes the His$_6$ region) and E. coli MurB. Dots in the sequences indicate gaps inserted in order to optimize the alignment. Identical residues are indicate by | and similar residues are indicated by . and : symbols. Sequence alignment was performed using the program GAP (GCG Version 9, Genetics Computational Group, Madison, Wis.). Residues corresponding to the FAD binding region (domains 1 and 2) are overlined and those corresponding to the substrate binding region (domain 3) are dash underlined. Structural features that are present in the E. coli but not the S. aureus protein are boxed and were omitted from superpositions. In regions where there are significant deletions in the S. aureus protein compared to the E. coli protein, no significance should be given to the placement of the connecting residues in the S. aureus sequence. Protein sequences not observed due to disordered electron density for the N and C termini of S. aureus MurB are underlined.

"Atom" refers to the element whose coordinates are measured. The second column defines the number of the atom in the structure. The letters in the third column define the element. The fourth and fifth columns define the amino acid and the number of the amino acid in the structure, respectively.

"X, Y, Z" crystallographically define the atomic position of the element measured.

"Occ" is an occupancy factor that refers to the fraction of the molecules in which each atom occupies the position specified by the coordinates. A value of "1" indicates that each atom has the same conformation, i.e., the same position, in all molecules of the crystal.

"B" is a thermal factor that measures movement of the atom around its atomic center.

Figure 5A:
Figure 5B:

FIG. 5 shows ribbon diagrams of a) S. aureus MurB structure with bound FAD cofactor and b) E. coli MurB structure with bound FAD cofactor and EP-UDPGlcNAc substrate.

Figure 6A:
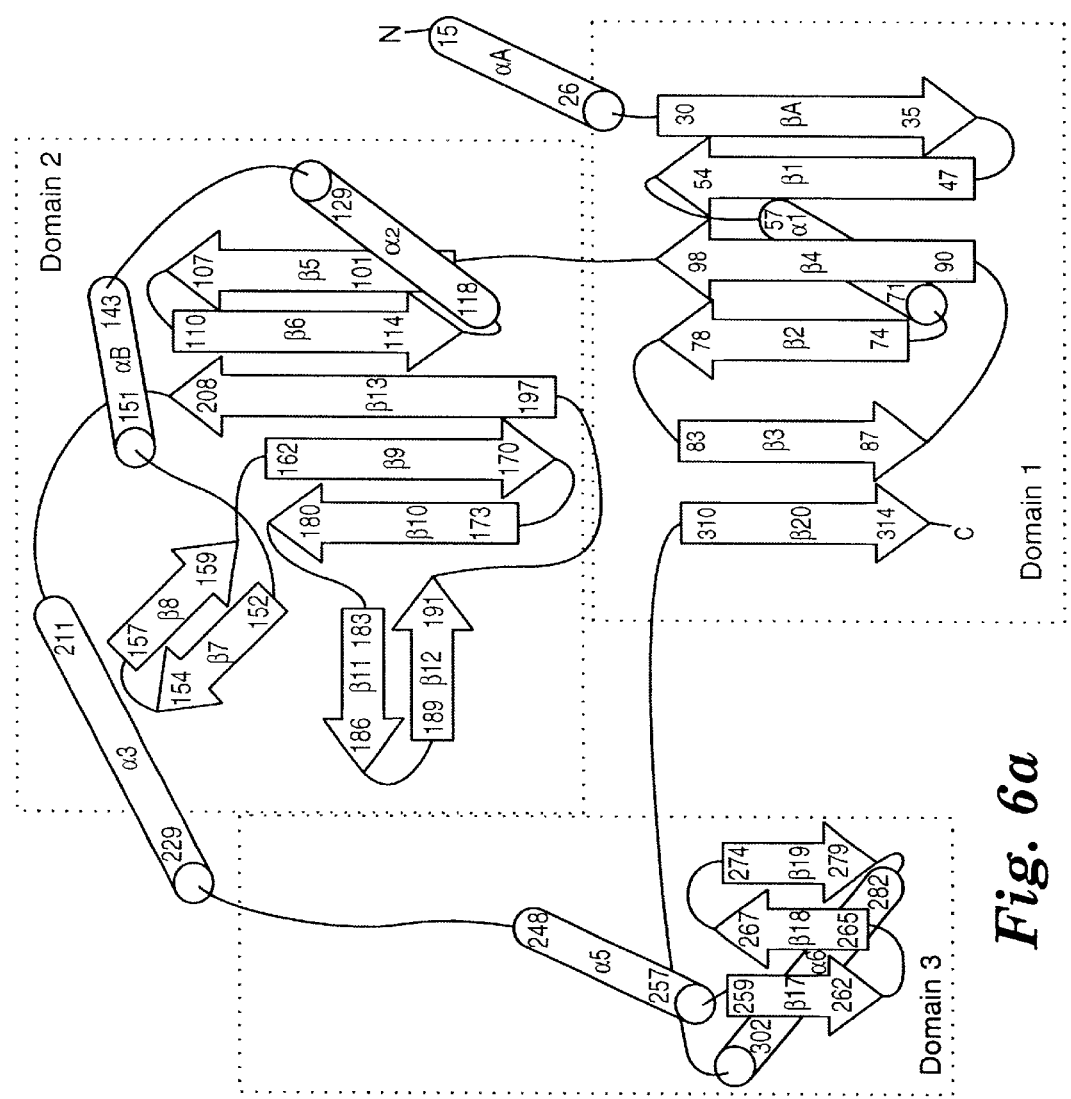
Figure 6B:
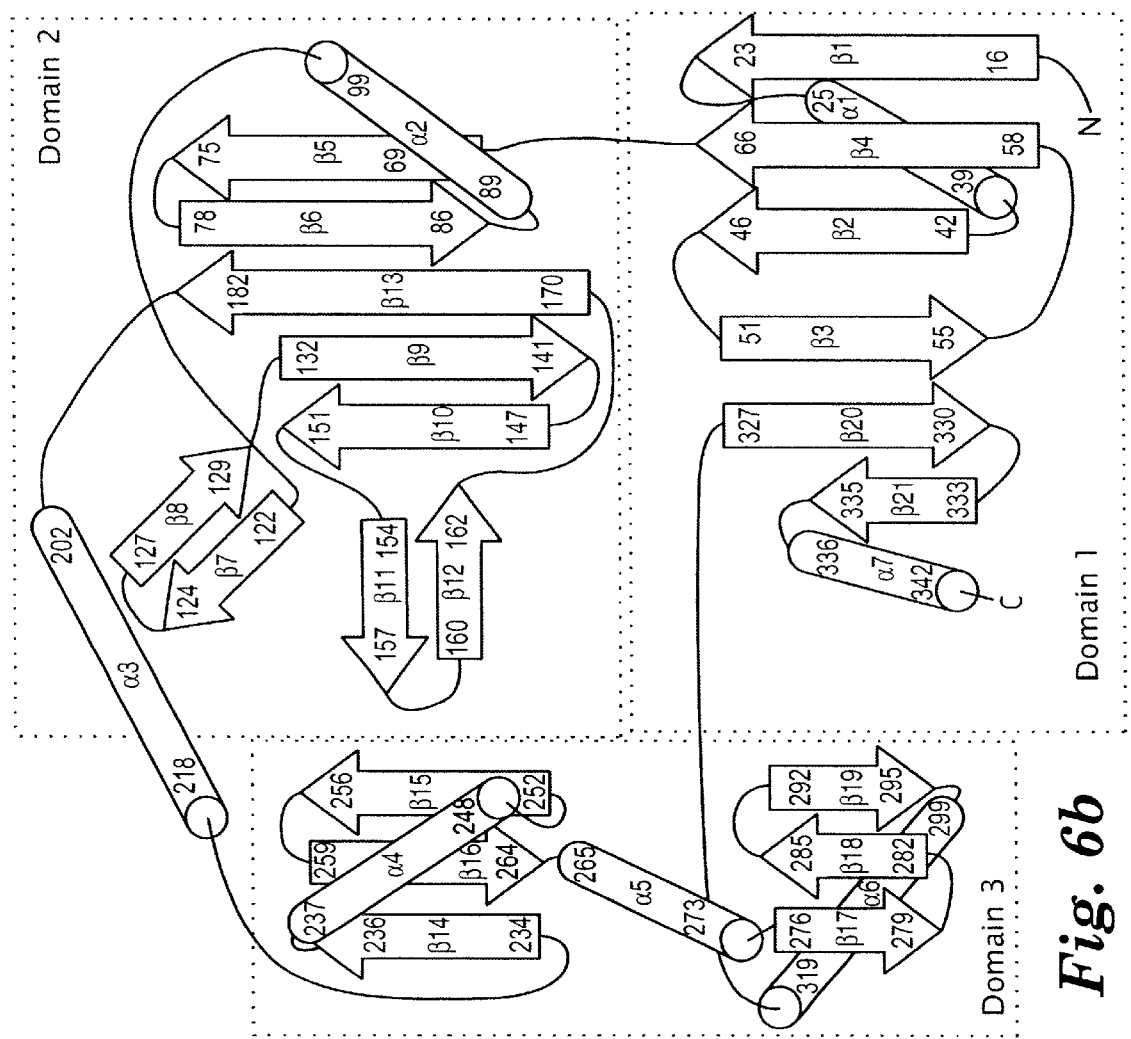

FIG. 6 shows secondary structure diagram for a) S. aureus MurB and b) E. coli MurB. The domain assignments are indicated with a dotted line. Naming of the secondary structure was made to correspond to the previously published *E. coli* MurB structure. Where new elements of secondary structure are present in the *S. aureus* structure, naming includes an "A."

FIG. 7 shows the superposition of *S. aureus* MurB (thick lines) and *E. coli* MurB (thin lines). Residues used for superpositions of the various domains are: a) All $C_\alpha$ atoms in common between the two structures. b) $C_\alpha$ atoms in domain 1 (lower right of molecule as shown in part a). The arrow points to the additional N-terminal α helix and β strand present in the *S. aureus* MurB structure. c) $C_\alpha$ atoms in domain 2 (upper center of molecule as shown in part a). The arrow points to the Tyr 190 loop in the *E. coli* MurB structure which is absent in the *S. aureus* MurB structure. d) $C_\alpha$ atoms in domain 3 (lower left of molecule as shown in part a). The arrow points to the single split βαββ fold in the *E. coli* MurB structure that is absent in the *S. aureus* MurB structure.

Figure 8:
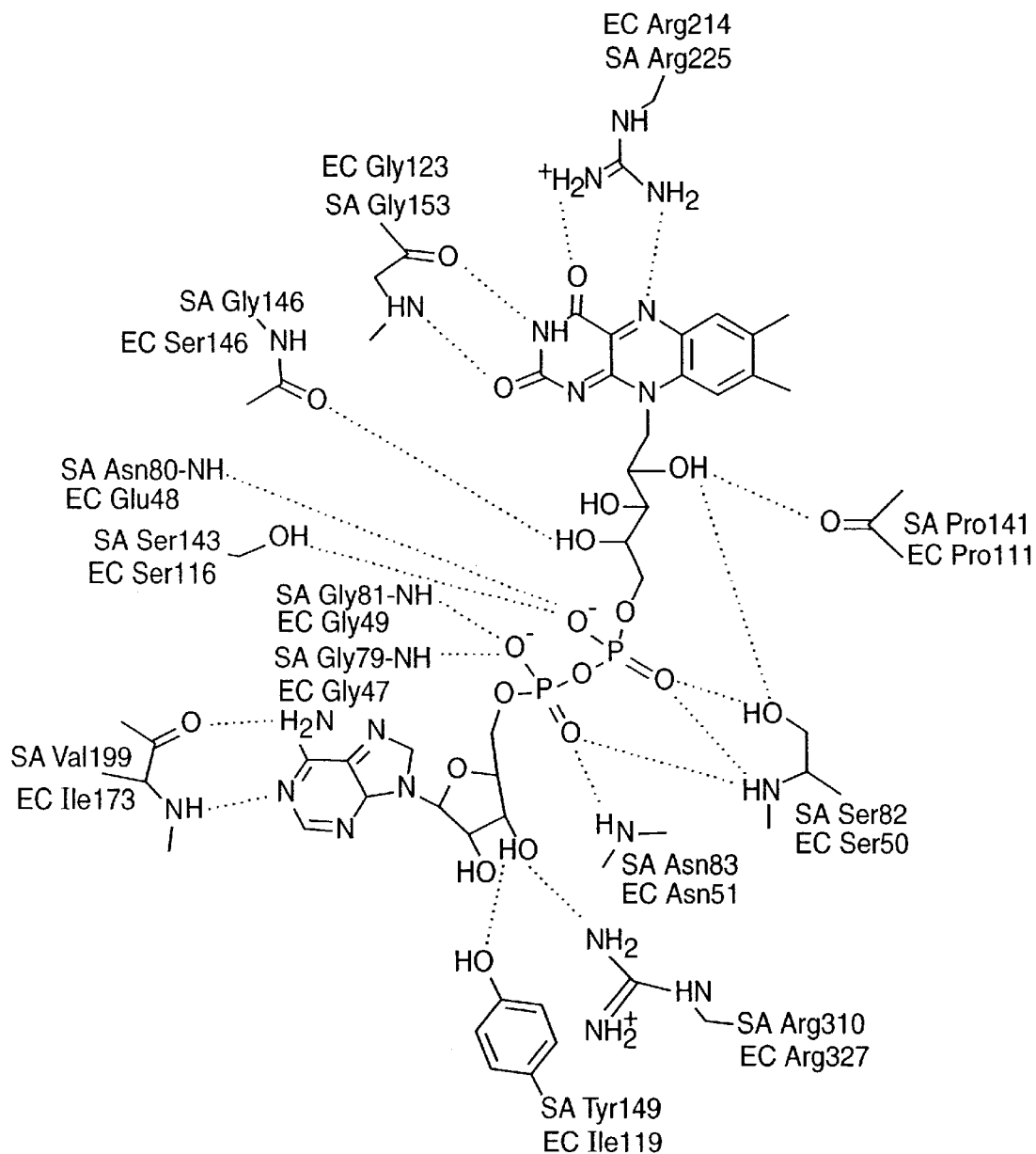

FIG. 8 shows a schematic view of side chain and main chain interactions between *S. aureus* MurB and the FAD cofactor. Residues for the *S. aureus* enzyme ("SA" prefix) are indicated adjacent to the amino acid along with the corresponding residues for the *E. coli* enzyme ("EC" prefix). Distances which would allow hydrogen bonds with the FAD are shown as dotted lines.

Figure 9:
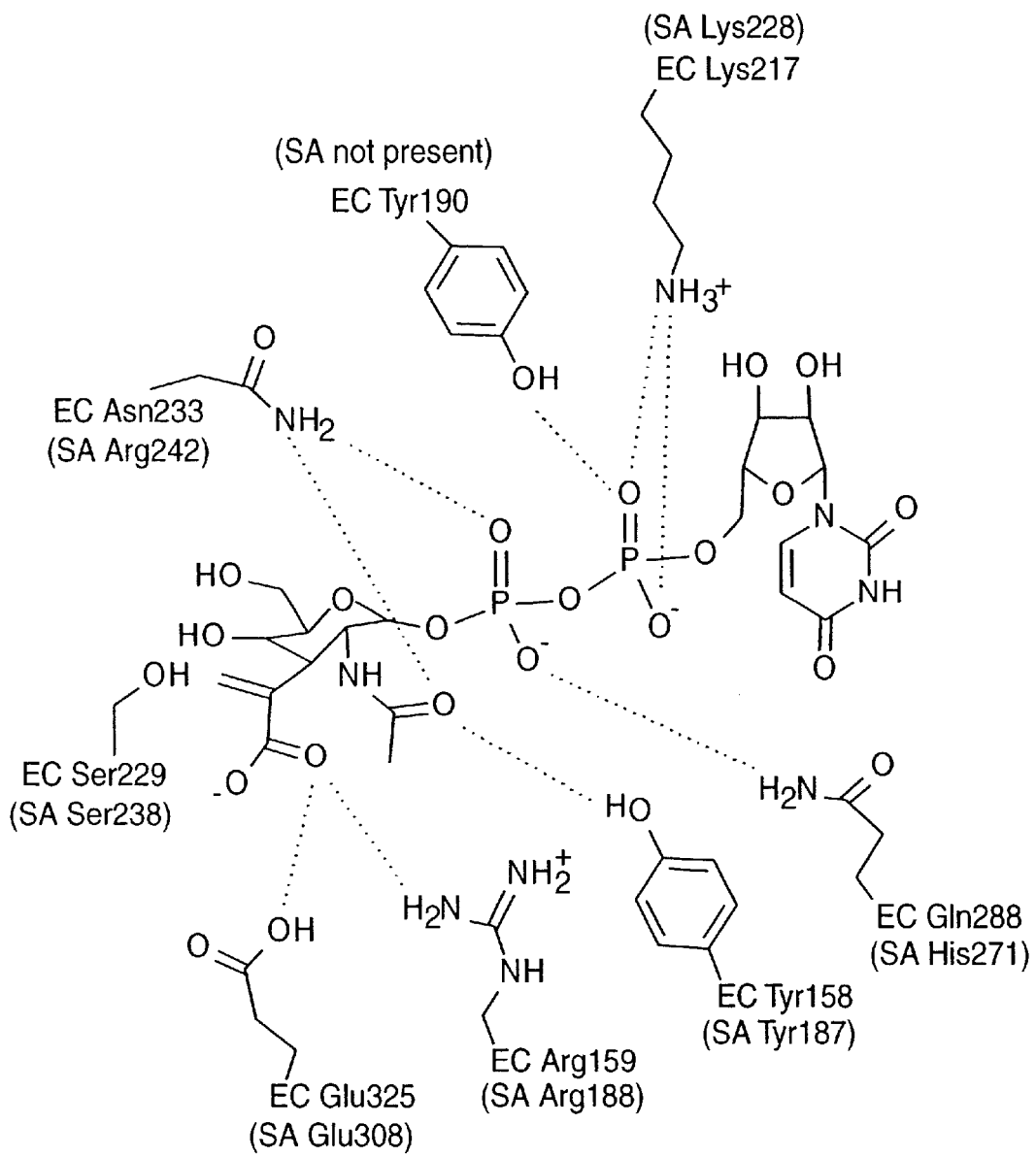

FIG. 9 shows proposed binding interactions of *S. aureus* MurB with the EP-UDPGlcNAc substrate ("SA prefix and parentheses) based on the *E. coli* MurB structure. Residues involved in EP-UDPGlcNAc binding in *E. coli* MurB are also shown ("EC" prefix).

FIG. 10 shows the sequence alignment of a representative sample of MurB sequences from Genbank: MURB_HELPY (*Helicobacter pylori*), MURB_AQUAE (*Aquifex aeolicus*), MURB_BACSU (*Bacillus subtilis*), MURB_BORBU (*Borrelia burgdorferi*), MURB_CHLPN (*Chlamydia pneumoniae*), MURB_RICPR (*Rickettsia prowazekii*), MURB_SAURE (*Staphylococcus aureus*), MURB_ECOLI (*Escherichia coli*), MURB_HAEIN (*Haemophilus influenzae*), MURB_SALTY (*Salmonella typhimurium*), and MURB_BORDE (*Bordetella pertussis*). Asterisks indicate the proposed active site residues involved in catalysis. Several other MurB sequences were not included in this alignment including *Treponema pallidum* MurB (class II MurB) and *Mycobacterium tuberculosis* MurB (class I MurB) because of additional insertions or deletions in these protein sequences which complicated the multiple sequence alignment.

Figure 11:
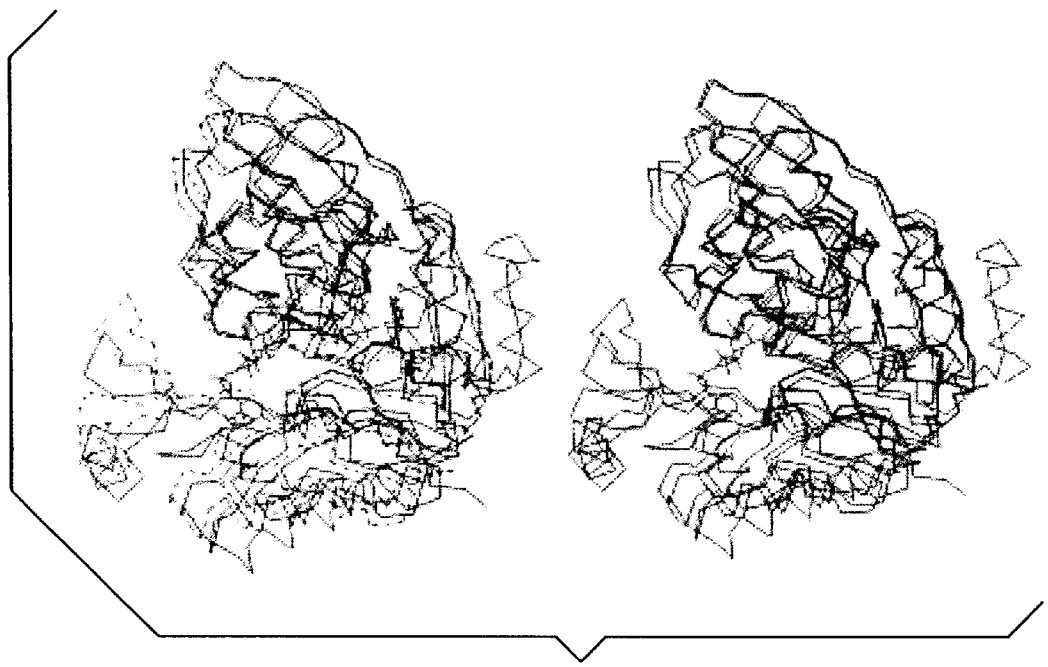

FIG. 11 shows $C_\alpha$ backbone traces from three MurB structures (superposition based on the flavin binding domains). The two *E. coli* MurB structures (substrate free *E. coli* MurB shown as dotted lines, EP-UDPGlcNAc bound MurB shown as thin lines) show that the substrate binding domain is actually closer to the flavin binding domain in the absence of substrate than when the substrate is bound. The *S. aureus* MurB structure reveals the greatest displacement of the substrate binding domain from the flavin domain of the three structures.

Figure 12:
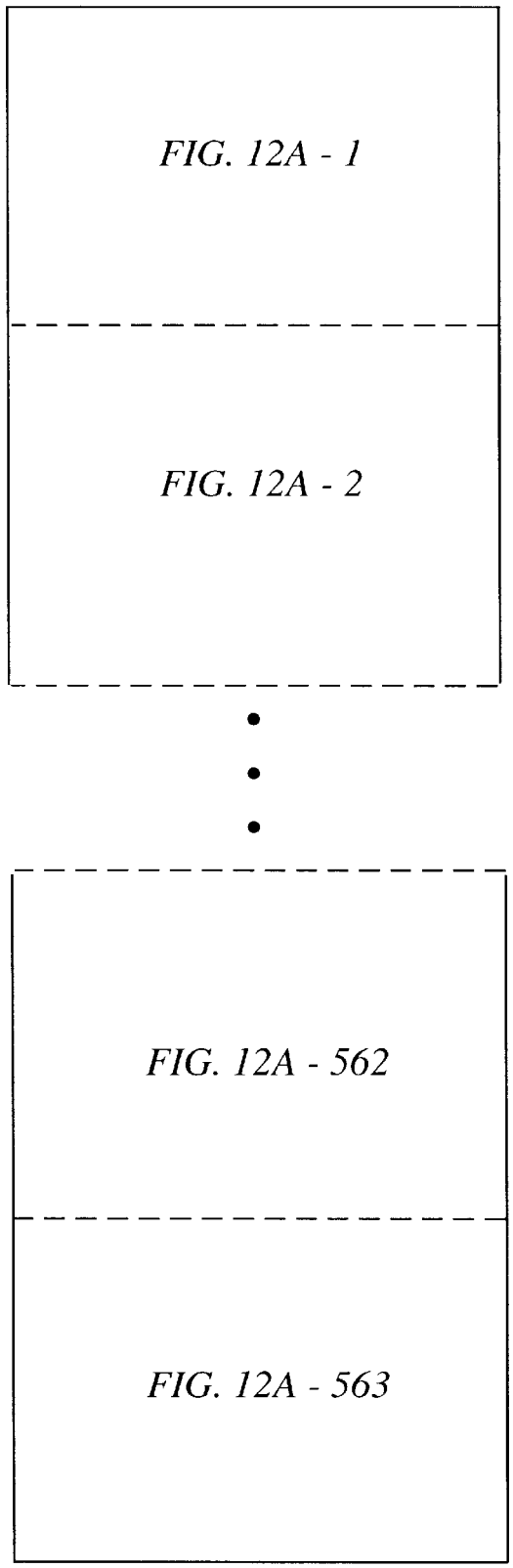

FIG. 12 lists the structure factors and multiple anomalous dispersion phases for the crystal structure of *S. aureus* MurB. "INDE" refers to the indices h, k, and l (columns 2, 3, and 4 respectively) of the lattice planes. "FOBS" refers to the structure factor of the observed reflections. "SIGMA" is the standard deviation for the observations. "PHAS" refers to the phase used for the observations. "FOM" refers to the figure of merit.

DETAILED DESCRIPTION OF THE INVENTION

Crystalline Form(s) and Method of Making

Applicants have produced crystals comprising *S. aureus* MurB that are suitable for x-ray crystallographic analysis. The three-dimensional structure of *S. aureus* MurB was solved using high resolution x-ray crystallography. Preferably, the crystal has the cubic space group $I2_13$. More preferably, the crystal comprises cubic shaped unit cells, each unit cell having the dimensions a=b=c=178.9±20 Å with a=β=γ=90°. The crystallized enzyme has one molecule in the asymmetric unit and includes a bound FAD cofactor.

Purified *S. aureus* MurB, preferably at a concentration of about 1 mg/ml to about 50 mg/ml, may be crystallized, for example, using the sitting or hanging drop procedure from a solution including about 1 wt. % to about 50 wt. % polyethylene glycol (PEG, preferably having a number average molecular weight between about 200 and about 20,000), 0 to about 40 wt. % DMSO, about 100 mM to about 1 M ammonium or lithium sulfate, about 0 mM to about 20 mM 2-mercaptoethanol, about 0.005 mM to about 40 mM EP-UDPGlcNAc substrate, and buffered to a pH of about 5 to about 8. Use of a buffer having a $pK_a$ of between about 4 and 9 is preferred. Variation in buffer and buffer pH as well as other additives such as PEG is apparent to those skilled in the art and may result in similar crystals.

Accordingly, one embodiment of the invention provides an *S. aureus* MurB or *S. aureus* MurB/ligand crystal.

The invention further includes an *S. aureus* MurB crystal or *S. aureus* MurB/ligand crystal that is isomorphous with an *S. aureus* MurB crystal characterized by a unit cell having the dimensions a=b=c=178.9±20 Å with a=β=γ=90°.

X-ray Crystallographic Analysis

Figure 1:
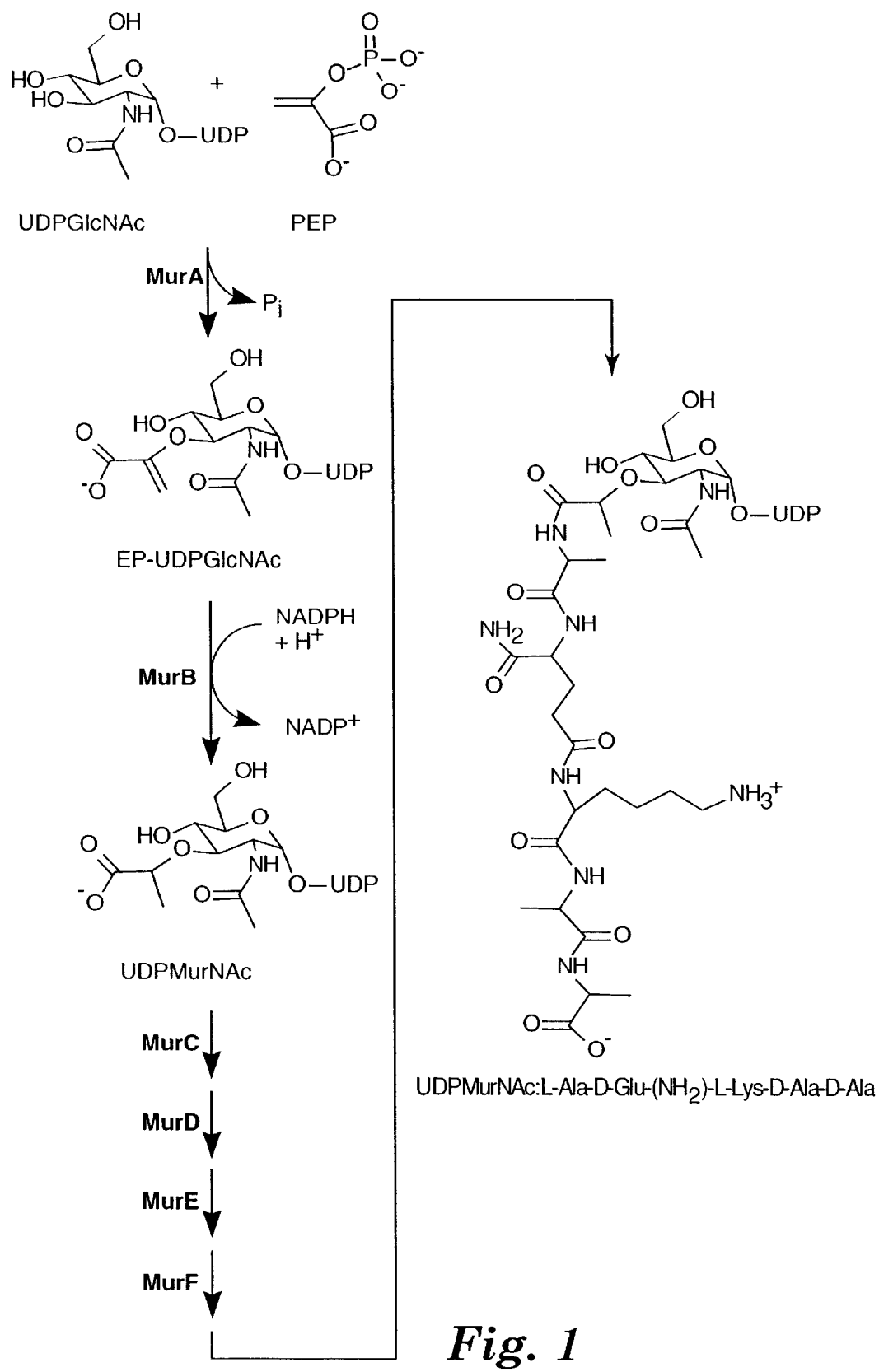
FIG. 1 shows the pathway for the biosynthesis of the UDP-N-acetylmuramyl pentapeptide, detailing the first two steps catalyzed by the enzymes MurA and MurB.
Figure 3A:
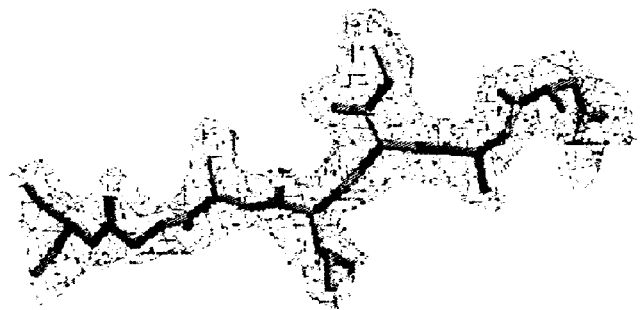
FIG. 3 shows a) solvent flattened MAD electron density map at 2.3 Å resolution for residues 110–115 with the final model and b) final $2F_o-F_c$ electron density map at 2.3 Å for residues 110–115 with the final model.
Figure 3B:

Crystals of *S. aureus* MurB in the cubic space group $I2_13$ with cell constants a=b=c=178.9 Å, α=β=γ=90° diffracted to 2.3 Å resolution. Initial attempts with molecular replacement using the *E. coli* MurB coordinates (T. E. Benson et al., *Nat. Struct. Biol.* 2, 644–53 (1995)) were unsuccessful despite the near 50% similarity with the *S. aureus* sequence (FIG. 2). Therefore, an independent set of phases was derived using multiple anomalous dispersion (MAD) with selenomethionine incorporated protein. *S. aureus* selenomethionine MurB was prepared by inhibiting endogenous methionine biosynthesis while supplementing the expressing cells with selenomethionine (G. D. Van Duyne et al., *J. Mol. Biol.* 229, 105–24(1993); T. E. Benson et al., *Nat. Struct. Biol.* 2, 644–53 (1995)). Methionine biosynthesis down regulation eliminates the need for transferring the protein expression vector into a met⁻ strain. This technique reduces the time and effort required for producing selenomethionine incorporated protein and results in near quantitative incorporation of selenomethionine into the overexpressed protein. Anomalous and dispersive difference Pattersons revealed the presence of four selenium sites. Solvent-flattened multiple anomalous dispersion phases to 2.3 Å revealed an exceptionally clear electron density map with no significant breaks in the main chain. A portion of the electron density map is shown in FIG. 3. The structure was refined to 2.3 Å resolution with an R-factor of 20.3% and a Free R-factor of 22.3% as described in Tables 7 and 8.

TABLE 7

Data collection and phasing statistics

|  | λ 1.0332 Å (12,000 eV) | λ 0.97939 Å (12,659.4 eV) | λ 0.97928 Å (12,660.8 eV) |
| --- | --- | --- | --- |
| Resolution | 2.3 Å | 2.3 Å | 2.3 Å |
| No. observations | 252,156 | 267,578 | 268,391 |
| No. unique refl. | 39,984 | 40,336 | 40,394 |
| % completeness | 94.4% | 95.2% | 95.3% |
| $R_{sym}$ | 7.5% | 9.5% | 9.4% |
| $R_{cullis}$ acentrics | — | 0.77 | 0.83 |
| $R_{cullis}$ anomalous | 0.99 | 0.84 | 0.84 |
| Phasing power |  |  |  |
| Centrics | — | 0.87 | 0.69 |
| acentrics | — | 0.77 | 0.83 |
| Mean figure of merit (to 2.3 Å resolution) |  |  |  |
| before solvent flattening |  | 0.464 |  |
| after solvent flattening |  | 0.605 |  |

TABLE 8

Refinement Statistics

|  | R-factor | Free R-factor | No. of reflections |
| --- | --- | --- | --- |
| 10–2.3 Å F ≧ 2σ | 20.3% | 22.3% | 33,156 |
| r.m.s deviation from ideal geometry |  | Bonds (Å) 0.008 | Angles(°) 1.37 |

|  | Number of atoms | Average B-factor |
| --- | --- | --- |
| Protein | 2345 | 28.4 |
| Waters | 213 | 36.6 |
| FAD | 53 | 23.6 |
| Total | 2611 | 29.0 |

Figure 4:
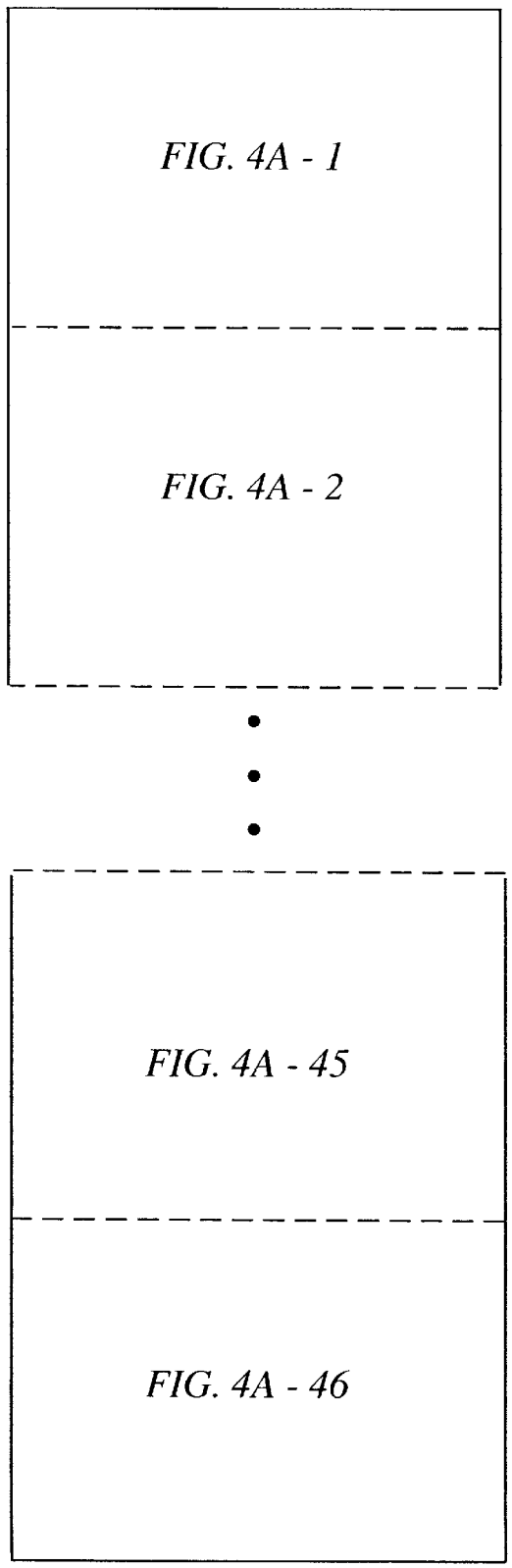
FIG. 4 lists the atomic structure coordinates for molecule S. aureus MurB as derived by x-ray diffraction from a crystal of that complex. The following abbreviations are used in FIG. 4.

Each of the constituent amino acids of S. aureus MurB is defined by a set of structure coordinates as set forth in FIG. 4. The term "structure coordinates" refers to Cartesian coordinates derived from mathematical equations related to the patterns obtained on diffraction of a monochromatic beam of x-rays by the atoms (scattering centers) of an S. aureus MurB complex in crystal form. The diffraction data are used to calculate an electron density map of the repeating unit of the crystal. The electron density maps are then used to establish the positions of the individual atoms of the S. aureus MurB protein or protein/ligand complex.

Slight variations in structure coordinates can be generated by mathematically manipulating the S. aureus MurB or S. aureus MurB/ligand structure coordinates. For example, the structure coordinates set forth in FIG. 4 could be manipulated by crystallographic permutations of the structure coordinates, fractionalization of the structure coordinates, integer additions or subtractions to sets of the structure coordinates, inversion of the structure coordinates or any combination of the above. Alternatively, modifications in the crystal structure due to mutations, additions, substitutions, and/or deletions of amino acids, or other changes in any of the components that make up the crystal, could also yield variations in structure coordinates. Such slight variations in the individual coordinates will have little effect on overall shape. If such variations are within an acceptable standard error as compared to the original coordinates, the resulting three-dimensional shape is considered to be structurally equivalent. Structural equivalence is described in more detail below.

It should be noted that slight variations in individual structure coordinates of the S. aureus MurB or S. aureus MurB/ligand complex, as defined above, would not be expected to significantly alter the nature of chemical entities such as ligands that could associate with the binding pockets. In this context, the phrase "associating with" refers to a condition of proximity between a chemical entity, or portions thereof, and an S. aureus thymidylate kinase molecule or portions thereof. The association may be non-covalent, wherein the juxtaposition is energetically favored by hydrogen bonding, van der Waals forces, or electrostatic interactions, or it may be covalent. Thus, for example, a ligand that bound to or interfered with the active site binding pocket of S. aureus MurB would also be expected to bind to or interfere with another binding pocket whose structure coordinates define a shape that falls within the acceptable error.

It will be readily apparent to those of skill in the art that the numbering of amino acids in other isoforms of S. aureus thymidylate kinase may be different than that of S. aureus thymidylate kinase expressed in E. coli.

Overview of the Structure

Figure 7A:
Figure 7B:
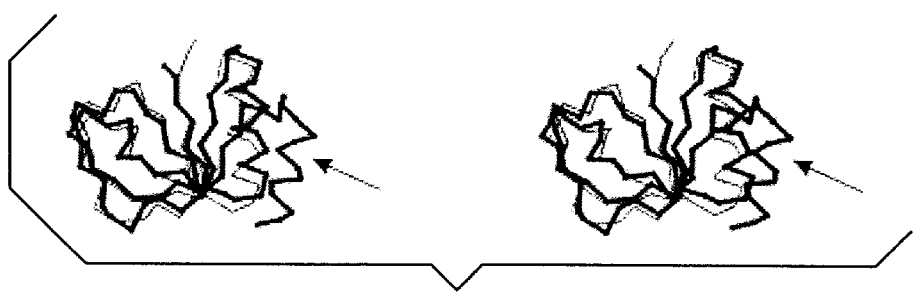
Figure 7C:
Figure 7D:
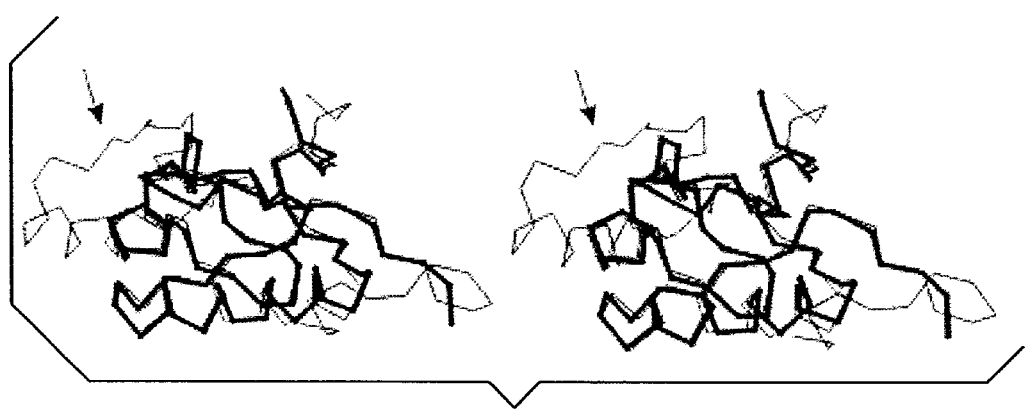

S. aureus MurB is composed of three domains (FIGS. 5 and 6). Domains 1 and 2 are responsible for binding of the flavin adenine dinucleotide (FAD) cofactor while domain 3 is responsible for substrate binding. The r.m.s. deviation for all $C_\alpha$ atoms in common between the E. coli and S. aureus structures (236 residues out of the 326 S. aureus residues) is 2.20 Å (FIG. 7a). Superpositions for each of the three domains in S. aureus compared to their respective domains in the E. coli enzyme resulted in slightly better superpositions for domains 2 and 3 (FIG. 7b–d). Domain 1 (residues 14–98) of S. aureus MurB has a r.m.s. deviation of 2.20 Å for the $C_\alpha$ atoms compared to E. coli MurB. The second domain of S. aureus MurB (residues 101–229) has a r.m.s. deviation of 1.80 Å for the $C_\alpha$ atoms of the corresponding residues in E. coli MurB. The r.m.s. deviation for domain 3 of the S. aureus enzyme (residues 230–316) is 1.05 Å for the $C_\alpha$ atoms corresponding to the portion of this domain present in the E. coli structure.

While the overall fold of the S. aureus MurB enzyme is similar to that of E. coli MurB, several exceptions indicate that the S. aureus MurB structure represents a significant structural variation for the UDP-N-acetylenolpyruvylglucosamine reductases. The first major difference is the additional 32 amino acids that are present at the N-terminus of S. aureus MurB which are not present in the E. coli enzyme. While only 18 of these amino acids are observed in the electron density map (the remaining 14 amino acids are disordered), these residues form an additional a helix (αA) and β strand (βA) at the beginning of the peptide chain. Similar secondary structure elements in S. aureus MurB have been given the corresponding names from E. coli MurB (T. E. Benson et al., Nat. Struct. Biol. 2, 644–53 (1995)) in order to facilitate the discussion and new elements of secondary structure have been assigned lettered names. The βA strand adds an antiparallel strand to the central parallel β barrel which forms the base of domain 1. This β barrel has an extremely hydrophobic core burying the side chains of residues Leu 37, Leu 78, Ile 84, Ile 86, Ile 91, Val 95, and Ile 312.

The second major structural difference in S. aureus MurB is the absence of the loop between β13 and α3 (residues 183 to 203 of E. coli MurB). To compensate for the loss of this loop, an additional turn of helix is added to α3 in order to make the connection between β13 and α3 in S. aureus MurB. This loop serves an important role in E. coli MurB by positioning Tyr 190 to interact directly with the α phosphate of the EP-UDPGlcNAc ligand and to close the active site upon substrate binding (T. E. Benson et al., *Structure* 4, 47–54 (1996)). Observations of the *S. aureus* MurB structure do not reveal any direct substitutes for Tyr 190 suggesting that this specific mechanism for substrate binding observed in *E. coli* MurB is not utilized in the *S. aureus* enzyme. In the *E. coli* MurB structure, the a phosphate of the EP-UDPGlcNAc also interacts with the side chain of Lys 217. This residue is conserved in the *S. aureus* MurB structure as residue Lys 228. Therefore, one would expect that the absence of Tyr 190 would lead to an increased importance for Lys 228 in the formation of a productive enzyme-substrate complex in *S. aureus* MurB. The third major structural difference is the deletion of a portion of the substrate binding domain in the *S. aureus* MurB protein structure. One of the α+β motifs present in the *E. coli* structure, the single split βαββ fold (β14, α4, β15, β16) is absent in the *S. aureus* MurB structure. This portion of the *E. coli* structure provides several van der Waals contacts with the EP-UDPGlcNAc ligand. In the absence of this portion of the substrate binding domain, the ligand binding surface on *S. aureus* MurB is notably more narrow.

Several minor differences in the main chain between the two structures are also observed. First, in the *E. coli* MurB, two residues in β5 and β6 are not found in the *S. aureus* MurB structure resulting in two shorter β strands for the *S. aureus* enzyme. Second, the hydrogen bonding distances and geometries for residues 143–151 in *S. aureus* MurB are consistent with a secondary structure assignment of an α helix (αB) for these residues in the core of the protein. This same region in the *E. coli* structure (residues 113–121) shows secondary structure similar to an α helix with allowed phi and psi angles, but with poor hydrogen bonding distances and geometries; therefore, this region was not assigned as an α helix in the original *E. coli* MurB structure (T. E. Benson et al., *Nat. Struct. Biol.* 2, 644–53 (1995)). Third, a single residue deletion in the *S. aureus* structure occurs in the loop between β9 and β10 leading to a shorter connection between these two strands. Finally, the last beta strand (β21) and alpha helix (α7) in the *E. coli* MurB structure are not observed in the *S. aureus* MurB structure. The exact secondary structure of these residues is unknown since the last nine residues of the C terminus of *S. aureus* MurB are disordered in the electron density map.

Flavin Cofactor Binding

The conserved protein fold of MurB in the *S. aureus* enzyme is particularly pronounced for the flavin binding portion of the molecule (domains 1 and 2—FIGS. 7*b,c*). Not only is the flavin binding fold conserved, but also the conformation of the flavin adenine dinucleotide ligand is nearly identical between the two structures (r.m.s. deviation for all of the cofactor atoms comparing the *S. aureus* FAD and the *E. coli* FAD is 0.30 Å). This FAD binding fold in both MurB structures is a member of a new superfamily of flavin adenine dinucleotide binding proteins (A. G. Murzin, *Cur. Op. Struct. Biol.* 6, 386–94 (1996)). The other members of this FAD binding protein family for which protein structures have been solved include p-cresol methylhydroxylase from *Pseudomonas putida* (F. S. Matthews et al., *Biochemistry* 30, 238–47 (1991)), vanillyl-alcohol oxidase from *Penicllium simplicissimum* (A. Mattevi et al., *Structure* 5, 907–20(1997)), and CO dehydrogenase from *Oligotropha carboxidovorans* (H. Dobbek et al., *Proc. Natl. Acad. Sci USA* 96,8884–89 (1999)).

The protein side chain and main chain interactions with the FAD cofactor found in the *S. aureus* enzyme are mostly similar to those interactions observed in *E. coli* MurB. The N5 and O4 of the isoalloxazine ring of the flavin adenine dinucleotide interact with the guanidinium moiety of Arg 225 in a manner similar to that observed for Arg 214 in the *E. coli* MurB structure (FIG. 8). The sequence and positional conservation of this arginine in the structure suggests that it plays a role in the binding of the flavin and stabilization of the reduced cofactor during catalysis. Two other interactions to the isoalloxazine ring (N3 and O2) are maintained by the main chain nitrogen and carbonyl oxygen of Gly 153. Interactions with the ribityl sugar moiety are also similar to those observed in the *E. coli* MurB. The carbonyl oxygen of Pro 141 and the hydroxyl group of Ser 82 make hydrogen bonds to the first hydroxyl group and the carbonyl of Gly 146 interacts with the third hydroxyl moiety. The extensive interactions between the protein and the diphosphoadenine portion of the molecule are also well conserved with the main chain atoms of residues 79–83 which include the Gly-X-Gly motif found in the Rossman fold and provide important stabilizing interactions with the two phosphates. Two serines (Ser 82 and Ser 143) again serve to make specific contacts with the β phosphate moiety, but using a geometry different from *E. coli* MurB. The placement of Ser 82 is conserved with respect to its counterpart in *E. coli* MurB (Ser 50), but Ser 143 is three residues away (one turn of α helix B) from the position corresponding to the *E. coli* MurB Ser 116. While this places the serine hydroxyl on the opposite site of the phosphate (when compared to the *E. coli* MurB), the hydrogen bonding interaction is maintained. Finally, two residues make contacts to the 3' hydroxyl of the ribityl sugar, Tyr 149 and Arg 310. The corresponding residues in *E. coli* MurB for Tyr 149 is Ile 149 which does not make any hydrogen bonds to the ribityl sugar, but does make hydrophobic interactions with this part of the flavin. The substitution of tyrosine in *S. aureus* MurB at this position allows for both hydrogen bonding and hydrophobic contacts.

Active Site Arrangement and Implications for Substrate Binding

The electron density map in the active site of *S. aureus* MurB reveals regions of disconnected electron density that did not clearly resemble the EP-UDPGlcNAc substrate despite the presence of the substrate in the crystallization conditions. Therefore, the exact location and interactions between *S. aureus* MurB and the EP-UDPGlcNAc and/or NADPH substrate in the active site cannot be determined at this time. Analysis of the packing in the crystal lattice reveals that a symmetry related molecule protrudes into the active site of *S. aureus* MurB in this crystal. Specifically, two strands of the major beta sheet (β5 and β6) are situated at the active site opening. Superimposing the *E. coli*-EP-UDPGlcNAc bound structure on the *S. aureus* MurB structure indicates that these strands from the symmetry related molecule would interfere with the binding of the uridine portion of the substrate. Many attempts were made to obtain a ligand bound crystal form of *S. aureus* MurB, but no crystallization conditions were identified which would support both crystallization of the protein and binding of EP-UDPGlcNAc.

Although this crystal form of *S. aureus* MurB does not contain either of the MurB substrates EP-UDPGlcNAc or NADPH, comparison of the *S. aureus* and *E. coli* structures reveals strict conservation of the active site residues. The three catalytic active site residues in *E. coli*, Arg 159 and Glu 325 that would stabilize the C2 acicarbanionic species and Ser 229 that would provide a proton to quench the intermediate, are strictly conserved in the *S. aureus* active site—Ser 238, Arg 188, and Glu 308 (FIG. 9) (T. E. Benson et al., *Nat. Struct. Biol.* 2, 644–53 (1995)). In addition, two residues that were shown to play a role in substrate binding in the *E. coli* enzyme are also strictly conserved in the active site of *S. aureus* MurB (Tyr 187 and Lys 288). Two other residues shown to be important for substrate binding—Asn 233 and Gln 288—are replaced in the *S. aureus* structure by Arg 242 and His 271 respectively. The only critical substrate binding residue that is not found in the *S. aureus* structure is the *E. coli* Tyr 190 which is absent due to the deletion of the loop between β13 and α3 in *S. aureus* protein as previously noted. The absence of this single residue does not appear to compromise the ability of the enzyme to bind substrate since all of the other hydrogen bond interactions observed in the *E. coli* MurB structure would be maintained.

A comparison of the two MurB structures reveals that the *S. aureus* MurB possesses the same general fold that was observed in the *E. coli* MurB structure—an α+β protein with three domains. Two of these domains create a binding site for the flavin adenine dinucleotide cofactor and the third domain participates in substrate binding. Based on the high similarity between the two protein sequences, a related fold was clearly expected. Yet it is not surprising that differences between the two structures are evident in the substrate binding regions of the enzymes, since the sequence alignment reveals regions of significant deletions. The most relevant deletions that occur in the *S. aureus* MurB structure involve portions of the enzyme that play an important part in the binding of EP-UDPGlcNAc in *E. coli* MurB. The loop between β13 and α3 in *E. coli* MurB contains Tyr 190 which undergoes a dramatic motion upon substrate binding. The absence of this loop and its key residue in the *S. aureus* structure suggests that ligand binding in this bacterial species has adapted to compensate for the loss of Tyr 190. The $K_m$ for EP-UDPGlcNAc with *S. aureus* MurB is 15 μM (S. Swaney, personal communication) which is of the same magnitude as the $K_m$ for EP-UDPGlcNAc with *E. coli* MurB. This kinetic parameter suggests that the loss of Tyr 190 has little impact on the enzyme's ability to bind substrate. It is also possible that charged residues from other parts of the molecule could play a role in ligand binding. Interestingly, the other significant deletion also involves a part of the enzyme involved in substrate binding—the single split βαββ fold (β14, α4, β15 and β16 in *E. coli* MurB). This portion of protein structure has a less specific purpose in the mechanism of action of MurB, but does serve to provide a surface on which the uridine portion of the EP-UDPGlcNAc substrate rests.

Although the MurB crystals were grown in the presence of the substrate EP-UDPGlcNAc, no interpretable electron density for the substrate was observed. The failure to obtain a substrate complex could be either the result of weak substrate binding to the enzyme under the conditions necessary for crystallization or the result of crystallization conditions which select for a crystal form that excludes substrate. Monitoring ligand binding by UV-visible spectroscopy shows the expected red shift of the flavin absorption spectrum associated with EP-UDPGlcNAc as observed with the *E. coli* MurB enzyme (T. E. Benson et al., *Biochemistry* 36, 796–805 (1997)) suggesting that the substrate should be bound to the oxidized form of the *S. aureus* MurB. When the initial crystals did not show the presence of substrate in the active site, higher concentrations of substrate were employed in an attempt to produce a substrate complex. Since the original crystallization buffer was at pH 6.5, crystals were also grown at pH 8.0 within the optimal pH range for the *S. aureus* MurB enzymatic activity. Unfortunately, neither of these changes resulted in formation of a substrate complex in the crystals that were obtained. These results strongly suggest that the crystal form which is favored during crystallization selects against preserving the *S. aureus* MurB-EP-UDPGlcNAc complex.

Placement of the EP-UDPGlcNAc substrate can be inferred from the *E. coli* MurB-EP-UDPGlcNAc structure. The active site for MurB is defined by residues which stabilize the intermediate produced when a hydride is transferred from N1 to C3 of the enolpyruvyl group and facilitate the quenching of this intermediate. Based on *S. aureus* MurB structure, a mechanism was proposed for stabilization of this acicarbanionic species by charge neutralization and/or by protonation. As in the *E. coli* model, two residues, Arg 188 and Glu 308, exist which could serve this mechanistic purpose. Similarly, Ser 238 corresponds to *E. coli* MurB Ser 229 which is proposed to serve as a general acid catalyst in conjunction with an active site water (T. E. Benson et al., *Biochemistry* 36, 806–11 (1997)). The Ser 238 hydroxyl is 6.3 Å away from N1 of the FAD cofactor in the *S. aureus* MurB structure. Since the corresponding serine hydroxyl is similarly positioned (6.1 Å from N1) in the *E. coli* MurB structure, it appears that *S. aureus* MurB is well-positioned for reduction of the enolpyruvyl group.

An analysis of available MurB sequences in Genbank provides increasing evidence that these three active site residues play critical roles in stabilization and reduction of the C2 acicarbanion intermediate during catalysis. In the sequence alignment shown in FIG. 10, the active site glutamate (Glu 308 in *S. aureus* MurB and Glu 325 in *E. coli* MurB) is strictly conserved. The active site arginine (Arg 188 in *S. aureus* MurB and Arg 159 in *E. coli* MurB) is conserved in all species with the exception of *Borrelia burgdorfei* MurB in which a conservative substitution to a lysine is made. The active site serine is equally well conserved across species with the only exception being the MurB sequence from *Chlamydia pneumoniae* where a conservative Cys substitution is present. This conservation of active site residues suggests that mechanistically the UDP-N-acetylenolpyruvylglucosamine reductases are equivalent with respect to the reduction of the enolpyruvyl group.

In contrast, these sequence alignments also suggest that there are at least two structural scaffolds for the MurB family. Comparison of the sequences from Genbank reveals that the *S. aureus* MurB is not the only MurB sequence in which the *E. coli* Tyr 190 loop and the single split βαββ fold from the substrate binding domain (β14, α4, β15 and β16 in *E. coli* MurB) are absent (FIG. 10). This striking similarity among sequences indicates that many of these MurBs from other species would adopt the *S. aureus* MurB type three-dimensional structure as opposed to the *E. coli* MurB type three-dimensional structure. Thus, the trend suggests that at least two distinct classes of MurB protein structures exist—that of the *E. coli* type (type I MurB) and that of the *S. aureus* type (type II MurB)—which distinguishes the construction of the substrate binding domain and the manner in which these enzymes bind their substrates.

This classification of two types of MurB consists not only of secondary structural elements that are present or absent, but also of how these structural elements define a mode of substrate binding. A comparison of the substrate domain positions between *S. aureus* MurB and the two forms of *E. coli* MurB (substrate free and EP-UDPGlcNAc bound forms) is shown in FIG. 11. This superposition reveals that *S. aureus* MurB's substrate binding domain is notably more displaced from domains 1 and 2 in either of the substrate free or the EP-UDPGlcNAc bound forms of *E. coli* MurB. While interactions between crystallographically related molecules hold domain 3 in this open conformation, this displacement reveals the flexibility of the enzyme to achieve an open conformation of the *S. aureus* enzyme with ready access to the ligand binding site. The process of binding ligand in the *S. aureus* MurB most likely involves closing of the enzyme by direct movement of domain 3 towards the flavin binding domains. In contrast, *E. coli* MurB facilitates ligand binding by an indirect mechanism involving the movement of domain 3 away from the flavin binding domain leading to the disruption of the stacking interaction between Tyr 190 and Tyr 254. This motion allows Tyr 190 to adopt a new rotameric configuration which provides a hydrogen bond to the a phosphate and closes off the active site from the solvent.

Binding Pockets/Active Sites/Other Structural Features

Applicants' invention has provided, for the first time, information about the shape and structure of the cofactor and substrate binding pockets of *S. aureus* MurB.

Binding pockets are of significant utility in fields such as drug discovery. The association of natural ligands or substrates with the binding pockets of their corresponding receptors or enzymes is the basis of many biological mechanisms of action. Similarly, many drugs exert their biological effects through association with the binding pockets of receptors and enzymes. Such associations may occur with all or any parts of the binding pocket. An understanding of such associations helps lead to the design of drugs having more favorable associations with their target, and thus improved biological effects. Therefore, this information is valuable in designing potential inhibitors of *S. aureus* MurB-like binding pockets, as discussed in more detail below.

A "molecular complex" means a protein in covalent or non-covalent association with a chemical entity or compound. The term "binding pocket" or "active site" as used herein, refers to a region of a molecule or molecular complex, that, as a result of its shape, favorably associates with another chemical entity. Thus, a binding pocket may include or consist of features such as cavities, surfaces, or interfaces between domains. Chemical entities that may associate with a binding pocket include, but are not limited to, cofactors, substrates, inhibitors, agonists, antagonists, etc.

The FAD binding pocket of *S. aureus* MurB is located on the interface between domains 1 and 2, and preferably includes the amino acids listed in Table 1, more preferably the amino acids listed in Table 2, and most preferably the amino acids listed in Table 3, as represented by the structure coordinates listed in FIG. 4. It will be readily apparent to those of skill in the art that the numbering of amino acids in other isoforms of *S. aureus* MurB may be different than that of recombinant *S. aureus* MurB expressed in *E. coli*. Alternatively, the FAD binding pocket of *S. aureus* MurB includes those amino acids whose backbone atoms are situated within about 4 Å, more preferably within about 7 Å, most preferably within about 10 Å, of one or more constituent atoms of a bound FAD cofactor or analog, as determined from the structure coordinates listed in FIG. 4. Alternatively, the FAD binding pocket comprises those amino acids whose backbone atoms are situated within a sphere centered on the coordinates representing the alpha carbon atom of residue Asn 80, the sphere having a radius of about 16 Å, preferably about 20 Å, and more preferably about 25 Å.

The substrate binding pocket of *S. aureus* MurB is located in domain 3, and preferably includes the amino acids listed in Table 4, more preferably the amino acids listed in Table 5, and most preferably the amino acids listed in Table 6, as represented by the structure coordinates listed in FIG. 4. Alternatively, the substrate binding pocket of *S. aureus* MurB includes those amino acids whose backbone atoms are situated within about 4 Å, more preferably within about 7 Å, most preferably within about 10 Å, of one or more constituent atoms of a bound substrate or inhibitor, as determined from the structure coordinates listed in FIG. 4. Alternatively, the substrate binding pocket comprises those amino acids whose backbone atoms are situated within a sphere centered on the coordinates representing the alpha carbon atom of residue Ser 238, the sphere having a radius of about 12 Å, preferably about 20 Å, and more preferably about 25 Å.

The amino acid constituents of an *S. aureus* MurB binding pocket as defined herein, as well as selected constituent atoms thereof, are positioned in three dimensions in accordance with the structure coordinates listed in FIG. 4. In one aspect, the structure coordinates defining the binding pocket of *S. aureus* MurB include structure coordinates of all atoms in the constituent amino acids; in another aspect, the structure coordinates of the binding pocket include structure coordinates of just the backbone atoms of the constituent atoms.

The term "*S. aureus* MurB-like binding pocket" refers to a portion of a molecule or molecular complex whose shape is sufficiently similar to at least a portion of a cofactor or substrate binding pocket of *S. aureus* MurB as to be expected to bind a structurally related cofactor such as FAD or structurally related substrates such EP-UDPGlcNAc and/or NADPH. A structurally equivalent binding pocket is defined by a root mean square deviation from the structure coordinates of the backbone atoms of the amino acids that make up the binding pockets in *S. aureus* MurB (as set forth in FIG. 4) of at most about 1.5 Å. How this calculation is obtained is described below.

Accordingly, the invention thus provides molecules or molecular complexes comprising an *S. aureus* MurB binding pocket or *S. aureus* MurB-like binding pocket, as defined by the sets of structure coordinates described above.

Three-Dimensional Configurations

X-ray structure coordinates define a unique configuration of points in space. Those of skill in the art understand that a set of structure coordinates for protein or an protein/ligand complex, or a portion thereof, define a relative set of points that, in turn, define a configuration in three dimensions. A similar or identical configuration can be defined by an entirely different set of coordinates, provided the distances and angles between coordinates remain essentially the same. In addition, a scalable configuration of points can be defined by increasing or decreasing the distances between coordinates by a scalar factor while keeping the angles essentially the same.

The present invention thus includes the scalable three-dimensional configuration of points derived from the structure coordinates of at least a portion of an *S. aureus* MurB molecule or molecular complex, as listed in FIG. 4, as well as structurally equivalent configurations, as described below. Preferably, the scalable three-dimensional configuration includes points derived from structure coordinates representing the locations of a plurality of the amino acids defining an *S. aureus* MurB binding pocket.

In one embodiment, the scalable three-dimensional configuration includes points derived from structure coordinates representing the locations of the backbone atoms of a plurality of amino acids defining the *S. aureus* MurB FAD binding pocket, preferably the amino acids listed is Table 1, more preferably the amino acids listed in Table 2, and most preferably the amino acids listed in Table 3; in another embodiment, the three-dimensional configuration includes points derived from structure coordinates representing the locations of the side chain and the backbone atoms (other than hydrogens) of a plurality of the amino acids defining the *S. aureus* MurB FAD binding pocket, preferably the amino acids listed is Table 1, more preferably the amino acids listed in Table 2, and most preferably the amino acids listed in Table 3.

In another embodiment, the scalable three-dimensional configuration includes points derived from structure coordinates representing the locations of the backbone atoms of a plurality of amino acids defining the *S. aureus* MurB substrate binding pocket, preferably the amino acids listed is Table 4, more preferably the amino acids listed in Table 5, and most preferably the amino acids listed in Table 6; in another embodiment, the three-dimensional configuration includes points derived from structure coordinates representing the locations of the side chain and the backbone atoms (other than hydrogens) of a plurality of the amino acids defining the *S. aureus* MurB substrate binding pocket, preferably the amino acids listed is Table 4, more preferably the amino acids listed in Table 5, and most preferably the amino acids listed in Table 6.

Likewise, the invention also includes the scalable three-dimensional configuration of points derived from structure coordinates of molecules or molecular complexes that are structurally homologous to *S. aureus* MurB, as well as structurally equivalent configurations. Structurally homologous molecules or molecular complexes are defined below. Advantageously, structurally homologous molecules can be identified using the structure coordinates of *S. aureus* MurB (FIG. 4) according to a method of the invention.

The configurations of points in space derived from structure coordinates according to the invention can be visualized as, for example, a holographic image, a stereodiagram, a model or a computer-displayed image, and the invention thus includes such images, diagrams or models.

Structurally Equivalent Crystal Structures

Various computational analyses can be used to determine whether a molecule or the binding pocket portion thereof is "structurally equivalent," defined in terms of its three-dimensional structure, to all or part of *S. aureus* MurB or its binding pockets. Such analyses may be carried out in current software applications, such as the Molecular Similarity application of QUANTA (Molecular Simulations Inc., San Diego, Calif.) version 4.1, and as described in the accompanying User's Guide.

The Molecular Similarity application permits comparisons between different structures, different conformations of the same structure, and different parts of the same structure. The procedure used in Molecular Similarity to compare structures is divided into four steps: (1) load the structures to be compared; (2) define the atom equivalences in these structures; (3) perform a fitting operation; and (4) analyze the results.

Each structure is identified by a name. One structure is identified as the target (i.e., the fixed structure); all remaining structures are working structures (i.e., moving structures). Since atom equivalency within QUANTA is defined by user input, for the purpose of this invention equivalent atoms are defined as protein backbone atoms (N, Cα, C, and O) for all conserved residues between the two structures being compared. A conserved residue is defined as a residue that is structurally or functionally equivalent. Only rigid fitting operations are considered.

When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by QUANTA.

For the purpose of this invention, any molecule or molecular complex or binding pocket thereof, or any portion thereof, that has a root mean square deviation of conserved residue backbone atoms (N, Cα, C, O) of less than about 1.5 Å, when superimposed on the relevant backbone atoms described by the reference structure coordinates listed in FIG. 4, is considered structurally equivalent" to the reference molecule. That is to say, the crystal structures of those portions of the two molecules are substantially identical, within acceptable error. Particularly preferred structurally equivalent molecules or molecular complexes are those that are defined by the entire set of structure coordinates listed in FIG. 4, ± a root mean square deviation from the conserved backbone atoms of those amino acids of not more than 1.5 Å. More preferably, the root mean square deviation is less than about 1.0 Å.

The term "root mean square deviation" means the square root of the arithmetic mean of the squares of the deviations. It is a way to express the deviation or variation from a trend or object. For purposes of this invention, the "root mean square deviation" defines the variation in the backbone of a protein from the backbone of *S. aureus* MurB or a binding pocket portion thereof, as defined by the structure coordinates of *S. aureus* MurB described herein.

Machine Readable Storage Media

Transformation of the structure coordinates for all or a portion of *S. aureus* MurB or the *S. aureus* MurB/ligand complex or one of its binding pockets, for structurally homologous molecules as defined below, or for the structural equivalents of any of these molecules or molecular complexes as defined above, into three-dimensional graphical representations of the molecule or complex can be conveniently achieved through the use of commercially-available software.

The invention thus further provides a machine-readable storage medium comprising a data storage material encoded with machine readable data which, when using a machine programmed with instructions for using said data, is capable of displaying a graphical three-dimensional representation of any of the molecule or molecular complexes of this invention that have been described above. In a preferred embodiment, the machine-readable data storage medium comprises a data storage material encoded with machine readable data which, when using a machine programmed with instructions for using said data, is capable of displaying a graphical three-dimensional representation of a molecule or molecular complex comprising all or any parts of an *S. aureus* MurB binding pocket or an *S. aureus* MurB-like binding pocket, as defined above. In another preferred embodiment, the machine-readable data storage medium is capable of displaying a graphical three-dimensional representation of a molecule or molecular complex defined by the structure coordinates of all of the amino acids listed in FIG. 4, ± a root mean square deviation from the backbone atoms of said amino acids of not more than 1.5 Å.

In an alternative embodiment, the machine-readable data storage medium comprises a data storage material encoded with a first set of machine readable data which comprises the Fourier transform of the structure coordinates set forth in FIG. 4, and which, when using a machine programmed with instructions for using said data, can be combined with a second set of machine readable data comprising the x-ray diffraction pattern of a molecule or molecular complex to determine at least a portion of the structure coordinates corresponding to the second set of machine readable data.

For example, a system for reading a data storage medium may include a computer comprising a central processing unit ("CPU"), a working memory which may be, e.g., RAM (random access memory) or "core" memory, mass storage memory (such as one or more disk drives or CD-ROM drives), one or more display devices (e.g., cathode-ray tube ("CRT") displays, light emitting diode ("LED") displays, liquid crystal displays ("LCDs"), electroluminescent displays, vacuum fluorescent displays, field emission displays ("FEDs"), plasma displays, projection panels, etc.), one or more user input devices (e.g., keyboards, microphones, mice, touch screens, etc.), one or more input lines, and one or more output lines, all of which are interconnected by a conventional bidirectional system bus. The system may be a stand-alone computer, or may be networked (e.g., through local area networks, wide area networks, intranets, extranets, or the internet) to other systems (e.g., computers, hosts, servers, etc.). The system may also include additional computer controlled devices such as consumer electronics and appliances.

Input hardware may be coupled to the computer by input lines and may be implemented in a variety of ways. Machine-readable data of this invention may be inputted via the use of a modem or modems connected by a telephone line or dedicated data line. Alternatively or additionally, the input hardware may comprise CD-ROM drives or disk drives. In conjunction with a display terminal, a keyboard may also be used as an input device.

Output hardware may be coupled to the computer by output lines and may similarly be implemented by conventional devices. By way of example, the output hardware may include a display device for displaying a graphical representation of a binding pocket of this invention using a program such as QUANTA as described herein. Output hardware might also include a printer, so that hard copy output may be produced, or a disk drive, to store system output for later use.

In operation, a CPU coordinates the use of the various input and output devices, coordinates data accesses from mass storage devices, accesses to and from working memory, and determines the sequence of data processing steps. A number of programs may be used to process the machine-readable data of this invention. Such programs are discussed in reference to the computational methods of drug discovery as described herein. References to components of the hardware system are included as appropriate throughout the following description of the data storage medium.

Machine-readable storage devices useful in the present invention include, but are not limited to, magnetic devices, electrical devices, optical devices, and combinations thereof. Examples of such data storage devices include, but are not limited to, hard disk devices, CD devices, digital video disk devices, floppy disk devices, removable hard disk devices, magneto-optic disk devices, magnetic tape devices, flash memory devices, bubble memory devices, holographic storage devices, and any other mass storage peripheral device. It should be understood that these storage devices include necessary hardware (e.g., drives, controllers, power supplies, etc.) as well as any necessary media (e.g., disks, flash cards, etc.) to enable the storage of data.

Structurally Homologous Molecules, Molecular Complexes, and Crystal Structures

The structure coordinates set forth in FIG. 4 can be used to aid in obtaining structural information about another crystallized molecule or molecular complex. The method of the invention allows determination of at least a portion of the three-dimensional structure of molecules or molecular complexes which contain one or more structural features that are similar to structural features of S. aureus MurB. These molecules are referred to herein as "structurally homologous" to S. aureus MurB. Similar structural features can include, for example, regions of amino acid identity, conserved active site or binding site motifs, and similarly arranged secondary structural elements (e.g., α helices and β sheets). Optionally, structural homology is determined by aligning the residues of the two amino acid sequences to optimize the number of identical amino acids along the lengths of their sequences; gaps in either or both sequences are permitted in making the aligmnent in order to optimize the number of identical amino acids, although the amino acids in each sequence must nonetheless remain in their proper order. Preferably, two amino acid sequences are compared using the Blastp program, version 2.0.9, of the BLAST 2 search algorithm, as described by Tatusova et al., *FEMS Microbiol Lett* 174, 247–50 (1999), and available at http://www.ncbi.nlm.nih.gov/gorf/b12.html. Preferably, the default values for all BLAST 2 search parameters are used, including matrix=BLOSUM62; open gap penalty=11, extension gap penalty=1, gap x_dropoff=50, expect=10, wordsize=3, and filter on. In the comparison of two amino acid sequences using the BLAST search algorithm, structural similarity is referred to as "identity." Preferably, a structurally homologous molecule is a protein that has an amino acid sequence sharing at least 65% identity with a native or recombinant amino acid sequence of S. aureus MurB (for example, SEQ ID NO:1). More preferably, a protein that is structurally homologous to S. aureus MurB includes at least one contiguous stretch of at least 50 amino acids that shares at least 80% amino acid sequence identity with the analogous portion of the native or recombinant S. aureus MurB (for example, SEQ ID NO:1). Methods for generating structural information about the structurally homologous molecule or molecular complex are well-known and include, for example, molecular replacement techniques.

Therefore, in another embodiment this invention provides a method of utilizing molecular replacement to obtain structural information about a molecule or molecular complex whose structure is unknown comprising the steps of:

(a) crystallizing the molecule or molecular complex of unknown structure;

(b) generating an x-ray diffraction pattern from said crystallized molecule or molecular complex; and (c) applying at least a portion of the structure coordinates set forth in FIG. 4 to the x-ray diffraction pattern to generate a three-dimensional electron density map of the molecule or molecular complex whose structure is unknown.

By using molecular replacement, all or part of the structure coordinates of S. aureus MurB or the S. aureus MurB/ligand complex as provided by this invention (and set forth in FIG. 4) can be used to determine the structure of a crystallized molecule or molecular complex whose structure is unknown more quickly and efficiently than attempting to determine such information ab initio.

Molecular replacement provides an accurate estimation of the phases for an unknown structure. Phases are a factor in equations used to solve crystal structures that cannot be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a structurally homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of S. aureus MurB or the S. aureus MurB/ligand complex according to the structure coordinates listed in FIG. 4 within the unit cell of the crystal of the unknown molecule or molecular complex so as best to account for the observed x-ray diffraction pattern of the crystal of the molecule or molecular complex whose structure is unknown. Phases can then be calculated from this model and combined with the observed x-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex (E. Lattman, "Use of the Rotation and Translation Functions," in Meth. Enzymol., 115, pp. 55–77 (1985); M. G. Rossman, ed., "The Molecular Replacement Method," Int. Sci. Rev. Ser., No. 13, Gordon & Breach, New York (1972)).

Structural information about a portion of any crystallized molecule or molecular complex that is sufficiently structurally homologous to a portion of S. aureus MurB can be resolved by this method. In addition to a molecule that shares one or more structural features with S. aureus MurB as described above, a molecule that has similar bioactivity, such as the same catalytic activity, substrate specificity or ligand binding activity as S. aureus MurB, may also be sufficiently structurally homologous to S. aureus MurB to permit use of the structure coordinates of S. aureus MurB to solve its crystal structure.

In a preferred embodiment, the method of molecular replacement is utilized to obtain structural information about a molecule or molecular complex, wherein the molecule or molecular complex comprises at least one S. aureus MurB subunit or homolog. A "subunit" of S. aureus MurB is an S. aureus MurB molecule that has been truncated at the N-terminus or the C-terminux, or both. In the context of the present invention, a "homolog" of S. aureus MurB is a protein that contains one or more amino acid substitutions, deletions, additions, or rearrangements with respect to the amino acid sequence of S. aureus MurB, but that, when folded into its native conformation, exhibits or is reasonably expected to exhibit at least a portion of the tertiary (three-dimensional) structure of S. aureus MurB. For example, structurally homologous molecules can contain deletions or additions of one or more contiguous or noncontiguous amino acids, such as a loop or a domain. Structurally homologous molecules also include "modified" S. aureus MurB molecules that have been chemically or enzymatically derivatized at one or more constituent amino acid, including side chain modifications, backbone modifications, and N- and C-terminal modifications including acetylation, hydroxylation, methylation, amidation, and the attachment of carbohydrate or lipid moieties, cofactors, and the like.

A heavy atom derivative of S. aureus MurB is also included as an S. aureus MurB homolog. The term "heavy atom derivative" refers to derivatives of S. aureus MurB produced by chemically modifying a crystal of S. aureus MurB. In practice, a crystal is soaked in a solution containing heavy metal atom salts, or organometallic compounds, e.g., lead chloride, gold thiomalate, thiomersal or uranyl acetate, which can diffuse through the crystal and bind to the surface of the protein. The location(s) of the bound heavy metal atom(s) can be determined by x-ray diffraction analysis of the soaked crystal. This information, in turn, is used to generate the phase information used to construct three-dimensional structure of the protein (T. L. Blundell and N. L. Johnson, Protein Crystallography, Academic Press (1976)).

Because it is expected that S. aureus MurB can crystallize in more than one crystal form, the structure coordinates of S. aureus MurB as provided by this invention are particularly useful in solving the structure of other crystal forms of S. aureus MurB or S. aureus MurB complexes.

The structure coordinates of S. aureus MurB as provided by this invention are particularly useful in solving the structure of S. aureus MurB mutants. Mutants may be prepared, for example, by expression of S. aureus MurB cDNA previously altered in its coding sequence by oligonucleotide-directed mutagenesis. Mutants may also be generated by site-specific incorporation of unnatural amino acids into MurB proteins using the general biosynthetic method of C. J. Noren et al., Science, 244:182–188 (1989). In this method, the codon encoding the amino acid of interest in wild-type S. aureus MurB is replaced by a "blank" nonsense codon, TAG, using oligonucleotide-directed mutagenesis. A suppressor tRNA directed against this codon is then chemically aminoacylated in vitro with the desired unnatural amino acid. The aminoacylated tRNA is then added to an in vitro translation system to yield a mutant S. aureus thymidylate kinase with the site-specific incorporated unnatural amino acid.

Selenocysteine or selenomethionine may be incorporated into wild-type or mutant S. aureus MurB by expression of S. aureus MurB-encoding cDNAs in auxotrophic E. coli strains (W. A Hendrickson et al., EMBO J., 9(5):1665–1672 (1990)). In this method, the wild-type or mutagenized S. aureus MurB cDNA may be expressed in a host organism on a growth medium depleted of either natural cysteine or methionine (or both) but enriched in selenocysteine or selenomethionine (or both). Alternatively, selenomethionine analogues may be prepared by down regulation methionine biosynthesis. (T. E. Benson et al., Nat. Struct. Biol., 2:644–53 (1995); G. D. Van Duyne et al., J. Mol. Biol. 229:105–24 (1993)).

The structure coordinates of S. aureus MurB listed in FIG. 4 are also particularly useful to solve the structure of crystals of S. aureus MurB, S. aureus MurB mutants or S. aureus MurB homologs co-complexed with a variety of chemical entities. This approach enables the determination of the optimal sites for interaction between chemical entities, including candidate S. aureus MurB inhibitors and S. aureus MurB. Potential sites for modification within the various binding site of the molecule can also be identified. This information provides an additional tool for determining the most efficient binding interactions, for example, increased hydrophobic interactions, between S. aureus MurB and a chemical entity. For example, high resolution x-ray diffraction data collected from crystals exposed to different types of solvent allows the determination of where each type of solvent molecule resides. Small molecules that bind tightly to those sites can then be designed and synthesized and tested for their S. aureus MurB inhibition activity.

All of the complexes referred to above may be studied using well-known x-ray diffraction techniques and may be refined versus 1.5–3 Å resolution x-ray data to an R value of about 0.20 or less using computer software, such as X-PLOR (Yale University, ©1992, distributed by Molecular Simulations, Inc.; see, e.g., Blundell & Johnson, supra; *Meth. Enzymol.,* Vol. 114 & 115, H. W. Wyckoff et al., eds., Academic Press (1985)). This information may thus be used to optimize known *S. aureus* MurB inhibitors, and more importantly, to design new *S. aureus* MurB inhibitors.

The invention also includes the unique three-dimensional configuration defined by a set of points defined by the structure coordinates for a molecule or molecular complex structurally homologous to *S. aureus* MurB as determined using the method of the present invention, structurally equivalent configurations, and magnetic storage media comprising such set of structure coordinates.

Further, the invention includes structurally homologous molecules as identified using the method of the invention.

Homology Modeling

Using homology modeling, a computer model of an *S. aureus* MurB homolog can be built or refined without crystallizing the homolog. First, a preliminary model of the *S. aureus* MurB homolog is created by sequence alignment with *S. aureus* MurB, secondary structure prediction, the screening of structural libraries, or any combination of those techniques. Computational software may be used to carry out the sequence alignments and the secondary structure predictions. Structural incoherences, e.g., structural fragments around insertions and deletions, can be modeled by screening a structural library for peptides of the desired length and with a suitable conformation. For prediction of the side chain conformation, a side chain rotamer library may be employed. Where the *S. aureus* MurB homolog has been crystallized, the final homology model can be used to solve the crystal structure of the homolog by molecular replacement, as described above. Next, the preliminary model is subjected to energy minimization to yield an energy minimized model. The energy minimized model may contain regions where stereochemistry restraints are violated, in which case such regions are remodeled to obtain a final homology model. The homology model is positioned according to the results of molecular replacement, and subjected to further refinement comprising molecular dynamics calculations.

Rotational Drug Design

Computational techniques can be used to screen, identify, select and design chemical entities capable of associating with *S. aureus* MurB or structurally homologous molecules. Knowledge of the structure coordinates for *S. aureus* MurB permits the design and/or identification of synthetic compounds and/or other molecules which have a shape complementary to the conformation of an *S. aureus* MurB binding site. In particular, computational techniques can be used to identify or design chemical entities, such as inhibitors, agonists and antagonists, that associate with an *S. aureus* MurB binding pocket or an *S. aureus* MurB-like binding pocket. Inhibitors may bind to or interfere with all or a portion of the active site of *S. aureus* MurB, and can be competitive, non-competitive, or uncompetitive inhibitors. Once identified and screened for biological activity, these inhibitors/agonists/antagonists may be used therapeutically or prophylactically to block *S. aureus* MurB activity and, thus, inhibit the growth of the bacteria or cause its death. Structure-activity data for analogs of ligands that bind to or interfere with *S. aureus* MurB or *S. aureus* MurB-like binding pockets can also be obtained computationally.

The term "chemical entity," as used herein, refers to chemical compounds, complexes of two or more chemical compounds, and fragments of such compounds or complexes. Chemical entities that are determined to associate with *S. aureus* MurB are potential drug candidates.

Data stored in a machine-readable storage medium that is capable of displaying a graphical three-dimensional representation of the structure of *S. aureus* MurB or a structurally homologous molecule, as identified herein, or portions thereof may thus be advantageously used for drug discovery. The structure coordinates of the chemical entity are used to generate a three-dimensional image that can be computationally fit to the three-dimensional image of *S. aureus* MurB or a structurally homologous molecule. The three-dimensional molecular structure encoded by the data in the data storage medium can then be computationally evaluated for its ability to associate with chemical entities. When the molecular structures encoded by the data is displayed in a graphical three-dimensional representation on a computer screen, the protein structure can also be visually inspected for potential association with chemical entities.

One embodiment of the method of drug design involves evaluating the potential association of a known chemical entity with *S. aureus* MurB or a structurally homologous molecule, particularly with an *S. aureus* MurB binding pocket (e.g., an FAD binding pocket, a substrate binding pocket, etc.) or *S. aureus* MurB-like binding pocket. The method of drug design thus includes computationally evaluating the potential of a selected chemical entity to associate with any of the molecules or molecular complexes set forth above. This method comprises the steps of: (a) employing computational means to perform a fitting operation between the selected chemical entity and a binding pocket, or a pocket nearby the substrate binding pocket, of the molecule or molecular complex; and (b) analyzing the results of said fitting operation to quantify the association between the chemical entity and the binding pocket.

In another embodiment, the method of drug design involves computer-assisted design of chemical entities that associate with *S. aureus* MurB, its homologs, or portions thereof. Chemical entities can be designed in a step-wise fashion, one fragment at a time, or may be designed as a whole or "de novo."

To be a viable drug candidate, the chemical entity identified or designed according to the method must be capable of structurally associating with at least part of an *S. aureus* MurB or *S. aureus* MurB-like binding pockets, and must be able, sterically and energetically, to assume a conformation that allows it to associate with the *S. aureus* MurB or *S. aureus* MurB-like binding pocket. Non-covalent molecular interactions important in this association include hydrogen bonding, van der Waals interactions, hydrophobic interactions, and electrostatic interactions. Conformational considerations include the overall three-dimensional structure and orientation of the chemical entity in relation to the binding pocket, and the spacing between various functional groups of an entity that directly interact with the *S. aureus* MurB-like binding pocket or homologs thereof.

Optionally, the potential binding of a chemical entity to an *S. aureus* MurB or *S. aureus* MurB-like binding pocket is analyzed using computer modeling techniques prior to the actual synthesis and testing of the chemical entity. If these computational experiments suggest insufficient interaction and association between it and the *S. aureus* MurB or *S. aureus* MurB-like binding pocket, testing of the entity is obviated. However, if computer modeling indicates a strong interaction, the molecule may then be synthesized and tested for its ability to bind to or interfere with an *S. aureus* MurB or *S. aureus* MurB-like binding pocket. Binding assays to determine if a compound actually binds to *S. aureus* MurB can also be performed and are well known in the art. Binding assays may employ kinetic or thermodynamic methodology using a wide variety of techniques including, but not limited to, microcalorimetry, circular dichroism, capillary zone electrophoresis, nuclear magnetic resonance spectroscopy, fluorescence spectroscopy, and combinations thereof.

One skilled in the art may use one of several methods to screen chemical entities or fragments for their ability to associate with an *S. aureus* MurB or *S. aureus* MurB-like binding pocket. This process may begin by visual inspection of, for example, an *S. aureus* MurB or *S. aureus* MurB-like binding pocket on the computer screen based on the *S. aureus* MurB structure coordinates listed in FIG. 4 or other coordinates which define a similar shape generated from the machine-readable storage medium. Selected fragments or chemical entities may then be positioned in a variety of orientations, or docked, within the binding pocket. Docking may be accomplished using software such as QUANTA and SYBYL, followed by energy minimization and molecular dynamics with standard molecular mechanics forcefields, such as CHARMM and AMBER.

Specialized computer programs may also assist in the process of selecting fragments or chemical entities. Examples include GRID (P. J. Goodford, *J. Med. Chem.* 28:849–857 (1985); available from Oxford University, Oxford, UK); MCSS (A. Miranker et al., *Proteins: Struct. Funct. Gen.,*11:29–34 (1991); available from Molecular Simulations, San Diego, Calif.); AUTODOCK (D. S. Goodsell et al., *Proteins: Struct. Funct. Genet.* 8:195–202 (1990); available from Scripps Research Institute, La Jolla, Calif.); and DOCK (I. D. Kuntz et al., *J. Mol. Biol.* 161:269–288 (1982); available from University of California, San Francisco, Calif.).

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of *S. aureus* MurB. This would be followed by manual model building using software such as QUANTA or SYBYL (Tripos Associates, St. Louis, Mo.).

Useful programs to aid one of skill in the art in connecting the individual chemical entities or fragments include, without limitation, CAVEAT (P. A. Bartlett et al., in *Molecular Recognition in Chemical and Biological Problems,*" Special Publ., Royal Chem. Soc., 78:182–196 (1989); G. Lauri et al., *J. Comput. Aided Mol. Des.* 8:51–66 (1994); available from the University of California, Berkeley, Calif.); 3D database systems such as ISIS (available from MDL Information Systems, San Leandro, Calif.; reviewed in Y. C. Martin, *J. Med. Cham.* 35:2145–2154 (1992)); and HOOK (M. B. Eisen et al., *Proteins: Struc. Funct., Genet.* 19:199–221 (1994); available from Molecular Simulations, San Diego, Calif.).

*S. aureus* MurB binding compounds may be designed "de novo" using either an empty binding site or optionally including some portion(s) of a known inhibitor(s). There are many de novo ligand design methods including, without limitation, LUDI (H.-J. Bohm, *J. Comp. Aid. Molec. Design.* 6:61–78 (1992); available from Molecular Simulations Inc., San Diego, Calif.); LEGEND (Y. Nishibata et al., *Tetrahedron,* 47:8985 (1991); available from Molecular Simulations Inc., San Diego, Calif.); LeapFrog (available from Tripos Associates, St. Louis, Mo.); and SPROUT (V. Gillet et al., *J. Comput. Aided Mol. Design* 7:127–153 (1993); available from the University of Leeds, UK).

Once a compound has been designed or selected by the above methods, the efficiency with which that entity may bind to or interfere with an *S. aureus* MurB or *S. aureus* MurB-like binding pocket may be tested and optimized by computational evaluation. For example, an effective *S. aureus* MurB or *S. aureus* MurB-like binding pocket inhibitor must preferably demonstrate a relatively small difference in energy between its bound and free states (i.e., a small deformation energy of binding). Thus, the most efficient *S. aureus* MurB or *S. aureus* MurB-like binding pocket inhibitors should preferably be designed with a deformation energy of binding of not greater than about 10 kcal/mole; more preferably, not greater than 7 kcal/mole. *S. aureus* MurB or *S. aureus* MurB-like binding pocket inhibitors may interact with the binding pocket in more than one conformation that is similar in overall binding energy. In those cases, the deformation energy of binding is taken to be the difference between the energy of the free entity and the average energy of the conformations observed when the inhibitor binds to the protein.

An entity designed or selected as binding to or interfering with an *S. aureus* MurB or *S. aureus* MurB-like binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole, and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. 15106); AMBER, version 4.1 (P. A. Kollman, University of California at San Francisco, 94143); QUANTA/CHARMM (Molecular Simulations, Inc., San Diego, Calif. 92121); Insight II/Discover (Molecular Simulations, Inc., San Diego, Calif. 92121); DelPhi (Molecular Simulations, Inc., San Diego, Calif. 92121); and AMSOL (Quantum Chemistry Program Exchange, Indiana University). These programs may be implemented, for instance, using a Silicon Graphics workstation such as an $Indigo^2$ with "IMPACT" graphics. Other hardware systems and software packages will be known to those skilled in the art.

Another approach encompassed by this invention is the computational screening of small molecule databases for chemical entities or compounds that can bind in whole, or in part, to a *S. aureus* MurB or *S. aureus* MurB-like binding pocket. In this screening, the quality of fit of such entities to the binding site may be judged either by shape complementarity or by estimated interaction energy (E. C. Meng et al., *J. Comp. Chem.,* 13, pp. 505–524 (1992)).

This invention also enables the development of chemical entities that can isomerize to short-lived reaction intermediates in the chemical reaction of a substrate or other compound that interferes with or with *S. aureus* MurB. Time-dependent analysis of structural changes in *S. aureus* MurB during its interaction with other molecules is carried out. The reaction intermediates of *S. aureus* MurB can also be deduced from the reaction product in co-complex with *S. aureus* MurB. Such information is useful to design improved analogs of known *S. aureus* MurB inhibitors or to design novel classes of inhibitors based on the reaction intermediates of the *S. aureus* MurB and inhibitor co-complex. This provides a novel route for designing *S. aureus* MurB inhibitors with both high specificity and stability.

Yet another approach to rational drug design involves probing the *S. aureus* MurB crystal of the invention with molecules comprising a variety of different functional groups to determine optimal sites for interaction between candidate *S. aureus* MurB inhibitors and the protein. For example, high resolution x-ray diffraction data collected from crystals soaked in or co-crystallized with other molecules allows the determination of where each type of solvent molecule sticks. Molecules that bind tightly to those sites can then be further modified and synthesized and tested for their MurB inhibitor activity (J. Travis, *Science*, 262:1374 (1993)).

In a related approach, iterative drug design is used to identify inhibitors of *S. aureus* MurB. Iterative drug design is a method for optimizing associations between a protein and a compound by determining and evaluating the three-dimensional structures of successive sets of protein/compound complexes. In iterative drug design, crystals of a series of protein/compound complexes are obtained and then the three-dimensional structures of each complex is solved. Such an approach provides insight into the association between the proteins and compounds of each complex. This is accomplished by selecting compounds with inhibitory activity, obtaining crystals of this new protein/compound complex, solving the three dimensional structure of the complex, and comparing the associations between the new protein/compound complex and previously solved protein/compound complexes. By observing how changes in the compound affected the protein/compound associations, these associations may be optimized.

A compound that is identified or designed as a result of any of these methods can be obtained (or synthesized) and tested for its biological activity, e.g., inhibition of MurB activity.

Pharmaceutical Compositions

Pharmaceutical compositions of this invention comprise an inhibitor of *S. aureus* MurB activity identified according to the invention, or a pharmaceutically acceptable salt thereof, and a pharmaceutically acceptable carrier, adjuvant, or vehicle. The term "pharmaceutically acceptable carrier" refers to a carrier(s) that is "acceptable" in the sense of being compatible with the other ingredients of a composition and not deleterious to the recipient thereof. Optionally, the pH of the formulation is adjusted with pharmaceutically acceptable acids, bases, or buffers to enhance the stability of the formulated compound or its delivery form.

Methods of making and using such pharmaceutical compositions are also included in the invention. The pharmaceutical compositions of the invention can be administered orally, parenterally, by inhalation spray, topically, rectally, nasally, buccally, vaginally, or via an implanted reservoir. Oral administration or administration by injection is preferred. The term parenteral as used herein includes subcutaneous, intracutaneous, intravenous, intramuscular, intra-articular, intrasynovial, intrasternal, intrathecal, intralesional, and intracranial injection or infusion techniques.

Dosage levels of between about 0.01 and about 100 mg/kg body weight per day, preferably between about 0.5 and about 75 mg/kg body weight per day of the *S. aureus* MurB inhibitory compounds described herein are useful for the prevention and treatment of *S. aureus* MurB mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

In order that this invention be more fully understood, the following examples are set forth. These examples are for the purpose of illustration only and are not to be construed as limiting the scope of the invention in any way.

EXAMPLES

Example 1

Analysis of the Structure of *S. aureus* MurB

Expression of MurB and Incorporation of Selenomethionine

*S. aureus* MurB was expressed using UC 15169, *E. coli* construct K12S (F' lacI$^q$) (pQE-10 murBb). Genes and polypeptides derived from *S. aureus*, including *S. aureus* and MurB, are published in EP 786519 A2 and WO 0012678, both assigned to Human Genome Sciences. MurB cloned into pQE-10 (Qiagen) was obtained from Human Genome Sciences. For expression, the plasmid was transformed into the *E. coli* K12S F' cell line which has an ampicillin resistance marker. Stock supplies of the culture were maintained at −80° C. in Luria Broth containing ampicillin at 100 μg/mL with 10% glycerol added as a cryopreservative agent.

Seed fermentations were prepared in 100 mL volumes of M9 medium contained in 500 mL wide mouth fermentation flasks. The formulation of basal M9 utilized for these studies was $Na_2HPO_4$, 6 g; $KH_2PO_4$, 3 g; $NH_4Cl$, 1.0 g; and NaCl, 0.5 g per liter of deionized water. The pH was adjusted to 7.4 with concentrated KOH. The medium was sterilized by autoclaving for 30 minutes. Prior to inoculation, the following filter sterilized solutions were added per liter of basal medium: 1M $MgSO_4$, 1.0 mL; 1M $CaCl_2$, 0.3 mL; trace metal salts solution, 0.3 mL and 20% glucose, 20 mL. The trace metal salts solution contained per liter of deionized water: $MgCl_2.6H_2O$, 39.44 g; $MnSO_4.H_2O$, 5.58 g; $FeSO_4.7H_2O$, 1.11 g; $Na_2MoO_4.2H_2O$, 0.48 g; $CaCl_2$, 0.33 g; NaCl, 0.12 g; and ascorbic acid, 1.0 g. Filter sterilized ampicillin was added to the medium at a final concentration of 100 μg/mL. A 0.1 mL aliquot of the stock culture was inoculated into the medium and allowed to grow at 37° C. for 18–20 hours with a shaking rate of 200 rpm. The mature seed culture was harvested by centrifugation and then resuspended in an equal volume of M9 medium. The resuspended seed was used to inoculate expression fermentations at a rate of 3%.

For expression of selenomethionine MurB, M9 media was again utilized in 100 mL volumes containing 100 μg/mL of ampicillin. Multiple flasks were employed to achieve the desired production volume. Since UC 15169 is not a methionine auxotroph, incorporation of selenomethionine was accomplished through down-regulation of methionine biosynthesis just prior to induction of MurB expression with IPTG, isopropyl thio-β-D-galactosidase (G. D. Van Duyne et al., *J. Mol. Biol.* 229, 105–24 (1993); T. E. Benson et al., *Nat. Struct. Biol.* 2, 644–53 (1995)). The culture was grown at 37° C. with a shaking rate of 200 rpm until an $A_{600}$ of ~0.6. At this point, the following filter sterilized amino acids were added. L-lysine, L-threonine, and L-phenylalanine were added to final concentrations of 100 μg/mL. L-leucine, L-isoleucine, and L-valine were added to final concentrations of 50 μg/mL. Filter sterilized L-selenomethionine was added simultaneously to a final concentration of 50 μg/mL. After 15–20 minutes, protein expression was induced by the addition of filter sterilized IPTG to a final concentration of 1 mM. Growth of the culture was continued at 200 rpm for an additional 4 hours until an $A_{600}$ of ~2.0. This coincided with maximum growth and maximum expression of MurB. Cells were then harvested by centrifugation and frozen at −80° C. Under these conditions, the average yield of cell paste was 4–4.5 g/L. Selenomethionyl MurB comprised roughly 2–5% of the total cell protein with >75% expressed in the soluble form.

Purification of Selenomethionine MurB

All operations were performed at 4° C. and 2-mercaptoethanol and DTT were added to buffers immediately before use. Three hundred milliliters of quilibration buffer (50 mM Tris, pH 7.8, 500 mM NaCl, 10% glycerol, 25 mM imidazole, 5 mM 2-mercaptoethanol) containing 0.2 mg/mL DNAse I (Boehringer Mannheim #104159) was added to 26 g of cell paste obtained from 6 L of fermentation broth and was resuspended by using a Tekmar Tissumizer set on a power setting of 60. The suspension was homogenized by passing it twice through a Rannie homogenizer at 10,000 PSI. The homogenate was centrifuged at 39,200× g for 60 minutes in a JA20 rotor in a Beckman J2-21 centrifuge. The supernatant was filtered by using a Nalgene 0.2 μm CN filter unit and applied to a Qiagen NTA Superflow column charged with nickel (column volume of 7.9 mL). The column was then washed with 4 column volumes of equilibration buffer and 22 column volumes of wash buffer (50 mM Tris, pH 7.8, 500 mM NaCl, 10% glycerol, 50 mM imidazole, 5 mM 2-mercaptoethanol) at a flow rate of 108 mL/hr and eluted with 2.5 column volumes of elution buffer (50 mM Tris, pH 7.8, 500 mM NaCl, 10% glycerol, 300 mM imidazole, 5 mM 2-mercaptoethanol) at a flow rate of 60 mL/hr. DTT was added to the eluted material to a final concentration of 10 mM and the treated material was dialyzed for 22 hours against two changes of nitrogen sparged dialysis buffer (50 mM Tris pH 7.8, 500 mM NaCl, 10% glycerol, and 10 mM DTT). After dialysis the sample was sterile filtered, fractionated, and stored at −80° C.

The protein concentration was 2.42 mg/mL as determined by amino acid analysis. The prepared MurB protein had the correct N-terminal sequence for the first 20 residues. The mass, as measured by electrospray mass spectrometry, was 36,220 Da, in excellent agreement with the theoretical mass of 36,207 Da, indicating full incorporation of the five selenomethionines into the protein. Amino acid analysis gave a correlation coefficient of 0.99 between the recovered and theoretical amino acid composition, indicative not only of high purity but also of the correct amino acid composition in the protein.

Protein Crystallization

Protein samples were buffer exchanged into 20 mM HEPES pH 7.5, 5 mM 2-mercaptoethanol and concentrated to 20 mg/mL using an Ultrafree 0.5 centrifugal filters with a Biomax 10K membrane (Millipore, Bedford, Mass.). Selenomethionine MurB crystals were grown in 3 μL+3 μL sitting drops in 9.75% PEG 8000, 0.1 M cacodylic acid pH 6.5, 0.55 M ammonium sulfate, 20% DMSO, 5 mM 2-mercaptoethanol with 1 mM EP-UDPGlcNAc substrate. These conditions were originally identified by screening for crystallization conditions with the methionine incorporated S. aureas MurB. The hexagonal shaped crystals grew over a period of two to three weeks. The mother liquor served as the cryoprotectant for freezing during data collection at 100 K in liquid nitrogen.

Data Collection and Structure Determination

Access to synchrotron radiation at the Advance Photon Source at Argonne National Labs (IMCA-CAT, Beamline 17-ID) afforded the opportunity to solve the S. aureus MurB structure by multiple anomalous dispersion (AD) phasing. EXAFS analysis revealed a sharp selenium K edge for the selenomethionine MurB (data not shown). A three wavelength experiment was carried out with a low energy wavelength (12,000 eV, 1.0332 Å), a wavelength corresponding to the inflection point of the absorption edge (12,659.4 eV, 0.97939 Å), and a wavelength collected at the peak of the absorption edge (12,660.8 eV, 0.97928 Å). All diffraction data were collected on a 2 k by 2 k Brüker CCD detector.

Data sets at each wavelength were processed separately with the program SAINT (Siemens Analytical X-ray Systems, Madison, Wis.) while keeping the anomalous pairs separate (Table 7). The inflection point and peak data sets were scaled to the remote energy data set using SCALEIT in CCP4 (Collaborative Computational Project, N.4 Acta Cryst. D50, 760–63 (1994)) by treating the remote wavelength as native. Anomalous and dispersive difference Patterson maps showed strong signals for 4 of the 5 selenium atoms suggesting the N-terminal methionine was disordered. Locations of the selenium sites were determined using the automated Patterson solution routine in SHEIX (G. M. Sheldrick & R. O. Gould, Acta. Cryst. B51, 423–31 (1995)). The location of each selenium site was confirmed by the ability of individual sites to generate phases which could identify the other sites in cross difference Fourier calculations. All heavy atom parameter refinement and phasing calculations were carried out with MLPHARE (Z. Otwinowski, in Isomorphous Replacement and Anomalous Scattering 80–86 (W. Wolf et al., eds., SERC Daresbury Laboratory, Warrington) (1991); Collaborative Computational Project, N.4 Acta Cryst. D50, 760–63 (1994)) by treating the remote wavelength as native and the edge and peak wavelengths as derivatives (V. Ramakrishnan et al., Nature 362, 219–23 (1993)). The phases were subsequently subjected to solvent flattening using the program DM (K. D. Cowtan & P. Main, Acta. Cryst. D49, 148–57 (1993); K. D. Cowtan & P. Main, Acta Cryst. D54, 487–93 (1998); Collaborative Computational Project, N.4 Acta Cryst. D50, 760–63 (1994)).

Model building was performed using the program CHAIN (J. S. Sack, J. Mol Graph. 6, 224–25 (1988)). The E. coli MurB model was used as a template for model building in order to speed the placement of the main chain atoms. All refinement steps were carried out using XPLOR 3.8.5.1 and XPLOR 98.0 (A. T. Brunger, Methods. Mol. Biol. 56, 245–6 (1996)) against the 1.0332 Å (low energy) data set. Several rounds of torsional dynamics (L. M. Rice & A. T. Brunger, Proteins 19, 277–90 (1994)) and simulated annealing (A. T. Brunger, J. Mol. Biol. 203, 803–16 (1988)) with rebuilding after each round of refinement were carried out. In the later stages of refinement, a bulk solvent model was included in order to properly account for inclusion of lower resolution data (J. S. Jiang & A. T. Brunger, J. Mol. Biol. 243, 100–15 (1994)). Progress of the refinement was monitored by the Free R factor which was calculated for 10% of the reflections that were not included in refinement (A. T. Brunger, Nature 355, 472–75 (1992)). Analysis by PROCHECK showed good main chain geometry and side chain torsion angles (R. A. Laskowski et al., J. App. Cryst. 26, 283–91 (1993)). FIG. 3 was made with Setor (S. V. Evans, J. Mol. Graph. 11, 134–38 (1993)). FIG. 5 was made with Molscript 2.1 (P. Kraulis, J. Appl. Cryst. 24, 946–50 (1991)) and Raster3D (E. A. Merritt & D. J. Bacon, Meth. Enzymol. 277, 505–24 (1997)), and FIGS. 7 and 11 were made with Molscript 2.1 only.

SEQUENCE LISTING FREE TEXT

SEQ ID NO:1 Recombinant S. aureus MurB protein including polyhistidine ($His_6$) region.

SEQ ID NO:2 *E. Coli* MurB protein.
SEQ ID NO:3 *Helicobacter pylori* MurB protein.
SEQ ID NO:4 *Aquifex aeolicus* MurB protein.
SEQ ID NO:5 *Bacillus subtilis* MurB protein.
SEQ ID NO:6 *Borrelia burgdorferi* MurB protein.
SEQ ID NO:7 *Chlamydia pneumoniae* MurB protein.
SEQ ID NO:8 *Rickettsia prowazekii* MurB protein.
SEQ ID NO:9 *Haemophilus influenzae* MurB protein.
SEQ ID NO:10 *Salmonella typhimurium* MurB protein.
SEQ ID NO:11 *Bordetella pertussis* MurB protein.

What is claimed is:

1. A method for crystallizing an *Staphylococcus aureus* UDP-N-acetylenolpyruvylglucosamine reductase molecule or molecular complex comprising:

preparing purified *S. aureus* MurB at a concentration of about 1 mg/ml to about 50 mg/ml; and crystallizing *S. aureus* MurB from a solution comprising about 1 wt. % to about 50 wt. % PEG, 0 wt. % to about 40 wt. % DMSO, about 100 mM to about 1 M ammonium or lithium sulfate, about 0 mM to about 20 mM 2-mercaptoethanol, about 0.005 mM to about 40 mM EP-UDPGlcNAc, and buffered to a pH of about 5 to about 8.

2. A crystal of *Staphylococcus aureus* UDP-N-acetylenolpyruvylglucosamine reductase.

3. The crystal of claim 2 having the trigonal space group symmetry $I2_13$.

4. The crystal of claim 2 comprising a unit cell having dimensions $a=b=c=178.9\pm20$ Å, and $\alpha=\beta=\gamma=90°$.

5. The crystal of claim 2 comprising the atoms listed in FIG. 4 arranged in a spatial relationship represented by the structure coordinates listed in FIG. 4.

6. The crystal of claim 2 wherein UDP-N-acetylenolpyruvylglucosamine reductase has amino acid sequence of SEQ ID NO:1.

7. The crystal of claim 2 wherein UDP-N-acetylenolpyruvylglucosamine reductase has amino acid sequence of SEQ ID NO:1, except that at least one methionine in SEQ ID NO:1 is replaced with selenomethionine.

* * * * *